US005477858A

United States Patent [19]
Norris et al.

[11] Patent Number: 5,477,858
[45] Date of Patent: Dec. 26, 1995

[54] ULTRASOUND BLOOD FLOW/TISSUE IMAGING SYSTEM

[75] Inventors: Paul R. Norris, Issaquah; John Folline, Kent; Richard H. Chesarek, Seattle; Michael J. Veraya, Kent; James R. Chekerylla, Issaquah; Richard A. Revell, Issaquah; Thomas R. Clary, Issaquah; Richard K. Johnson, Issaquah; Lee D. Dunbar, Bothell; David R. Axness, Tukwila; John C. Lazenby, Bellevue; Donald R. Gardner, Renton; William E. Crone, Redmond; W. Gerrit Barrere, Kirkland; Charles C. Myrick; Bruce M. Pirie, both of Renton; Leonard D. Seader, Maple Valley; Louis A. Heaton, Carnation; David M. Polakowski, Renton; Brian J. Sargent, Redmond, all of Wash.

[73] Assignee: Siemens Medical Systems, Inc., Iselin, N.J.

[21] Appl. No.: 728,830

[22] Filed: Jul. 9, 1991

Related U.S. Application Data

[63] Continuation of Ser. No. 515,311, Apr. 26, 1990, abandoned, which is a continuation of Ser. No. 892,753, Aug. 1, 1986, abandoned, which is a continuation-in-part of Ser. No. 892,211, Jul. 30, 1986, abandoned.

[51] Int. Cl.⁶ .............................. A61B 8/06; G01N 29/00
[52] U.S. Cl. ............................. 128/660.05; 128/661.09; 73/626; 73/6; 333/138
[58] Field of Search ................ 128/660.04, 660.05, 128/660.07, 661.09, 661.1; 73/625, 626, 631; 333/138

[56] References Cited

U.S. PATENT DOCUMENTS

| | | | |
|---|---|---|---|
| 4,208,602 | 6/1980 | Stoller | 128/660.09 X |
| 4,416,286 | 11/1983 | Iimuma et al. | 128/661.09 X |
| 4,446,395 | 5/1984 | Hadjicostis | 128/662.03 X |
| 4,459,854 | 7/1984 | Richardson et al. | 128/662.03 X |
| 4,481,823 | 11/1984 | Alais | 73/625 X |
| 4,501,278 | 2/1985 | Yamaguchi et al. | 128/662.05 |
| 4,505,156 | 3/1985 | Questo | 73/626 |
| 4,519,260 | 5/1985 | Fu et al. | 128/661.1 X |
| 4,534,357 | 8/1985 | Powers | 128/661.09 |
| 4,583,552 | 4/1986 | Iimuma | 128/661.09 |

Primary Examiner—Francis Jaworski
Attorney, Agent, or Firm—Seed A. Berry; Lawrence C. Edelman

[57] ABSTRACT

An ultrasound imaging system is provided which produces gray scale images of the anatomy simultaneous with Doppler signal processing so as to provide a single real-time image that shows not only the vascular anatomy and surrounding tissue but also flow events in the vascular compartment. A phased linear array having near-continuous focus over the scanning field provides high resolution and very small Doppler sample volumes. The system tests incoming signals from throughout the scanning field for amplitude, phase and frequency so as to determine B-mode data, motion presence and direction, and echo source velocity.

52 Claims, 987 Drawing Sheets

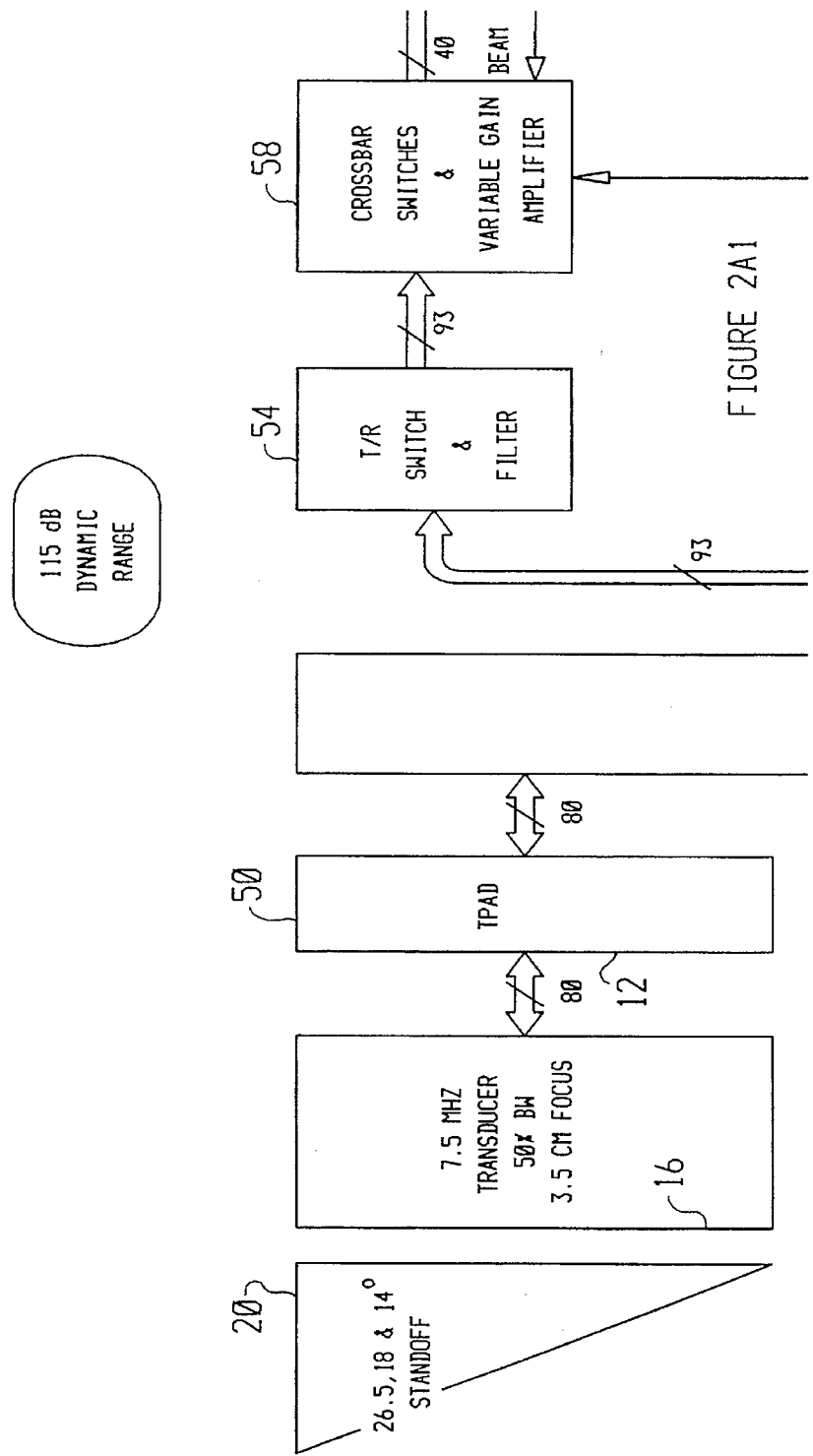

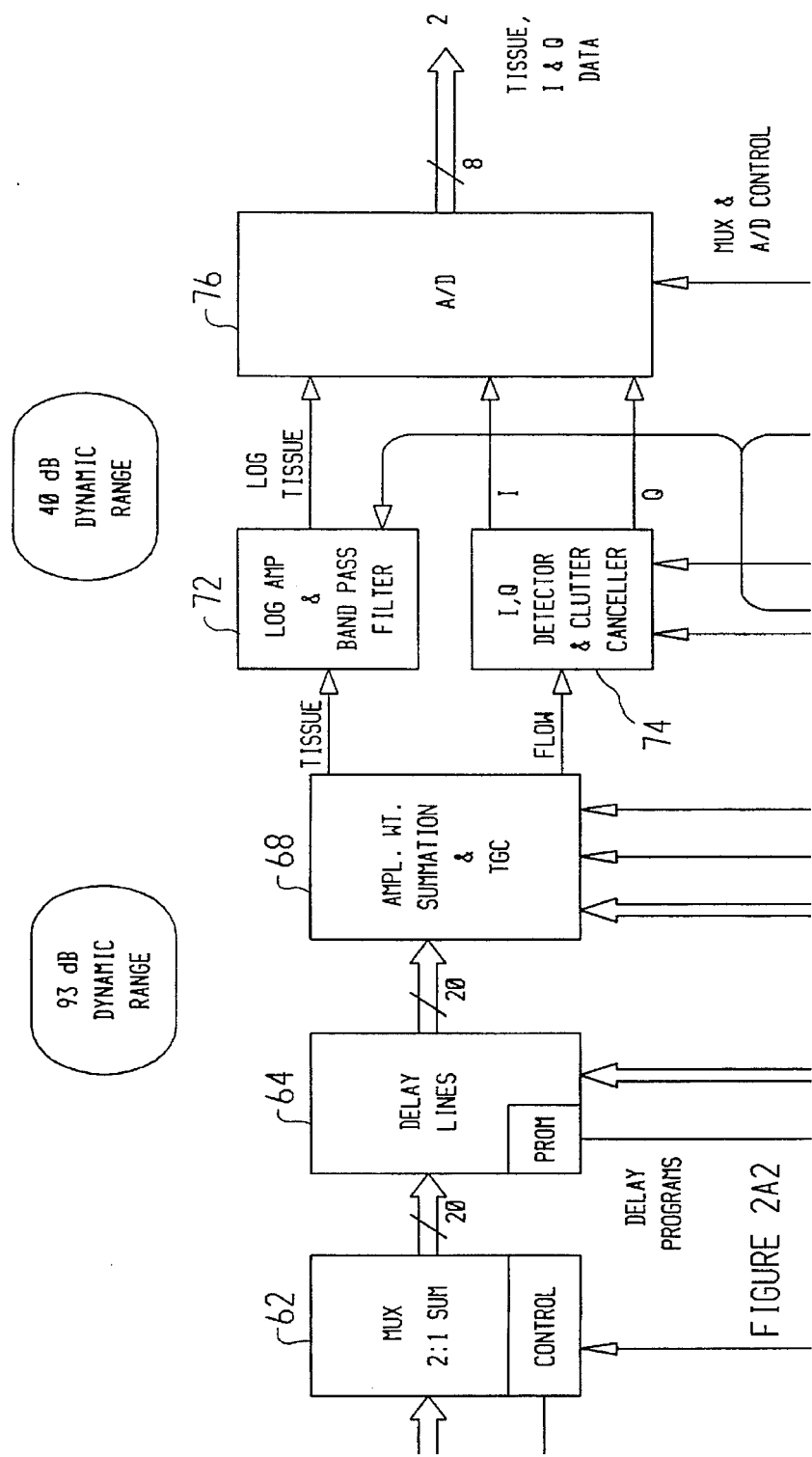
FIGURE 2A2

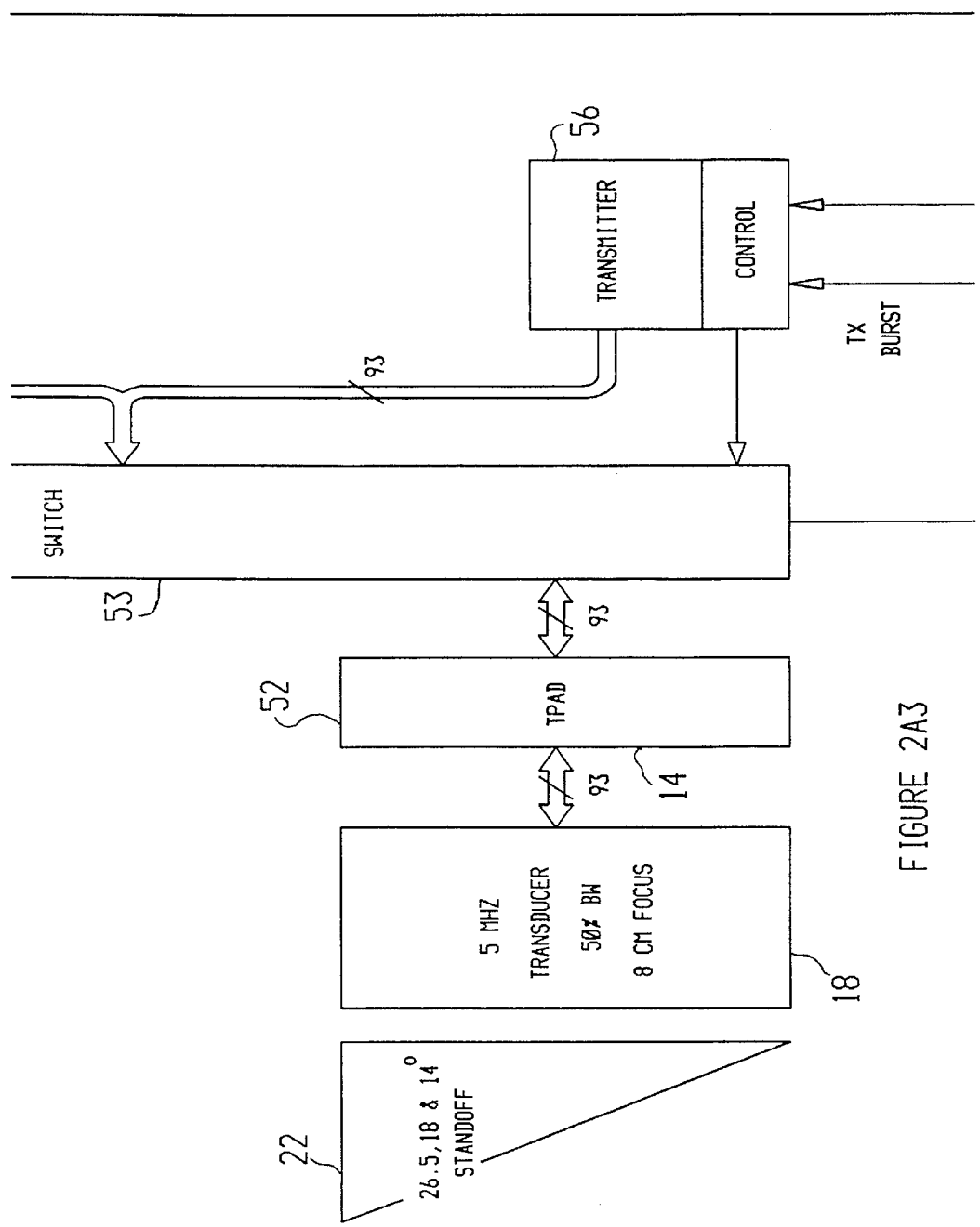

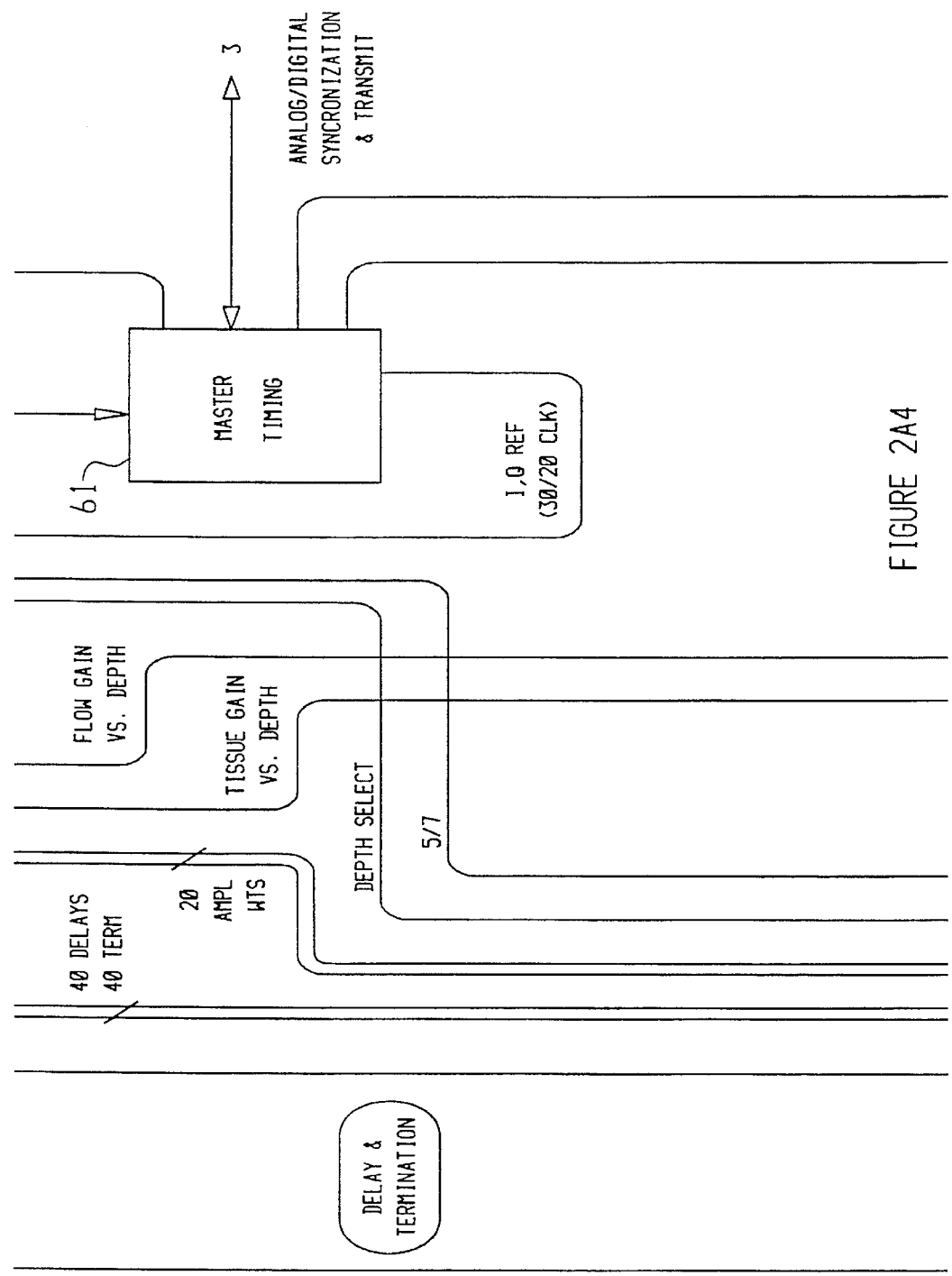

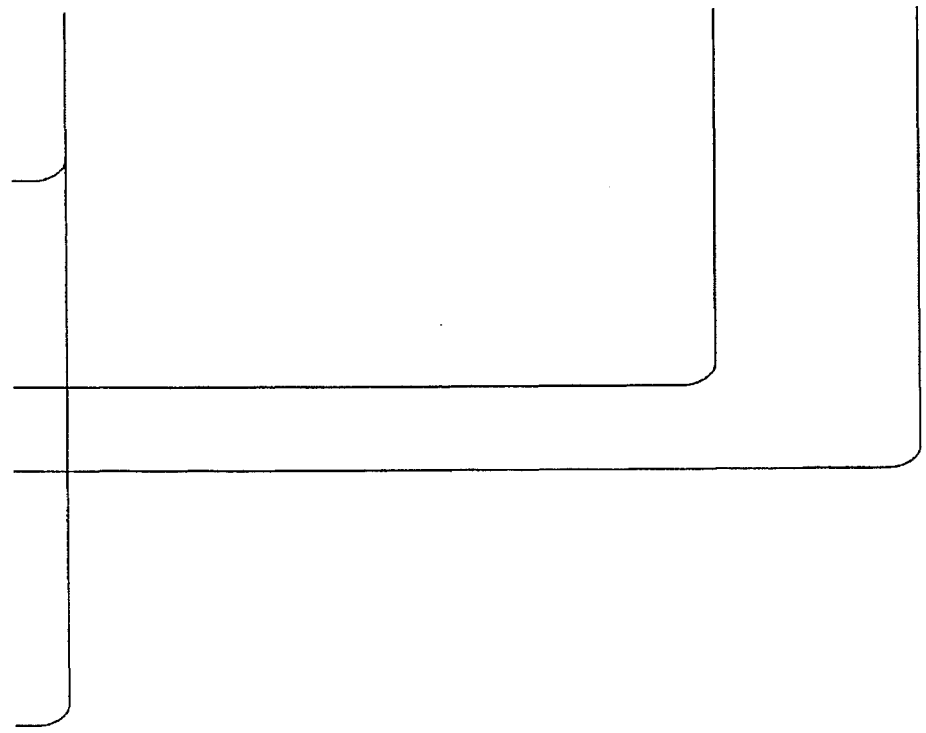
FIGURE 2A5

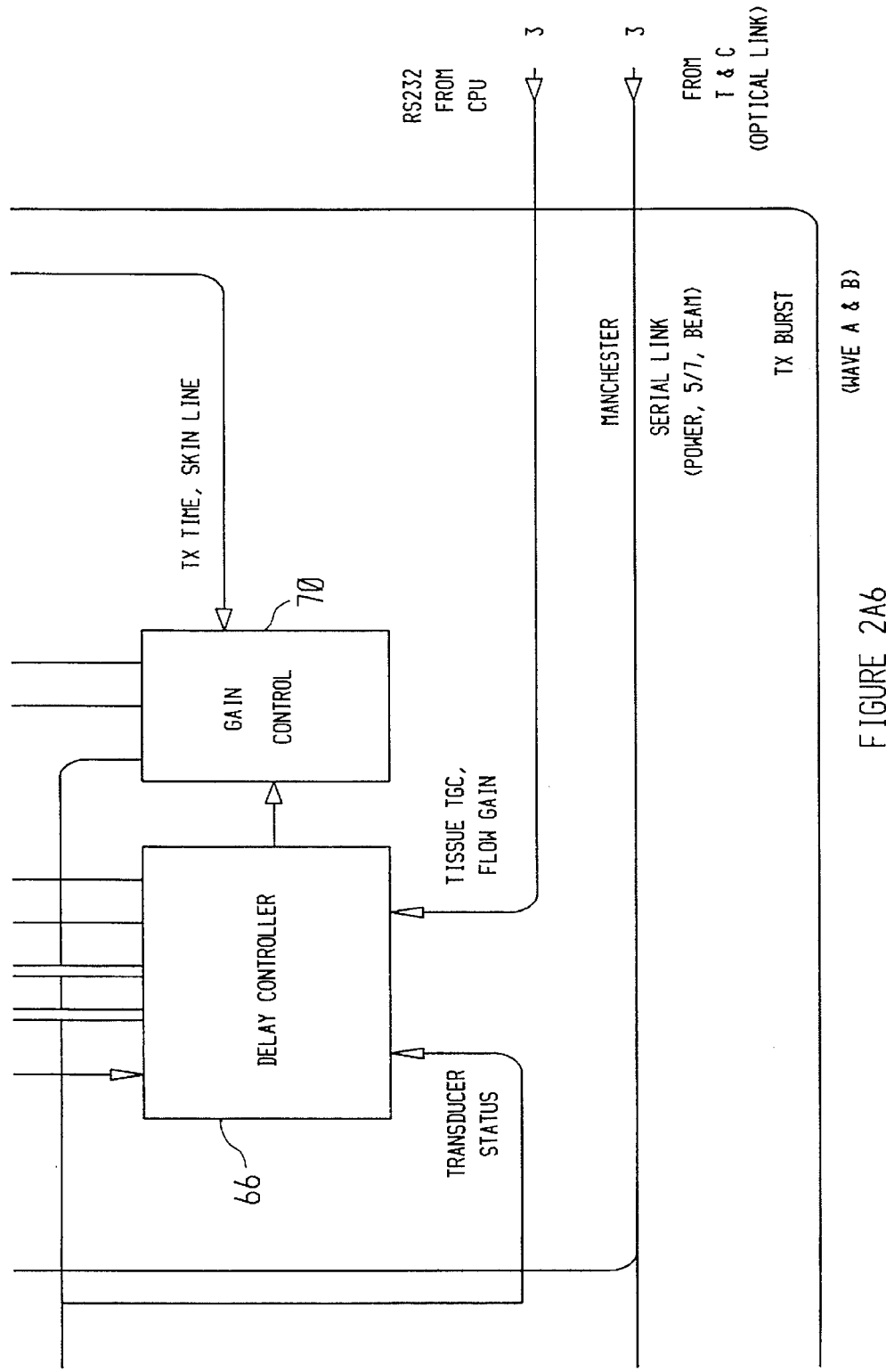
FIGURE 2A6

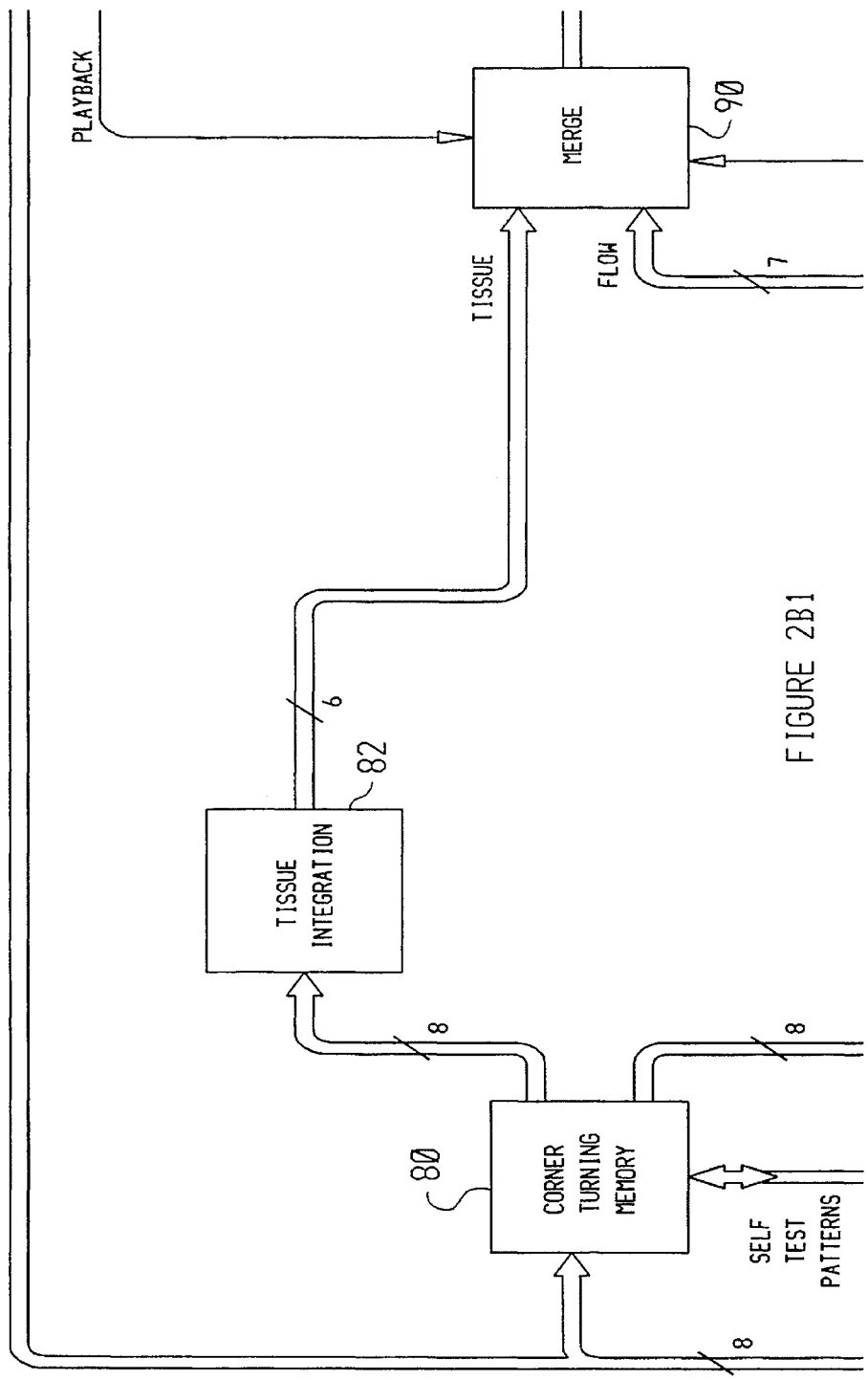
FIGURE 2B1

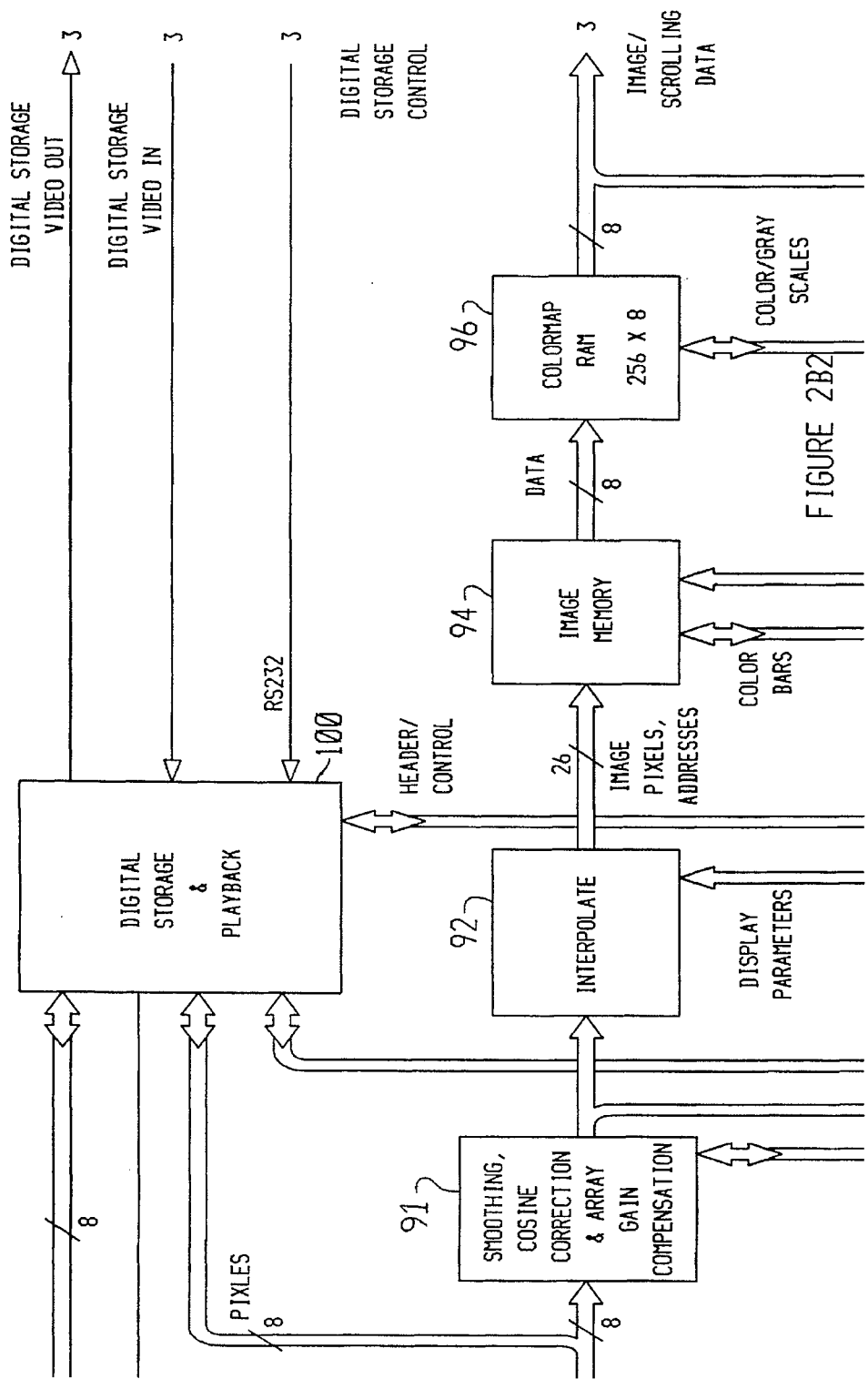
FIGURE 2B2

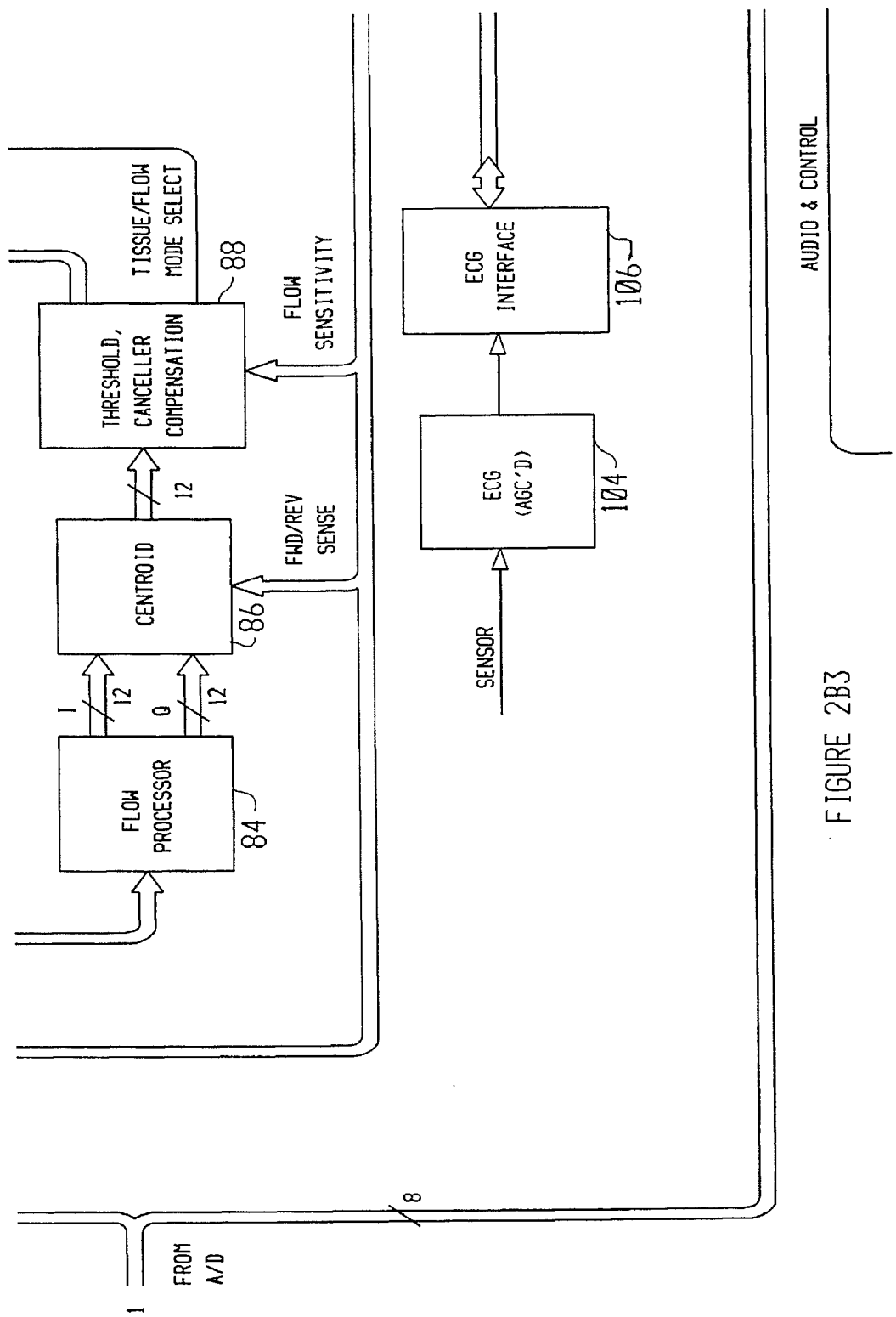
FIGURE 2B3

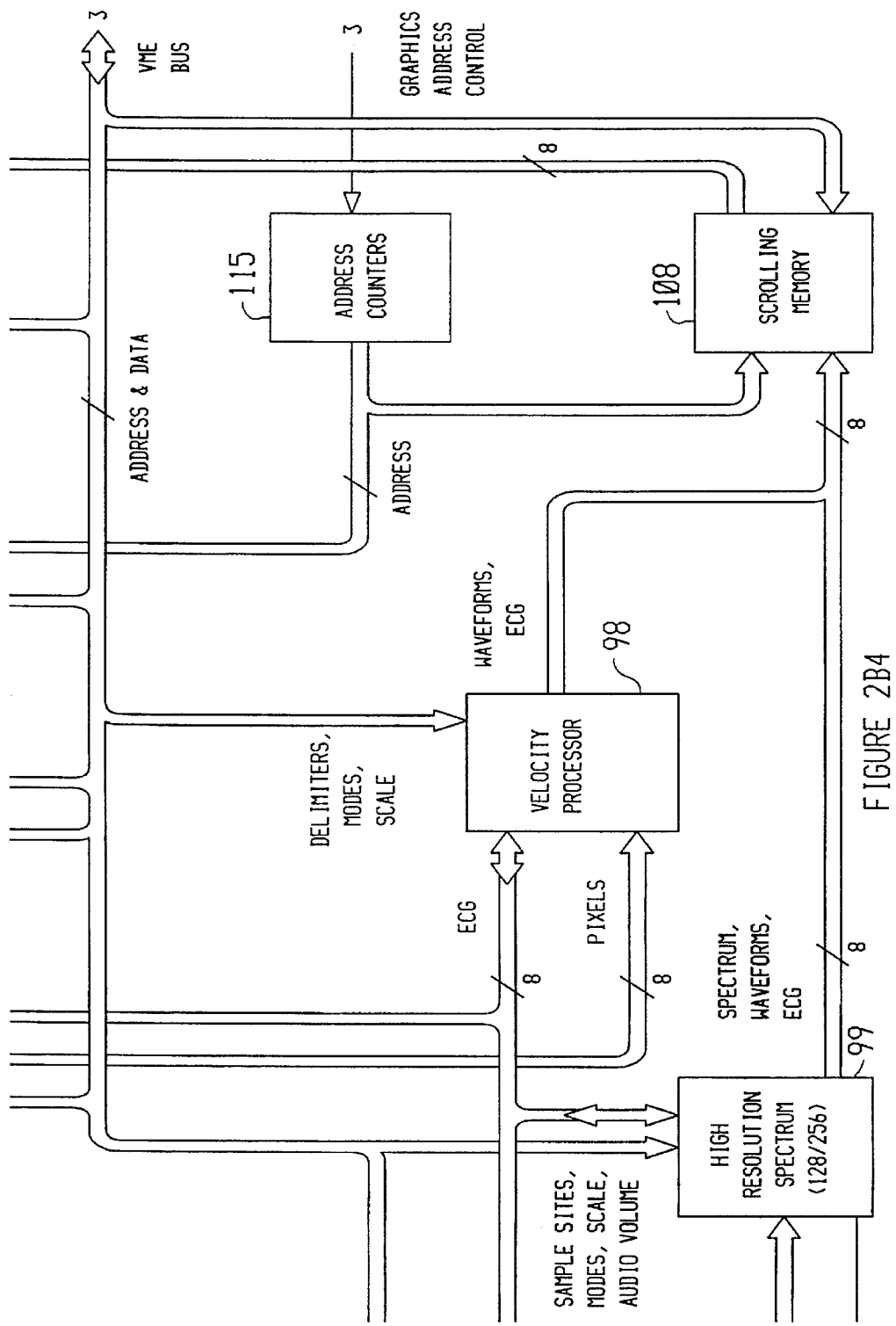

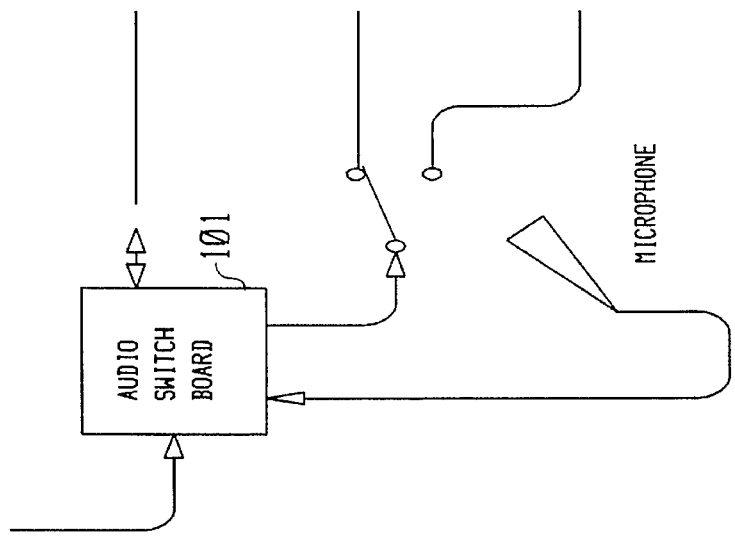
FIGURE 2B5

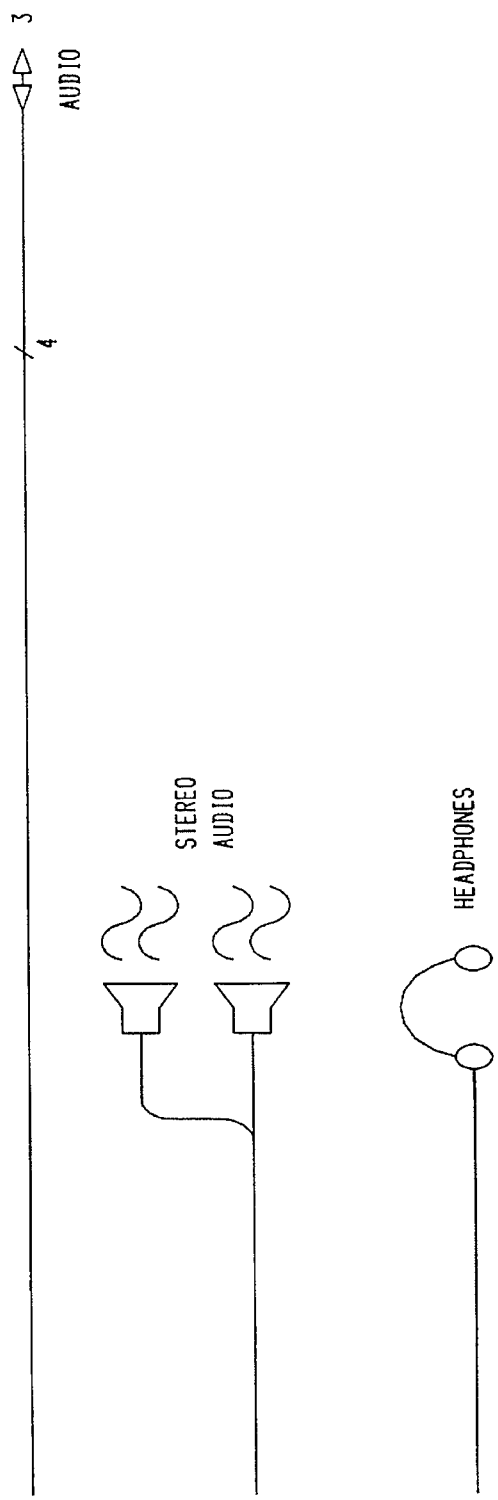
FIGURE 2B6

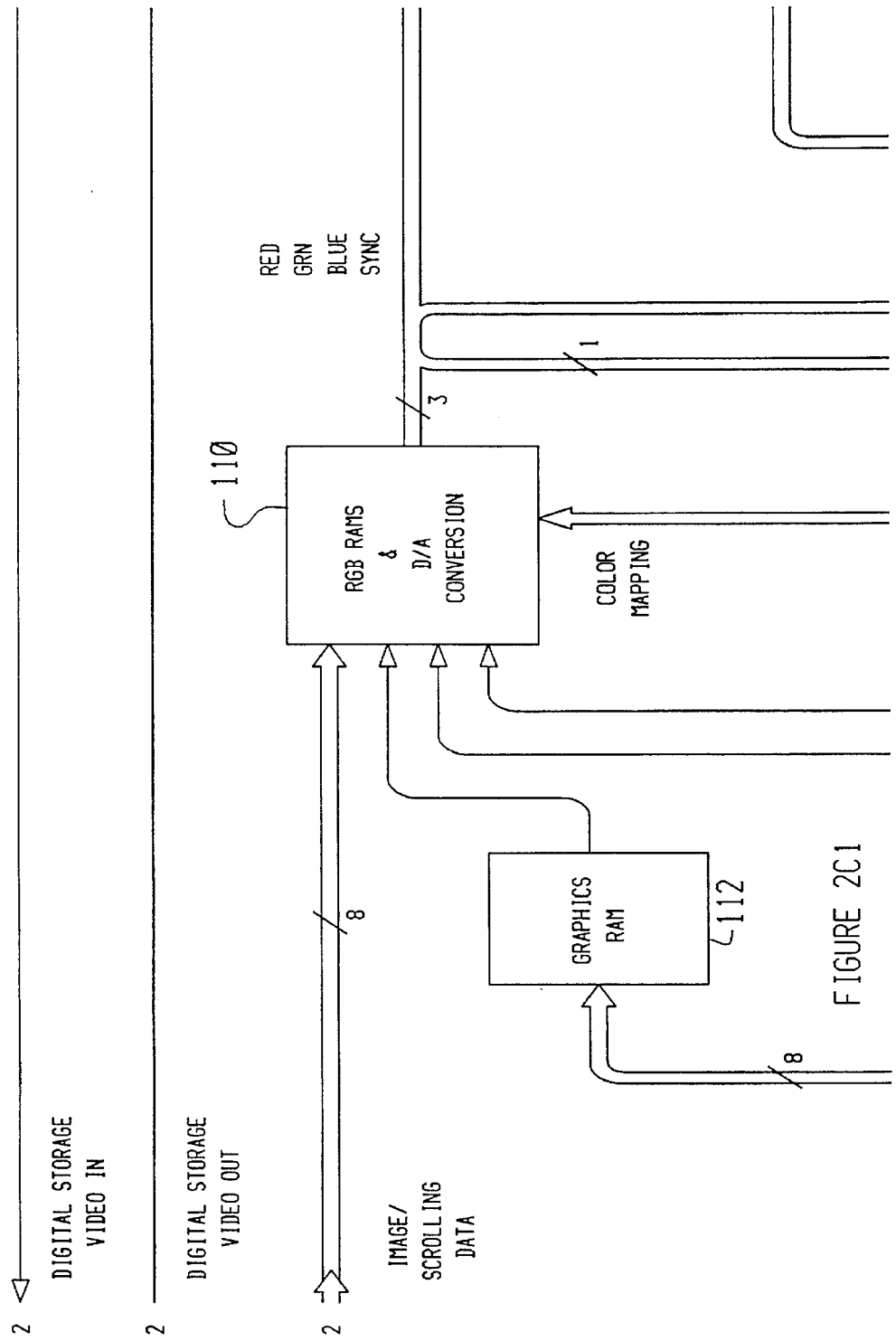
FIGURE 2C1

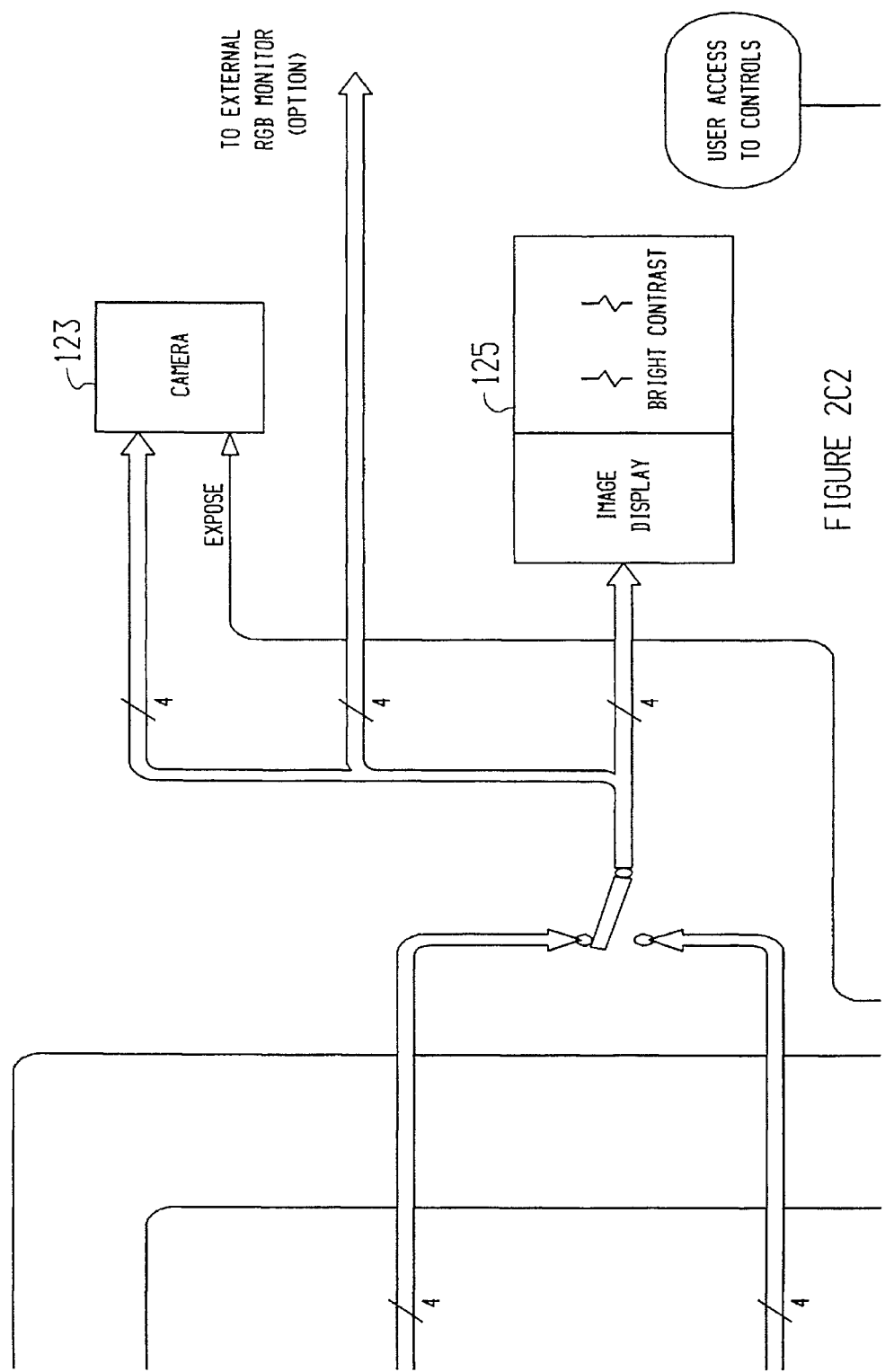
FIGURE 2C2

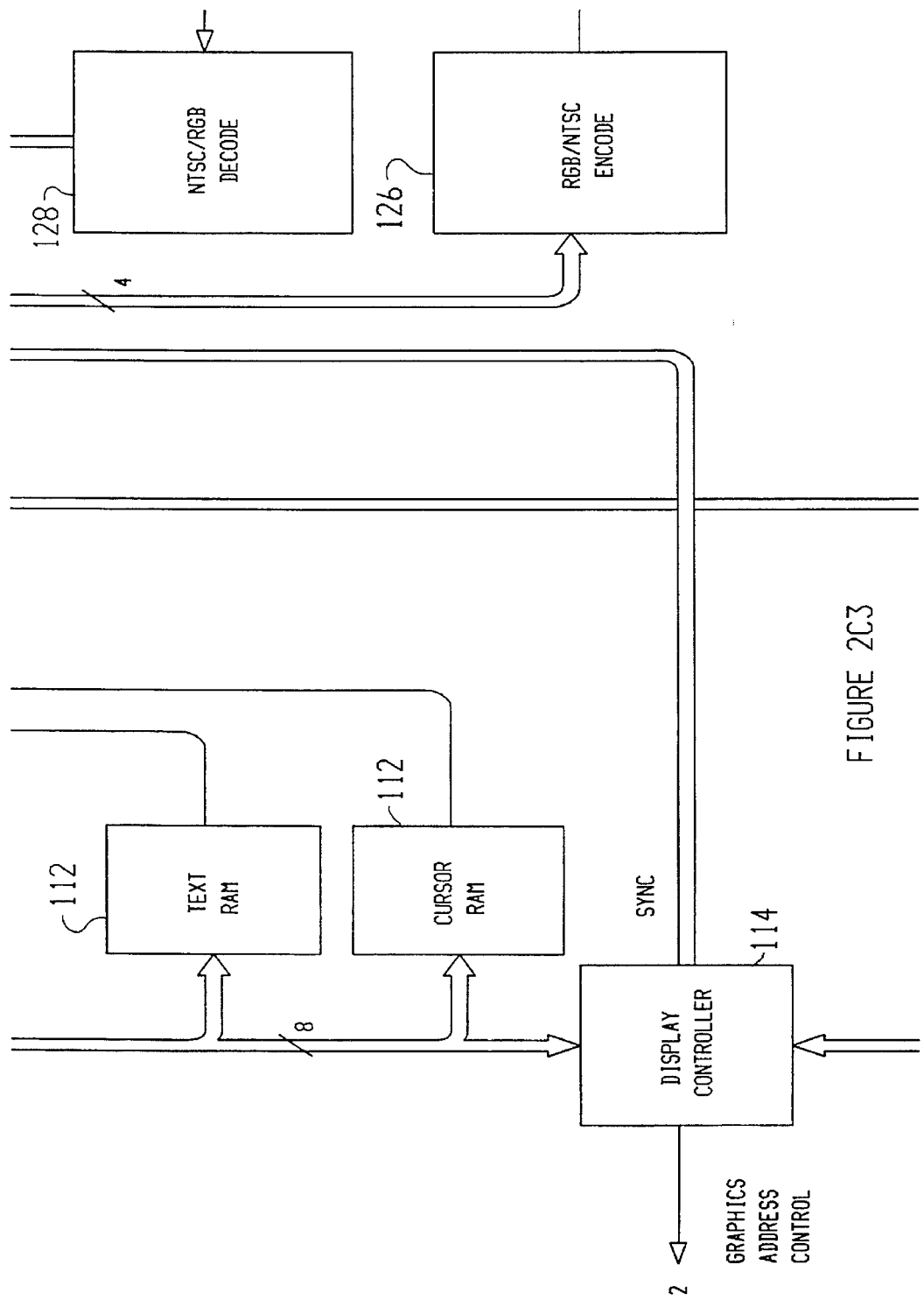
FIGURE 2C3

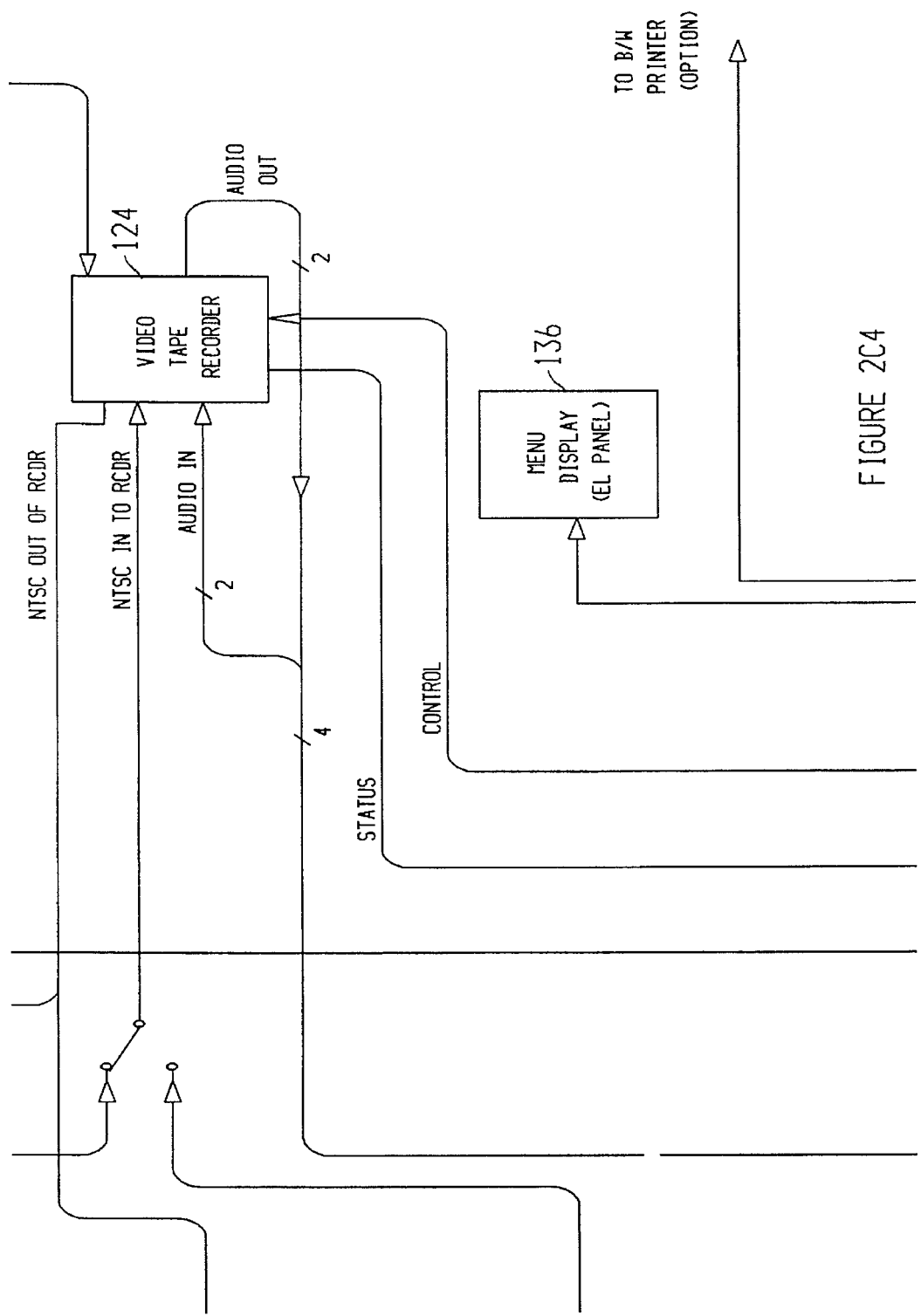

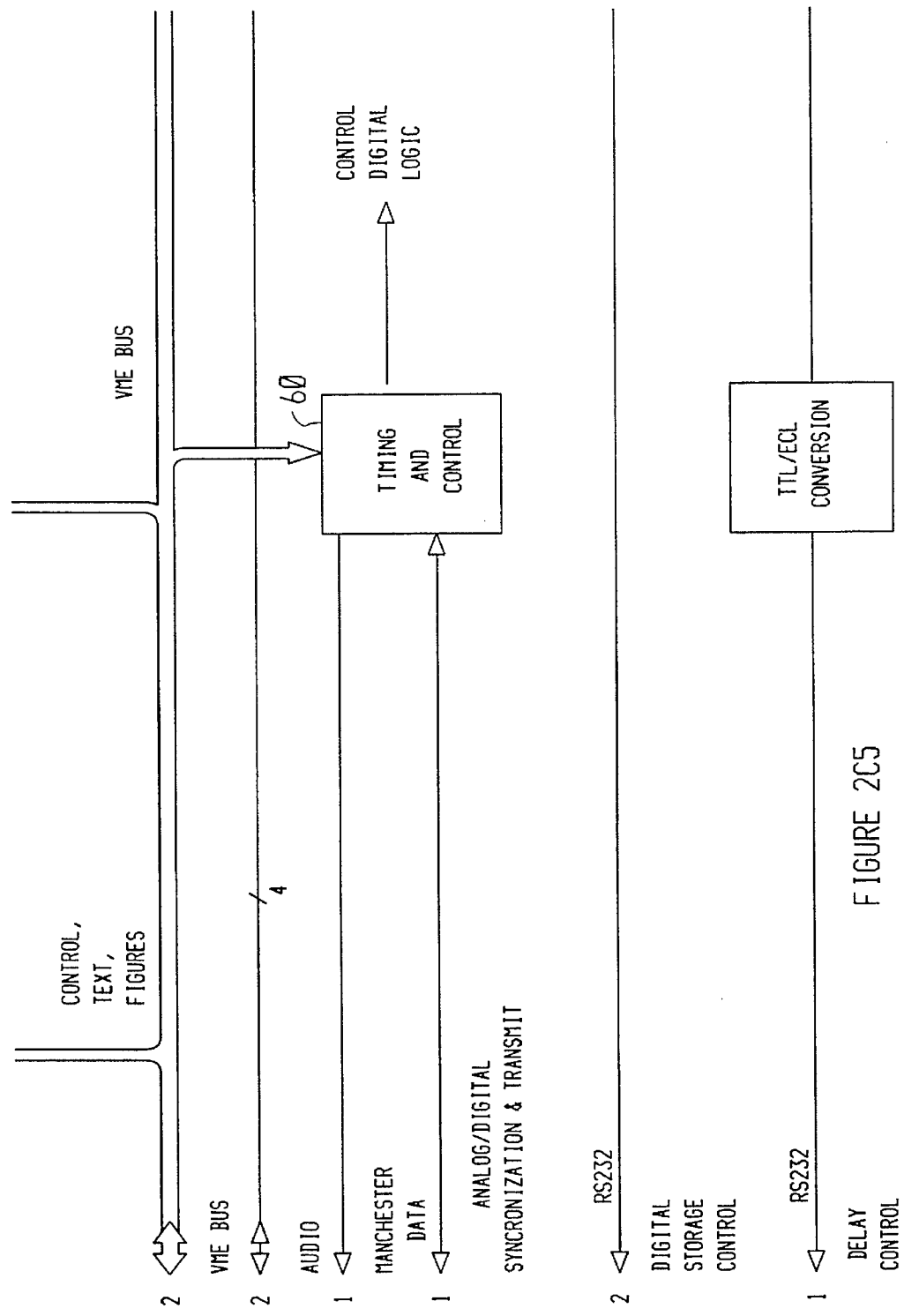
FIGURE 2C5

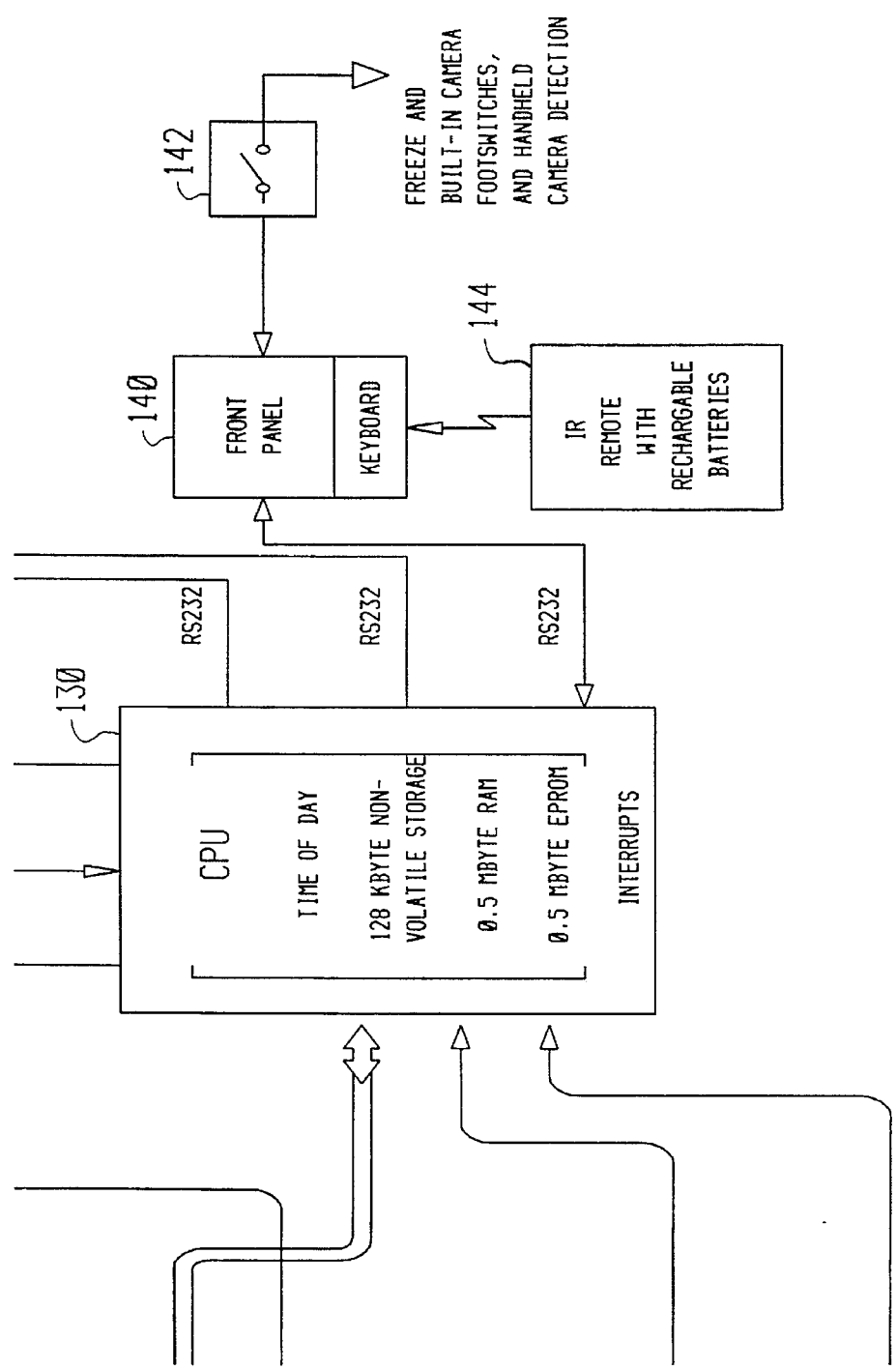
FIGURE 2C6

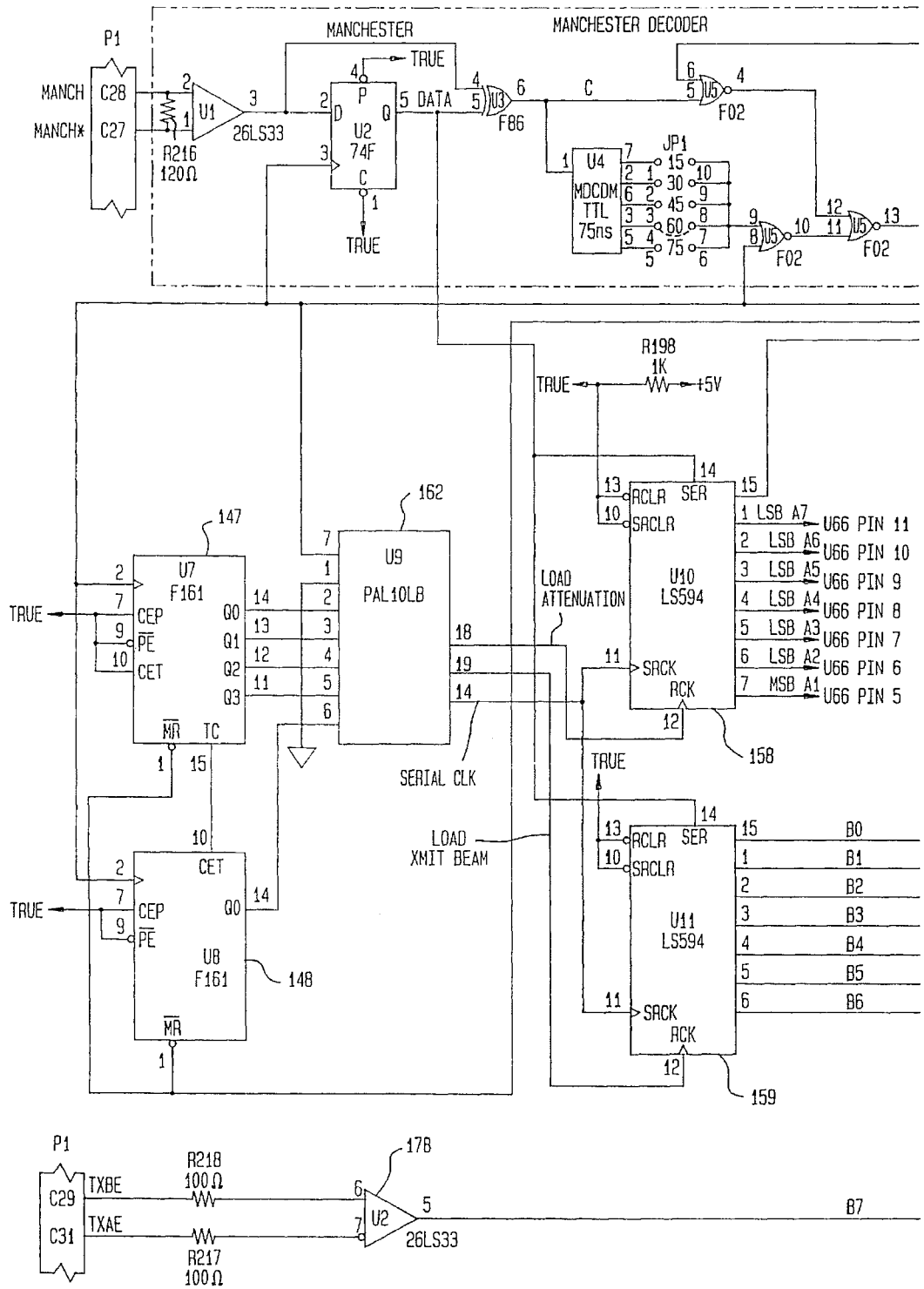
FIG. 4B1

FIG. 4B2
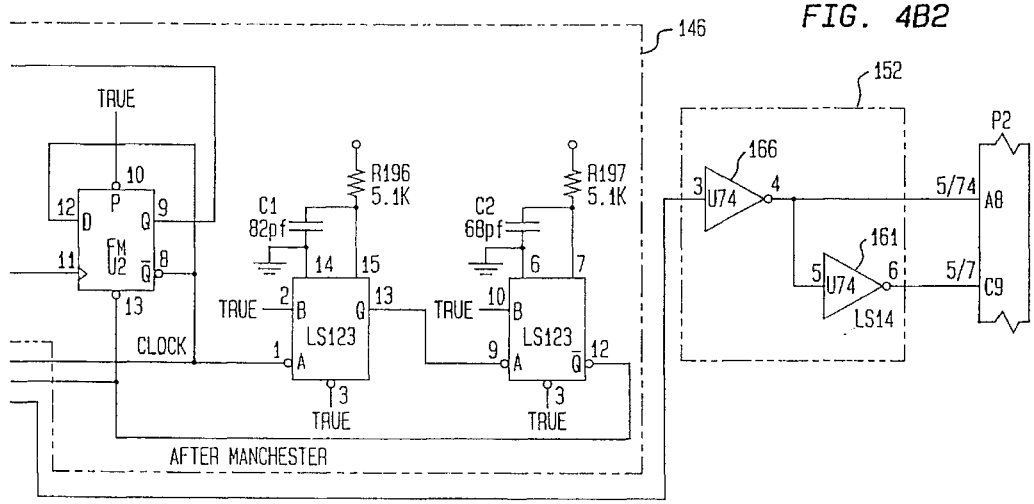
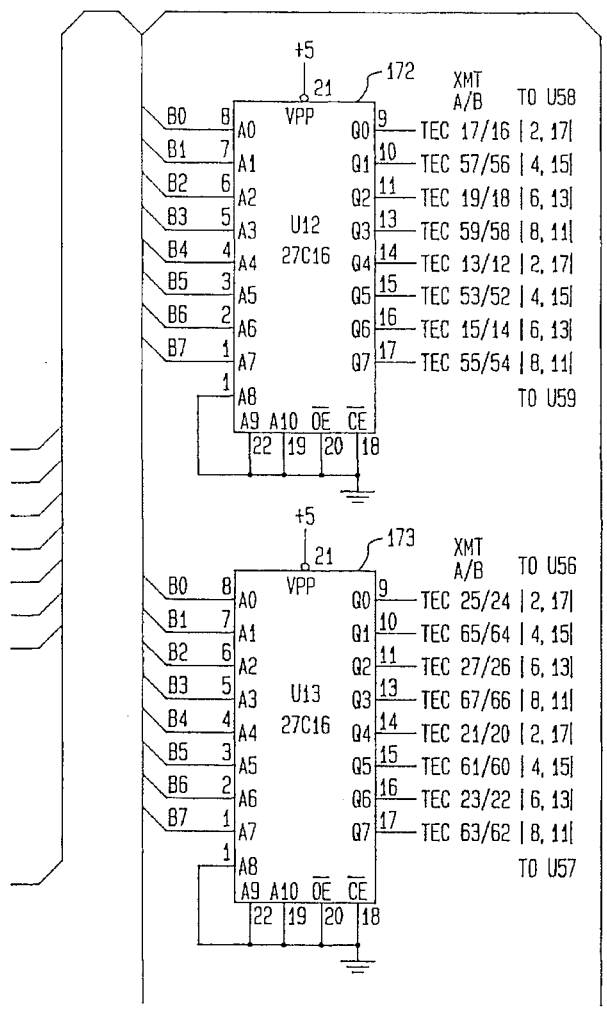
| REF. DES. | TYPE | +5V | DIG GND | BYPASS CAP |
|---|---|---|---|---|
| U1 | 26LS33 | 16 | 8 | C139 |
| U2 | 74F74 | 14 | 7 | C140 |
| U3 | 74F86 | 14 | 7 | C141 |
| U4 | MDLDM TTL 75 | | | |
| U5 | 74F02 | 14 | 7 | C142 |
| U6 | LS123 | 16 | 8 | C143 |
| U7, U8 | 74F161 | 16 | 8 | C144, C145 |
| U9 | PAL10L8 | 20 | 10 | C146 |
| U10, U11 | LS594 | 16 | 8 | C147, C148 |
| U12-U16 | 2716 | 24 | 12 | C149-C153 |
| U17-U20 | DS0026CN | | | C159-C162 |
| U21-U24 | | | | |
| U25-U28 | | | | |
| U29-U32 | | | | |
| U33-U36 | | | | |
| U37-U40 | | | | |
| U41-U44 | | | | |
| U45-U48 | | | | |
| U49-U52 | | | | |
| U53-U55 | | | | |
| U70 | DS0026CN | | | C159-C162 |
| U56-U59 | 74F244PC | 20 | 10 | C155-C158 |
| U60-U63 | 74F244PC | 20 | 10 | C175-C178 |
| U64 | 74F244PC | 20 | 10 | C195 |
| U65 | 74F244PC | 20 | 10 | C196 |
| U66 | DAC0807LCN | | | |
| U67 | LF35IN | | | |
| U68 | LM317HVK | | | |
| U69 | 74F04 | 14 | 7 | C215 |
| U71 | MDLDM TTL 75 | | | |
| U72 | 74F11 | 14 | 7 | C238 |
| U73 | 74F74 | 17 | 7 | C239 |
| U74 | 74LS14 | 14 | 7 | C154 |
| U75 | 74F164 | 14 | 7 | C240 |

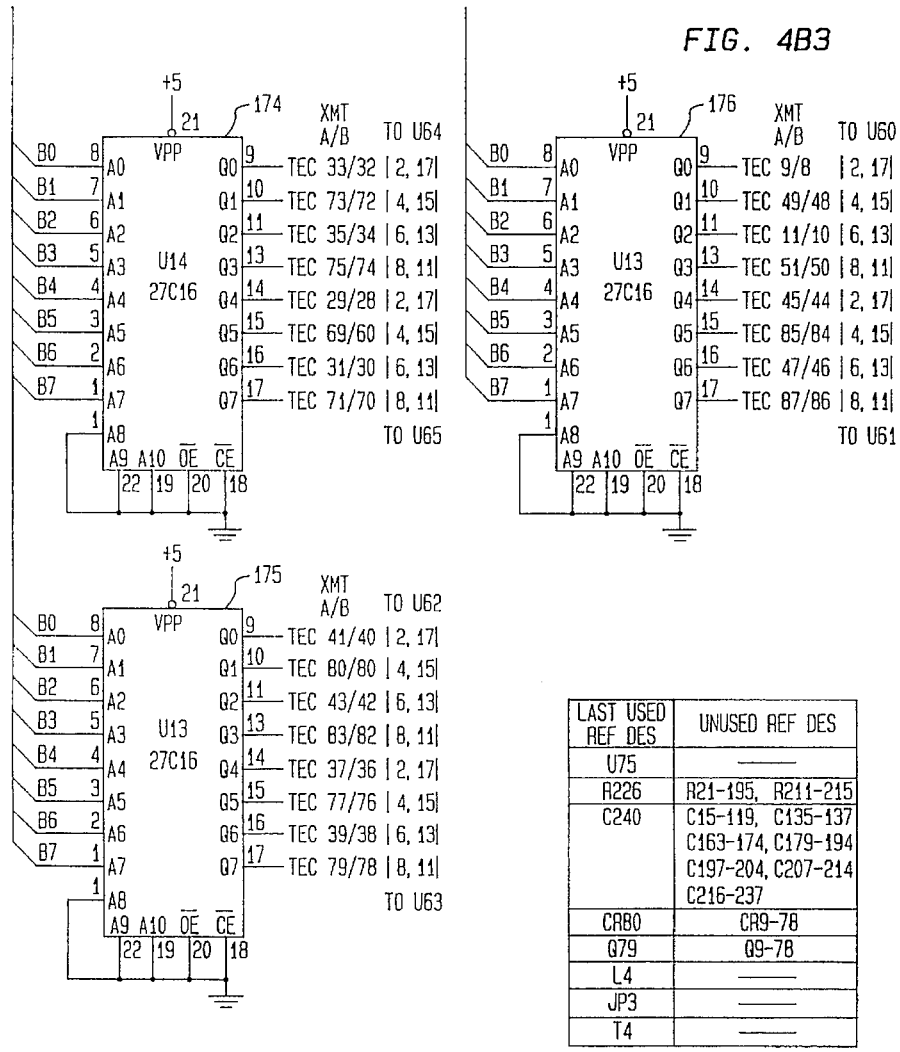
FIG. 4B3

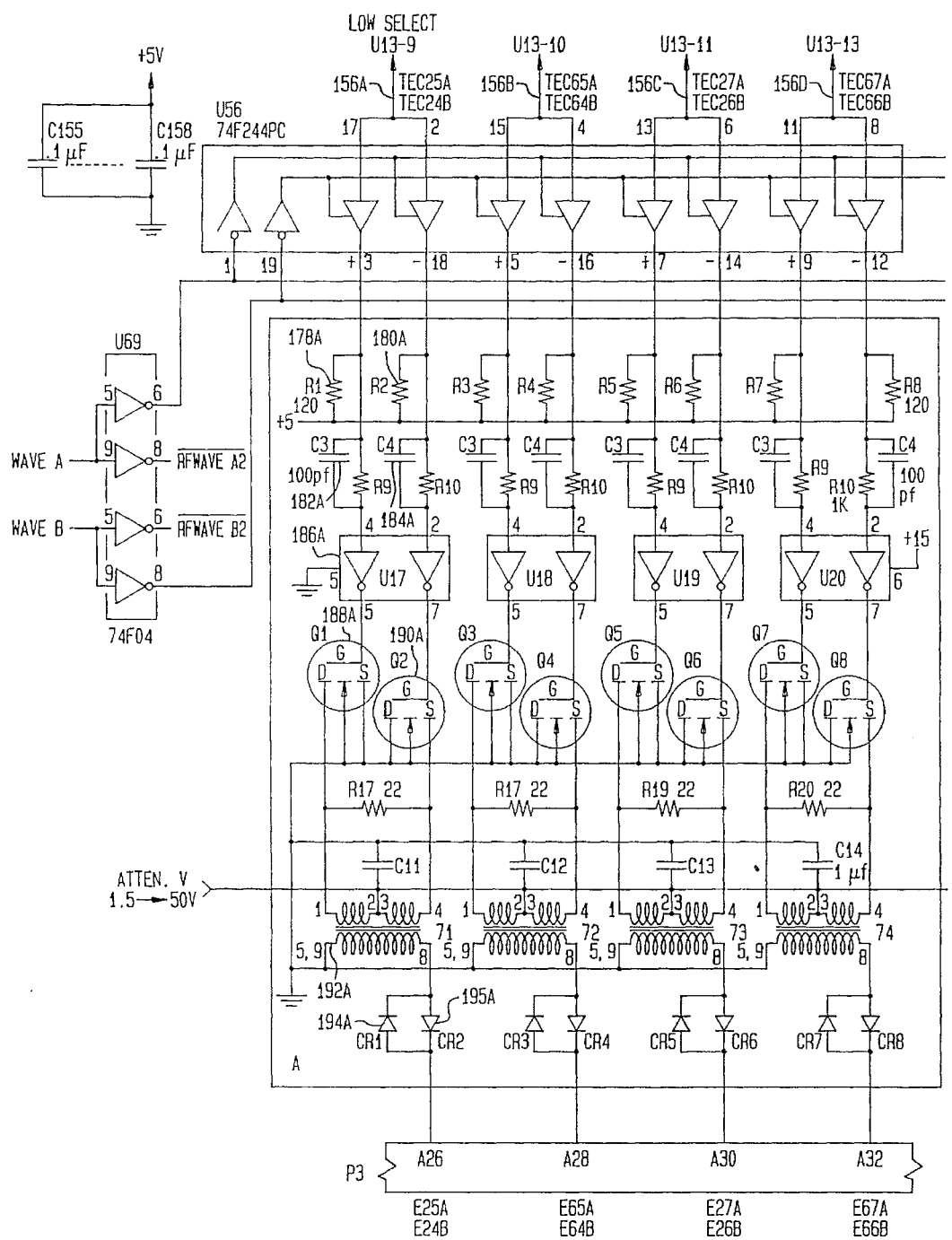
FIG. 4C1

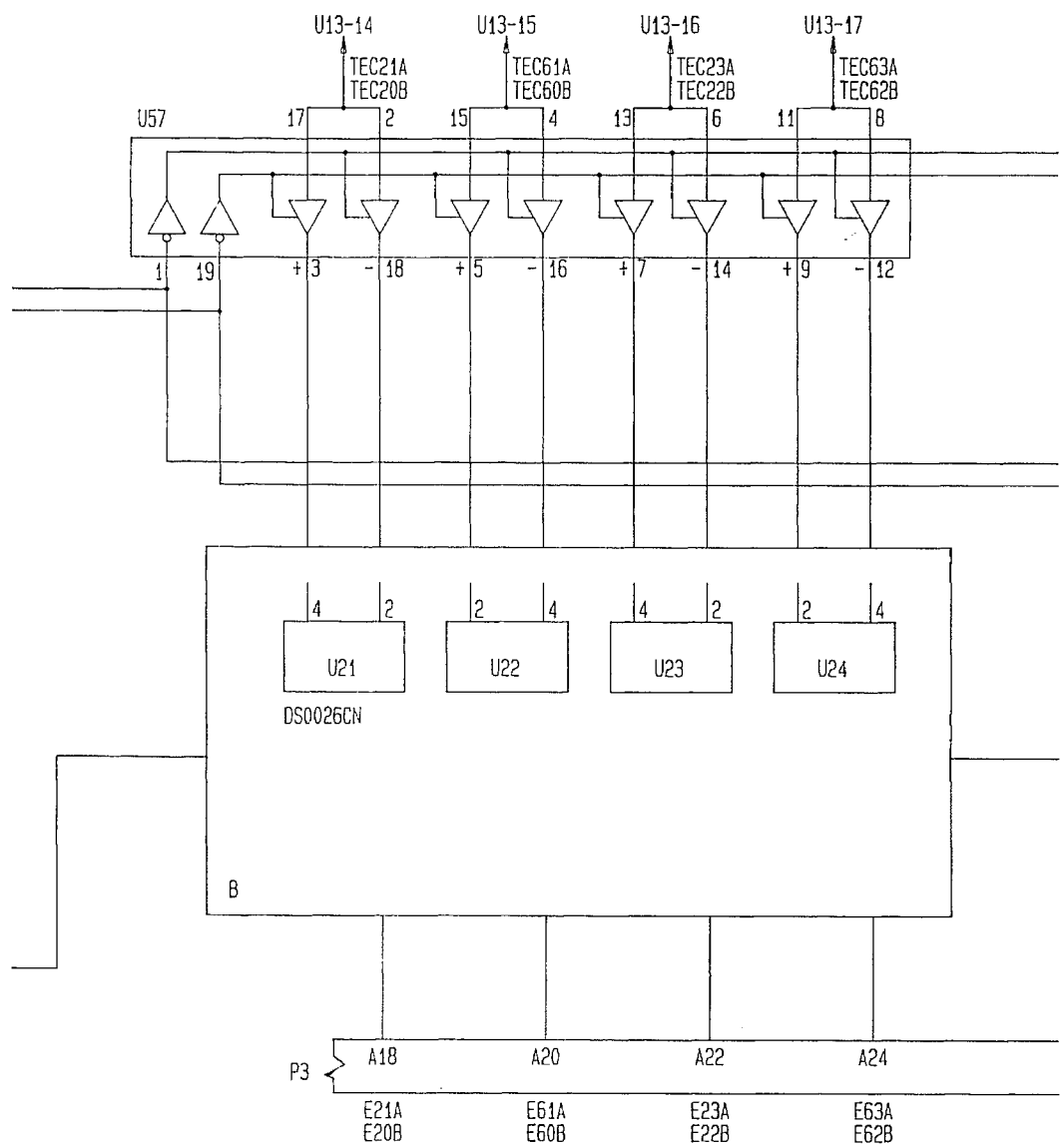
FIG. 4C2

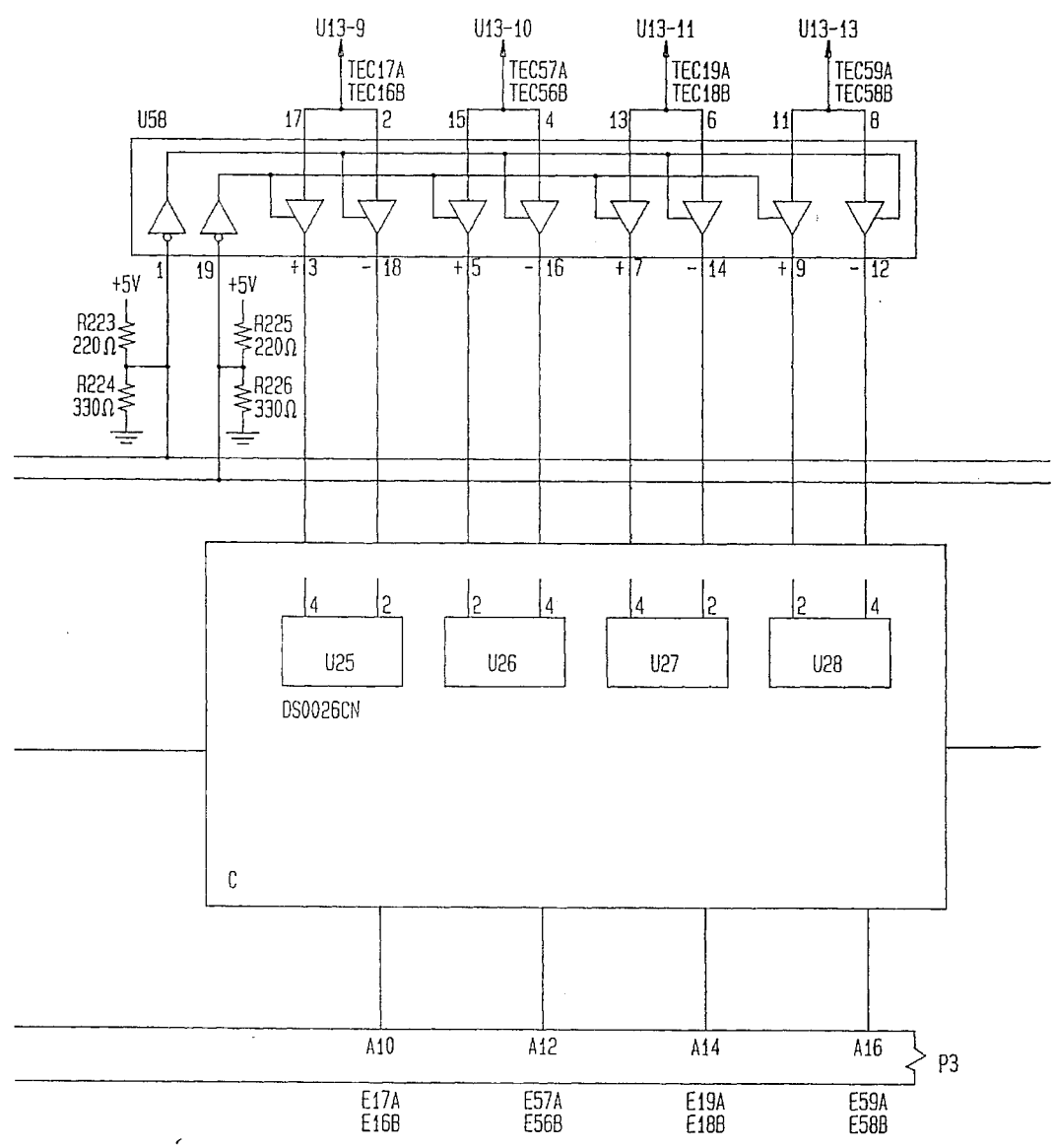
FIG. 4C3

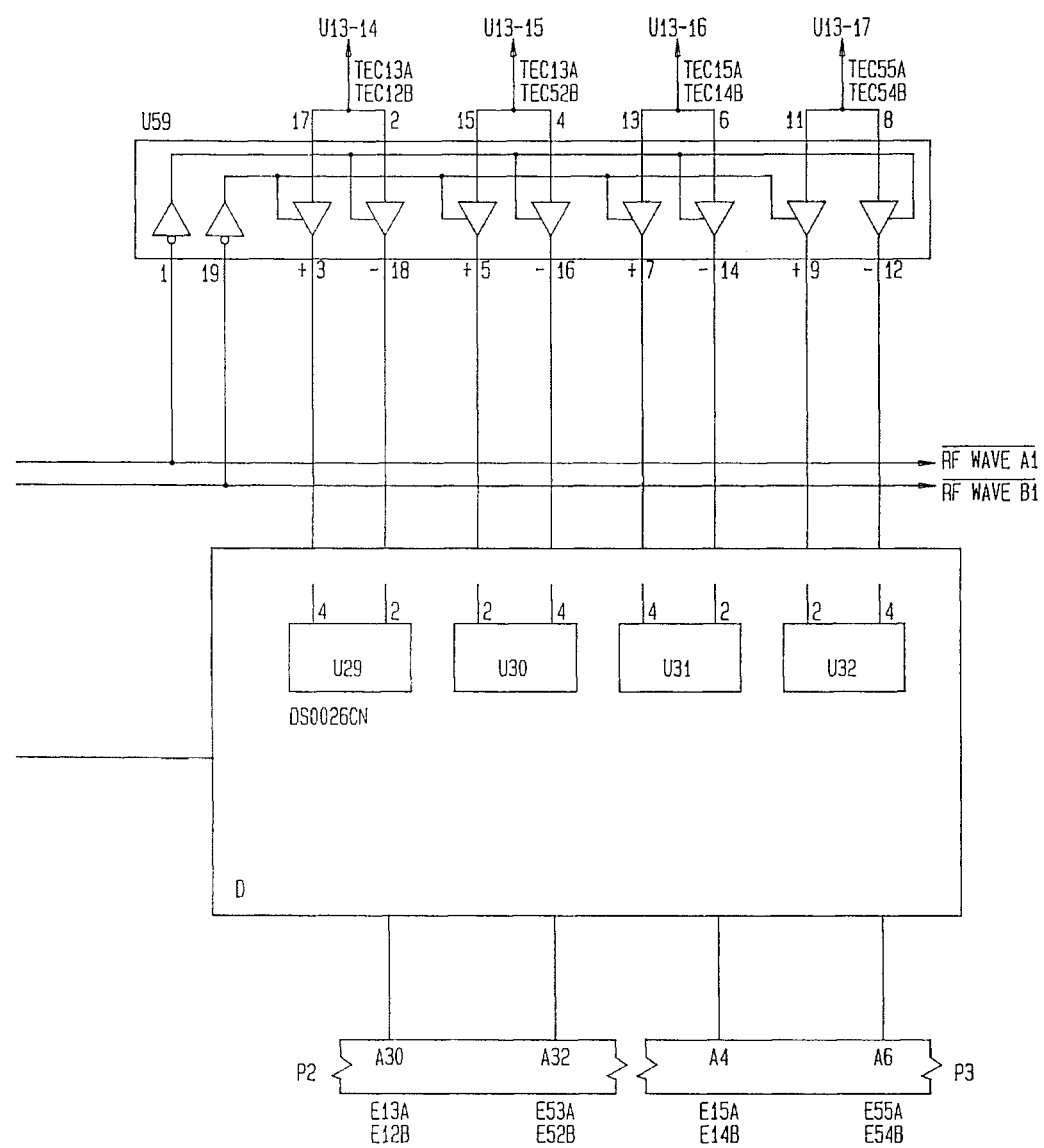
FIG. 4C4

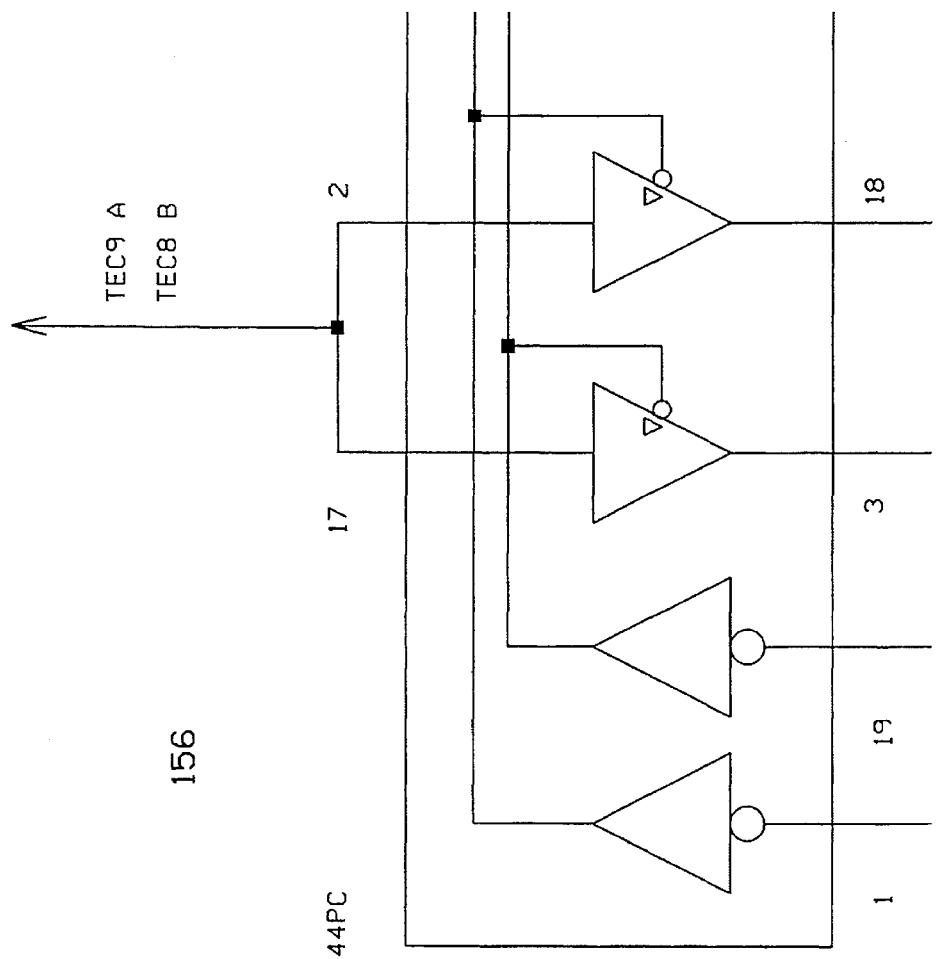
FIGURE 4D1

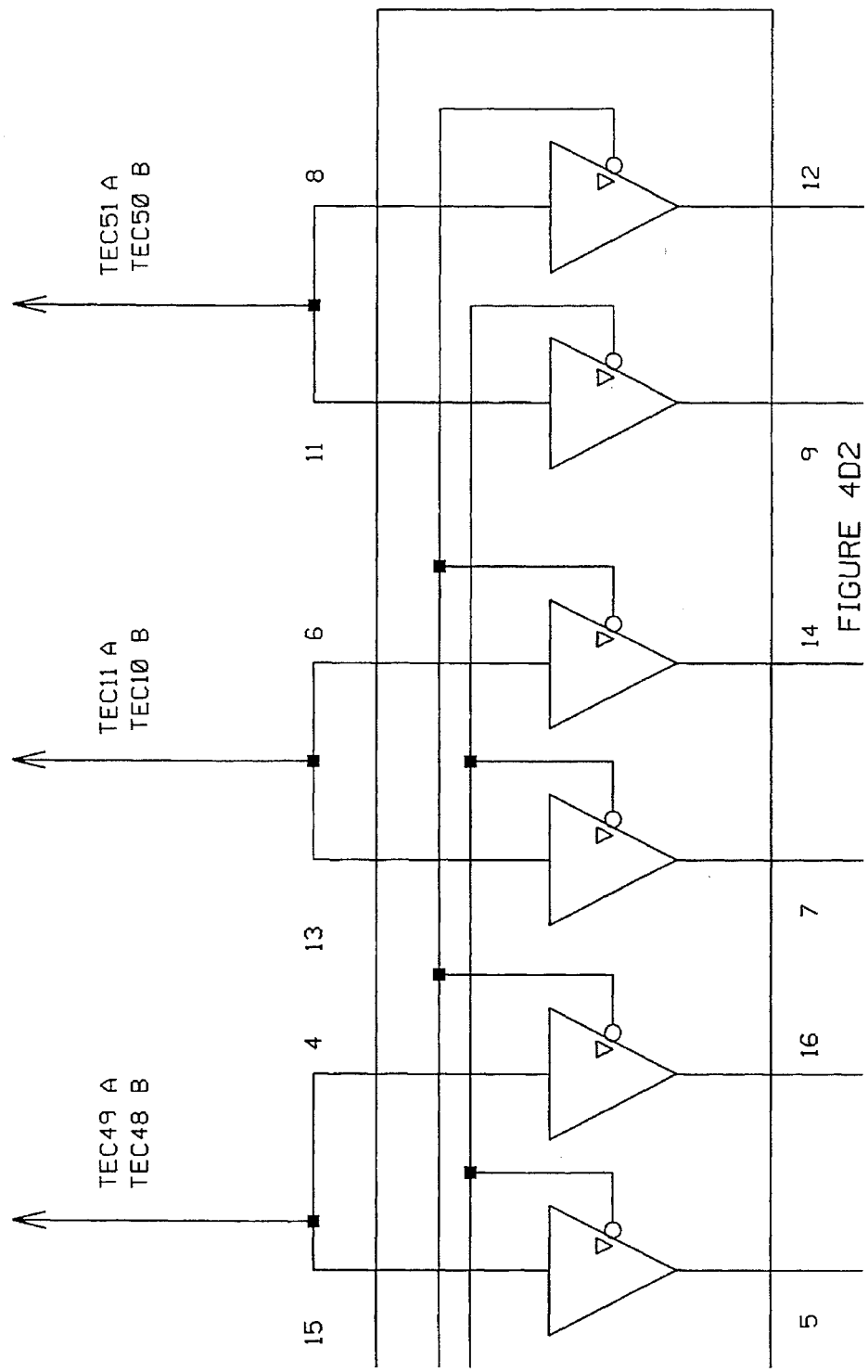
FIGURE 4D2

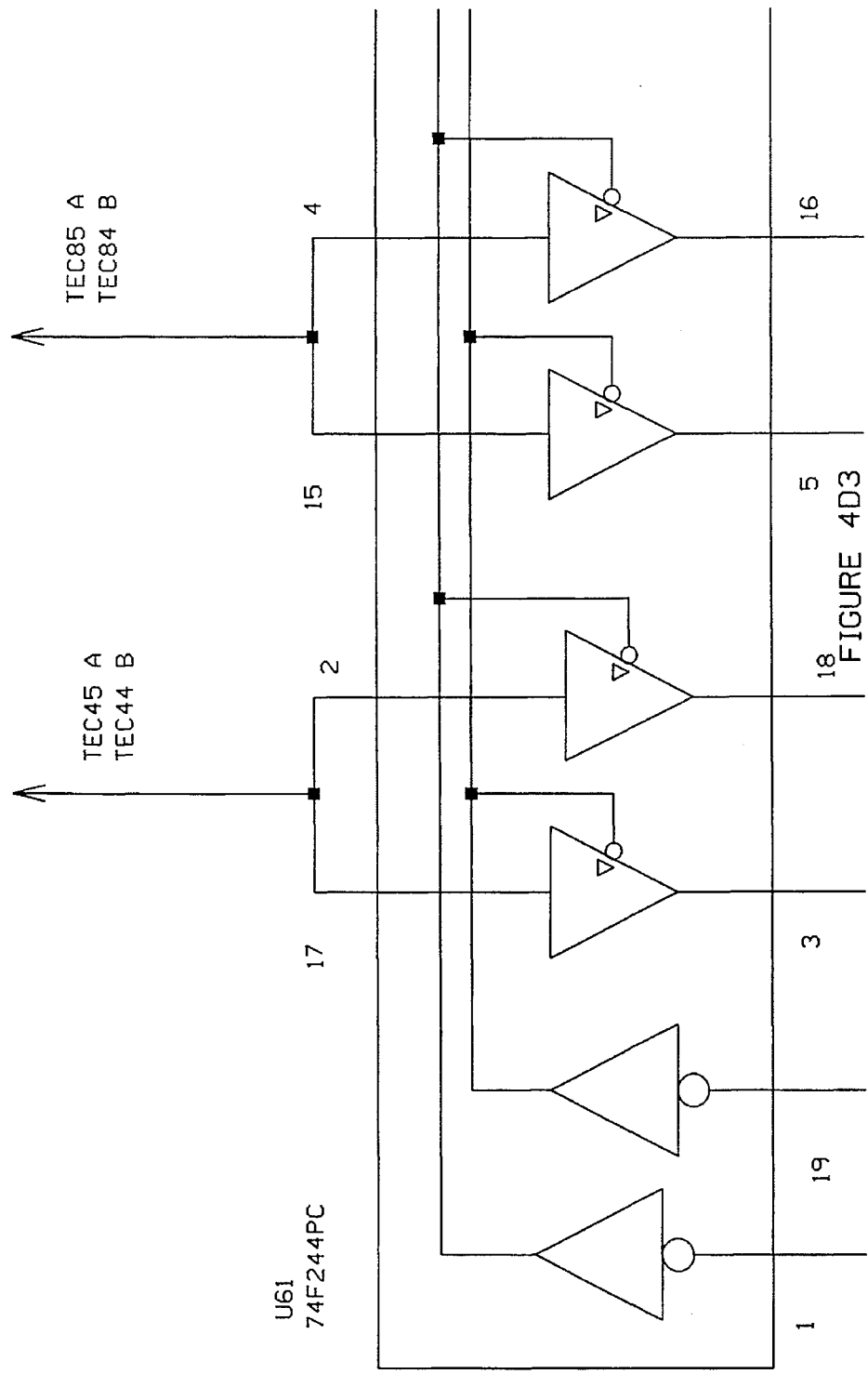
FIGURE 4D3

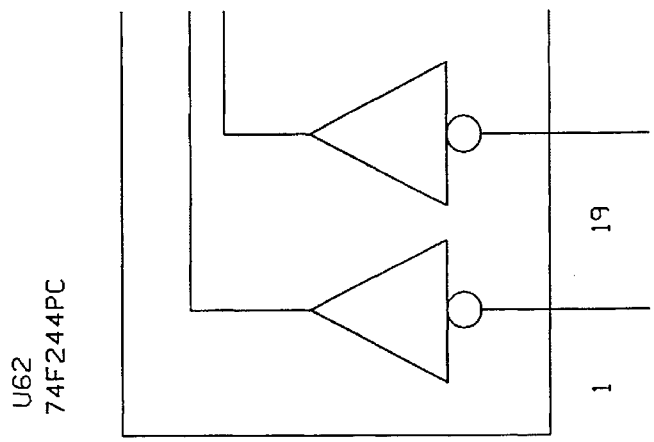
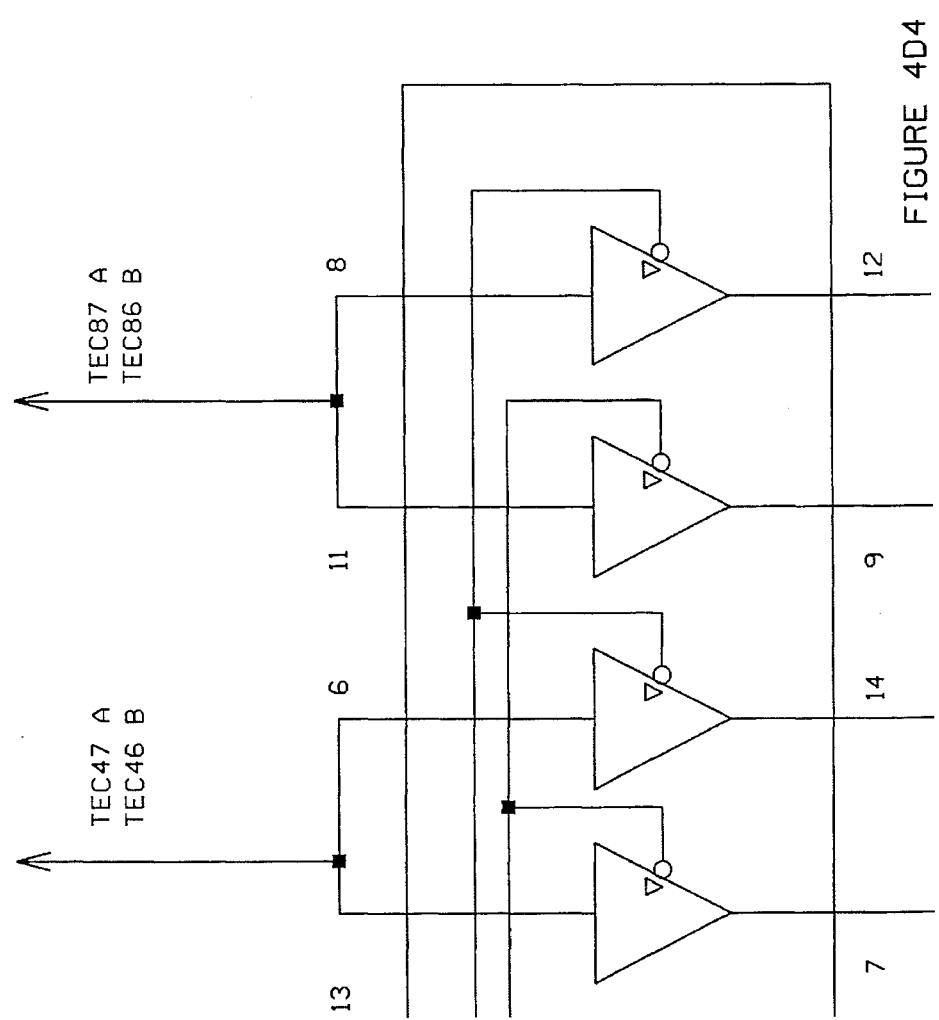
FIGURE 4D4

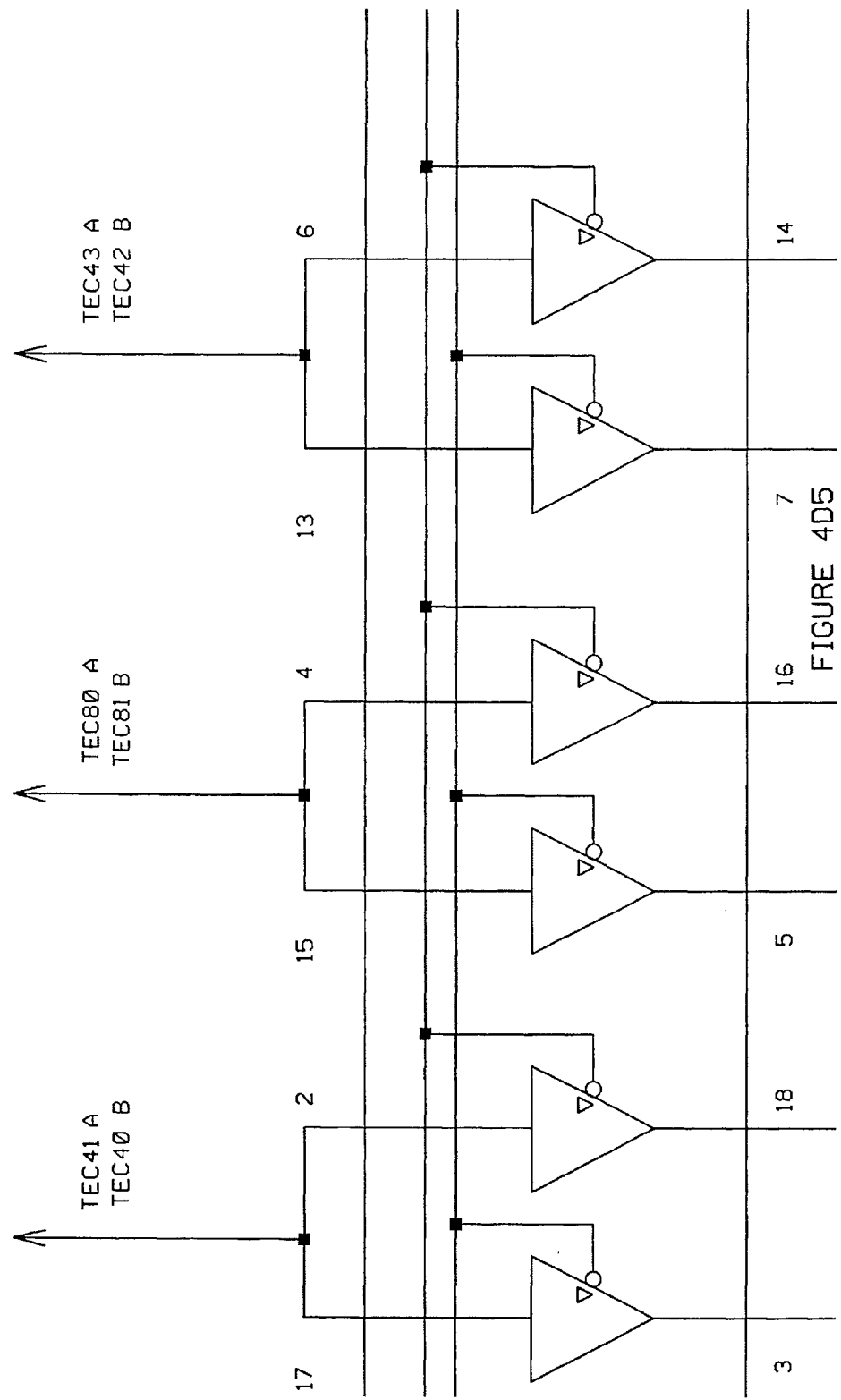
FIGURE 4D5

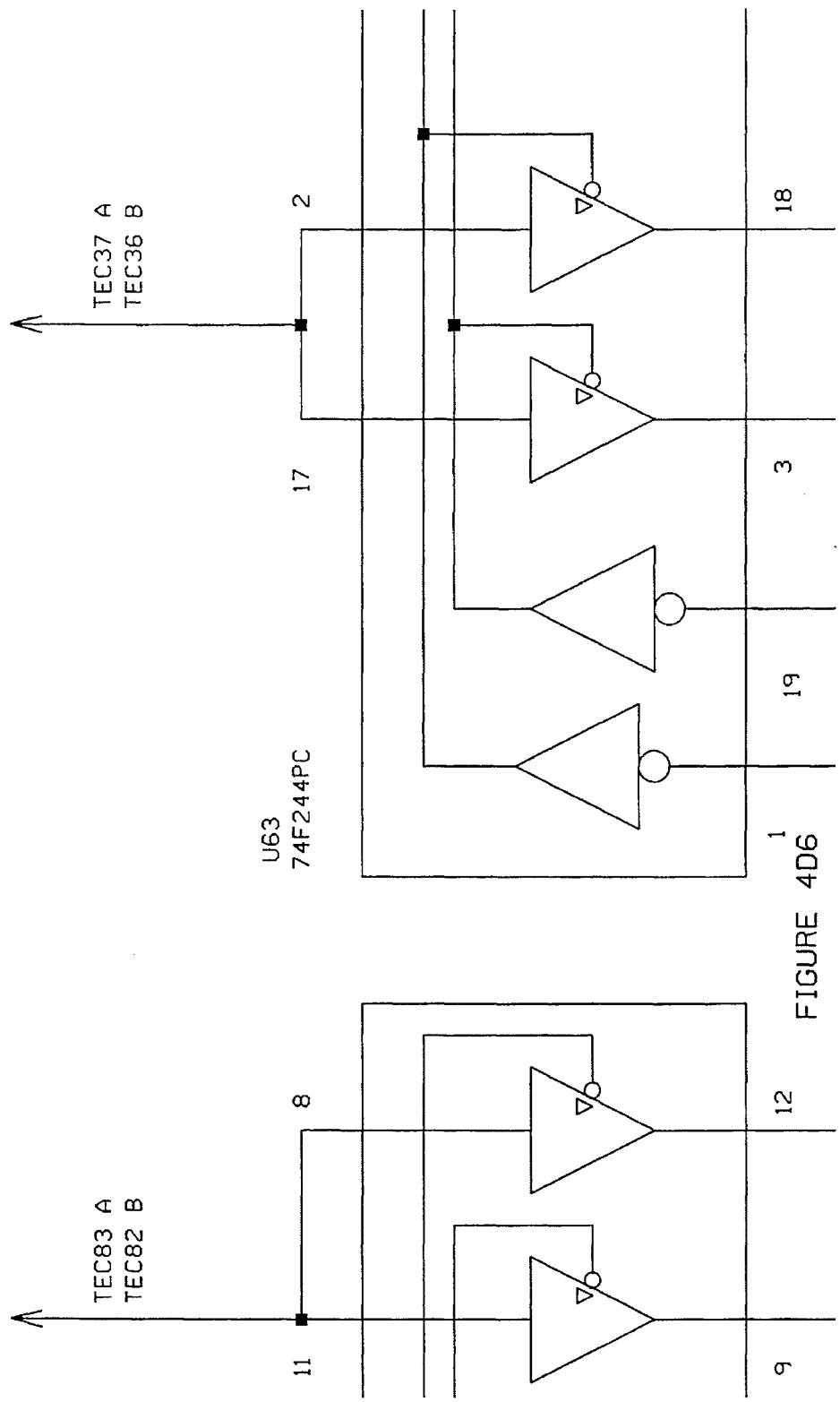
FIGURE 4D6

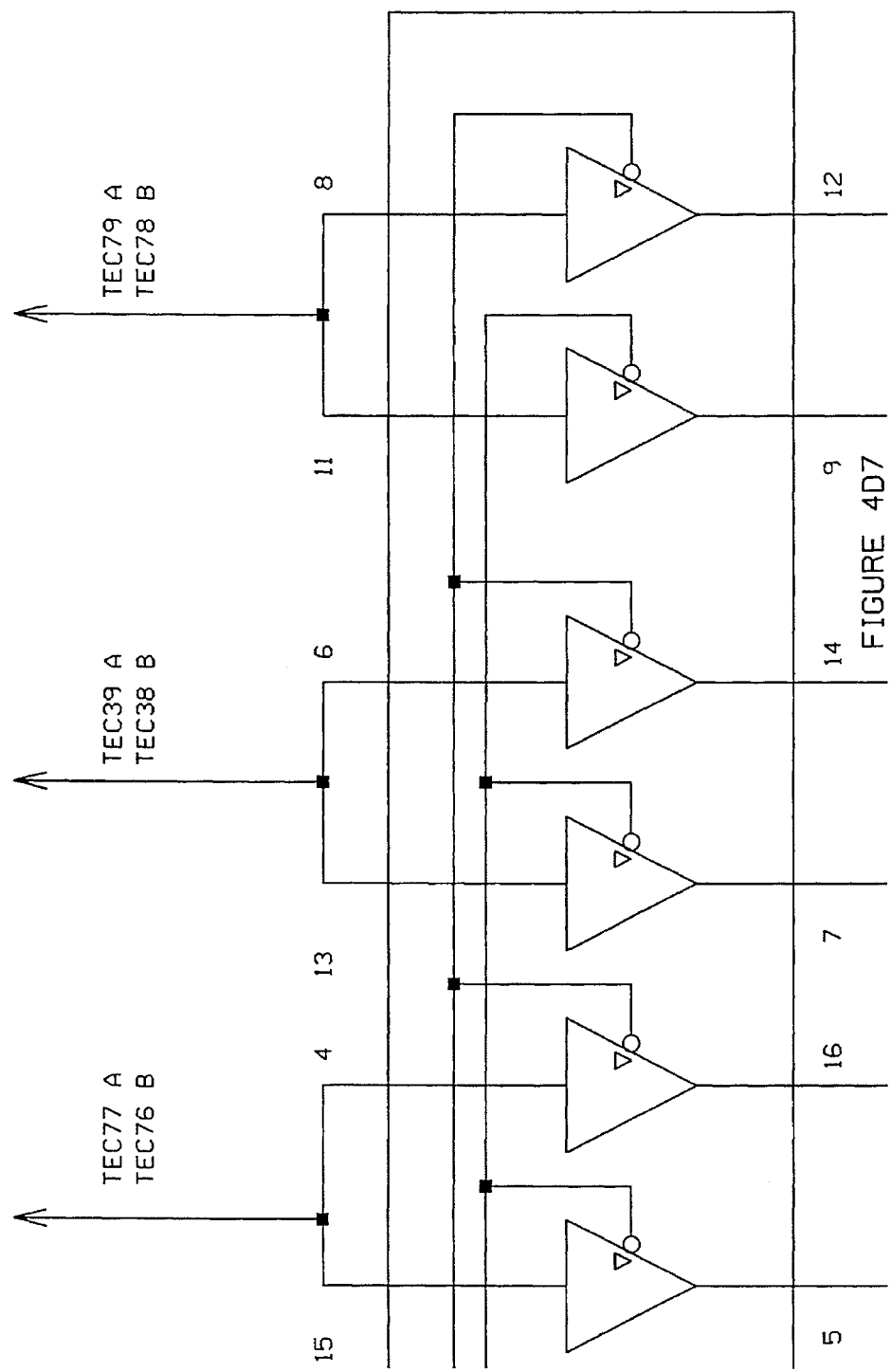

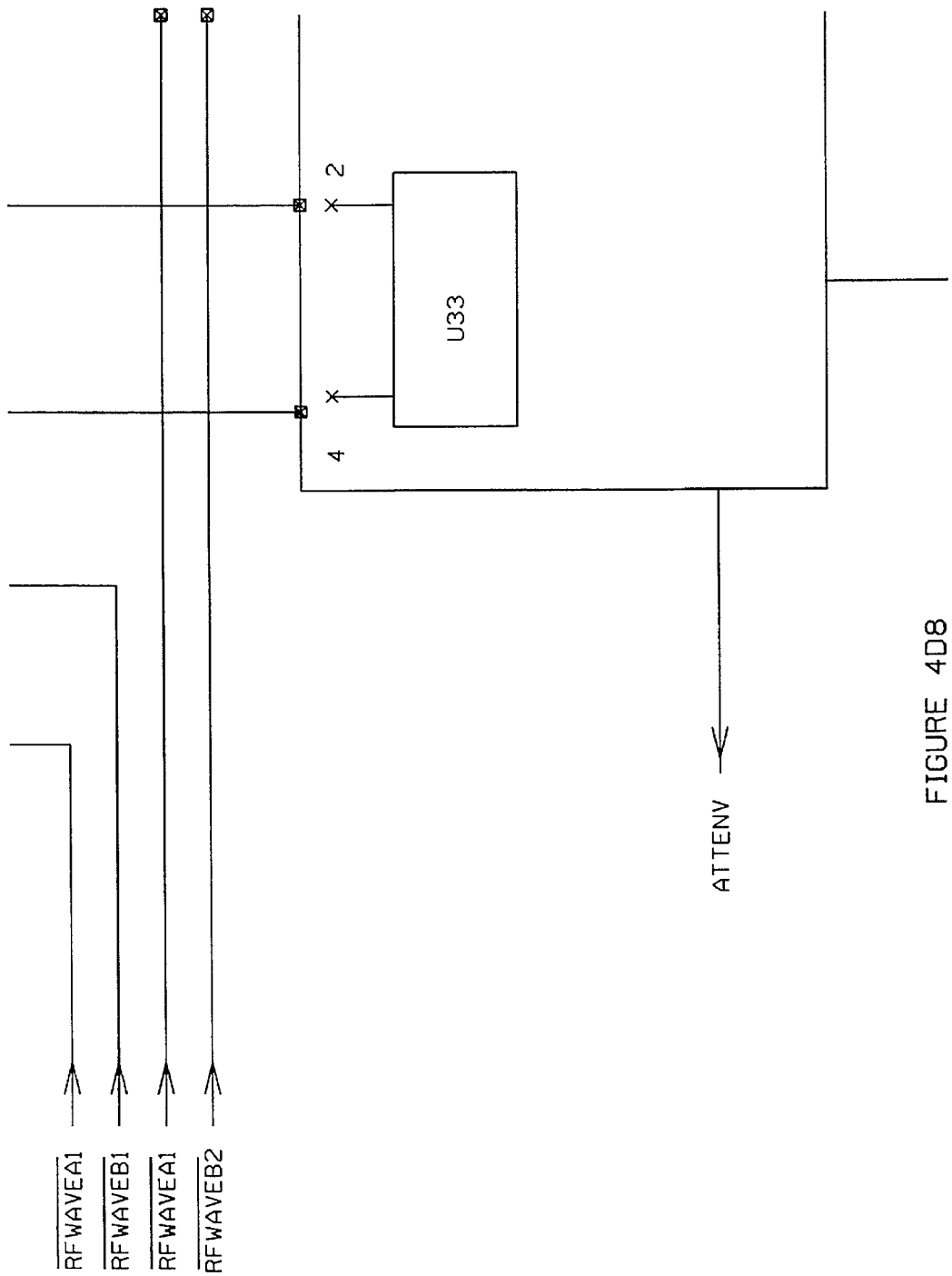

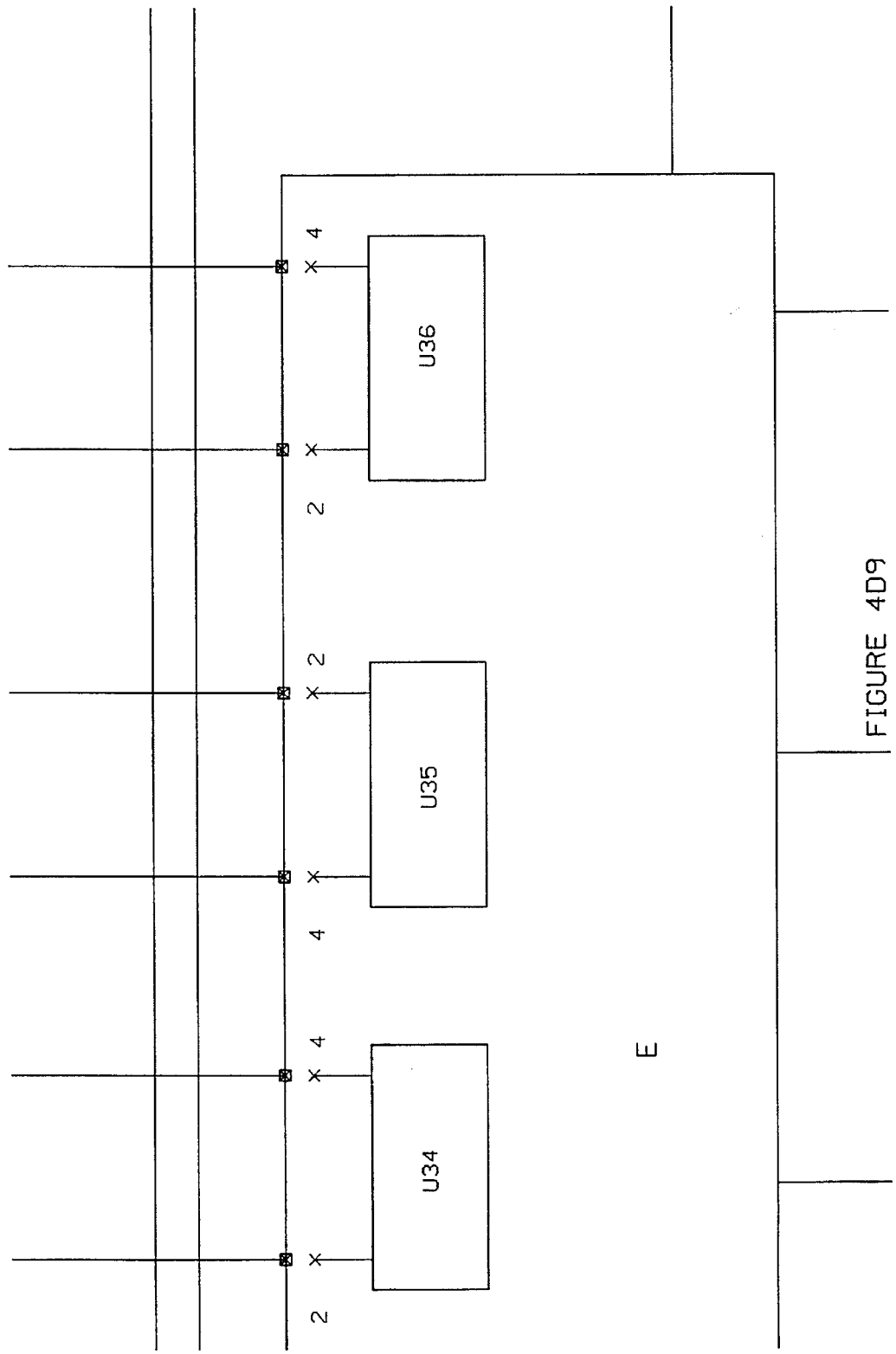
FIGURE 4D9

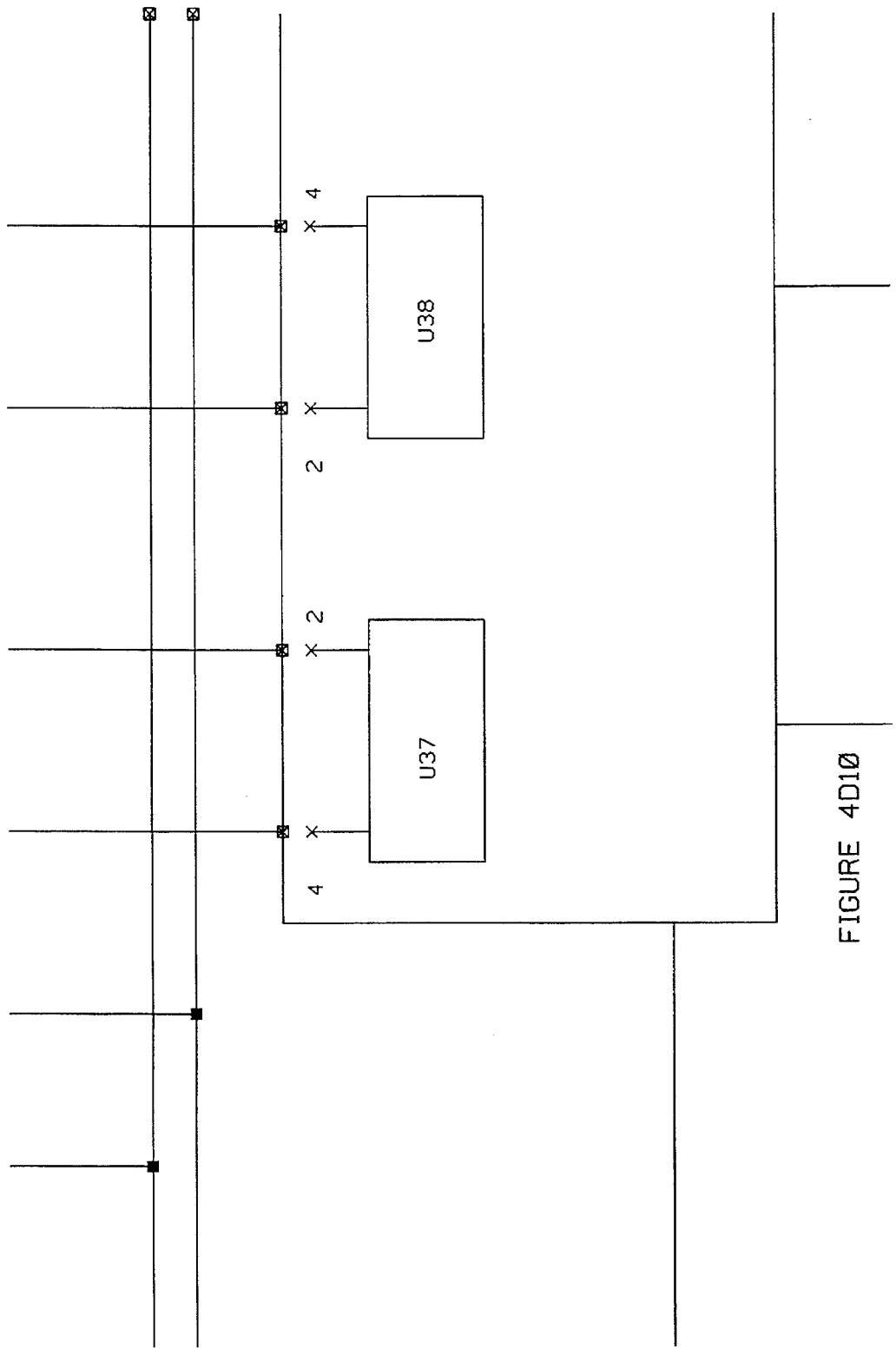
FIGURE 4D10

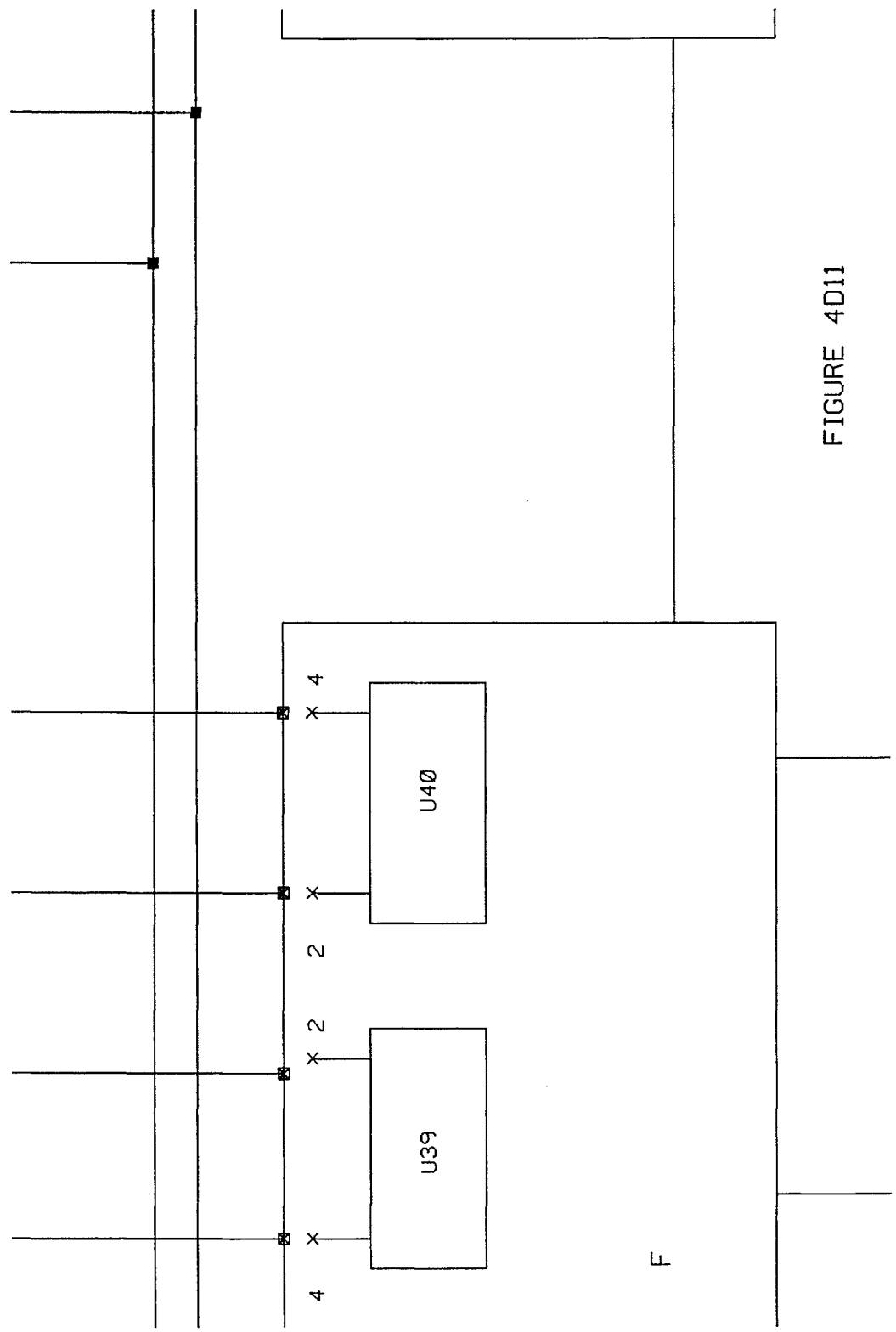

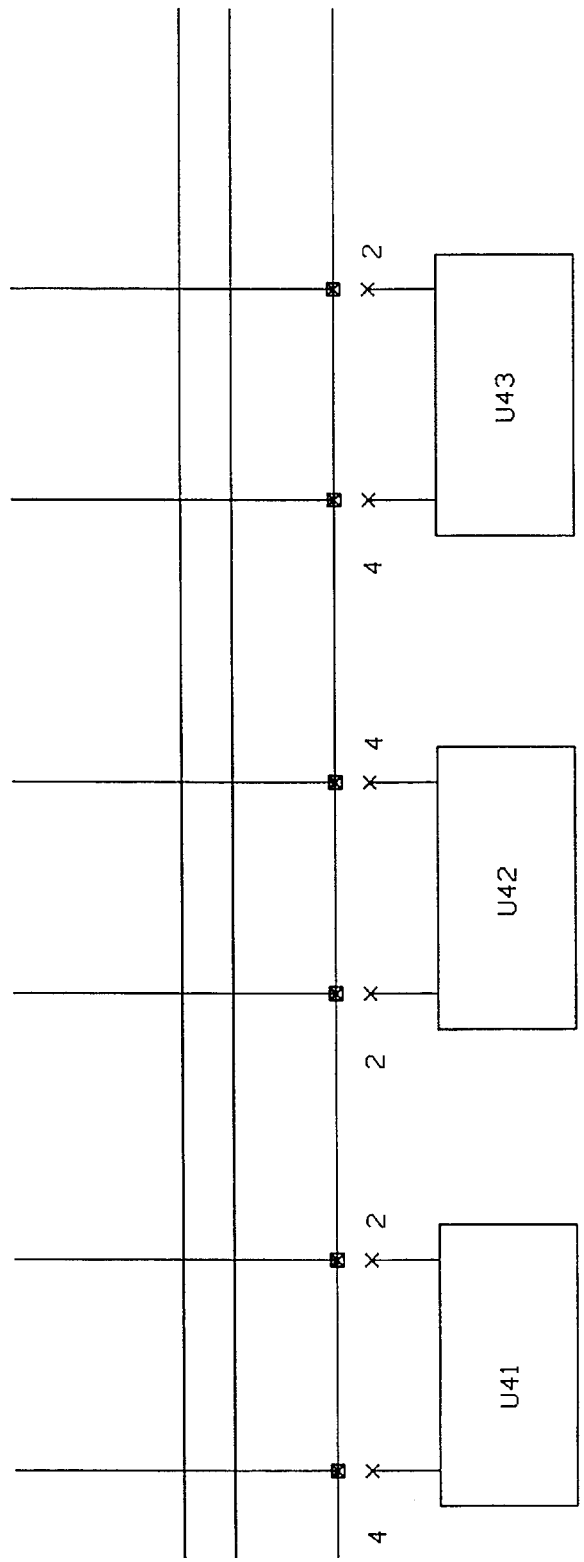
FIGURE 4D12

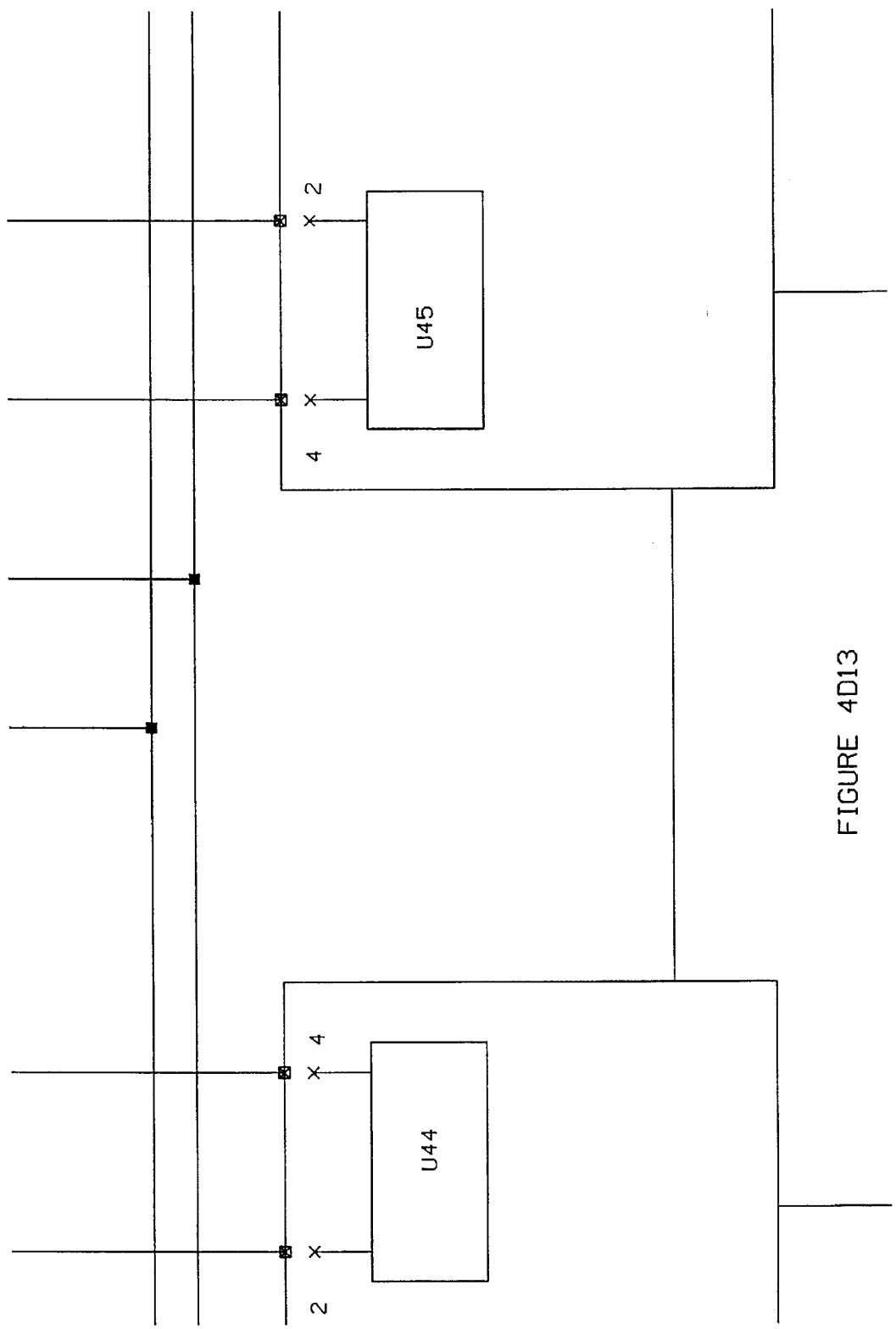
FIGURE 4D13

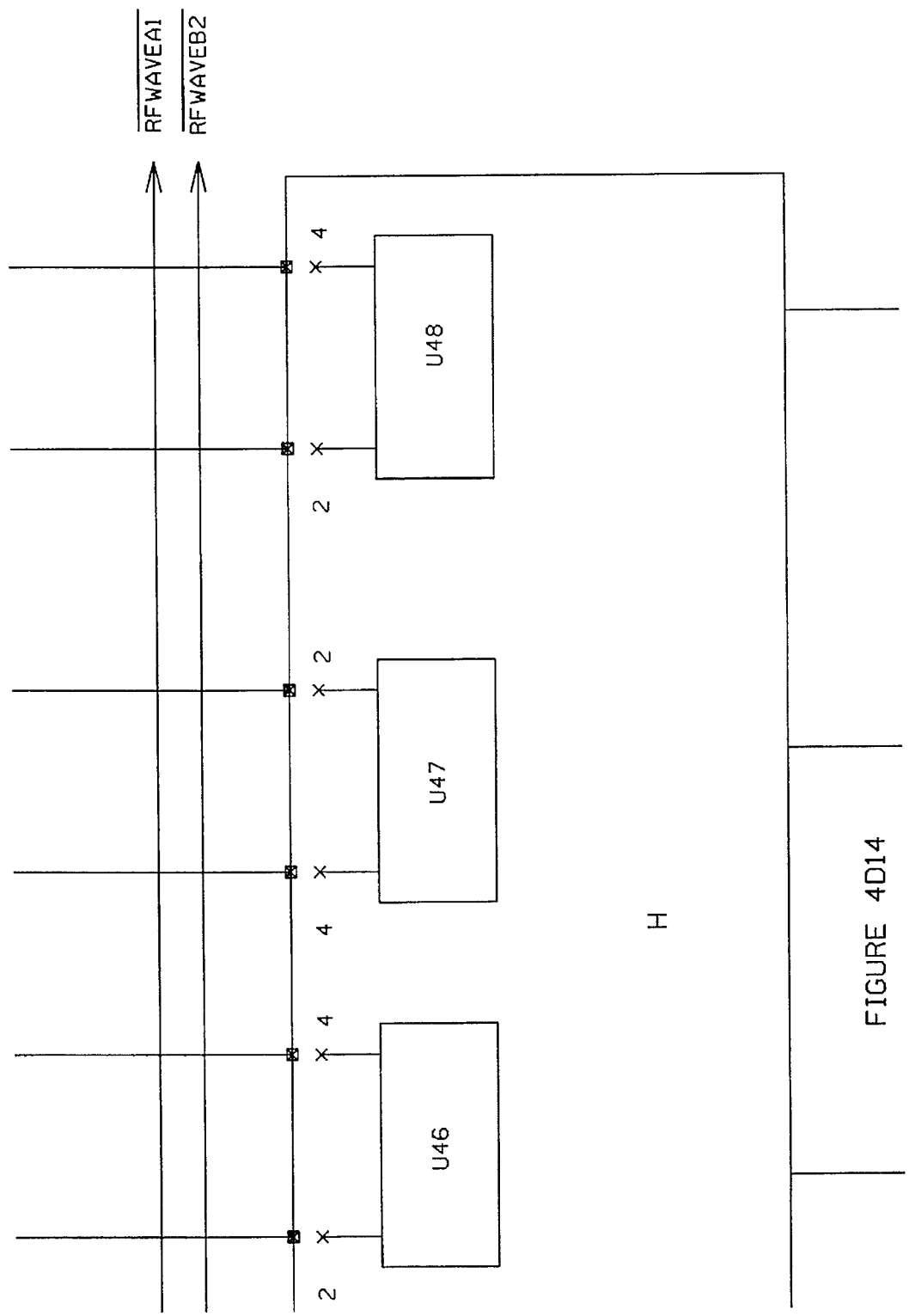
FIGURE 4D14

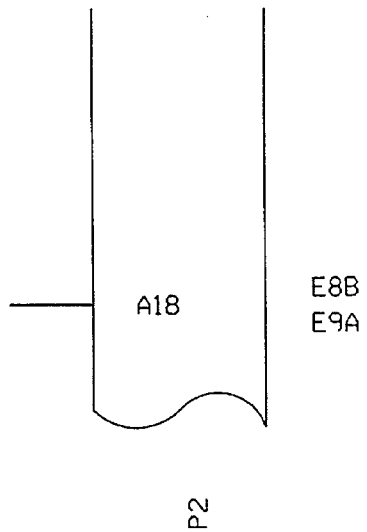
FIGURE 4D15

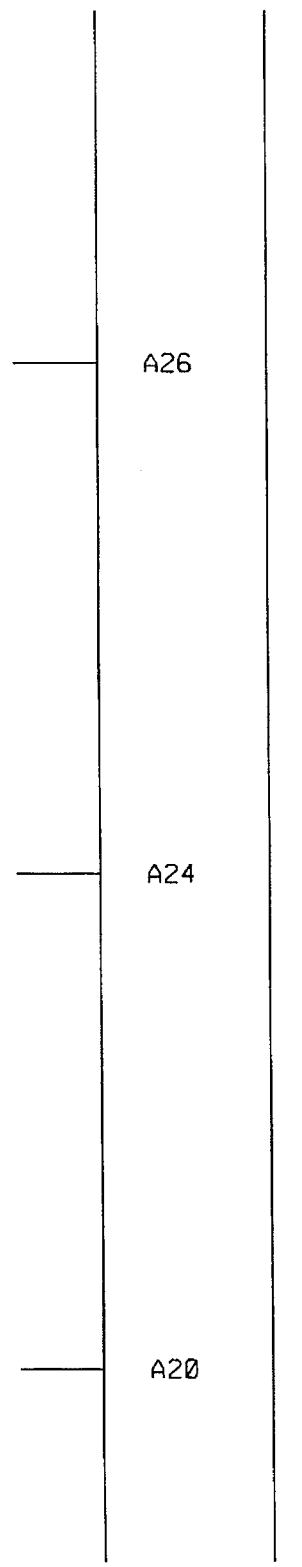
FIGURE 4D16

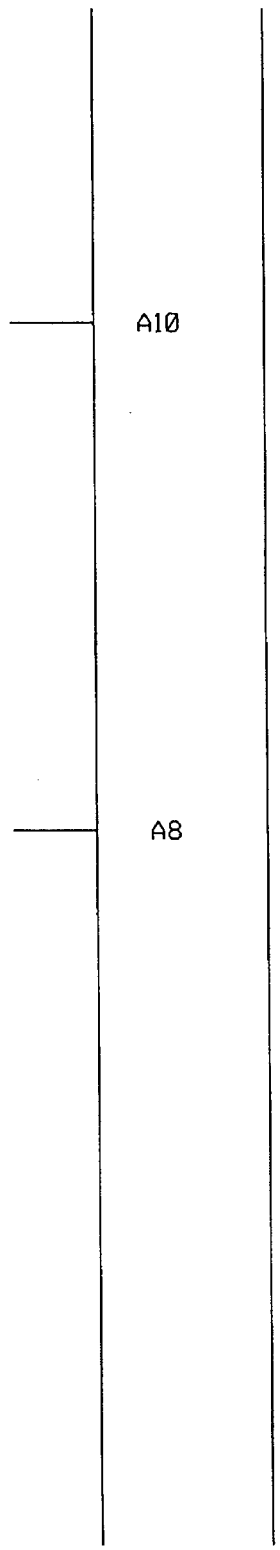
FIGURE 4D17

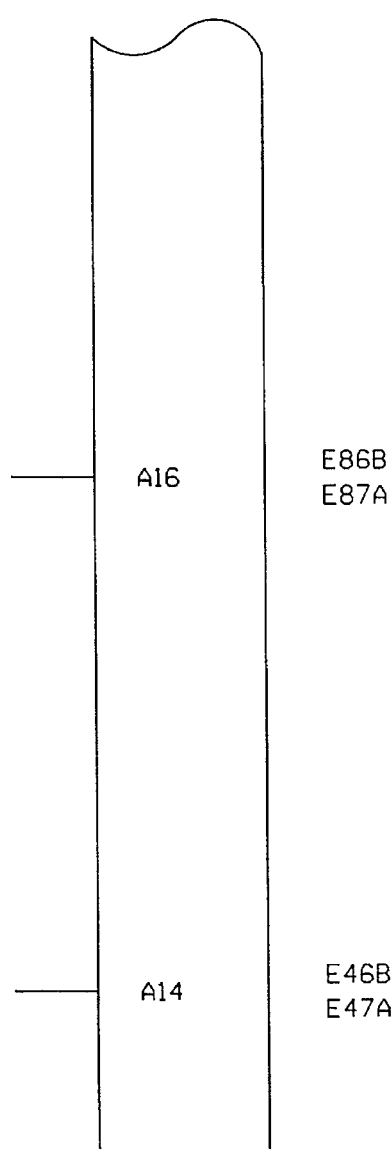
FIGURE 4D18

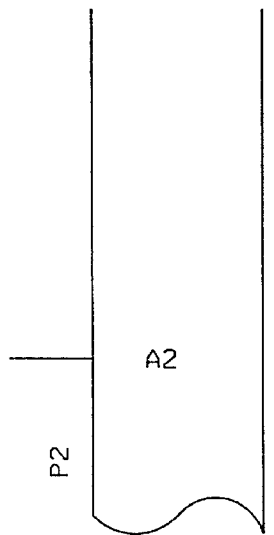
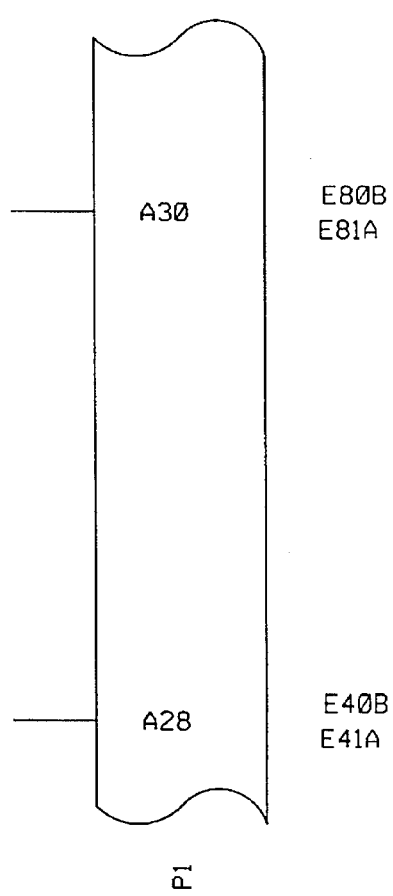
FIGURE 4D19

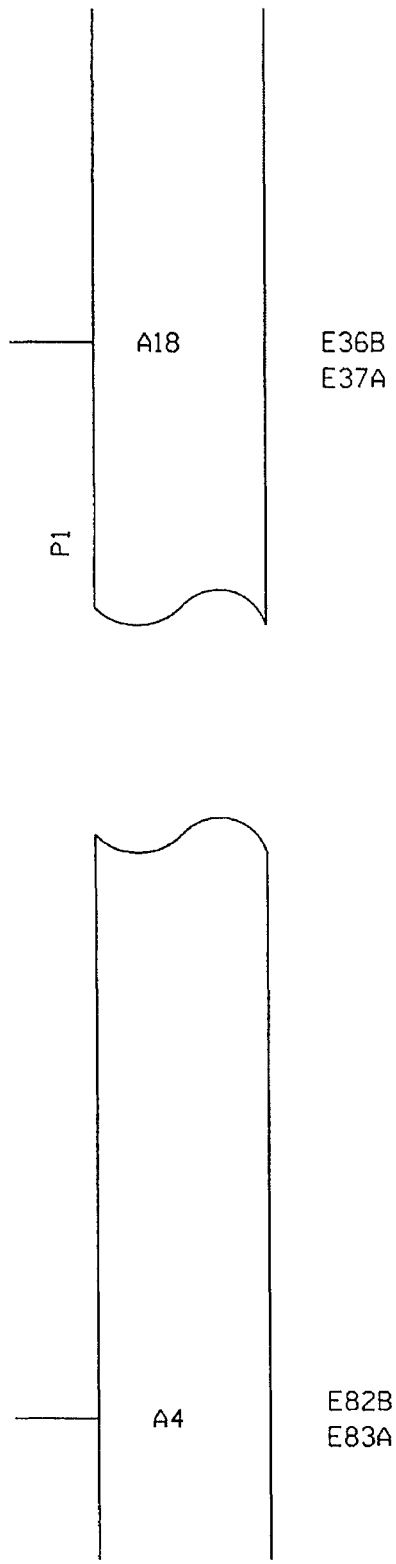
FIGURE 4D20

FIGURE 4D21

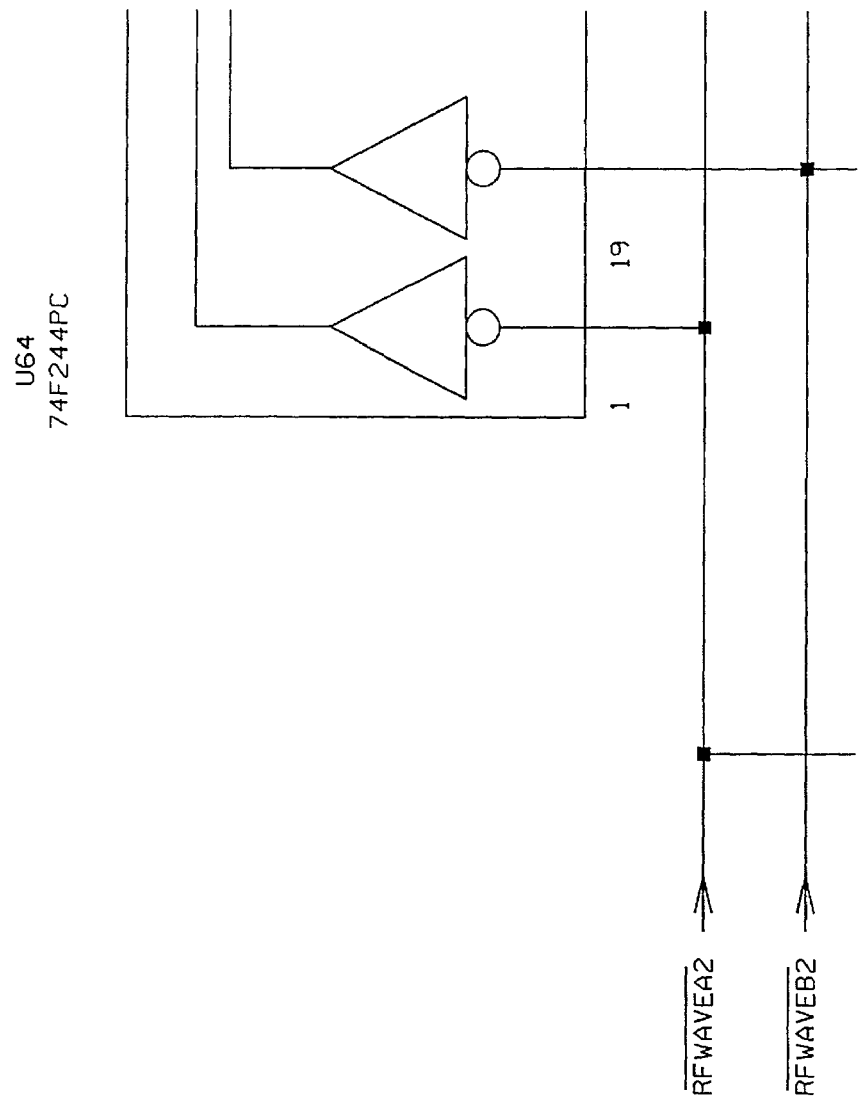
FIGURE 4E1

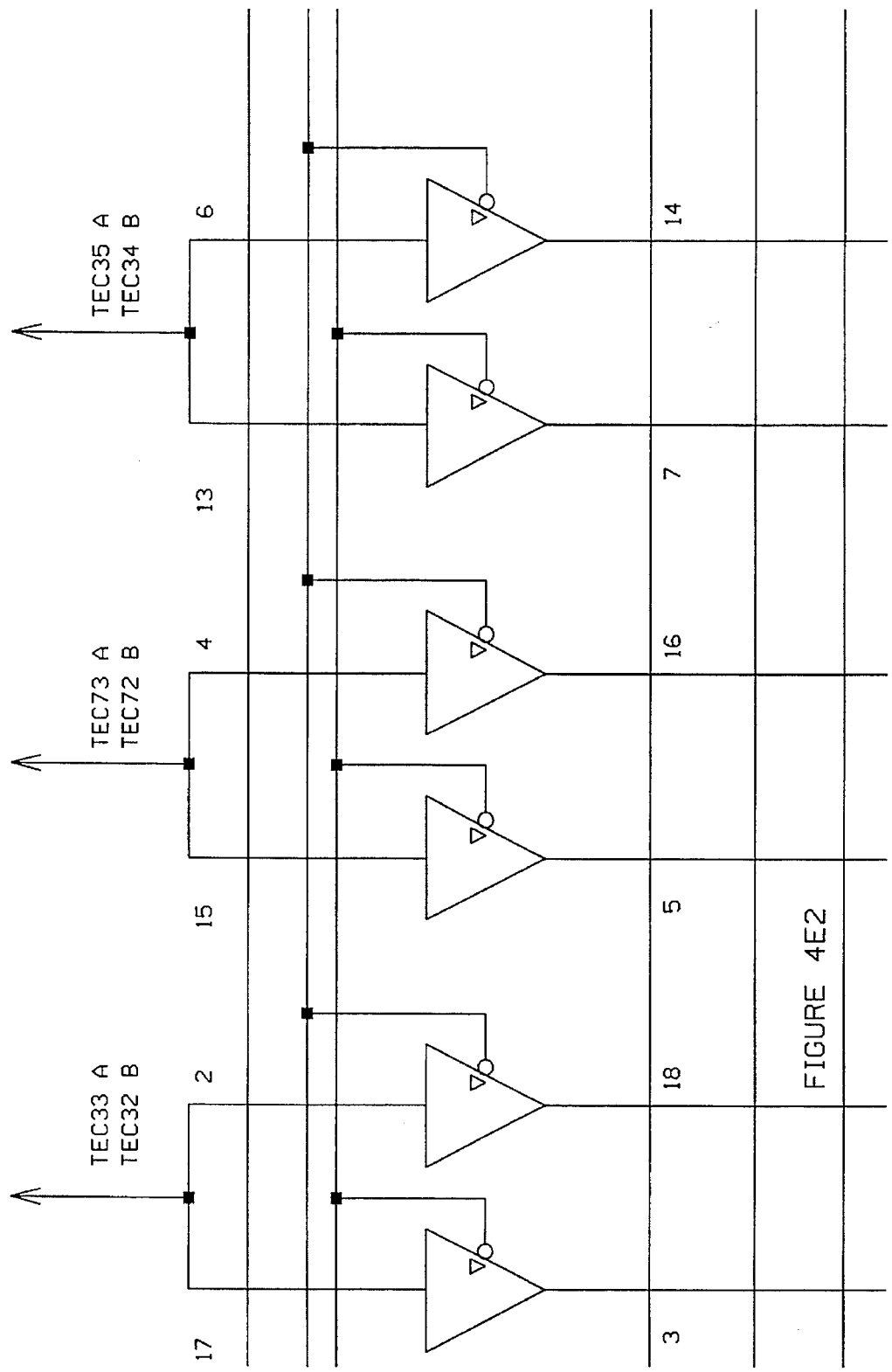

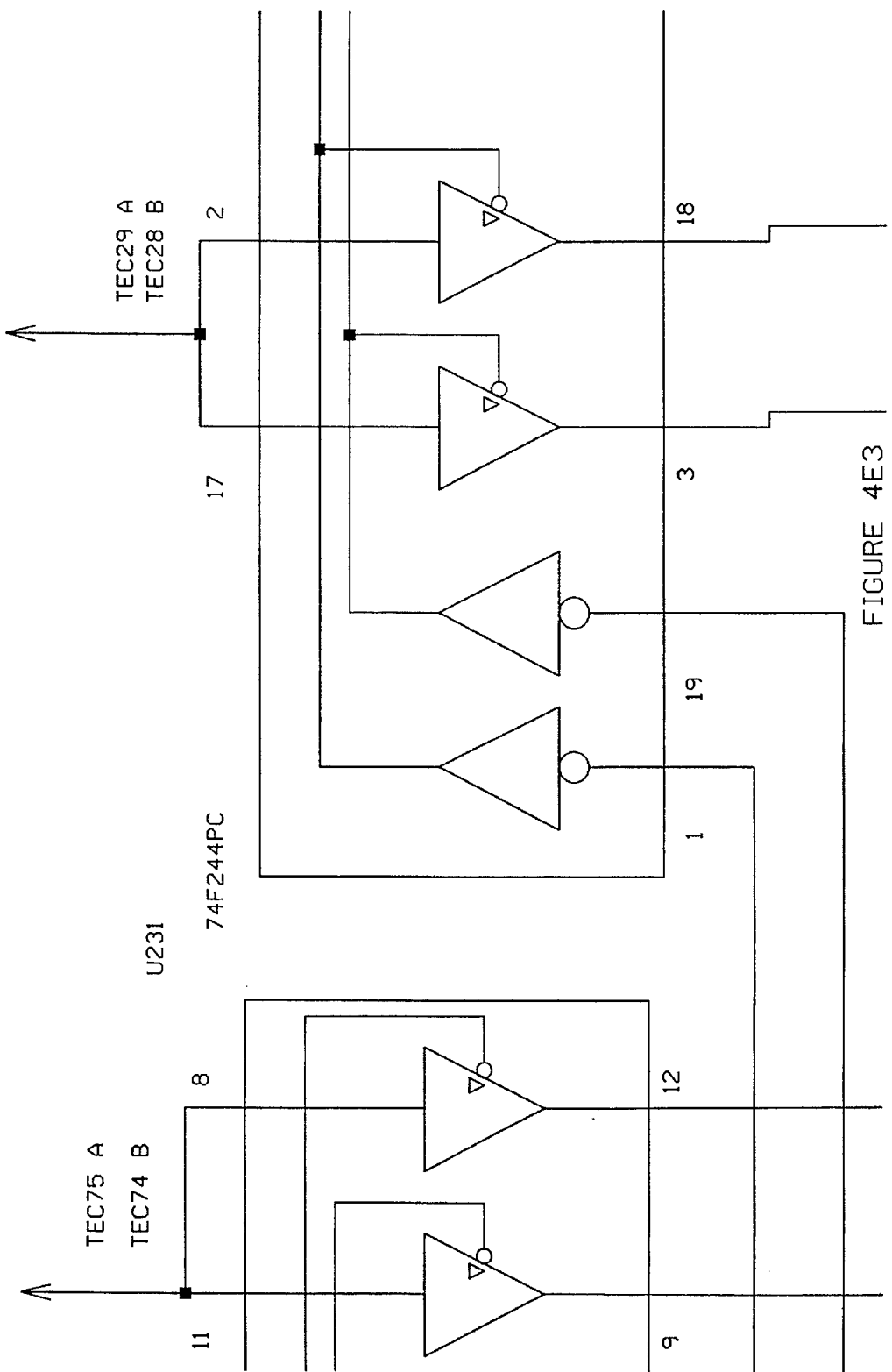
FIGURE 4E3

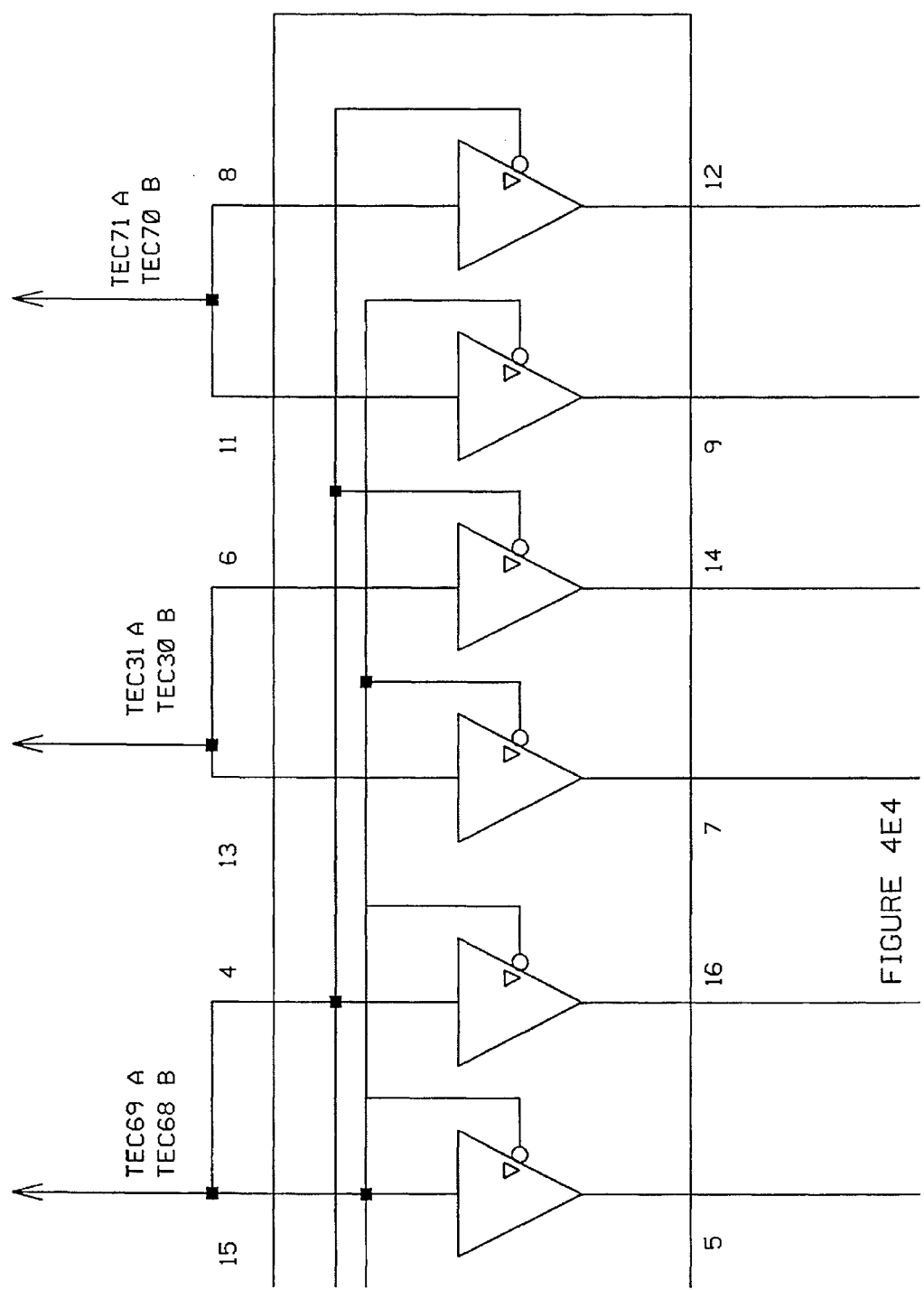
FIGURE 4E4

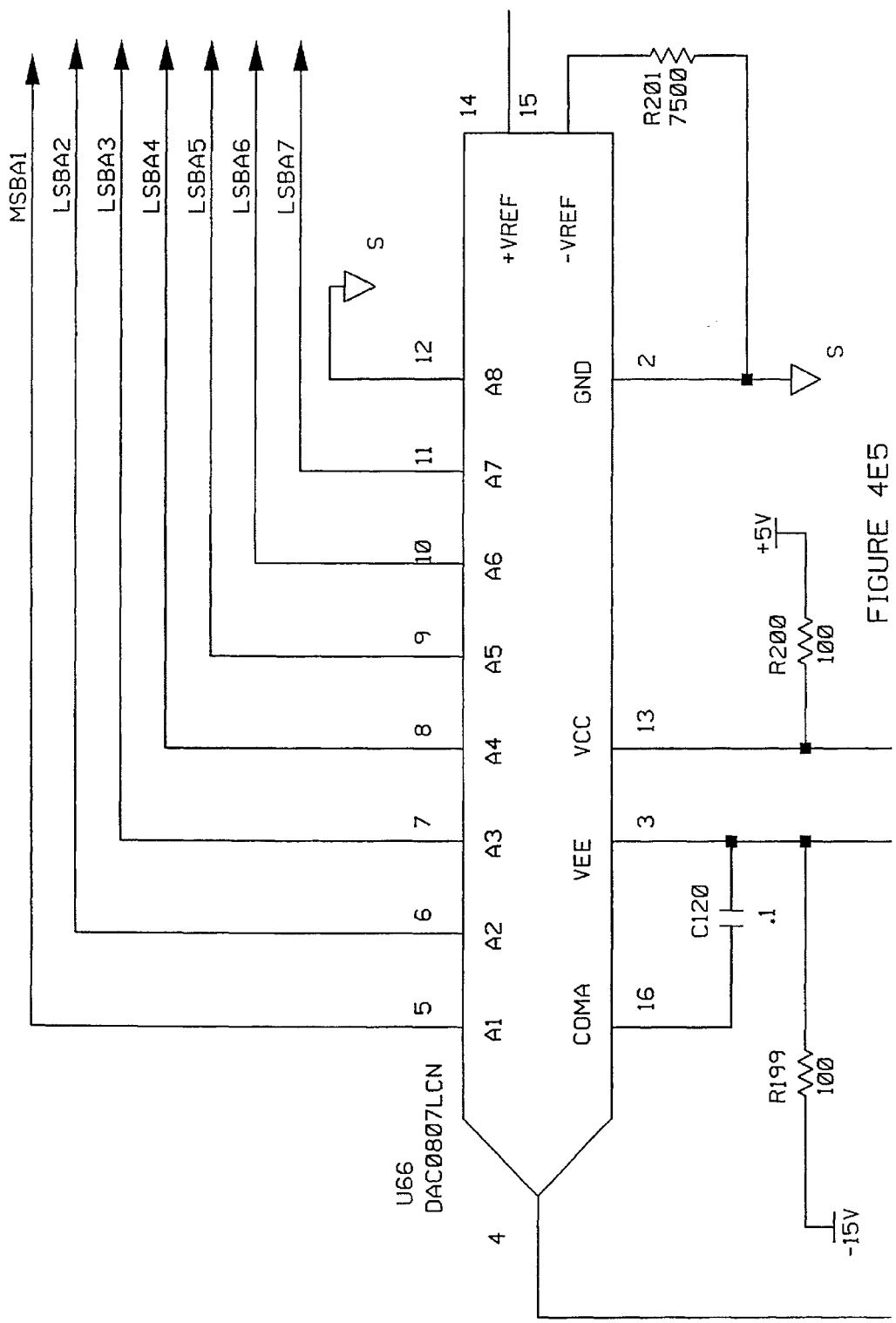
FIGURE 4E5

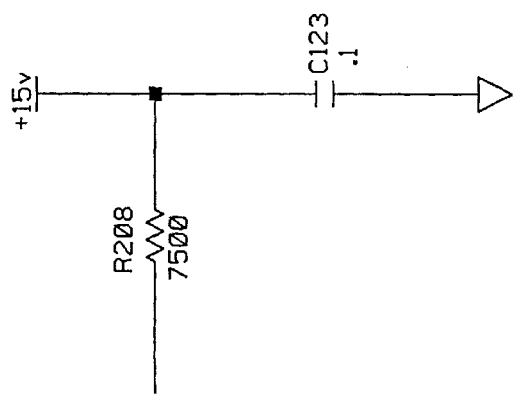
FIGURE 4E6

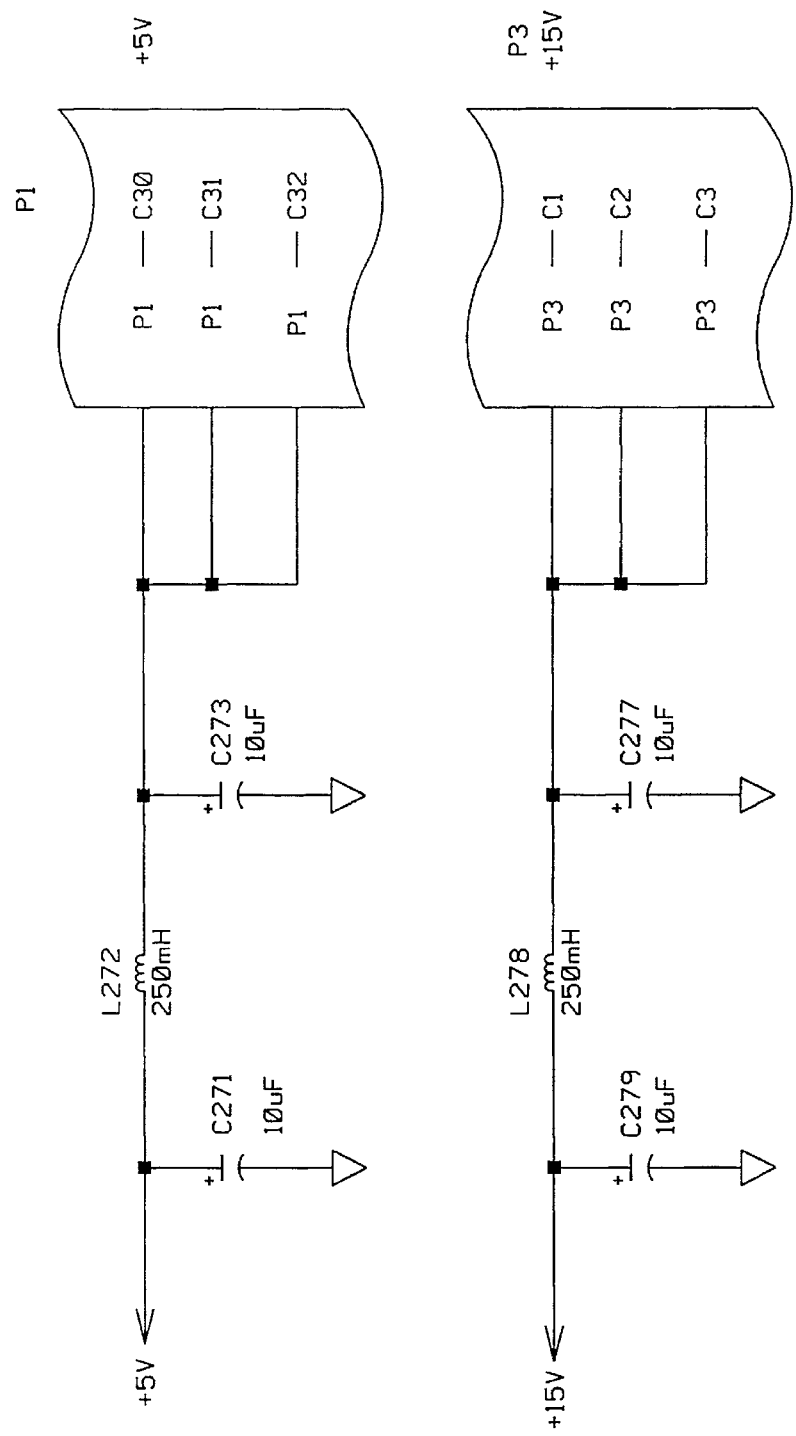
FIGURE 4E7

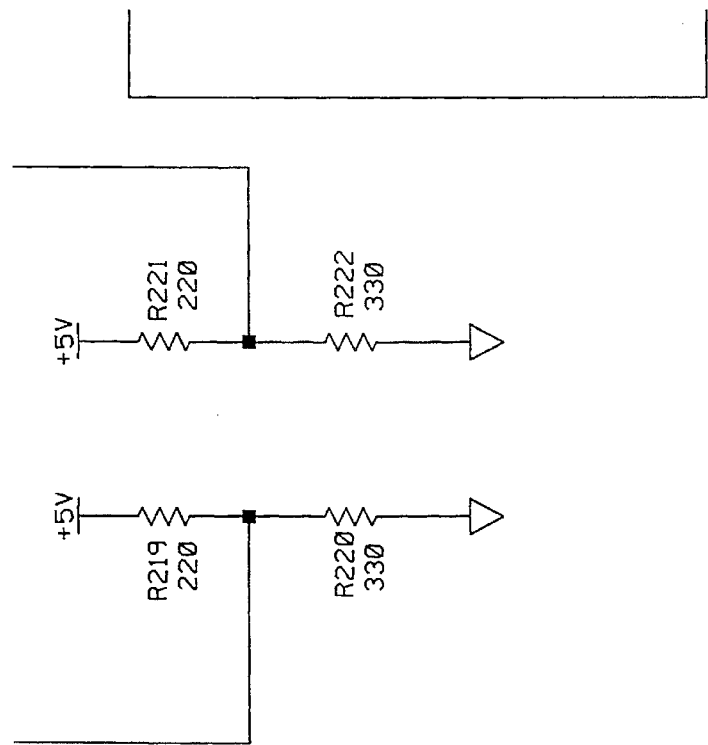
FIGURE 4E8

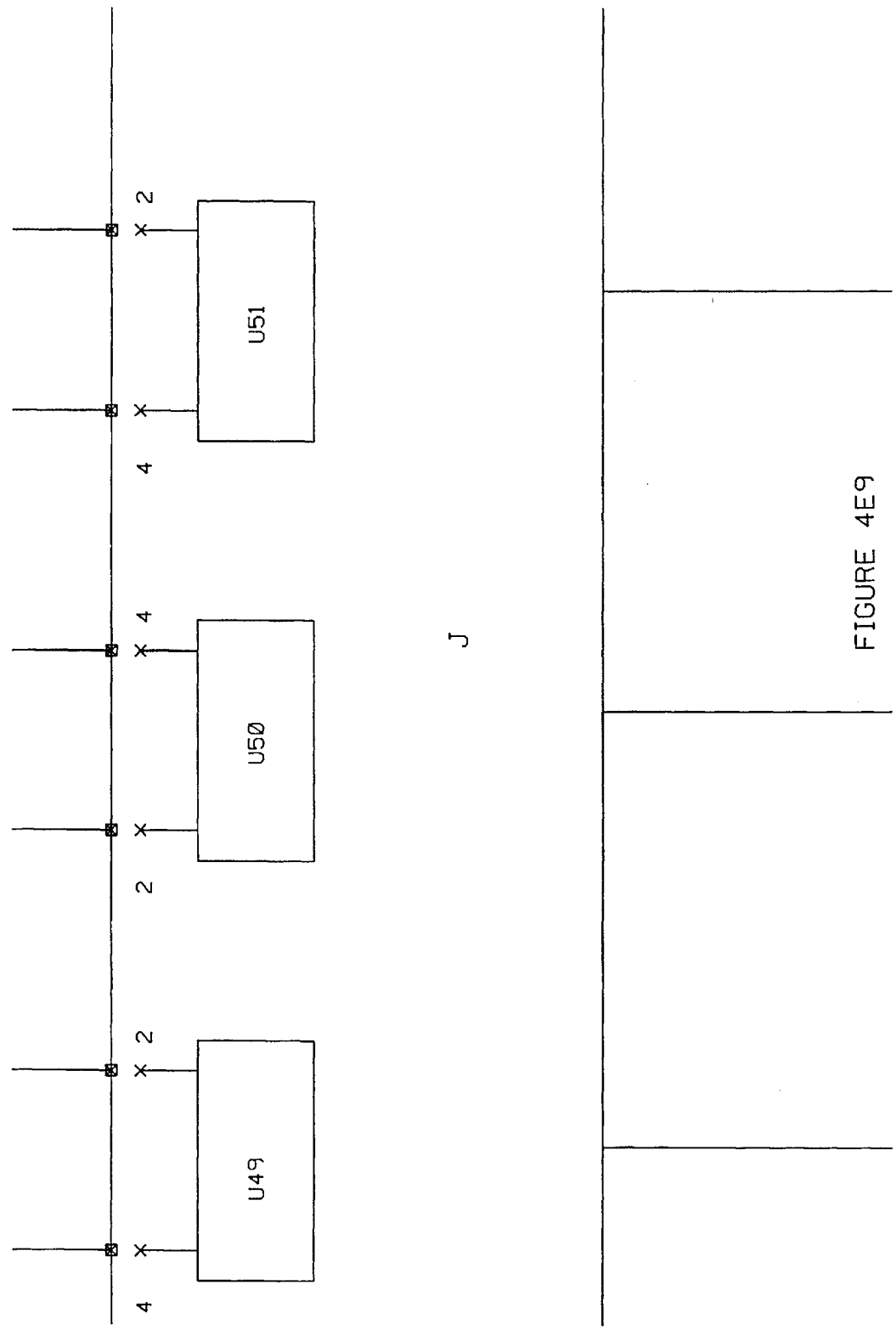
FIGURE 4E9

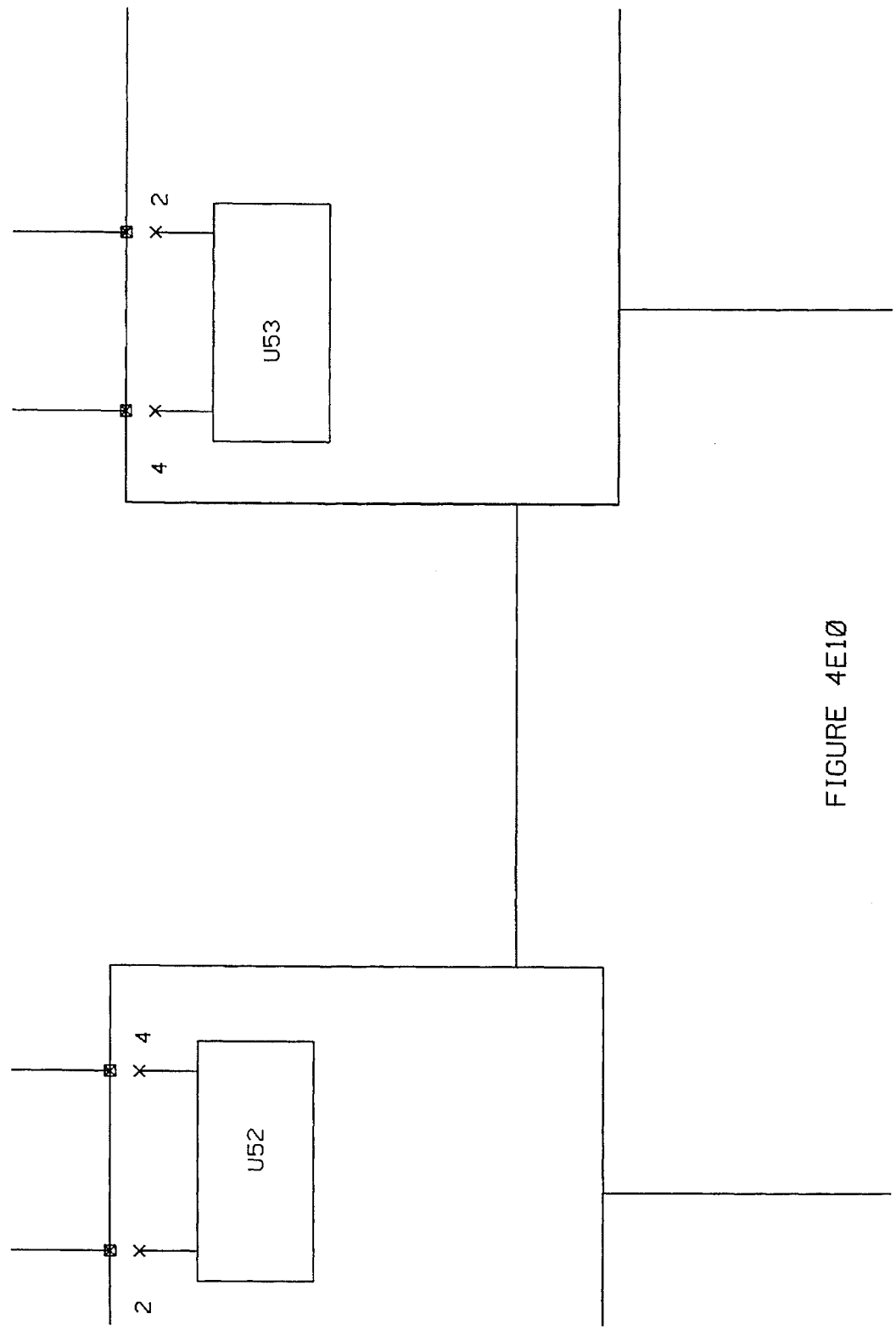
FIGURE 4E10

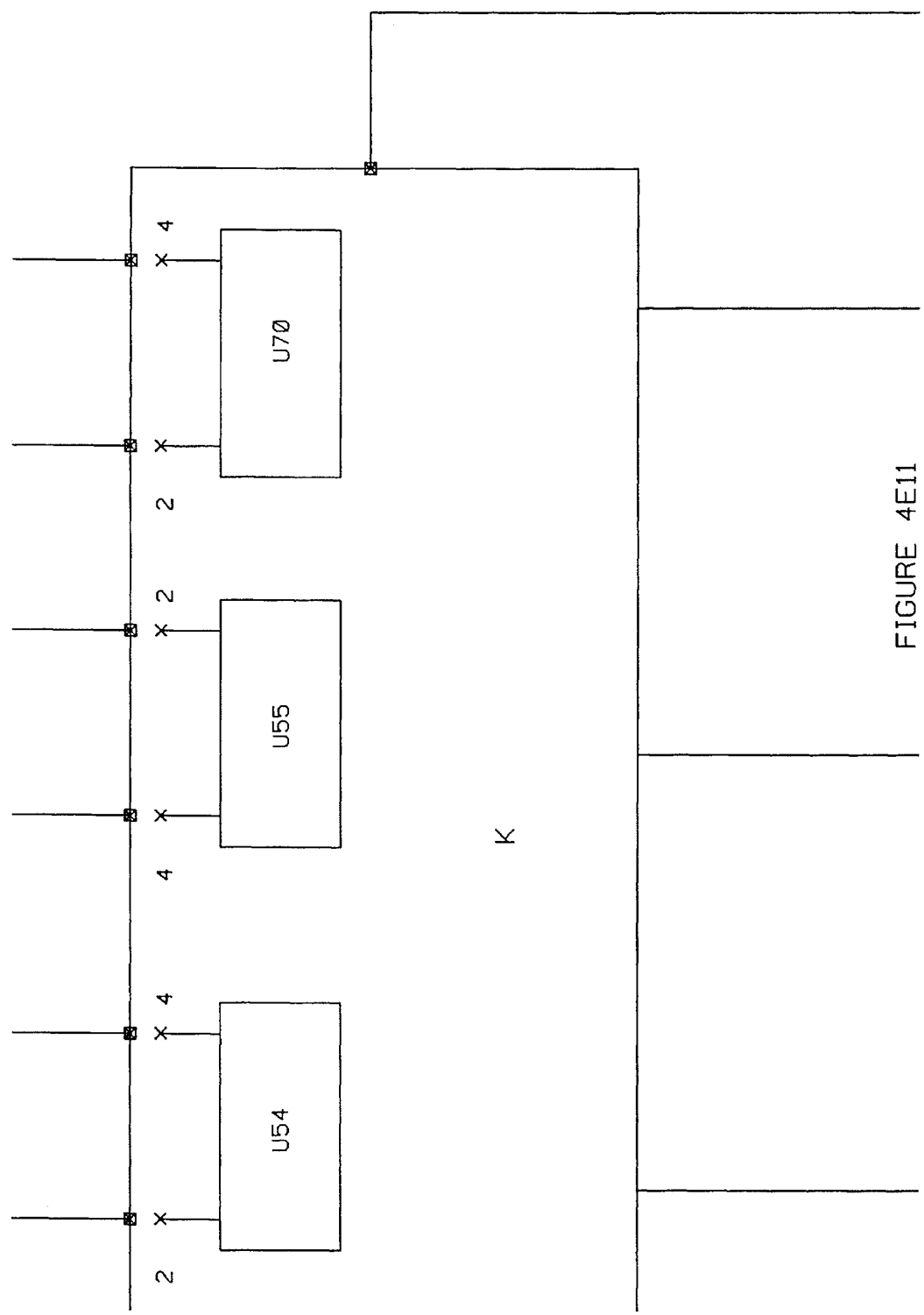
FIGURE 4E11

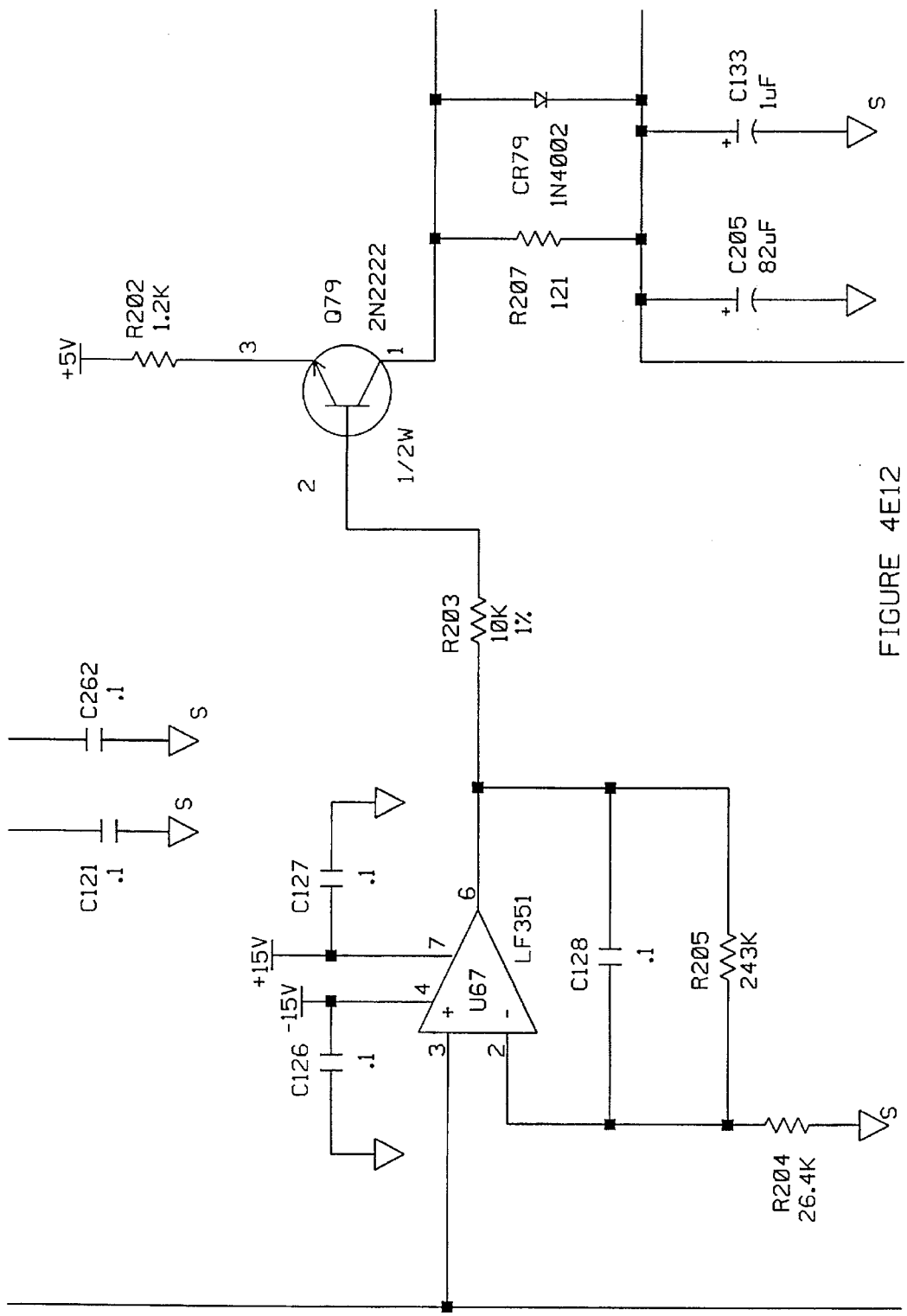
FIGURE 4E12

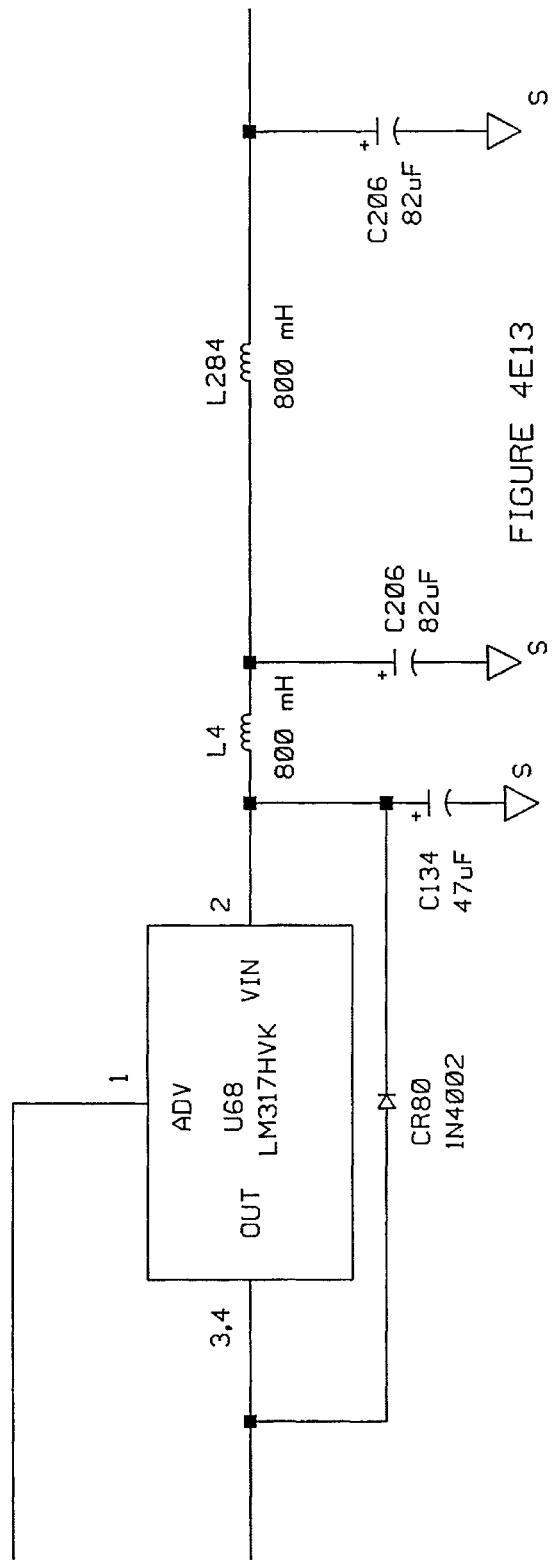
FIGURE 4E13

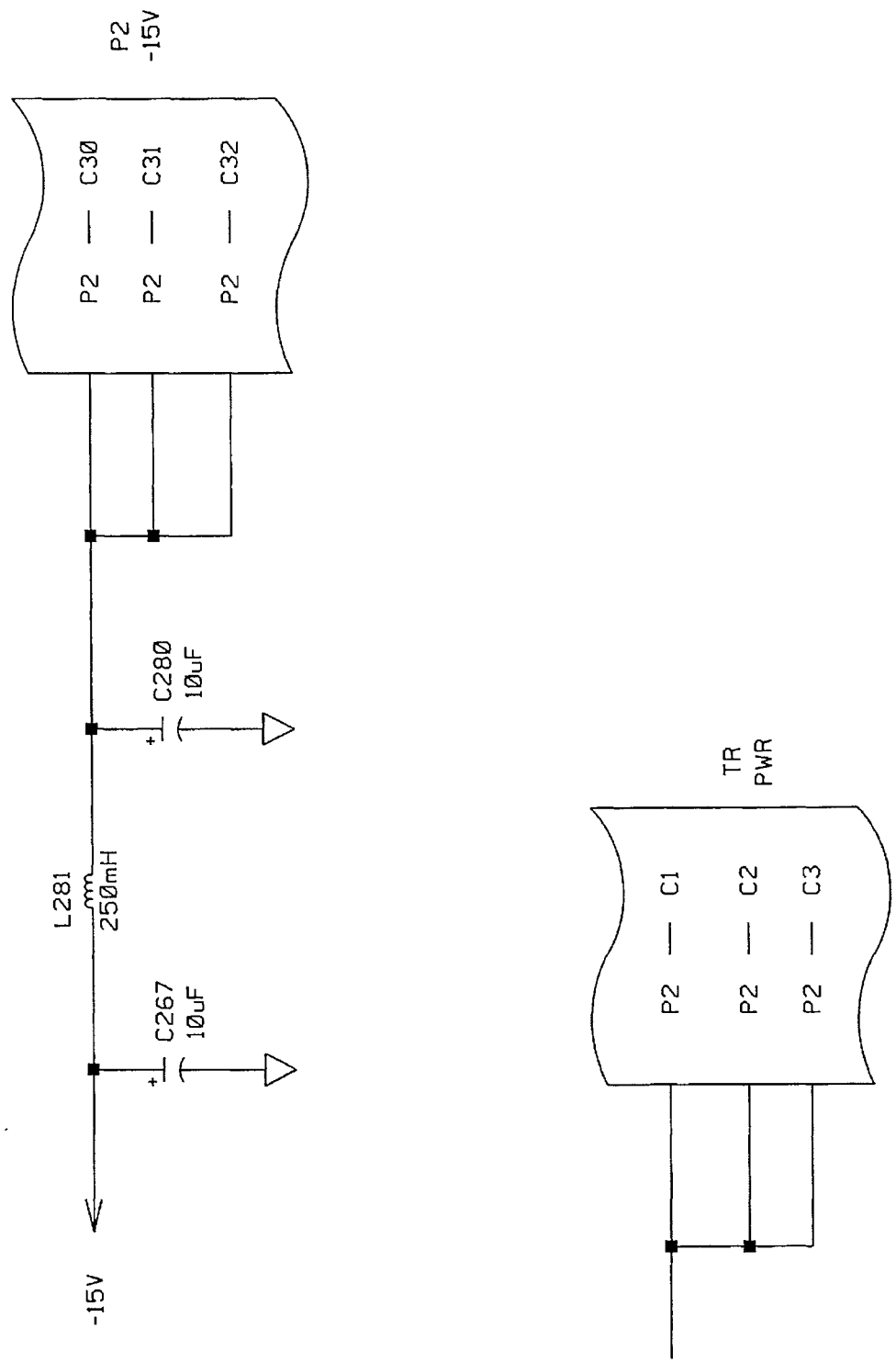
FIGURE 4E14

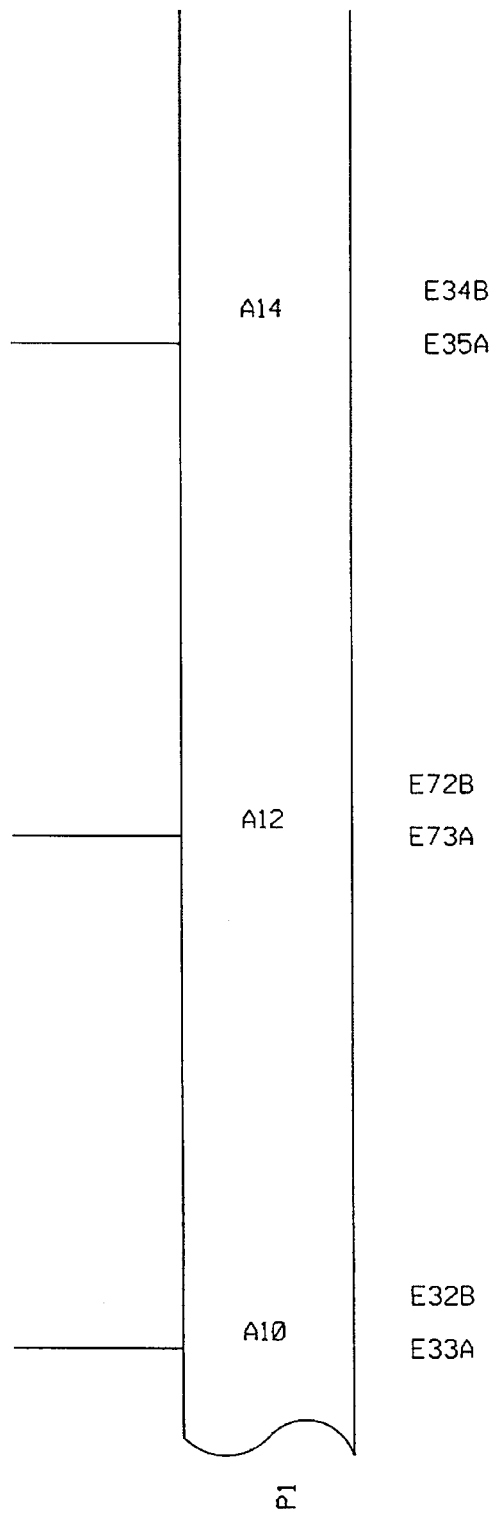
FIGURE 4E15

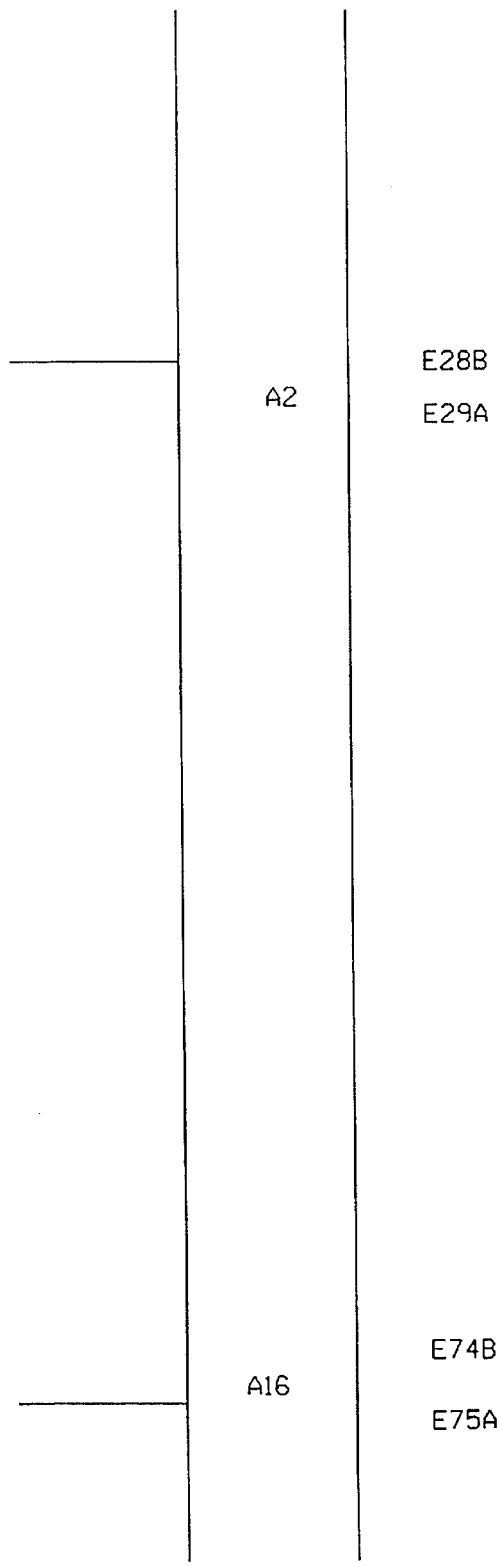
FIGURE 4E16

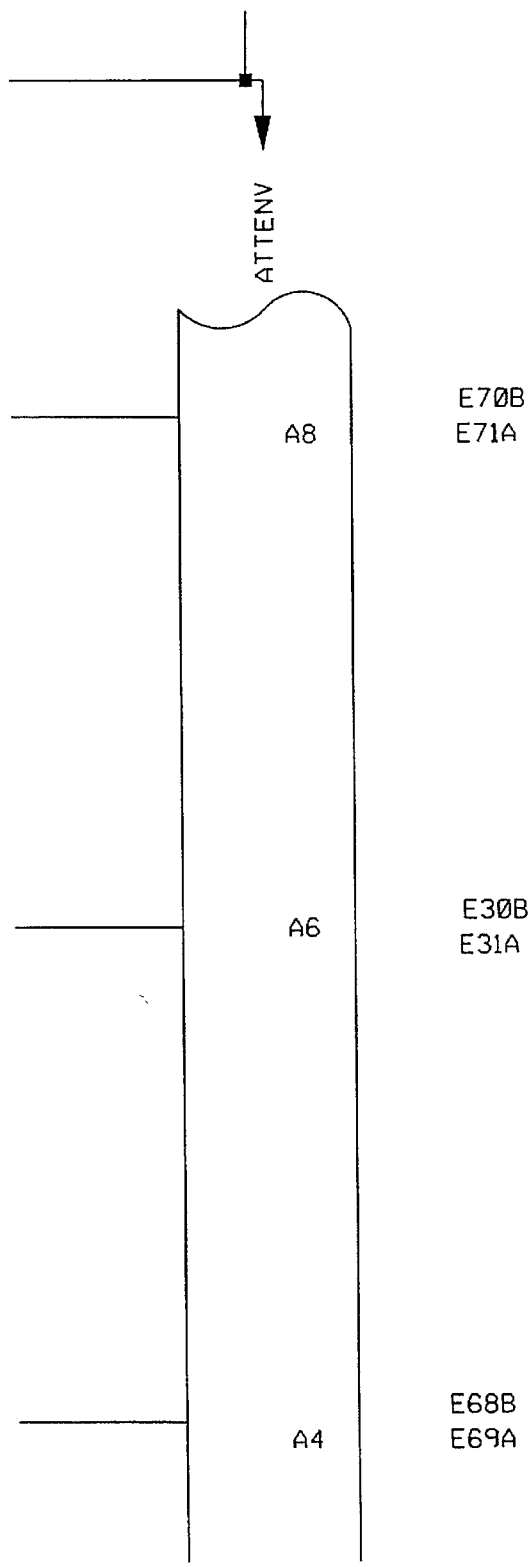
FIGURE 4E17

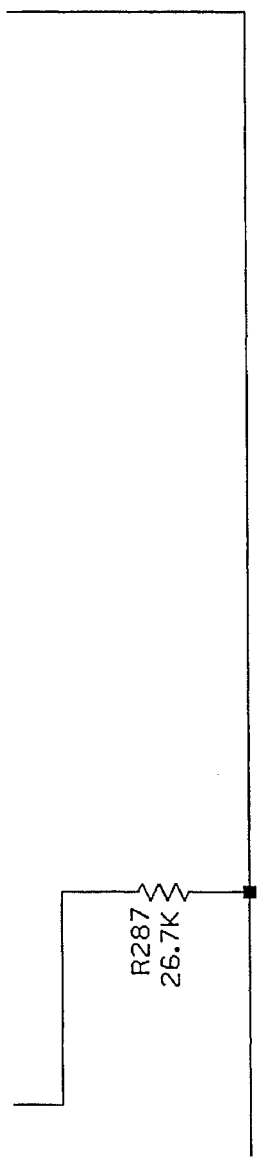
FIGURE 4E18

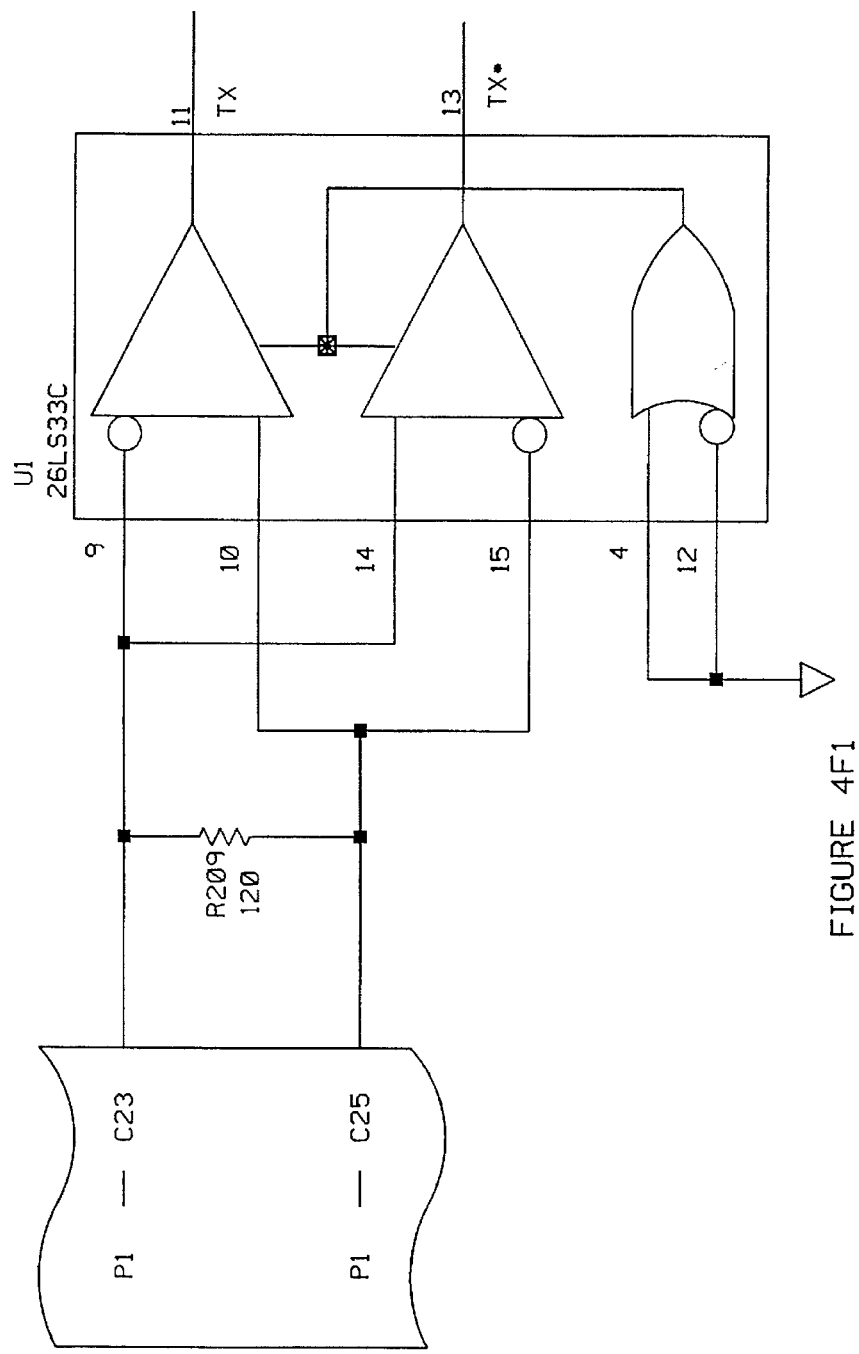
FIGURE 4F1

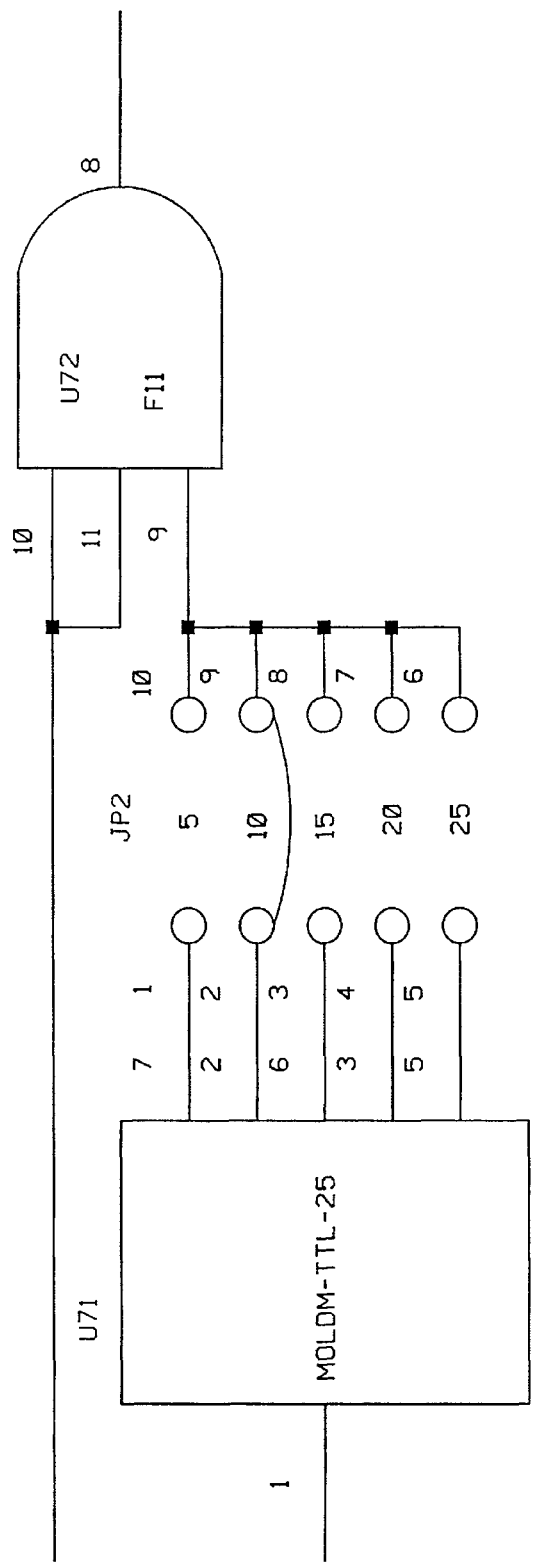
FIGURE 4F2

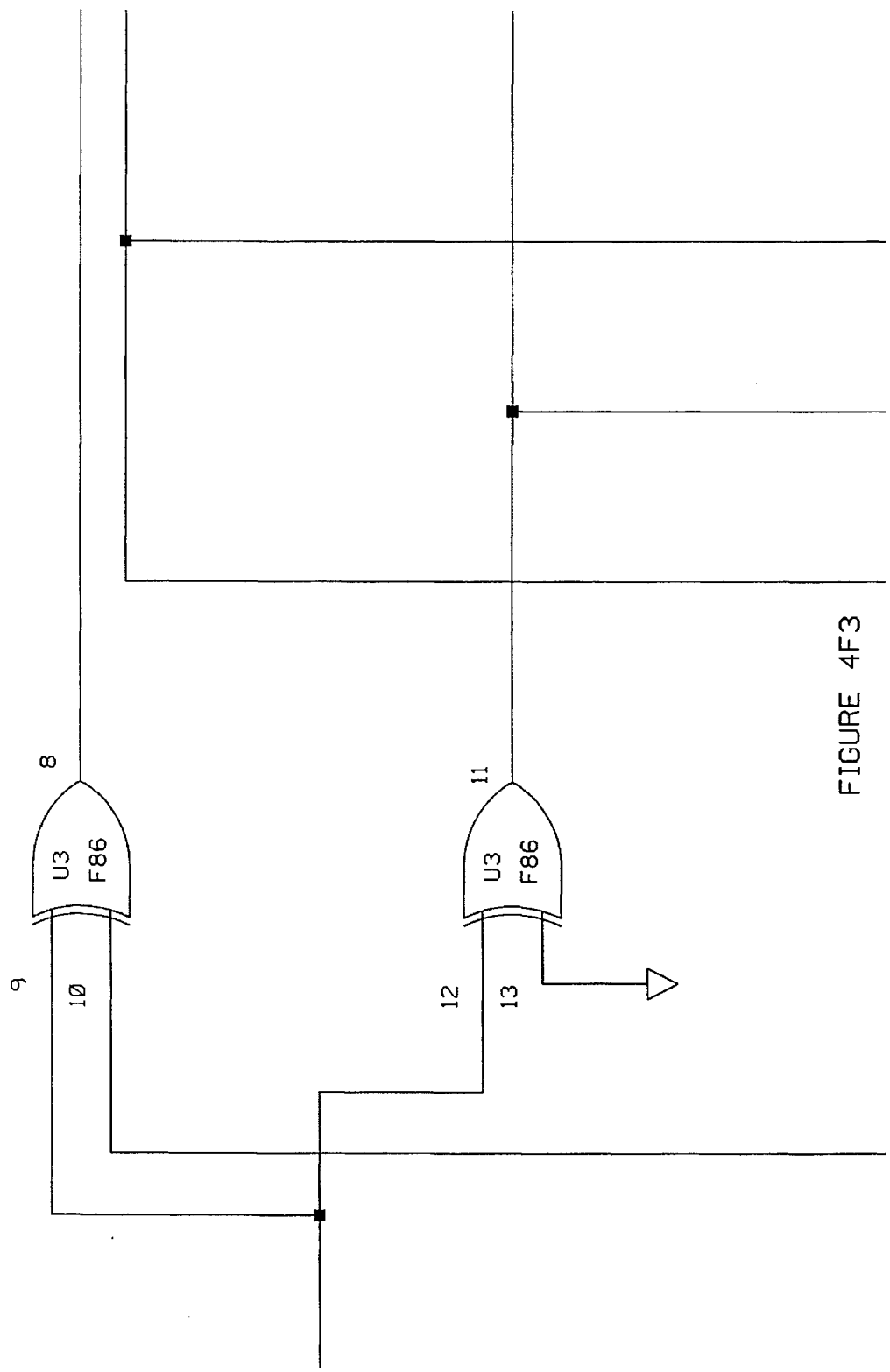
FIGURE 4F3

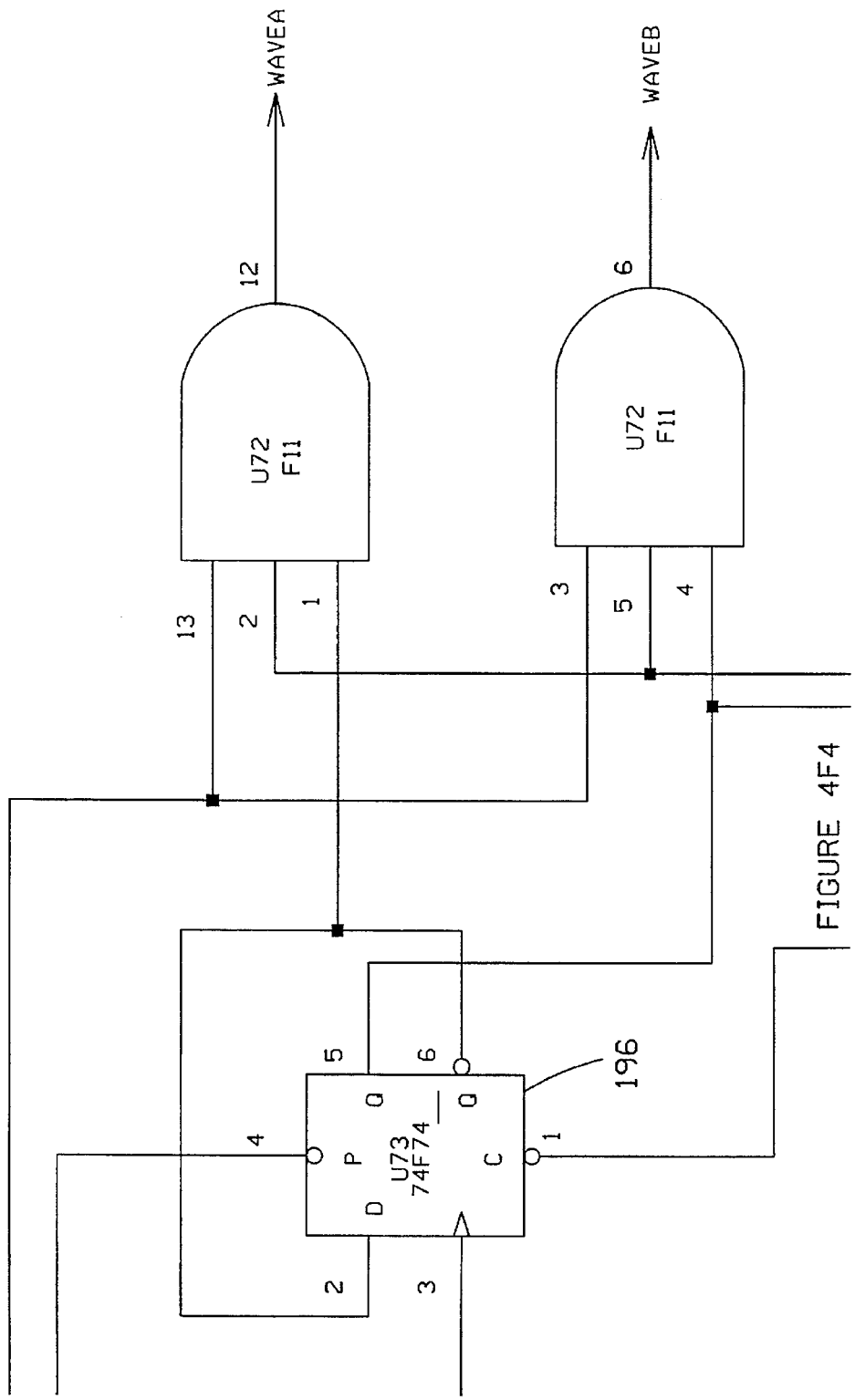
FIGURE 4F4

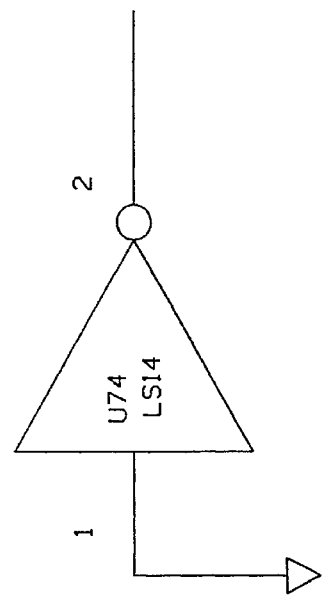
FIGURE 4F5

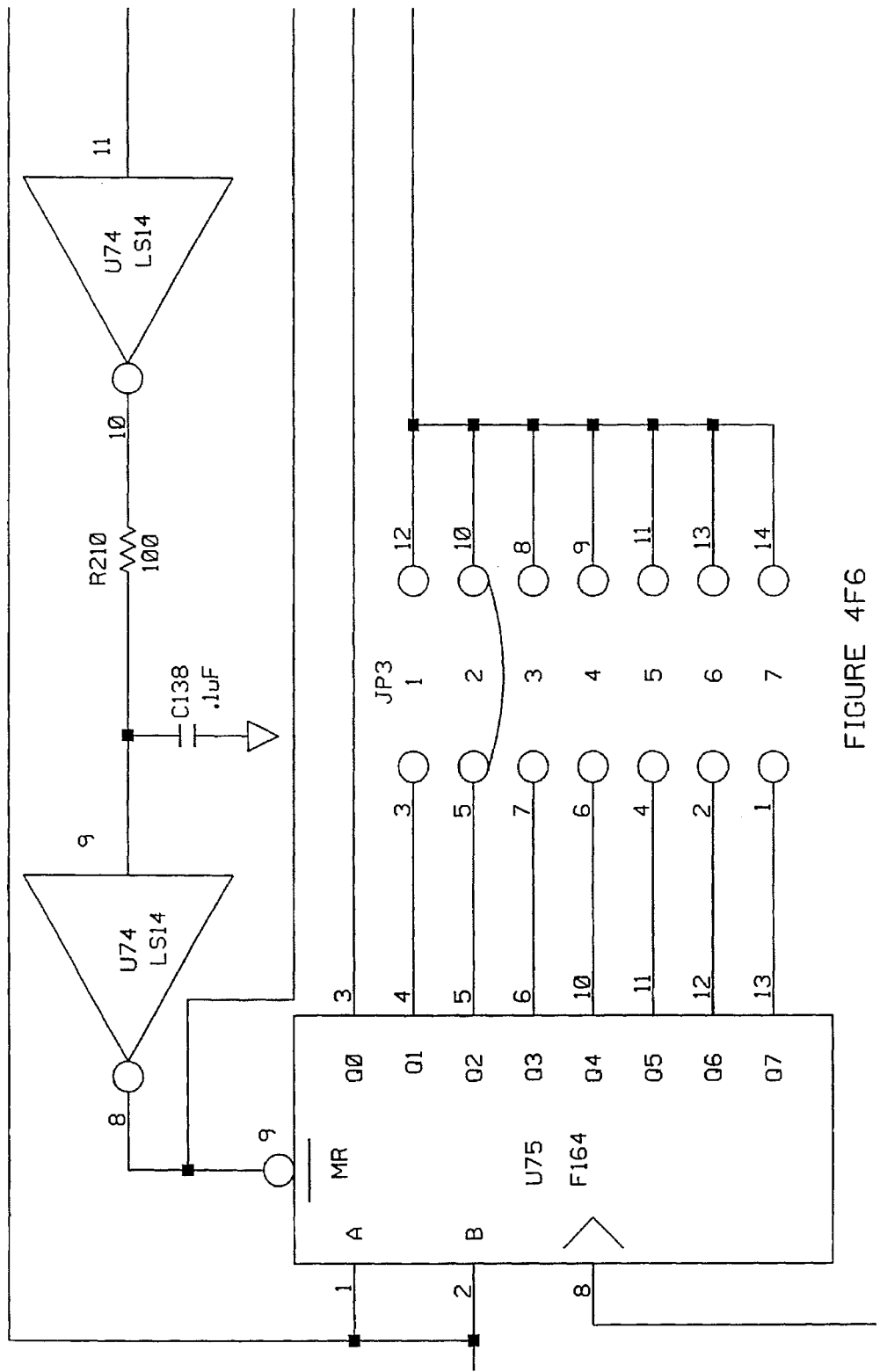
FIGURE 4F6

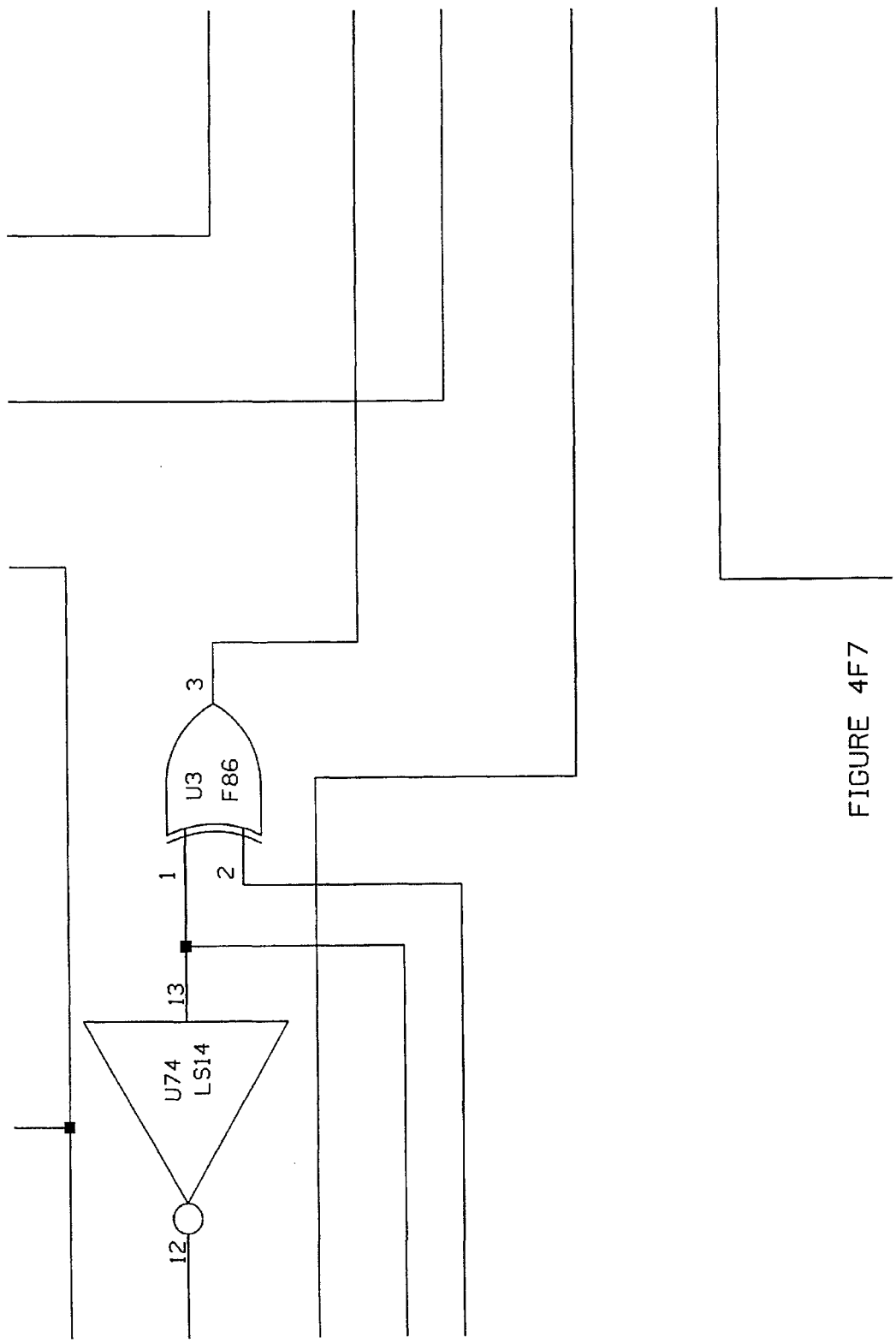
FIGURE 4F7

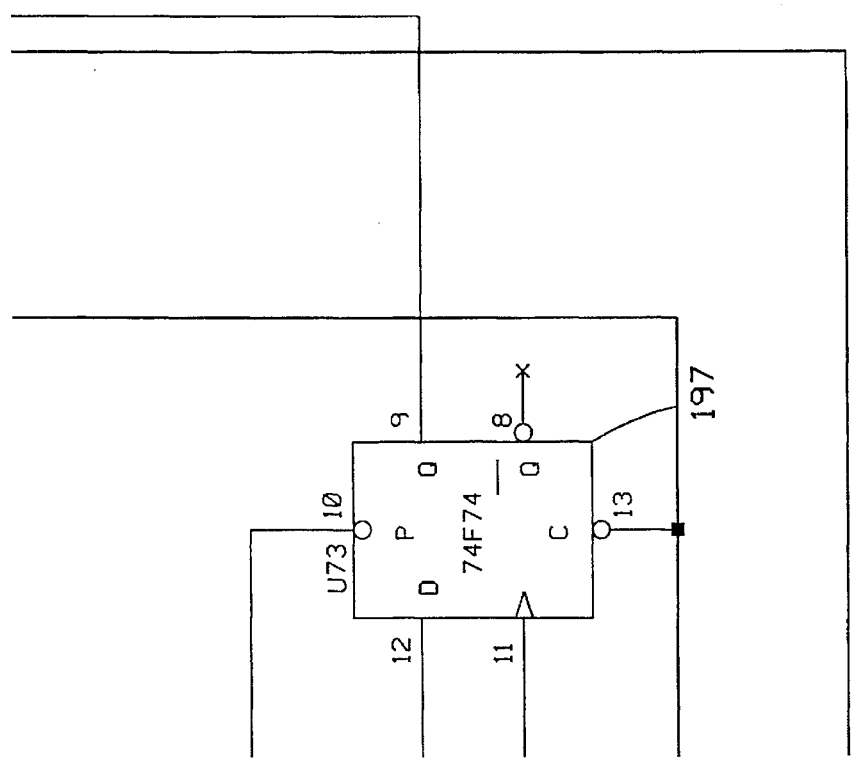
FIGURE 4F8

CYCLES PER TRANSMIT PULSE

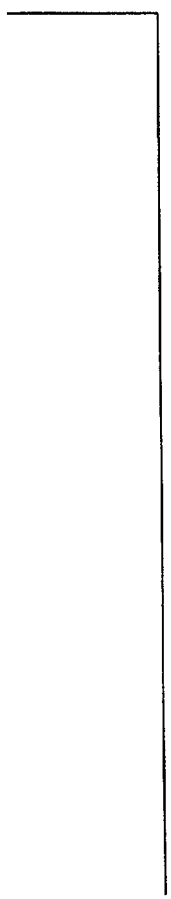
FIGURE 4F10

TYPICAL TRANSDUCER ELEMENT SWITCH

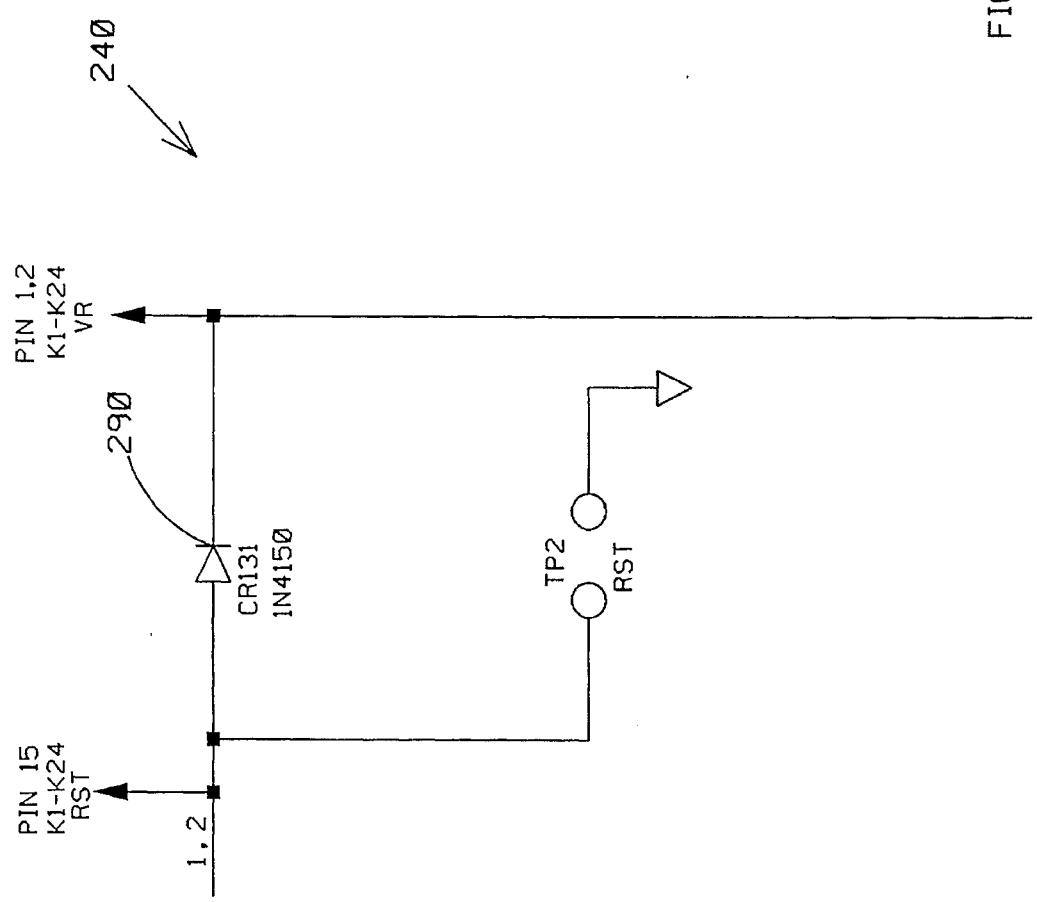

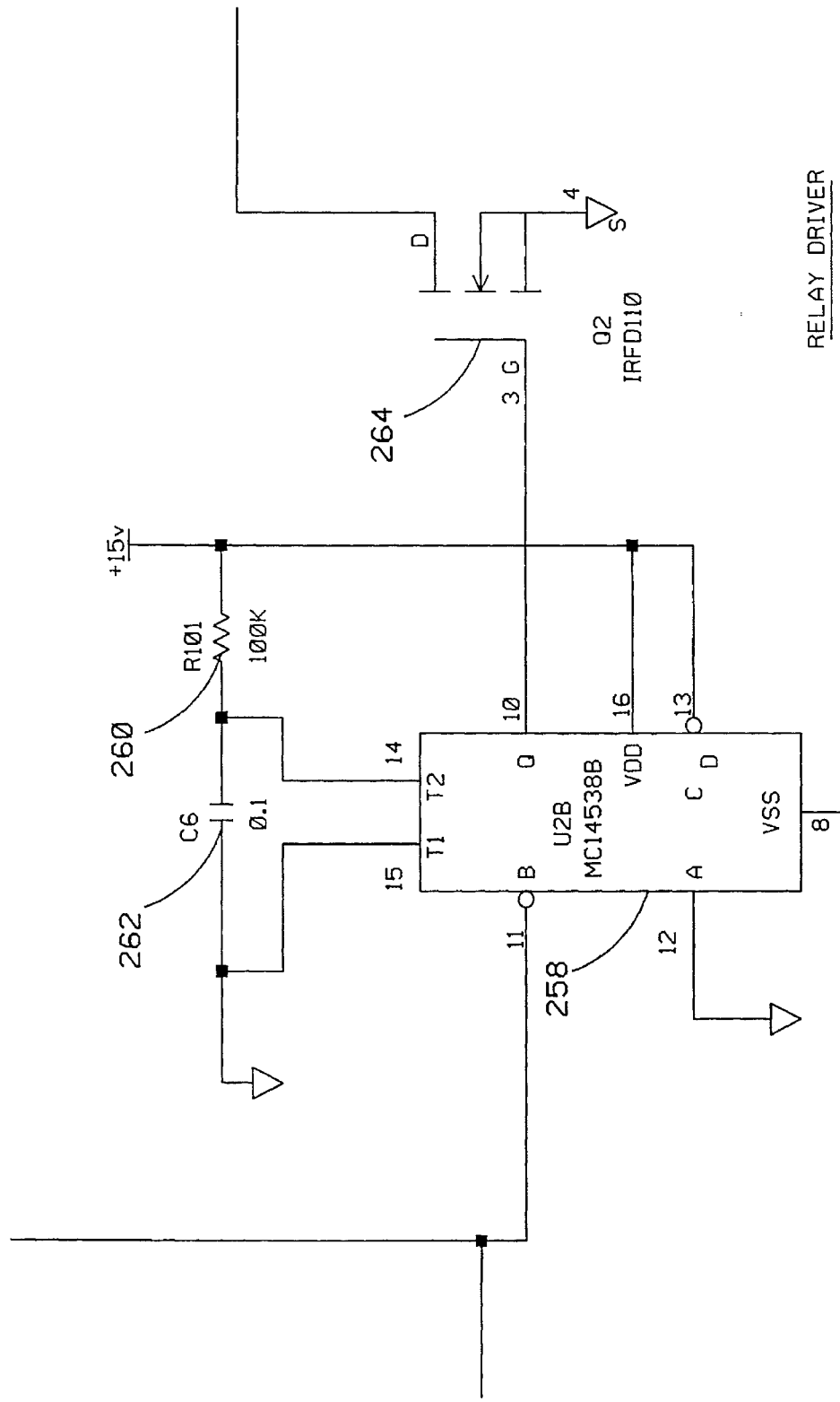

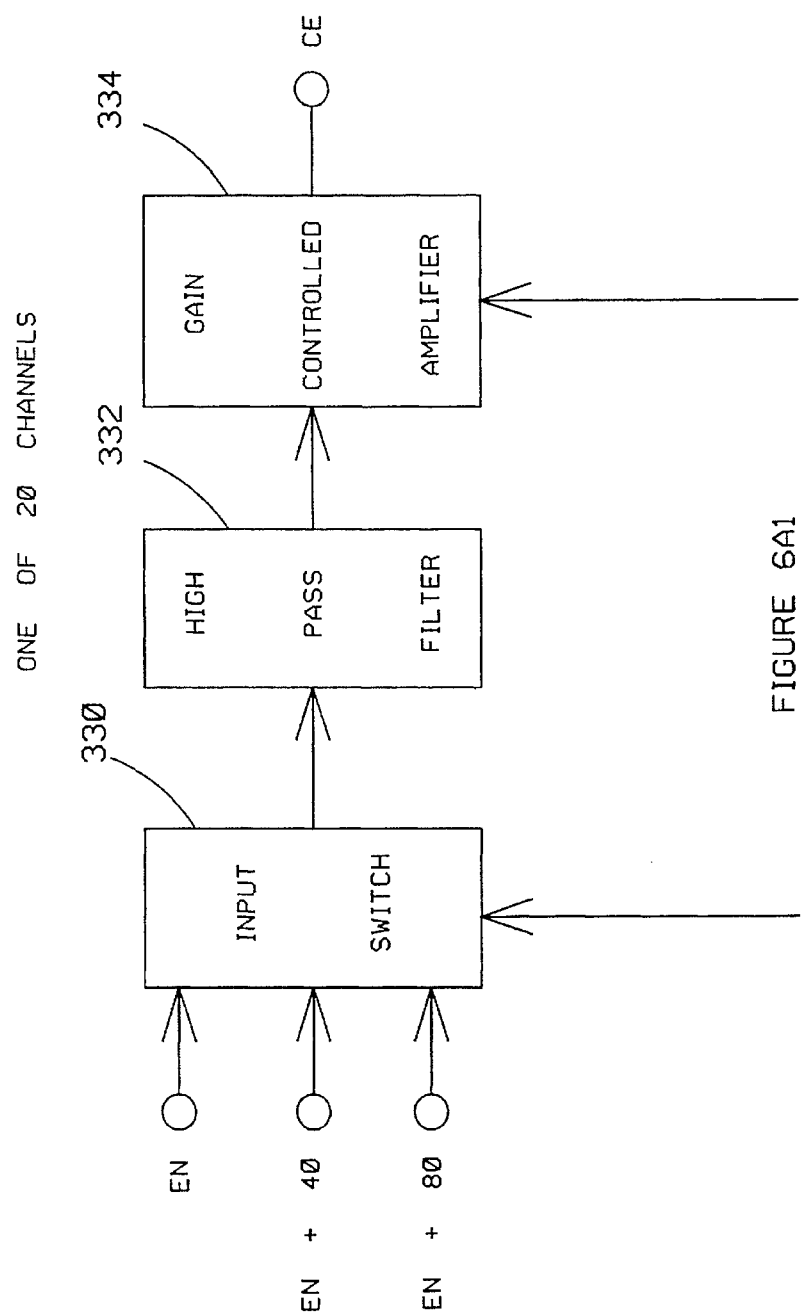
FIGURE 6A1

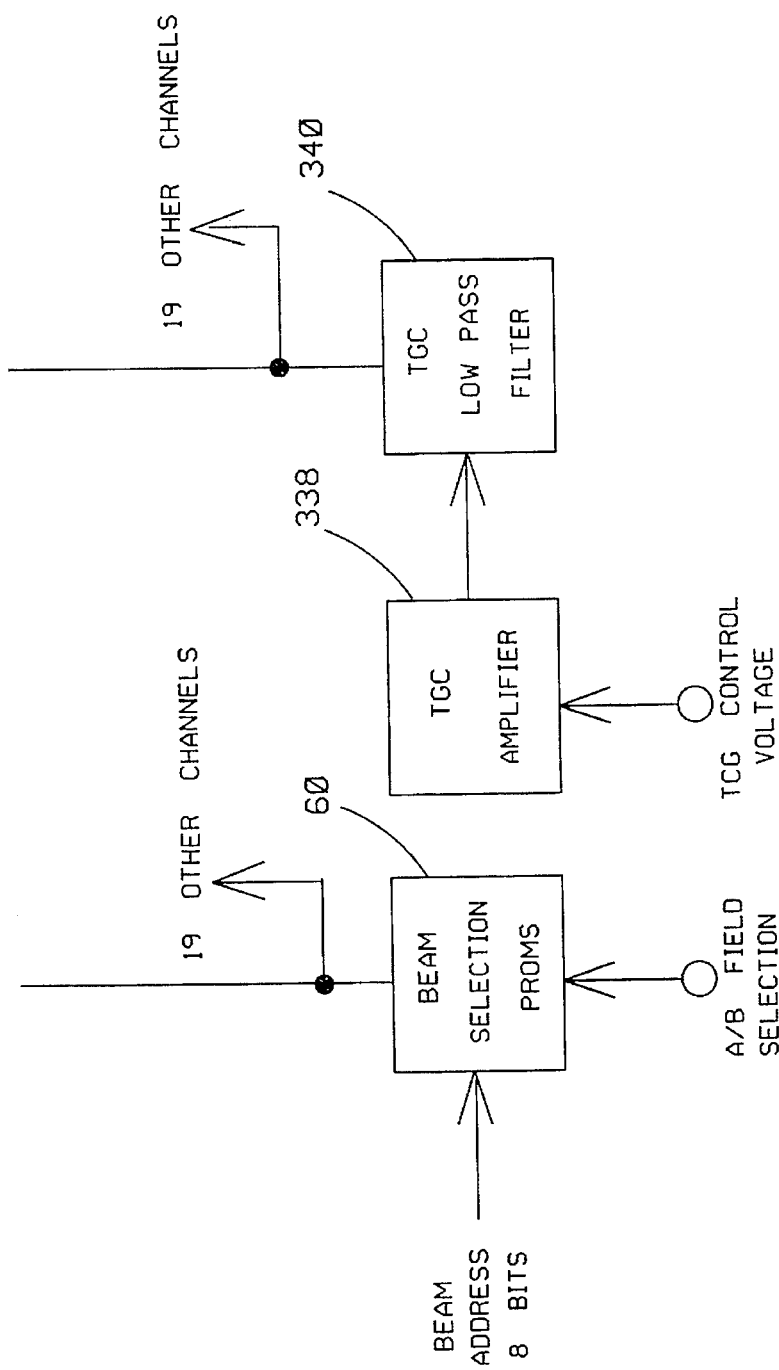
CROSSBAR PCB BLOCK DIAGRAM
FIGURE 6A2

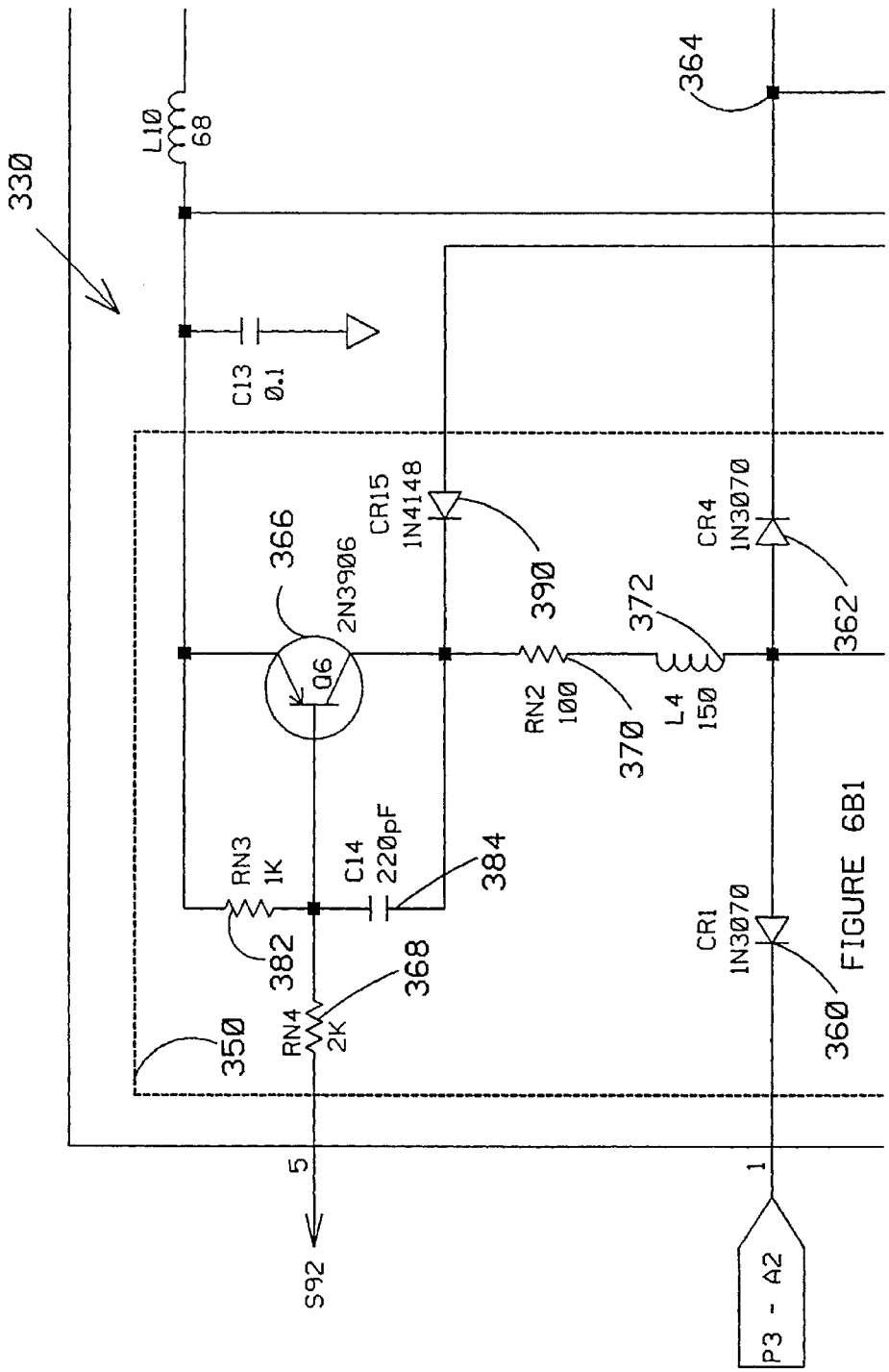

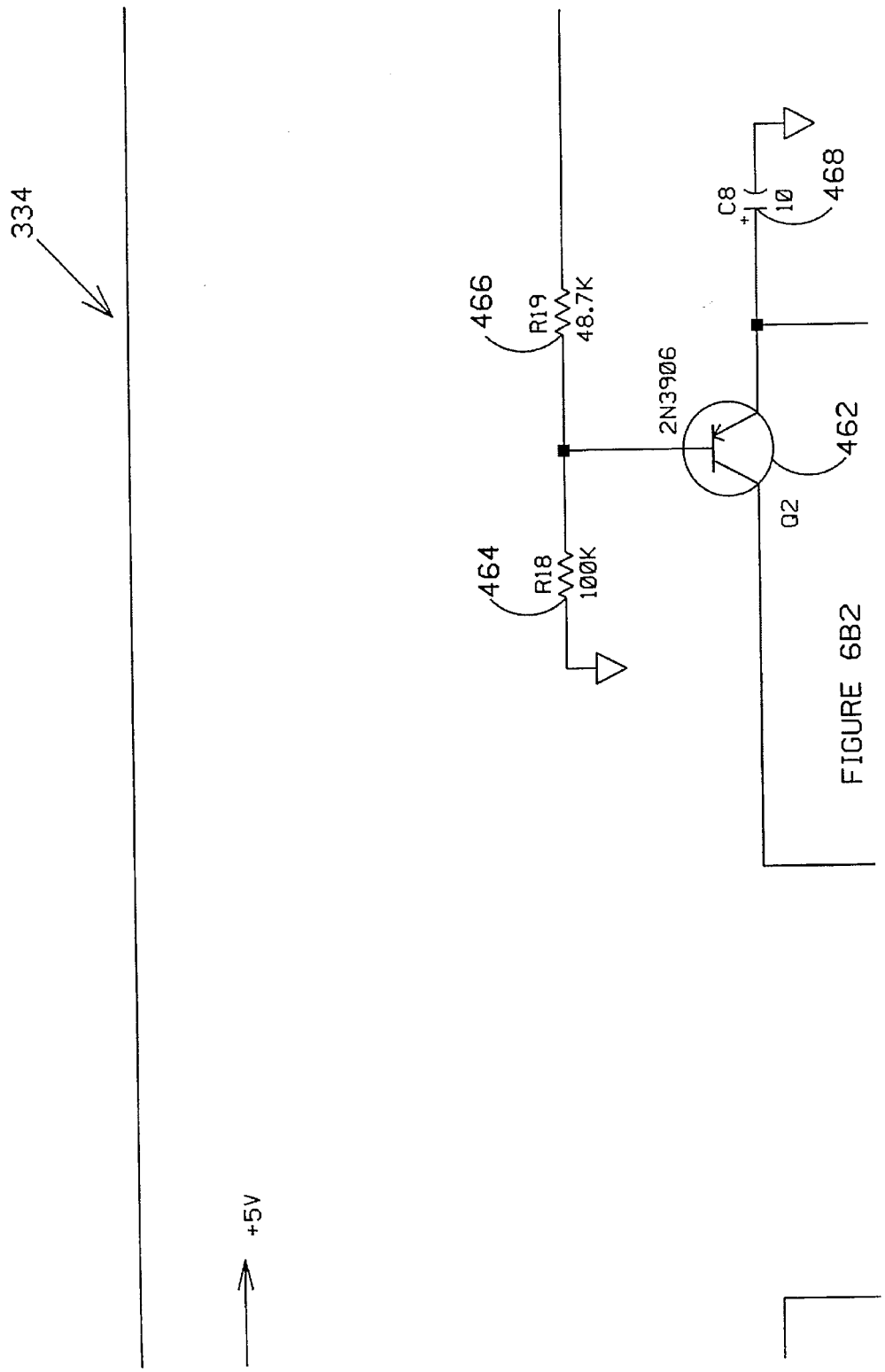
FIGURE 6B2

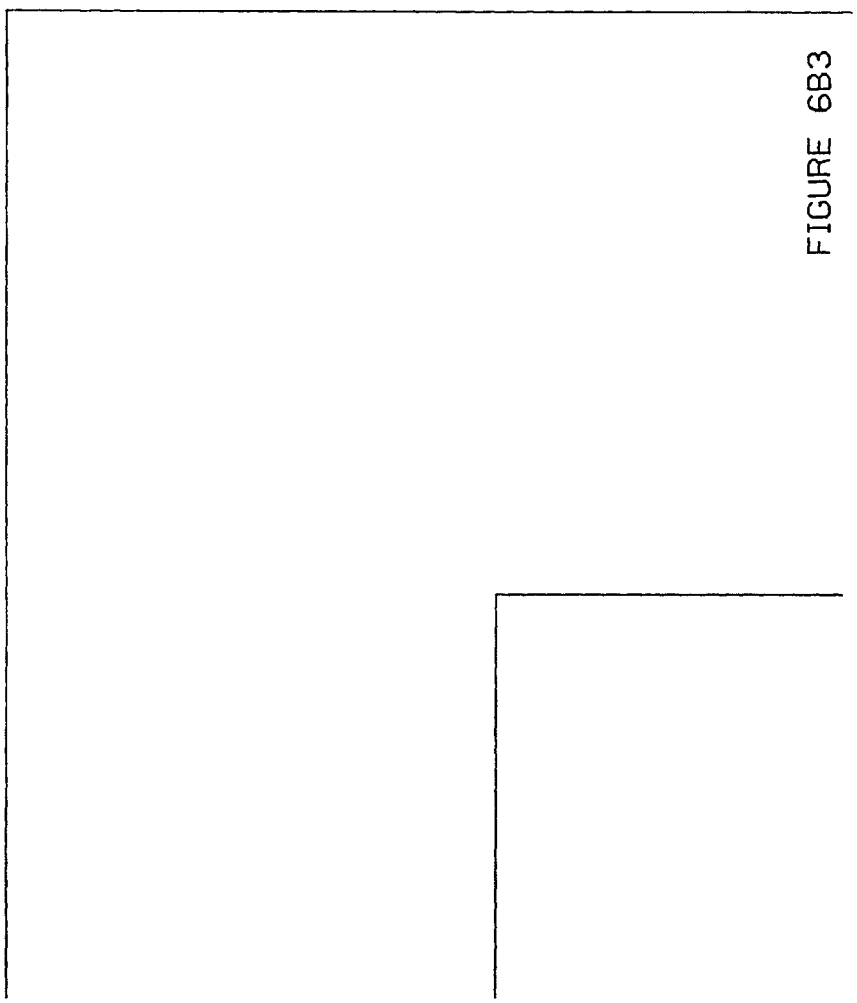

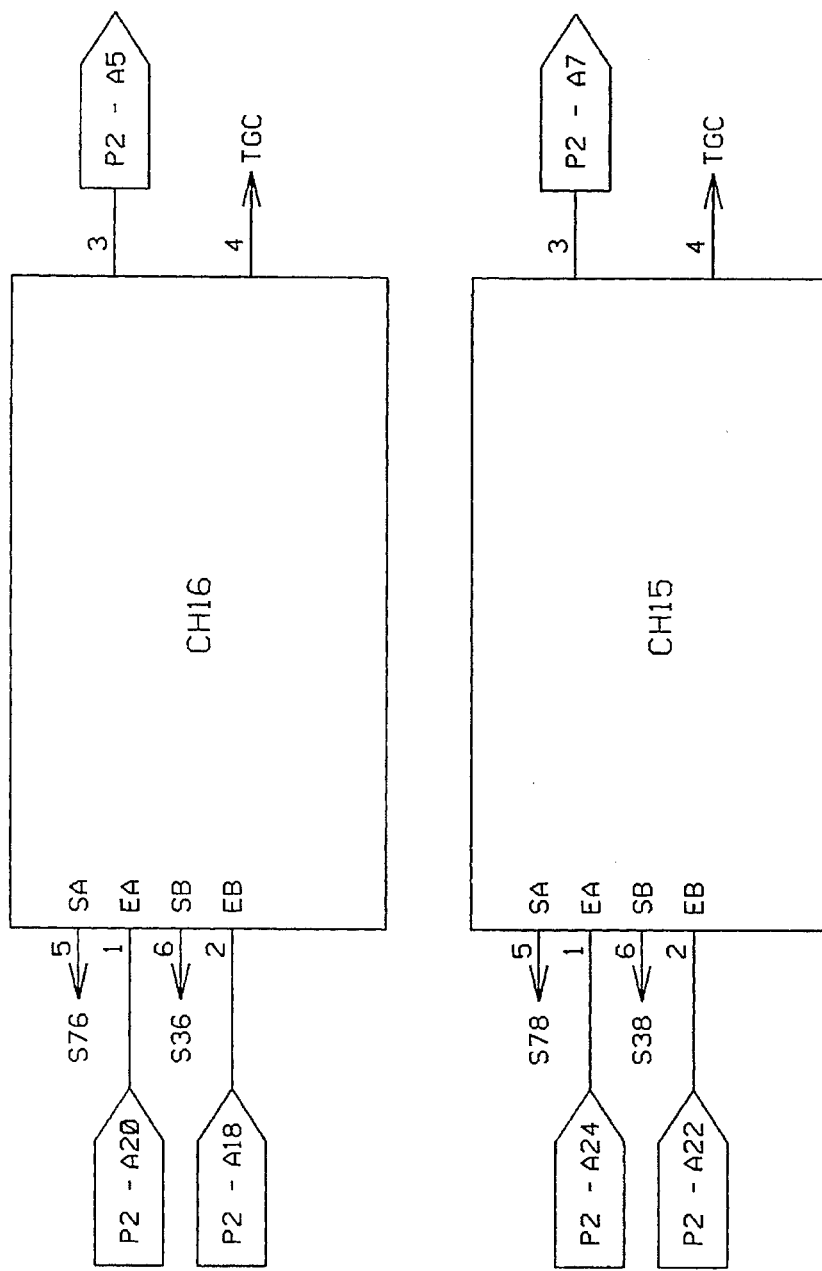
FIGURE 6B4

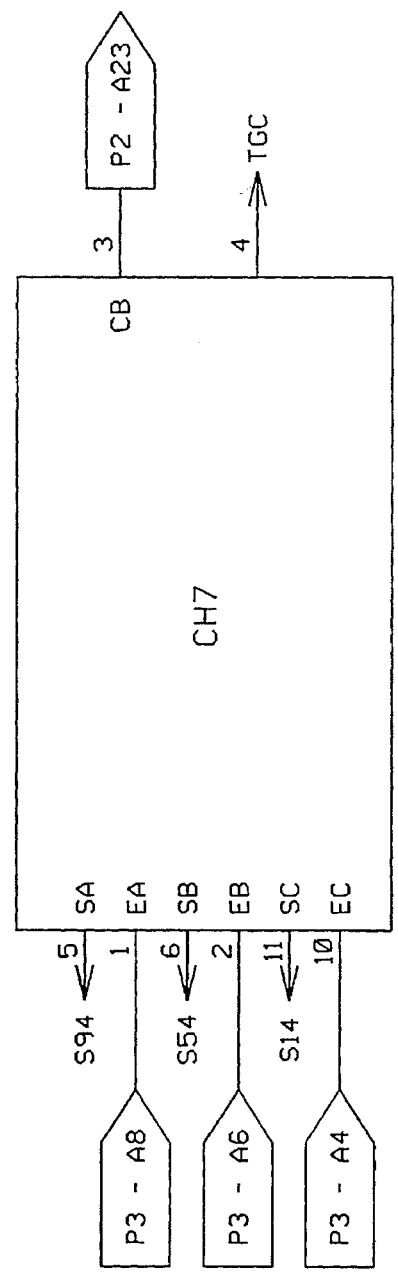
FIGURE 6B5

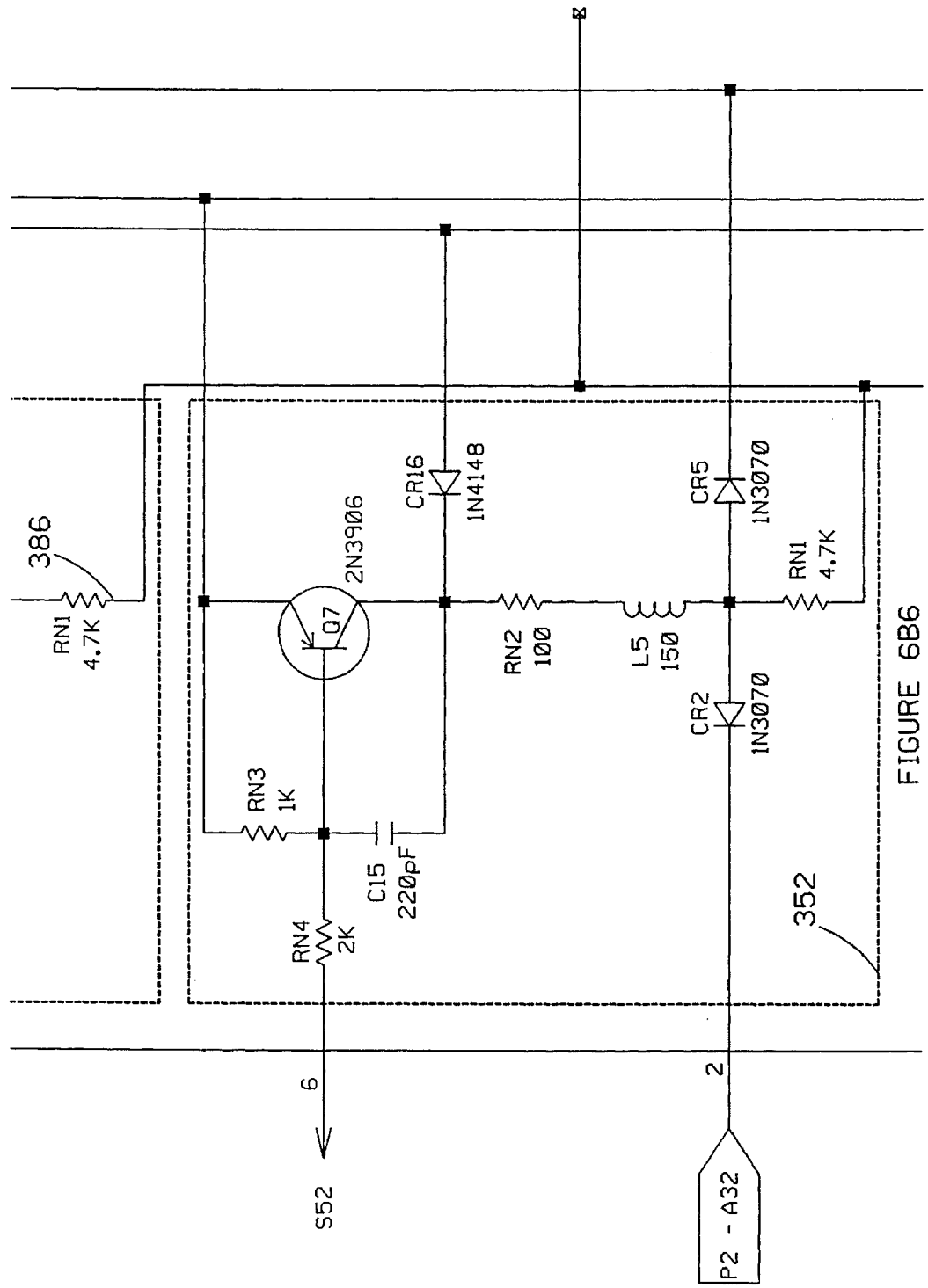
FIGURE 6B6

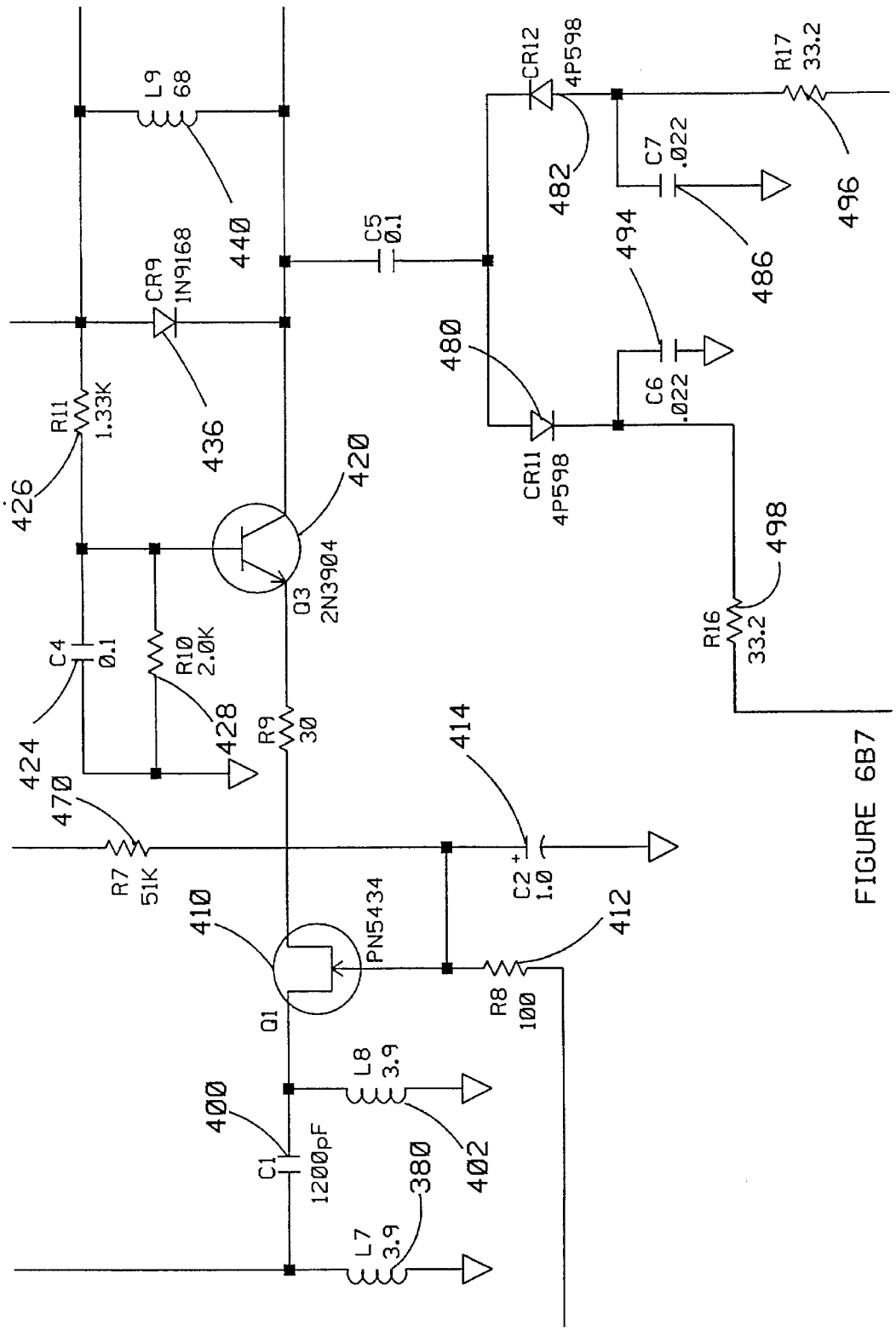
FIGURE 6B7

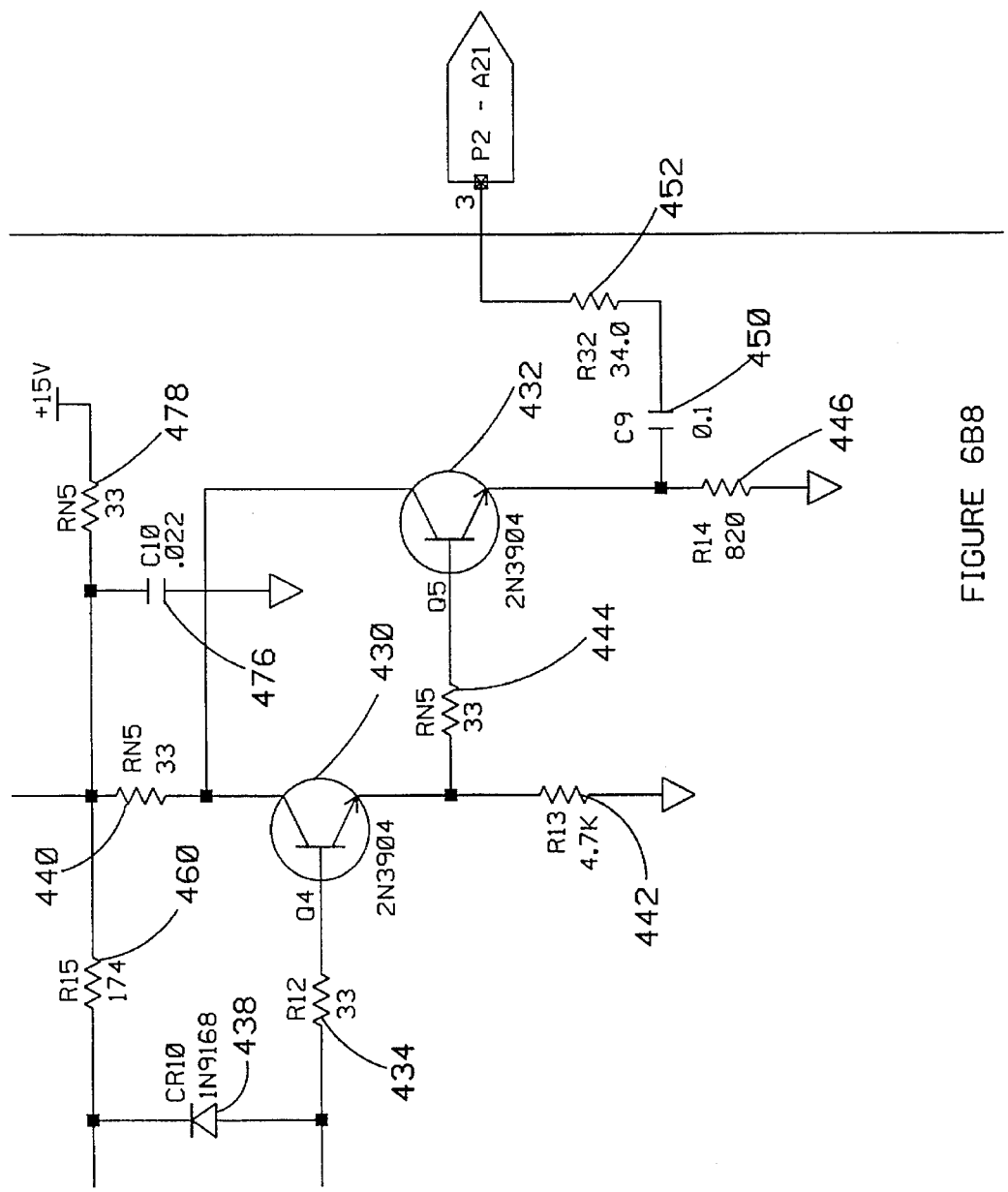
FIGURE 6B8

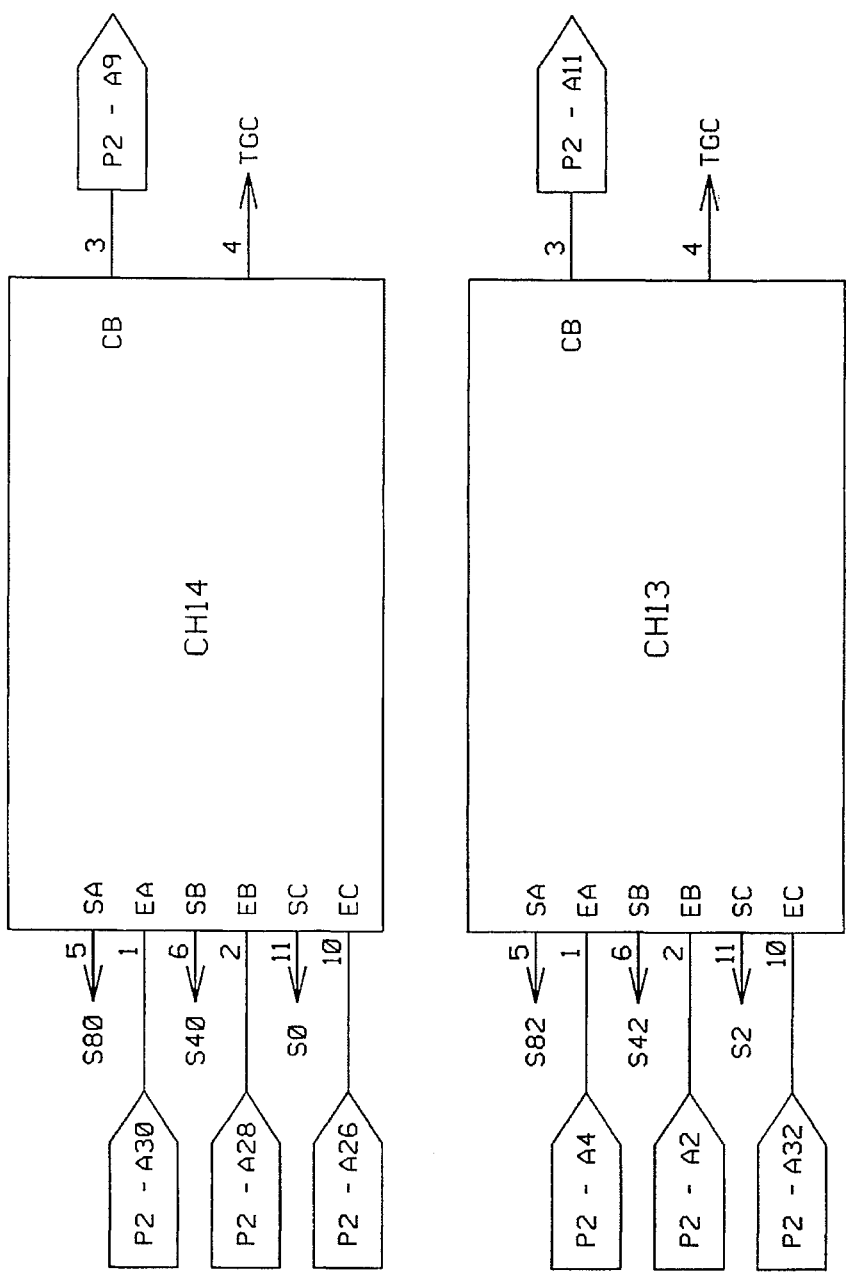
FIGURE 6B9

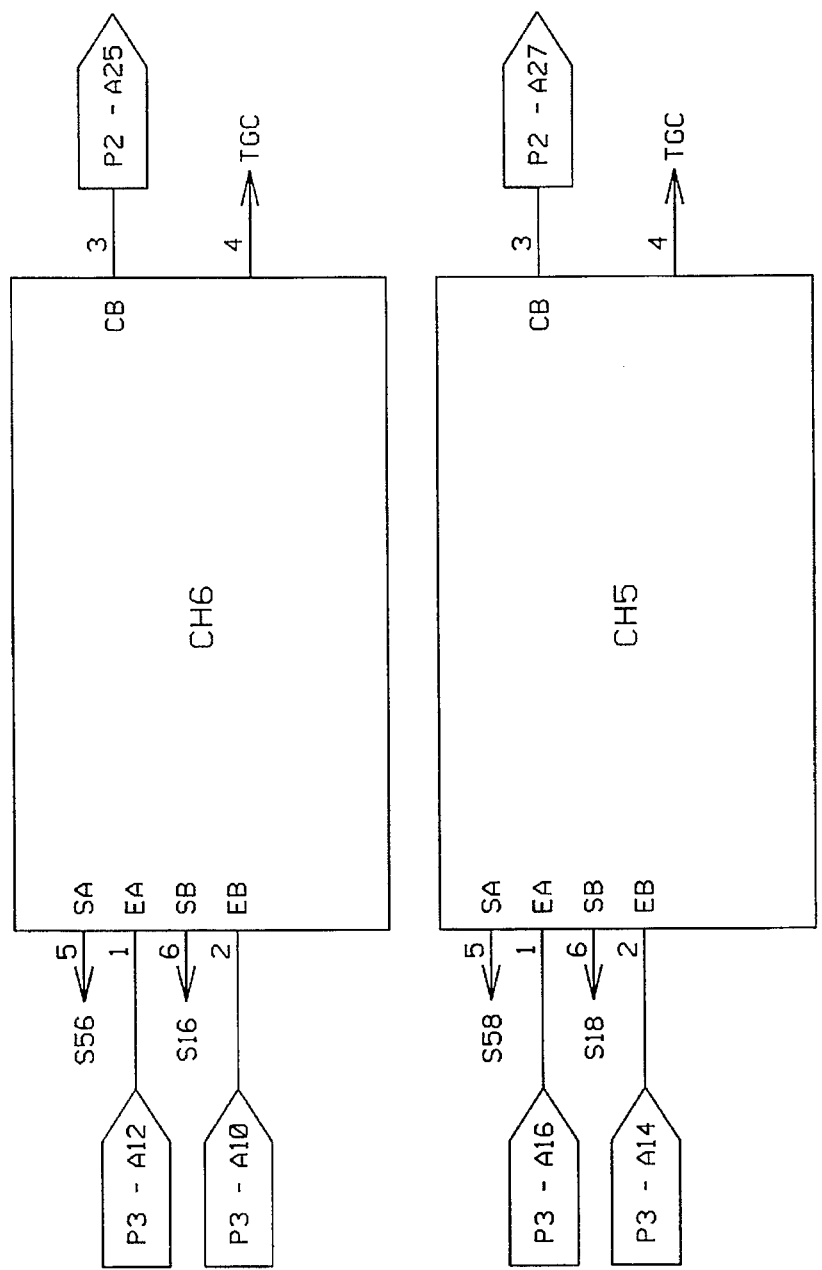
FIGURE 6B10

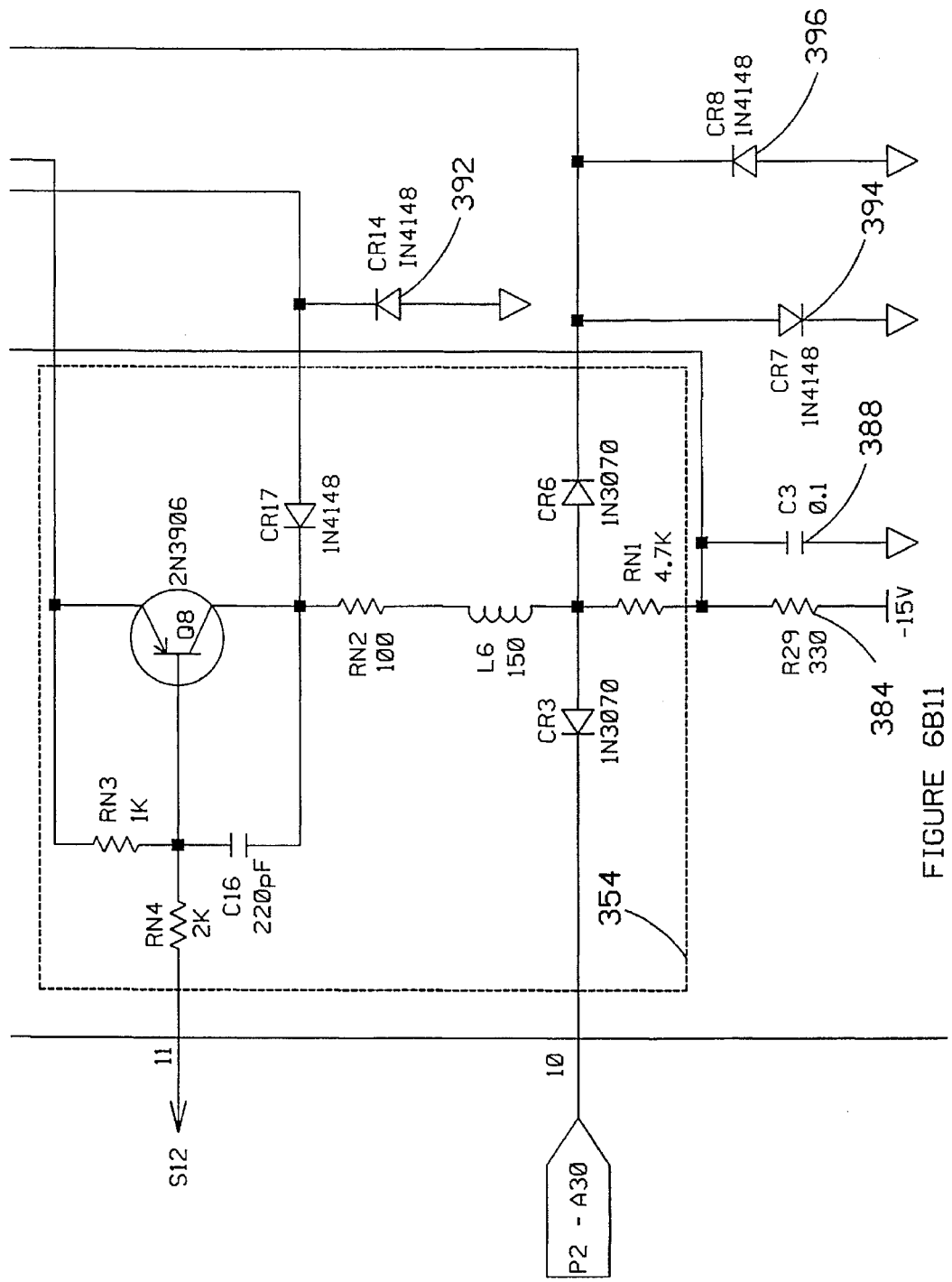
FIGURE 6B11

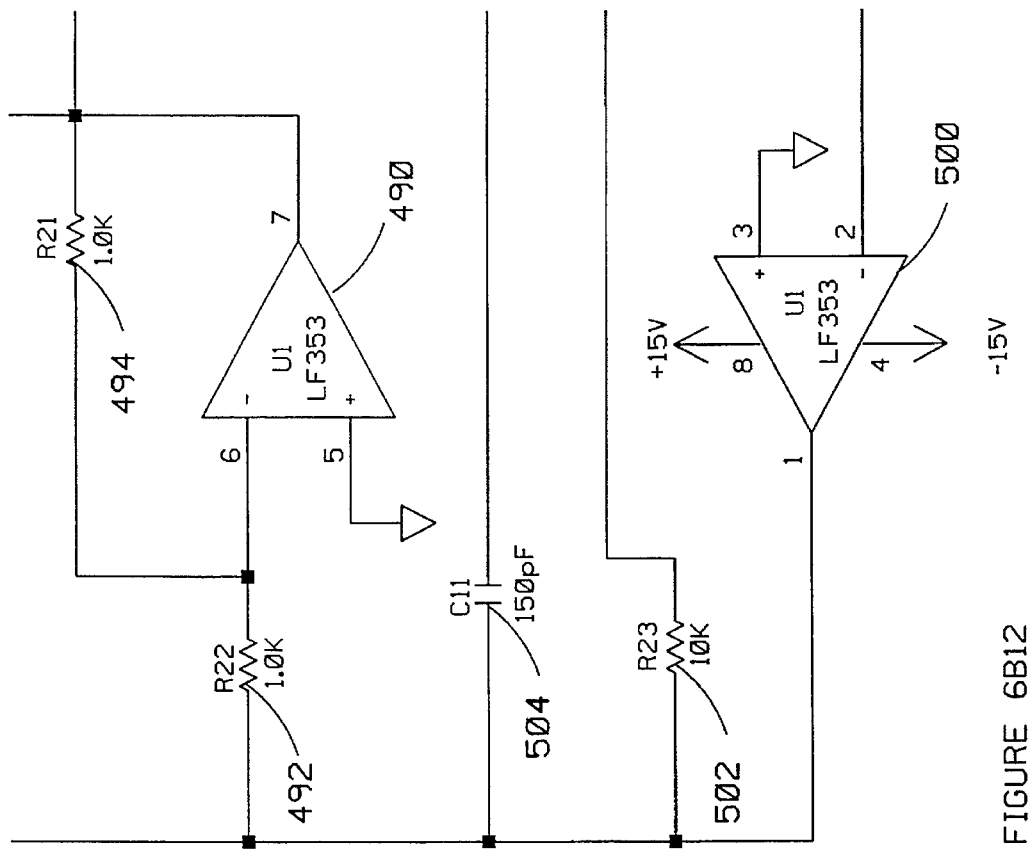
FIGURE 6B12

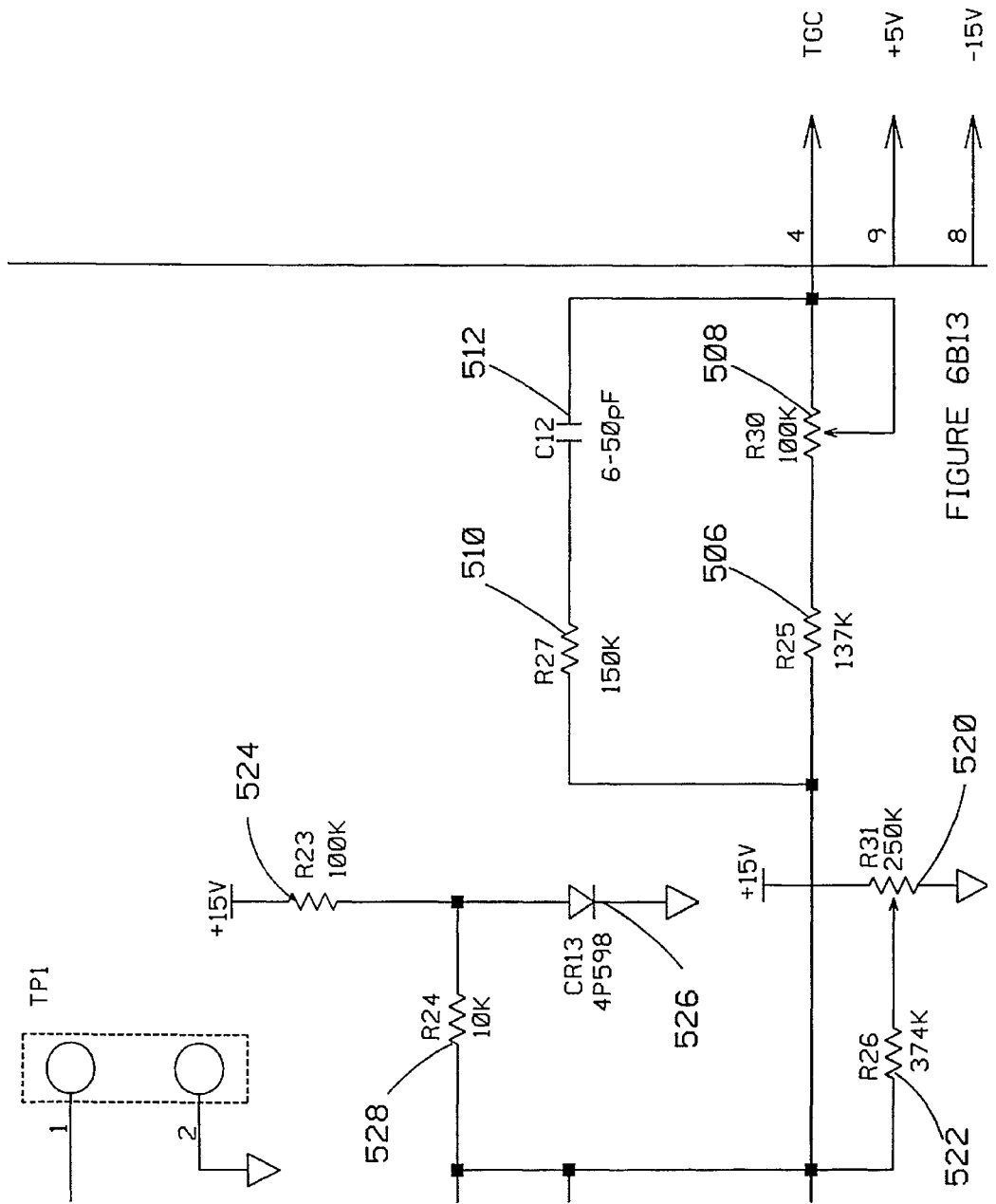
FIGURE 6B13

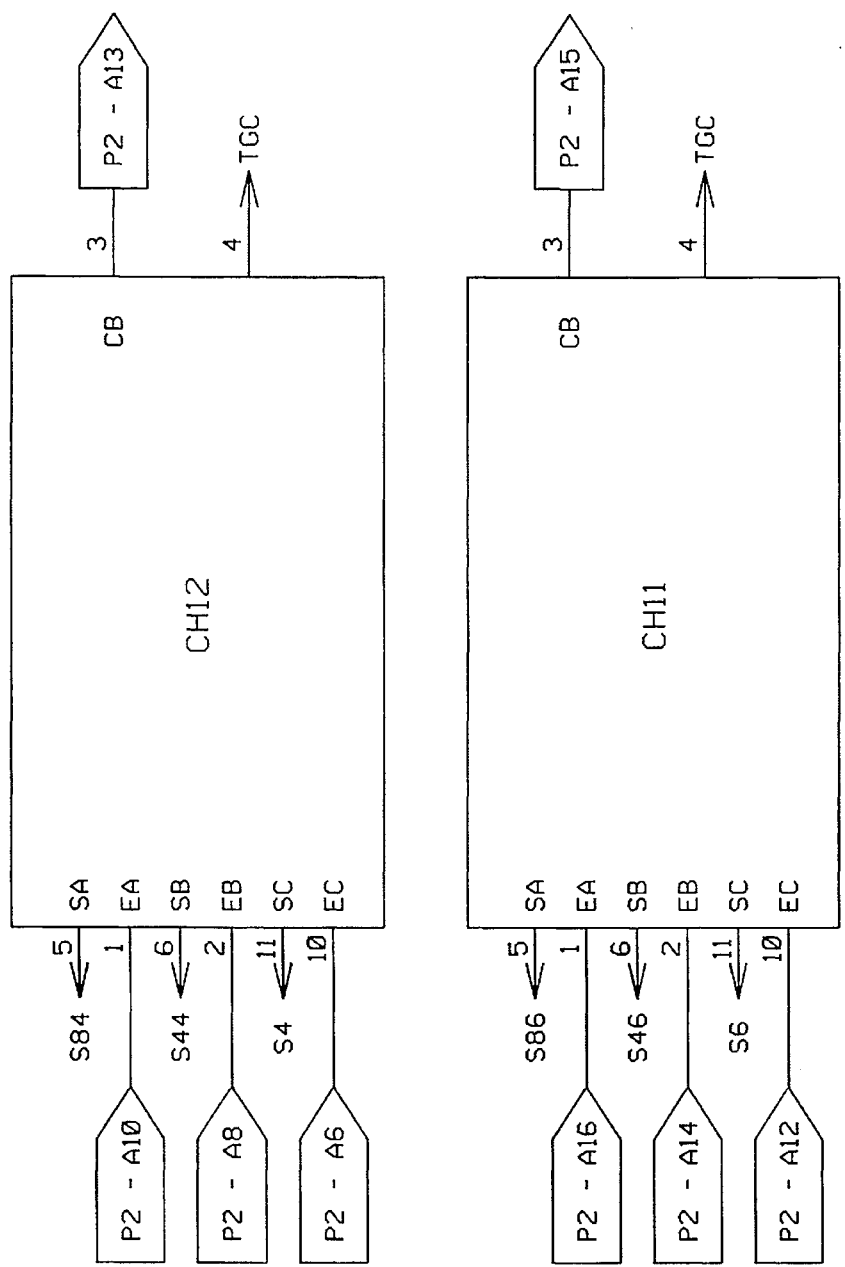
FIGURE 6B14

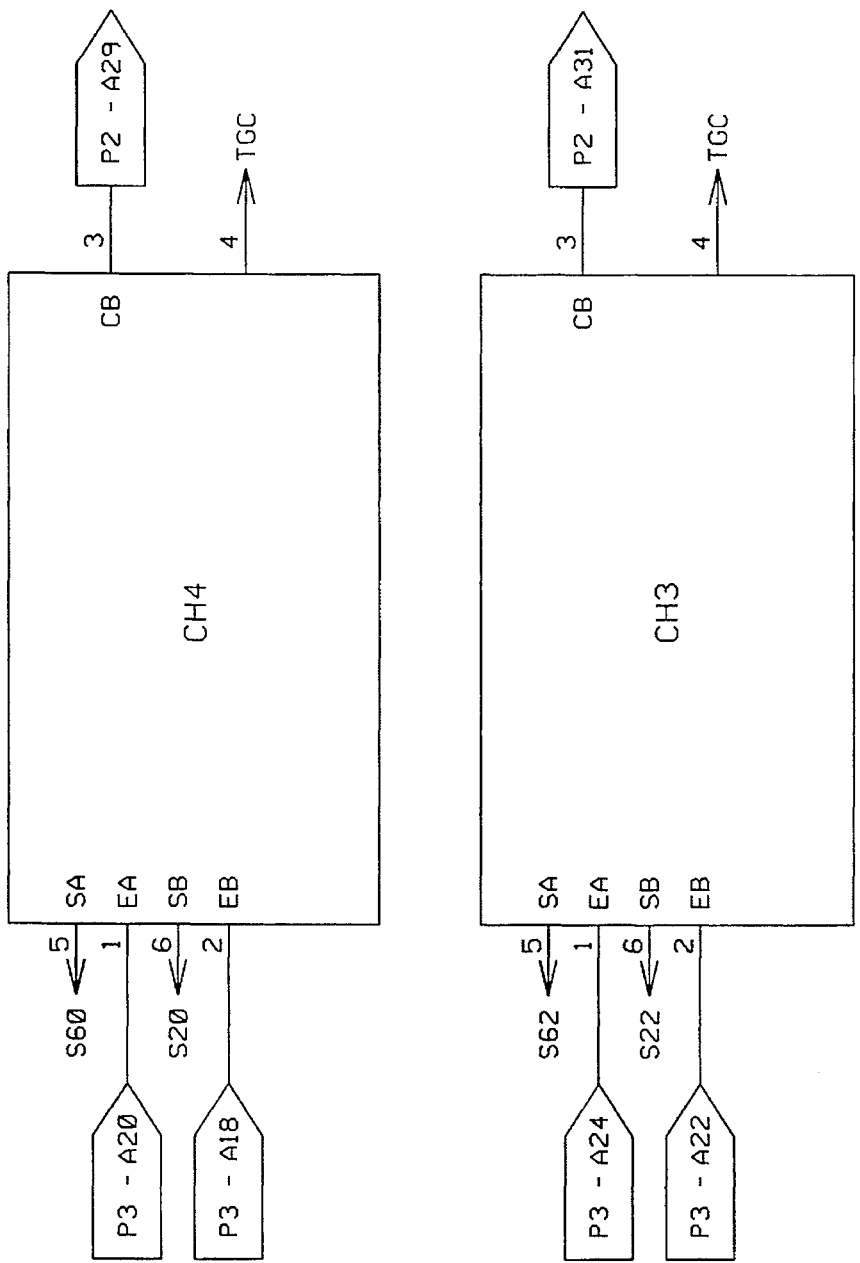
FIGURE 6B15

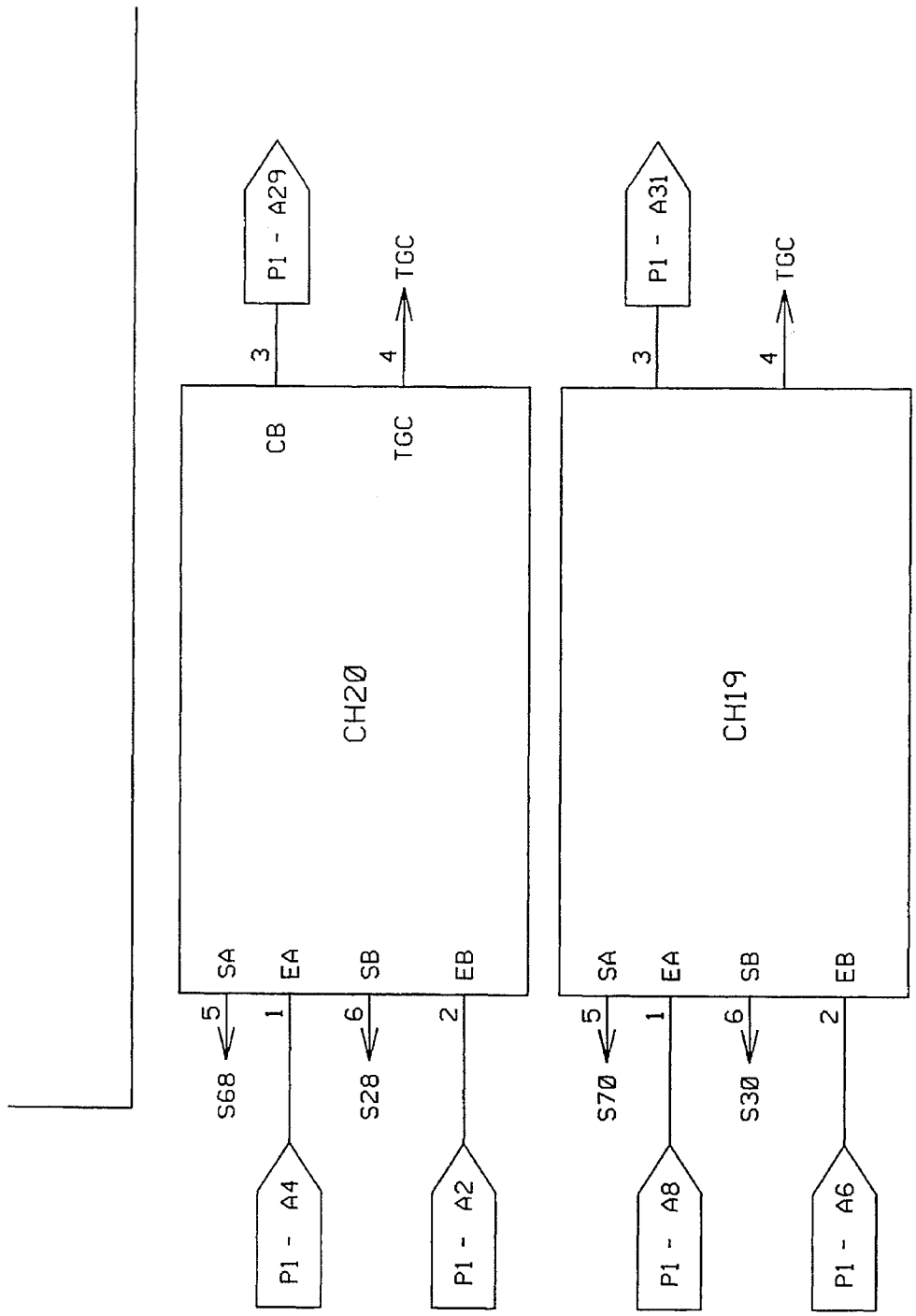
FIGURE 6B16

FIGURE 6B17

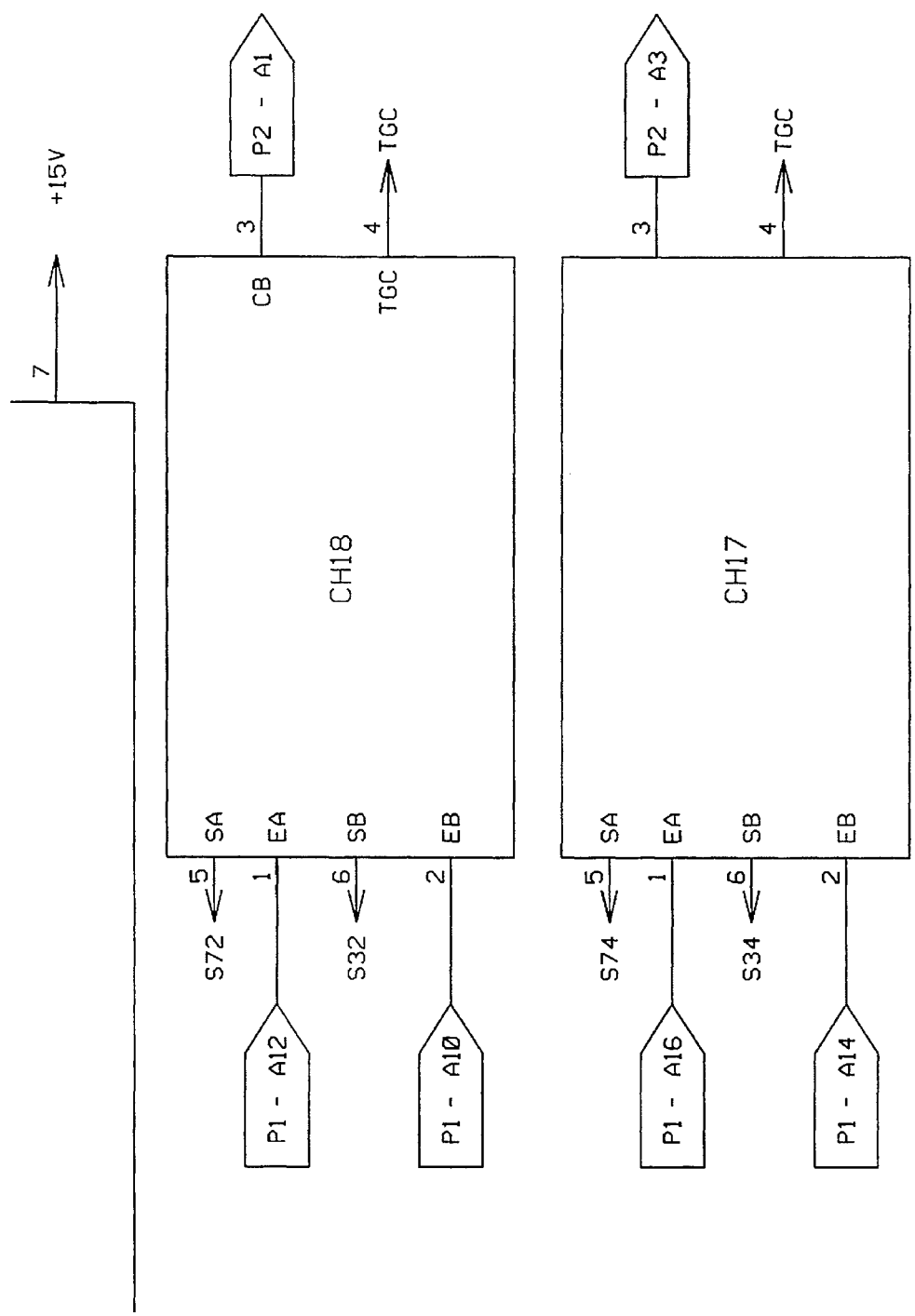
FIGURE 6B18

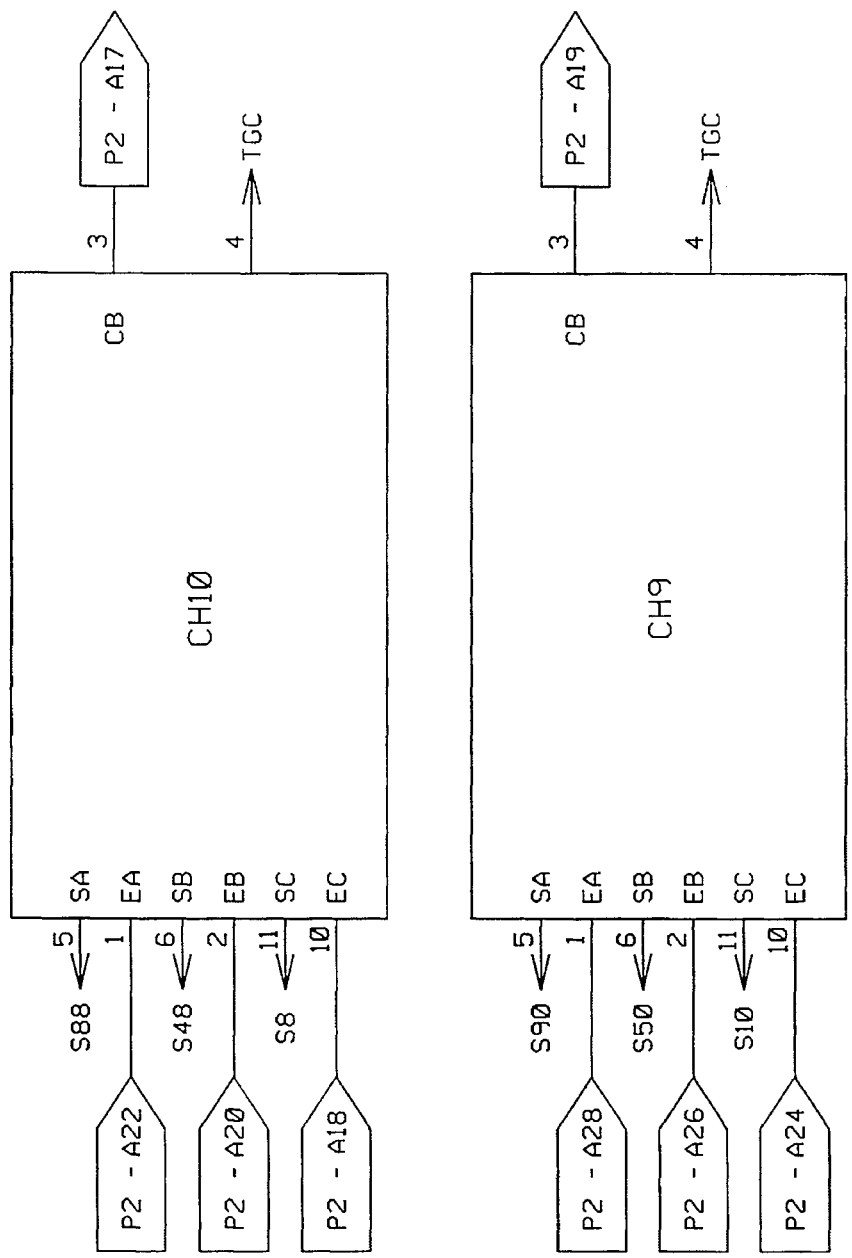
FIGURE 6B19

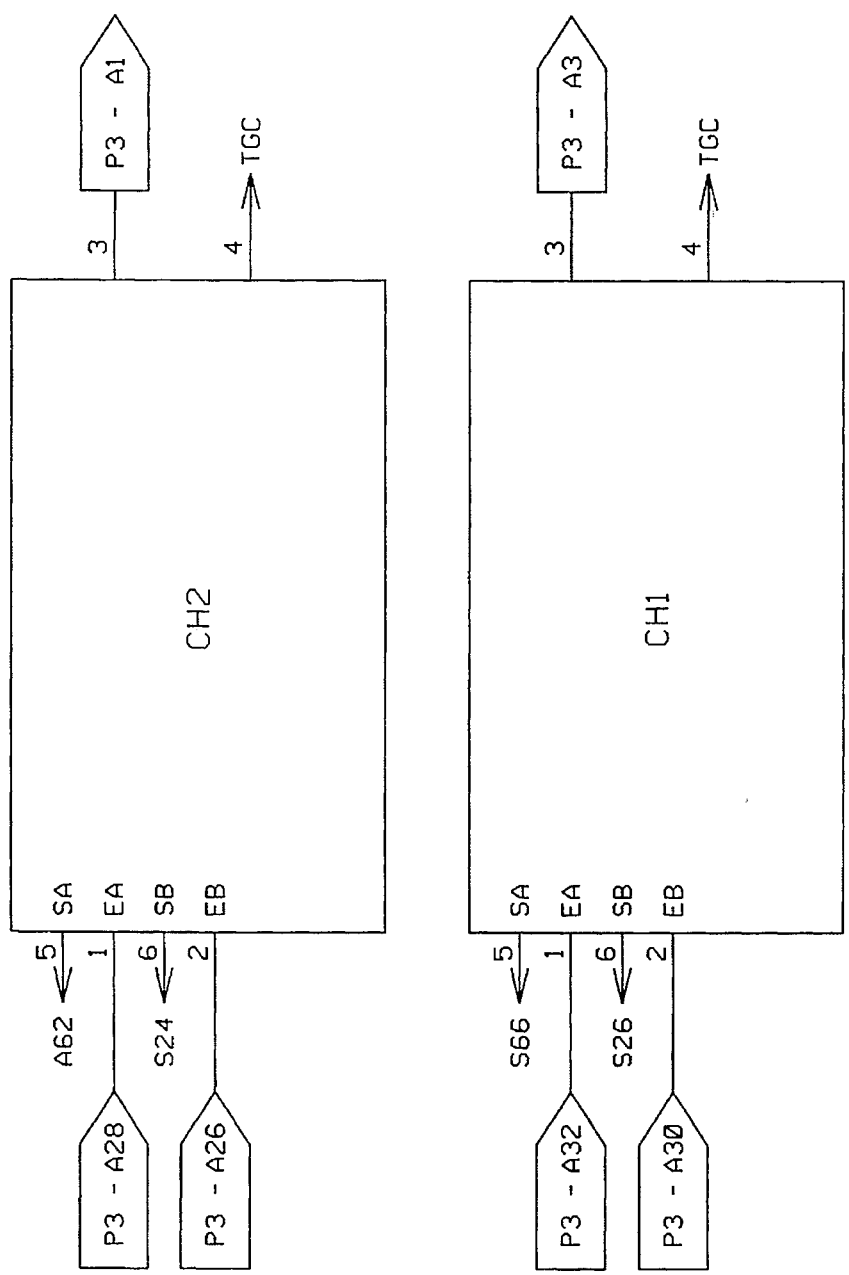
FIGURE 6B20

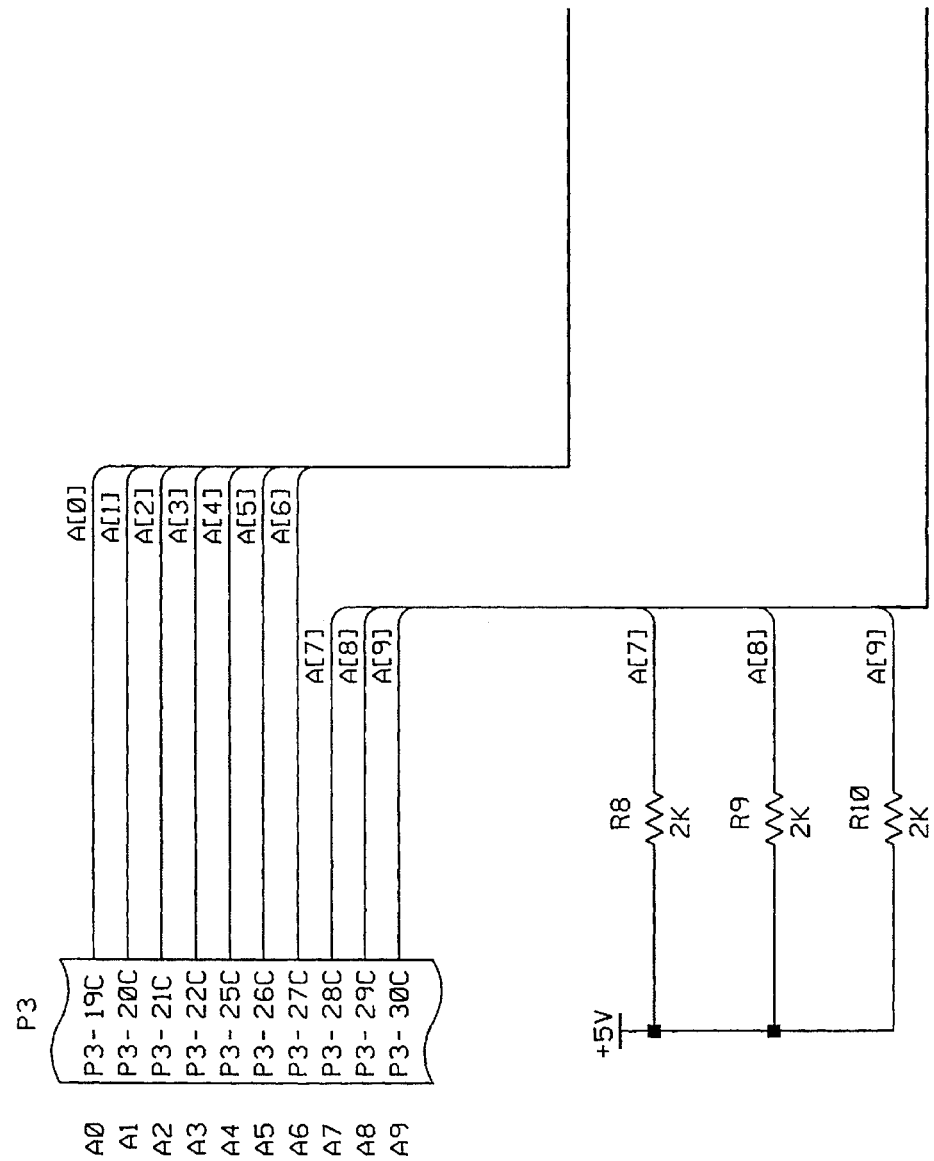
FIGURE 6C1

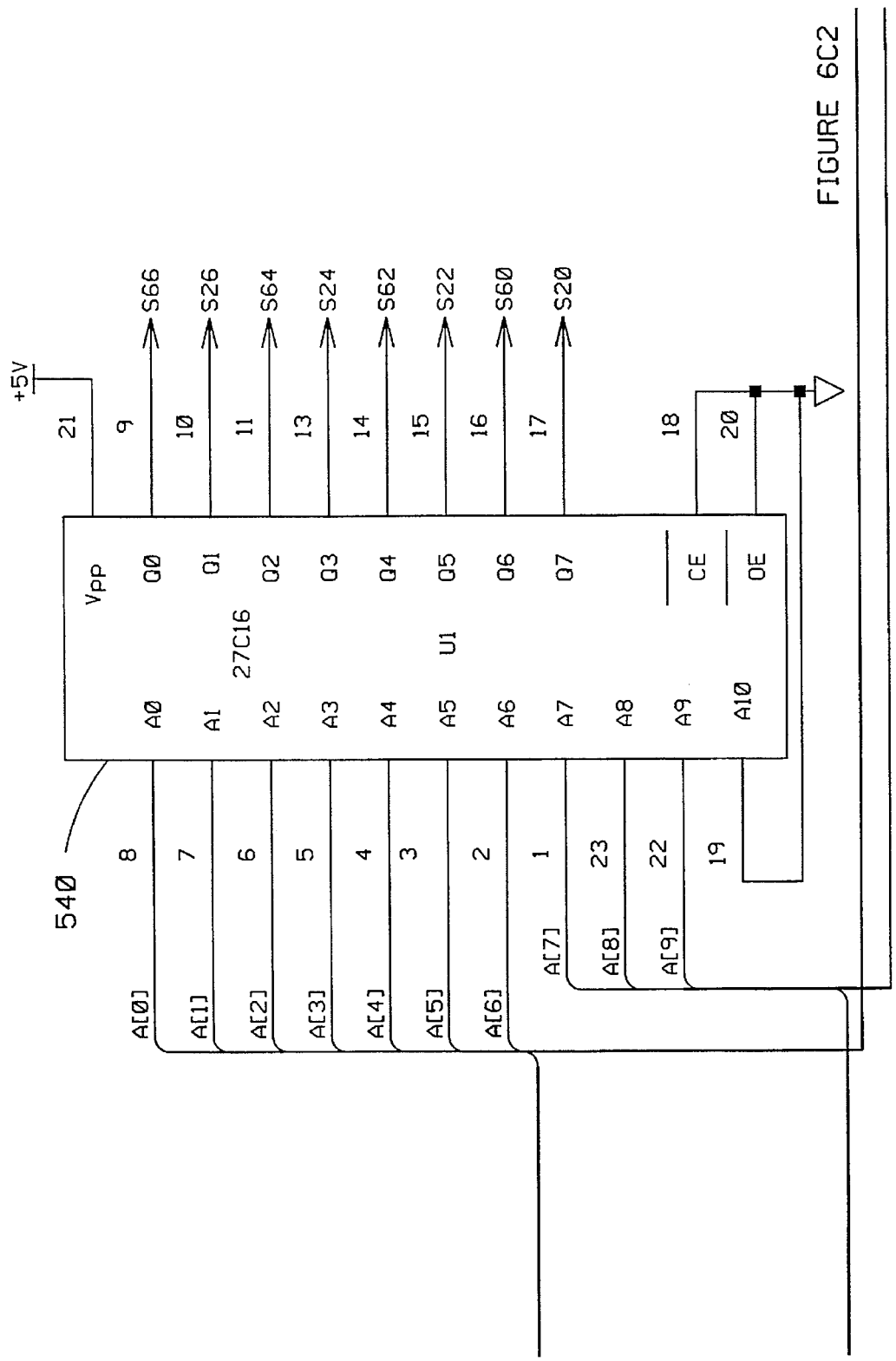

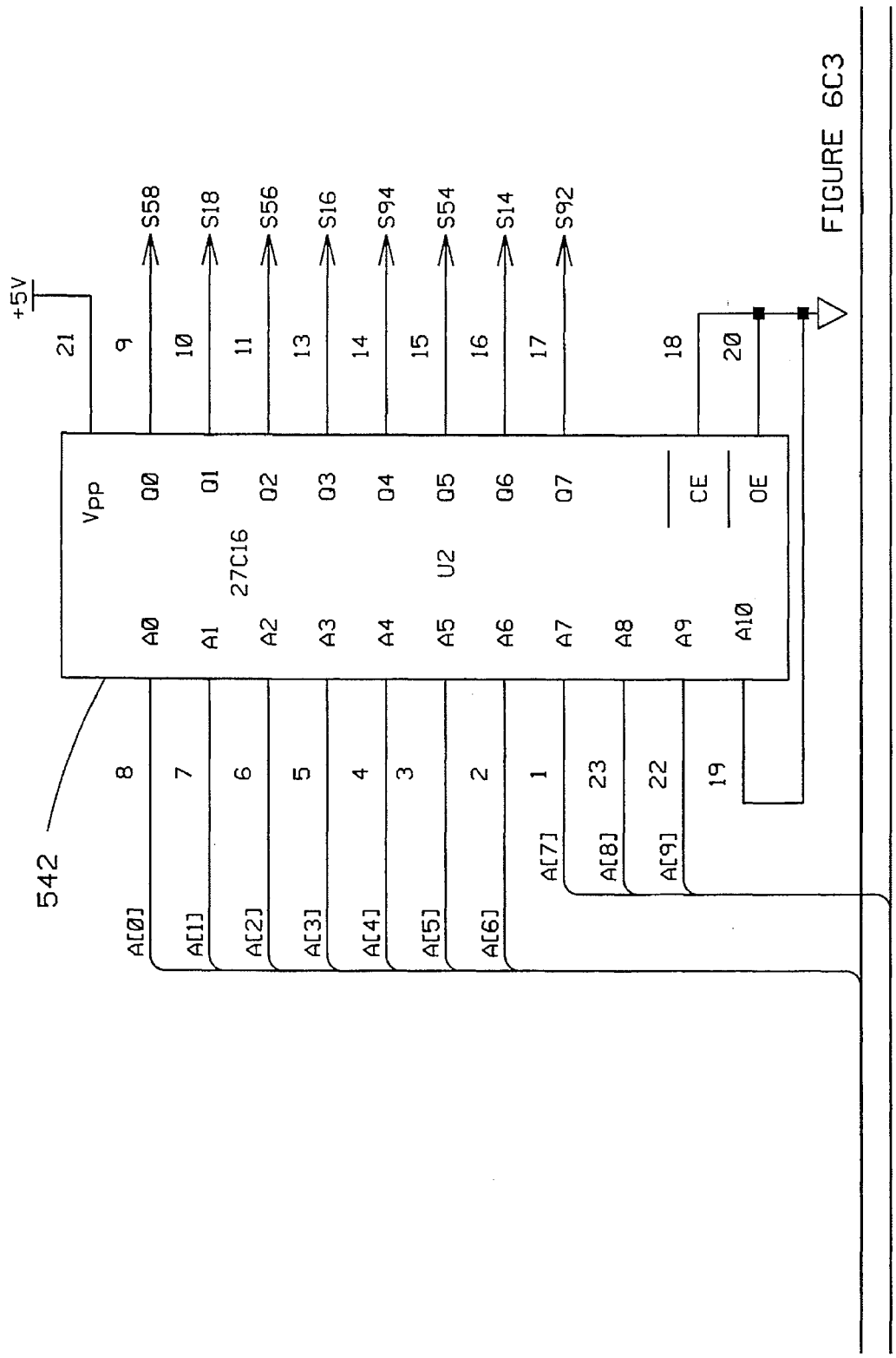
FIGURE 6C3

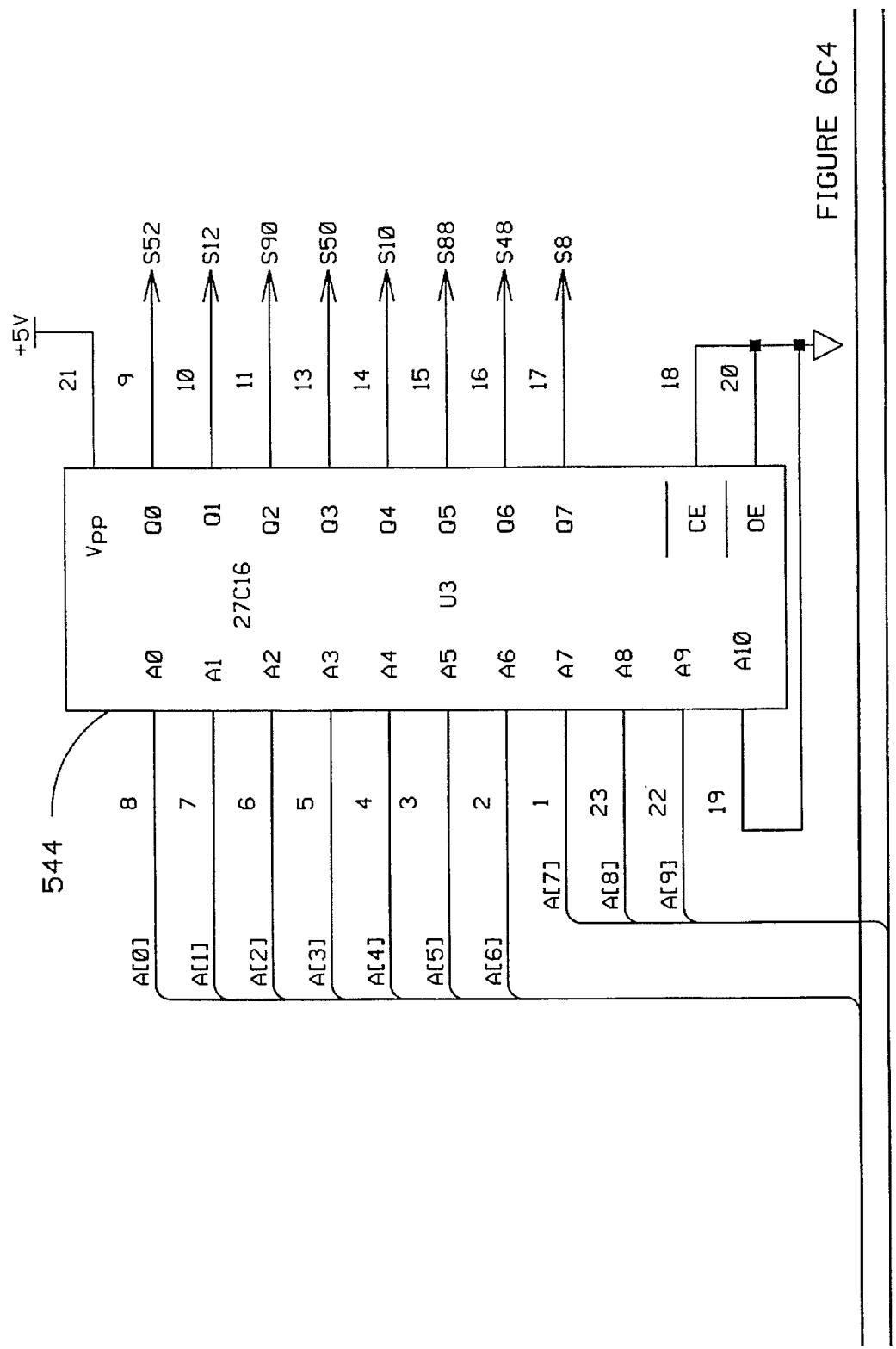
FIGURE 6C4

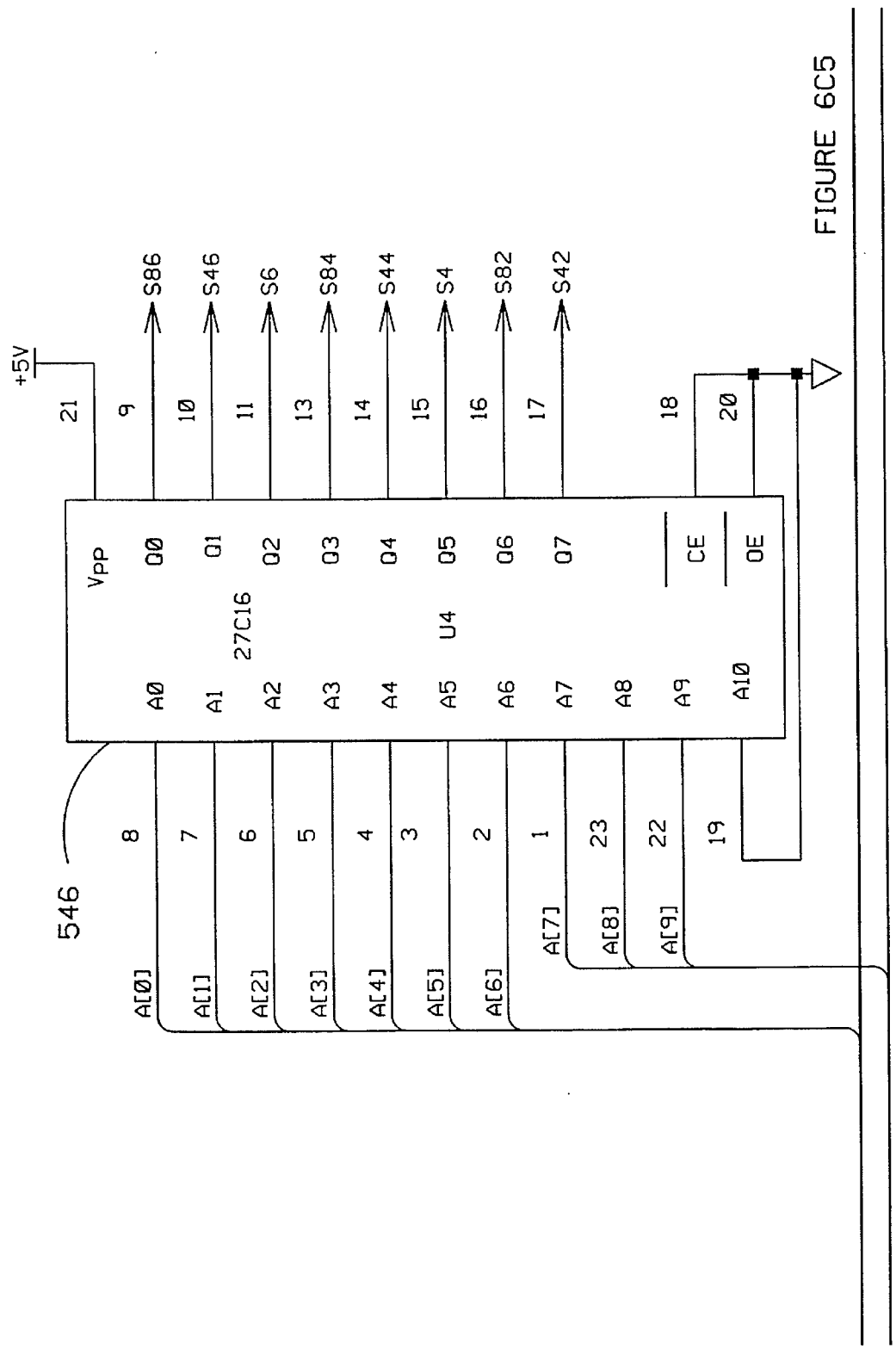
FIGURE 6C5

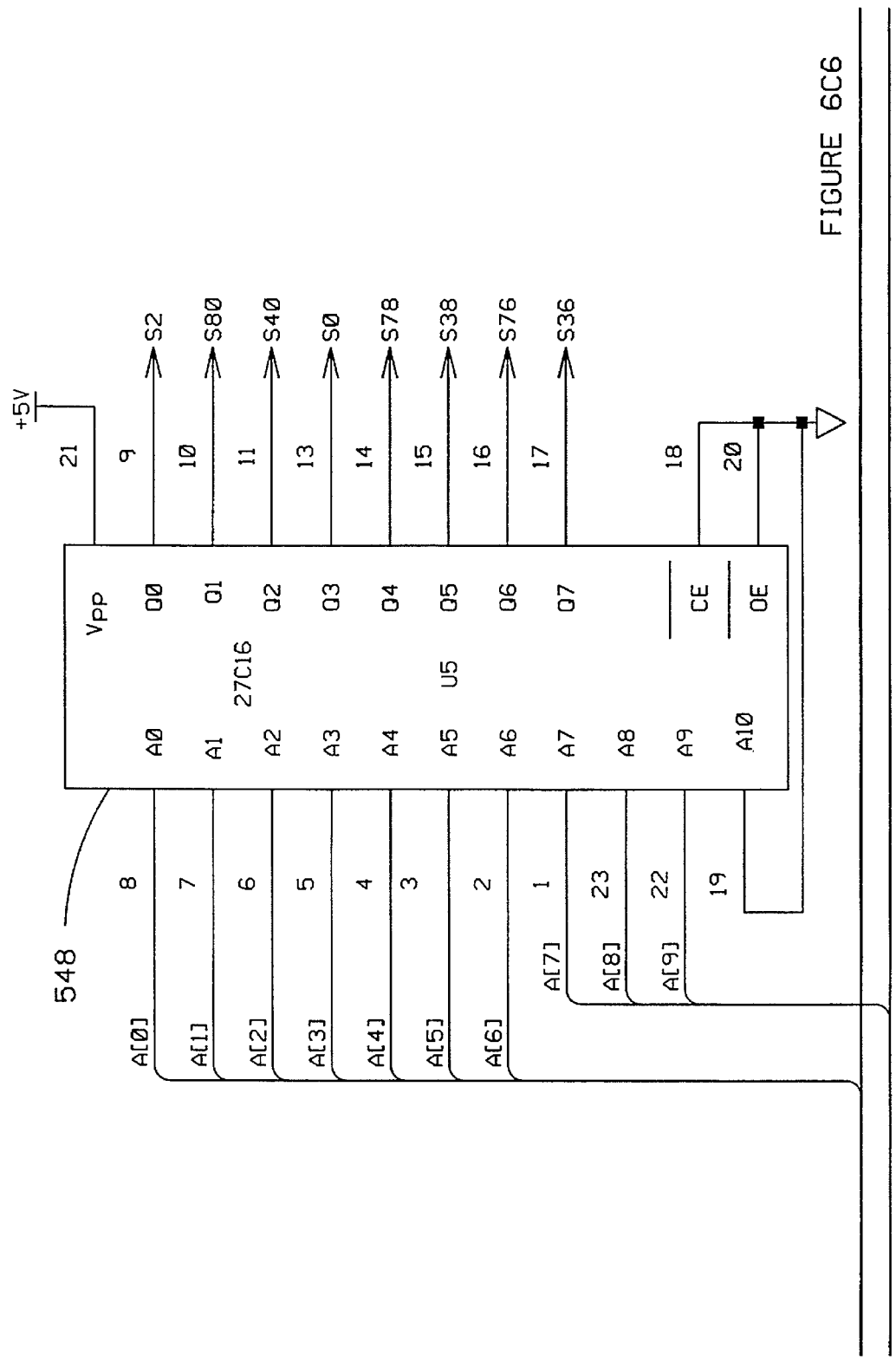
FIGURE 6C6

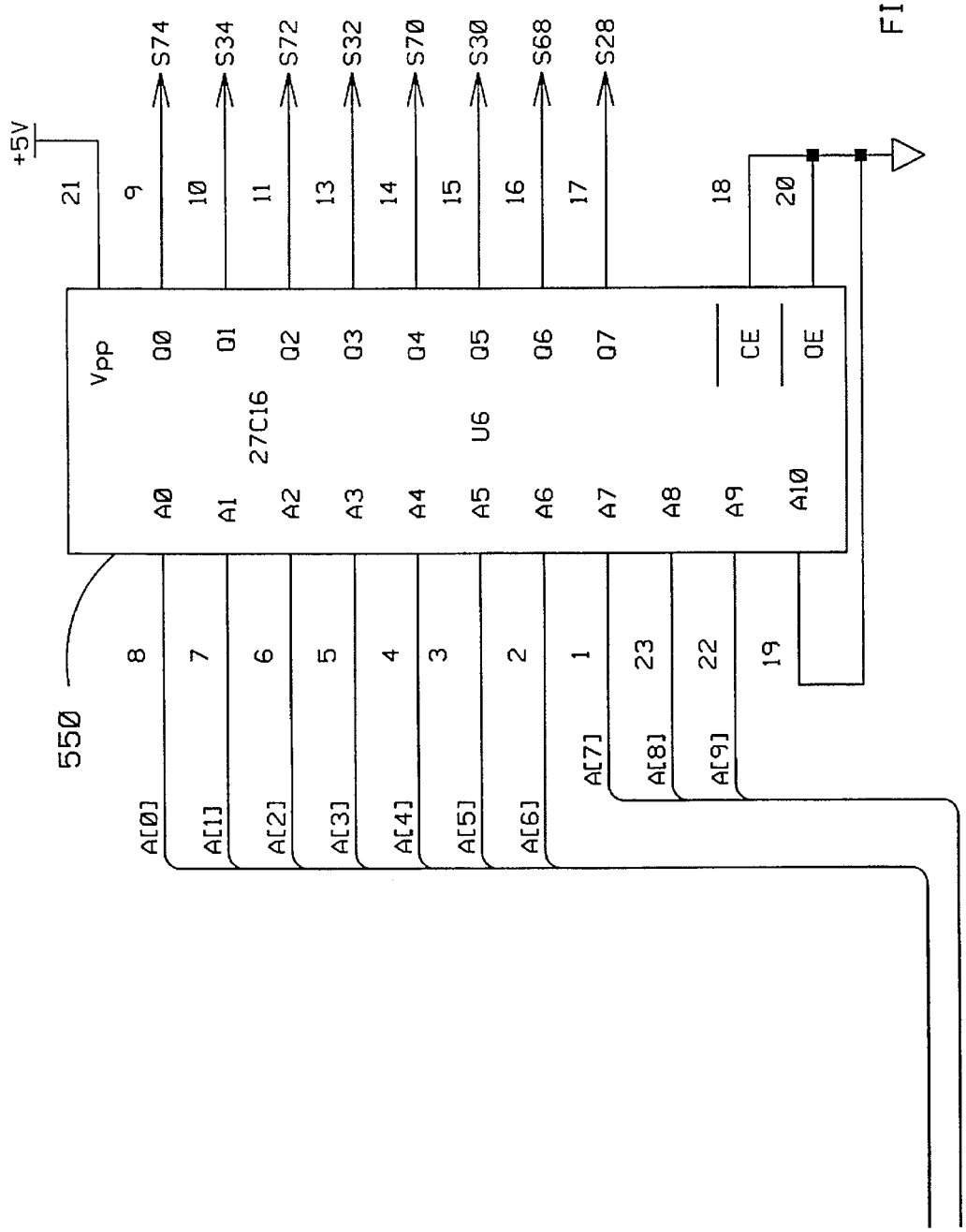
FIGURE 6C7

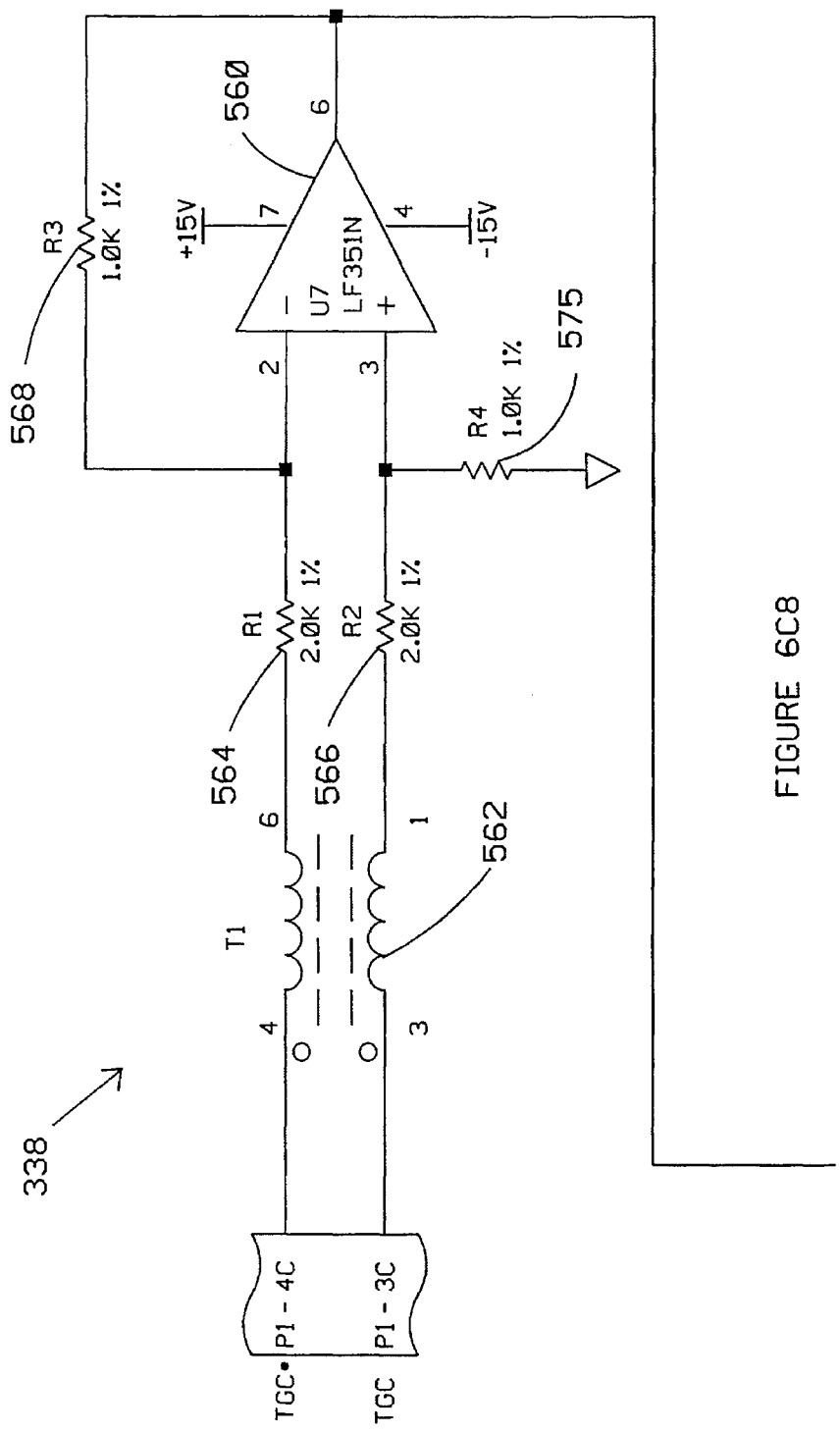
FIGURE 6C8

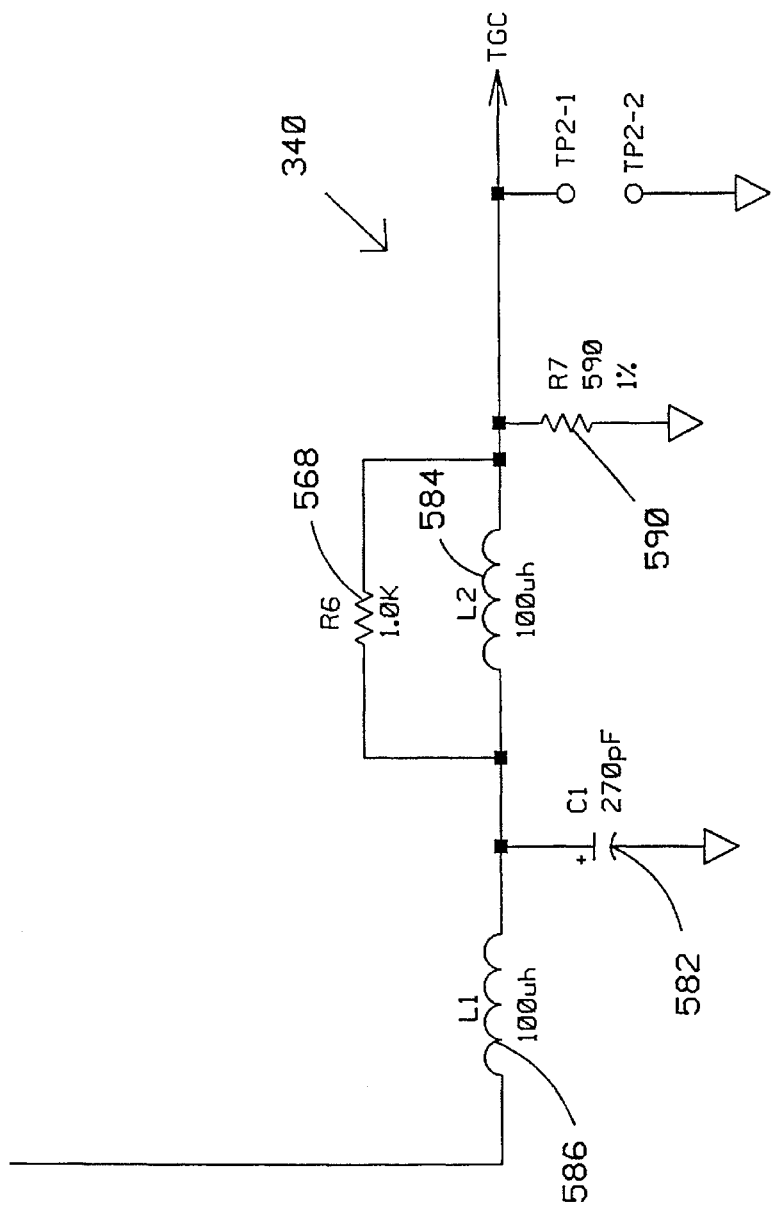
FIGURE 6C9

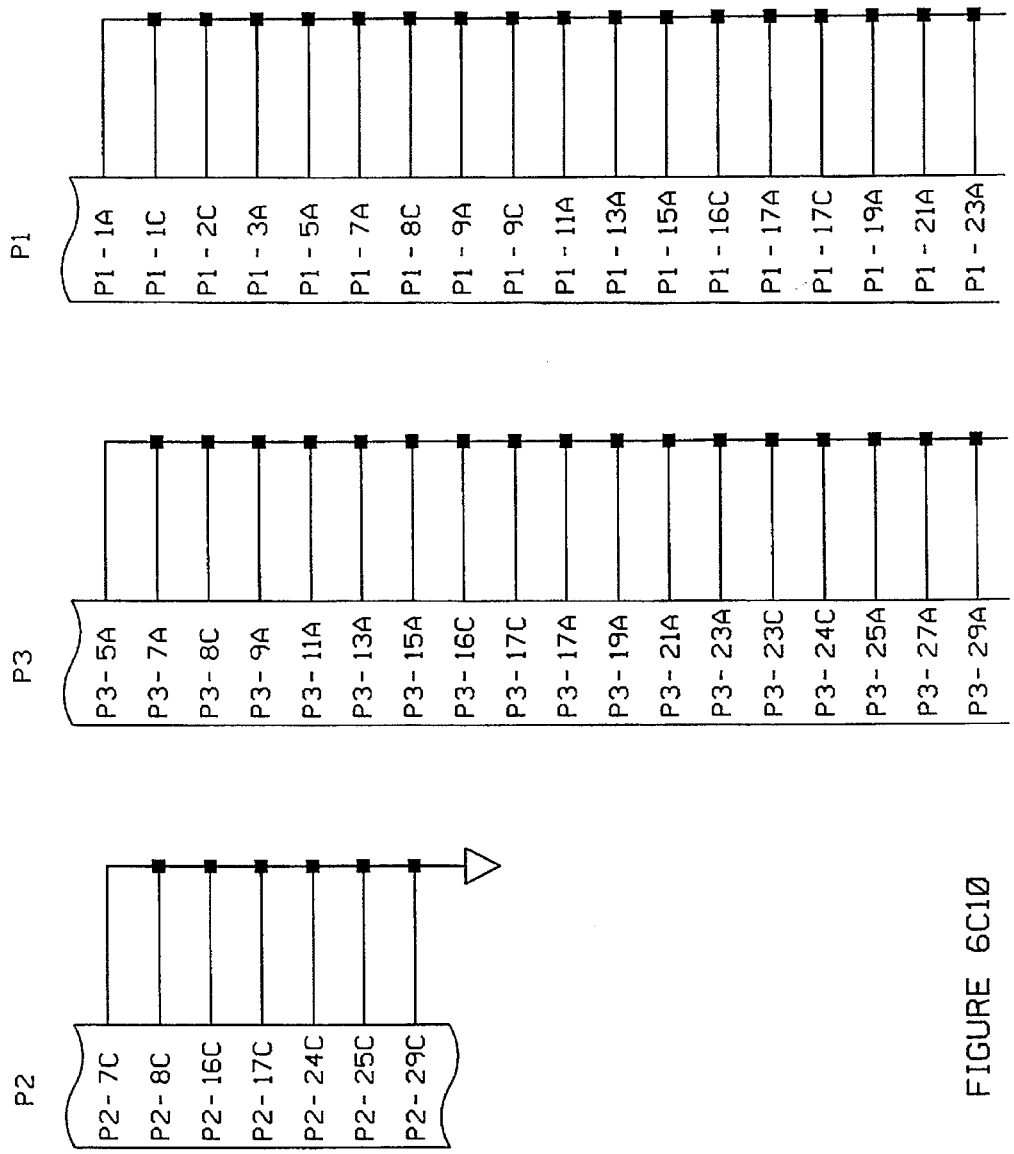
FIGURE 6C10

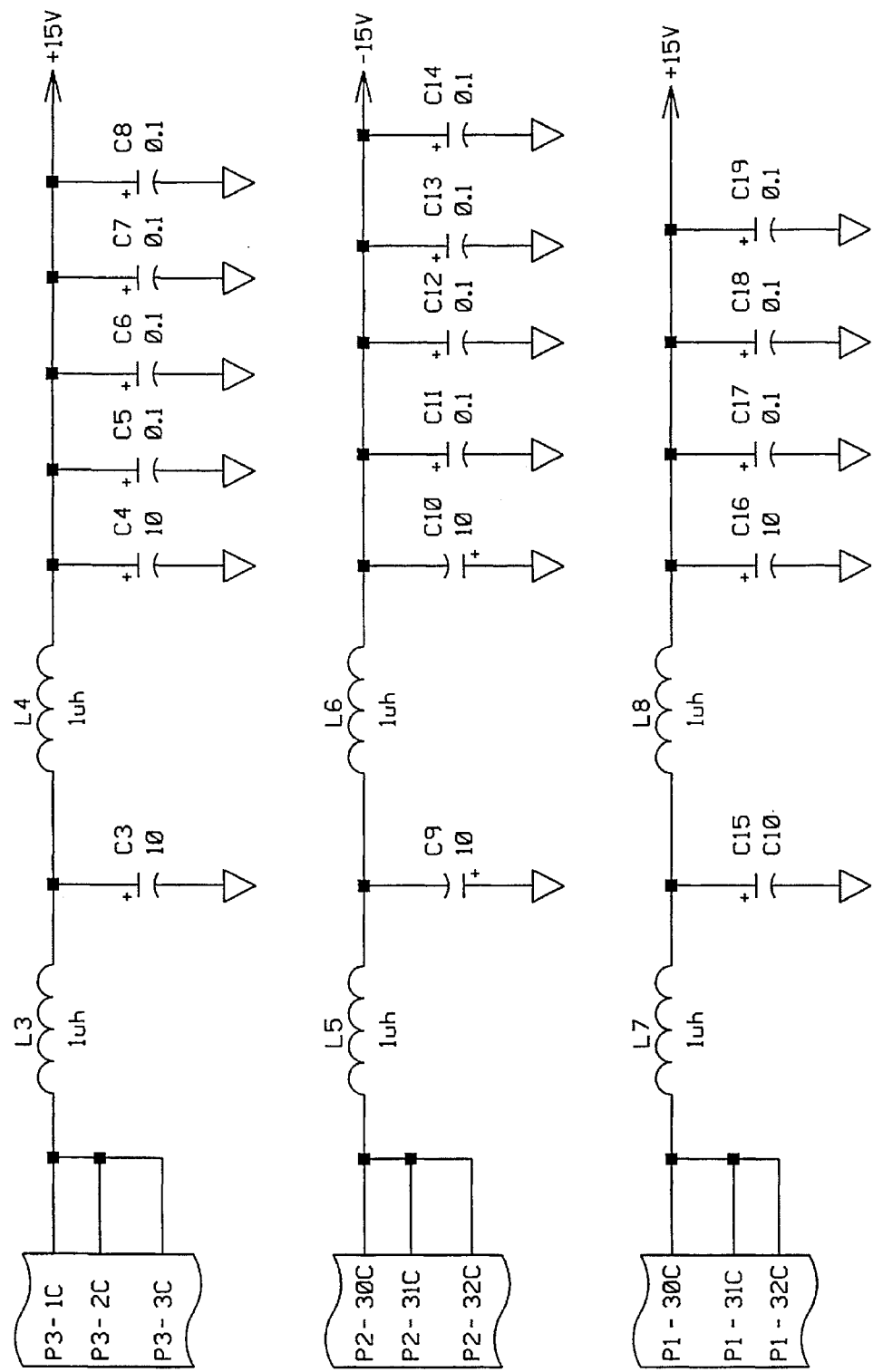
FIGURE 6C11

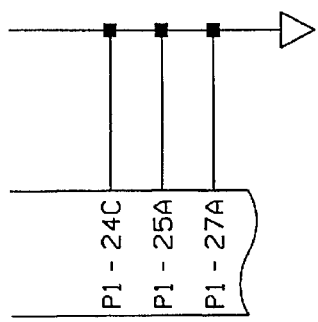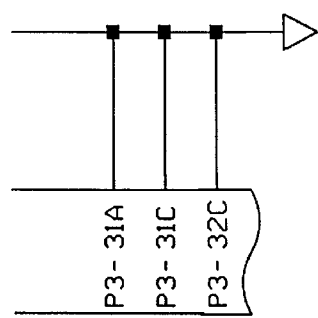
FIGURE 6C12

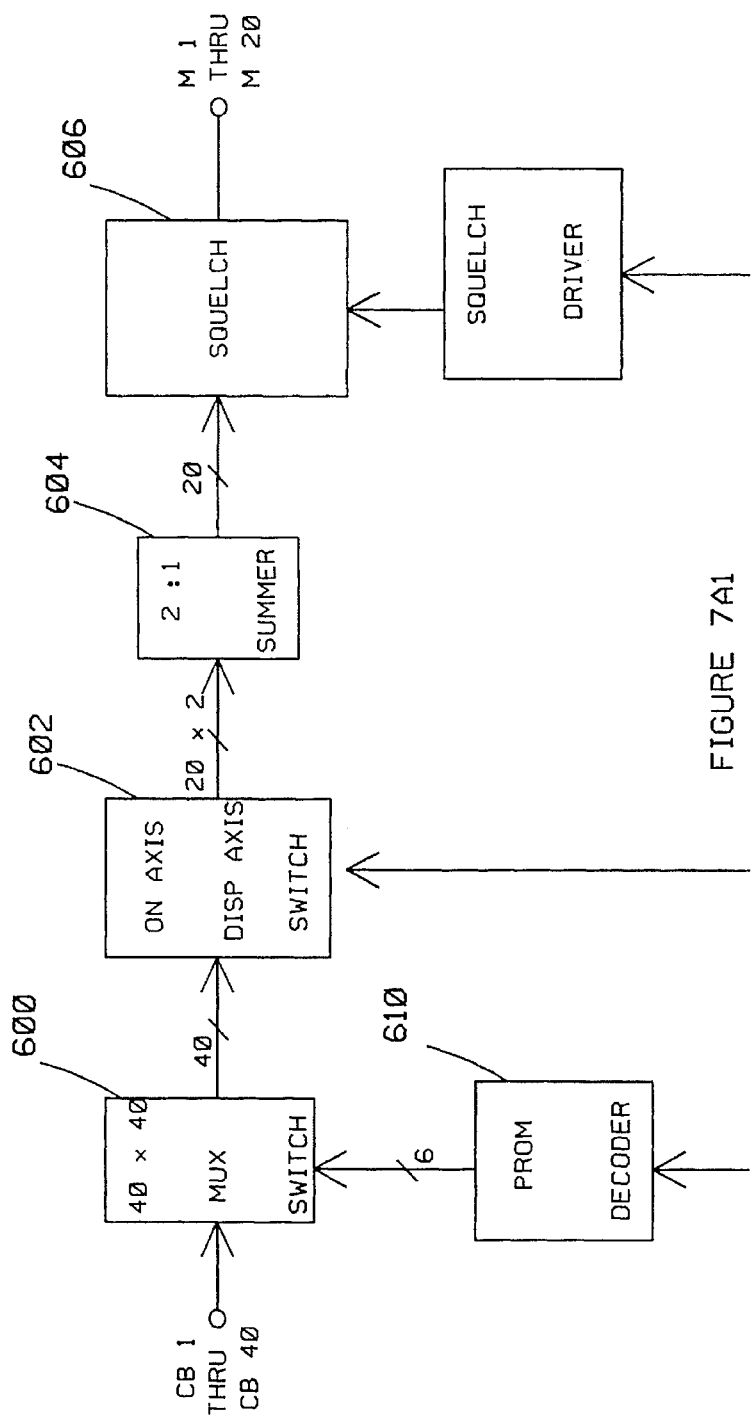
FIGURE 7A1

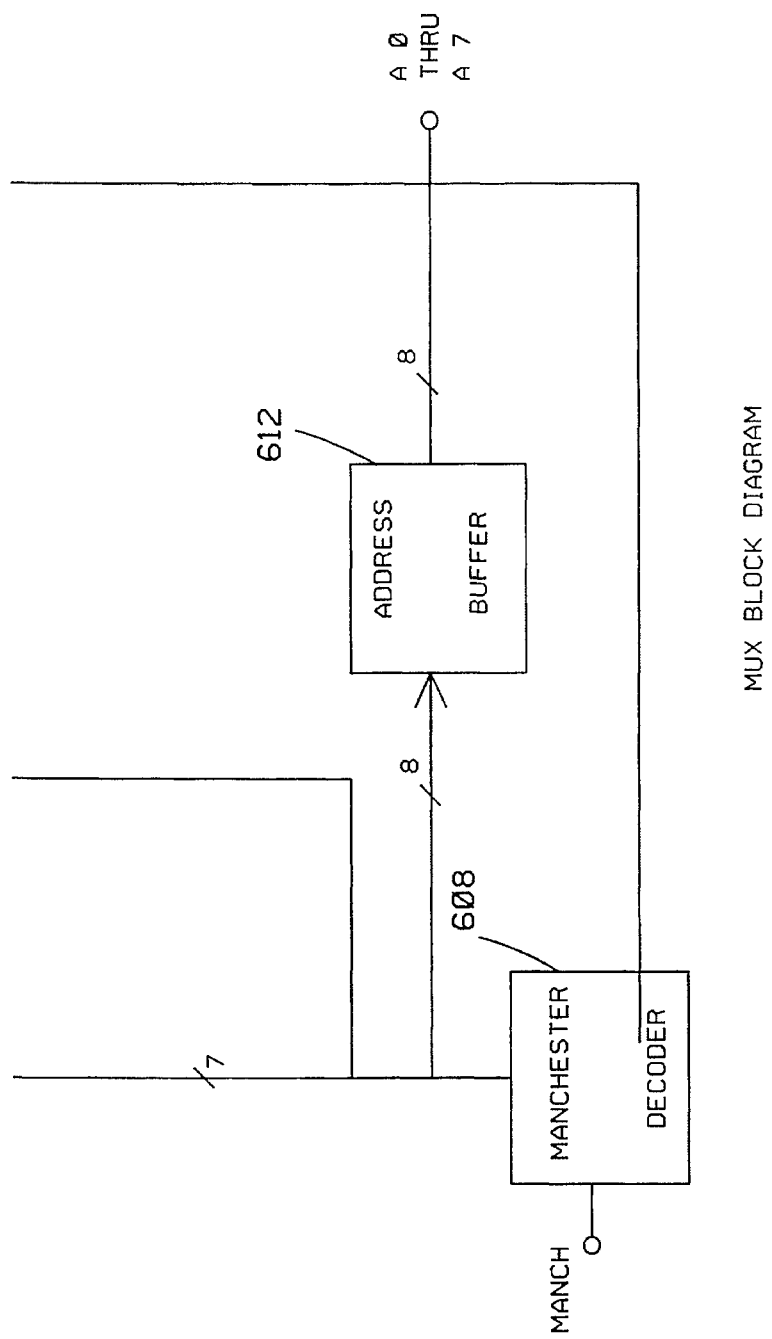
FIGURE 7A2

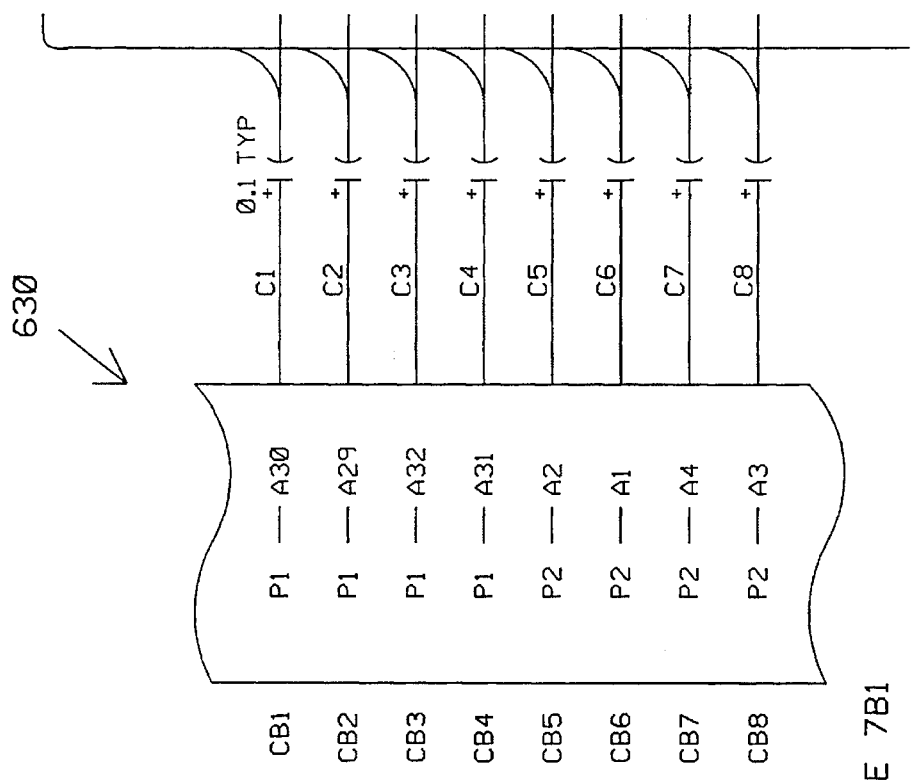
FIGURE 7B1

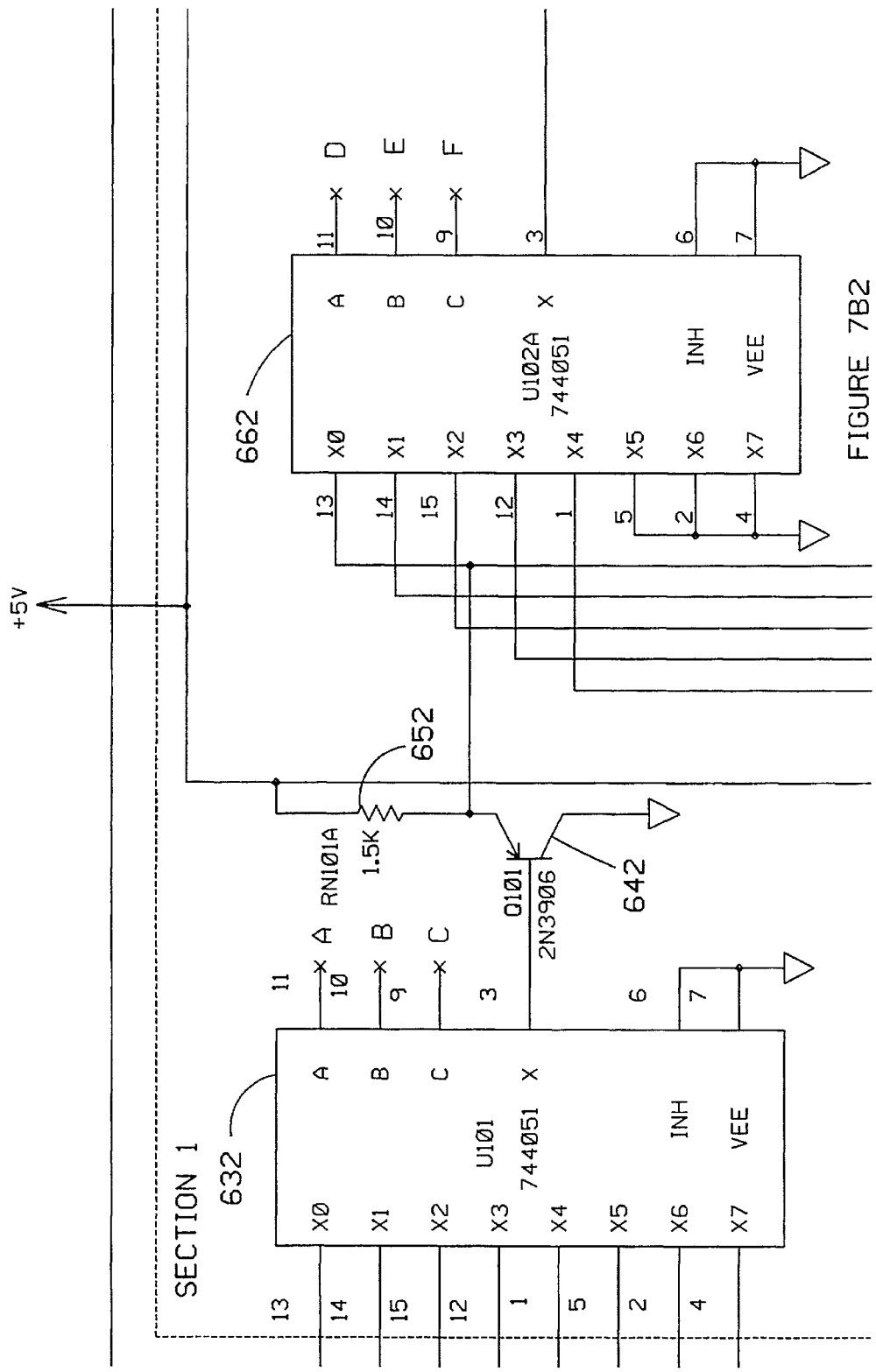
FIGURE 7B2

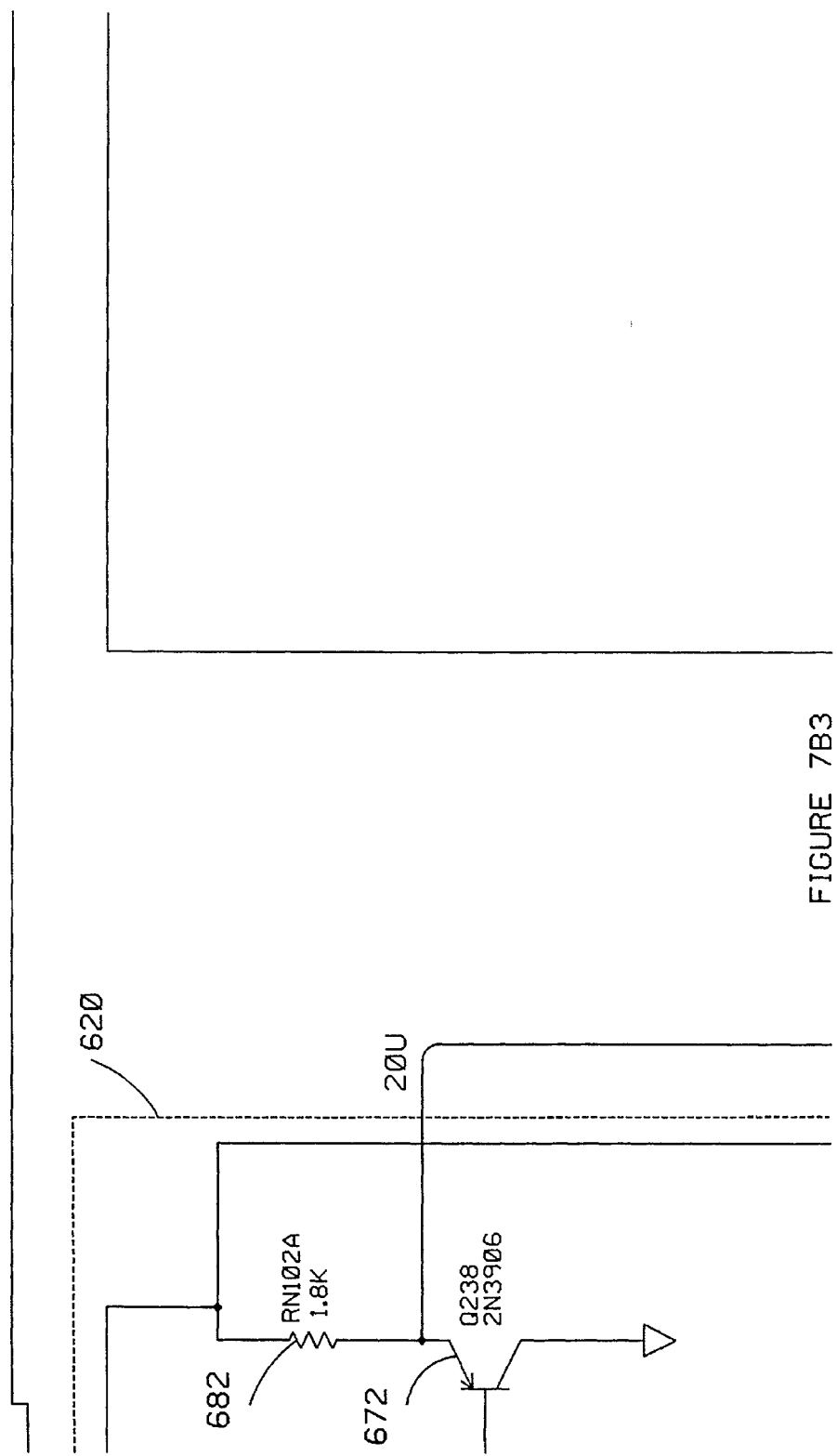

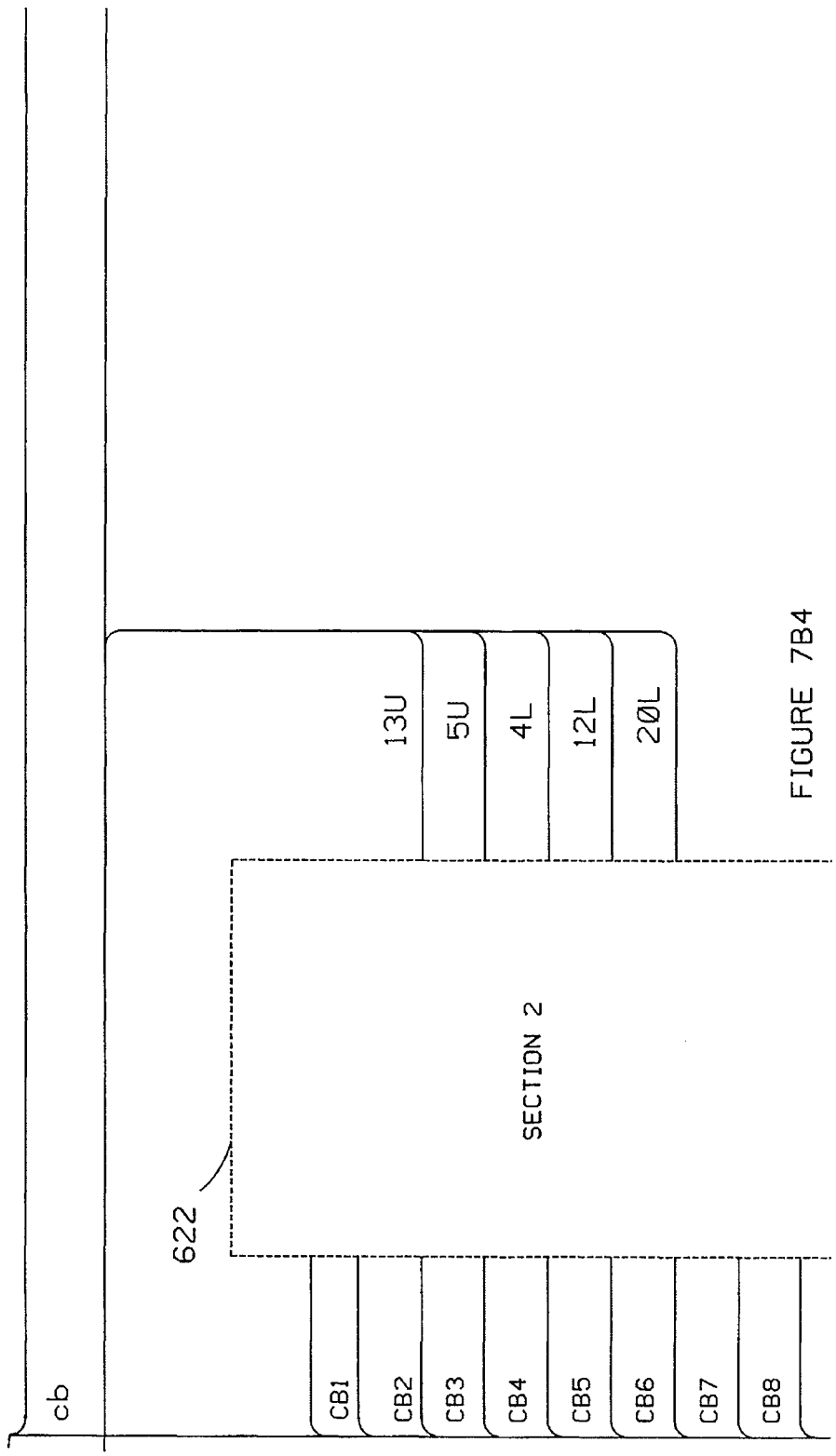

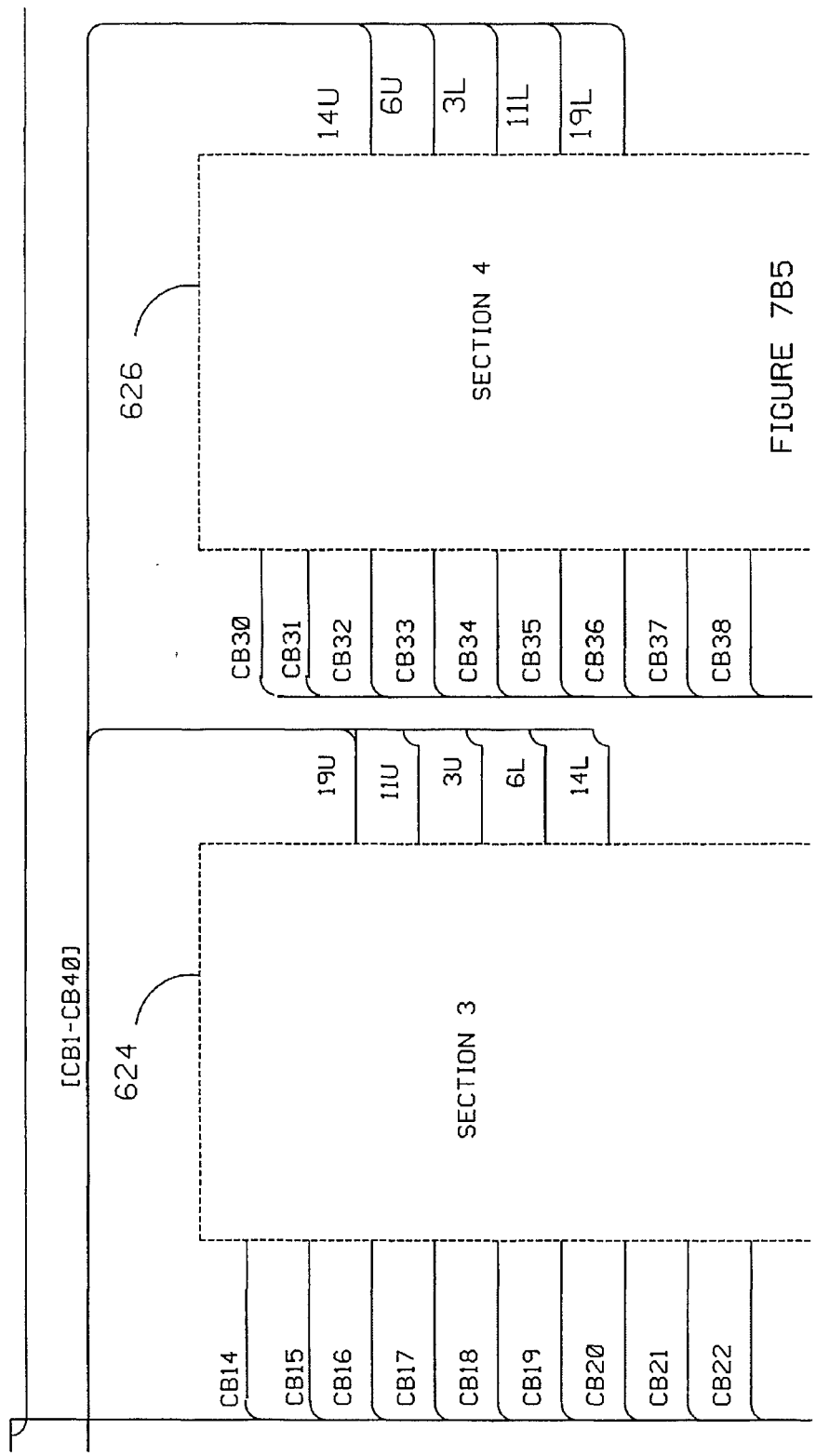
FIGURE 7B5

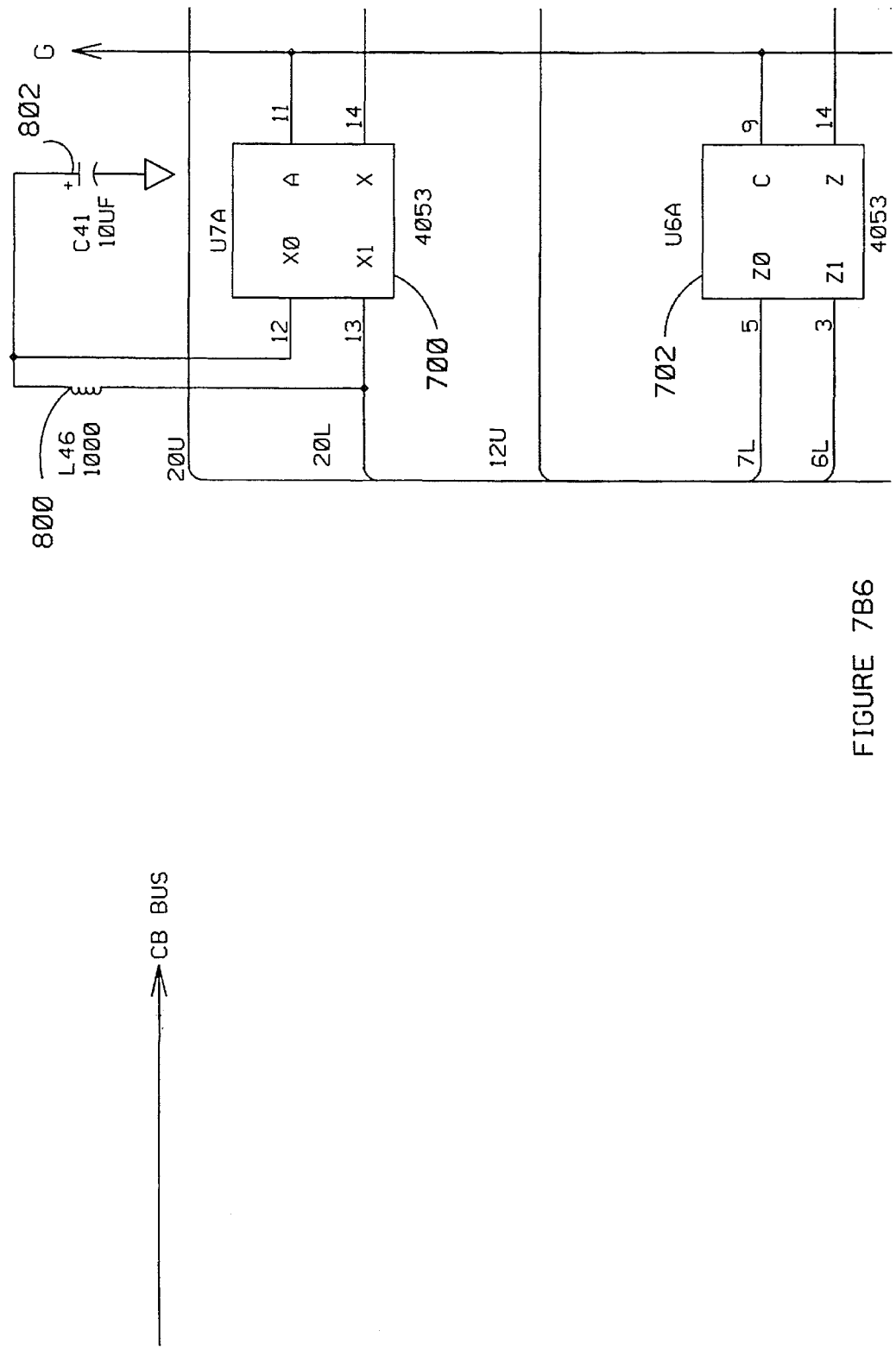
FIGURE 7B6

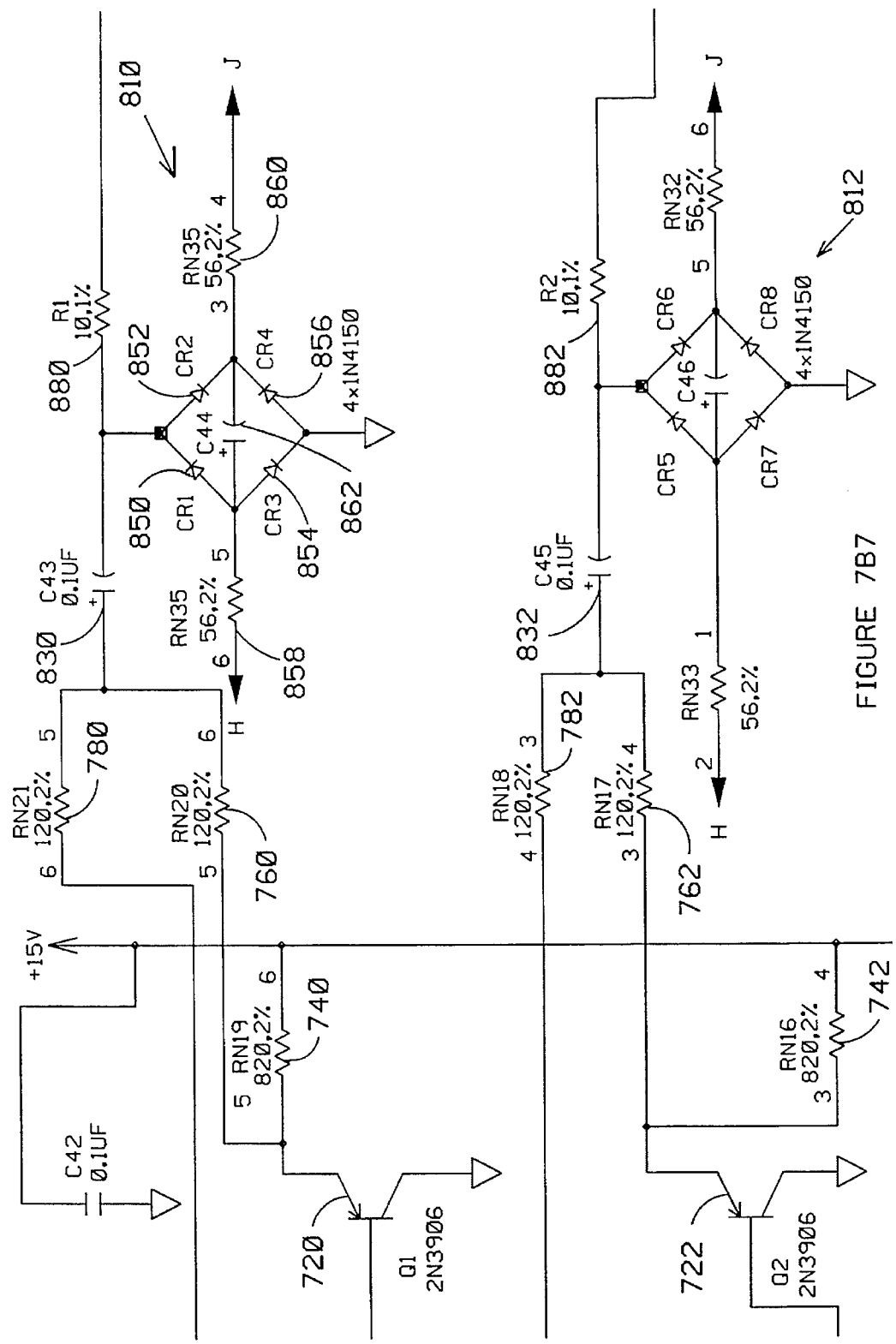
FIGURE 7B7

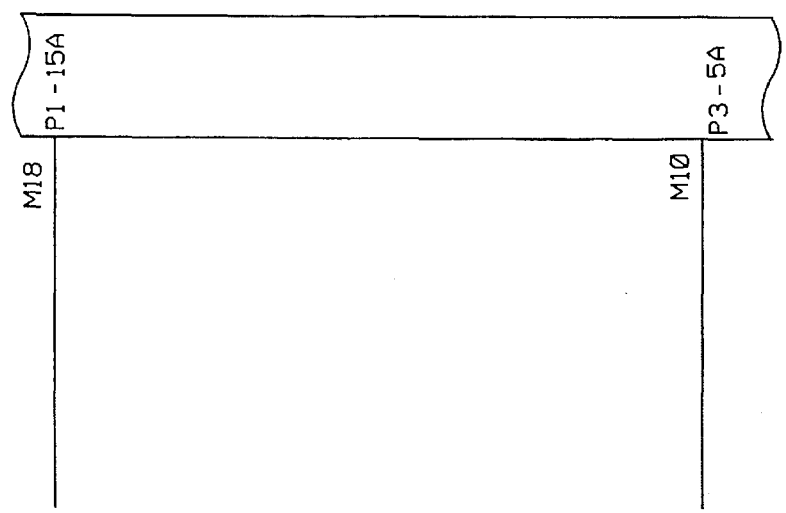
FIGURE 7B8

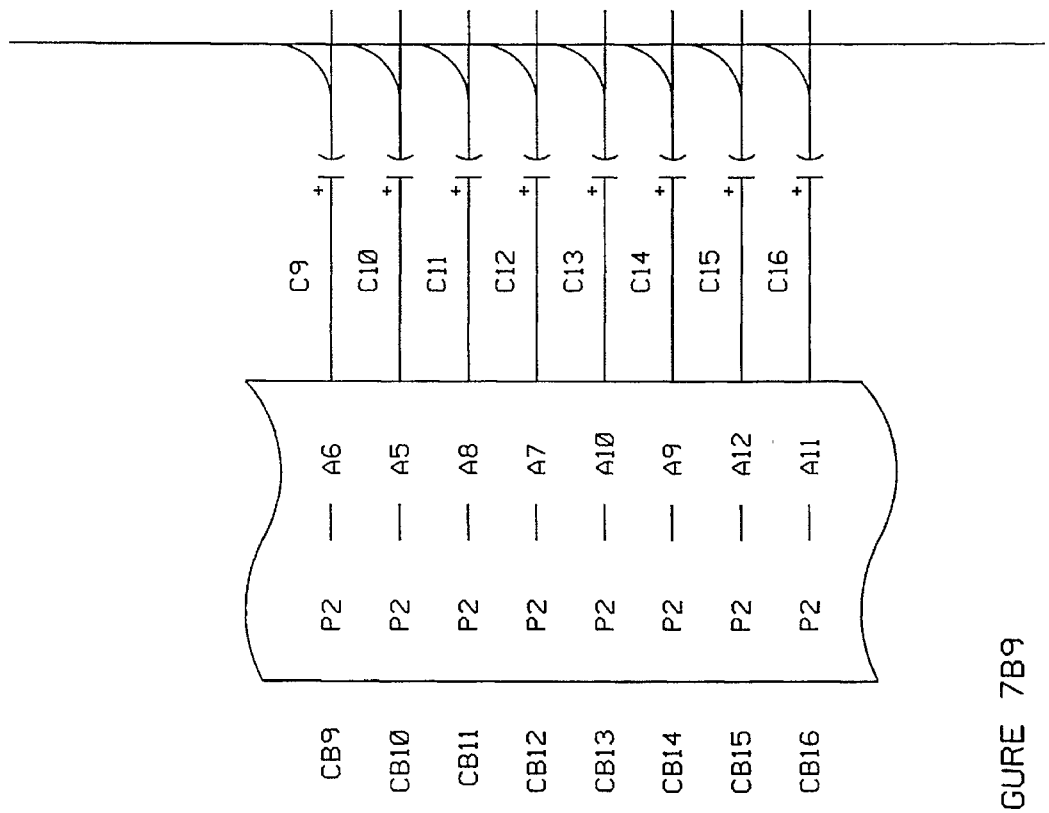
FIGURE 7B9

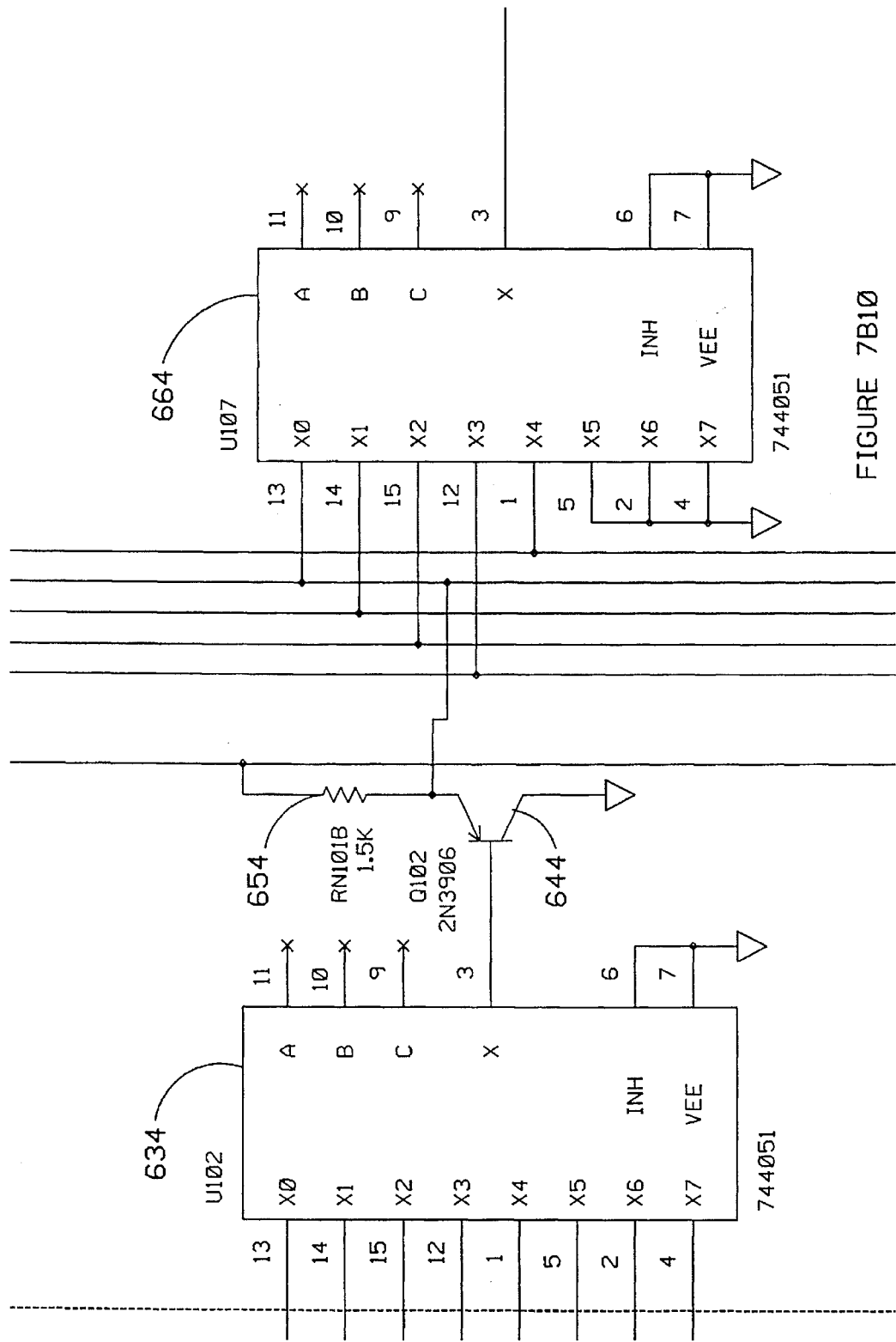
FIGURE 7B10

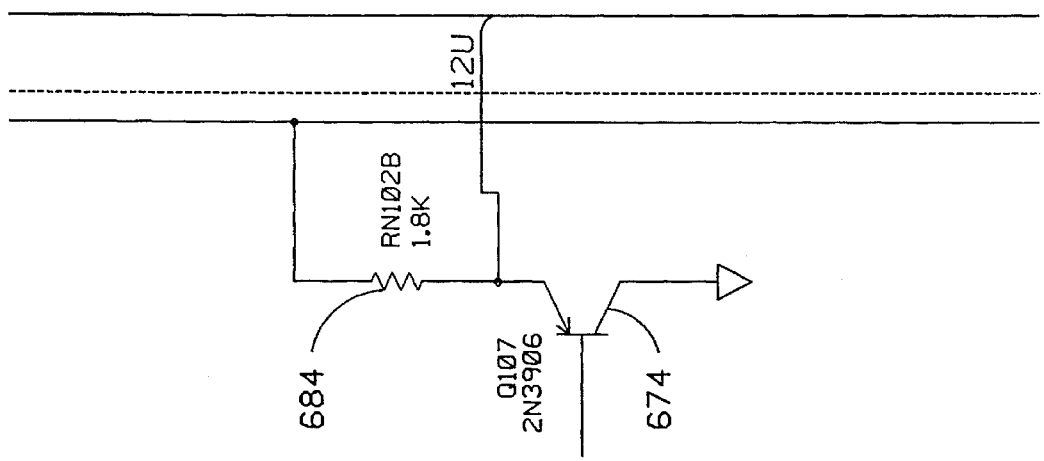
FIGURE 7B11

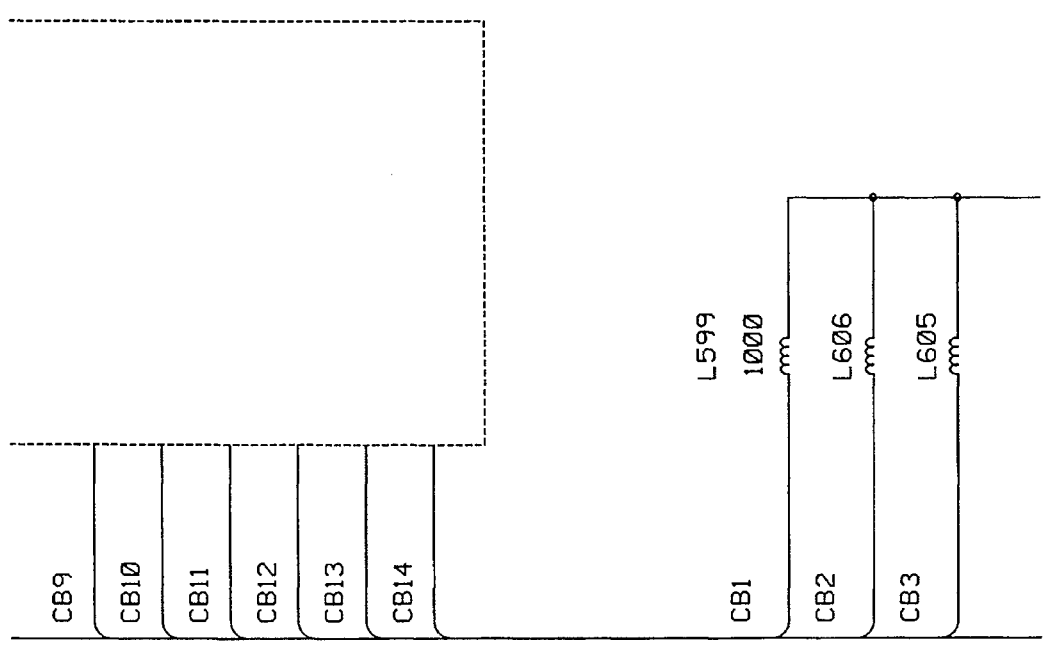
FIGURE 7B12

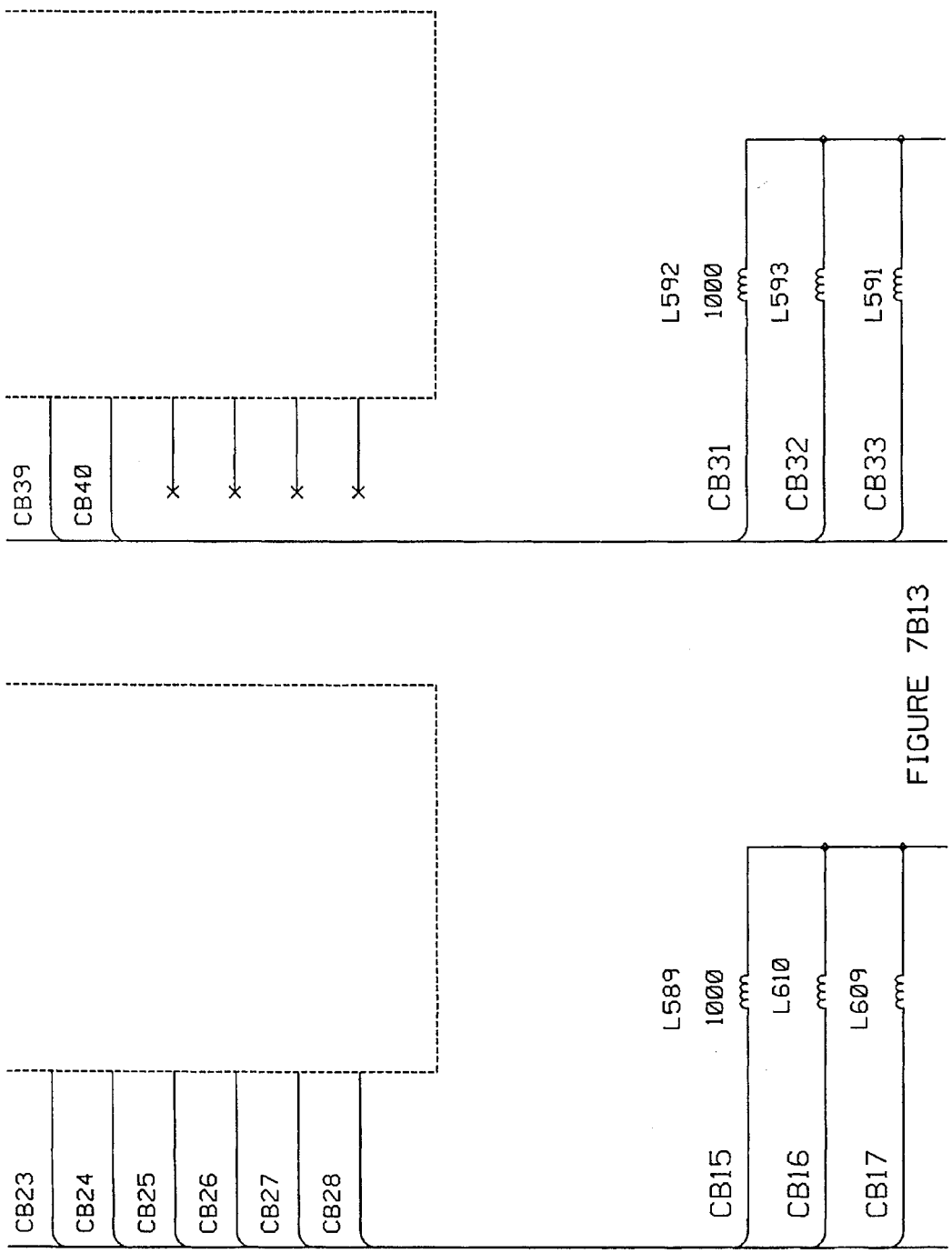
FIGURE 7B13

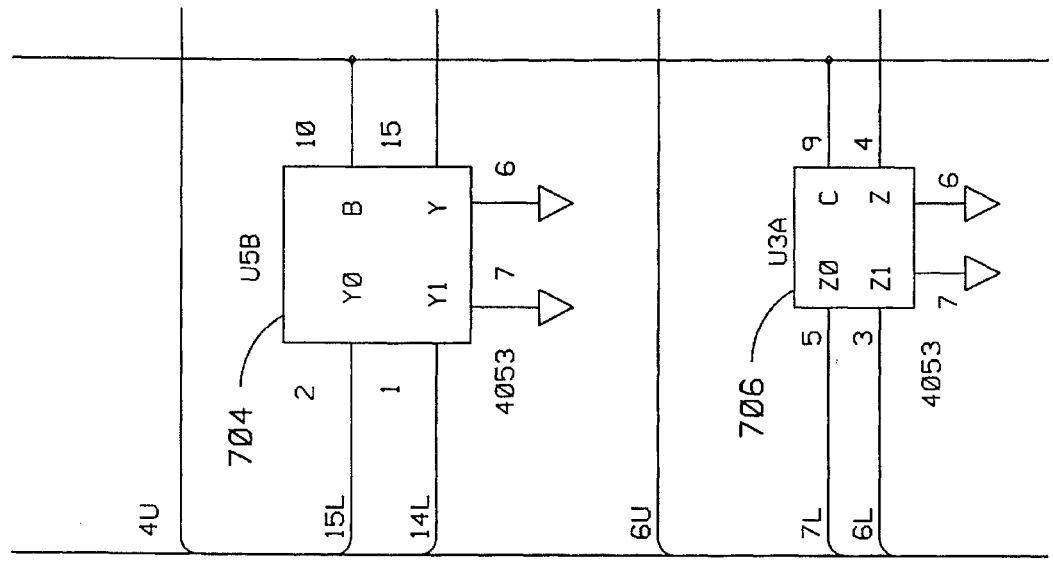
FIGURE 7B14

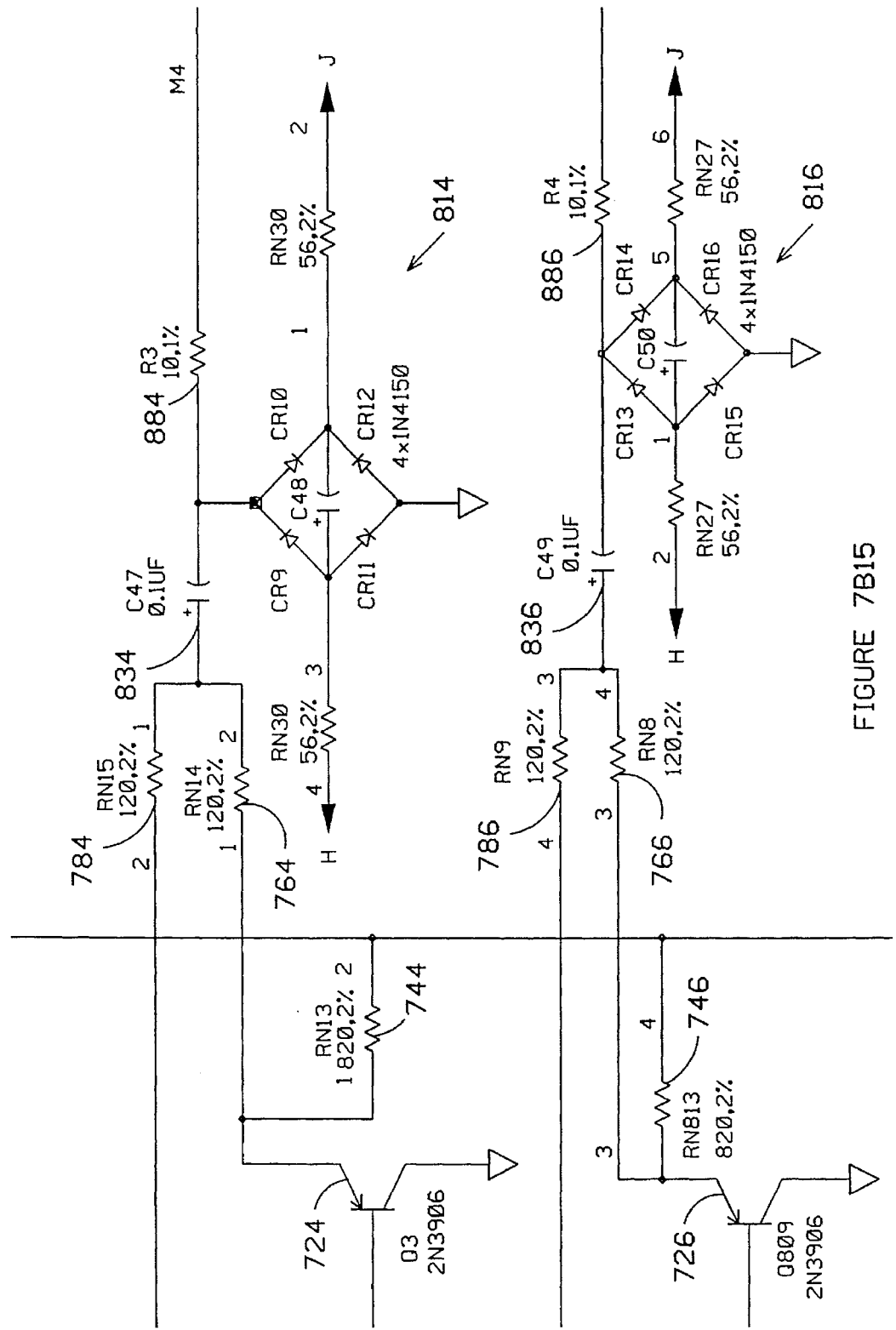
FIGURE 7B15

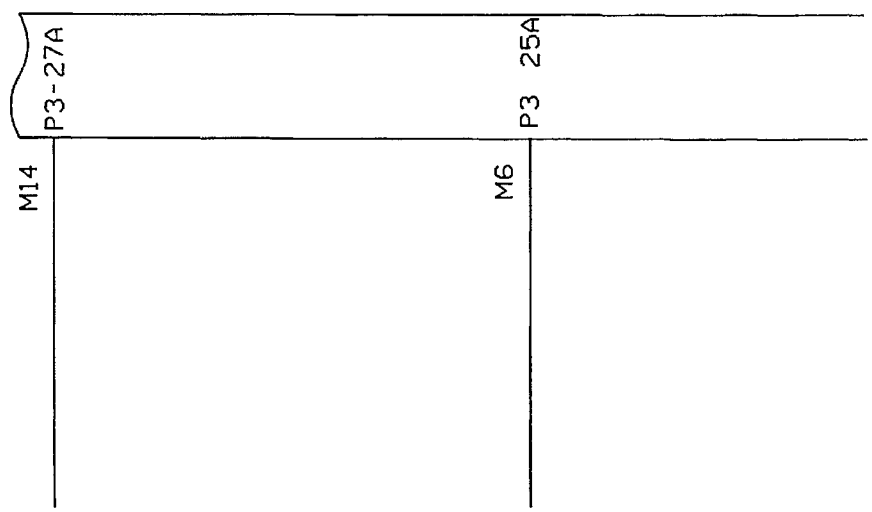

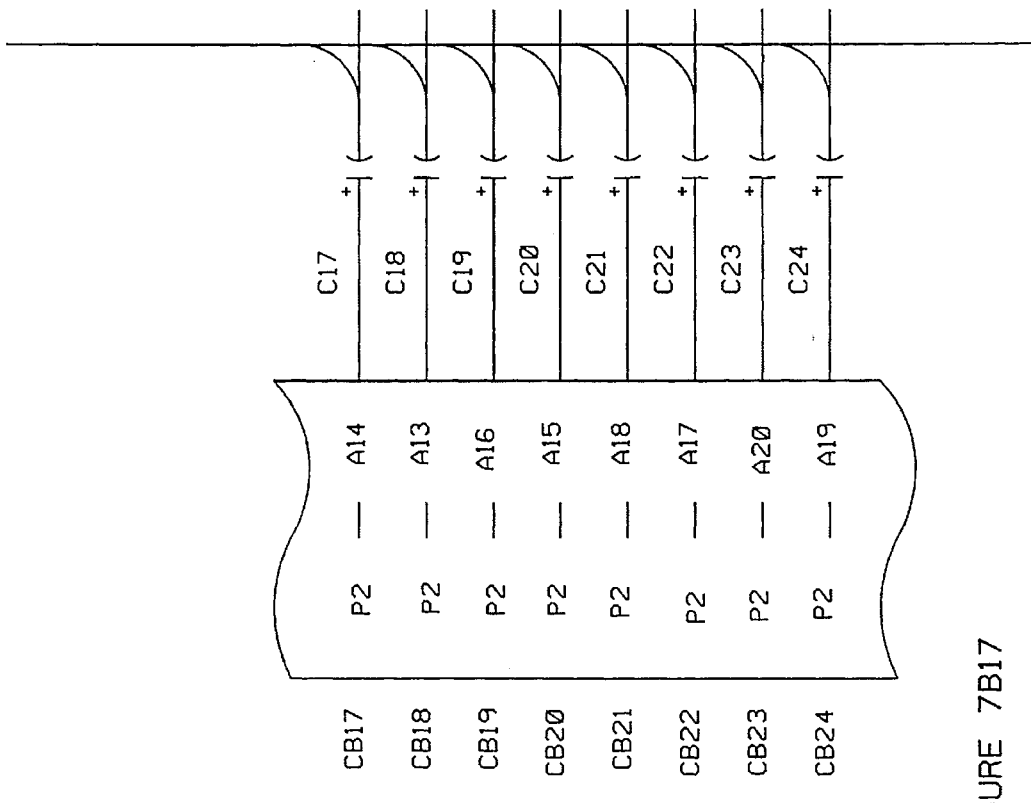
FIGURE 7B17

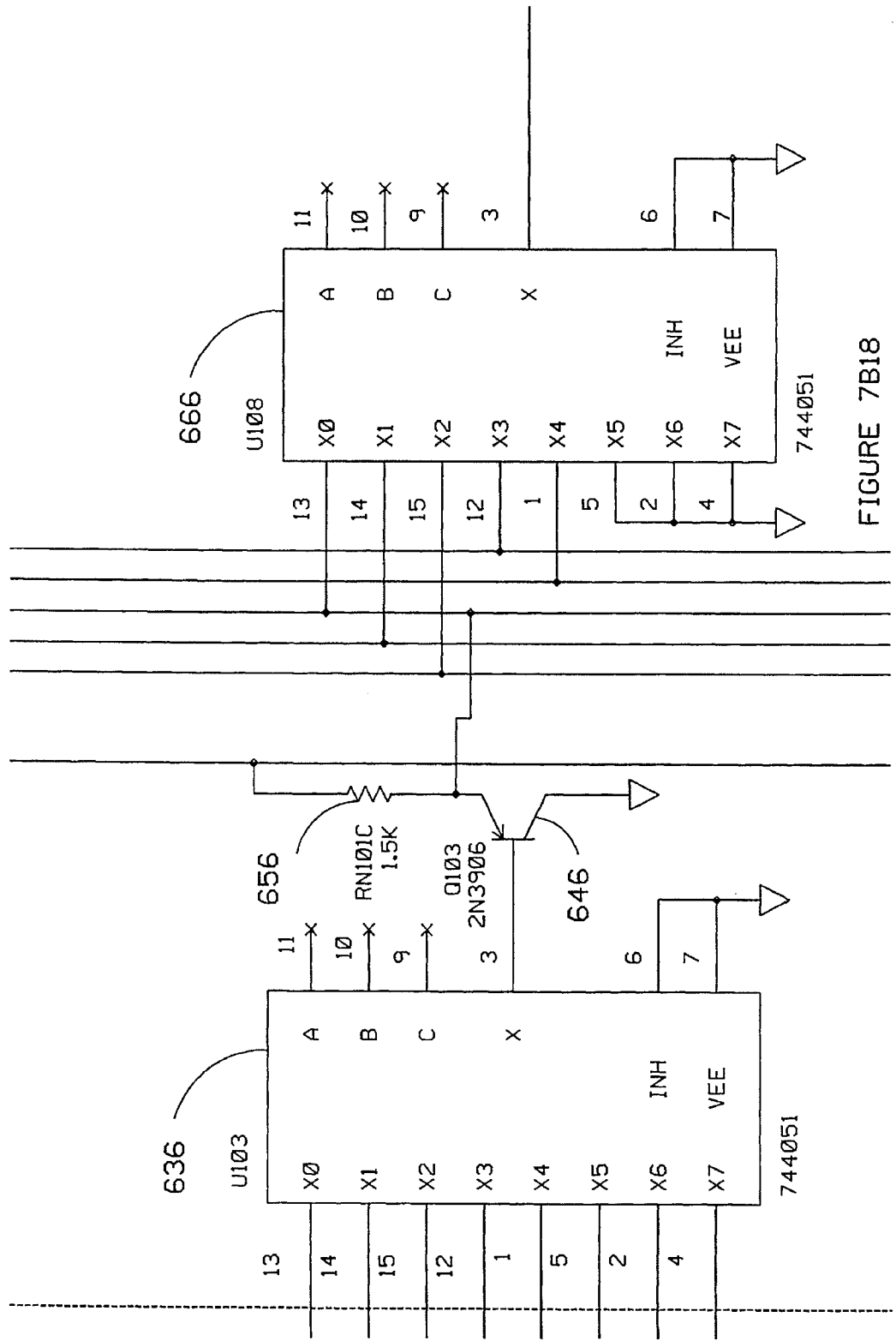
FIGURE 7B18

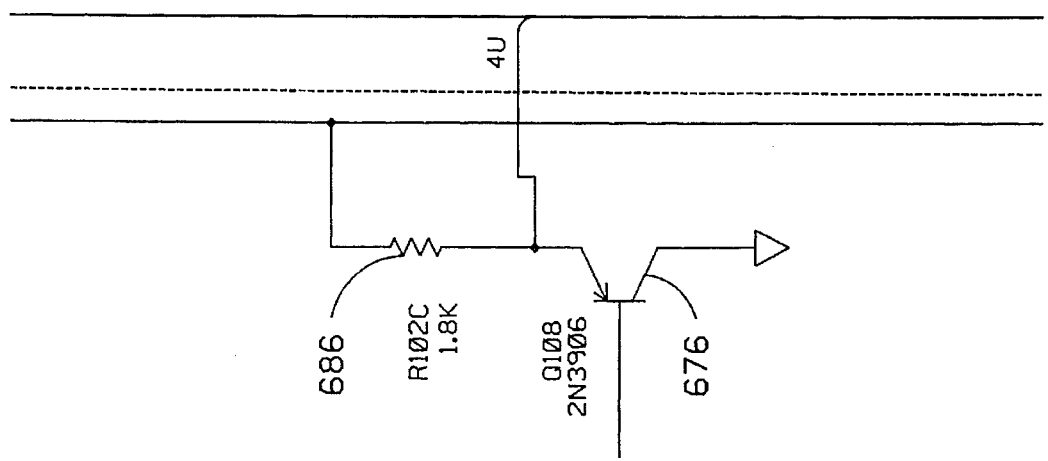
FIGURE 7B19

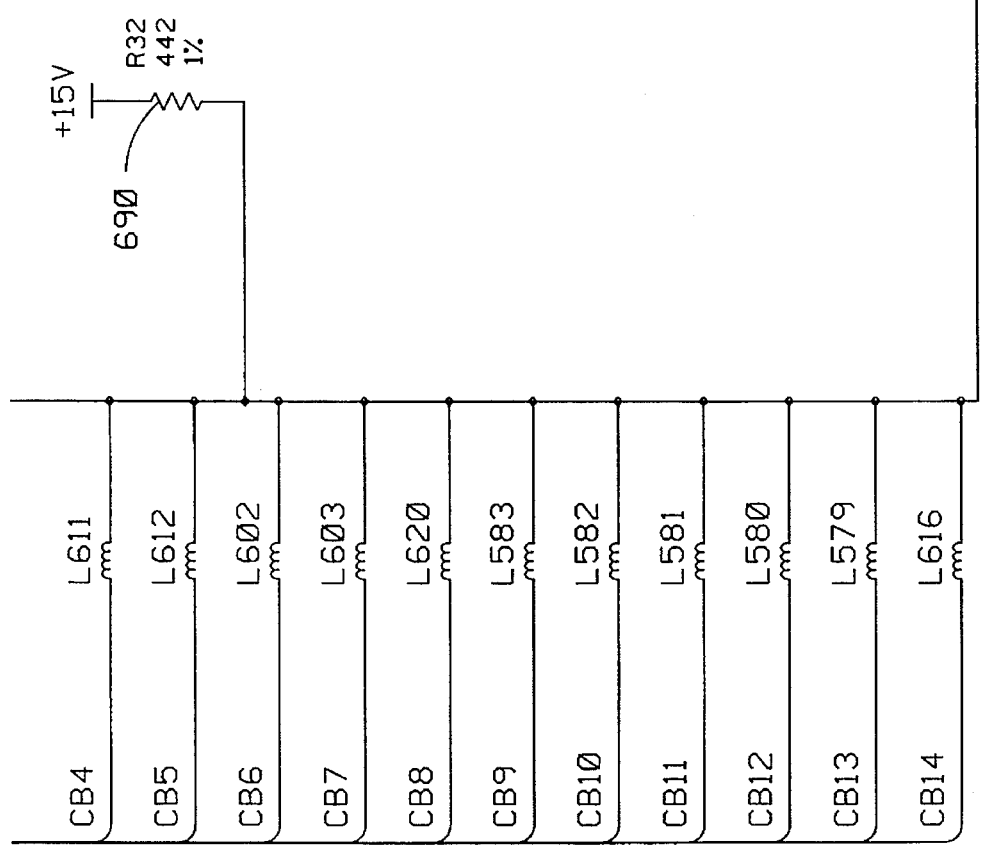
FIGURE 7B20

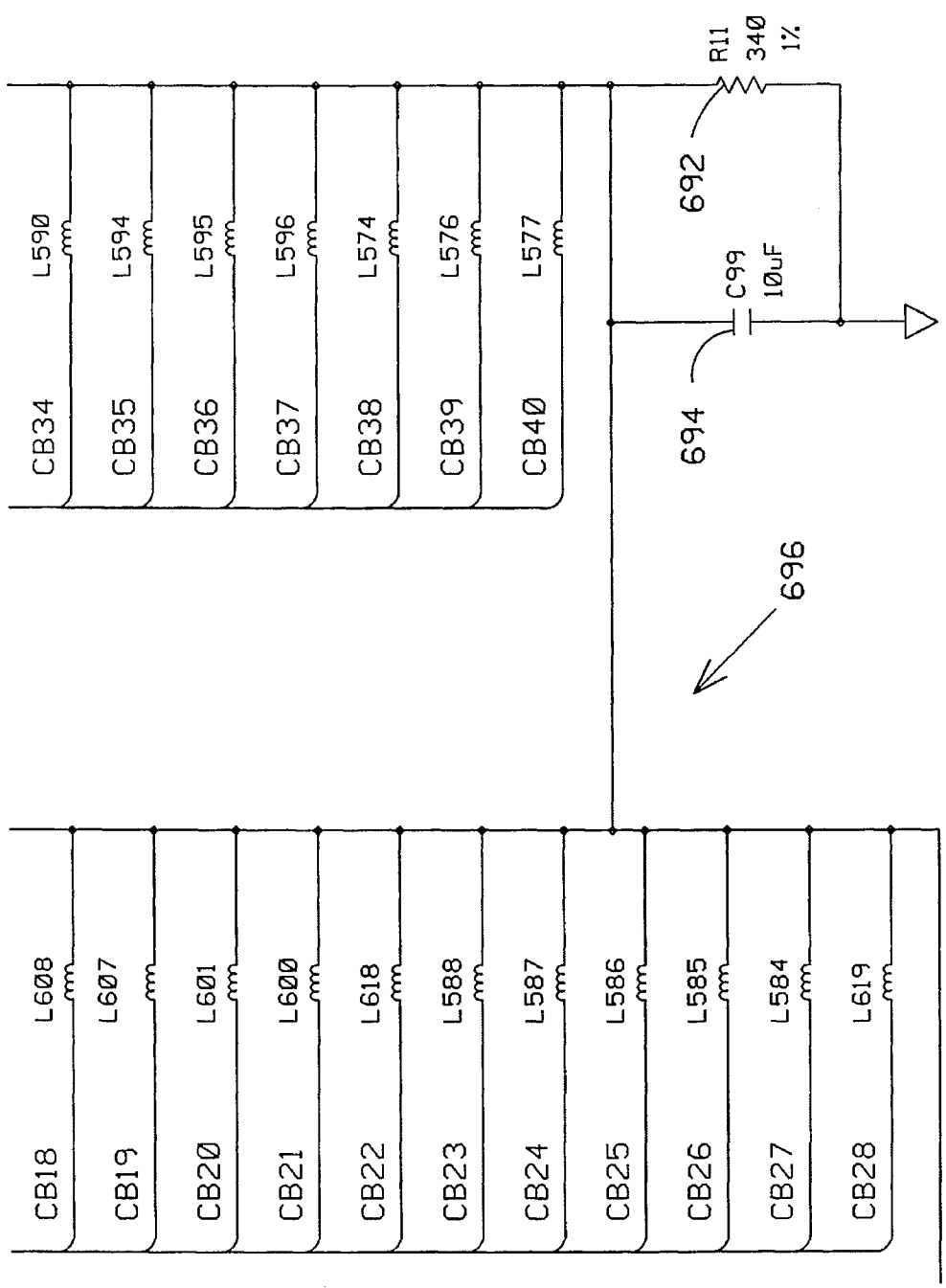
FIGURE 7B21

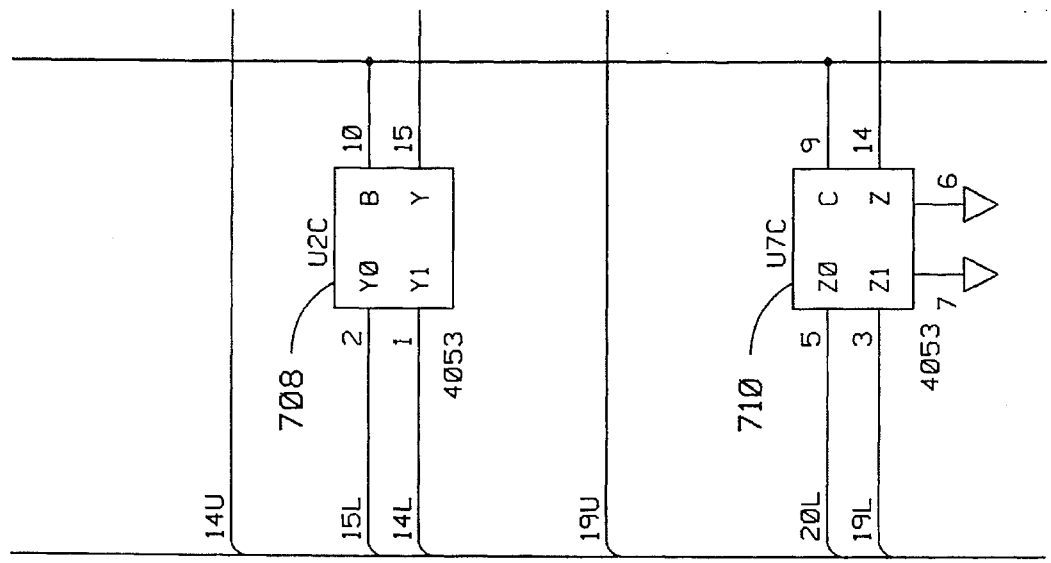
FIGURE 7B22

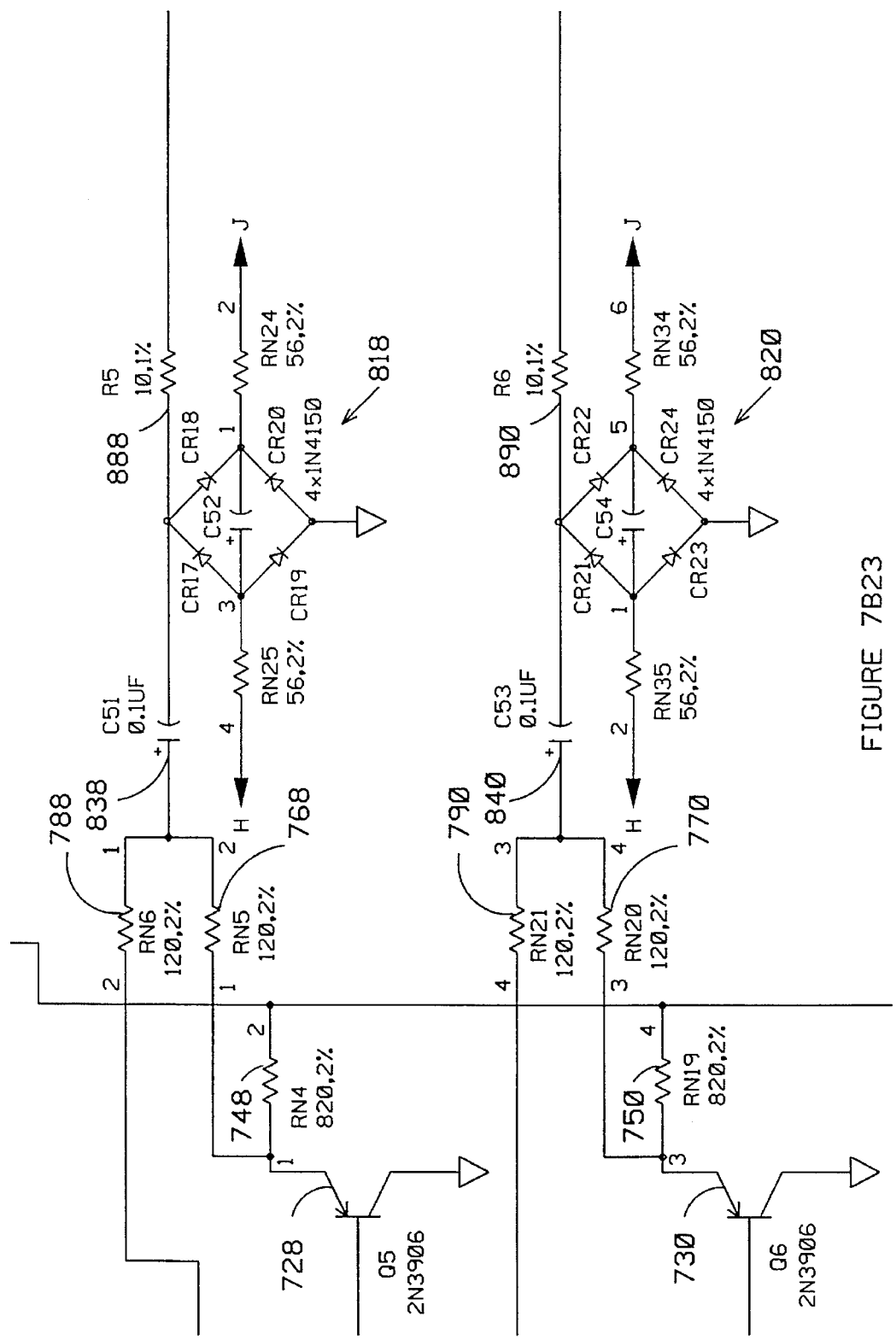
FIGURE 7B23

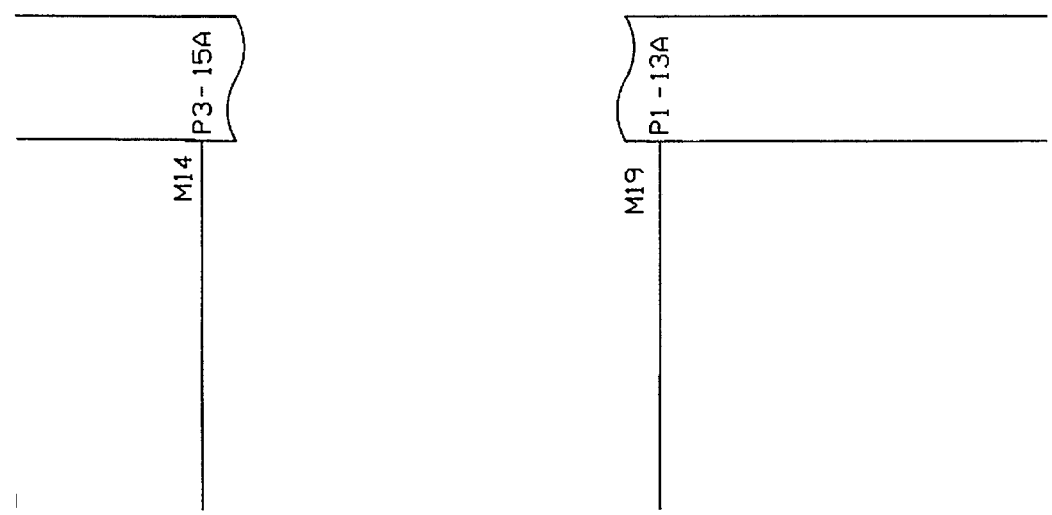
FIGURE 7B24

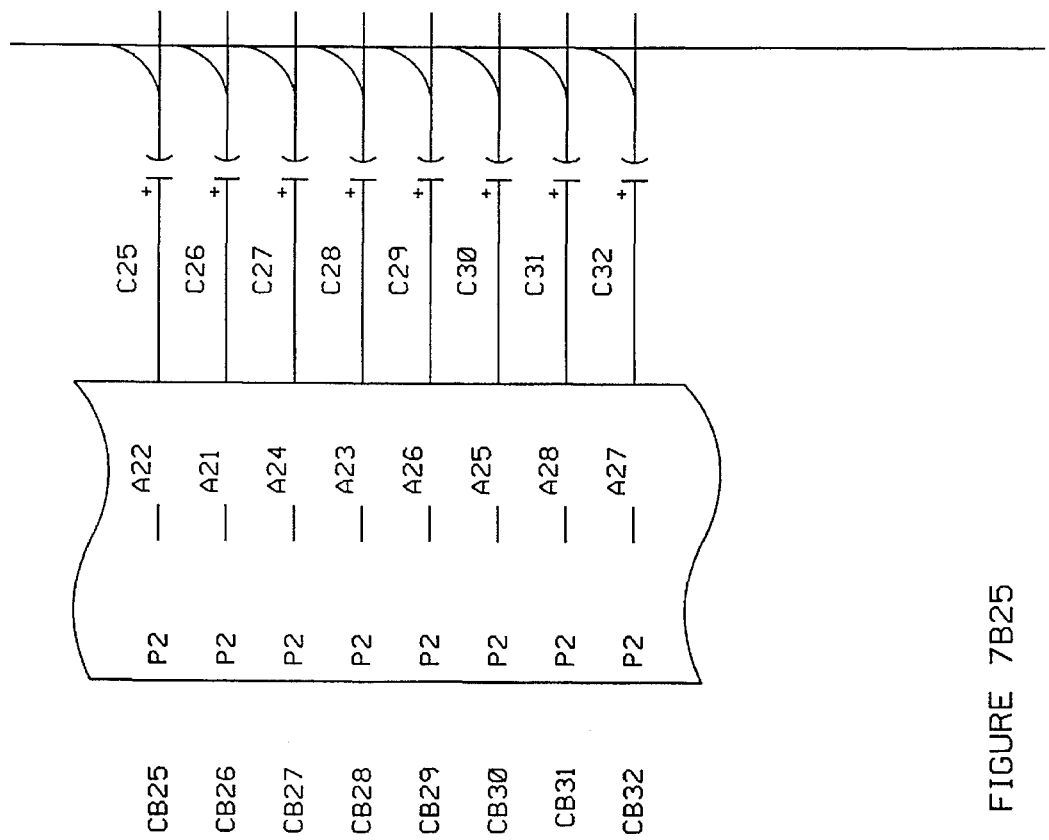
FIGURE 7B25

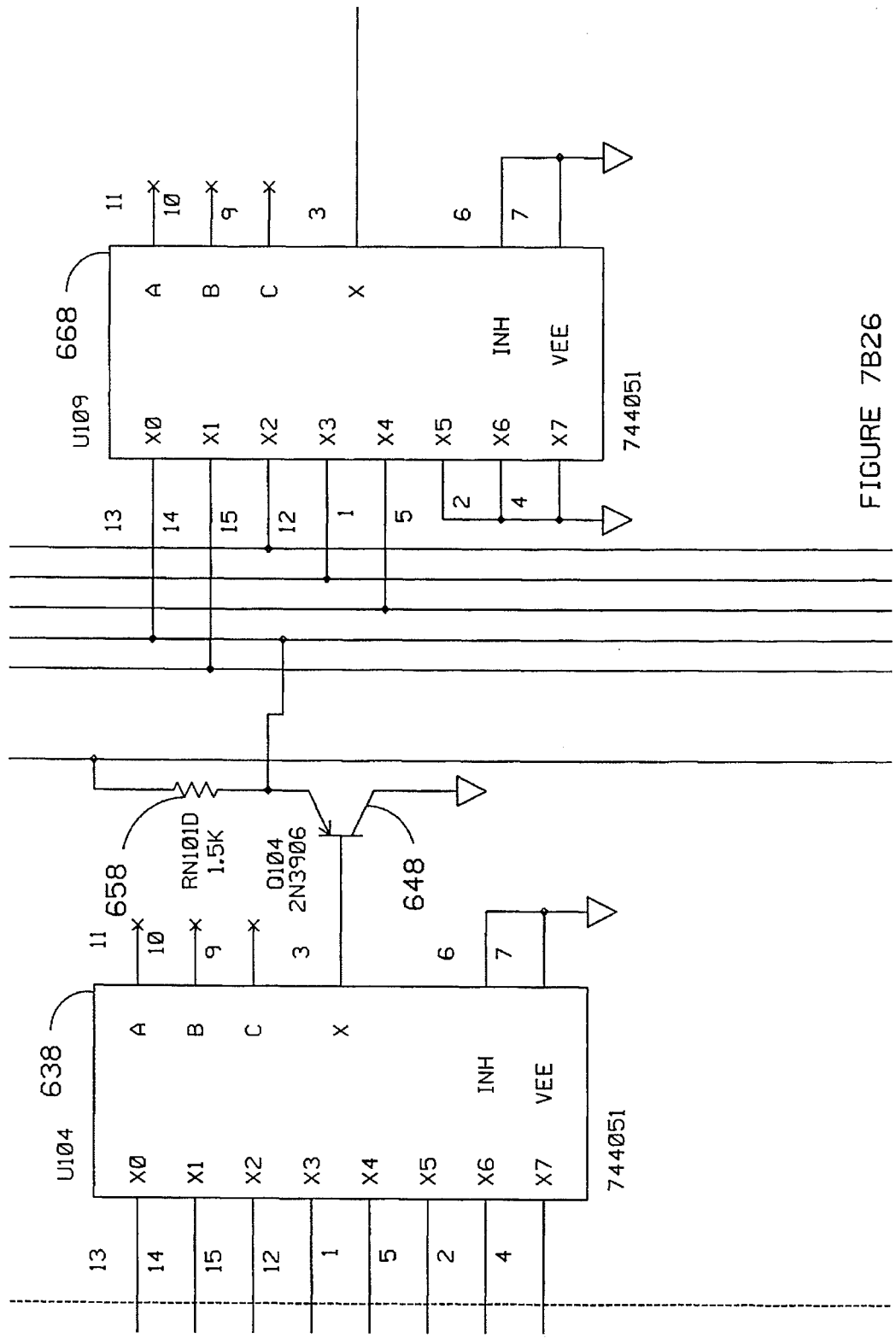
FIGURE 7B26

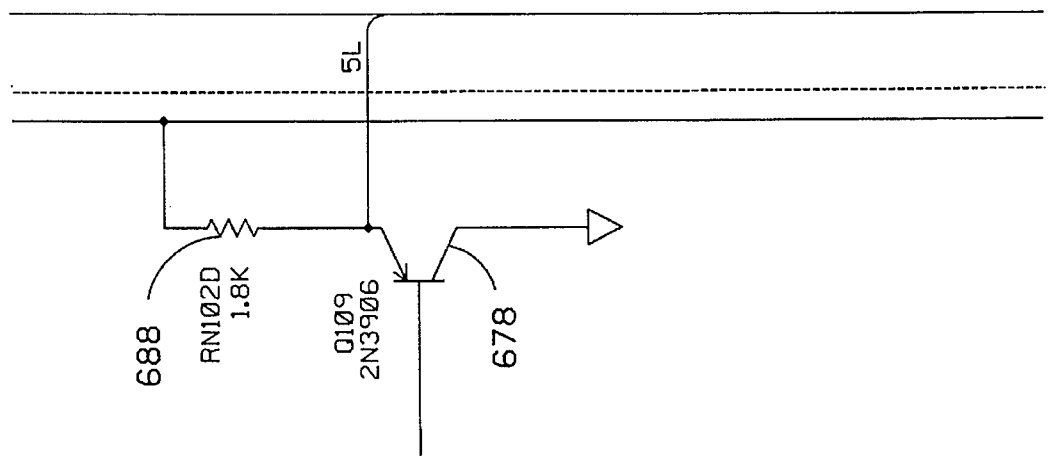
FIGURE 7B27

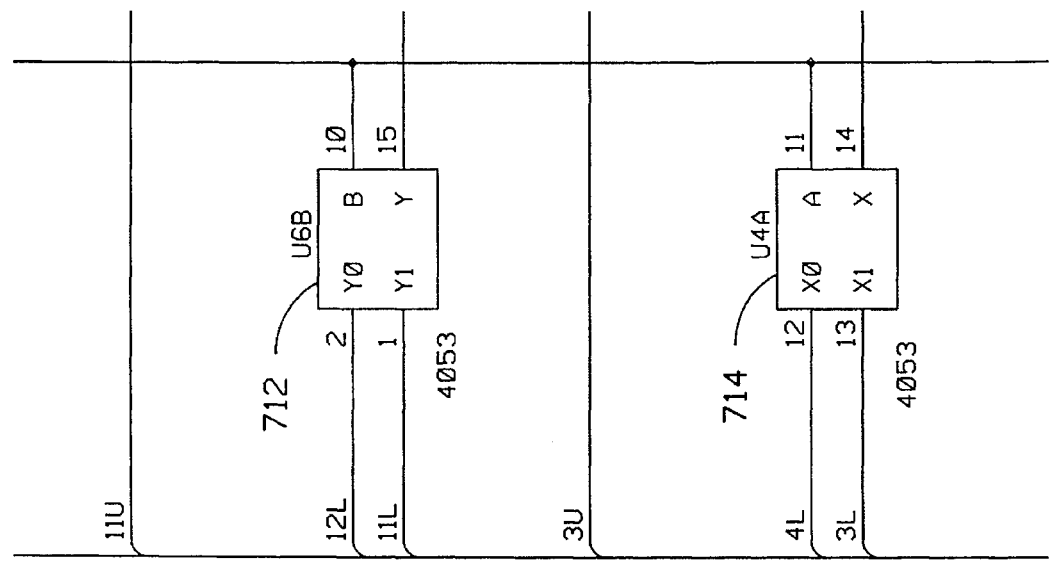
FIGURE 7B28

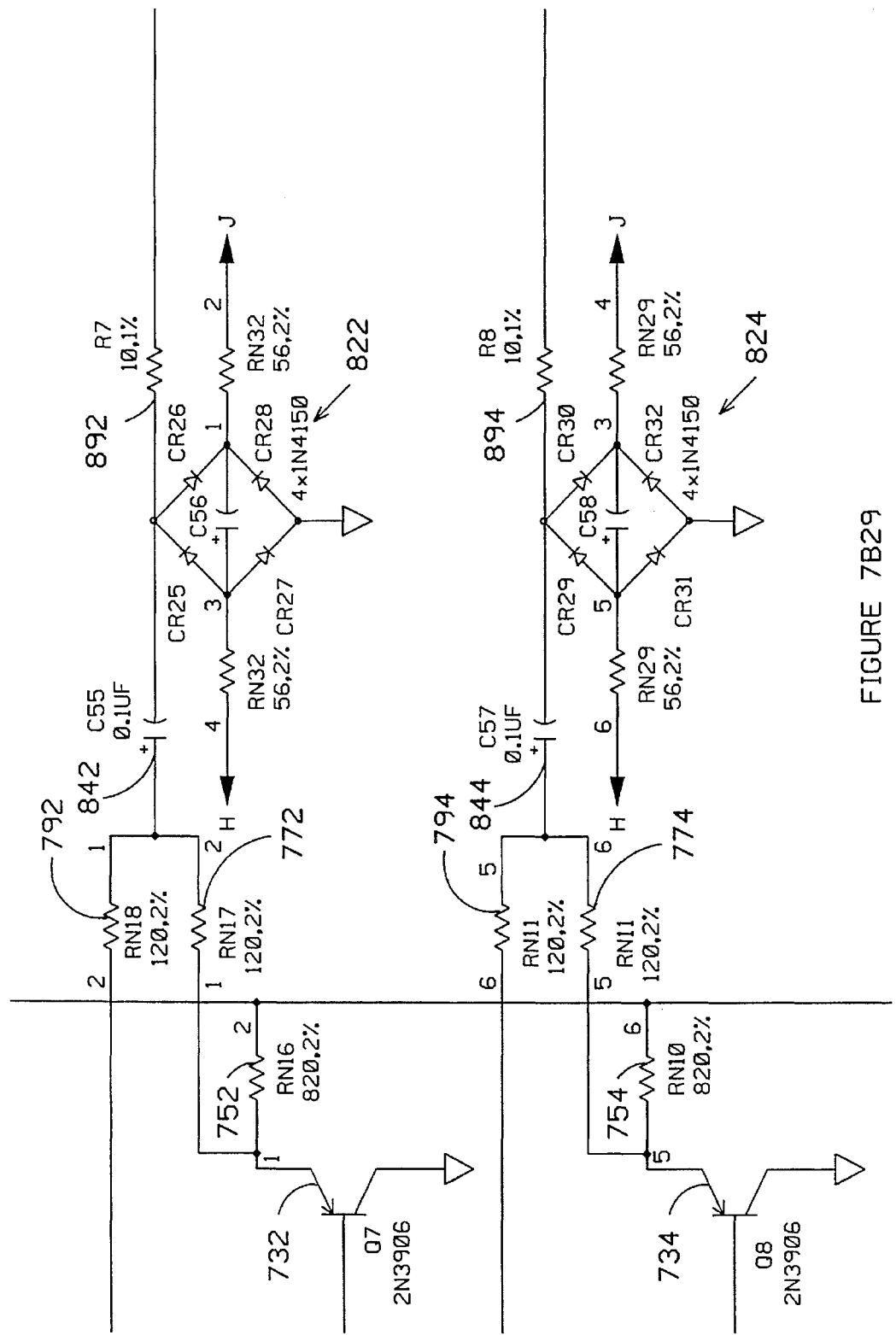
FIGURE 7B29

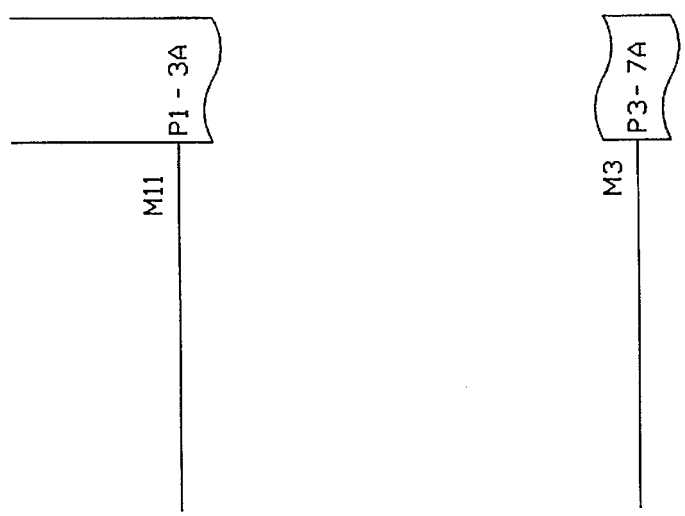
FIGURE 7B30

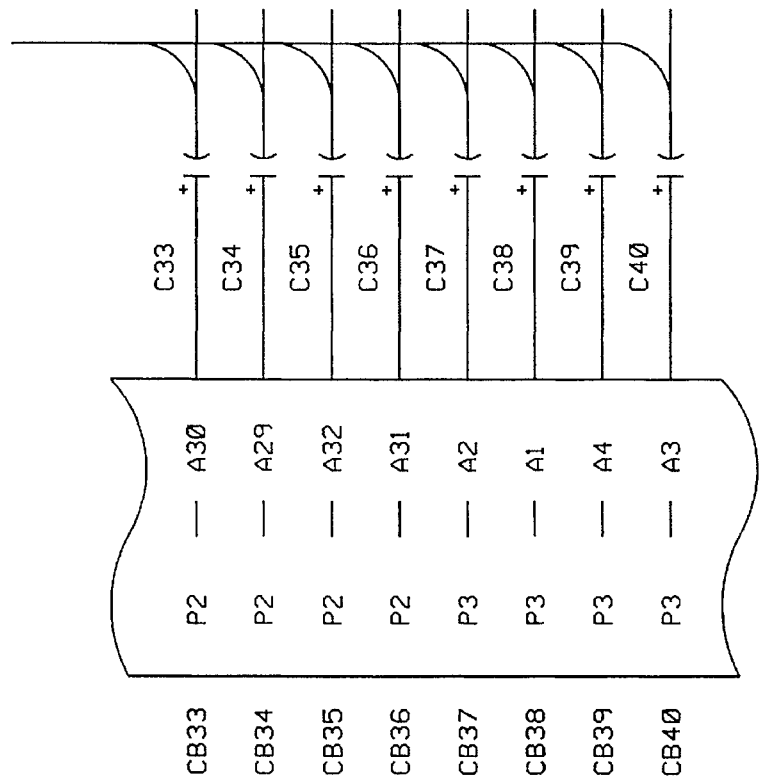
FIGURE 7B31

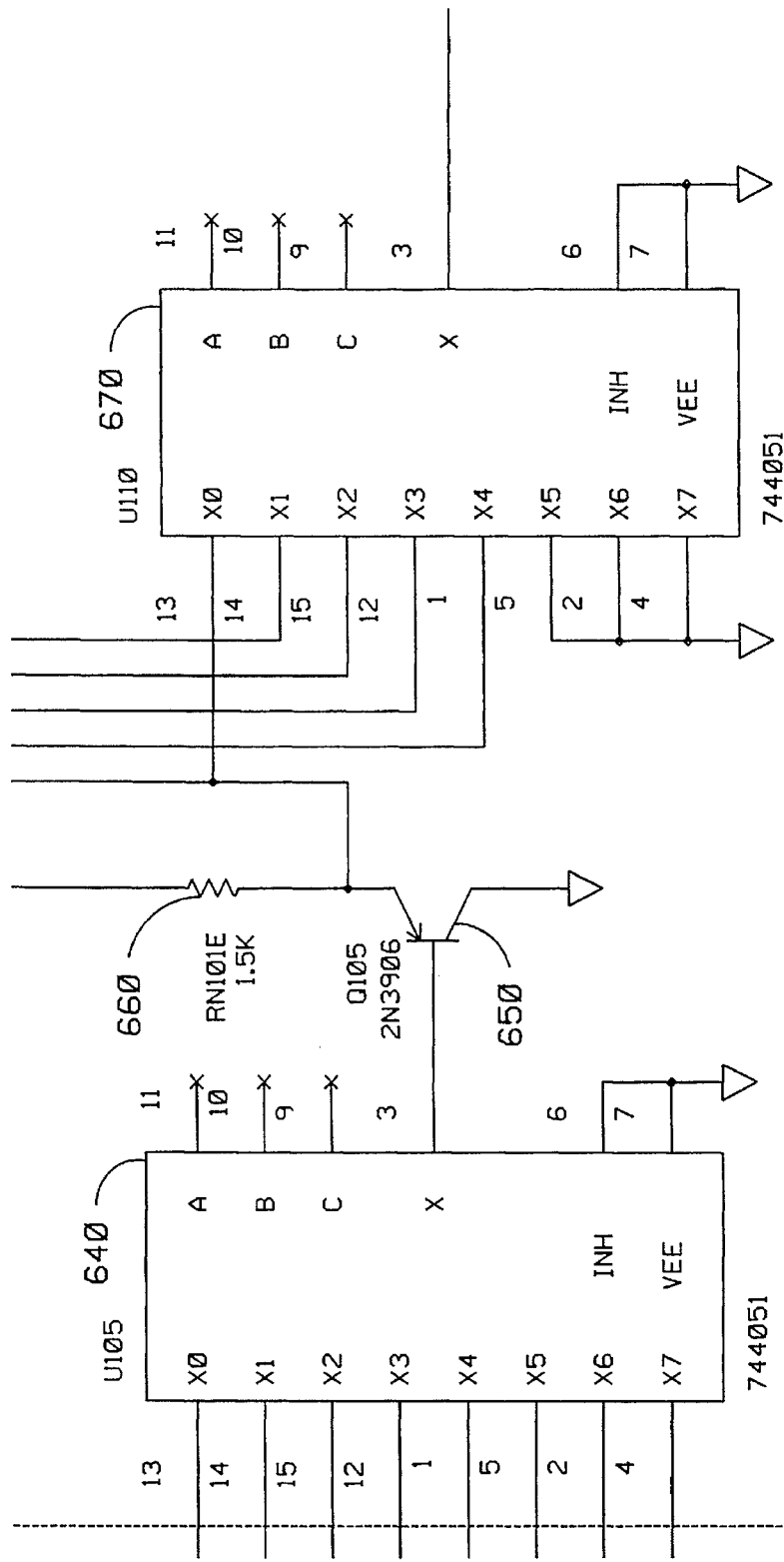
FIGURE 7B32

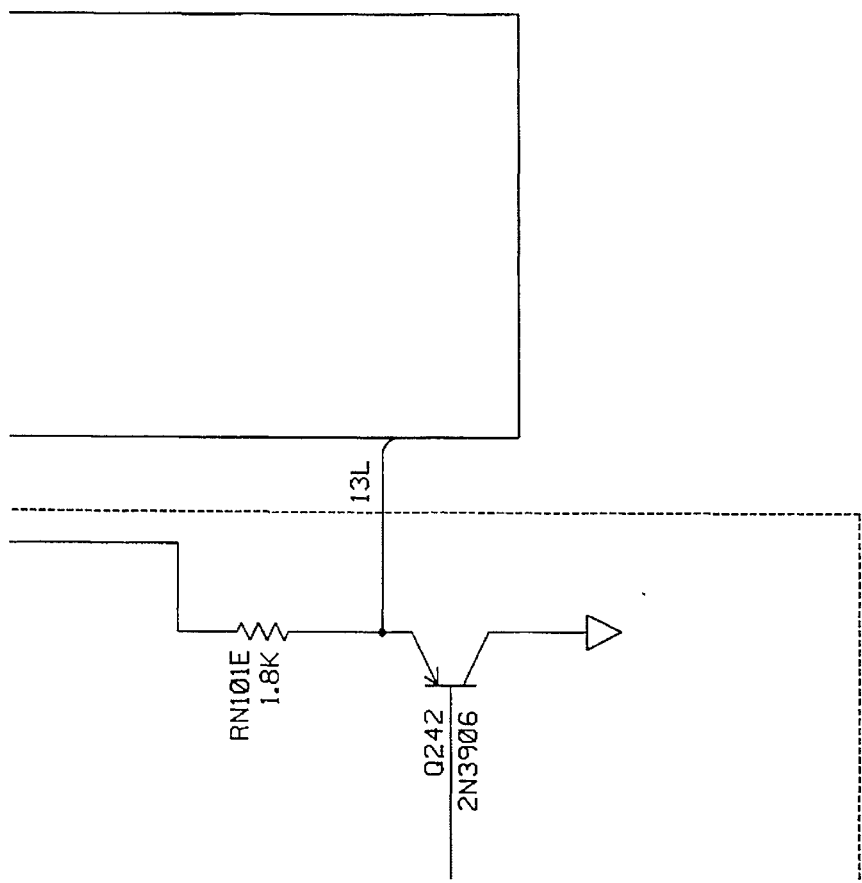
FIGURE 7B33

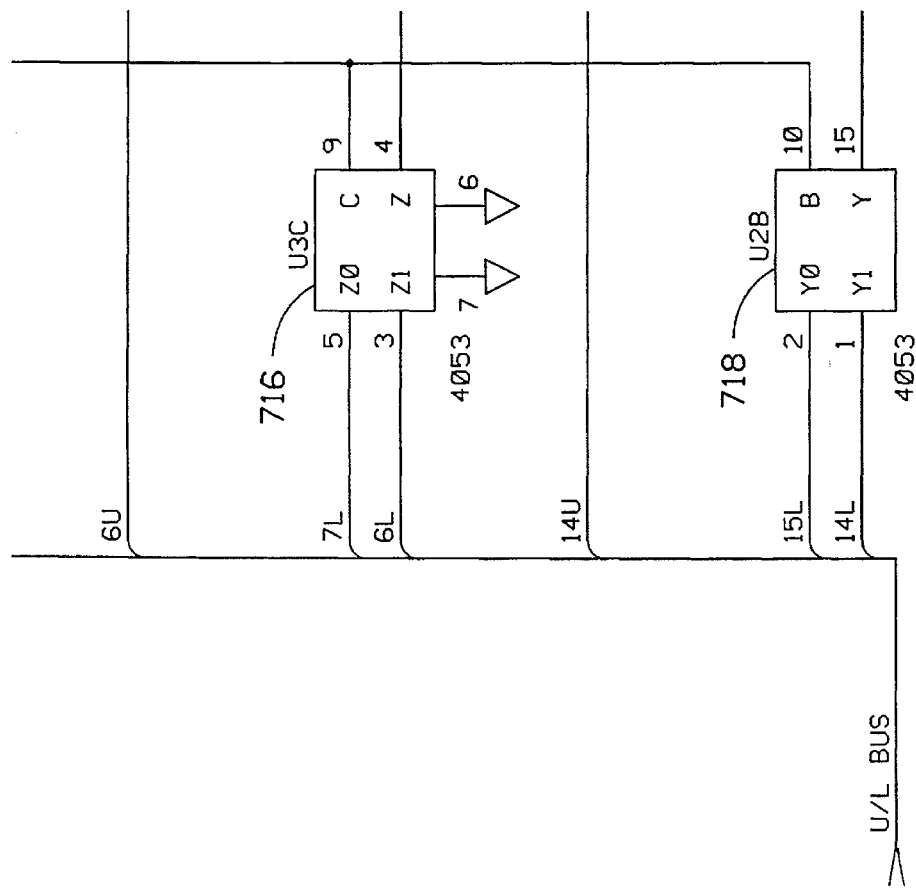
FIGURE 7B34

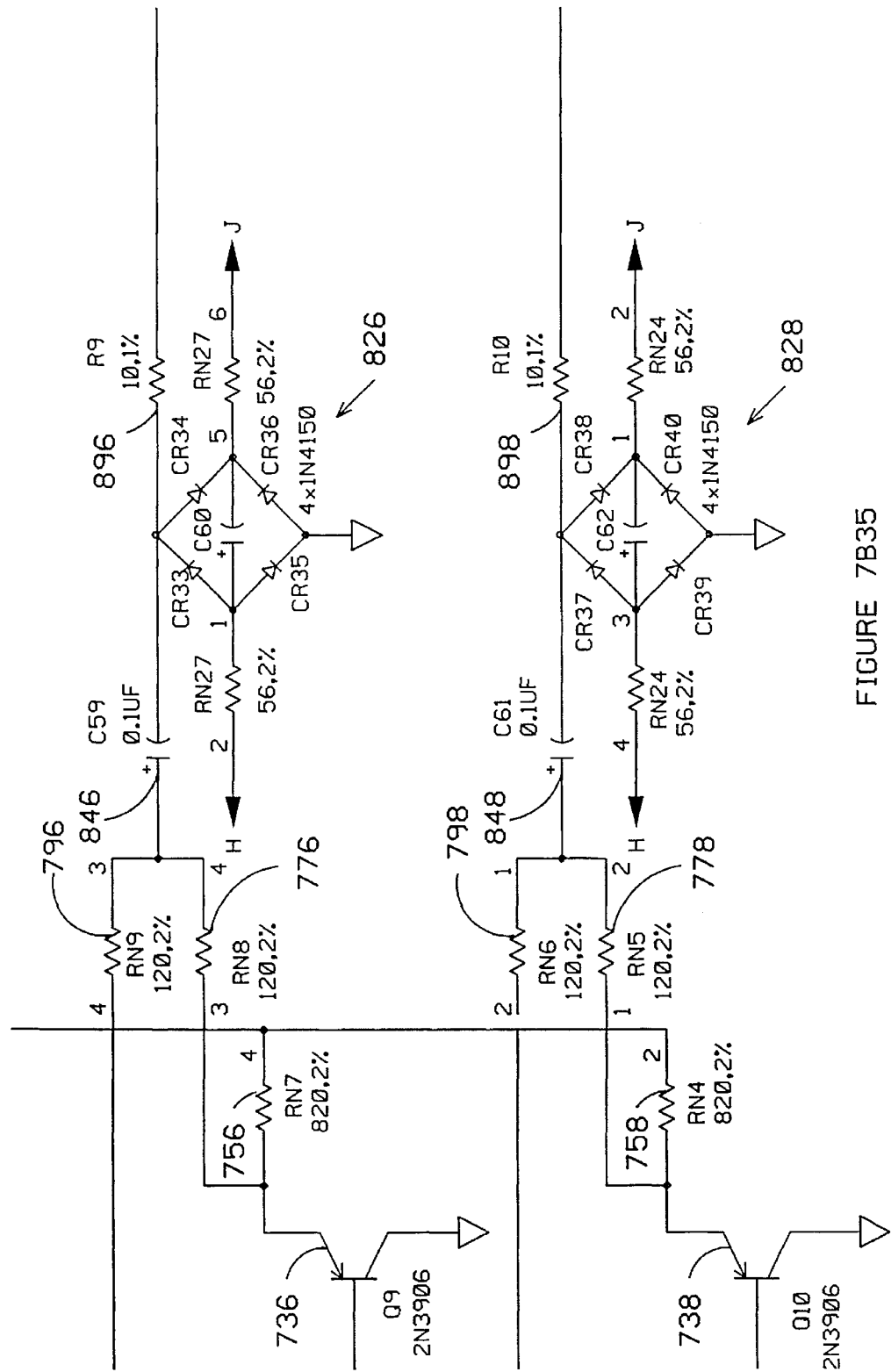
FIGURE 7B35

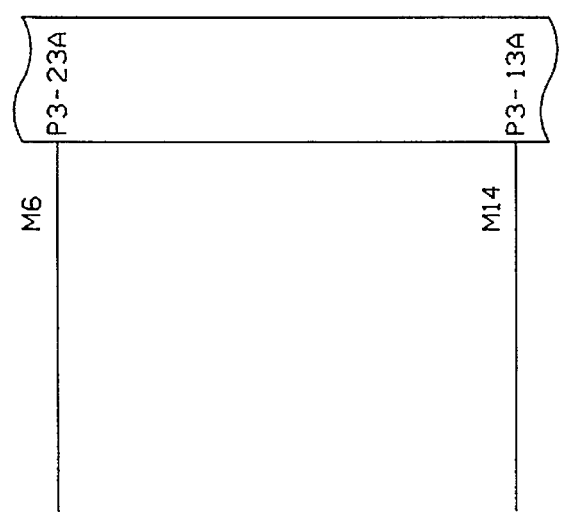
FIGURE 7B36

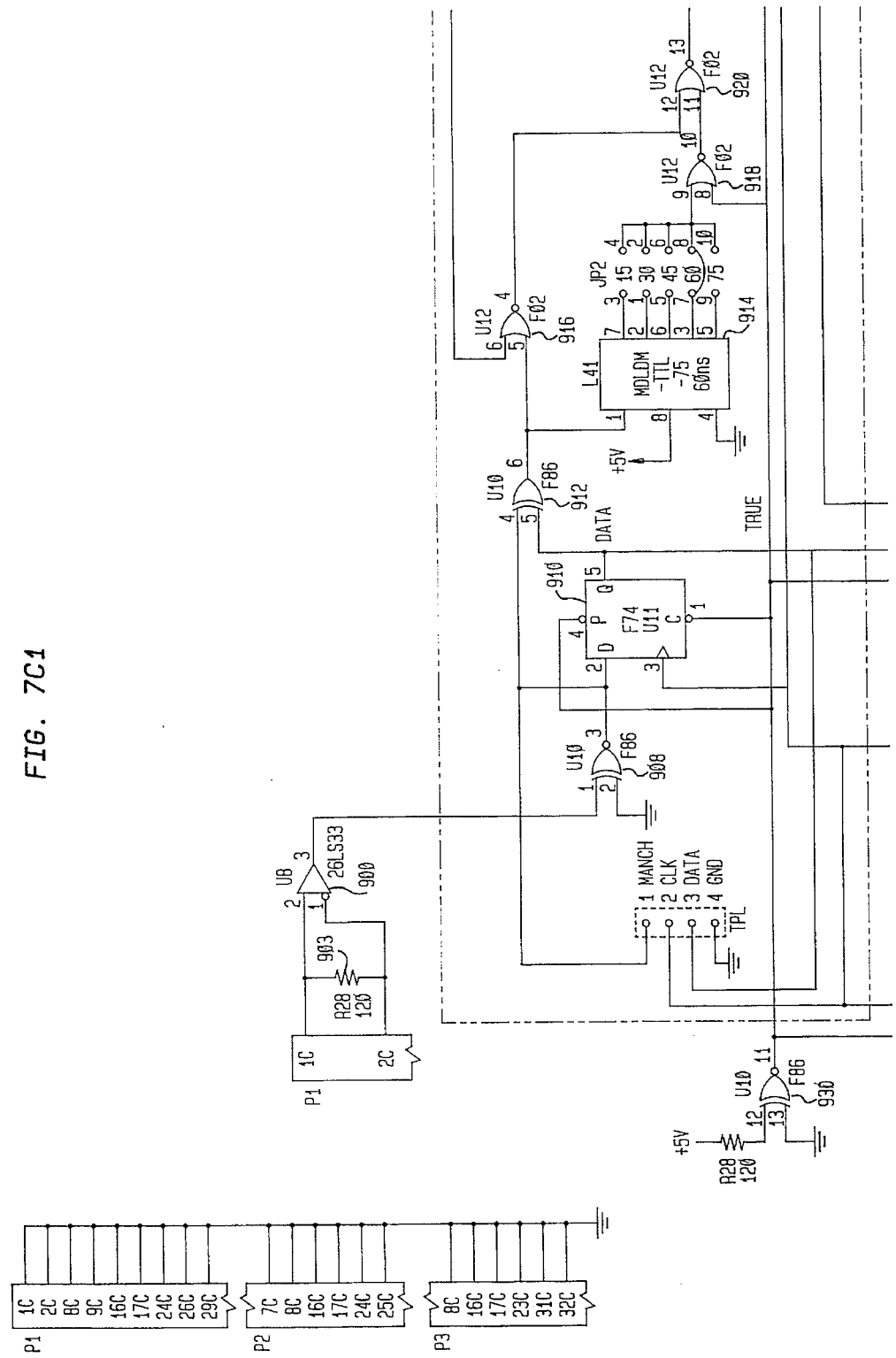
FIG. 7C1

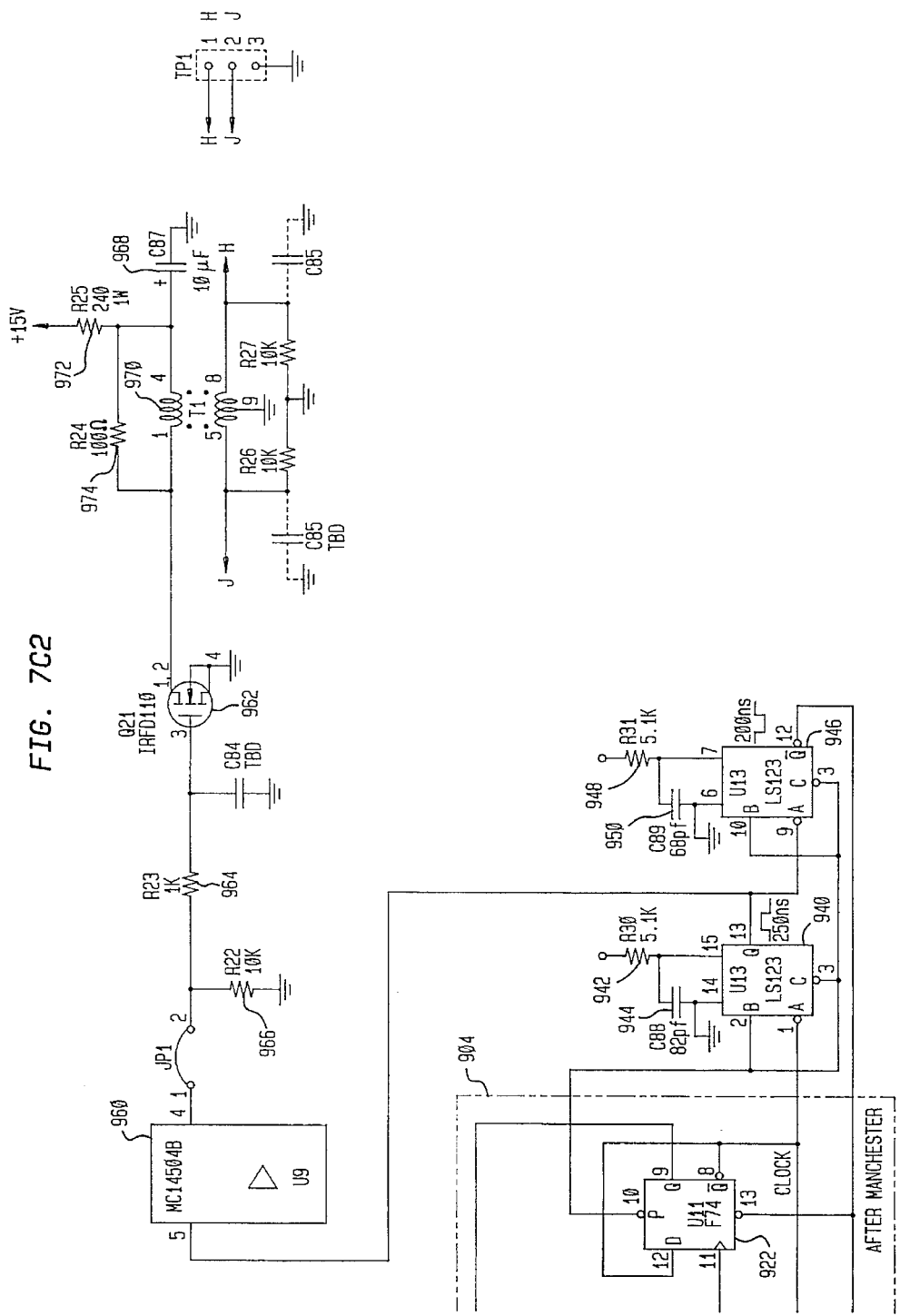
FIG. 7C2

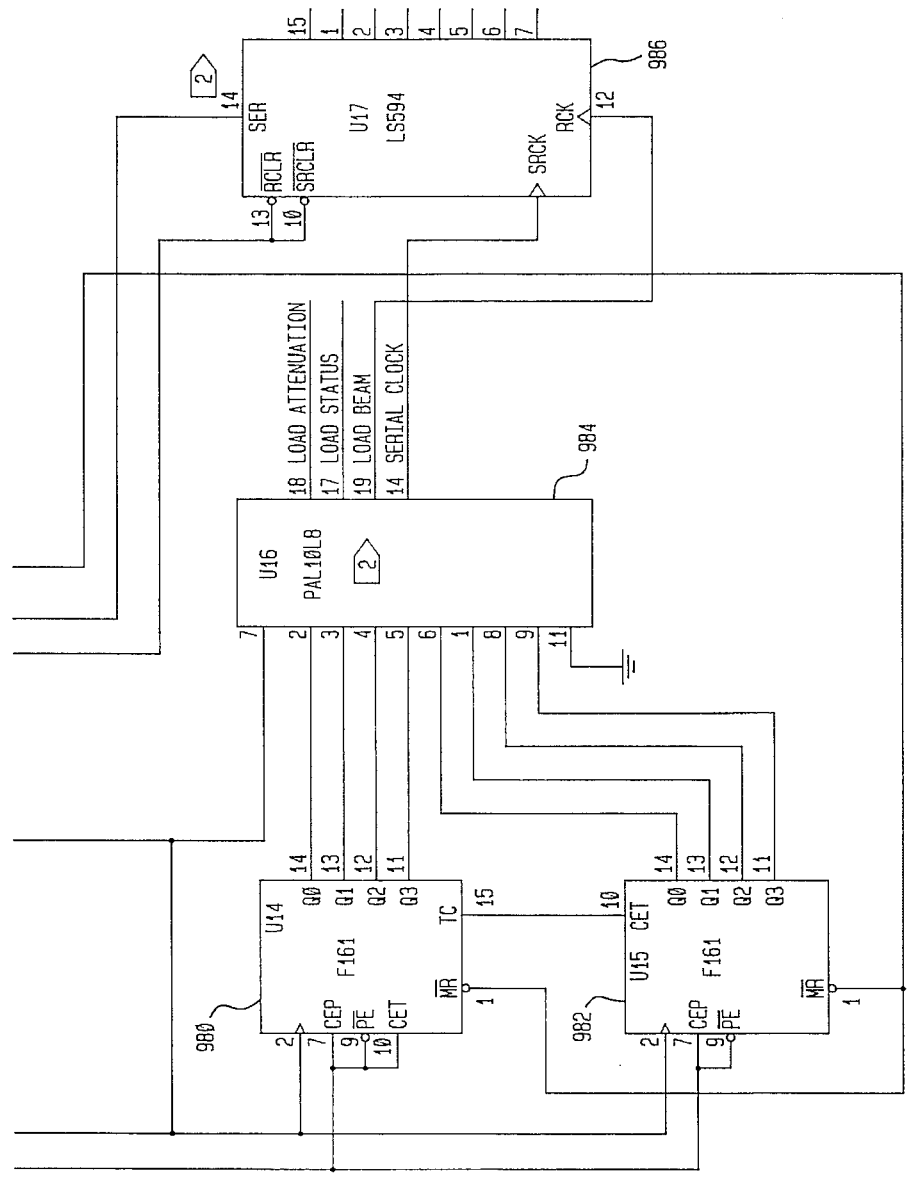
FIG. 7C3

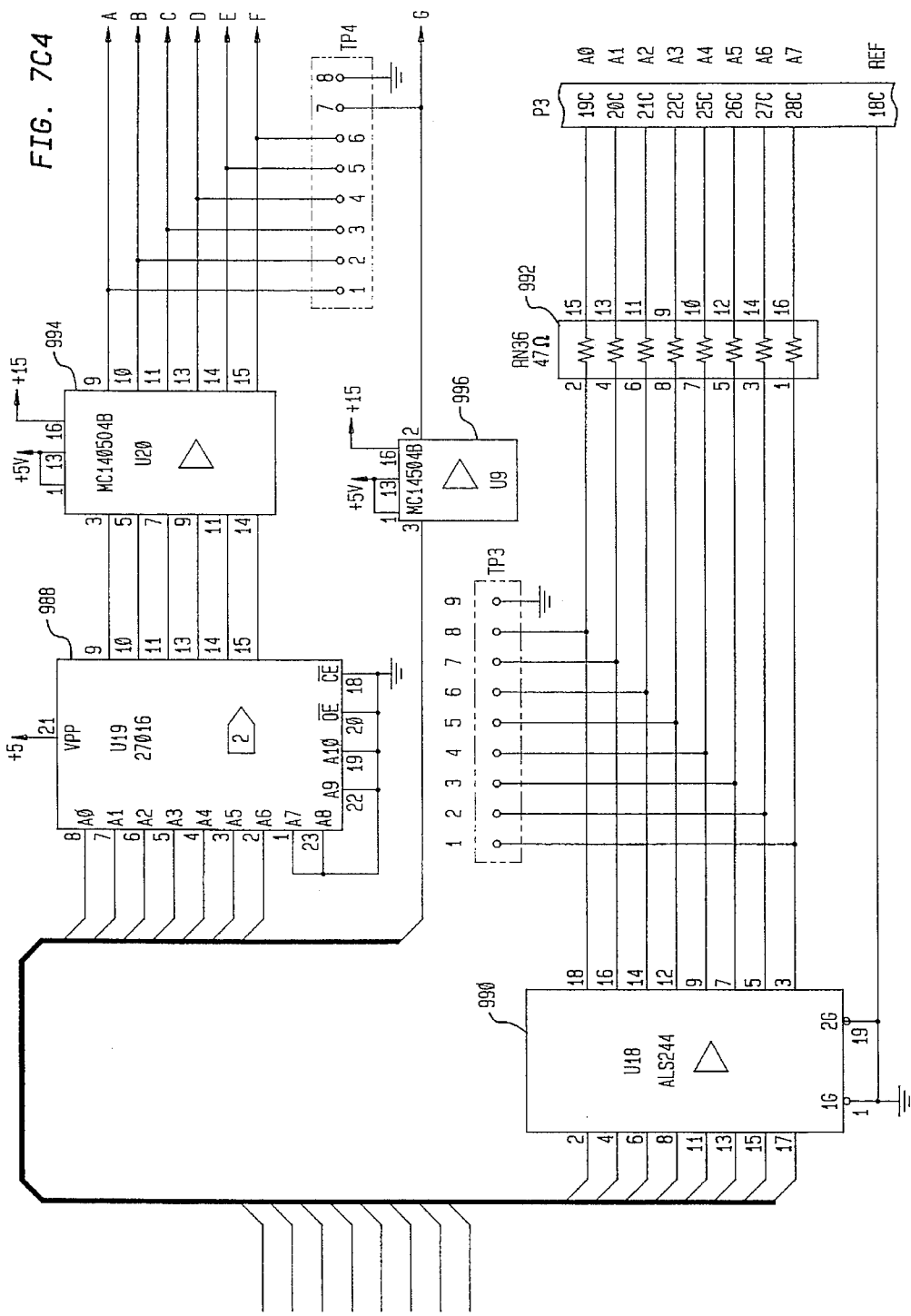

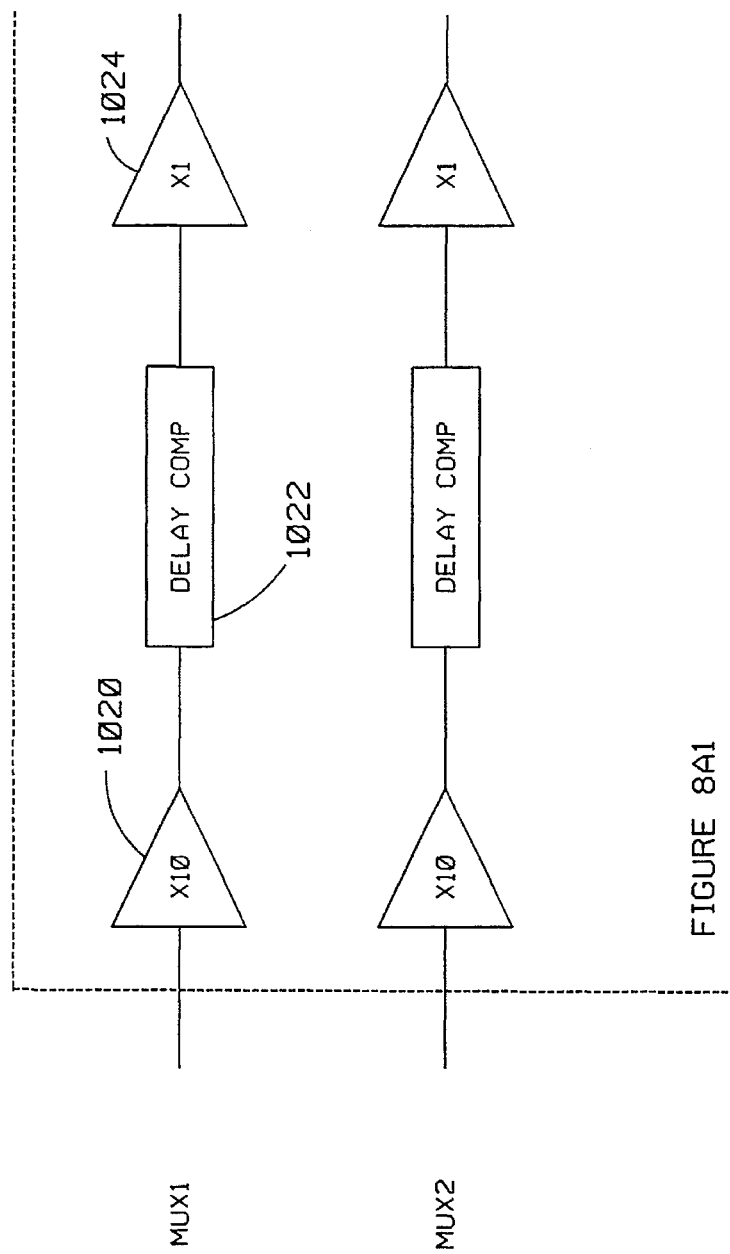

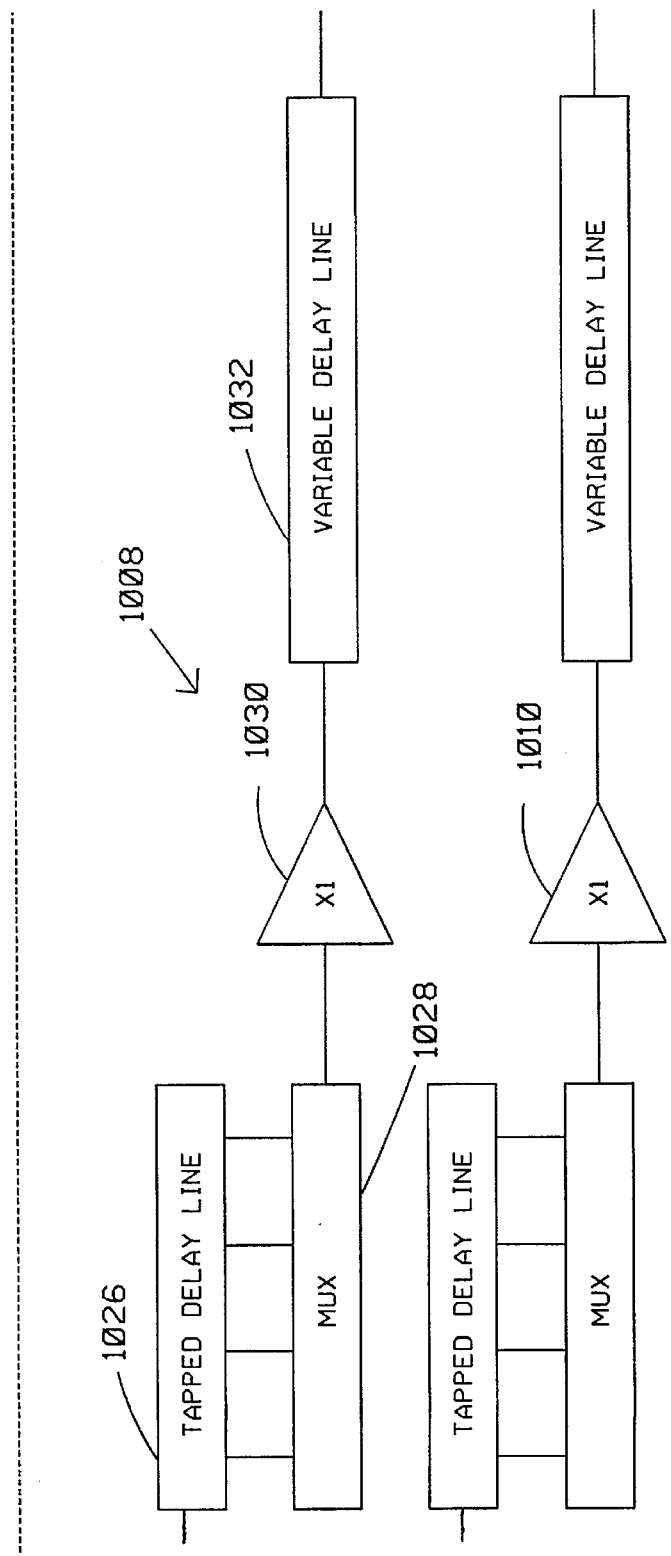

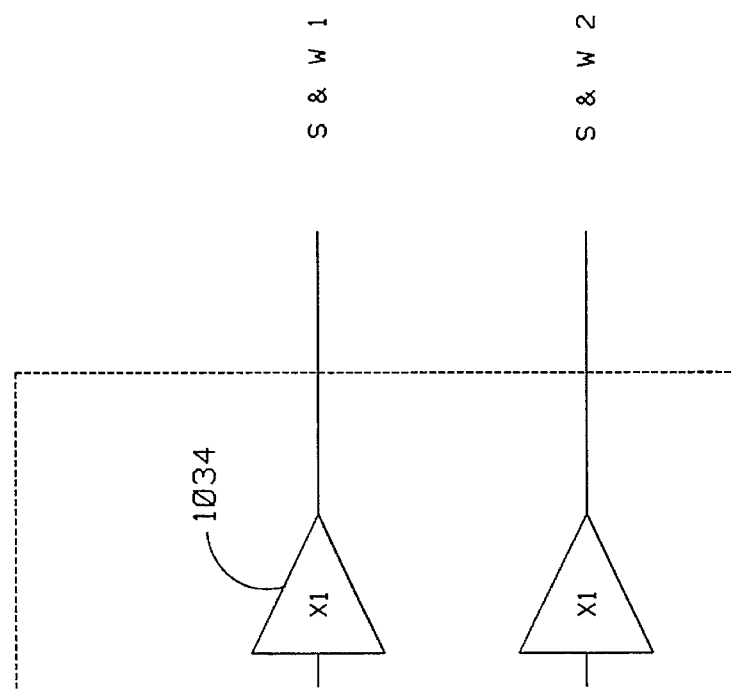
FIGURE 8A3

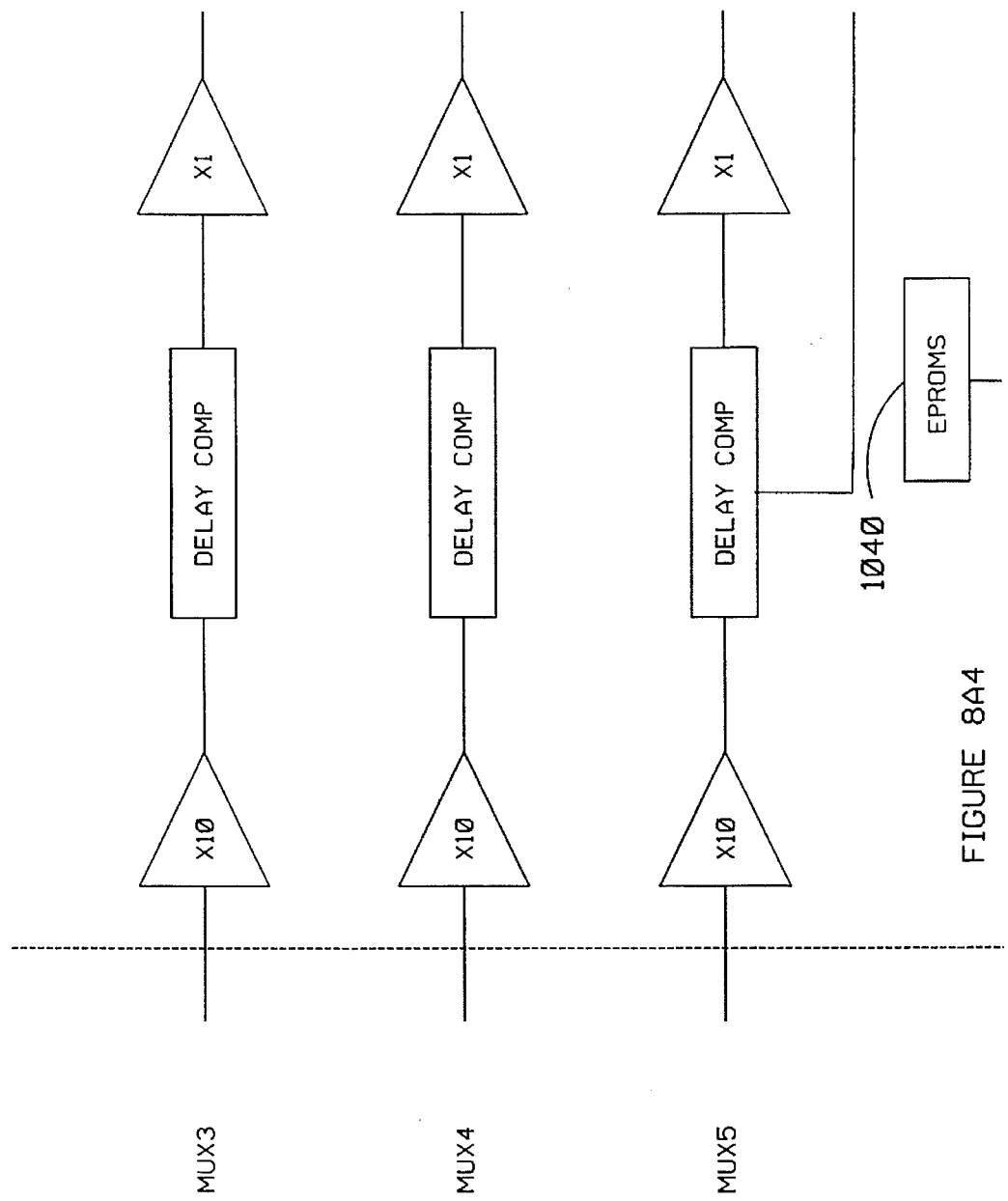
FIGURE 8A4

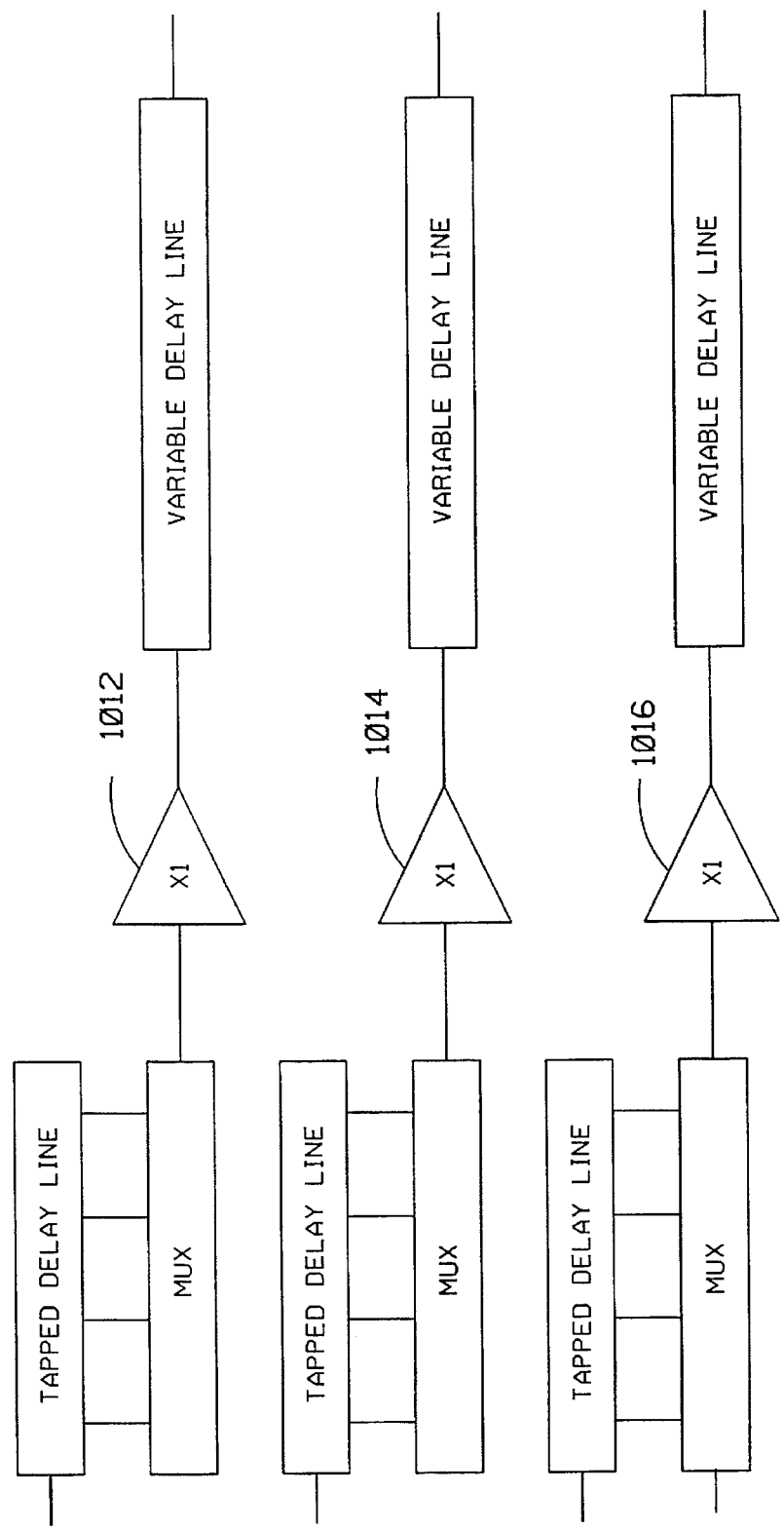
FIGURE 8A5

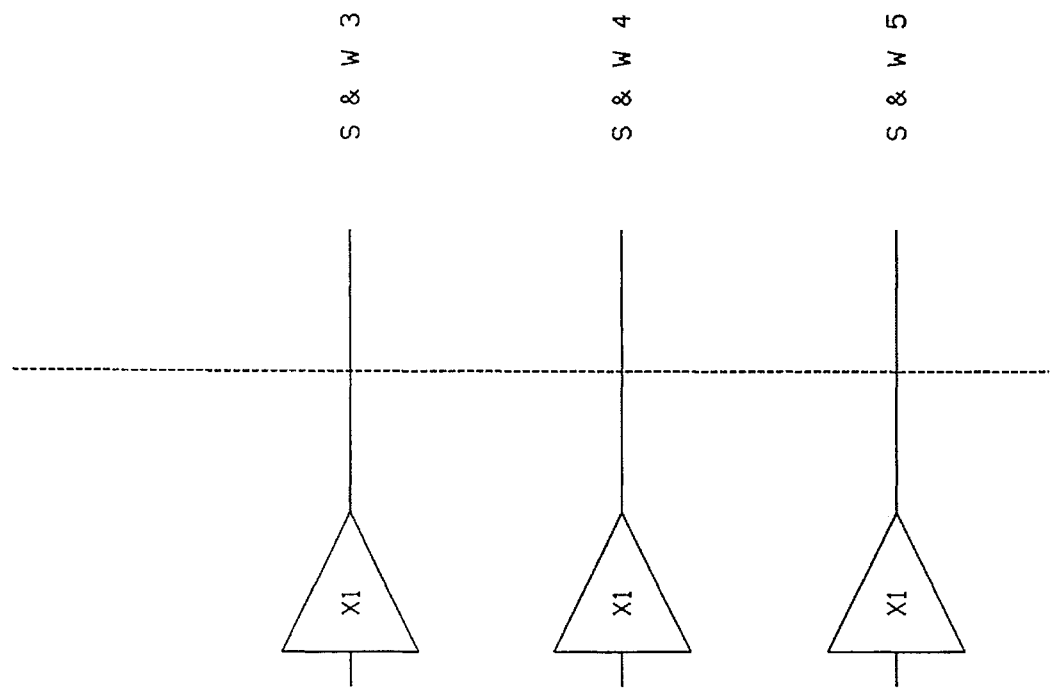

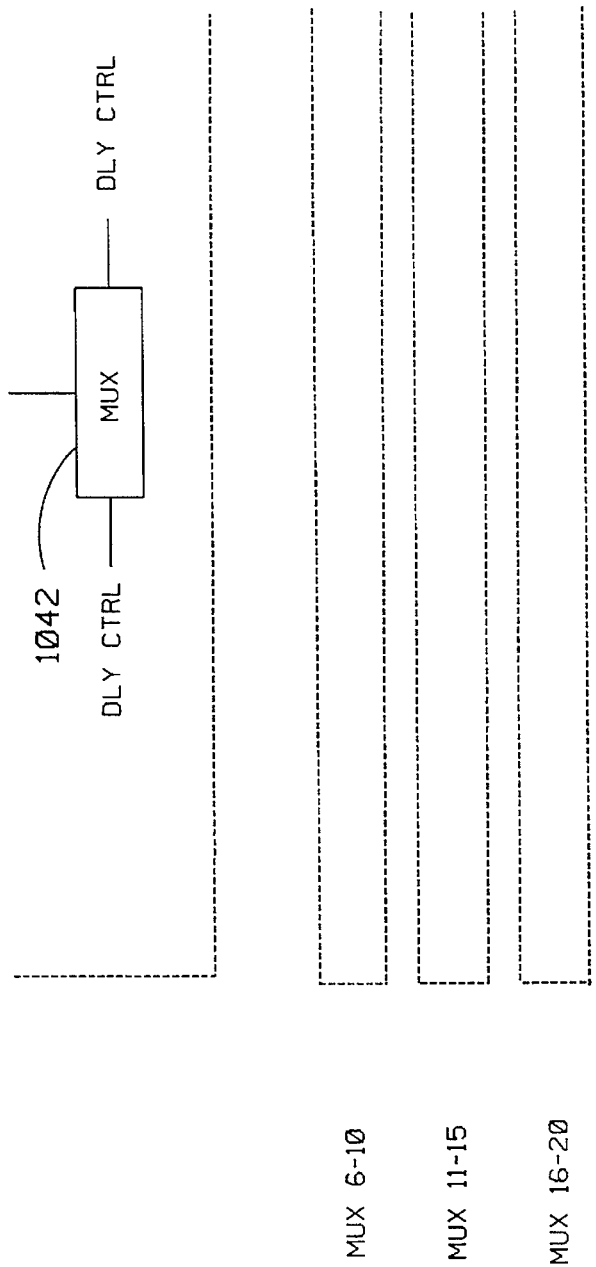
FIGURE 8A7

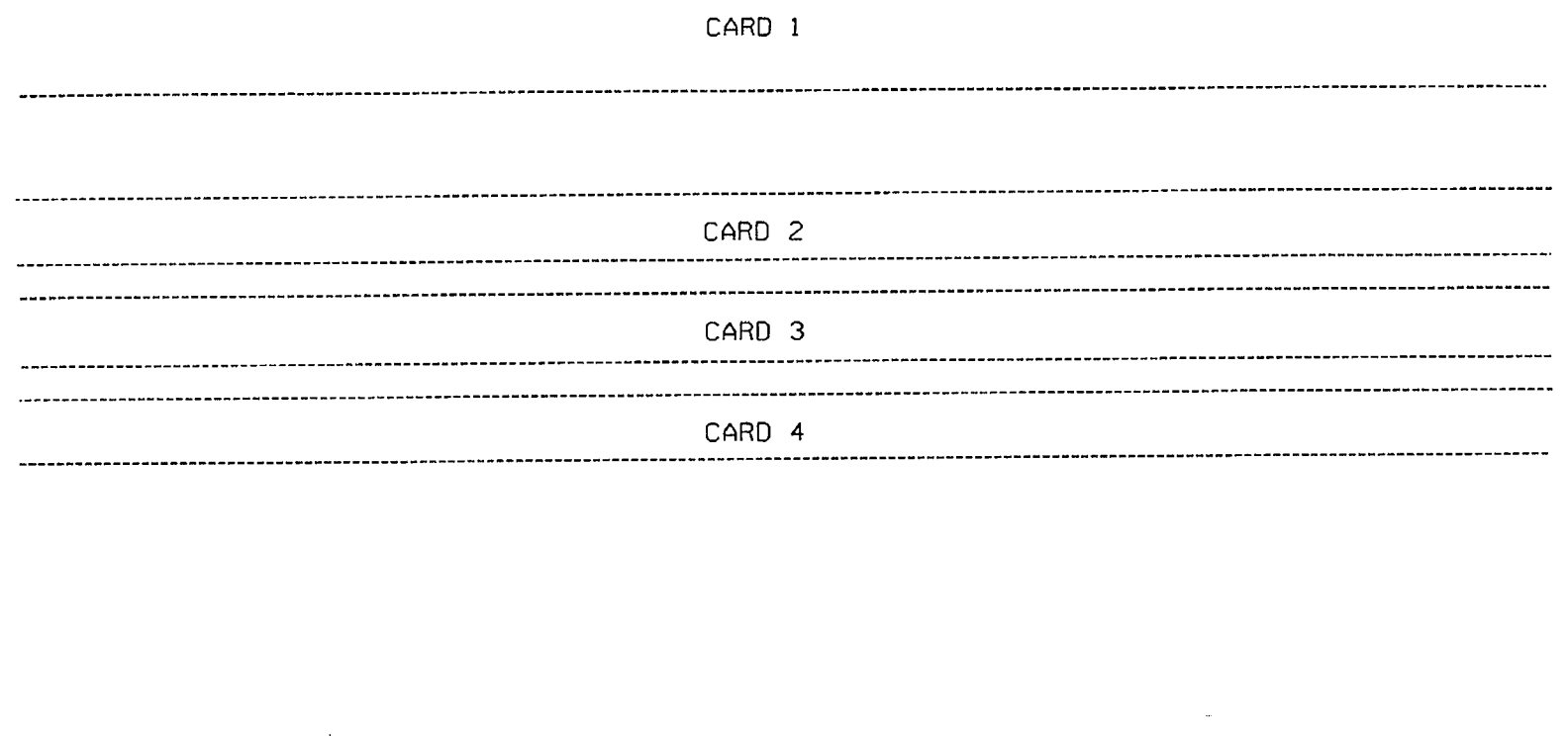

CARD 1

CARD 2

CARD 3

CARD 4

FIGURE 8A8

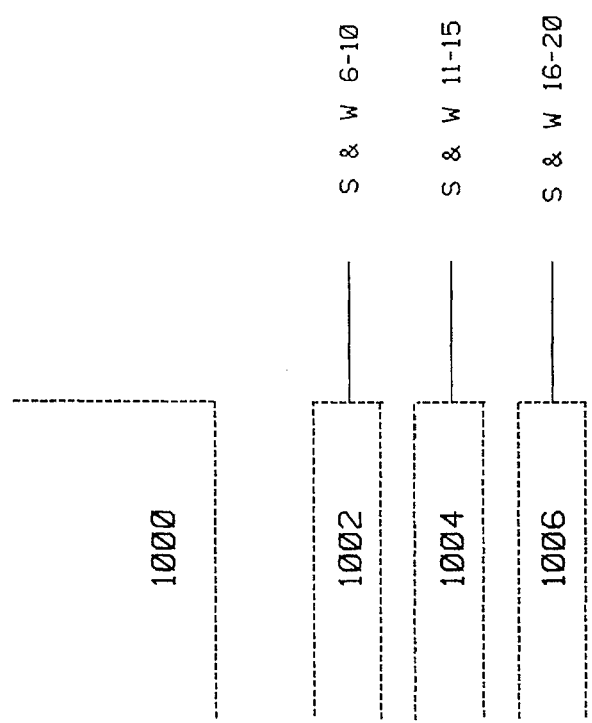
FIGURE 8A9

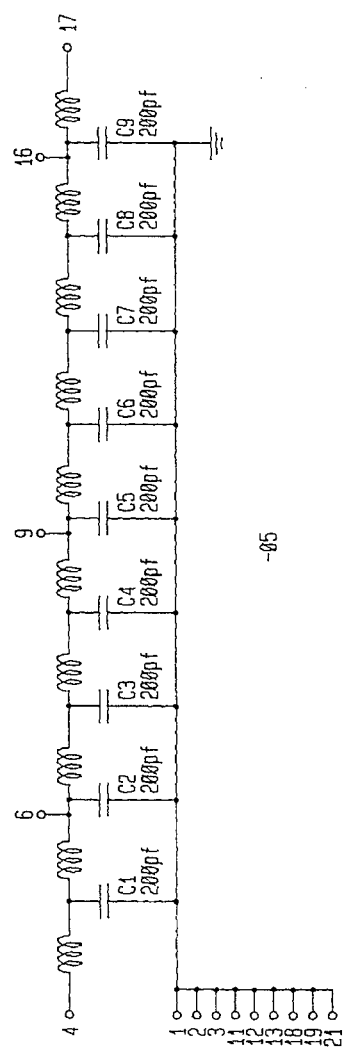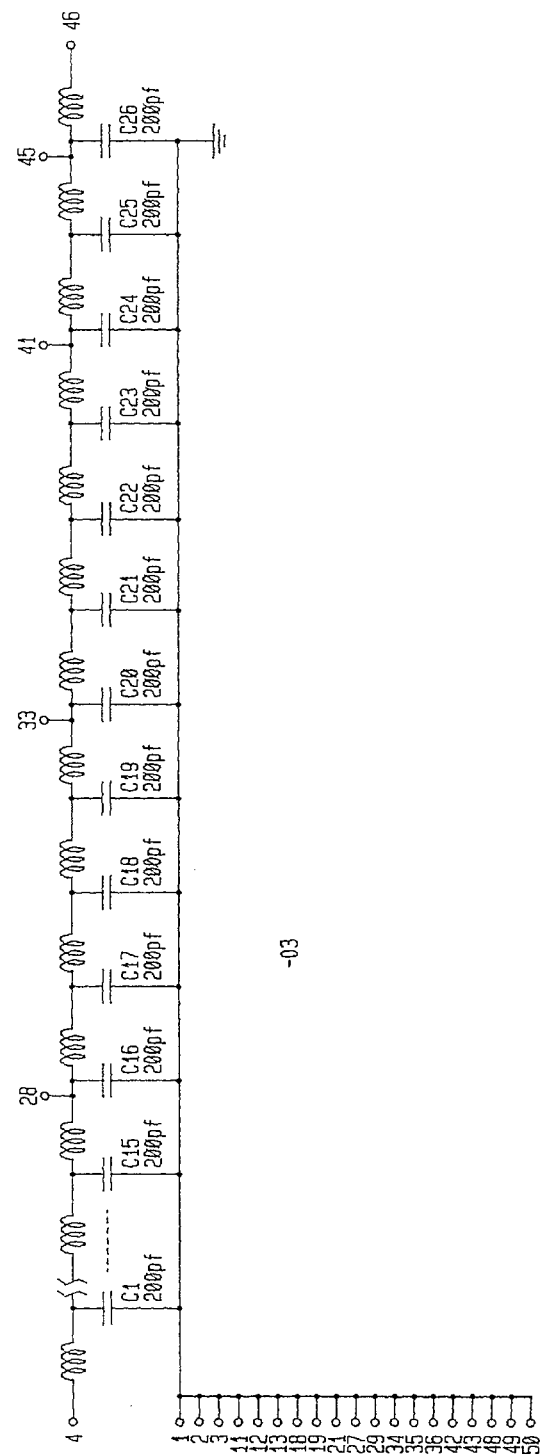
FIG. 8B1

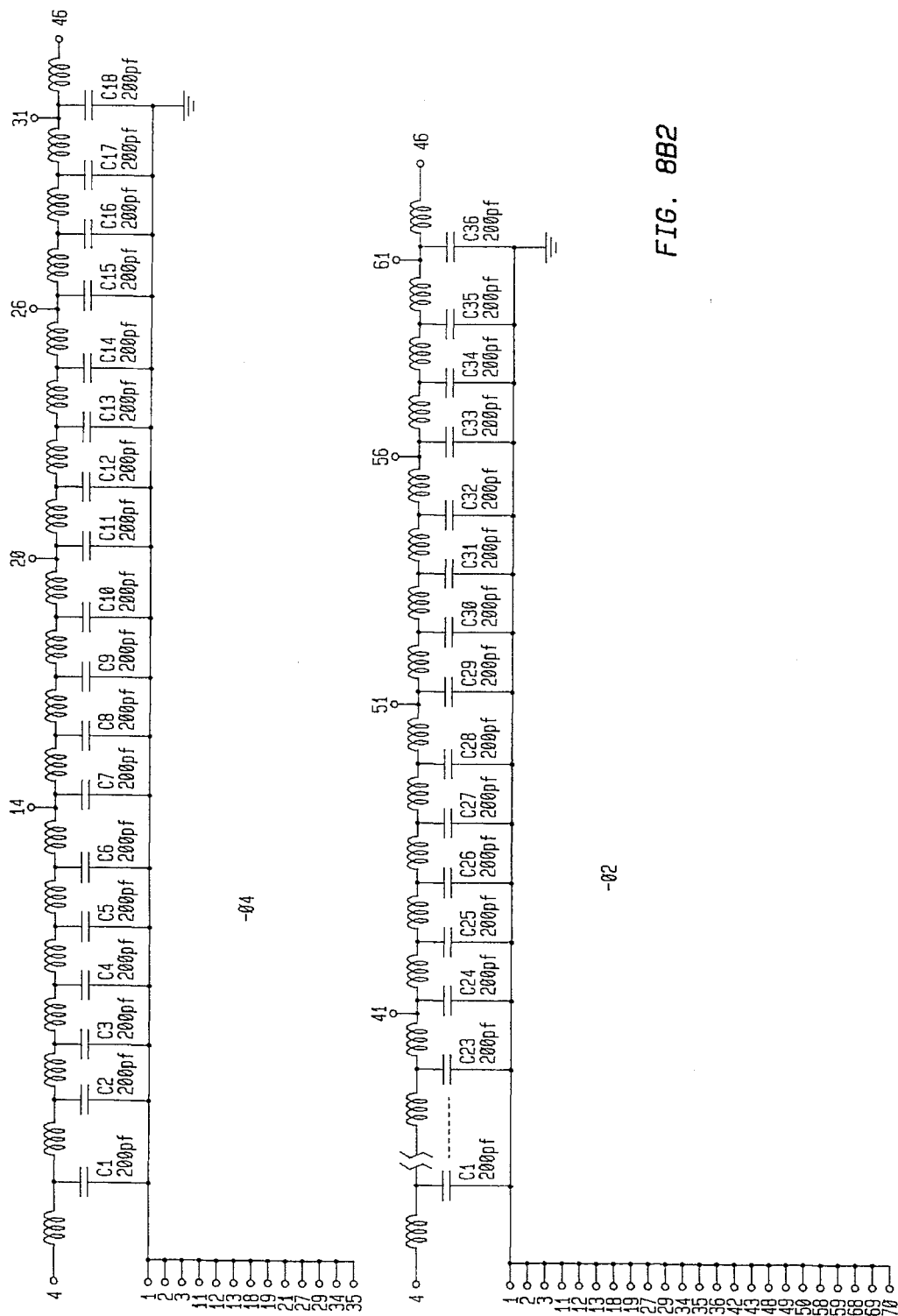
FIG. 8B2

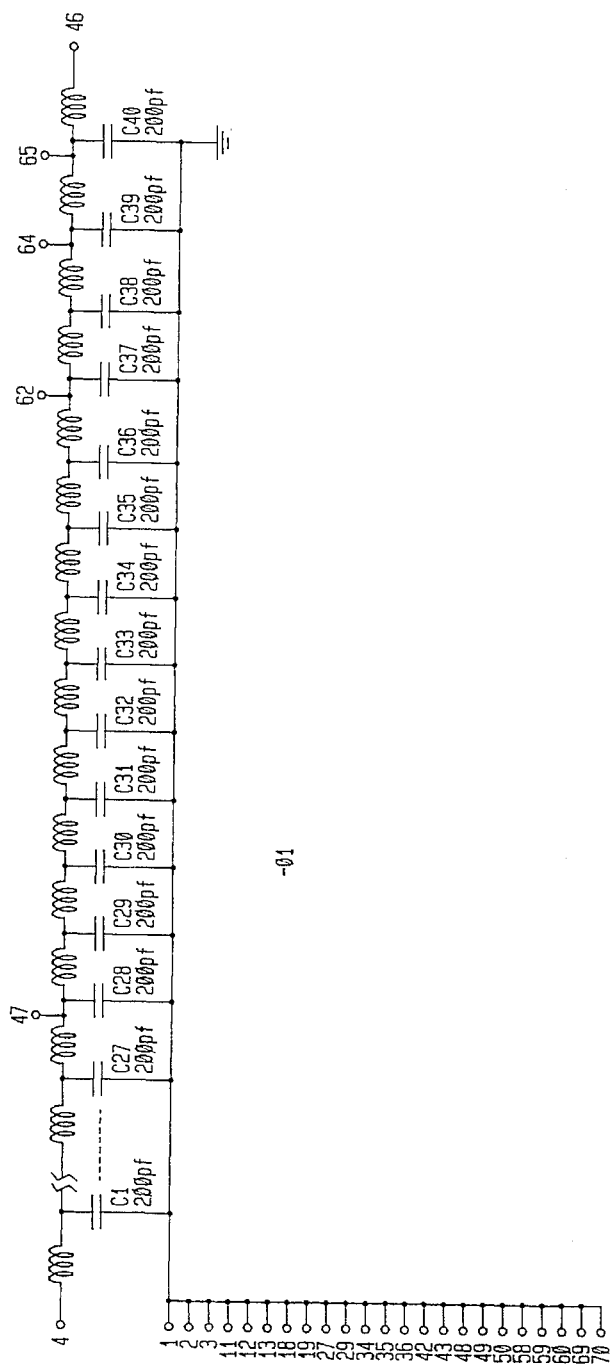
FIG. 8B3

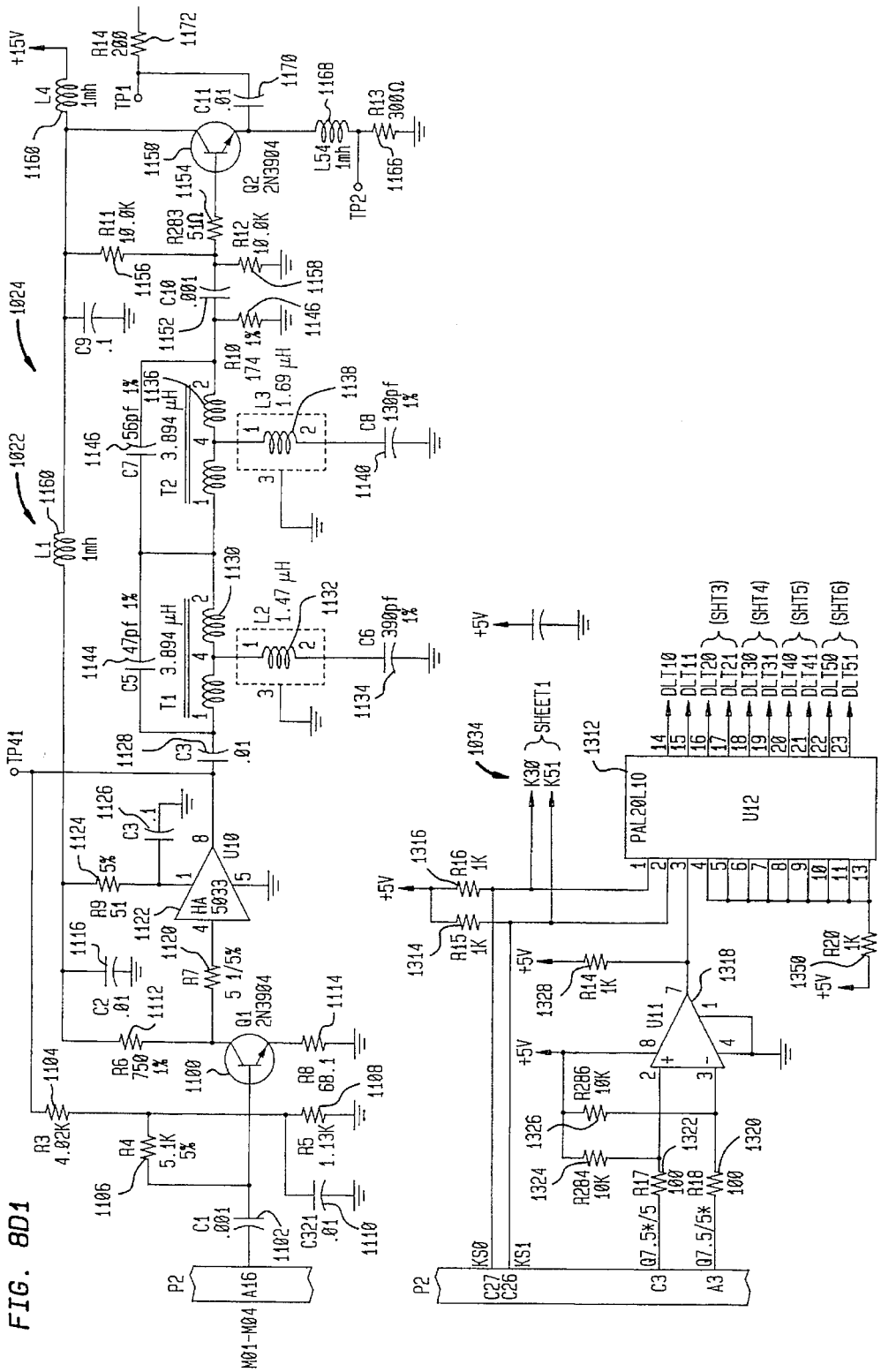
FIG. 8D1

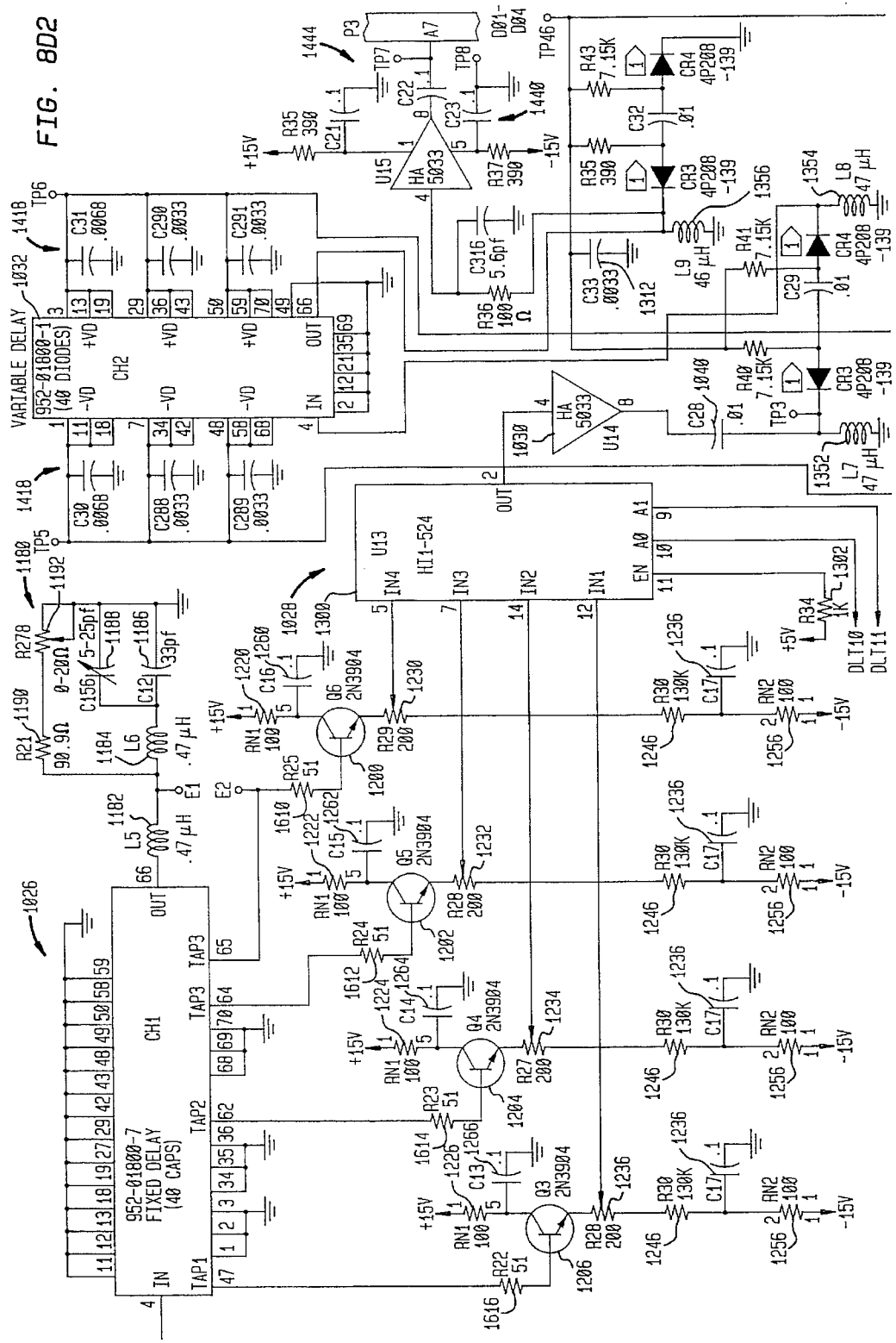
FIG. 8D2

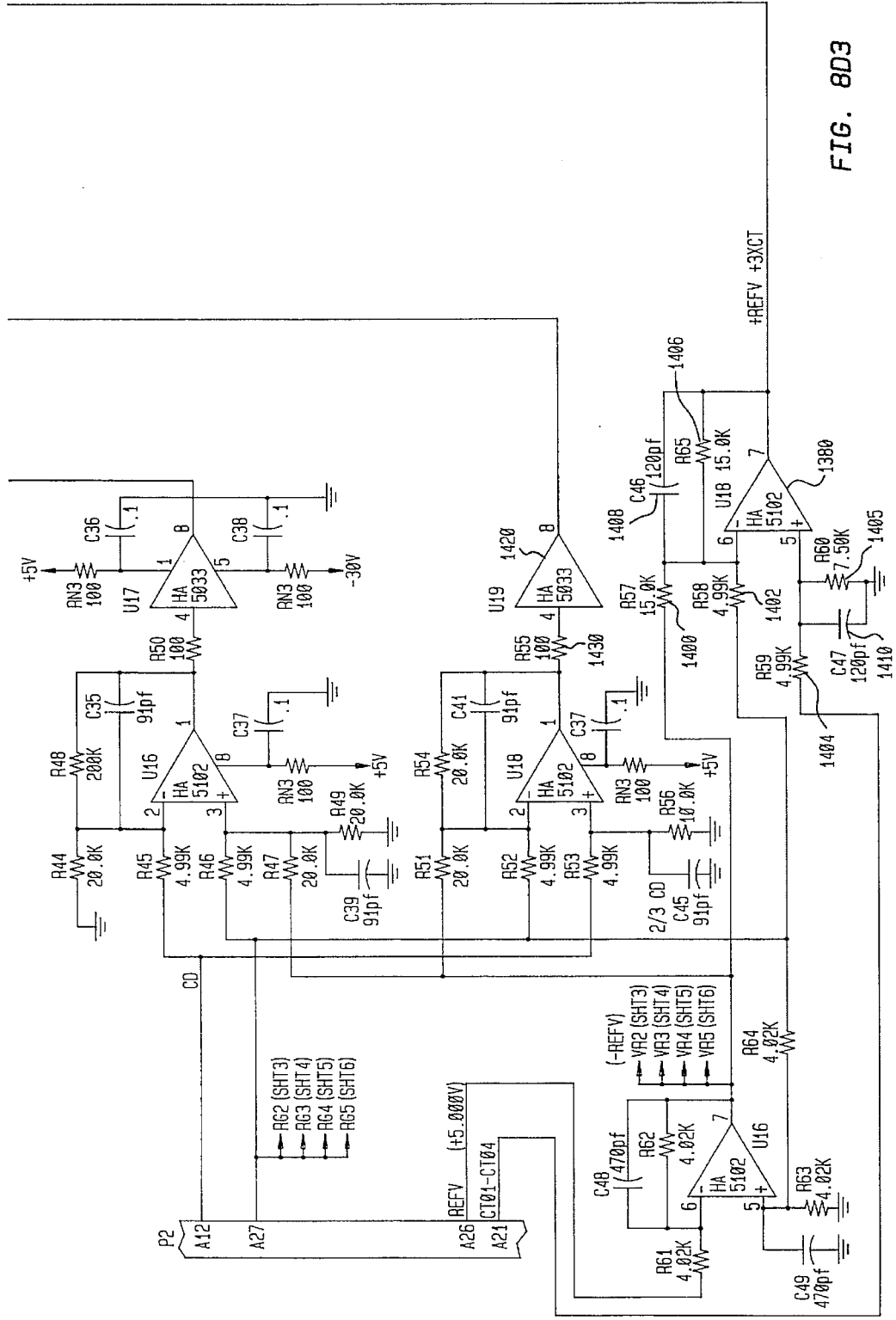
FIG. 8D3

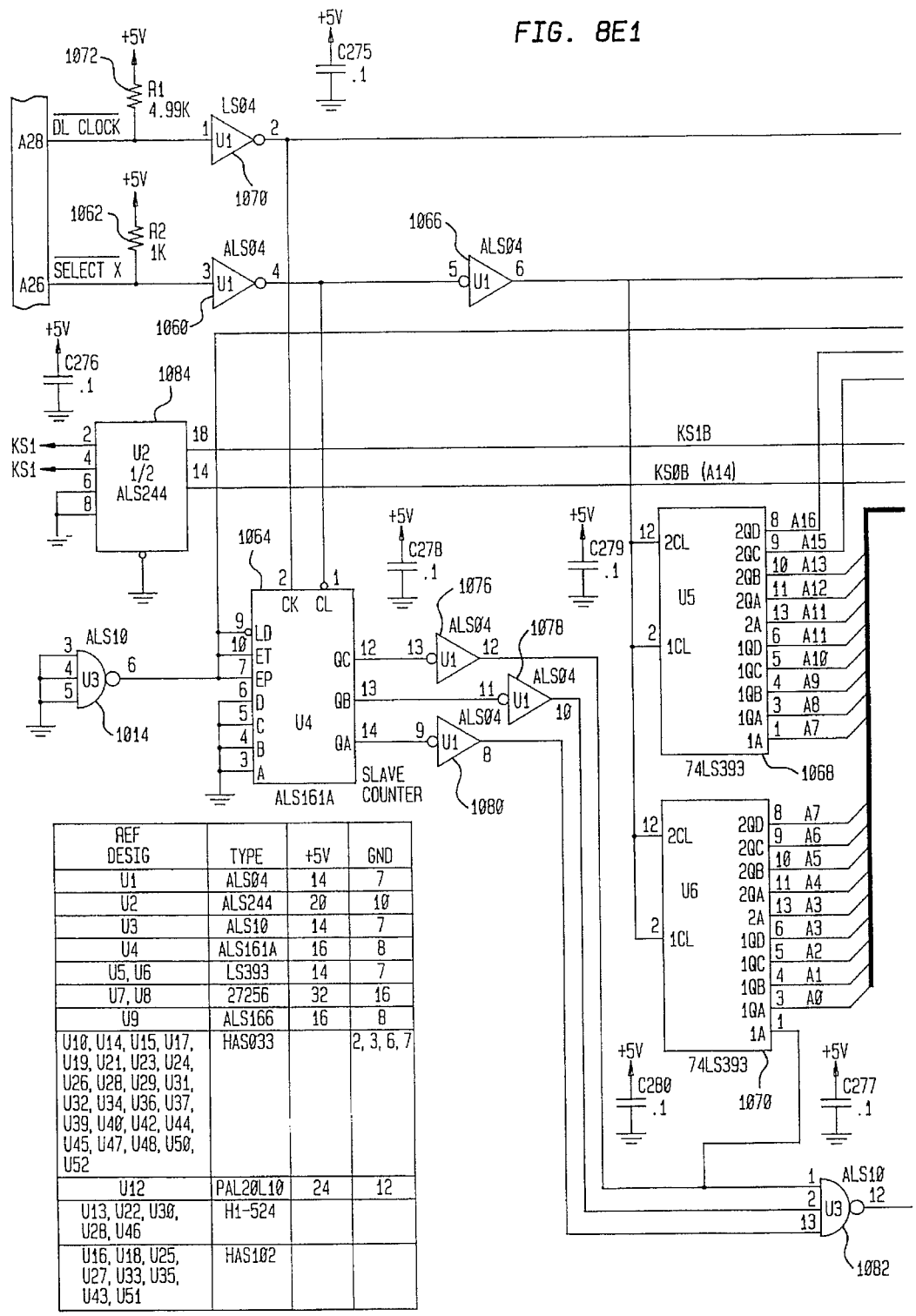
FIG. 8E1

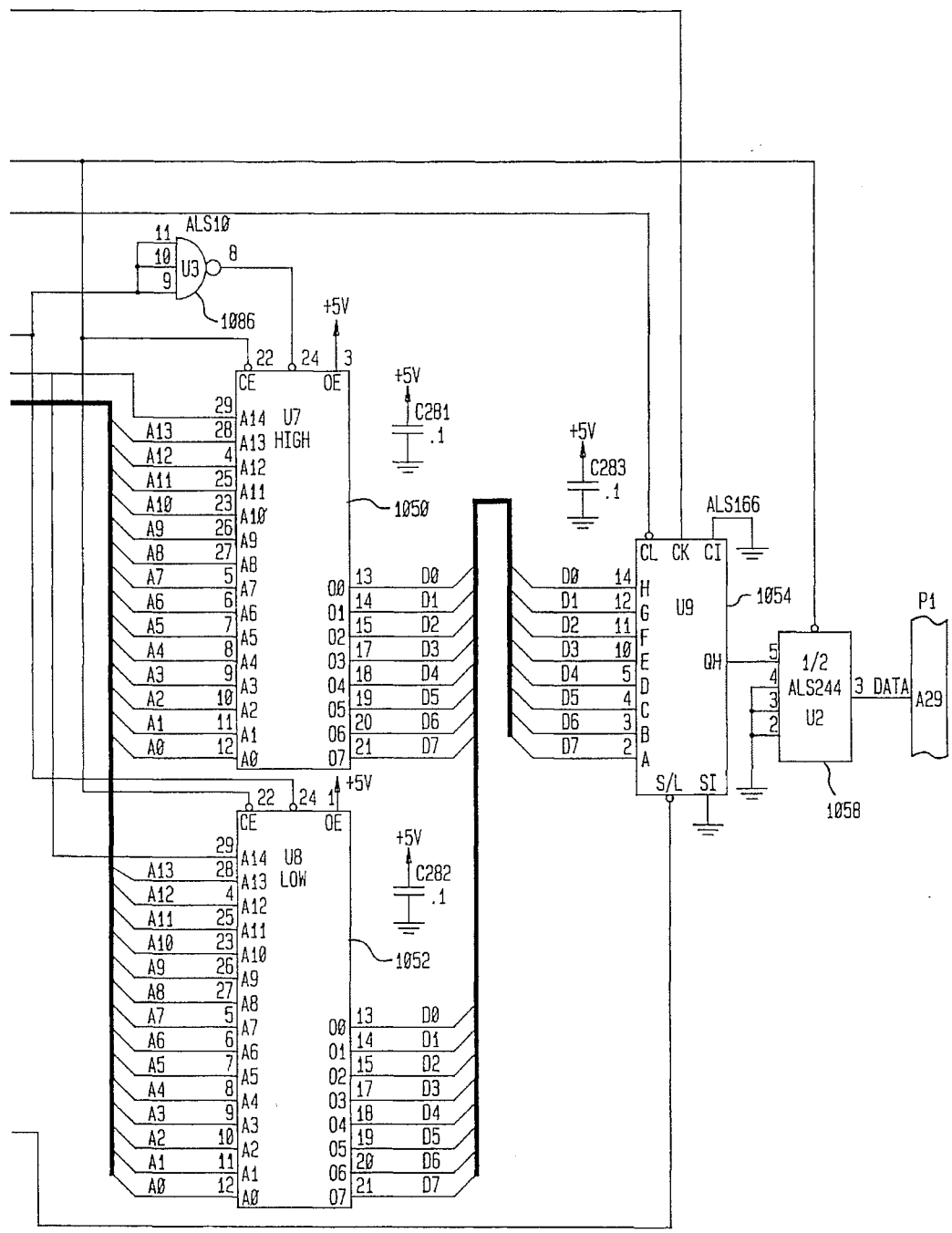
FIG. 8E2

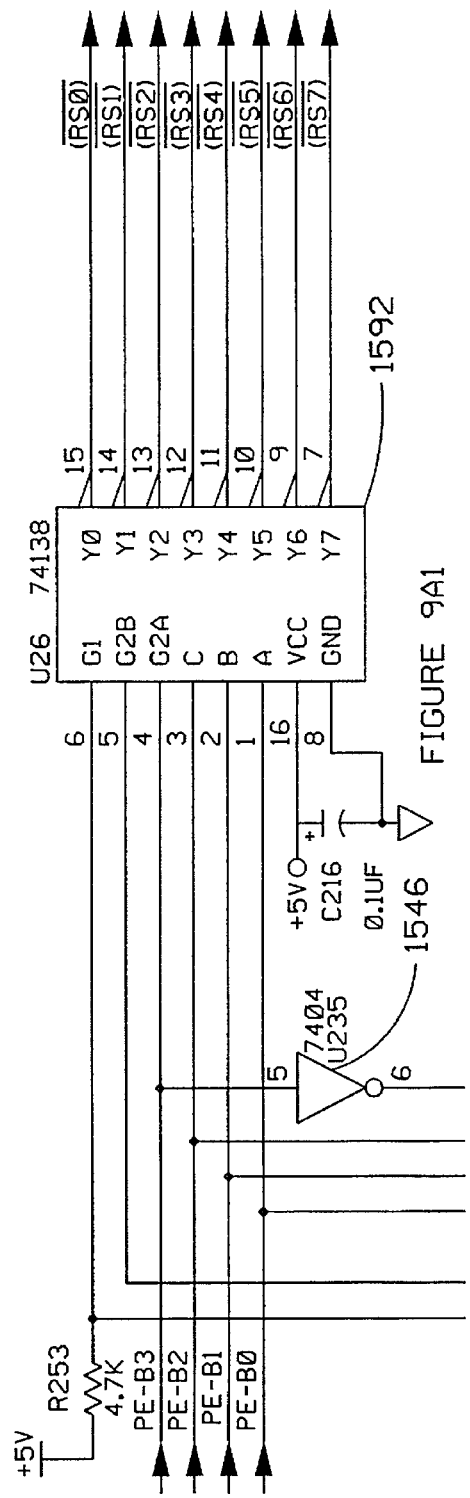
FIGURE 9A1

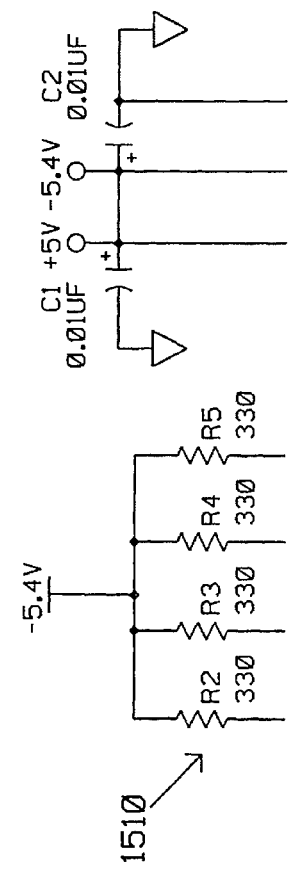
FIGURE 9A2

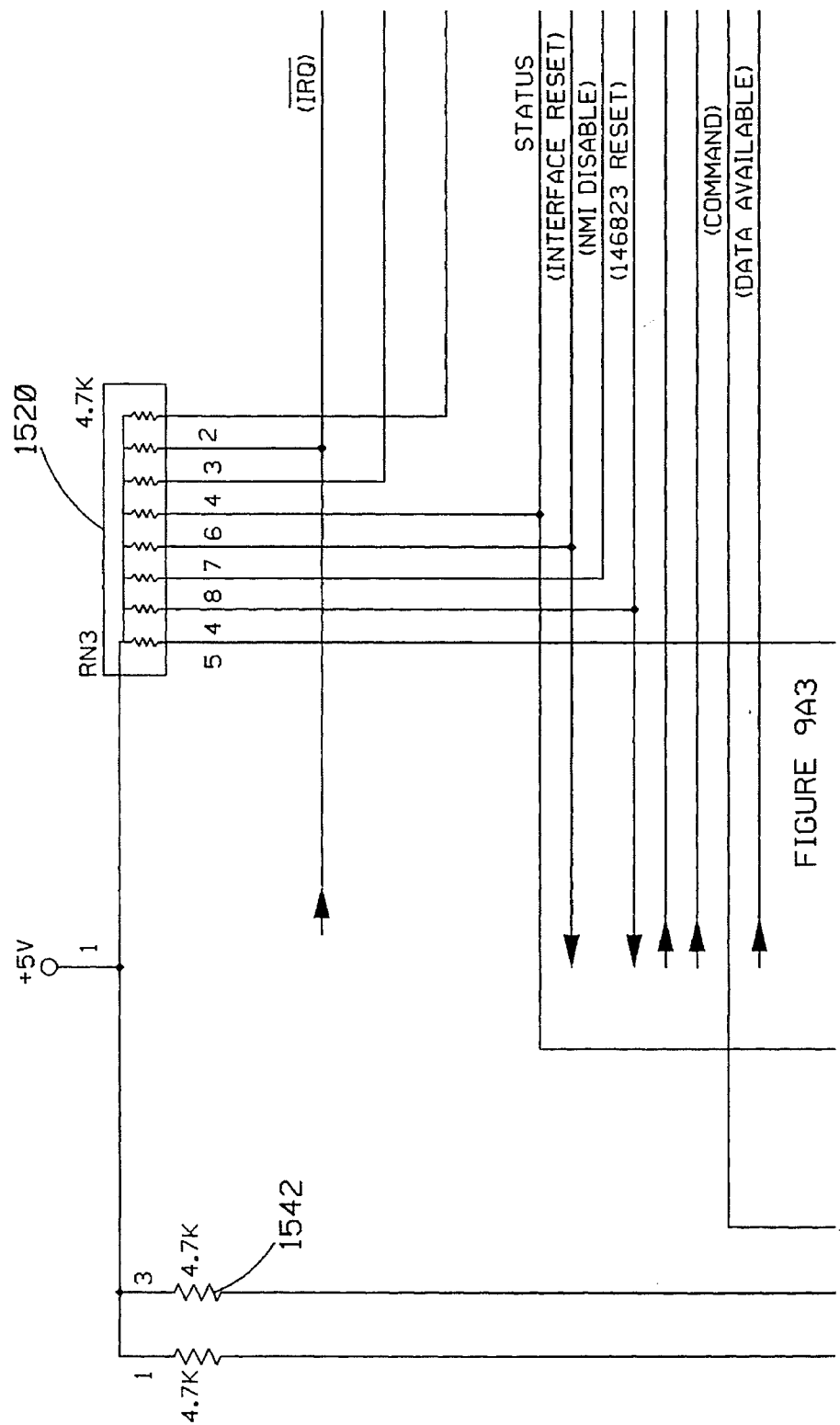
FIGURE 9A3

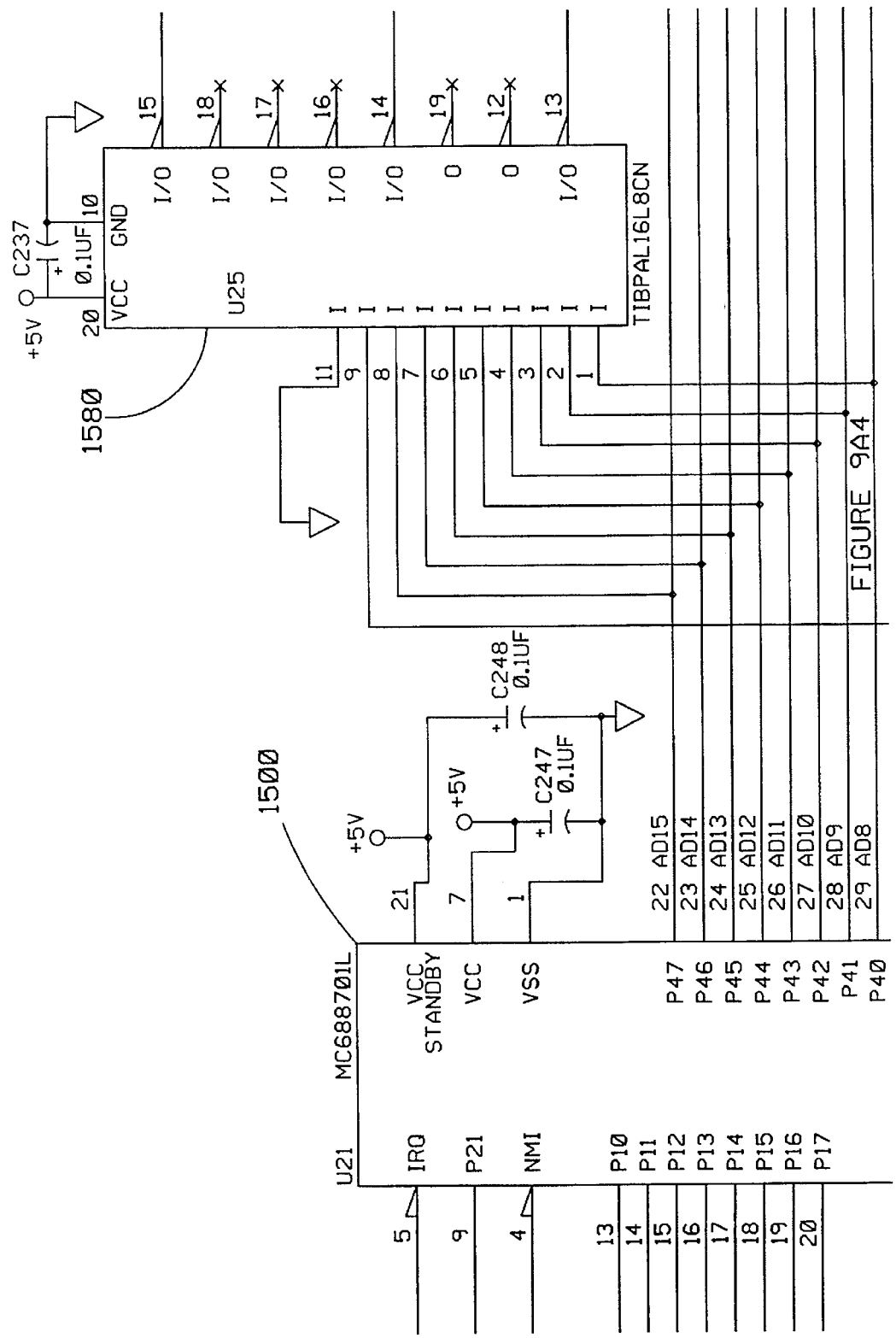

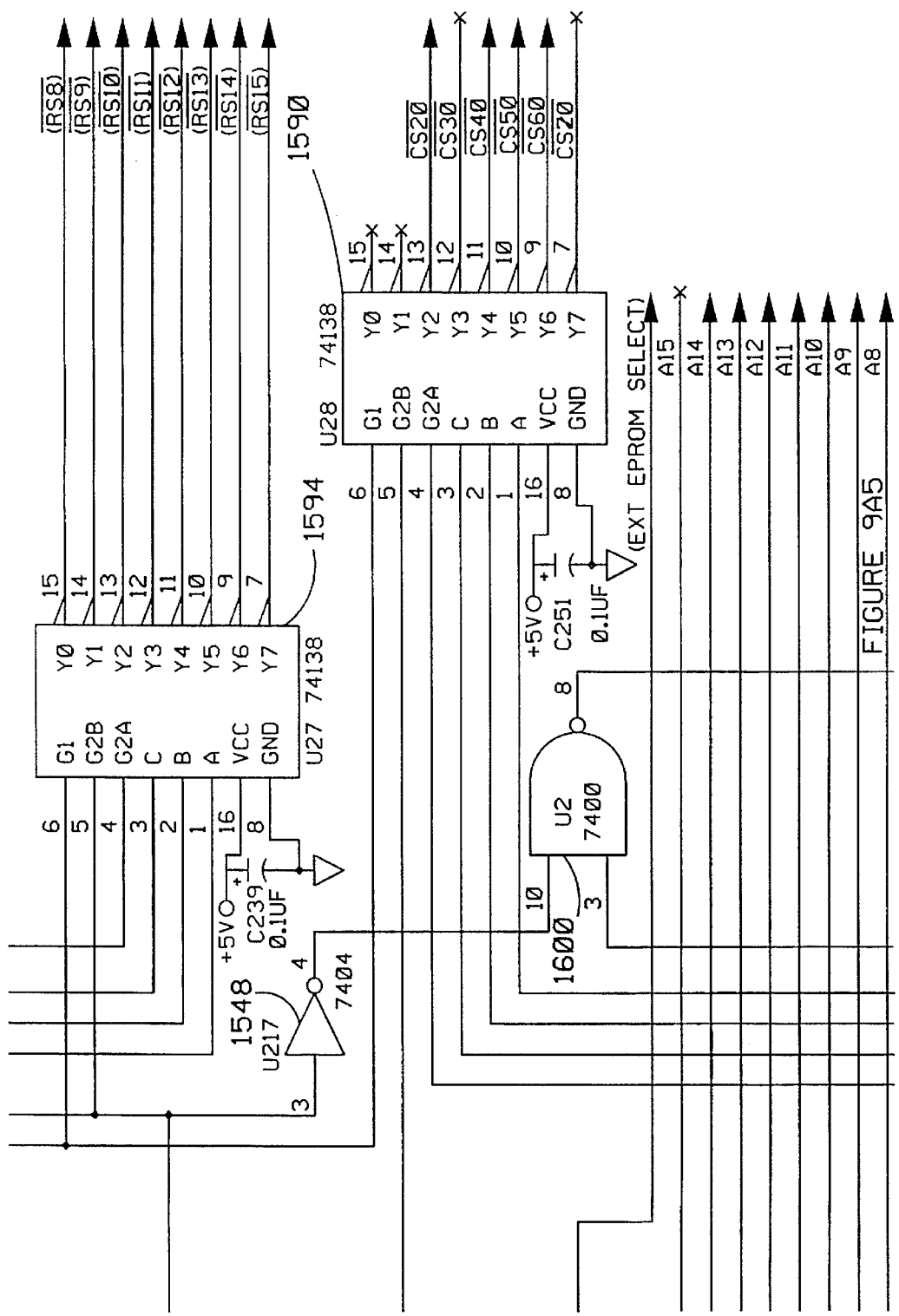
FIGURE 9A5

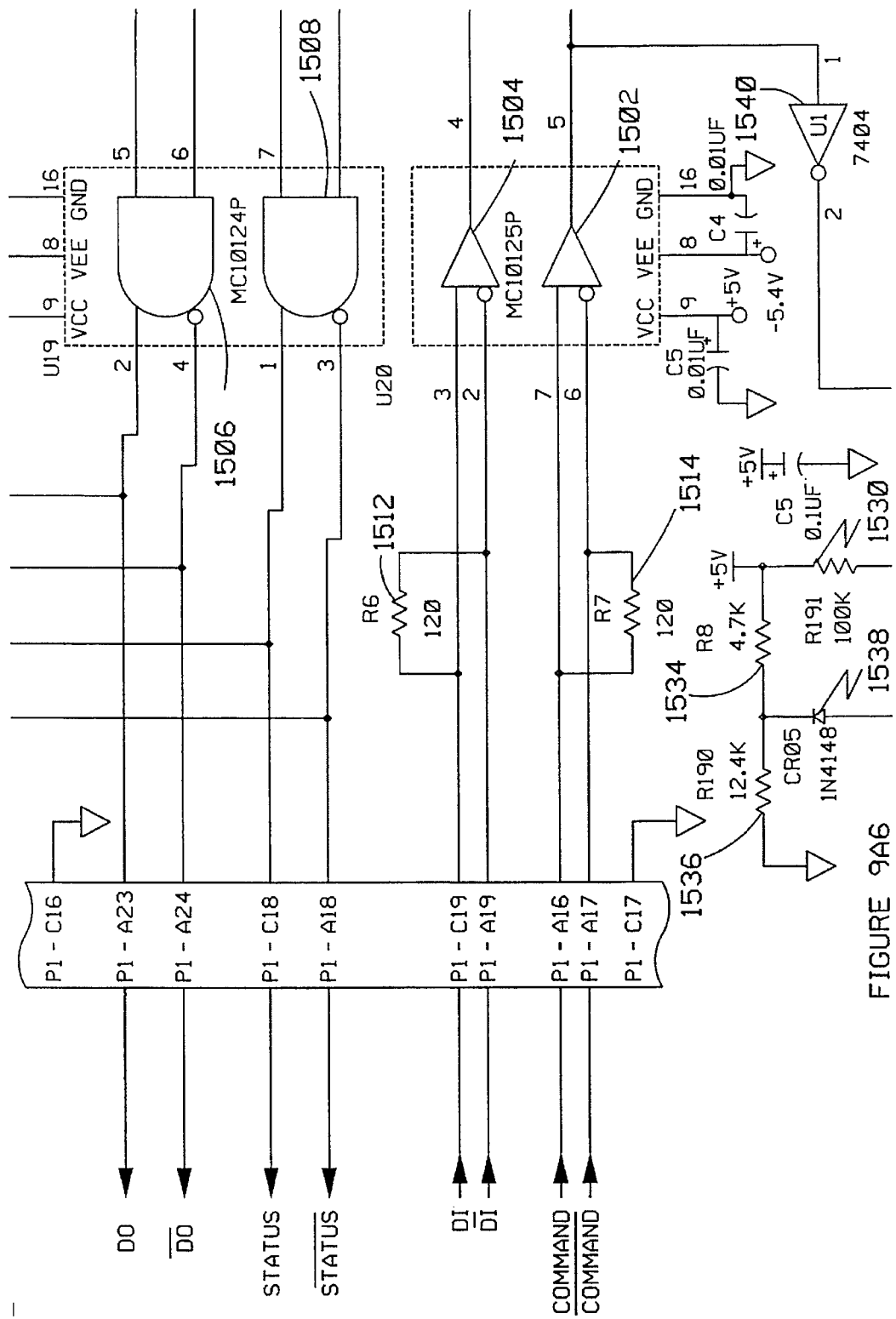
FIGURE 9A6

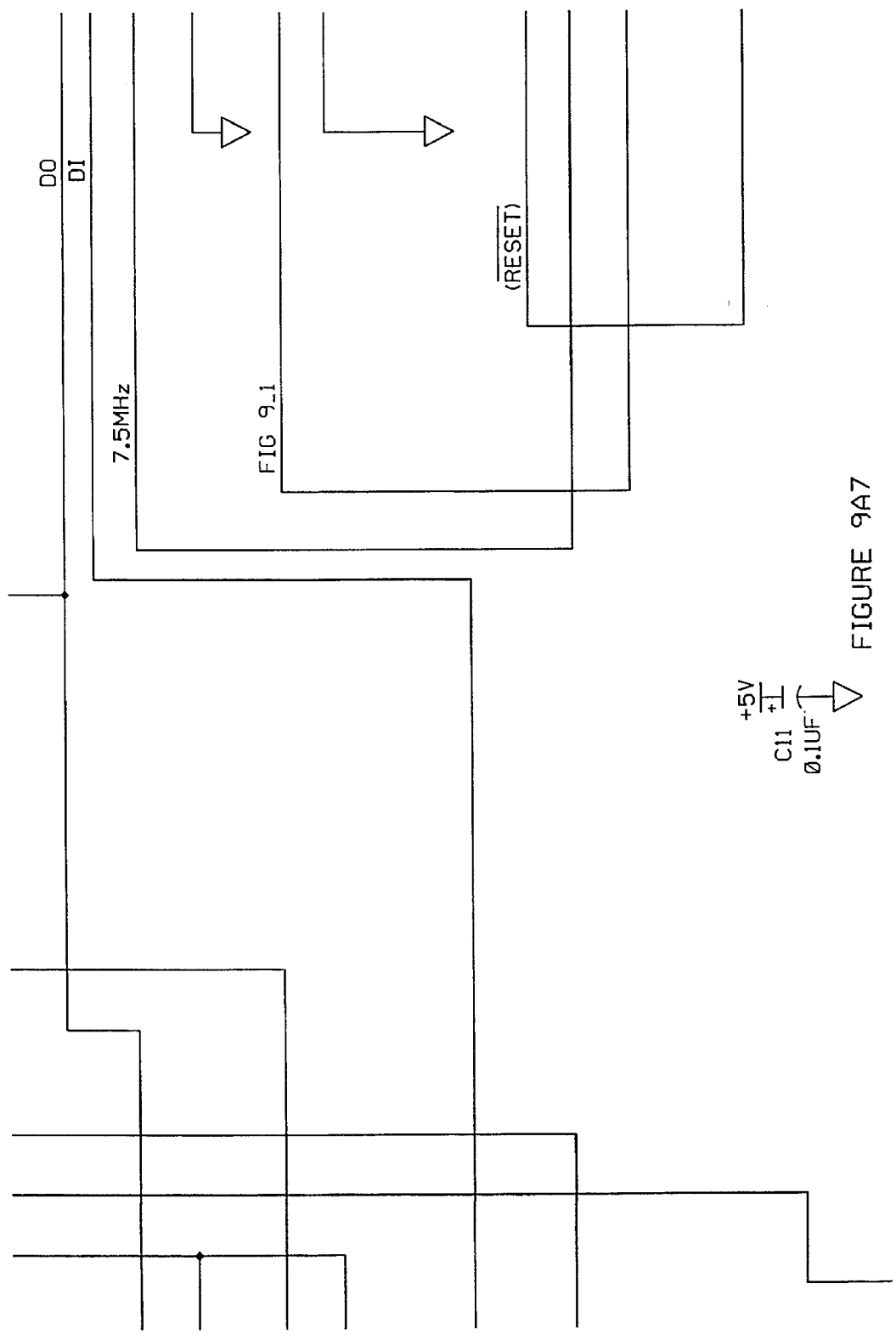
FIGURE 9A7

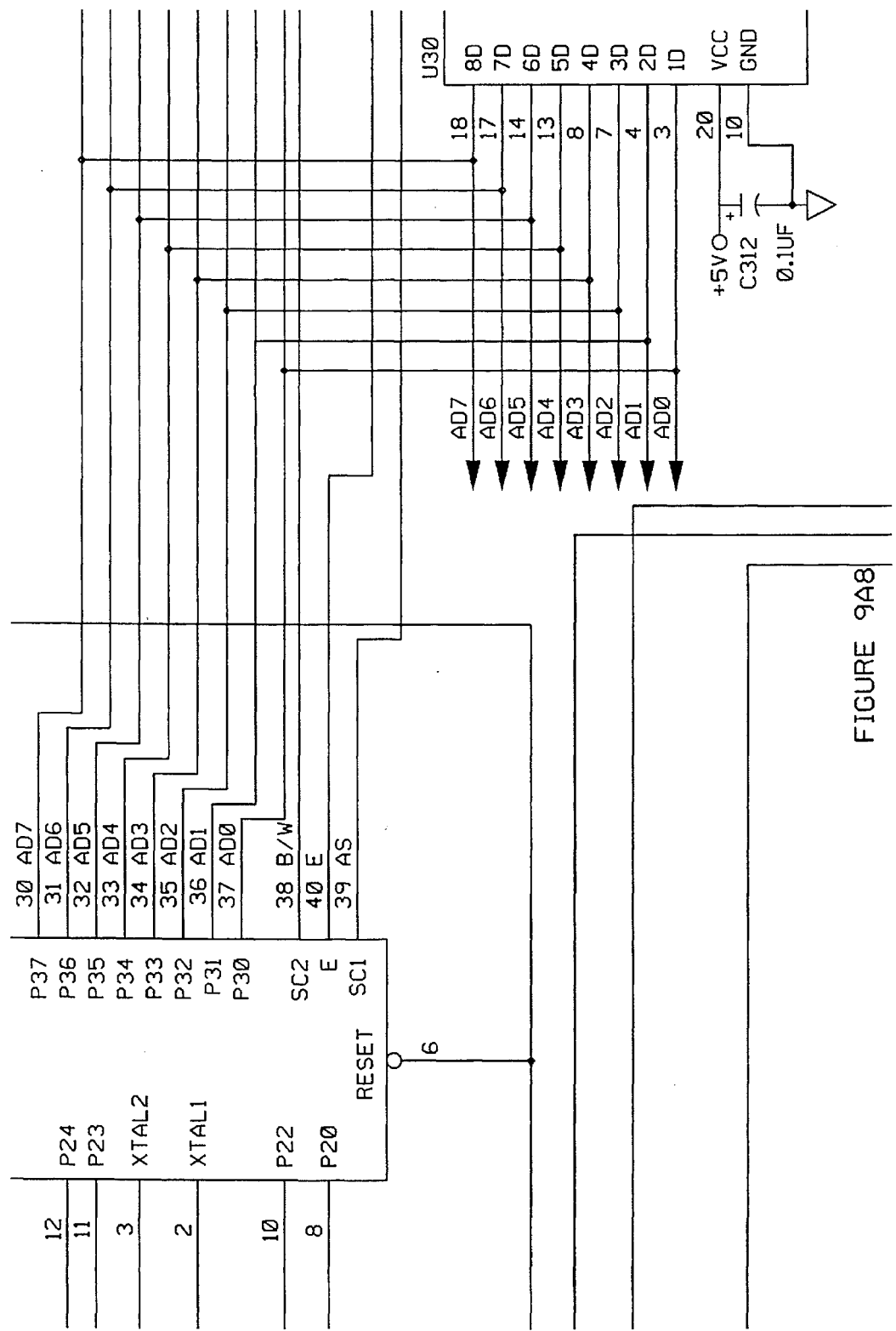
FIGURE 9A8

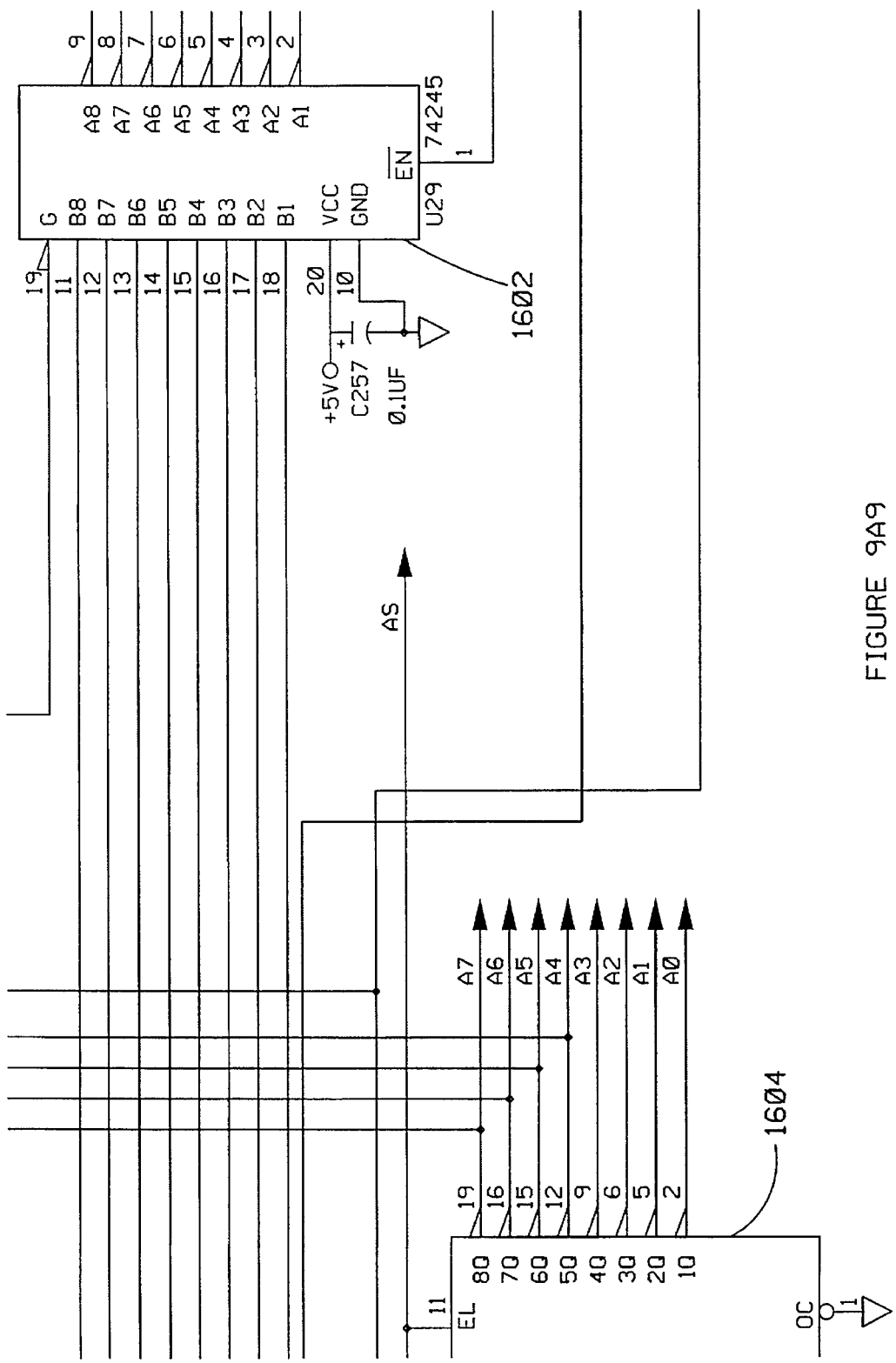
FIGURE 9A9

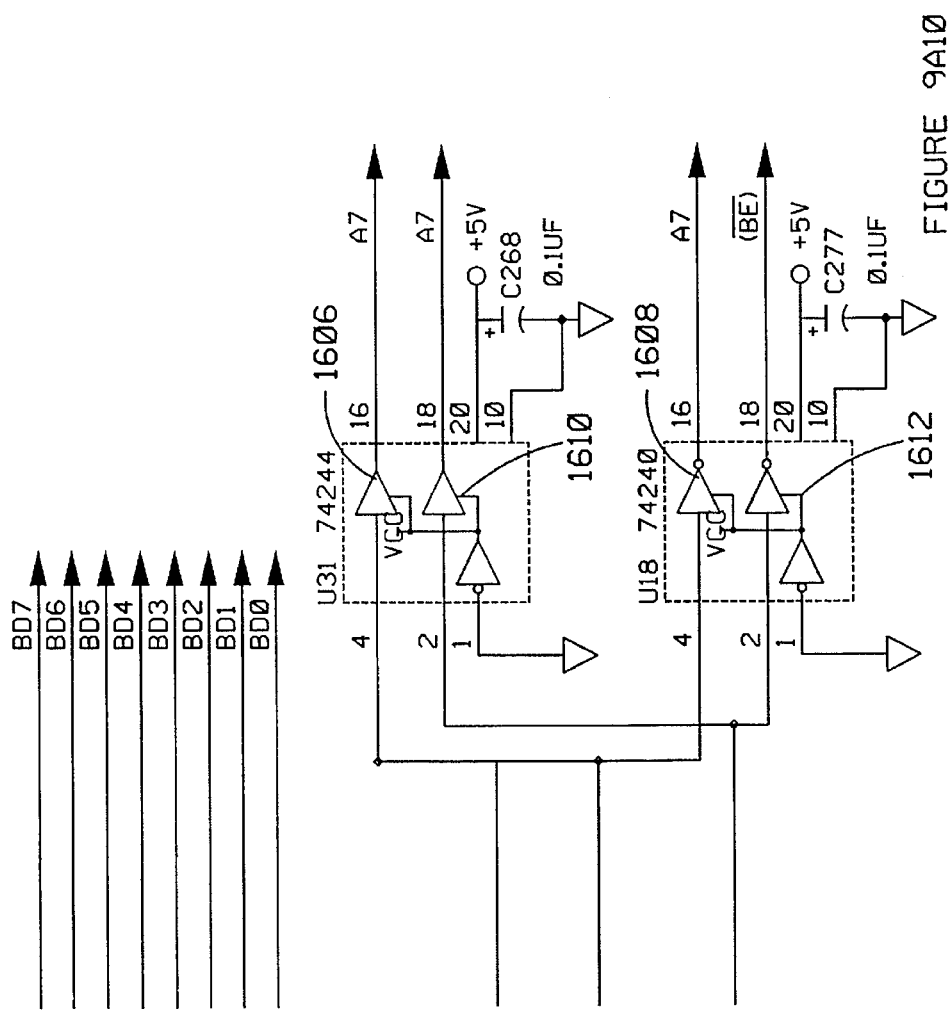

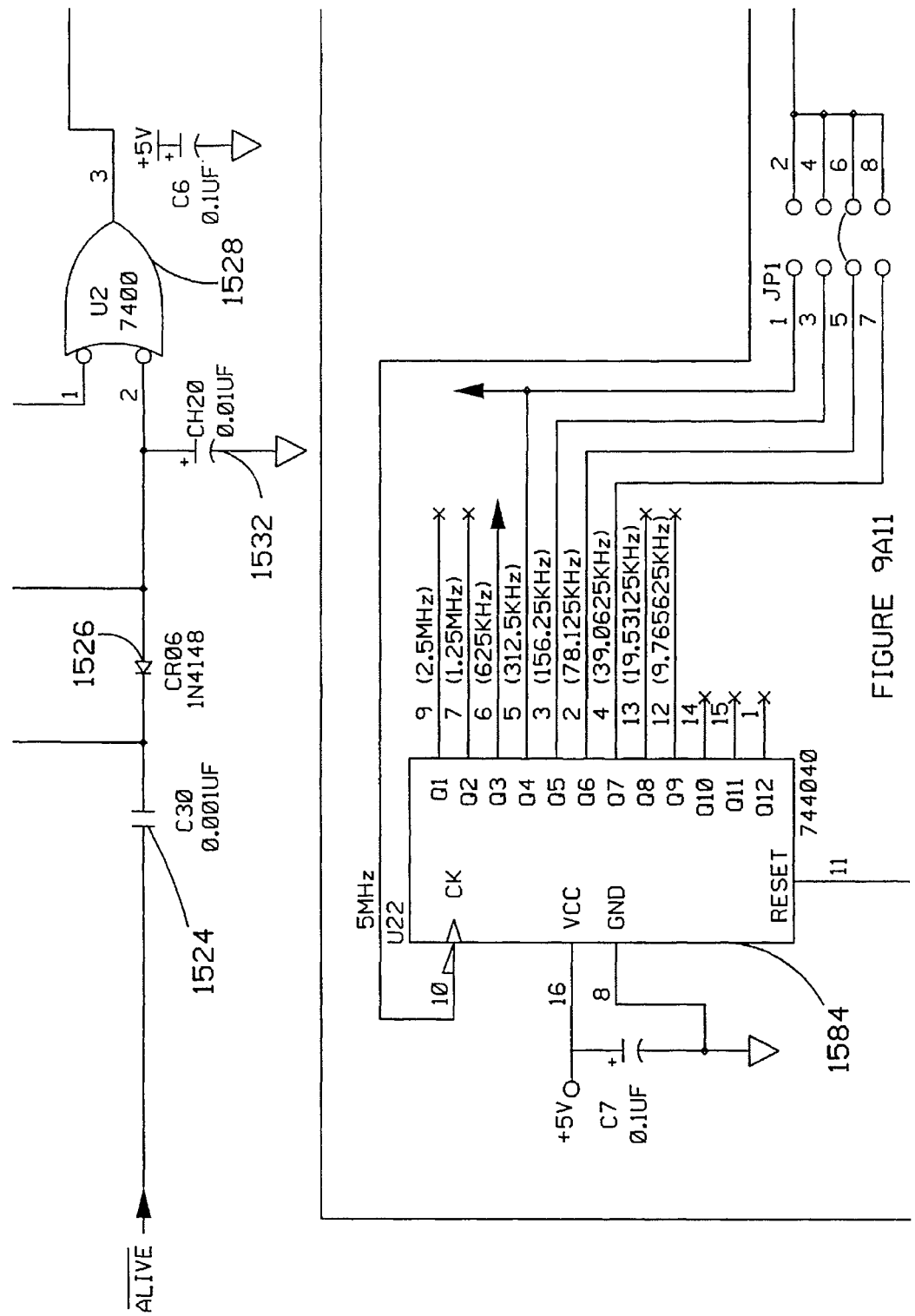
FIGURE 9A11

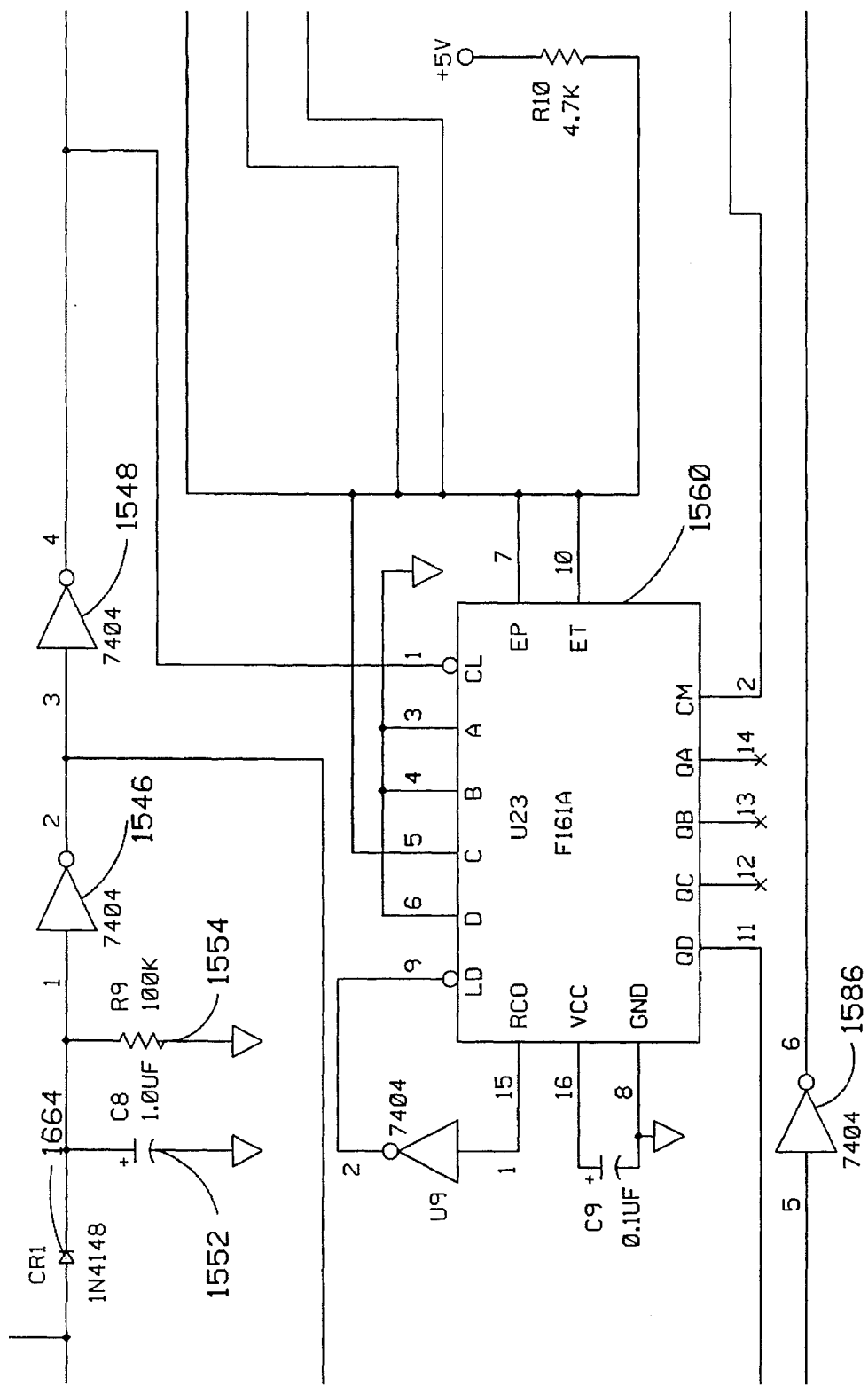
FIGURE 9A12

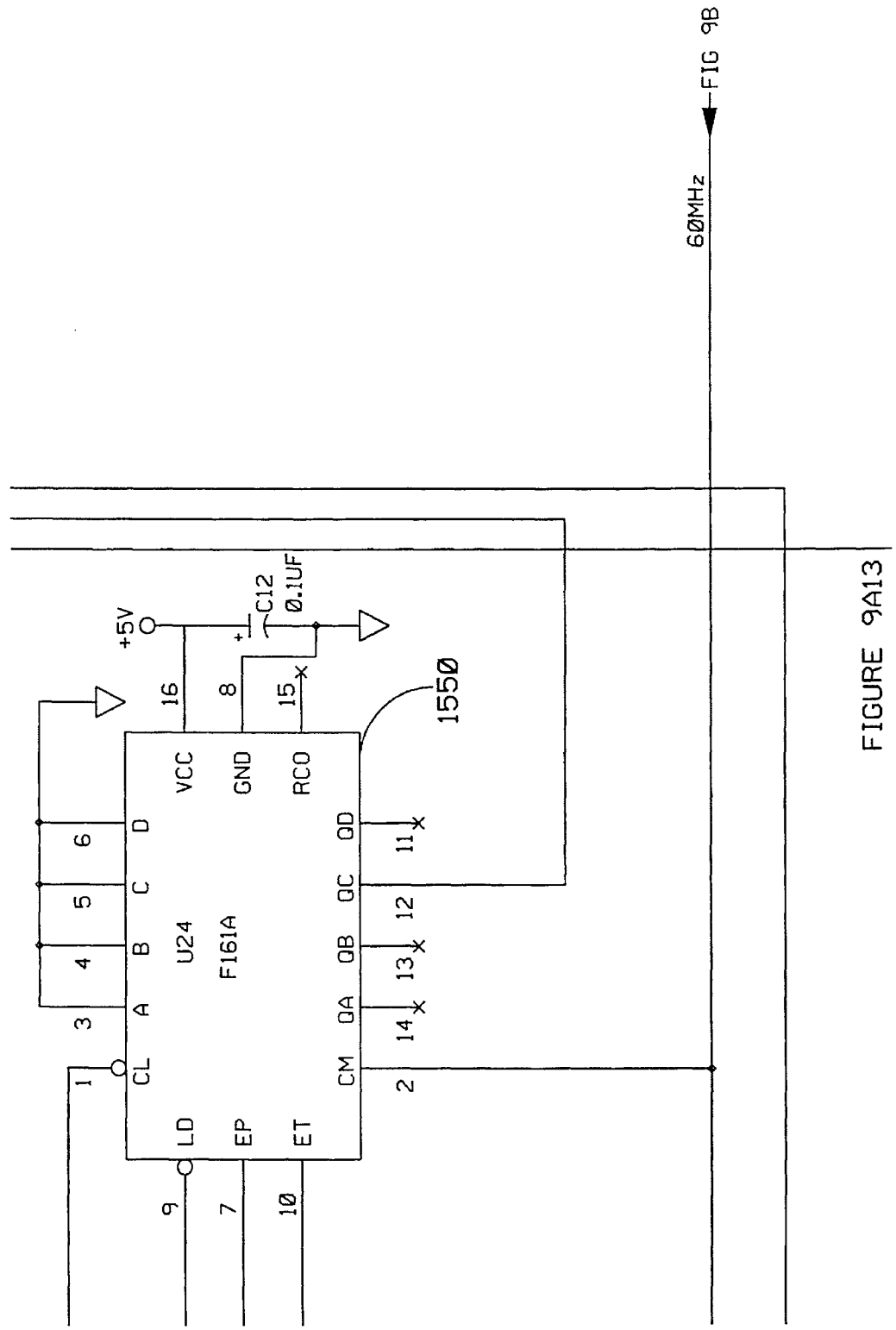
FIGURE 9A13

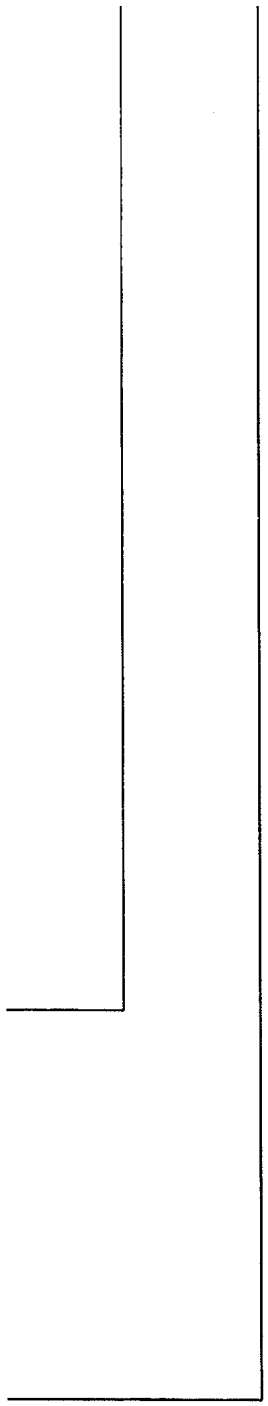
FIGURE 9A14

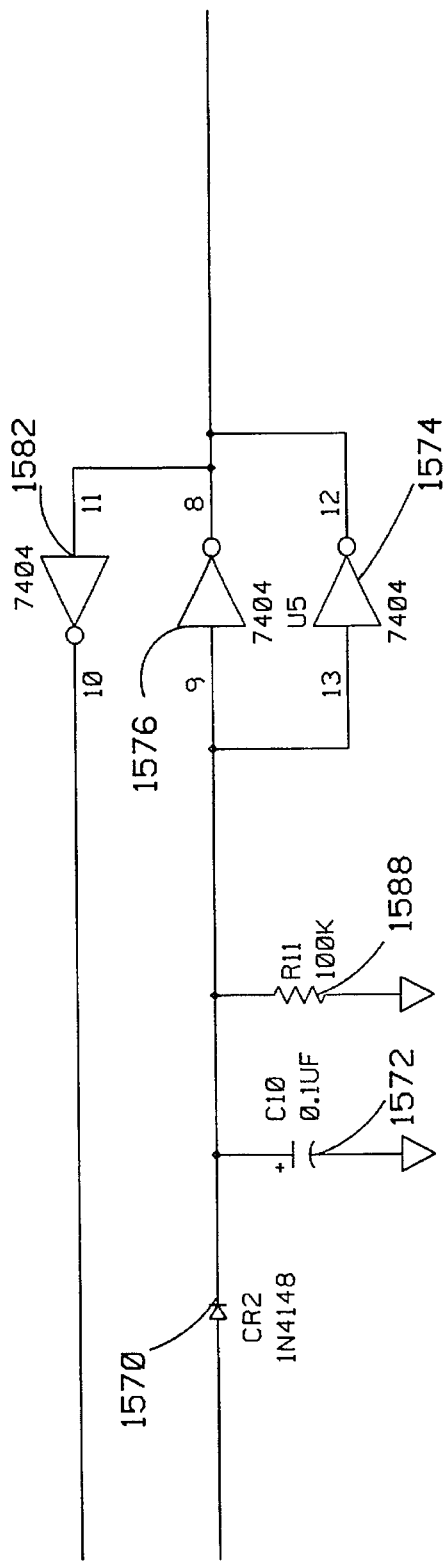
FIGURE 9A15

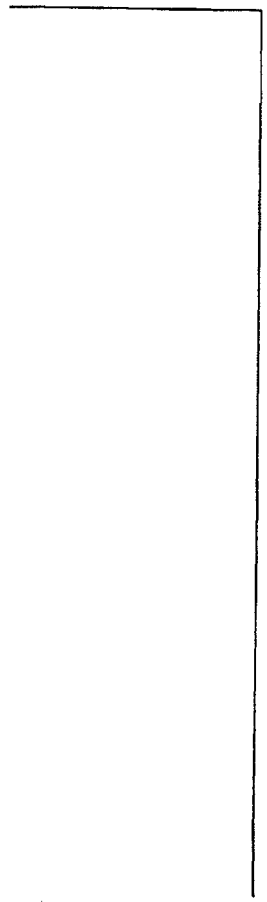
FIGURE 9A16

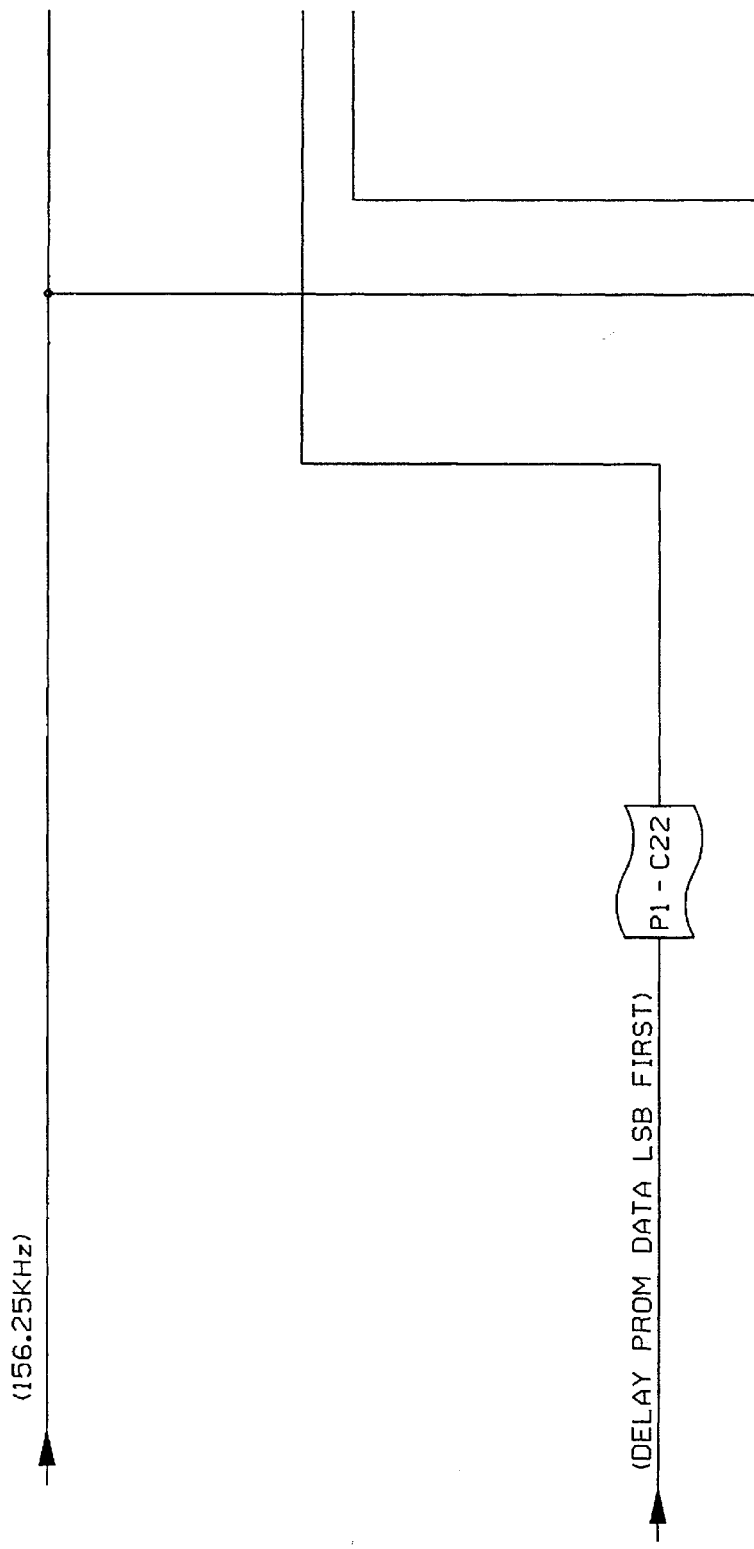

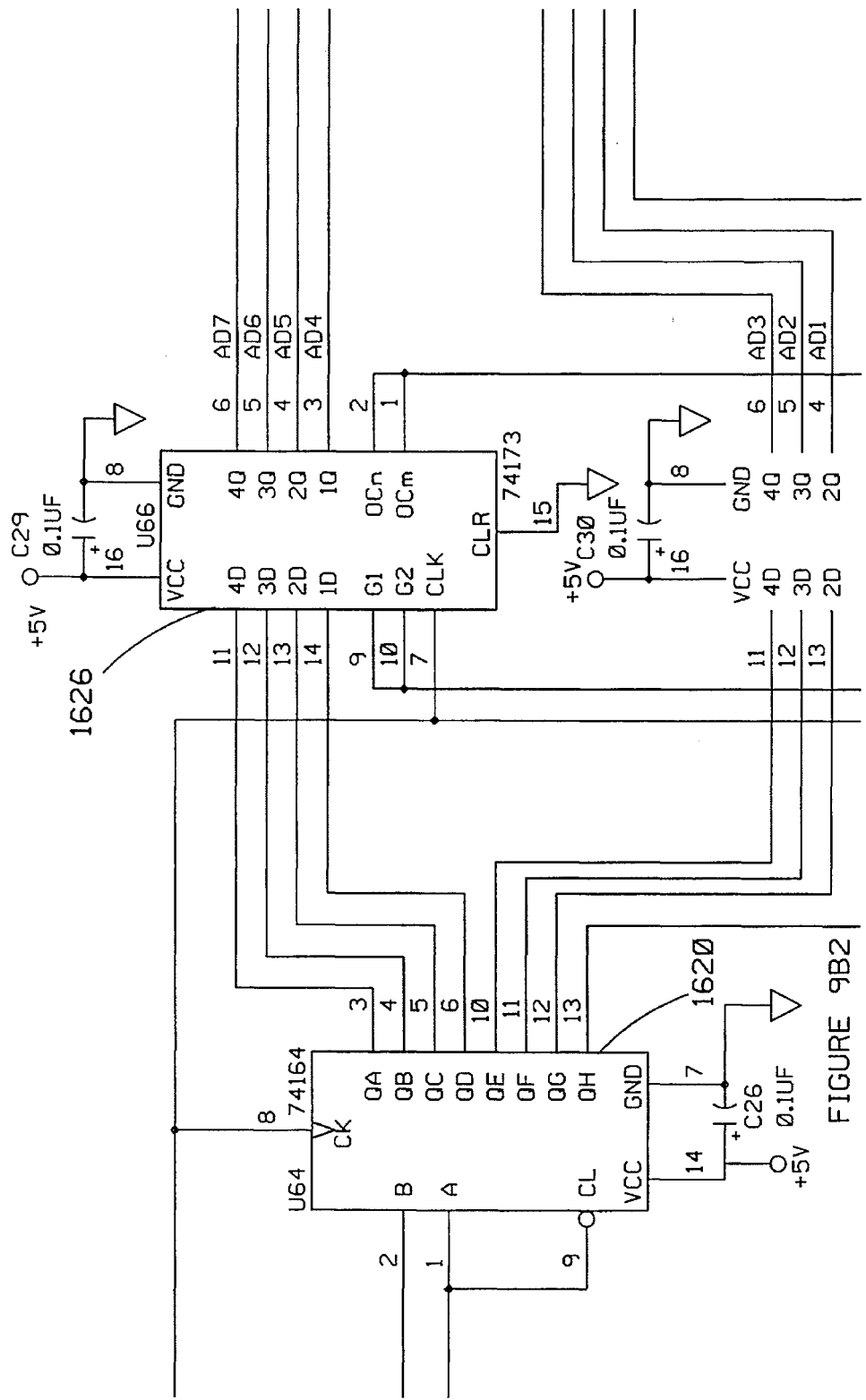
FIGURE 9B2

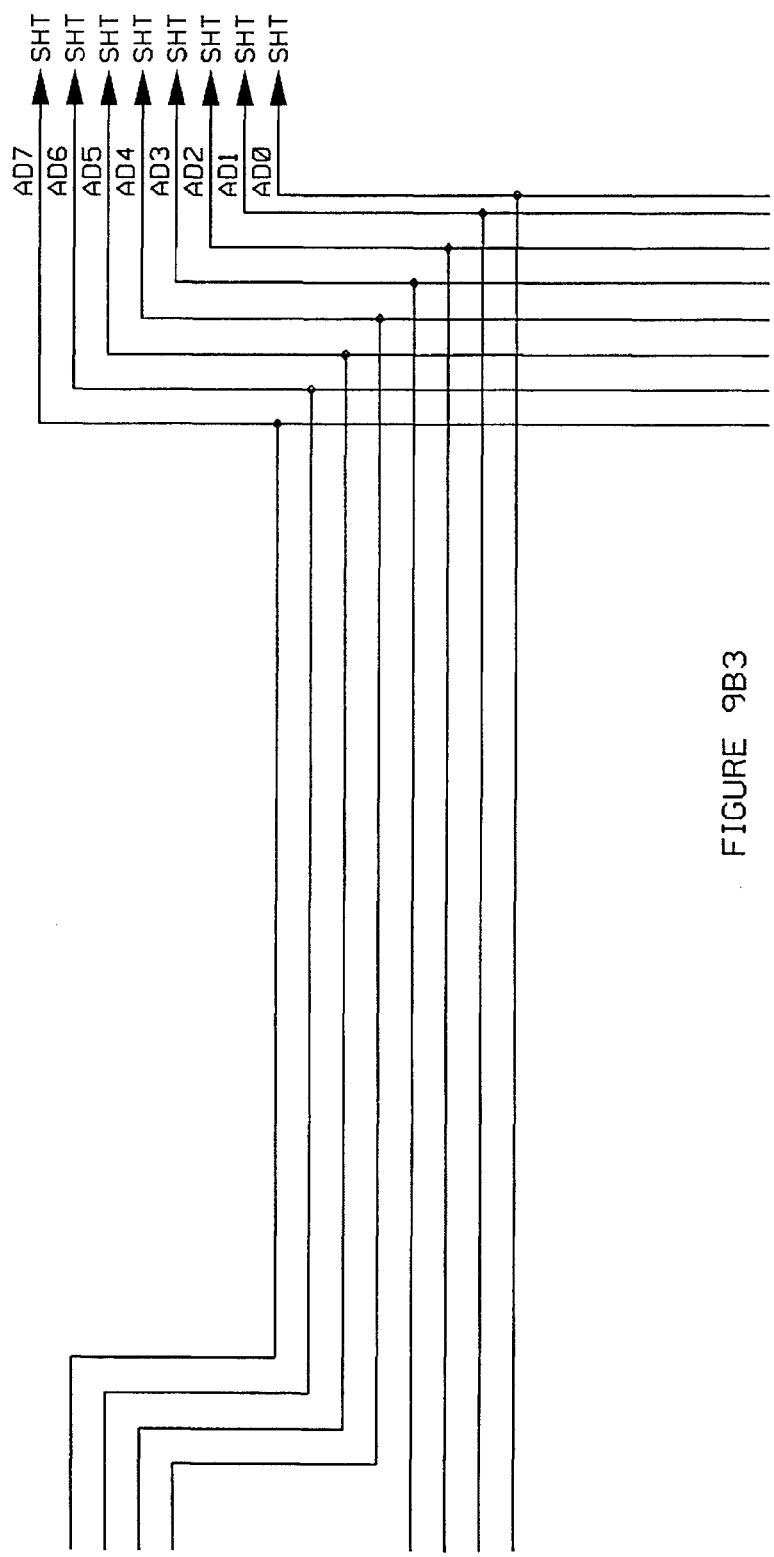
FIGURE 9B3

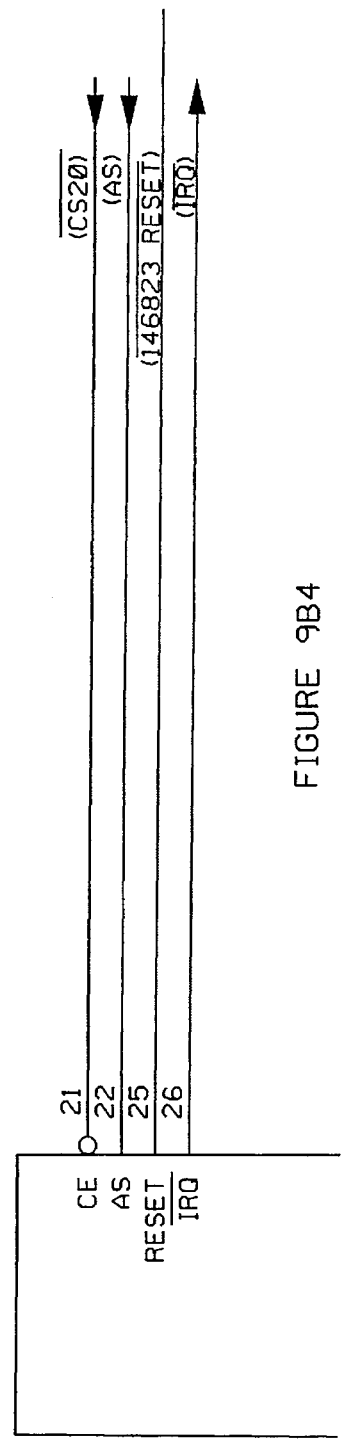
FIGURE 9B4

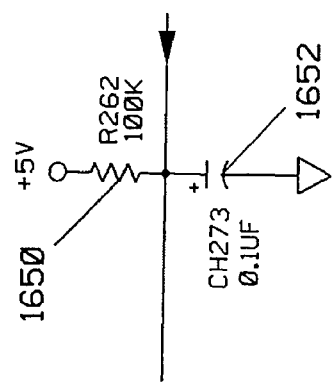

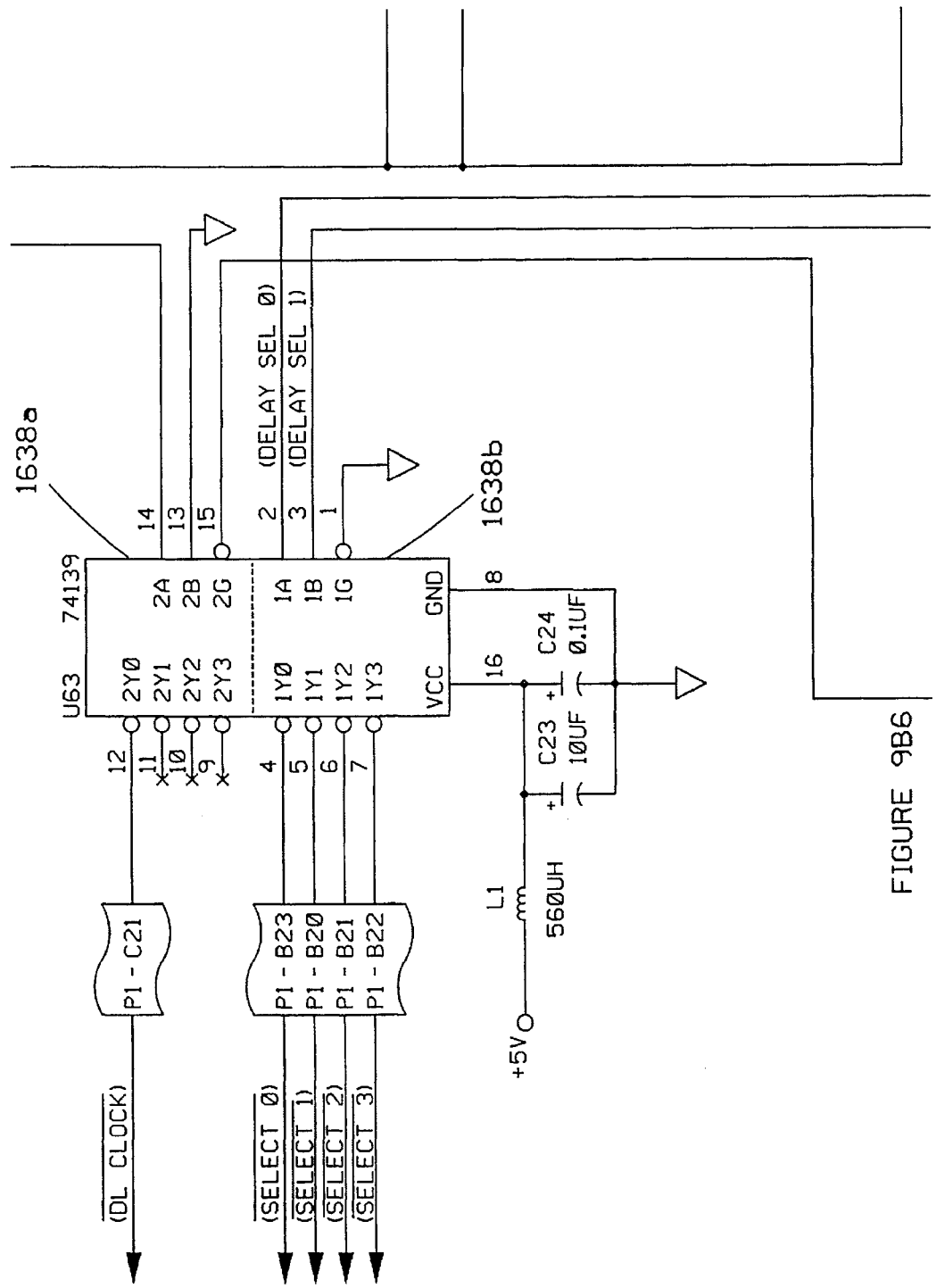
FIGURE 9B6

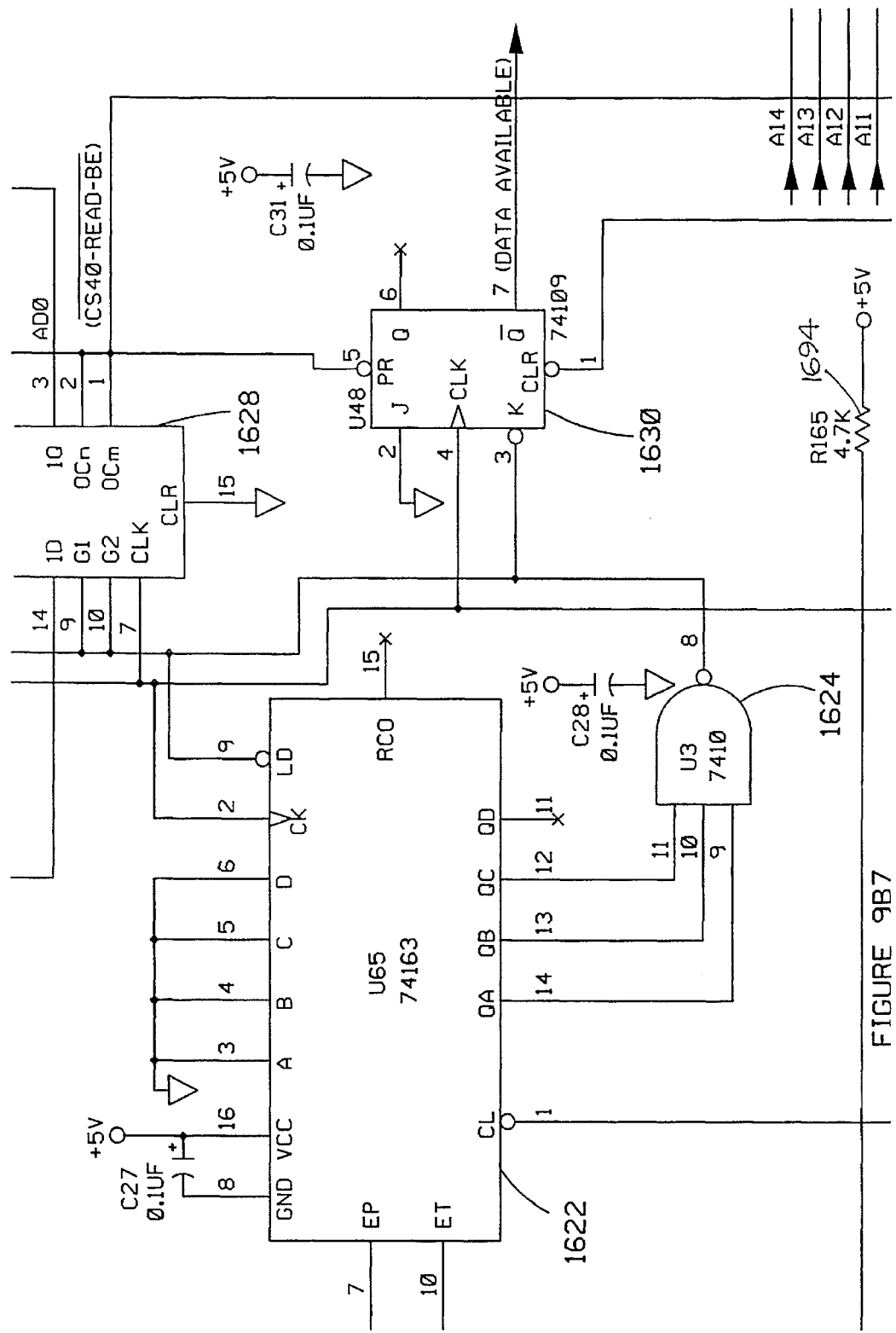
FIGURE 9B7

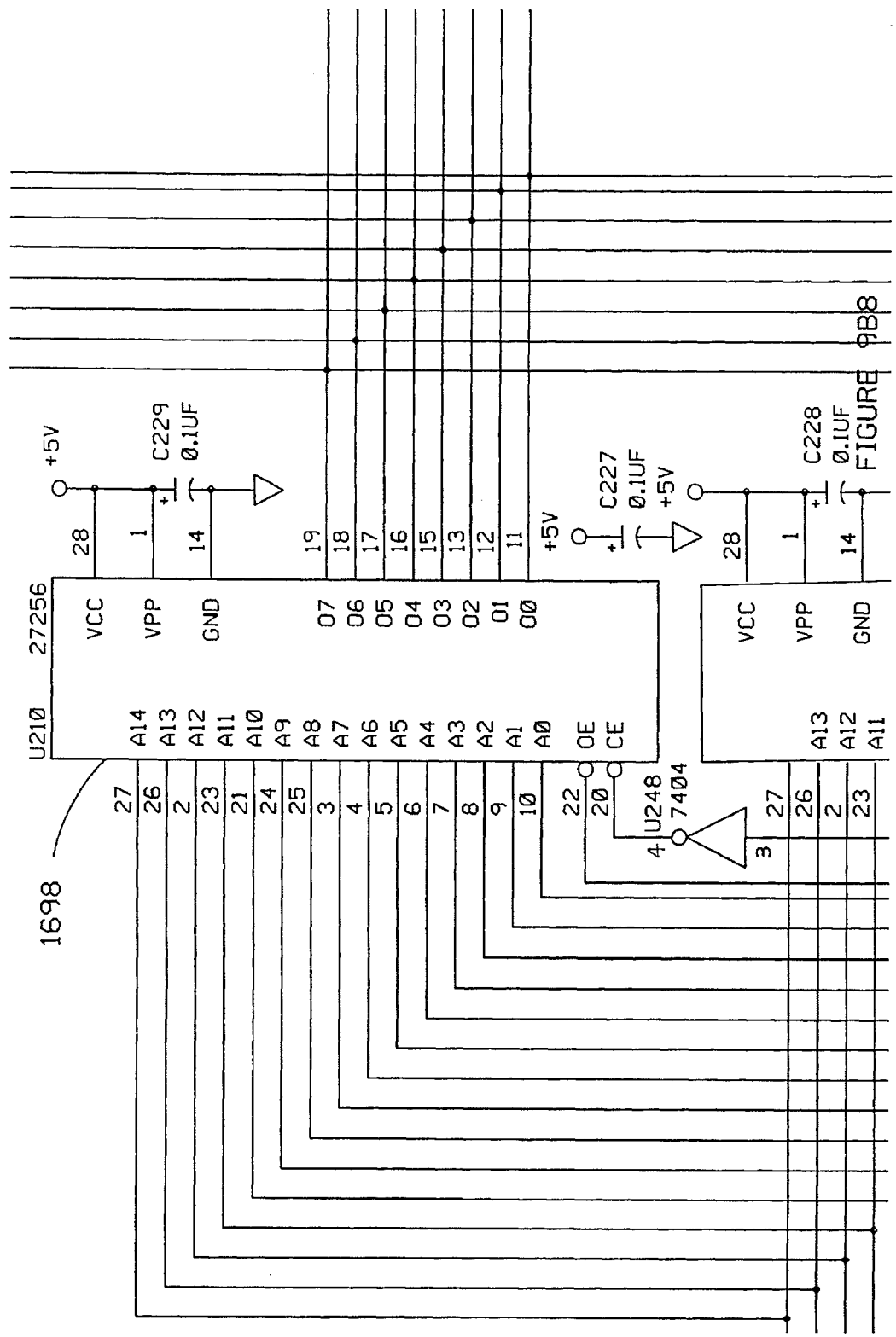

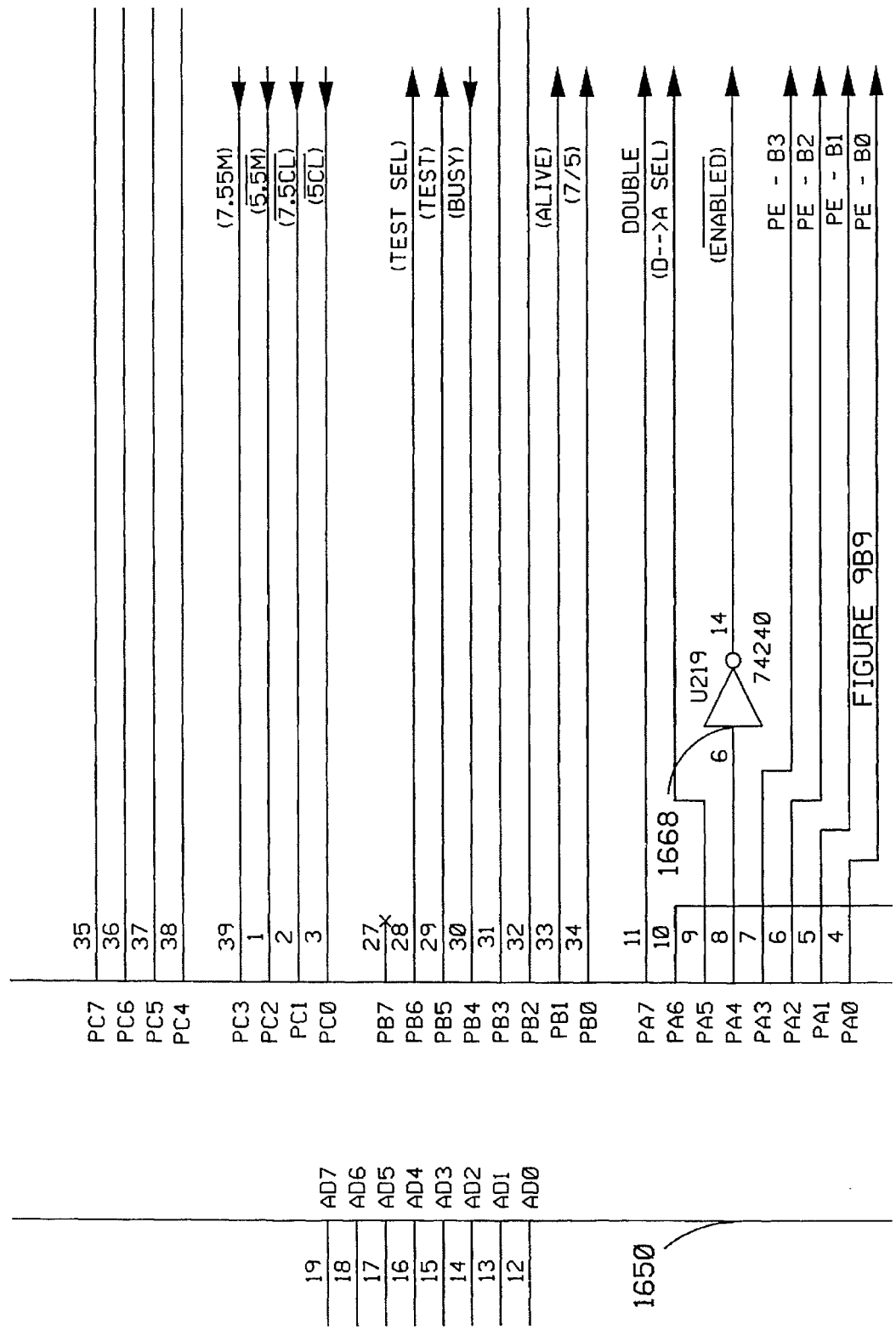

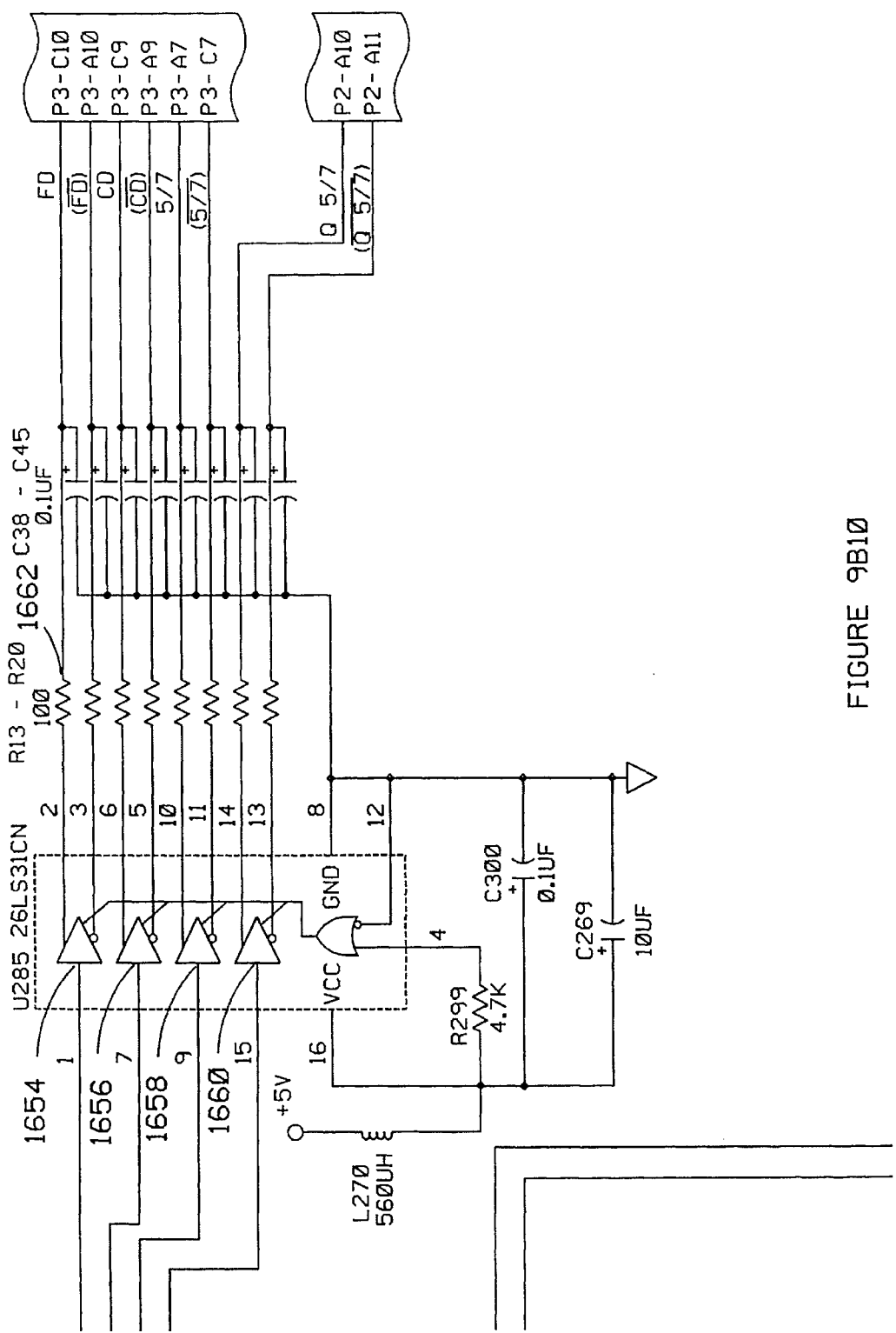
FIGURE 9B10

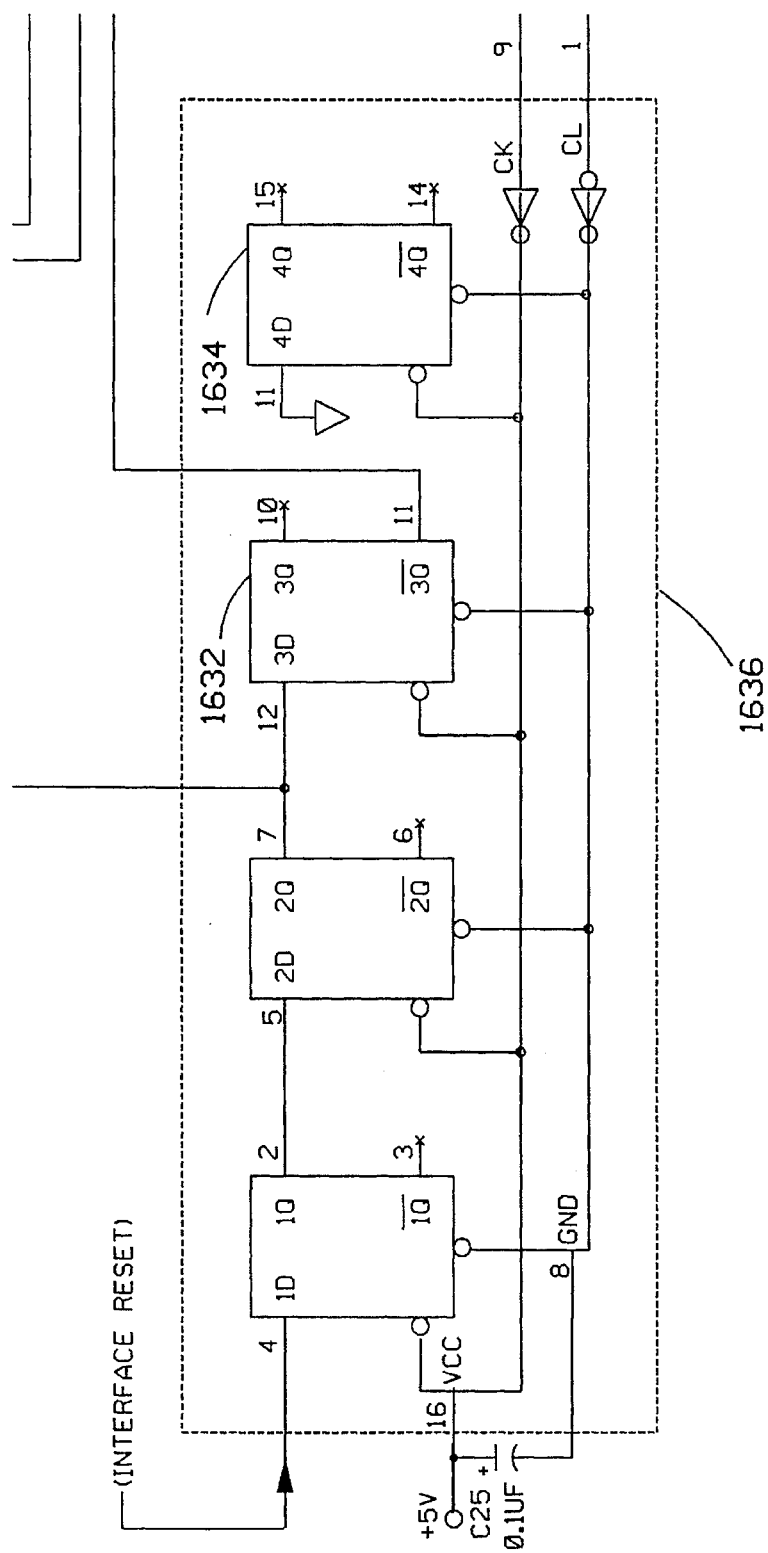
FIGURE 9B11

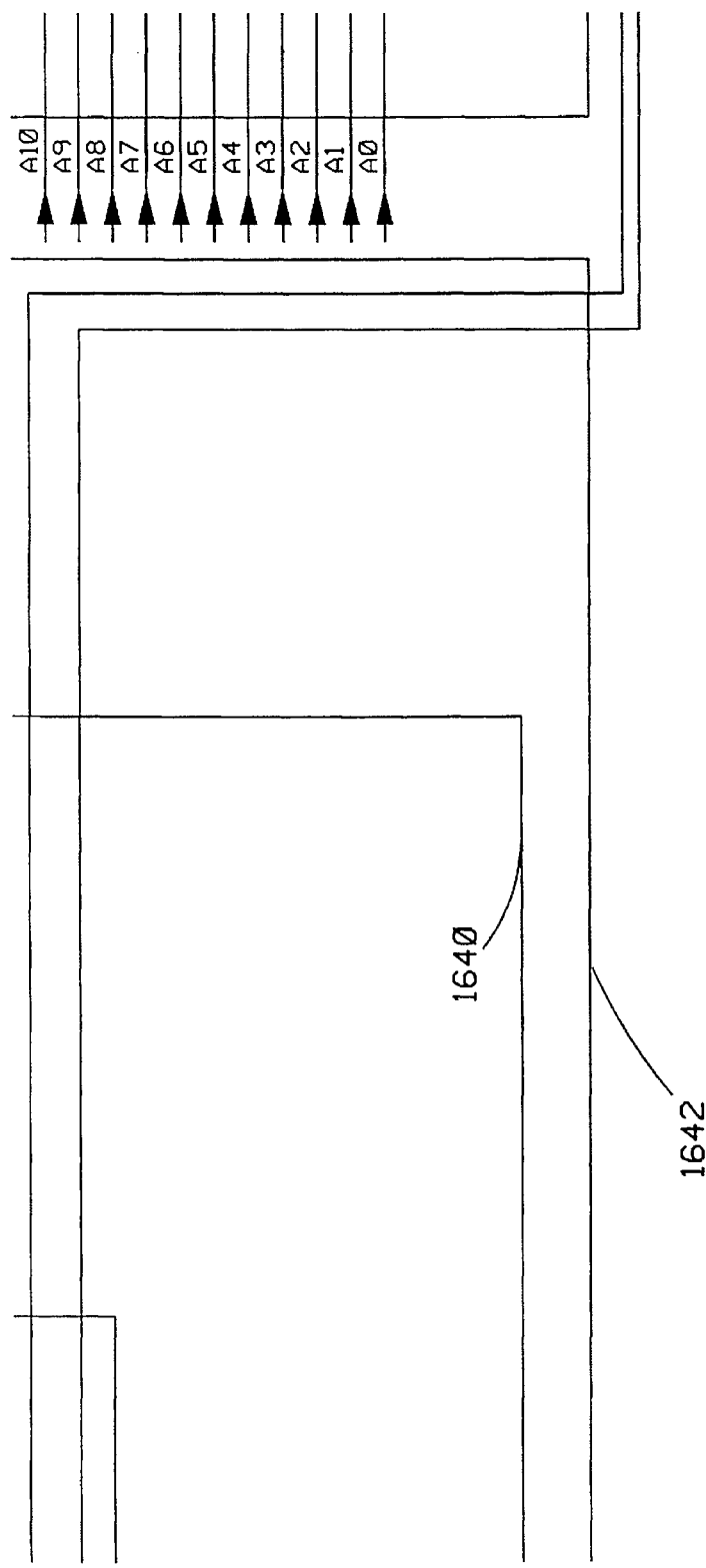
FIGURE 9B12

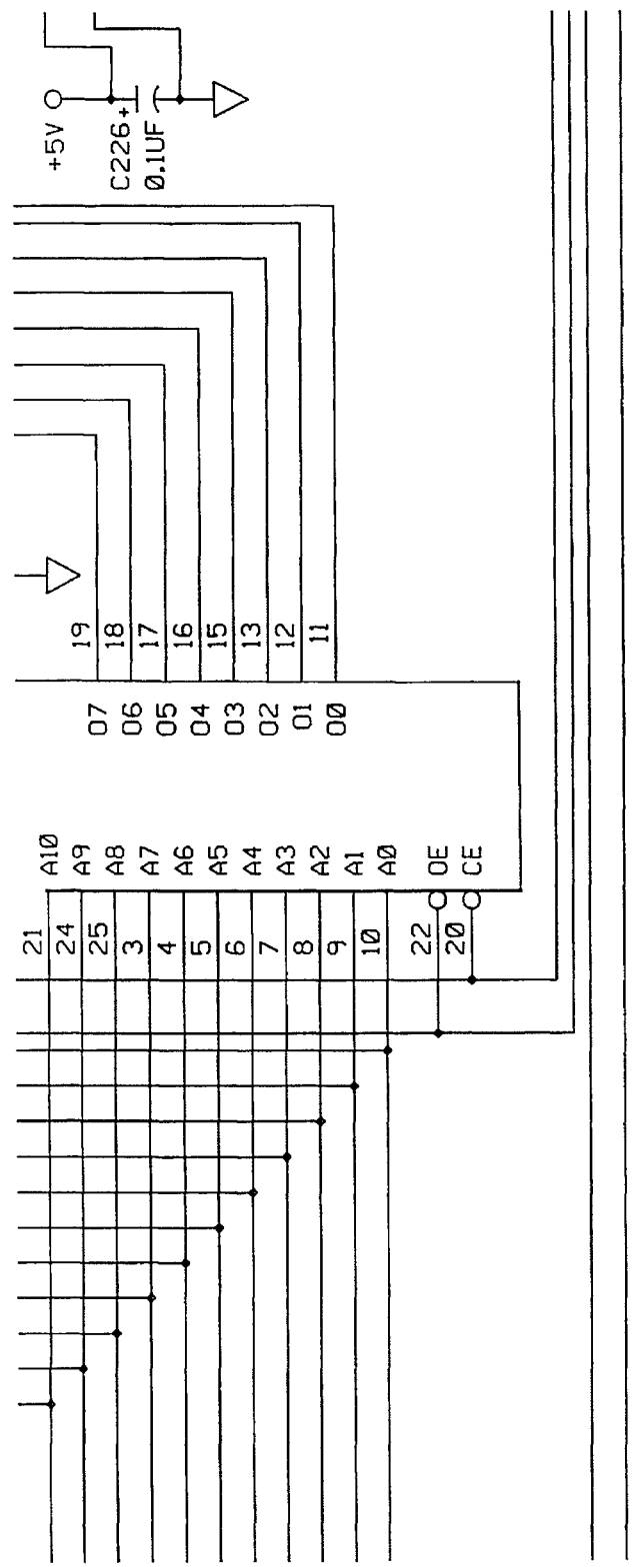
FIGURE 9B13

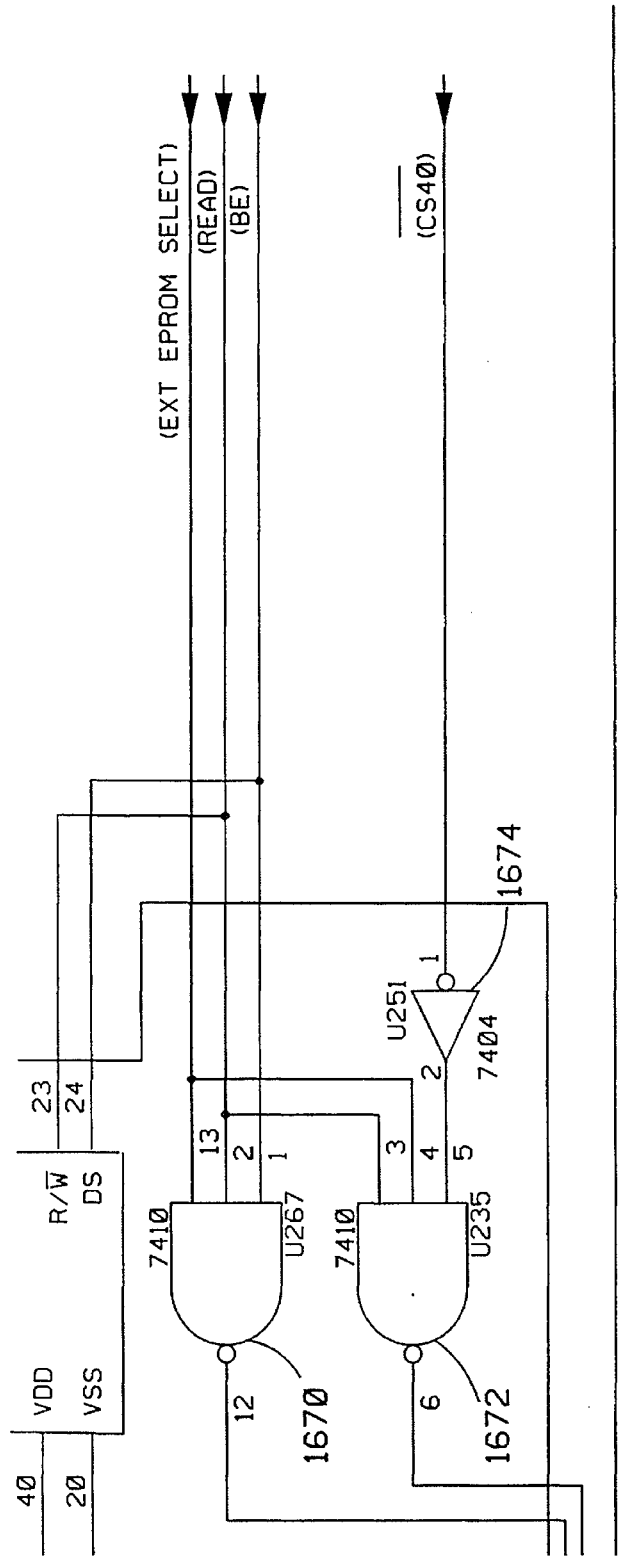
FIGURE 9B14

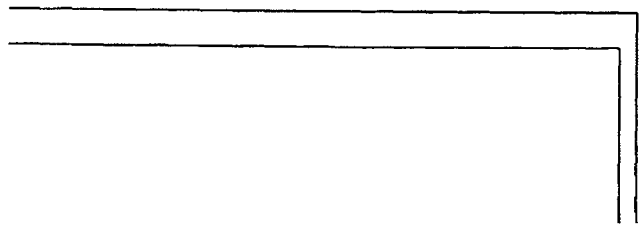
FIGURE 9B15

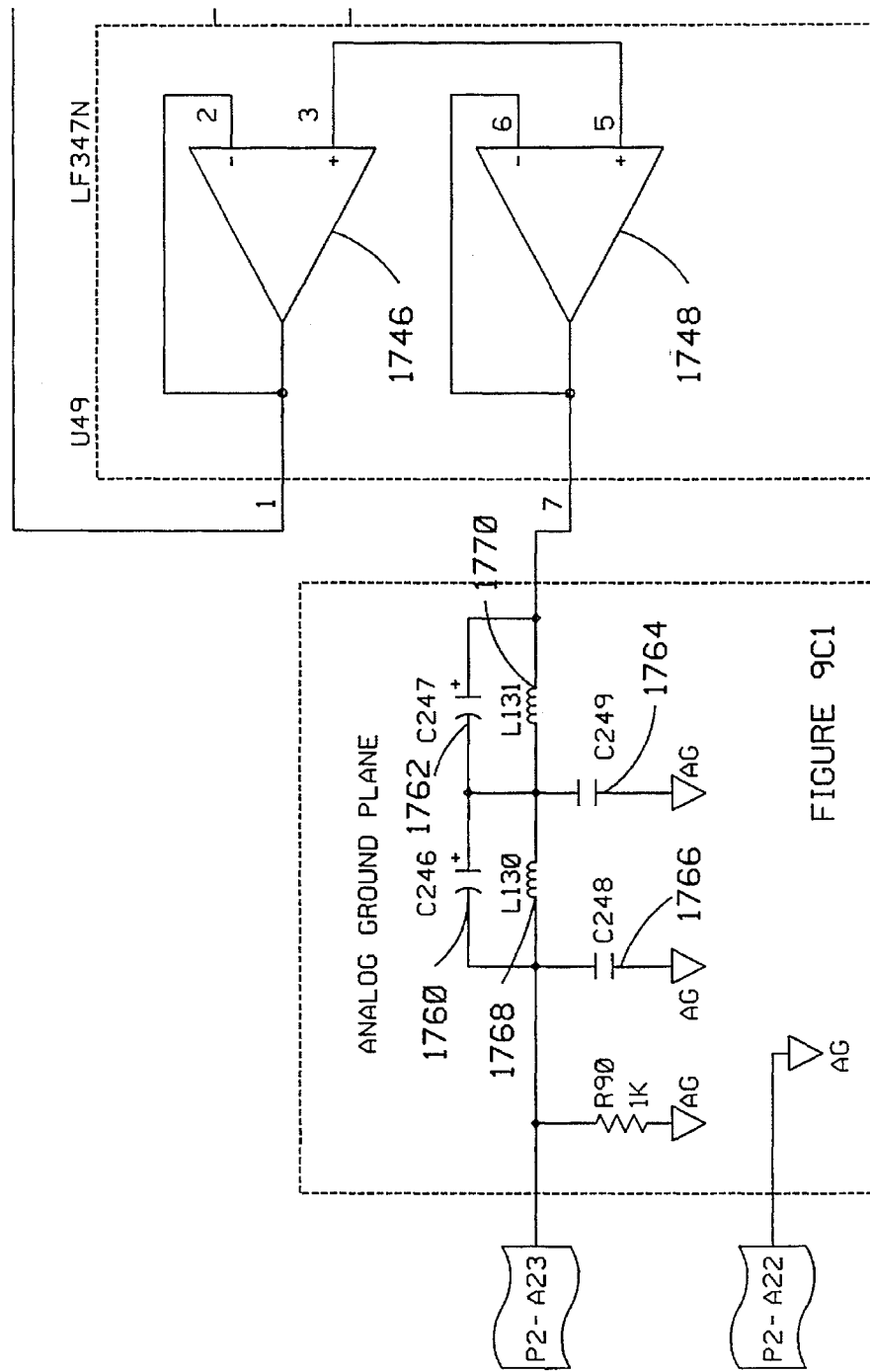
FIGURE 9C1

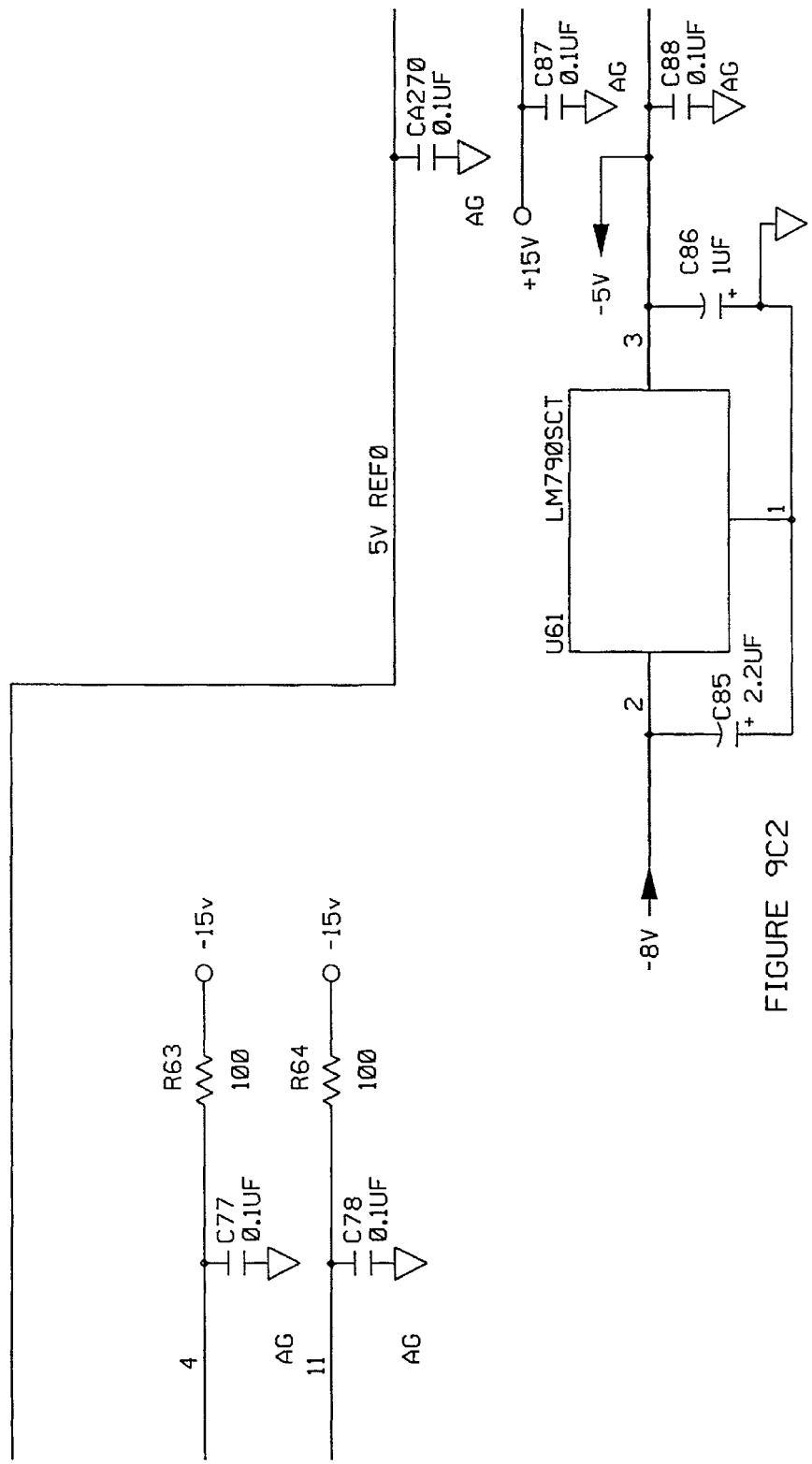
FIGURE 9C2

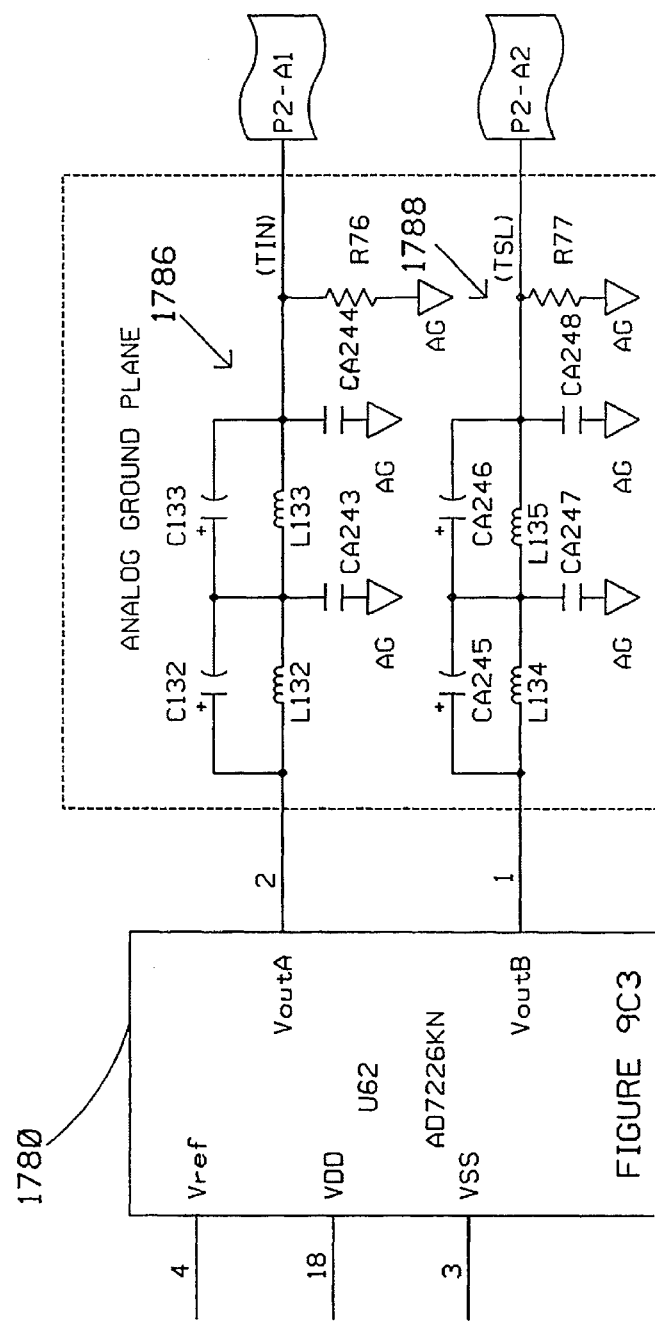
FIGURE 9C3

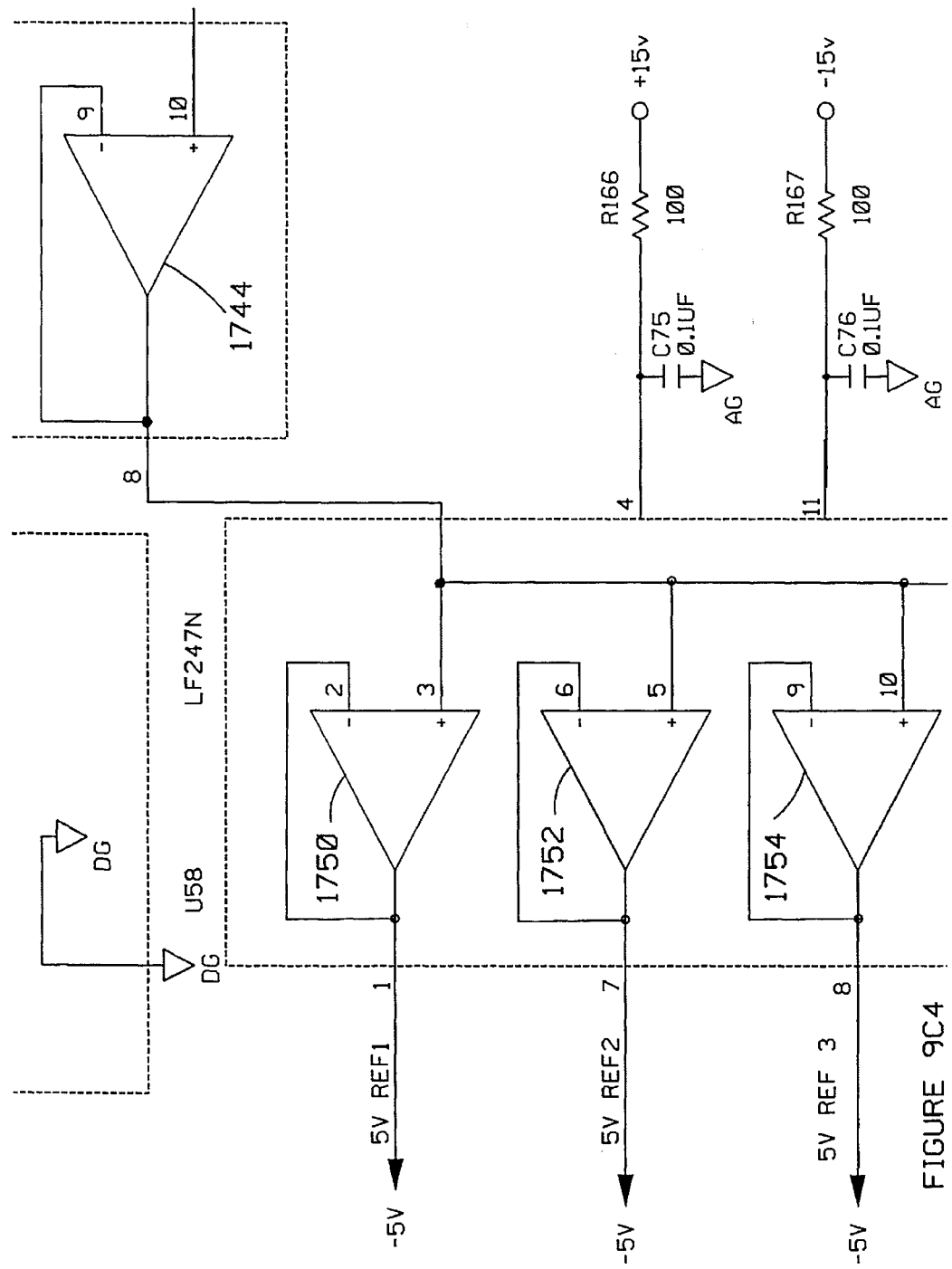
FIGURE 9C4

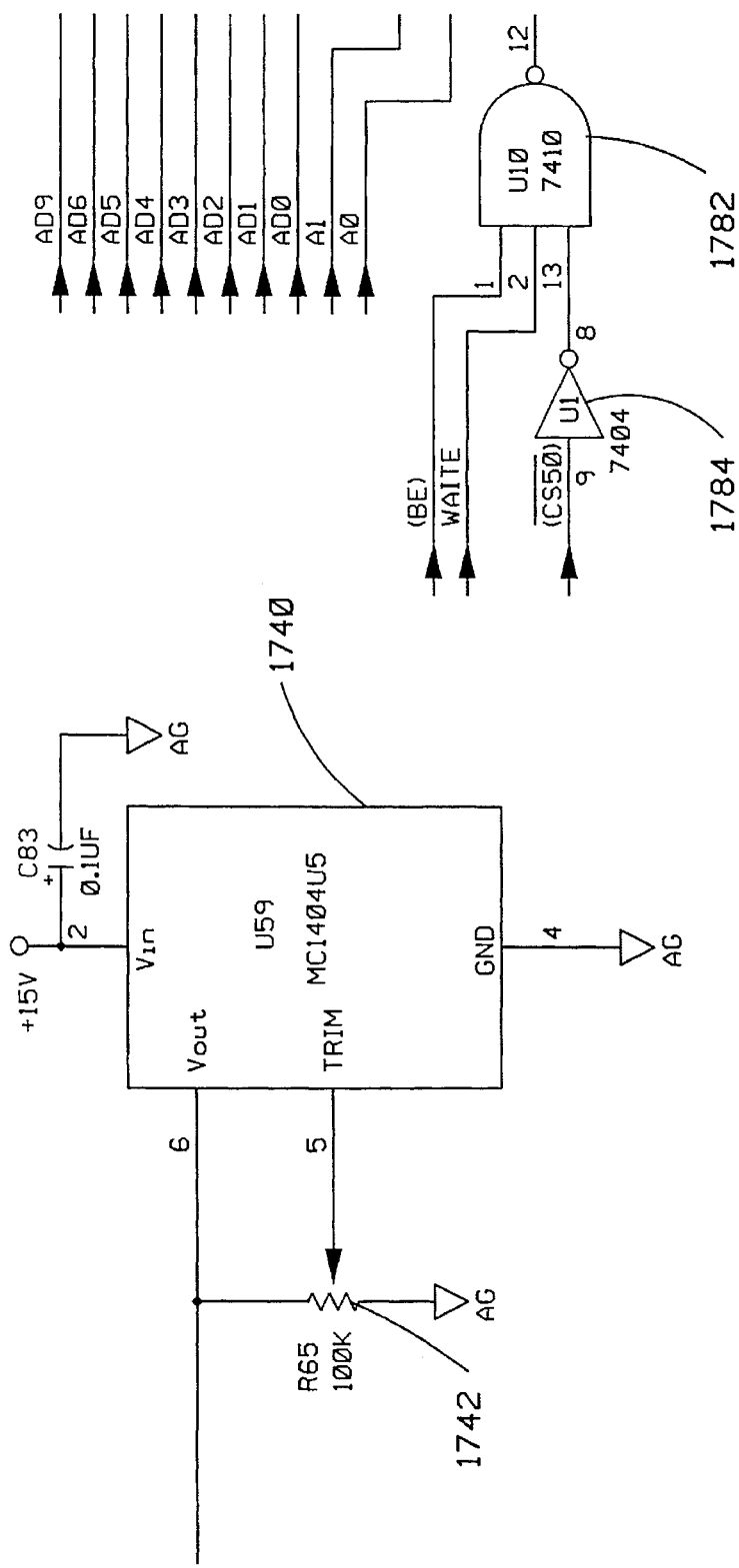
FIGURE 9C5

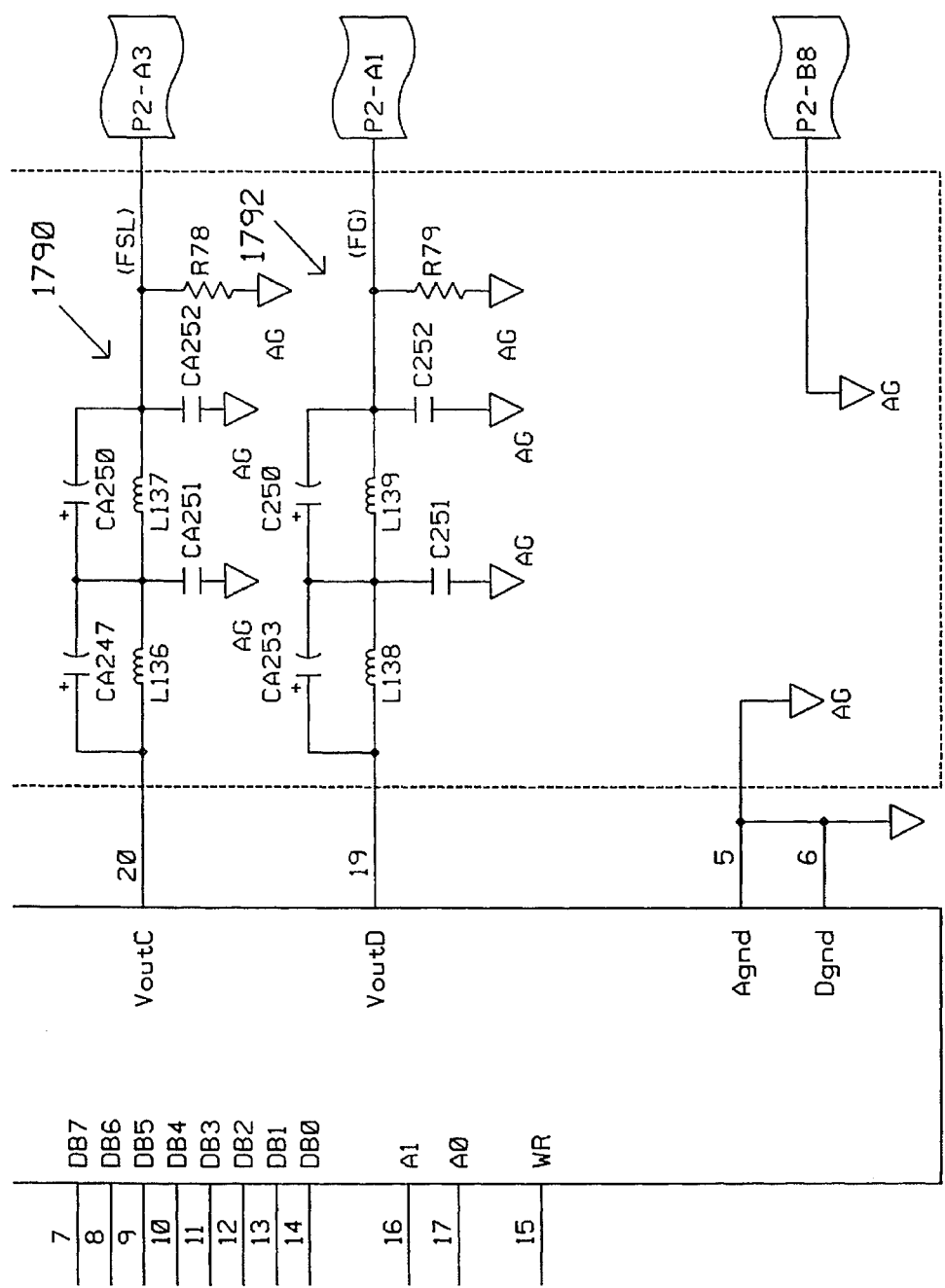
FIGURE 9C6

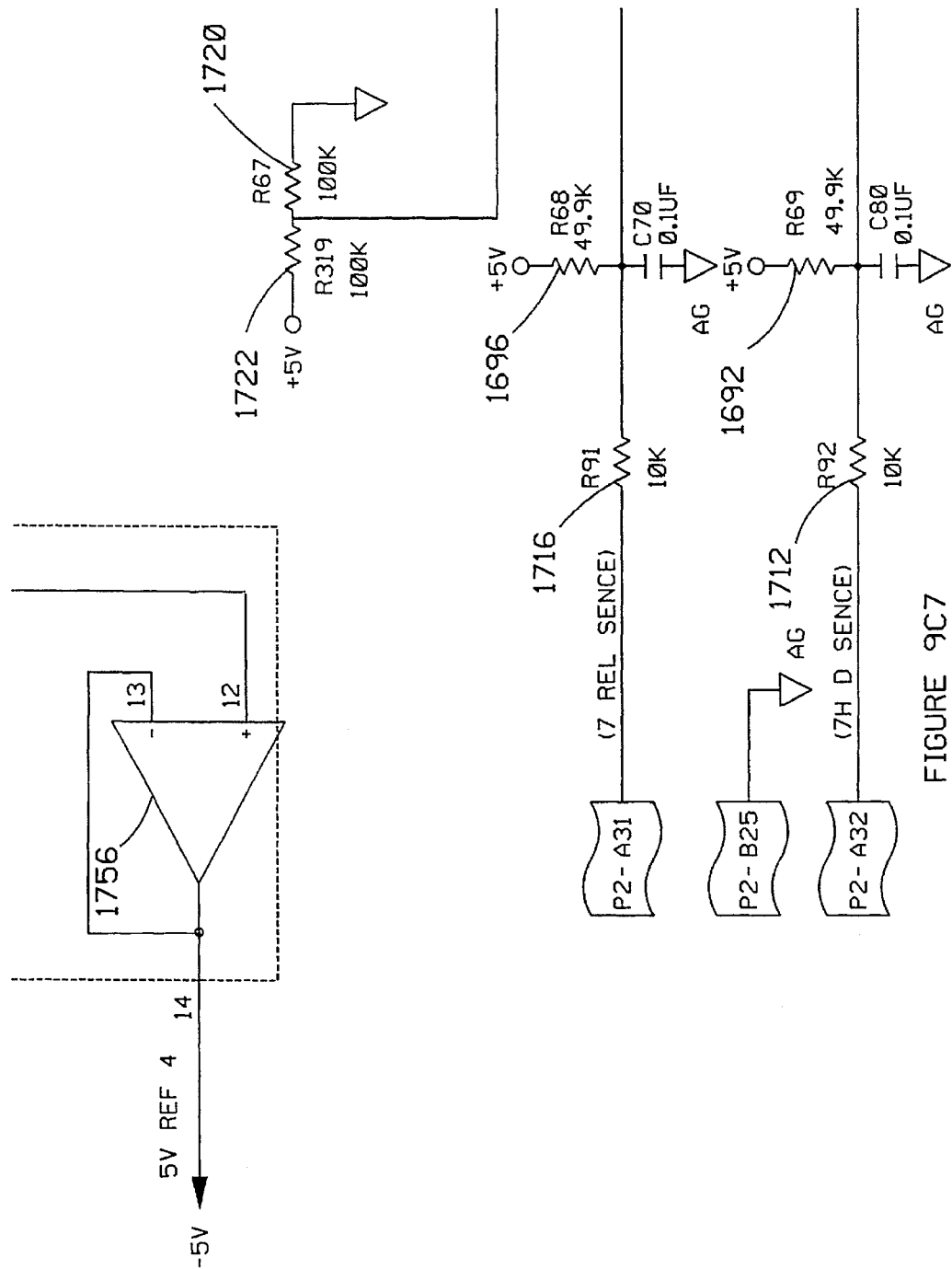
FIGURE 9C7

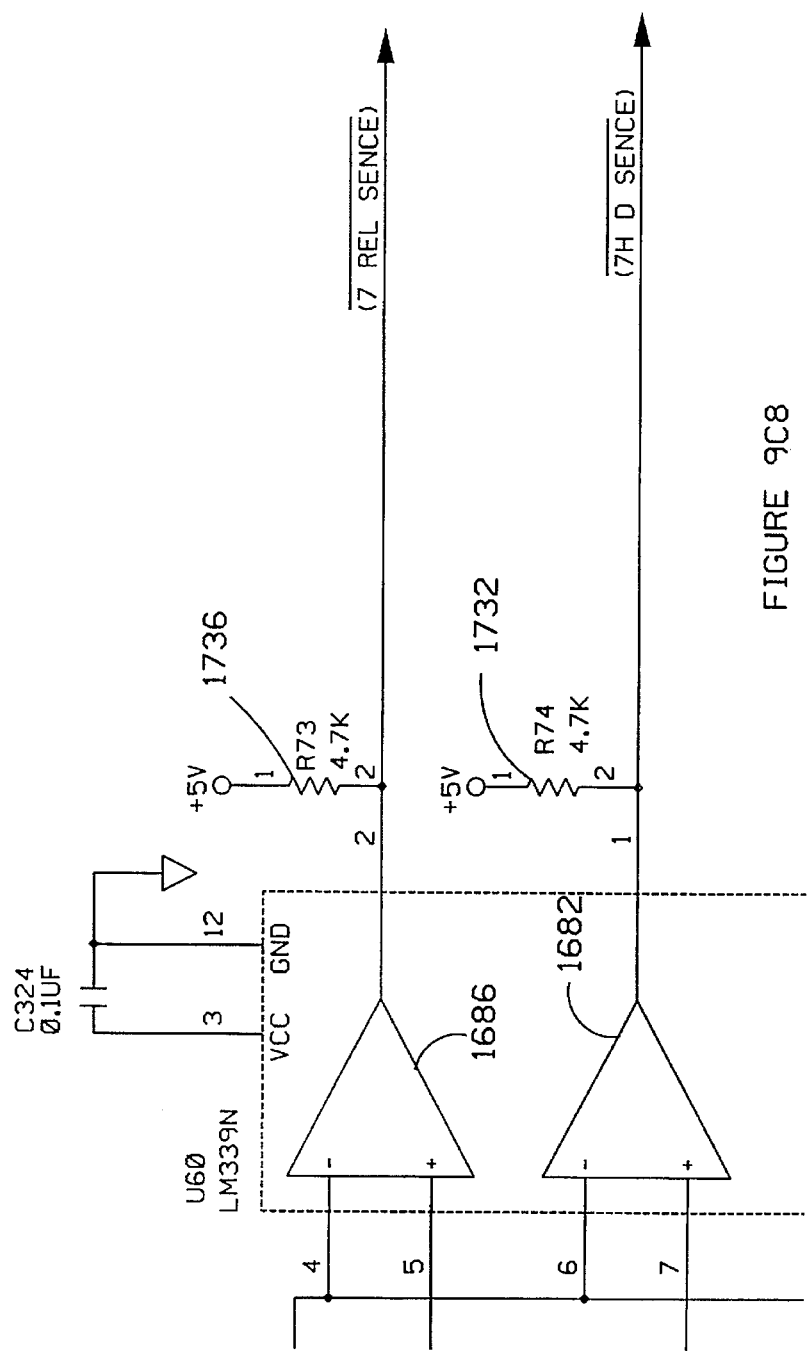
FIGURE 9C8

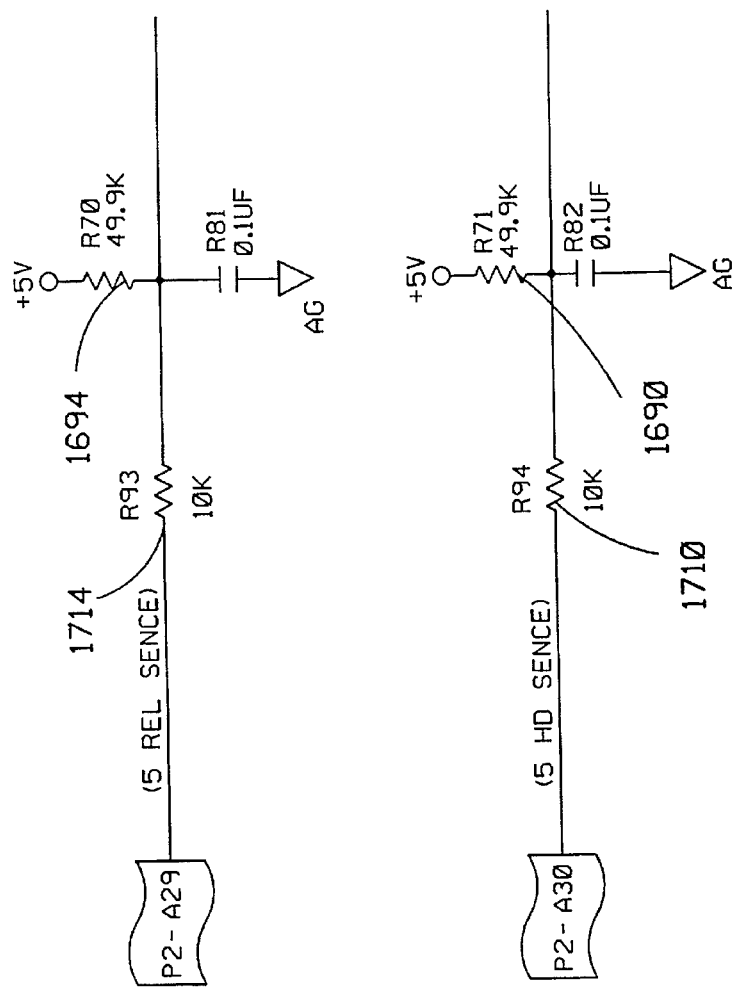
FIGURE 9C9

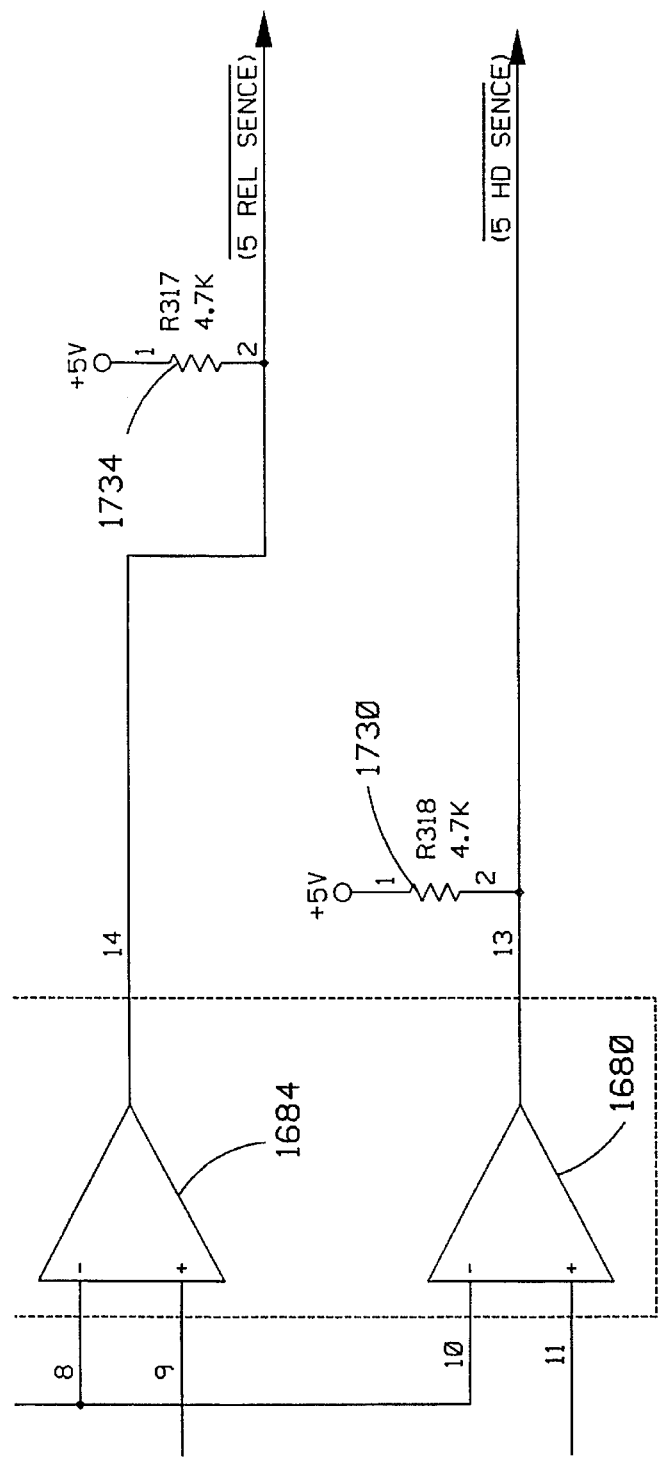
FIGURE 9C10

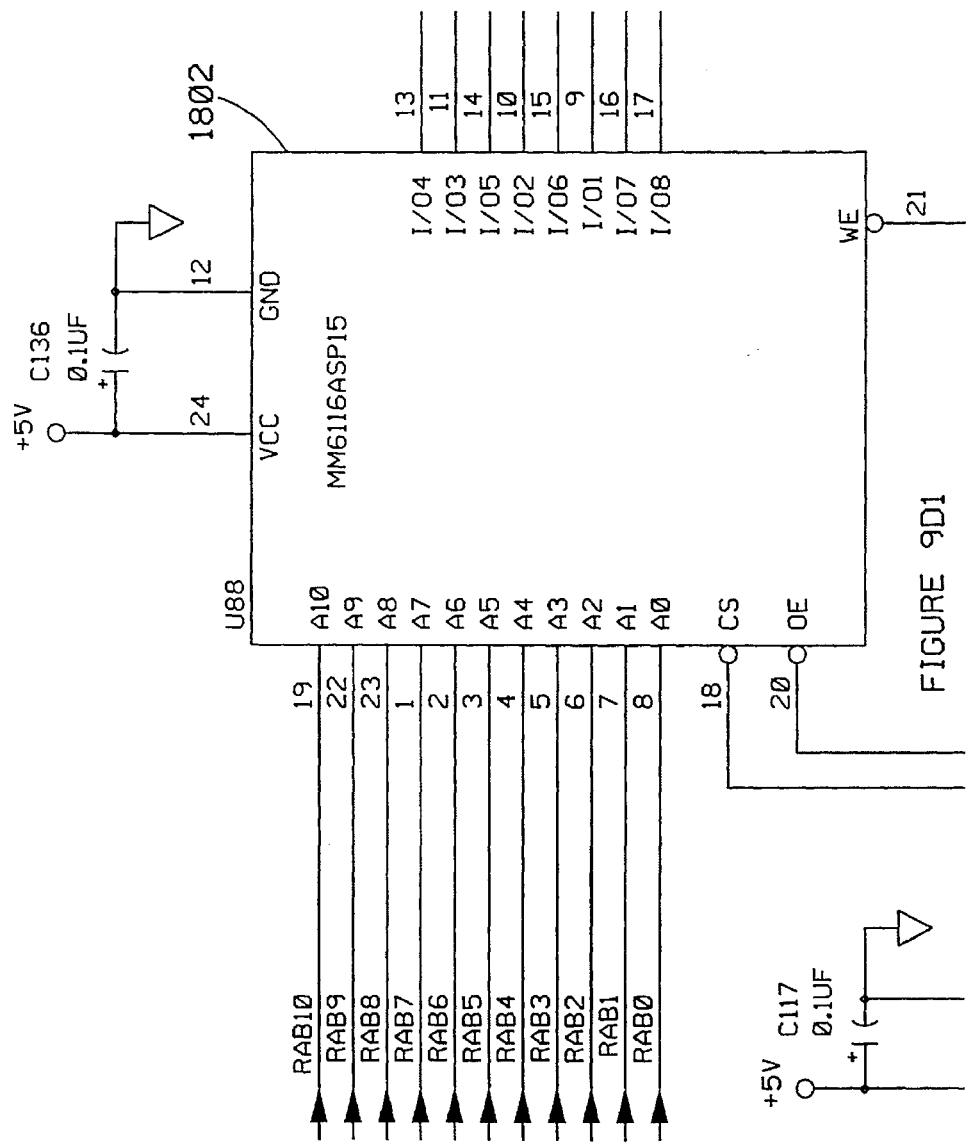
FIGURE 9D1

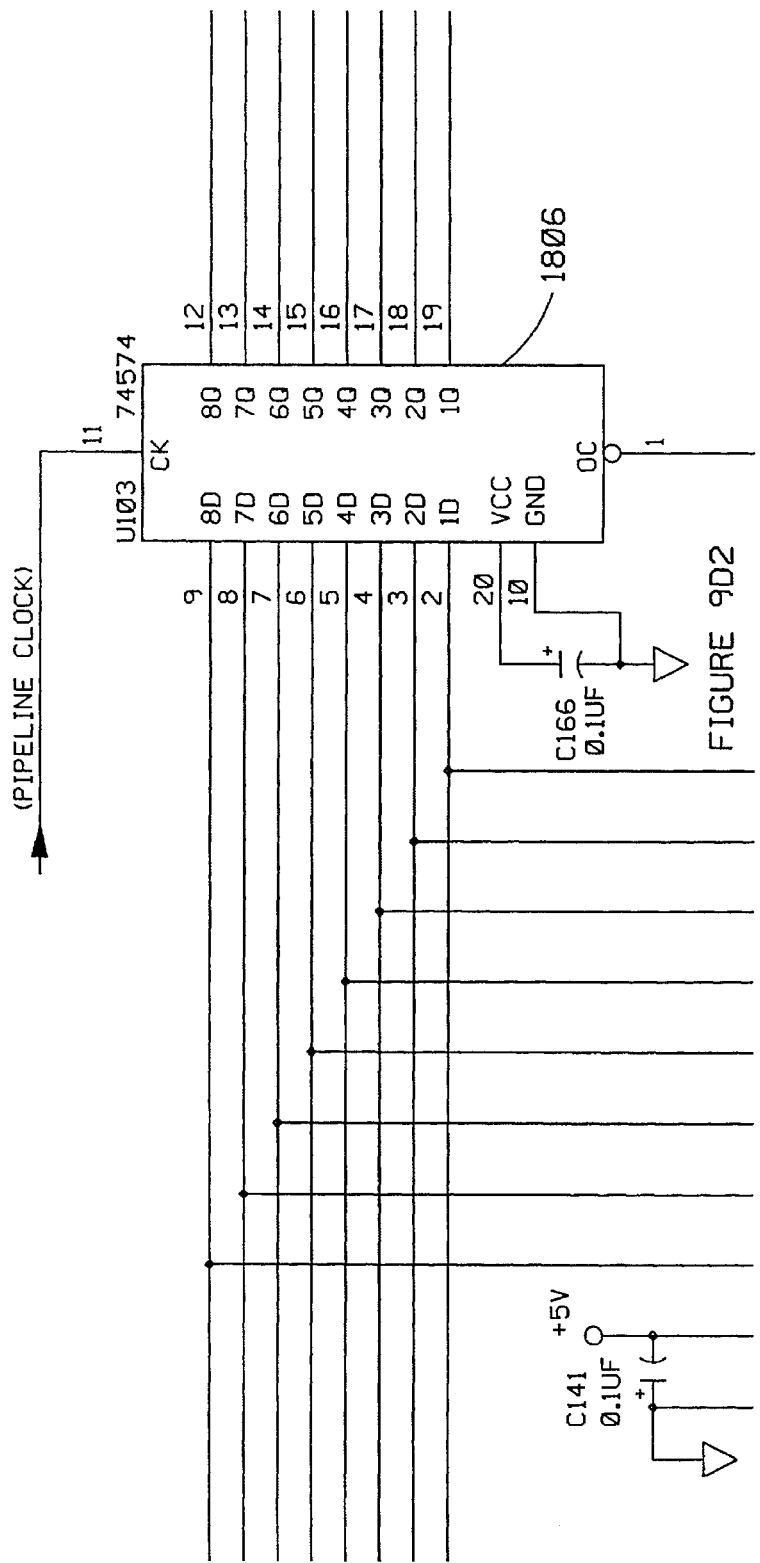

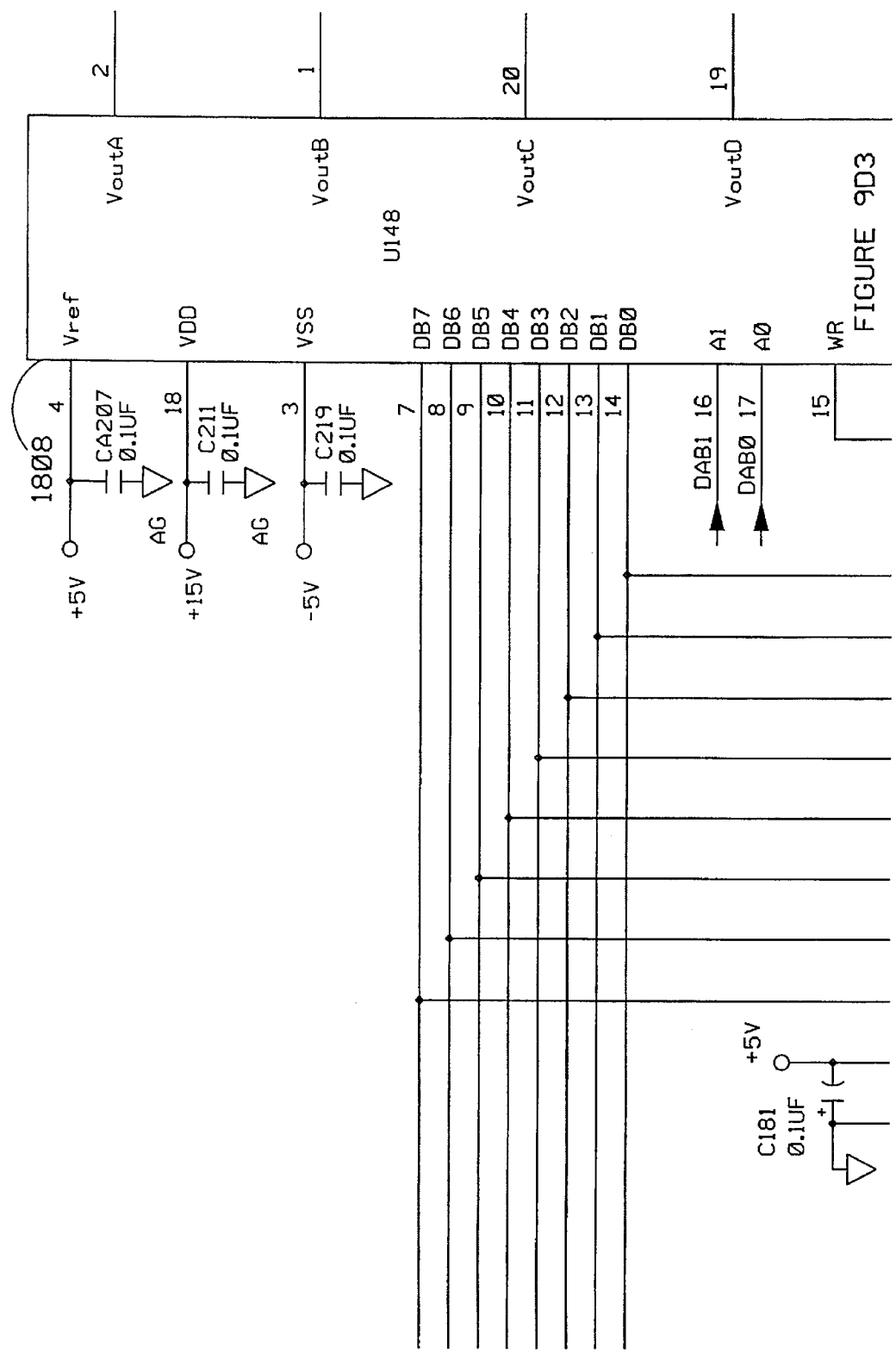
FIGURE 9D3

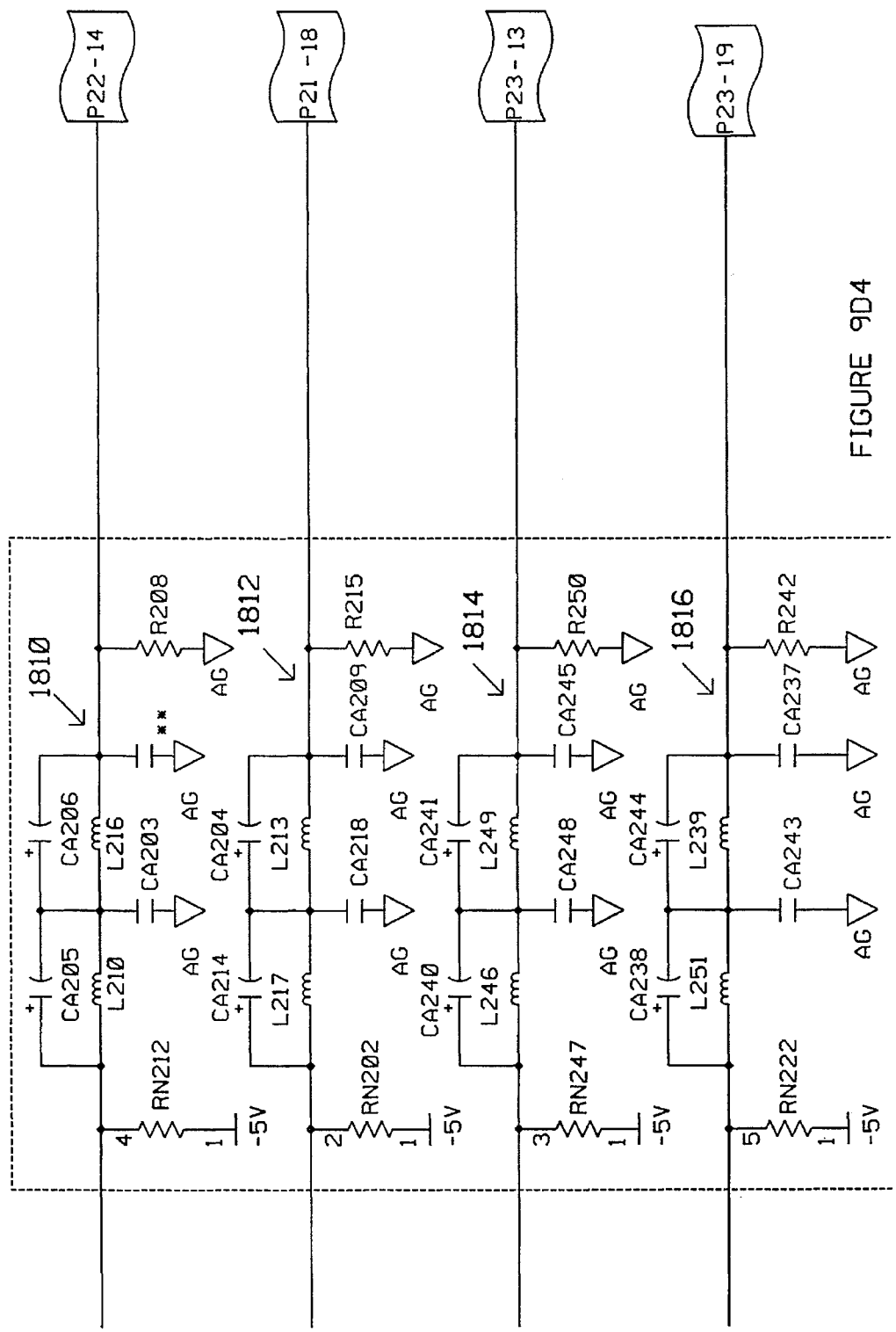
FIGURE 9D4

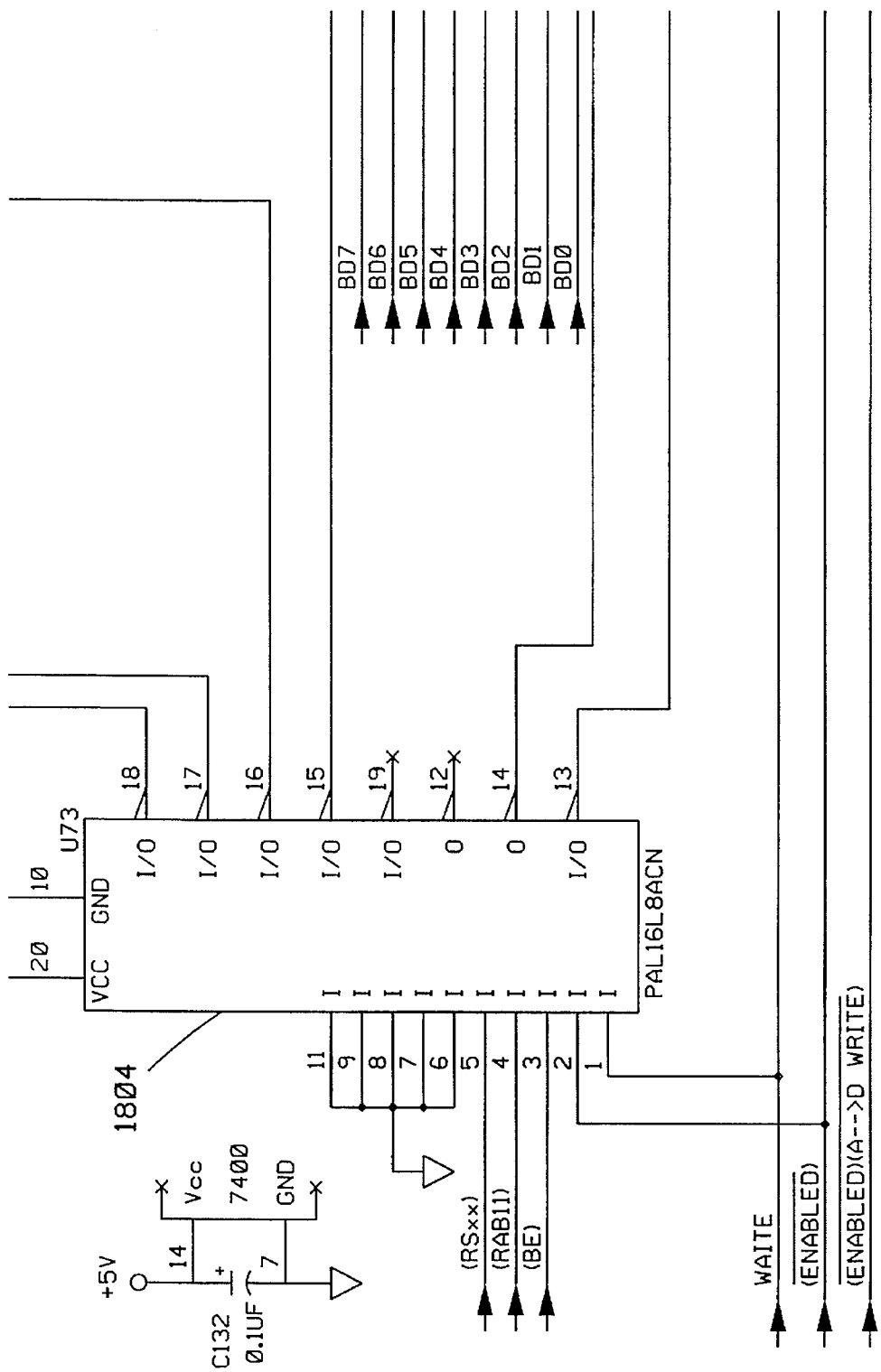
FIGURE 9D5

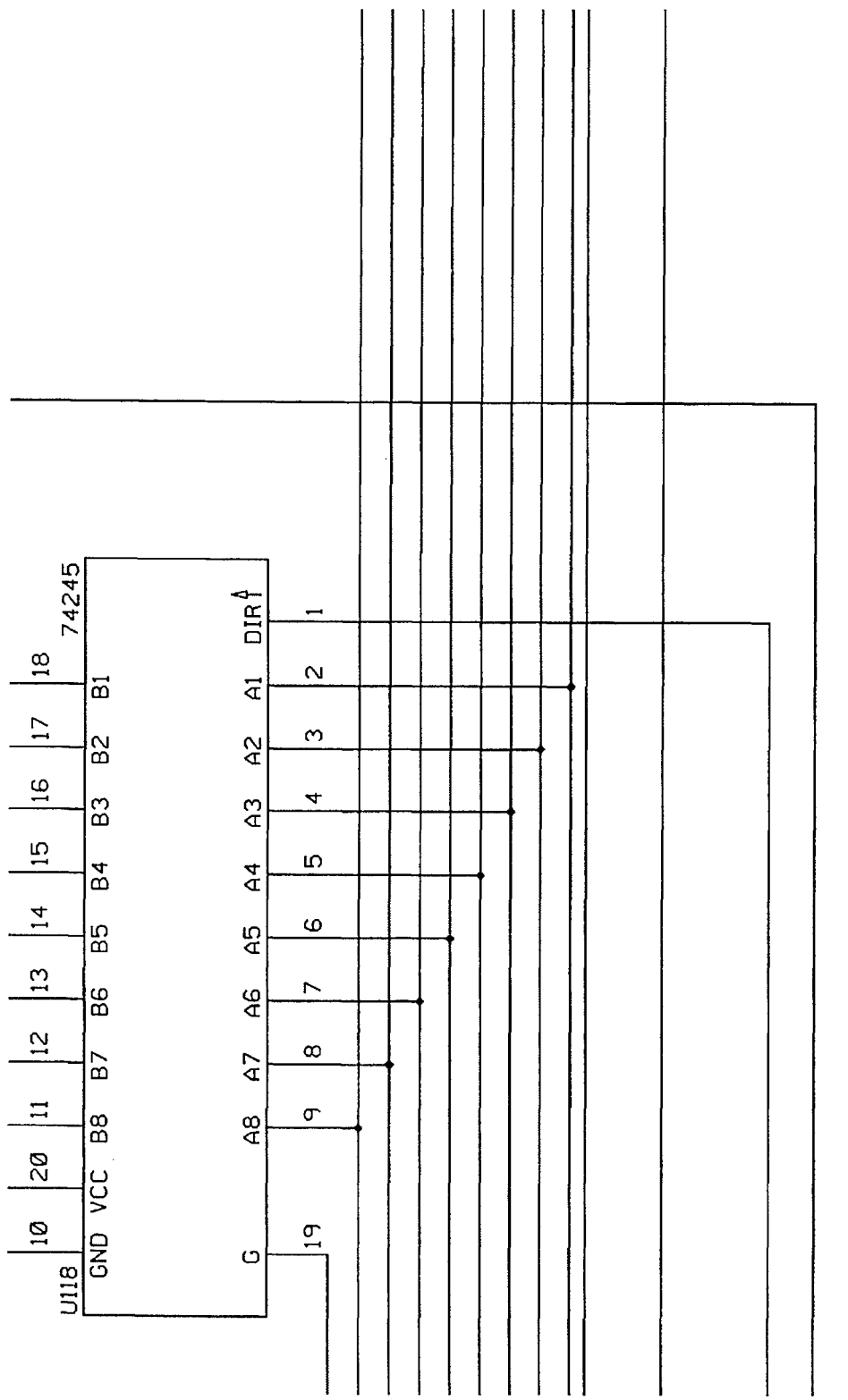

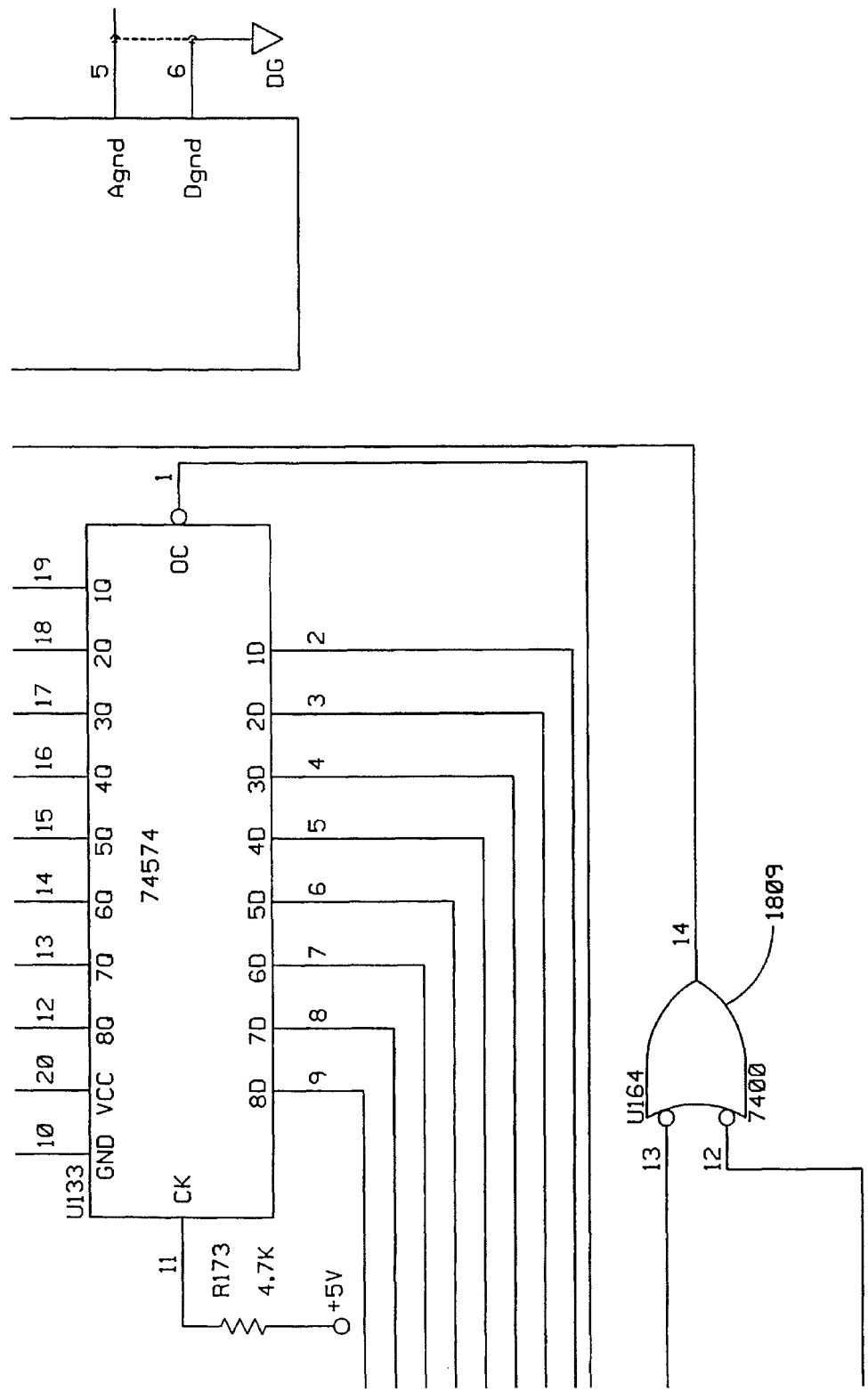
FIGURE 9D7

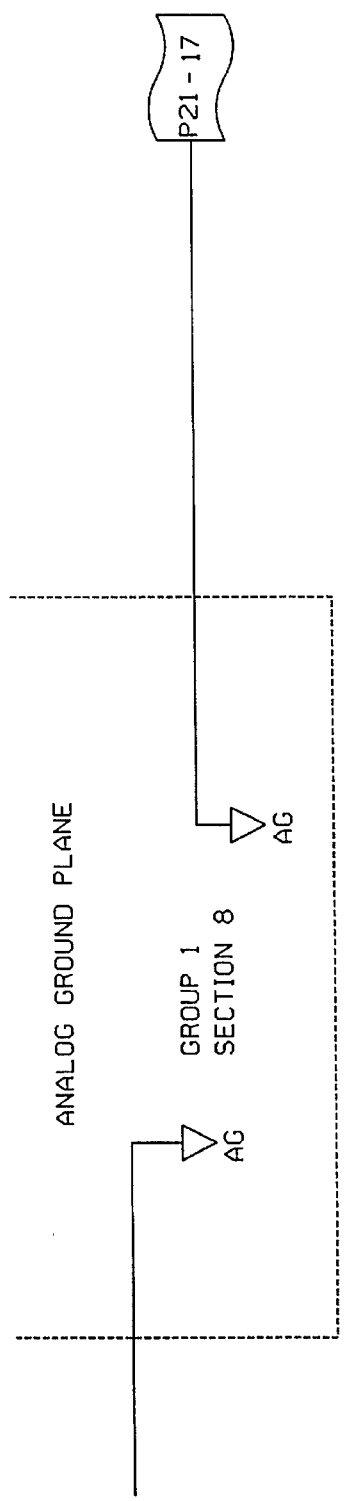
FIGURE 9D8

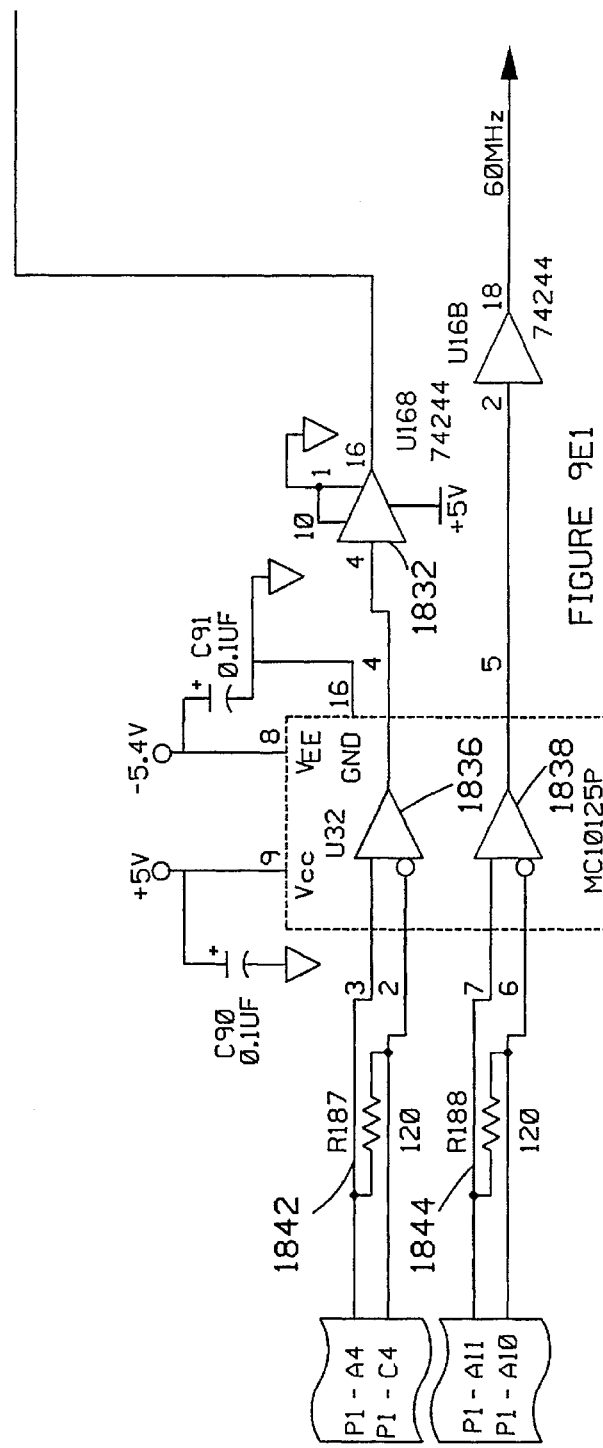
FIGURE 9E1

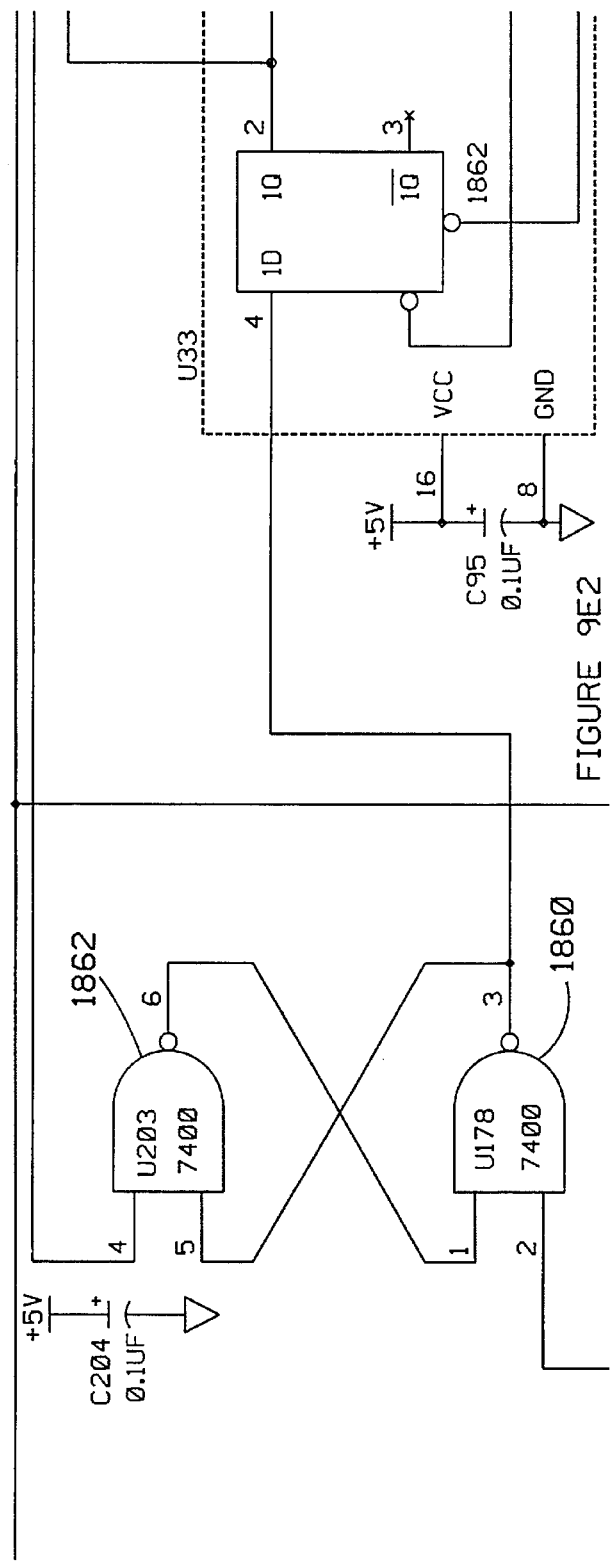
FIGURE 9E2

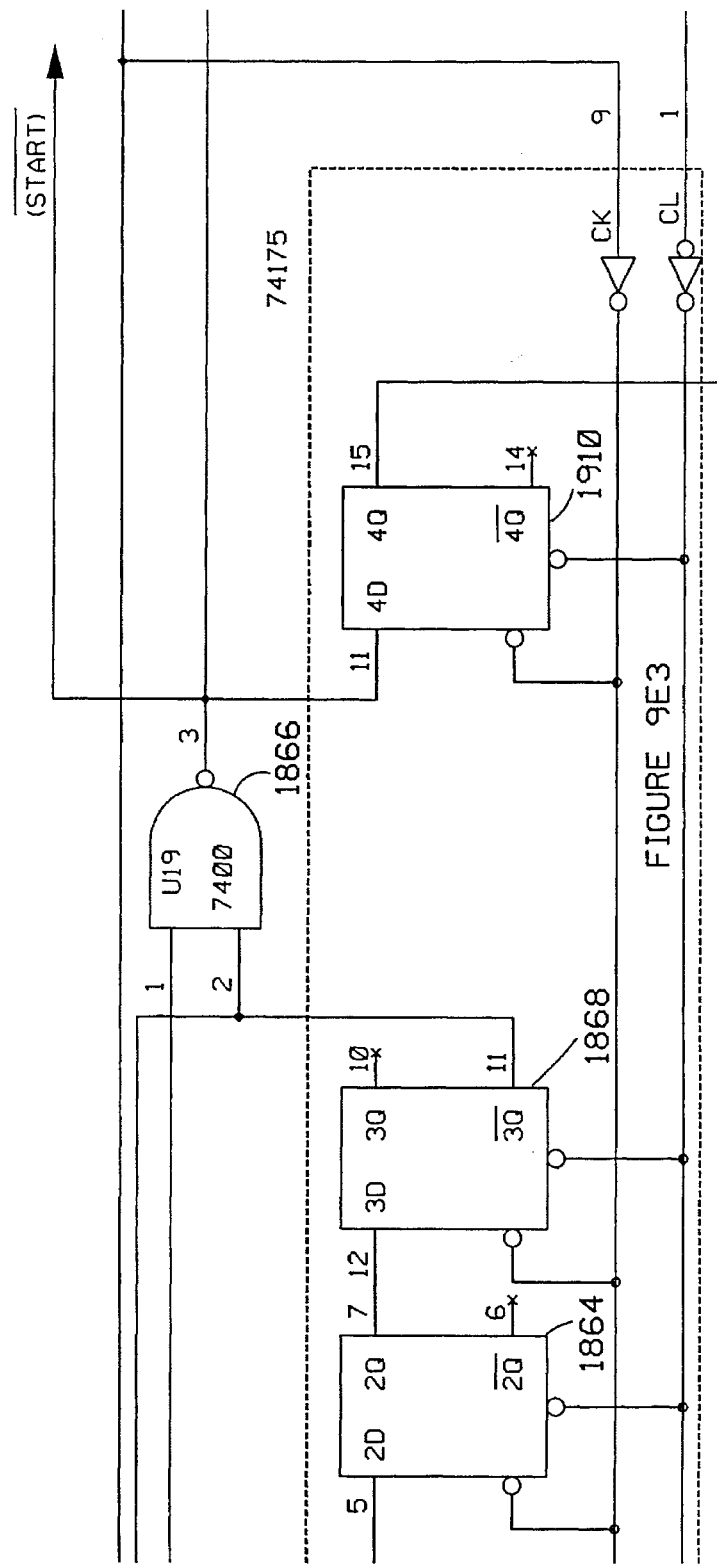
FIGURE 9E3

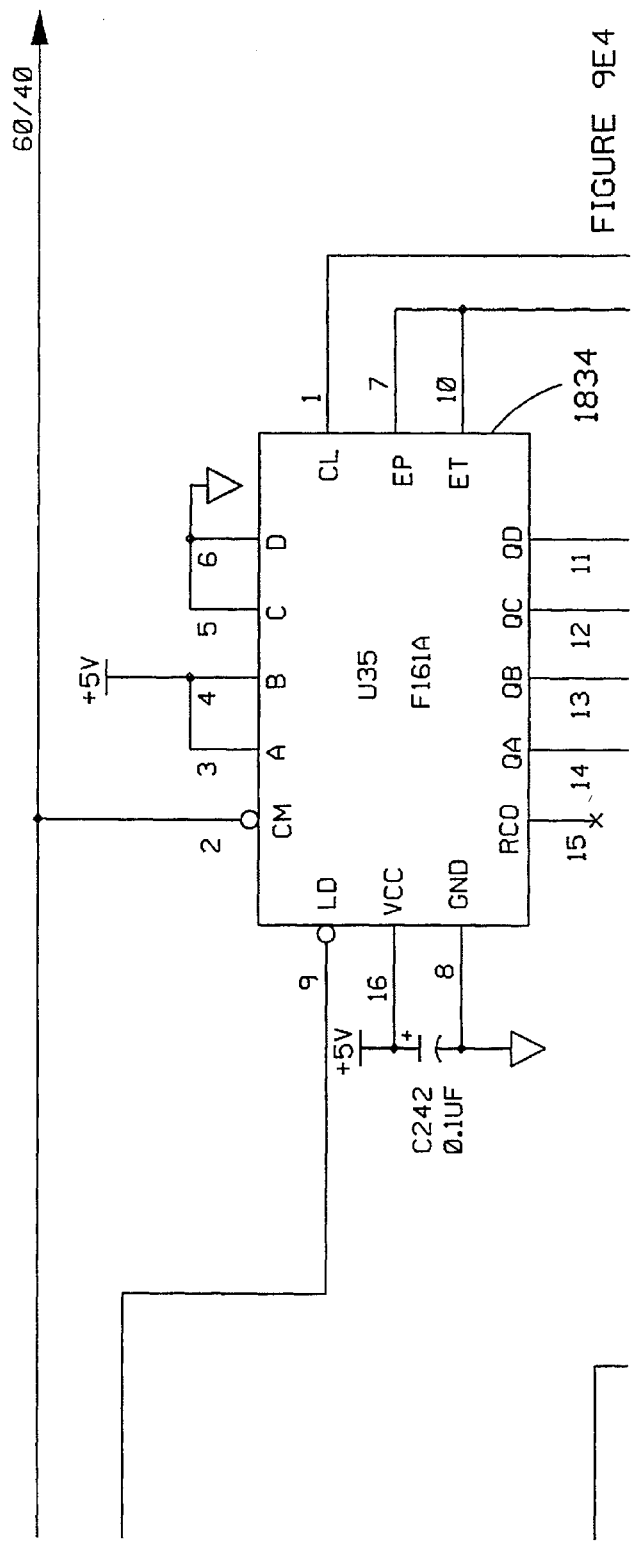
FIGURE 9E4

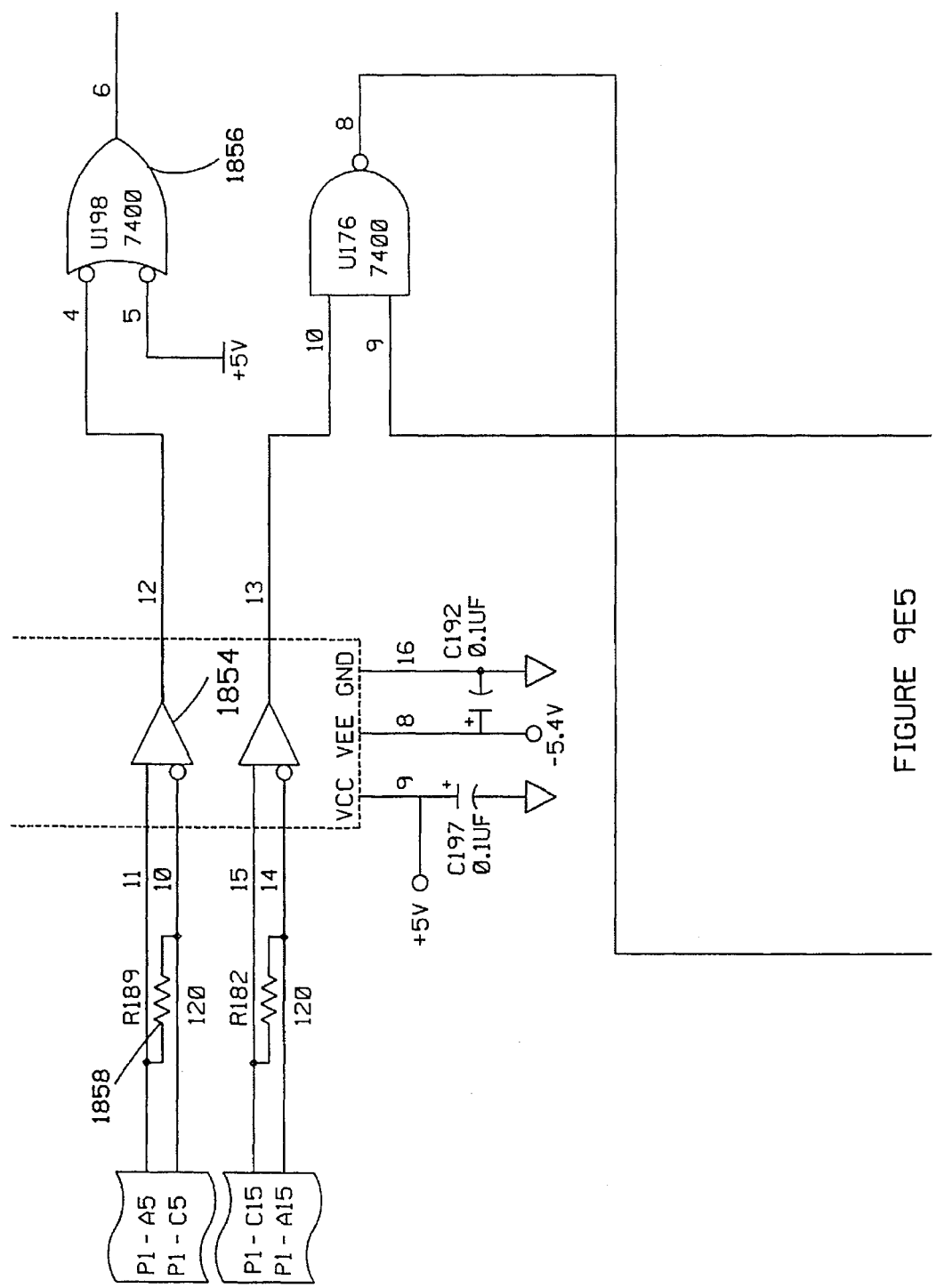
FIGURE 9E5

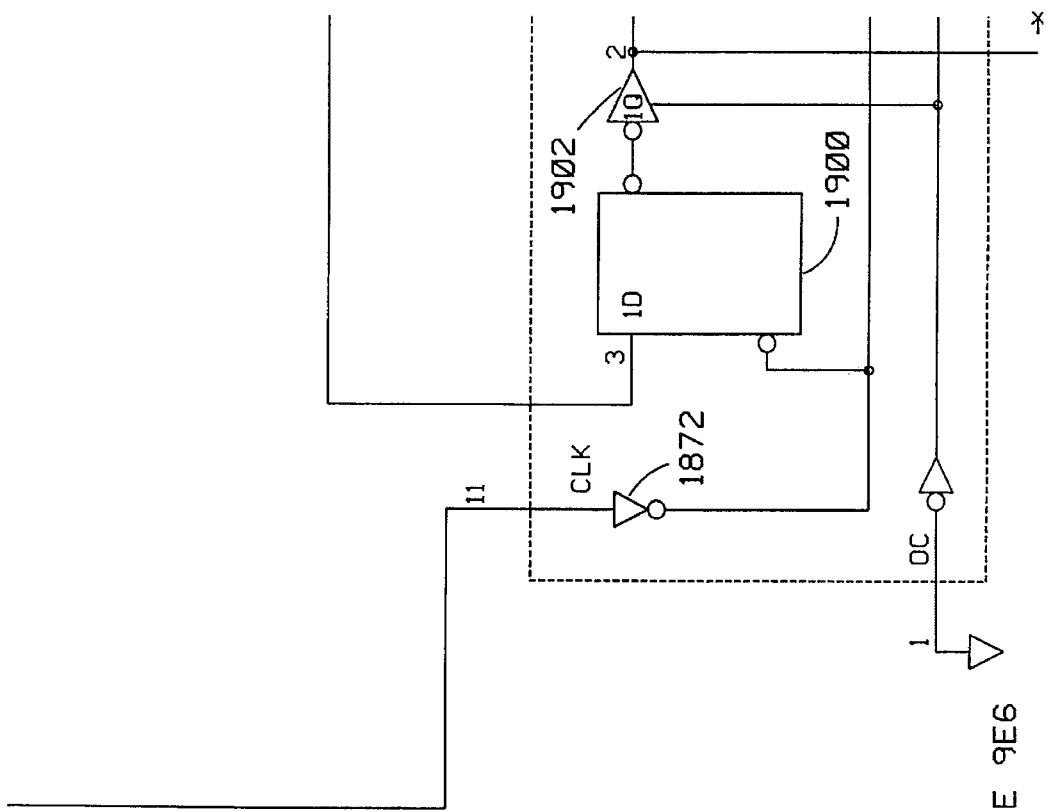
FIGURE 9E6

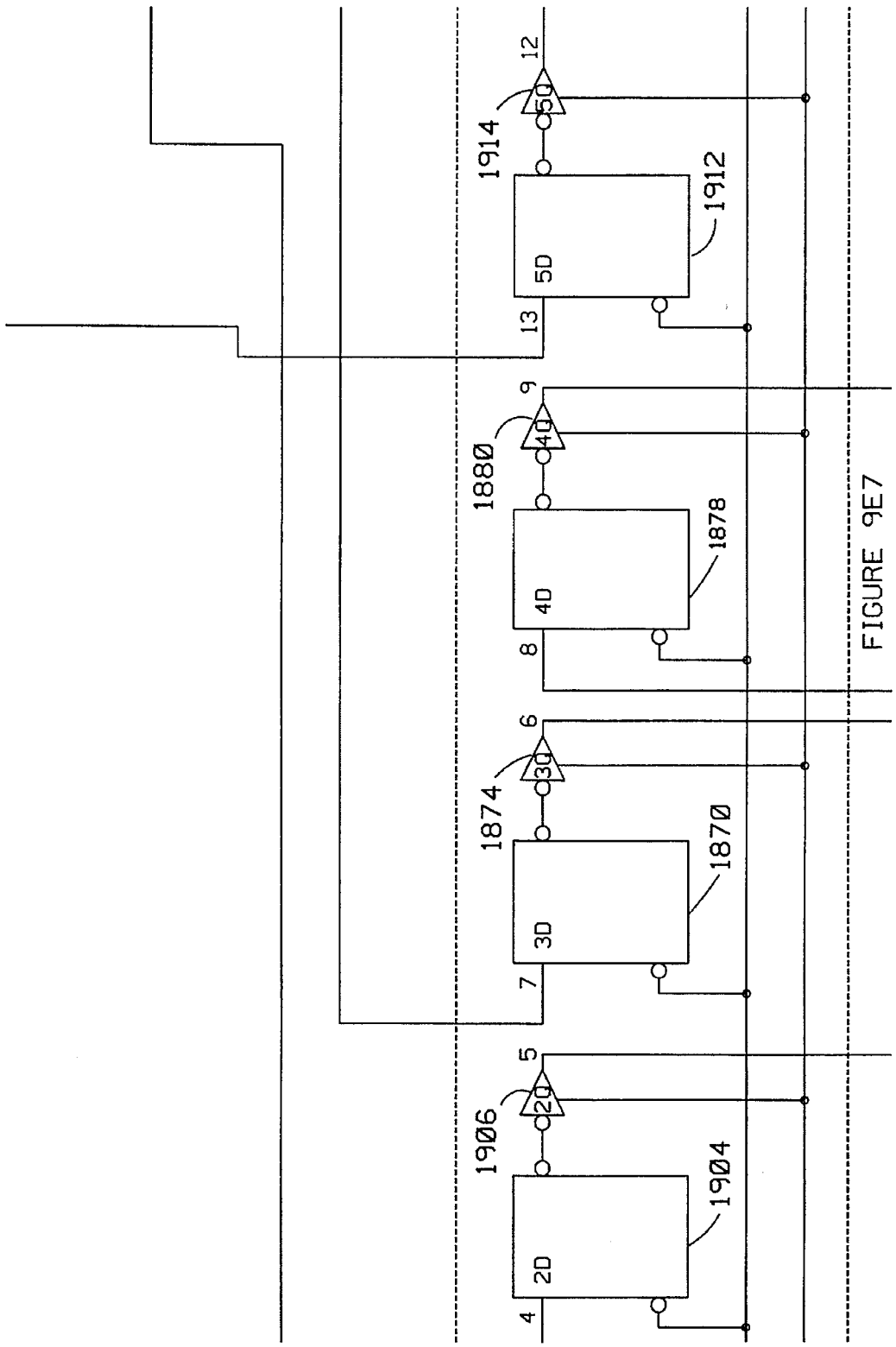
FIGURE 9E7

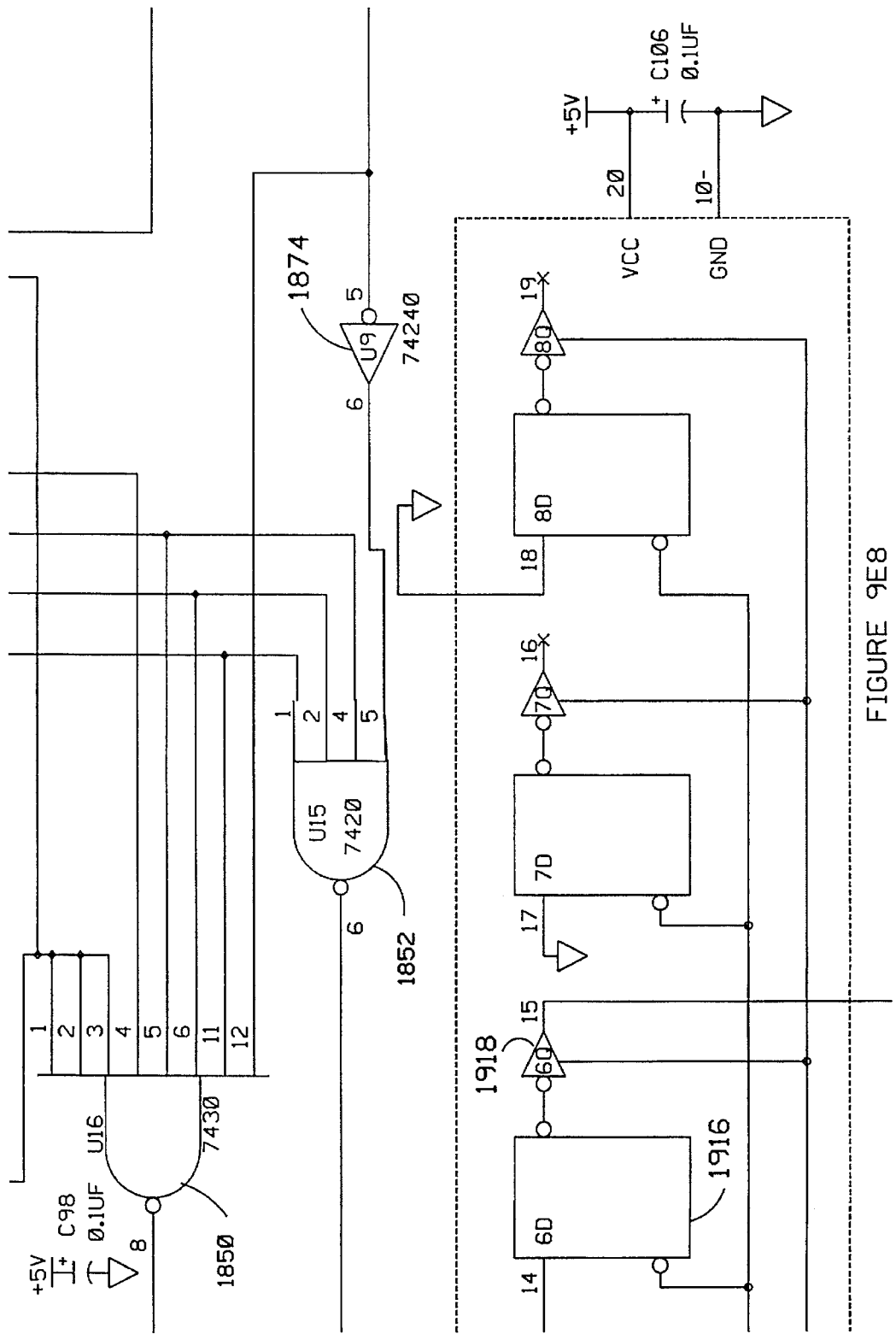
FIGURE 9E8

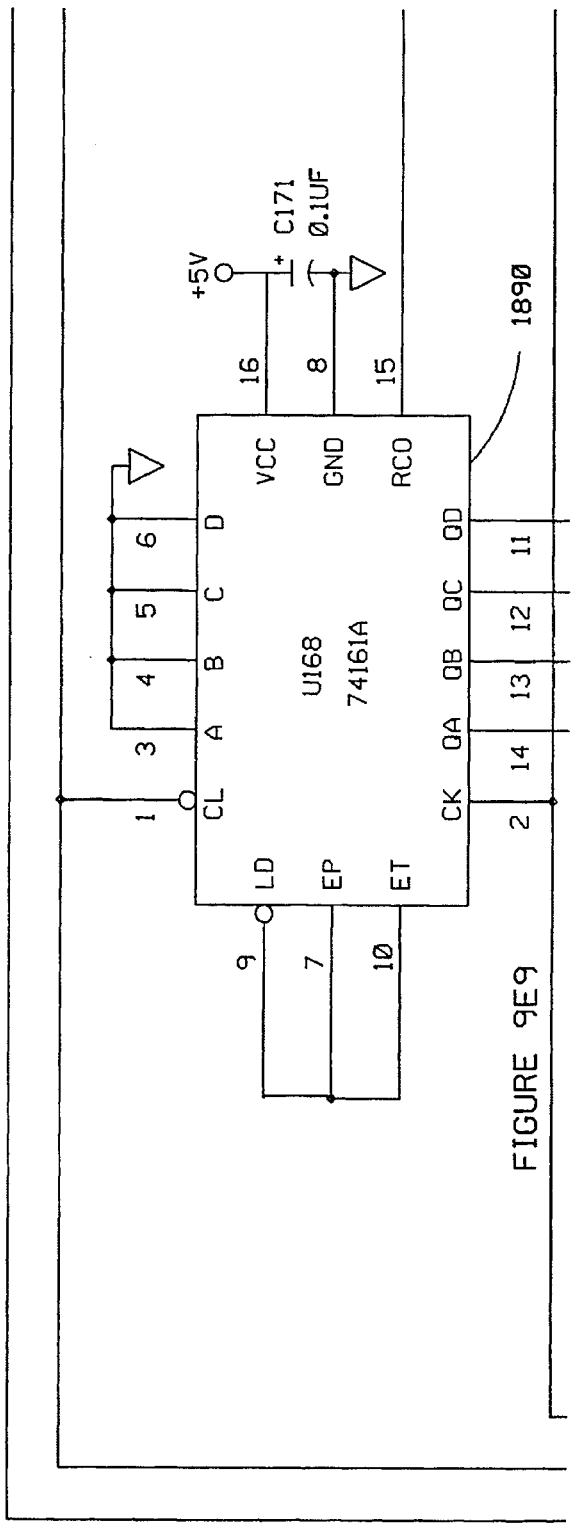
FIGURE 9E9

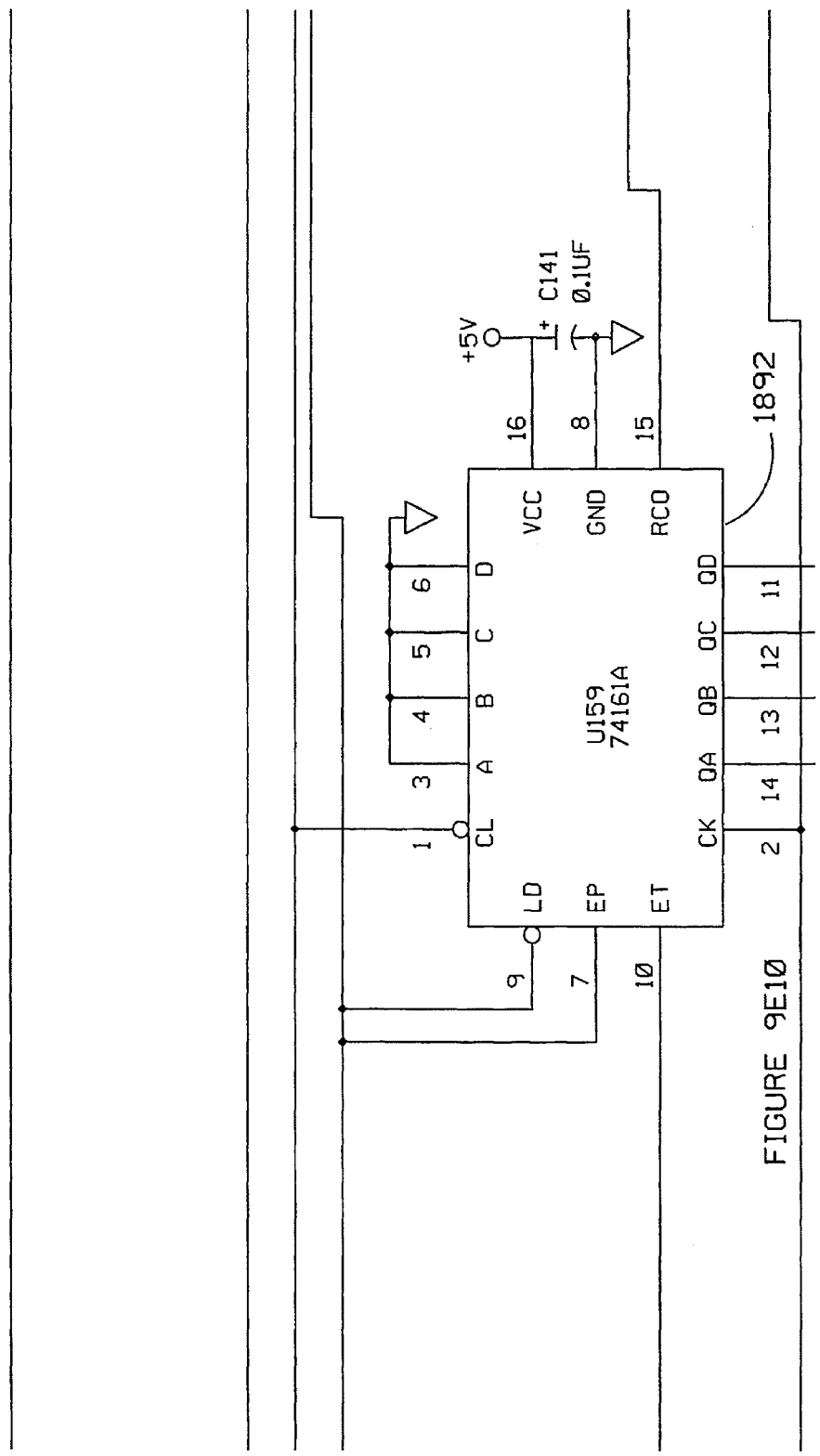
FIGURE 9E10

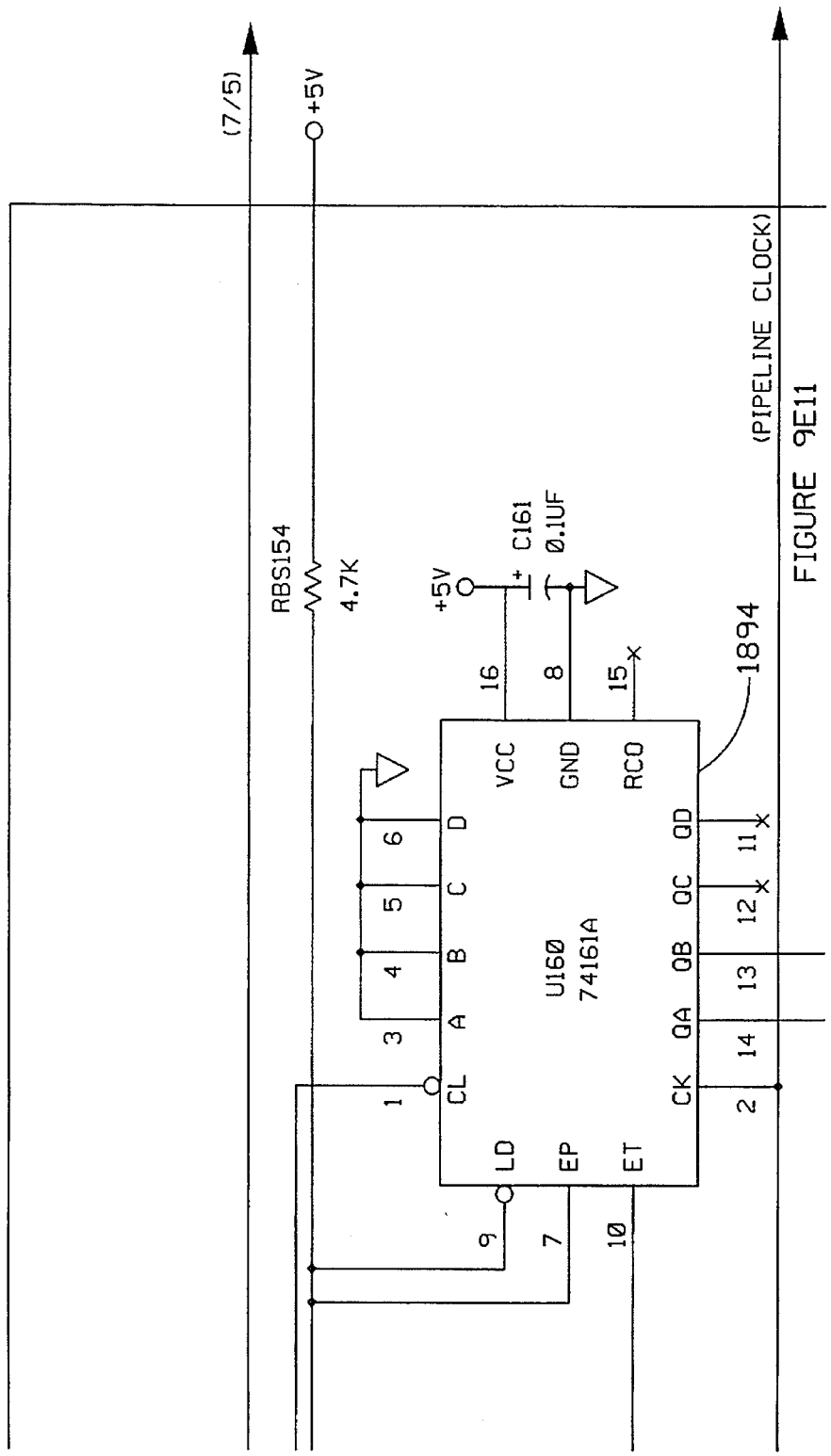
FIGURE 9E11

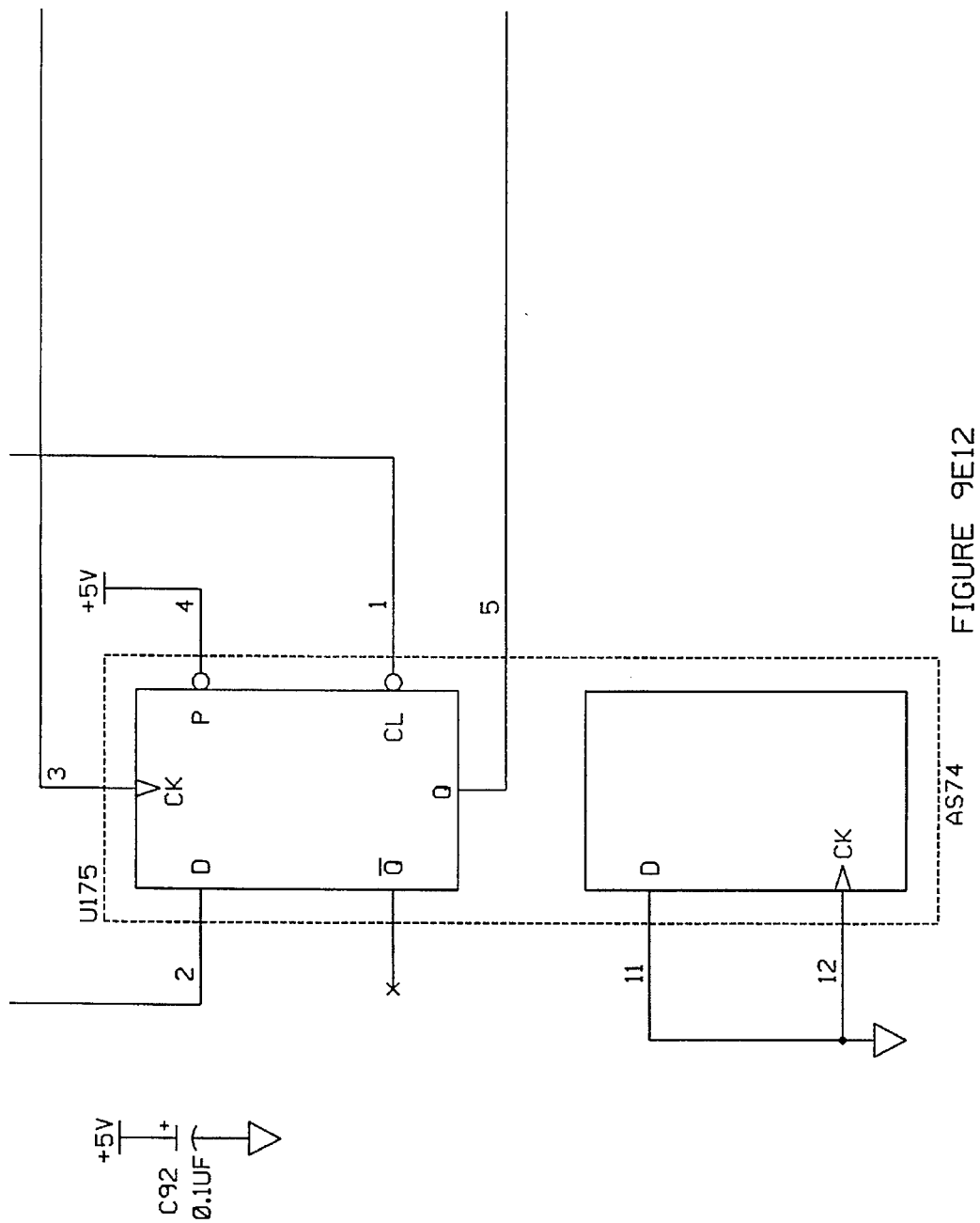

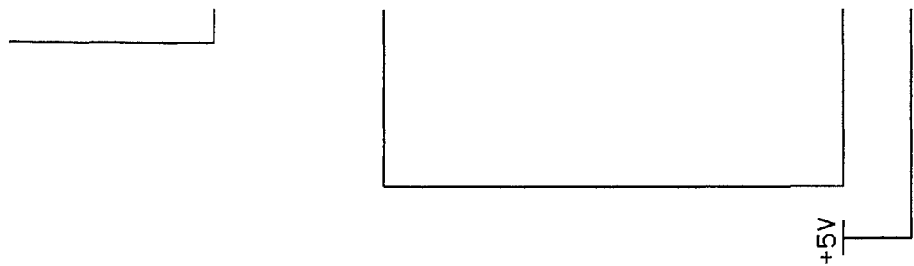
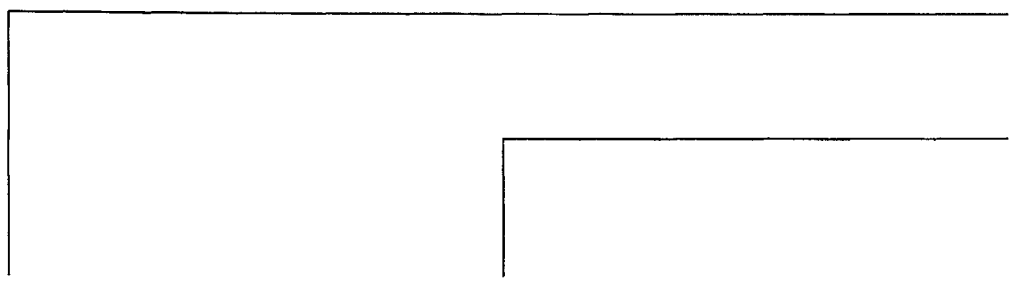
FIGURE 9E13

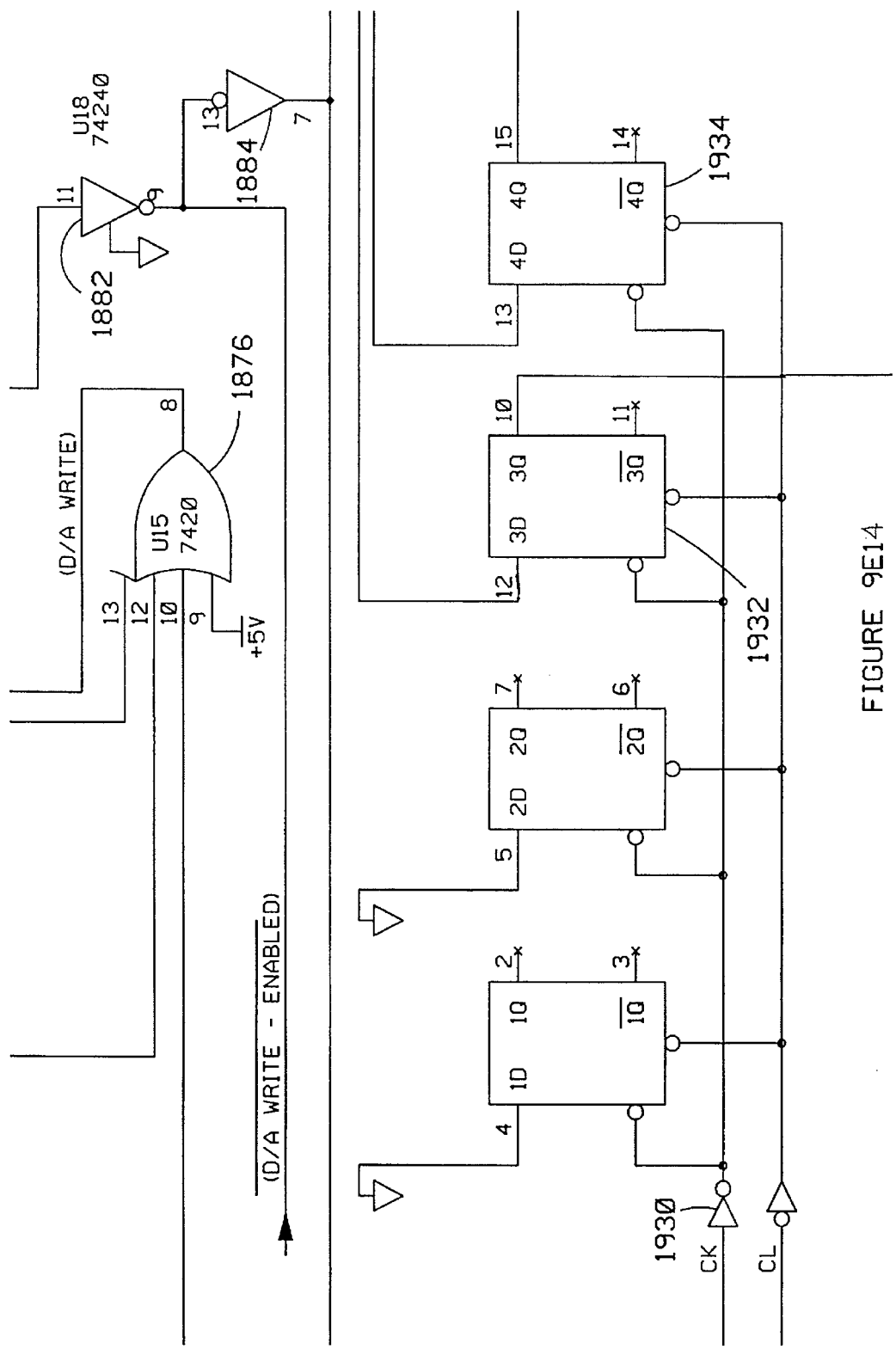
FIGURE 9E14

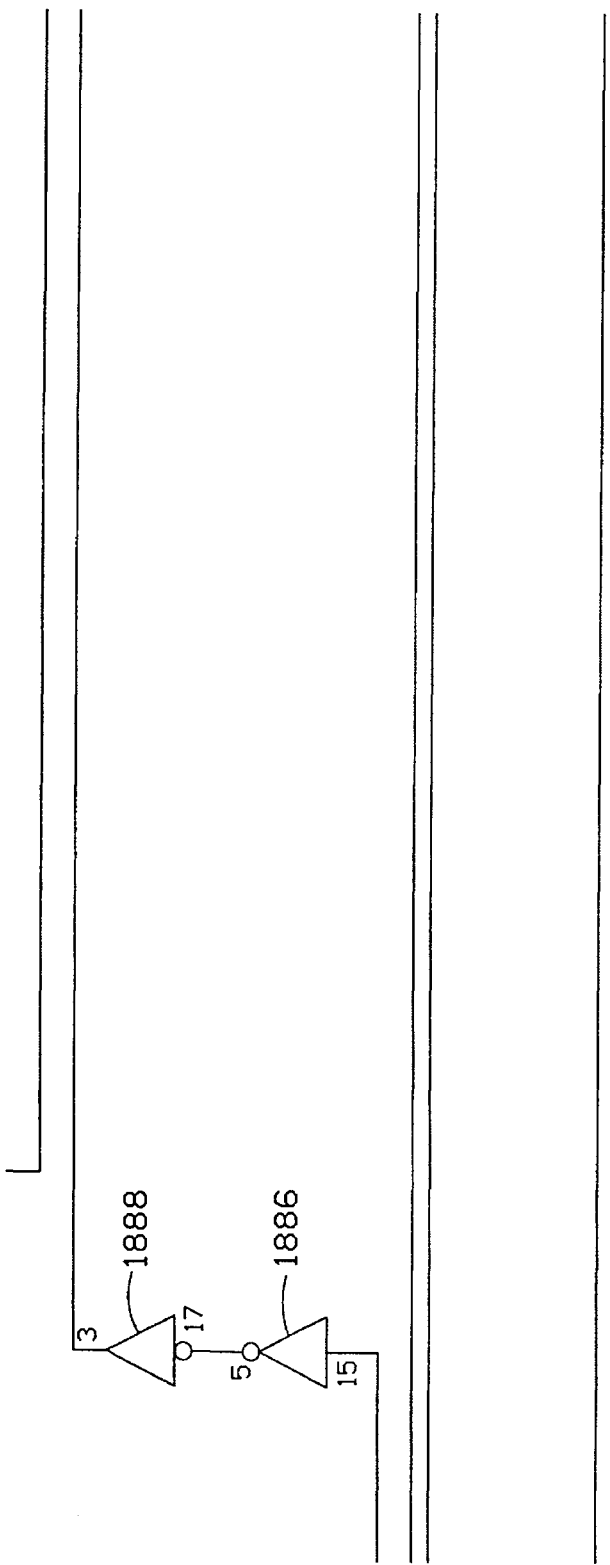
FIGURE 9E15

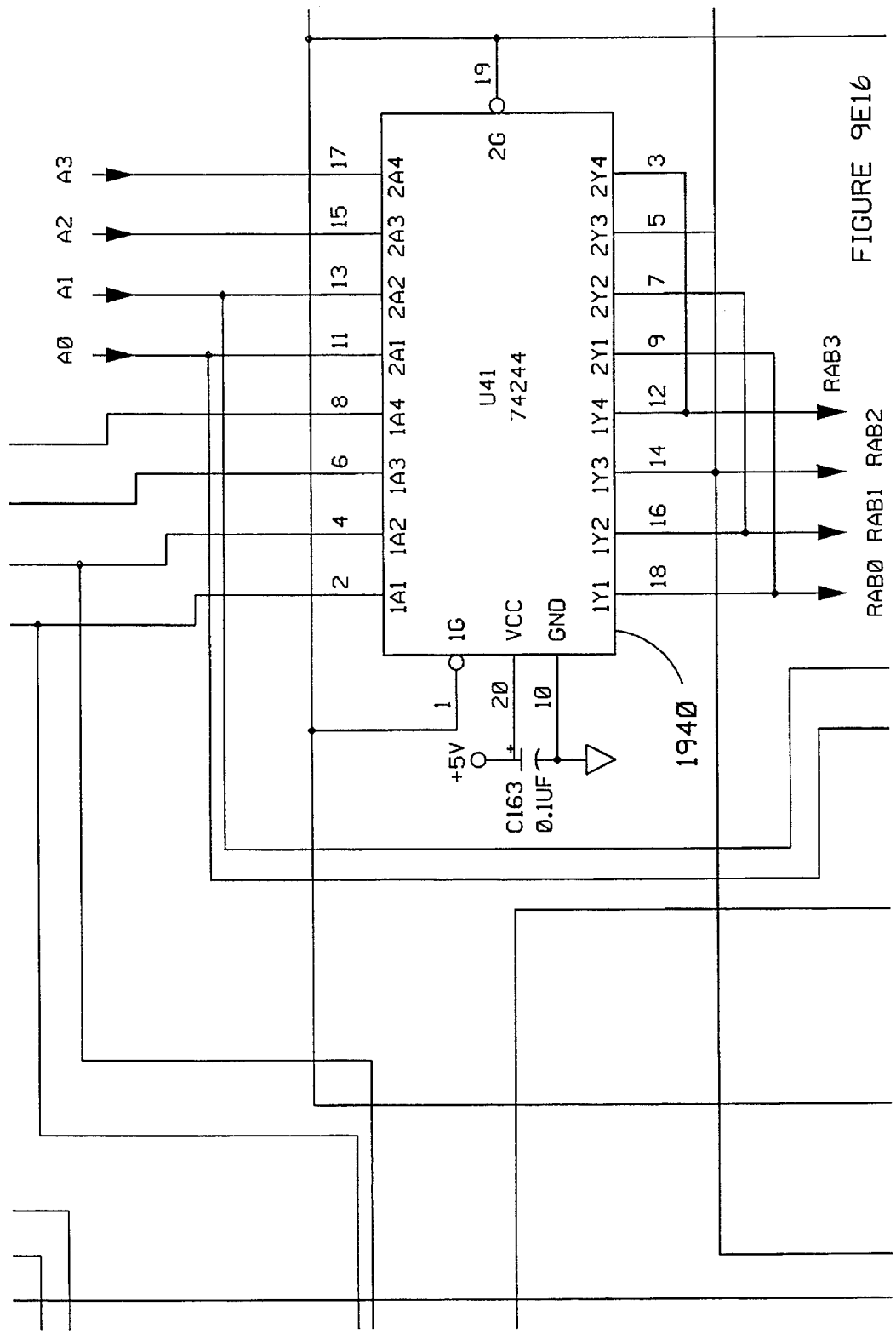
FIGURE 9E16

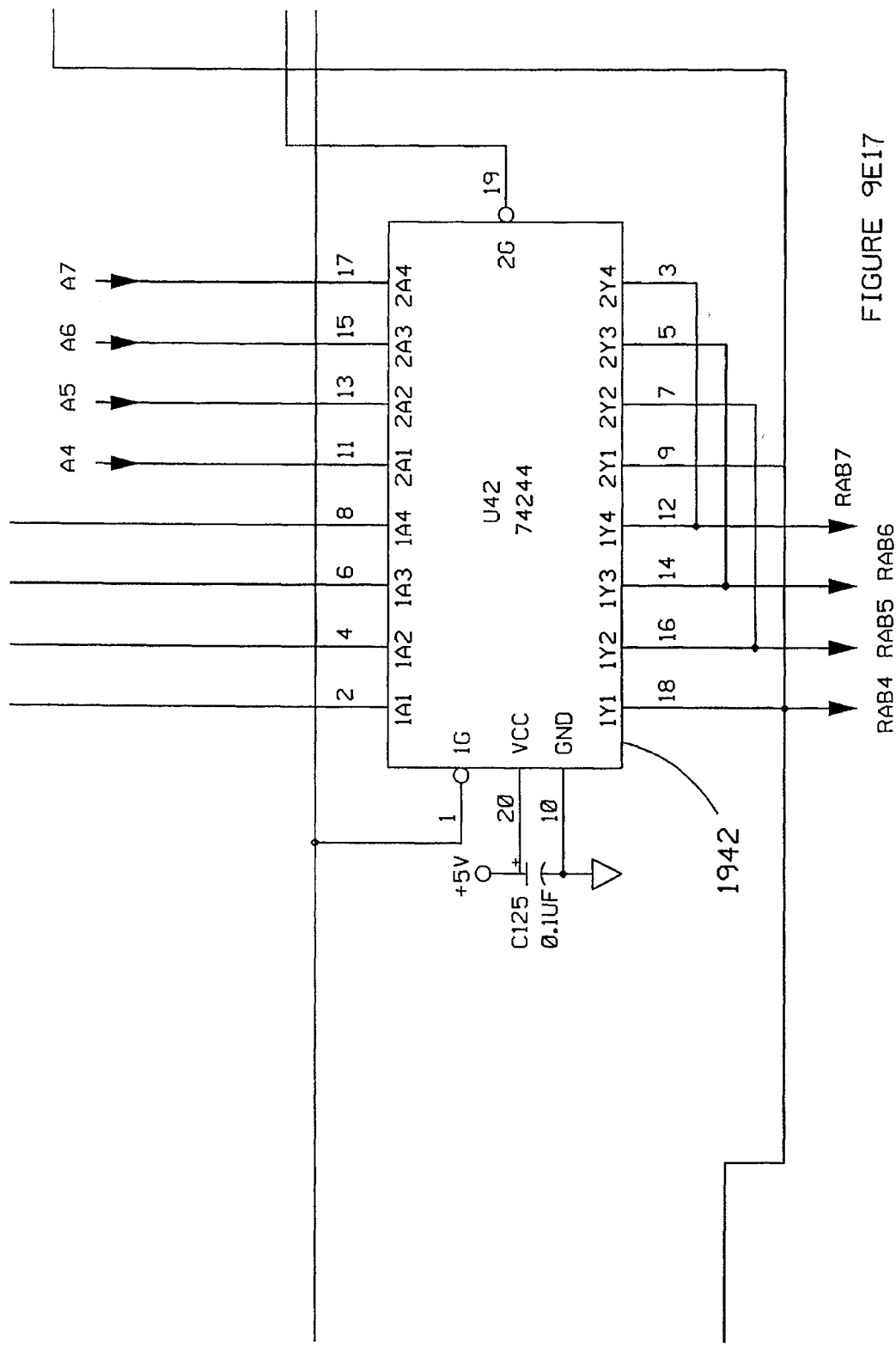
FIGURE 9E17

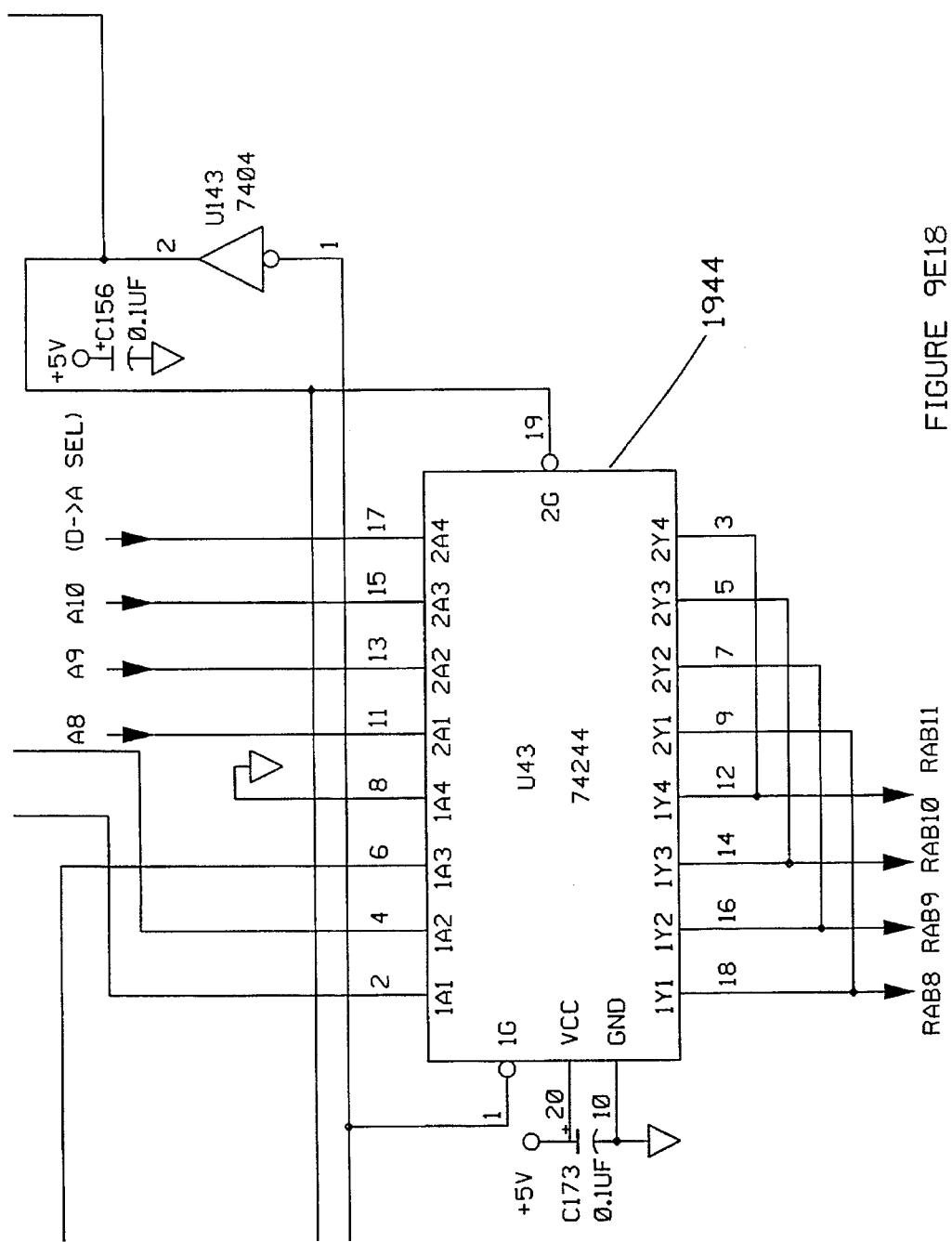
FIGURE 9E18

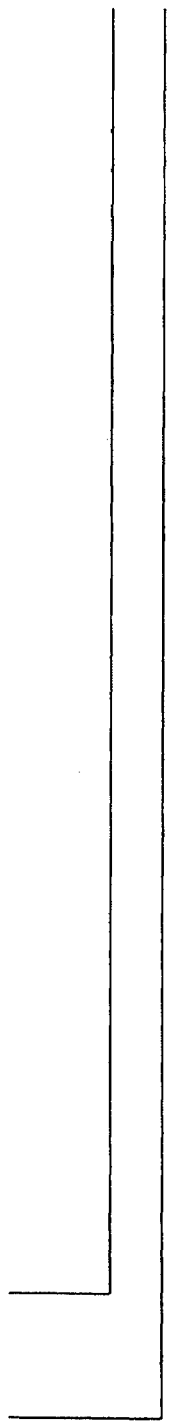
FIGURE 9E19

FIGURE 9E20

FIGURE 9E21

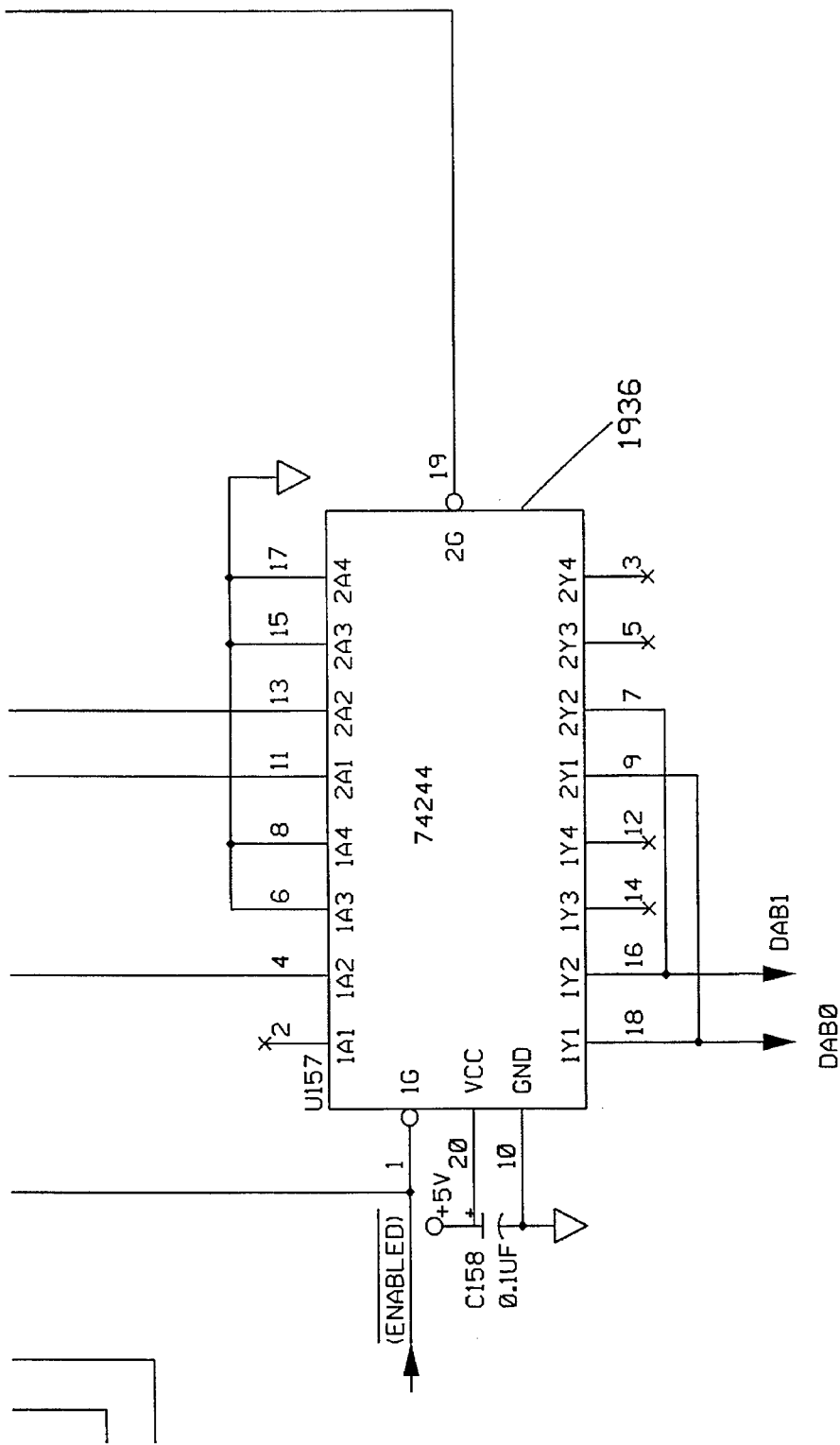
FIGURE 9E22

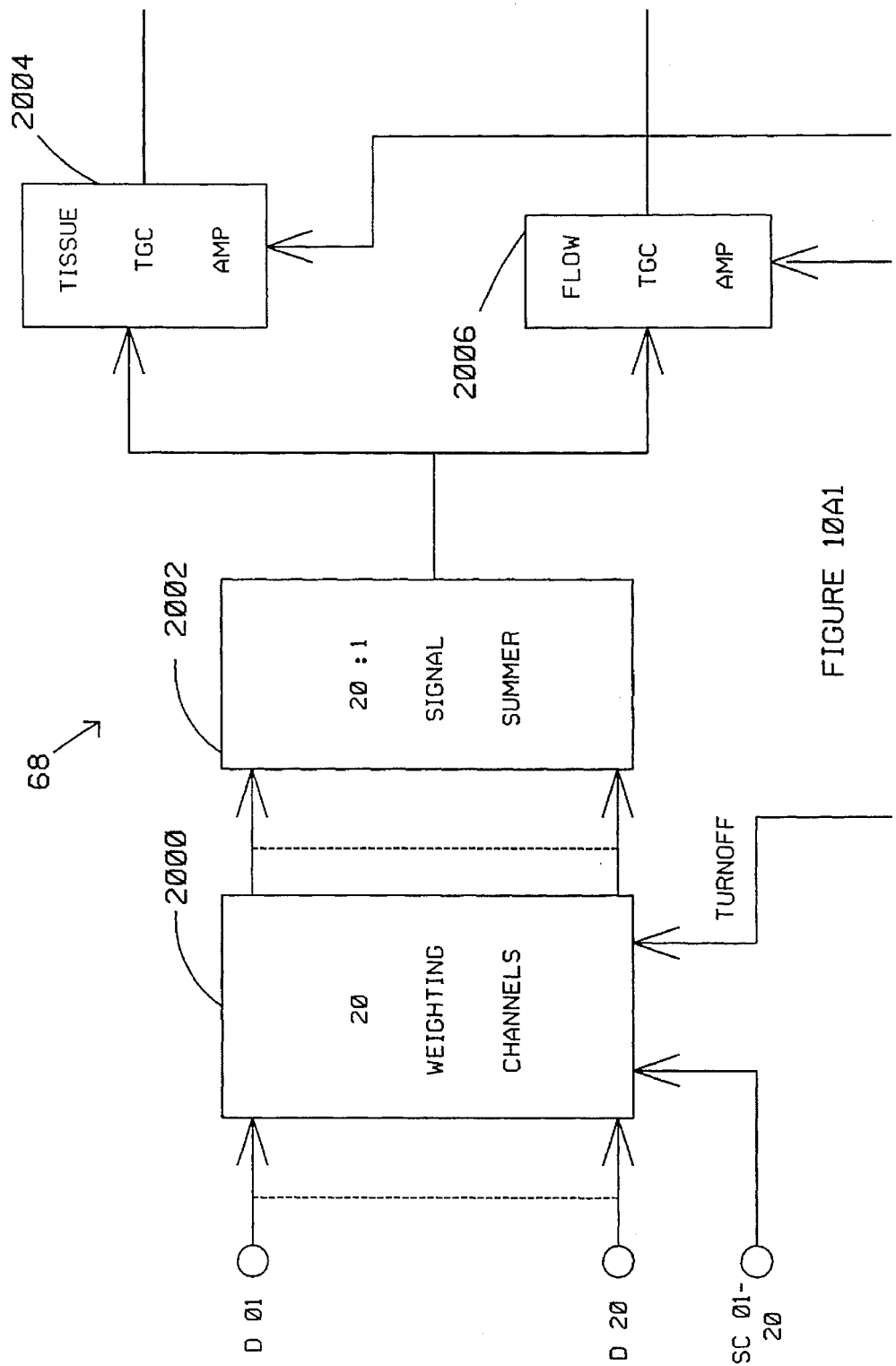

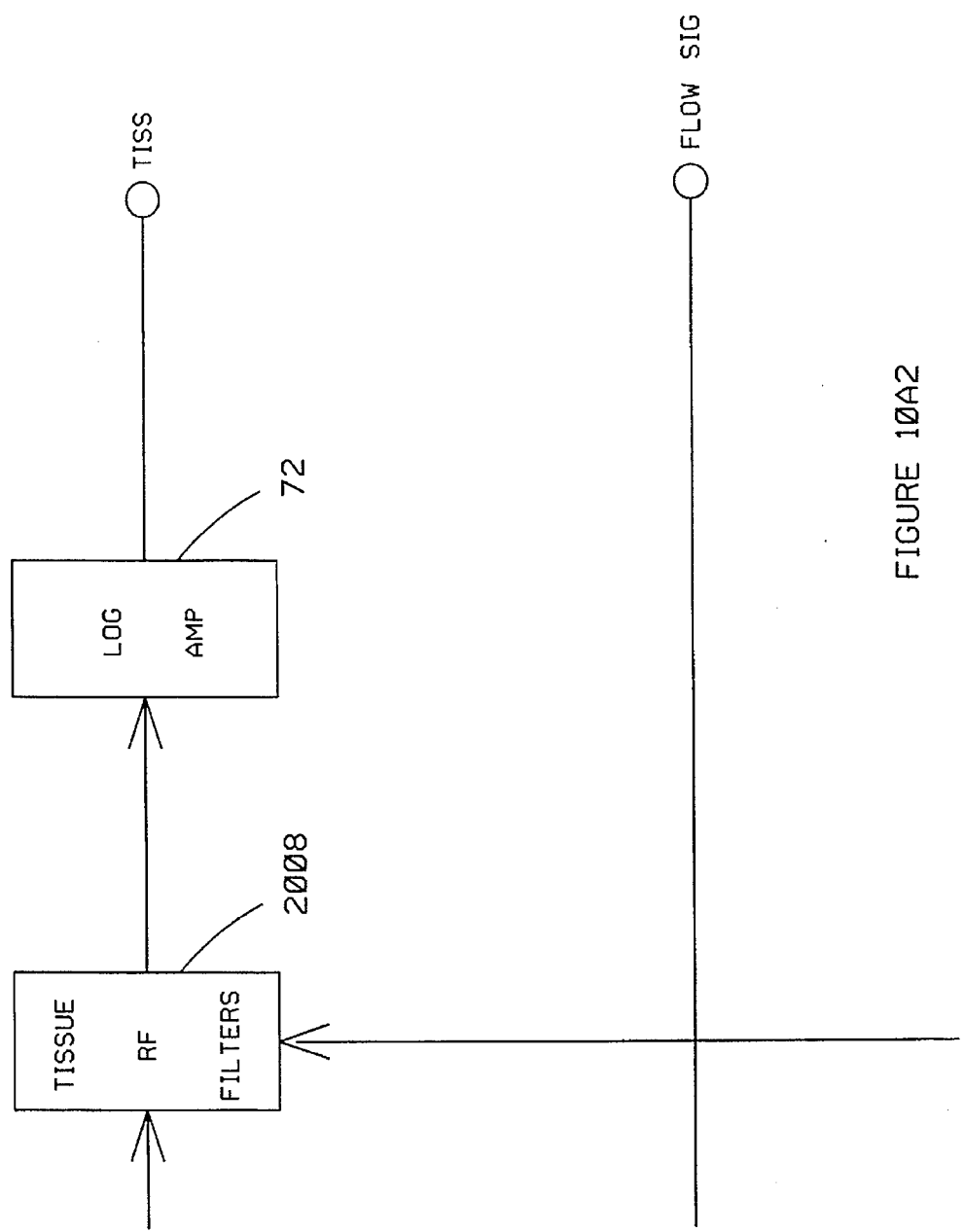
FIGURE 10A2

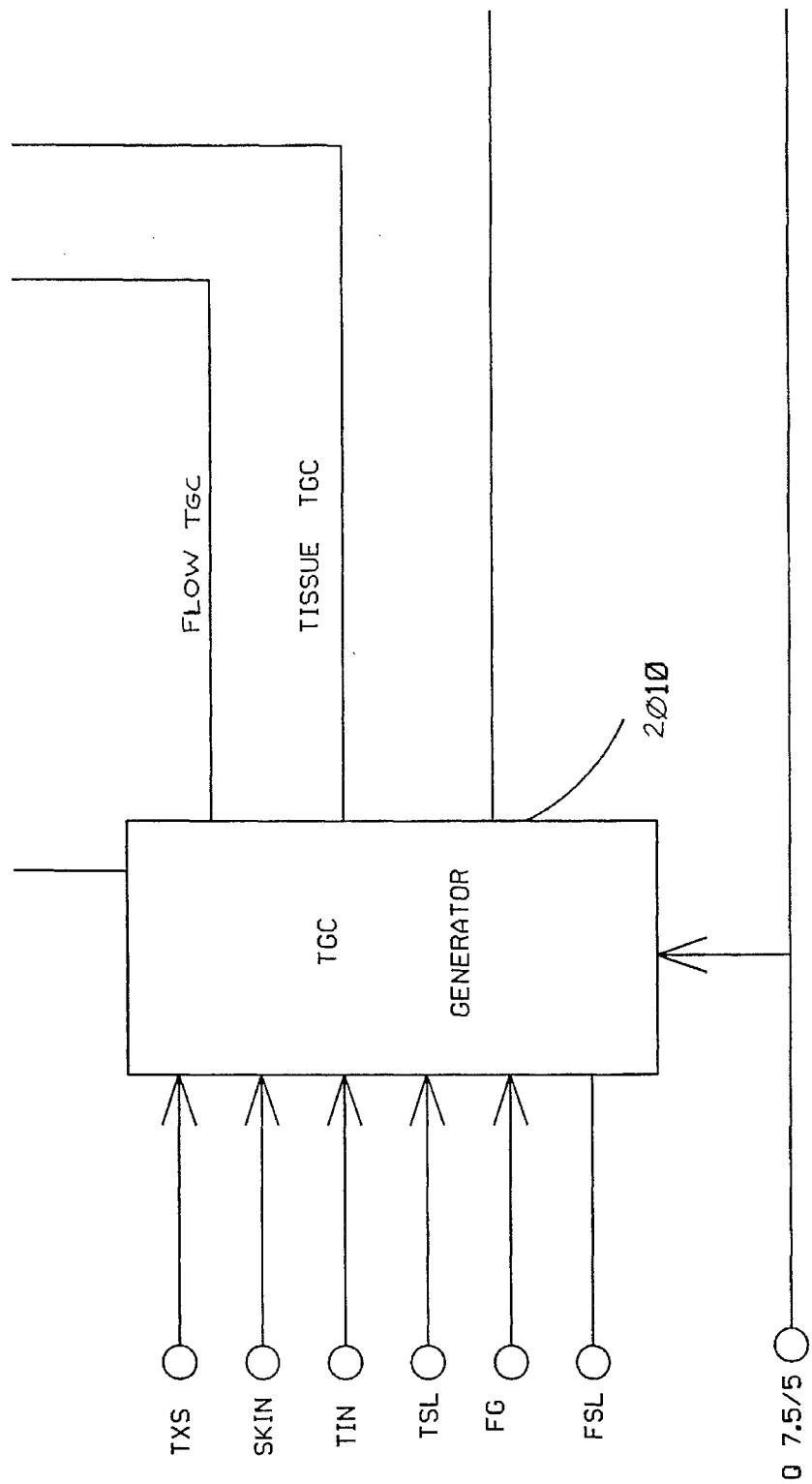
FIGURE 10A3

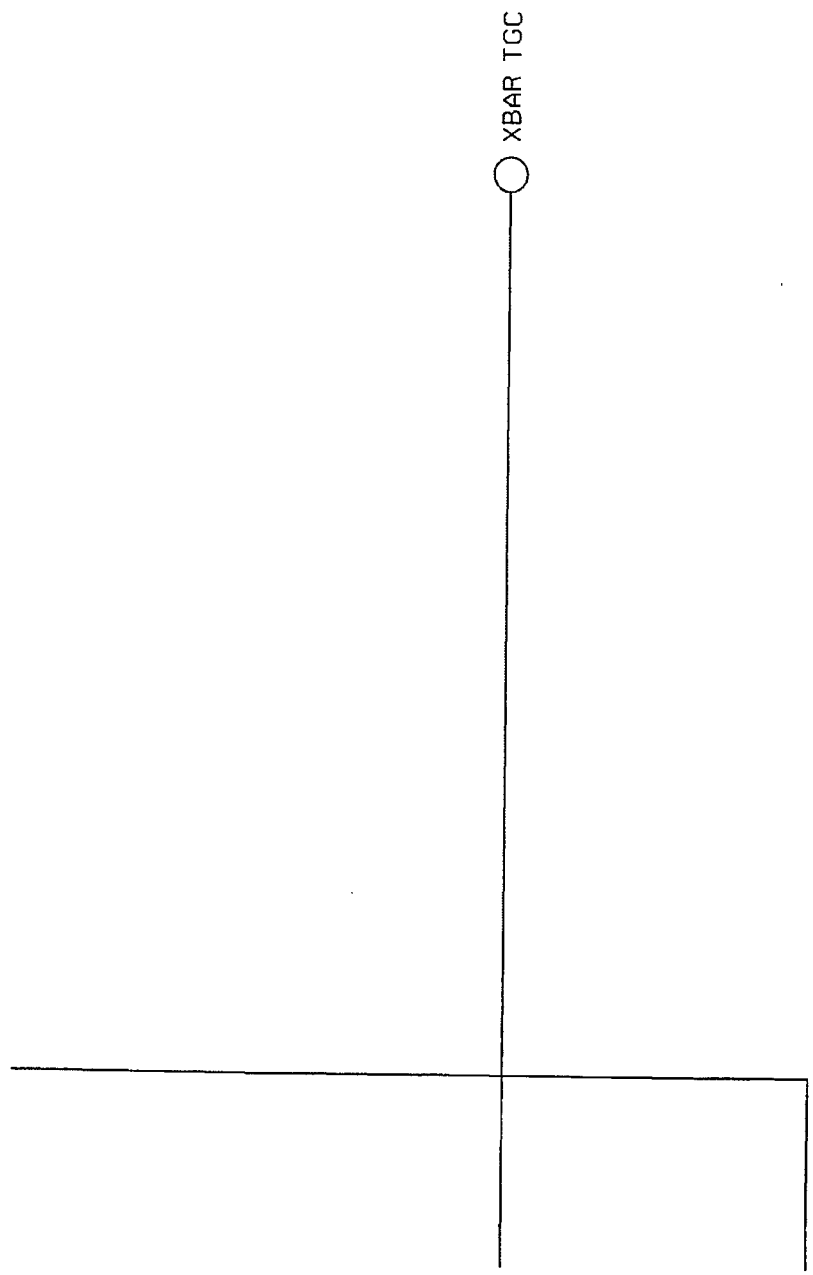

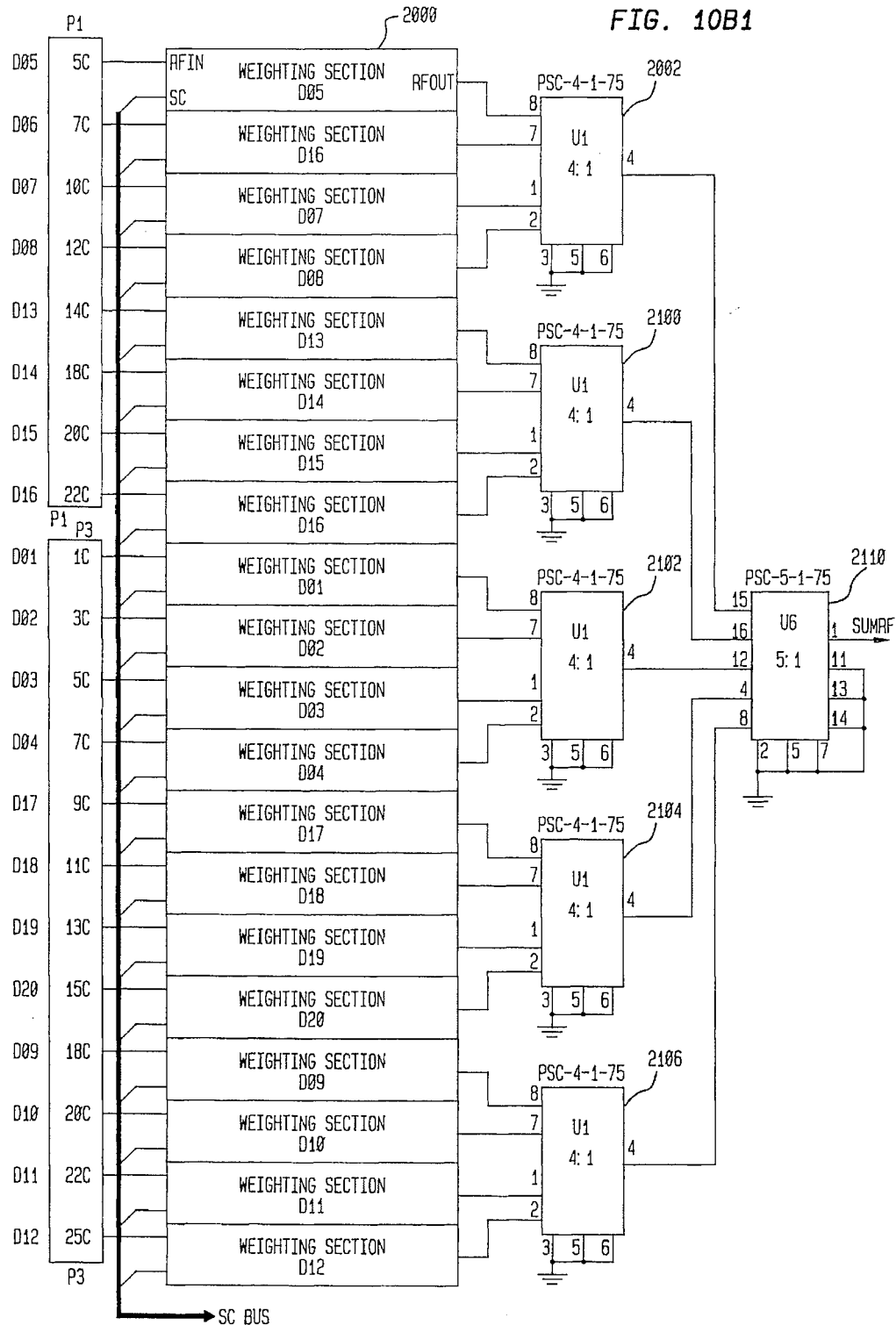
FIG. 10B1

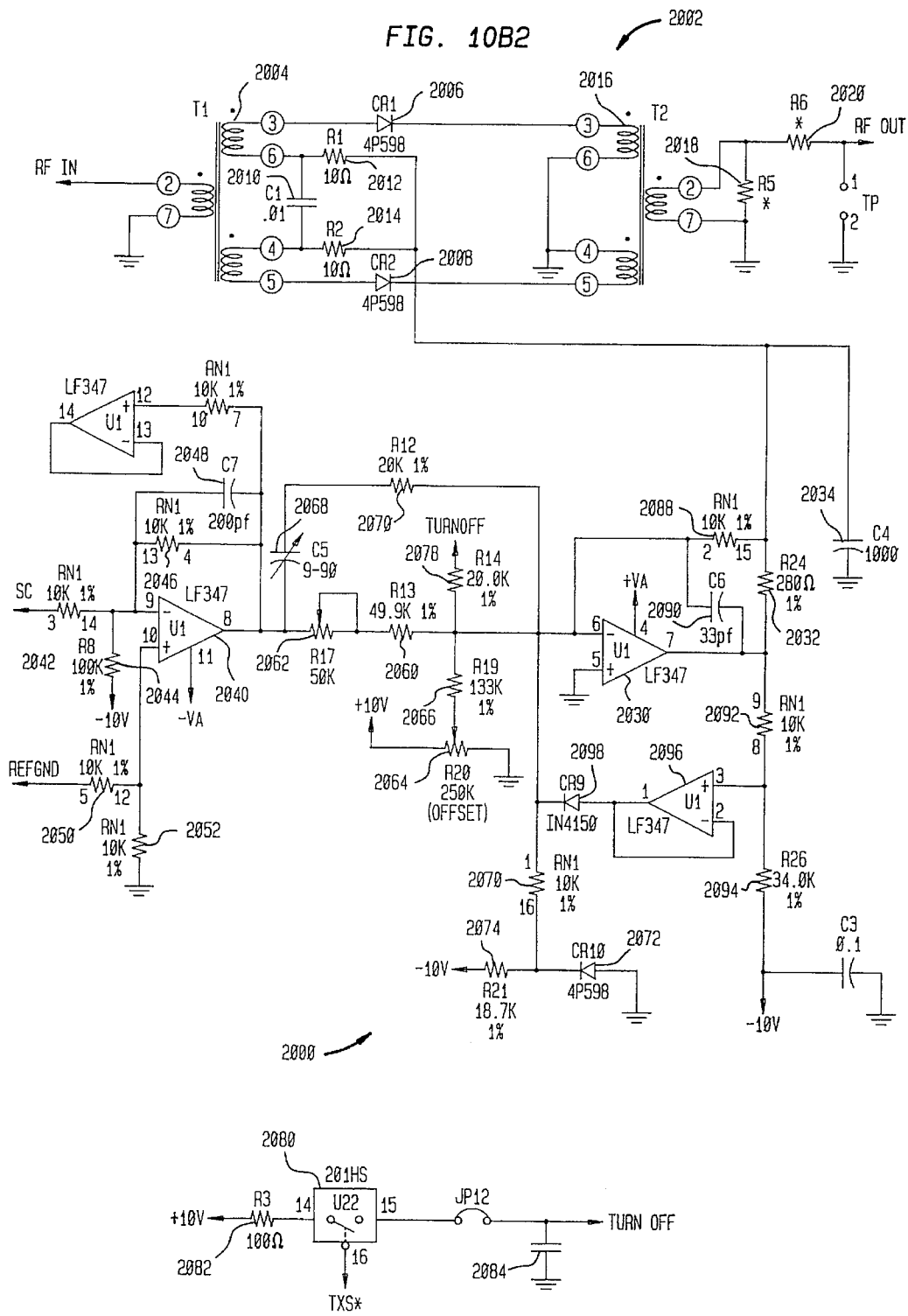
FIG. 10B2

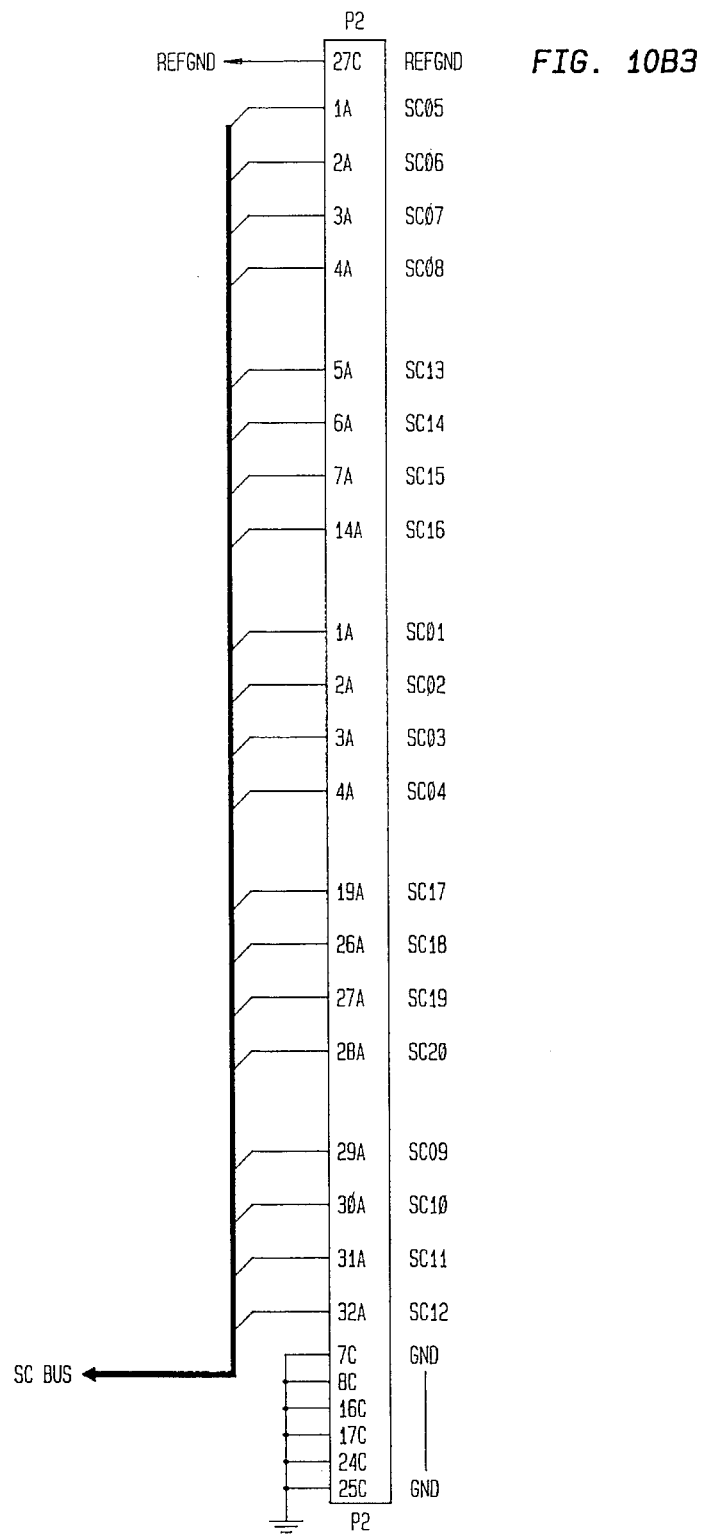
FIG. 10B3

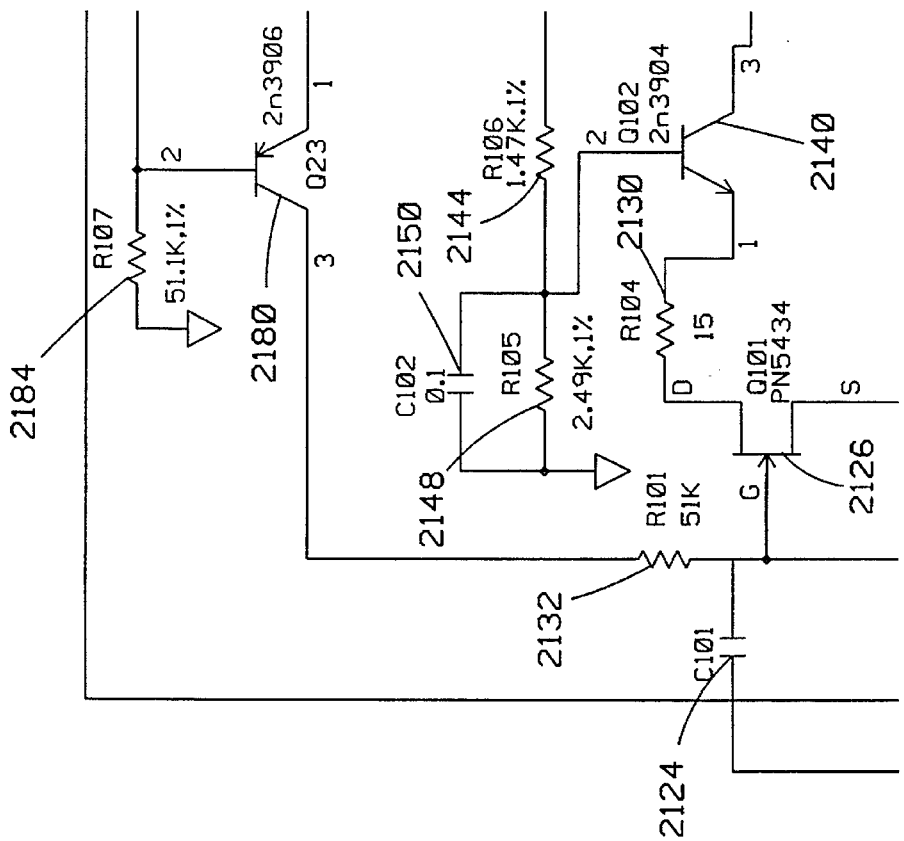
FIGURE 10C1

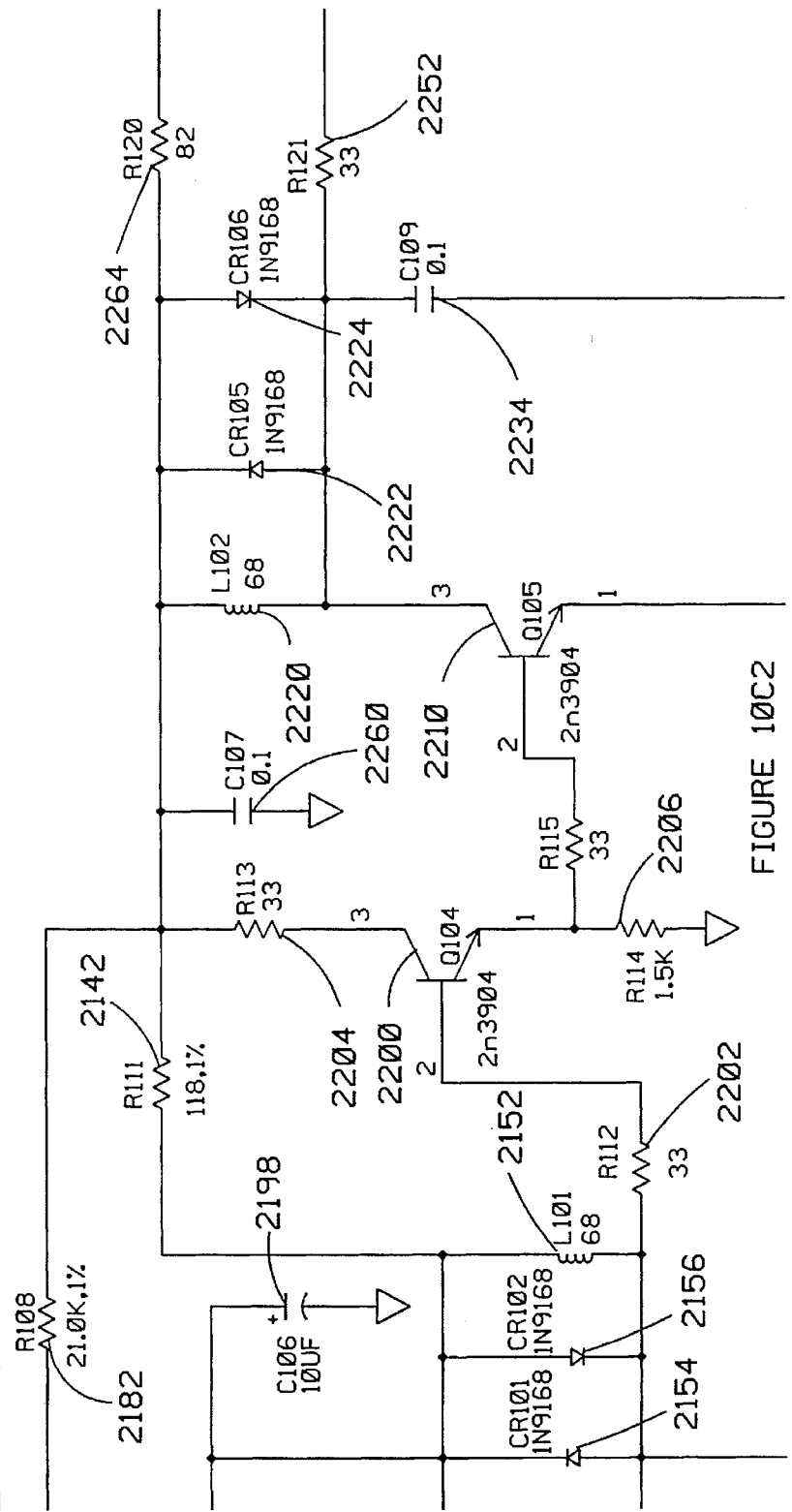
FIGURE 10C2

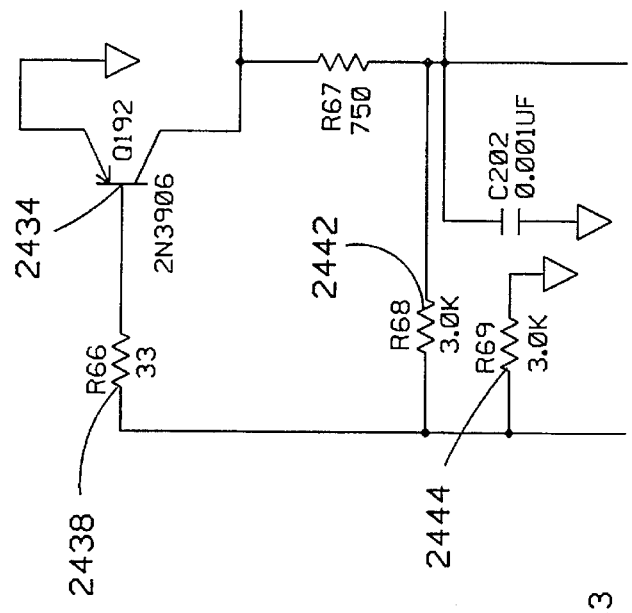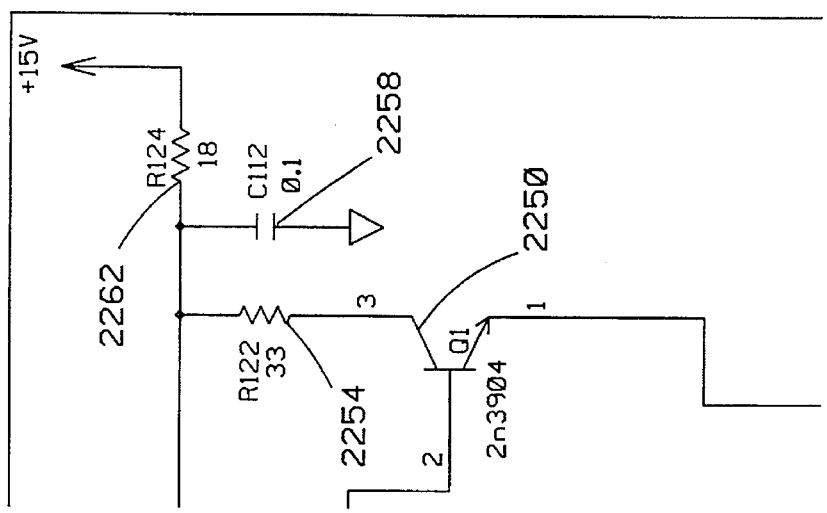
FIGURE 10C3

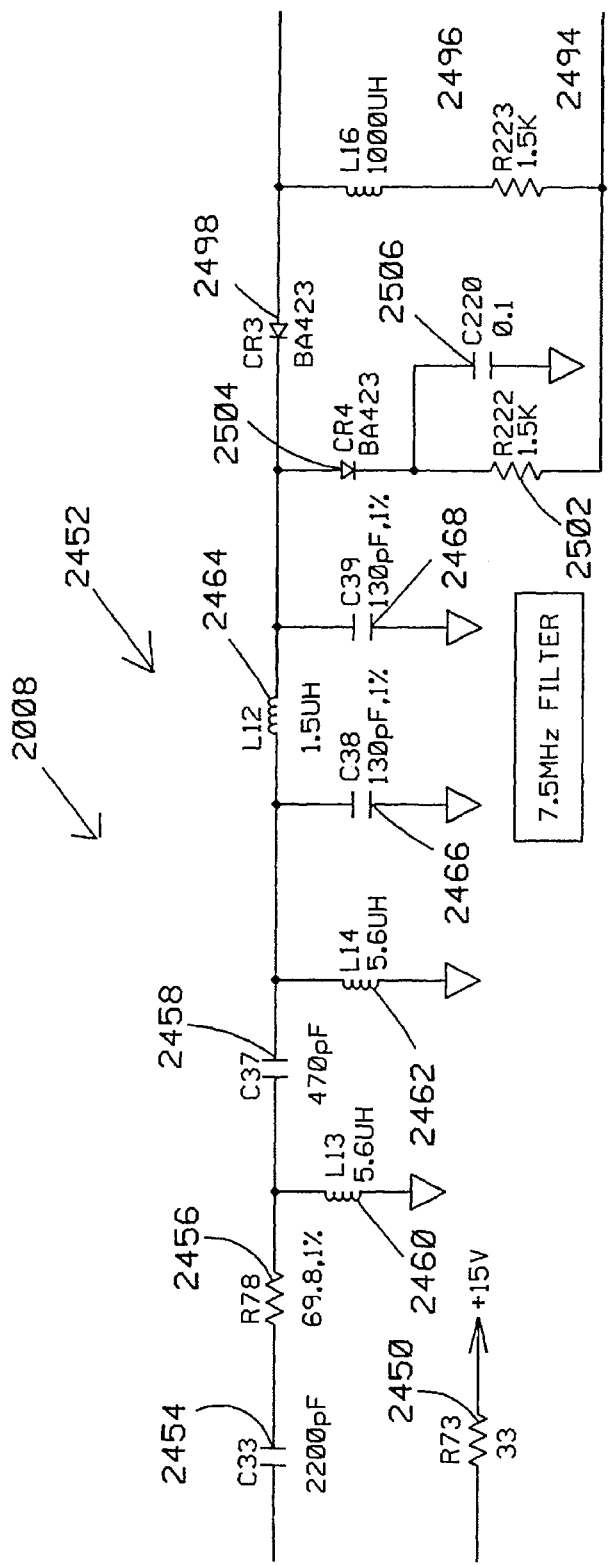
FIGURE 10C4

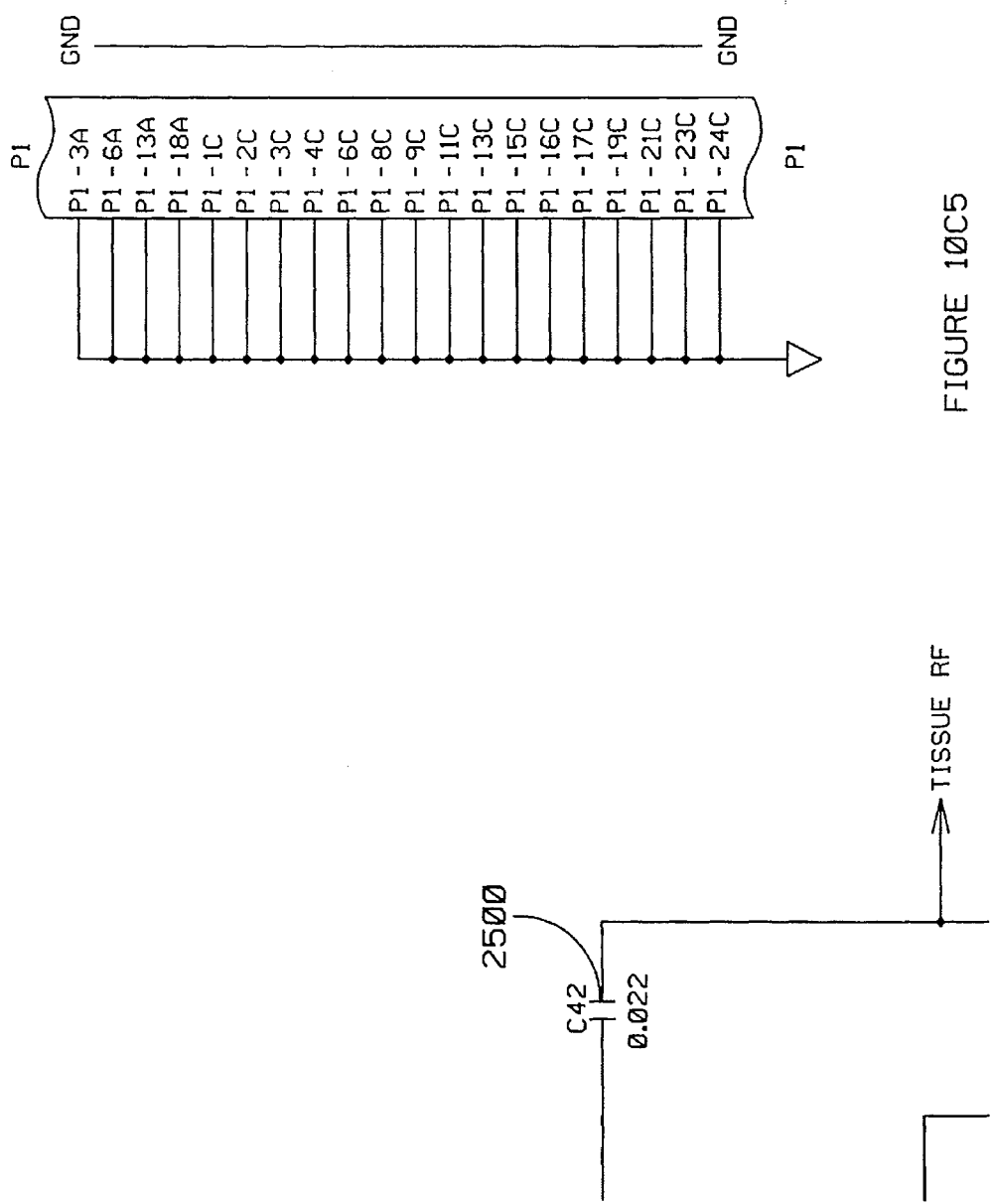
FIGURE 10C5

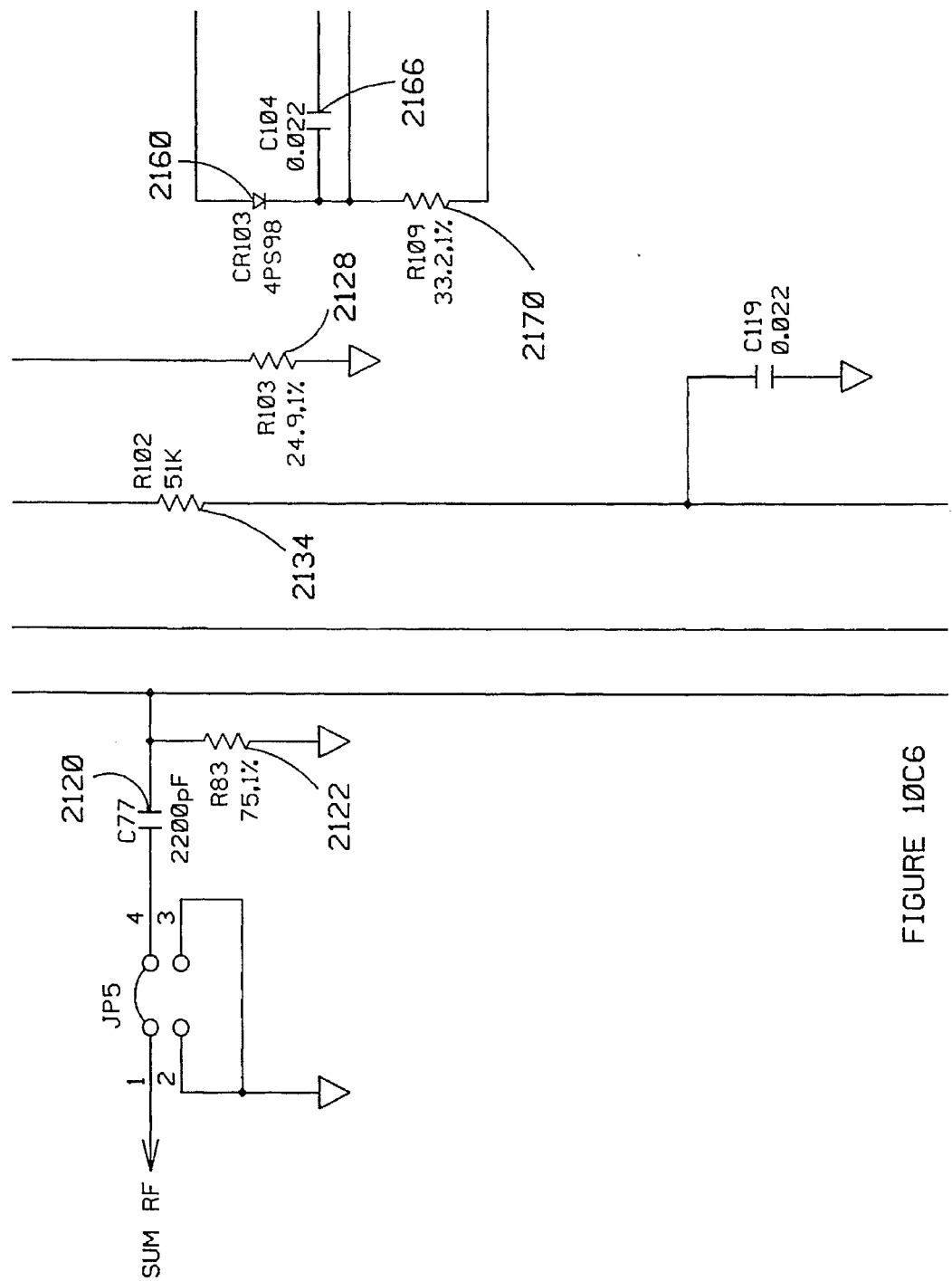
FIGURE 10C6

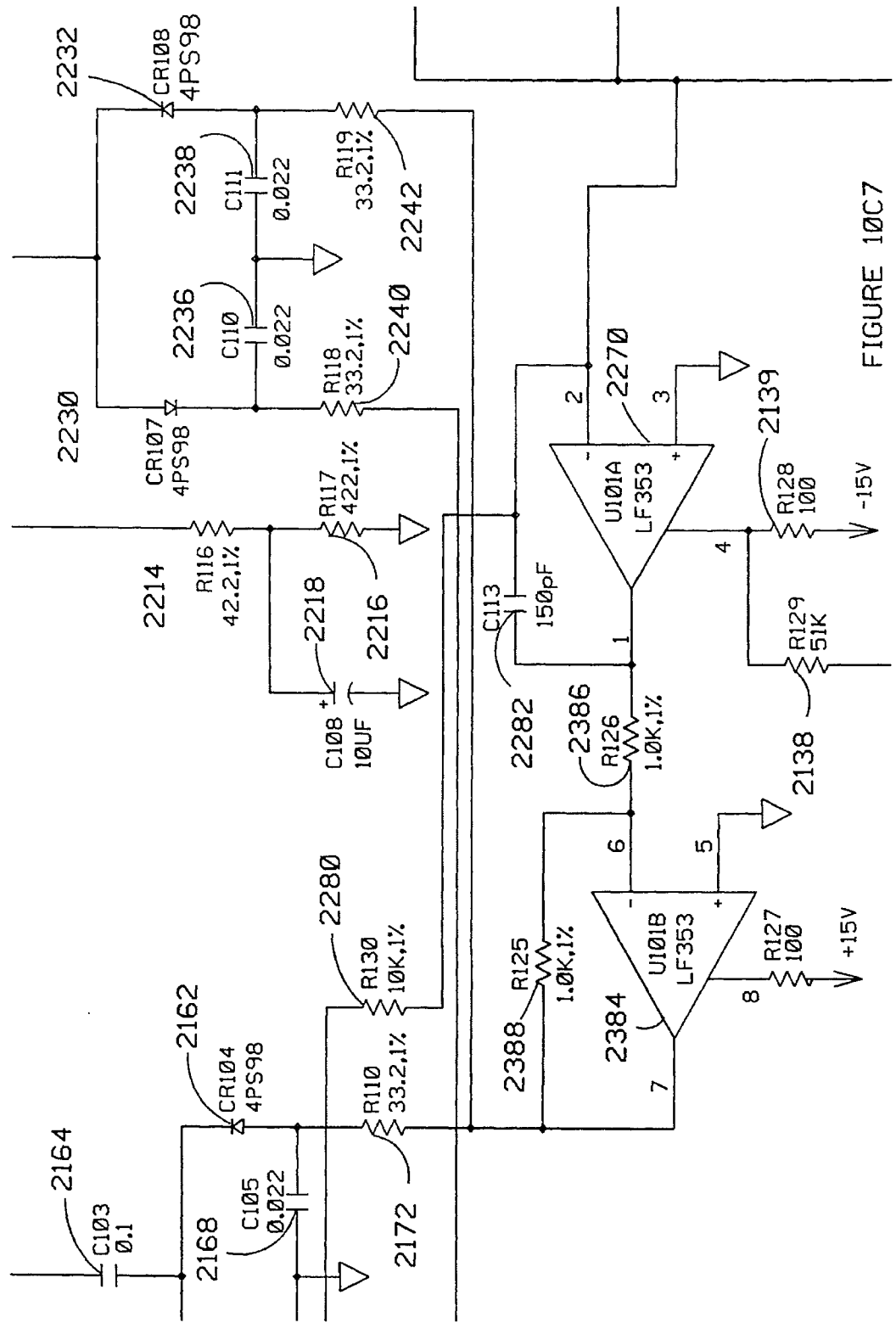
FIGURE 10C7

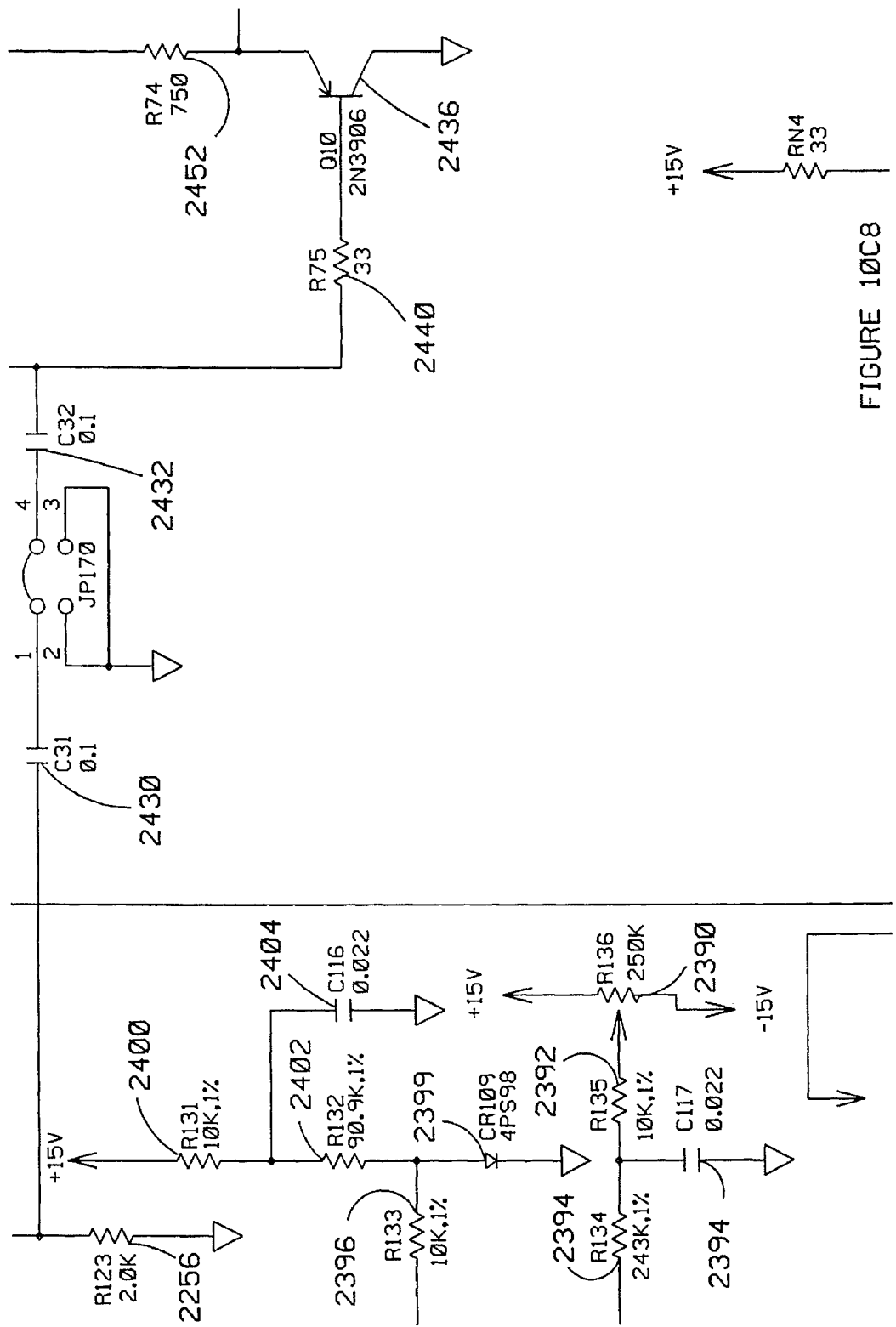
FIGURE 10C8

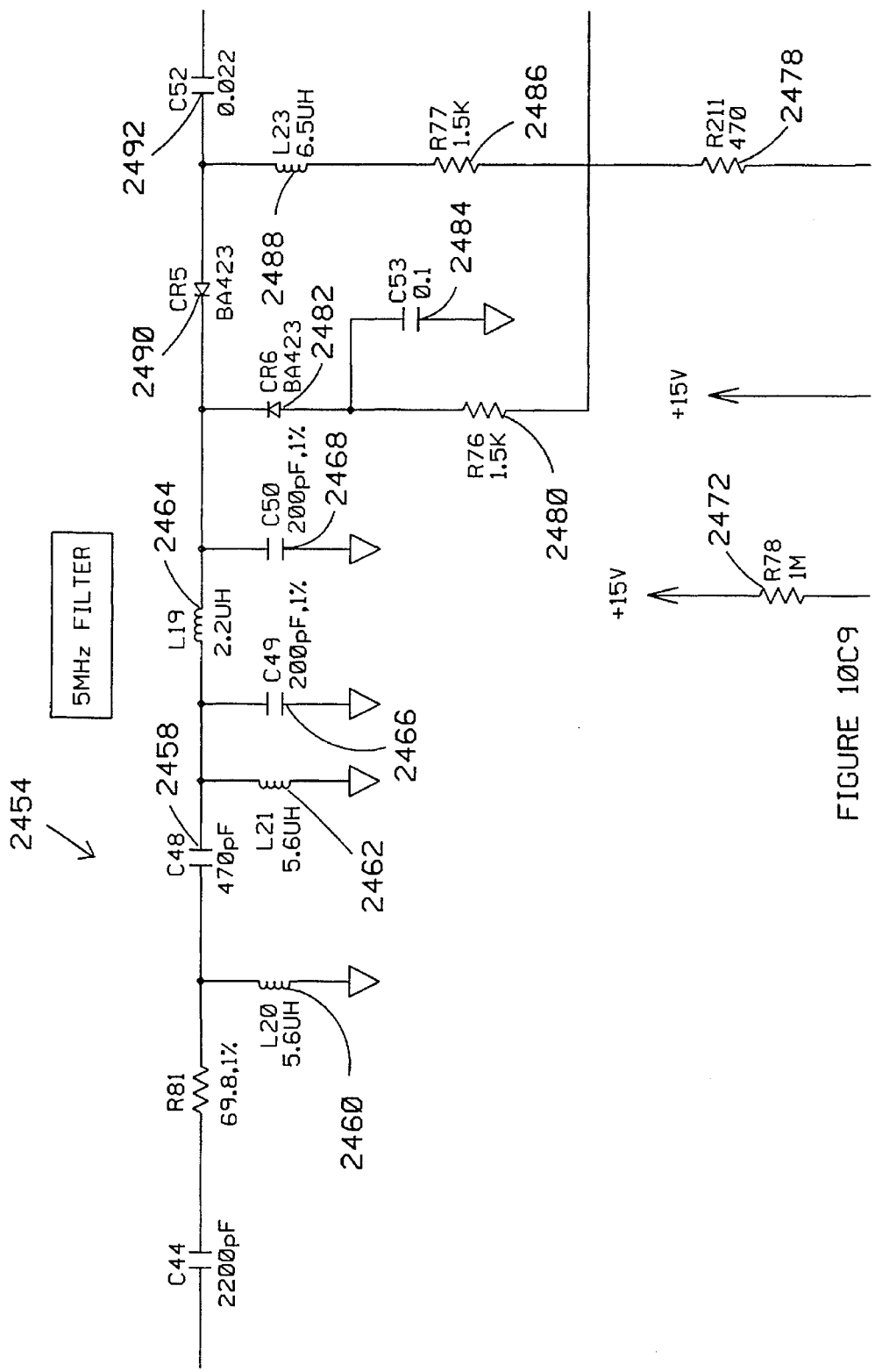
FIGURE 10C9

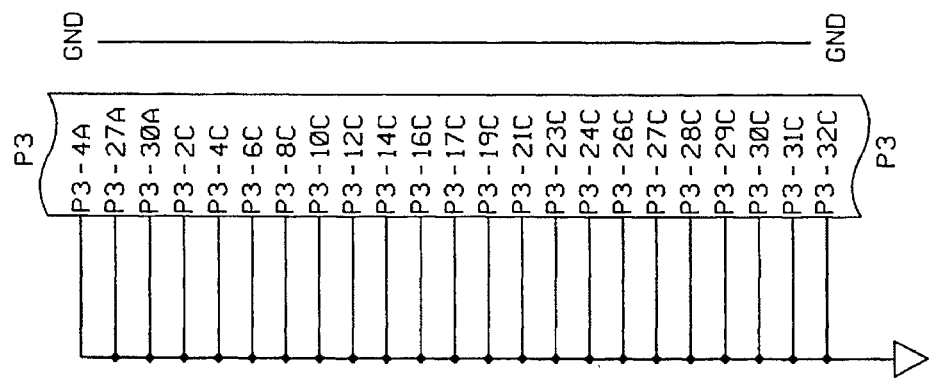
FIGURE 10C10

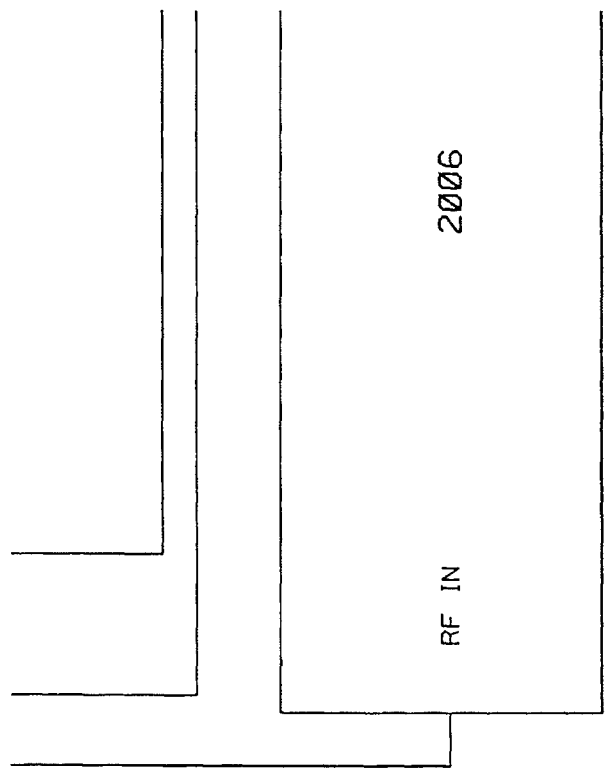
FIGURE 10C11

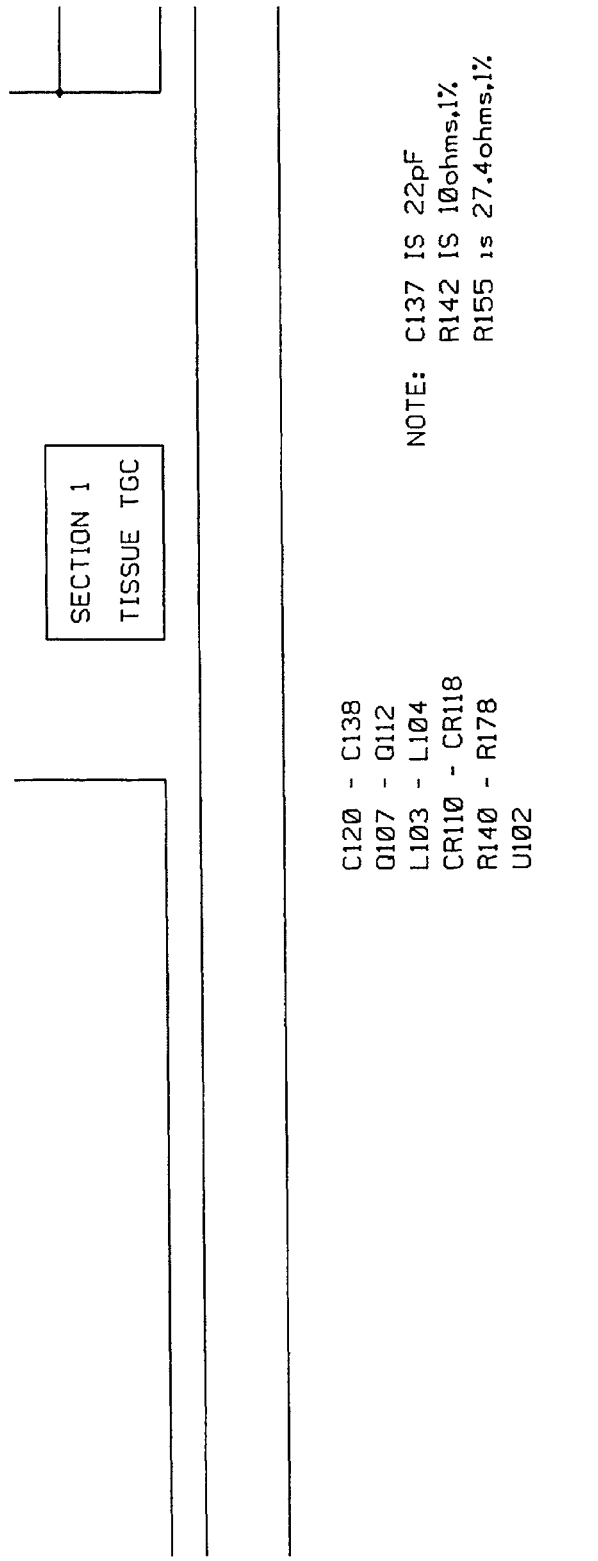
FIGURE 10C12

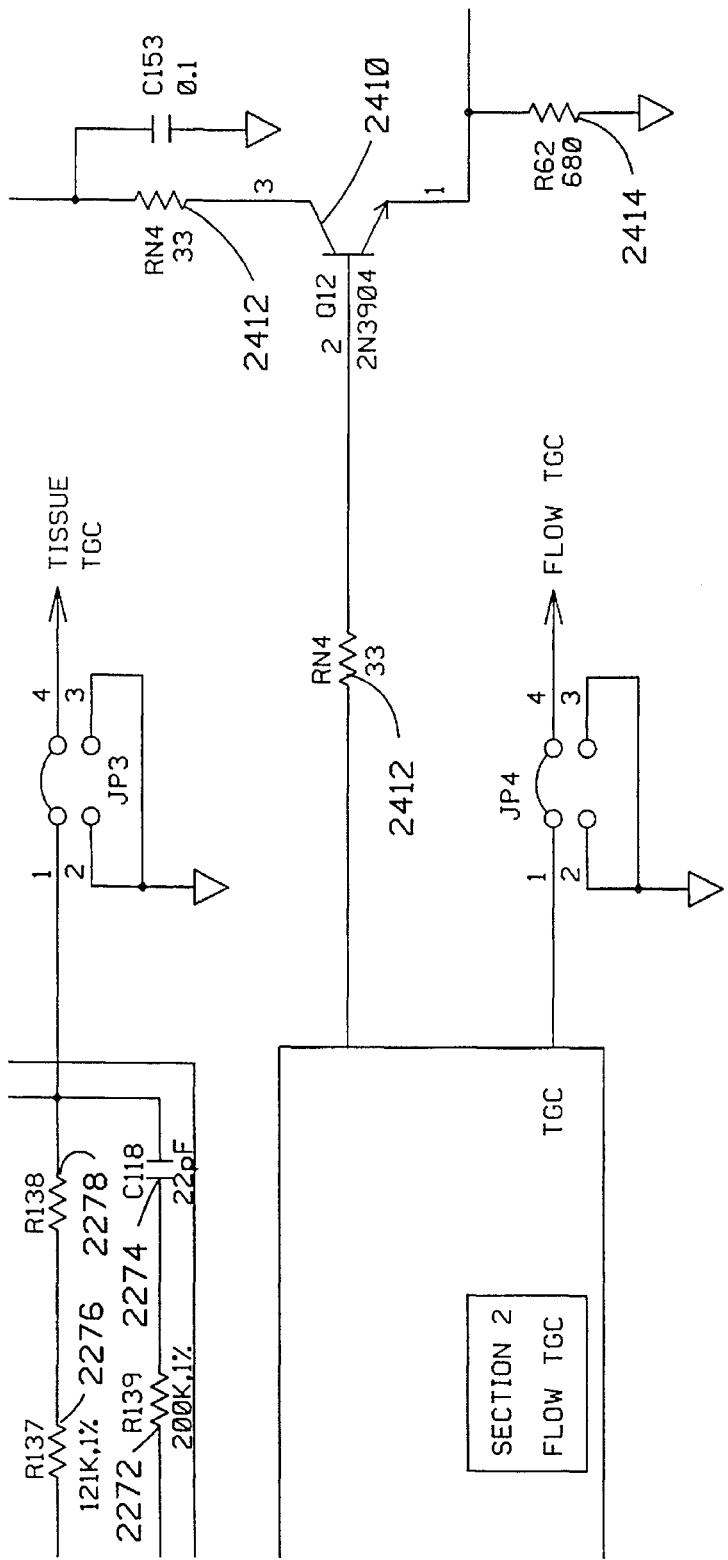
FIGURE 10C13

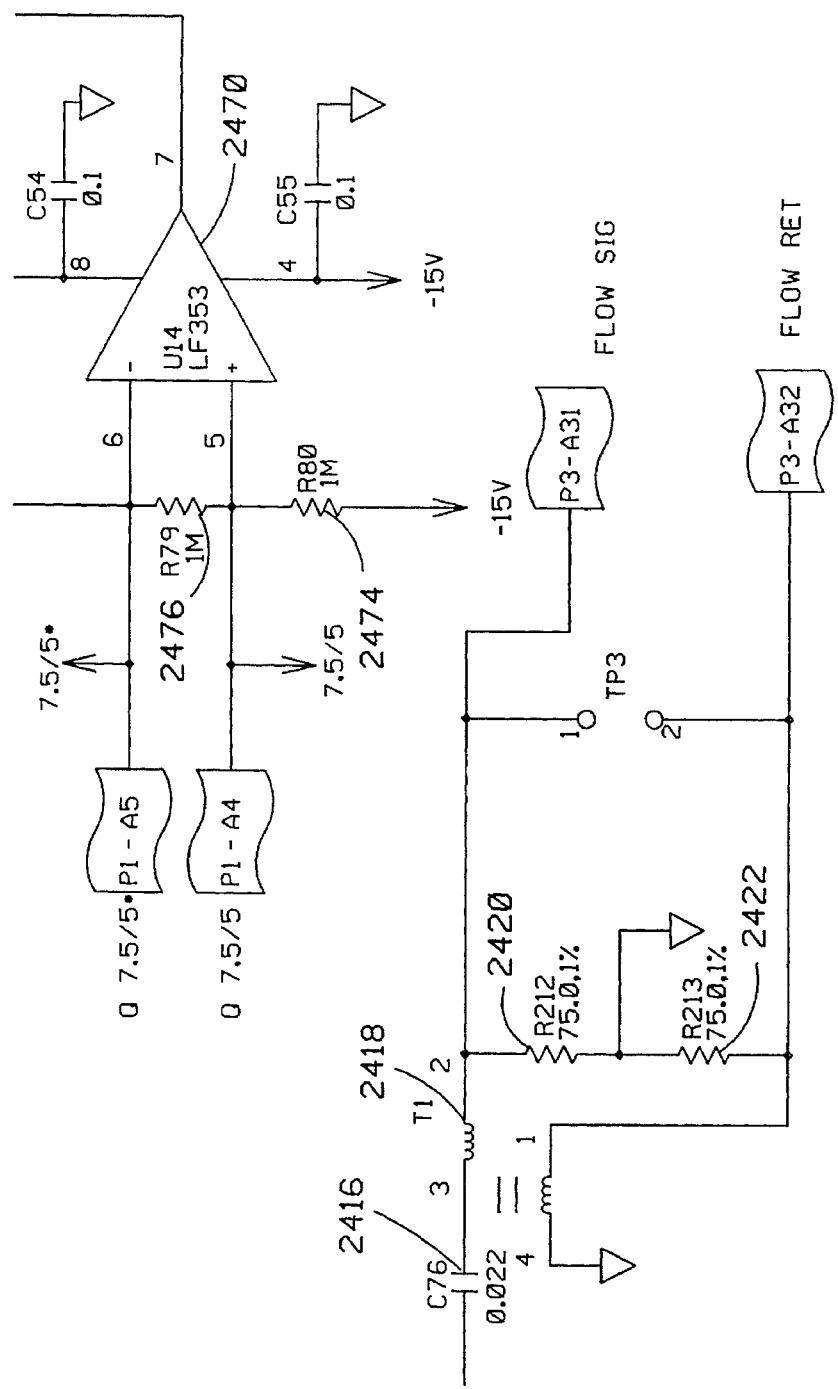
FIGURE 10C14

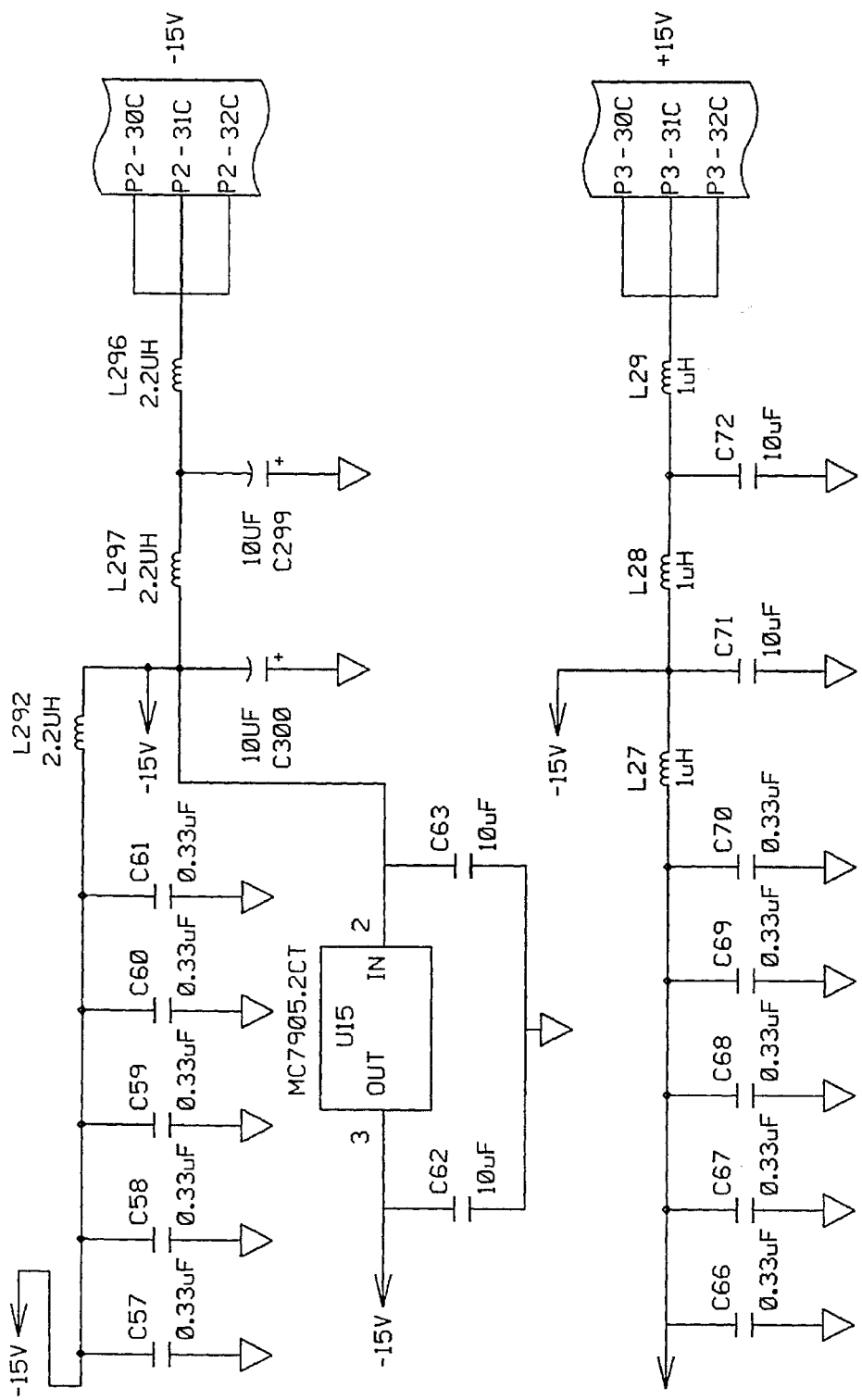
FIGURE 10C15

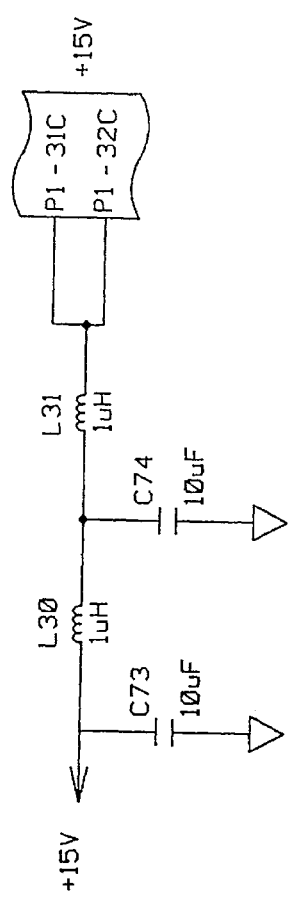
FIGURE 10C16

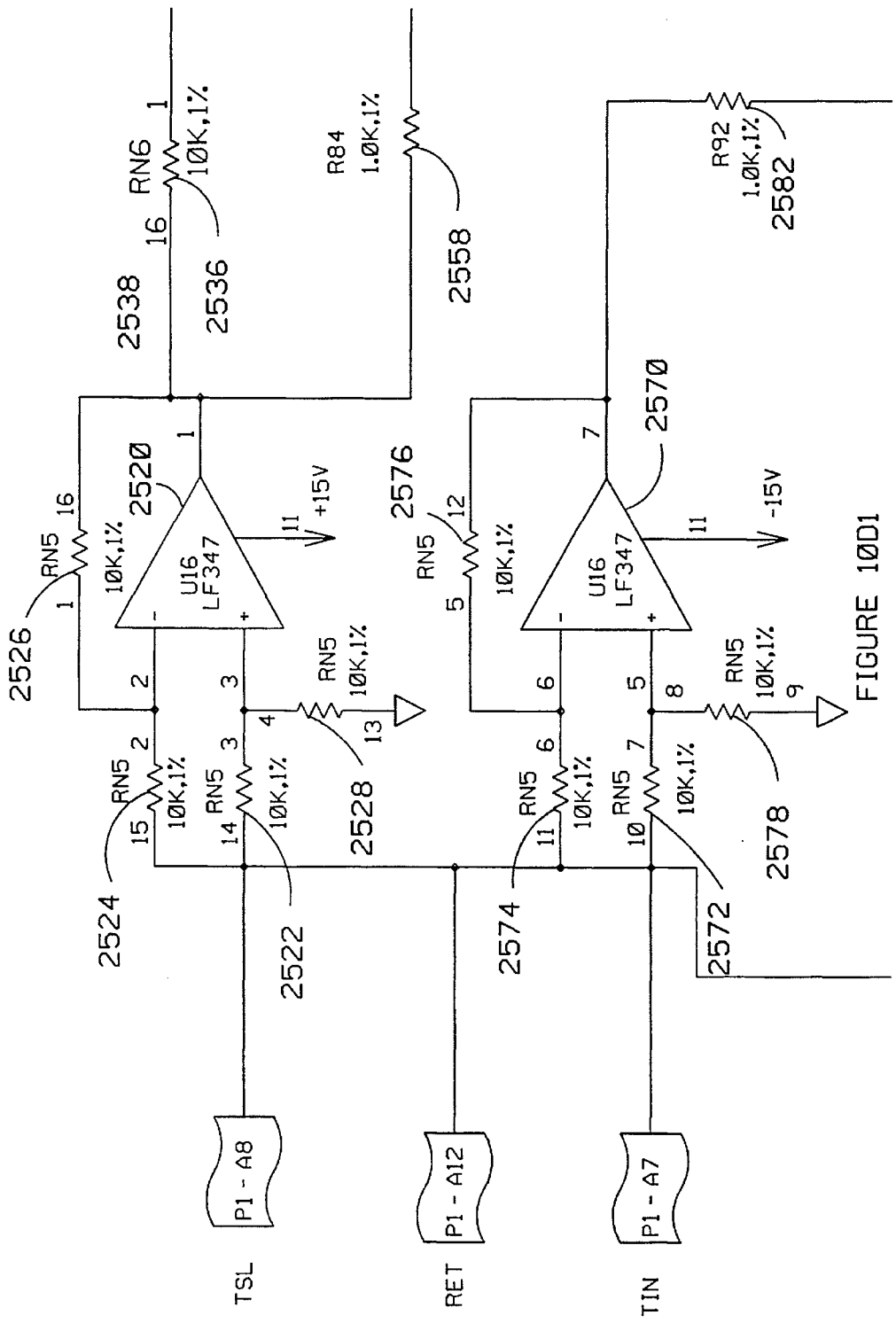
FIGURE 10D1

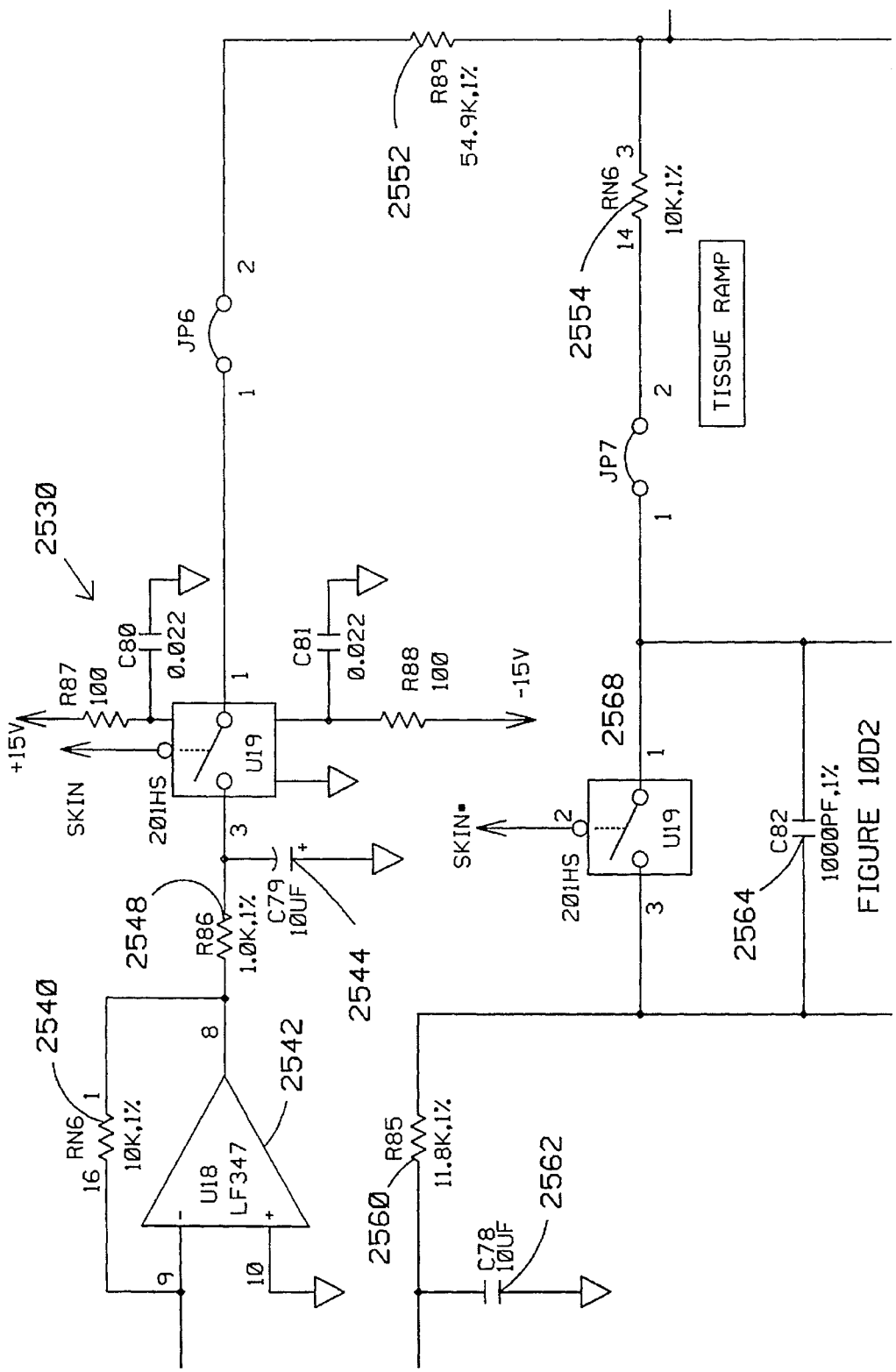
FIGURE 10D2

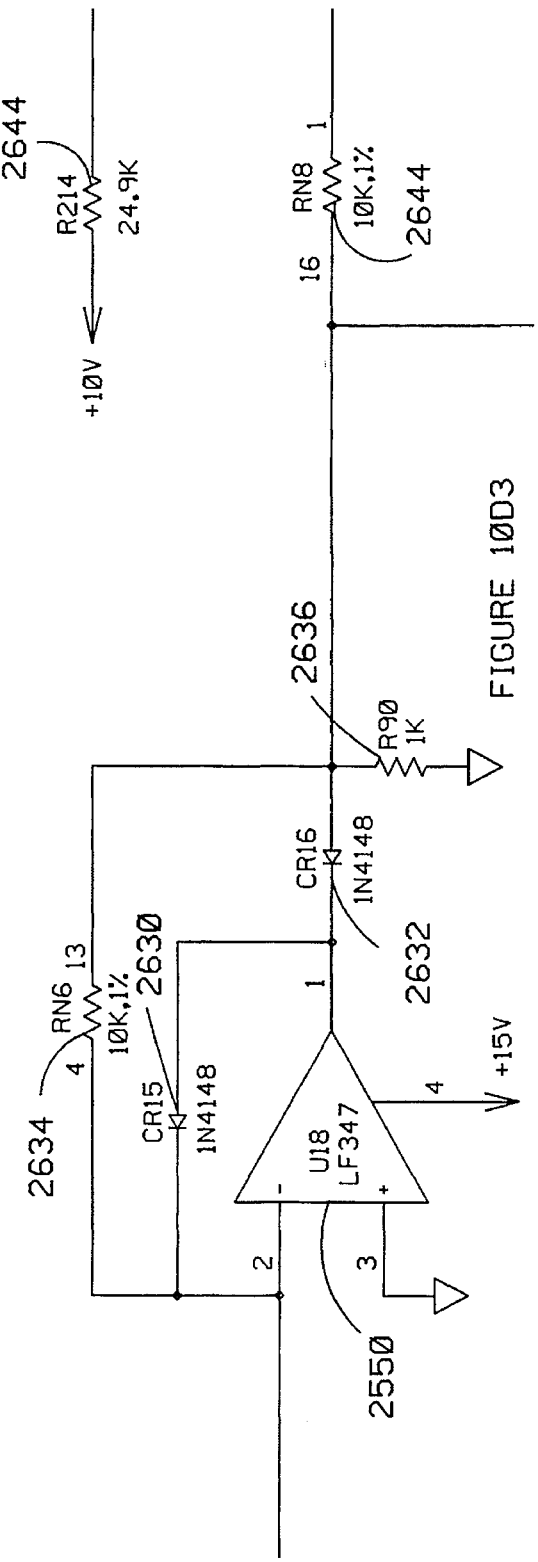
FIGURE 10D3

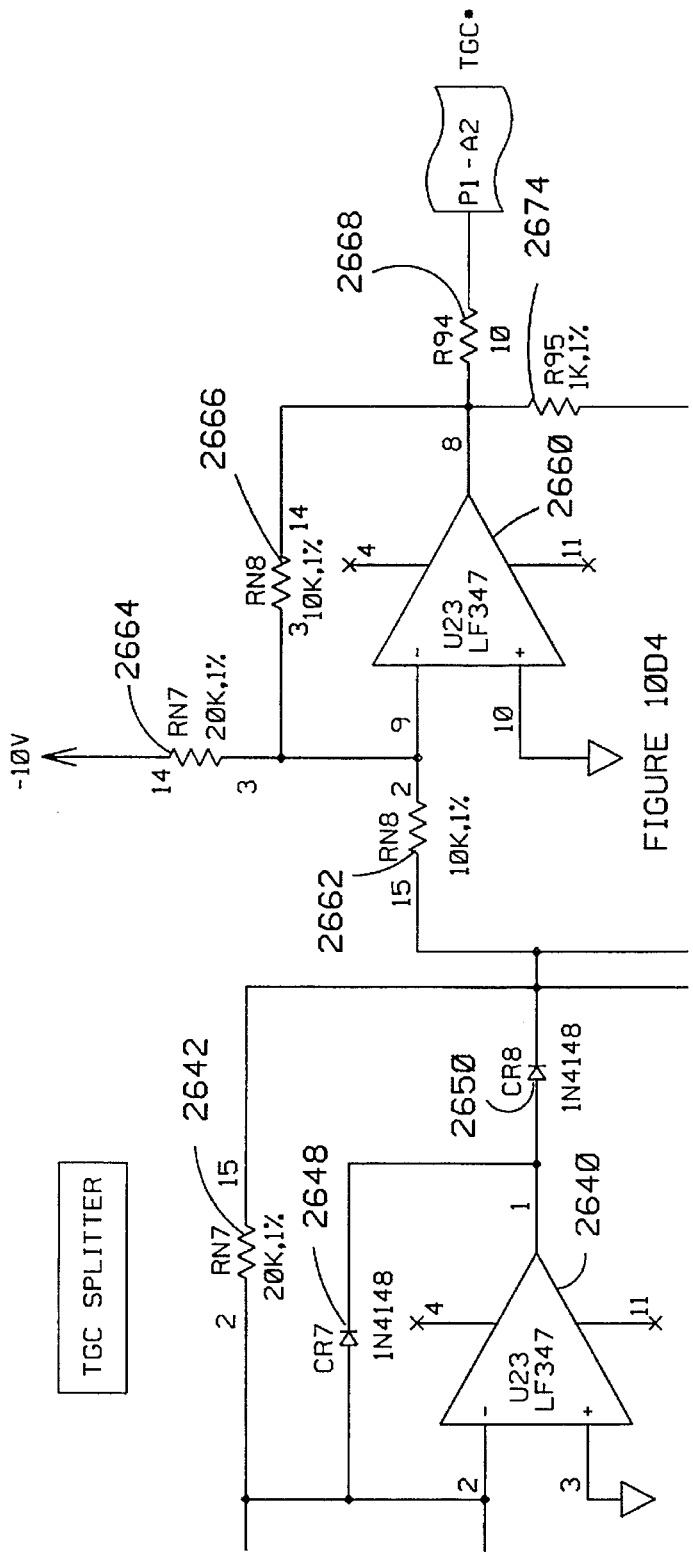

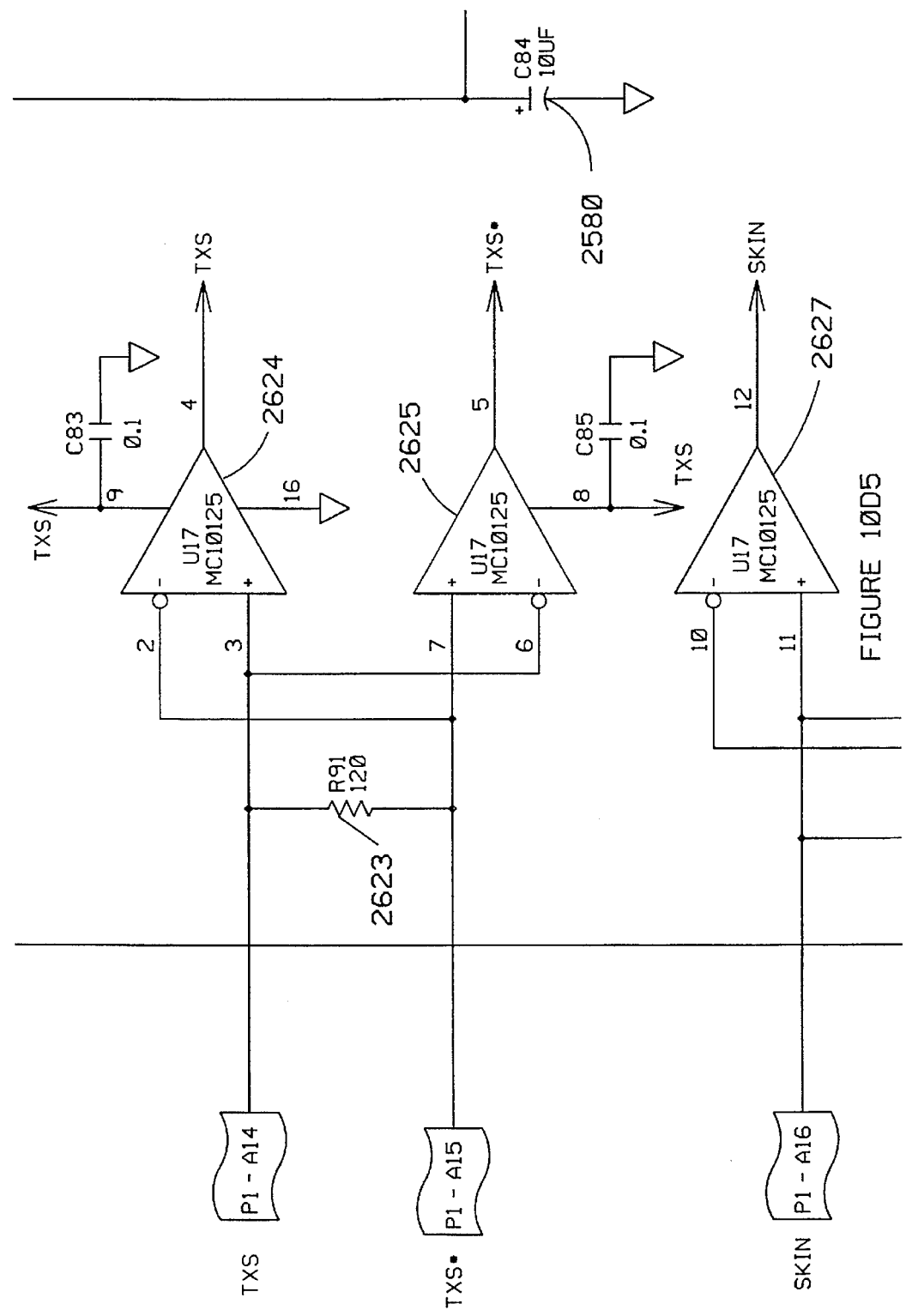
FIGURE 10D5

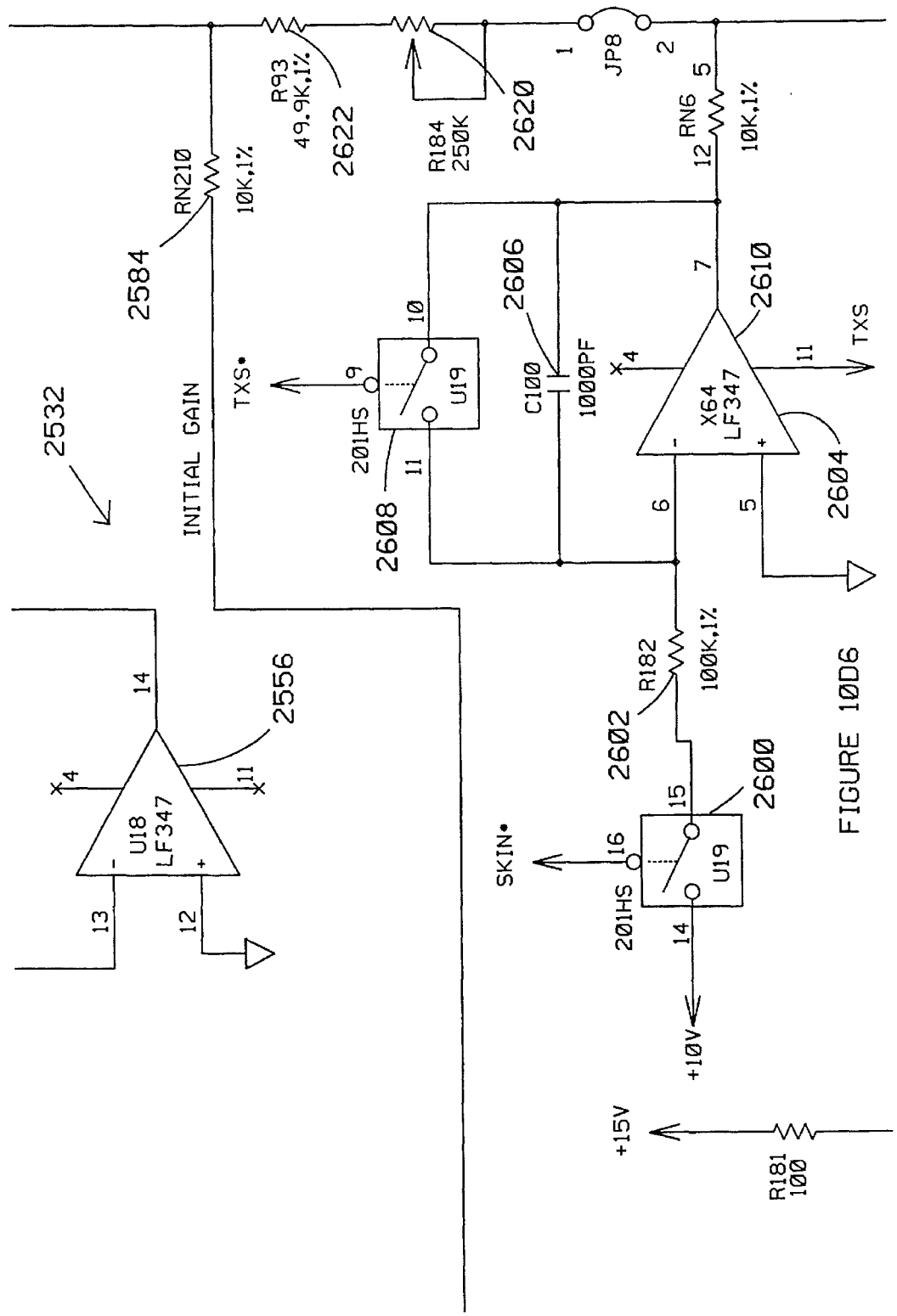
FIGURE 10D6

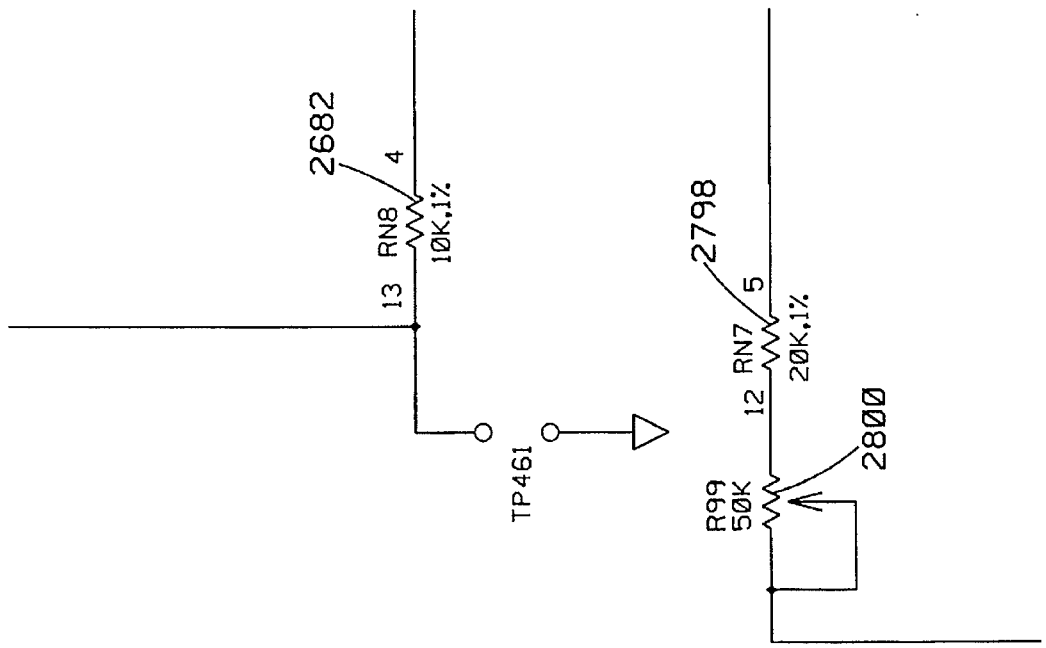
FIGURE 10D7

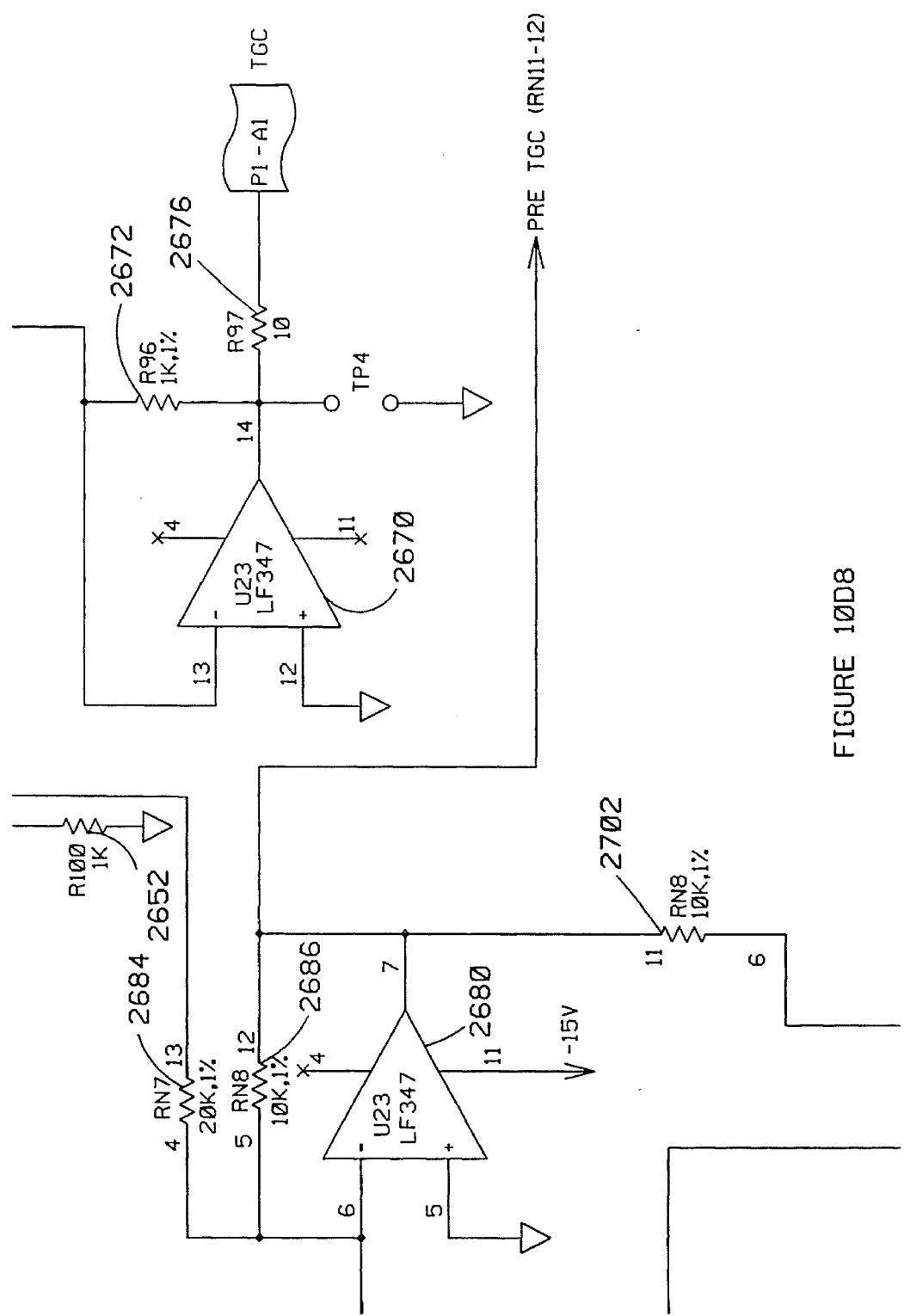
FIGURE 10D8

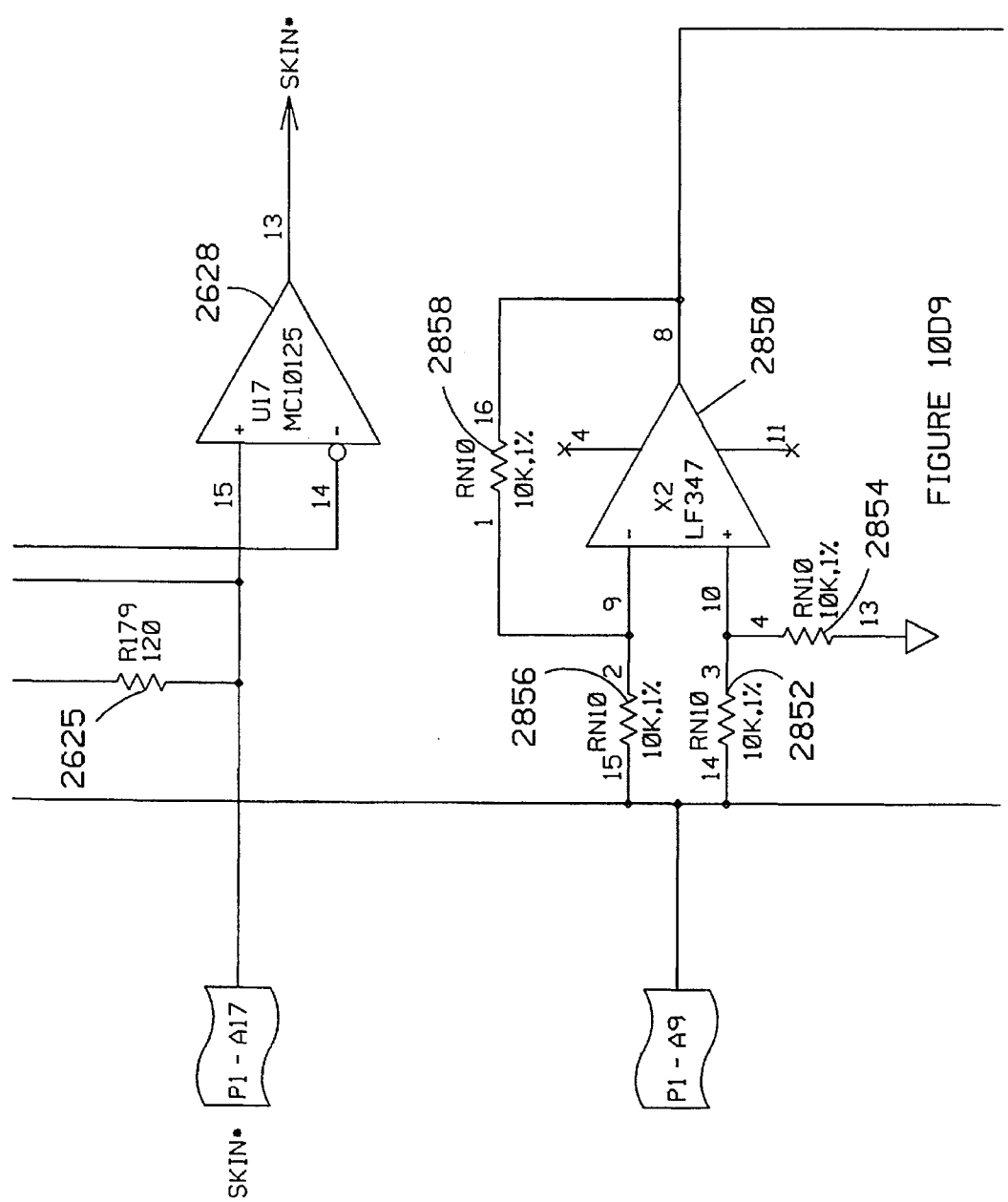
FIGURE 10D9

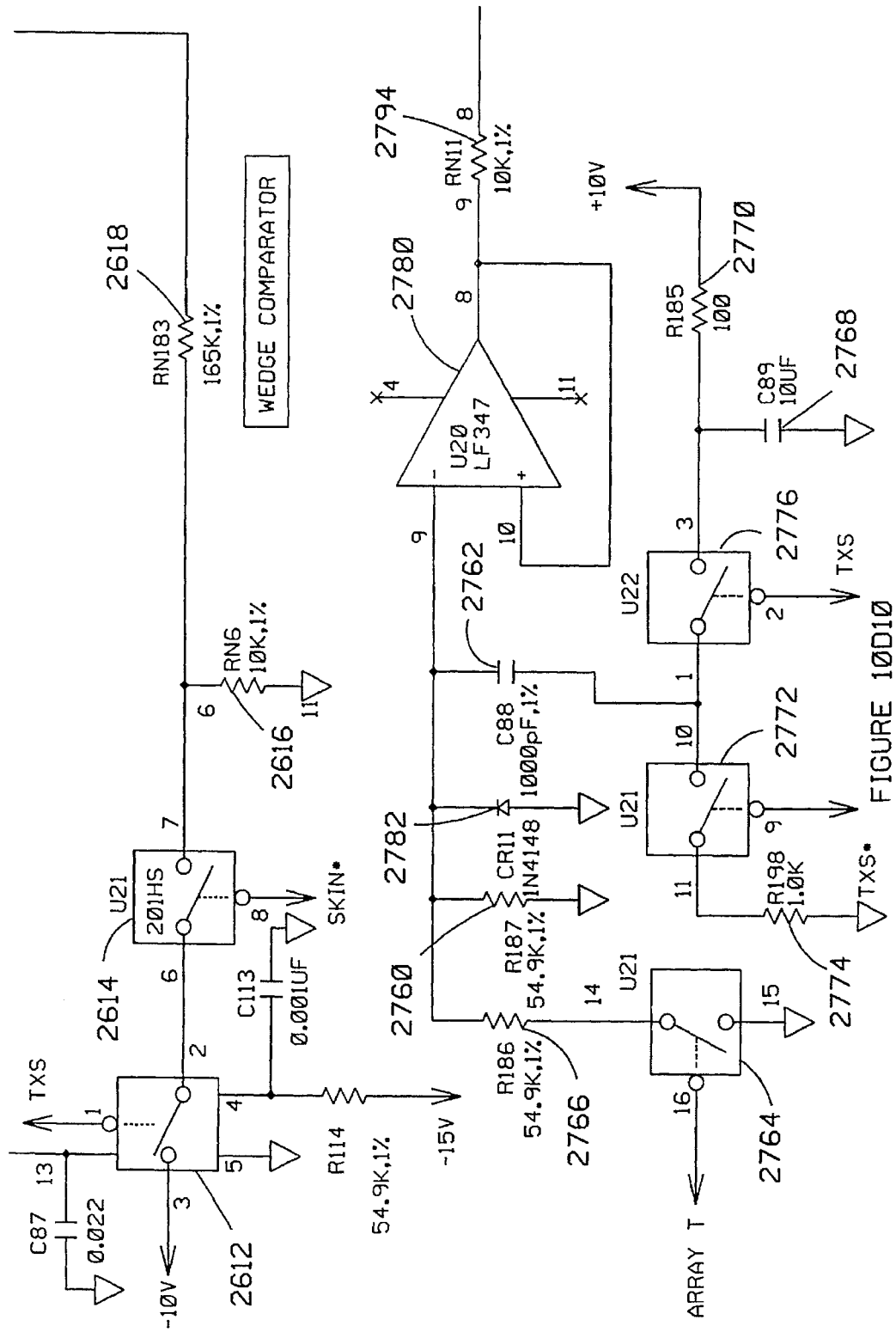

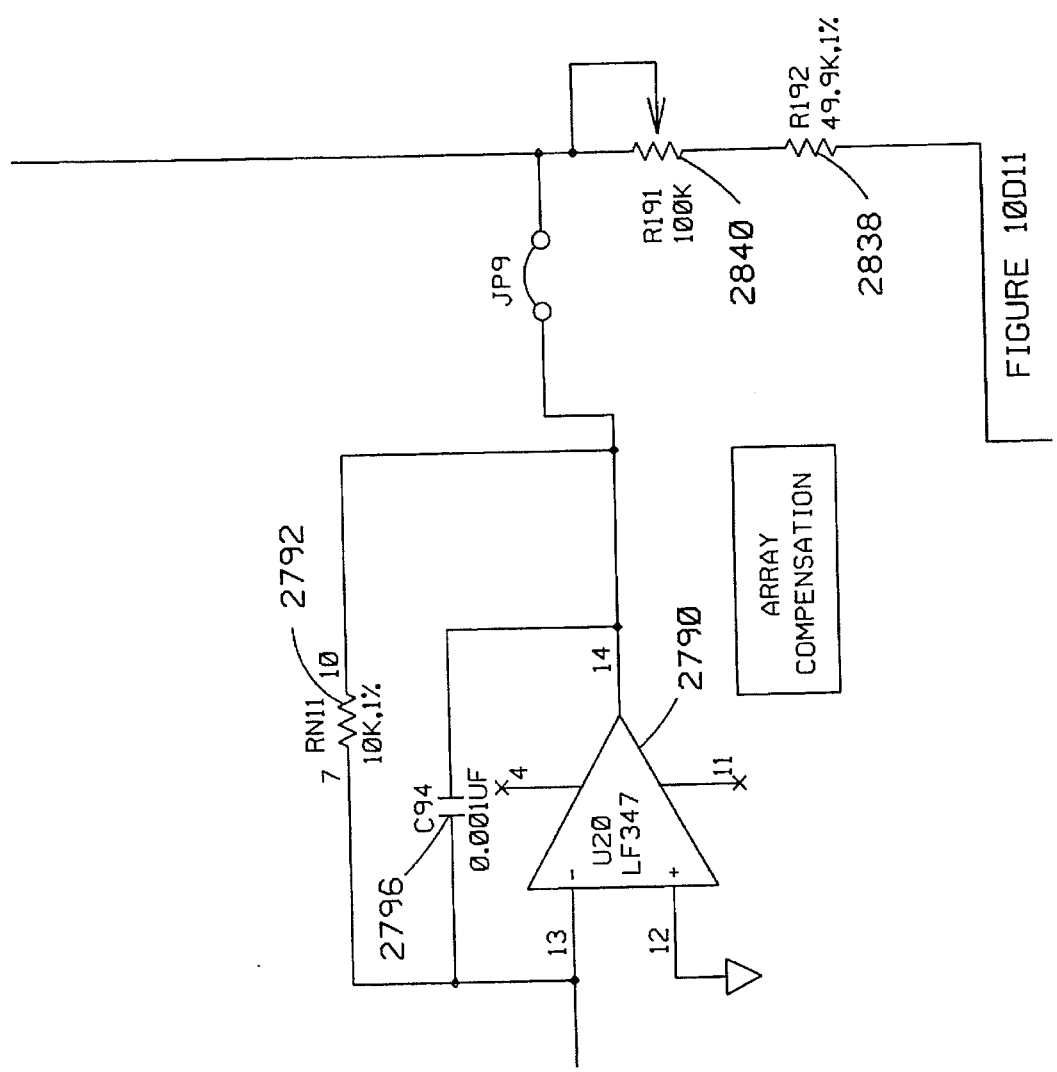

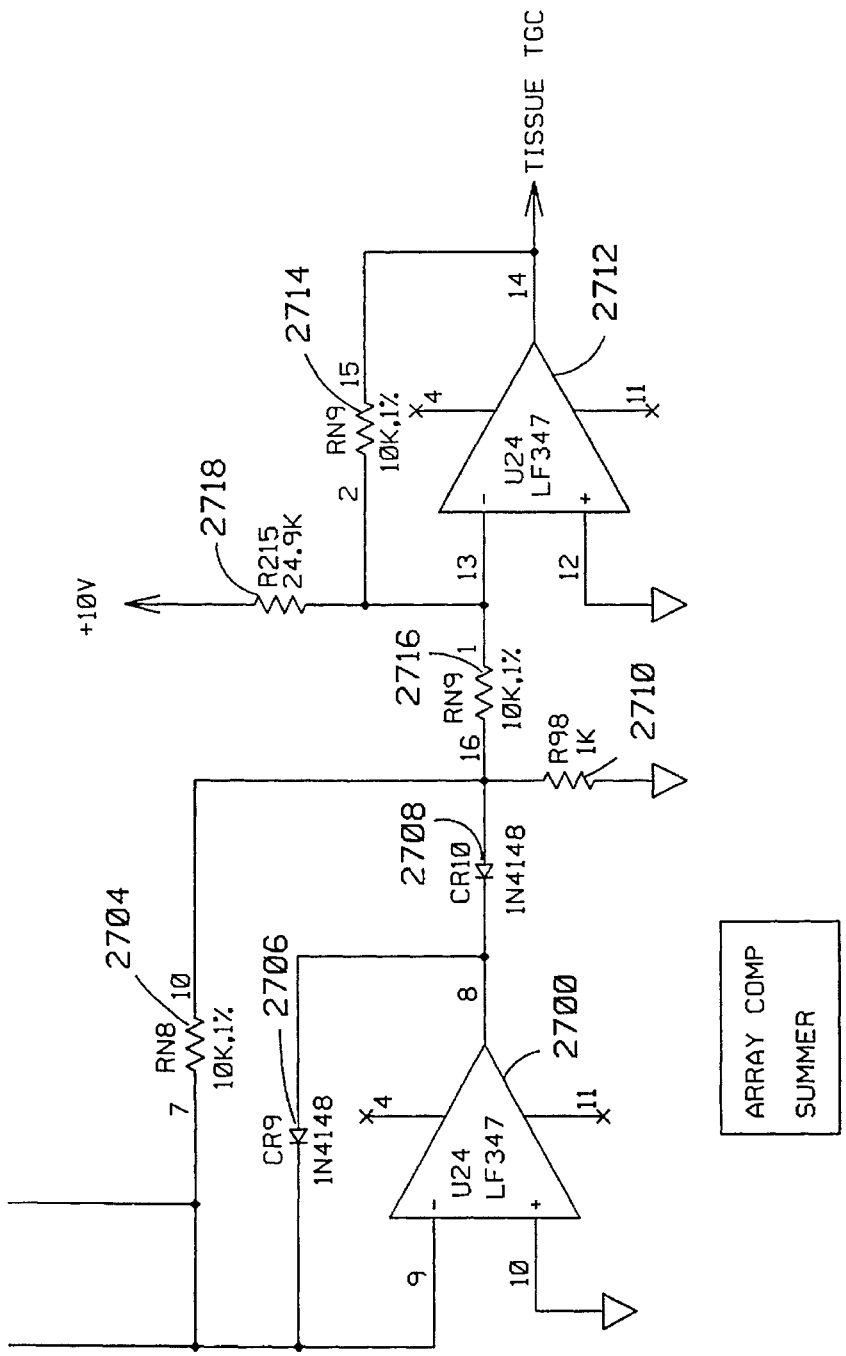
FIGURE 10D12

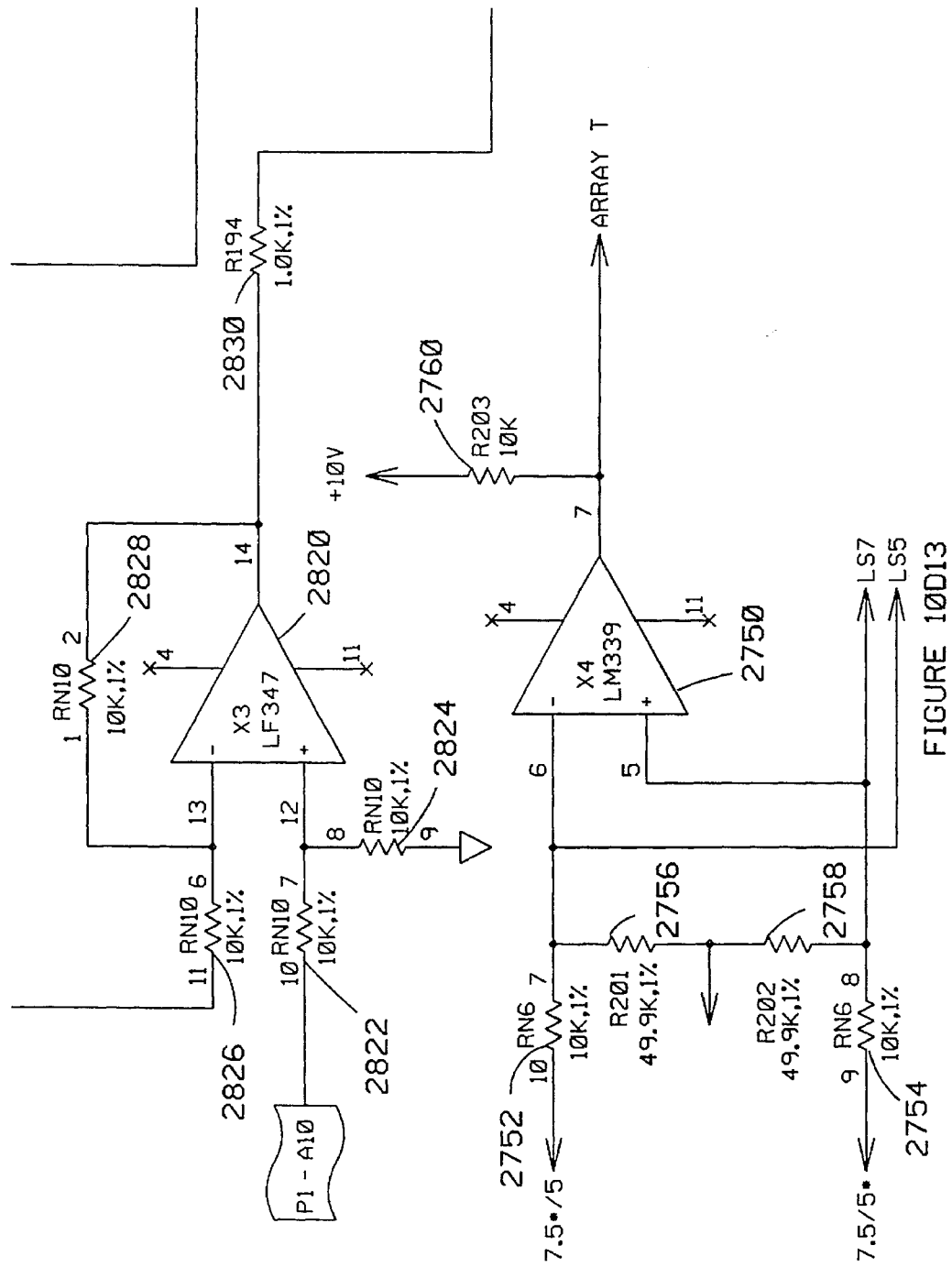
FIGURE 10D13

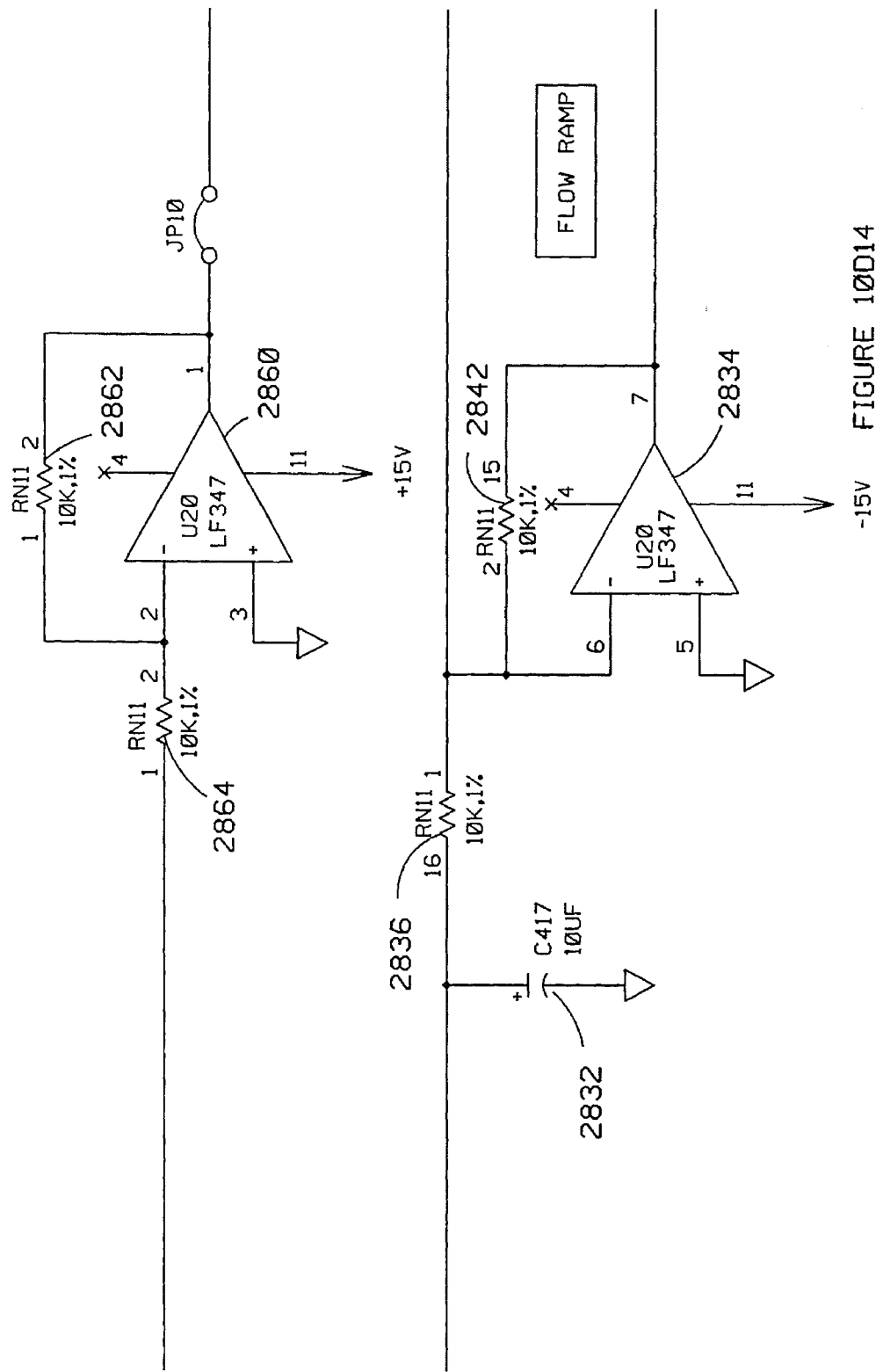

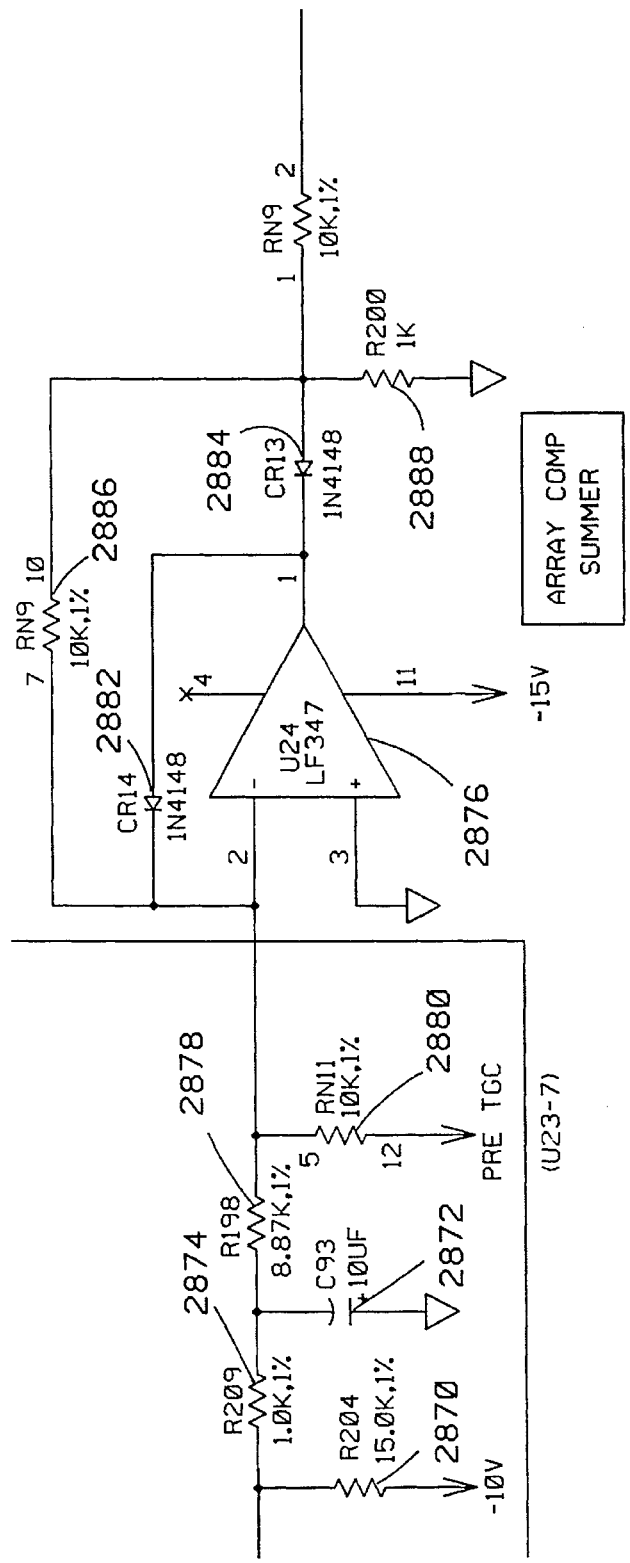
FIGURE 10D15

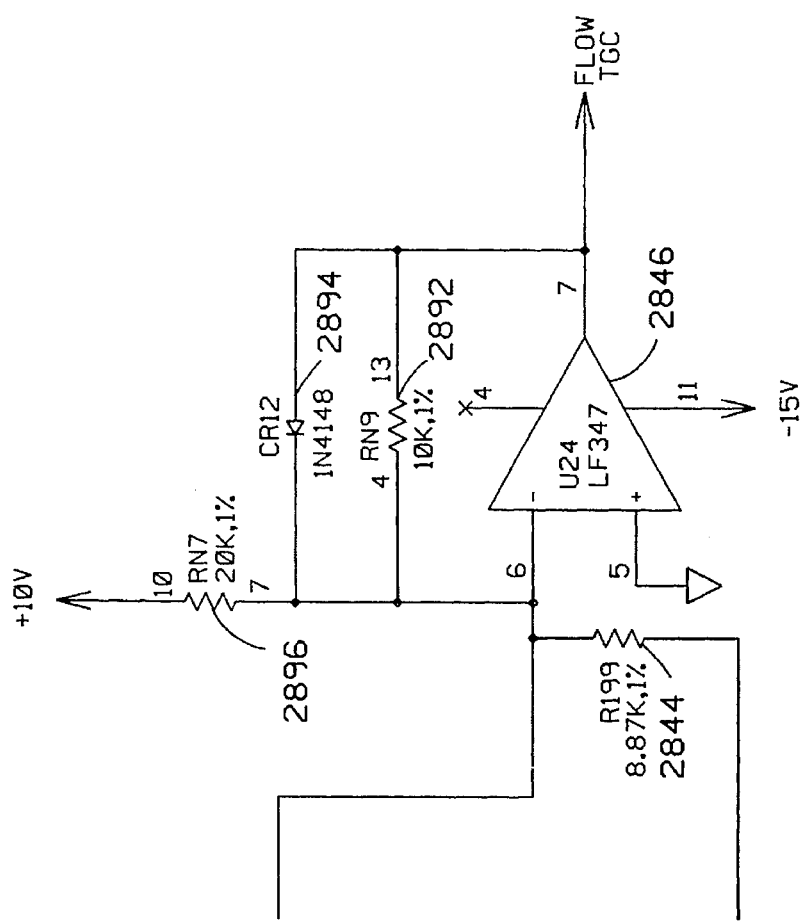
FIGURE 10D16

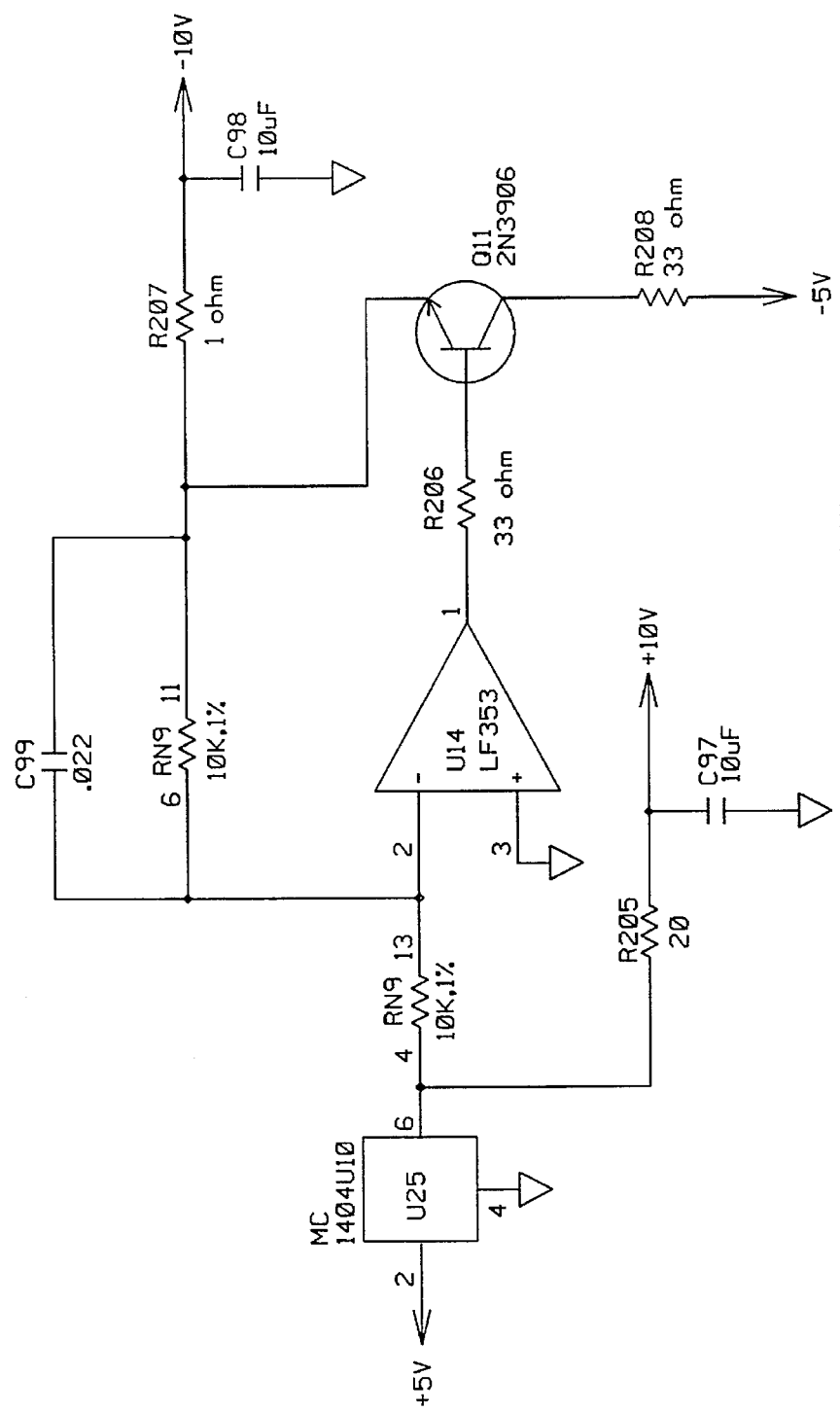
FIGURE 10D17

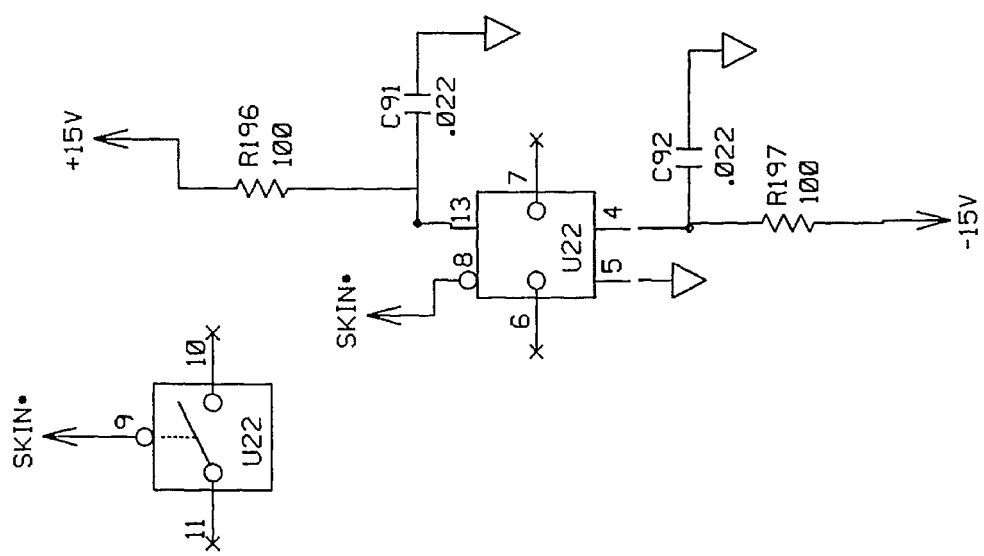
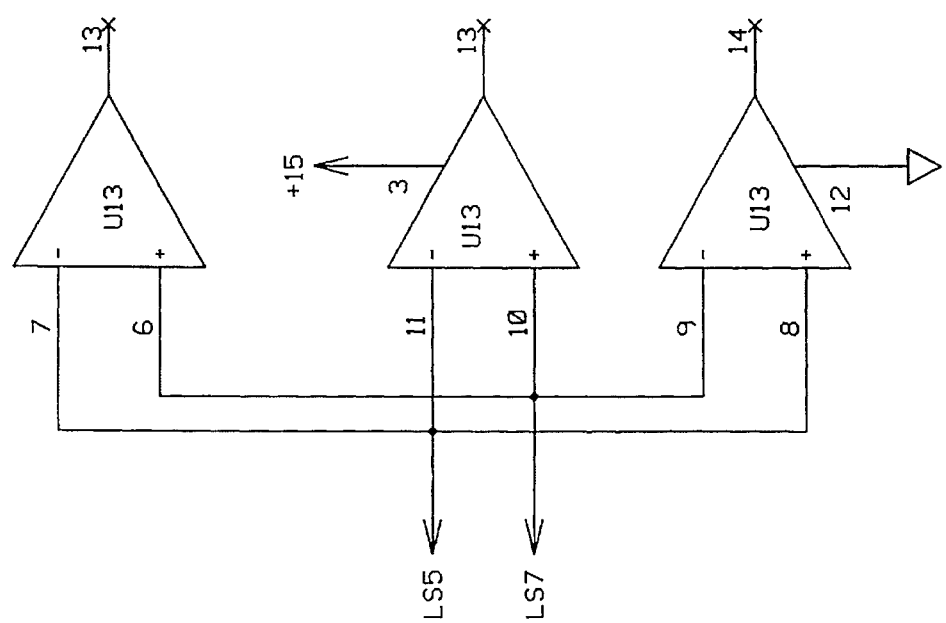
FIGURE 10D18

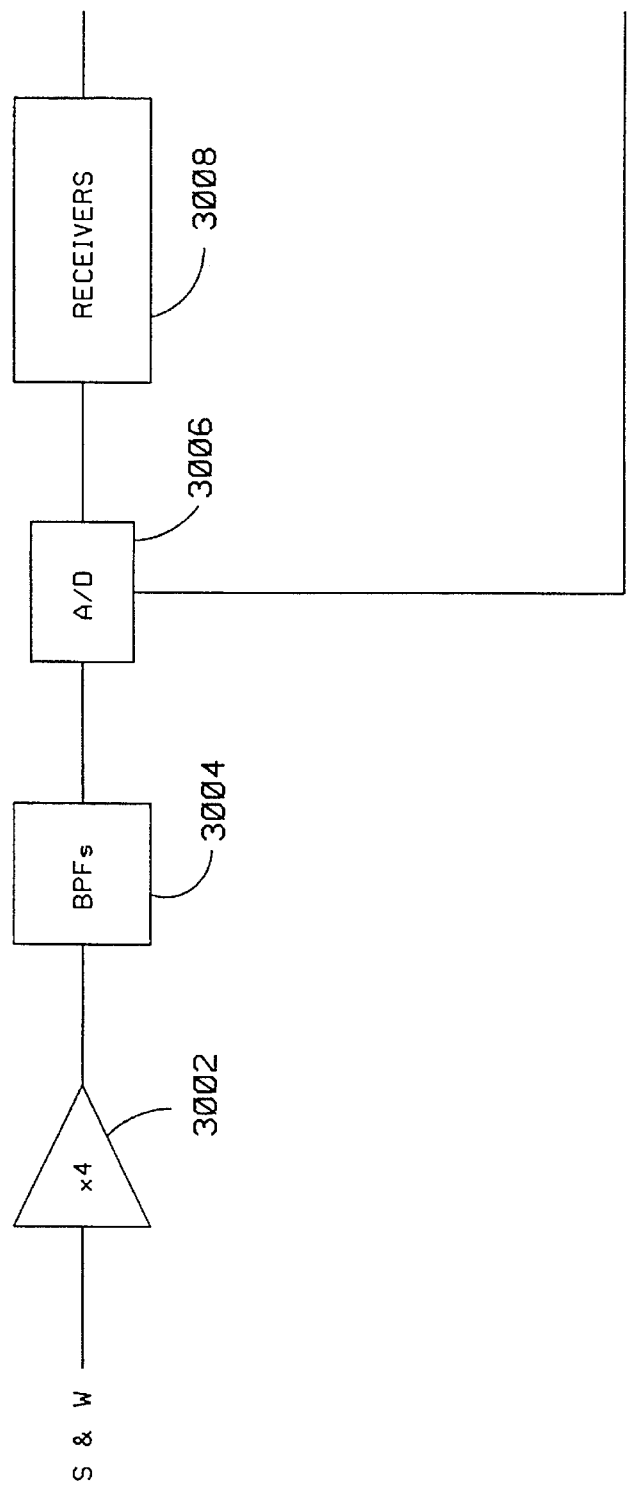
FIGURE 11A1

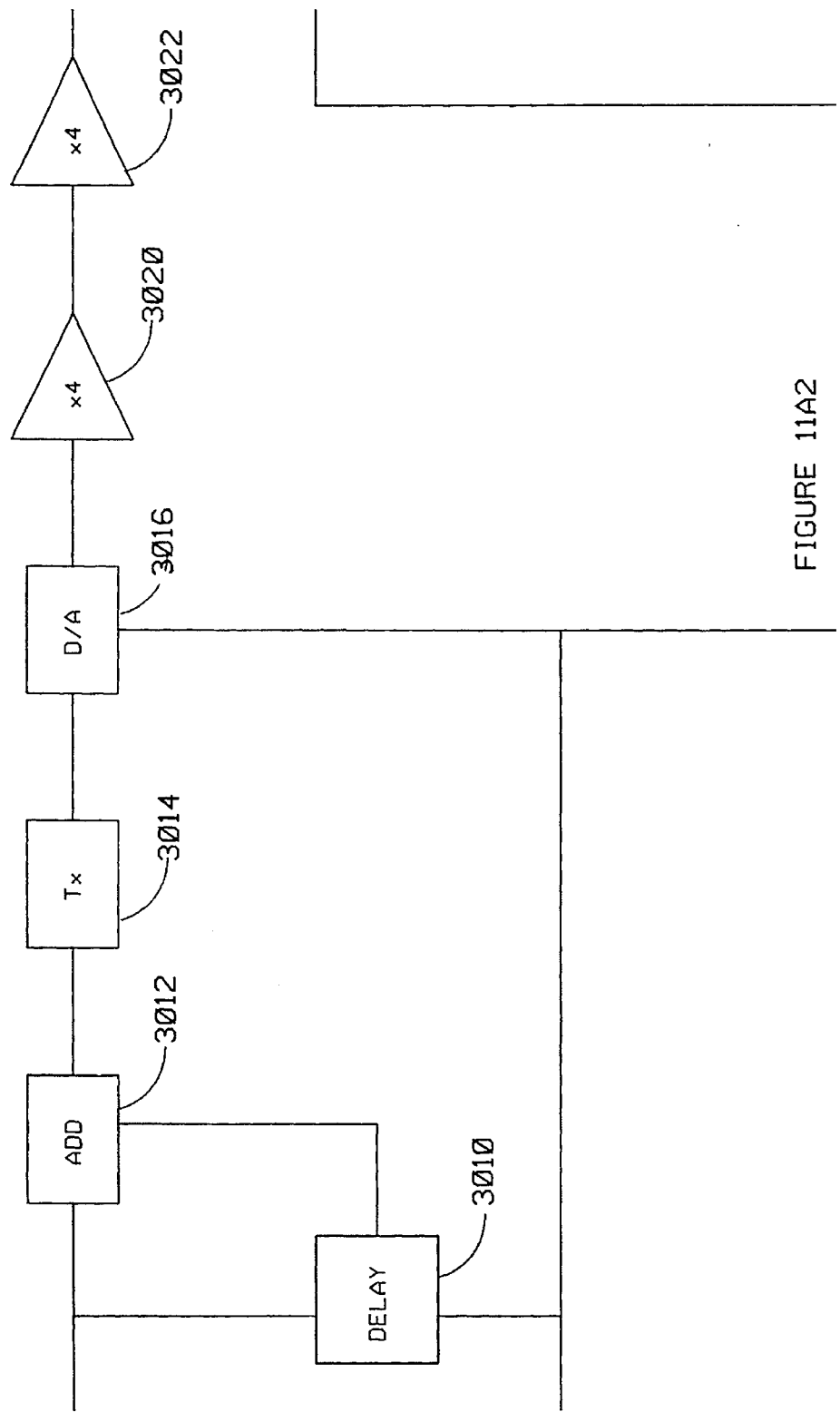
FIGURE 11A2

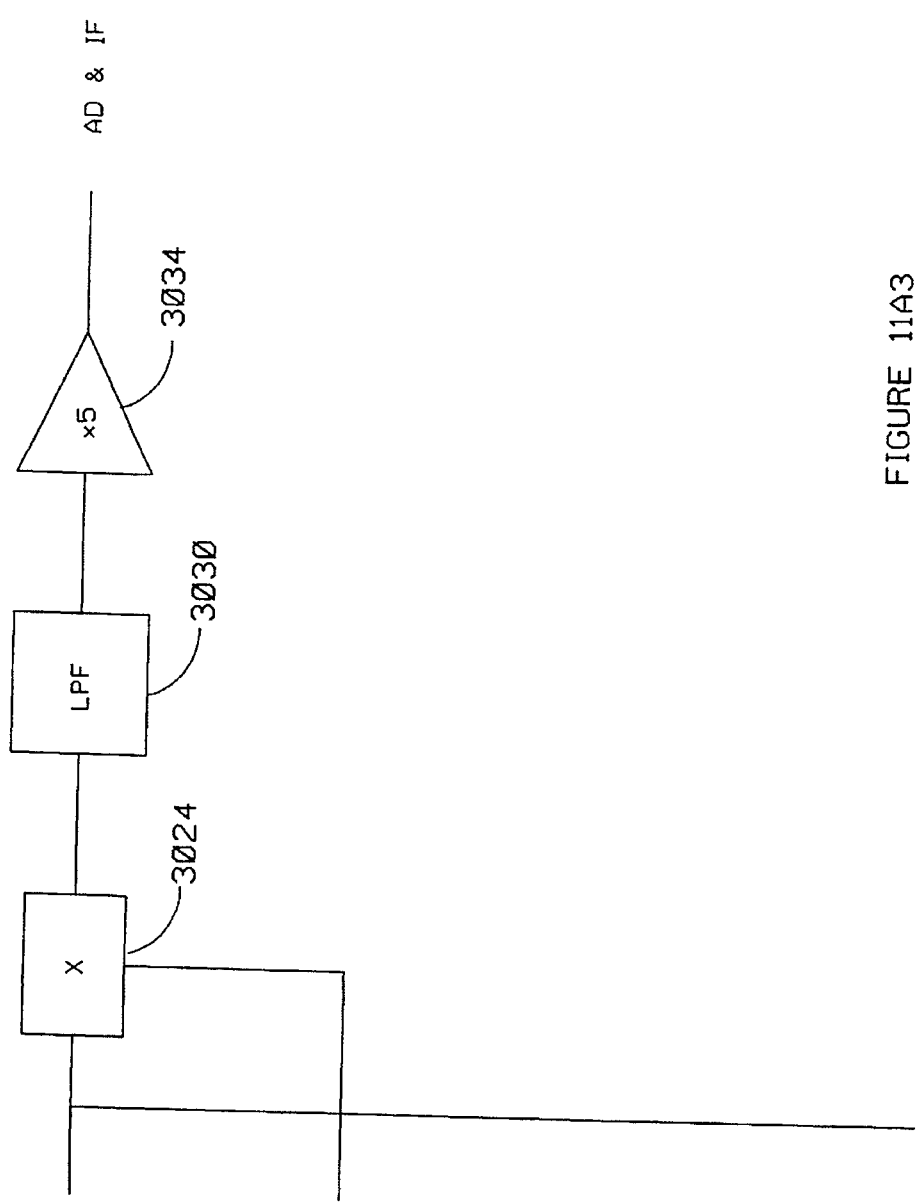
FIGURE 11A3

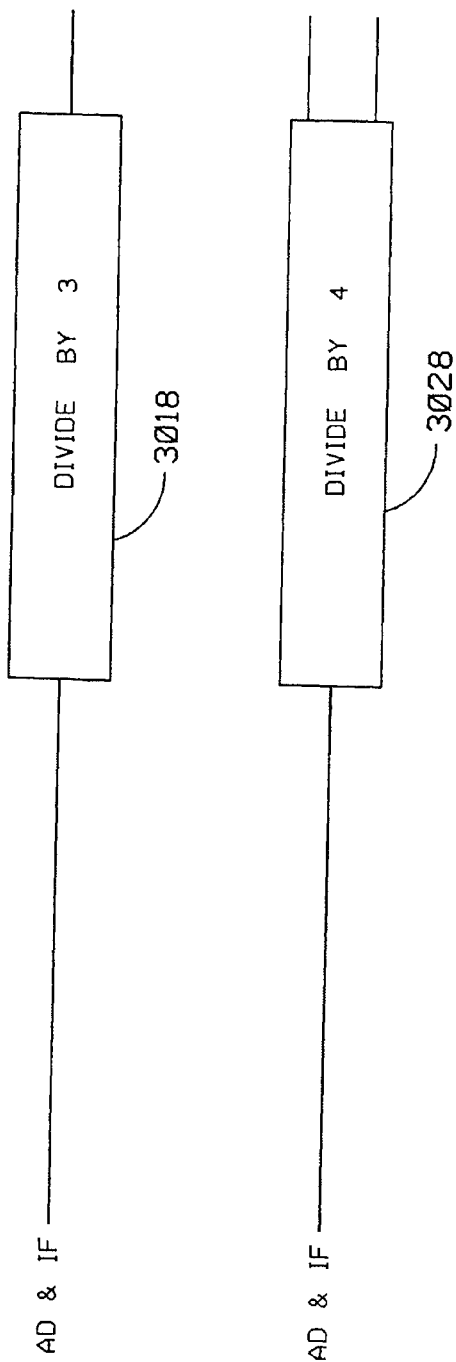
FIGURE 11A4

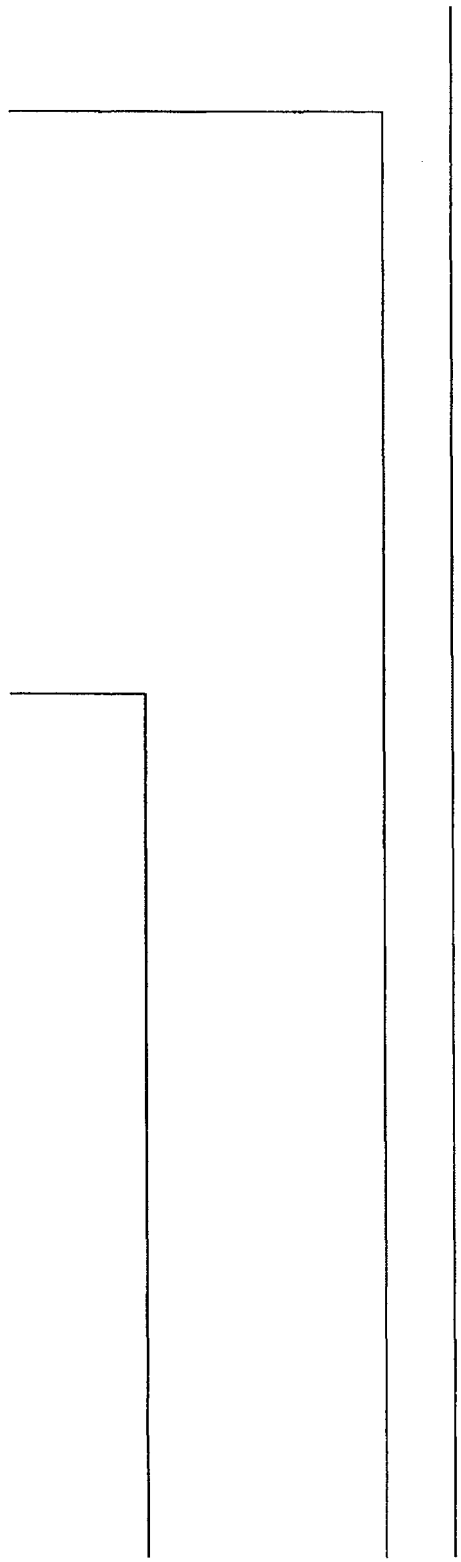
FIGURE 11A5

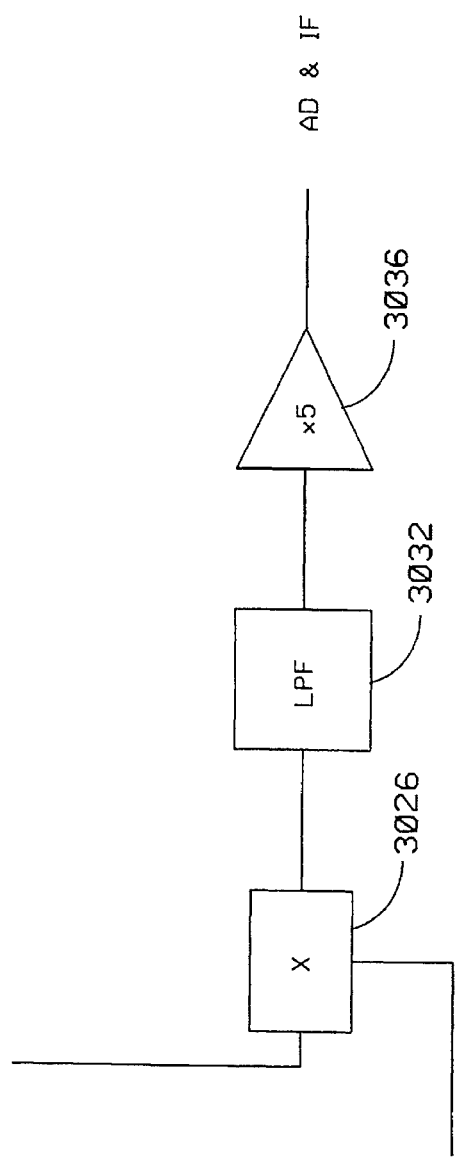
FIGURE 11A6

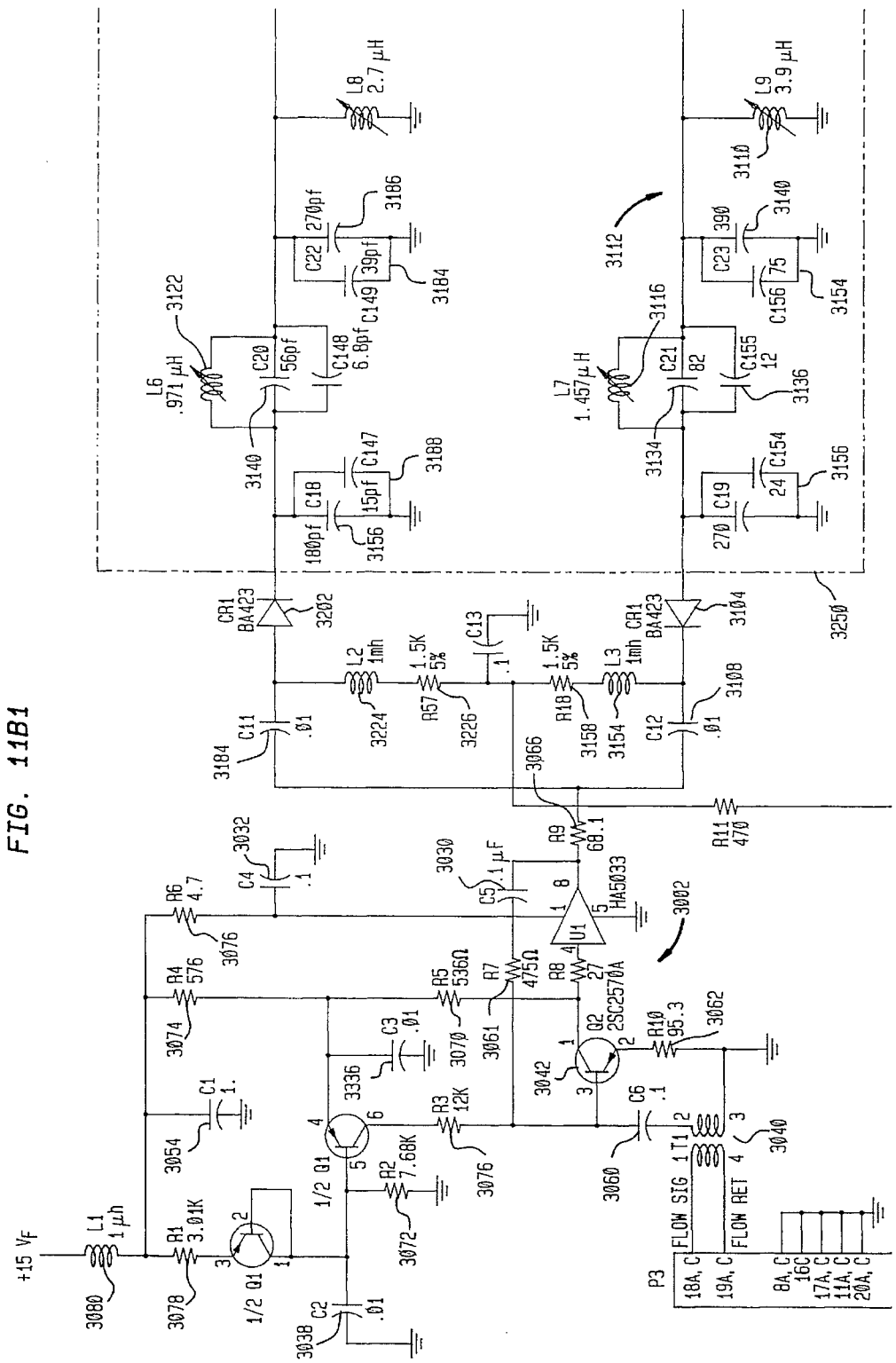
FIG. 11B1

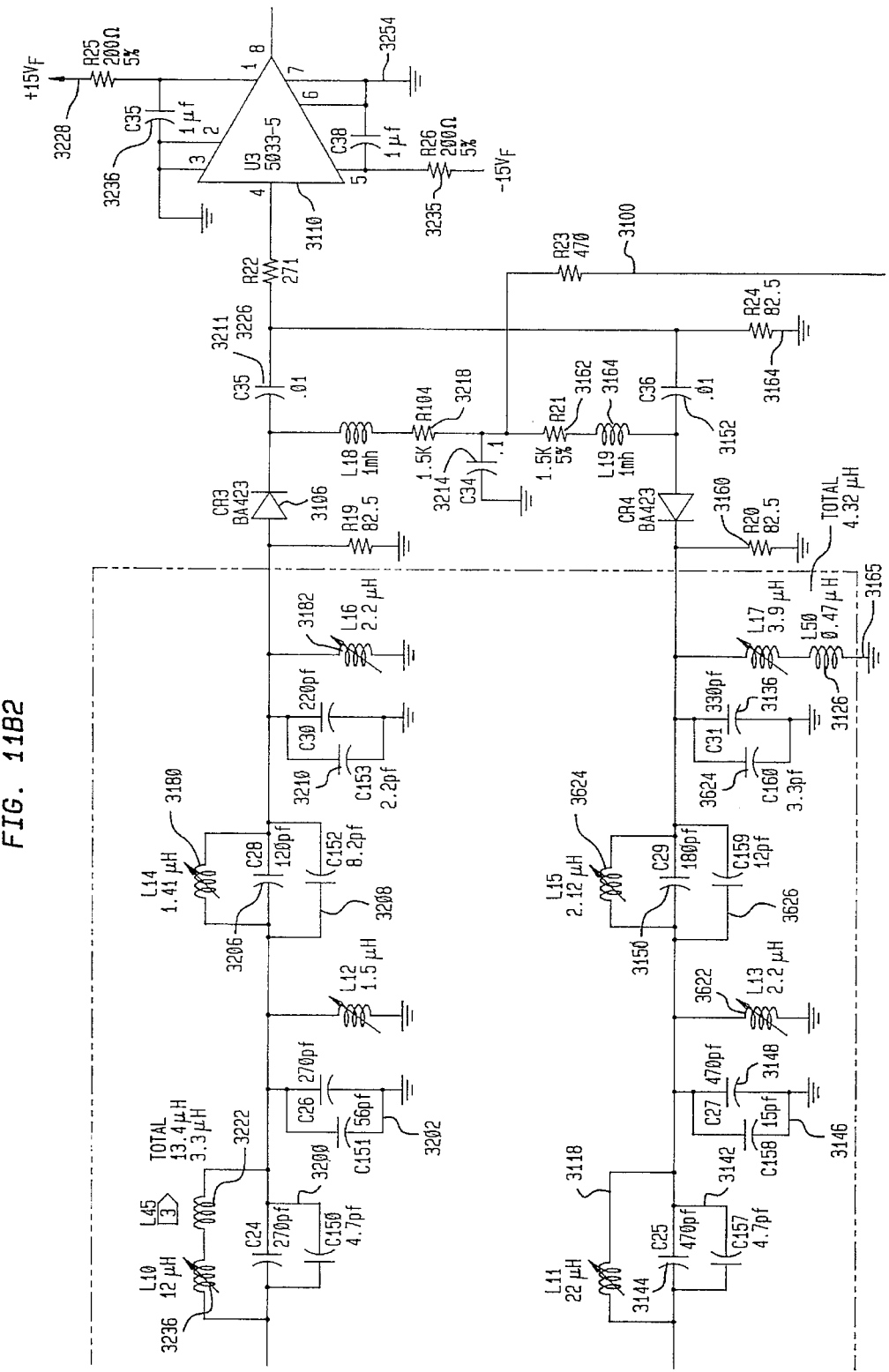
FIG. 11B2

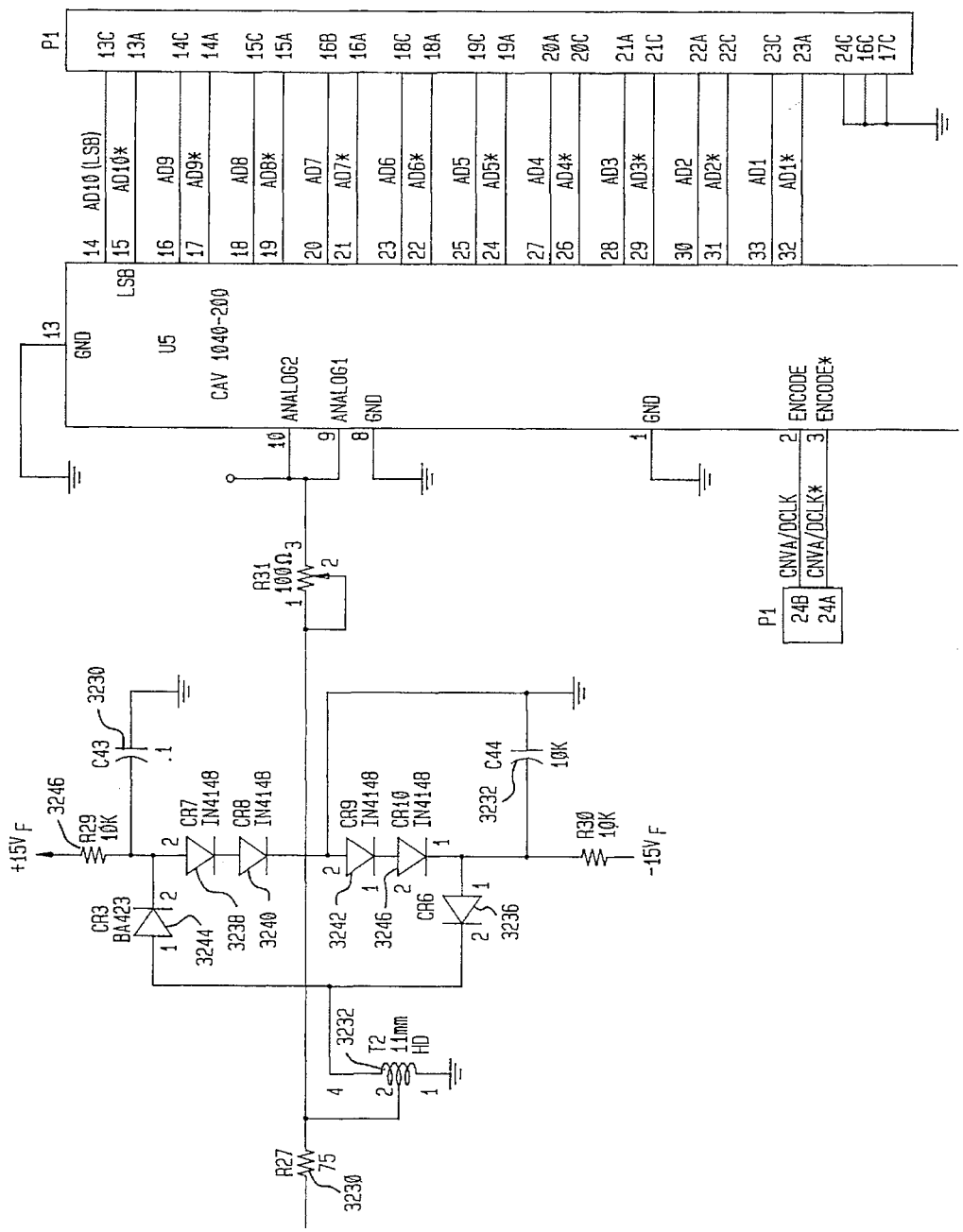
FIG. 11B3

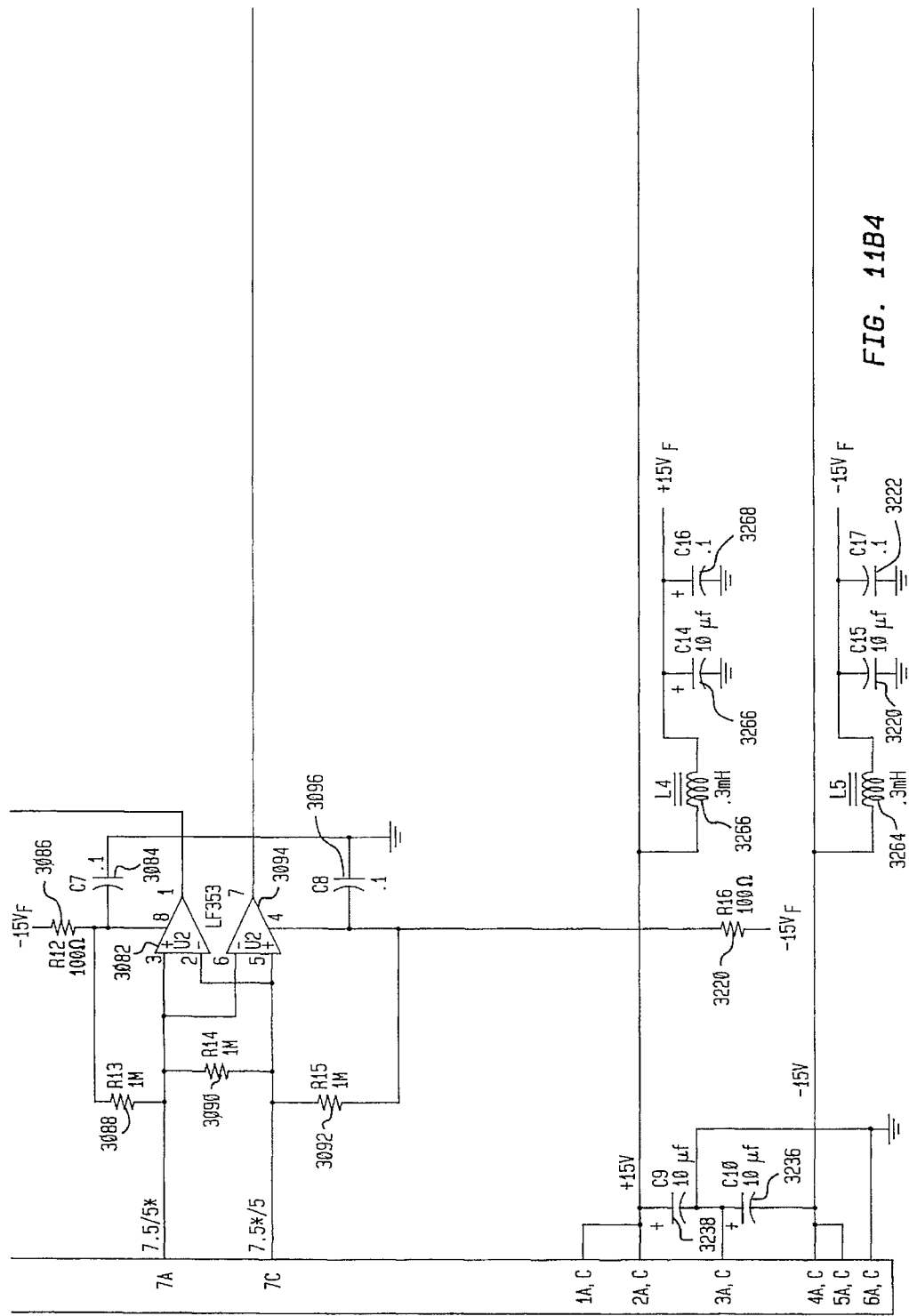
FIG. 11B4

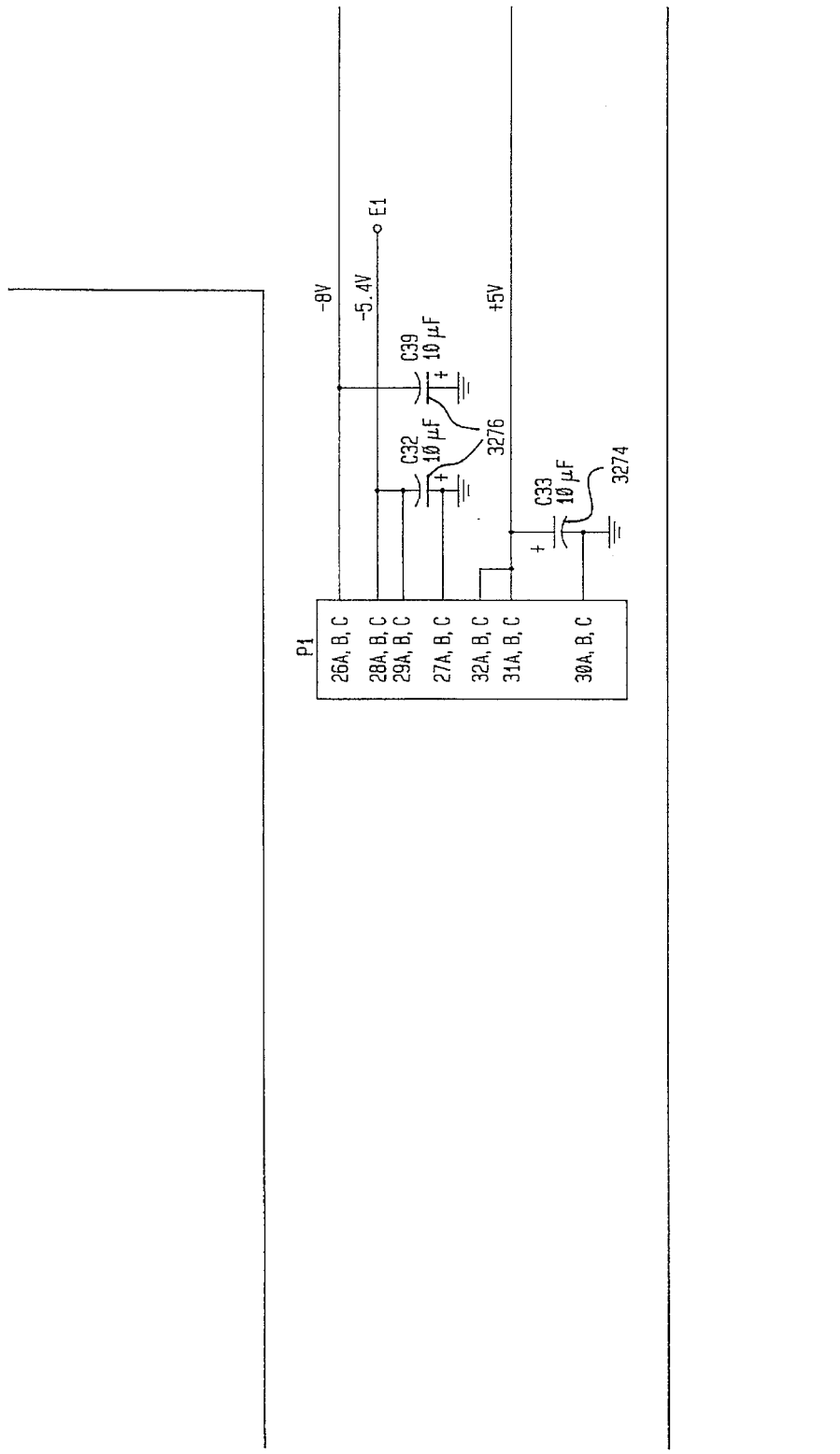
FIG. 11B5

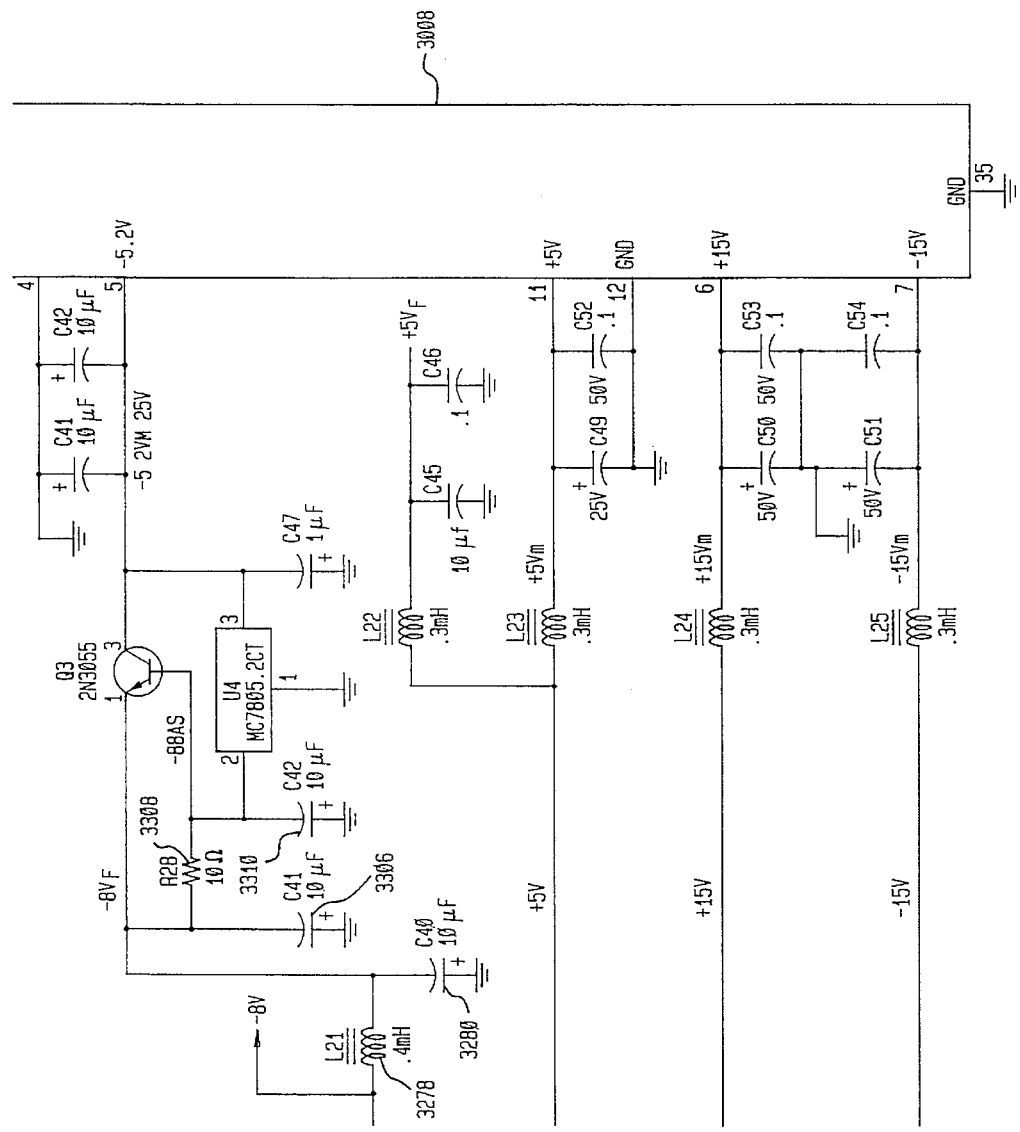
FIG. 11B6

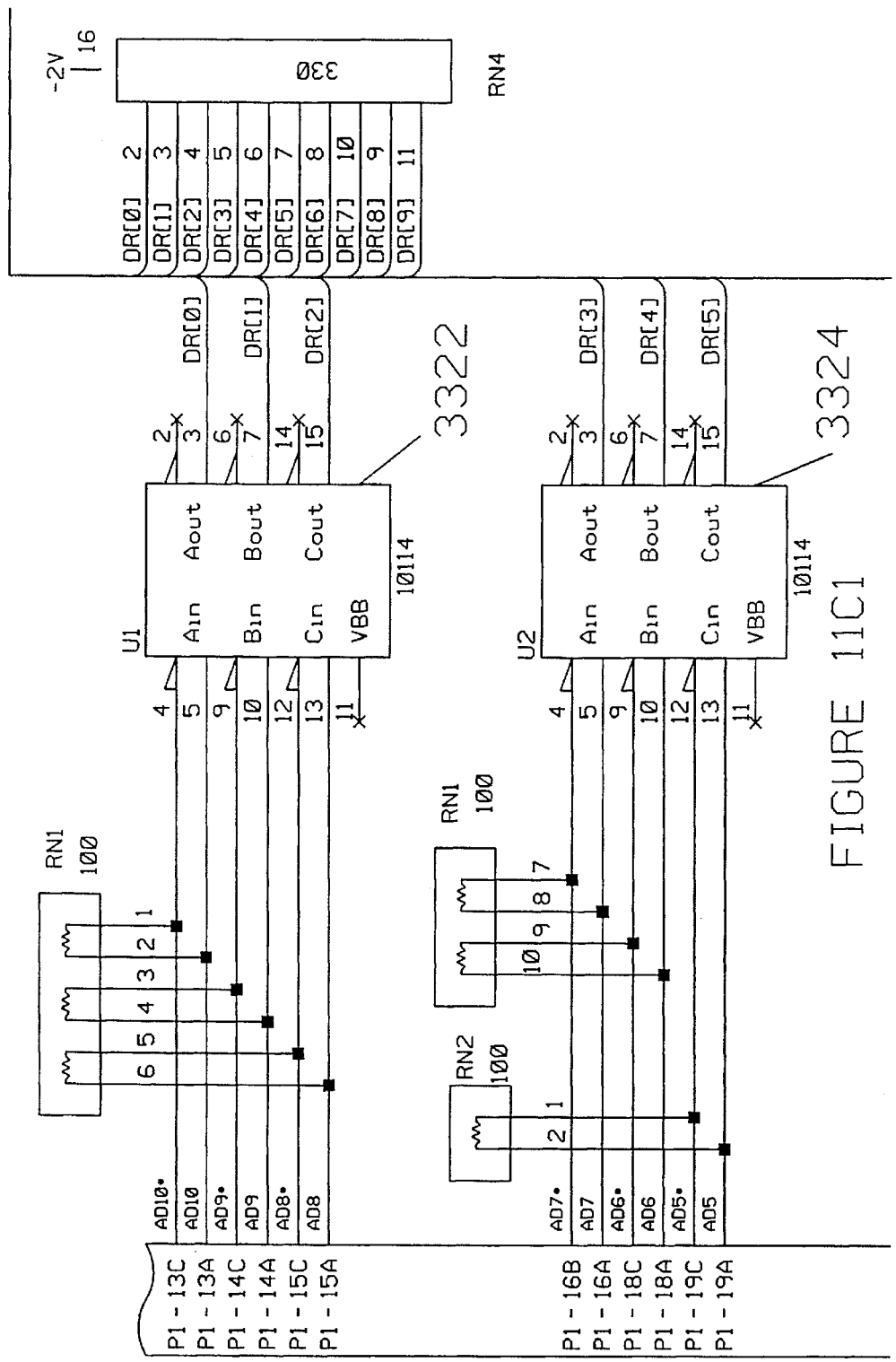
FIGURE 11C1

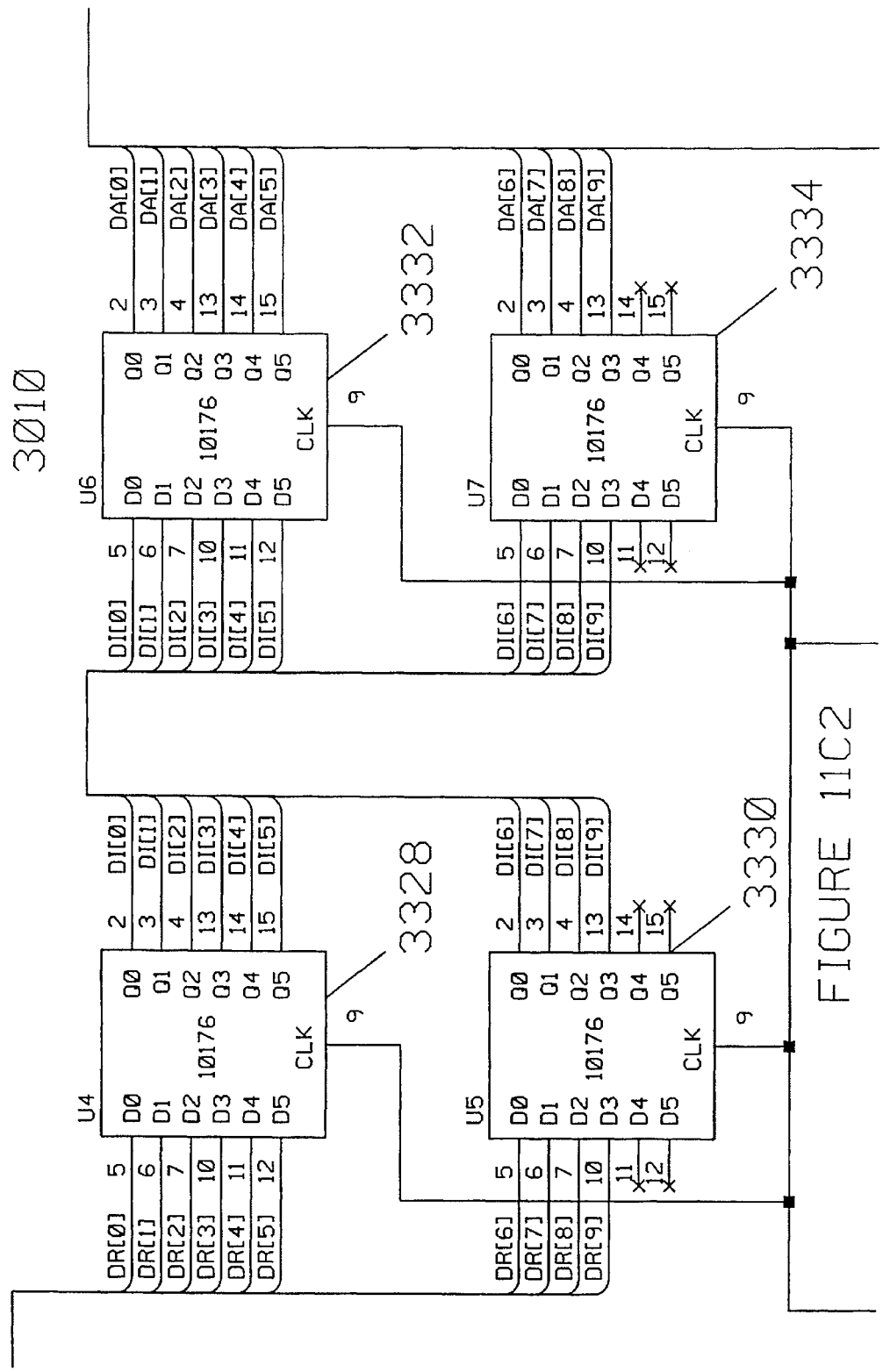
FIGURE 11C2

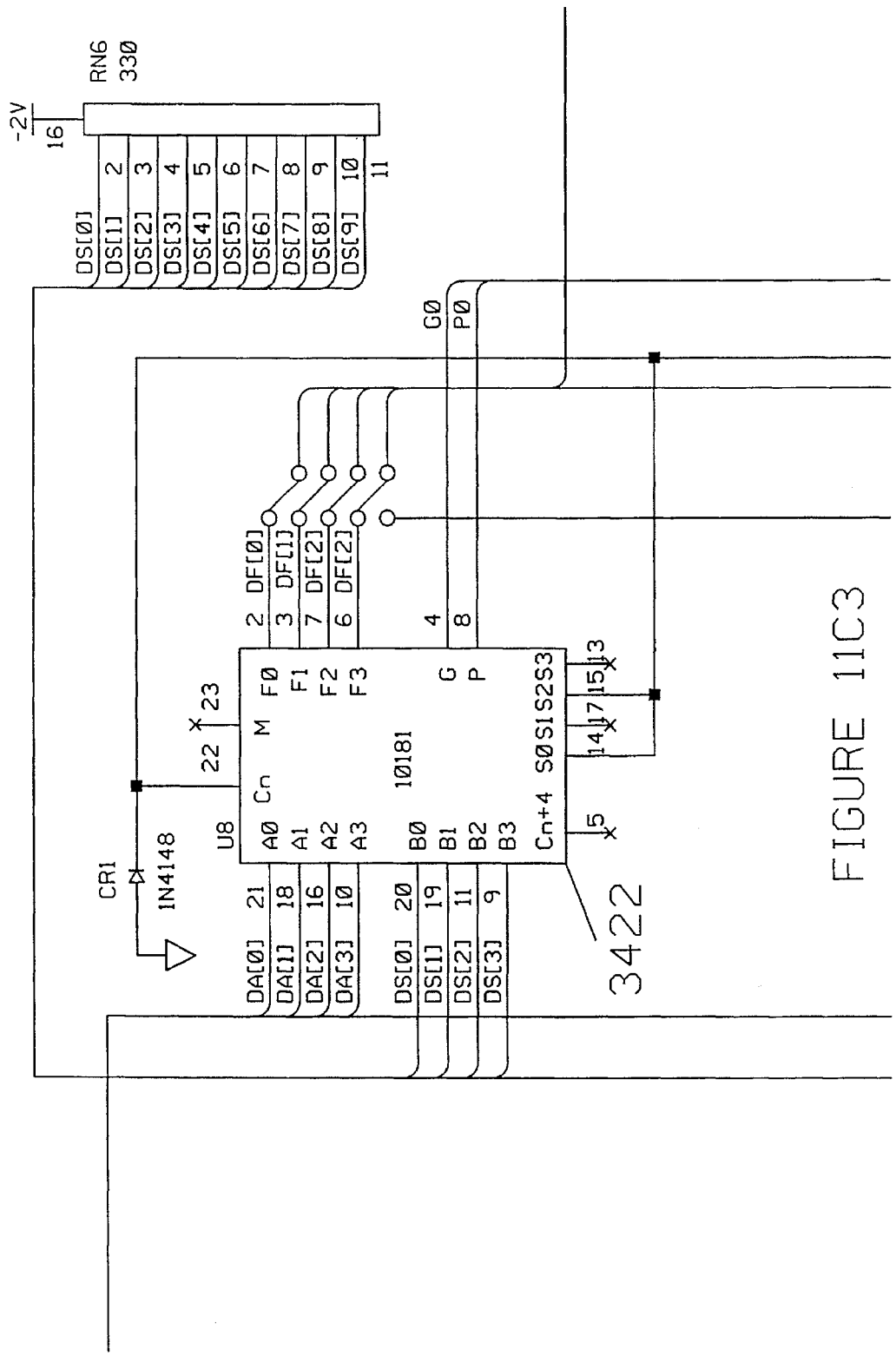
FIGURE 11C3

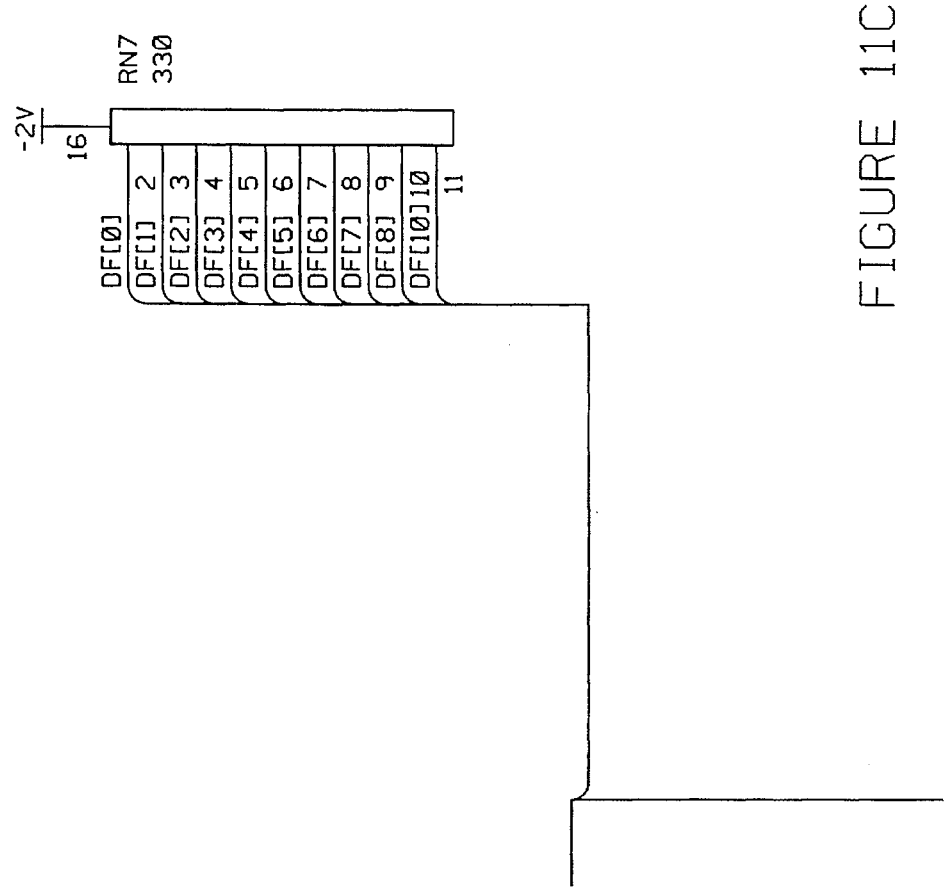
FIGURE 11C4

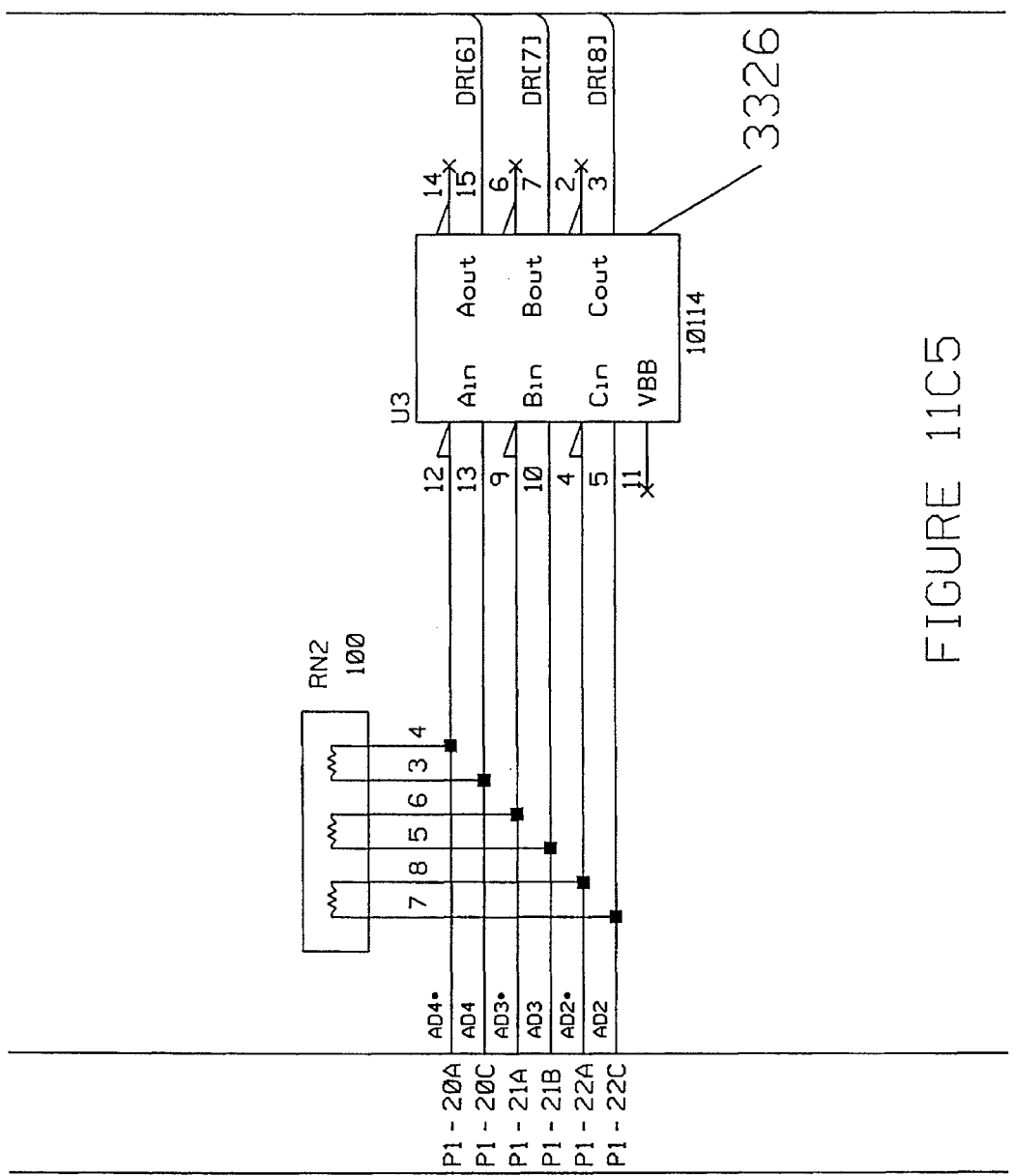
FIGURE 11C5

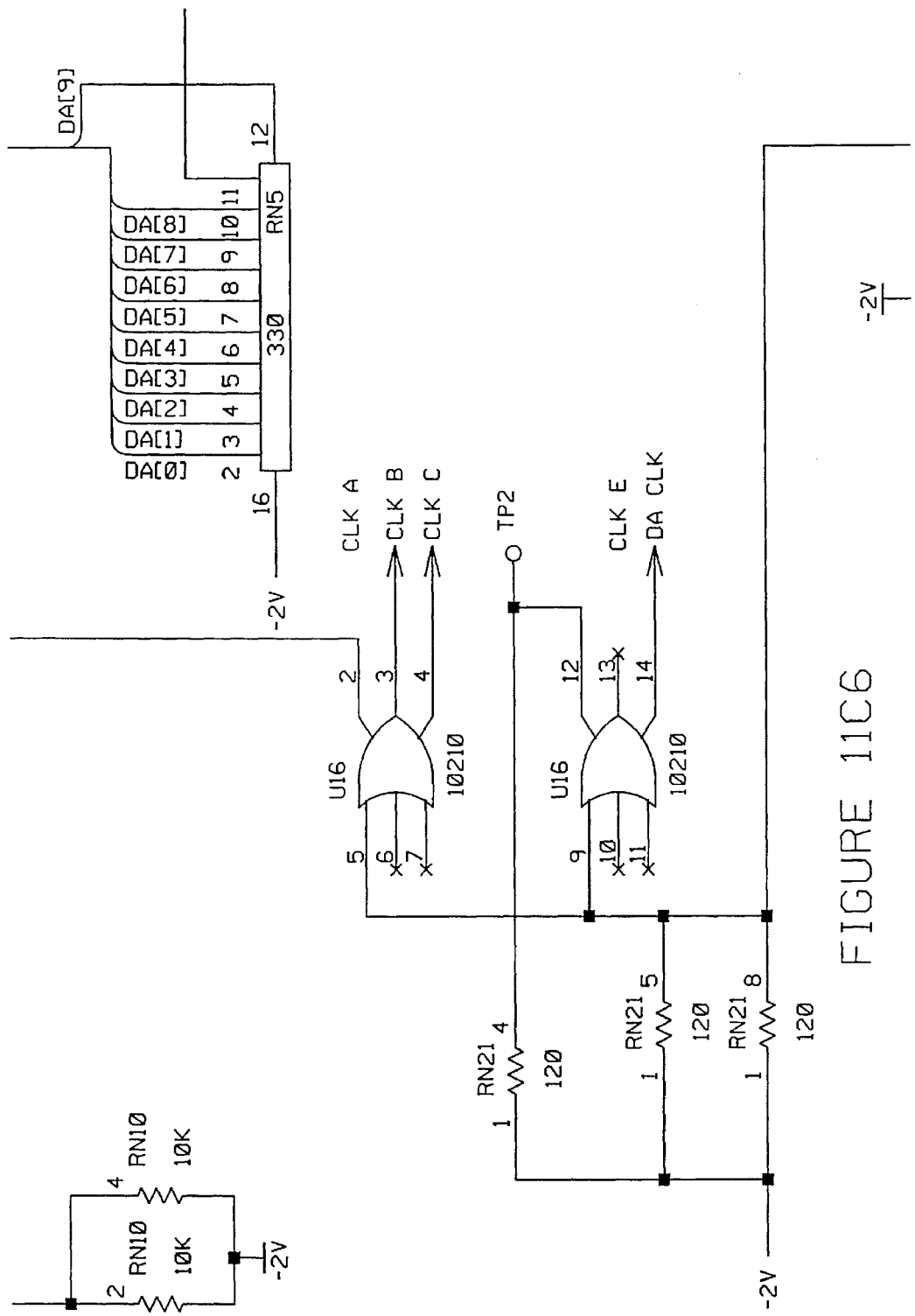
FIGURE 11C6

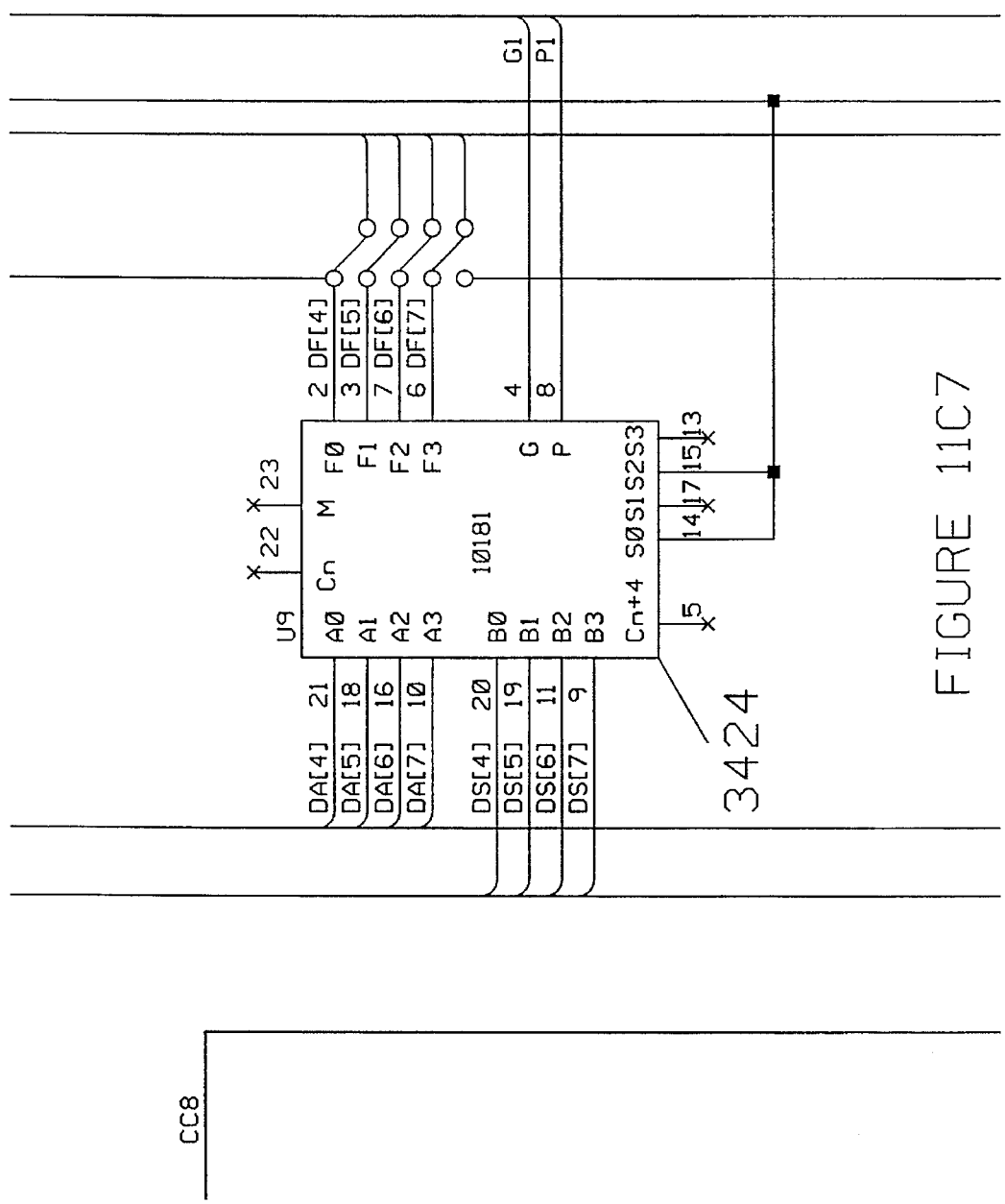
FIGURE 11C7

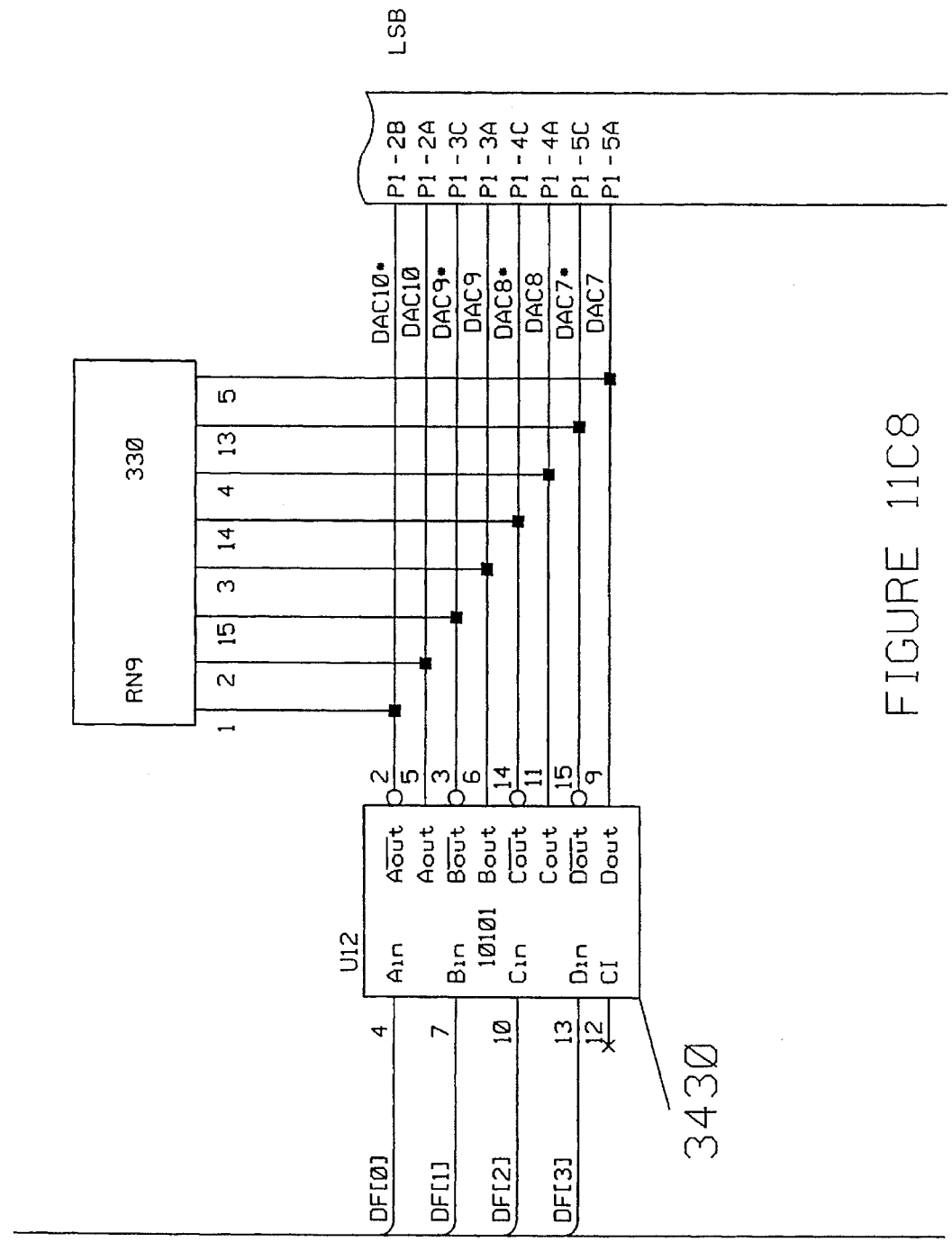
FIGURE 11C8

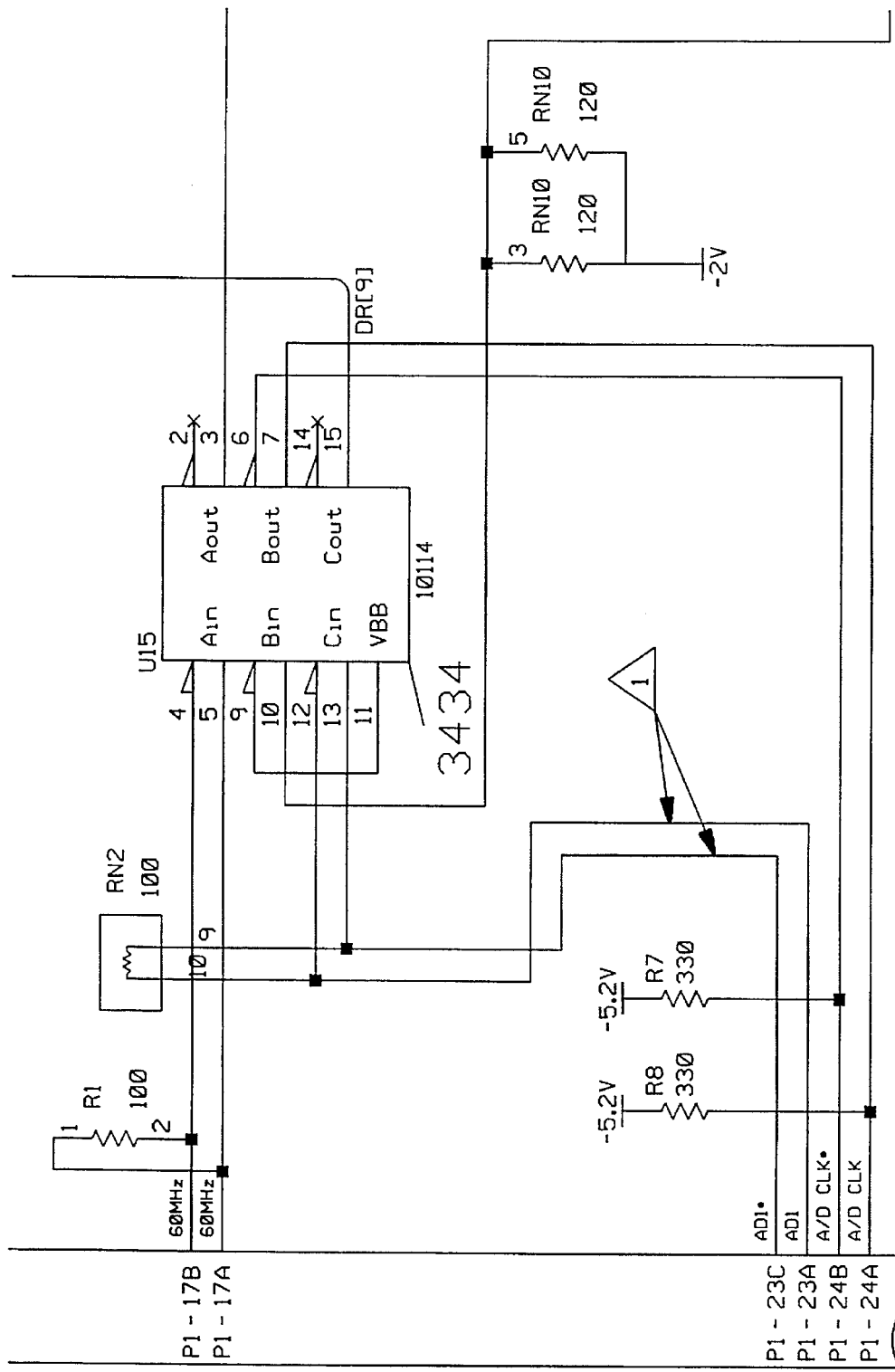
FIGURE 11C9

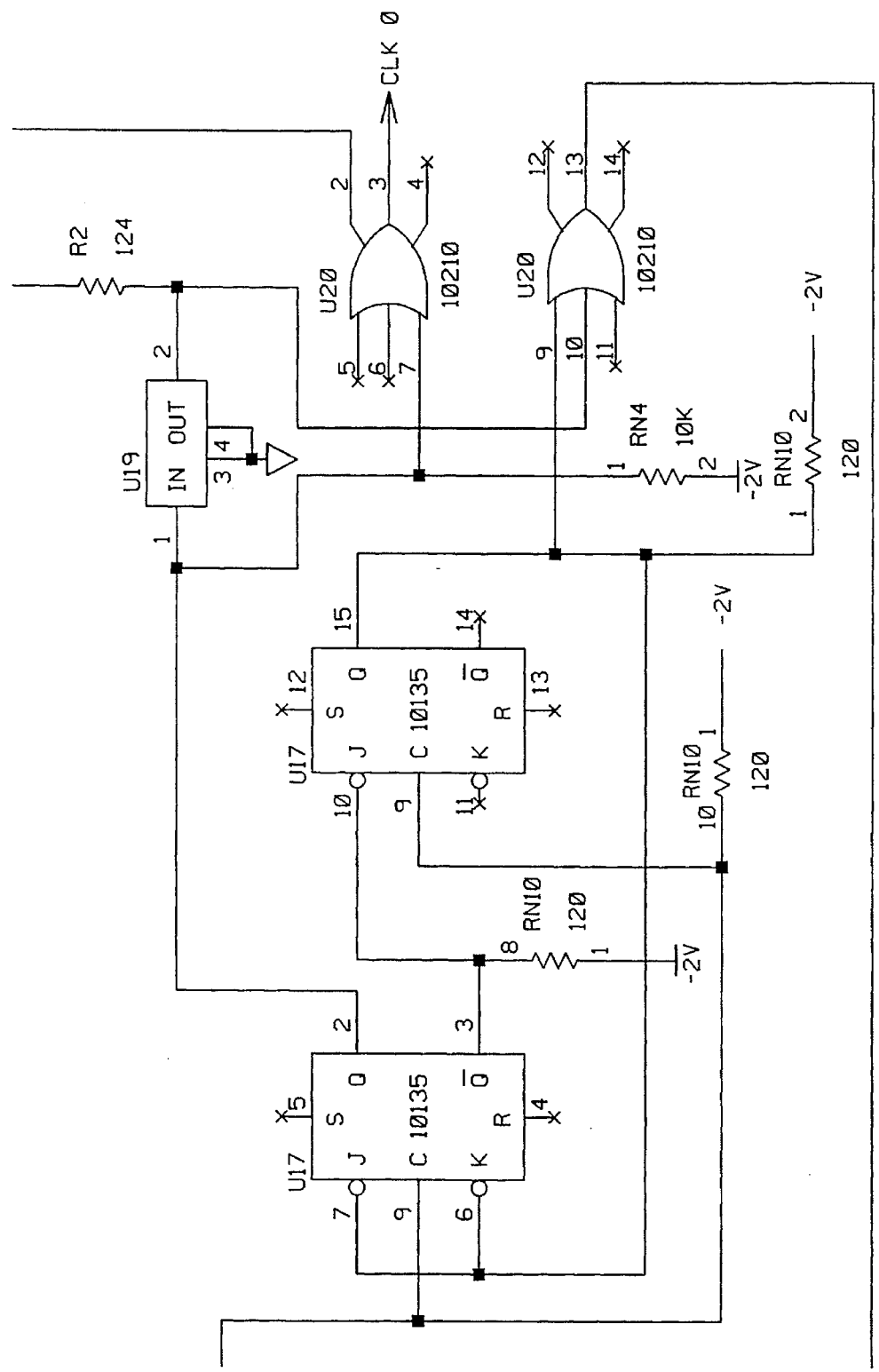
FIGURE 11C10

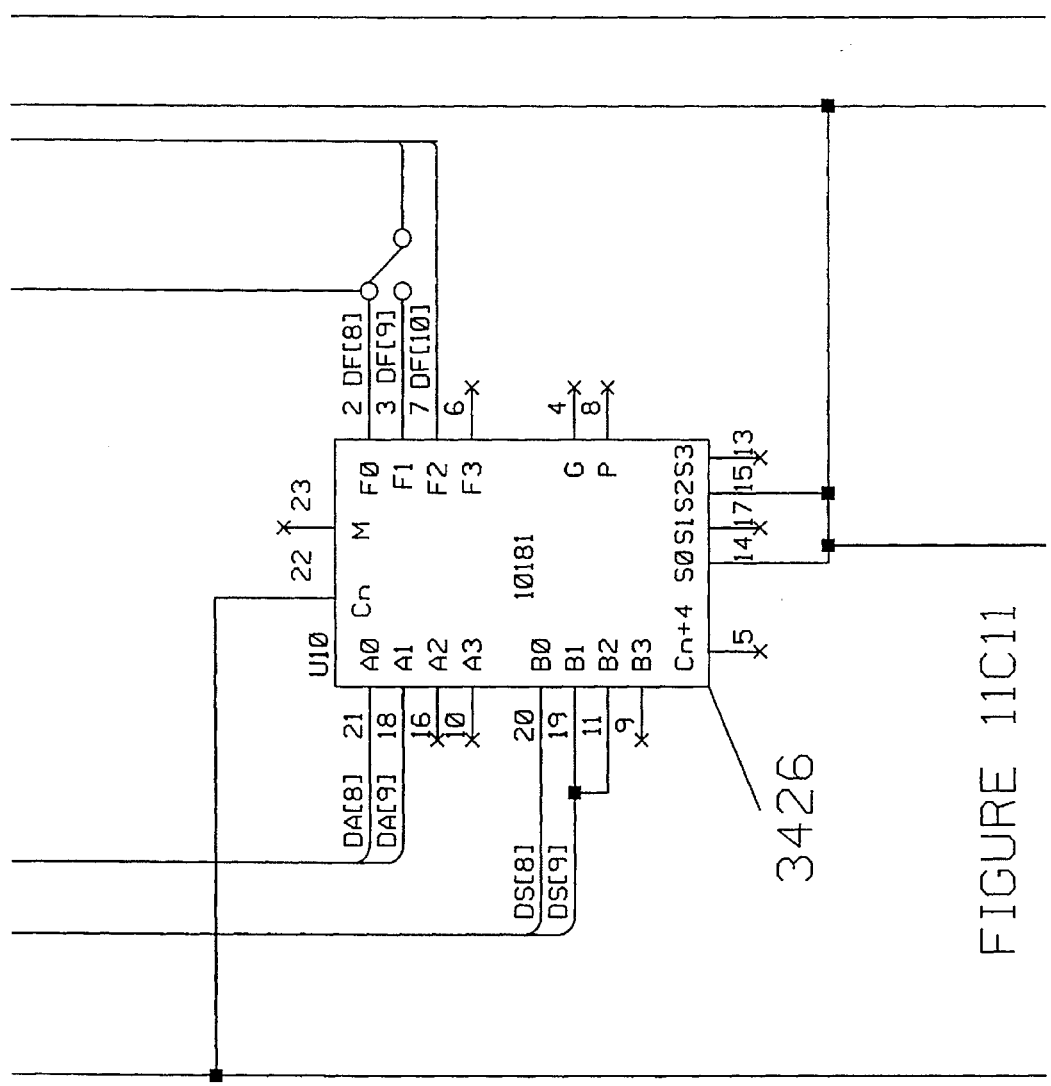
FIGURE 11C11

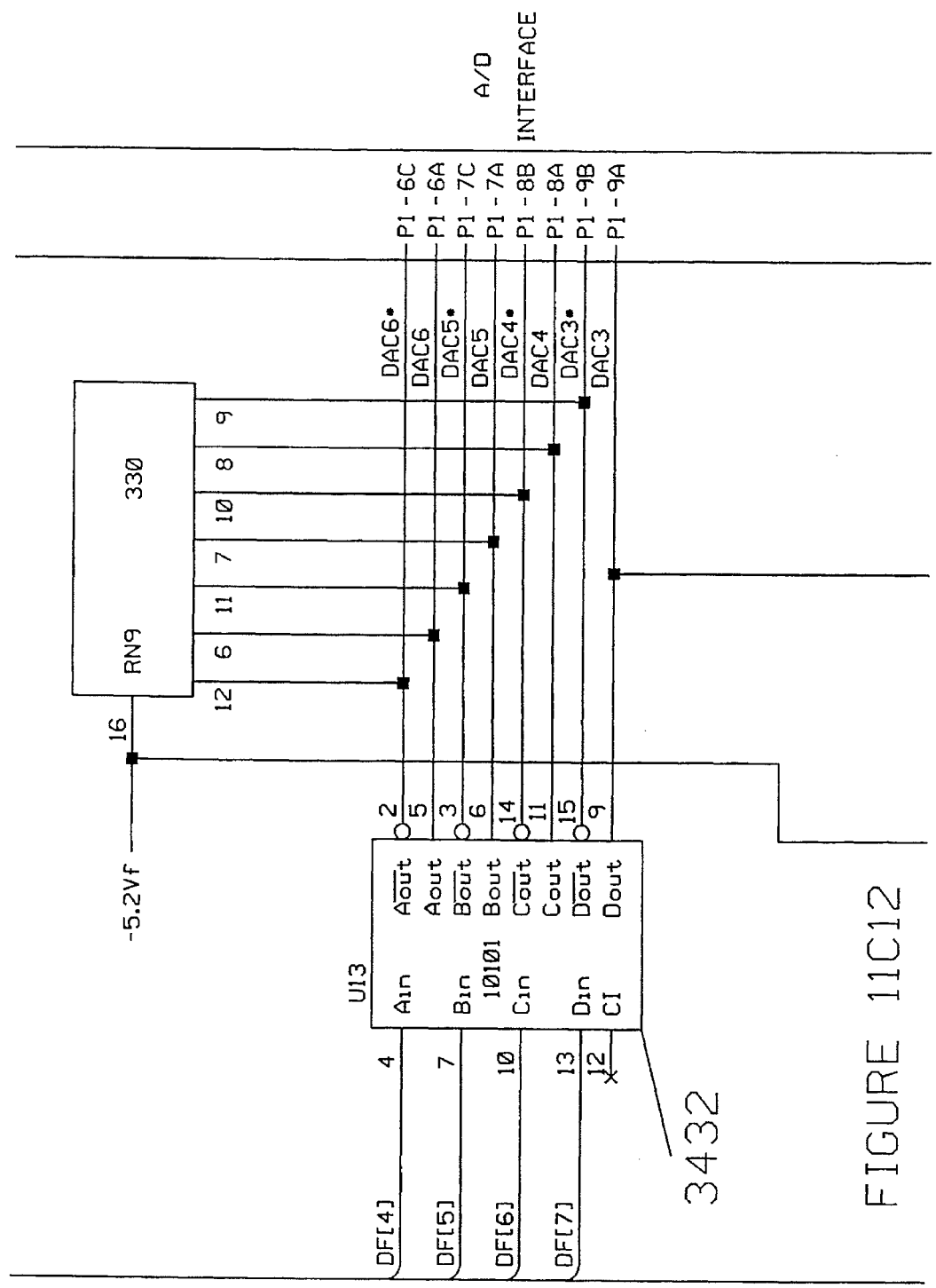
FIGURE 11C12

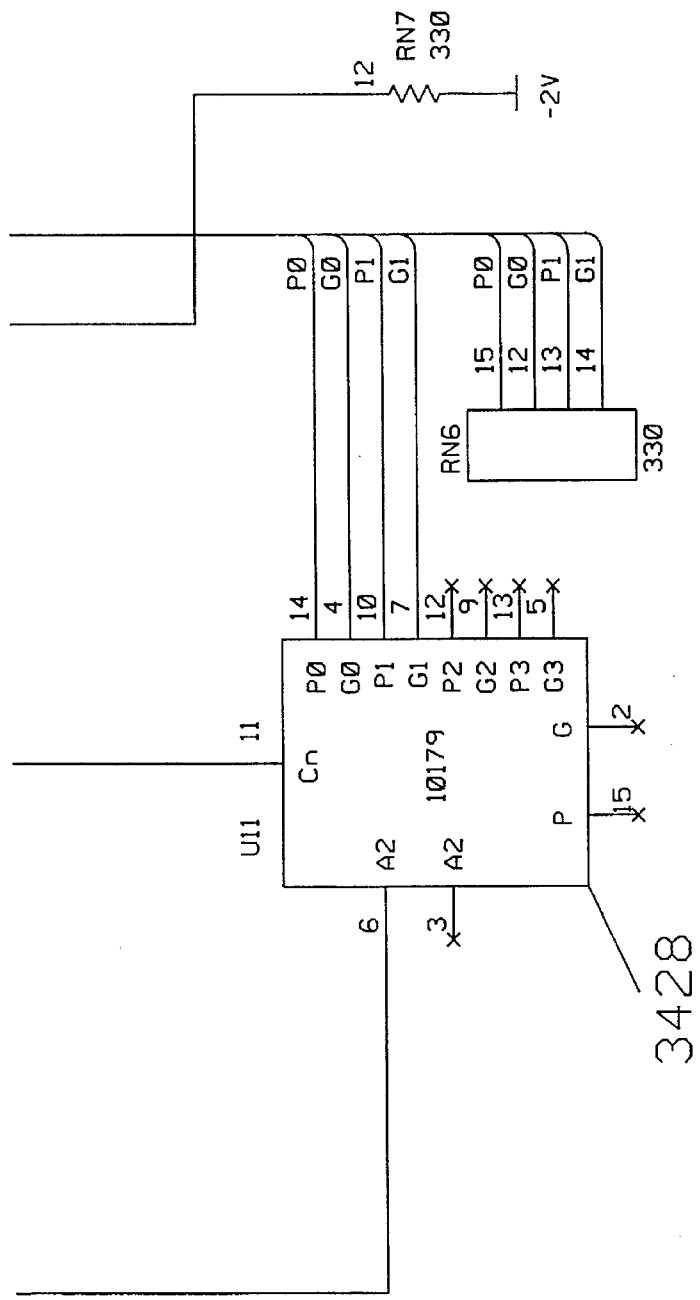
FIGURE 11C13

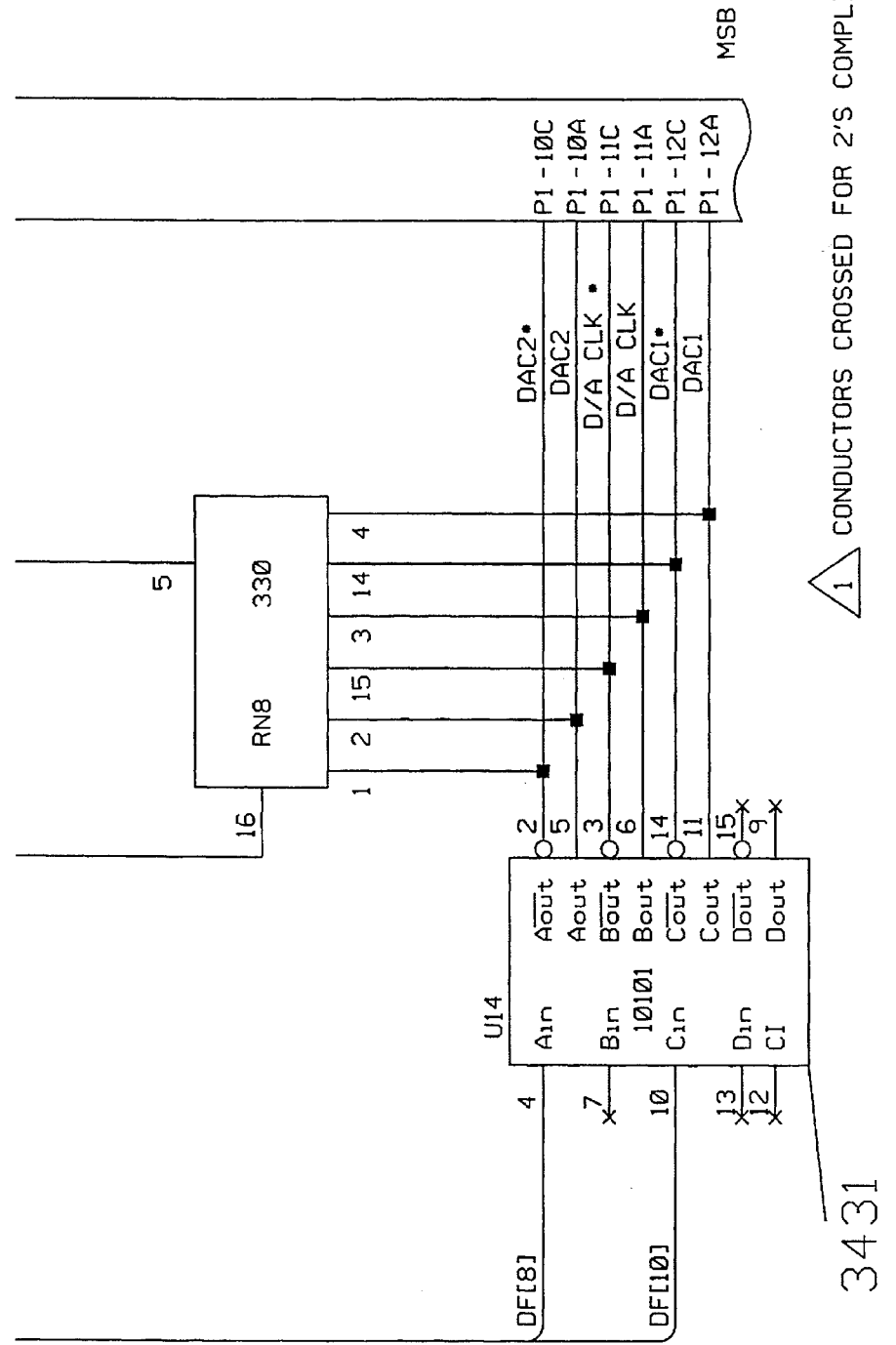
FIGURE 11C14

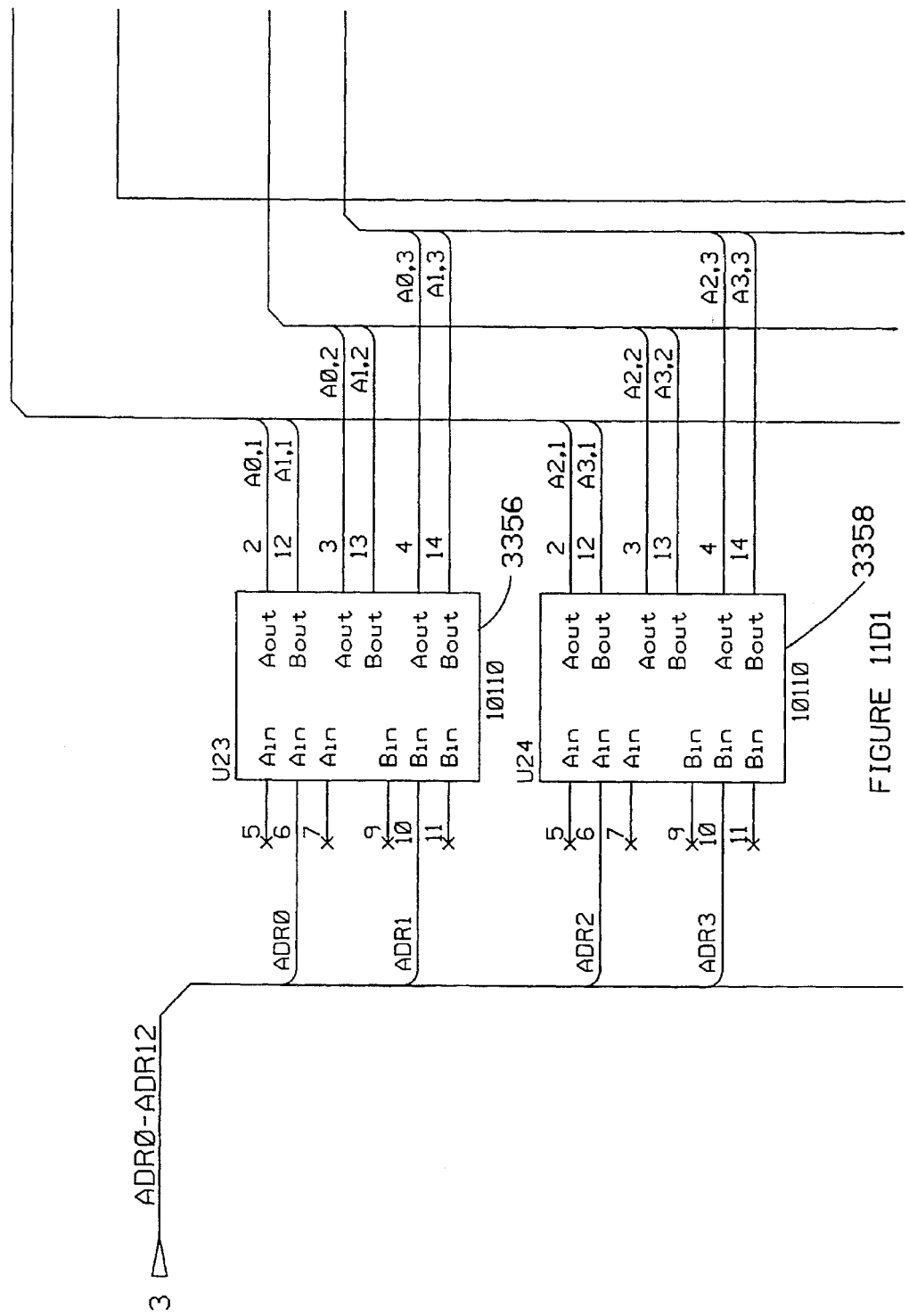
FIGURE 11D1

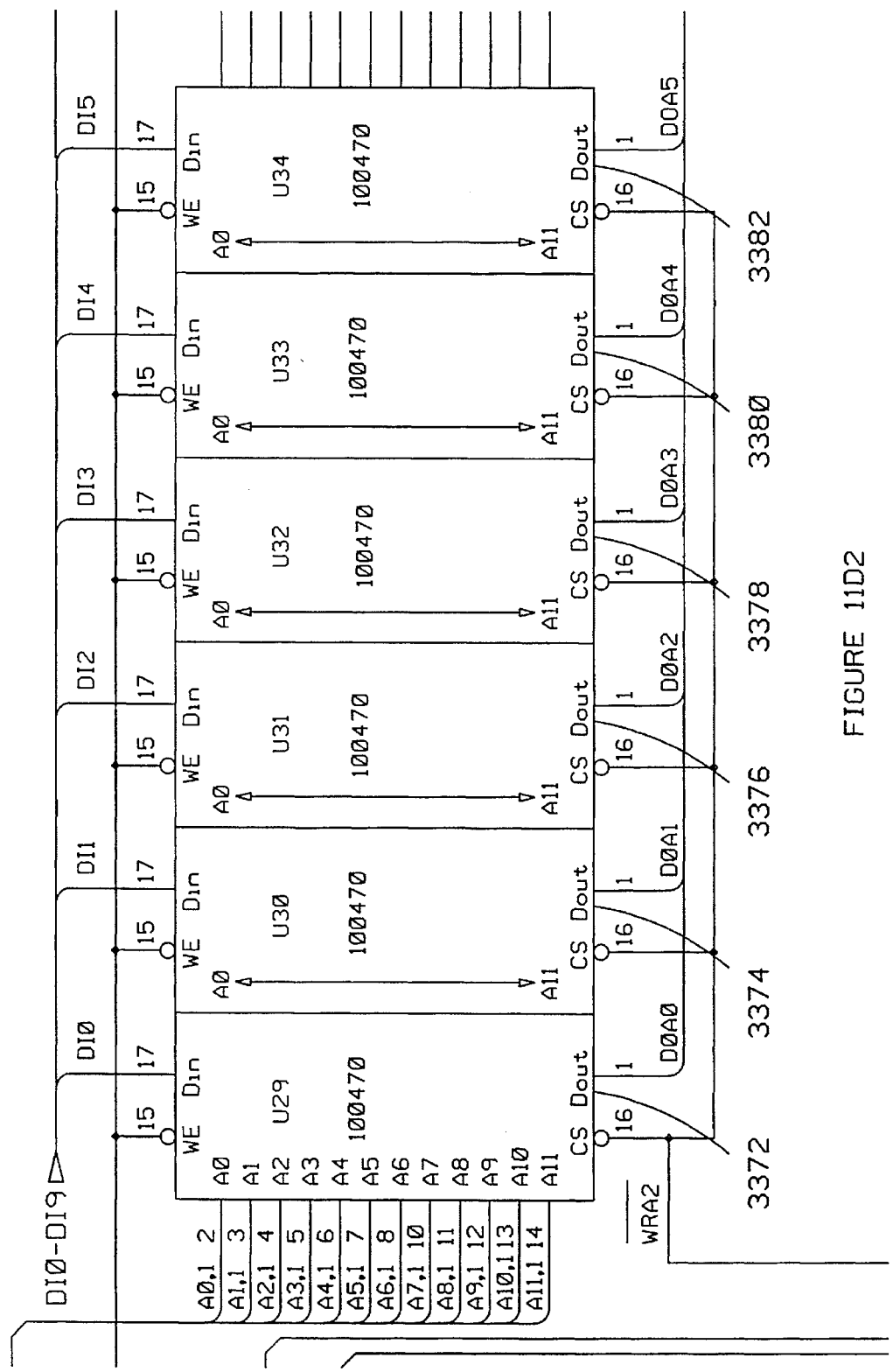
FIGURE 11D2

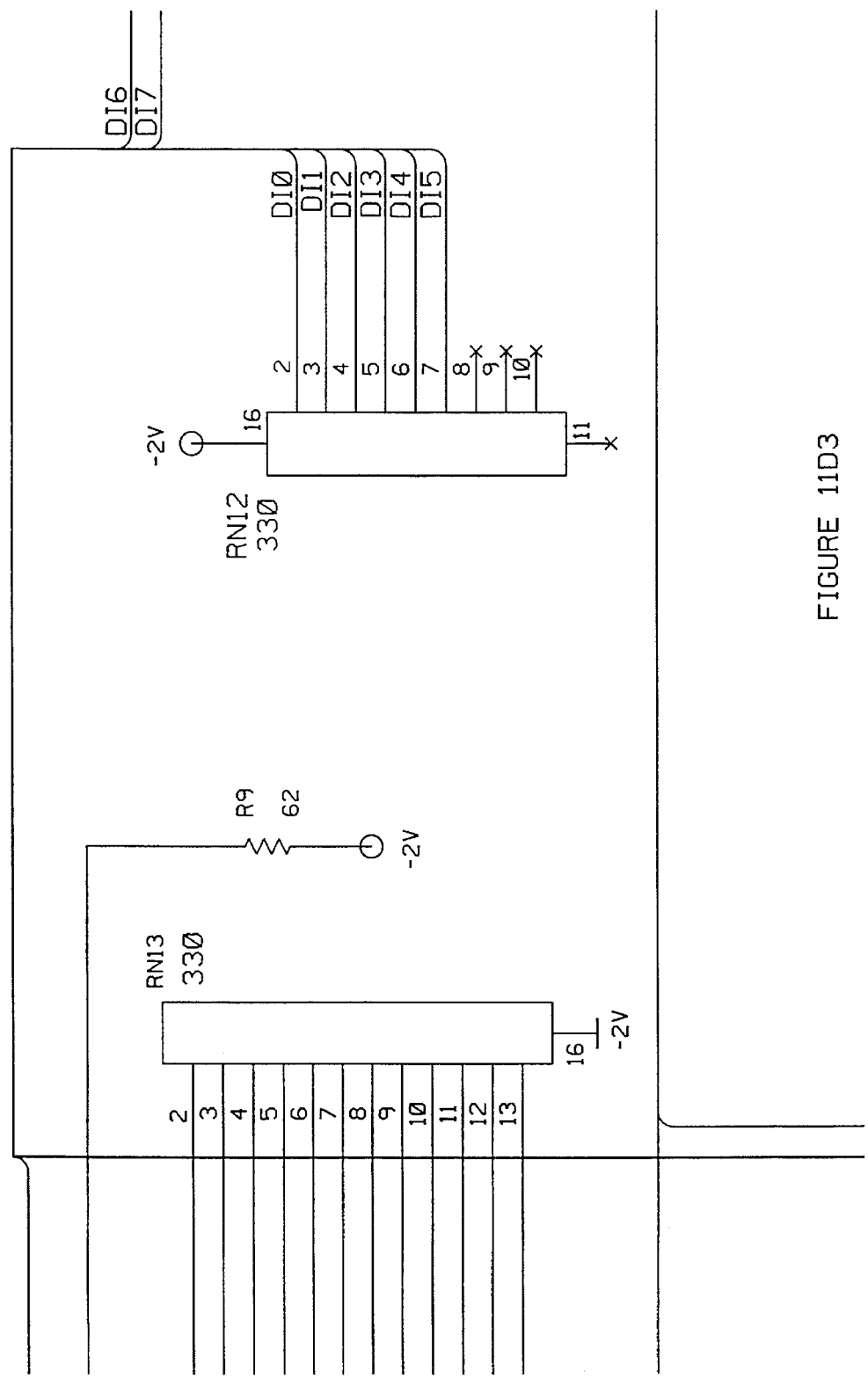
FIGURE 11D3

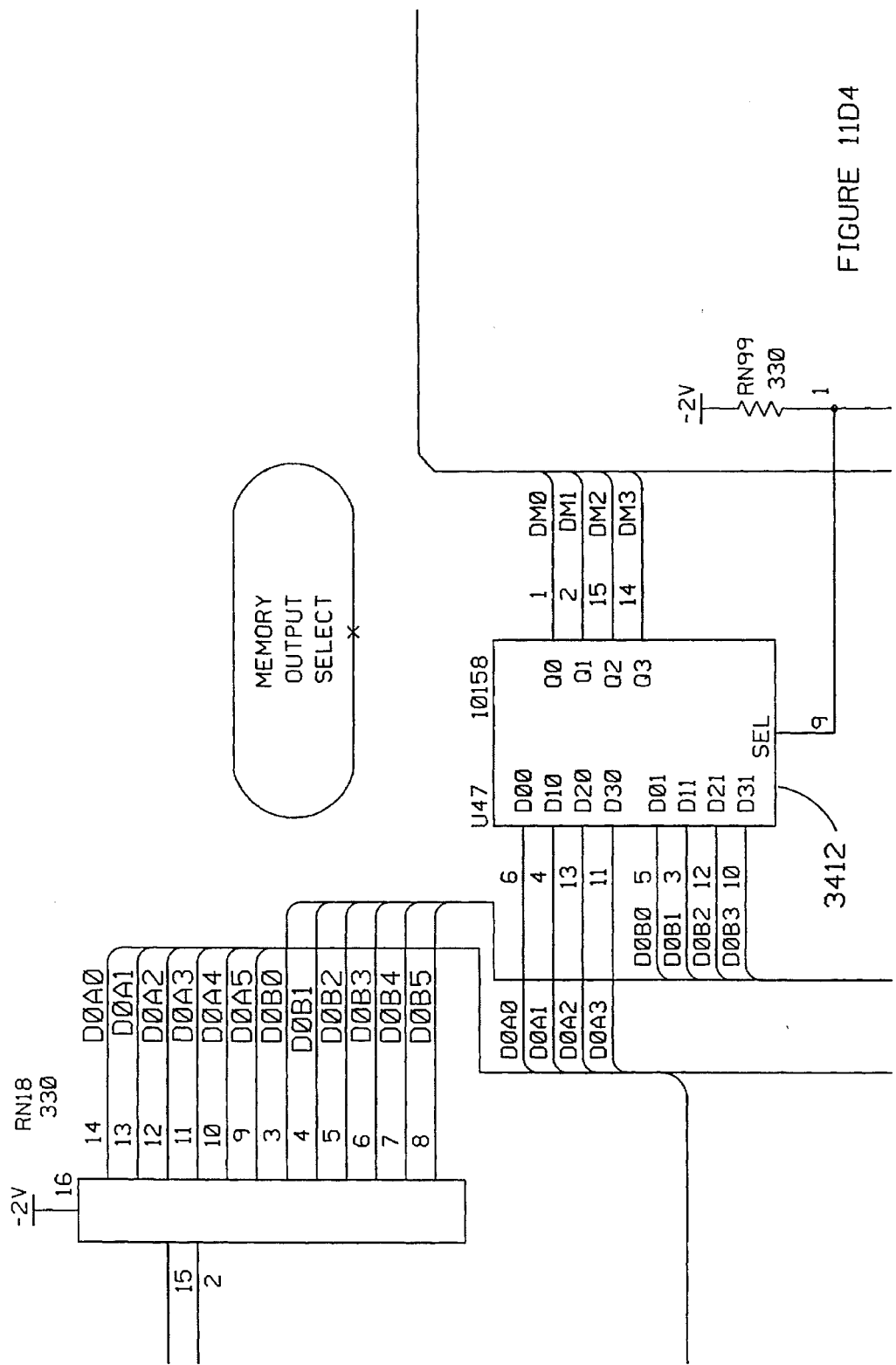

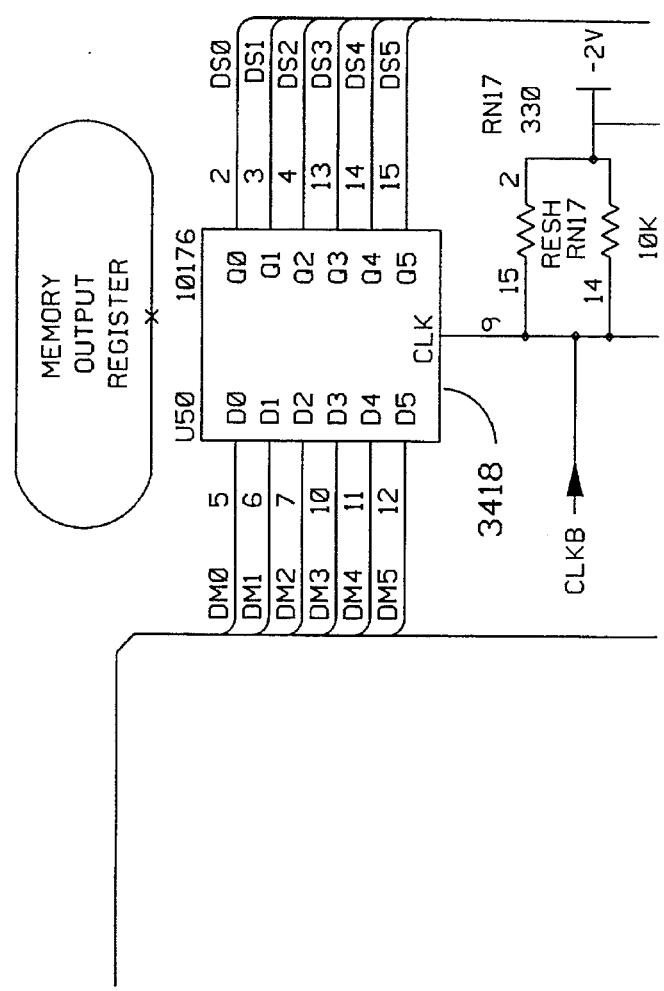
FIGURE 11D5

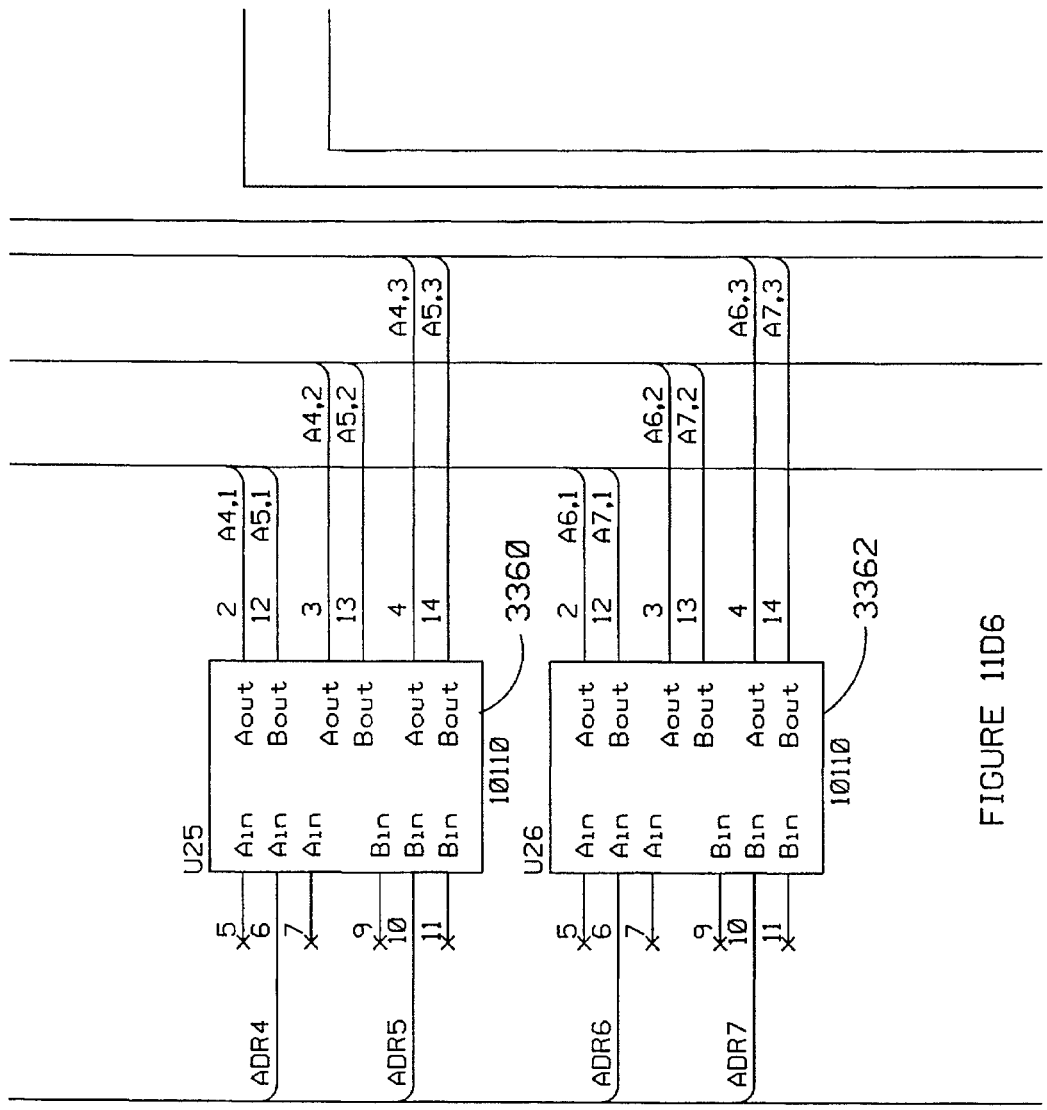
FIGURE 11D6

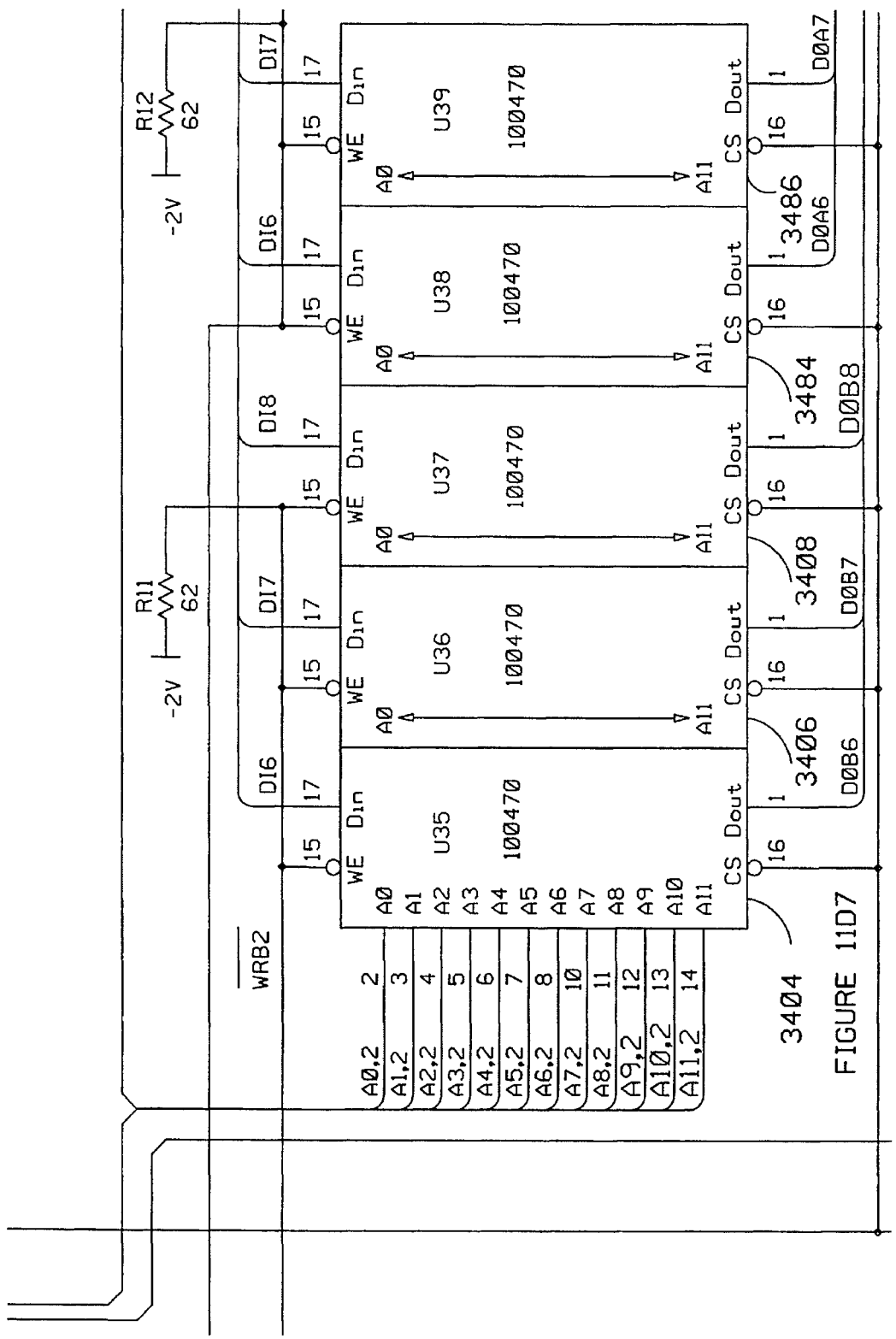
FIGURE 11D7

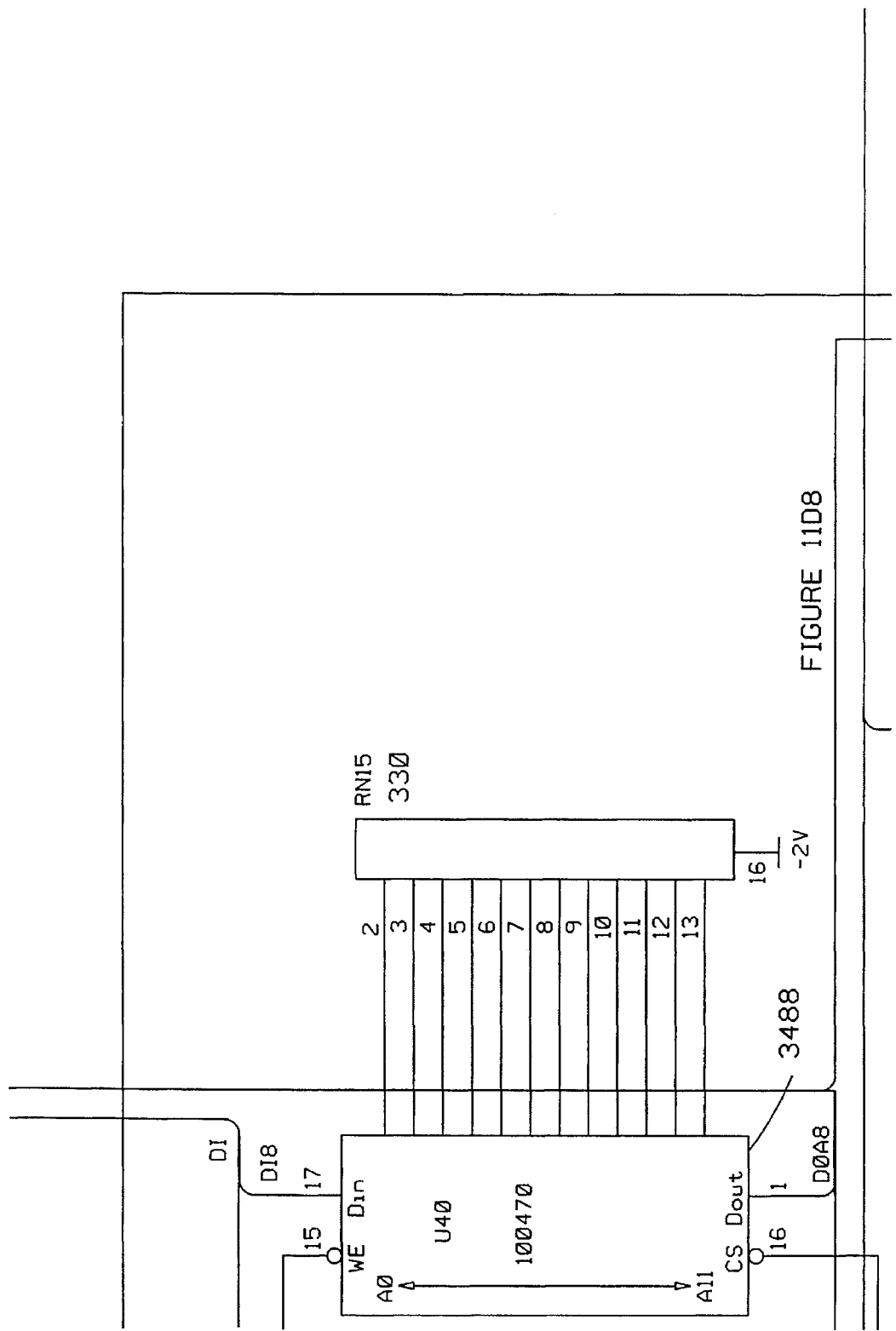
FIGURE 11D8

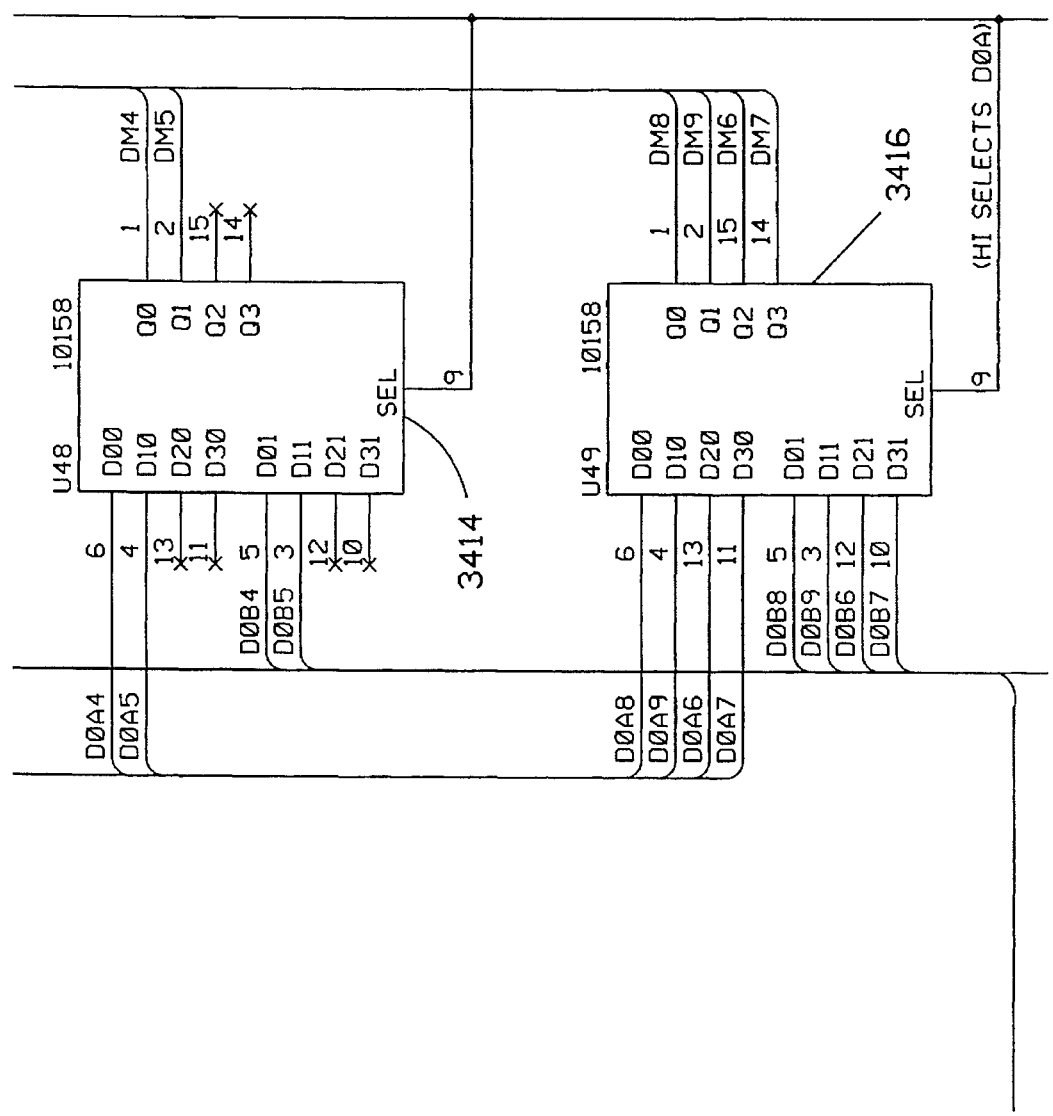
FIGURE 11D9

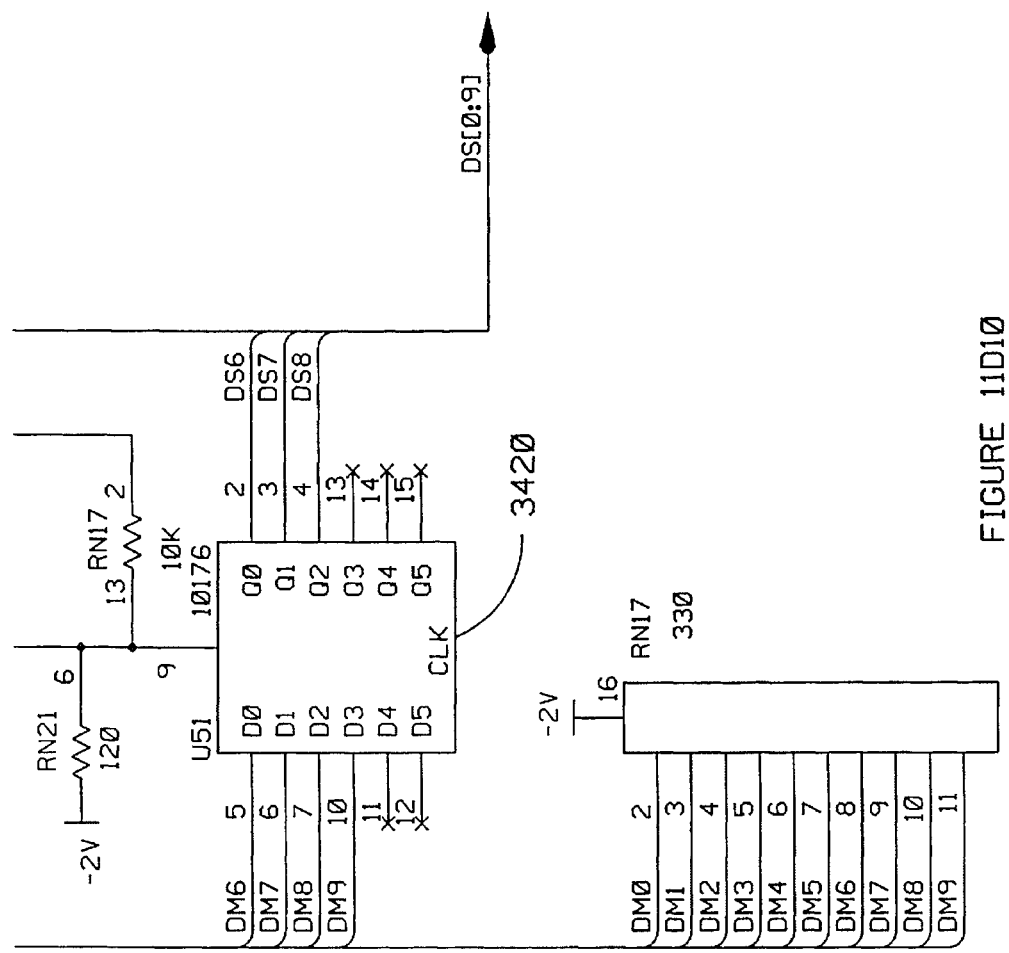
FIGURE 11D10

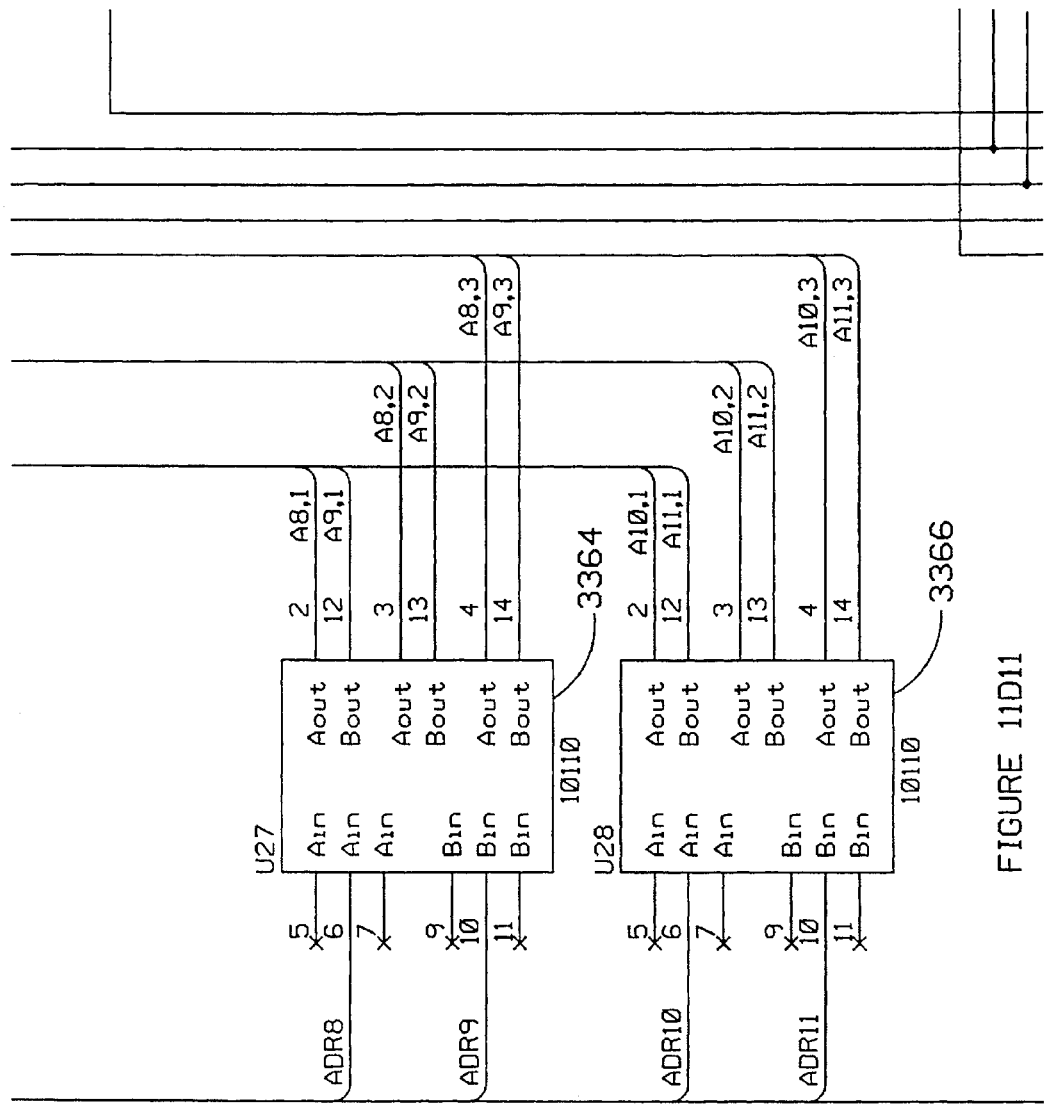
FIGURE 11D11

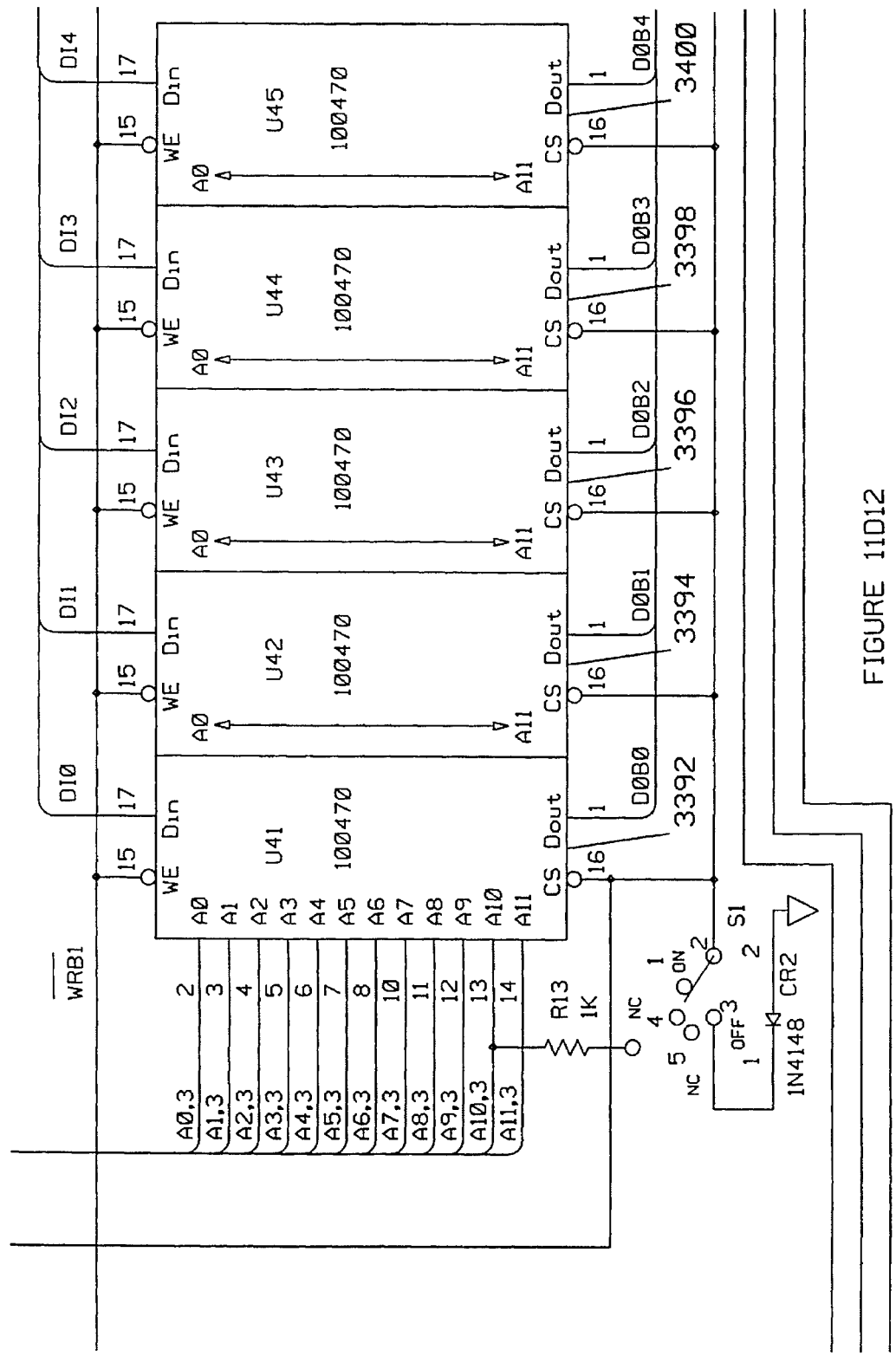
FIGURE 11D12

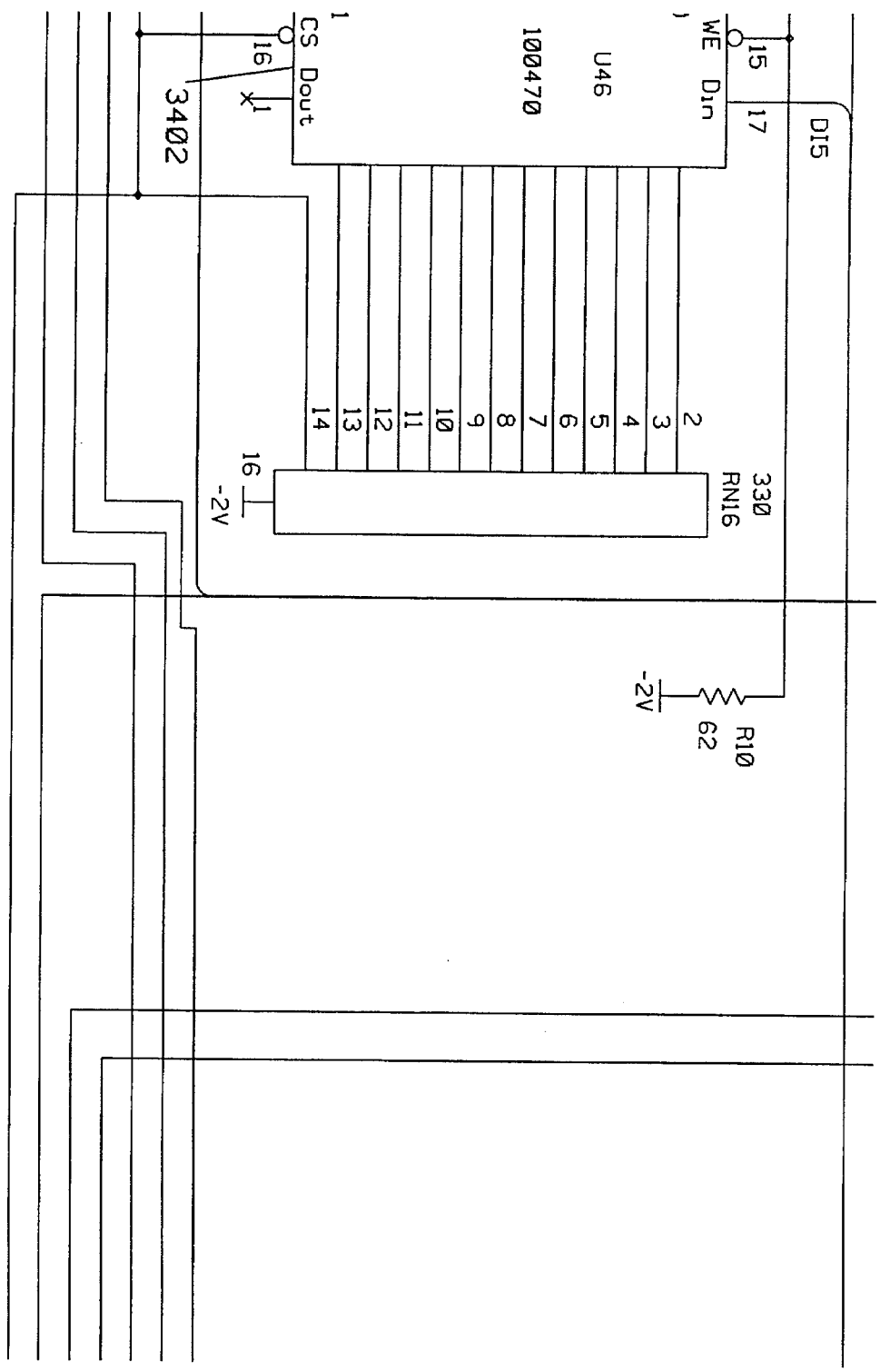
FIGURE 11D13

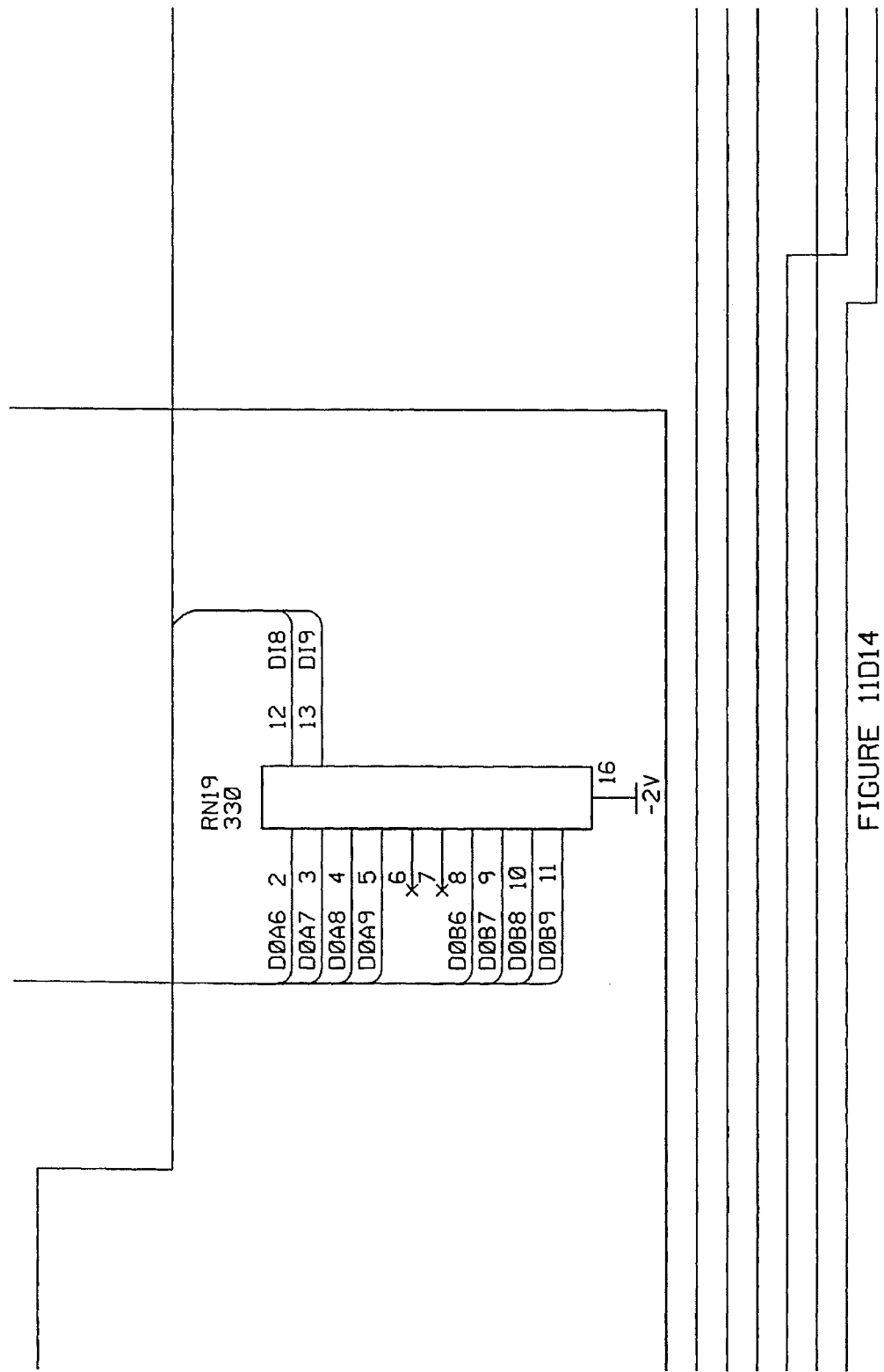
FIGURE 11D14

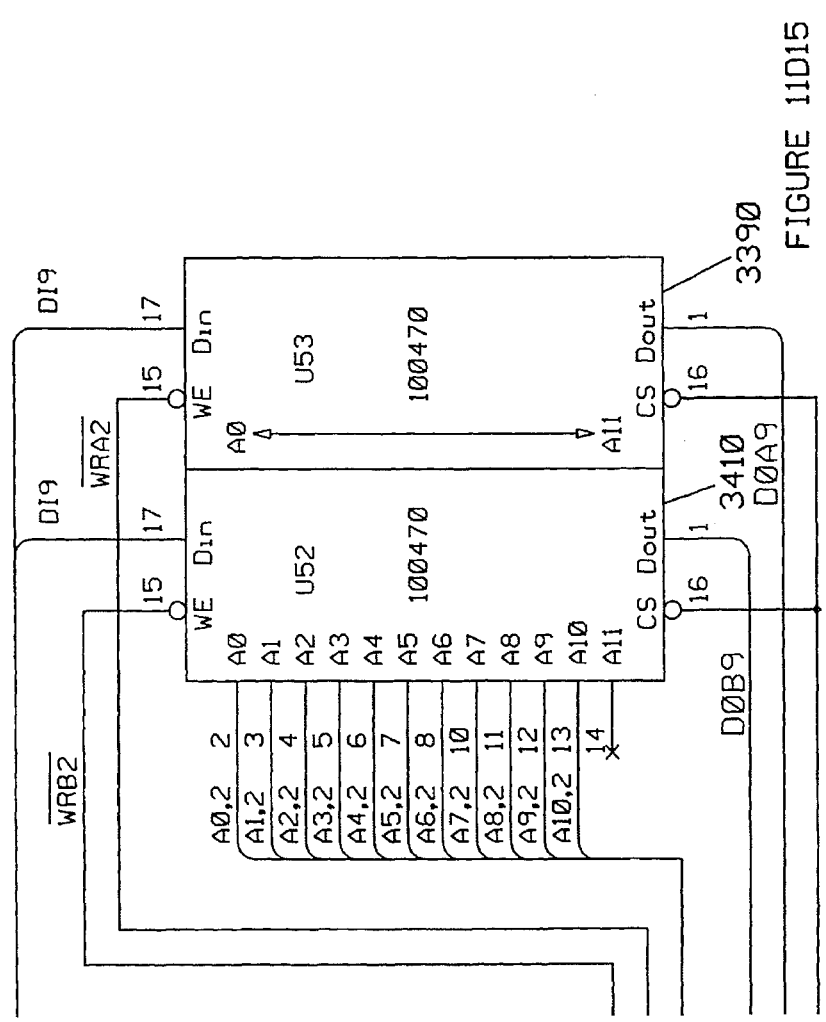
FIGURE 11D15

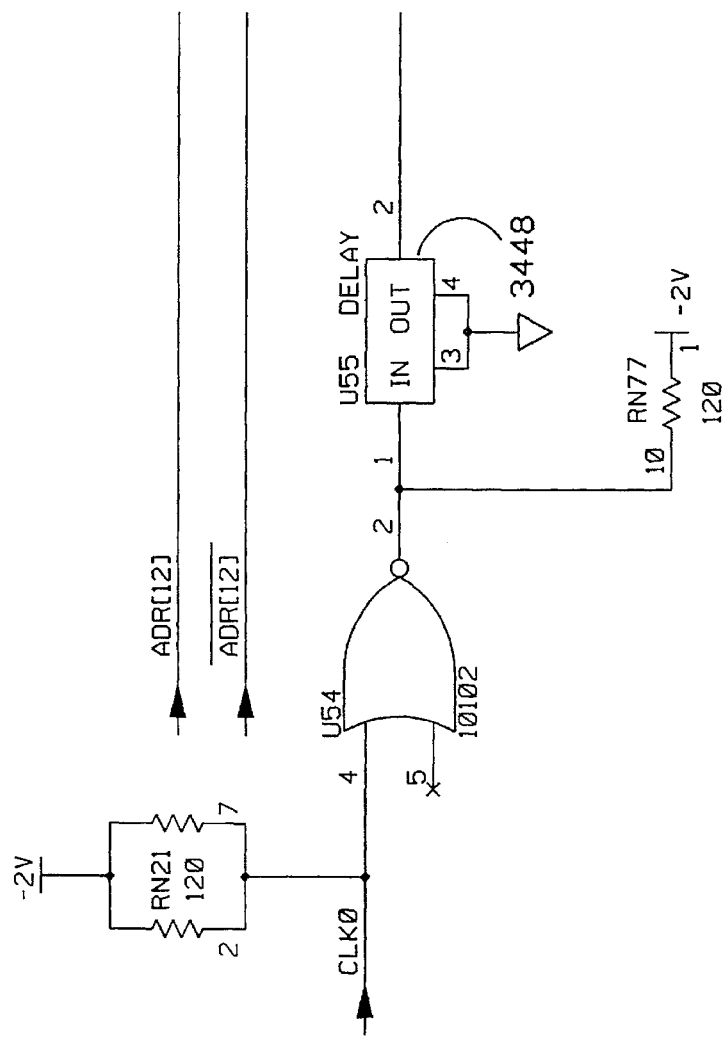
FIGURE 11D16

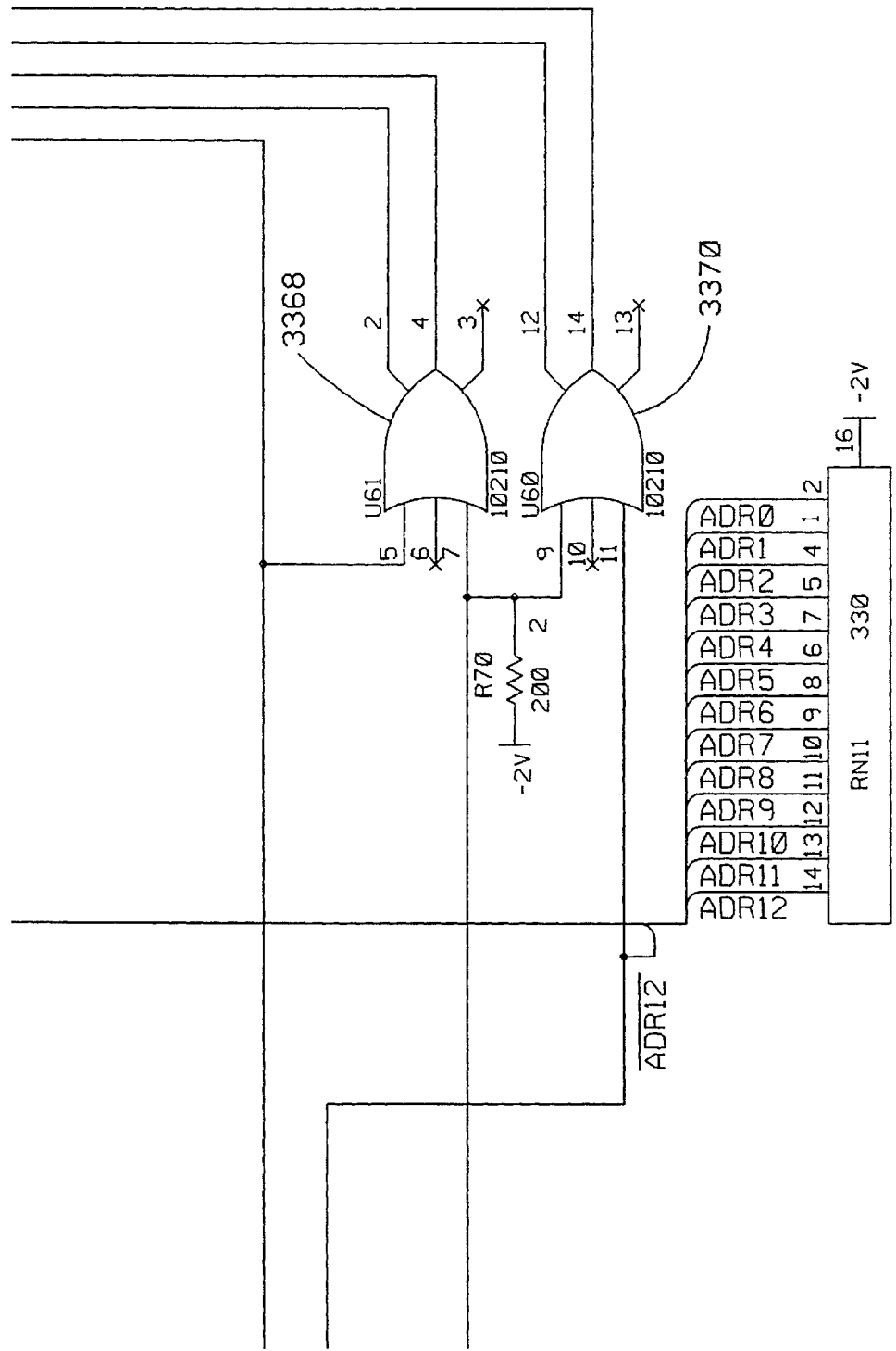
FIGURE 11D17

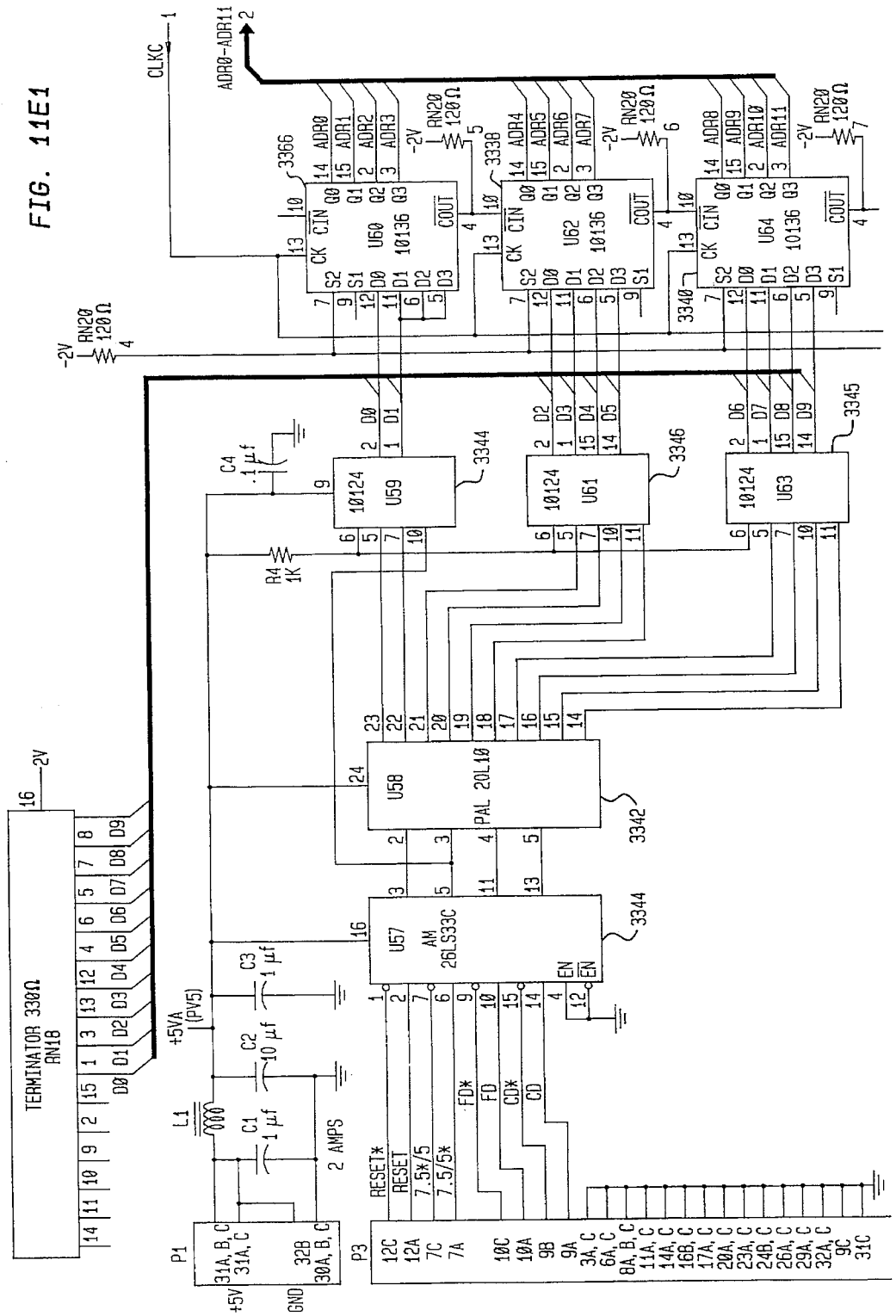
FIG. 11E1

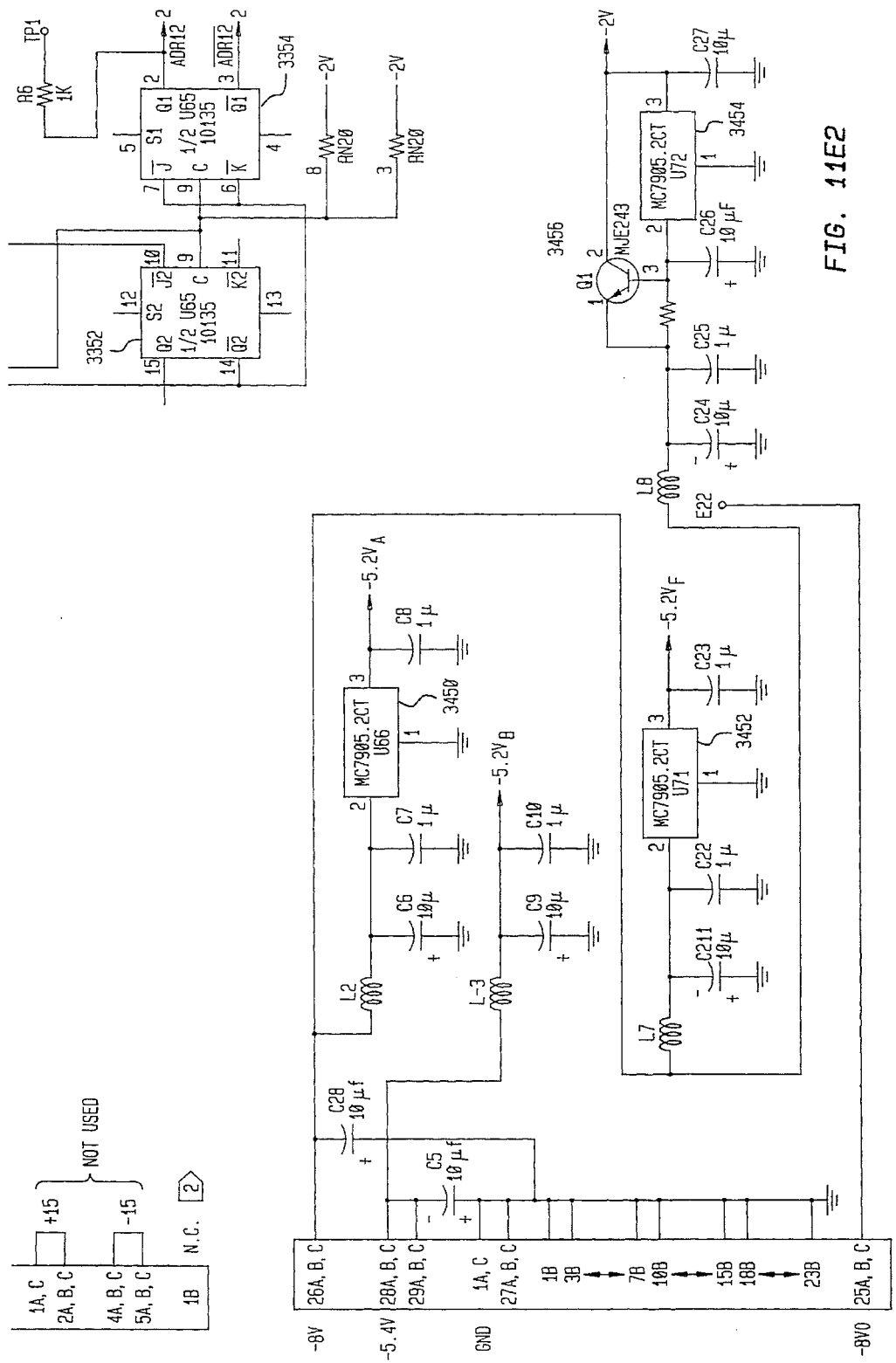
FIG. 11E2

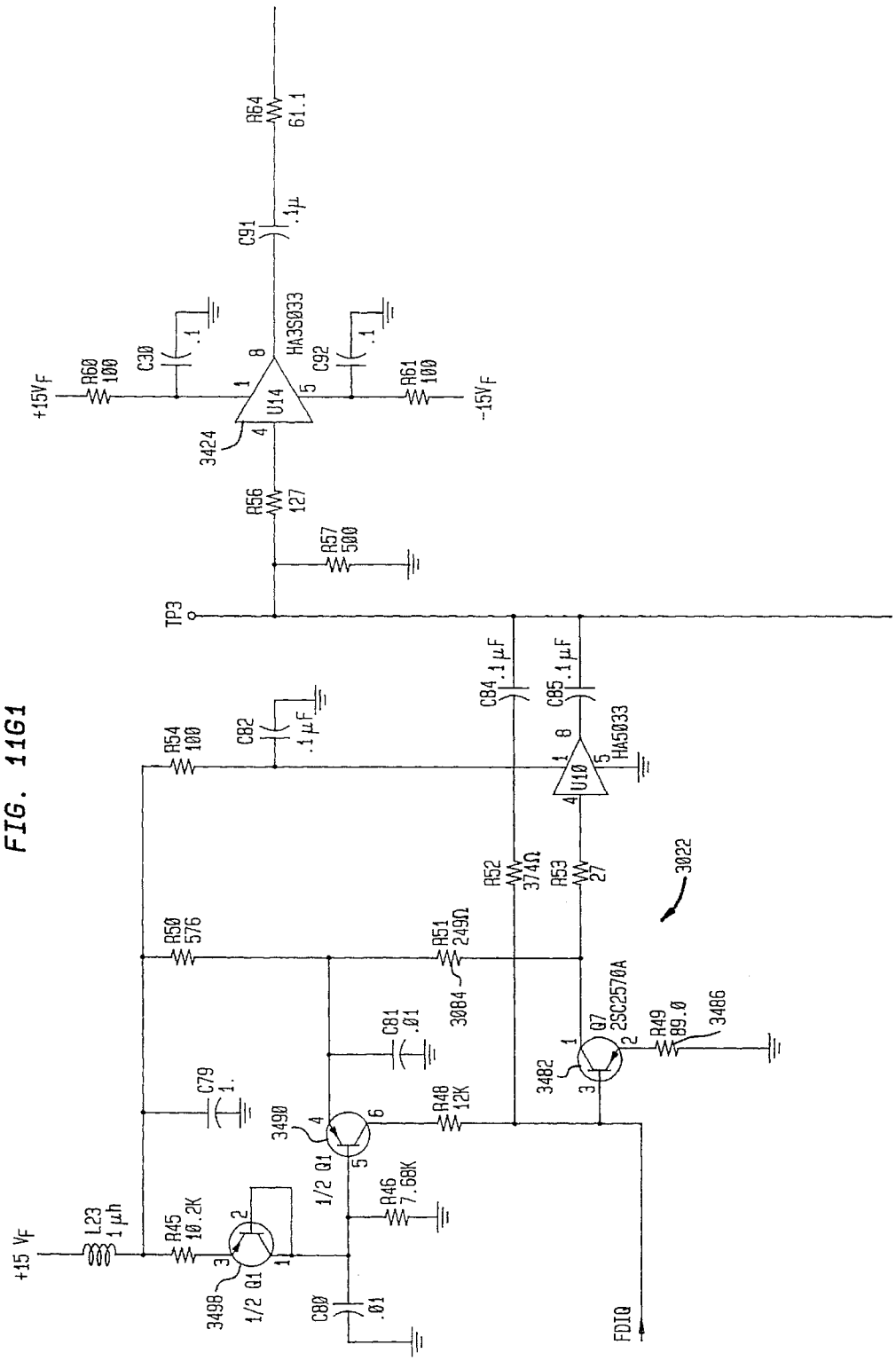
FIG. 11G1

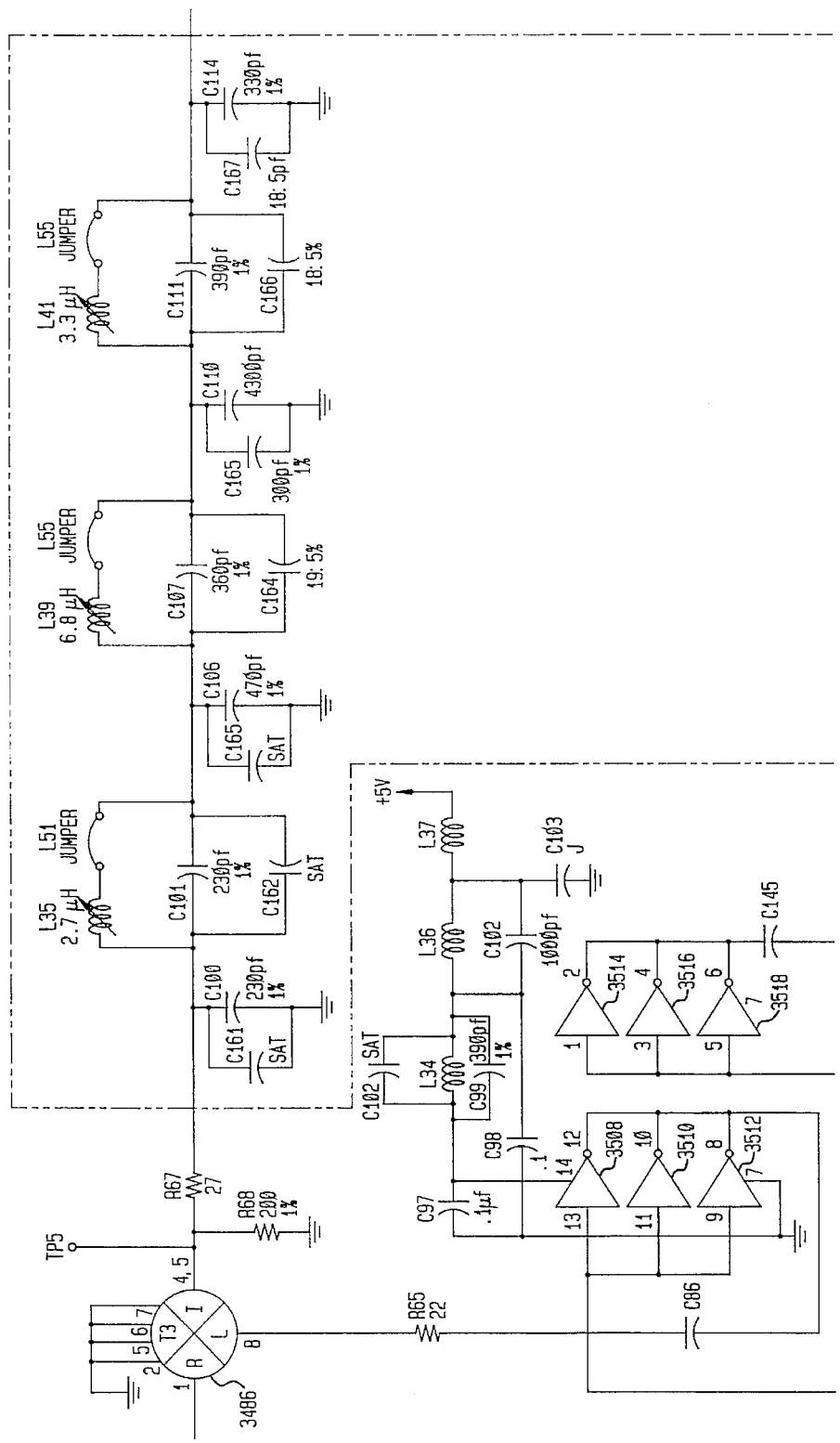
FIG. 1162

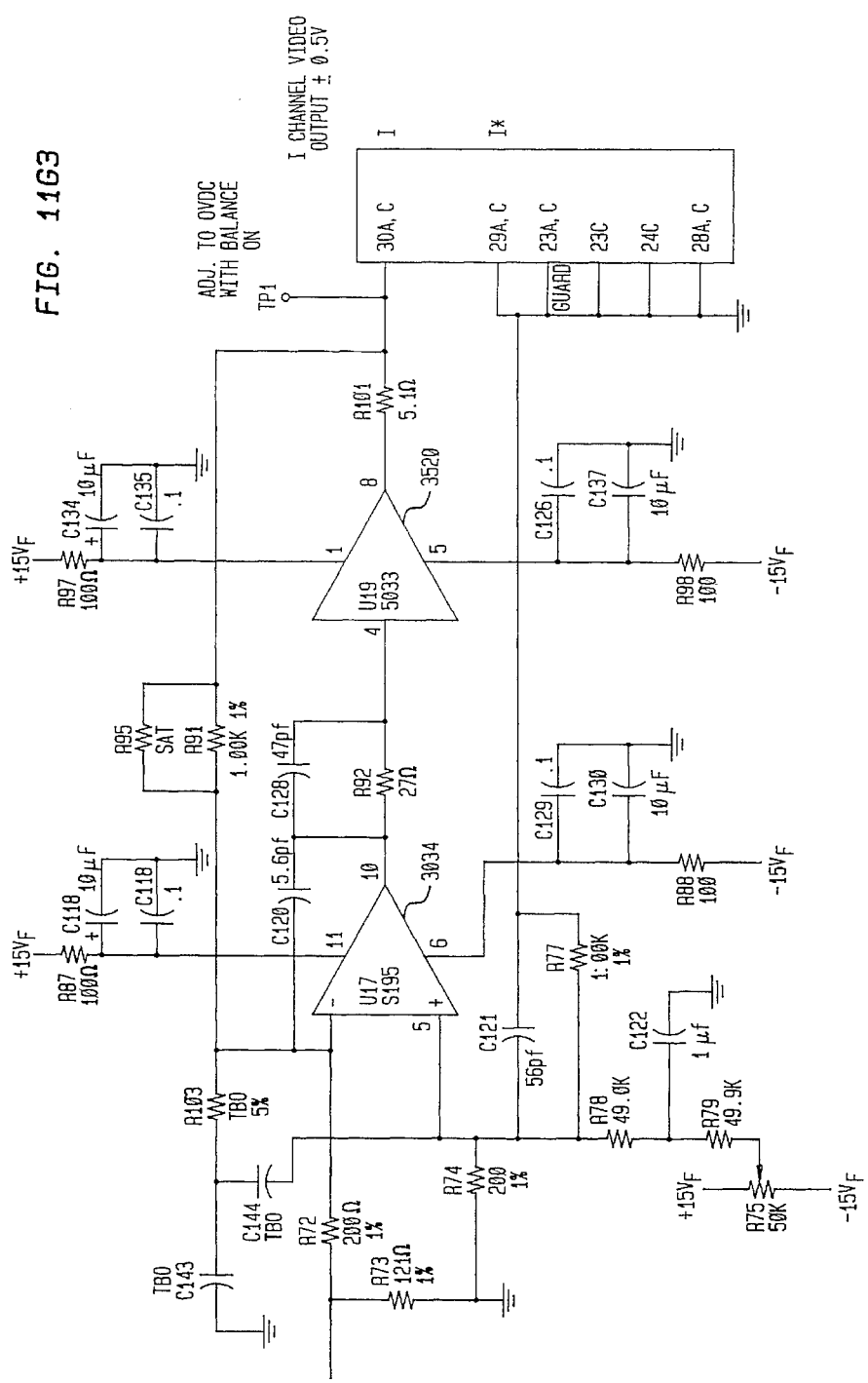
FIG. 1163

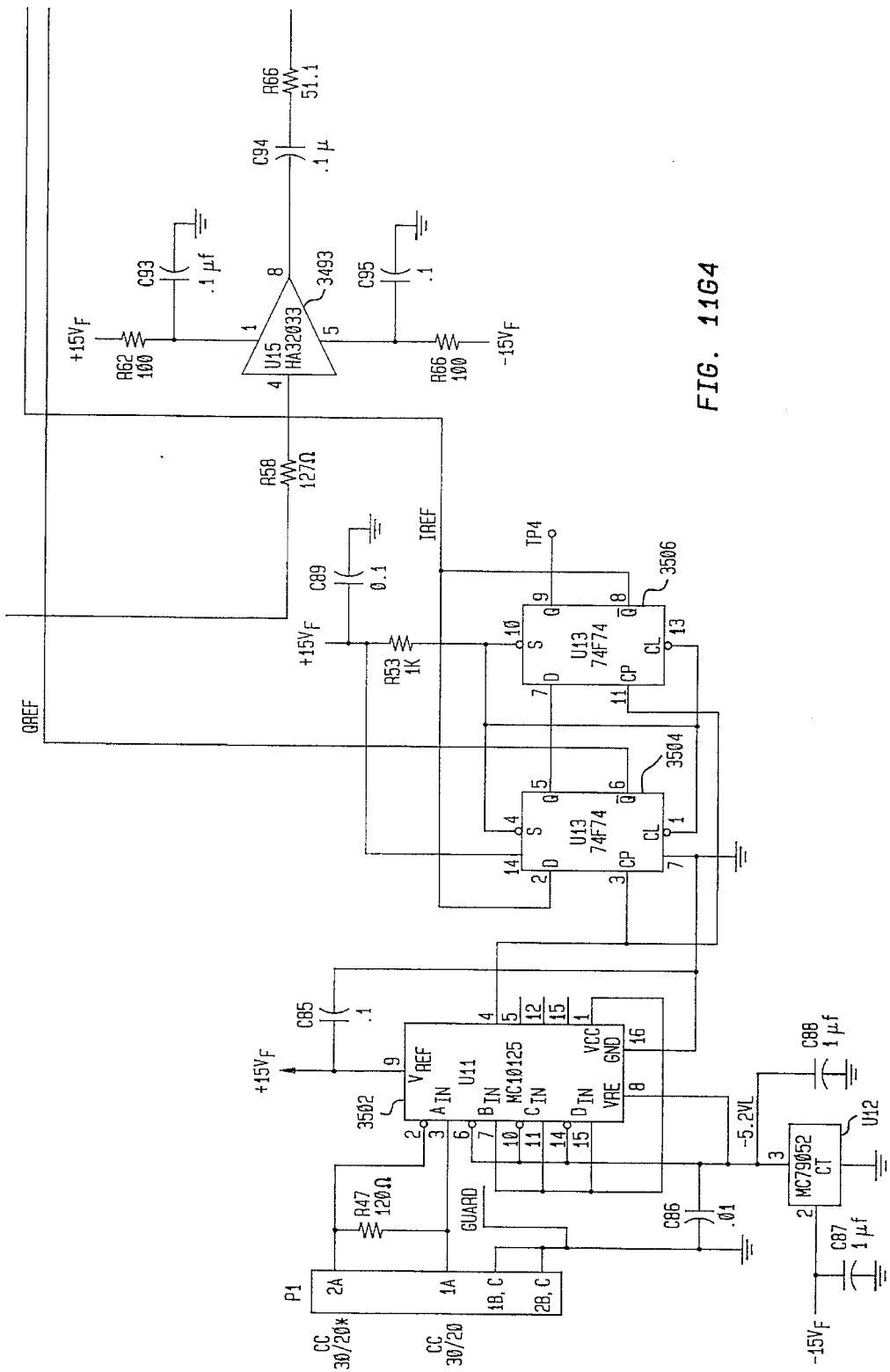
FIG. 1164

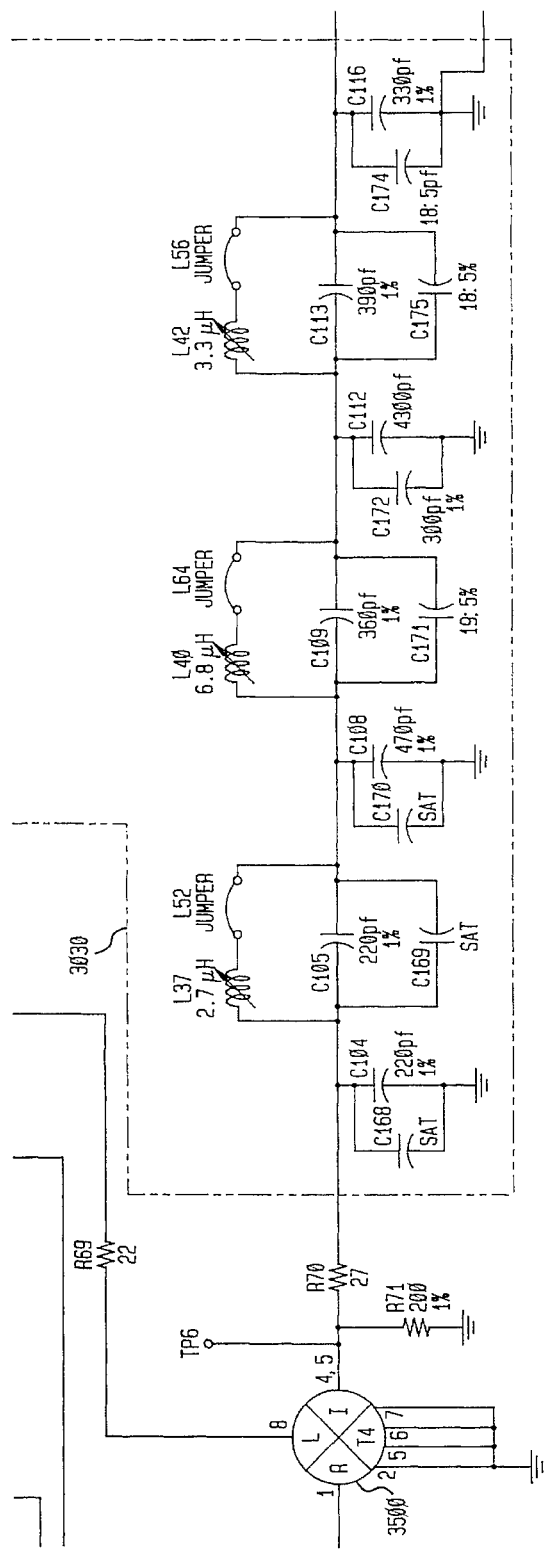
FIG. 1165

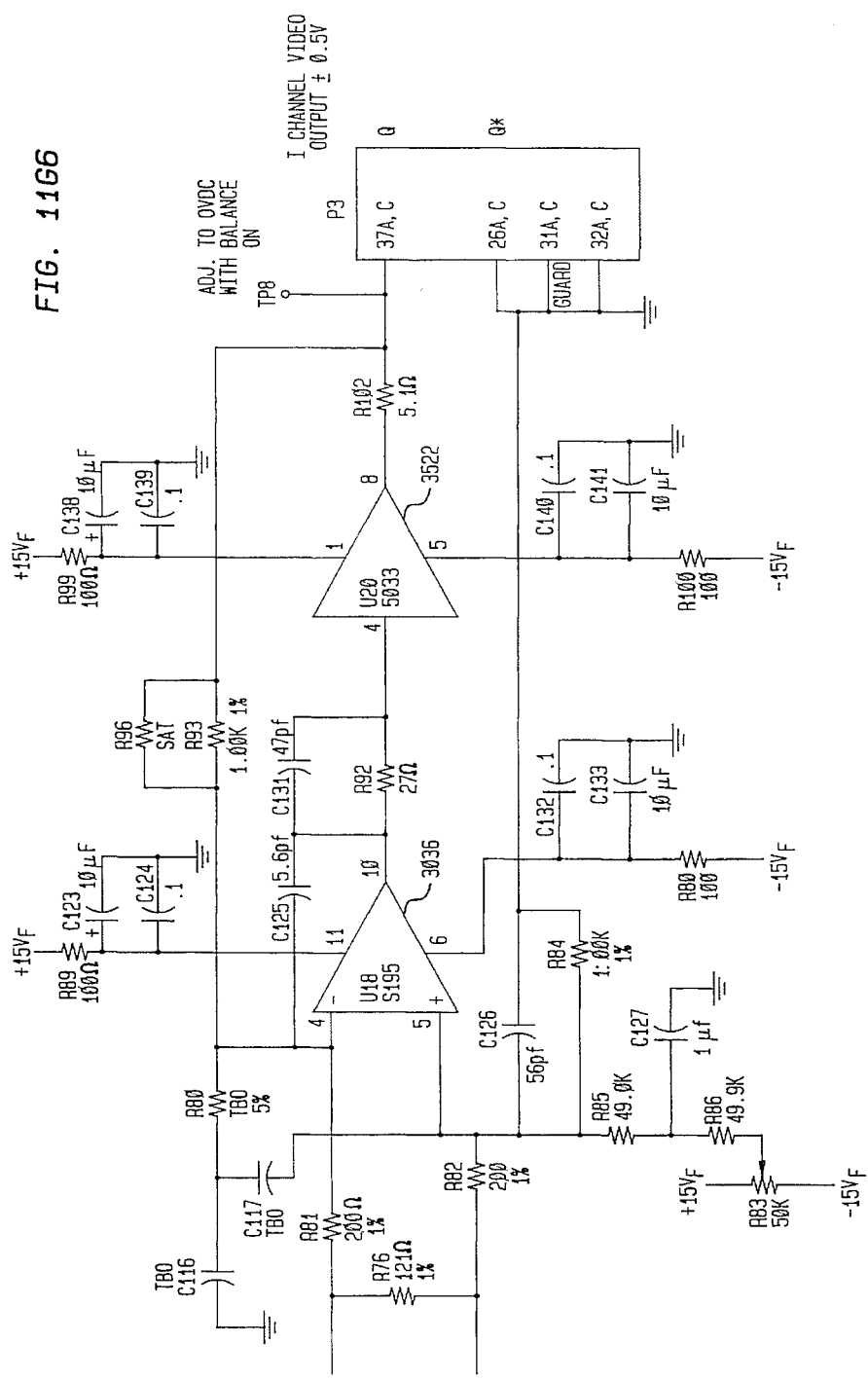
FIG. 1166

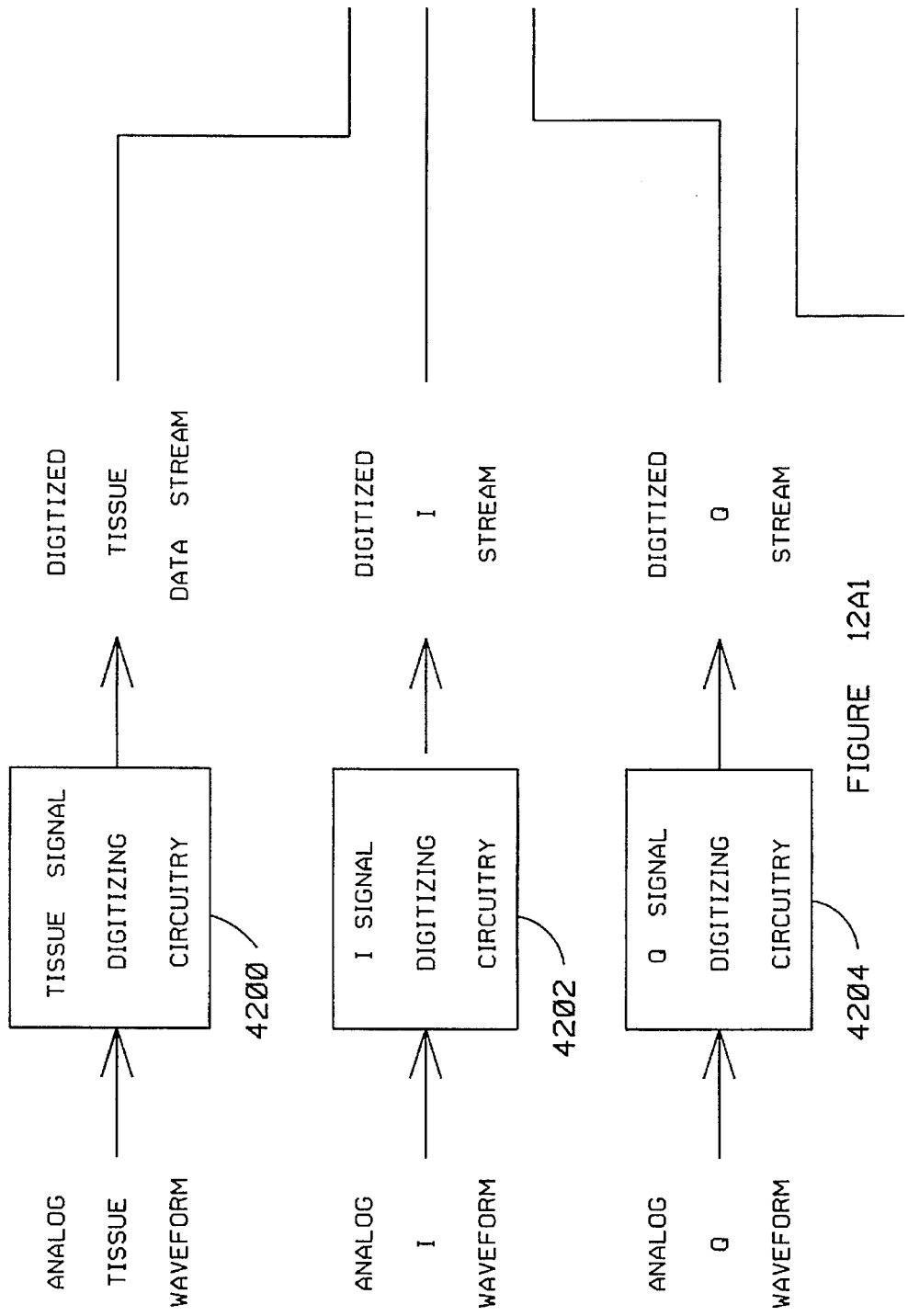
FIGURE 12A1

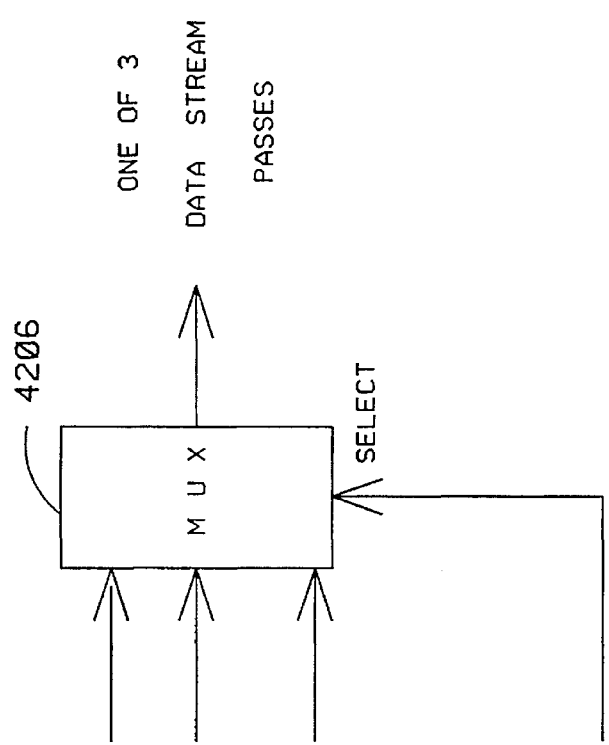

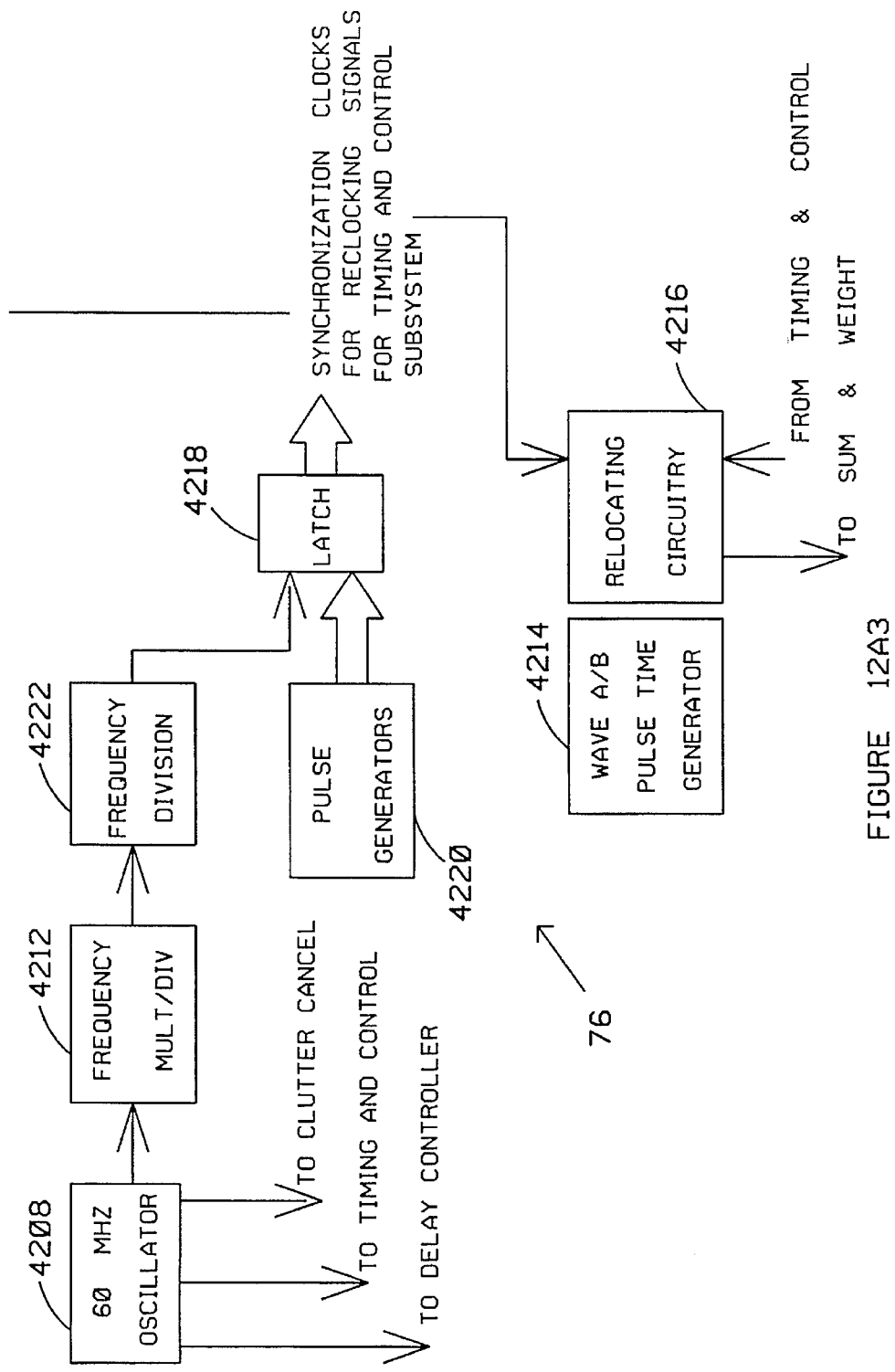
FIGURE 12A3

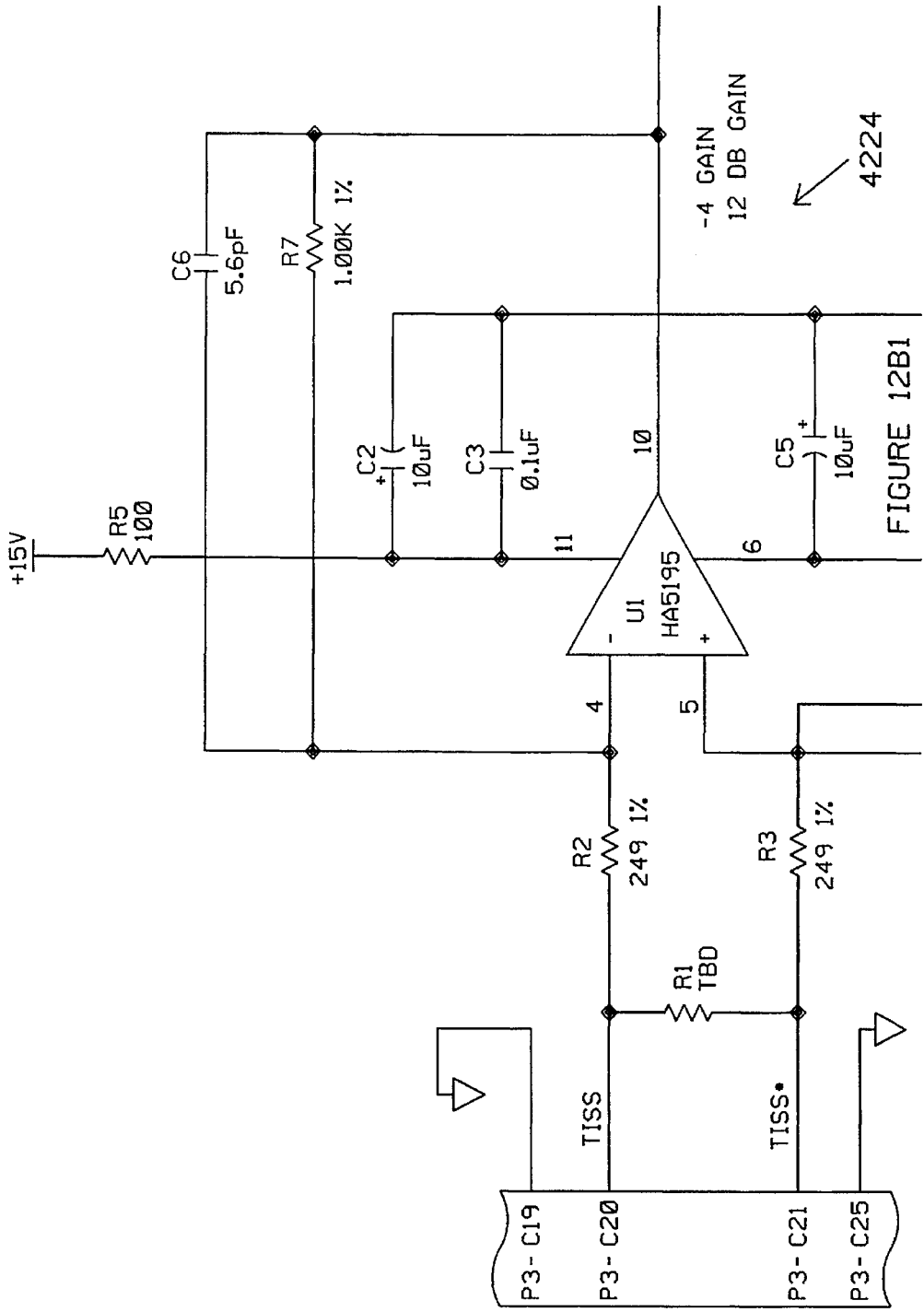
FIGURE 12B1

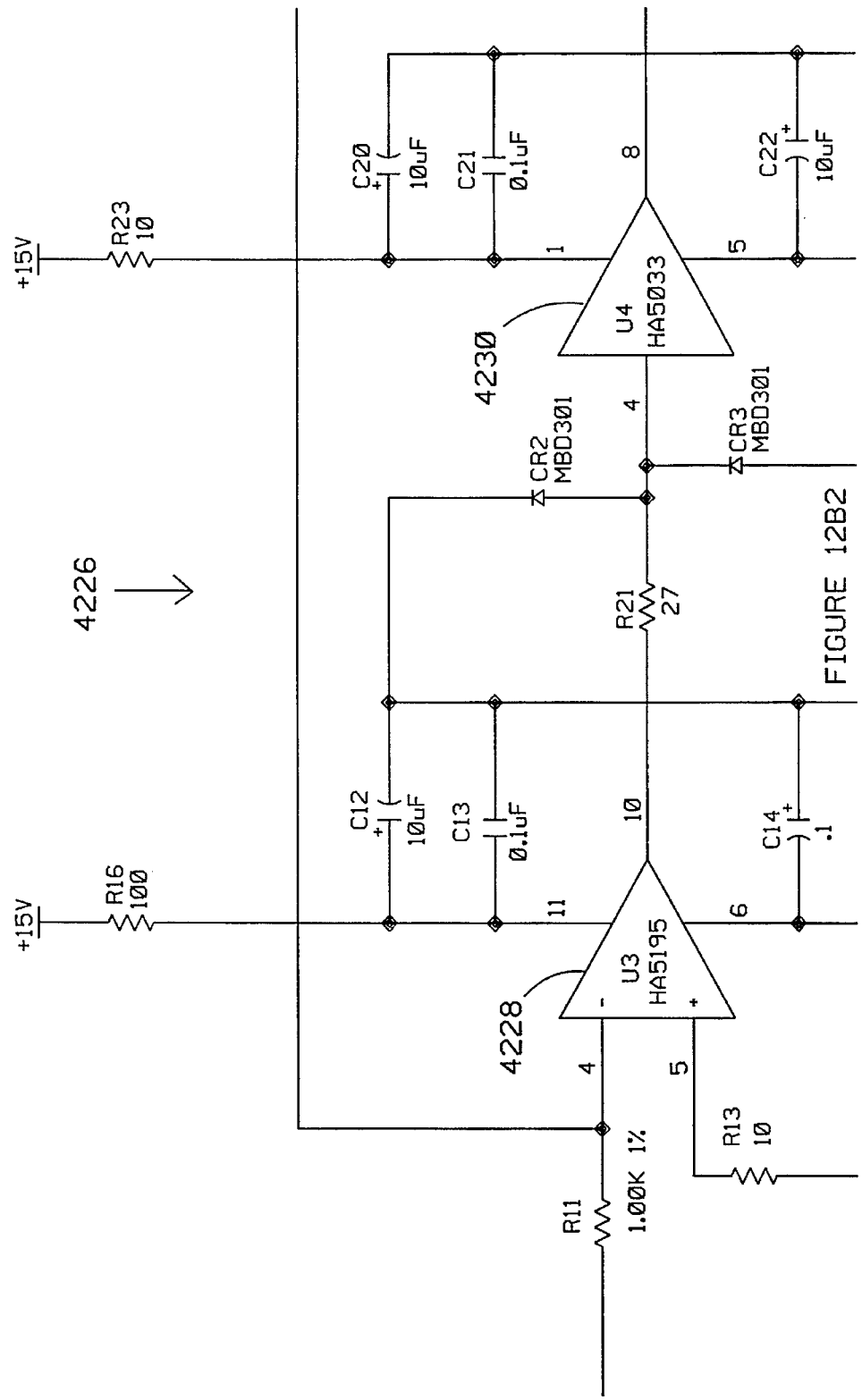
FIGURE 12B2

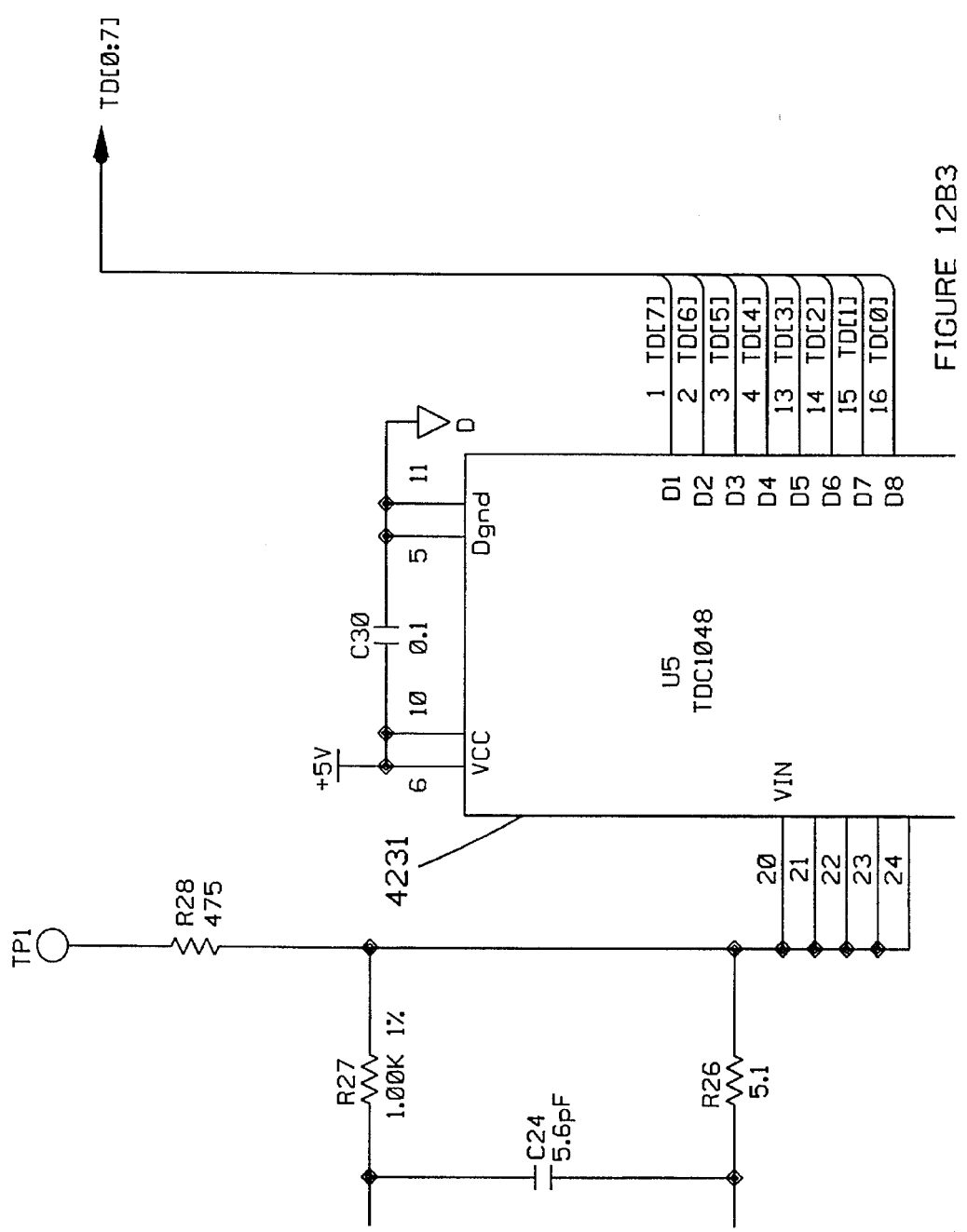
FIGURE 12B3

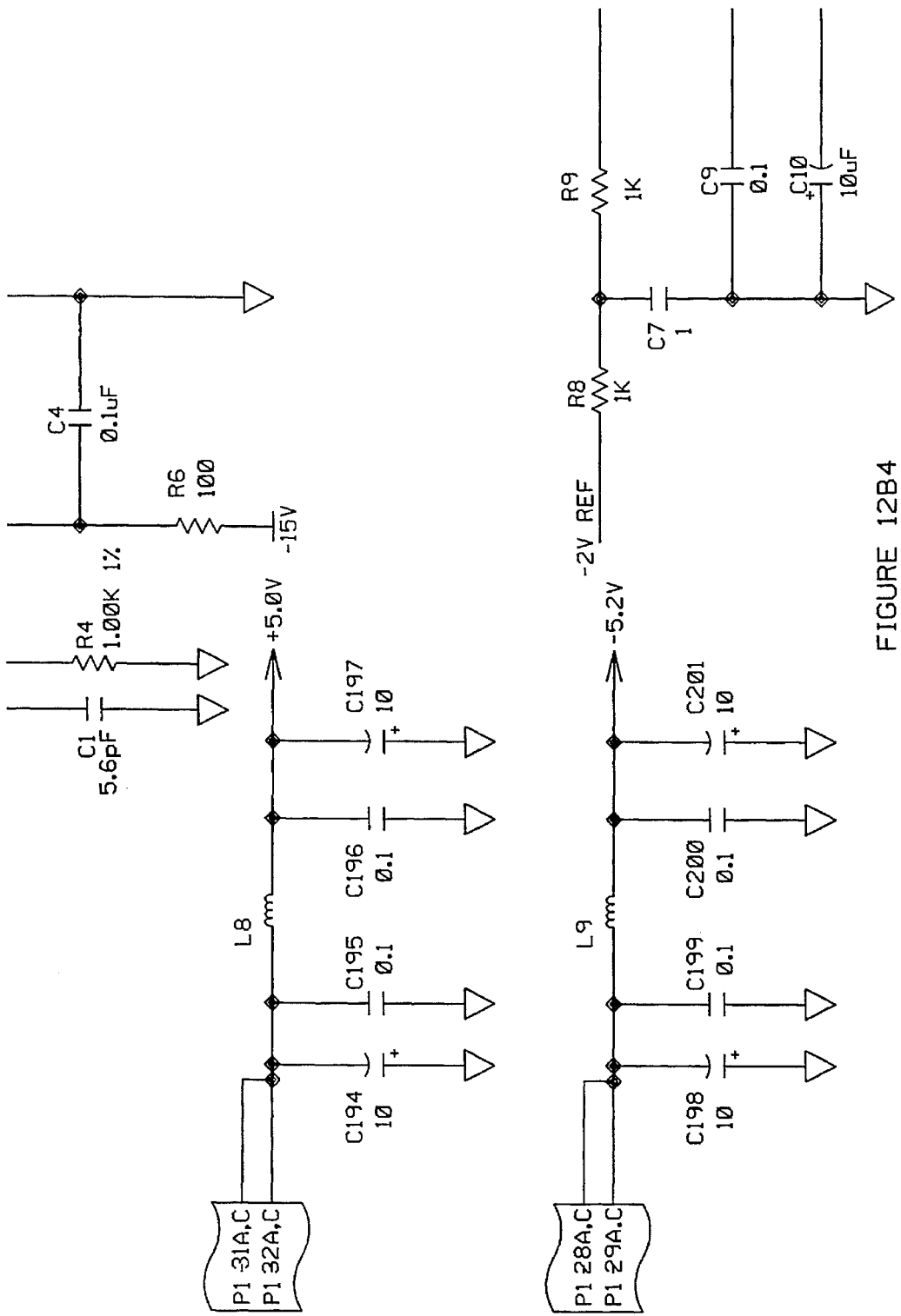
FIGURE 12B4

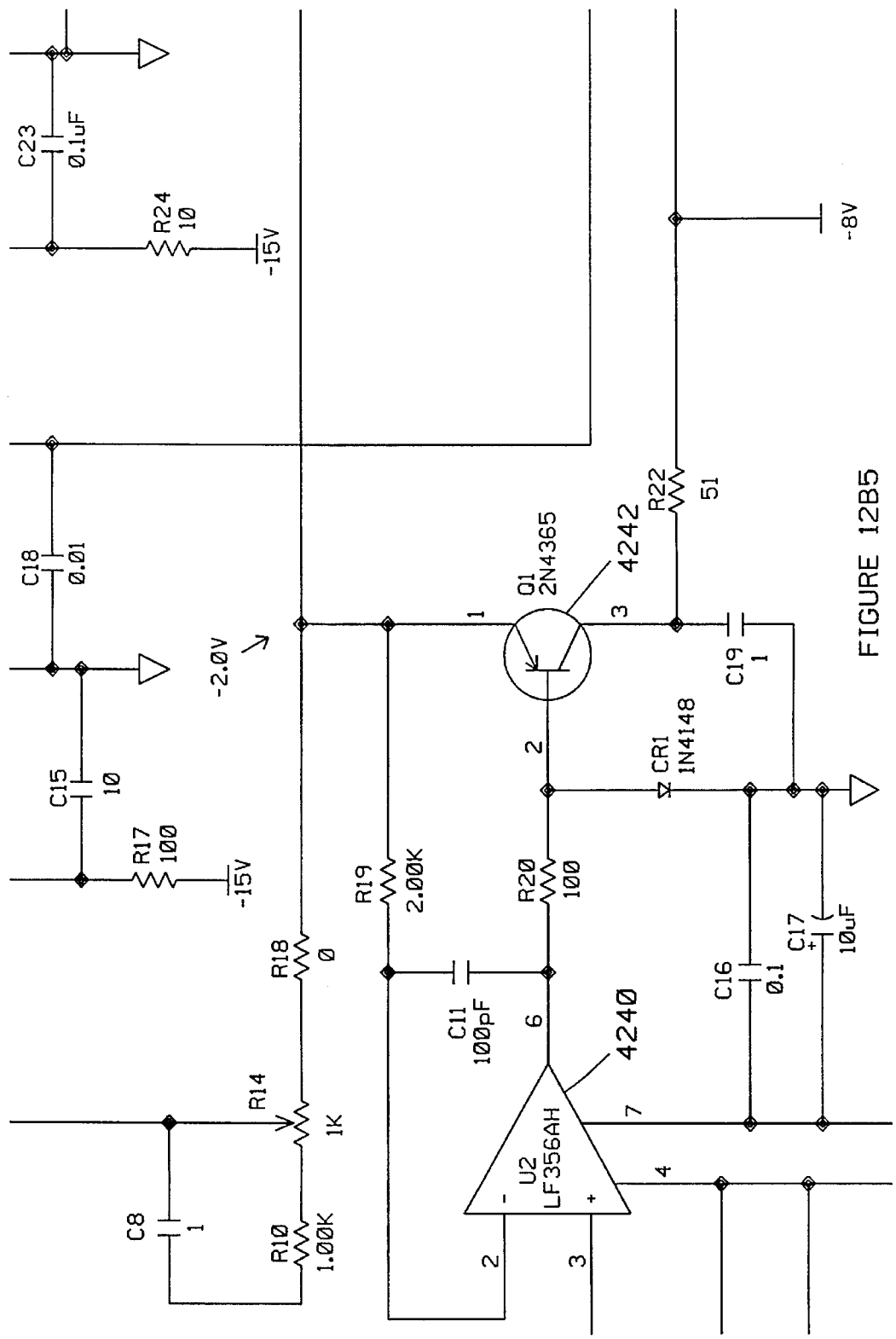
FIGURE 12B5

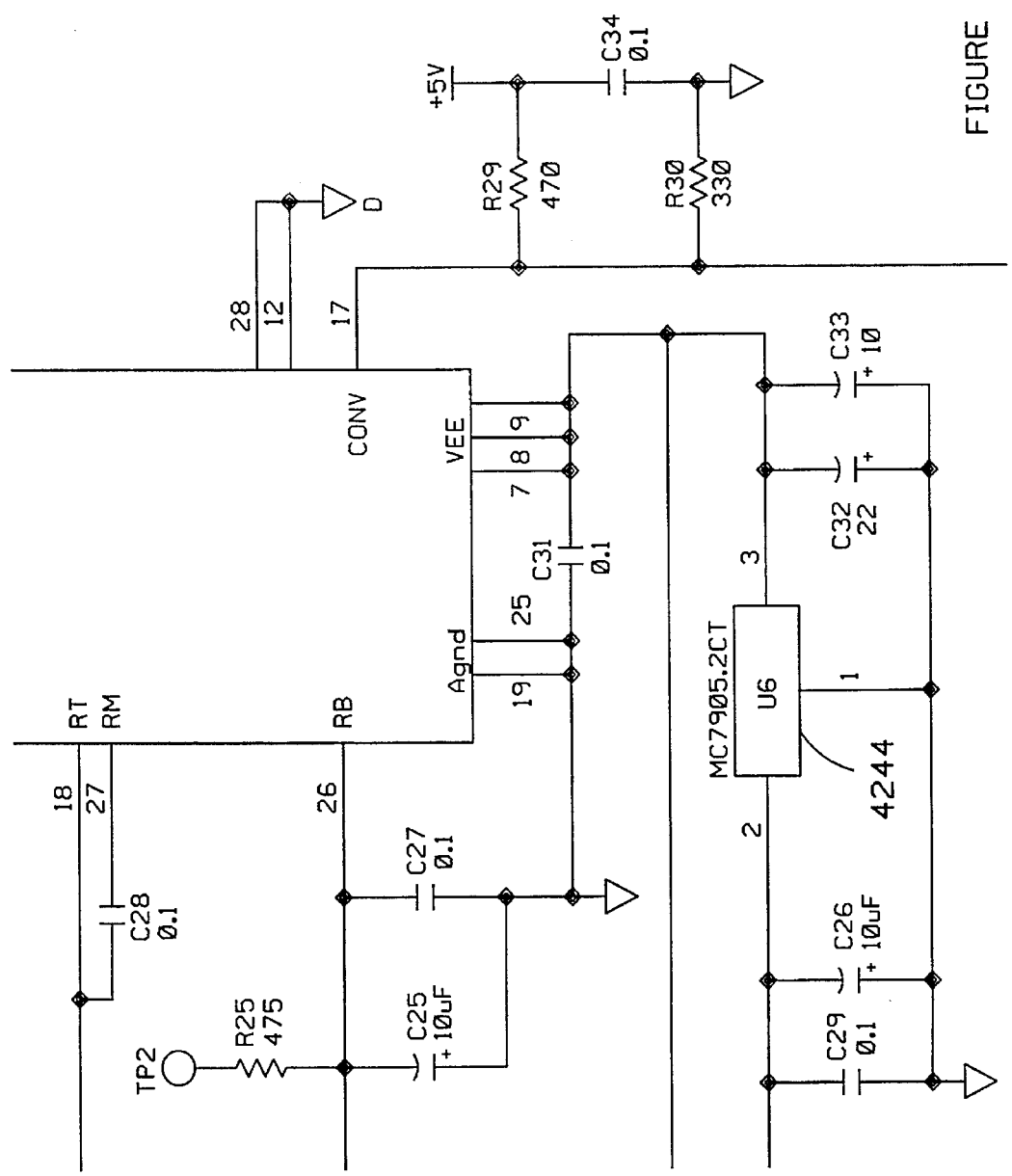
FIGURE 12B6

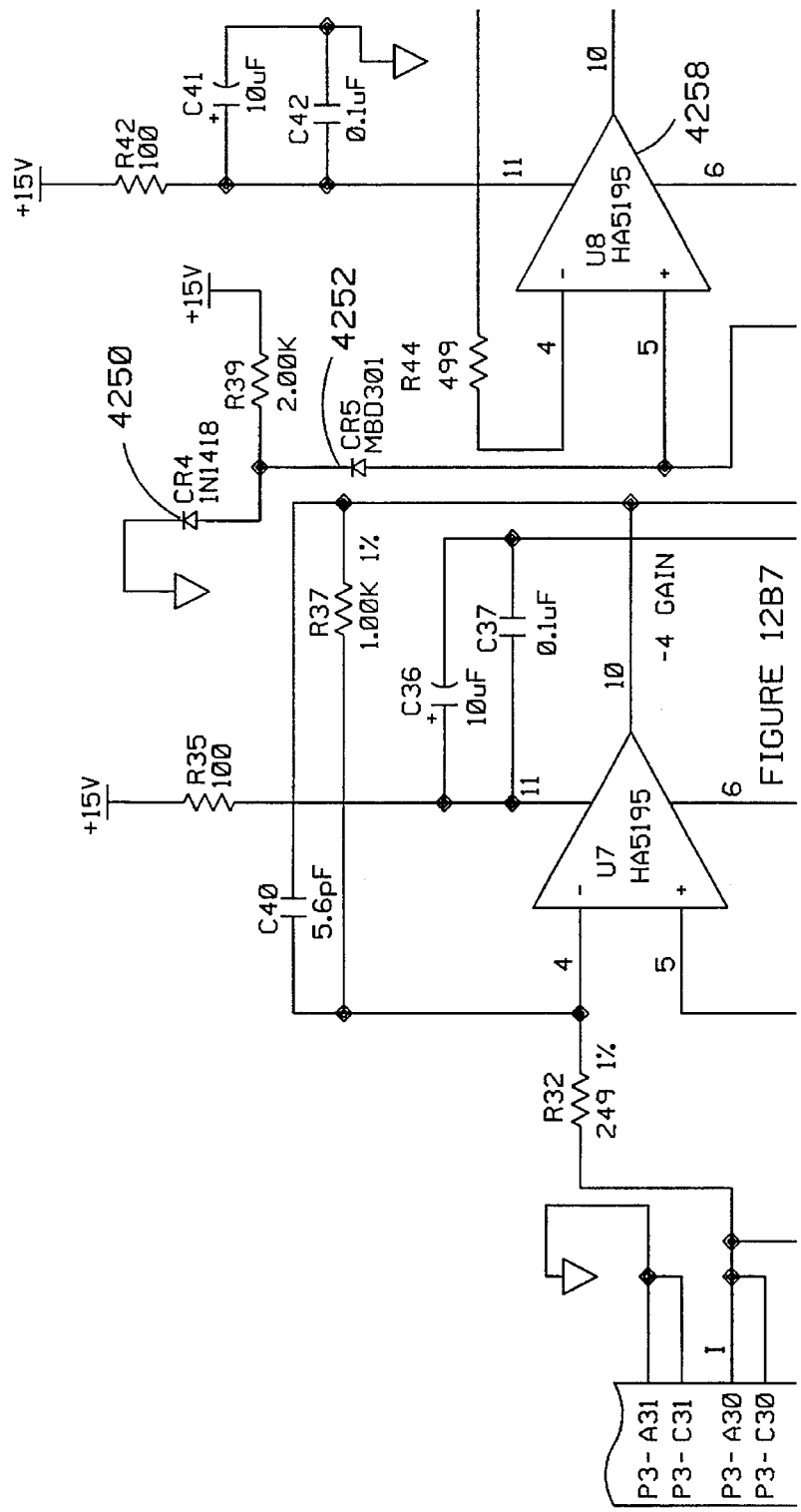
FIGURE 12B7

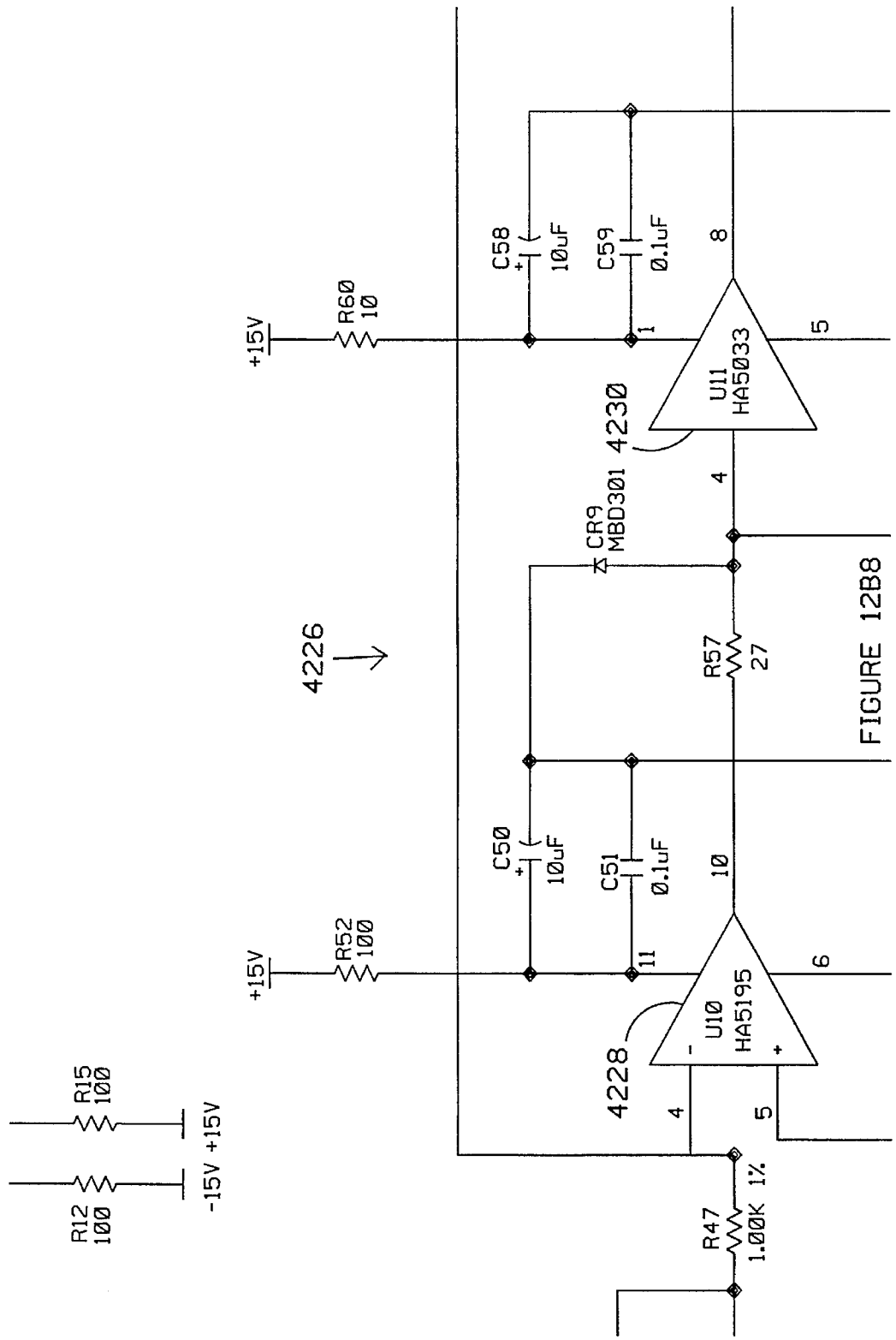

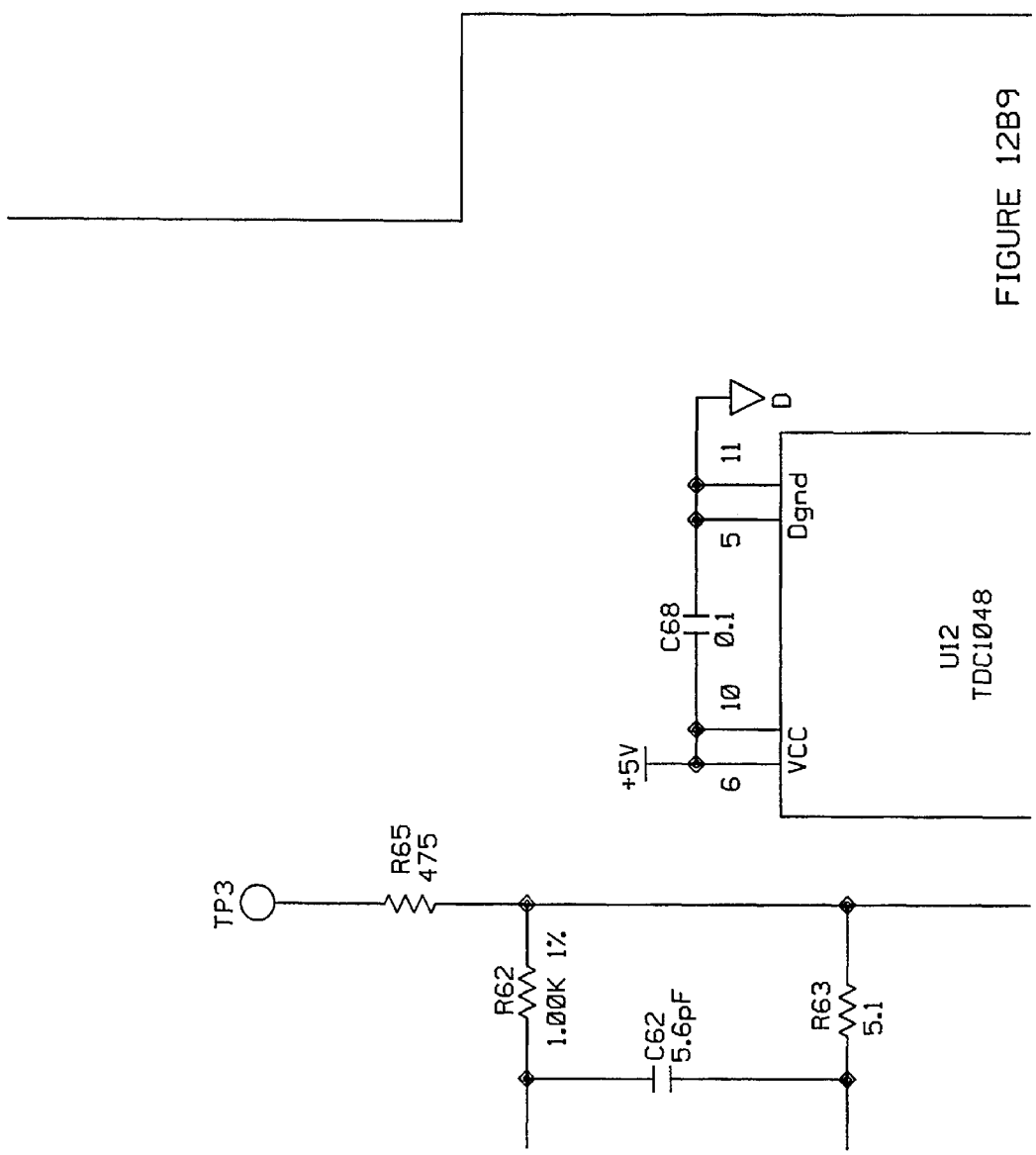
FIGURE 12B9

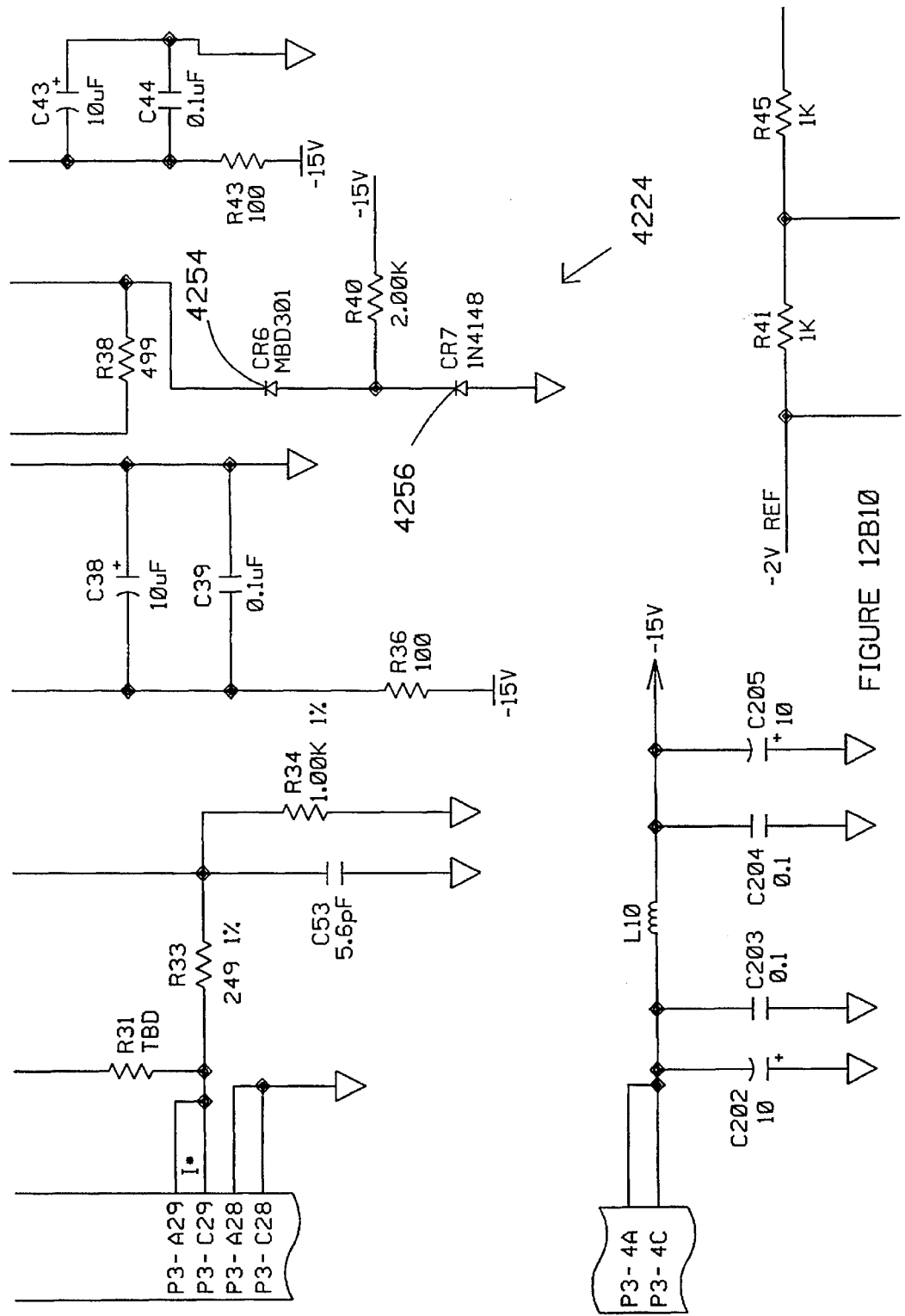
FIGURE 12B10

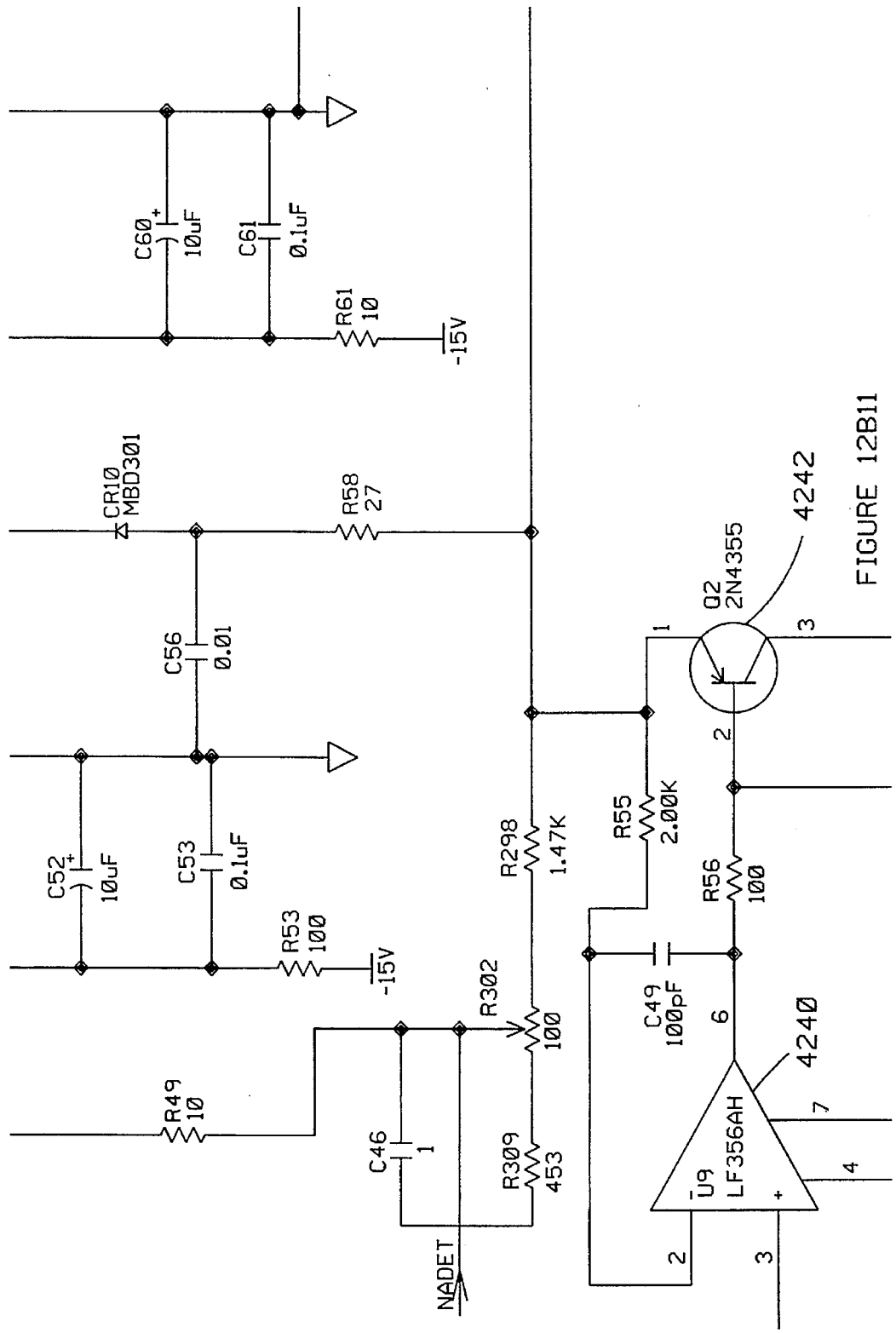
FIGURE 12B11

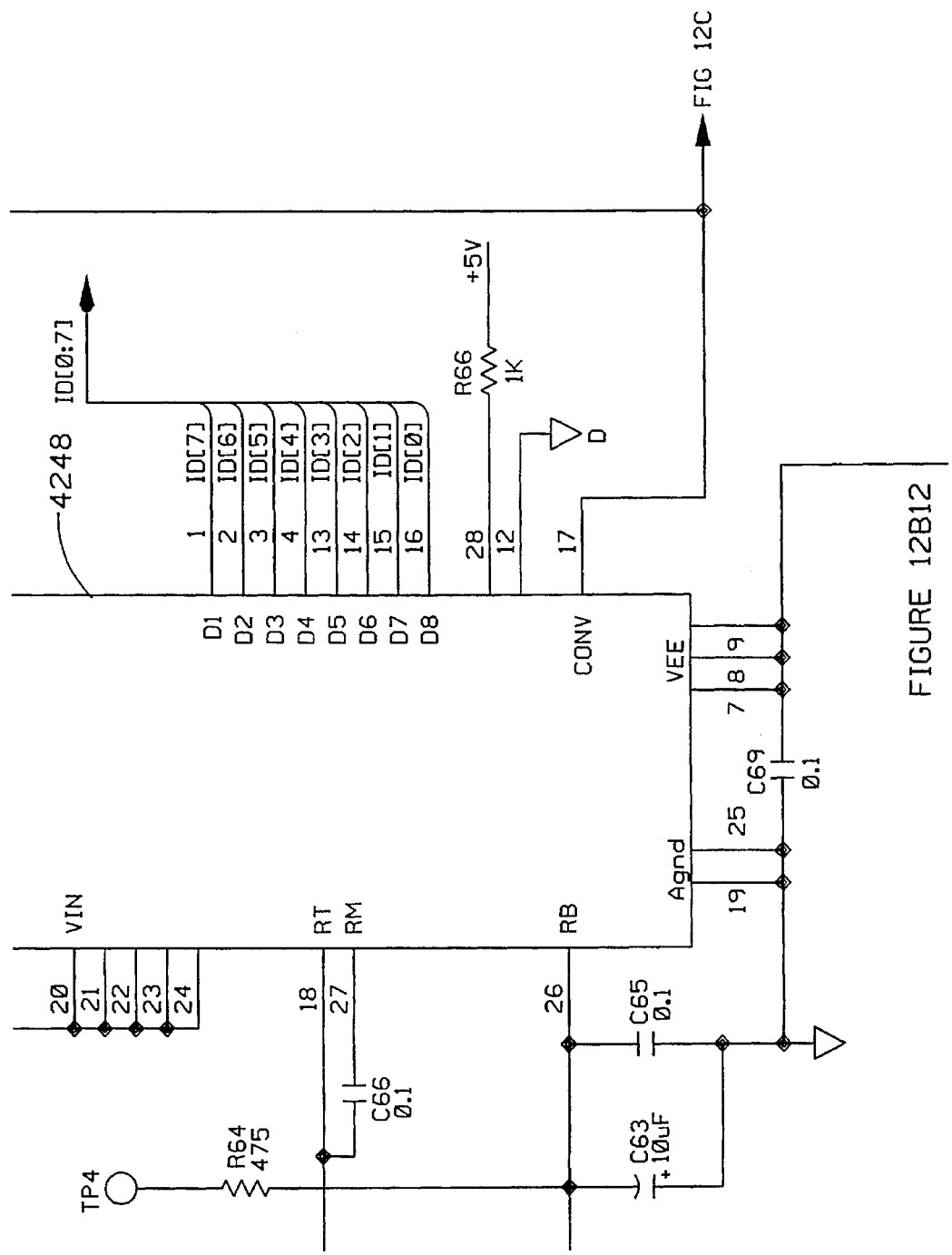
FIGURE 12B12

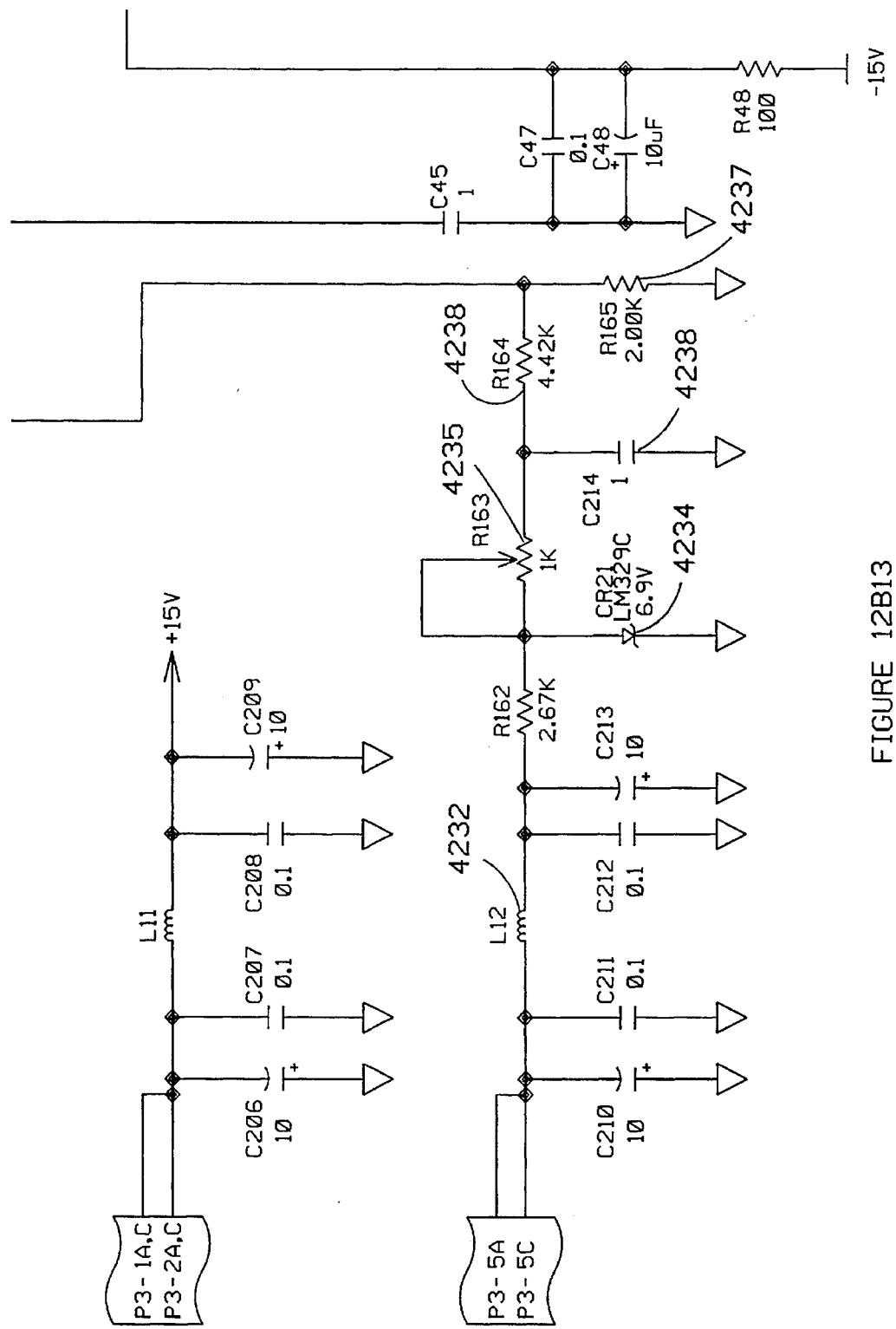
FIGURE 12B13

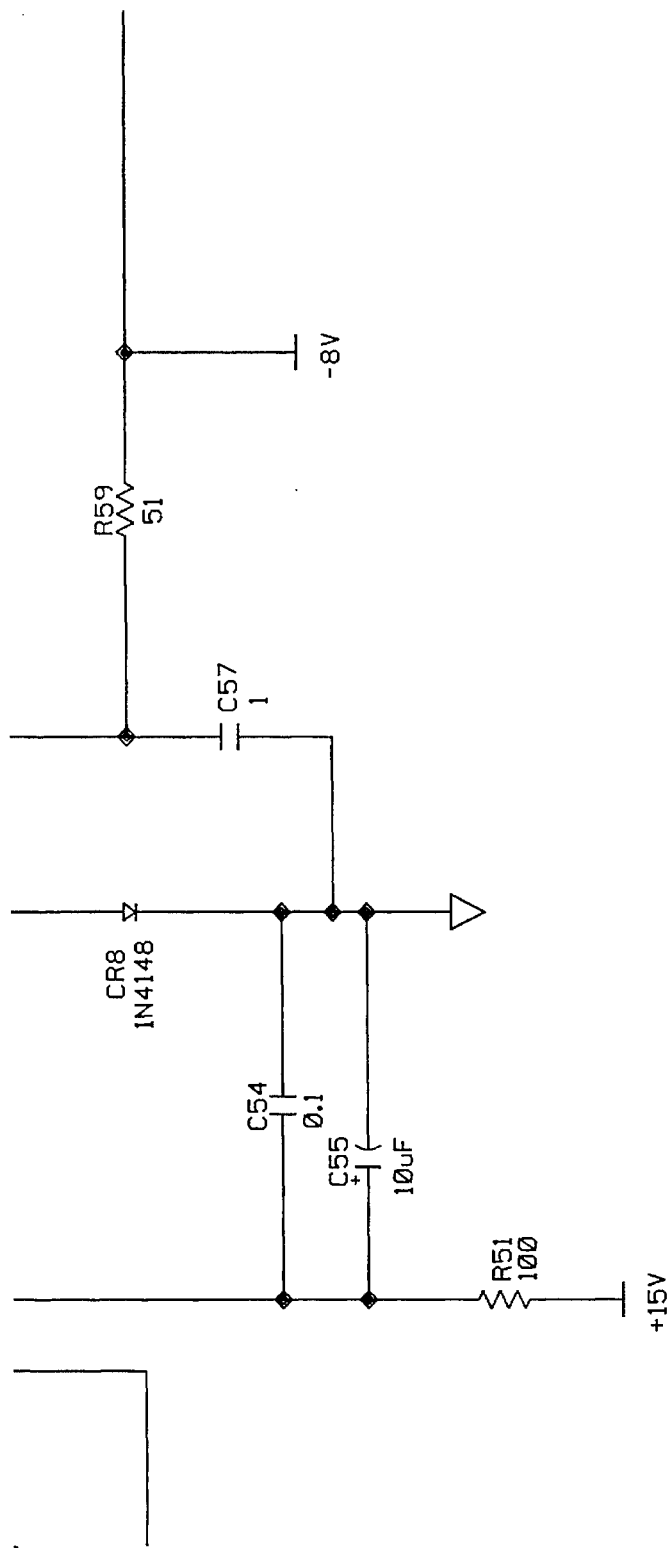
FIGURE 12B14

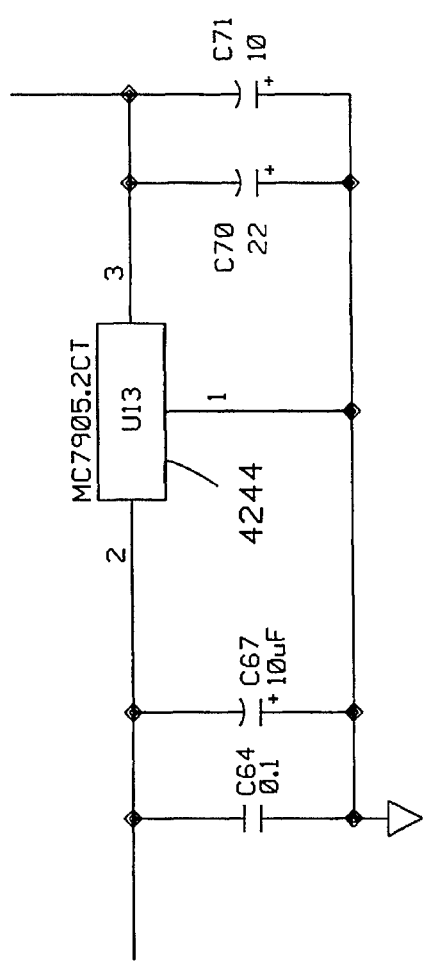
FIGURE 12B15

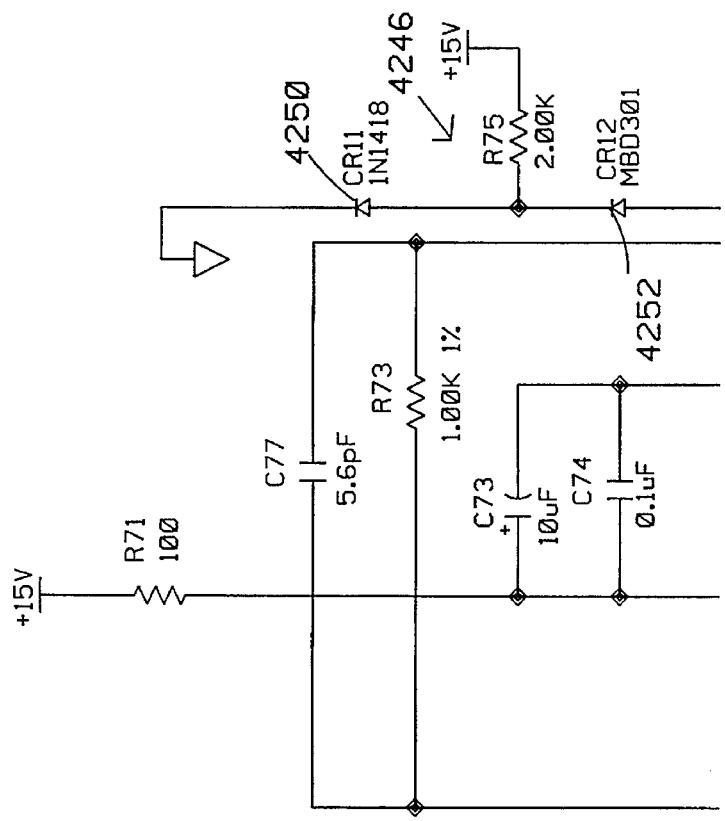
FIGURE 12C1

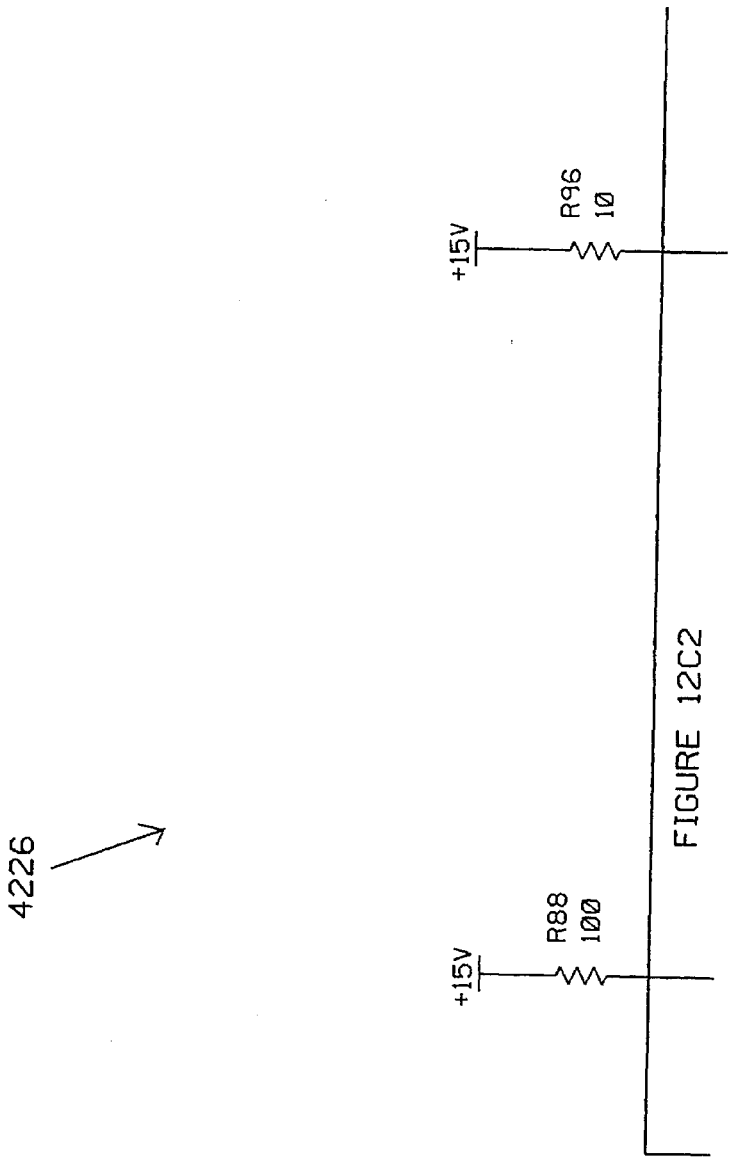

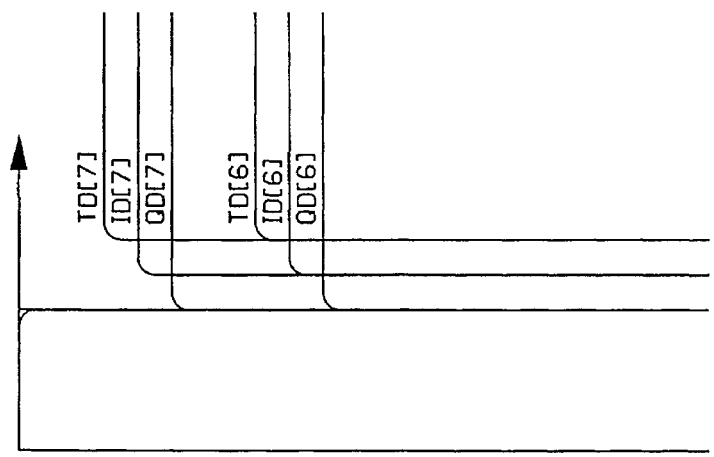
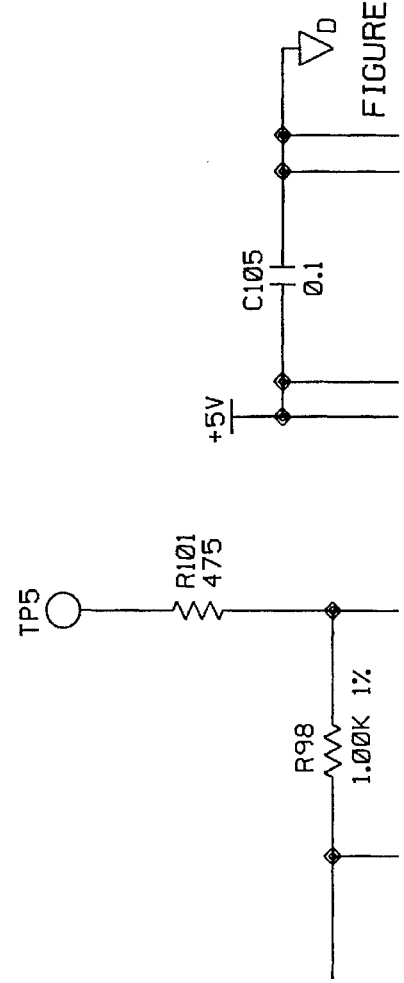
FIGURE 12C3

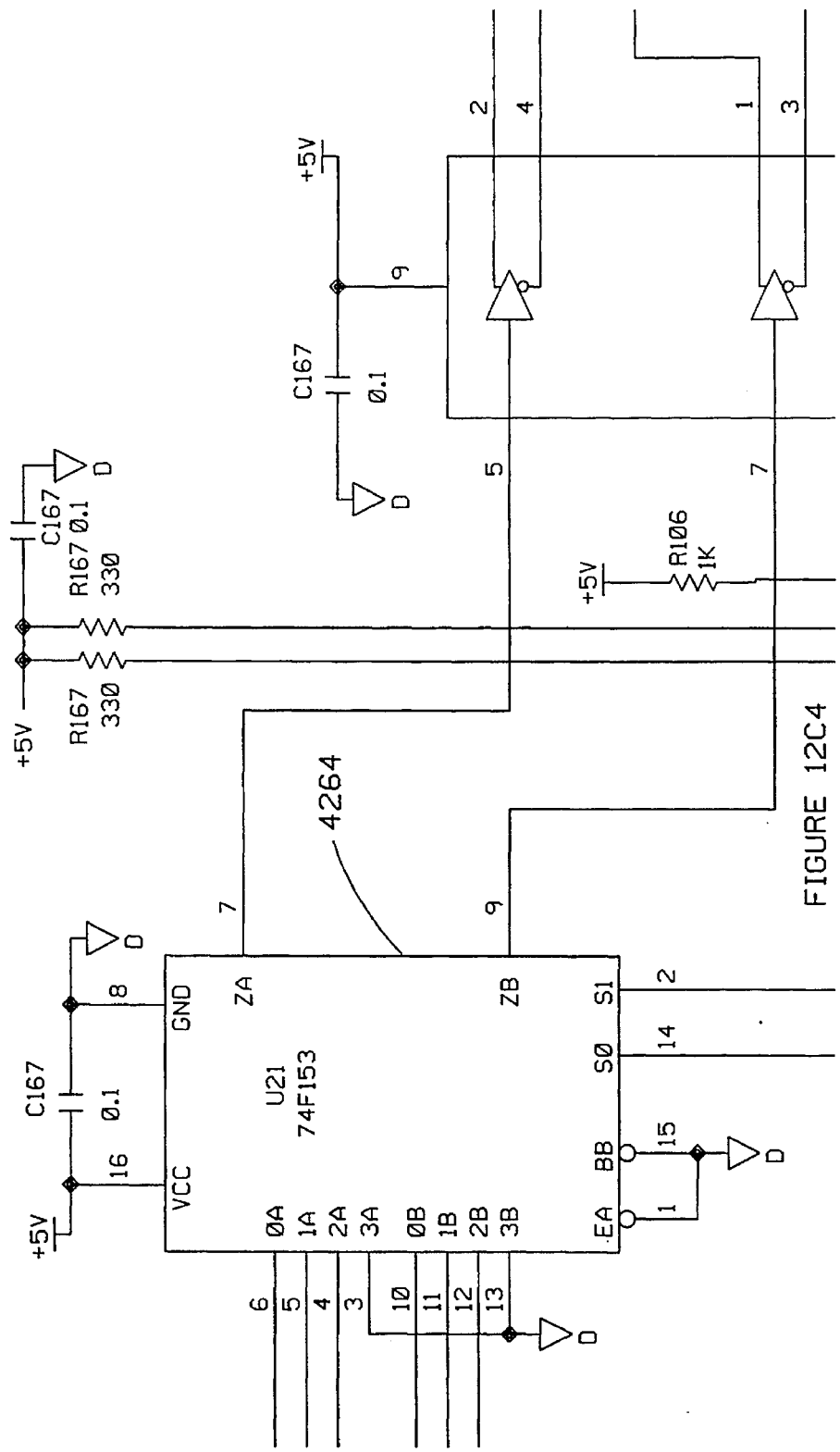
FIGURE 12C4

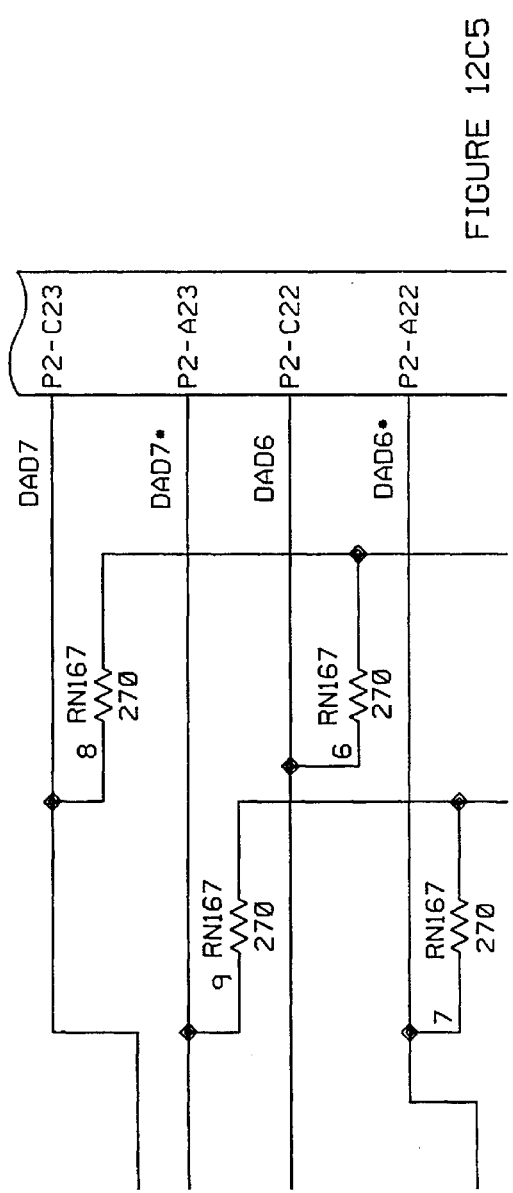

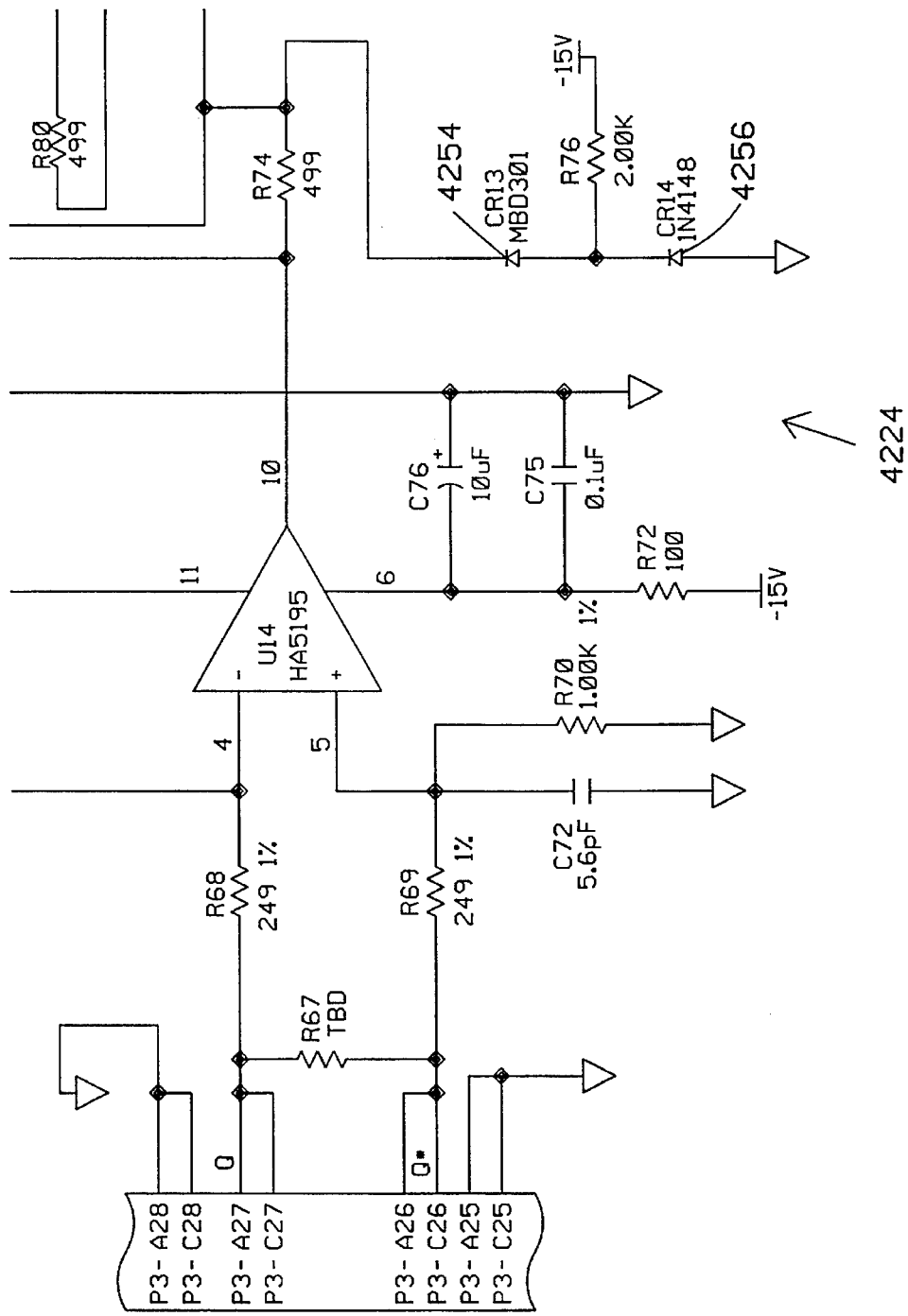
FIGURE 12C6

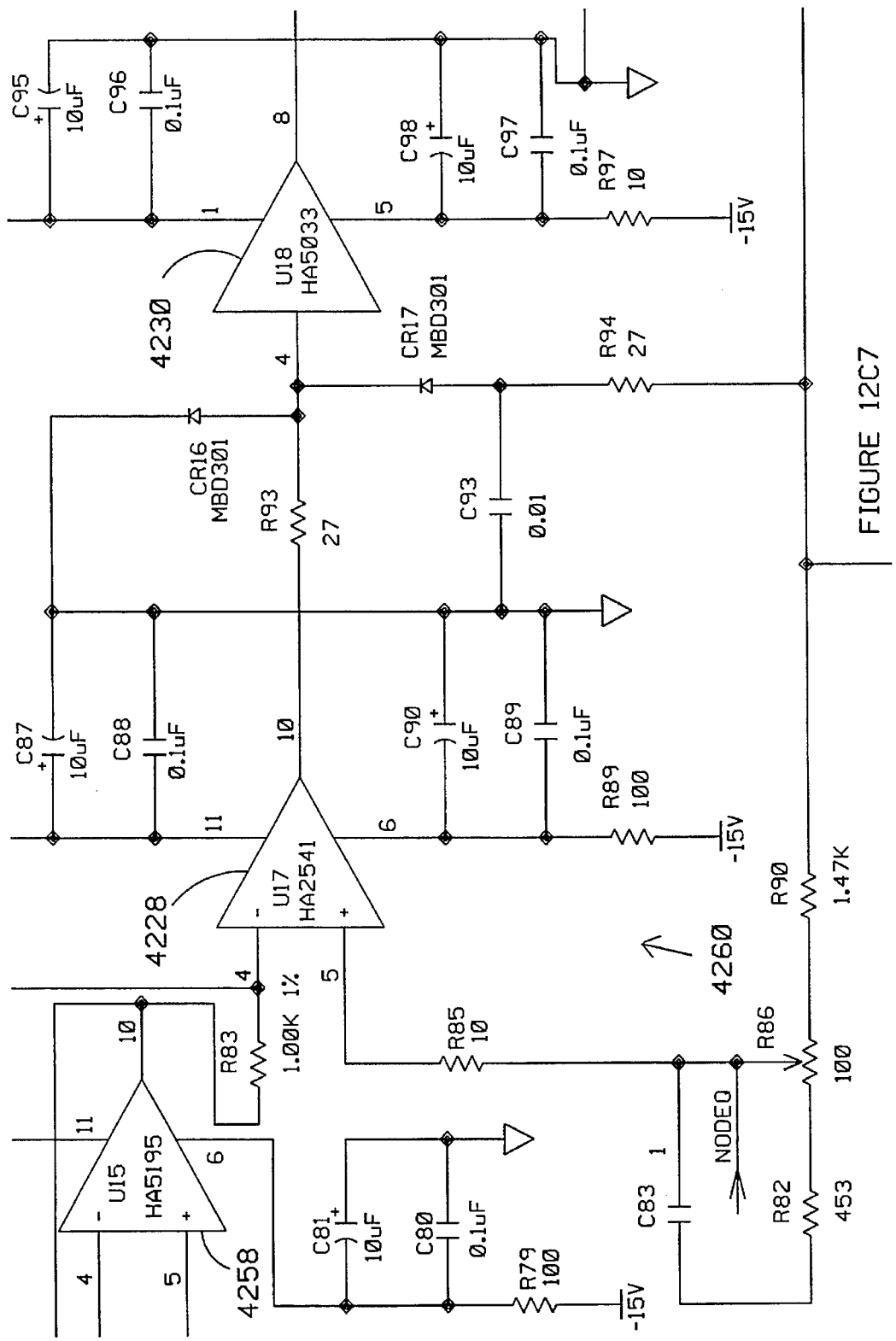
FIGURE 12C7

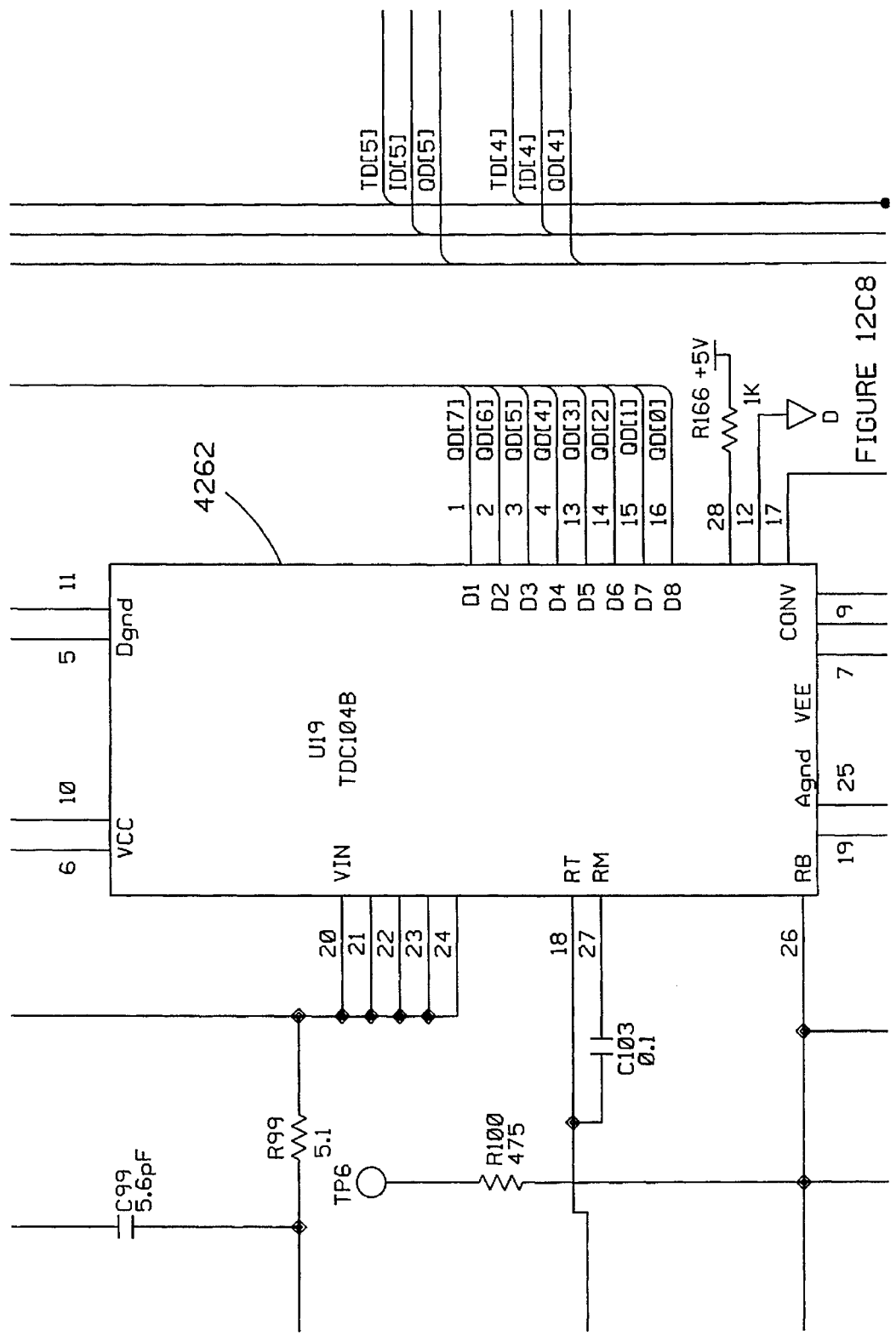
FIGURE 12C8

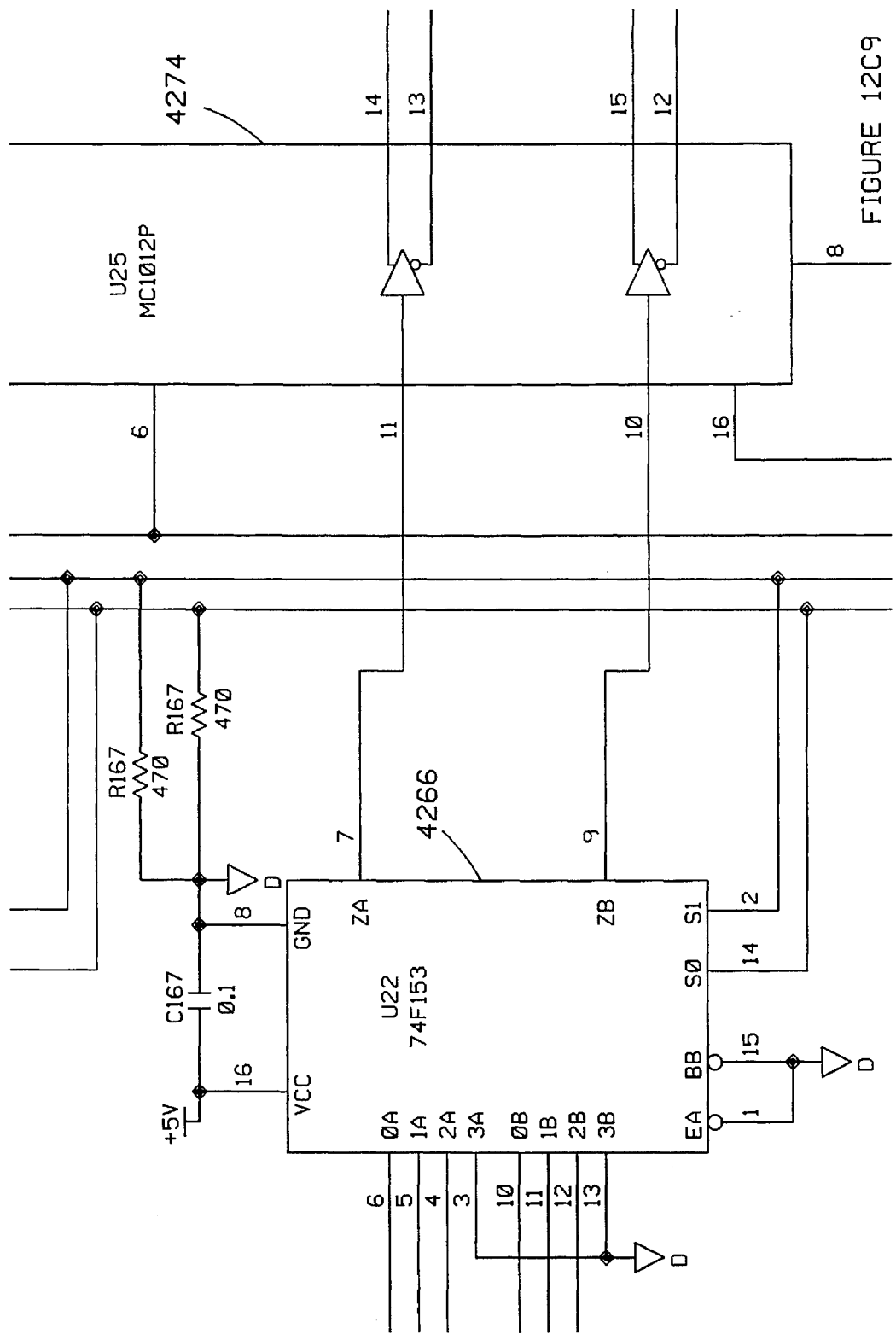
FIGURE 12C9

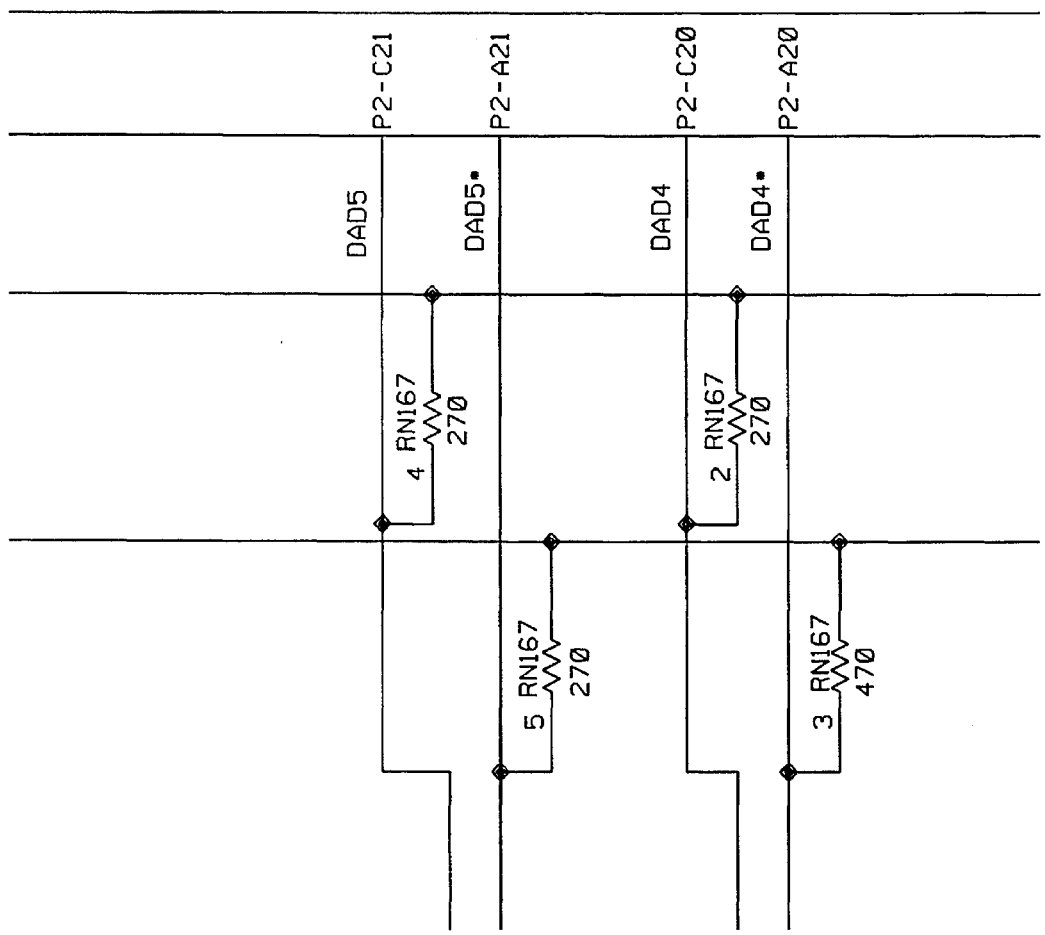
FIGURE 12C10

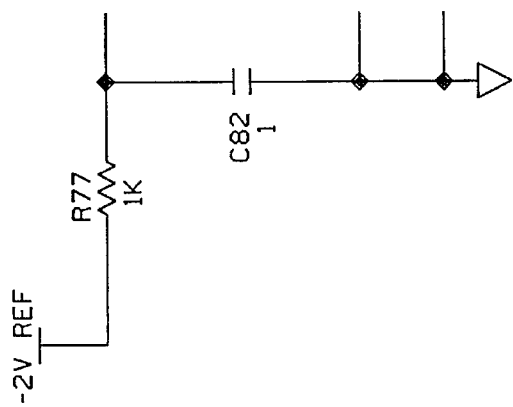
FIGURE 12C11

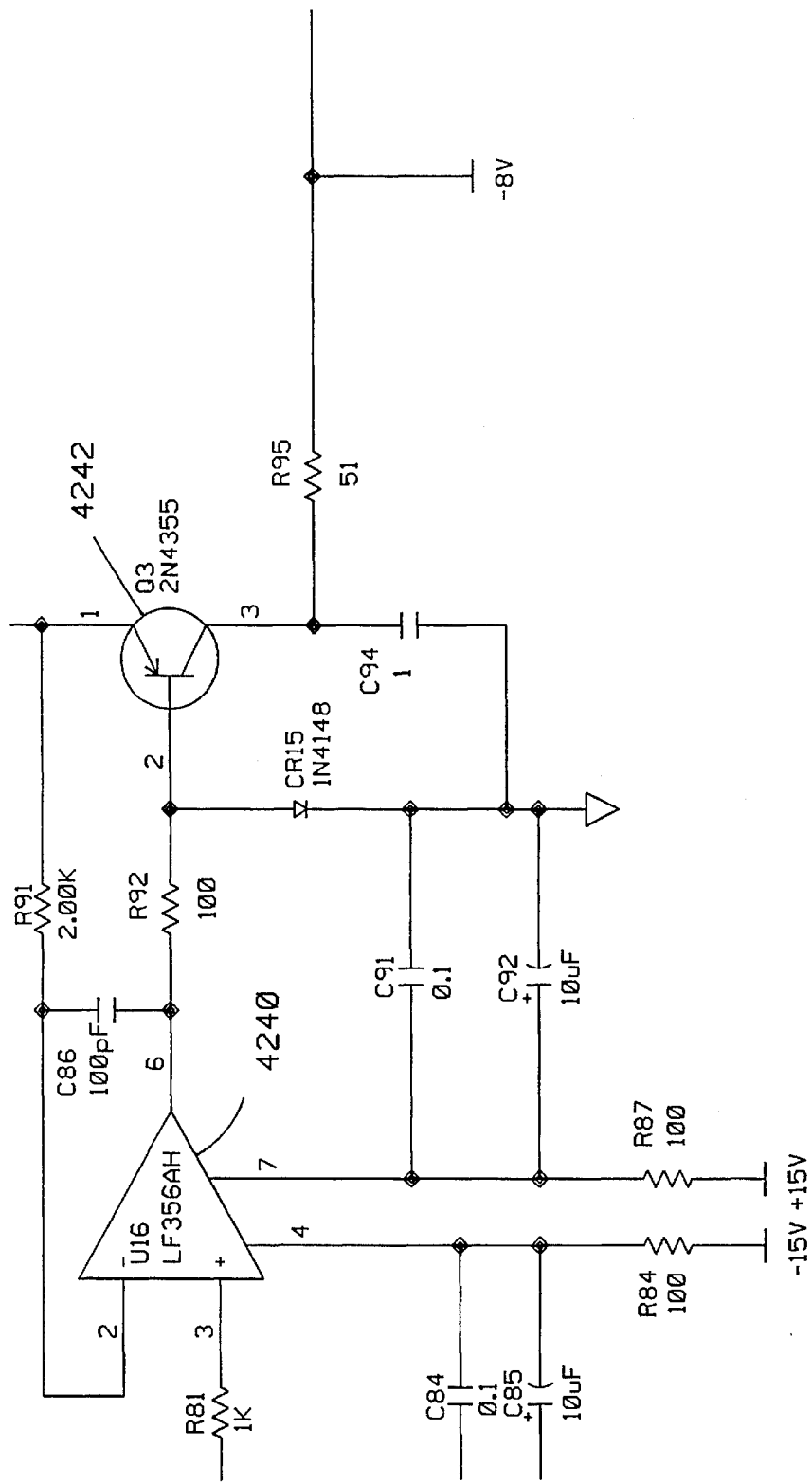
FIGURE 12C12

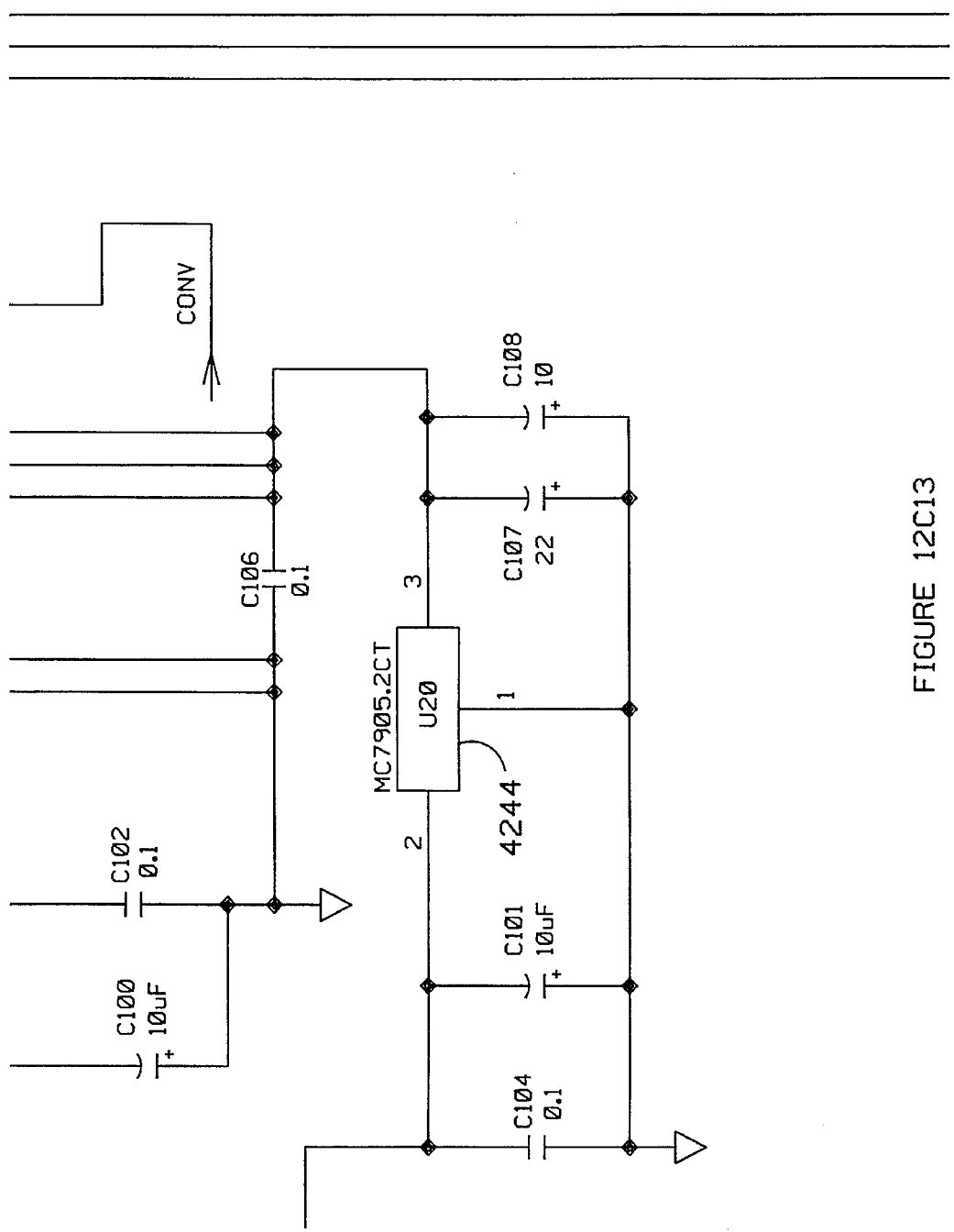
FIGURE 12C13

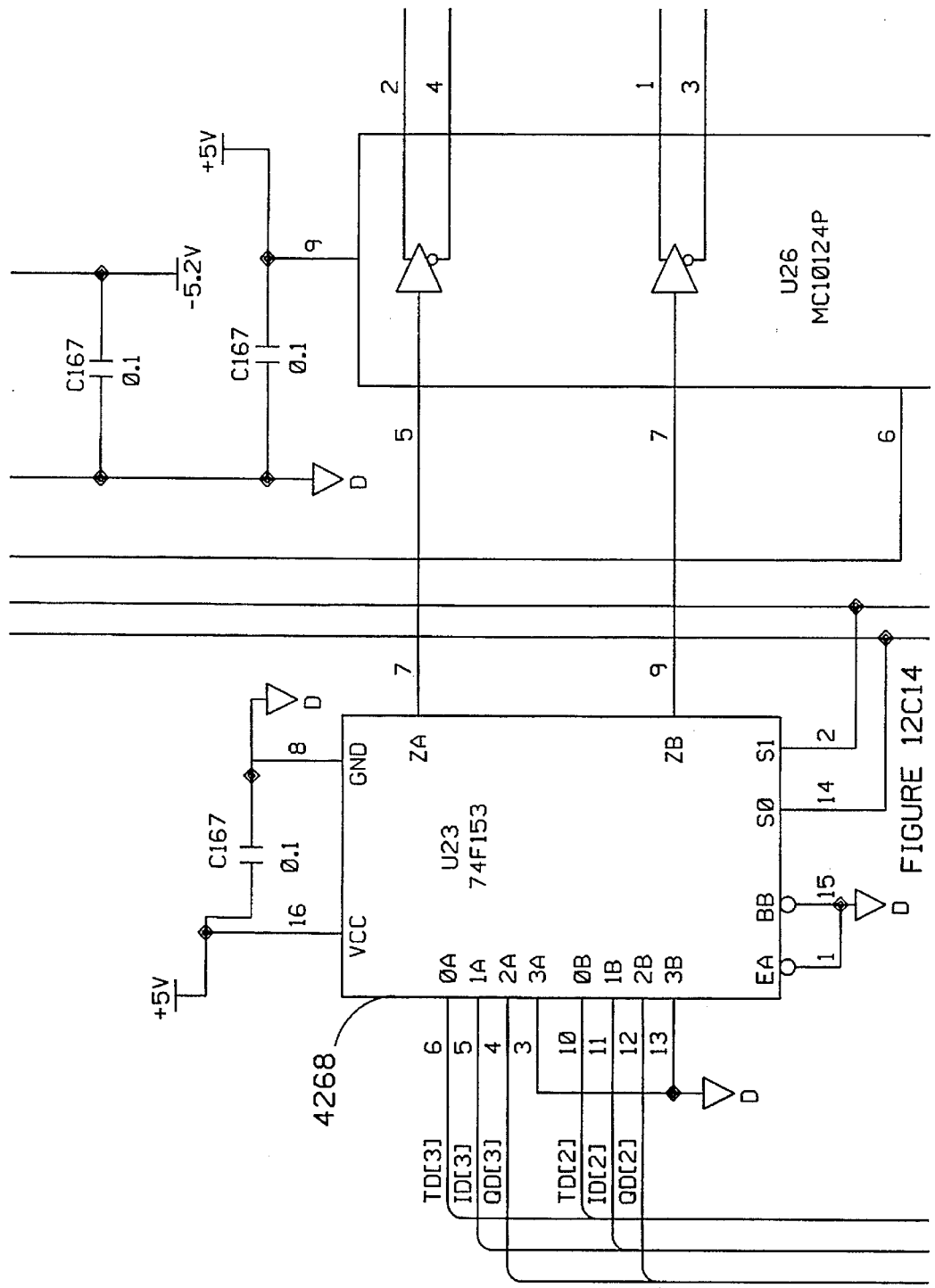
FIGURE 12C14

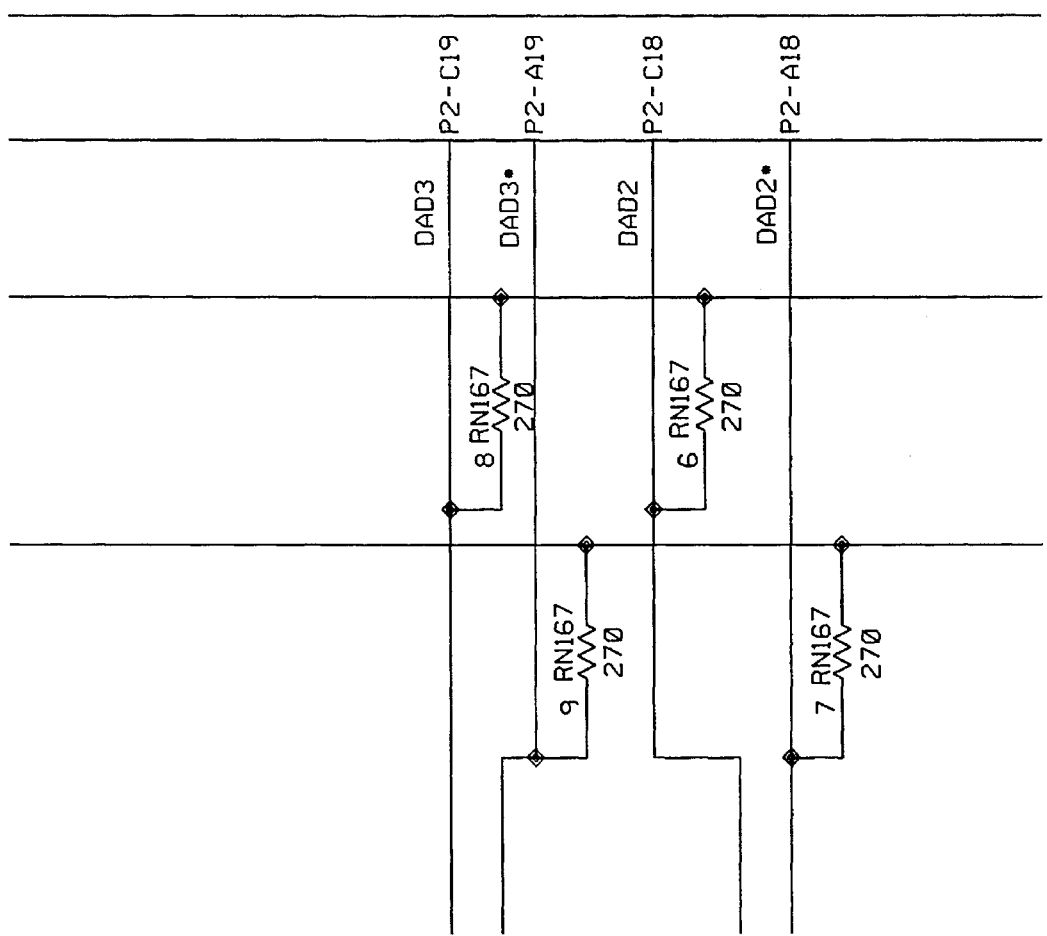
FIGURE 12C15

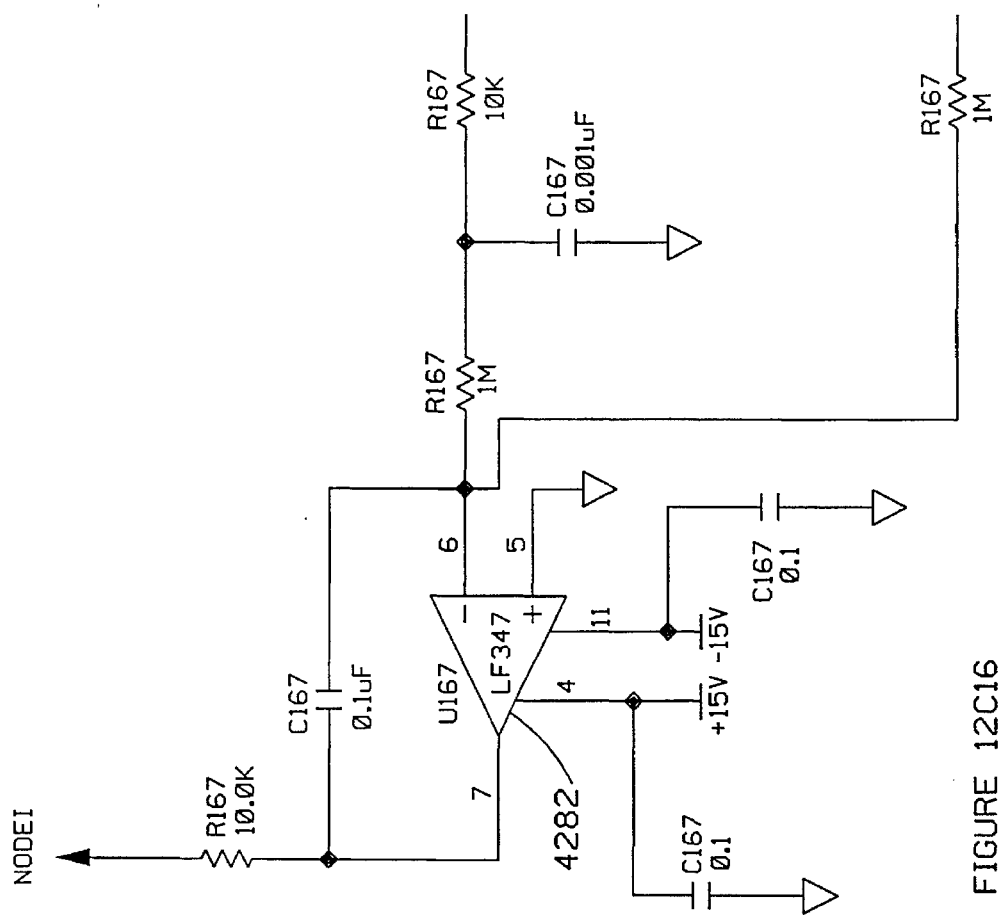
FIGURE 12C16

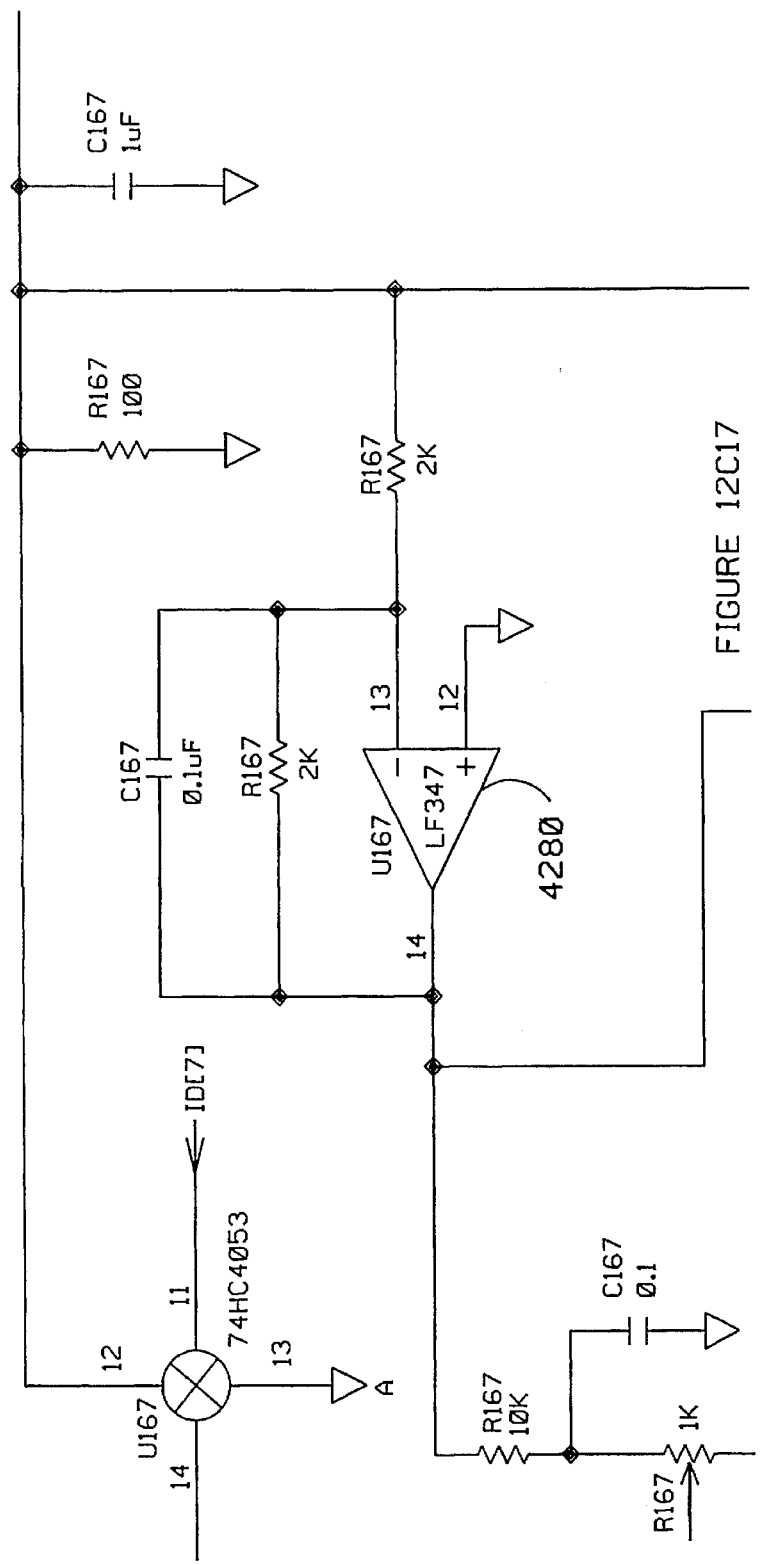
FIGURE 12C17

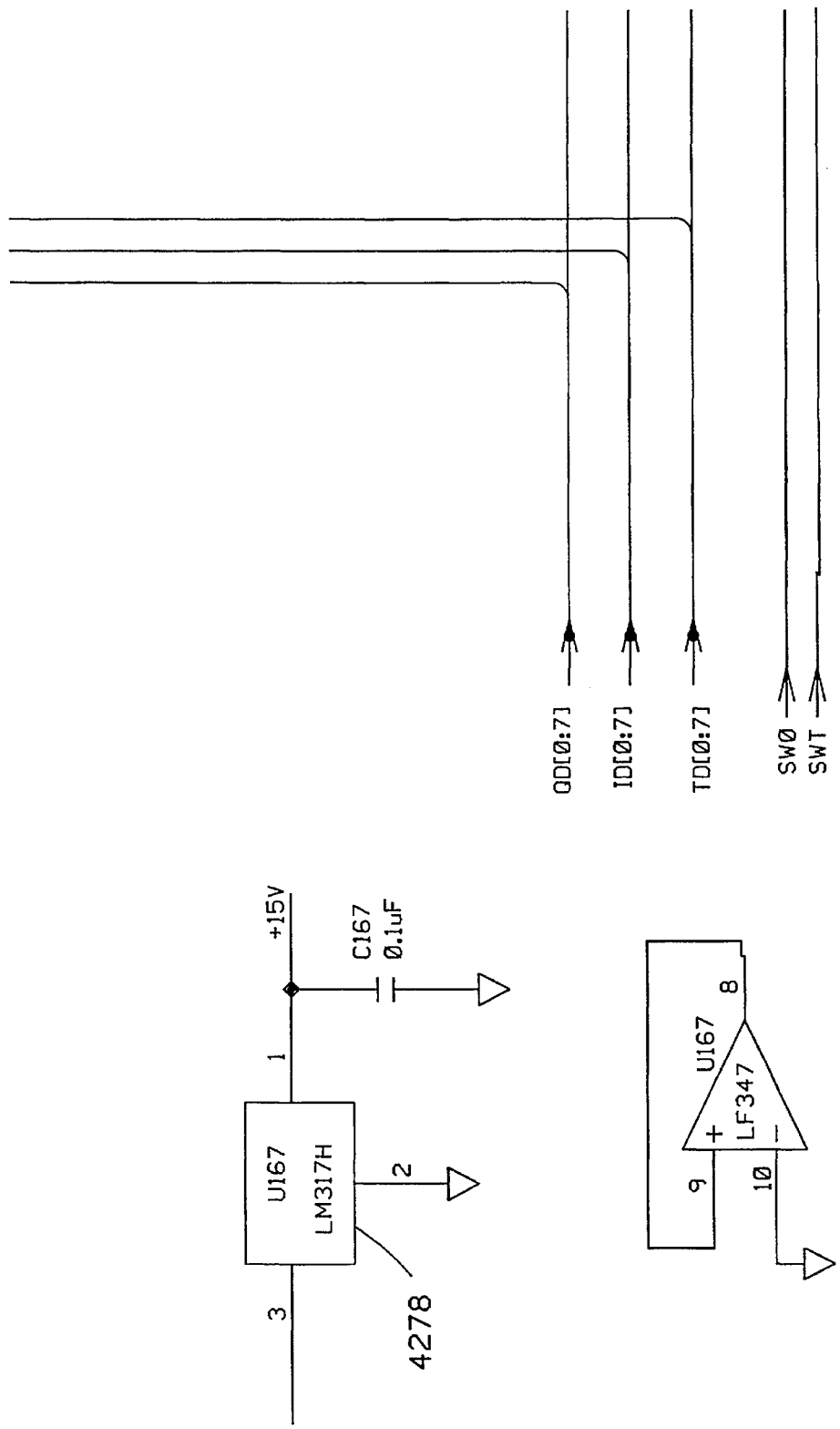
FIGURE 12C18

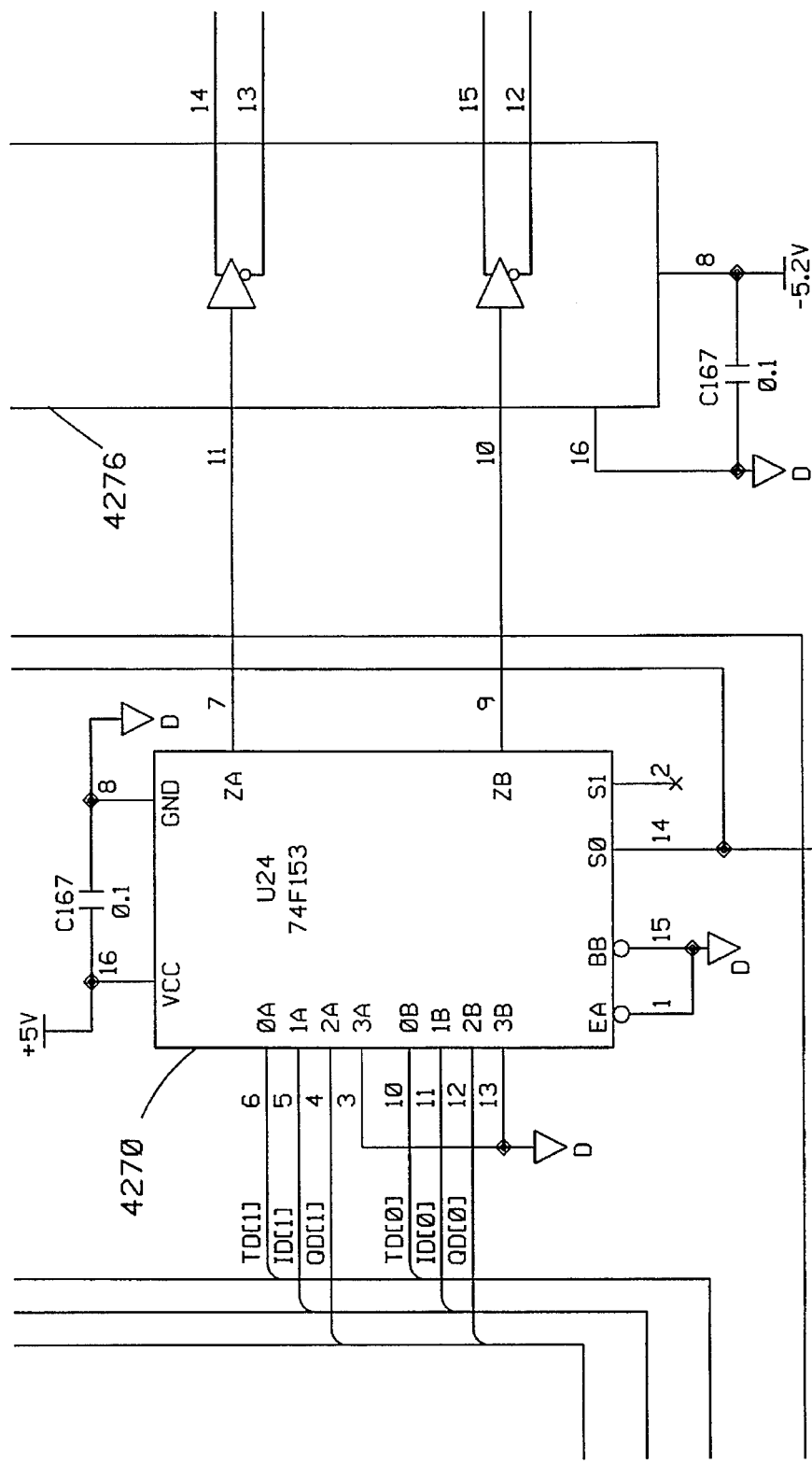
FIGURE 12C19

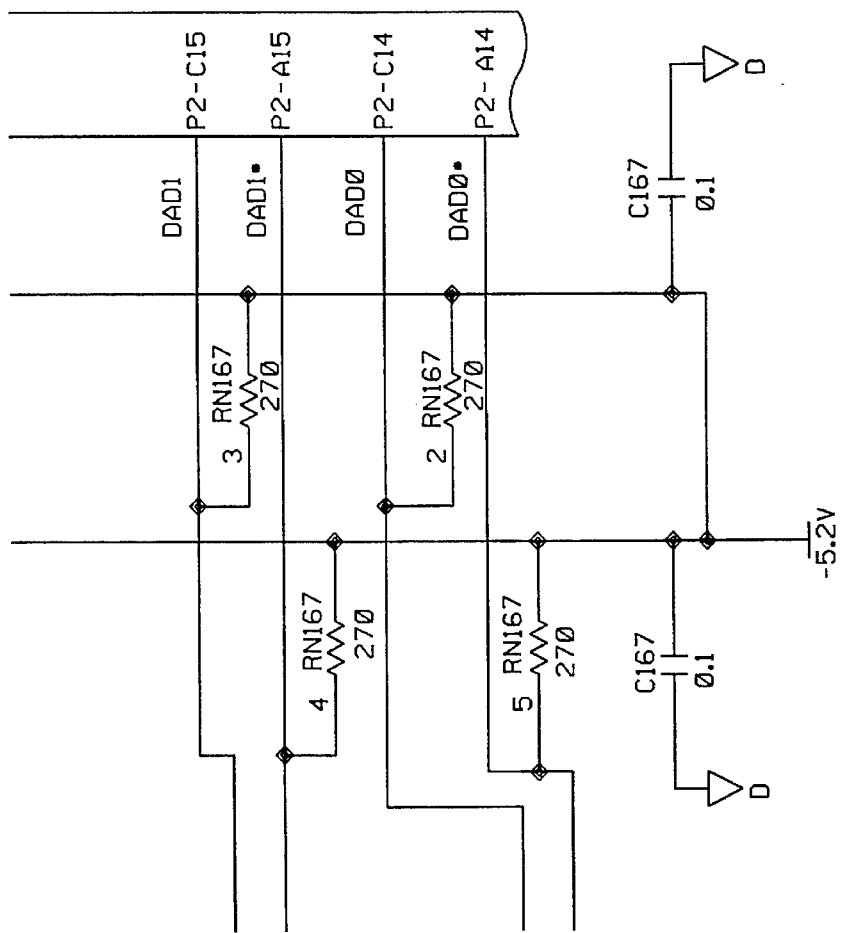
FIGURE 12C20

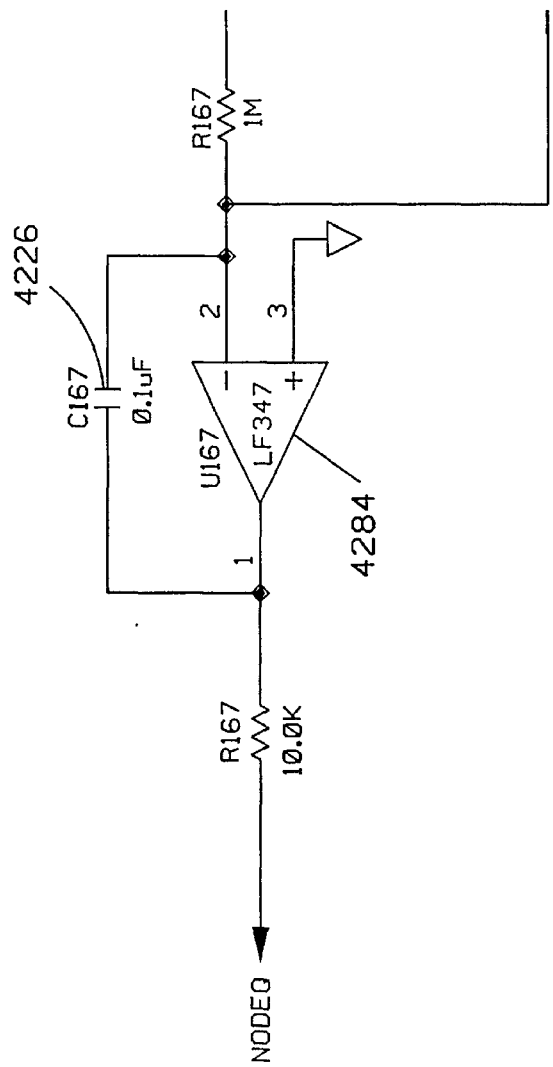
FIGURE 12C21

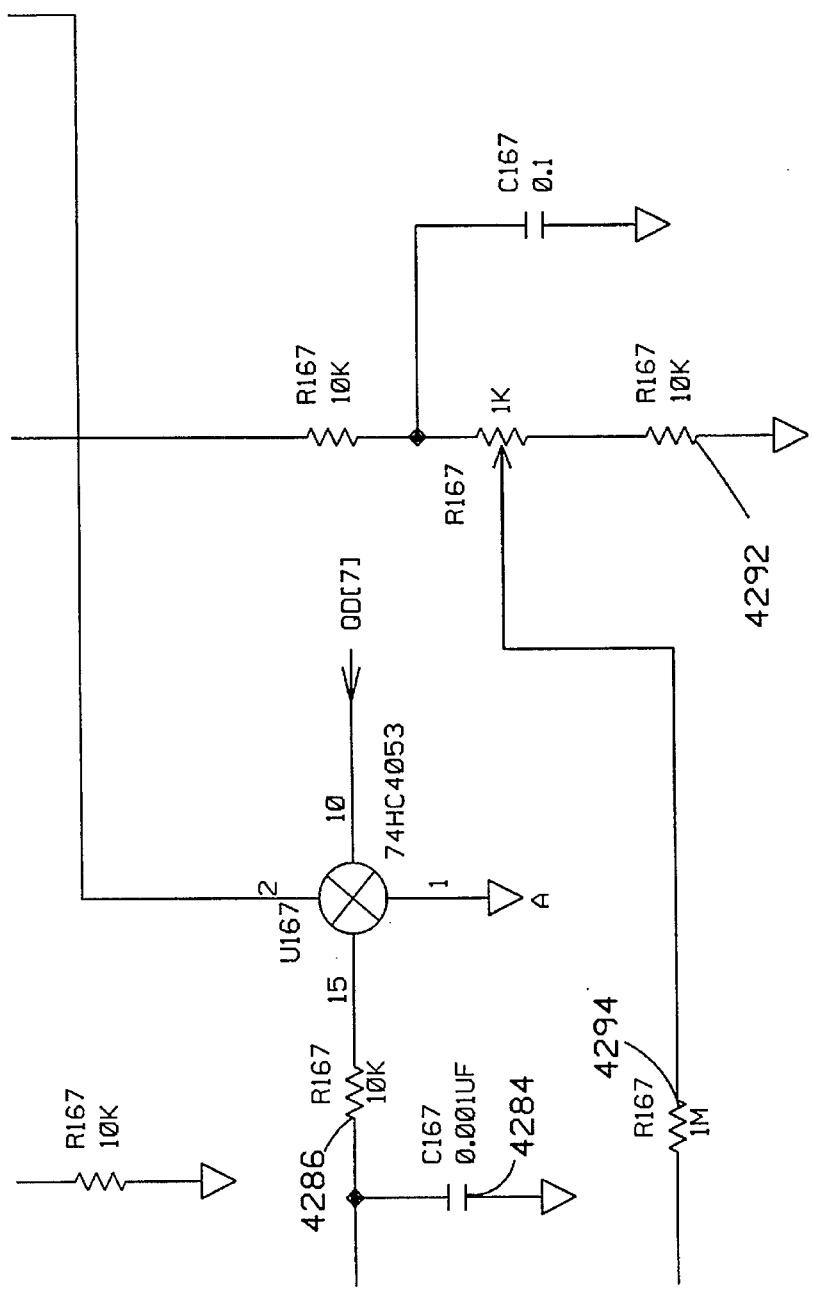
FIGURE 12C22

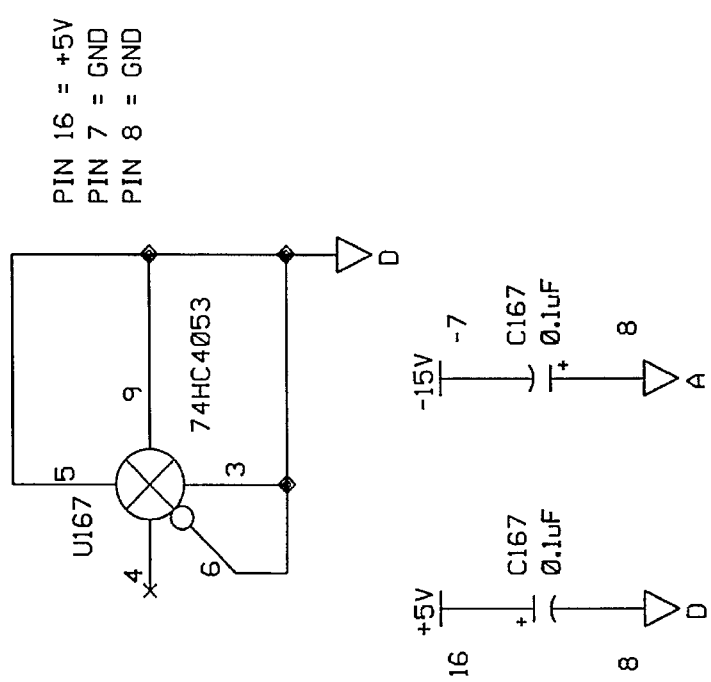
FIGURE 12C23

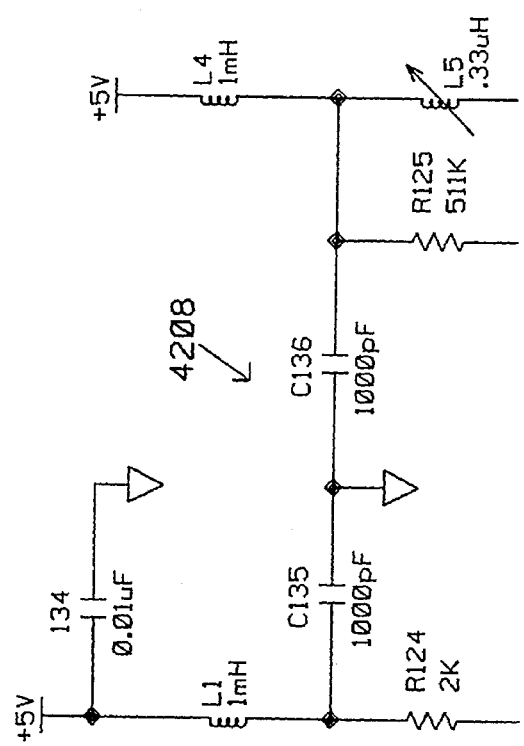

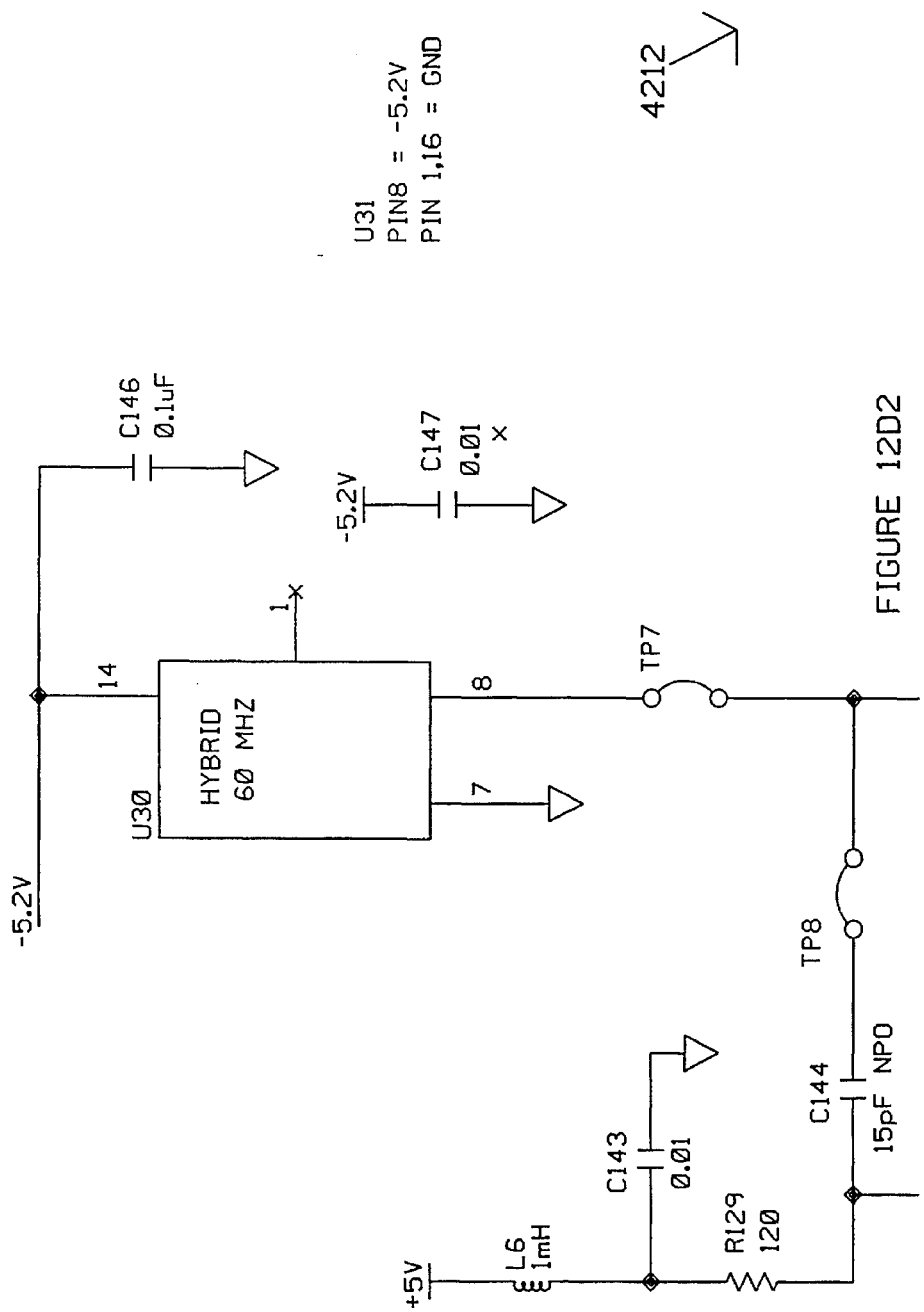
FIGURE 12D2

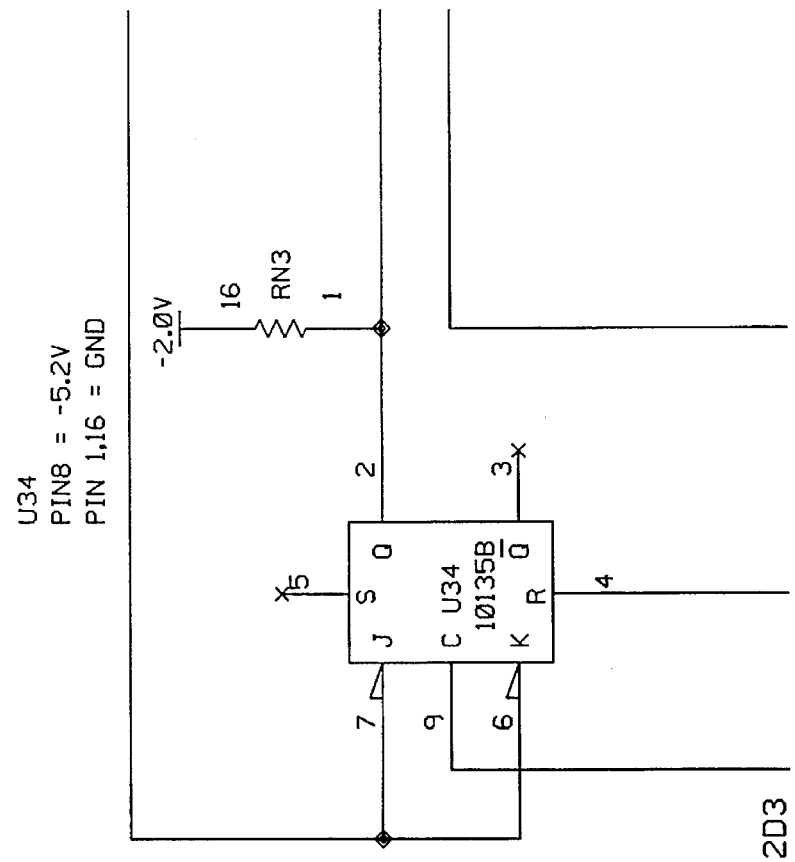
FIGURE 12D3

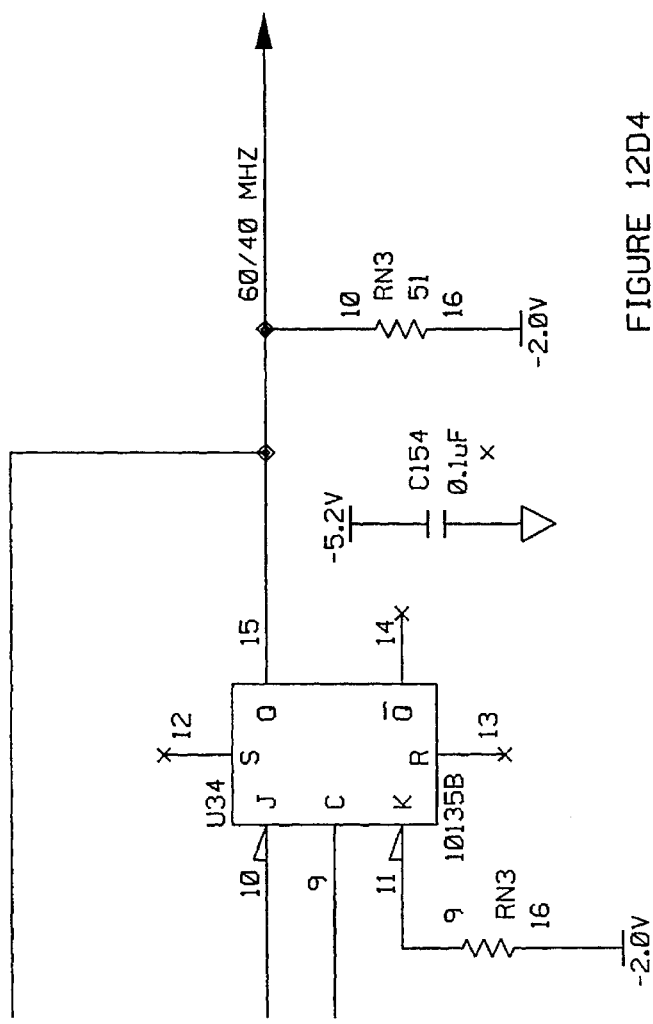
FIGURE 12D4

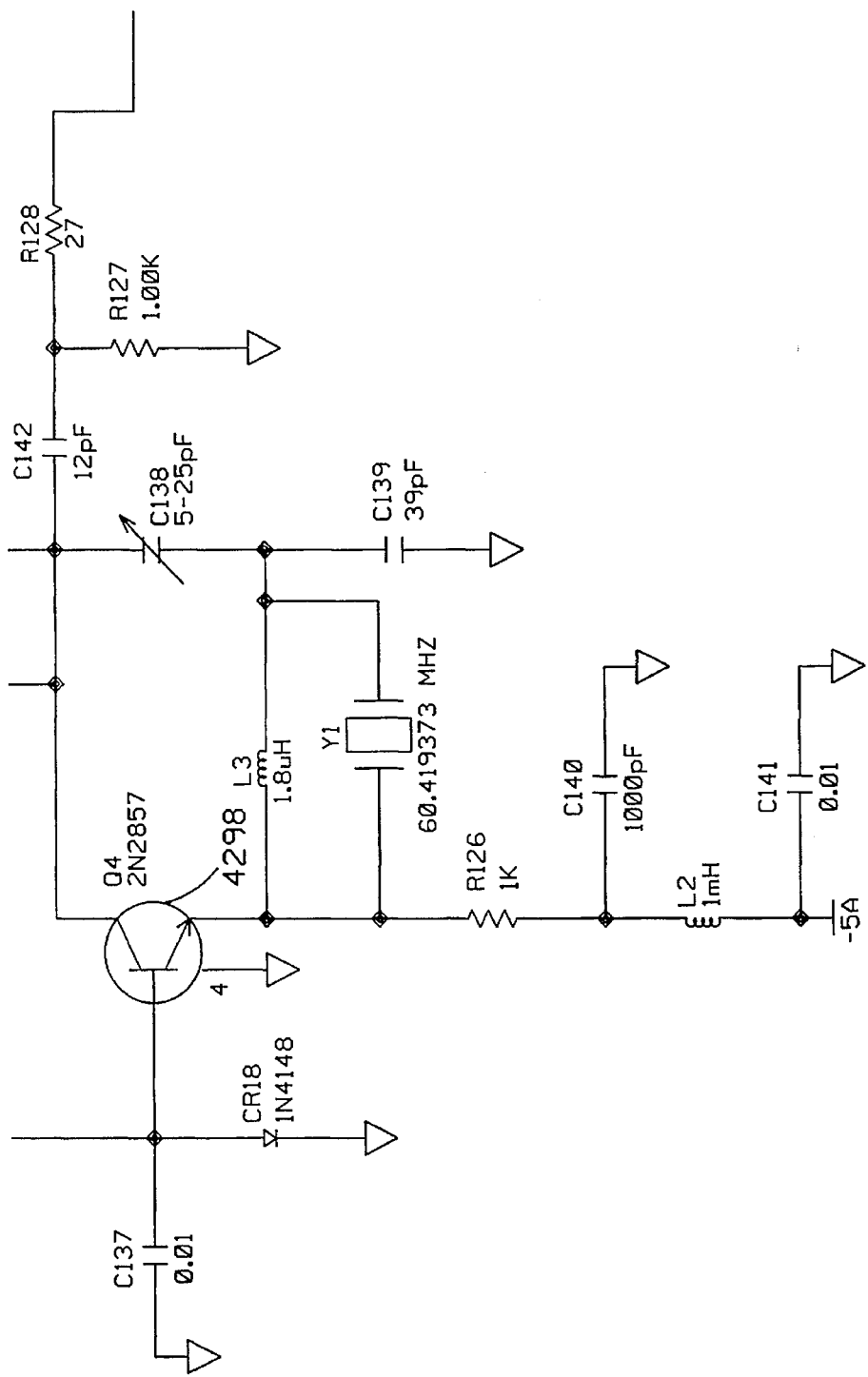
FIGURE 12D5

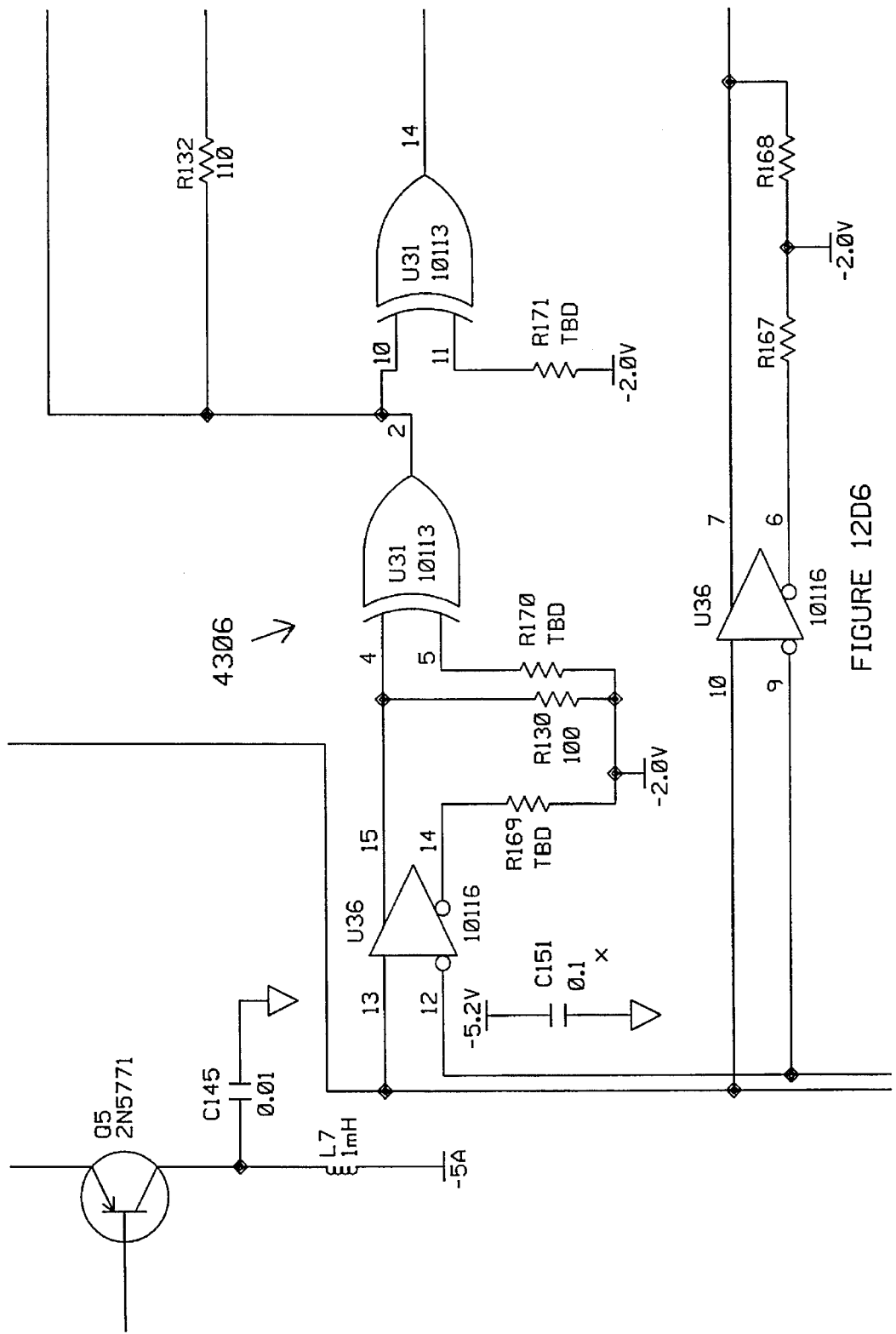
FIGURE 12D6

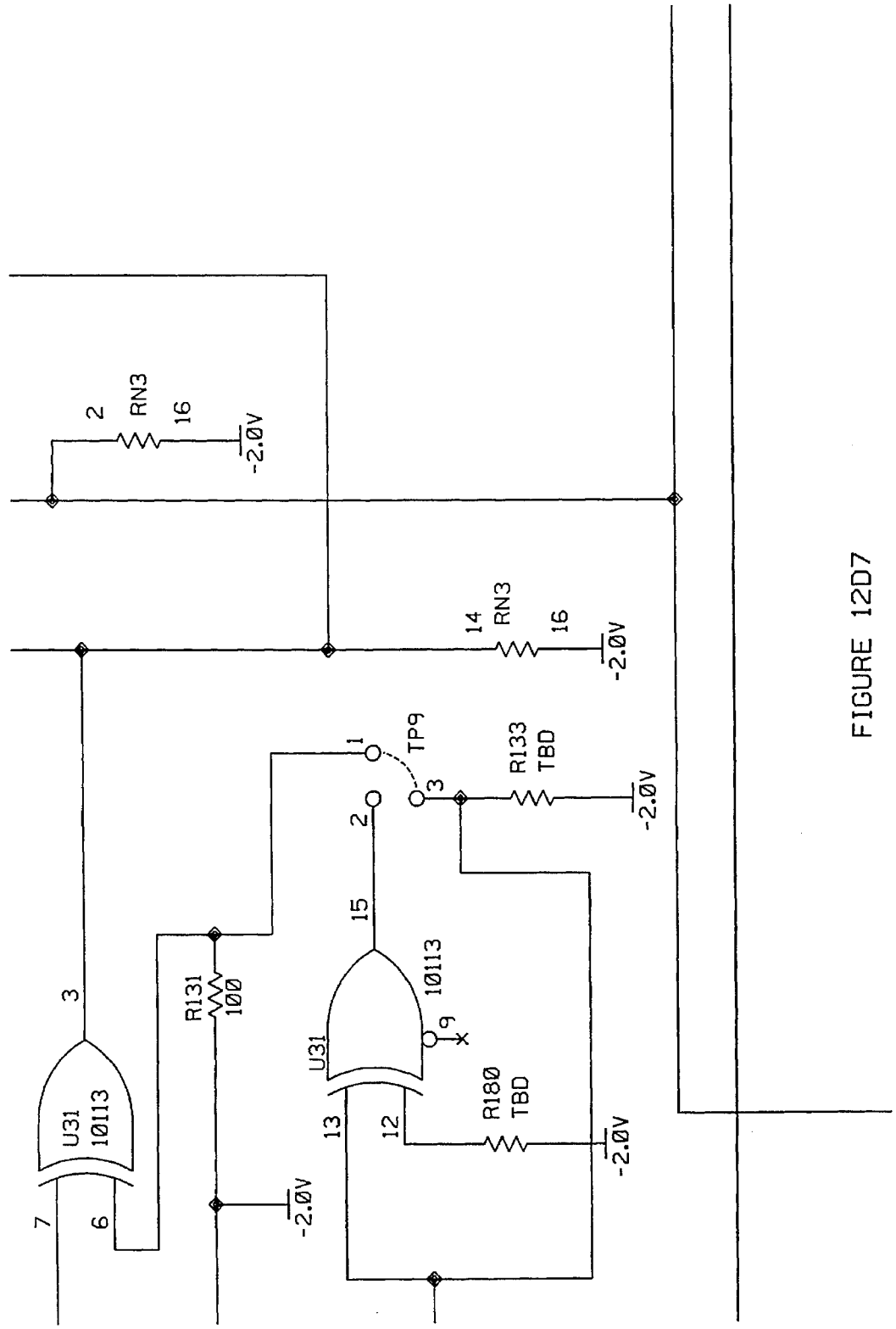
FIGURE 12D7

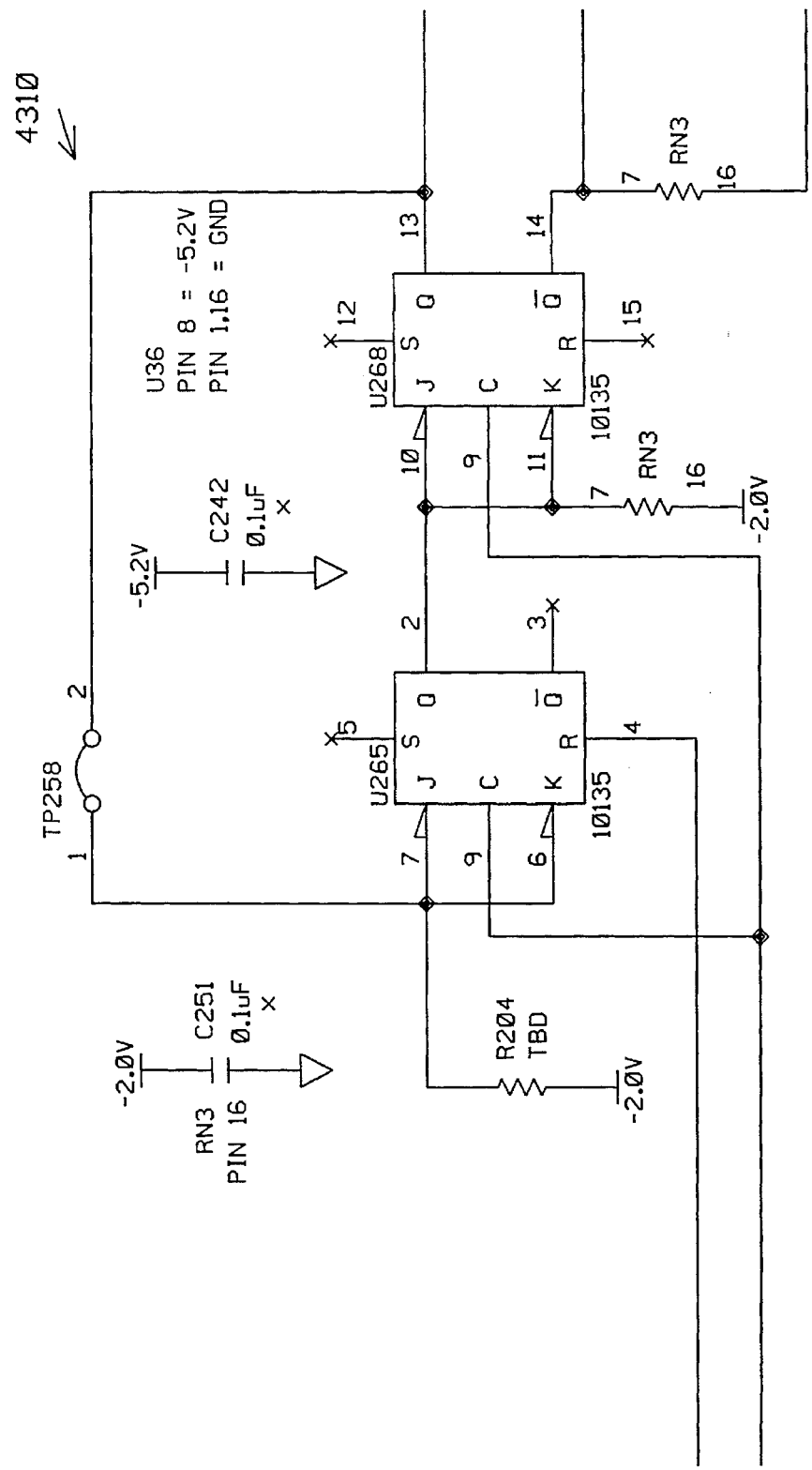
FIGURE 12D8

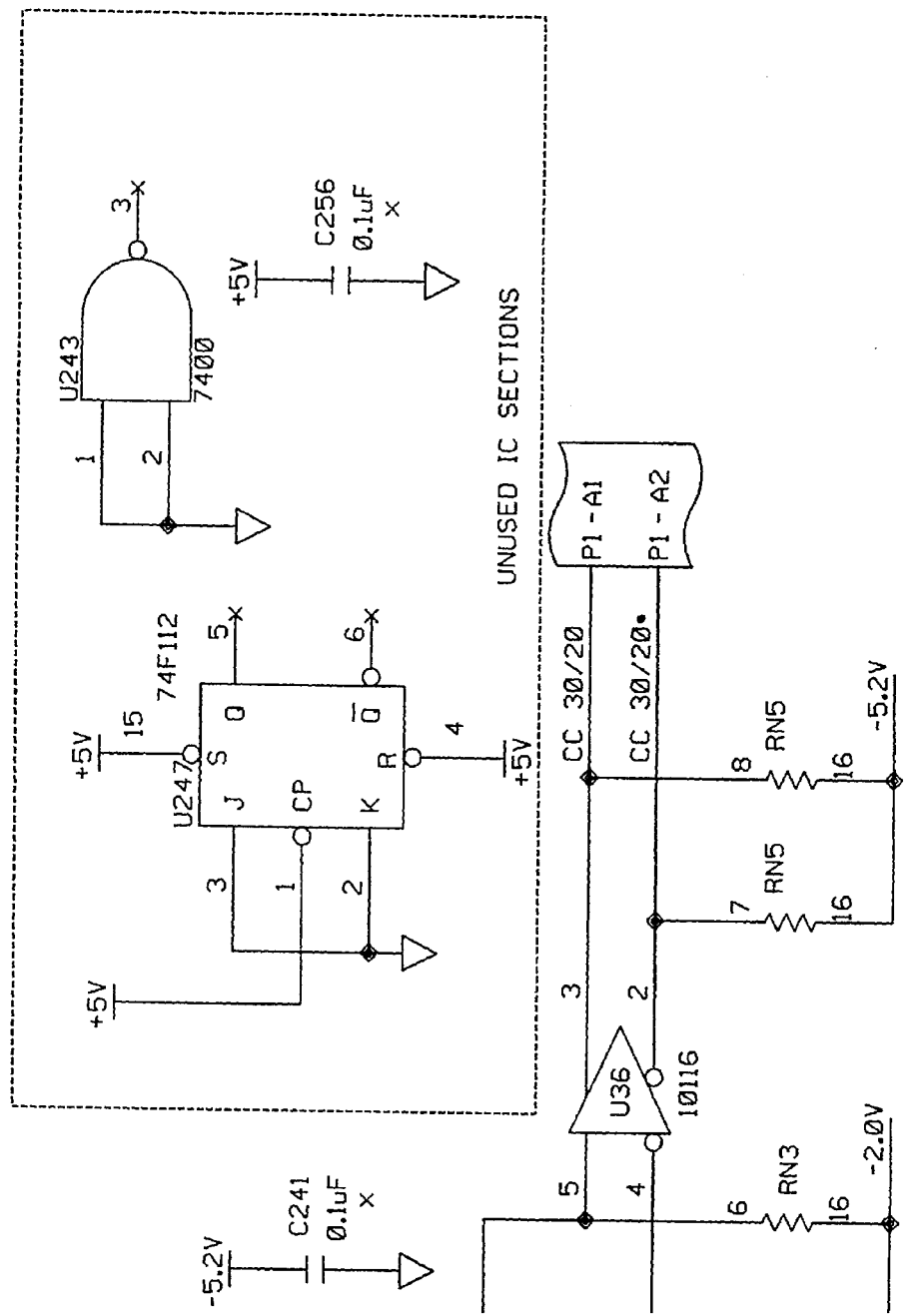

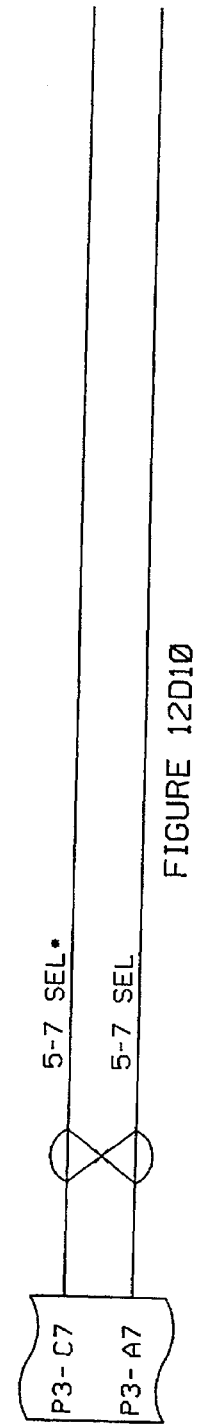

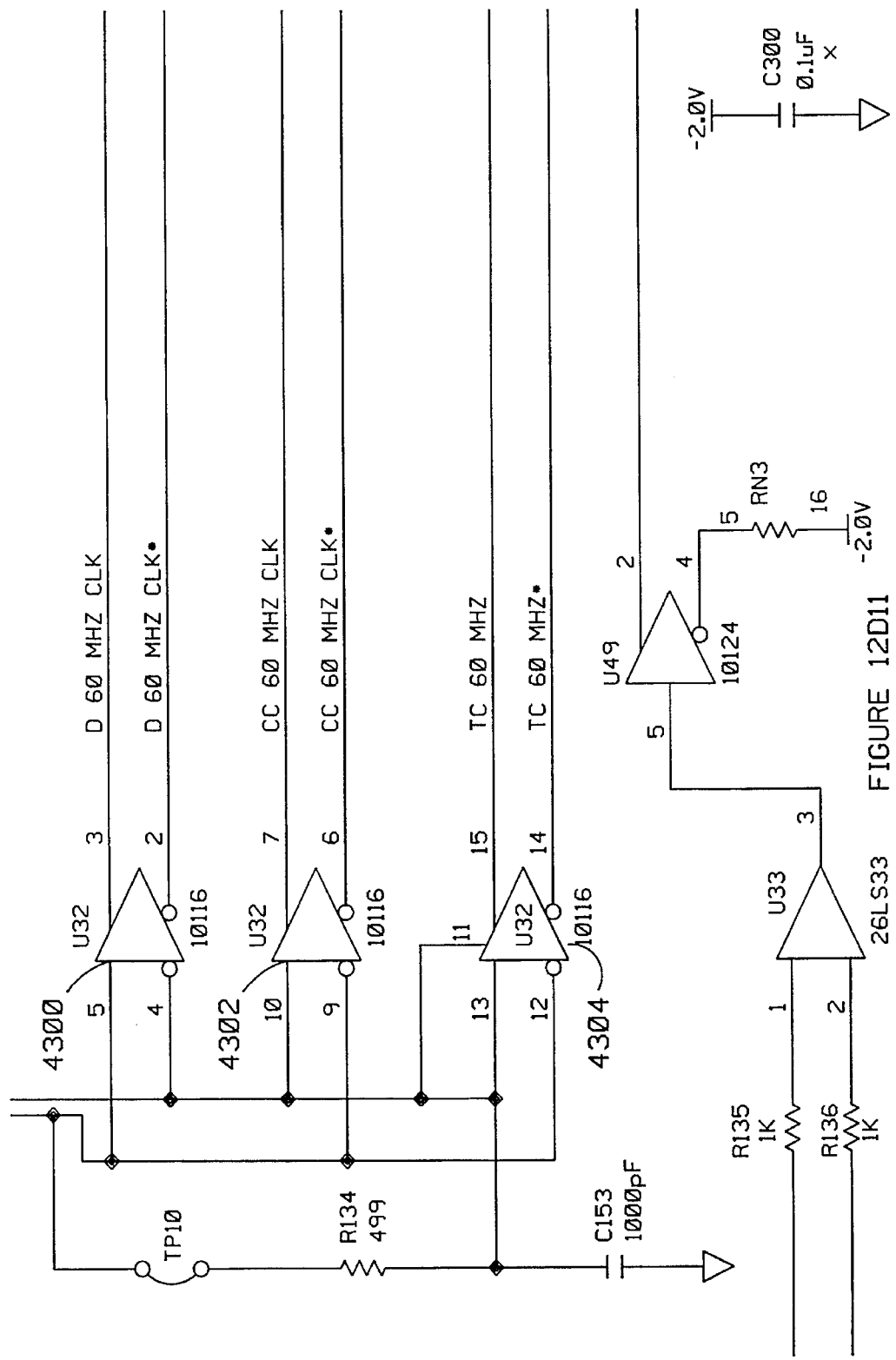
FIGURE 12D11

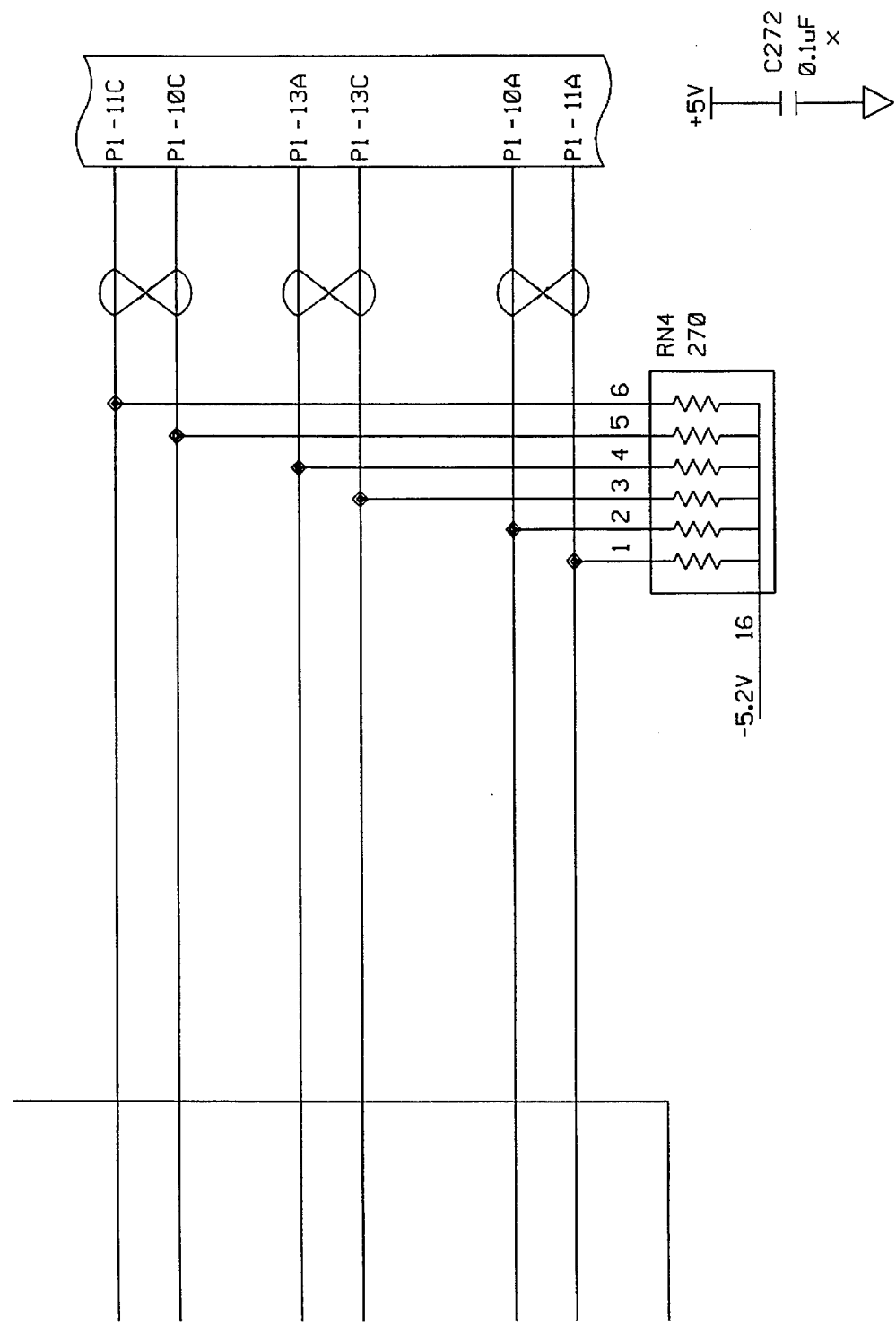
FIGURE 12D12

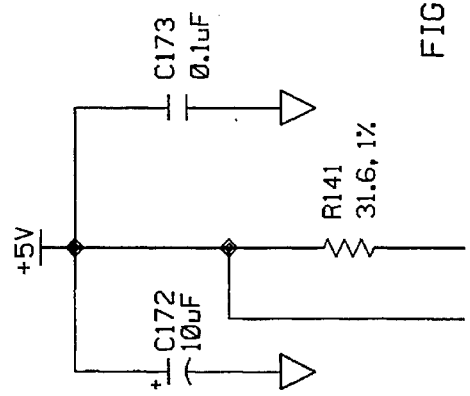

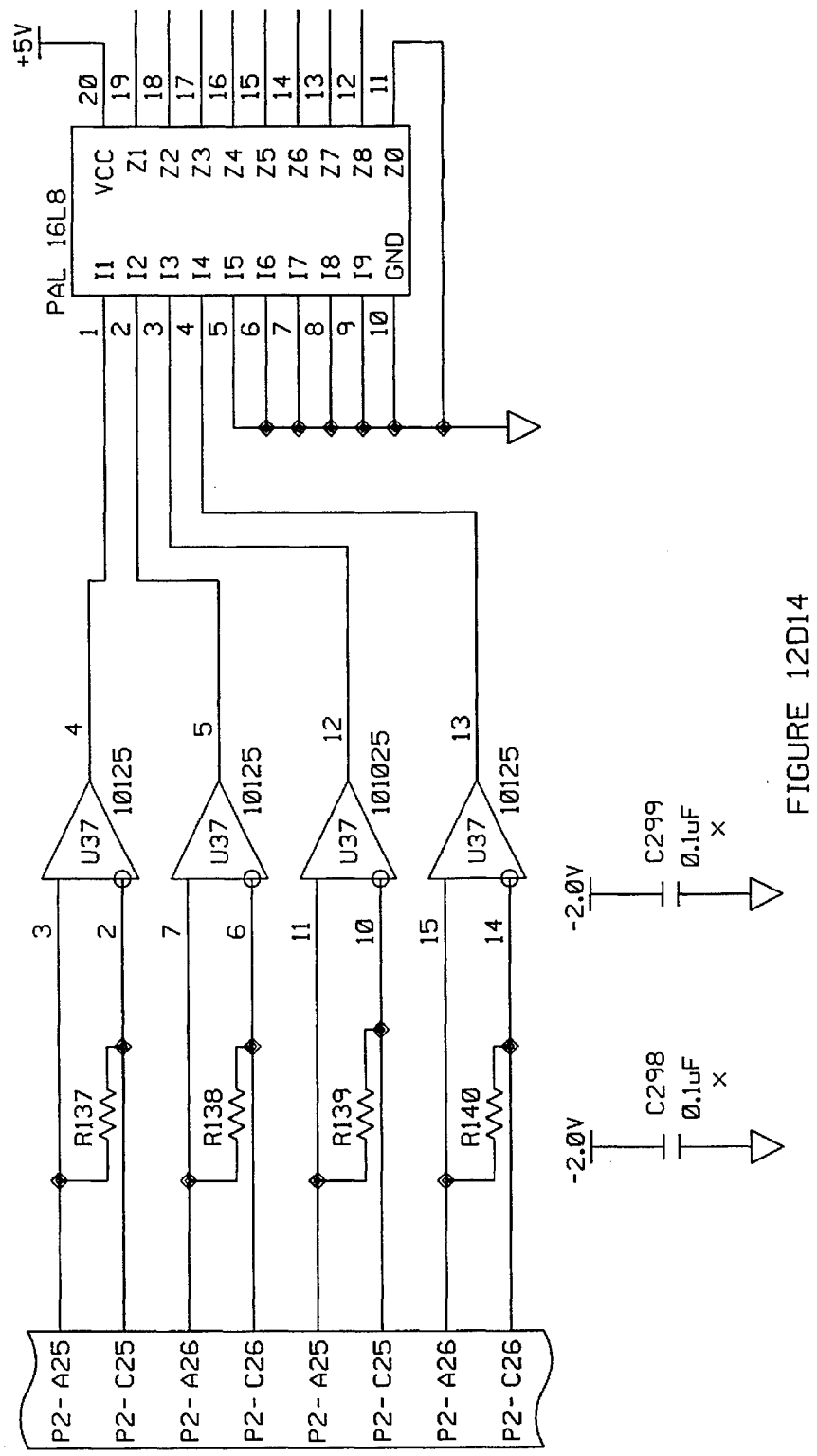
FIGURE 12D14

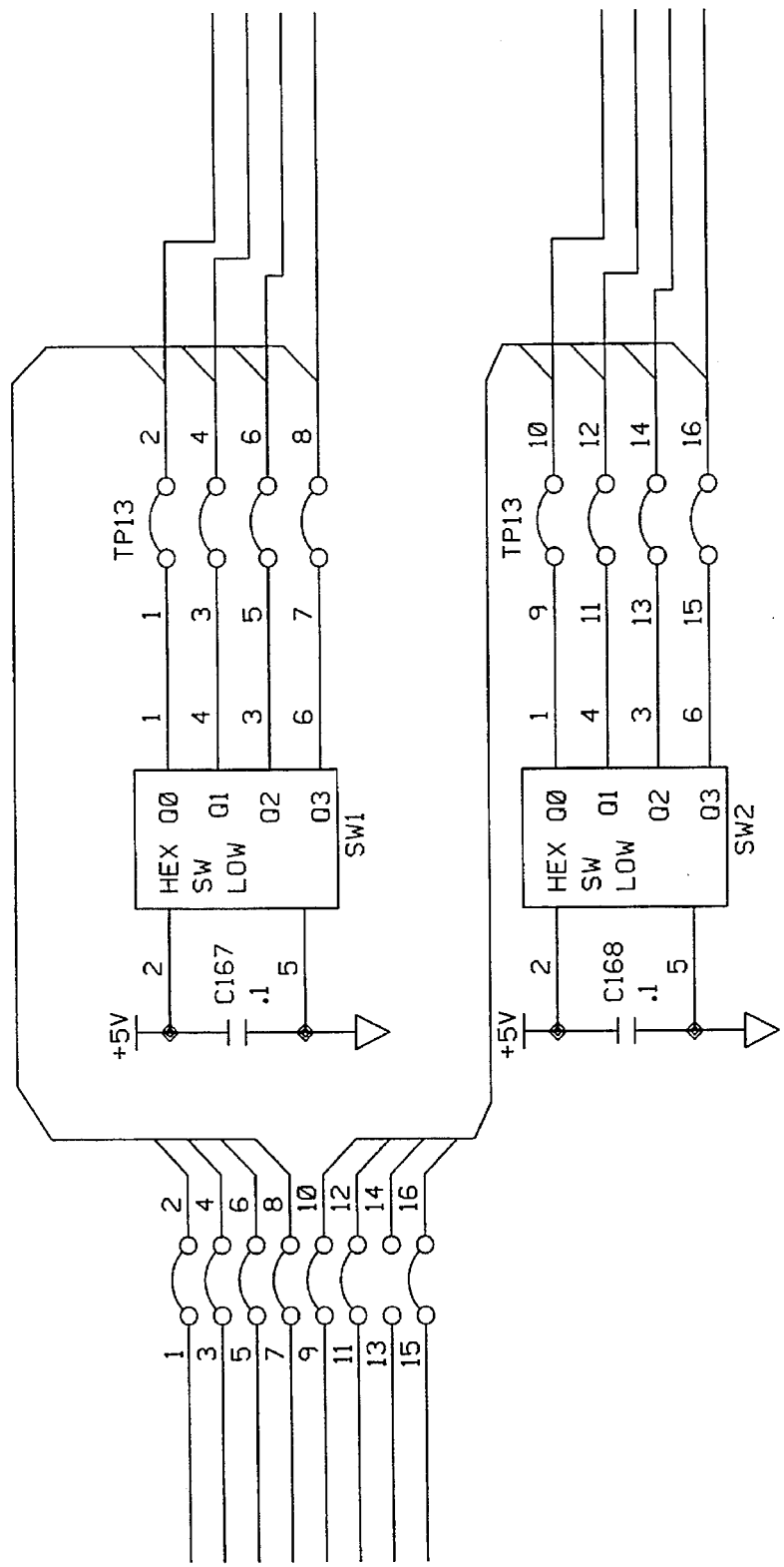
FIGURE 12D15

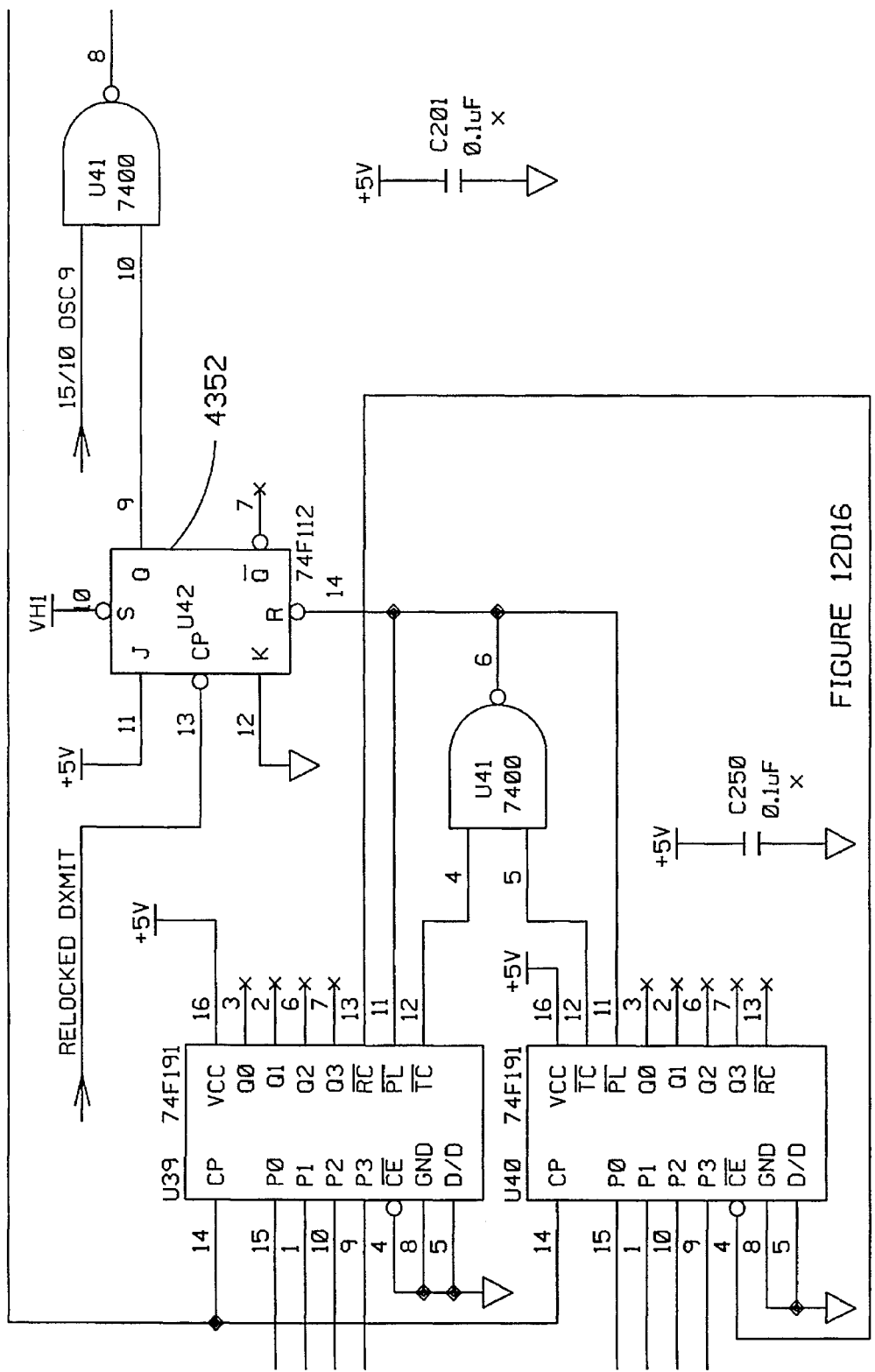
FIGURE 12D16

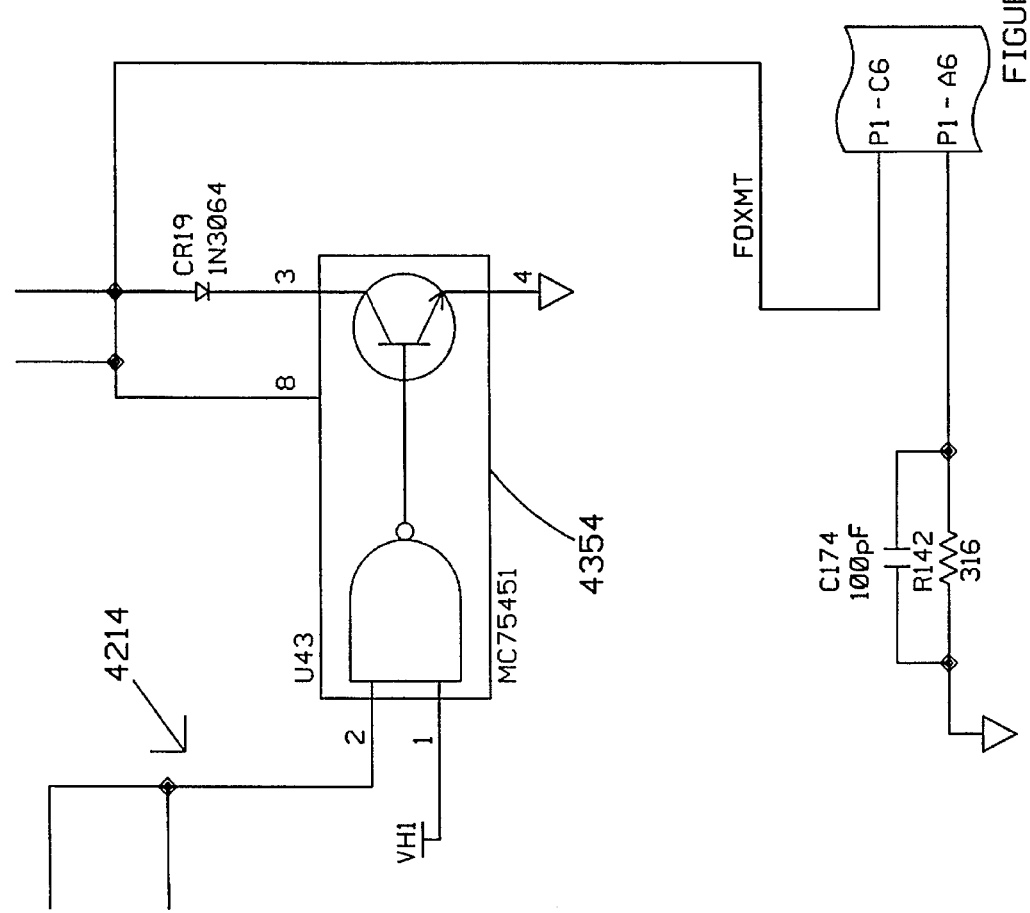
FIGURE 12D17

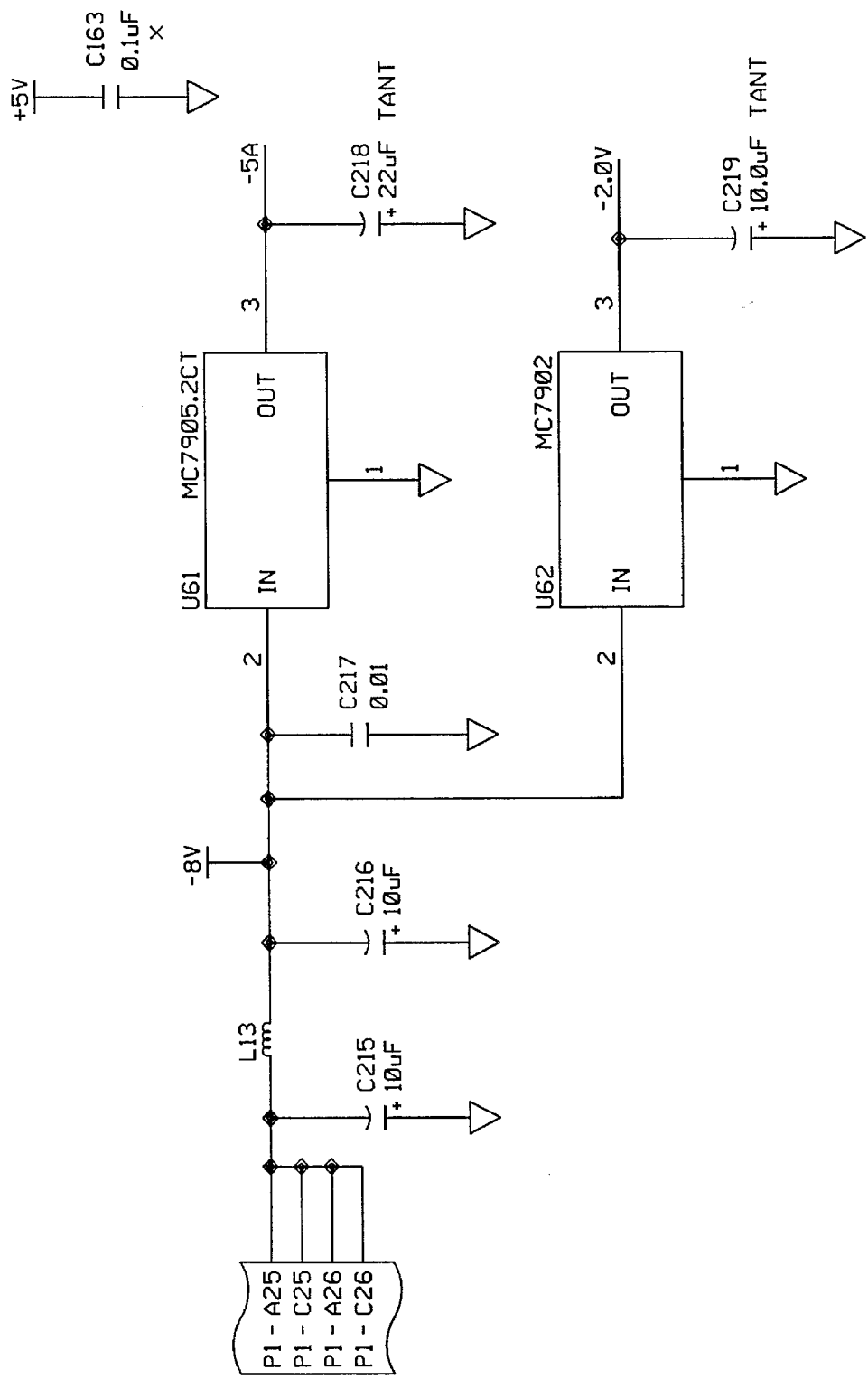
FIGURE 12D18

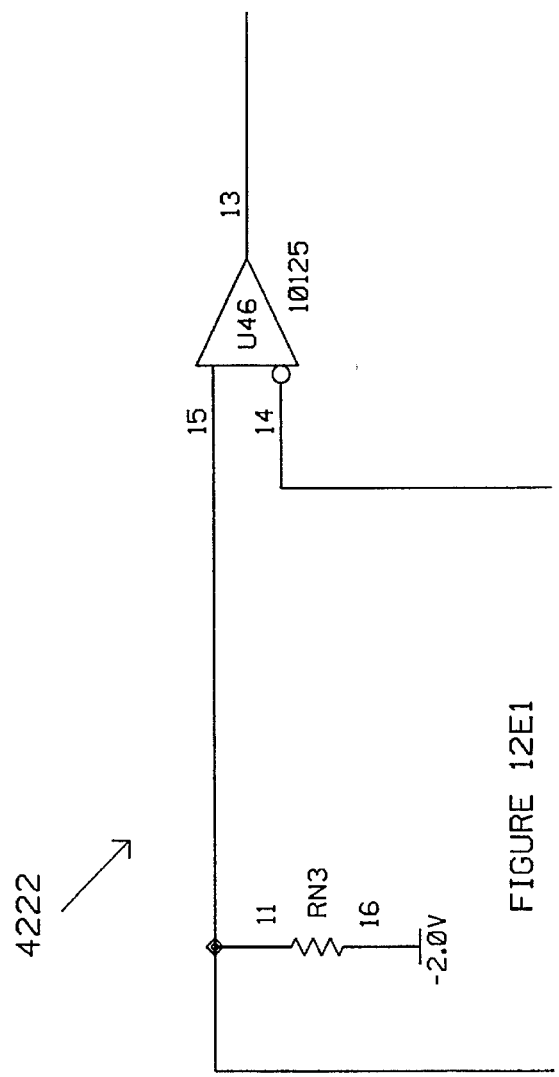
FIGURE 12E1

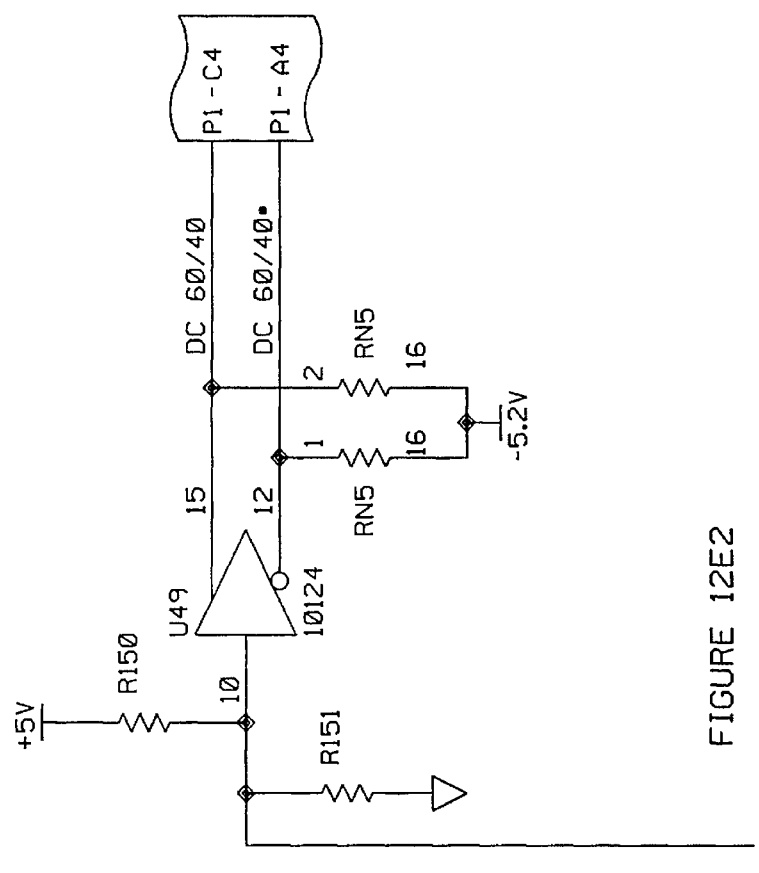
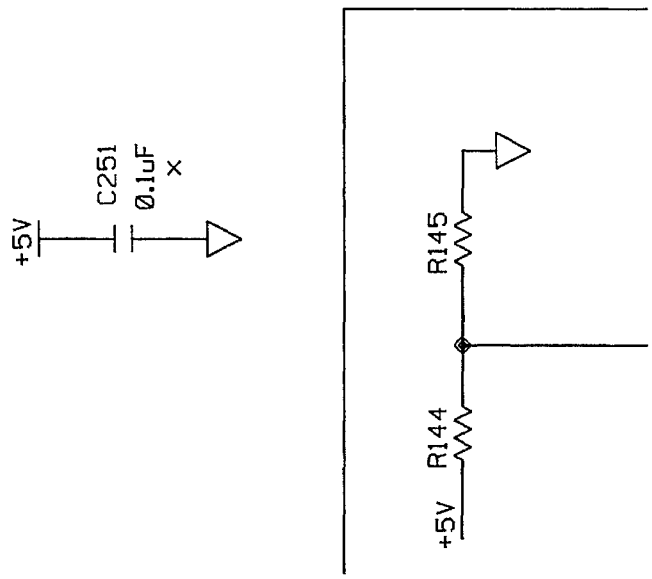
FIGURE 12E2

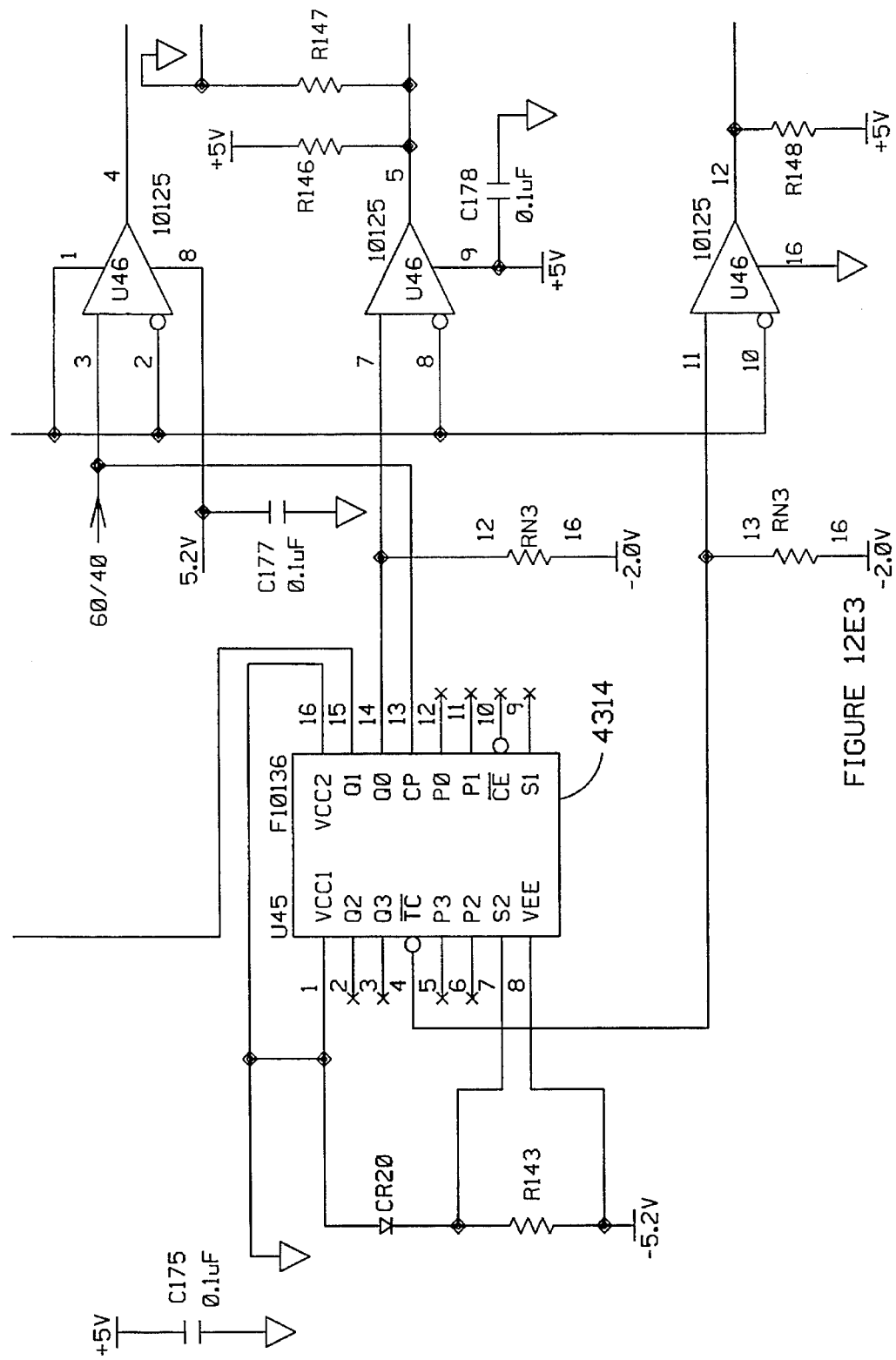
FIGURE 12E3

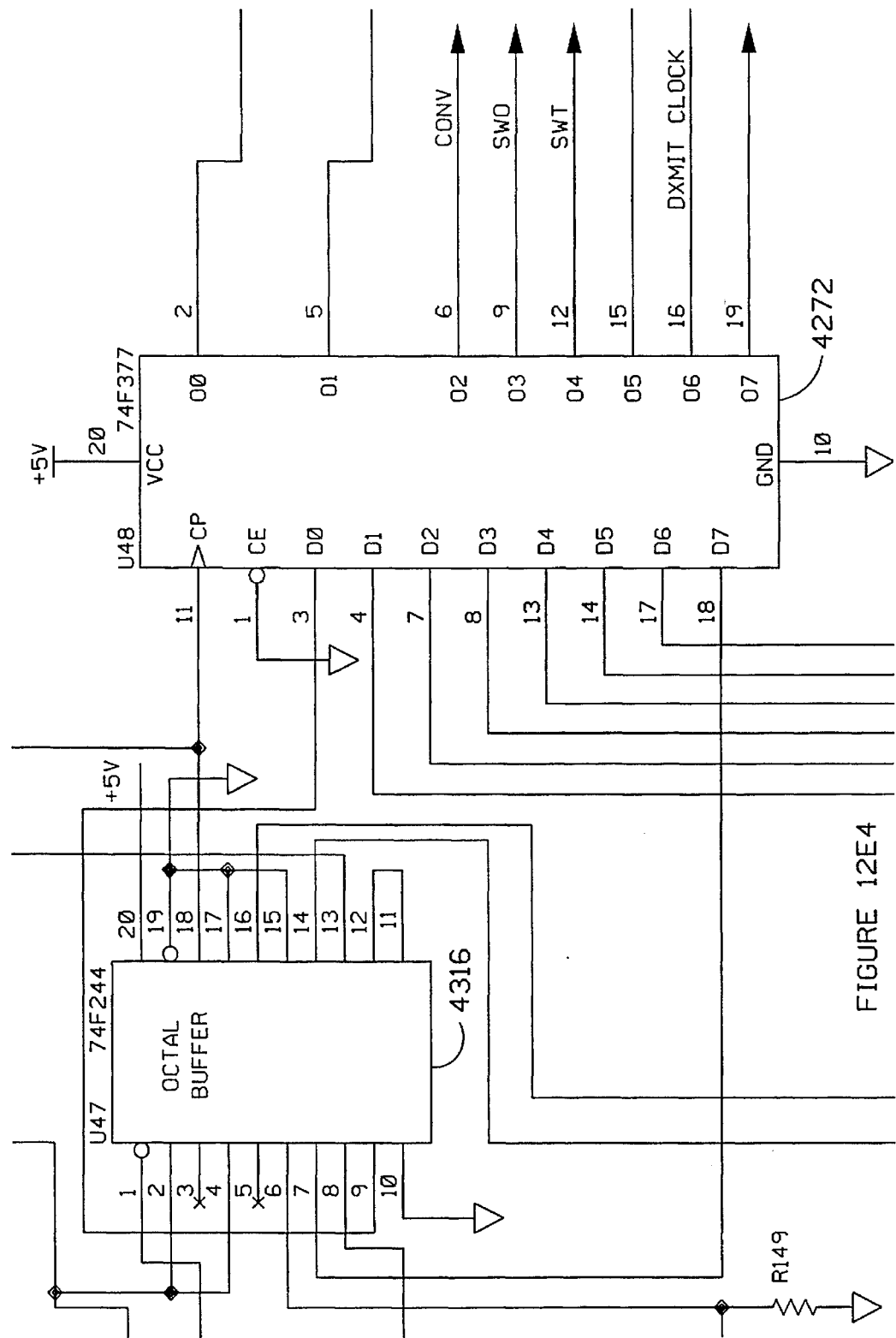
FIGURE 12E4

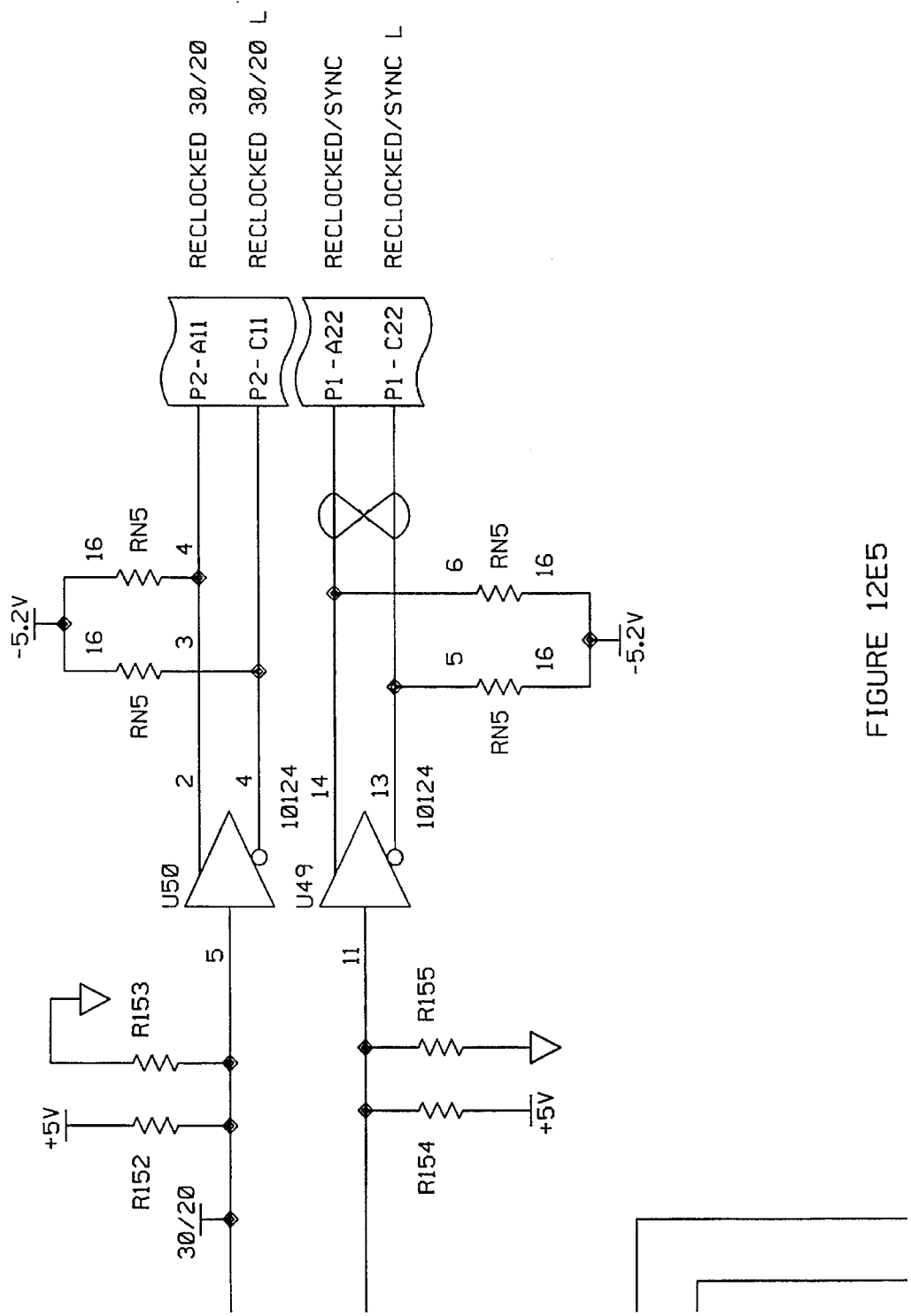
FIGURE 12E5

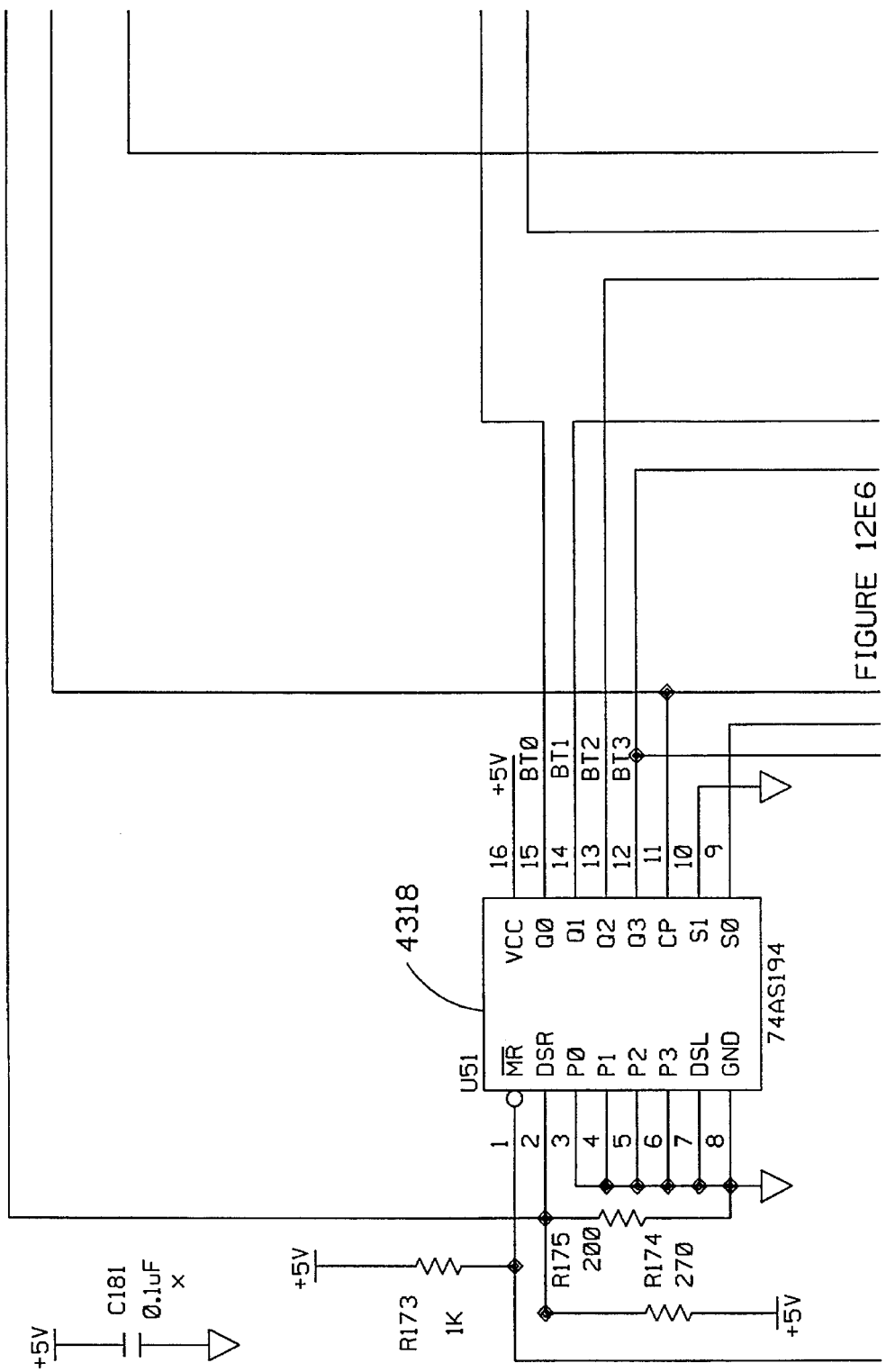
FIGURE 12E6

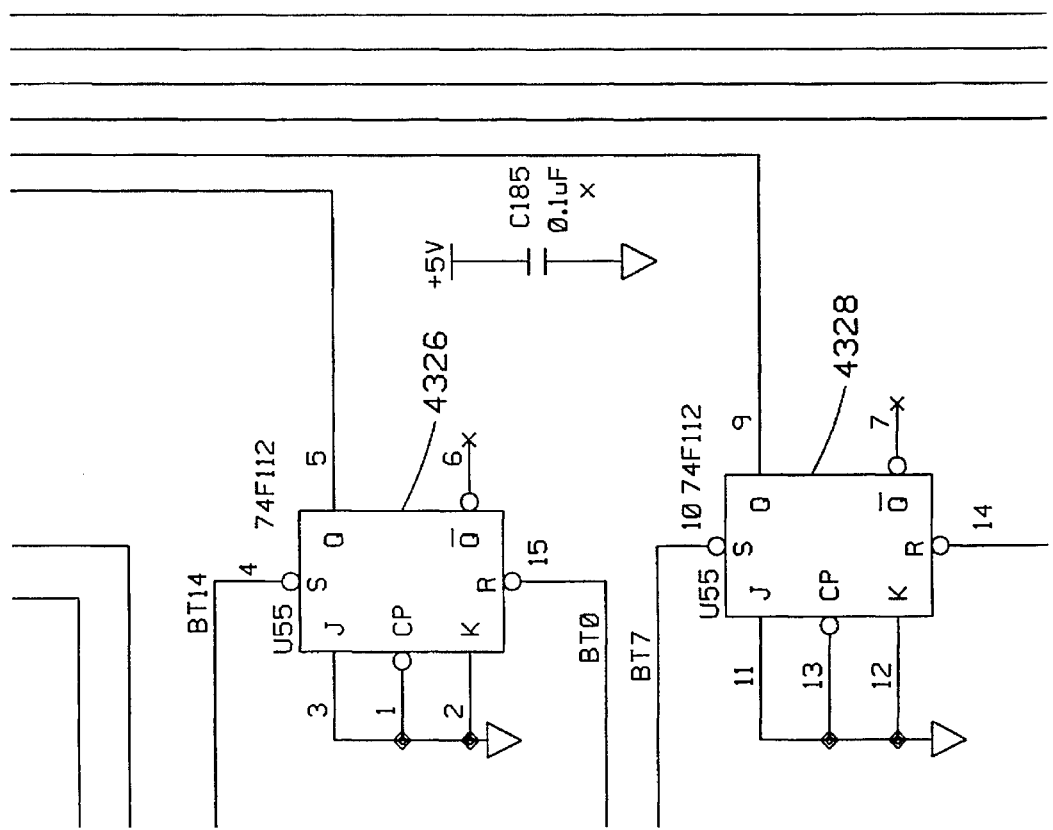
FIGURE 12E7

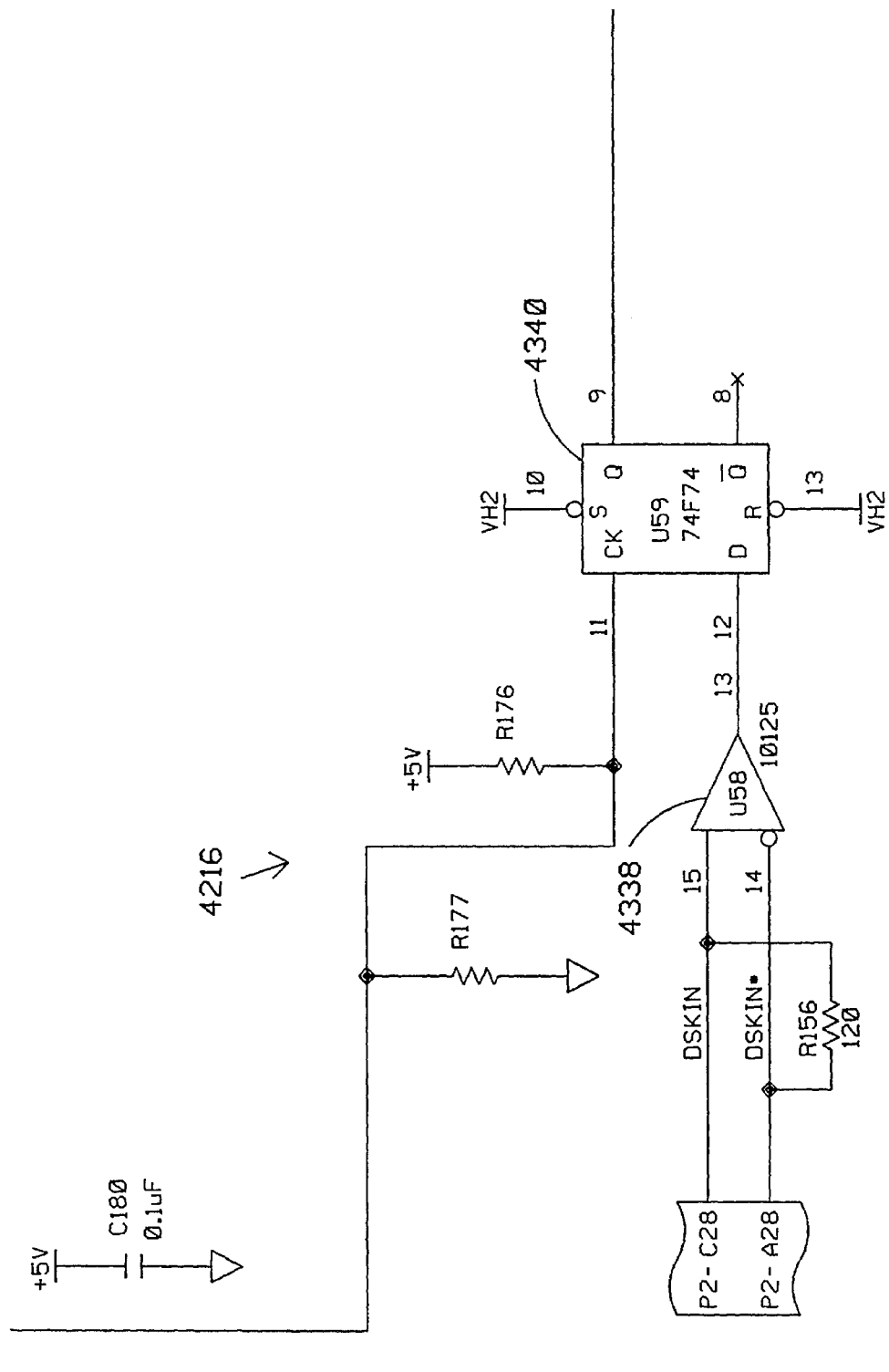
FIGURE 12E8

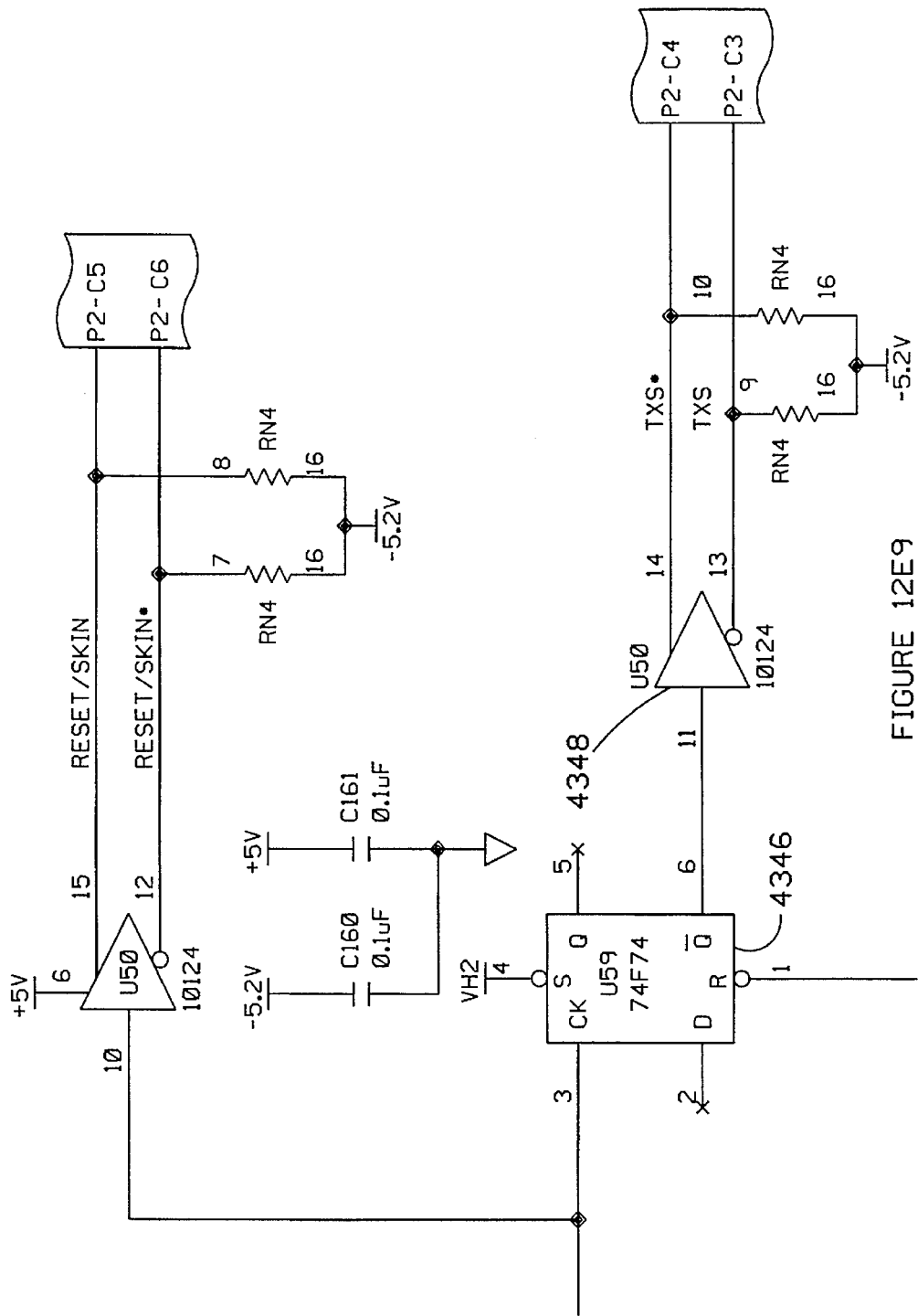
FIGURE 12E9

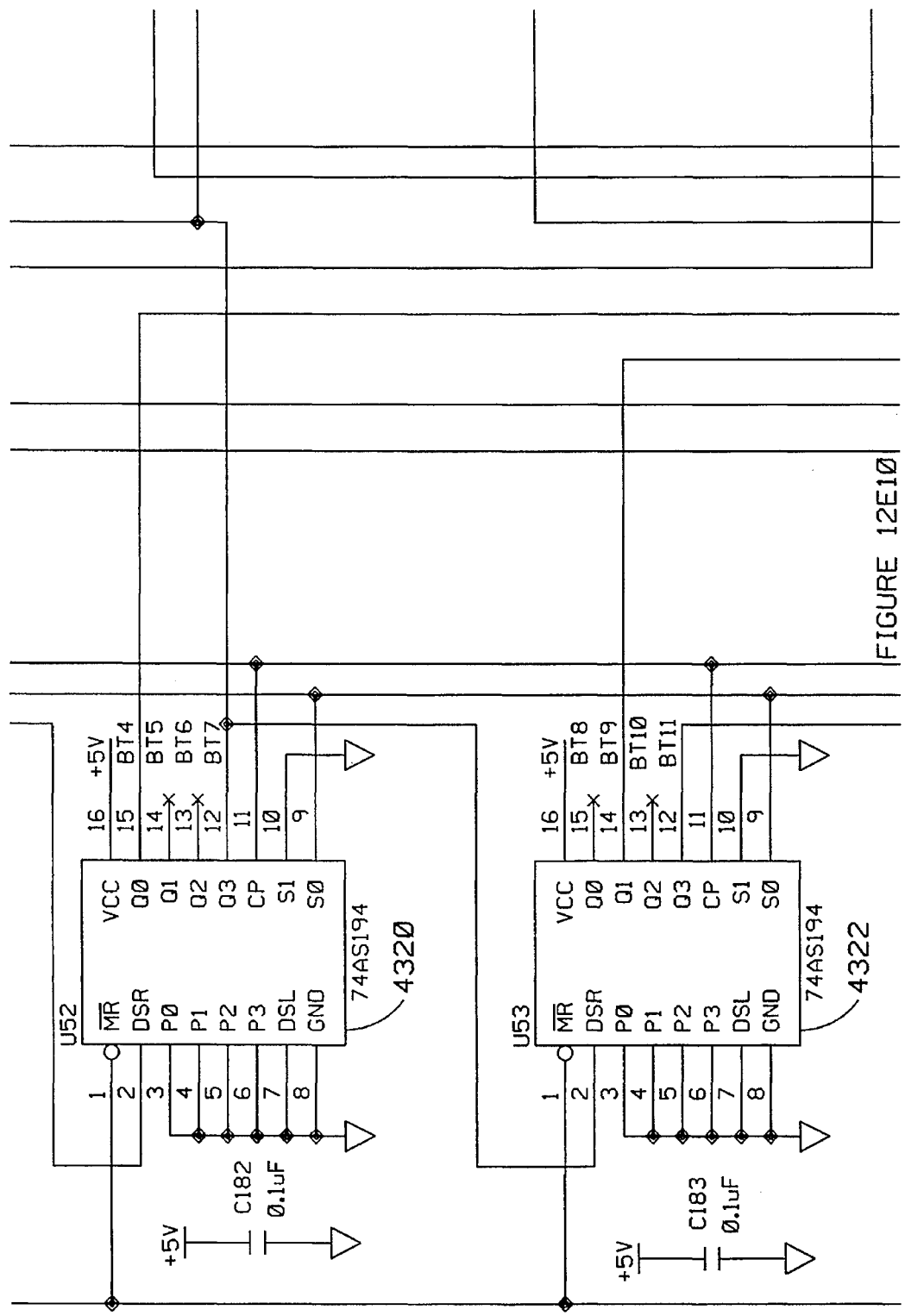

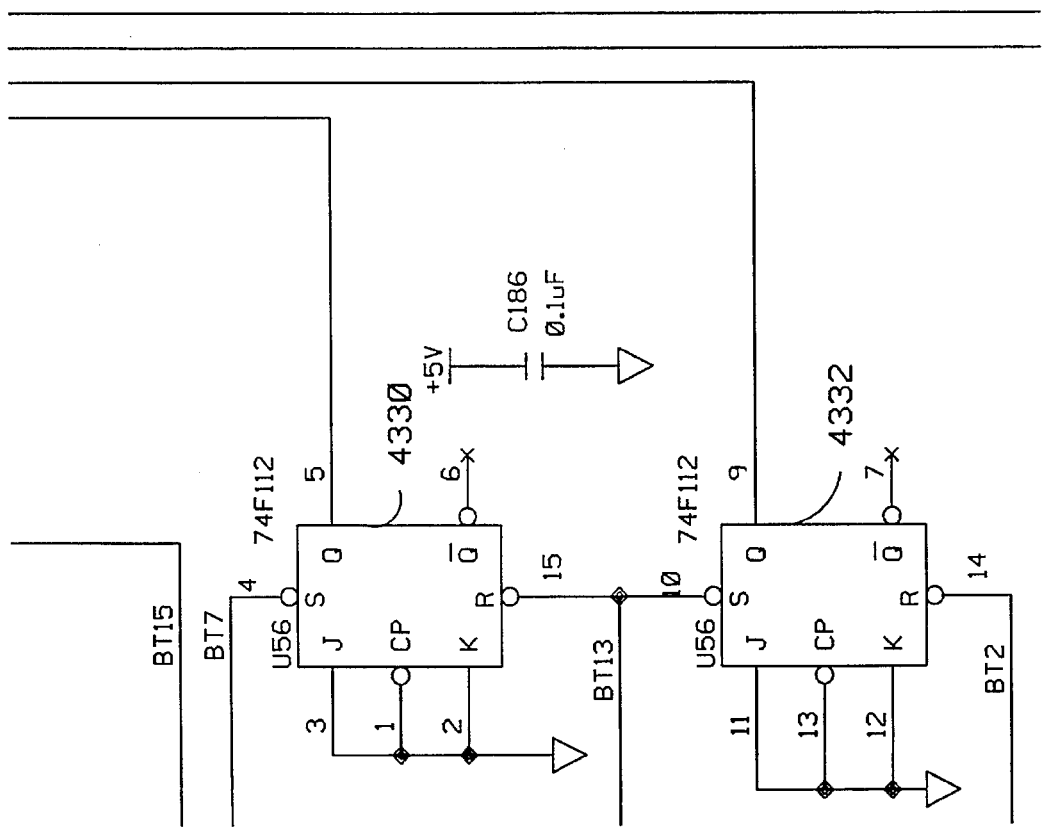
FIGURE 12E11

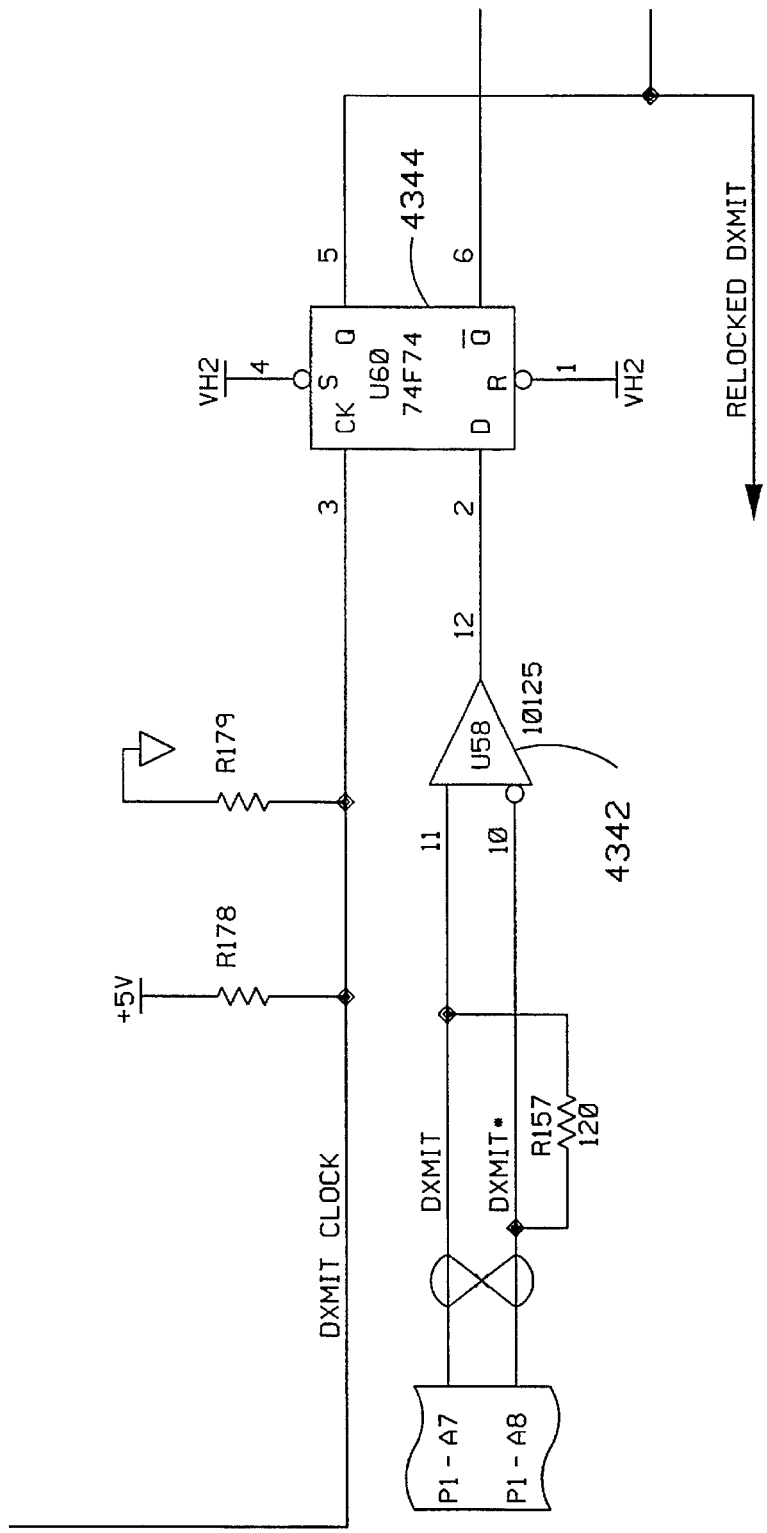
FIGURE 12E12

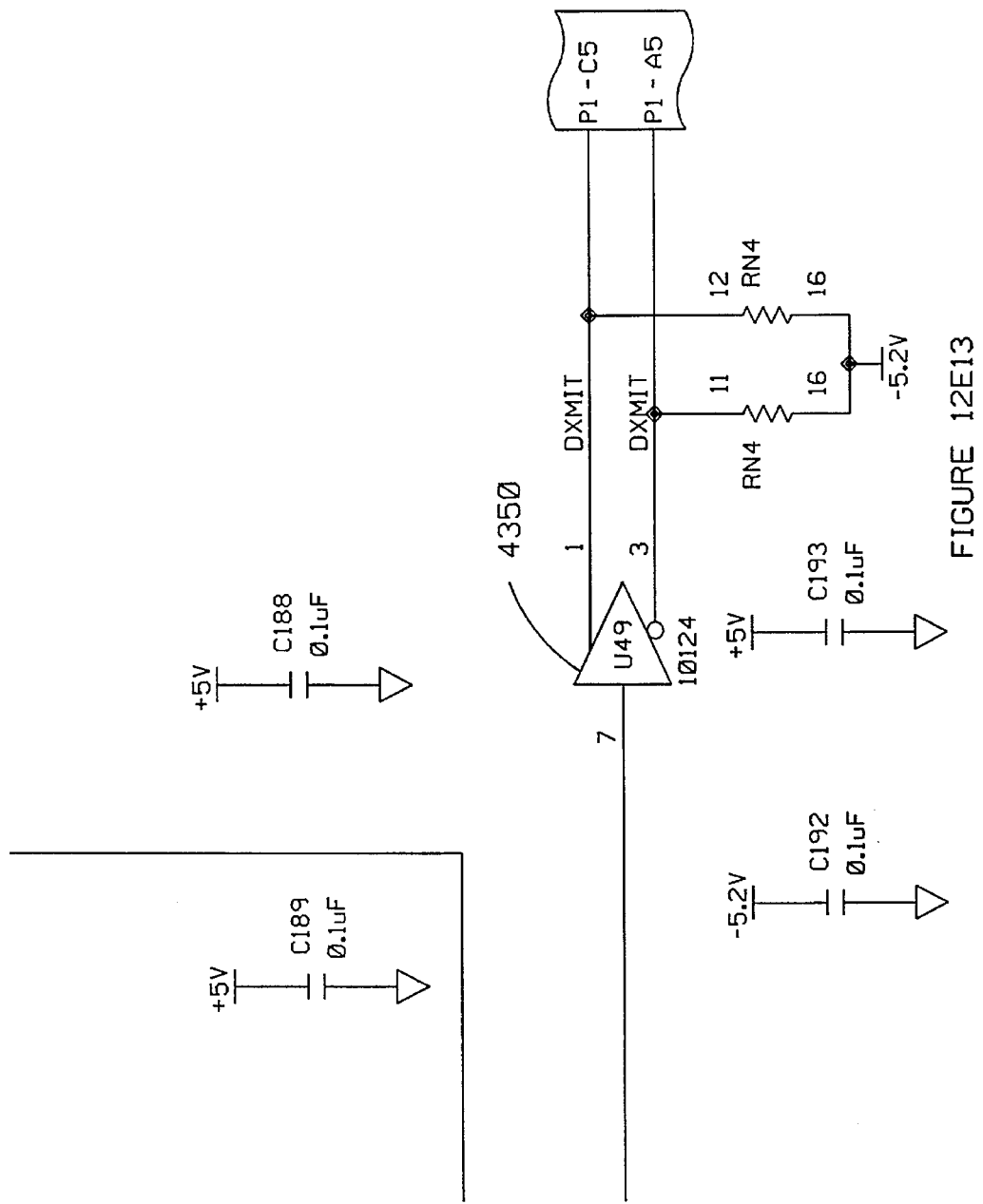
FIGURE 12E13

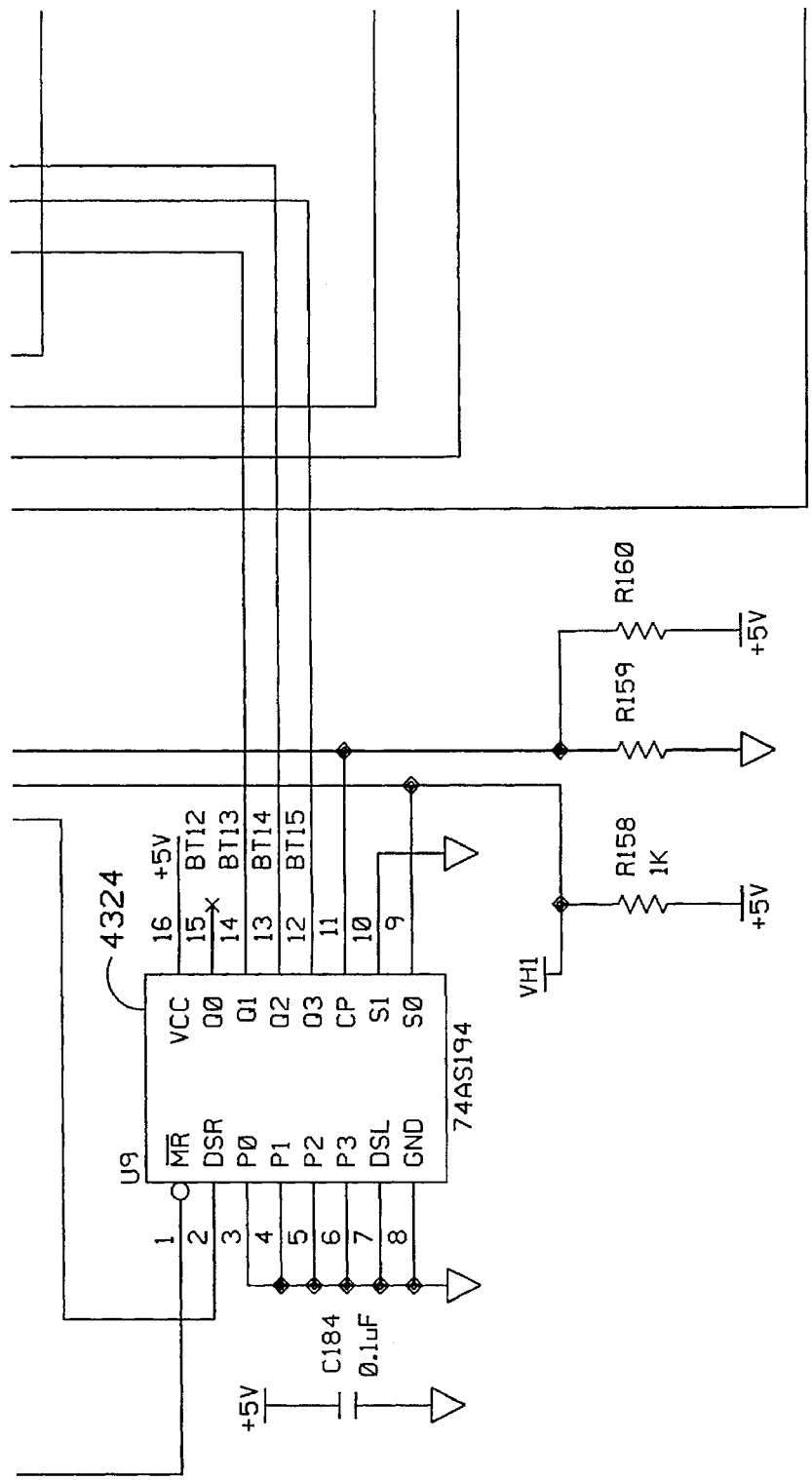
FIGURE 12E14

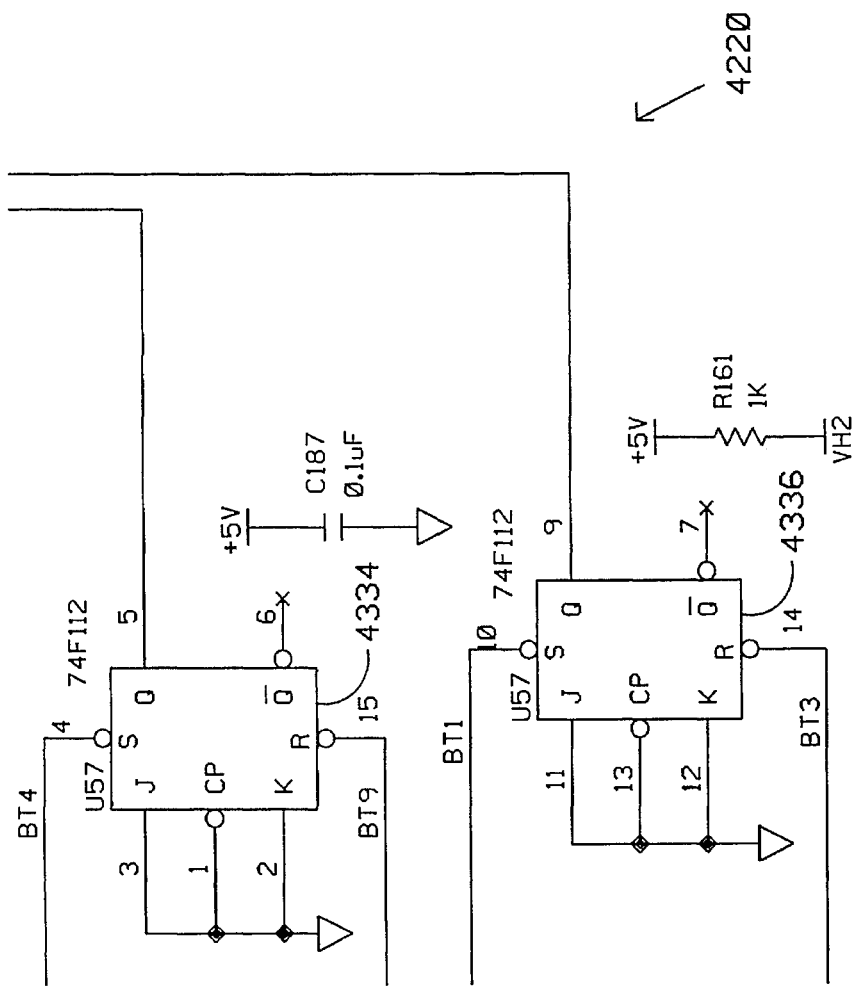
FIGURE 12E15

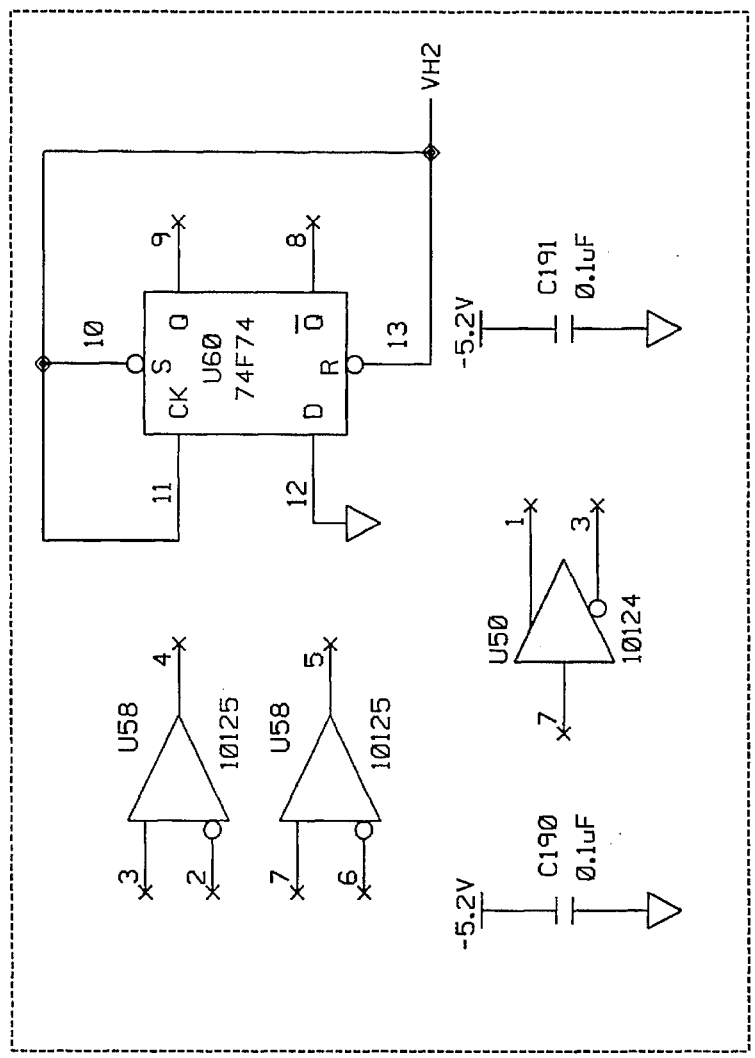
FIGURE 12E16

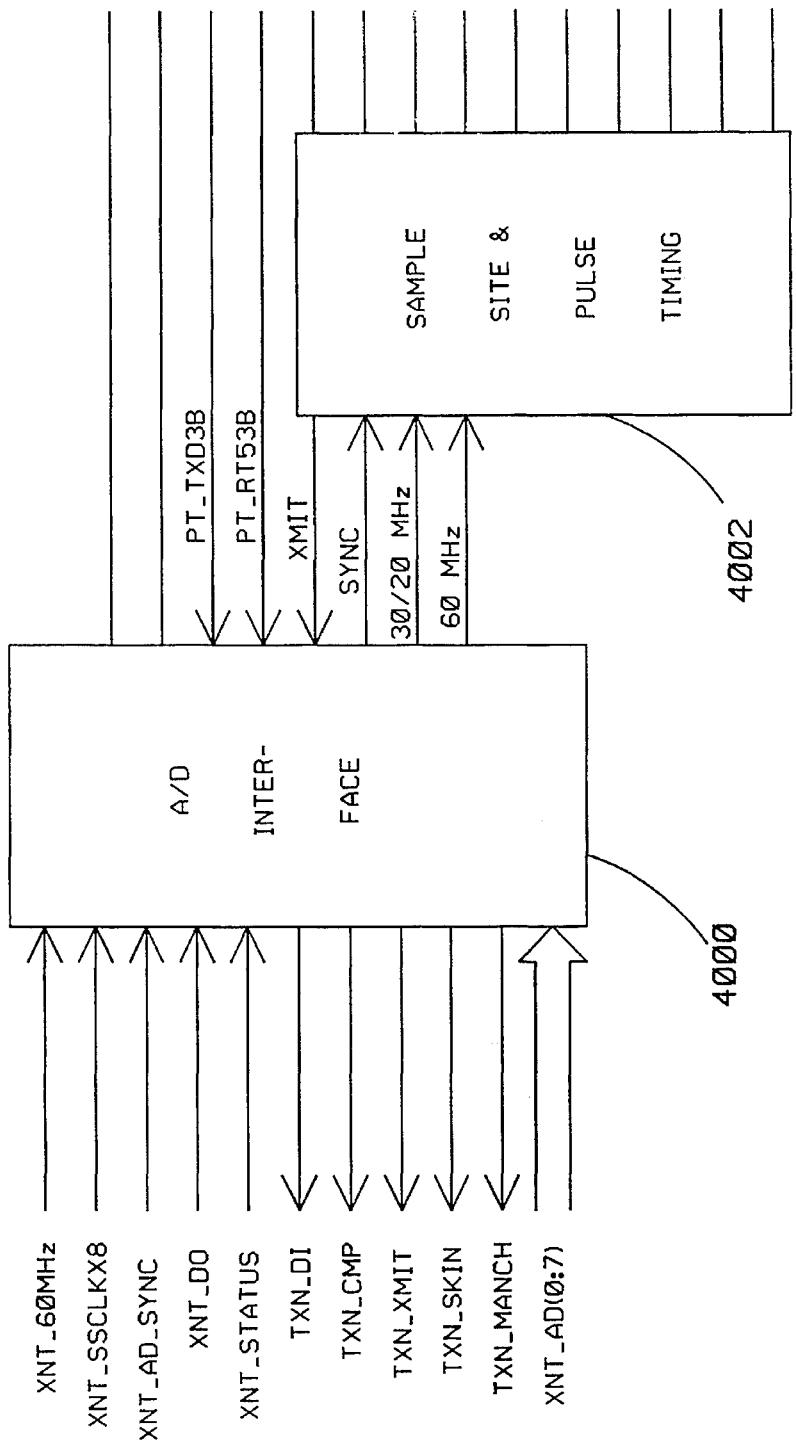
FIGURE 13A1

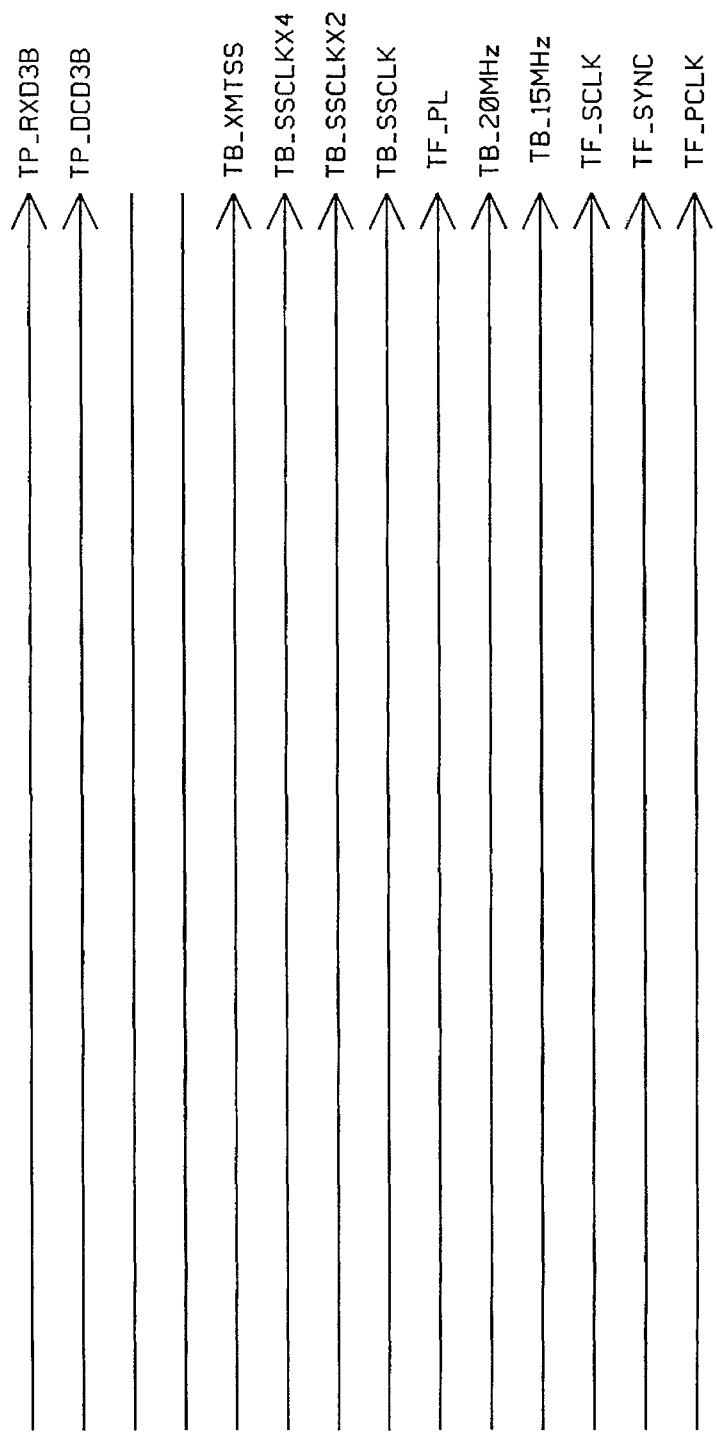
FIGURE 13A2

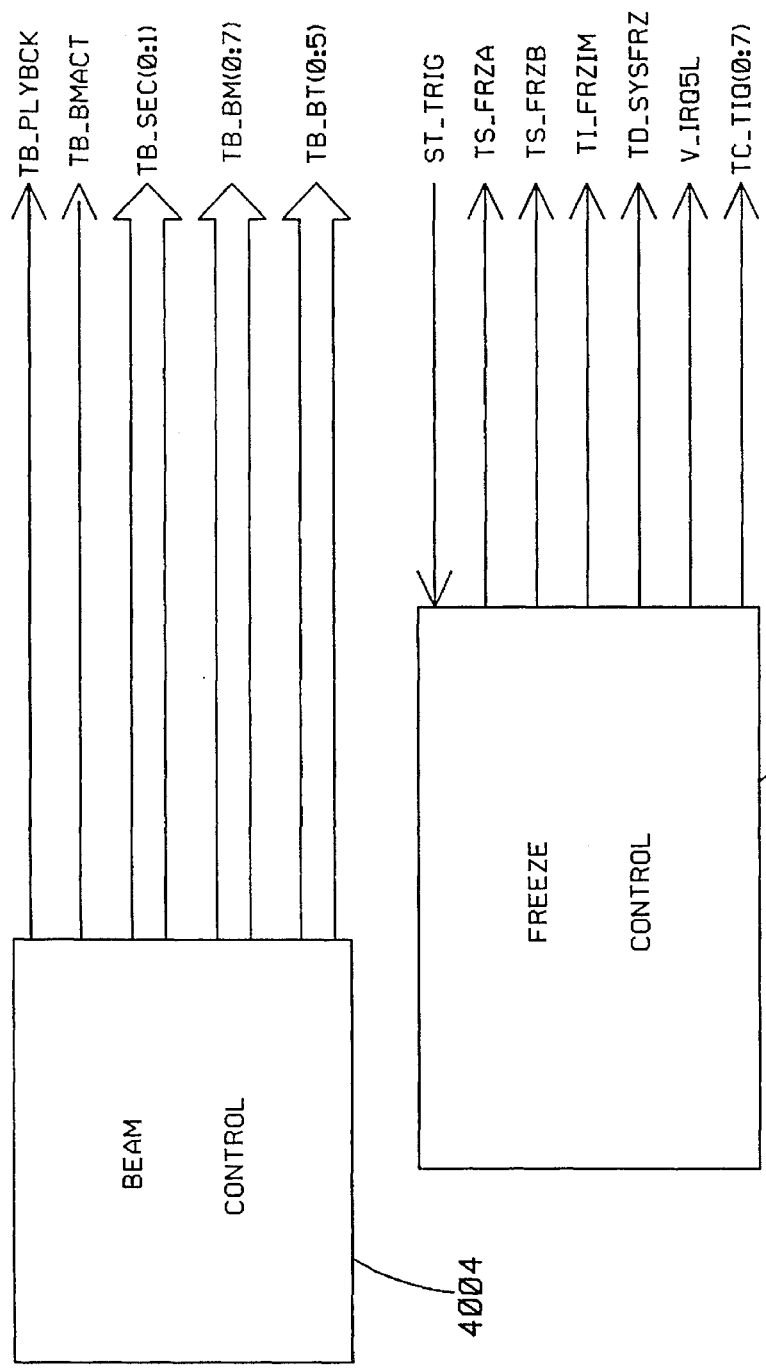
FIGURE 13A3

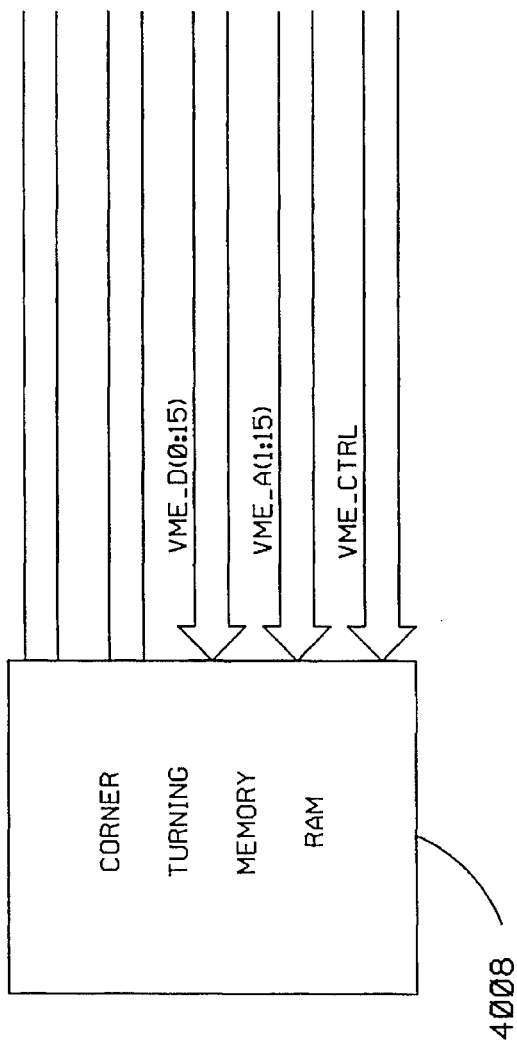
FIGURE 13A4

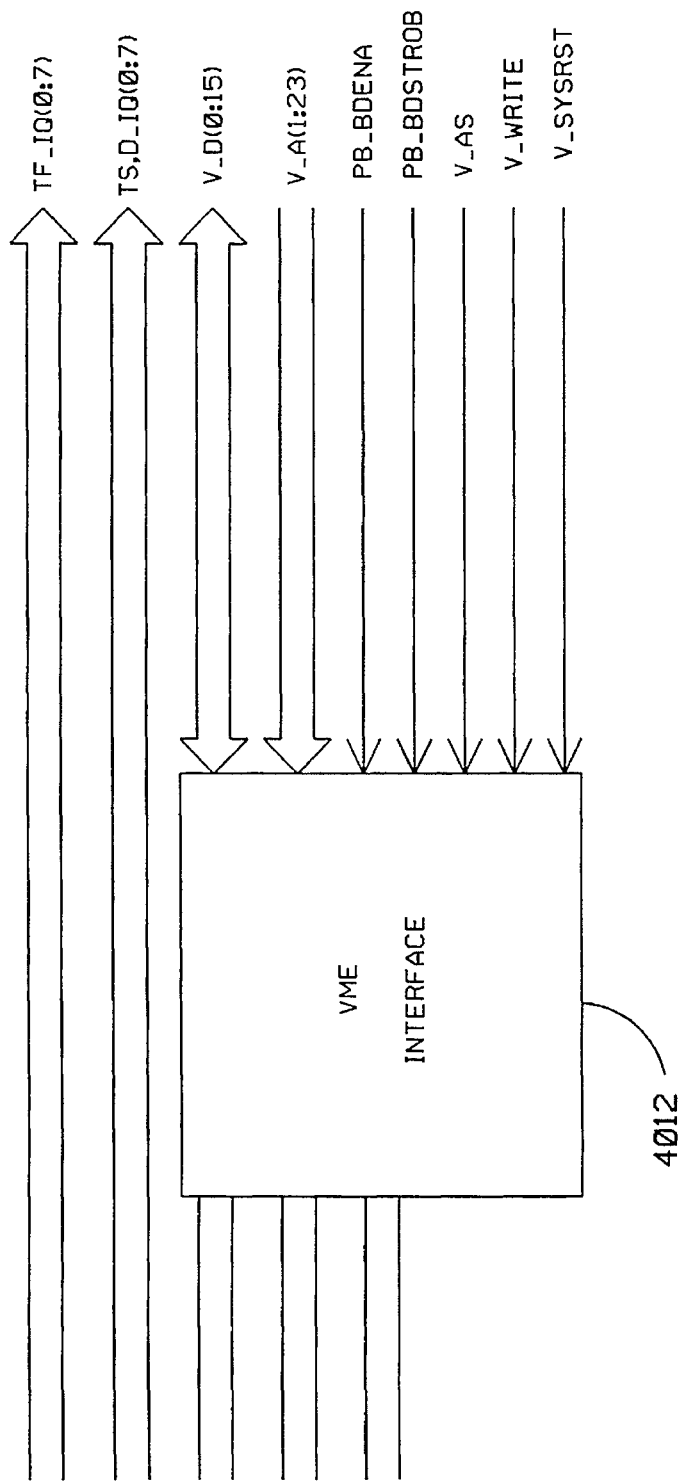
FIGURE 13A5

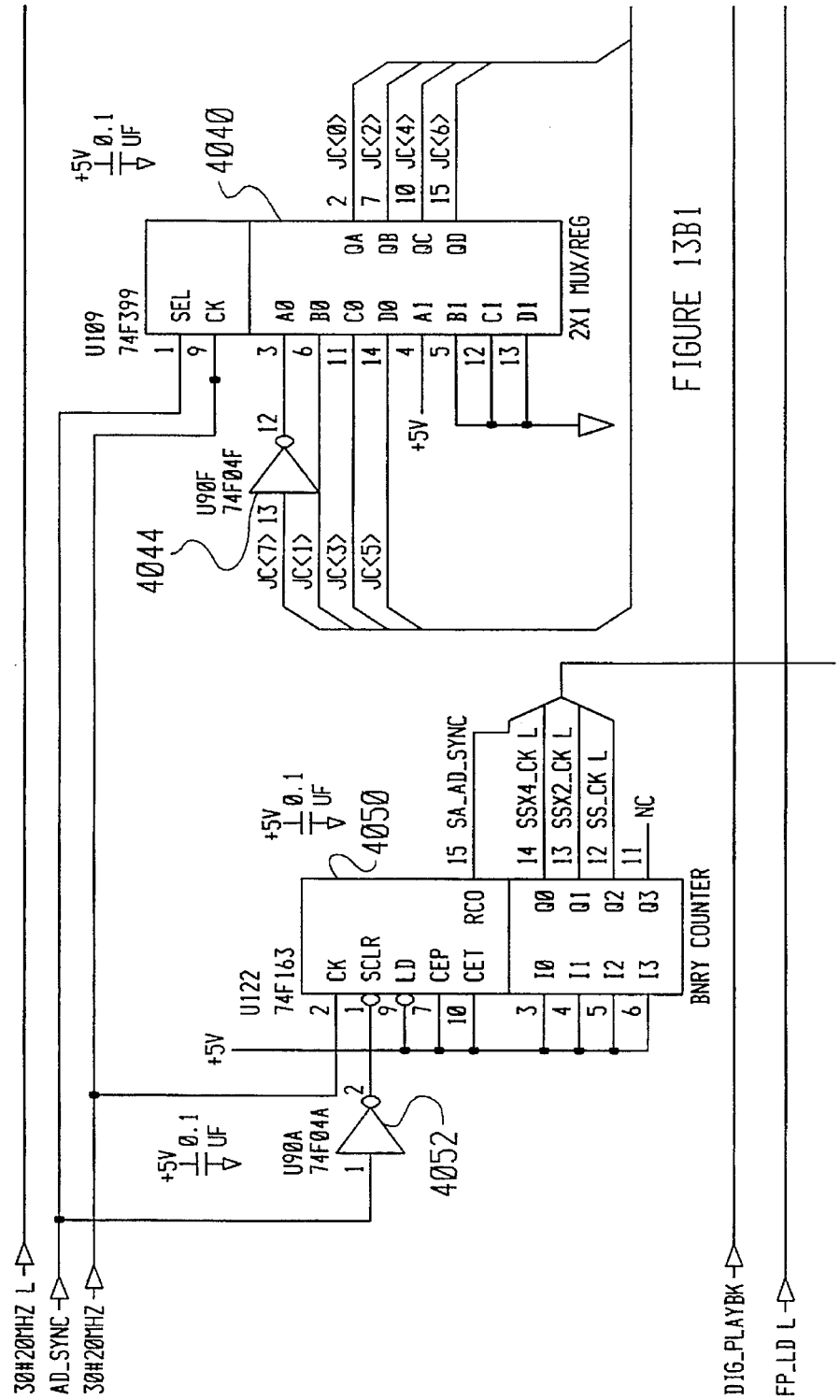
FIGURE 13B1

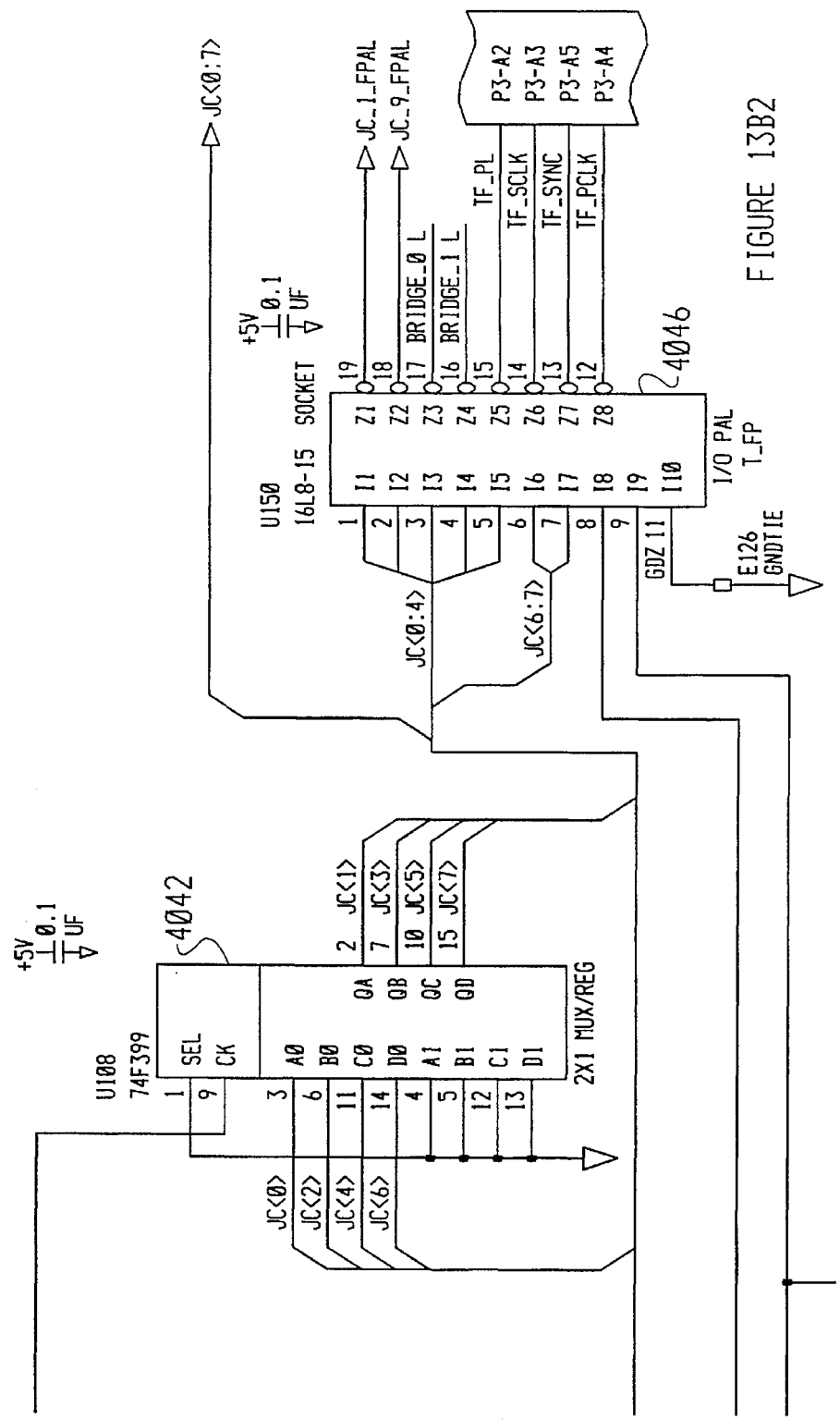
FIGURE 13B2

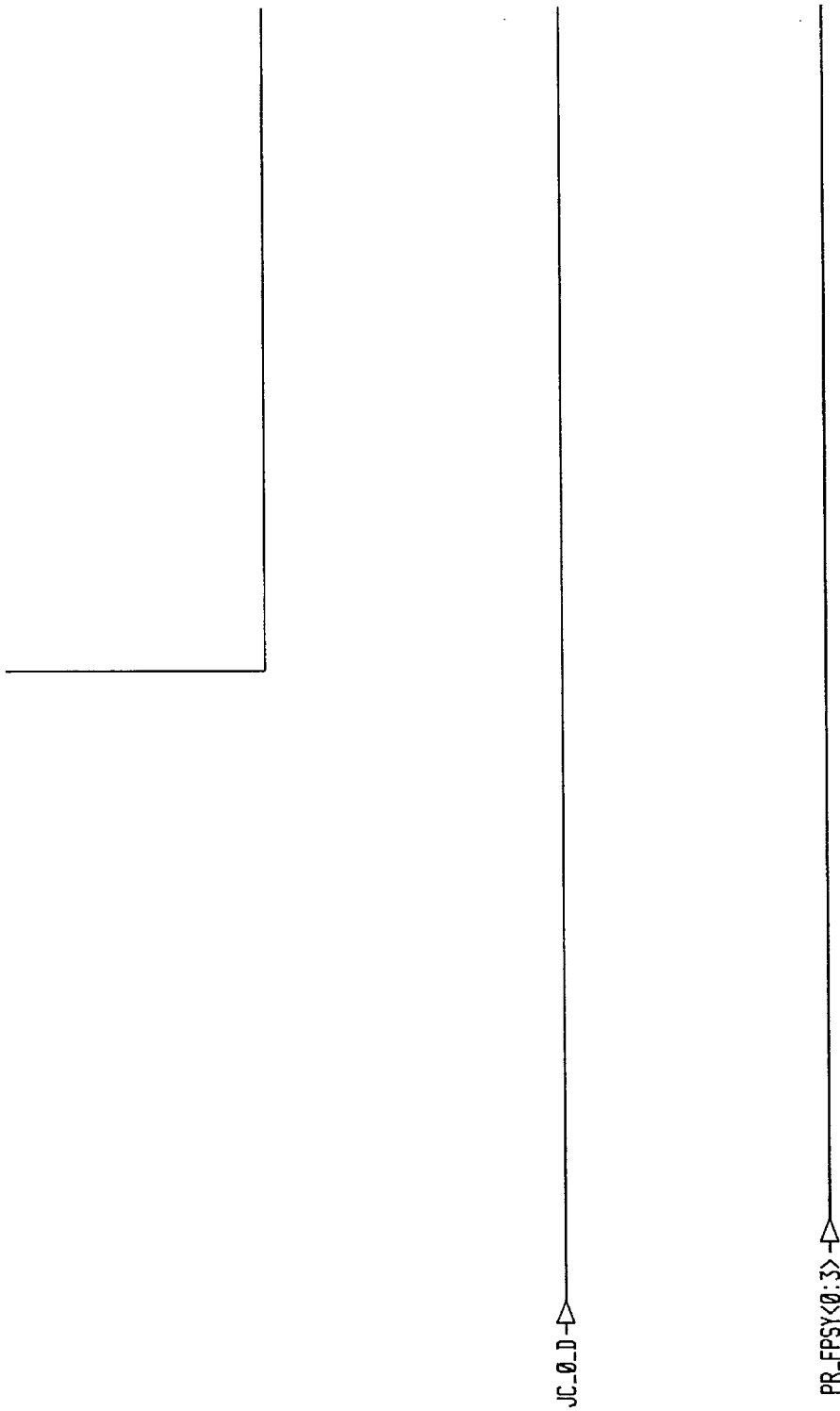
FIGURE 13B3

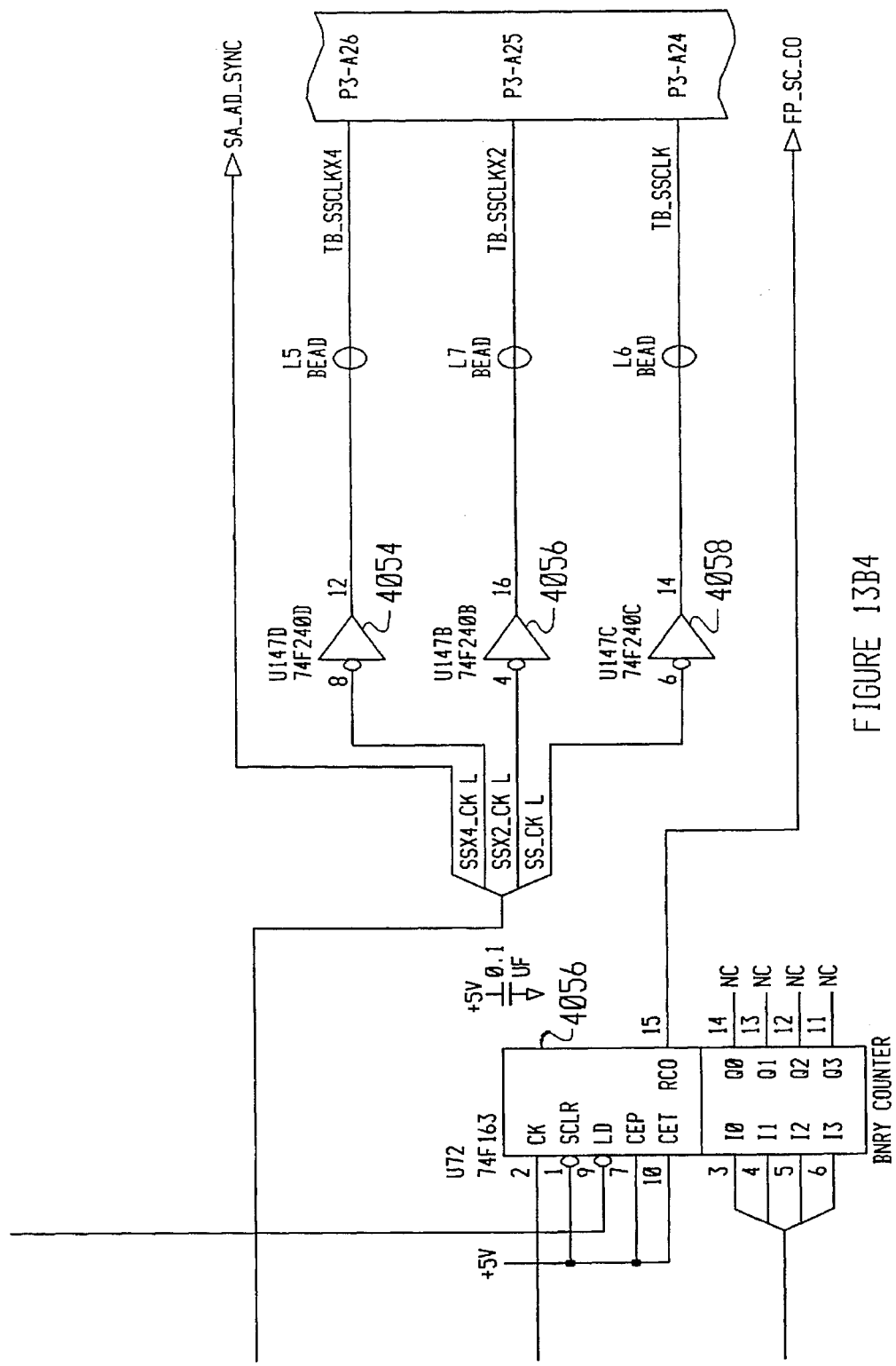
FIGURE 13B4

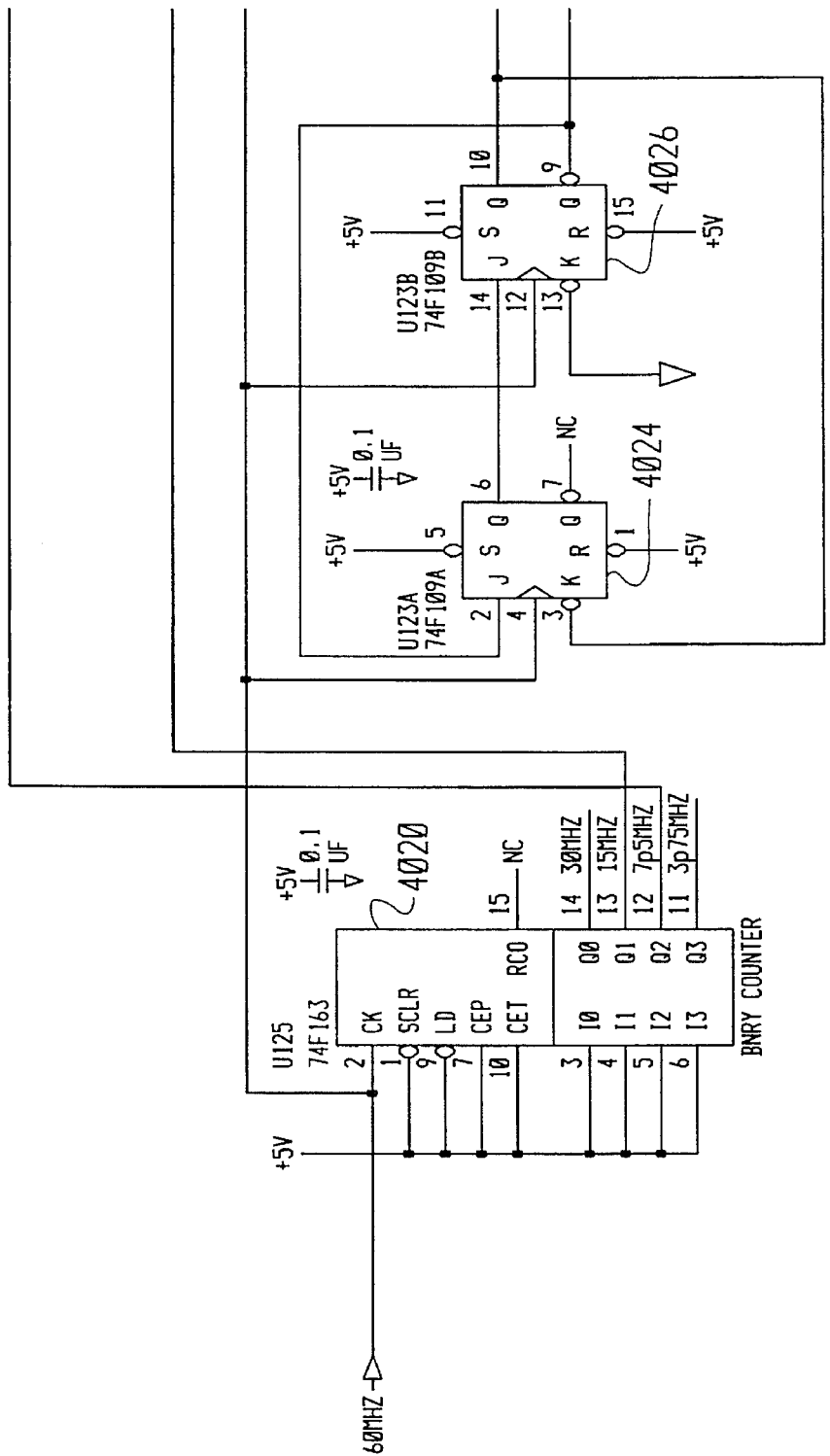
FIGURE 13B5

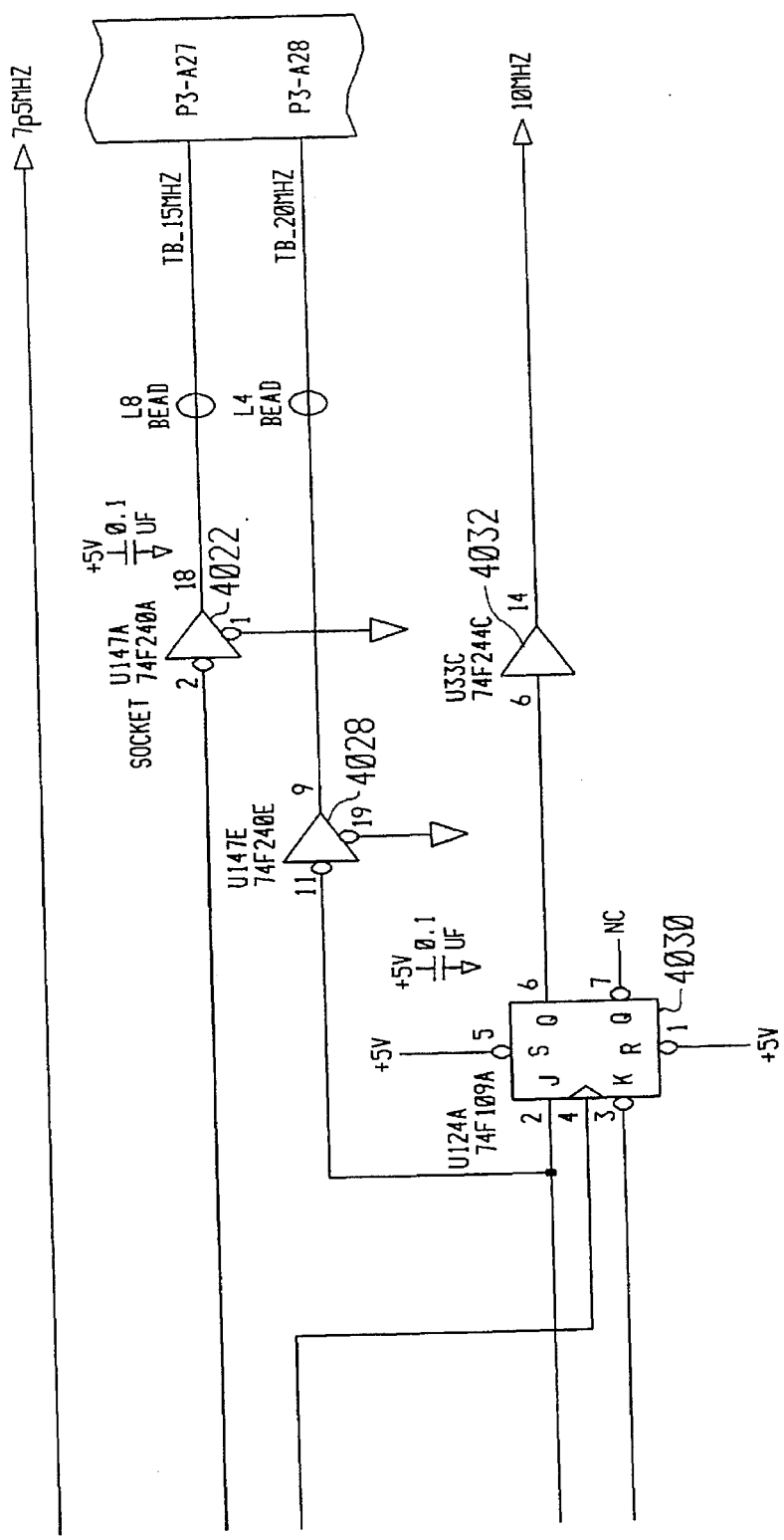
FIGURE 13B6

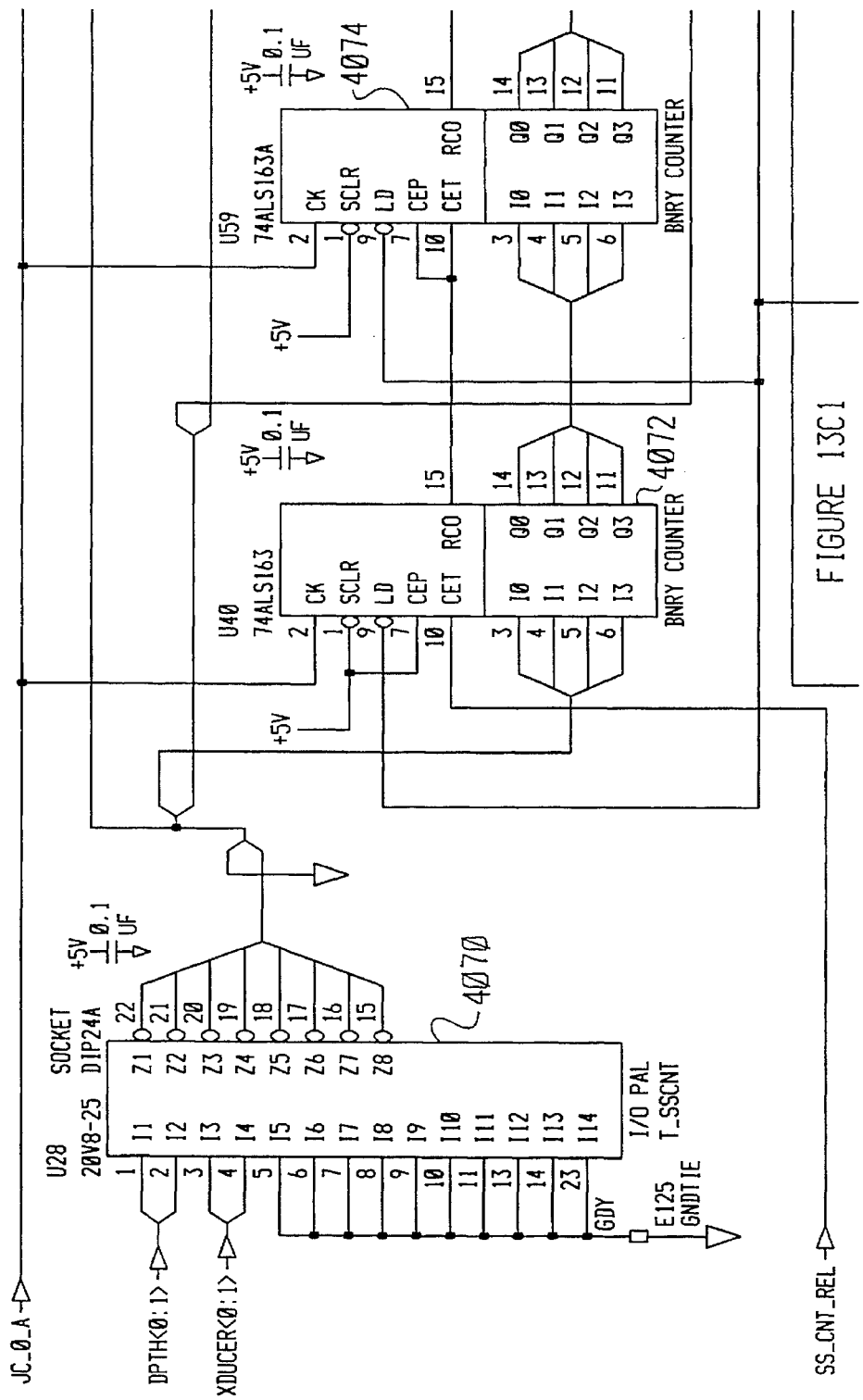
FIGURE 13C1

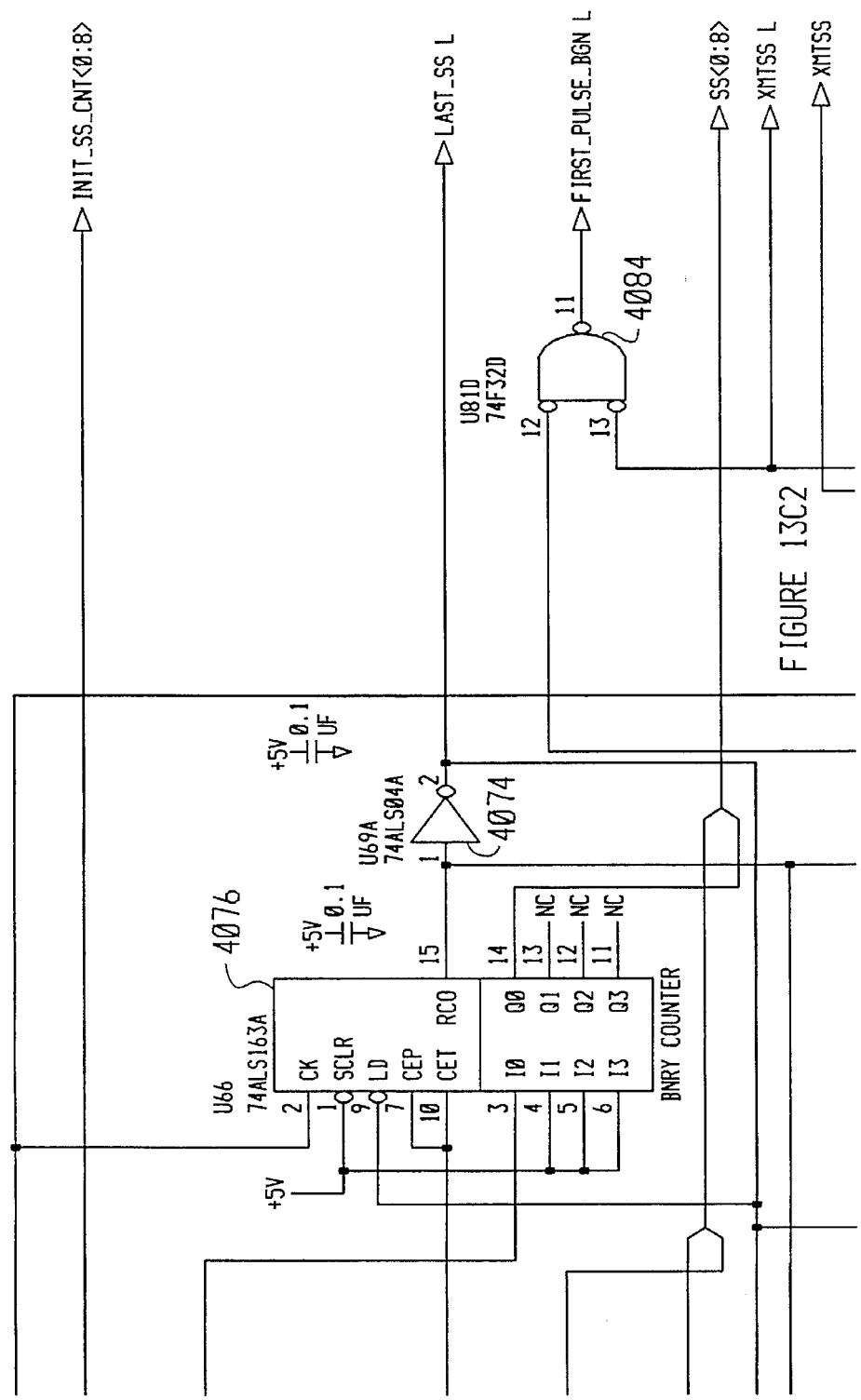
FIGURE 13C2

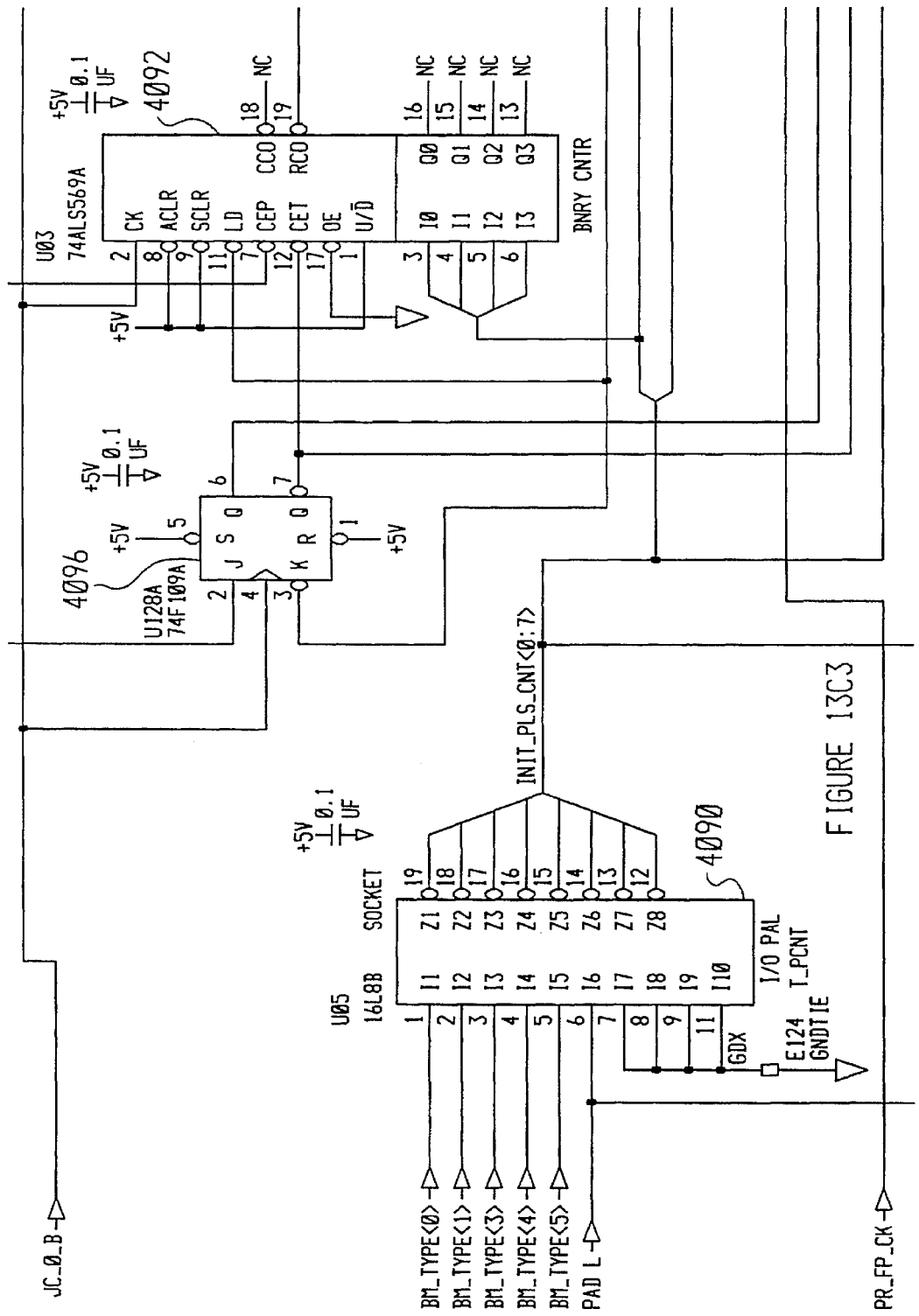
FIGURE 13C3

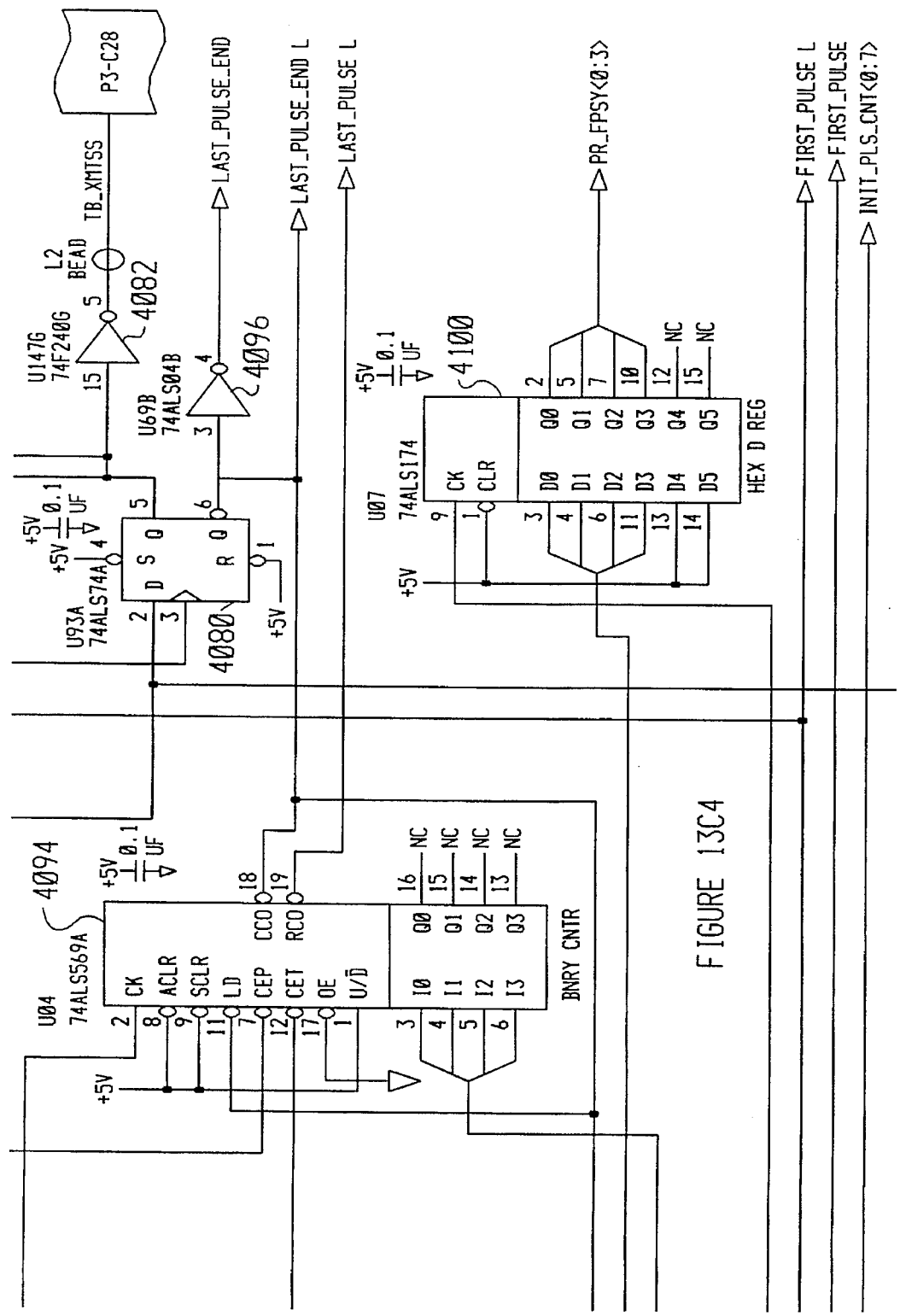
FIGURE 13C4

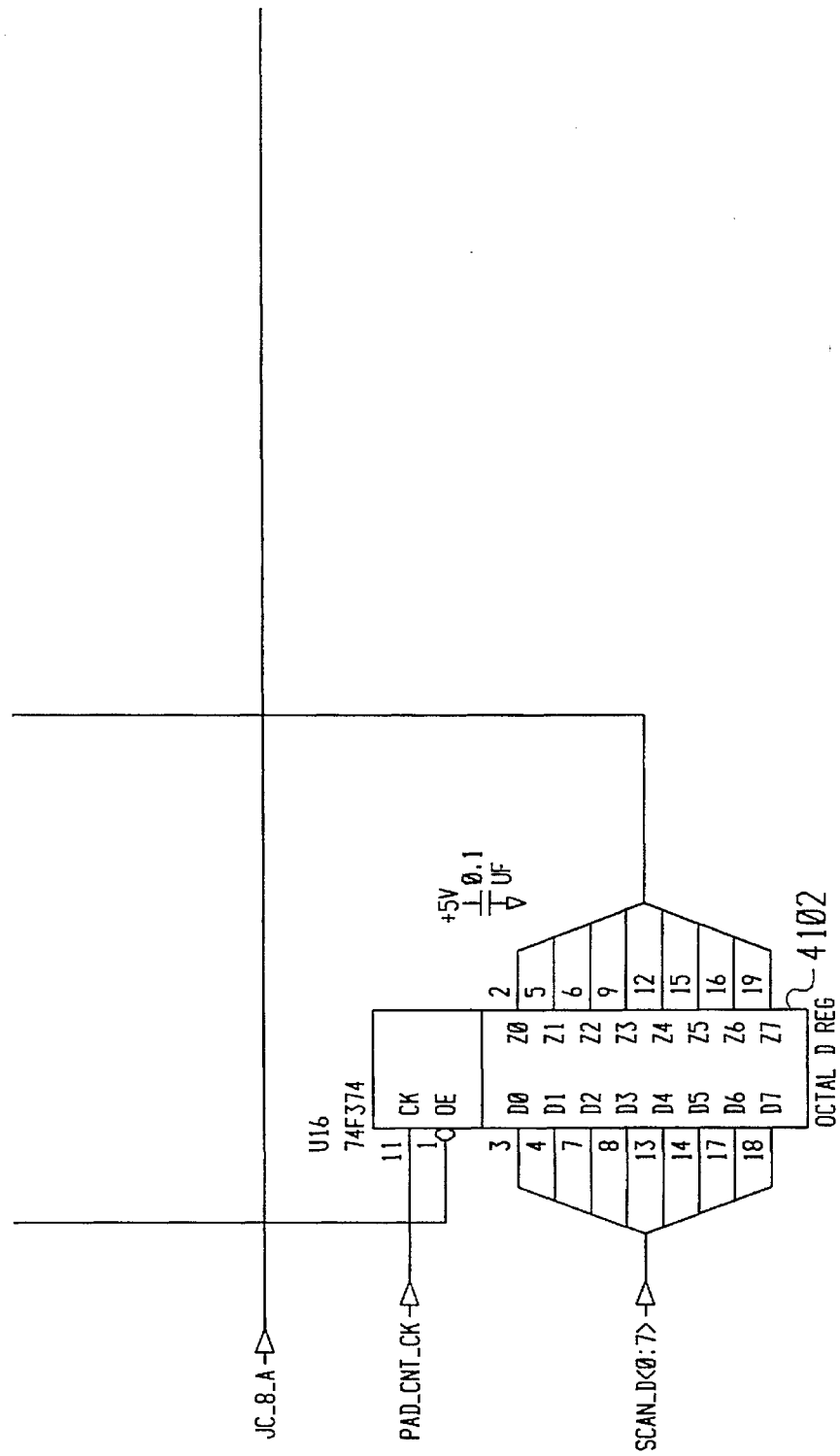
FIGURE 13C5

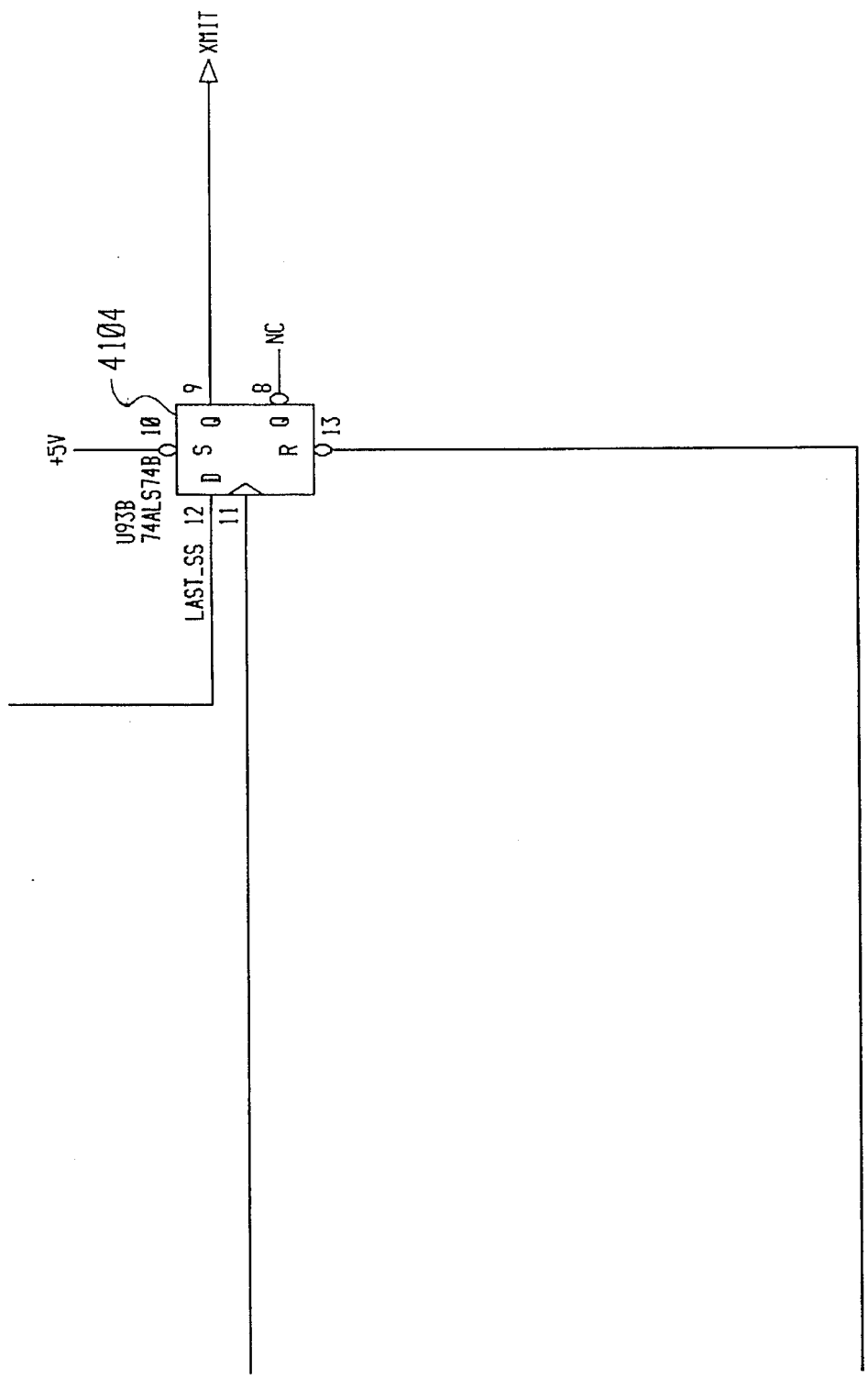
FIGURE 13C6

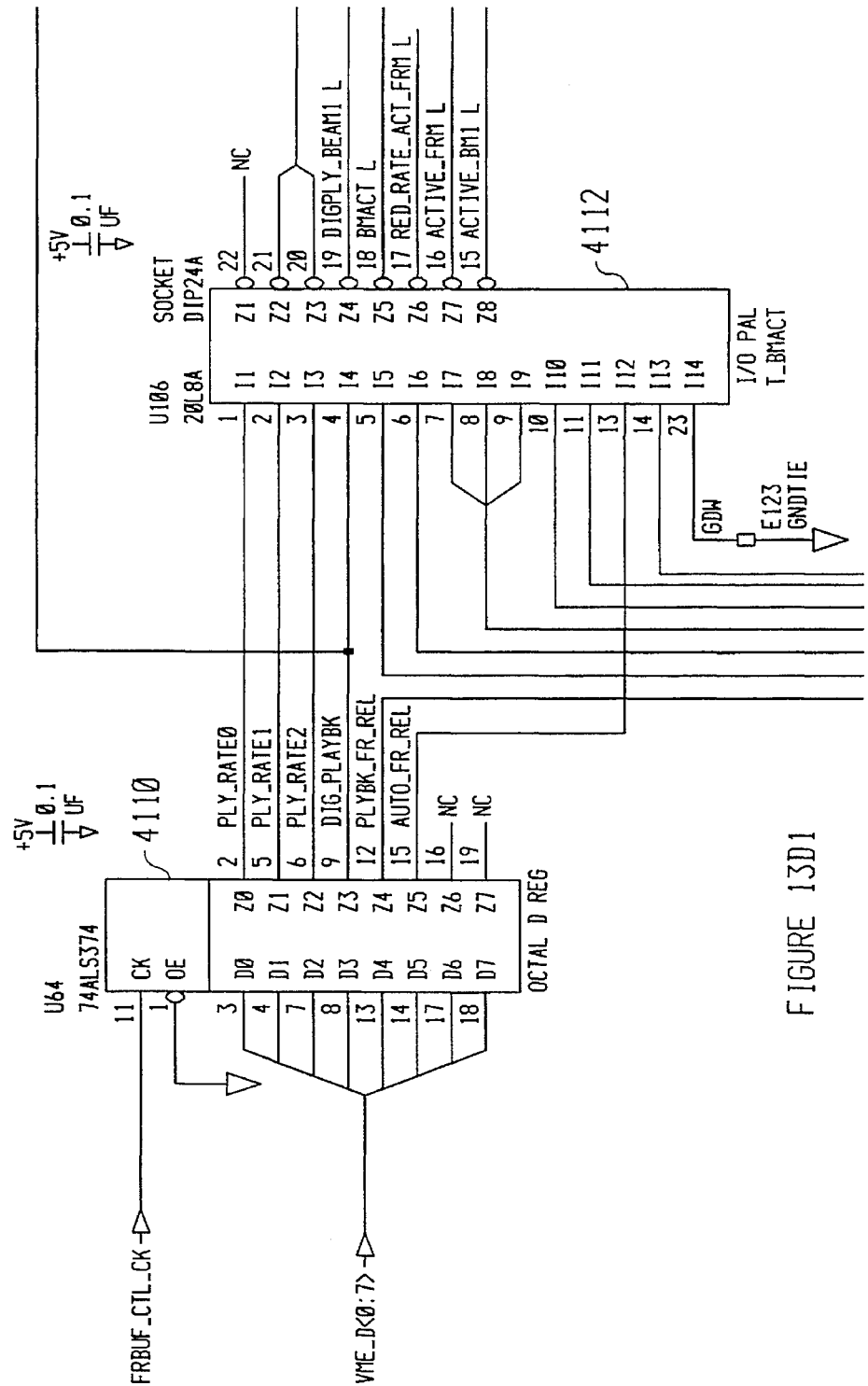
FIGURE 13D1

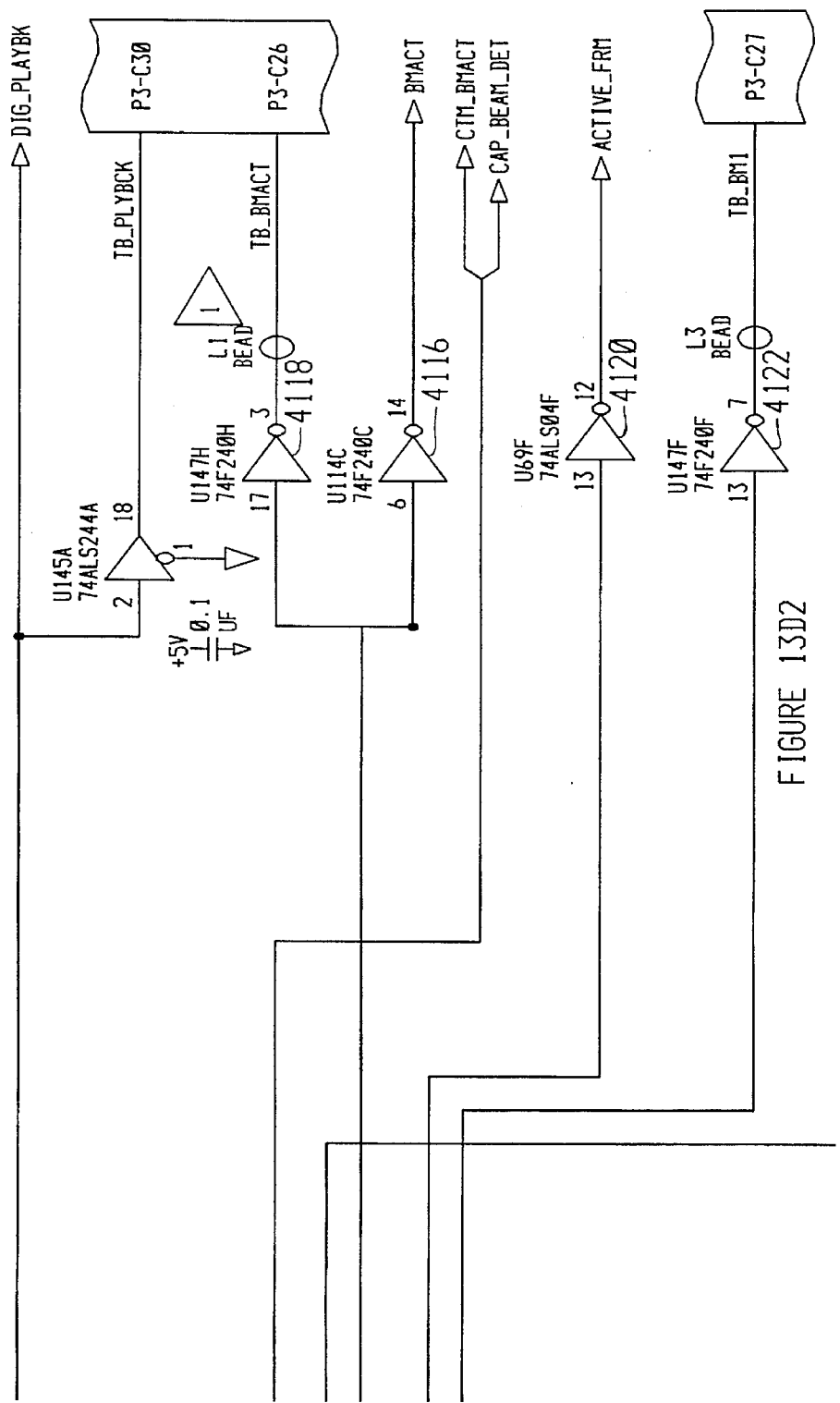
FIGURE 13D2

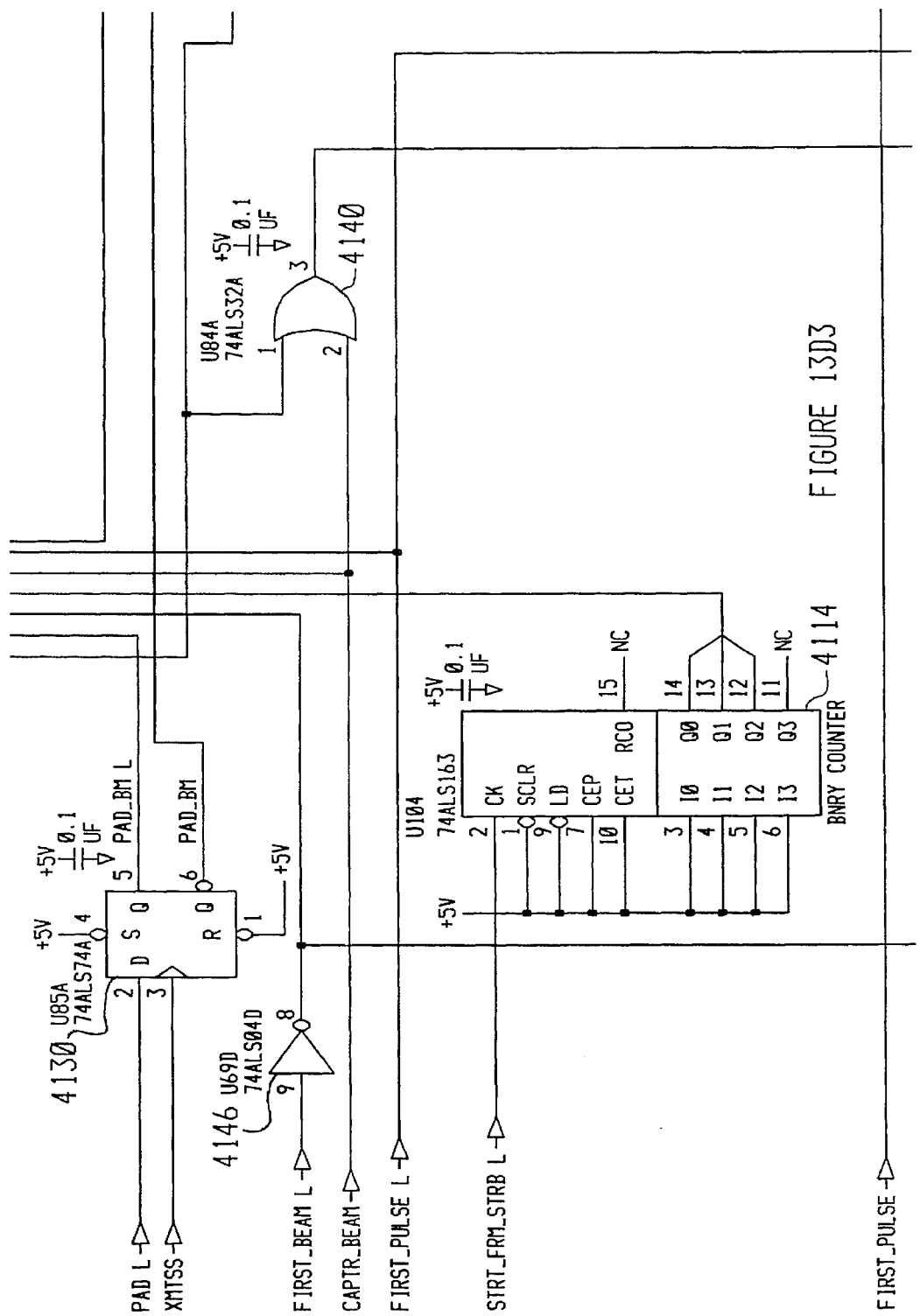
FIGURE 13D3

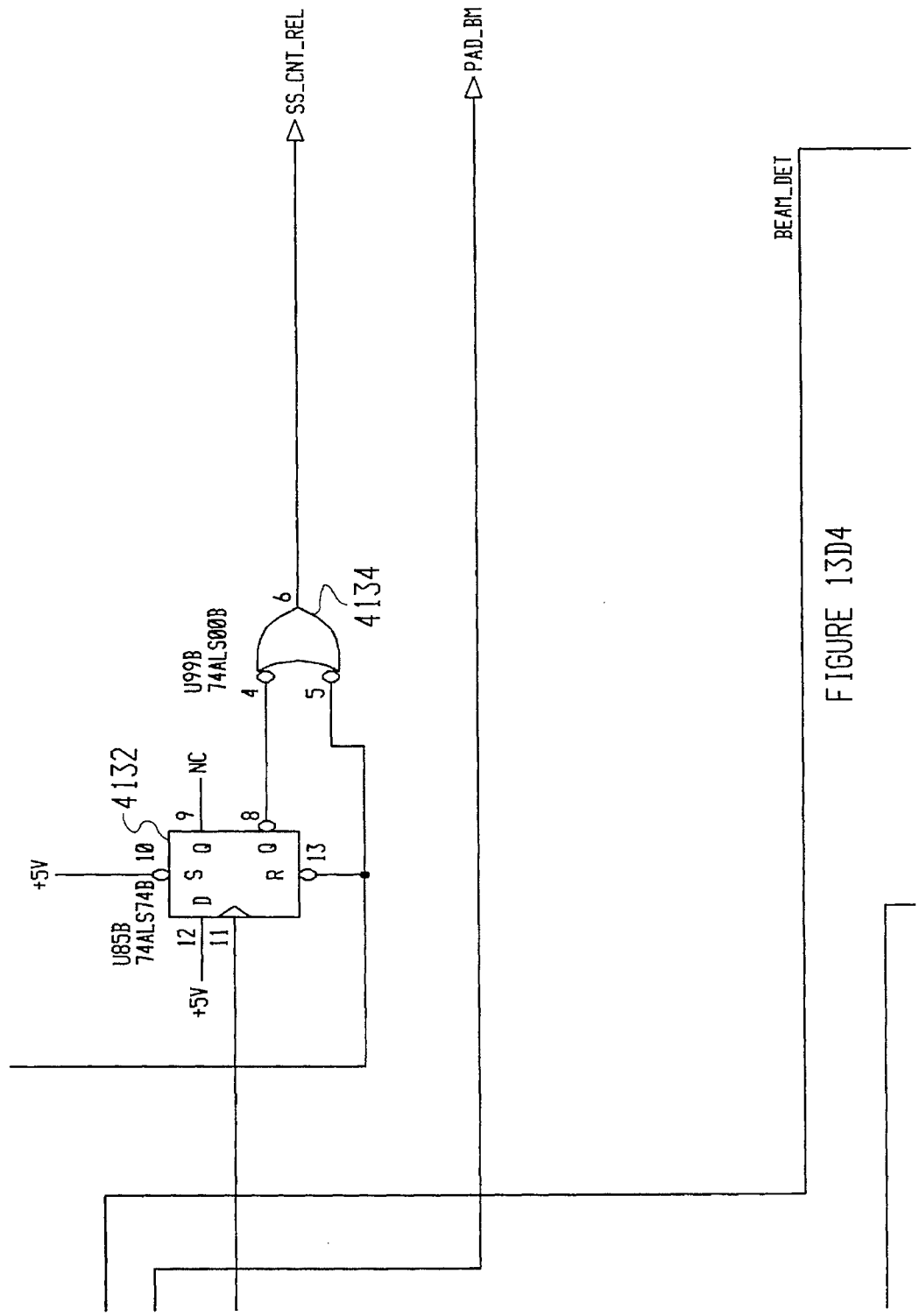
FIGURE 13D4

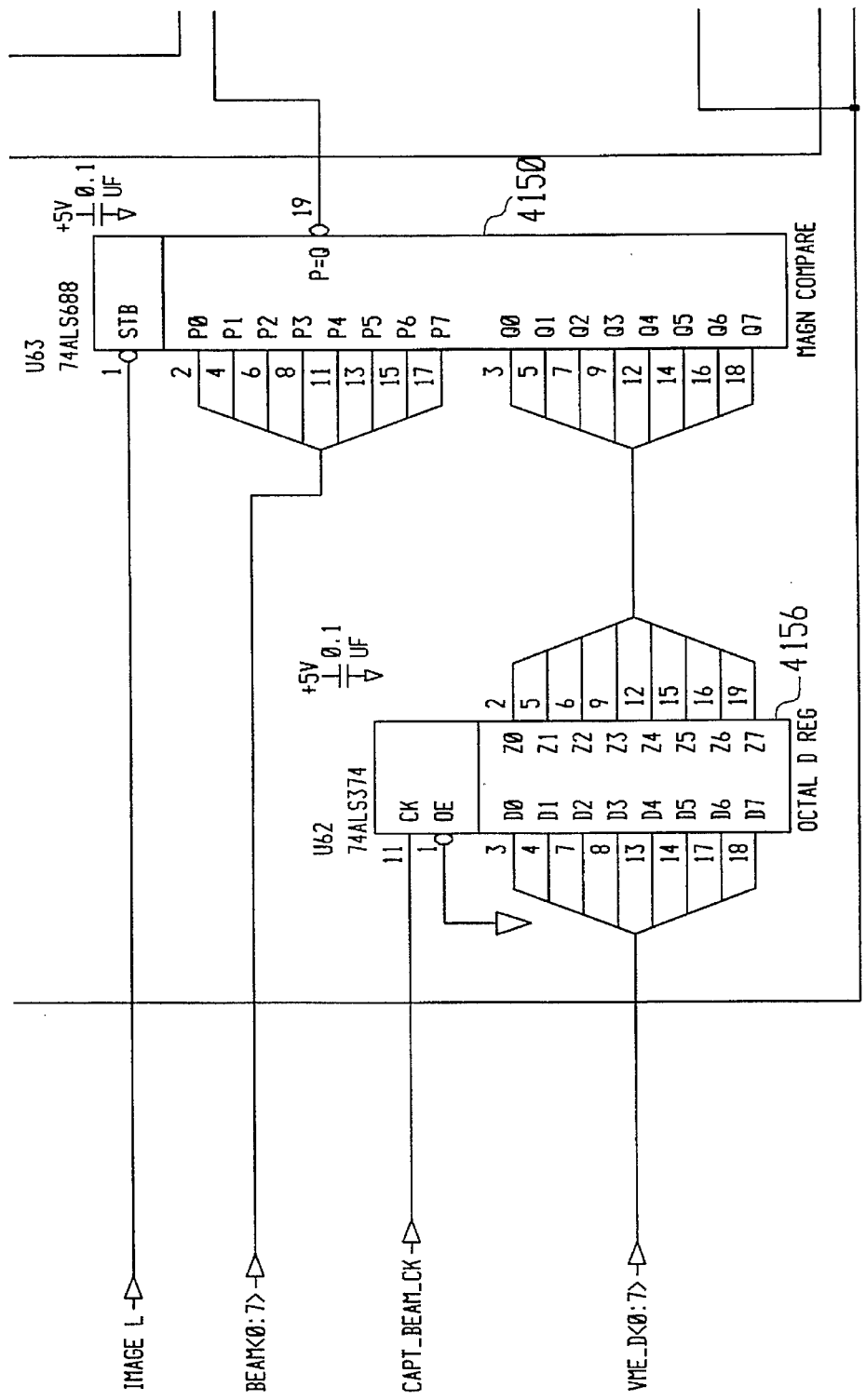
FIGURE 13D5

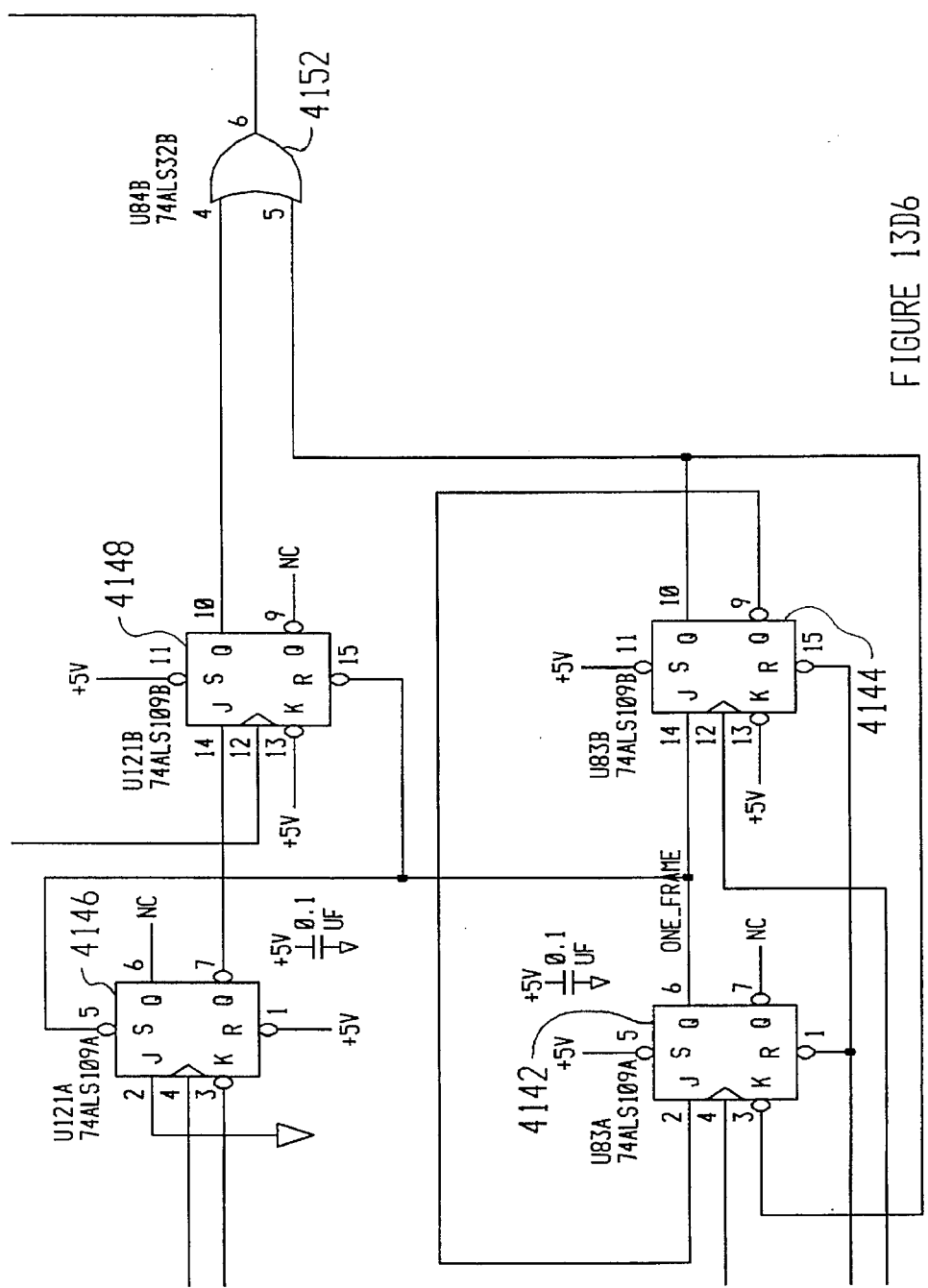
FIGURE 13D6

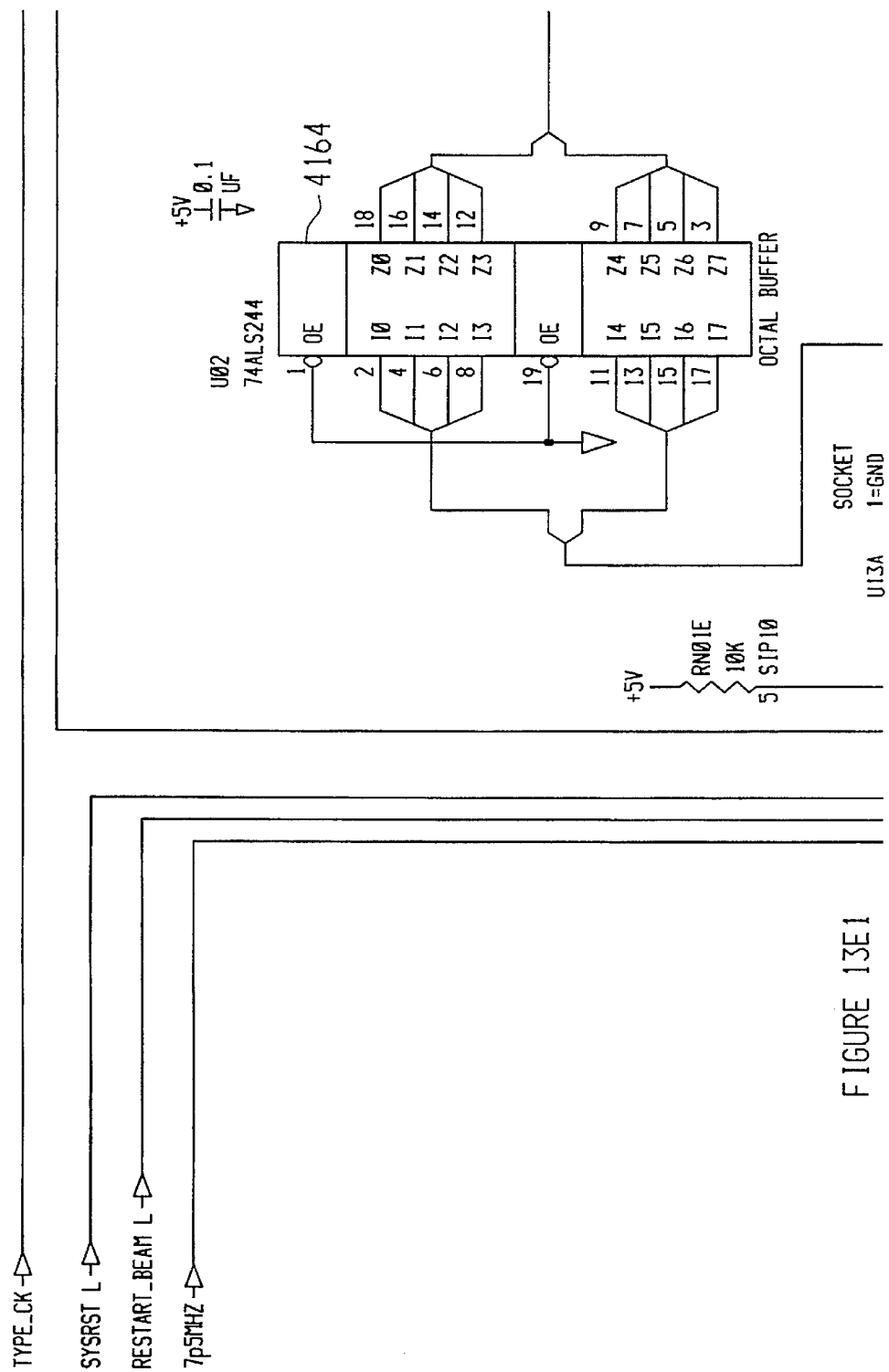
FIGURE 13E1

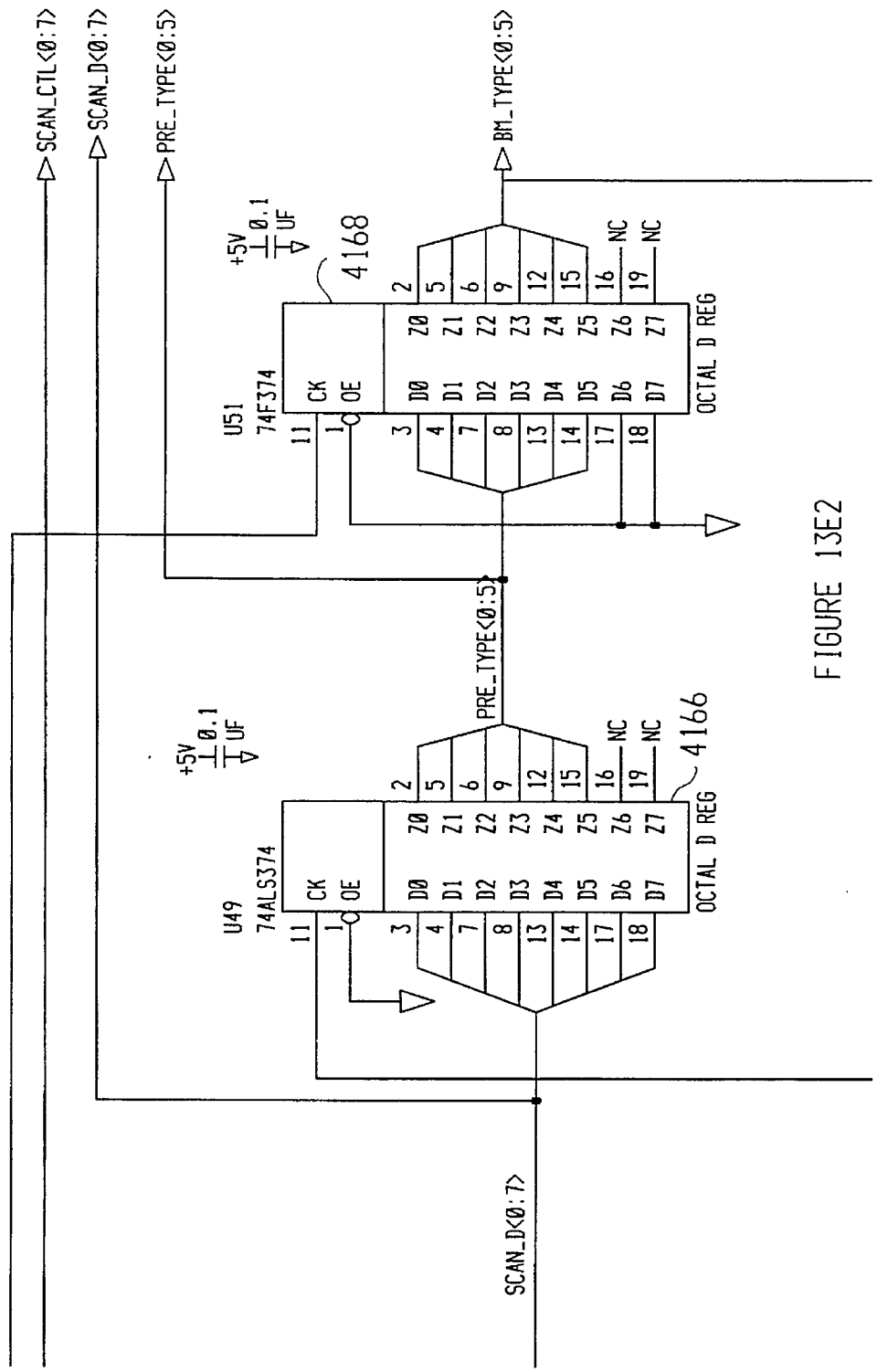
FIGURE 13E2

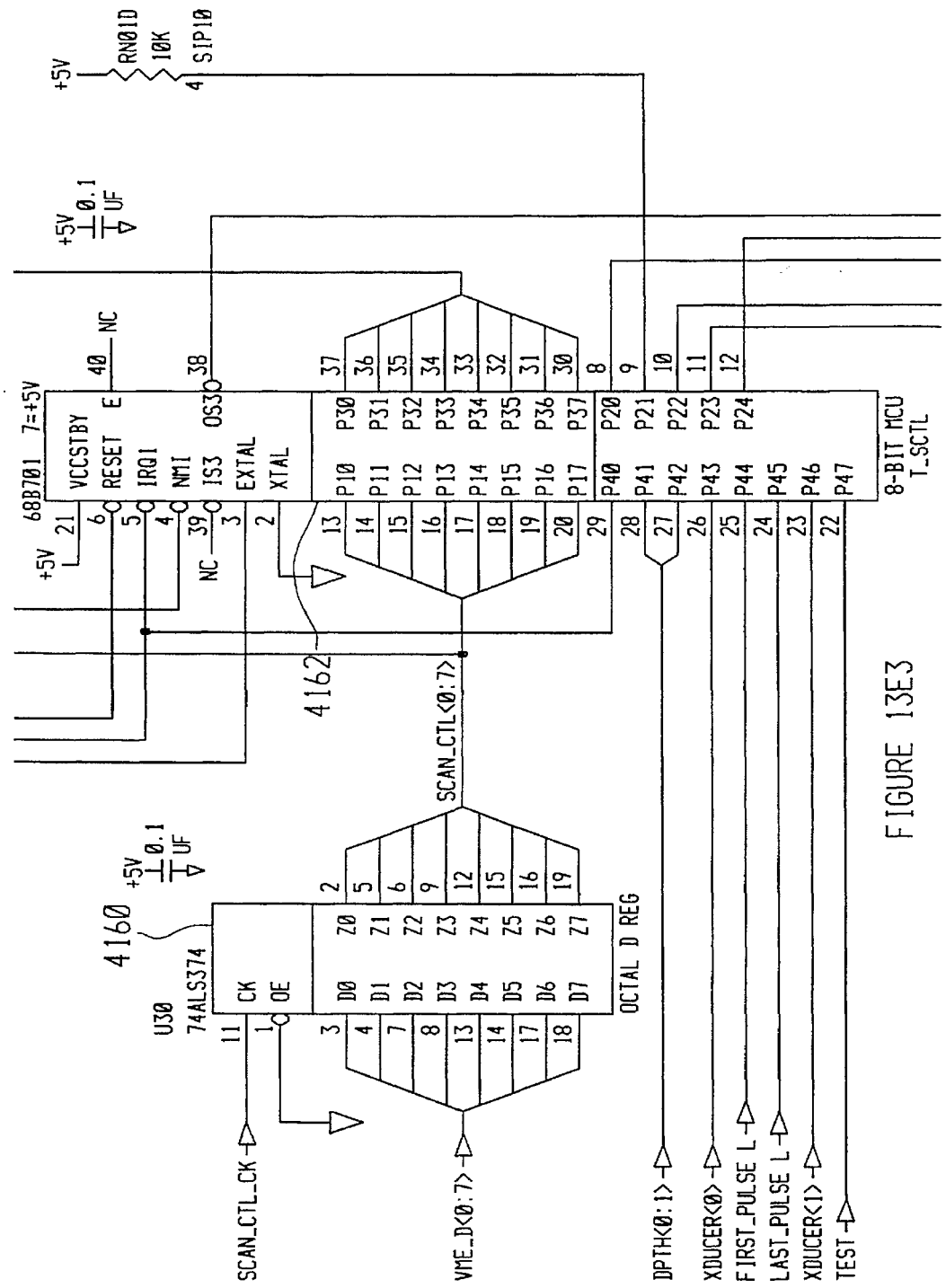
FIGURE 13E3

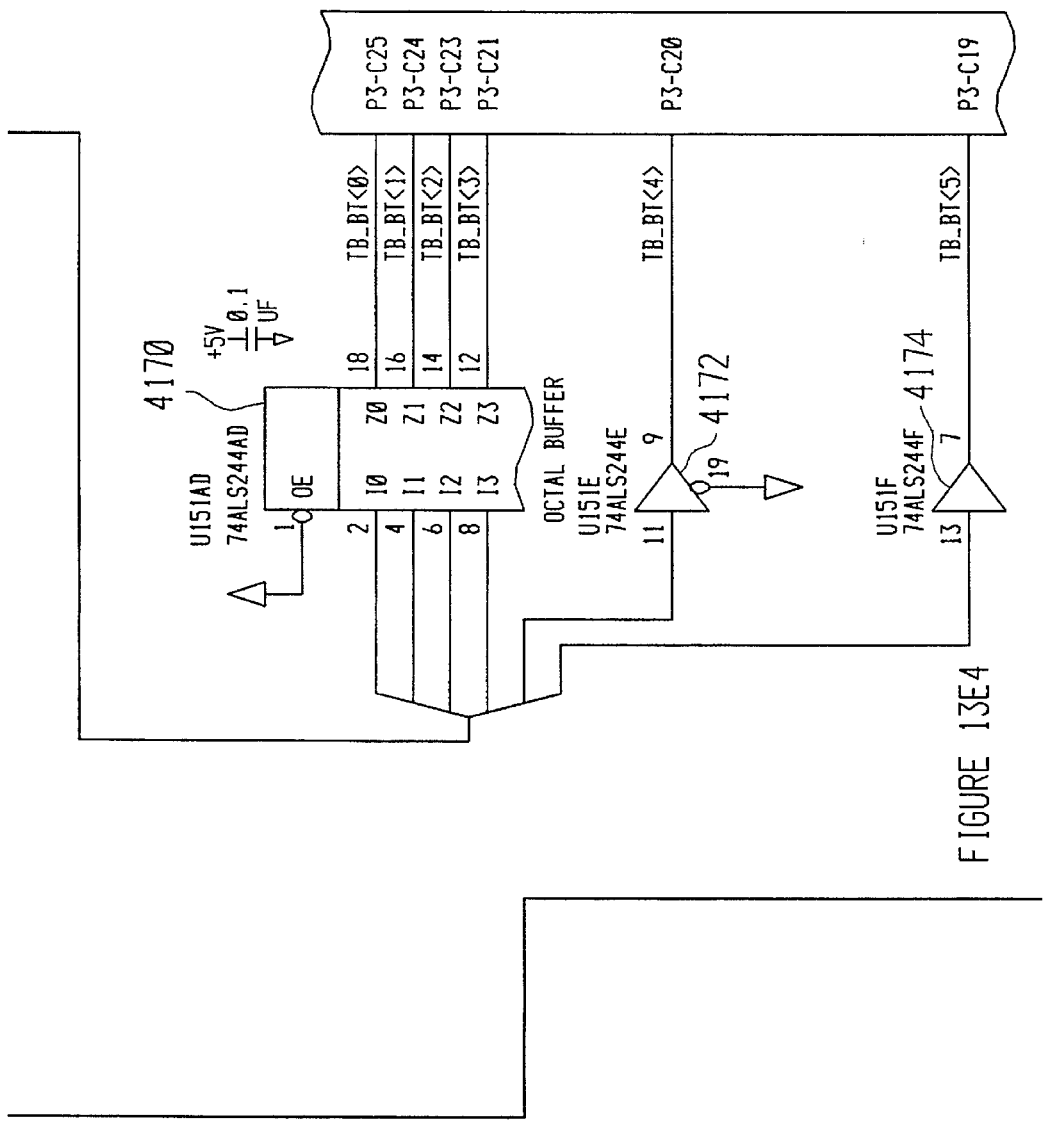
FIGURE 13E4

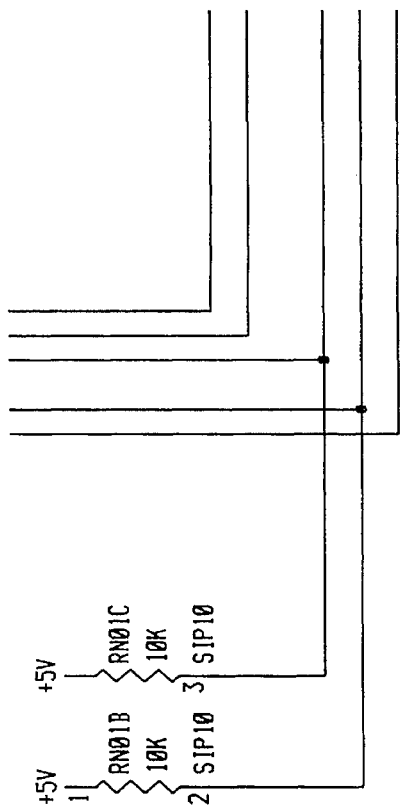
FIGURE 13E5

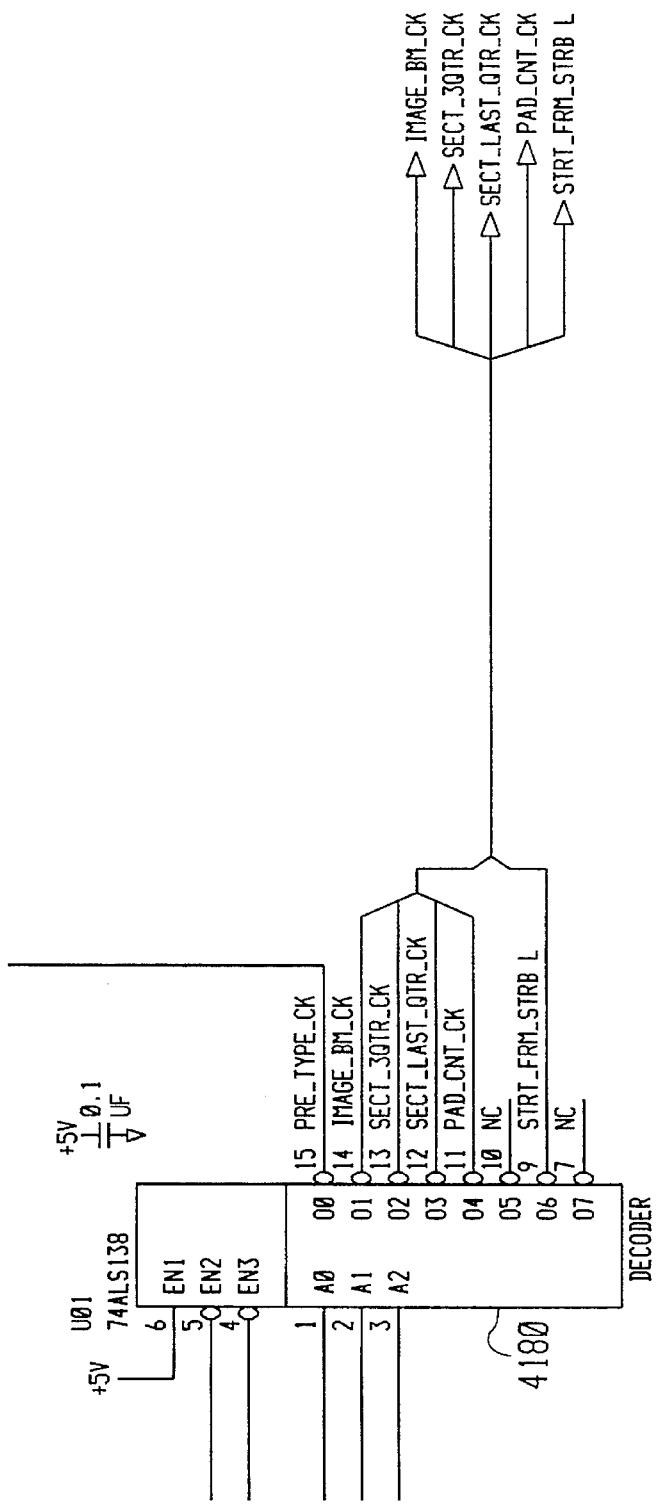
FIGURE 13E6

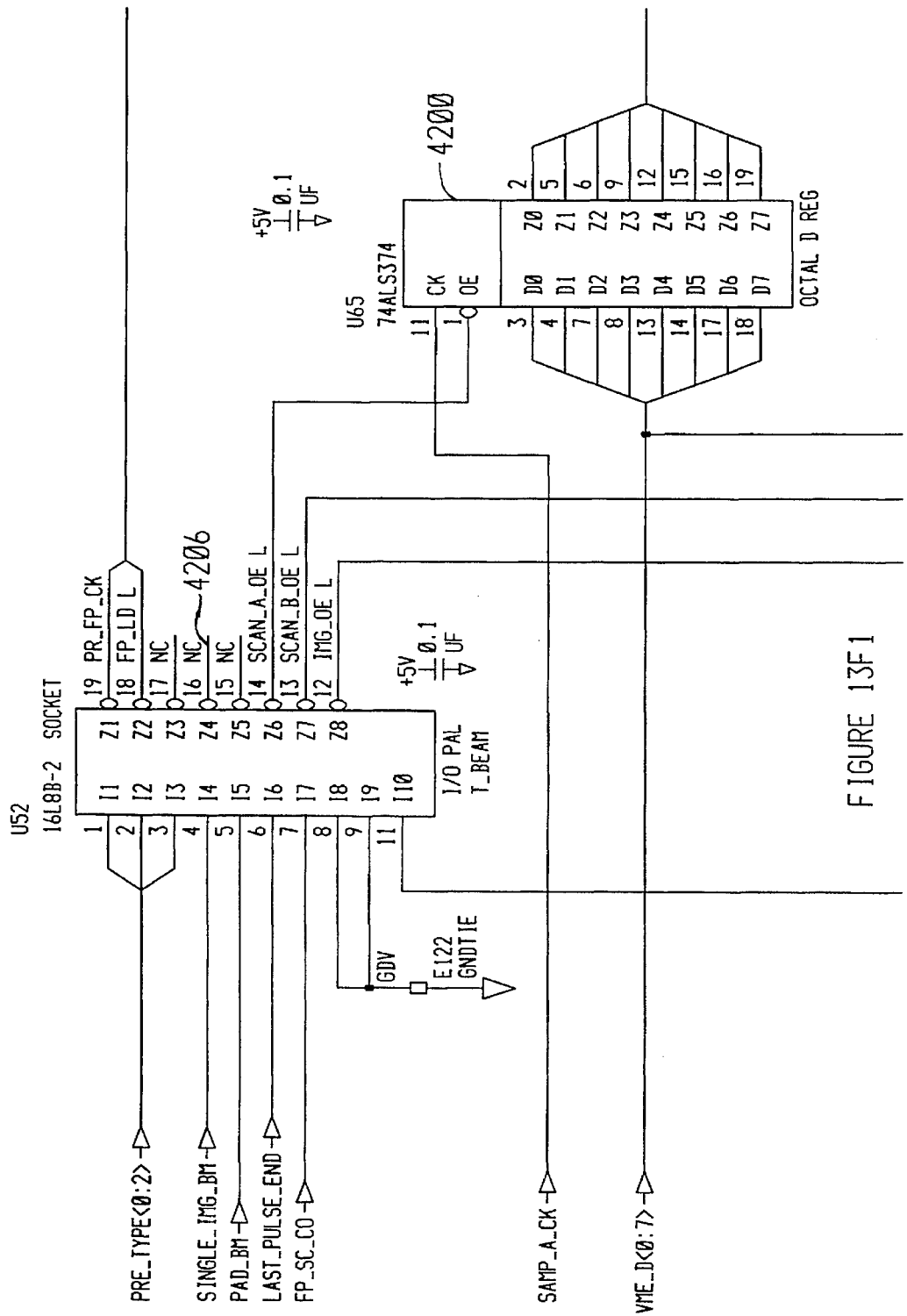
FIGURE 13F1

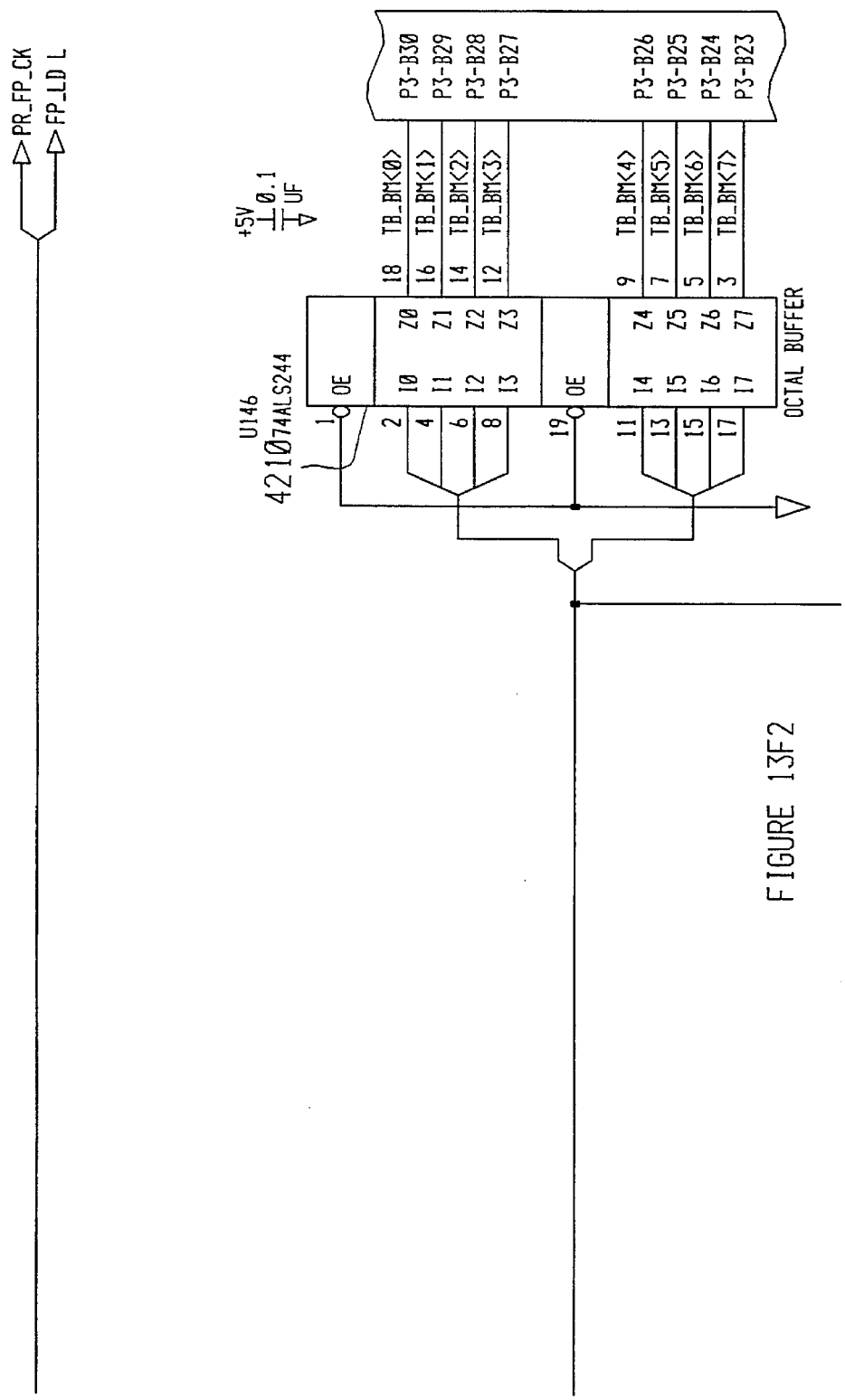
FIGURE 13F2

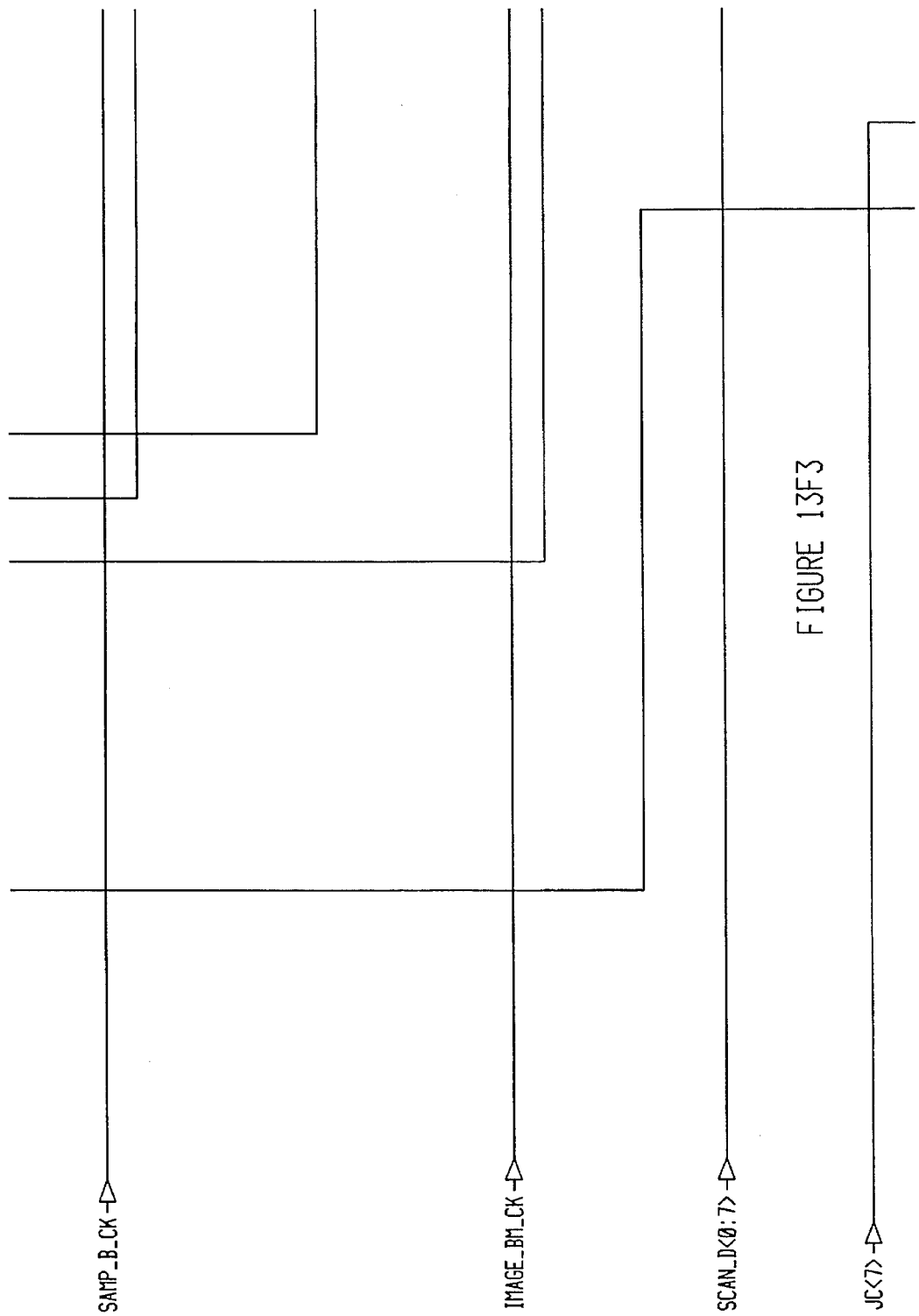

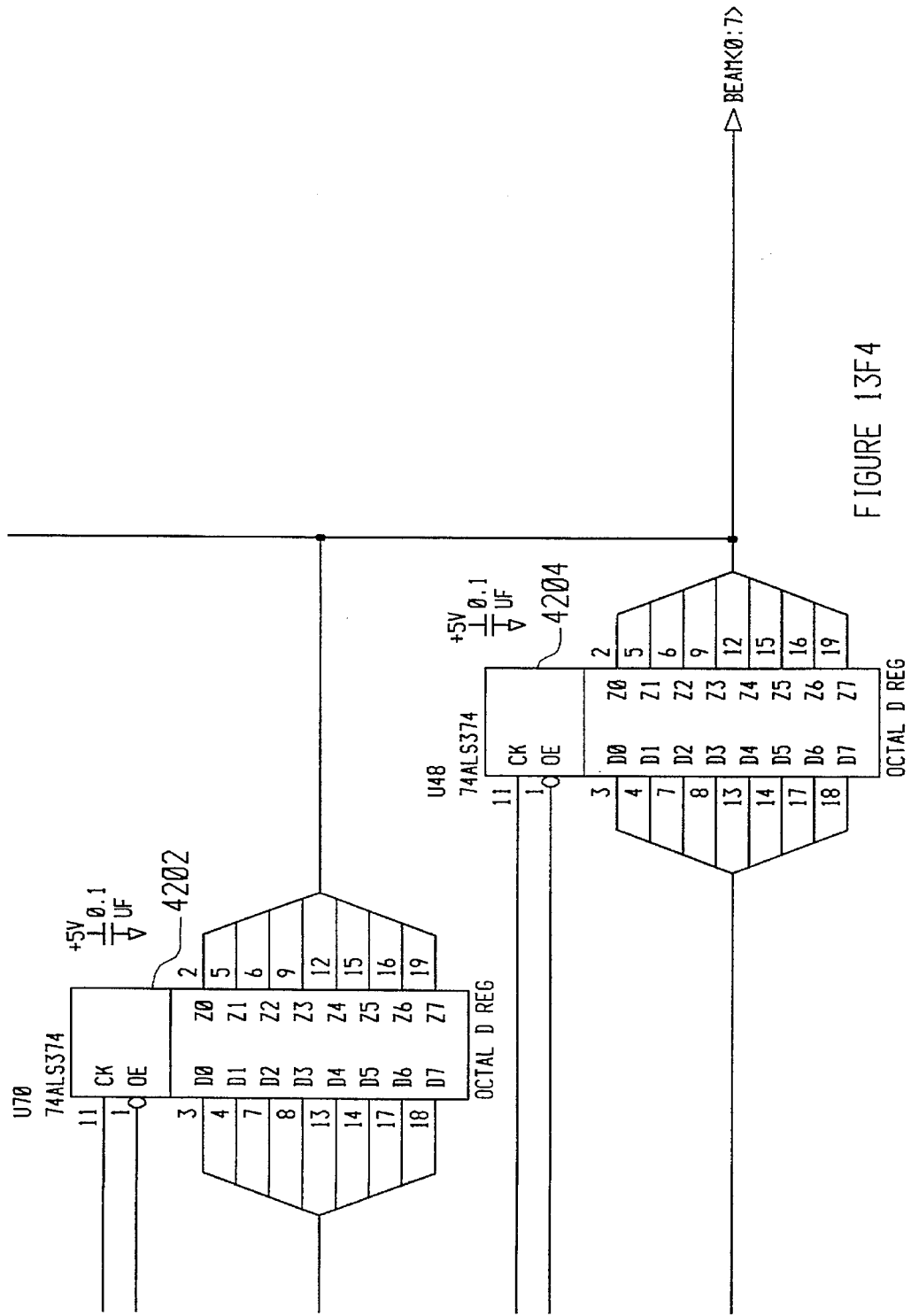
FIGURE 13F4

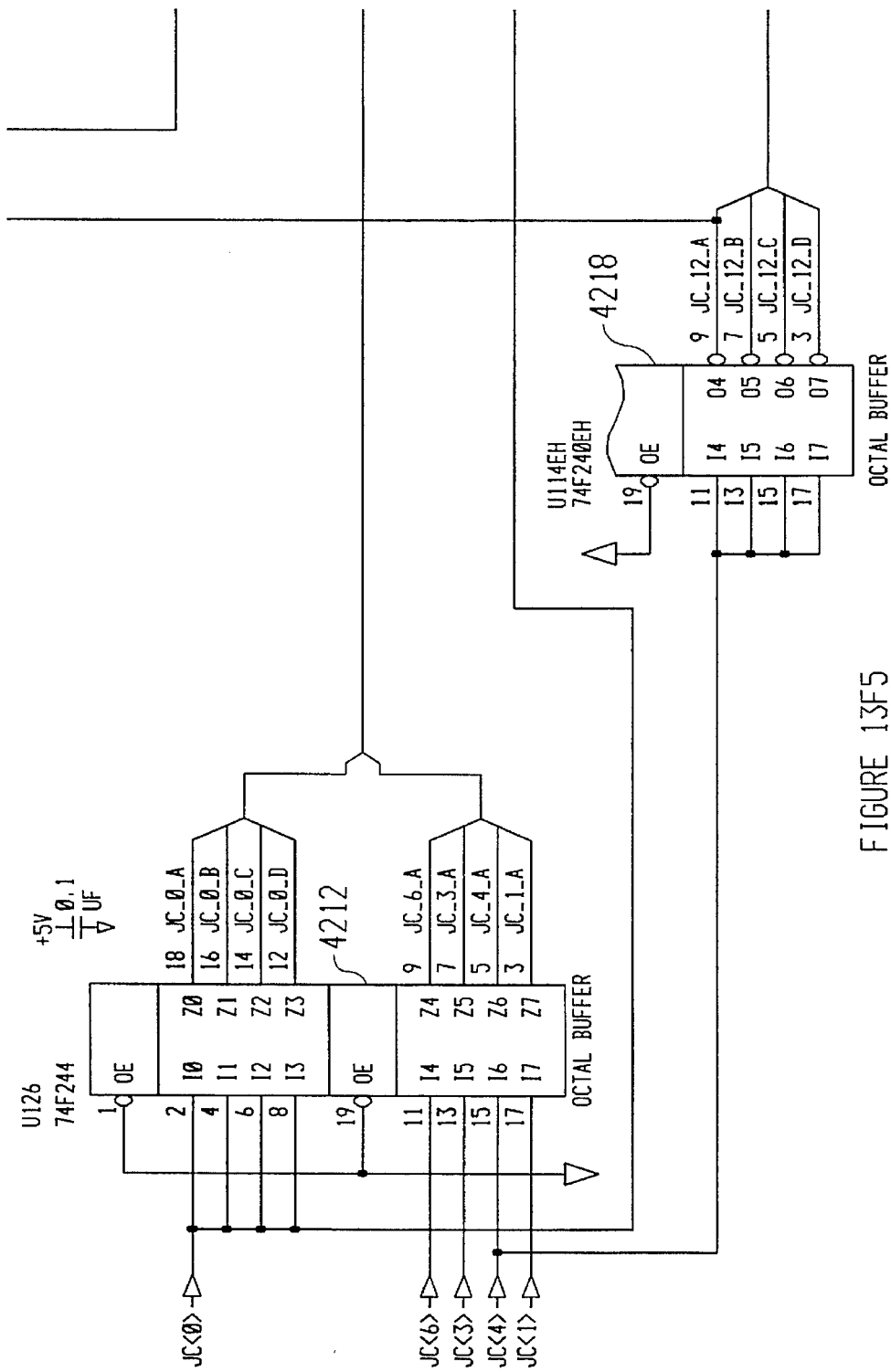
FIGURE 13F5

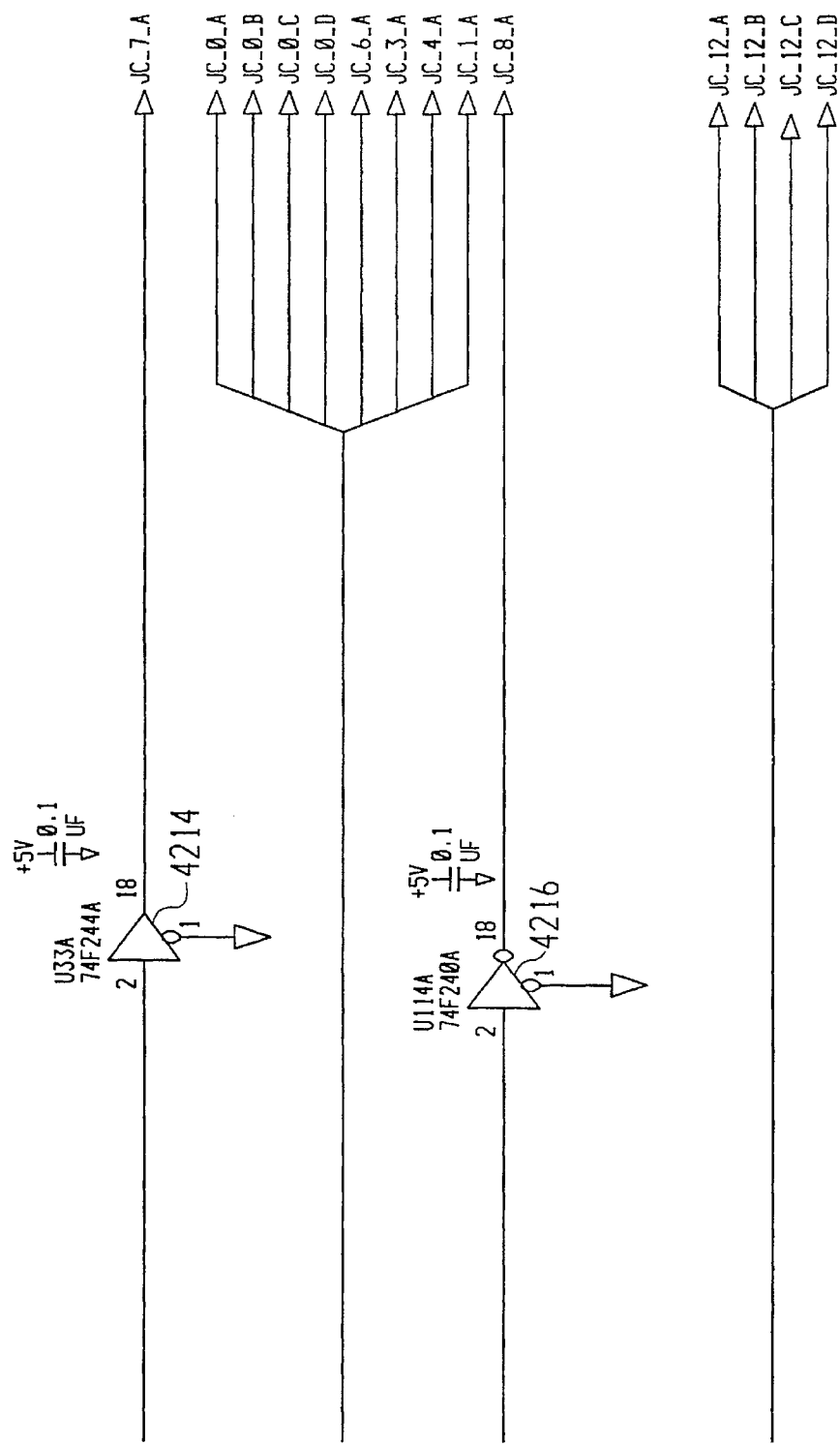
FIGURE 13F6

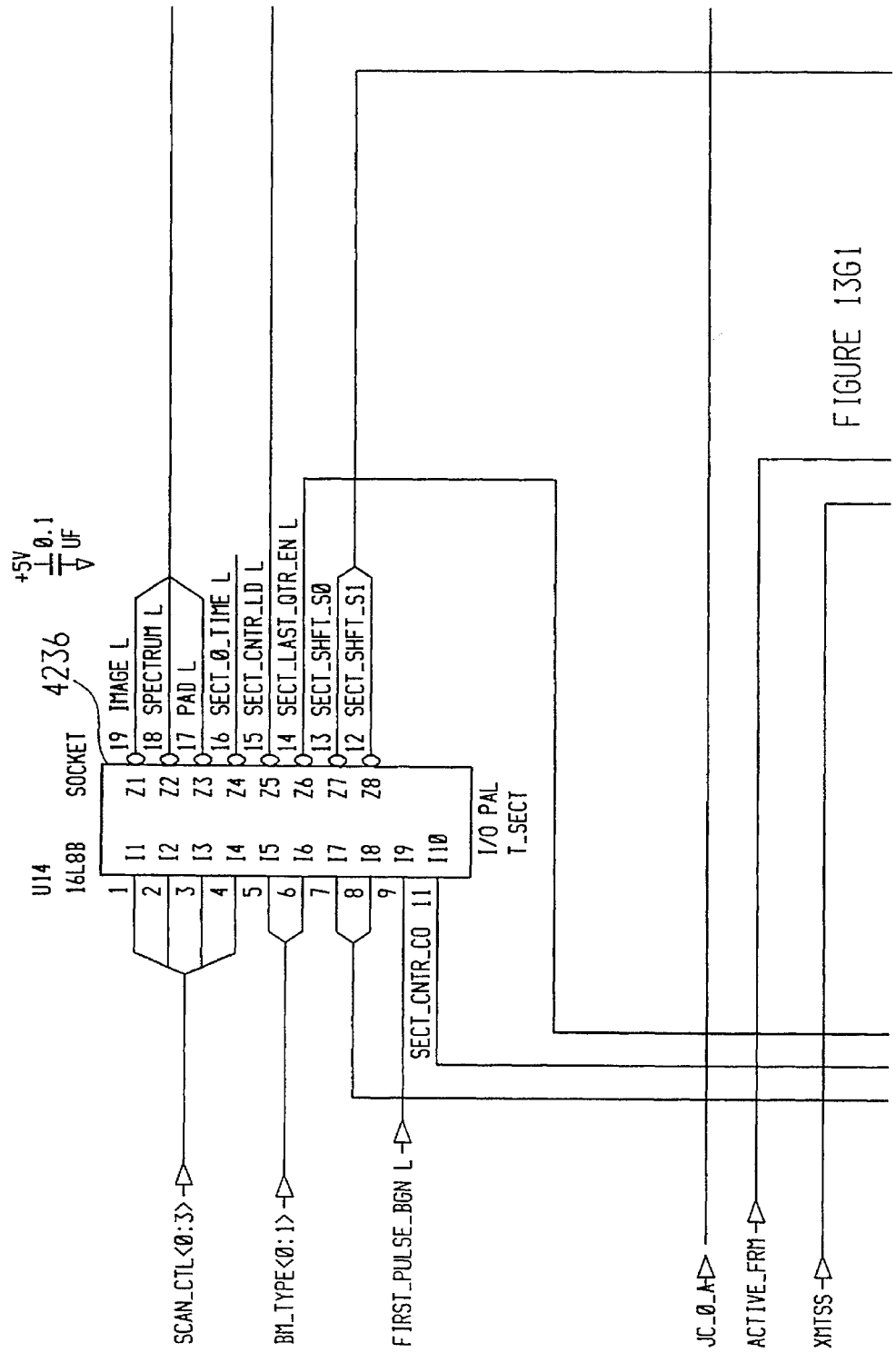
FIGURE 13G1

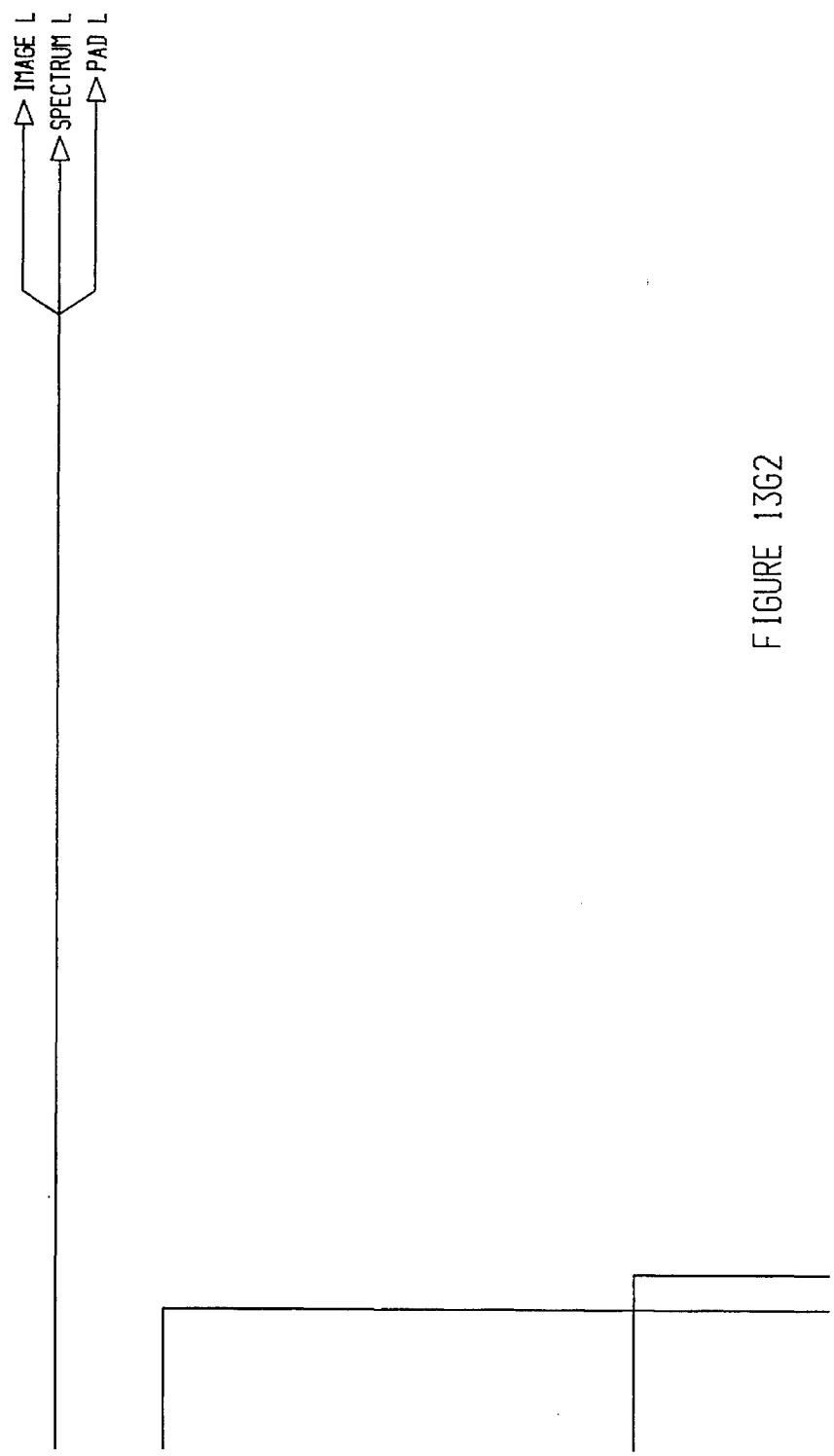

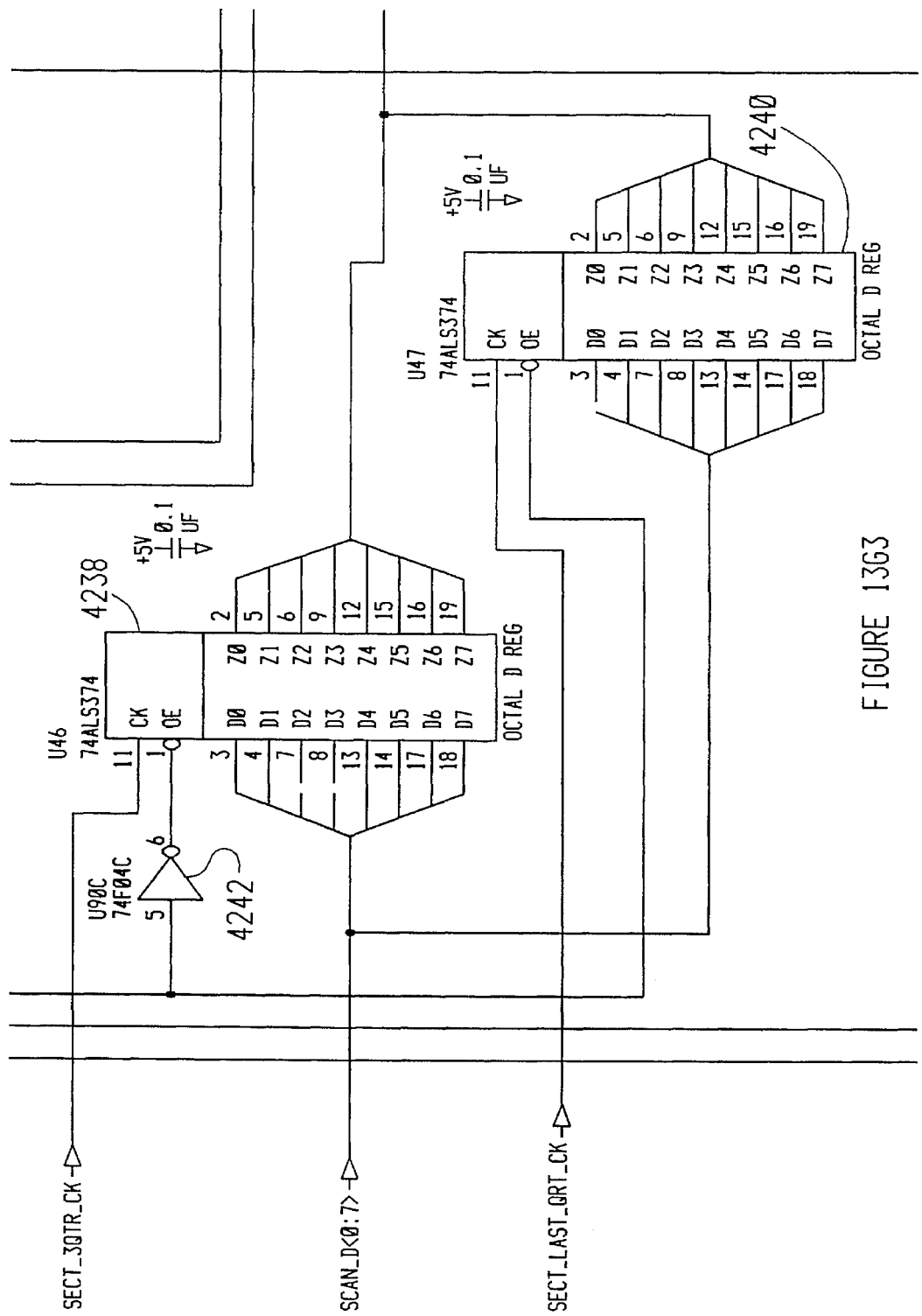
FIGURE 1363

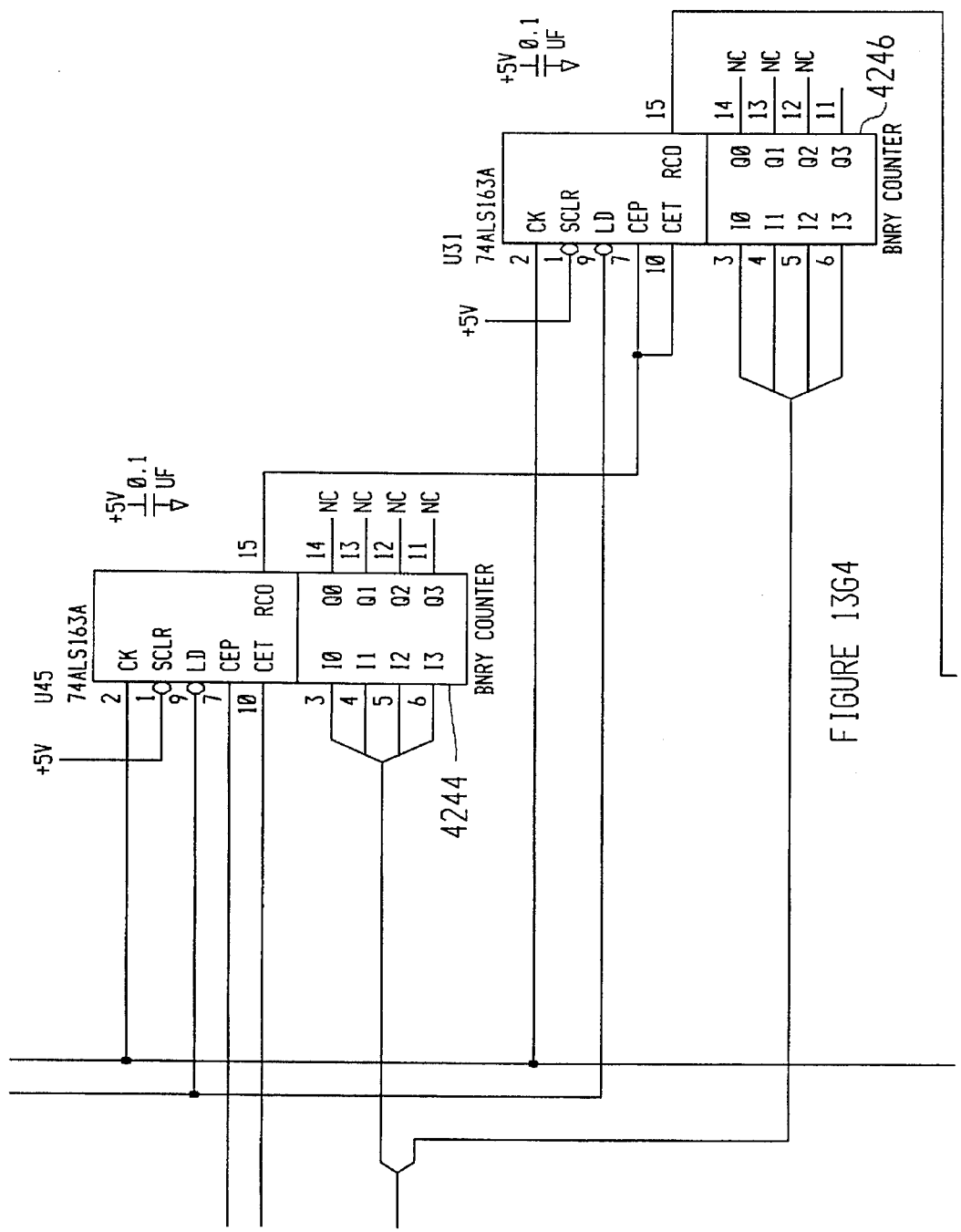
FIGURE 13G4

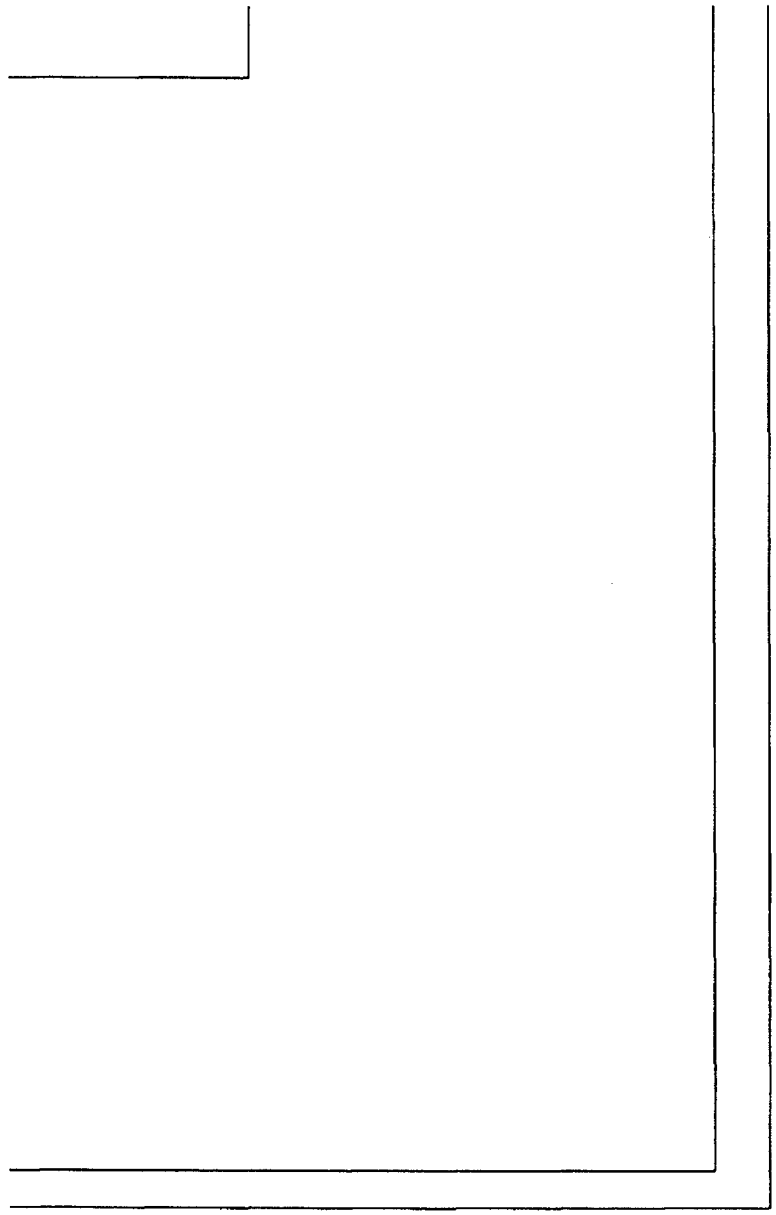
FIGURE 1365

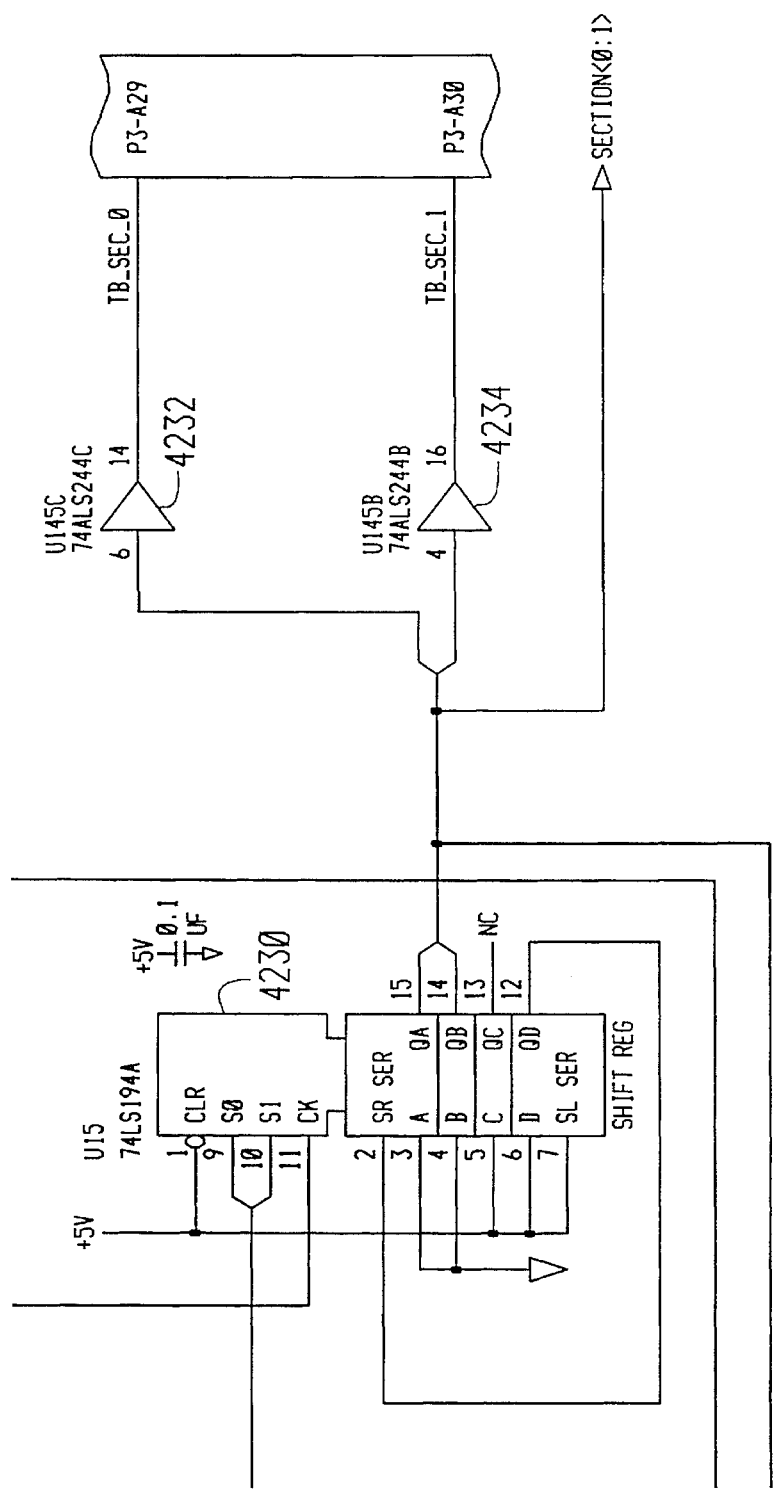
FIGURE 13G6

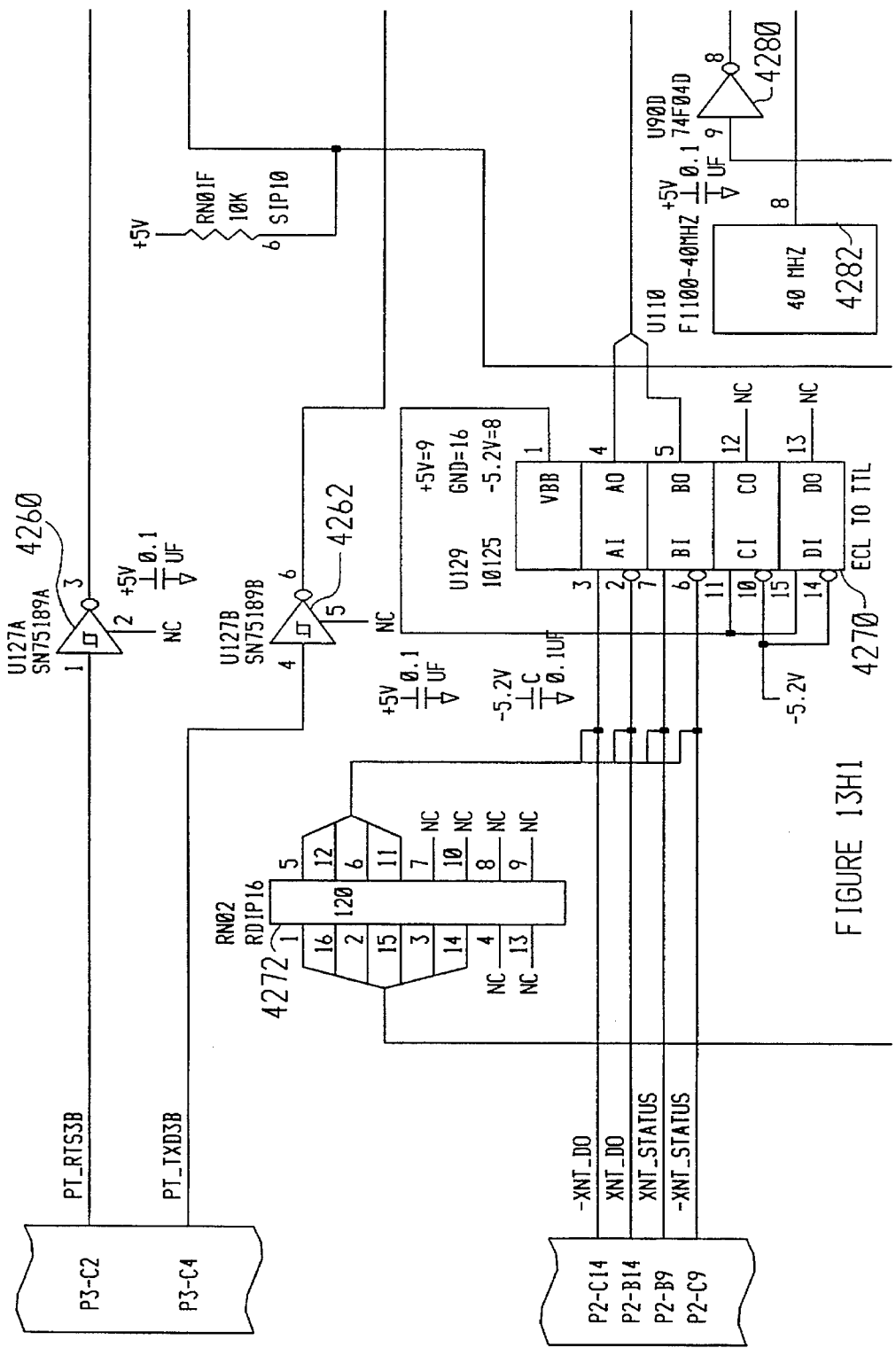
FIGURE 13H1

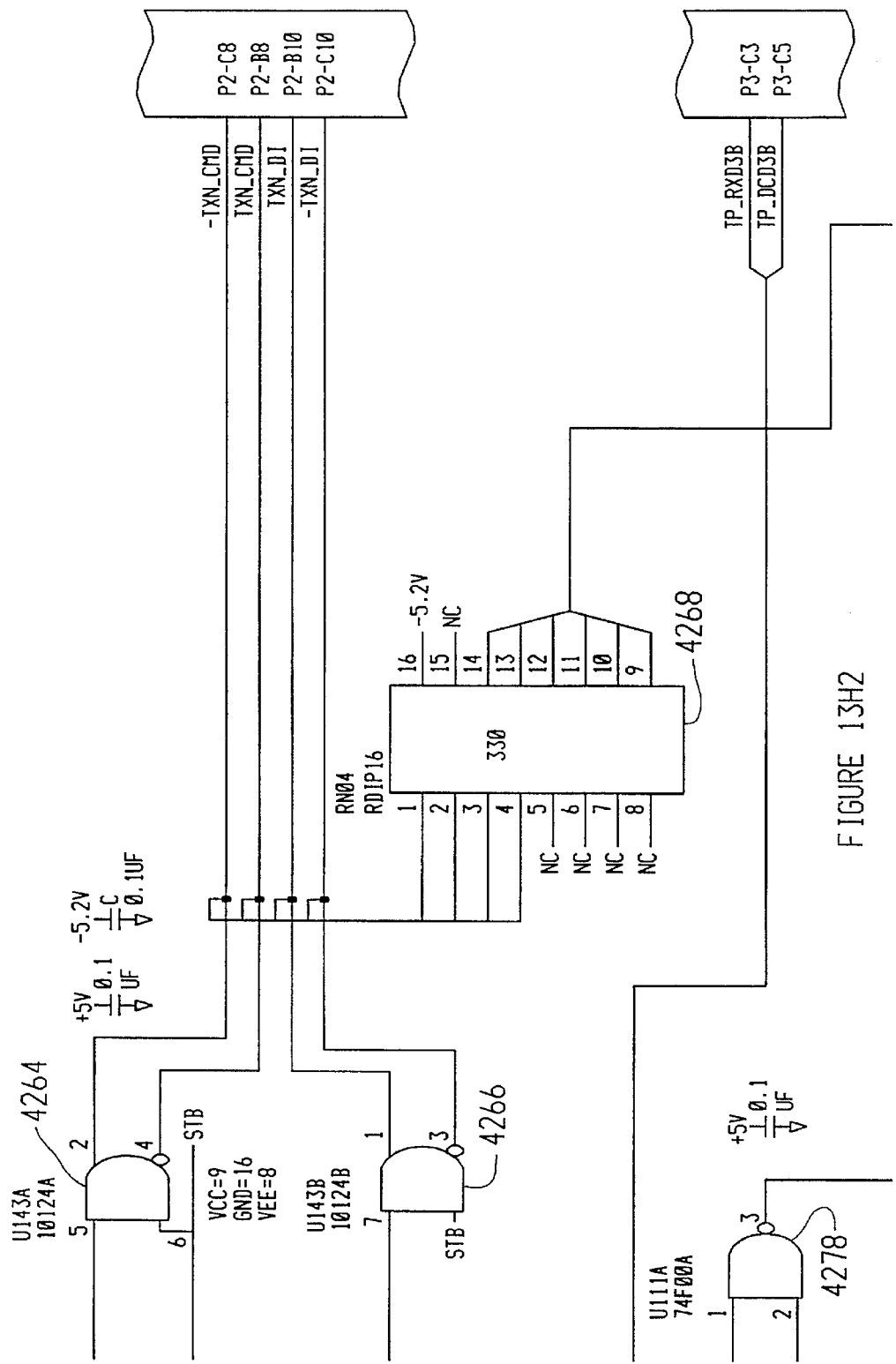
FIGURE 13H2

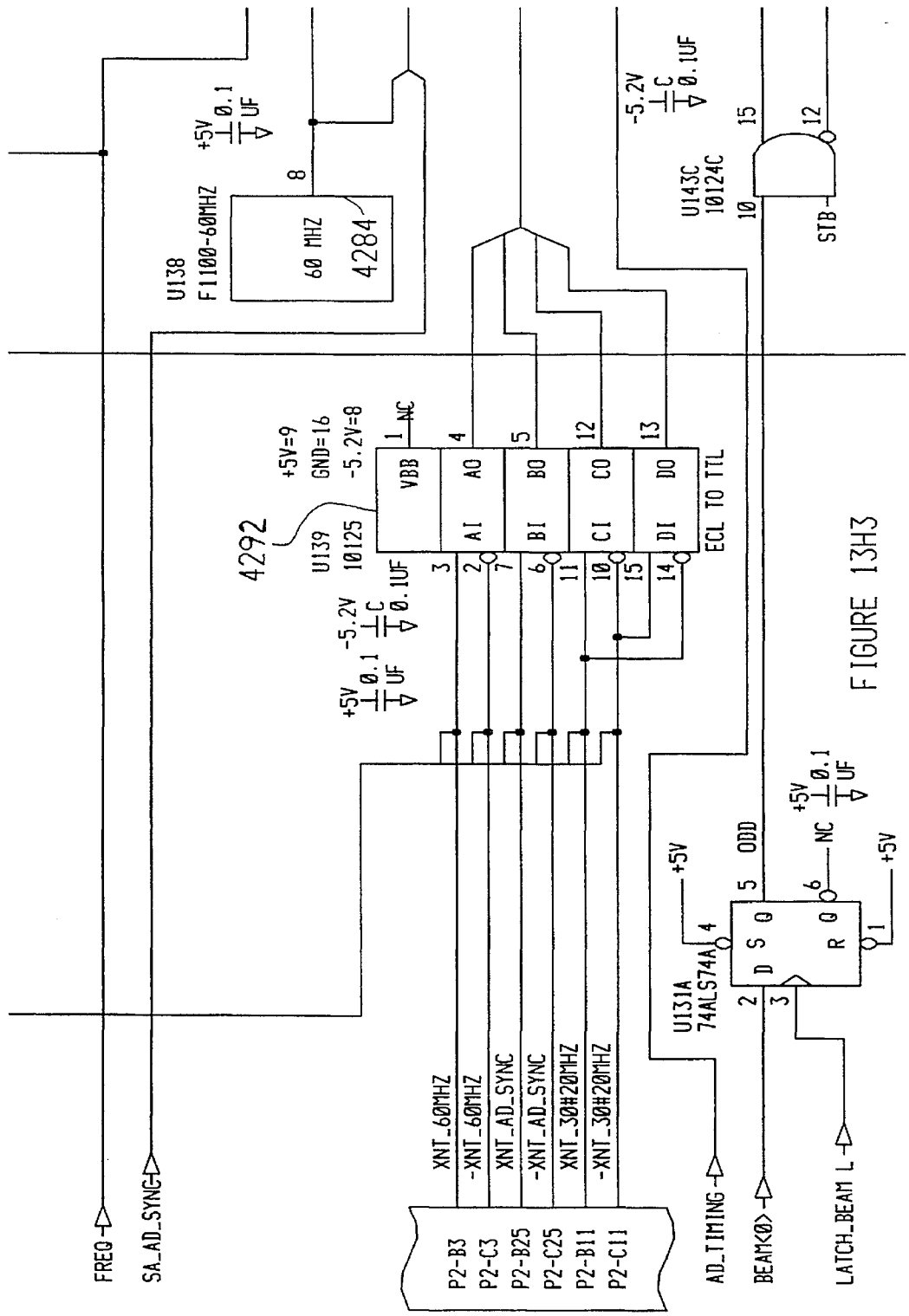
FIGURE 13H3

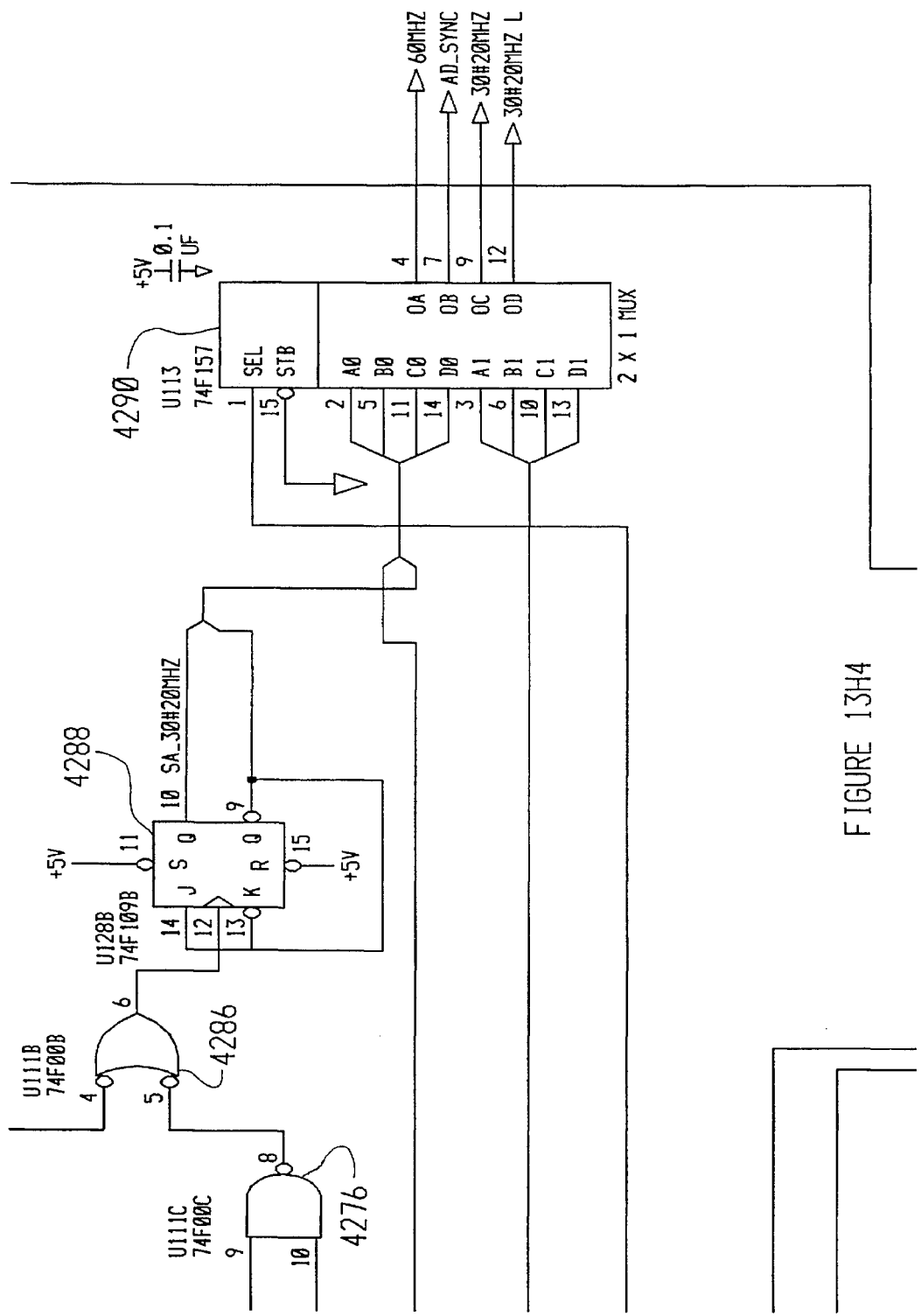
FIGURE 13H4

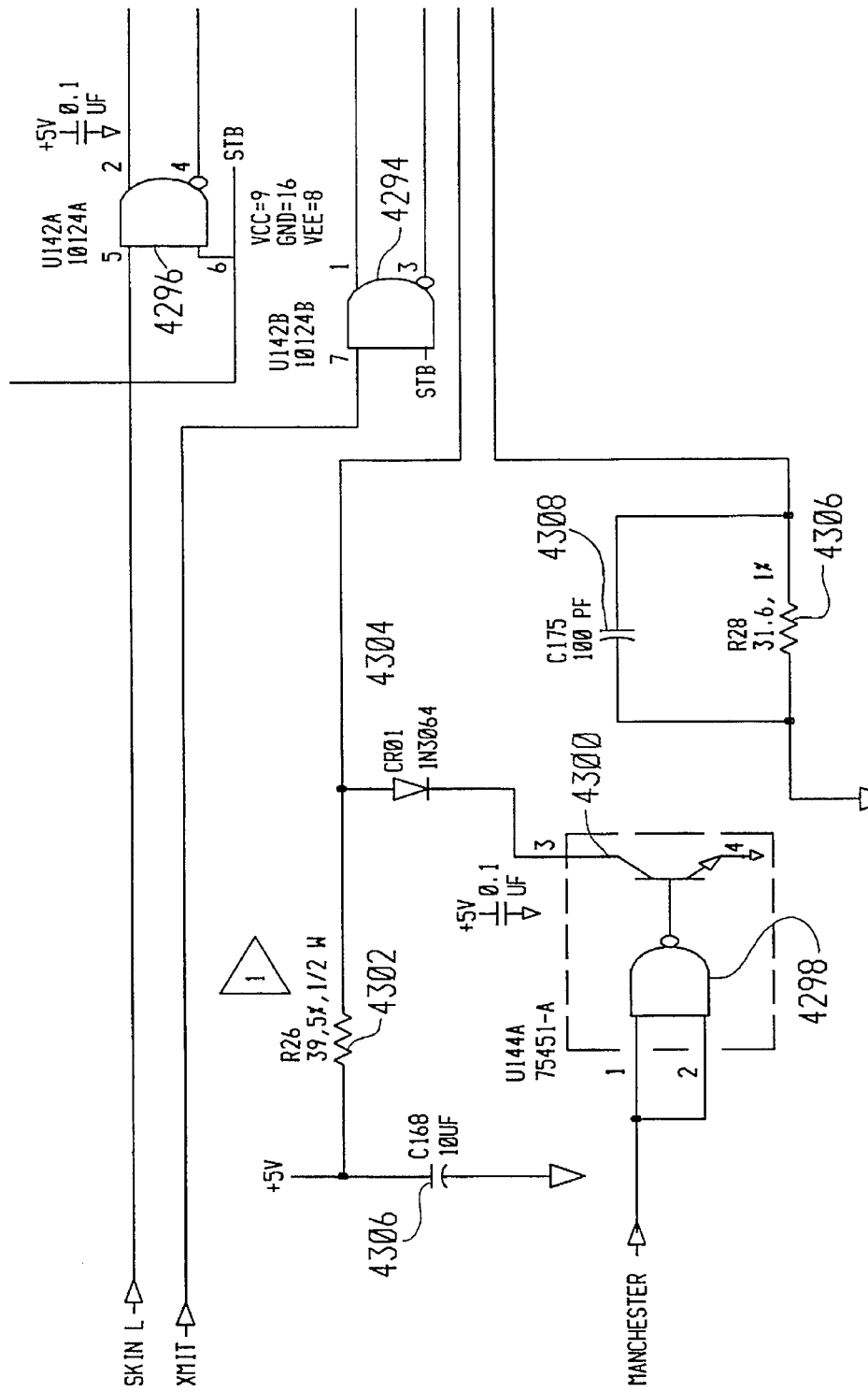
FIGURE 13H5

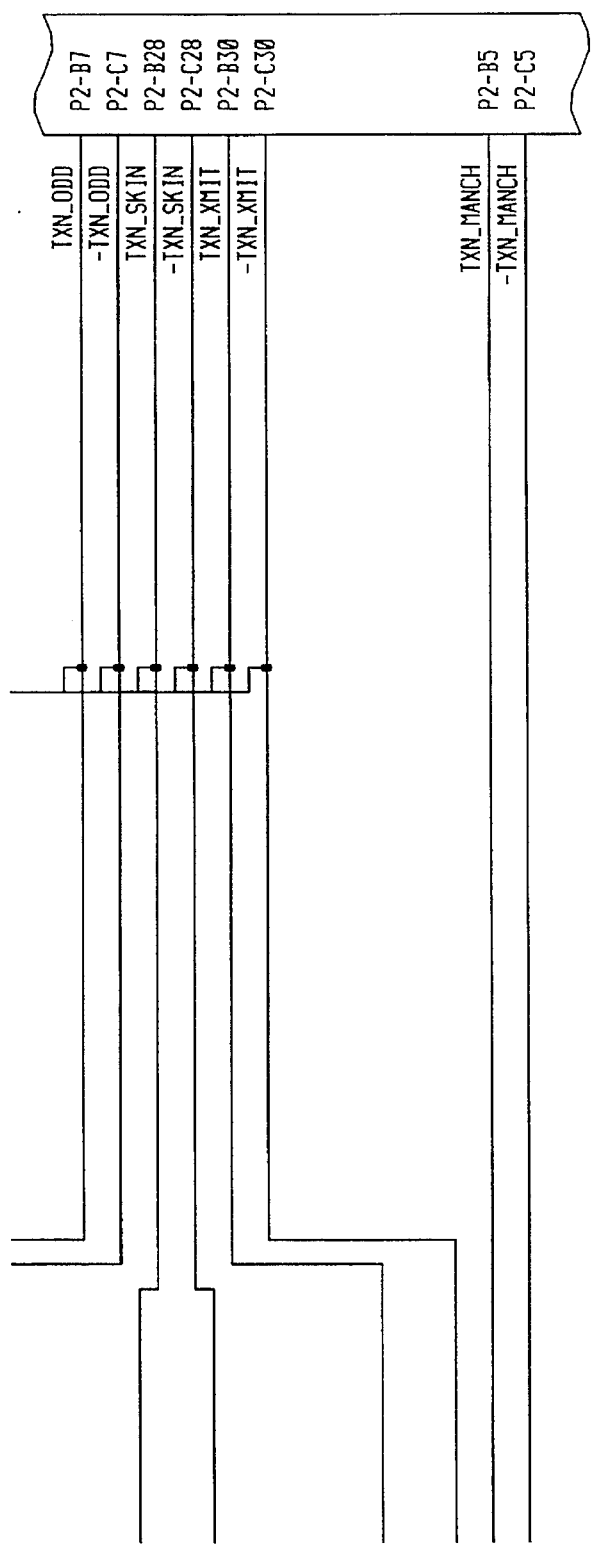
FIGURE 13H6

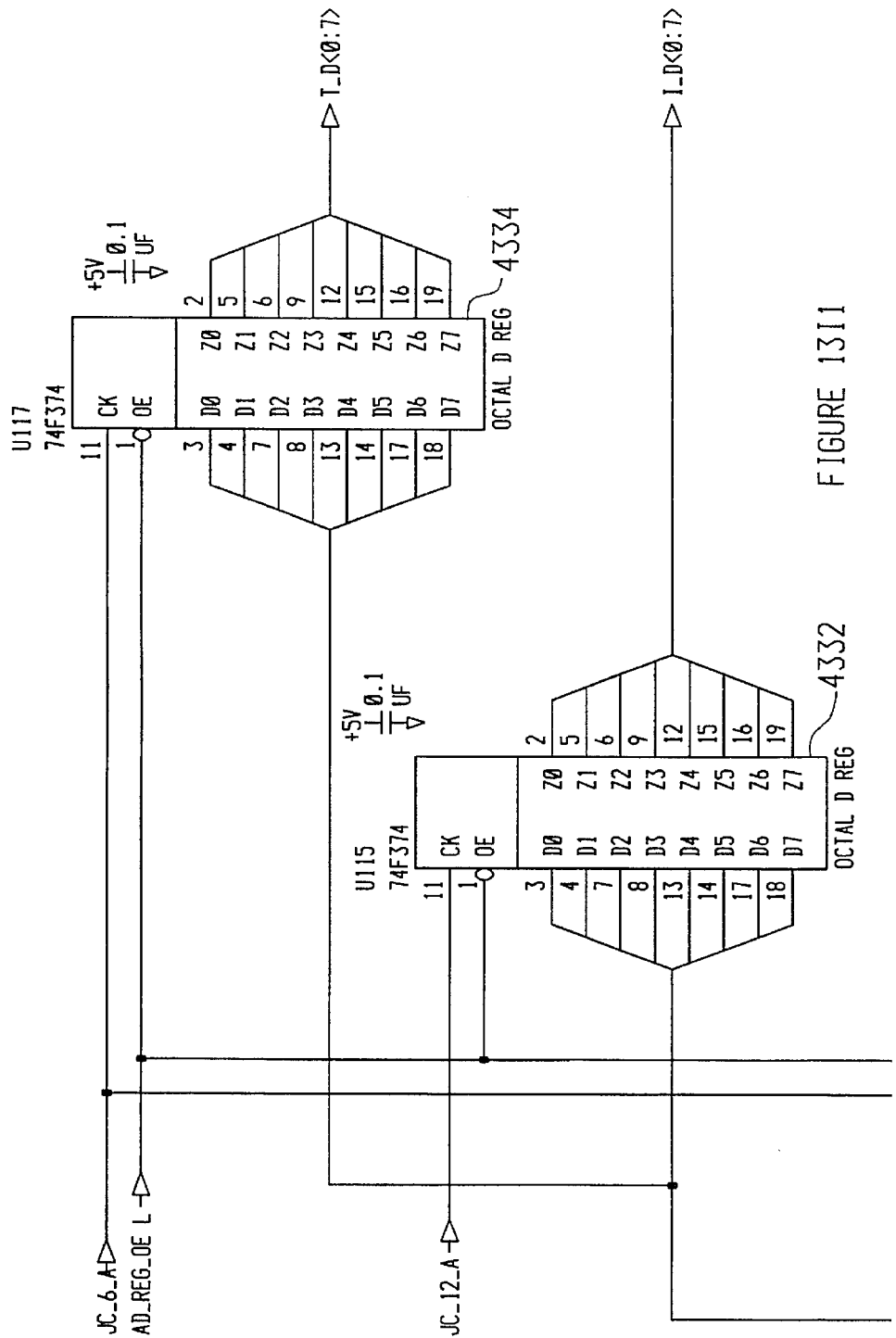
FIGURE 1311

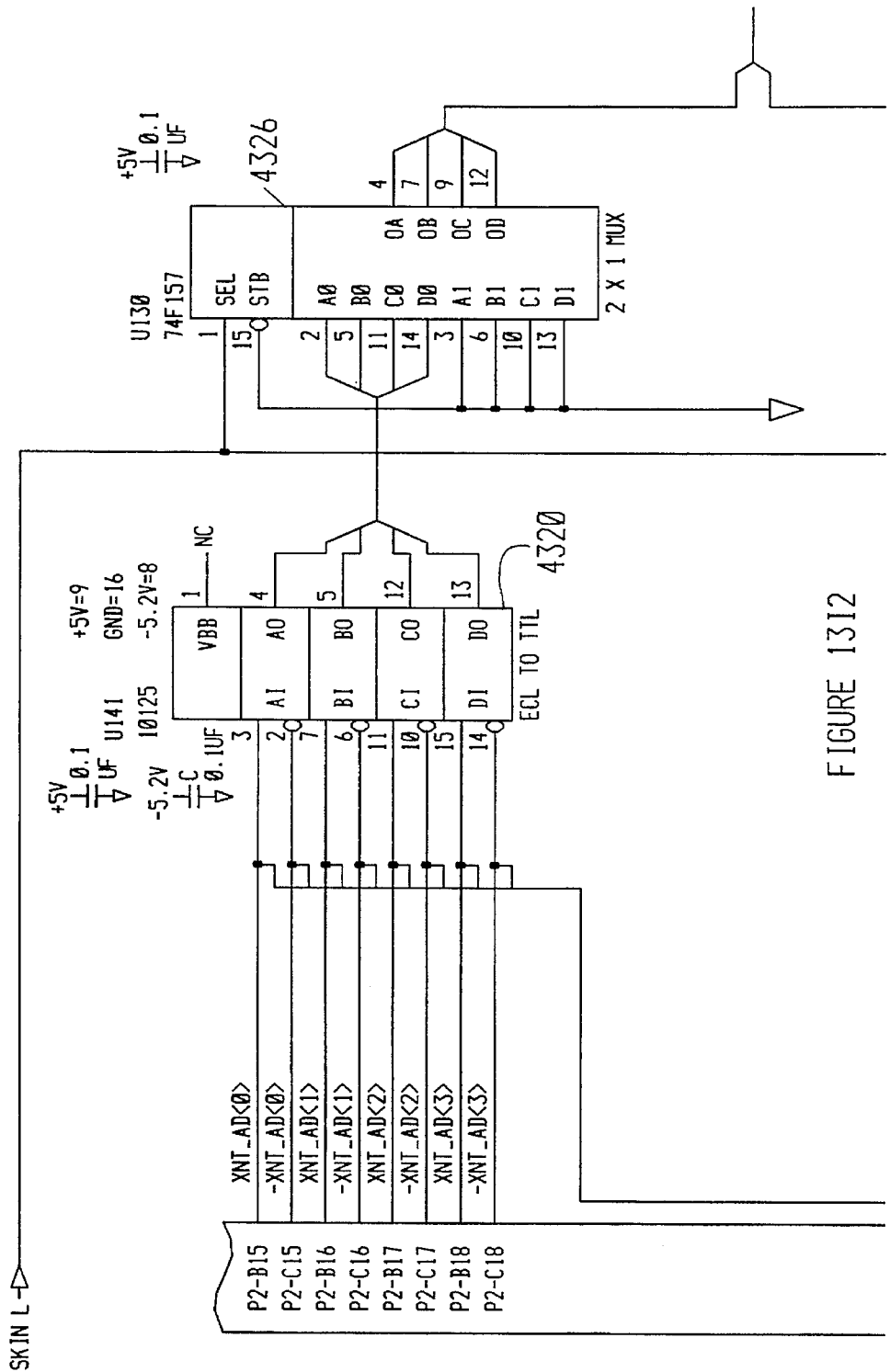
FIGURE 1312

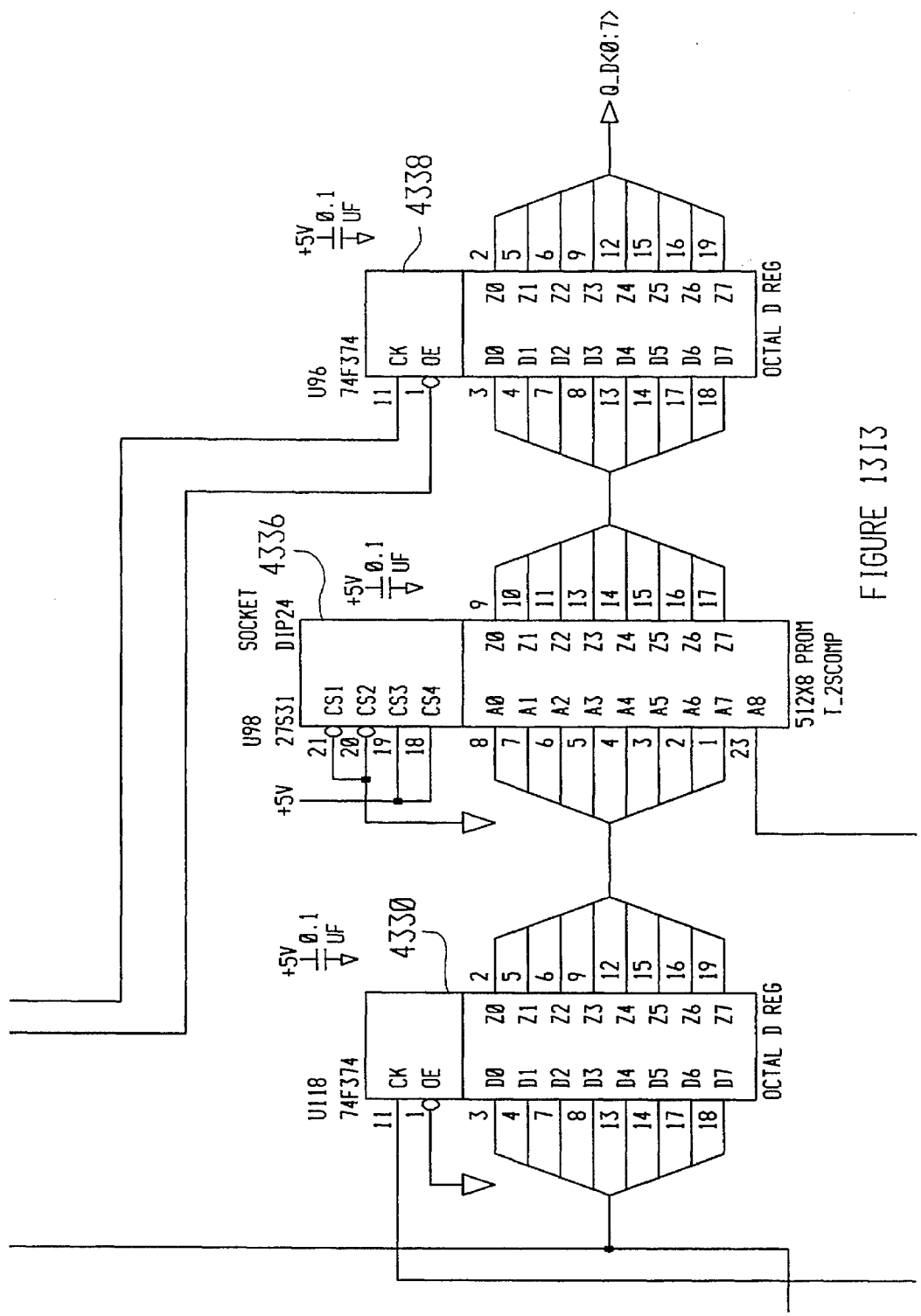
FIGURE 1313

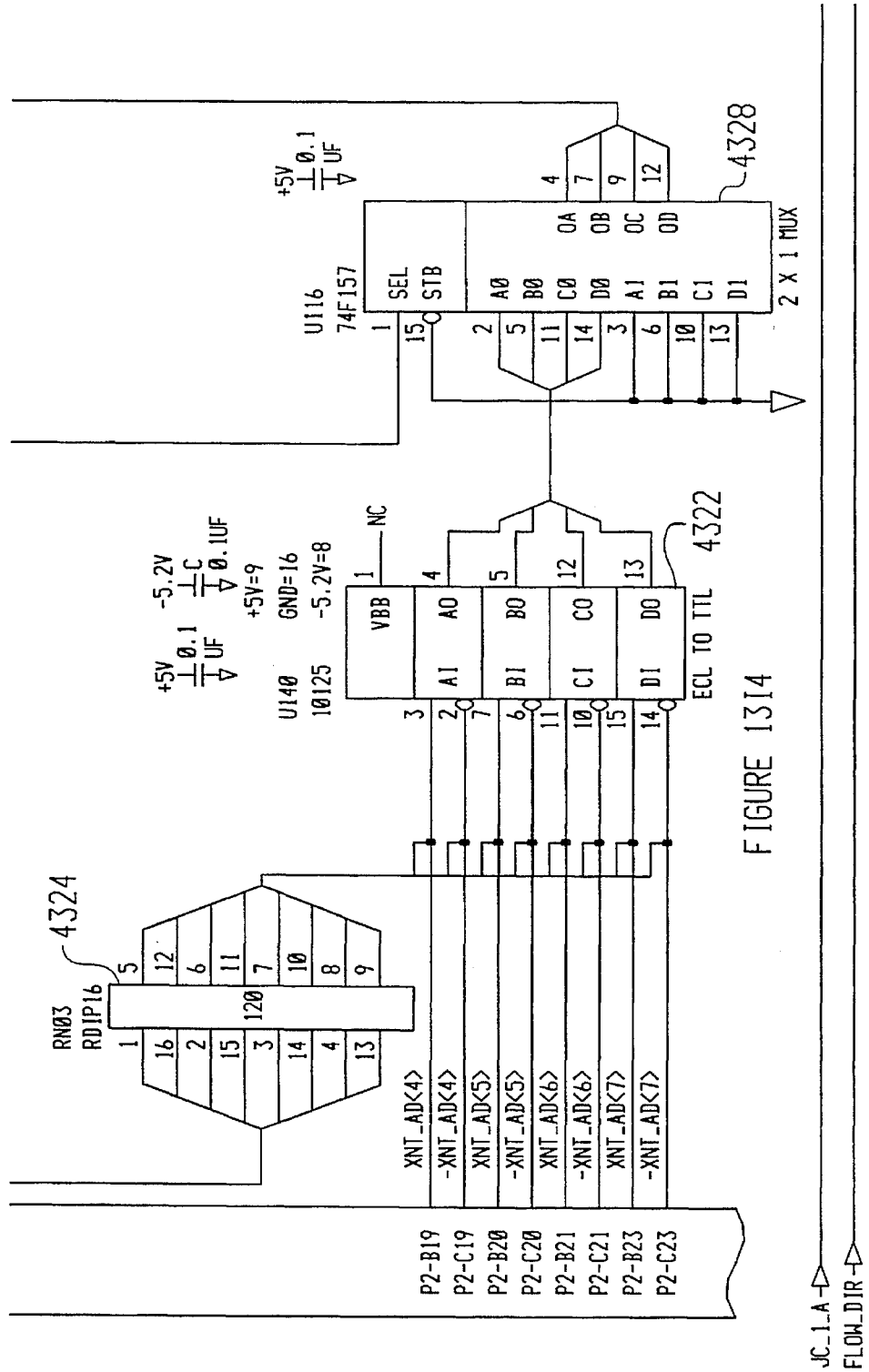
FIGURE 1314

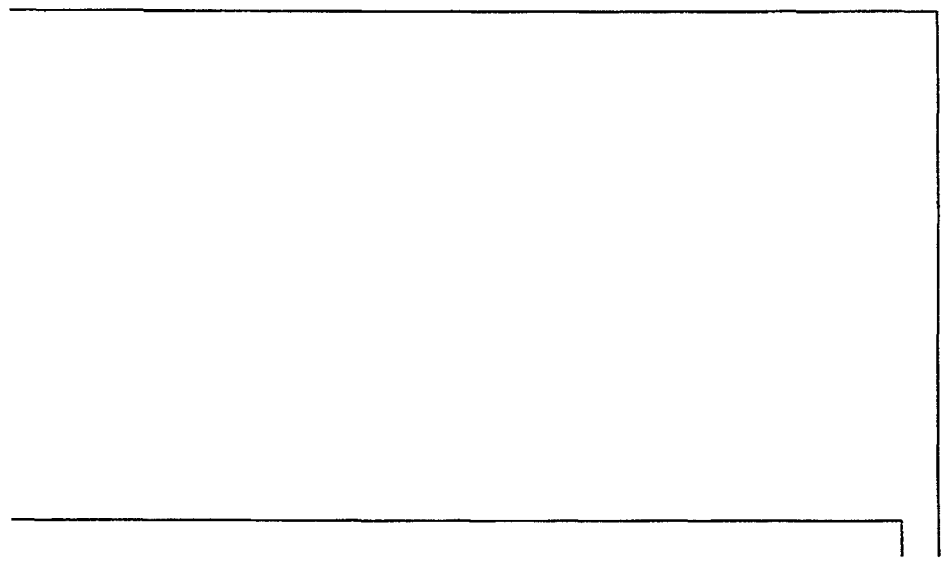
FIGURE 1315

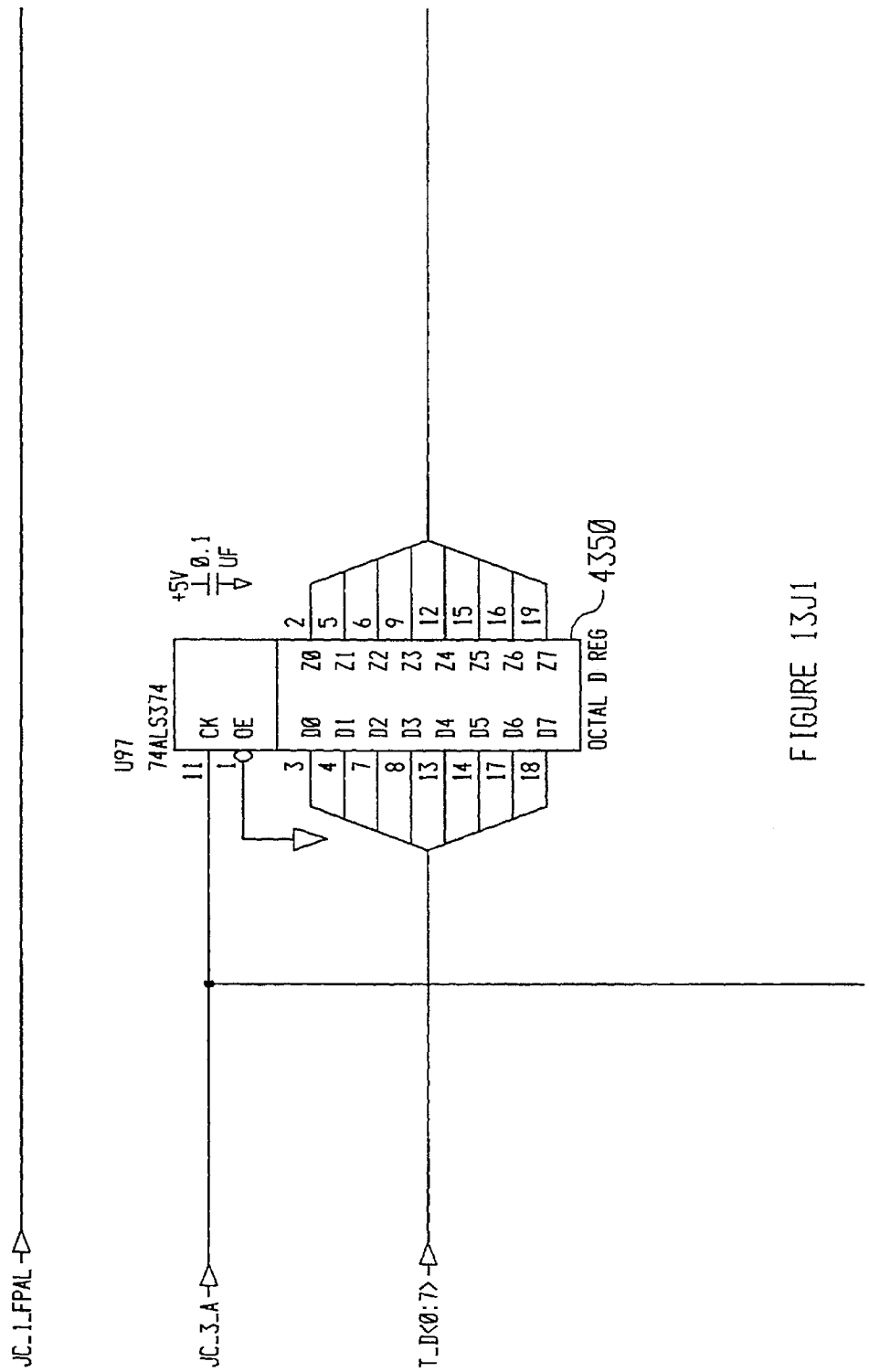
FIGURE 13J1

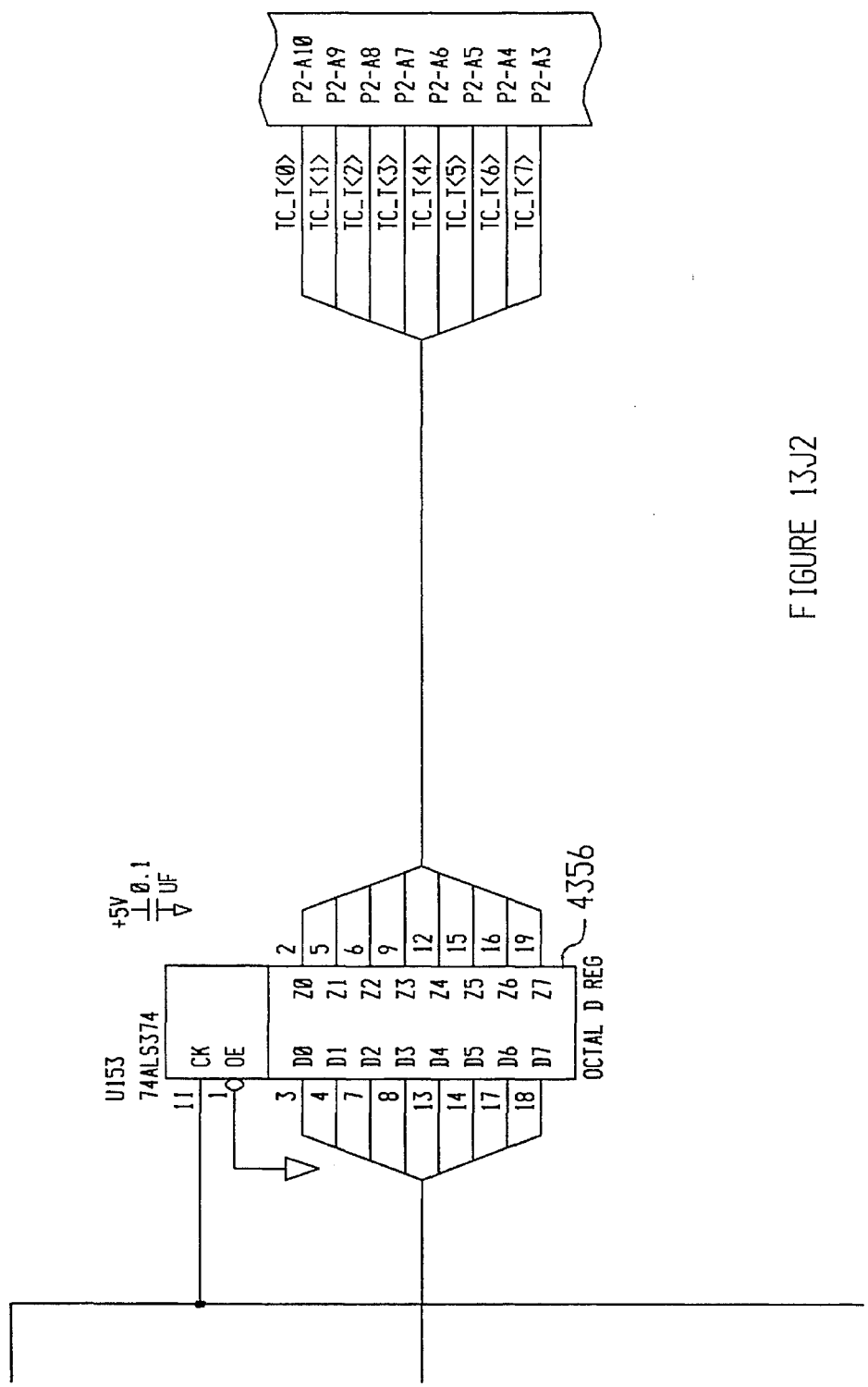
FIGURE 13J2

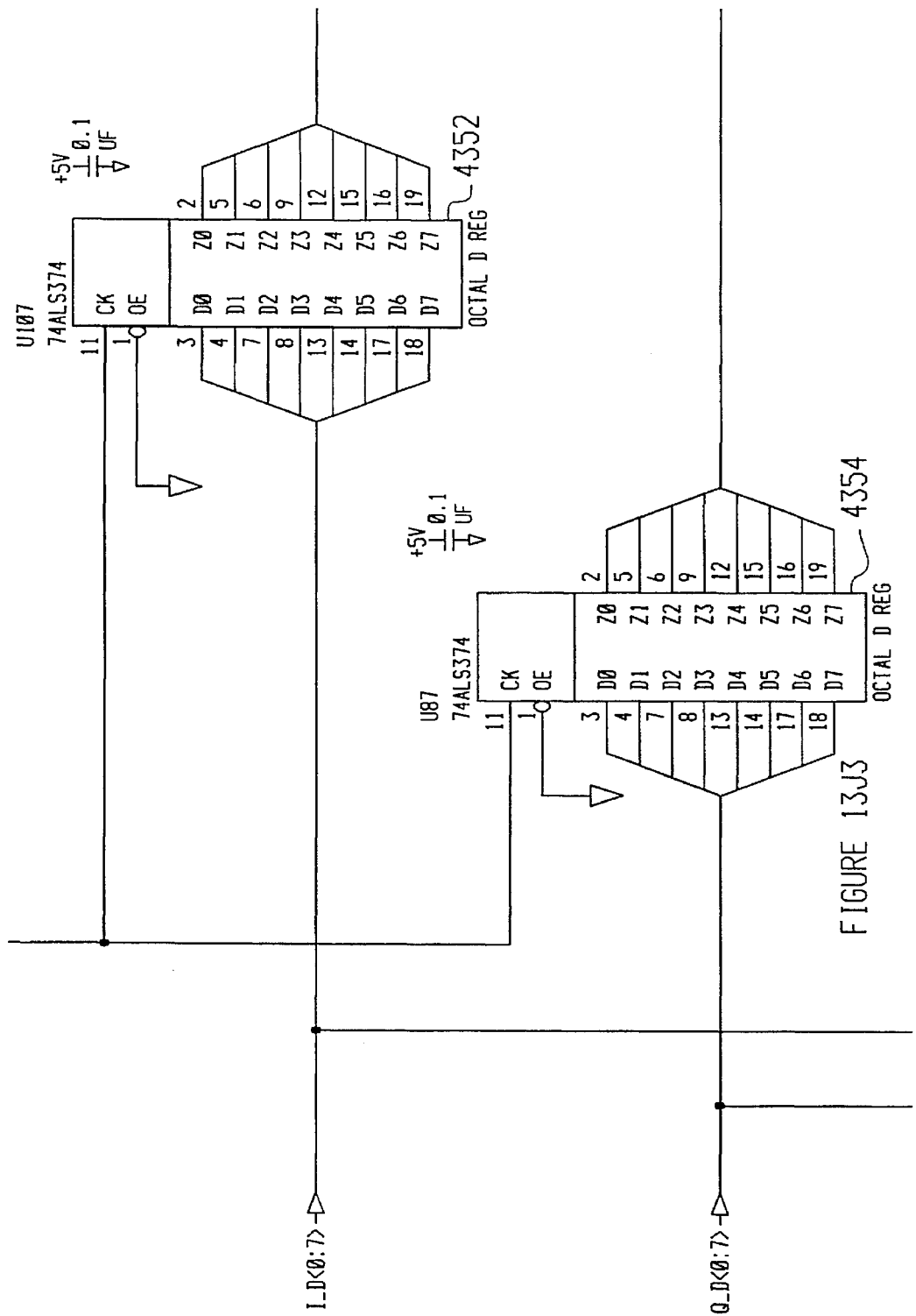
FIGURE 13J3

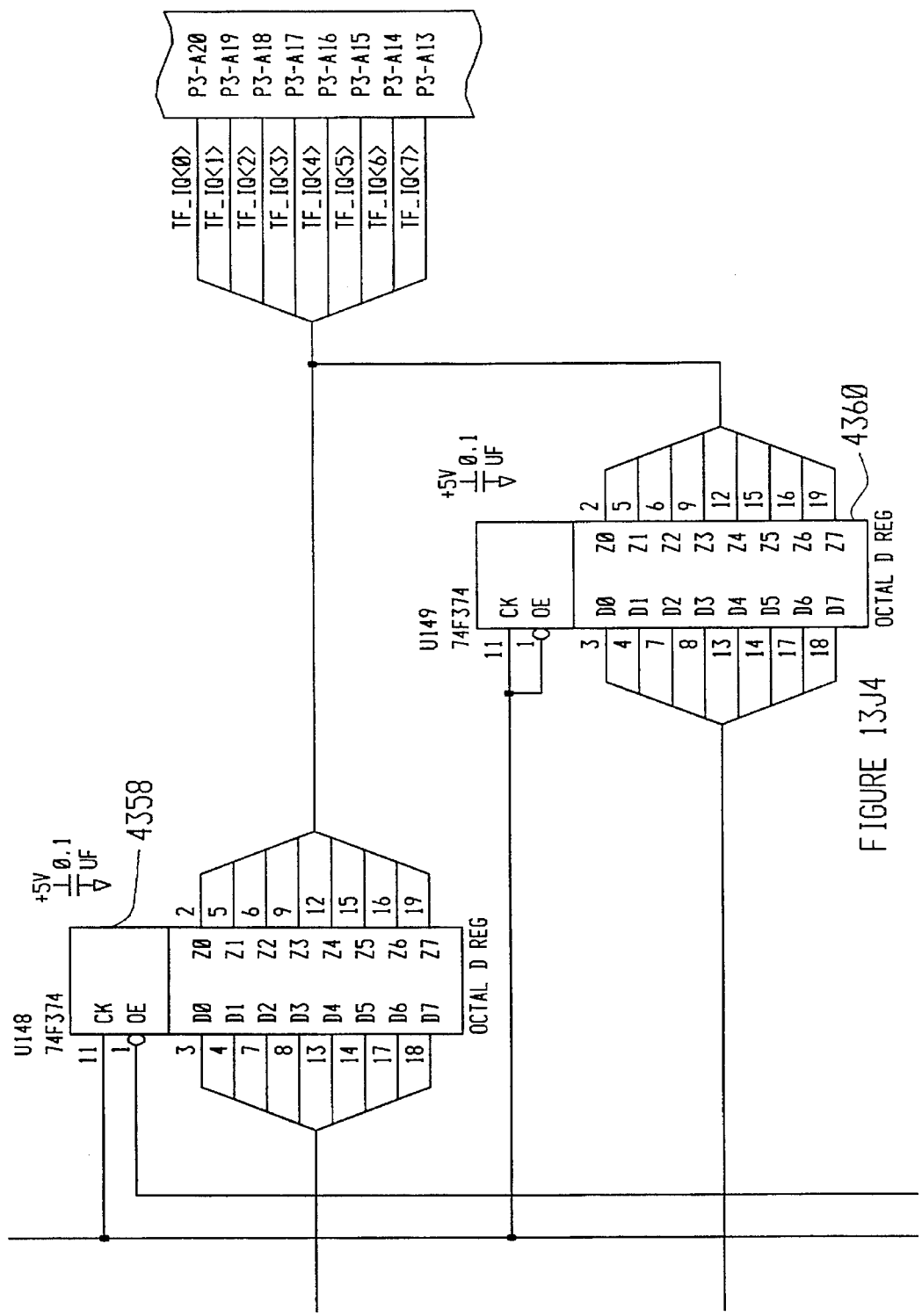
FIGURE 13J4

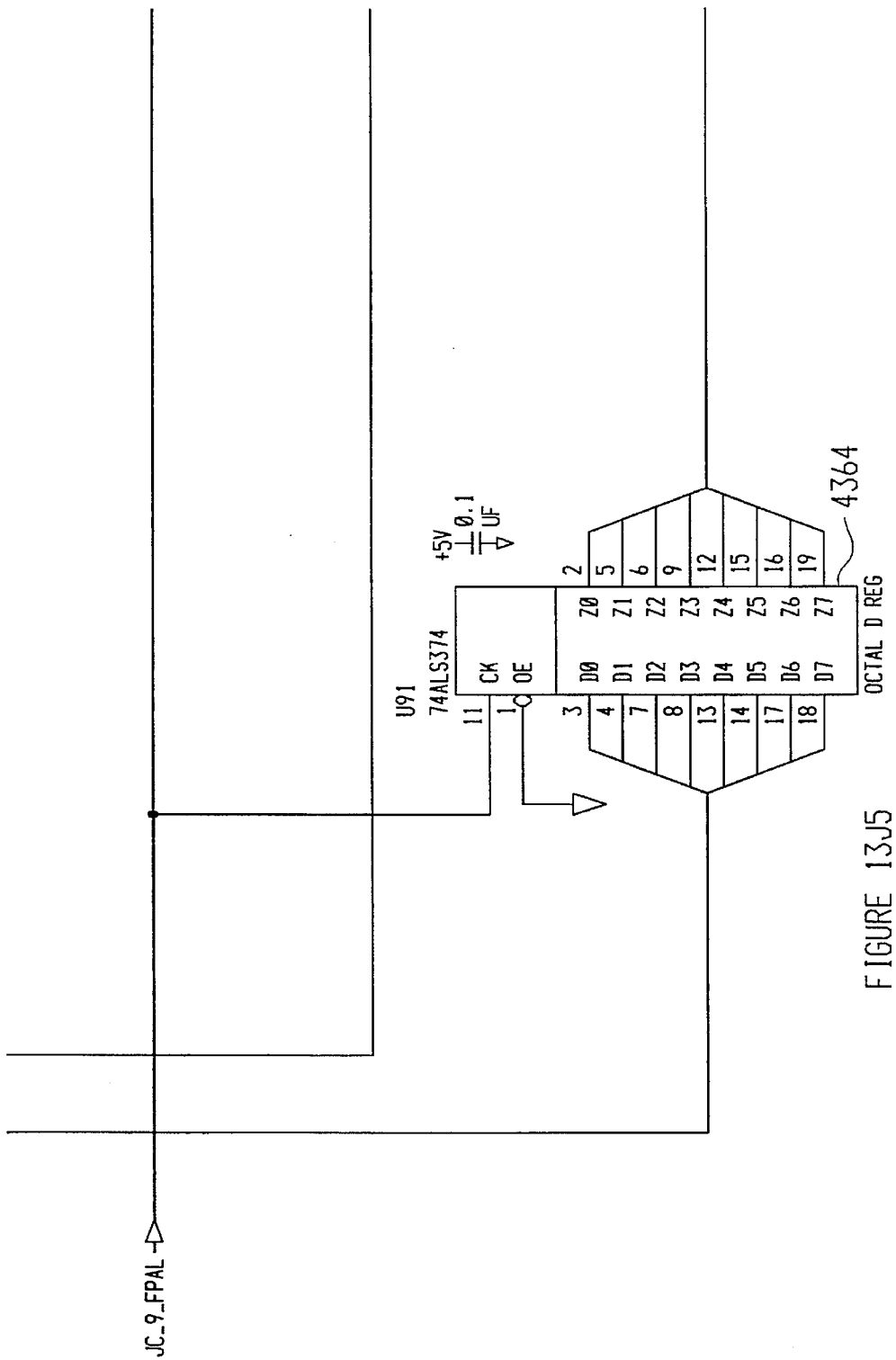
FIGURE 13J5

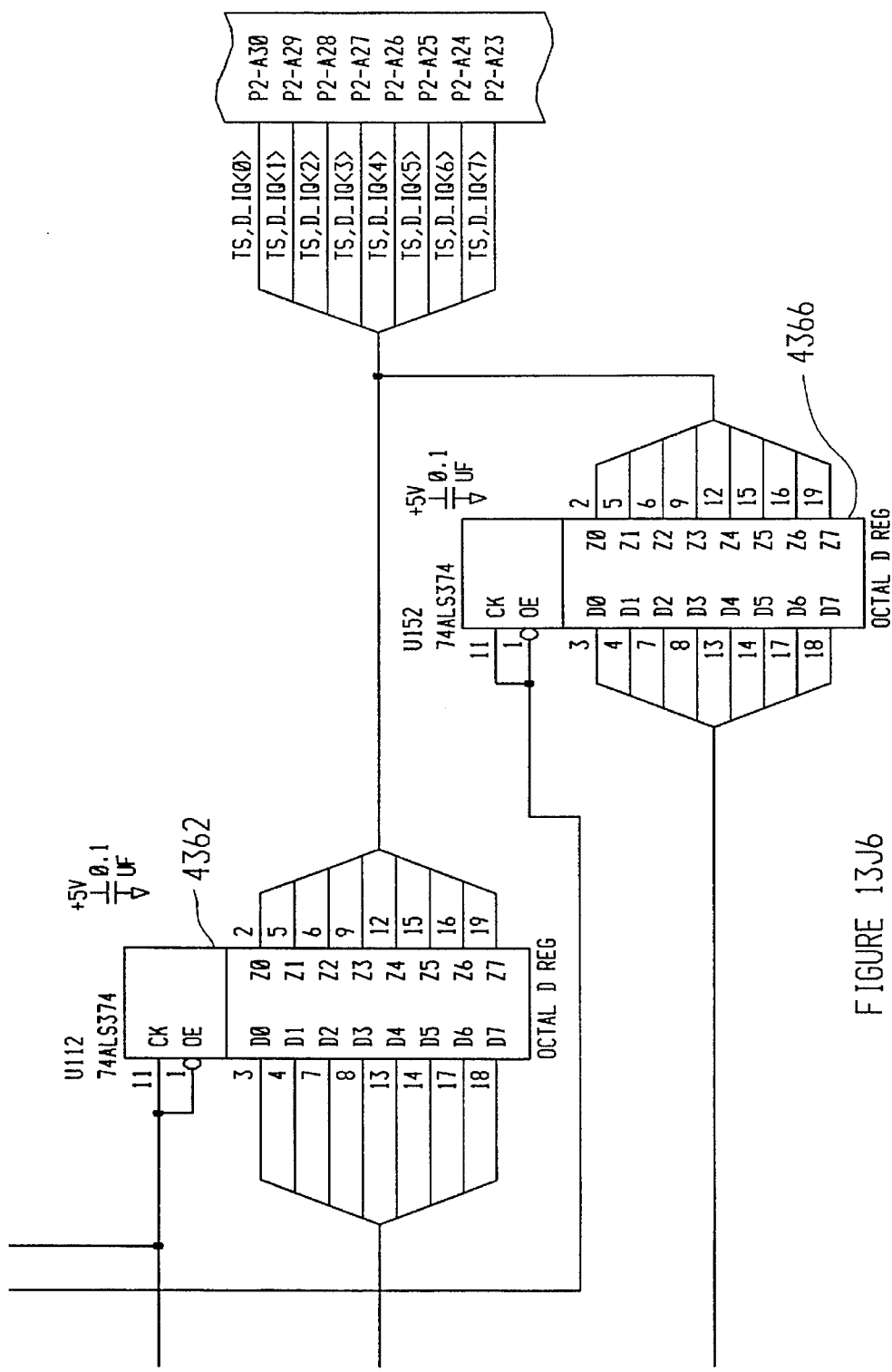
FIGURE 13J6

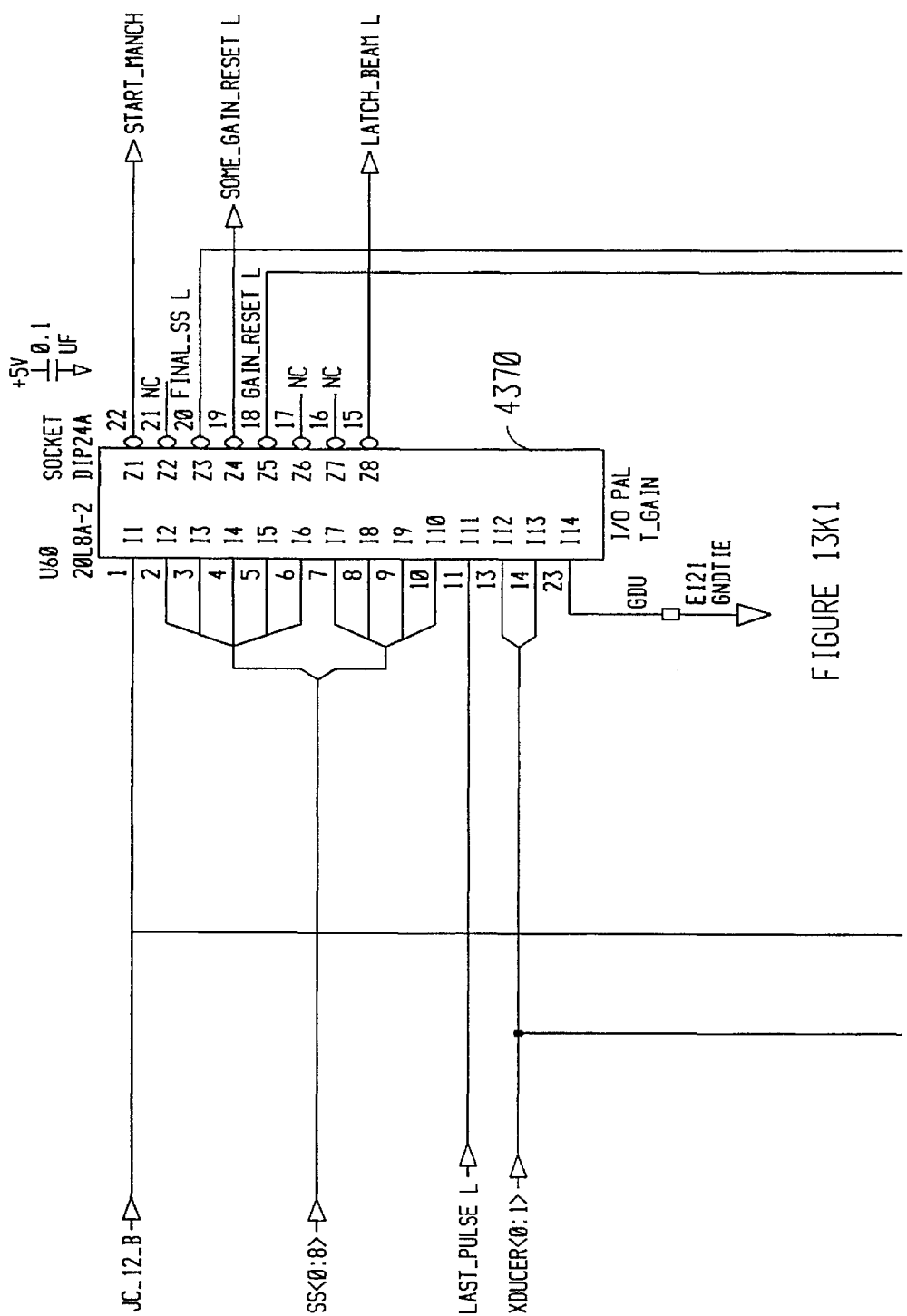
FIGURE 13K1

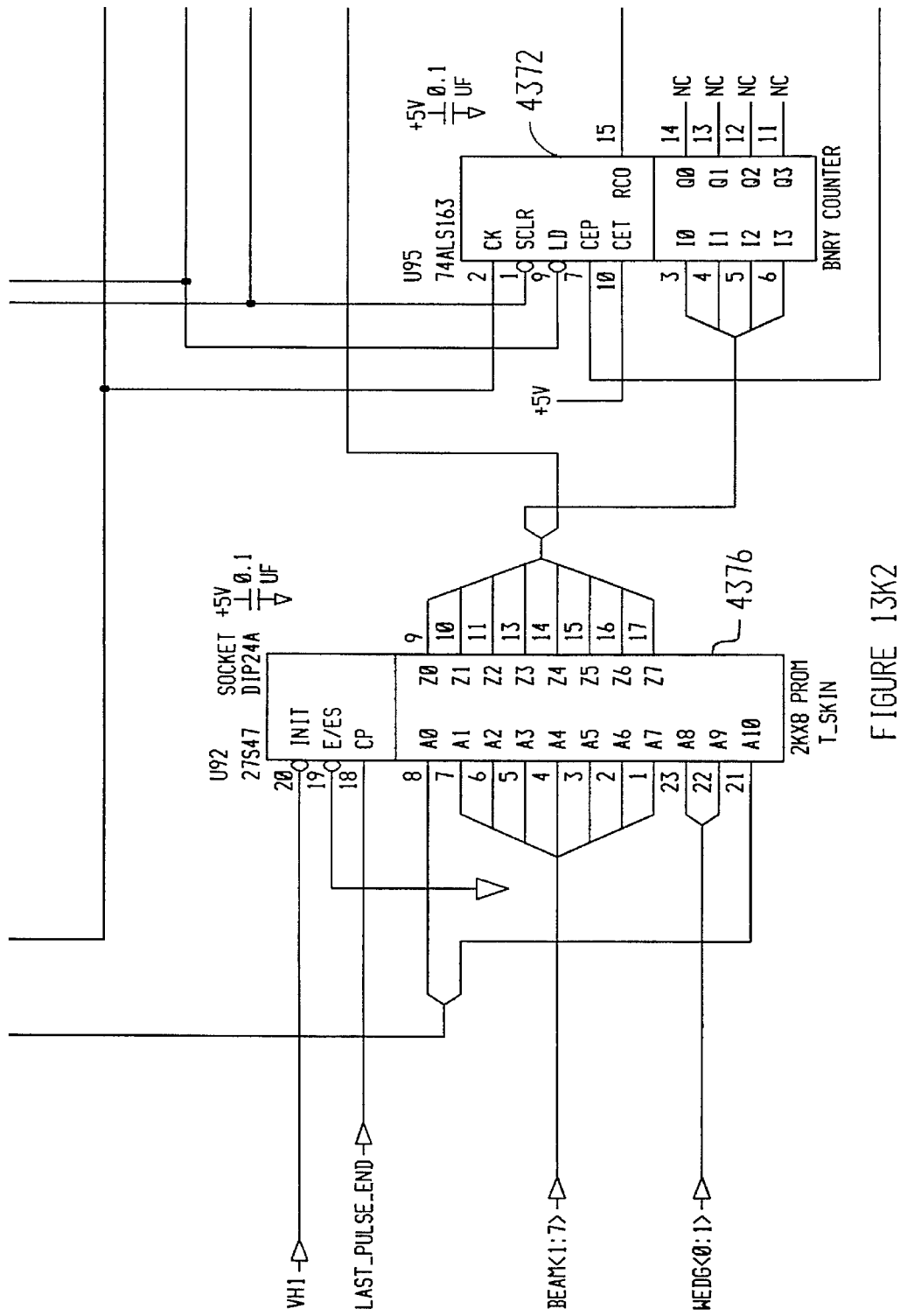
FIGURE 13K2

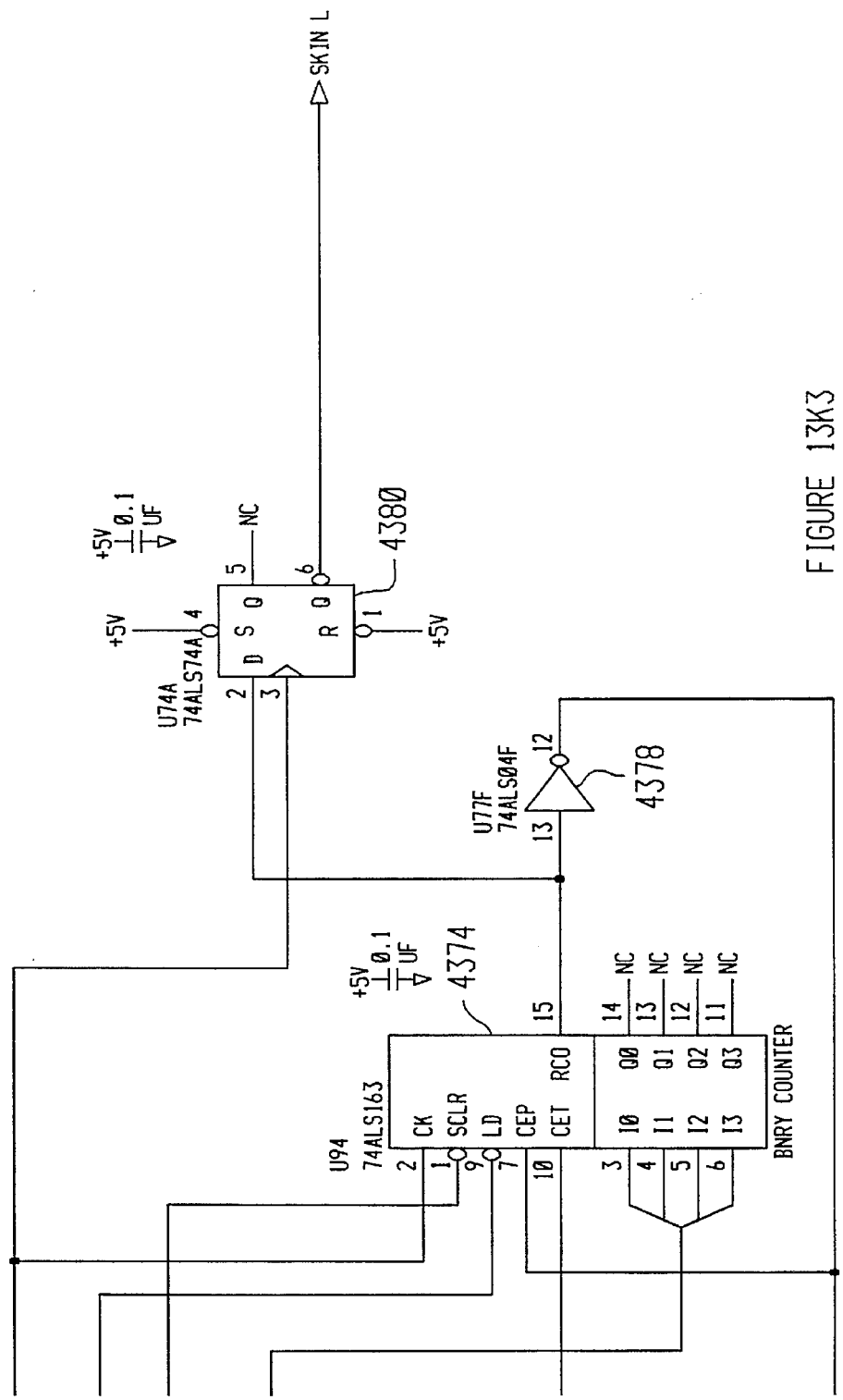
FIGURE 13K3

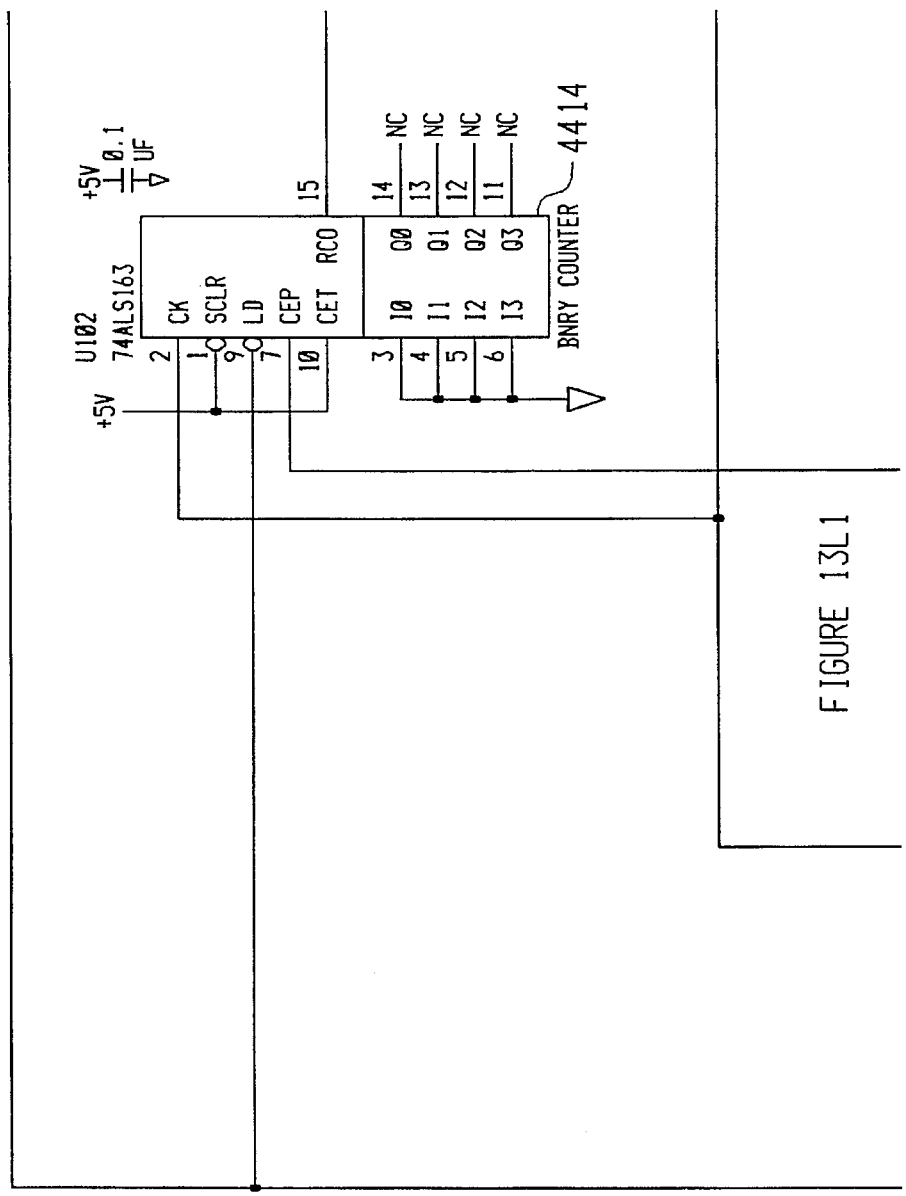
FIGURE 13L1

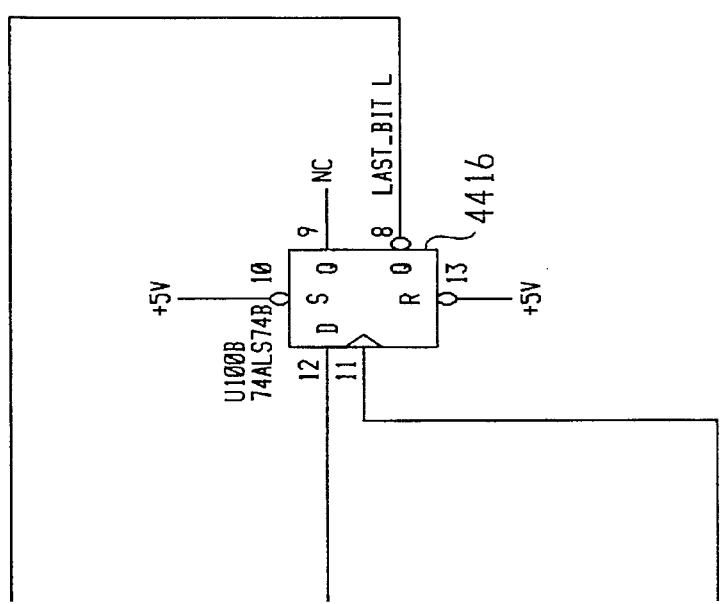
FIGURE 13L2

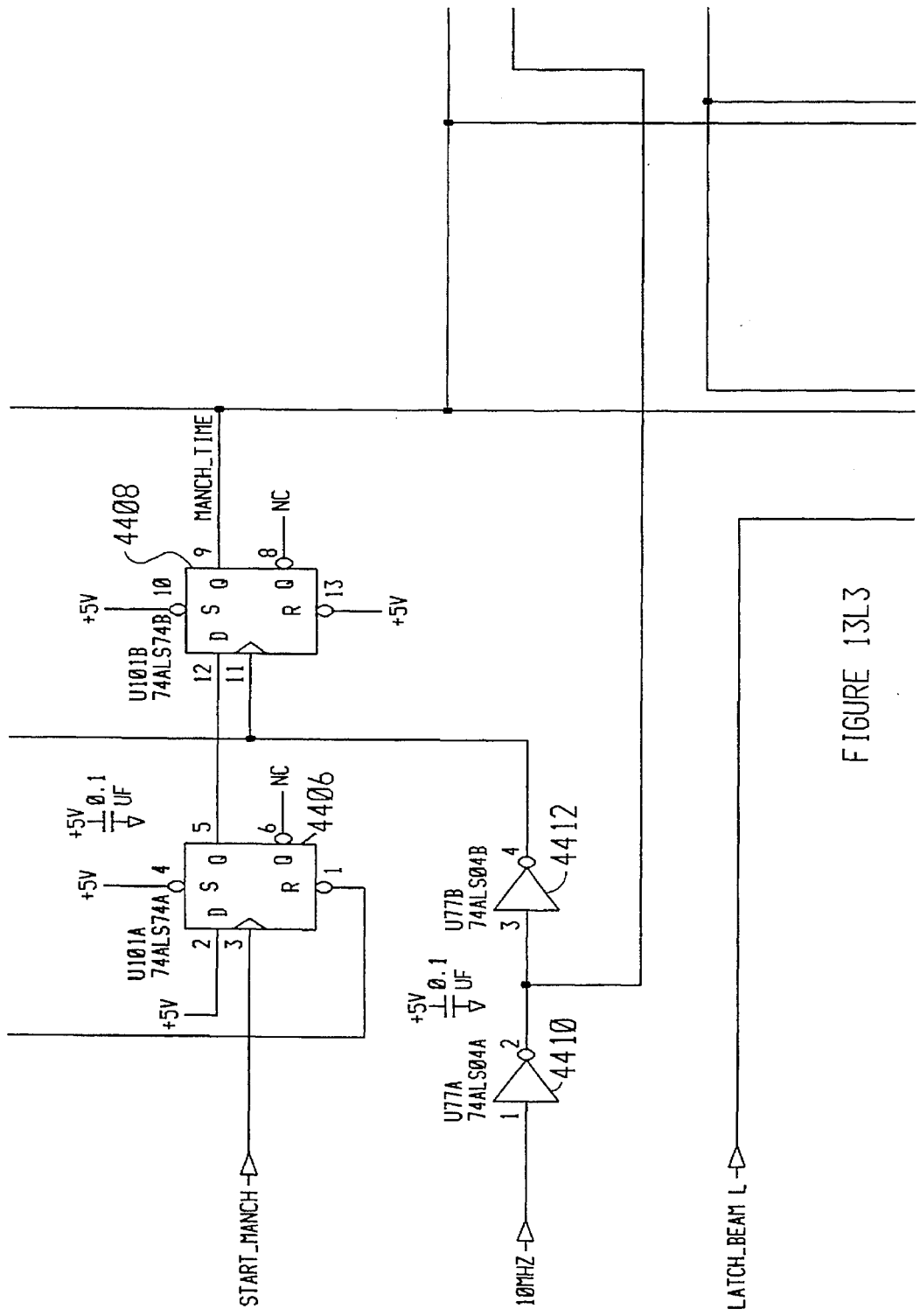
FIGURE 13L3

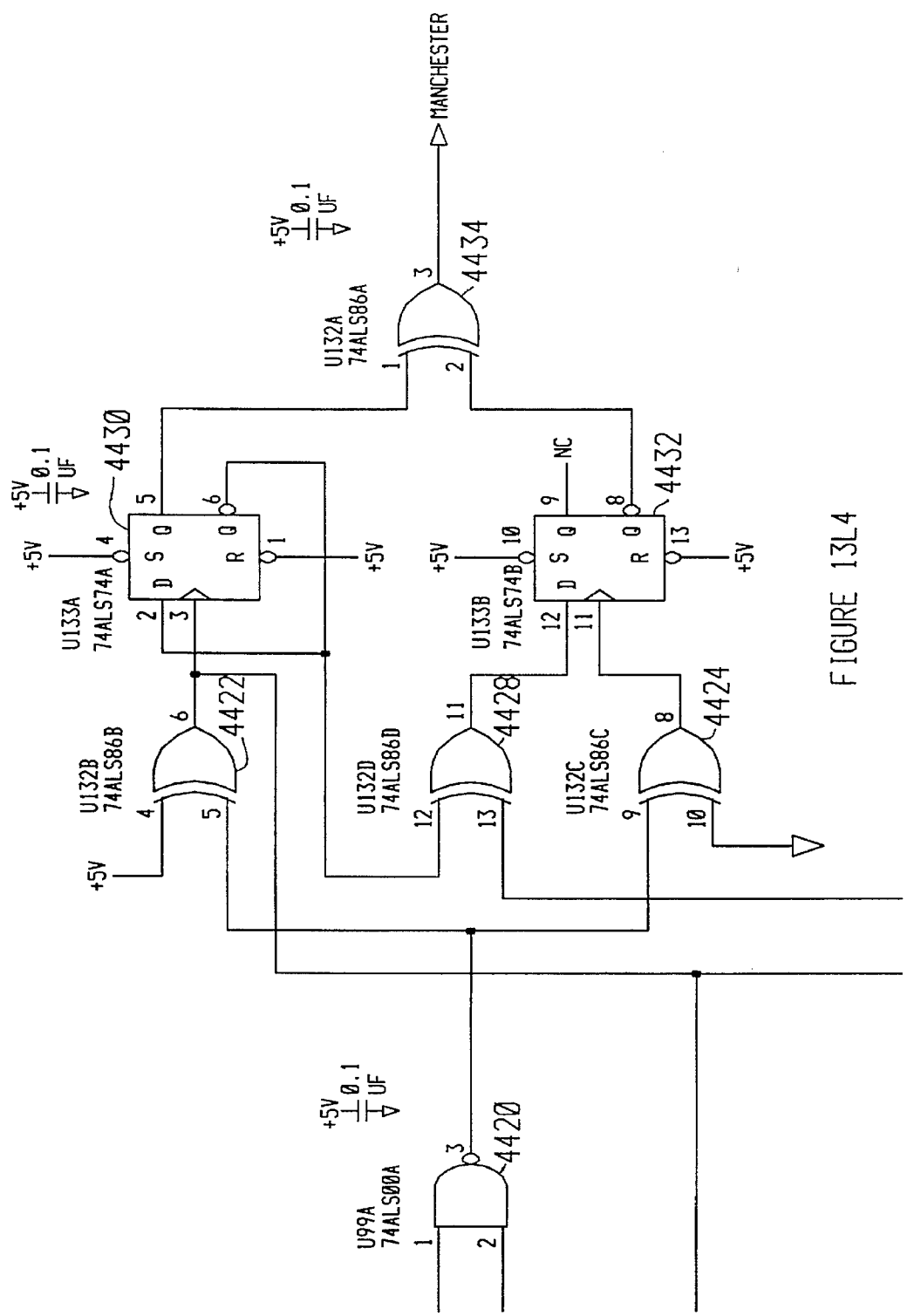
FIGURE 13L4

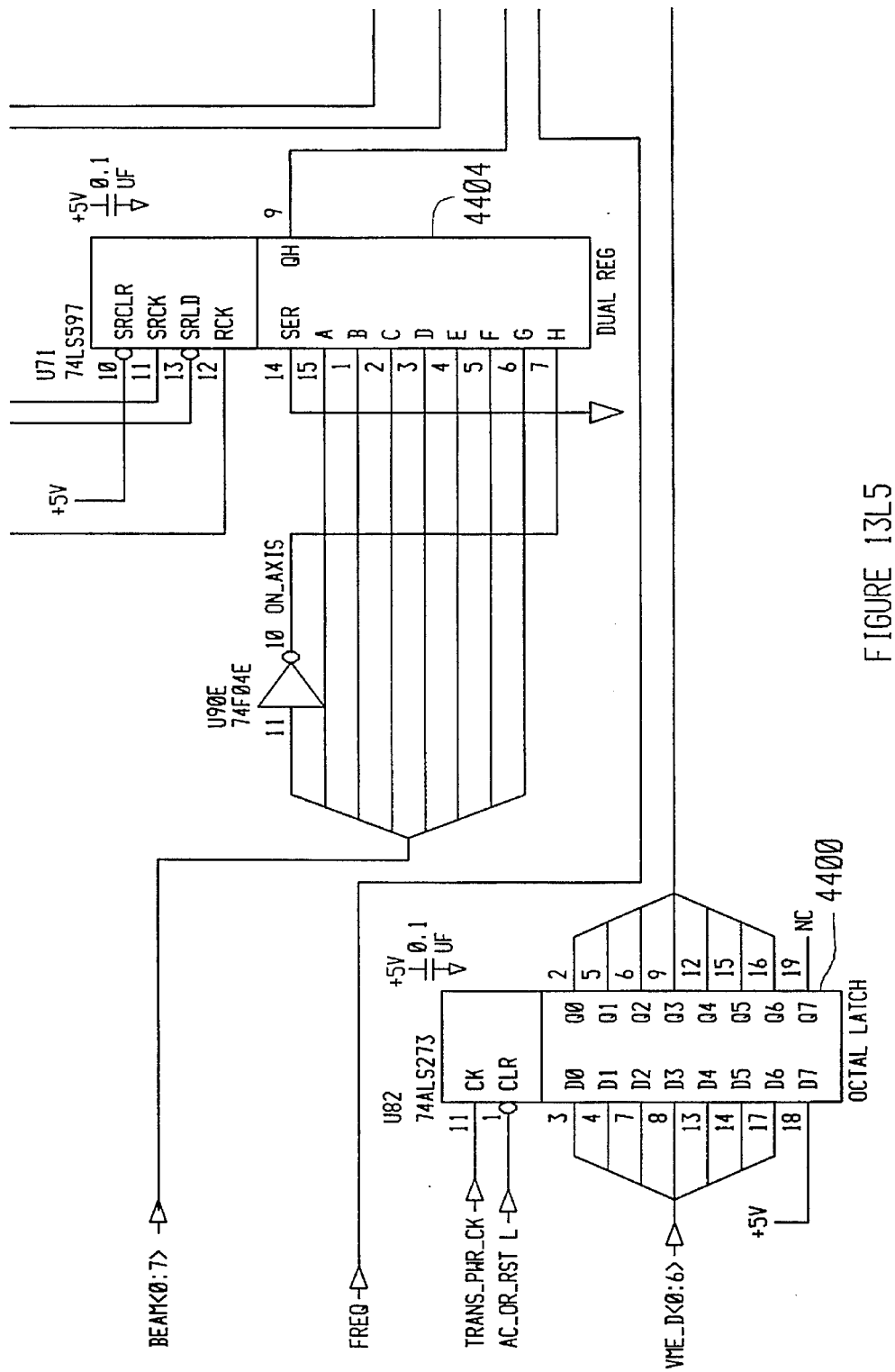
FIGURE 13L5

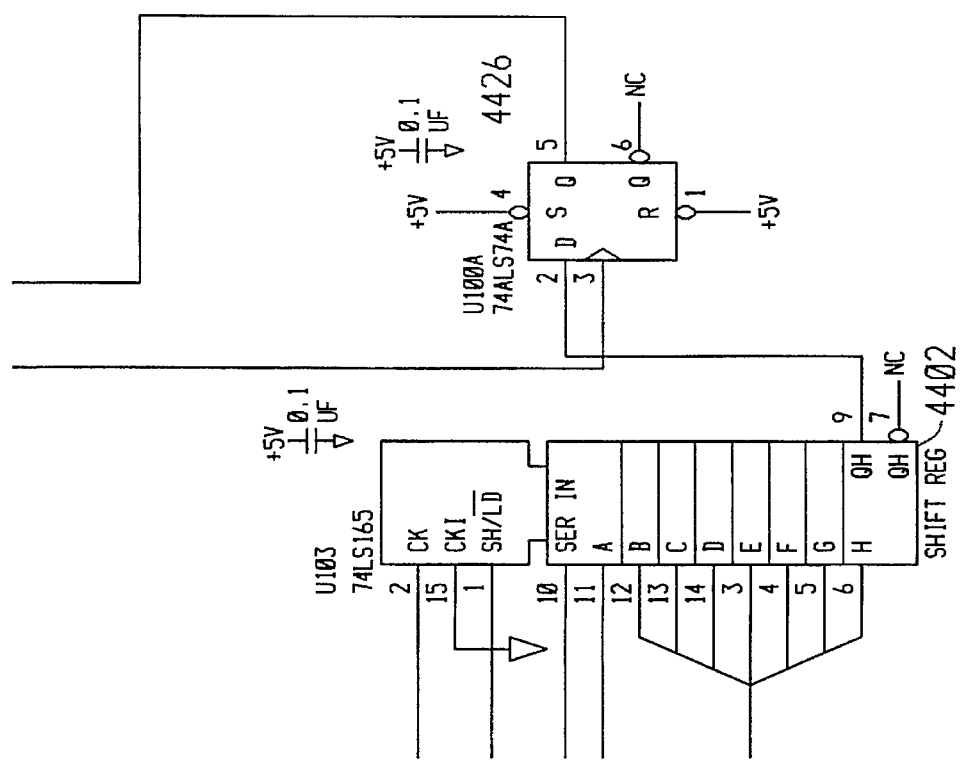
FIGURE 13L6

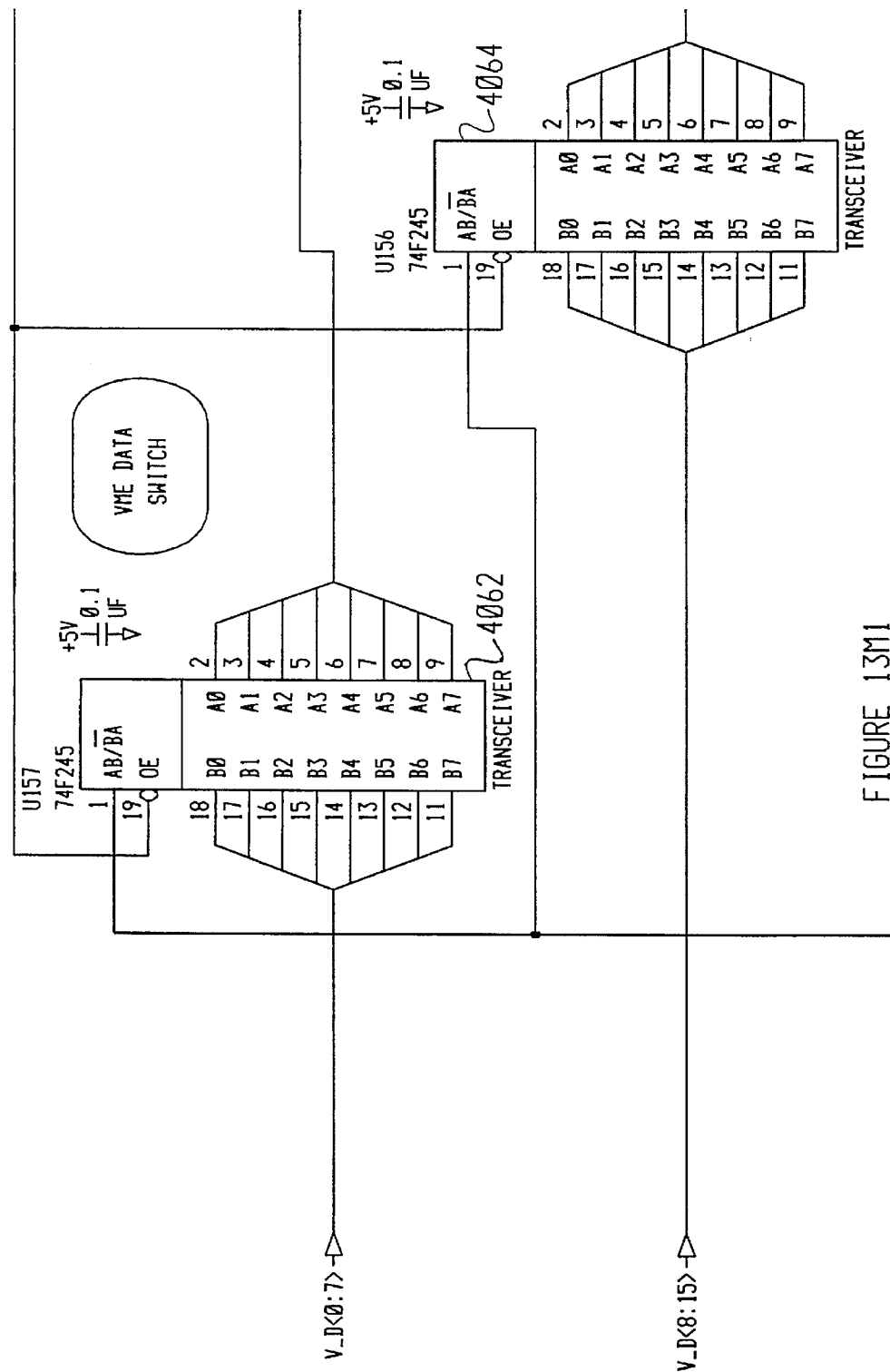
FIGURE 13M1

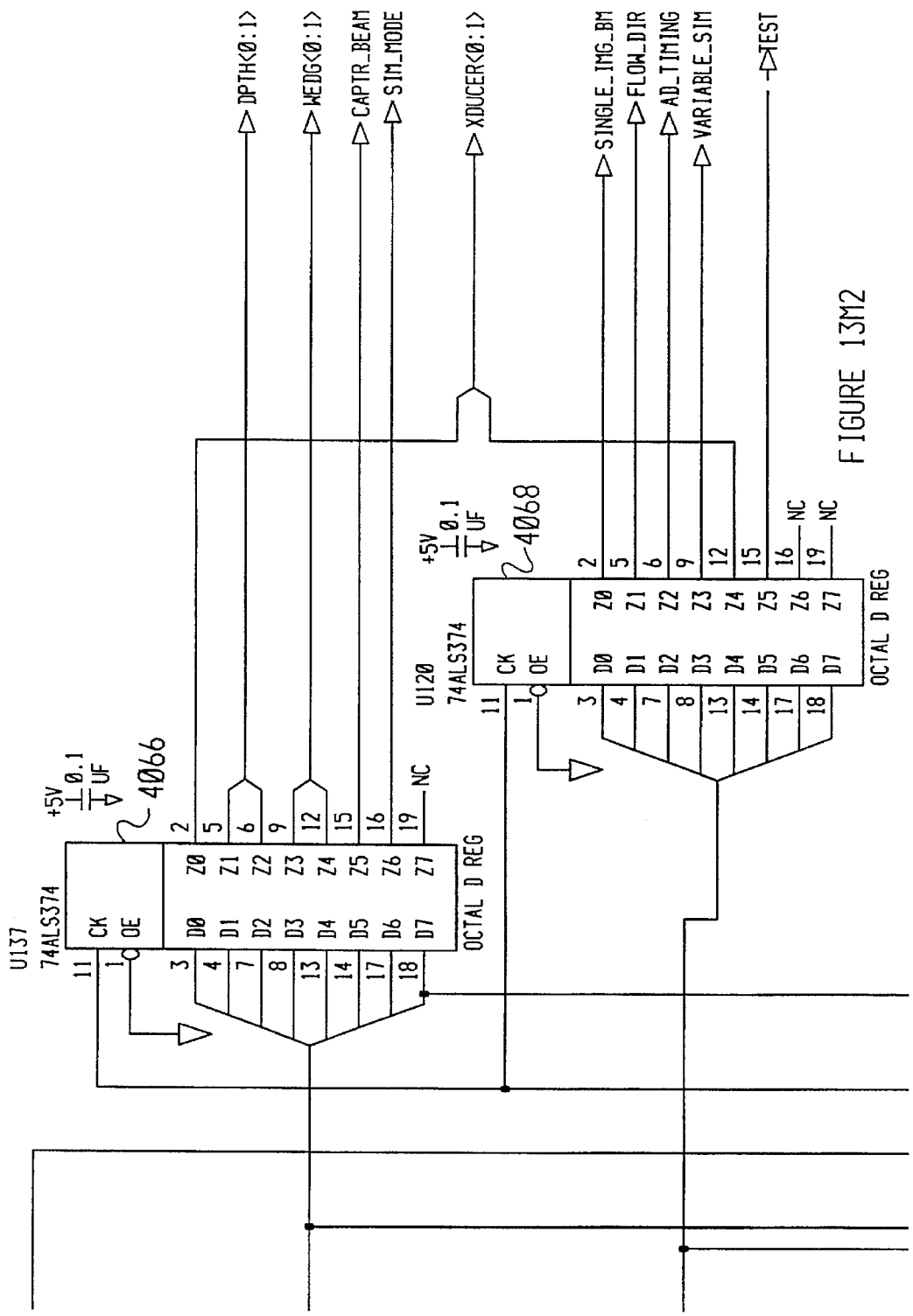
FIGURE 13M2

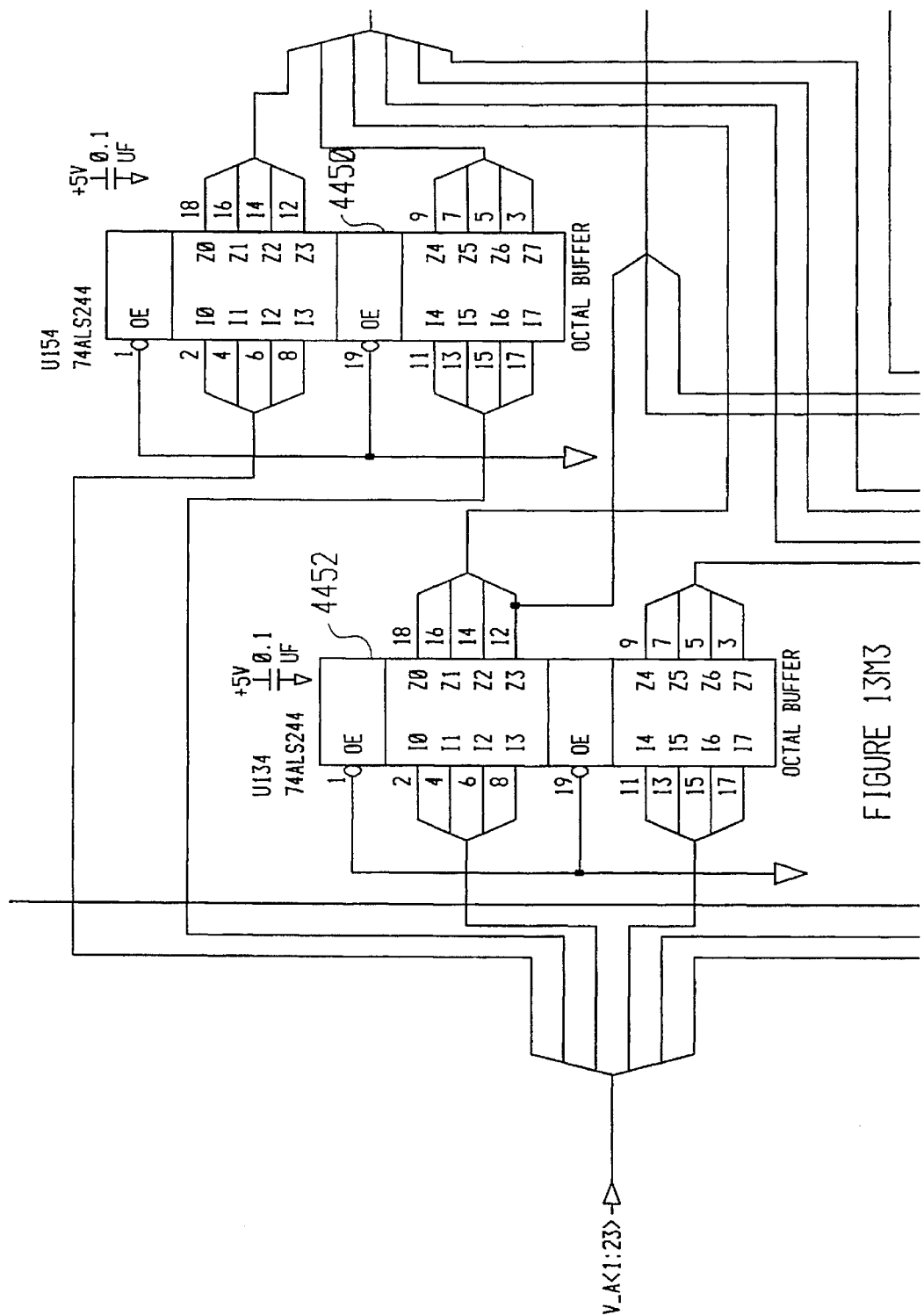
FIGURE 13M3

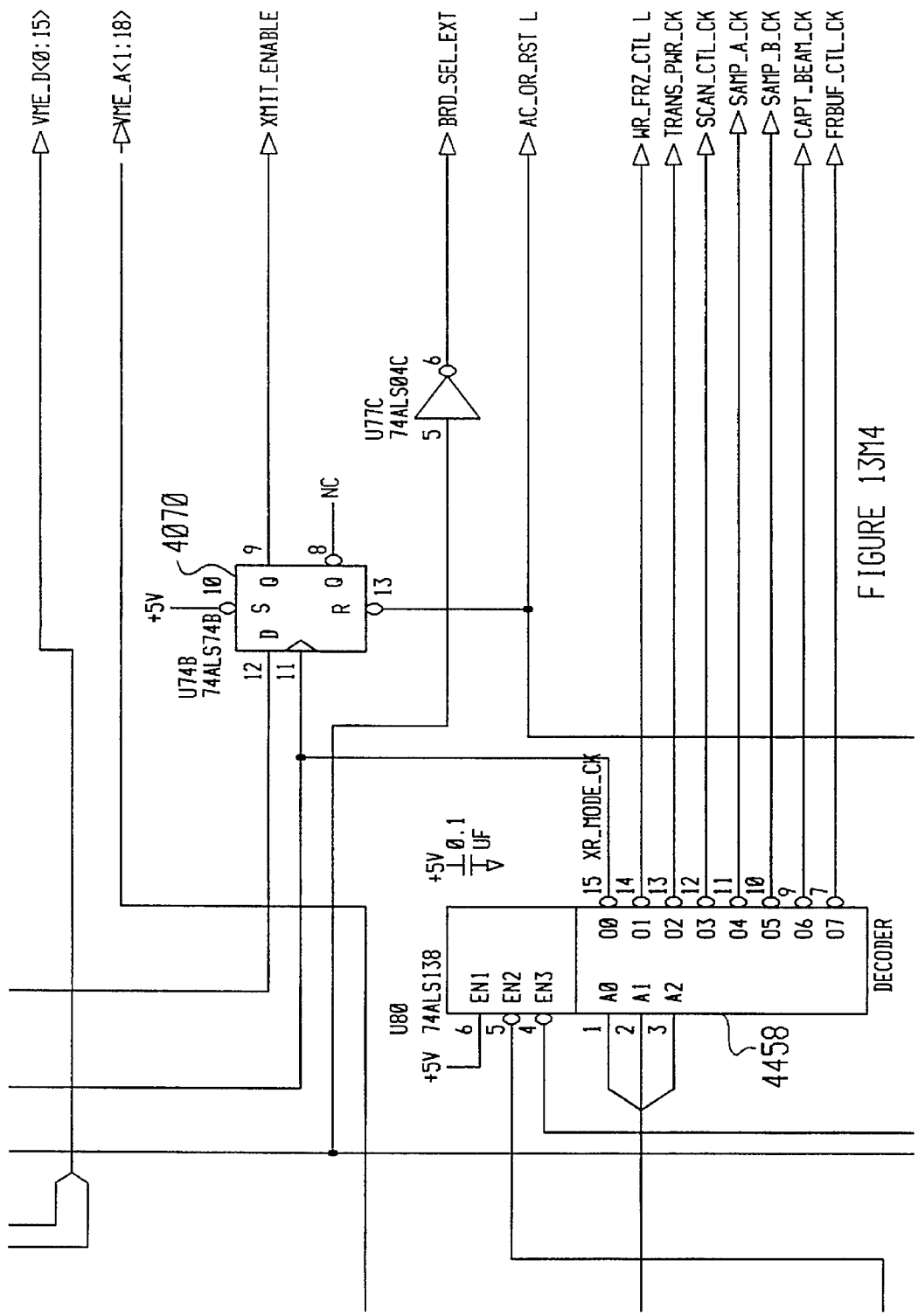
FIGURE 13M4

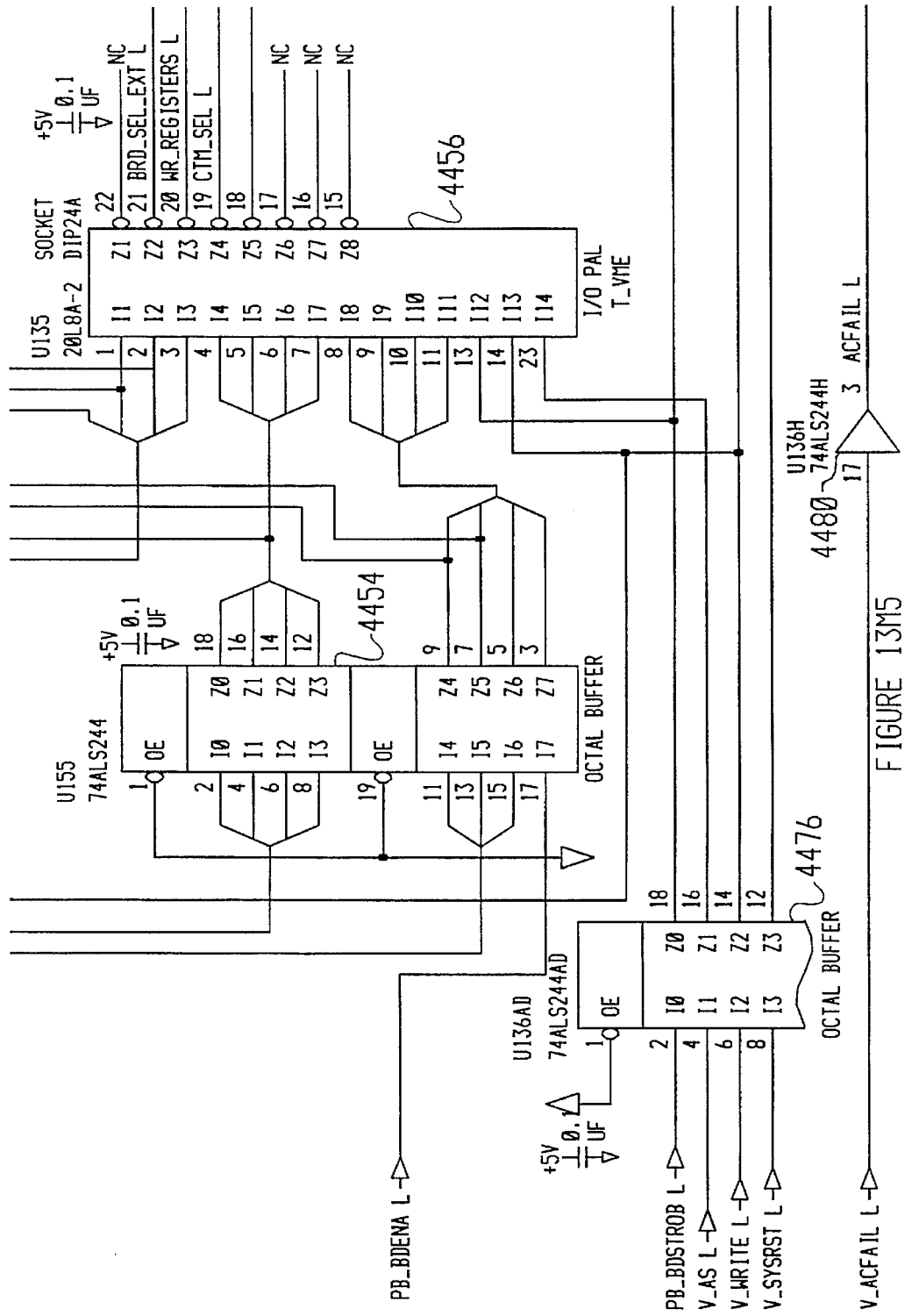
FIGURE 13M5

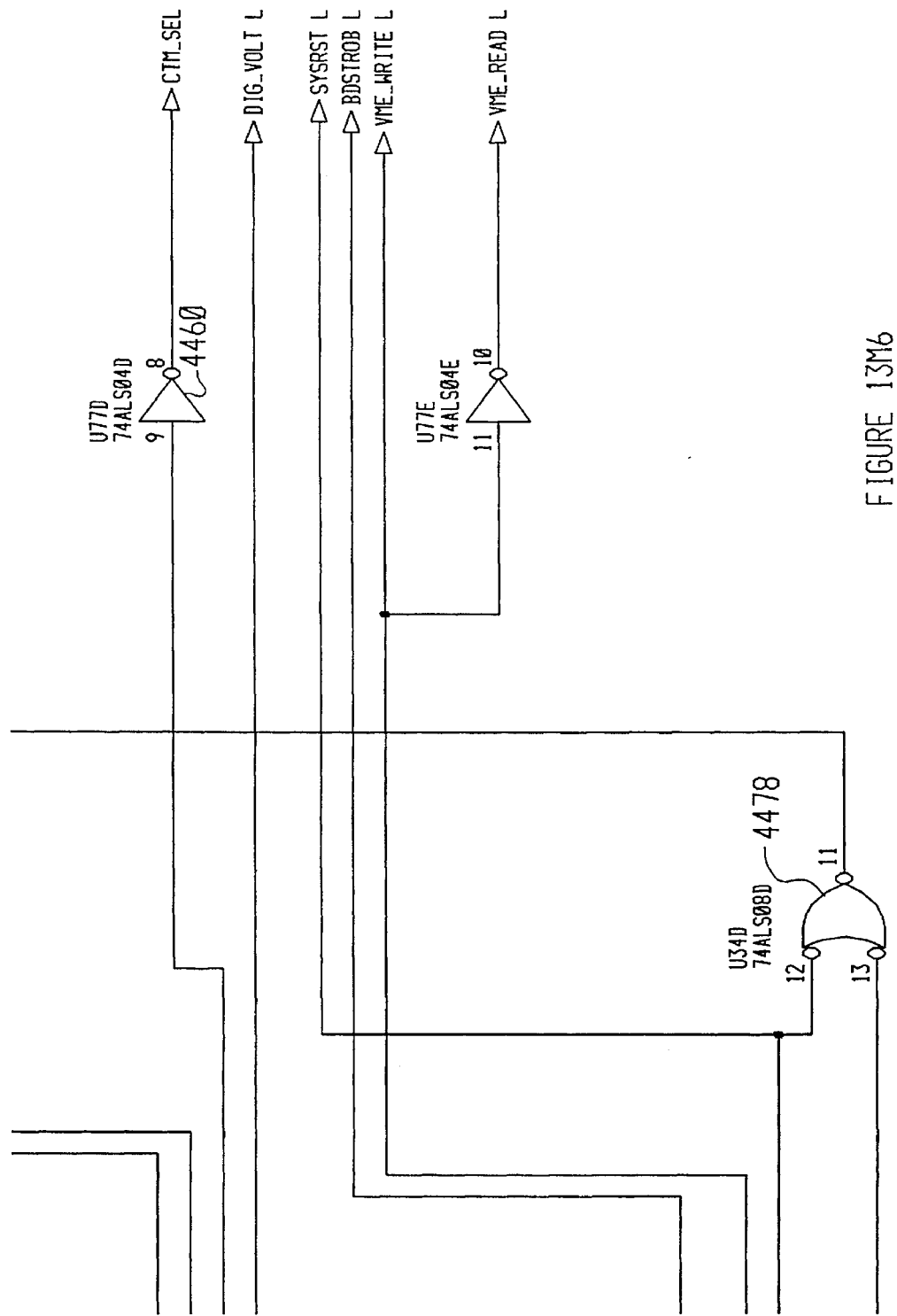
FIGURE 13M6

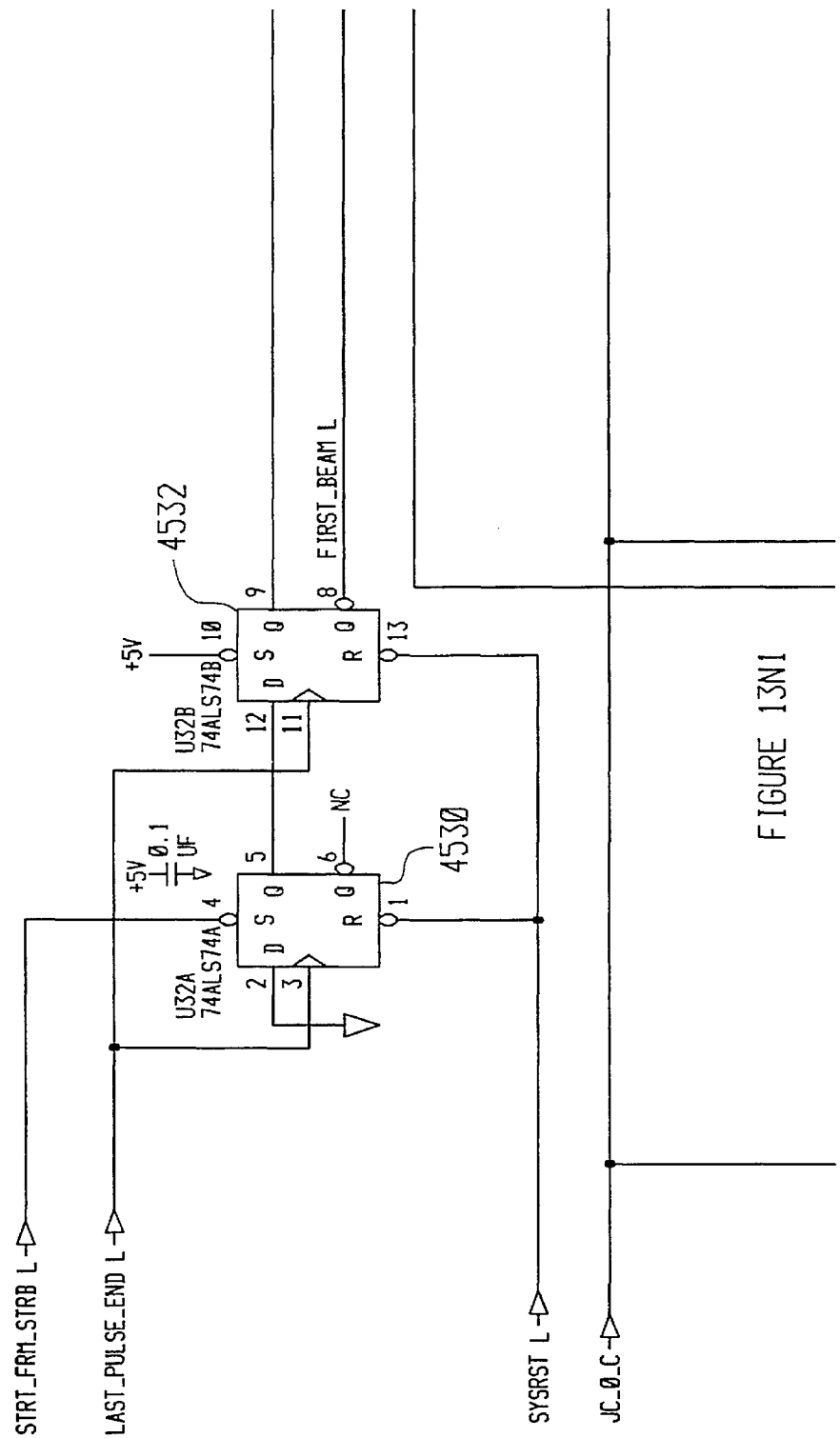

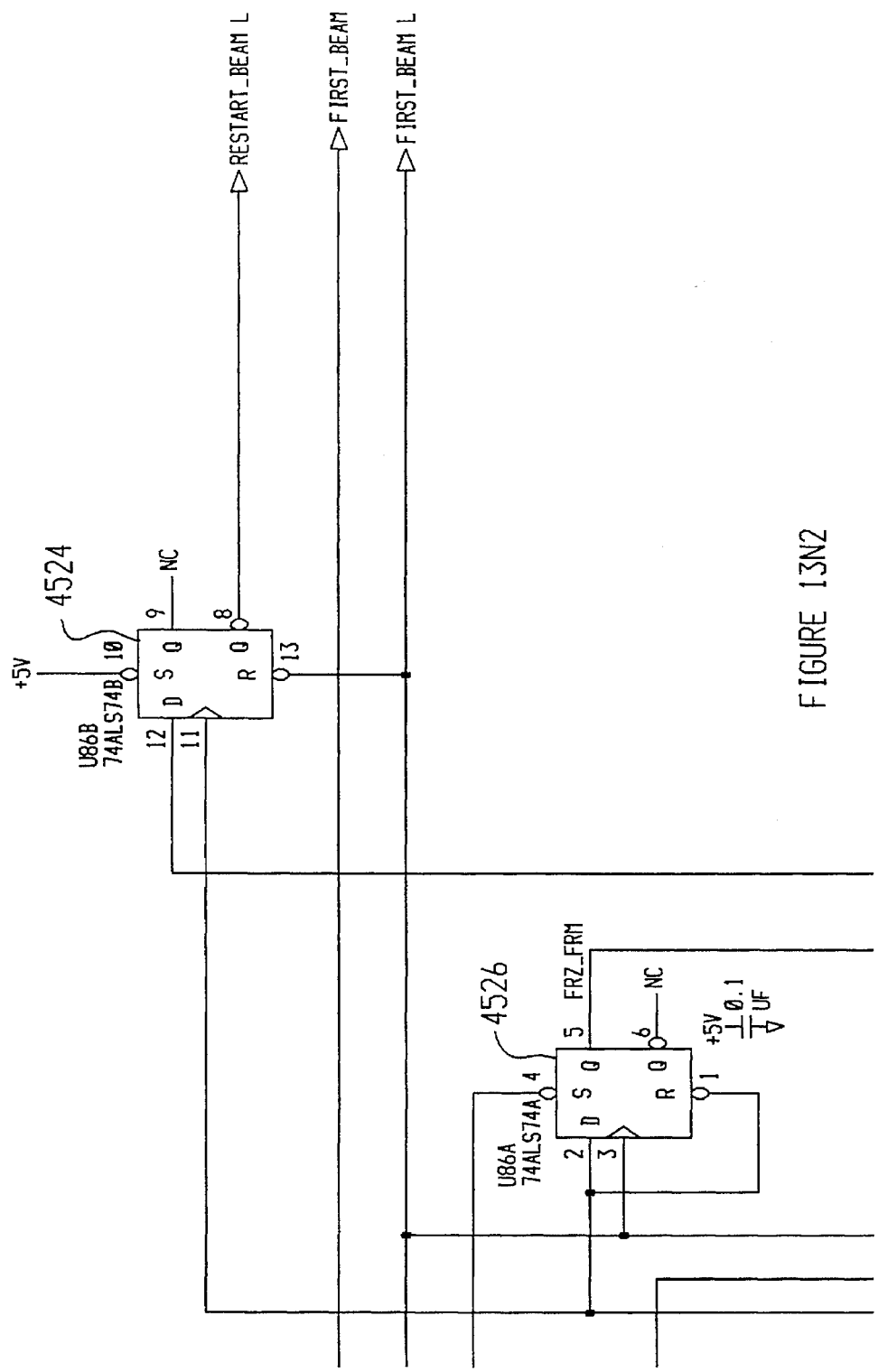
FIGURE 13N2

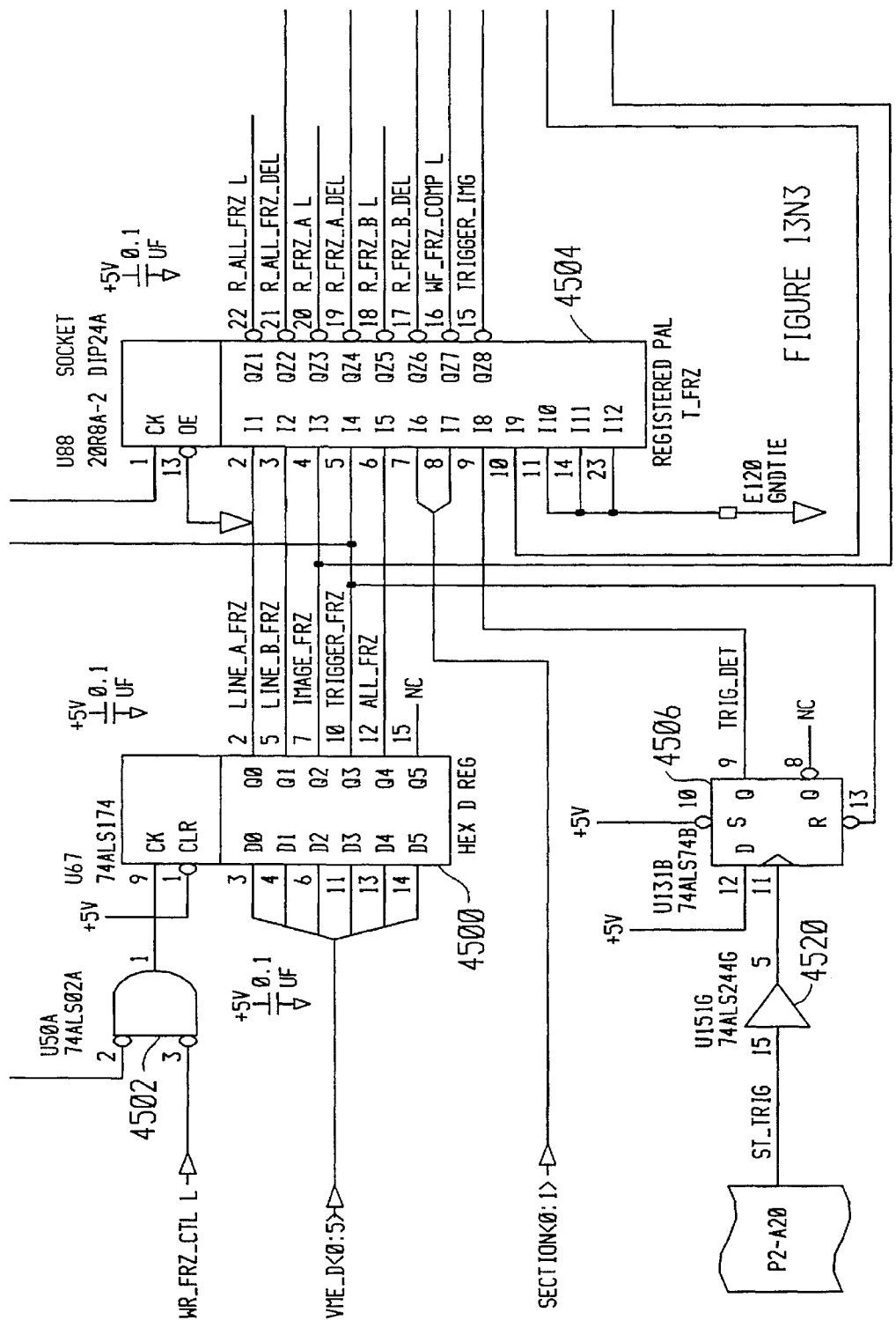

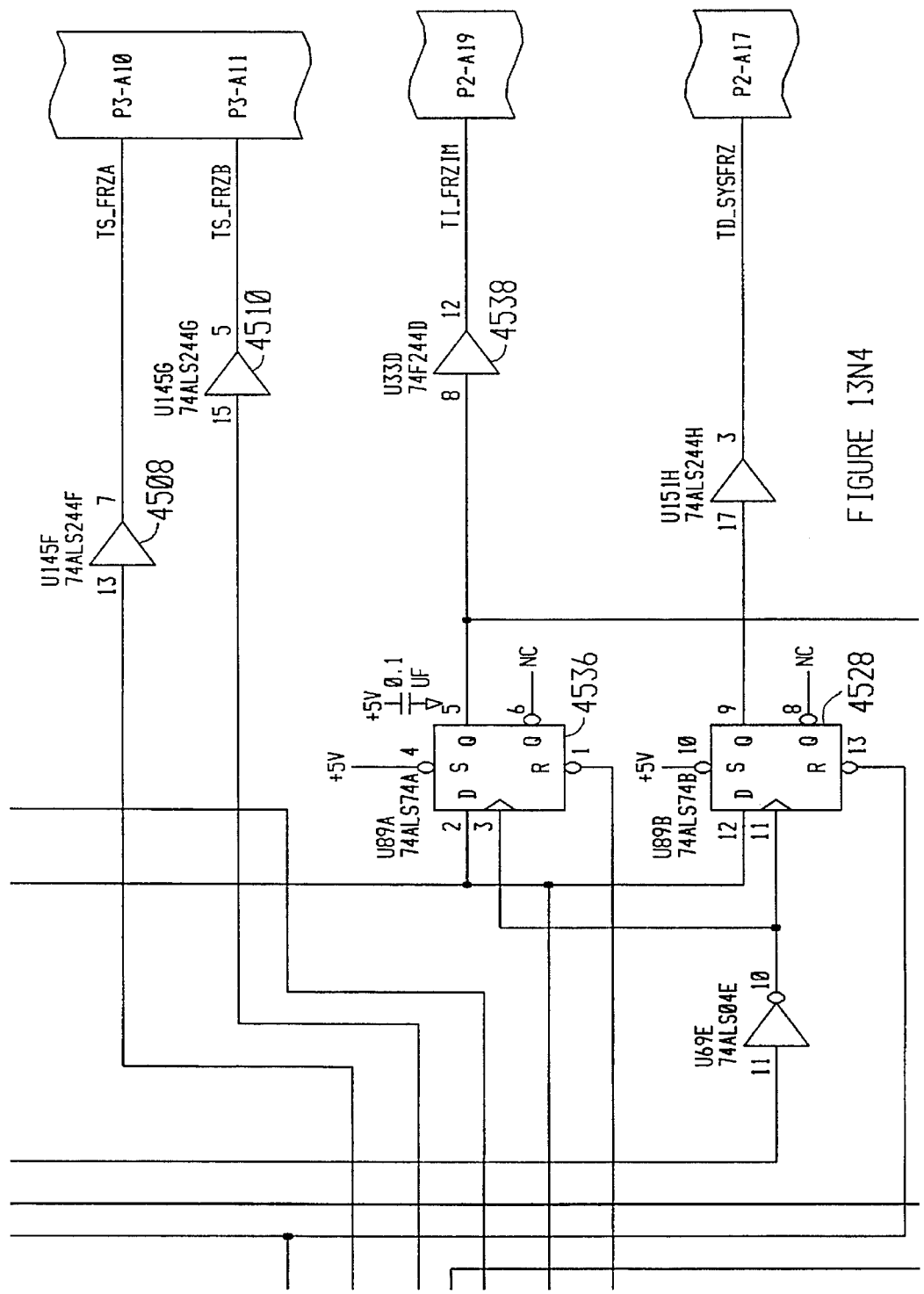
FIGURE 13N4

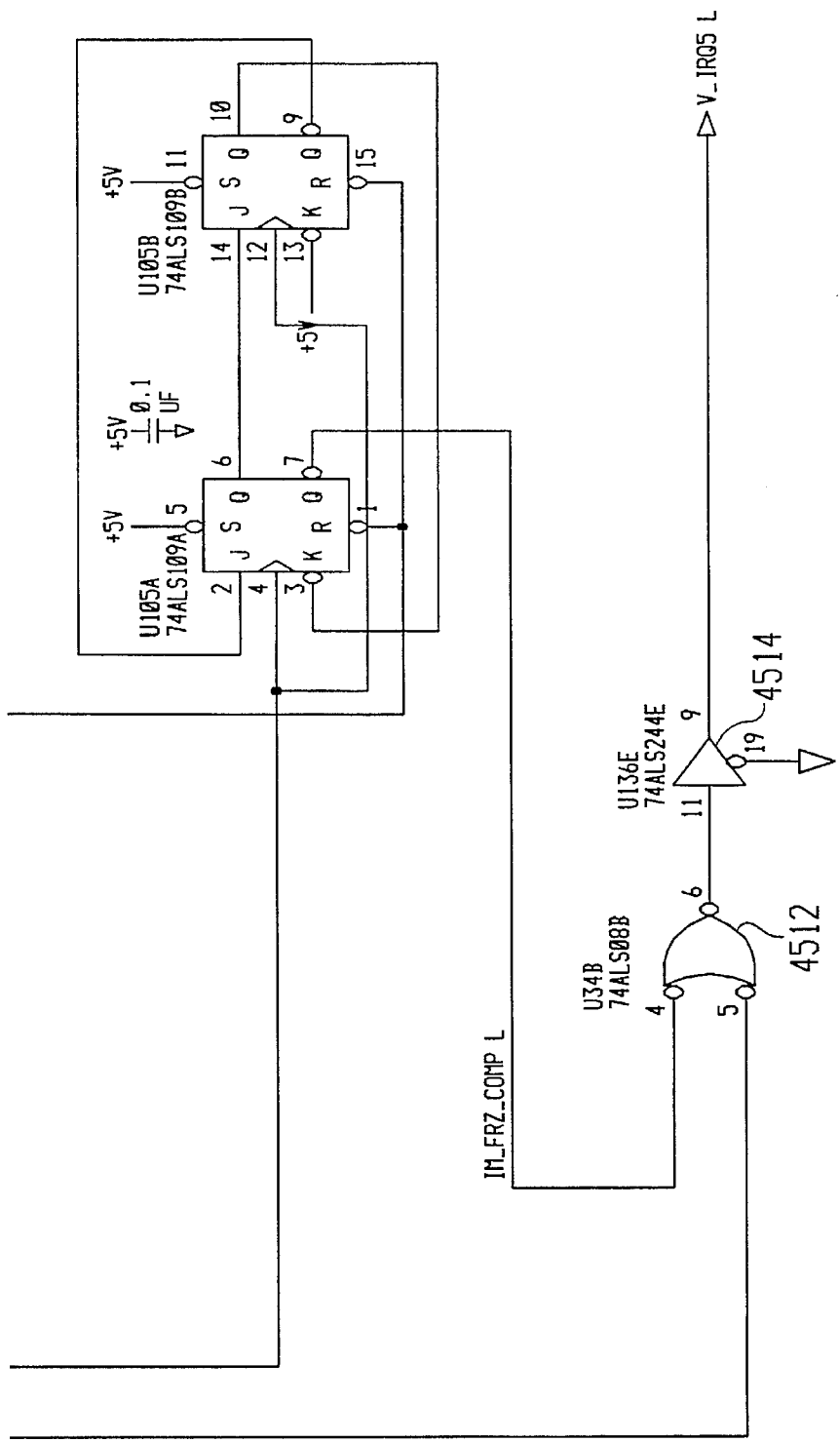
FIGURE 13N5

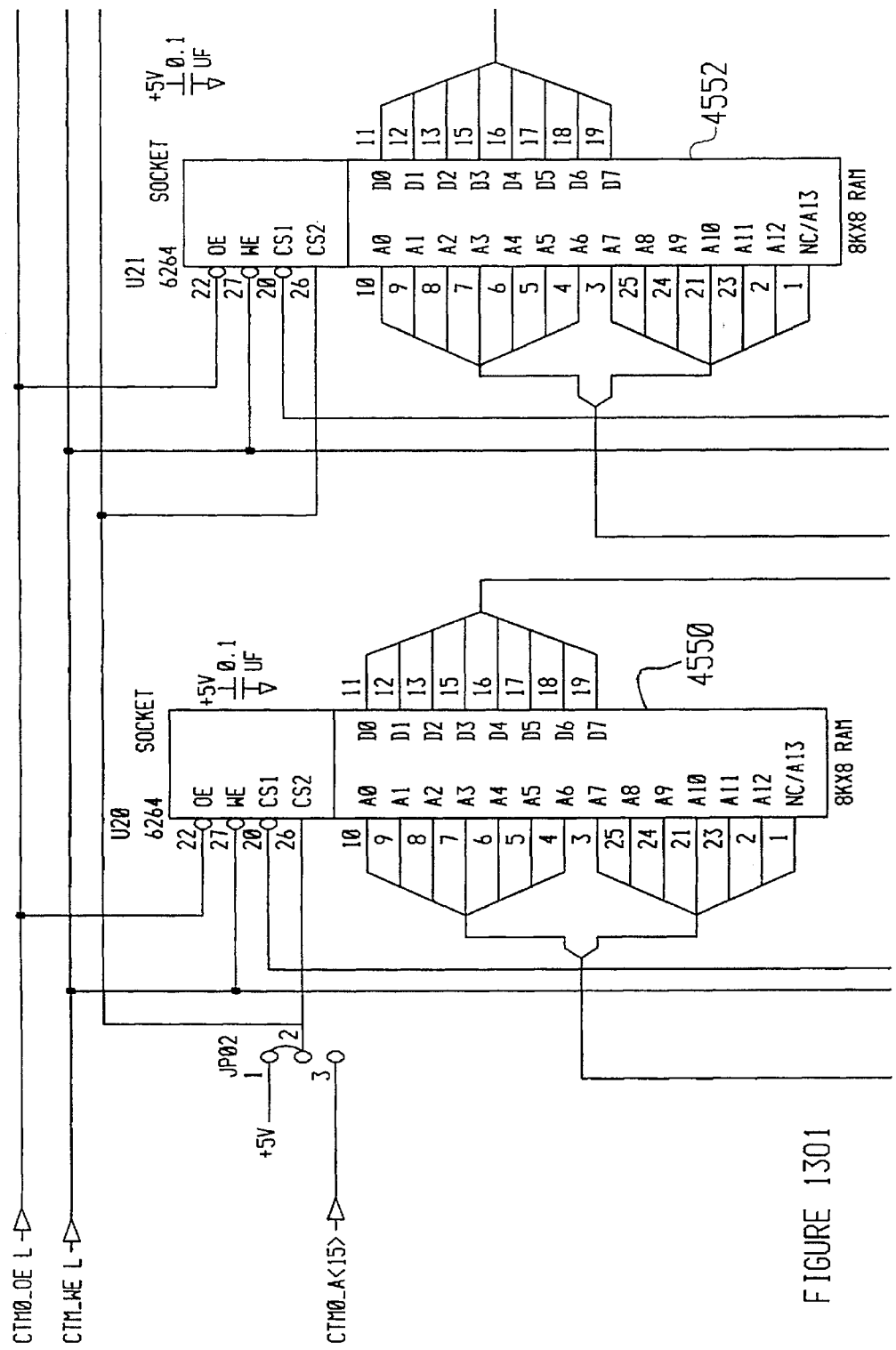
FIGURE 1301

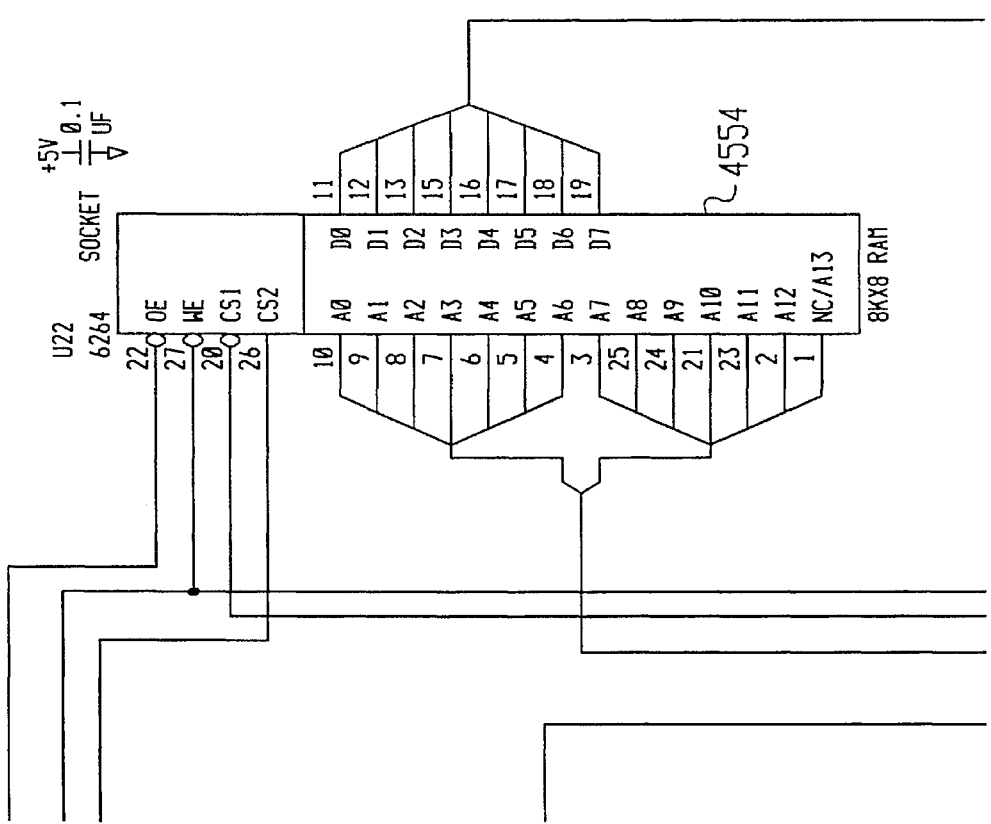
FIGURE 1302

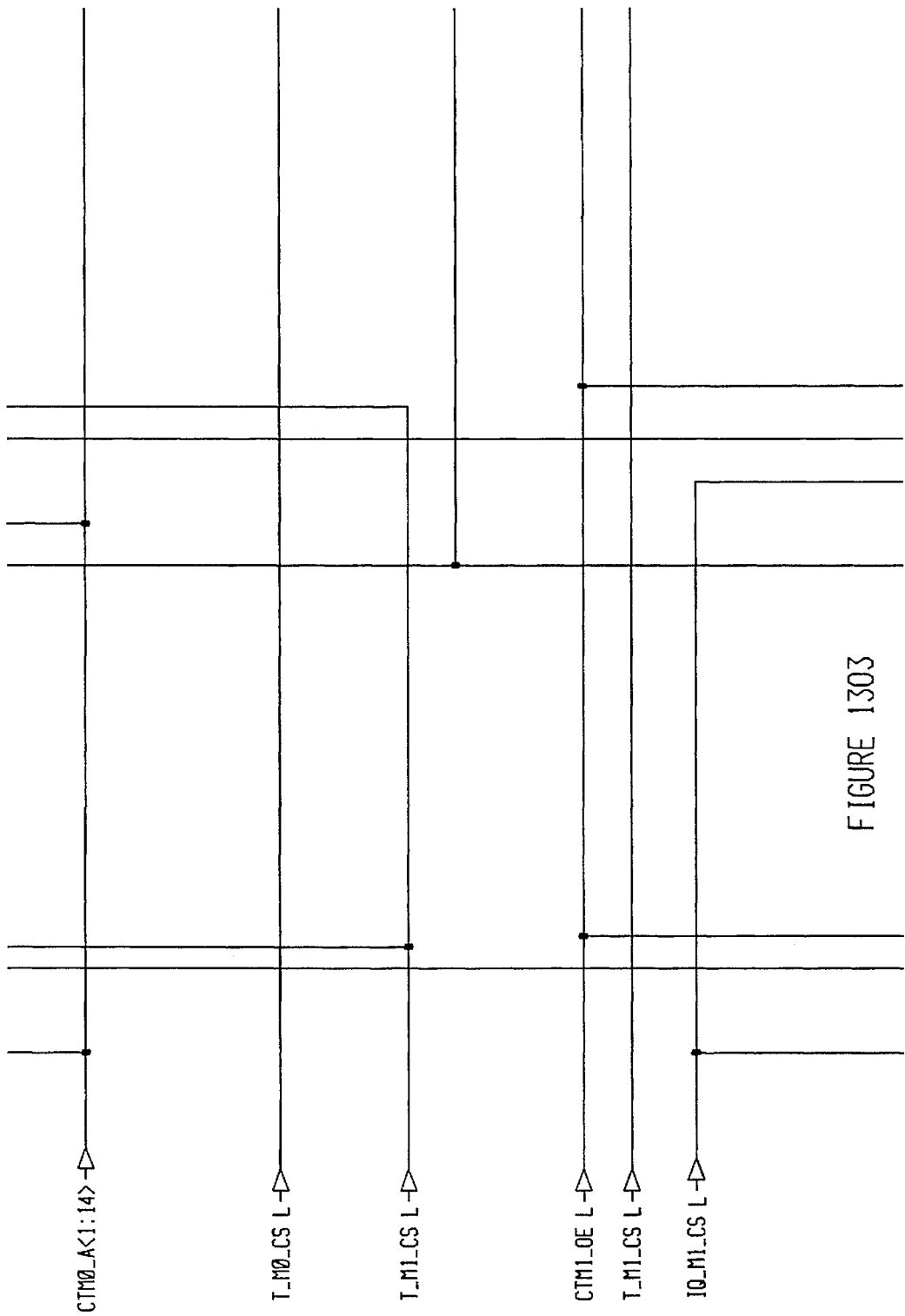
FIGURE 1303

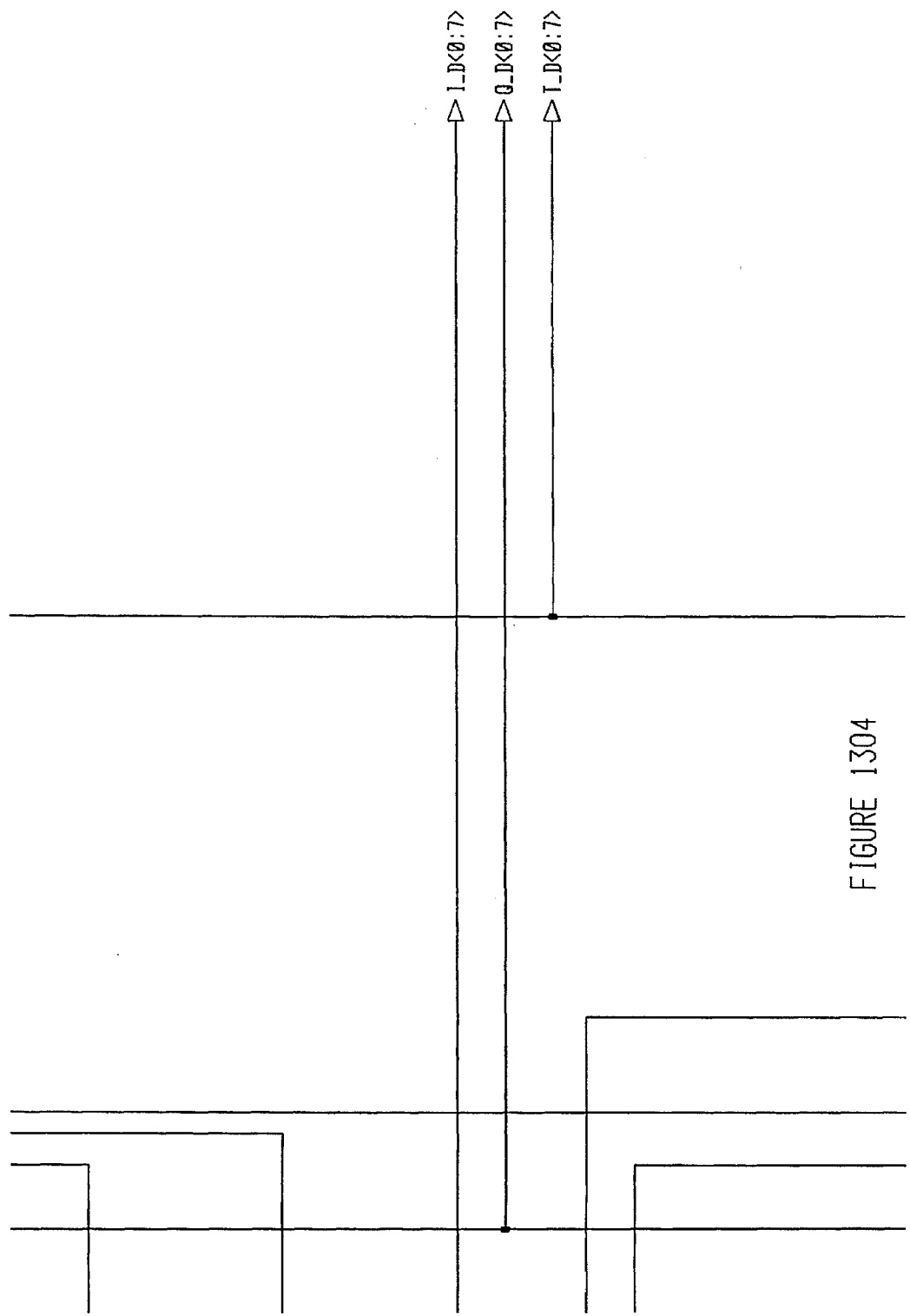
FIGURE 1304

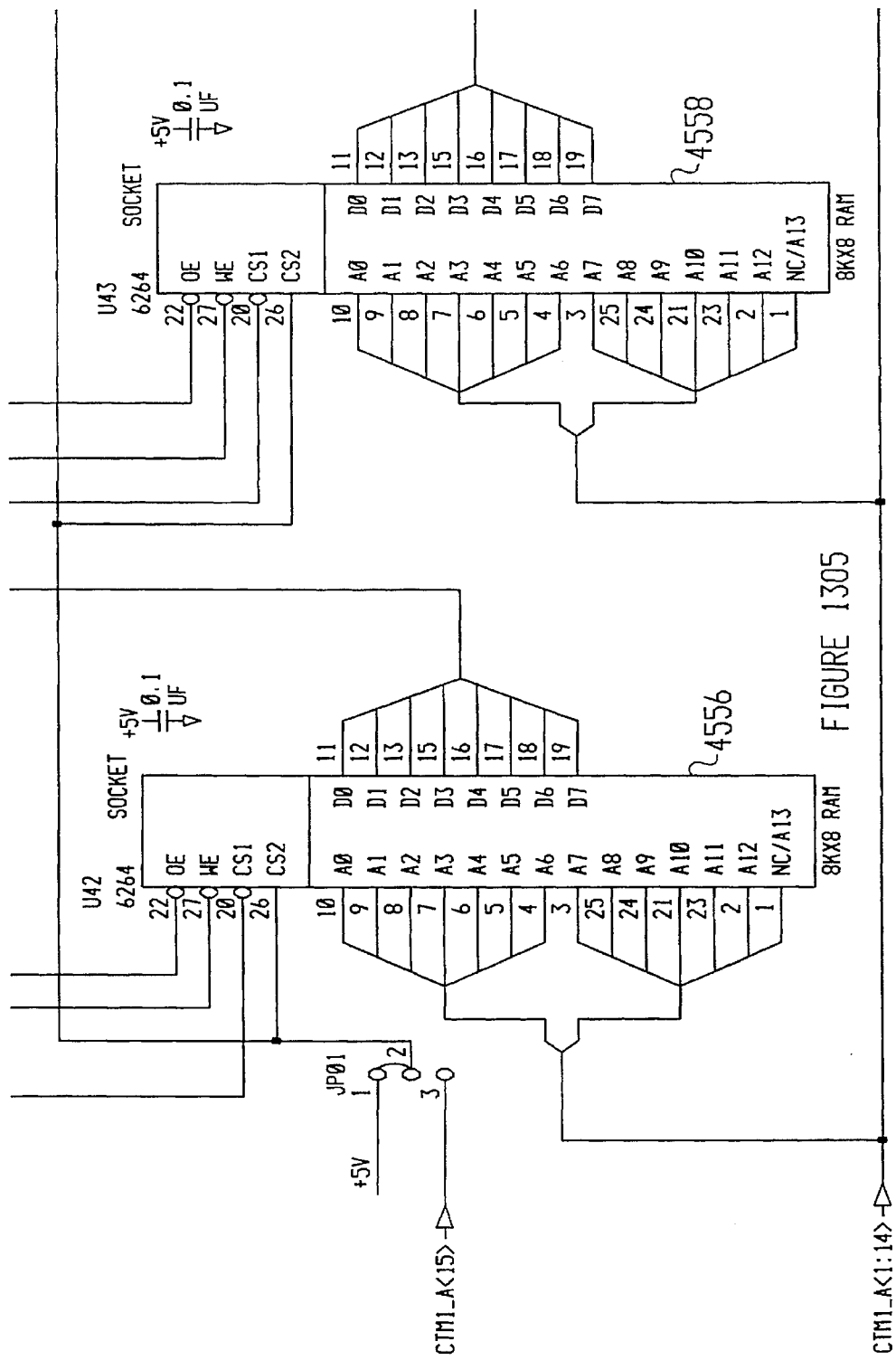
FIGURE 1305

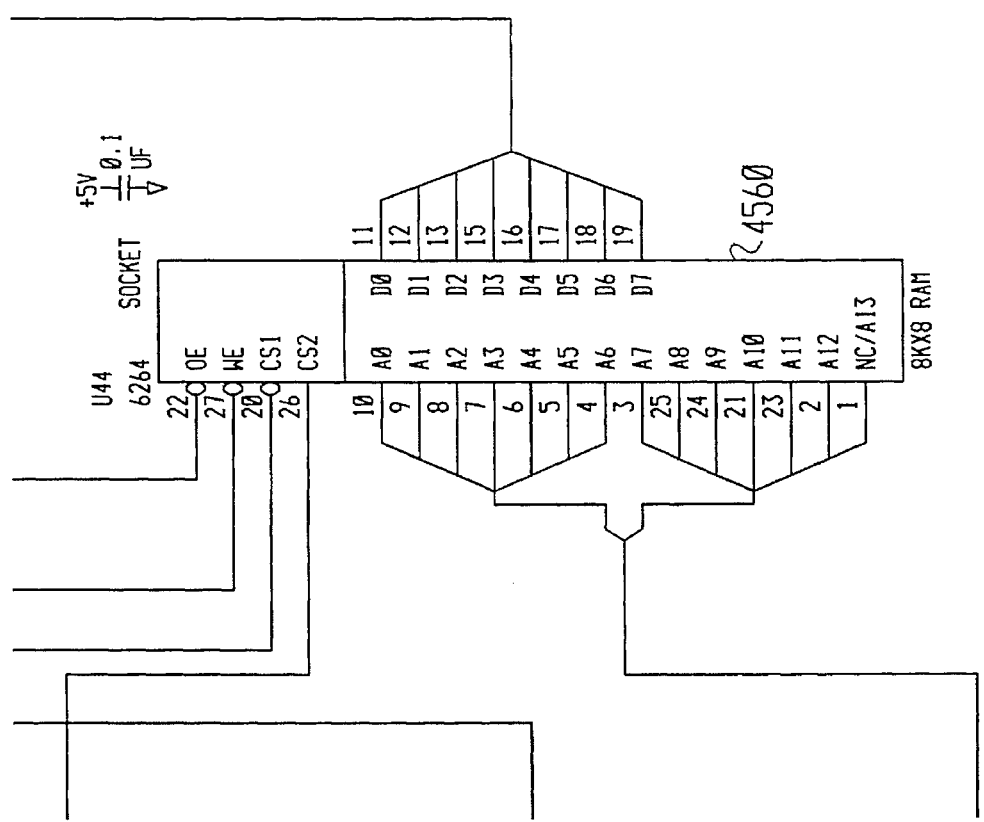
FIGURE 1306

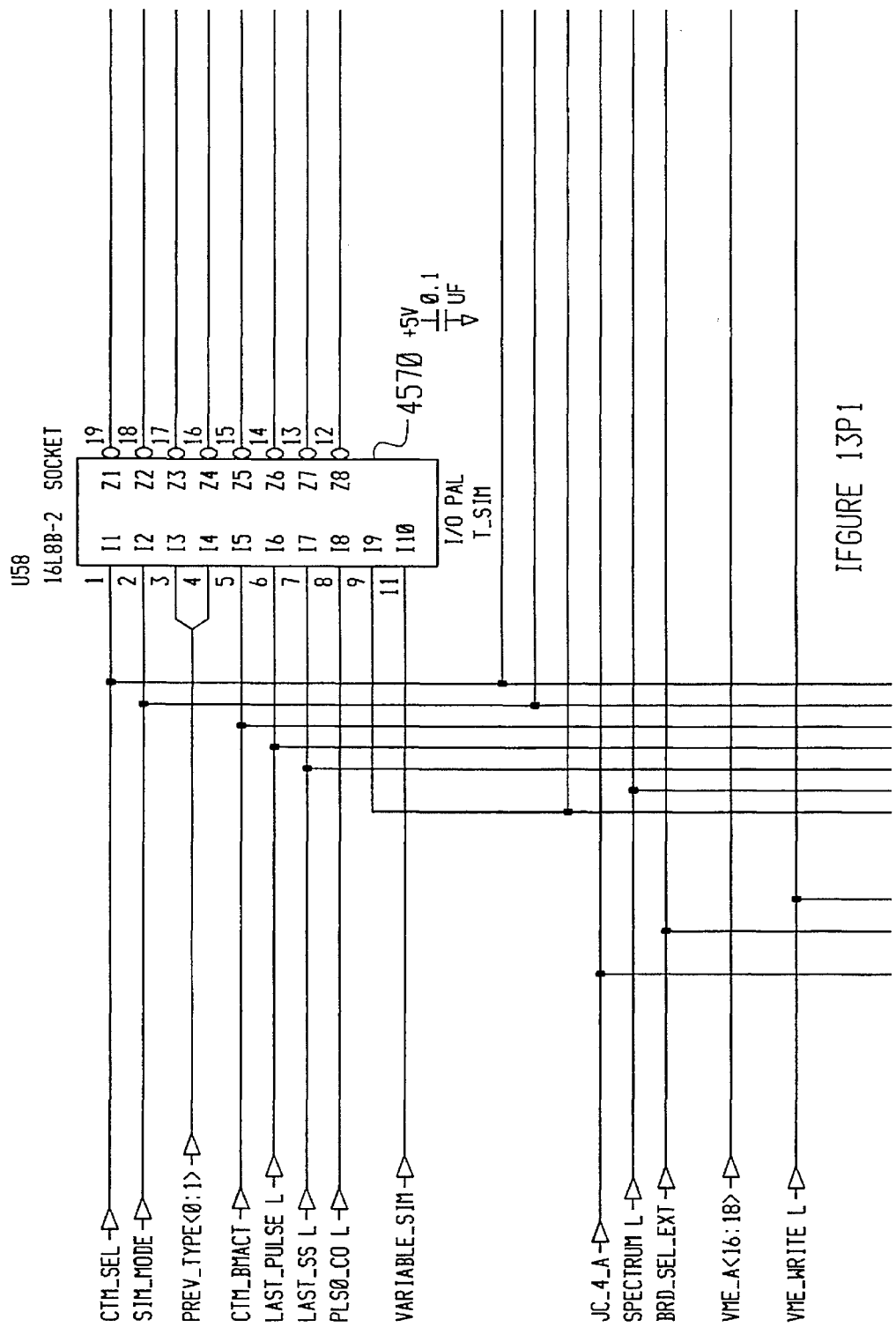

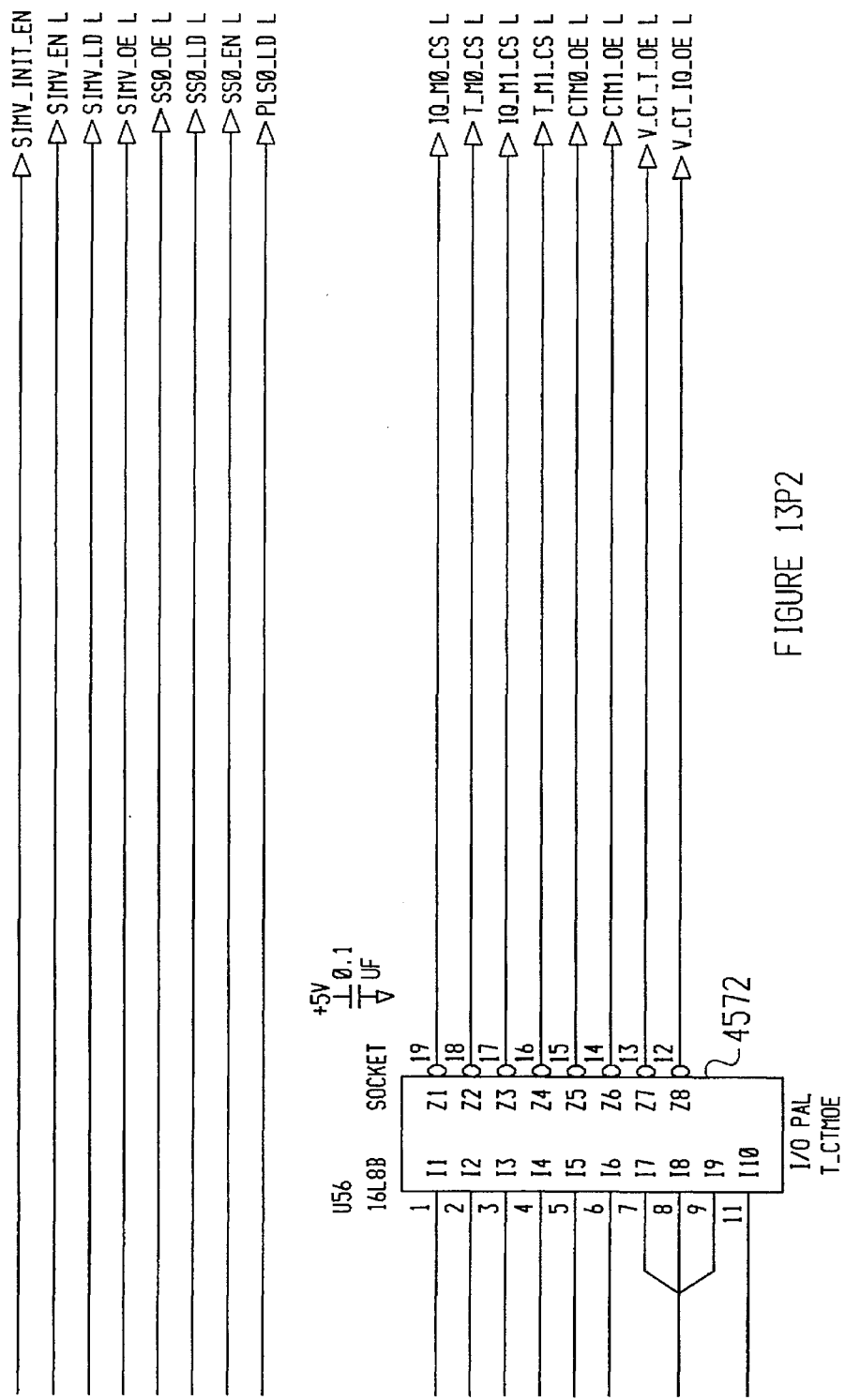
FIGURE 13P2

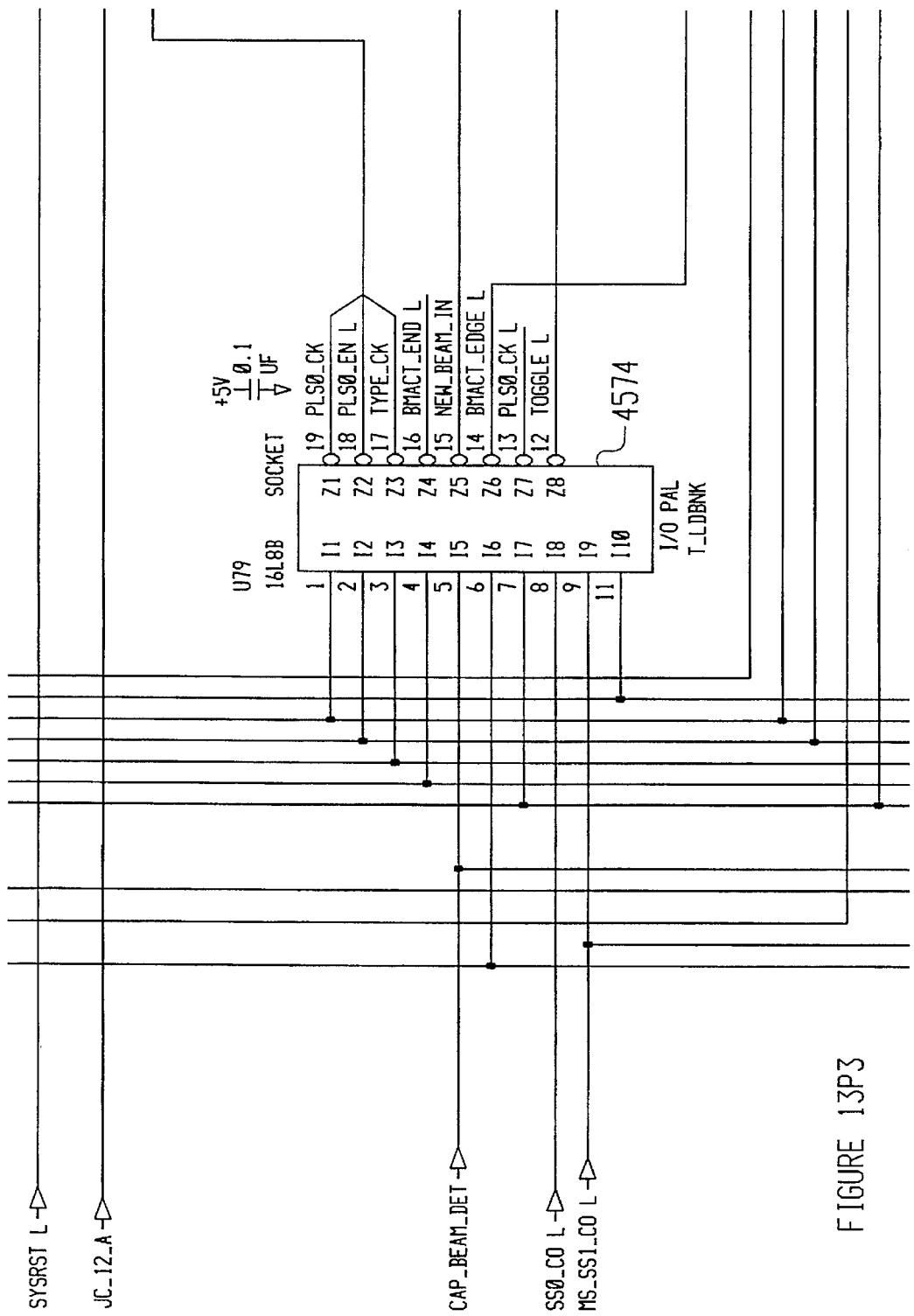
FIGURE 13P3

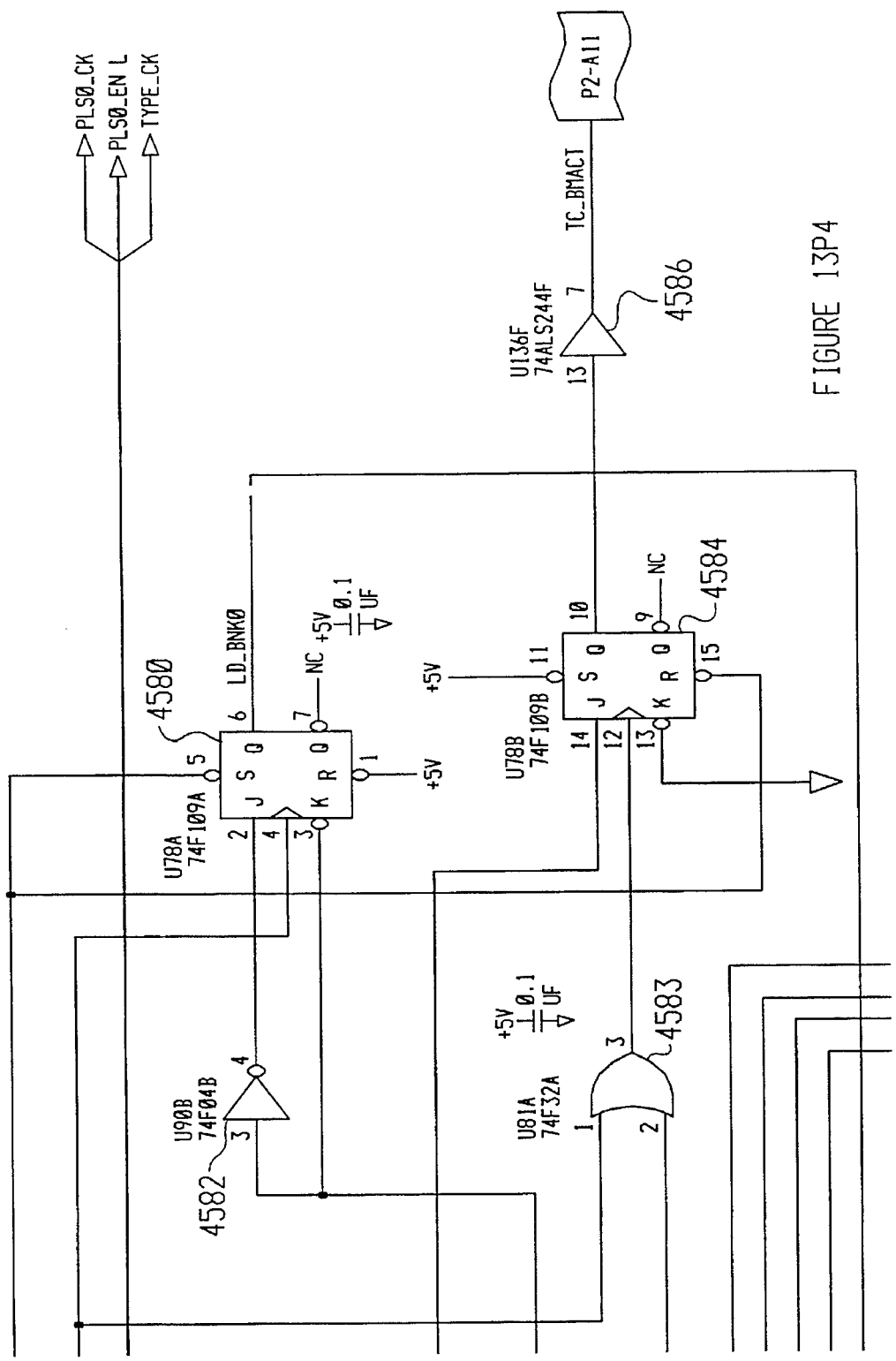
FIGURE 13P4

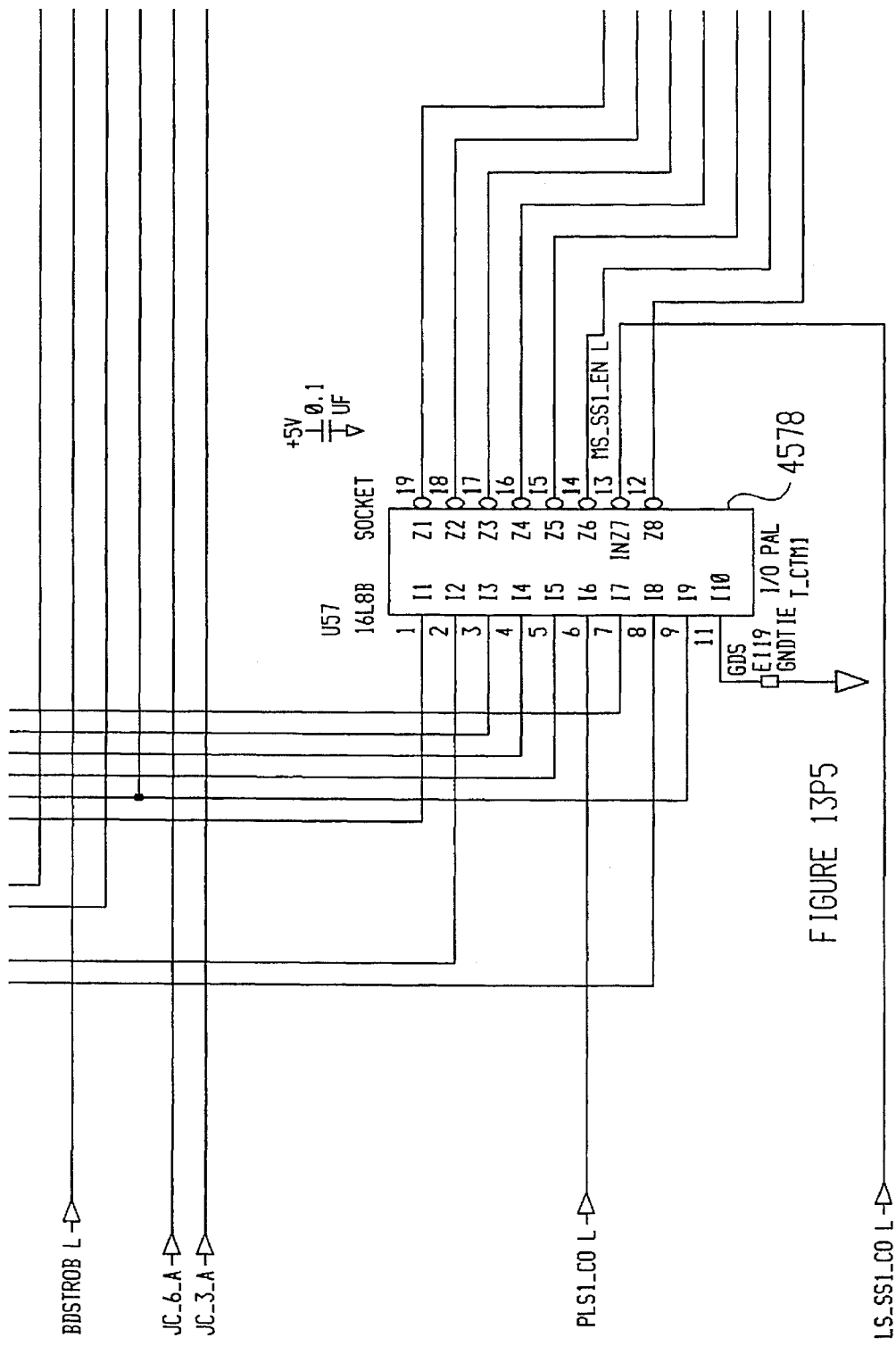
FIGURE 13P5

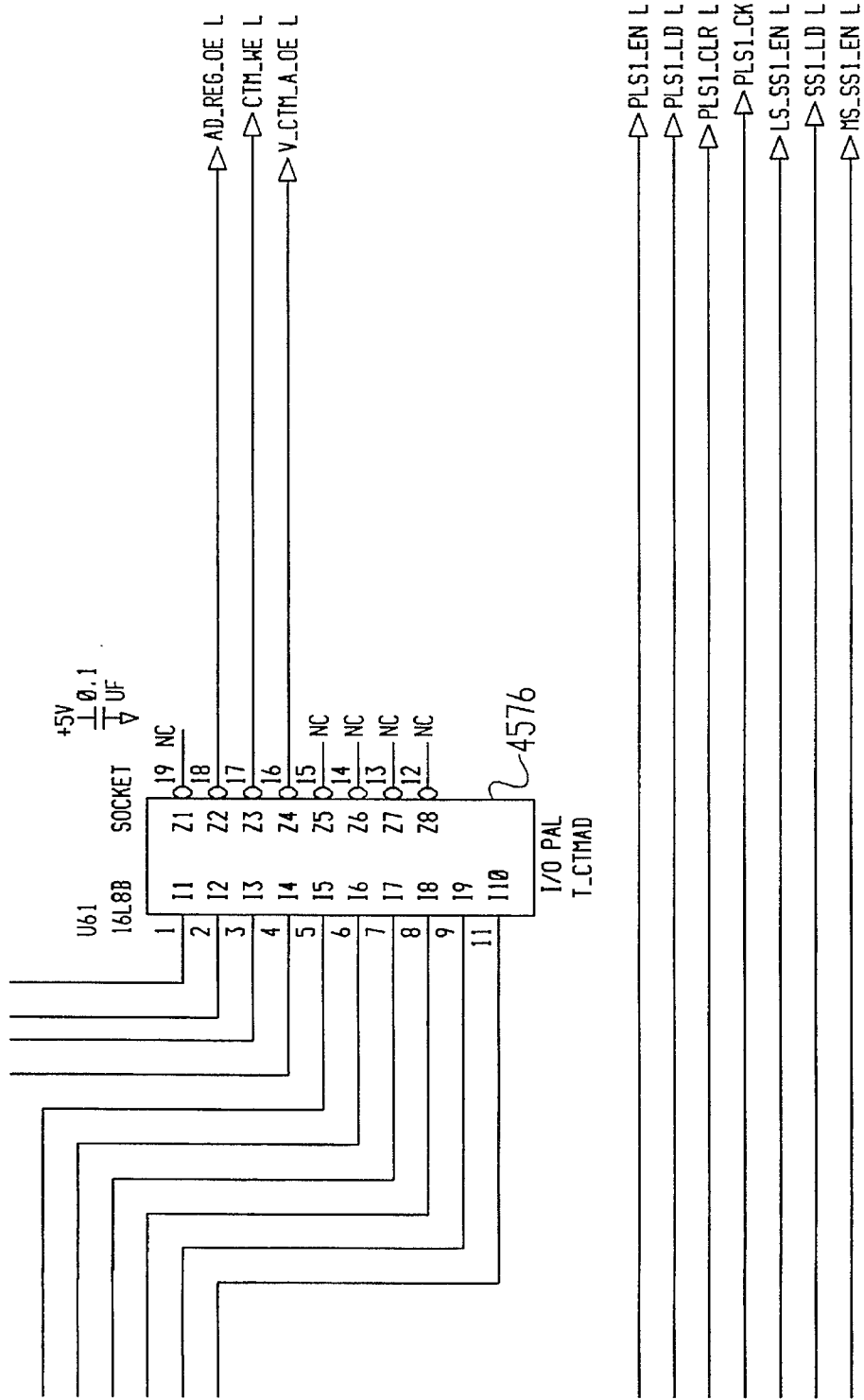
FIGURE 13P6

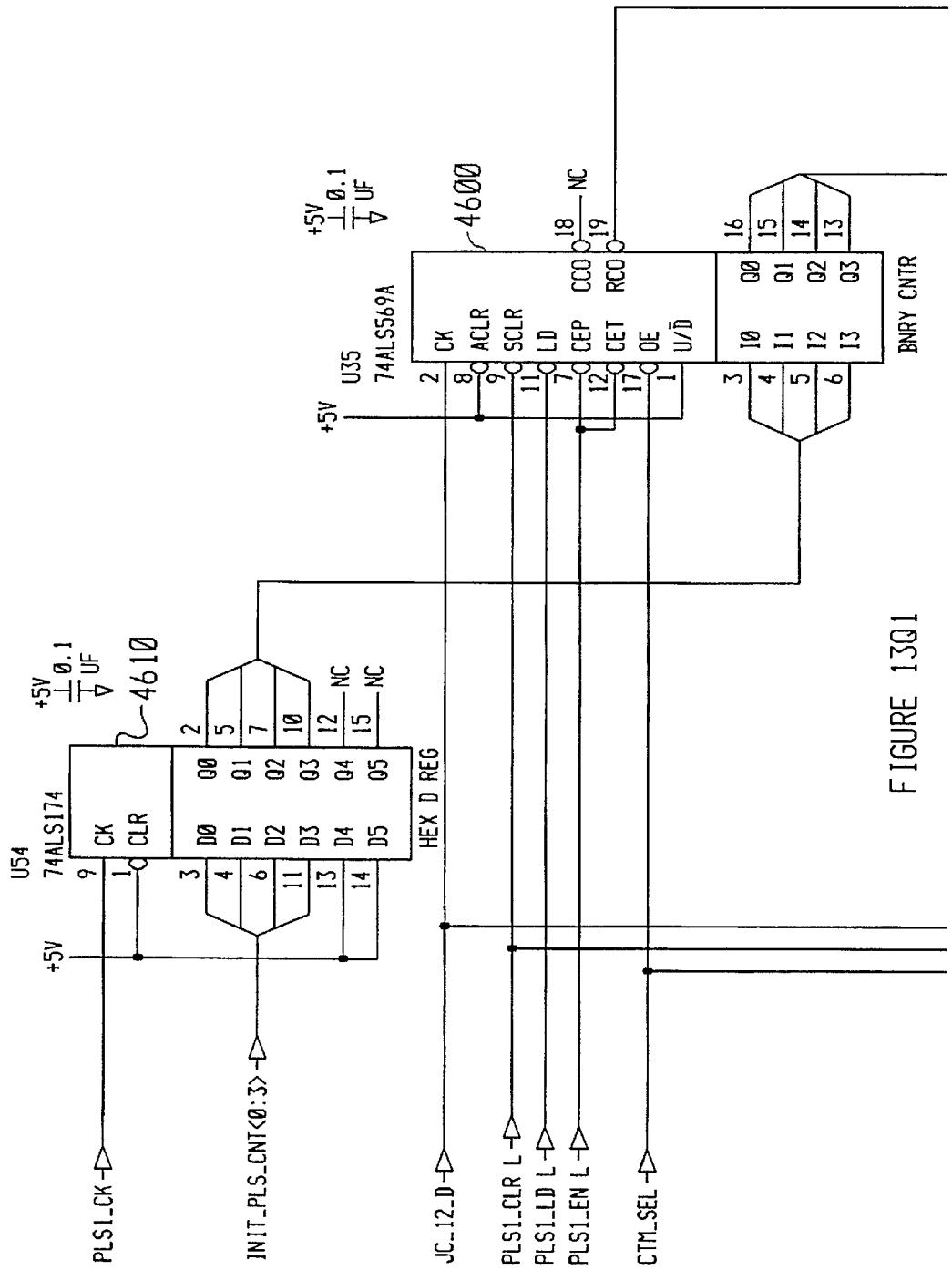
FIGURE 13Q1

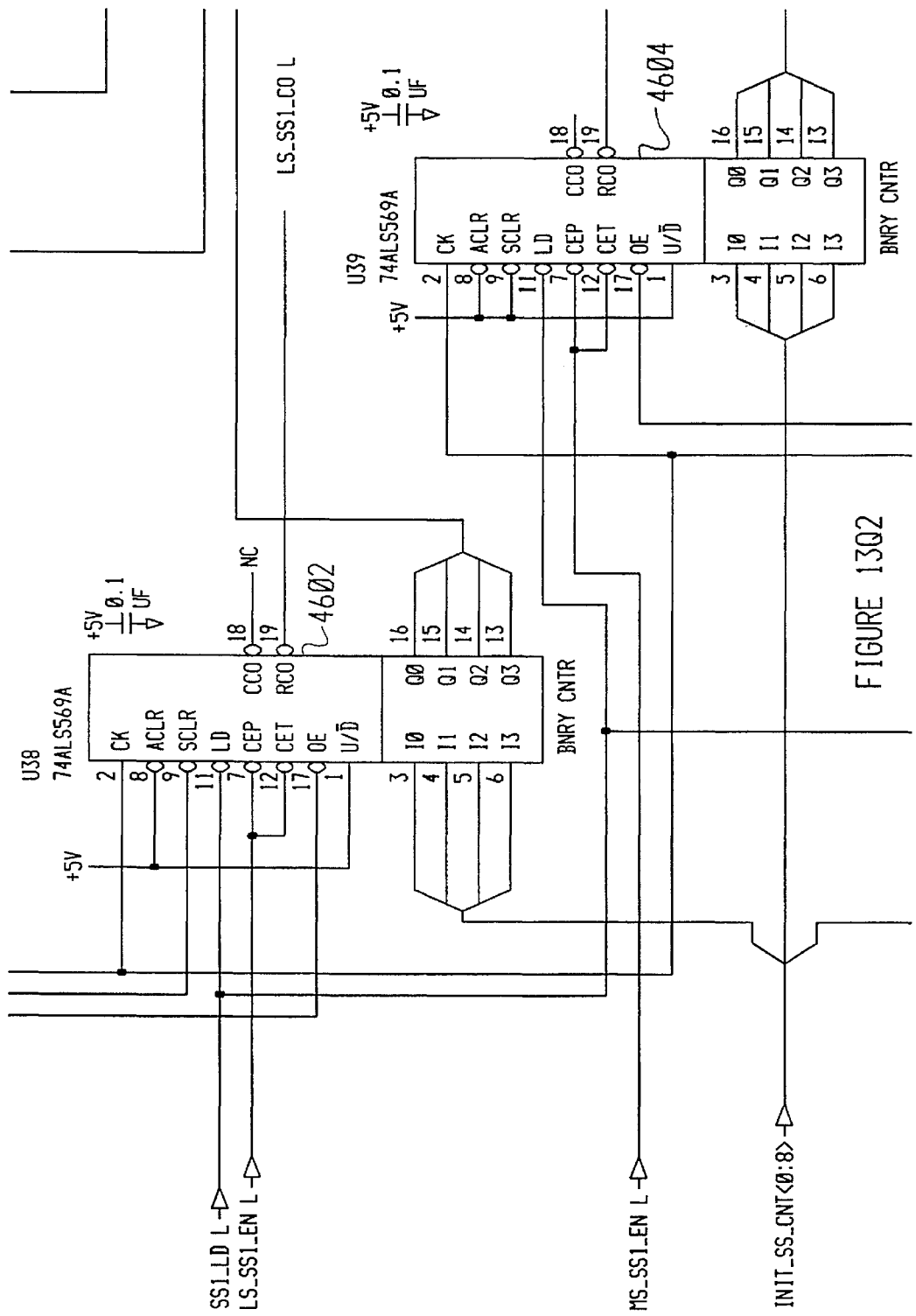
FIGURE 1302

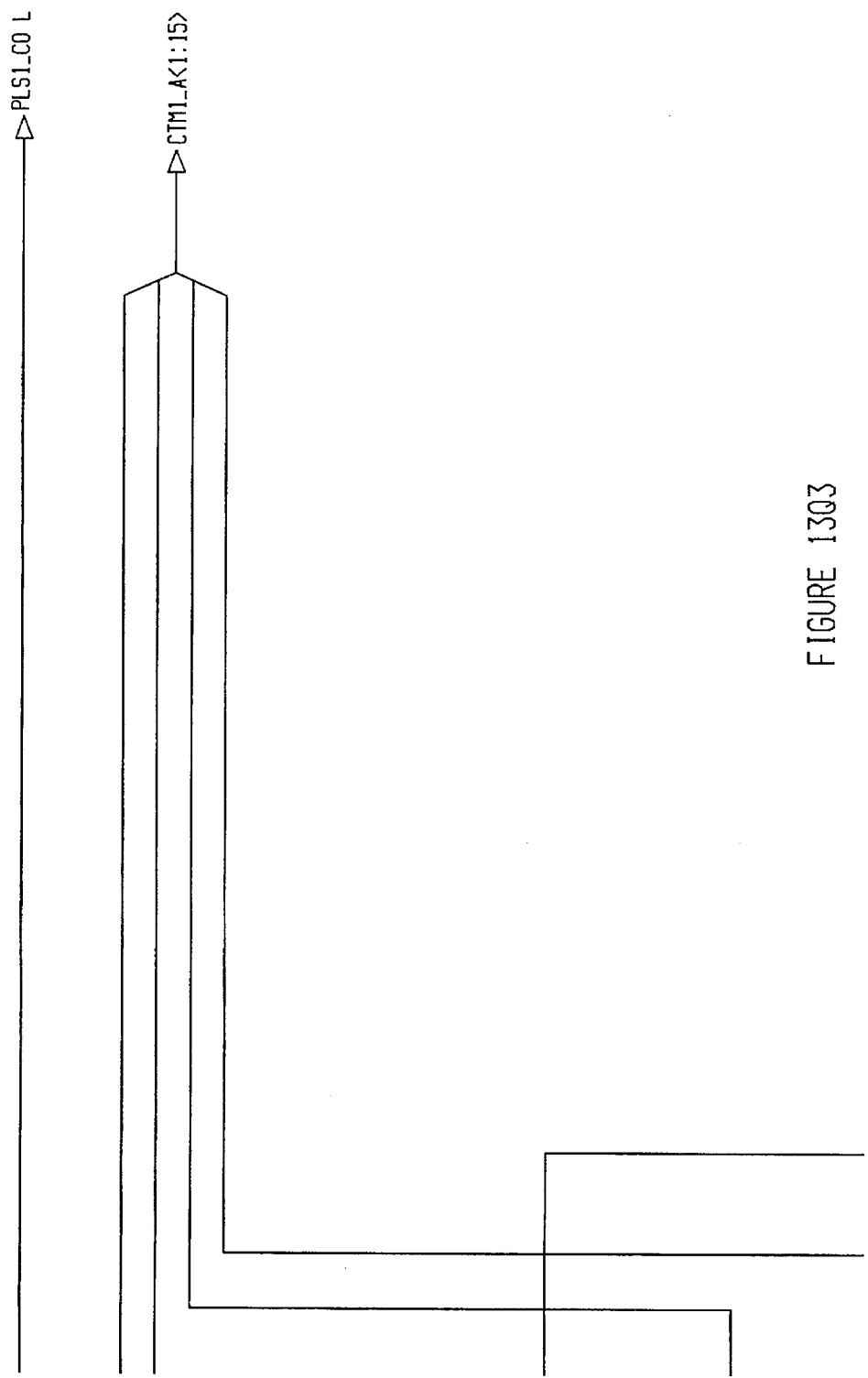
FIGURE 1303

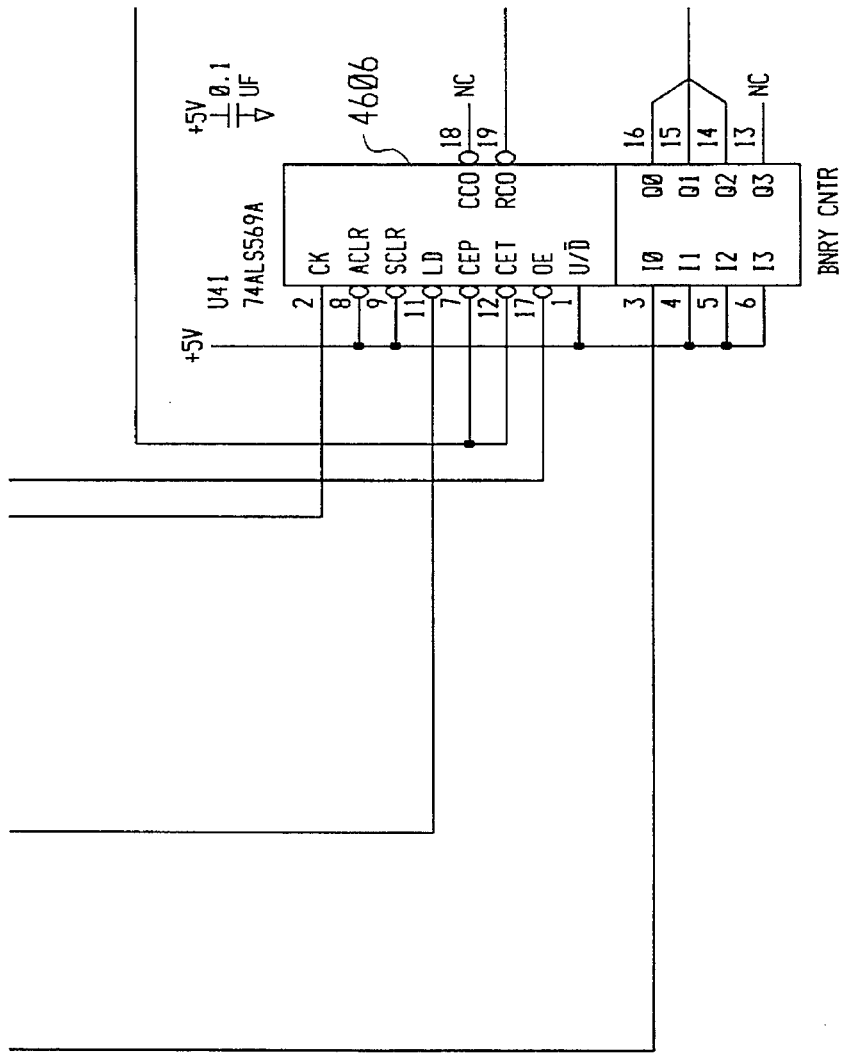
FIGURE 1304

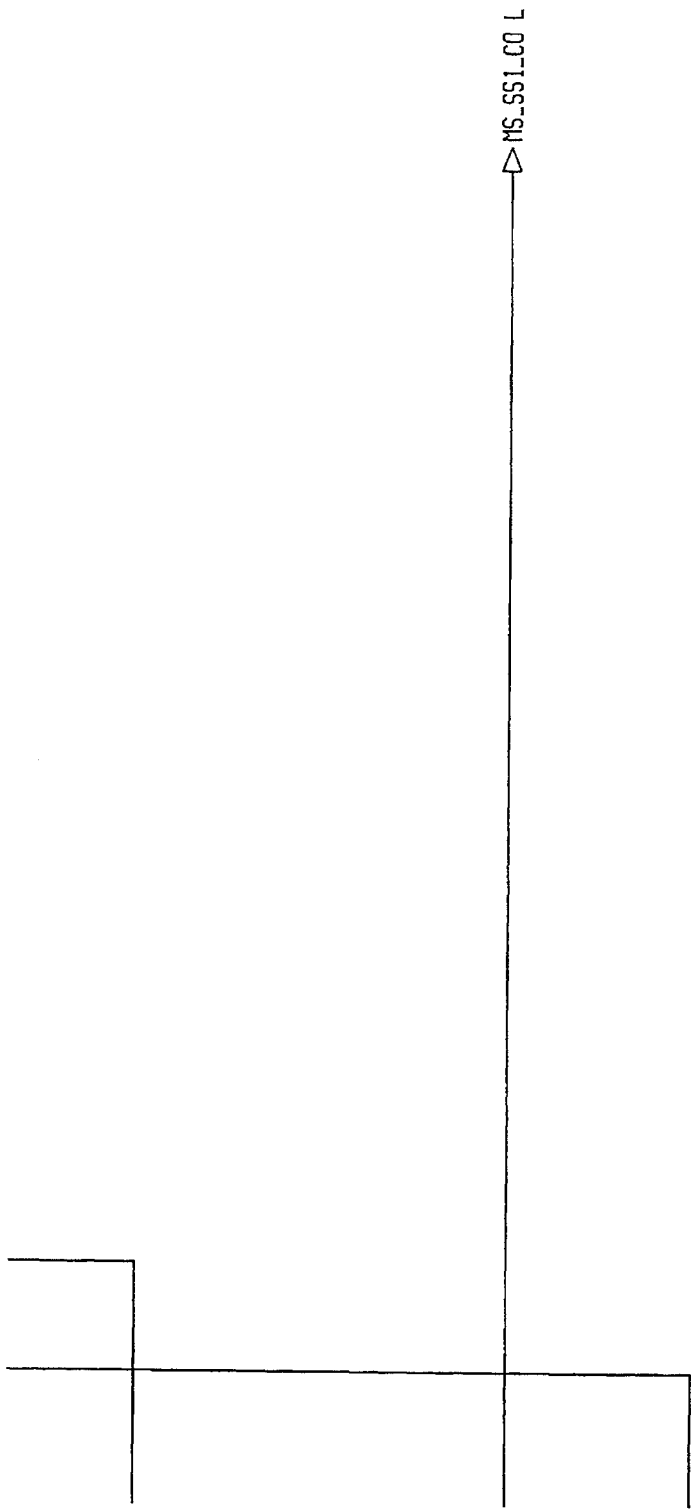

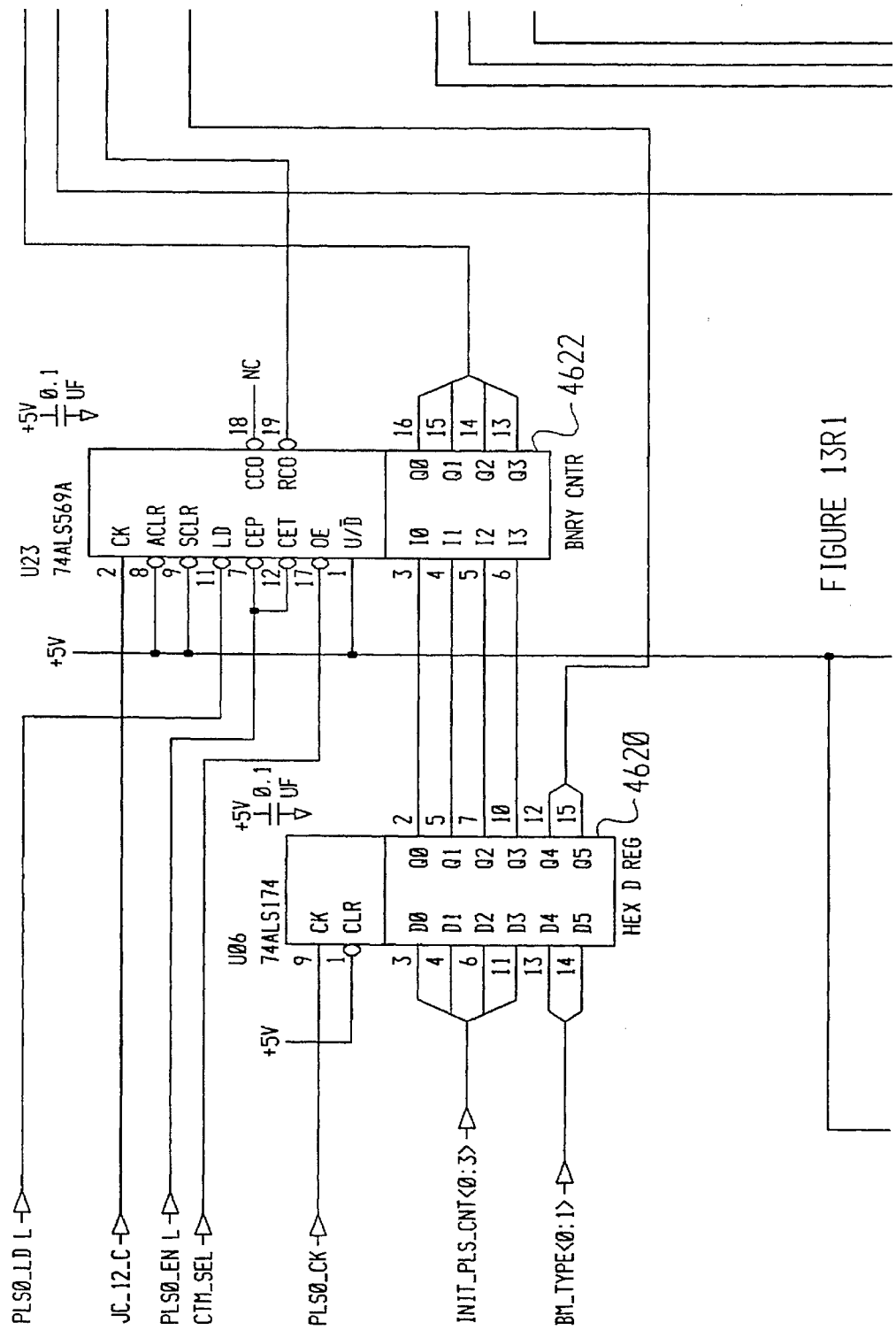
FIGURE 13R1

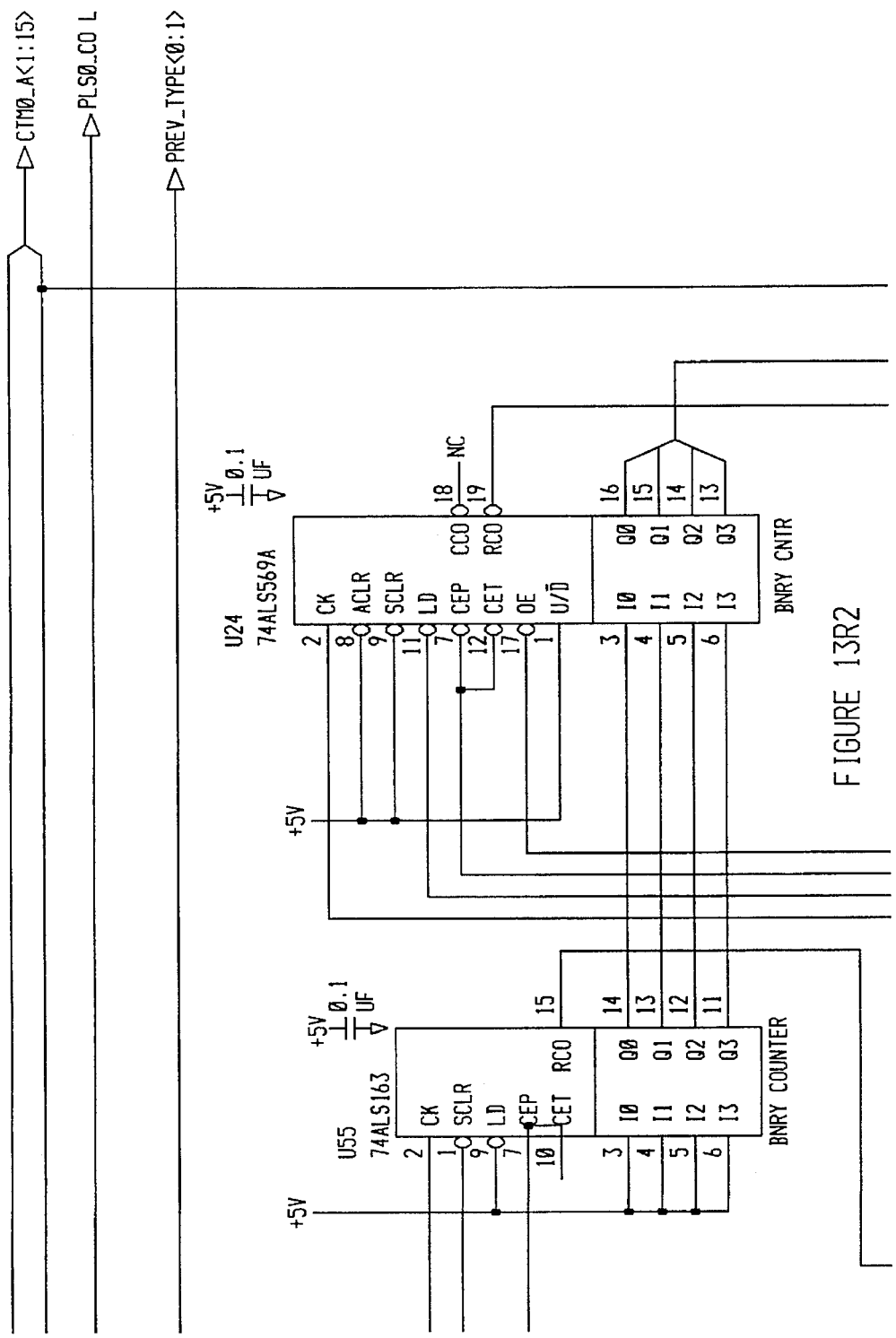
FIGURE 13R2

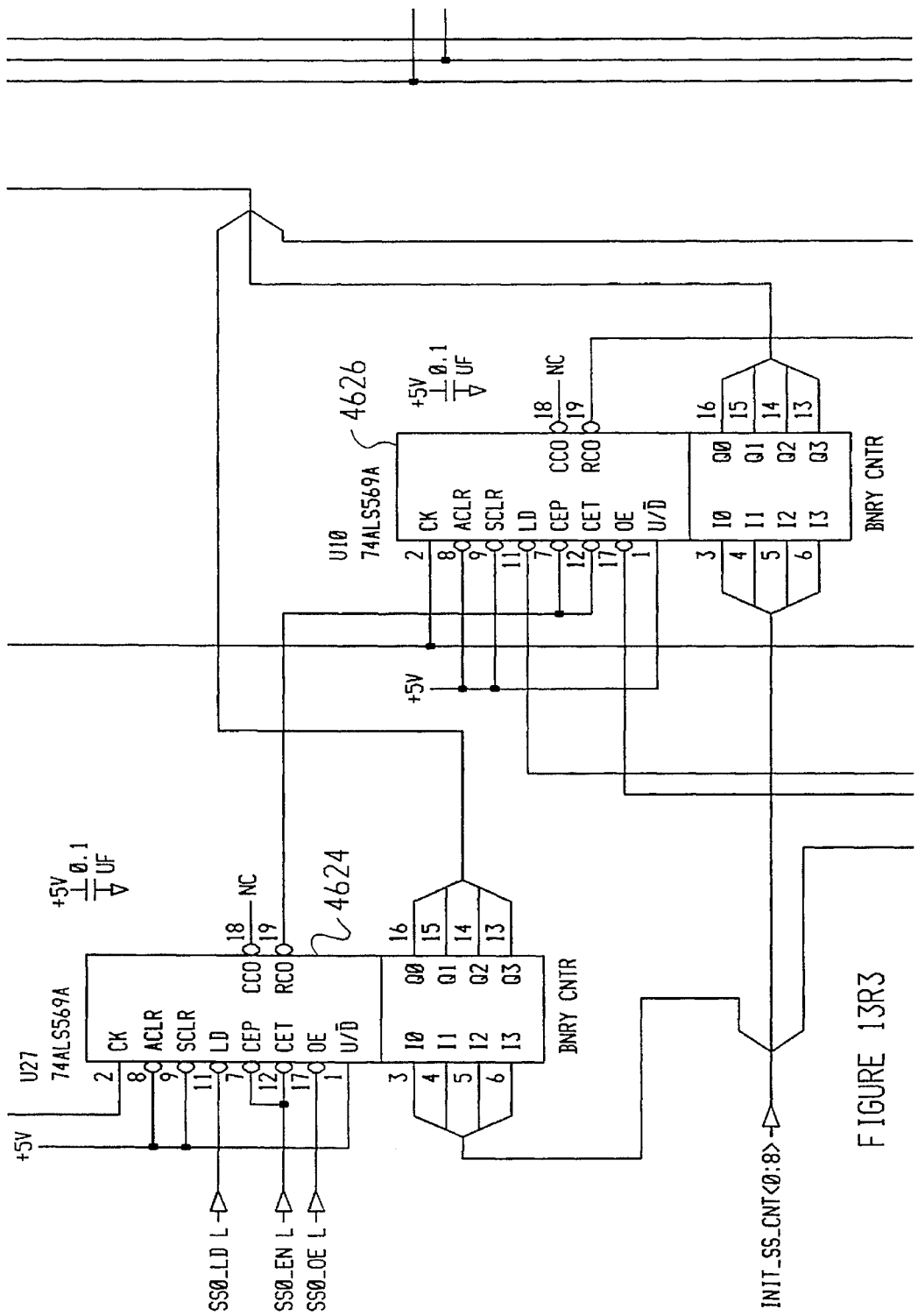

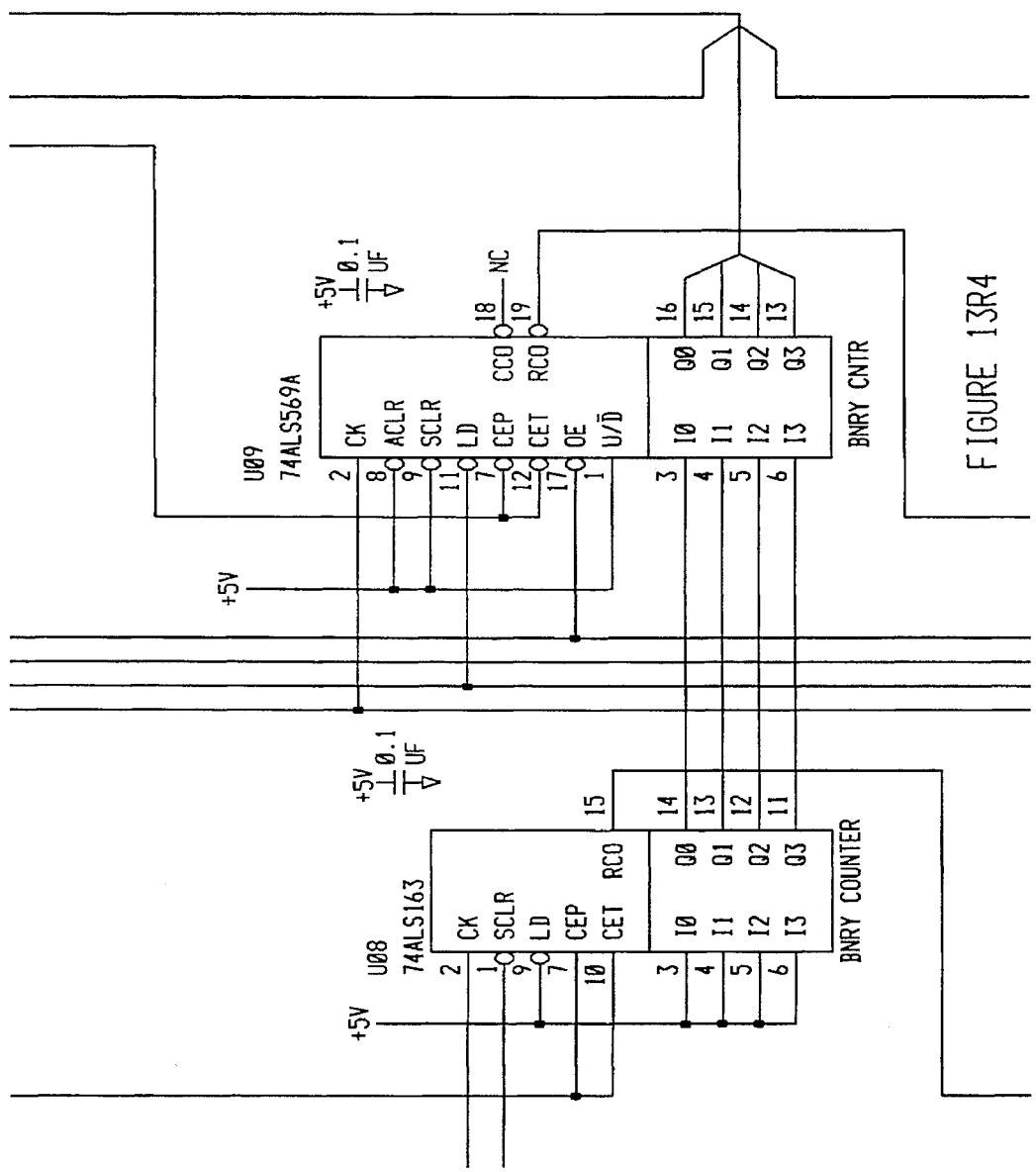
FIGURE 13R4

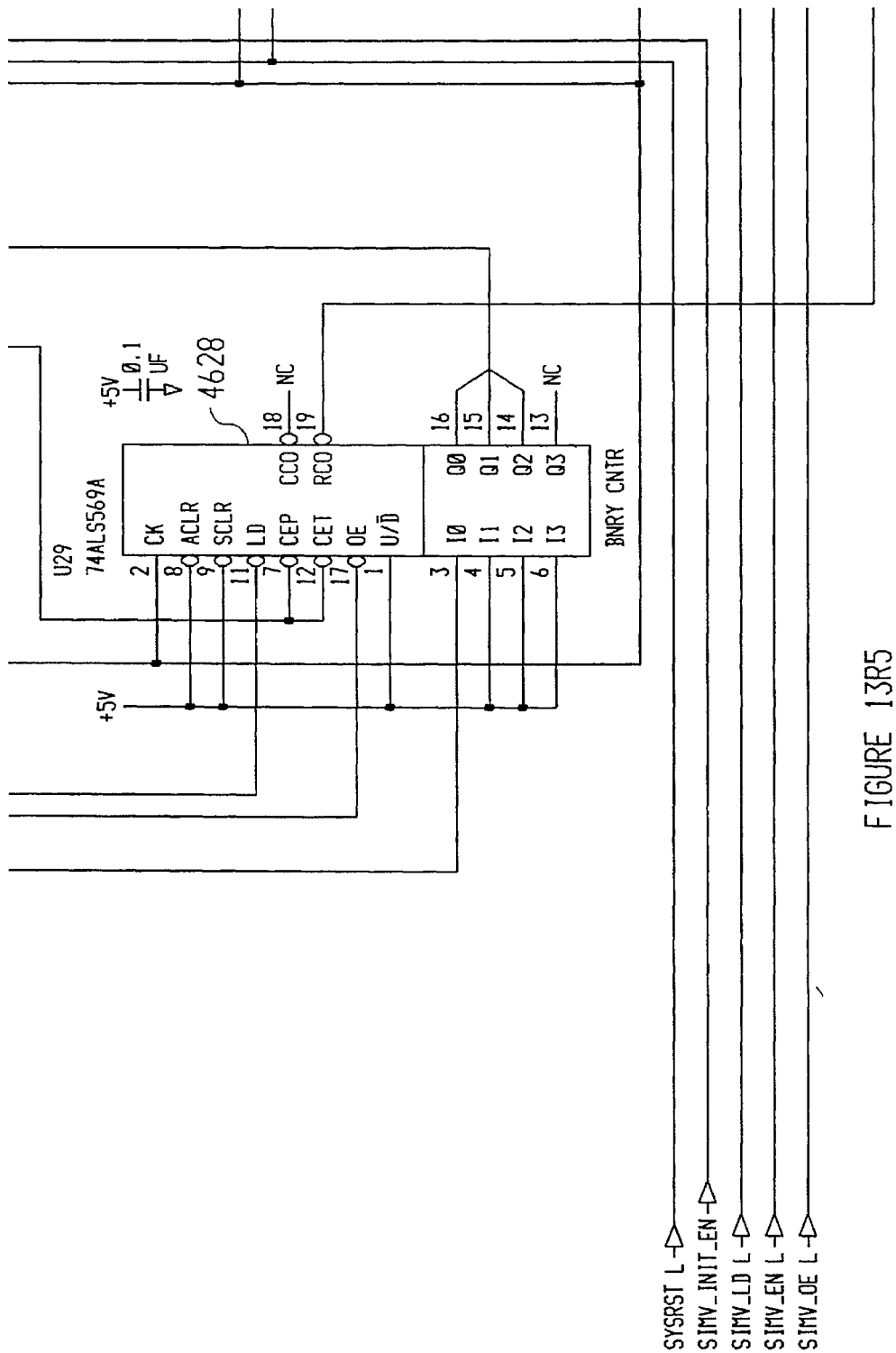
FIGURE 13R5

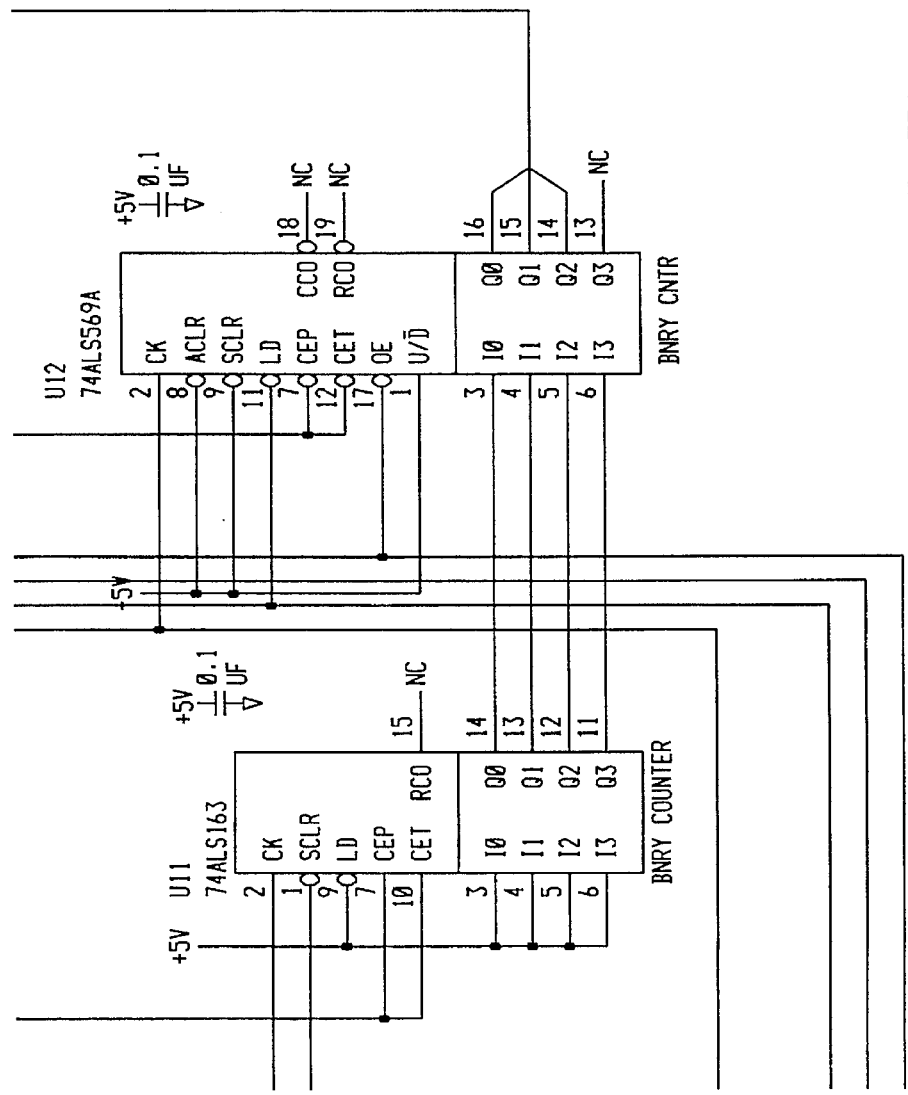
FIGURE 13R6

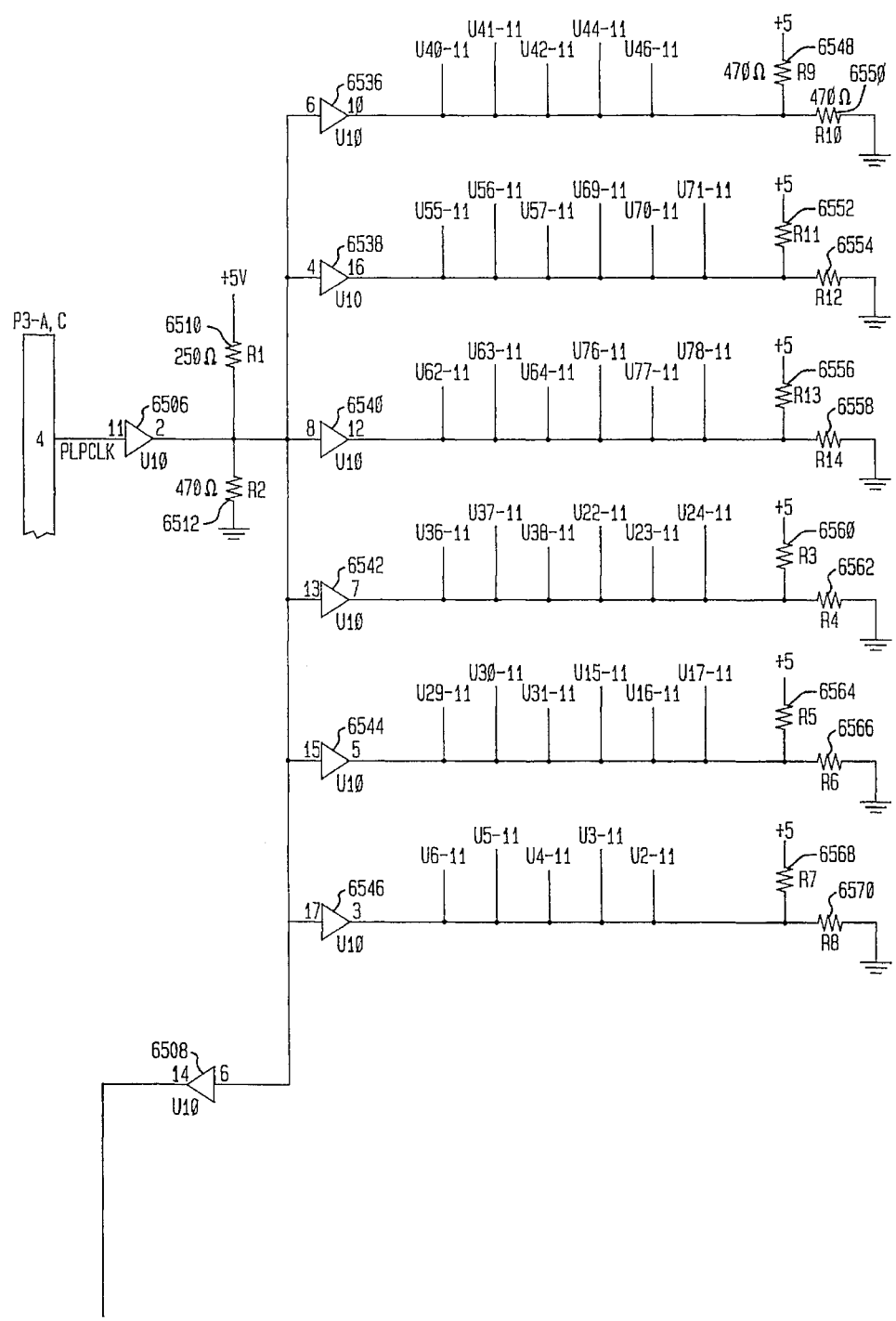
FIG. 14A1

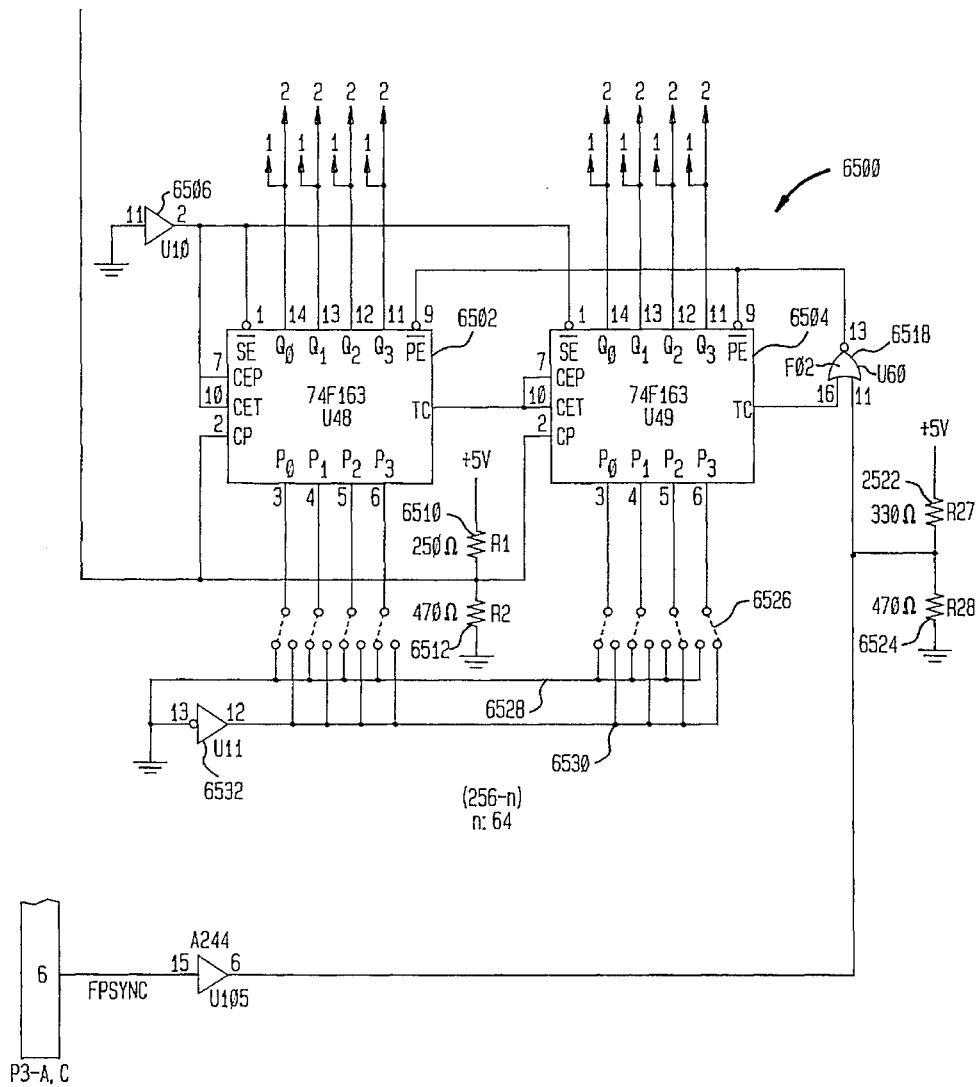
FIG. 14A2

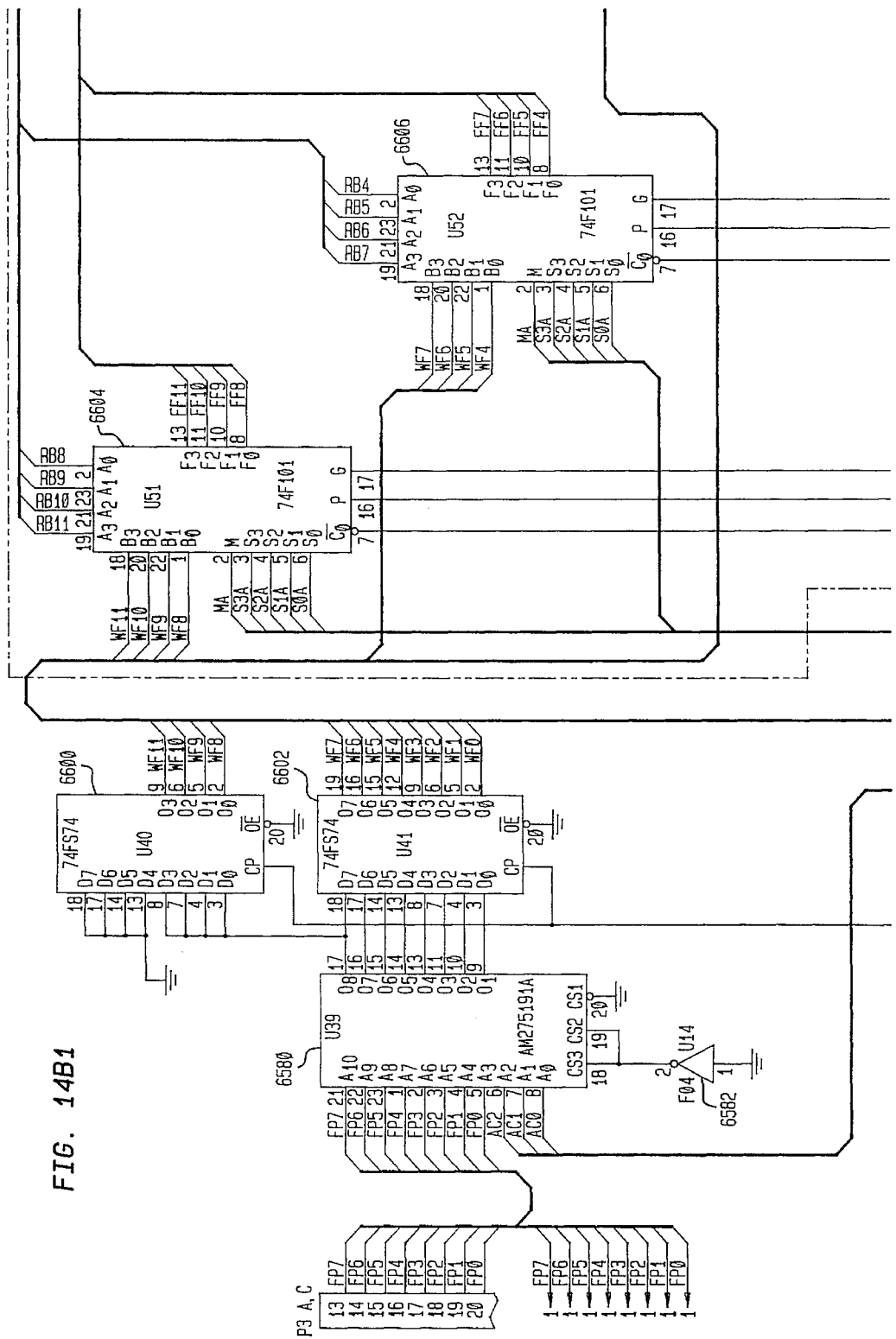
FIG. 14B1

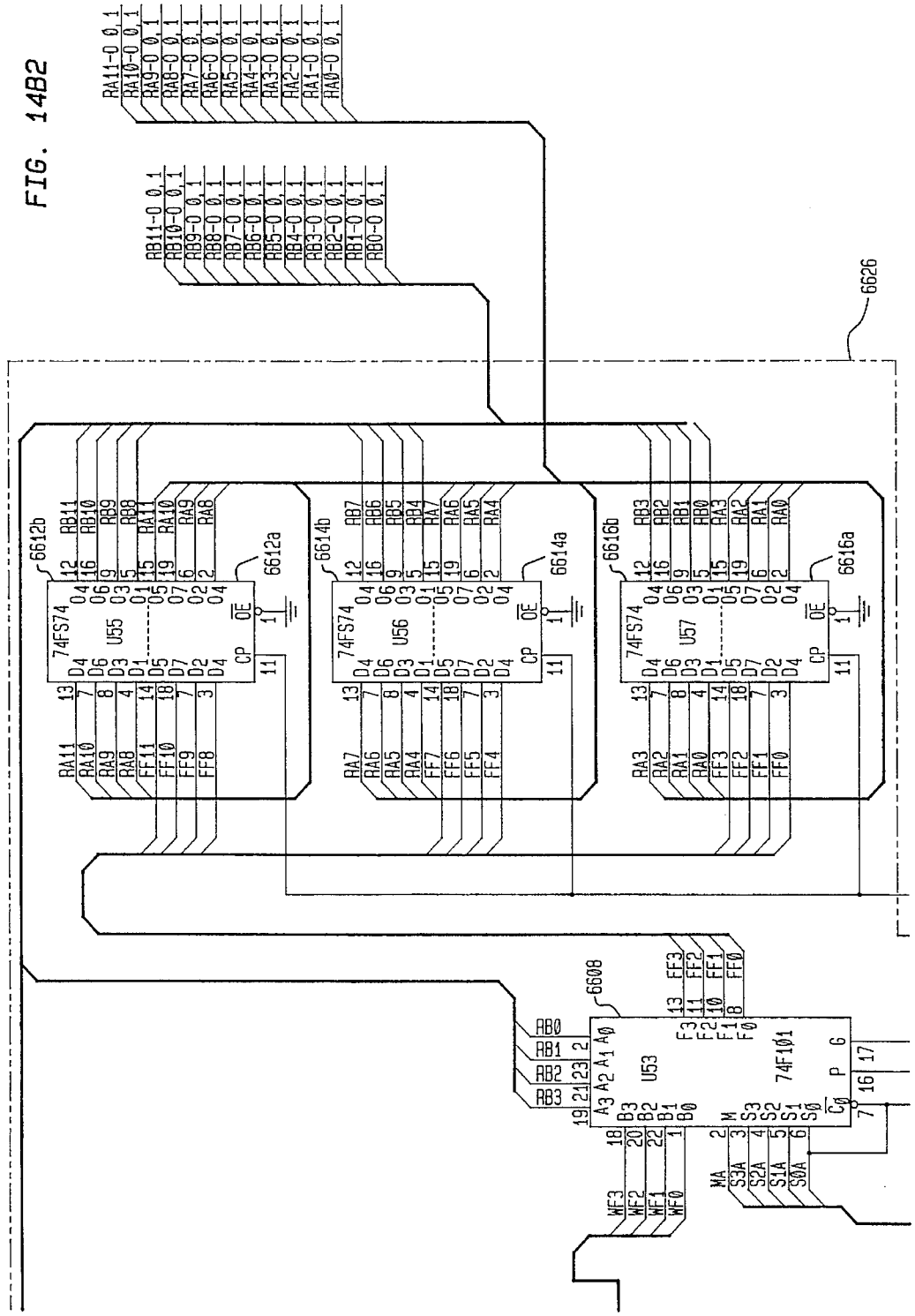
FIG. 14B2

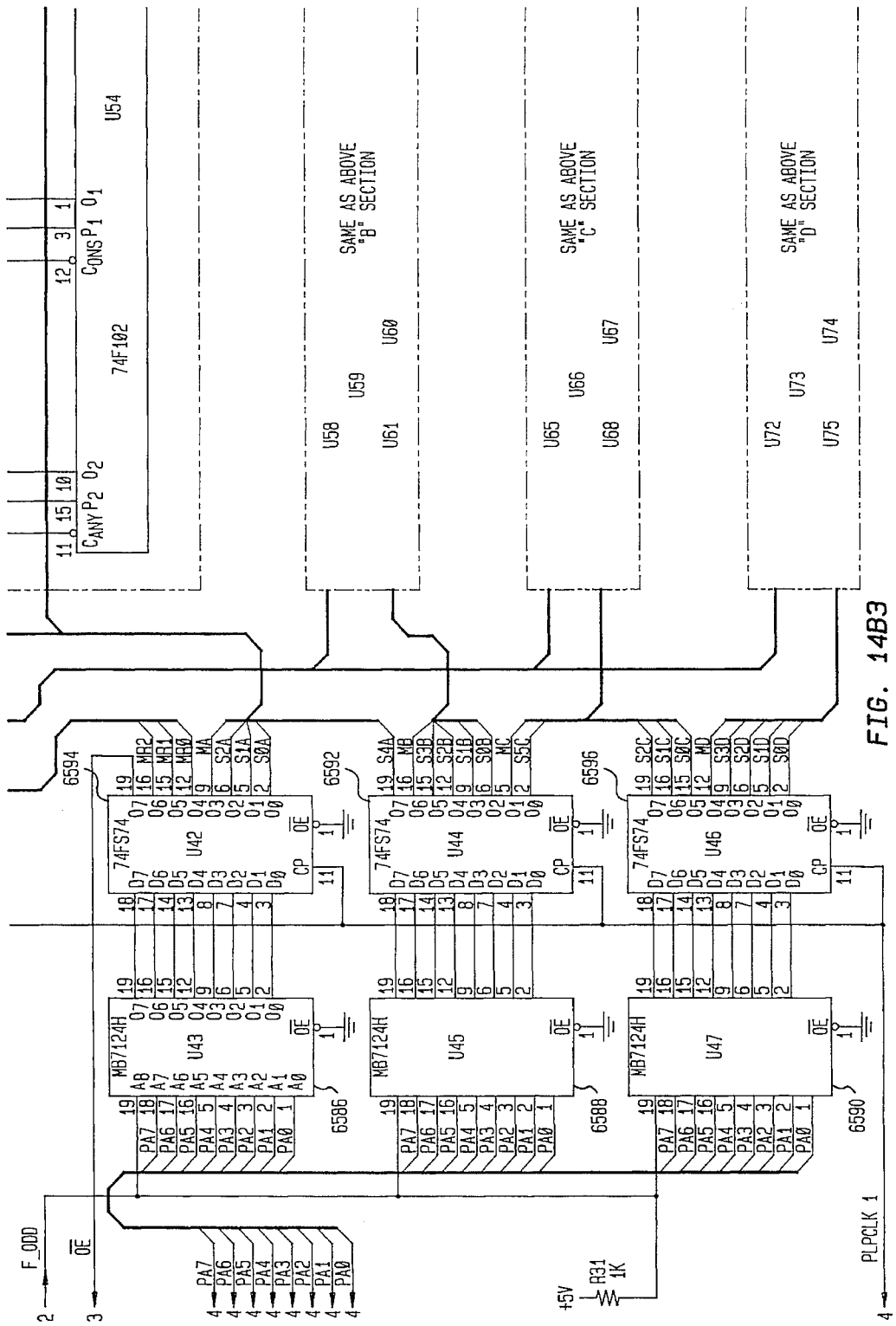
FIG. 14B3

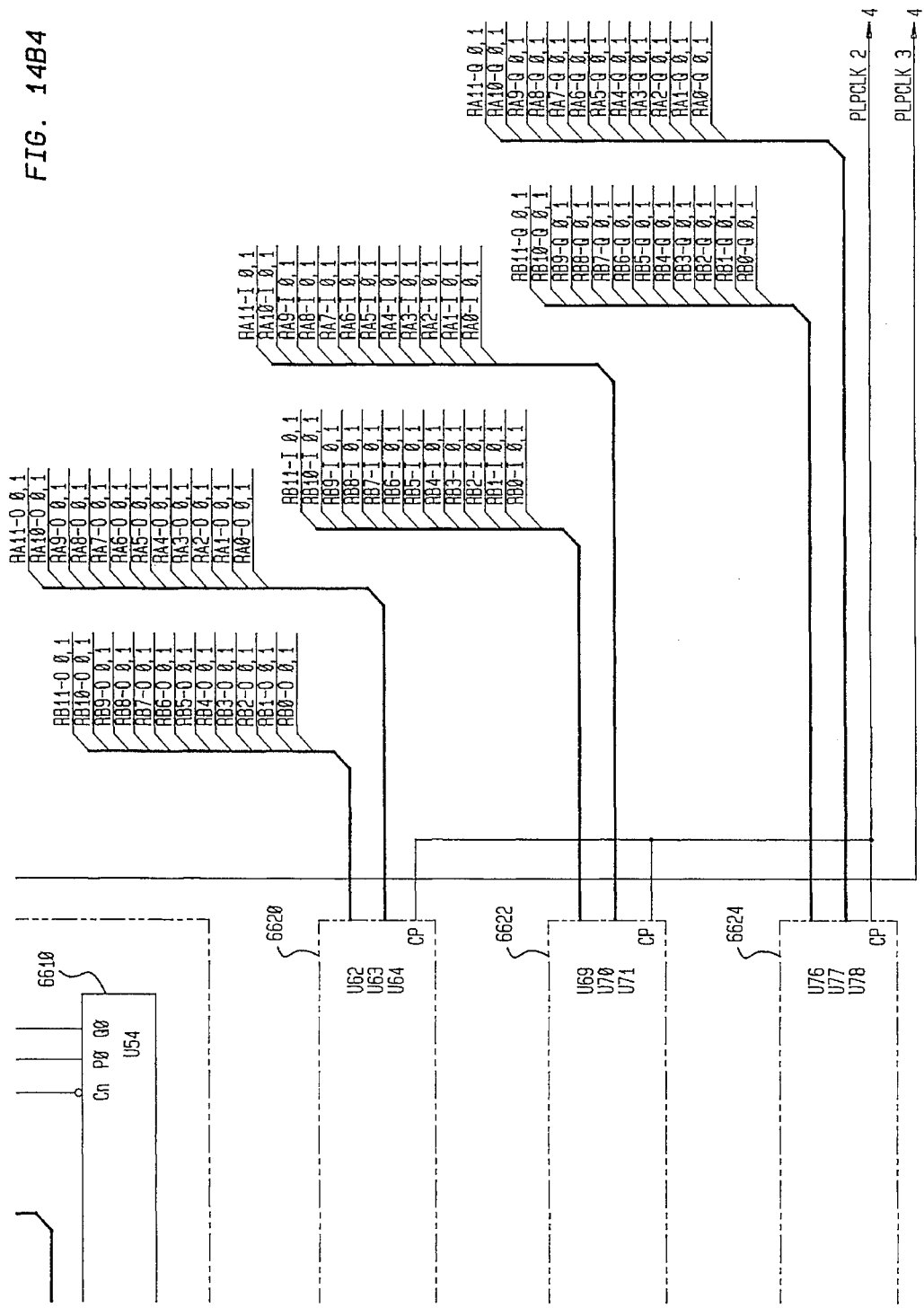
FIG. 14B4

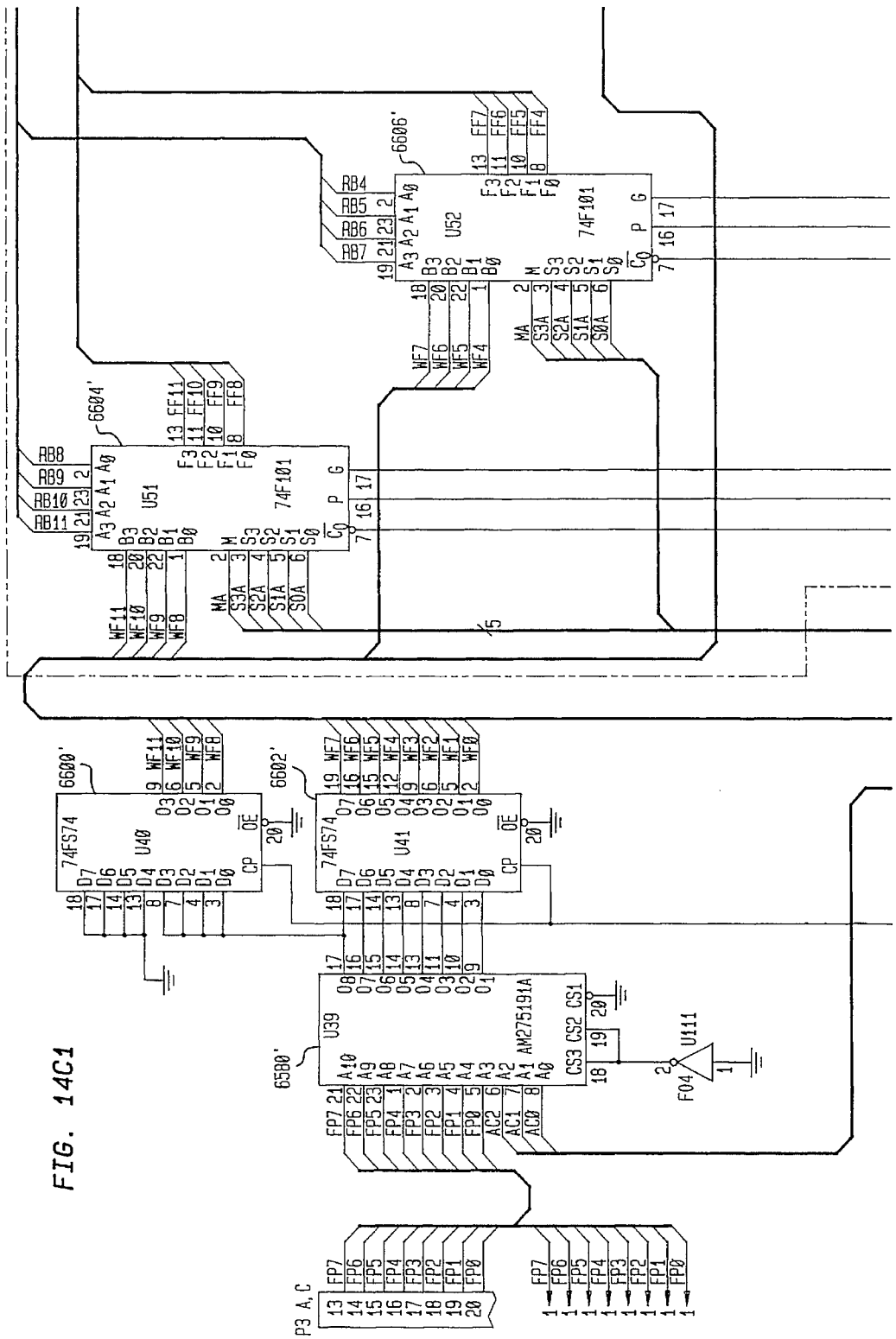
FIG. 14C1

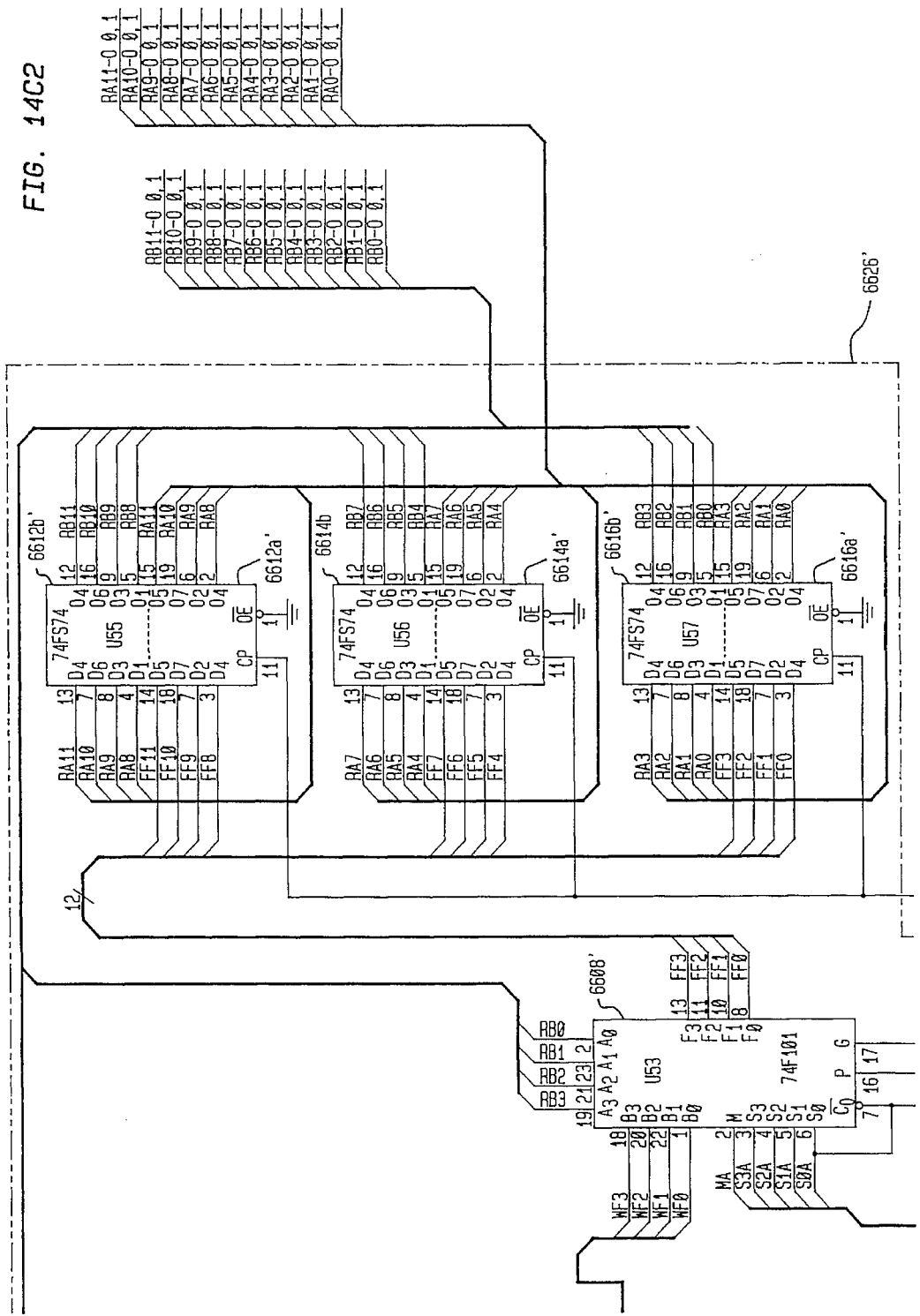
FIG. 14C2

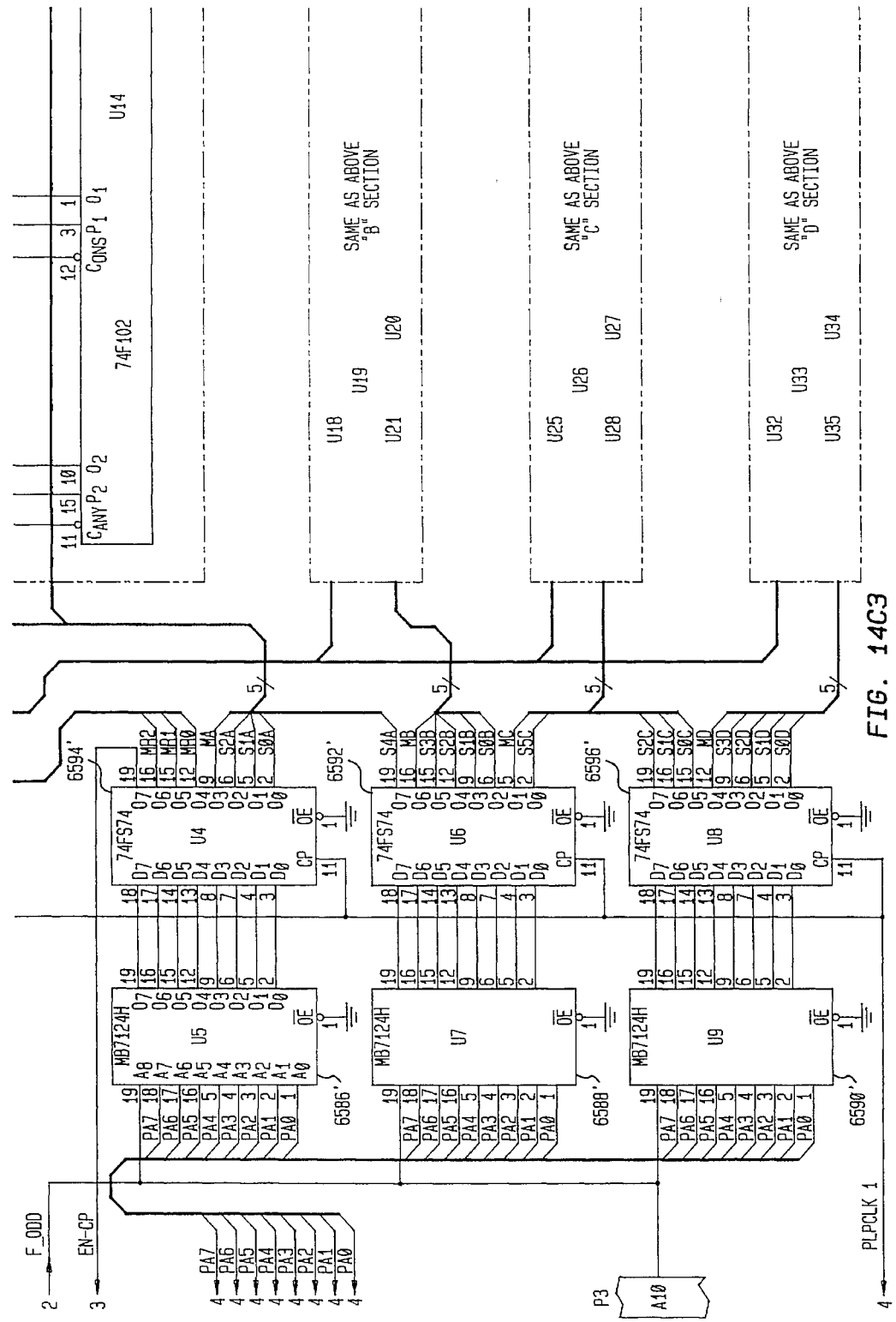
FIG. 14C3

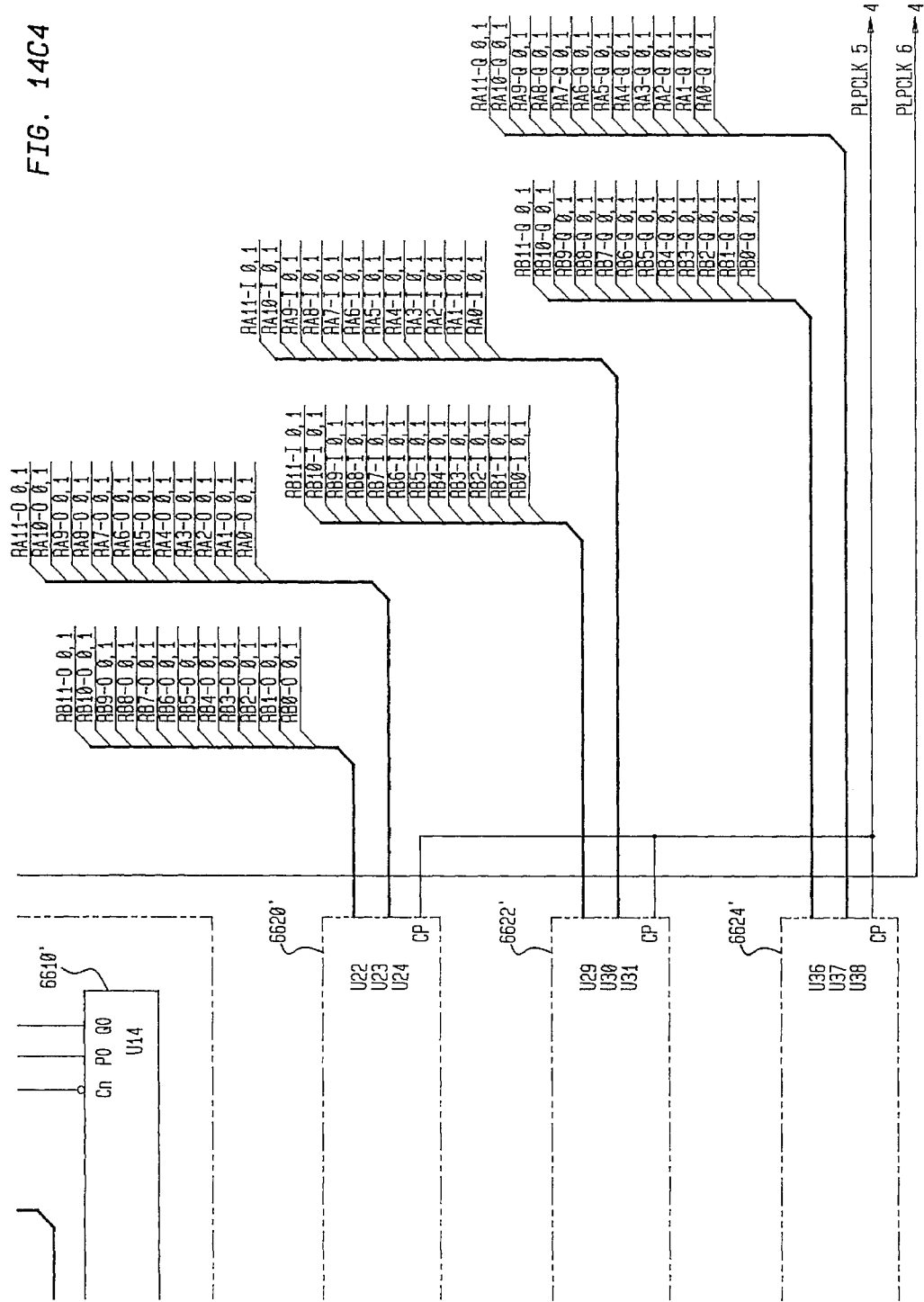
FIG. 14C4

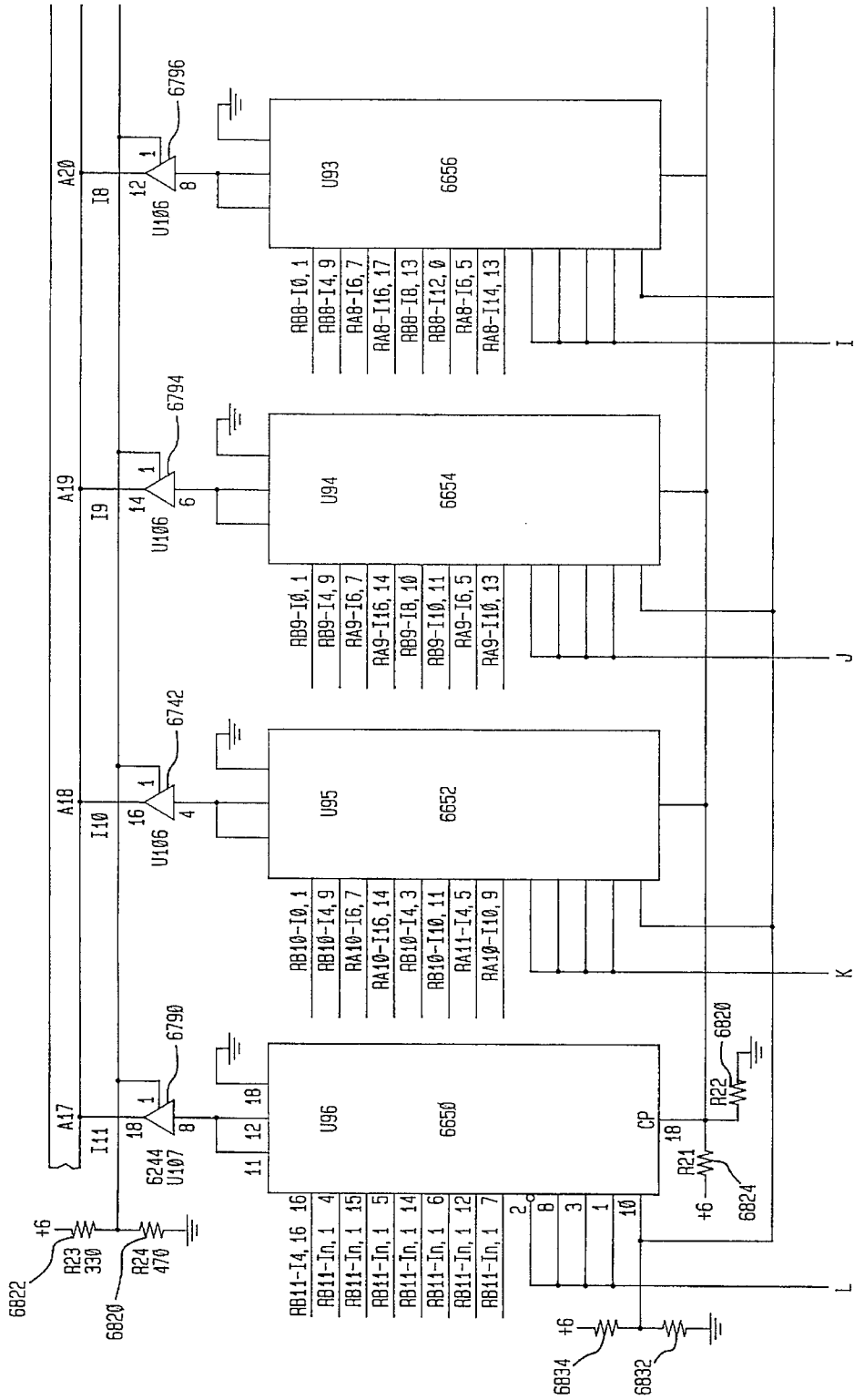
FIG. 14D1

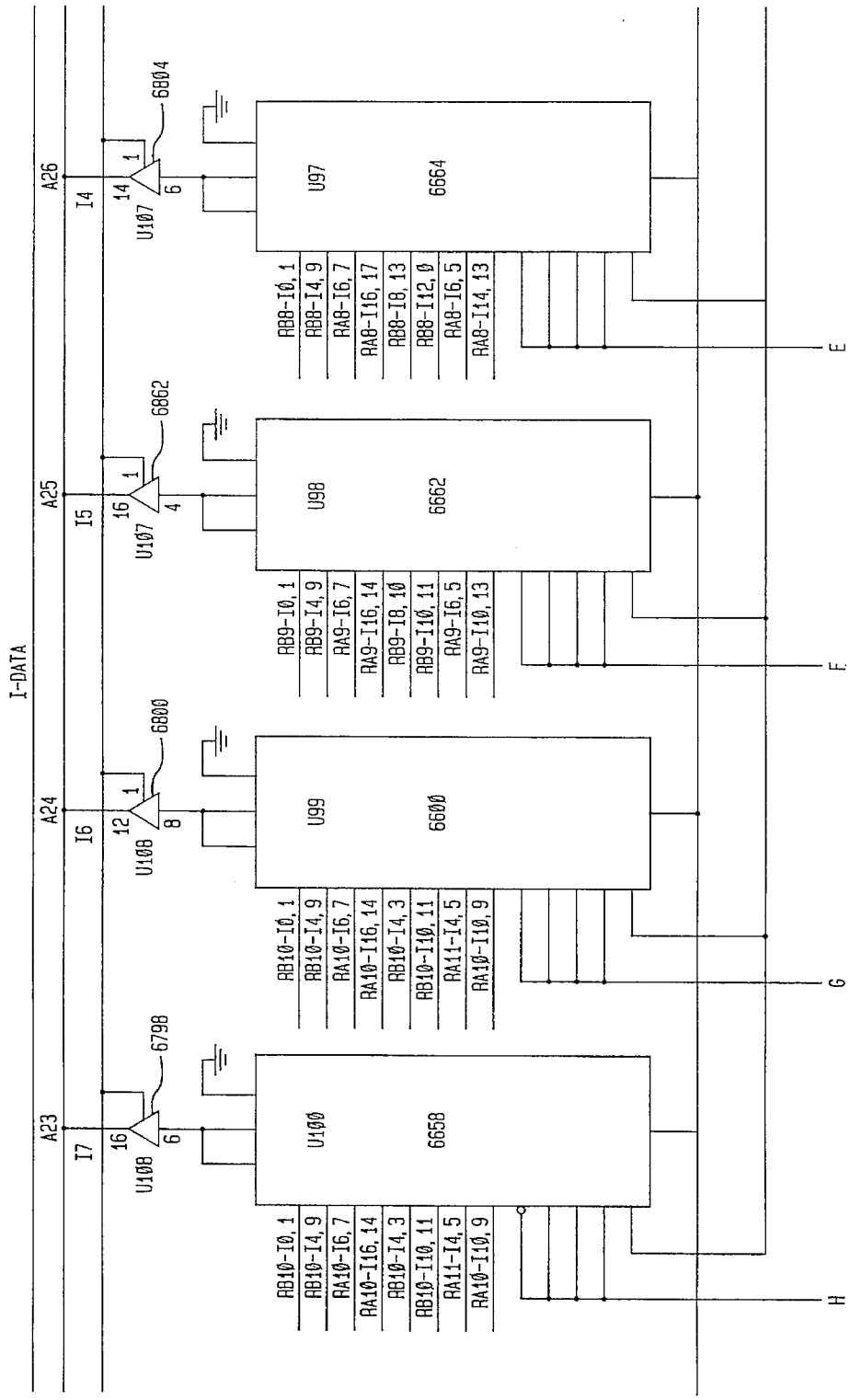

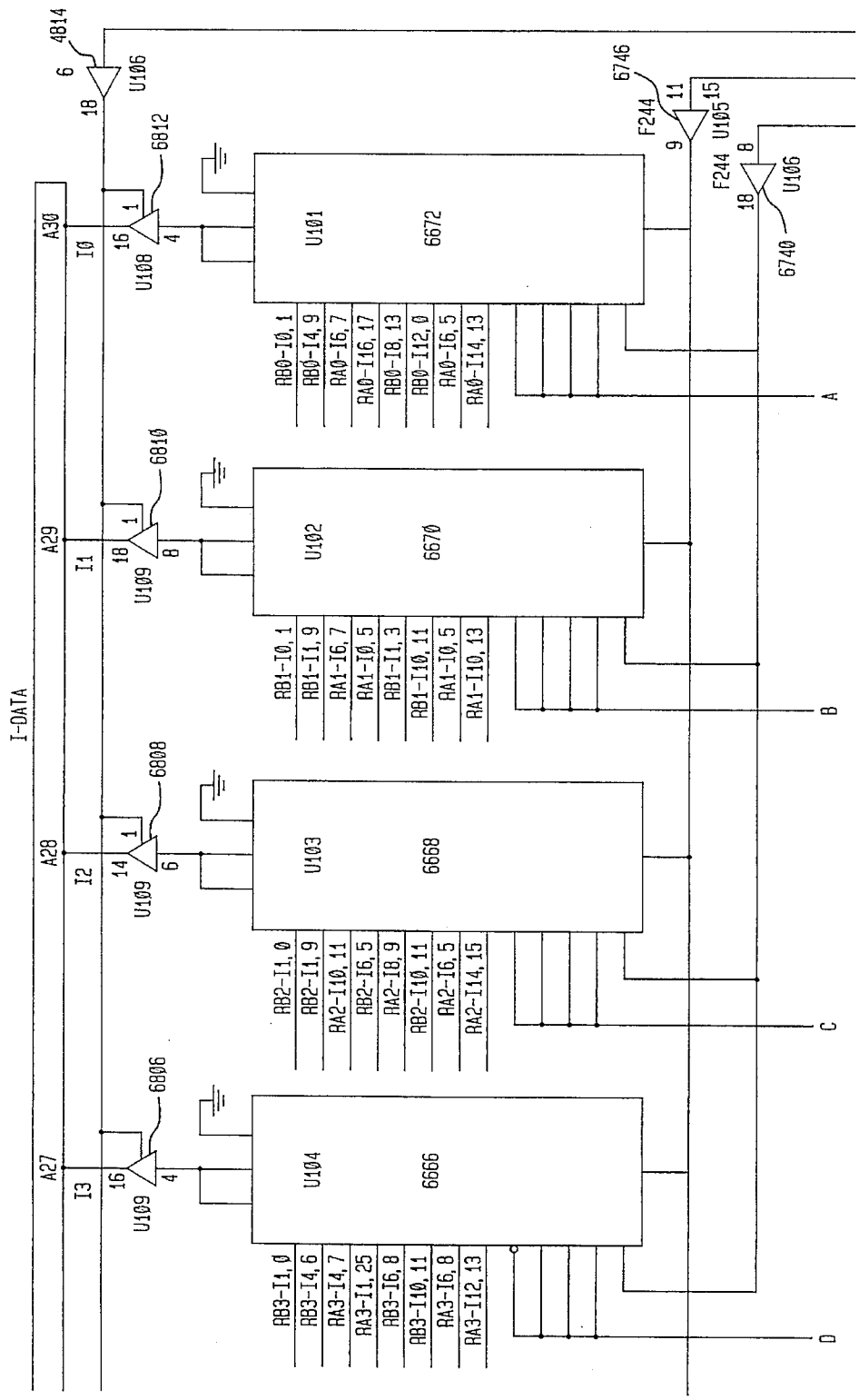
FIG. 14D3

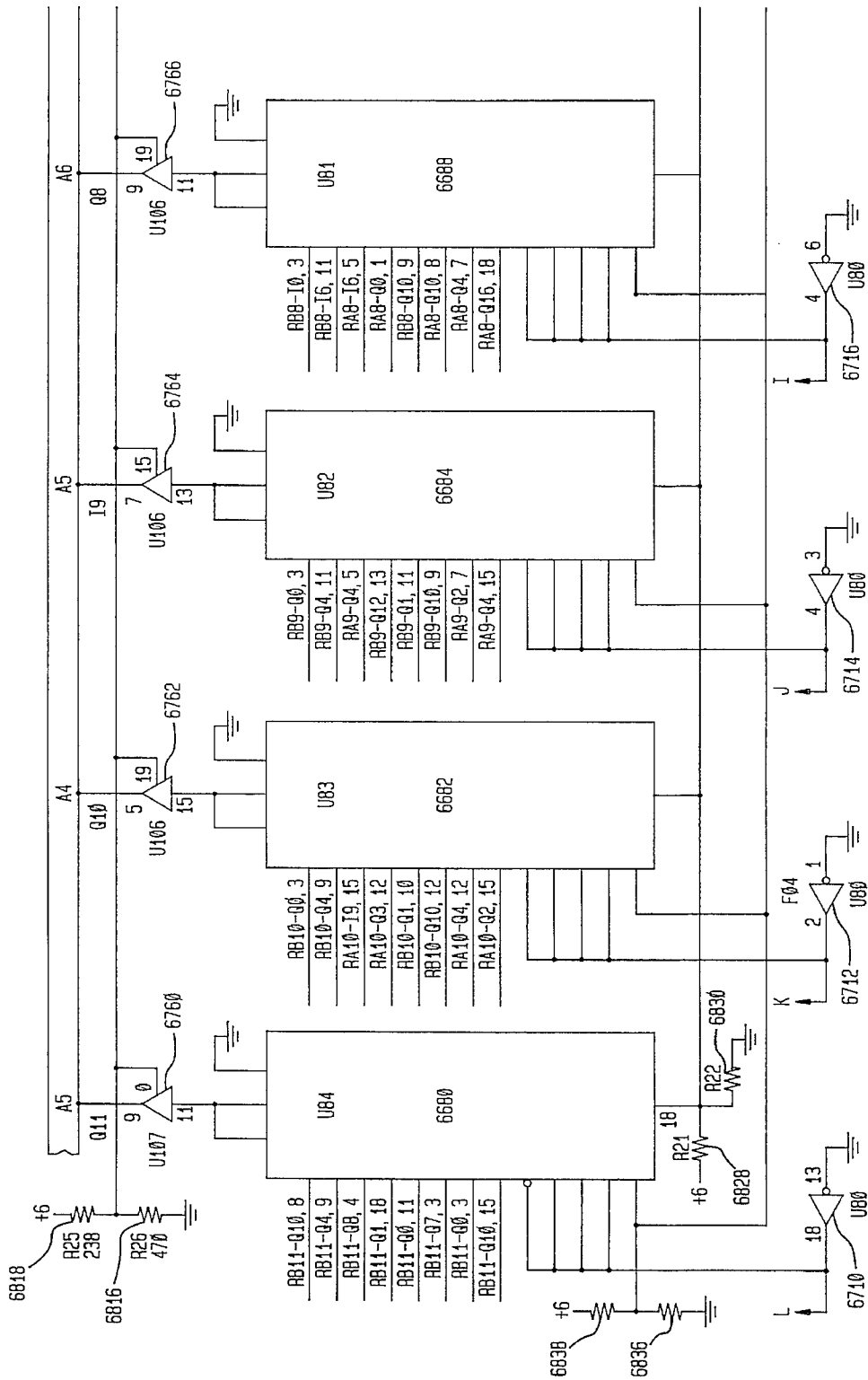
FIG. 14D4

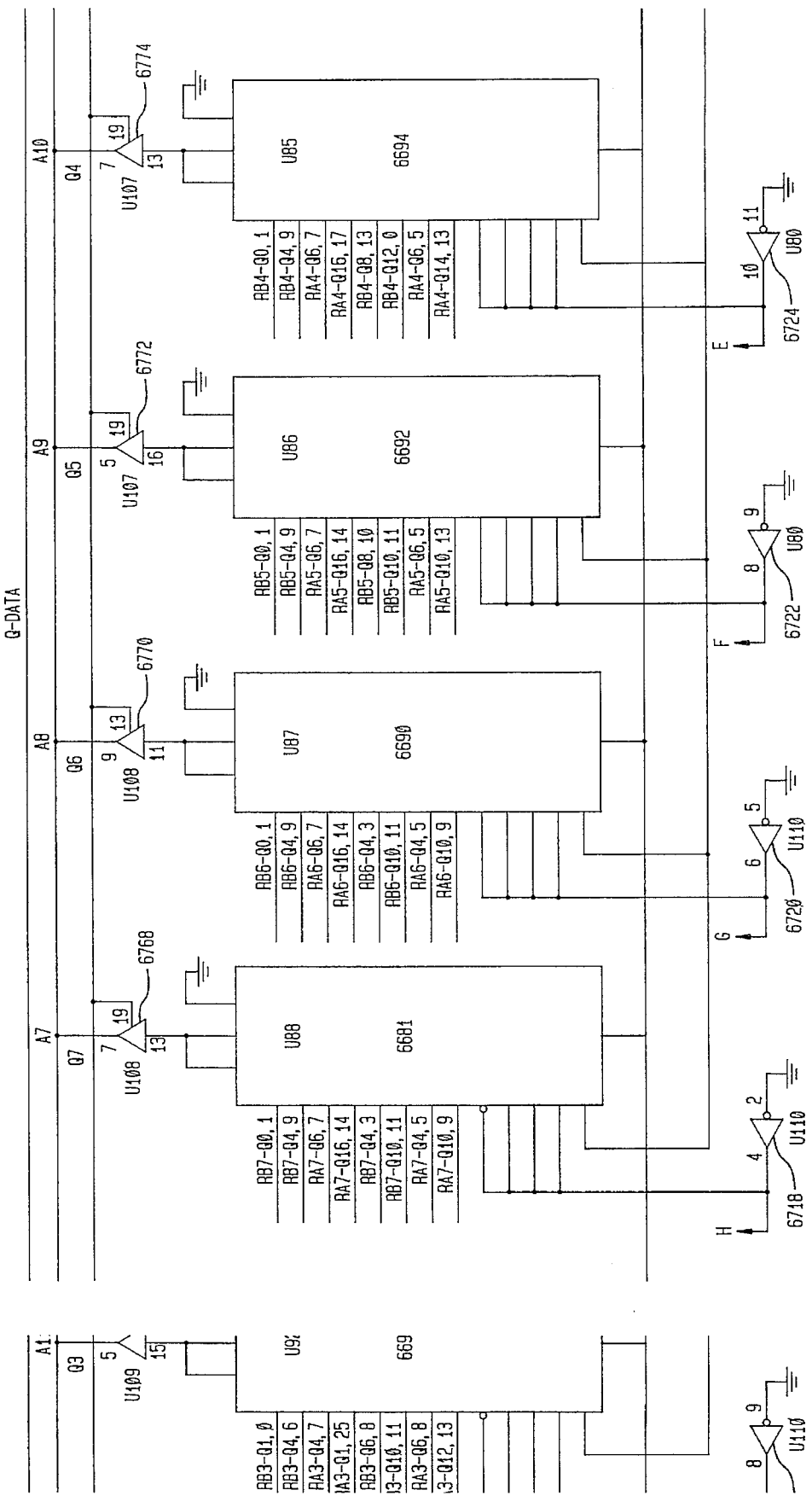
FIG. 14D5

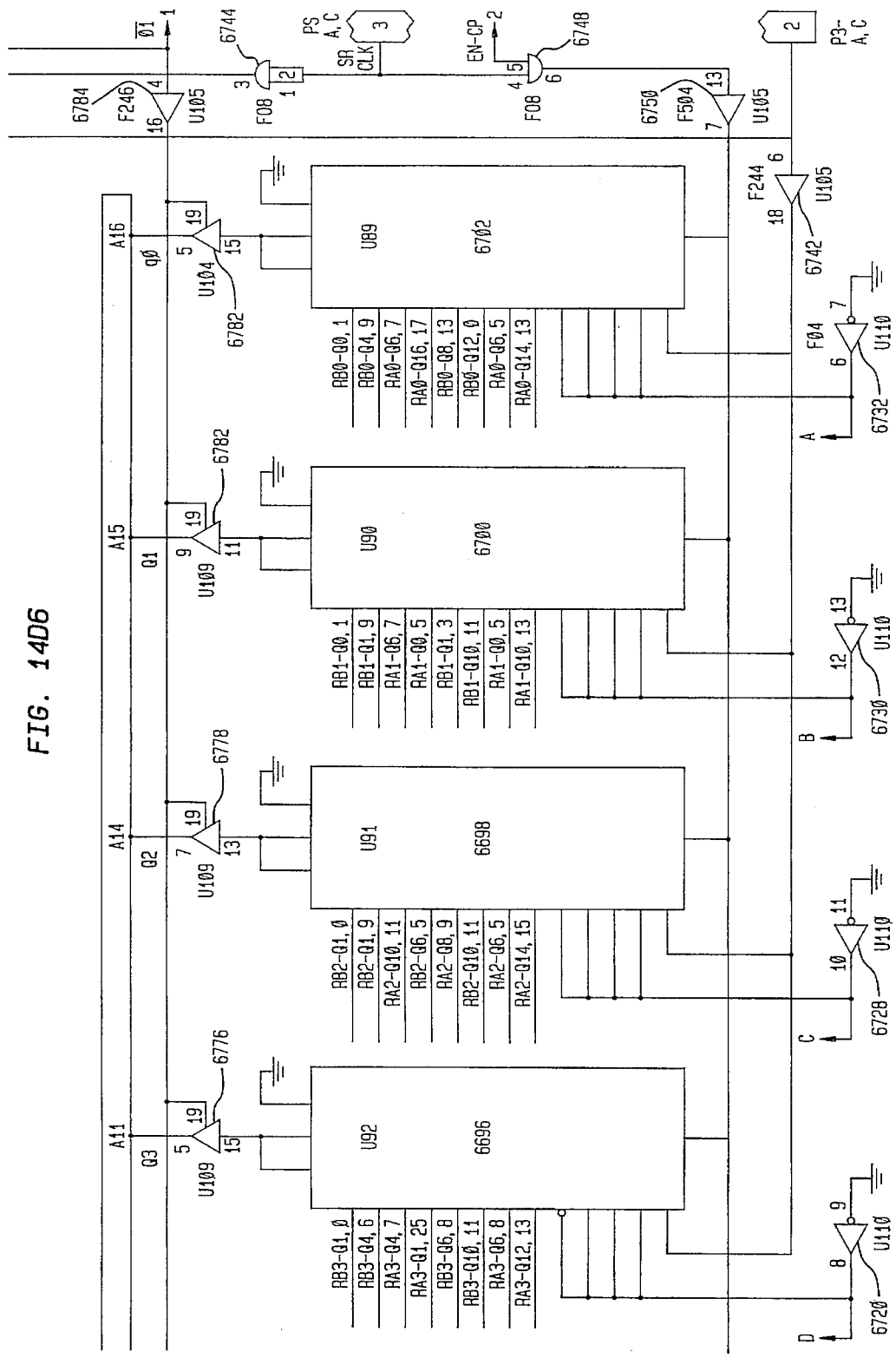
FIG. 14D6

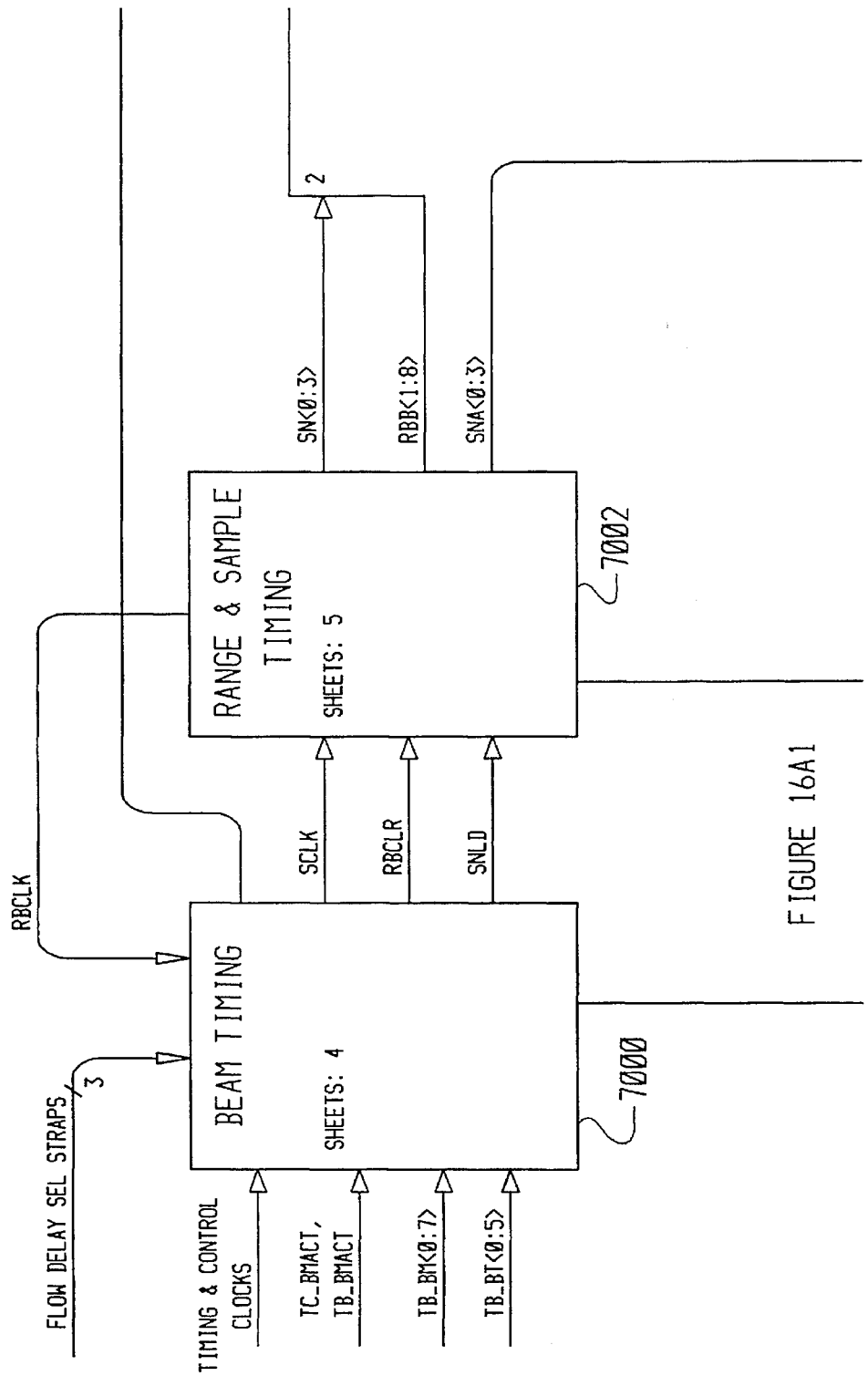
FIGURE 16A1

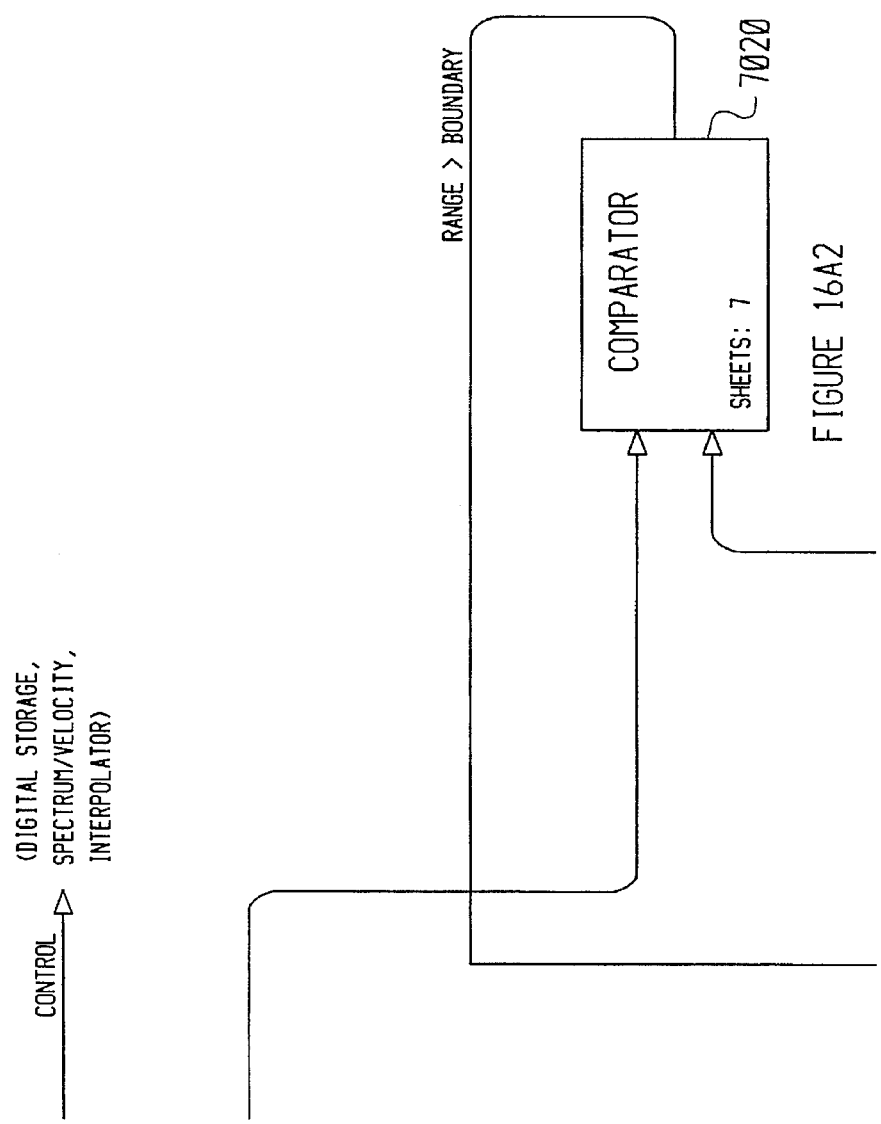
FIGURE 16A2

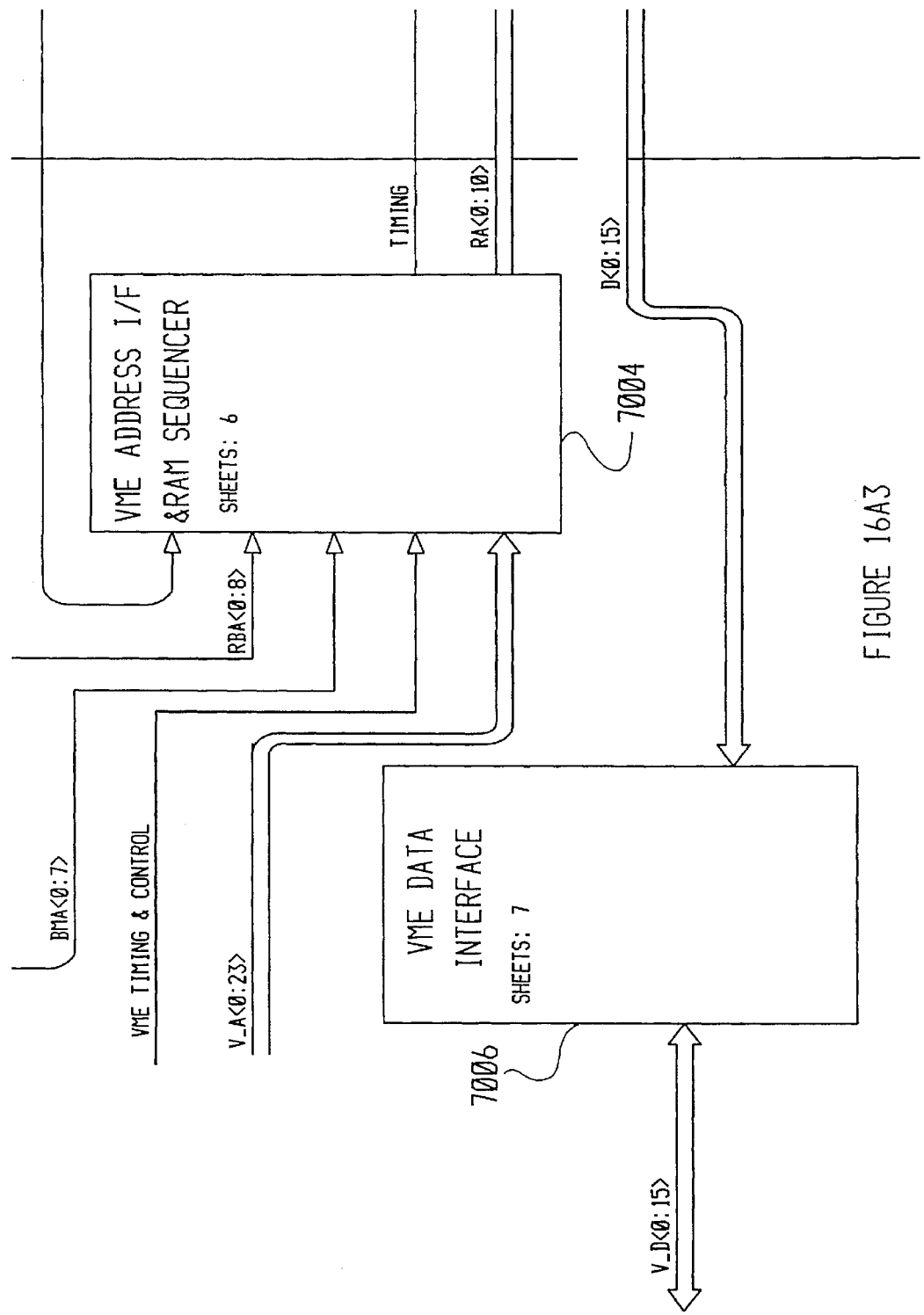

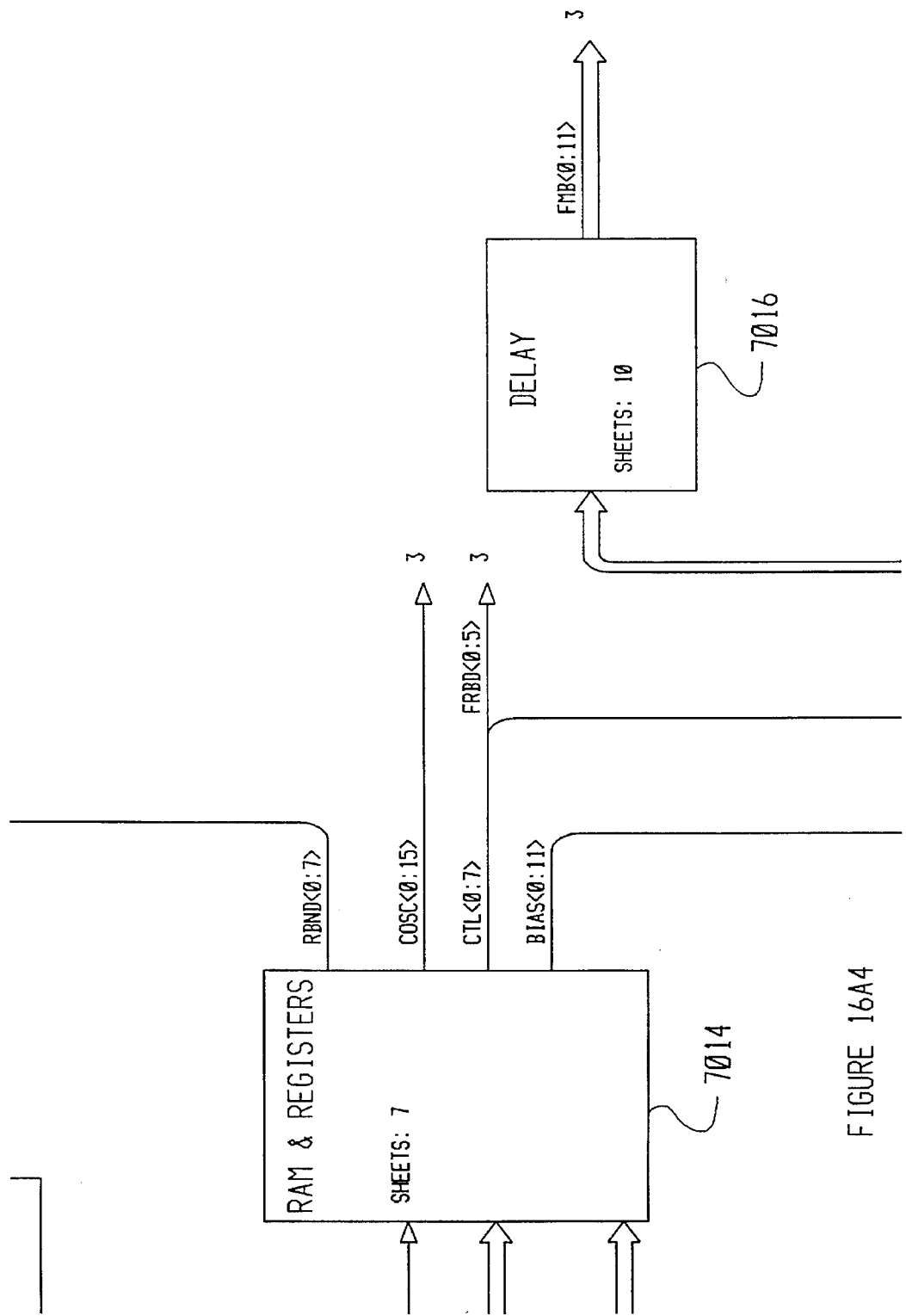
FIGURE 16A4

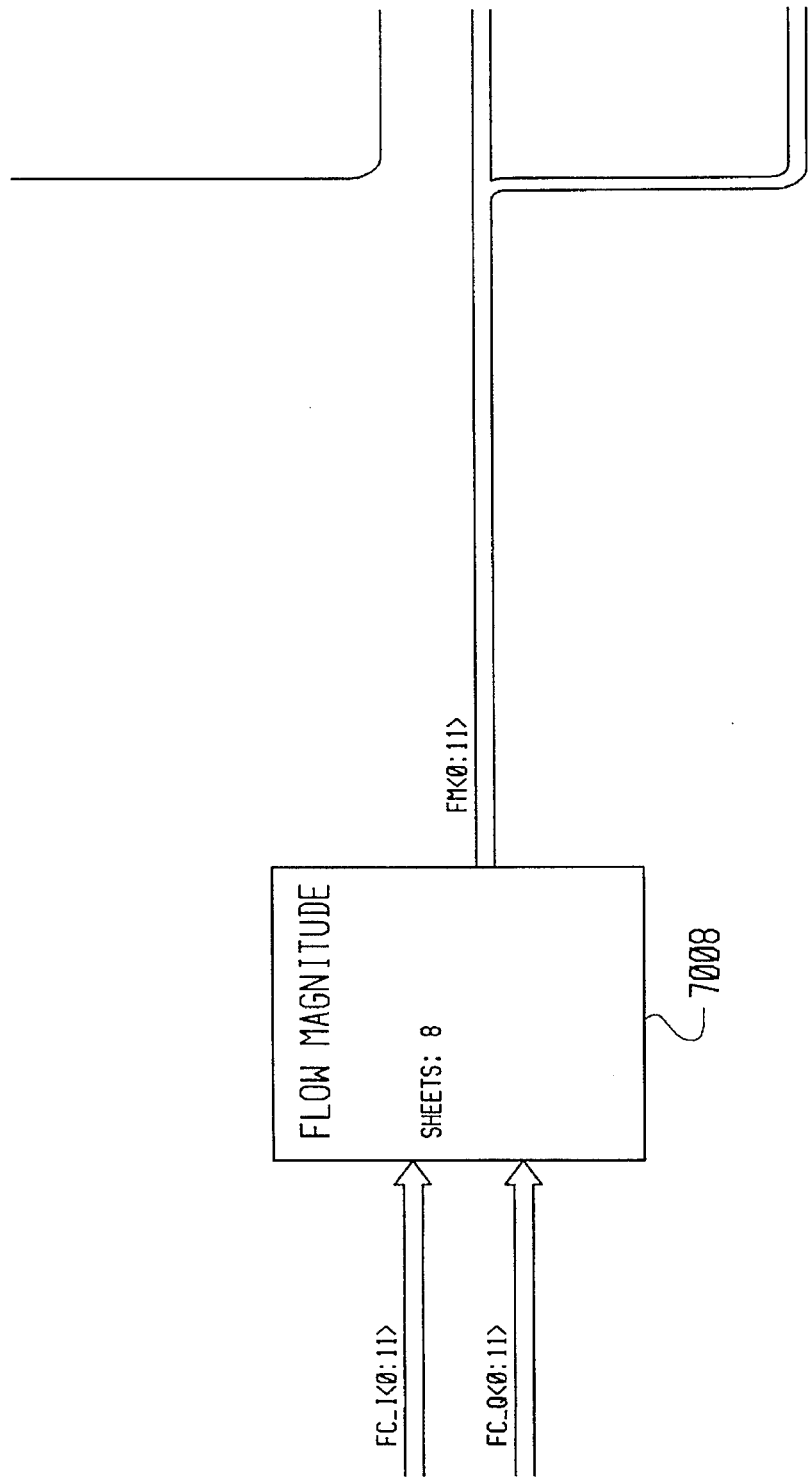
FIGURE 16A5

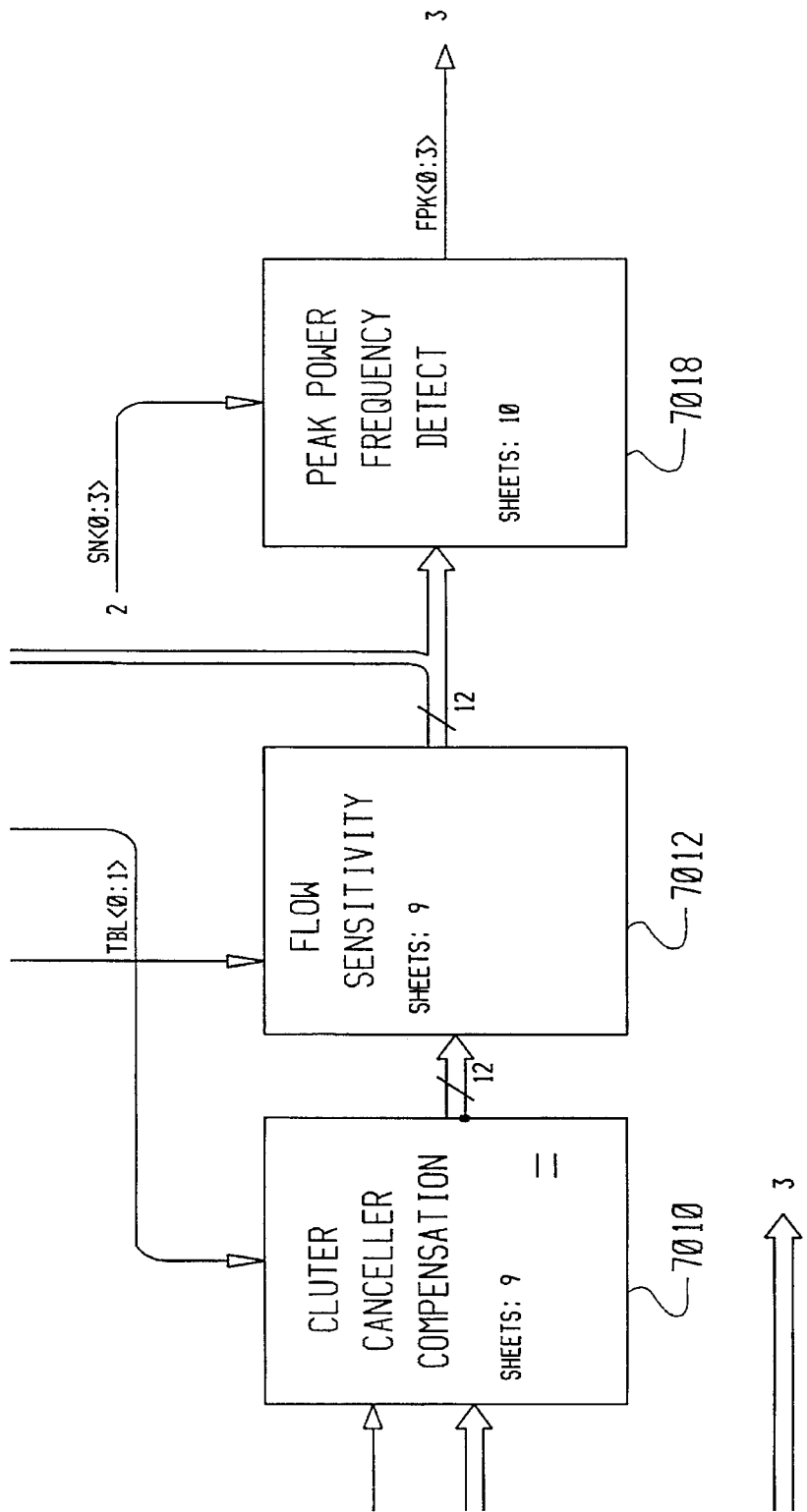
FIGURE 16A6

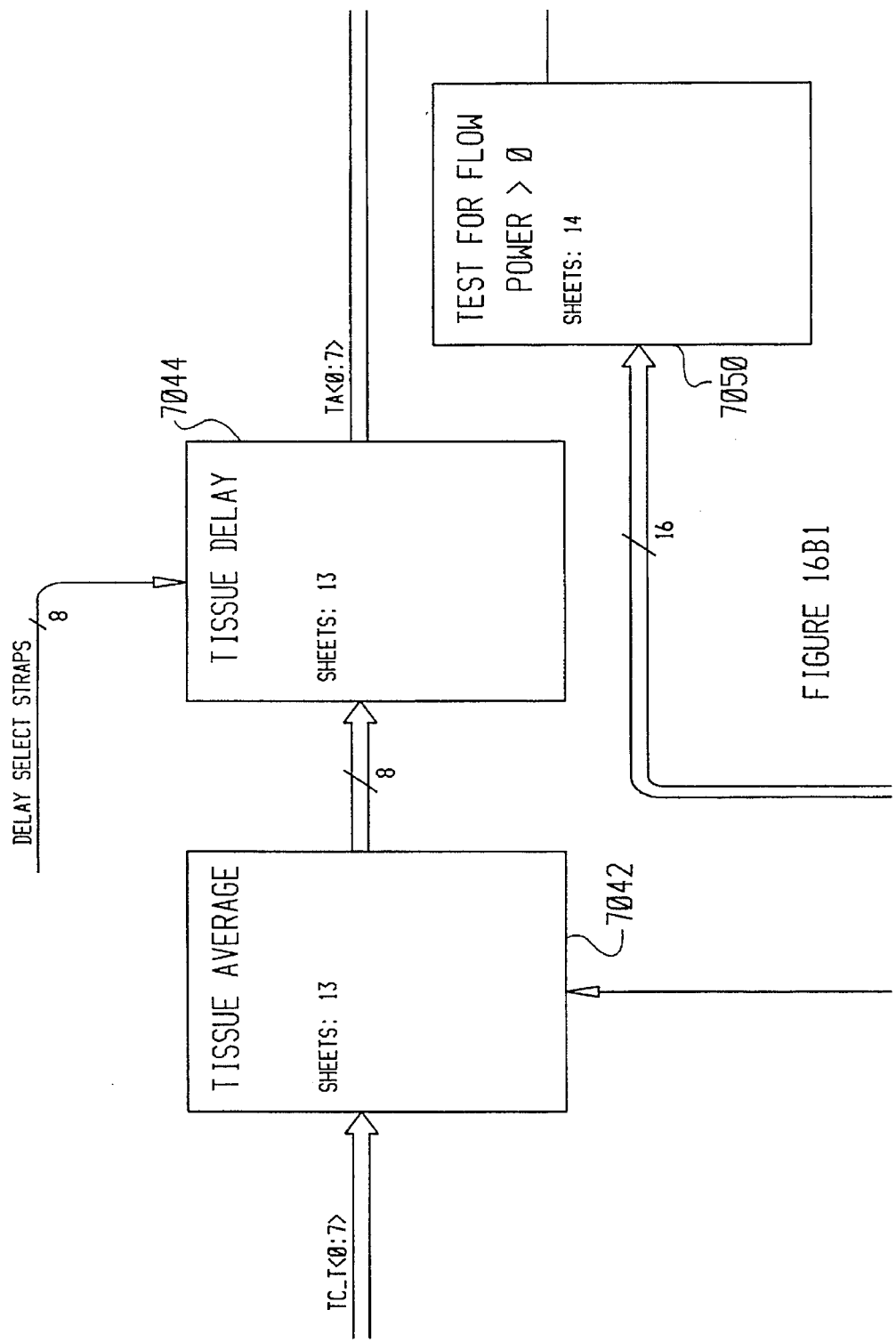
FIGURE 16B1

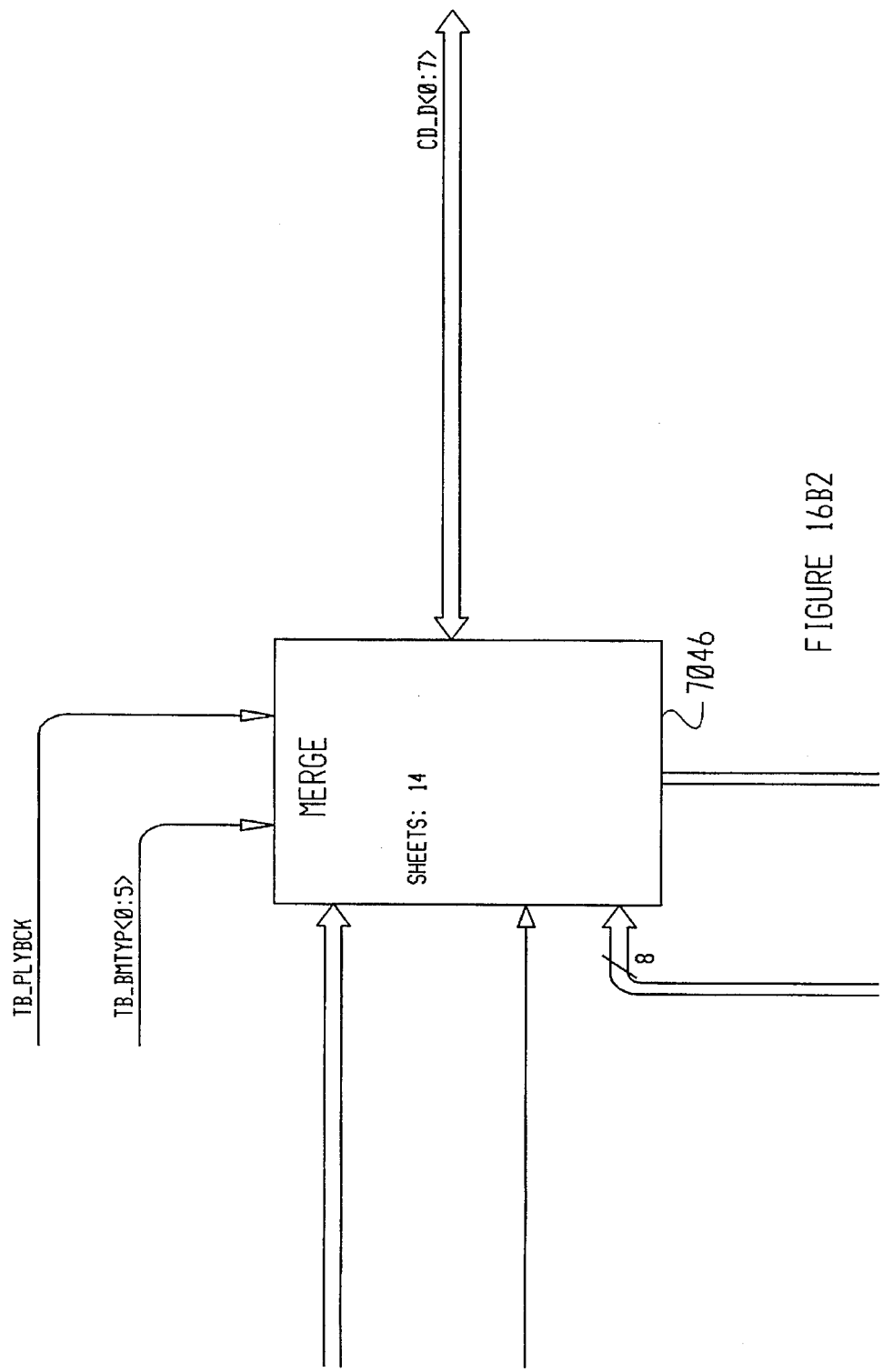
FIGURE 16B2

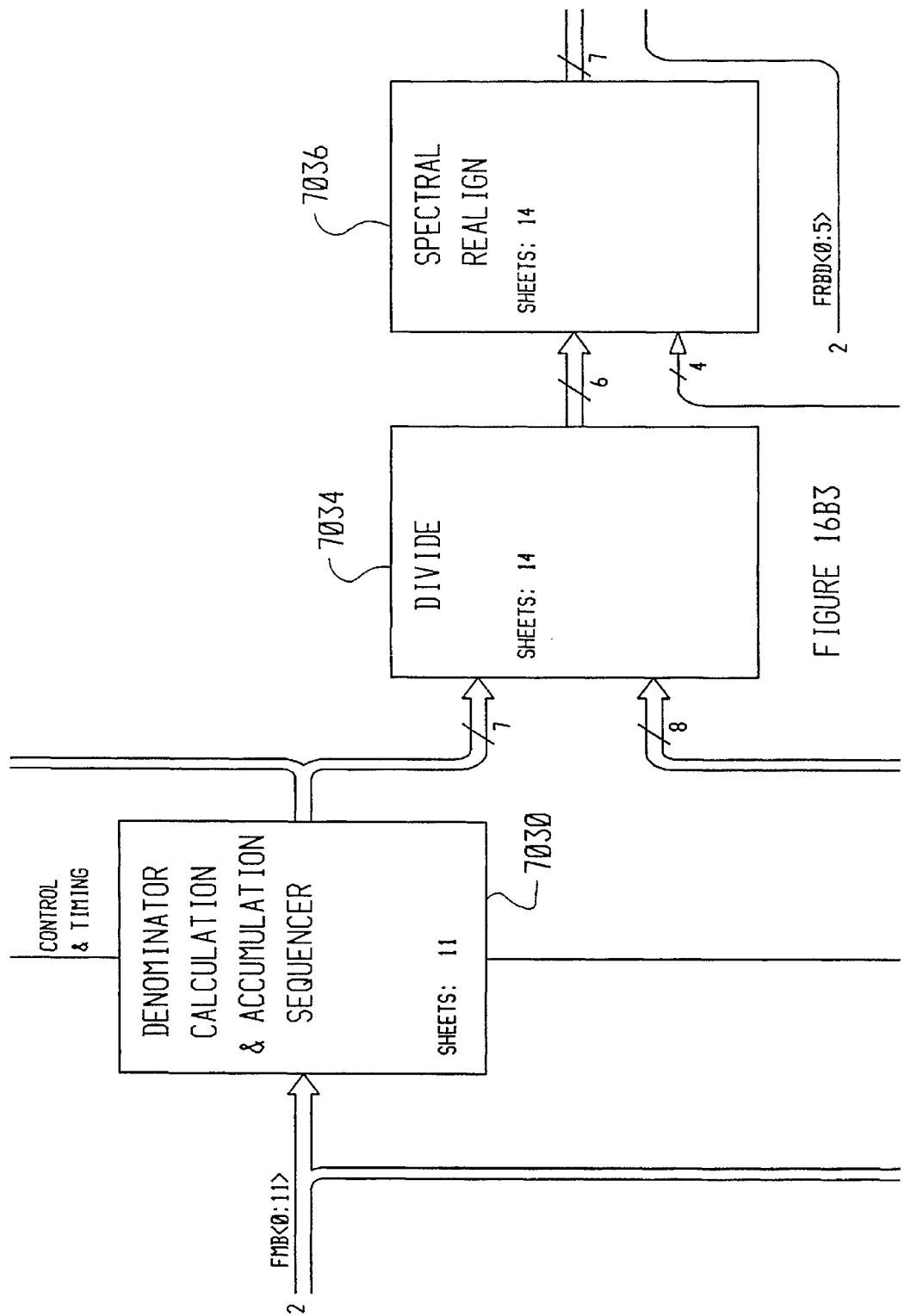
FIGURE 16B3

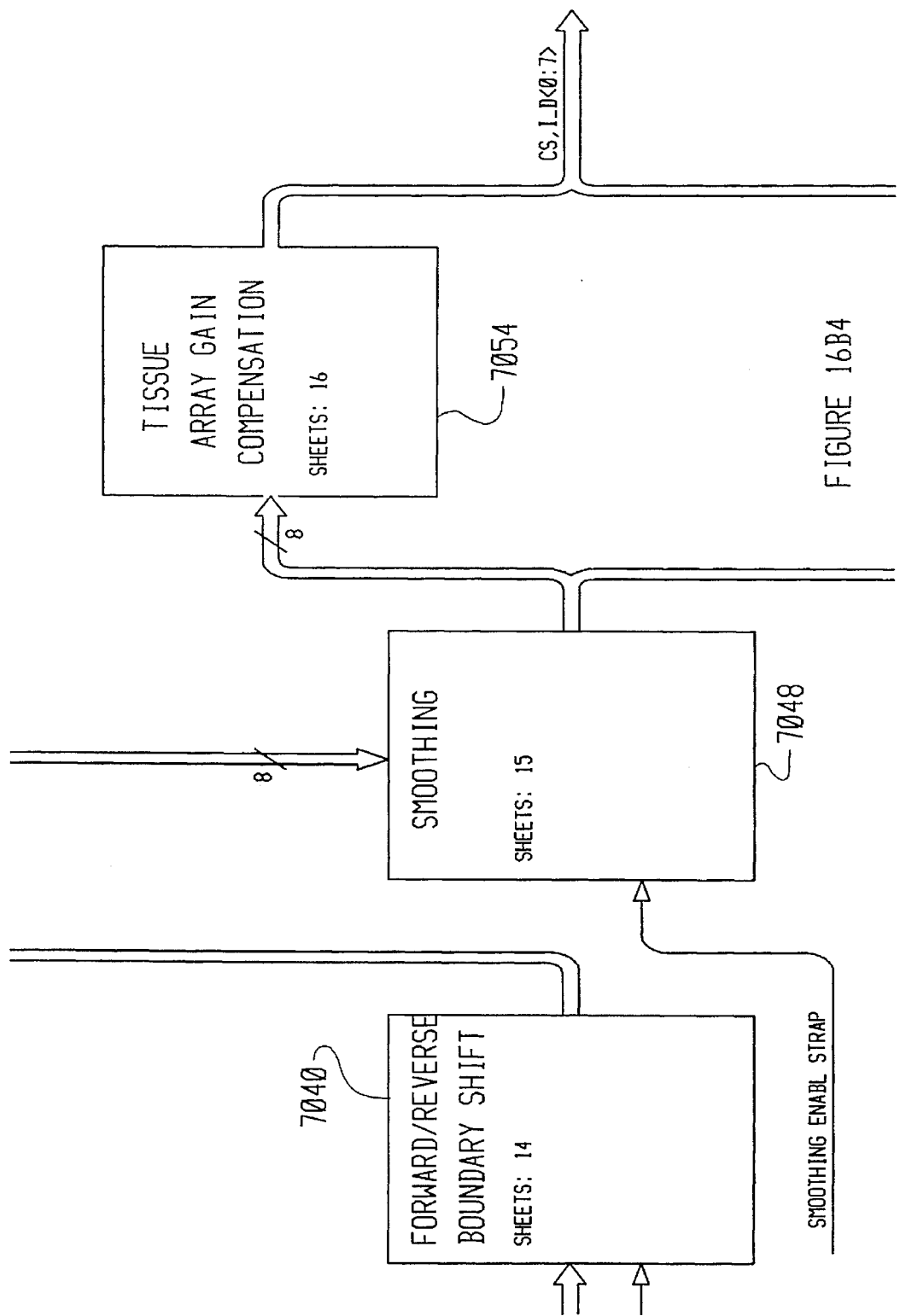
FIGURE 16B4

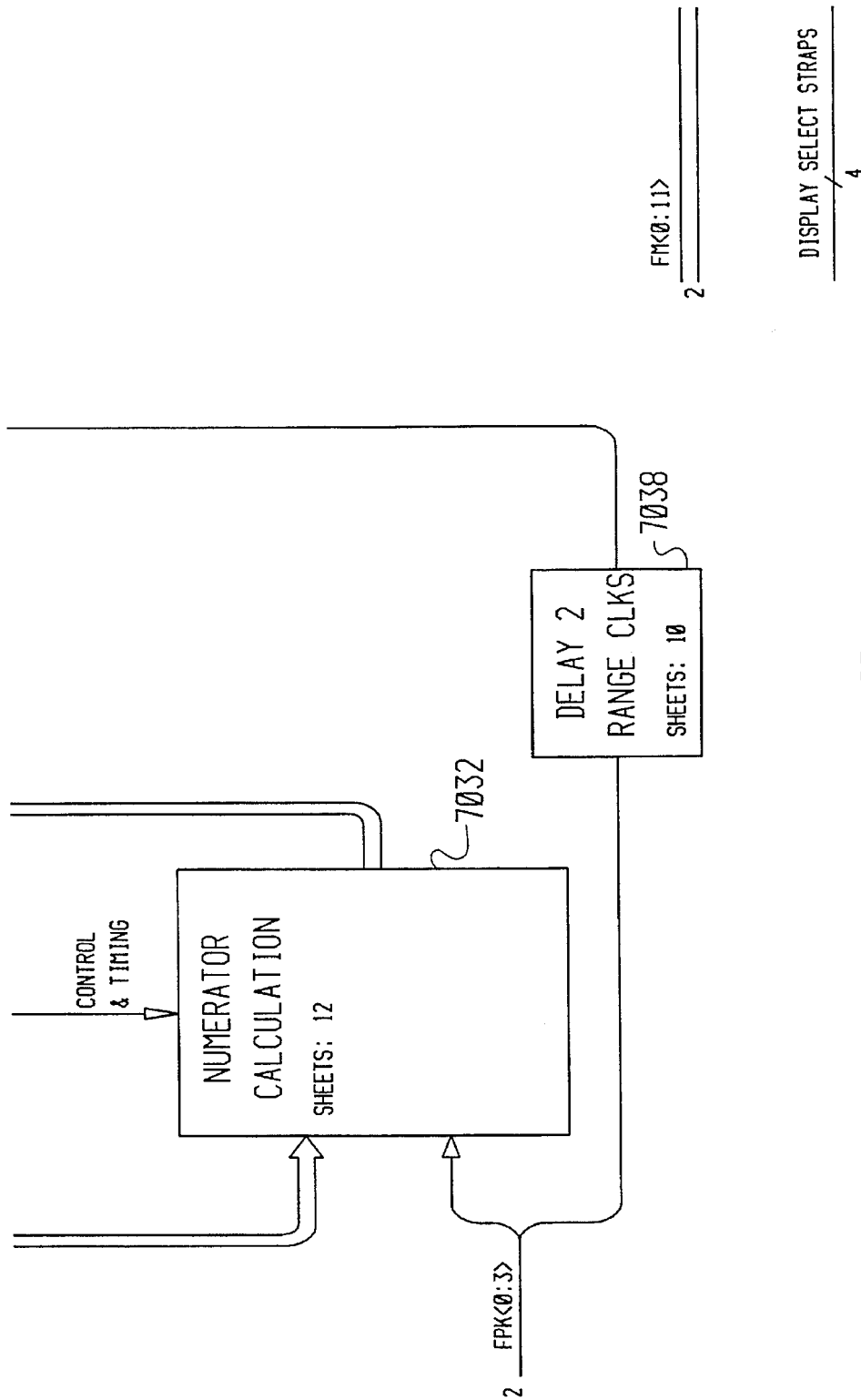
FIGURE 16B5

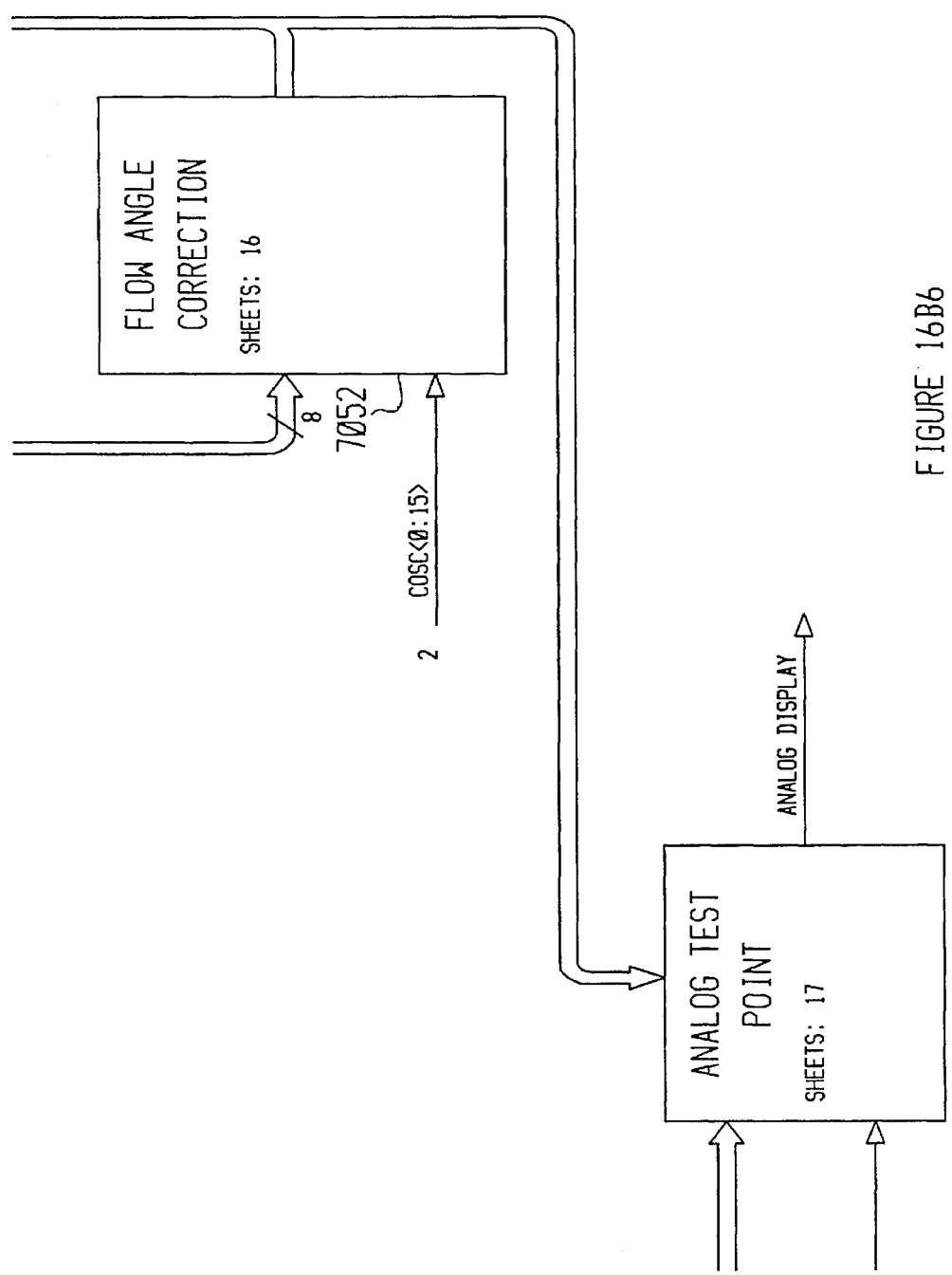
FIGURE 16B6

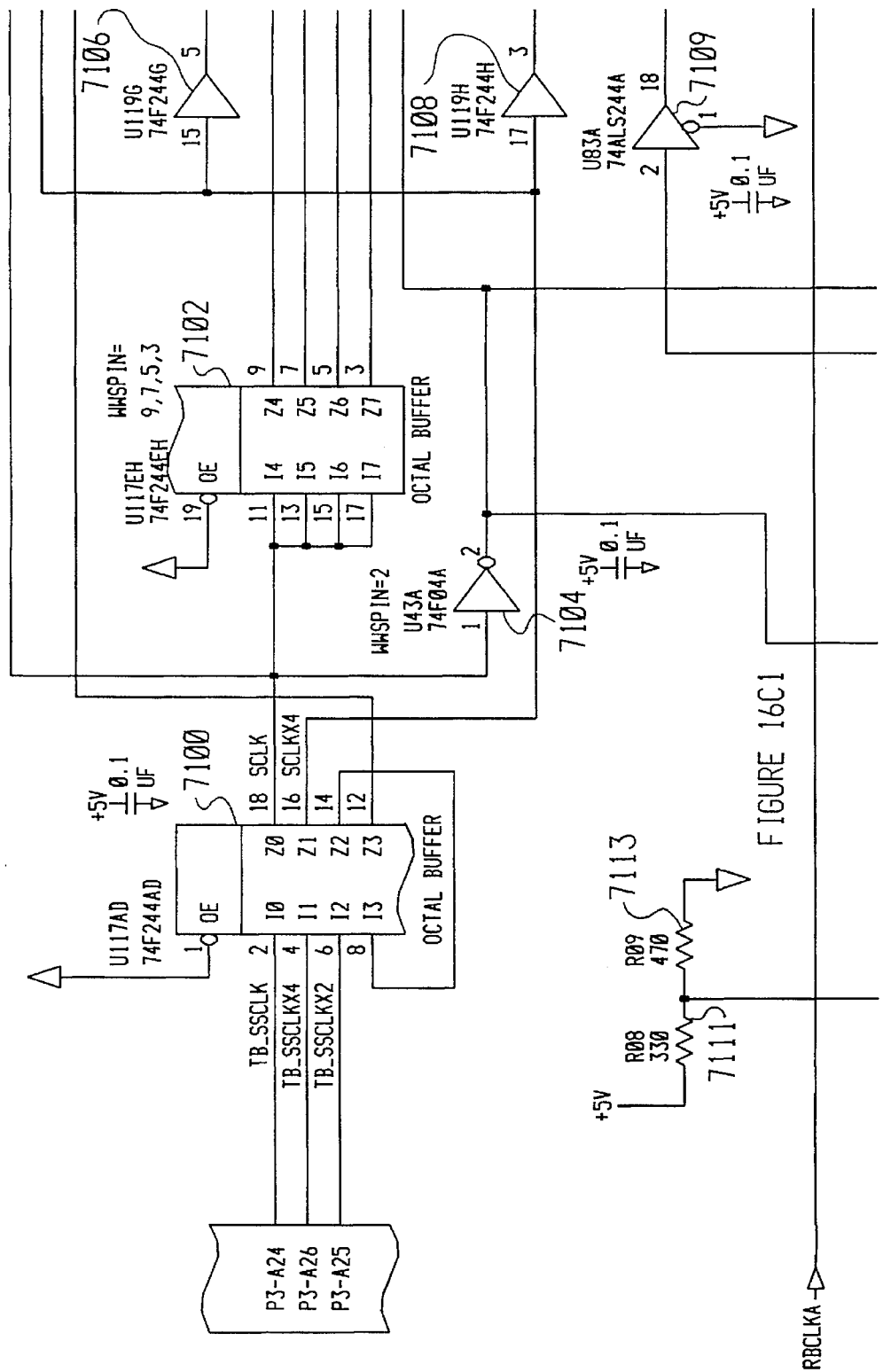
FIGURE 16C1

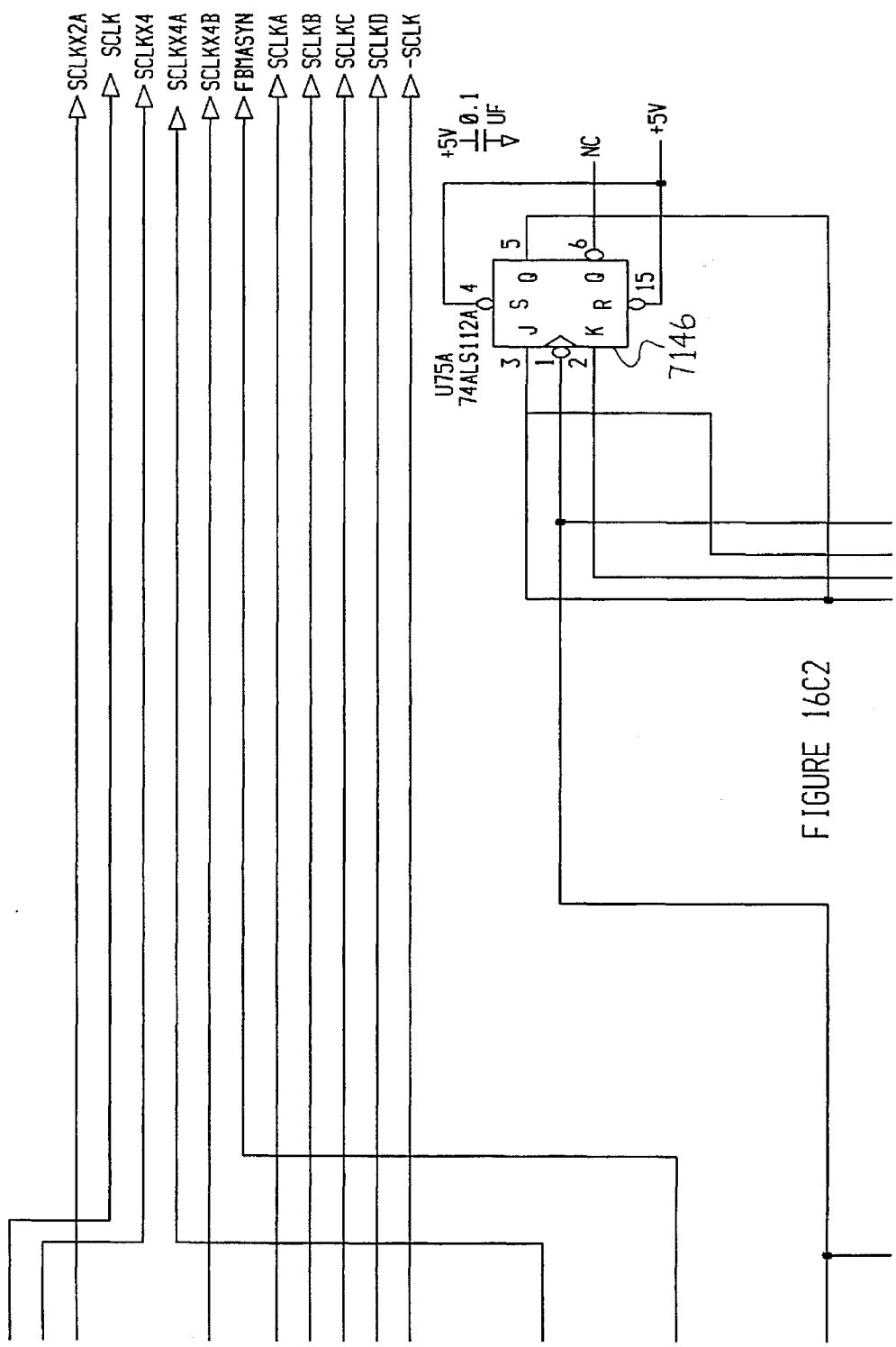
FIGURE 16C2

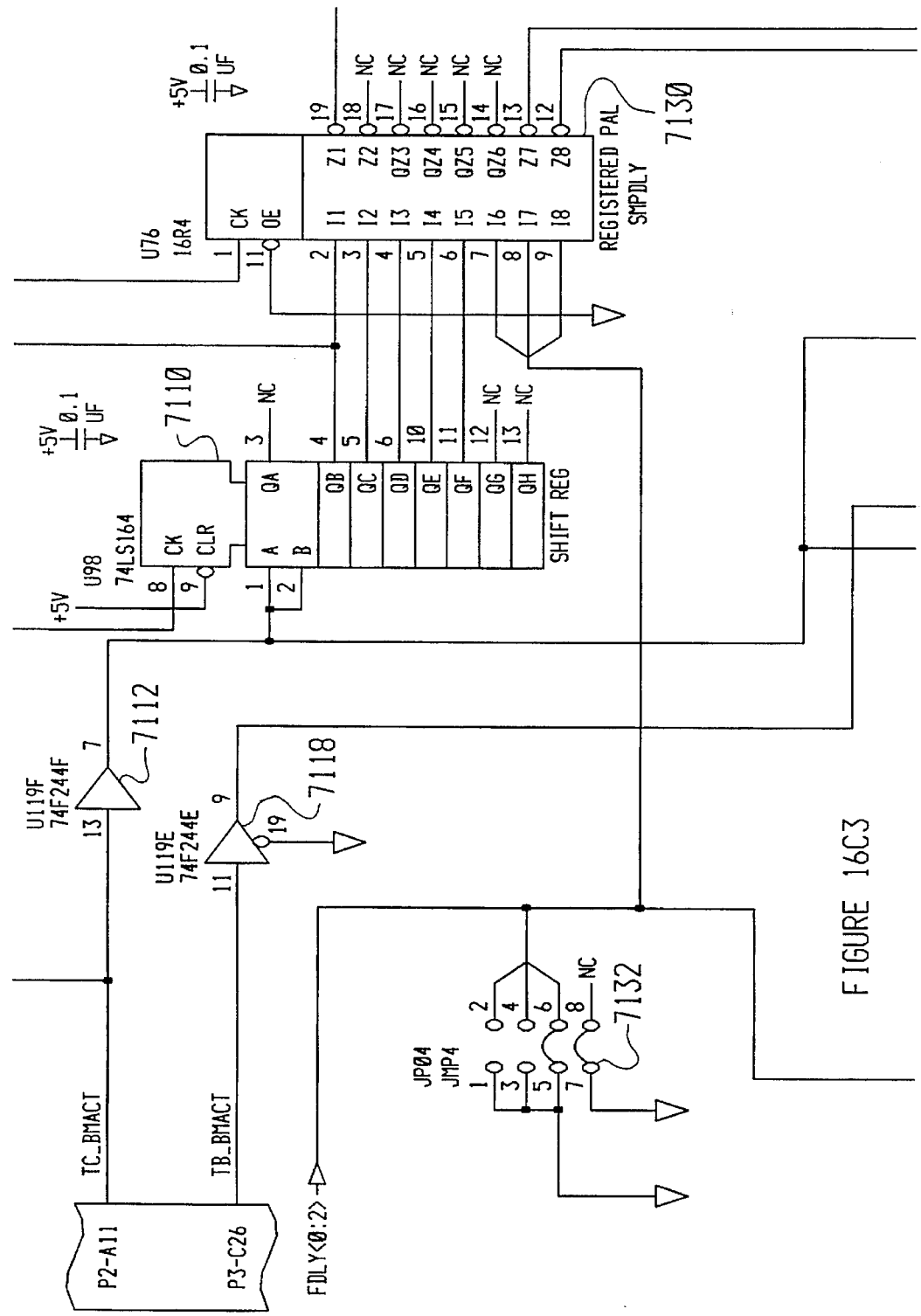
FIGURE 16C3

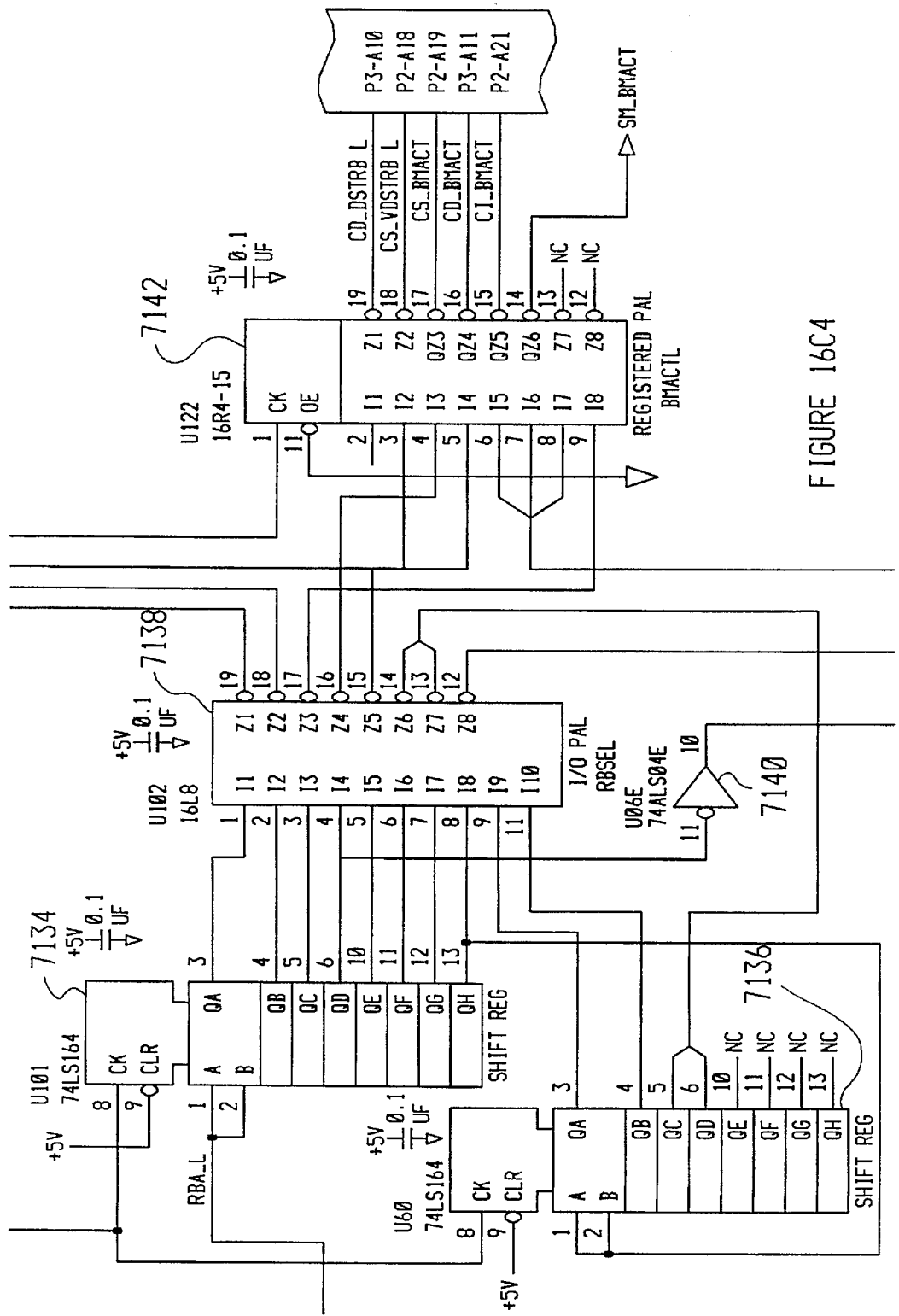
FIGURE 16C4

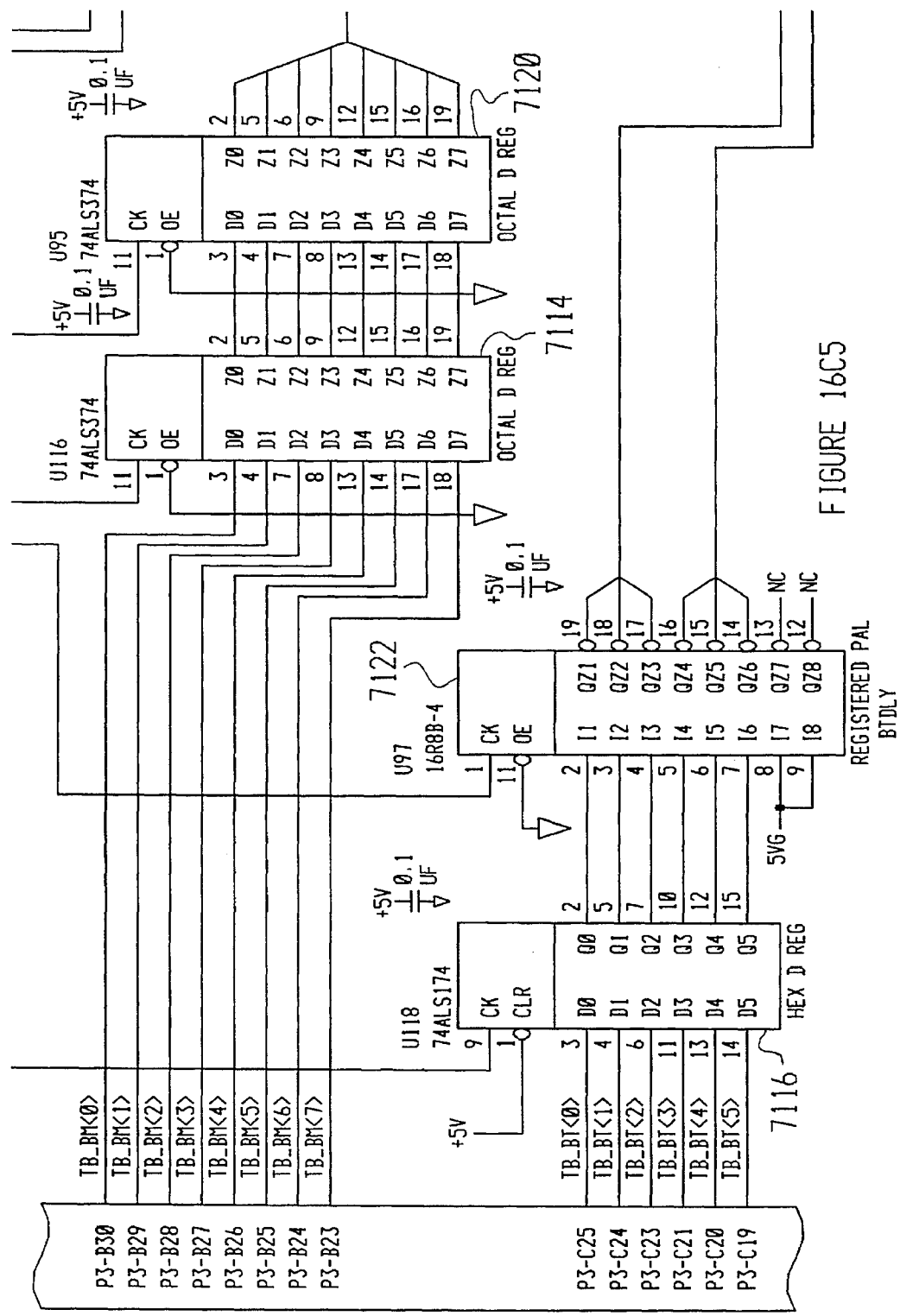
FIGURE 16C5

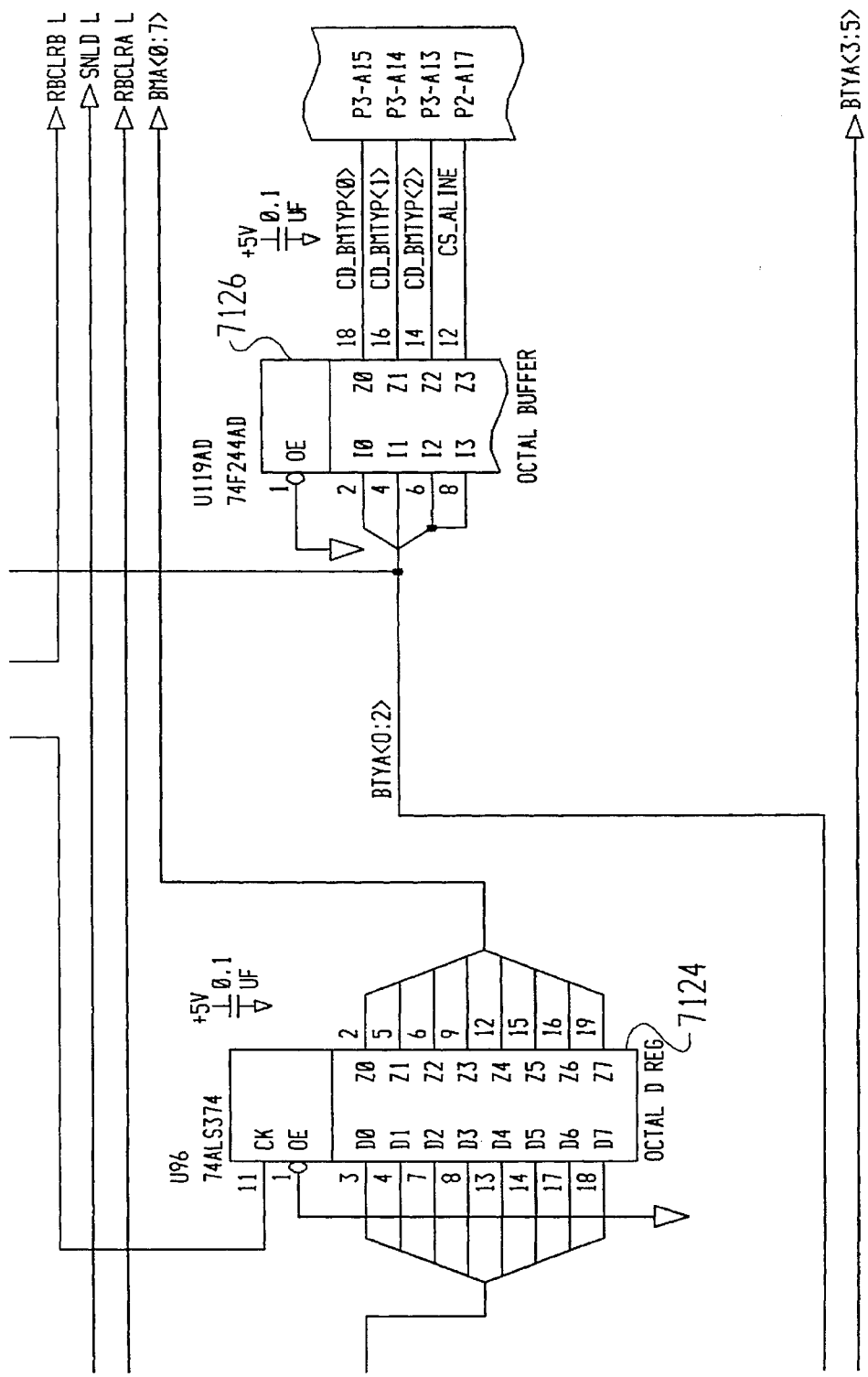
FIGURE 16C6

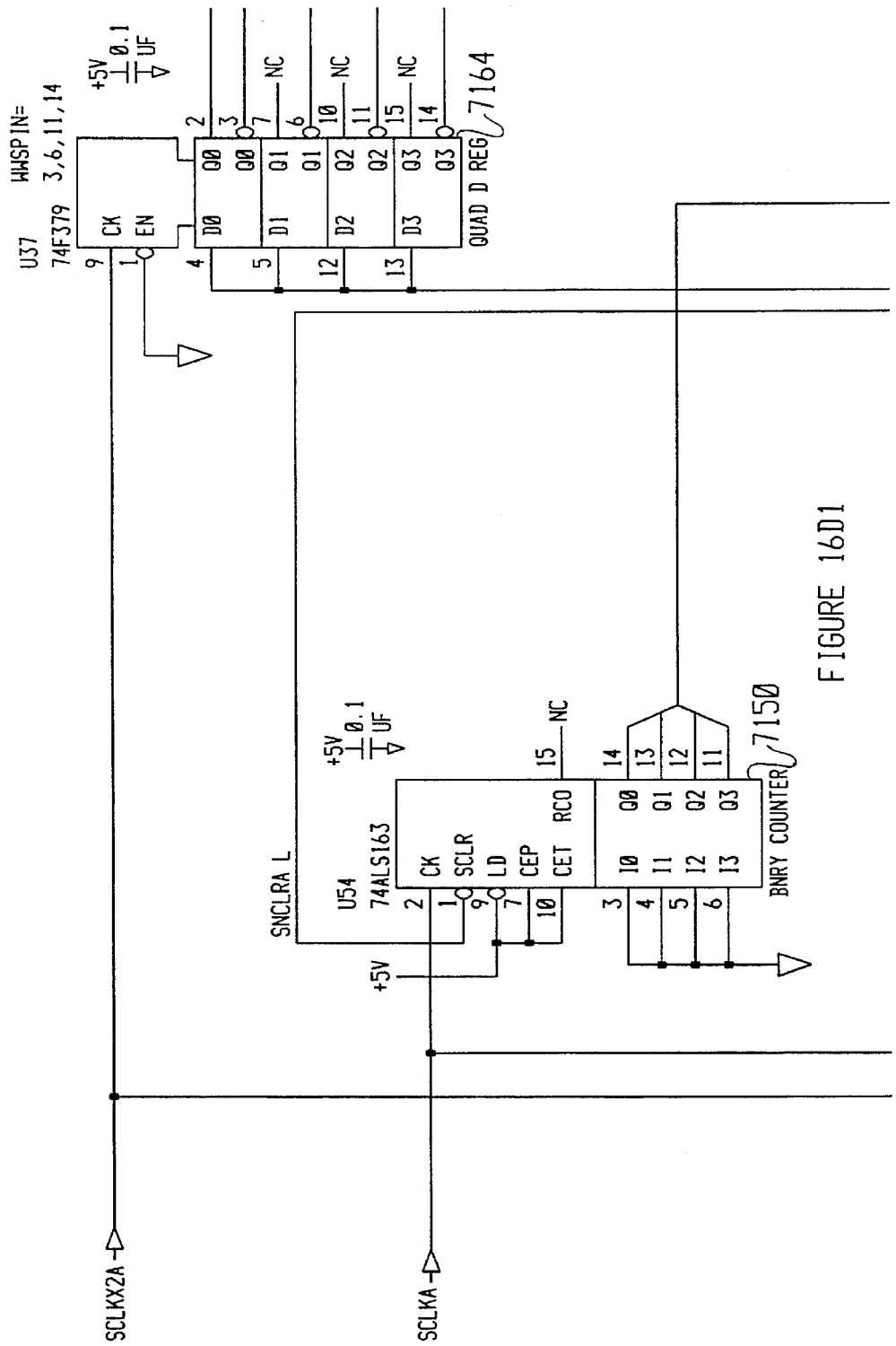
FIGURE 16D1

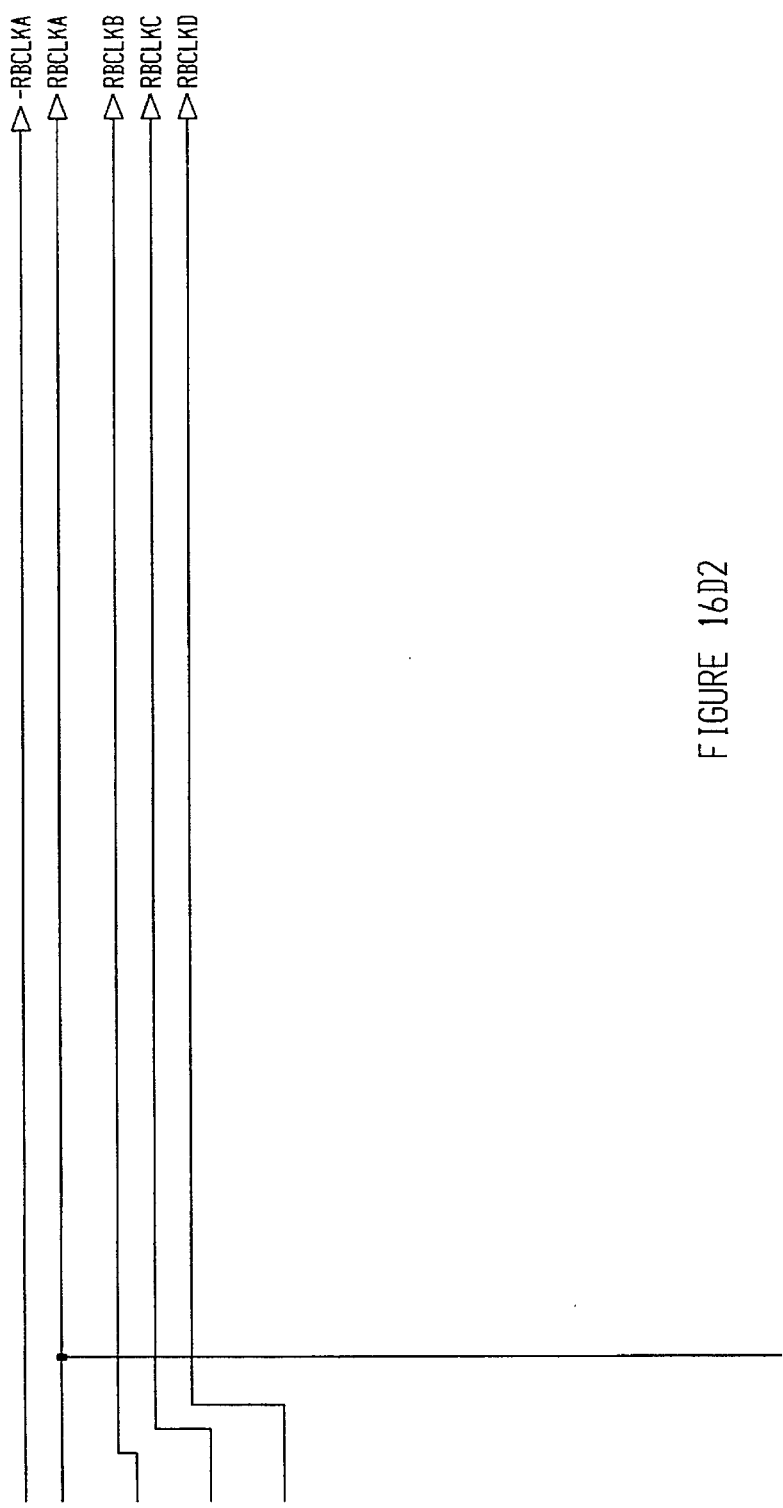
FIGURE 16D2

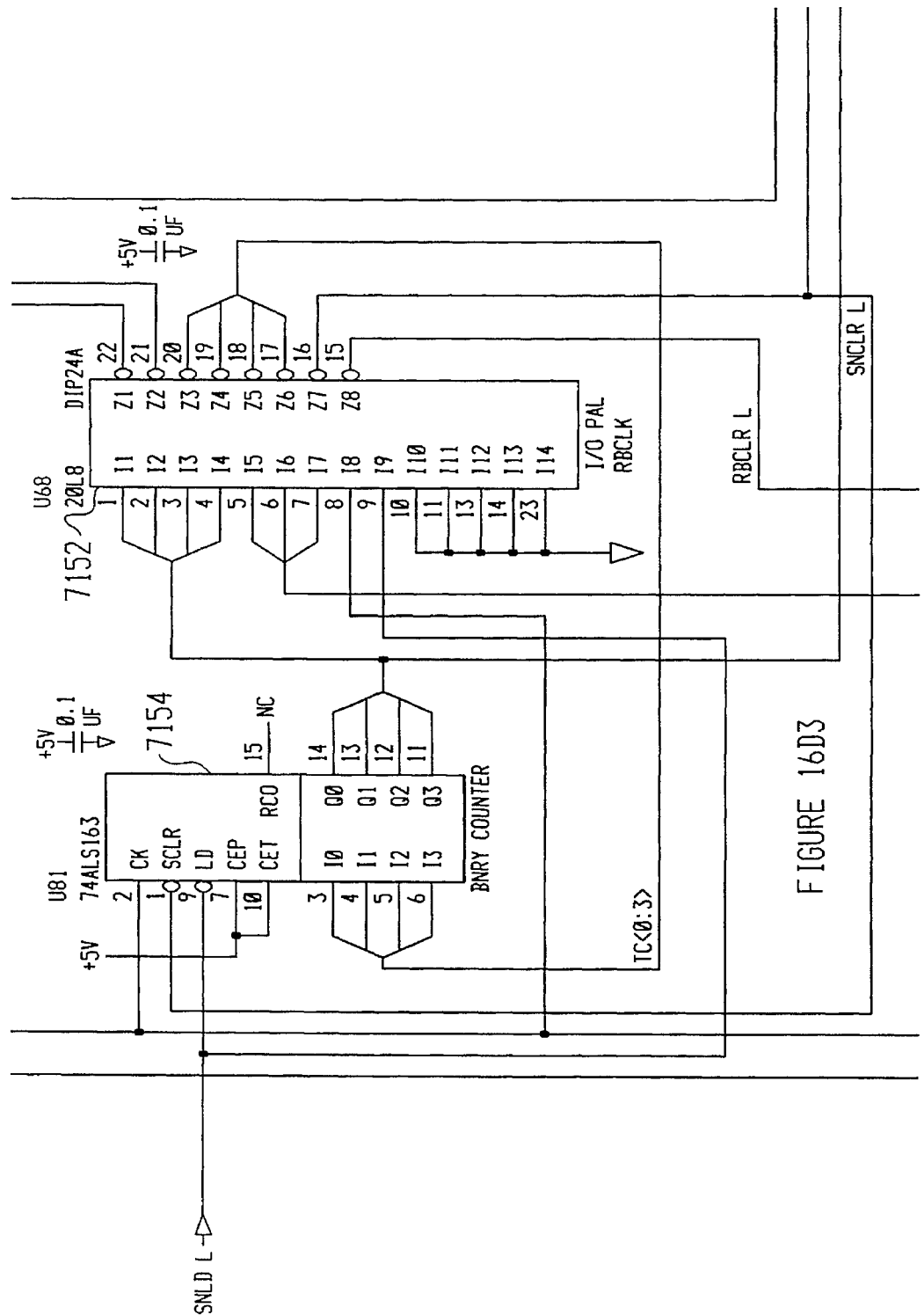
FIGURE 16D3

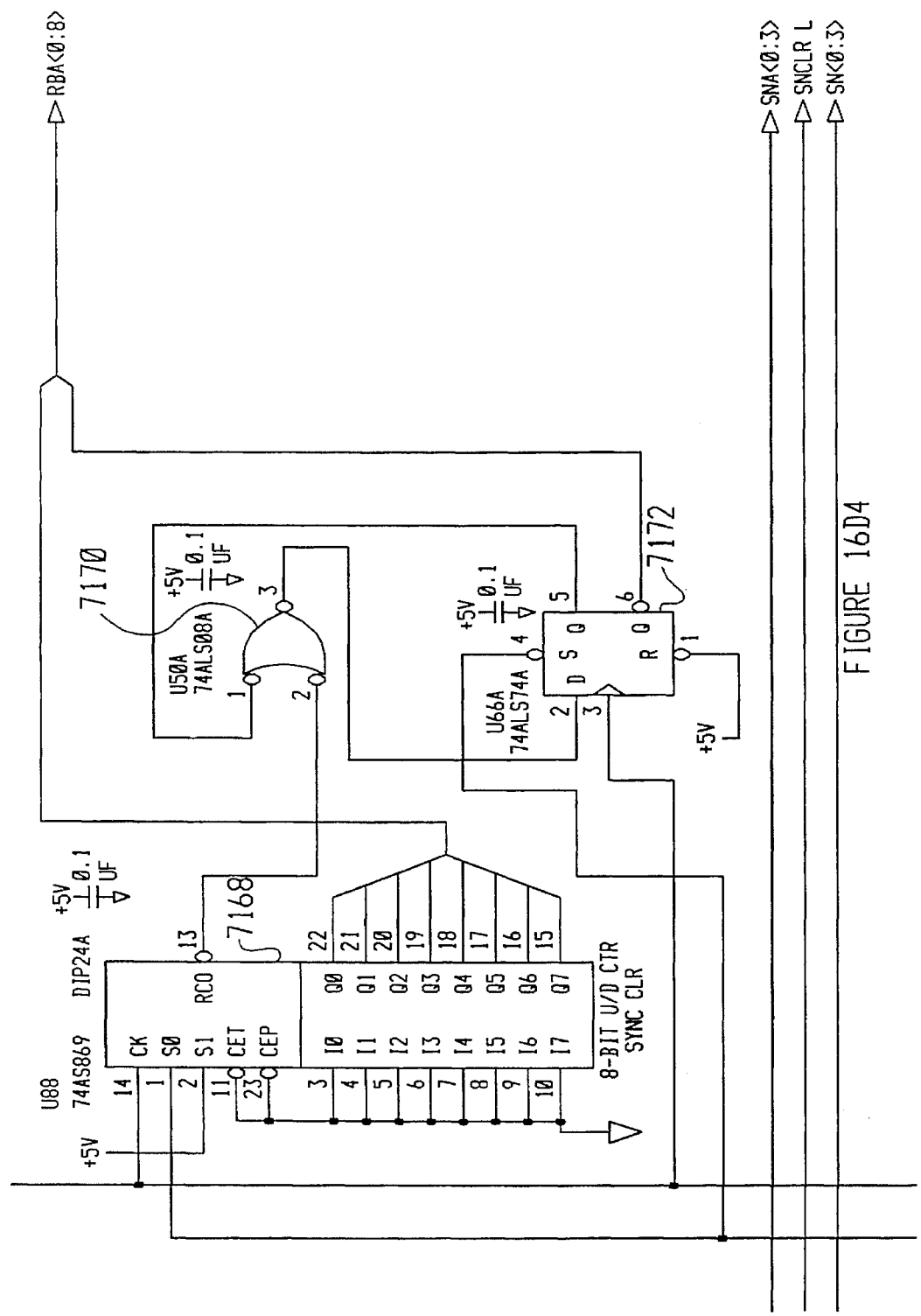
FIGURE 16D4

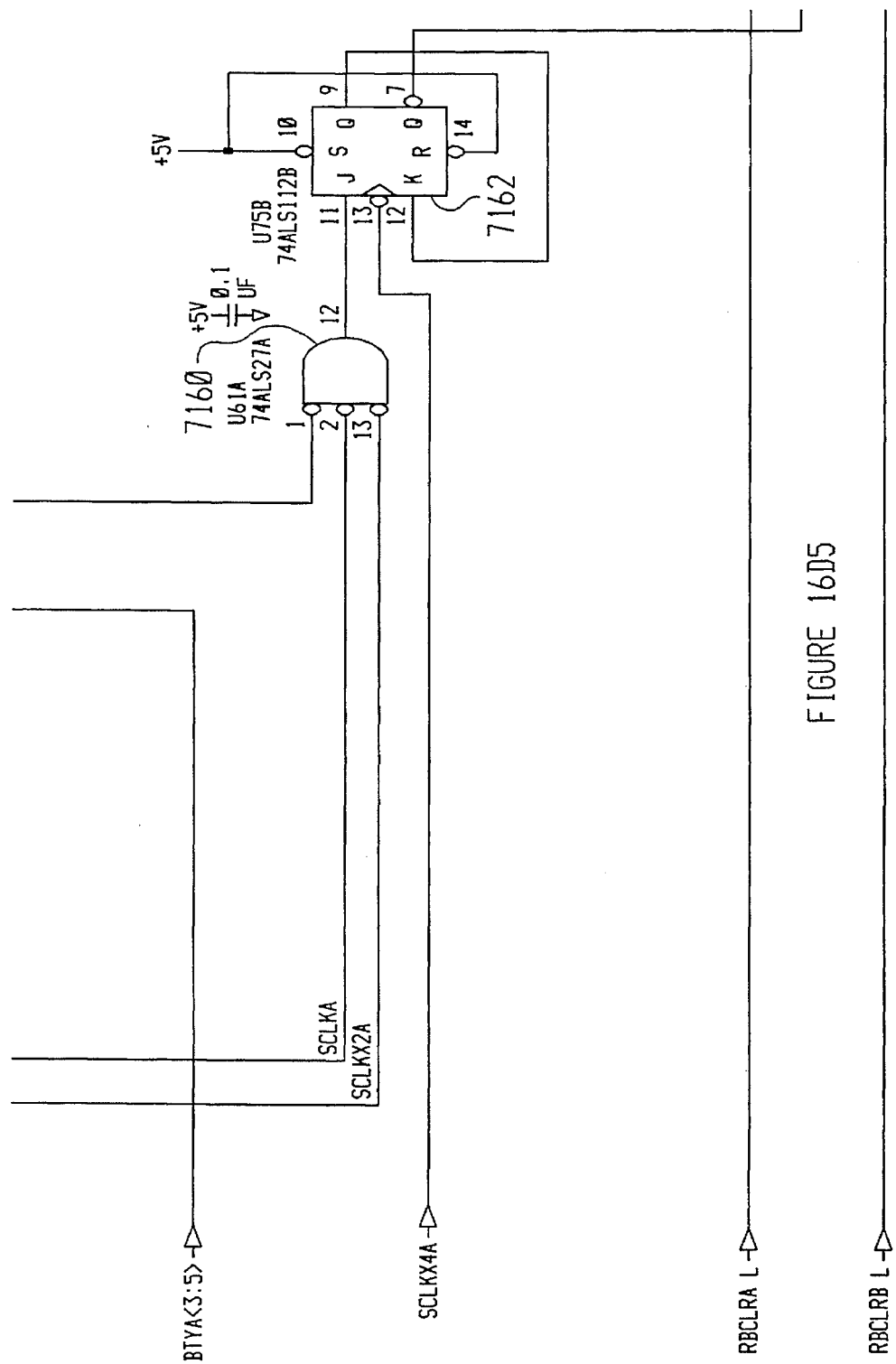
FIGURE 16D5

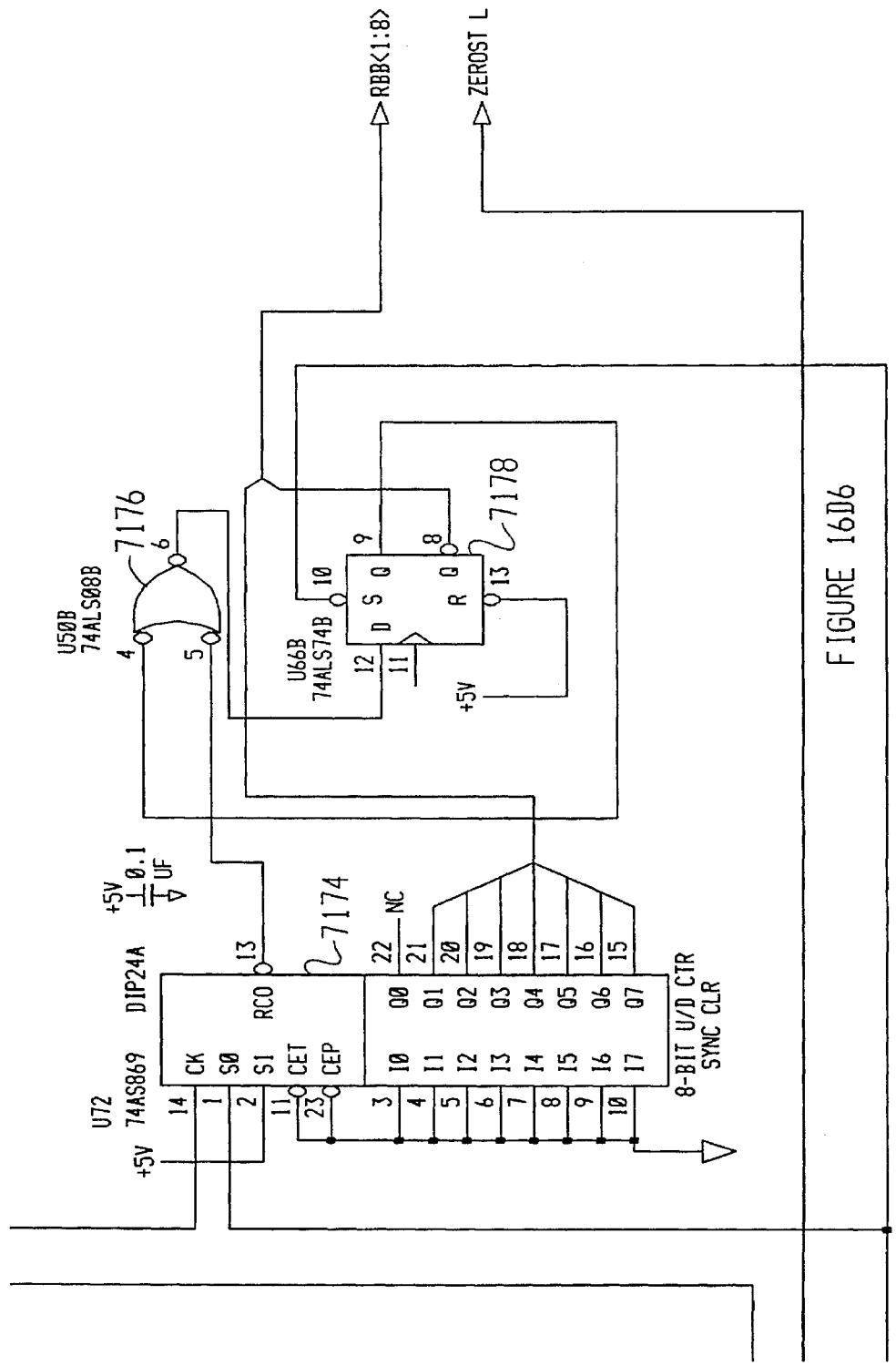
FIGURE 1606

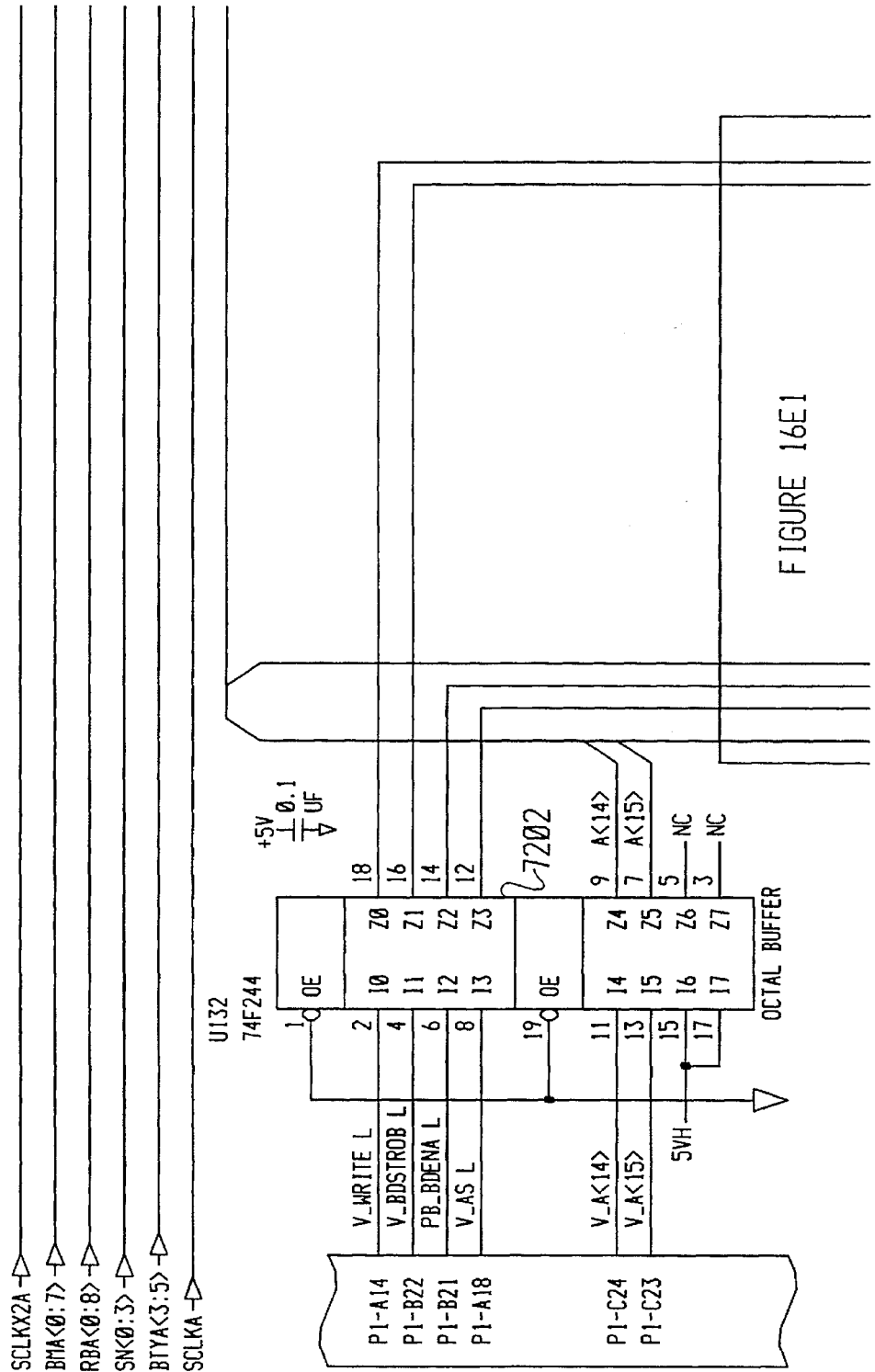

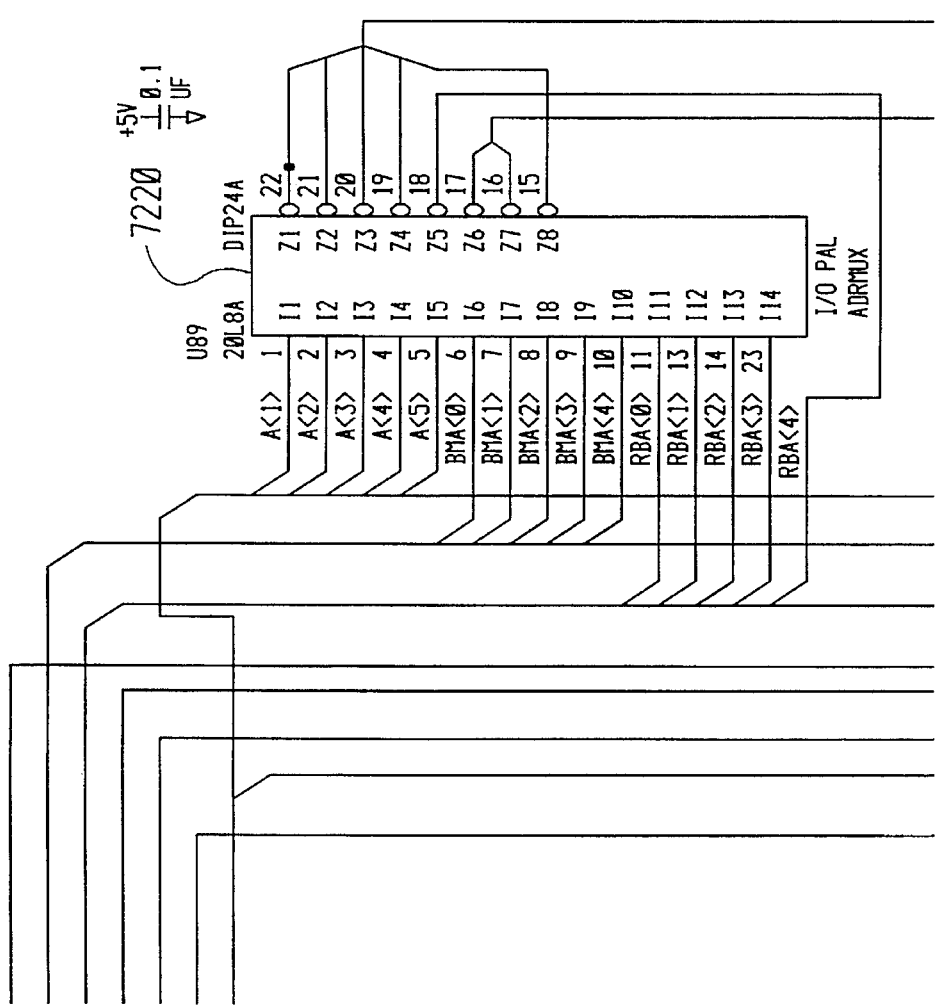
FIGURE 16E2

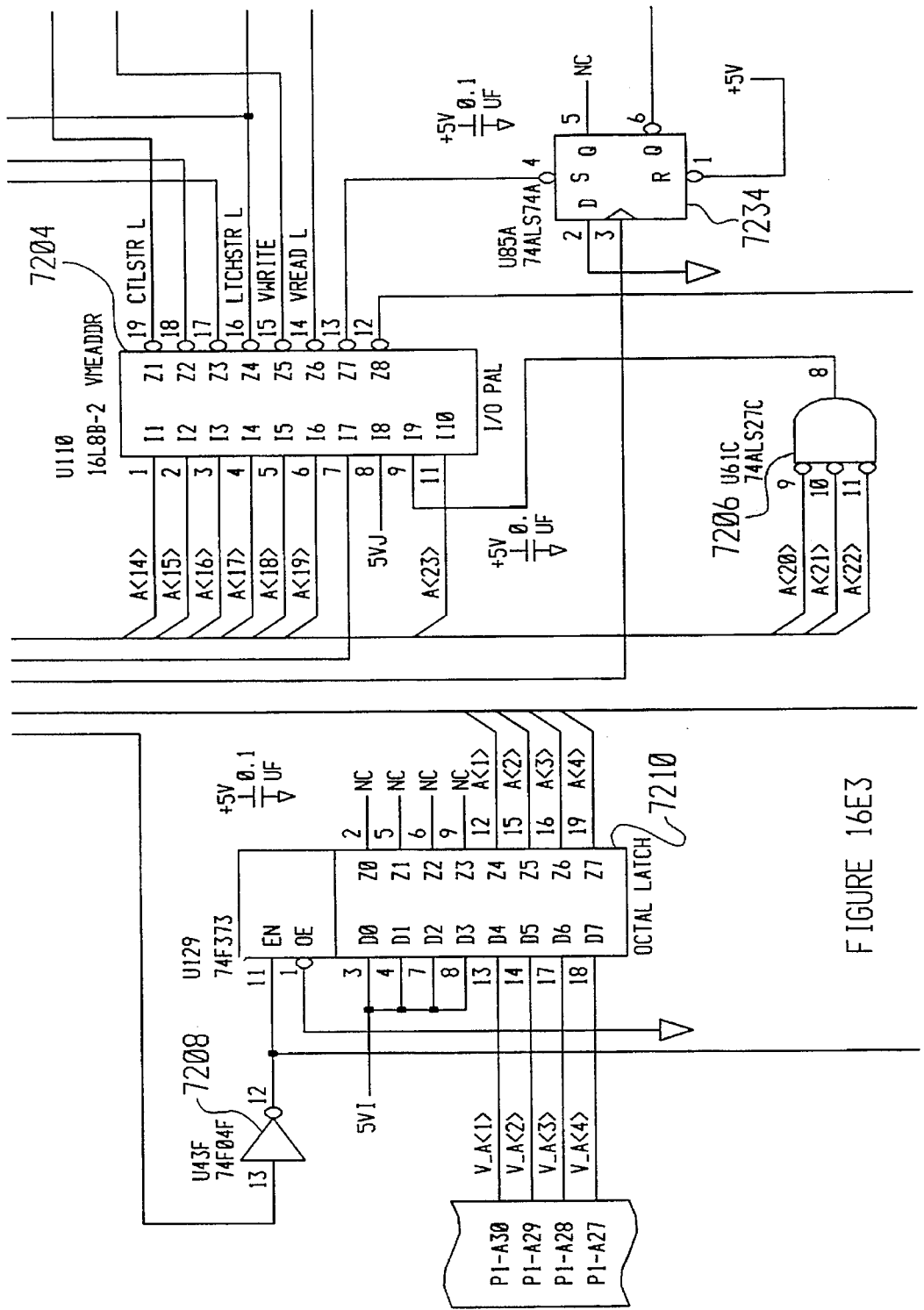
FIGURE 16E3

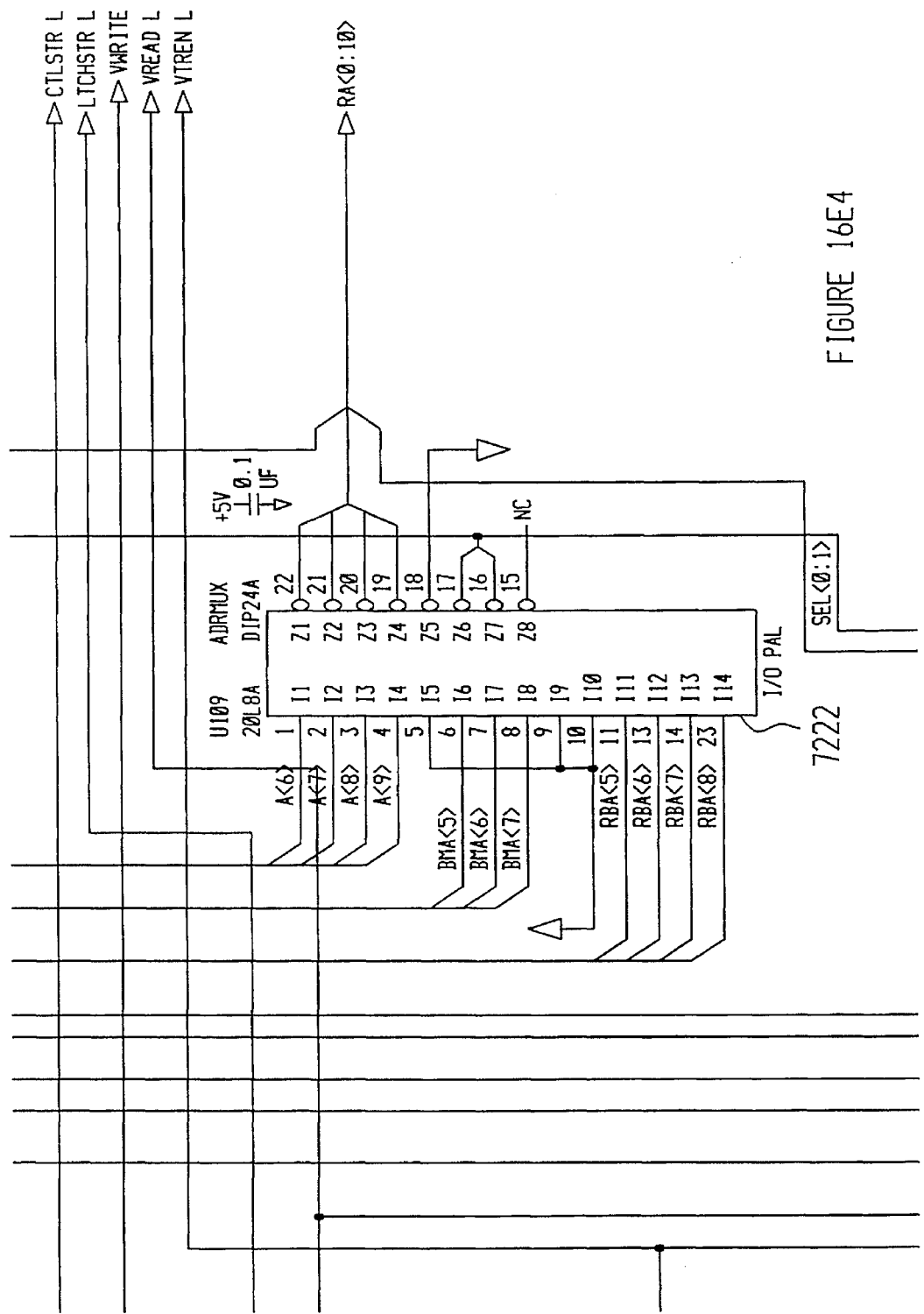
FIGURE 16E4

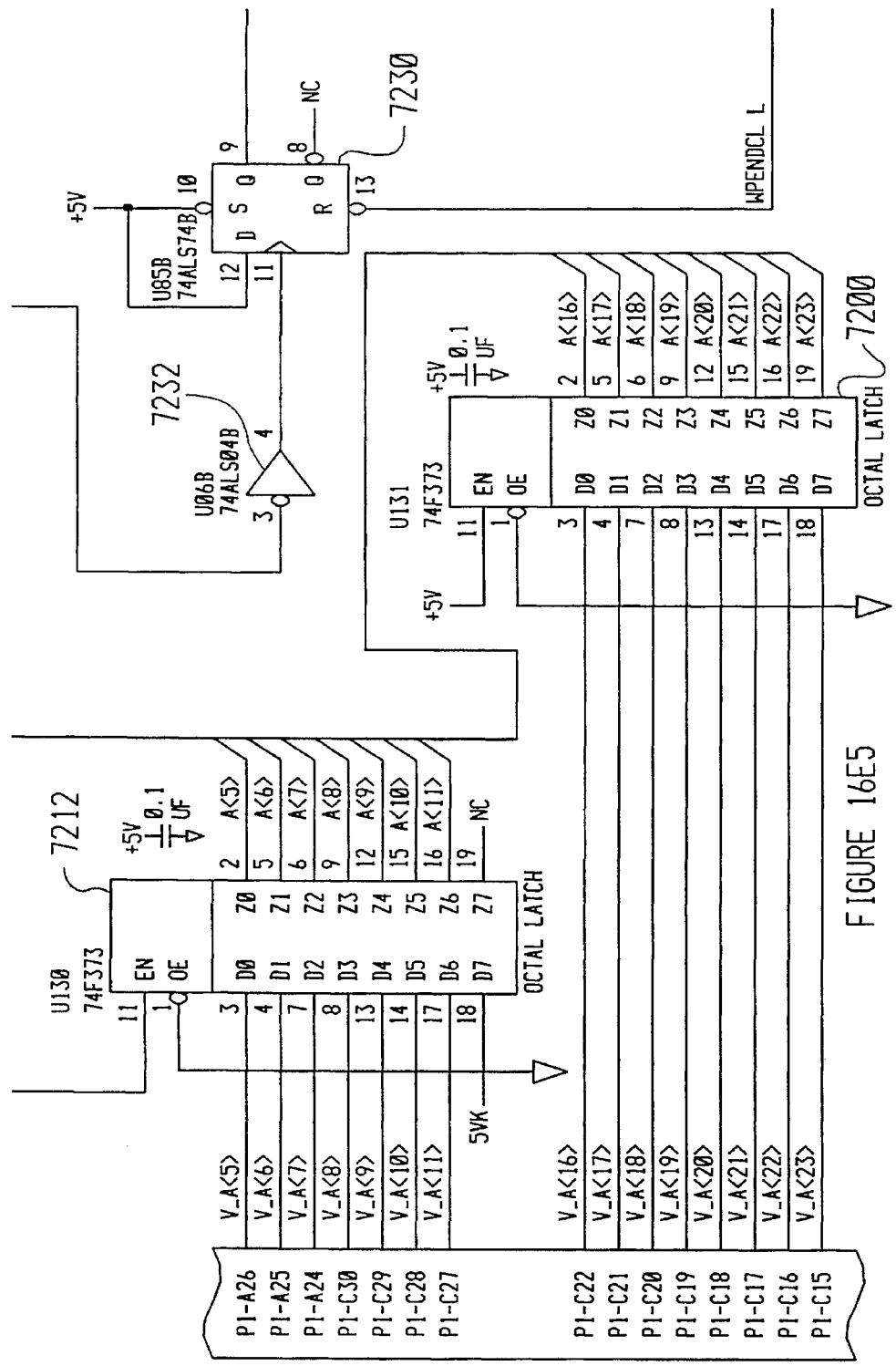
FIGURE 16E5

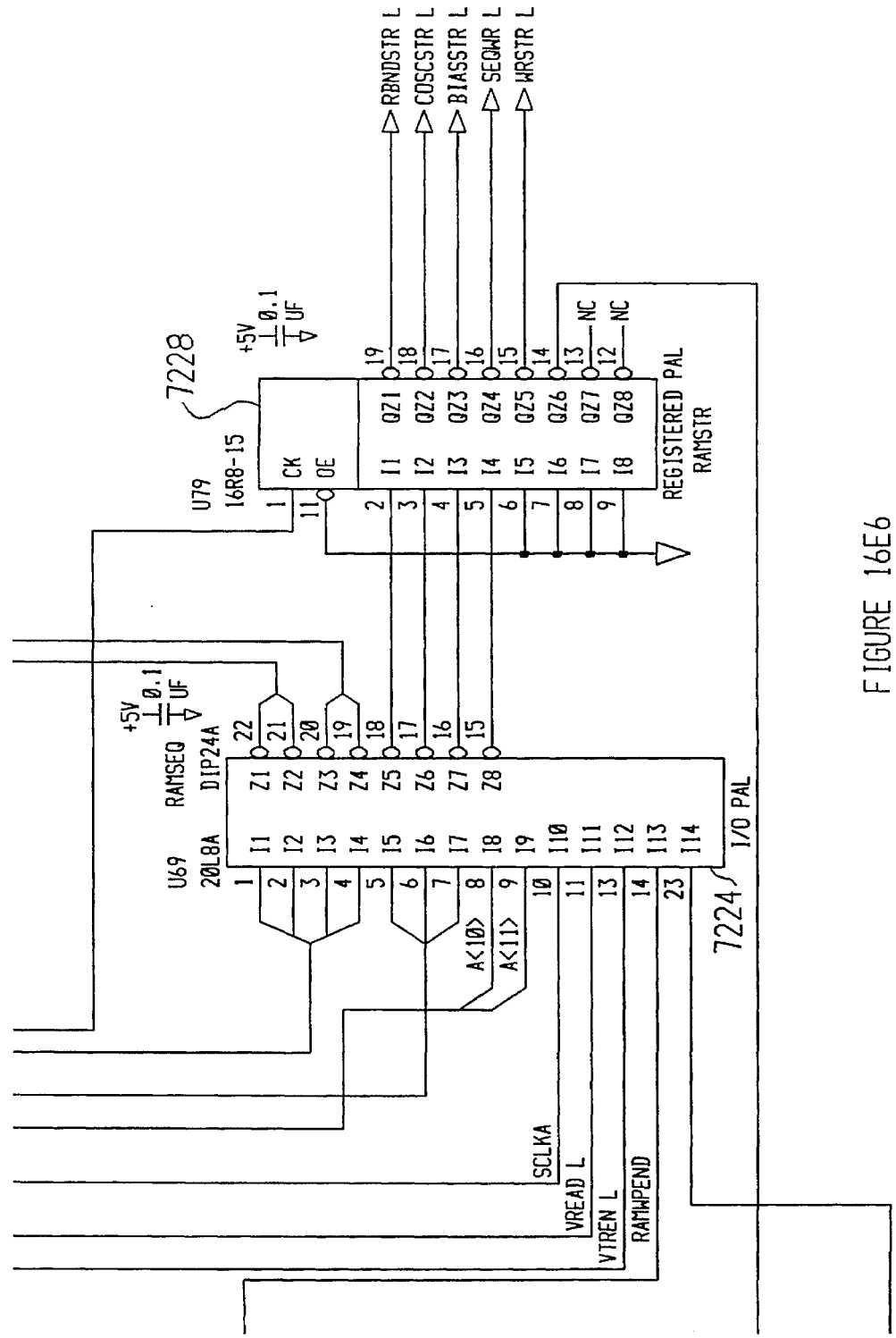
FIGURE 16E6

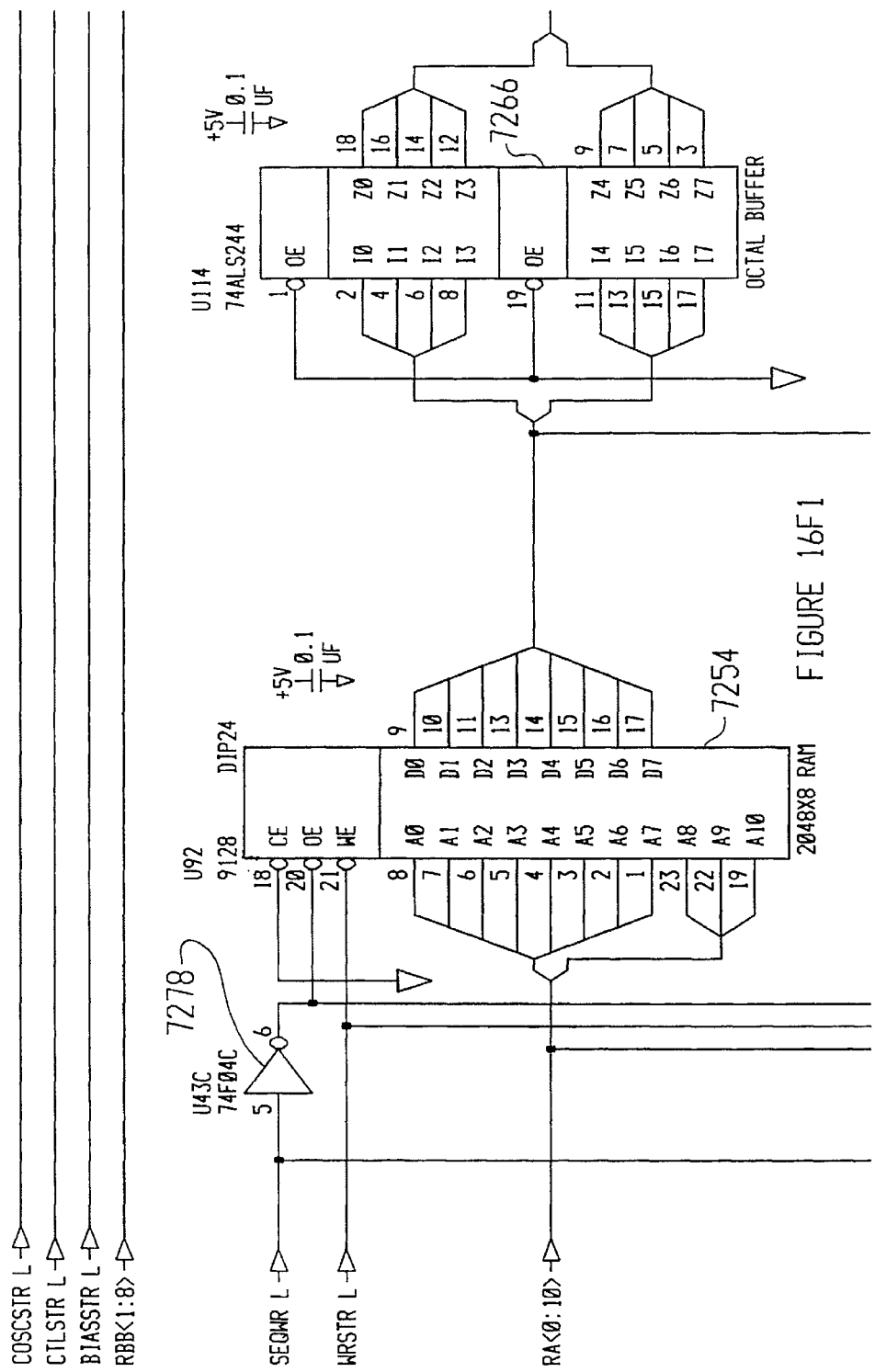
FIGURE 16F1

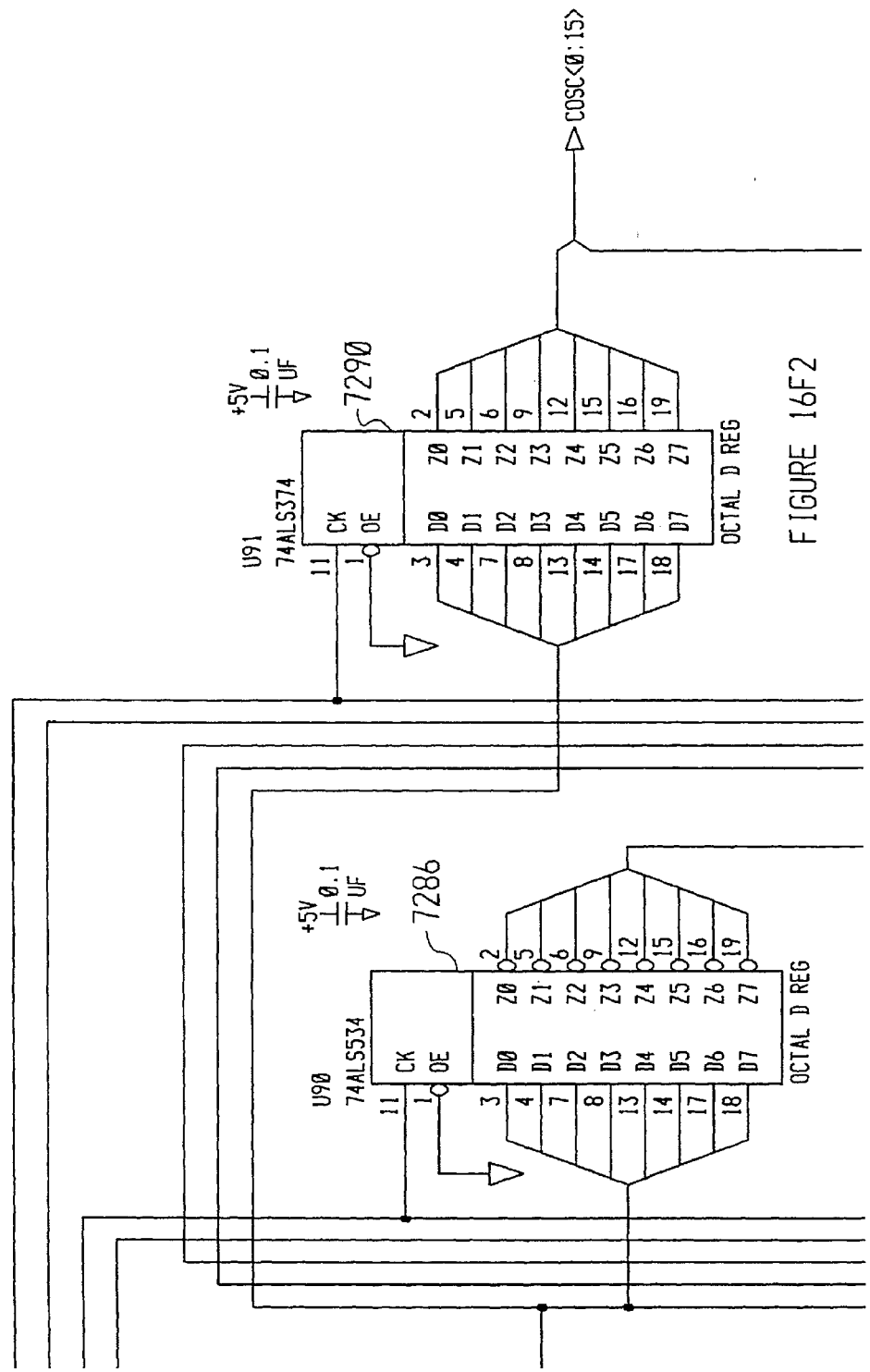

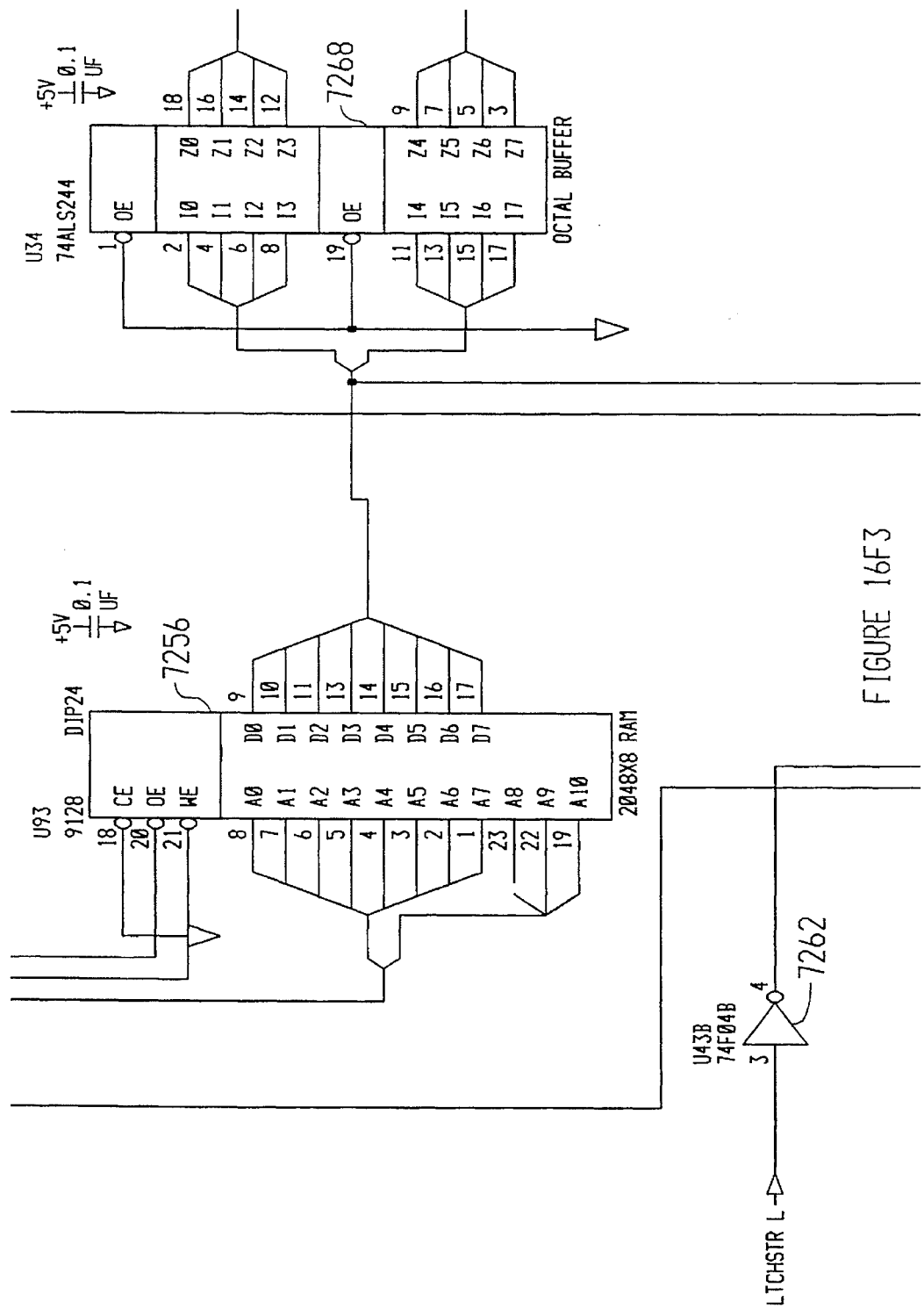
FIGURE 16F3

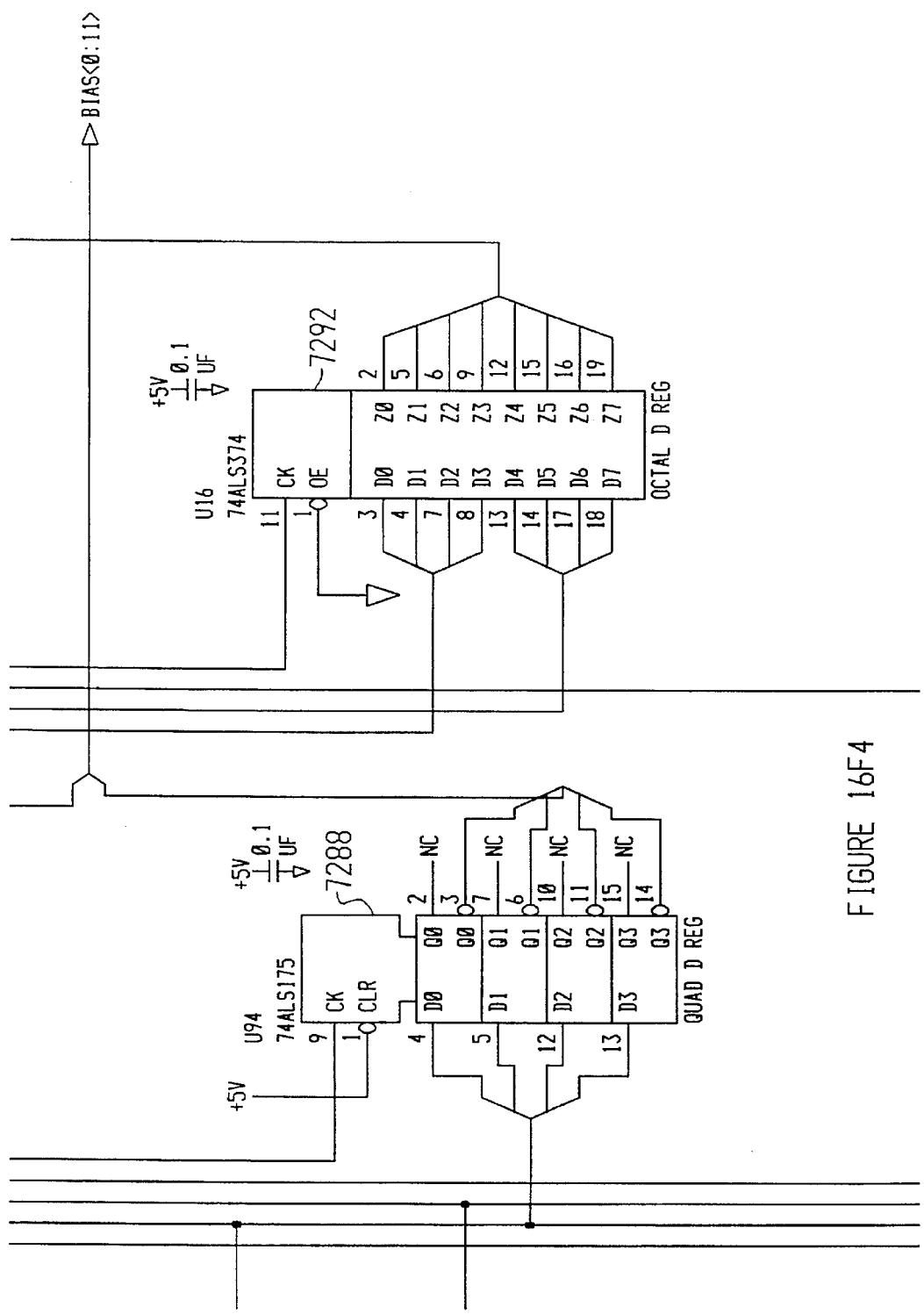
FIGURE 16F4

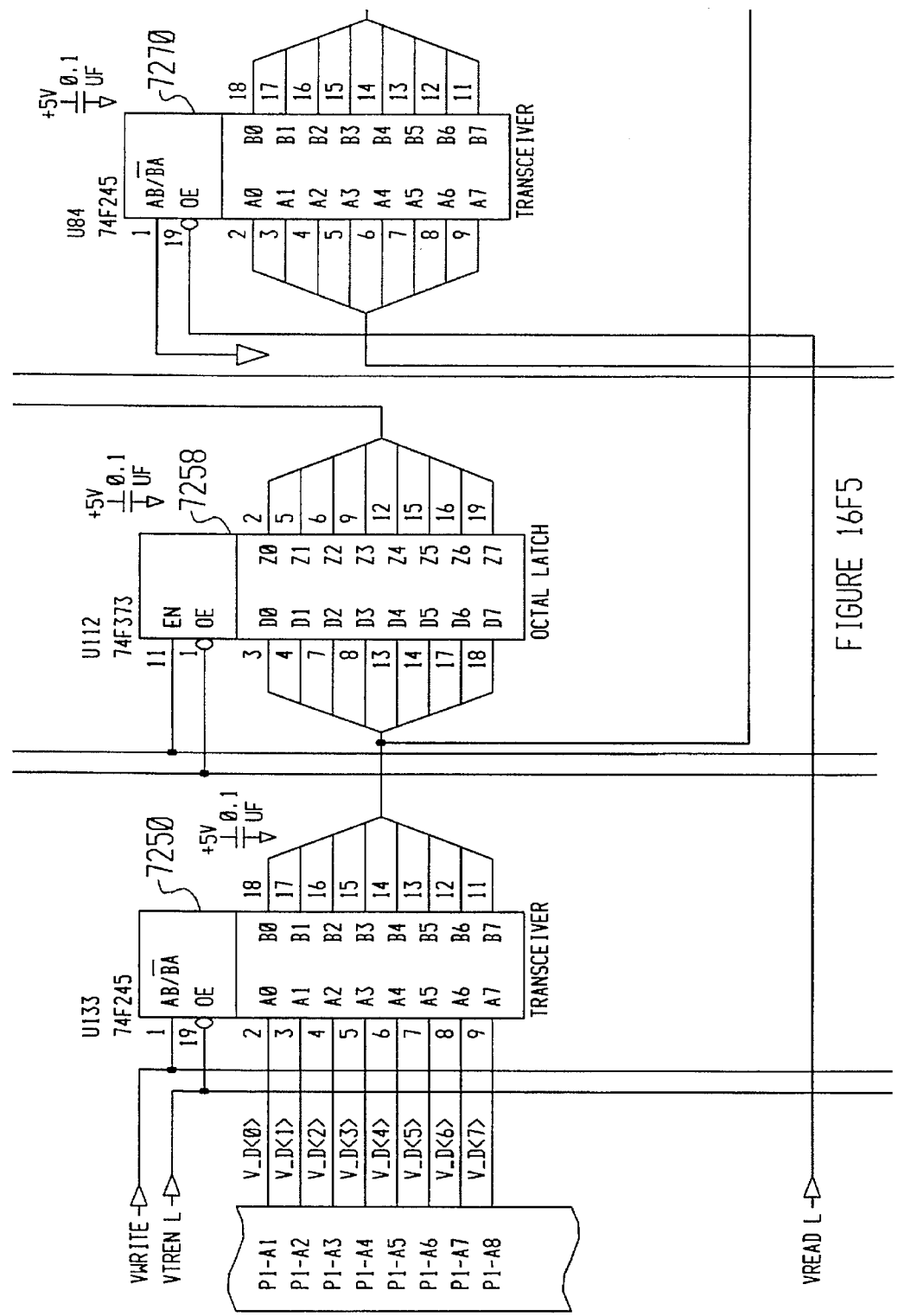

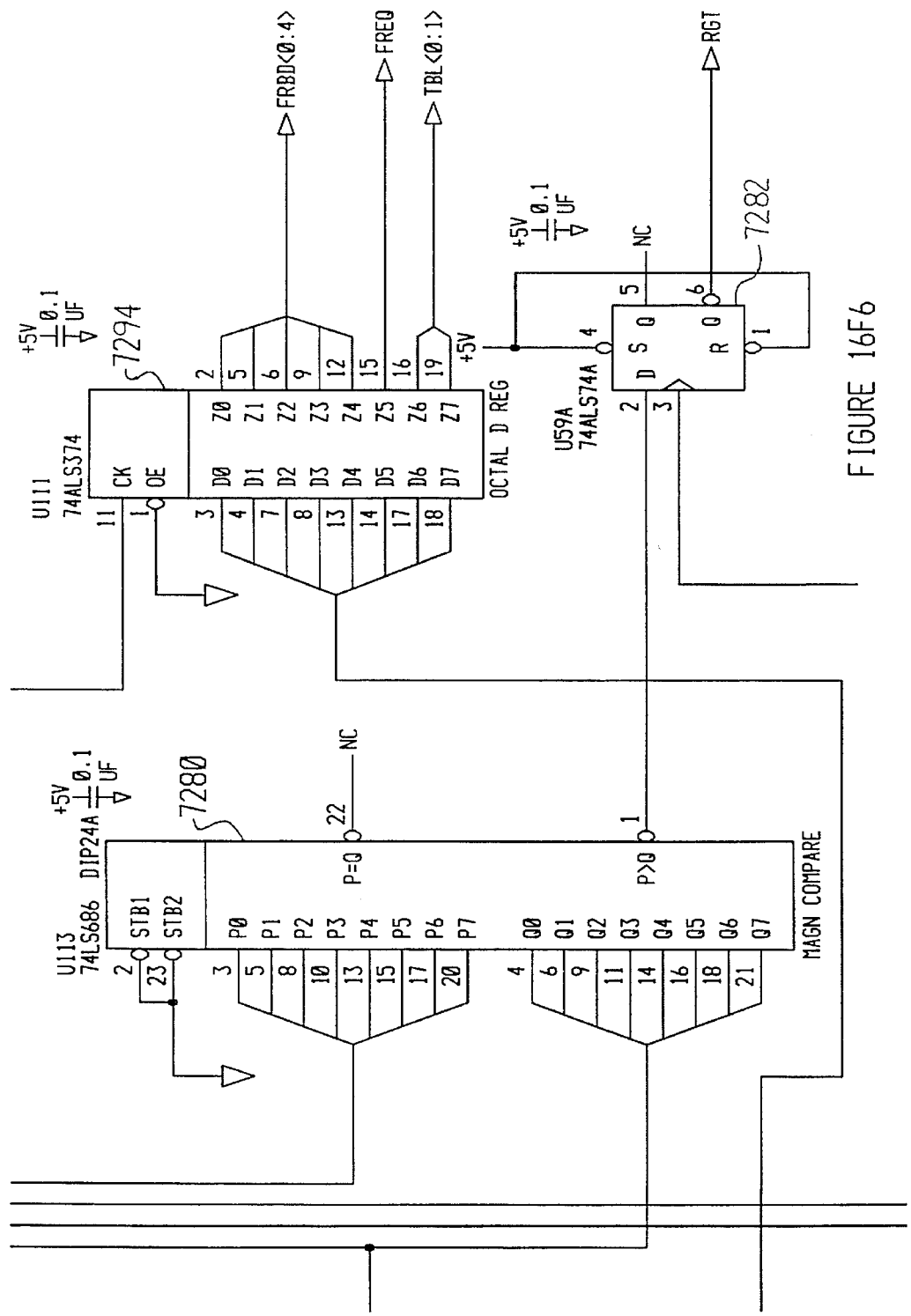

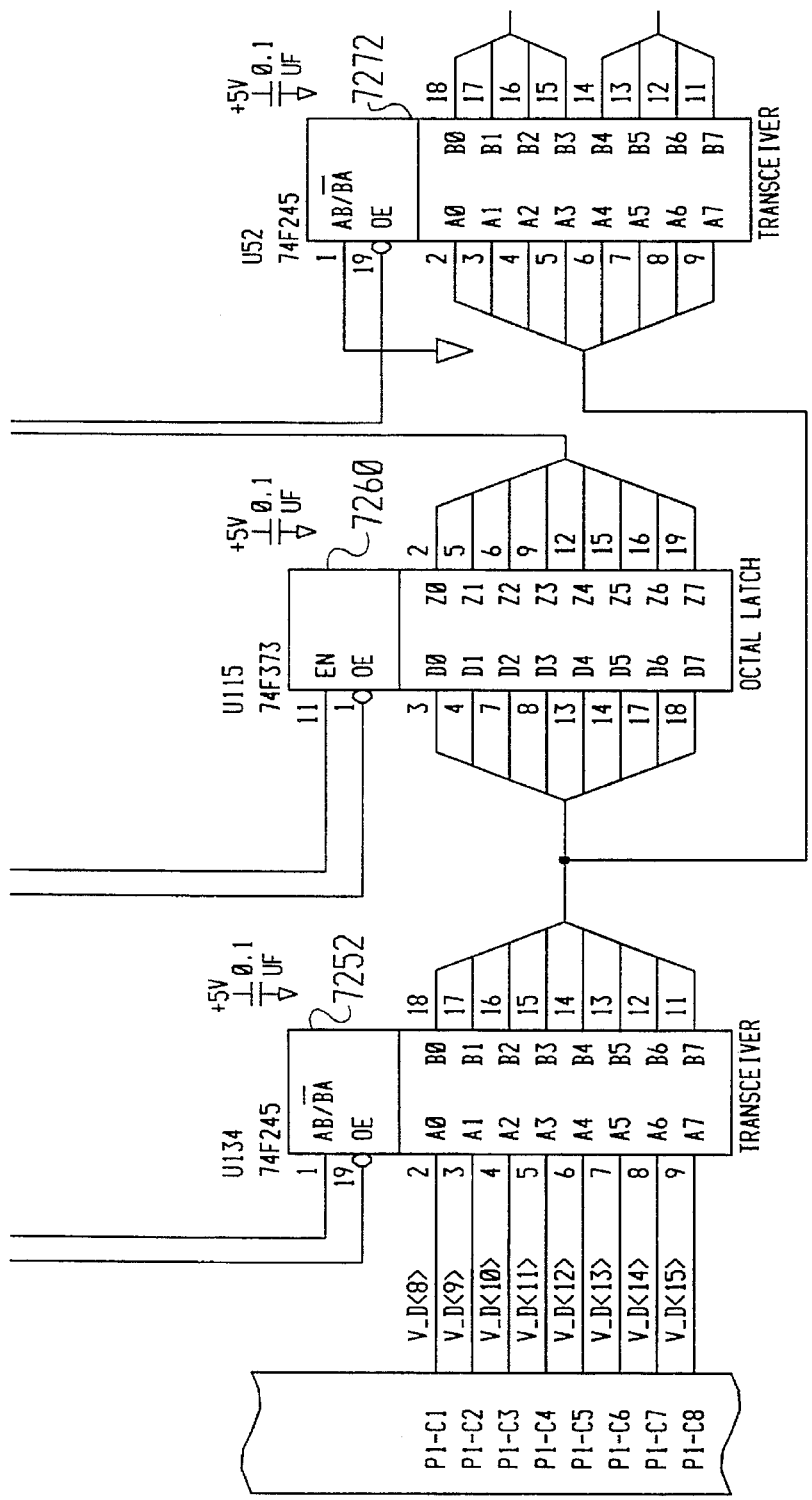
FIGURE 16F7

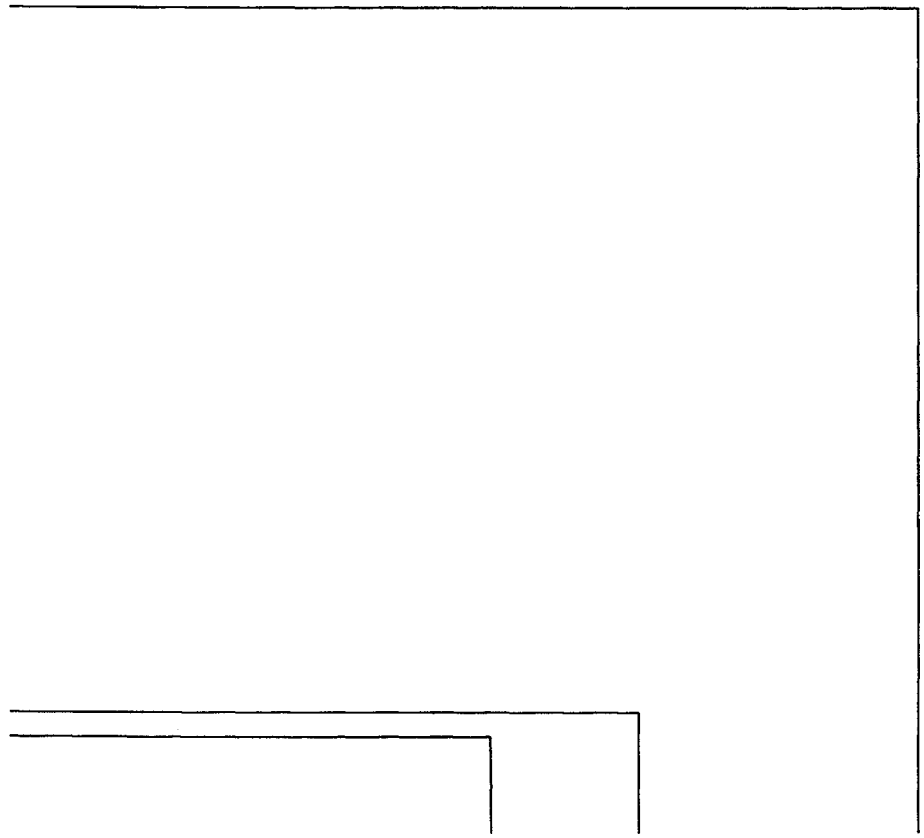

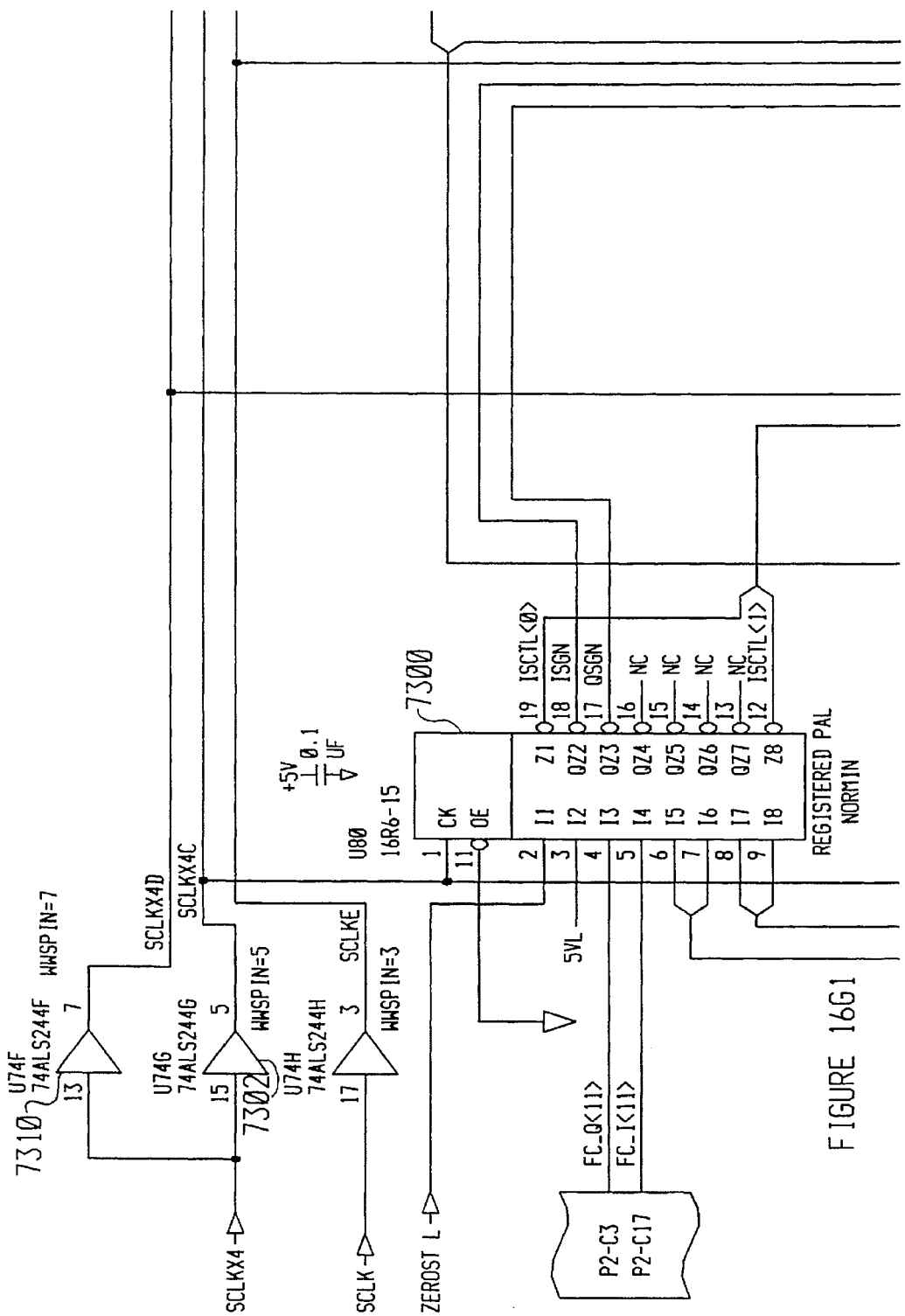
FIGURE 16G1

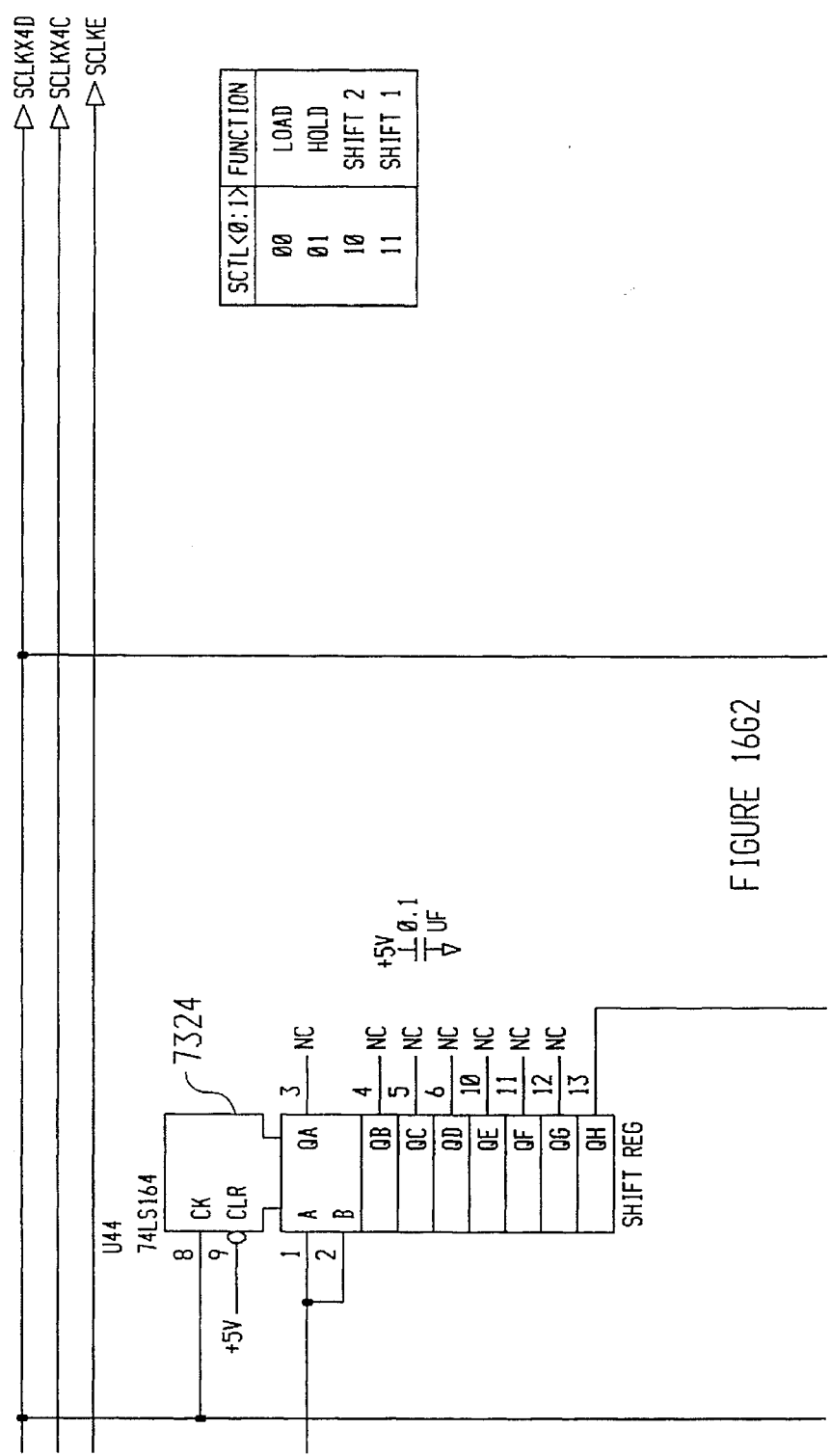
FIGURE 1662

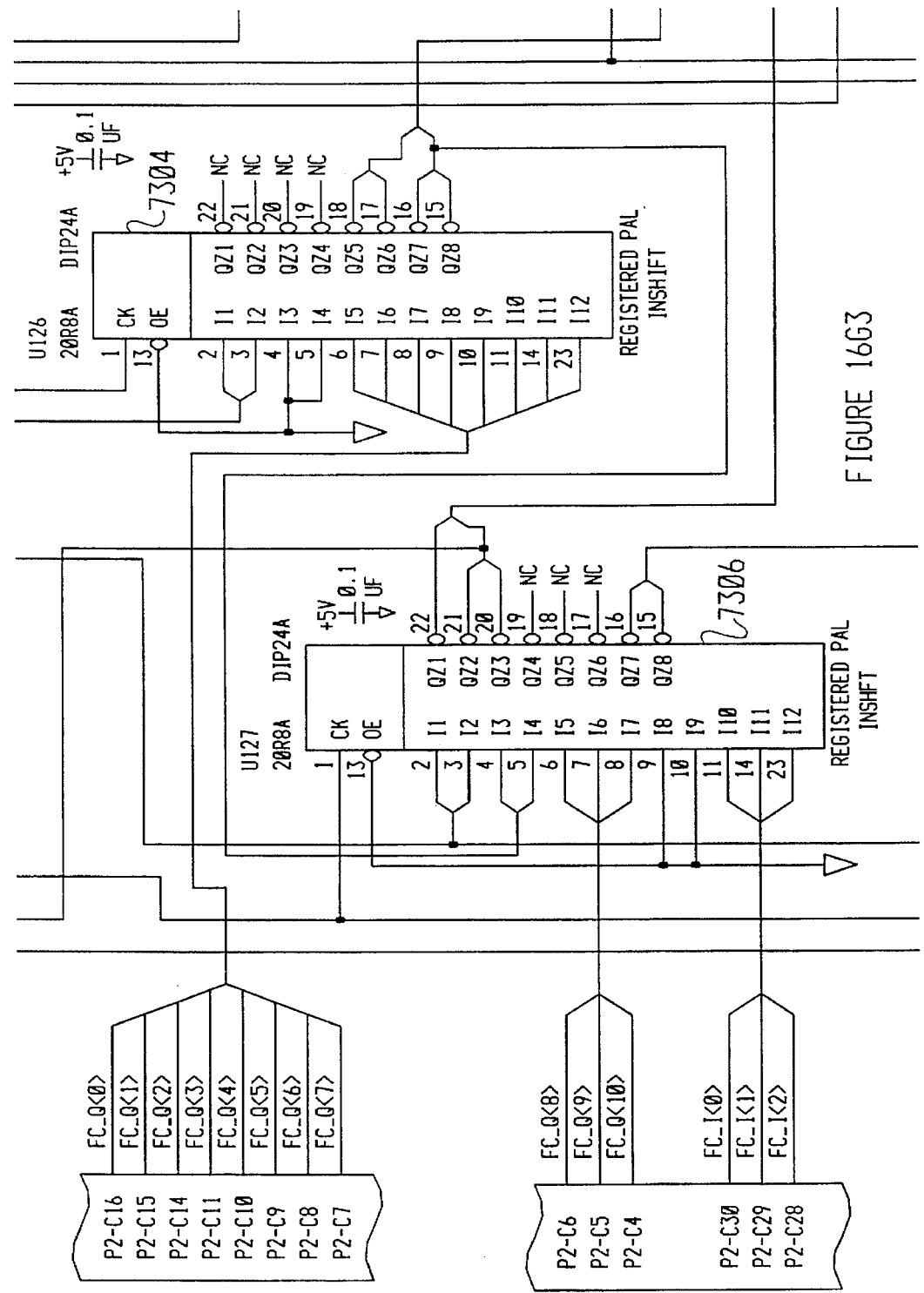
FIGURE 1663

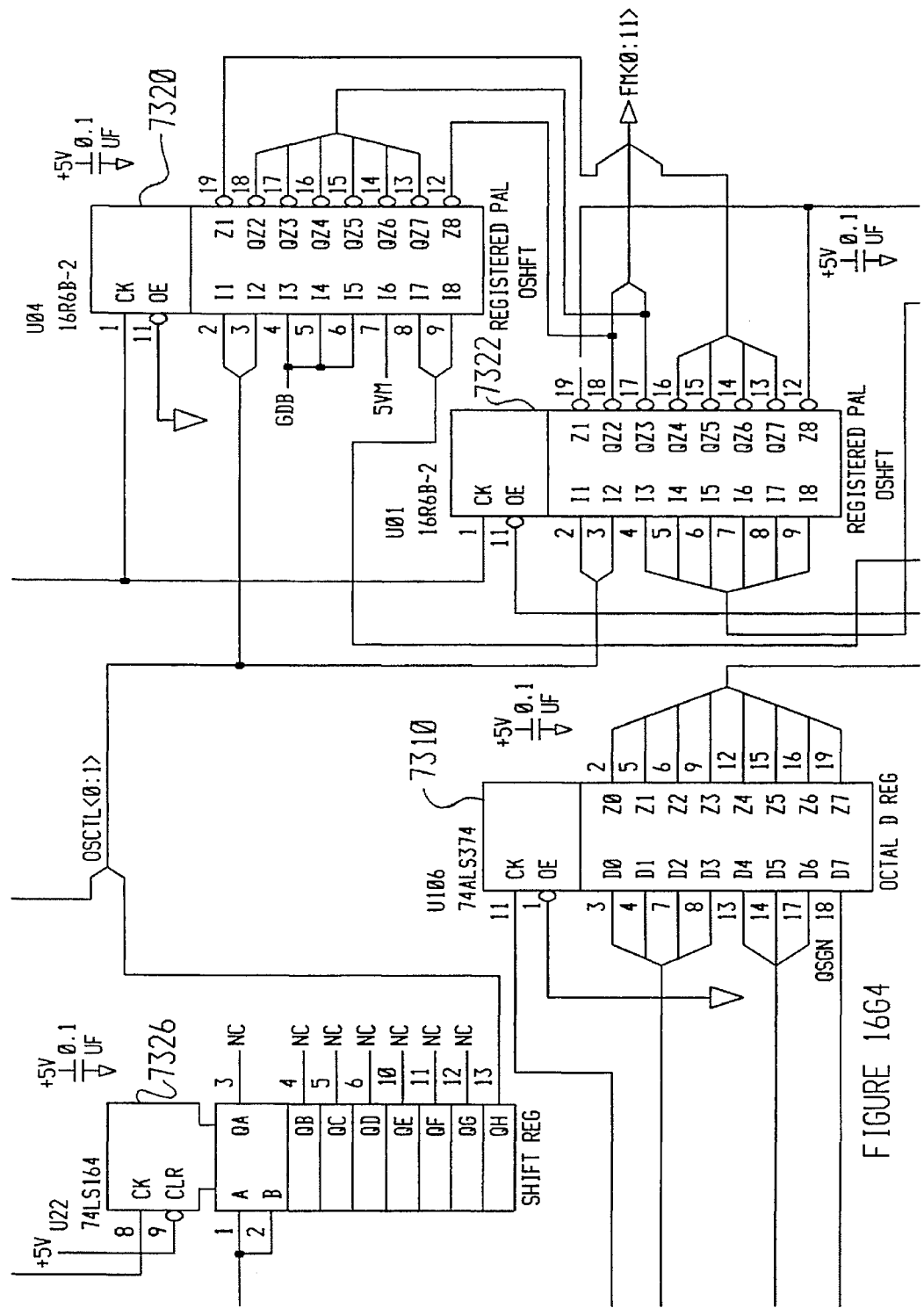
FIGURE 16G4

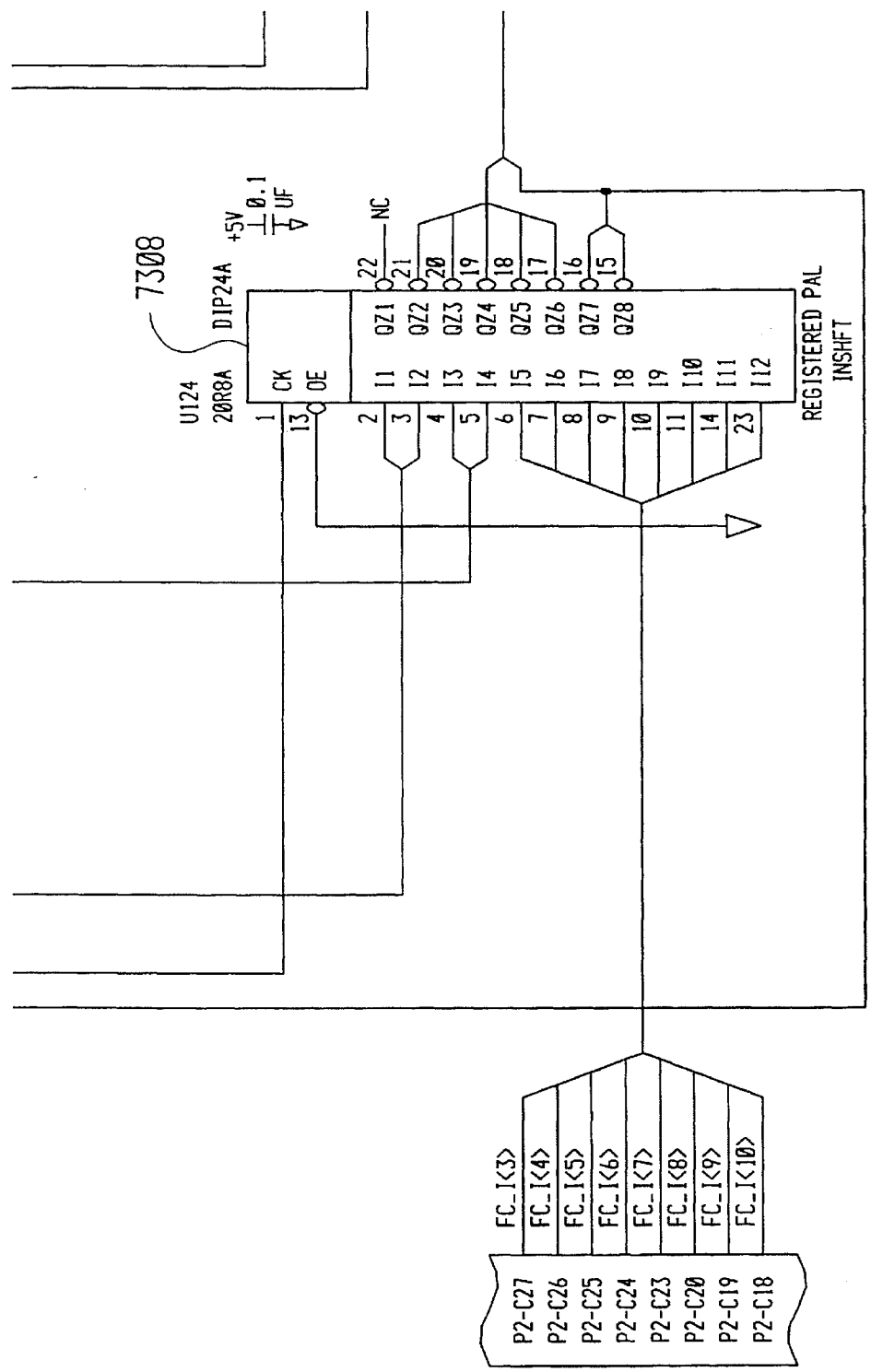
FIGURE 1665

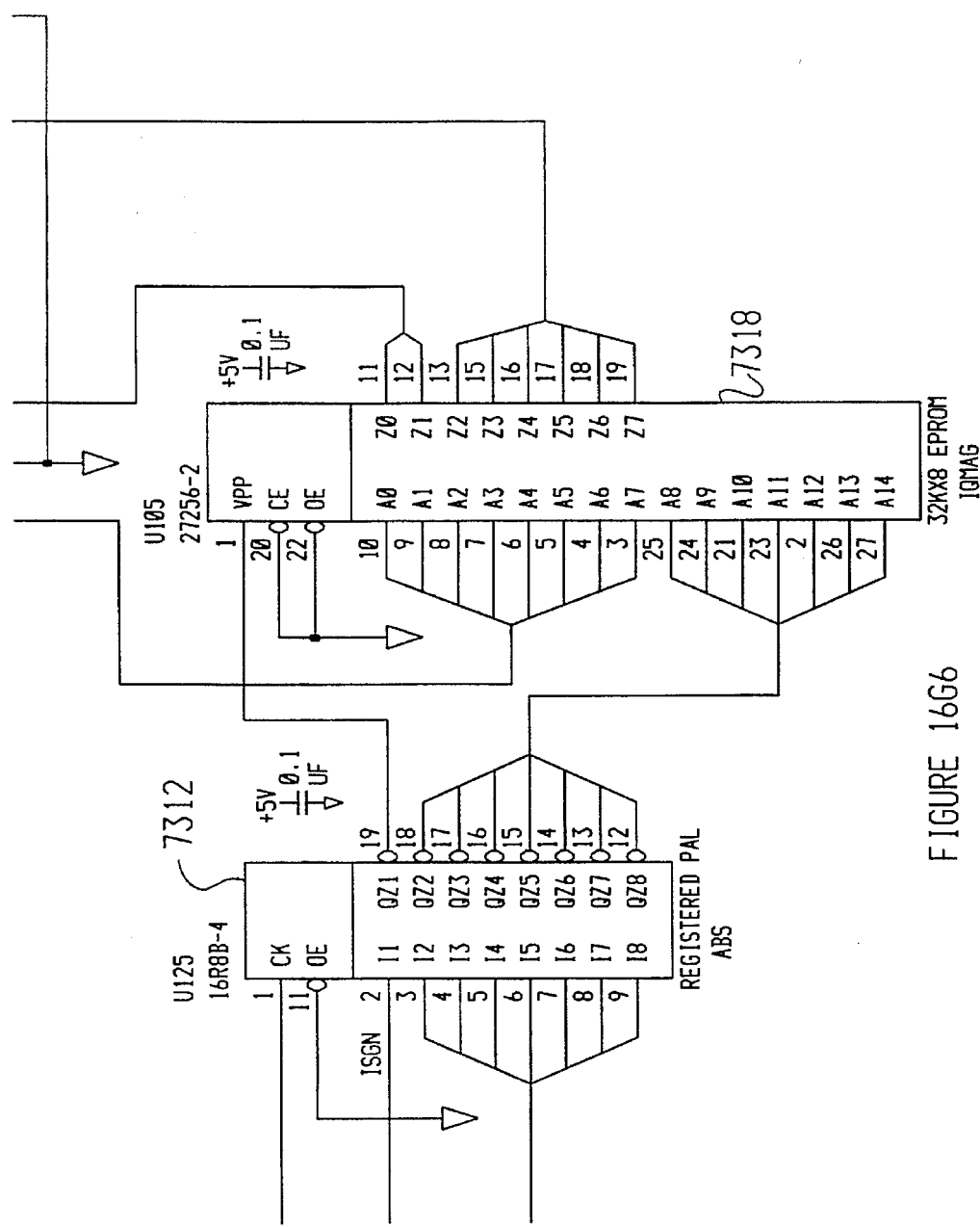
FIGURE 16G6

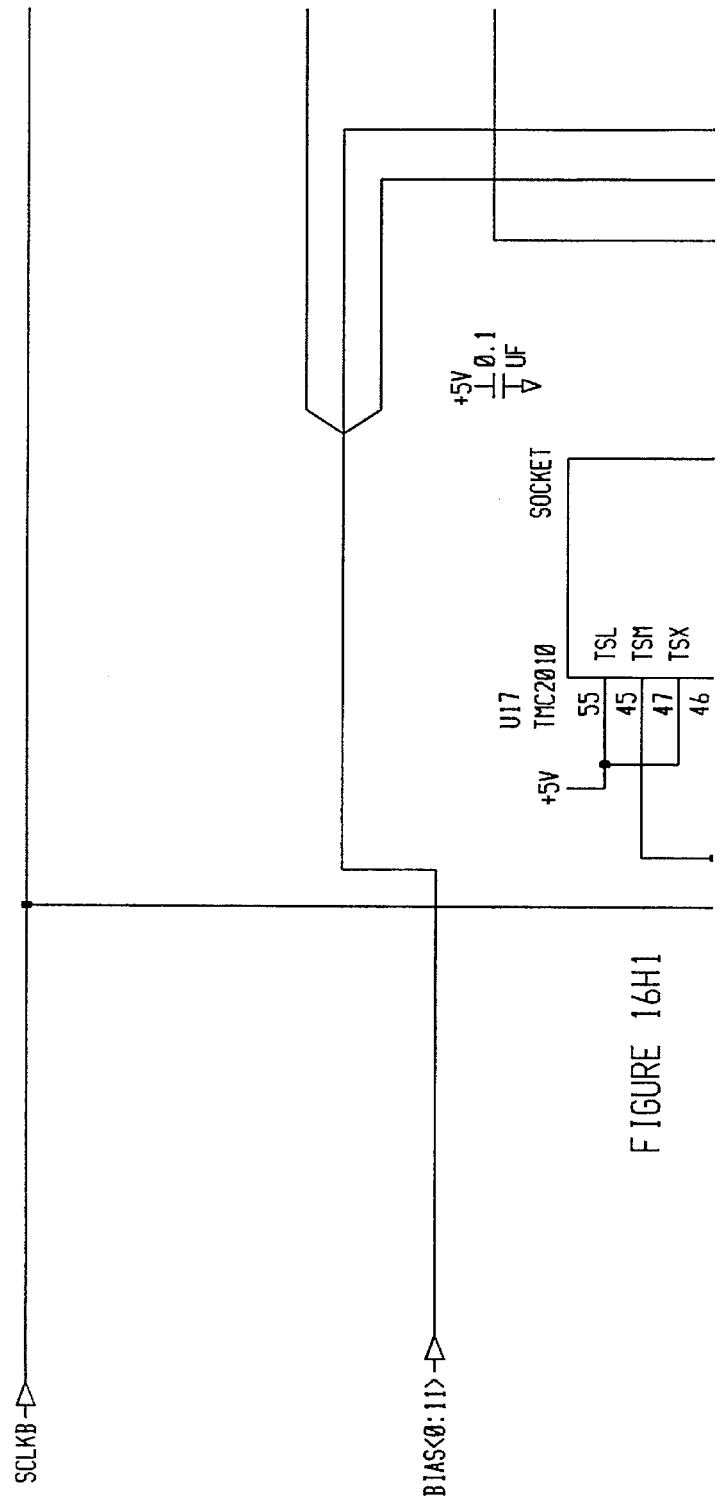
FIGURE 16H1

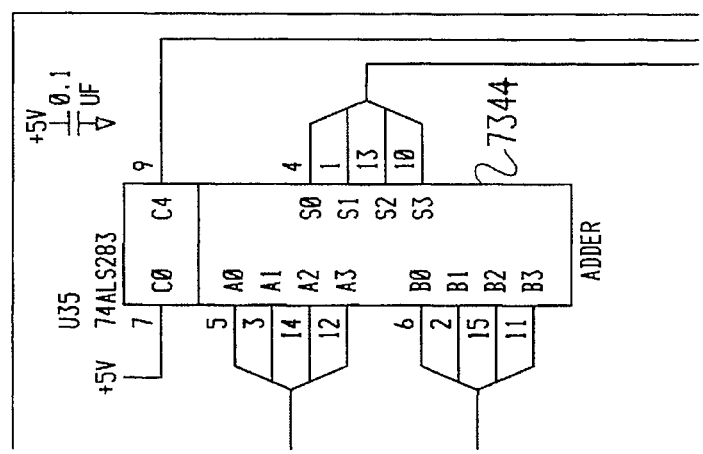
FIGURE 16H2

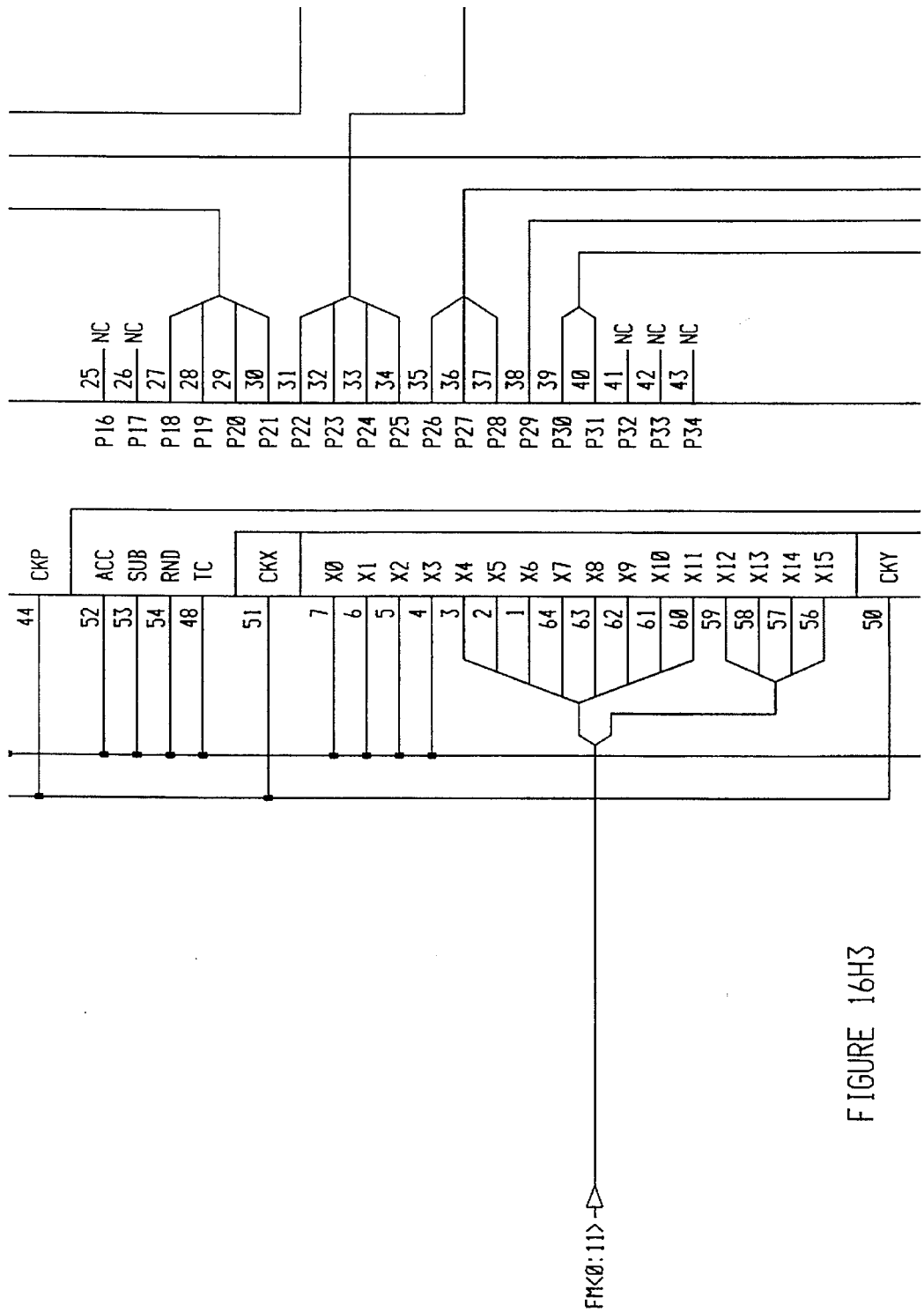
FIGURE 16H3

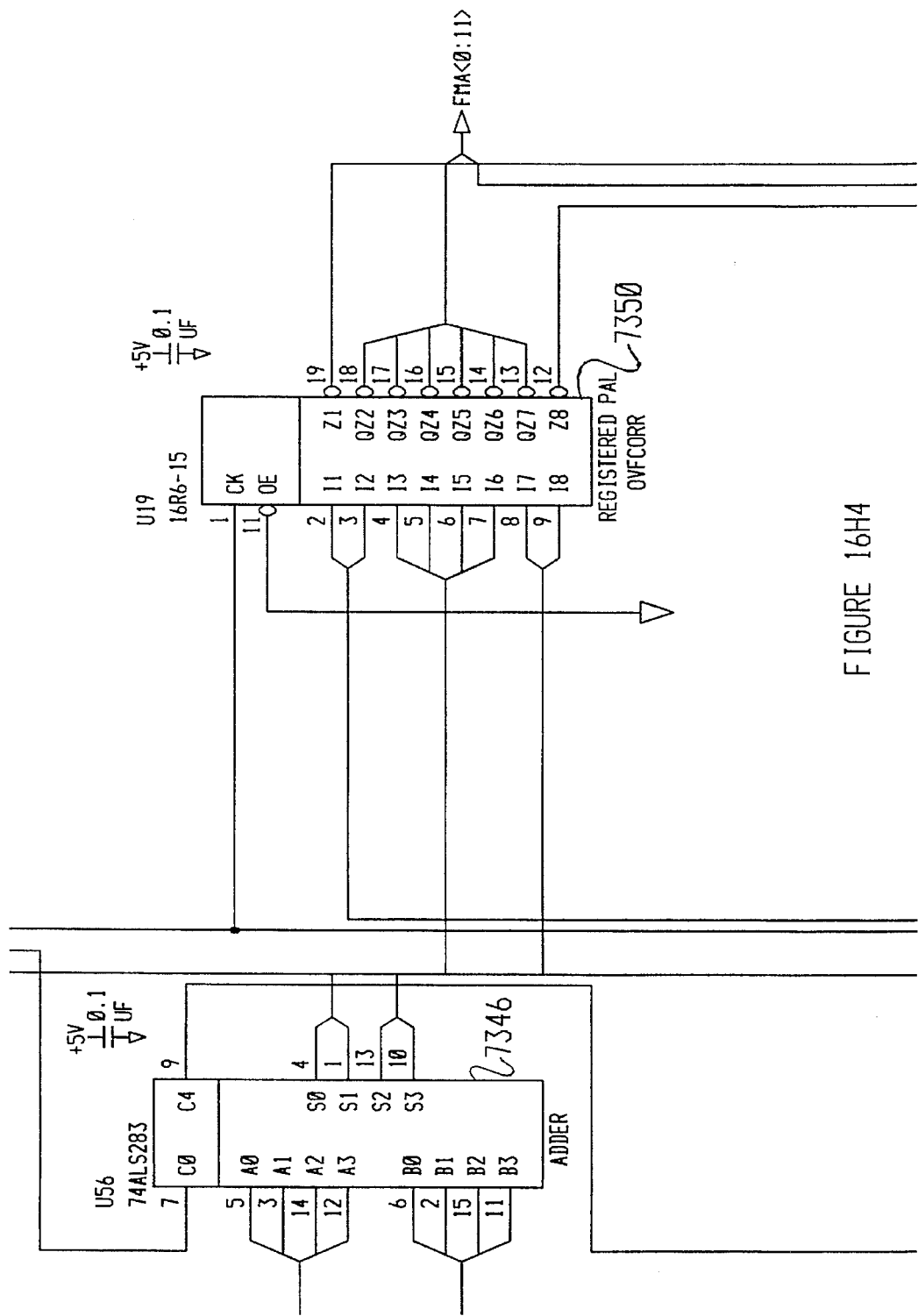
FIGURE 16H4

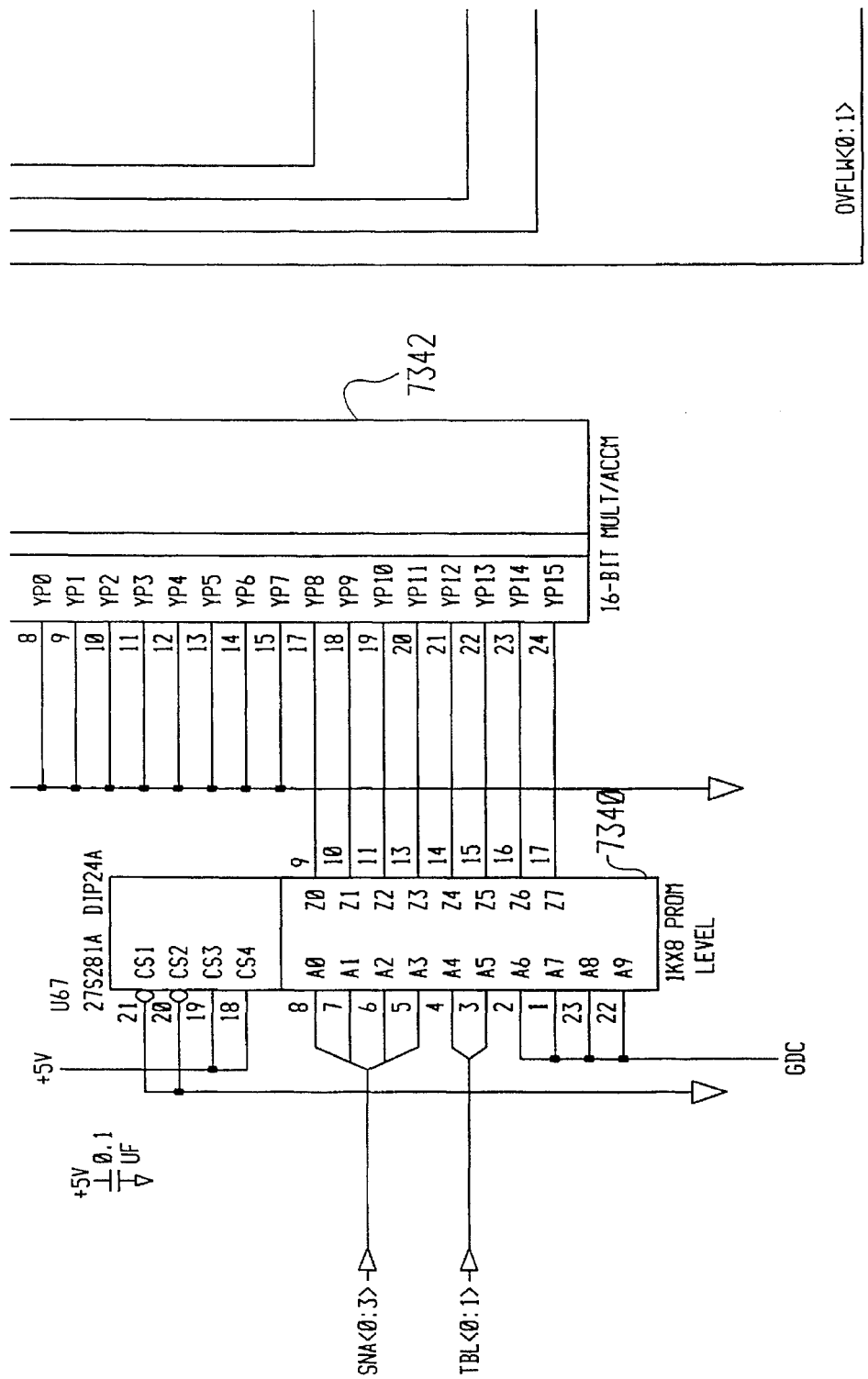
FIGURE 16H5

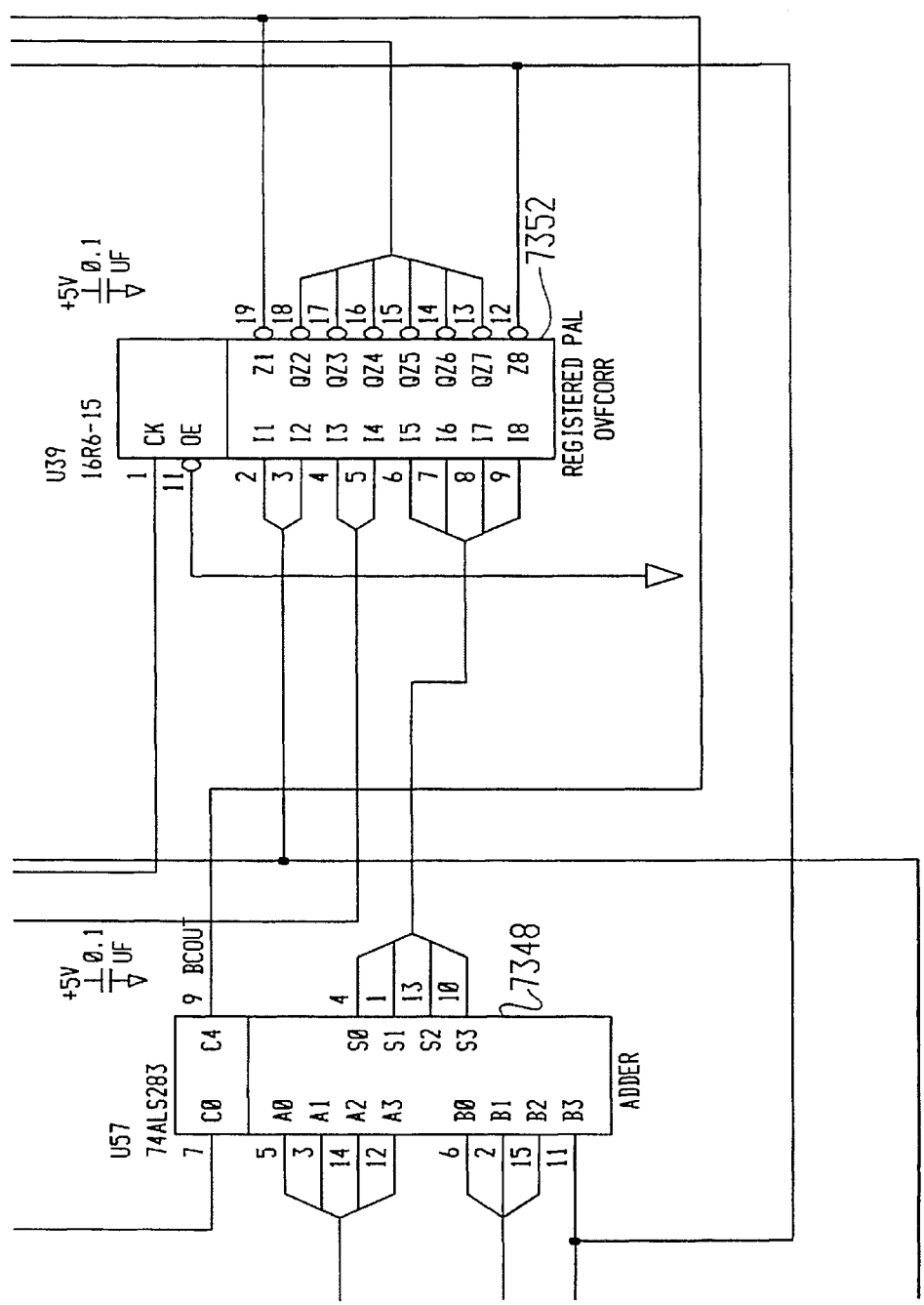
FIGURE 16H6

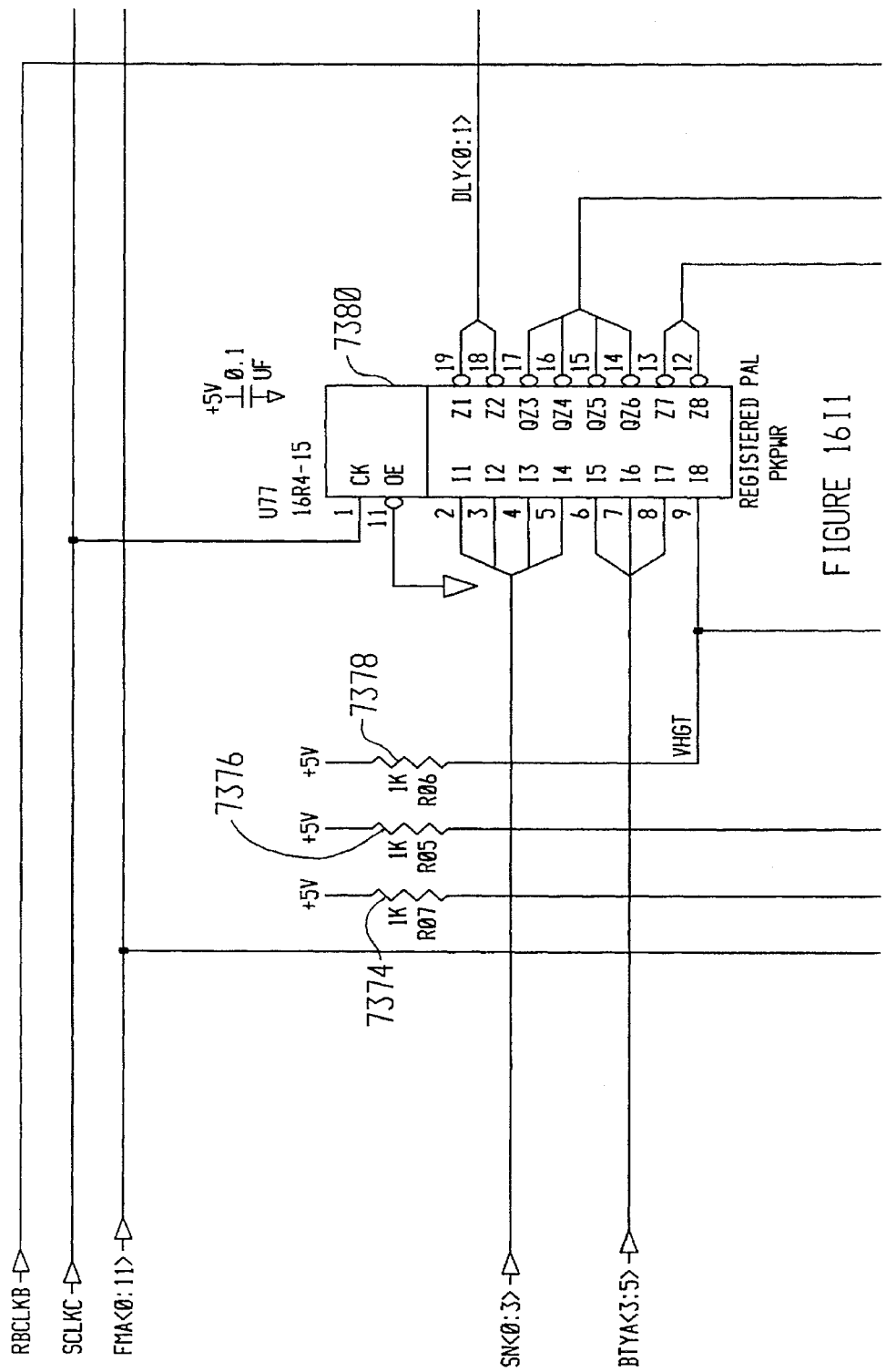
FIGURE 1611

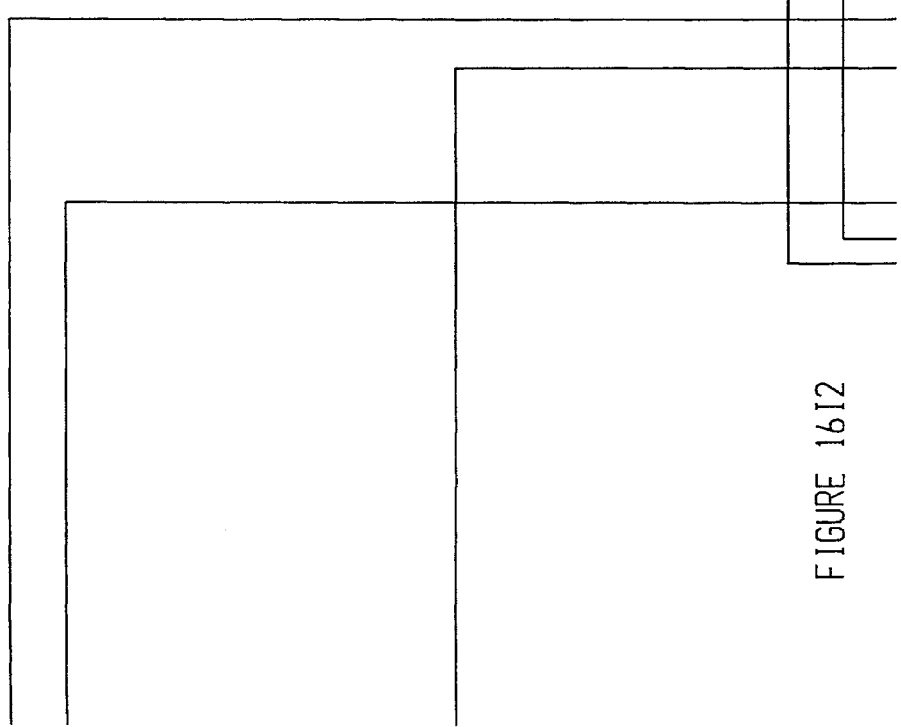
FIGURE 16I2

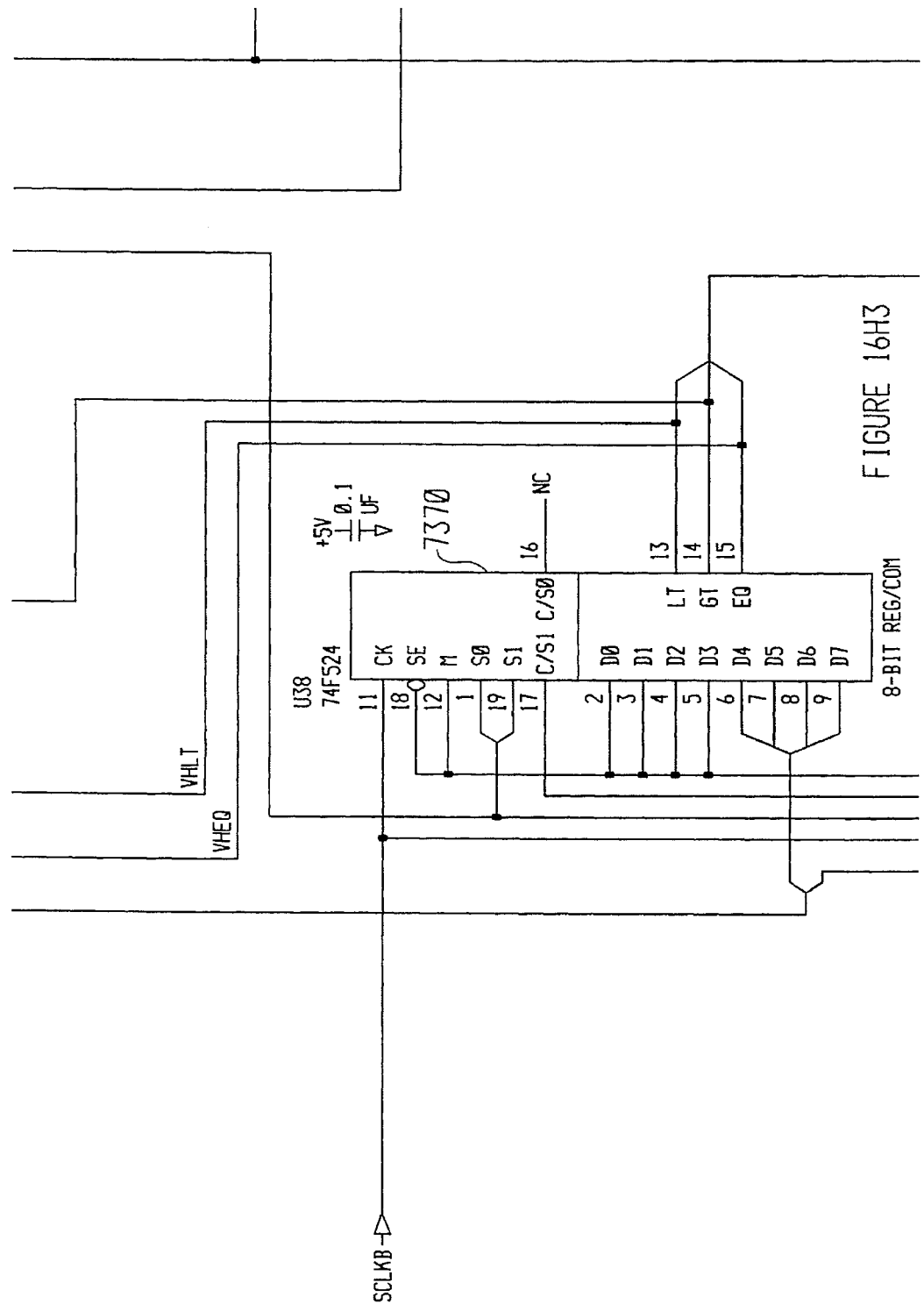
FIGURE 16H3

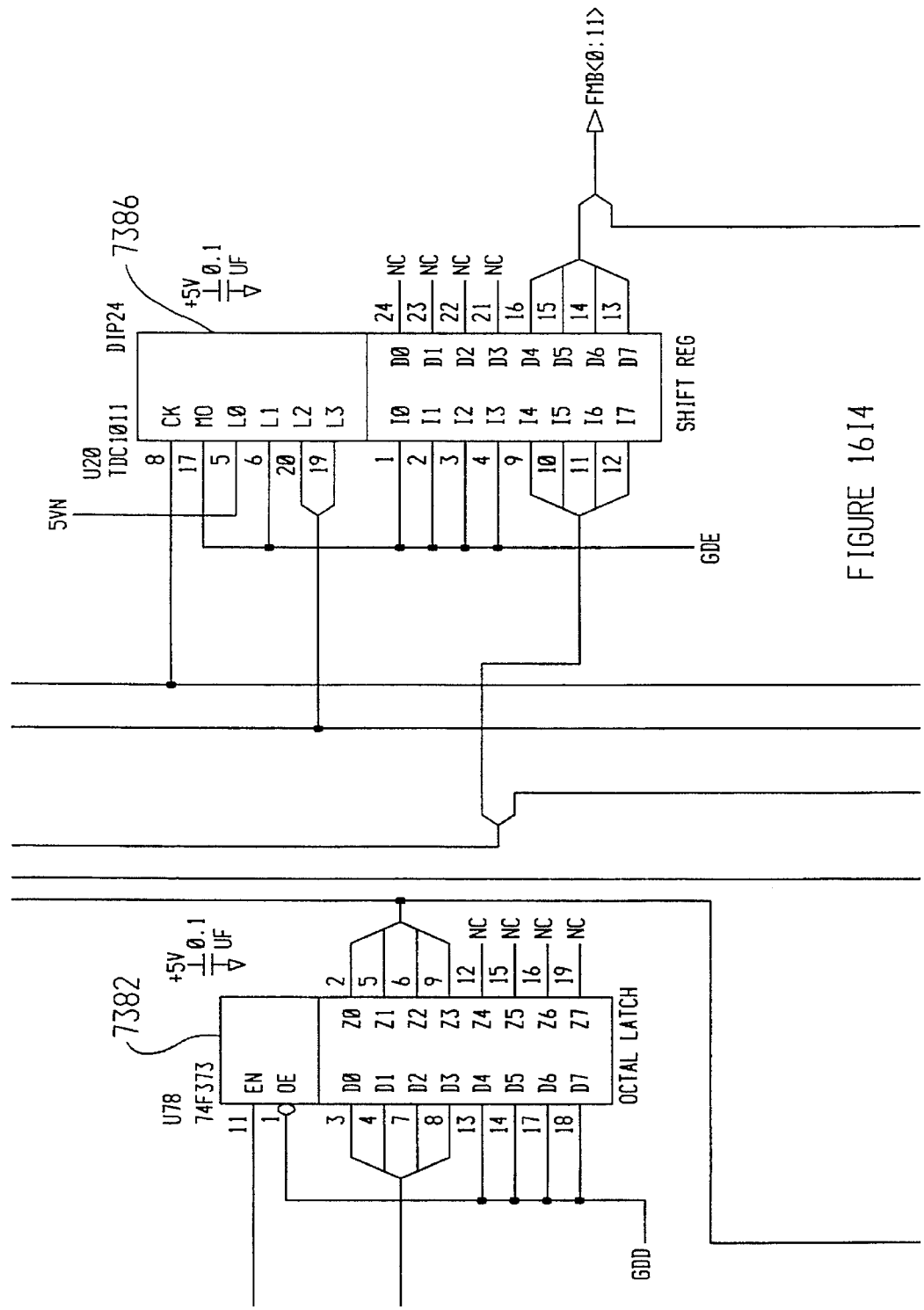
FIGURE 1614

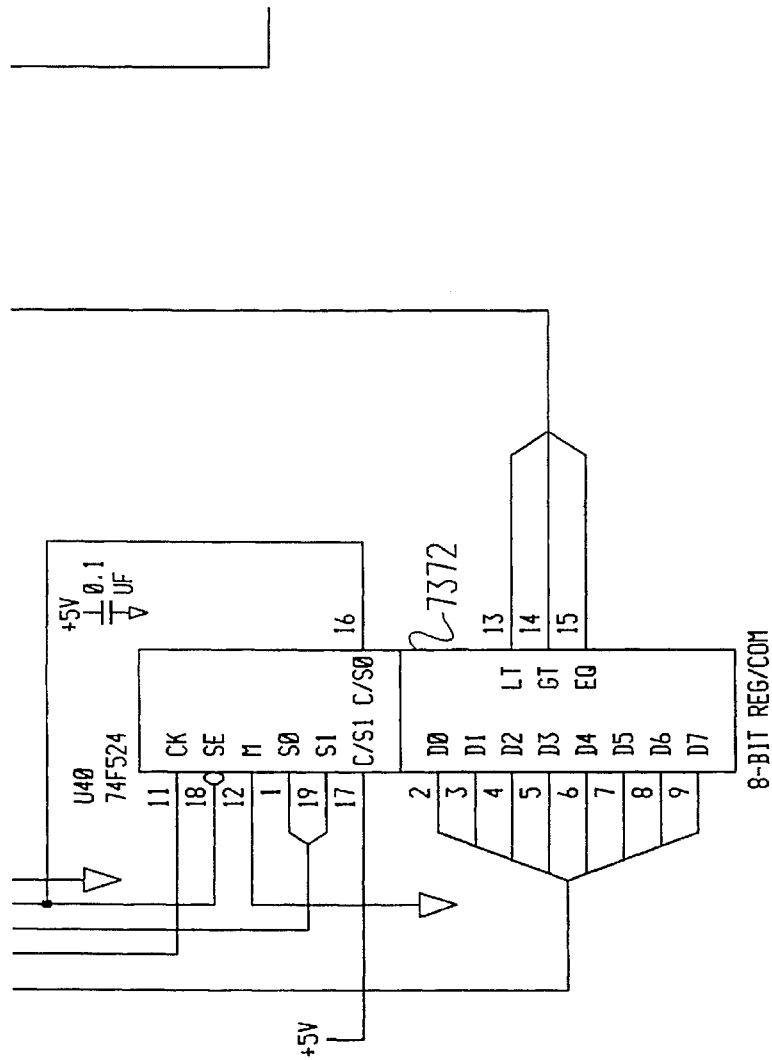
FIGURE 1615

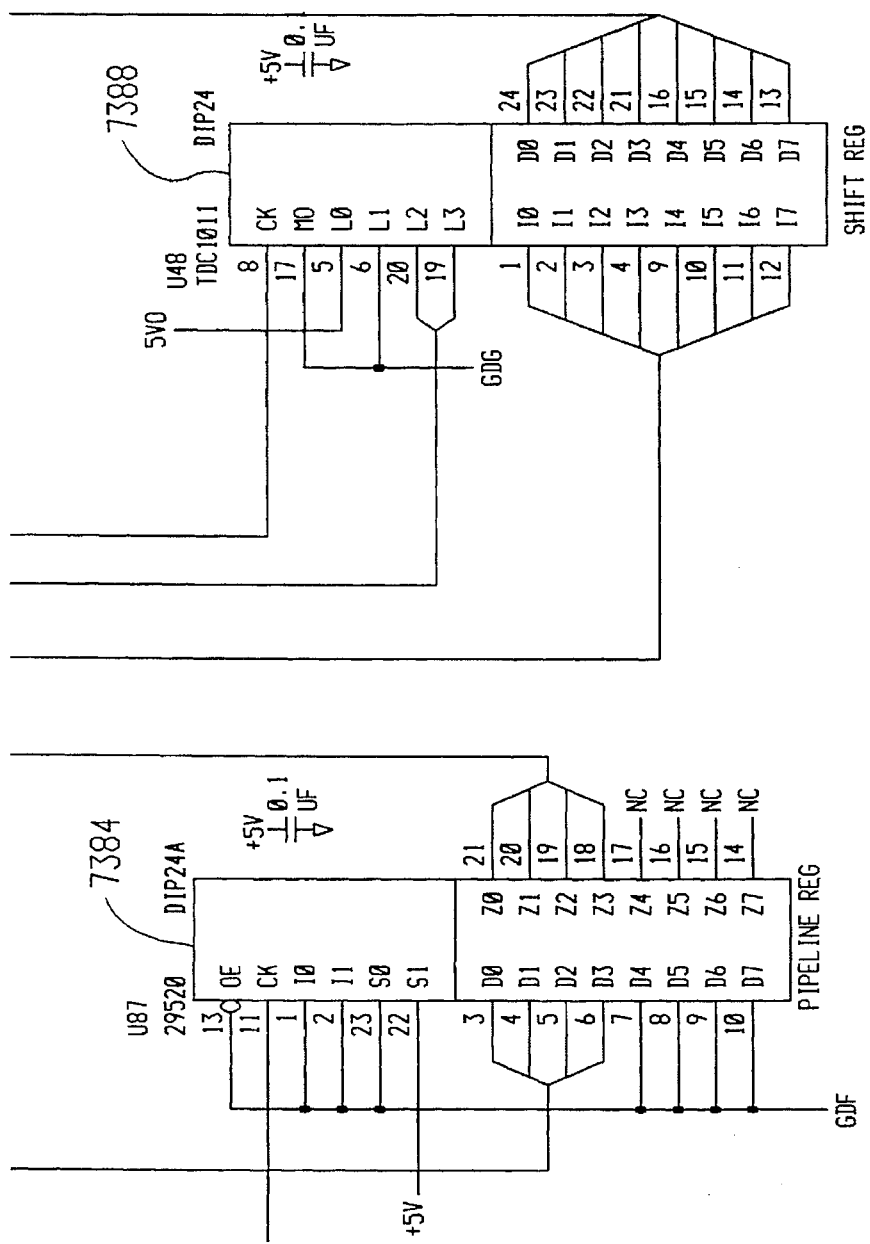
FIGURE 1616

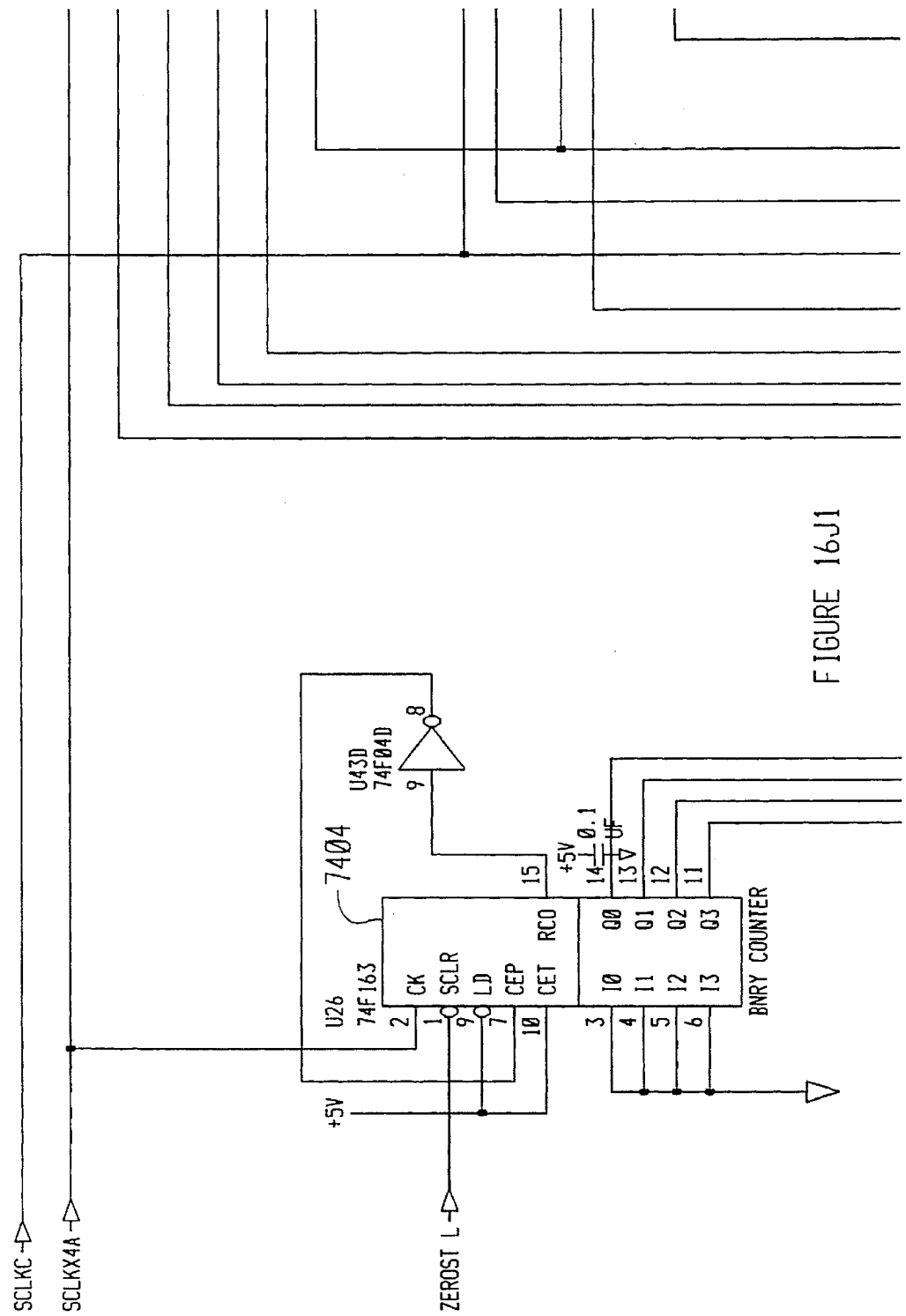
FIGURE 16J1

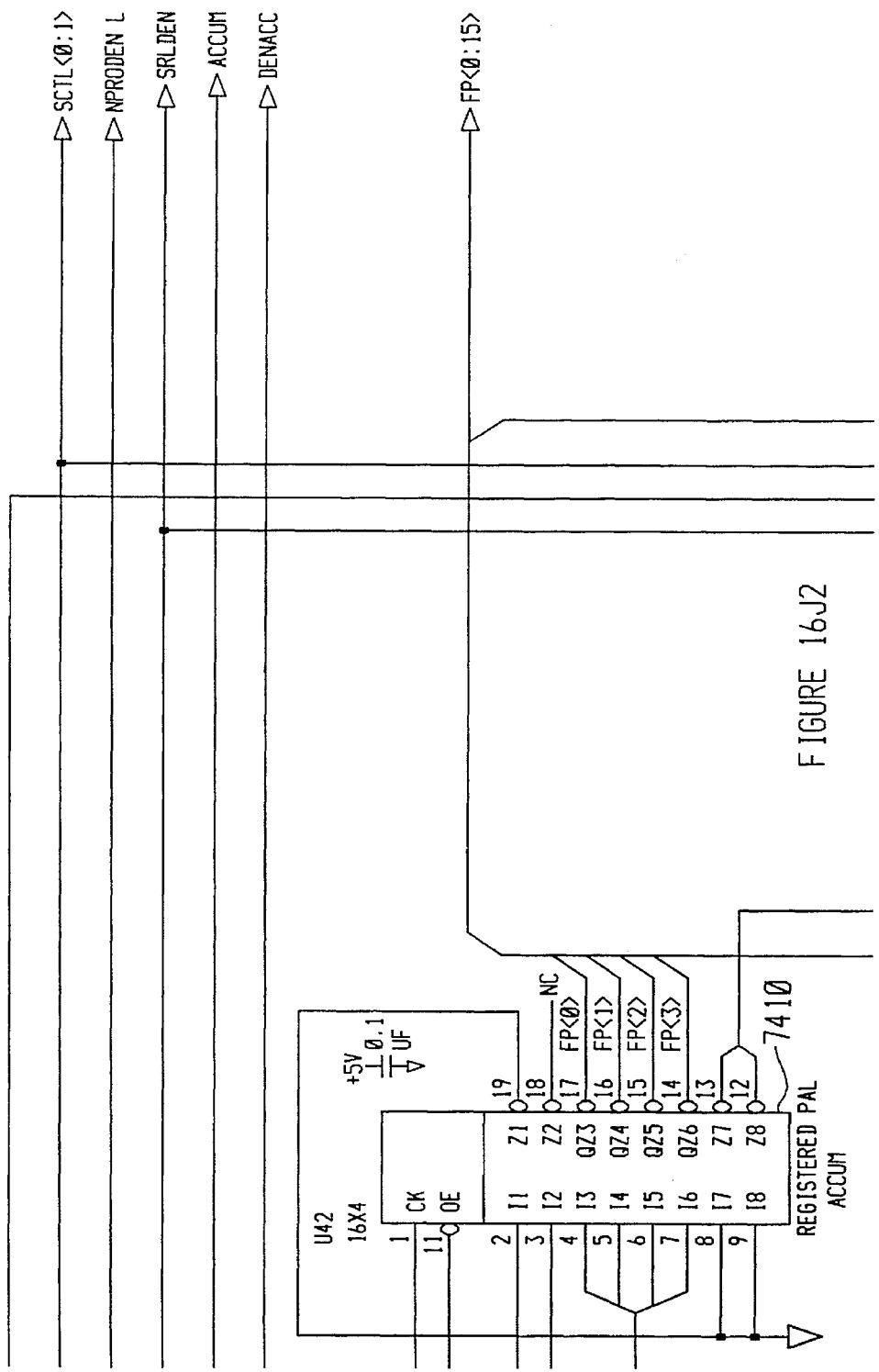
FIGURE 16J2

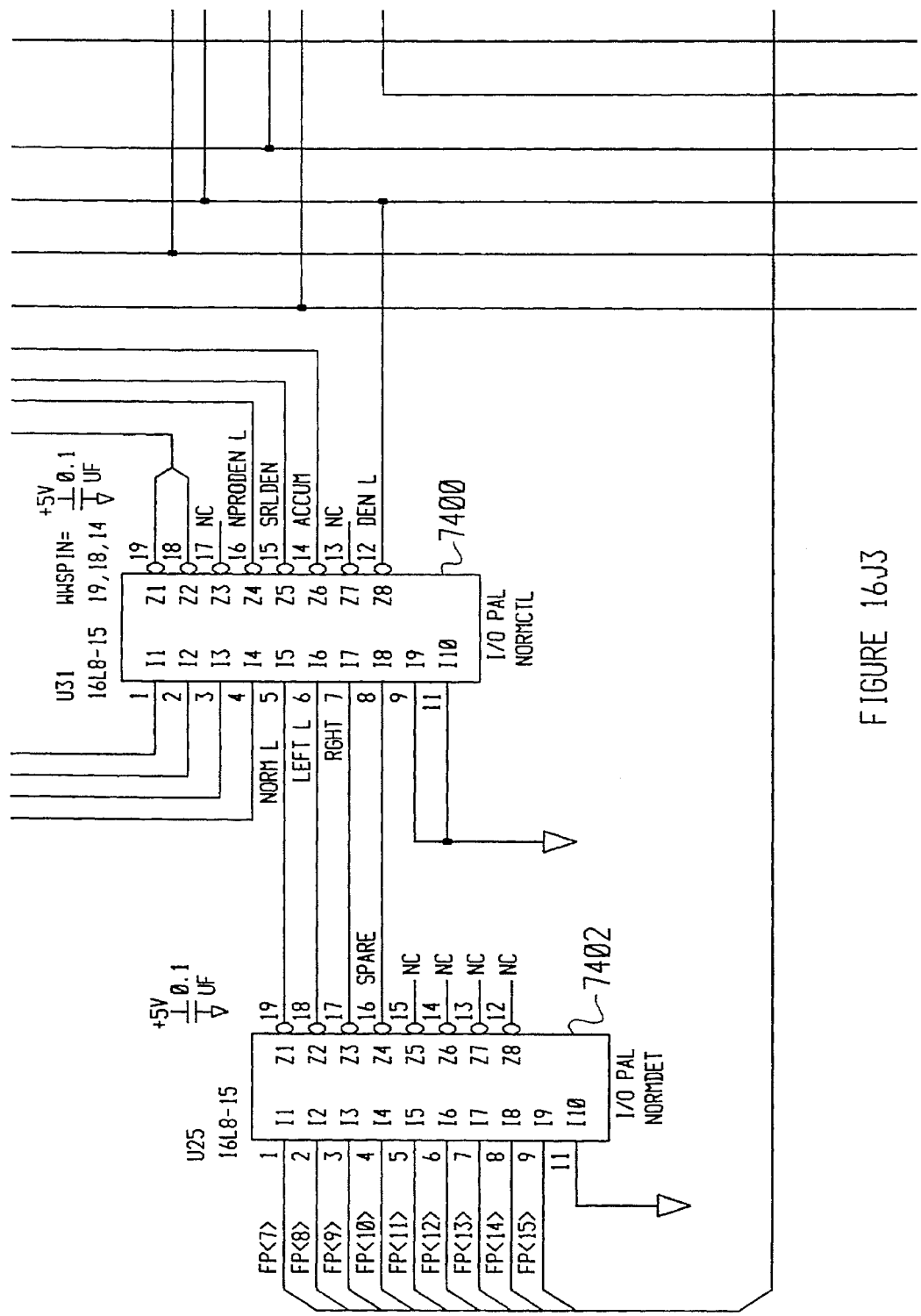
FIGURE 16J3

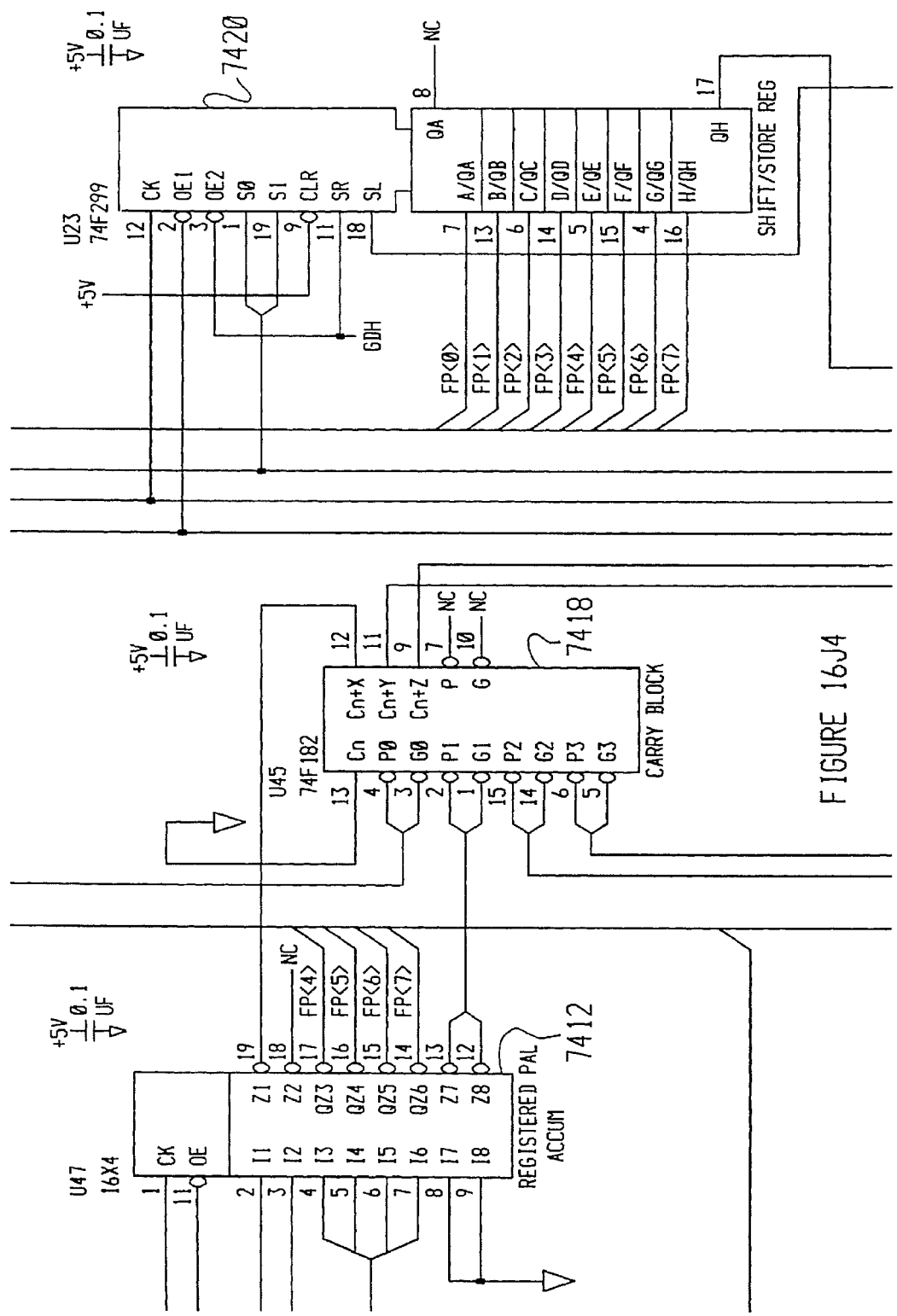
FIGURE 16J4

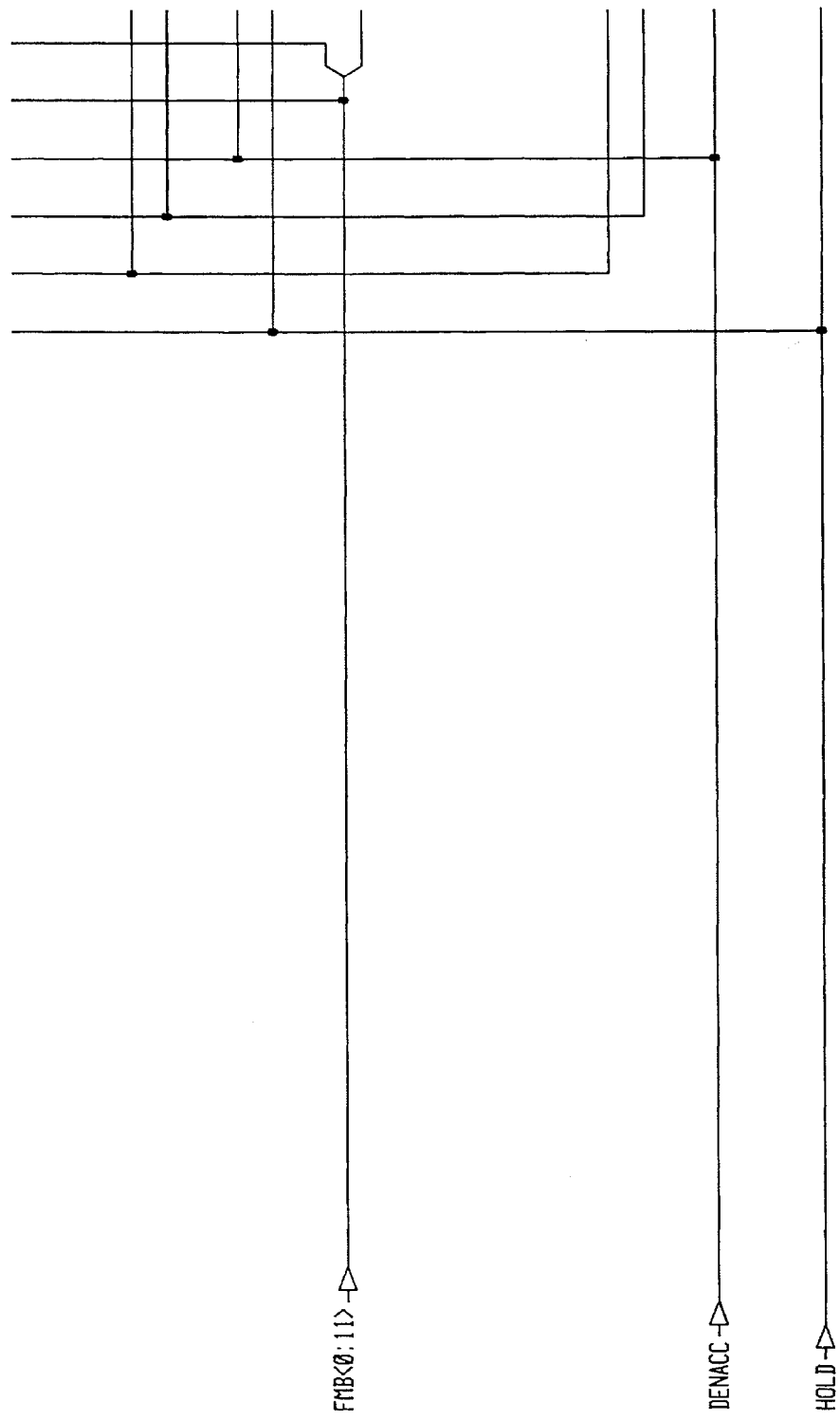
FIGURE 16J5

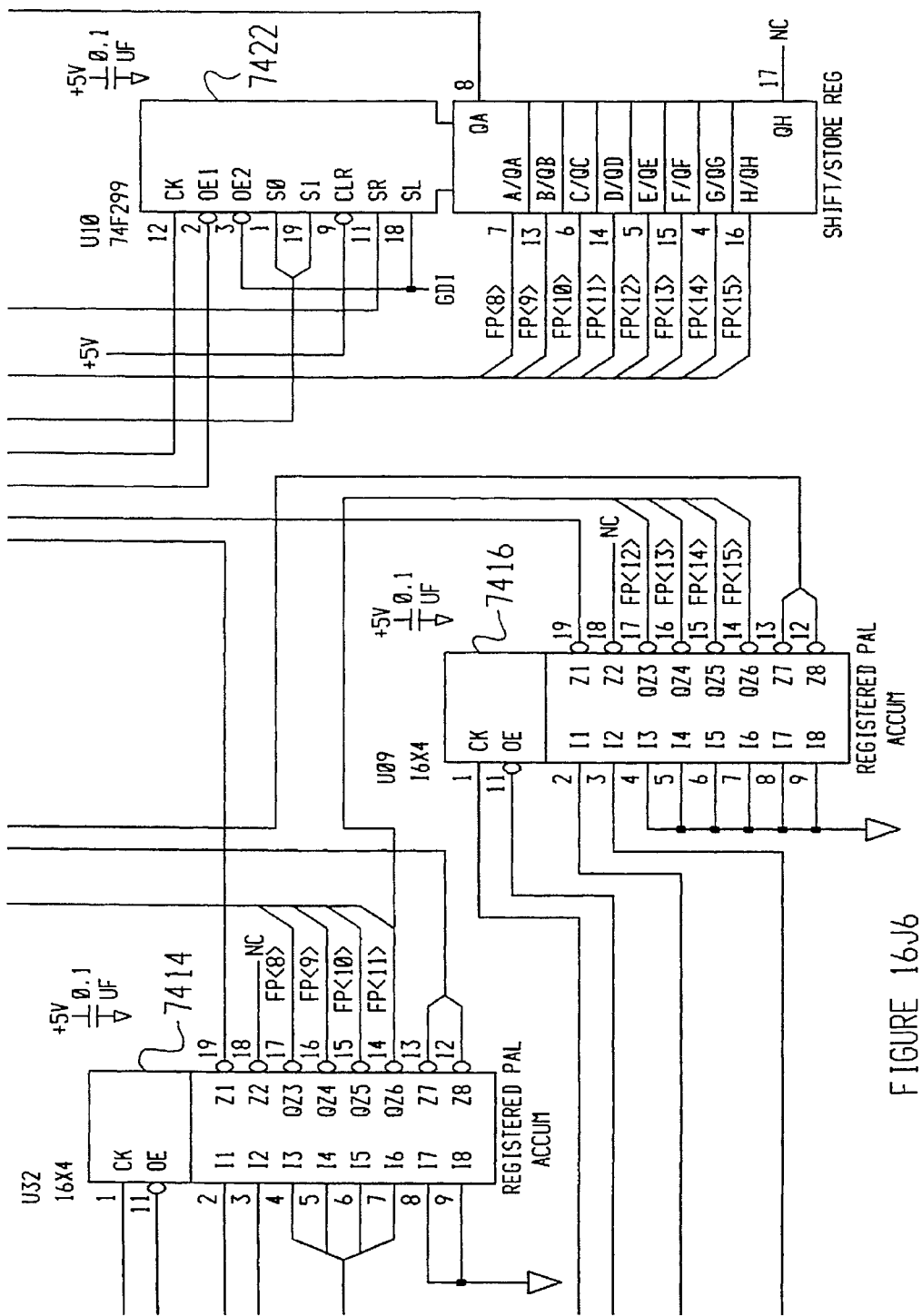
FIGURE 16J6

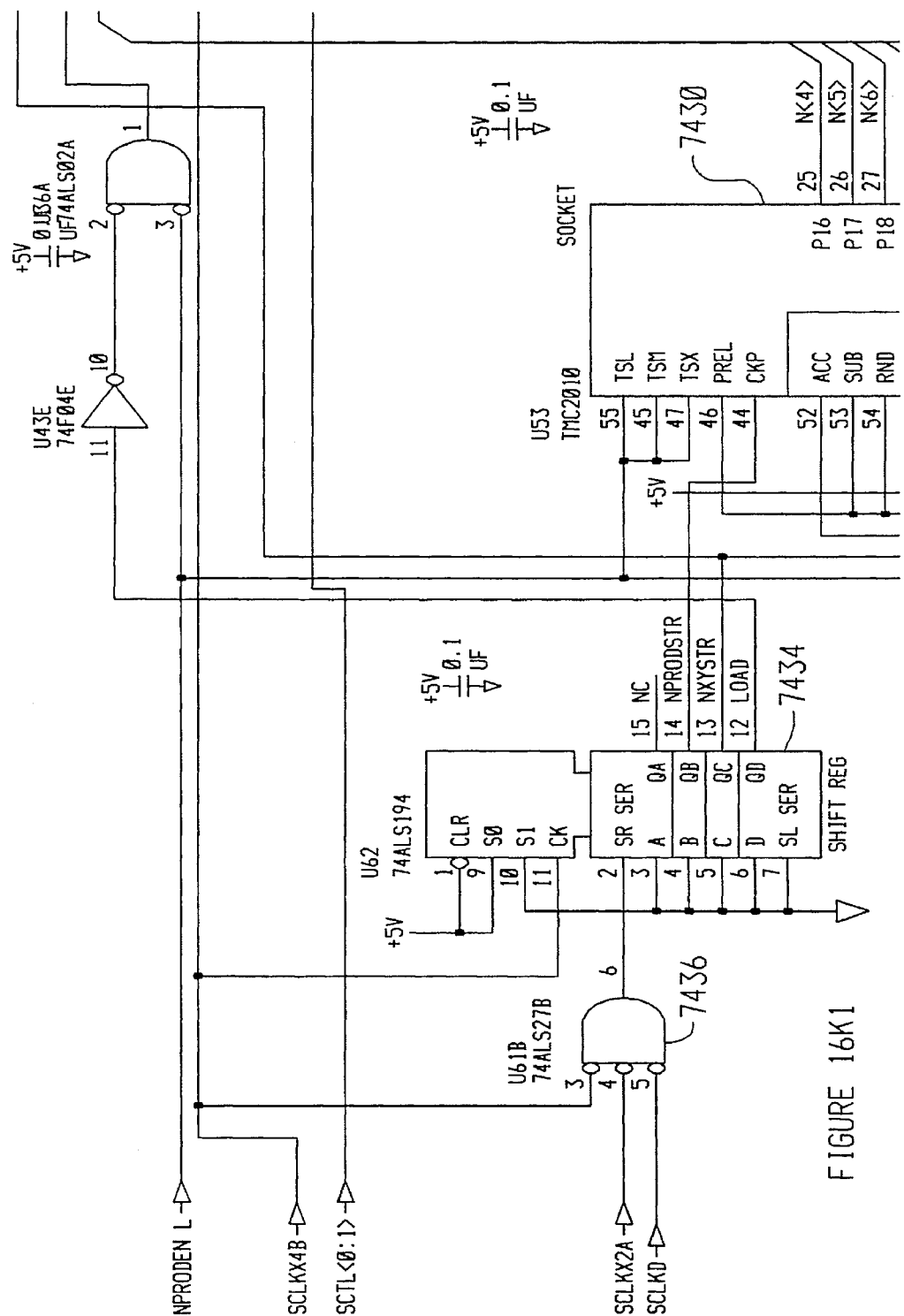
FIGURE 16K1

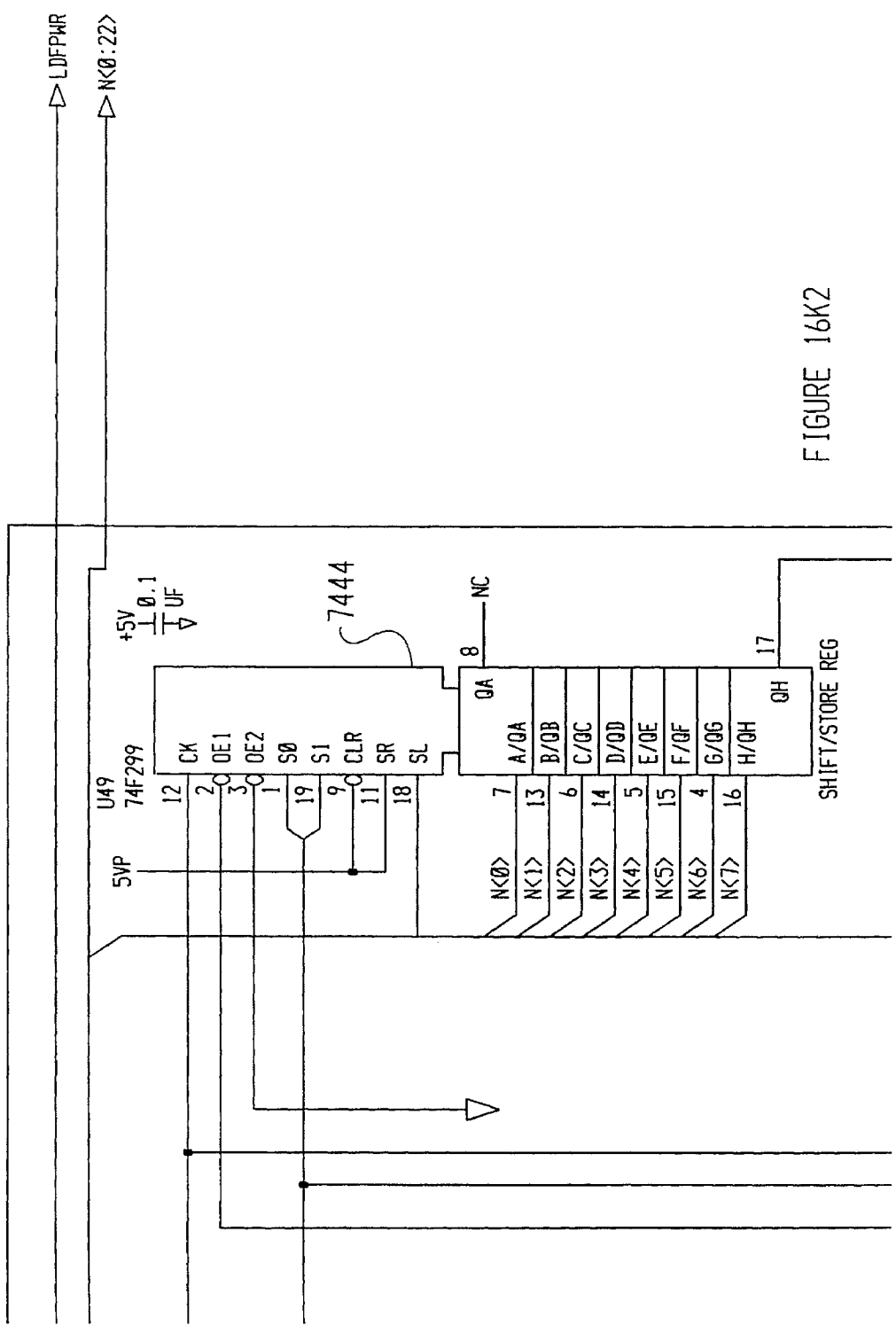
FIGURE 16K2

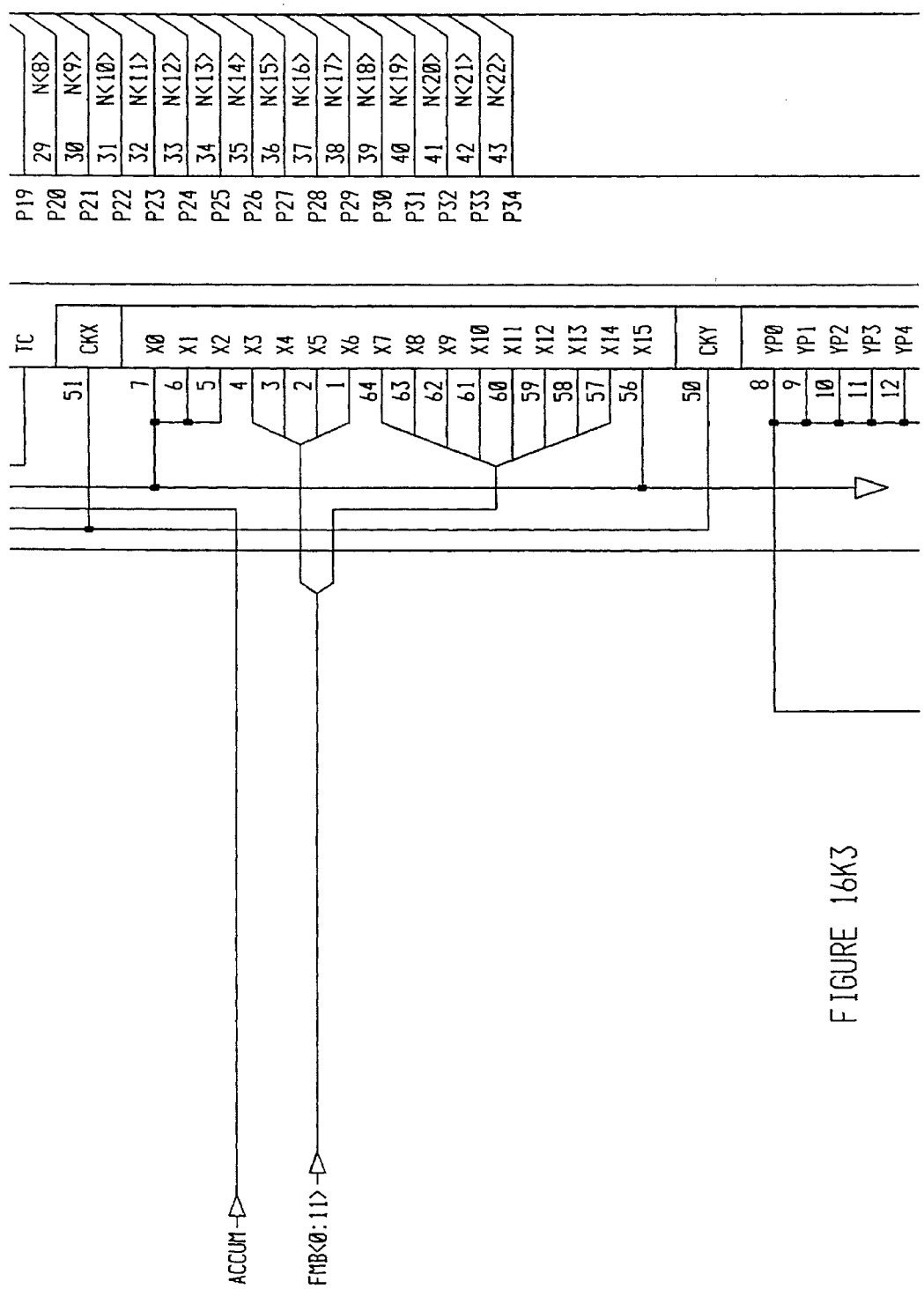
FIGURE 16K3

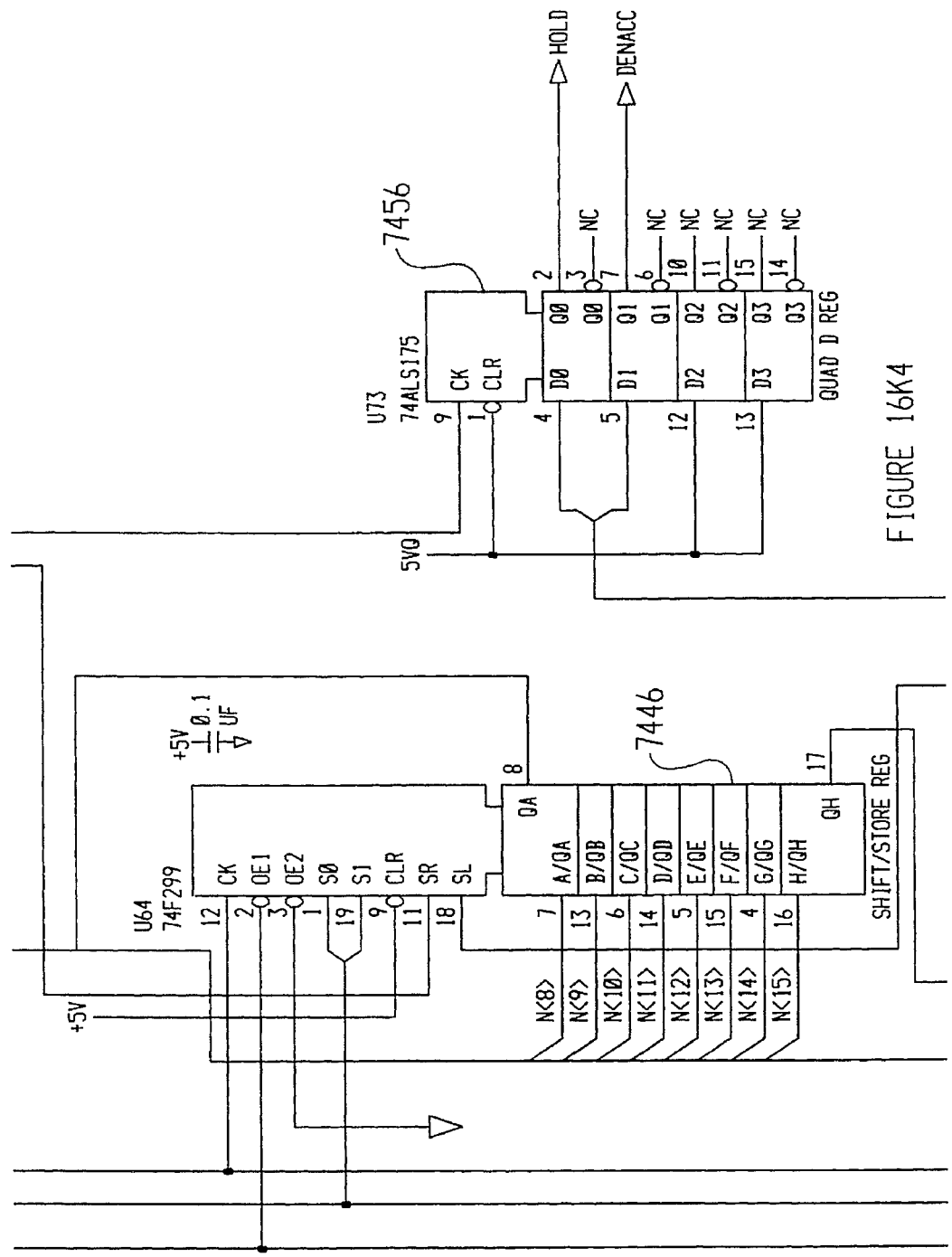

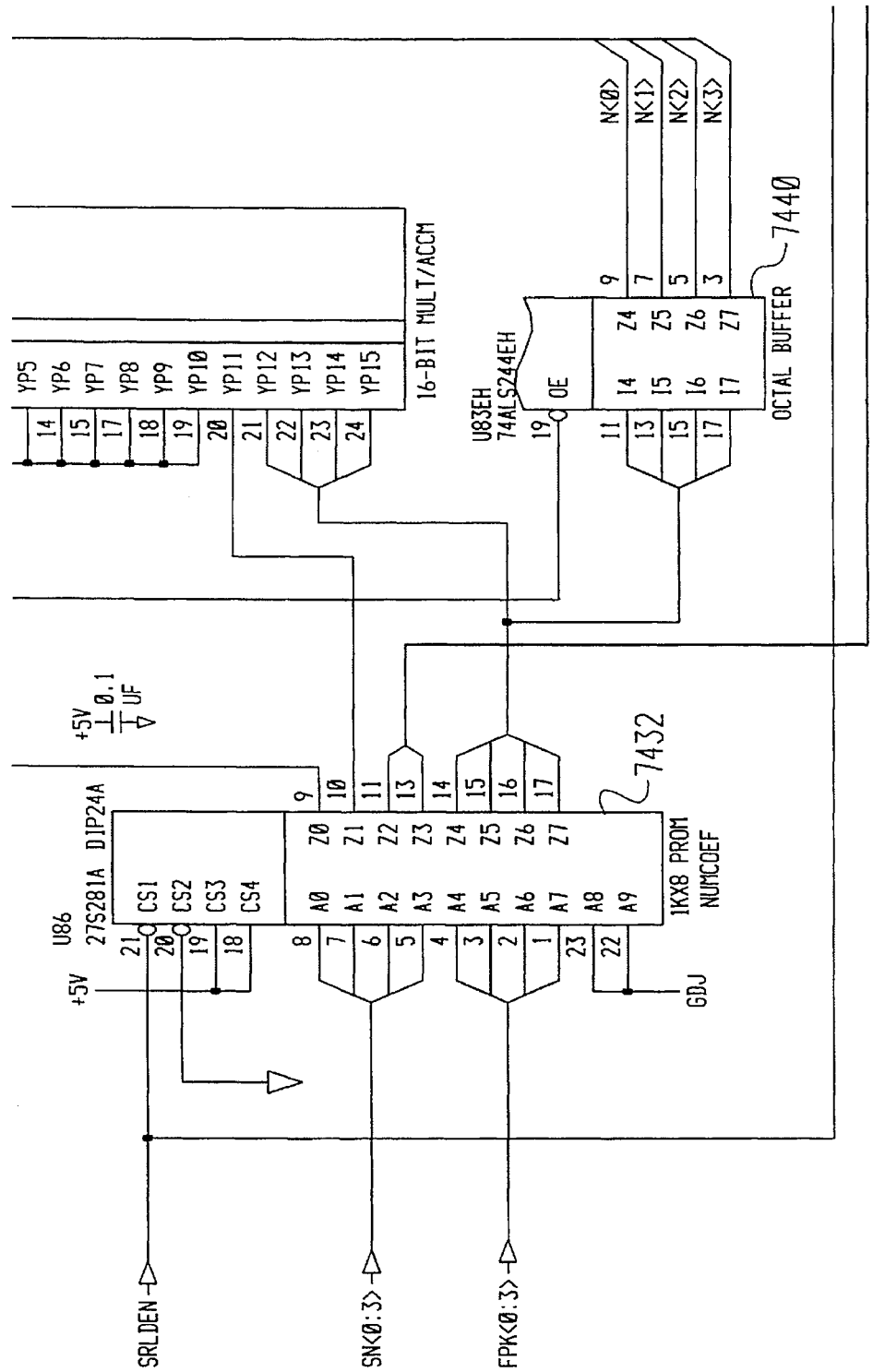
FIGURE 16K5

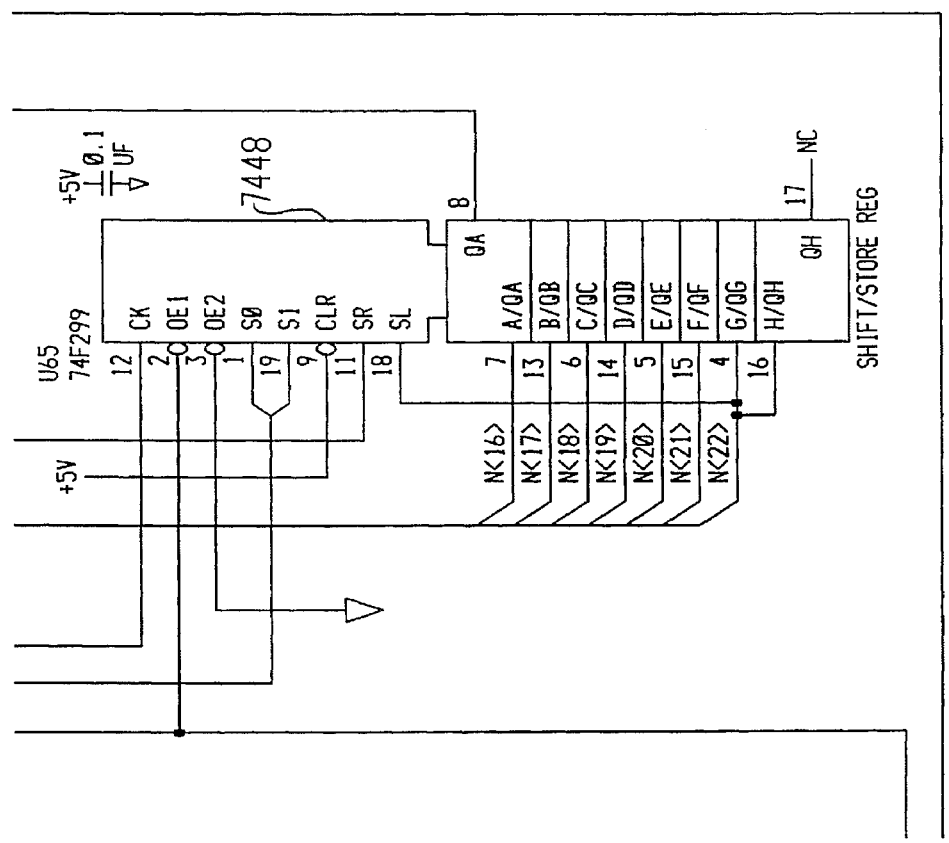
FIGURE 16K6

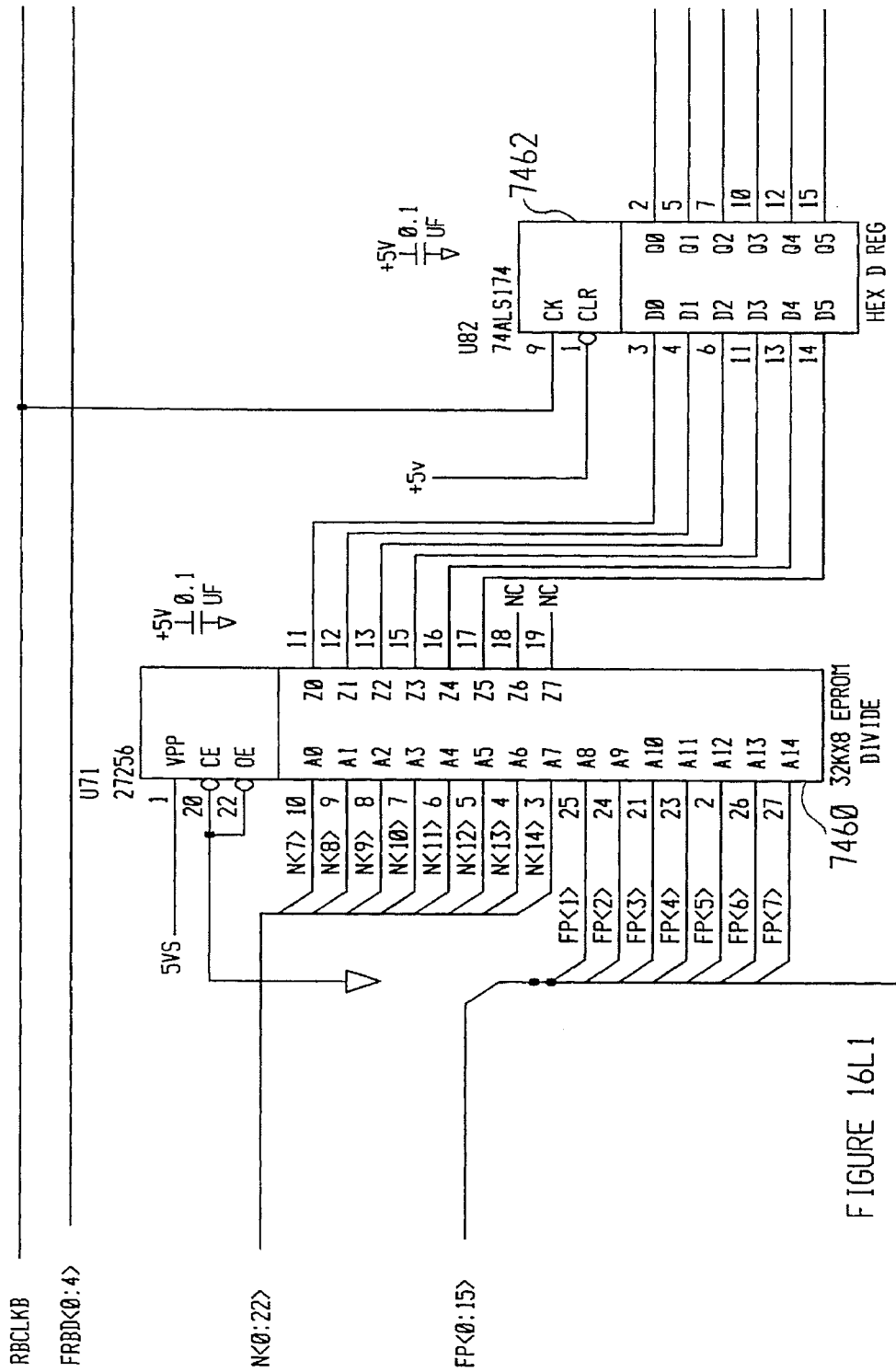
FIGURE 16L1

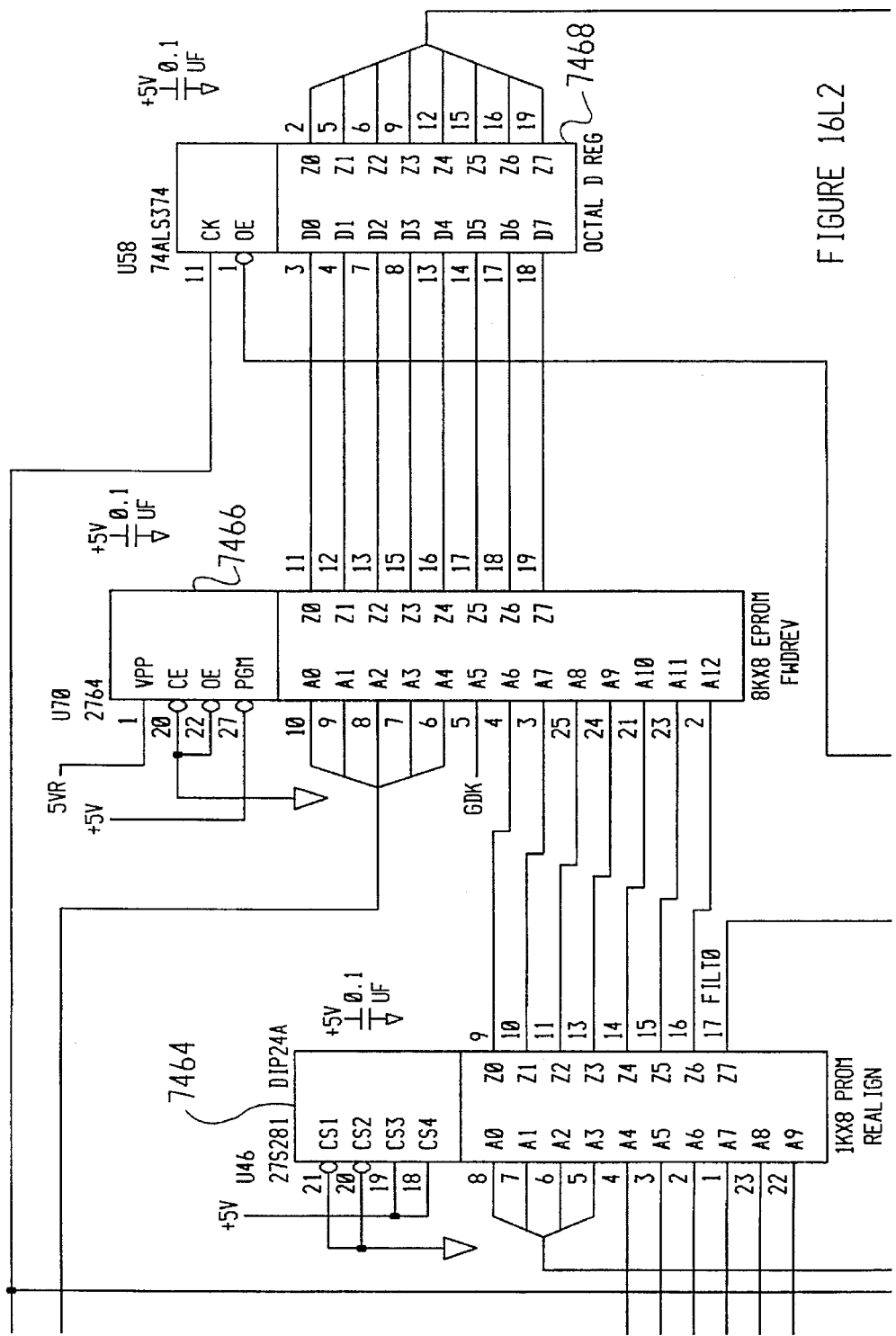

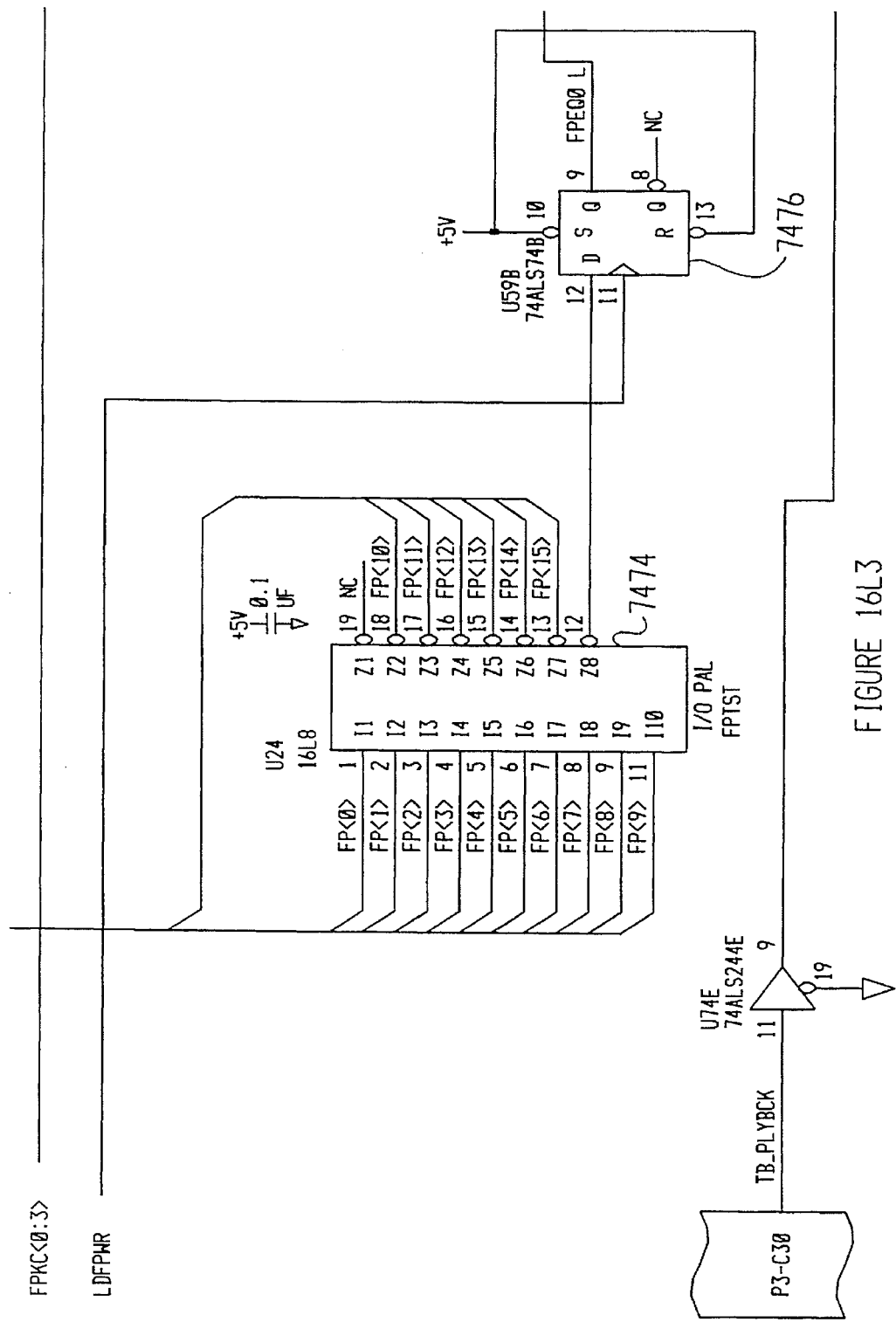
FIGURE 16L3

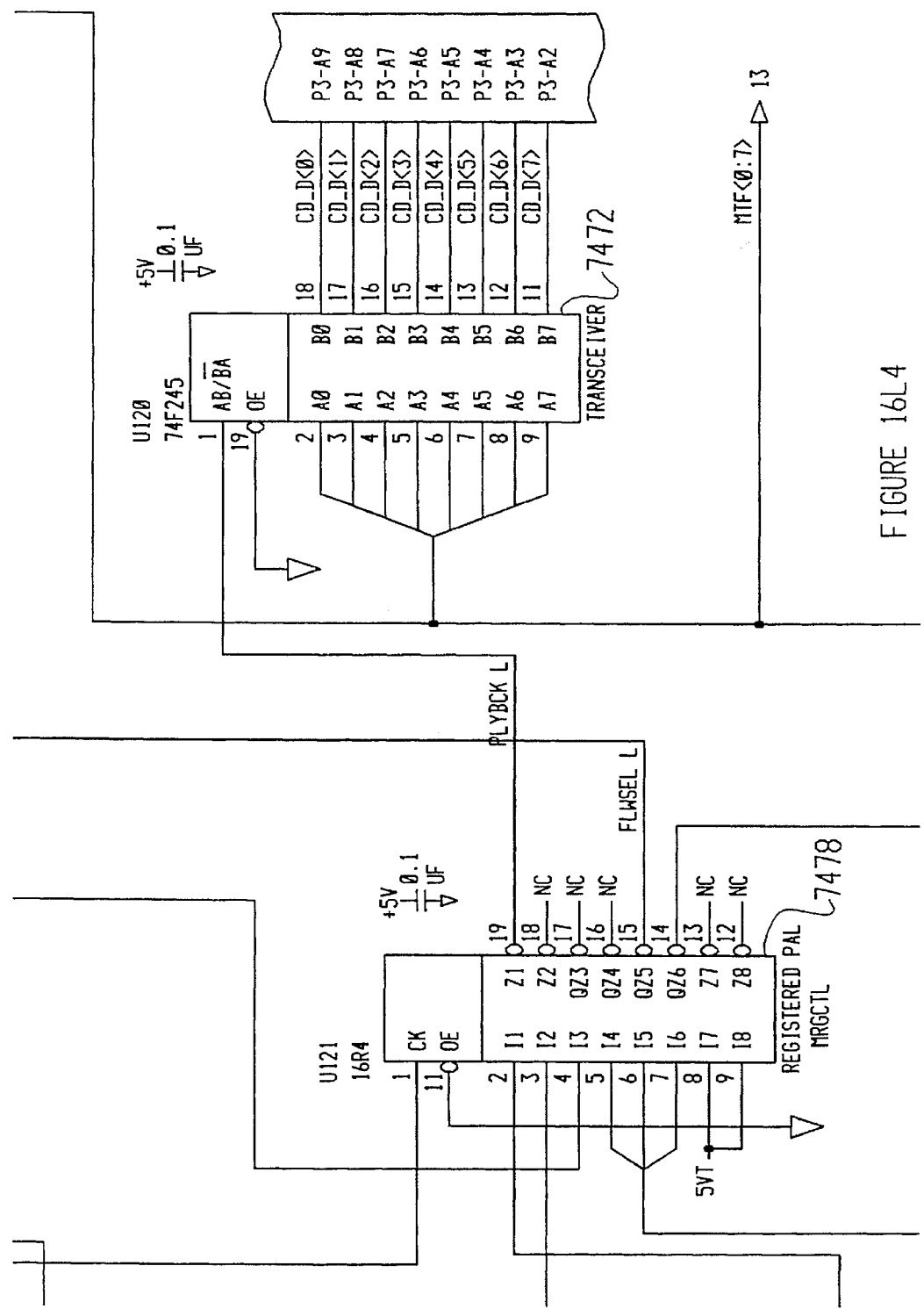
FIGURE 16L4

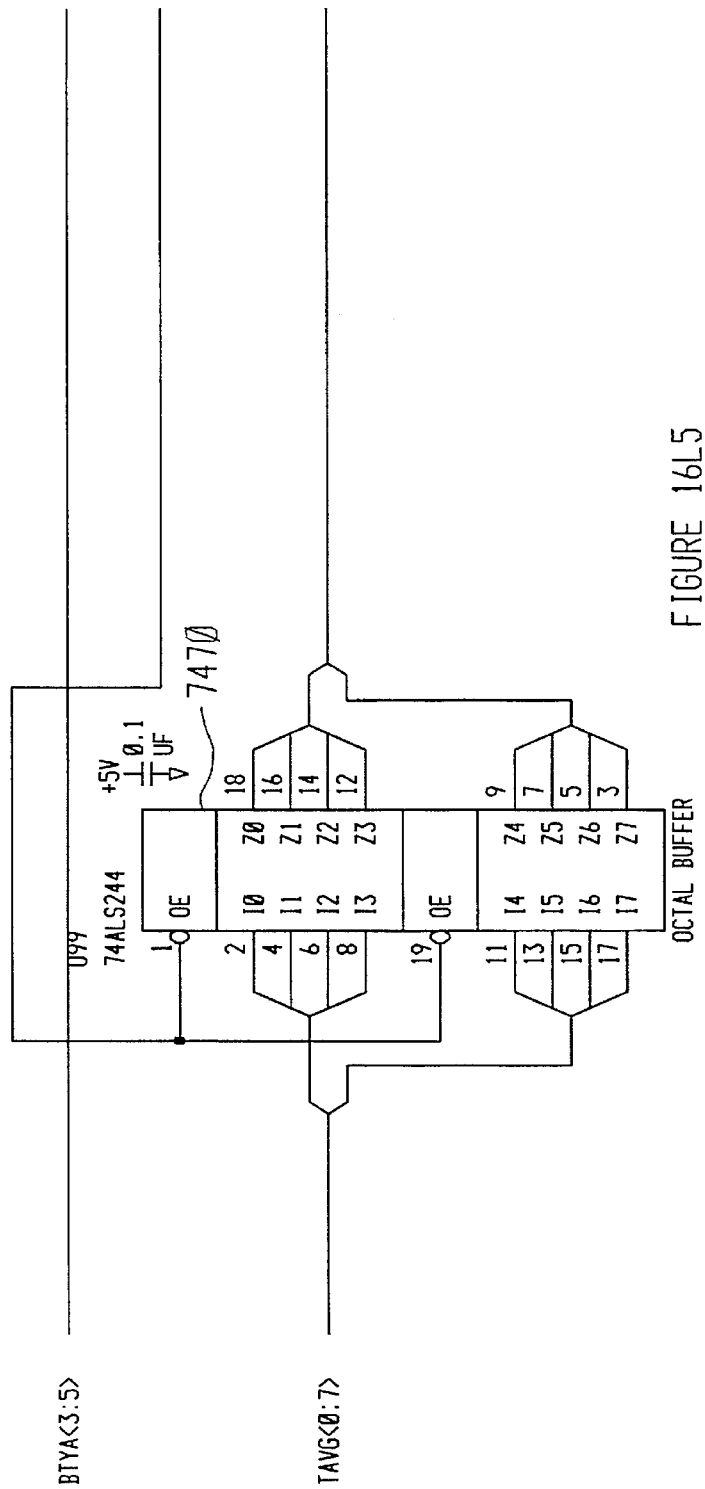

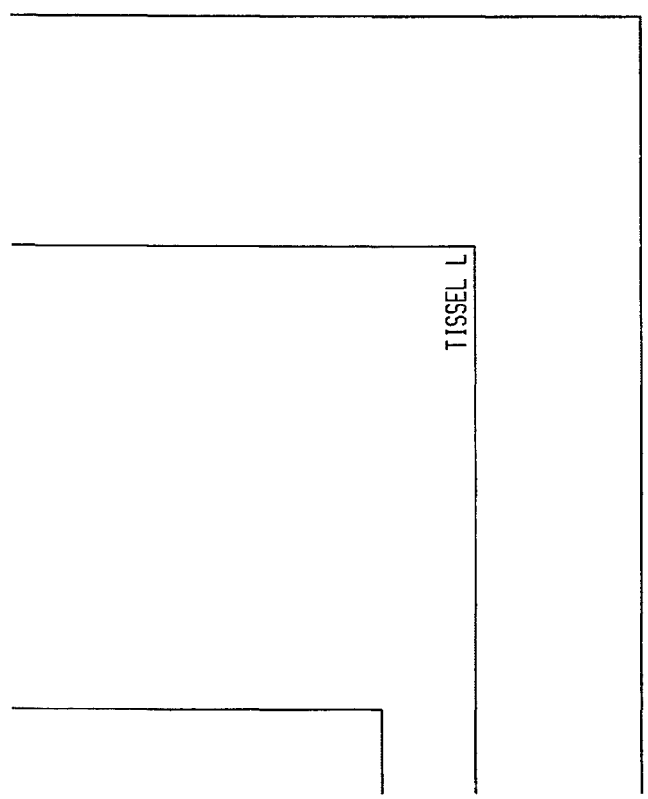
FIGURE 16L6

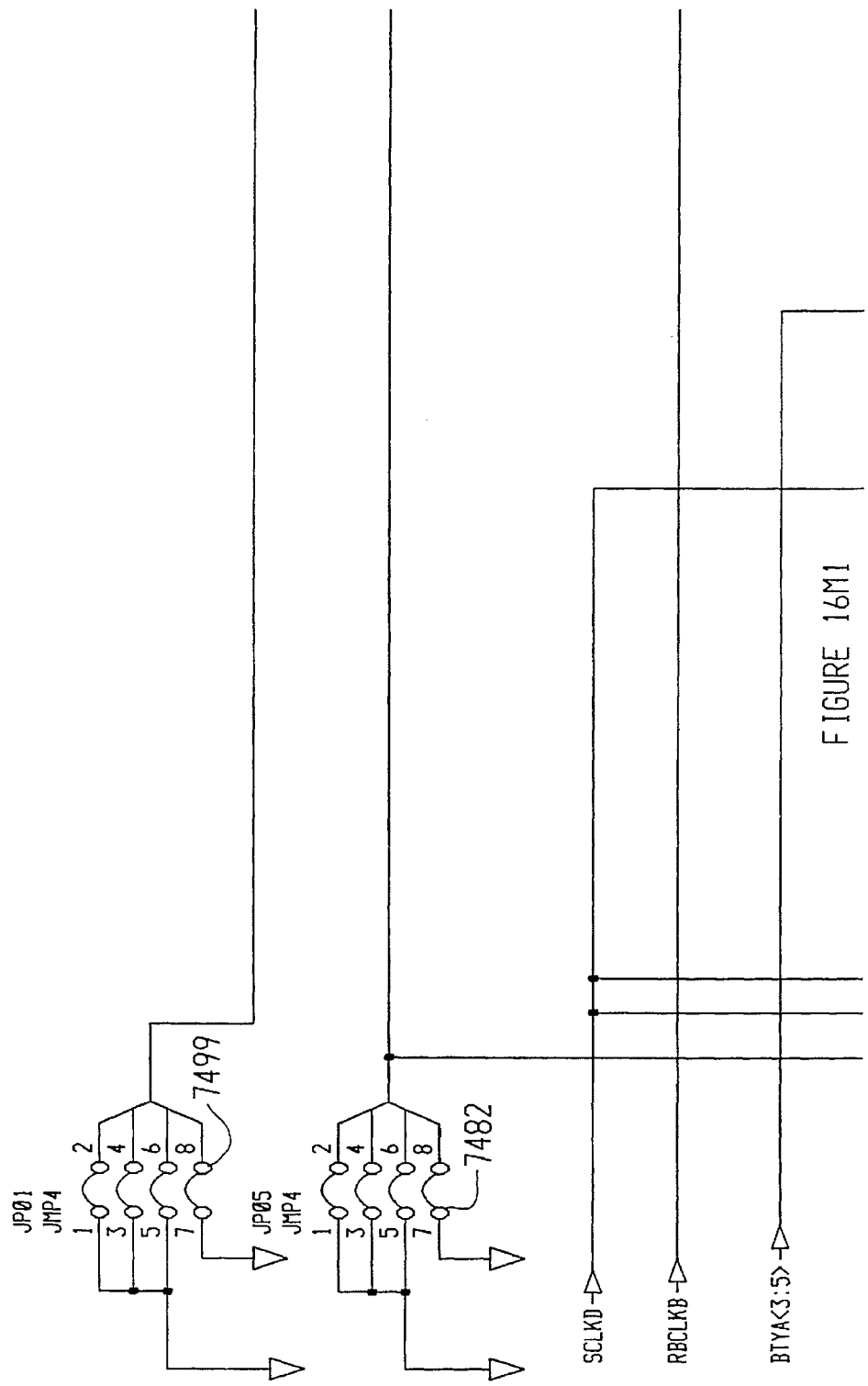

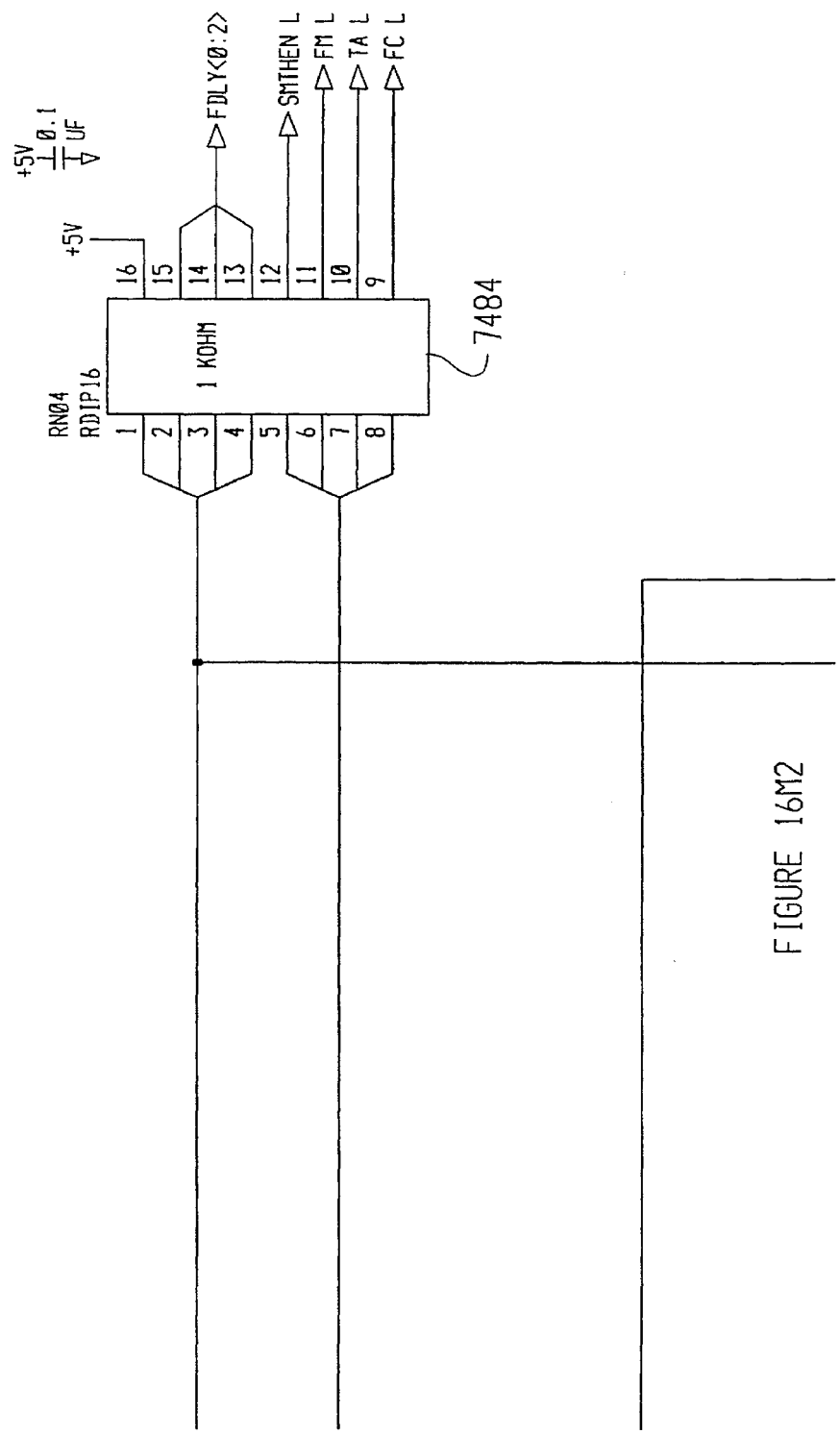
FIGURE 16M2

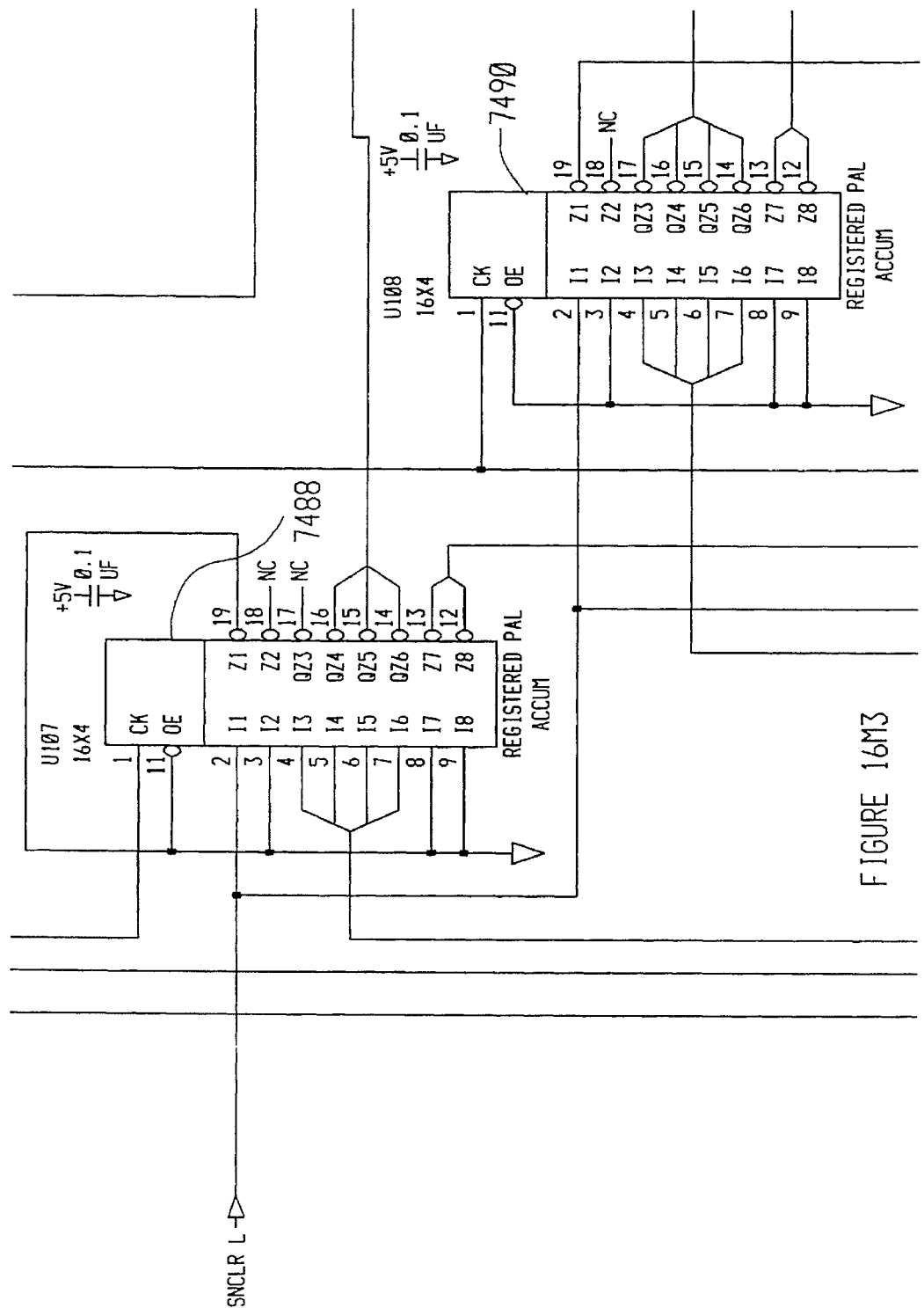
FIGURE 16M3

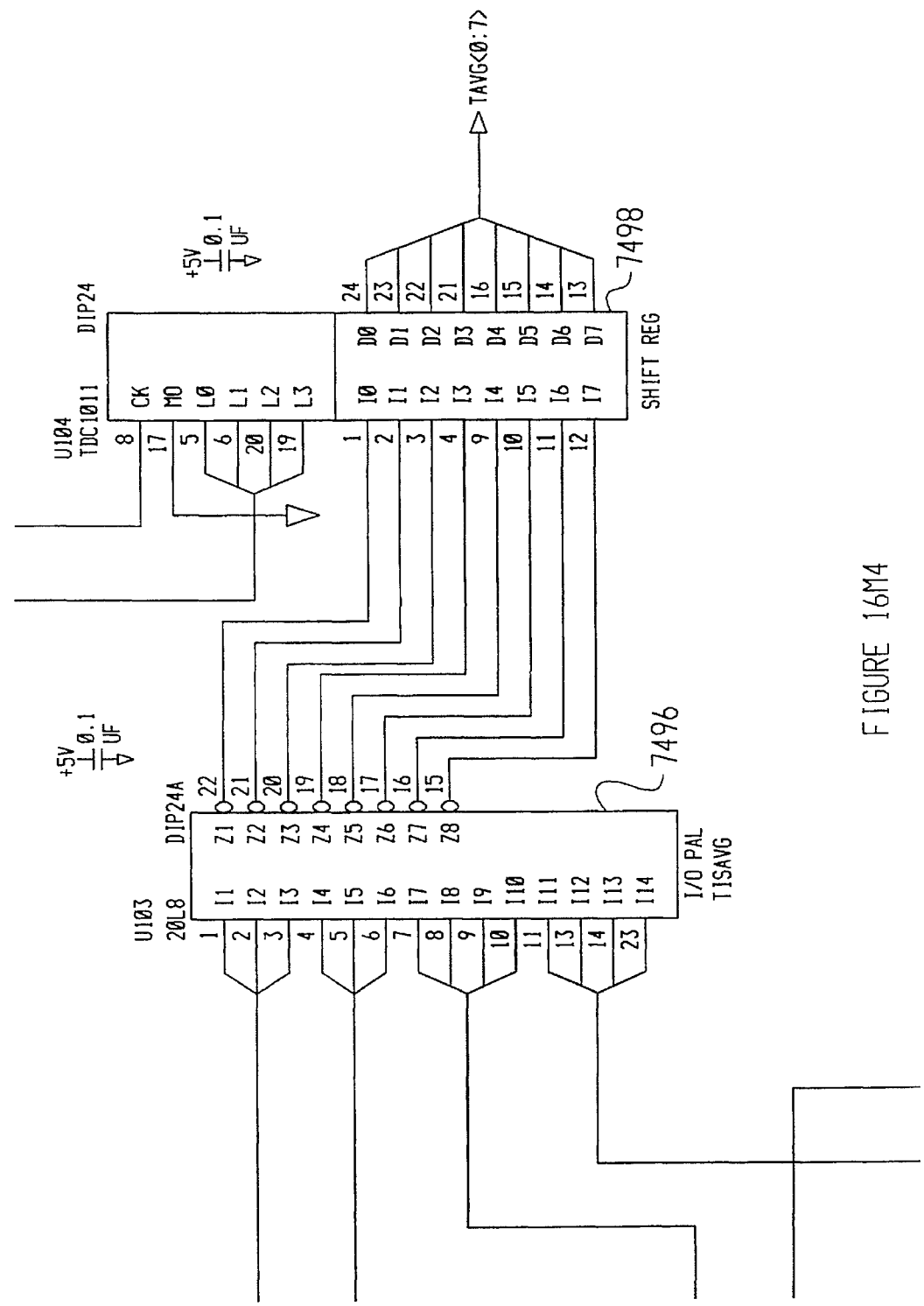
FIGURE 16M4

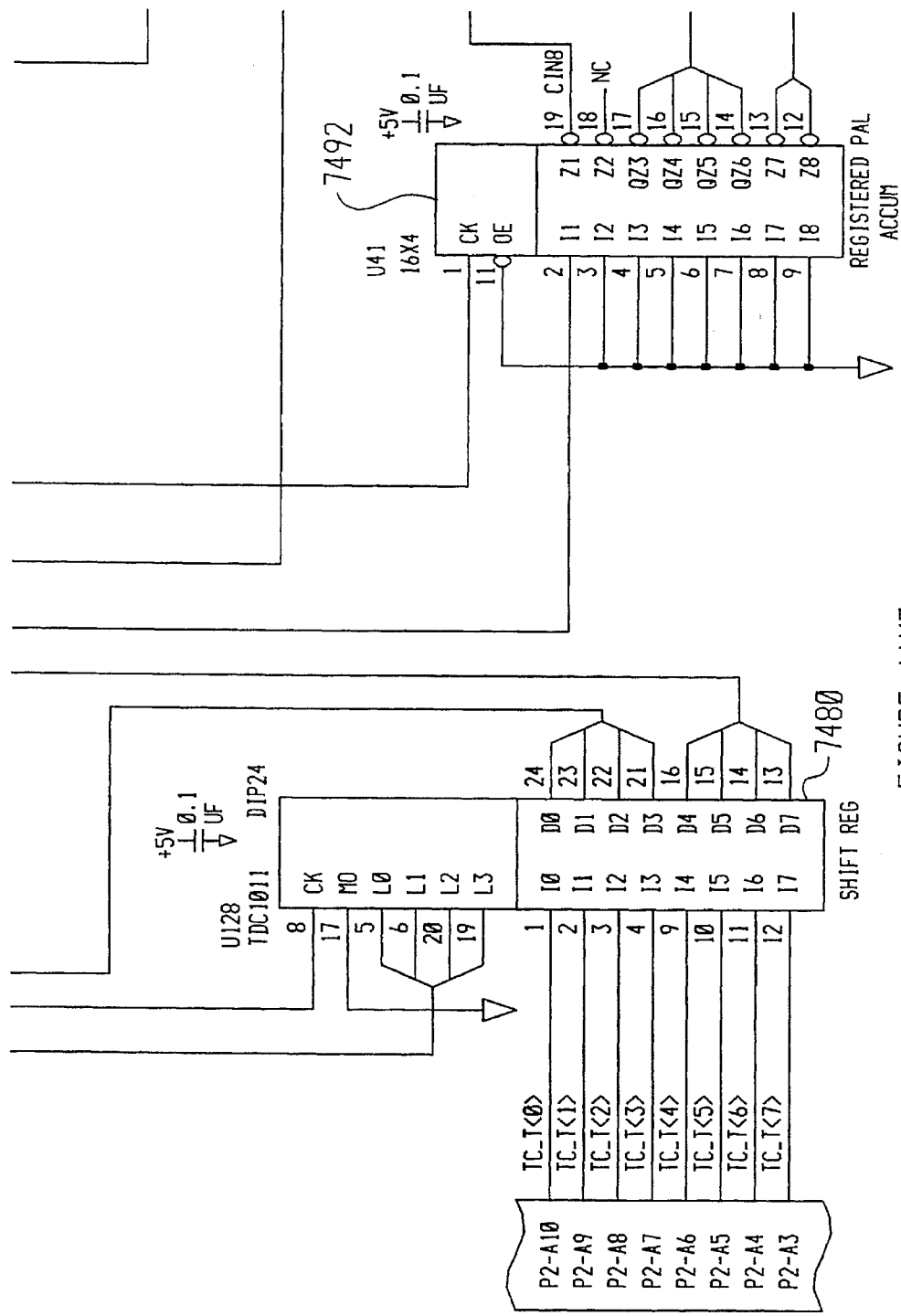
FIGURE 16M5

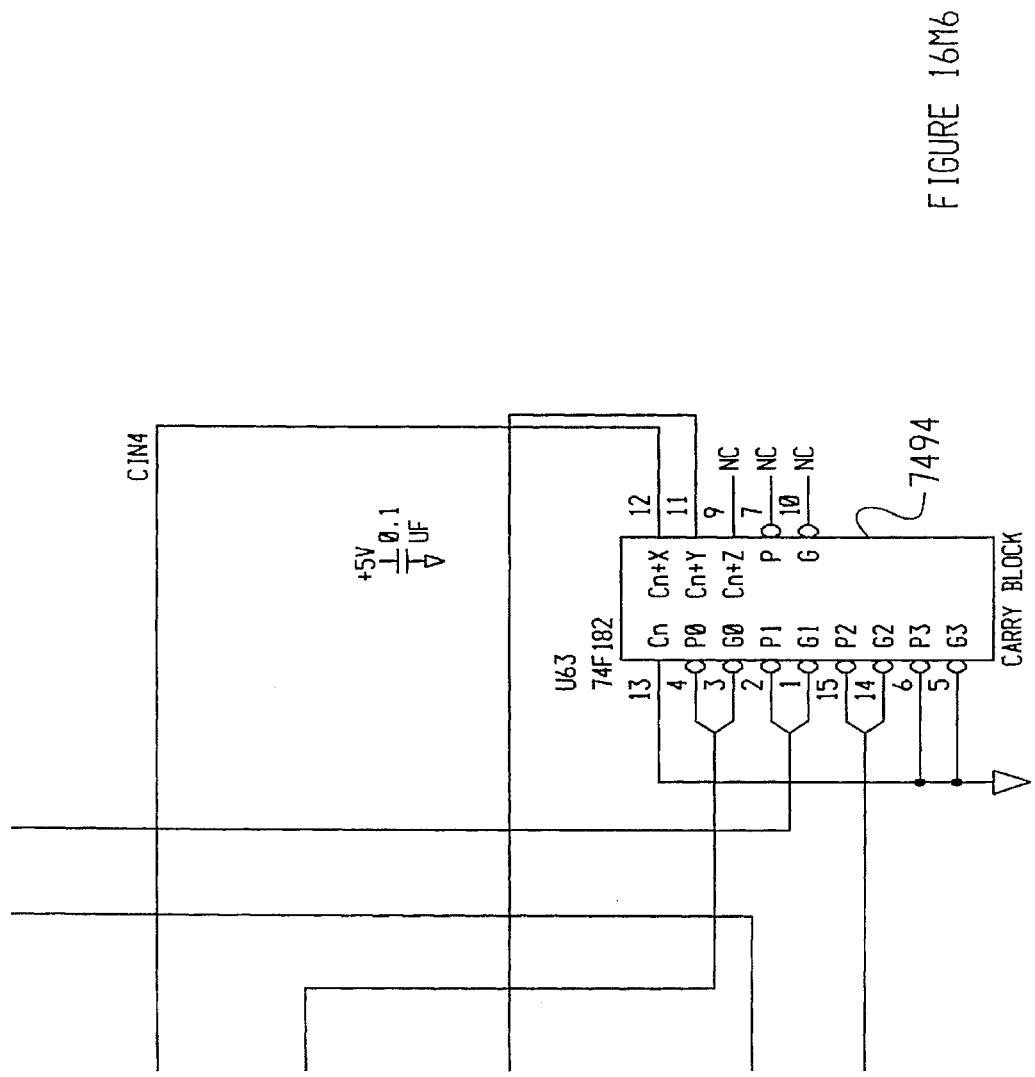
FIGURE 16M6

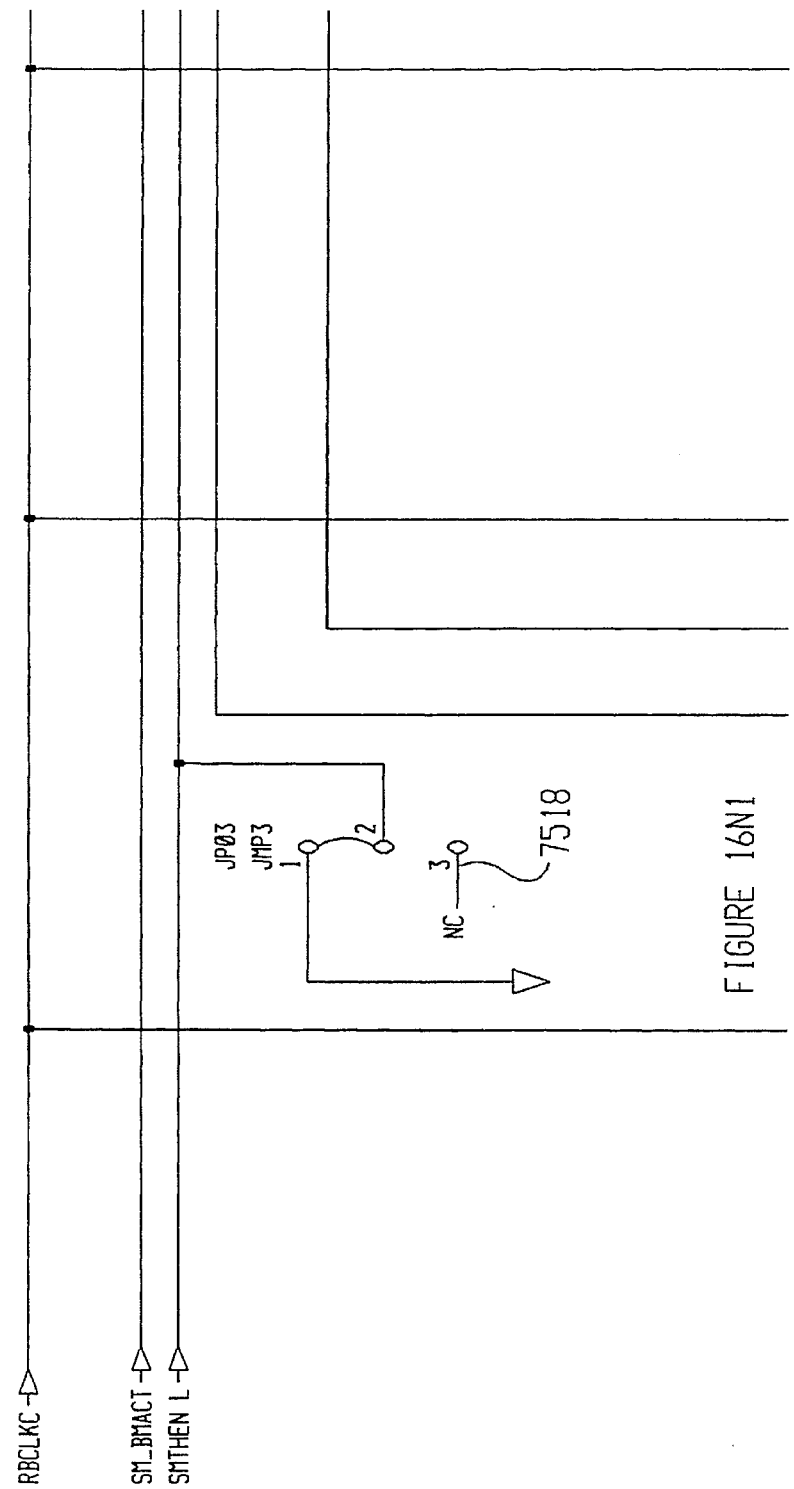
FIGURE 16N1

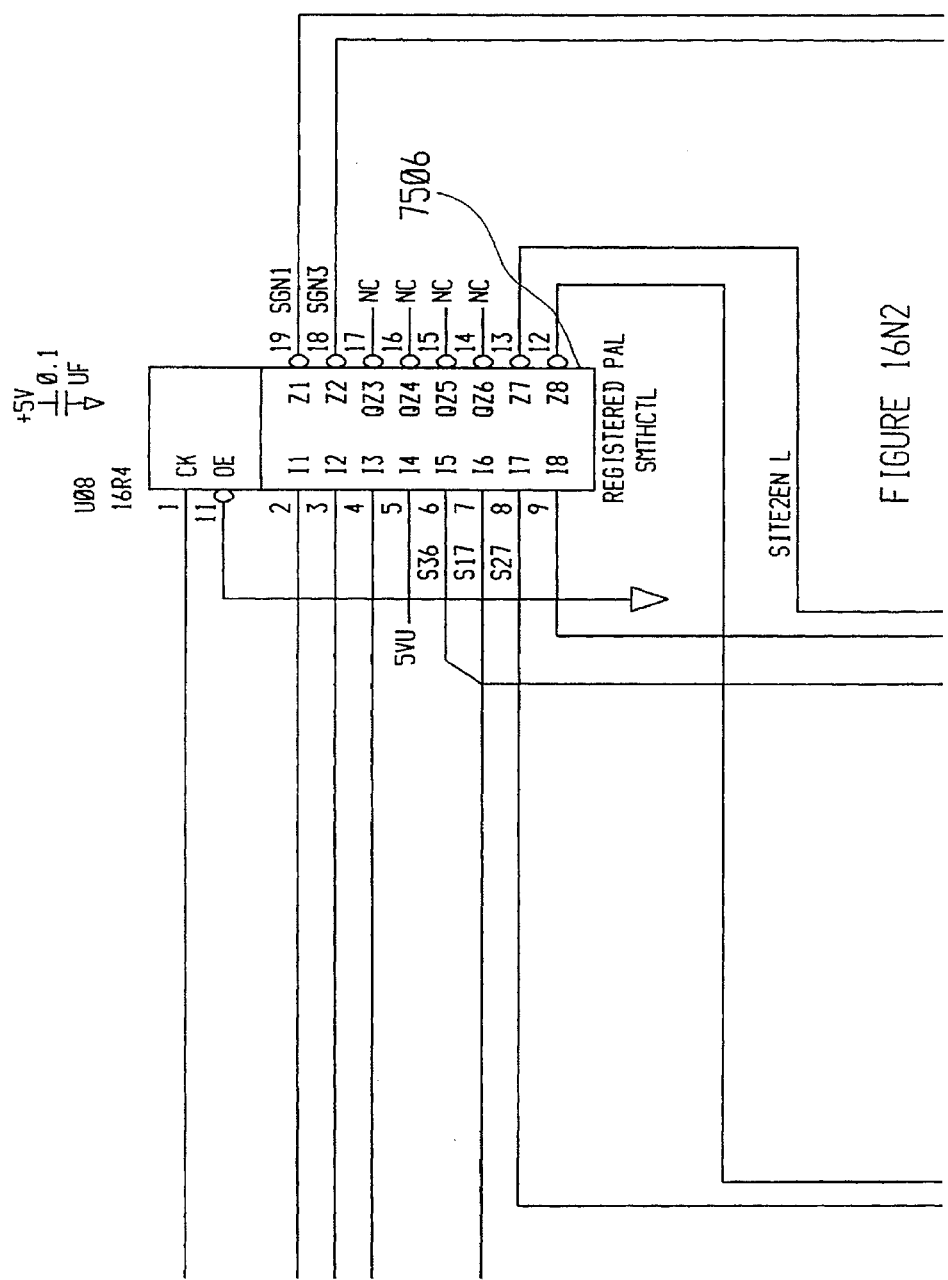

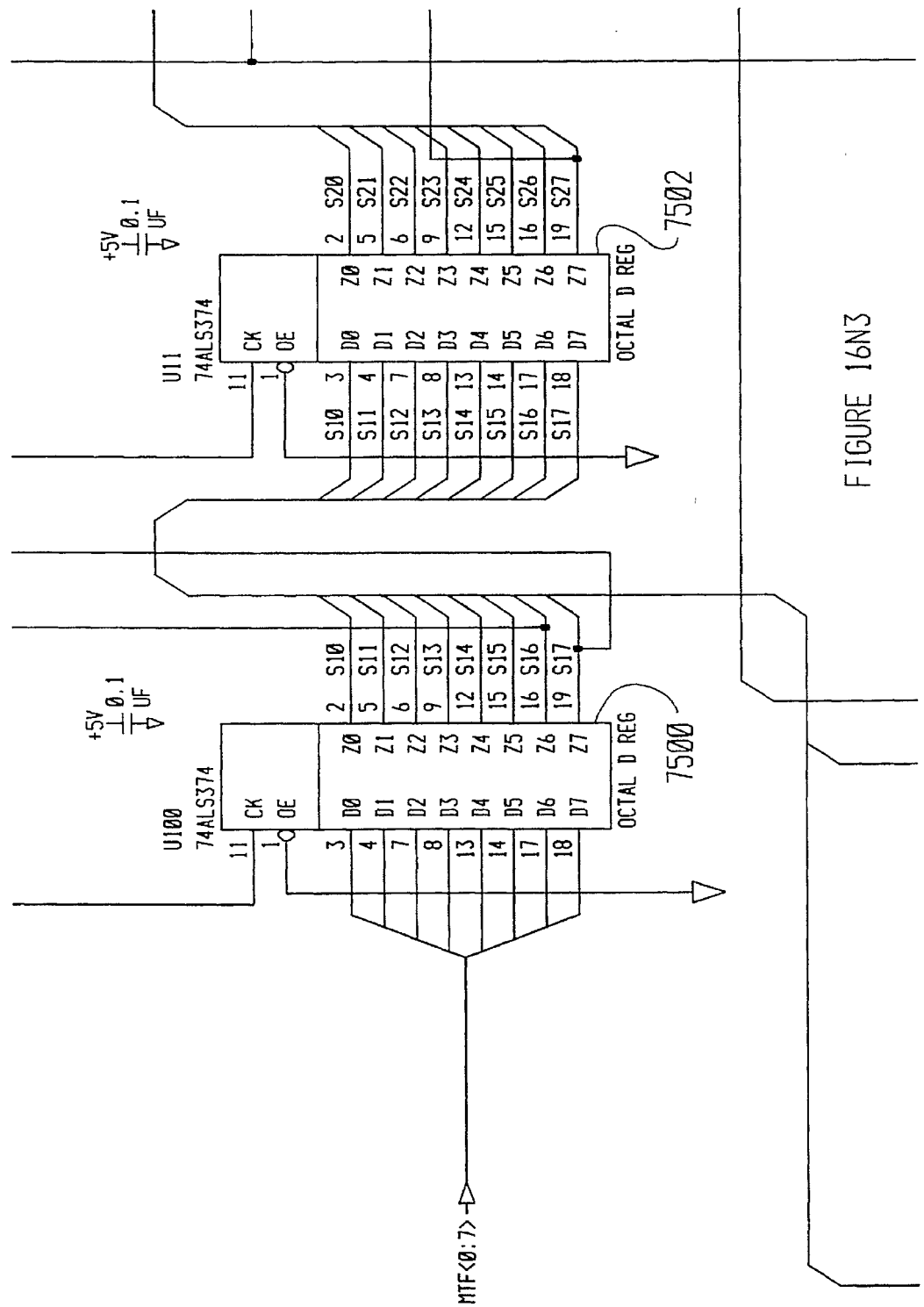
FIGURE 16N3

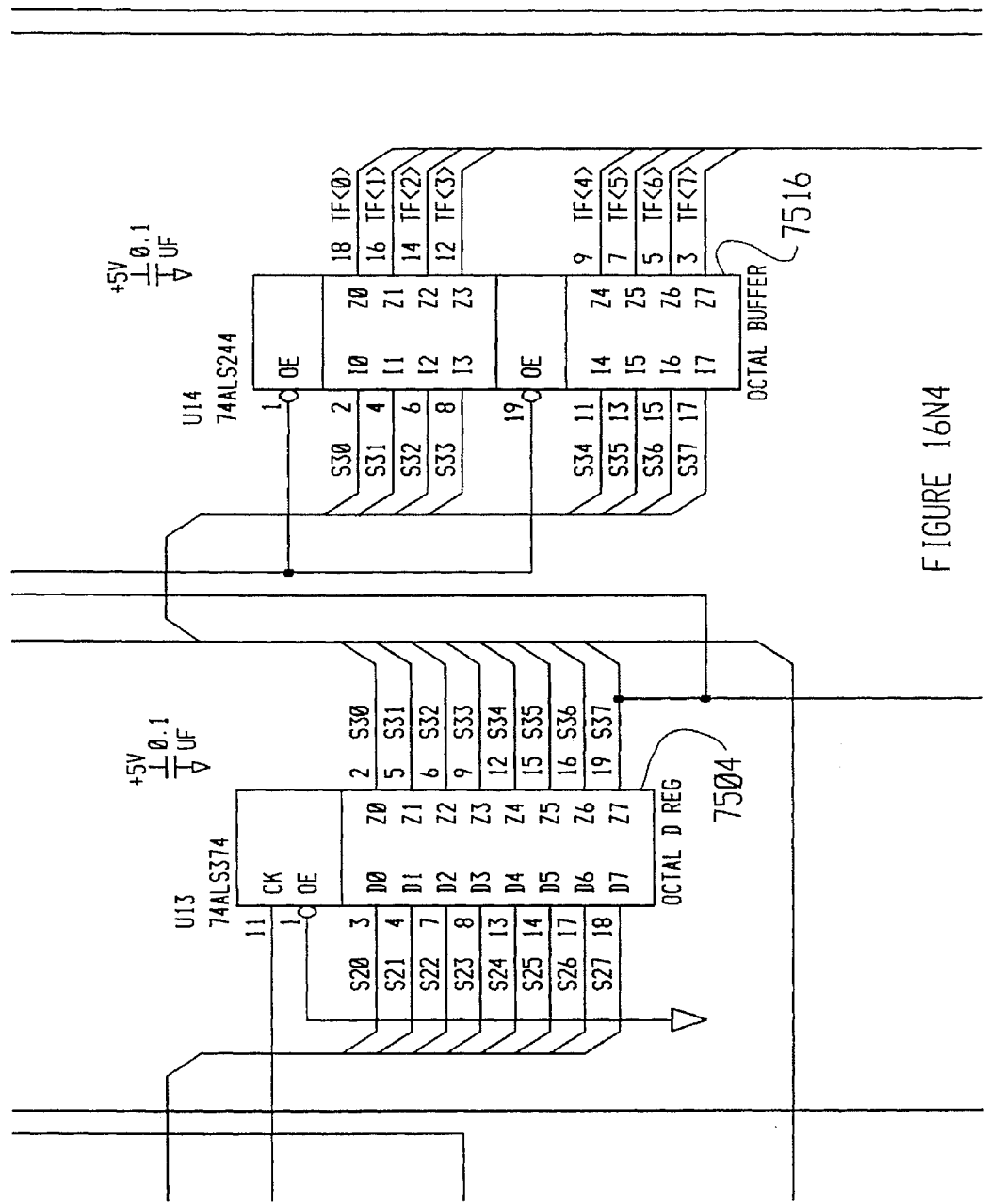
FIGURE 16N4

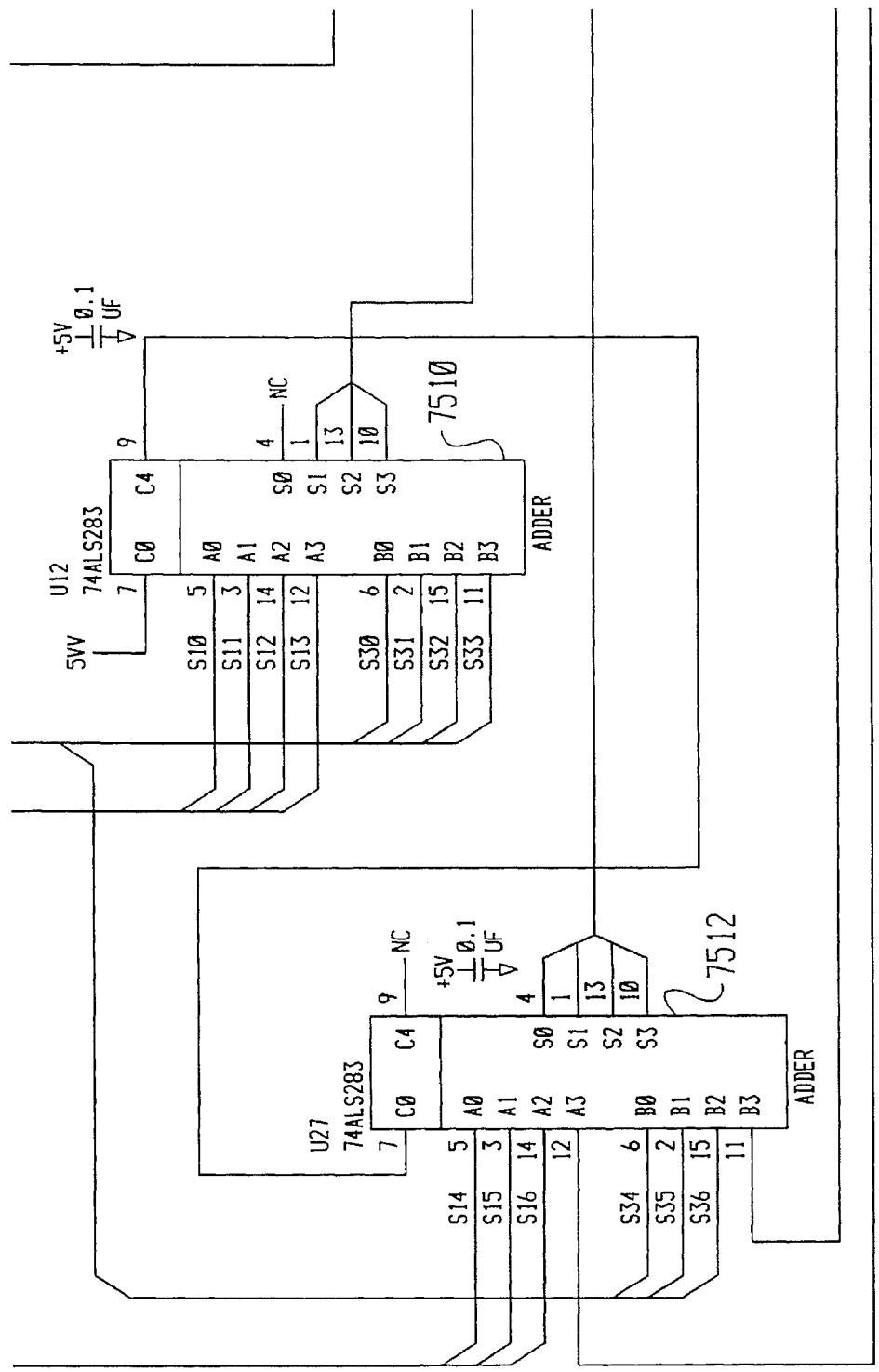
FIGURE 16N5

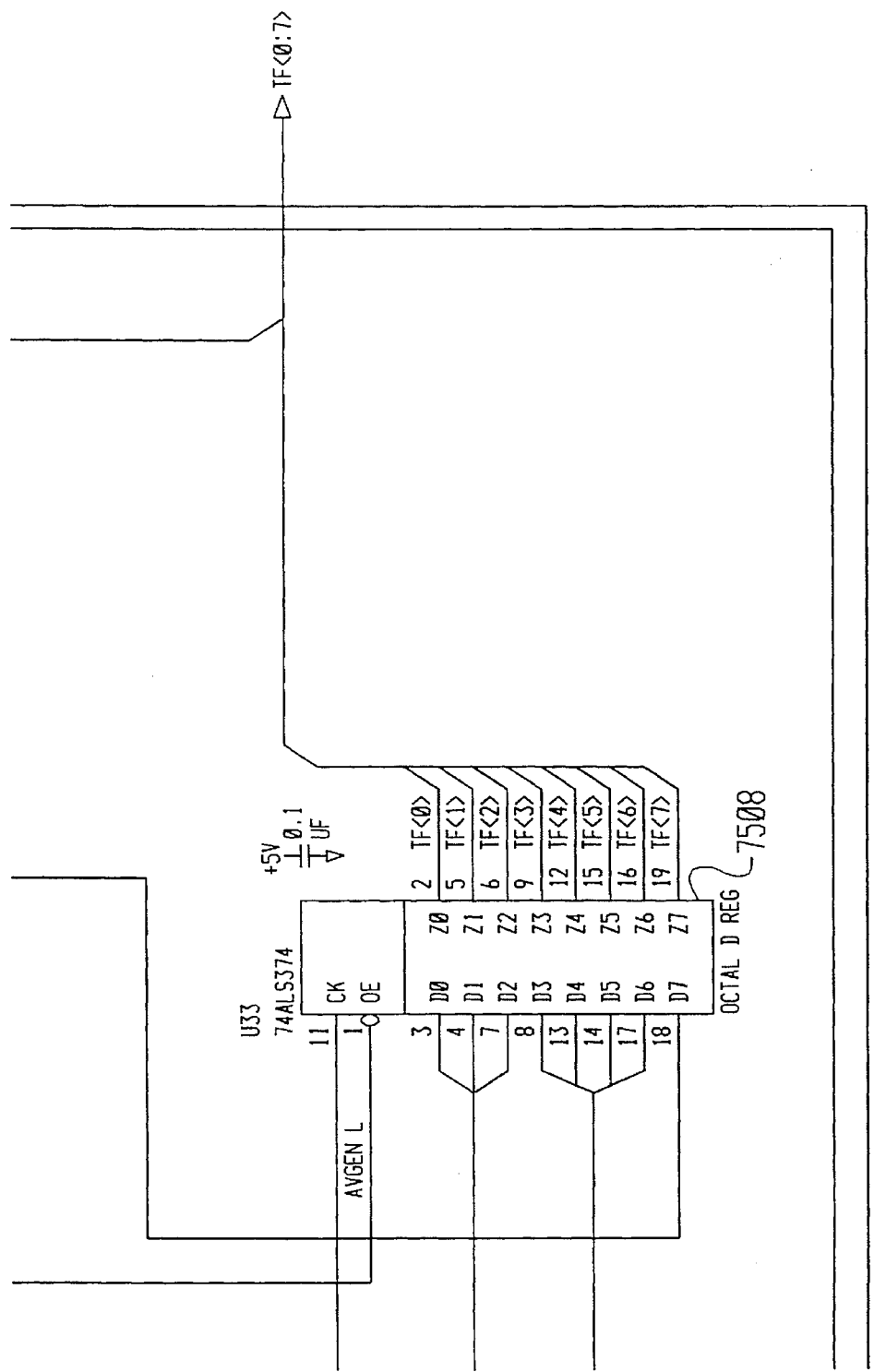
FIGURE 16N6

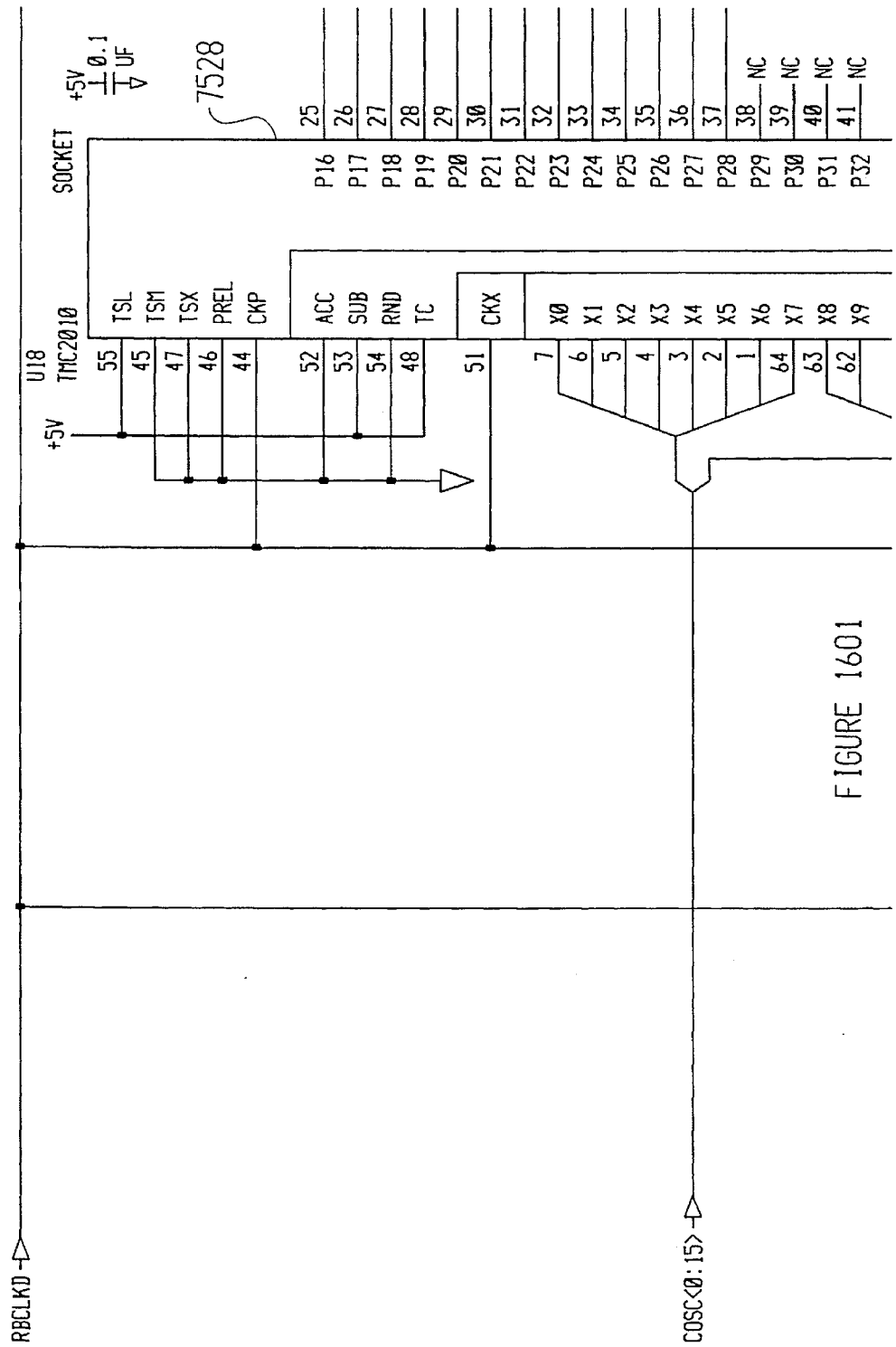
FIGURE 1601

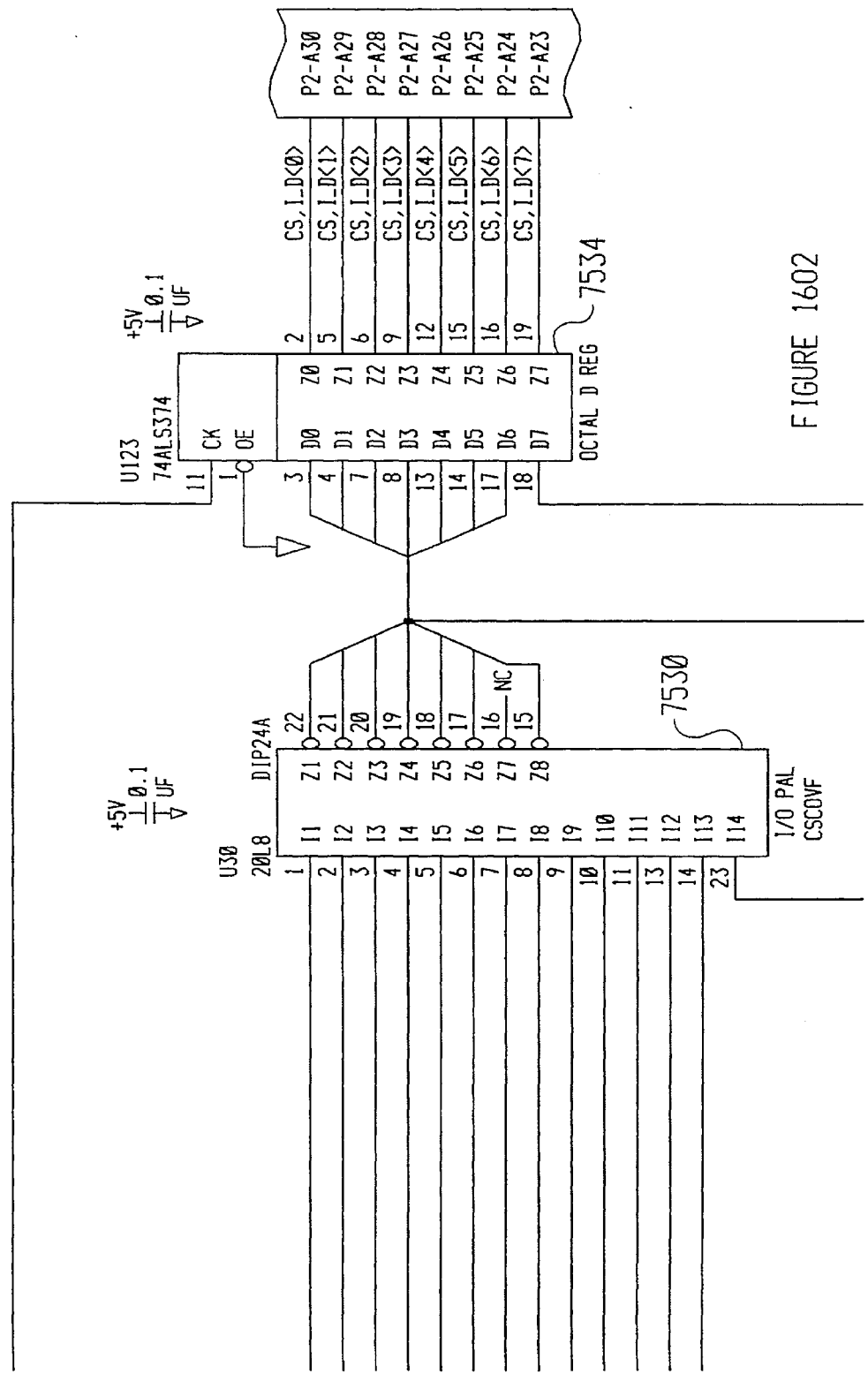
FIGURE 1602

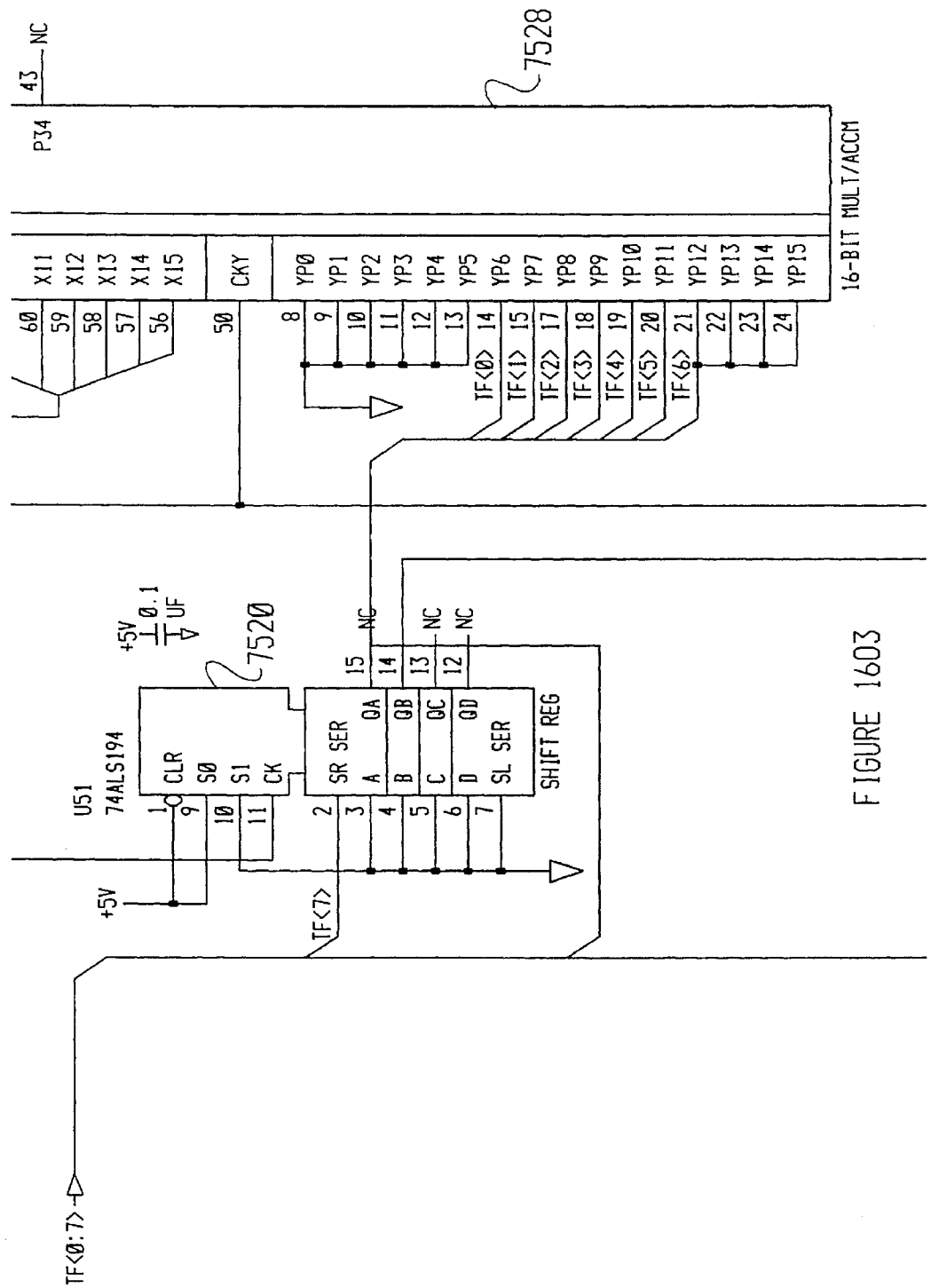
FIGURE 1603

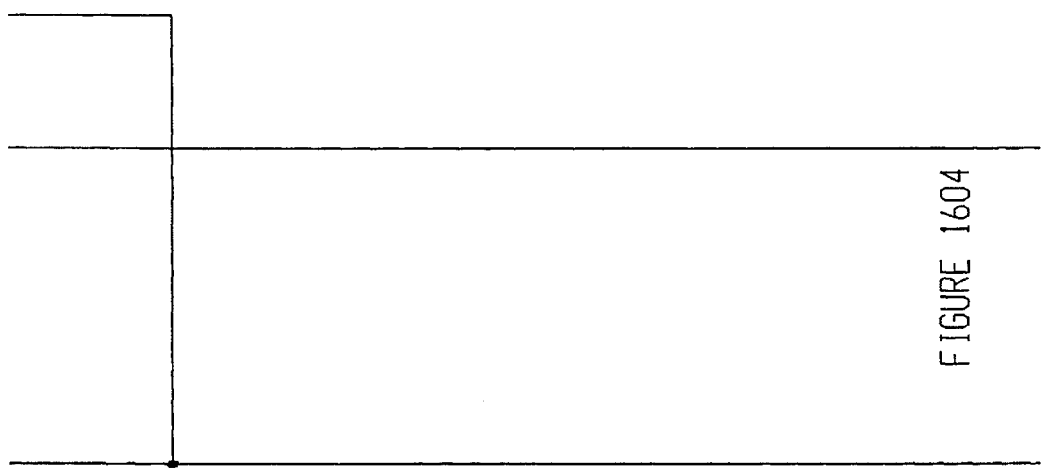

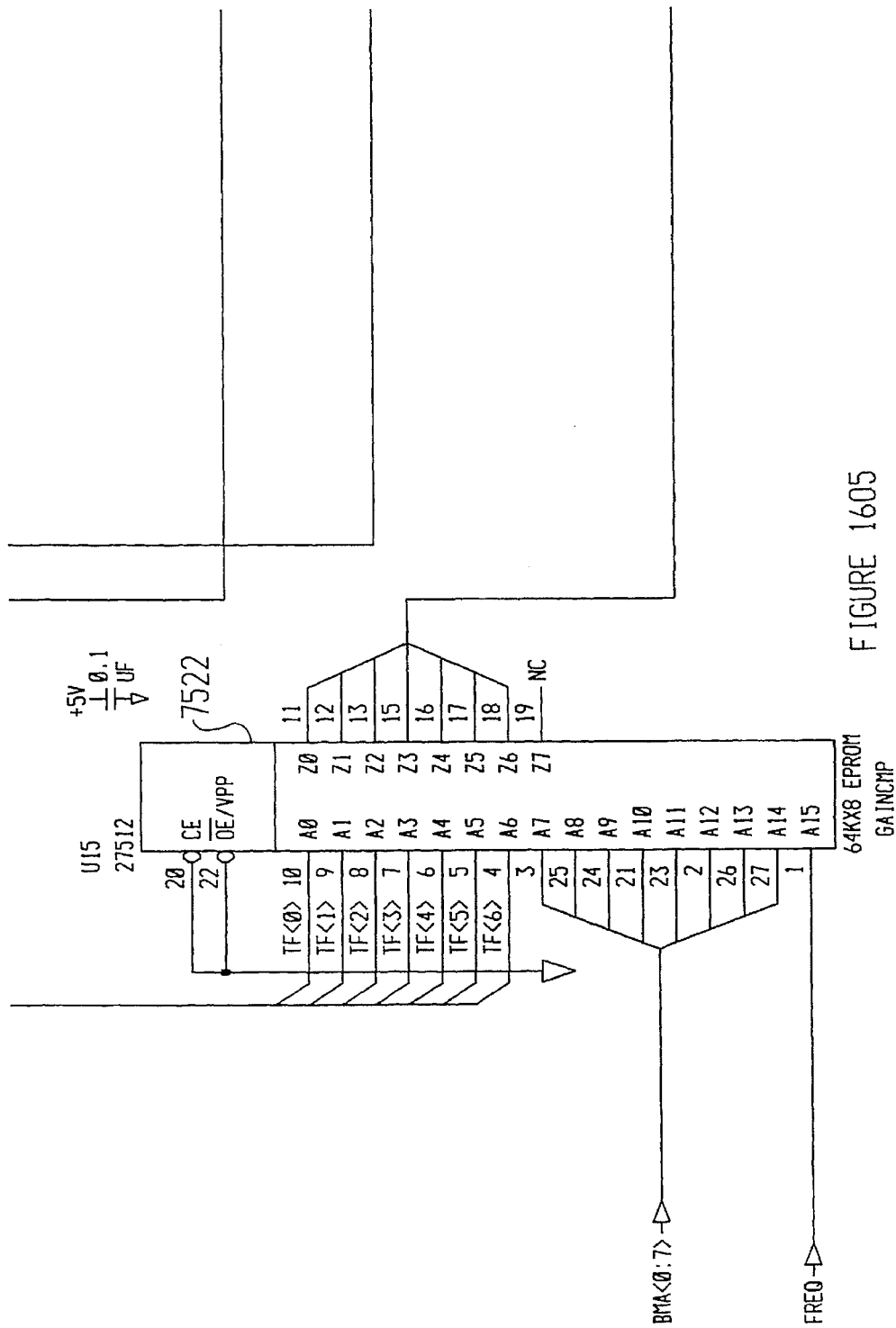
FIGURE 1605

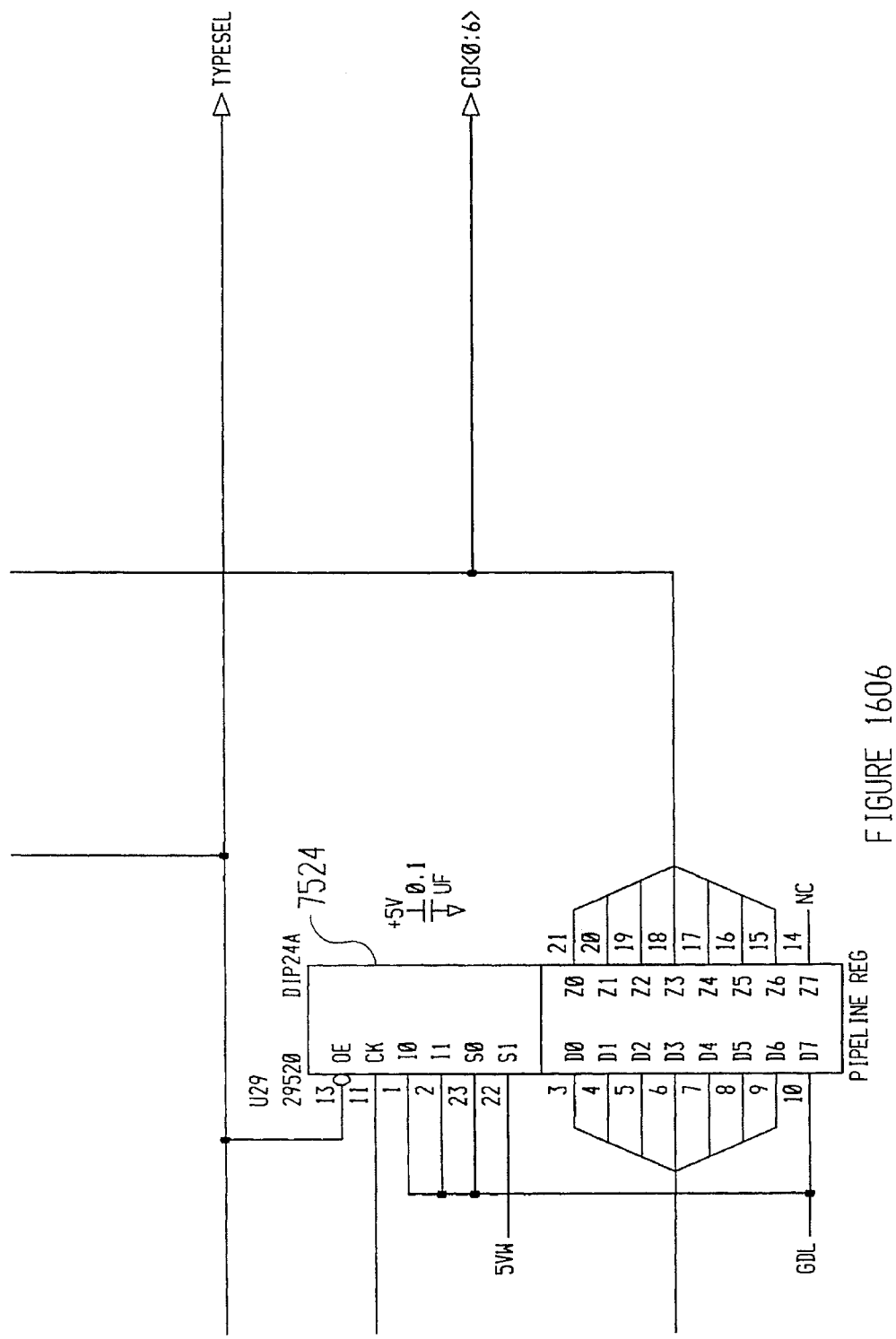
FIGURE 1606

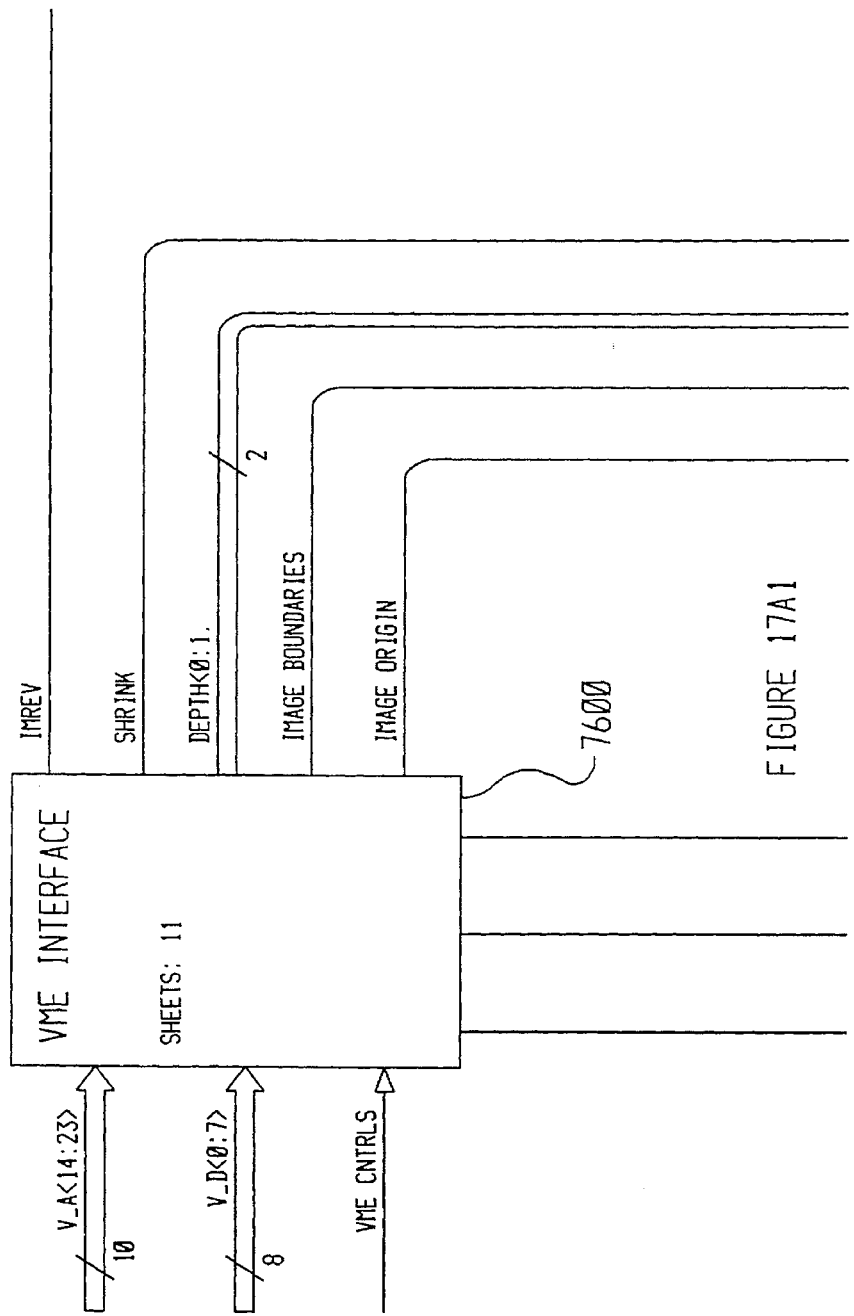

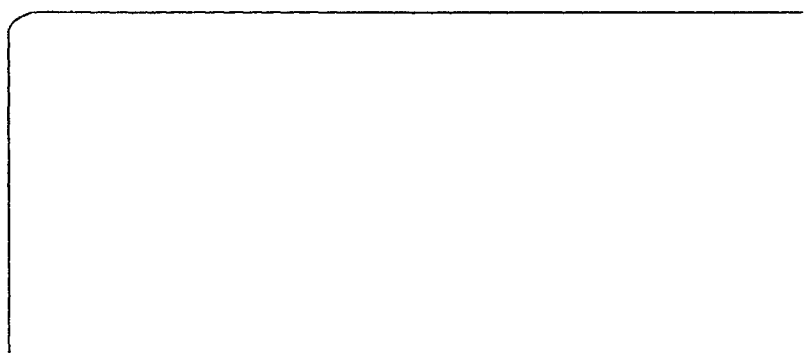

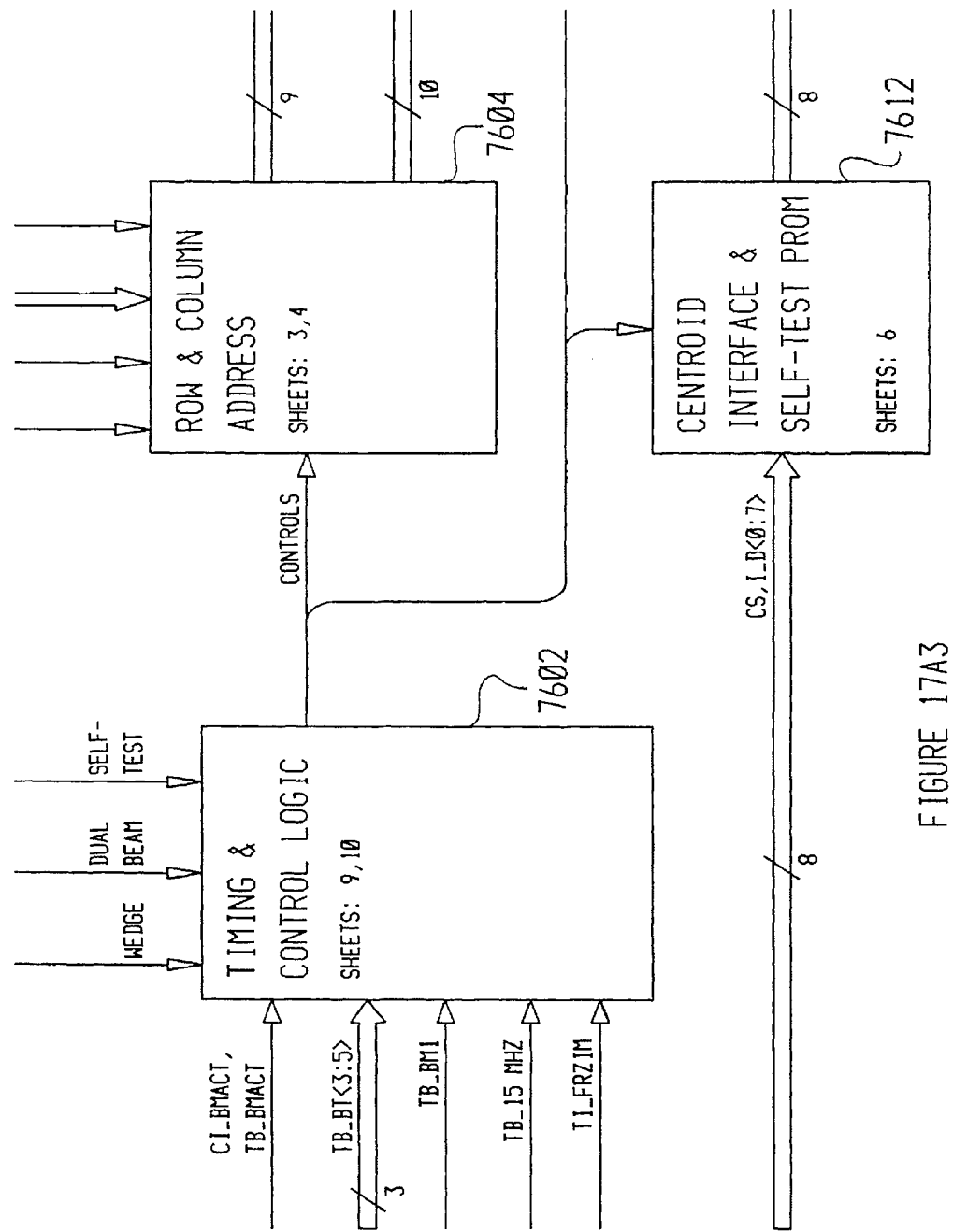
FIGURE 17A3

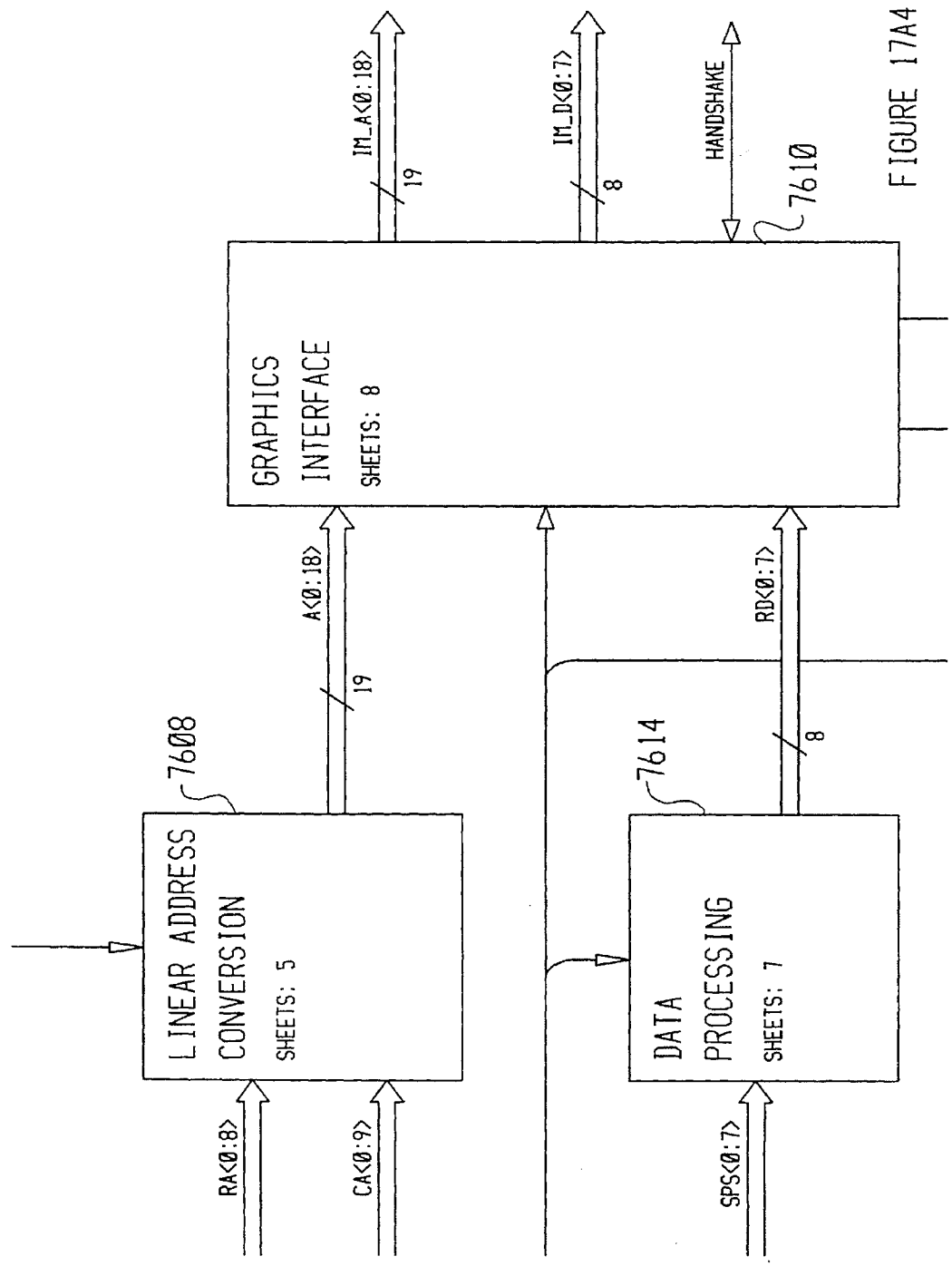
FIGURE 17A4

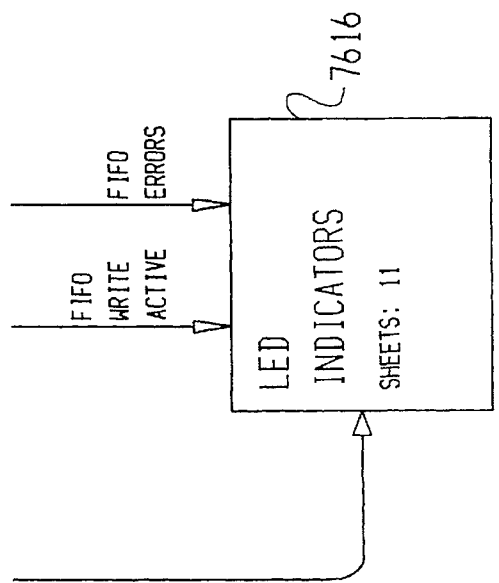
FIGURE 17A5

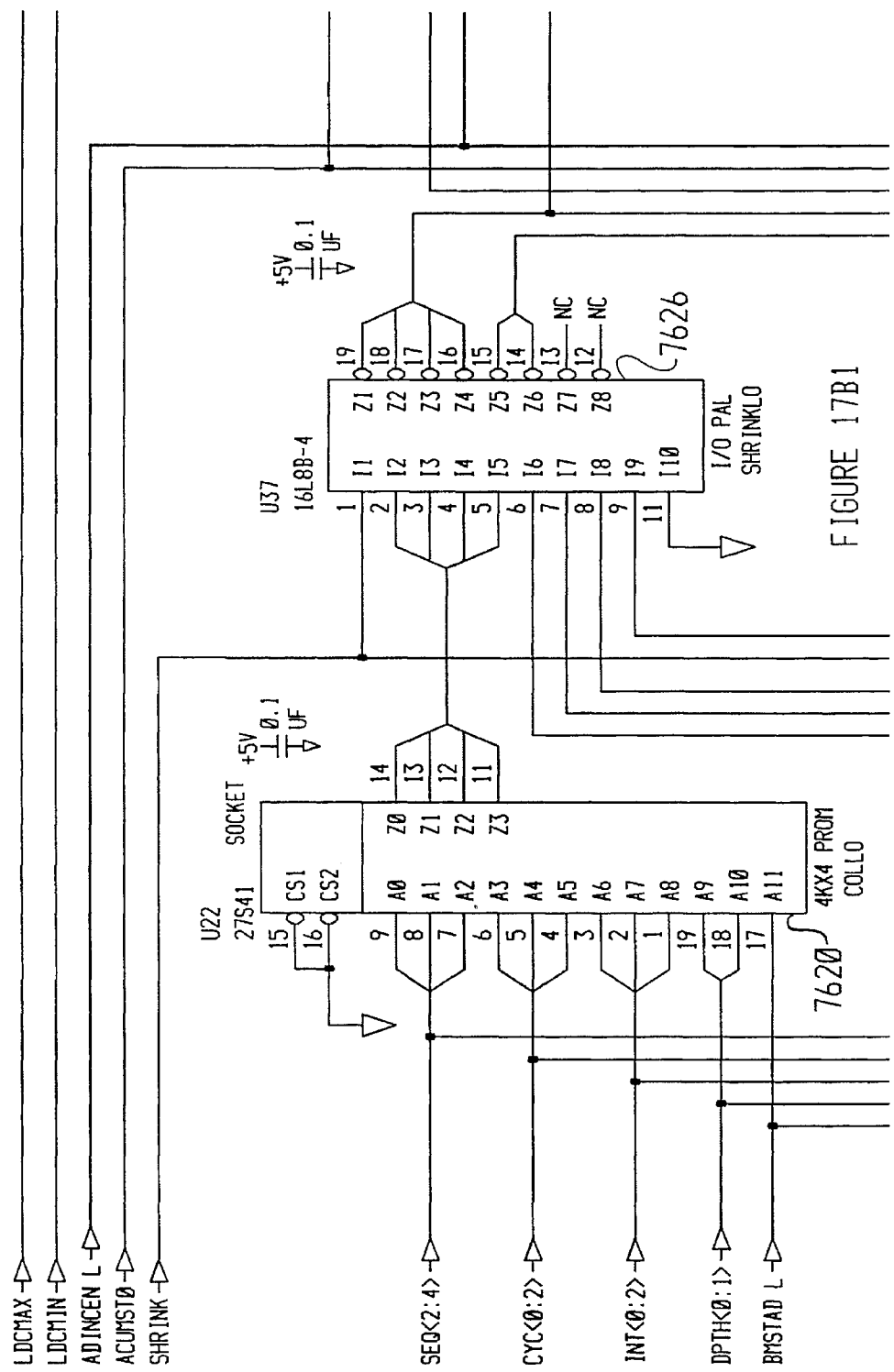

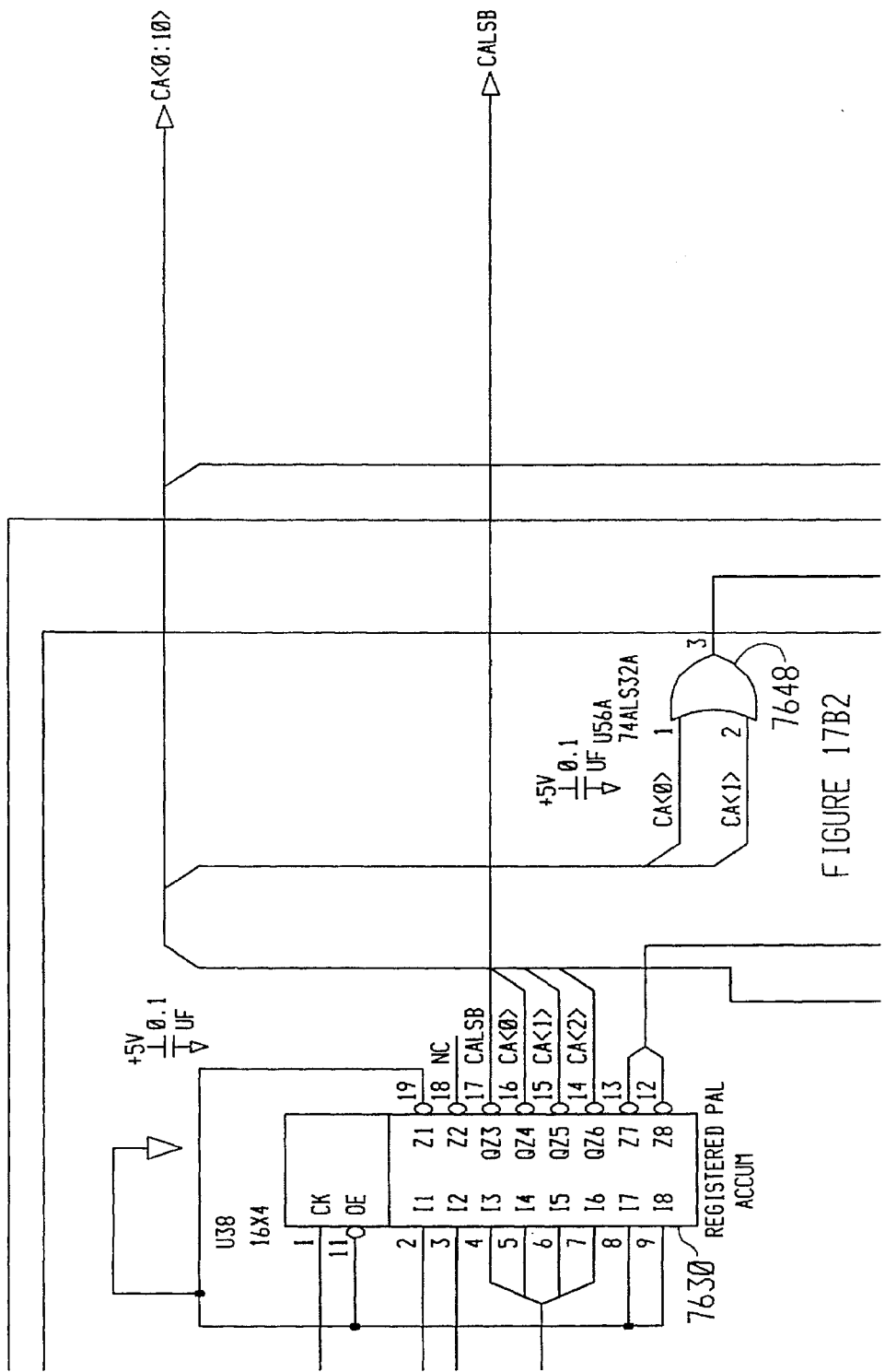
FIGURE 17B2

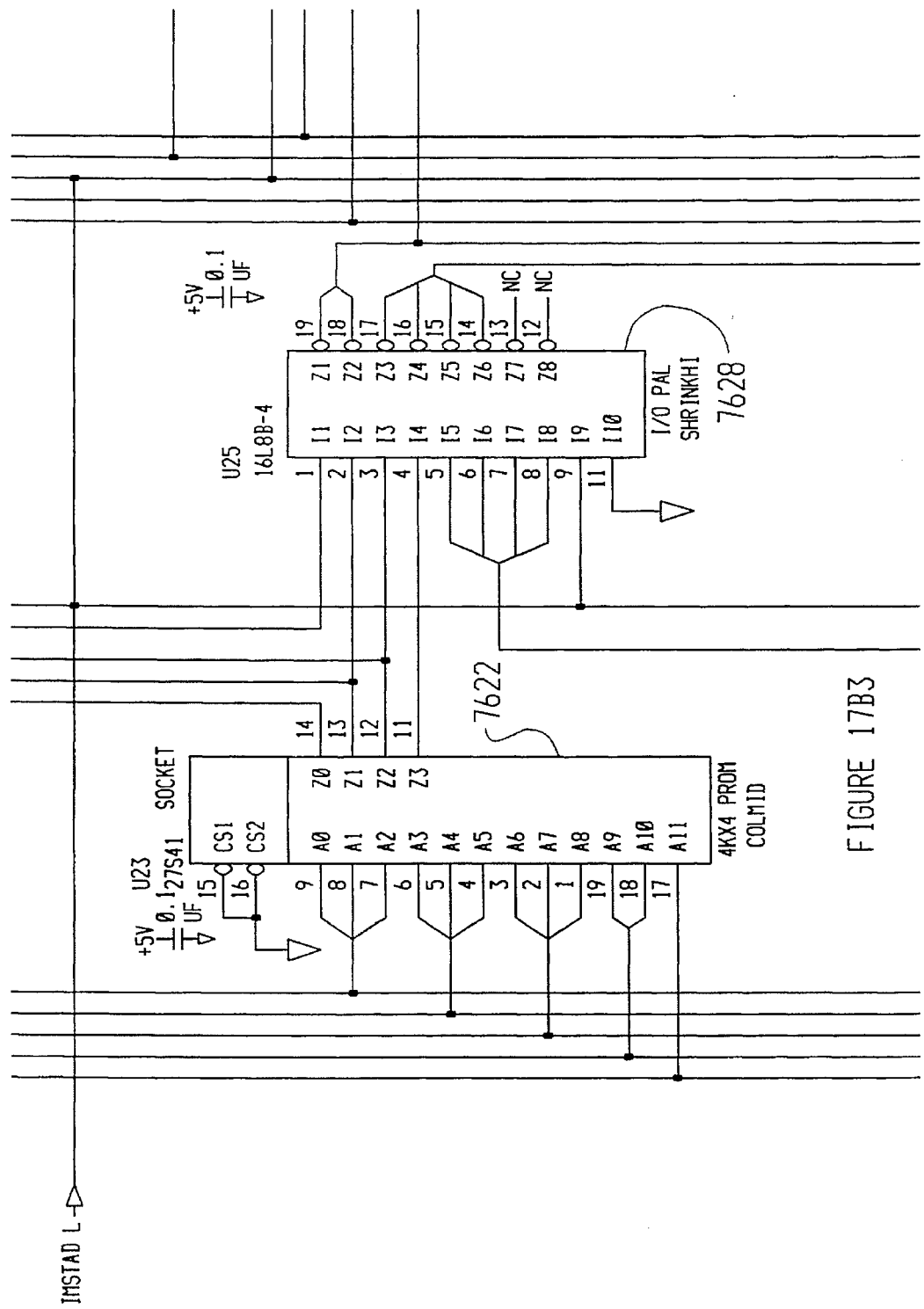
FIGURE 17B3

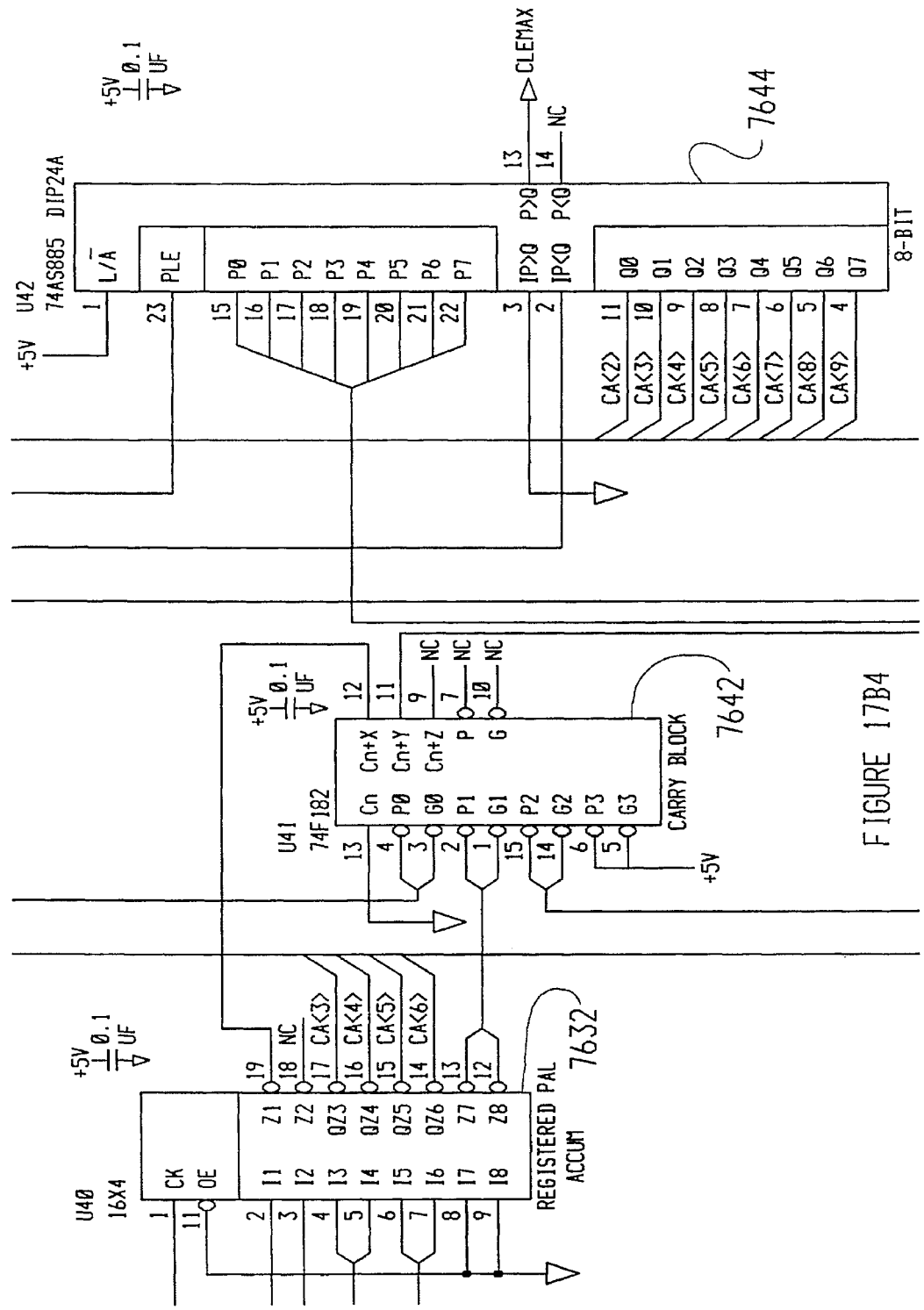
FIGURE 17B4

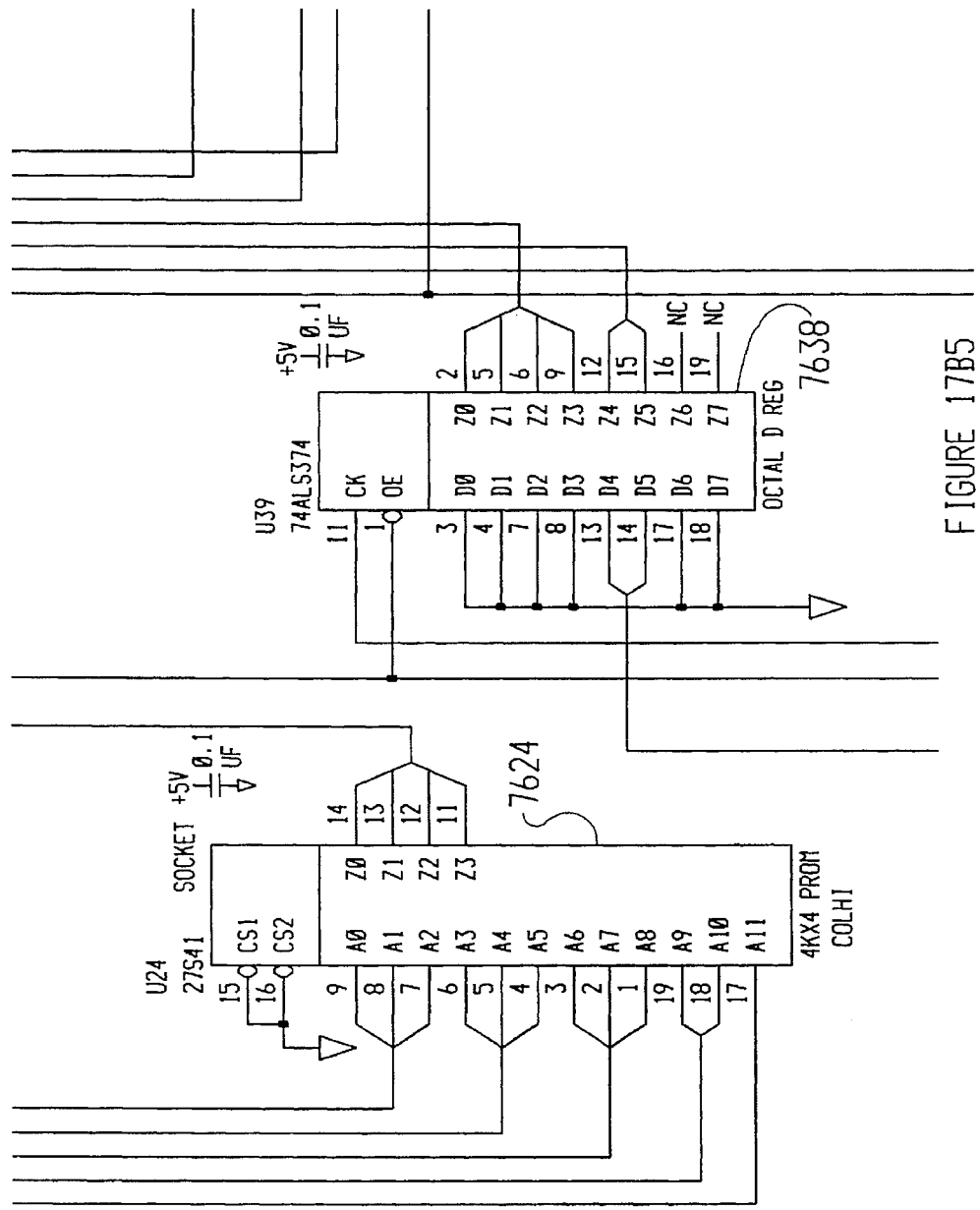

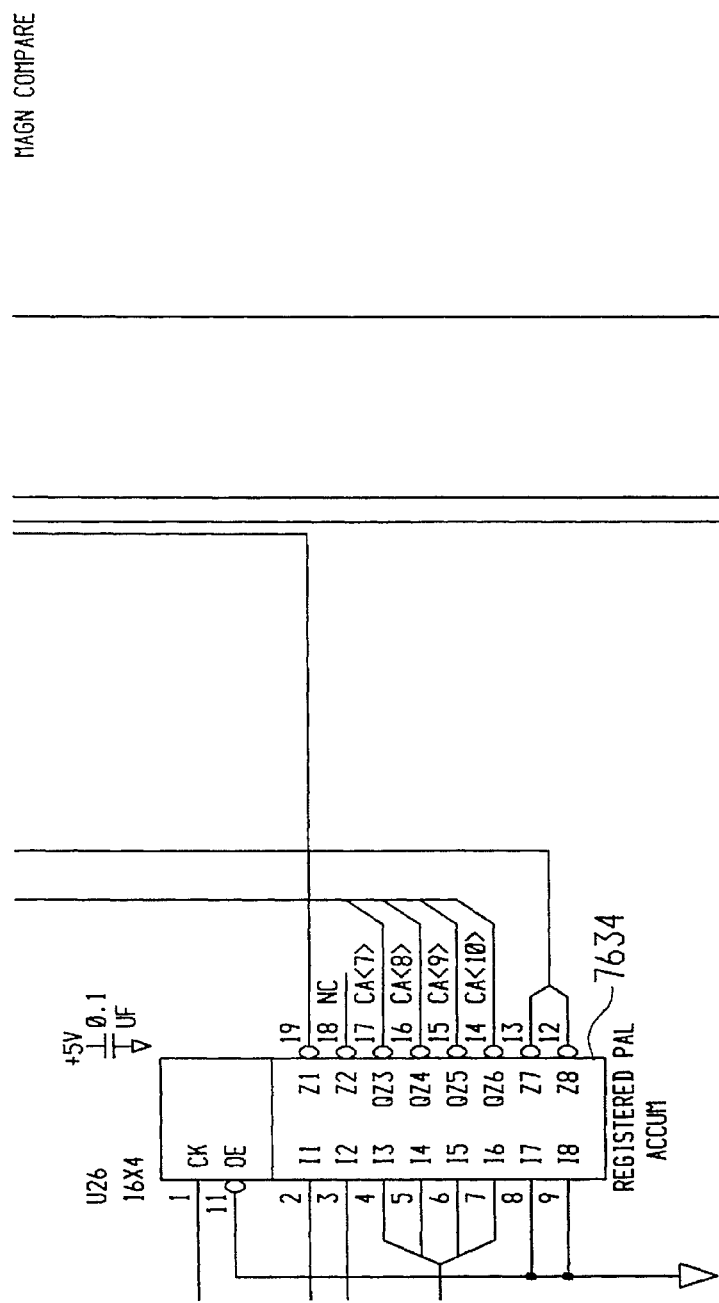
FIGURE 17B6

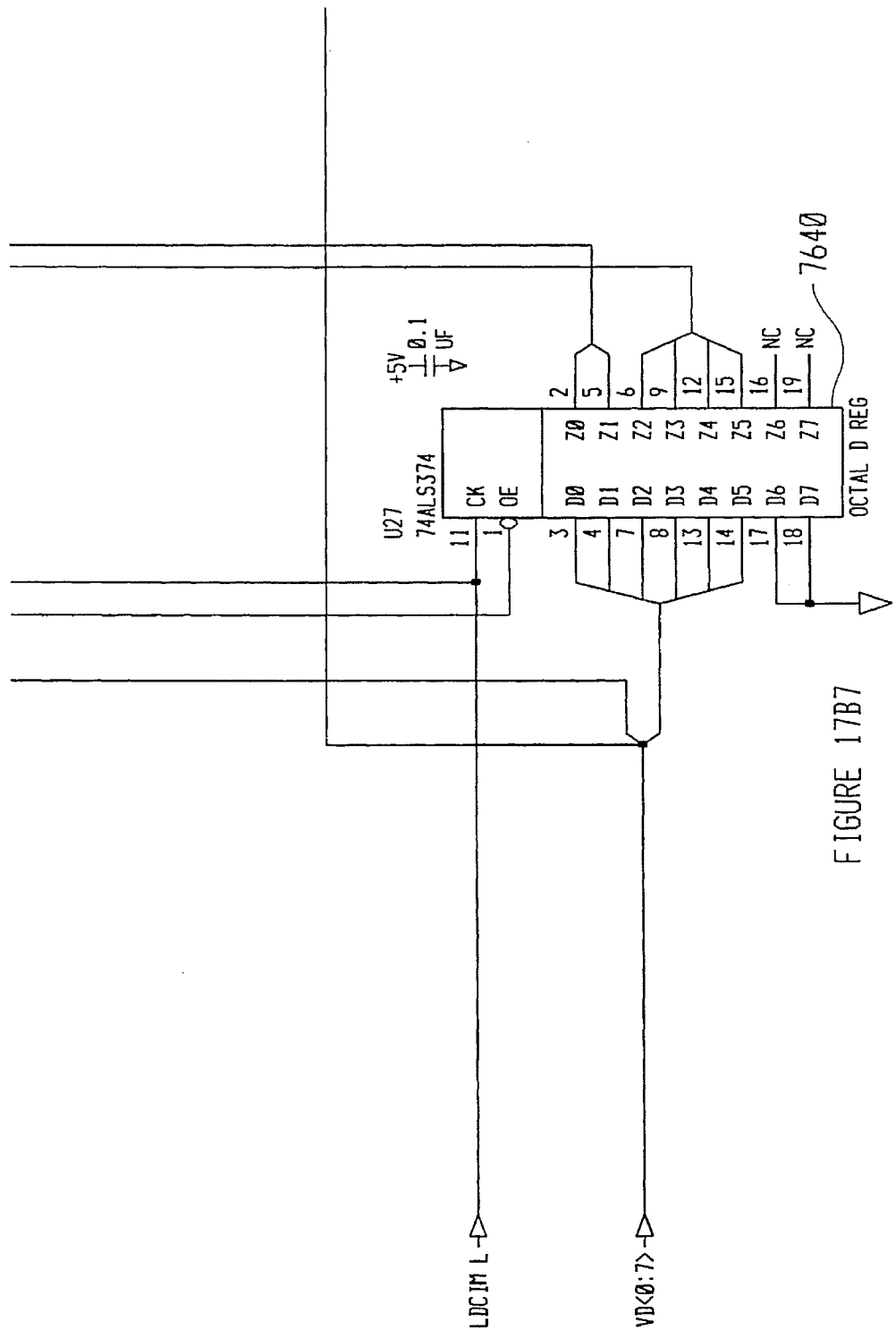
FIGURE 17B7

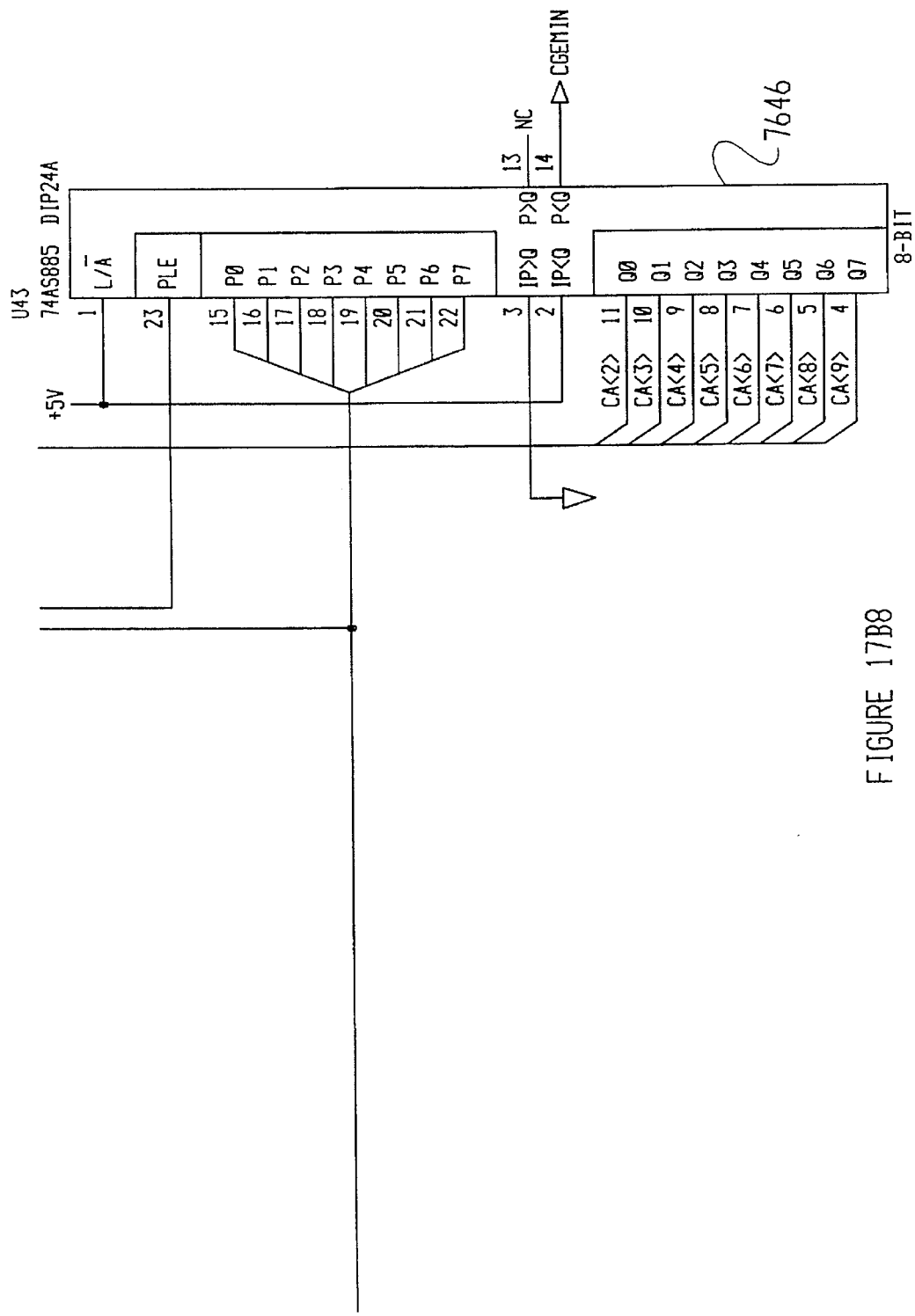
FIGURE 17B8

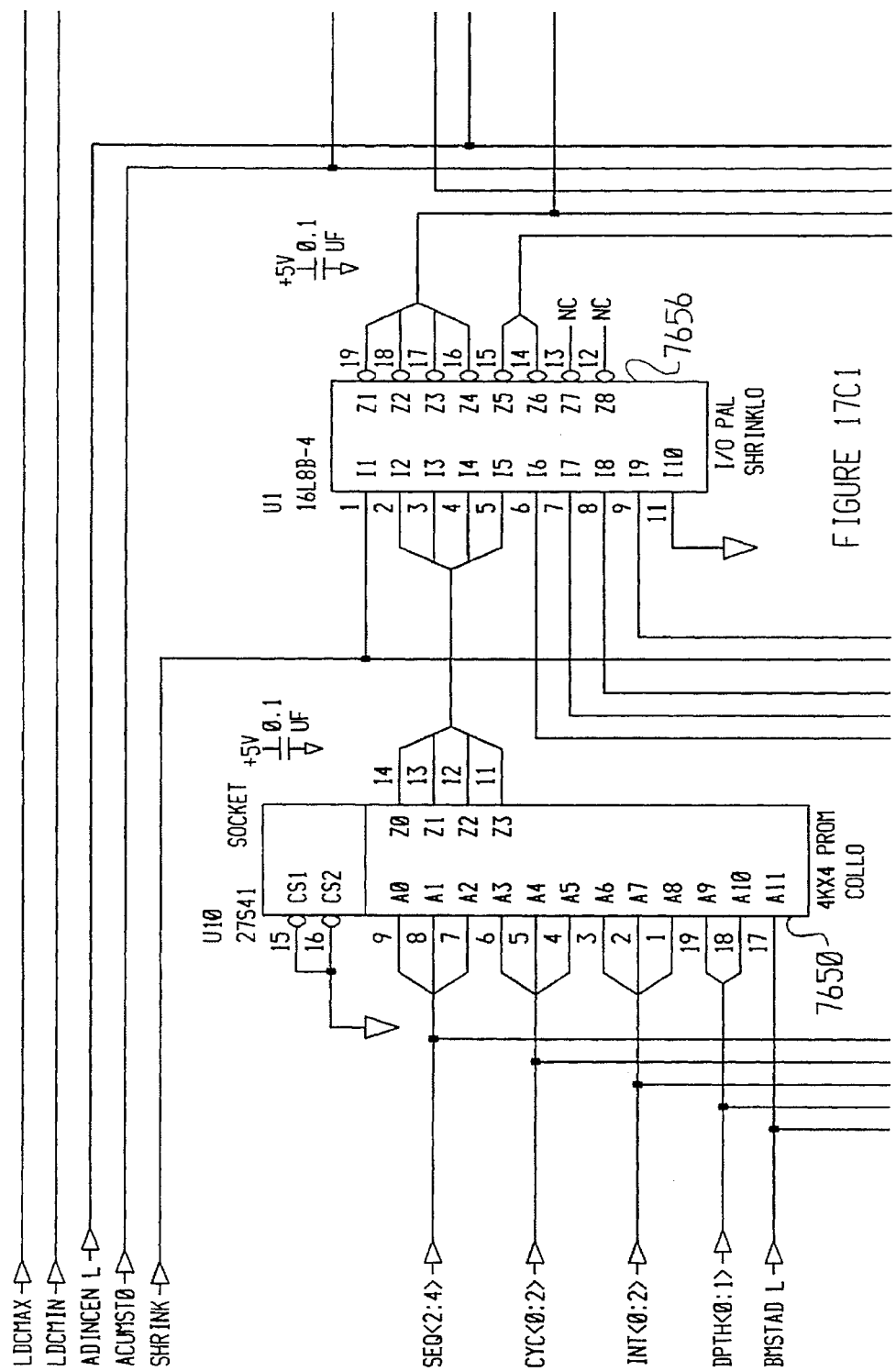

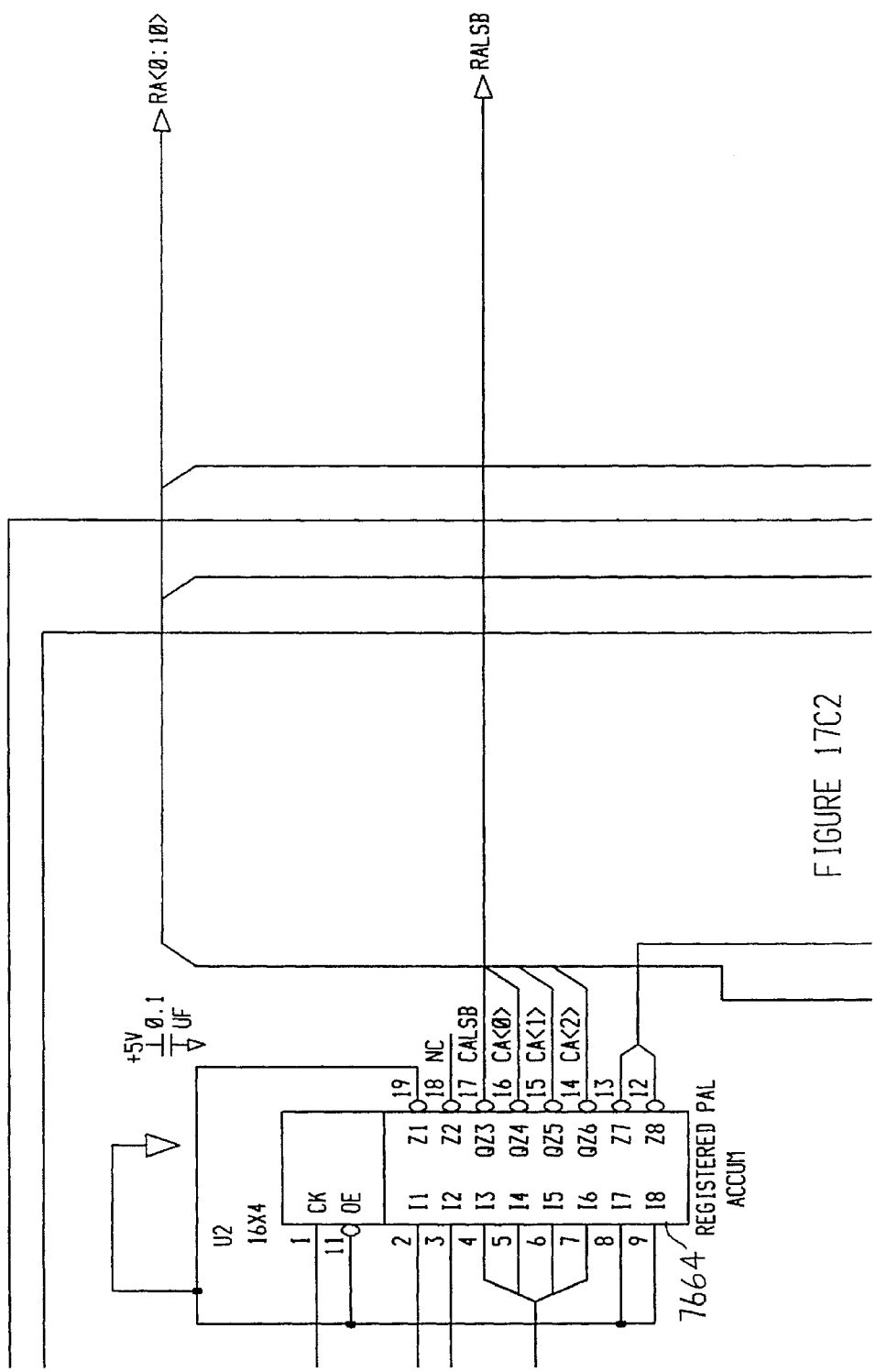
FIGURE 17C2

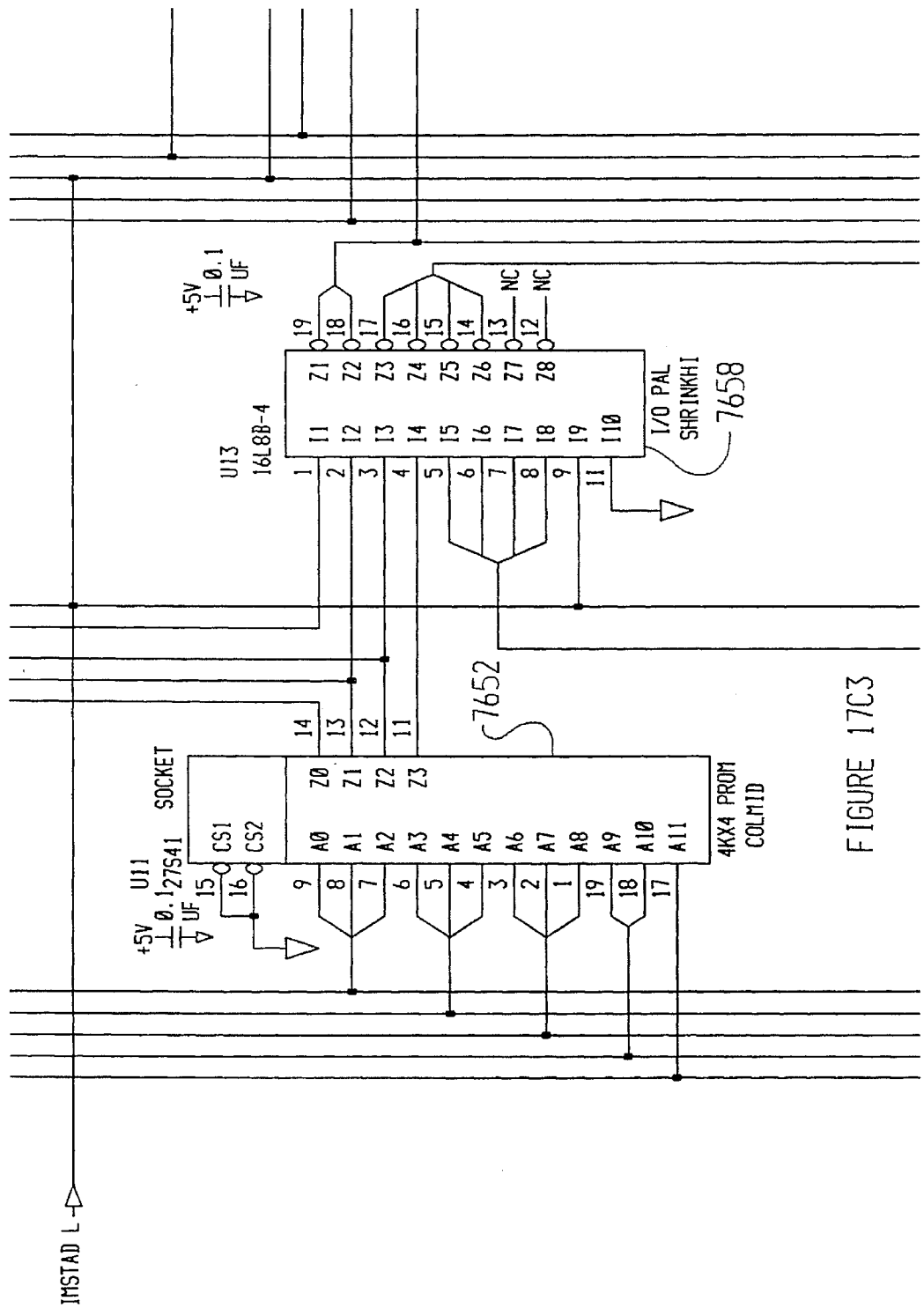
FIGURE 17C3

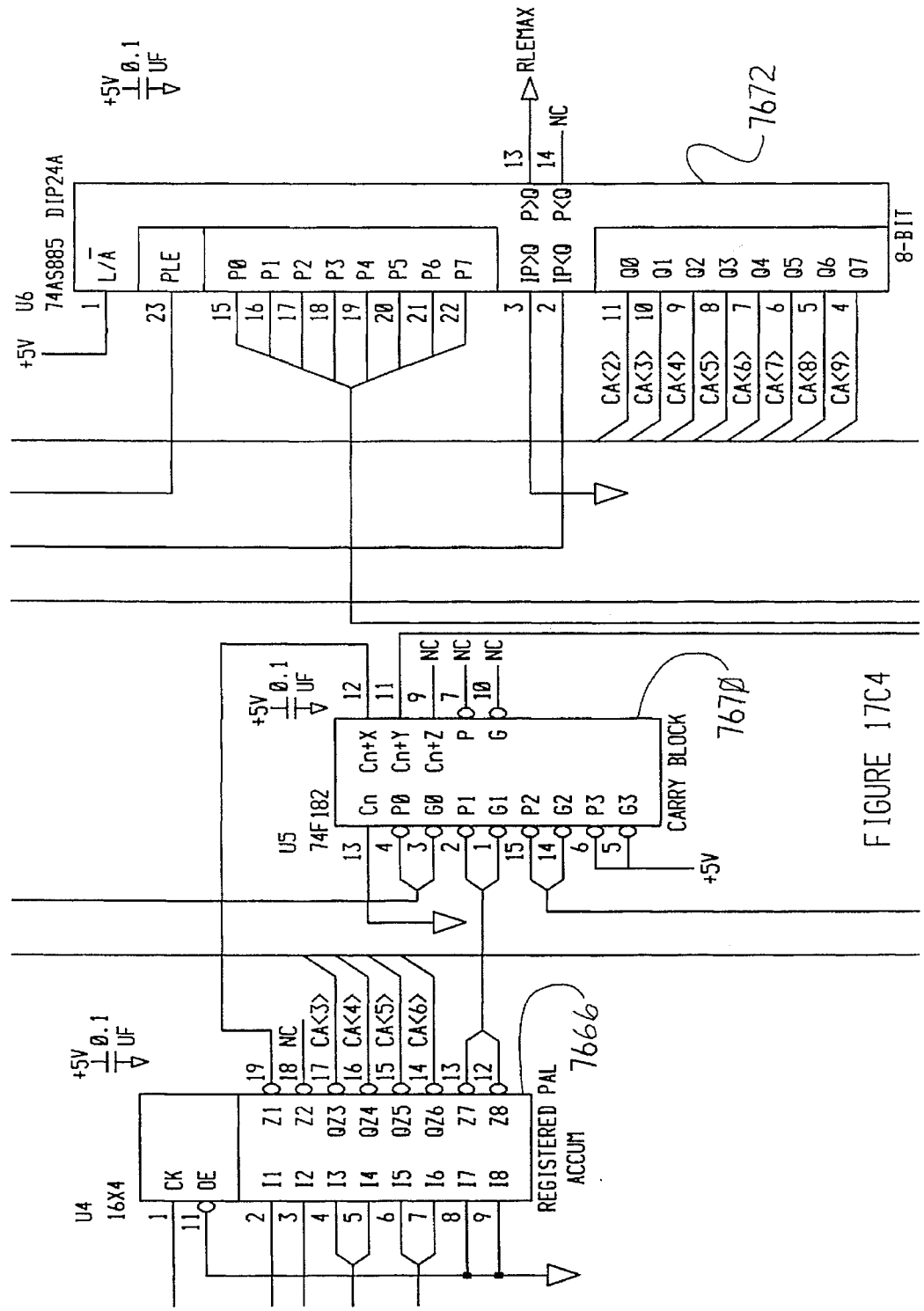
FIGURE 17C4

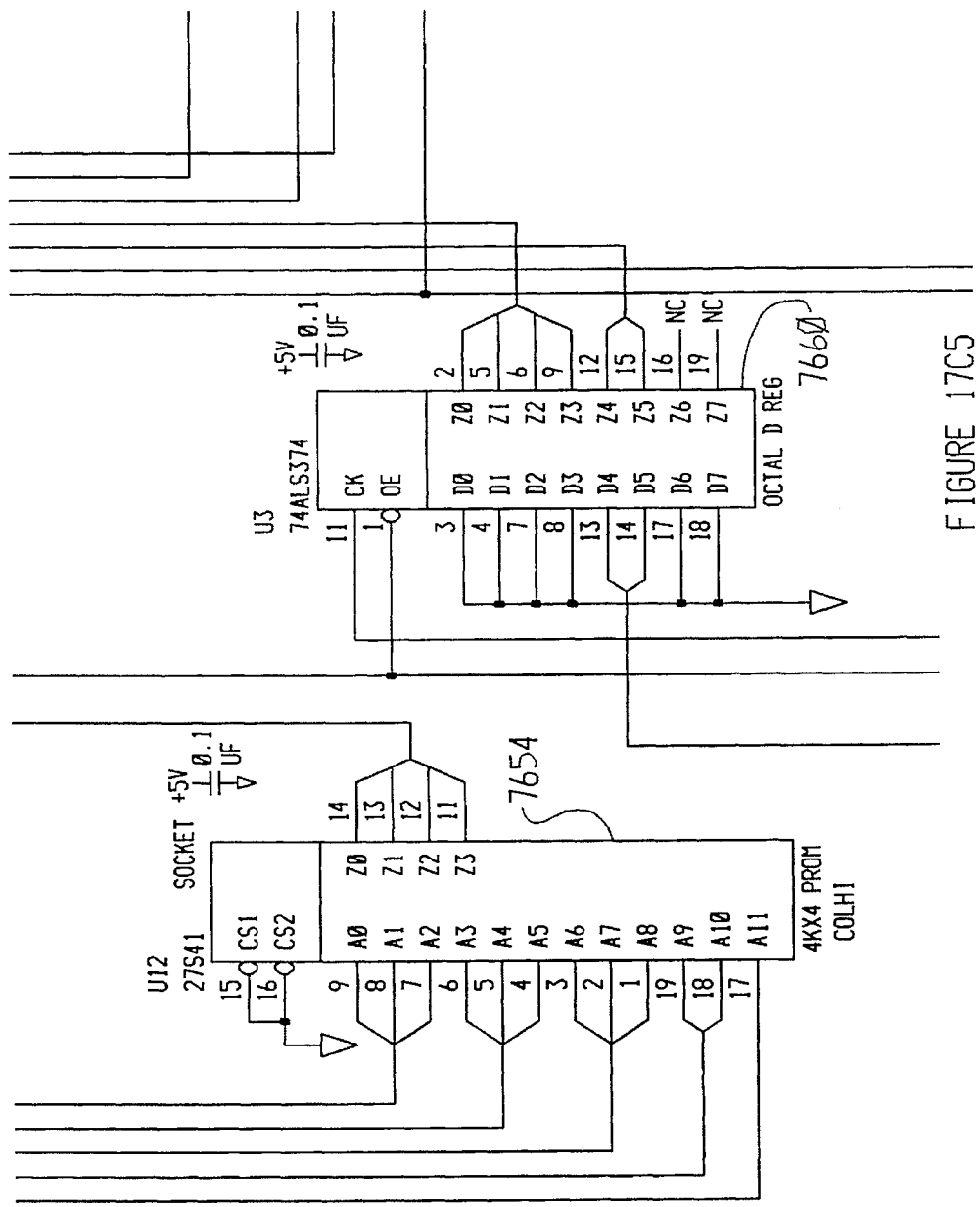

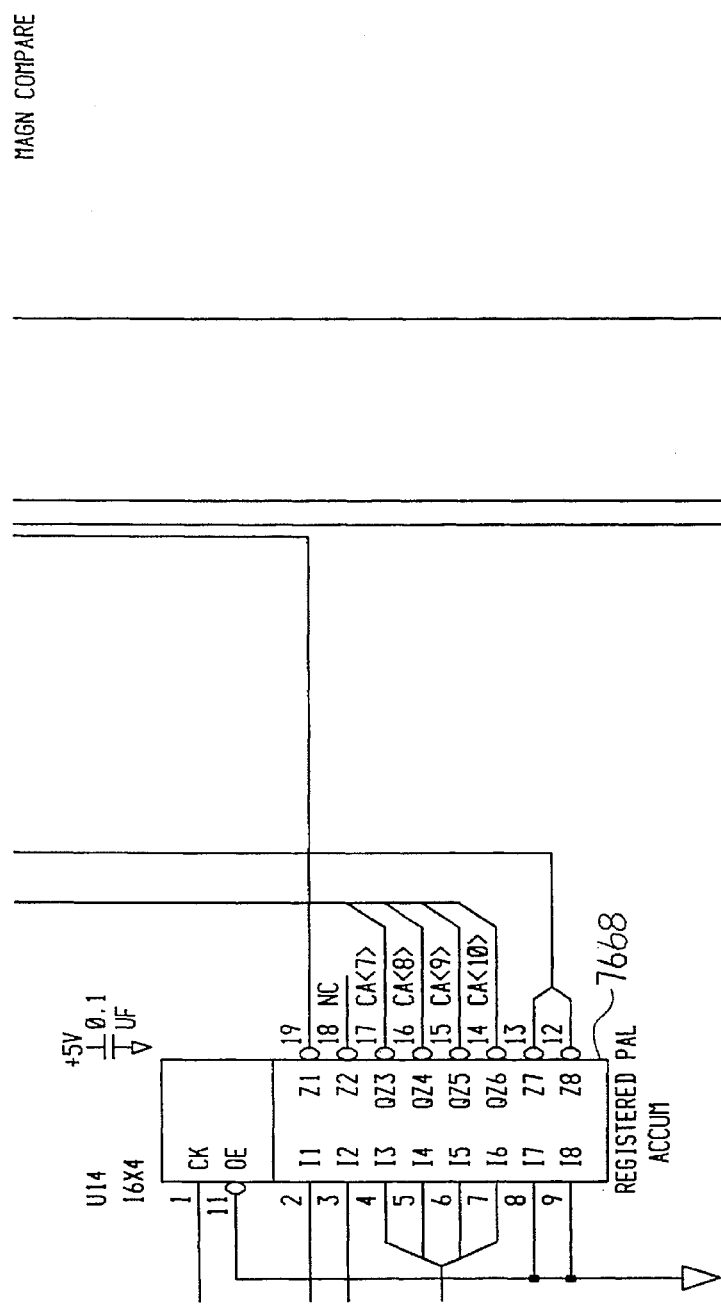
FIGURE 17C6

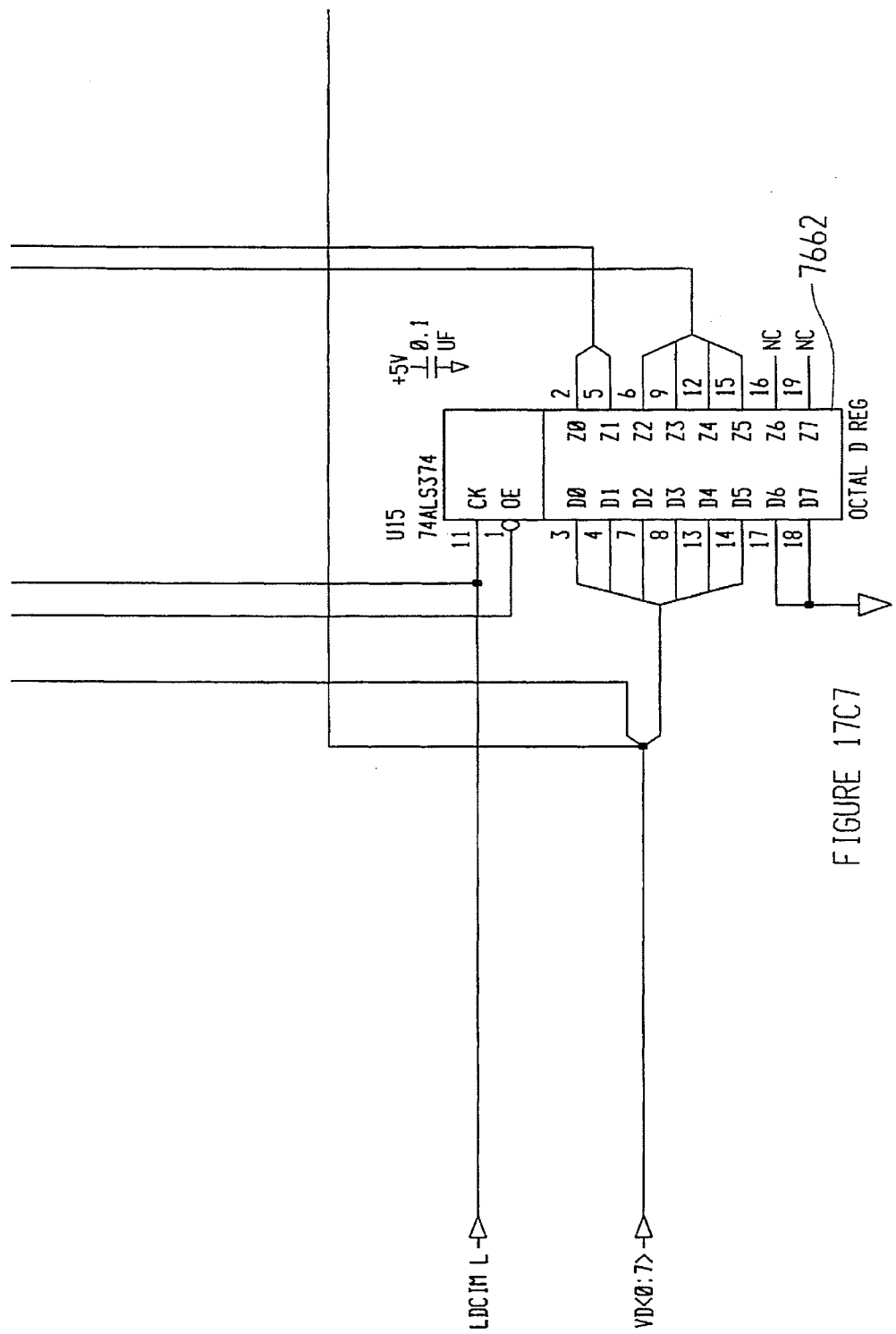
FIGURE 17C7

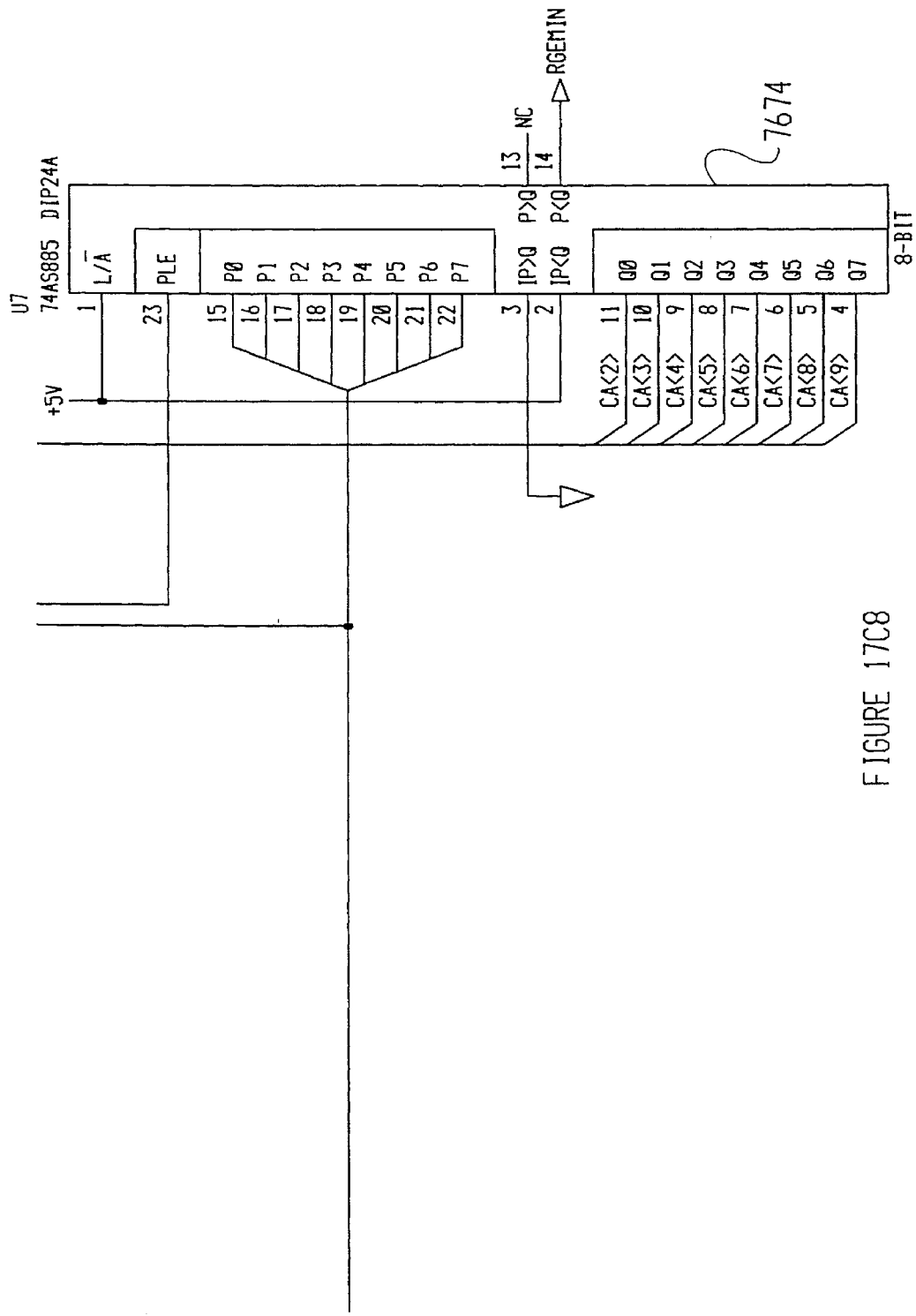
FIGURE 17C8

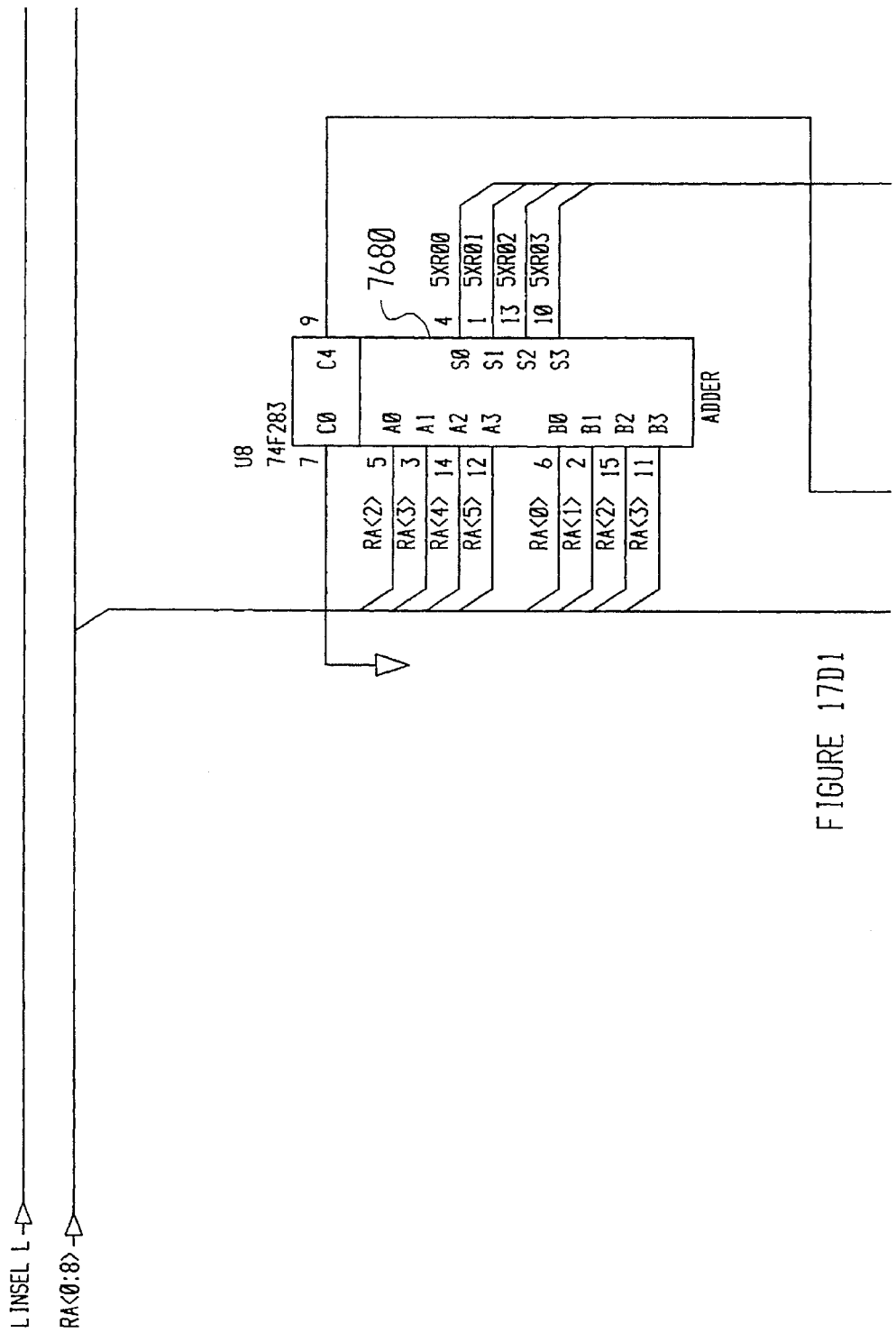
FIGURE 17D1

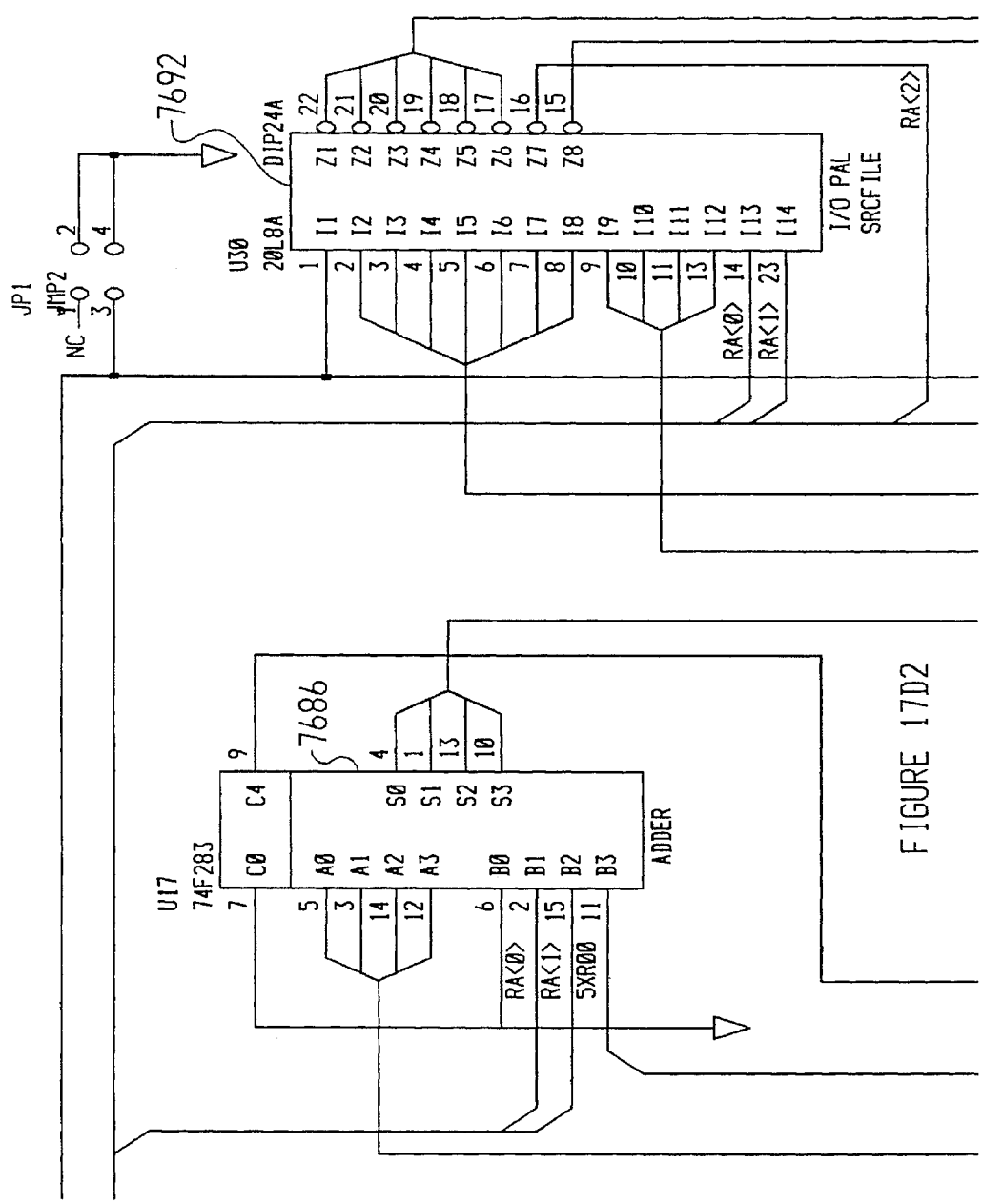
FIGURE 17D2

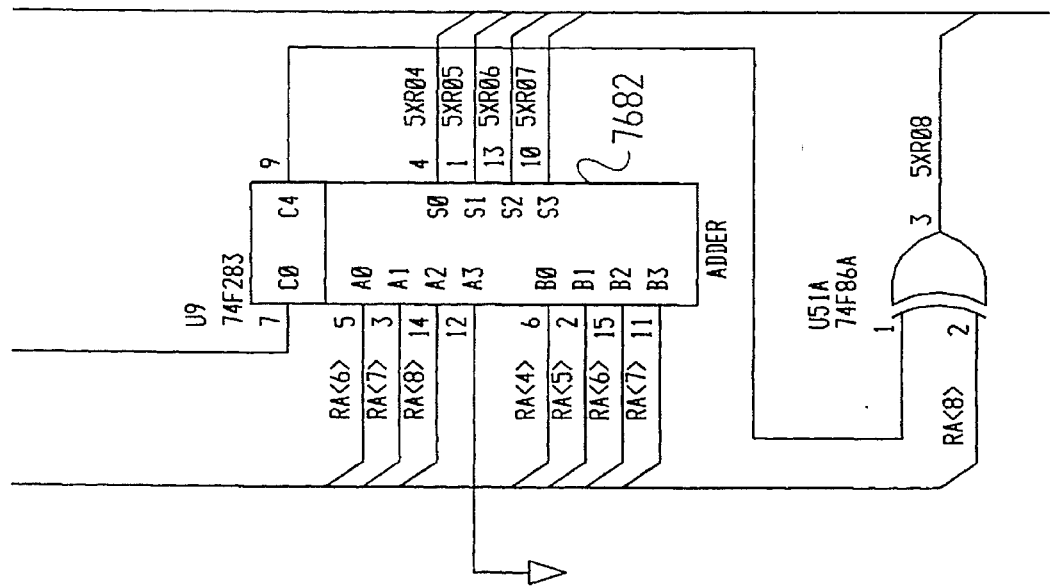
FIGURE 17D3

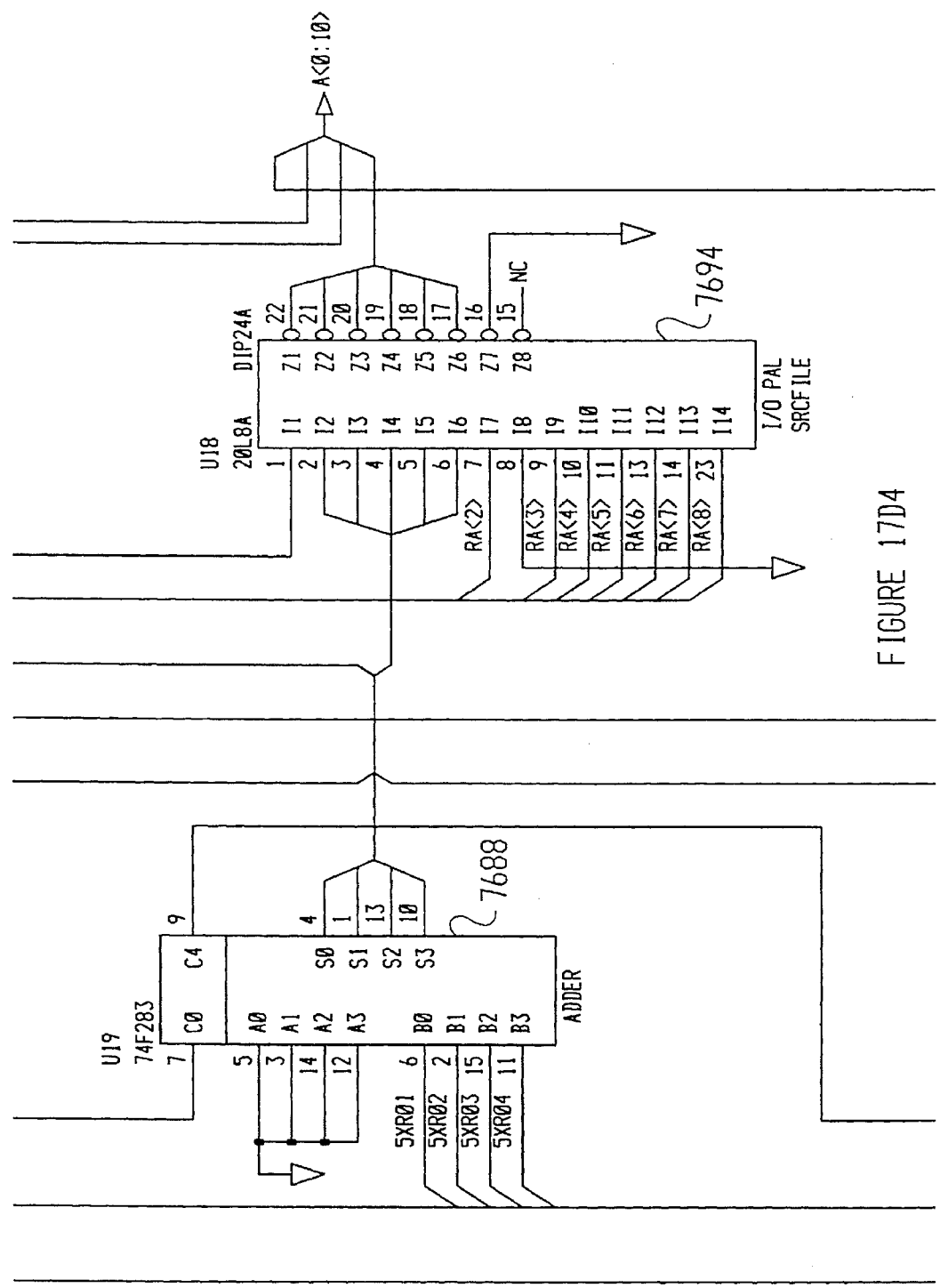
FIGURE 17D4

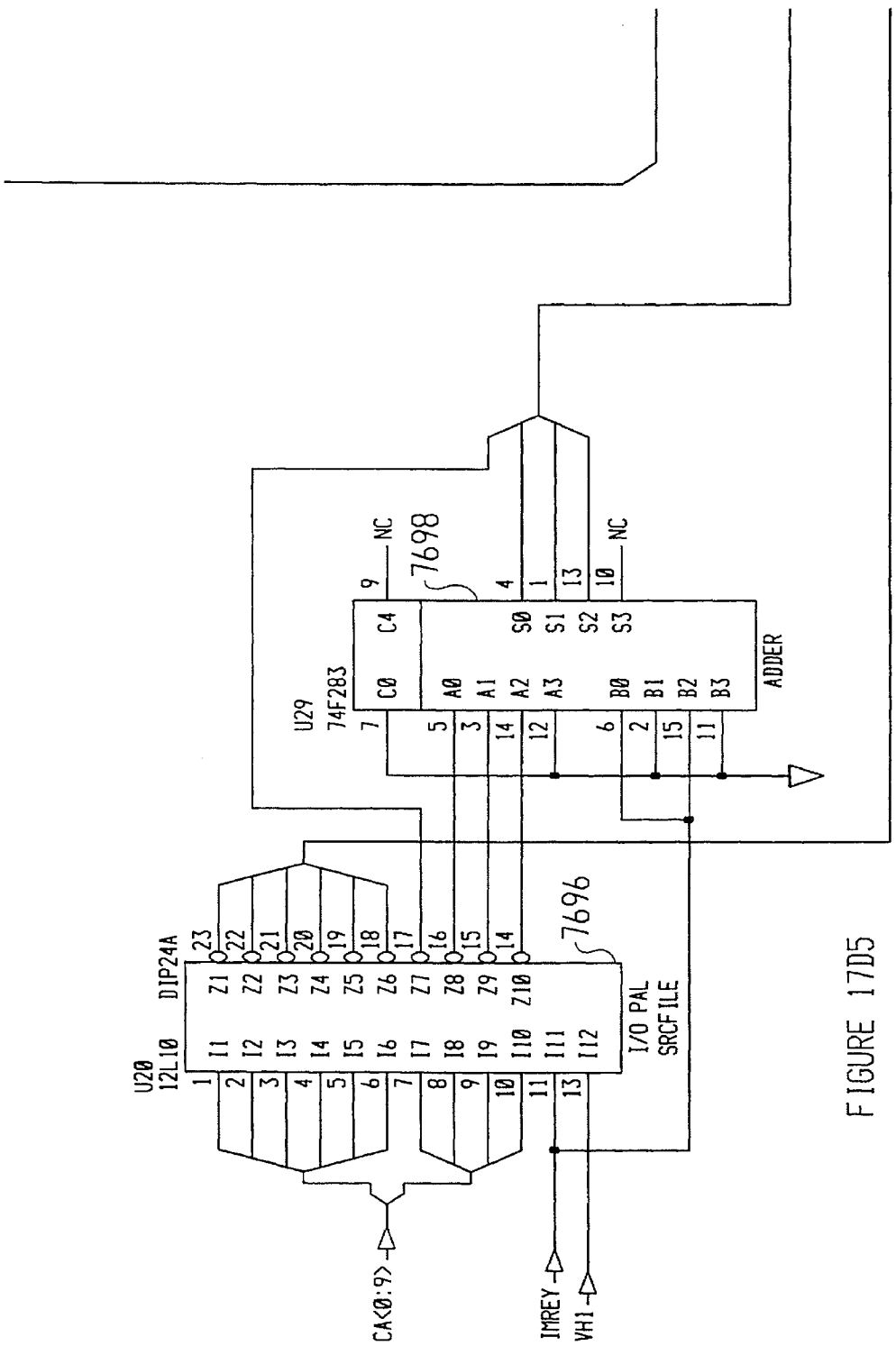
FIGURE 17D5

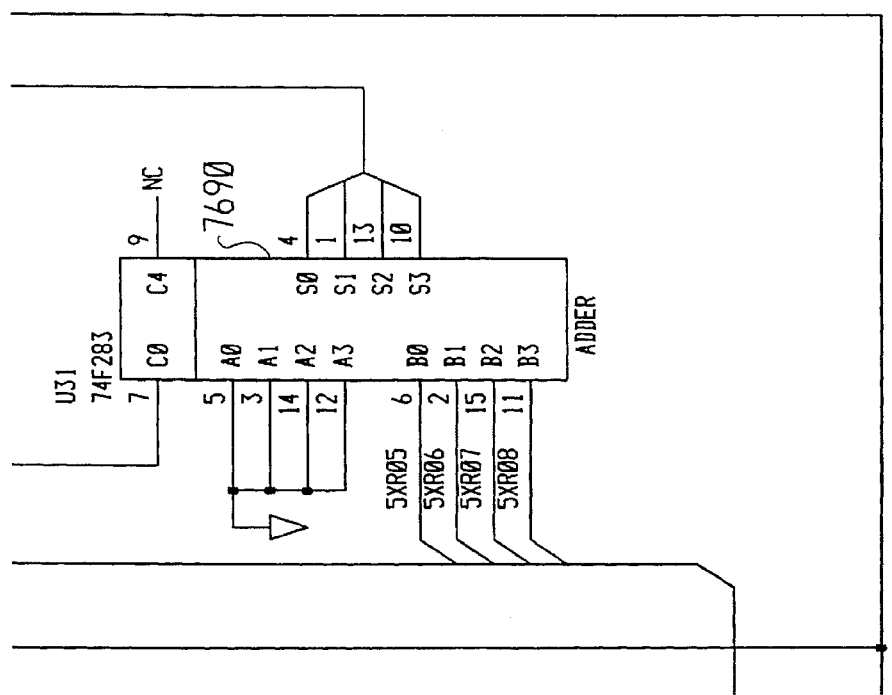
FIGURE 17D6

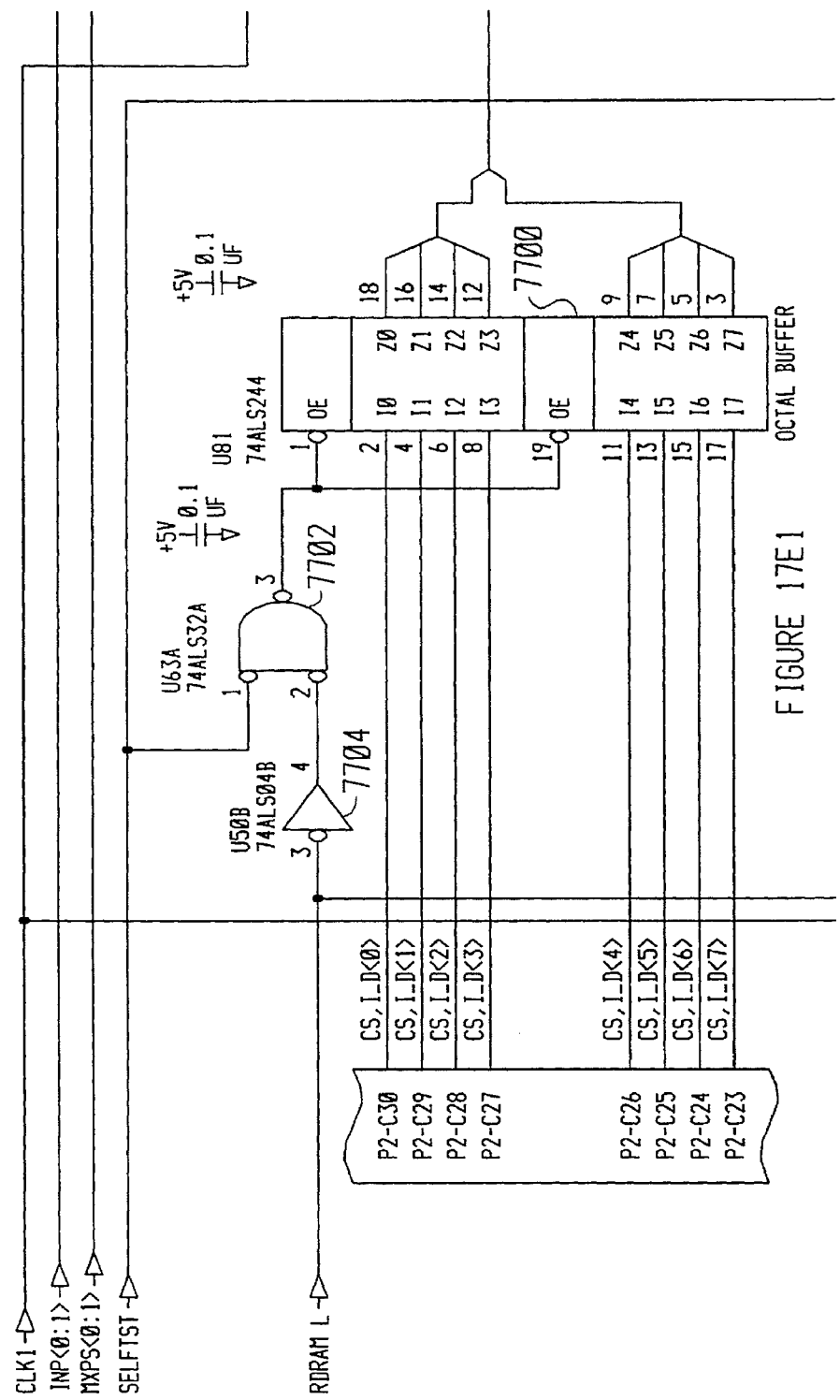
FIGURE 17E1

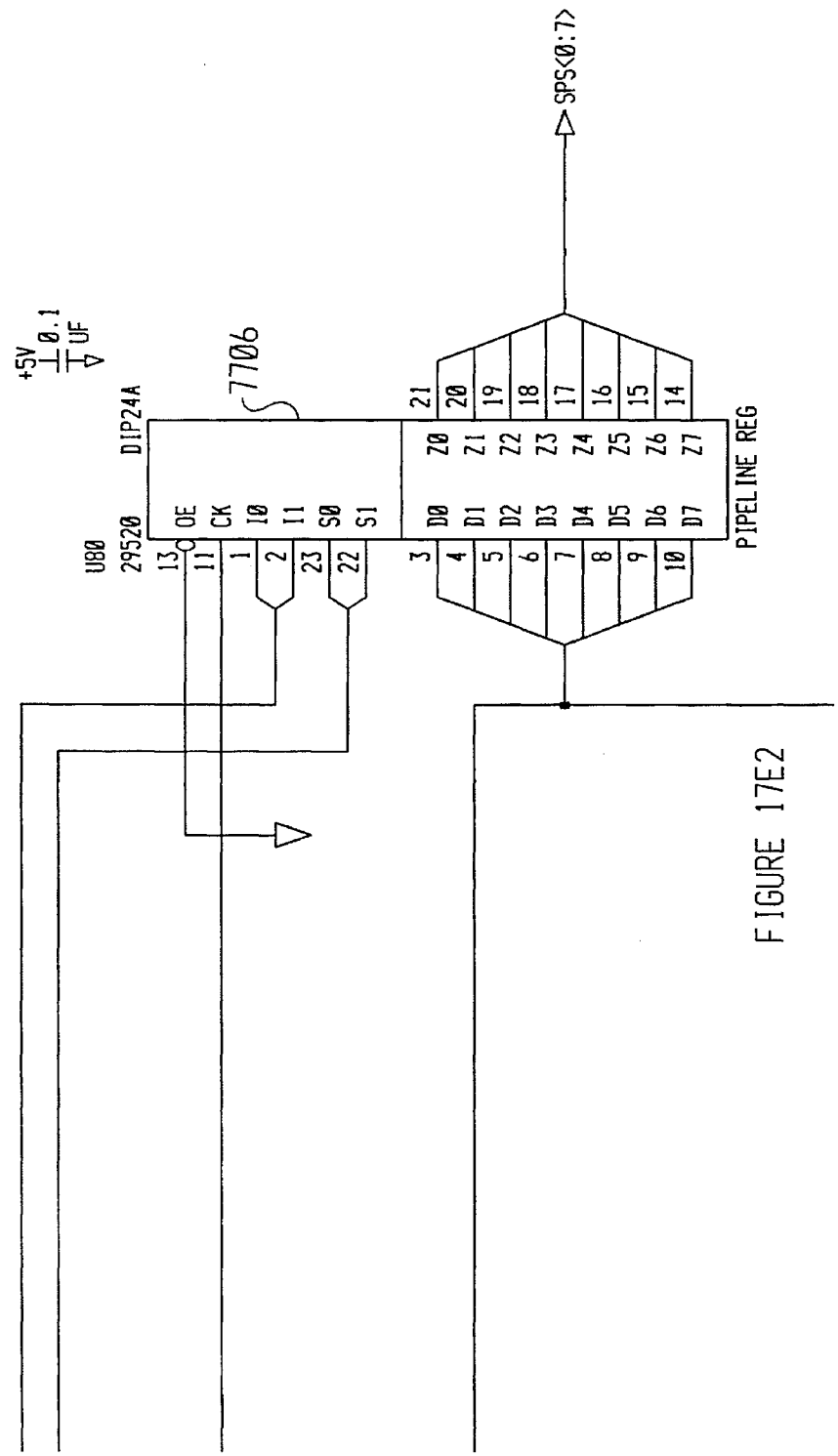
FIGURE 17E2

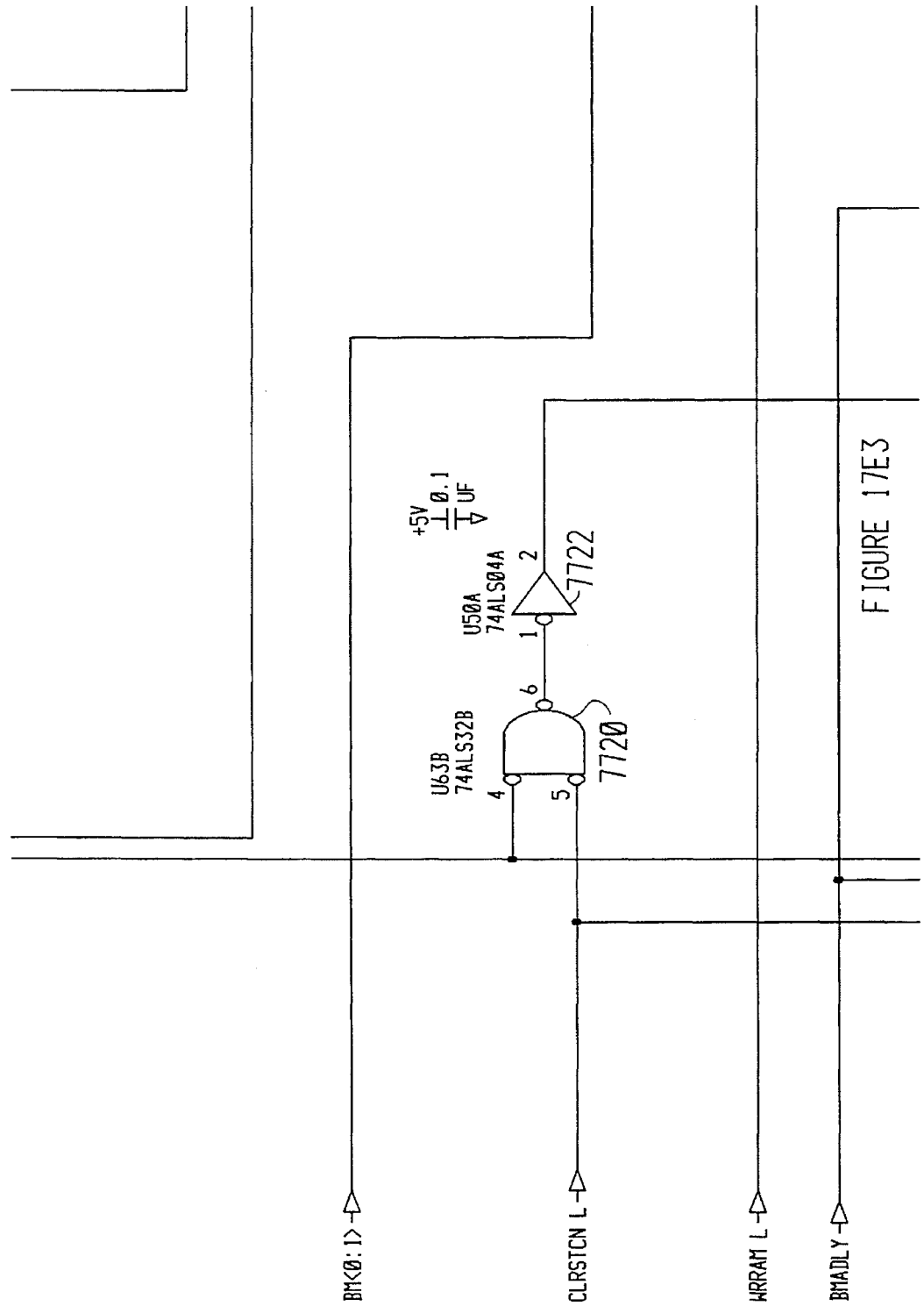

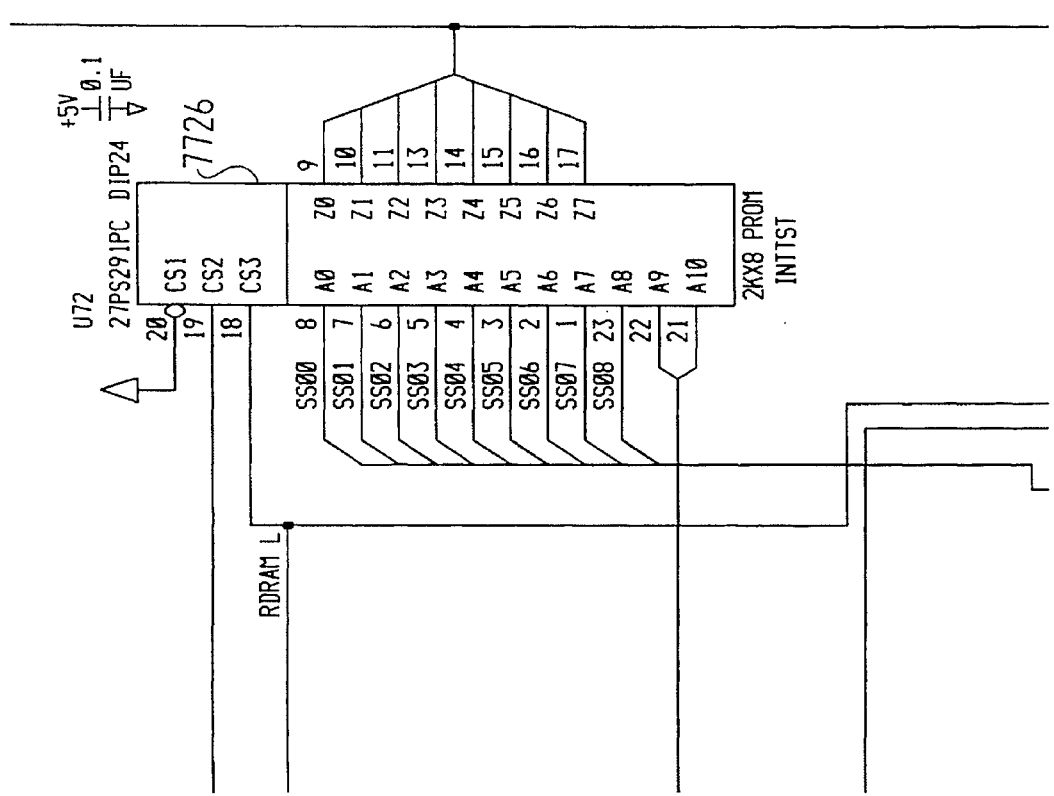
FIGURE 17E4

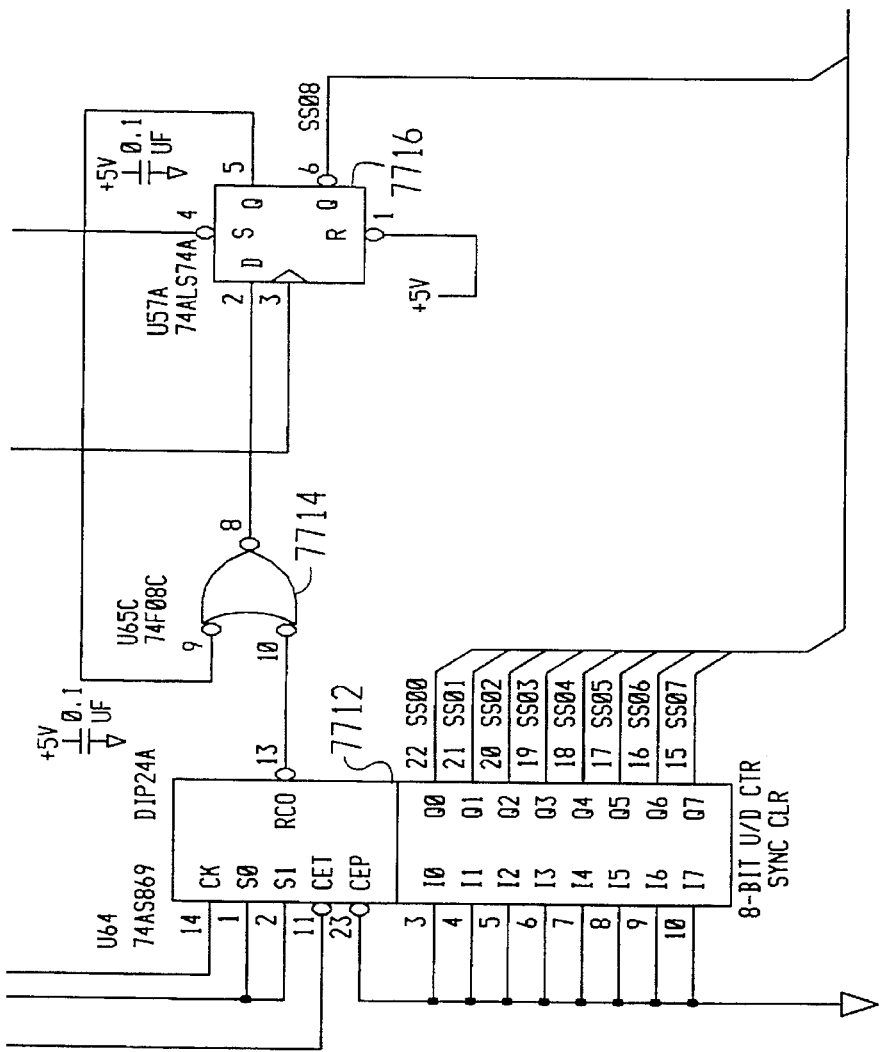
FIGURE 17E5

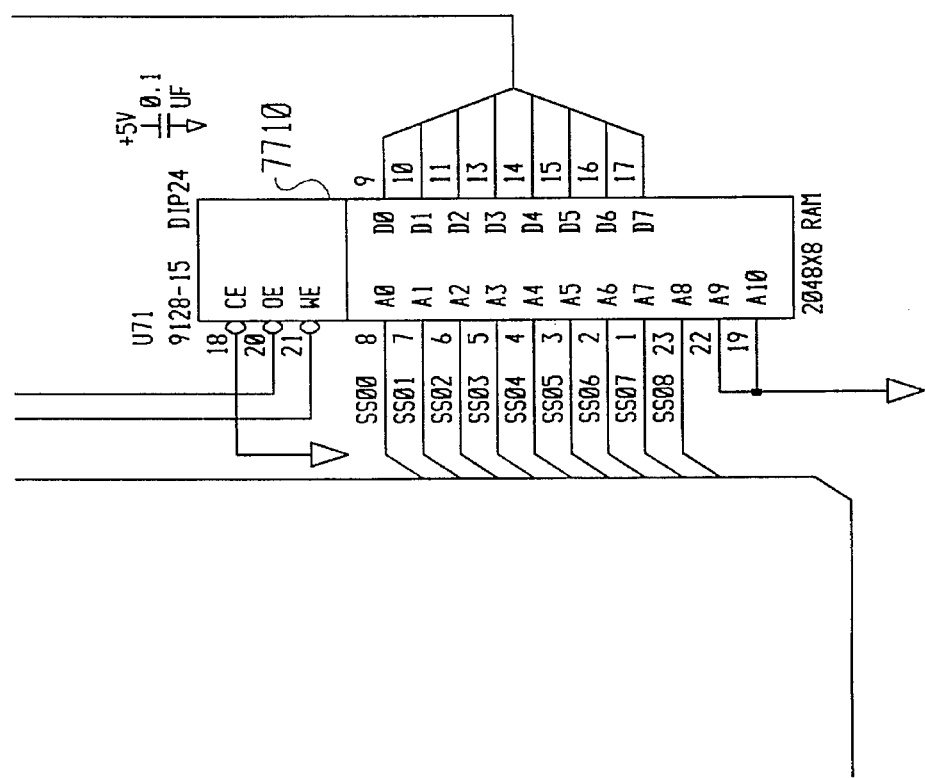
FIGURE 17E6

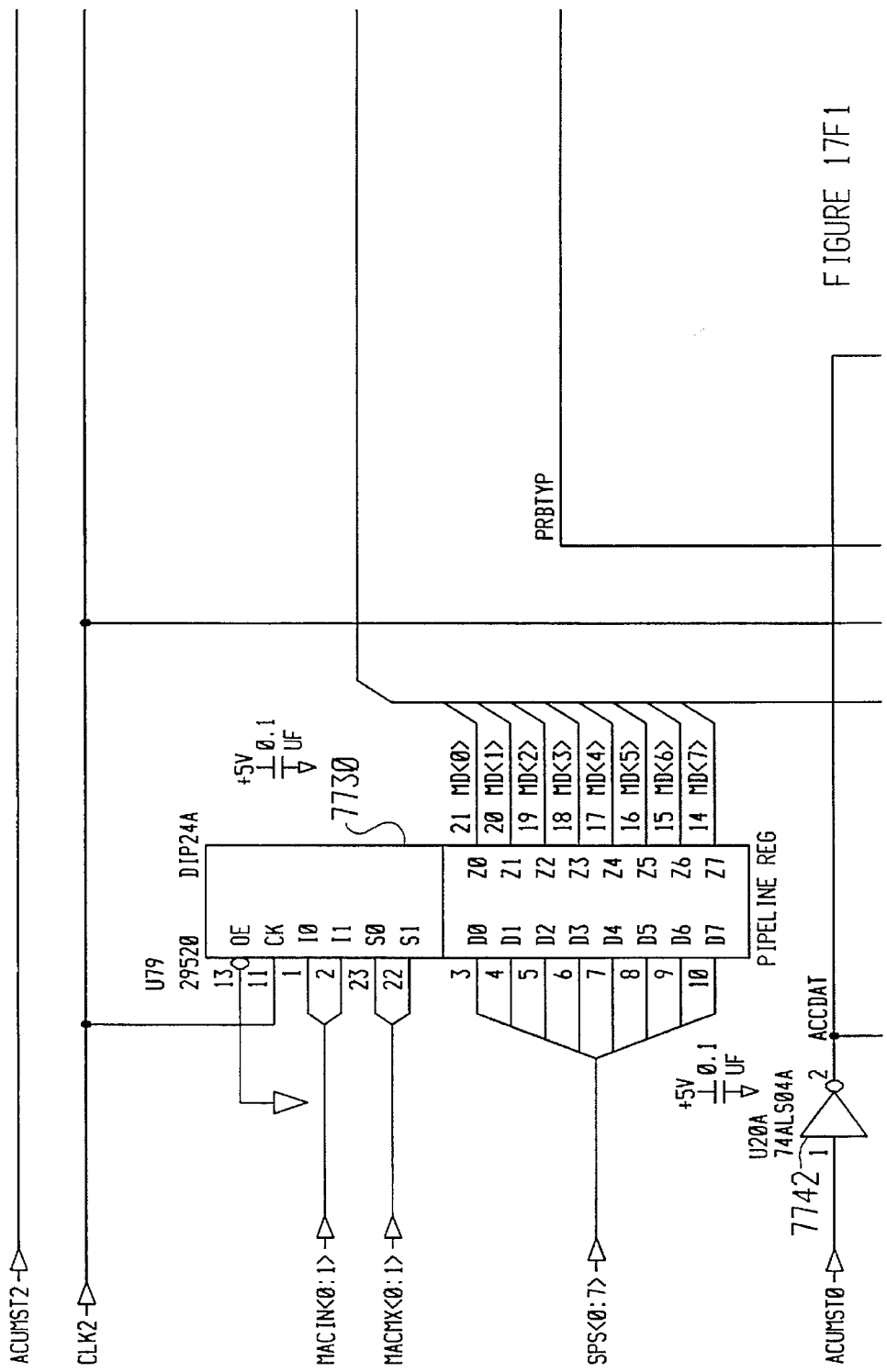
FIGURE 17F1

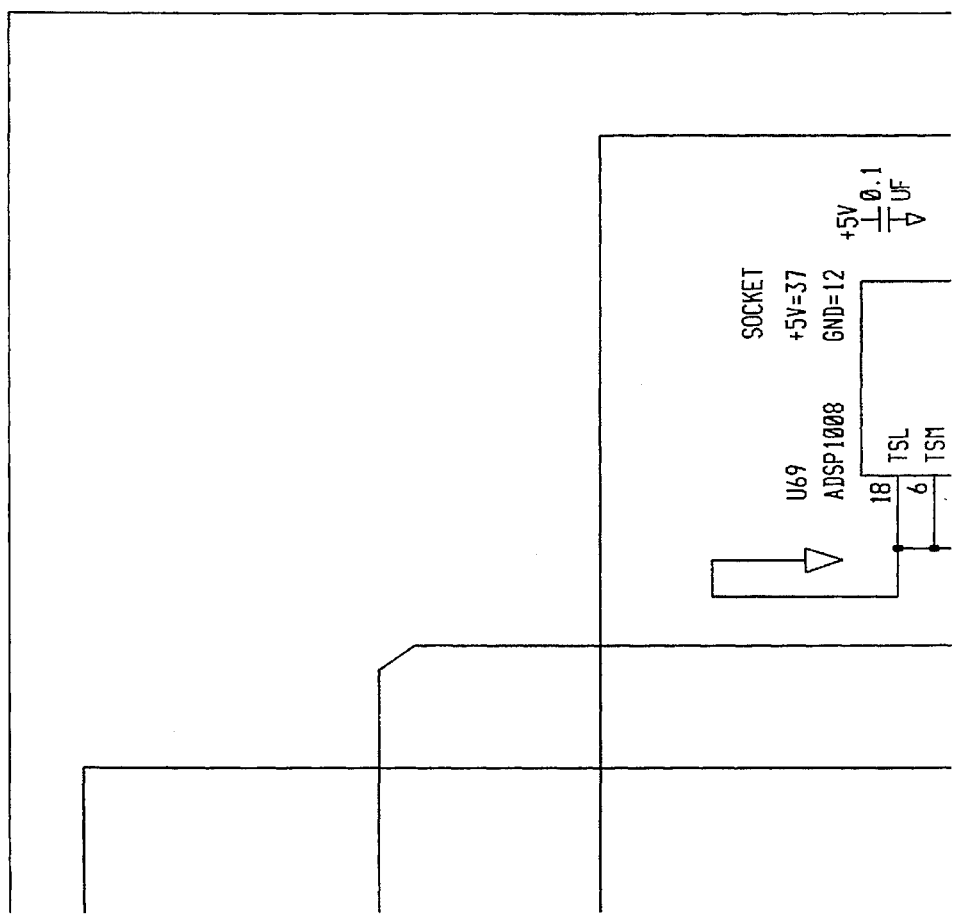

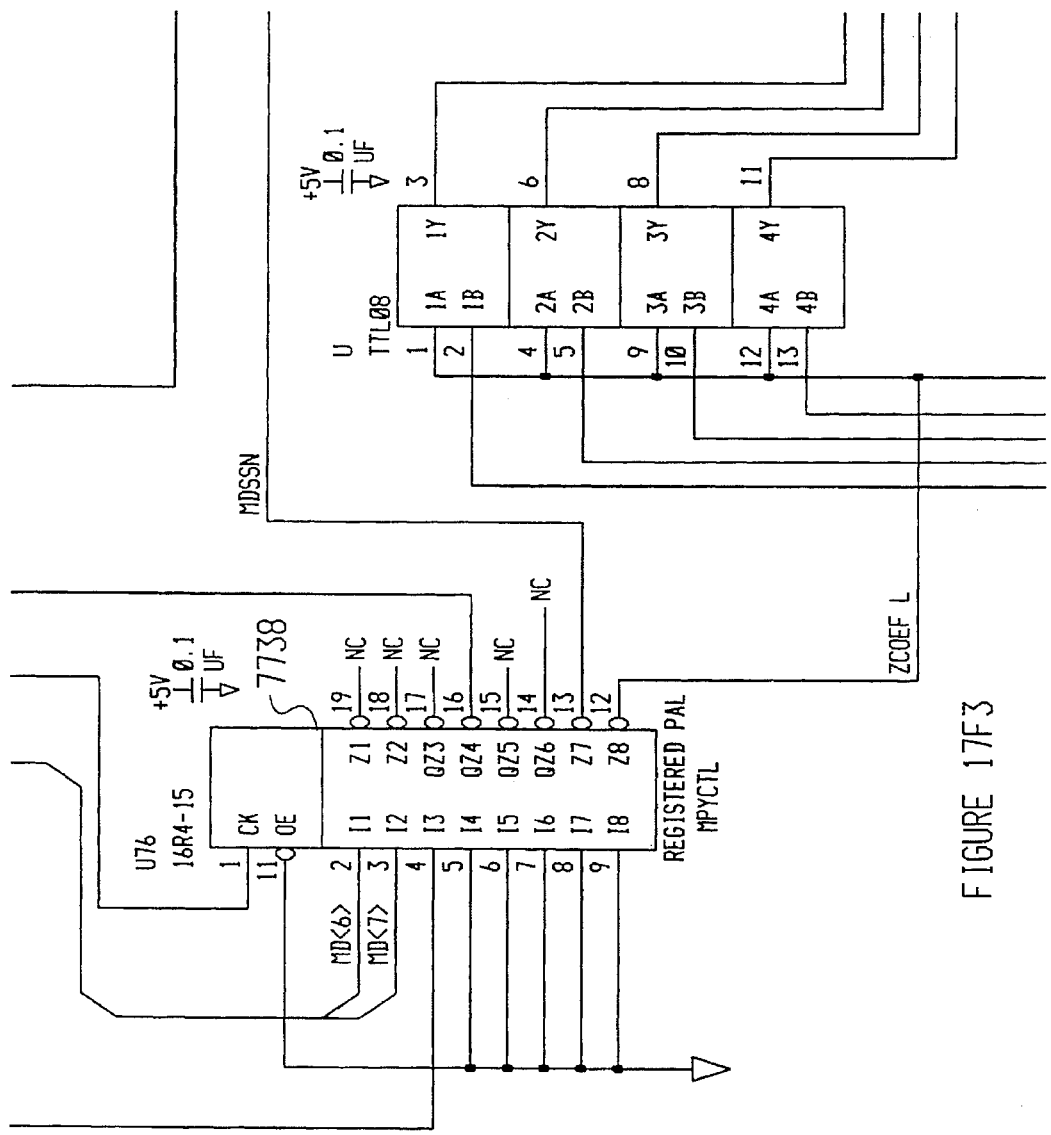
FIGURE 17F3

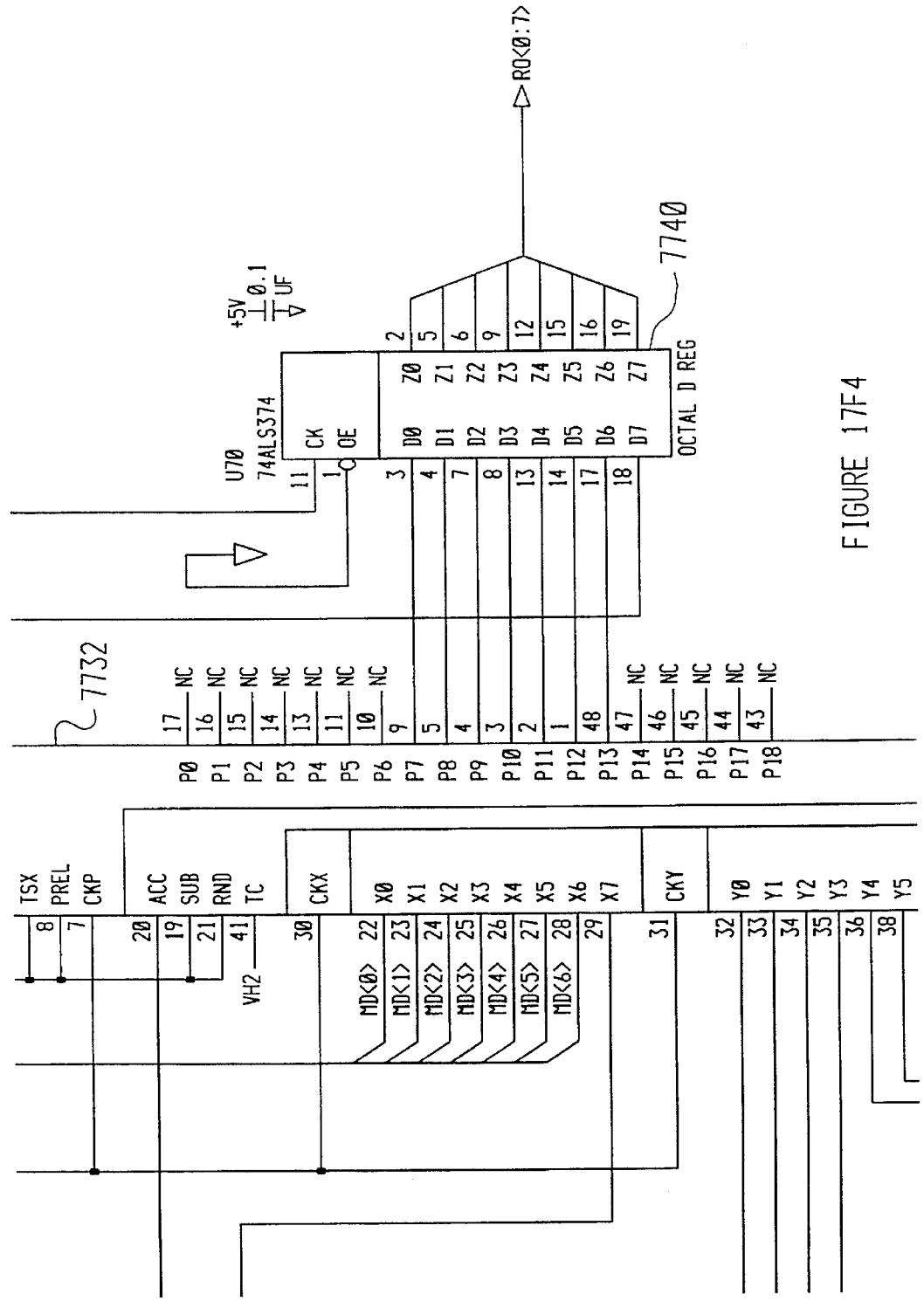
FIGURE 17F4

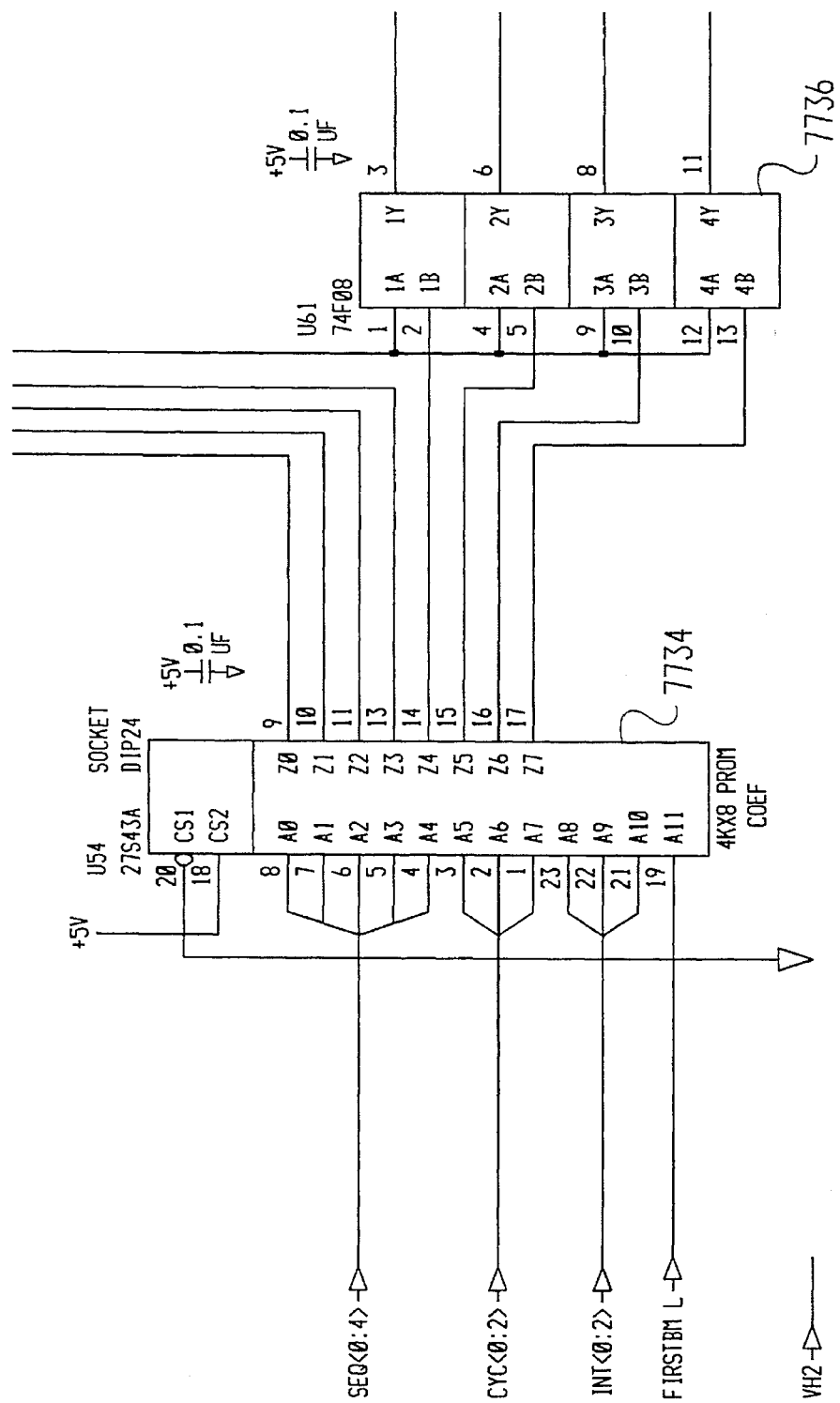
FIGURE 17F5

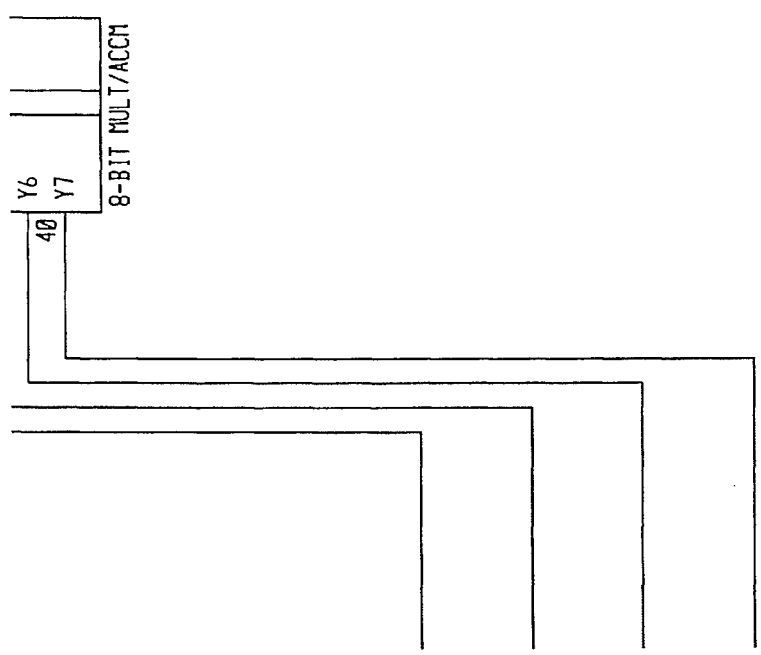
FIGURE 17F6

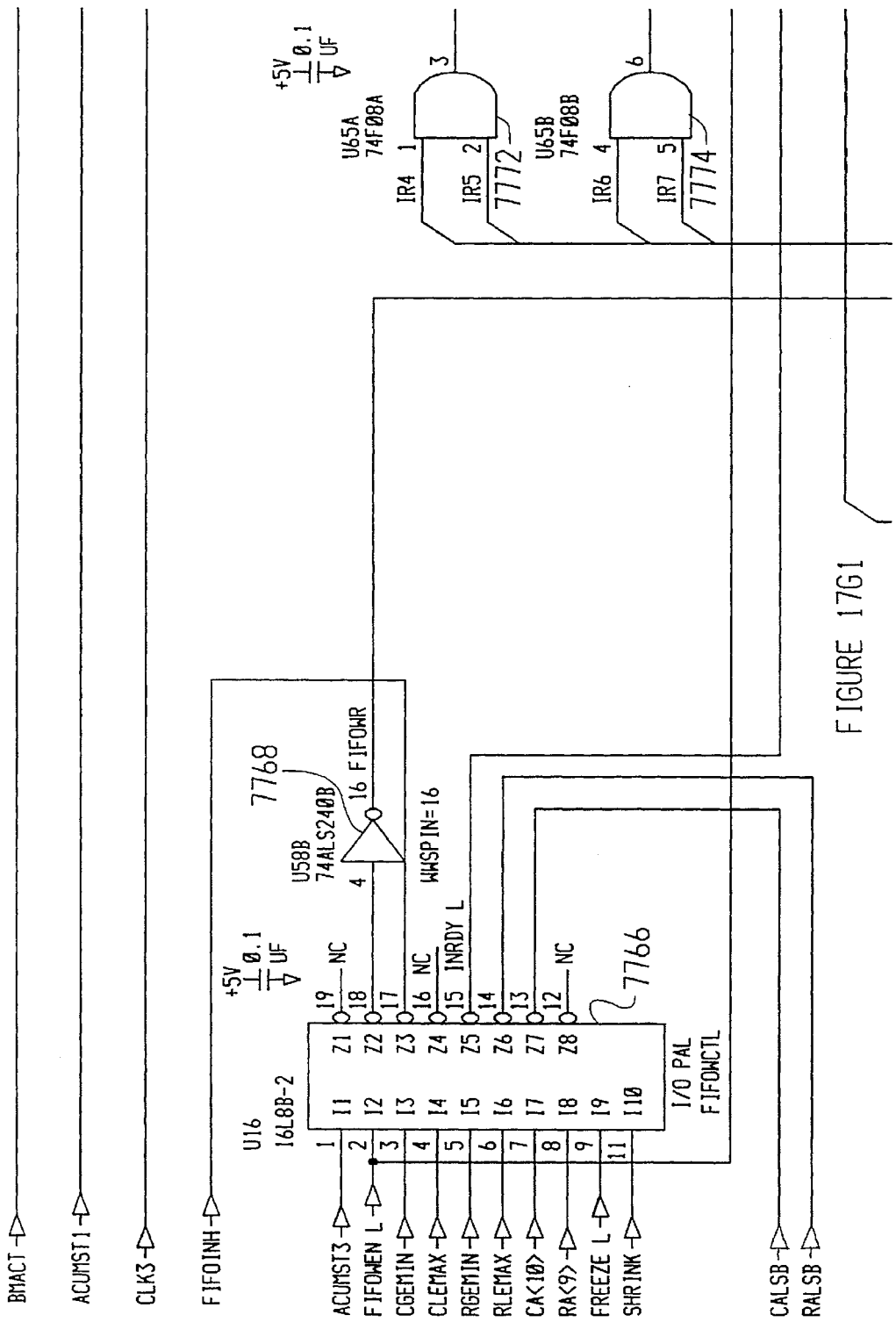

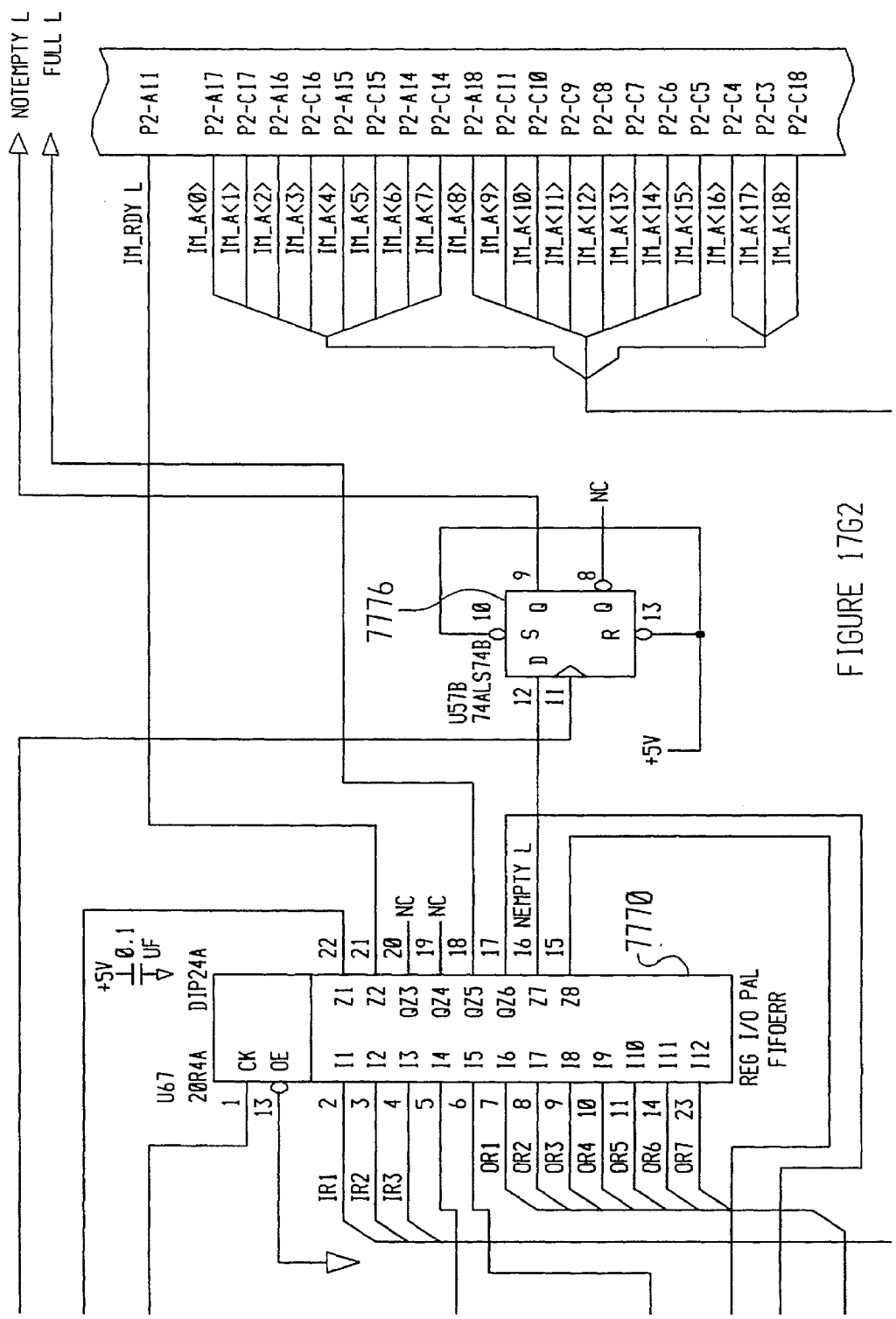
FIGURE 17G2

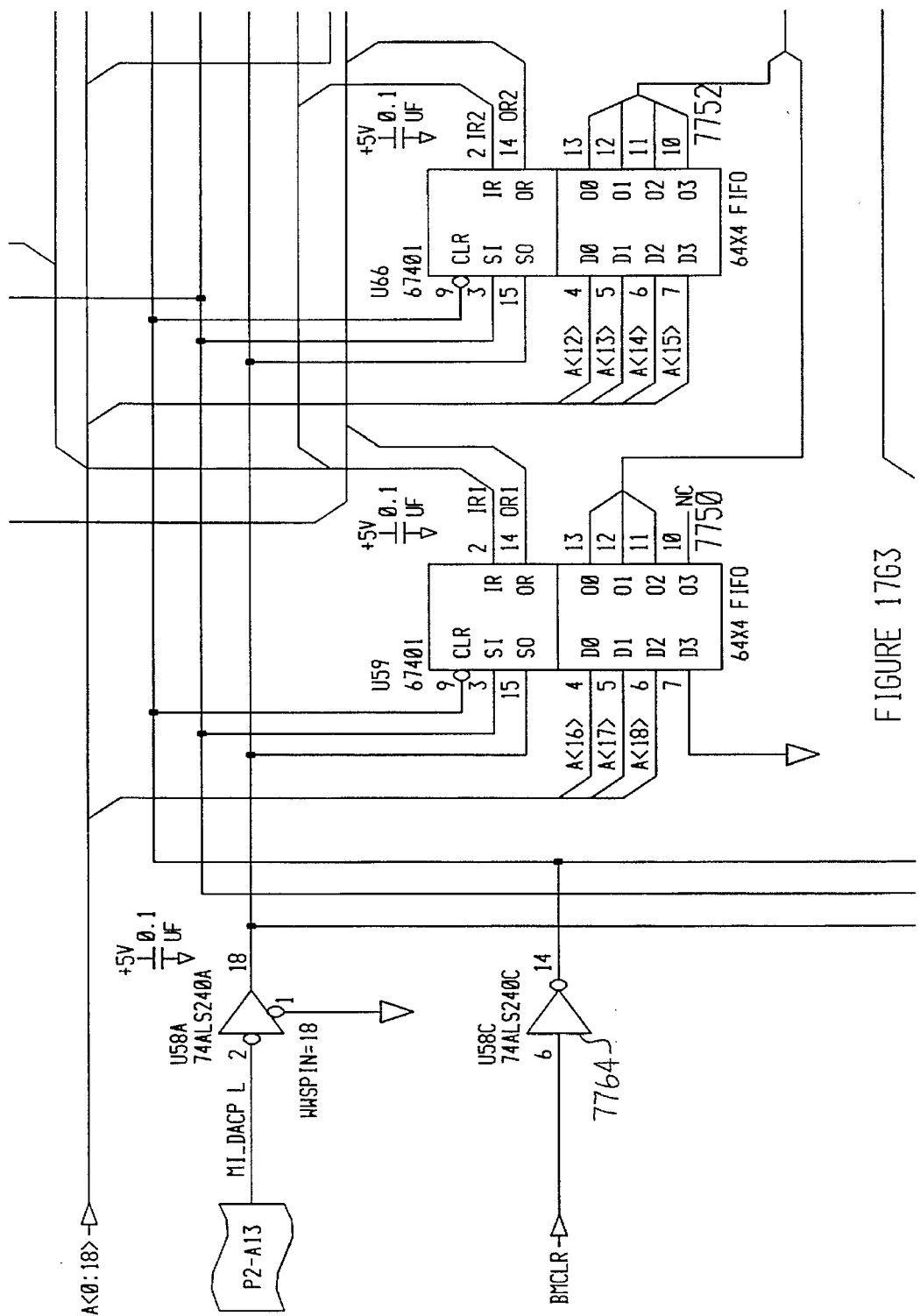
FIGURE 17G3

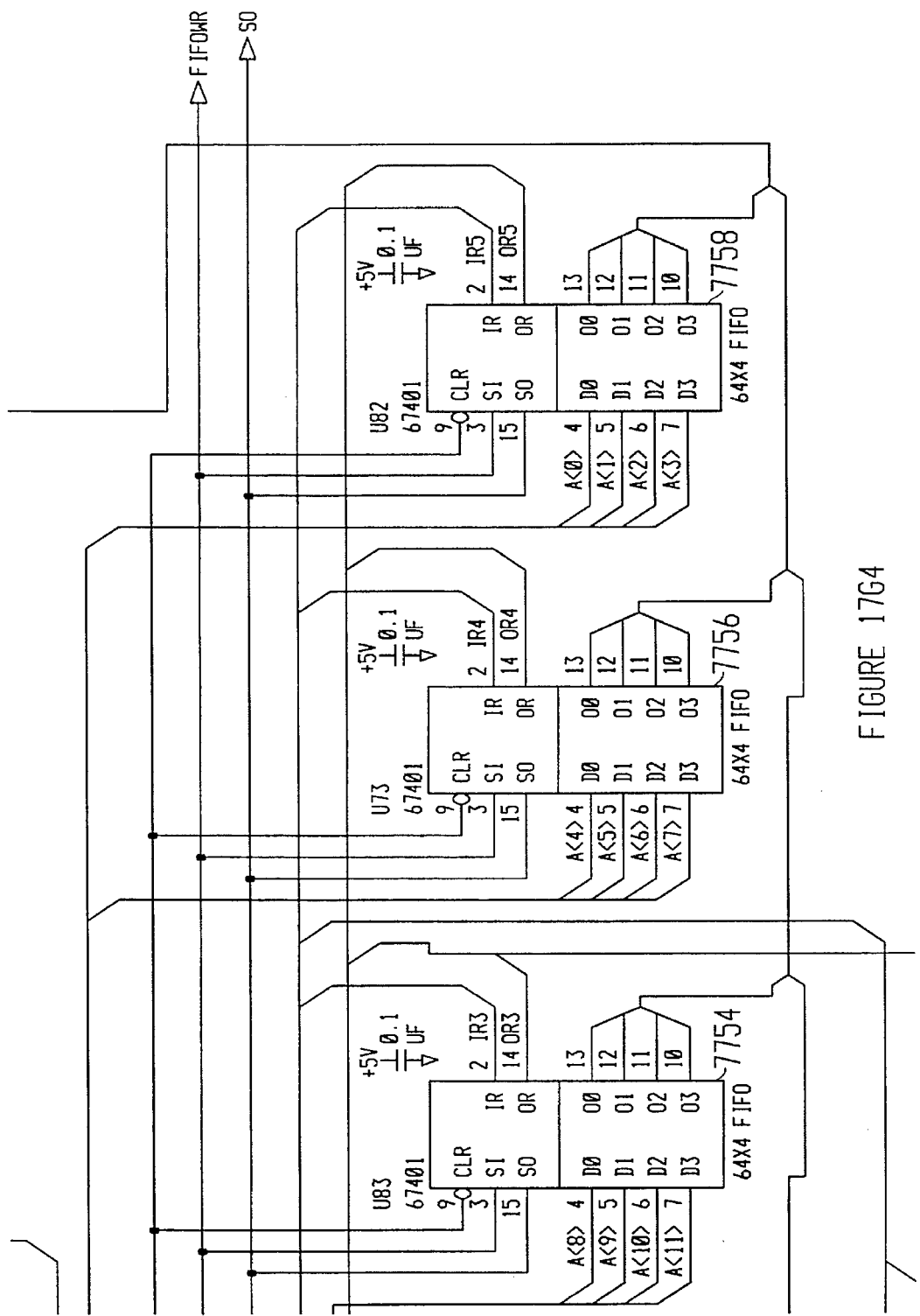
FIGURE 17G4

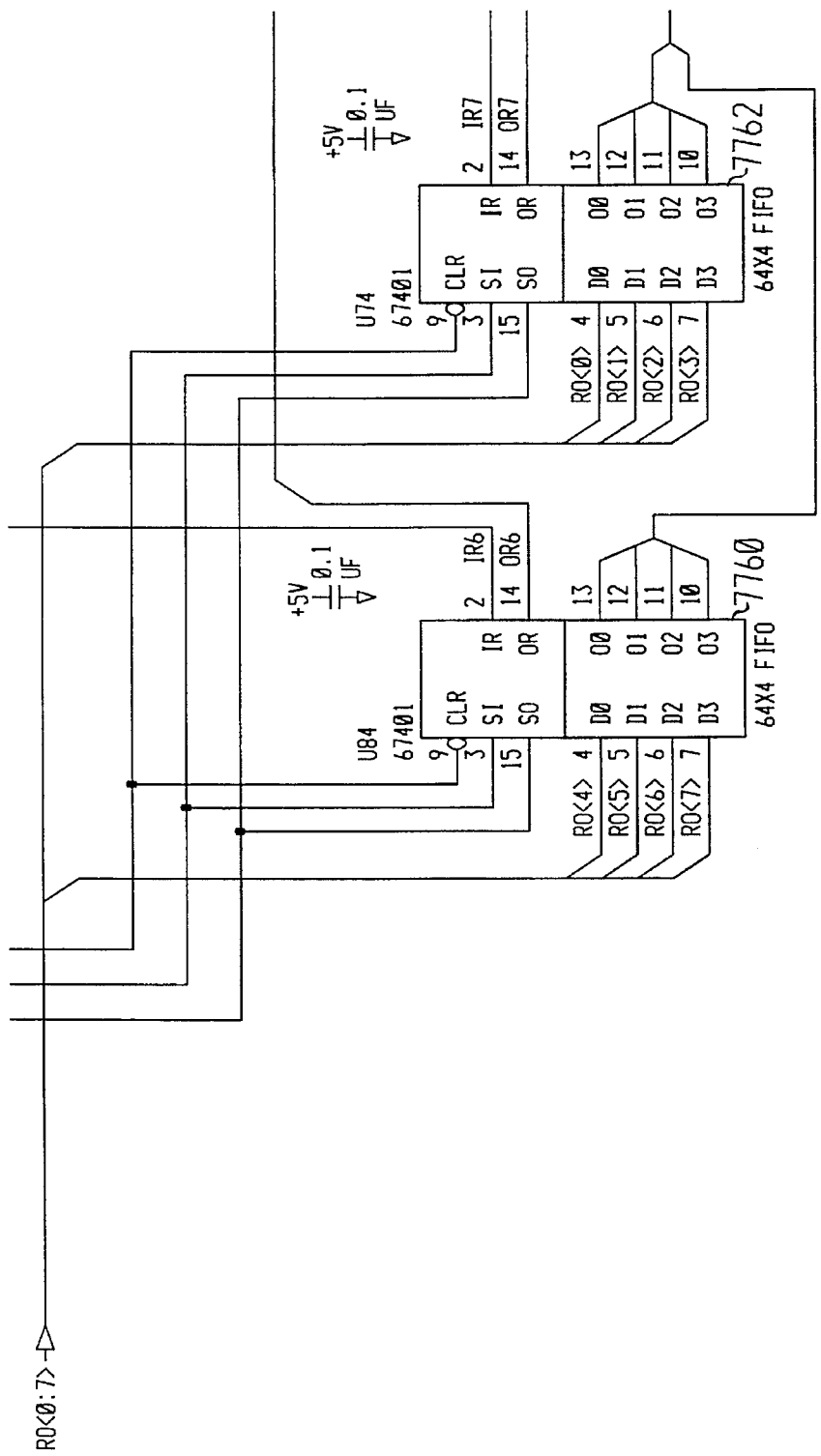
FIGURE 17G5

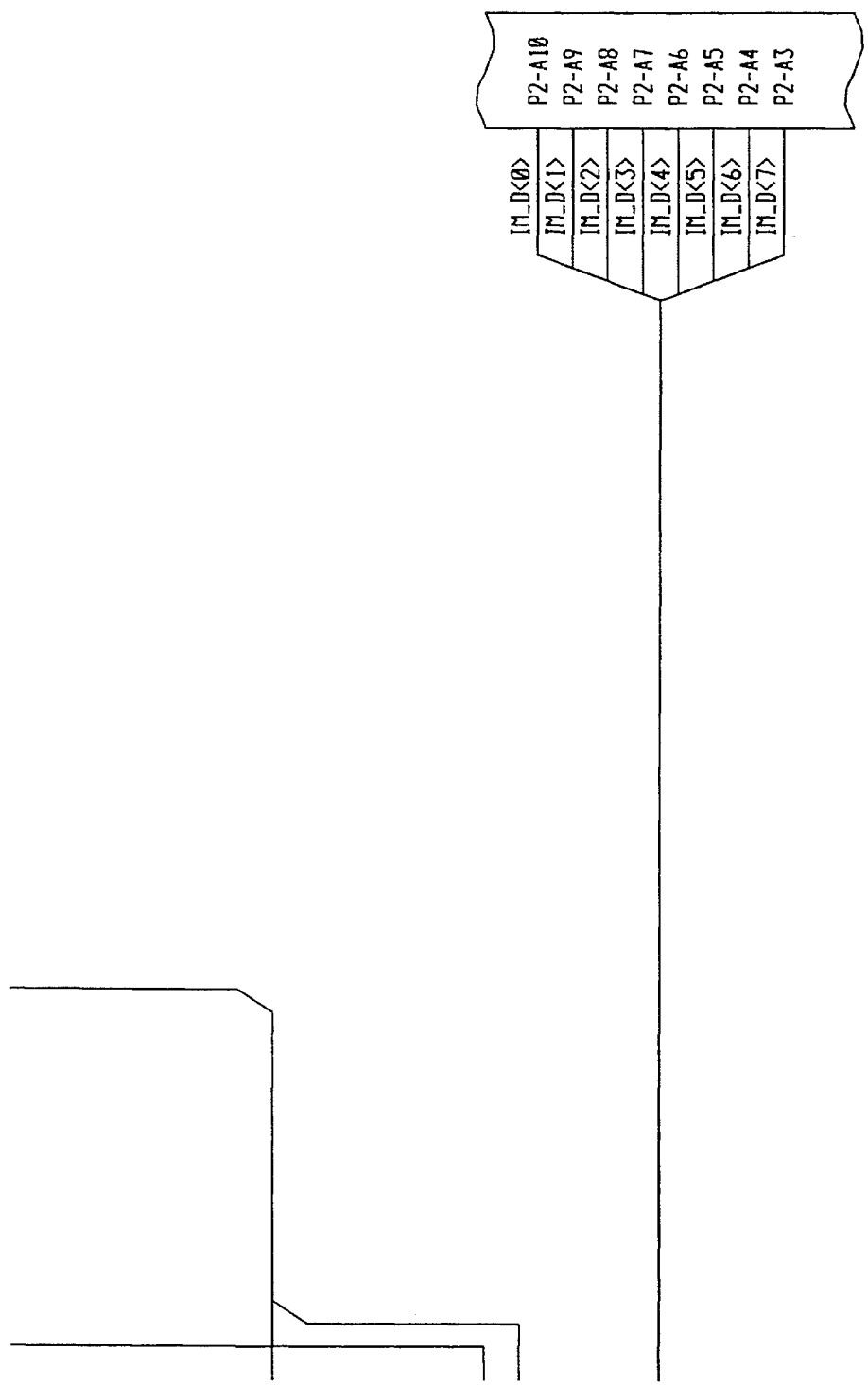
FIGURE 1766

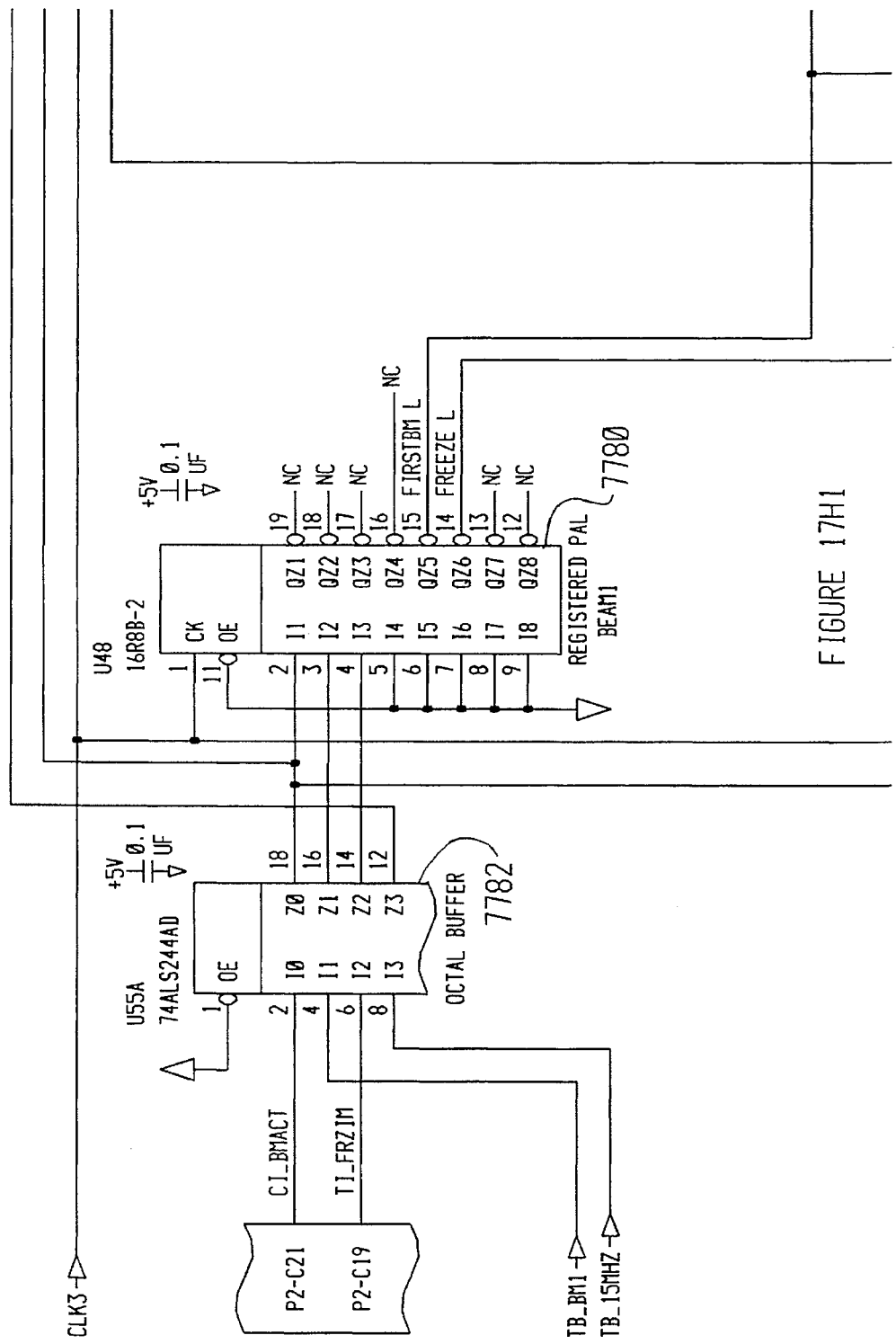

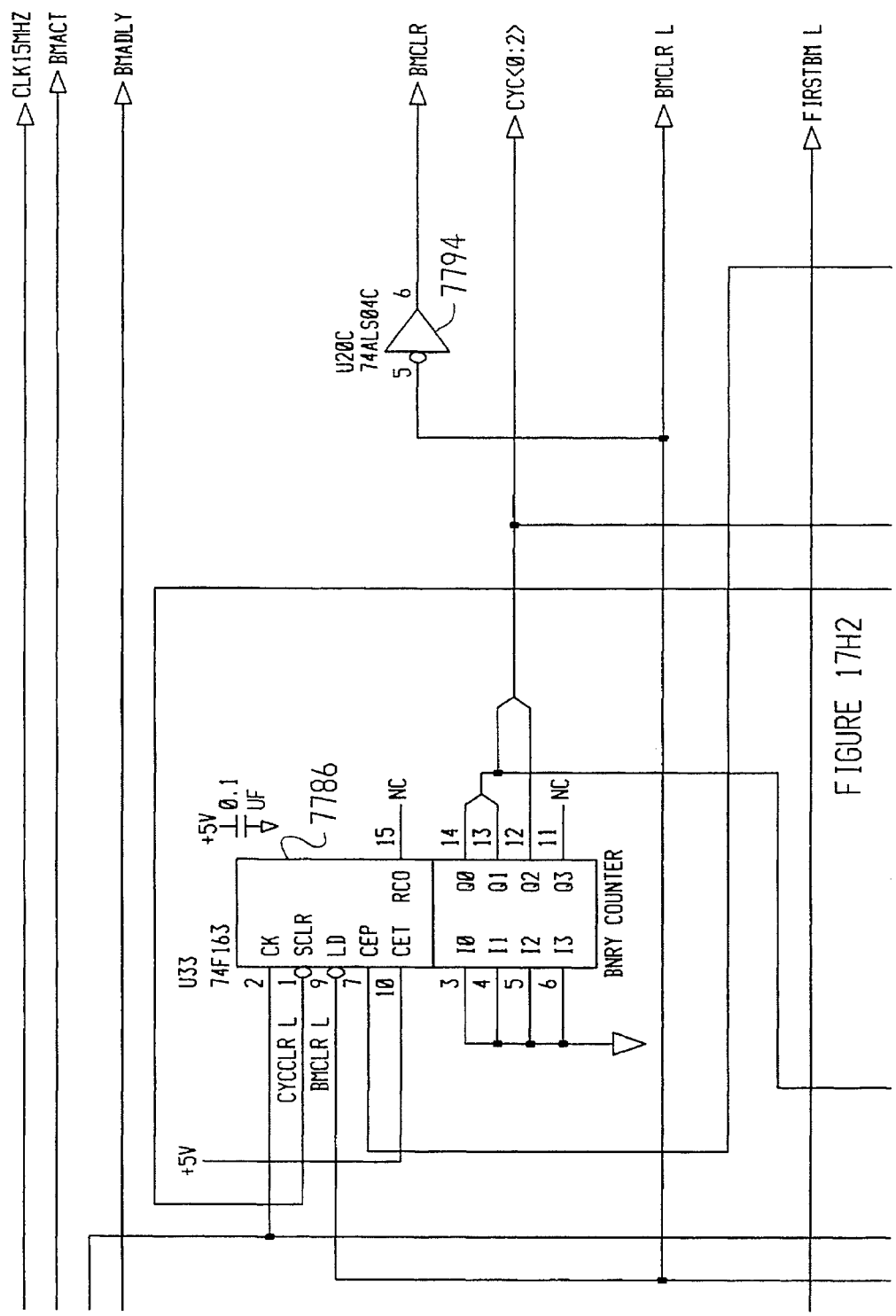
FIGURE 17H2

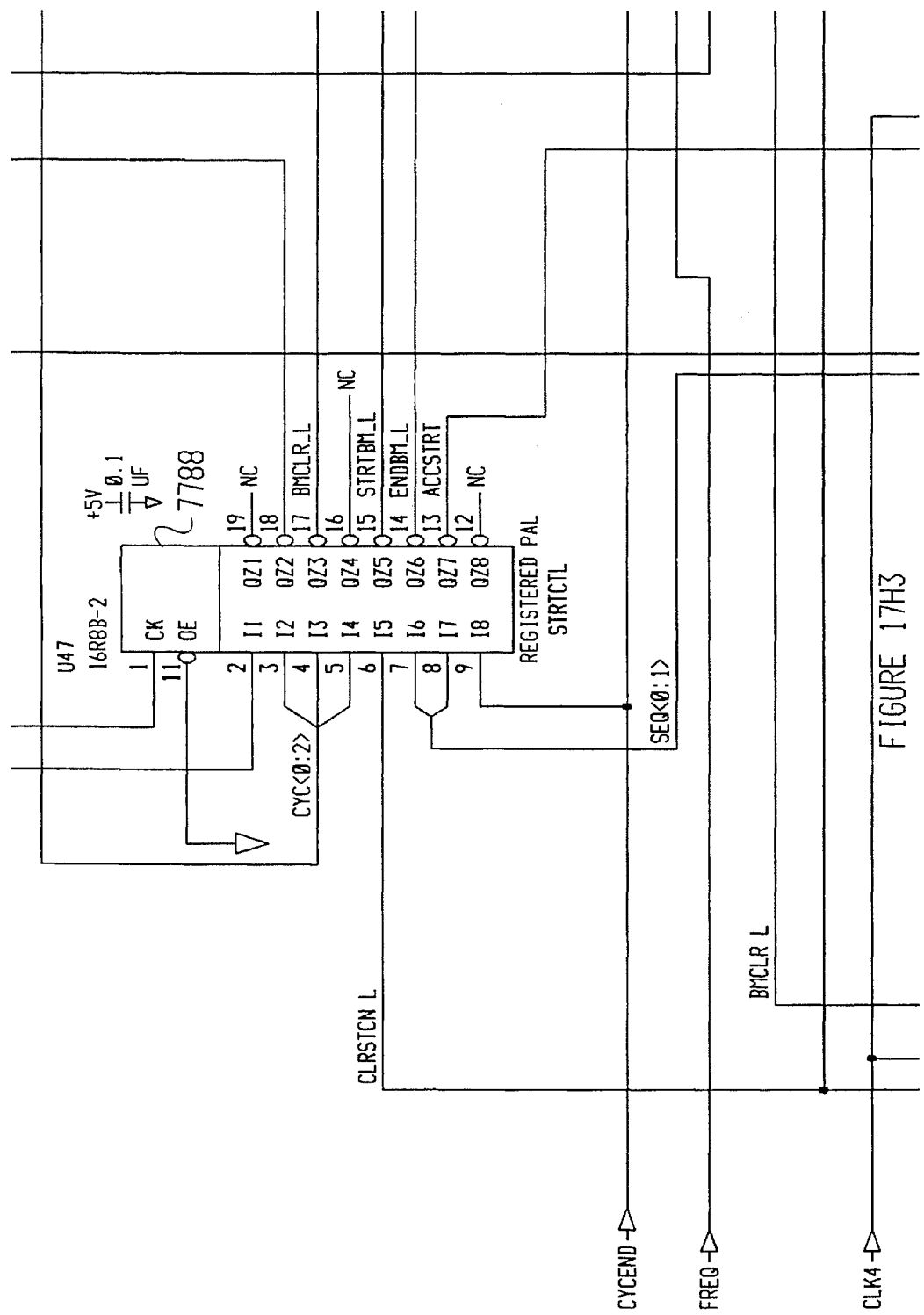
FIGURE 17H3

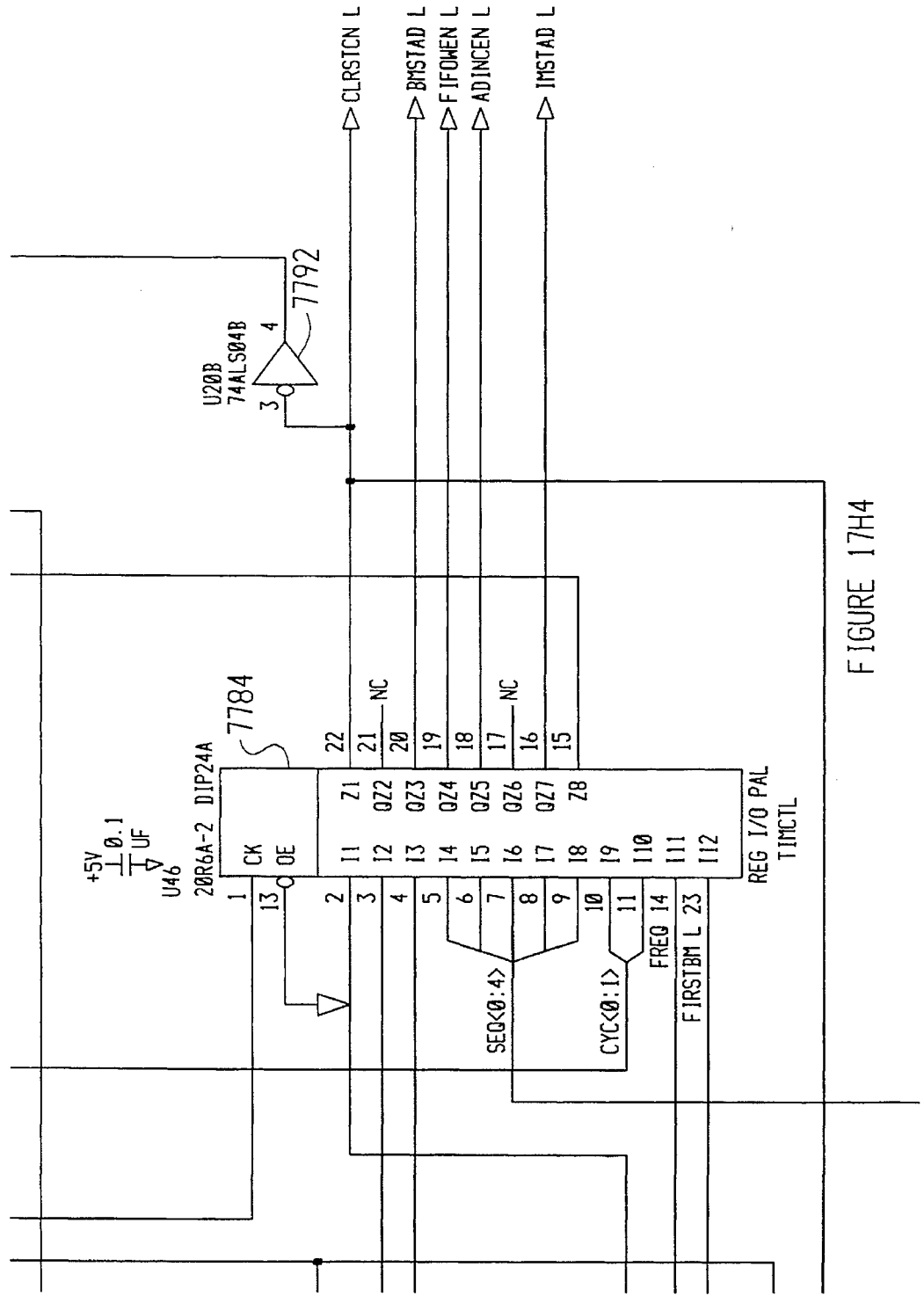
FIGURE 17H4

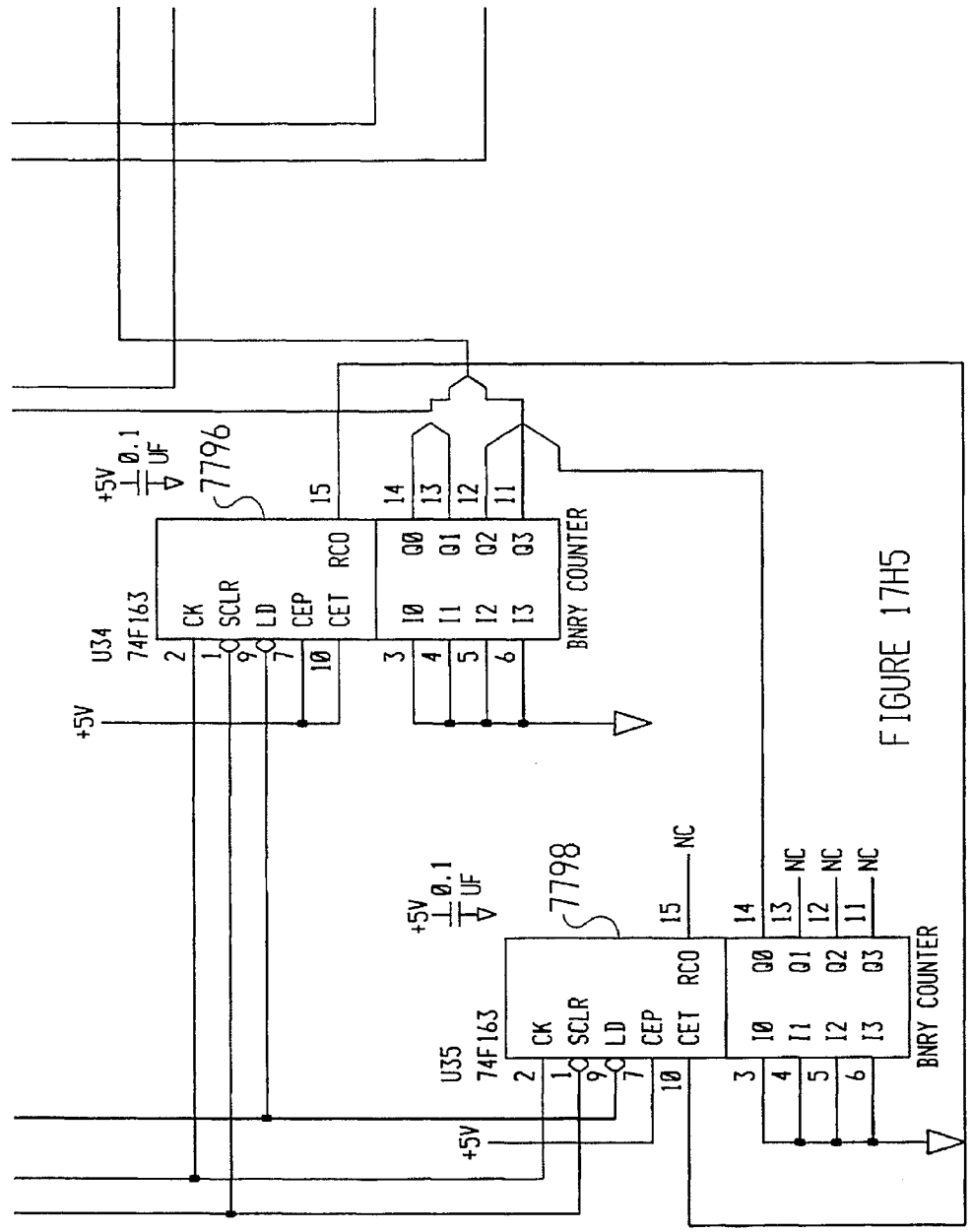

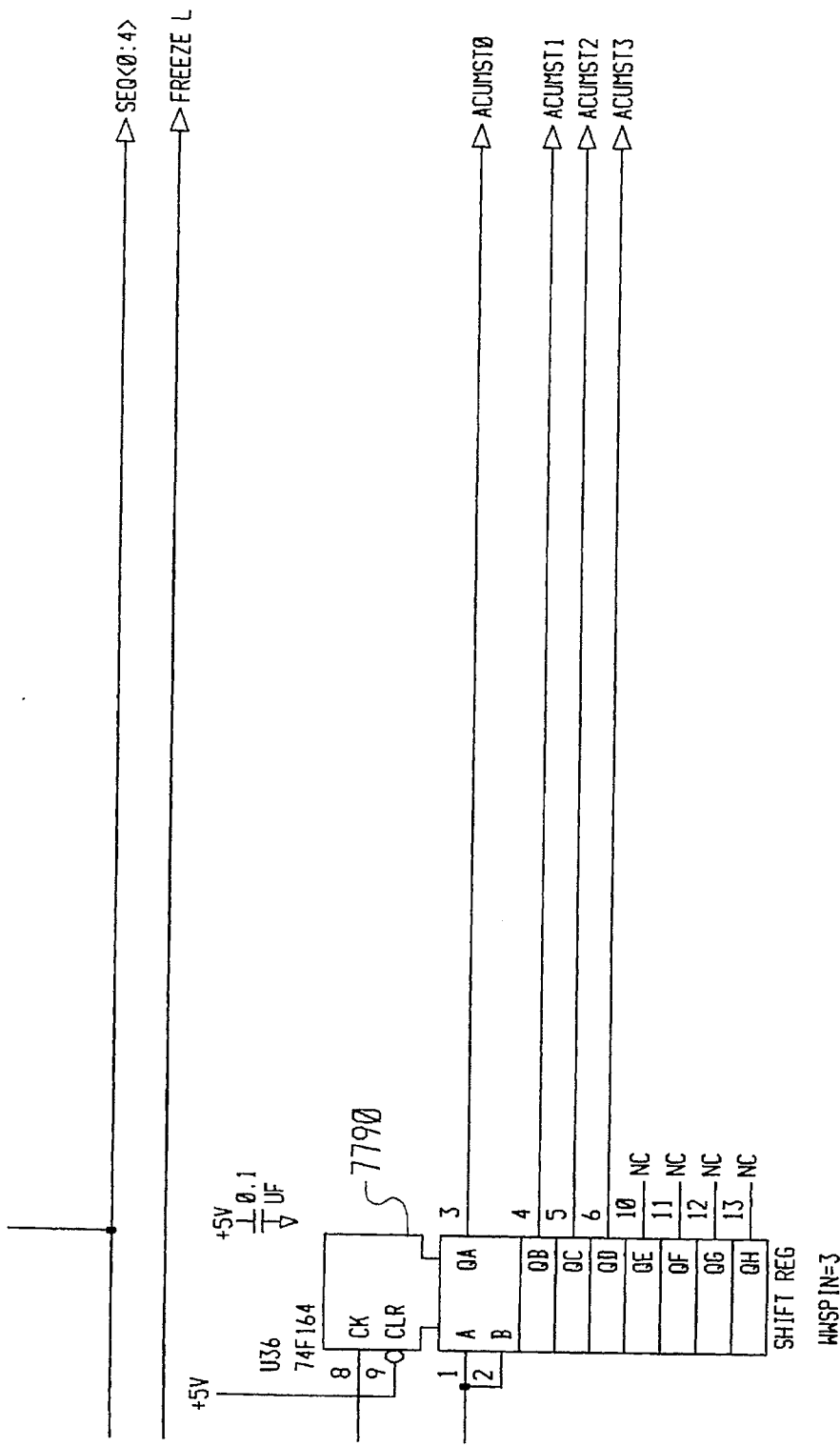
FIGURE 17H6

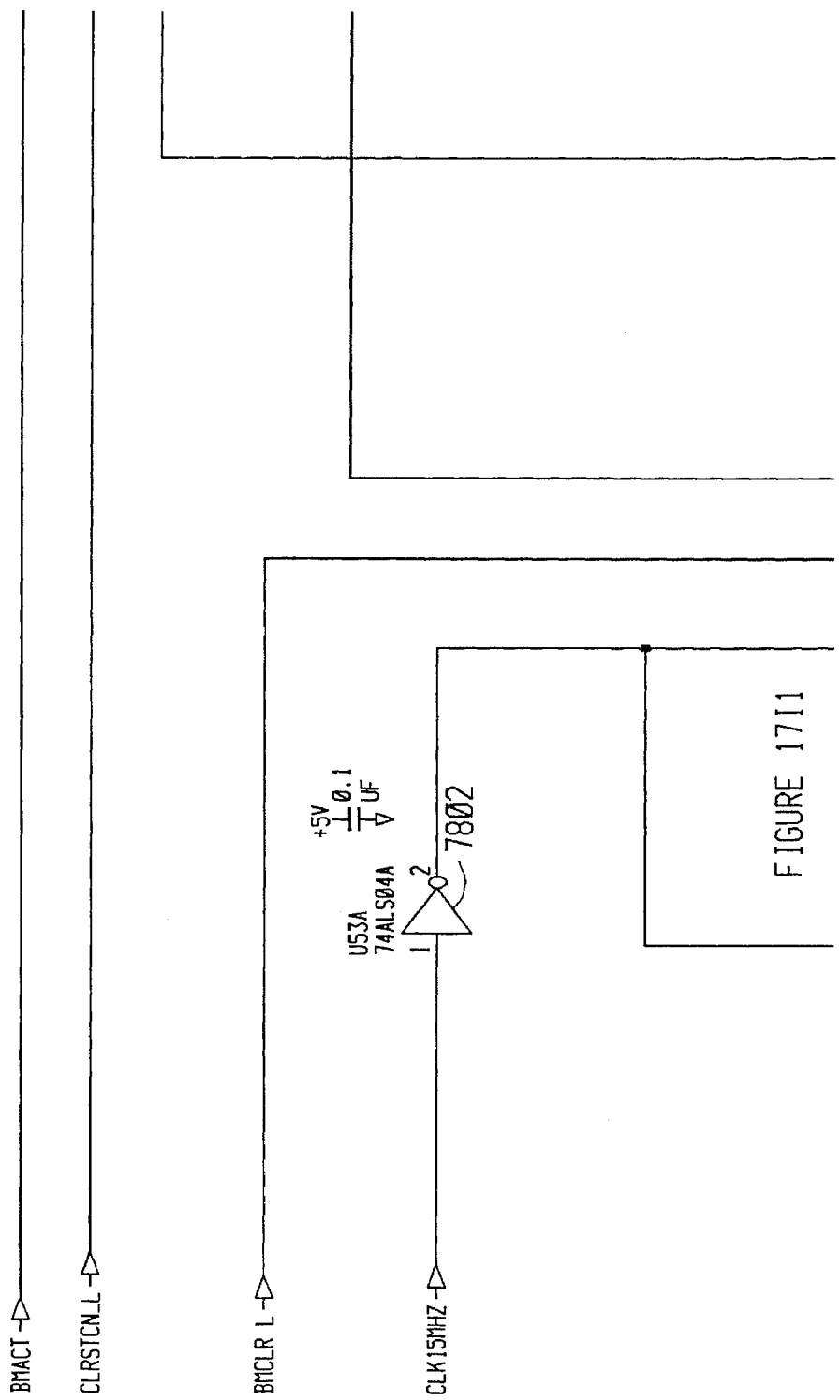
FIGURE 17I1

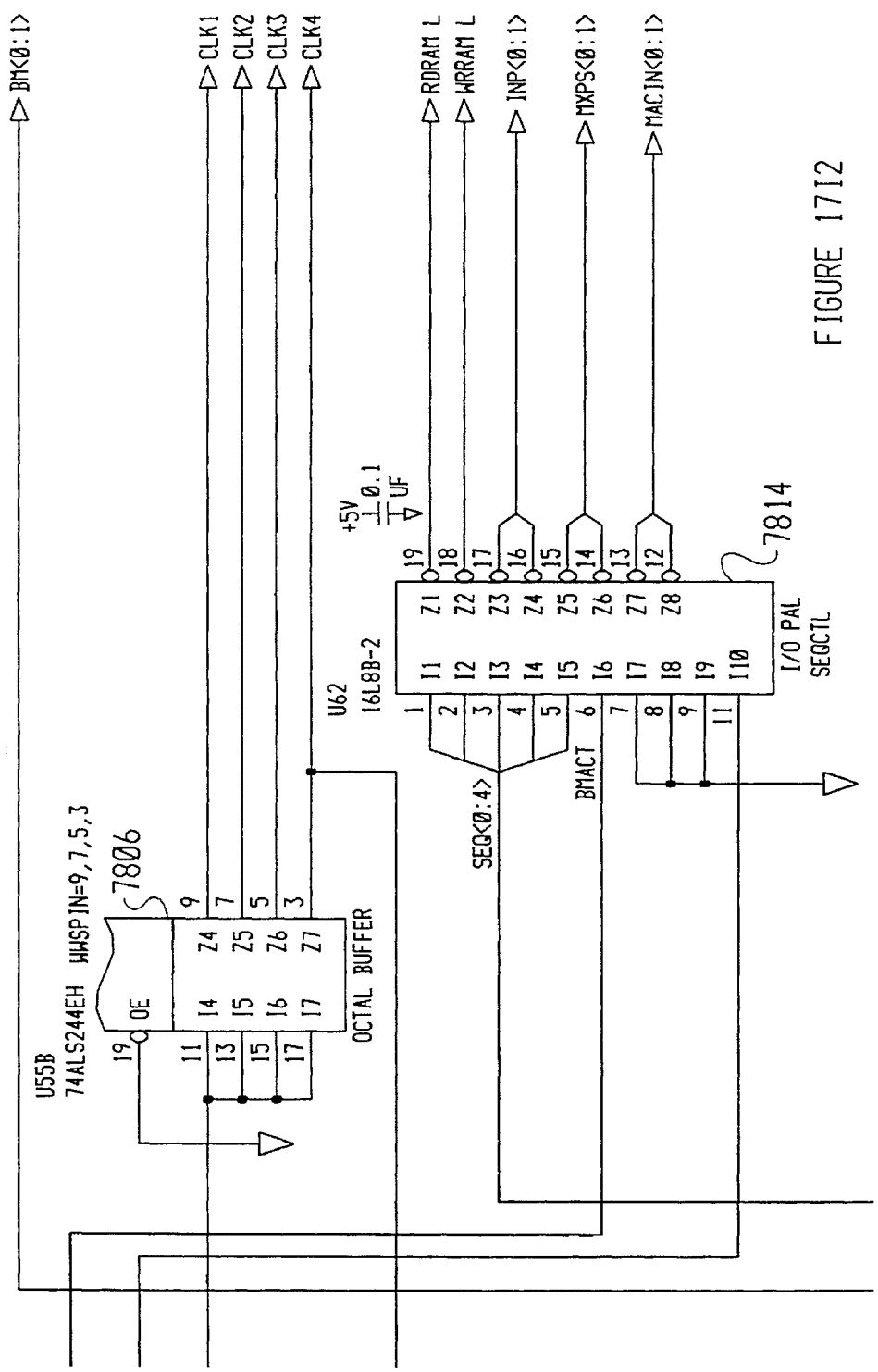
FIGURE 1712

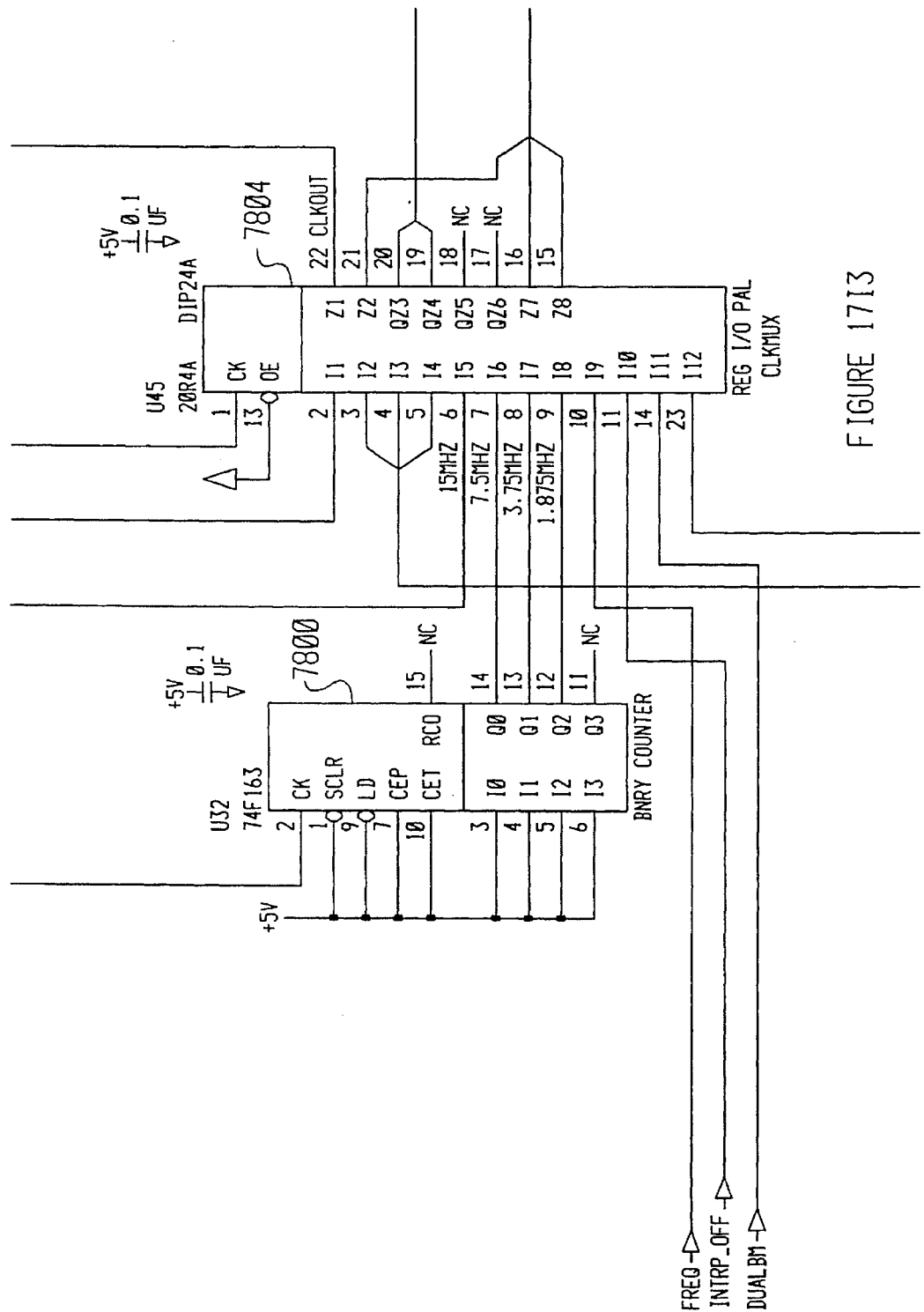
FIGURE 1713

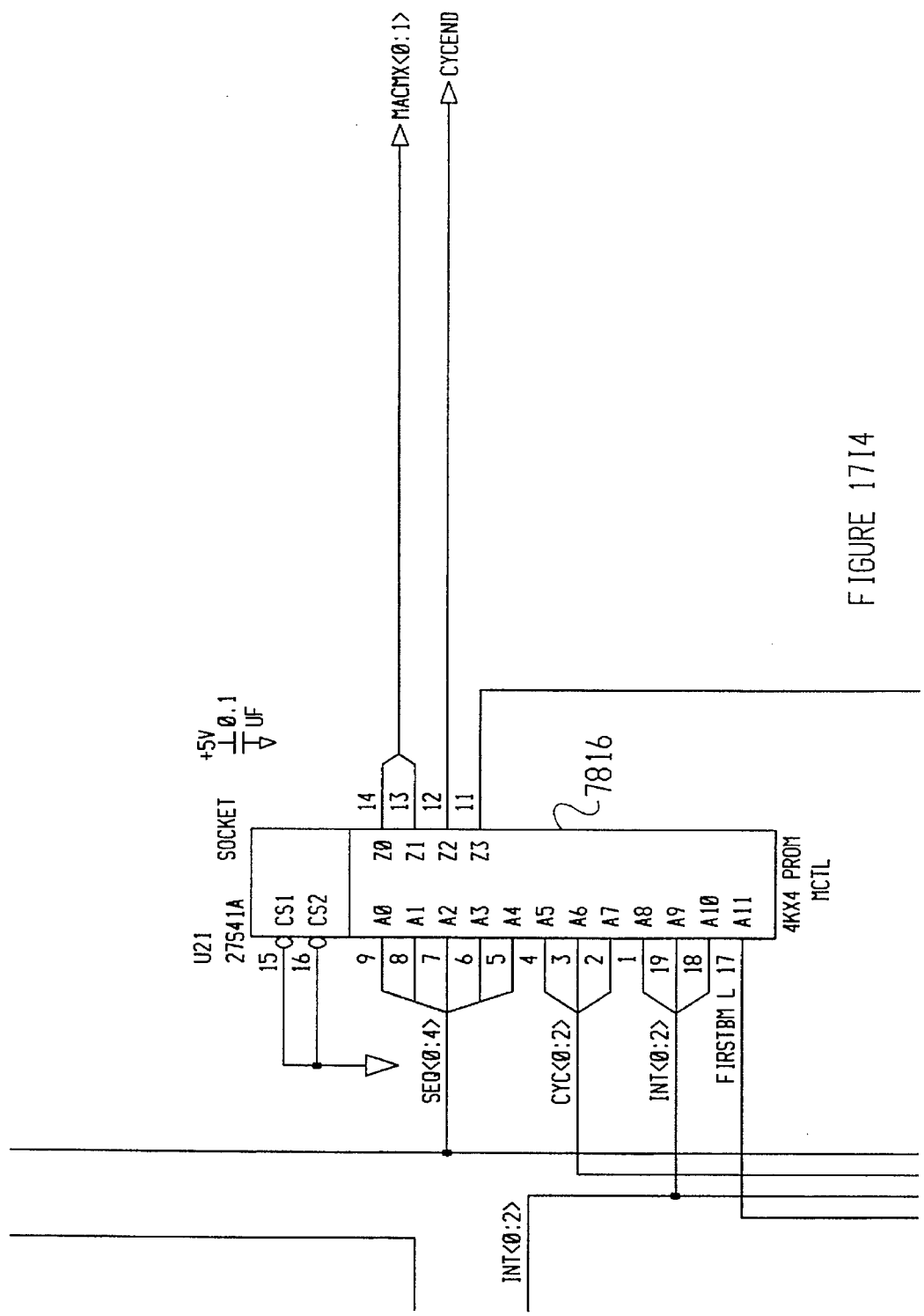
FIGURE 1714

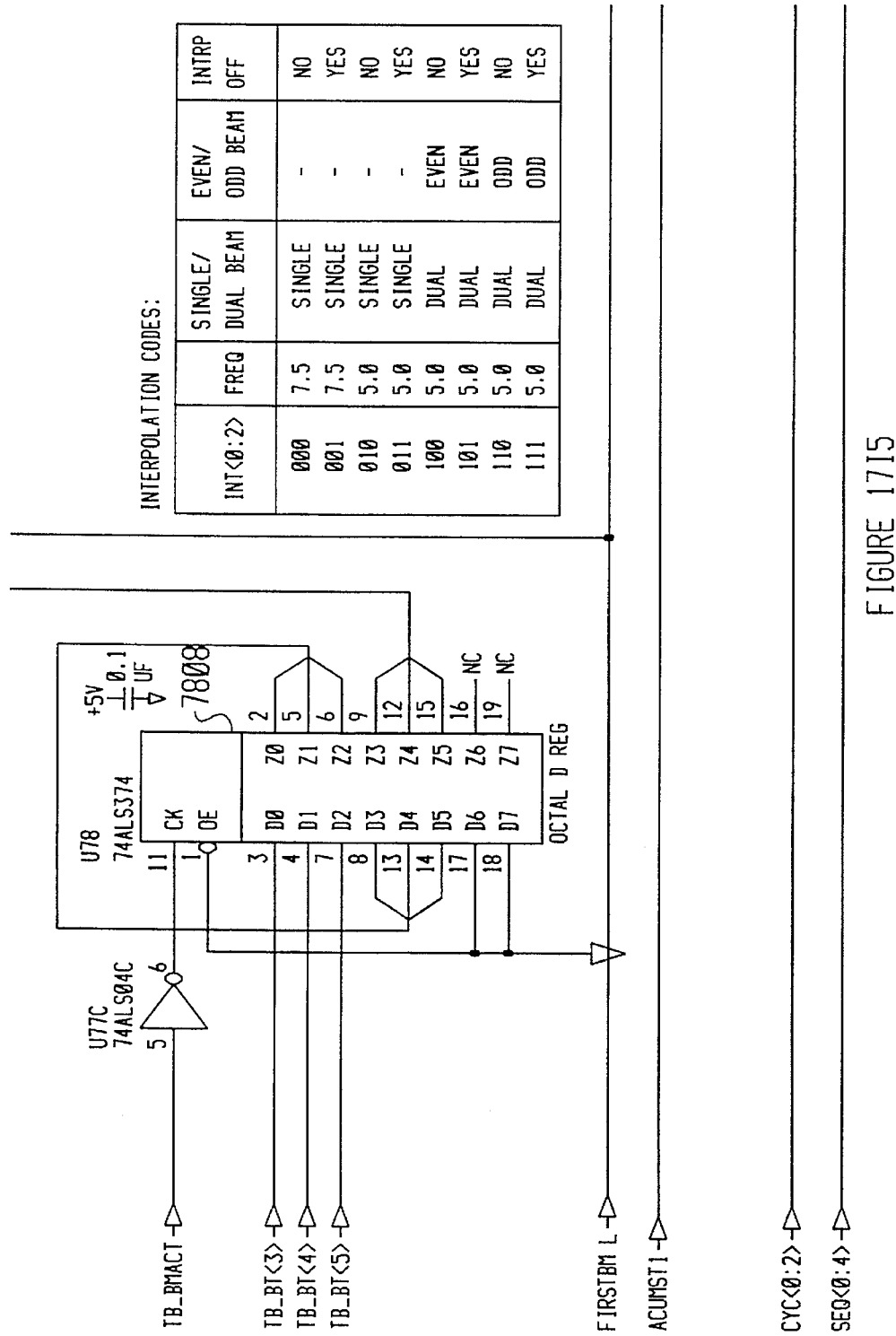
FIGURE 1715

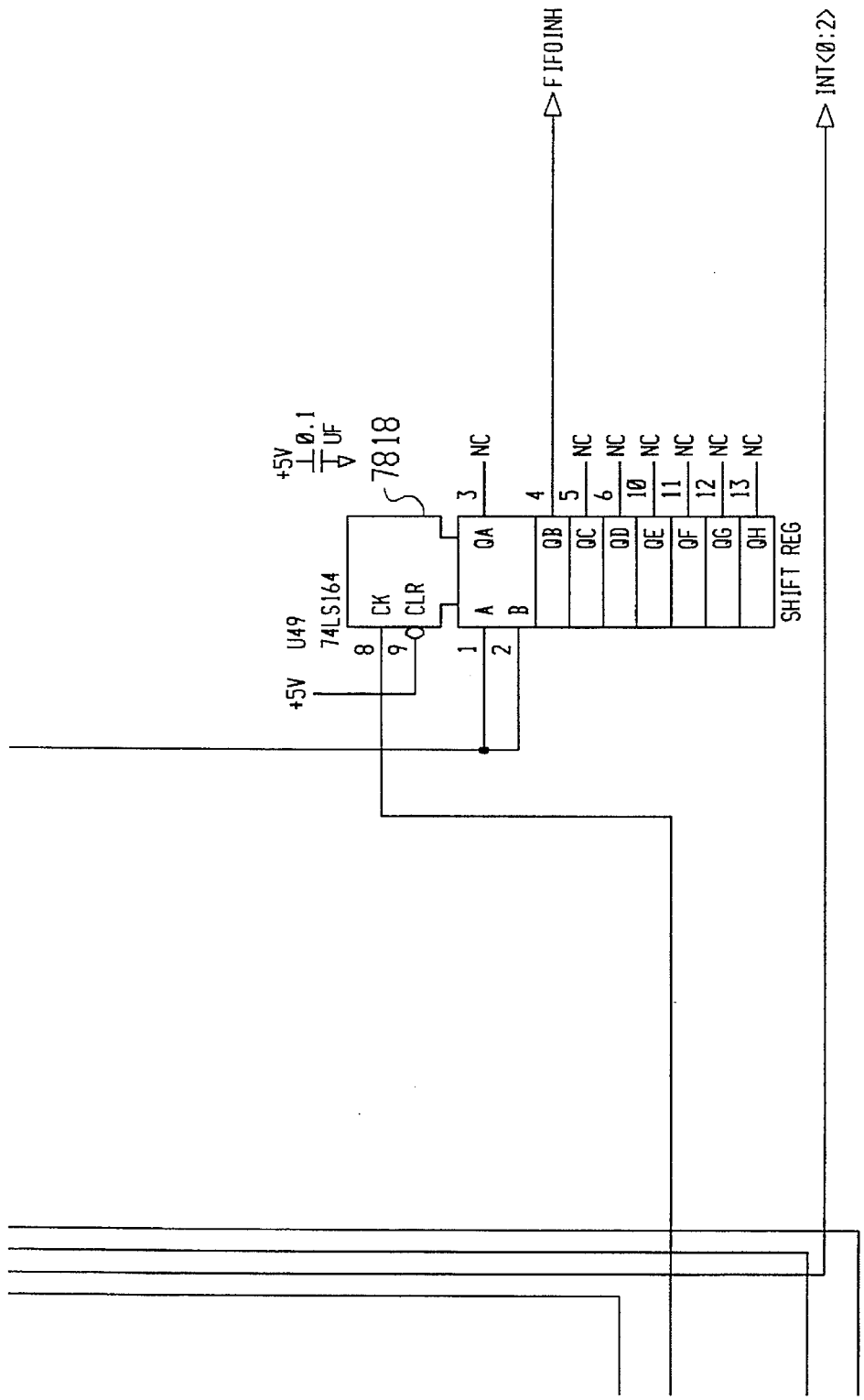
FIGURE 1716

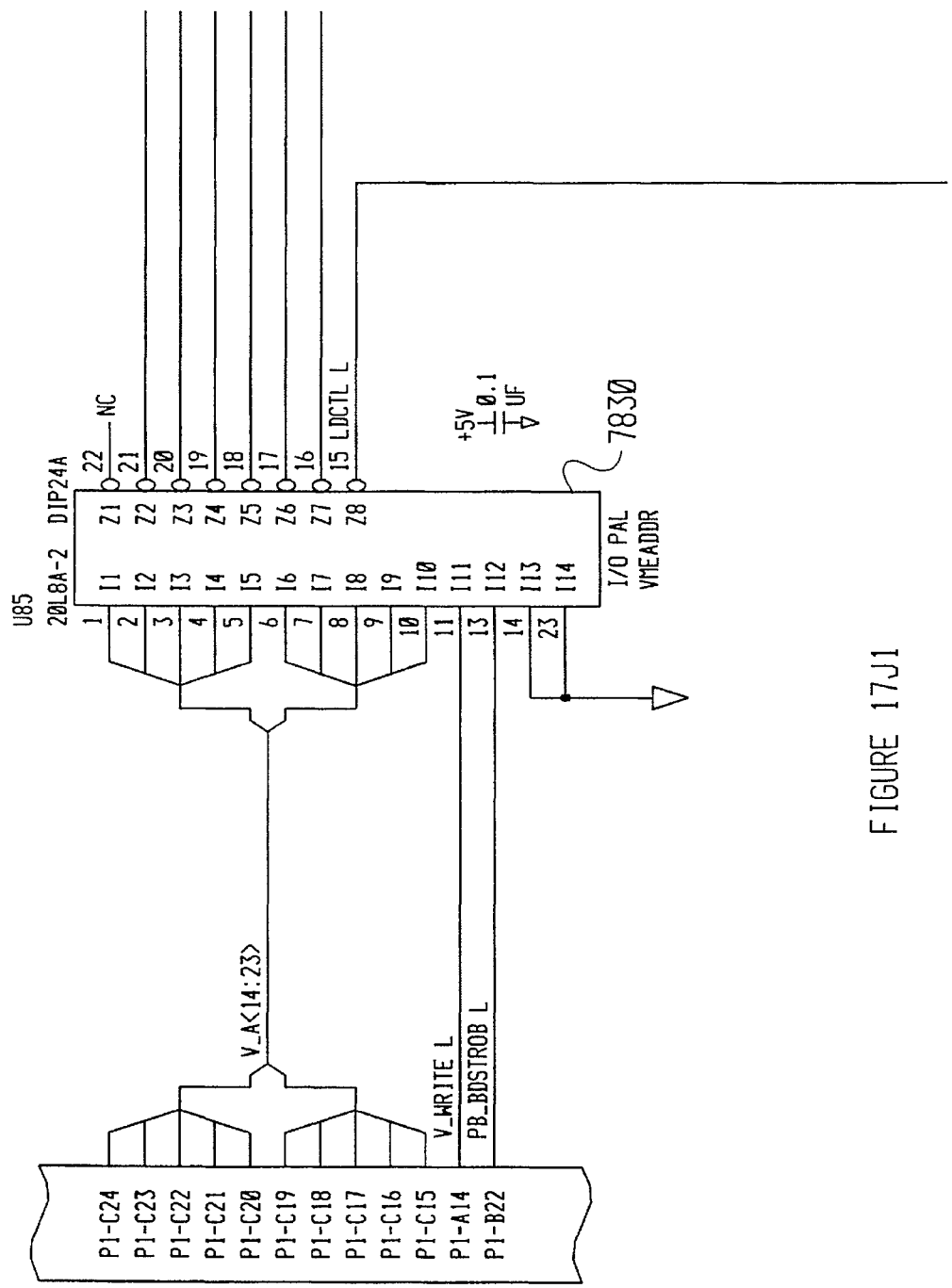
FIGURE 17J1

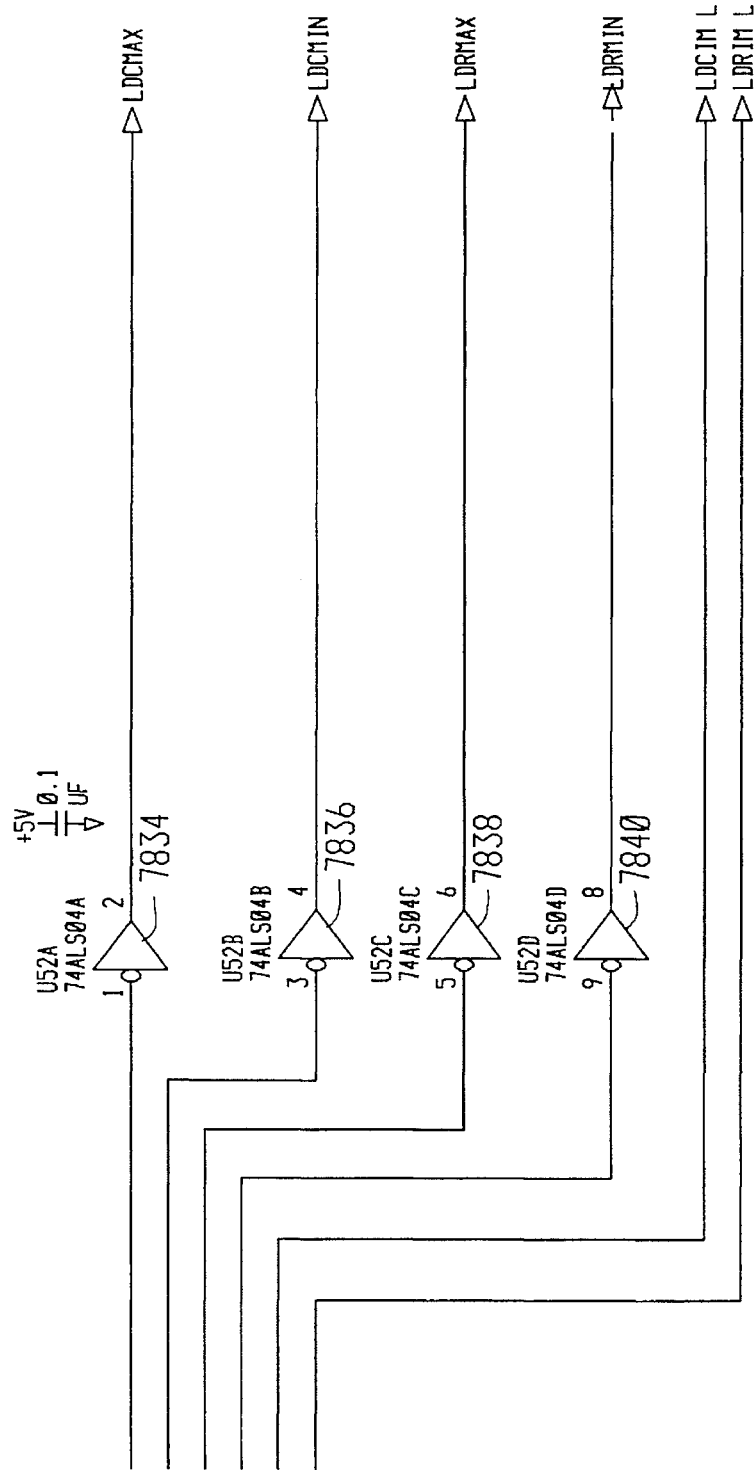
FIGURE 17J2

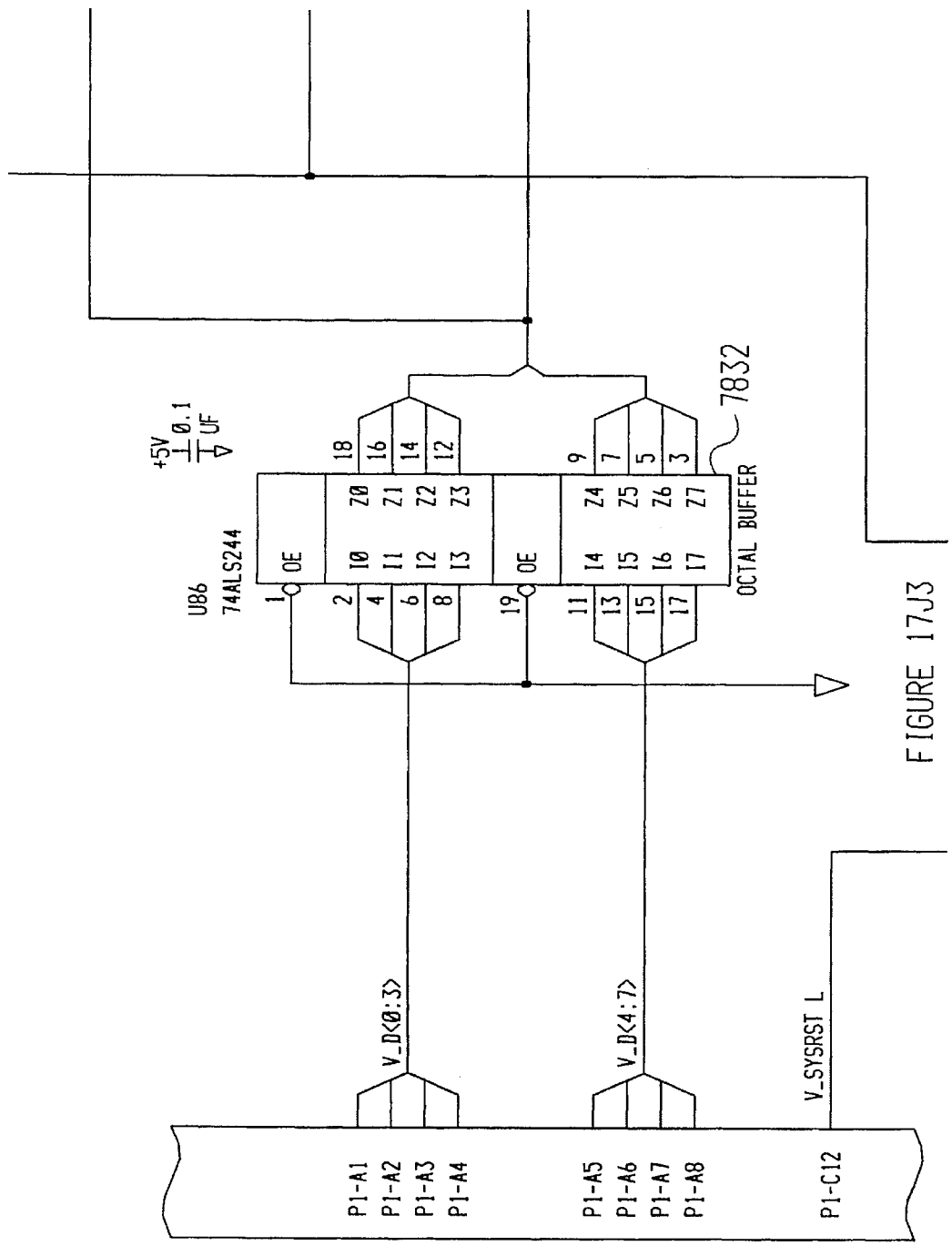
FIGURE 17J3

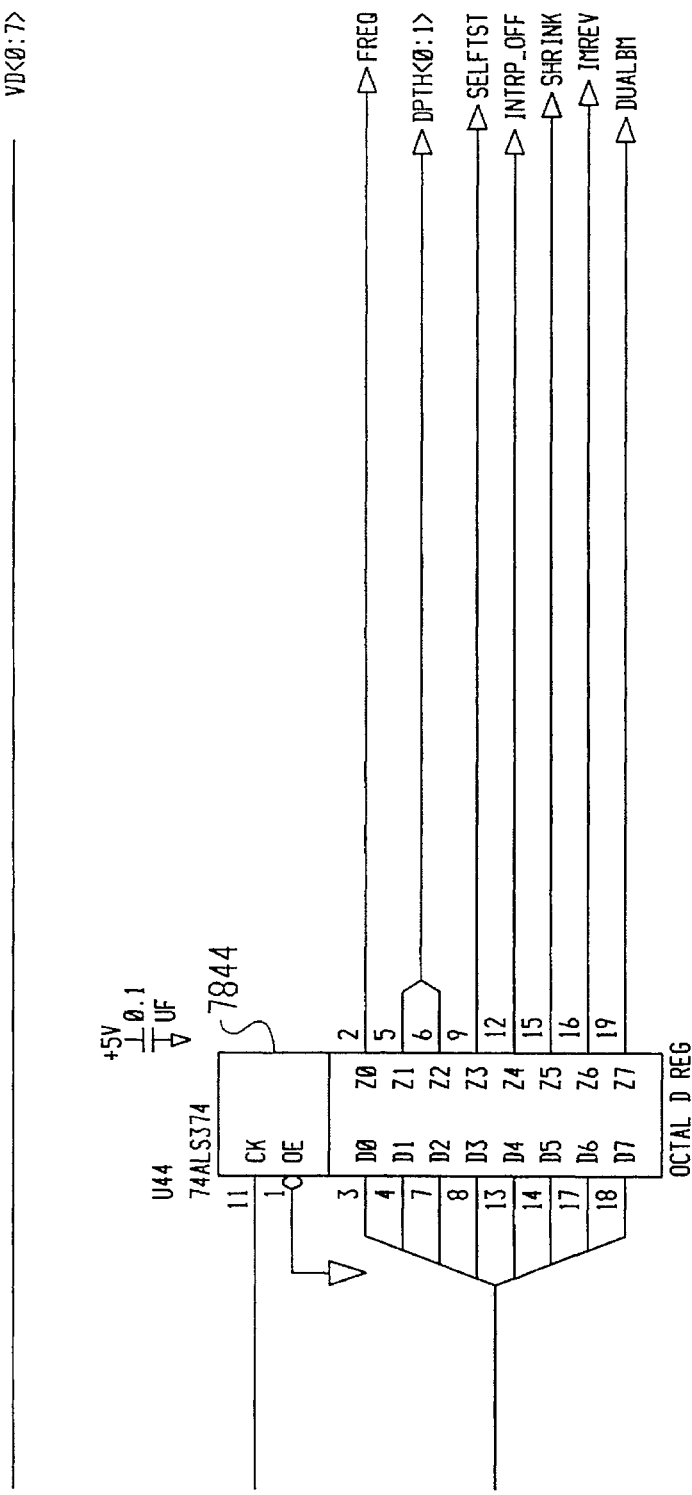
FIGURE 17J4

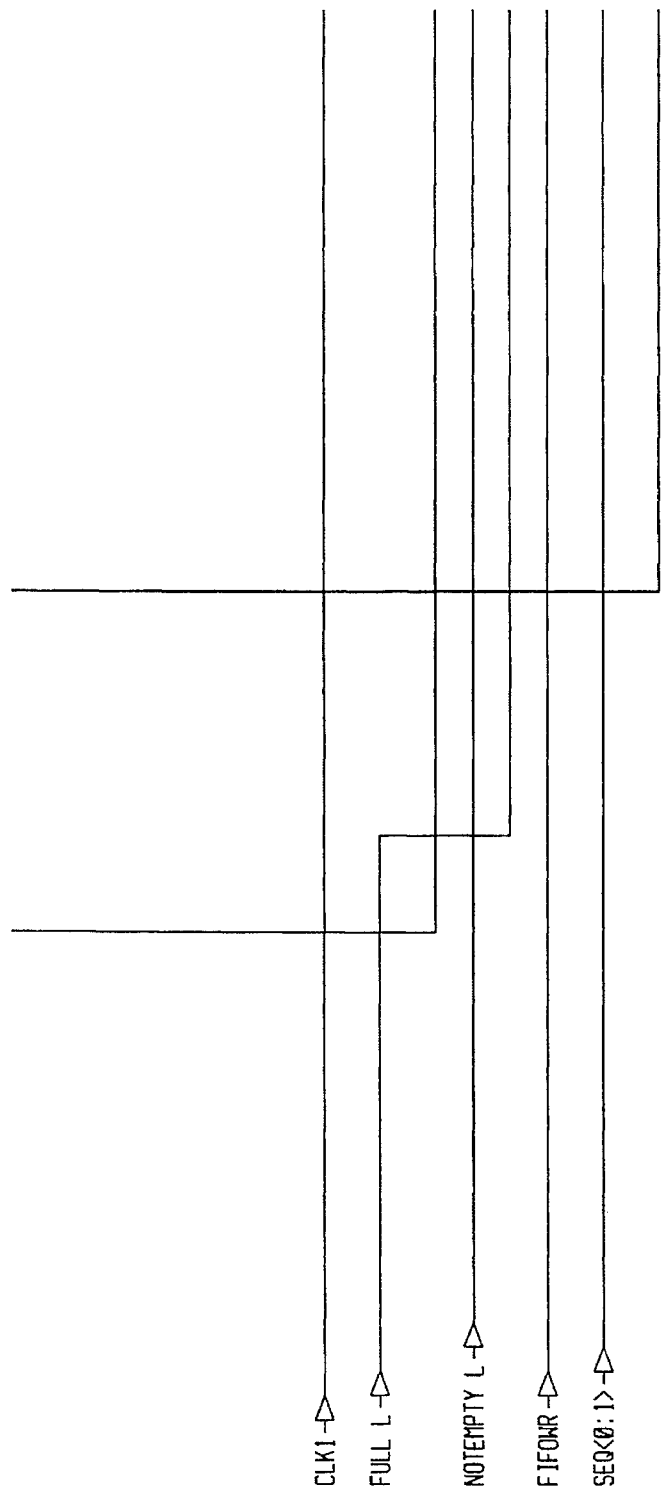
FIGURE 17J5

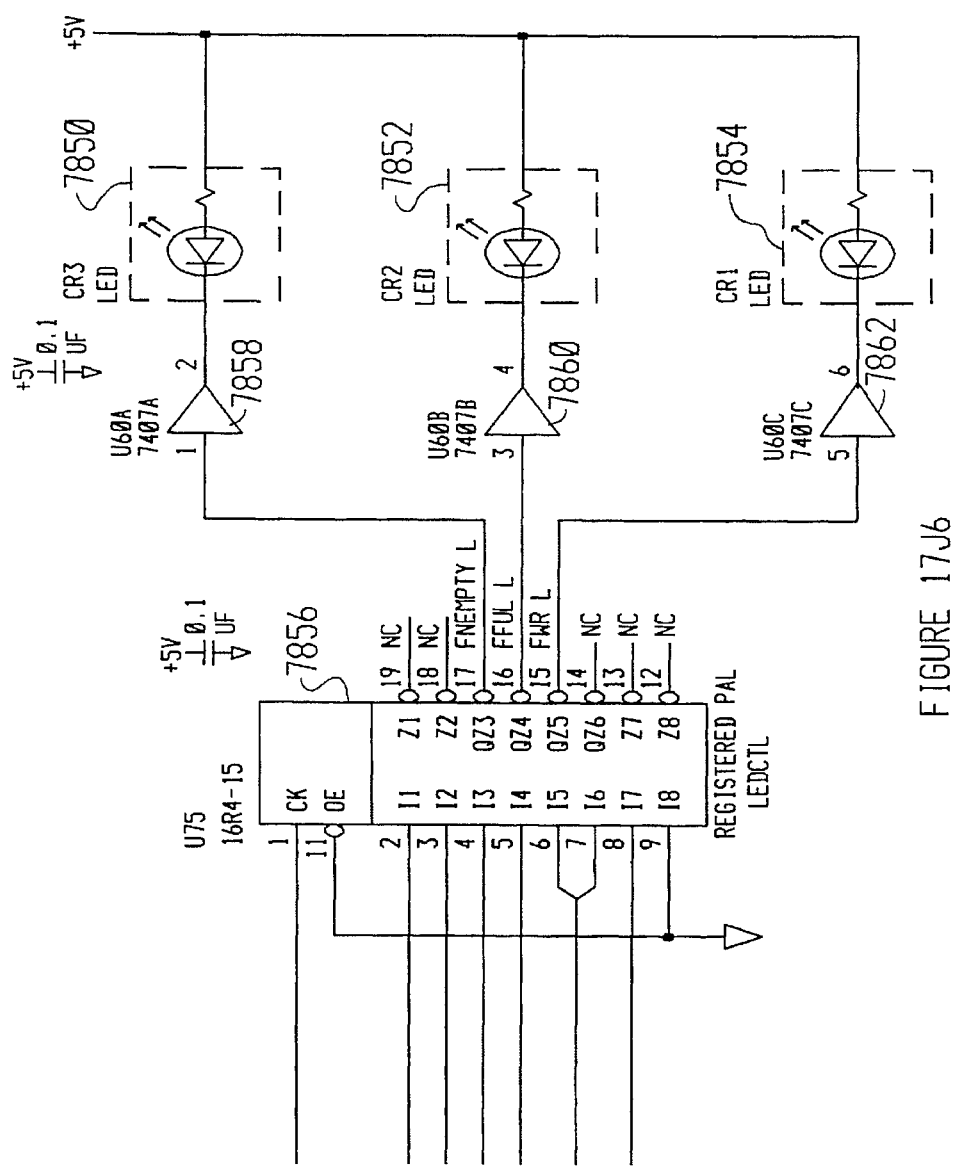
FIGURE 17J6

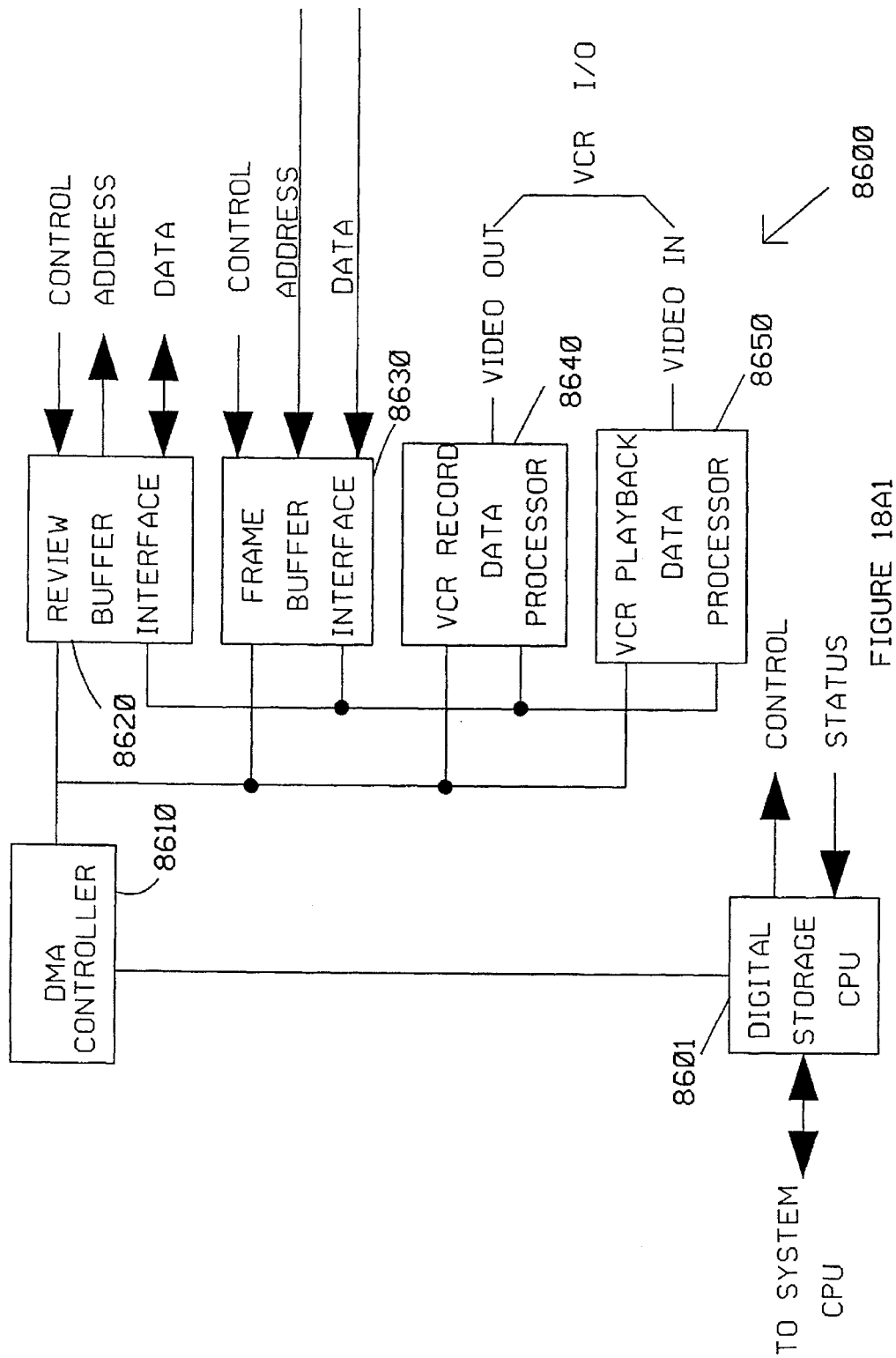
FIGURE 18A1

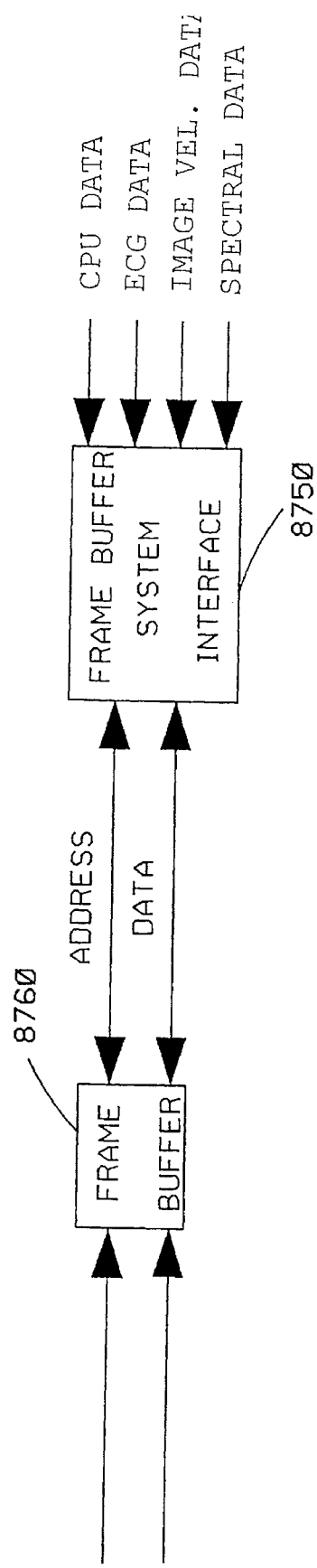
FIGURE 18A2

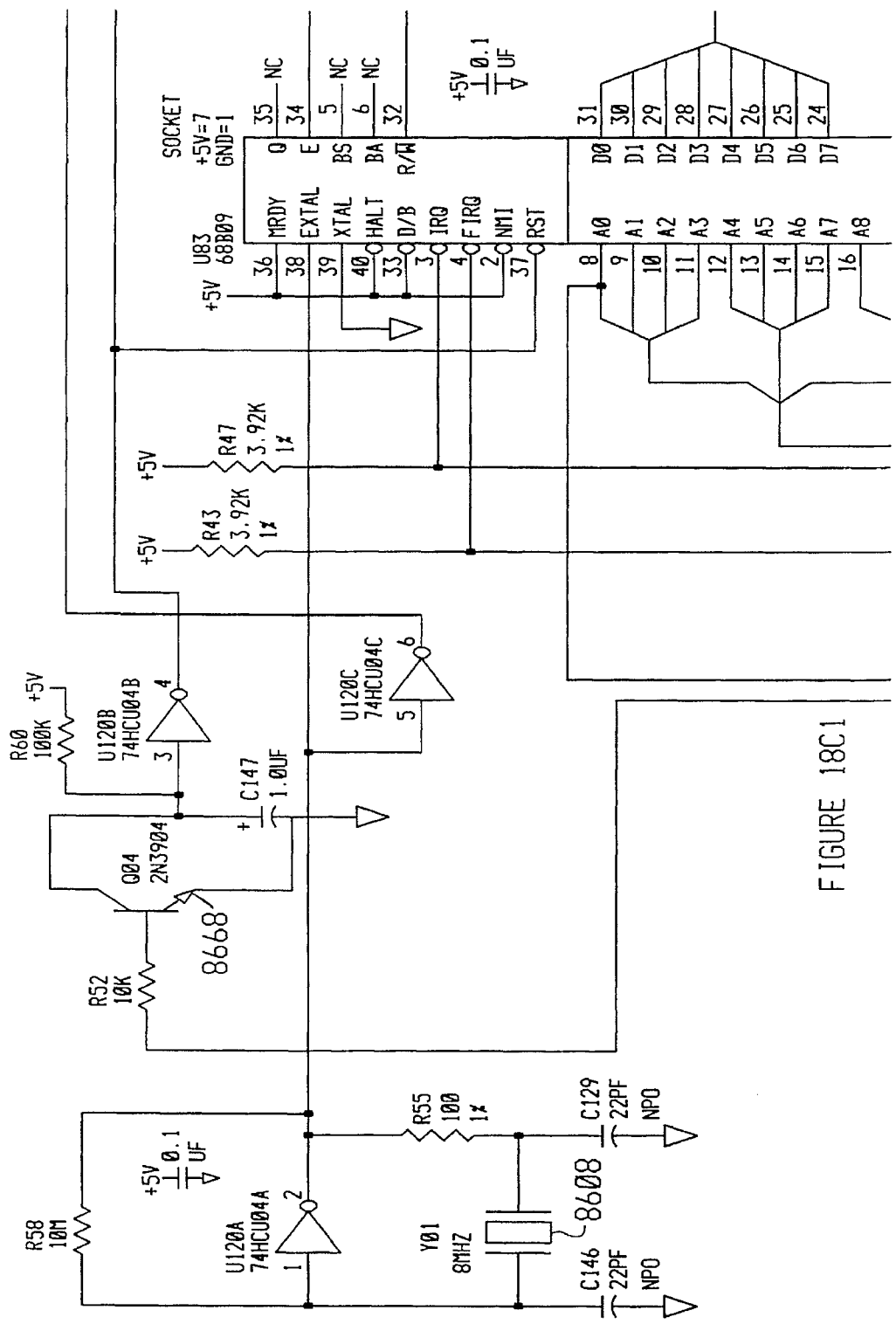
FIGURE 18C1

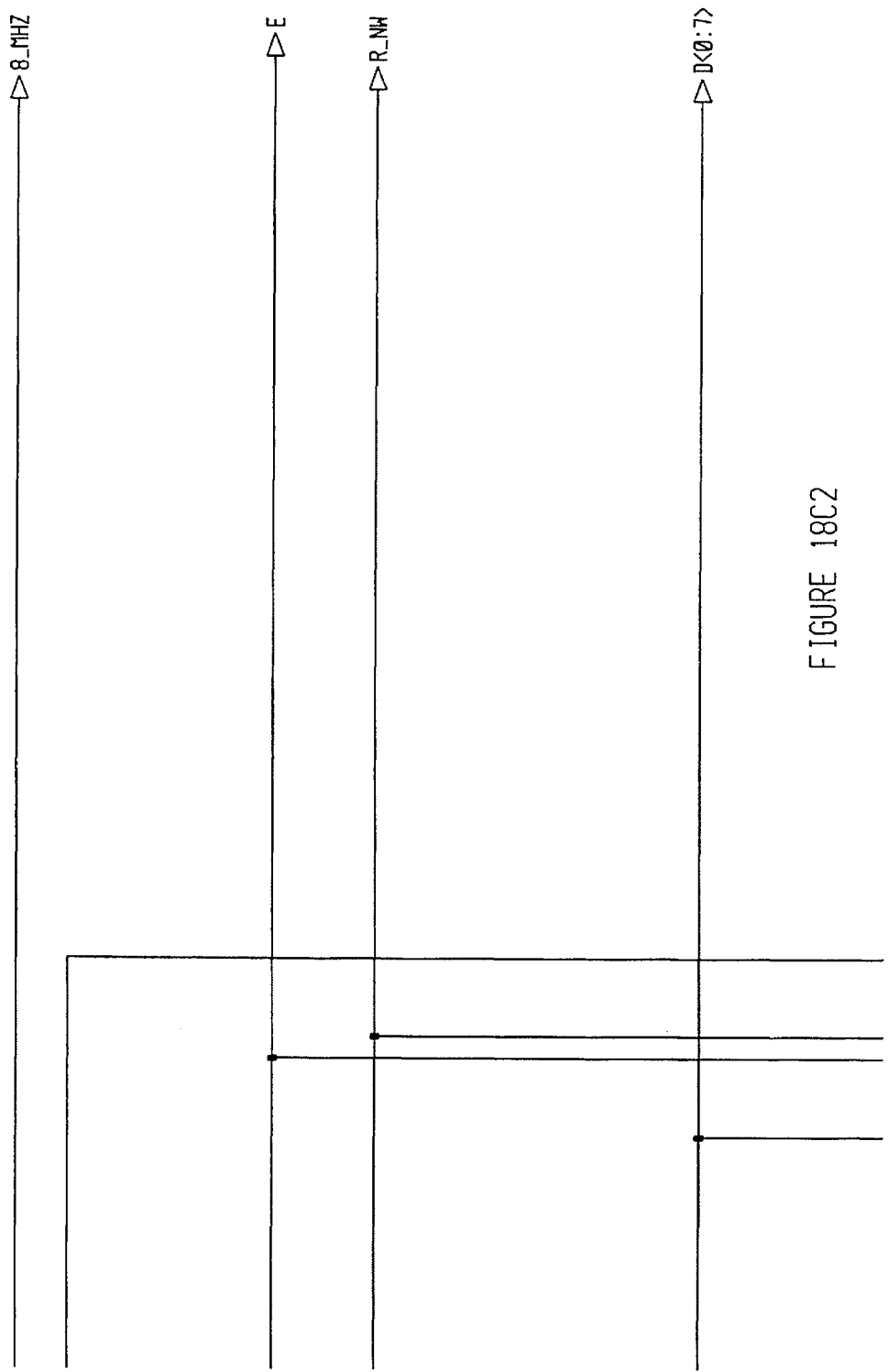

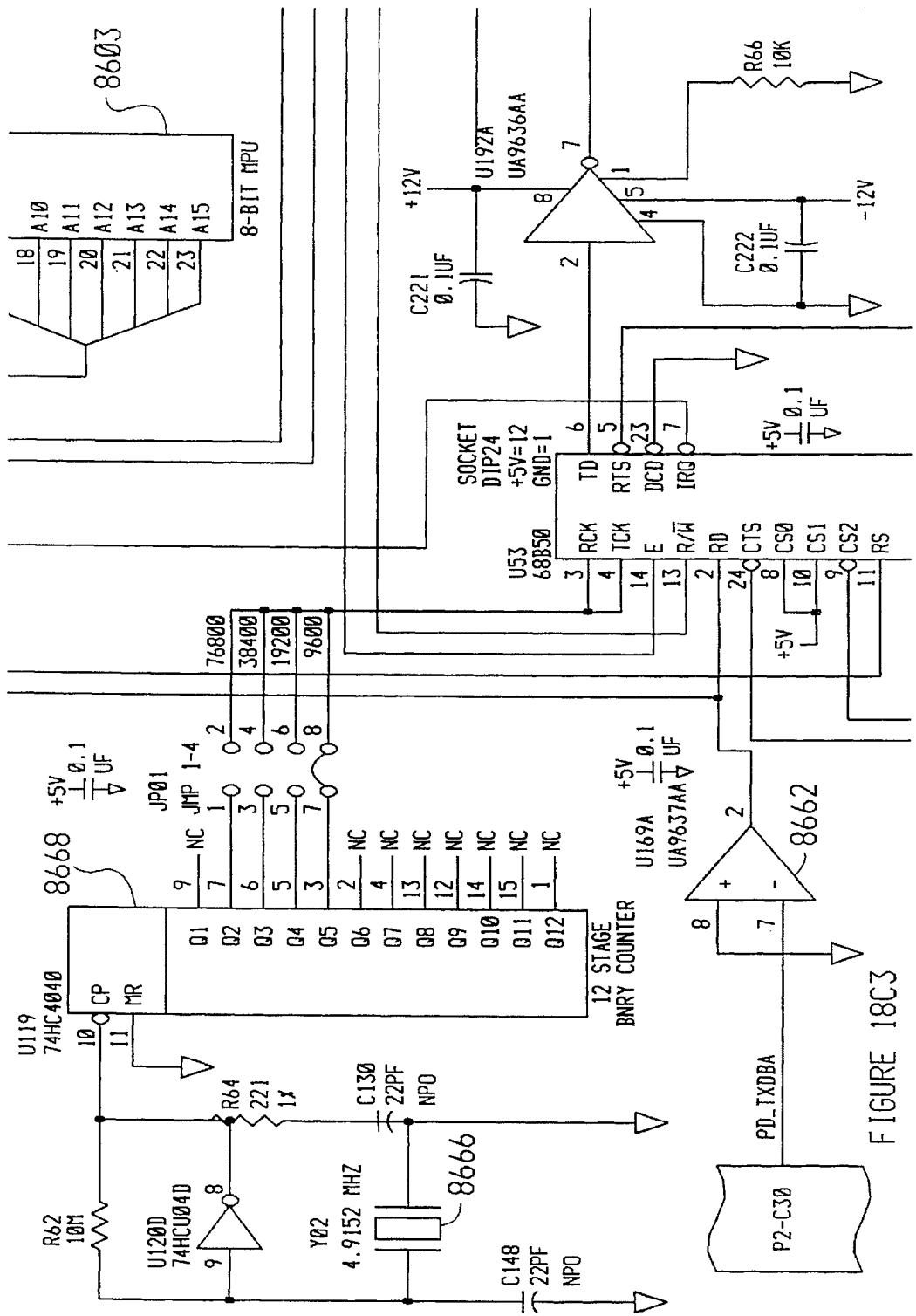
FIGURE 18C3

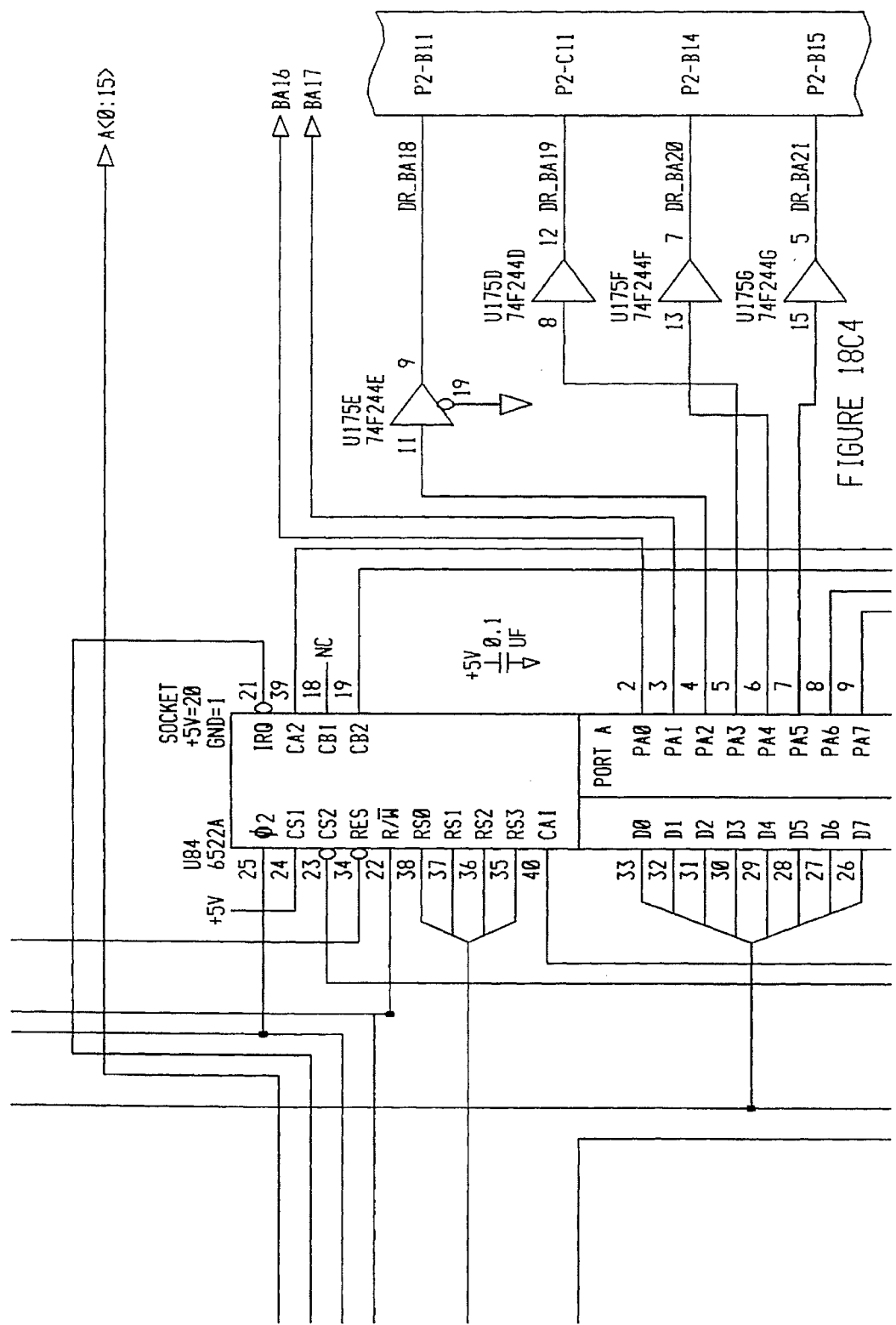
FIGURE 18C4

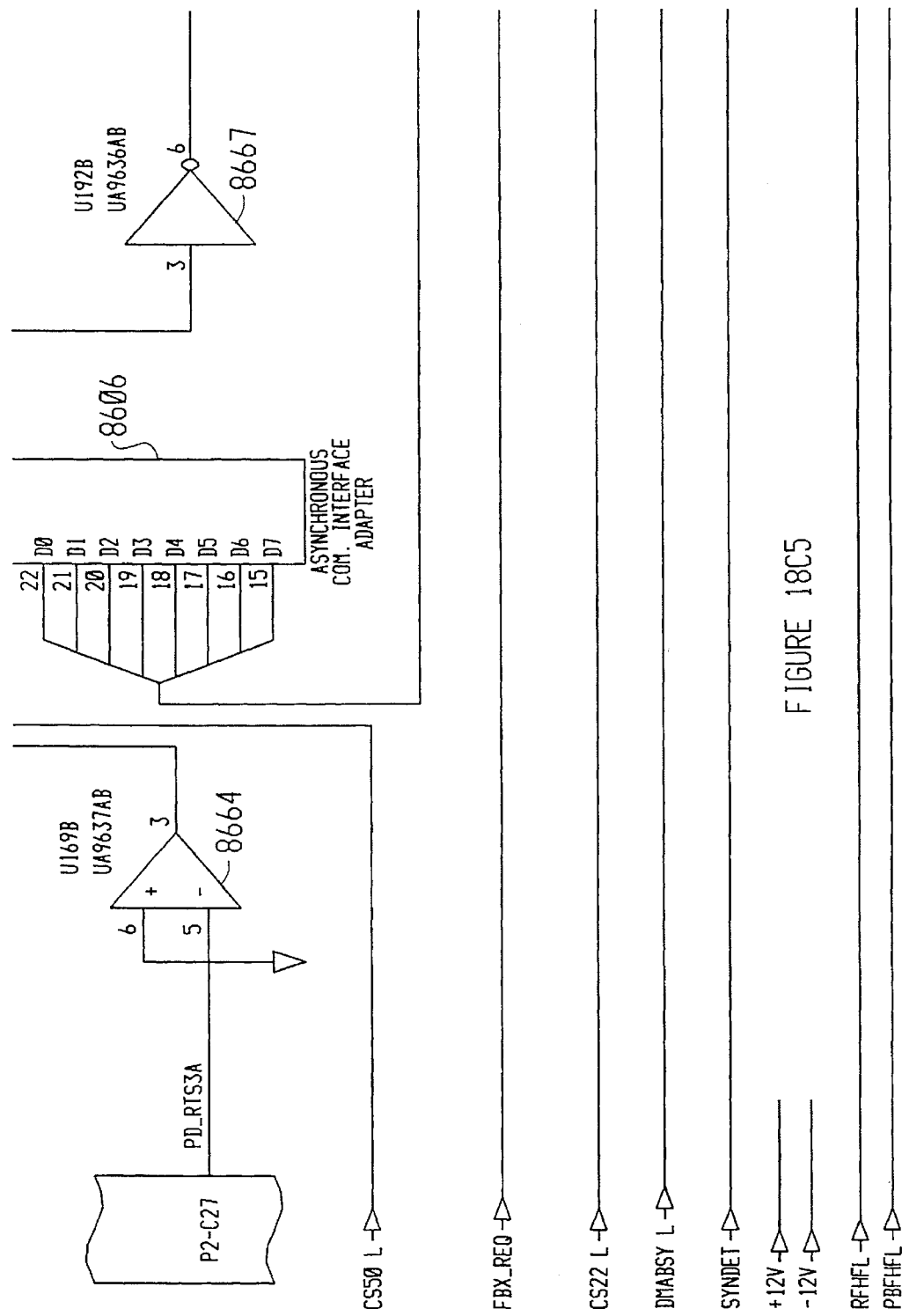
FIGURE 18C5

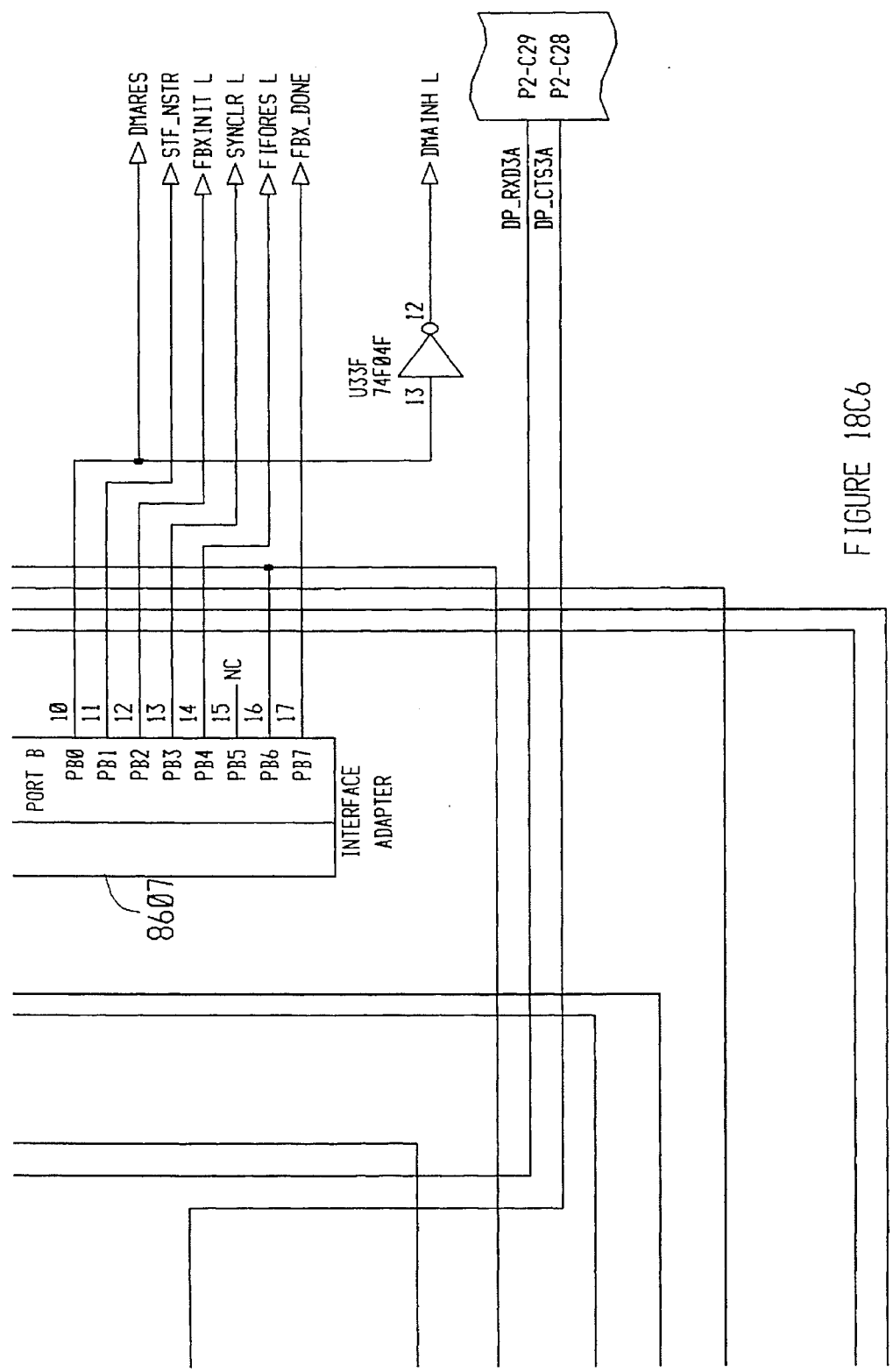
FIGURE 18C6

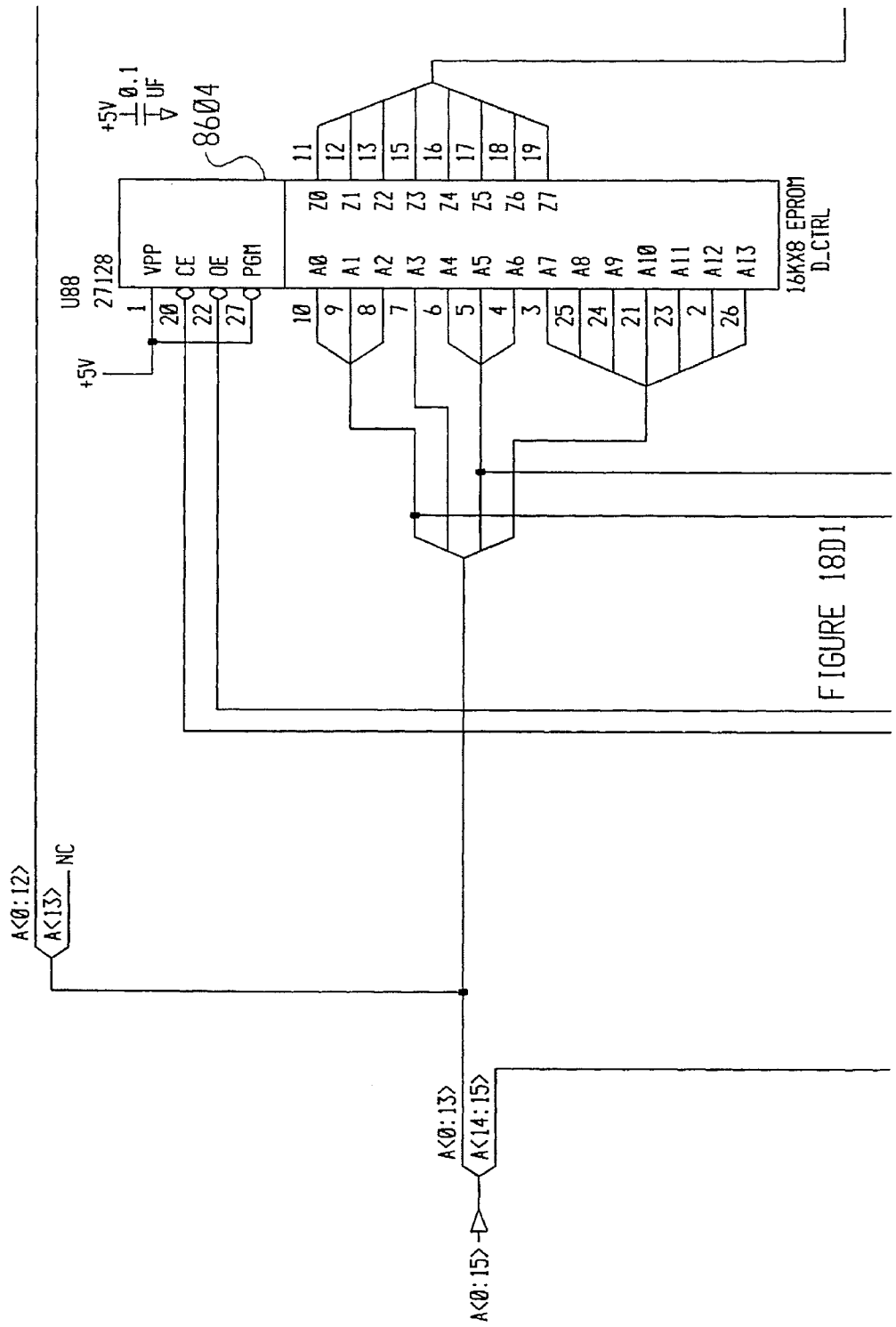
FIGURE 18D1

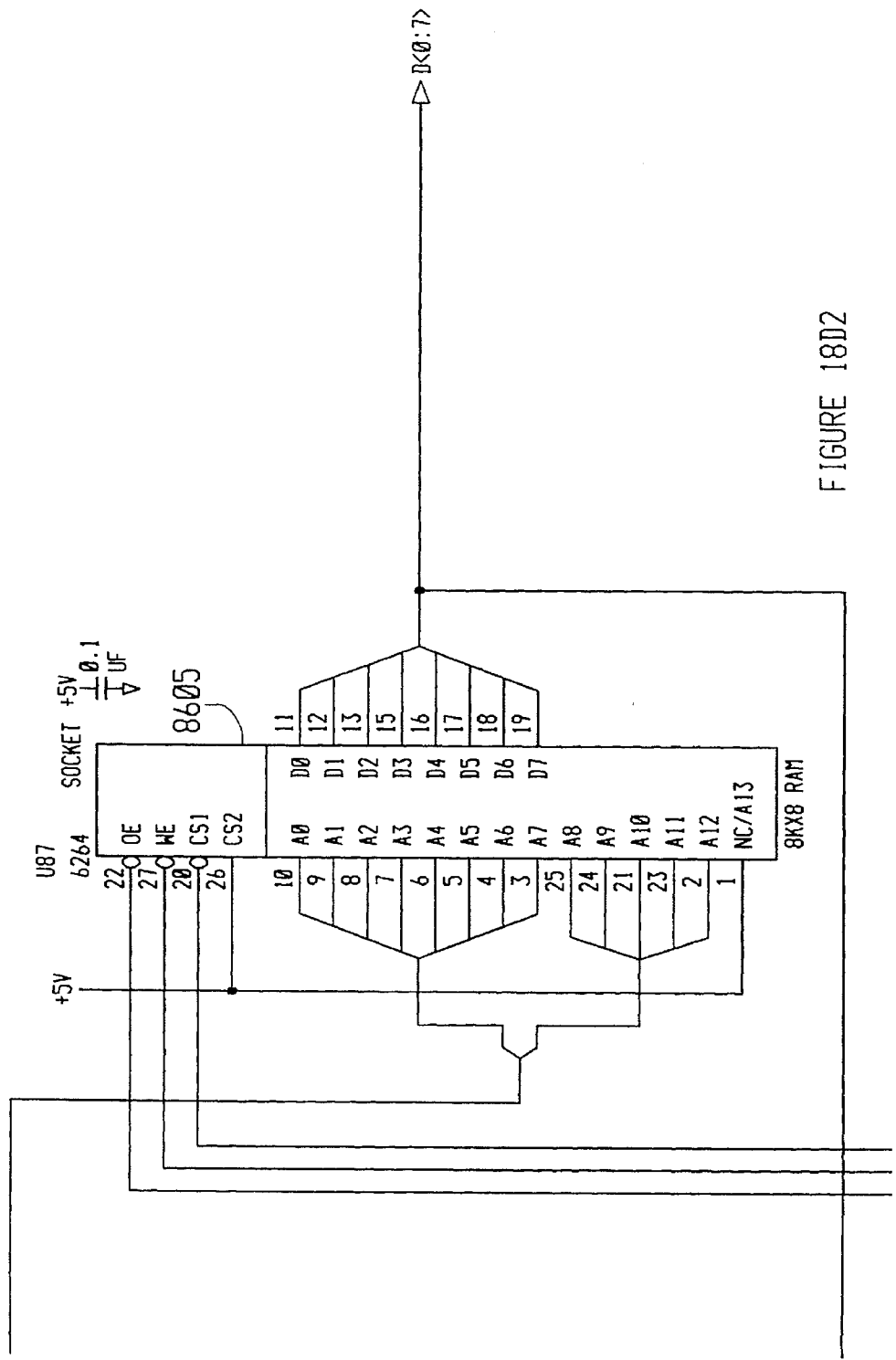
FIGURE 18D2

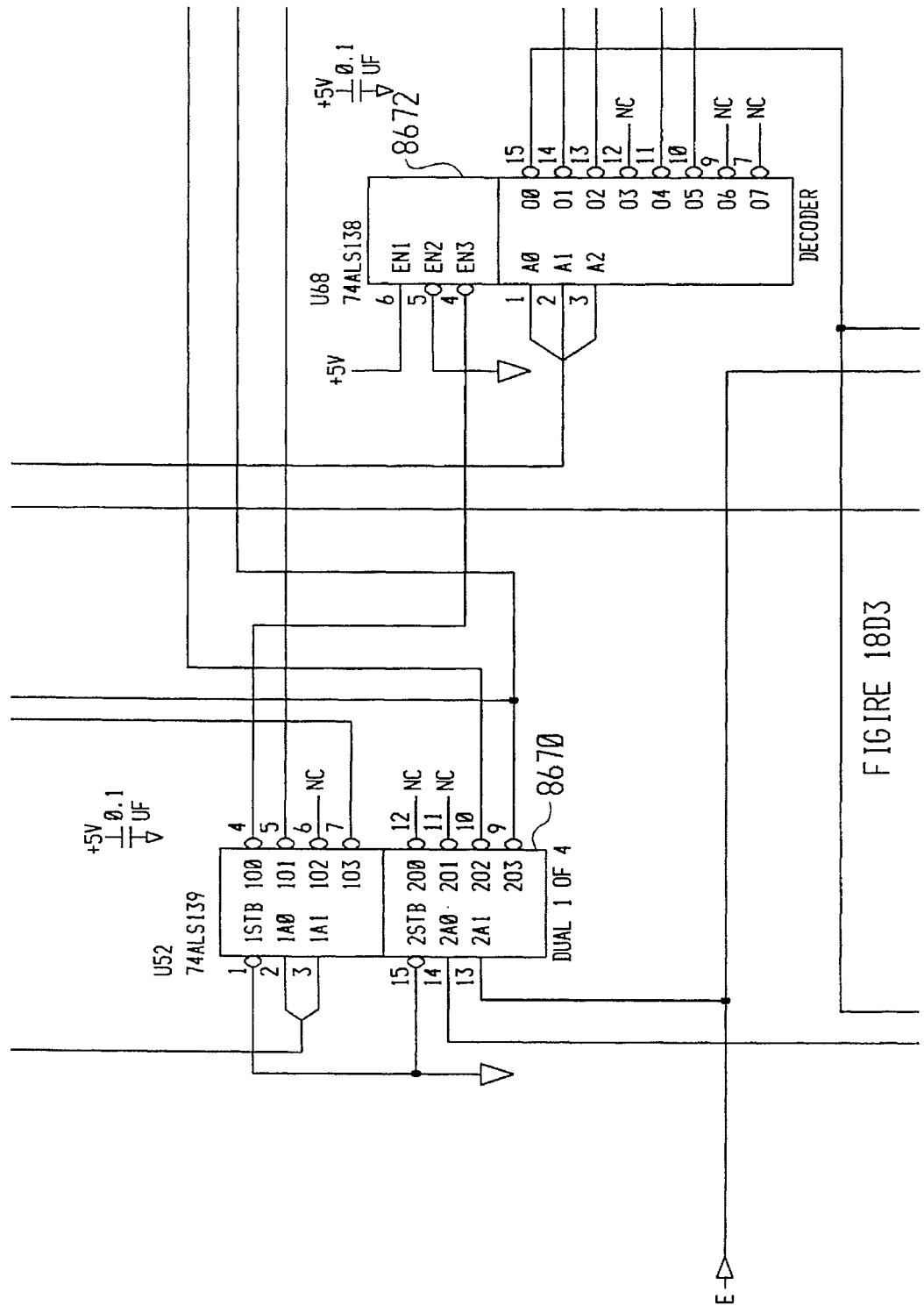

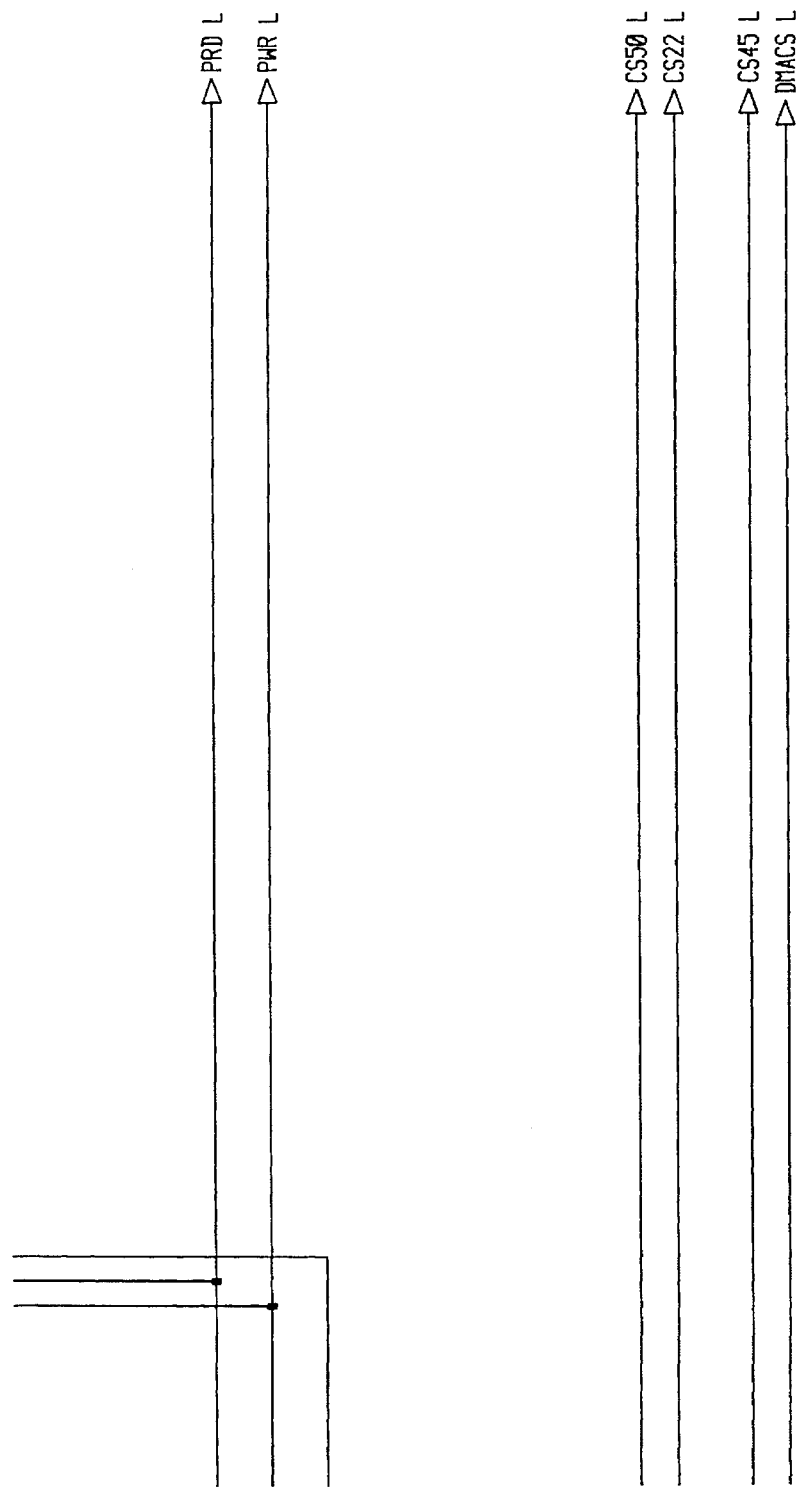
FIGURE 18D4

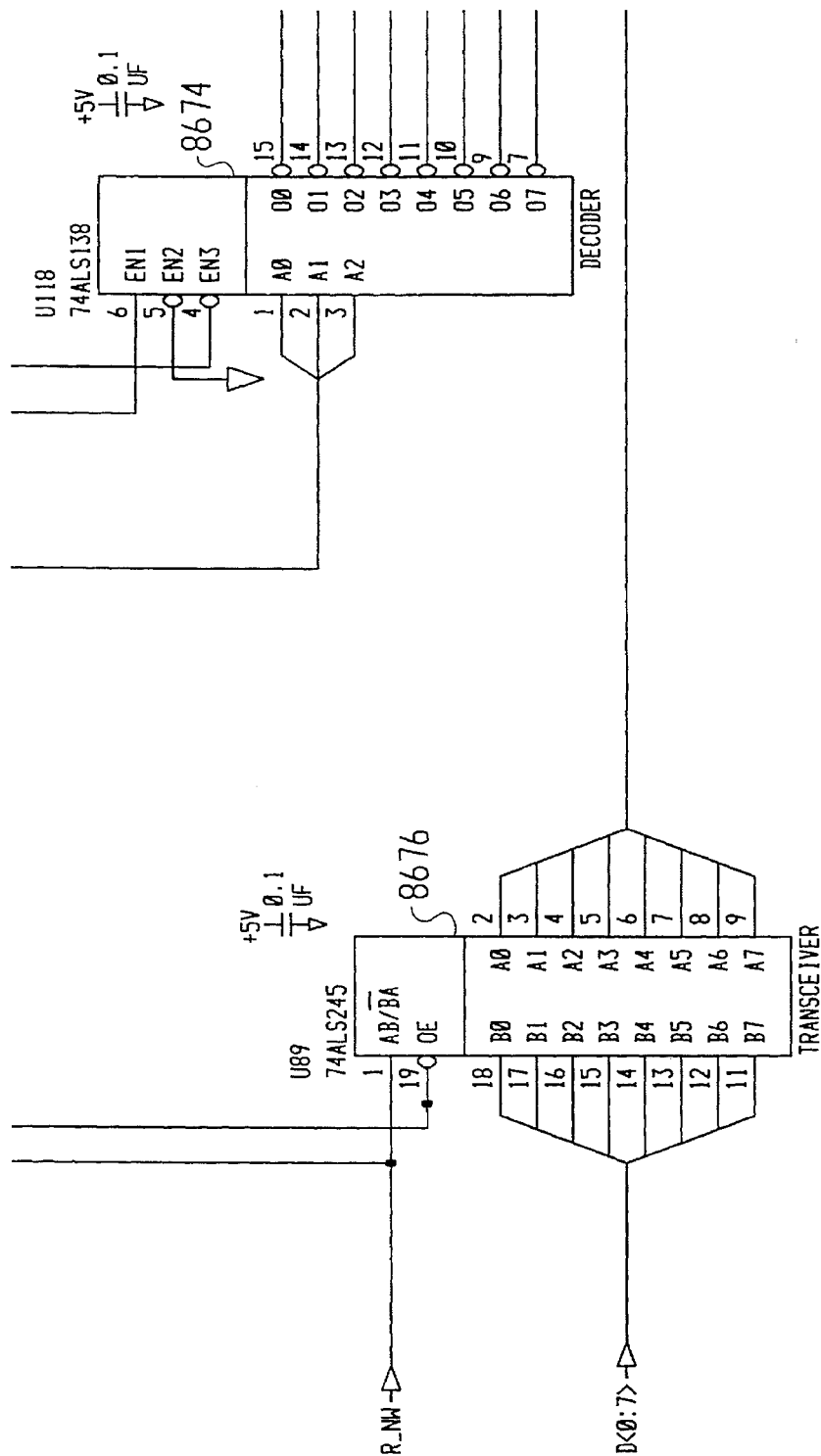
FIGURE 18D5

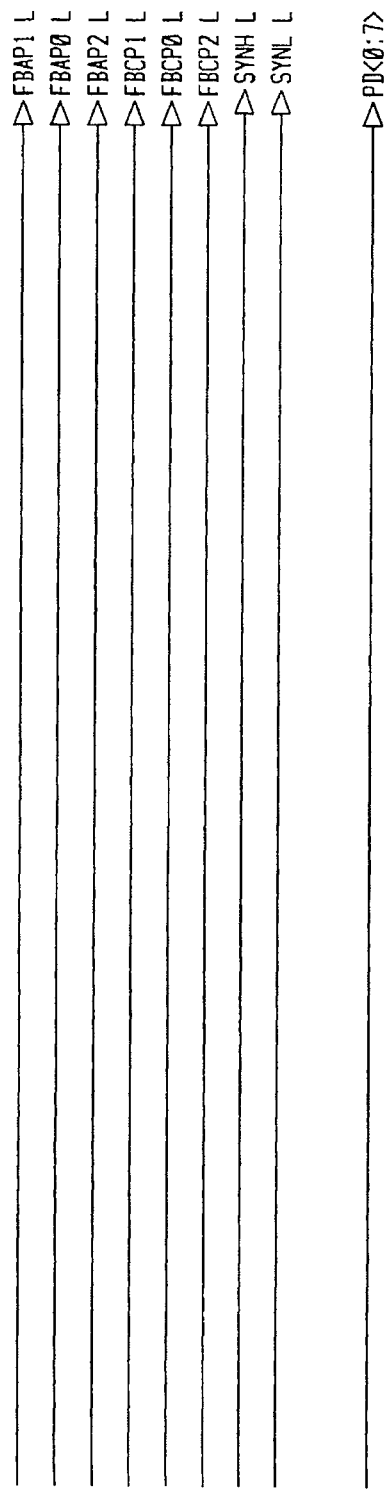
FIGURE 18D6

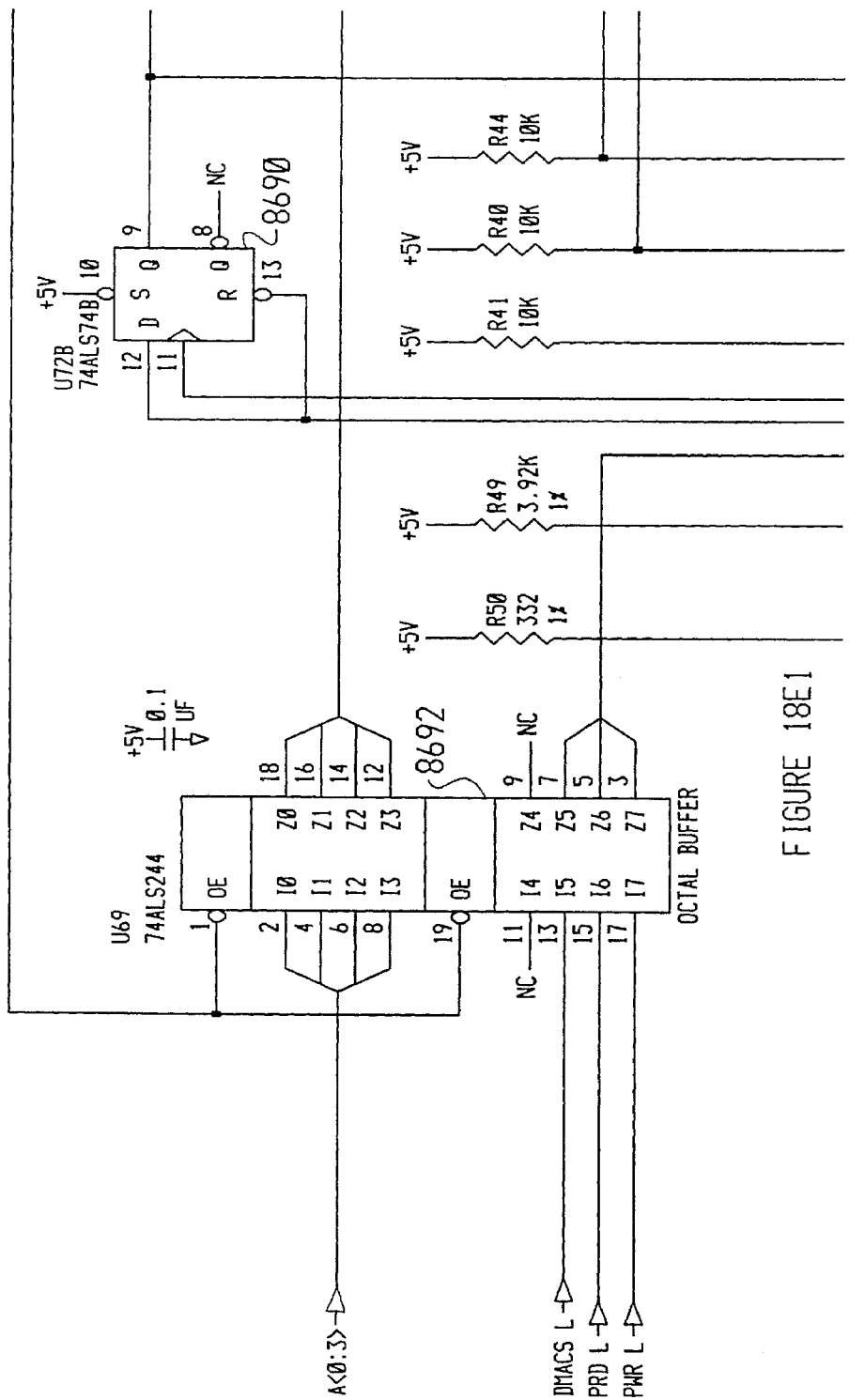
FIGURE 18E1

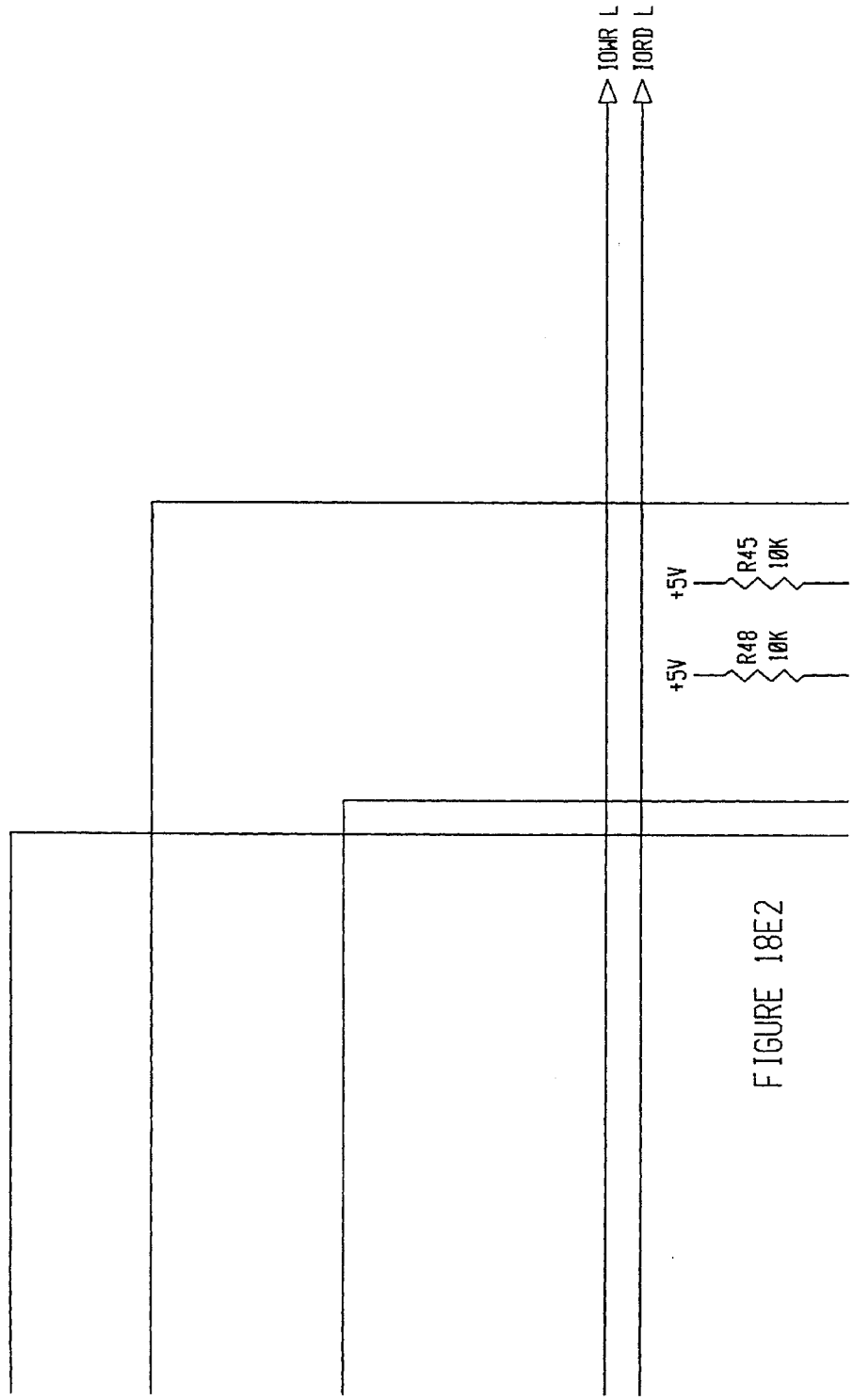
FIGURE 18E2

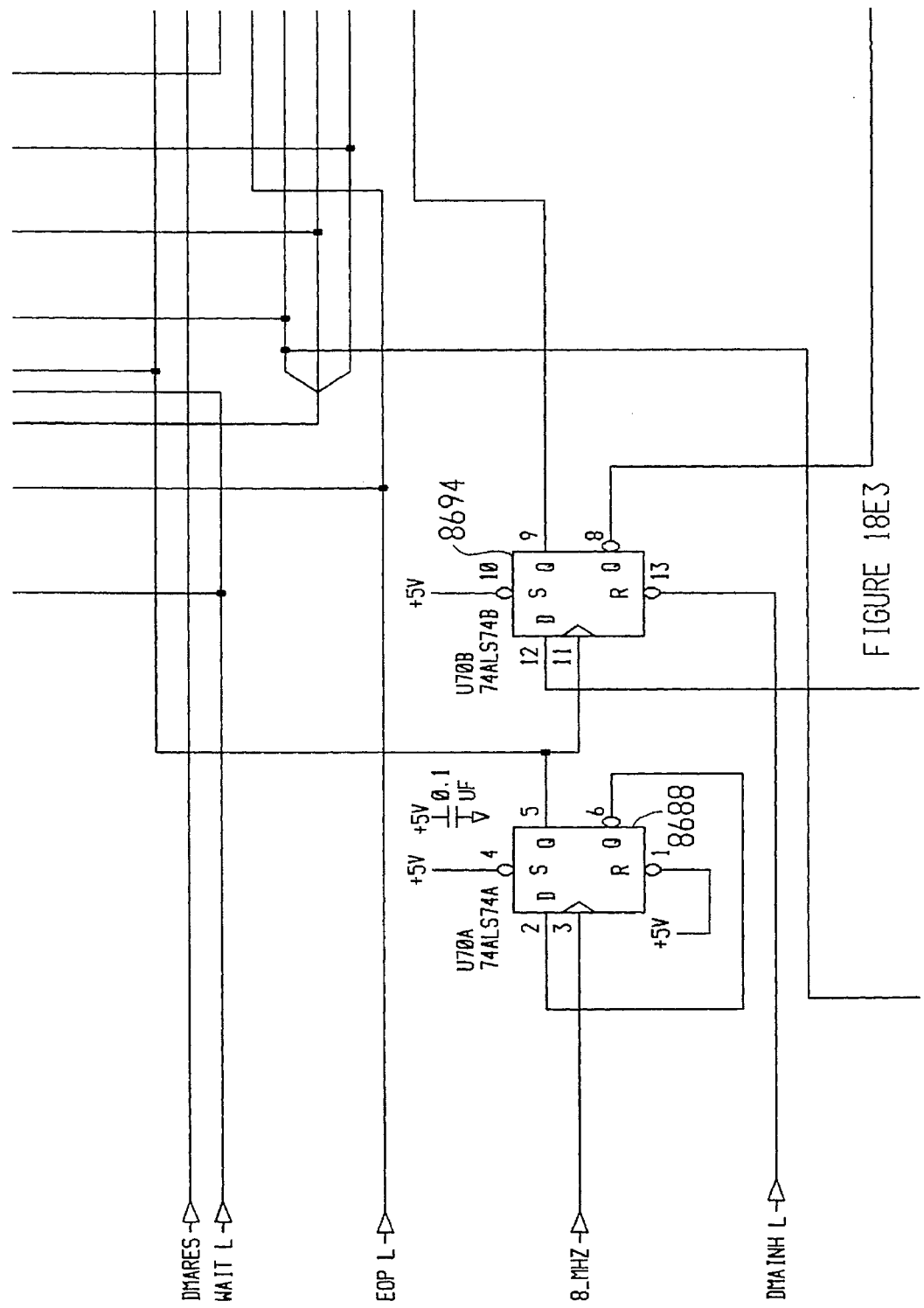

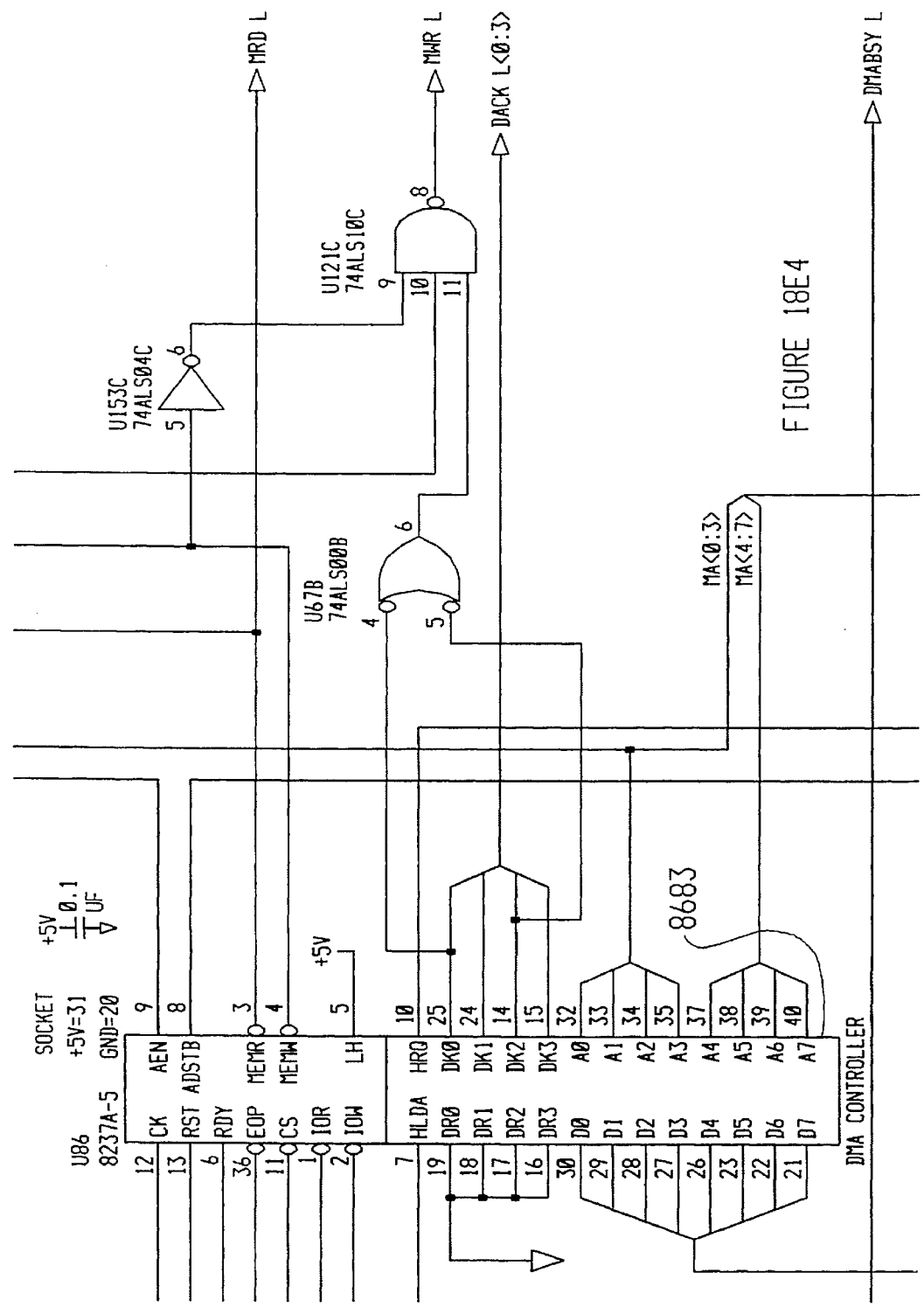
FIGURE 18E4

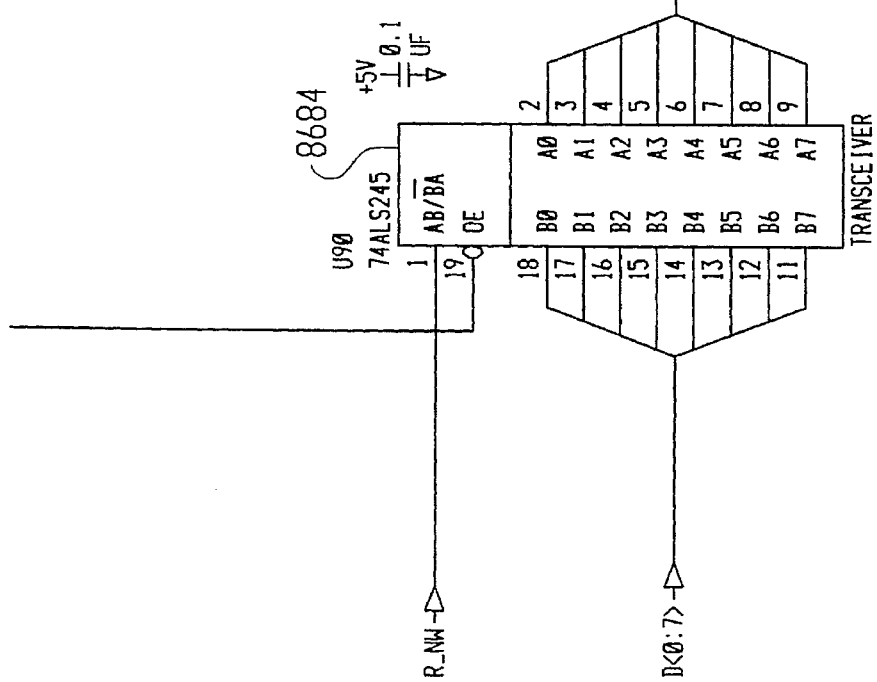
FIGURE 18E5

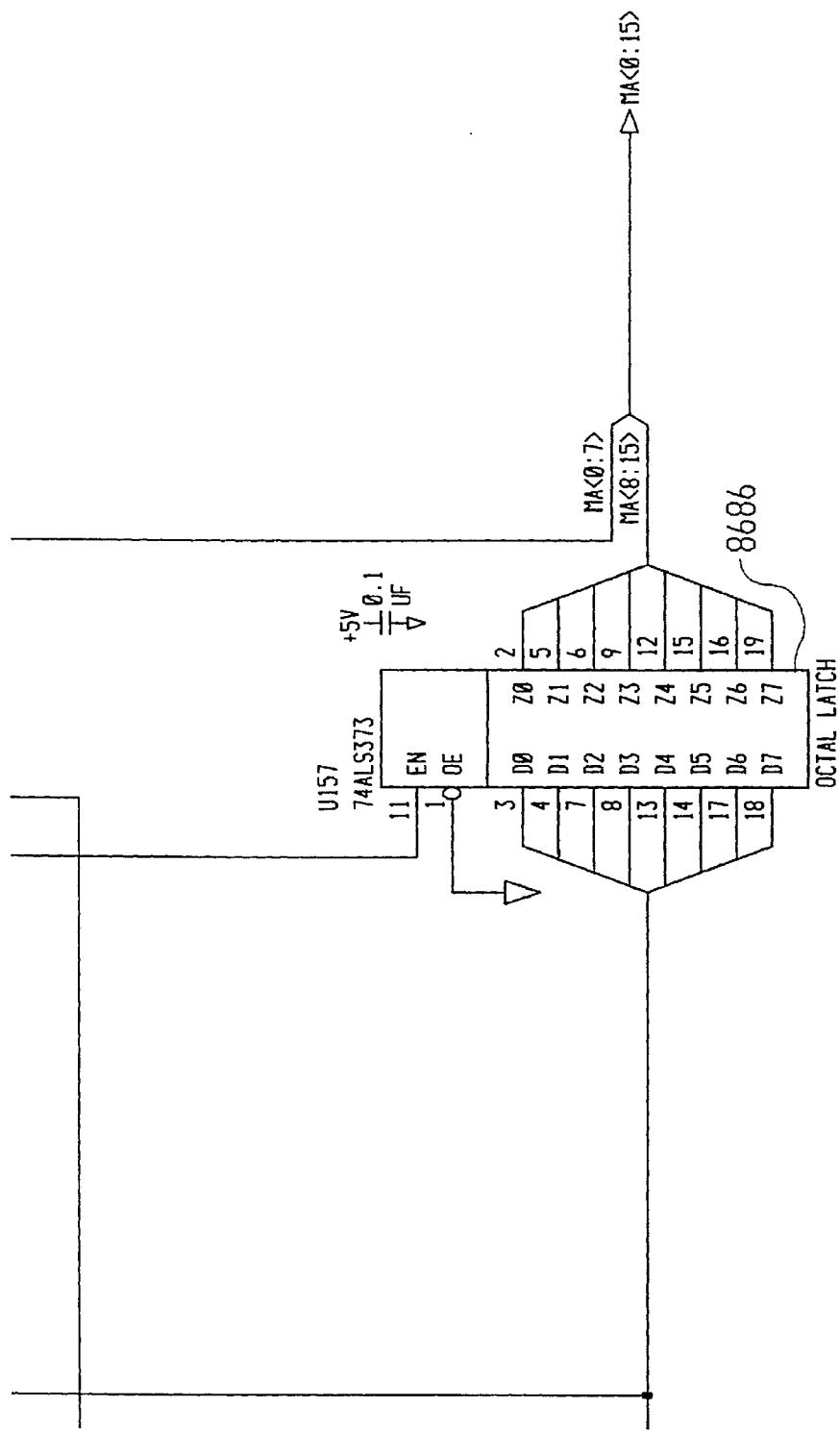
FIGURE 18E6

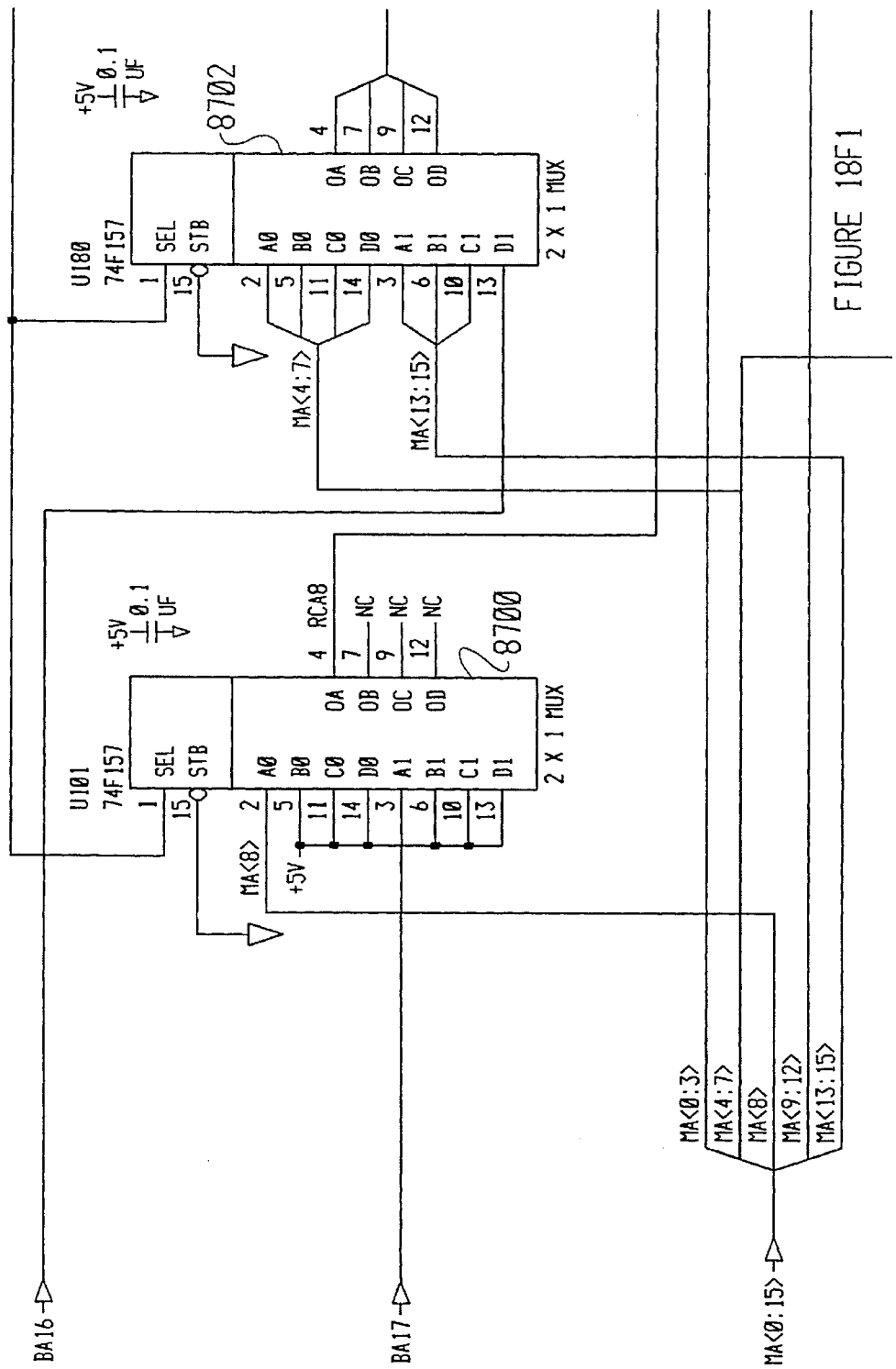
FIGURE 18F1

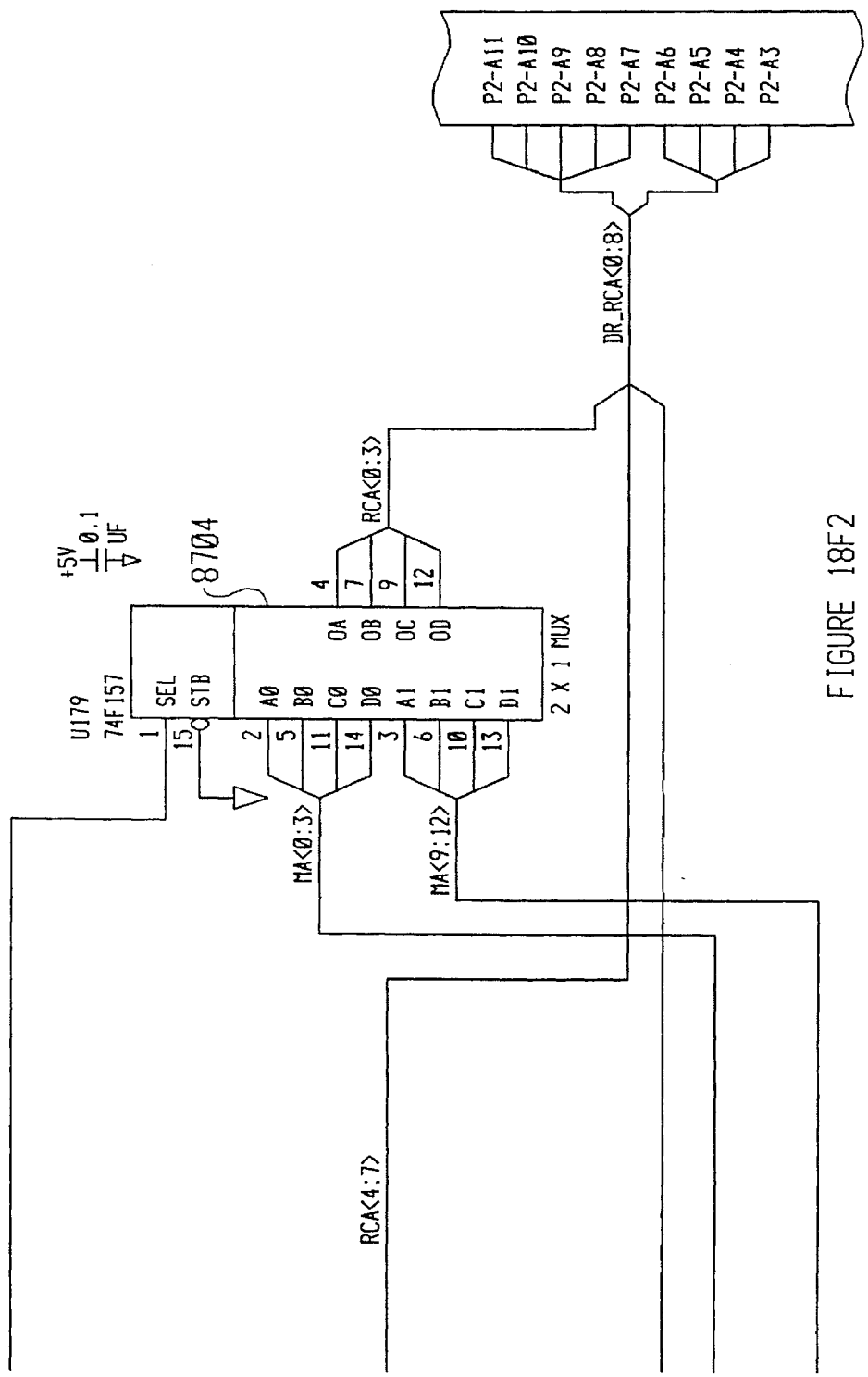
FIGURE 18F2

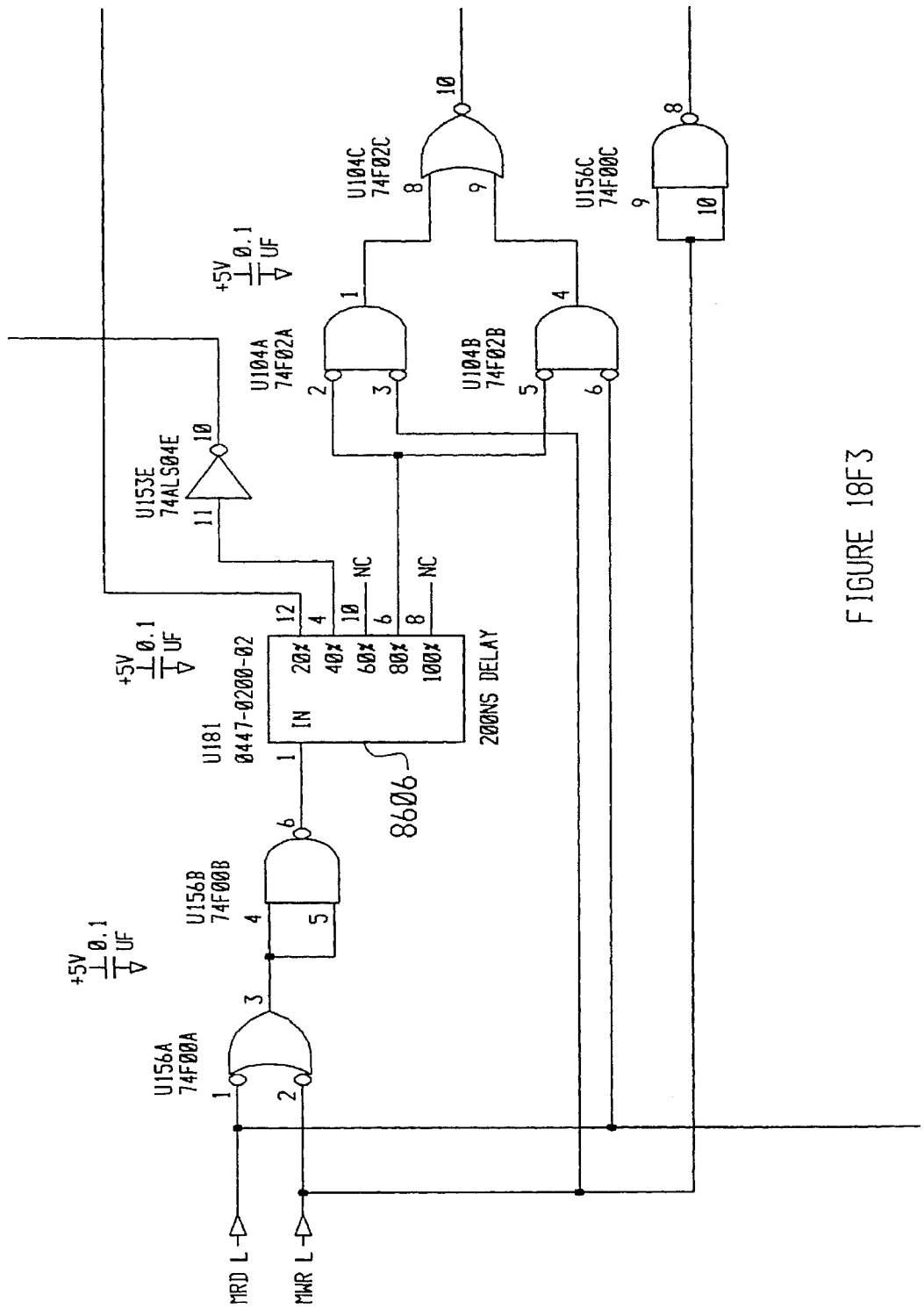
FIGURE 18F3

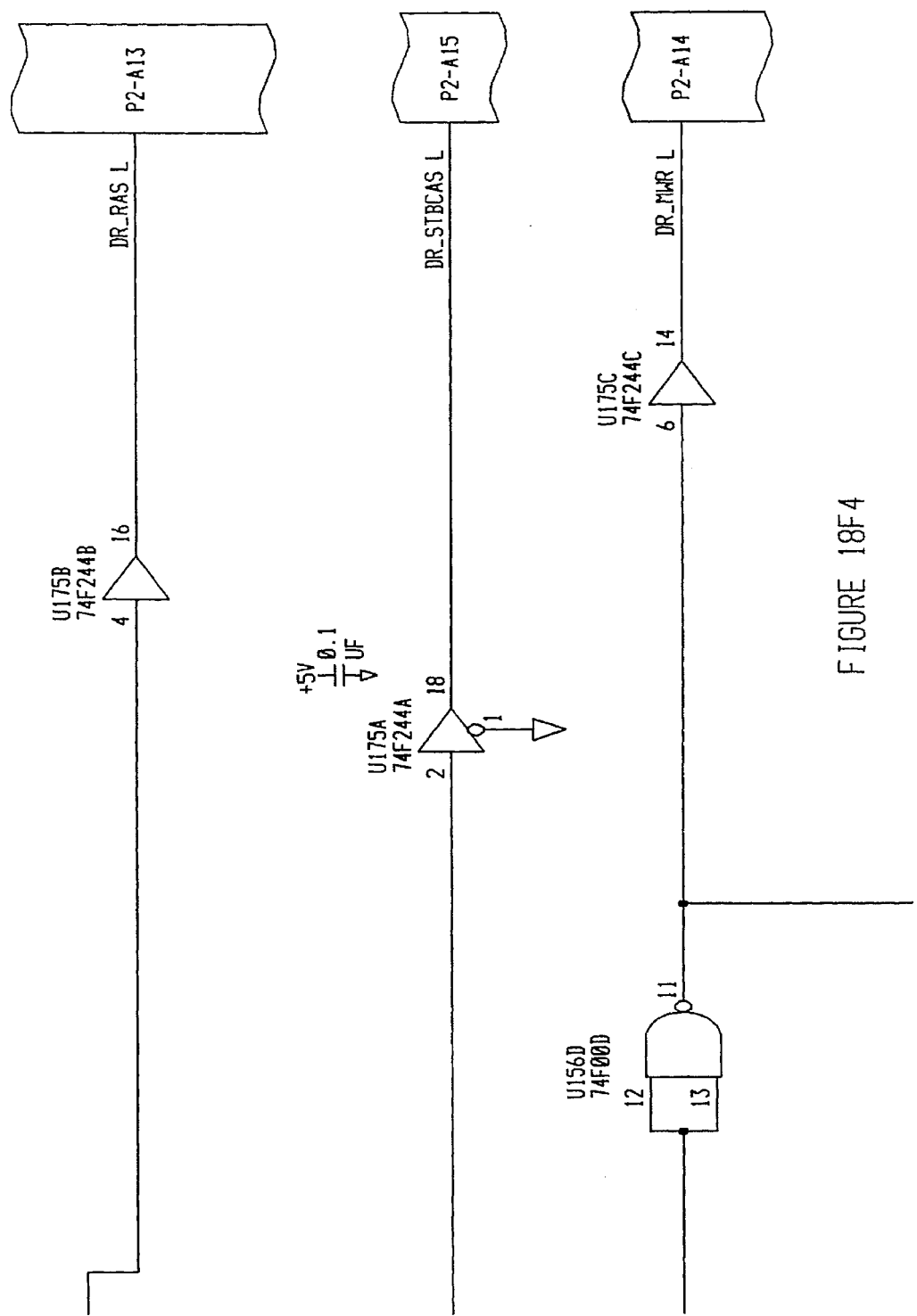
FIGURE 18F4

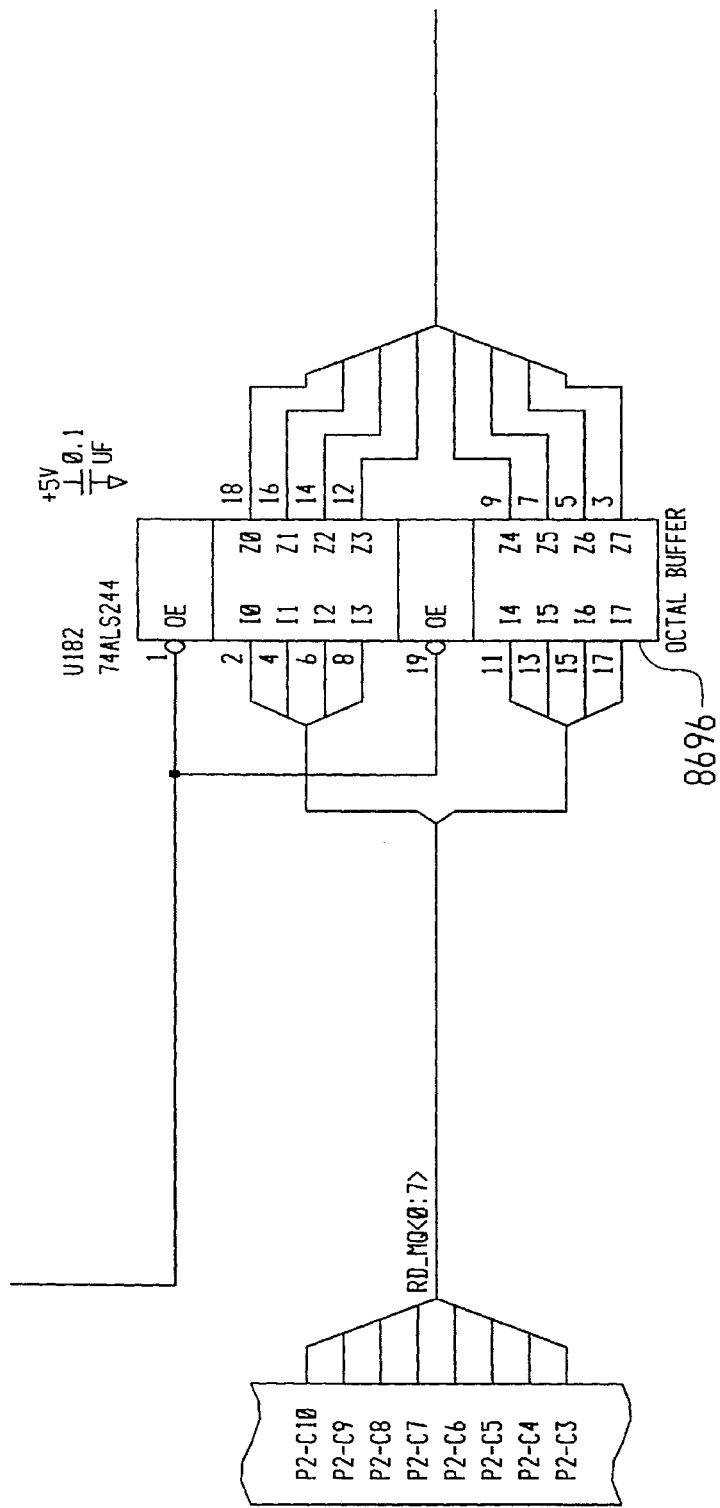
FIGURE 18F5

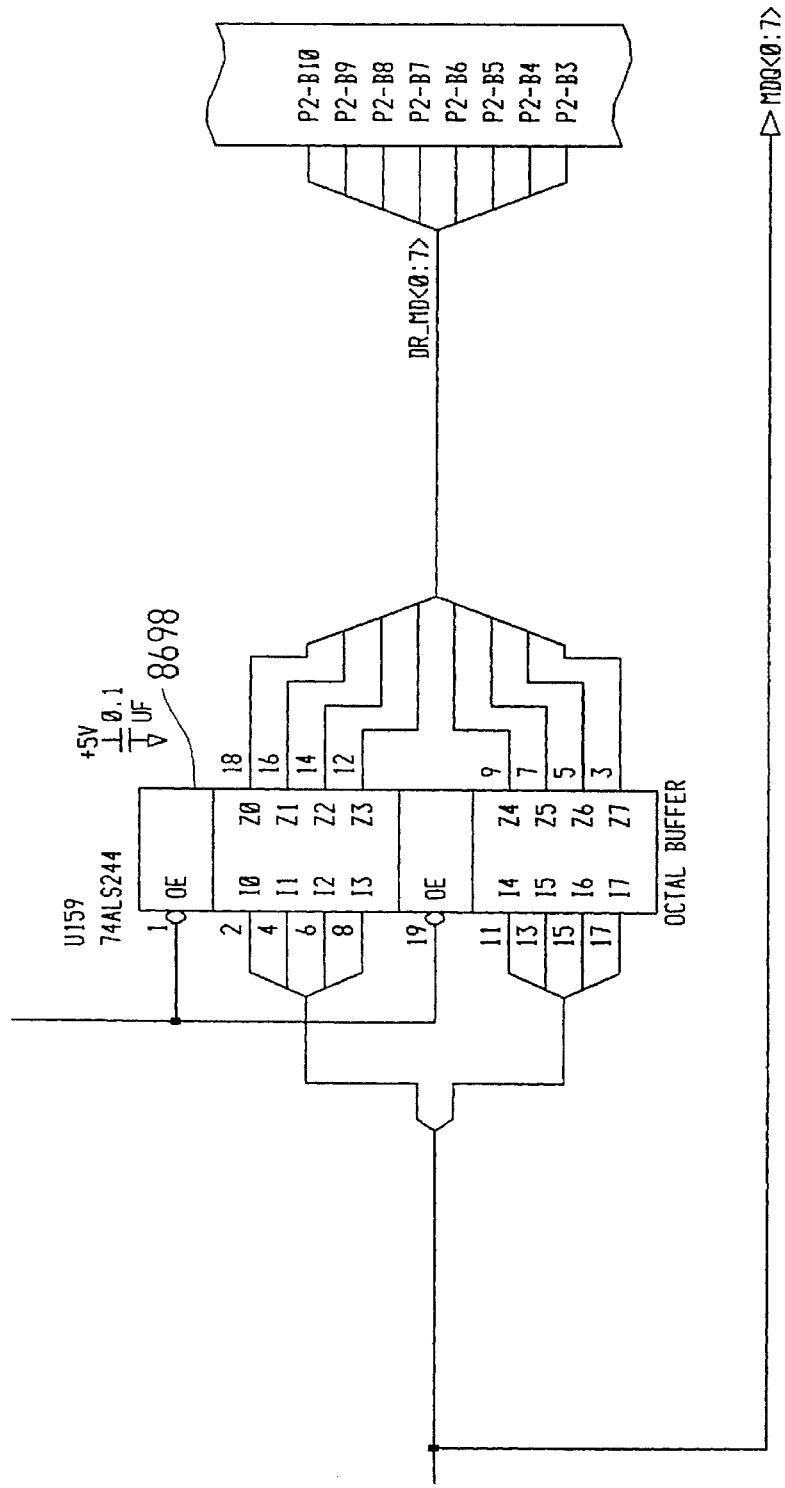
FIGURE 18F6

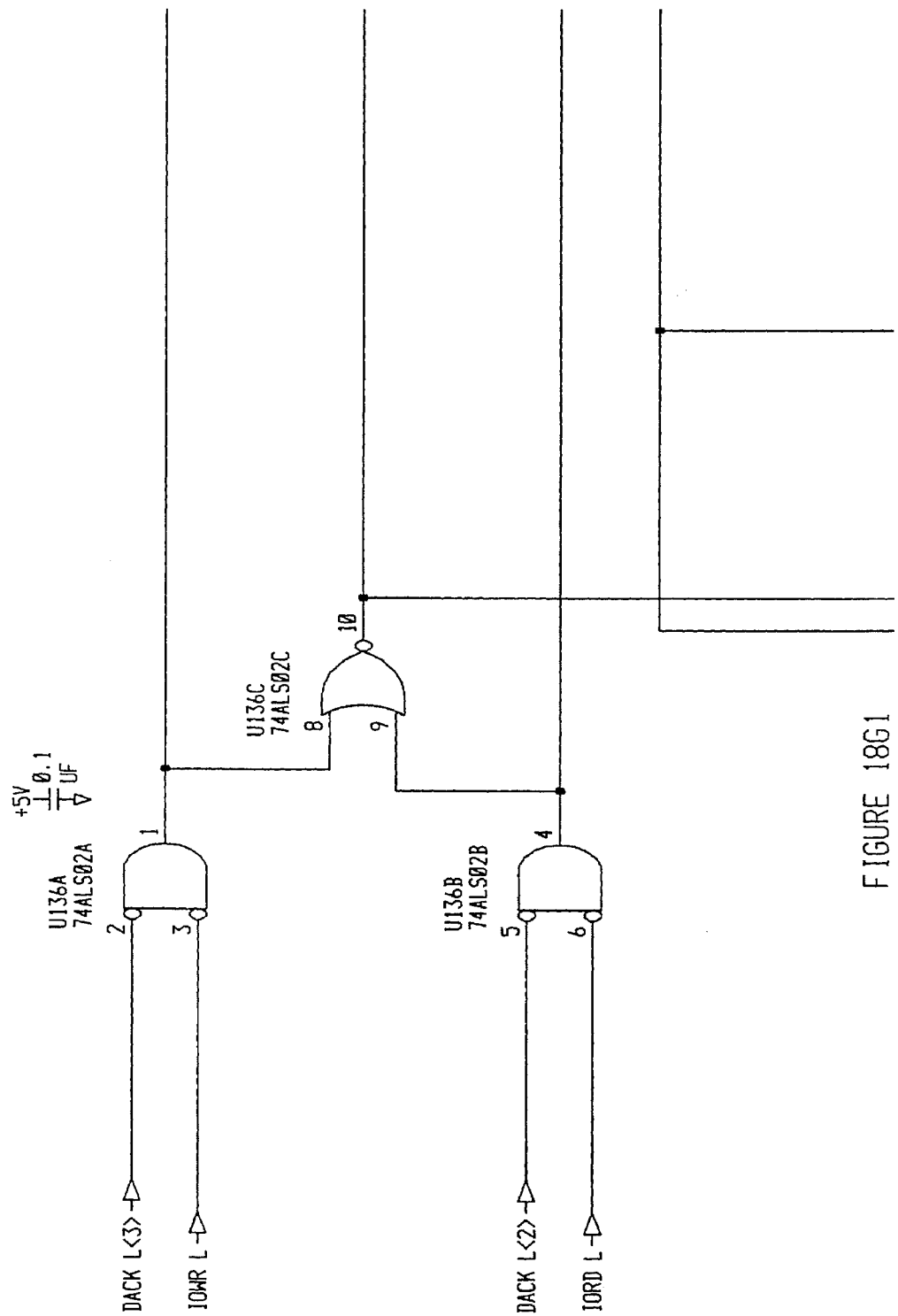
FIGURE 18G1

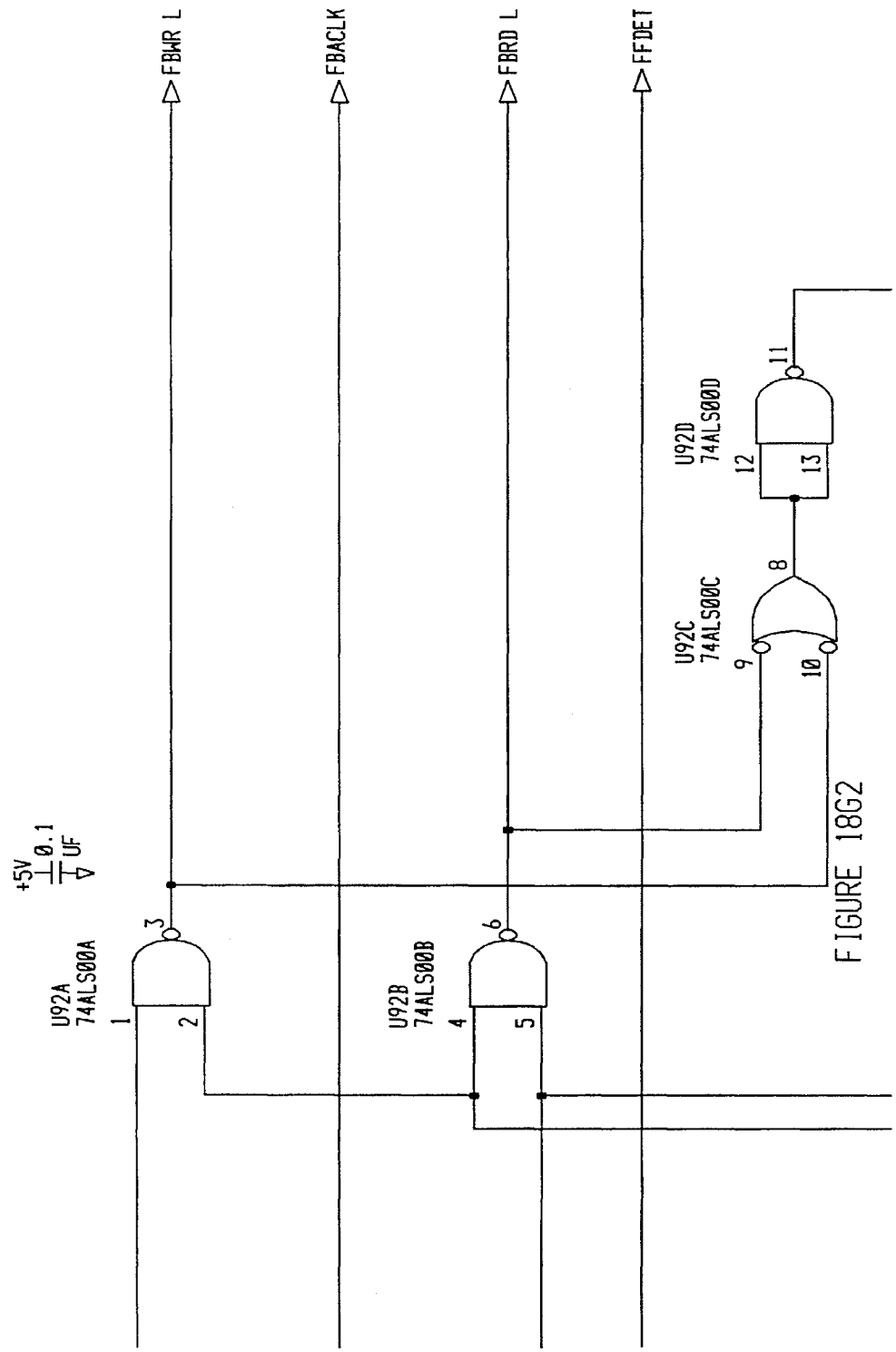
FIGURE 18G2

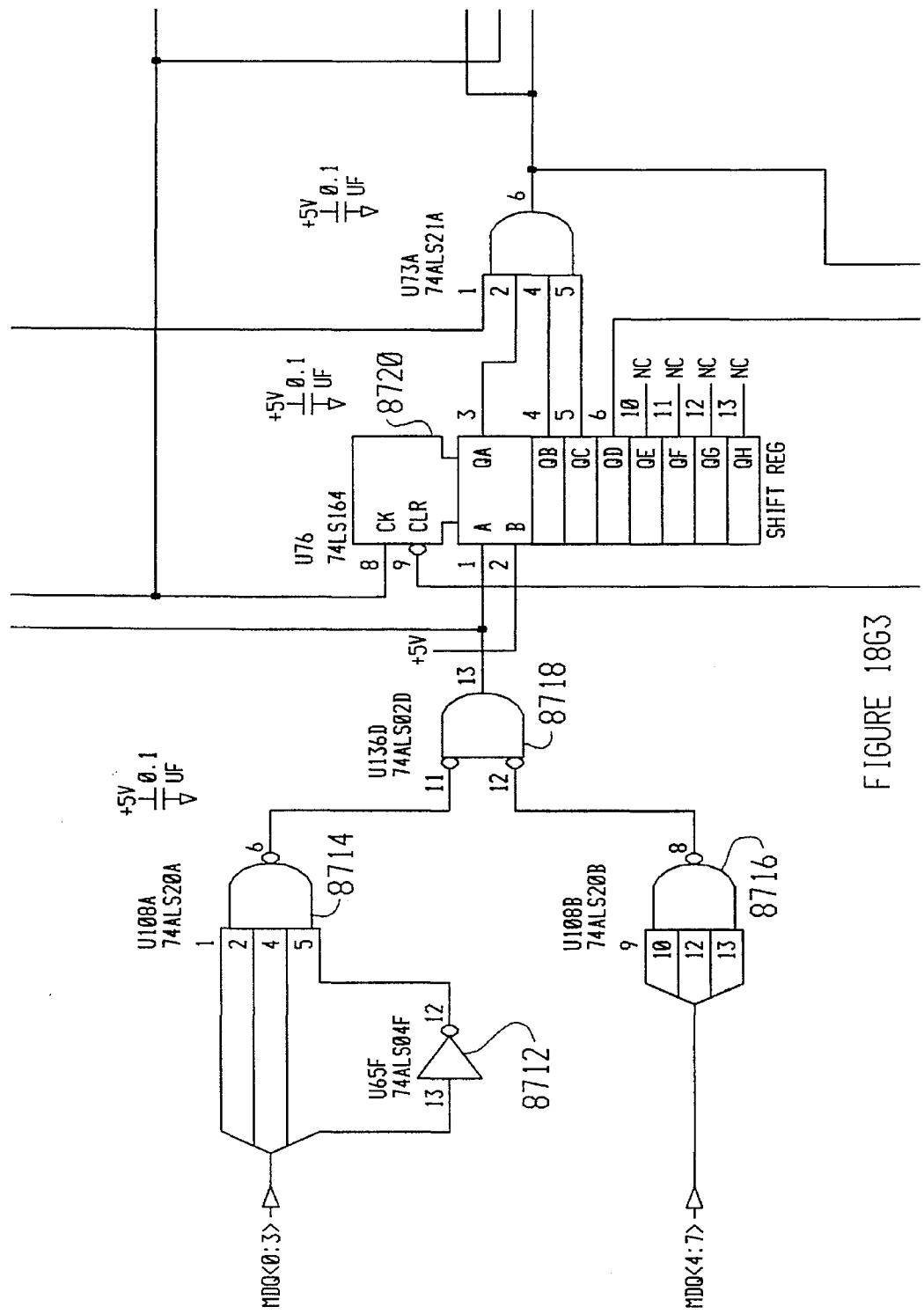
FIGURE 18G3

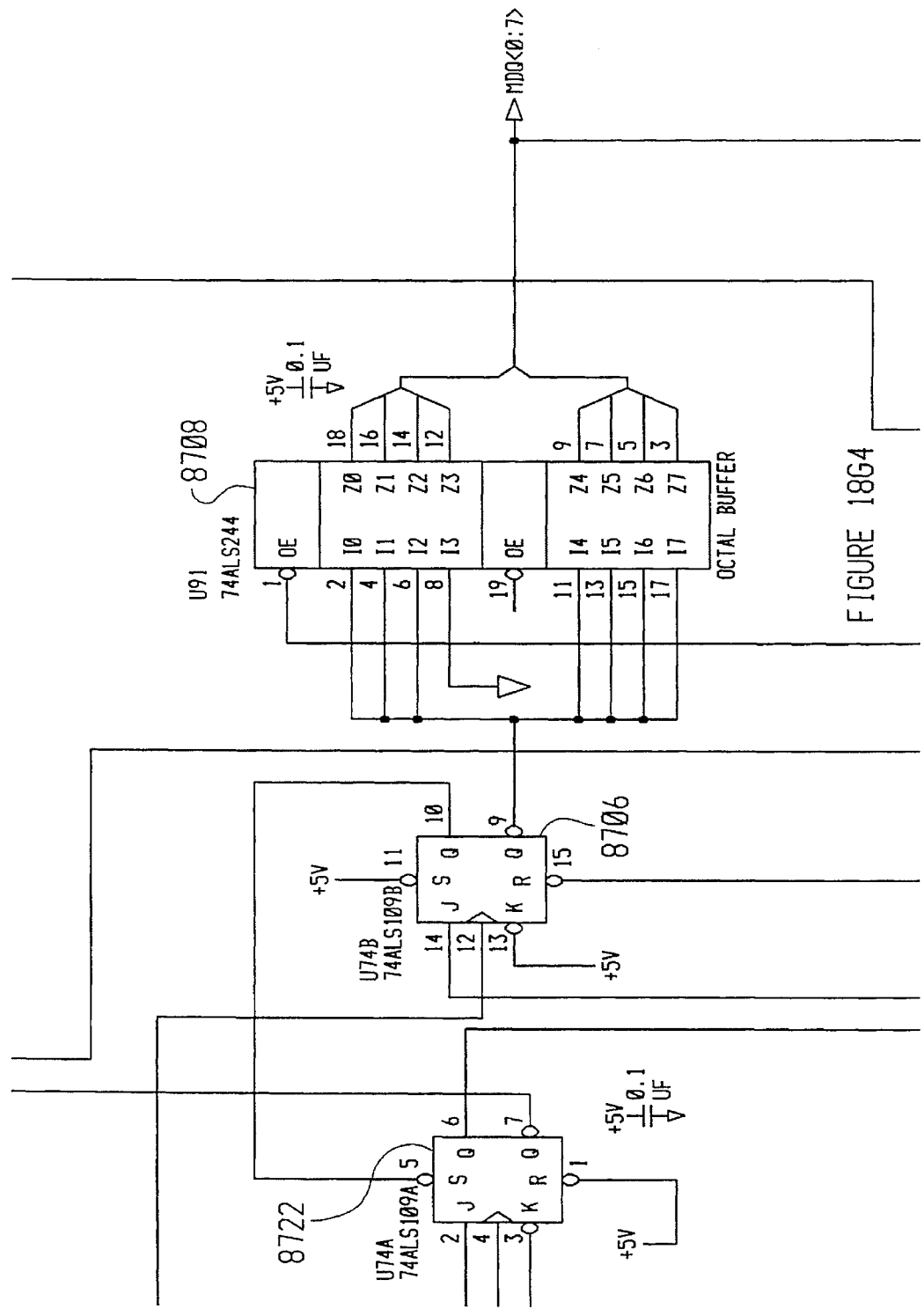

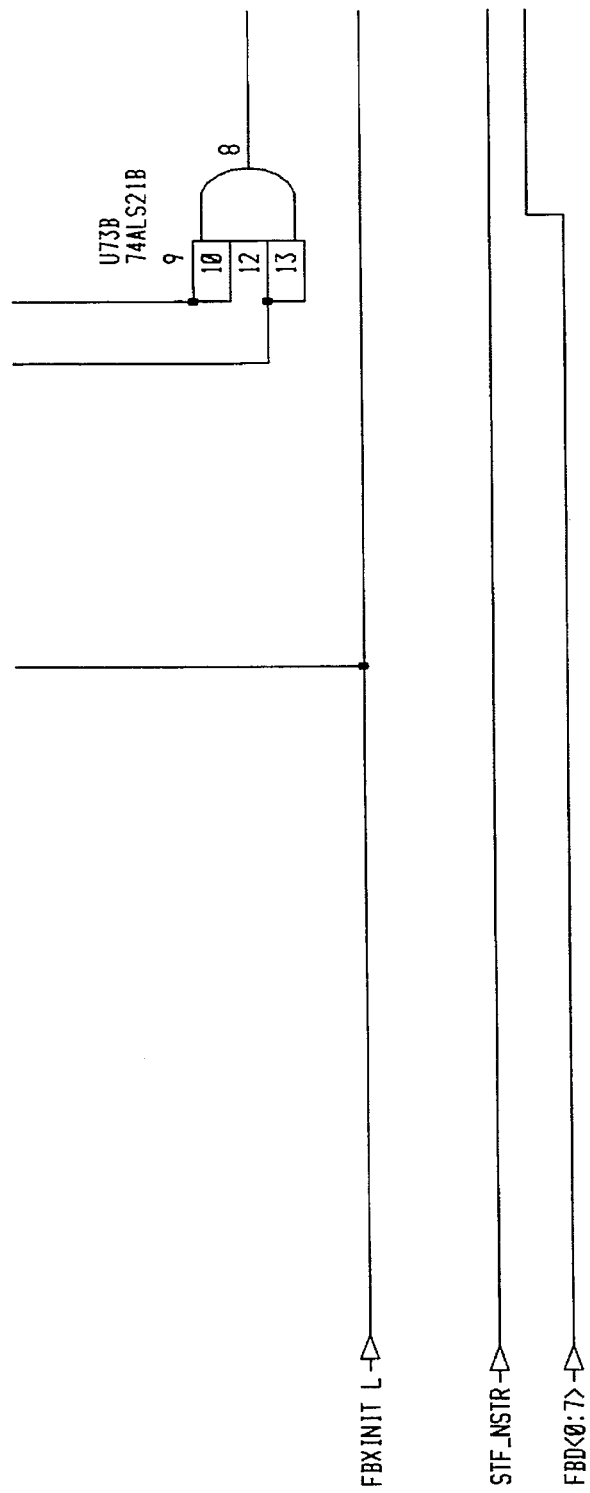
FIGURE 1865

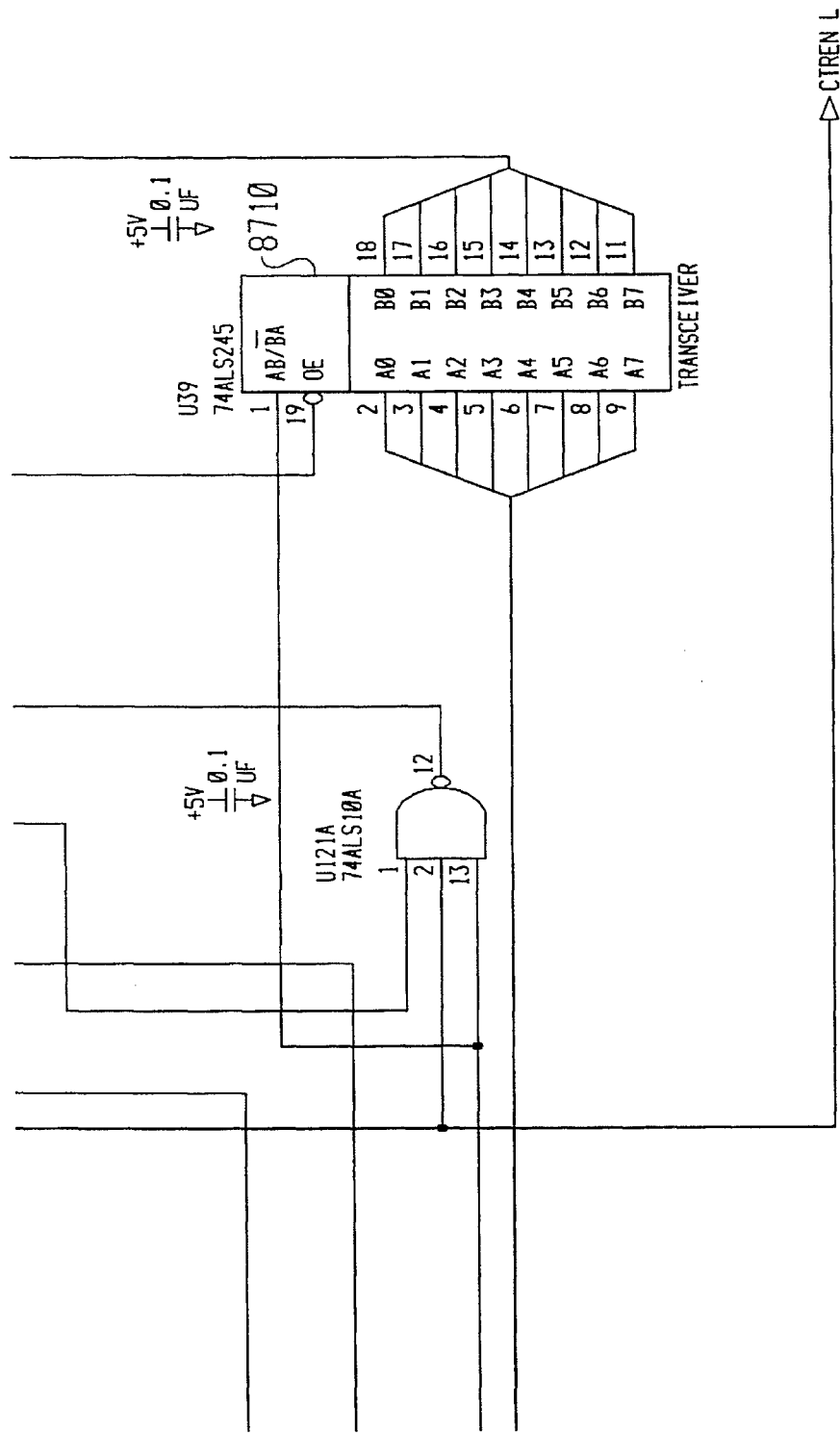
FIGURE 1866

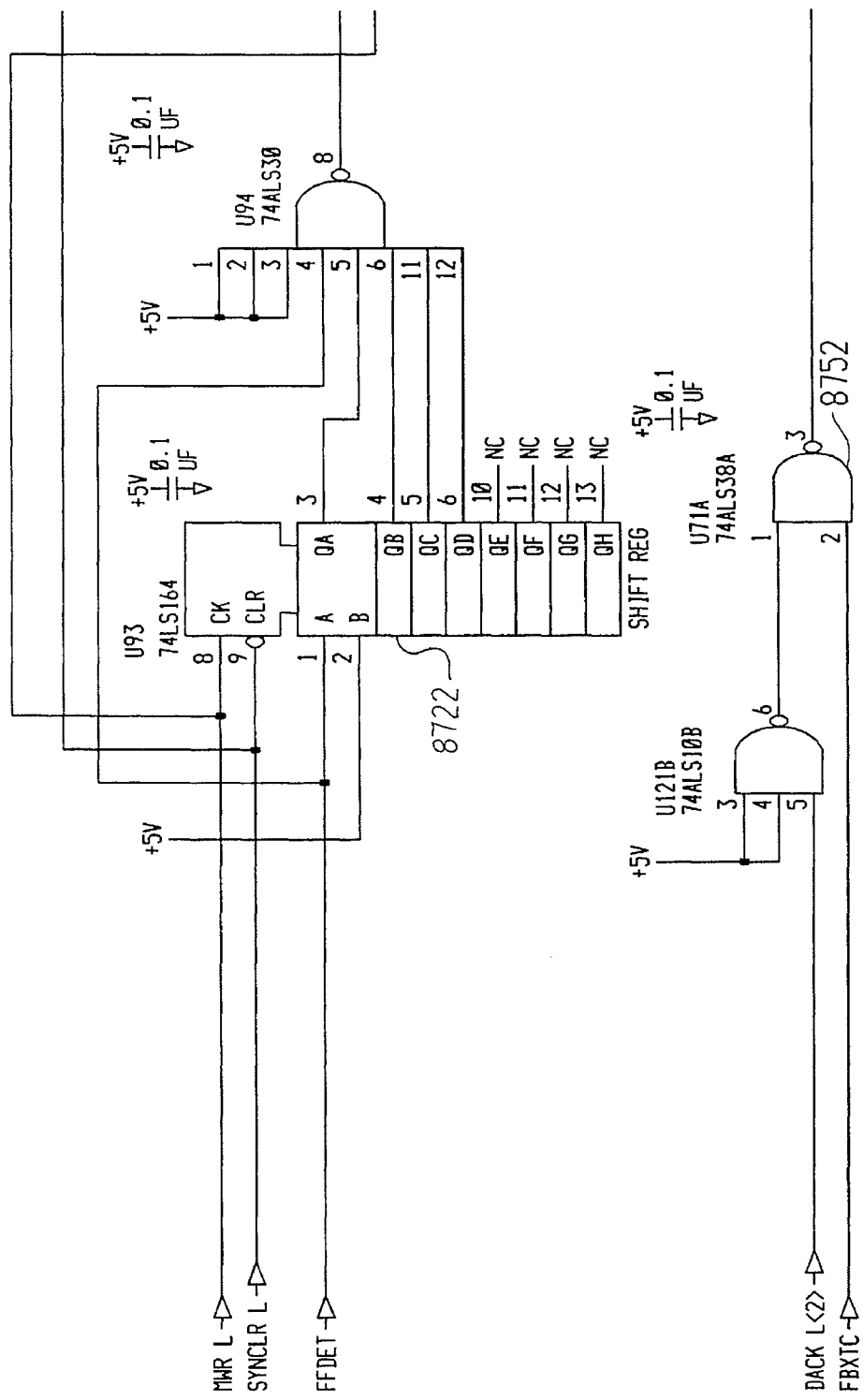
FIGURE 18H1

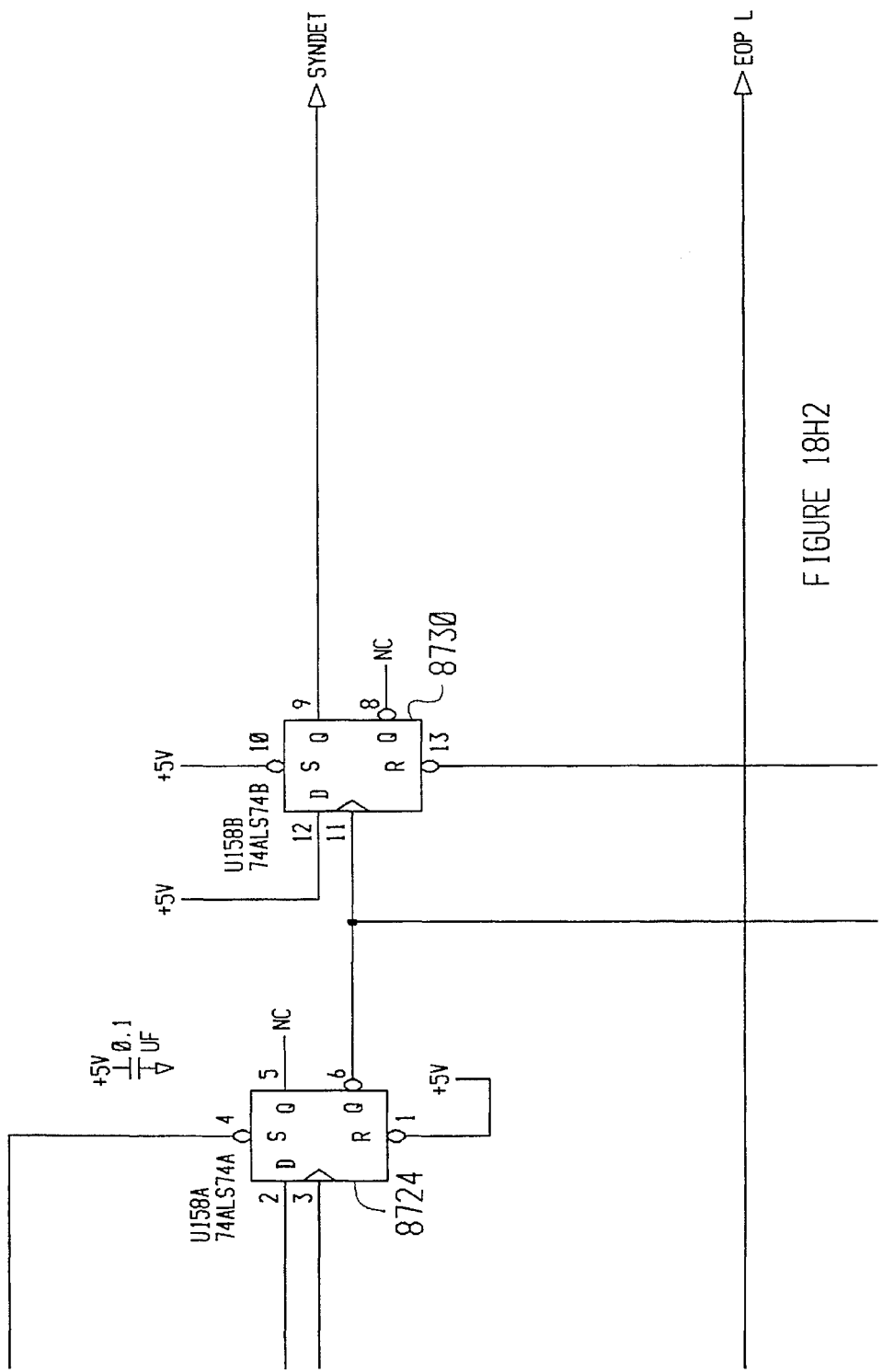
FIGURE 18H2

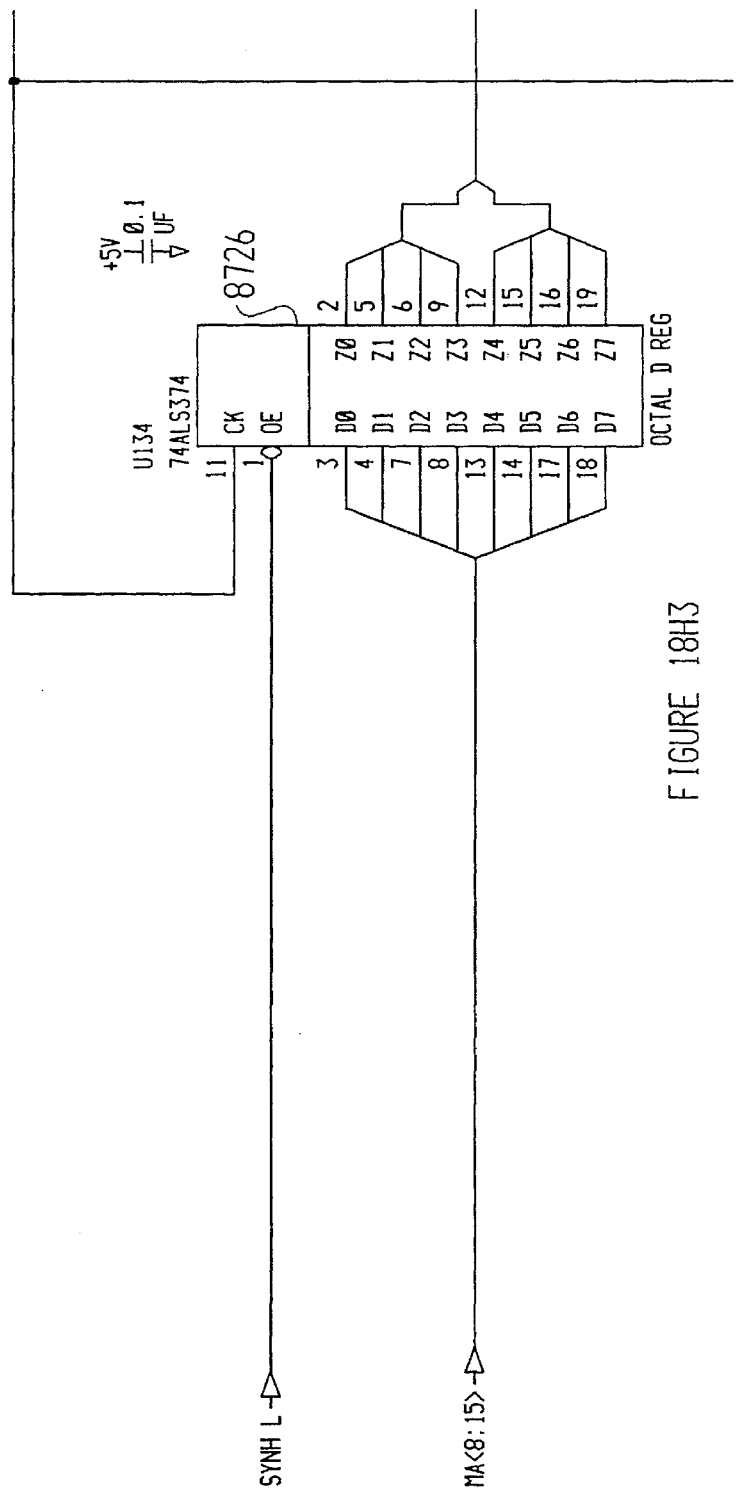
FIGURE 18H3

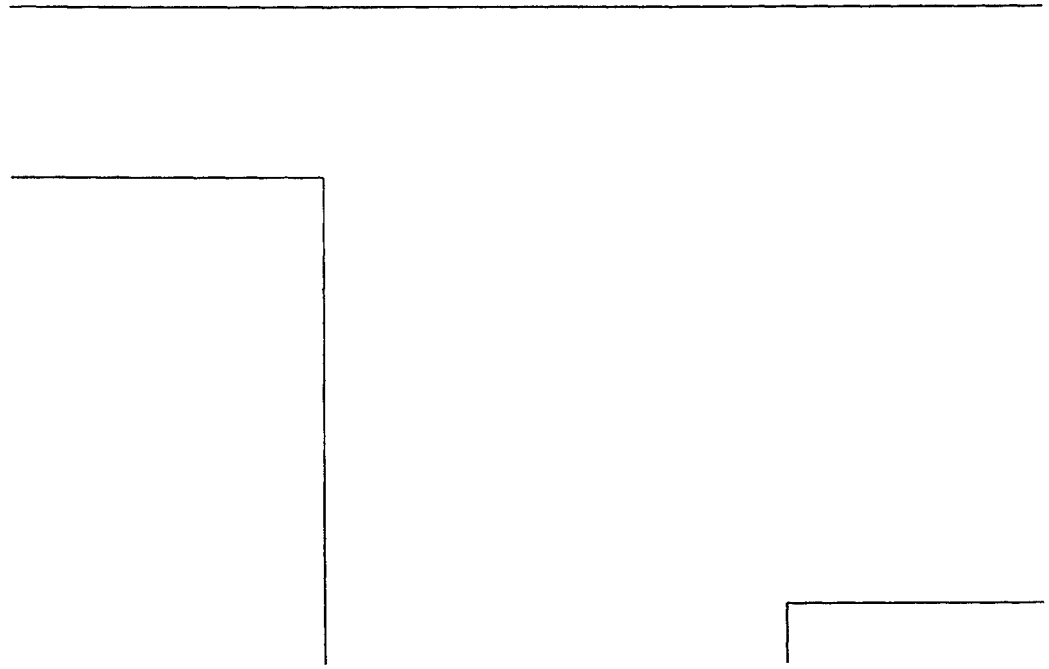
FIGURE 18H4

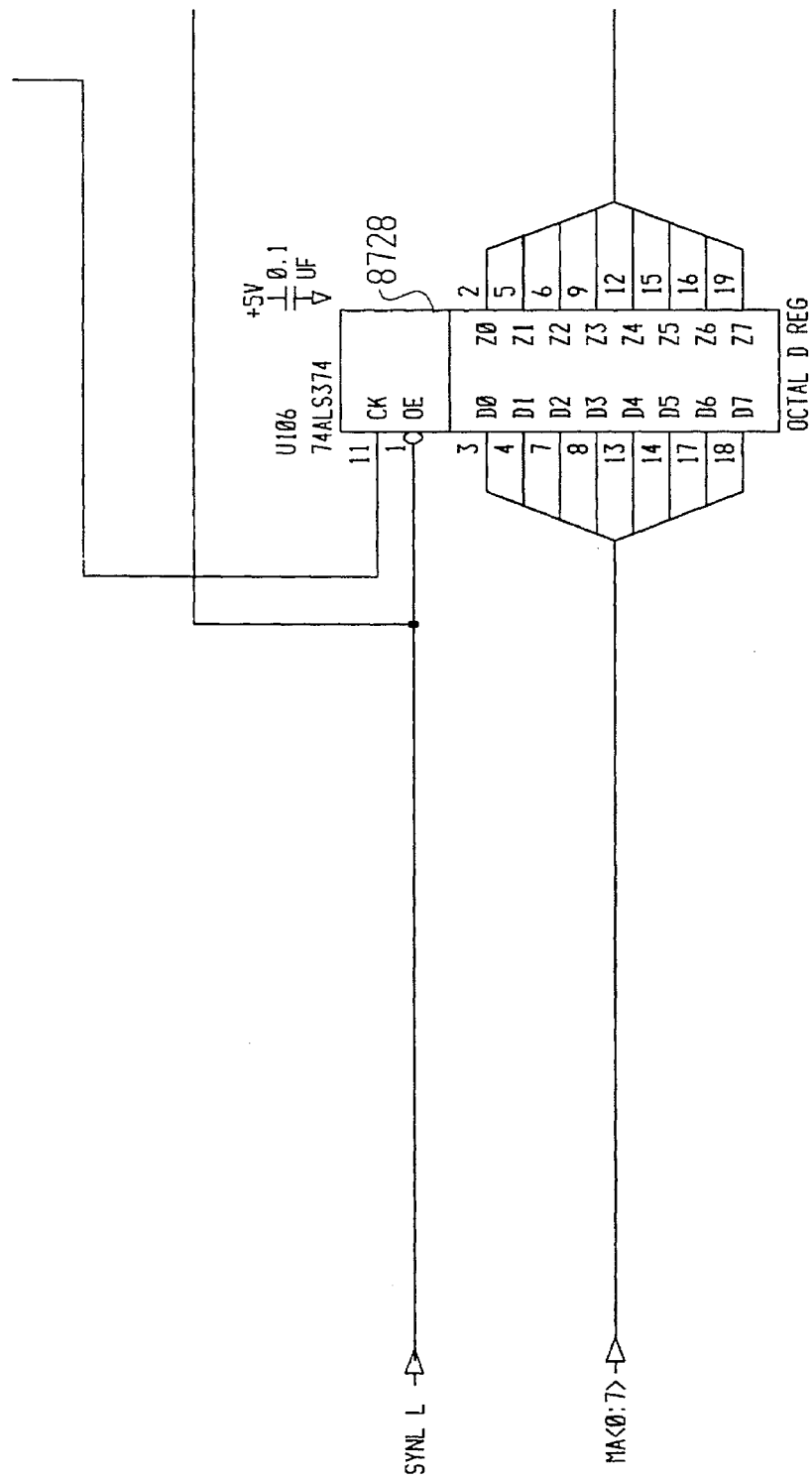
FIGURE 18H5

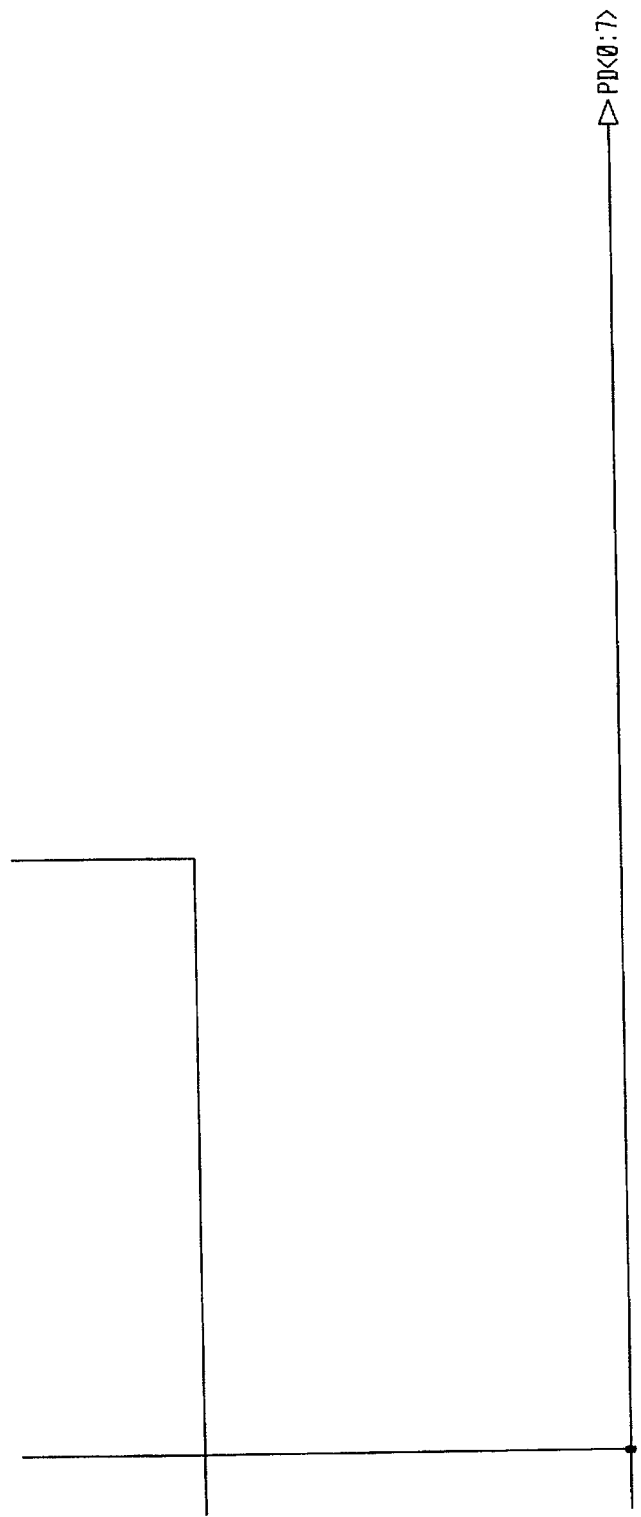
FIGURE 18H6

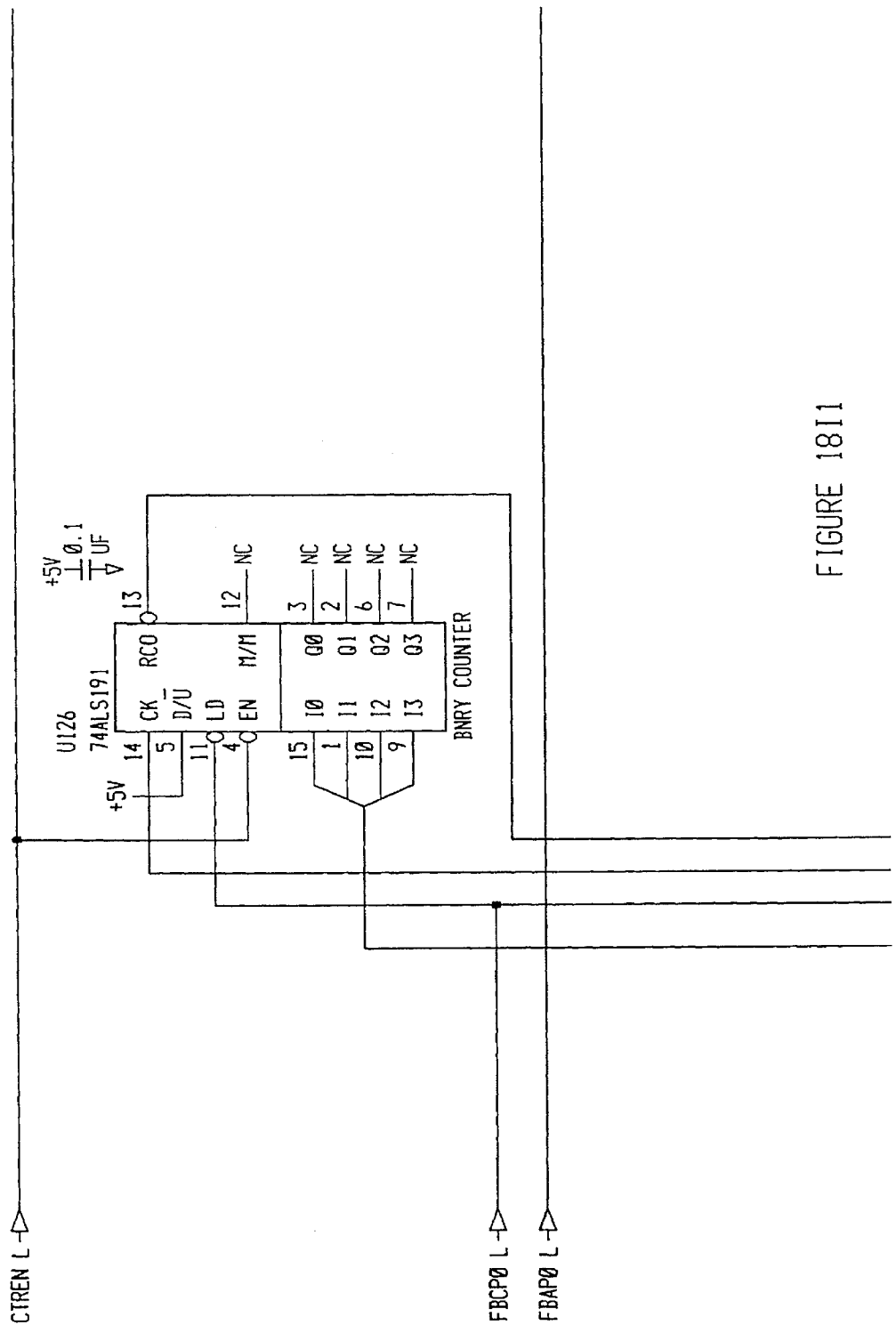
FIGURE 18I1

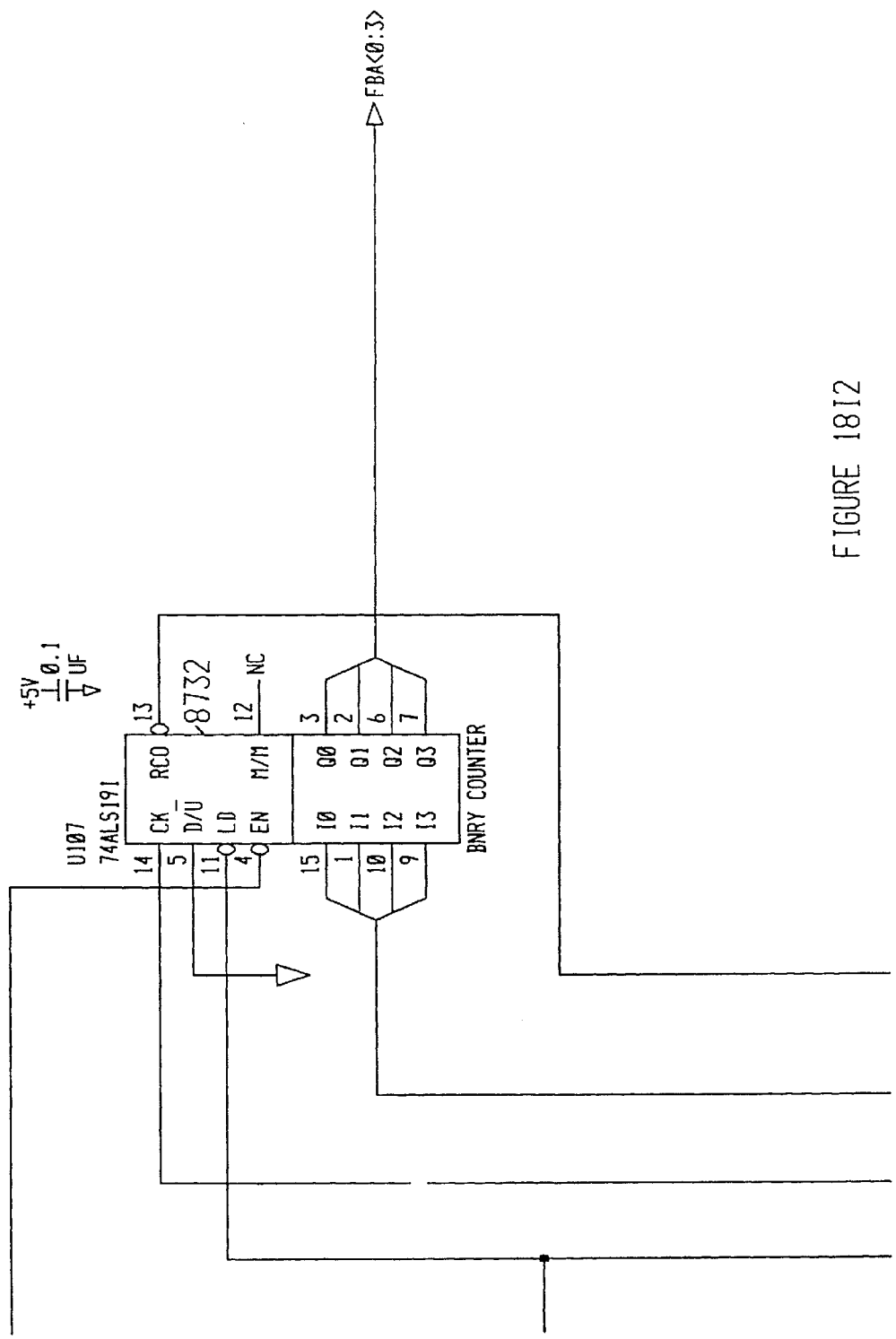
FIGURE 1812

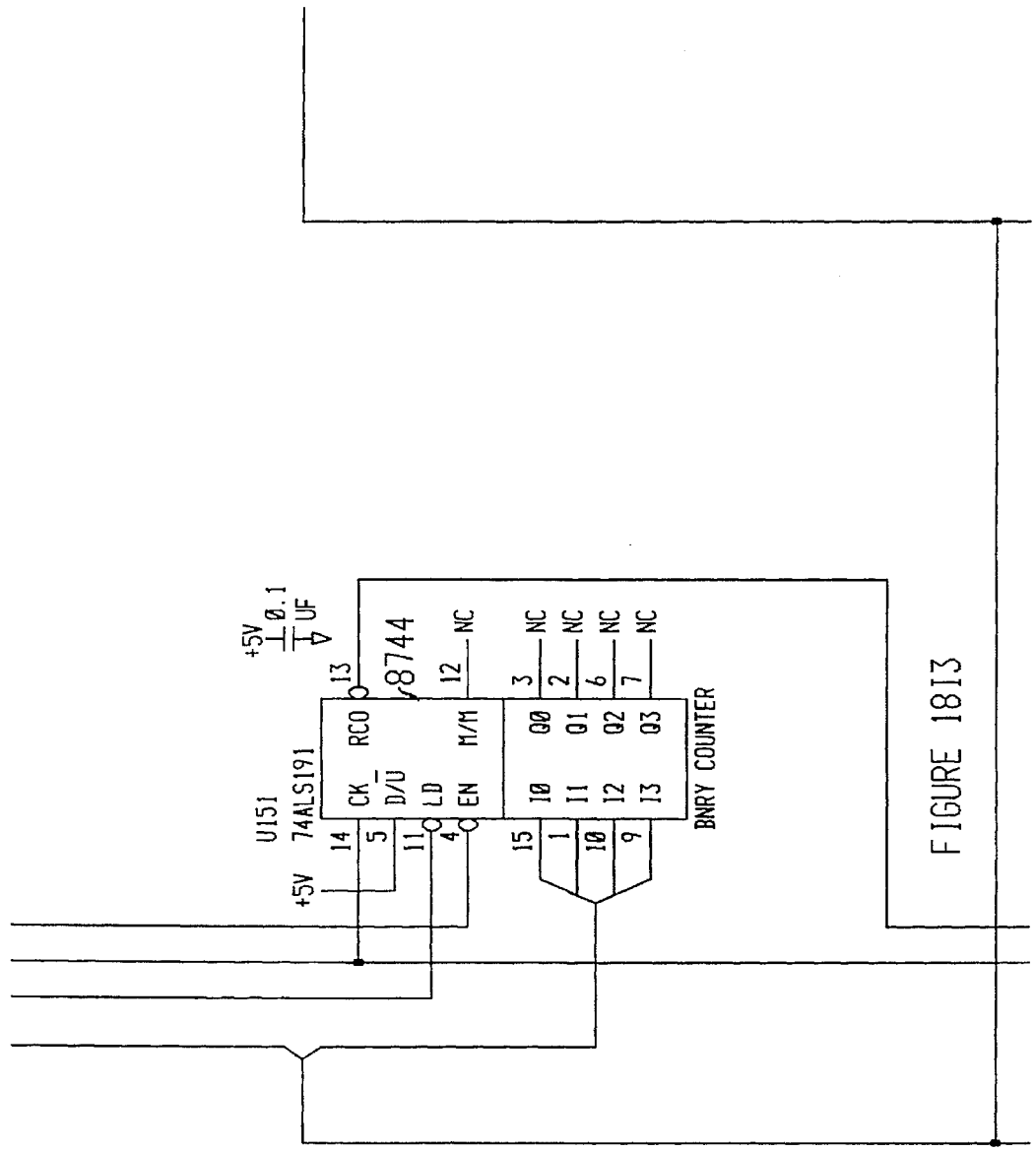

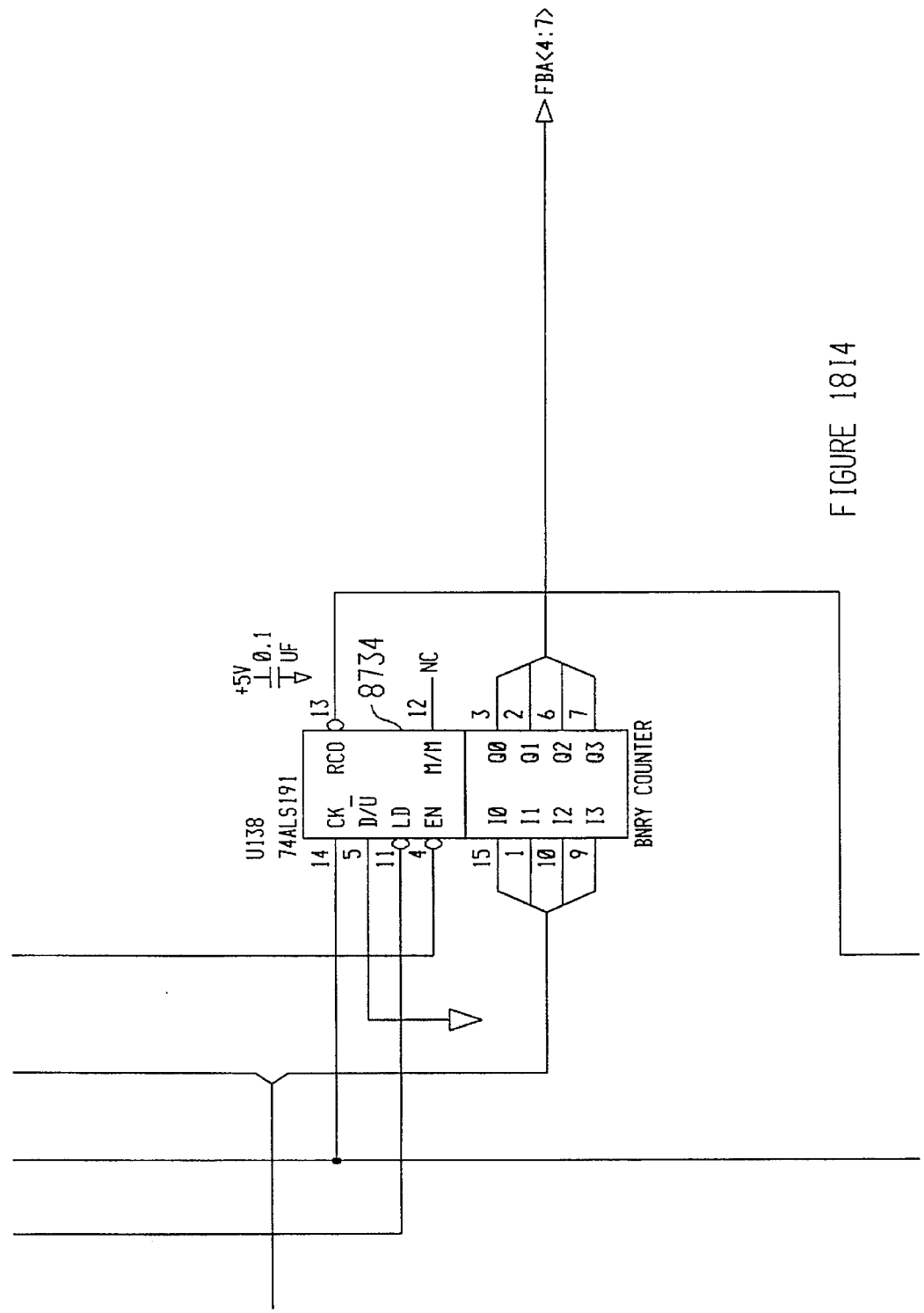
FIGURE 1814

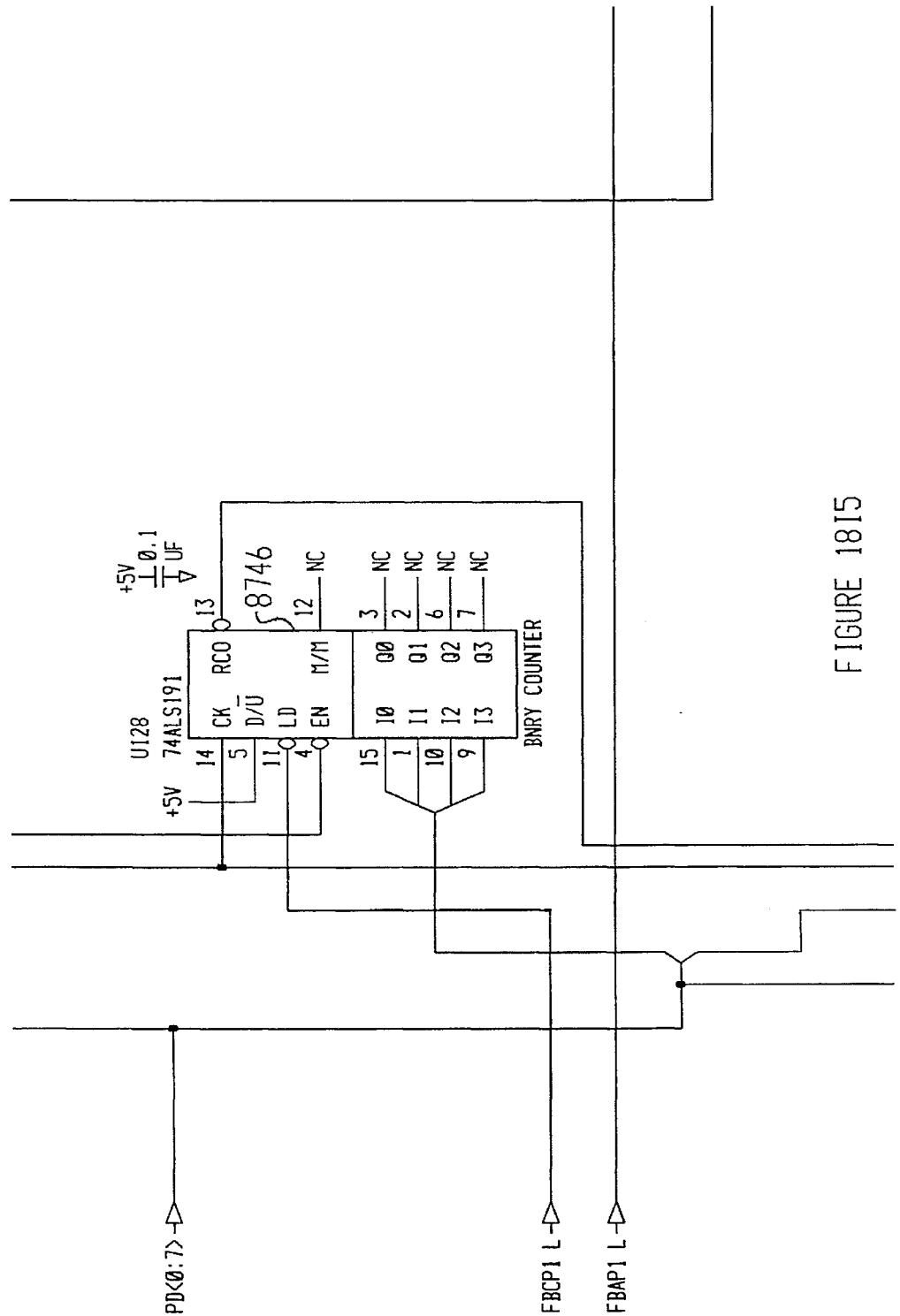
FIGURE 1815

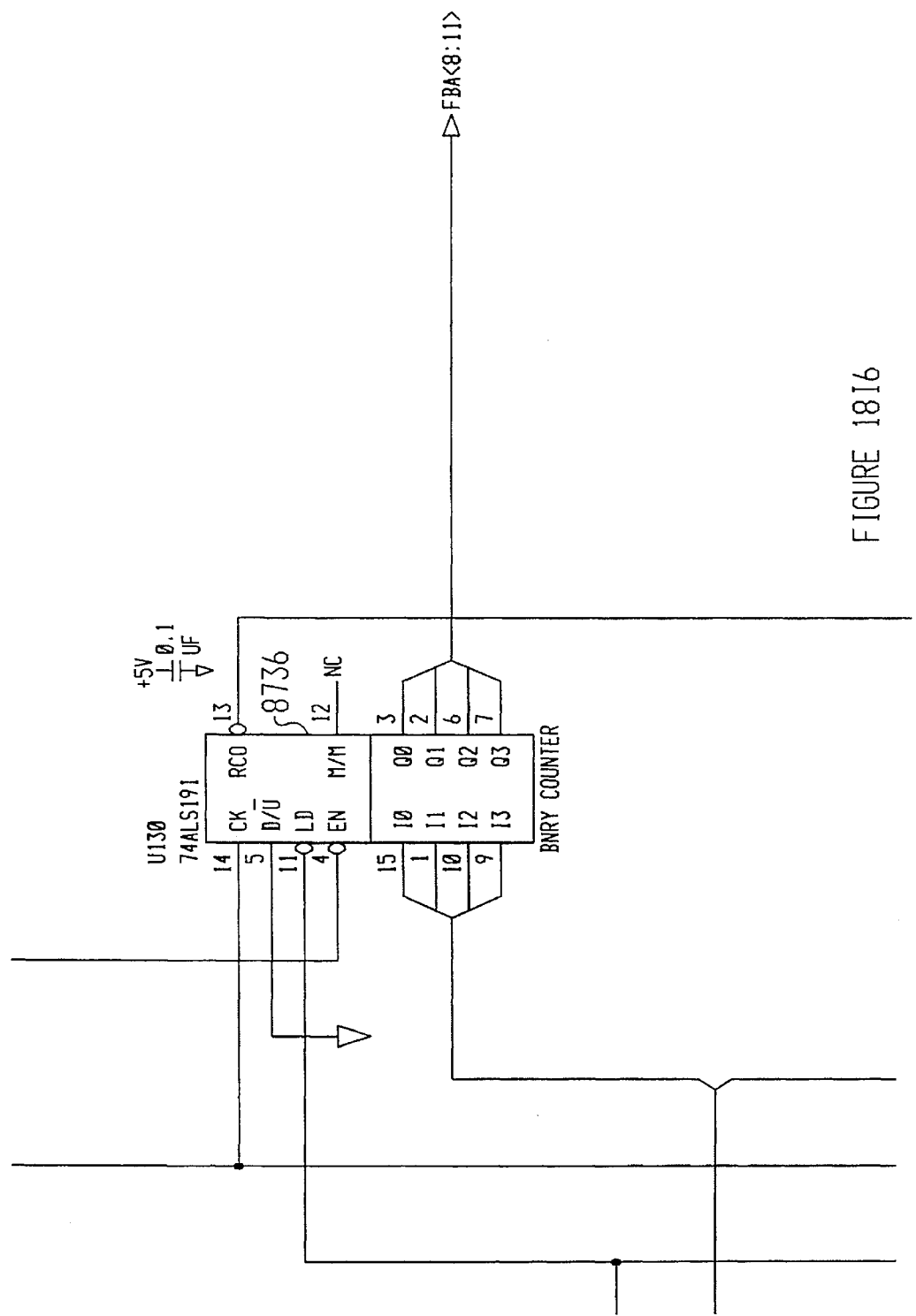
FIGURE 1816

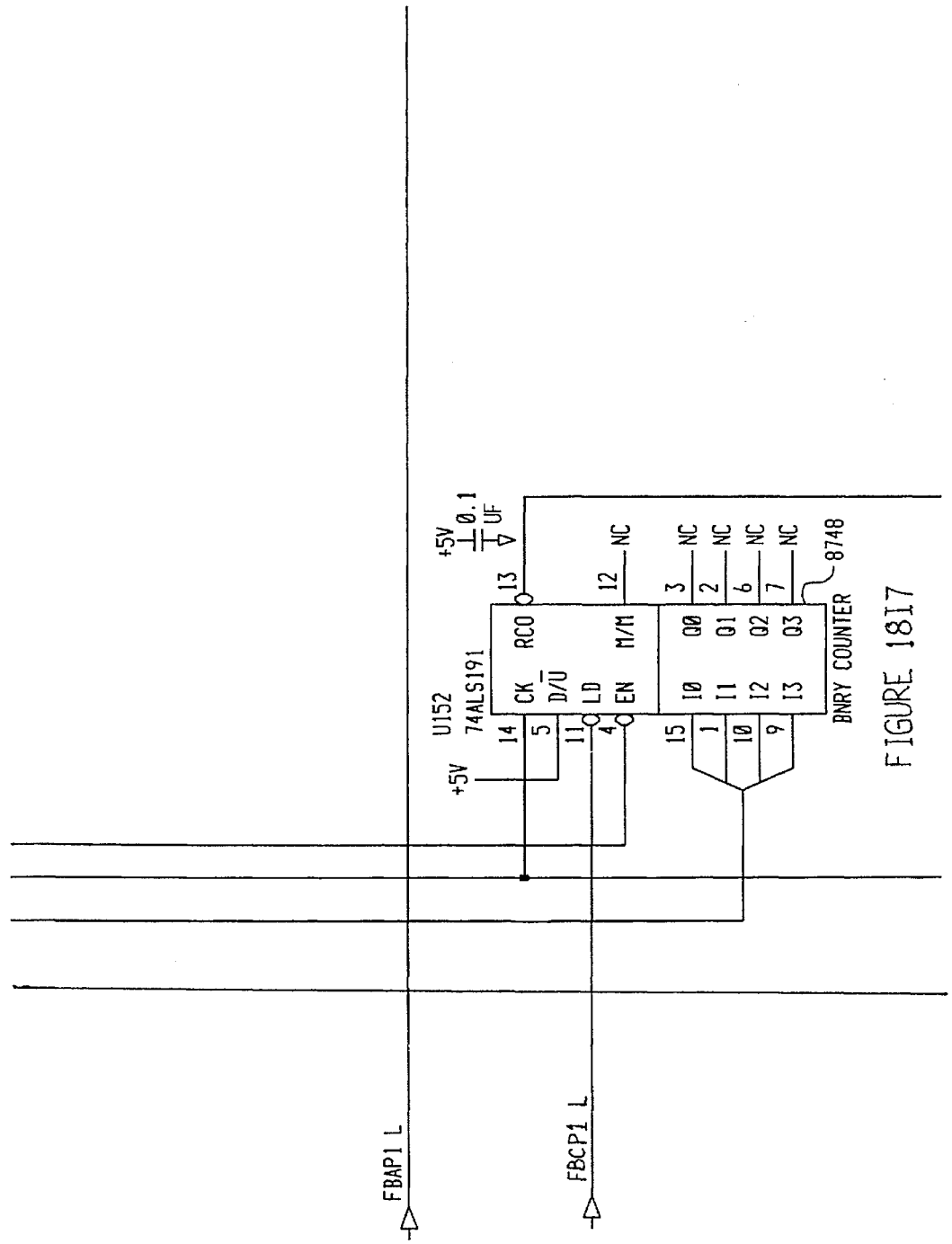
FIGURE 1817

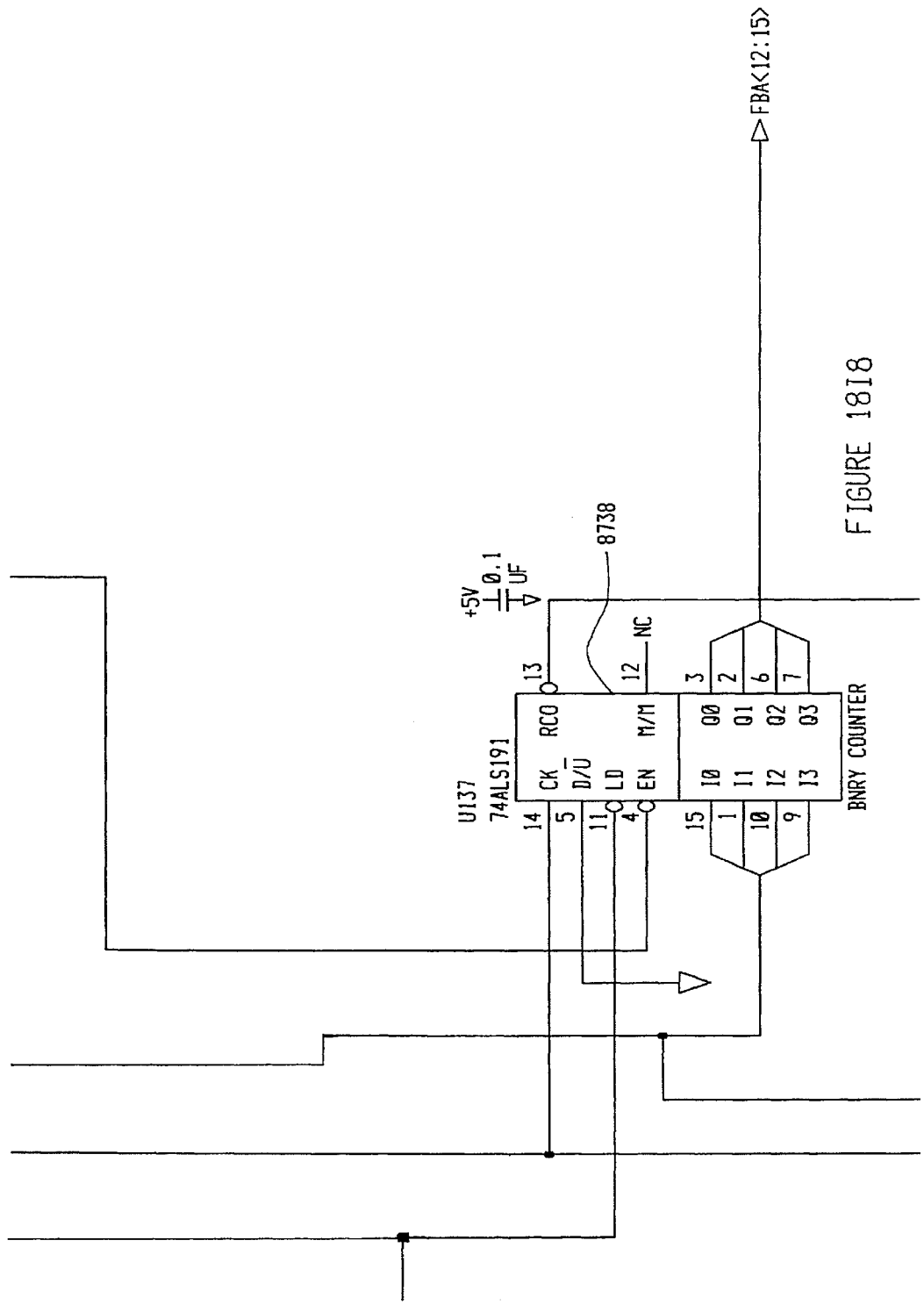
FIGURE 1818

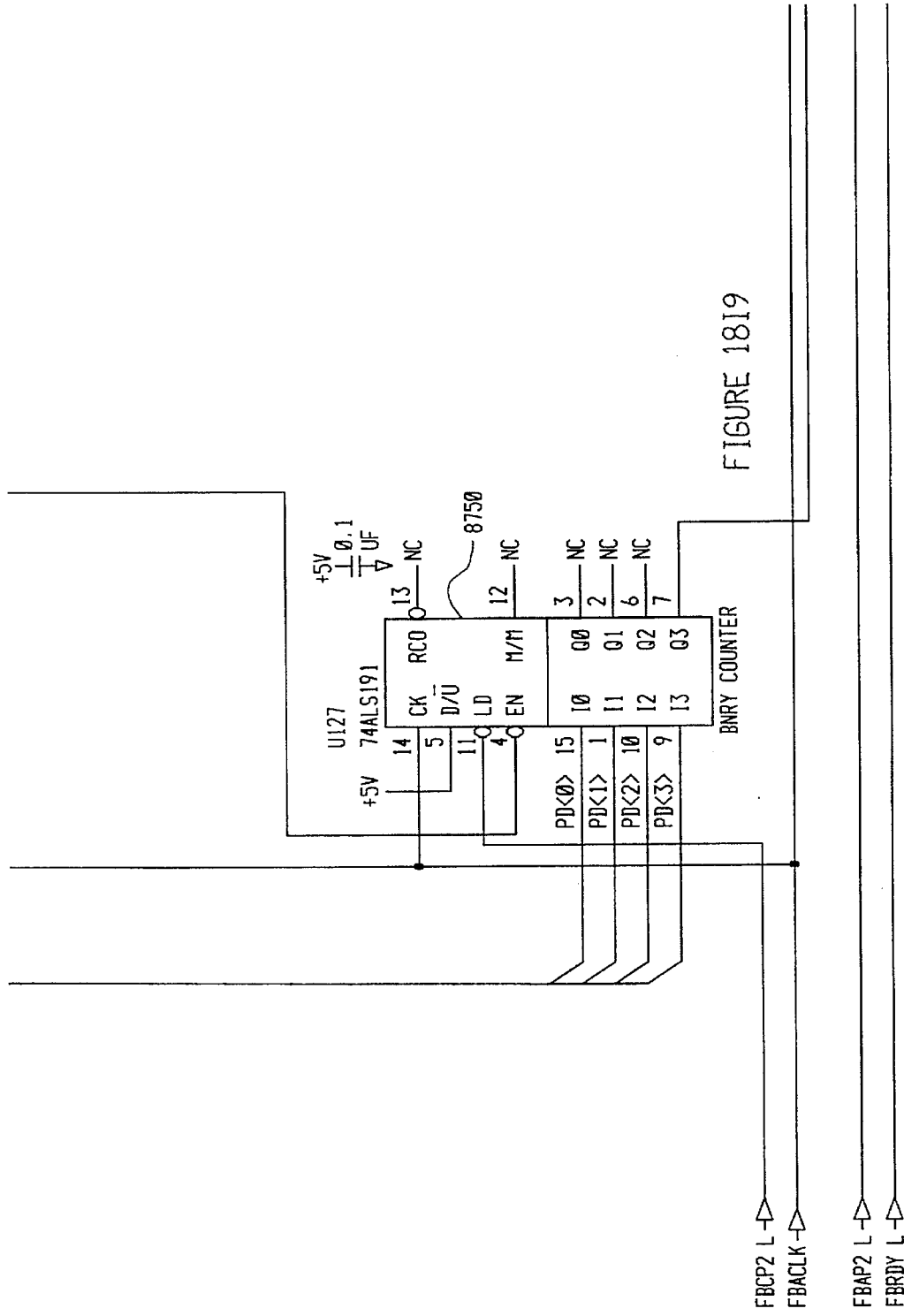

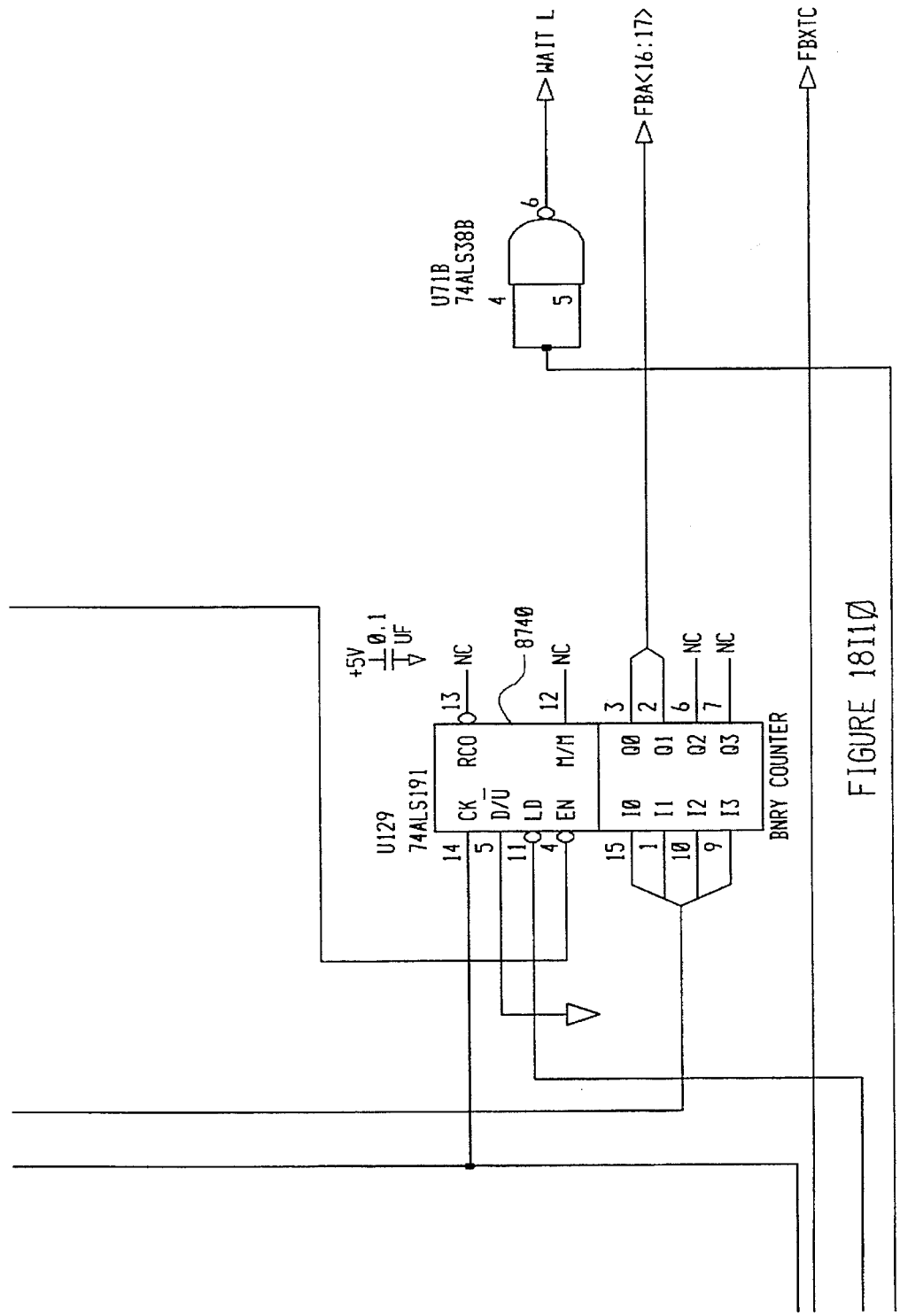

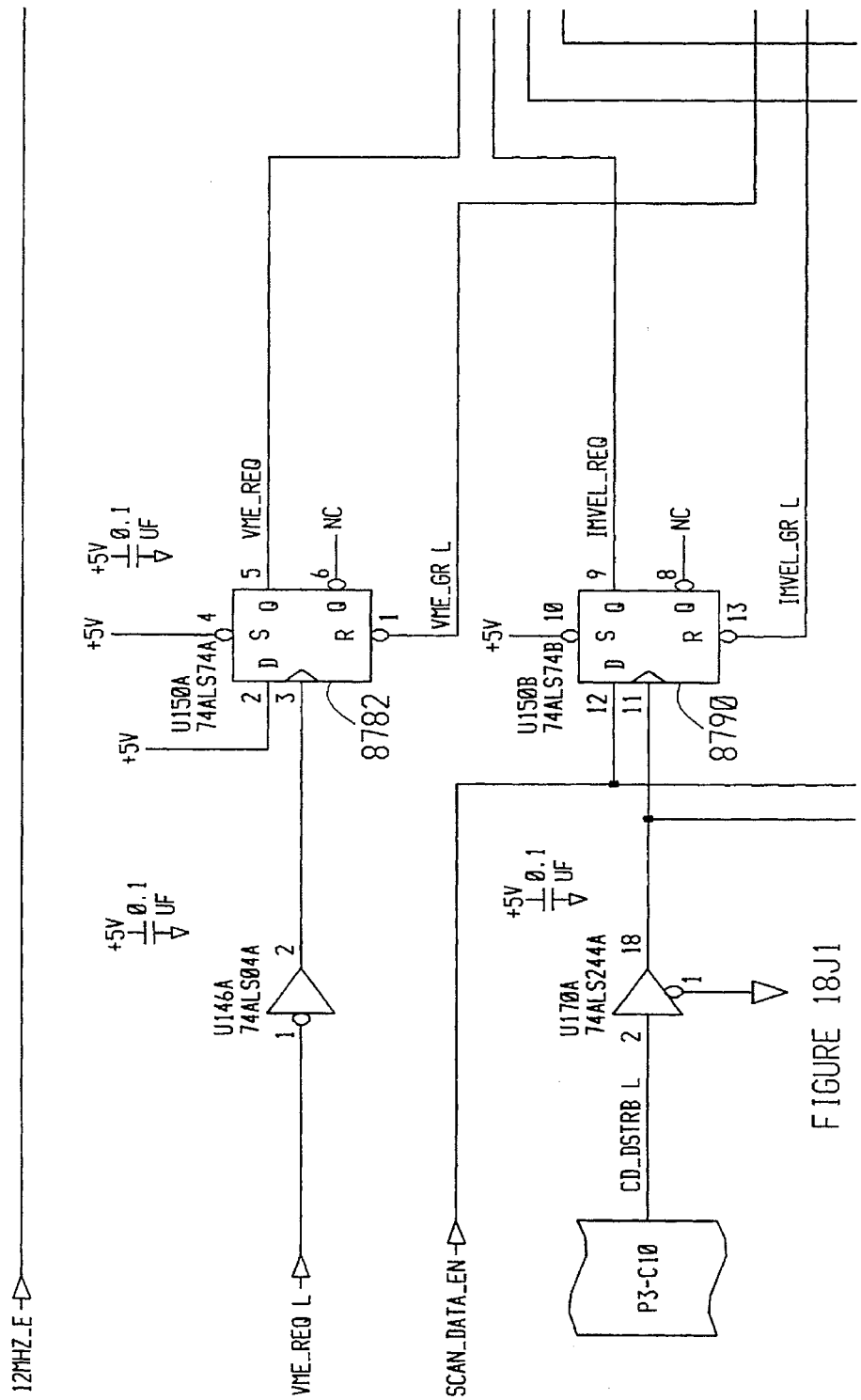
FIGURE 18J1

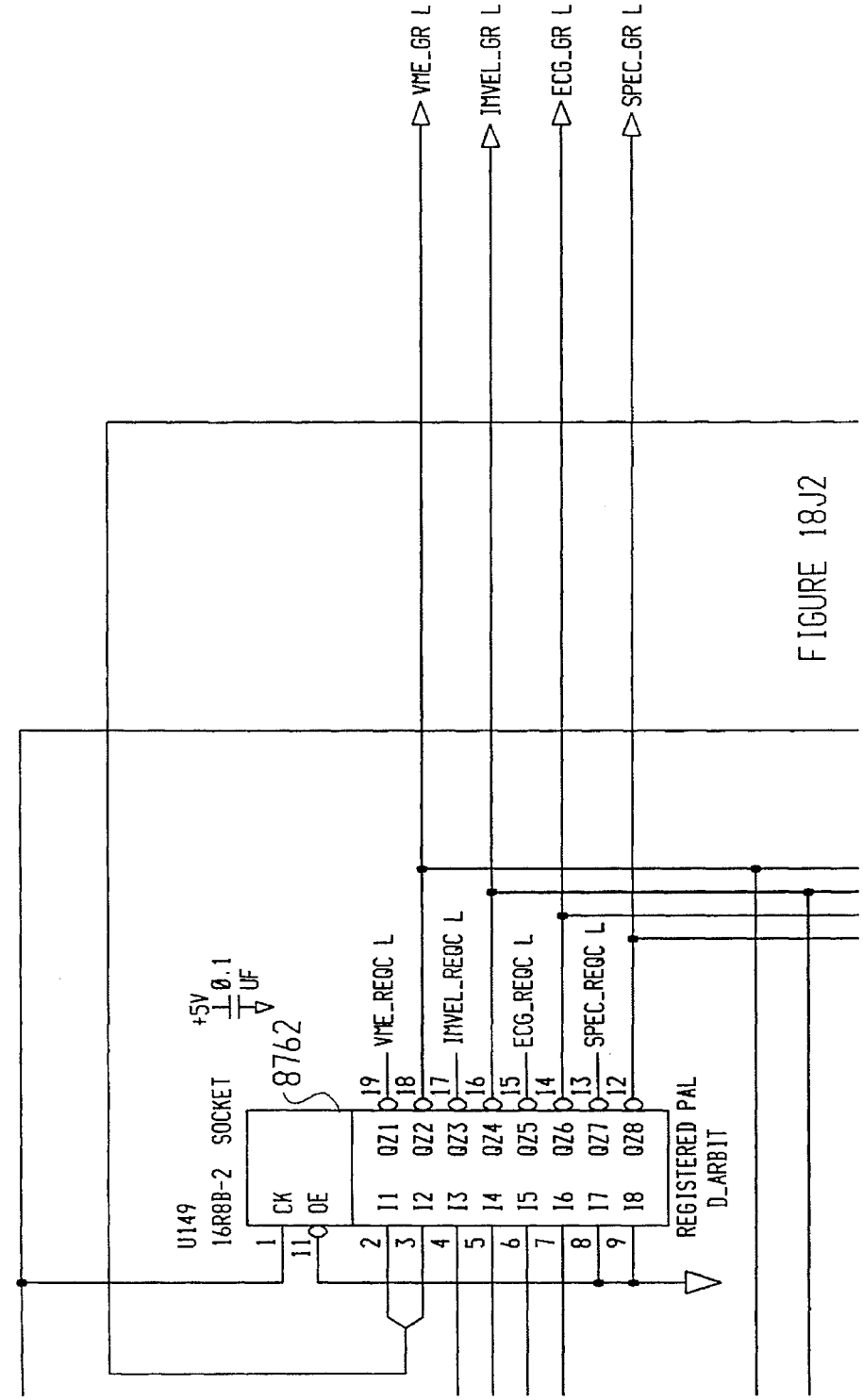

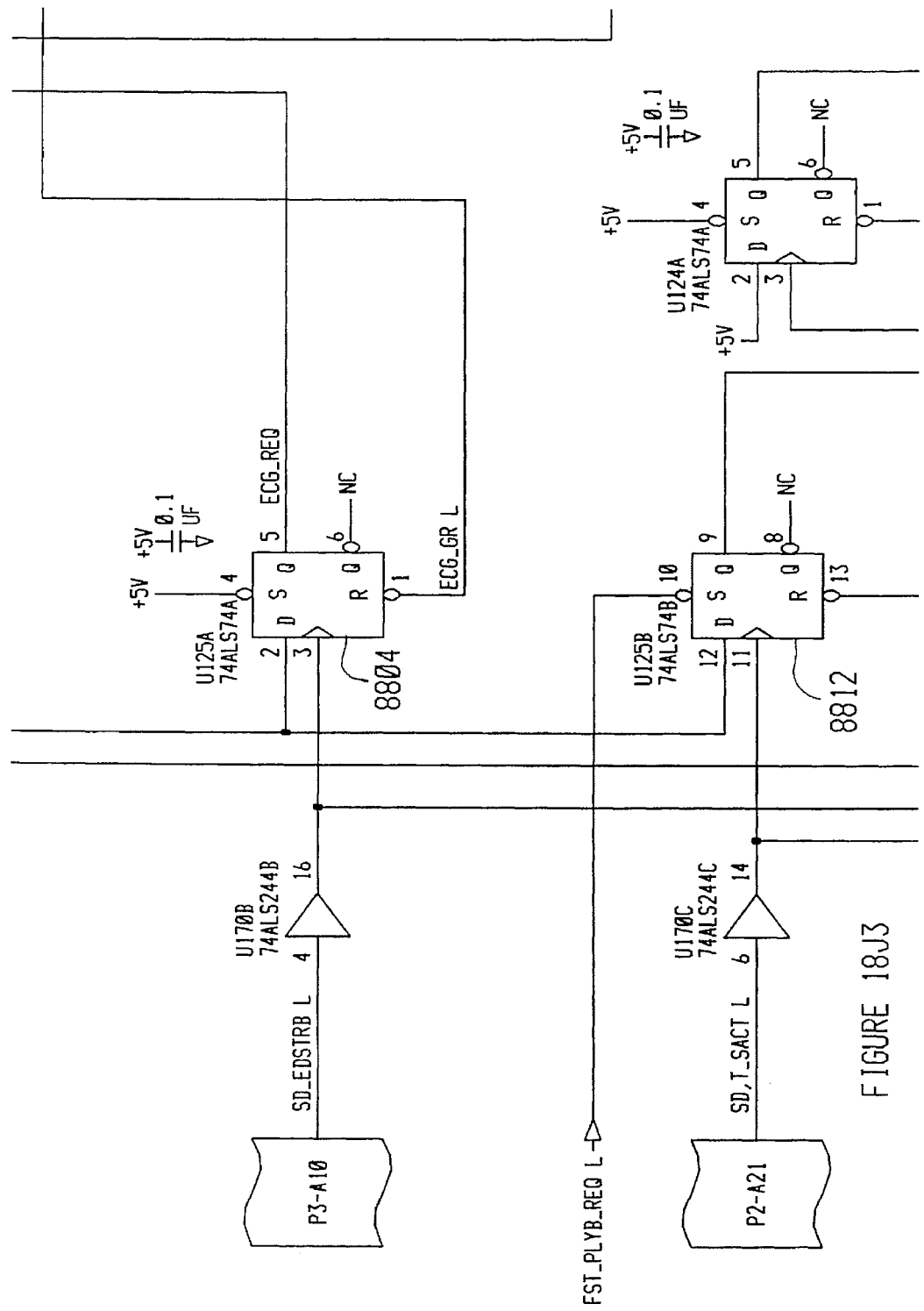
FIGURE 18J3

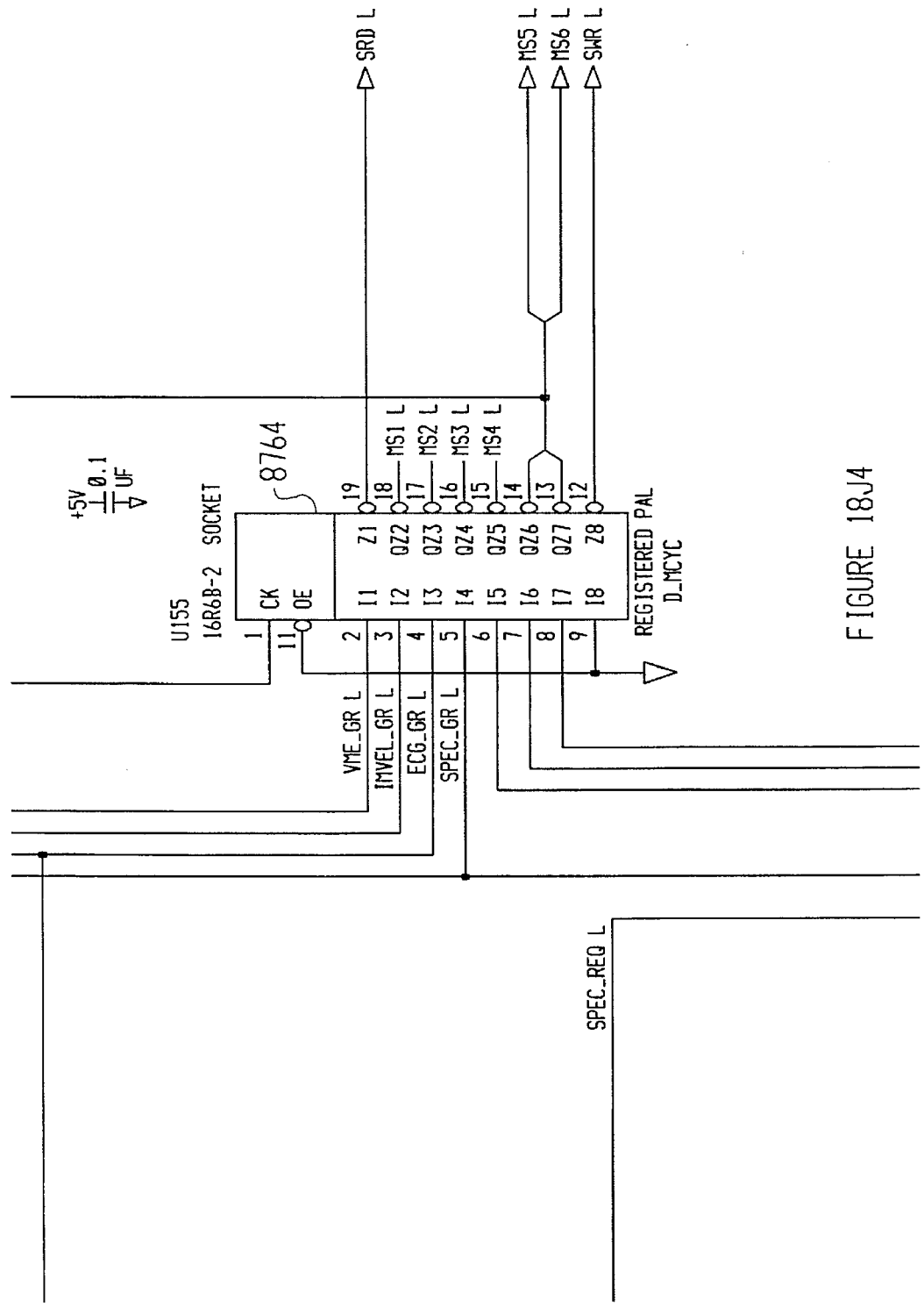
FIGURE 18J4

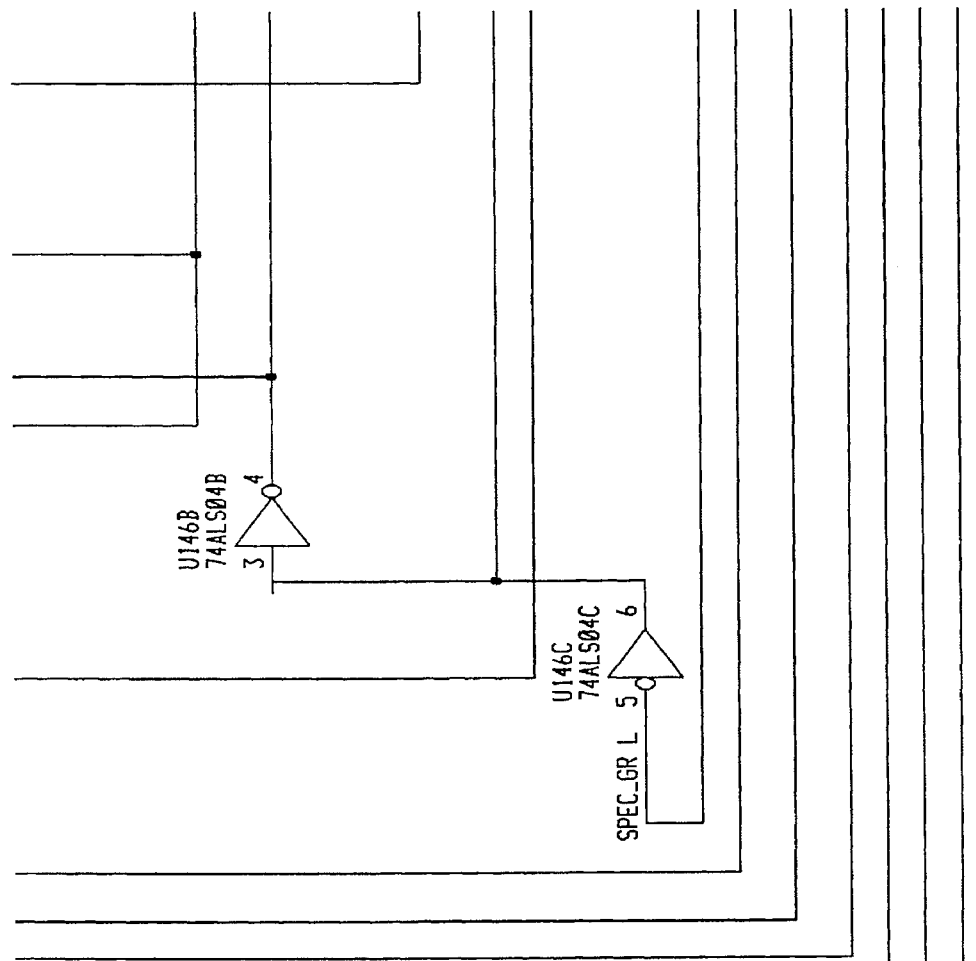
FIGURE 18J5

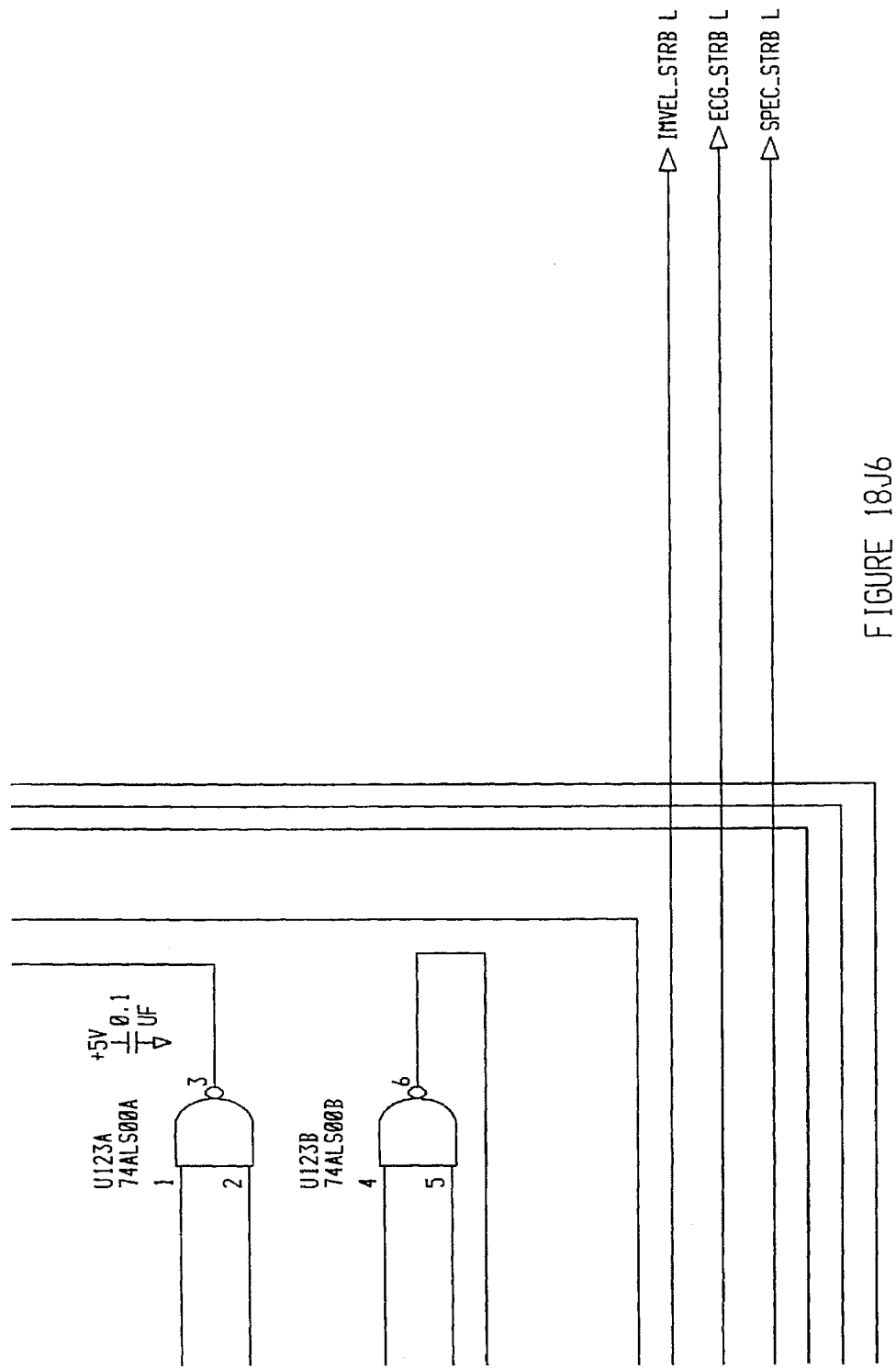
FIGURE 18J6

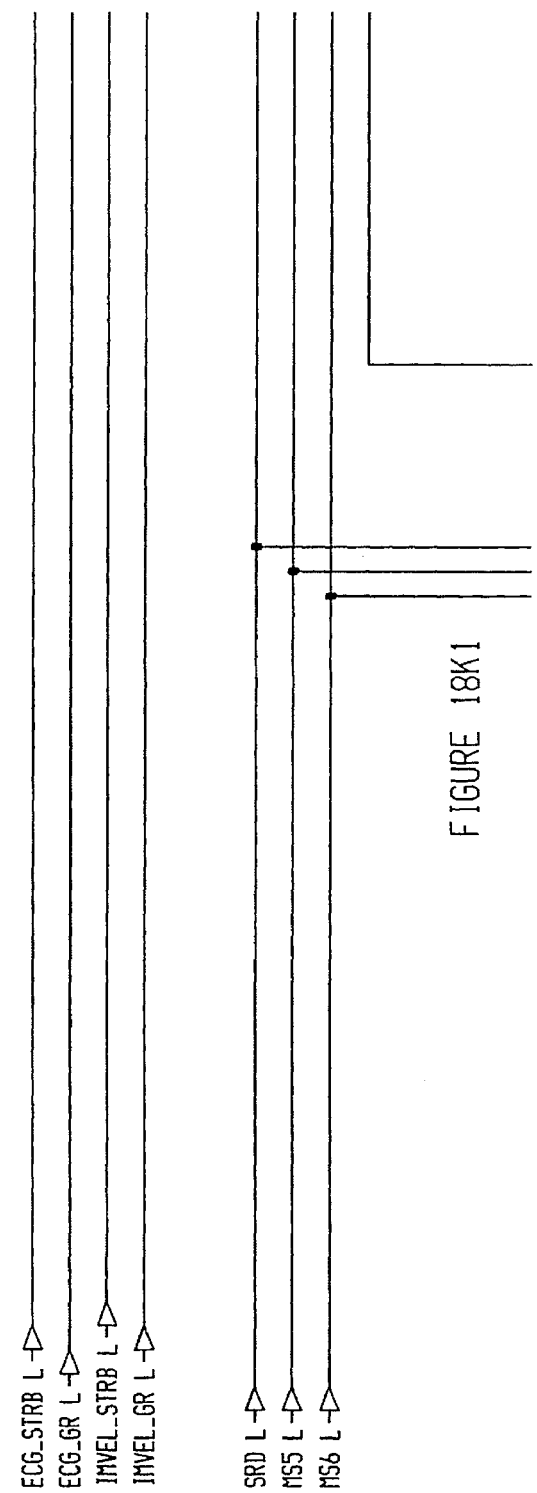

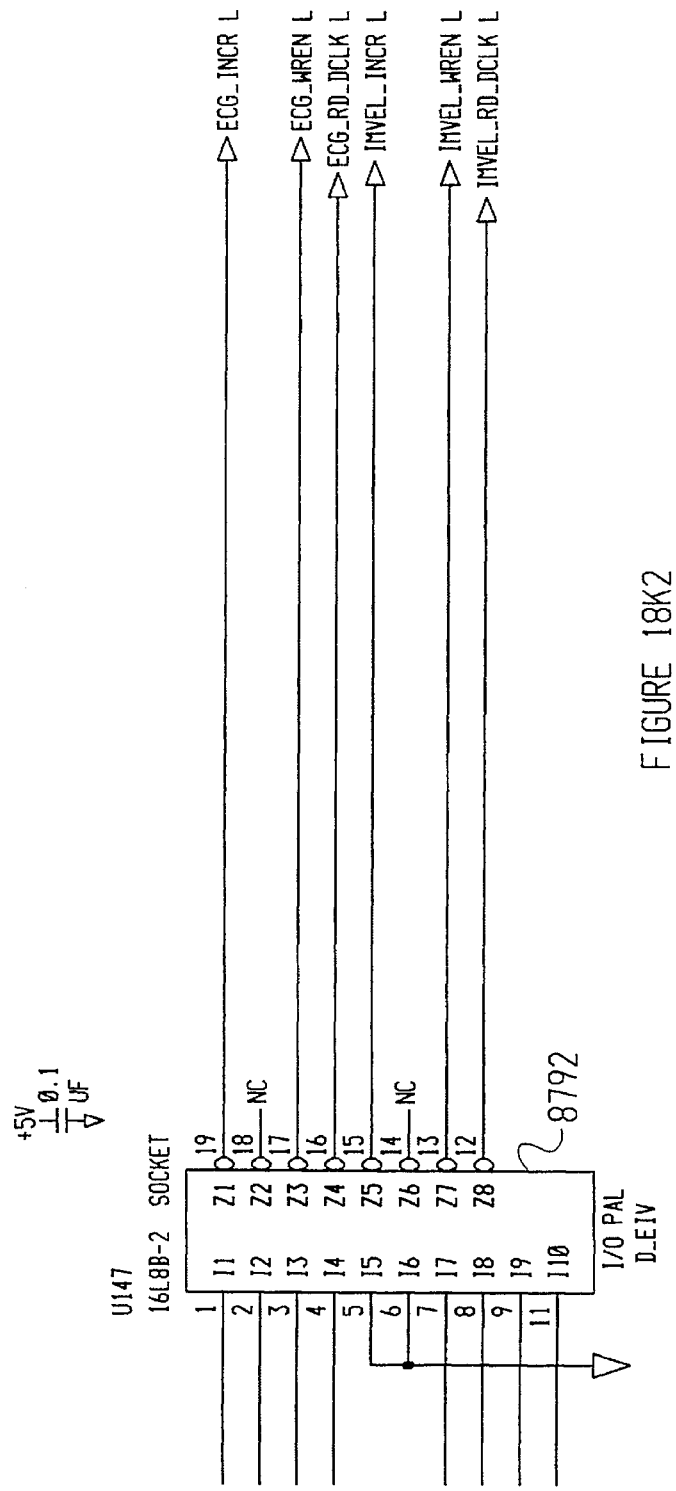
FIGURE 18K2

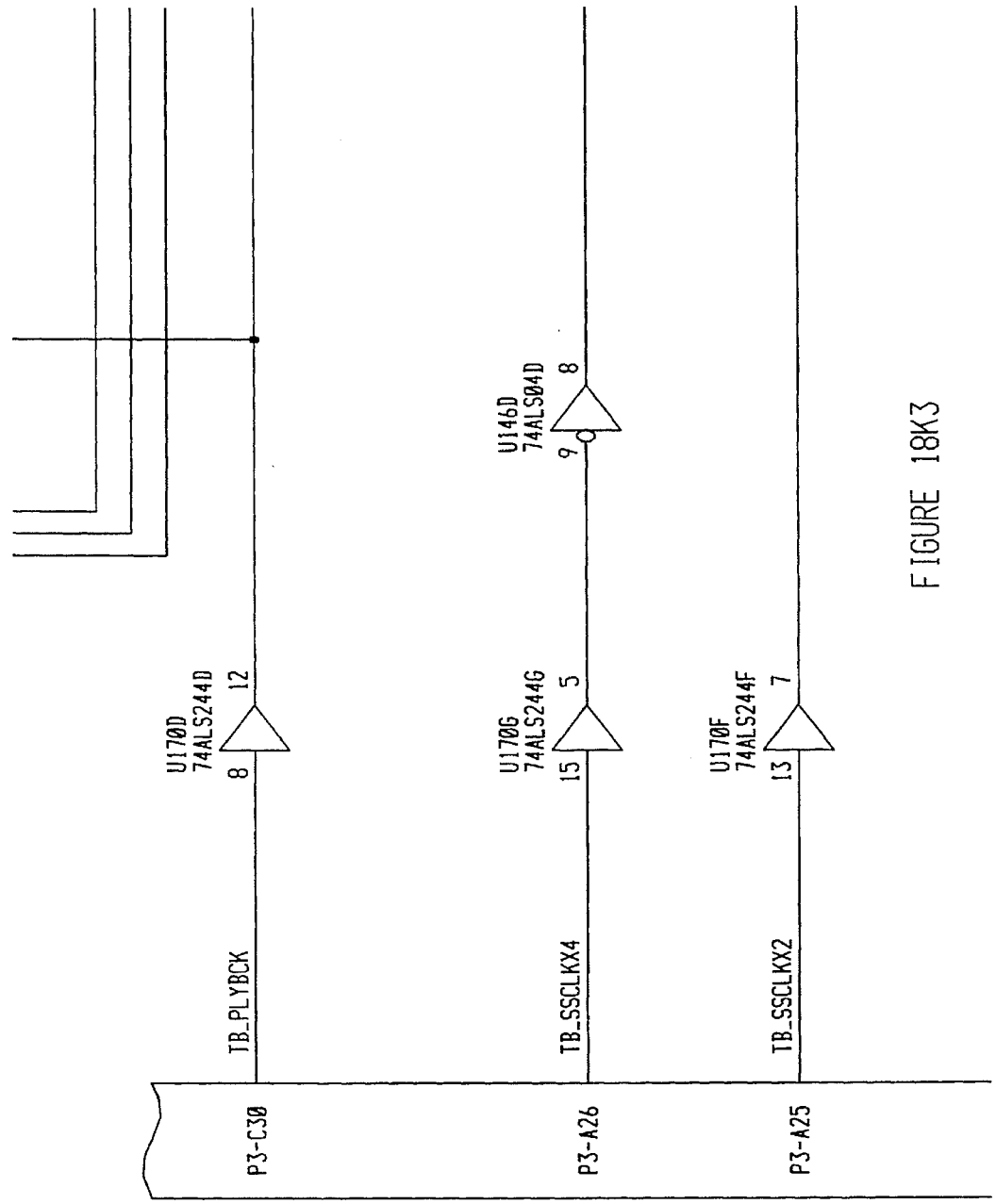
FIGURE 18K3

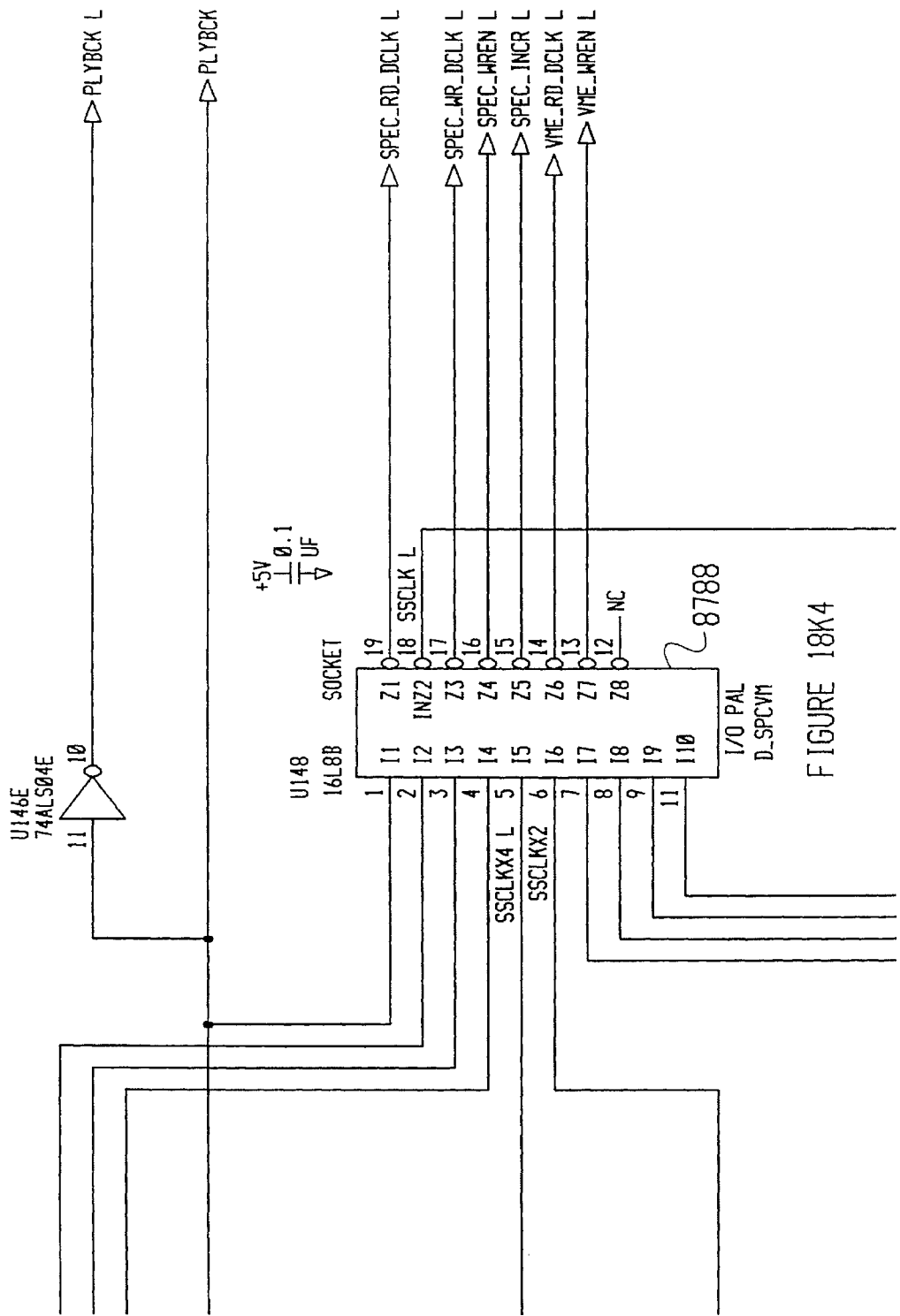

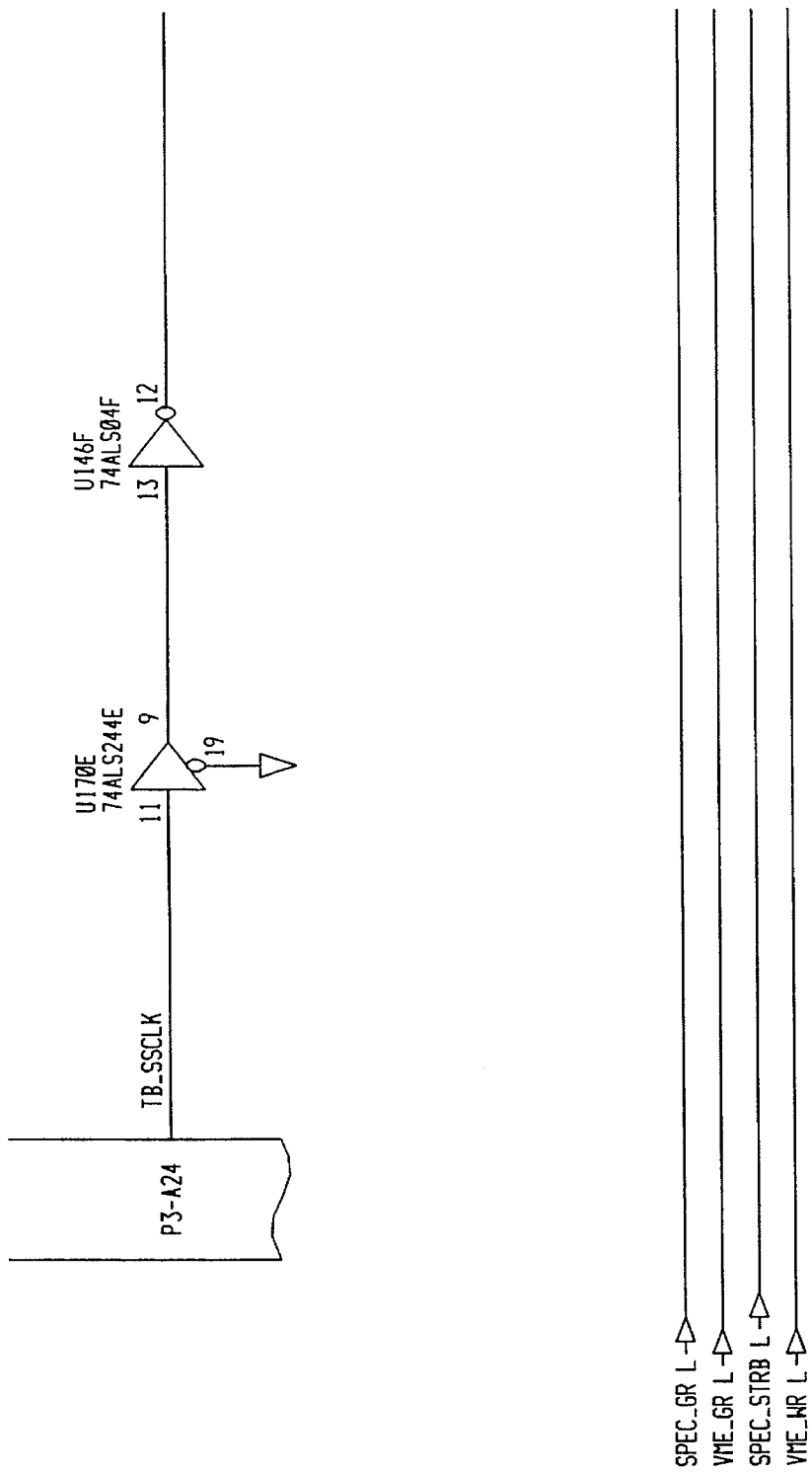
FIGURE 18K5

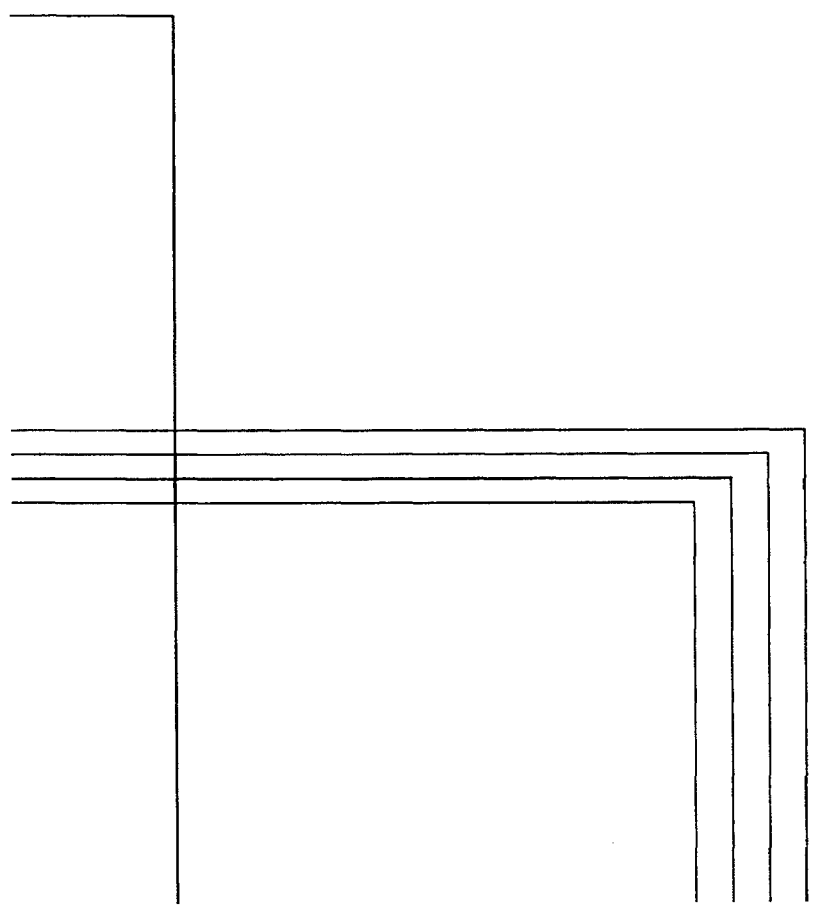
FIGURE 18K6

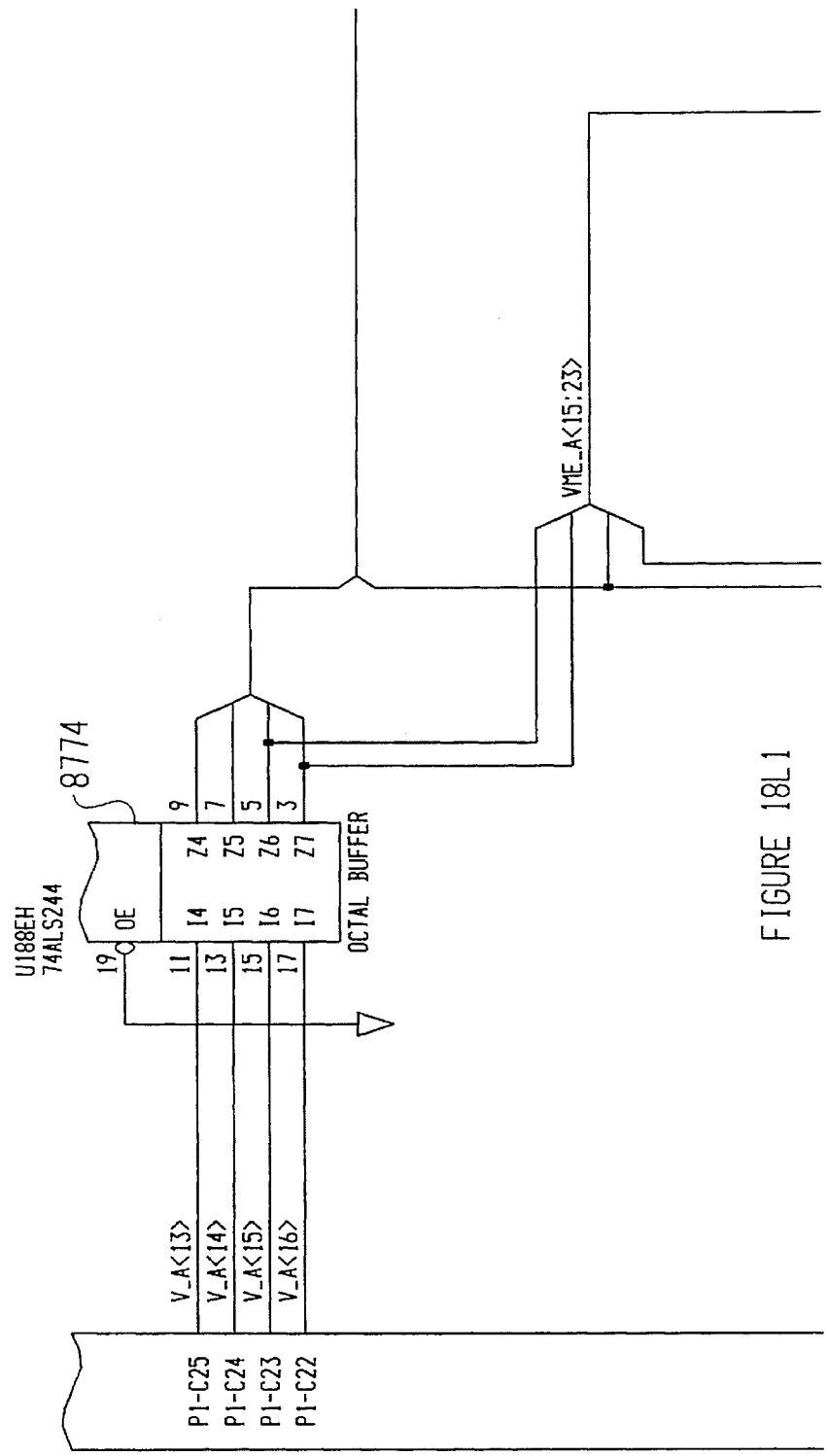
FIGURE 18L1

VME_A<13:19>

VME_WR_L

FIGURE 18L2

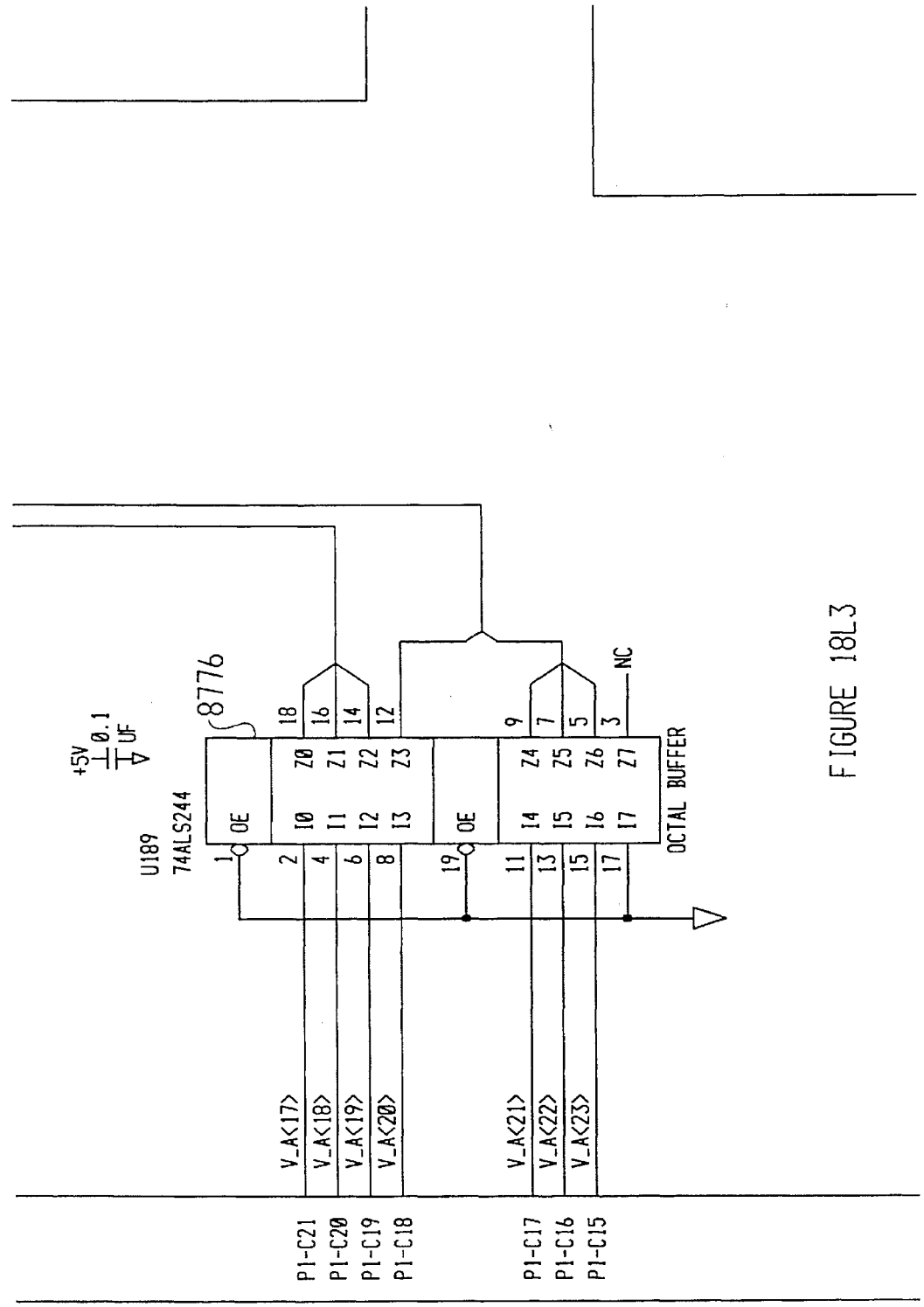
FIGURE 18L3

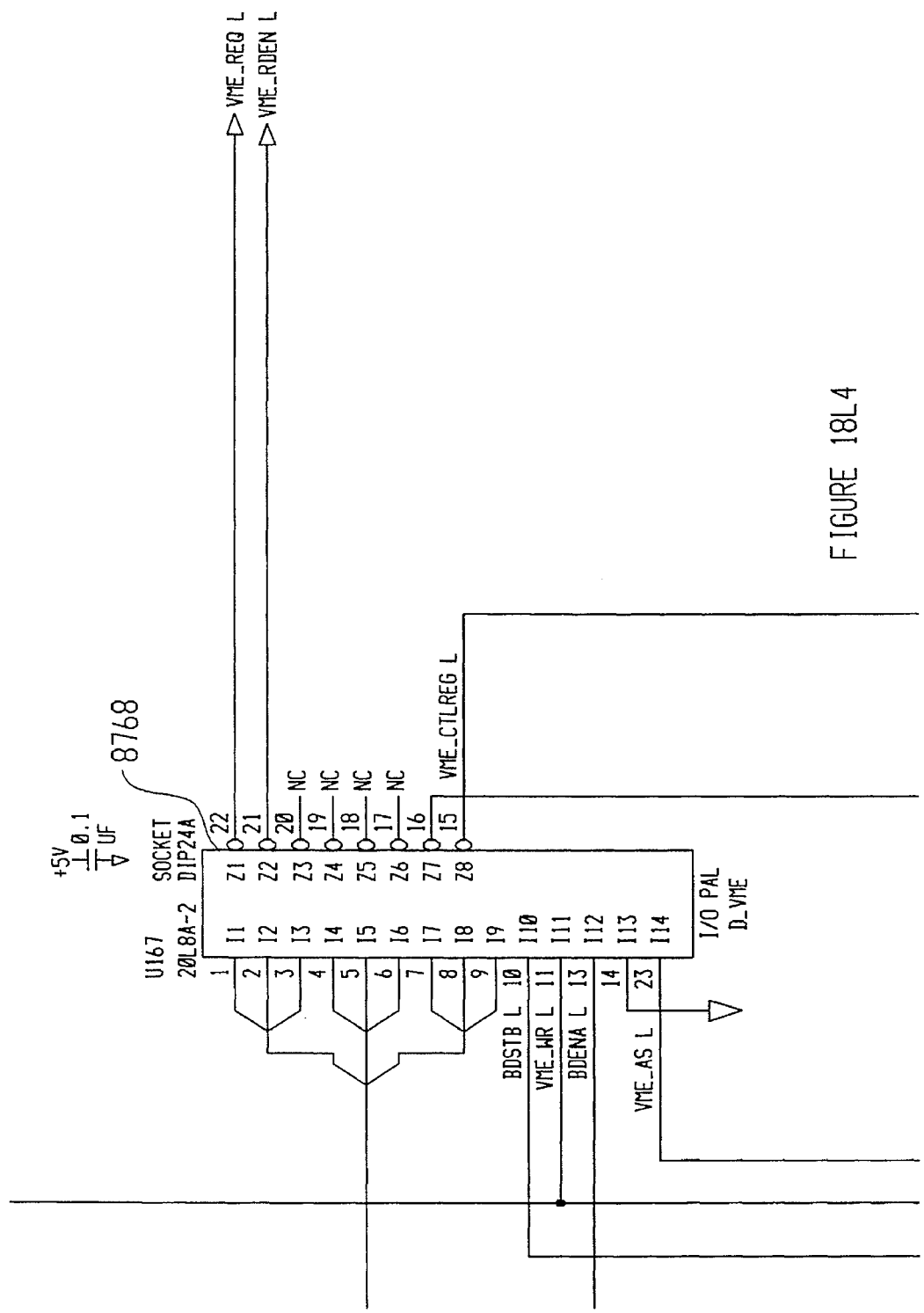
FIGURE 18L4

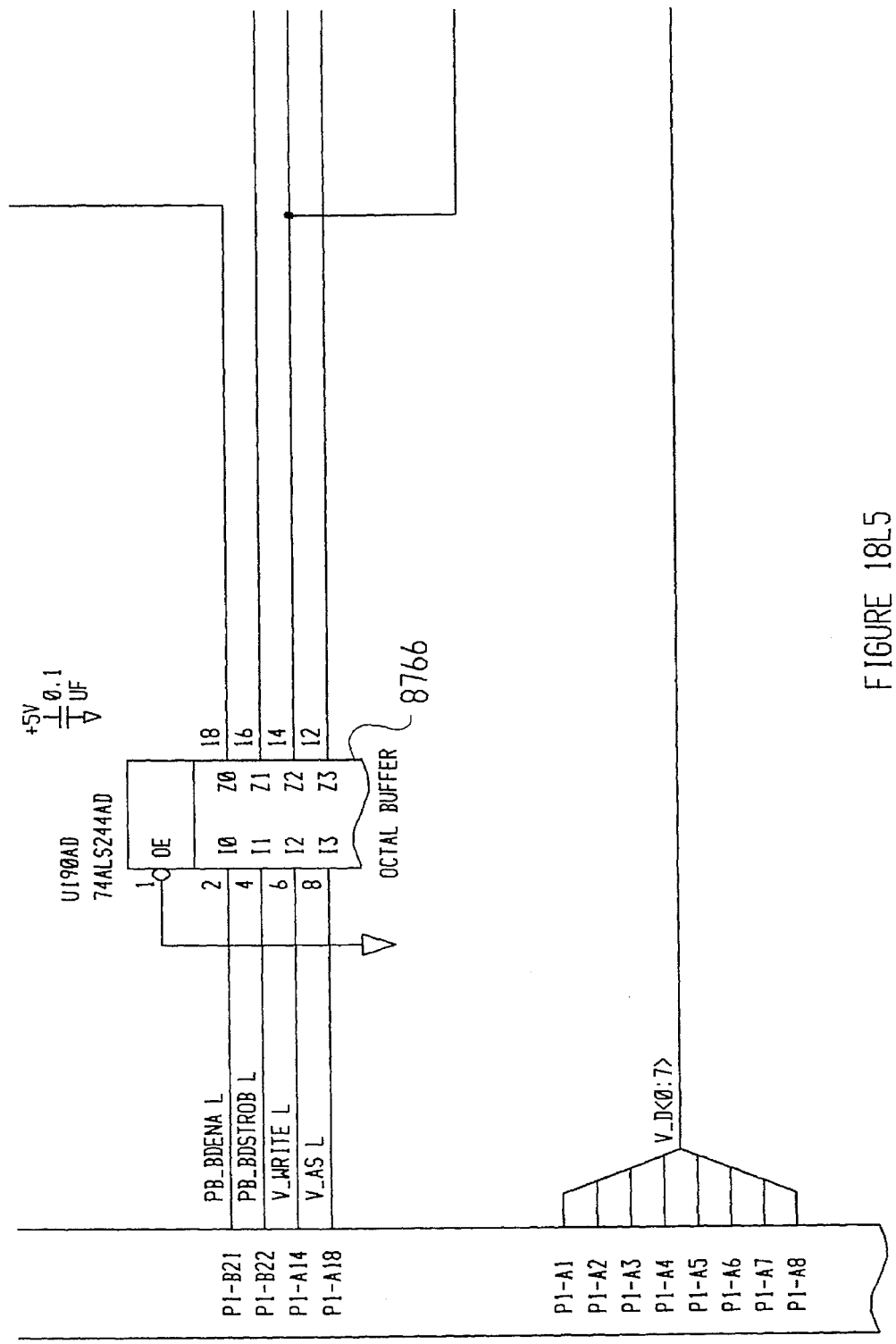
FIGURE 18L5

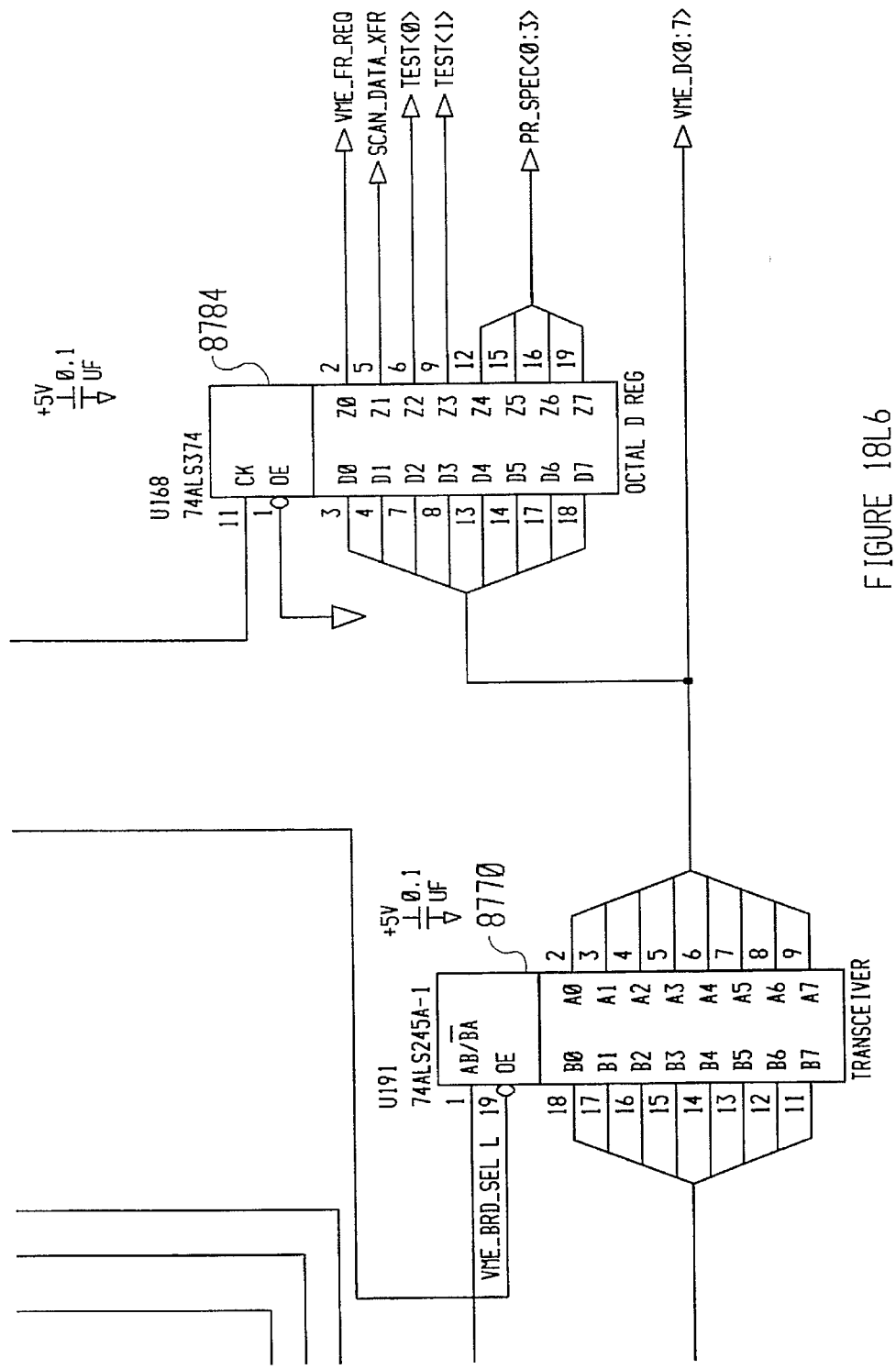
FIGURE 18L6

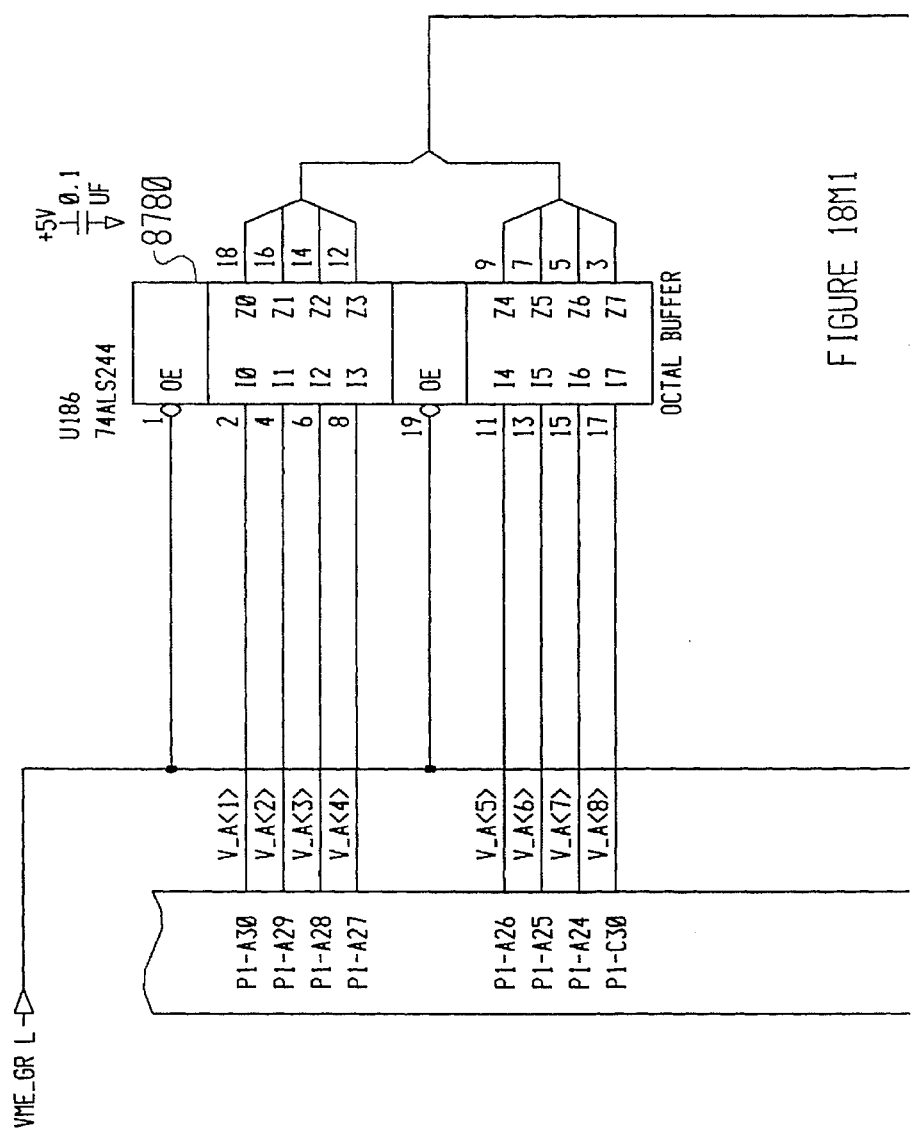
FIGURE 18M1

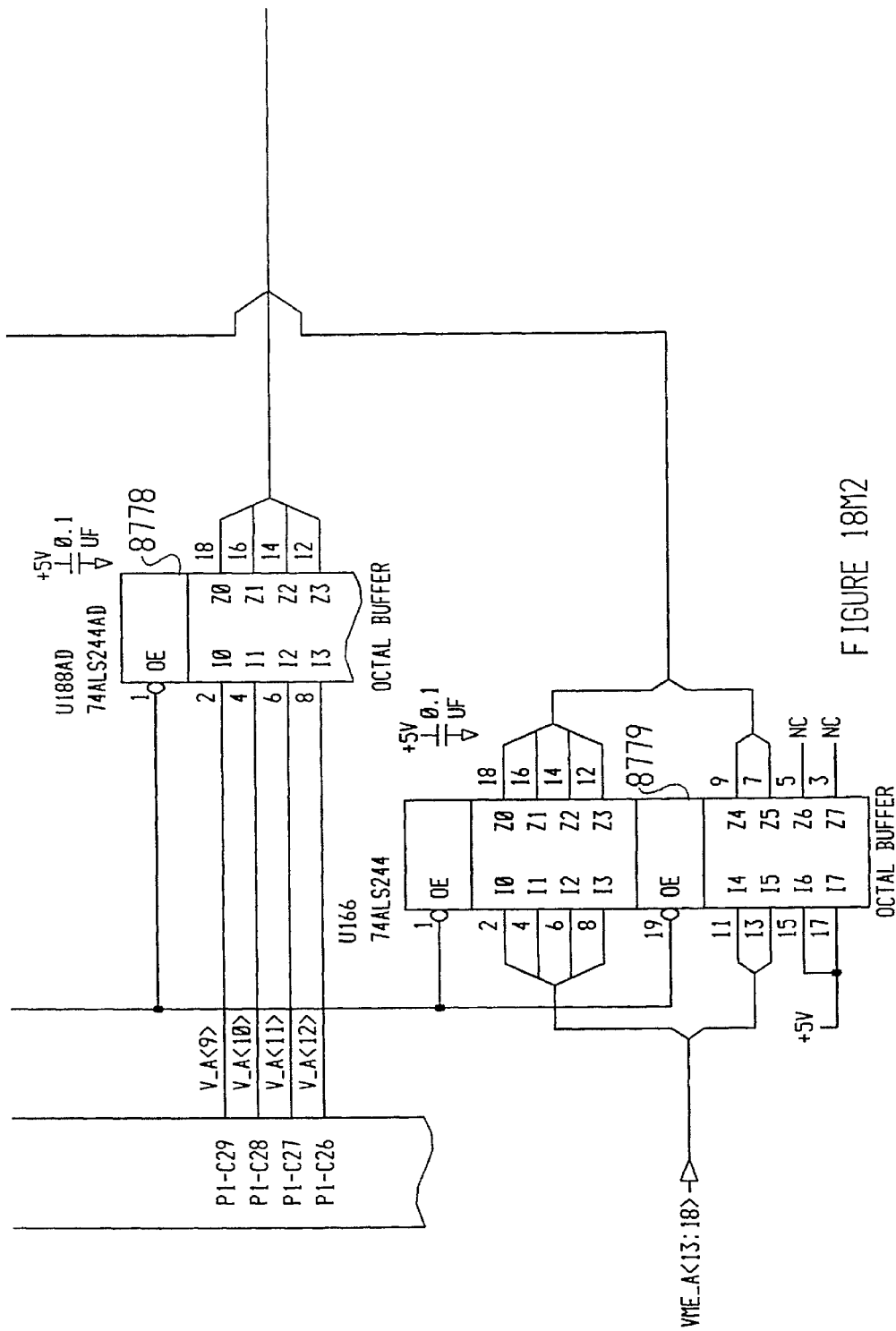
FIGURE 18M2

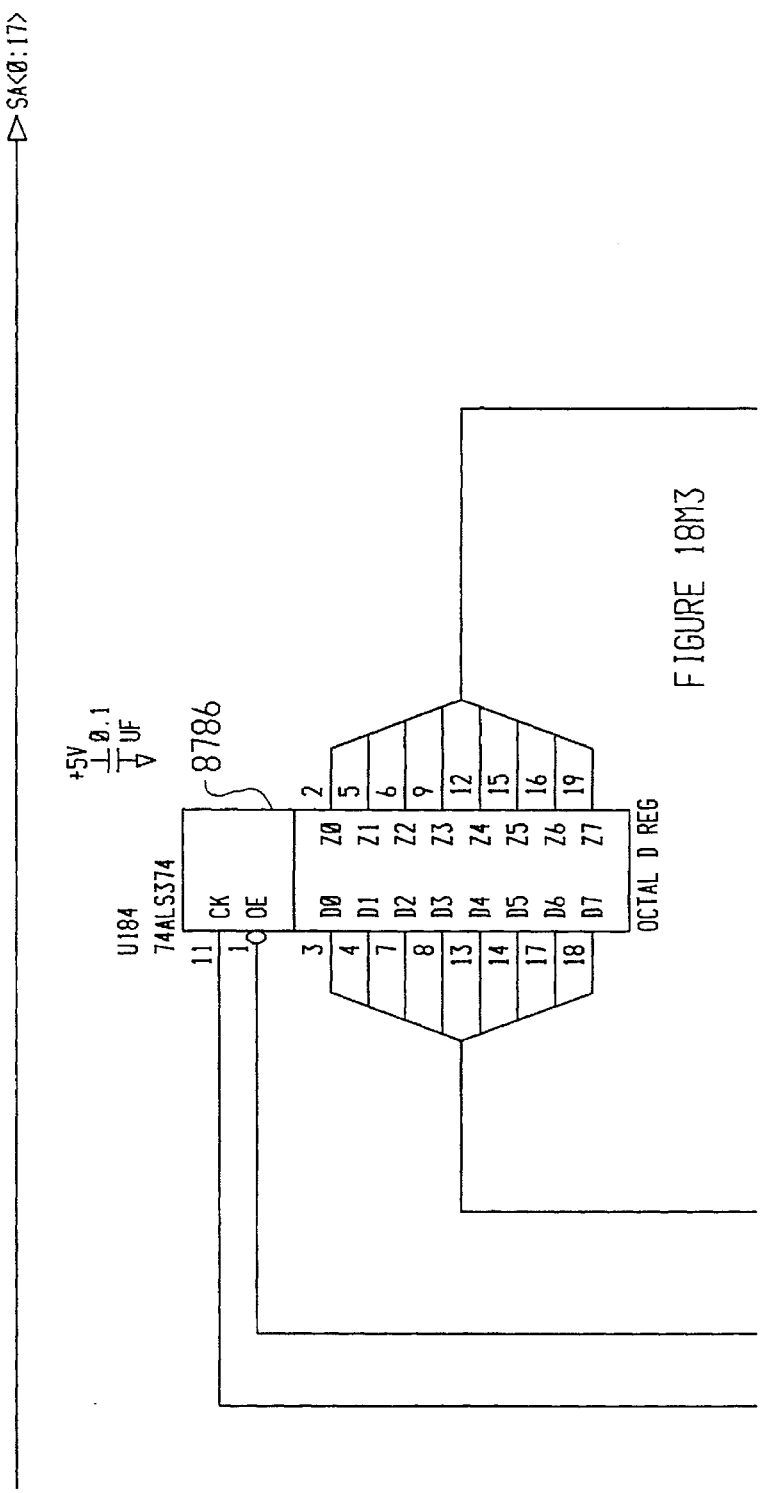
FIGURE 18M3

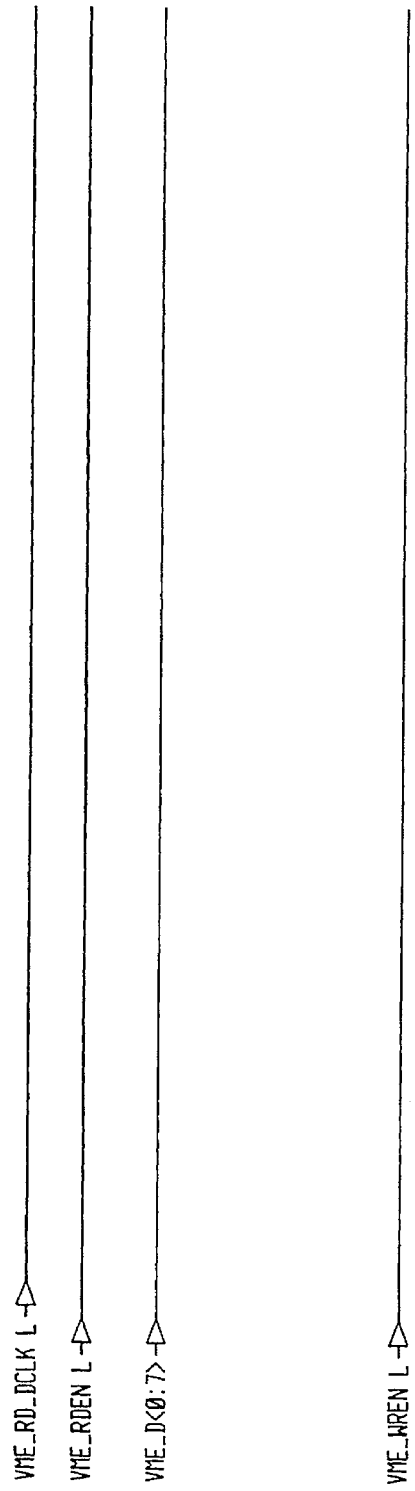

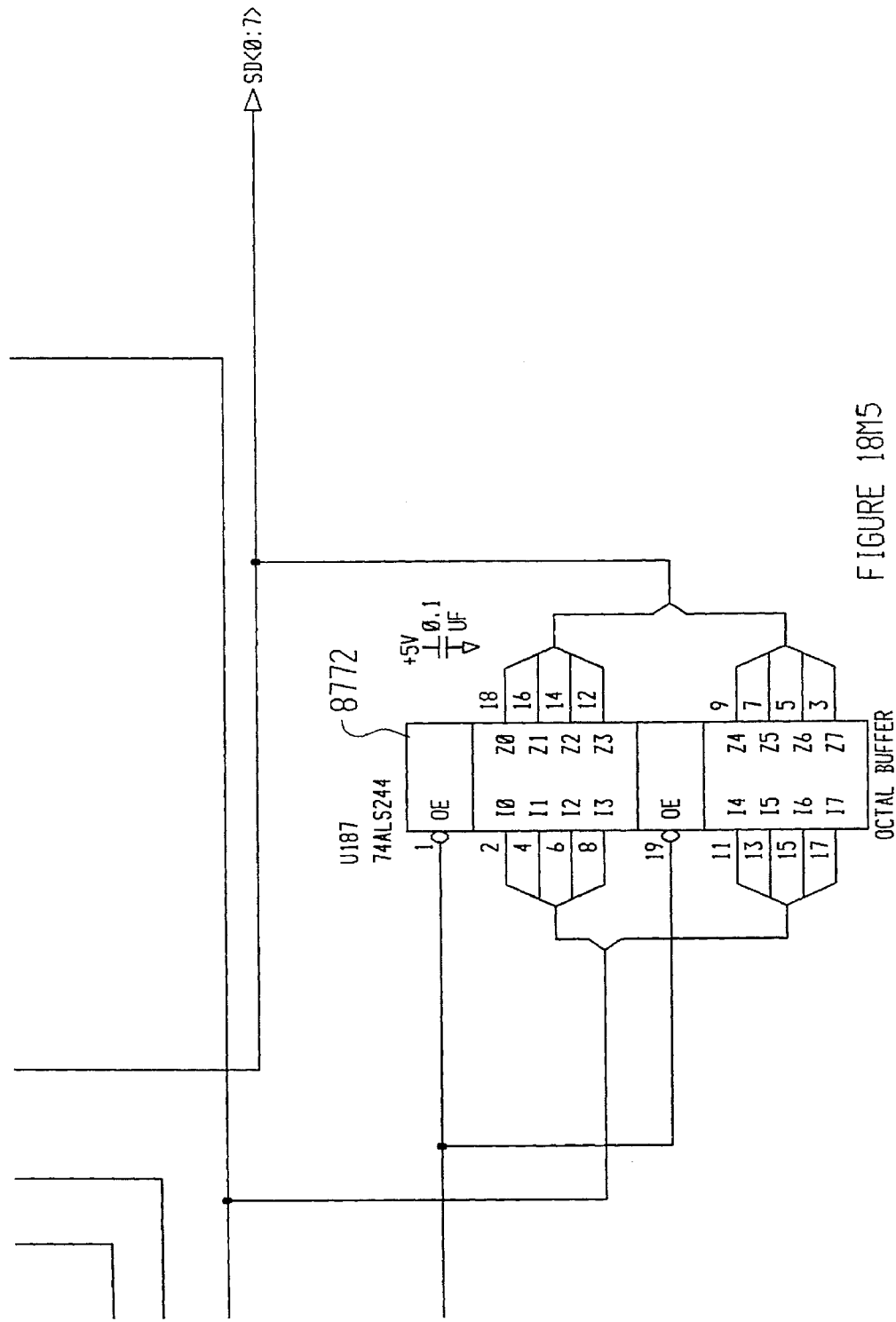
FIGURE 18M5

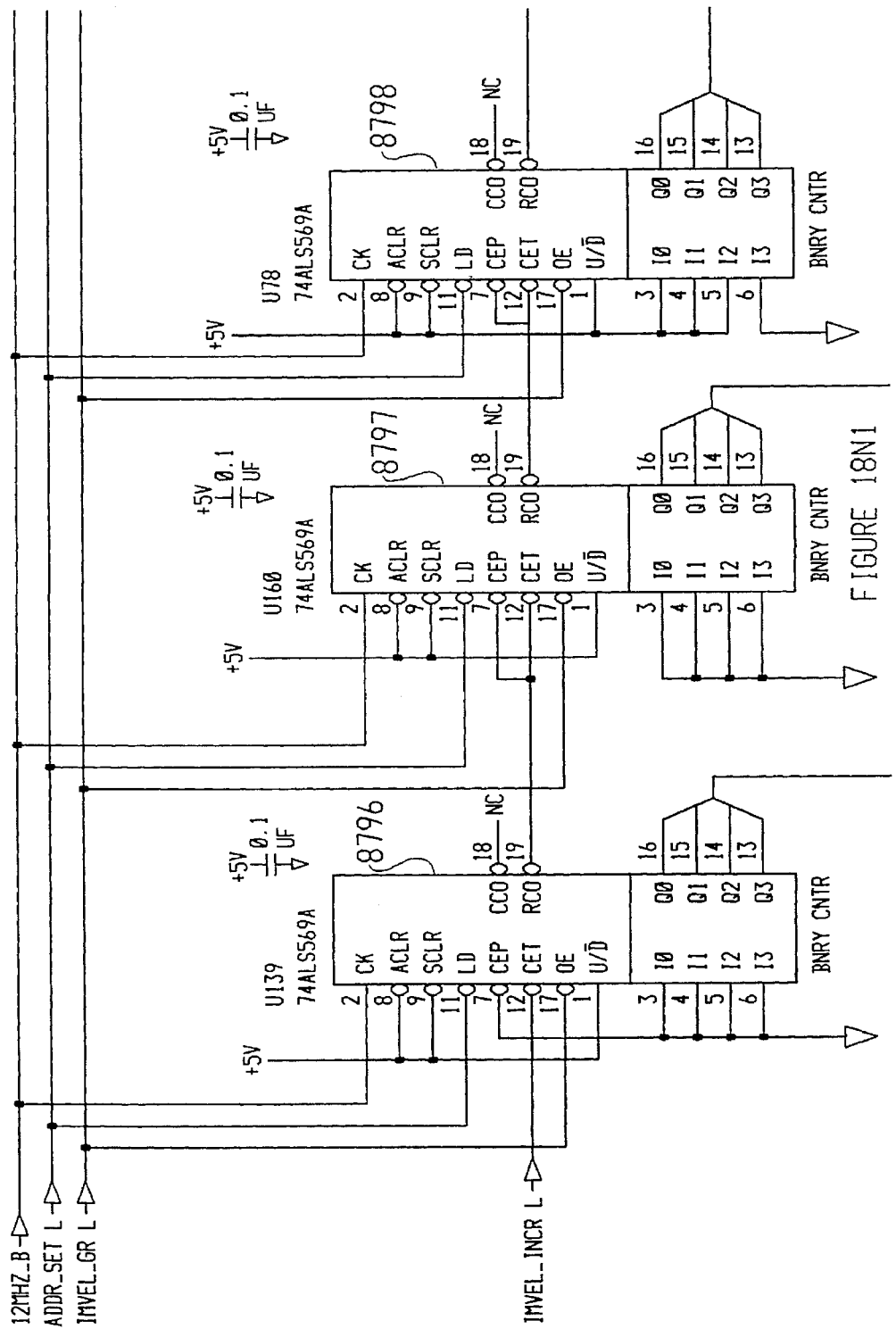

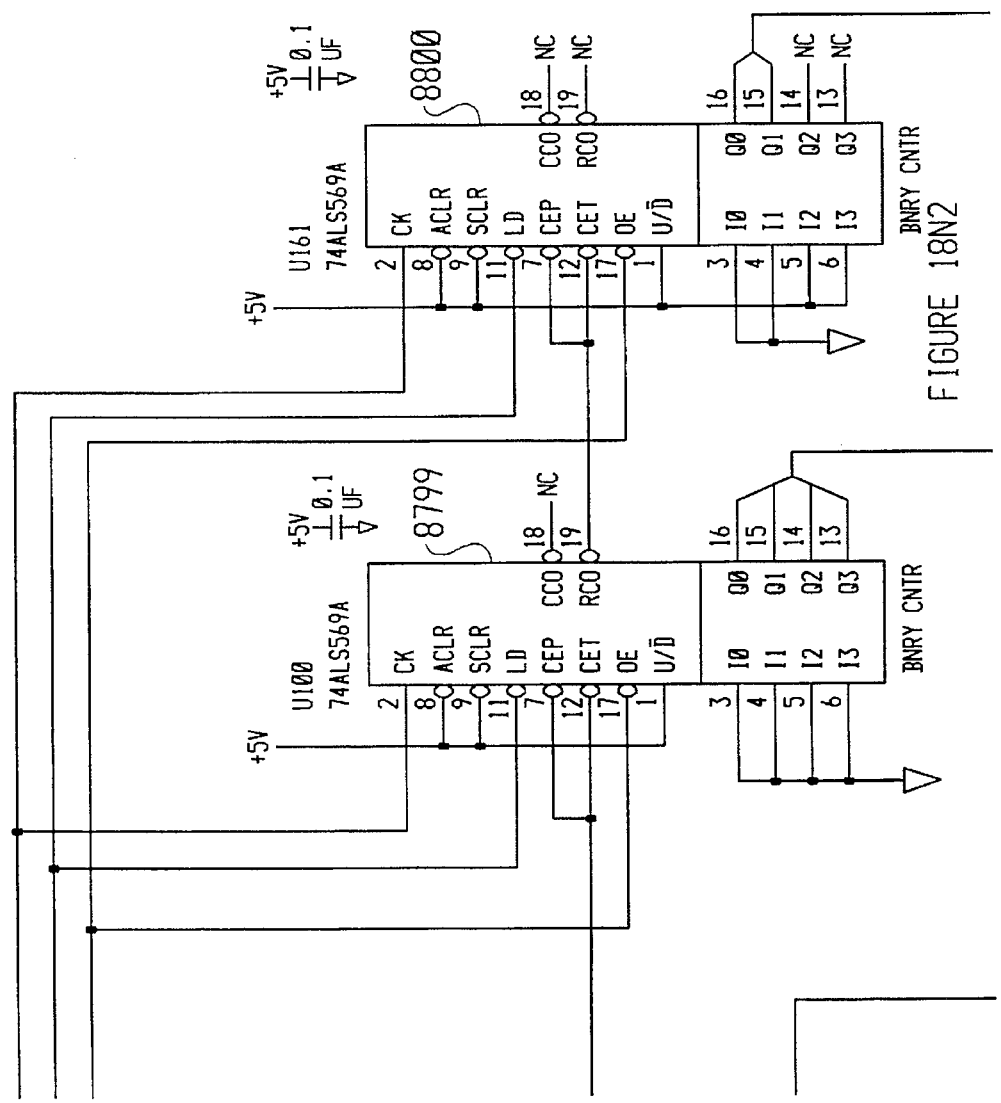

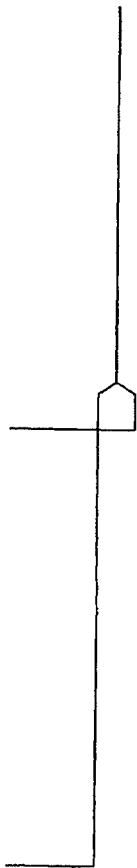
FIGURE 18N3

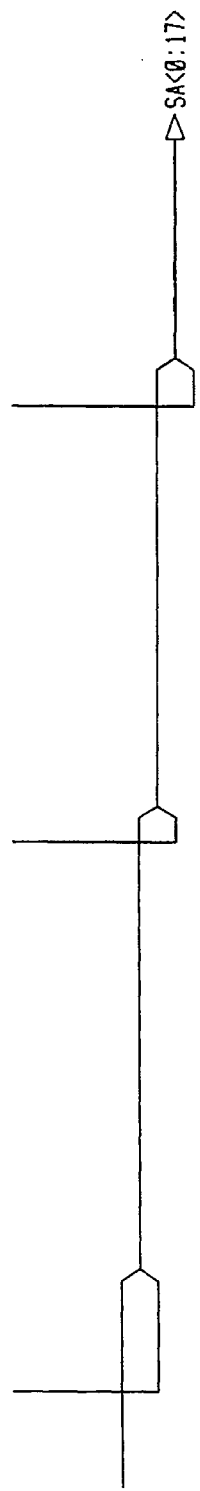
FIGURE 18N4

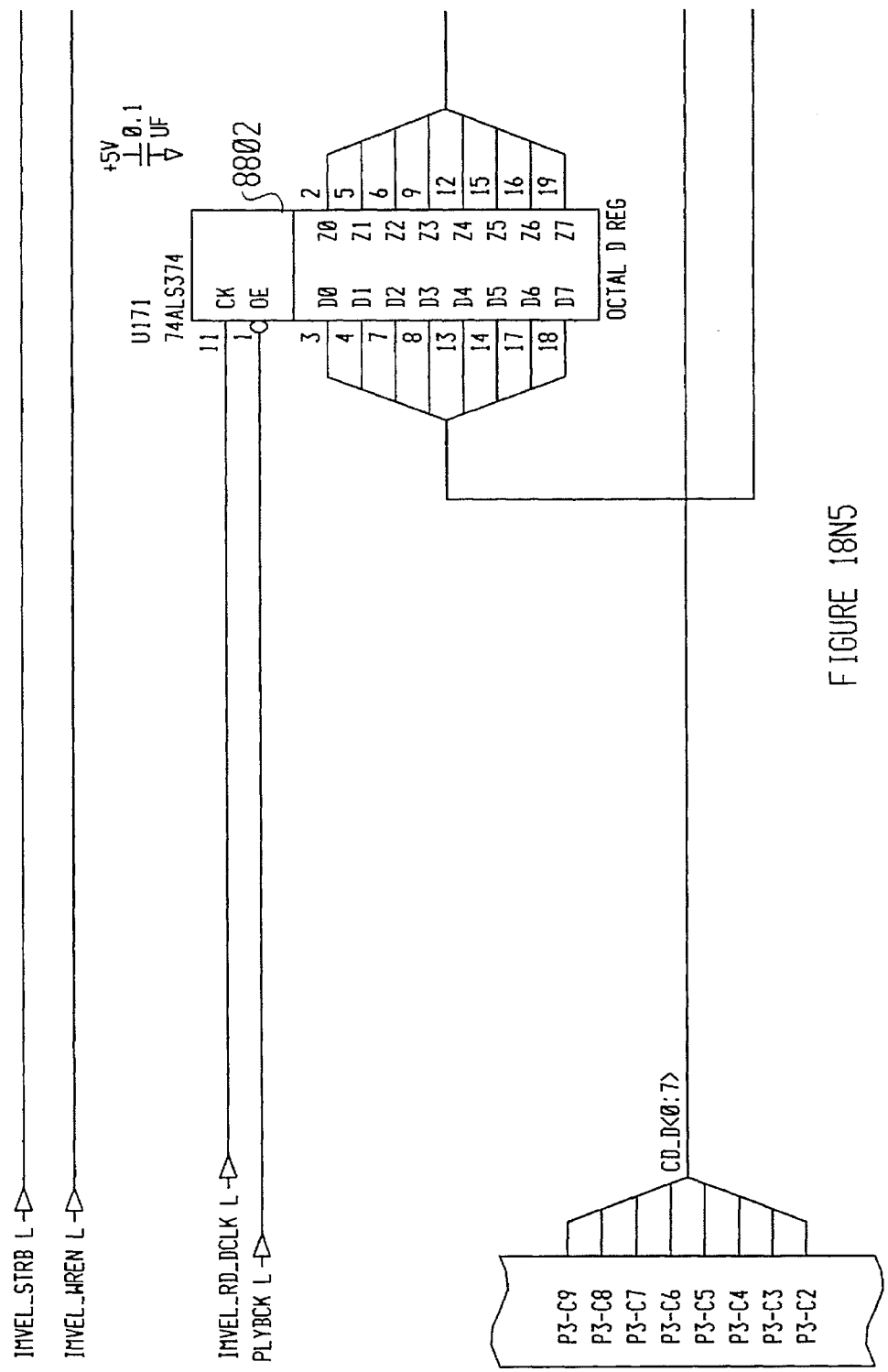
FIGURE 18N5

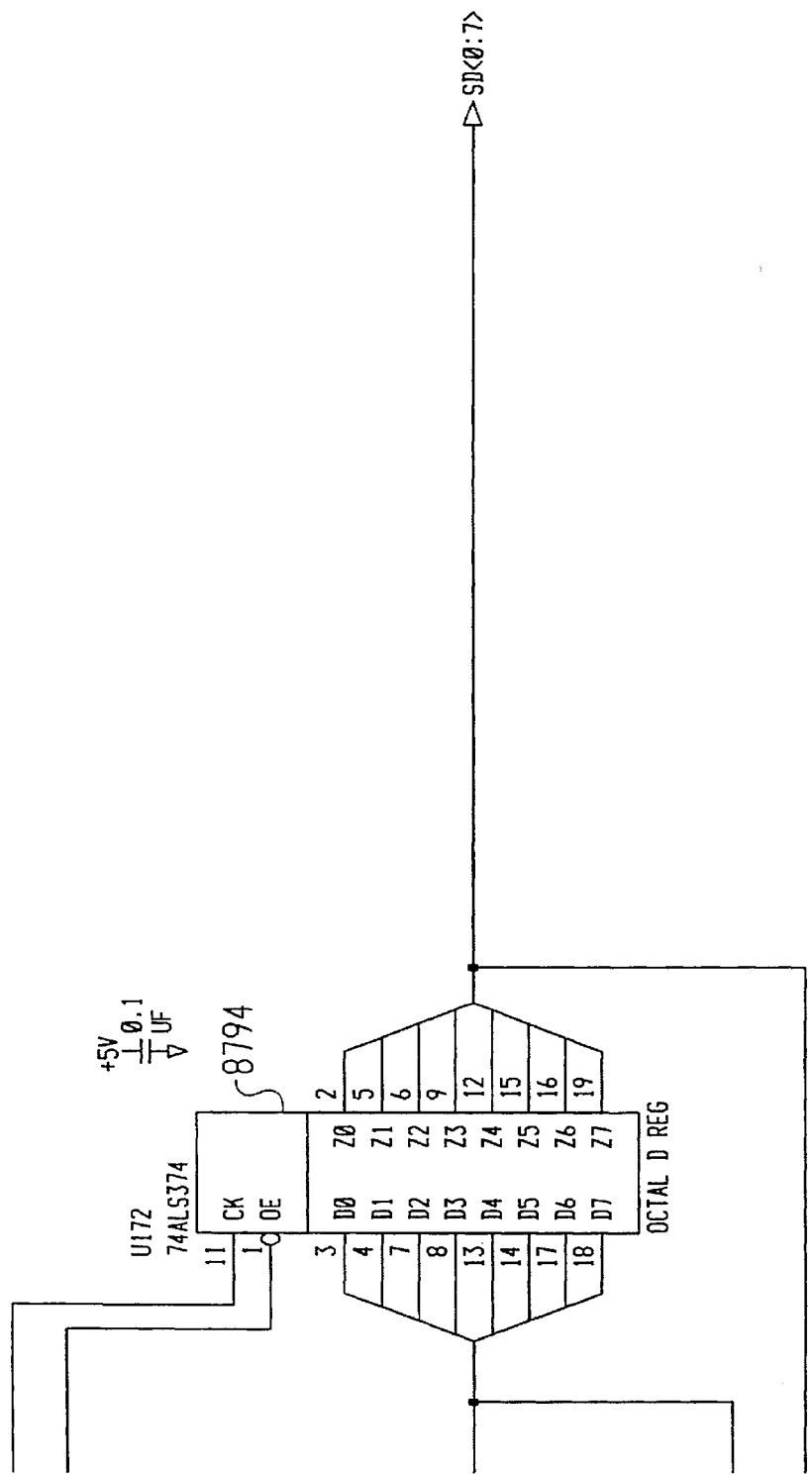
FIGURE 18N6

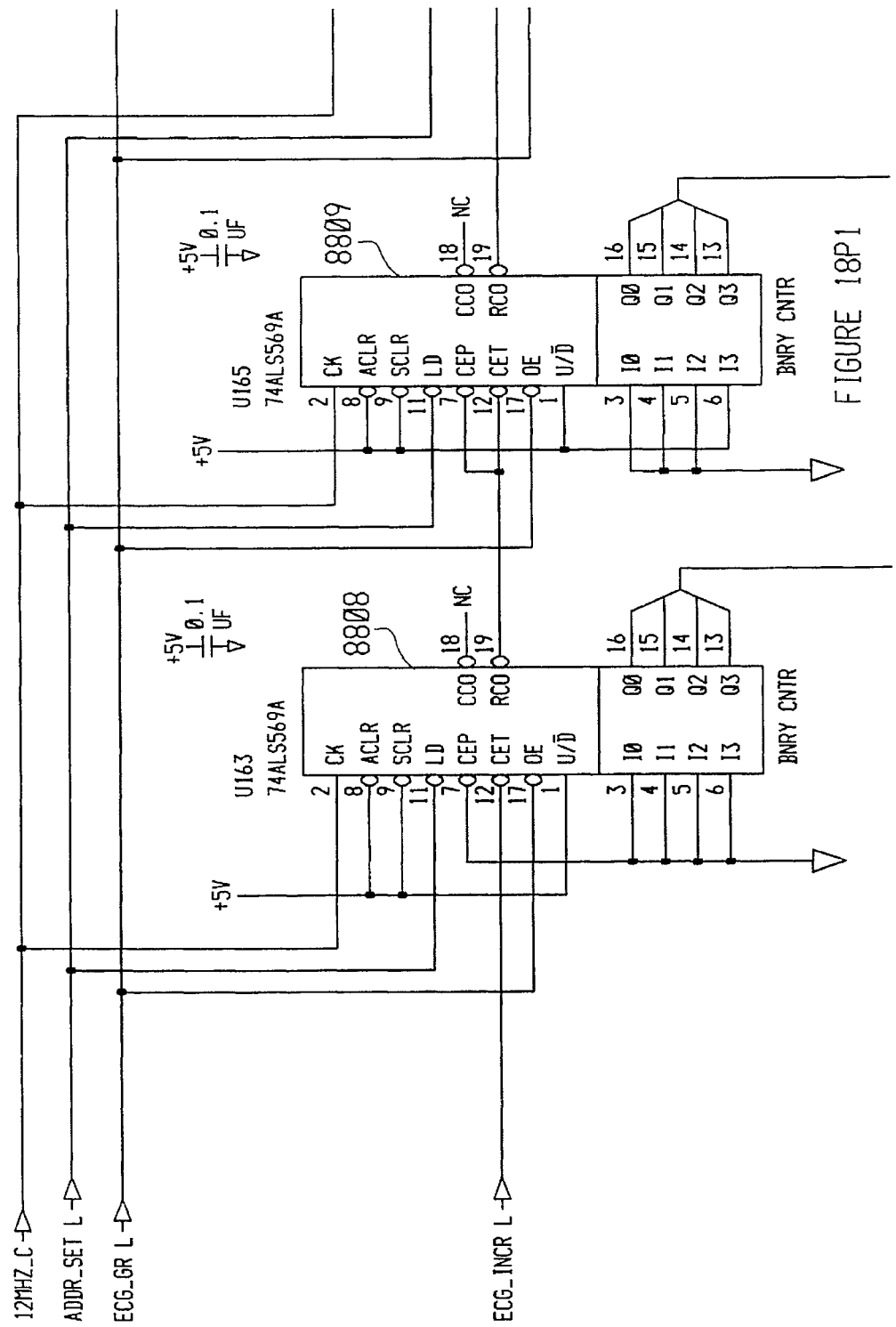

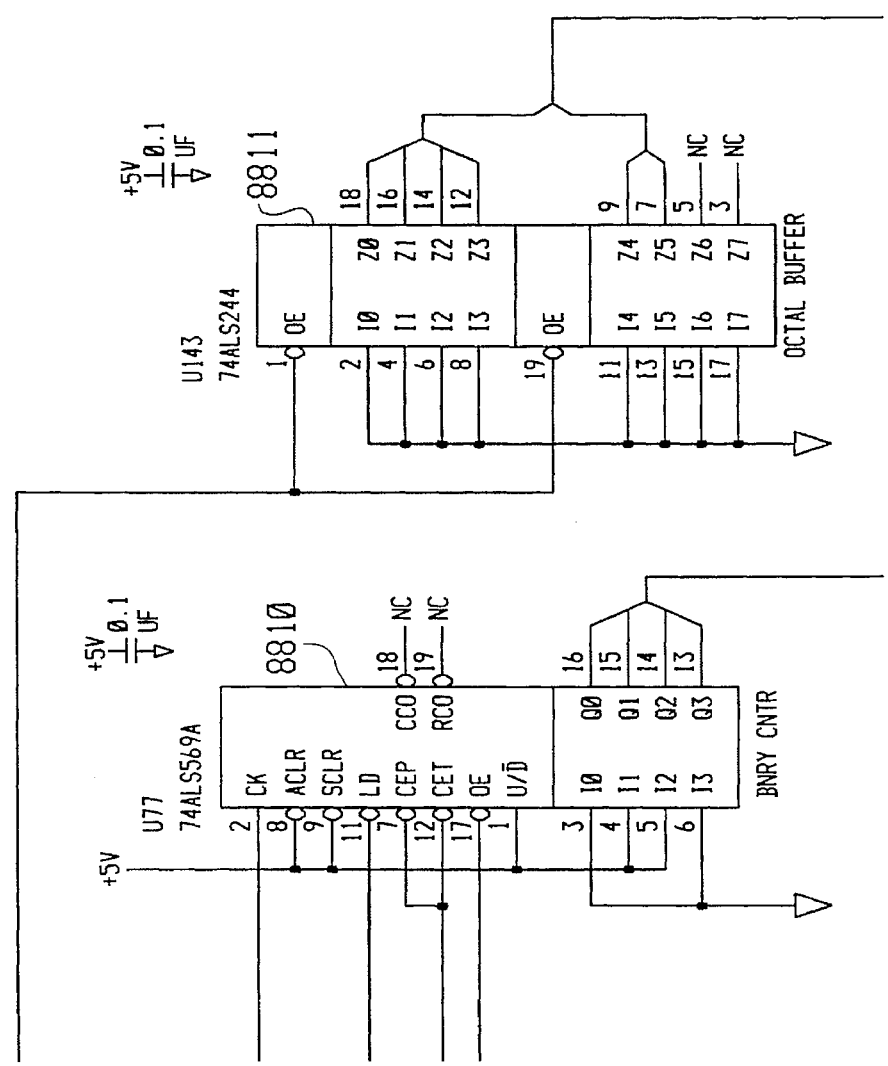
FIGURE 18P2

FIGURE 18P3

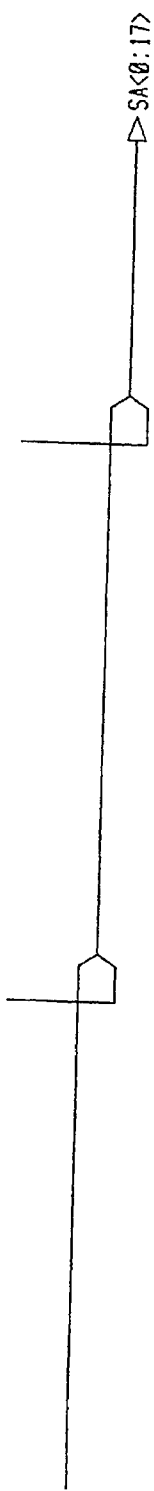
FIGURE 18P4

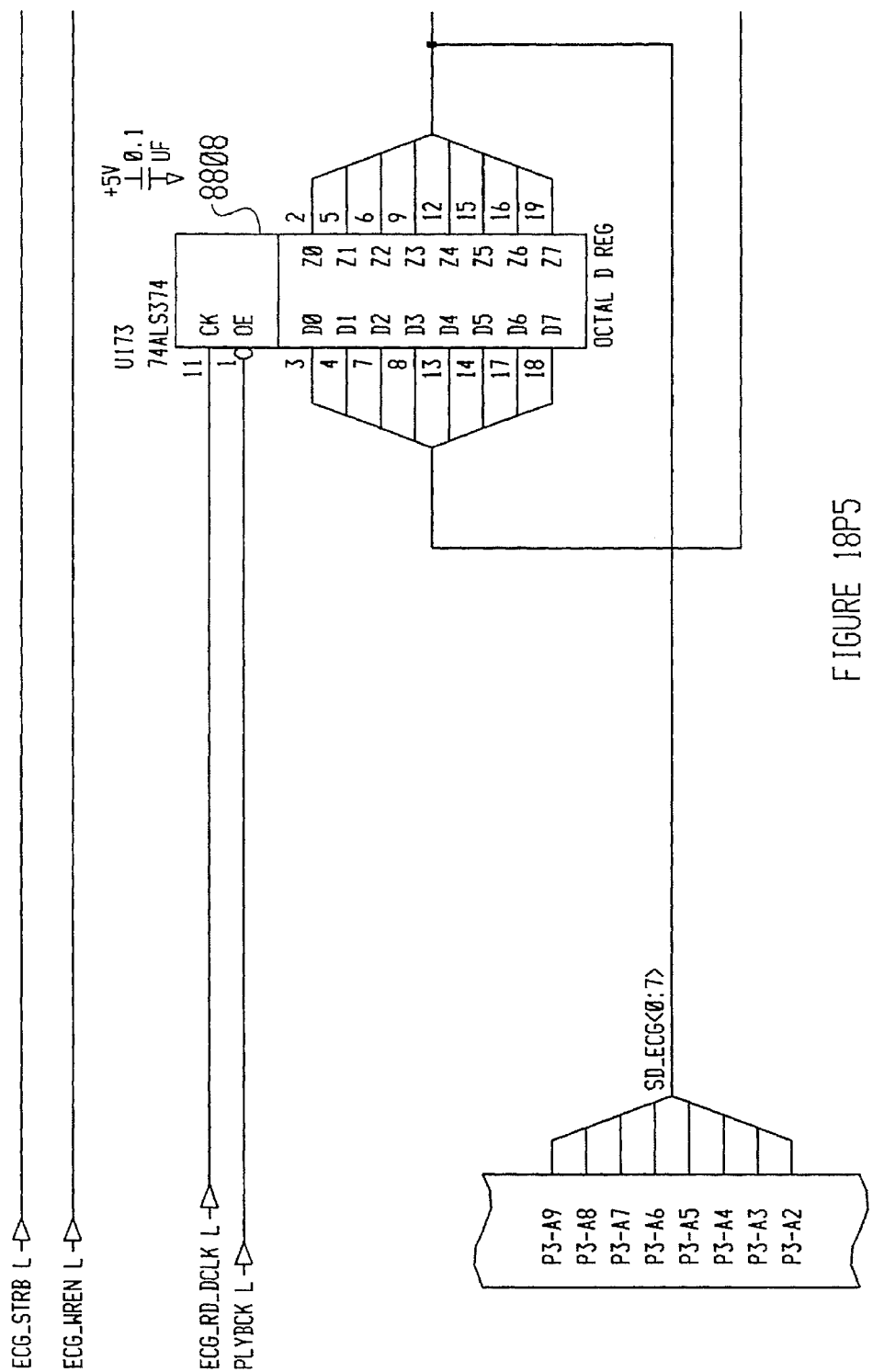
FIGURE 18P5

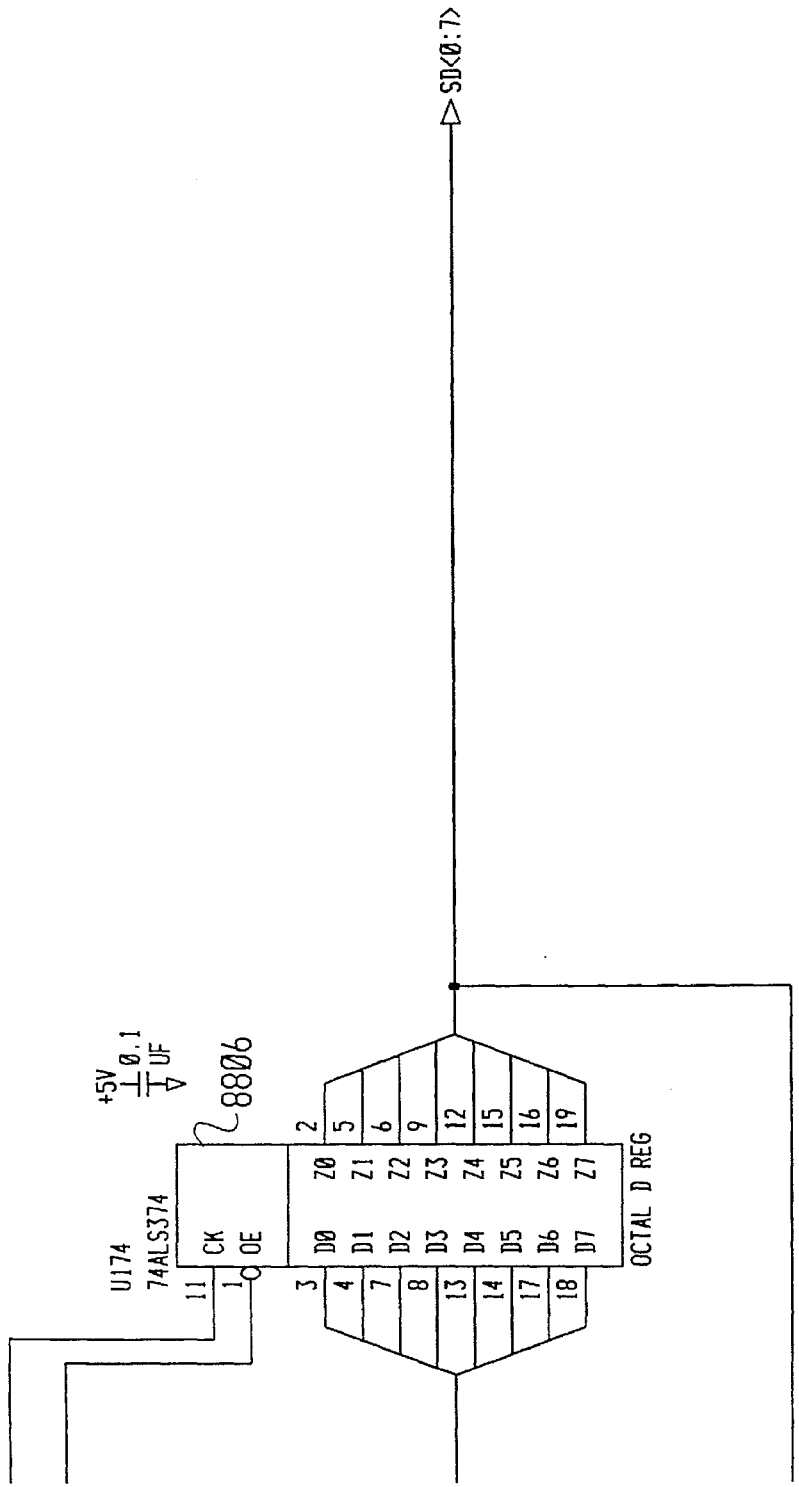
FIGURE 18P6

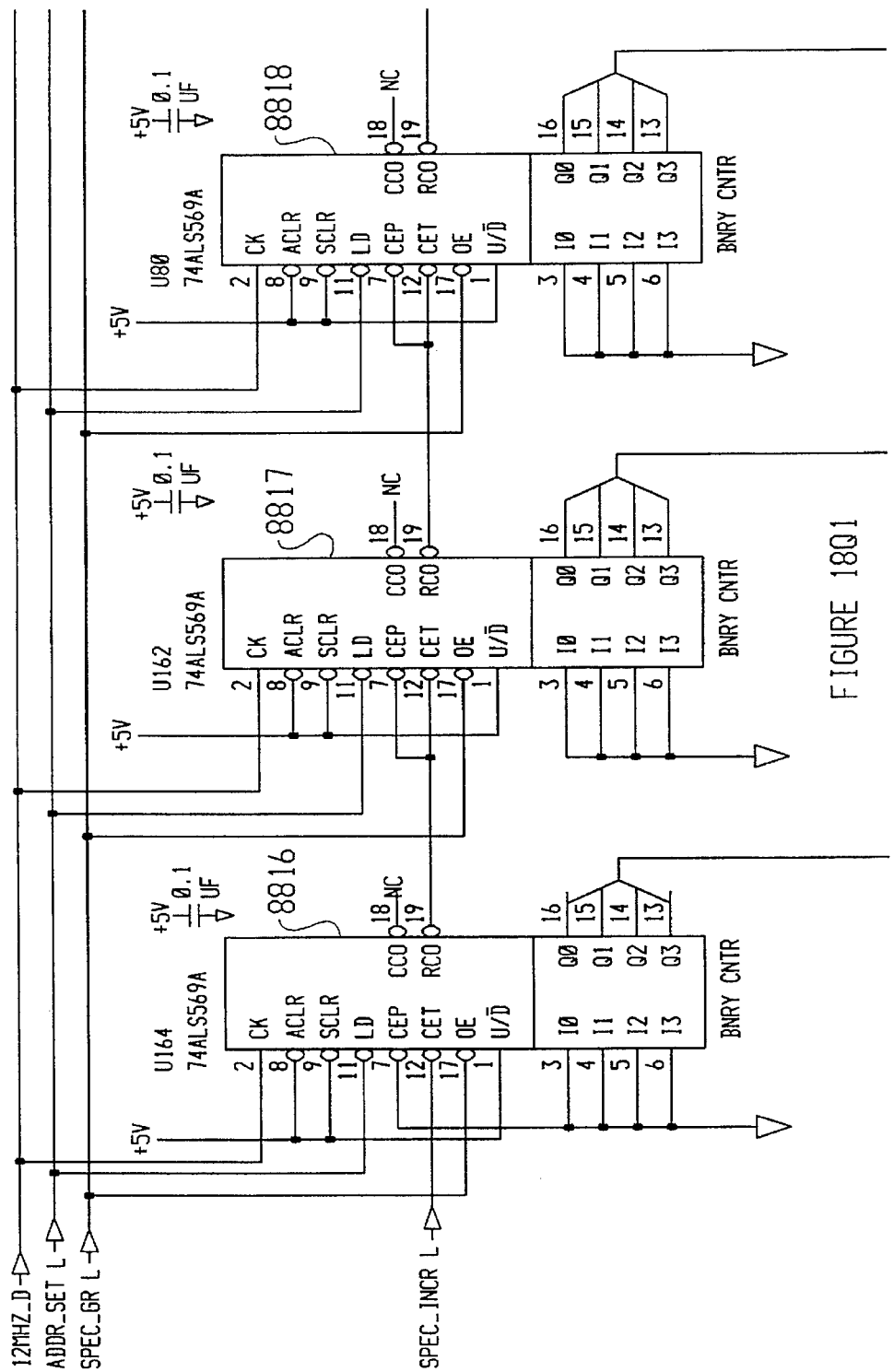
FIGURE 18Q1

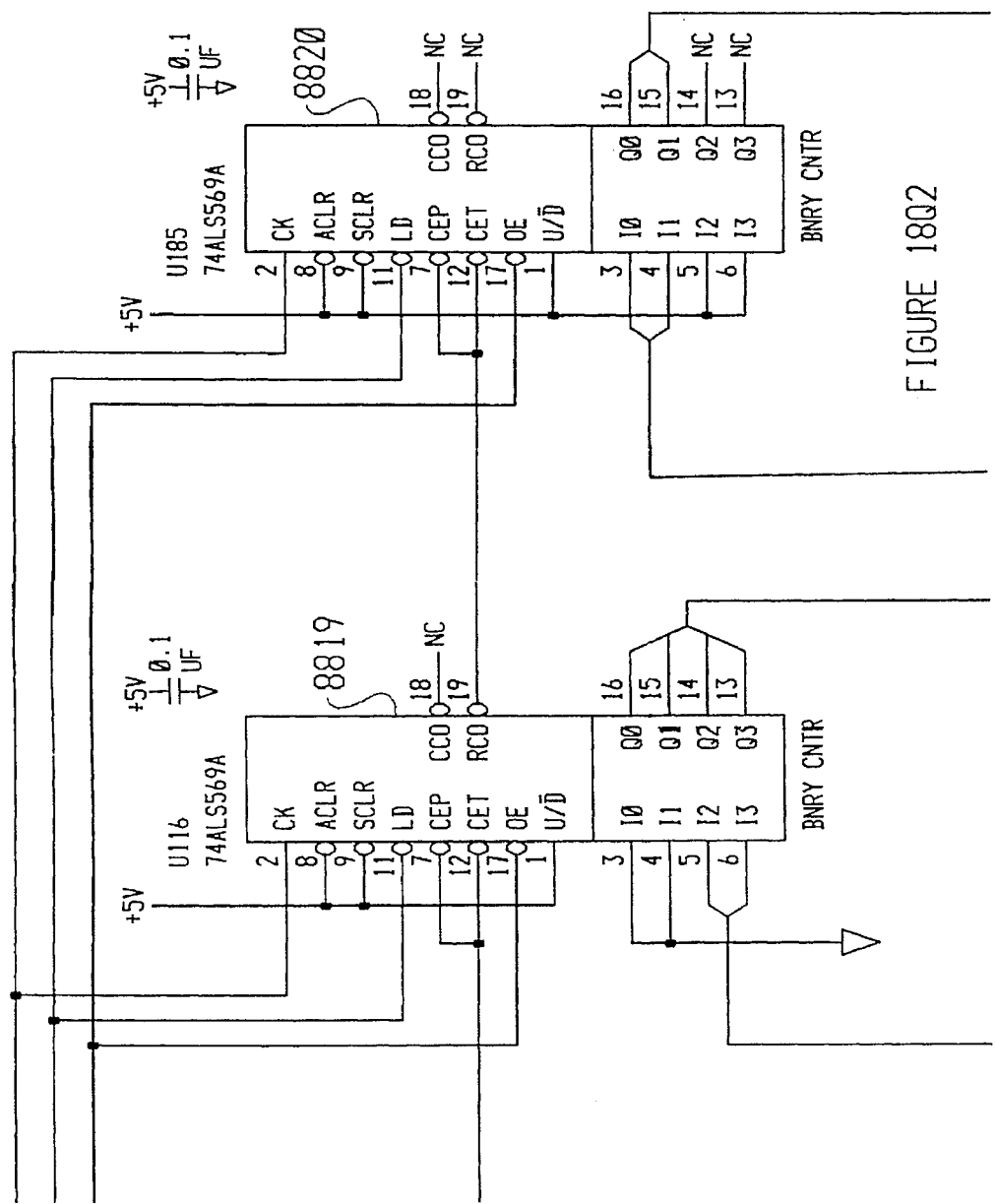
FIGURE 1802

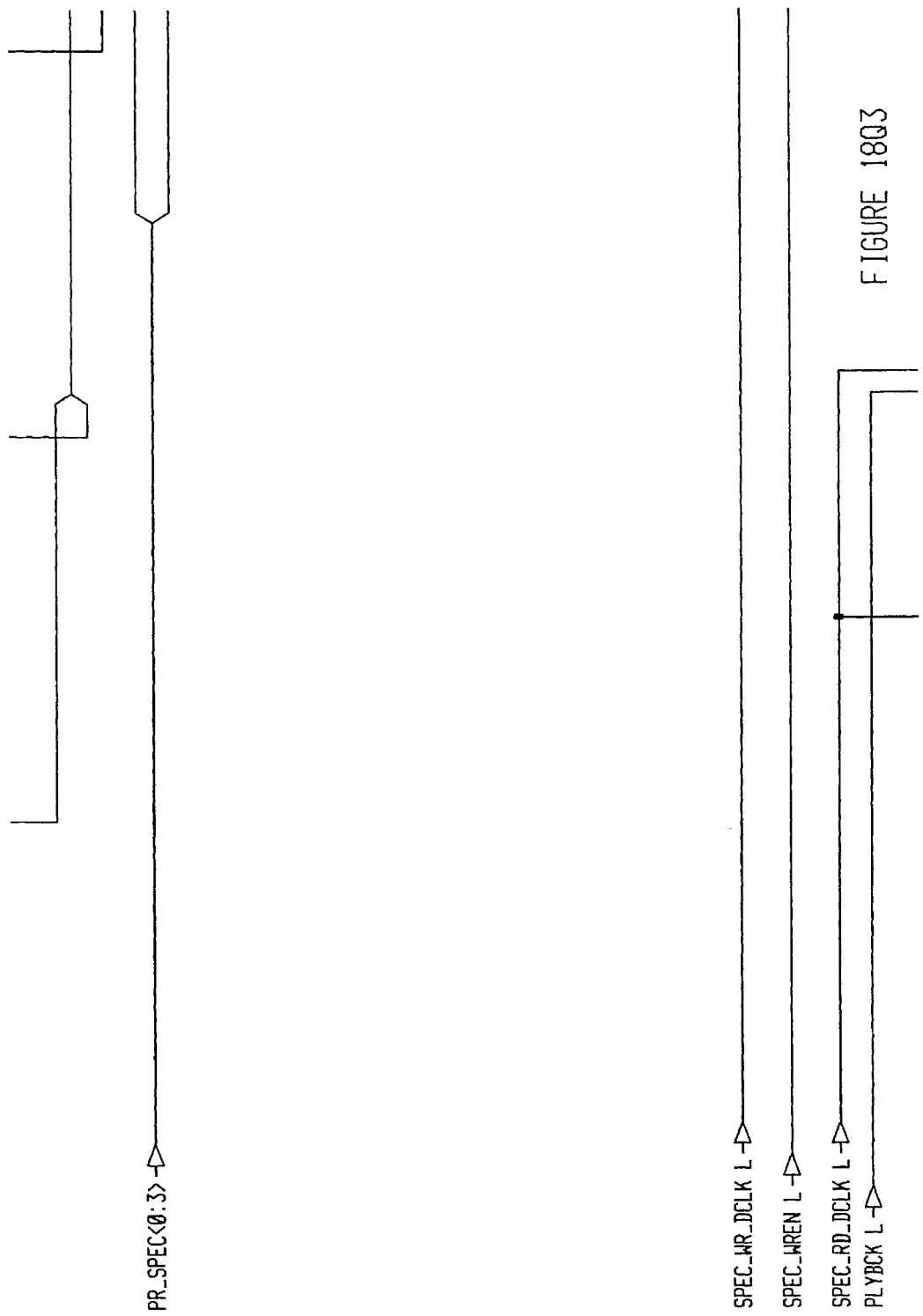

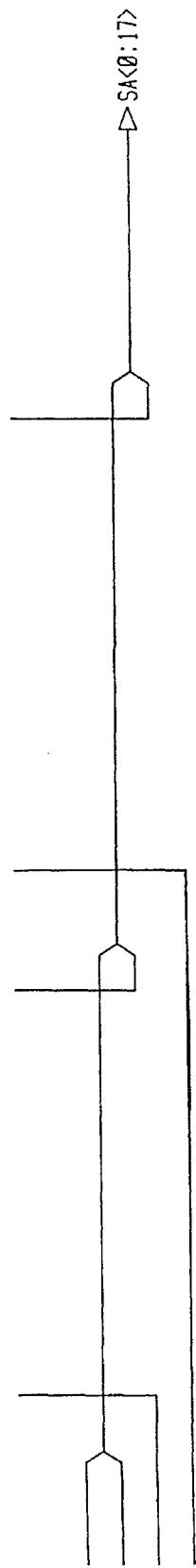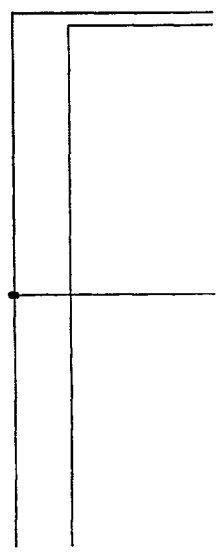
FIGURE 1804

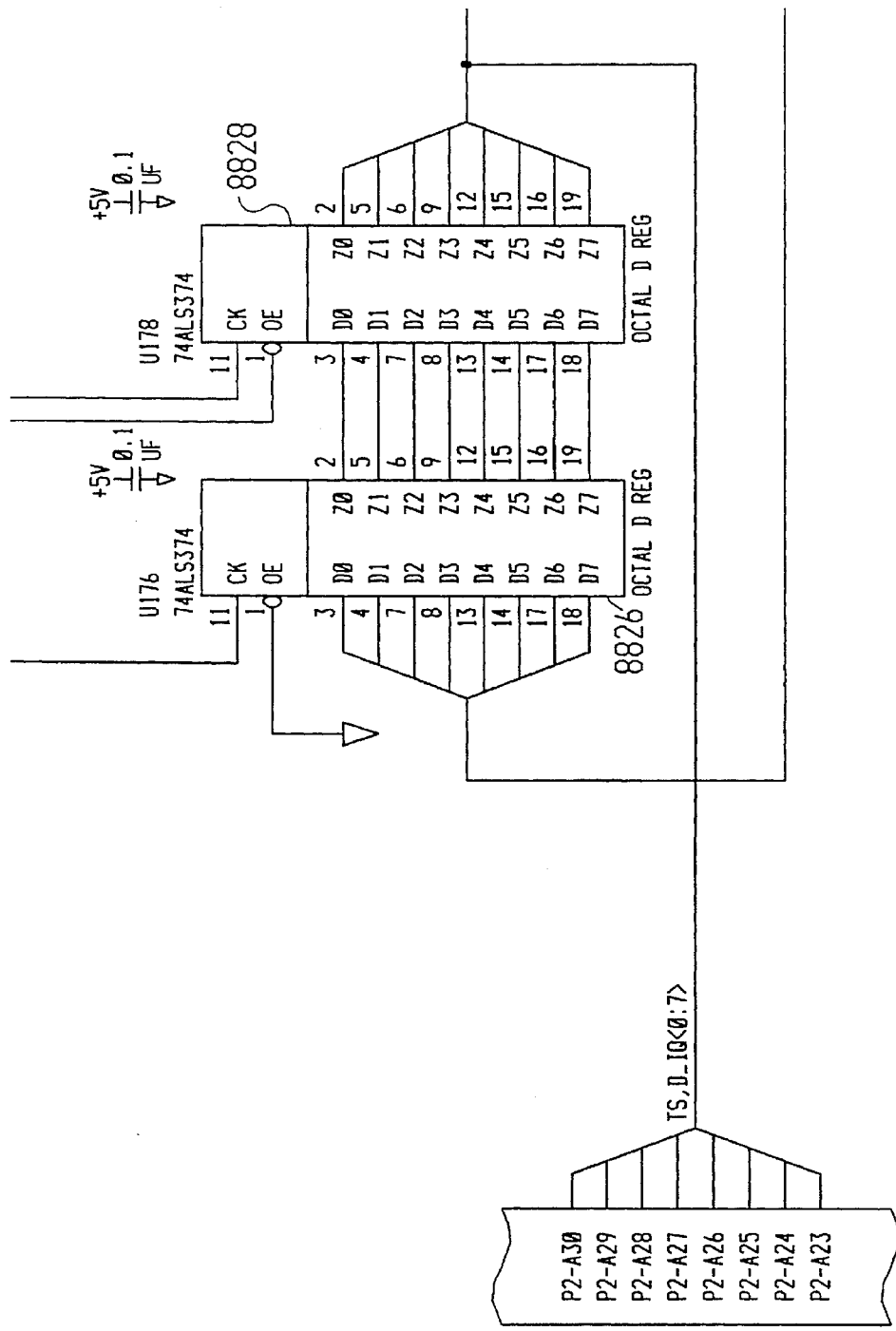
FIGURE 18Q5

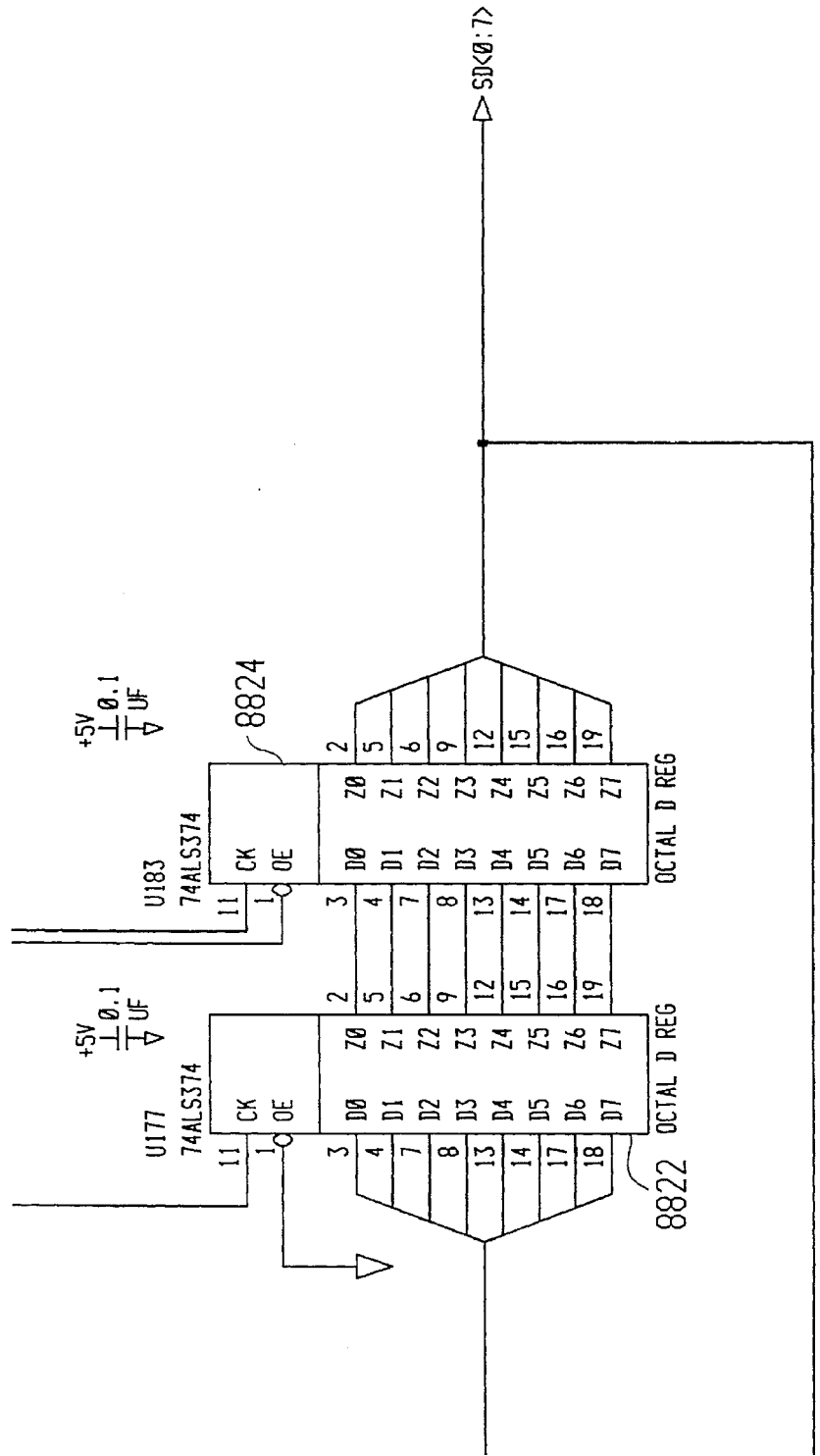
FIGURE 18Q6

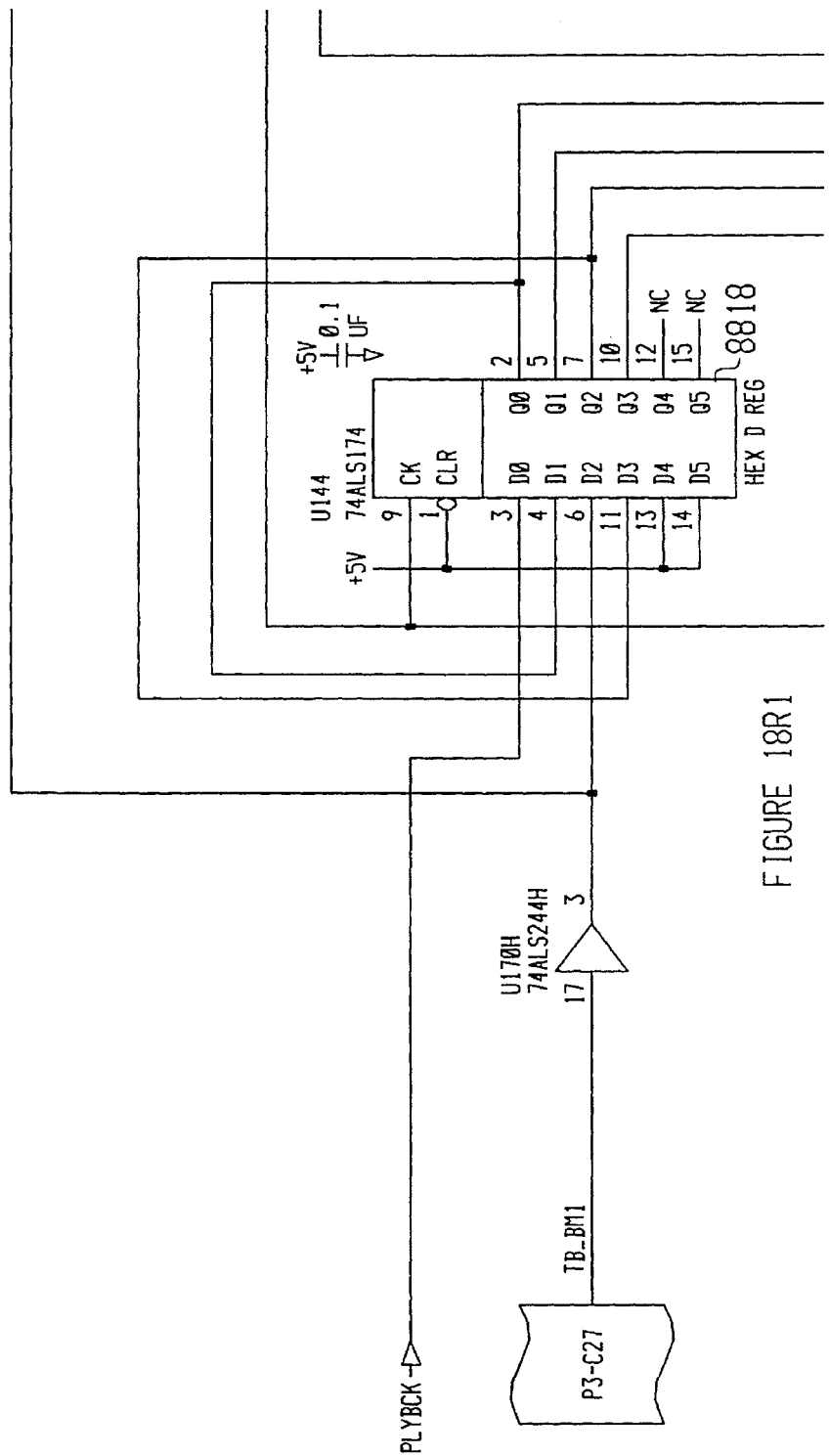
FIGURE 18R1

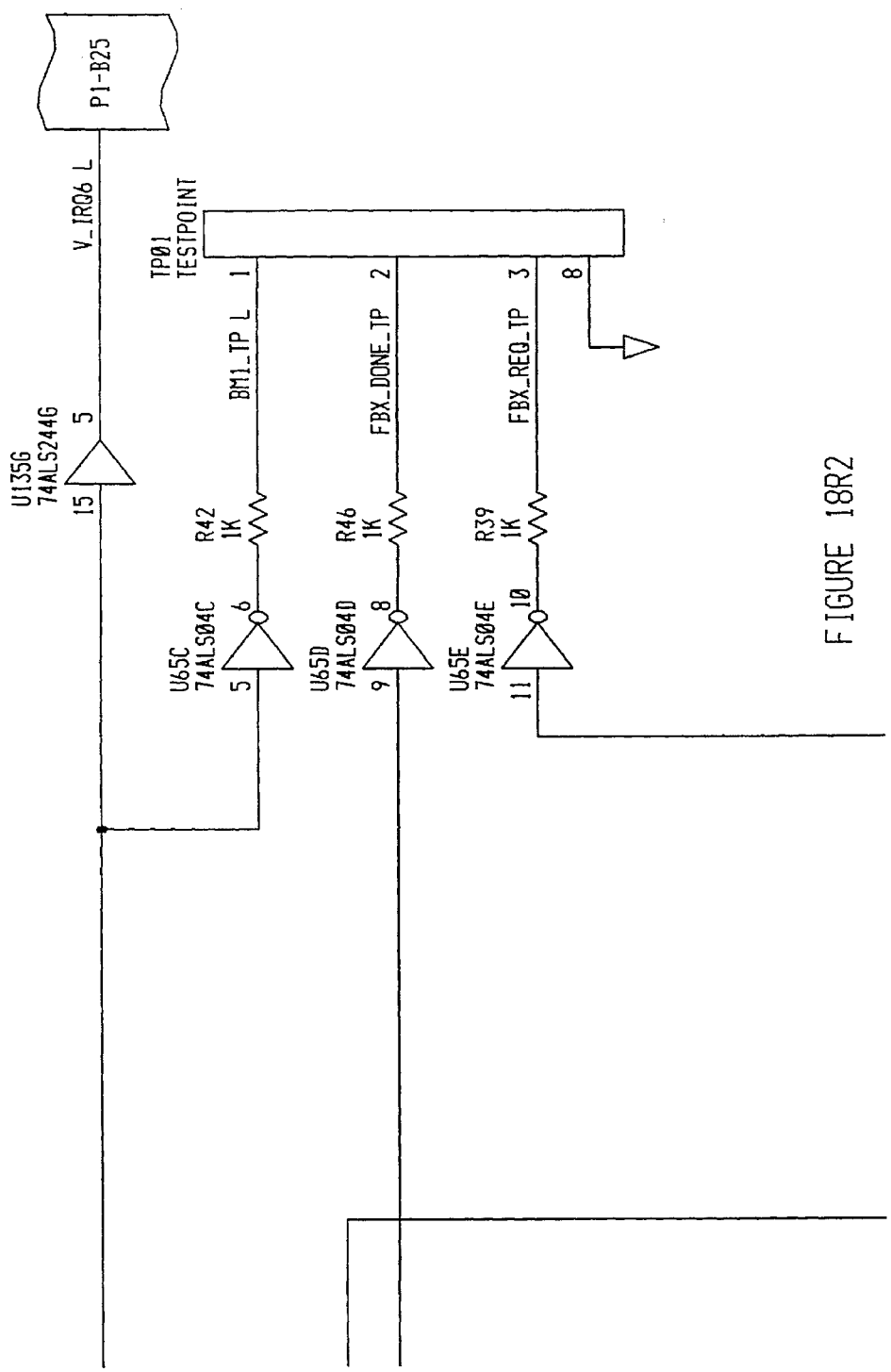
FIGURE 18R2

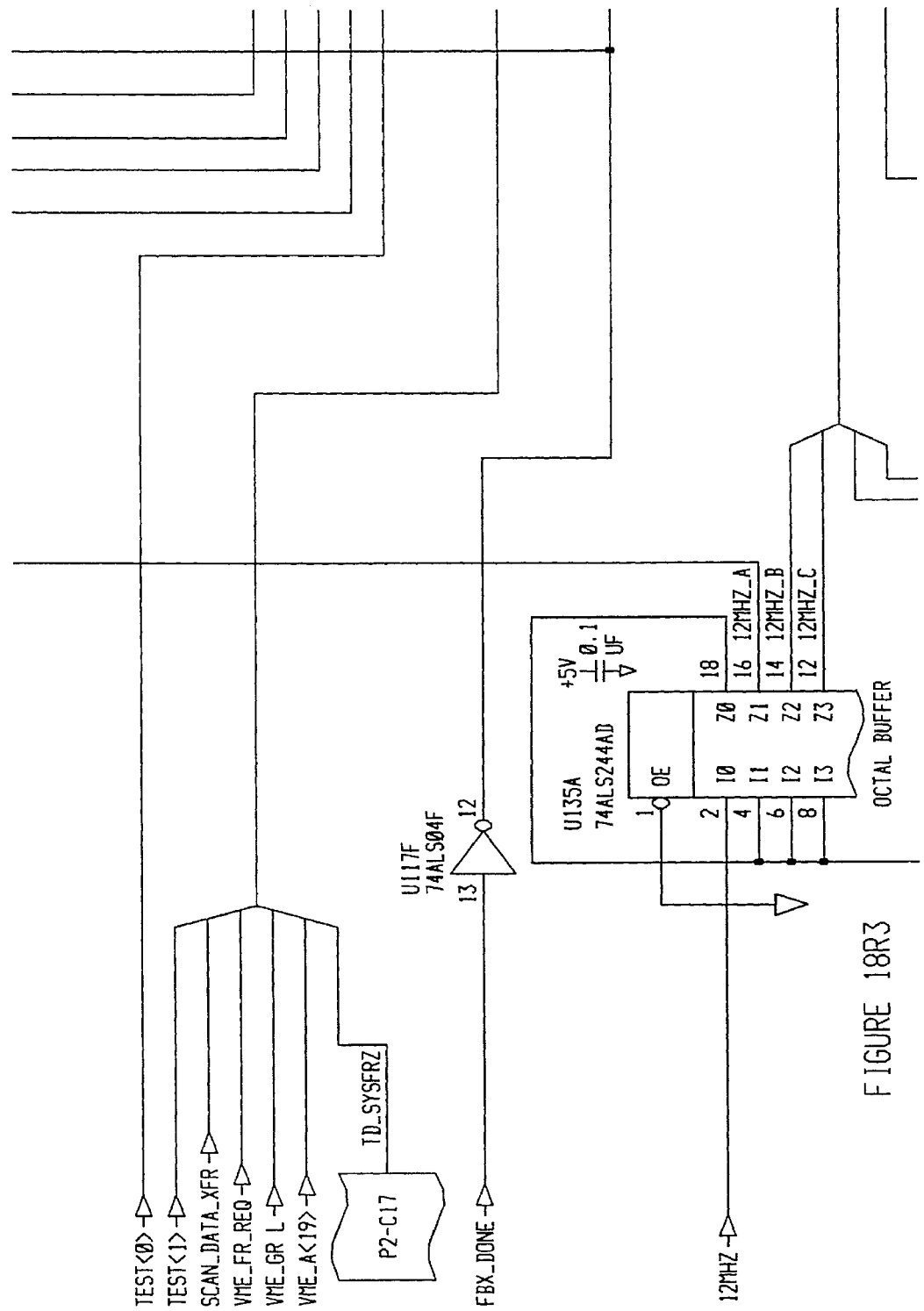
FIGURE 18R3

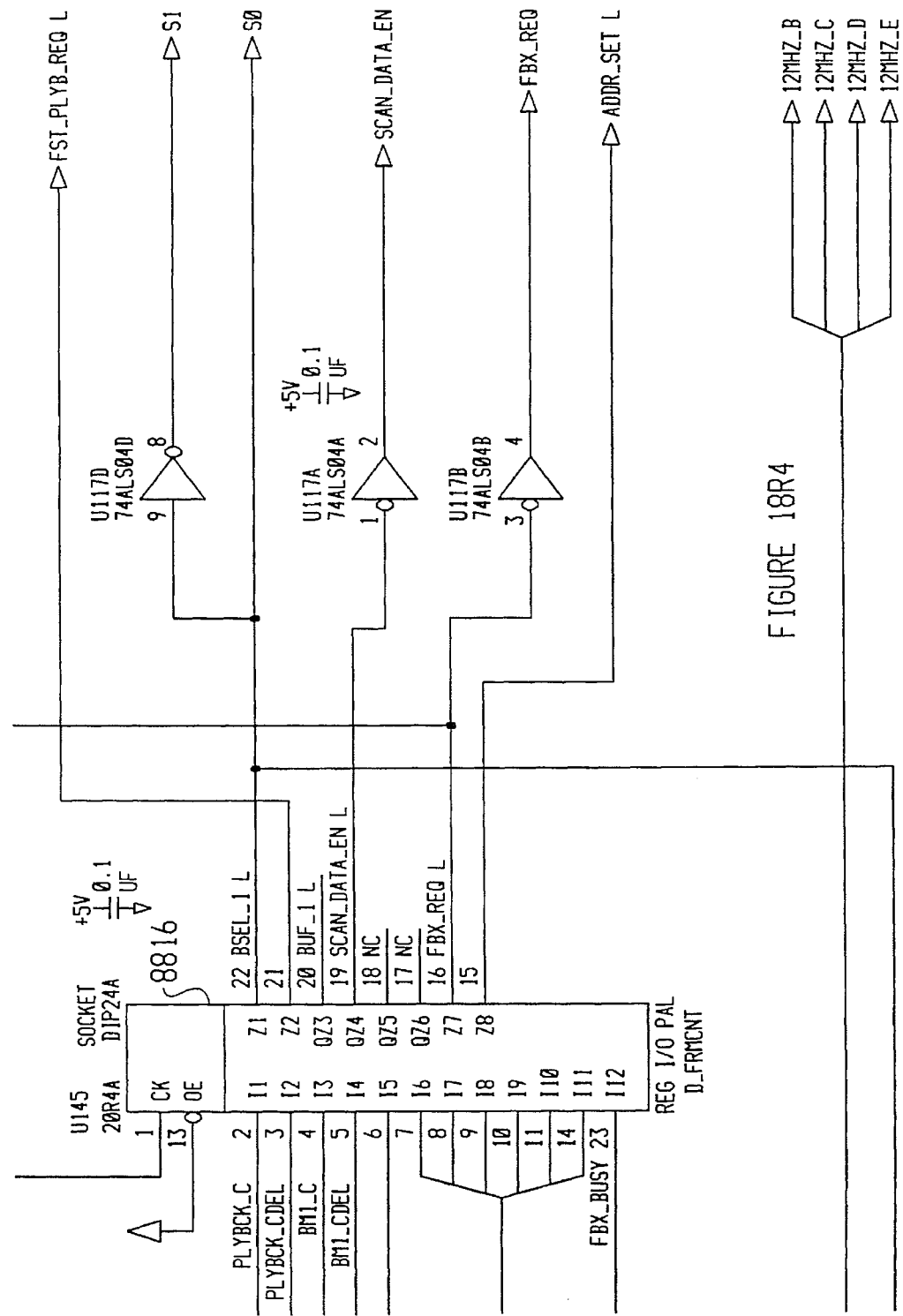
FIGURE 18R4

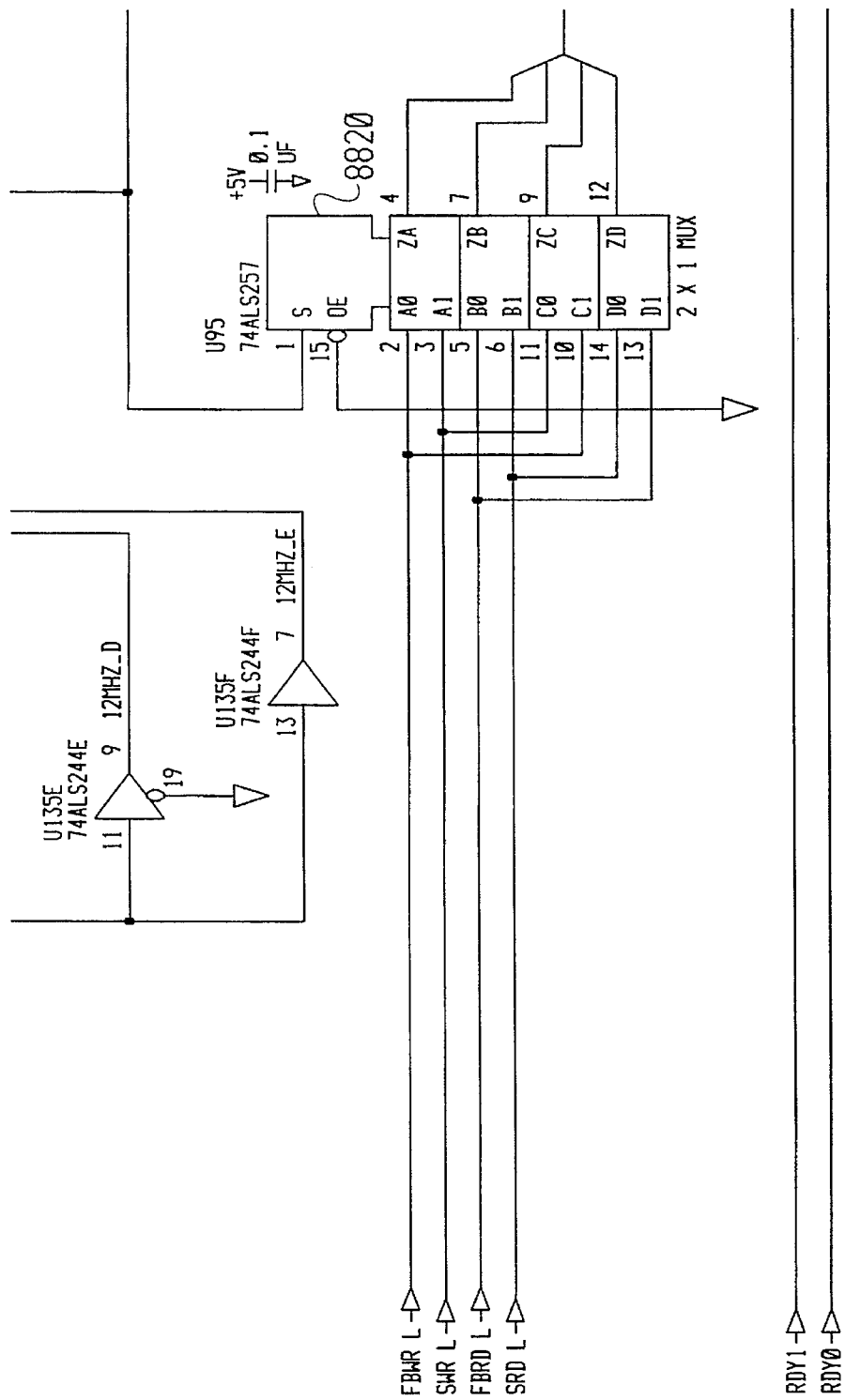
FIGURE 18R5

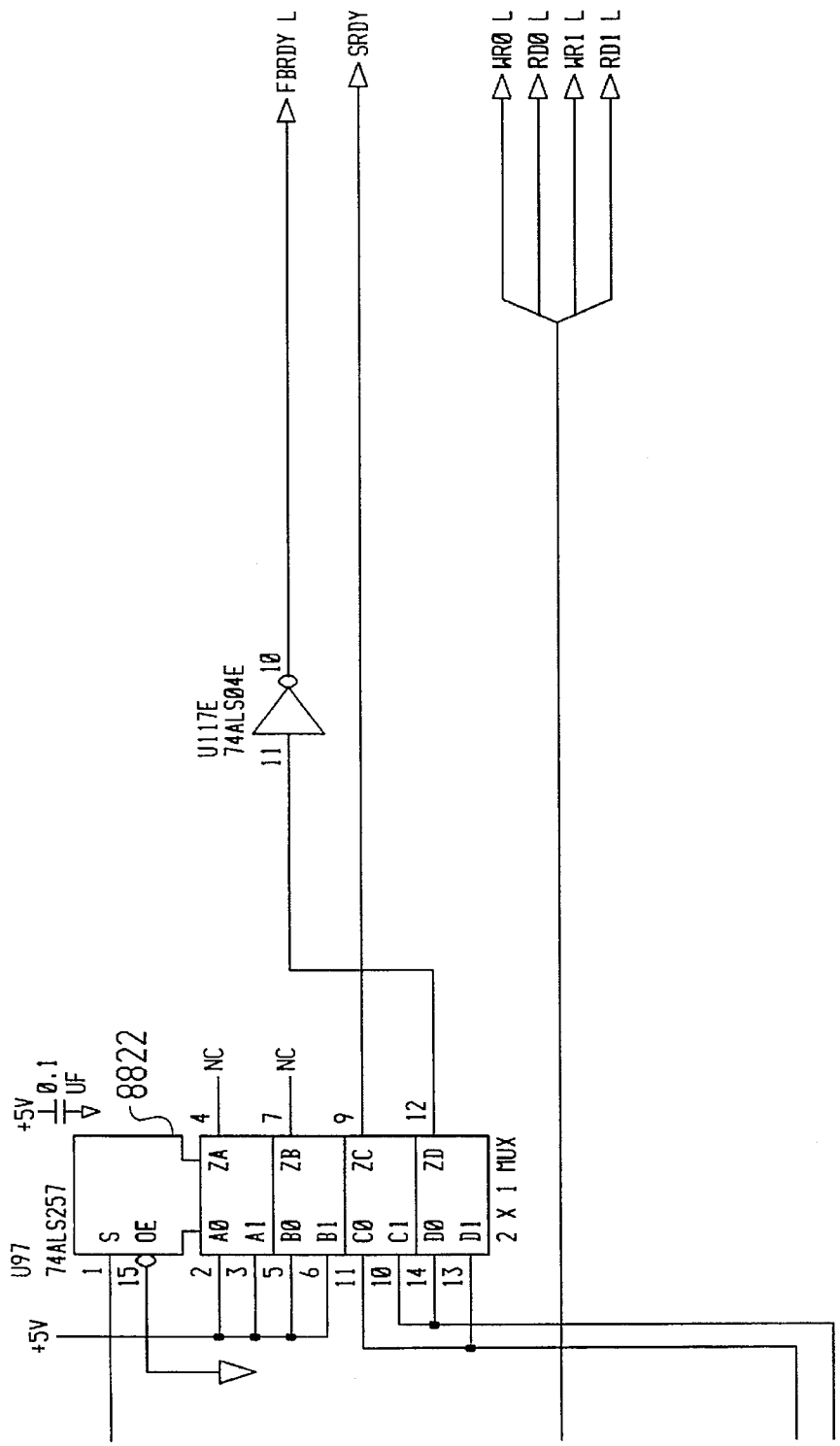
FIGURE 18R6

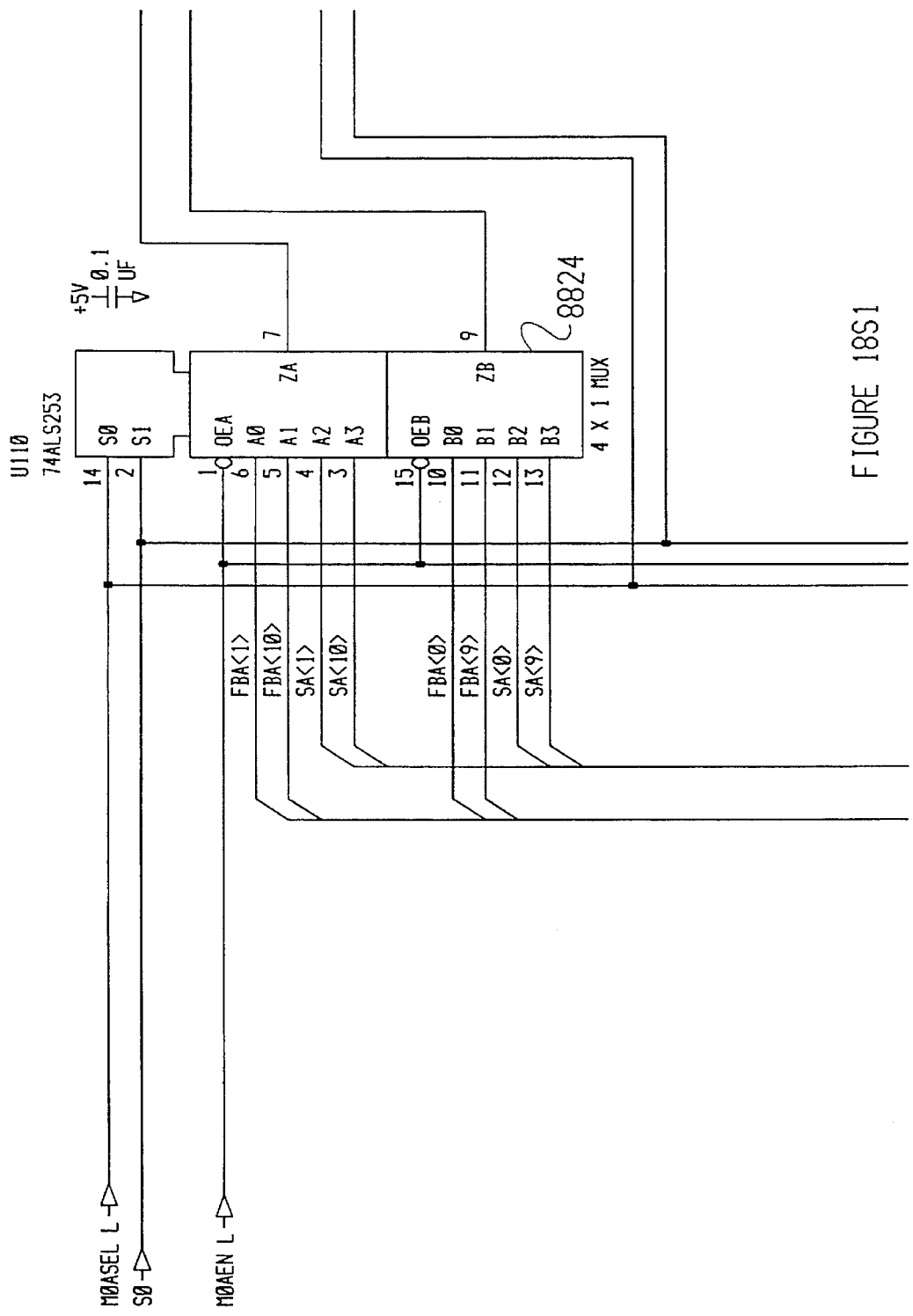
FIGURE 18S1

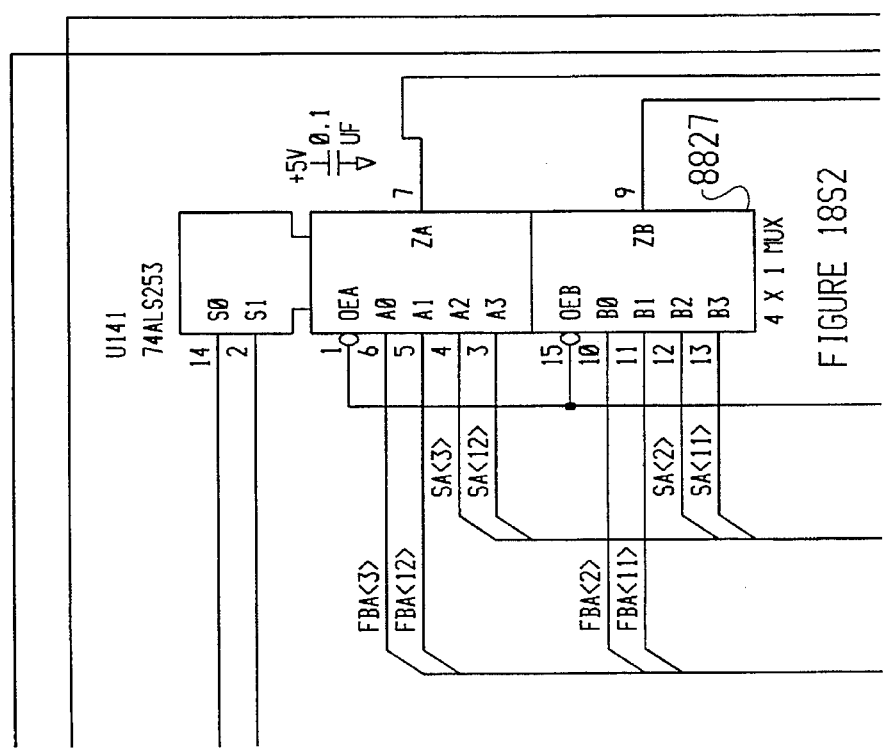
FIGURE 18S2

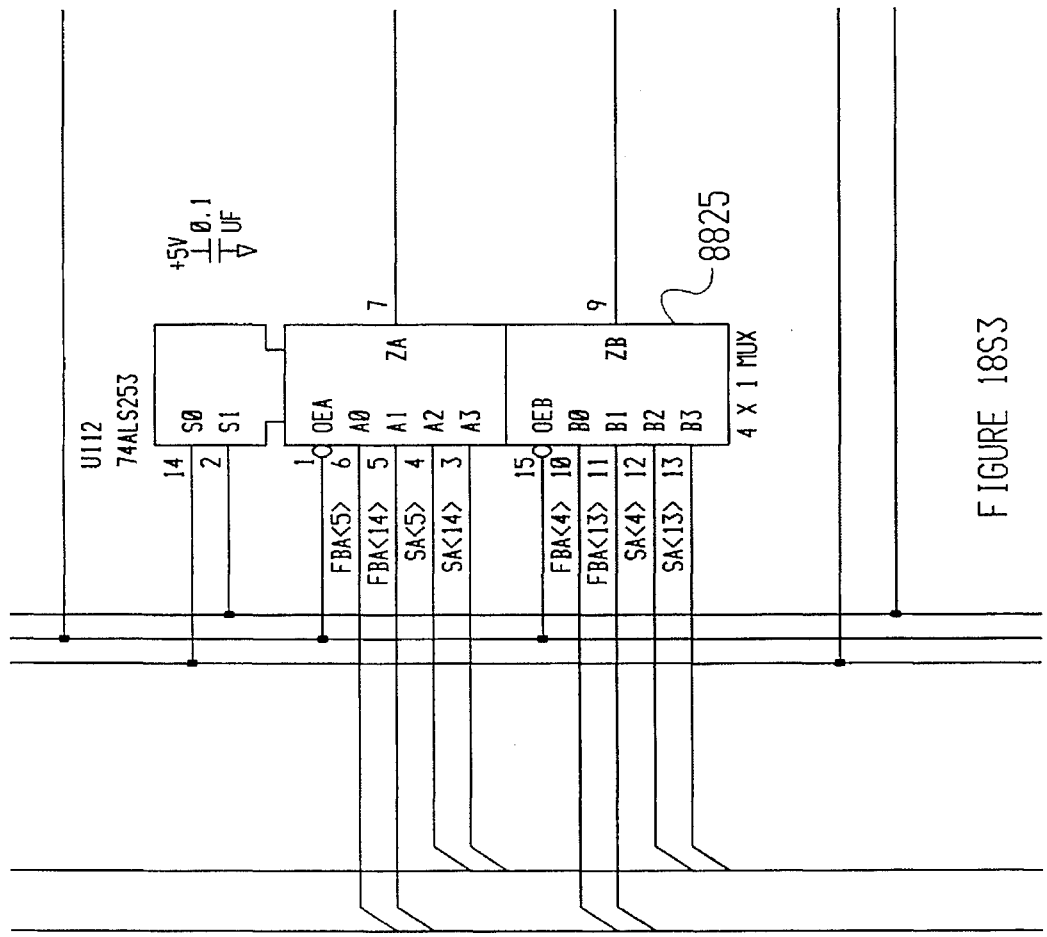
FIGURE 18S3

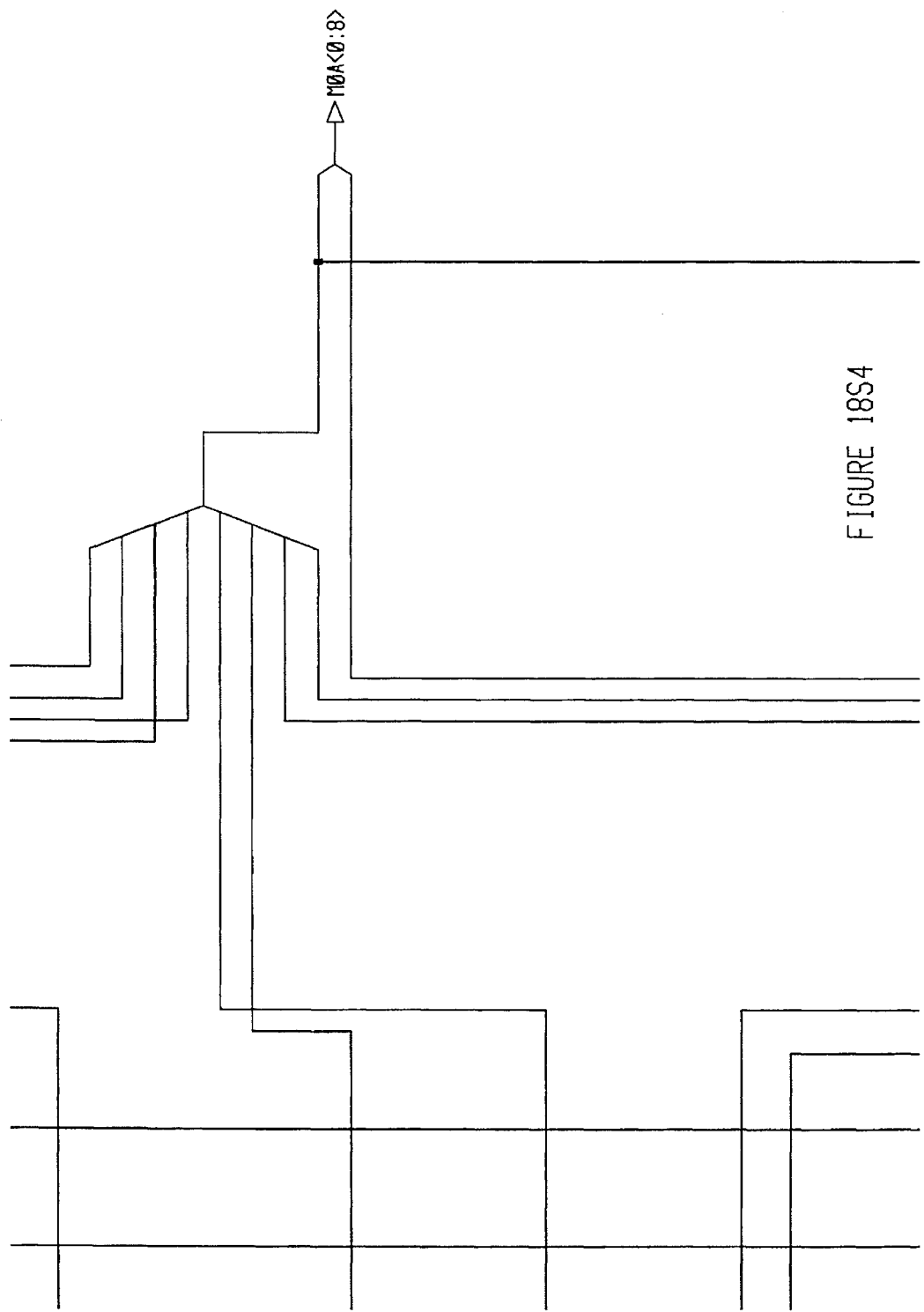
FIGURE 18S4

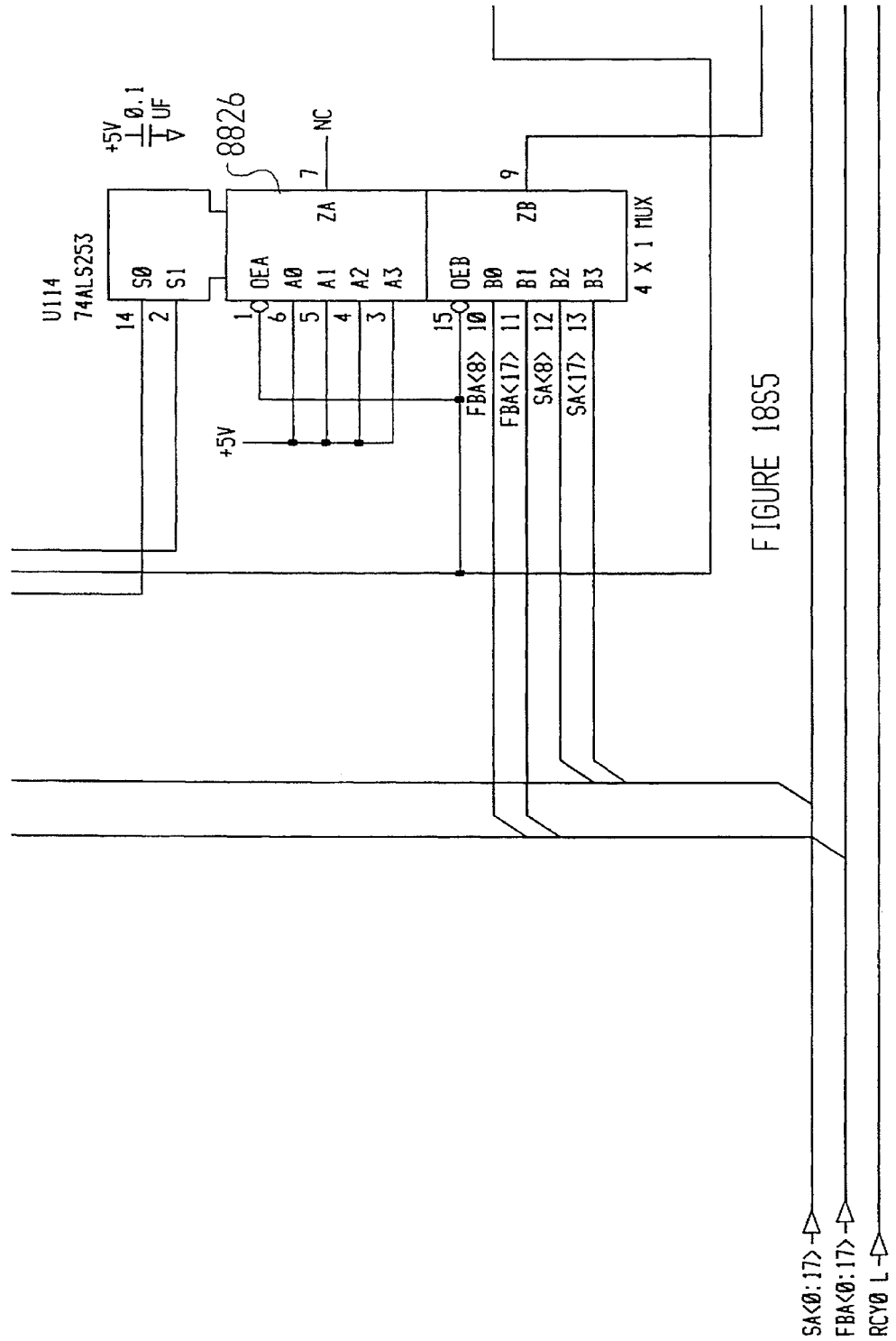
FIGURE 1855

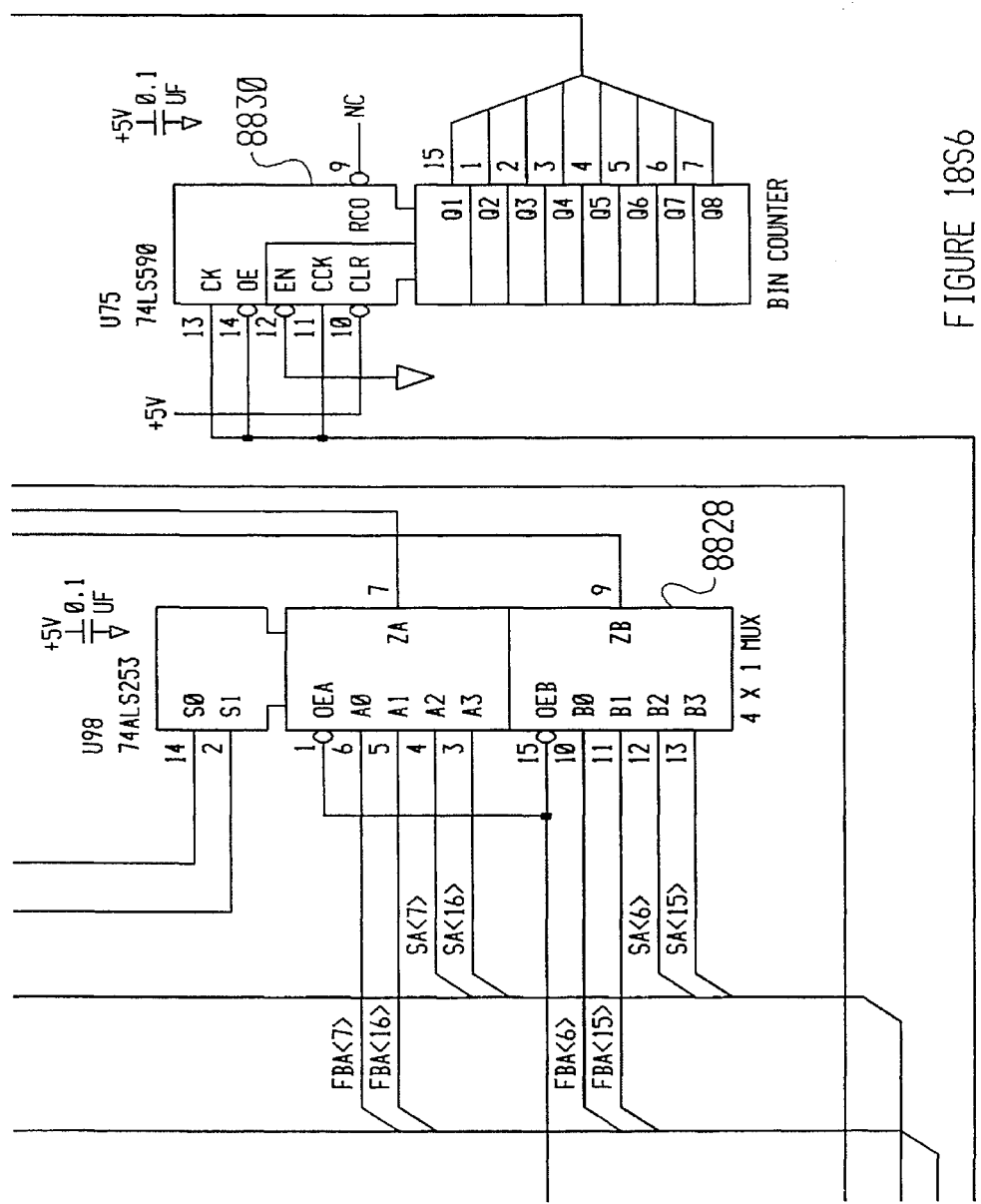
FIGURE 18S6

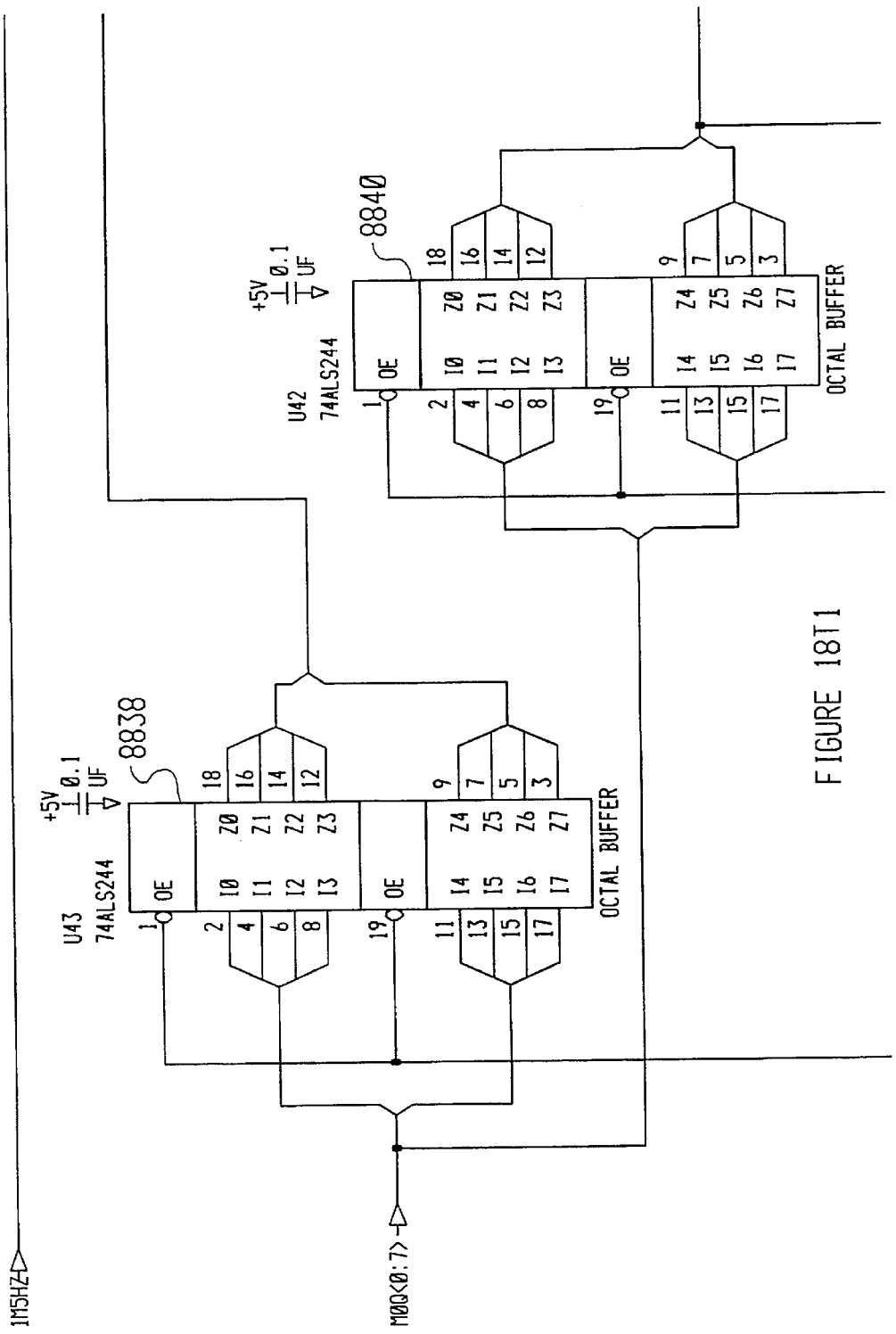

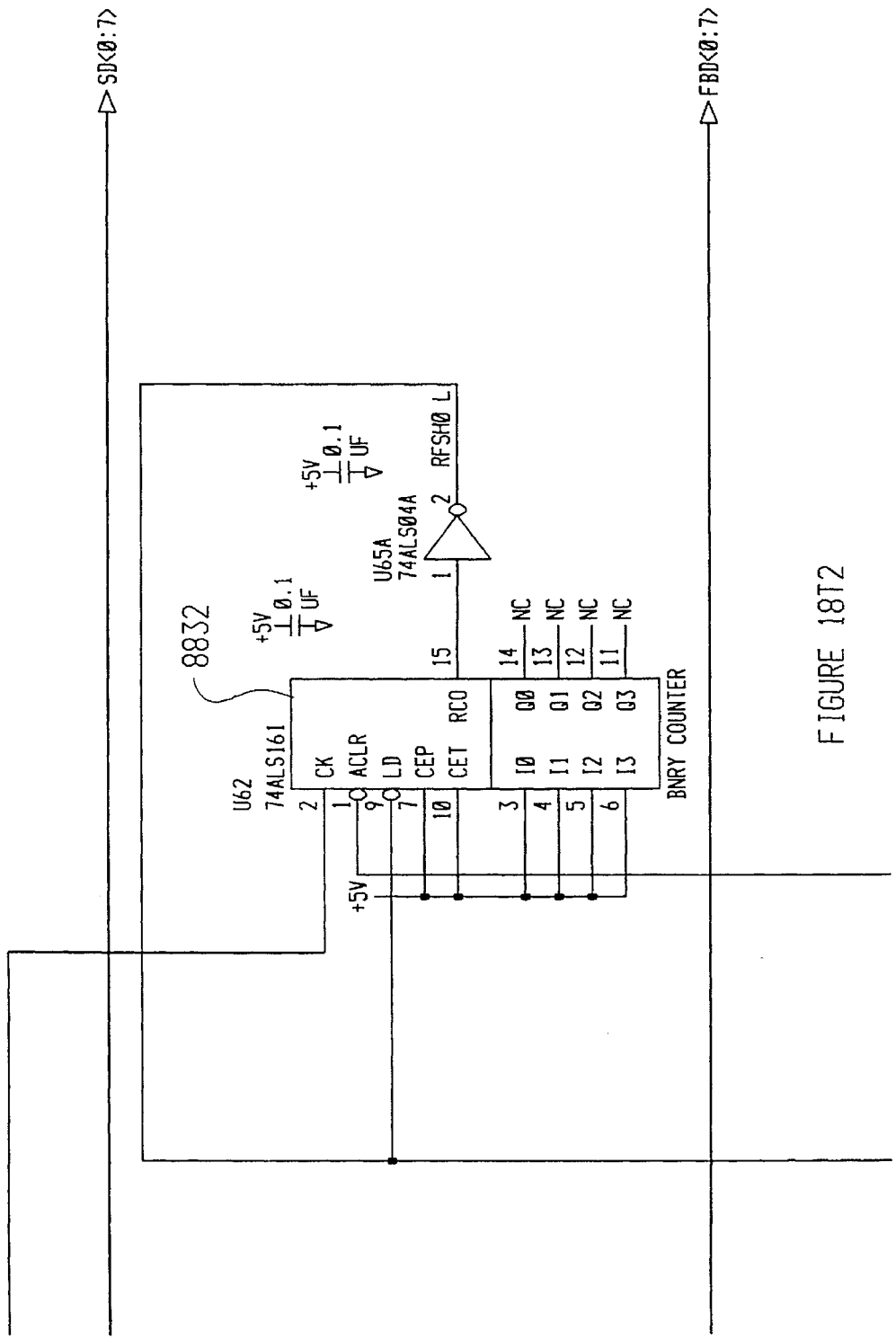
FIGURE 18T2

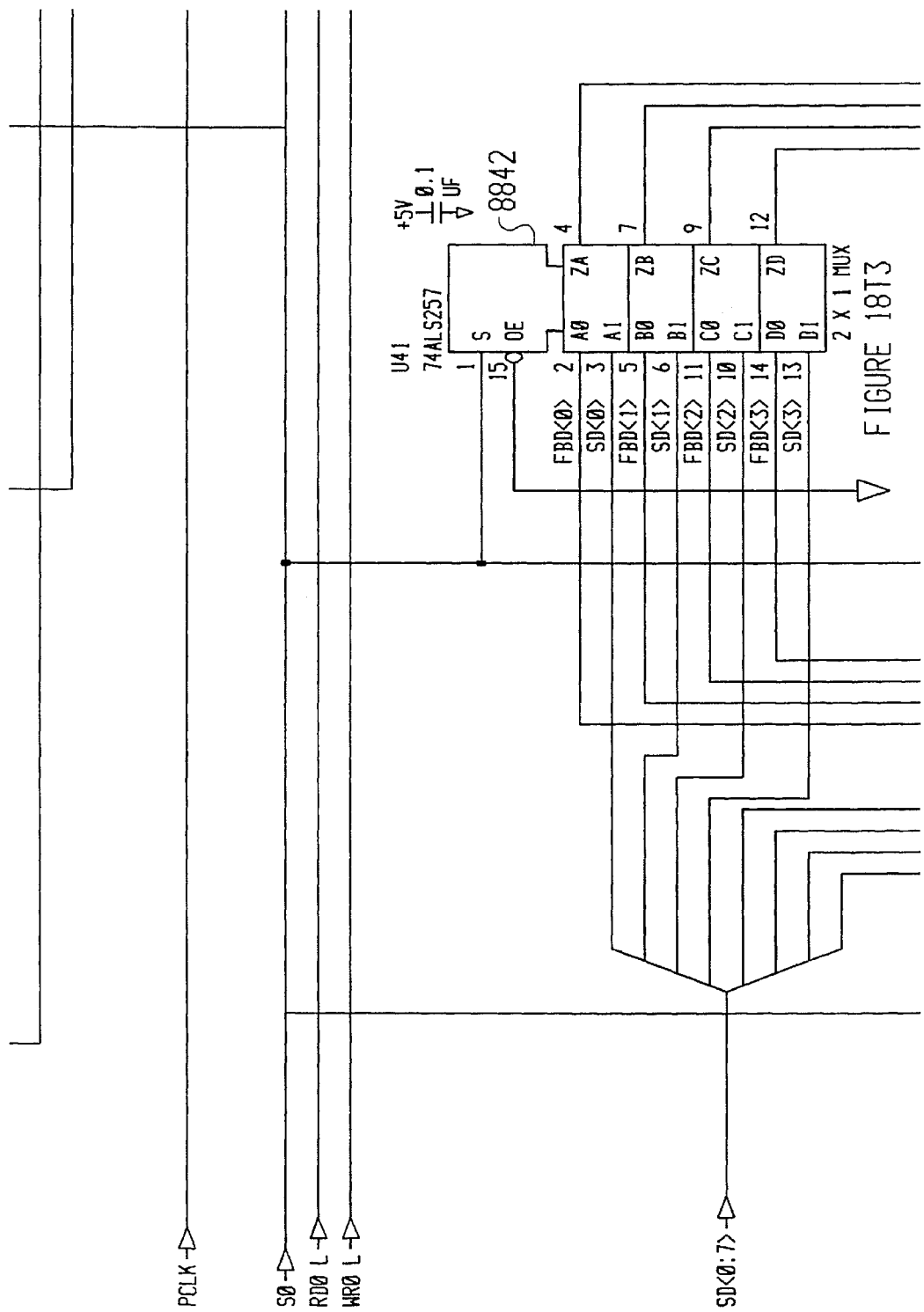

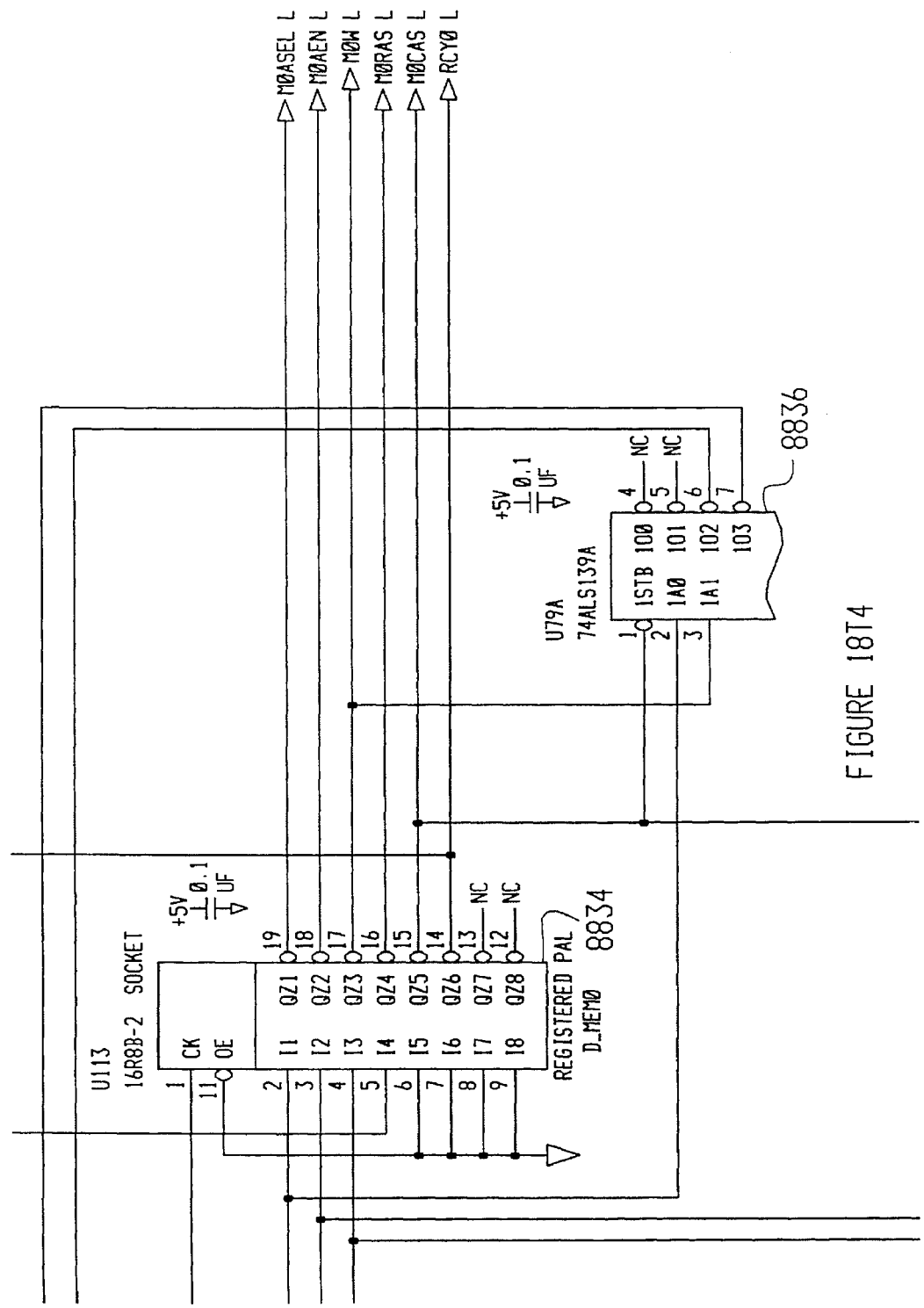
FIGURE 18T4

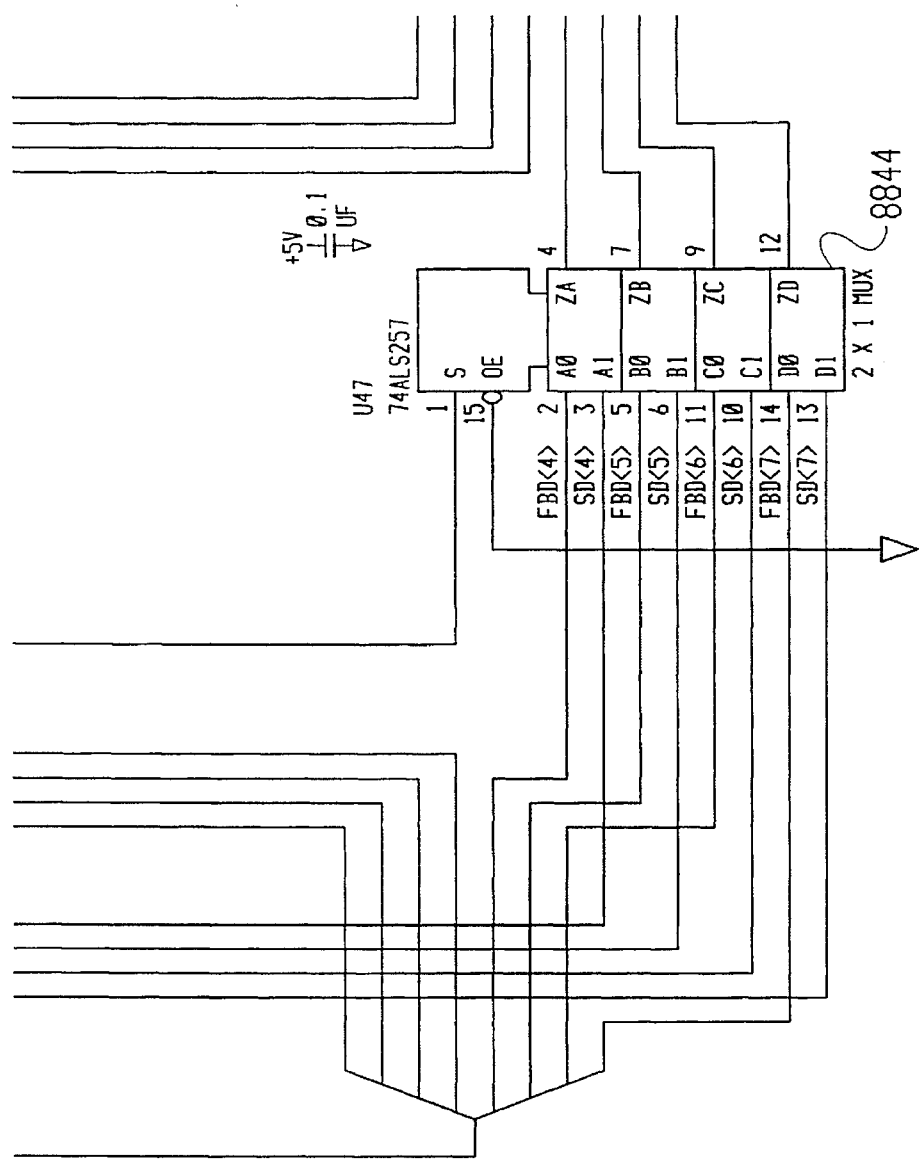
FIGURE 18T5

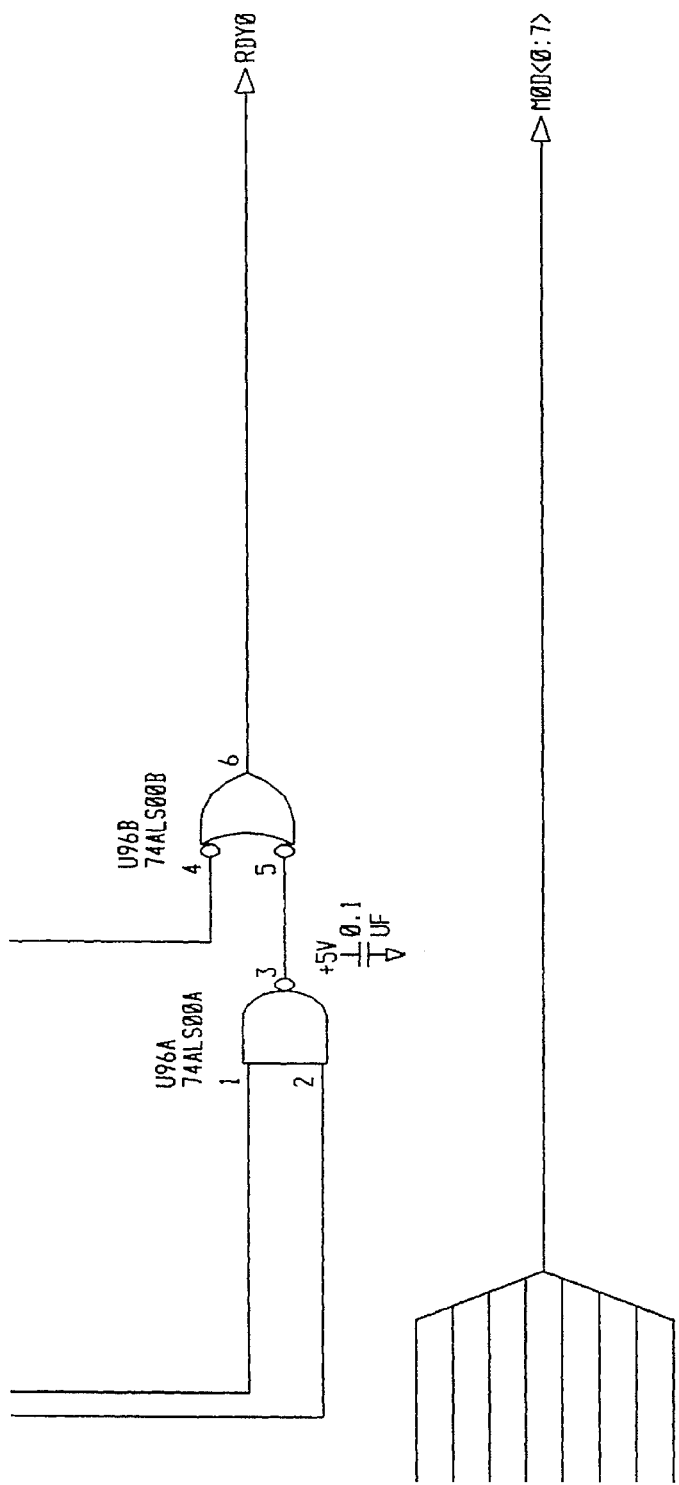
FIGURE 18T6

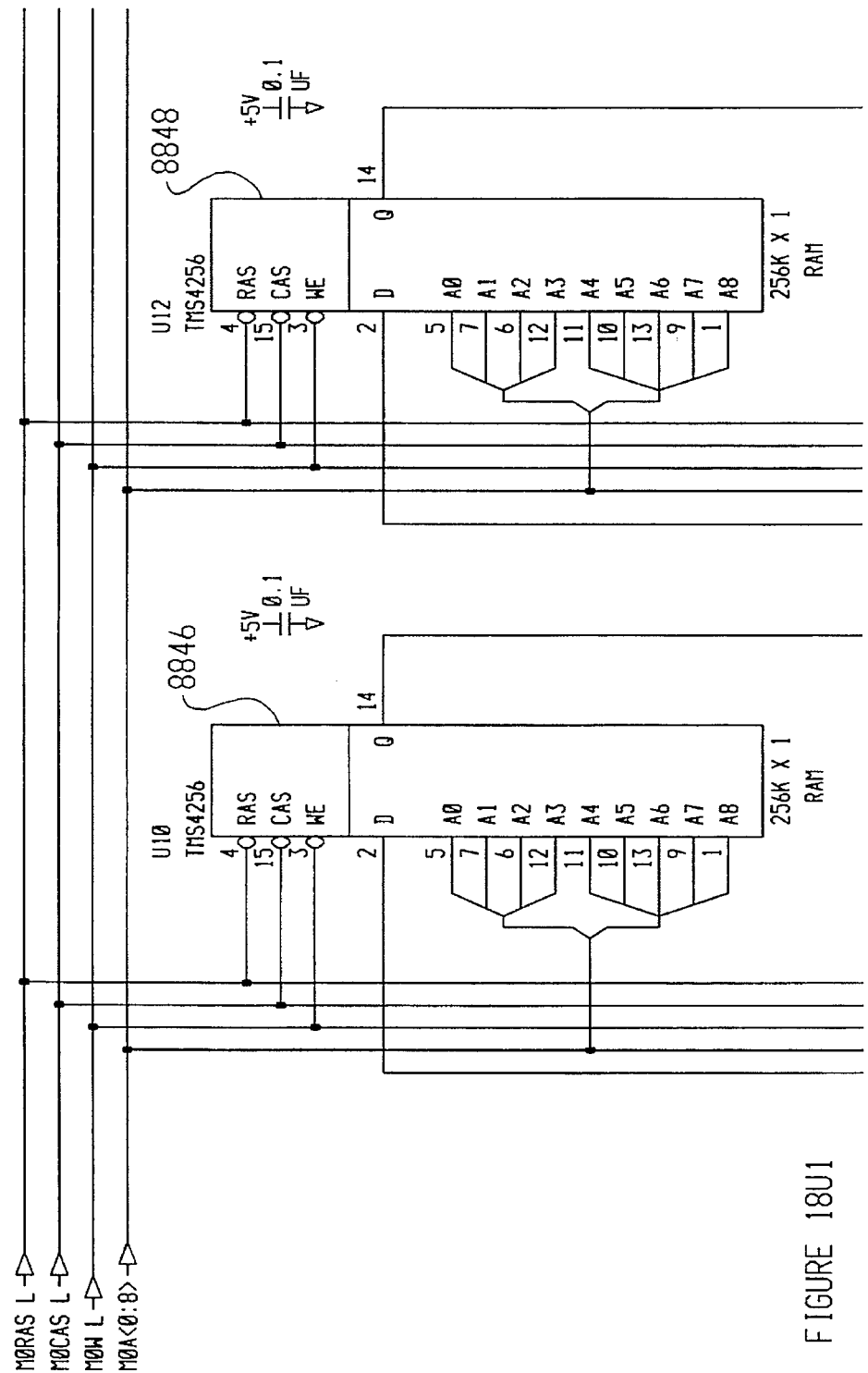
FIGURE 18U1

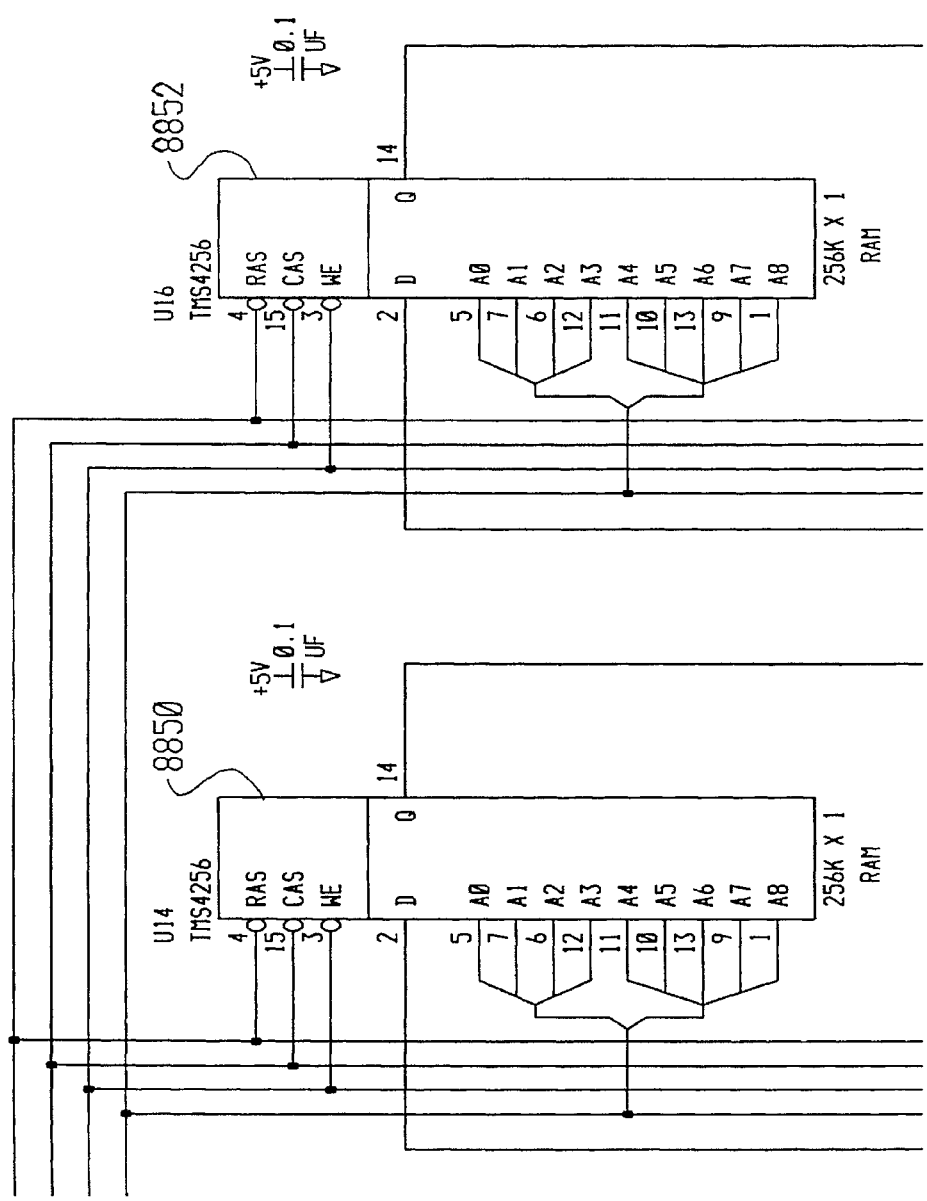
FIGURE 18U2

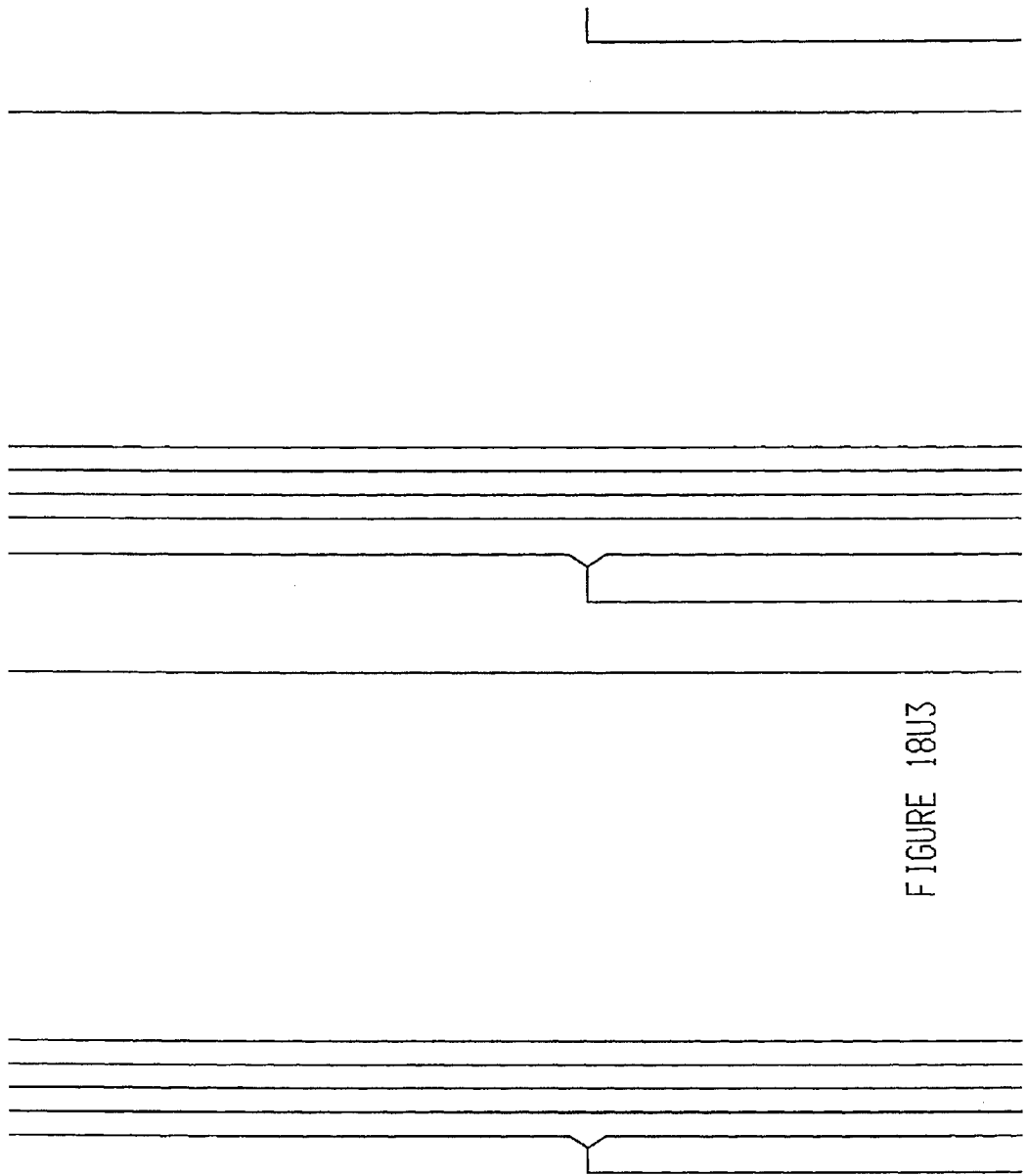
FIGURE 18U3

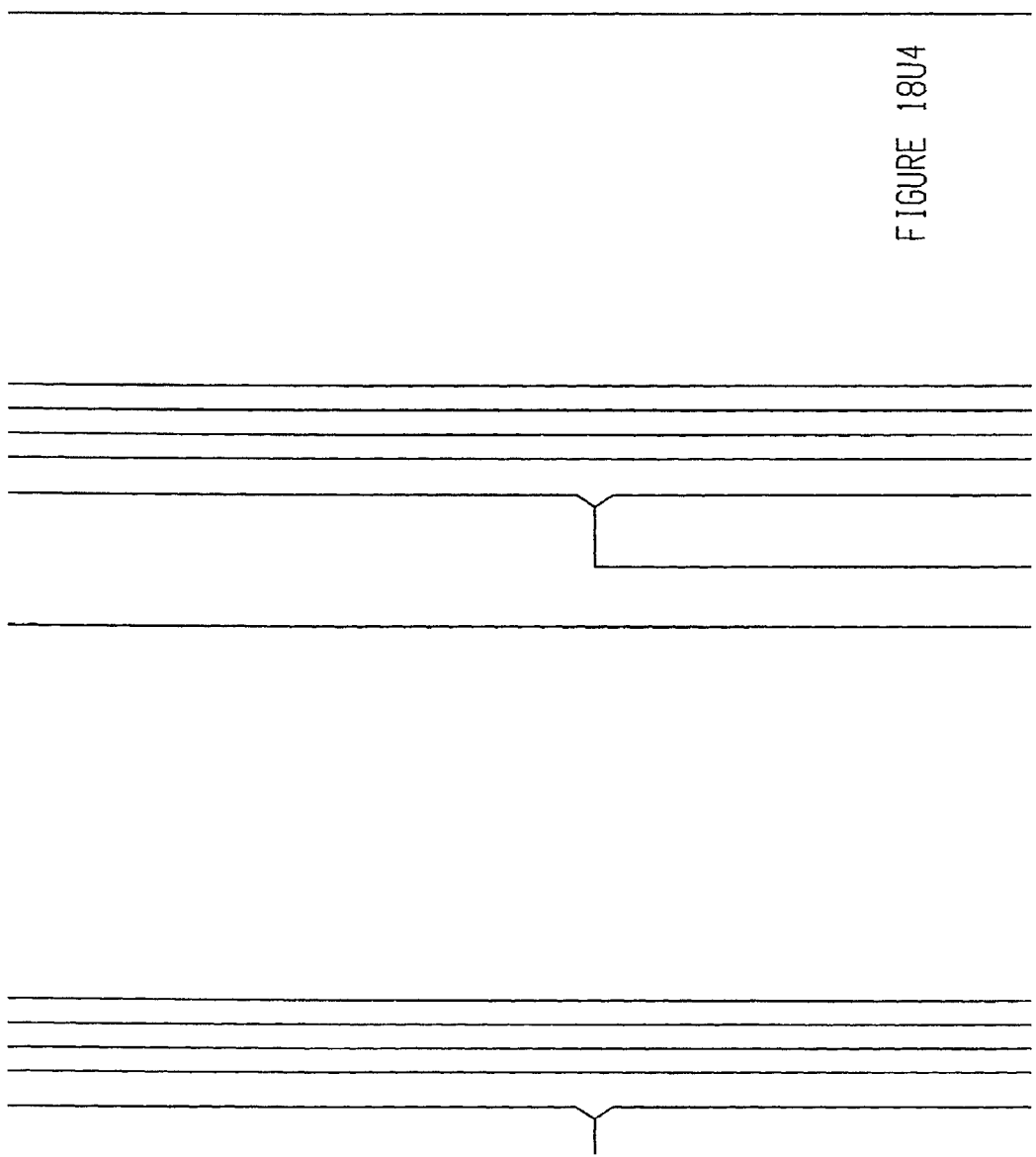
FIGURE 18U4

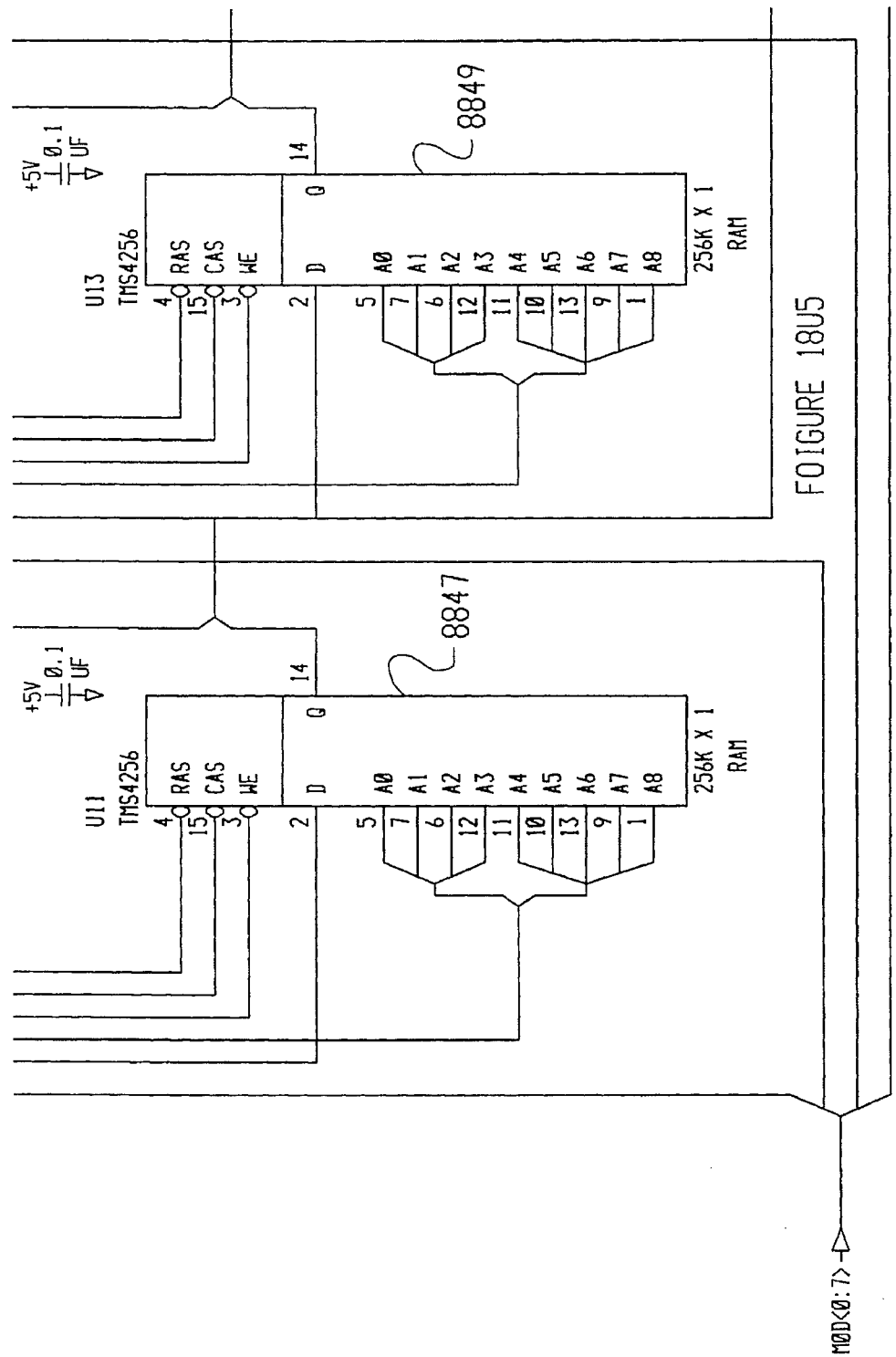
FOIGURE 18U5

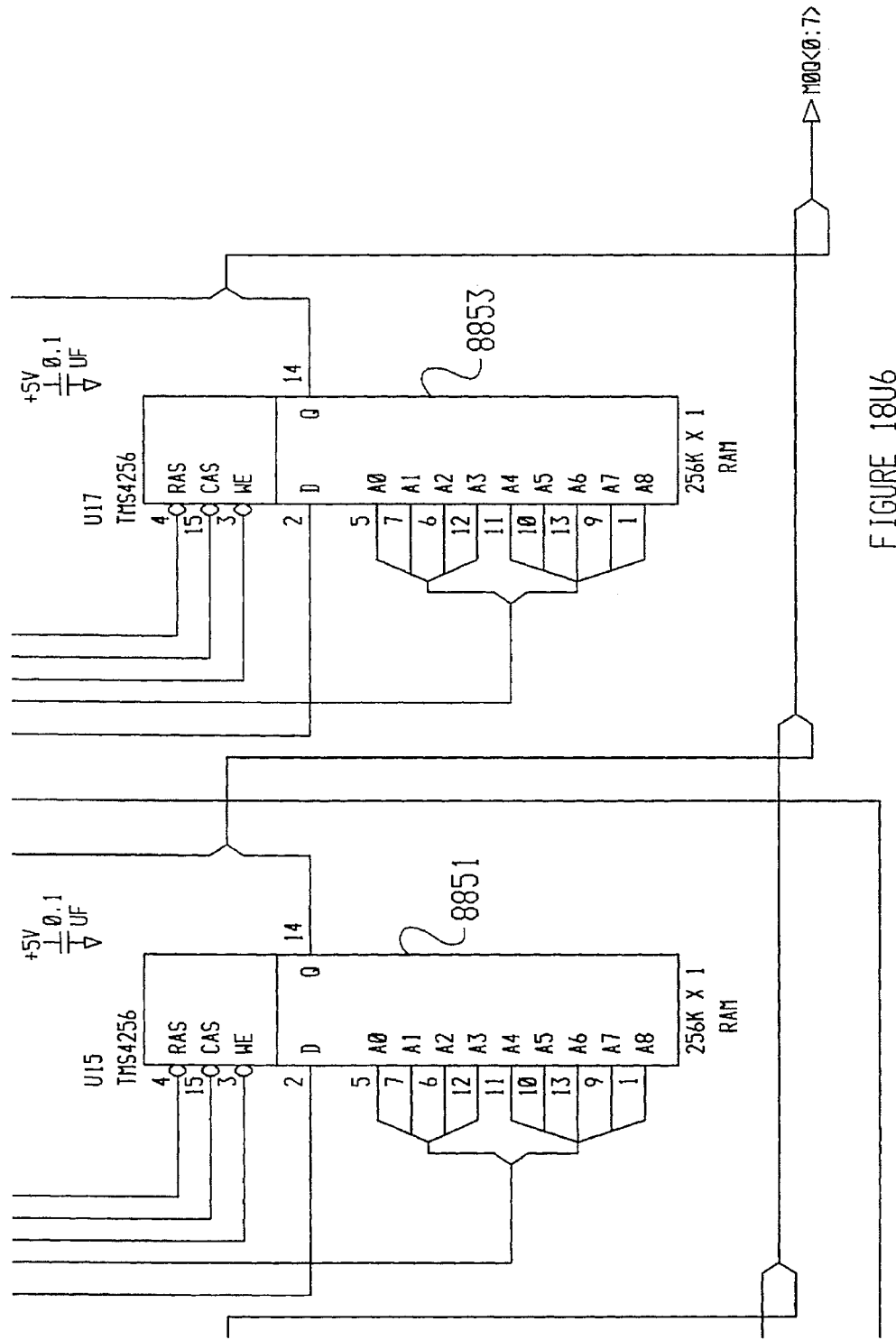
FIGURE 18U6

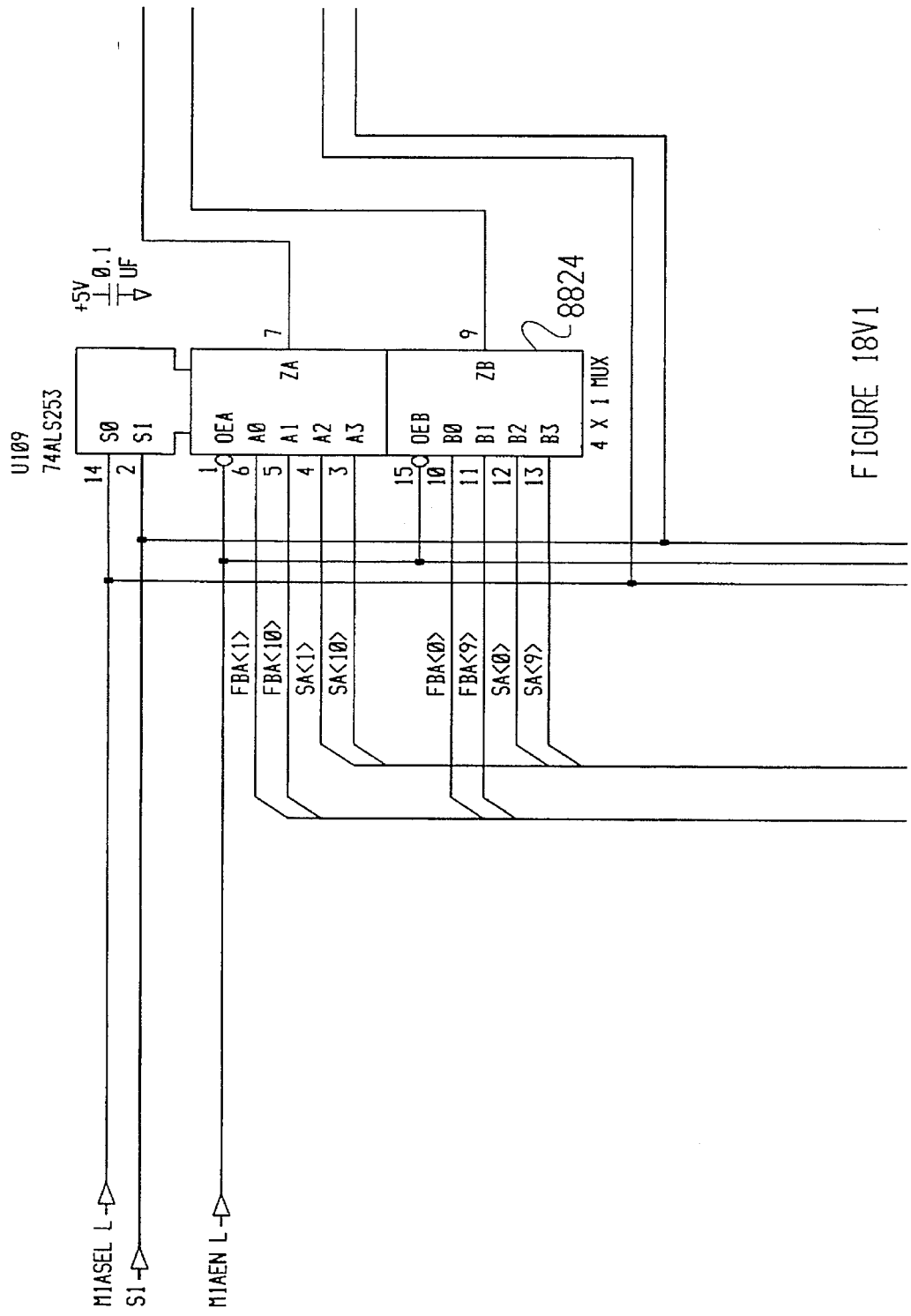
FIGURE 18V1

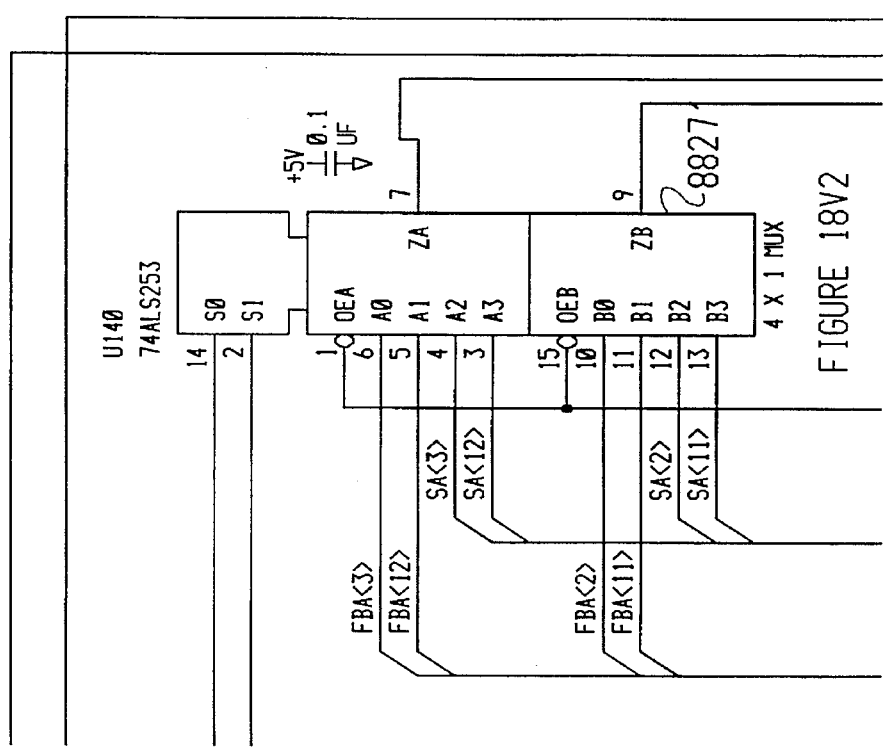

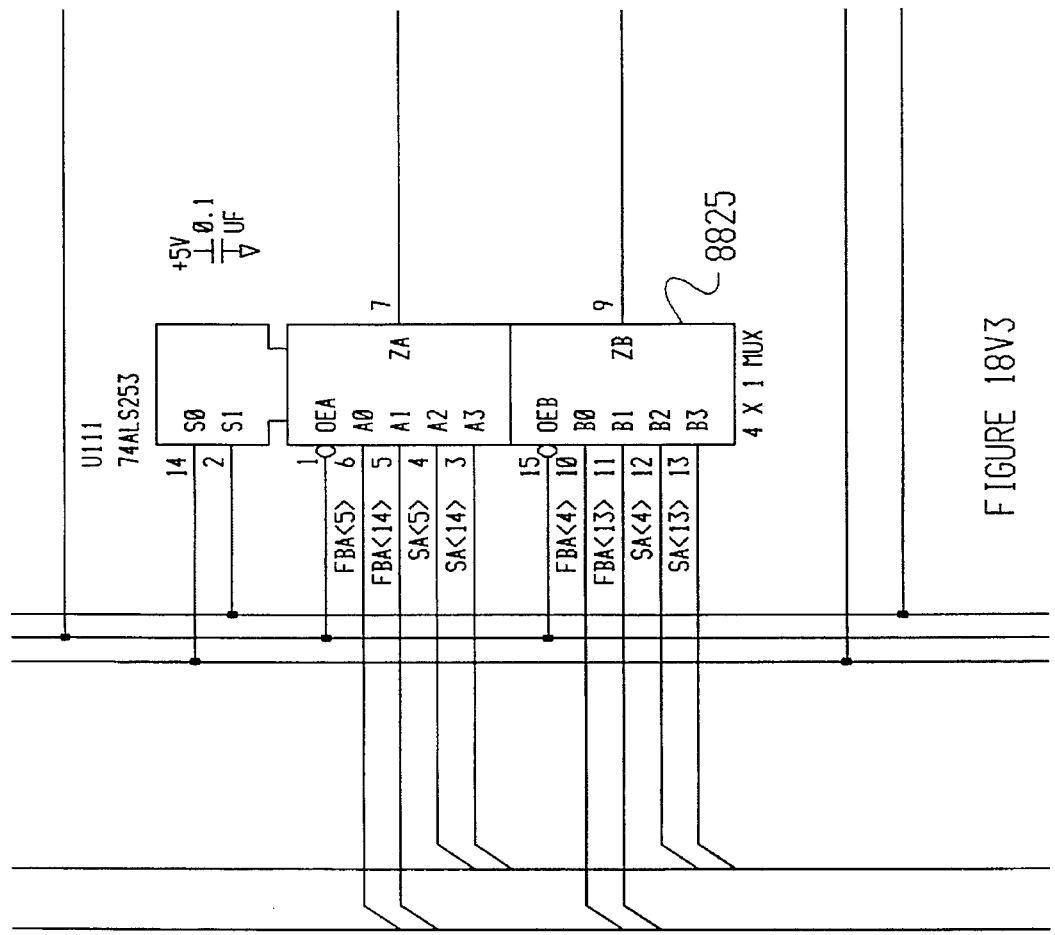
FIGURE 18V3

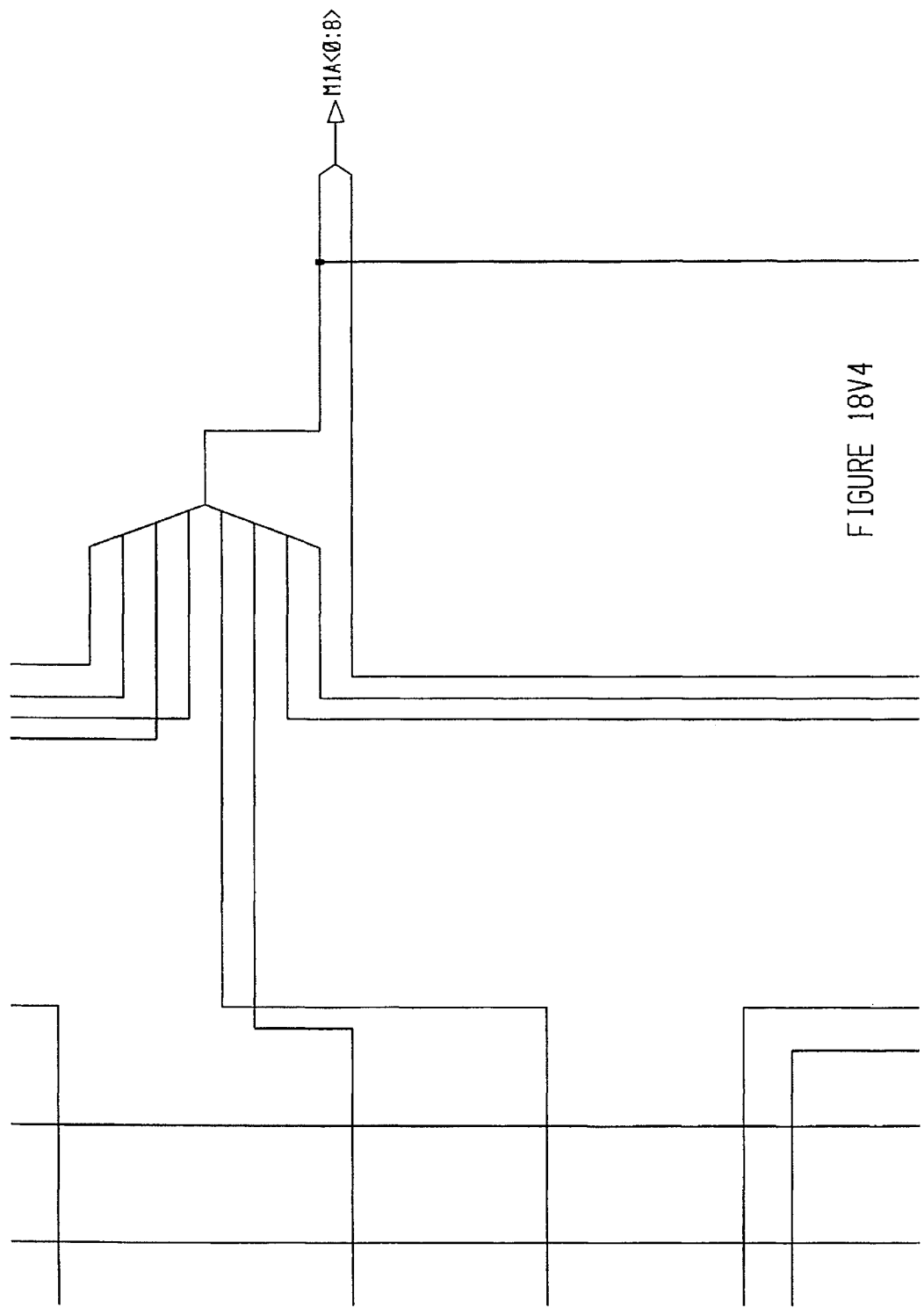
FIGURE 18V4

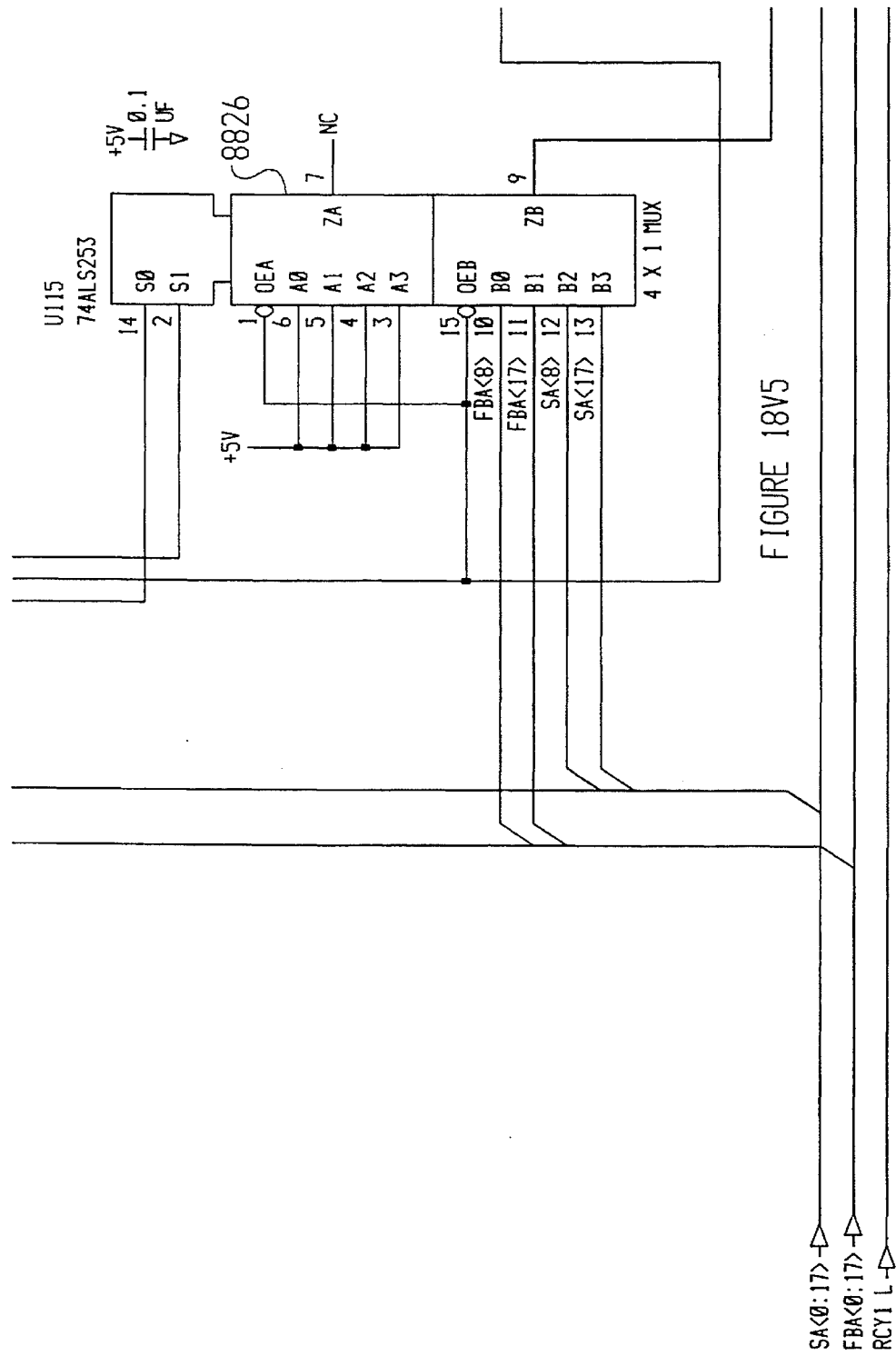

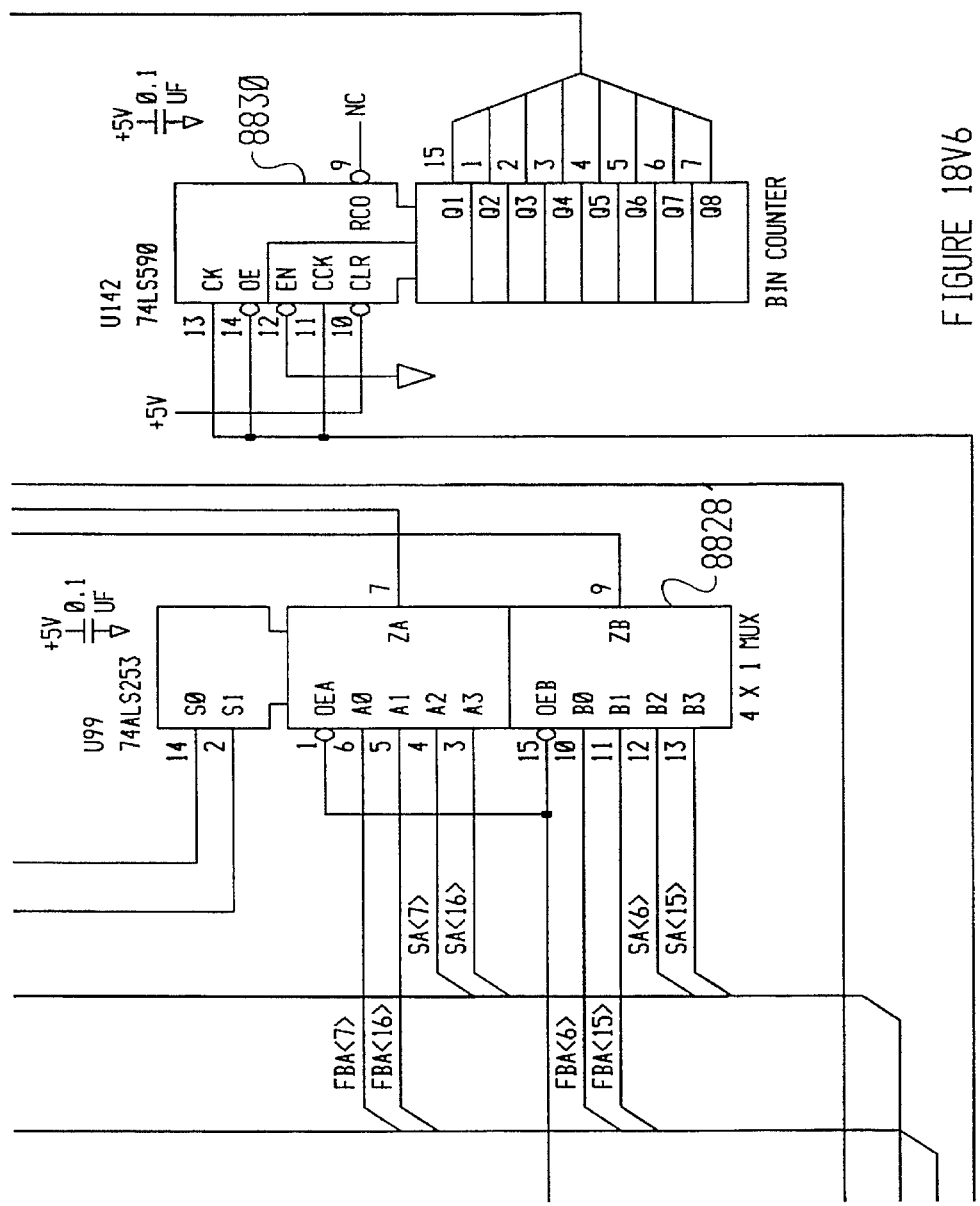
FIGURE 18V6

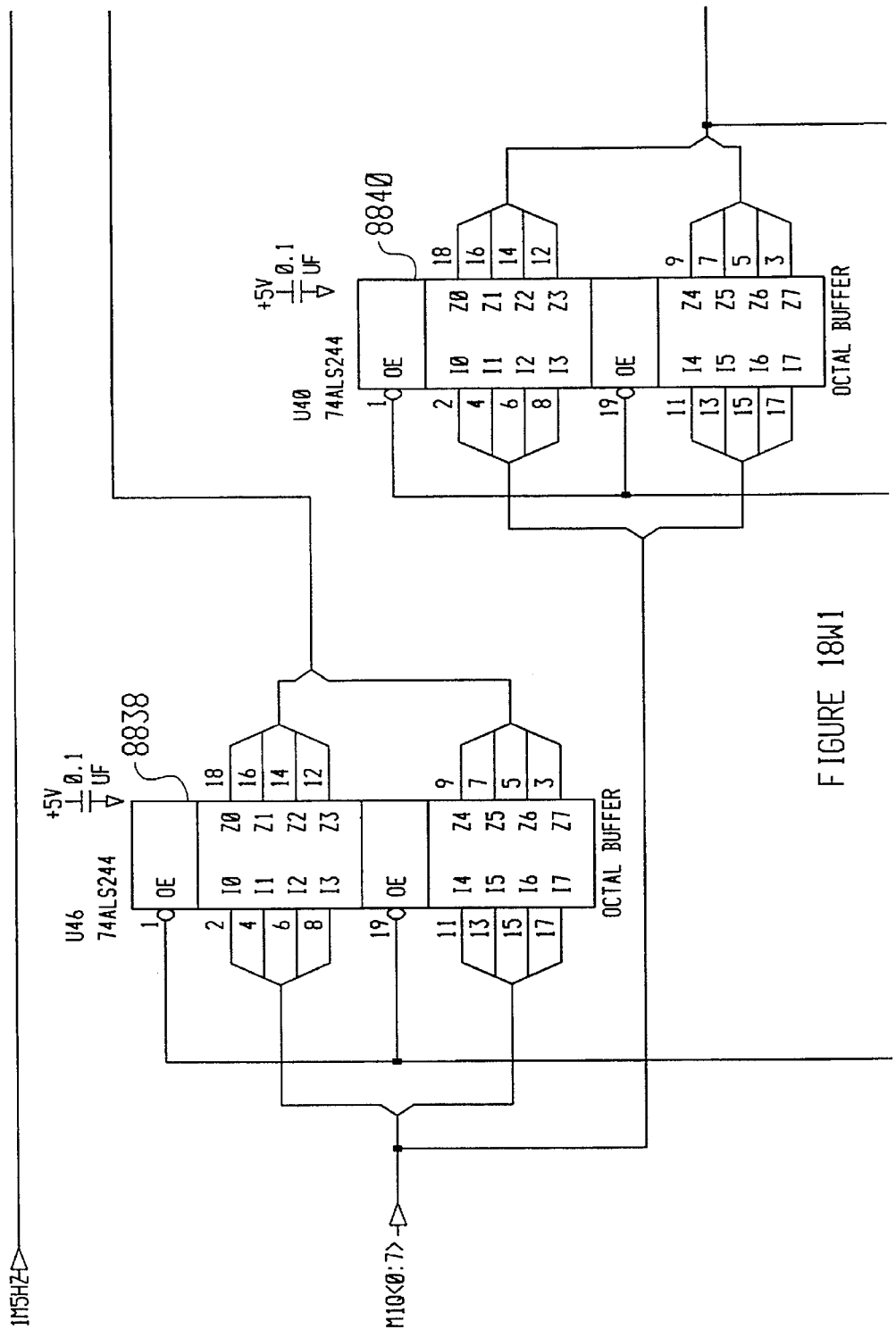
FIGURE 18W1

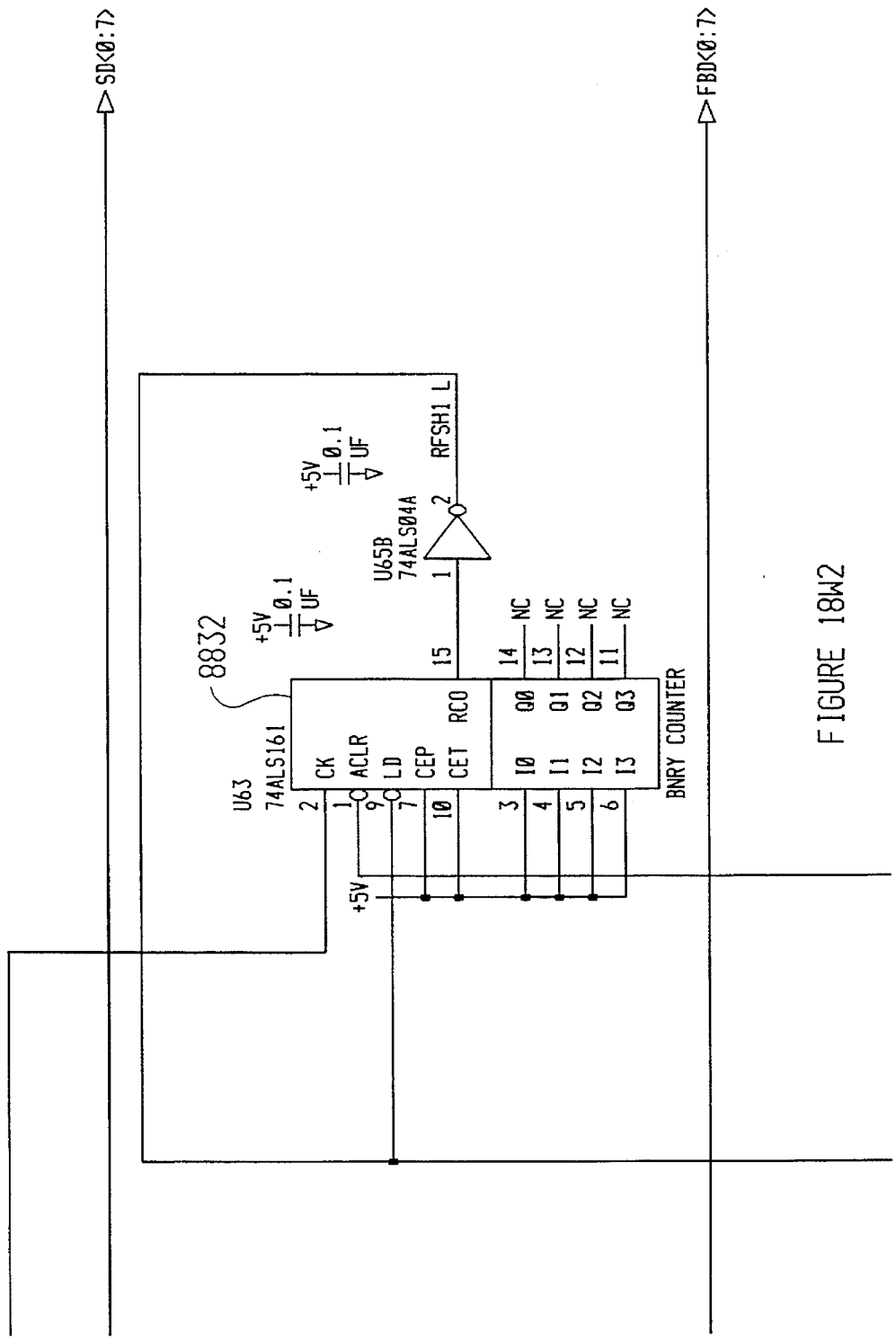
FIGURE 18W2

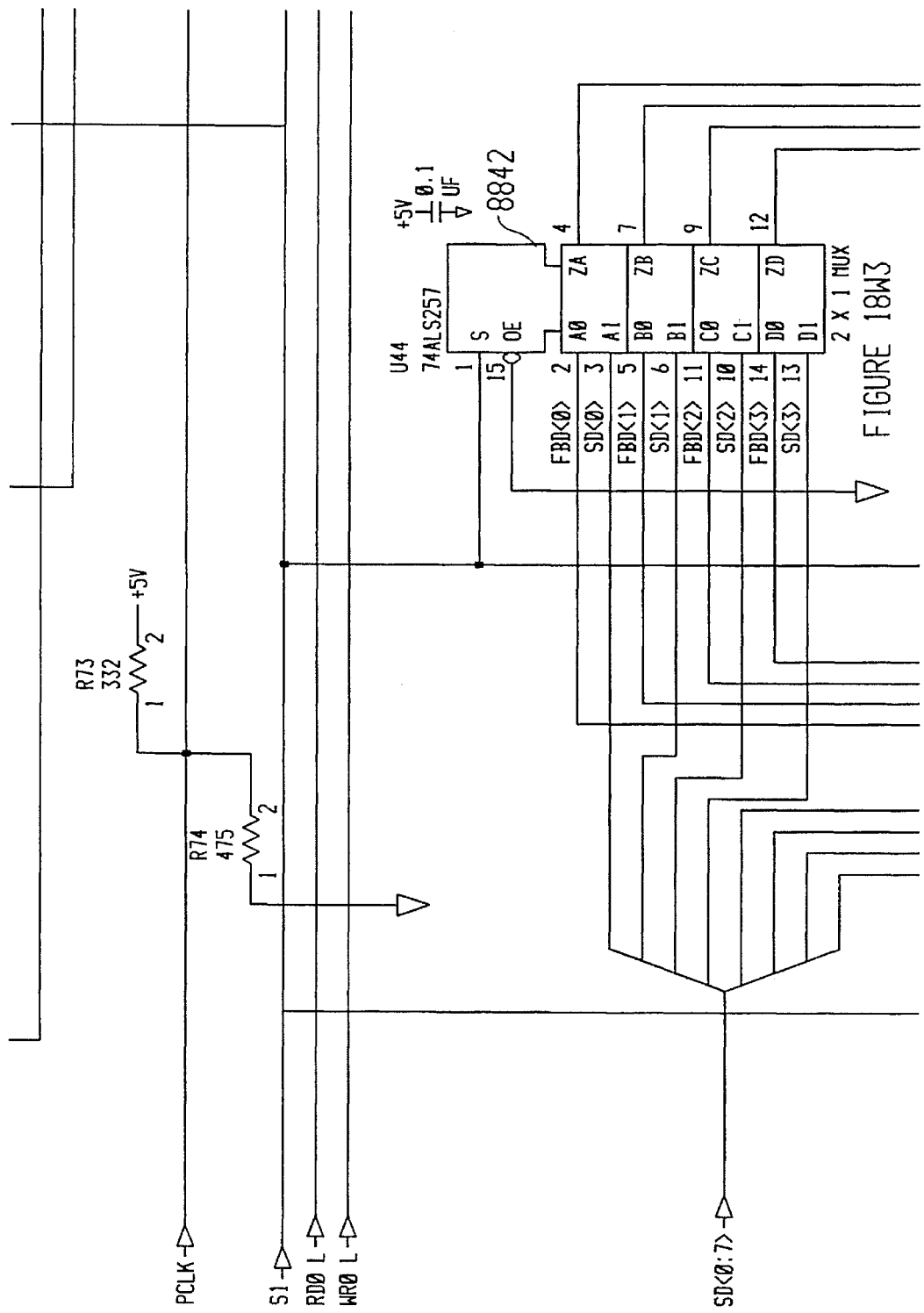

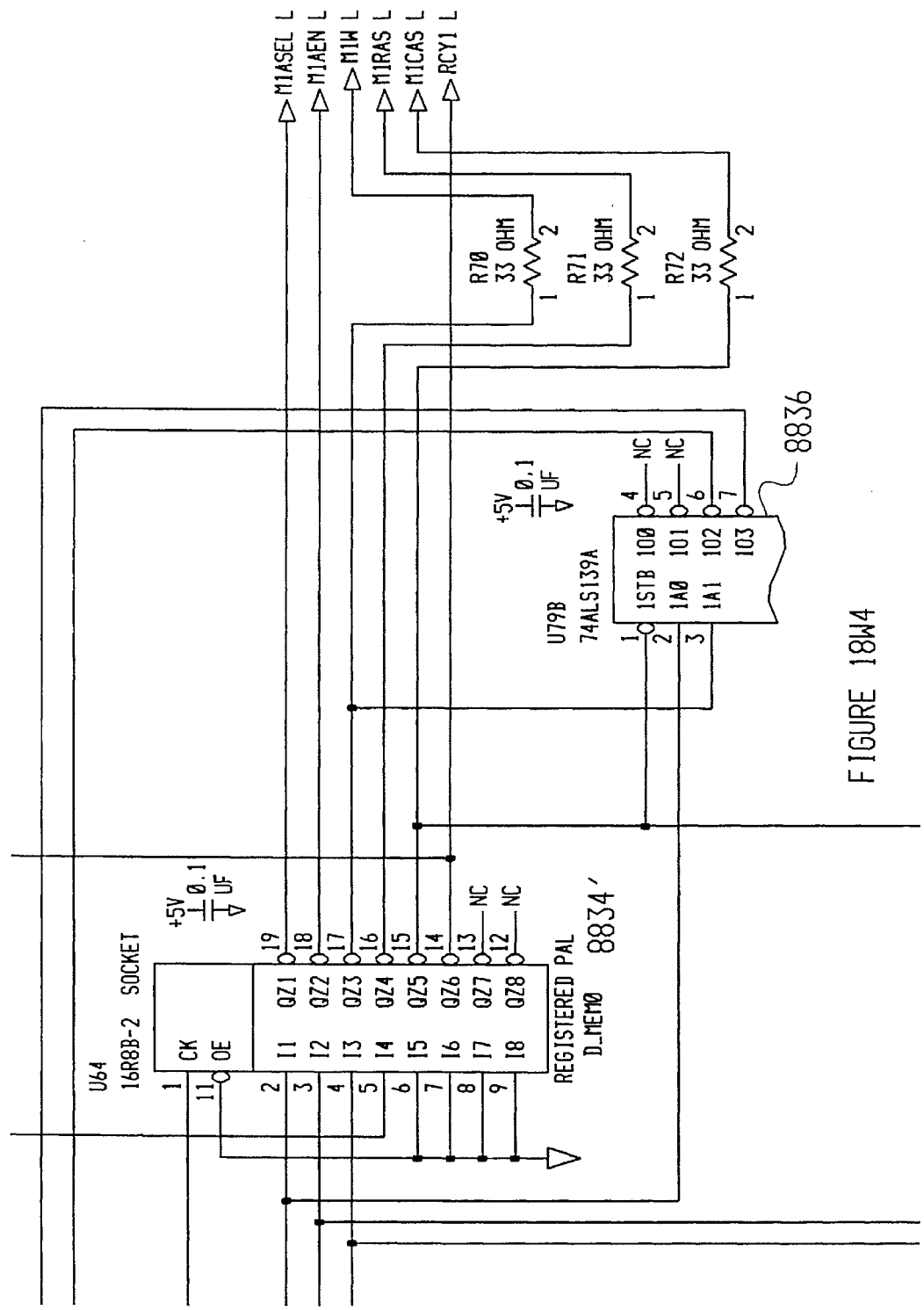
FIGURE 18W4

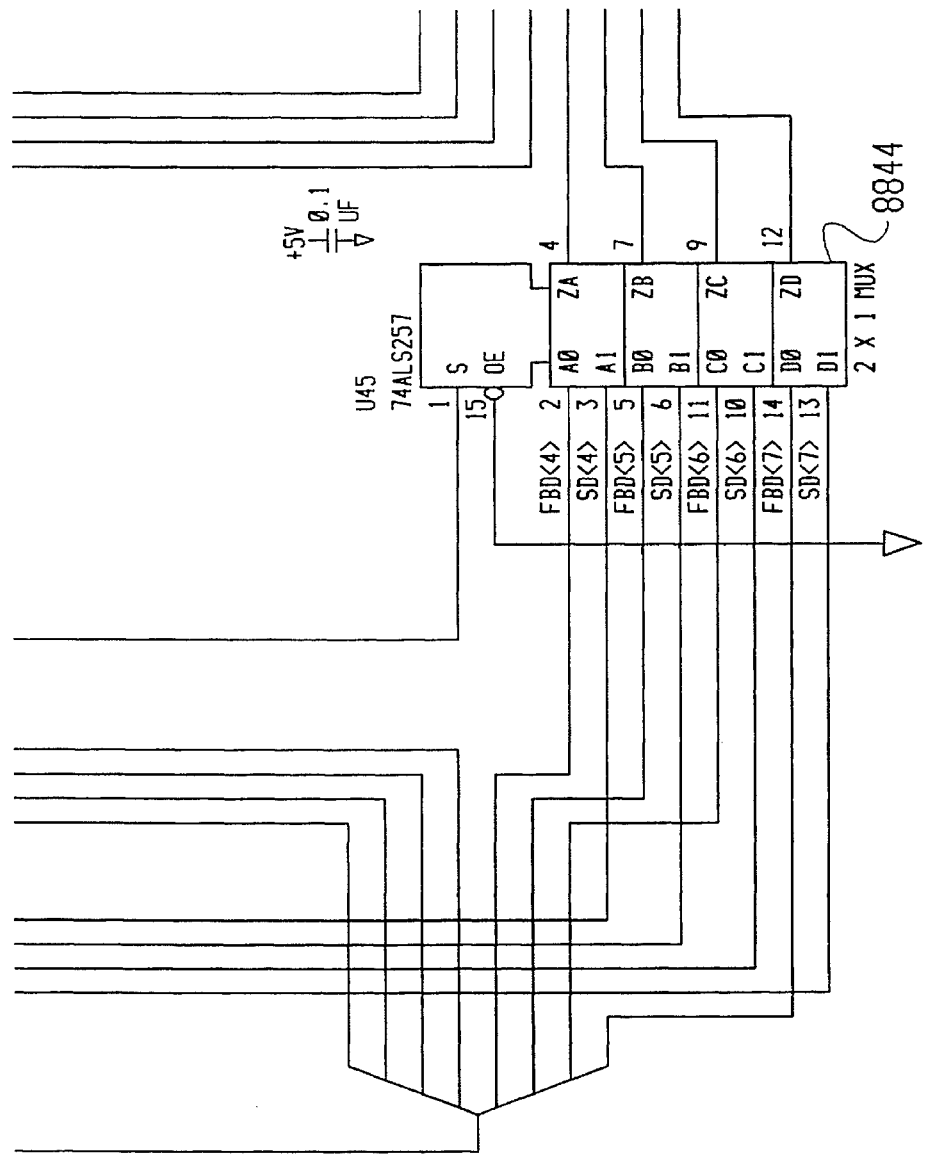
FIGURE 18W5

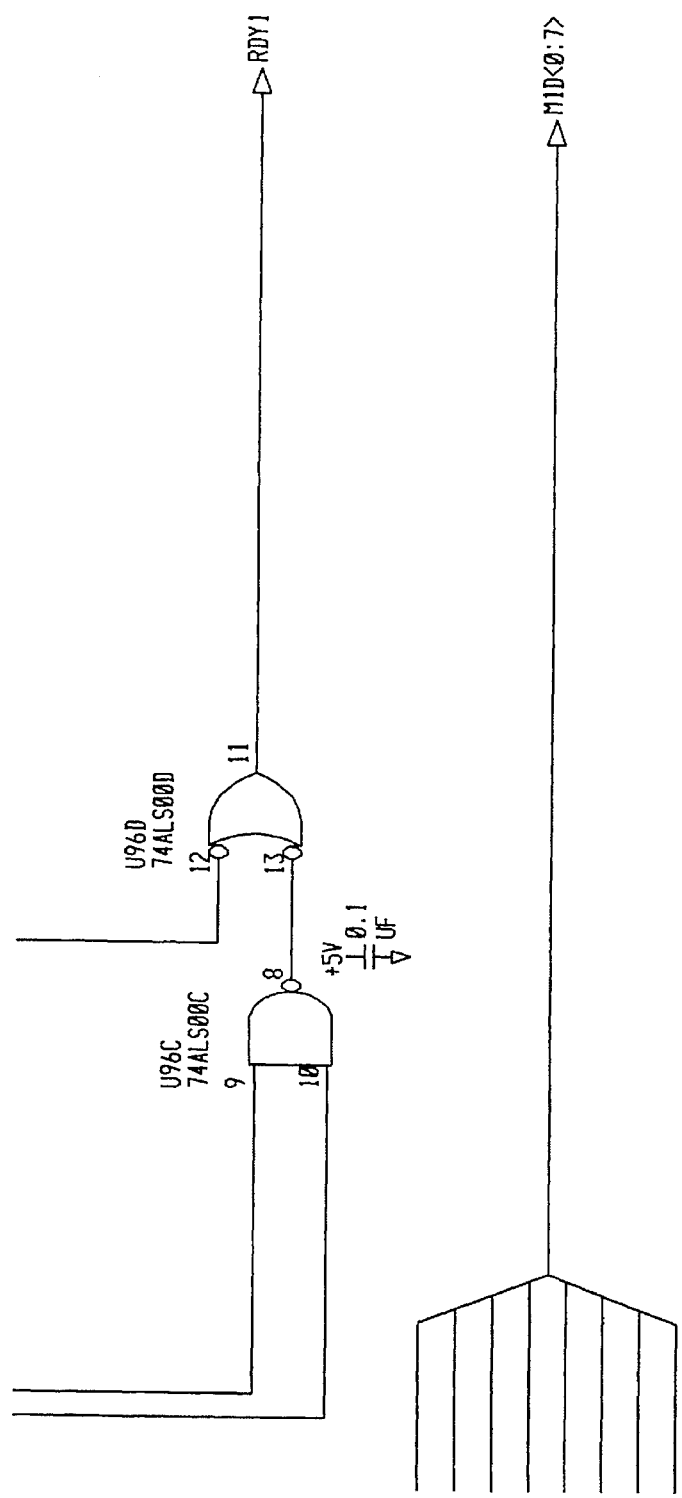
FIGURE 18W6

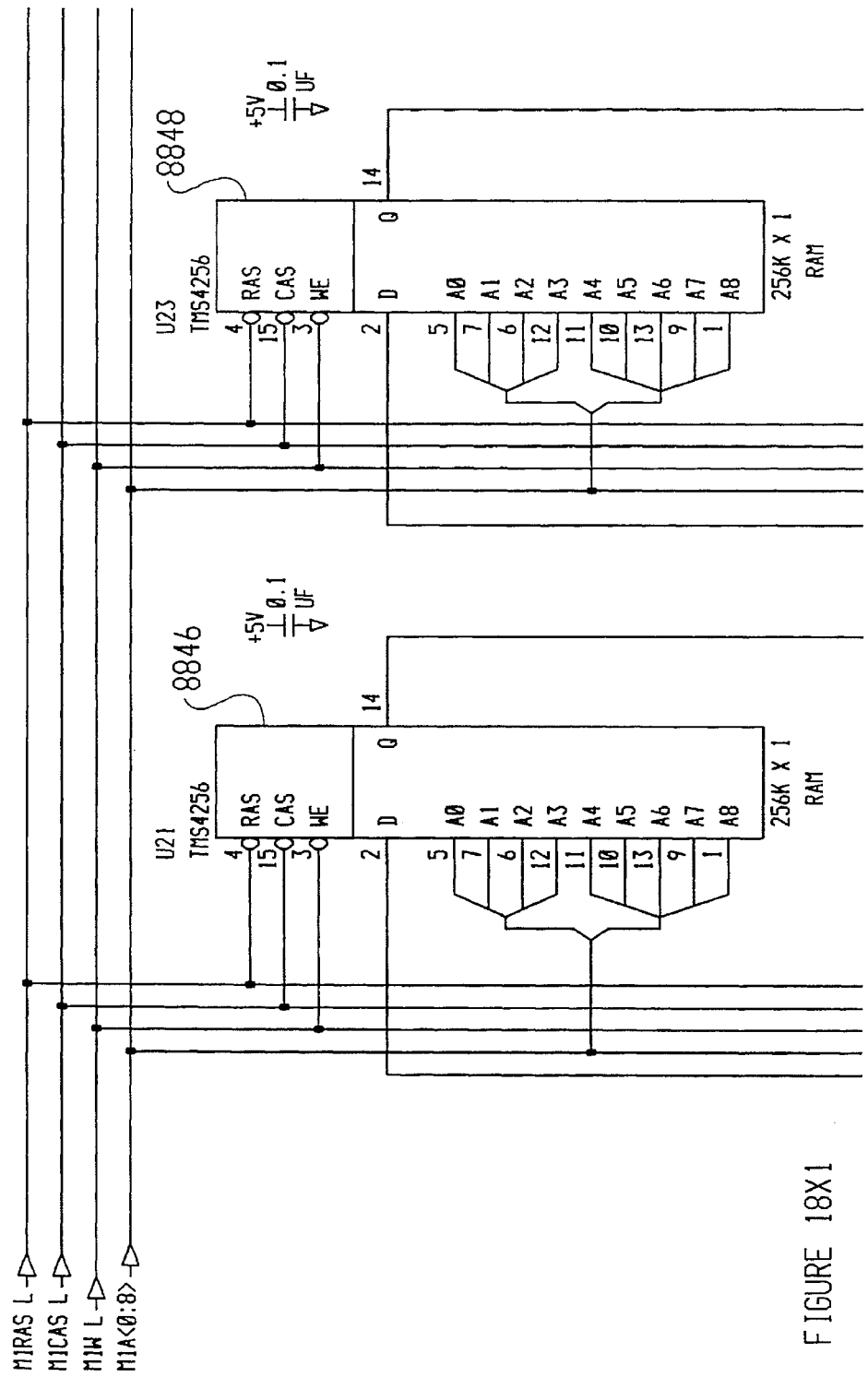
FIGURE 18X1

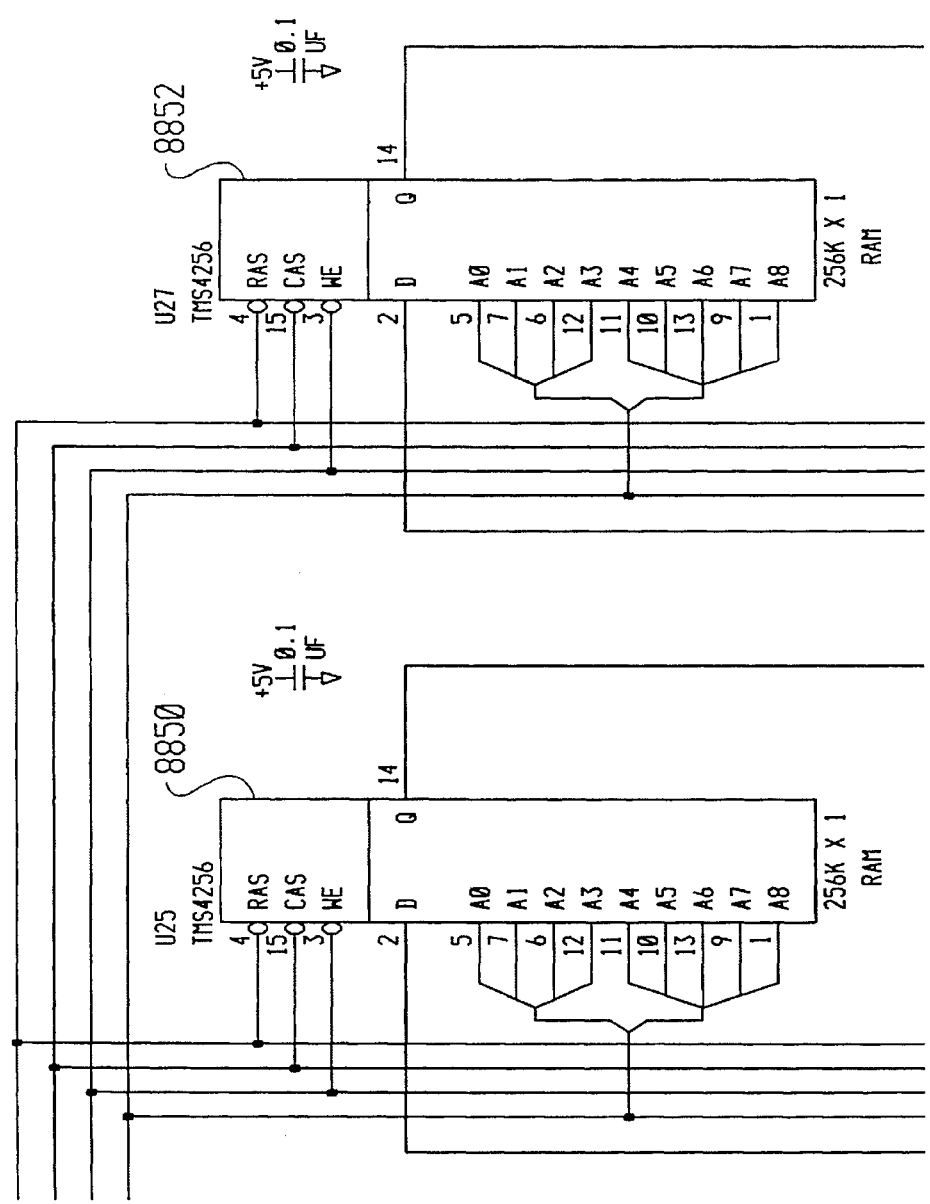
FIGURE 18X2

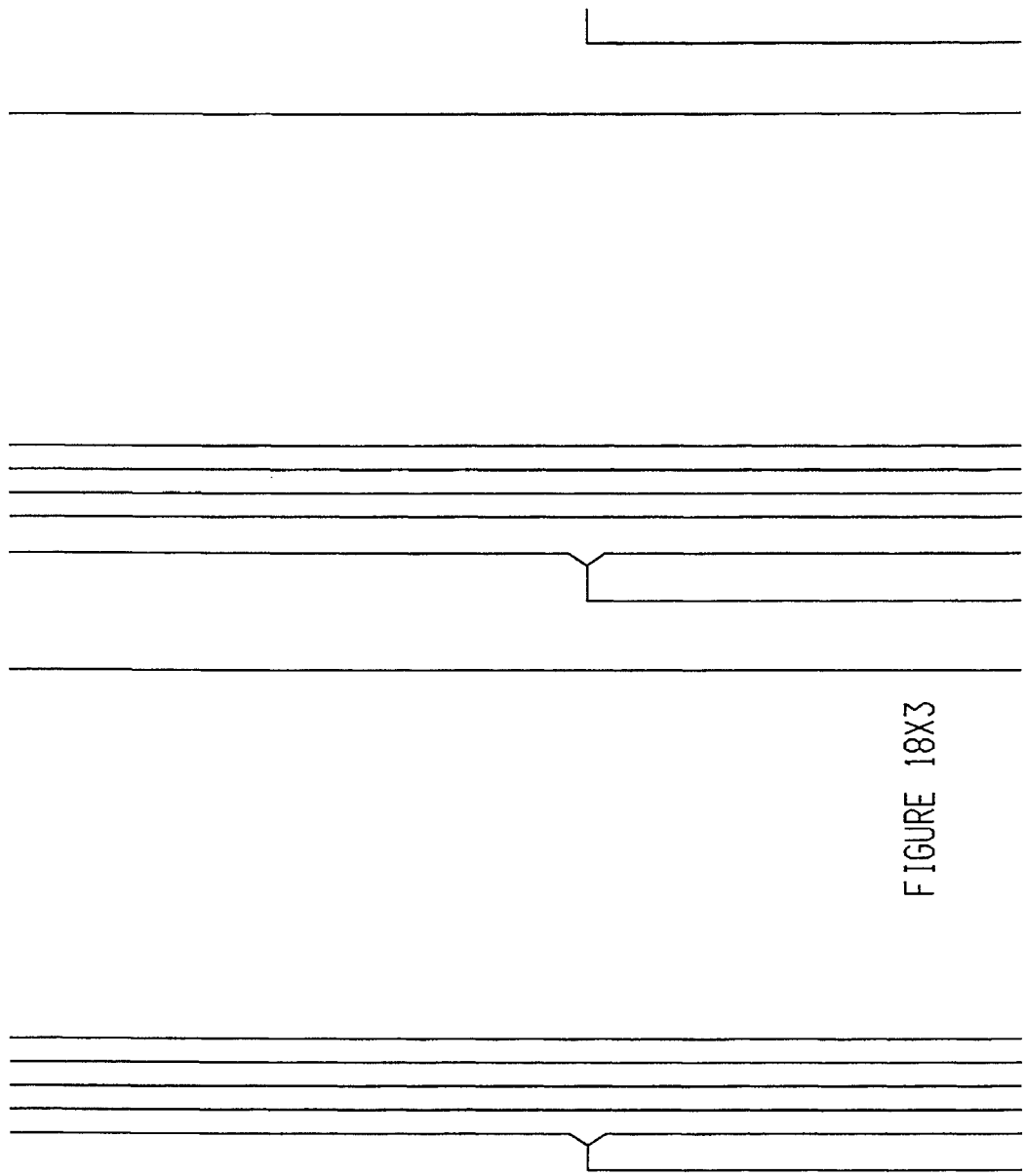
FIGURE 18X3

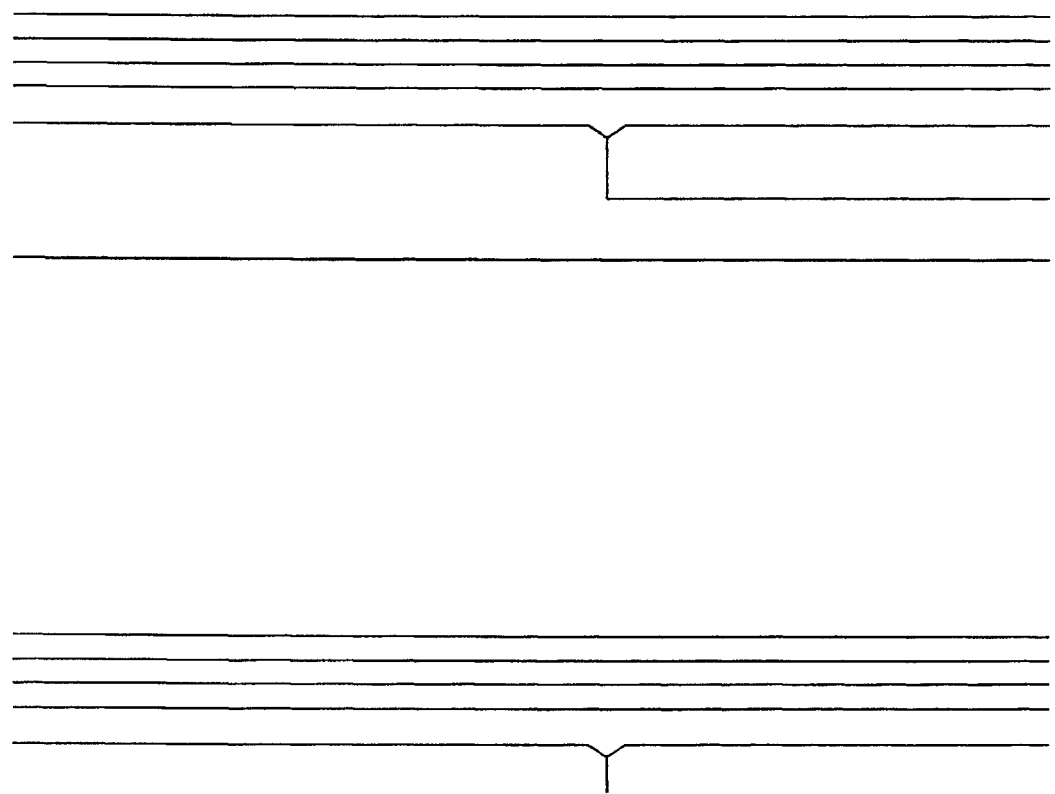
FIGURE 18X4

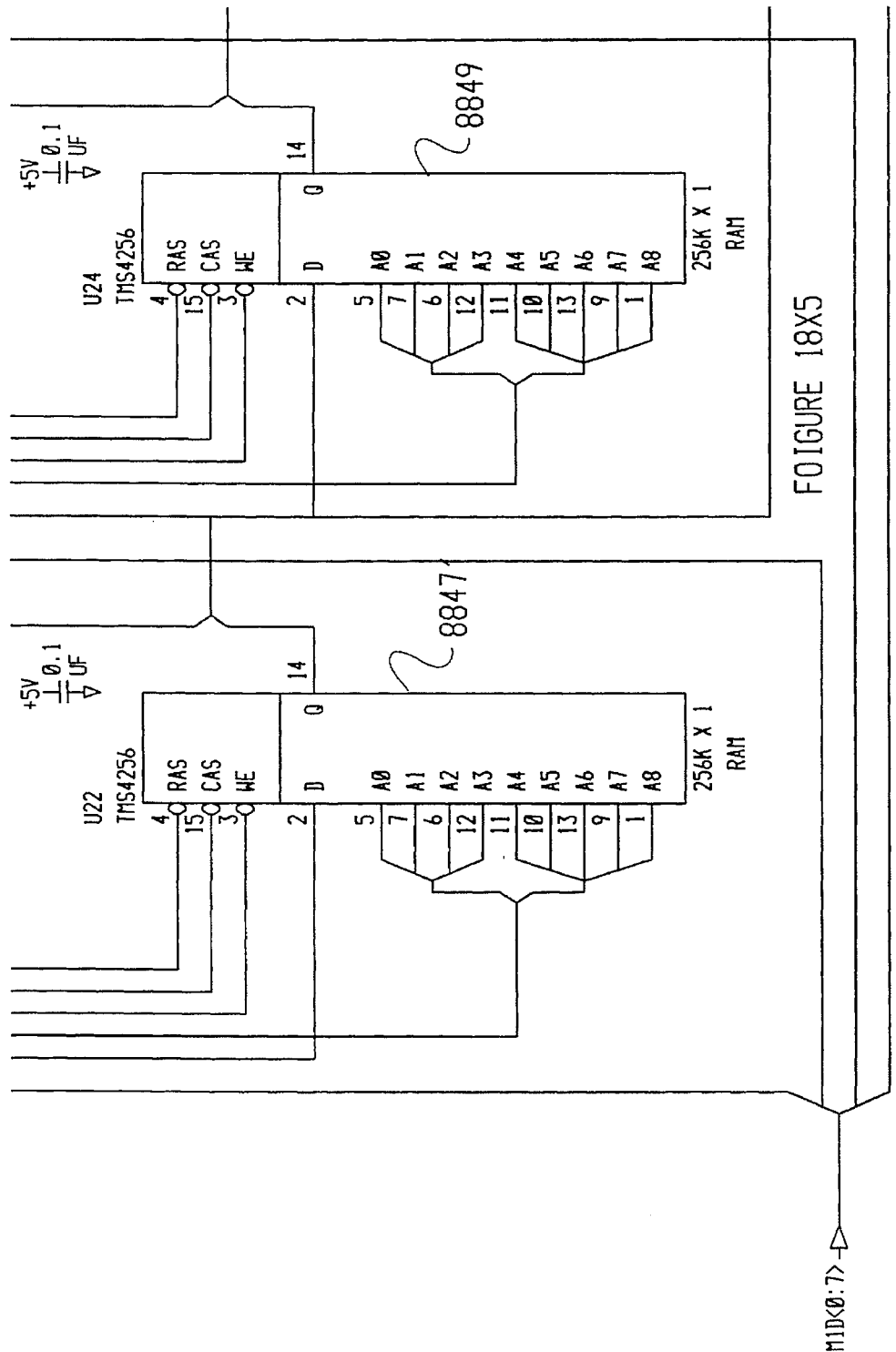
FOIGURE 18X5

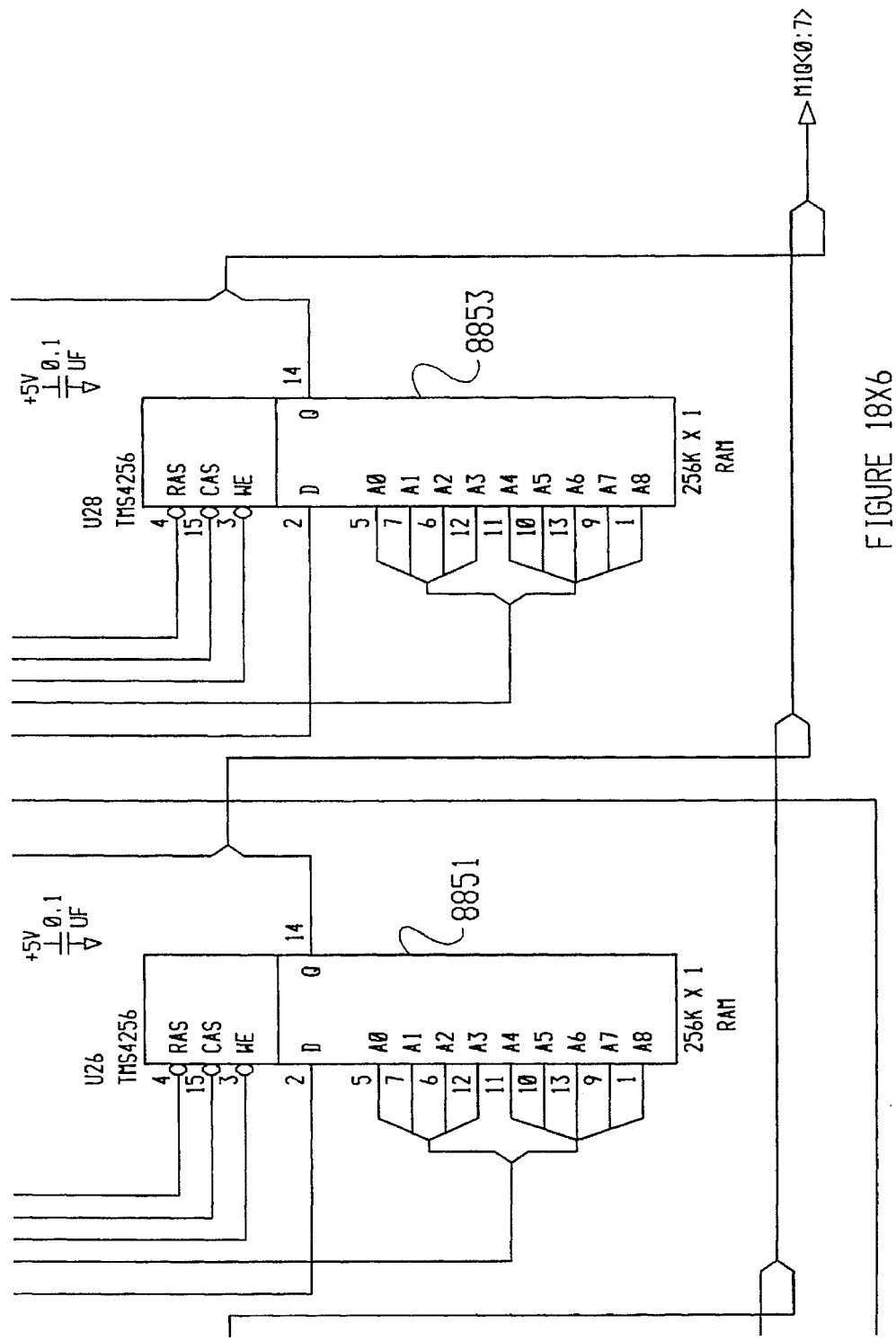
FIGURE 18X6

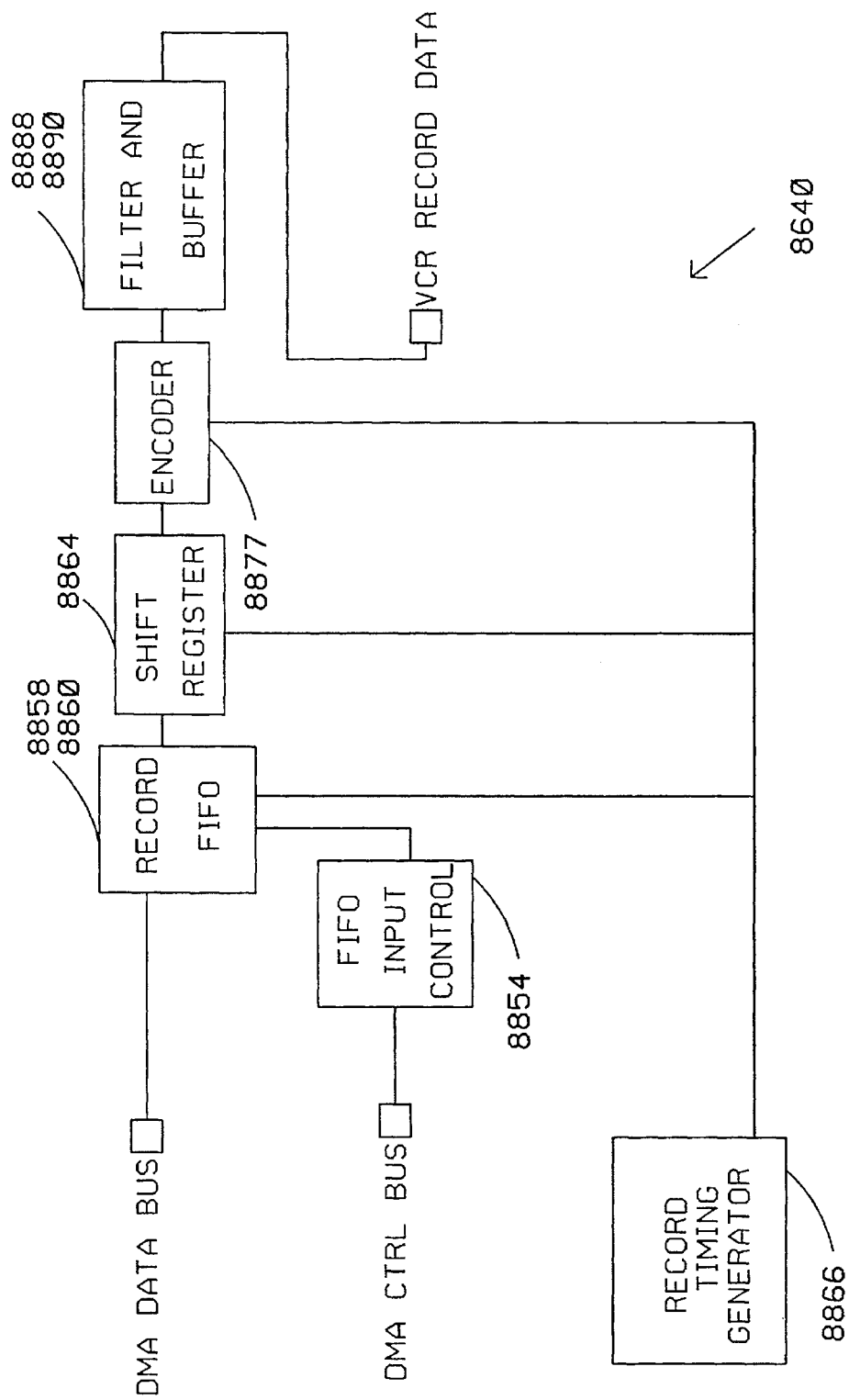

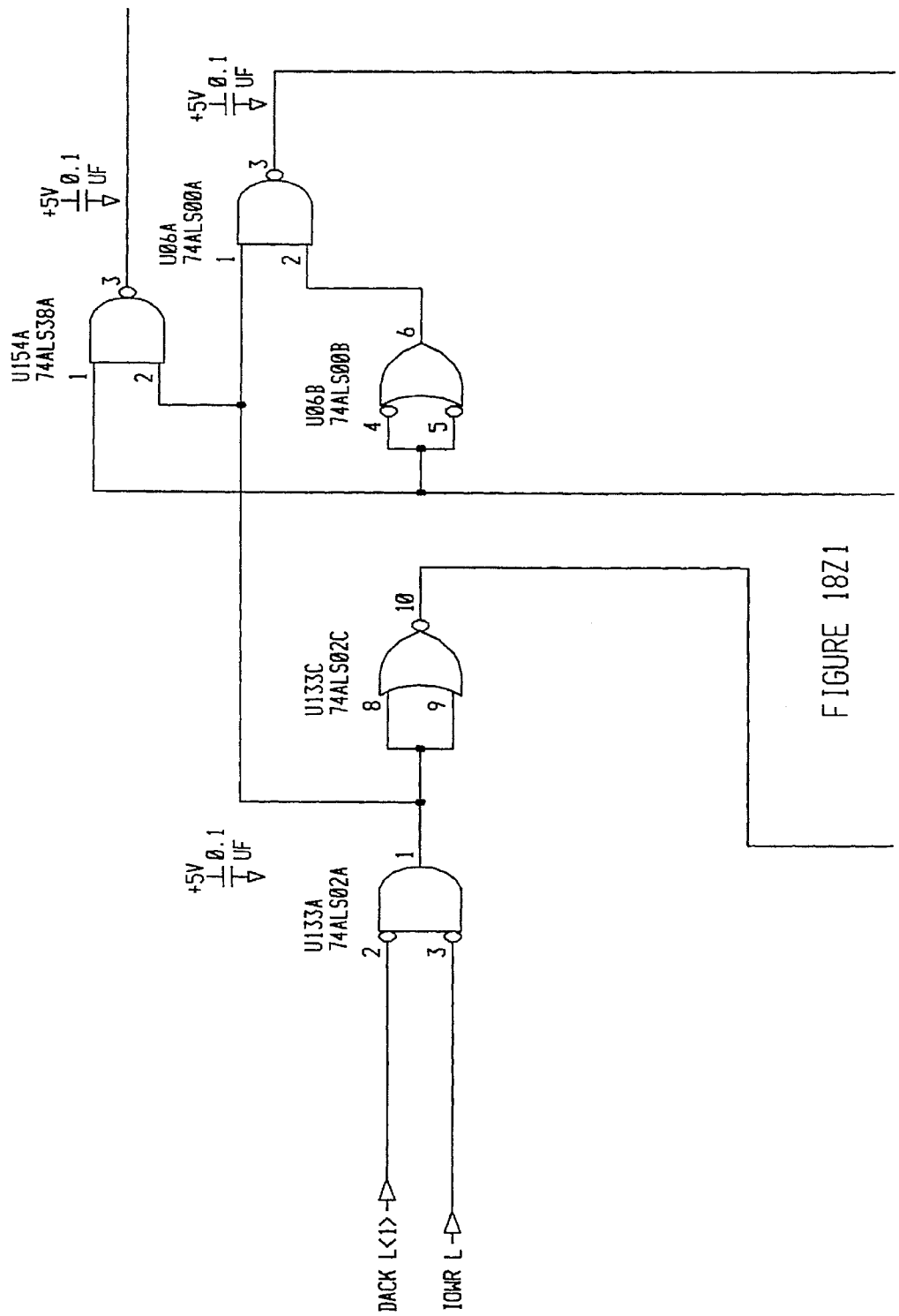

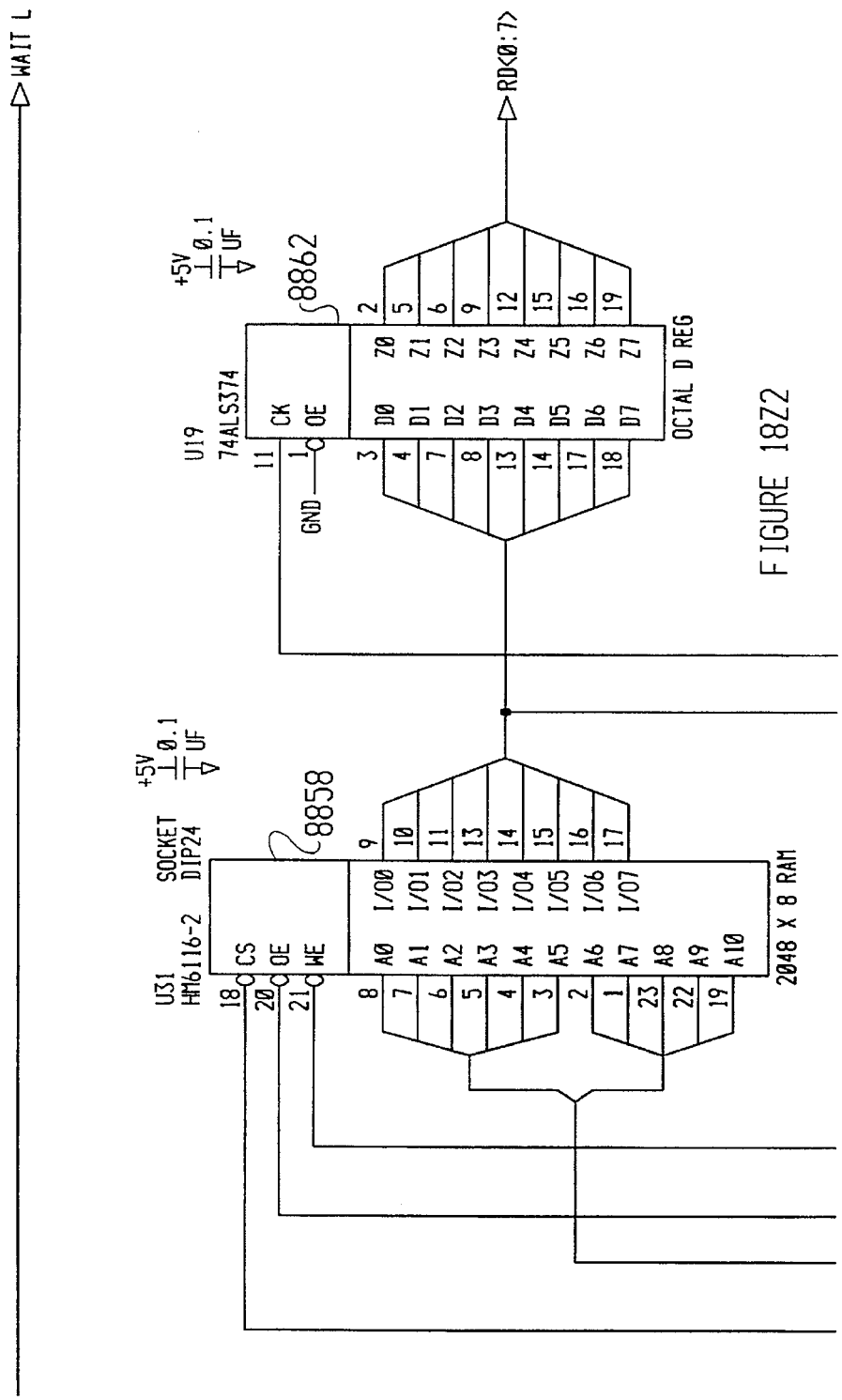
FIGURE 1822

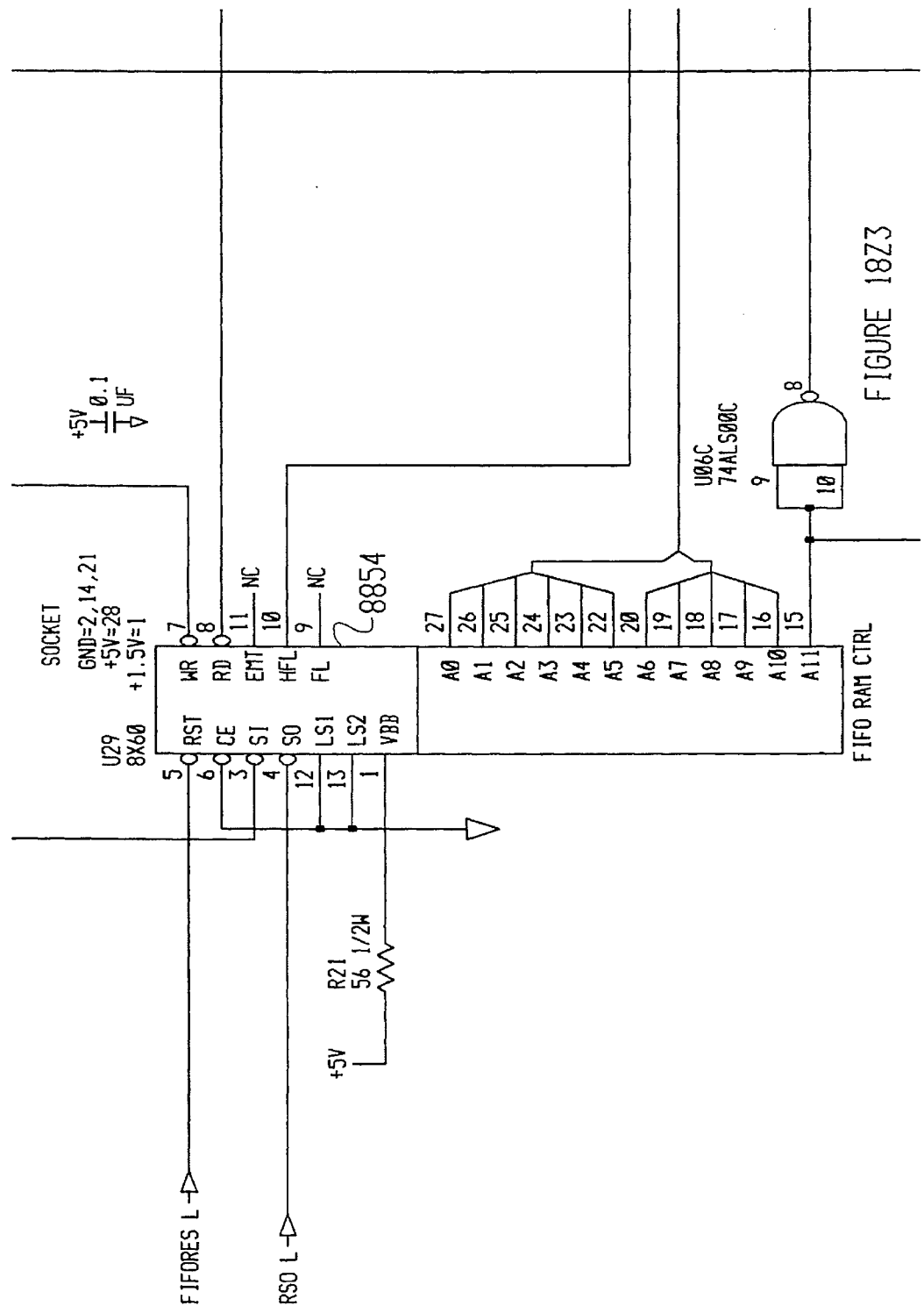
FIGURE 18Z3

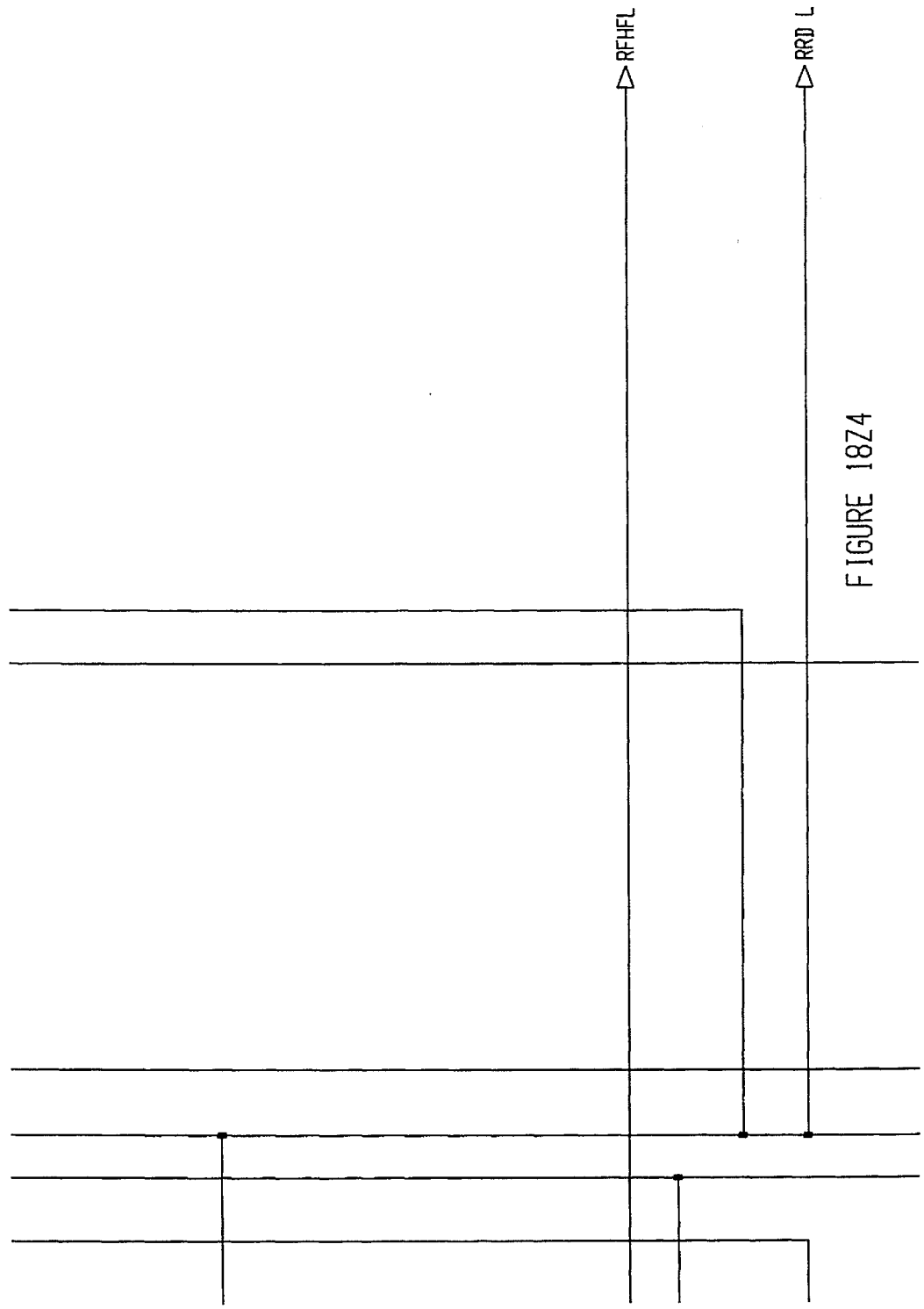

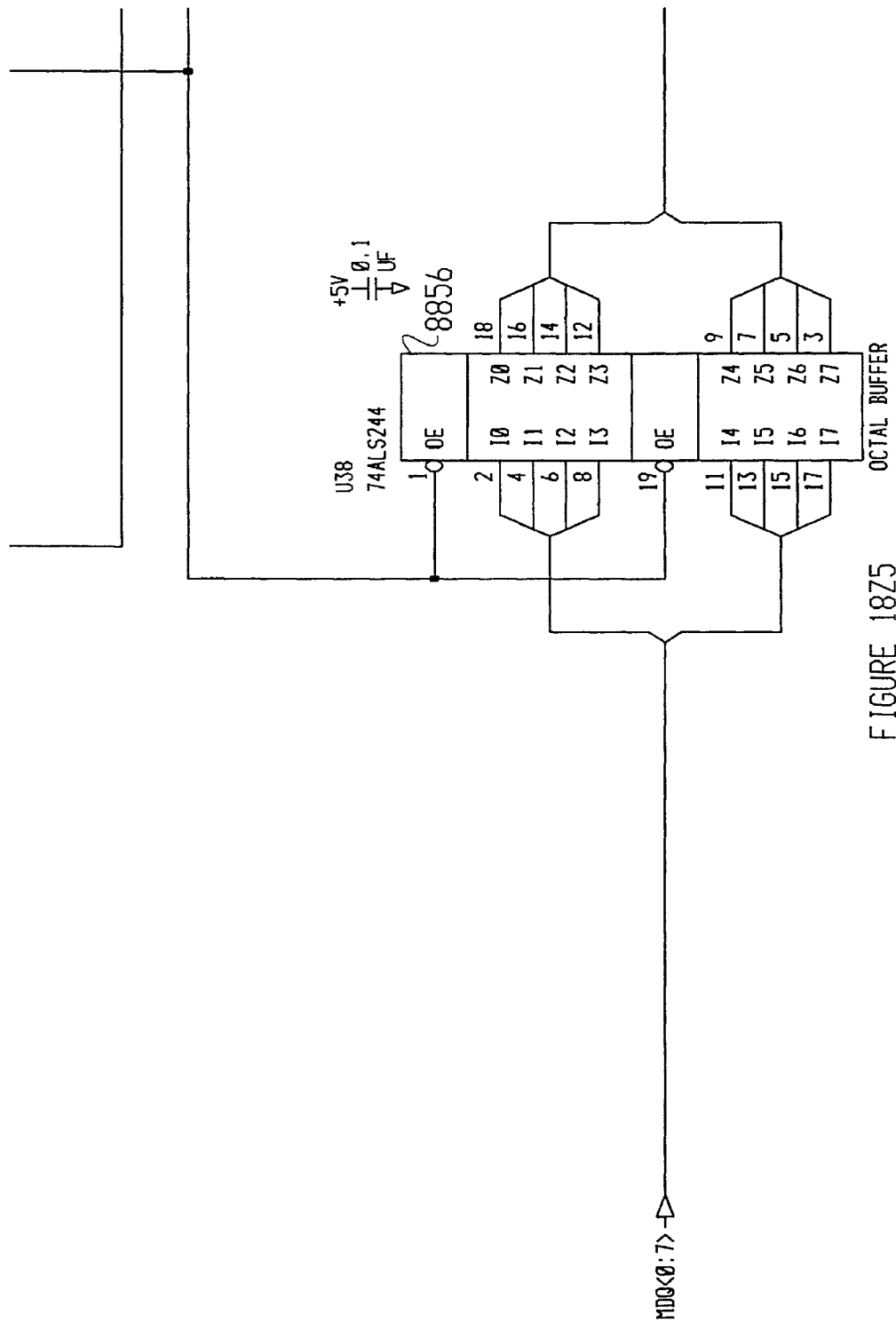
FIGURE 1875

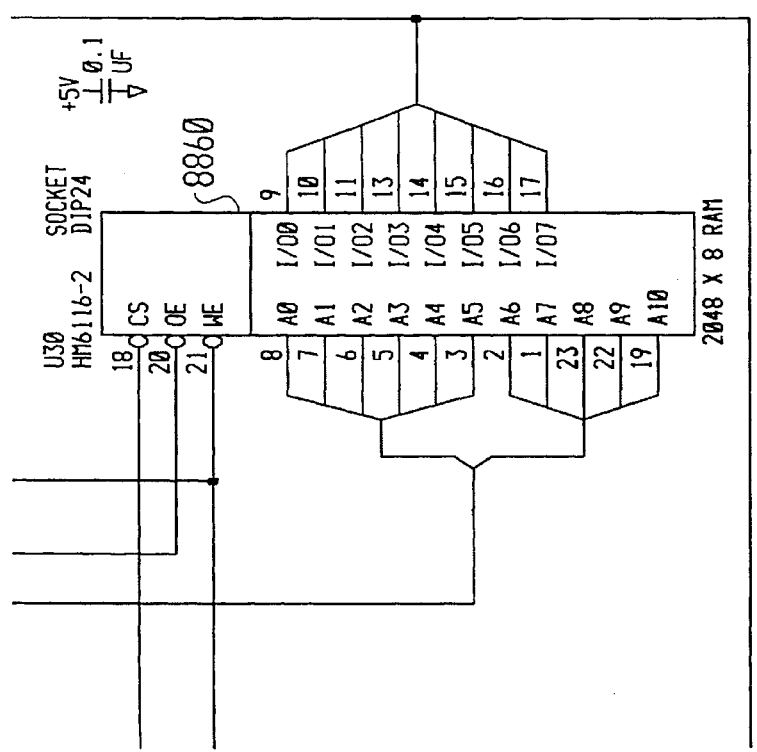
FIGURE 18Z6

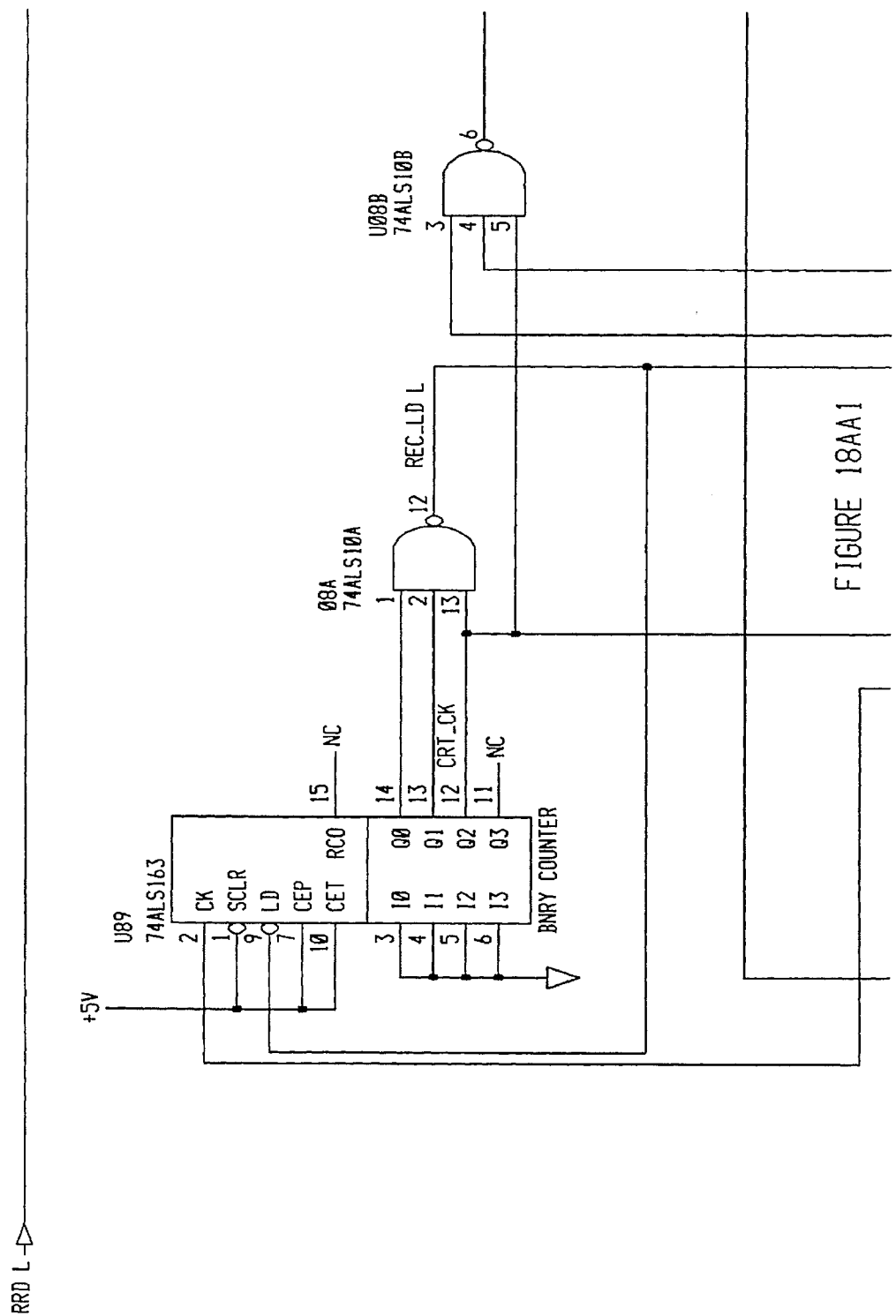

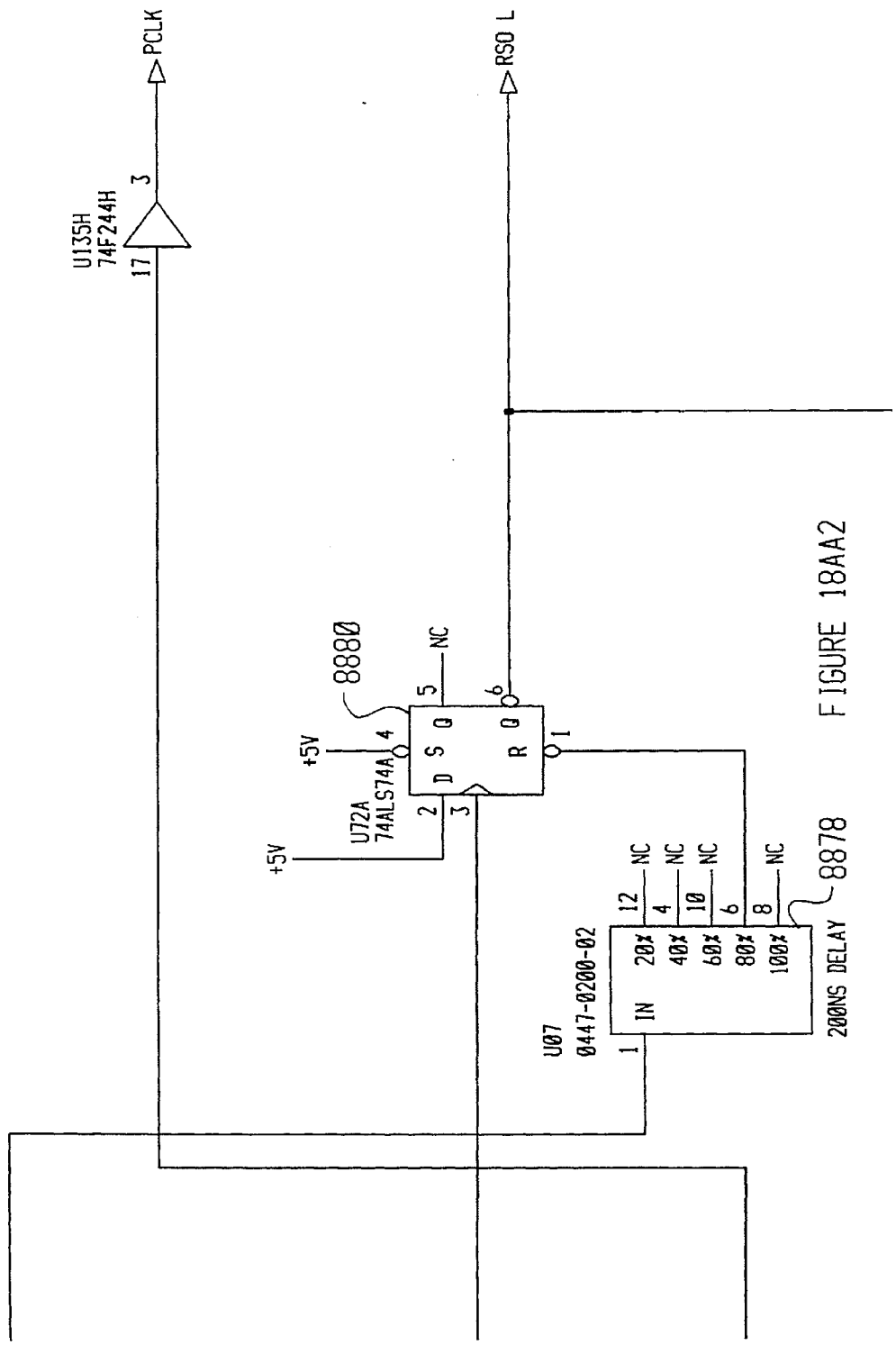

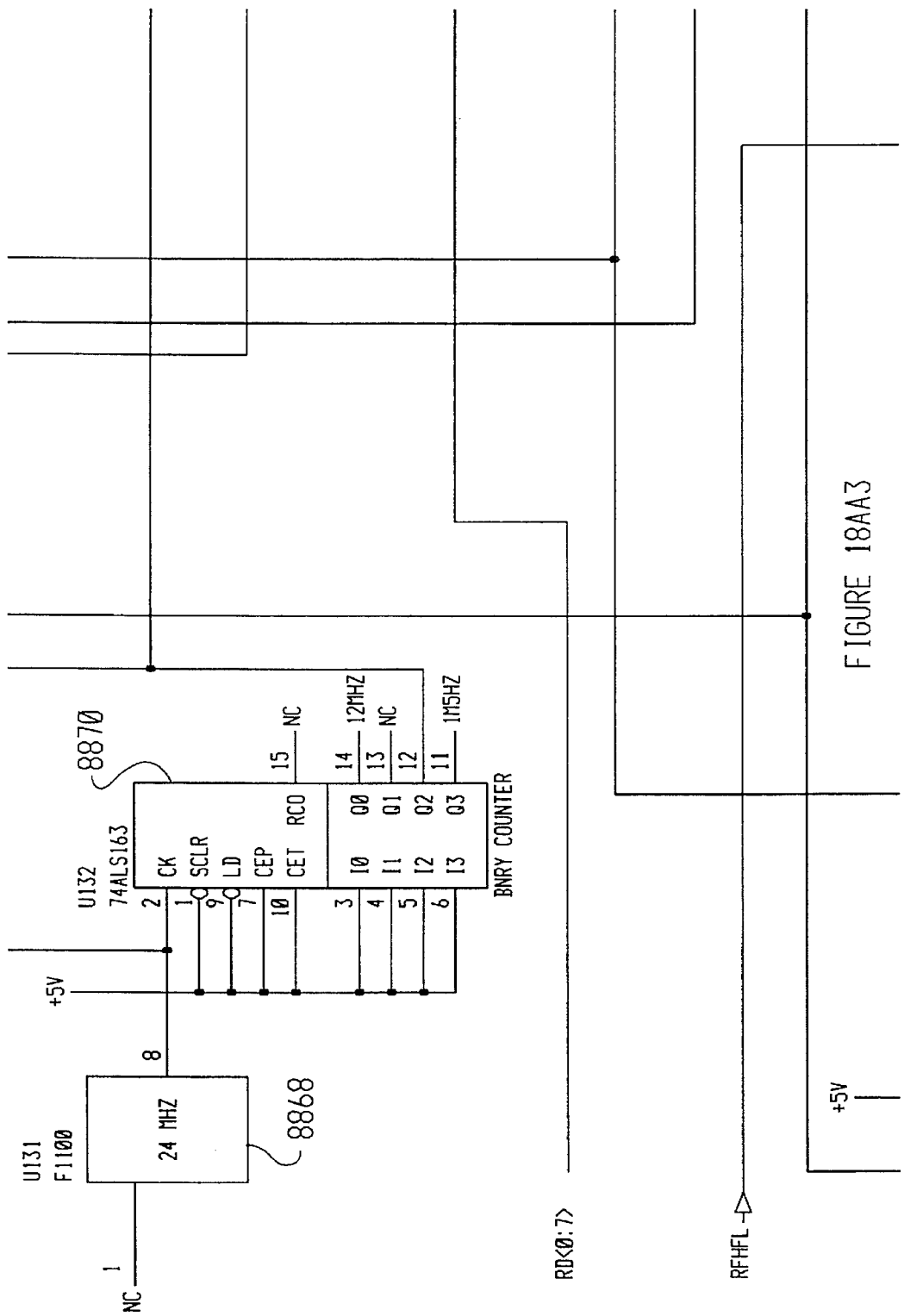

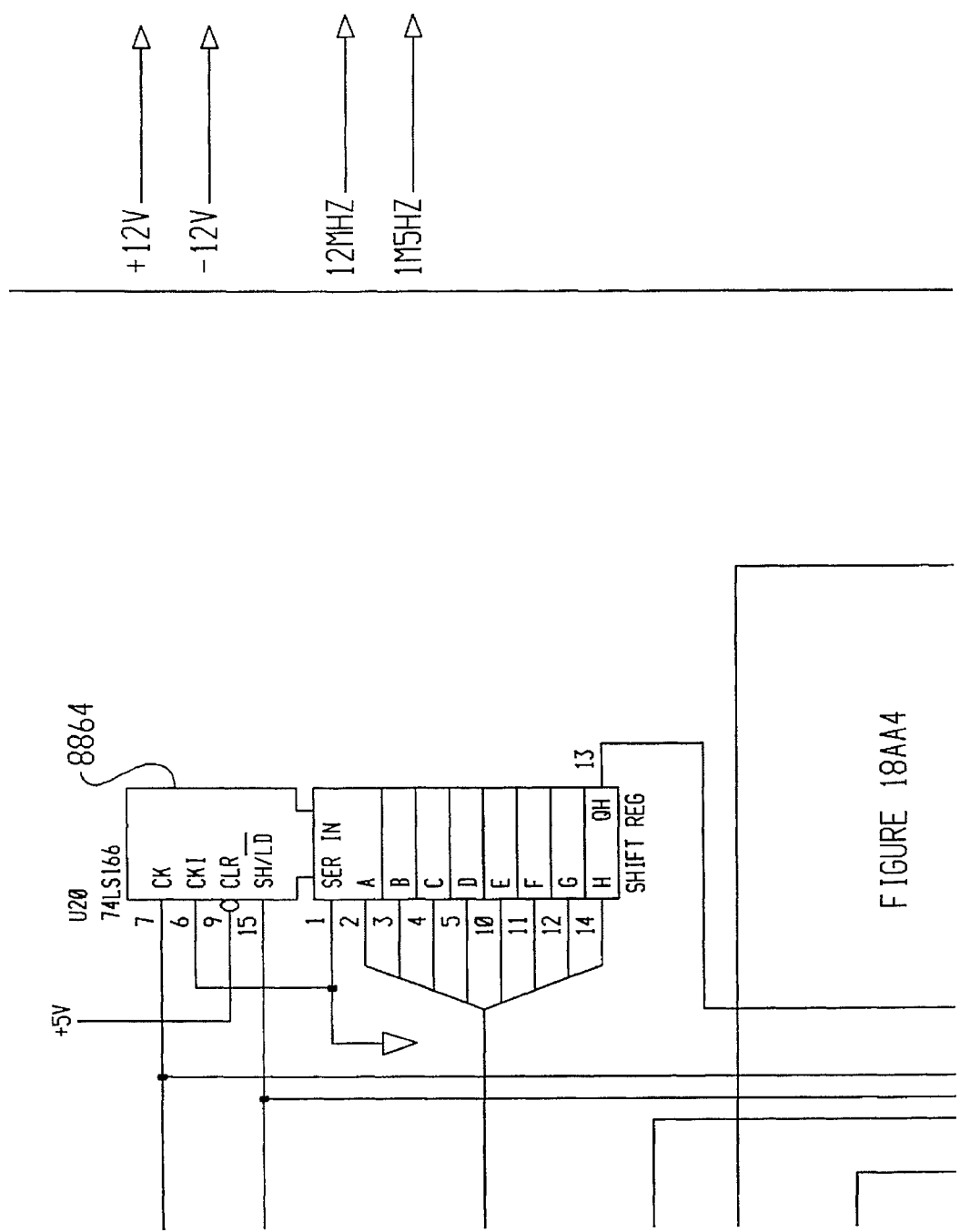
FIGURE 18AA4

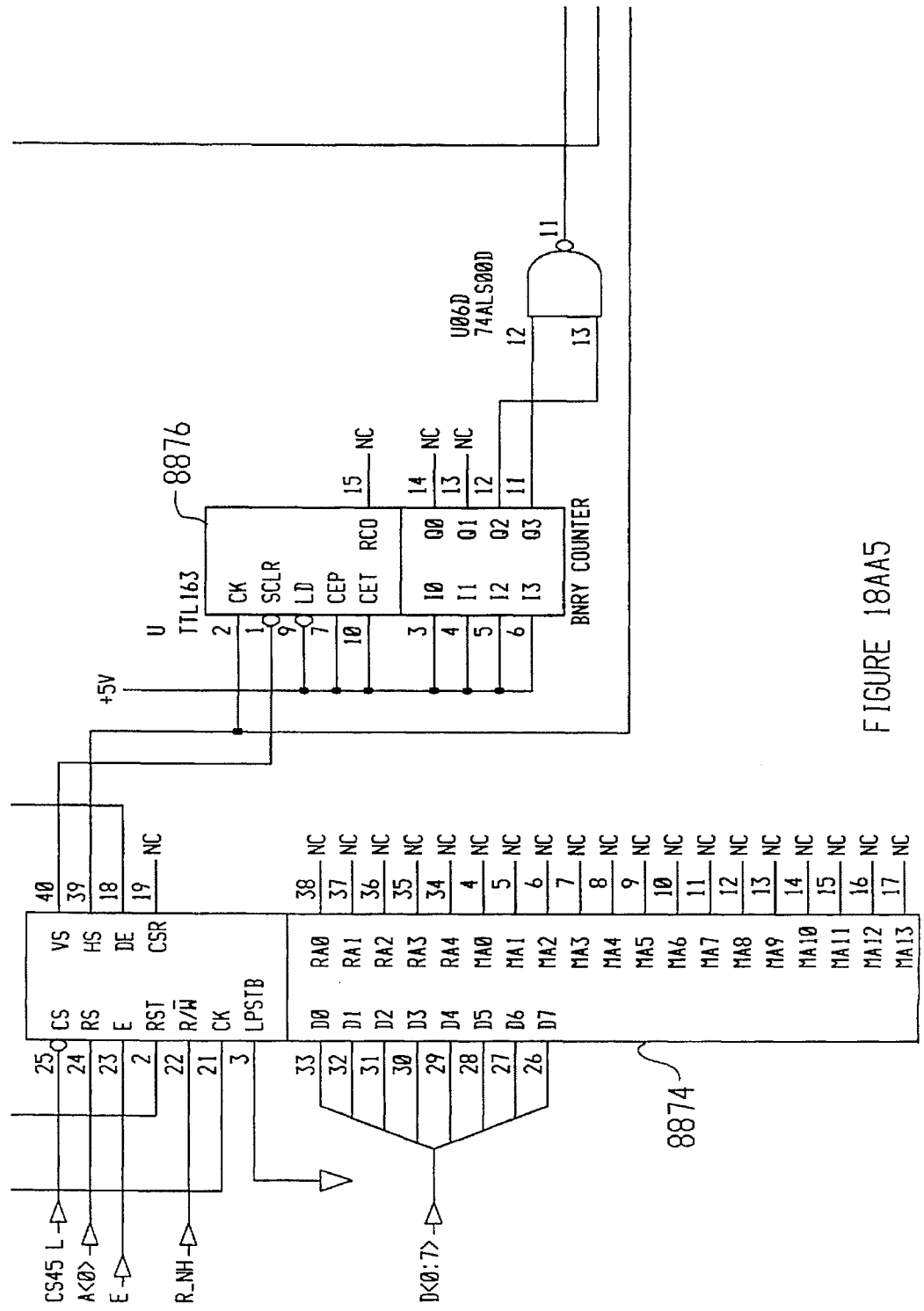
FIGURE 18AA5

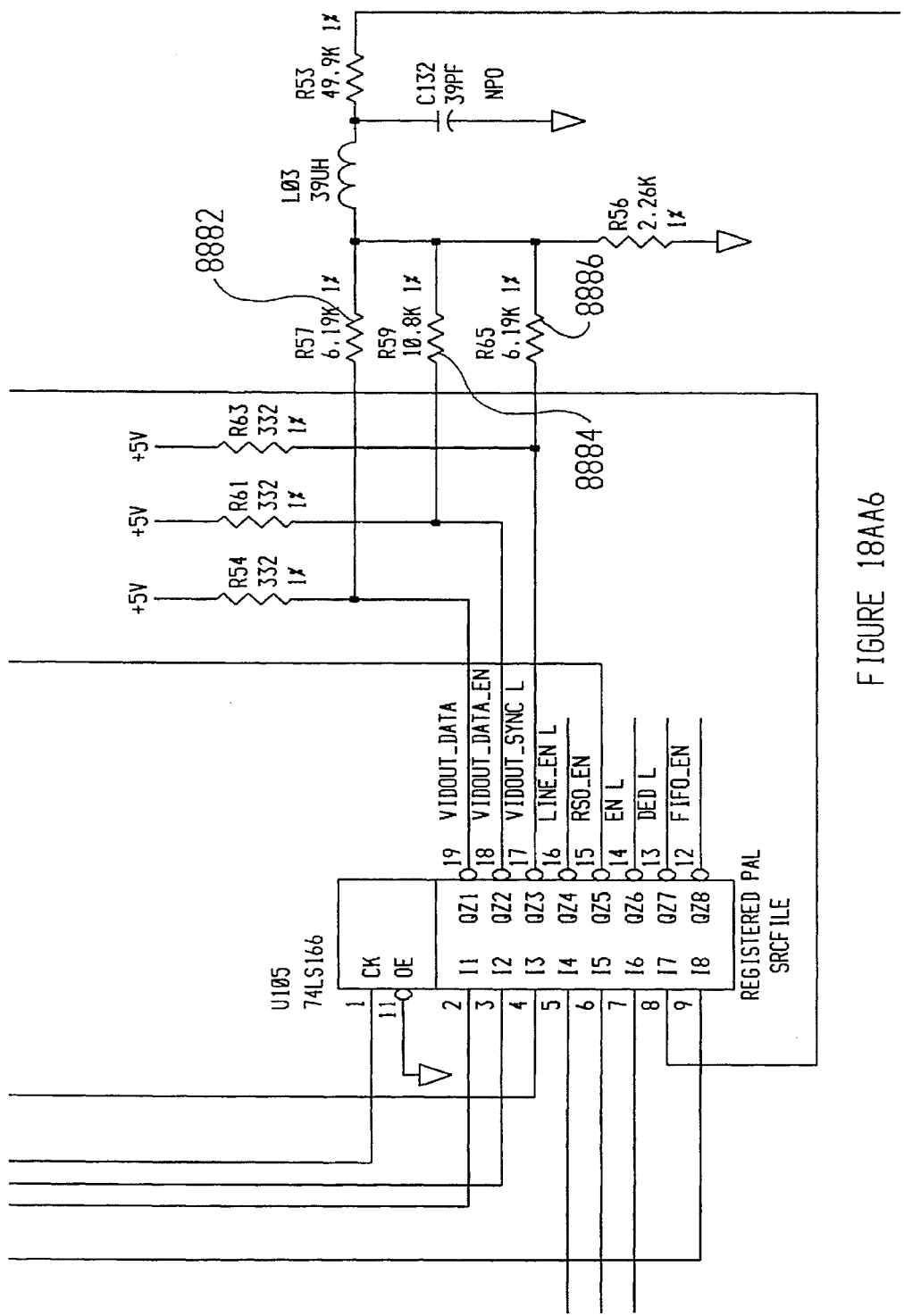
FIGURE 18AA6

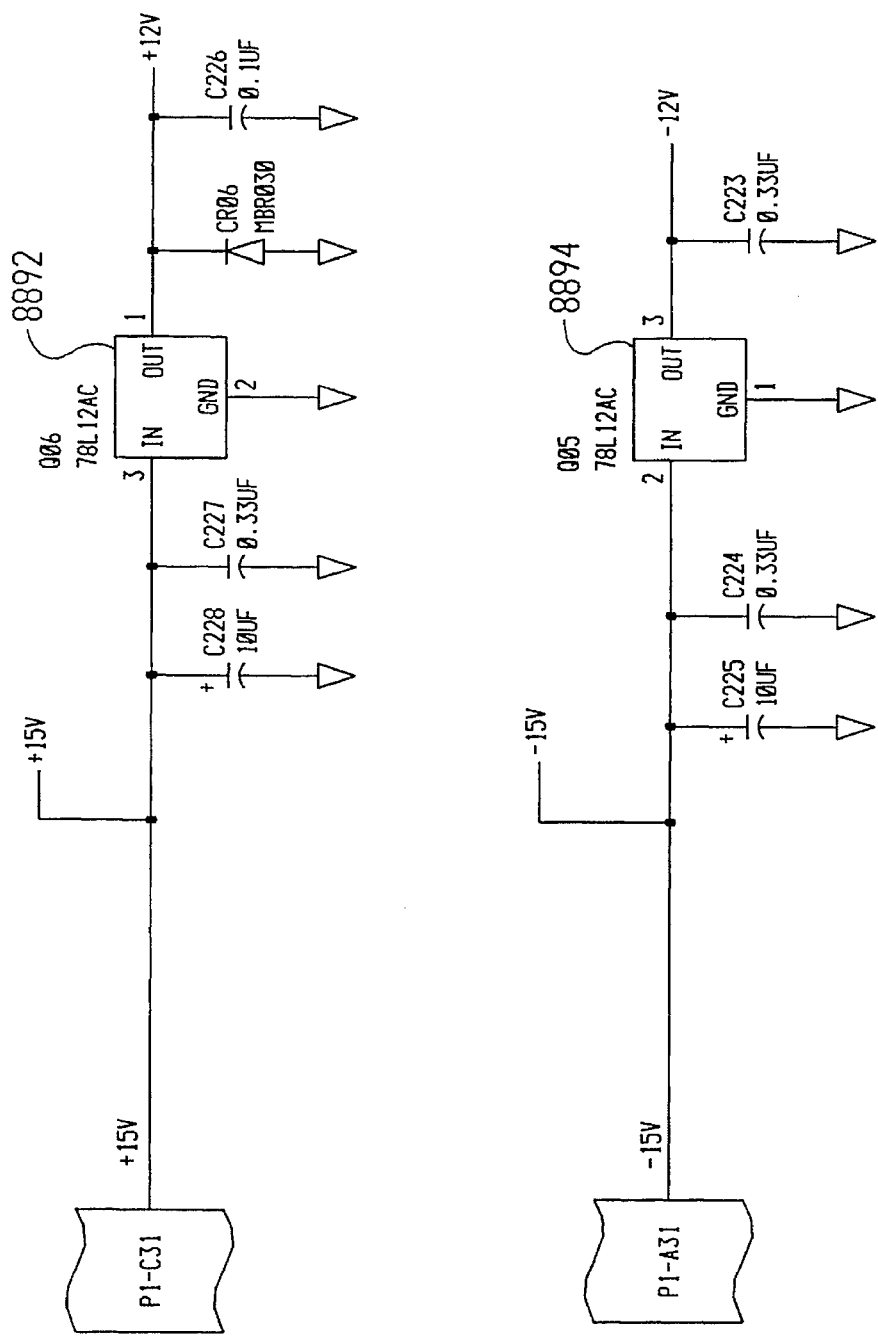
FIGURE 18AA7

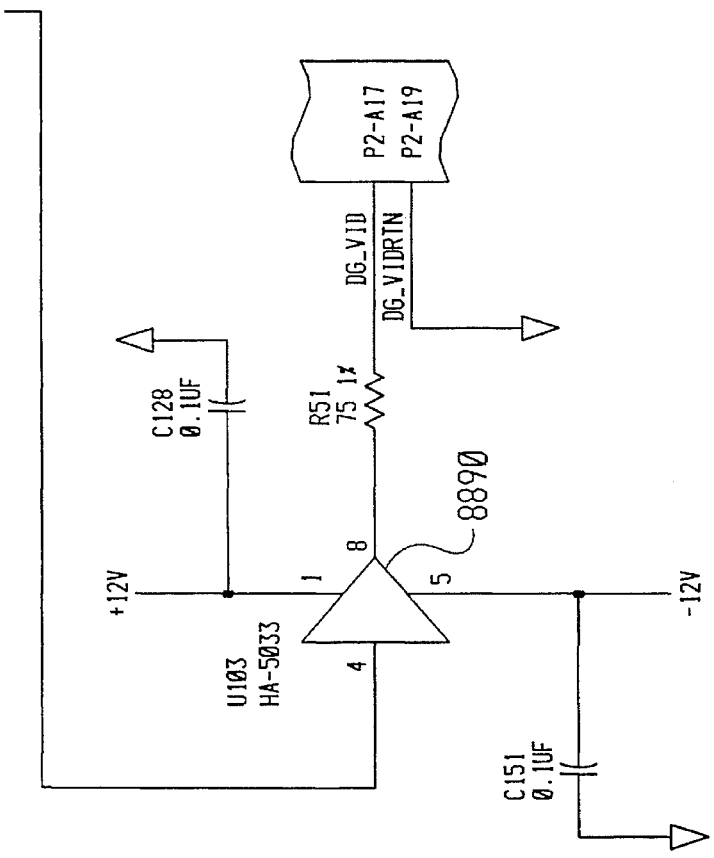
FIGURE 18AA8

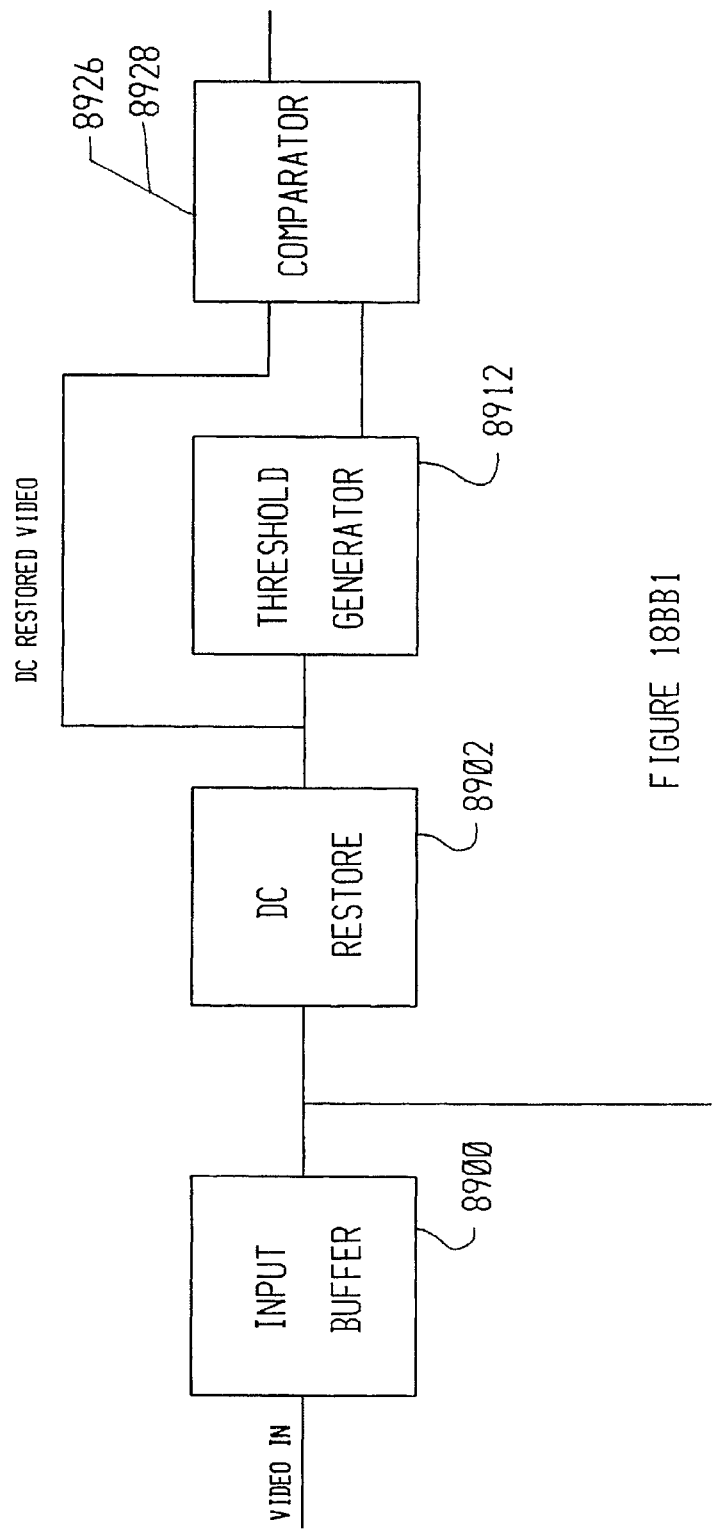
FIGURE 18BB1

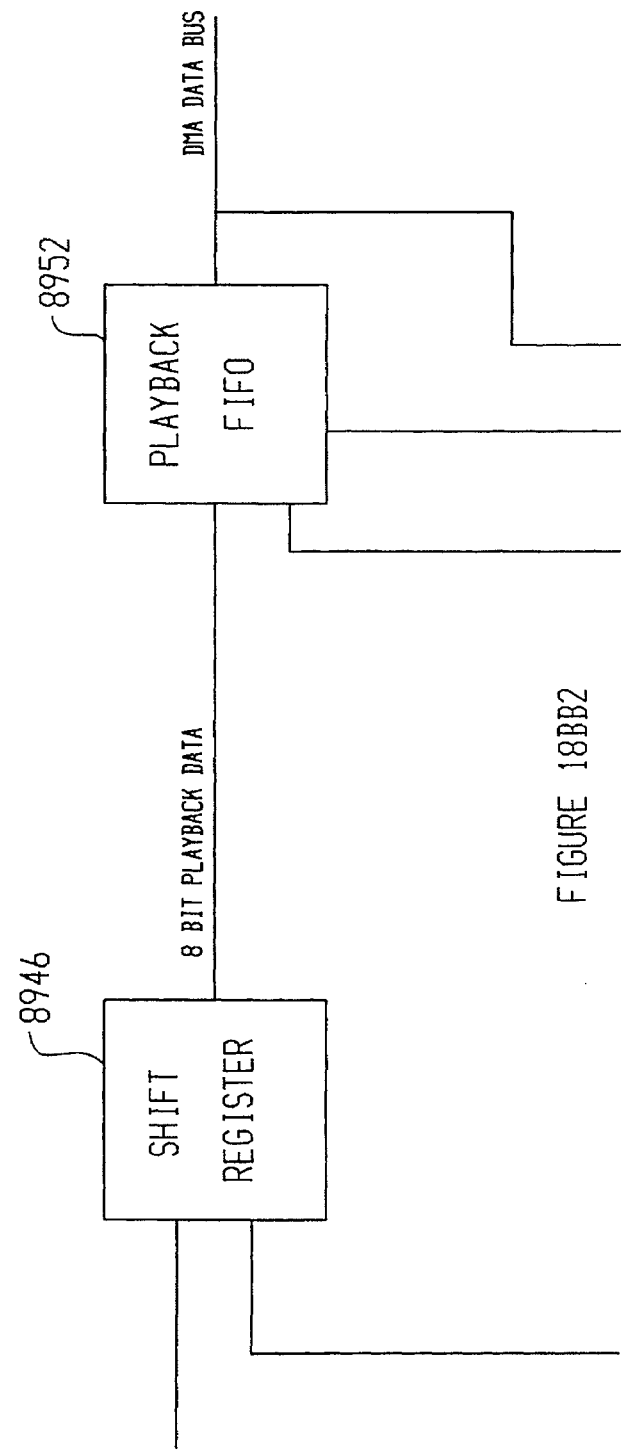
FIGURE 18BB2

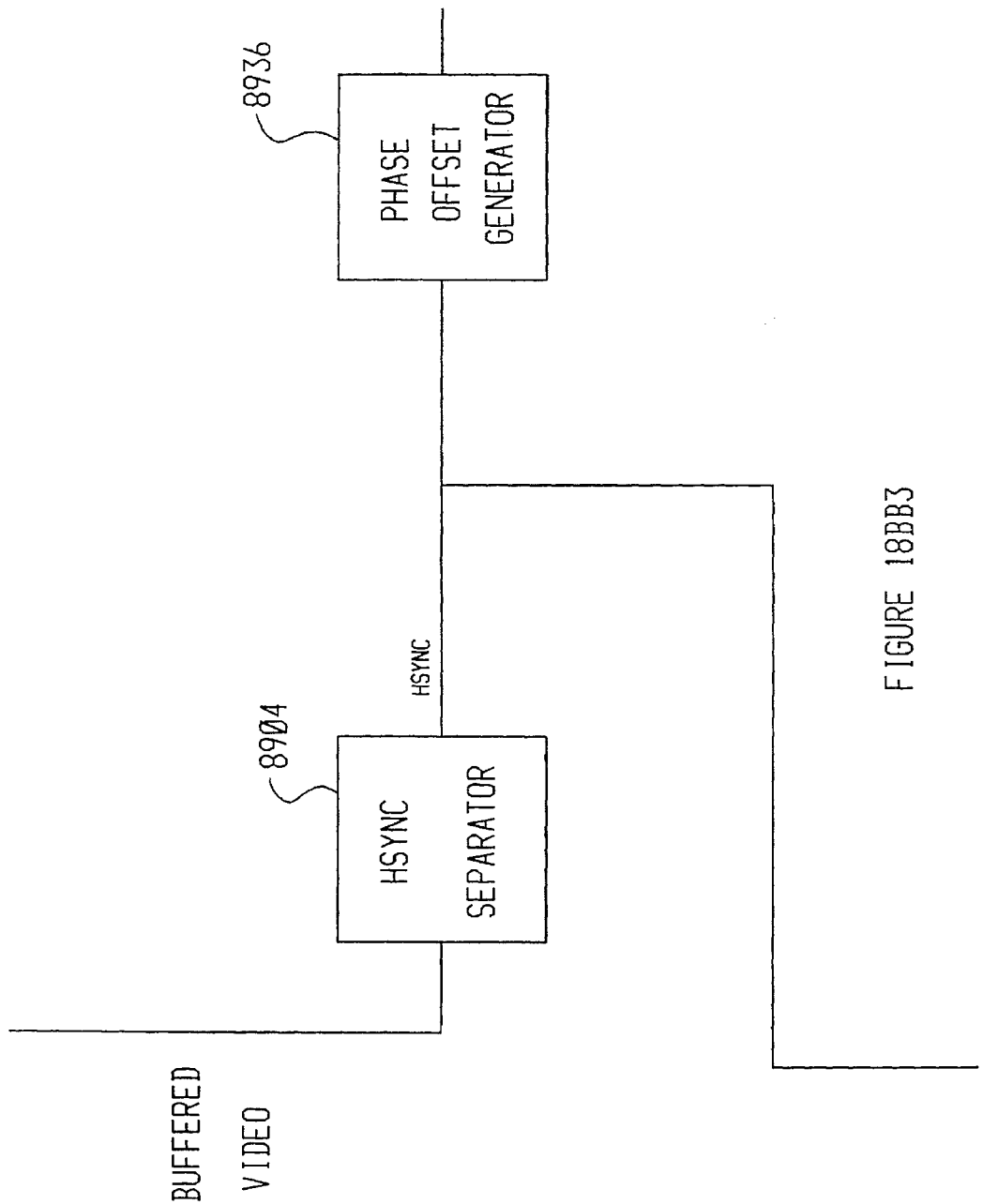

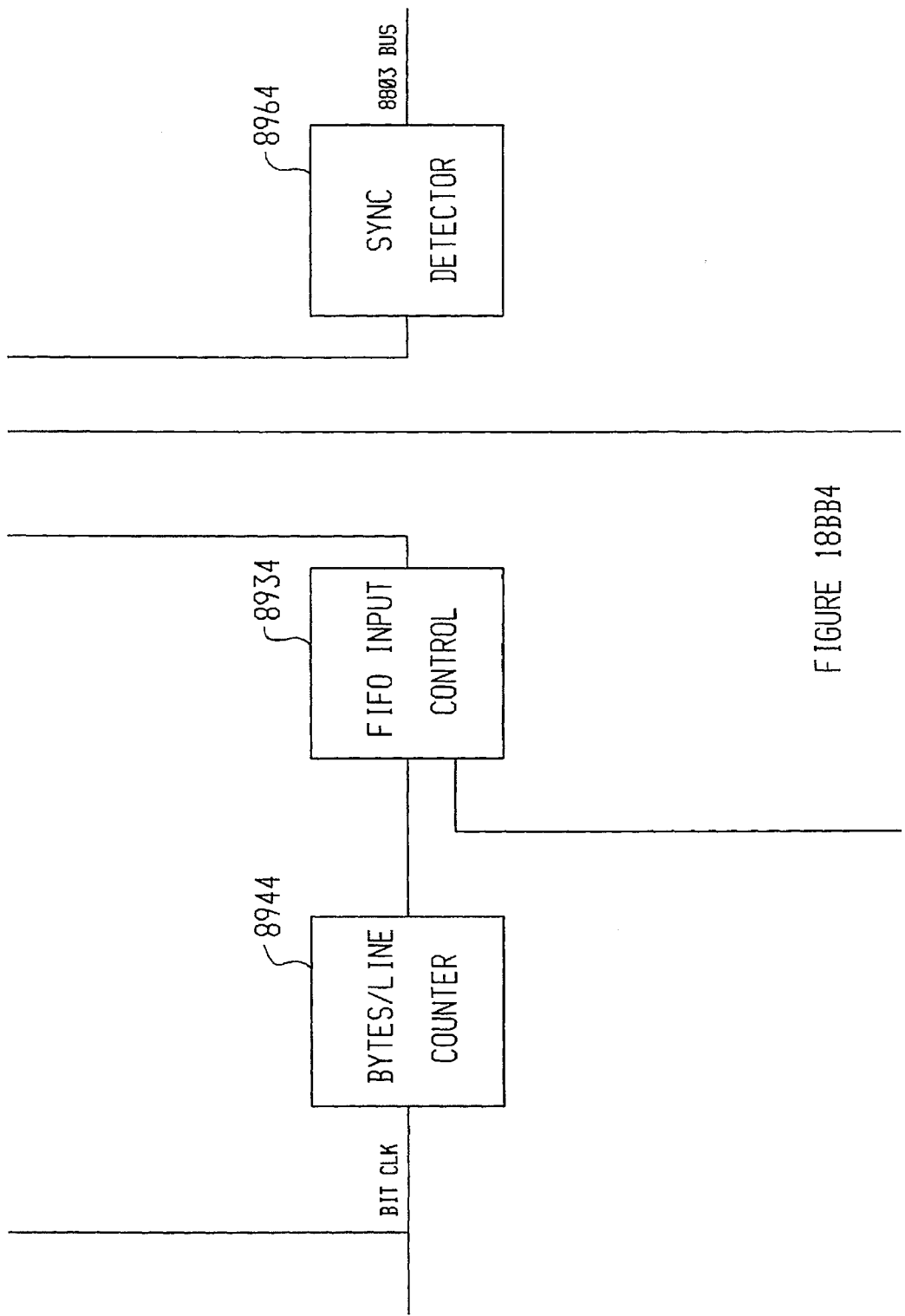
FIGURE 18BB4

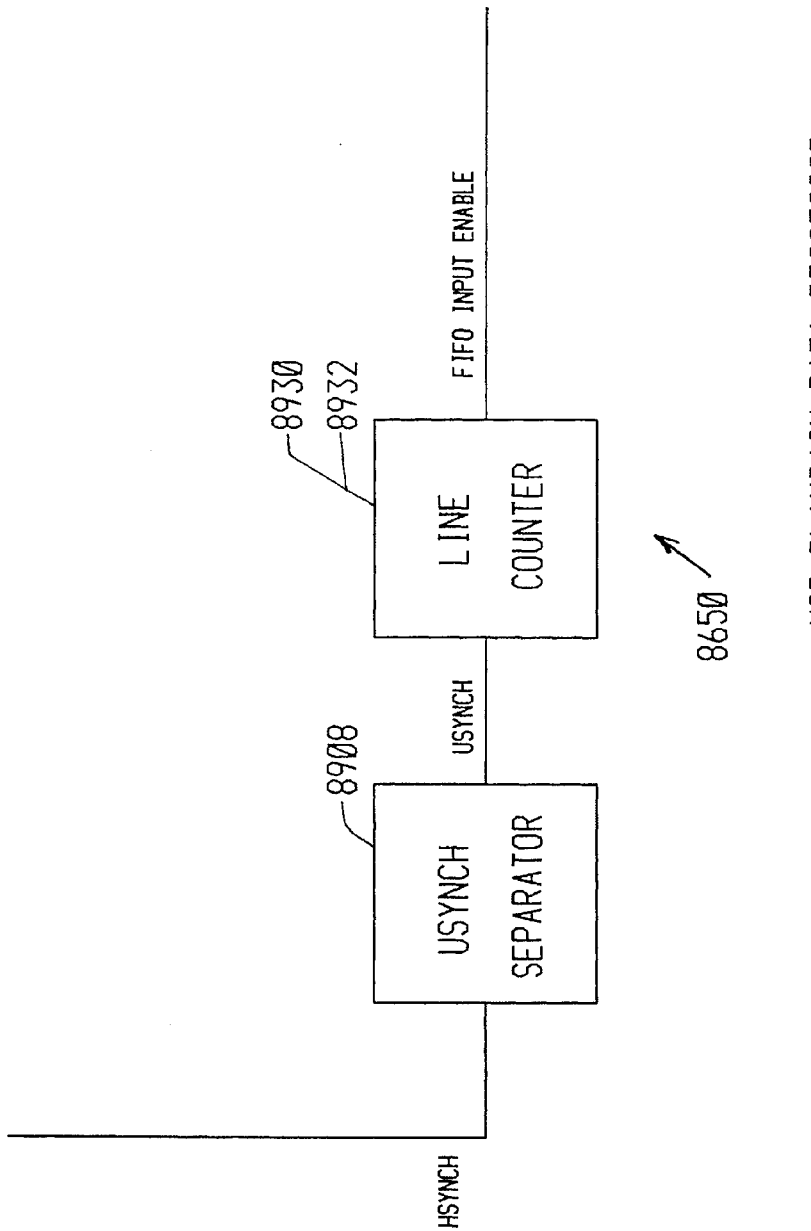
FIGURE 18BB5

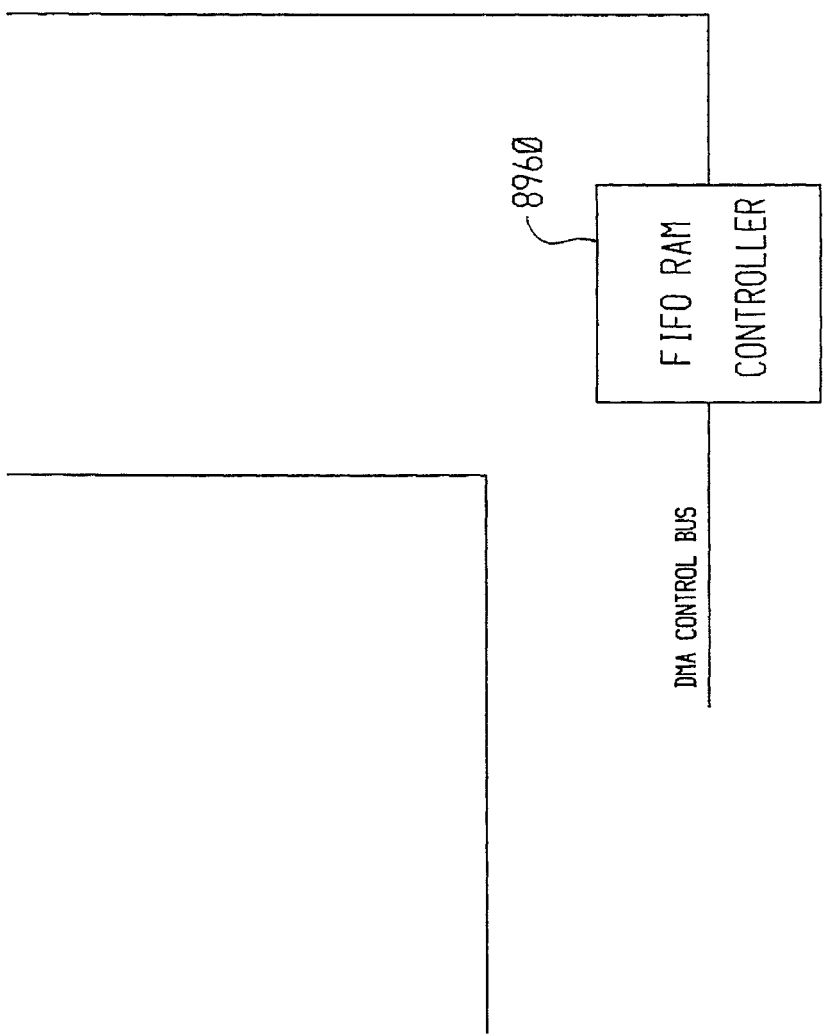
FIGURE 18BB6

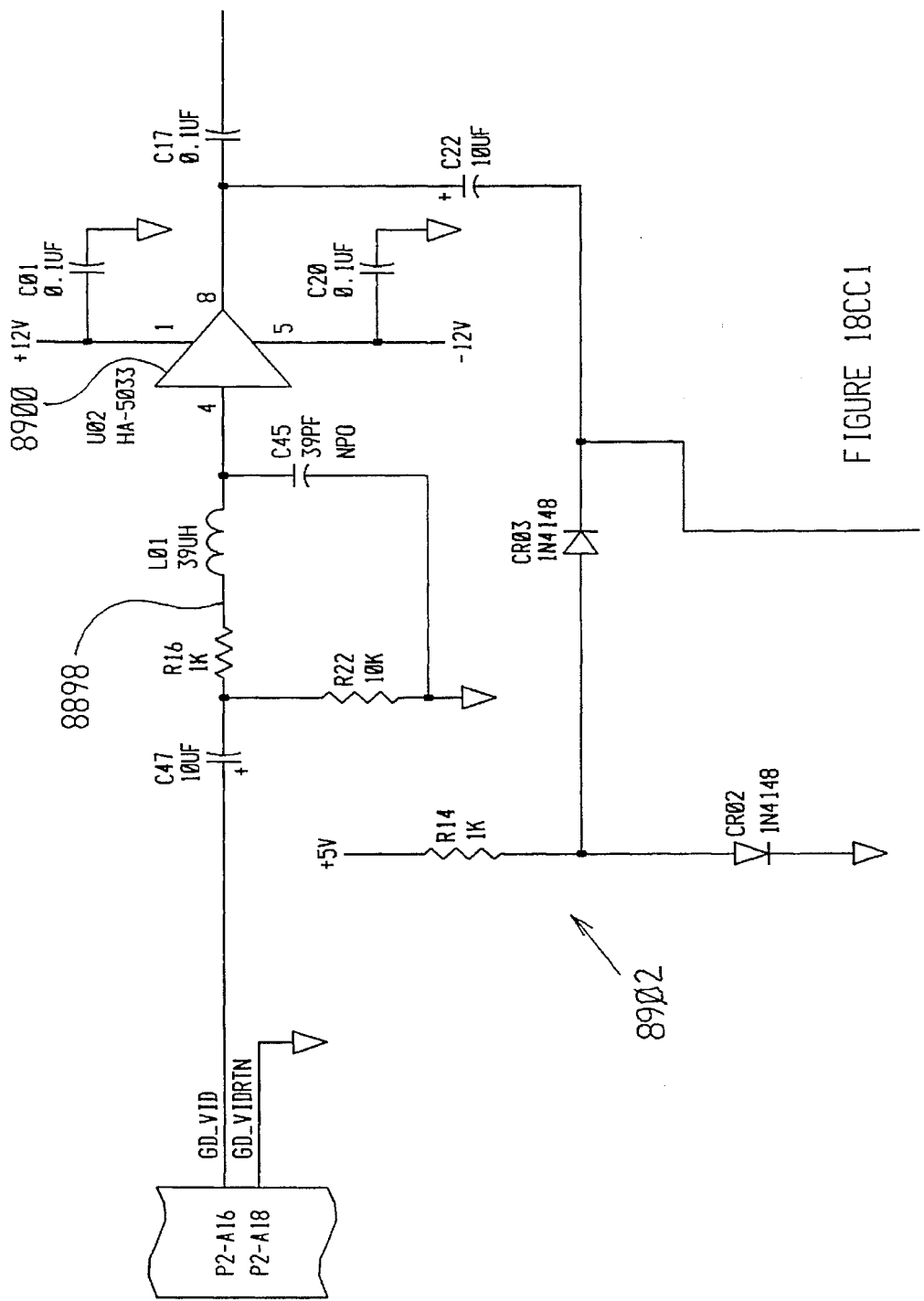

△ FILTER_VIDIN

FIGURE 18CC2

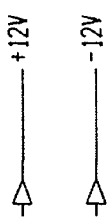
FIGURE 18CC3

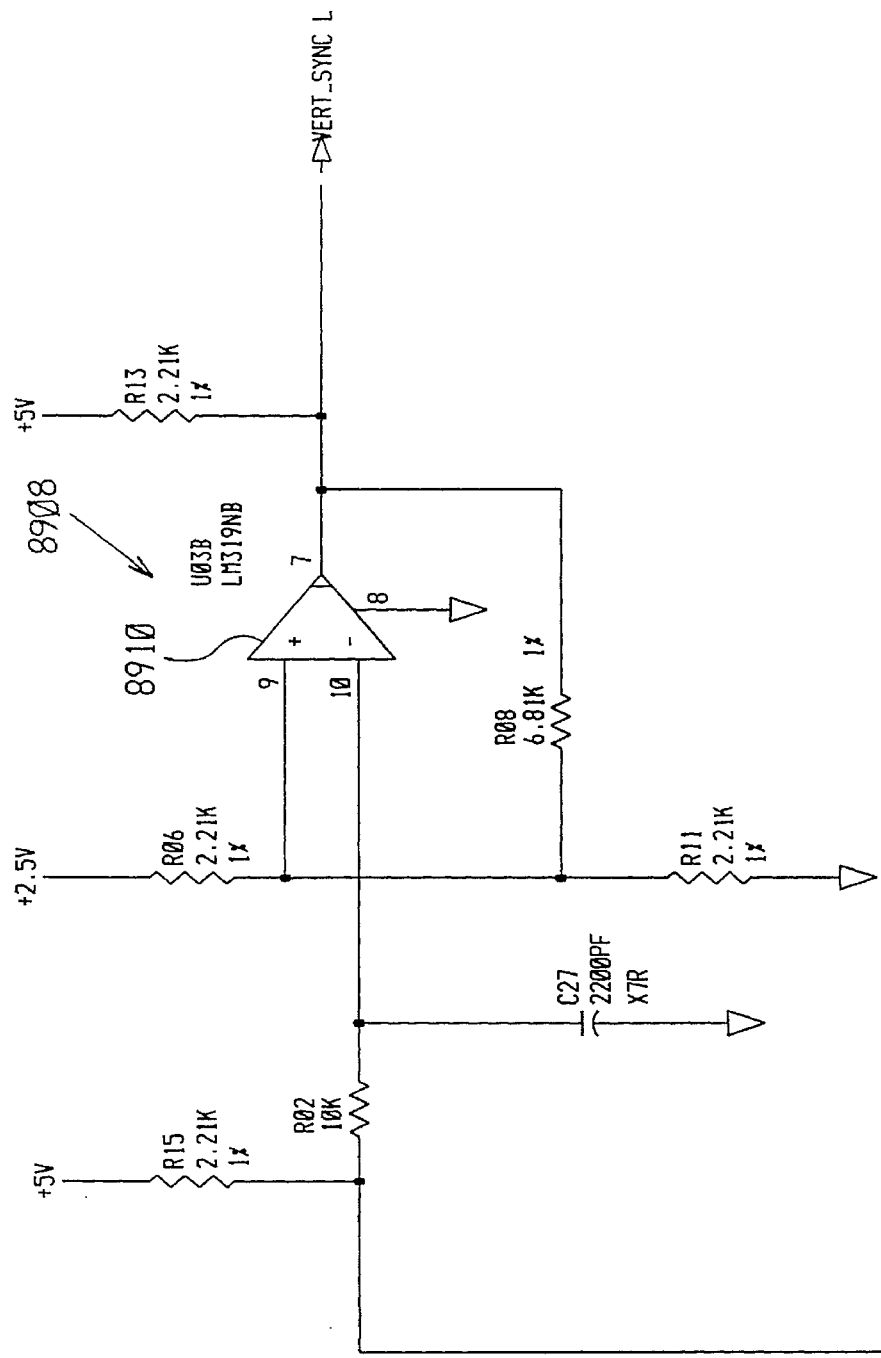
FIGURE 18CC4

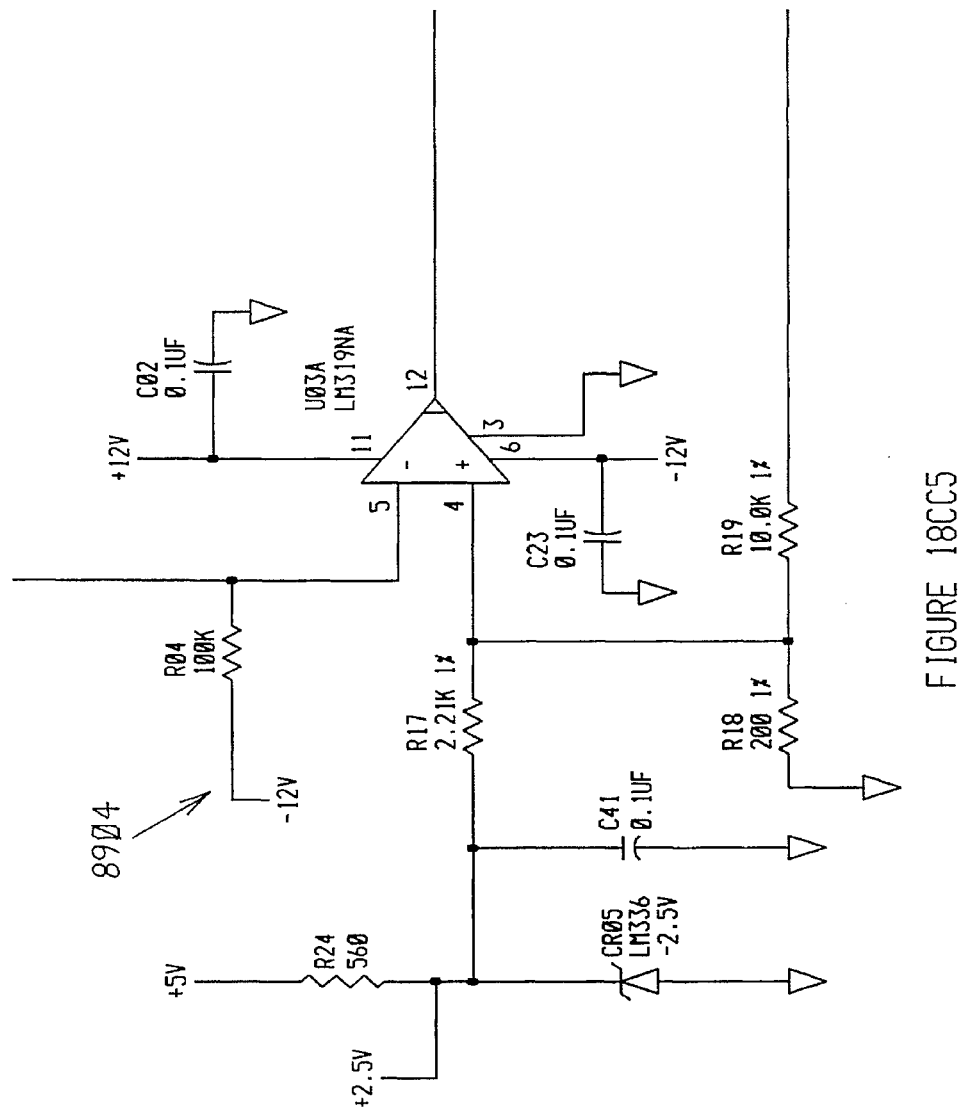

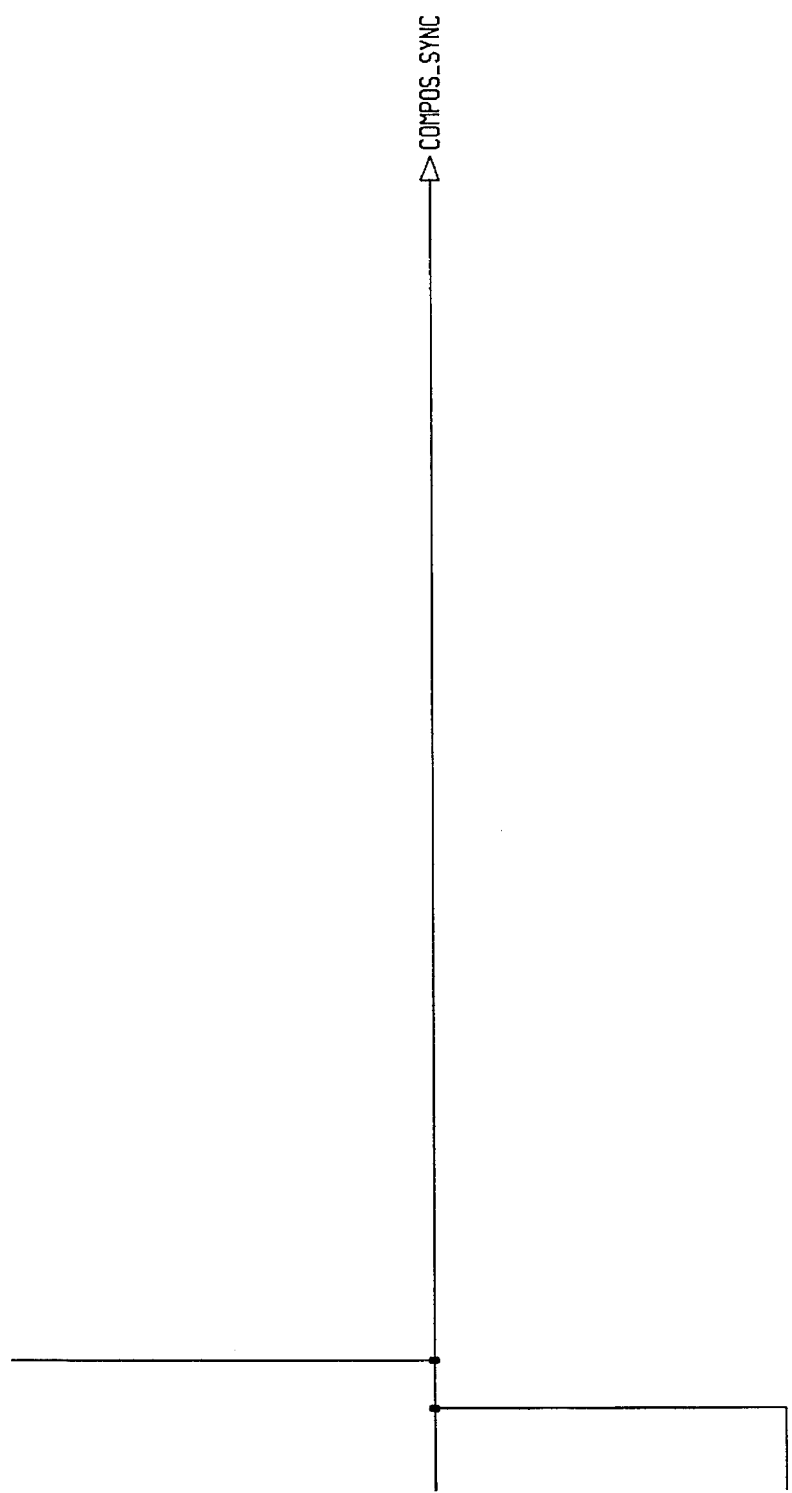
FIGURE 18CC6

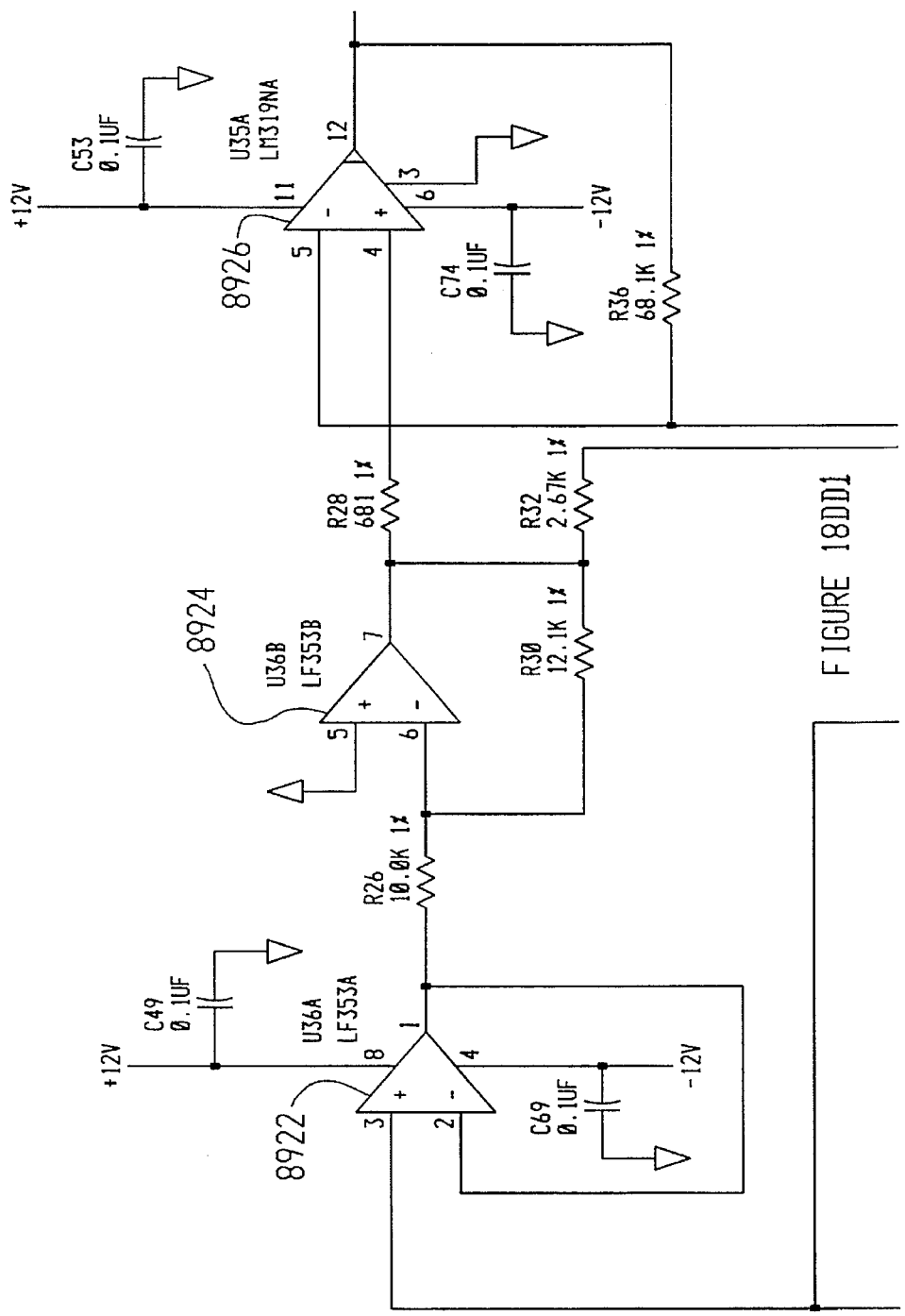
FIGURE 18DD1

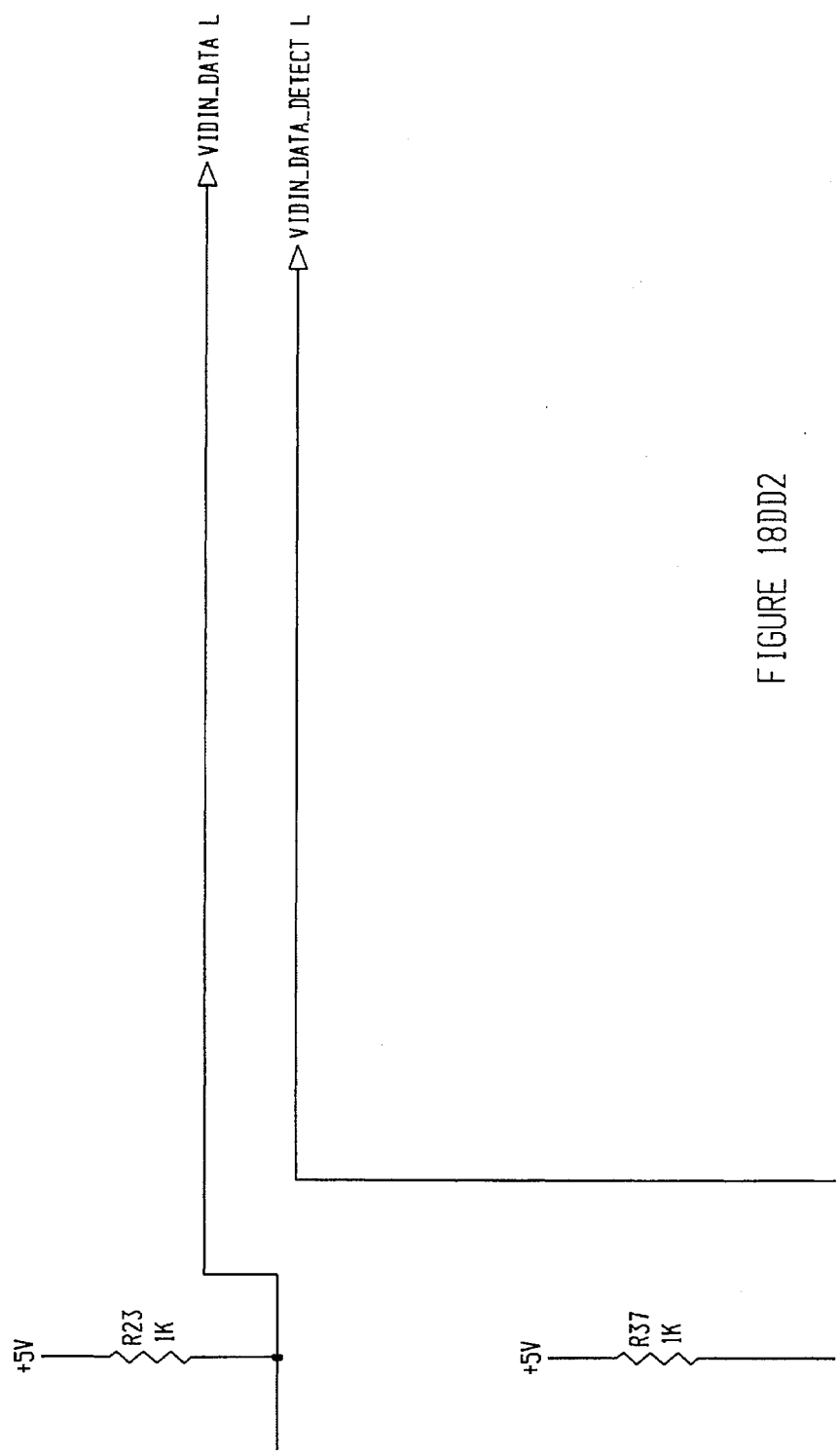
FIGURE 18DD2

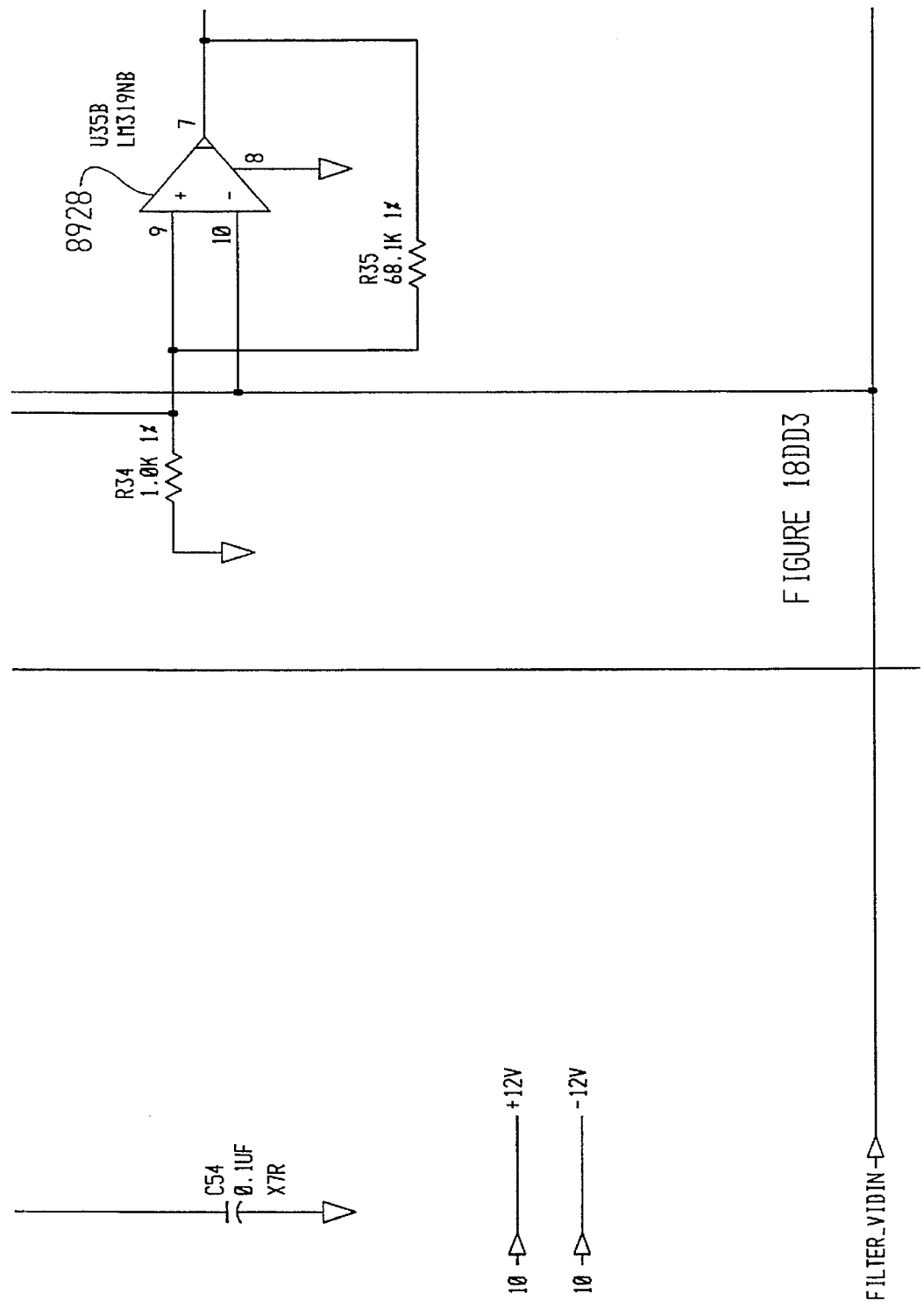
FIGURE 18DD3

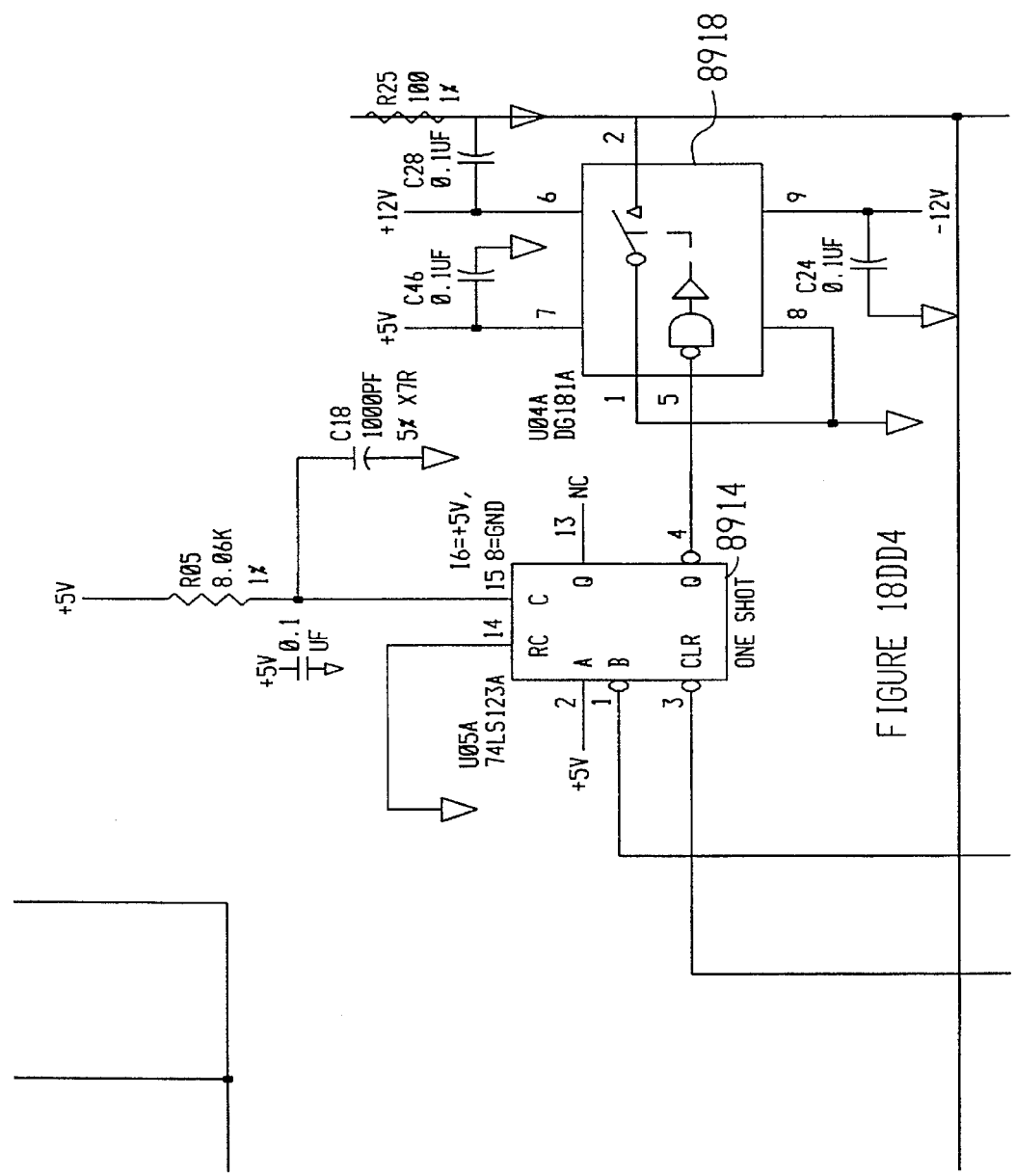
FIGURE 18DD4

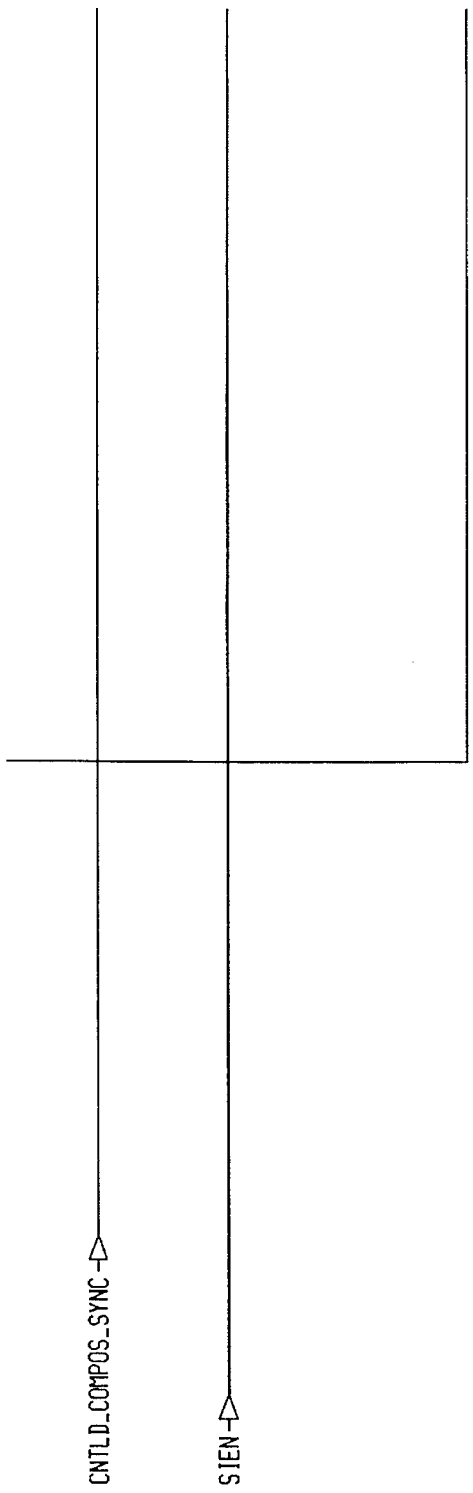
FIGURE 18DD5

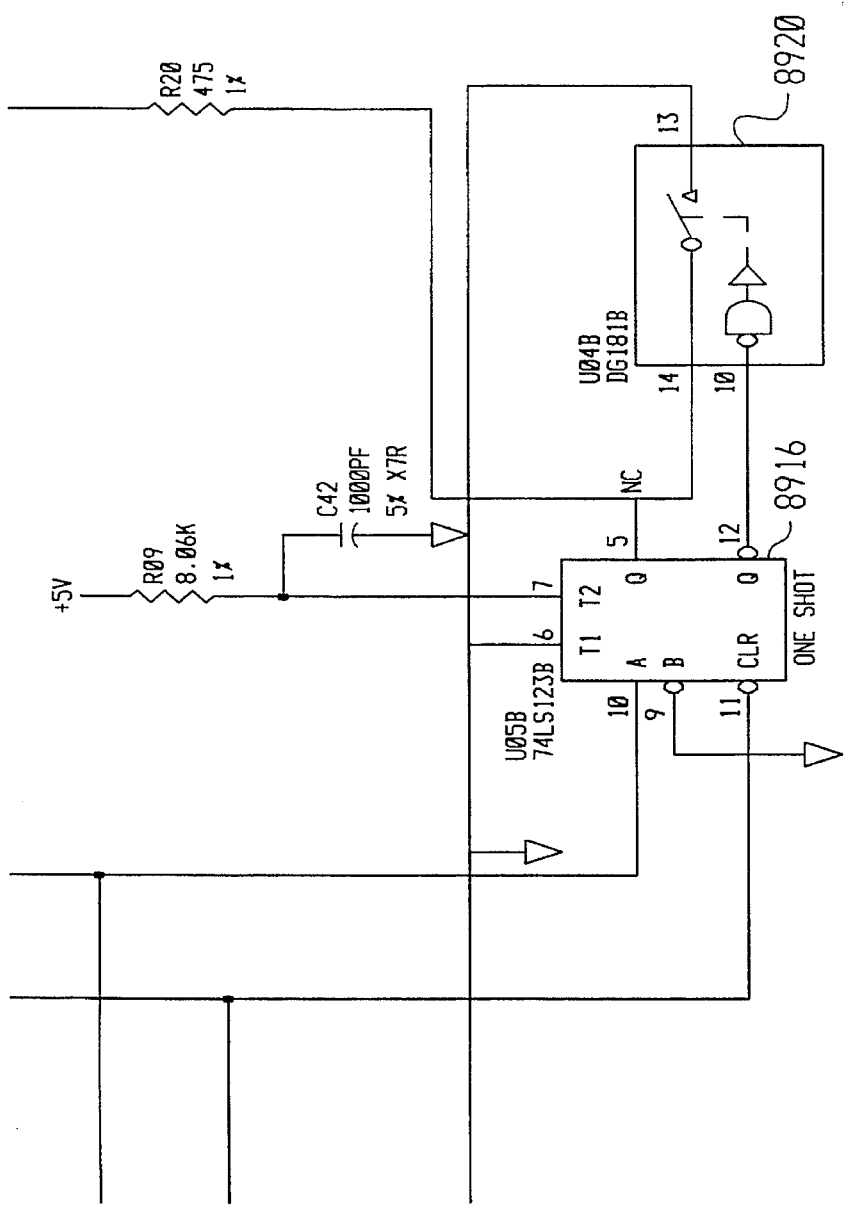
FIGURE 18DD6

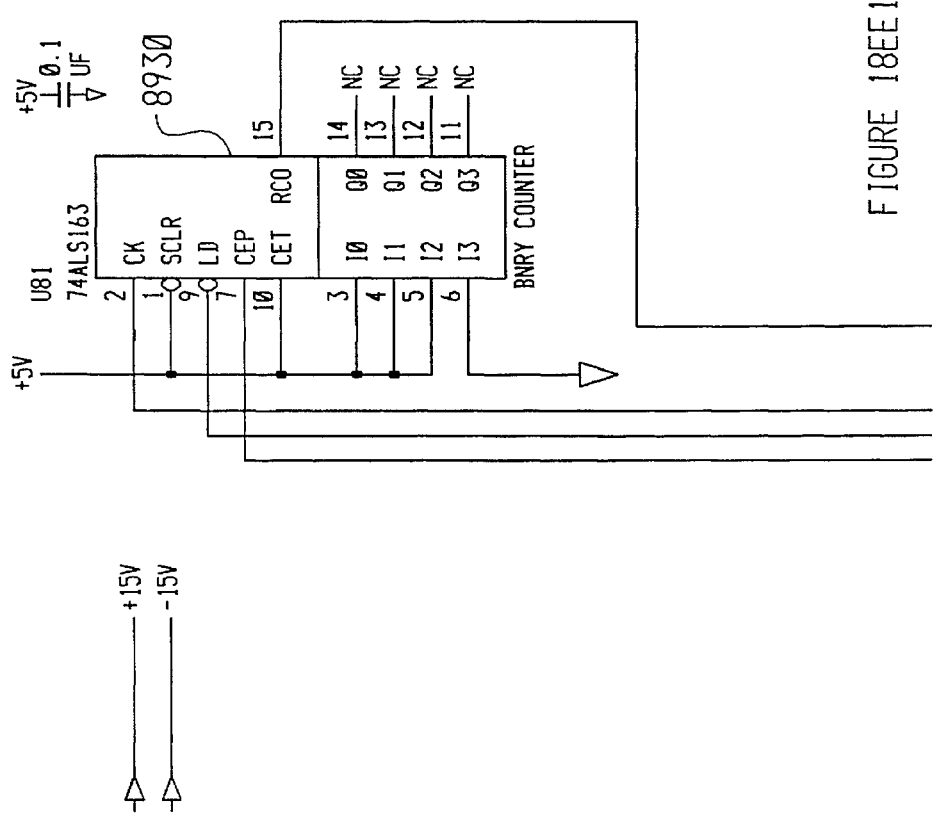
FIGURE 18EE1

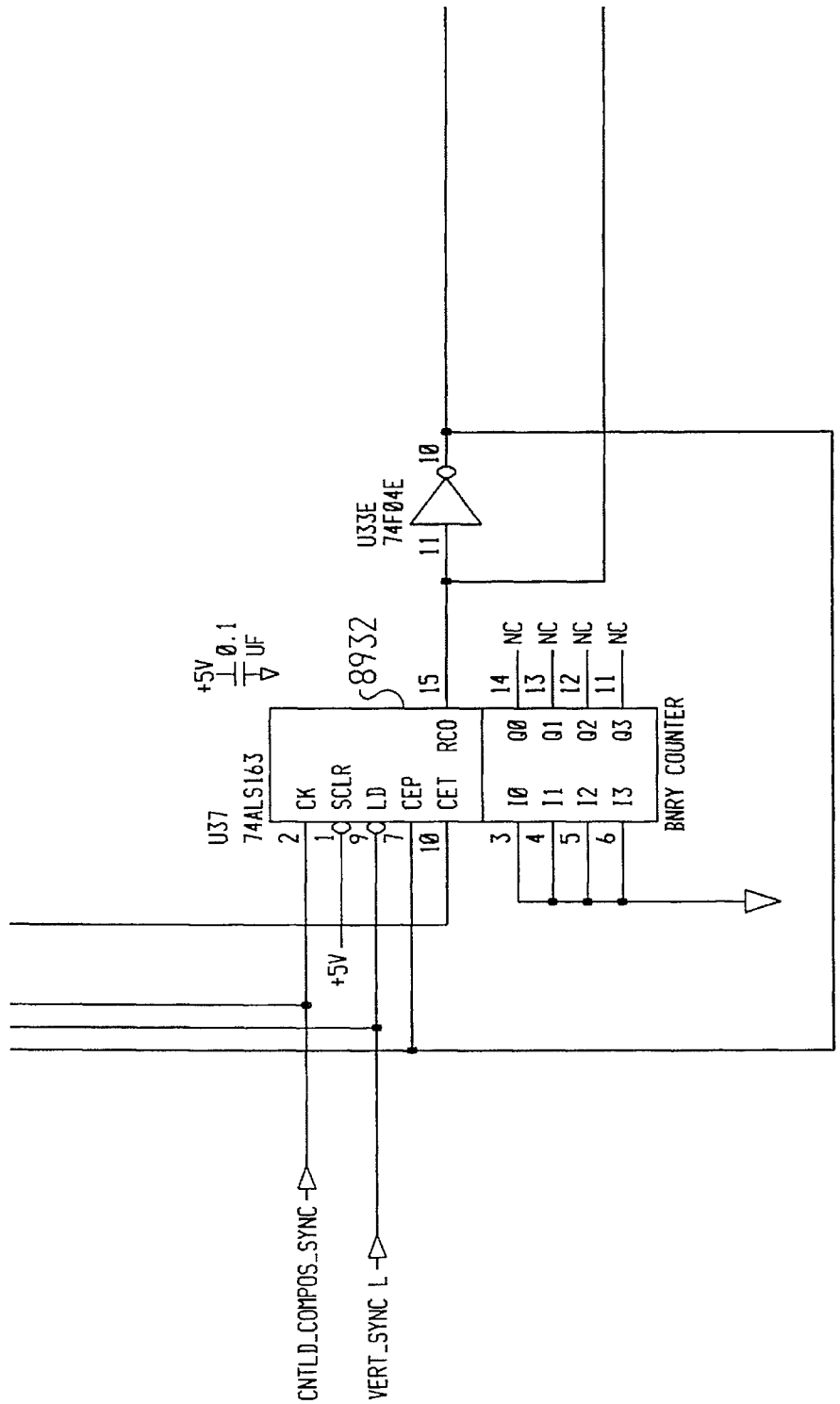
FIGURE 18EE2

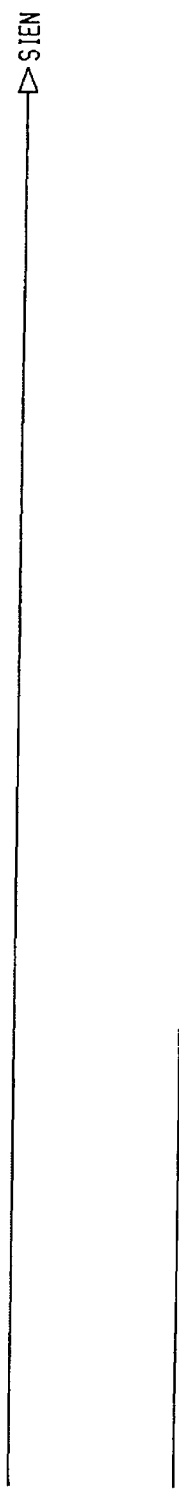
FIGURE 18EE3

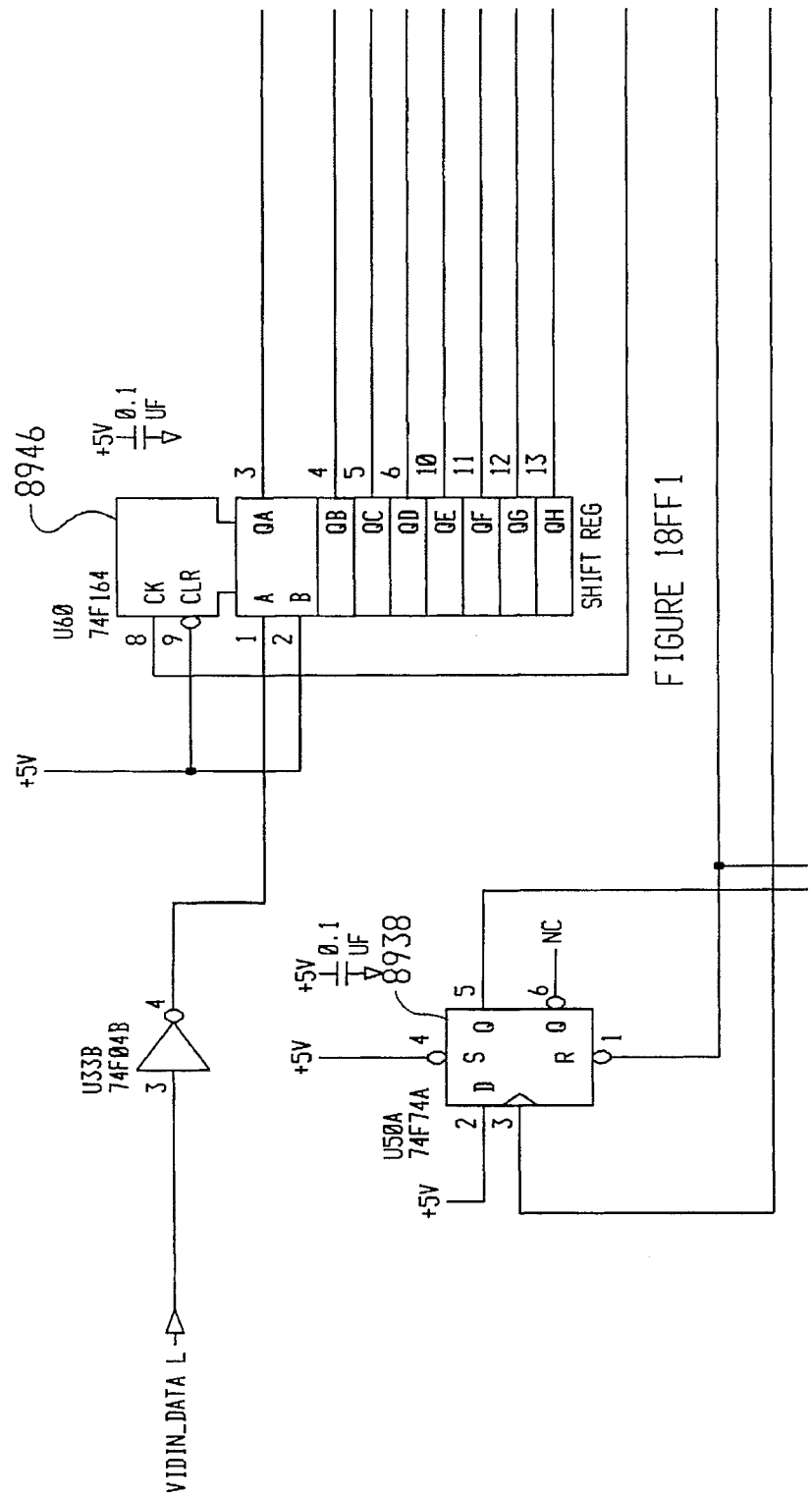
FIGURE 18FF1

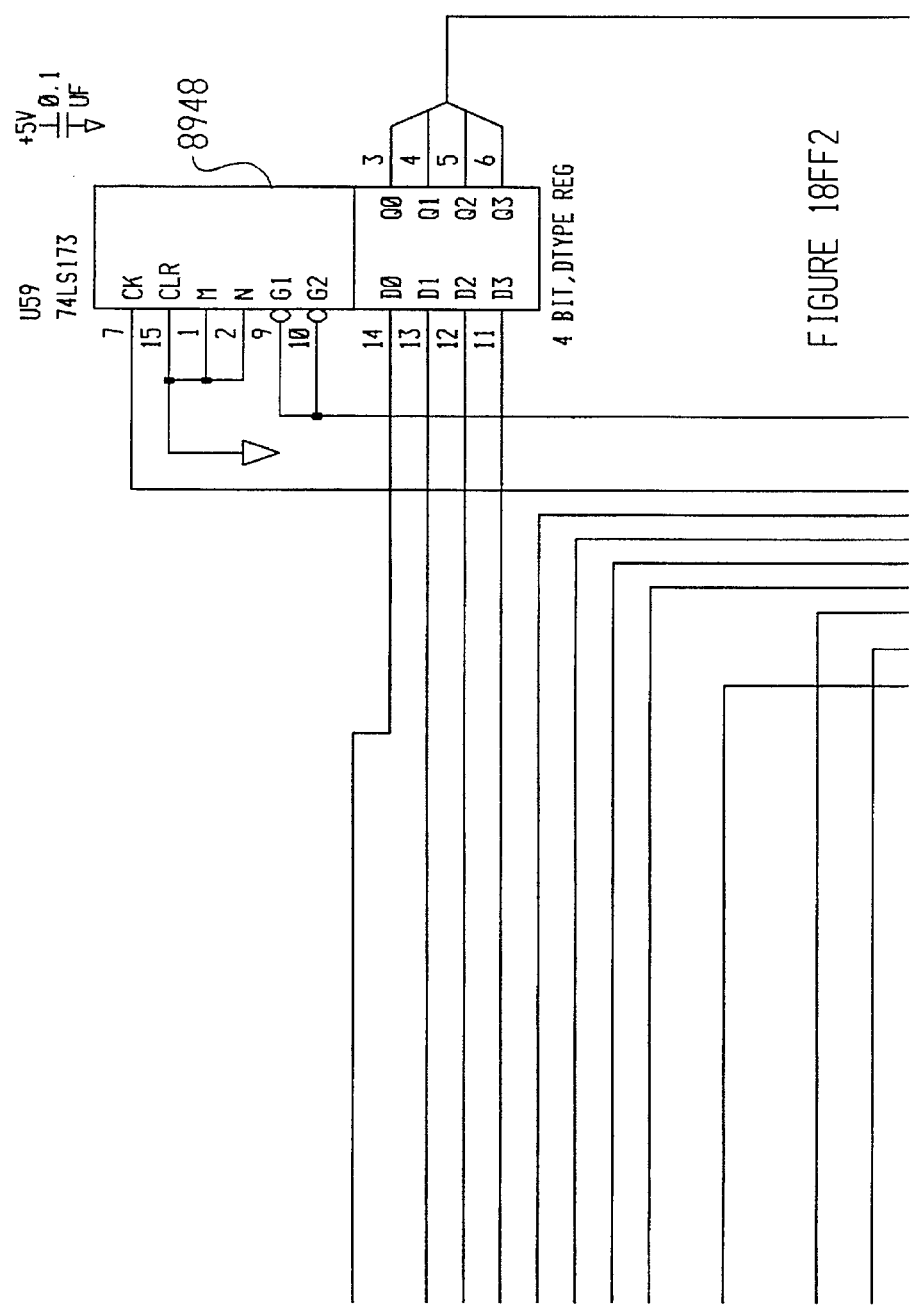
FIGURE 18FF2

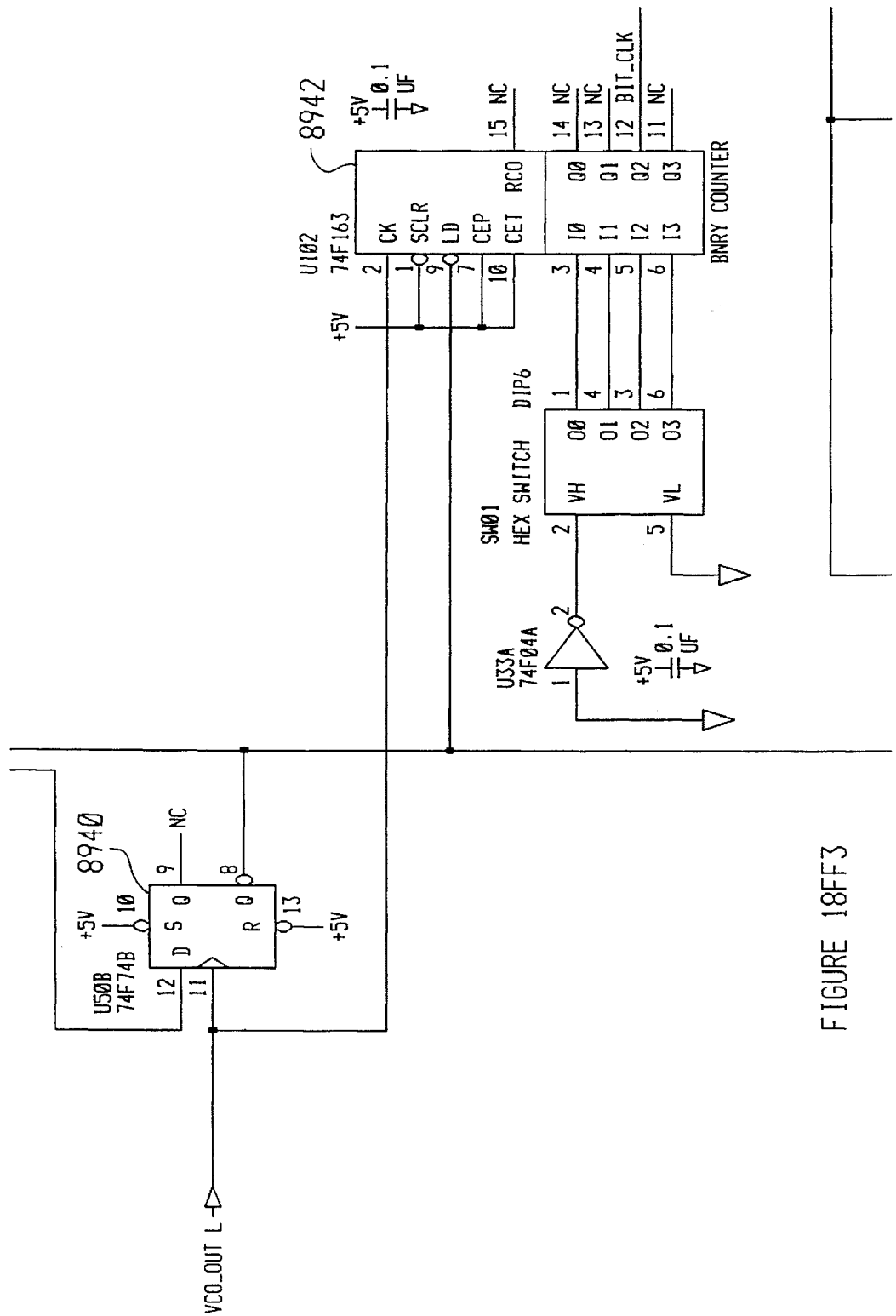
FIGURE 18FF3

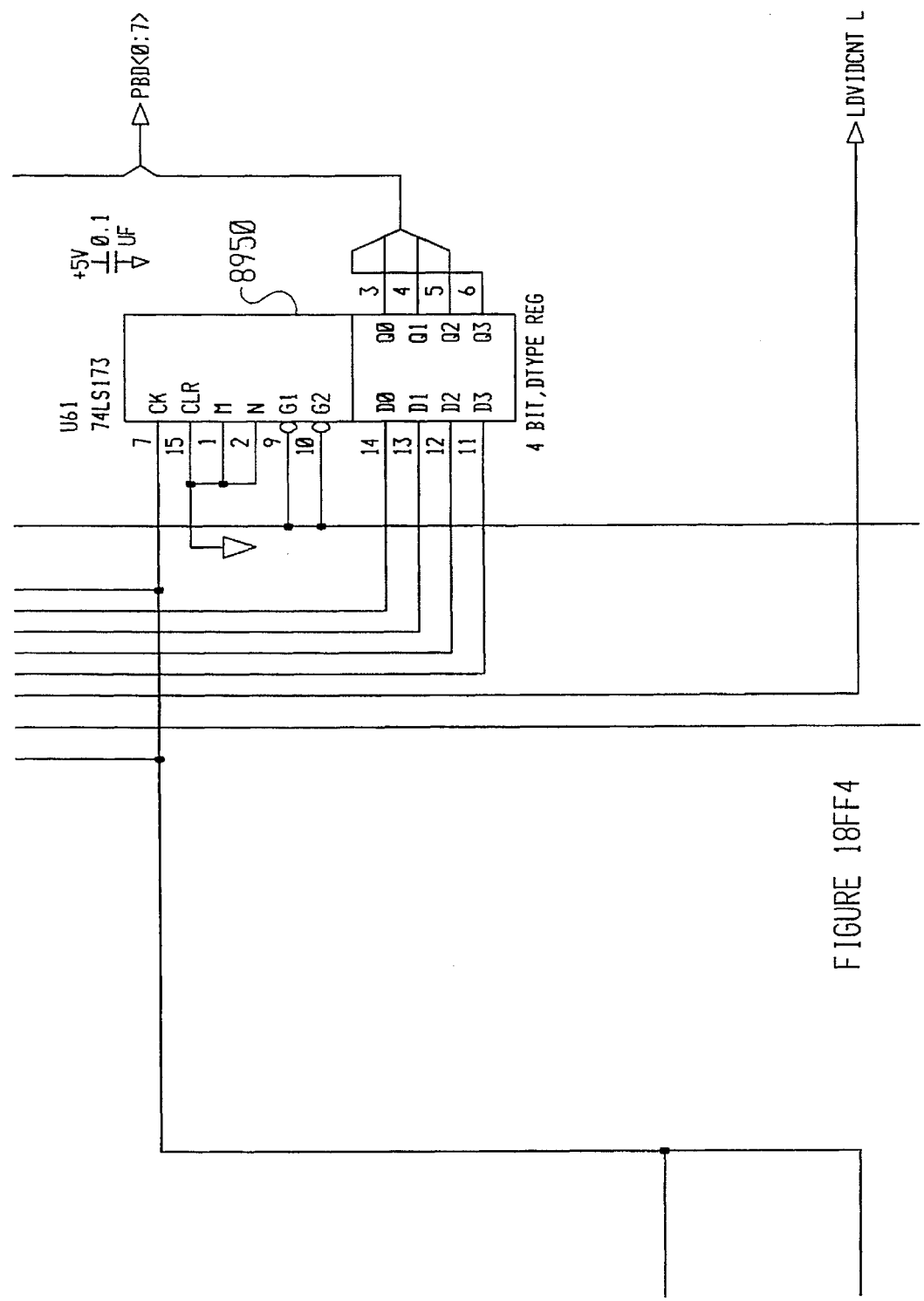
FIGURE 18FF4

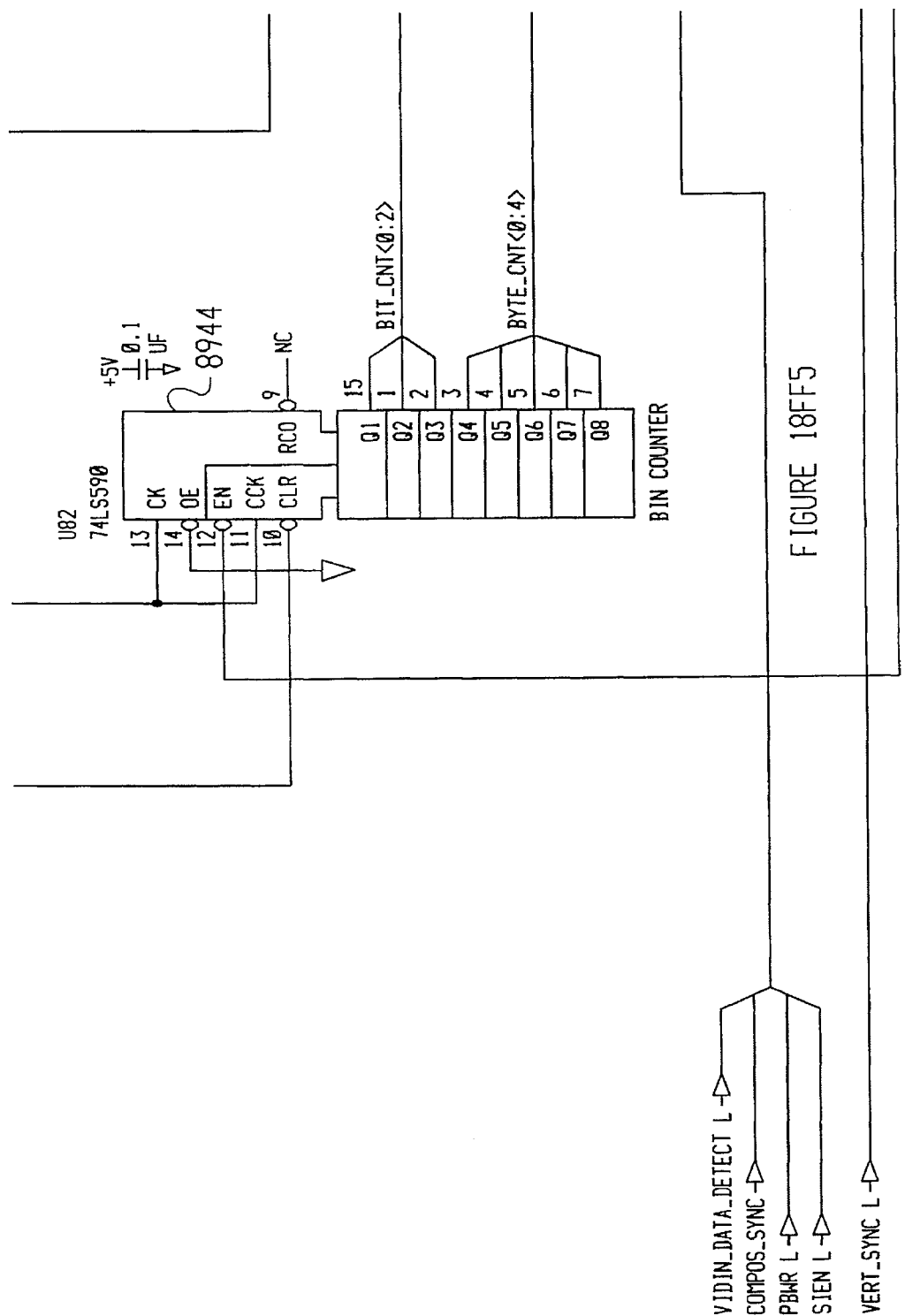
FIGURE 18FF5

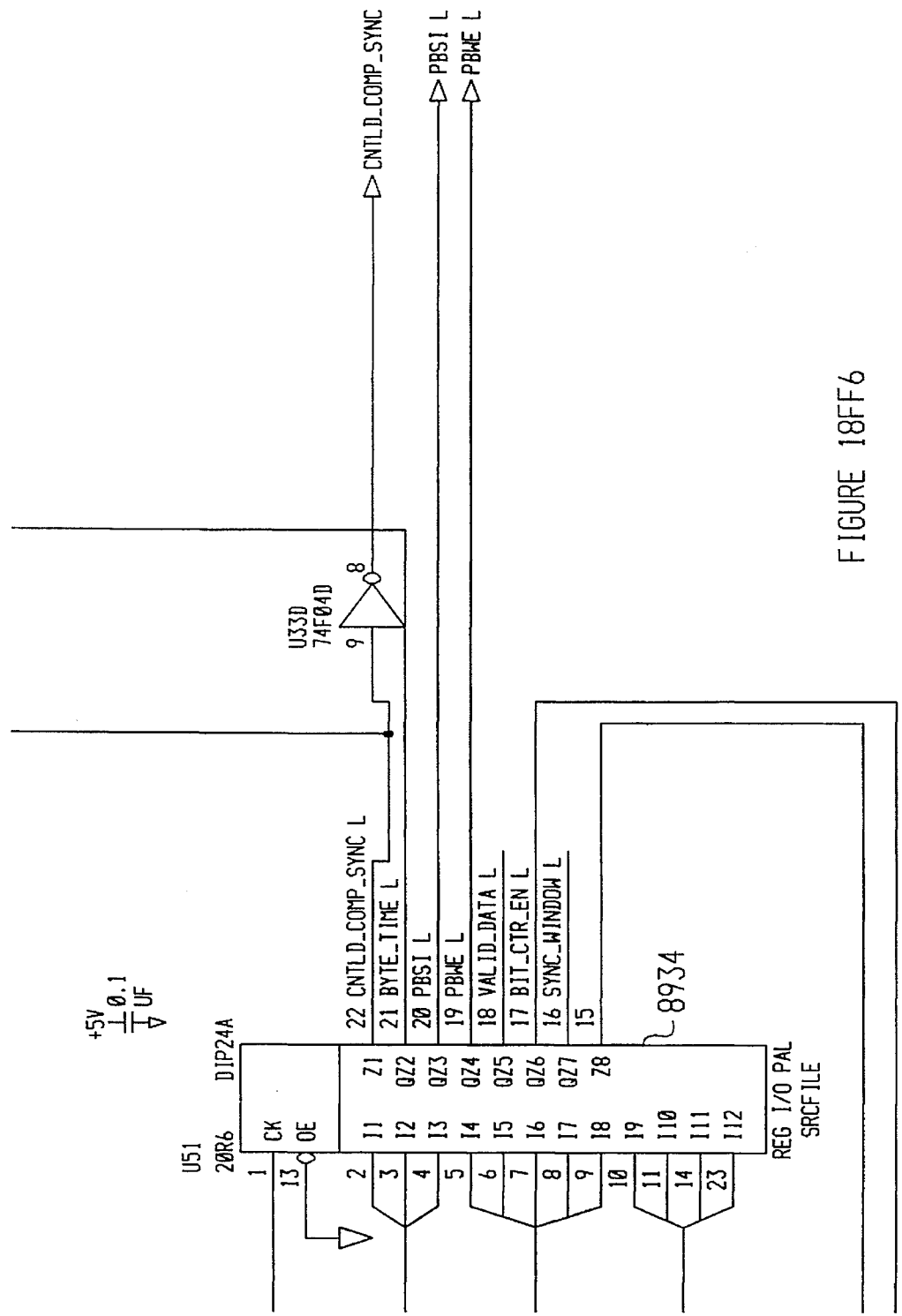
FIGURE 18FF6

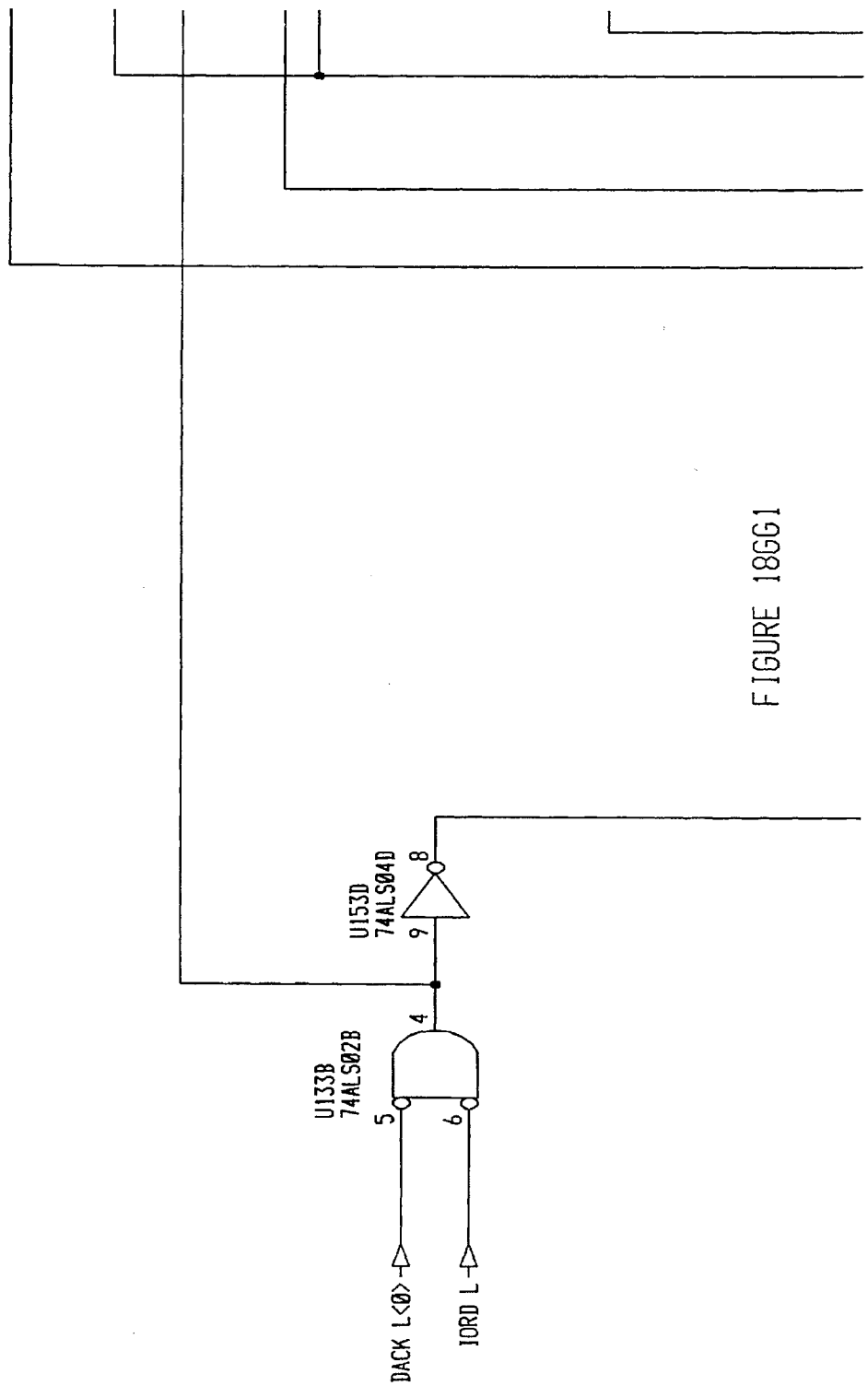

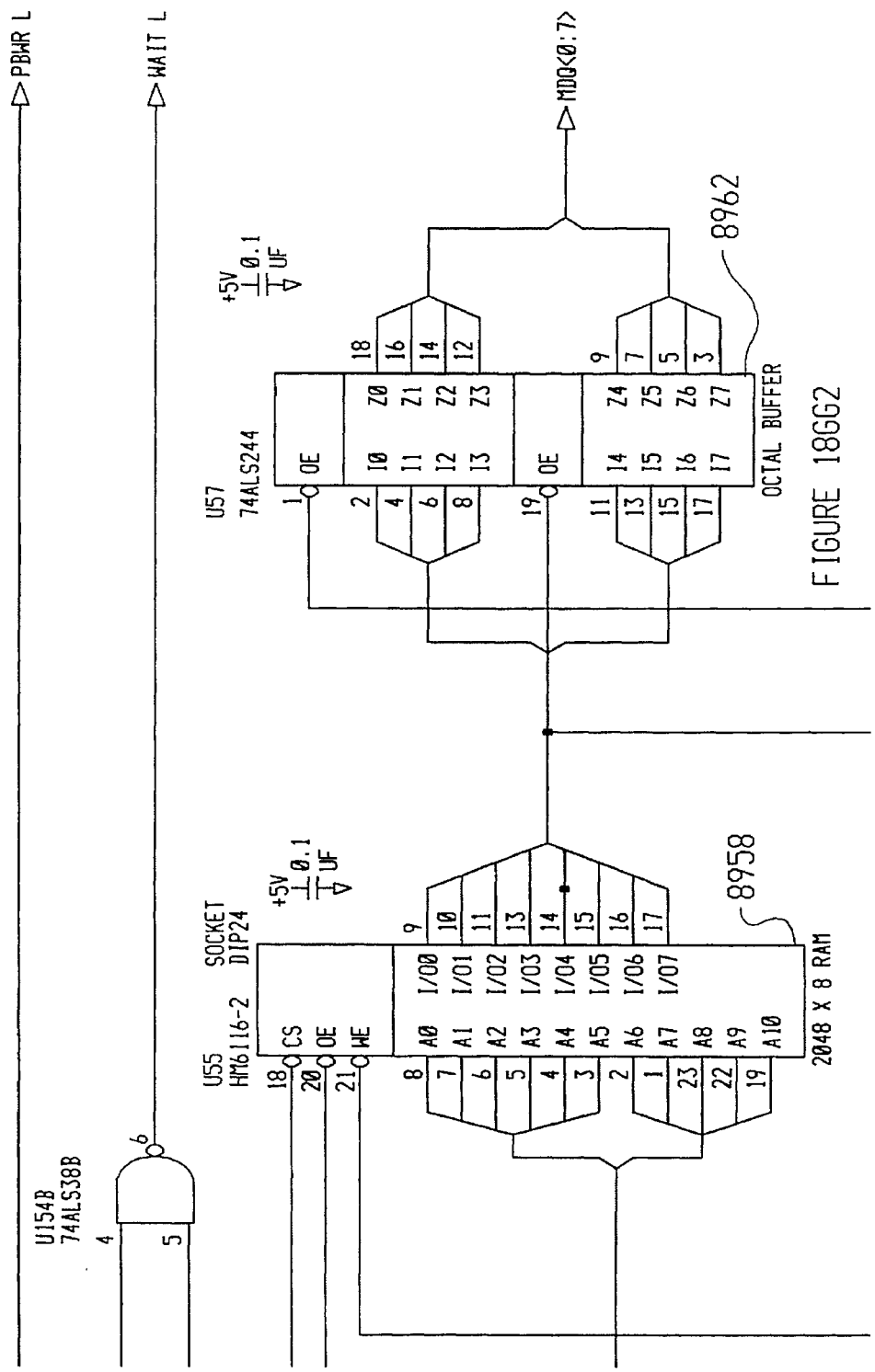
FIGURE 18GG2

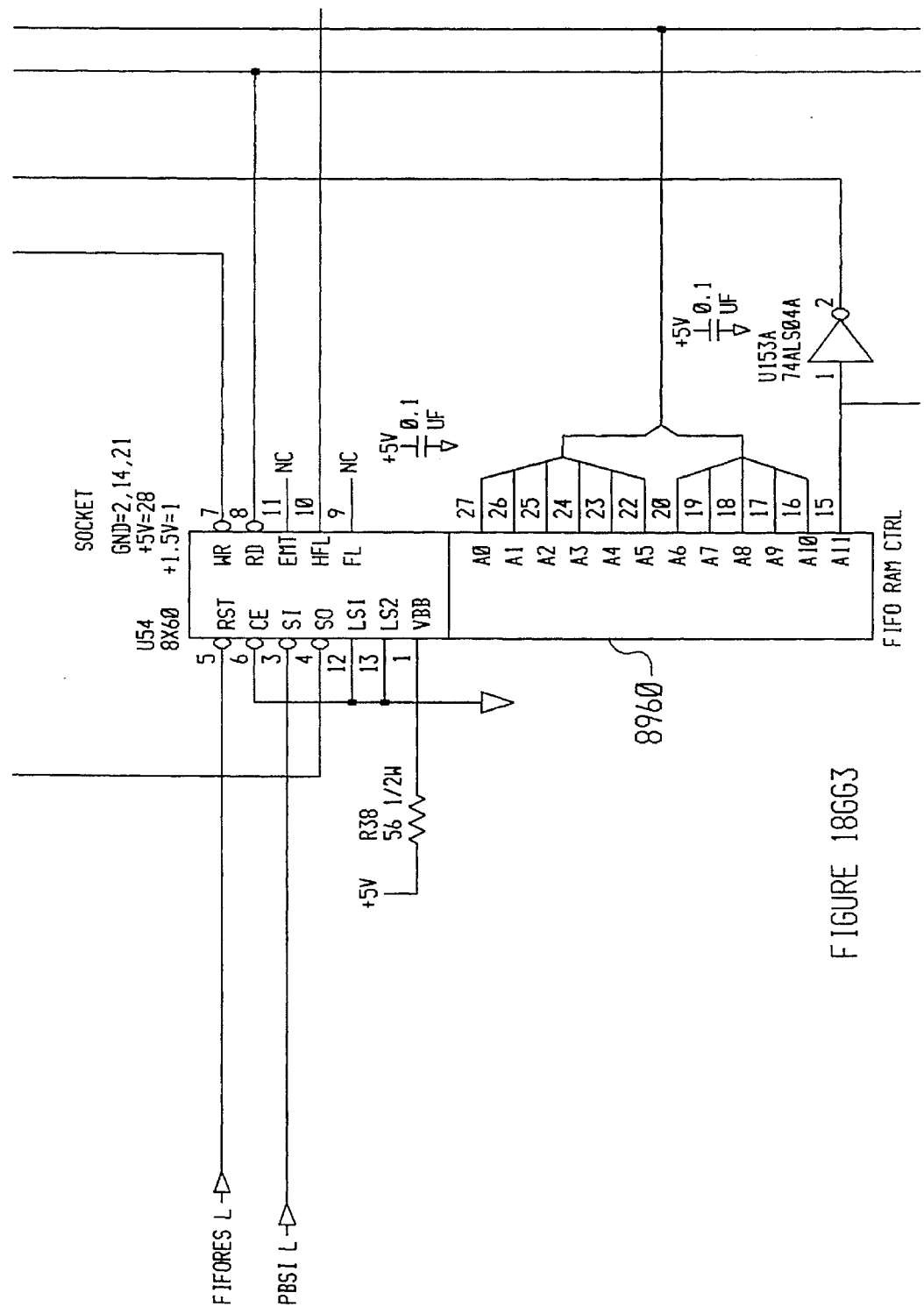
FIGURE 18663

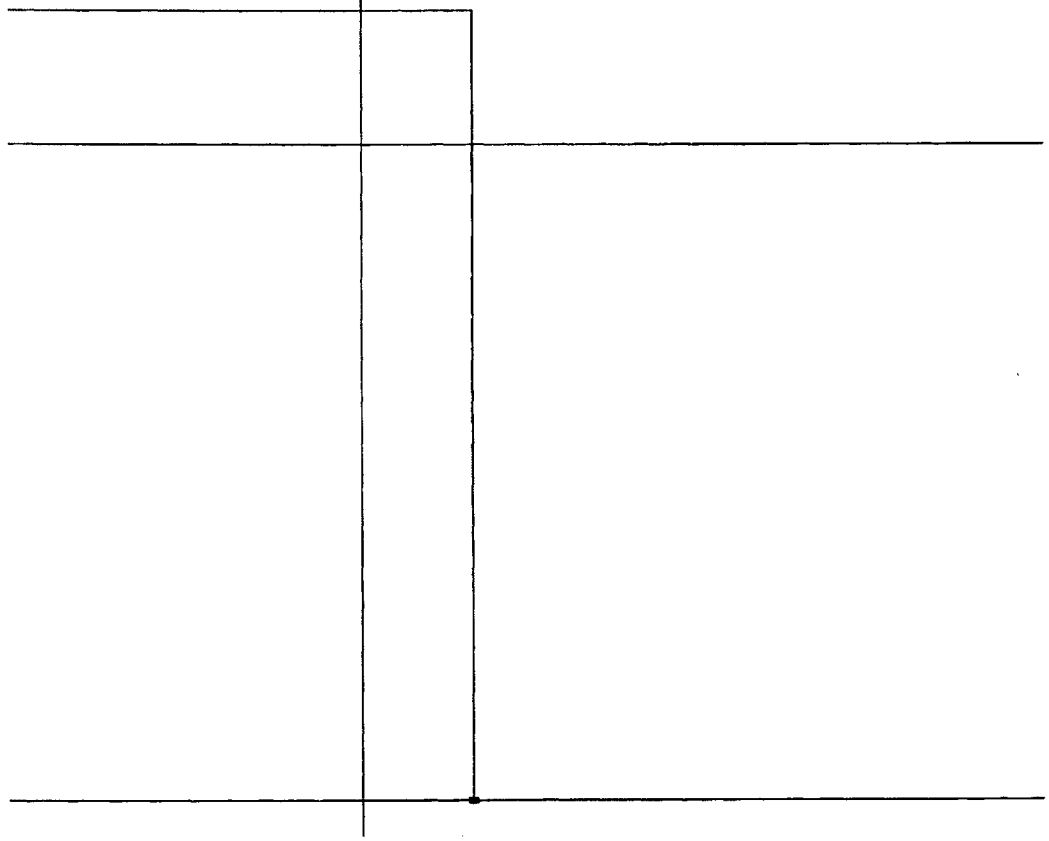
FIGURE 18G64

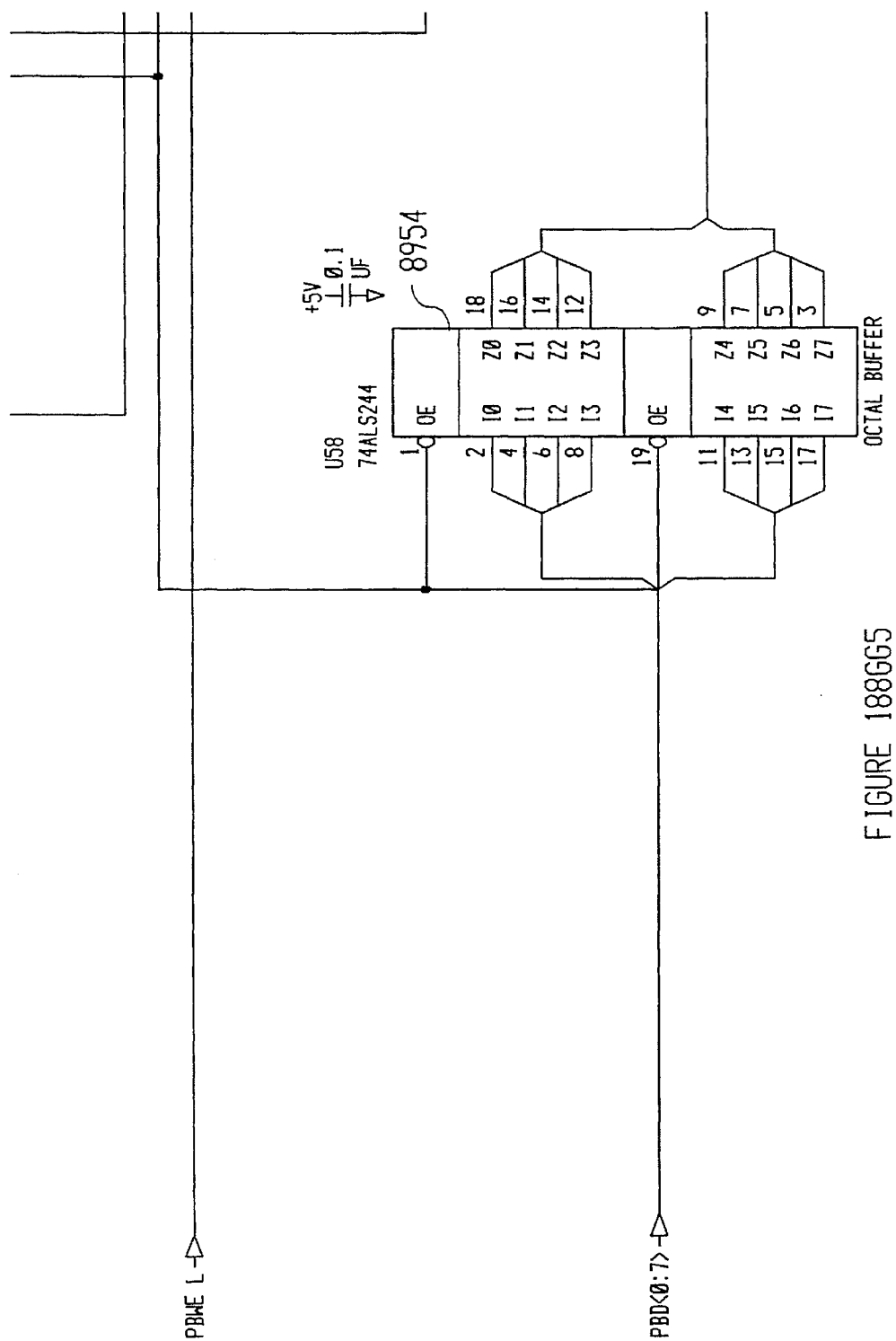
FIGURE 188GG5

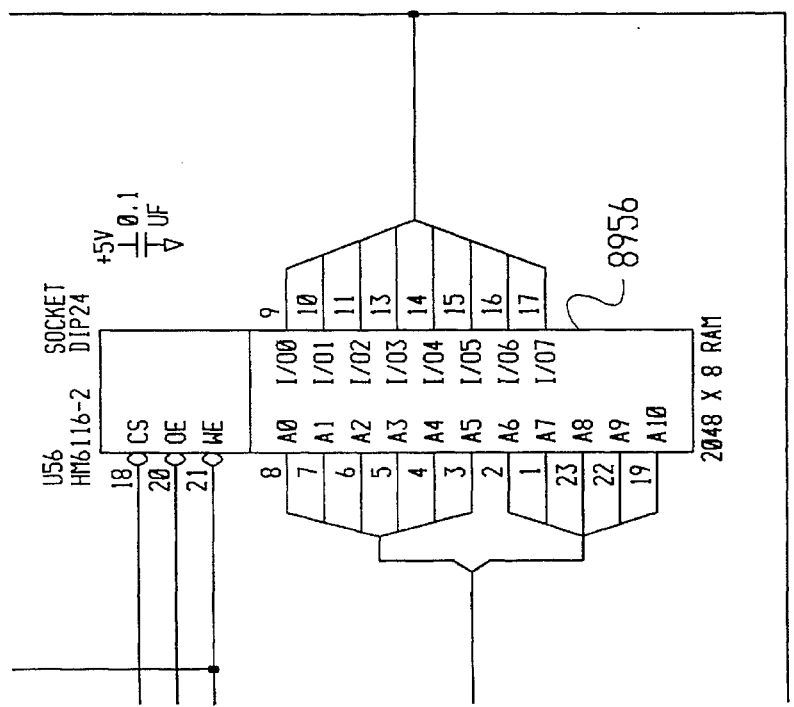
FIGURE 18GG6

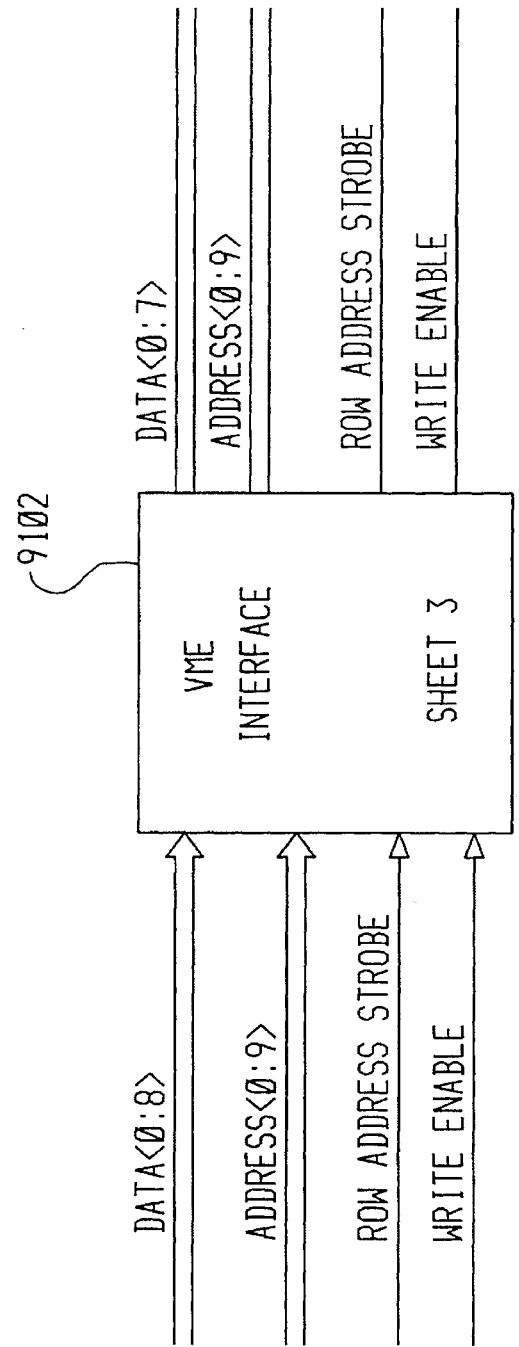

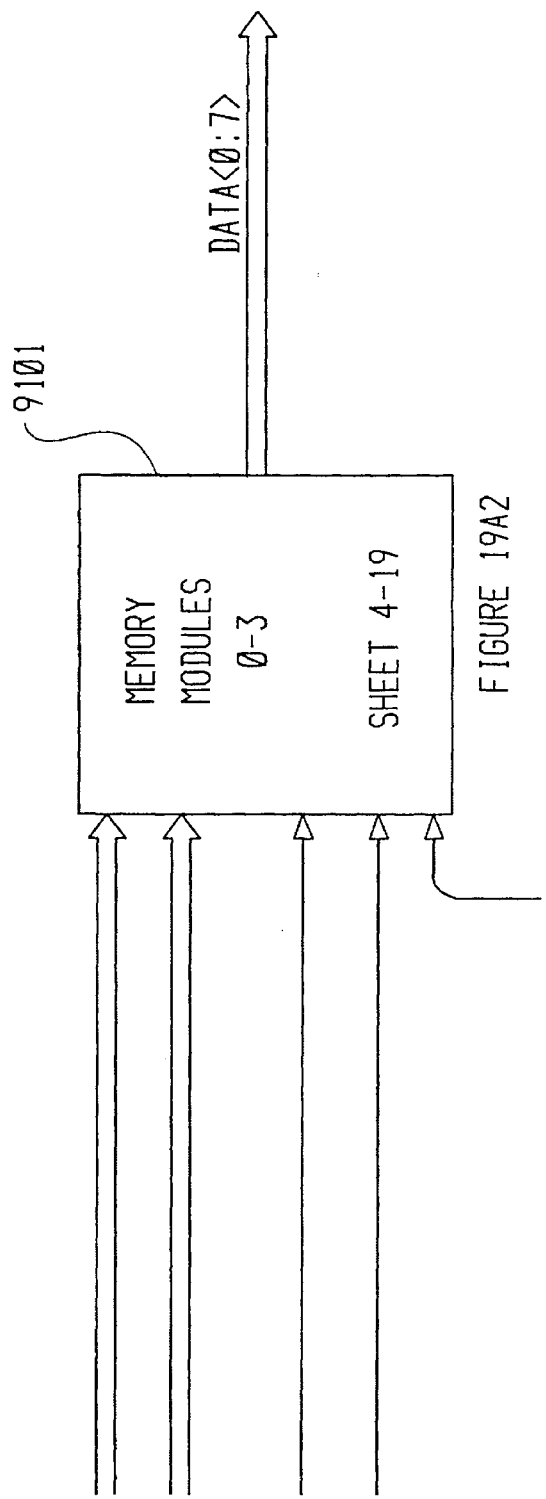

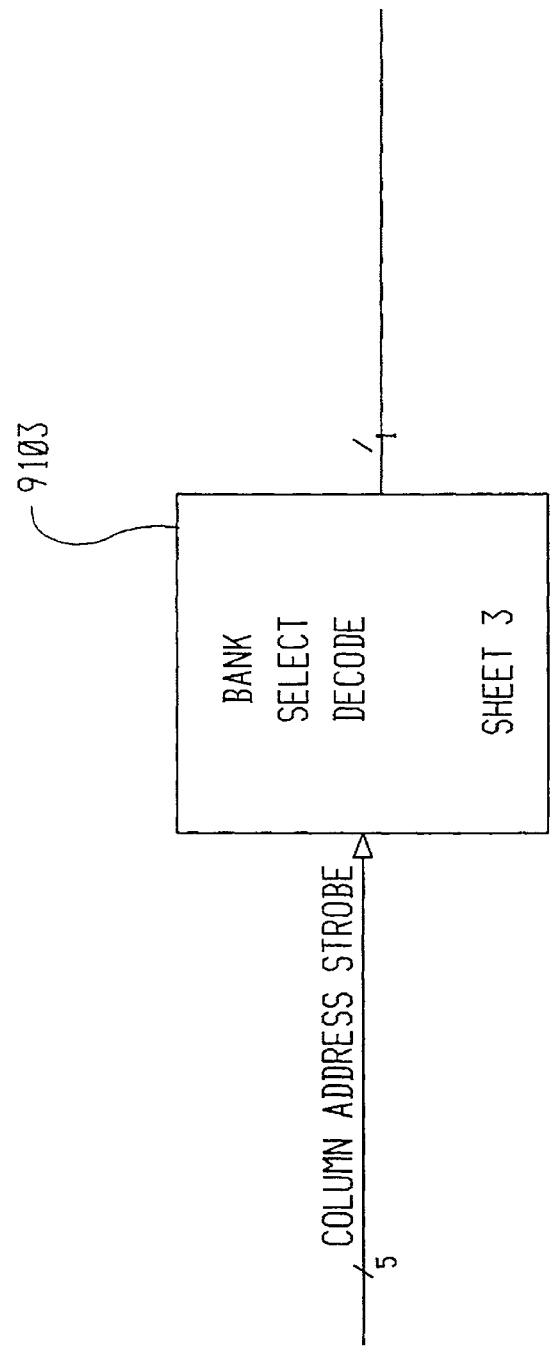
FIGURE 19A3

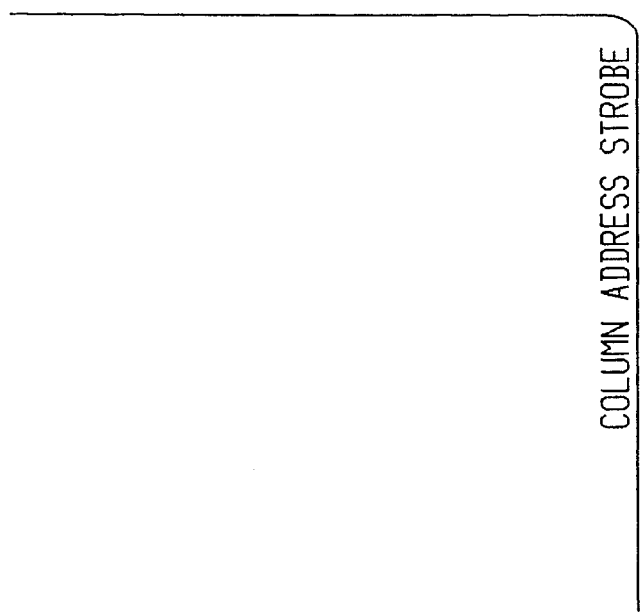

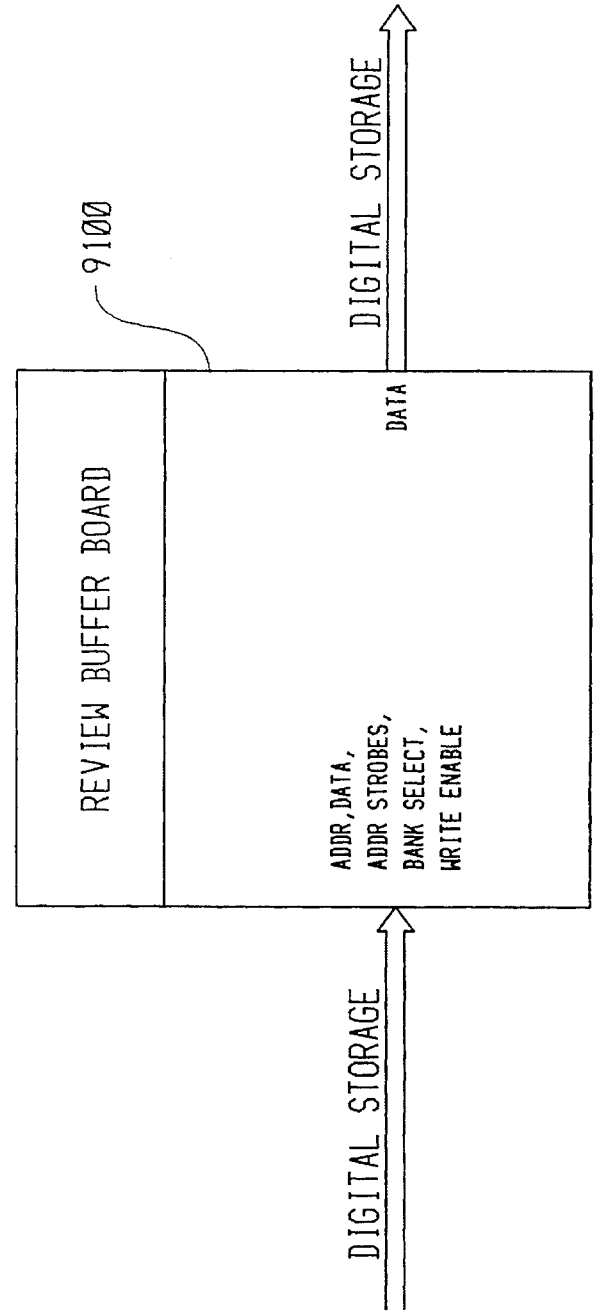

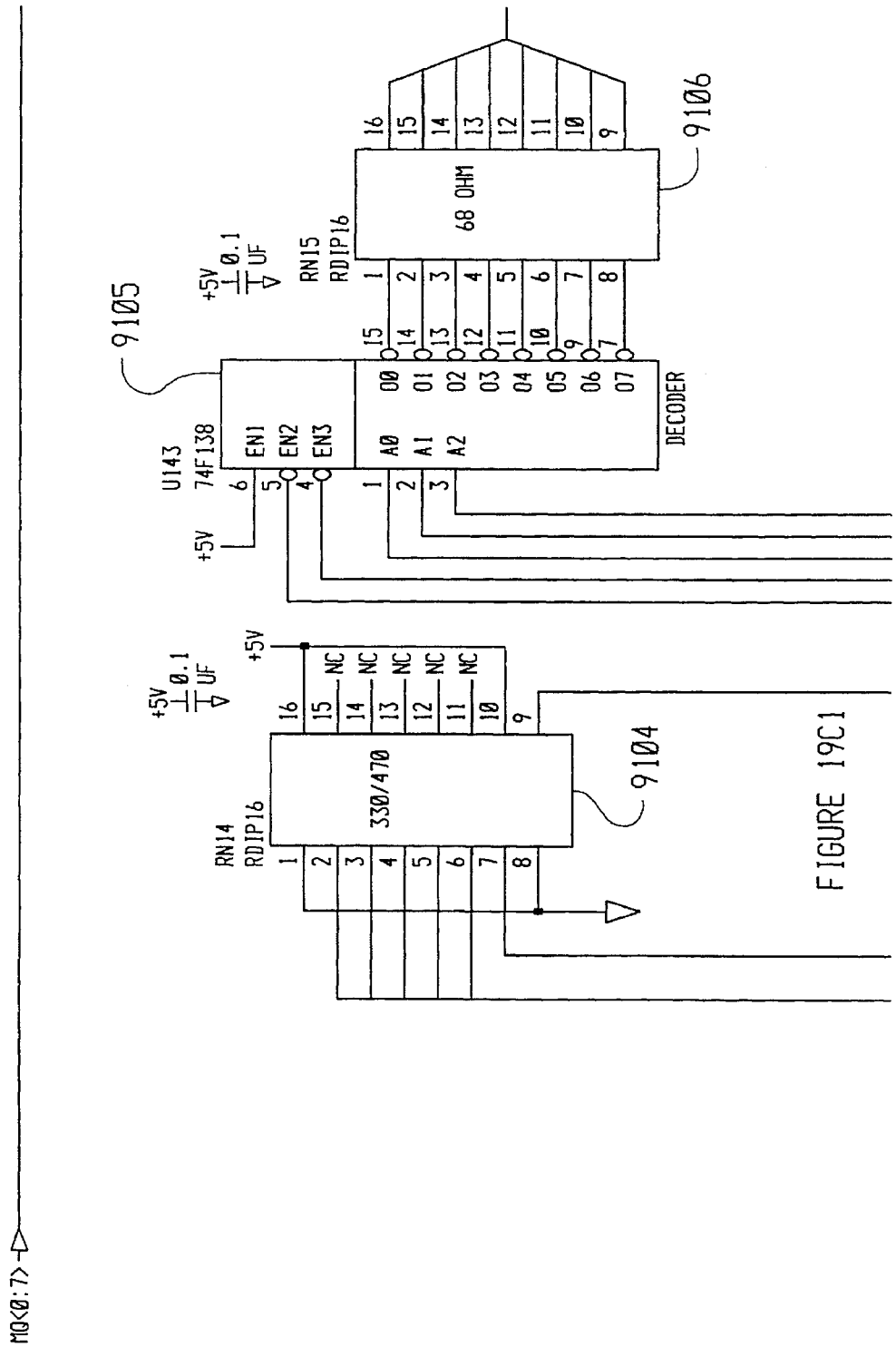
FIGURE 19C1

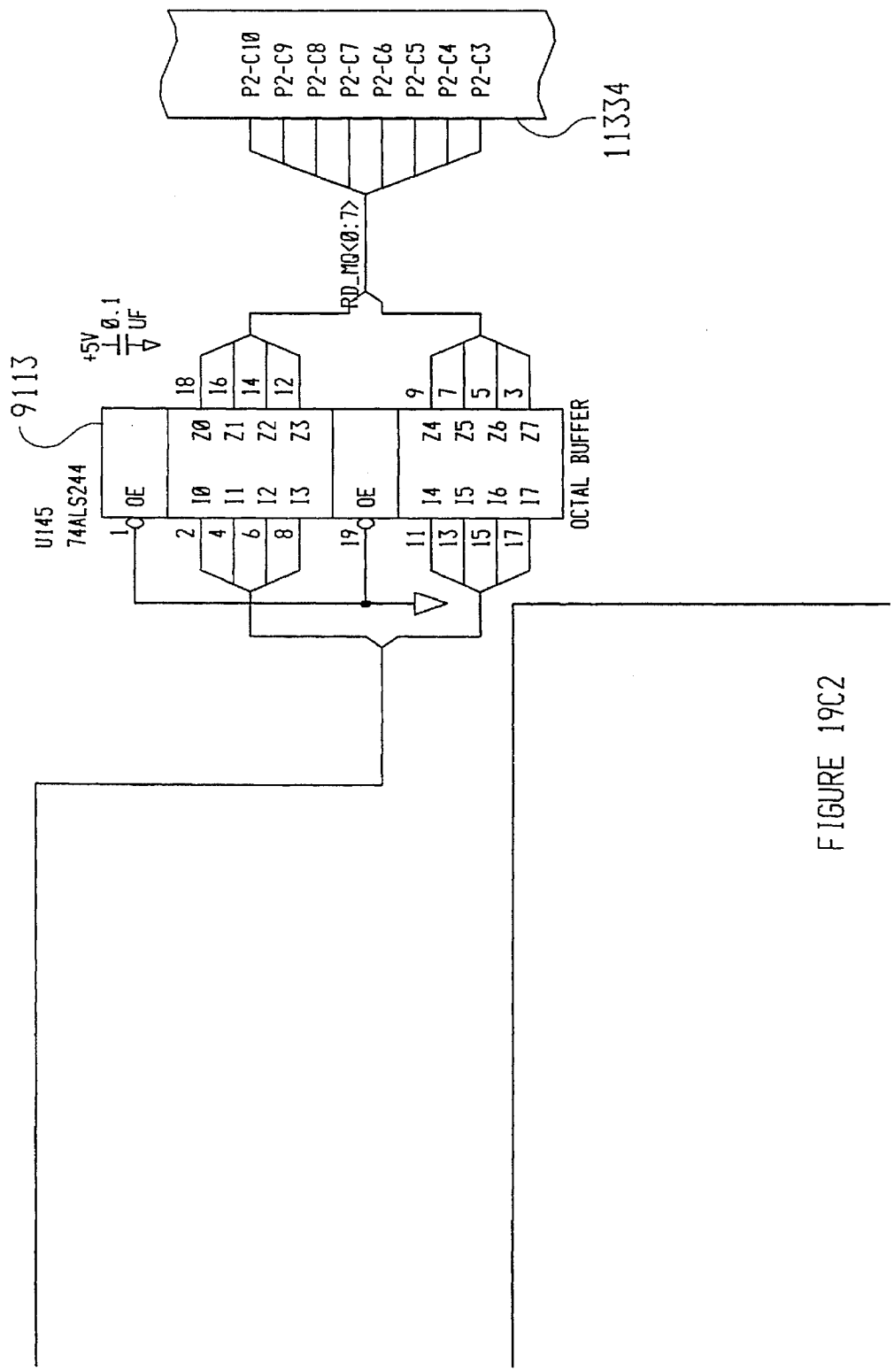
FIGURE 19C2

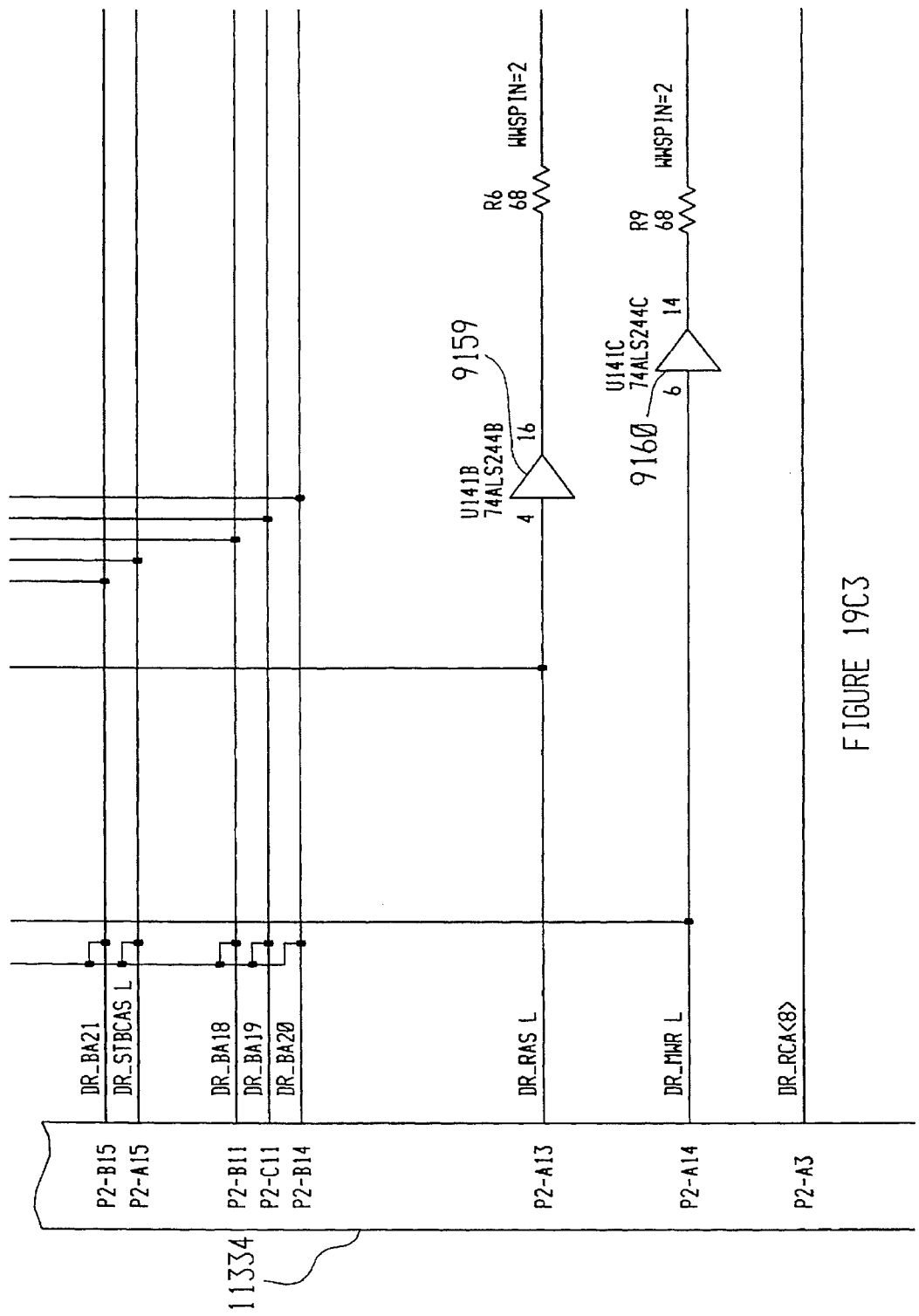
FIGURE 19C3

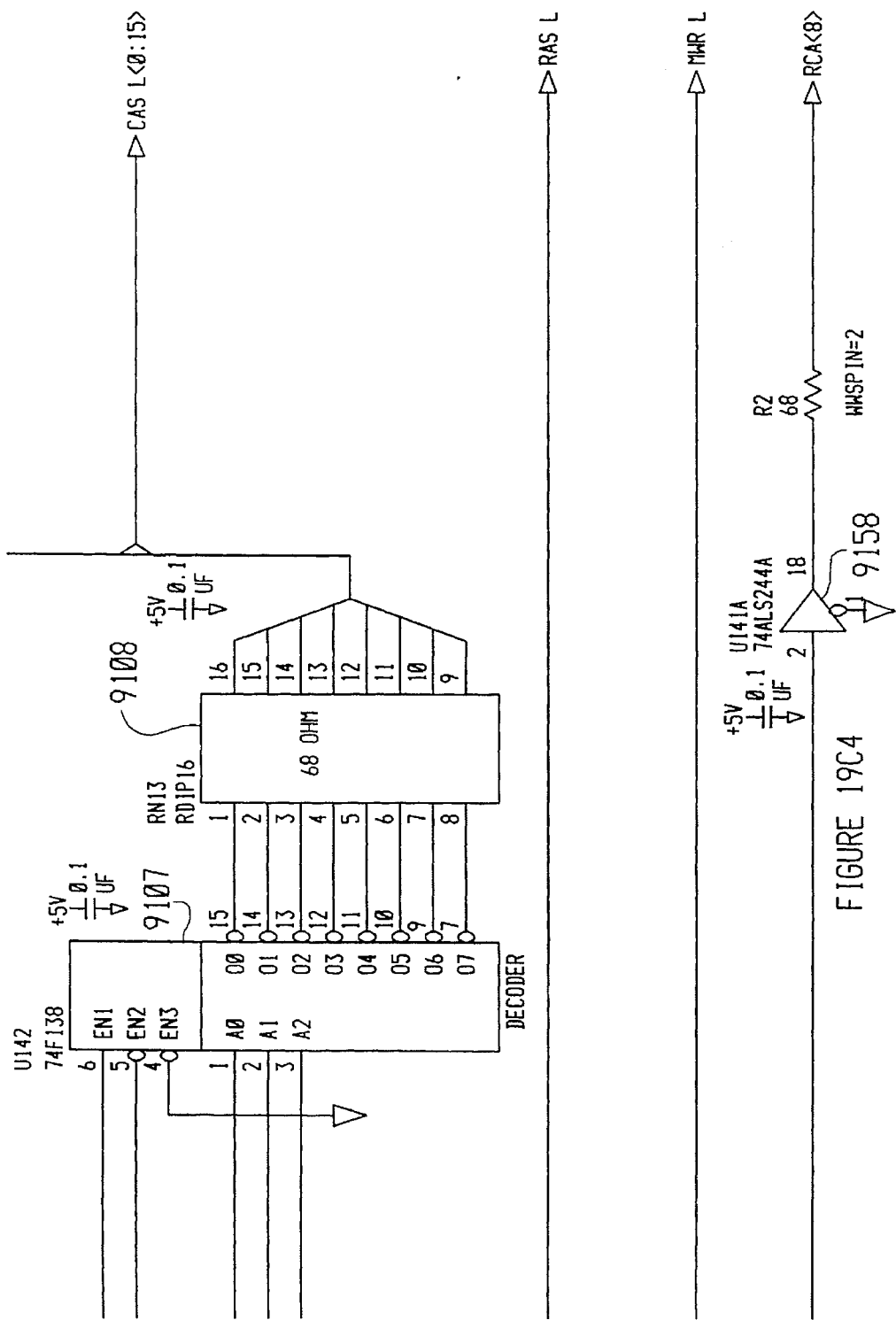
FIGURE 19C4

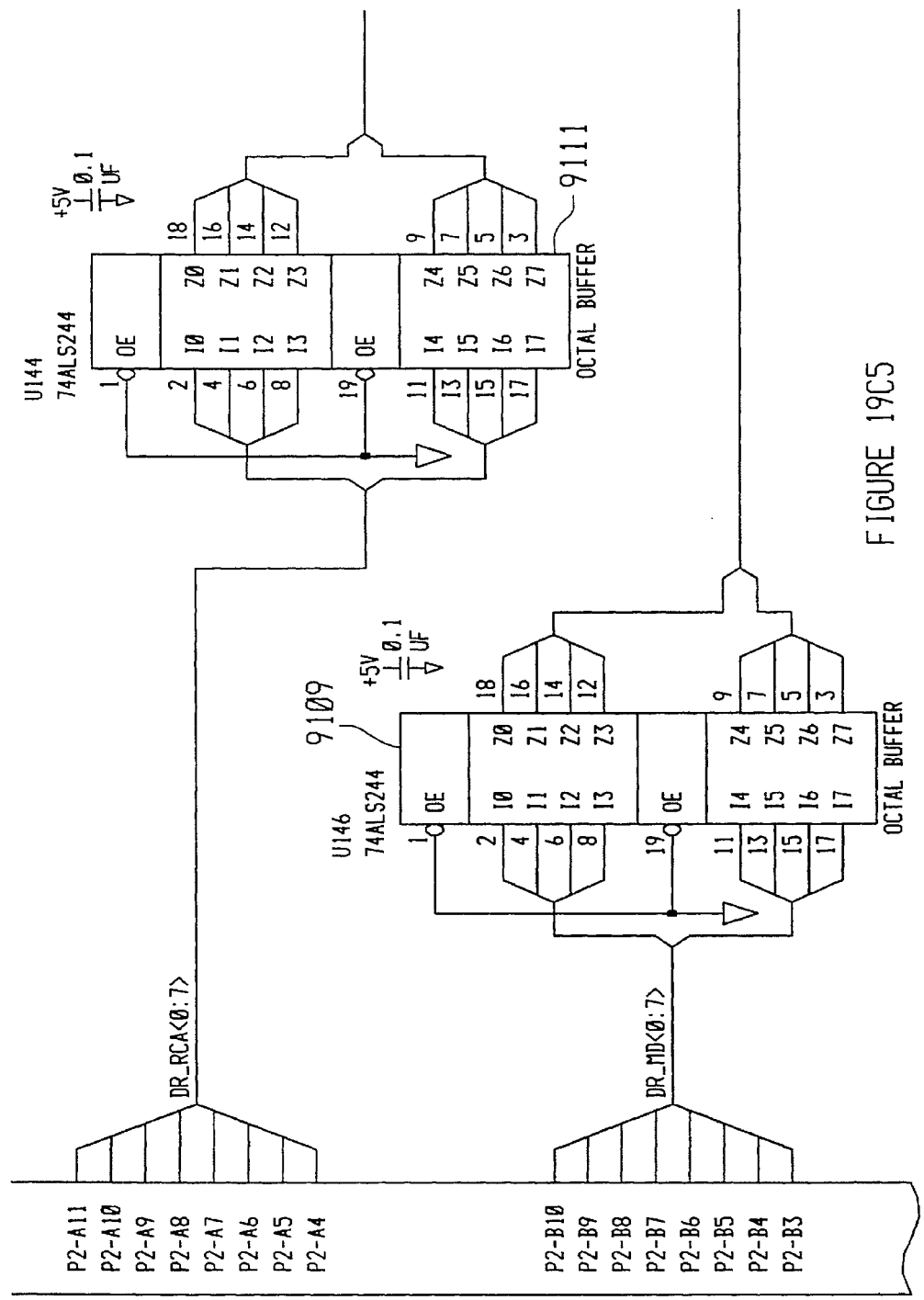

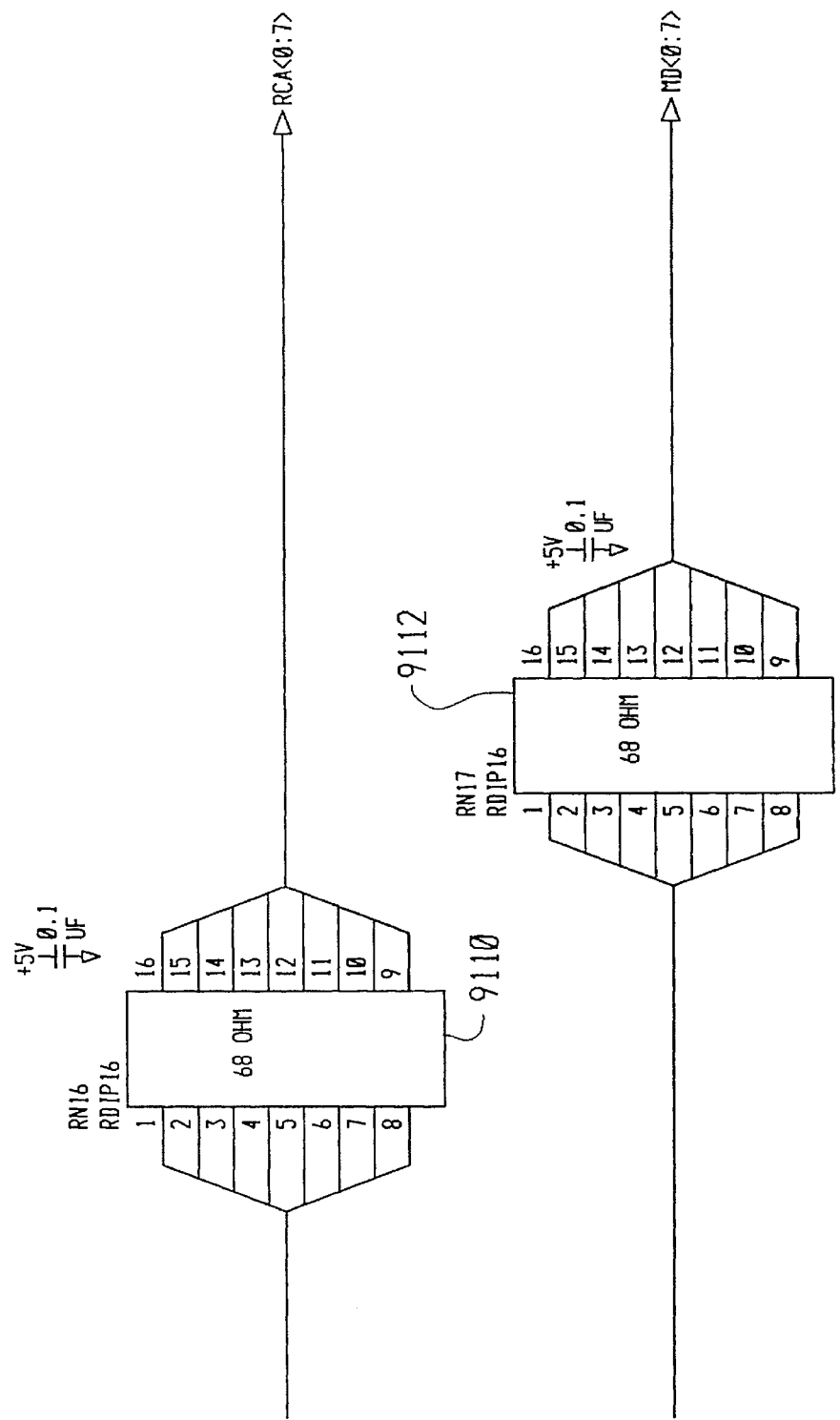
FIGURE 19C6

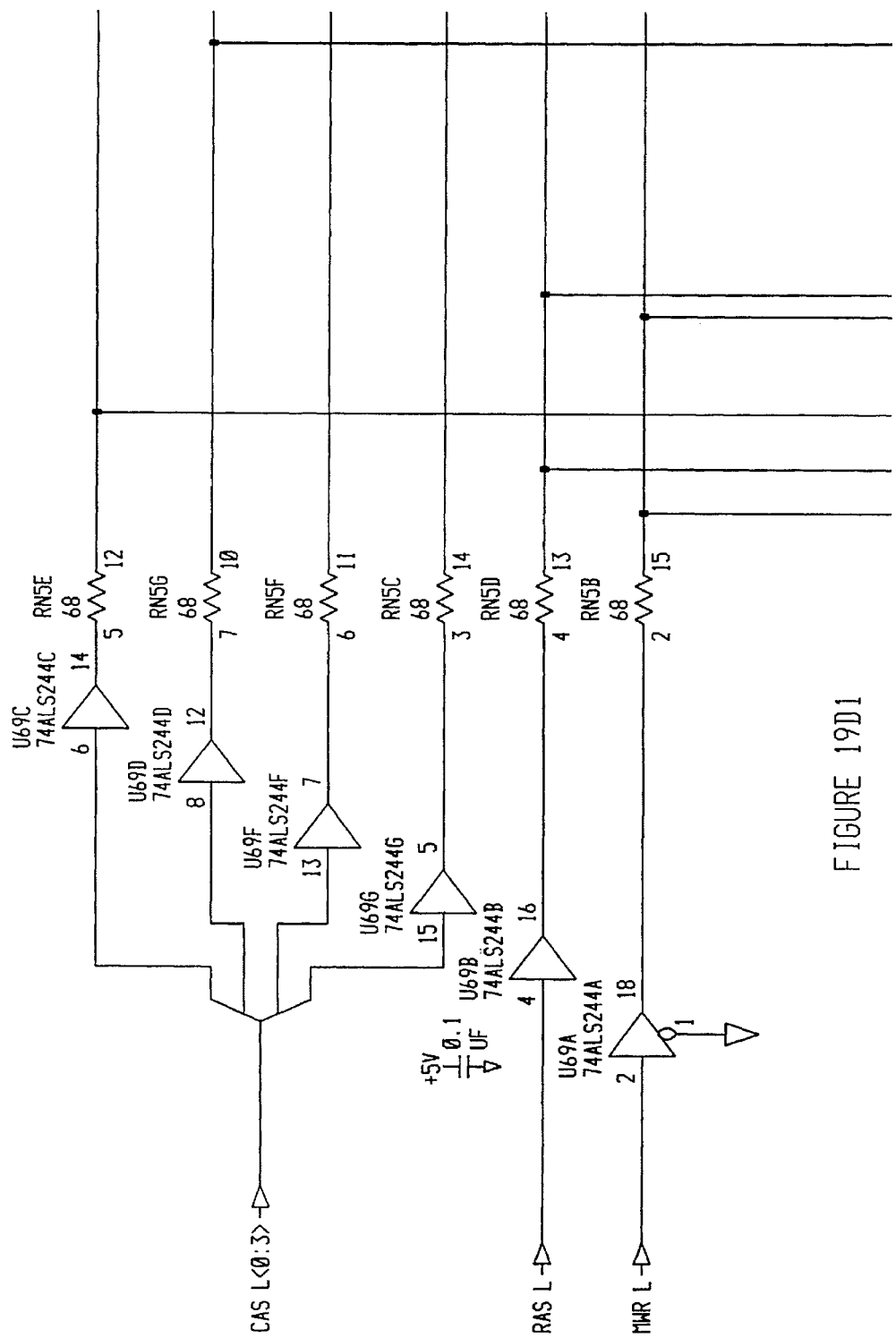
FIGURE 19D1

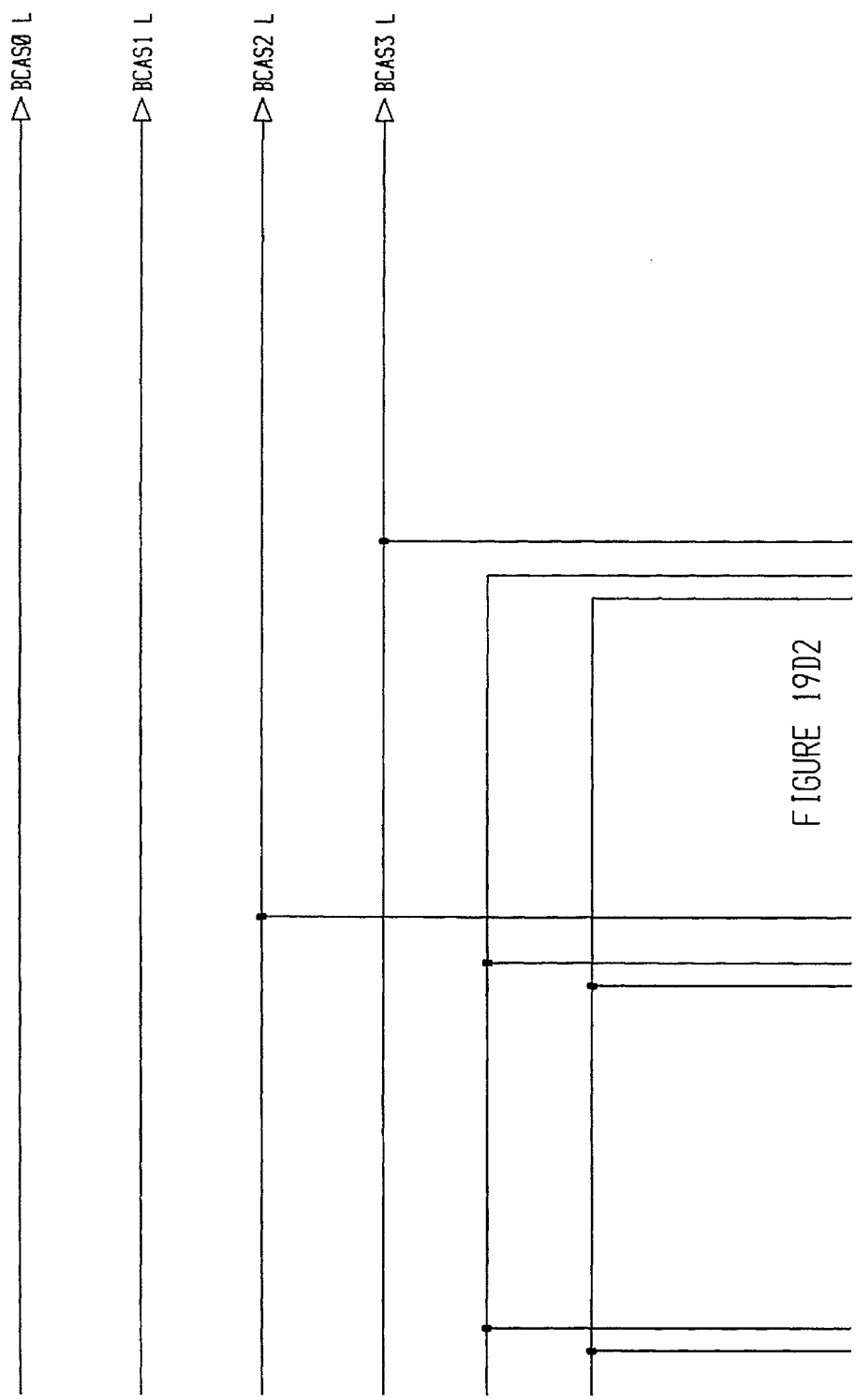

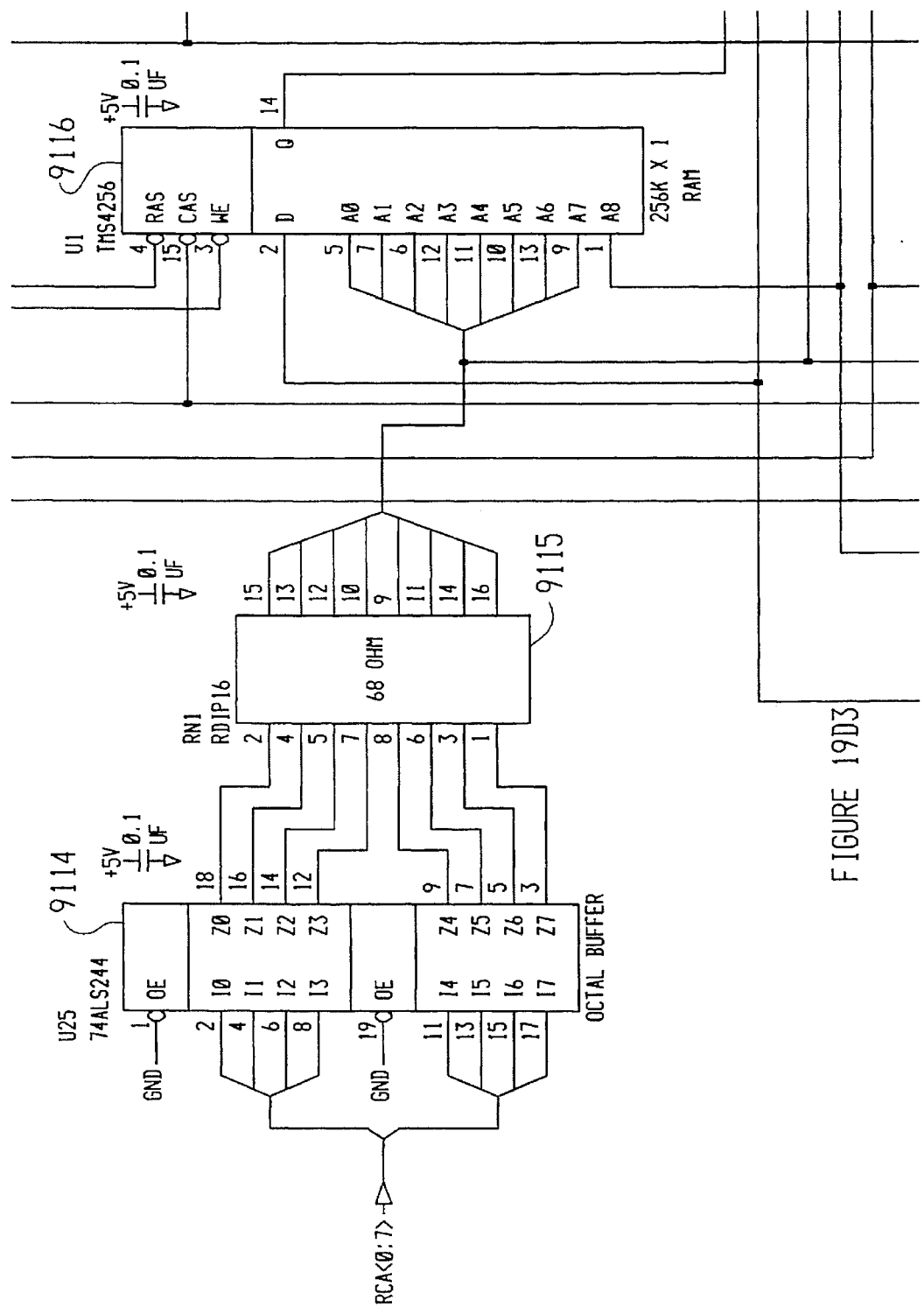
FIGURE 19D3

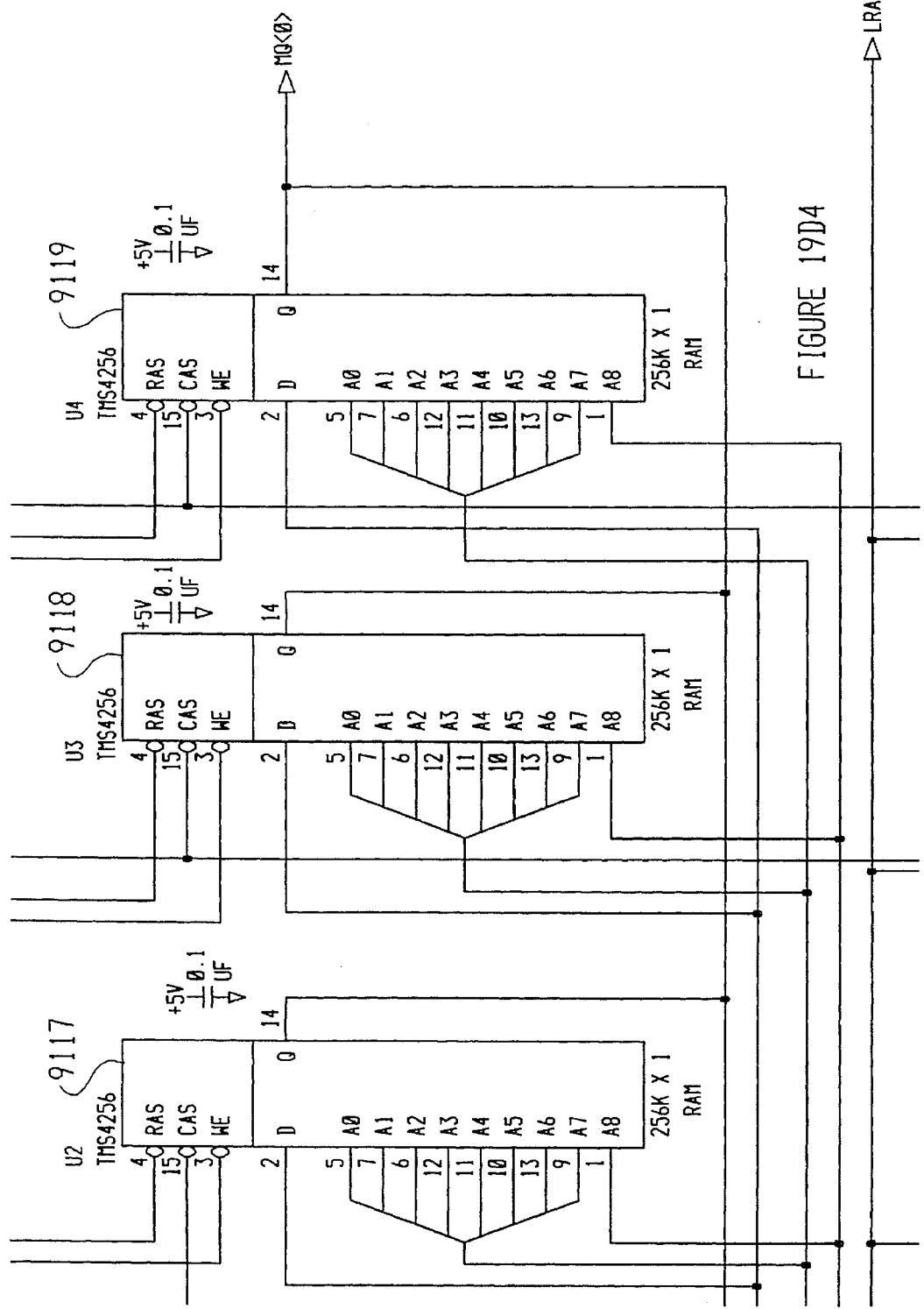
FIGURE 19D4

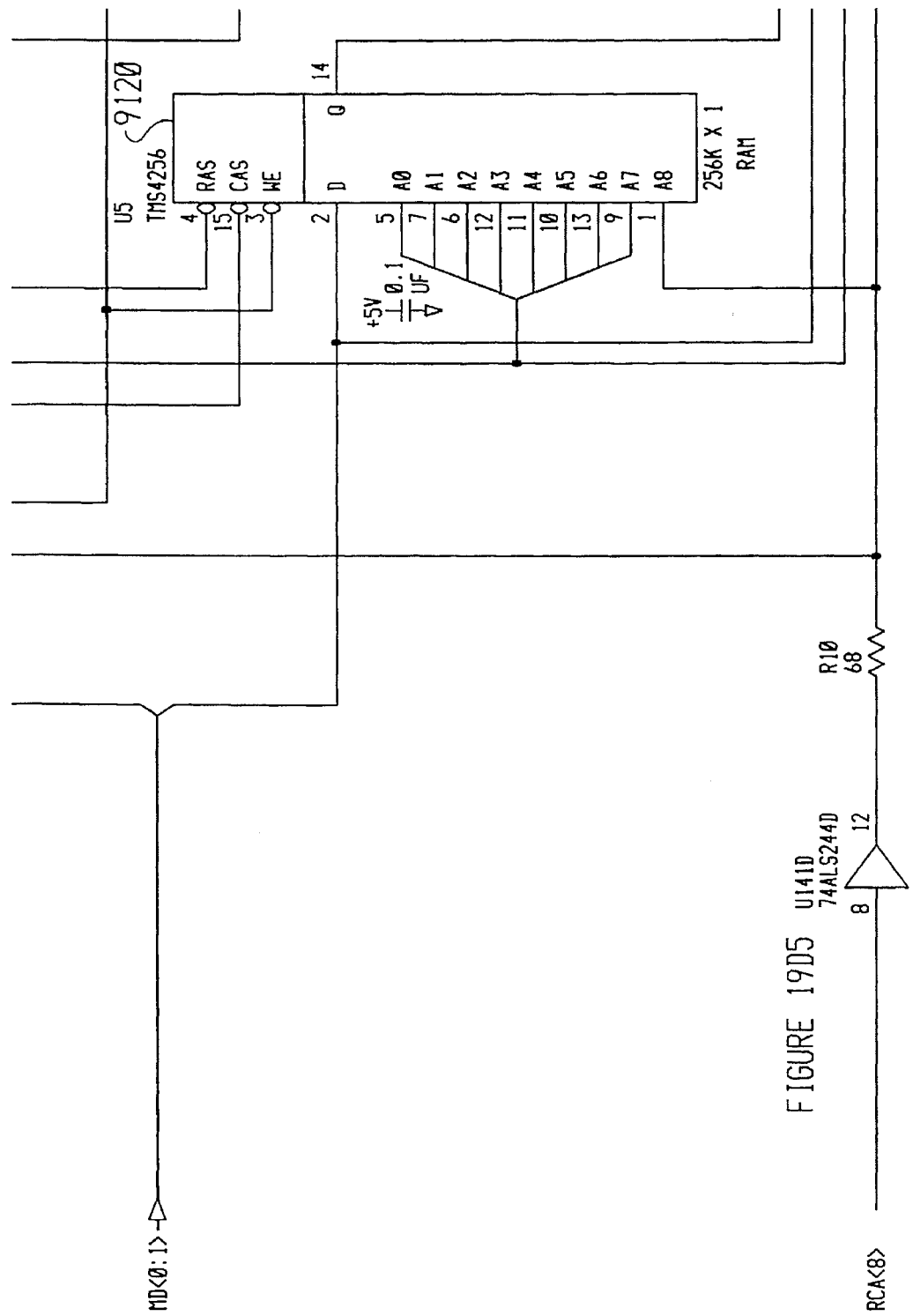
FIGURE 19D5

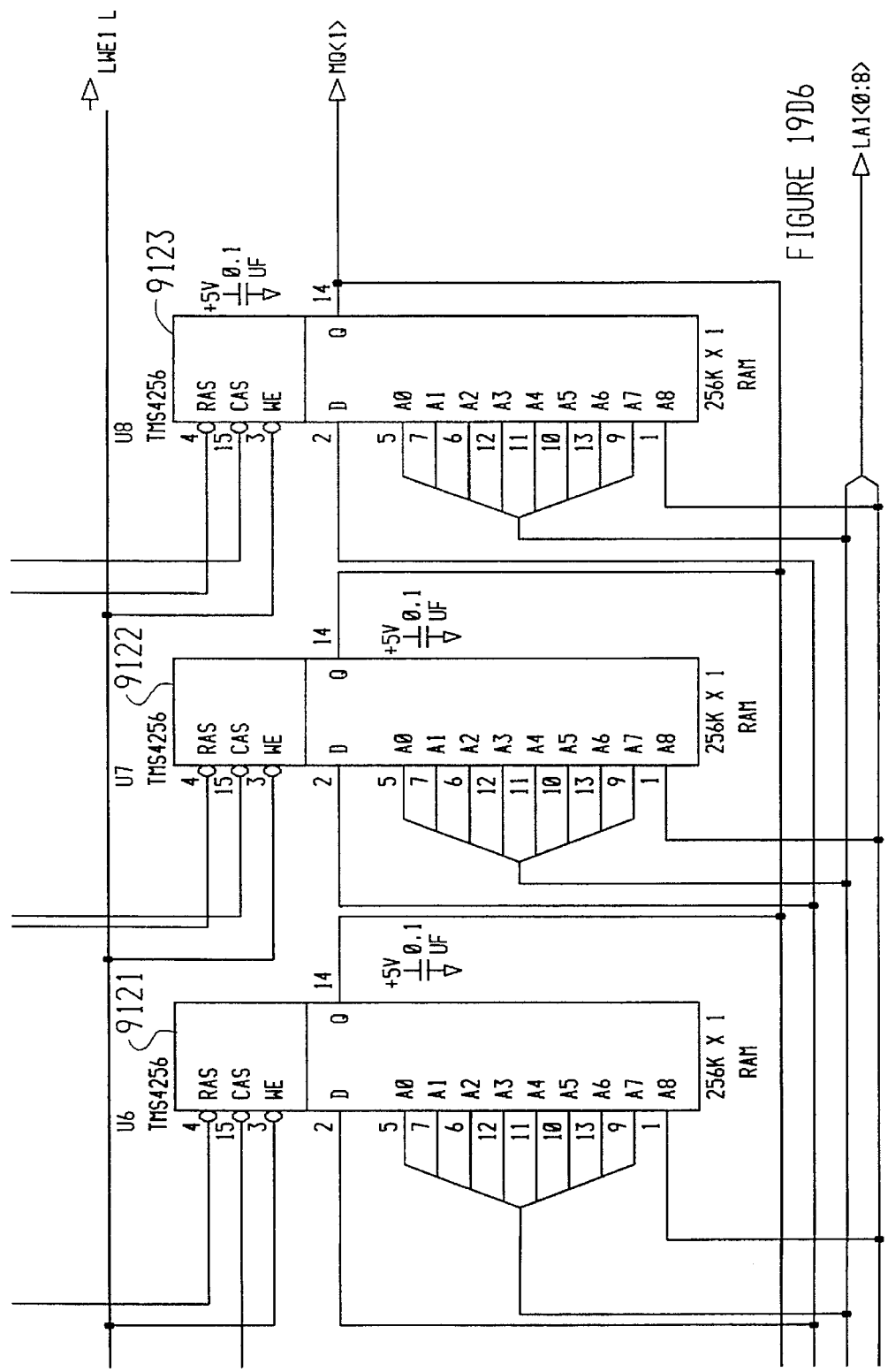
FIGURE 19D6

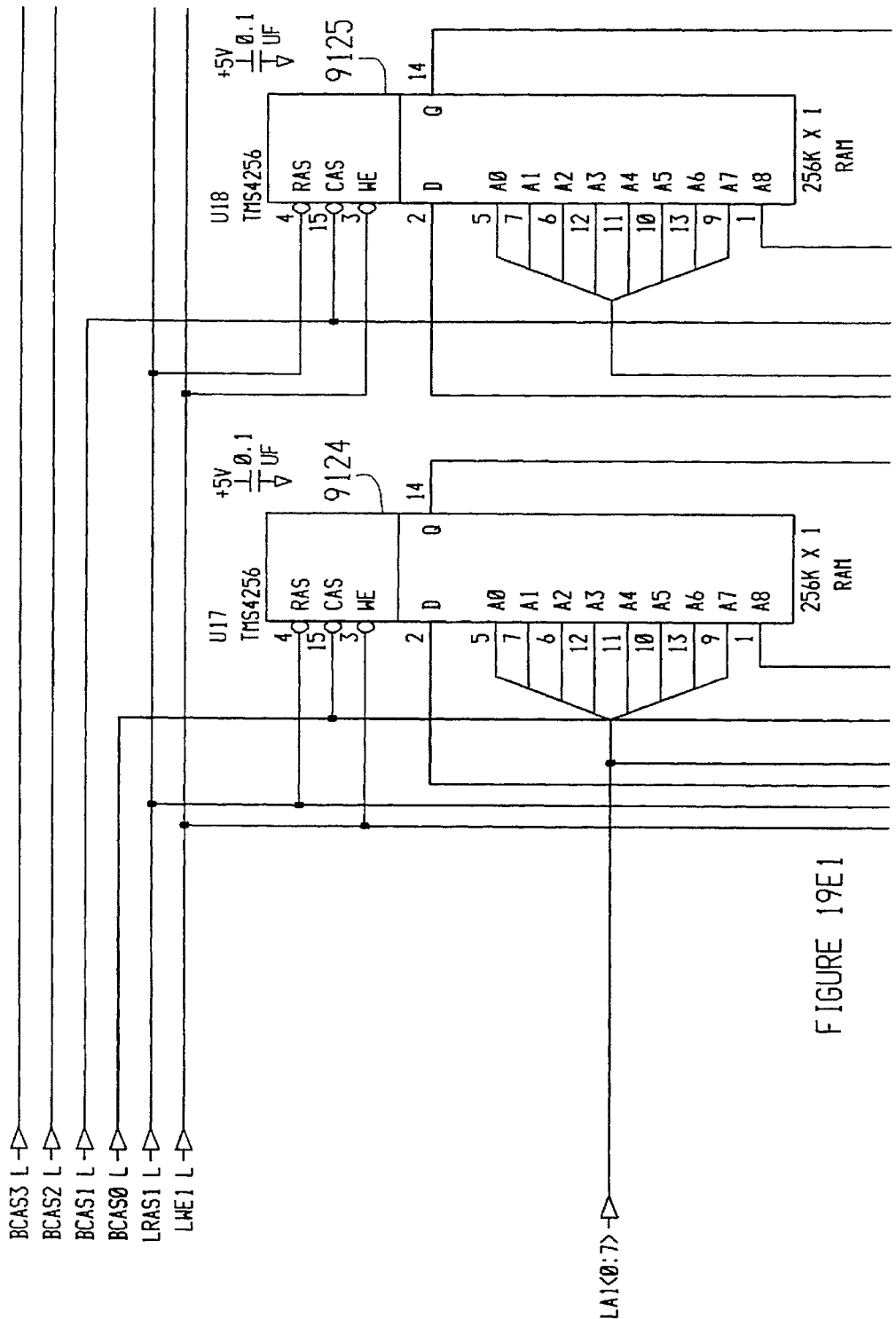
FIGURE 19E1

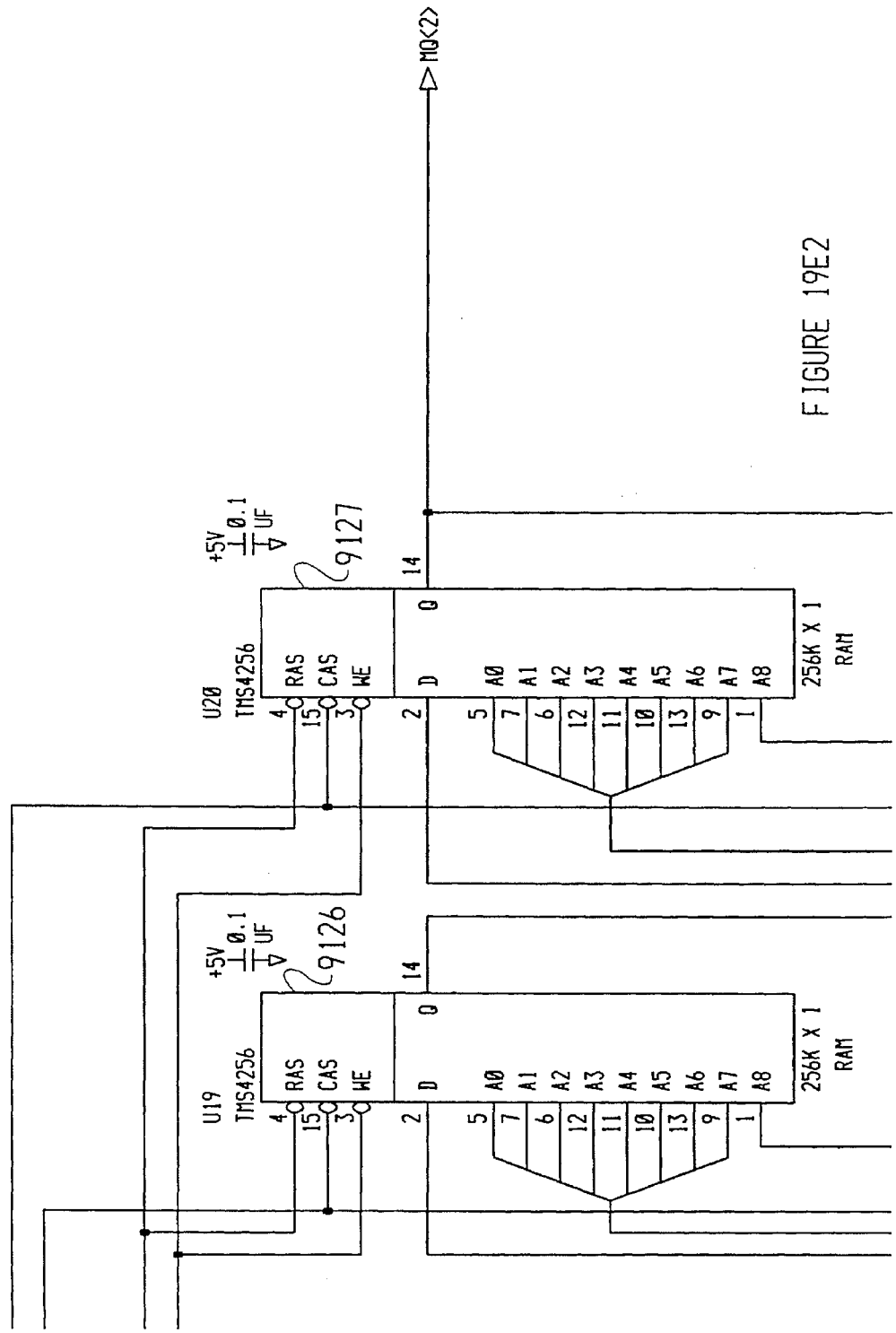
FIGURE 19E2

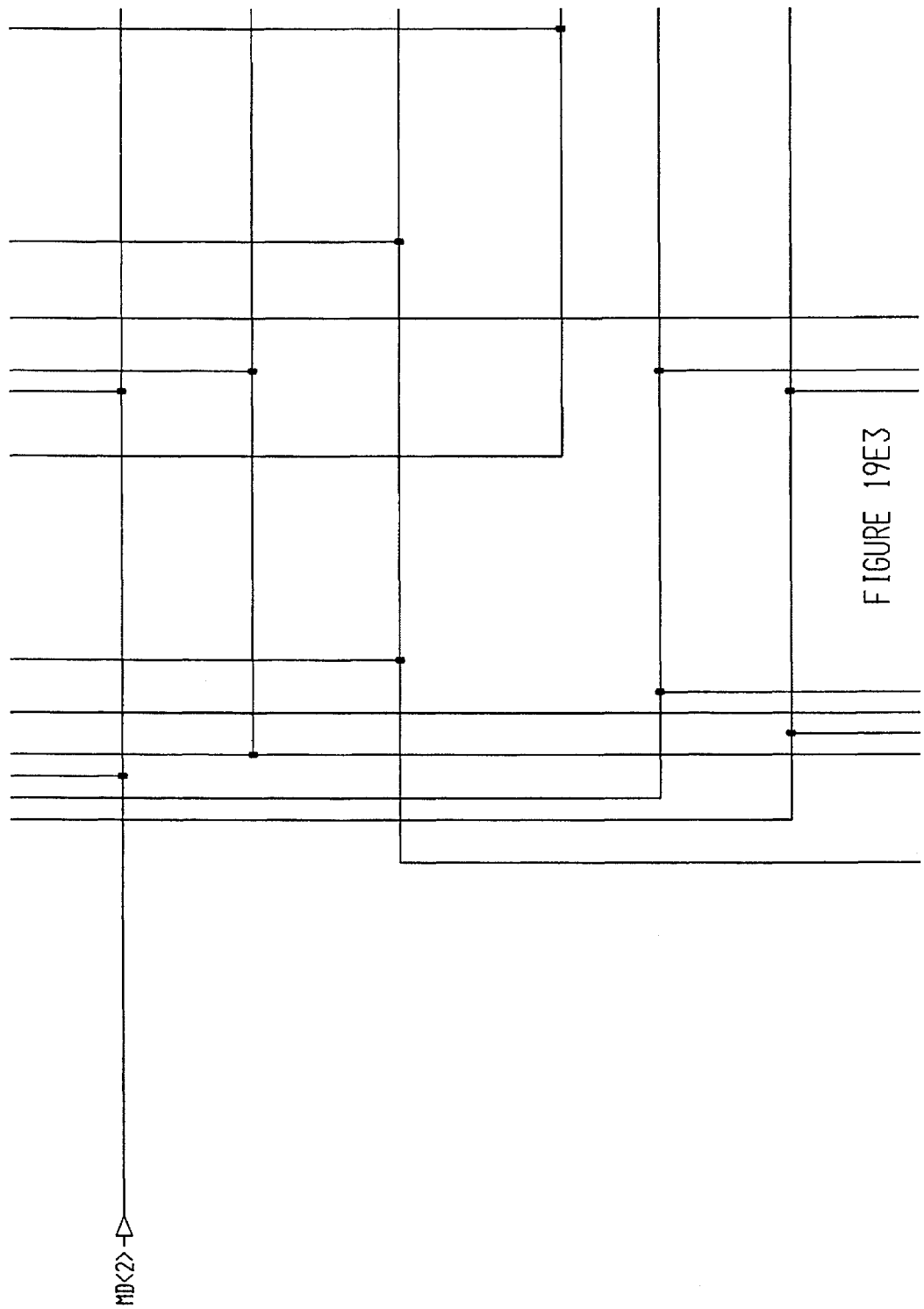
FIGURE 19E3

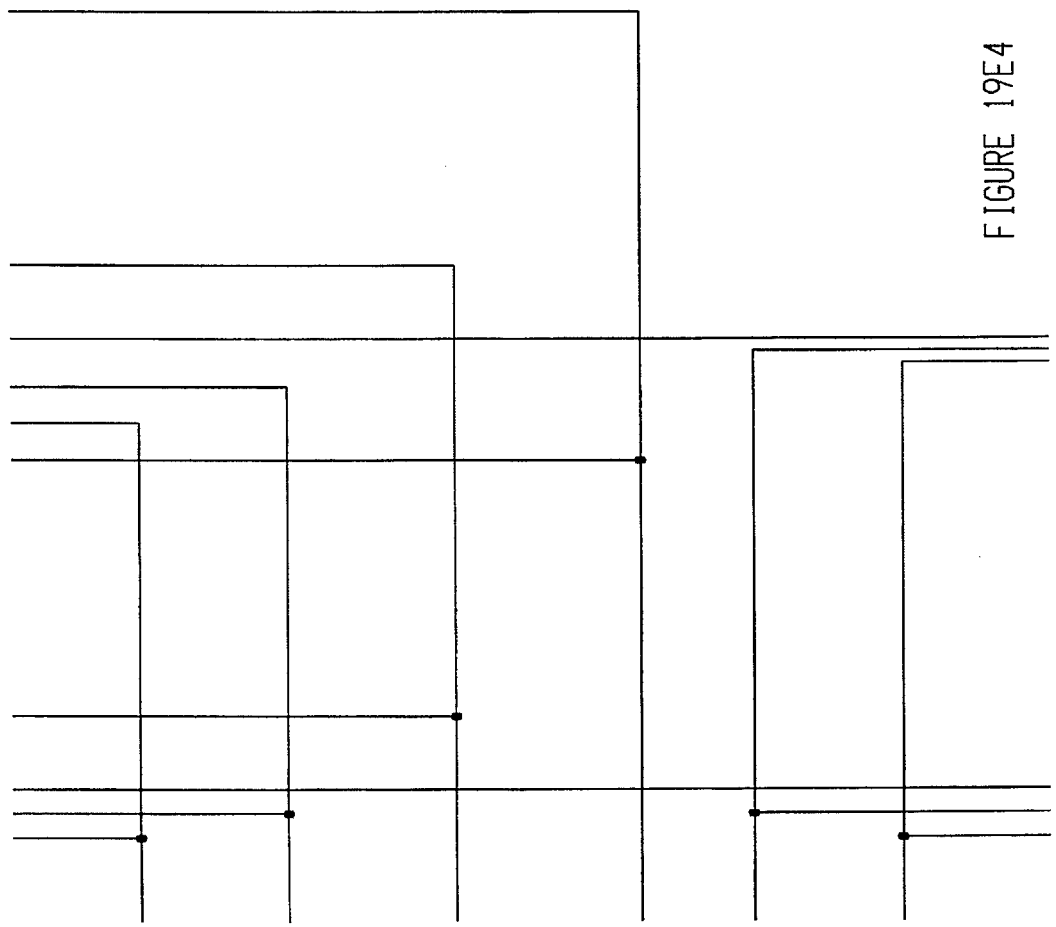

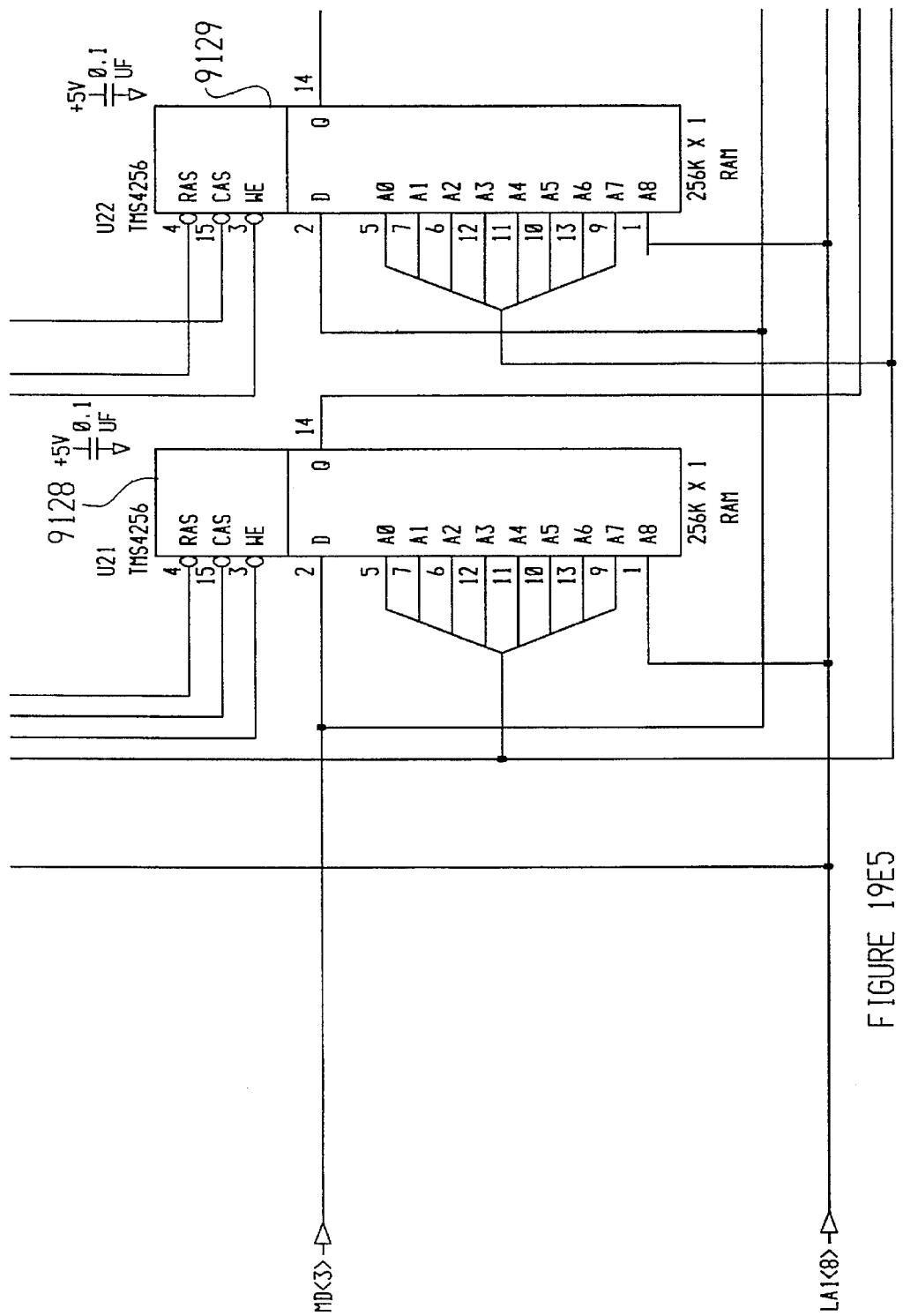
FIGURE 19E5

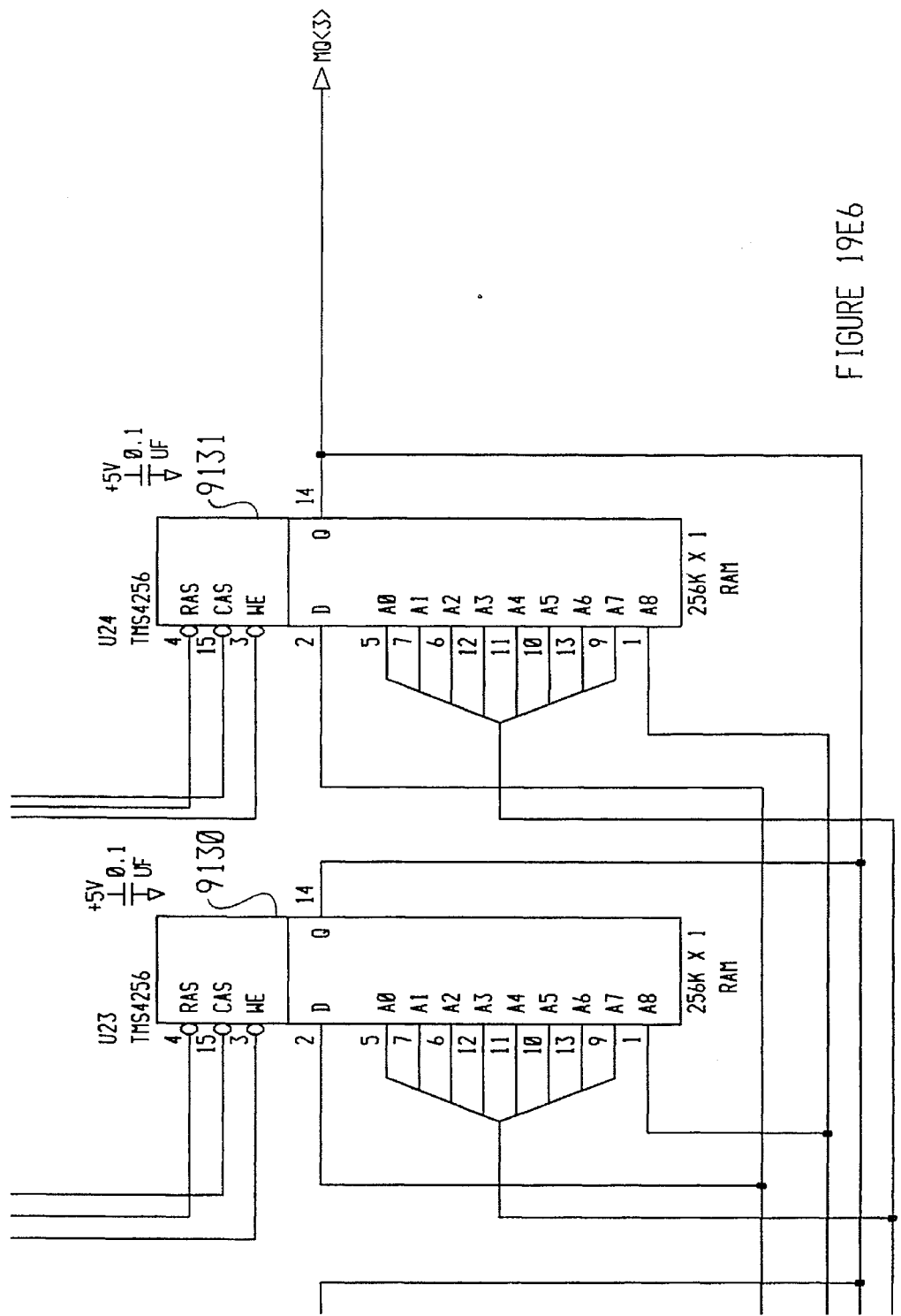
FIGURE 19E6

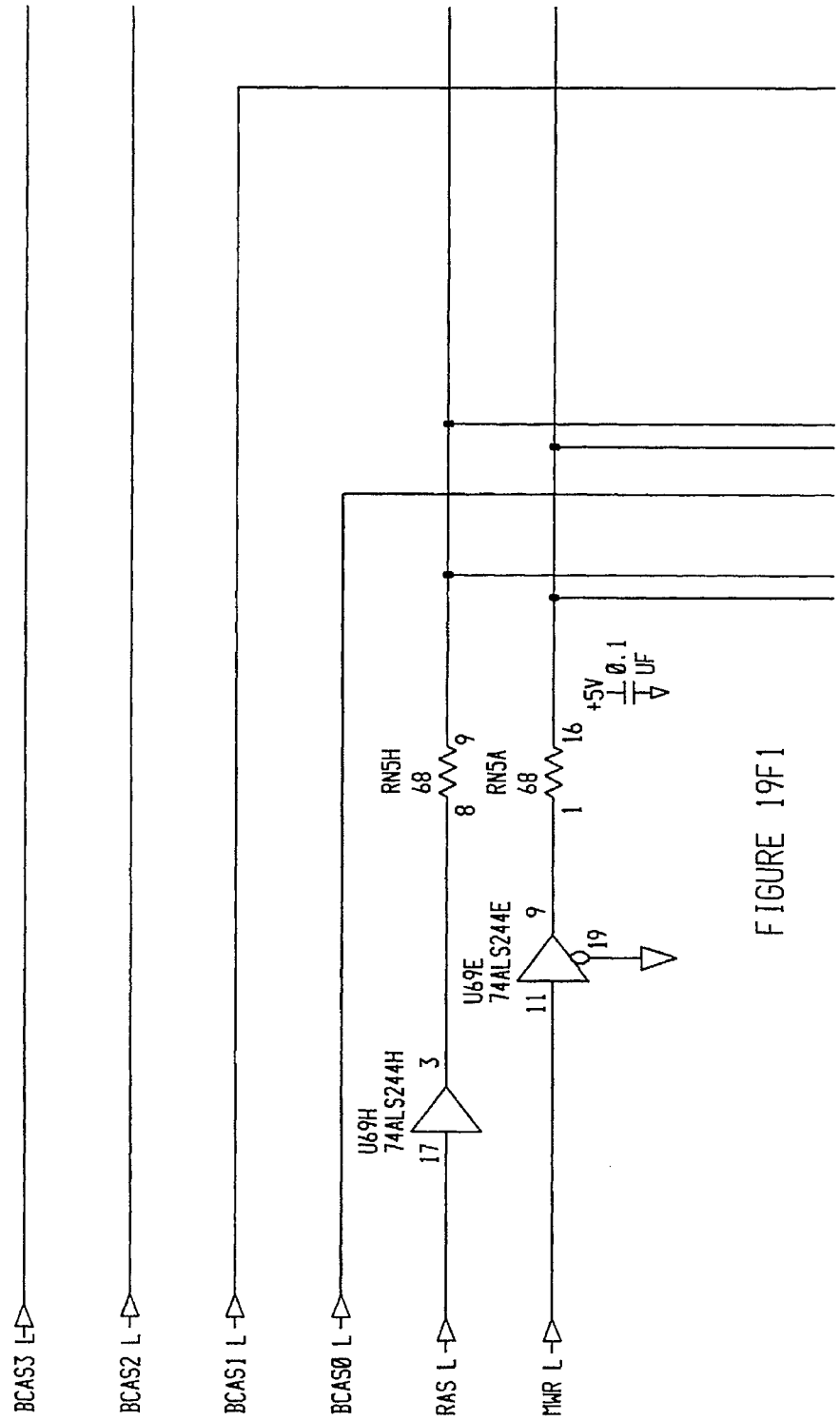
FIGURE 19F1

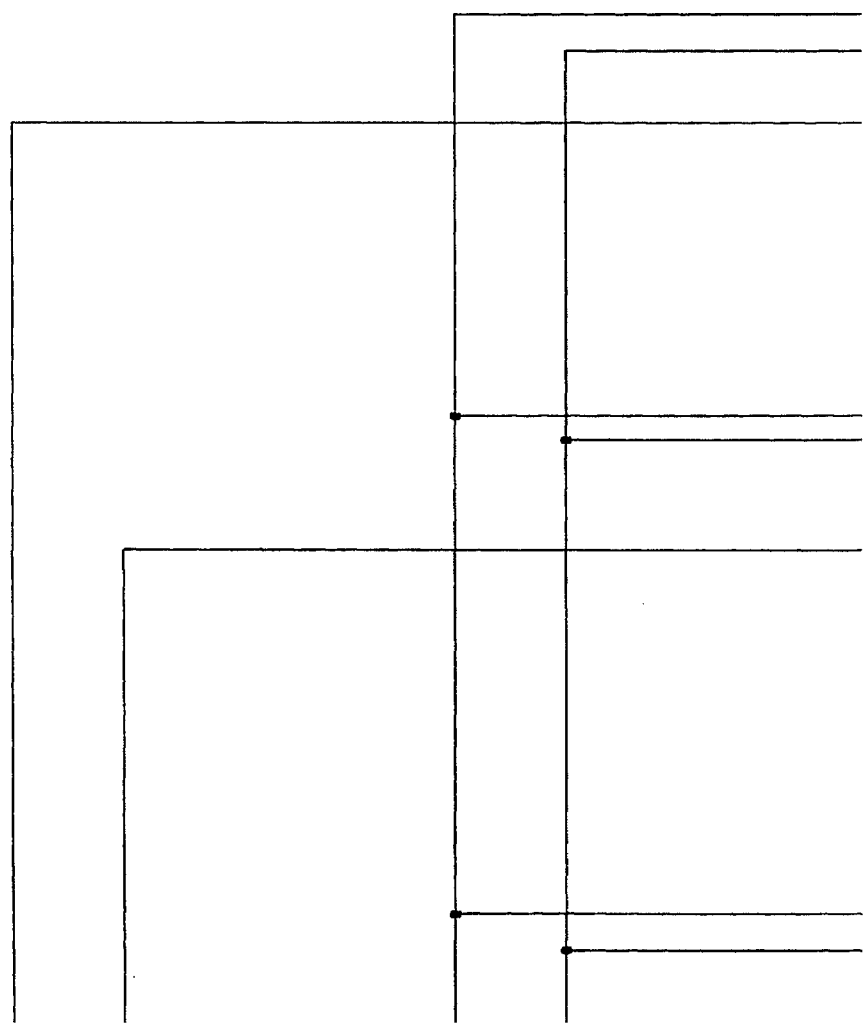

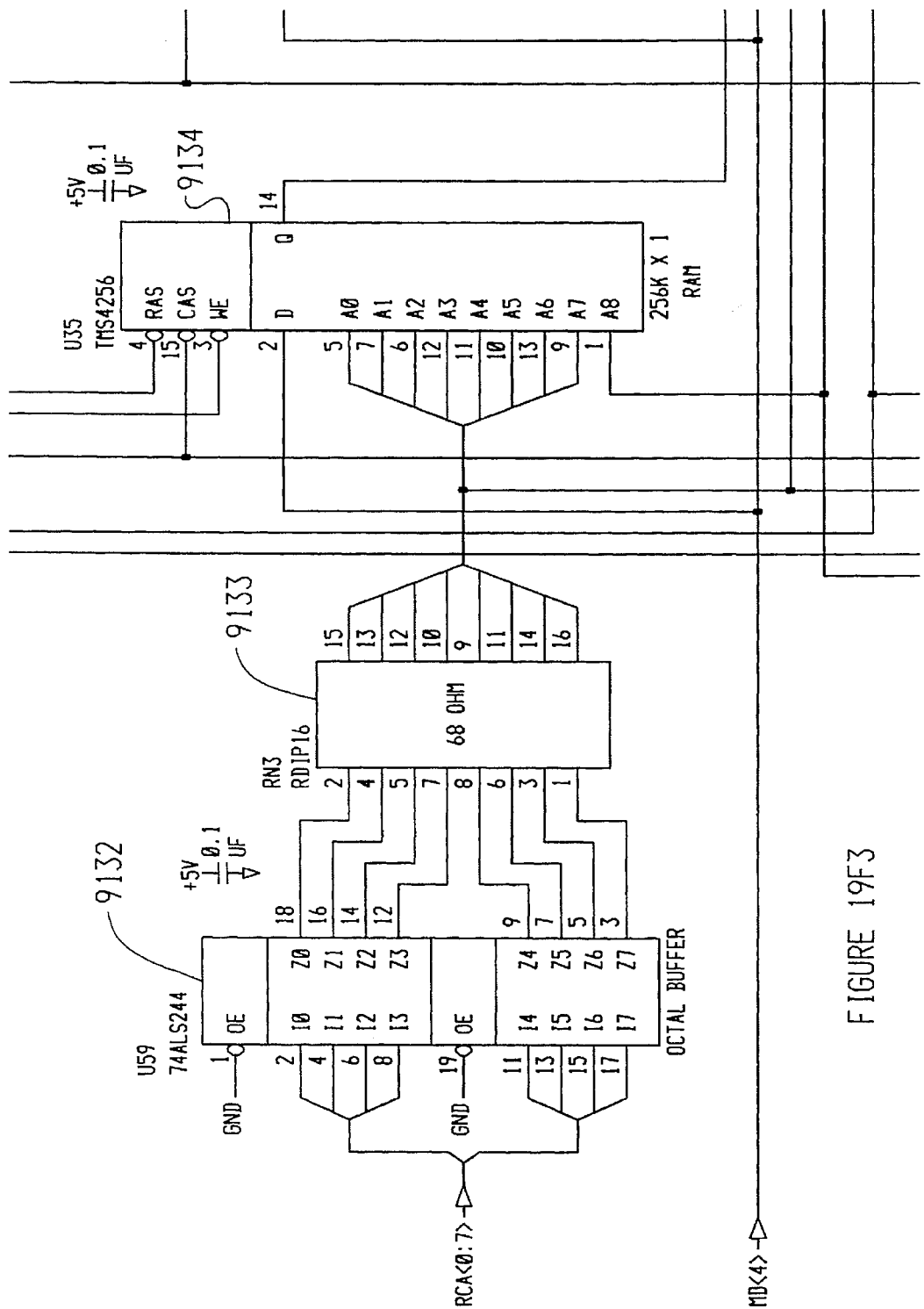
FIGURE 19F3

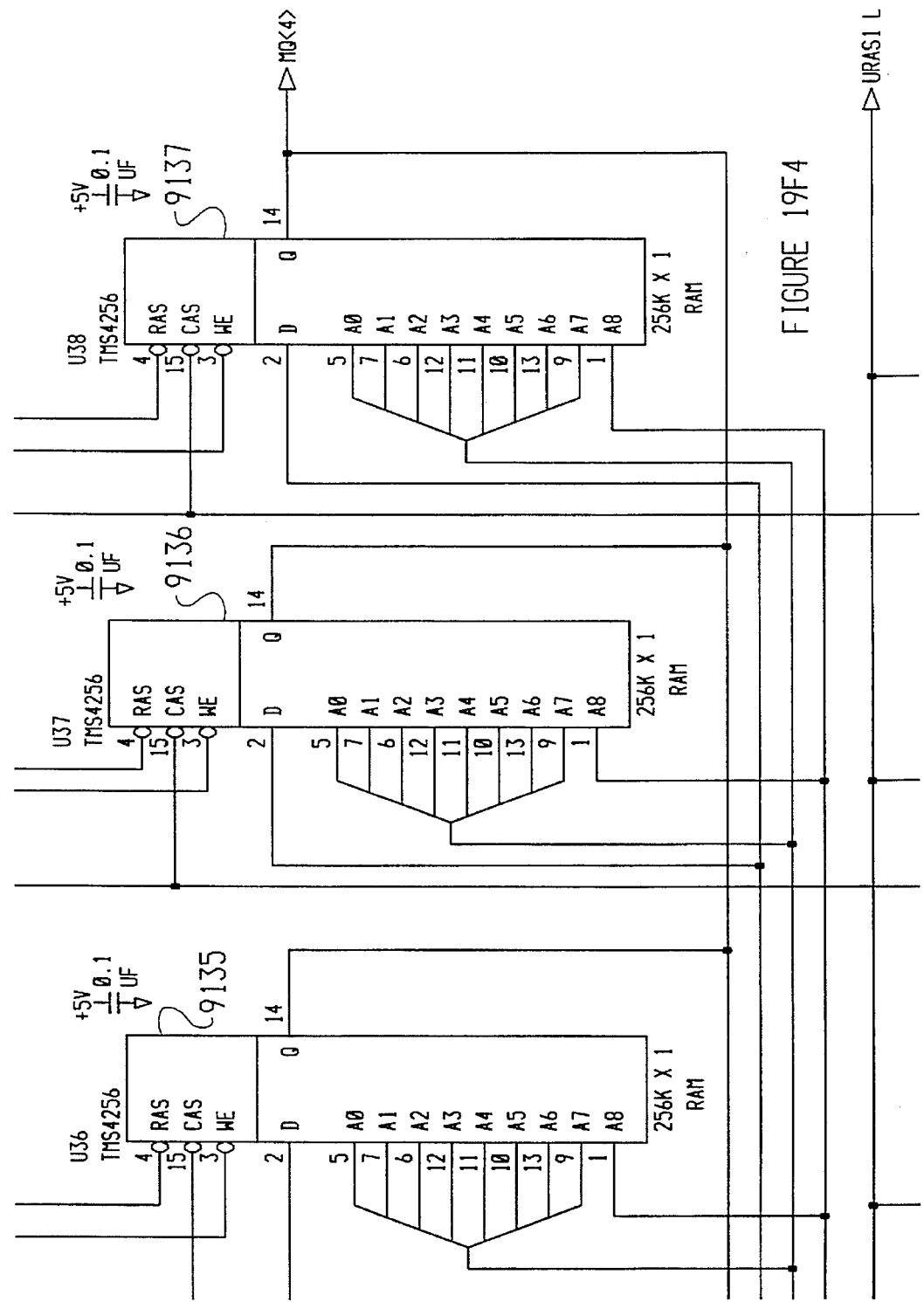
FIGURE 19F4

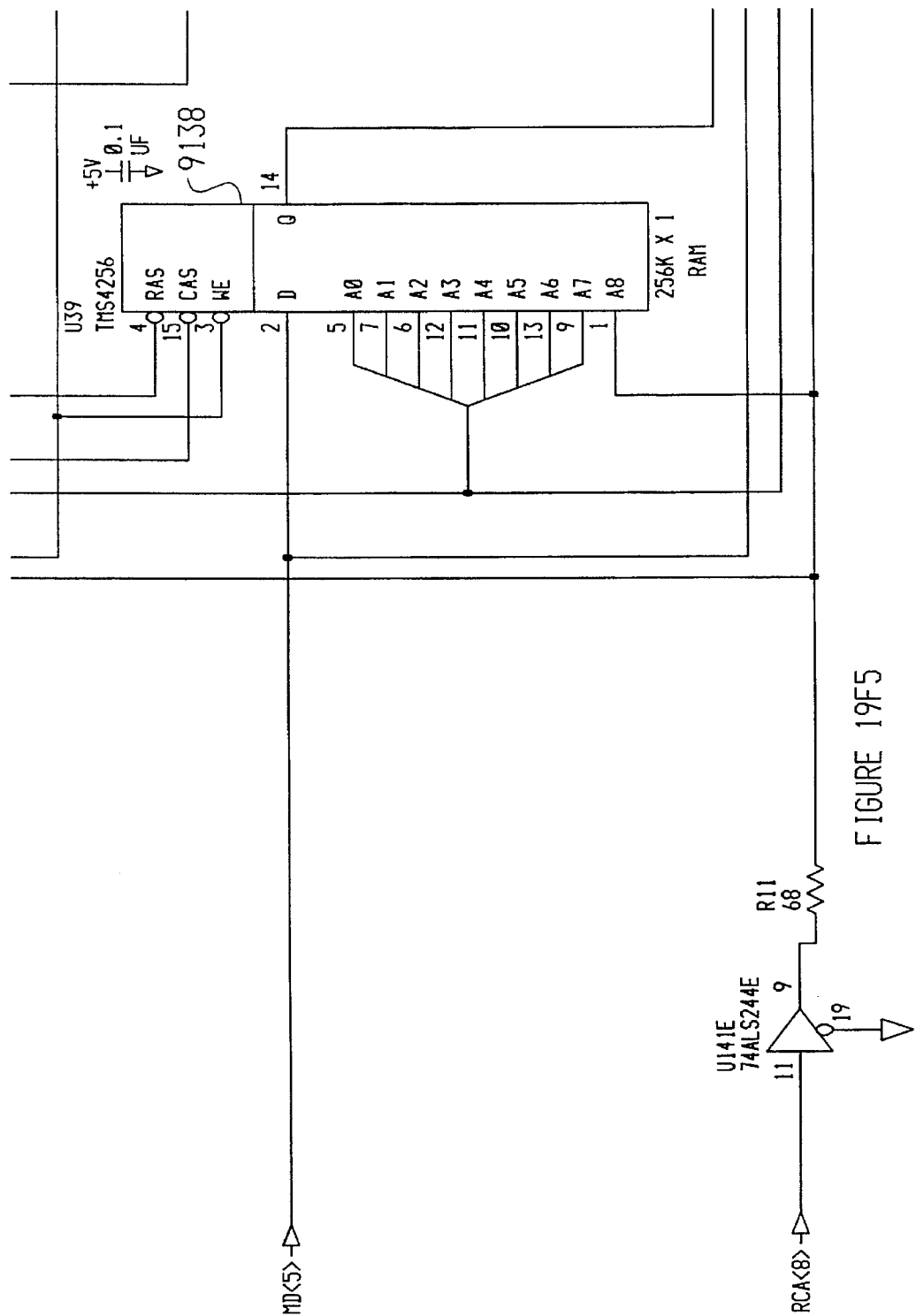
FIGURE 19F5

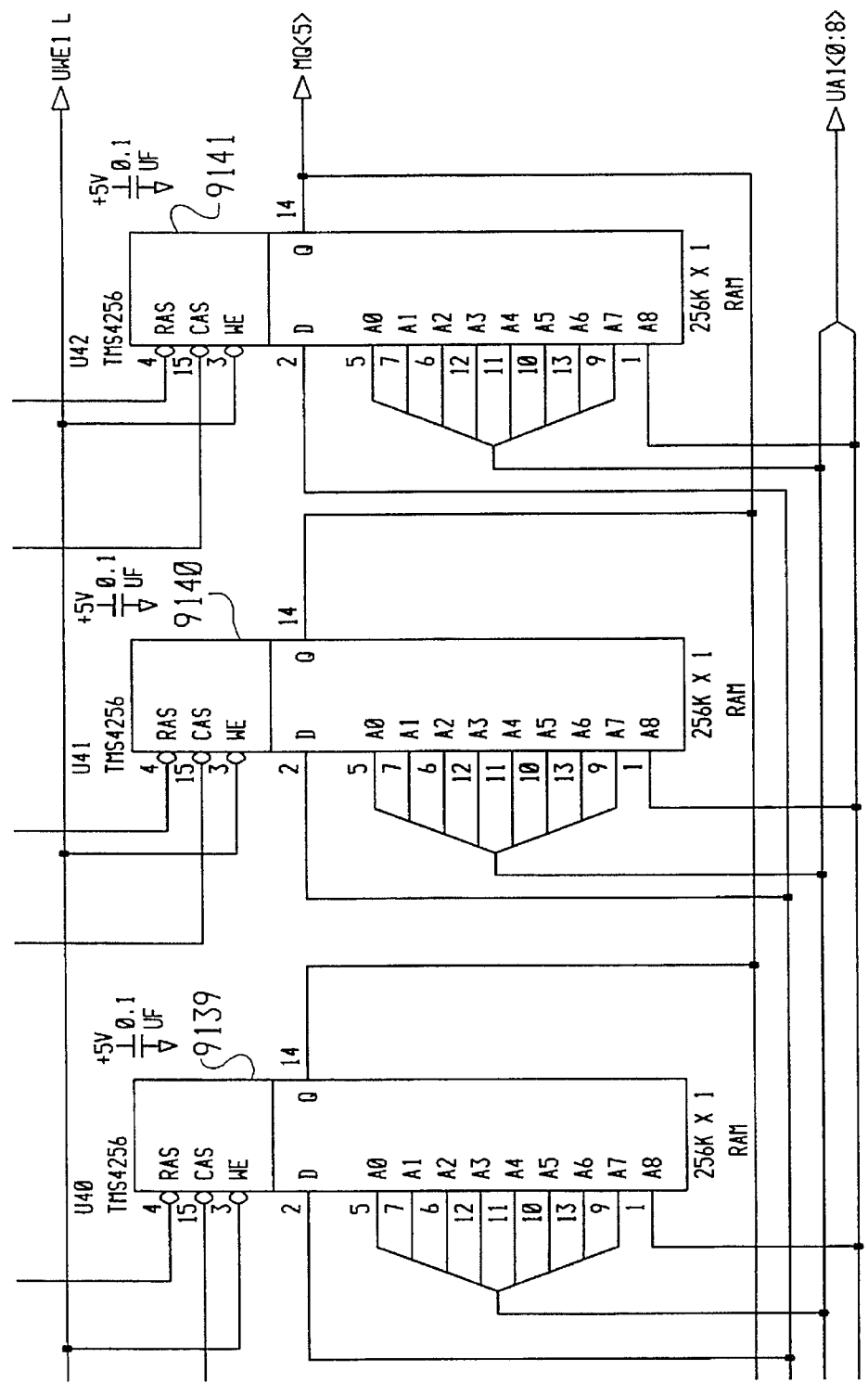
FIGURE 19F6

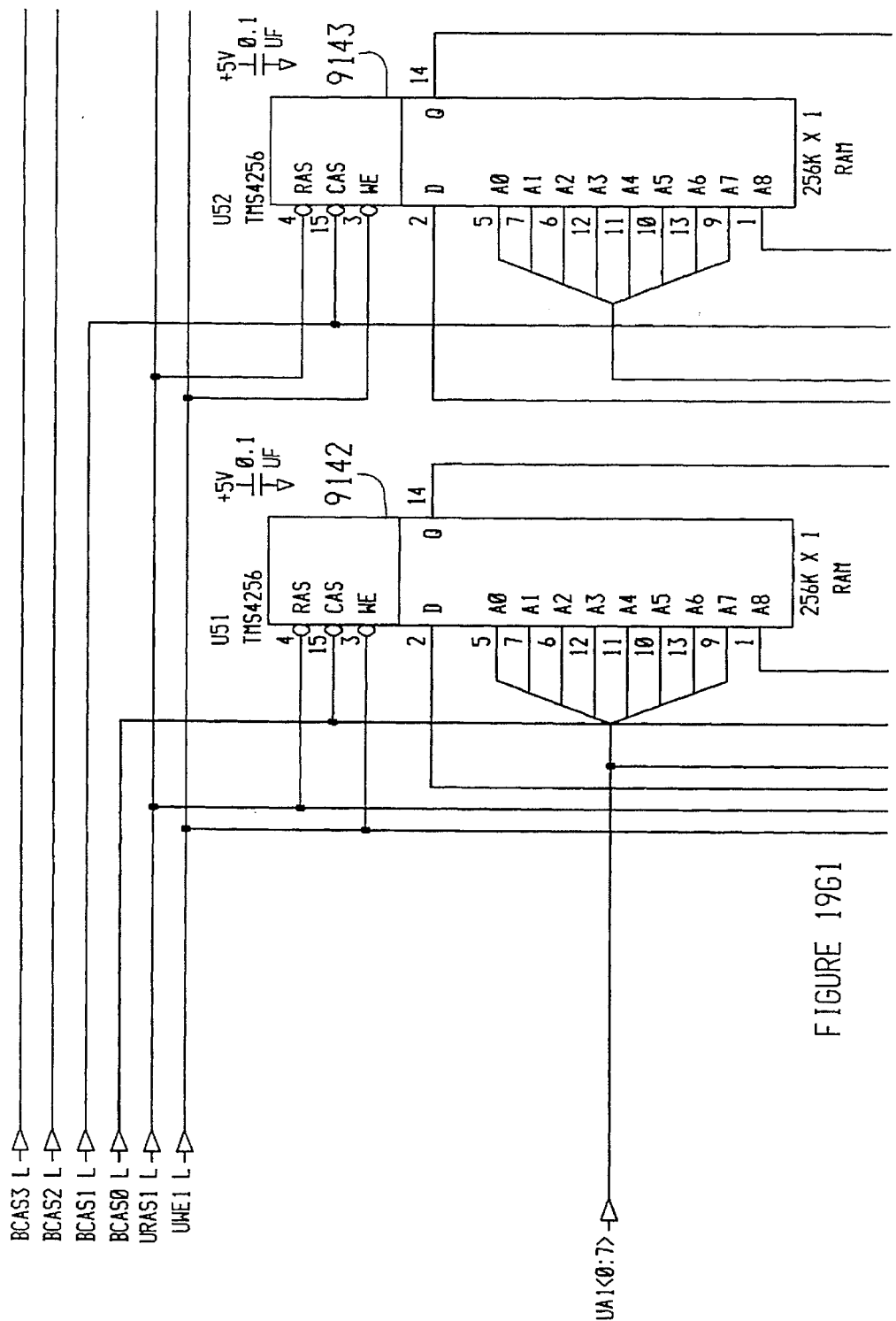
FIGURE 1961

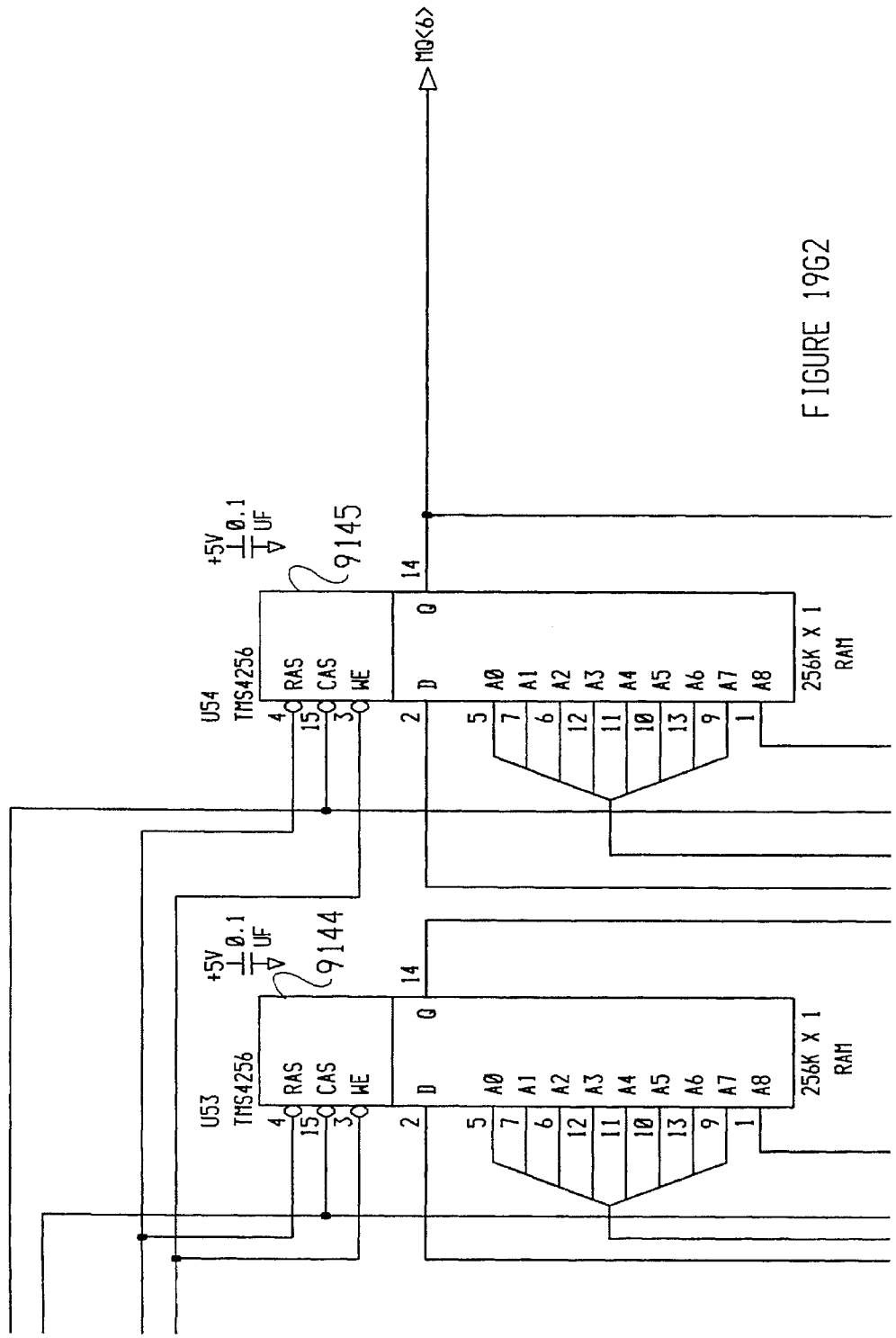
FIGURE 1962

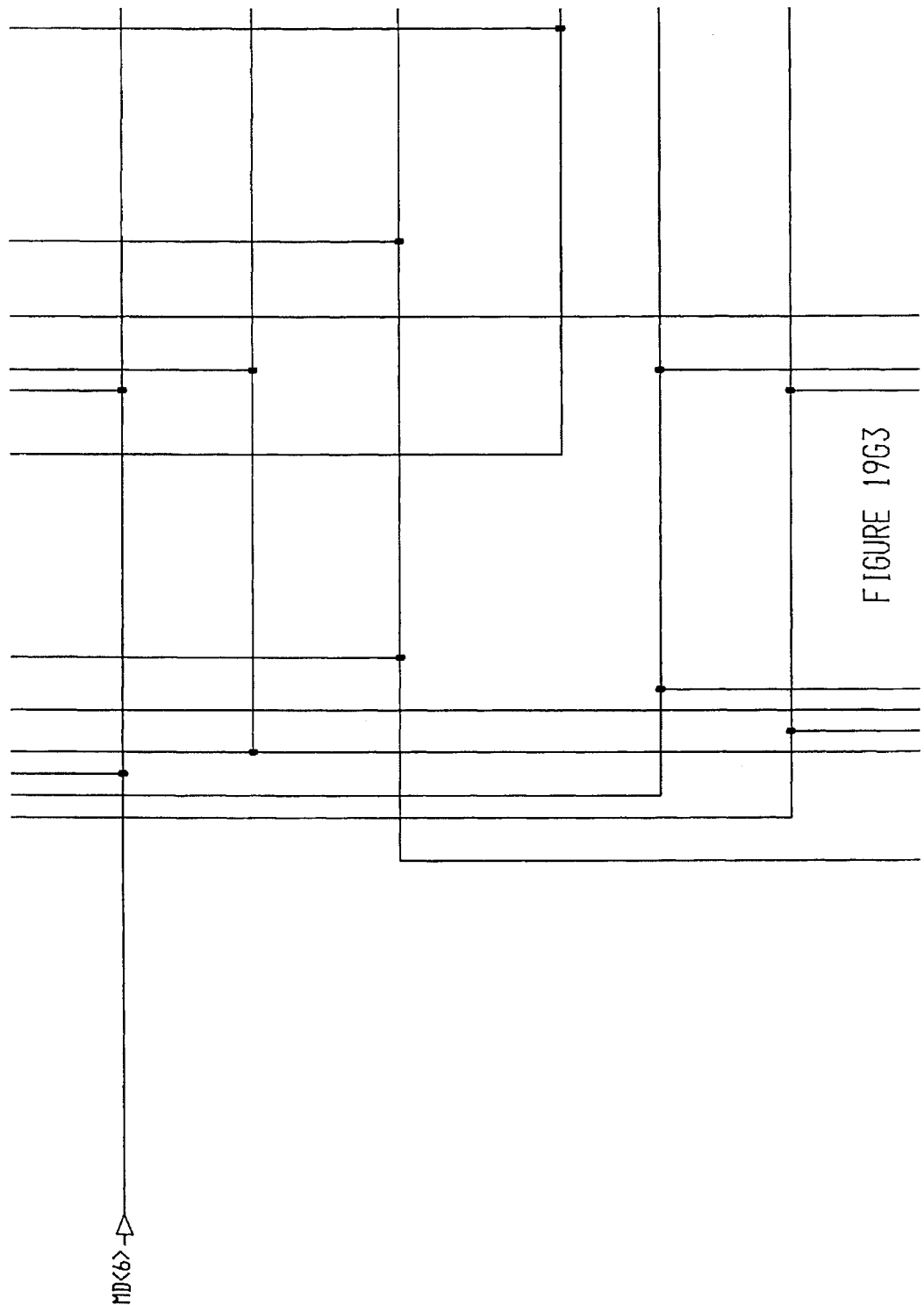
FIGURE 19G3

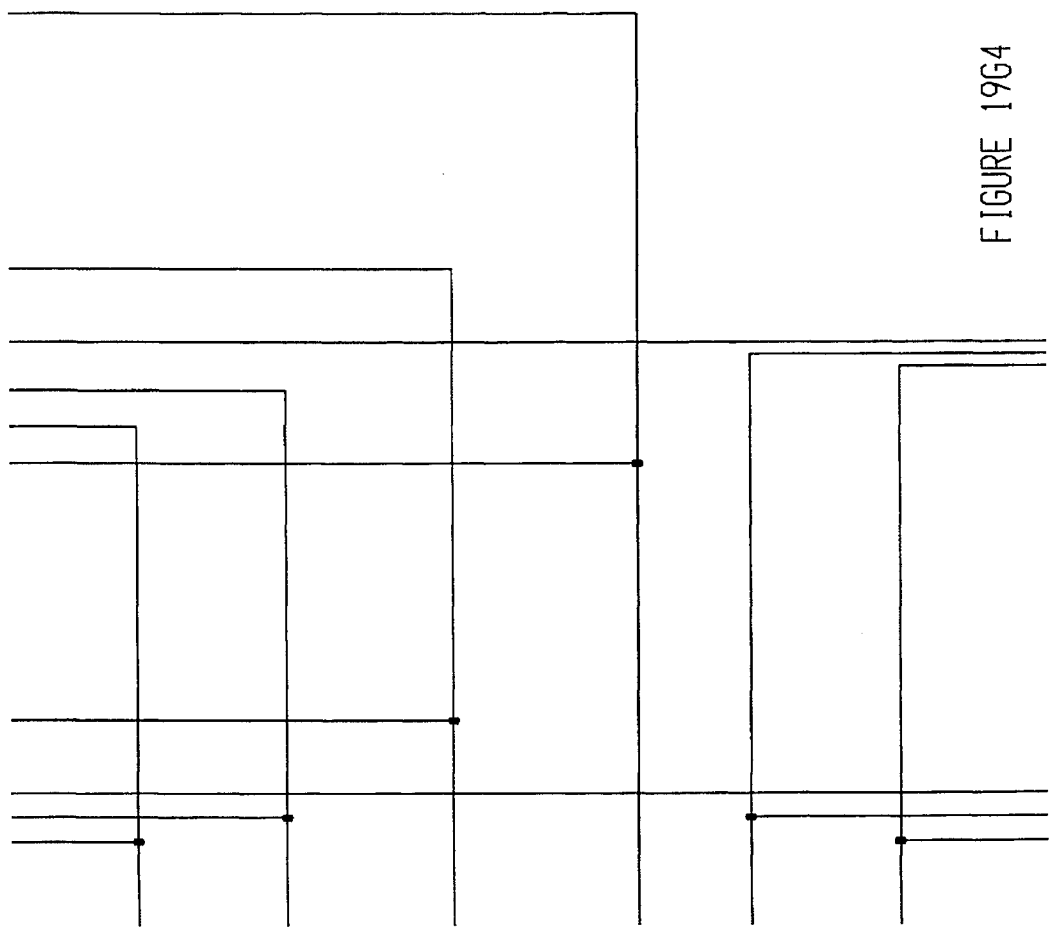

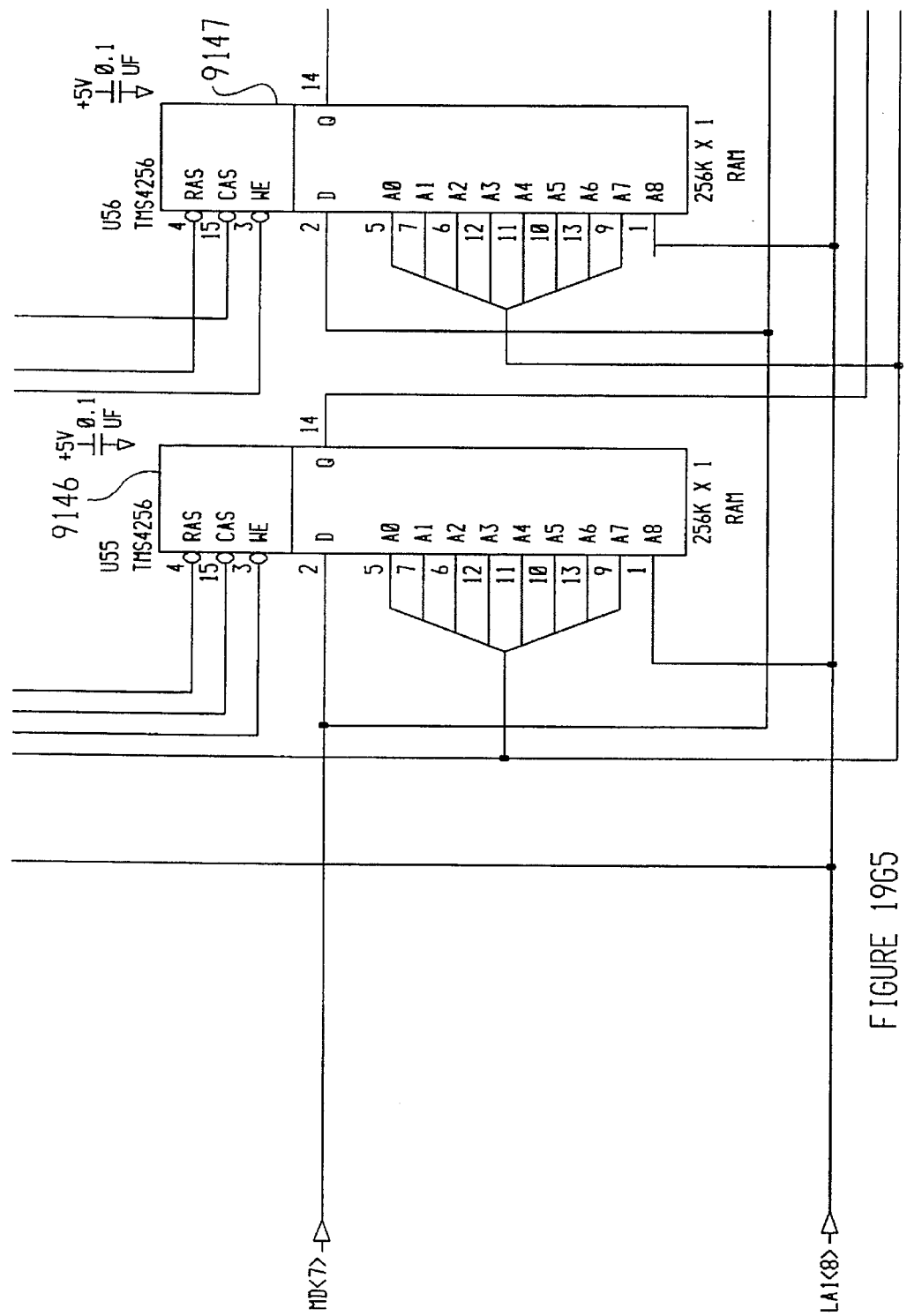
FIGURE 1965

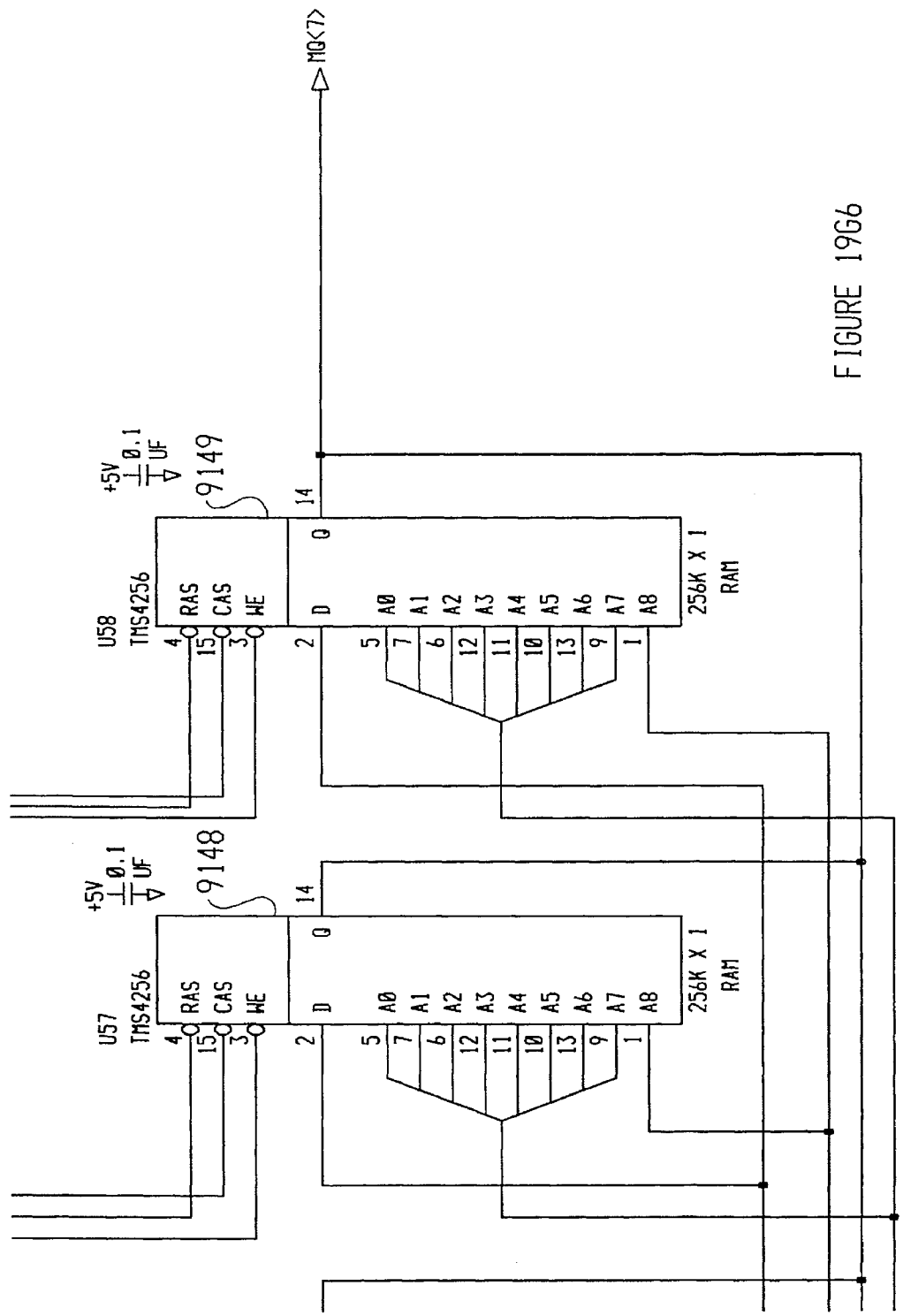
FIGURE 1966

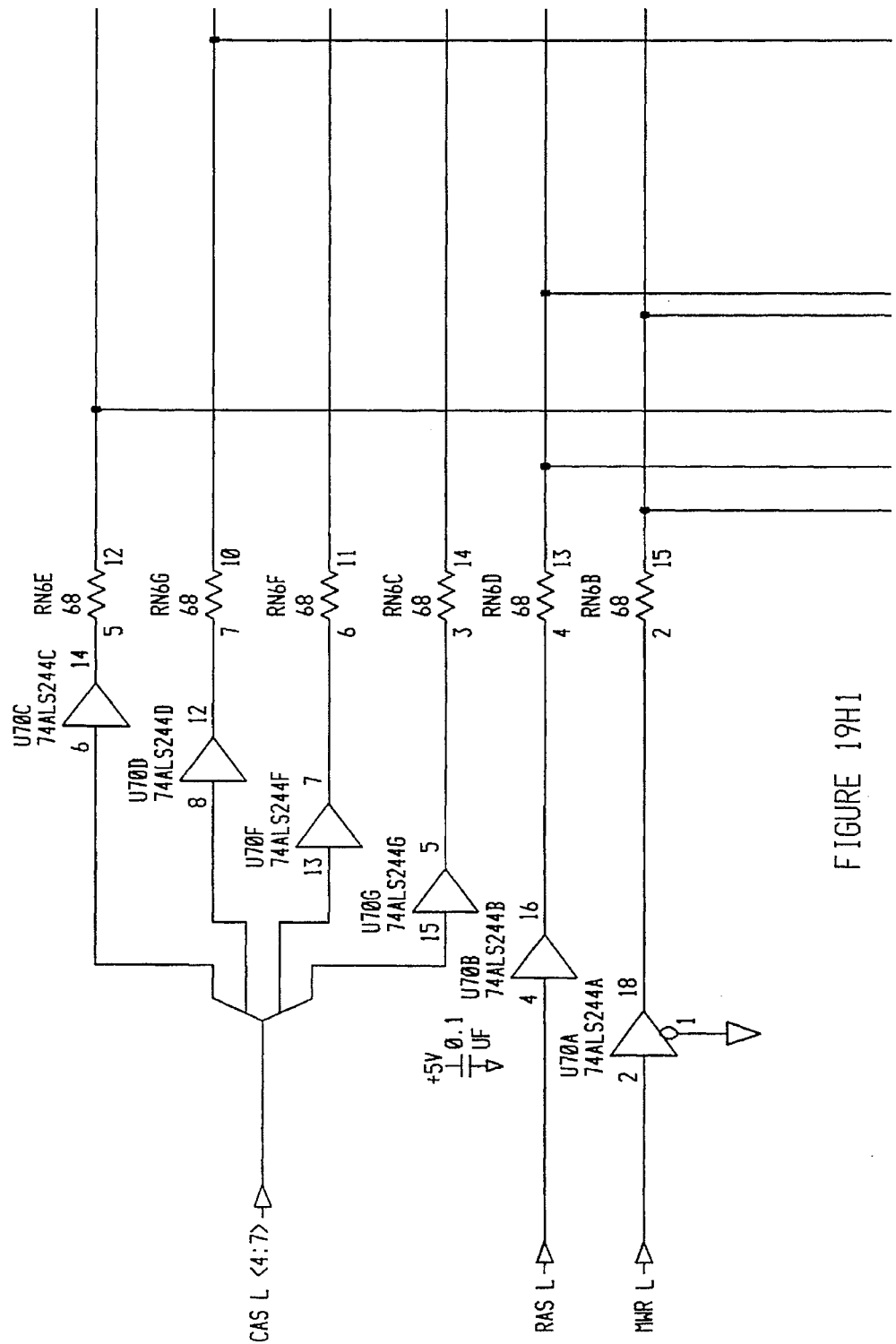
FIGURE 19H1

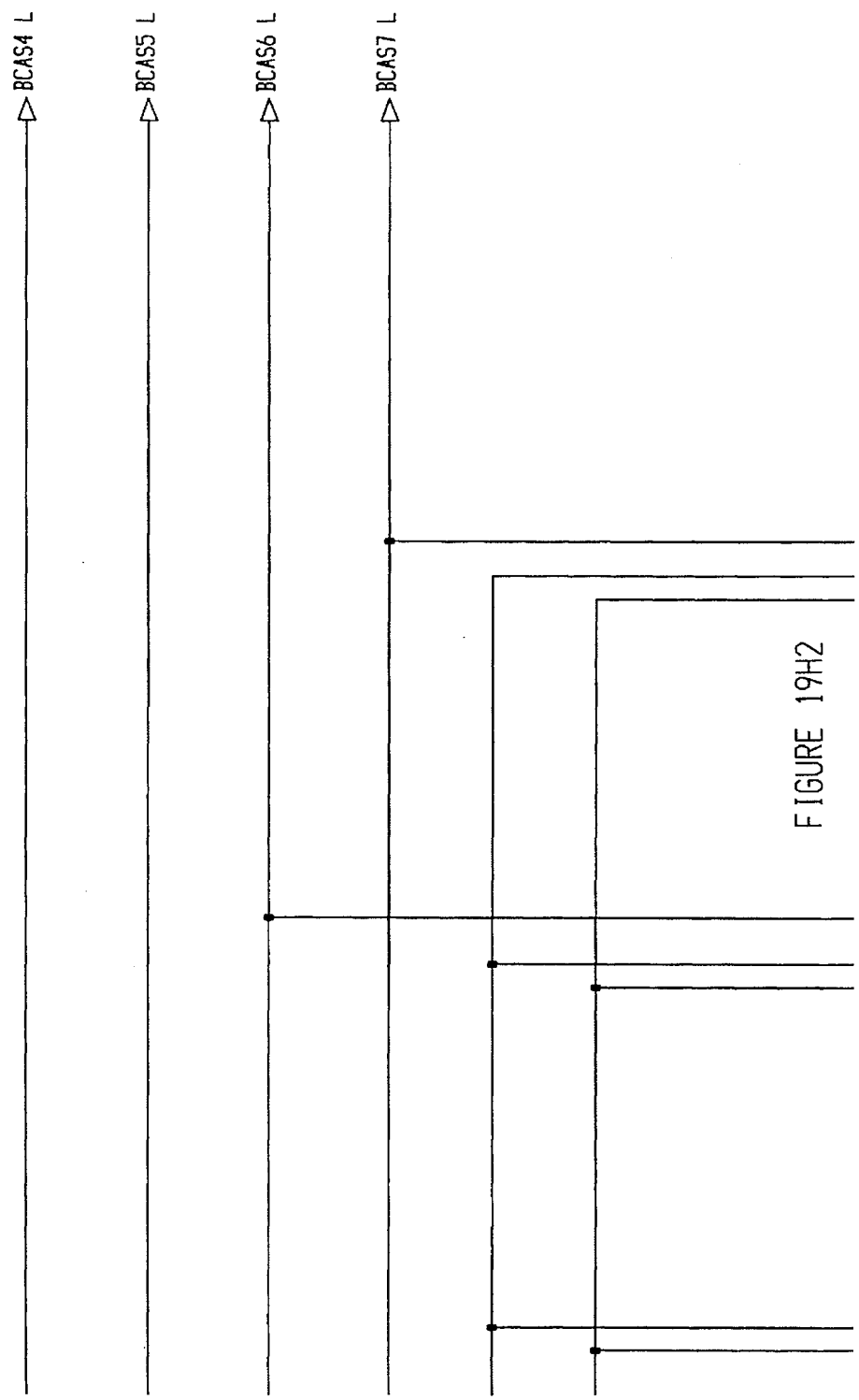

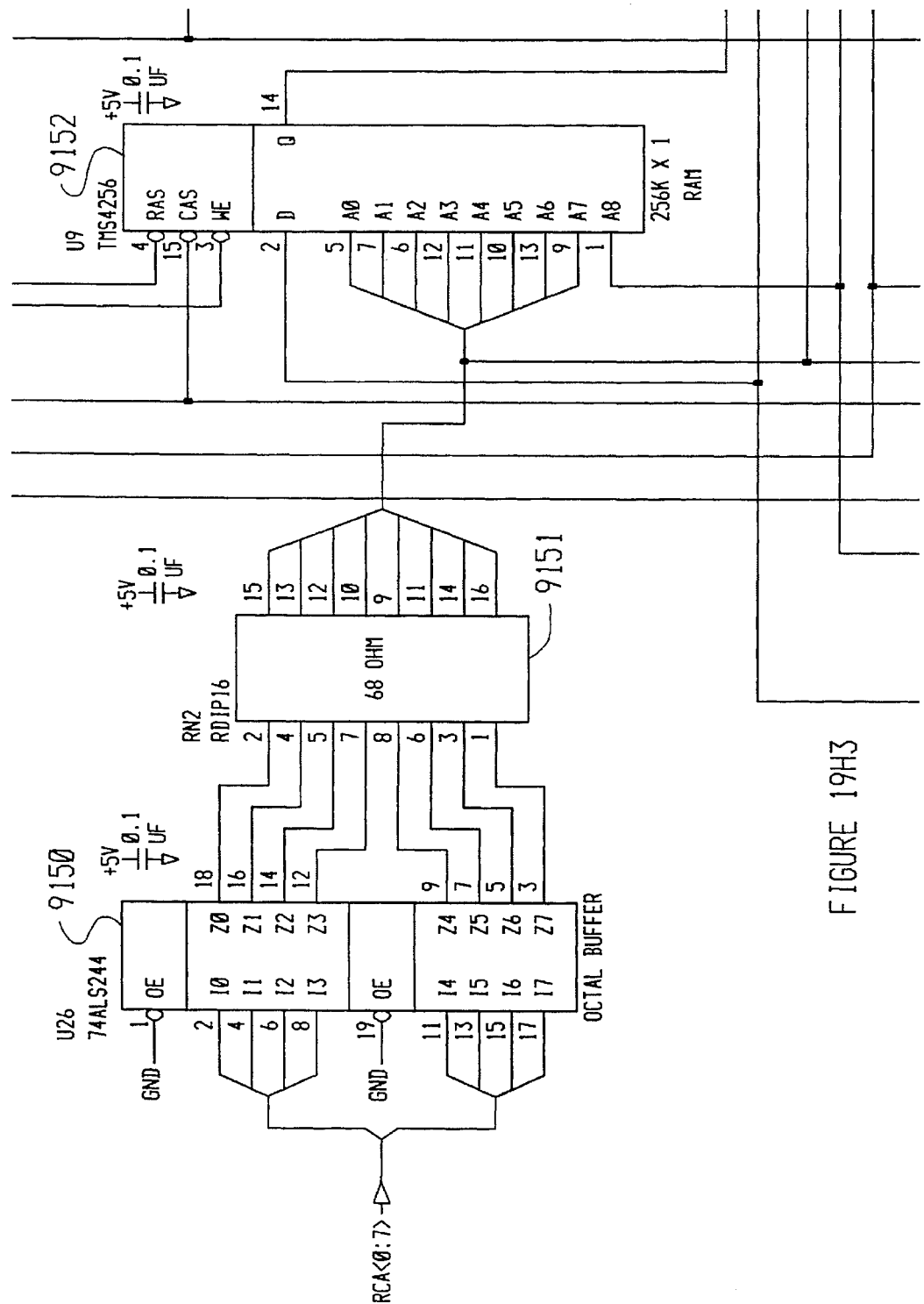
FIGURE 19H3

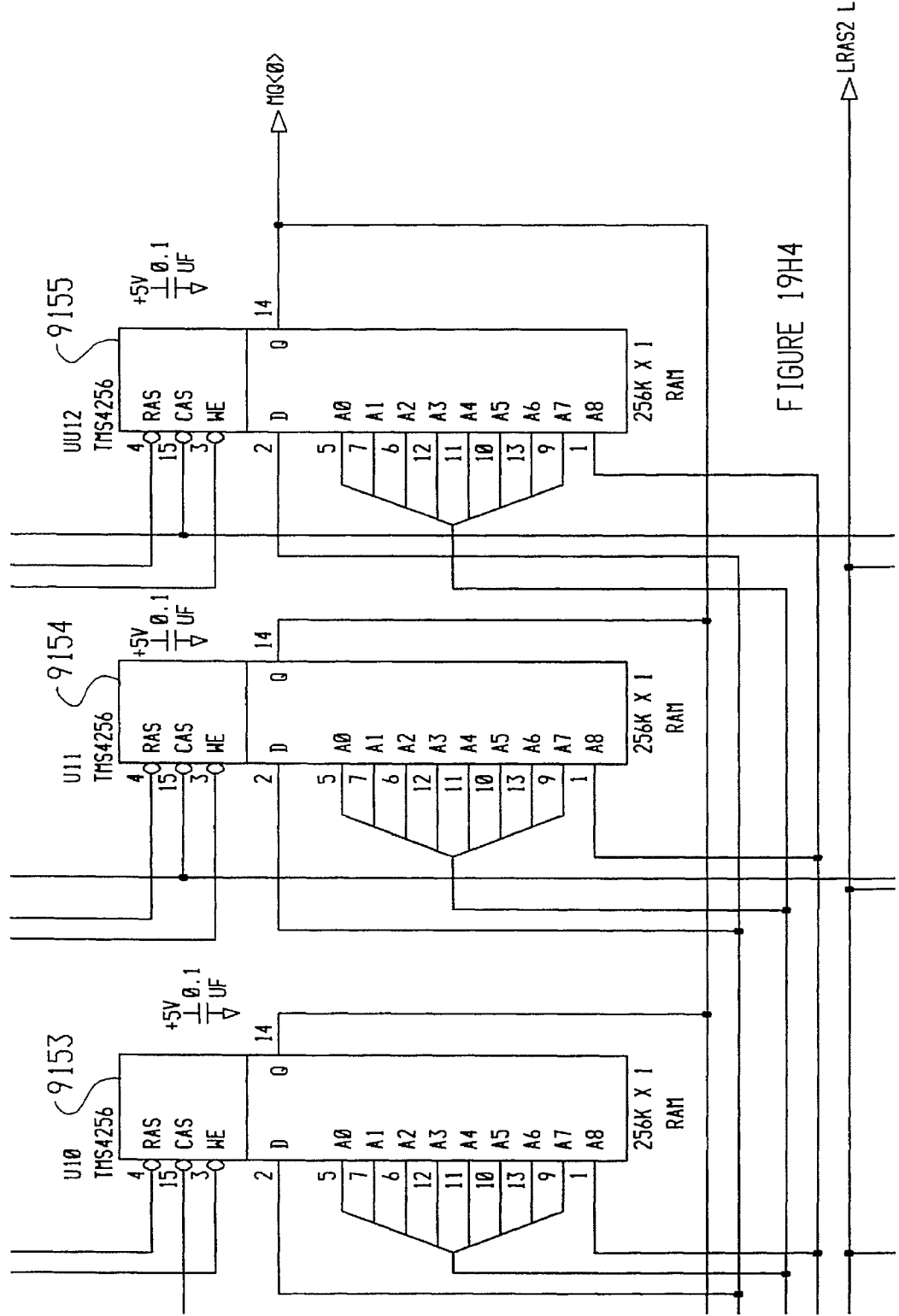
FIGURE 19H4

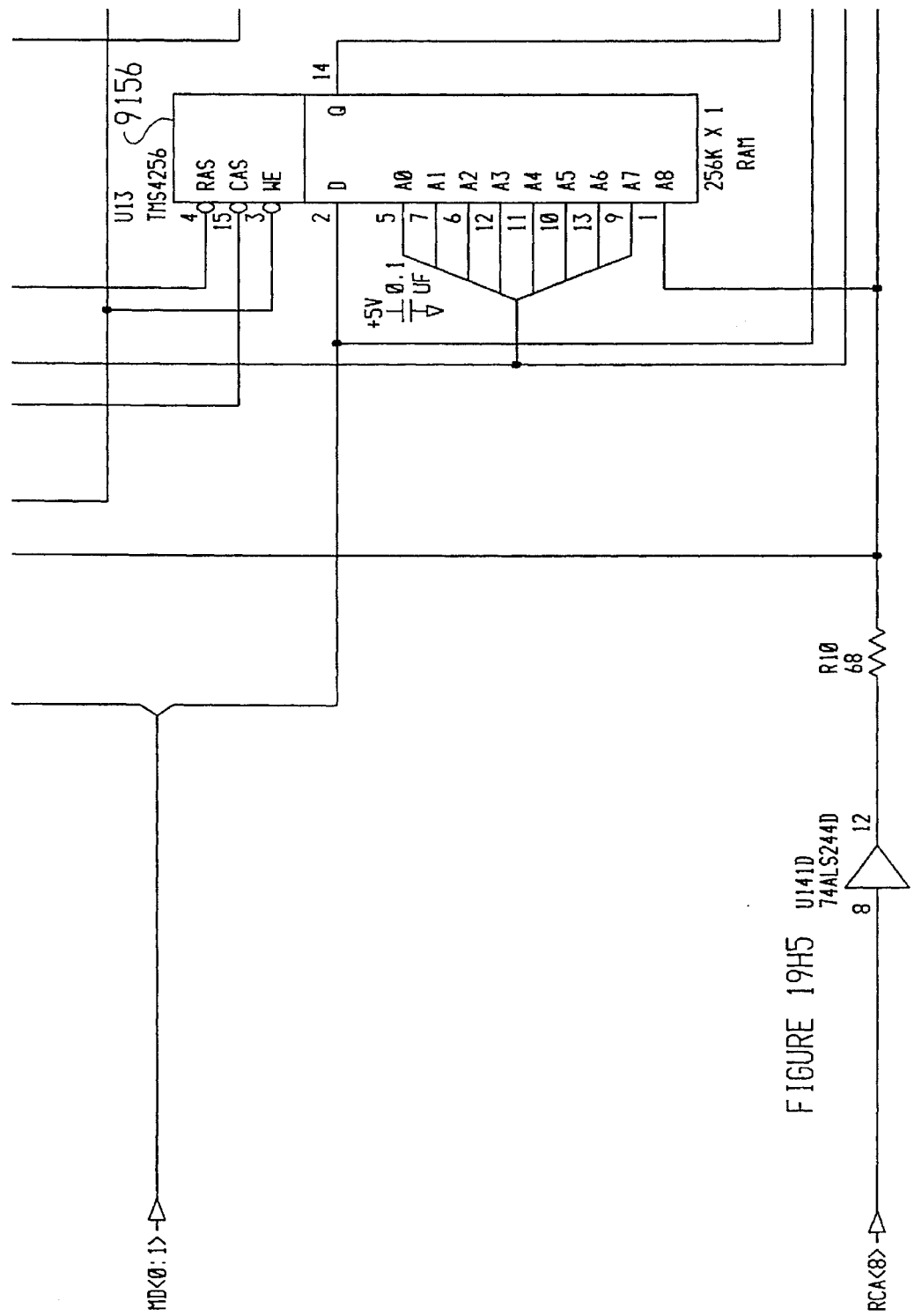
FIGURE 19H5

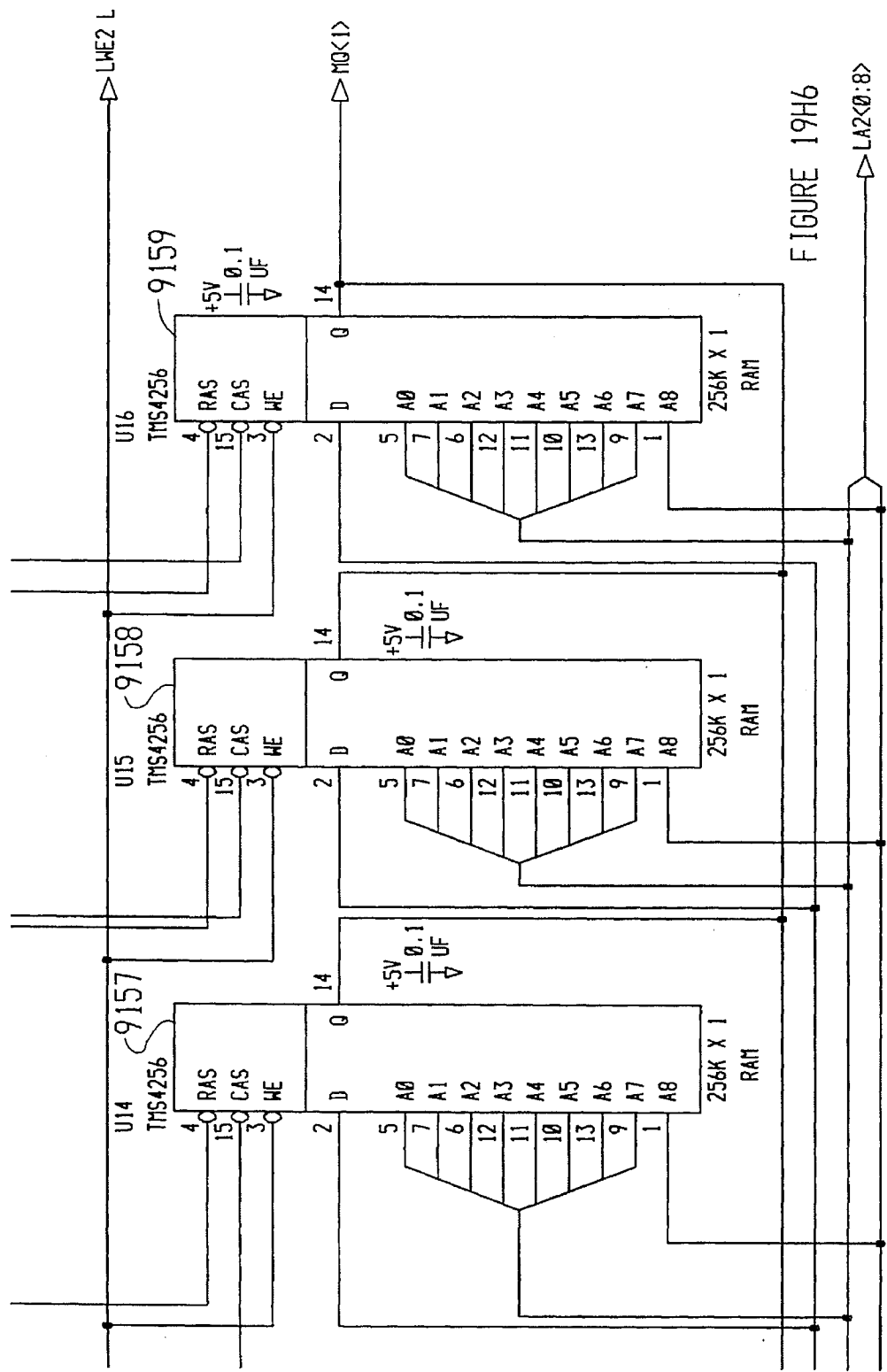
FIGURE 19H6

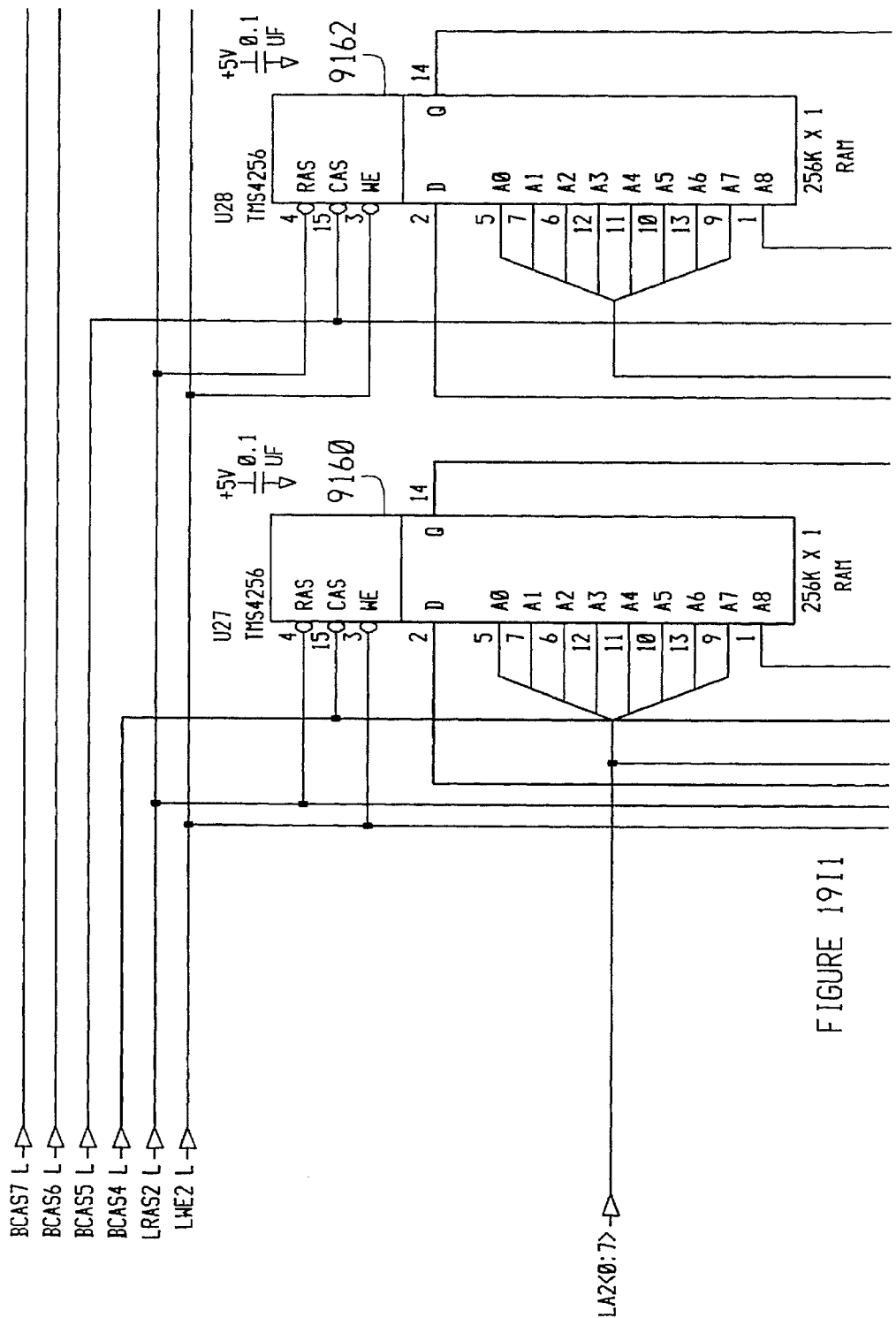
FIGURE 1911

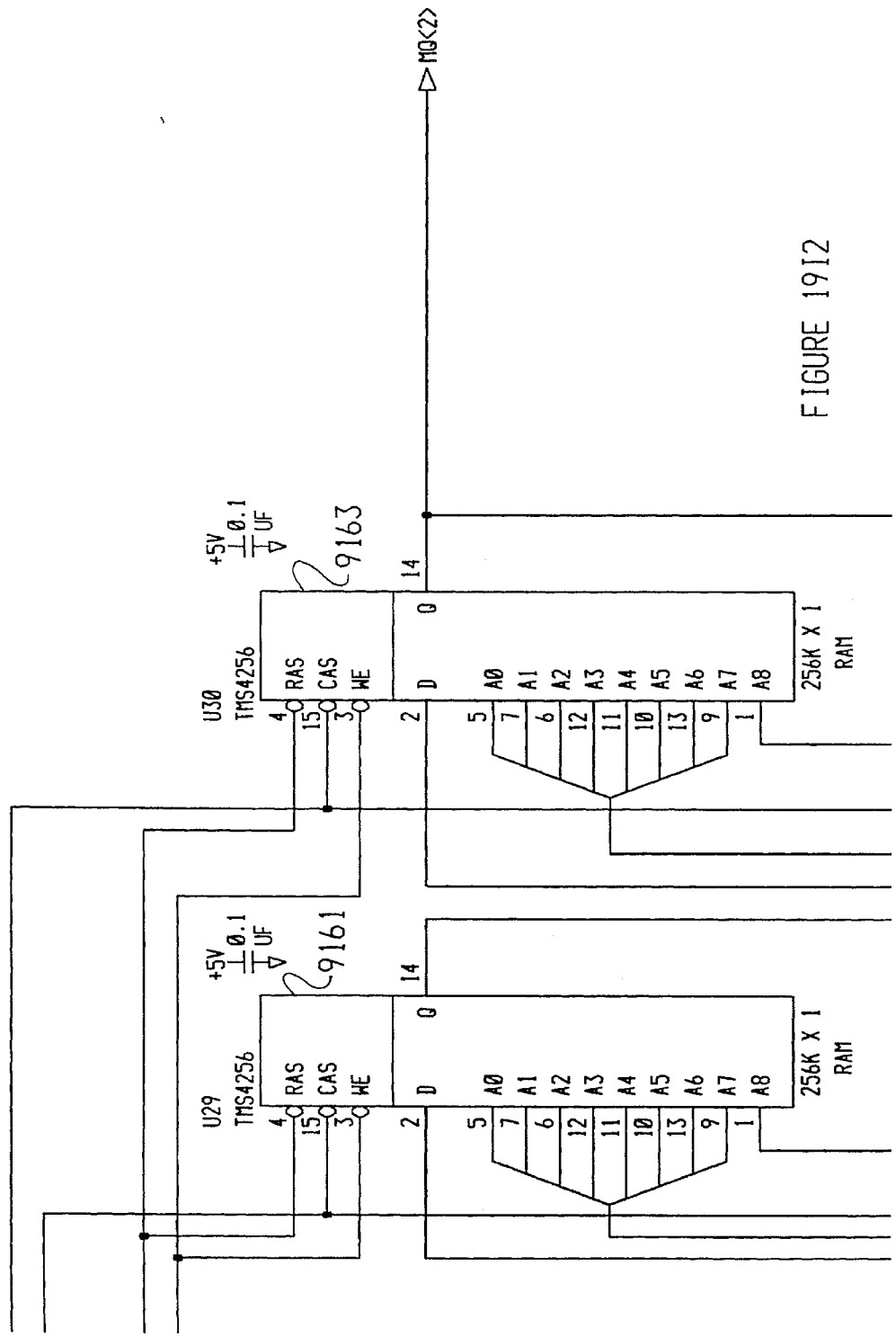
FIGURE 1912

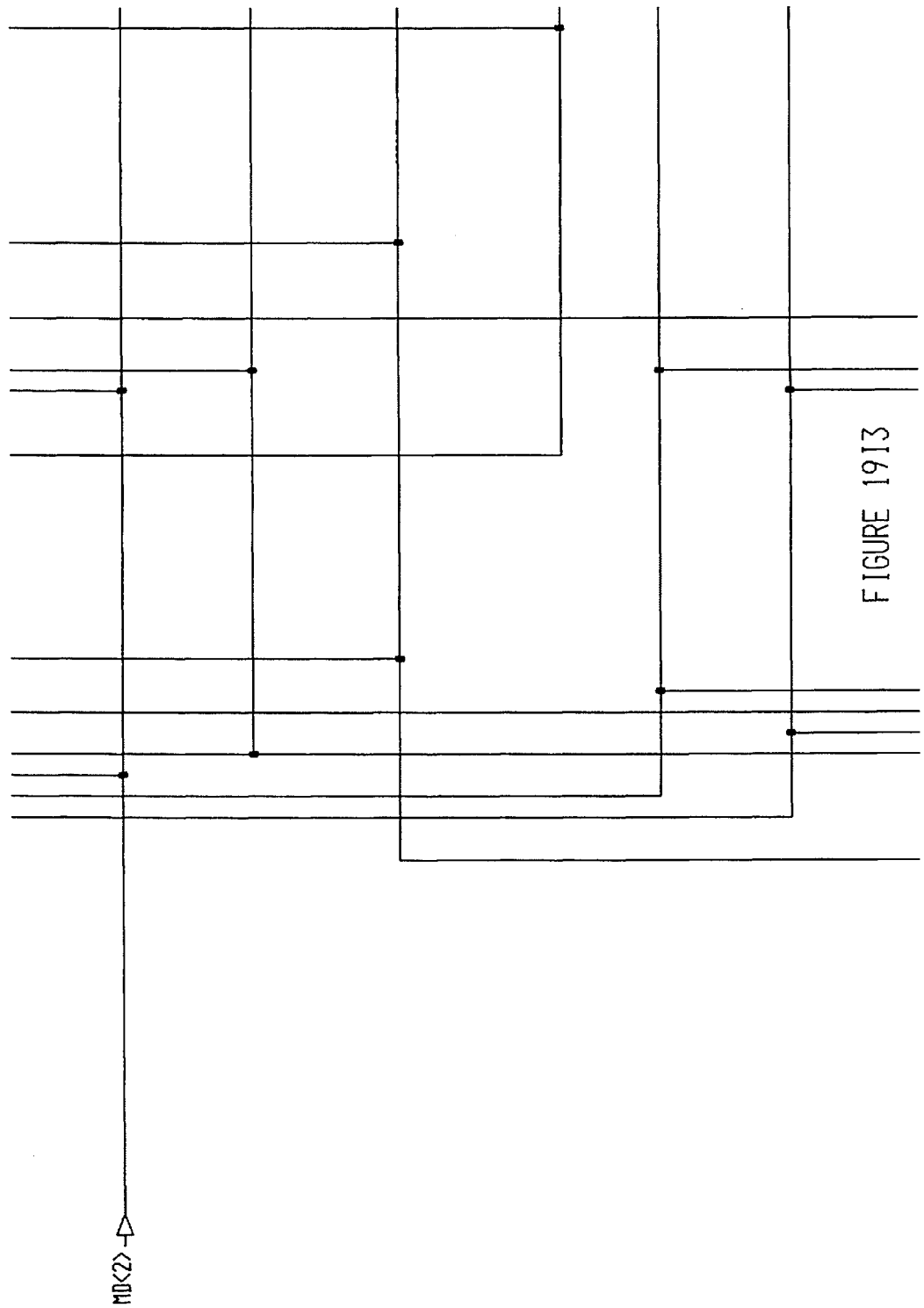

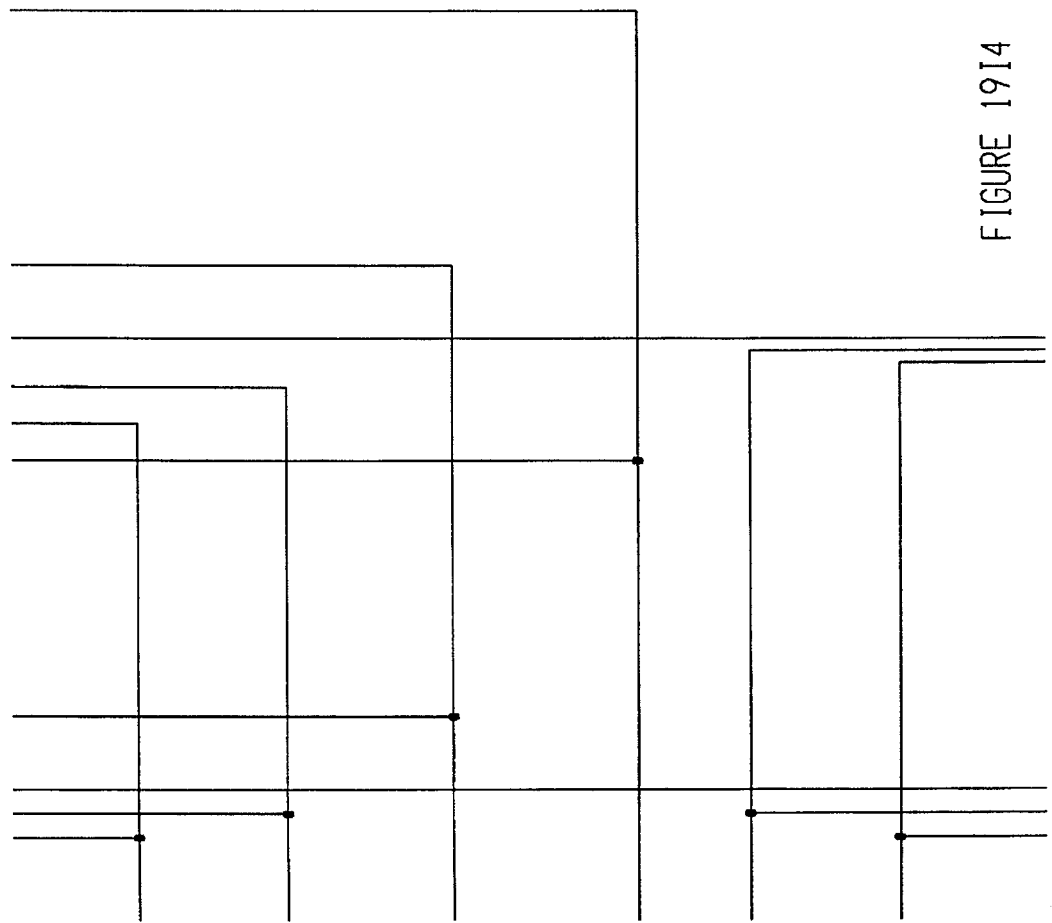
FIGURE 1914

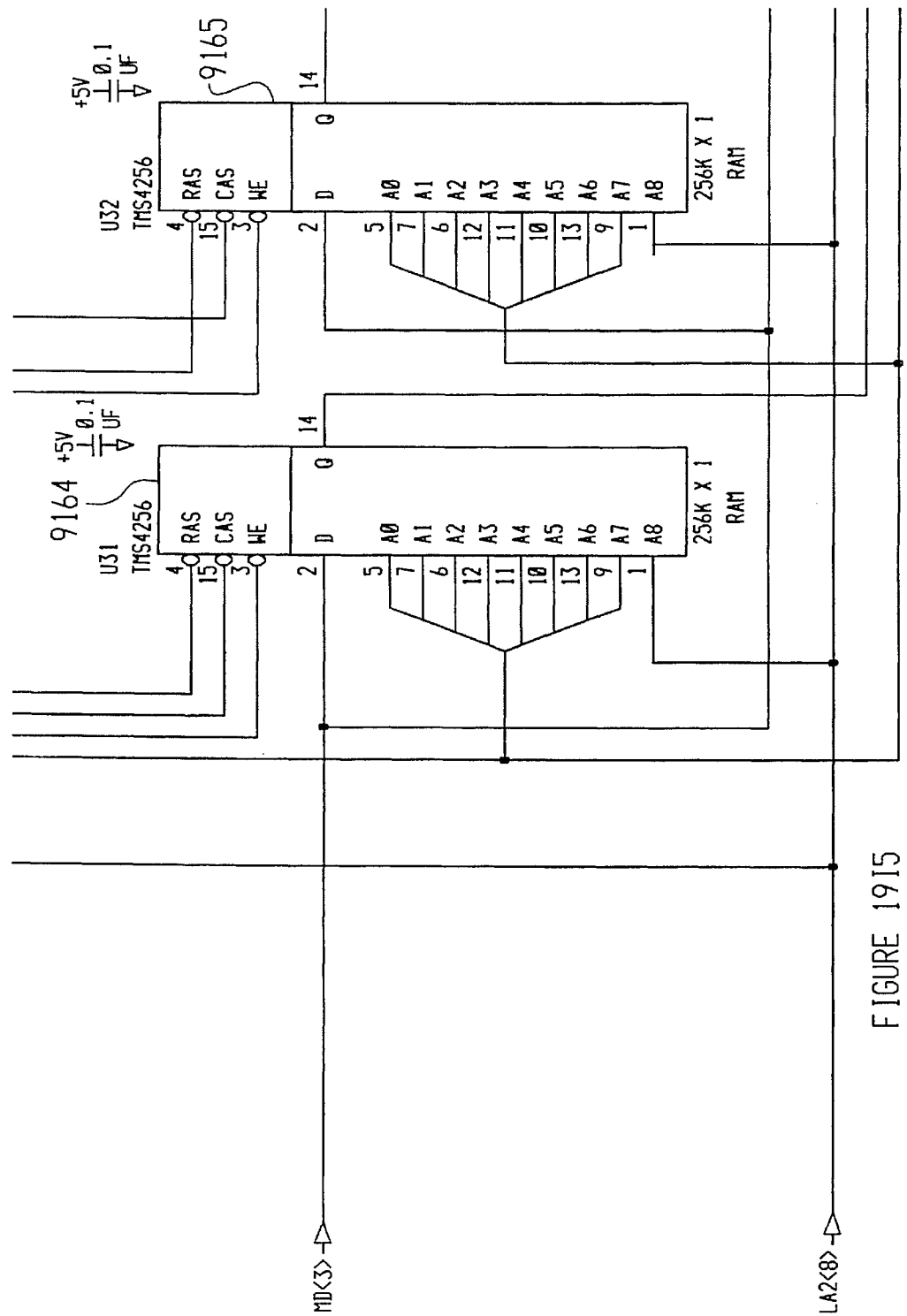
FIGURE 1915

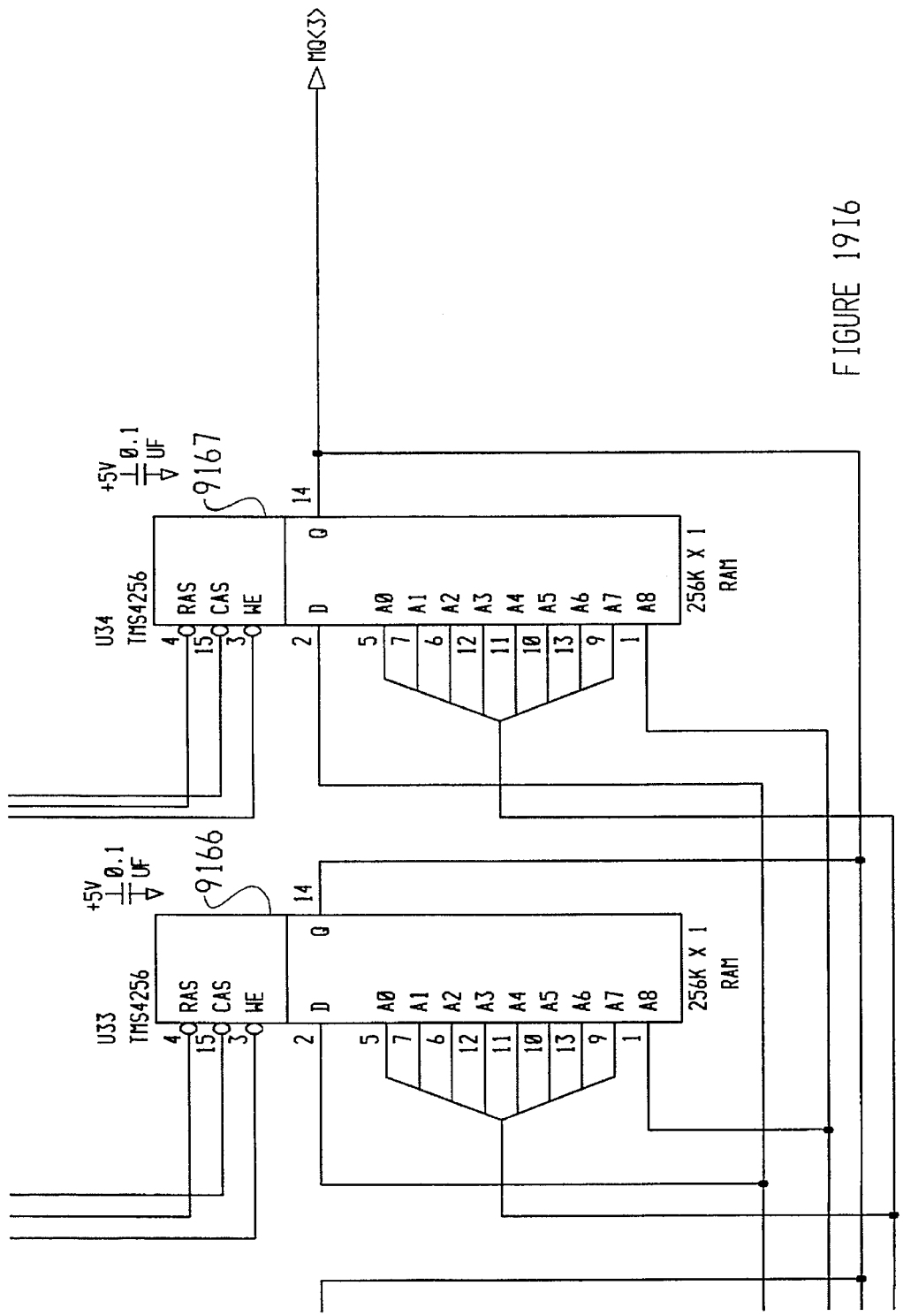
FIGURE 1916

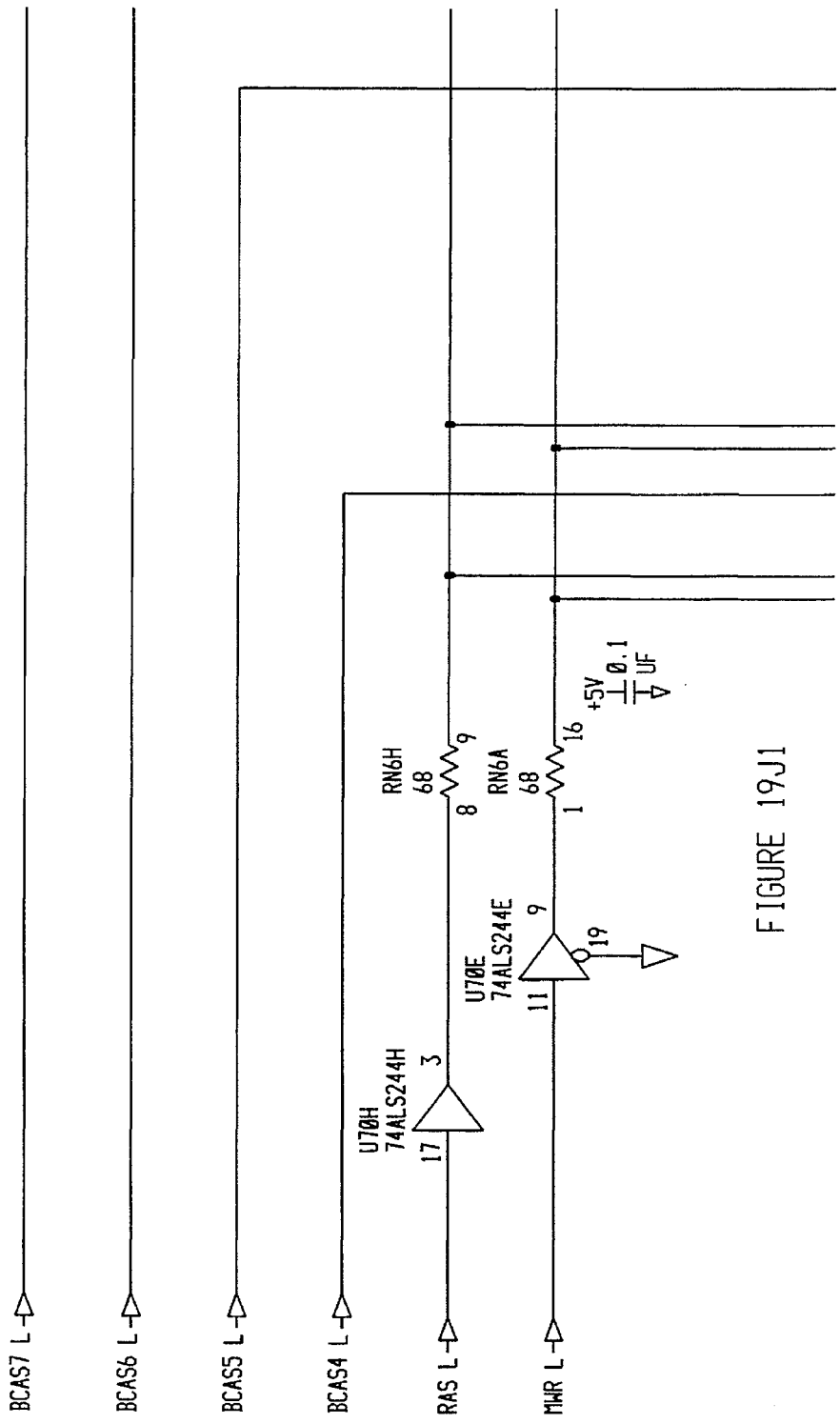
FIGURE 19J1

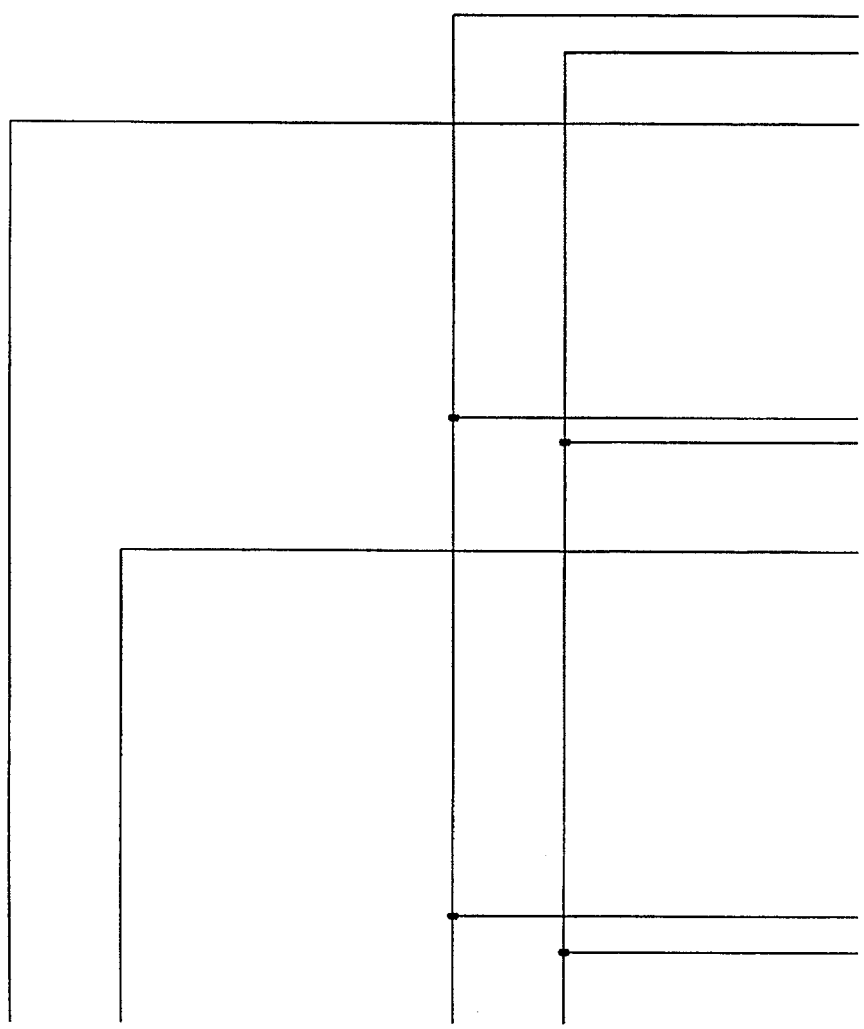
FIGURE 19J2

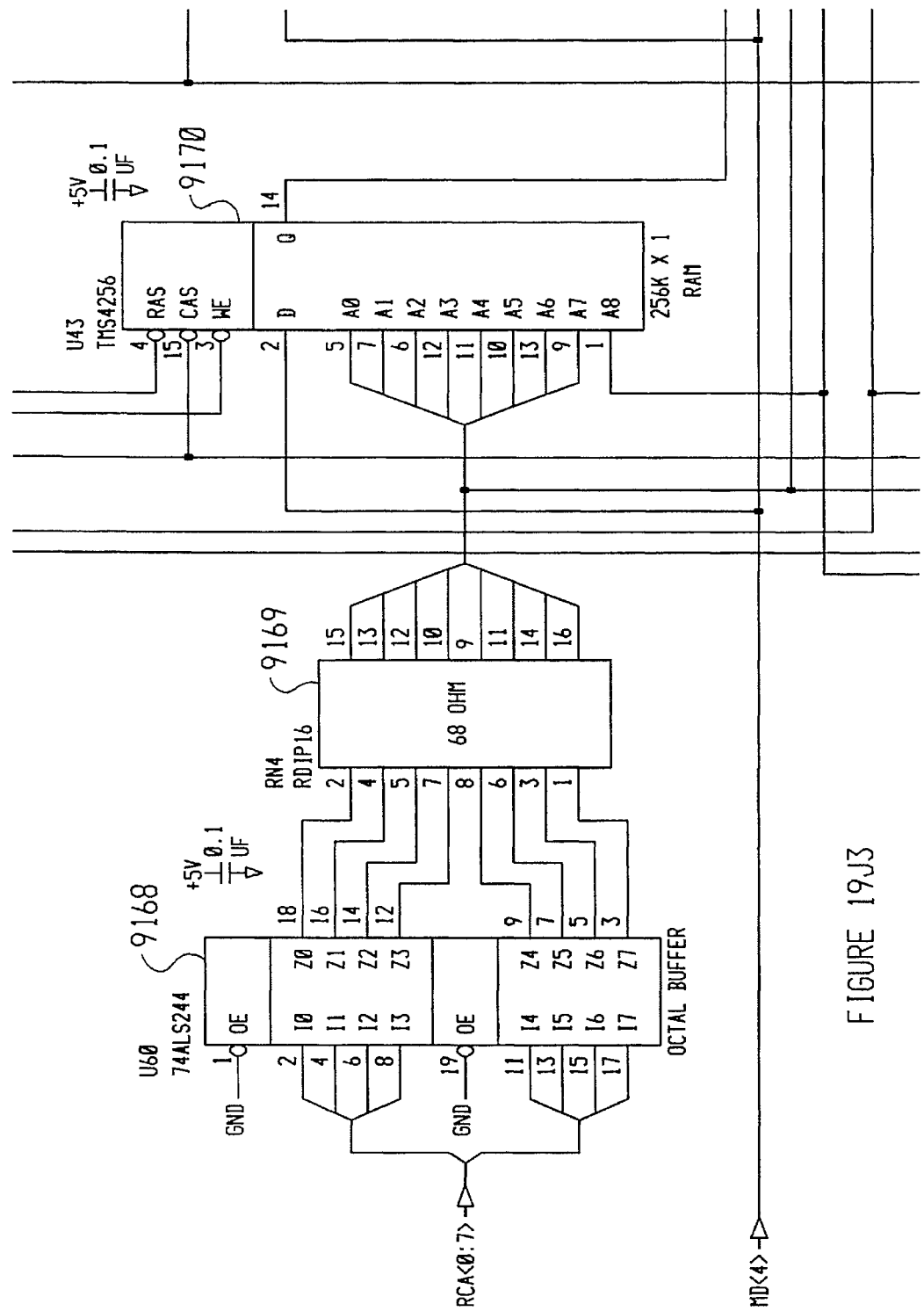
FIGURE 19J3

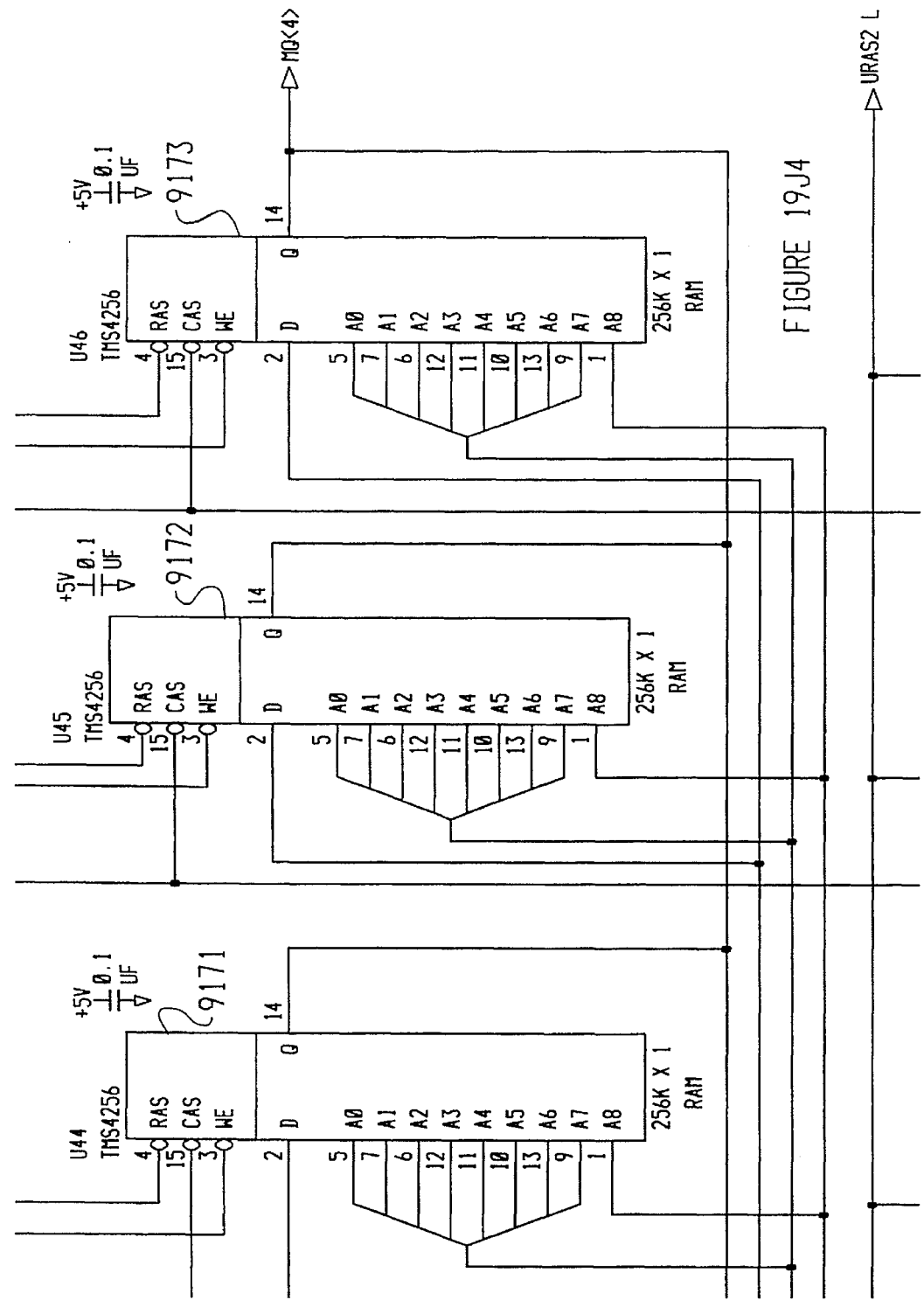
FIGURE 19J4

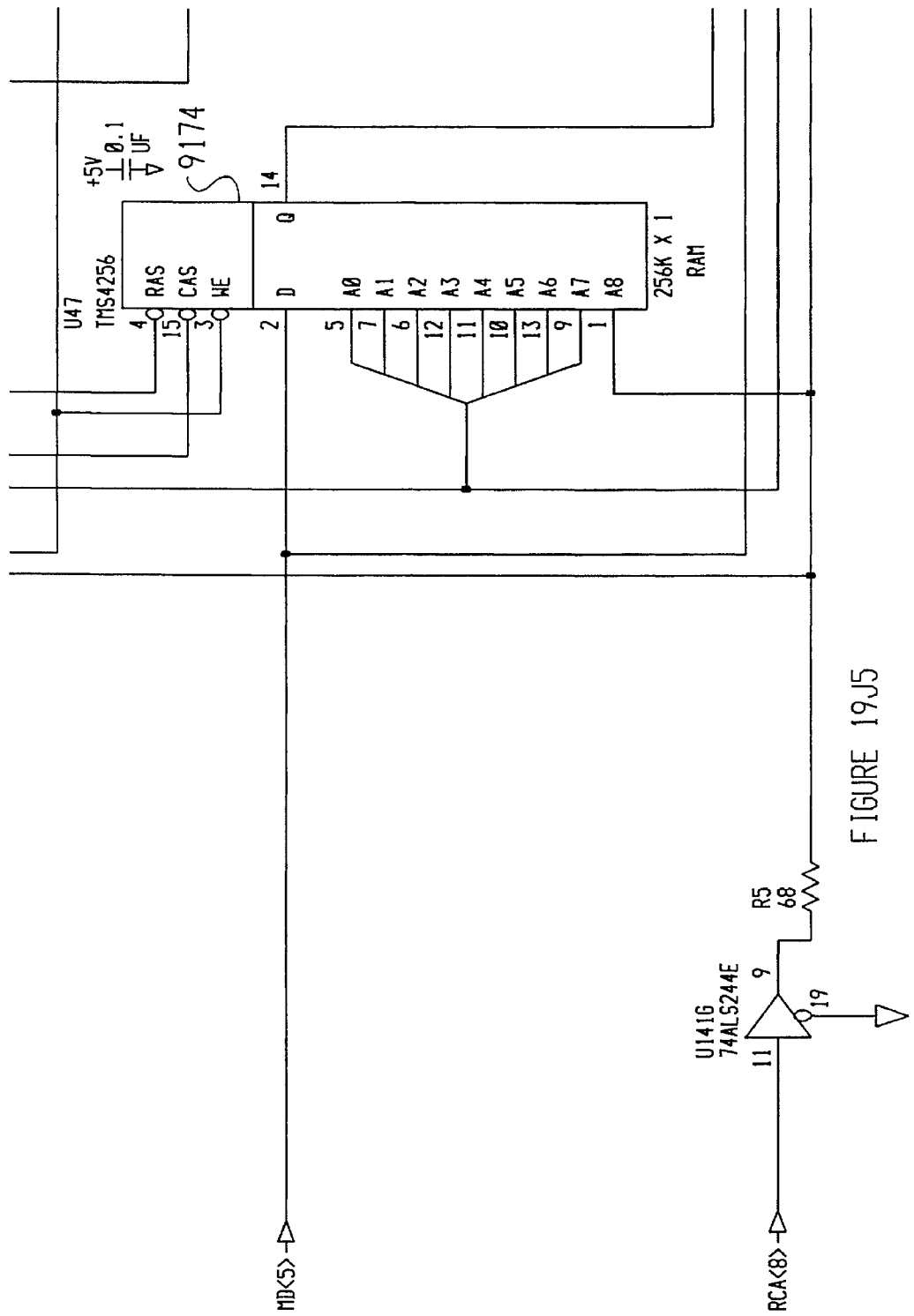
FIGURE 19J5

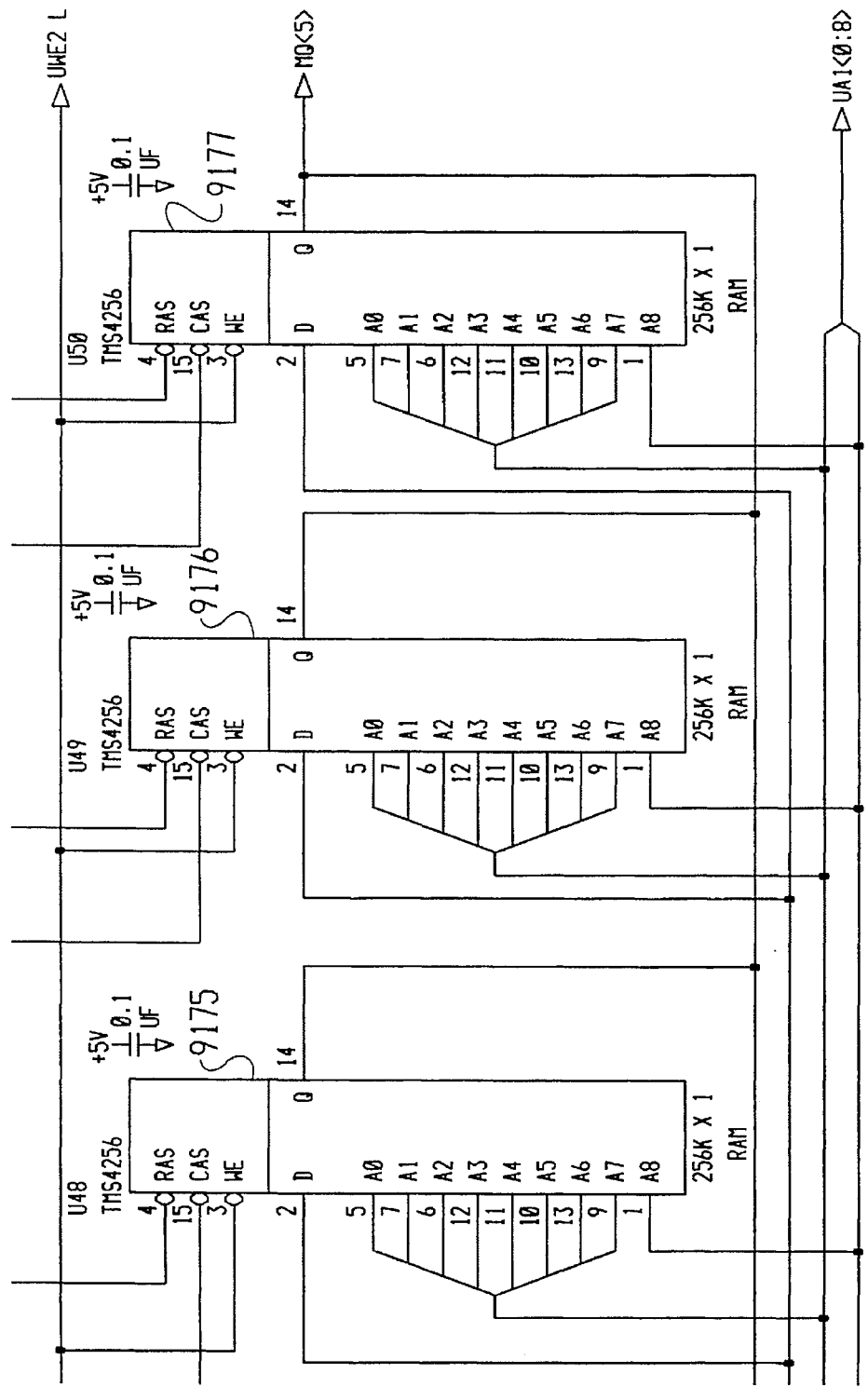
FIGURE 19J6

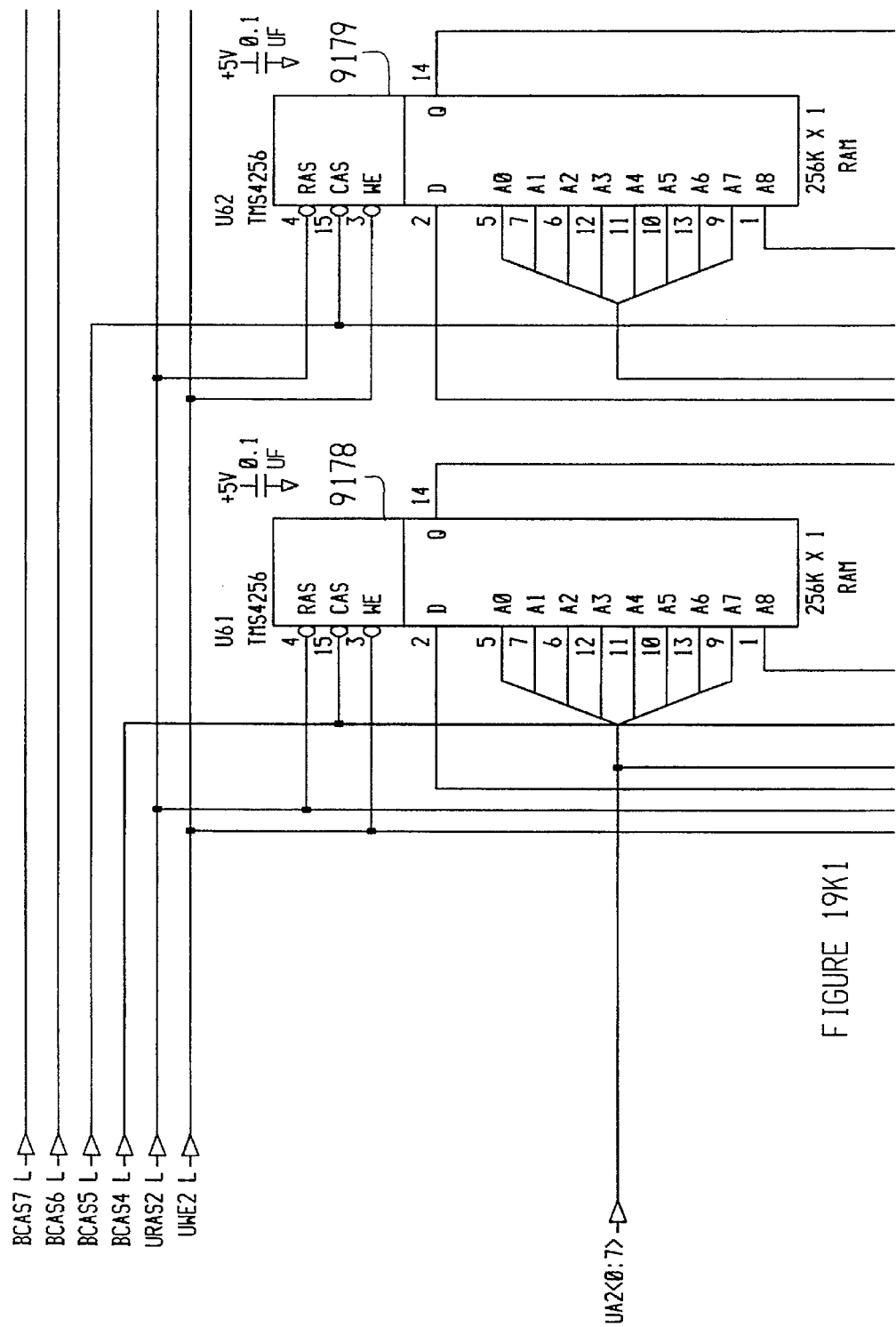
FIGURE 19K1

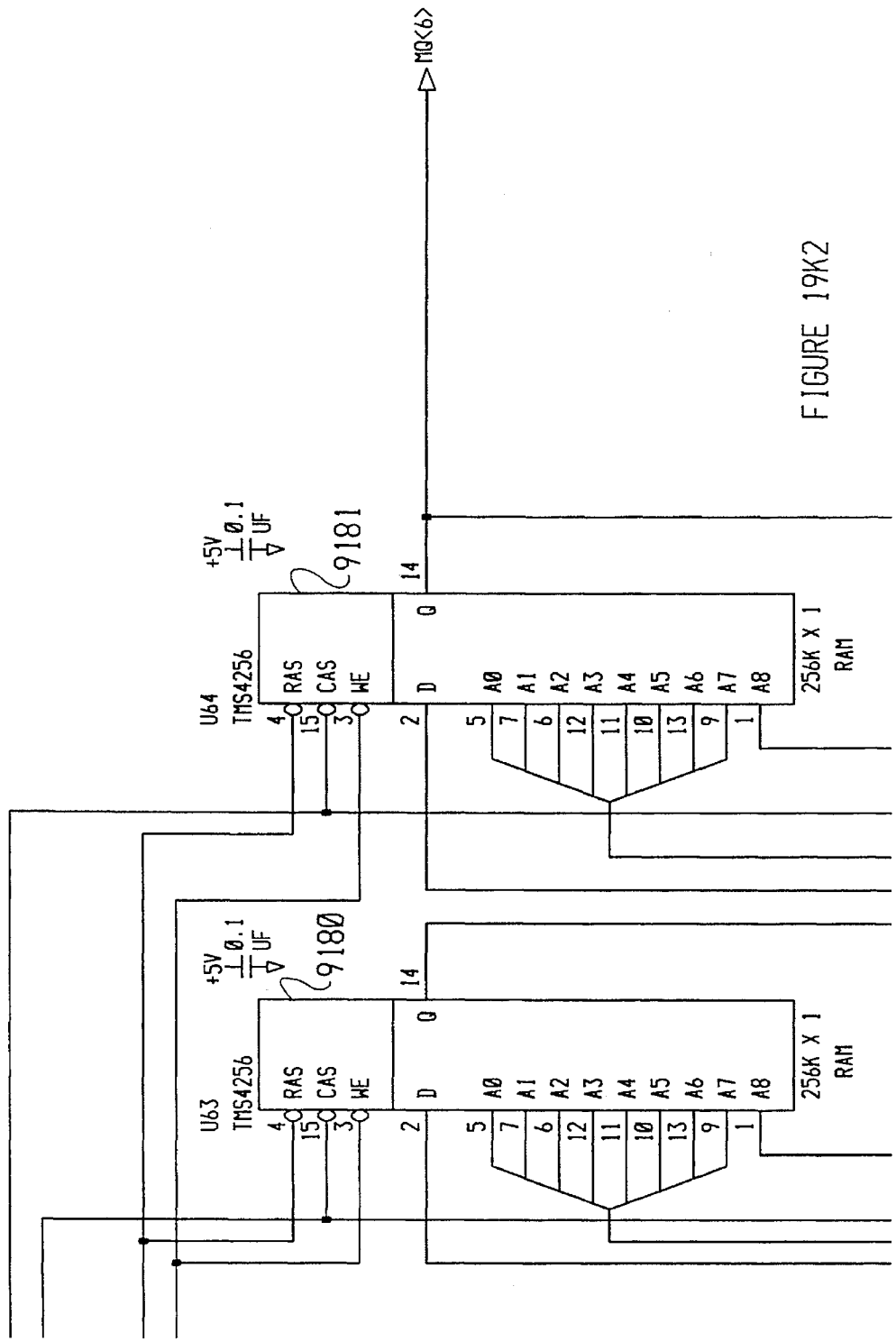
FIGURE 19K2

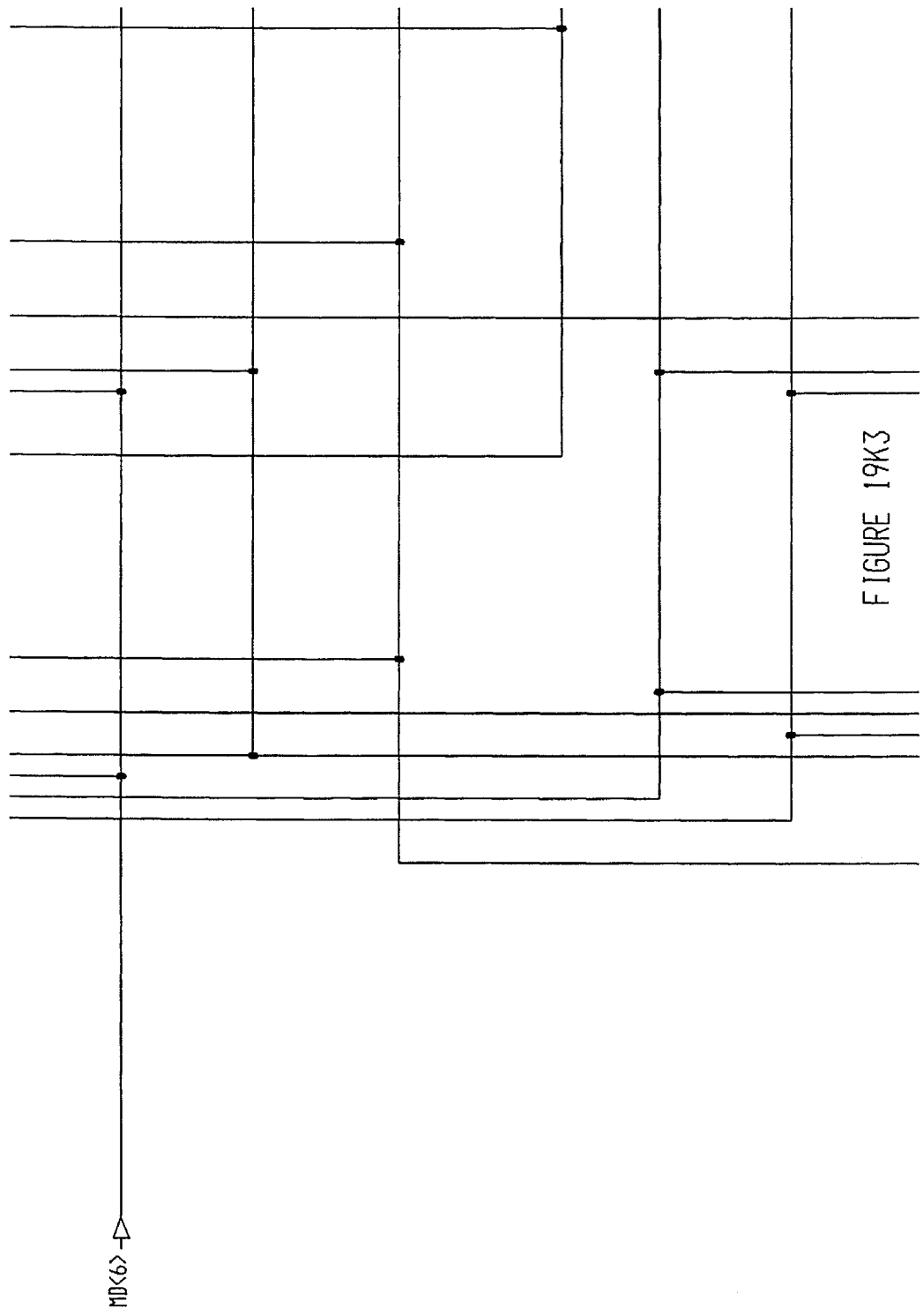

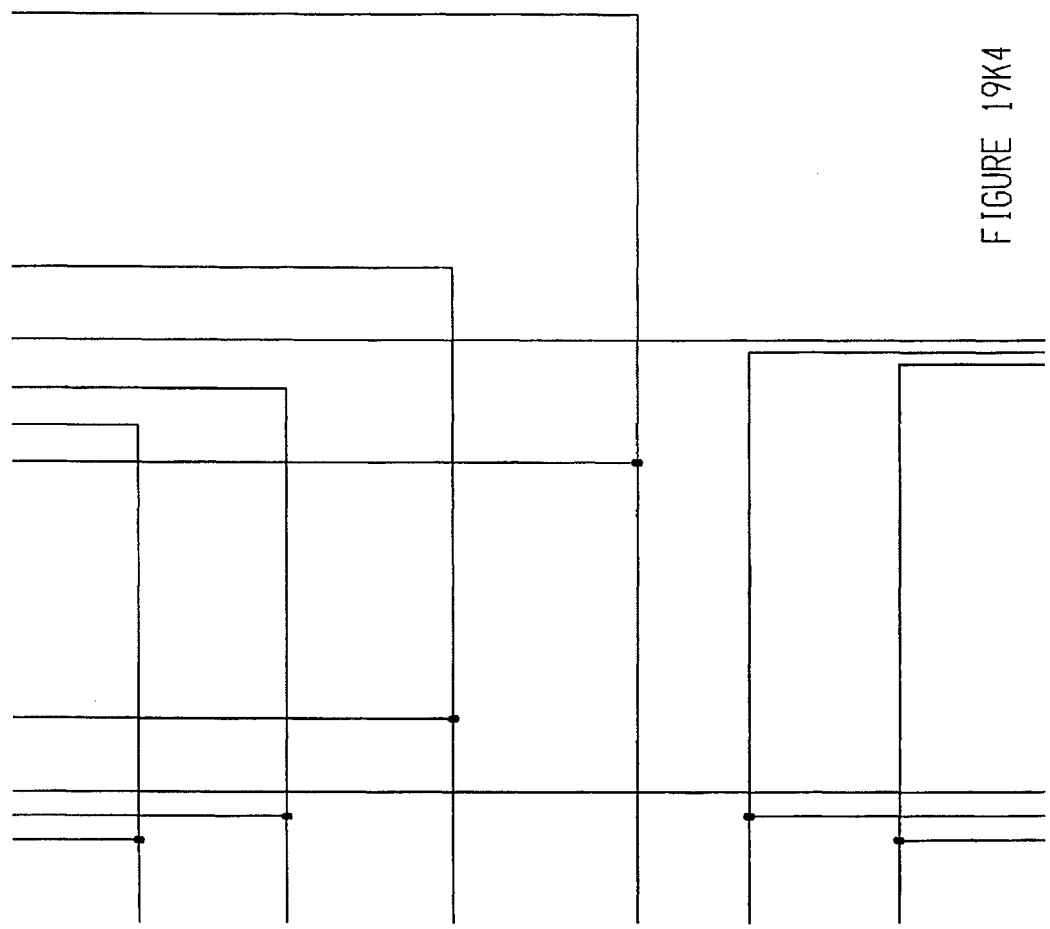

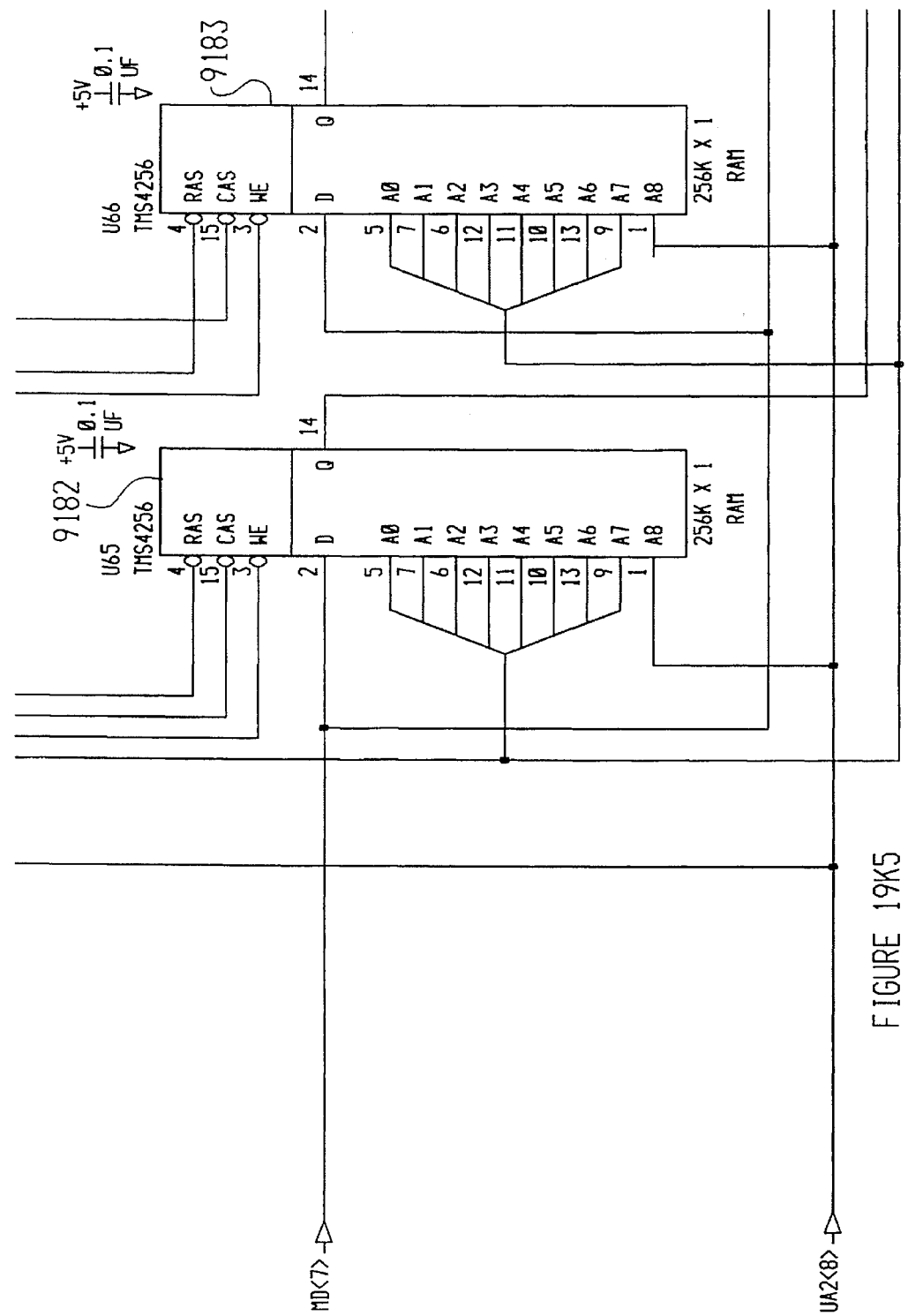
FIGURE 19K5

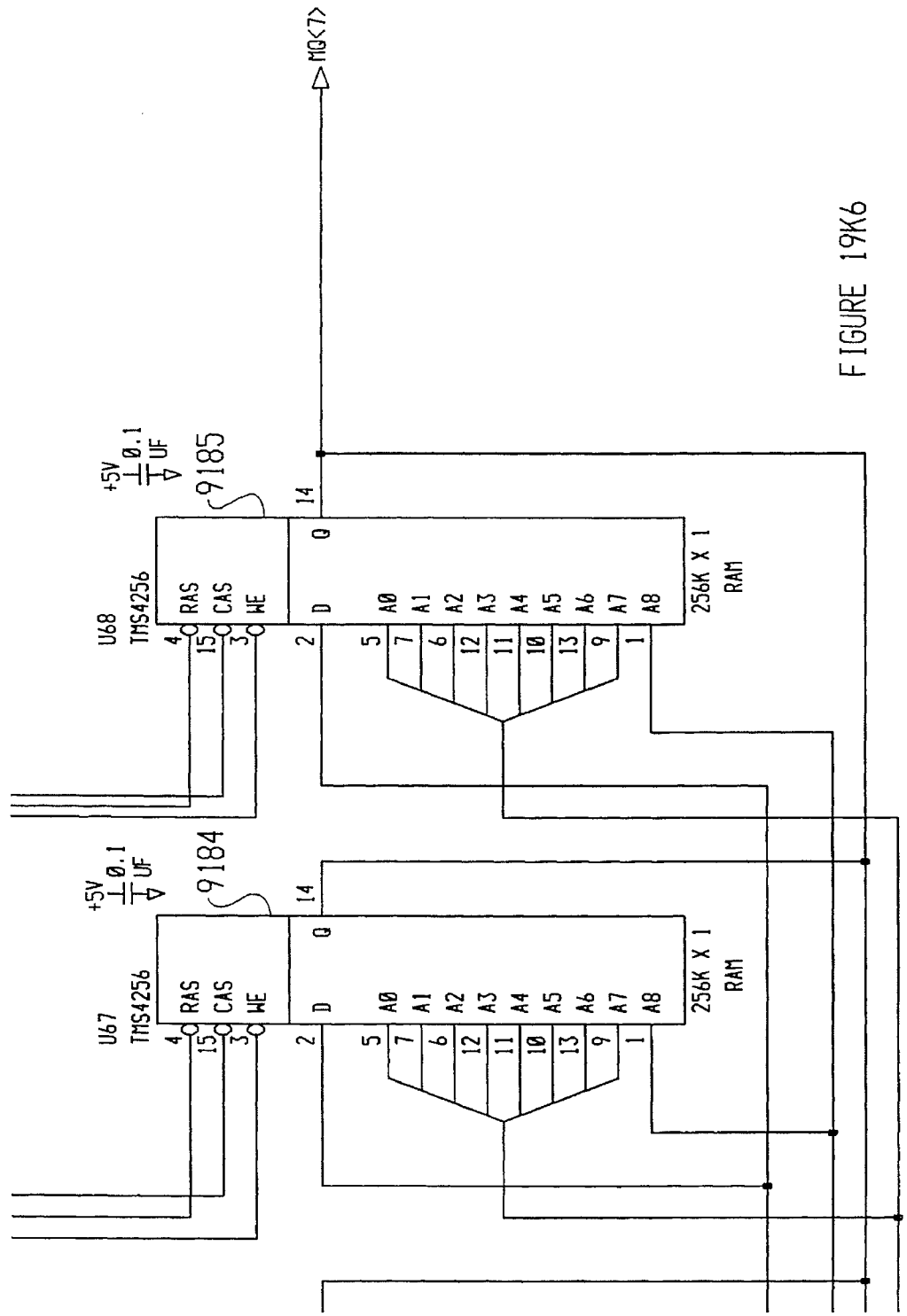
FIGURE 19K6

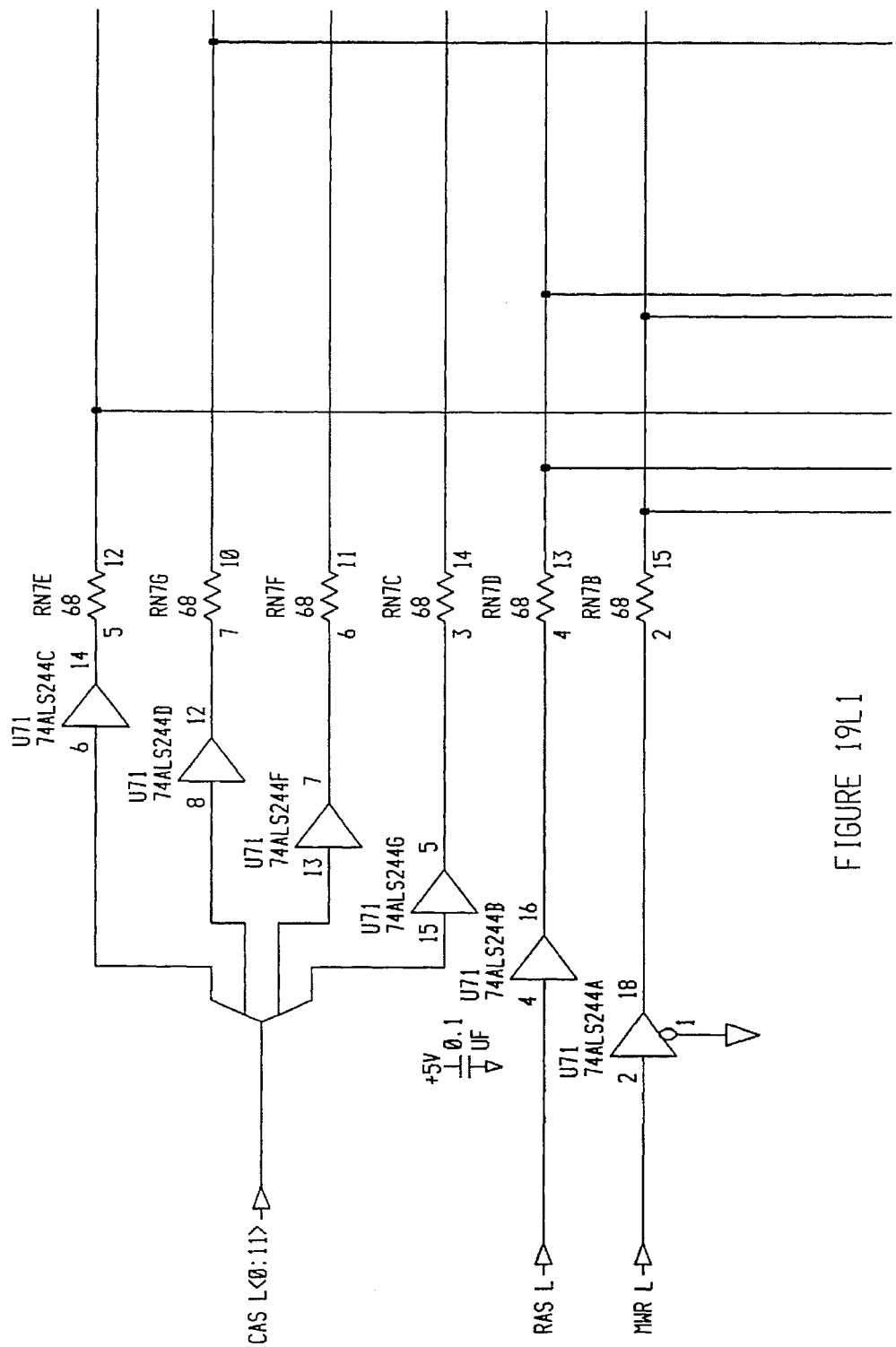
FIGURE 19L1

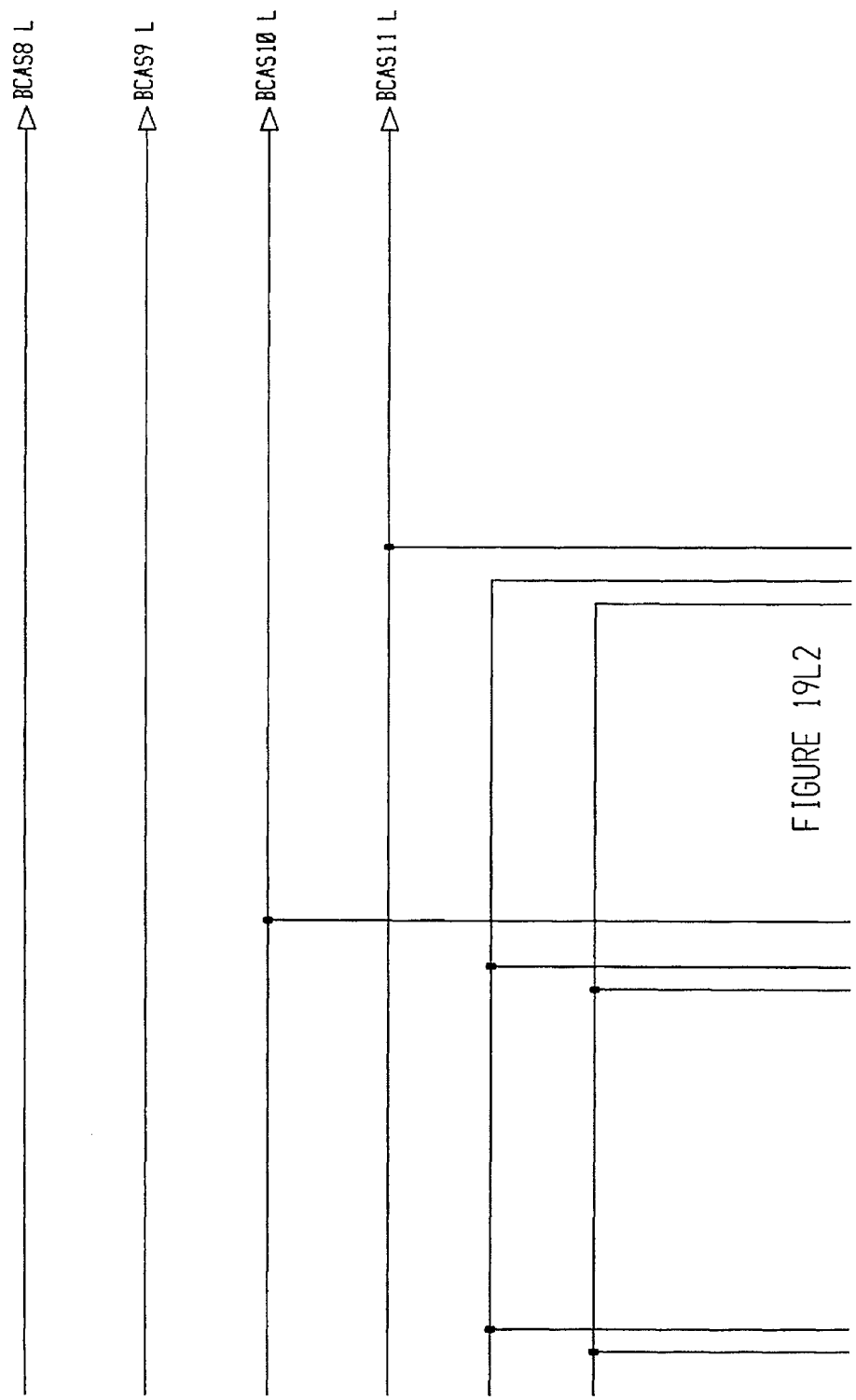
FIGURE 19L2

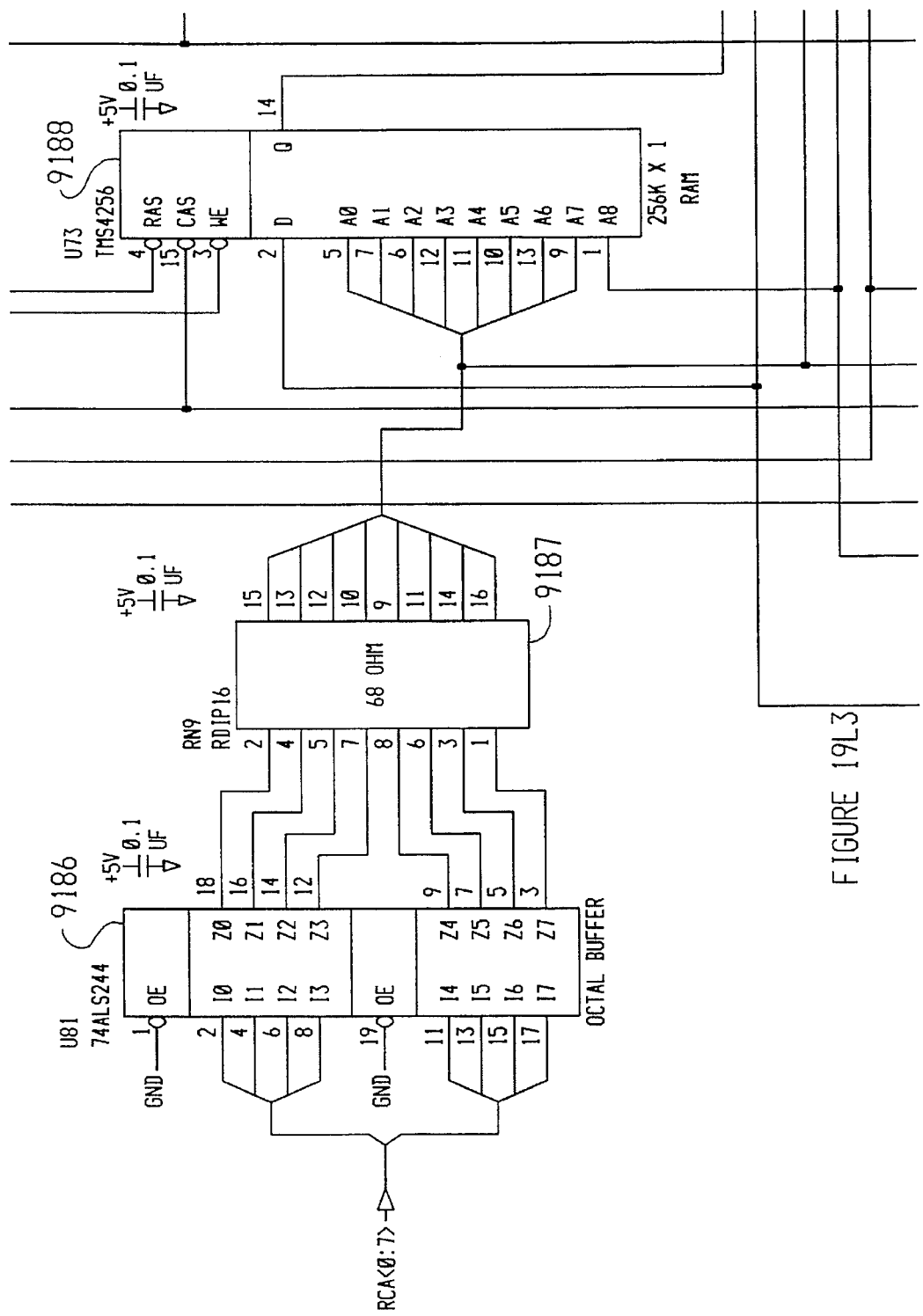
FIGURE 19L3

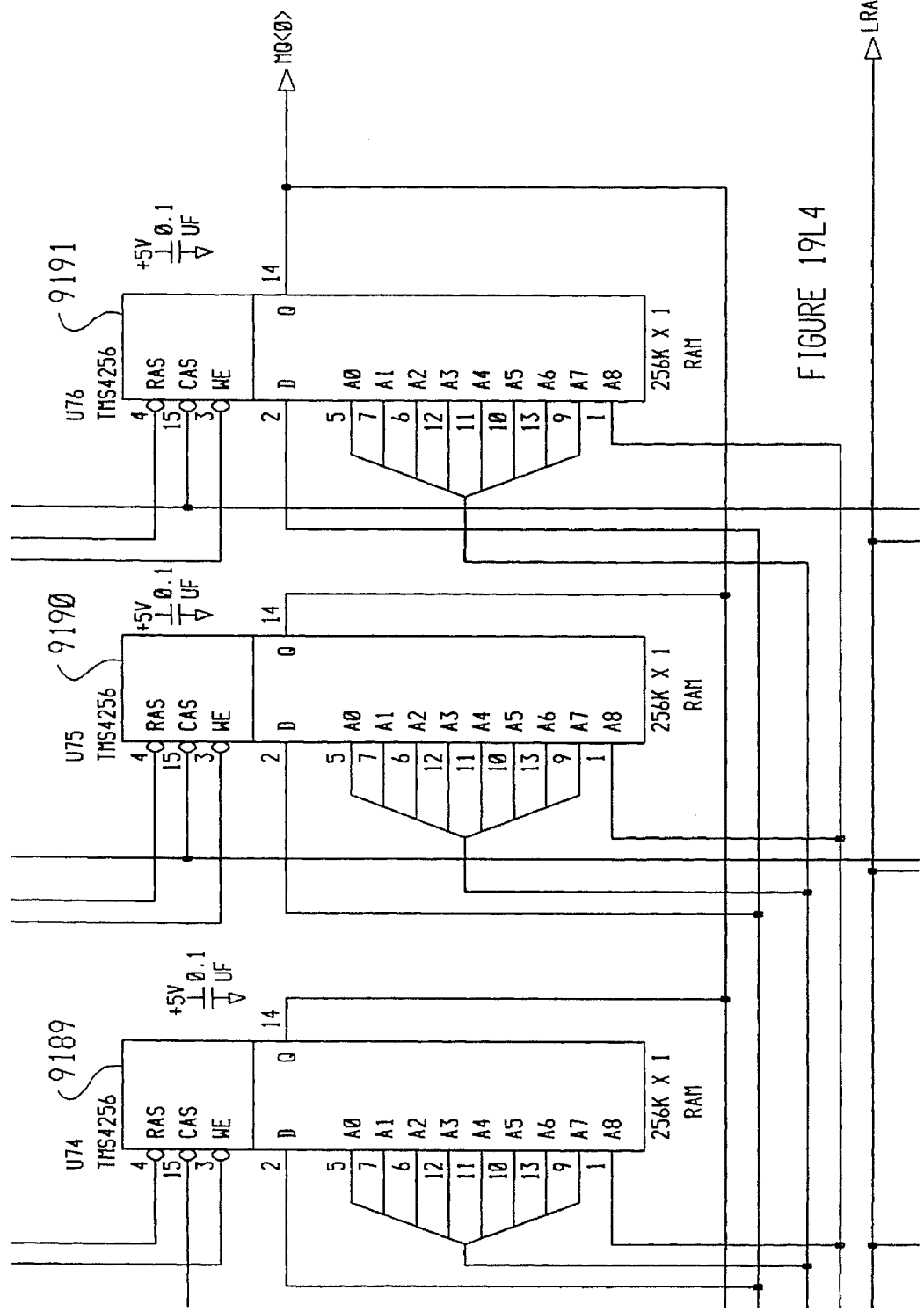
FIGURE 19L4

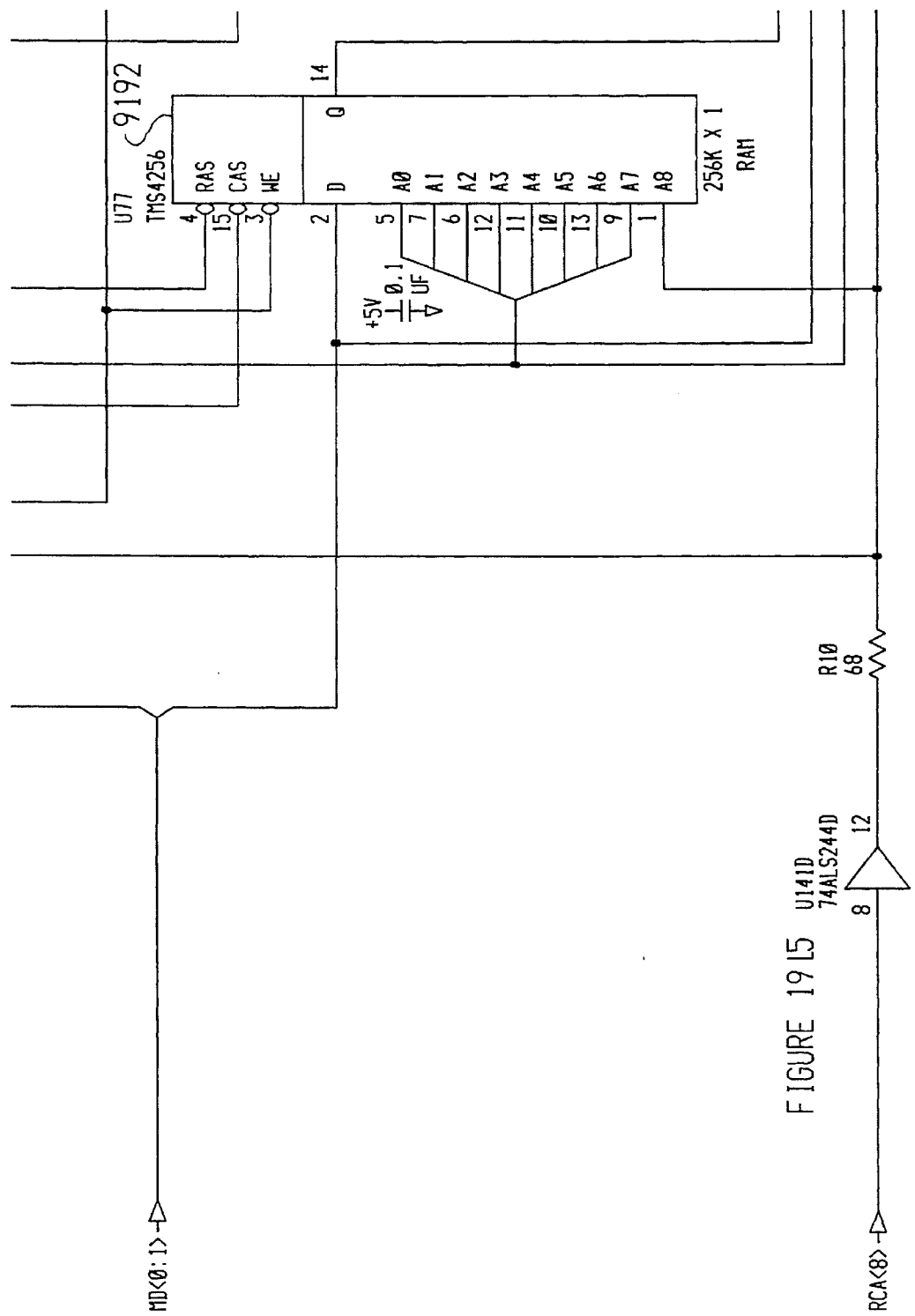

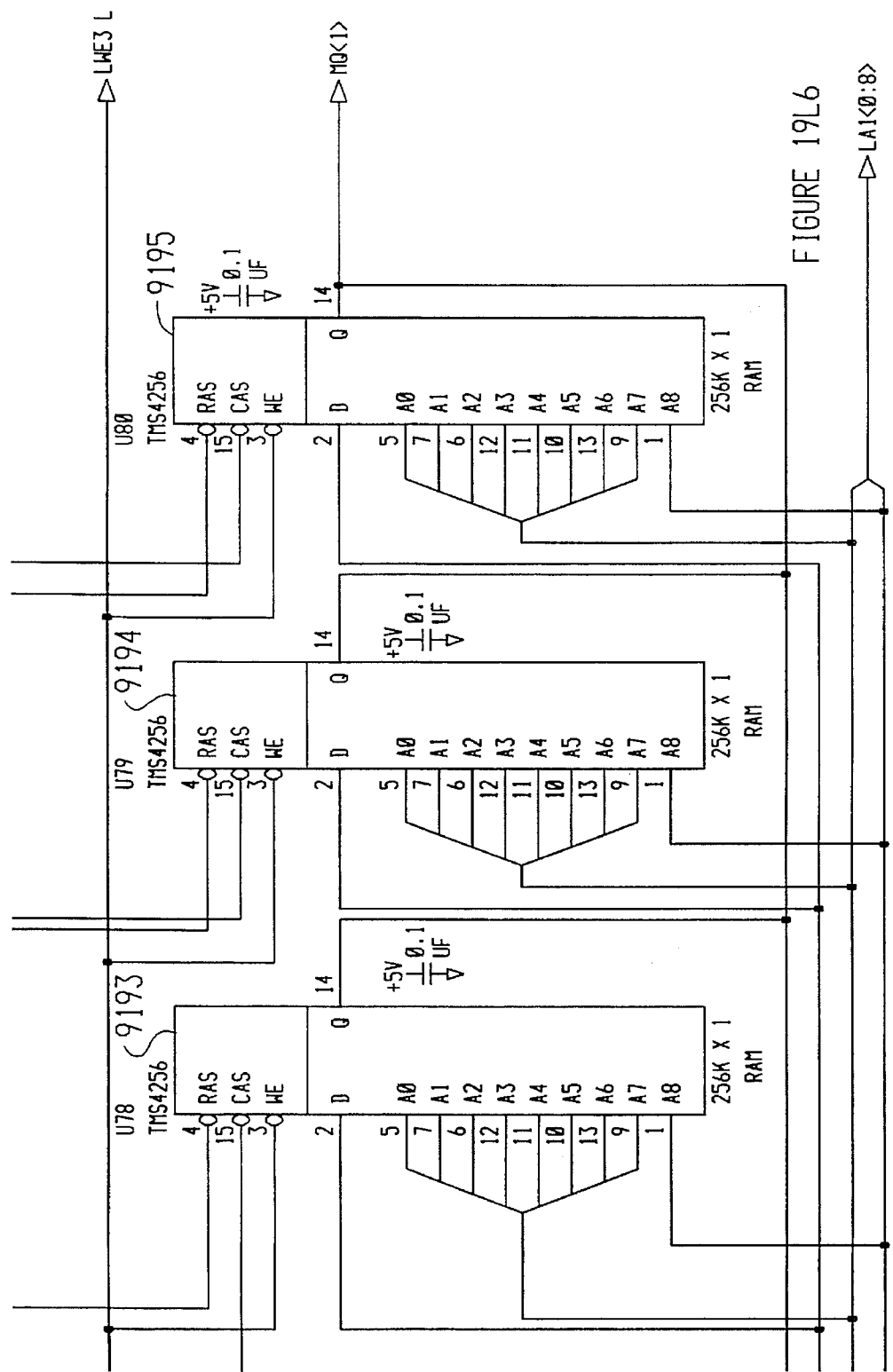
FIGURE 19L6

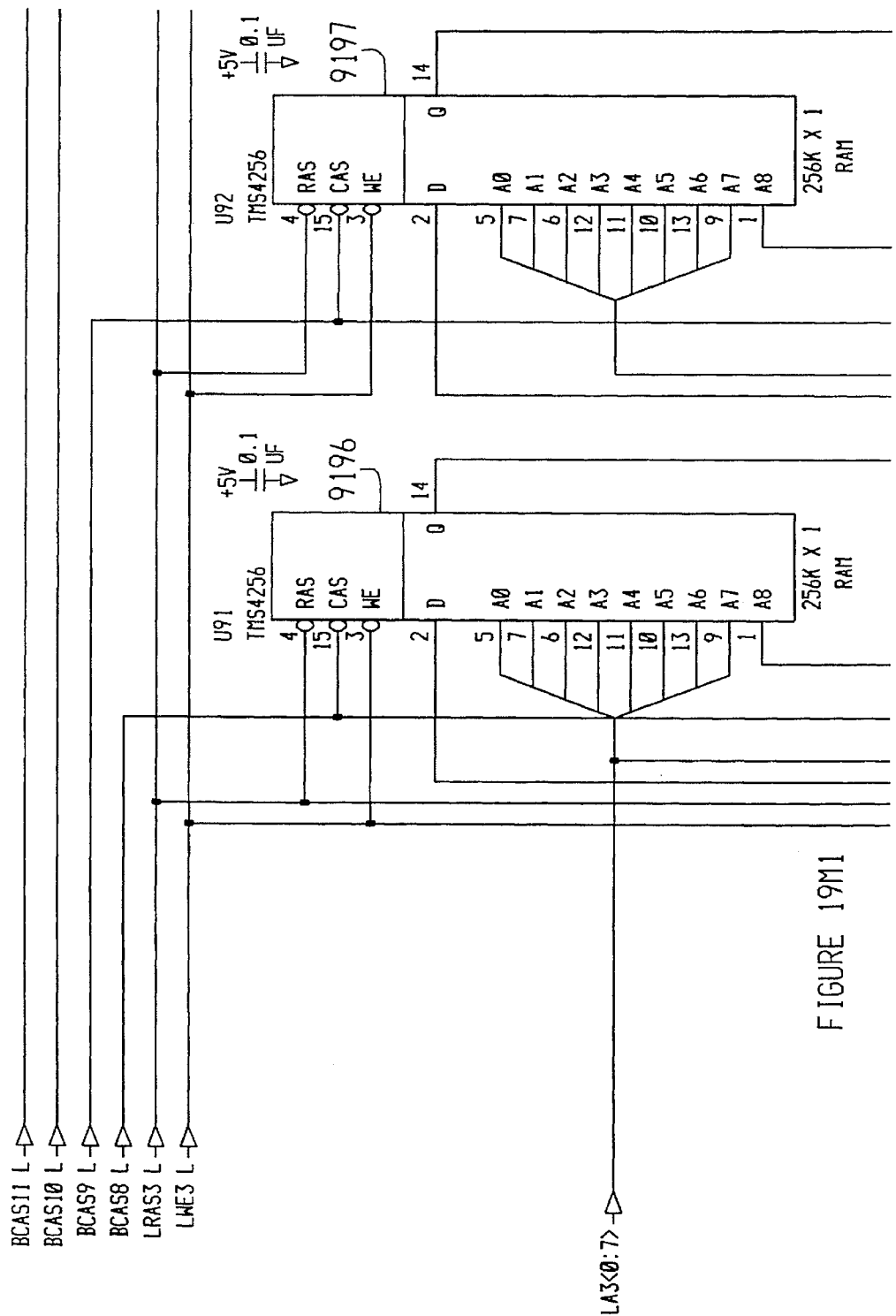
FIGURE 19M1

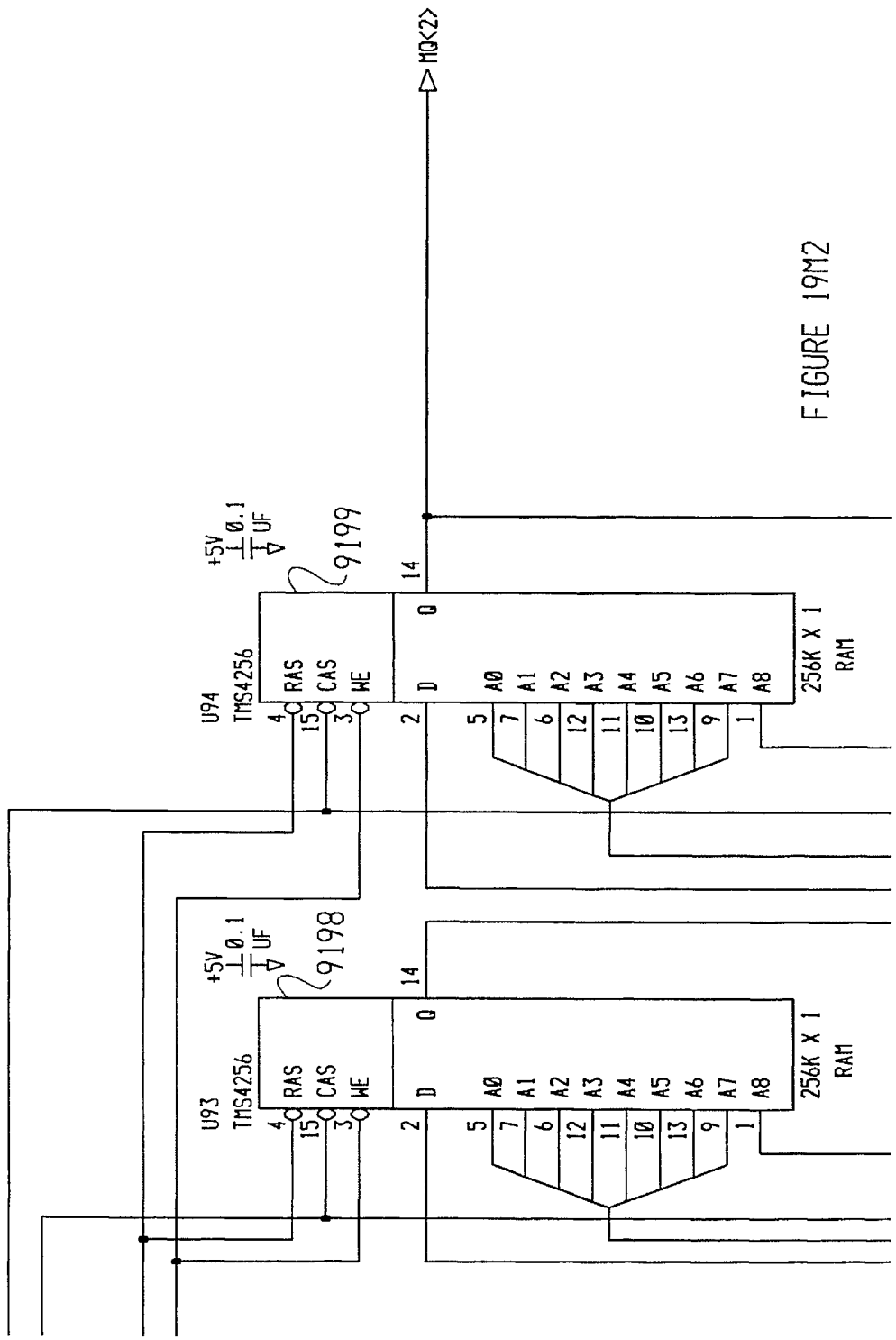
FIGURE 19M2

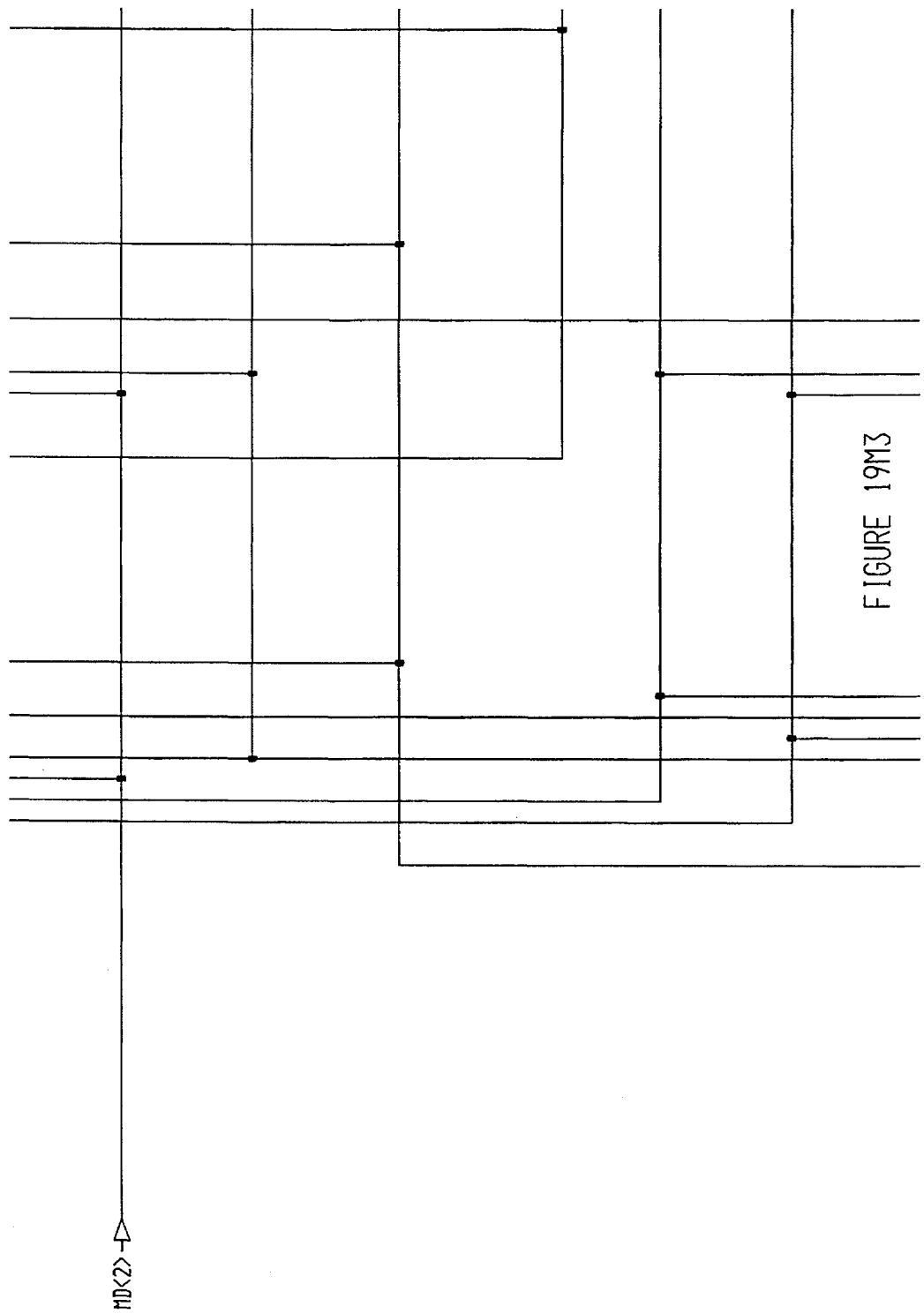
FIGURE 19M3

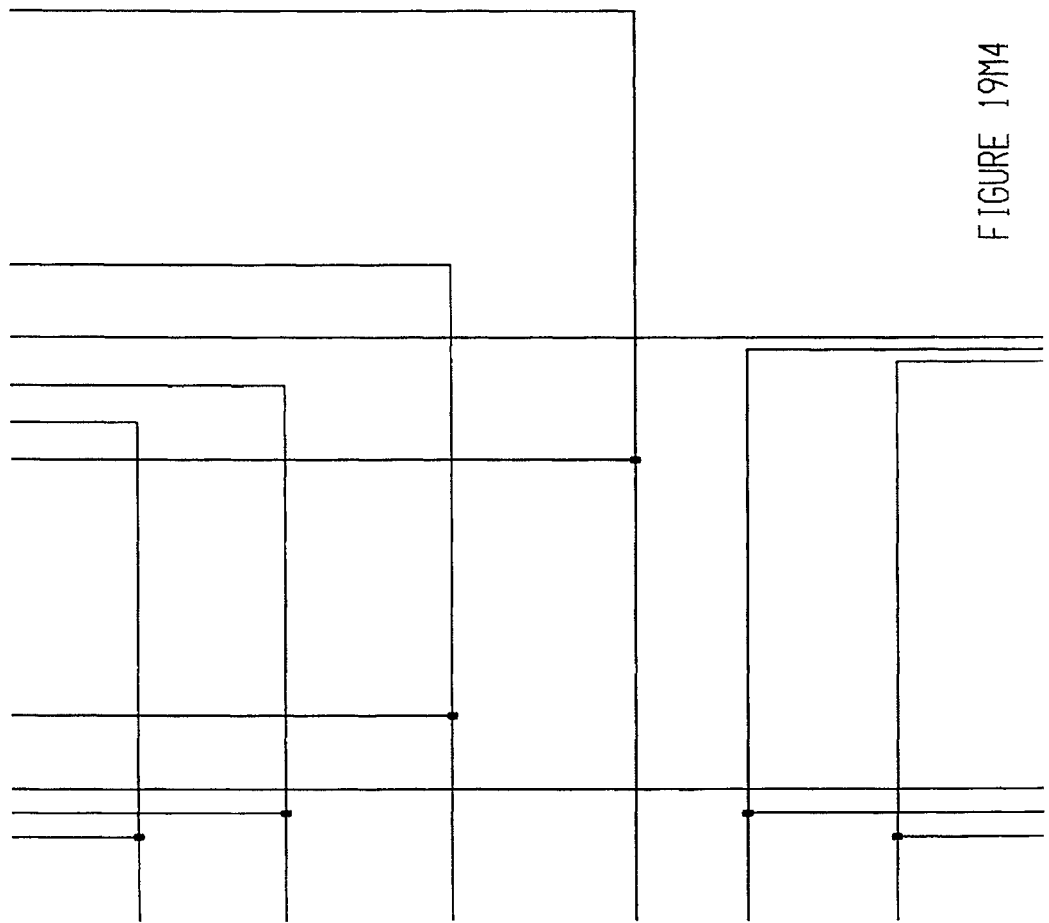

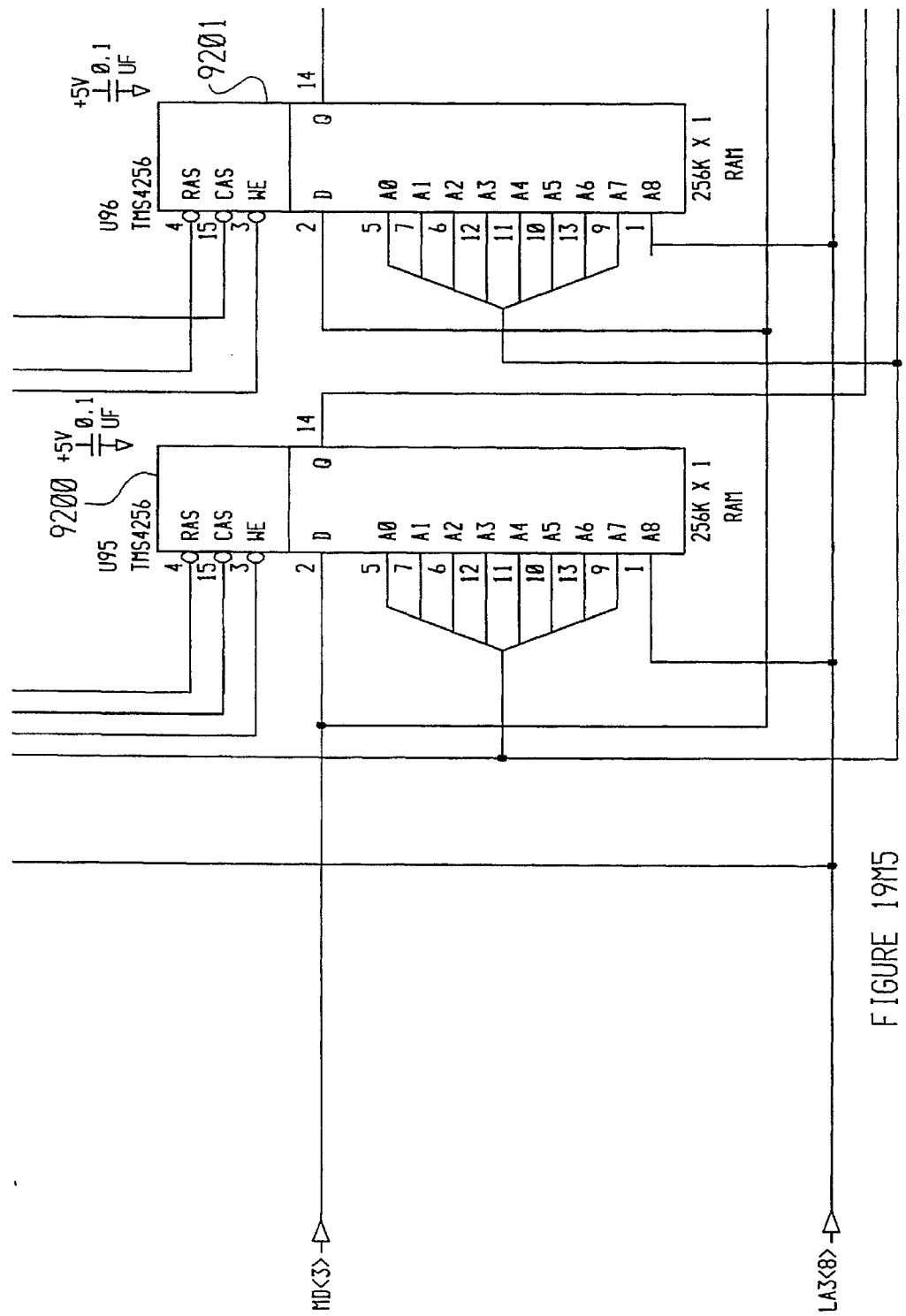
FIGURE 19M5

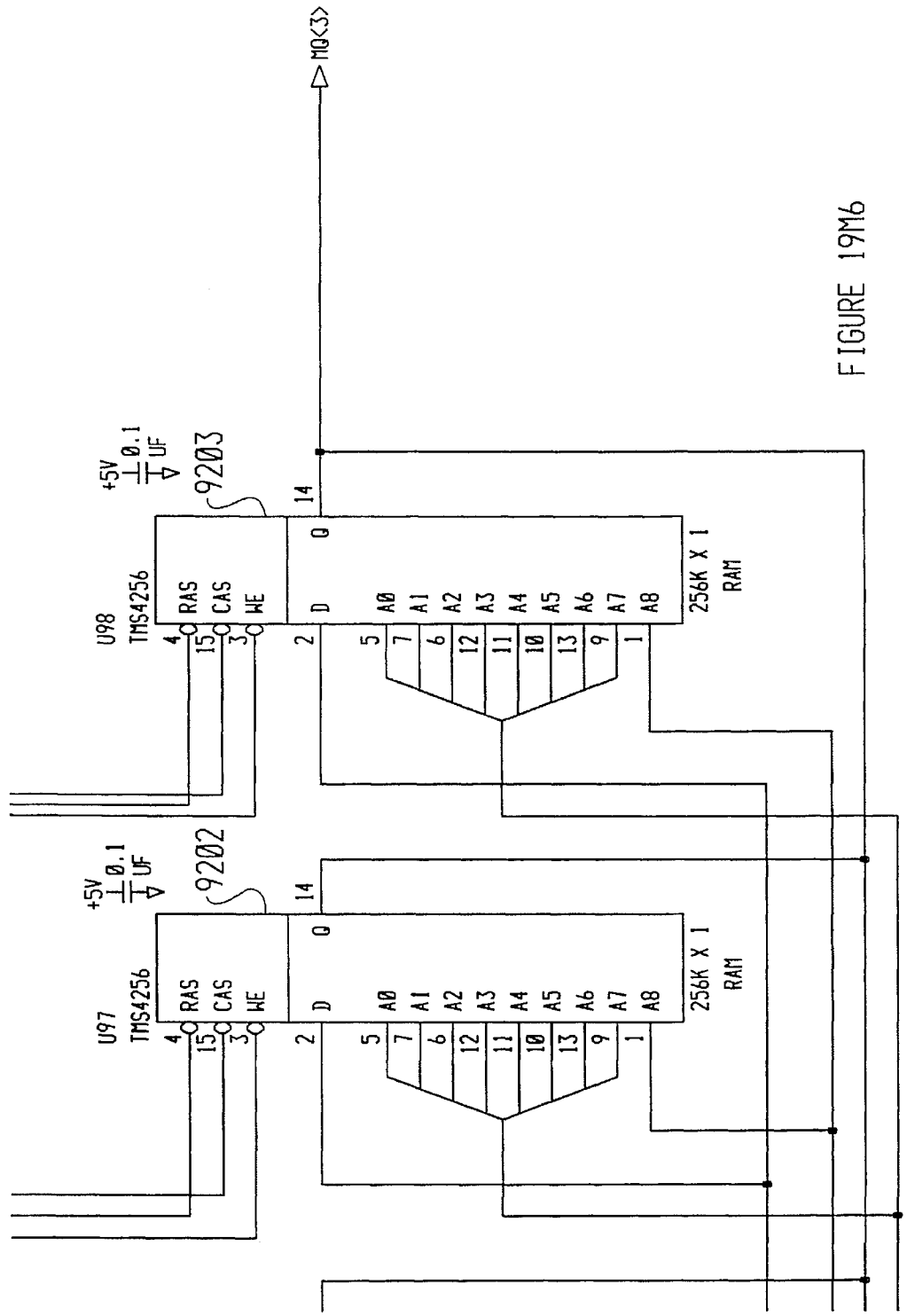
FIGURE 19M6

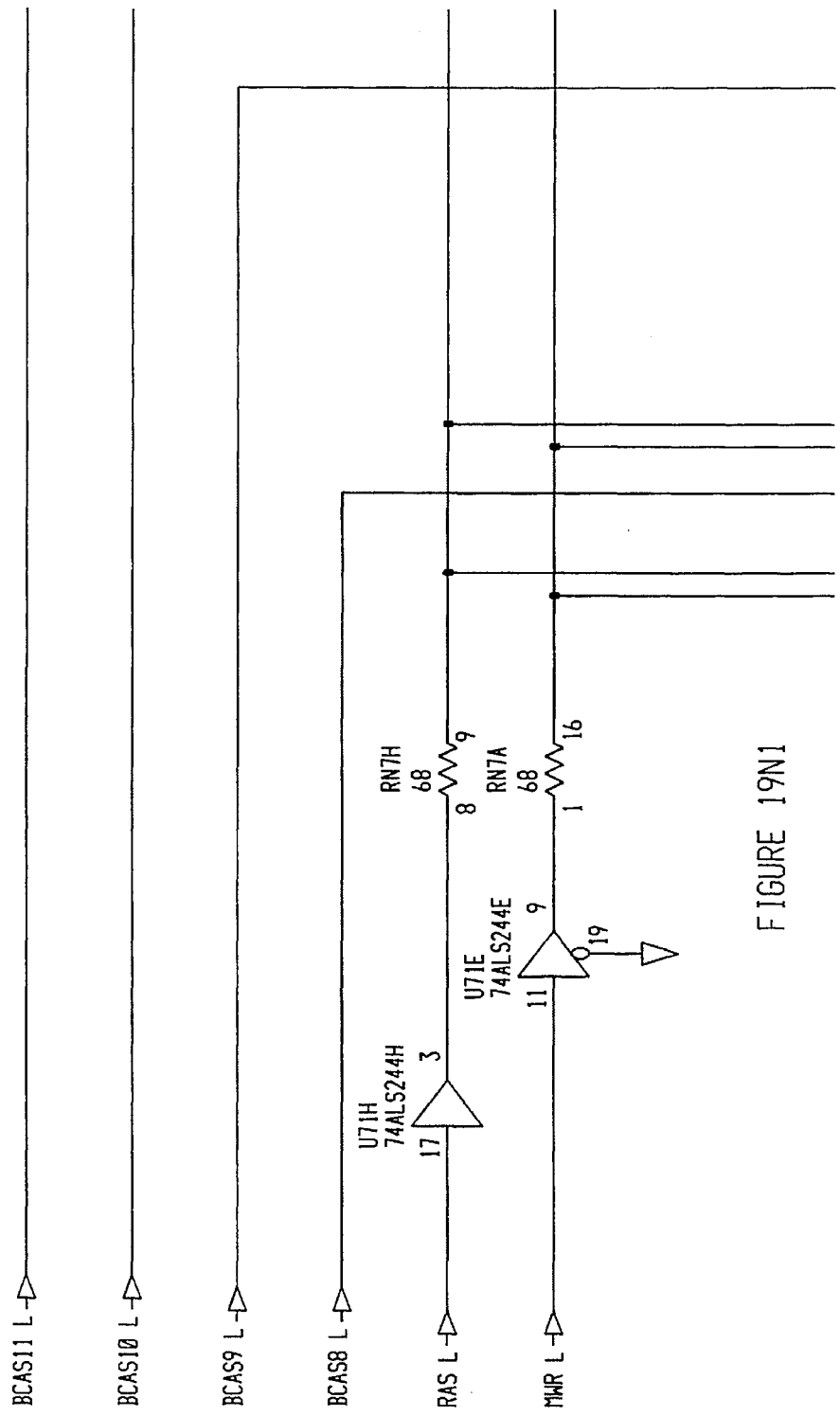
FIGURE 19N1

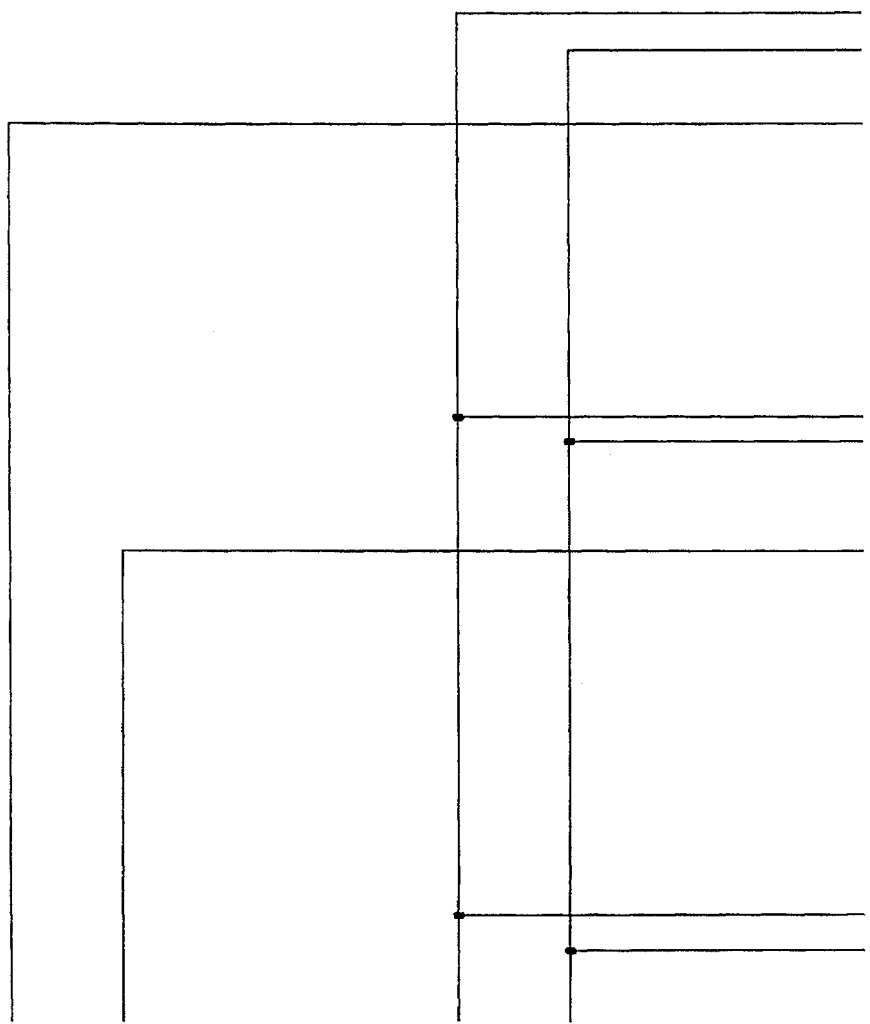
FIGURE 19N2

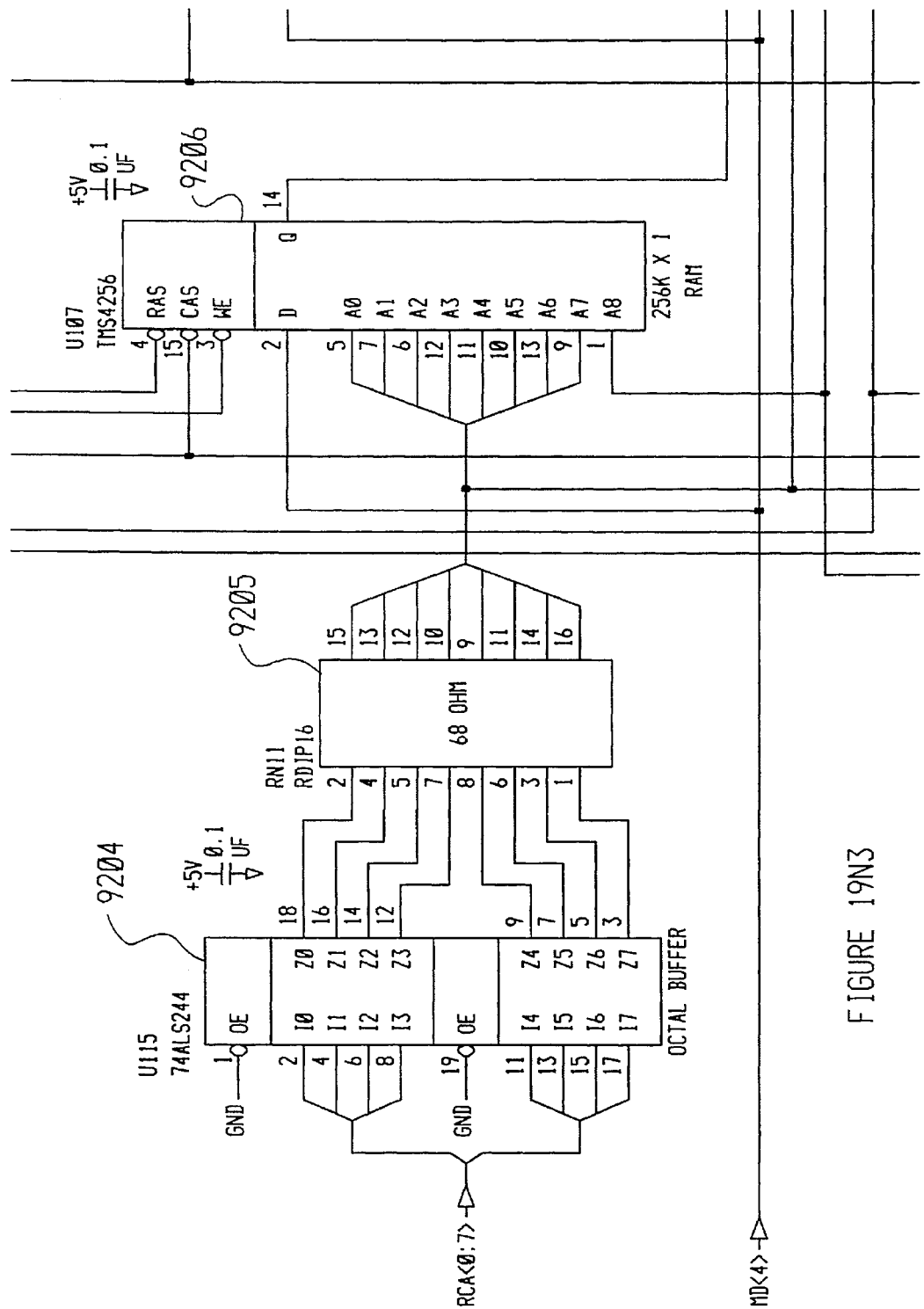
FIGURE 19N3

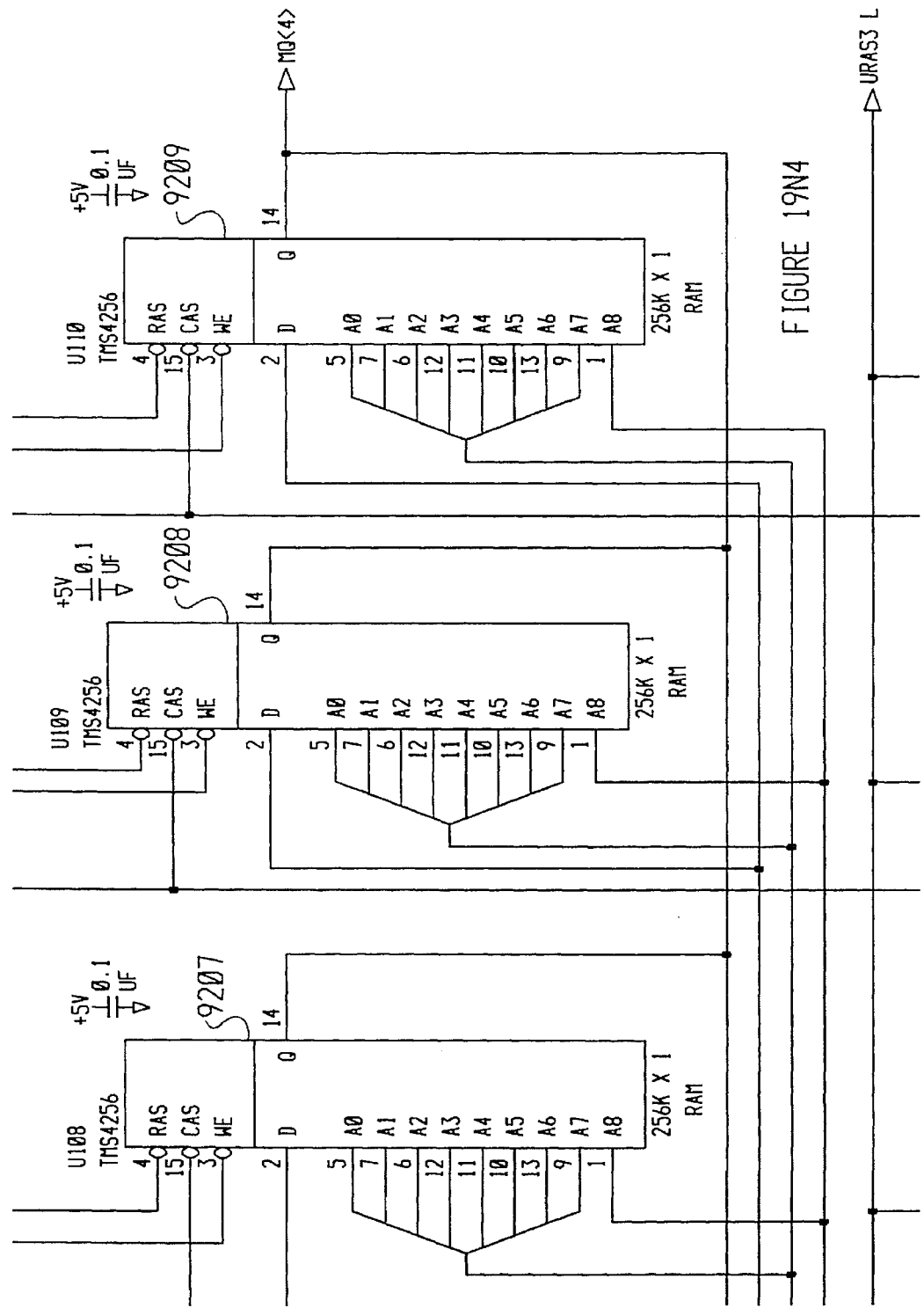
FIGURE 19N4

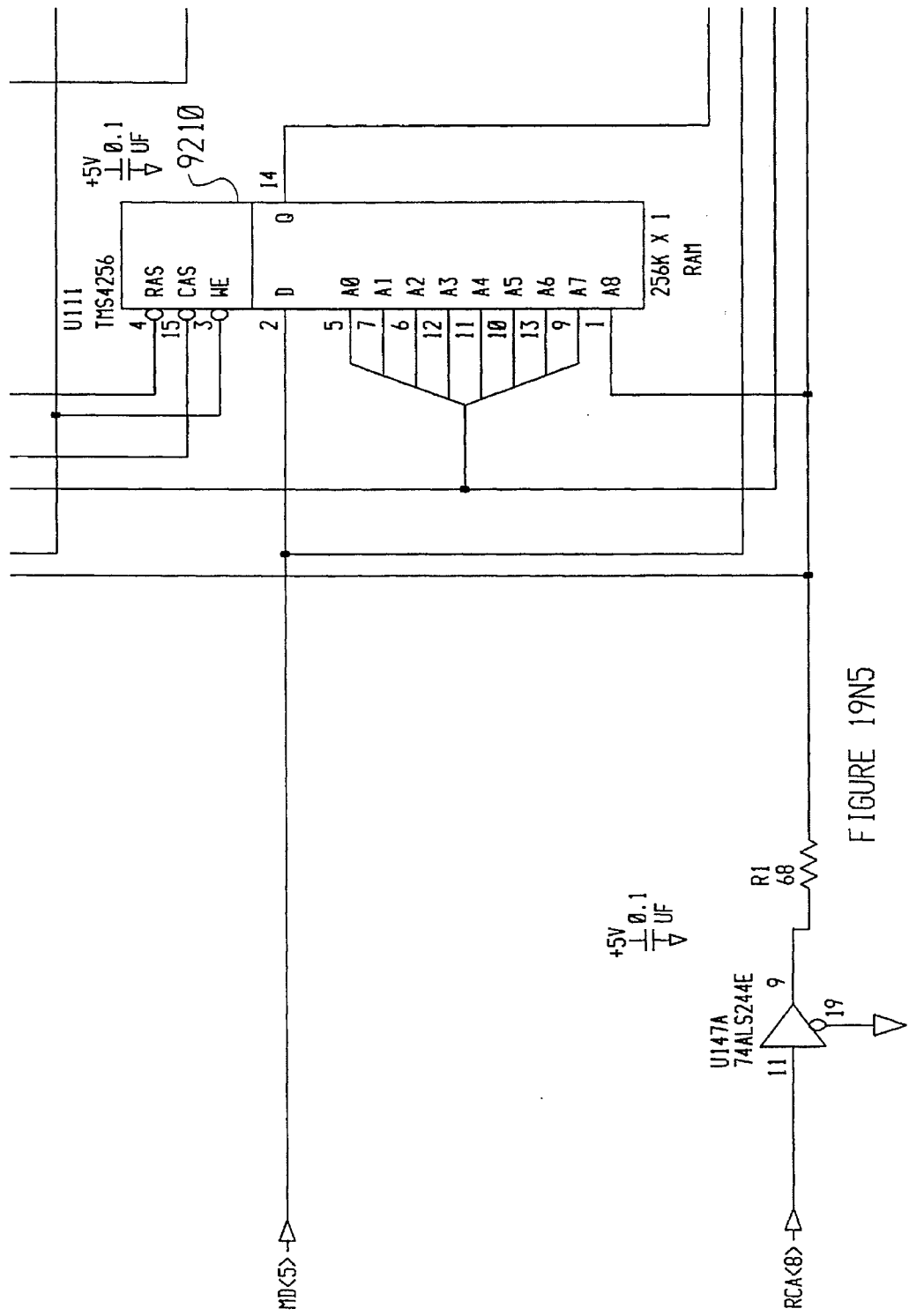
FIGURE 19N5

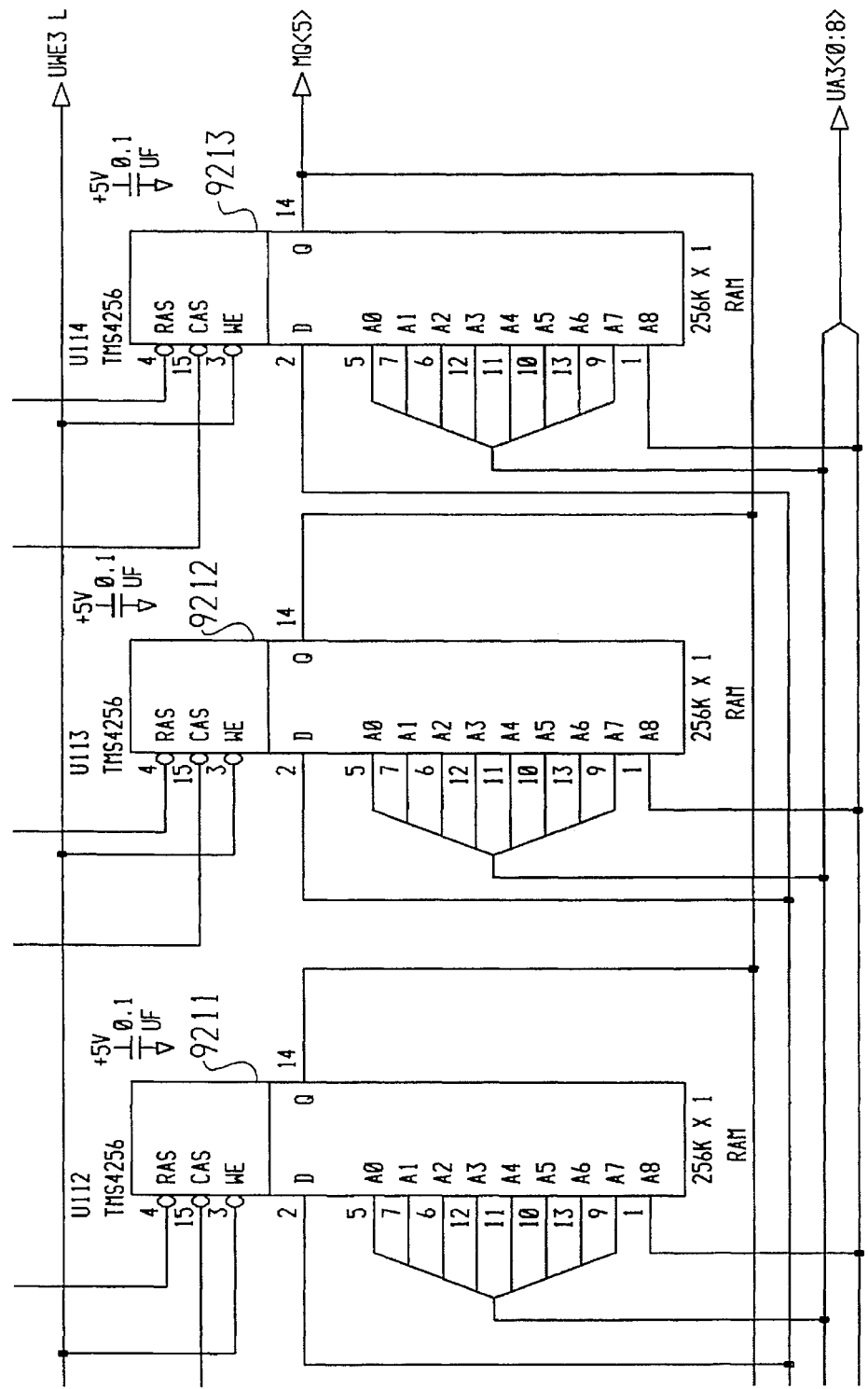
FIGURE 19N6

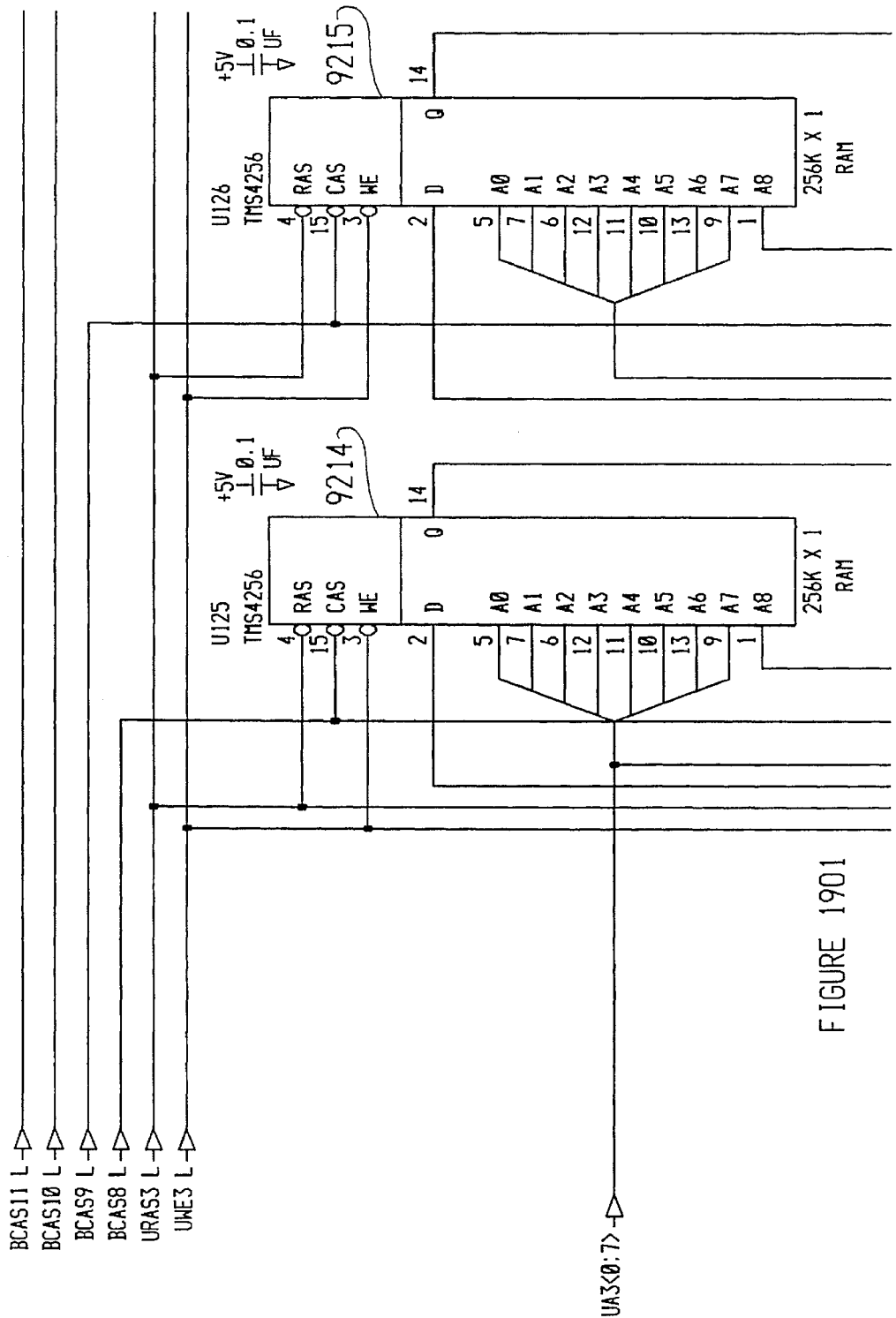
FIGURE 1901

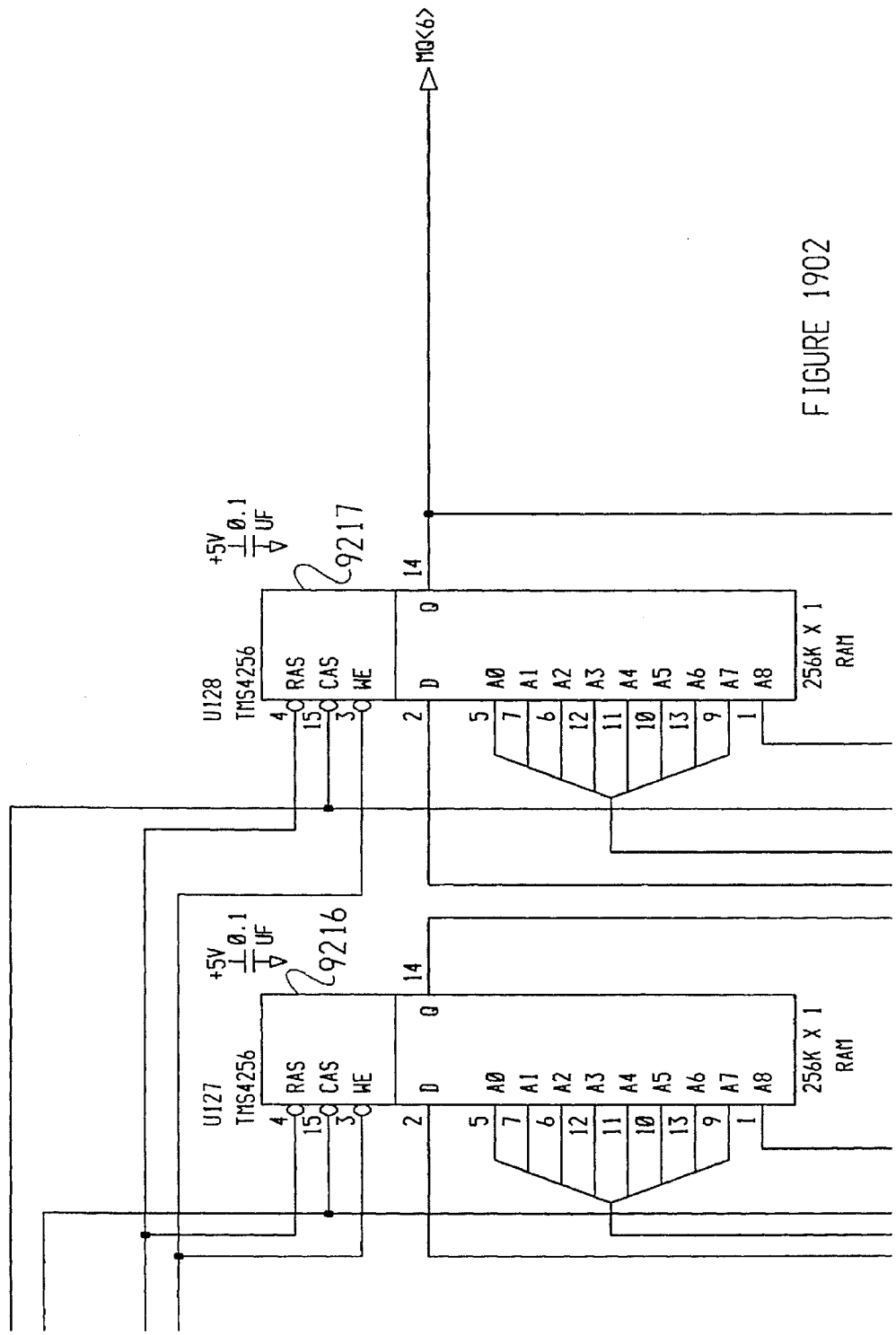
FIGURE 1902

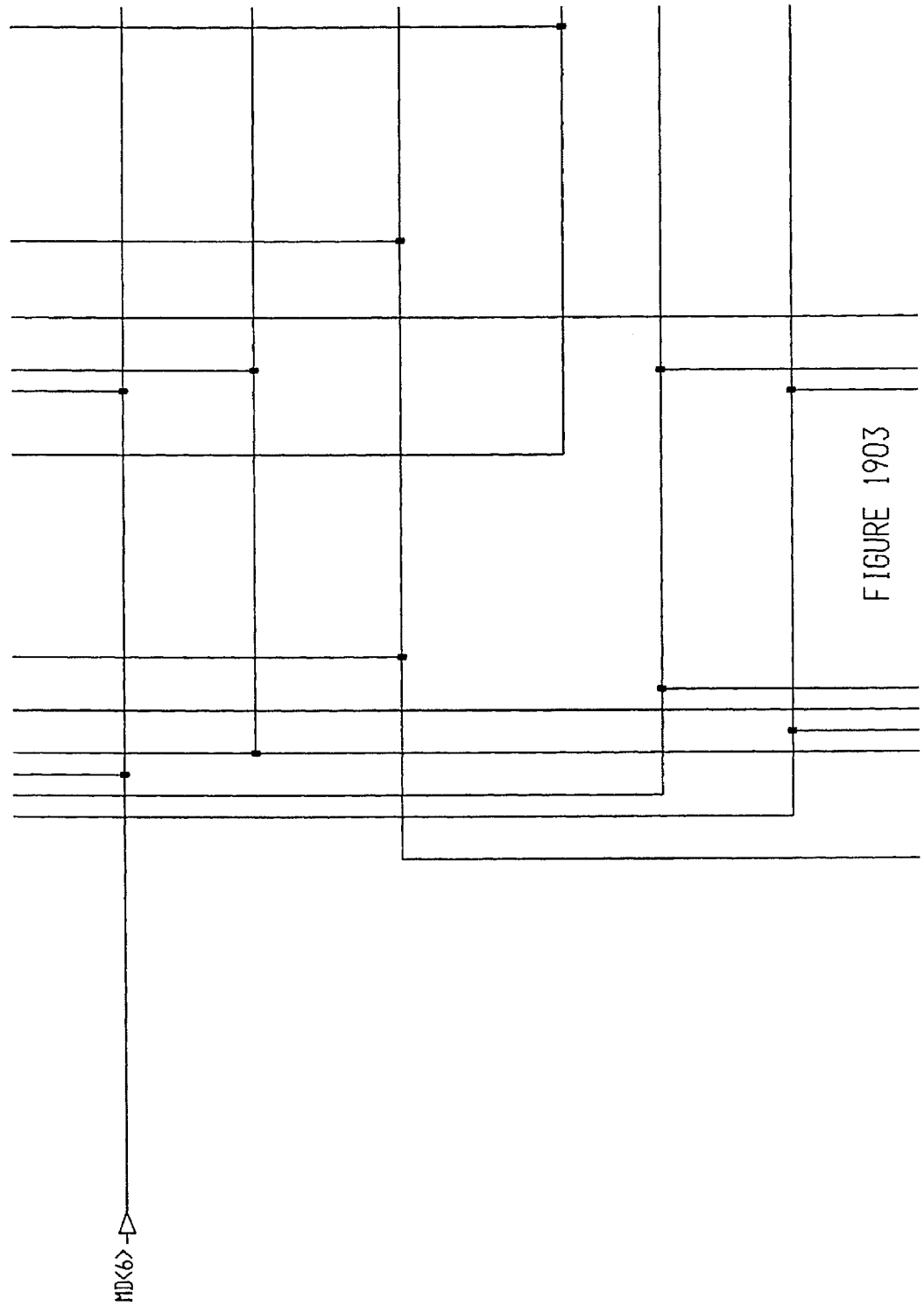

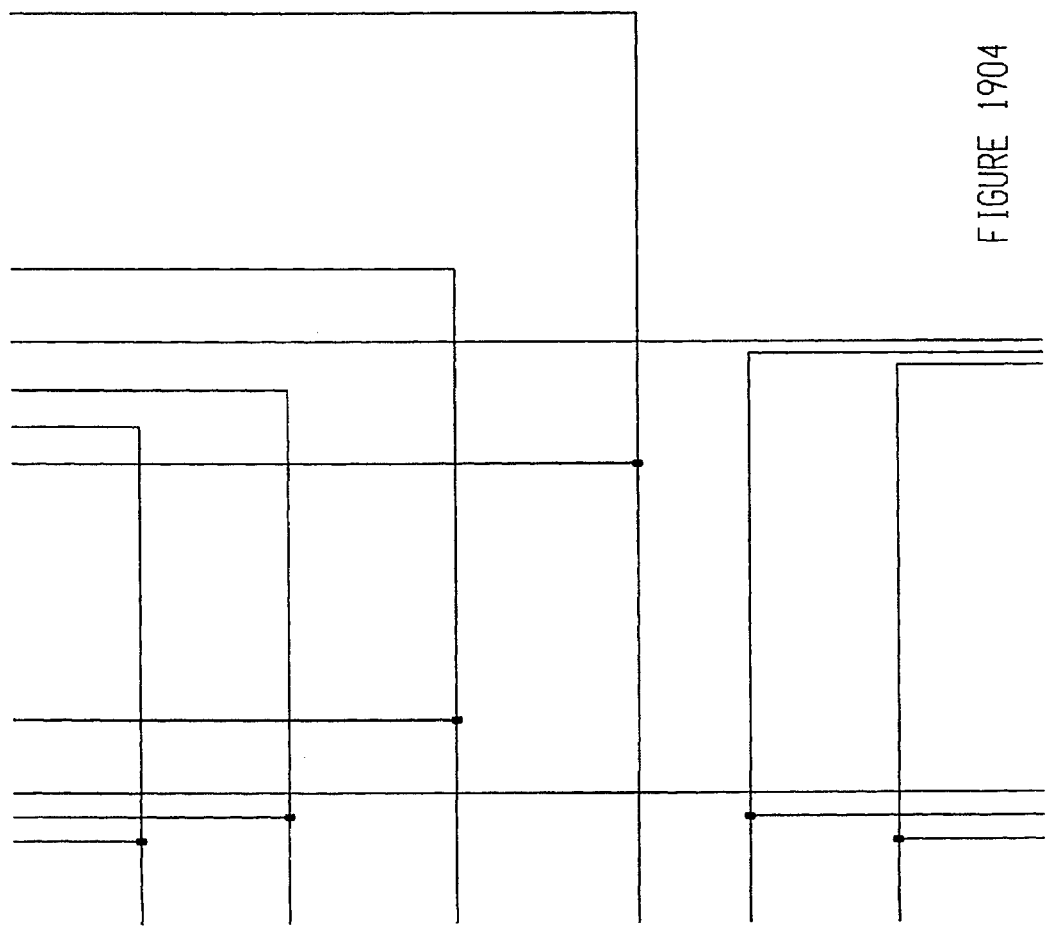

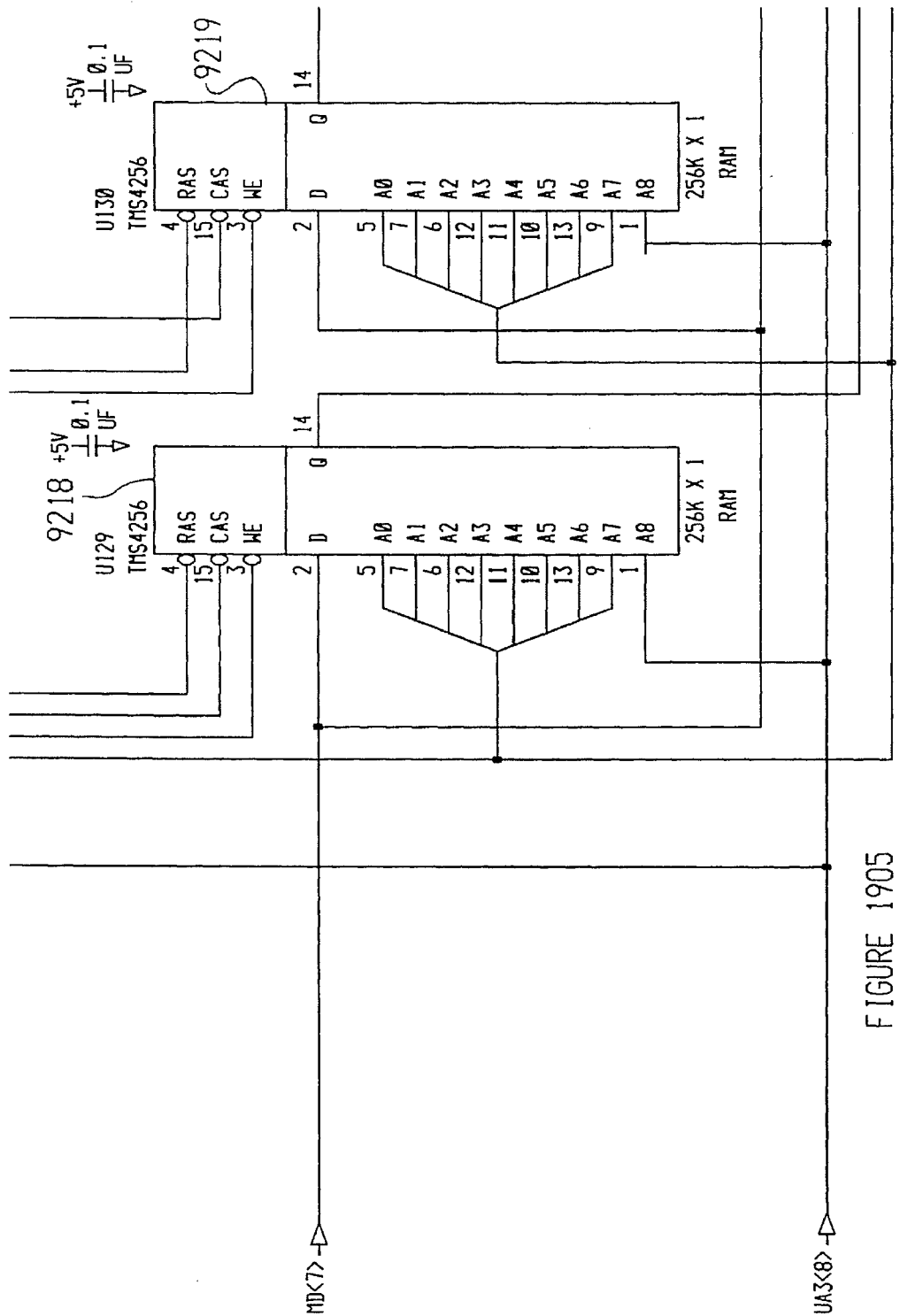
FIGURE 1905

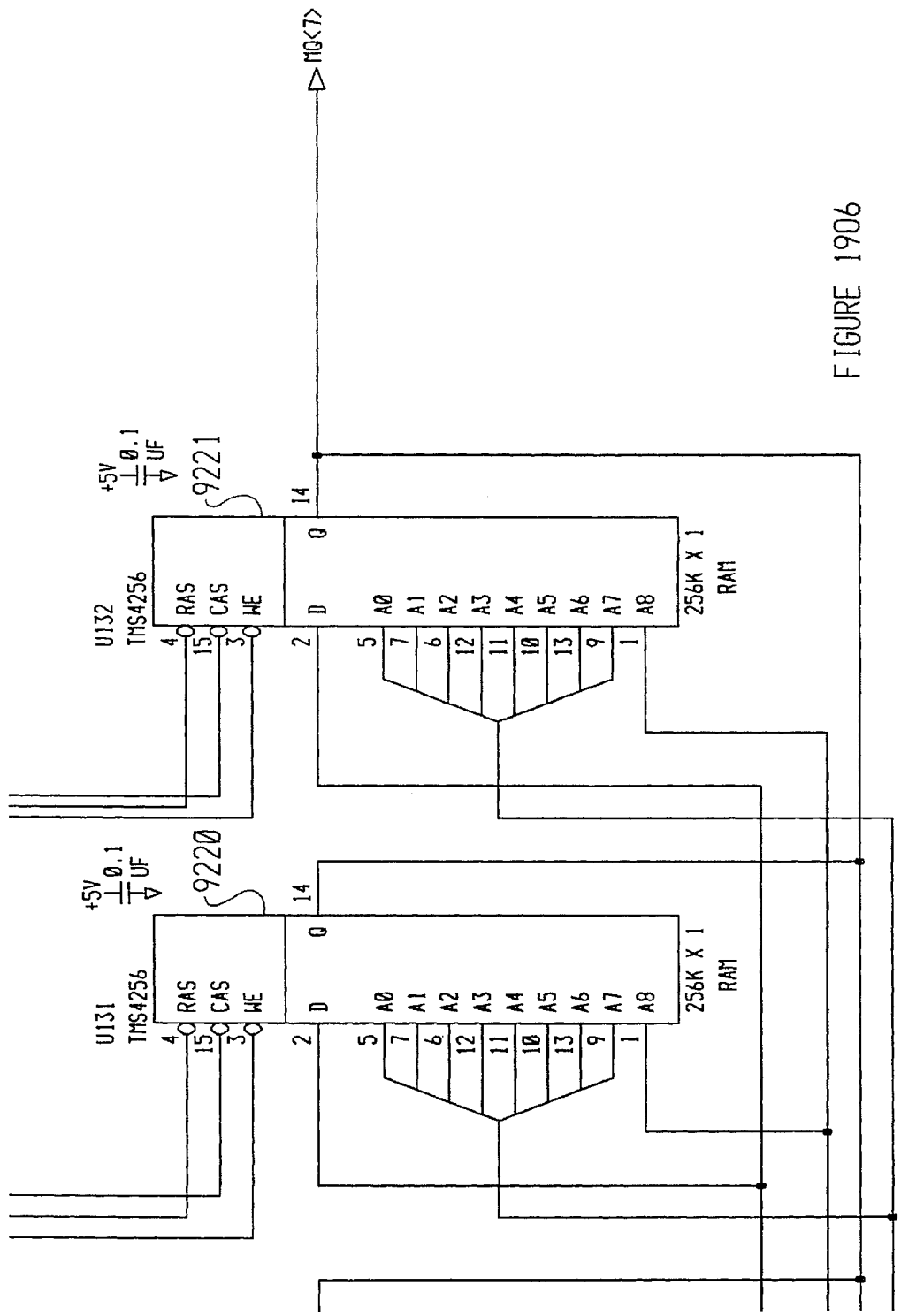
FIGURE 1906

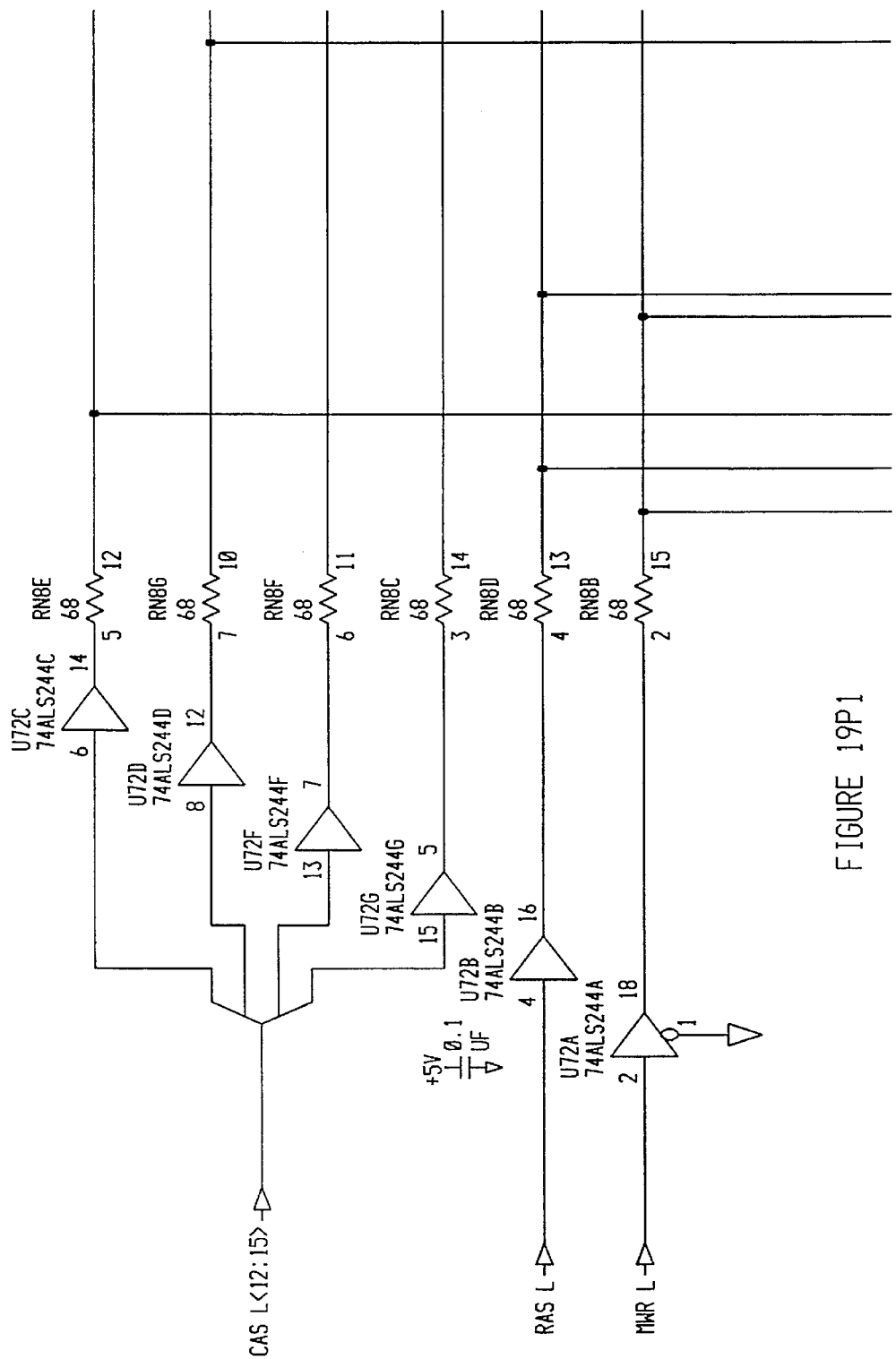
FIGURE 19P1

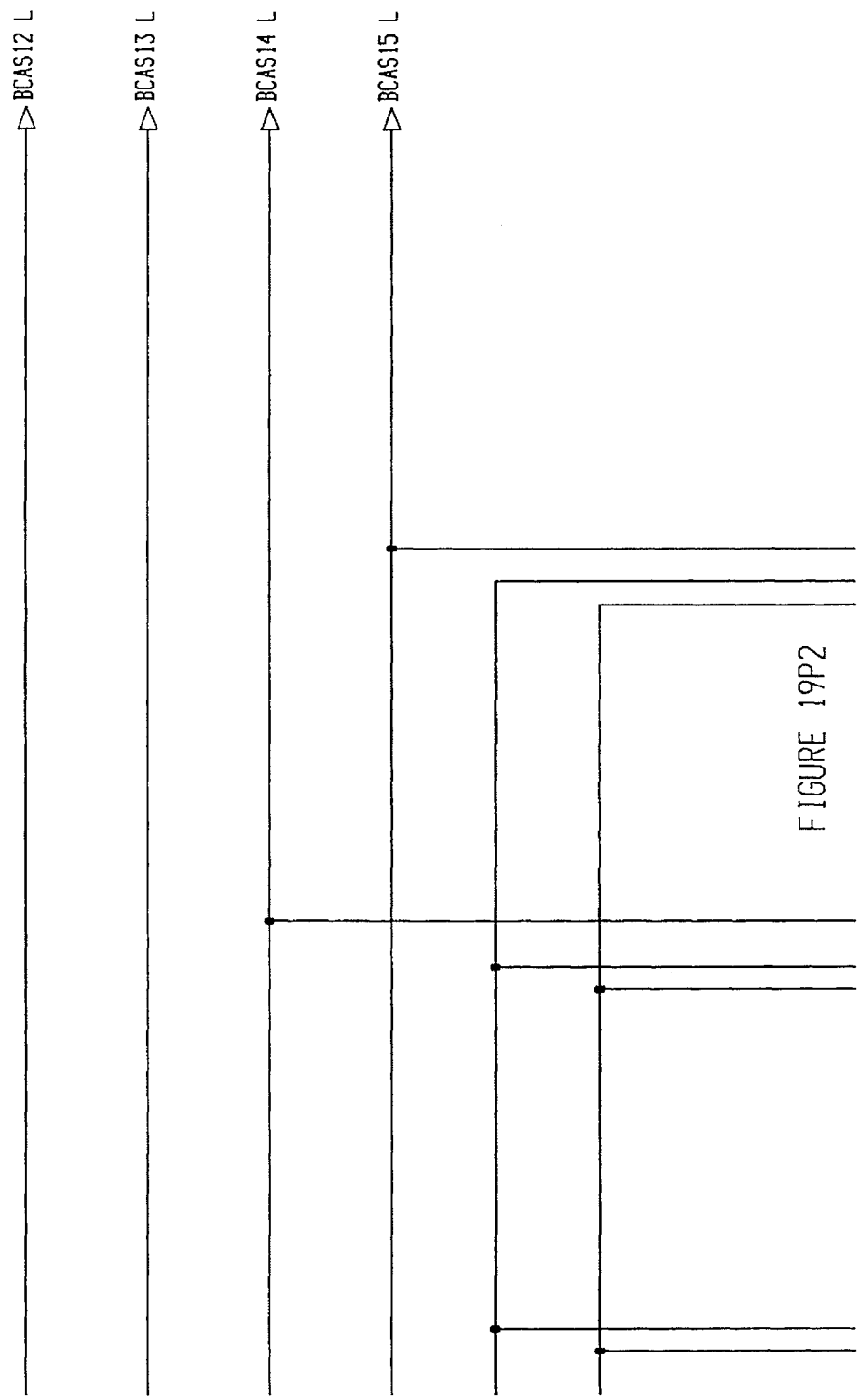

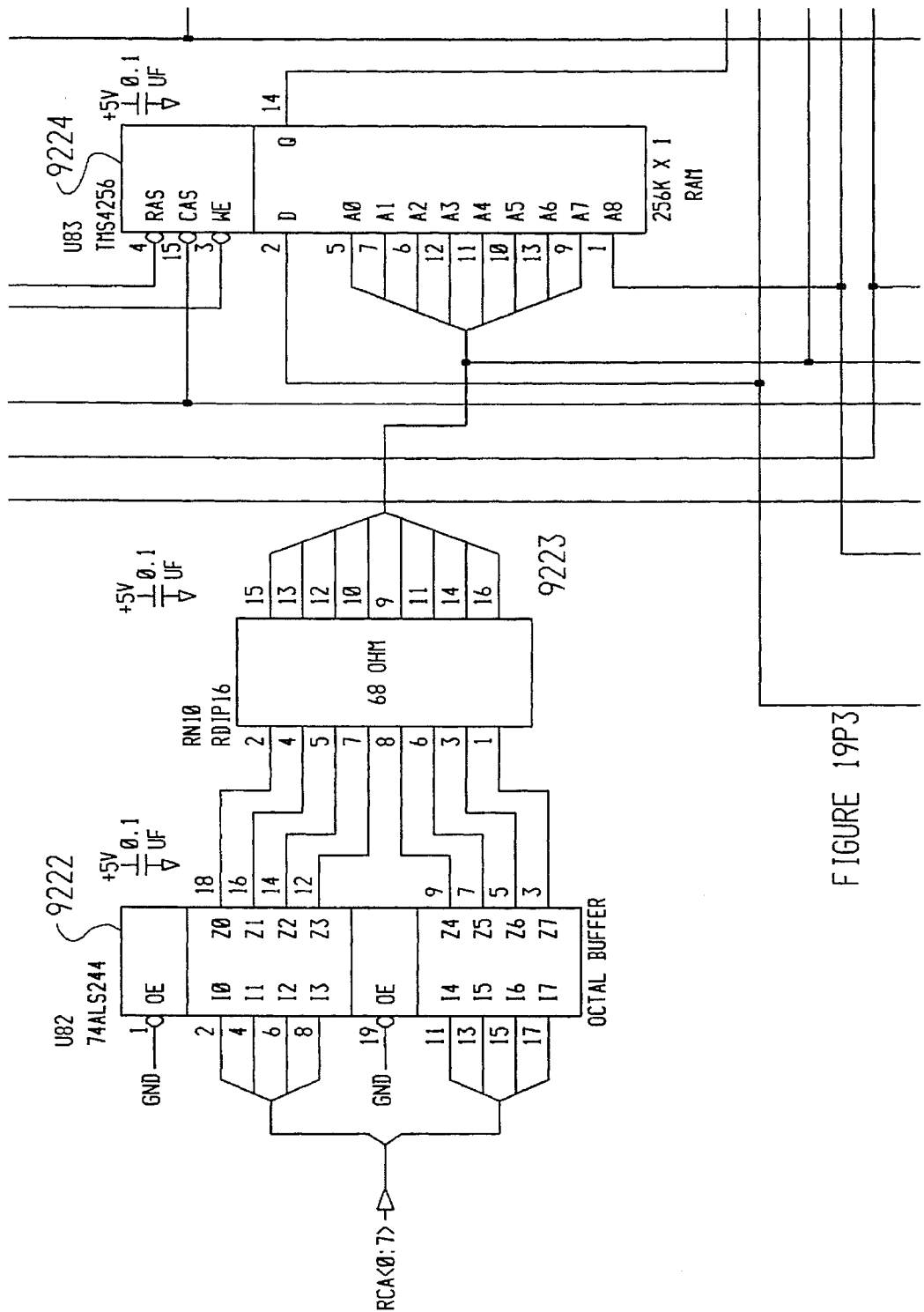
FIGURE 19P3

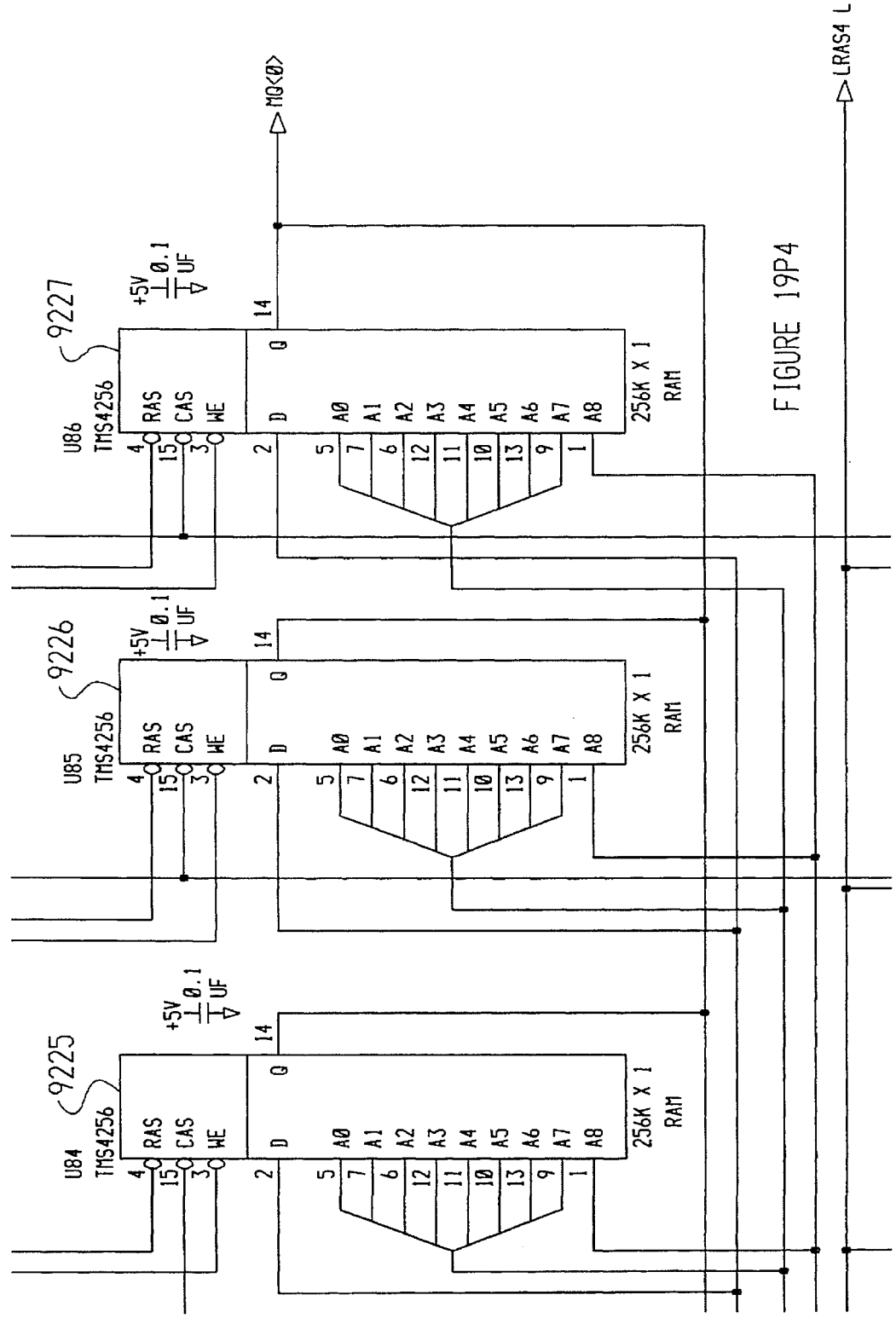
FIGURE 19P4

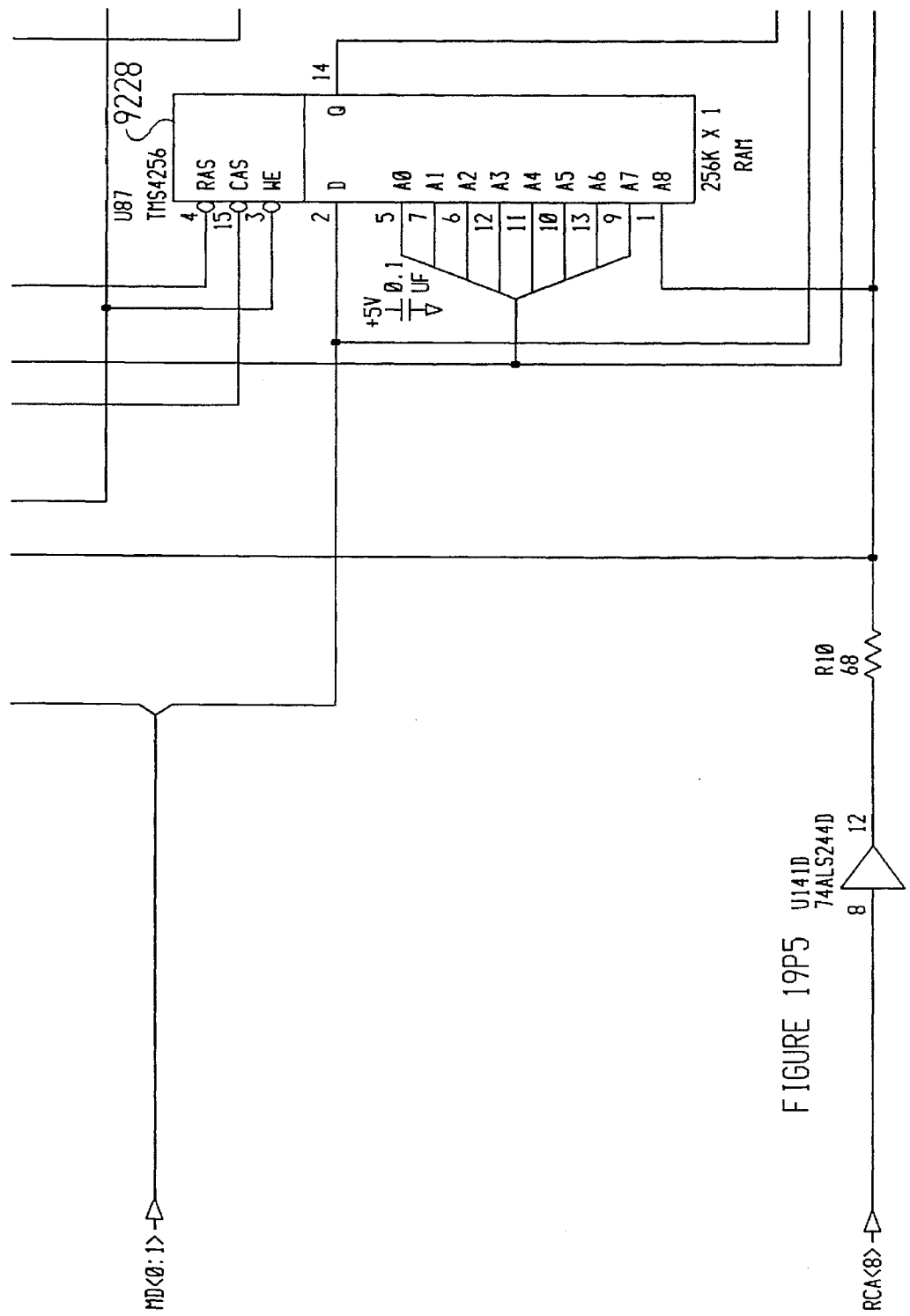
FIGURE 19P5

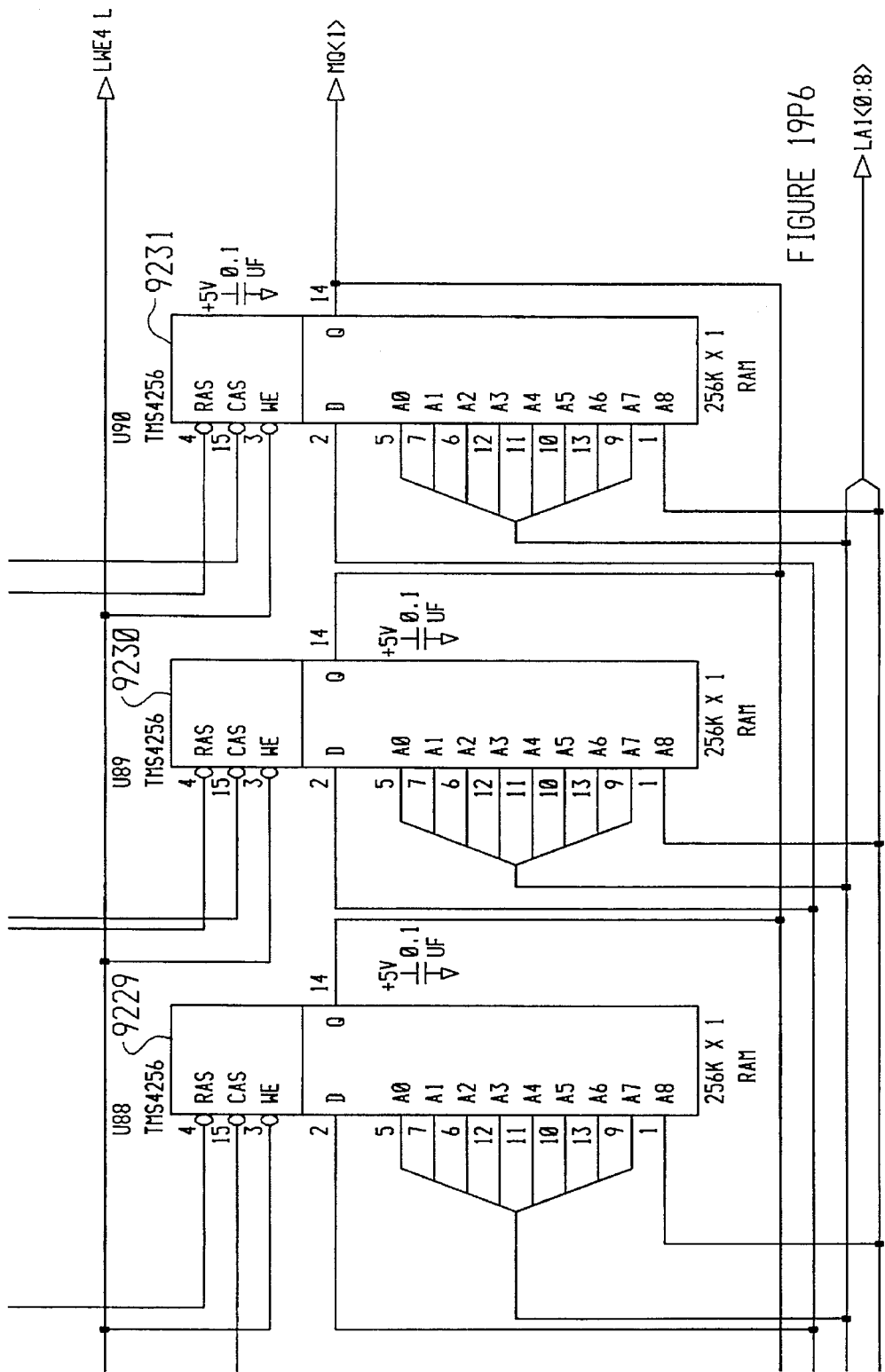
FIGURE 19P6

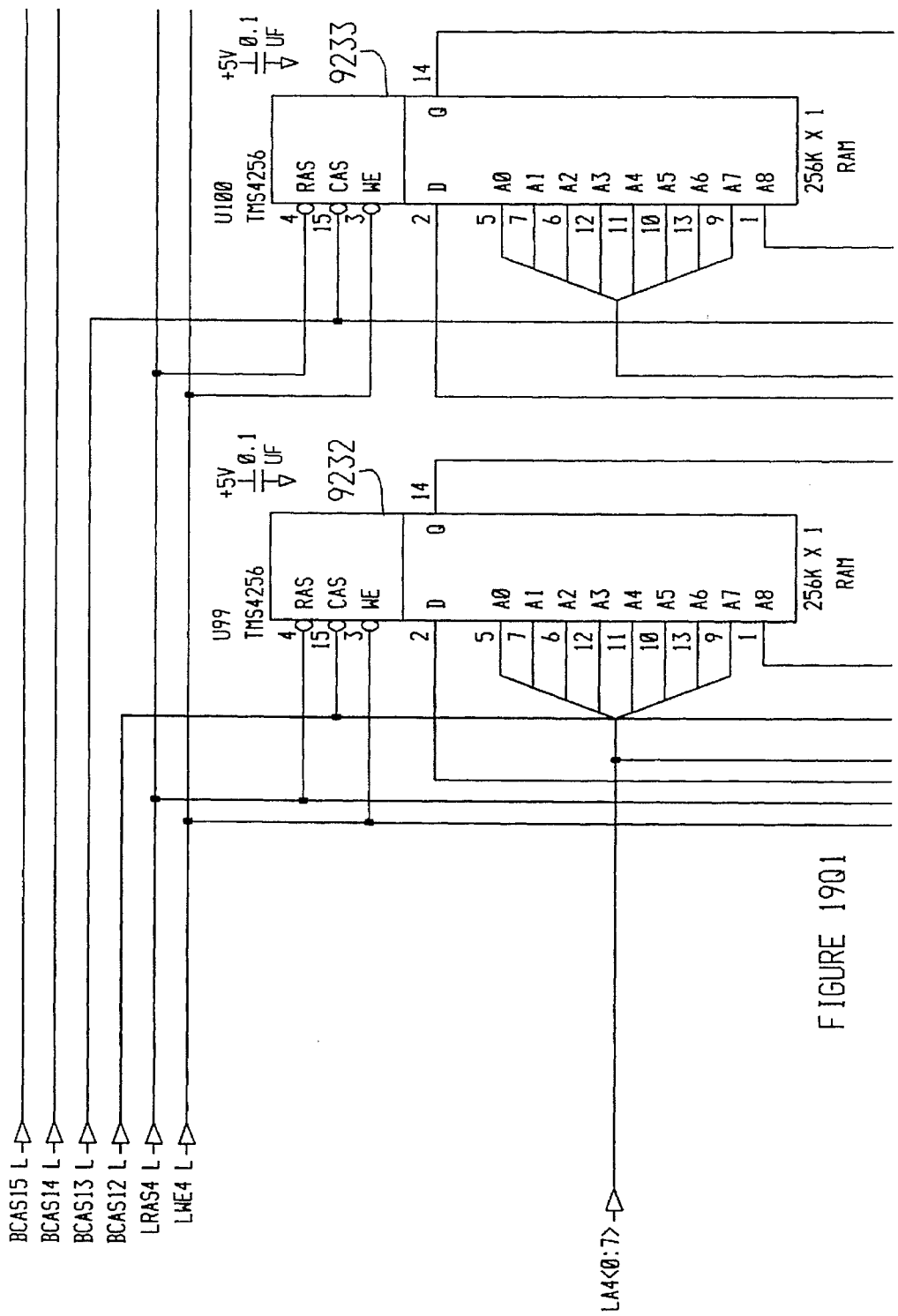
FIGURE 1901

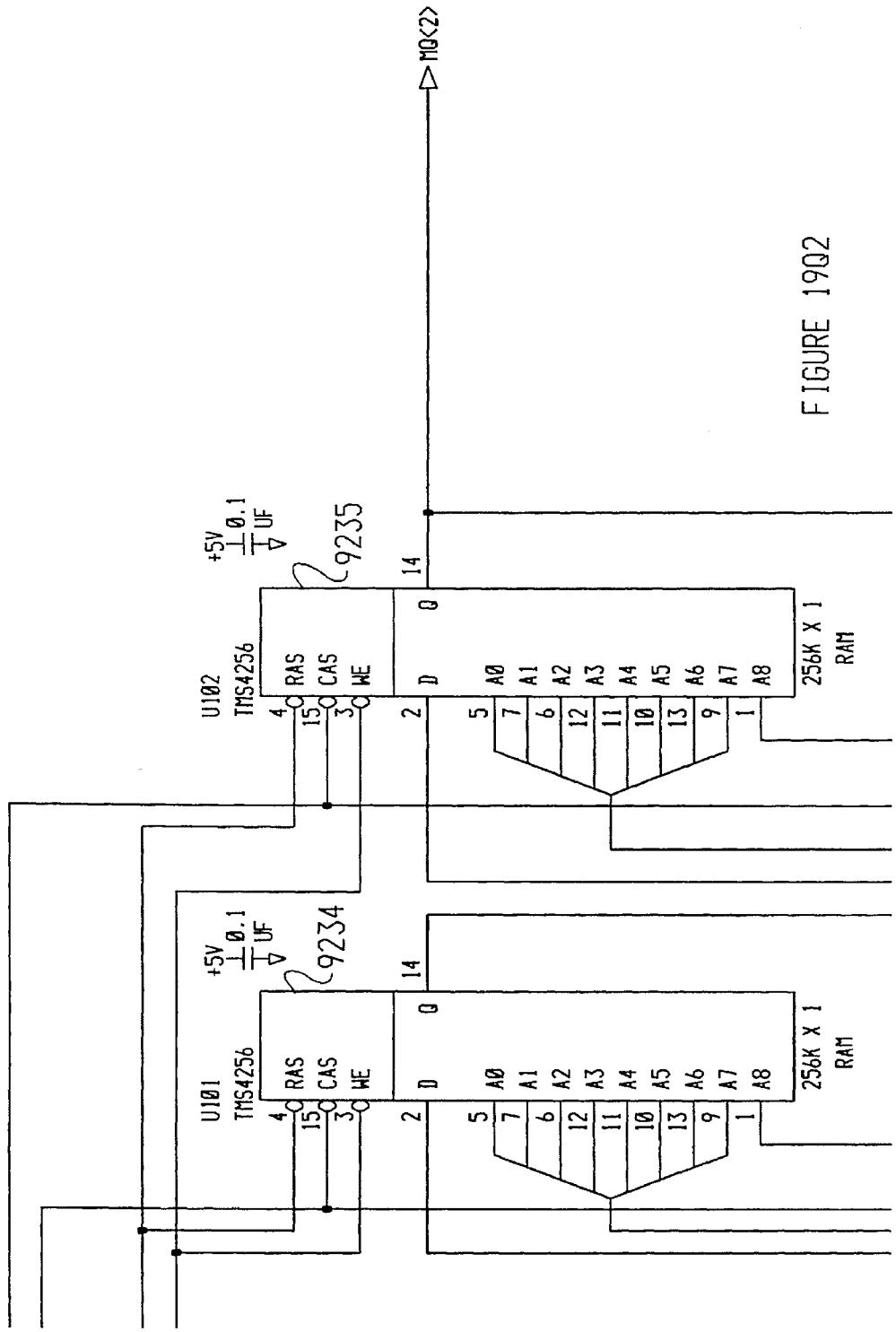
FIGURE 1902

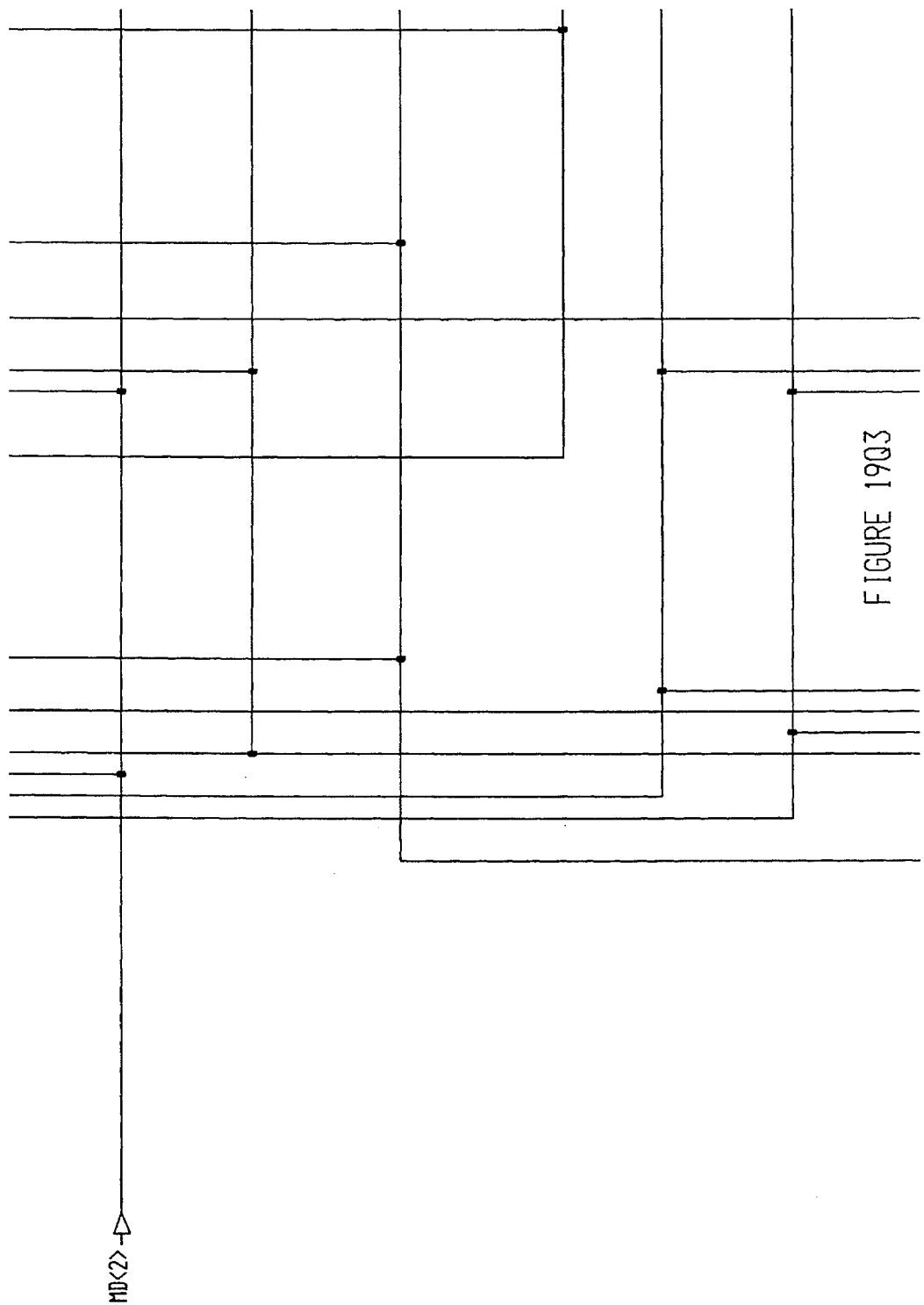
FIGURE 19Q3

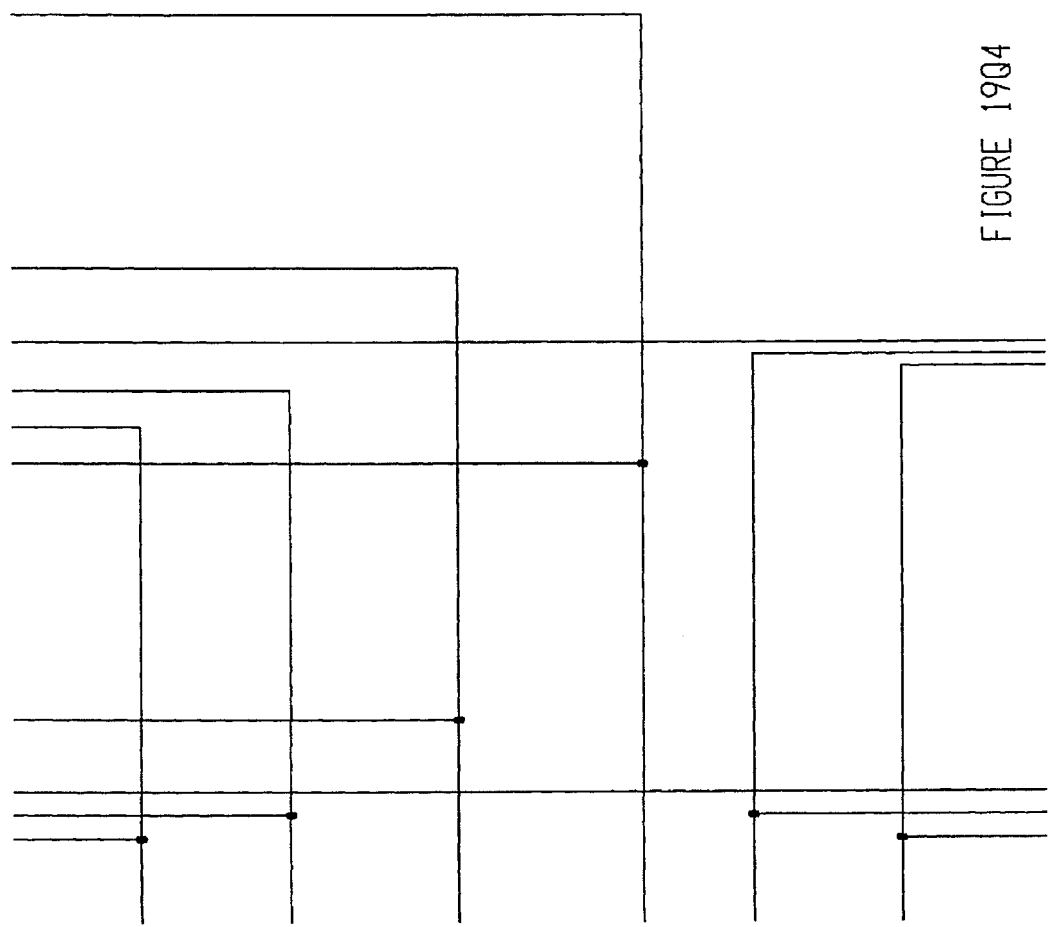
FIGURE 19Q4

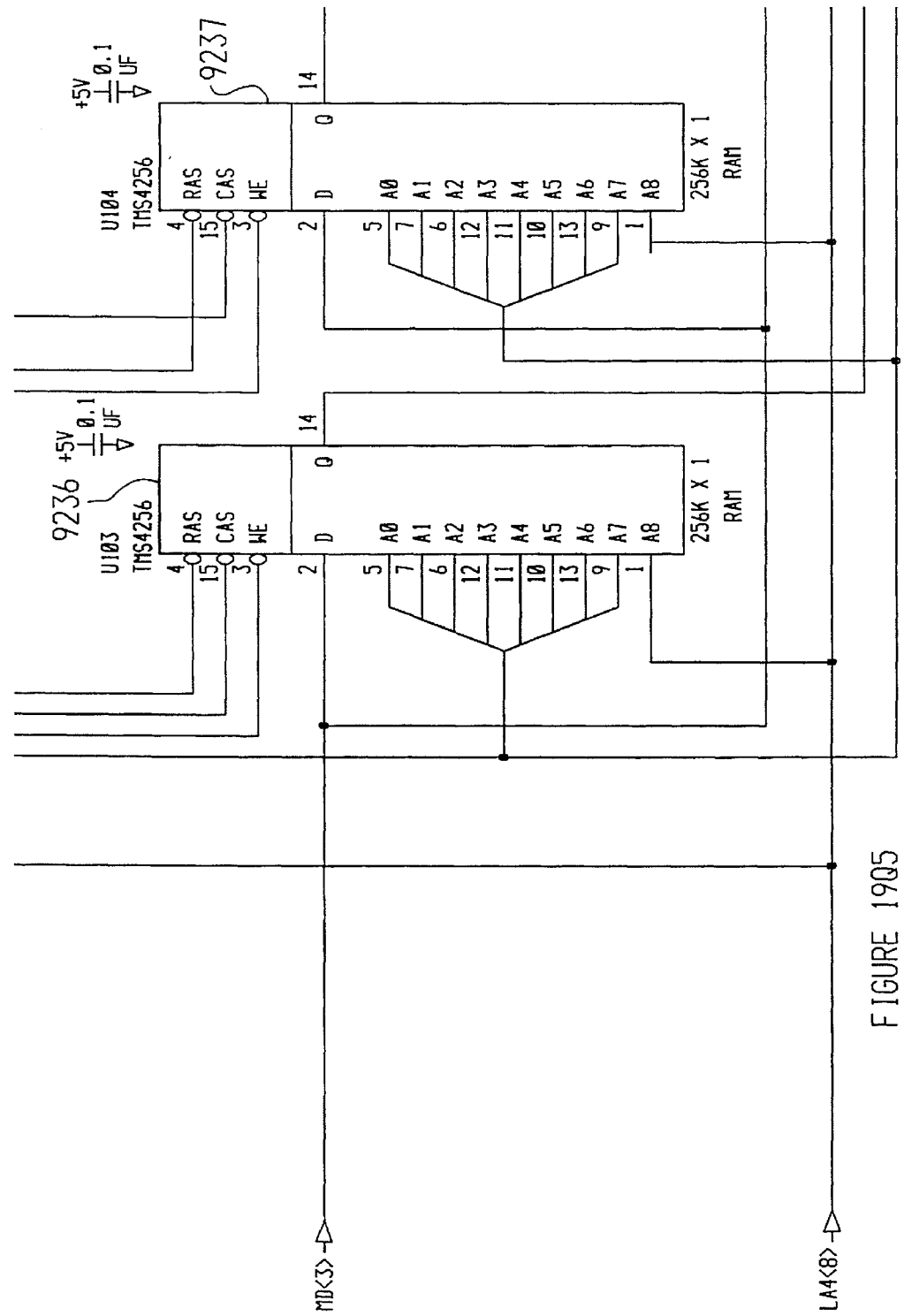
FIGURE 1905

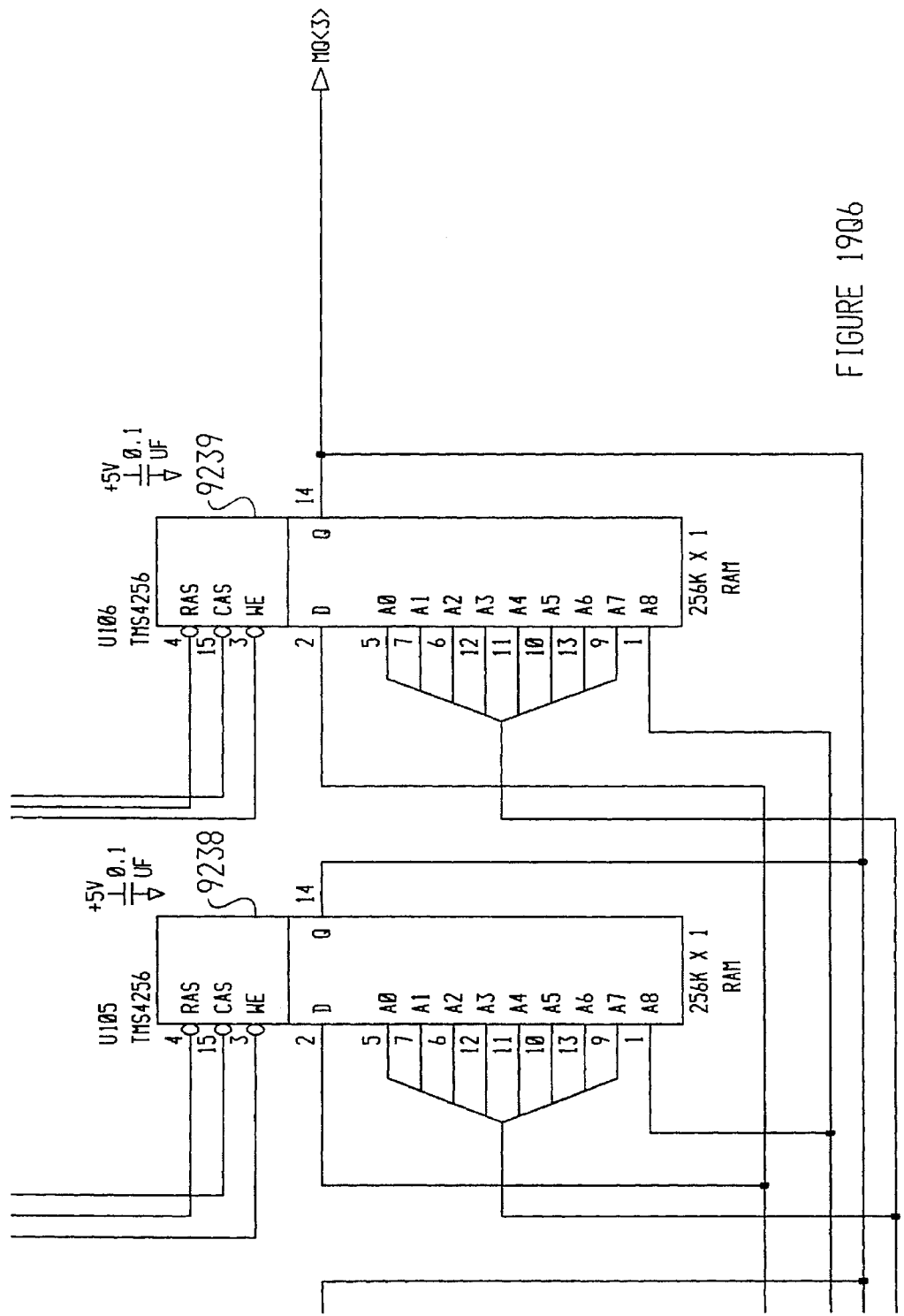
FIGURE 1906

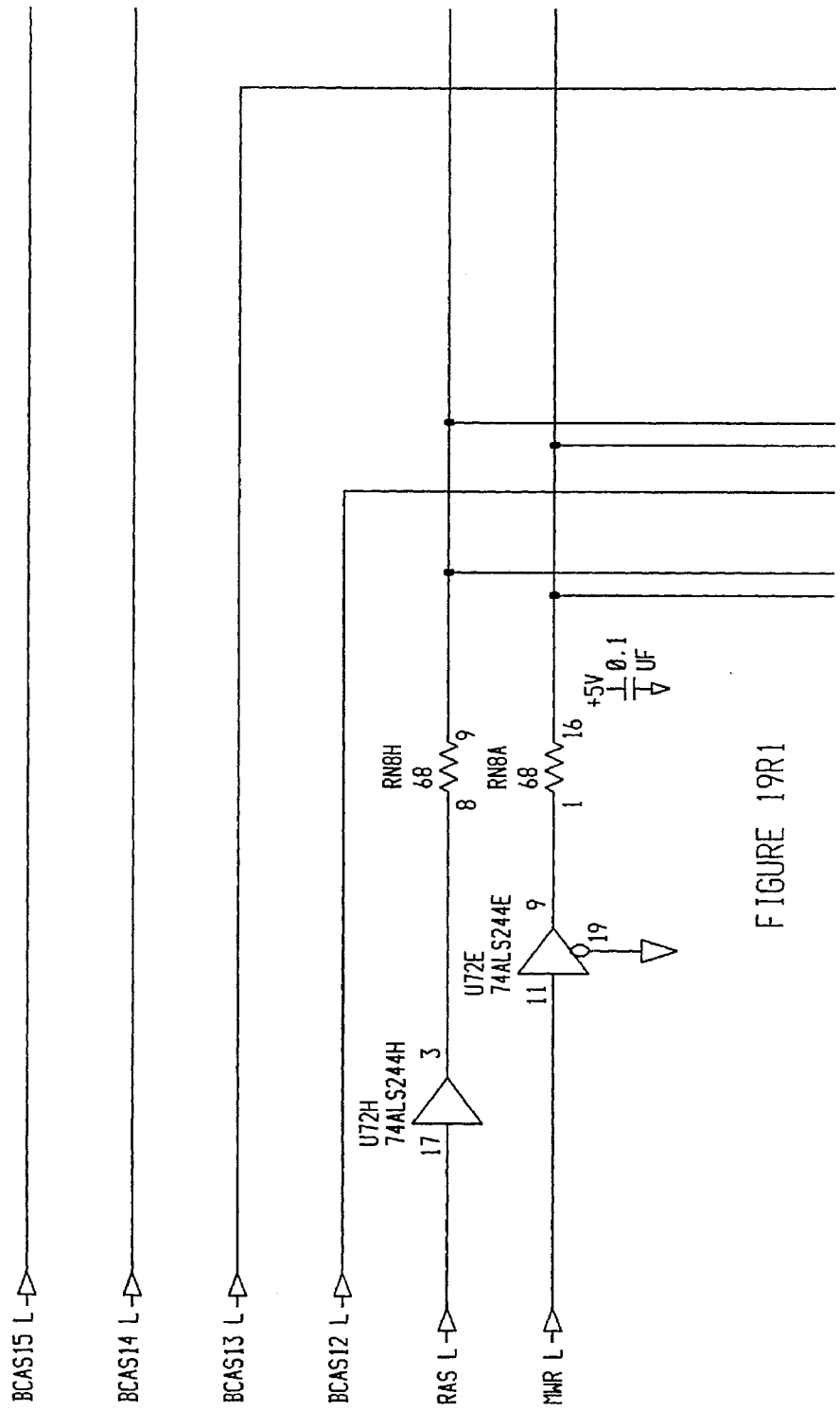
FIGURE 19R1

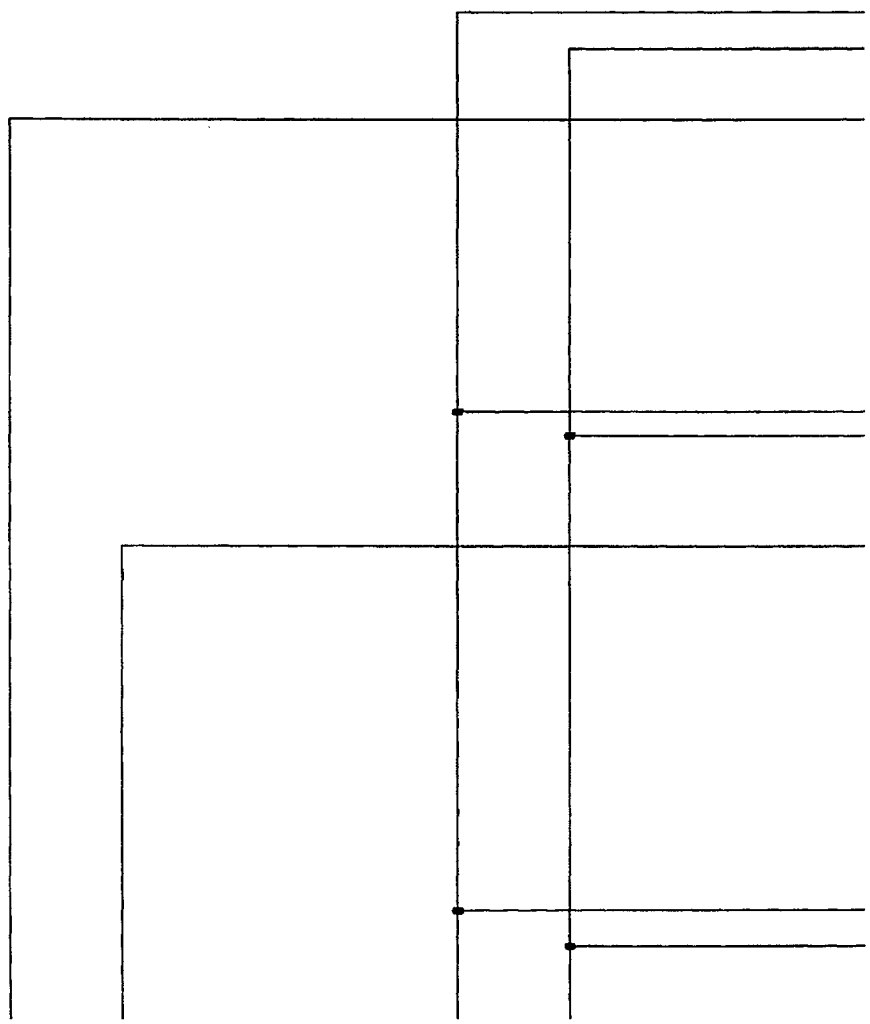
FIGURE 19R2

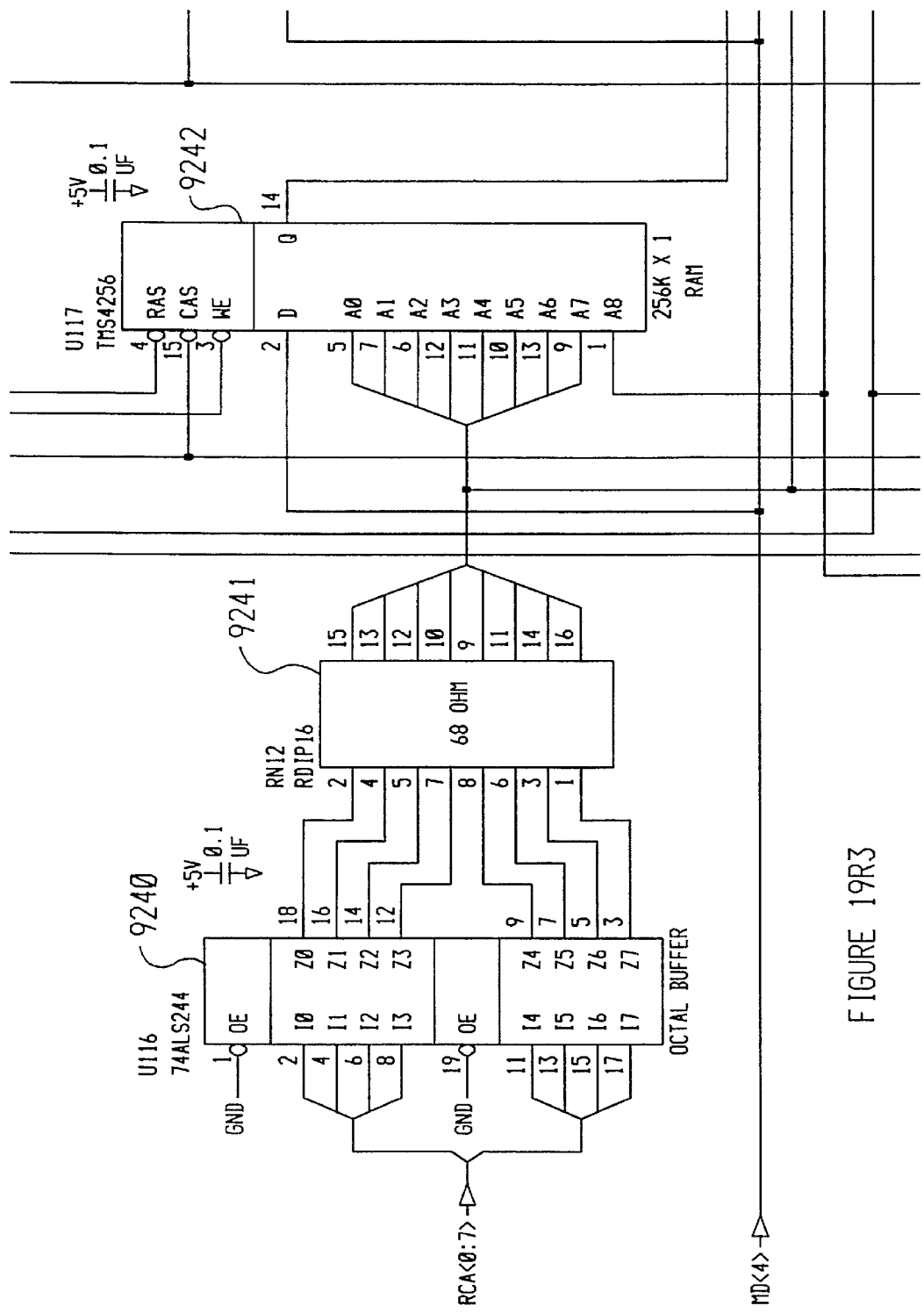
FIGURE 19R3

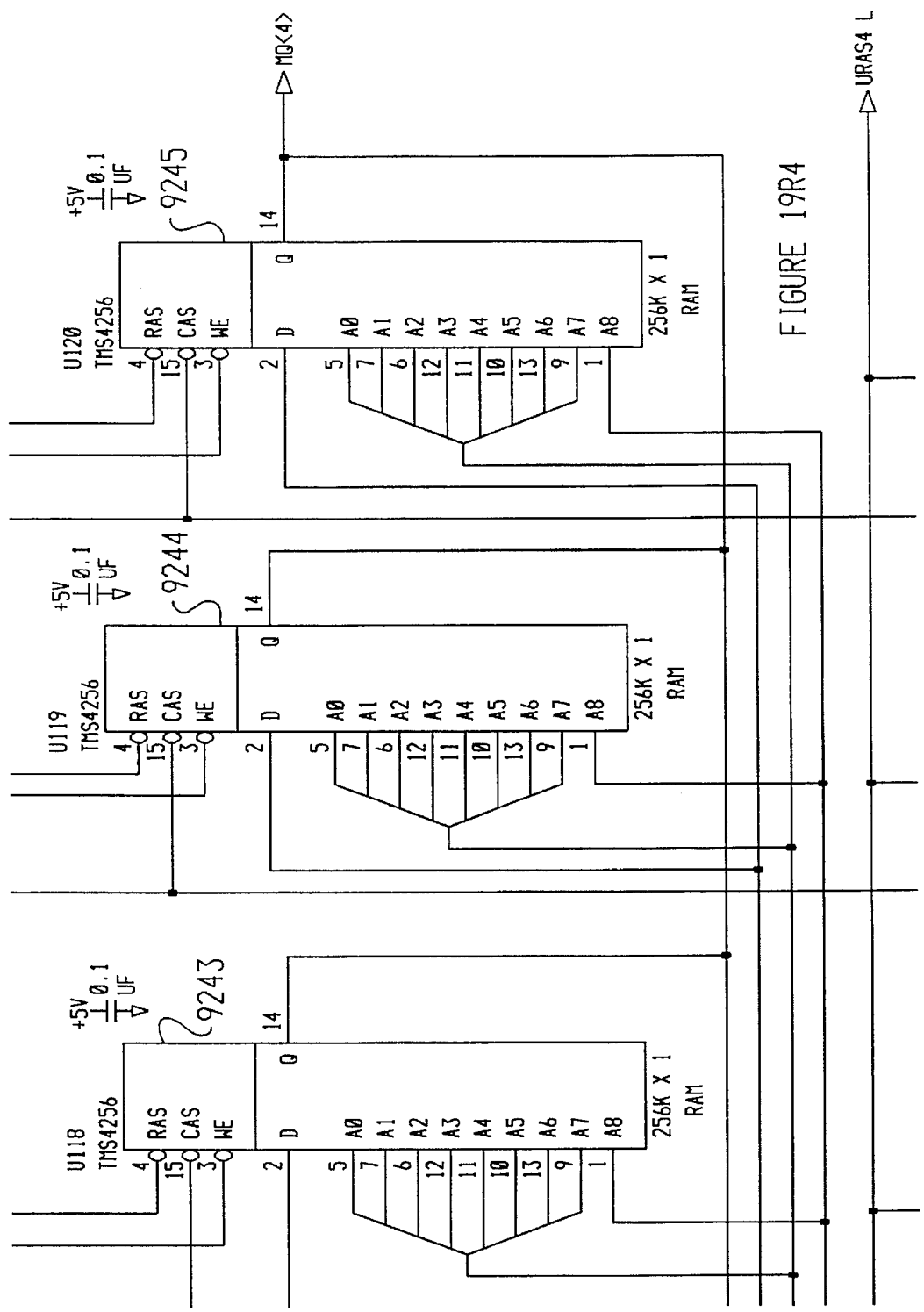
FIGURE 19R4

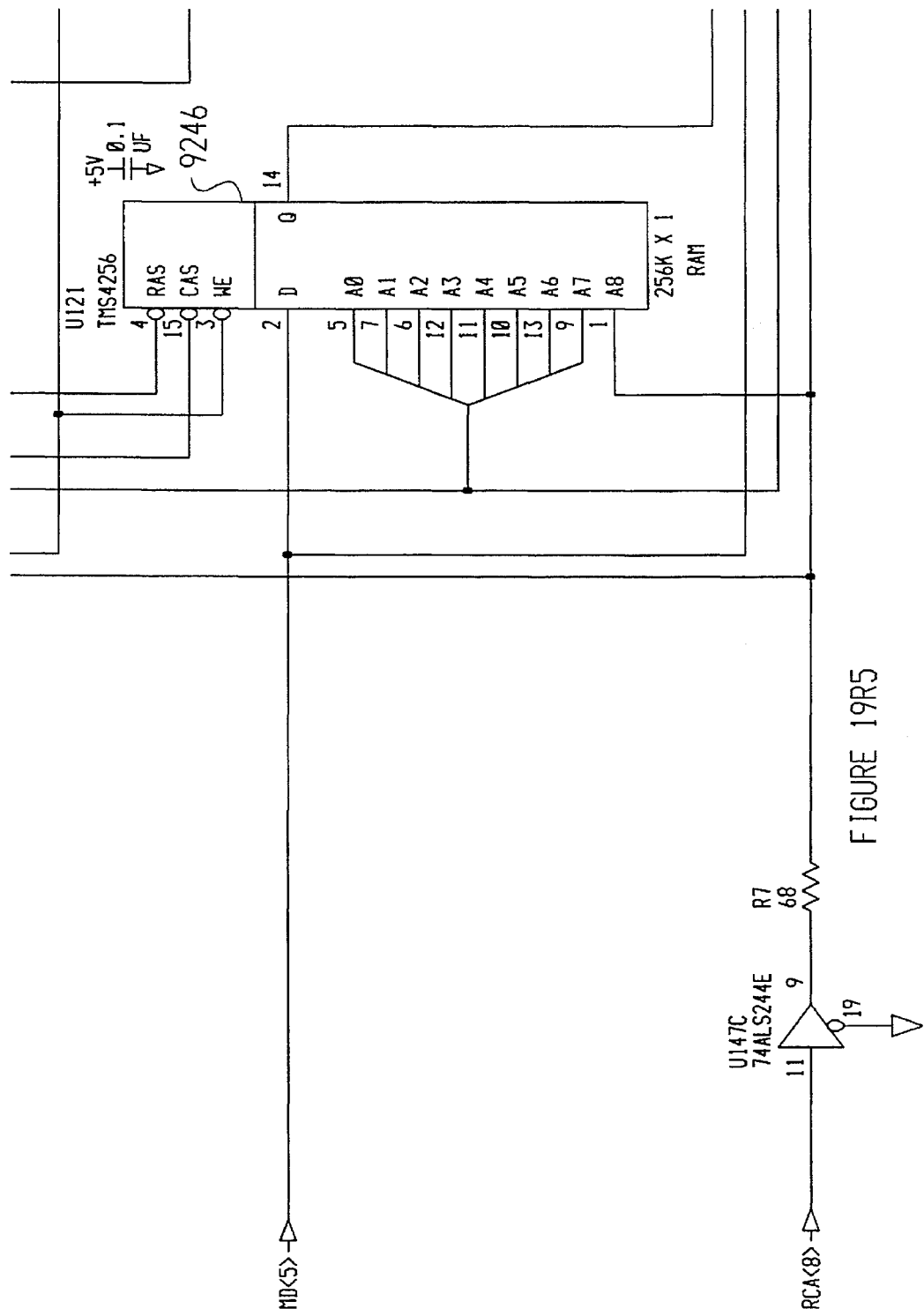

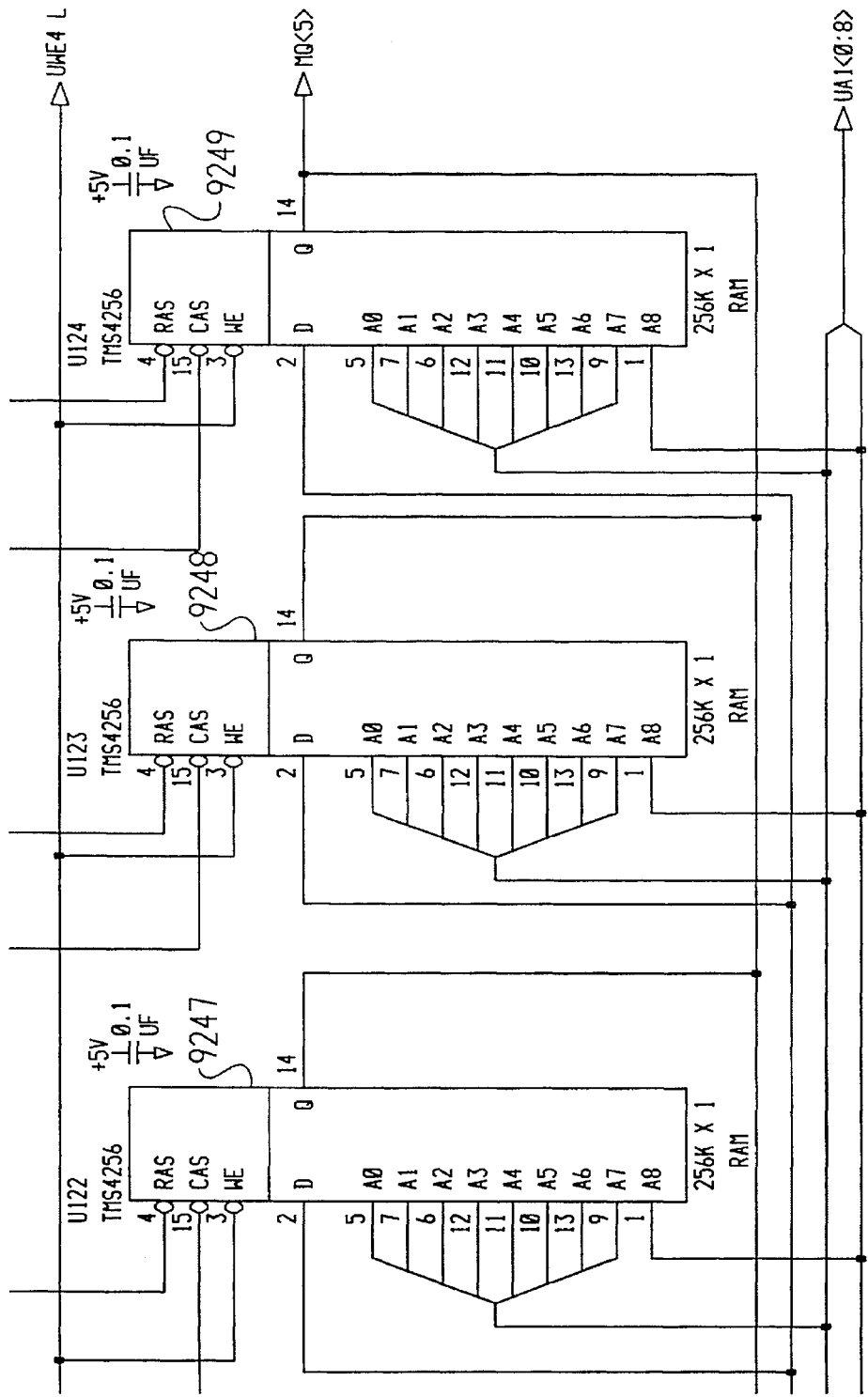
FIGURE 19R6

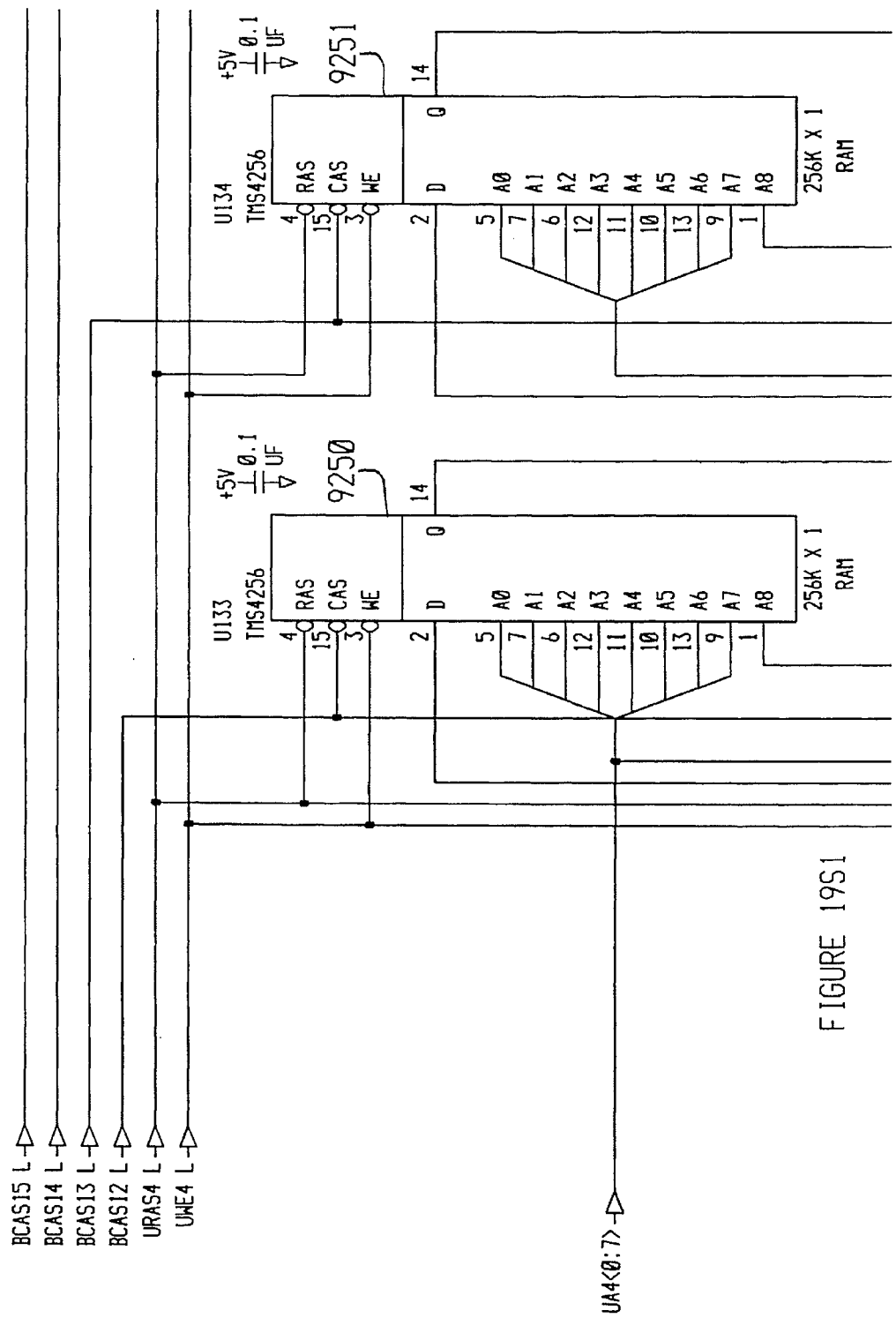
FIGURE 1951

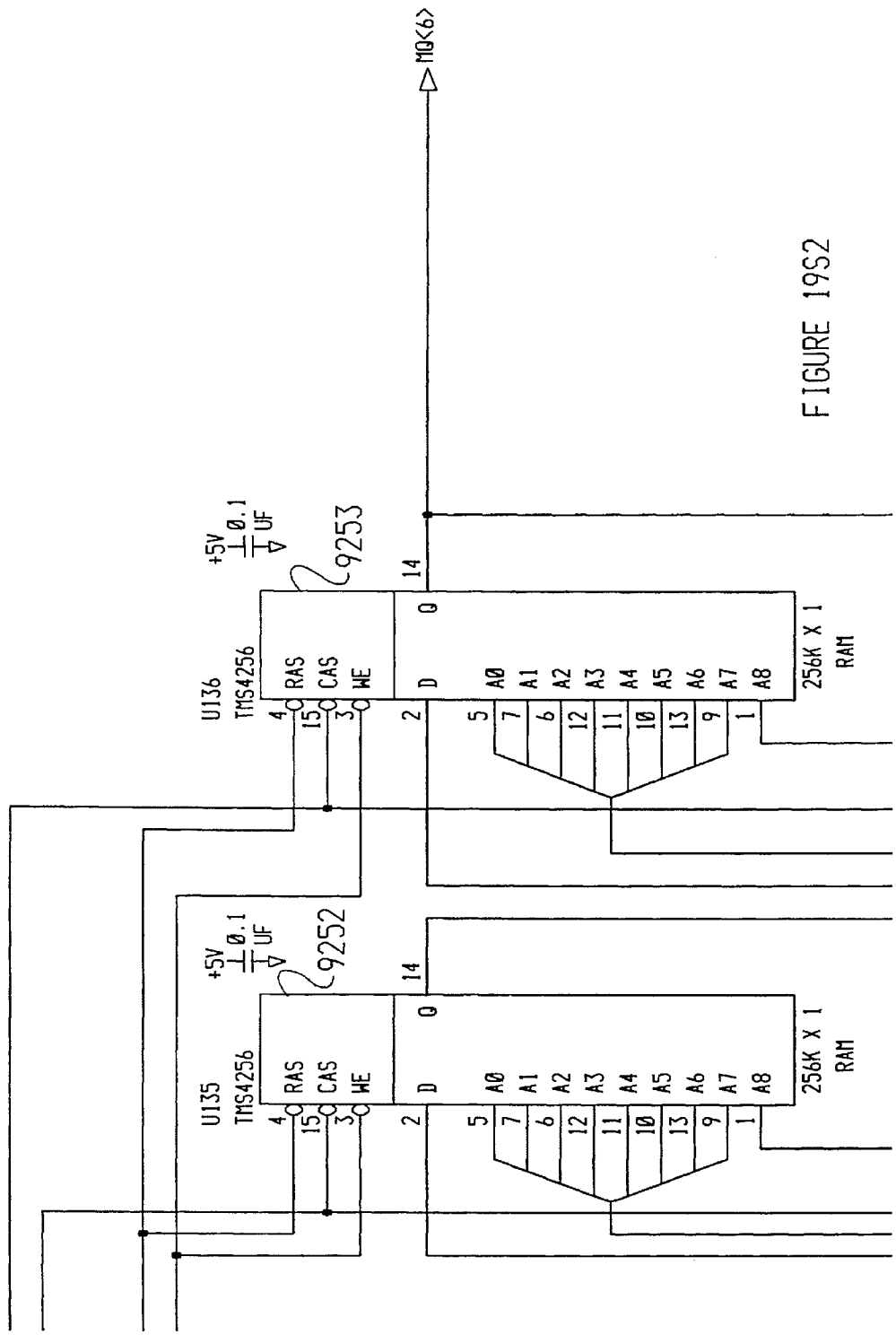
FIGURE 1952

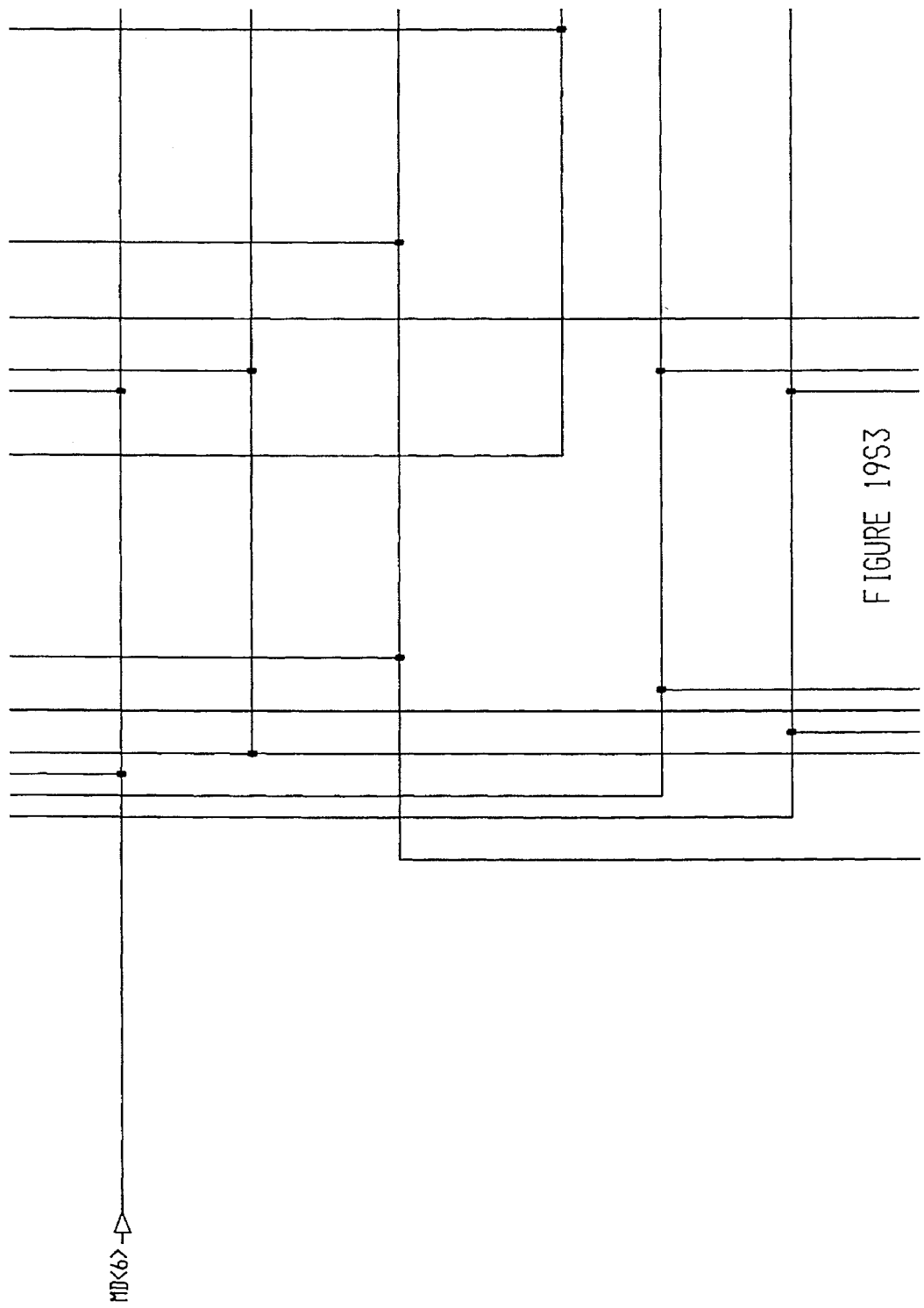
FIGURE 1953

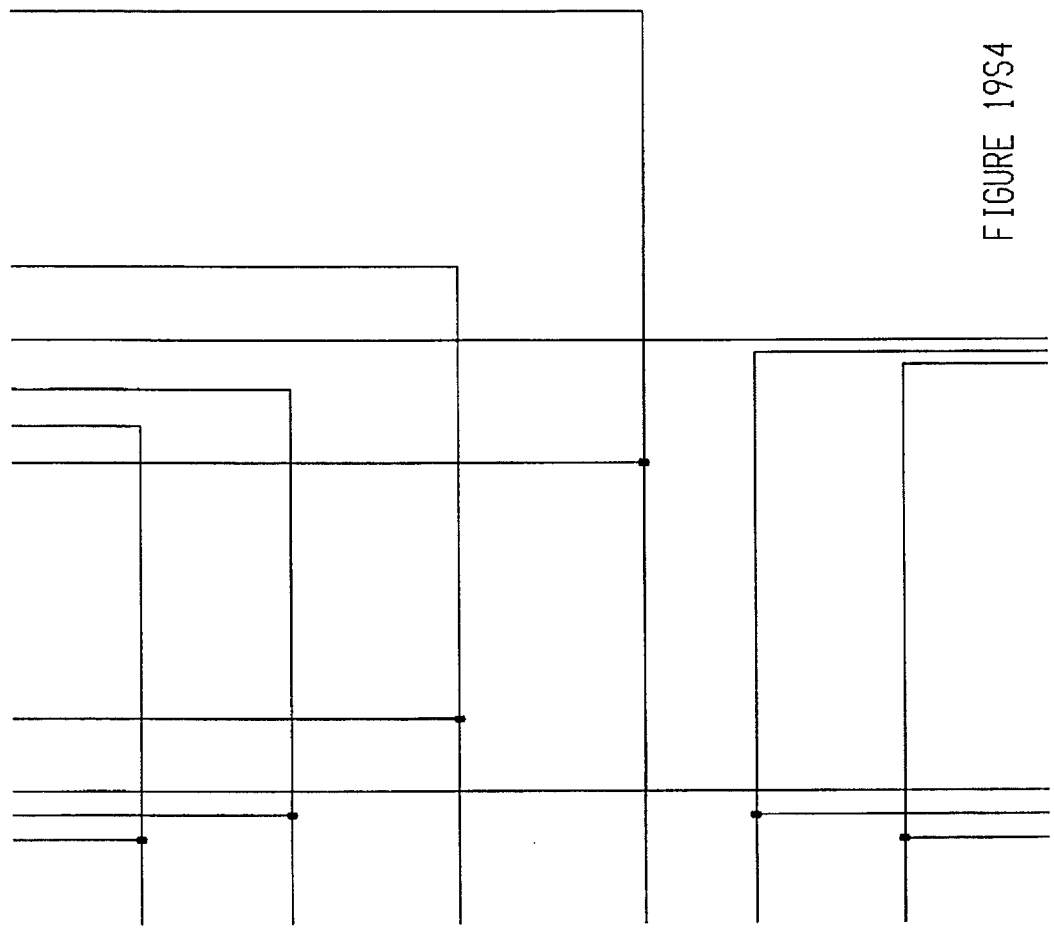
FIGURE 19S4

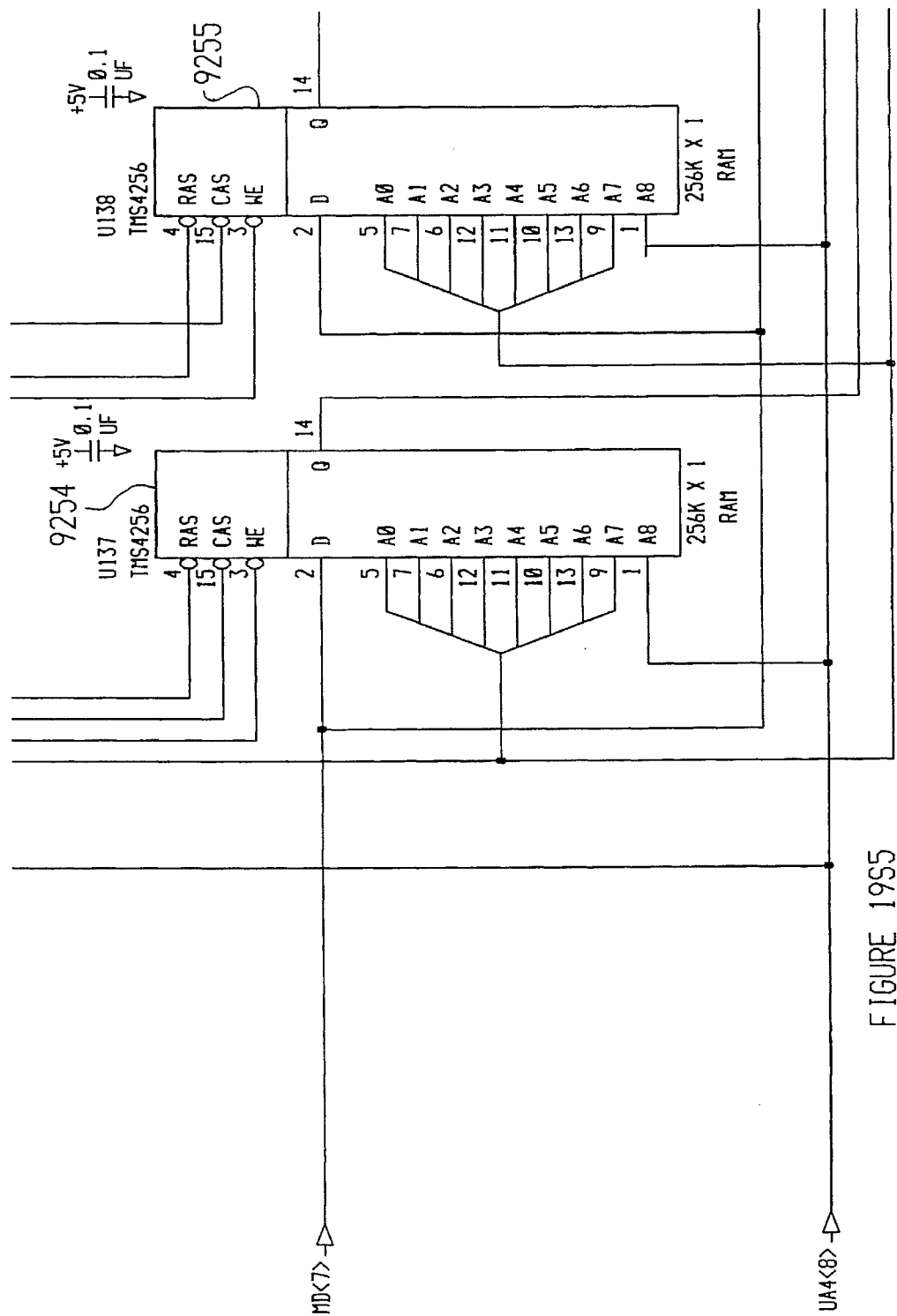
FIGURE 1955

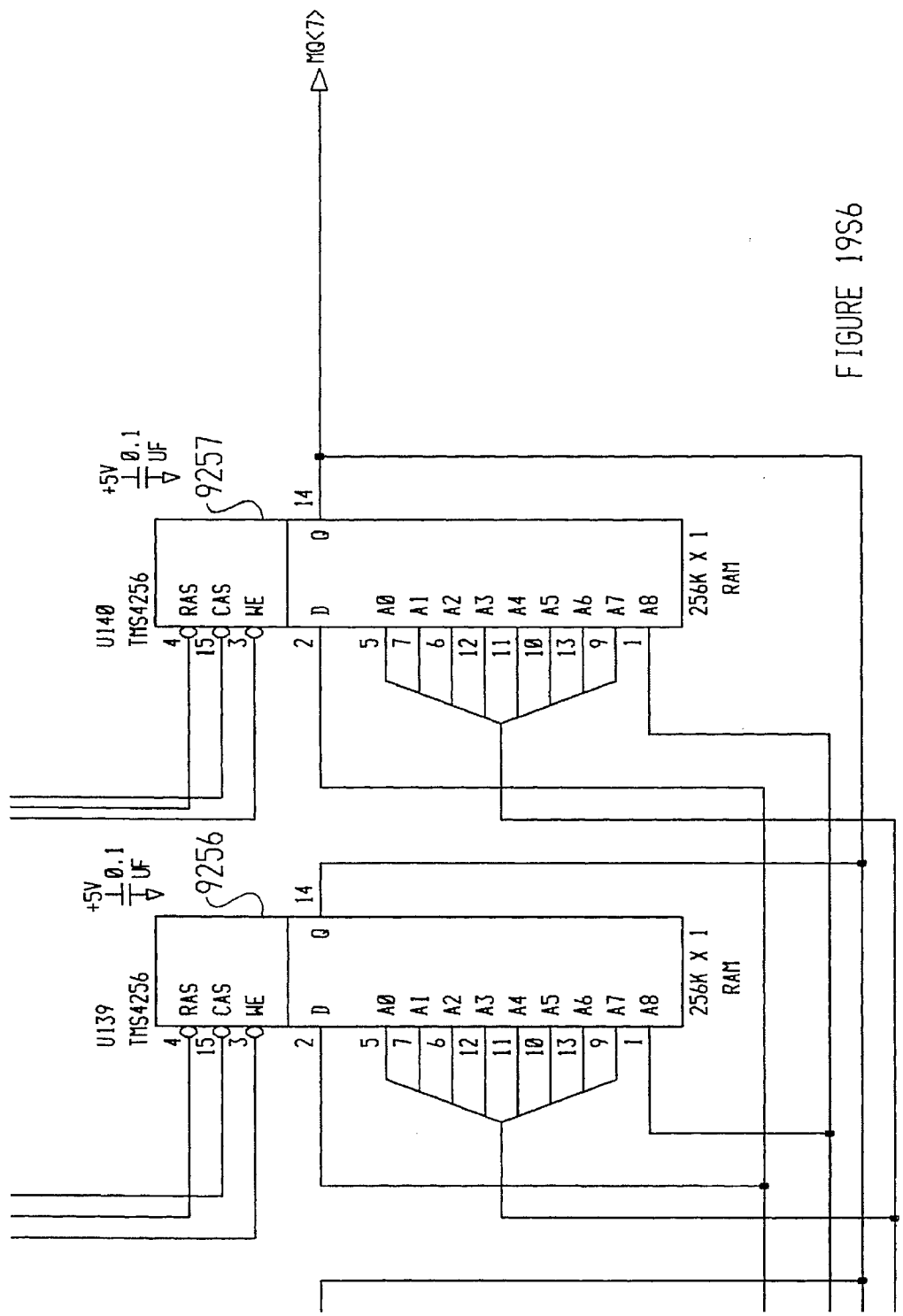
FIGURE 19S6

| SERIAL I/O<br>6 CHANNELS<br>RS232<br>BI-DIRECTIONAL<br>CHANNELS<br>12026-12031 | VME<br>INTERFACE<br>(84000-FFFFFF)<br>-ADDRESS-<br>-DATA-<br>-CONTROL-<br>12044 | |
|---|---|---|
| TIME-OF-DAY<br>132 | 68000<br>130 | INTERRUPT<br>CONTROLLERS<br>(16 INPUTS)<br>FIELDS INTERRUPTS FOR<br>OTHER CARD AND<br>PERIPHERALS WITHIN CPU<br>12040-12041 |
| DYNAMIC RAM<br>512K BYTES<br>(0000-7FFFF)<br>-STACKS-<br>-BUFFERS-<br>-LOCAL DATA-<br>12036 | EPROM<br>512K BYTES<br>(200000-27FFFF)<br>-PROGRAM-<br>12038 | NON-VOLATILE<br>RAM<br>128K BYTES<br>134 |

FIGURE 20A

ULTRASOUND BLOOD FLOW/TISSUE IMAGING SYSTEM

CROSS-REFERENCE TO RELATED APPLICATION

This application is a continuation of U.S. patent Ser. No. 07/515,311 filed Apr. 26, 1990, and now abandoned, which is a continuation of Ser. No. 06/892,753, filed Aug. 1, 1986, now abandoned under C.F.R. §1.62, which is a continuation-in-part of U.S. patent application Ser. No. 892,211, filed Jul. 30, 1986, and titled ULTRASOUND BLOOD FLOW/TISSUE IMAGING SYSTEM, and now abandoned, the specification and drawings of which are included by reference.

TECHNICAL FIELD

This invention relates to medical diagnostic systems using ultrasound. More particularly, this invention relates to an ultrasound imaging system for creating real-time images of tissue and blood flow.

BACKGROUND ART

Ultrasonography is a well-known medical diagnostic technique in which pulses of ultrasonic energy are directed into the body, and returning echoes are detected. In the past, medical systems using ultrasonography have produced black and white (gray scale) images illustrating the tissue surrounding portions of the vascular system. Tissue, being a relatively good reflector of ultrasound, appeared on images in varying shapes and shades of gray depending on the return echo amplitudes. Blood, however, being a poor reflector of ultrasound, would not appear in these images. The vessel interior, instead, appears black in the image where ultrasound was poorly reflected. A gray scale image alone does not provide sufficient information to diagnose the vascular system because soft plaque, which builds up in vessel walls and which is a poor reflector of ultrasound, cannot always be distinguished from the blood.

In the mid-1970's, ultrasound technology began to utilize the Doppler principle to obtain information on blood flow from moving scatterers in the blood. In one technique a continuous wave Doppler ultrasound signal is transmitted into the body and the echoed signal is processed to separate out the signals which are Doppler shifted (those having a change in frequency from the transmitted ultrasound signal). This continuous wave technique did not provide spatial information and was somewhat difficult to use. To improve spatial resolution, a pulsed Doppler ultrasound technique was developed, wherein reflected energy from a sample volume within a vessel is analyzed for changes in intensity and frequency relative to the transmitted ultrasound signal. Using the continuous wave or the pulsed Doppler technique, an analysis of one axial line or sample site is respectively performed. The output normally is a waveform showing the changes in frequency versus time and changes in intensity versus time. Neither pulsed nor continuous wave Doppler, however, provide real-time anatomical information about the vessel. A skilled technician analyzes the peak velocities of the intensity and the waveform spreading over time in the frequency versus time waveform for indications of disease.

One of the problems with these techniques is that the peak frequencies which are proportional to blood flow velocities may be inaccurate. When plaque builds up in the vessels, the direction and speed of blood flow are altered. The peak velocity at the sample site, as calculated parallel to the vessel, may have a direction different from the line of the vessel. For the case where plaque is not symmetrical, the velocity component parallel to the wall is an inaccurate measure when measured using the assumption that flow is of peak velocity.

Another problem with these methods is that a relatively few sample sites, usually one, are analyzed for blood flow characteristics.

Another problem is that the relative position of the sample site within the vessel as shown in a gray scale image may vary from the actual site within the vessel due to the movement of the blood vessel due to heart pulsation or the ultrasound transducer between samplings. Thus the gray scale image needs to be displayed in close to real time. This has imposed a limit on the number of sample sites that can be processed using conventional technology.

X-ray angiography, another vascular system diagnosis methodology, is a well-known technique in which a contrast dye (opaque to X-ray) is injected into the vascular system and X-ray pictures are taken of the dye passing through the vasculature. This approach is invasive and does not provide software tissue anatomical or blood flow velocity information needed for accurate disease diagnosis.

In summary, the contemporary evaluations of the vascular system are hampered by an inability to see all the influences on blood flow in a global fashion. X-ray angiography and tissue imaging provide a view of the vascular tree, but miss the details of flow within a vascular compartment and show none of the surrounding soft tissue. Continuous wave Doppler ultrasound provides evidence of flow events, but tells nothing about the non-anatomical characteristics of the vessel and surrounding tissue. Duplex imaging offers a view of the surrounding anatomy and waveform output of flow within a sample volume. A single sample volume and a corresponding waveform output provide little information about the dynamic flow within the vessel and the influences of those dynamics on the Doppler spectral output.

DISCLOSURE OF THE INVENTION

An object of this invention is to provide an ultrasound imaging system capable of producing gray scale images of the anatomy along with color images of blood flow simultaneously in a single image.

Another object of this invention is to provide an ultrasound imaging system that samples every point in the scanning field for amplitude, phase, and frequency, as opposed to the sampling of one, two, or three sites.

Another object of this invention is to provide an ultrasound imaging system which time shares between the processes of building the image and analyzing the velocity information intake to build an image in close to real time so that the image accurately depicts both tissue and blood flow.

These and other objects of the invention are provided by an ultrasound blood flow/tissue imaging system for producing angiodynograms. Angiodynography contains some of the conventional elements of real-time ultrasonography and duplex imaging, such as echo-ranging, B-mode real-time displays, range-gating, and Doppler signal processing. New to this approach is the synchronization of all these signal processing events into a single real-time image that shows not only the vascular anatomy and surrounding tissue but also the flow events within the vascular compartment. The ultrasound imaging device uses array processing techniques to perform the necessary signal processing and image updating at 18 times per second.

The system uses a linear array of ultrasound transducers for both imaging and Doppler. The linear array provides a uniform scanning field having a small size to permit easy access to the carotid arteries and peripheral vessels. Focusing within the array is done by phasing of the array elements to produce a nearly continuous focus over the scanning field to maintain conventional image resolution and to produce very small Doppler sample volumes.

The system tests signals throughout the scanning field for amplitude, phase, and frequency. Slow moving or stationary tissue signals provide the basis for the B-mode real-time image. The phase of the signal yields information about the presence of motion and its direction. Any change in the echo signal frequency relates through a Doppler equation to an echo source velocity.

The stationary echo signals are assigned a gray scale intensity proportional to the echo signal amplitude. The resulting gray scale image displays a mix of signals that includes soft tissue specular reflectors and small scattering bodies.

Detecting a change in the phase of a returning echo signal is performed based upon the given phase and frequency of the transmitted signal. Phase changes between the transmitted burst and the returning echo signals represent movement toward or away from the transducer array. In one embodiment, the directions are distinguished by assigning the colors red and blue to represent forward and reverse flow, respectively, or vice versa. The frequency change (Doppler frequency shift) in the echo signal is related to the closing velocity of the echo source and the transducer array through the Doppler equation. In an angiodynogram, an increasing Doppler shift frequency produces an increasing shift in color saturation toward white or another synthetically assigned color.

The angiodynogram enables a person to see how the blood flow varies over time, how velocity varies over the lumen, and how blood flow has been modified by anatomy or disease. Not only can the direction of flow be seen, but also the presence and pattern of flow disturbance. The angiodynogram lets one see the transient instability that may occur during only portions of a cardiac cycle, as well as the turbulence caused by significant disease. The abnormal flow architecture, including flow separations and reversals within a normal vessel, can also be seen. Rough endothelial surfaces become visible through the eddy currents they create. Heterogeneous plaque can be seen and, in some diseased vessels, non-echogenic regions appear, suggesting flow stagnation or homogeneous soft plaque. The flow and tissue information are displayed simultaneously, eliminating the search and sample strategies of conventional duplex imaging.

BRIEF DESCRIPTION OF THE DRAWINGS

NOTE: When a figure is referred to in the following description, the reference is also meant to include the sub-figures, e.g., FIG. 2A is actually composed of FIGS. 2A1 through 2A6.

FIG. 10 is the circuit schematic for the amplitude weighting, summing, and time-gain control circuits.

FIG. 12 is a block diagram and circuit chematic of the A/D board.

FIG. 13 is a block diagram and circuit chematic of the timing and control subsystem.

FIG. 14 is a block diagram and circuit chematic of the flow processor subsystem.

FIG. 16 is a block diagram and circuit schematic of the centroid subsystem.

FIG. 17 is a block diagram and circuit schematic of the interpolator subsystem.

FIG. 19 is a circuit schematic of the review buffer.

BEST MODE FOR CARRYING OUT THE INVENTION

Introduction

Figure 1:
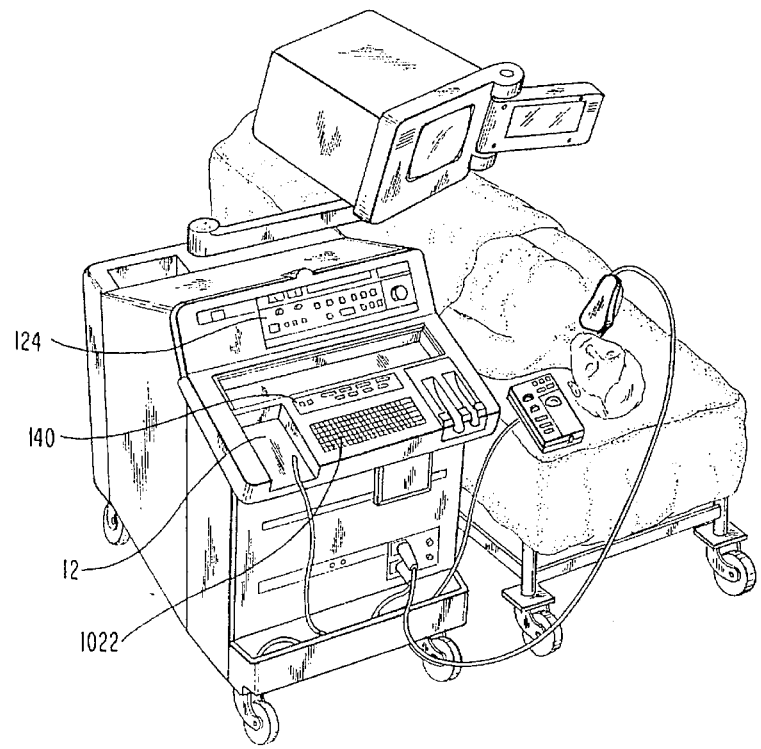
FIG. 1 is an isometric view of the ultrasound blood flow/tissue imaging system of this invention.

Referring to FIG. 1, the ultrasound flow imaging system 10 provides imaging, spectral analysis, measurement and calculations, and output storage and retrieval for diagnosing and evaluating the vascular system. The imaging capability includes angiodynography and tissue-only imaging. Regarding angiodynography, in one embodiment the system provides high resolution, real-time gray scale images of tissue simultaneously with real-time color depiction of blood flow. In one embodiment, both tissue and flow depiction have identical spatial resolution, with the image updating at eighteen frames per second for a 7.5 megahertz (referred to throughout as mHz) ultrasound beam. Regarding tissue-only imaging, the system provides high resolution, real-time gray scale images of tissue using 120 gray levels at thirty frames per second.

The spectral analysis capability in one embodiment allows for point by point analysis of the image using 128 point or 256 point resolution. A spectral sampling capability enables the operator to record from any two sample sites simultaneously and perform comparative analysis between two spectral displays, two velocity displays, or a combination of spectral and velocity displays. The spectral analysis capability also includes automatic waveform analysis for calculating and displaying maximum, minimum, mode and mean waveforms for spectral and velocity displays. When spectrum analysis is selected, a stereo audio signal of blood velocity is processed and heard through two speakers.

The ultrasound flow imaging system 10 performs linear and area measurements, percent stenosis, spectral and velocity calculations, post-processing, and vessel diameter and volume flow calculations. Percent stenosis is calculated from either diameter reduction or cross-sectional area reduction. The spectral and velocity calculations can be performed on single- or dual-spectral data or on velocity data. The system 10 calculates: percent window, velocity profile, acceleration, pulsatility index, and Pourcelot's ratio for any sample site. Post-processing calculations and analysis can be performed from digitally stored images. Vessel diameter and blood flow may be calculated from spatial flow diameter and corrected velocity profile.

The system 10 provides for Doppler audio stereo output of forward and reverse blood flow, patient reports, cine loop, digital storage, video tape storage, and high resolution photographic storage. A cine loop output is derived from an internal storage of up to 10 seconds or real-time images or spectrum, with image freeze and variable playback frame rates. Digital storage records real-time data on one-half inch video tape which can later be retrieved for further analysis or manipulation without image quality loss. Video tape storage 124 records data in standard NTSC format for archiving. High resolution photographic storage is provided by an RGB camera for recording color images on either 35 mm slides, SX70 Polaroid prints, or 4"×5" transparencies. A handheld camera may also be used.

In one embodiment, an operator communicates with the system 10 using a keyboard 1022, front panel buttons 140, foot switches, remote control unit, which contains buttons, rotary switches, and a trackball. The image is displayed on a cathode-ray tube (CRT) screen 120 while operational menus are displayed on a liquid crystal display (LCD) screen 136. The image is derived from a transducer 12 placed in contact with the skin of the patient.

Table 1, below, lists the sections of the detailed description, along with the figures and part numbers introduced in the respective section:

TABLE 1

| Section | FIGS. | Part Numbers Introduced |
|---|---|---|
| Introduction | 1 | 10 |
| System Overview | 2A–C, 3A–C | 12–145 |
| TPAD Switch | 5 | 146–198 |
| Transmitter | 4A–F | 200–320 |
| Crossbar Switches | 6A–C | 300–590 |
| MUX | 7A–C | 600–998 |
| Delay Lines | 8A–E | 1,000–1,498 |
| Delay Controller | 9A–E | 1,500–1,998 |
| Amplitude Weighting, Summing and TGC | 10A–D | 2,000–2,898 |
| Log Amp | — | — |
| Clutter Canceller | 11A–G | 3,000–3,598 |
| Timing and Control Subsystem | 13A–R | 5,000–5,650 |
| Flow Processor Subsystem | 14A–D, 15A–F | 6,500–6,800 |
| Centroid Subsystem | 16A–O | 7,000–7,500 |
| Interpolator Subsystem | 17A–J | 7,600–7,898 |
| Digital Storage Subsystem | 18A–Z, 18AA–HH | 8,600–9,000 |

System Overview

Figures 1, 5:
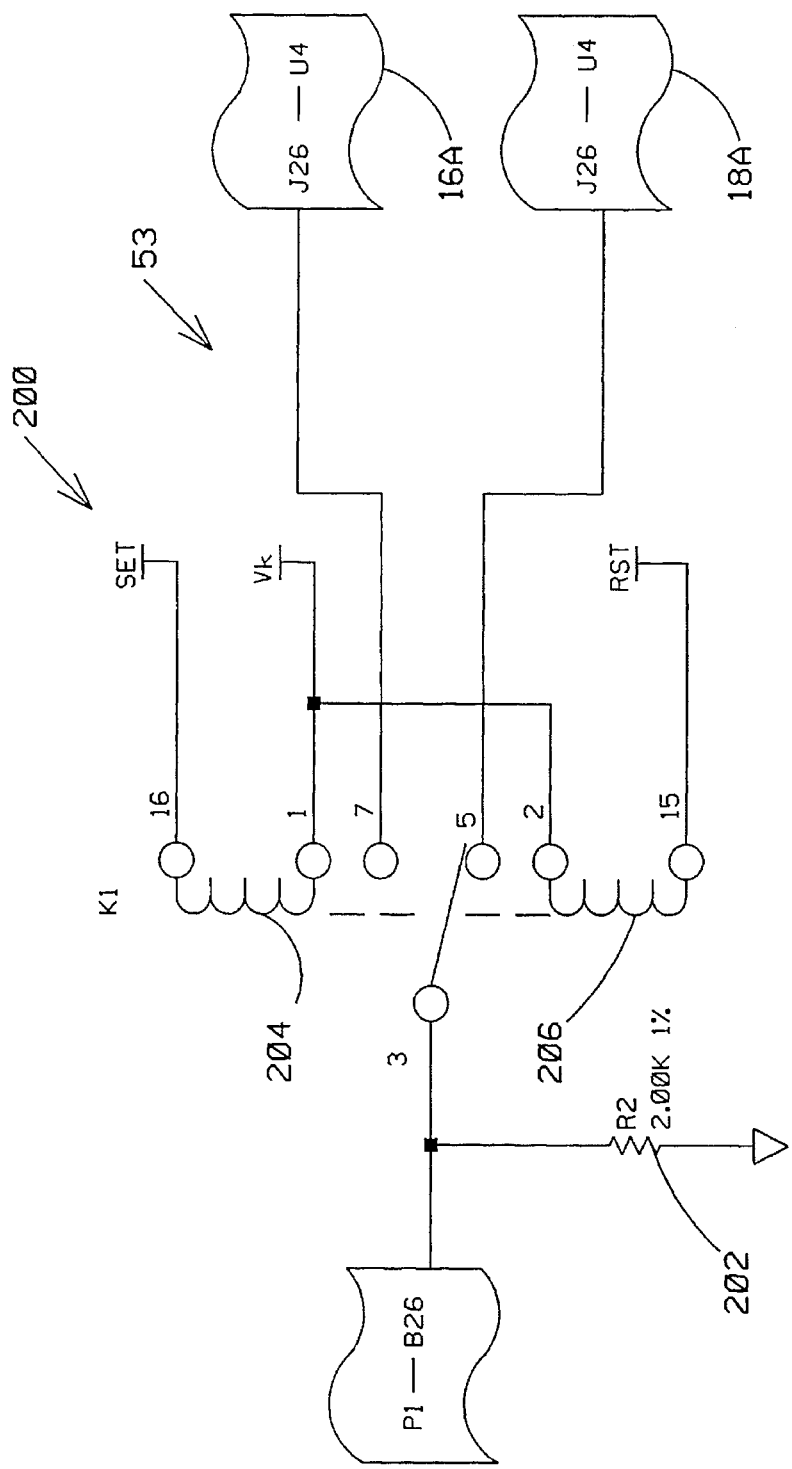
FIG. 5 includes the block diagram and circuit schematics for the transmitter.
Figures 2, 5:
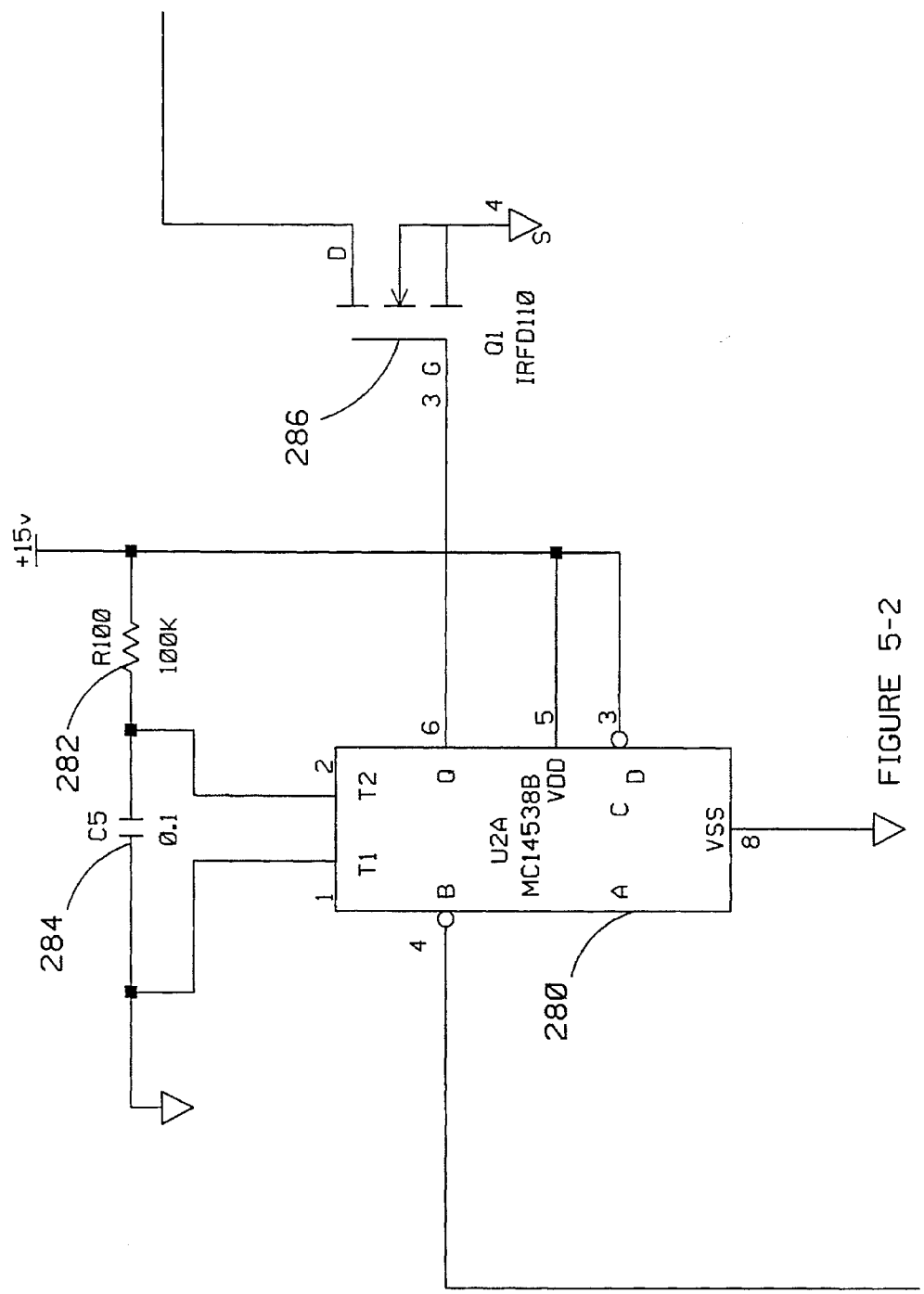
FIG. 2 is a block diagram of the ultrasound imaging system.

A block diagram of the imaging system is illustrated in FIG. 2. With reference to FIG. 2A, the system includes a pair of transducers 12, 14, each of which includes a large number of transducer elements 16, 18, respectively. Although the number of elements 16, 18 can vary with specific designs, in one operational embodiment the transducer 12 includes eighty sequentially arranged transducer elements 16. The other, a lower frequency transducer 14, includes ninety-four sequentially arranged transducer elements 18. As explained in greater detail below, some of the transducer elements 16 receive a respective 7.5 mHz pulse for transmission, thereby generating a beam of ultrasound energy at 7.5 mHz. Similarly, some of the elements 18 of the transducer 14 receive a respective 5 mHz pulse, thereby generating a beam of ultrasound energy at 5 mHz. The elements 16, 18 of the transducers 12, 14 then receive echoes from the transmitted pulses and generate respective electrical return signals corresponding thereto.

The beam pattern of the transducer elements 16, 18 is relatively narrow, although the beams of adjacent elements 16, 18 overlap each other, particularly at distances well away from the surface of the transducer elements 16, 18. As is well understood in the art, the individual beams from the transducer elements 16, 18 can be combined, and a combined beam can be formed by adjusting the delay of the signal coupled from one transducer element 16, 18 with respect to the delay of the signals coupled from adjacent transducer elements 16, 18.

The flow imaging system operates on the Doppler principle in which the frequency of the acoustic energy reflected from acoustic scatterers in the flowing blood differs from the frequency of the transmitted acoustic signal by an amount that is indicative of the blood flow velocity. Clearly there will be no Doppler shift in the received signal if the acoustic beam intersects the blood flow at a 90° angle. In other words, it is necessary for the velocity vector of the blood to have a component lying along the axis of the beam, i.e., toward or away from the transducer elements 16, 18. Further, in order to ensure accurate measurement of velocity, it is desirable to maintain the angle of the blood flow velocity vector and the axis of the acoustic beam at a known, relatively constant value. The inventive imaging system achieves this result by placing the transducers 12, 14 against respective, uniquely designed coupling wedges 20, 22, which are, in turn, placed in contact with the skin S of a patient P adjacent a blood vessel V. The wedges 20, 22 maintain the transducers 12, 14 at a fixed geometric relationship to he vessels V so that the Doppler shift of the received signal bears a fixed relationship to the blood flow velocity in the vessel V.

Figure 3A:
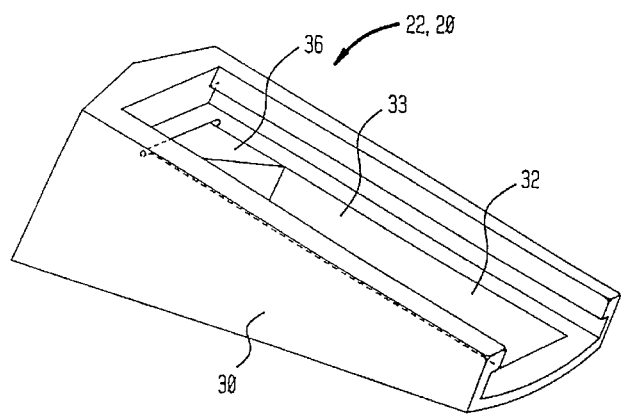
FIG. 3 is an isometric view of the coupling wedges.

The acoustic properties of the coupling wedges 20, 22 are somewhat critical since they cannot adversely affect the transfer of acoustic energy from the transducers 12, 14 to the patient. As illustrated in FIG. 3, the wedge consists of a wedge-shaped body 30 defining a cavity that is filled with a fluid 32. The inner and outer surfaces of the cavity are covered by respective membranes 33, 35. The fluid 32 must be a low-loss medium so that the transmitted and received acoustic energy is not unduly attenuated in the coupling wedges 20, 22. It should also have the property of transmitting sound at substantially the same speed as the body. In one embodiment, water was found to have acceptable properties for use as the fluid 32. The membrane 33 should be of a low-loss material and it should have a thickness that is a multiple of quarter wavelengths of the acoustic energy in order to cancel reflections from the walls of the membrane 33. Finally, both the fluid 32 and the membrane 33 should have an acoustic impedance that is approximately equal to the acoustic impedance of the patient P.

One material that may be advantageously used to form both the body 30 and the membrane 33 is NVCREL, sold by DuPont, since it has low permeability to water, is easily bonded to itself, and has substantially the right acoustic properties.

Figure 3B:
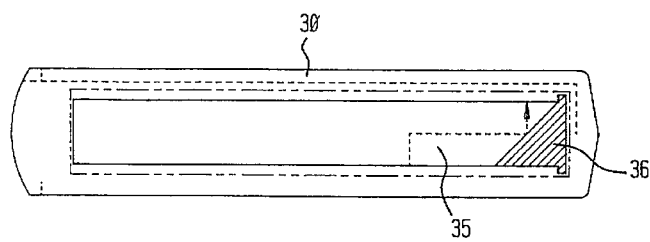
Figure 3C:
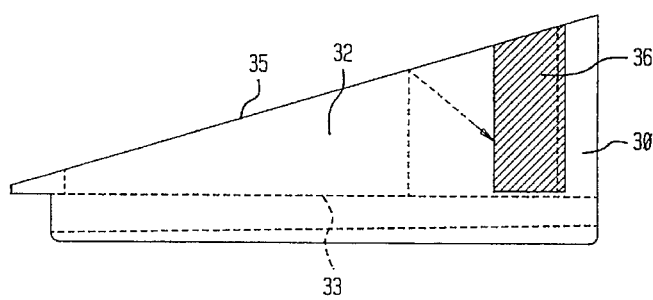
Figure 4A:
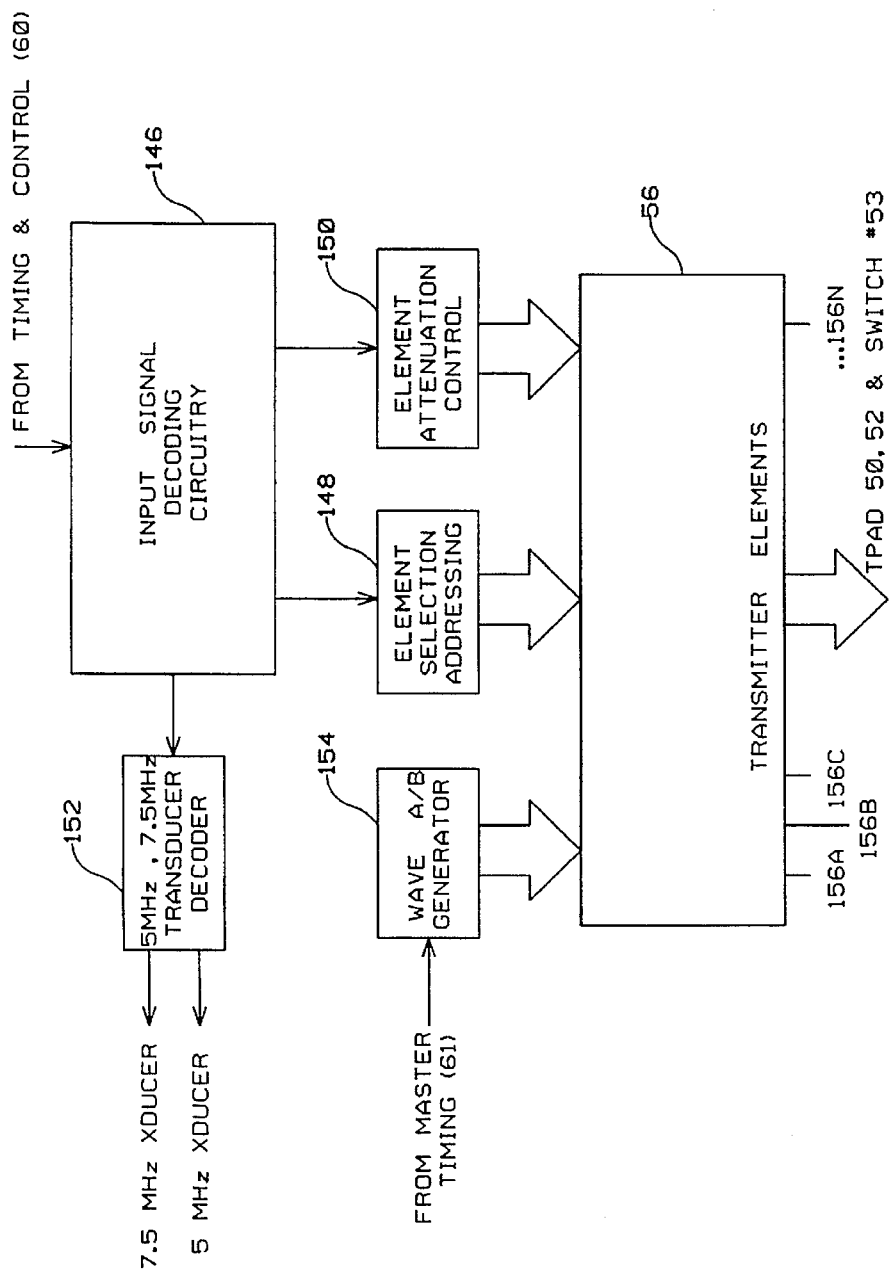
FIG. 4 is the circuit schematic for the T-pad switch.

Even though great care is taken to ensure that the fluid 32 and membranes 33, 35 are of low-loss substances and have an acoustic impedance matching the acoustic impedance of the body, there are nevertheless reflections from the membranes 33, 35 as well as from the interfaces between the outer membranes 35 and the patient p and the inner membrane 33 and the transducer. A unique aspect of the coupling wedge 20, 22 is the selection of the angles of the wedges 20, 22 to direct reflected signals from patient at the outer membrane 35 at the interface 34 to a sound-absorbent material 36 placed on one side of the wedges 20, 22, as illustrated in FIG. 3C In one embodiment, the sound-absorbent material 36 is sound absorbing material No. 149WS30, sold by B. F. Goodrich. Although the sound-absorbent material 36 absorbs most of the ultrasound energy that is incident on it, it nevertheless reflects a small portion of the incident ultrasound. For this reason, the surface 37 of the material 36 is formed at an angle to direct any reflected ultrasound toward the sidewall of the body 30, as illustrated in FIG. 3B. Although the material 36 is illustrated as reflecting ultrasound toward the sidewall, it will be understood that other angles can be selected to direct the reflected ultrasound at other angles to the sidewall or toward the inner membrane 33, as long as the reflected ultrasound is not directed back along the same path in which it was incident on the material 36.

The transducers 12, 14 receive tissue and blood flow ultrasound signals in real time at frame rates varying from 35 to 1 frame per second. In one embodiment, more than 50 lines of uninterpolated ultrasound data will be received for each frame of image, such that: axial resolution of the beam does not exceed three wavelengths; lateral resolution is uniform throughout the image; and transverse axis resolution, for 7.5 mHz, is less than 3 millimeters.

Returning now to FIG. 2A, the signals coupled to and from the transducers 12, 14 pass through respective T-pads 50, 52 and switches 53, which basically provide three functions. First, the switches 53 connect either the transducer 12 or the transducer 14 (but not both) to a transmitter 56 and a receiver front end 54. Thus only one of the transducers 12, 14 is used at any time, depending on the frequency of the signal applied to the transducers 12, 14. Second, the T-pads 50, 52 and switches 53 include a conventional "T-pad" resistor circuit that maintains the output and input impedances of the transducers at a predetermined value, such as 50 ohms, to minimize standing waves in the tones from the transducer elements 16, 18. Third, the T-pads function as adjustable attenuators to equalize the gains of the transducer elements 16, 18.

The T-pads and switches 50, 52 are connected in parallel to a series of crossbar switches and filters 58, one of which is provided for each element 16, 18 of the transducers 12, 14.

Each of the transmitters 56 receives two input streams. One stream, from timing and control 60 (FIG. 2c) specifies the power attenuation level and the transducer element 16, 18 selection to the transmitter 56. The second stream from Master Timing 60, specifies the on-time of the transmitter 56. The transmitters 56 thus generate respective signals for the transducer elements 16, 18 in combination so that the beam of acoustic energy is shifted from one side of the transducer to the other. However, unlike in the receiving mode, in the transmitting mode the transducer elements 16, 18 operate in the same phase.

The transmitter 56 beam selection control activates the crossbar switches 58 that select the transducer elements 16, 18 used to form the receive beam. Basically, the crossbar switches 58 are controlled so that a beam formed by forty adjacent elements 16, 18 steps sequentially from one side of the transducers 12, 14 to the other side. In other words, the crossbar switches 58 initially connect elements 1–40, then 1–41, then 3–42, etc.

The crossbar switch and variable gain amplifier 58 performs a number of functions in addition to selecting forty of the transducer elements 16, 18 to form the receive beam. First, the crossbar switch and variable gain amplifier 58 functions as a transmitter/receiver switch to protect the receiver by limiting the magnitude of the transmitted signal that is coupled to the receiver. Second, the crossbar switch and variable gain amplifier 58 adjusts the gain of the received signal to reduce the dynamic range of the received signal. Finally, the switch and variable gain amplifier 58 bandpasses the frequencies of interest in the received signal to improve the signal-to-noise ratio.

The crossbar switch 58 multiplexes the ninety-four incoming lines to forty output lines so that the remainder of the system requires forty or fewer processing channels. The forty outputs of the crossbar switch 58 are further reduced in number to twenty by a multiplexer 62 which basically sums the outputs from the transducer elements that are positioned equidistant from the center of the beam and thus presumably carry the same information signal. The outputs from the multiplexer 62 are applied to respective delay lines 64. The delay lines 64 are operated by a delay controller 66, which, in turn, is controlled by the CPU. The delay lines 64 effectively focus the beam to a relatively small area. The signal received by the transducer elements are delayed for a successively longer period of time toward the center of the beam. As a result, an acoustic signal reflected from a sound scatterer and received by a transducer element at the center of the beam is delayed so that the signal from the transducer element is output by the delay line 64 at the same time that the signals from the transducer elements at opposite sides are output by the delay lines 64.

The outputs of the delay lines 64 are applied to an amplitude weighting, summation, and time gain control circuit 68, which, in turn, is controlled by the delay controller 66 and a gain control circuit 70. The amplitude weighting, summation, and time gain control circuit performs a number of functions. First, it provides a "weighting" function in that it attenuates the signals from some of the transducer elements to a lesser or greater degree than the attenuation of the signals from the other transducer elements. More specifically, the weighting function approximates a cosine squared function having a peak at the transducer element at the center of the beam so that the signal from the transducer element 16, 18 at the center of the beam has a greater effect on the output of the circuit 68 than do signals from transducer elements 16, 18 on either side of the beam center. As explained in greater detail below, the purpose of the cosine squared weighting function is to suppress received beam side lobes, as is well understood by those skilled in the art.

Another function performed by the amplitude weighting circuit 68 is to vary the number of effective transducer elements as a function of the depth of tissue being examined. A beam formed by relatively few transducer elements 16, 18 is used to examine a tissue at a shallow depth, while a beam formed by a relatively large number of transducer elements is used to examine tissues at a greater depth. Varying the number of transducer elements, depending upon the depth of the tissue being examined, results in a "dynamic aperture," which optimizes the performance.

Still another function performed by the circuit 68 is to sum all of the outputs of the delay lines 64 after the amplitude weighting function has been performed. Thus the signals from all of the transducer elements 16, 18 are added constructively.

The final function performed by the circuit 68 is a time gain compensation to compensate for attenuation of the signal in the body as a function of depth. This attenuation compensation is accomplished by increasing the gain of the receiver as a function of time commencing at the start of the transmitted ultrasound. The time gain compensation circuit also compensates for changes in the gain of the transducer 12, 14 resulting from changes in the aperture, which, as mentioned above, varies dynamically. In other words, the gain of the transducer 12, 14 when multiple transducer elements 16, 18 are being used is substantially greater than the gain of the transducers 12, 14 when a relatively few transducer elements 16, 18 are being used. As a result, the gain of the receiver must be increased in inverse proportion to the number of transducer elements 16, 18 being used. Furthermore, the signal-to-noise ratio of the transducers 12, 14 increases with the aperture of the transducers 12, 14 (i.e., the number of transducer elements 16, 18 being used) since the transducer elements add the reflected ultrasound coherently, but add noise signals incoherently. Insofar as optimum sensitivity requires that the threshold of the receiver be maintained just above the noise level, it is desirable to compensate for the noise signals generated by tissues differently from flow signals generated by moving sound scatterers in the blood.

The amplitude weighting, summation, and time gain control circuit 68 generates two outputs, one of which is the received, weighted, and summed signal, gain compensated for tissue, and the other weighted, summed and gain compensated for flow, as explained above. The tissue gain compensated signal is applied to a logarithmic amplifier and band pass filter 72, which provide spectral noise limiting and data compression, thereby reducing the data storage requirements. The output of the log-amp 72 is used as a gray scale signal to image tissues rather than imaging moving sound scatterers in the blood.

The flow gain compensated signal from the circuit 68 is applied to a synchronous detector and clutter canceller circuit 74, which basically performs two functions. First, it eliminates the signals generated by non-moving sound scatterers, such as tissues, thus leaving only the signal reflected from moving sound scatterers in the blood. Second, it generates in-phase and quadrature components of these flow signals. Basically, the clutter cancelling function is provided by subtracting a return from the previous return. Since successive returns from non-moving scatterers will be identical, the only difference in the two returns will be signals generated by moving sound scatterers. The circuit 74 then reconstructs an RF signal indicative of the returns from only the moving sound scatterers without the presence of clutter from stationary tissue. More specifically, the incoming flow gain compensated signal is applied to an analog-to-digital ("A/D") converter which samples and digitizes each return signal. The digital signal is then alternately applied to one of two digital memories so that the other memory will contain the previous digitized sample. The output of the memory containing the previous digitized sample is then subtracted from the current digitized sample. The difference signal is then applied to a digital-to-analog ("D/A") converter which generates an analog signal indicative of the return from moving sound scatterers exclusive of returns from stationary tissues.

In-phase and quadrature components (sine and cosine components) of the analog flow signal are then generated by mixing the RF signal with an in-phase and quadrature local oscillator signal. On one operational embodiment, the signal applied to the transducer 12 is a pulse of 7.5 mHz repeating at a 16 kHz repetition rate. The spectrum of the transmitted signal is thus a series of lines 16 kHz apart centered at 7.5 mHz. The spectrum of the signal received from non-moving tissue has the same spectral components as the spectrum of the transmitted signal. The spectrum of the signal received from moving scatterers in the blood is the spectrum of the transmitted signal shifted upwardly or downwardly by a Doppler shift that is a function of the velocity (speed and direction) of the blood. The spectrum of the return signal from the tissue is eliminated by the clutter cancellet 74, thus leaving only the Doppler shifted spectrum from signals reflected from flowing blood. It is this Doppler shifted spectrum mixed down to baseband that is present in the in-phase and quadrature signals generated by the I.Q. detector and clutter cancellet circuit 74.

The logarithmic tissue signal and the in-phase and quadrature flow signals are then applied to a sample-and-hold and analog-to-digital converter circuit 76. Basically, the circuit 76 samples each of its three inputs, digitizes the samples, and then time multiplexes 8-bit words indicative of the samples. All of the processing of the signals downstream from the A/D computer 76 is thus done digitally.

Critical timing and control circuits (including the coherent master oscillator) are provided for digital and analog circuits by master timing 61.

With reference now to FIG. 2B, the digitized data from the sample-and-hold and A/D circuit 76 are applied to a "corner turning memory" 80 which stores the data in an order that allows comparison of sequentially received returns generated at the same physical location. More specifically, the corner turning memory 80 first receives a set of digital words indicative of the returns from a sequence of discrete tissue depths at a given beam location. The next set of digital words corresponds to the returns from the same sequence of discrete tissue depths at the same beam location. The corner turning memory 80 thus stores a total of sixteen sets of digital words indicative of the sixteen sets of returns from discrete tissue depths at the same beam location. The sixteen samples taken at the same depth are then read from the memory 80 in sequence. The memory 80 then outputs the sixteen samples taken at the next depth until the sixteen samples at the final (e.g., 320th) discrete depth have been read. The corner turning memory 80 then receives returns from sixteen transmitted pulses (i.e., sixteen samples) at the next beam location and outputs the data in the same manner as described above.

The corner turning memory 80 outputs the digitized samples indicative of the log tissue signal to a tissue integration circuit 82 which basically averages the received signals over sixteen successive returns. The digitized in-phase and quadrature samples indicative of the log of the flow signal are applied to a flow processor circuit 84.

The flow processor 84, together with the remaining circuitry, performs a discrete Fourier transform on the digitized flow signals. Basically, the flow processor 84 applies the in-phase and quadrative signals to sixteen digital comb filters. The operation of the flow processor 84 is best explained with an understanding of the spectrum of the signals transmitted and received by the transducers. The signal applied to the transducers may be a series of 7.5 mHz pulses having a repetition rate of 16 kHz. The resulting spectrum is a series of spectral lines centered at ±7.5 mHz and multiples thereof and spaced 16 kHz apart from each other. The spectrum of the received signal is the same as the spectrum of the transmitted signal, with the addition of spectral lines at $f_d$+N 16 kHz where $f_d$ is the Doppler frequency generated by reflections from moving scatterers in the blood and N is 0, 1, 2 . . . . After the received signal is processed by the clutter canceller and mixed down to baseband in the synchronous detector 74 and low-pass filtered, all that remains are the spectral lines at $f_d$+N 16 kHz. The filter processor 82 implements a series of 16 comb filters which bandpasses signals of $f_o$+N 16 kHz, where $f_o$ are discrete frequencies between 0 and 15 kHz spaced 1 kHz apart from each other. Thus, the first comb filter is centered at 0 Hz, 16 kHz, 32 kHz, 48 kHz, . . . , the fourth comb filter is centered at 4 khz, 20 kHz, 36 kHz, 52 kHz, . . . , and the sixteenth comb filter is centered at 15 kHz, 31 kHz, 47 kHz, 63 kHz, . . . . A Doppler frequency of 4 kHz will produce spectral lines at 4 kHz, 20 kHz, 36 kHz, 52 kHz, . . . , all of which will pass through the fourth comb filter.

The use of comb filters accomplishes at least two useful functions. First, the identity of the comb filter(s) generating outputs identifies the velocity or velocities of the moving scatters in the blood from which the ultrasound is reflected. Second, since all of the signal from a moving scatter passes through a single filter but the filter passes only a small portion of the noise bandwidth, the signal-to-noise ratio is improved.

The outputs of the digital comb filters in the filter processor 84 are applied to a centroid circuit 86. The centroid circuit 86 determines a single flow velocity (speed and direction) from a return that may be indicative of a range of blood flow velocities. The frequency spectrum of the in-phase and quadrature flow signals may vary from frequencies of −8 kHz to +8 kHz, indicative of fast moving scatterers moving in one direction, through center frequencies of +8 kHz from the center frequencies generated by scatterers moving at a relatively high velocity in the opposite direction. The centroid circuit 86 calculates a best estimate frequency based upon the first moment average of the spectrum.

The output of the centroid circuit 86 is applied to a threshold circuit 88 which functions to prevent an output from being generated from returns generated by tissue rather than moving sound scatterers. If flow signal strength exceeds the threshold at a sample site, a merge circuit 90 passes flow signals instead of tissue signals. Otherwise, tissue signals are passed for display.

The outputs of the merge circuit 90 are a series of 8-bit words, each corresponding to a sample site. These outputs are smoothed to reject isolated flow data occurring in tissue, corrected for the user-specified doppler angle in the smoothing and cosine correction function 91. These 8-bit words are applied to an interpolator circuit 92 that generates data for display pixels that correspond to locations between adjacent beams generated by the transducers 12, 14. For example, the transducers 12, 14 may receive along a series of beams centered at 1 millimeter from each other. Yet the pixels of the CRT exist for locations that may be 0.3 millimeters apart from each other. The interpolator circuit recognizes that if the adjacent beams positioned 1 millimeter apart are both receiving a signal at a given location indicative of a predetermined flow, then the flow at locations between the two beams can be calculated from those values. The interpolator circuit 92 then applies a signal to the pixel corresponding to the positions between the beams. Similarly, the interpolator circuit will generate a pseudo return for a tissue depth in-between two tissue depths from which actual returns are generated so that the pixel for the location between the pixels corresponding to the actual returns receives an appropriate signal.

The output of the interpolator circuit 92 is applied to an image memory 94 which has a memory location for each pixel. Each pixel word consists of either a number of bits indicative of the color saturation for displaying flow returns or a number of bits indicative of gray scale brightness for displaying stationary tissues. The pixel words stored in the image memory 94 are output to a color map random access memory (RAM) 96 that translates data indicative of the velocity of a return into saturation (i.e., the quantity of white) added to a pixel.

The display also includes an illustration of the spectrum, velocity, or flow in a cross section of a blood vessel as a function of time. These displays scroll across the bottom of the screen. Basically, the scrolling flow and velocity displays are created in the velocity processor 98 from the data generated by the flow processor 84. The scrolling spectrum displays are created in the high resolution spectrum 99 from data provided by the A/D 76. All scrolling displays are stored and buffered in scrolling memory 108 for display. The A/D 76 data also drives audio circuits 101 which convert the digital flow data to analog forward and reverse signals which are applied to speakers or headphones. The scrolling displays are periodically interrupted to allow the system to update the image display.

The output of the merge circuit 90 is also applied to a digital record and playback circuit 100, which, in turn, drives a conventional video cassette recorder 102. A signal recorded on the VCR 102 may also be applied to the system through the digital record and playback circuit 100 and merge circuit 90. It should be noted that the data recorded by the VCR 102 are the raw data generated before interpolation, thereby preserving the original quality of the receive signal. The digital record and playback circuit 100 may be triggered by an output from a conventional ECG monitor 104 to view flow at certain periods relative to the R-wave of an ECG waveform. The ECG signal may also be stored in the velocity processor 98 and displayed using a scrolling memory 108.

Referring to FIGS. 2B and 2C, the outputs from the color map RAM 96 are applied to a red, green, blue, and sync generator 110 which also receives signals from graphics planes 112. The graphics planes are for displaying graticule or "TIC" marks on the screen as well as other alphanumerics and markings that overlie the data being displayed. The circuitry illustrated in FIG. 2C also includes a display controller 114 that provides addresses for the image memory 94 and scrolling memory 108 through address counters 115. Each memory location in the image memory 94 is periodically addressed in sequence to maintain a continuously appearing, non-flickering display. The output of the RGB and sync generation circuit 110 is a video signal that may be applied to one or more CRT monitors 120, 122. A picture of the display on the CRT monitors 120, 122 may be taken with a camera 123. The video signal from the generator 110 may also be applied to a conventional video tape recorder 124 through an NTSC encoder circuit 126. The signal recorded in recorder 124 may then be played back through an NTSC decoder circuit 128.

The circuitry illustrated in FIG. 2C also includes the CPU 130, which employs a conventional model MC 68000 manufactured by Motorola. The CPU is driven by an external clock 132 and accesses non-volatile memory 134, which contains various test and user protocols. The CPU 130 also drives a conventional electroluminescent panel display 136 and an optional printer 138. Inputs to the CPU 130 are provided through a front panel 140 having a conventional keyboard and a foot switch 142 as well as a remote control panel 144.

Table 2, below, is a cross-reference of the units illustrated in the system overview figures (2A–2C) to the section where the detail description for the unit is included:

TABLE 2

SYSTEM BLOCK DIAGRAM CROSS-REFERENCE

| Unit | Part # | Detailed Description |
|---|---|---|
| Wedges | 20, 22 | System Overview |
| Transducers and Elements | 12, 14, 16, 18 | System Overview |
| T-pad and Switch | 50, 52, 53 | T-pad and Switch |
| Transmitter | 56 | Transmitter |
| Front End Receiver | 54 | Crossbar Switches |
| Crossbar Switches | 58 | Crossbar Switches |
| Timing and Control | 60 | Timing and Control |
| Master Timing | 61 | A/D Board |
| MUX | 62 | MUX |
| Delay Lines | 64 | Delay Lines |
| Delay Controller | 66 | Delay Controller |
| Amplitude Weighting, Summing and TGC | 68 | Amplitude Weighting, Summing and TGC |
| Gain Control | 70 | Amplitude Weighting Summing and TGC |
| Log Amp | 72 | Log Amp |
| Clutter Canceller | 74 | Clutter Canceller |
| A/D | 76 | A/D |
| Corner Turning Memory | 80 | Timing and Control |
| Flow Processor | 84 | Flow Processor Subsystem |
| Tissue Integration | 82 | Centroid Subsystem |
| Centroid | 86 | Centroid Subsystem |
| Threshold | 88 | Centroid Subsystem |
| Merge | 90 | Centroid Subsystem |
| Smothing, Correction and Compensation | 91 | Centroid Subsystem |
| Interpolate | 92 | Interpolator Subsystem |
| VCR | 102 | Operator Input/Peripherals |
| Digital Record and Playback | 100 | Digital Storage |
| ECG | 104 | ECC Subsystem |
| ECG RAM | 106 | Digital Storage |
| Image Memory | 94 | Graphics Memory Subsystem |
| Color Map RAM | 96 | Graphics I/O Subsystem |
| Spectrum | 99 | Spectrum/Velocity Subsystem |
| Velocity Processor | 98 | Spectrum/Velocity Subsystem |
| Scrolling Memory | 108 | Graphics Memory Subsystem |
| Audio Switch Board | 101 | Spectrum/Velocity Subsystem |
| Display Controller | 114 | Graphics I/O Subsystem |
| BW, RGB and Sync Generation | 110 | Graphics I/O Subsystem |
| NTSC Decode | 128 | Graphics I/O Subsystem |
| NTSC Encode | 126 | Graphics I/O Subsystem |
| System CPU | 130 | System CPU Subsystem |
| Photo Camera | | Operator Input/Peripherals |
| Image Display | 120 | Operator Input/Peripherals |
| Second Image Display | 122 | Operator Input/Peripherals |
| Video Tape Recorder | 124 | Operator Input/Peripherals |
| TV | | Operator Input/Peripherals |
| Menu Display | 136 | Operator Input/Peripherals |
| Printer | 138 | Operator Input/Peripherals |
| Front Panel | 140 | Operator Input/Peripherals |
| Foot Switch | 142 | Operator Input/Peripherals |
| Remote | 144 | Operator Input/Peripherals |

T-Pad and Switch

Figures 4, 5:
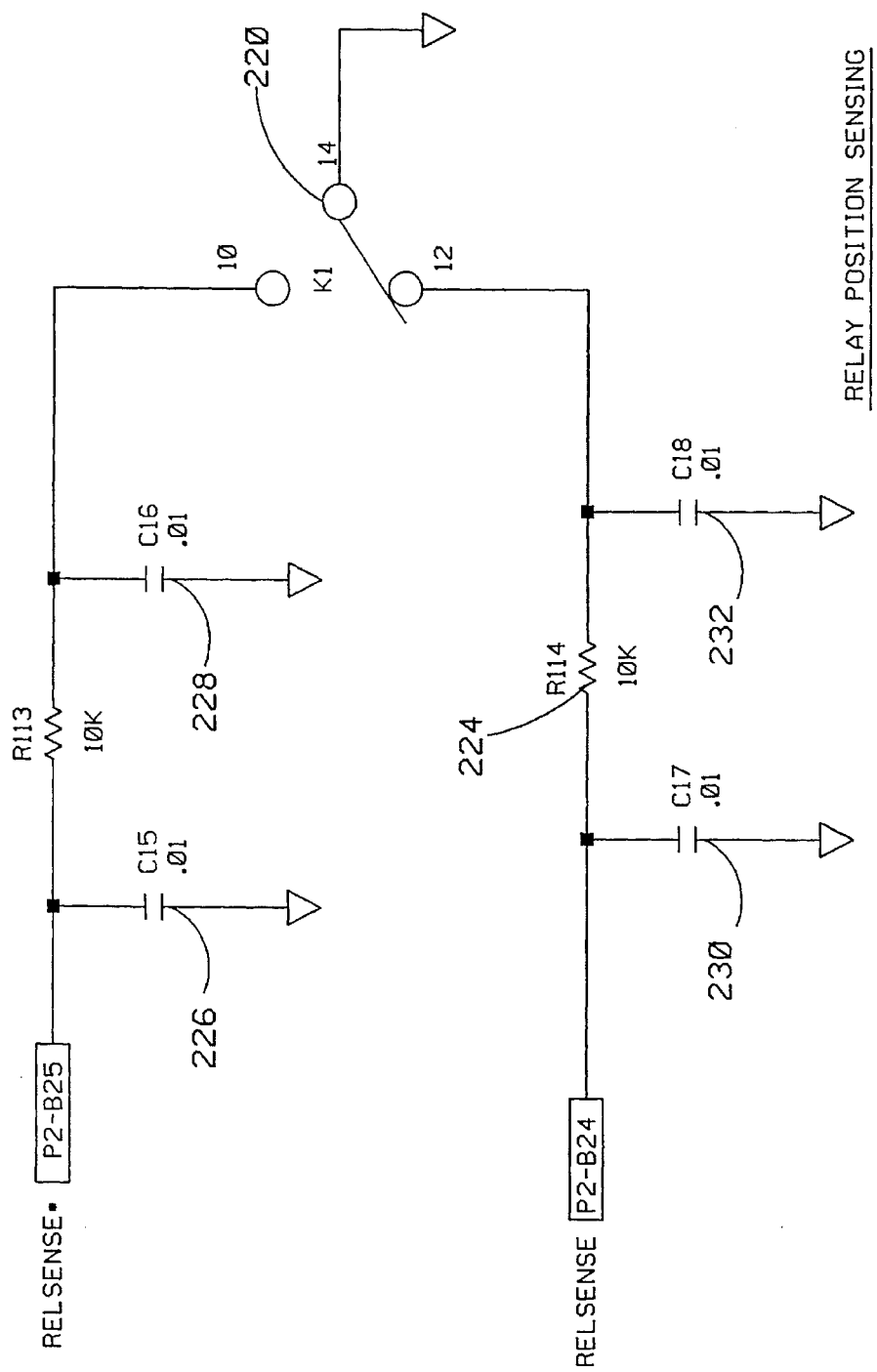
Figure 4F9:
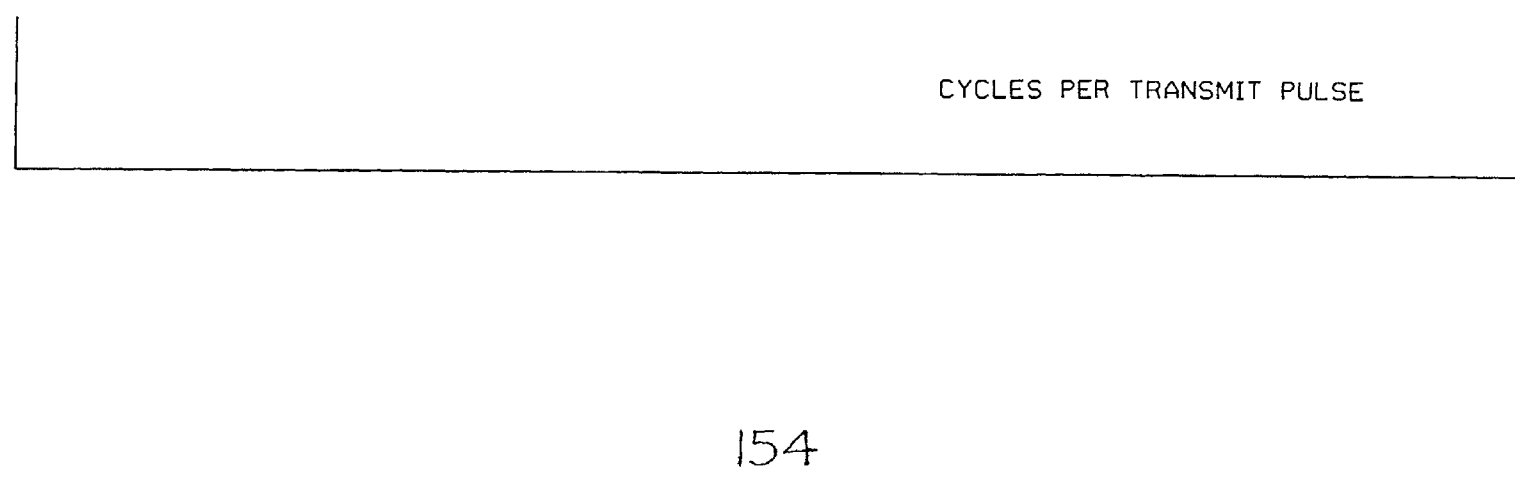
Figure 5:
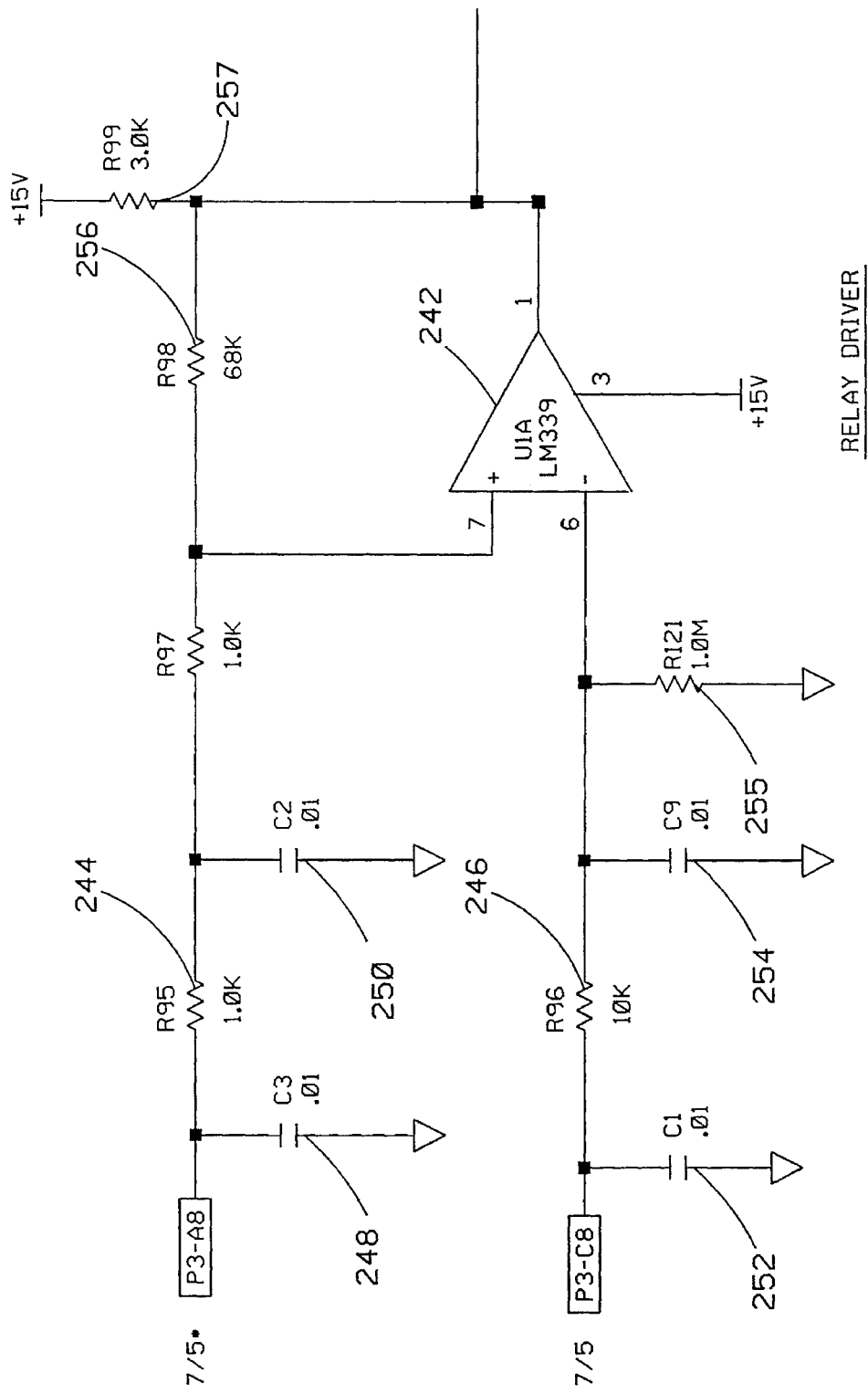

A schematic of the T-pad switch 53 (FIG. 2A) is illustrated in FIG. 4. The primary function of the T-pad switch circuitry is to connect the transducer elements of either the 5 mHz or 7.5 mHz transducers to the outputs of the transmitter 56 and the inputs of the crossbar switches 58. With reference to FIG. 4, corresponding elements 16a, 18a of the 7.5 mHz and 5 mHz transducers, respectively, are connected to two contacts of a conventional latching relay 200. The relay 200 connects either the 5 mHz transducer element 18a or the 7.5 mHz transducer element 16a to an output port 202 which is, as explained in greater detail below, connected to both an output of the transmitter 56 and an input of the crossbar switches 58. The relay contact of relay 200 is placed in its "set" condition to connect the 5 mHz transducer elements to the system by applying a negative-going SET pulse to relay coil 204. Similarly, the relay 200 connects the 7.5 mHz transducer elements to the system by applying a negative-going RST pulse to relay coil 206. The relay contact then remains in whatever position to which it was last switched. Although only a single relay contact is illustrated, it will be understood that there is a relay contact for each of the ninety-four transducer elements in the transducers 20, 22. In addition, another relay contact 210 is provided to cause current to flow through the series combination of current limiting resistor 212 and light-emitting diode 214 when the relay 200 is in the set position, thereby providing a indication that the system is operating at 7.5 mHz. Finally, another relay contact 220 is provided to connect either resistor 222 or resistor 224 to ground in order to provide relay-sensing outputs RELSENSC and RELSENSC* to the CPU to verify the state of the relay 200. Capacitors 226–232 are provided for filtering. In actuality, there are twenty-four relays 200, each of which contains several relay contacts.

The SET and RST signals for switching the relay 200 are provided by a relay driver circuit 240. The control signal for the relay driver circuit 240 is differentially applied to a comparator 242 through respective resistors 244, 246. The inputs are filtered by capacitors 248–254 to prevent the relay driver circuit from responding to noise or other transients. A positive feedback resistor 256 provides hysteresis to cause the output of the comparator 242 to clean the transition between states.

When the 7.5 mHz transducer is to be selected, the 7/5 input goes high and the 7/5* input goes low, thereby causing the output of comparator 242 to go low. The high-to-low transition at the output of comparator 242 triggers one-shot 258, which then generates a positively going 10 millisecond pulse, as determined by the time constant of resistor 260 and capacitor 262. The 10 millisecond pulse at the output of one-shot 258 turns on field effect transistor (FET) 264, thereby pulling the SET input to the relays low and causing the relay contacts to switch a position that connects the 7.5 mHz transducer elements to the system. Diode 266 is provided to protect the FET 264 from spikes generated by the coils 204 of the relay 200. Relay current is stored in capacitor 268, which is charged through resistor 270.

When the 5 mHz transducer is to be selected, the 7/5 input goes low and the 7/5* input goes high, thereby causing the output of comparator 242 to go high. The output of comparator 242 is connected to the input of a second one-shot 280, which, unlike the one-shot 258, is triggered on a low-to-high transition at the output of comparator 242. Thus, one-shot 280 generates a 10 millisecond pulse, as determined by the time constant of resistor 282 and capacitor 284 to turn on FET 286 and draw the RST inputs to the relays 200 low. Current then flows through relay coils 206 to connect the 5 mHz transducer elements to the system. Diode 290 protects FET 286 from spikes generated by the relay coil 206.

The system also includes circuitry to verify that the transducers are connected to the system in order to prevent the transmitter from generating an output in an open circuit condition. The transducers include a pair of input terminals 300, 302 that are connected to ground. If the transducers are connected to the system, these inputs 300, 302 are connected to the 5 HDSENSC and 7 HDSENSC inputs through resistors 304, 306, respectively. Capacitors 308, 304 provide filtering. The 5HDSENSC and 7 HDSENSC inputs are applied to the CPU to allow the CPU to verify that the transducers are connected before generating transmit pulses via transmitter 56.

Transmitter

Referring to FIG. 2A, the transmitter 56 drives the transducer elements 16, 18 of transducers 12, 14 through T-pad and switches 50, 52. In one embodiment, the imaging system 10 includes two identical transmitter PC boards capable of driving either the 5 mHz or 7.5 mHz transducer. Selection of the transducer driven by each transmitter PC board is determined by the card slot in which each transmitter PC board resides.

Referring to FIG. 5A, a block diagram typical for either transmitter 56 is illustrated. Each transmitter board receives data from two optical receivers. One receiver provides a signal from the timing and control subsystem into input signal decoding circuits 146. The second receiver provides the wave A/B pulse train used to generate the number of pulses per pulse repetition rate. The signal from the timing and control subsystem is received into input signal decoding circuitry 146 in a conventional Manchester coded format. This data signal is decoded to provide a data stream to element selection addressing circuitry 148, element attenuation control circuitry 150, and 5 mHz, 7.5 mHz transducer decoding circuitry 152. The element addresses, and element attenuations, and wave A/B signals from wave A/B generator 154 then drive select transmitter elements 156 to output to either T-pad and switch 52 or T-pad and switch 50, depending upon whether the 5 mHz or 7.5 mHz output frequency is selected and upon the transmitter PC board slot.

The circuit schematics for the typical transmitter PC board are shown in FIGS. 5B through 5F. Referring to FIG. 5B, the Manchester coded signal from the timing and control subsystem enters into input signal decoding circuitry 146 at a conventional, self-clocking, data formatting, Manchester decoder circuit. The decoded data, which is in the form of two 8-bit words, are serially input into shift registers 158 and 159. PAL 162 acts as a decoder to send the appropriate 8-bit word to the appropriate shift register 158, 159. The inputs to the PAL 162 are a 5-bit word from counters 147, 148, which increment with each CLOCK pulse from the decoder 146.

The 8-bit word received into shift register 158 comprises a 7-bit word for setting the transmitter element attenuation level and a single bit for selecting either the 5 mHz or 7.5 mHz transducers. The single bit selection is fed into inverters 160 and 161, which comprise the transducer decoding circuitry 152.

Referring to FIGS. 5B and 5E, the 7-bit attenuation level word output from shift register 158 is input to D/A converter 162 (FIG. 5E). The dynamic range of D/A converter 162 is 0 to 29.4 volts at a 7-bit resolution while sinking between 0 to 7 milliamps. Gain amplifier 164, voltage amplifier 165, and voltage regulator 166 comprise a feedback loop to force pin 3 of the gain amplifier 164 to 0 volts and force pin 1 of voltage regulator 166 to be 1.2 volts less than the voltage output from regulator 166. Diodes 168 and 169 protect voltage regulator 166 against latch-up. Capacitor 170 is a local bypass capacitor for providing a storage capacitance to handle peak currents. The output of the voltage regulator 166 is the attenuation voltage level fed into the center tap of transformers 192A through 192N (FIG. 5C).

Referring again to FIG. 5B, the decoded data word serially input into shift register 159 is output as a 7-bit word which addresses PROMs 172, 173, 174, 175, and 176. An eighth and most significant bit, for addressing the PROMs, identifies one of the two transmitter cards, shown as an output from line receiver 178. The PROMs 172–176 comprise the element selection addressing circuitry 148 of FIG. 5A. The PROMs function logically as decoders for selecting transmitter elements to comprise the beam output from imaging system 10. Referring to FIGS. 5C, 5D, and 5E, the PROMs 172–176 select specific transmitter elements 156. Each line out of a PROM selects up to three elements total on either of the two cards. With reference to transmitter element 156A as a typical circuit for each of the elements 156, the element 156A comprises pullup resistors 178A and 180A, RC circuits 182A and 184A for quickly turning on and off buffers 186A. Buffers 186A are current drivers for driving HEXFETs 188A and 190A. When the HEXFETs 188A, 190A are turned on, the attenuation voltage output from voltage regulator 166 of FIG. 5E passes through step-up transformer 192A, which is wired in a push/pull configuration. The transformer 192A steps up the voltage by a factor of three and outputs two cycles. Diodes 194A and 195A isolate the transformer from beam signal echoes. Even though a transmitter element 156A is selected from PROM, the output from step-up transformer 192A is enabled only during the active levels of wave A and wave B.

Referring to FIG. 5F, wave A/B generator 154 receives a pulse stream of eight pulses from A-to-D converters 76 and outputs a wave A and a wave B of two pulses which are input into transmitter elements 156. The first two pulses of the 8-pulse wave train set up flip-flops 196 and 197. The next six pulses of the 8-pulse wave train define the edges for two 2-pulse outputs. One 2-pulse output defines wave A, while the other 2-pulse output defines wave B. Wave B is phase-shifted from wave A such that when combined with transmitter elements 16, 18, result in two full cycles of transmit energy.

Crossbar Switches

Figures 5, 6, 7:
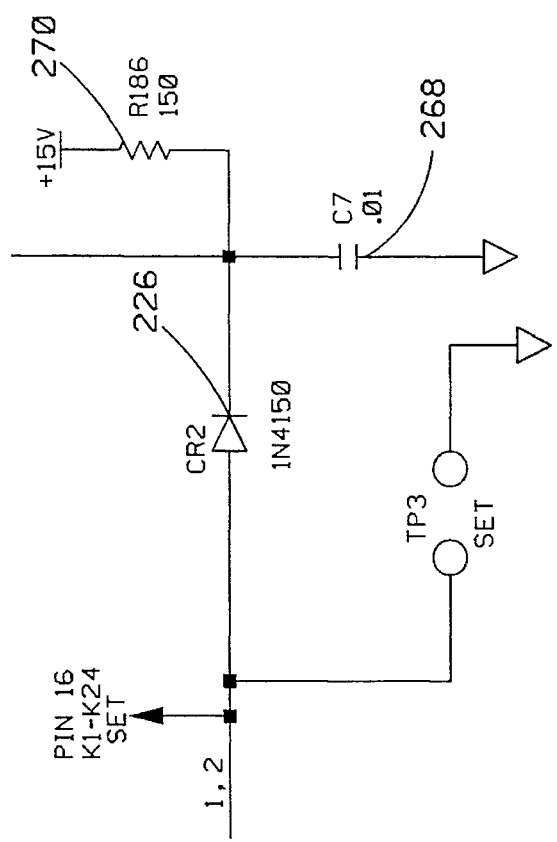
FIG. 6 is the circuit schematic for the crossbar switches.
FIG. 7 is the circuit schematic for the MUX.

The outputs of the T-pad switches 53 are applied to a set of crossbar switches 58, a block diagram for which is illustrated in FIG. 6A. Each of two crossbar modules contains twenty channels, which are identical except that channels 7–14 select one of three possible inputs and channels 1–6 and 15–20 select one of two possible inputs. Input selection is accomplished through an input switch 330, with the inputs to each switch 330 being connected to transducer elements separated from each other by forty transducer elements. In other words, the input to switch 330 for channel 7 is connected to transducer elements 14, 54, and 94. The selected signal from the input switch 330 is applied to a high-pass filter 332 to reduce switching transients. The output of the filter 332 passes through a gain-controlled amplifier 334, which boosts the output of the high-pass filter 332 by a magnitude determined by a gain control signal. The output of the gain control amplifier 334 for each channel is applied to the multiplexer 62 (FIG. 2A), as explained in greater detail below.

The input switch 330 is controlled by a set of programmable read-only memories 60, which are, in turn, controlled by an 8-bit beam address supplied to the PROMs 60 by the multiplexer 62. A ninth address bit is controlled by the location of the module containing the twenty channels so that each of the crossbar modules (each of which contains twenty channels) are identical. If the module is plugged into a slot for the first twenty channels, the ninth bit will be a logic "0." If the crossbar module is plugged into a slot for channels 21–40, the ninth bit will be a logic "1."

The control signal for the gain control amplifier 334 is supplied by the amplitude weighting and summing subsystem 68 (FIG. 2A) and is applied to a TGC amplifier 338. The TGC amplifier converts the differential input signal to a single-ended signal in order to reject any common mode noise. The output of the TGC amplifier 338 passes through a TGC filter 340 for noise attenuation purposes before the control voltage is applied to each of the gain control amplifiers 334 for the twenty channels.

A schematic of one channel of input switch 330, bypass filter 332, and gain control amplifier 334 is illustrated in FIG. 6B. It will be recalled that the input switch 330 for each channel is connected to either two or three transducer elements, each of which is spaced forty elements apart from each other. Thus, for the channel illustrated in FIG. 6B, the input switch 330 is connected to transducer elements 8, 48, and 88. The input switch 330 includes three switching circuits 350, 352, 354, connected to transducer elements 8, 48, and 88, respectively. Channels connected to only two transducer elements will, of course, have only two switching circuits 350, 352. Each of the switching circuits 350, 352, 354 operates in the same manner. Transducer element 8 is selected by forward biasing diodes 360, 362, thereby allowing the input from transducer element 8 to be applied to an output line 364. More specifically, current in the diodes 360, 362 is controlled by a transistor 366. Transistor 366 is turned on by a low S92 control signal applied to the base of transistor 366 through resistor 368. Current then flows in sequence through transistor 366, resistor 370, RF choke 372, and then splits between diodes 360 and 362. Current through diode 360 flows to ground through impedance matching transformers in each of the transducer elements. Current flowing through diode 362 flows to ground through inductor 380.

When the control input S92 is either high or floating, transistor 366 is turned off, either by the high S92 input or by the bias provided through resistor 382. Capacitor 384 is provided to reduce the switching speed in order to minimize transients. Since transistor 366 is turned off, diodes 360, 362 are reverse biased by the negative voltage through resistor 384 and resistor 386. Capacitor 388 provides filtering by attenuating noise and other high-frequency transients. The reverse bias of diodes 360, 362 is provided by diodes 390 and 392. In other words, diodes 390, 392 clamp the voltage on the cathode of diode 390 to approximately −1.4 volts.

Each of the transducer elements is connected to not only the crossbar switches 330, but they are also connected to an output of the transmitter 56 (FIG. 2A). In order to prevent the relatively high-amplitude transmission pulse from damaging the circuitry in the crossbar, diodes 394, 396 are connected in parallel across output line 364 in order to limit the amplitude of the transmitted pulse on line 364 to approximately 0.7 volt.

As explained above with reference to FIG. 6A, the output of the input switch 330 is applied to a high-pass filter 332. The high-pass filter is formed by inductor 380, capacitor 400, and inductor 402. The high-pass filter 332 has a low-frequency cutoff frequency of about 1.5 mHz and functions to block extraneous electromagnetic interference, such as broadcast interference. The filter 332 also blocks switching transients generated by the input switch 330.

The remainder of the circuitry illustrated in FIG. 6B is the gain control amplifier 334 that receives the output of the high-pass filter 332. The first stage of the gain control amplifier 334 is a FET 410 in a common gate configuration in order to provide a low input impedance of about 20 ohms and a low noise figure. The FET 410 is biased through resistor 412 and its gate is held at AC ground through capacitor 414. The drain of FET 410 is connected to the emitter of transistor 420 through resistor 422. Transistor 420 operates in a common base configuration, with its base AC grounded through capacitor 424 and its DC bias set by voltage divider resistors 426, 428. The common base configuration of transistor 420 provides a low input impedance to reduce the effect of the high drain capacitance of FET 410 and also provides a high output impedance to facilitate controlled gain adjustments over a wide range.

The output signal on the collector transistor 420 is applied to a pair of emitter follower transistors 430, 432 through resistor 434. Back-to-back diodes 436, 438 are provided to limit the interstage RF voltage to avoid saturation of the amplifier transistors which could result in long recovery times. Inductor 440 resonates with the interstage shunt capacitance to form a low-Q, single-pole bandpass filter centered at about 5 mHz.

Emitter follower transistors 430, 432 provide a high input impedance and a low output impedance. The signal on the emitter of transistor 430 is applied to the base of transistor 432 through resistor 444. The signal at the output of transistor 432 is AC coupled to the multiplexer through a capacitor 450 in series with resistor 452.

The gain control amplifier 334 is biased through a negative feedback DC bias circuit in order to provide good temperature stability. The bias current for transistor 420 and FET 410 flows through resistor 460, inductor 440, transistor 420, resistor 422, FET 410, and inductor 402. The voltage across resistor 460 is thus proportional to the bias current. The voltage across resistor 460 is compared to the voltage on the base of transistor 462, which is, in turn, determined by voltage divider resistors 464, 466. Capacitor 468 is provided for filtering. In the event that the bias current decreases, the voltage on the emitter of transistor 362 increases, thereby increasing the flow of current through transistor 462 and resistor 470 to increase the voltage on the gate of FET 410. Conversely, if the bias current increases, the base emitter junction of transistor 462 becomes less forward biased, thereby decreasing the bias current flowing through resistor 470. Capacitor 476 and resistor 478 are used for filtering the power supply voltage.

It will be recalled that the output impedance of transistor 420 is relatively high. The gain of transistor 420 is controlled by adjusting the impedance of diodes 480, 482, which are connected to ground at the RF frequency of the signal from transistor 420 through bypass capacitors 484, 486, respectively. The diodes 480, 482 are PIN diodes wherein the resistance is inversely proportional to the current through the diode. The current through the diodes 480, 482 is controlled by the voltage at the output of operational amplifier 490, which has equal summing junction and feedback resistors 492, 494, respectively, to set the gain of amplifier 490 at unity. Since the amplifier is inverting, the voltage at the output of amplifier 490 is the inverse of its input voltage. Thus, the positive voltage applied to diode 482 through resistor 496 has the same absolute value as the negative voltage applied to diode 480 through resistor 498. Since resistors 496, 498 are precision resistors of the same value, the voltage at the junction between diodes 480, 482 remains at zero regardless of the magnitude of the current flowing through diodes 480, 482. In this manner, coupling of the TGC control signal to the output stage is avoided.

The TGC control signal that is applied to amplifier 490 is generated by operational amplifier 500, which, together with resistor 502 and capacitor 504, implement the low-pass filter 340 (FIG. 6B). The output of amplifier 500 is the sum of three input signals. One of these input signals is the time-gain control signal that is applied to the summing junction of amplifier 500 through the parallel combination of resistor 506 in series with potentiometer 508 and resistor 510 in series with variable capacitor 512. Potentiometer 508 sets the gain of the amplifier 500 at 25 DB when the TGC control voltage is −5 volts. Capacitor 512 provides frequency compensation for the capacitance in the PIN diodes 480, 482.

The second signal that is applied to the summing junction of amplifier is a DC offset provided by potentiometer 520 and resistor 522. The potentiometer 520 is adjusted so that the amplifier 500 has a gain of zero DB when the TGC voltage is at zero volts.

The final input the summing junction of amplifier 500 is a temperature-compensating signal derived by resistor 524 and diode 526 which is applied to the summing junction of operational amplifier 500 through resistor 528. The offset voltage generated across diode 526 is a function of temperature and it compensates for temperature-induced changes in the voltage across diodes 480, 482 in order to make the circuit look relatively temperature insensitive.

The output of the gain control amplifier 334 of FIG. 6B is thus the output of a selected transducer element boosted by a gain of between 0 and 25 DB, depending upon the magnitude of the TGC signal. The inputs to the input switch 330 are selected so that forty crossbar channels can be used to switch ninety-six transducer elements so that a beam of up to forty transducer elements steps across the transducer.

As mentioned above with reference to FIG. 6A, the input switch 330 is controlled by beam selection PROMs 60, which designate the transducer elements used to form each of a large number of beams. The PROM outputs are controlled by a 9-bit word, eight bits of which are provided by the multiplexer and the last bit of which is provided by the slot in which the crossbar board is inserted in order to program the board for being associated with either channels 1–20 or channels 21–40. Referring to FIG. 6C, the 9-bit address is applied to PROMs 540–550, each of which generates an 8-bit output for a total of forty-eight outputs. Each of the outputs is connected to a respective switching circuit 350, 352, 354 (FIG. 6B) to select the transducer element that is applied to the respective channel. The six PROMs 540–550 for channels 1–20 and the other six PROMs (not shown) for channels 21–40 each output eight control signals for a total of ninety-six control signals corresponding to the ninety-six transducer elements. Elements ED and E95 are not used but are required to make the two crossbar PCBs identical. Basically, the PROMs 540–550 each contain a bit pattern that outputs a control signal to the appropriate switching circuit when the transducer element connected to that switching circuit is to be included in the beam designated by the PROM address.

The time-gain control signal from the amplitude-weighing and summing subsystem 68 is applied to the TGC amplifier 338 differentially. It is then applied to a differential amplifier 560 through a balun transformer 562 and respective input resistors 564, 566. The gain of the amplifier 560 is set by feedback resistor 568 and voltage divider resistor 570 at one half.

The TGC low-pass filter 340 (FIG. 6A) is implemented by inductor 580, capacitor 582, inductor 584, resistor 586, and resistor 590. The filter has a cutoff frequency of about 0.7 mHz and a rise and fall time of about 0.5 microsecond. The TGC filter 340 further suppresses any noise or interference which might otherwise be coupled into the signal path. The TGC signal at the output of the filter 340 is applied to the operational amplifier 500 (FIG. 6B) for each channel.

Mux

A block diagram of the multiplexer is illustrated in FIG. 7A. The multiplexer receives the forty outputs of the crossbar subsystem, switches their order depending on beam number so that the proper beam forming can occur, sums the output of symmetrically positioned transducer elements, and outputs the resulting 20 RF signals to the delay line subsystem 64. The beam number is obtained over an optical Manchester link from the timing control subsystem 80 (FIG. 2B) and the decoded beam address is supplied by the multiplexer to the crossbar subsystem to control crossbar switching of transducer elements based on beam number.

The multiplexer subsystem includes a 40×40 RF switch 600 that reorders the 40 crossbar signal so that each output line of the switch represents a particular element in the 40-element beam array. The forty ordered lines are labeled 20 lower through 1 lower and 1 upper through 20 upper, with 1 being the center elements and 20 being the outer elements of the beam array. Thus, 20 lower of the first beam will consist of transducer element 1 and 20 upper of the first beam will consist of transducer element 40. Transducer element 20 lower of the tenth beam will consist of transducer element 10 and 20 upper of the tenth beam will consist of transducer element 50.

The forty output lines from the multiplexer switch 600 are applied to an ON AXIS/DISPLACED AXIS switch 602 that determines which outputs of the multiplexer switch 600 are combined in subsequent processing for on-axis operation. The correspondingly numbered upper and lower lines are summed so that the center of the beam is between 1 upper and 1 lower. For displaced axis operation, the lower set of multiplexer outputs is displaced one position so that 1 upper and 2 lower are summed, thus making the center of the beam 1 lower. Consequently, a displaced axis beam is displaced by one-half of a transducer element from the on-axis beam.

The forty outputs from the ON AXIS/DISPLACED AXIS switch are combined in a 2:1 summer 604 that combines the signals from symmetrical elements (for symmetrical elements displaced by 1 in the case of displaced axis processing) so that only 20 delay channels are required in the system beam format. A squelch circuit 606 is provided on each of the 20 output lines to reduce the switching transient that occurs when the beam address is changed.

The outputs of the summer 604 are applied to the squelch circuit 606, as explained above with reference to FIG. 7A. The squelch circuit consists of a 4-diode bridge 810–828 shunting each combined beam element signal to ground when the Manchester decoder 608 generates a squelch activation signal. The combined beam element signals are connected to the squelch circuit through respective DC blocking capacitors 830–848.

The operation of the 40×40 multiplexer switch 600, the ON AXIS/DISPLACED AXIS switch 602, and the squelch 606 is controlled by the Manchester signal from the timing and control subsystem 80 (FIG. 2B). The beam address portion of the signal is decoded into an 8-bit binary code by a Manchester decoder 608. The beam address portion of the Manchester signal is decoded into an 8-bit binary code, with the seven least significant bits defining the beam address. These seven least significant bits drive the address lines of a prompt decoder 610 whose six output lines control the 40×40 multiplexer switch 600. The most significant bit from the Manchester decoder 608 designates either the on-axis or displaced axis mode. All eight bits from the Manchester decoder 608 pass through a buffer 612 and supply outputs to the crossbar subsystem to control the crossbar switches. The Manchester decoder 608 also provides an output to turn on the squelch circuit 606 when the beam address is changed.

Figures 5, 6, 7, 8:
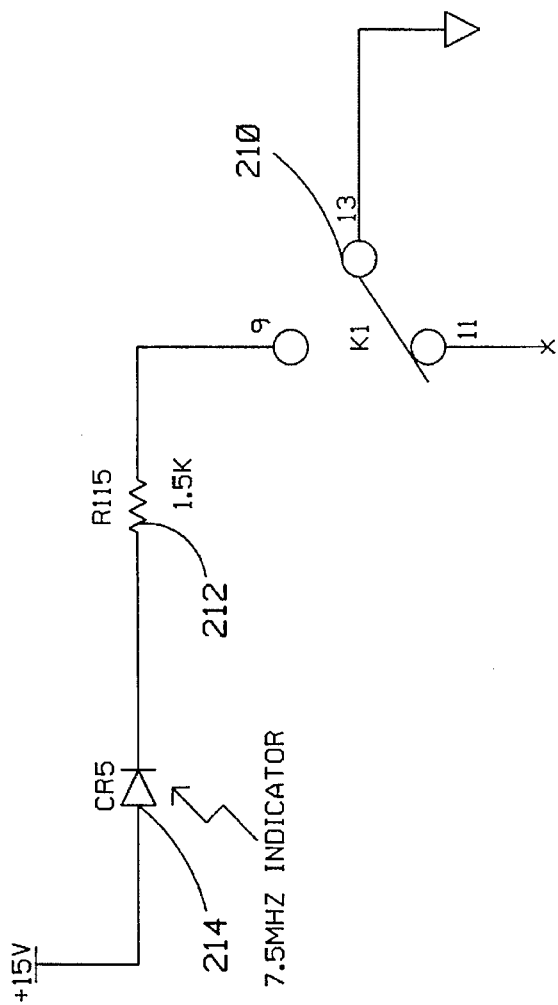
FIG. 8 is the circuit schematic for the delay lines.

A schematic of the 40×40 multiplexer switch, as illustrated in FIG. 7B, includes eight analog multiplexer circuits, four of which (620–626) are illustrated in FIG. 8. Multiplexer circuit 620 is illustrated in detail, although it should be understood that the other multiplexer circuits 622–626 and the four multiplexer circuits that are not shown are identical. The forty crossbar outputs are applied through respective DC blocking capacitors, indicated generally at 630. The inputs are applied in groups of eight to respective one of eight CMOS multiplexers 632, 634, 636, 638, 640. The multiplexers 632–640 connect one of their inputs to their output, as designated by a 3-bit word "A, B, C," depending on the beam number, as explained in greater detail below. The outputs of the multiplexers 632–640 are applied to the base of respective emitter follower transistors 642, which have their input impedance set by resistors 652–660 to a value sufficiently high to avoid loading the multiplexers 632–640.

Each emitter follower transistor 642–650 drives one input of five additional one of eight analog multiplexers 662–670, respectively. These multiplexers 662–670 are controlled by a 3-bit word, "D, E, F," to connect one of their inputs to their output. Since the crossbar switching repeats its pattern every forty beams, only forty unique addresses are required by the multiplexer switch 600 to accomplish the reordering. By a judicious choice of input and output connections, all eight sections of the multiplexer switch can use the same 6-bit address code "A–F." The outputs of the multiplexers 662–670 are once again applied to respective emitter follower transistors 672–680, respectively, having their input impedance set by respective resistors 682–690. The five outputs of the multiplexer section 620 can each be connected to any one of forty crossbar elements to provide great flexibility in multiplexer switching. Moreover, since the outputs of each multiplexer section 620–626 are each eight transducer elements apart from each other, the same 6-bit control words "A–F" can be used to control all of the multiplexer sections. In other words, for the center where beam control word "A–F" is all zeros, multiplexer section 620 will output crossbar element 1 as element 20 upper, crossbar element 9 as beam element 12 upper, crossbar element 17 as beam element 4 upper, crossbar element 25 as beam element 5 lower, and crossbar element 33 as beam element 13 lower. In the same manner, for the center beam, multiplexer section 622 will output crossbar element 8 as beam element 13 upper, crossbar element 16 as beam element 5 upper, crossbar element 24 as beam element 4 lower, crossbar element 32 as beam element 12 lower, and crossbar element 40 as beam element 20 lower.

The input lines to the multiplexers are biased high through voltage divider resistor 690, 692 with low-pass filtering being provided by capacitor 694 and respective RF chokes, indicated generally at 696.

The ON AXIS/DISPLACED AXIS 602 is implemented by a series of double-throw switches 700–718 which select either the in lower or in +1 lower beam element for combination with the in upper beam element. The relays are controlled by a single bit "G" from the Manchester decoder 608 (FIG. 7A). For example, switch 718 selects either the 14 lower or the 15 lower beam element, which is then combined with the 14 upper beam element.

The outputs of the switches 700–718 are applied to the bases of respective emitter follower transistors 720–728, respectively, which have their input impedances set to a relatively high value by resistors 740–758, respectively. The emitter follower transistors 720–738 provide a low output impedance for their respective signals. The outputs from the transistors 720–738 are applied through respective summing resistors 760–778 to respective summing junctions. The summing junctions also receive the outputs from the multiplexer sections 620–626 through respective resistors 780–798. The summing resistors 760–778 and 780–798 add the in upper output from the multiplexer sections 620–626 with either the in lower or in −1 lower output from the multiplexer sections 620–626, as selected by the switches 700–718. In the on-axis mode, switch 700 combines the 20 upper beam element with the 20 lower beam element signal. In the displaced axis mode, the 20 upper beam element signal is combined with a signal that has the same DC value as the 20 lower beam element signal because of the presence of inductor 800, but it is effectively at AC ground because of the presence of capacitor 802.

As explained above, the multiplexer 62 includes eight multiplexer sections, only four of which (620–626) are illustrated in FIG. 7B, since the other four are identical. Likewise, the multiplexer 62 also includes ten additional ON AXIS/DISPLACED AXIS switches that are identical to switches 700–718 and drive the same associated summing circuitry and squelch circuits.

The squelch circuit 810 consists of four diodes 850, 852, 854, 856 arranged in a bridge, with the control signals being applied to opposite sides of the bridge through resistors 850–860. One end of the bridge is connected to the output signal line, while the other end of the bridge is connected to ground. Capacitor 862 reduces the response time of the bridge in order to prevent high-frequency transients from being generated on the output lines. In normal operation, the control signals "H, J" are at ground so that the diodes 850–856 are nonconductive and thus have no effect on the circuit. When the multiplexers are switched responsive to a change in the beam number "H," a differential squelch signal is applied to the squelch circuit 810 in which the "H" input goes high and the "J" input goes low, thereby forward biasing all of the diodes 850–856 and providing a low impedance path from the output signal line to ground. Note that the balanced nature of the input and the bridge causes the cathode of diode 850 and the anode of 852 to remain at approximately zero volts in order to minimize the coupling of the squelch signal to the output signal lines. The other squelch circuits 812–828 (and the squelch circuits on the other multiplexer board) are identical to the squelch circuit 810 and are thus not individually described. The outputs of the squelch circuits 810–828 are applied through respective resistors 880–898 to the delay lines 64 (FIG. 2).

A schematic of the Manchester decoder 608 (FIG. 7A) is illustrated in FIG. 7C. Serial Manchester data is applied in differential form to a comparator 900 having a terminating resistor 902 connected between its inputs. The output of the comparator 900 is applied to a conventional Manchester decoder 904 consisting of OR-gate 908, exclusive OR-gate 912, 60 nanosecond timer 914, OR-gates 916, 918, 920 and flip-flop 922, all connected to each other in a conventional manner. The Manchester code is a well-known type of self-clocking code. As transmitted, the serial Manchester data contains its own clock and encoded data. To "demodulate" the "data" from the encoded Manchester requires that the clock be extracted from the Manchester data. The Manchester decoder 904 extracts both the clock and the data from the serial Manchester data. The data is output from flip-flop 910, while the clock is output from flip-flop 922. Exclusive OR-gate 930, in combination with resistor 932, applies a power-up reset to the components of the Manchester decoder 904, as well as other circuitry illustrated in FIG. 7C.

The first clock pulse from the Manchester decoder 904 triggers a one-shot 940 and it is retriggered by succeeding clock pulses so that its output lasts for 250 nanoseconds beyond the last clock pulse, as determined by the time constant of resistor 942 and capacitor 944. The trailing edge of the pulse output by one-shot 940 triggers a second one-shot 946, which outputs a negative-going 200 nanosecond pulse, as determined by the time constant of resistor 948 and capacitor 950. The 200 nanosecond pulse output by one-shot 946 normally occurs after the Manchester data has been received, and it is used to clear the flip-flops 910, 922 of the Manchester decoder 904 and to clear other components, illustrated in FIG. 7C, as explained in greater detail below.

The positive-going pulse at the output of the one-shot 940 is used to generate the squelch signals "H, J." The output of one-shot 940 is applied to a level shifting circuit 960, which then turns on FET 962 through resistor 964. Resistor 966 is connected between the output of level shifting circuit 960 and ground for biasing purposes. When FET 962 turns on, current stored in capacitor 968 is drawn through balun transformer 970 to generate the "H, J" squelch signals from the center-tapped secondary of the transformer 970. Capacitor 968 charges through resistor 972. Resistor 974 attenuates the high-frequency spikes generated by the balun transformer 970.

The clock generated at the output of flip-flop 922 of the Manchester decoder 904 increments a pair of 4-bit counters 980, 982, which have been reset by the 250 nanosecond pulse at the output of flip-flop 946 at the end of the previous transmission of Manchester data. The 8-bit count from the counters 980, 982 are applied to a PAL 984 that generates various timing and control signals to convert the serial Manchester data into parallel data. PAL 984 outputs a SERIAL CLOCK which is the inverse of the clock from the flip-flop 922. The SERIAL CLOCK clocks the data from the Manchester decoder 904 into a shift register 986. On the count 8 of the counters 980, 982, PAL 984 outputs a LOAD BEAM pulse that outputs the serial data stored in shift register 986 in parallel to a PROM 988 and a set of drivers 990. Since the first eight bits of the Manchester data constitute the beam number and the off-axis/displaced axis code, the beam number and on-axis/displaced axis code are applied to the crossbar through a set of resistors 992. The beam number is also used to address the PROM 988 to convert the beam number to a code indicative of the transducer elements forming the designated beam. The PROM 988 thus outputs the multiplexer control signals "A–F" through a set of buffers 994. The seventh bit, which constitutes the on-axis/displaced axis control bit, is applied through a buffer 996 to the on-axis/displaced axis switch 602.

Delay Lines

A block diagram of the delay lines 64 is illustrated in FIG. 8A. The delay lines 64 include four delay line cards 1000, 1002, 1004, and 1006, each of which includes five delay channels 1008, 1010, 1012, 1014, and 1016. The four delay line cards 1000–1005 include a total of twenty delay line channels for delaying the twenty multiplexer outputs, which are in turn paired from 40 transducer elements located symmetrically about the beam center.

The 20 outputs of the delay lines (paired from 40 transducer elements) are amplitude weighted and summed in the sum and weight subsystem 68, to form the beam, continuously and smoothly dynamically focussing on the ultrasound return echos from the transmitted burst as it encounters changes in the transmission characteristics as it progresses through the body.

To accomplish the dynamic focusing on either 5 or 7.5 mHz, and to minimize the amount of variable delay required in any one channel, and to allow any card to be used in any of the four delay line card slots, a combination of both fixed and variable delays are used, with four fixed taps on the fixed delay lines. The tap selection depends upon the frequency, and which of the four slots the card is plugged into. Then once the frequency and the card position in the chassis is known, the tap is selected accordingly. The variable delay line drive parameters are stored in an EPROM on the card, so that cards may be easily interchanged.

Each delay line channel 1008–1016 includes a voltage gain amplifier 1020 to make up for losses through the channel, a delay compensation circuit 1022 for providing phase and delay compensation for the delay lines, a tapped delay line 1026 to provide a fixed amount of delay as needed, a multiplexer 1028 to select the desired tap of the four taps on the 1026 tapped delay line, depending upon frequency and card location, and finally a variable delay line 1032. Interspersed in the above are buffer amplifiers 1024, 1027, 1030, and 1034. Following buffer amplifiers 1027 are gain adjustments 1029 to set the overall channel gain to unity at minimum delay.

The data for the tap selection on tapped delay line 1026 by multiplexer 1028 is stored in PAL 1039.

Delay control voltage vs. time and termination control voltage vs time for the variable delay lines 1032 are stored in EPROMS 1040 which is accessed through a multiplexer 1042. The multiplexer 1042 is controlled by outputs from the delay controller 66, and outputs the data stored in EPROMS 1040 to the delay controller, which then provides the control signals for the delay line cards 1000–1006.

A schematic of the tapped delay line 1026 is illustrated in FIG. 8B. The delay line 1026 contains a number of inductor-capacitor sections, utilizing closely coupled inductors, indicated generally at 1450, and capacitors at 1452, some of which are tapped to output signals of varying delay. The delay line 1026 for channel 71 contains 40 capacitors and four close coupled inductor sections. The delay lines 1026 for the other delay line channels on the delay line board 1000 will contain fewer close coupled indicators 1450 and capacitors 1452, since higher numbered channels process outputs from transducer elements that are further away from the center of the ultrasound beam. In other words, the channel 1 transducer elements are at the center of the ultrasound beam, while the channel 20 ultrasound elements are at the ends of the ultrasound beam. In order to allow a signal reflected from the center of the ultrasound beam to be output by the delay lines of all channels at the same time, it is necessary to delay the lowered numbered channels for a longer time than the delay of the higher numbered delay line channels.

Figure 8C:
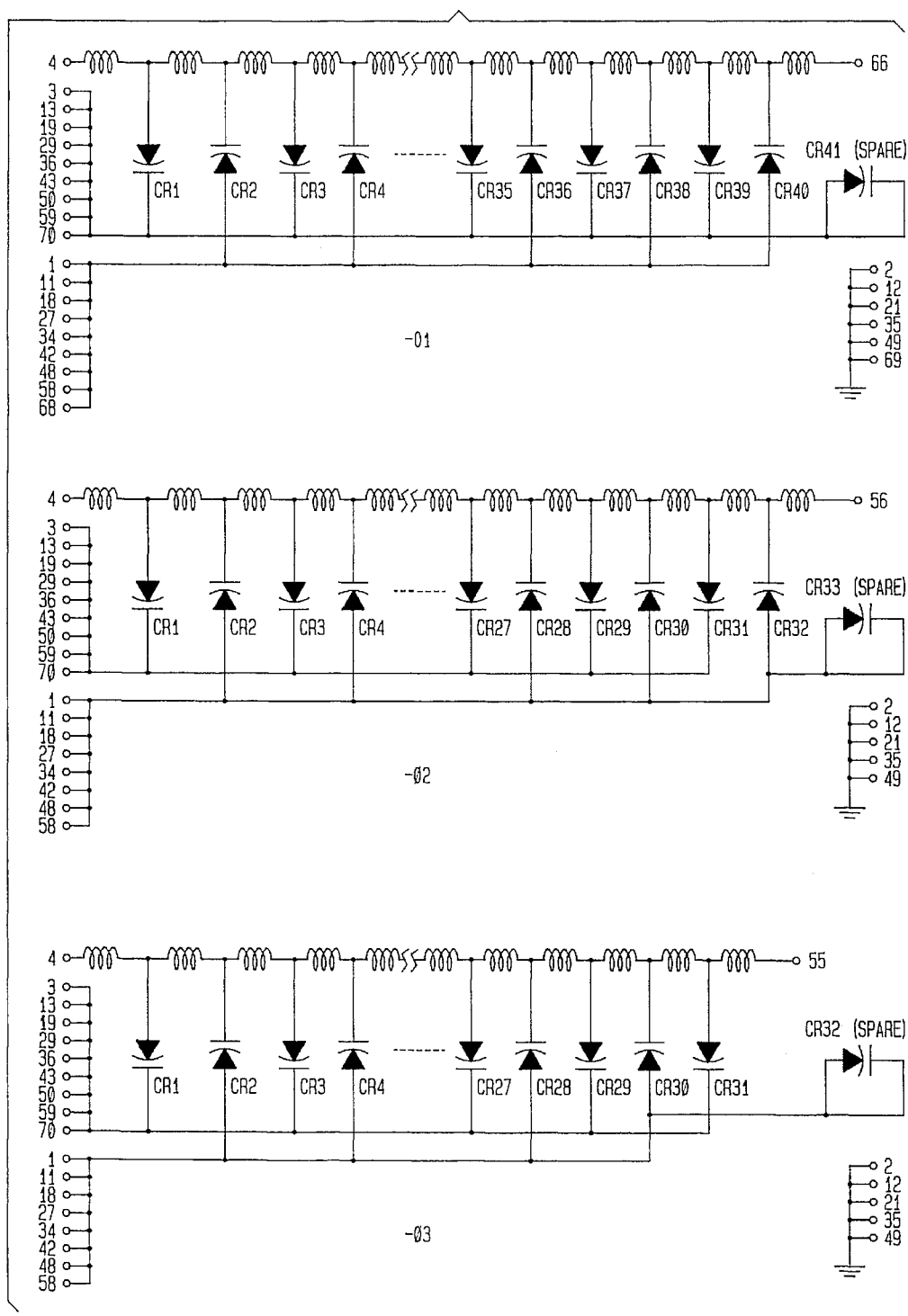

A schematic of the variable delay line 1032 is illustrated in FIG. 8C. The variable delay line 1032 is somewhat similar to the fixed delay line 1026 of FIG. 8D, except that instead of using fixed capacitors it utilizes vatactor diodes 1462. Again it utilizes close coupled indicators indicated generally at 1460. The diodes 1462 are arranged in alternating positions so that the varactor diodes 1462 receiving the positive control voltage VD+ alternate with vatactor diodes 1462 receiving the negative delay control voltage VD−. By using alternatingly positioned diodes, a positive signal applied to the delay line that increases the capacitance of one diode reduces the capacitance of the adjacent diode in order to make the delay of the delay line 1032 less sensitive to the magnitude of the delayed signal than it would be if all the diodes were controlled by only a single VD. Also, the control voltage tends to cancel out at the output, rather than add it to a single VD.

A diagram of one delay line channel 1008 is illustrated in FIG. 8D. The RF signal from the multiplexer channel is applied to the base of a transistor 1100 through a DC blocking capacitor 1102. Transistor 1100 is biased through resistors 1104, 1106, 1108. Capacitor 1110 is provided to create an AC ground to which the base is connected through resistor 1106 preventing AC feedback from reducing gain. Transistor 1100 is connected in an amplifier configuration having its gain set by resistors 1112, 1114. Capacitor 1116 provides power supply filtering.

The signal from transistor 1100 is applied through resistor 1120 to a unity gain buffer 1122 powered through resistor 1124, with filtering provided by capacitor 1126. DC feedback is provided through resistor 1104 for good temperature stability.

The output of buffer 1122 is applied through DC blocking capacitor 1128 to the delay compensation circuit 1022.

To preserve the pulse shape through a delay line circuit, two criteria must be satisfied. First, the delay of the signal path across the band of frequencies included in the pulse must be reasonably flat. Second, the phase projection of the signal path over the band of frequencies included in the pulse project through some multiple of 180° at zero frequency. The delay lines used in the delay line channel 1008–1016 do not satisfy either criteria. Consequently, the delay line compensator 1022 used in conjunction with the fixed line 1026 accomplishes the two criteria set forth above. The delay compensator 1022 substantially compensates for the variations in the delay through the delay line channel as a function of frequency. The compensator is an all-pass network formed by transformer 1130, inductor 1132, capacitor 1134, transformer 1136, inductor 1132, capacitor 1140, resistor 1142, capacitor 1144, and capacitor 1146. As is well known in the art, the all-pass network delay compensation circuit 1122 has a nearly flat amplitude vs frequency response and provides a nearly constant input impedance with frequency. It has zero degrees of phase shift at zero frequency, increasing to 180° of phase shift at its resonant frequency, and provides increasing phase shift toward 360° as the frequency goes substantially beyond the resonant frequency. At low frequencies, the transformers 1130, 1136 apply the input signal to the output, with virtually no phase shift. At high frequencies, capacitors 1144, 1146 carry the input signal to the output with little phase shift. At its resonant frequency, inductor 1132, in series with capacitor 1134, ground the center tap of tranformer 1130. At its resonant frequency, the center-tapped transformer 1130, with capacitors 1134, resonate and become open-circuited. With its center tap shorted to ground, the resonant transformer 1130 provides a 180° phase inversion to the signal driving it. The impedance levels are selected so that the desired phase shift of, for example, 90° and 270° is provided at the desired frequencies, giving the desired overall change in phase versus change of frequency over the desired band of interest. Similar operation is achieved with transformer 1136, inductor 1138, capacitor 1140, and capacitor 1146, but at a different set of frequencies. The delay compensation circuit 1122 is also designed to provide a constant input impedance. The compensation circuit is an all-pass network, which, due to losses, has slight signal attenuation.

The output of the delay line compensation circuit 1122 passes through a buffer 1124 (FIG. 8A, 8C) which is implemented by a transistor 1150 receiving the output from the delay line compensation circuit 1022 through capacitor 1152 and resistor 1154. The transistor 1150 is biased through resistors 1156, 1158. Power supply filtering is provided by inductors 1160, 1162. Transistor 1150 is also biased by current flowing through resistor 1166. An RF choke 1168 open-circuits the bias path at the signal frequency.

The buffered signal at the output of emitter follower transistor 1150 in 1024 is applied to tapped delay line 1026 through DC blocking capacitor 1170 and resistor 1172 to a tapped delay line 1174, described in greater detail below.

Since reflections from the end of the delay line 1174 can appear at the various taps without being attenuated, the tapped delay line uses an end compensating circuit 1180 consisting of inductor 1182, inductor 1184, capacitor 1186, variable capacitor 1188, fixed resistor 1190, and potentiometer 1192. The real portion of the termination impedance is controlled by resistor 1190 and series potentiometer 1192, which is adjusted to obtain the proper resistance. The reactive impedance is set by inductor 1182, inductor 1184, capacitor 1186, and capacitor 1188. Capacitor 1188 is adjusted to adjust the reactive impedance. Both the potentiometer 1192 and capacitor 1188 are adjusted to achieve minimum reflection.

The tapped delay line 1174 has four taps, which are buffered by emitter follower transistors 1200–1206, respectively. The taps are connected to the base of the transistors 1200–1206 through respective resistors 1210–1216. The transistors 1200–1206 are biased through resistors 1220–1226, respective potentiometers 1230–1236, resistors 1240–1246 and 1250–1256. Respective bypass capacitors 1260–1266 and 1270–1276 place the transistors 1200–1206 in emitter follower configuration at the operating frequency, with the collectors of the transistors 1200–1206 AC grounded and only the potentiometers 1230–1236 and resistors 1240–1246 in the emitter circuit. The attenuation of the emitter follower transistors 1200–1206 for each channel is adjusted by adjusting the respective potentiometers 1230–1236.

As explained above with reference to FIG. 8A, the taps of the delay line 1026 are applied to a multiplexer 1028, which selects one of the taps as the output signal. The multiplexer 1028 is implemented by a conventional one of four multiplexer 1300 enabled through resistor 1302 and controlled by 2-bit DLT10 and DLT11 inputs. The DLT10 and DLT11 inputs are generated by a PAL circuit 1039, which also generates the DLT signals for the other four multiplexers 1028 in the delay board 1000. The PAL 1312 selects the DLT tap control signals as a function of the delay line channels associated with the delay line board 1000 and the ultrasound frequency of the transmitted pulse. The delay line channels associated with the delay line board 1000 are determined by the KS0 and KS1 bits, which are set depending upon the slot into which the delay line board 1000 is inserted. The KS0 and KS1 lines are normally biased high through resistors 1314, 1316. The frequency inputs Q7.5*/5 and Q7.5/5* are applied differentially to a comparator 1318 through respective resistors 1320, 1322. The inputs to the comparators 1380 are biased high through respective resistors 1324, 1326. Similarly, the output of comparator 1318 is biased high through resistor 1328. The output of comparator 1318 is applied as the third control bit to the PAL 1312. The remaining inputs to the PAL 1312 are biased high through resistor 1330.

The output of the multiplexer 1028 passes through a unity gain buffer 1030 and is applied through DC blocking capacitor 1340 to the variable delay line 1032 through a source impedance control circuit 1342, which, as the name implies, sets the source impedance of the signal into the variable delay line 1032 in order to minimize reflections. The source impedance control circuit 1342 consists of a pair of back-to-back PIN diodes 1344, 1346 interconnected by capacitor 1348. Control current through the diodes 1344, 1346 is provided through respective resistors 1348, 1350, with the control current flowing through the diodes 1344, 1346 flowing to ground through respective RF chokes 1352, 1354. The impedance between the output of the buffer 1030 and the input to the variable delay line 1032 is a function of the impedance of the diodes 1344, 1346, which is, in turn, controlled by the magnitude of the control current flowing through the diodes 1344, 1346. The signal from the output of the variable delay line 1032 passes through an output impedance control circuit 1360 consisting of diodes 1362, 1364, capacitor 1366, resistors 1368, 1370, and RF choke 1372. The output impedance control circuit 1360 is substantially identical to the source impedance control circuit 1342 and operates in substantially the same manner. Moreover, the diodes 1344, 1346 in the source impedance control circuit 1342 are matched to the diodes 1362, 1364 in the output impedance control circuit 1360, again to minimize reflections and allow a single control voltage to set the impedance for each channel.

The control voltage for the source impedance control circuit 1342 and the output impedance control circuit 1360 is supplied by terminators control operational amplifier 1380, which receives its inputs from the termination control voltage input CT01 for channel 1, a reference ground from REFUND. The reference voltage amplifier 1382 receives a 5 volt reference from the timing and control subsystem through resistor 1384. The amplifier 1382 has a unity gain as set by resistors 1384, and feedback resistor 1386. Low-pass filtering is provided by capacitor 1390. The reference ground is applied to the noninverting input of the amplifier 1382 through resistor 1392, and it is low-pass filtered by capacitor 1394. Amplifier 1382 thus outputs a buffered negative precision reference voltage referenced to reference ground to impedence control amplifier 1380 and to the corresponding termination control amplifiers and delay control amplifiers for the other channels in the delay line board 1000.

The negative precision reference voltage from amplifier 1382 is applied to the summing junction of operational amplifier 1380 through a summing resistor 1400. Similarly, the reference ground is applied to the summing junction of operational amplifier 1380 through summing resistor 1402. The termination control voltage CT01 (or CTN for channel N) is applied to the noninverting input of the amplifier 1380 through resistive divider consisting of resistor 1404 and resistor 1405. A feedback resistor 1406 has a resistance selected with respect to the values of resistor 1400, 1402, 1404 and 1405, causing the amplifier 1380 to output the sum of the reference voltage and three times the terminating control voltage CT referenced to reference ground. Low-pass filtering is provided by capacitors 1408 and 1410. Thus, the control voltage for the source impedance control circuit 1342 and the output impedance control circuit 1360 is equal to the sum of the reference voltage and three times the termination control voltage CT.

As explained in greater detail below, the signal delay produced by the variable delay line 1032 is controlled by differential delay control voltages +VD and −VD, which are filtered by capacitors indicated generally at 1418. The positive and negative delay control voltages are generated at the output of buffers 1420, 1422, respectively, which, in turn, receive outputs from respective delay control amplifiers 1424, 1426. The delay control amplifiers 1424, 1426 are connected to circuitry that operates substantially in the same manner as termination control amplifier 1380 and its associated circuitry, except that the delay control amplifiers 1424, 1426 output their respective delay control signals to the buffers 1420, 1422 through respective resistors 1430, 1432 because the input impedance to the buffers 1420, 1422 can be negative under certain conditions. Delay control amplifier 1424 outputs a delay control signal through buffer 1420 that is the sum of the referenced voltage and four times the delay control signal for the first channel CD01 (or CDN for channel N) referenced to reference ground, while delay control amplifier 1426 outputs a delay control voltage through buffer 1422 that is the negative of the sum of the reference voltage and four times the delay control voltage CD. It is thus seen that the delay control voltages are applied to the variable delay line 1032 differentially.

The output of the variable delay line 1032 is, as explained above with reference to FIG. 8A, passed through a unity gain buffer 1034. The output signal is applied to the buffer 1034 from the output impedance control circuit 1360 through a resistor 1440 and capacitor 1442 to stabilize the buffer 1034 under varying load conditions. The output of the buffer 1034 is applied to one input of the amplitude weighing and summation subsystem 68 through a DC blocking capacitor 1444.

A schematic of the EPROMs 1040 and multiplexer 1042 is illustrated in FIG. 8E. EPROMs 1050, 1052 store data indicative of the operating parameters of the tapped delay lines 1026 and the variable delay lines 1032, such as delay times and termination impedances. As explained in greater detail below, the data in the PROMs 1050, 1052 is output to a shift register 1054 in parallel and then applied through a tri-state buffer 1056 in serial to the delay controller subsystem 66 (FIG. 2A).

When data stored in PROMs 1050, 1052 is to be output to the delay controller subsystem, the SELECTX* input to inverter 1060 goes low. The output of inverter 1060, which is normally biased low through resistor 1062, then goes high to remove the CLEAR signal from a counter 1064, and, through inverter 1066, remove the CLEARs from counters 1068, 1070, enable the PROMs 1050, 1052, and enable the tri-state buffer 1056. DLCLOCK* pulses are then applied through inverter 1070 to the clock input of counter 1064 and the clock input of shift register 1054. The input to inverter 1070 is normally biased high through resistor 1072. Since counter 1064 is normally enabled by NAND-gate 1074, it then begins incrementing in response to the DLCLOCK* pulses. Counter 1064 outputs its three least significant bits through inverters 1076, 1078, 1080 to a NAND-gate 1082 that detects the zero count of the counter 1064. Thus, each time the counter 1064 counts 8 DLCLOCK* pulses, the output of NAND-gate 1082 pulse is low. The negative-going pulse at the output of NAND-gate 1082 causes shift register 1054 to load the eight bits on the data bus of PROMs 1050, 1052. The data loaded into the shift register 1054 is then clocked out of the shift register in series during the next eight DLCLOCK* pulses, after which NAND-gate 1082 once again pulses low to reload the shift register 1054.

Addressing of the PROMs 1050, 1052 is accomplished by the counters 1068, 1070 and a buffer 1084 through NAND-gate 1086, acting as an inverter. The fourteen least significant bits of the address for PROMs 1050, 1052 are provided by the counters 1068, 1070. The counters are cleared when the SELECTX* input is high. However, when data transfer is to occur, the SELECTX* input goes low, thereby removing the CLEAR from the counters 1068, 1070 and allowing the counters 1068, 1070 to increment every eighth DLCLOCK* pulse since the counter 1070 is clocked by the output of inverter 1076, which, in turn, receives the third least significant bit of the counter 1064. The two most significant address bits are determined by the slot into which the delay line circuit 1000 is inserted. For example, if delay line board 1000 is inserted into the first slot, the KS0 and KS1 inputs are both at ground, thereby causing PROM 1052 to be enabled, with its most significant bit at logic "0" and PROM 1050 to be disabled through NAND-gate 1086. PROM 1052 then outputs data for delay line channels 1–5. If the delay line board 1000 is inserted into the second slot, KS0 will go high, thereby once again selecting PROM 1052, but the most significant address bit will now be logic "1," thereby causing PROM 1052 to output a set of data for delay line channel 6–10. If delay line board 1000 is inserted into the third slot, KS1 will be high and KS0 will be low, thereby enabling PROM 1050 through NAND-gate 1086 and disabling PROM 1052. PROM 1050 will then output a set of data for delay line channels 11–15 since its most significant bit is logic "0." Finally, if delay line card 1000 is inserted into the fourth slot, both KS1 and KS0 will be high, thus selecting the set of data in the high-order memory bank of PROM 1050 since the most significant data bit is now high. PROM 1050 then outputs a set of data for delay line channels 16–20. Thus, the position of the delay line board 1000 in the backplane determines the channels with which it is associated.

Delay Controller

The delay controller 66 (FIG. 2) includes the circuitry for generating the voltages controlling the delay for each of the twenty delay channels in the delay lines, the voltages for controlling the termination impedances for each of the twenty delay lines, the voltages for controlling the gain of the amplitude weighting circuitry in the amplitude weighting, sum, and TCG subsystem. The delay controller 66 also applies control signals to other subsystems in the analog portion of the ultrasound imaging system and is the only link between the analog and digital circuitry other than timing signals and the Manchester data link.

Figures 5, 6, 7, 8, 9:
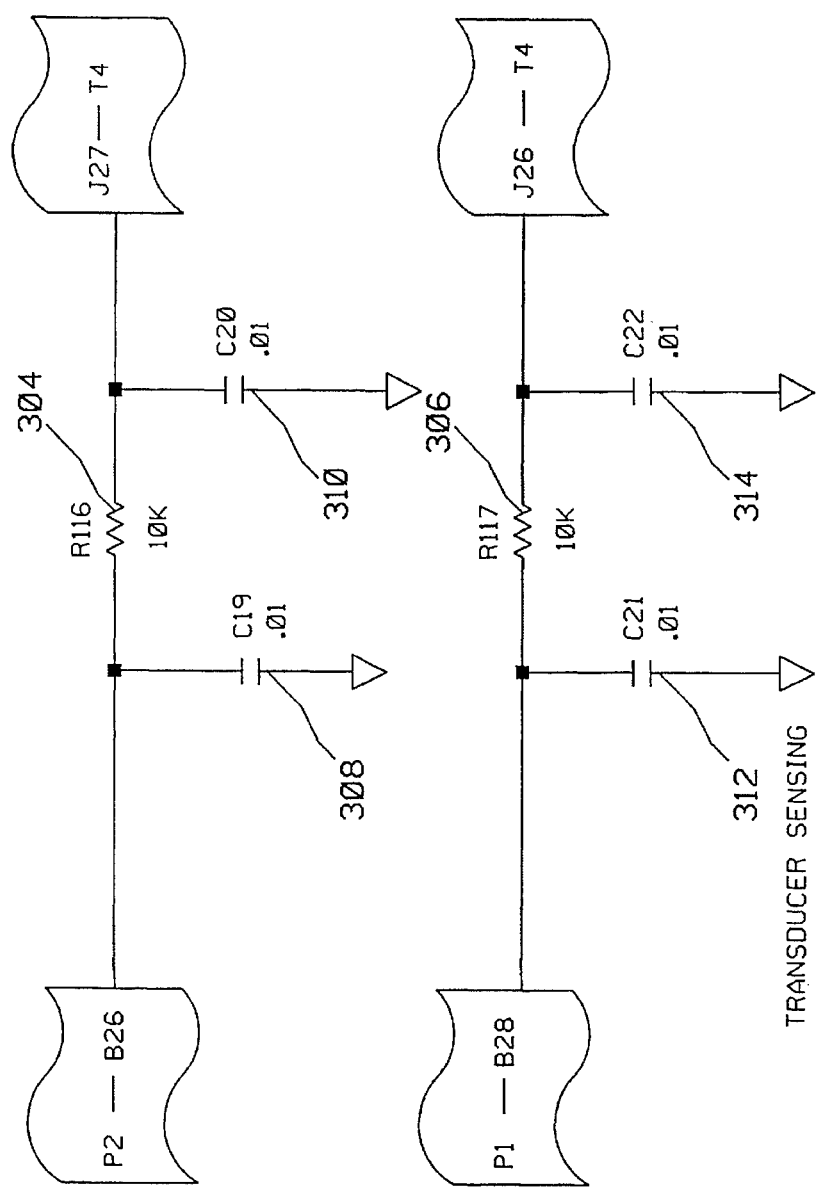
FIG. 9 is the circuit schematic for the delay controller.

Referring to FIG. 9A, the CPU communicates with a microprocessor 1500 through differential signal level translators 1502, 1504, 1506, 1508. Pulldown resistors, indicated generally at 1510, bias the outputs of the differential drivers 1506, 1508 low while resistors 1512, 1514 set the input impedance to the differential receivers 1502, 1504, respectively. The CPU applies data to the microprocessor 1500 through the differential receiver DI input, which is applied to the P23 input of the microprocessor 1500. Serial data from the microprocessor 1500 is applied to the CPU through the differential driver 1506. These differential signals are translated on the timing and control card. These signals are then passed on to the CPU through another set of signal level translators.

The microprocessor 1500 may be placed in a quiescent mode. In order to trigger the microprocessor 1500 out of the quiescent mode and into an active state, the CPU generates a differential COMMAND and COMMAND* input that is applied through level translator 1502 to the P16 port of the microprocessor 1500. Thereafter, the microprocessor 1500 is placed in the active condition. When the microprocessor 1500 is in the active mode and is ready to accept a COMMAND input or data D0, the microprocessor 1500 generates a differential STATUS and STATUS* output applied from the P10 port of the microprocessor 1500 through level translator 1508. Upon receiving the status bit, the CPU applies a serial COMMAND D0 to the microprocessor 1500. The I/O ports, P10, P11, P12, P21 and P24, the interrupt request input IRQ and the NMI input are pulled high through pullup resistors 1520.

As mentioned above, the microprocessor 1500 operates in a quiescent mode until it is requested to perform any computational or control functions. When requested to perform extended periods of computation or data manipulation, the microprocessor 1900 must maintain its active condition. For this purpose, a "keep alive" circuit is used to maintain the clock to the microprocessor 1500 and other circuitry in the delay controller in the active mode.

The microprocessor 1500 using the I/O expander 1650, FIG. 9B generates an alternating HIGH/LOW signal that is applied to the capacitor 1524. On the high transition of the signal the capacitor 1524 is discharged through diode 1528. On the low transition of the signal capacitor 1532 is discharged into capacitor 1524. The alternating charge/discharge of capacitor 1524 will keep capacitor 1532 discharged, this turns the "keep alive" input on. If the alternating signal is stopped in either a high or low state then capacitor 1532 will be allowed to charge through resistor 1530 and turn the "keep alive" input off. Resistors 1536 and 1534 supply a discharge path for capacitor 1524.

NAND-gate 1528 has two inputs: the COMMAND input through 1502 and inverter 1540 or the "keep alive" circuit described above. If either of these inputs become active (low) then the output of 1528 becomes active (high). This high signal applied at diode 1644 will charge capacitor 1552. When the charge on capacitor 1552 accumulates to a voltage of 3.7 volts, then a low will appear on the output of inverter 1546. This low is then applied to diode 1570 and inverter 1548. A low applied to diode 1570 will discharge capacitor 1572 and cause inverters 1576 and 1574 to take the microprocessor 1500 out of reset. The same low from 1546 applied at 1548 causes the counters 1560 and 1550 to divide the 60 mHz clock source down to the 7.5 mHz microprocessor 1500 clock and the 5 mHz input to the serial baud rate generator 1584.

If the signal from NAND-gate 1528 becomes inactive (low), then capacitor 1552 will discharge, causing capacitor 1572 to charge. When the charge on capacitor 1572 drops to a voltage of 0.8 volt, then a high will appear at the output of 1546. This high is then applied to diode 1570 and inverter 1548. A high applied to diode 1570 will charge capacitor 1572 and cause inverters 1576 and 1574 to put the microprocessor 1500 into reset. The same high from 1546 applied at 1548 causes the counters 1560 and 1550 to stop, which removes the 7.5 mHz microprocessor 1500 clock and the 5 mHz input to the serial baud rate generator 1584.

The microprocessor 1500 includes twenty-nine I/O ports P10–P47. Eight of these I/O ports P30–P37 are used as a combination 8-bit data bus and low-order eight bits of a 16-bit address bus. The eight high-order address bits are output on the P40–P47 I/O ports of the microprocessor 1500. The high-order address bits are applied to the PAL 1580, which decodes the address into three outputs. One output is an EXT EPROM SELECT output that is high whenever the address for microprocessor is greater than hexadecimal 4,000 and less than hexadecimal BFFFF. A second output enables an address decoder 1590 for addresses less than 256 whenever the inverters 1574, 1576 are not generating a RESET. Address decoder 1590 decodes address bits A4–A7 to generate a set of chips select signals which are used as explained below. Finally, the PAL 1580 enables a pair of address decoders 1592, 1594 for addresses of hexadecimal 2,000 and above whenever a reset is not being generated. The address decoders 1592, 1594 are alternately enabled by a PE-B3 input which is applied to the address decoder 1594 through inverter 1596. The inputs PE-B2, B1, B0 are decoded by the address decoders 1592, 1594 to generate one of sixteen chip selects for random access memories that store data indicative of the amplitude of various control signals as described in greater detail below. The output of PAL 1580 generated for hexadecimal 2,000 and above is also applied through inverter 1598 to a NAND-gate 1600, which also receives an output from the E output of microprocessor 1500. NAND-gate 1600 enables a buffer 1602 whenever microprocessor 1500 outputs an E high and the address is hexadecimal 2,000 and above. Buffer 1602 outputs a buffered data bus BD0–7 from the address data bus AD0–7 of the microprocessor 1500.

The address data bus AD0–7 of the microprocessor 1500 is also applied to an address latch 1604 that records the address data bus AD0–7 as the low-order address bus A0–A7 when it is clocked by an AS pulse from microprocessor 1500. In this manner, the address data bus AD0–7 is used to generate a 16-bit address at the same time that the microprocessor 1500 outputs eight bits of data.

The microprocessor 1500 also outputs a read/write* signal R/W* which is output through buffers 1606, 1608. Since buffer 1608 inverts its input, READ and WRITE are alternately high, depending upon whether the R/W* output of microprocessor 1500 is high or low, respectively. Similarly, microprocessor 1500 generates an enable signal E which is output through noninverting buffer 1610 and inverting buffer 1612 to output a BE and BE* depending upon whether the E output of microprocessor 1500 is high or low, respectively.

It will be recalled from the explanation of FIG. 11 that data indicative of the delay line control voltages, the delay line termination voltages and the amplitude weighting control voltages are stored in a pair of PROMS 1050, 1052 (FIG. 8B). The data stored in the PROMS 1050, 1052 are output by a tri-state buffer 1056 in serial. With reference, now, to FIG. 9B, this serial data is applied to a shift register 1620 which is clocked by a 156.25 kHz clock generated by counter 1584 (FIG. 9A). The serial data from the PROMs 1050, 1052 (FIG. 8B) is thus serially clocked into the shift register 1620 with each 156.25 kHz clock pulsed.

The 156.25 kHz clock pulses also increment a counter 1622. When the counter 1622 has counted to seven, all of the inputs to NAND-gate 1624 are high, thus causing NAND-gate 1624 to output a low that enables a pair of latches 1626, 1628. On the next pulse of the 156.25 kHz clock, the data that has been shifted into shift register 1620 is clocked into the now enabled latches 1626, 1628. In summary, data from the delay line PROMS is clocked into the shift register 1620 in serial with the counter 1622 being incremented for each bit of data shifted into the shift register 1620. After eight bits of data have been shifted into the shift register 1620, counter 1622 enables the latches 1626, 1628 through NAND-gate 1624, thereby allowing the contents of the shift register 1620 to be clocked into the latches 1626, 1628. Eight more bits of data are then shifted into the shift register 1620, in the above described procedure, then repeats. The latches 1626, 1628 output eight bits to the address/data bus AD0–7 of the microprocessor 1500 (FIG. 9A).

The low generated by NAND-gate 1624 on the seven count of the counter 1622, also loads the counter 1622 with zero and is clocked into flip-flop 1630 by the subsequent pulse of the 156.25 kHz clock to generate a high DATA AVAILABLE. The high DATA AVAILABLE output from flip-flop 1630 is applied to the P17 I/O port of the microprocessor 1500 (FIG. 9A) to inform the microprocessor 1500 that data from the delay line PROMS is available at the data latches 1628 and 1626.

The operation of the counter 1622 is controlled by the outputs from a set of flip-flops 1632, 1634, 1636. When data is to be read from the delay line PROMS, the microprocessor 1500 (FIG. 9A) outputs a high INTERFACE RESET at its P11 I/O port, thereby setting flip-flop 1632 on the trailing edge of the next 156.25 kHz clock pulse. After the end of the next 156.25 kHz clock pulse, the high at the output of flip-flop 1632 is clocked into flip-flop 1634, thereby generating a high that is applied to a decoder 1638A. The high switches the DLCLOCK* output of the decoder 1638A from its grounded input to the 156.25 kHz clock, thereby causing the decoder 1638A to output the 156.25 kHz clock as the DLCLOCK* signal. On the trailing edge of the next 156.25 kHz clock pulse, the high at the output of flip-flop 1634 is clocked into flip-flop 1636, thereby causing flip-flop 1636 to output a high that removes the clear from counter 1622 and allows the counter 1622 to count 156.25 kHz clock pulses. As explained in greater detail below, a decoder 1638B then decodes two inputs DELAYSEL0 and DELAYSEL1 to generate a low at one of its outputs SELECT0*–SELECT3*. As illustrated in FIG. 8B, the SELECT0*–SELECT3* output of decoder 1638B selects the PROMS 1050, 1052 for one of the four delay line cards, one of which is illustrated in FIG. 8B. At the same time, the DLCLOCK* output of decoder 1638A increments address counters that generate the addresses for the PROMS 1050, 1052. Thus, when the SELECT0* output of decoder 1638B goes low, data from the PROMS 1050, 1052 for delay line channels 1–5 are output in serial with each DLCLOCK* pulse. Similarly, when the SELECT3* output of decoder 1638B goes low, data is output from the PROMS 1050, 1052 for channels 16–20 in serial for each DLCLOCK* pulse.

The flip-flops 1632, 1634, 1636 are clocked through inverter 1640, and they are held in their non-cleared state by a high generated at the output of driver 1642 which receives the +5 volt power supply signal through resistor 1644. The high applied through resistor 1644 also enables counter 1622, shift register 1620 and flip-flop 1630.

Data indicative of the time-gain control parameters used to increase the gain of the amplitude weighting and summing channels as a function of depth is stored in a PROM 1648. The PROM 1648 is addressed by 15 bits of the 16-bit address generated by the microprocessor 1500 and address latch 1604 (FIG. 9A). The data stored in the PROM 1648 is output on the address/data bus AD0–7. As explained in greater detail below, the data on the address/data bus AD0–7 from the PROM 1648 is applied to a digital to analog converter that generates time-gain control signals having a magnitude determined by the data in the PROM 1648.

The address/data bus AD0–7 is also connected to an I/O expander 1650 which generates various control signals by decoding the address/data bus AD0–7. The I/O expander 1650 is enabled by the CS20 output from the decoder 1590 which decodes the 4–7 bits of the address bus. The I/O expander 1650 is strobed by the AS signal generated at the SC1 output of the microprocessor 1500. The I/O expander 1650 is held in its non-reset condition by a high applied to the RESET* input through resistor 1650. Capacitor 1652 causes the RESET input to go low at power up when power is initially applied to the system.

The I/O expander 1650 also includes three banks of I/O ports, the "A" bank PA0–PA7, the "B" bank PB0–PB7 and the "C" bank PC0–PC7. The PC0–PC7 I/O ports output various data bits designating the ultrasound frequency being transmitted by the transmitters and the number of sample sites currently being used. These outputs are generated differentially by a set of drivers 1654, 1656, 1658, 1660 which generate respective differential outputs through resistors 1662. The 7/5, 7/5*, Q7/5, and Q7/5* outputs designate the ultrasound frequency for the remainder of the analog circuitry. The FD, FD* CD, CD* outputs designate the number of sample sites for the remainder of the analog circuitry. The 7HD SENSC* and 5HD SENSC* indicate whether the 7.5 and 5 mHz transducers are connected to the ultrasound imaging system.

The 5REL SENSC* and 7REL SENSC* inputs to the I/O expander 1650 show the status of the position of the relays that connect either the 5 mHz transducer or the 7.5 mHz transducer to the crossbar subsystem.

The 7/5 output from the PB0 output of the I/O expender 1650 designates the operating ultrasound frequency for use internally by the delay controller 66. The ALIVE* signal generated at the PB1 output is the square wave that is applied to the capacitor 1524 (FIG. 9A) to keep the microprocessor 1500 in the active mode. The DELAYSEL0 and DELSEL1 output from the PB2 and PB3 ports, respectively, are decoded by the decoder 1638B to generate one of the SELECT0*–SELECT3* outputs that select one of the four sets of PROMs for respective five delay line channels.

The PE-B0 through PE-B3 outputs generated from the PA0–PA3 ports are decoded by the decoders 1592–1594 (FIG. 9A) to generate chip selects for random access memories that store serial data from the delay line PROMs as explained in greater detail below. The PA4 I/O port outputs a low ENABLED* output through inverter 1668 to output data from a random access memory storing values indicative of voltage levels to a digital-to-analog converter, as explained in greater detail below. The PA5 I/O port allows the microprocessor 1500 to directly access the above-mentioned digital-to-analog converters, as explained in greater detail below.

The I/O expander 1650 also receives the READ signal generated by the buffer 1606 (FIG. 9A) at its R/W* input in order to control the direction of data flow through the I/O expander 1650. The 2 mHz clock BE generated by buffer 1610 is applied to the data strobe DS input of the I/O expander 1650 to control the transfer of data through the I/O expander 1650. The READ inputs, BE and EXT EPROM SELECT output from PROM 1580 (FIG. 9A) are applied to a NAND-gate 1670 that output-enables PROM 1648 each BE clock pulse when READ is high and the external PROM has been selected by an EXT EPROM SELECT high.

The 2 mHZ clock BE, the READ input and the SC40* output from decoder 1590 (FIG. 9A) are applied to a NAND-gate 1672. The CS40* input is applied through inverter 1674. NAND-gate 1672 output-enables the latches 1626, 1628 and presets the flip-flop 1630 to apply data from shift register 1620 to the address/data buss AD0–AD7 on each BE pulse when READ is high and the chip select signal CS40* is low.

With reference to FIG. 9C, the five HDSENSE and seven HDSENSE outputs from the circuitry illustrated in FIG. 5 are applied to respective comparators 1680, 1682. As explained above with reference to FIG. 5, the five HDSENSE and seven HDSENSE inputs are low whenever the 5 mHz and 7.5 mHz, respectively, transducers are connected to the circuitry illustrated in FIG. 5. The 5REL SENSC and 7REL SENSC inputs from the circuitry illustrated in FIG. 5 are applied to respective comparators 1684, 1686. As explained above with reference to FIG. 5, the 5REL SENSC and 7REL SCENSC inputs designate the position of the relay 200 (FIG. 5) connecting either the 5 mHz or the 7.5 mHz transducer to the crossbars. The inputs to the comparators 1680–1686 are biased high through respective resistors 1690–1696 and they are low-pass filtered by respective capacitors 1700–1706. The signals are applied to the respective comparators through respective resistors 1710–1716.

The comparators 1680–1686 receive at their negative inputs a reference voltage generated by voltage divider resistors 1720, 1722. The comparators 1680–1686 thus act as level shifting buffers. The outputs of the comparators 1680–1686 are biased high through respective resistors 1730–1736 to generate the outputs that are applied to the I/O expander 1650, as explained above with reference to FIG. 26.

The circuitry illustrated in FIG. 9C also includes circuits for generating respective reference voltages. Accordingly, a conventional voltage regulator 1740 outputs a 5 volt reference as determined by potentiometer 1742 to a voltage follower 1744. Voltage follower 1744 then generates respective buffered 5 volt references from voltage followers 1746–1756. The output from voltage follower 1748 is further filtered by a low-pass filter consisting of capacitors 1760, 1762, 1764, 1766, inductors 1768, 1770 and resistor 1772.

The address/data bus AD0–AD7 is applied to a conventional four channel digital-to-analog ("D/A") converter 1780 that outputs a voltage on one of its VOUTA–VOUTD outputs. The magnitude of the voltage is designated by the data on the address/data bus AD0–AD7 and the channel on which the data is output is designated by the low-order address bits A0, A1, from the address latch 1604 (FIG. 9A). The A/D converter 1780 generates the voltage designated by the address/data bus on the output designated by the A0, A1 address bits when NAND-gate 1782 outputs a low. NAND-gate 1782 outputs a low on the BE clock pulse when inverting buffer 1608 (FIG. 9A) outputs a high WRITE and decoder 1590 decodes the A4–A7 address bits to generate a CS50* low which is inverted by inverter 1784. The outputs from the A/D converter are applied through respective low-pass filters 1786–1792. The filters 1706–1792 are identical to the low-pass filter receiving the output from voltage follower 1748 and they are thus not described in detail. The low-pass filters each provide for a 4 microsecond delay and, since they are identical to the low-pass filter receiving the output of voltage follower 1748, they have the same insertion loss. As a result, the +5 VREFEXT output and the TIN, TSL, FSL and FG outputs are subject to the same losses by the low-pass filters. As explained in greater detail below, the TIN and TSL outputs control the gain of amplifiers processing the tissue signals to increase the gain of signals received from greater depths. The FSL and FG outputs are similarly used to control the gain of amplifiers for the flow signals in order to increase the gain for flow signals received at greater depths.

As mentioned above, data designating the delay line delays and termination impedances and weighting values for the summing and weighting subsystem are stored in PROMS. One set of these PROMS 1050, 1052 for five channels is illustrated in FIG. 8B. As also explained above, the data is output from the PROMS illustrated in FIG. 8B in serial to the circuitry illustrated in FIG. 26 where it is converted from serial to parallel data and applied to the address/data bus AS0–AD7. The data on the address/data bus is then buffered by a set of buffers illustrated in FIG. 9A to generate eight bits of buffered data BD0–BD7. The buffer data BD0–BD7 thus contains data indicative of the delay line delays and termination impedance and the weighting values for the twenty channels. The buffer data The buffer data BD0–BD10 is input to microprocessor 1500, then to a bi-directional buffer 1800 illustrated in FIG. 9D. The circuitry illustrated in FIG. 9D is one of fifteen identical circuits. Each of the fifteen circuits illustrated in FIG. 9D generate four control voltages for a total of sixty (15×4) control voltages. Twenty of these control voltages are used to control the weighting values, twenty of these control voltages are used to control the delay of the variable delay line, illustrated in FIGS. 12 and 14, and twenty of these control voltages are used to control the termination impedances of the variable delay line illustrated in FIG. 12.

The buffered data BD0–BD7 is applied through bi-directional buffer 1800 to the data bus of a RAM 1802 that is addressed by an 11-bit address RAB0–RAB10 generated as described below. The direction of the bi-directional buffer 1800 is controlled by the WRITE signal generated by the microprocessor 1500 at the output of the inverting driver 1608 (FIG. 9A). When WRITE is high, the buffer 1800 is in a directional mode allowing data to be written from the buffer data bus BD0–BD7 to the data bus of the RAM 1802. The chip select signals for the various circuits illustrated in FIG. 9D are generated by a PAL 1804. PAL 1804 selects the RAM 1802 whenever the ENABLED* input from the I/O expander 1650 (FIG. 9D) is low. RAM 1802 is output enabled whenever the ENABLED* input is low and the WRITE input is low. RAM 1802 is placed in its WRITE ENABLE mode by PAL 1804 whenever ENABLED is high or WRITE is low or the BE input is low. The bi-directional buffer 1800 is enabled whenever the ENABLED input is high or the BE input to PAL 1804 is low. In summary, data from the buffer data bus BD0–BD7 is applied through the bi-directional buffer to the RAM 1802. Thereafter, as sample sites are accessed during a beam, the RAM 1802 outputs data indicative of the time delay, delay time and termination impedance and weighting values for the various sample sites and applies them to a latch 1806, which, in turn, applies the data to an analog-to-digital (A/D) converter 1808 that generates the control voltages for the delay lines, termination impedances and weighting values. The analog-to-digital converter 1808 is enabled whenever ENABLED is high or WRITE and BE are both high. The A/D converter output is selected by decoding the DAB0 and DAB1 inputs which are generated as described below. Each of the D/A converter outputs is applied through a respective low-pass filter 1810, 1812, 1814, 1816 described above with reference to FIG. 9C.

In operation, data is loaded into the RAM 1802 when commanded to by the CPU through the serial interface. The data in each RAM 1802 is then accessed during the beam to vary the delay line delays and termination impedances and the weighting as returns are received from sequentially deeper sample sites. The addresses for the RAM 1802 are generated by the. RAM address controller circuitry illustrated in FIG. 9F. A 60 or 40 mHz clock is applied through a buffer 1830 and driver 1832 to a counter 1834. Another 60 mHz clock is applied through buffer 1838 and driver 1840 to the counters 1550, 1560 illustrated in FIG. 25. Resistors 1842, 1844 control the input impedance of buffers 1830, 1838, respectively.

Counter 1834, in combination with AND-gates 1850, 1852, generate either a 7.5 mHz clock or a 5 mHz clock from the 60 mHz clock input. The counter 1834 is loaded with "1100" at the start of a transmit pulse XMIT and thereafter continuously counts as long as it is enabled by a low ENABLED input from the circuitry illustrated in FIG. 9B. Differential XMIT and XMIT* inputs are applied through buffer 1854 to a NAND-gate 1856 acting as an inverter. Resistor 1858 controls the input impedance of the buffer 1854. On the leading edge of the XMIT pulse, the output of NAND-gate 1856 goes low, thereby setting a flip-flop formed by NAND-gates 1860, 1862. NAND-gate 1860 then outputs a high that is clocked into flip-flop 1862 on the first 60 mHz clock pulse applied through inverter 1864. The high at the output of flip-flop 1862 is also applied to NAND-gate 1866 which is enabled by the high at the output of flip-flop 1868. Thus, on the leading edge of XMIT, the output of NAND-gate 1866 goes low. On the second 60 mHz clock pulse, the high at the output of flip-flop 1862 is clocked into flip-flop 1864. On the next 60 mHz clock pulse, the high at the output of flip-flop 1864 is clocked into flip-flop 1868 which then generates a low that resets the flip-flop formed by NAND-gates 1860, 1862 and also causes the output of NAND-gate 1866 to go high. Thus, NAND-gate 1866 outputs a low for two 60 mHz clock pulses (about 33 nanoseconds) starting at the leading edge of XMIT. The low at the output of NAND-gate 1866 loads counter 1834 with "0011" and, when the output of NAND-gate 1866 goes high, counter 1834 begins incrementing. Counter 1834 is loaded with decimal 3 in order to make the timing of the frequency divider circuitry operate properly.

The QA, QB, QC outputs of the counter 1834 are applied to NAND-gate 1852 along with a 7/5* input applied through inverter 1874. The 7/5* signals generated by the I/O expander 1650 designate the ultrasound frequency being transmitted by the transducers. When the 7/5* input is low, NAND-gate 1852, in combination with counter 1834, divides the 40 mHz clock by eight, thus generating a 5 mHz clock at the output of NAND-gate 1852. When the 7/5* input is high, NAND-gate 1850, in combination with counter 1834, divides the 60 mHz clock by 16 to generate a 3.75 mHz signal at the output of NAND-gate 1850. As explained in greater detail below, when the ultrasound frequency is 5 mHz, the RAM address controller is able to address the RAMS so that they output a new set of control signals for each two sample sites. Because of the higher operating frequency of 7.5 mHz, the RAM 1802 is addressed at 3.75 mHz at the 7.5 mHz ultrasound frequency so that the delay, termination impedance, weighting values and time-gain control values are updated every four sample sites in the 7.5 mHz operating mode.

The 5 mHz clock at the output of NAND-gate 1852 is applied to a flip-flop 1870 which is clocked by the 60 or 40 mHz clock through inverter 1872. The high at the output of flip-flop 1870 is then applied through inverter 1874 to NAND-gate 1876 and from there to flip-flop 1878. On the leading edge of the next 60/40 mHz clock, the low at the output of NAND-gate 1876 is clocked into flip-flop 1878 and applied through inverters 1880, 1882, 1884, 1886, 1888 to counters 1890, 1892, 1894. Counters 1890, 1892, 1894 then increment with each of the 5 mHz clock pulses to generate the addresses for the RAM 1802 (FIG. 9D) as explained in greater detail below. When the ultrasound frequency is at 7.5 mHz, NAND-gate 1850 outputs a low at a 3.75 mHz rate. On the leading edge of the next clock pulse, the low is clocked into flip-flop 1900 which then outputs a low through inverter 1902 to flip-flop 1904. On the next leading edge of the 60 mHz clock, the low is clocked into flip-flop 1904 and applied through inverter 1906 to NAND-gate 1876. NAND-gate 1876 outputs a high when the low is clocked into the output of flip-flop 1900 and when the low is clocked into the output of flip-flop 1904. As a result, NAND-gate 1876 outputs a pulse of about 33 nanoseconds. The use of two flip-flops 1900, 1904 is used to expand the width of the pulse generated at 7.5 mHz to allow relatively slow counters 1890, 1891, 1894 to be used. The high at the output of NAND-gate 1876 is then applied to flip-flop 1878 which, on the leading edge of the next 60 mHz clock pulse, outputs a clock pulse to the counters 1890, 1892, 1894.

As mentioned above, NAND-gate 1866 outputs a low for two of the 60/40 mHz clock pulses after the leading edge of the XMIT pulse. This low is clocked into flip-flop 1910 on the next leading edge of the 60/40 mHz clock. On the leading edge of the second 60/40 mHz clock pulse, the low at the output of flip-flop 1910 is clocked into flip-flop 1912. The low at the output of flip-flop 1912 is applied through inverter 1914 to flip-flop 1916 which then outputs a low on the leading edge of the third 60/40 mHz clock pulse after the XMIT pulse. The low is then applied to the clear inputs of the counters 1890, 1892, 1894 through inverter 1918. When XMIT once again goes high, the clear is removed from the counters 1890, 1892, 1894 after a delay of three 60/40 mHz clock pulses. Thus, the counters 1890, 1892, 1894 are held at clear for four pulses of the 60/40 mHz clock after the start of XMIT. Thereafter, the counters 1890, 1892, 1894 begin incrementing as explained above.

The clock output from inverter 1882 is also applied to AND-gate 1809 (FIG. 9D) to enable the D/A converters. The clock at the output of inverter 1884 is applied through inverter 1930 to a flip-flop 1932 that receives the low-order bit from the counter 1890. Similarly, the clock is applied through inverter 1930 to a flip-flop 1934 that receives the second order bit from the counter 1890. The outputs of the counters 1932, 1934 are applied to a multiplexer 1936 which applies them to the DAB0, DAB1 outputs whenever ENABLED* is low. The ENABLED* input is generated by the I/O expander 1650 (FIG. 9B). The DAB0 and DAB1 outputs select which of the outputs of the A/D converter 1808 (FIG. 9D) are active.

The outputs from the counters 1890, 1892, 1894 are applied to respective multiplexers 1940, 1942, 1944 which also receive the 11 bit address bus A0–A10 and the D/A SEL output from the I/O expander 1650 (FIG. 9B). The multiplexers 1940, 1942, 1944 apply the outputs of the counters 1890, 1892, 1894 to the address inputs RAB0–RAB11 of the RAMs 1902 (FIG. 9D) when the ENABLED* control input to the multiplexers is low. When the ENABLED* input is high, the multiplexers 1940, 1942, 1944 utilize the microprocessor generated address A0–A10 and D/ASEL to address the RAMs. Also, the DAB0 and DAB1 outputs of multiplexer 1936 are then connected to the A0 and A1 address bits. The multiplexers 1936, 1940, 1942, 1944 thus allow the microprocessor 1500 to directly access the RAMs 1802, although they are normally addressed by the counters 1890, 1892, 1894.

Below is a listing of the program design language for the delay controller microprocessor 1500:

```
-----------------------------------------------------------------
                         Initialization
-----------------------------------------------------------------
          This path taken on cold start or wake up
Port 2 serial port initialization
          Set rate and mode to external clock
          Set xmit/rcv cont/status reg to
          Read status reg
          Read receive buffer to clear the port
Port 1 initialization
          P10-p13 initialized outputs
          Initialize data in port 1
          P14-p17 initialized to inputs
          Initialize data in port 1
Port 4 initialization
          Must write ones to port 4 DR to allow uses as
              address lines
          Set the port 4 DDR
Stack initialization to $00ff
Check the cold/warm word to determine if the 146823 should
   be initialized
          Get the cold/warm word
          Is it the correct data?
          No, jump to 146823 initialization routine
-----------------------------------------------------------------
    If just waking up, check the 146823 for valid program-
       ming status
    If not programmed properly, then program and set the
       mode to the last program mode
-----------------------------------------------------------------
          Get port E data
          Run subroutine to check programming integrity
          Set error register 1 if check fails
          Get port F data
```

```
            Run subroutine to check programming integrity
            Set error register 1 if check fails
    ----------------------------------------------------------------
       Subroutine: Check_ports
05     Check the ports in the 146823 for possible unprogram-
          med state
       Note:  Can only check ports E and F.  G has control
          data that cannot be momentarily changed.
    ----------------------------------------------------------------
10            Get port data
              Reset data of interest
              Set some data
              Store the data
              Read it back
15            Check data stored
              Restore original data
              If what was stored is what is read, then
              146823 is programmed
              Return
20  ----------------------------------------------------------------
    Initialize 146823 interface hardware
    ----------------------------------------------------------------
    Toggle the 146823 reset line
    Initialize registers - cold start path only
25  Wake up error path or cold start path continued
            Get data to toggle p13 the 146823 reset
            Set active (about 1000 ns)
            Set inactive
    Initialize port F (port b)
30          01 is initial data and 6F is DDR
            Set the data
            Set the direction

35
```

```
     Initialize port E (port a)
             Initial data is 00; DDR is FF
             DDR is FF
             Set the data
05           Set the direction
     Initialize port g (port c)
             00 is initial data and F0 is DDR
             Set the data
             Set the direction
10           Set warm start data in RAM
             Get mode 7ss data
             Set the initial mode to 7ss
     ----------------------------------------------------------
     Command Processor
15           The command processor sets the DCD line active
     (low) when it encounters an active RTS line (high); else it
     is left inactive (high).  It also sets the keep alive
     inactive.
             After receiving an active RTS and setting the DCD
20   line active, the command processor will look at the SCI
     port for a command data byte.  If the data it receives is
     invalid, it will ignore it and reenter the command proces-
     sor by setting the DCD line inactive and waiting for an
     active RTS.
25           If the command is valid, it will use it to index
     into a table of commands.  It will set the DCD line
     inactive and the keep alive active.  Processor control will
     then be transferred to the received command routine by
     jumping to the address specified in the command table.
30   ----------------------------------------------------------

Reset the stack pointer and set the keep alive inactive
             Set top of stack
             Get the last written port F data
35           Set (alive) not inactive
             Store the data
```

```
         Wait for the RTS line to go active
         Processor may fall asleep in this loop
                   Latch in the RTS line status
                   Is RTS high?
05                 Wait for RTS to be high before setting DCD active
         Look for command data - RTS must be active for valid
            command
                   Get status register
                   Get RTS data
10                 Check for RTS low
                   RTS still high?  Go check for buffer full
                   Set DCD inactive
                   Go back and wait for RTS high
                   Is receive buffer full?
15                 Bit set means data is present
                   Check over run/framing error bit
                   Framing error
                   No data no error - try again
         Data available is set - check for over run error
20                 Check over run/framing error bit
                   Over run error, got to error processor
         No error - get command data and process for validity
                   Get command data from port
                   RTS high with data present means command
25                 Is it the over the maximum command?
                   Set error 2
                   If undefined command, then look for data
                   And return to command processor through error
                      processor
30       Valid command - push onto command logging FIFO and continue
            processing
                   Multiply by 2 to give 2-byte jump address
         --------------------------------------------------------------
            Note:  Maximum number of commands possible is limited
35          to 128 by this process
         --------------------------------------------------------------
```

```
                    Get address of jump table
                    Add the command offset
                    Get the data ointed to by x-reg
                    Get the last written port F data
05                  Set (alive) not active
                    Store the data
            Now have address of command routine - go run it
                    Jump to new program
            ------------------------------------------------------
10          Error table - error register zero
            ------------------------------------------------------
                    bit 0 .... Tbd
                    bit 1 .... Check sum error in during mode switch
                    bit 2 .... Command was not valid
15                  bit 3 .... Desired mode is undefined
                    bit 4 .... Expected command - not data (RTS low)
                    bit 5 .... Expected data - got command (RTS high)
                    bit 6 .... Framing error serial comm port
                    bit 7 .... Overrun error serial comm port
20          ------------------------------------------------------
            Subroutine - RCVDAT
                    Picks up the second or more data after a command
            - there will always be at least one byte
            ------------------------------------------------------
25                  Get the RTS data
                    Get data to set DCD inactive
                    Get status register
                    Latch in a low on RTS
                    Is receive buffer full?
30                  Bit set means data is present
                    Check overrun/framing error bit
                    No error get data
                    Check port 1 data
                    Is RTS high?
35                  Low, then jump over next statement
```

```
                    Go set error number 5 through error processor
                    RTS low with data present means data
                    Get data from port
                    Return
05      ---------------------------------------------------------
        Here begins the start of the command program code
        ---------------------------------------------------------
        Command #0 --- dummy command
            Required following data is unused so can be any value
10      ---------------------------------------------------------
                    Get dummy byte
                    Return to command processor
        ---------------------------------------------------------
        Command #1 --- write system status
15          Data received will be:
                    0   5/S/s       4   undefined     8   5/d/s
                    1   7/S/s       5   undefined     9   undefined
                    2   5/S/1       6   undefined    10   5/d/1
                    3   7/S/1       7   undefined    all other undefined
20      ---------------------------------------------------------
                    Get mode data - second byte
        Entry point for reprogramming an existing mode
                    Save mode data - in variable
        If mode > 4, then set double; else reset (set is 2, reset
25      is zero)
                        Reset mode change bit in status register
                            Get status byte
                            Reset bit 5
                        Set RAM address to zero
30                      Set start_RAM to zero
                        Set RAM module to zero (port E)
                            Get the last written port E data
                            Set RAM module address to zero
                            And (enable)not inactive
35                          And d/a select inactive
                            Store the data
```

```
          Set the delay card to card 'A' data
                    Reset delay selet lines
                  End of initialization
          ----------------------------------------------------------
05        Beginning of code to move control data from each delay card
          to the control RAM
          ----------------------------------------------------------
          Begin data movement (main loop)
                  Form array index of start_stop_tbl(mode)
10                Add RAM pointer offset to RAM address
                      Save as RAM address
                  Add number of bytes from table
                      Save as end_cmp
                  Get starting PROM location from table
15                    Save as start_PROM
          ----------------------------------------------------------
                  Now doing a delay card
          Set delay card interface reset inactive
          (Start of time critical code)
20        ----------------------------------------------------------
          Pass by data till the first valid PROM site is reached
          ----------------------------------------------------------
                  Begin
                      Get port 1 exiting data
25                    Set interface reset inactive
                      Set the data
                    While PROM_adr < start_PROM address
                      Read delay data
                        P17 is data available
30                      If zero, then data avaiable
                        Get data
                      Increment PROM_adr
                      Repeat
                  End
35
```

```
----------------------------------------------------------------
                    Start filling a RAM module
----------------------------------------------------------------
          Begin (do loop runs at least once for each RAM module
05            And twice if the mode is "double")
            While number of bytes received less than bytes per
              RAM
              Get byte of delay data
                P17 is data available
10              If zero, then data available
                Get data
              Store at RAM location
              Add to check sum
              Get second byte of delay data
15              P17 is data available
                If zero, then data available
                Get data
              Store at RAM location +1
              Add to check sum
20            Increment RAM address pointer by 4
            Repeat
          Check for double and do this module again if true
          Reset address and counters for the new module
          Set RAM_address to 1024 plus start_RAM
25        Decrement double
          Get data from interface to insure not missing one
              P17 is data available
              If zero, then data available
              Get data
30          If double <> zero
              Set double to 2
        Increment RAM mod by 2
      Until RAM mod < 10

35
```

```
              ------------------------------------------------------------
                    Get check sum for this card
                    End time critical code
              ------------------------------------------------------------
05                  P17 is data available
                    If zero, then data available
                    Get data
                    P17 is data available
                    If zero, then data available
10                  Get data
                Set interface reset active
                    Get port 1 exiting data
                    Set interface reset active
                    Set the data
15        ------------------------------------------------------------
          Compare check sums and set an error bit in error register
          1, if no match.  There is an error bit for each card.
          ------------------------------------------------------------
                    Increment delay card selection data
20                  If delay card selection data < card E
                        If lsb of delay card selection data is set
                            Set start_RAM to 2
                        Else
                            Set start_RAM to zero
25                      Then
                        If msb of delay card selection data is set
                            Start at RAM mod 1
                        Else
                            Start at RAM mod zero
30                      Then
                    Then
              Until Card < E
              Done

35
```

Sum/weight

This section of code moves the sum/weight data from the 32k x 8 EPROM to the last five RAM modules. Using the
05 current mode and a table of start and length values, the data is directly accessed and moved.
EPROM address $0000 to $3fff --> $8000 to $bfff map address
EPROM address $4000 to $7fff --> $4000 to $7fff map address
--> means translates to
10 ------------------------------------------------------------
    Initialization
        Get last mode command
        Multiply by 2
        Multiply by 4
15        Get address of sum weight table start adr
        Get data to set EPROM bank (U69)
        Reset RAM module address
        Set RAM module address to 10th one
        Add the RAM address base number for compare
20           purposes
        Save the base number times 4 channels
        Get PROM starting address
        Offset of EPROMs
        Get the starting RAM location
25        Clear check sum
    Begin {main loop}
        Get PROM address
        If equal to half way switch map address
        Get PROM data
30        Increment PROM address
        Save next address
        Get RAM address
        Move the data
        Increment RAM address
35        Save the address
        Add the cksum

```
             If not at end of RAM module
                  Is it at the module change point?
                  No GoTo beginning of main loop
             Else
05                Get RAM select data
                  Set new RAM select
                  Is any RAM module between A and F selected?
                  Get start adr of RAM module
                  Save the address
10   Until RAM module > $0E
     Begin {check sum calculation}
                  Get PROM address
                  Get dat
                  Get cksum
15                Increment
             If check sum error
                  Are the calculated and read check sums equal?
                 Set error bit in error register 1
             Then
20   End
     Begin {set scan clock freq on board}
                  Get mode data
                  Mask for 7/5 data
                  Set the data
25   End
     ----------------------------------------------------------------
     This next section of code shifts and rotates the mode data
     into port 6 to set the analog chassis status lines for
     frequency and depth
30   ----------------------------------------------------------------
     Begin
          If mode is 7 mHz
                  Get mode data
                  Set freq to 7 mHz
35                Set the carry bit
     Else
```

Clear carry bit
Then
    Shift in carry into bit zero
    Set the carry bit
    Shift in a 1 in bit zero
    Shift data left
    Shift data left
    Save data for double
    Shift data left
    Shift data left
    Roll out to fine depth fd
Data now in top nyble to set port 6
    Set cd and input part of port to zero
    Set data
Set double in needed set scan enable active
    Mask of other data dual axis data
    Get port E data
    Mask off old data
    Set new data
    Set (enable)not active
    Set the auto RAM running
Set status register
    Get status reg
    Set bit 5 for mode change complete
    Return to command processor

```
         ---------------------------------------------------------------
         Command #2 ---
         Read system status register
         Required second data is not used
05       ---------------------------------------------------------------
                   Get the status register pointer
         Obtain data for status of relay position and cable
            connection
                   Get port g data
10                 Mask status lines
                   Get the error register
                   If zero branch
                   Set error bit
         Obtain mode status bit
15                 Get status register
                   Is the mode status bit set?
                   Set mode change complete
         Obtain RAM access status
                   Get the RAM control bit (enable)not
20                 If running, set the running flag in the status
                      register
                   Else reset access RAM bit
                   Save data
         Send data to serial port
25                 Get SCI status reg.
                   Is buffer empty?
                   Try again
                   Send data
                   Return to command processor
30
```

```
Command #3 ---
    Write lsb to address register
    Required second data is the address
        Get lsb data, second byte from main CPU
        Save the address
        Return to command processor Command #4 ---
    Write msb to address register
    Required second data is the address
        Get msb data, second byte from Main CPU
        Save the address
        Return to command processor Command #5 ---
    Write byte via address register
    All following bytes are treated as data to be written
via the address register unless RTS goes active, then pro-
gram control is transferred back to the command processor.
Obtain the beginning address from the address register
        Get the most significant address byte
        Mask off the block information
        Add the base address for all RAM (2048)
        Move to the x-reg the RAM address
Obtain the module number from the msb of the address
    register
The module number is in the most significant five bits of
    the address
        Get the high byte again
        Shift byte to right three times
        Save RAM module select
```

```
     Begin
             Set the RAM select port to the new created value
                     Get RAM select data from port E
                     Mask the RAM select bits
05                   Set the new RAM module select
                     Set the port
             Check RTS line for end of write data command
             Begin
                     If RTS is high, go process as command
10                       RTS high on data transmission, therefore go
                             return to command processor
                     Else
                     Get serial port status for next byte
                     Is there data?
15                   No, try again
             Until data available
                     Get next data
                     Store the data
                     Check if incremented into next block
20                   Increment RAM block select
                     Set RAM address to zero
     ------------------------------------------------------------
     Command #6 ---
         Read byte via address register
25       Second byte is the number of byte to read.  This number
     will cause the address to transverse RAM module boundaries.
     ------------------------------------------------------------
     Obtain the beginning address from the address register
                     Get the most significant address byte
30                   Mask off the block information
                     Add the base address for all RAM (2048)
                     Move to the x-reg the RAM address
         Obtain the module number from the msb of the address
             register
35   The module number is in the most significant five bits of
             the address
```

```
            Get the high byte again
            Shift byte to right three times
            Save RAM module select
      Obtain second byte from serial port, which is the length
         byte
            Get length byte
      Begin
            Set the RAM select port to the new created value
            Get RAM select data from port E
            Mask the RAM select bits
            Set the new RAM module select
            Set the port
         Get data to return via the RAM address pointer in
            x-reg
         Begin
            Is XMIT buffer empty?
            Not ready to XMIT, then jump
         Until ready to transmit
            Get data to send
            Send the data
            Decrement the length
            Is it over?
            Yes, then return to command processor
            Check if incremented into next block
            Increment RAM block select
            Set RAM address to zero
      Until forever
------------------------------------------------------------
Command #7 ---
   Read power supply status
      The second byte will be used as the channel number of the
   monitor to be read.
------------------------------------------------------------
```

```
                Get power supply channel number
                Get base address of adc
                Add offset or channel number
                Start the conversion
05          Begin
                Get busy signal data
                Is it busy?
                Busy, try again
            Until not busy
10              Wait approximately 3 microseconds
            Begin
                Get busy signal data
                Is it busy?
                Busy, try again
15          Until not busy
                Get data to send
            Begin
                Is XMIT buffer empty?
                Not ready to XMIT, then jump
20          Until ready to transmit
                Send the data
                Return to command processor
```
---
Command #8 --
25    Write tgc slope
   Note:  Data in b-reg is then command number (times 2).
This data is used to determine the correct address to write
the second byte to.
   adr 50=54=58=5c, adr 51=55=59=5b, adr 52=56=5a=5e
30 and adr 53=57=5b=5f
---
```
            Begin common code
                Divide b-reg by 2
                Get base address of tgc and Doppler DACs
35              Add channel number (in b-reg) to base address (in
                    x-reg)
```

```
            Get scaled data to write, second byte from CPU
            Store the new data (via x-reg)
            Return to command processor
    ----------------------------------------------------------
    Command #9 --
       Write tgc initial scope
       Uses code of command 8 above
    ----------------------------------------------------------
            Use common code of cmd08
                Jump to cmd08
    ----------------------------------------------------------
    Command #10 --
       Write Doppler slope
       Uses code of command 8 above
    ----------------------------------------------------------
            Use common code of cmd08
                Jump to cmd08
    ----------------------------------------------------------
    Command #11 --
       Write Doppler offset
       Uses code of command 8 above
    ----------------------------------------------------------
            Use common code of cmd08
                Jump to cmd08
    ----------------------------------------------------------
    Command #12 --
       Toggle scan enable bit
       Second byte is not used
    ----------------------------------------------------------
            Get second byte from CPU
            Get port E data for (enable)not
            Reset if set or set if reset (exclusive OR)
            Set the new data
            Return to command processor
```

```
       Command #13 --
           Write test values to DACs
           Second byte:
 05            0 will return the version date in a 3-byte Julian code
               1 will set, then control DACs to values found in
                 control RAM
               2 will require two more data - a channel number and a
                 datum to set the DAC channel
 10    ----------------------------------------------------------------
       Check for which version is desired:  0, 1, or 2
       ----------------------------------------------------------------
       Second byte equals 0:
           Return version number as a 3-byte Julian code (year,
 15    dayhi, daylow)
       ----------------------------------------------------------------
       Get version number data
               Get data
               Is message done?
 20    Send the data
           Toggle alive line
               Port f, which contains alive
               Toggle the alive line
               Set the data
 25        Send data
           Go look for another command
       ----------------------------------------------------------------
       Second byte equals 1:
           Sets all sum/weight channels to $ff except ch 19,
 30    which is set to $00.  Uses a table of RAM address pointers
       to find the data to set each delay/termination channel to
       ----------------------------------------------------------------
       Turn off scan addressing, select direct DAC addressing and
           RAM module 10
 35    Check for option to set individual DAC channels and jump if
           desired
```

```
            System test selected set direct DAC access bit in port e
            And sum/weight DACs
                    Get the port data
                    Set the data
05          Set all sum/weight DACs to $ff
                    Select the DAC
                    Store at output 0
                    Store at output 1
                    Store at output 2
10                  Store at output 3
            Toggle alive line
                    Port f, which contains alive
                    Toggle the alive line
                    Set the data
15          Last sum/weight channel cludge - turn it off $00 in 5mHz
            Get mode and combine with table address
            Select RAM module zero
            Loop point
            Set port for RAM access
20                  Reset d/a select
                    Select new RAM module
            Toggle alive line
                    Port f, which contains alive
                    Toggle the alive line
25                  Set the data
            Get table data - this is an offset into the RAM
            Get RAM data at pointed to RAM address
            Data is for the first two channels of this DAC
            Get next offset into RAM from table
30          Get RAM data at pointed to RAM address
            Data is for second two channels of this DAC
            Set port e for direct DAC write

35
```

```
        Write the four data to the four DAC outputs
                Store at output 0
                Store at output 1
                Store at output 2
                Store at output 3
        Go do next DAC
        Clear direct DAC access bit in port e
    ------------------------------------------------------------
    Second byte equals 2:
        Expects two more bytes of data.  The first is the DAC
    channel number (ch 0 - 59).  The second byte is the data to
    write to the selected DAC channel.
        This routine is entered and will continue to expect a
    channel number and data until the channel number sent is
    greater than 59.
    ------------------------------------------------------------
        Obtain DAC channel number and the data to set the DAC
            too
                Get channel number
                Save it
                Get datum
                Save ig
        Select which quad DAC using channel #
                Restore ch #
                Divide by 2 to obtain module #
                Is it over module 14?
                Yes, jump to end
                Set d/a select bit
                Set port with data
        Select which output of selected quad DAC using channel #
                Restore ch #
                Mask for output #
        Add base address of DACs
                Add base address
```

```
          Set DAC output to previous received data
               Restore data
               Store data at d/a channel
          Go look for another channel and data to modify
               Loop to do another channel
---------------------------------------------------------------
Second byte equals 3:
     The next two bytes will first give the test number 0
or 1; the second will indicate to turn the test on (1) or
off (0).
---------------------------------------------------------------
               Check if valid command
               Go get test number
               Shift value up to correct bit pos.
               Safety instruction
               Go get on/off data
               Shift value up to correct bit pos.
               Safety instruction
               Get port data
               Mask data
               Set new test number
               Store data
---------------------------------------------------------------
Command #14 --
   Returns current mode
   Second byte is not used
---------------------------------------------------------------
               Get the mode
               Send it
---------------------------------------------------------------
Command #15 --
   Returns 32 bytes of last command
   Second byte is not used
---------------------------------------------------------------
               Get the pointer
               Pop first byte
```

```
                Send it
                Is pointer at start of buffer?
                Yes, get the end of buffer
                Is complete buffer output?
05              No, do next byte
                ----------------------------------------------
                        Subroutine to save last 32 command values
                ----------------------------------------------
                        Get the FIFO pointer
10                      Store data via pointer
                        Increment pointer
                        Compare to end of buffer
                        Jump if not at end
                        Set pointer to start of buffer
15                      Save pointer
                        Return from subroutine
   ----------------------------------------------------------
   Command #16 --
        Read error status registers
20      Second byte:
                0 returns error register zero
                1 returns error register one
   ----------------------------------------------------------
                Get the register number, second byte from CPU
25              Transfer to the b-reg
                If greater than the max error reg
                        Get the max number
                Get the address of the error reg
                Get data to send
30      Begin
                Is XMIT buffer empty?
                Not ready to XMIT, then jump
        Until XMIT buffer empty
                Store the data
35
```

Amplitude Weighting, Sum and TGC

The amplitude weighting, sum, and time-gain control subsystem 68 receives twenty parallel RF signals from the four delay line boards and converts them into a single output signal after they have been weighted, as explained in greater detail below. The system also generates an output that is the log of the summed and weighted signals, and it provides a time-gain control signal to the crossbars.

A block diagram of the amplitude weighting, sum, and time-gain control subsystem 68 is illustrated in FIG. 10A. The twenty RF signals from the delay line channels, D01–D20, are applied to similar weighting channels 2000. The attenuation of each weighting channel is controlled during the period that returns are reflected from the tissue and blood flow by weighting control signals SC01–20 from the delay control subsystem 60. At the beginning of the period, all of the channels except channel 1 have a high attenuation so that the beam is effectively relatively narrow for returns from shallow depths. As returns are received from deeper sample sites, the attenuation of the higher numbered channels is reduced in a controlled fashion. This weighting function not only provides a dynamic aperture for the transducer, but it also reduces the array side lobe levels in order to provide better quality images.

The outputs of the weighting channels 2000 are applied to a signal summer 2002, which combines the twenty channels into a single RF signal. The composite RF signal is applied in parallel to a tissue time-gain controlled amplifier 2004 and a flow time-gain controlled amplifier 2006. The flow time-gain controlled amplifier 2006 has a gain ranging between 0 and +50 db. The tissue time-gain controlled amplifier 2004 has a gain ranging between −7 to +33 db. The gains are varied during the period of time that ultrasound returns are being received to compensate for the greater attenuation of signals in the body at deeper levels. The output of the flow time-gain controlled amplifier is supplied to the clutter cancellet subsystem 74 for further processing. The output of the tissue time-gain controlled amplifier 2004 is supplied to tissue RF filters 1508. Two tissue RF filters 2008 are available, one for use at 5 mHz and the other for use at 7.5 mHz. The correct filter is switched by the Q7.5/5* from the delay controller 66. Each filter consists of a 3-pole low-pass and a 3-pole high-pass filter to limit the band that is required for high quality imaging.

The output of the tissue RF filters 2008 is applied to a logarithmic amplifier 72 (FIG. 2), which amplifies, compresses, and detects the RF to provide a log video signal to the A-to-D subsystem 76 (FIG. 2). The compression in the logarithmic amplifier 72 is adjusted so that the system tissue display has a dynamic range of 40 db.

The control signals for the amplitude weighting, sum, and time-gain control subsystem 68 are provided by a time-gain control generator circuit 1510. The time-gain control generator 2010 also generates the time-gain control signal for the crossbar circuitry explained above. Incorporated into the time-gain control generator 2010 is compensation for transducer array gain as a function of depth and loss across the transmission wedge used with the transducer array. TXS and SKIN timing signals from the A-to-D subsystem 76 provide timing information at the start of the period that returns are received in the location of a skin line when the transmission wedge is used. Control voltages TIN, TSL, FG, and FSL from the delay controller 66 control the initial tissue gain, tissue slope, initial flow gain, and relationship between tissue slope and flow gain slope.

A schematic of the weighting channel circuit 2000 and the signal summer 1502 is illustrated in FIG. 10B. As mentioned above, there are twenty weighting channels 2000, each of which receives an input from a respective delay line. The weighting circuits 2000 for all channels are substantially identical, except for some minor differences noted below.

The RF signal from the delay line is applied to a variable attenuator 2002 consisting of transformer 2004, PIN diodes 2006, 2008, capacitor 2010, and resistors 2012, 2014. The transformer 2004 converts the unbalanced input signal to a balance signal at the anodes of the diodes 2006, 2008 and also raises the impedance level from 75 ohms to 300 ohm. The RF resistance of diodes 2006, 2008 is controlled by the current flowing through the diodes 2006, 2008 from respective resistors 2012, 2014. When the current supplied through the resistors 2006, 2008 is low, the resistance of the diodes 2006, 2008 is high and, consequently, so is their attenuation. When the current through the diodes 2006, 2008 is high, the resistance of the diodes 2006, 2008 is low and so is their attenuation. Resistors 2012, 2014 cause the current flow through the diodes 2006, 2008 to be substantially equal, even where there are slight differences in the characteristics of the diodes 2006, 2008.

The RF signal applied to the diodes 2006, 2008 drive a second transformer 2016, which converts the 300 ohm balance signal back into a 75 ohm unbalance signal. A balance configuration is used for the attenuator 2002 to reduce even order distortion and to reduce the injection of the attenuator control signal into the signal path. The secondary of transformer 2016 is applied to a fixed attenuator formed by resistors 2018, 2020. The values of resistors 2018, 2020 are different for different weighting channels so that the fixed attenuation for higher numbered channels is greater than for lower number channels. As a result, the attenuation of the higher numbered channels, which process the signals from the ends of the transducer array, reduce the range required by the variable attenuator, and increase the isolation between channels.

The attenuation control current for the diodes 2006, 2008 is supplied by operational amplifier 2030 through resistor 2032. Capacitor 2034 provides noise filtering of the control signal. The output of the operational amplifier 2030 is derived from an attenuation control signal SC, one of which is generated for each weighting channel. The control voltages SC0–SC20 are generated by the delay controller 66 (FIG. 2). The control SC is applied to an operational amplifier 2040 through summing resistor 2042. A 1 volt offset of the amplifier 2040 is provided by a −10 volt signal applied through summing resistor 2044. The gain of the amplifier 2040 is set at unity by feedback resistor 2046. Additionally, a feedback capacitor 2048 forms the final pole of a filter having four poles contained on the delay controller 66. The control input to the operational amplifier 2040 is referenced to REFGND through voltage divider resistors 2050, 2052 to reduce the effects of differences in ground potential from one board to the next.

The output of the operational amplifier 2040 is applied to the second operational amplifier 2030 through resistor 2060 and potentiometer 2062. The potentiometer 2062 allows the gain of the weighting circuit 2000 to be adjusted for a given control signal SC voltage. An offset voltage generated by potentiometer 2064 is also provided through summing resistor 2066 to allow control of both the slope and offset of the attenuation as a function of the control signal. A variable capacitor 2068 and resistor 2070 provide a path for the control signal that is in parallel with resistor 2060 and potentiometer 2062 to compensate for the relatively slow response times of the PIN diodes 2006, 2008. Capacitor 2068 is adjusted to equalize the response times of all of the weighting channels 2000.

A temperature-compensating signal is also applied to the amplifier 2030 through summing resistor 2070. The temperature-compensating signal is generated across PIN diode 2072, through which a fixed current flows, as determined by resistor 2074. The pin diode 2072 compensates for temperature-induced variations in the impedance of diodes 2006, 2008.

The operational amplifier 2030 also receives a "TURN-OFF" signal through summing resistor 2078. The TURN-OFF signal is generated from a TXS* signal applied to solid-state switch 2080, which connects the +10 volt supply to resistor 2078 through resistor 2082. Capacitor 2084 is provided for response shaping. The TXS* signal is generated just prior to the triggering of the transmitters. The large positive pulse applied to resistor 578 during transmit effectively turns off the attenuator 2002 so that the attenuation is reset to zero at the start of the period during which returns are processed by the weighting, sum, and time-gain controls subsystem. Capacitor 2084 slows the recovery time when solid-state switch 2080 opens to compensate for the charge storage effects of the PIN diodes 2006, 2008. The gain of amplifier 2030 is set by resistor 532 in combination with resistor 2088. Capacitor 2090 is provided to stabilize the operational amplifier 2030.

As mentioned above, the voltage at the output operational amplifier 2030 is proportional to the current through the PIN diodes 2060, 2008. This voltage is applied through voltage divider resistors 2092, 2094 to an operational amplifier 2096 configured as a voltage follower. The output of the operational amplifier 2096 is applied directly to the summing junction of operational amplifier 2030 through diode 2098. When the current through the PIN diodes 2006, 2008 reaches a value causing the output of operational amplifier 2096 to be greater than about 0.5 volt, current flows from the output of operational amplifier 2096 to the summing junction of operational amplifier 2030 through diode 2098, thereby effectively clamping the positive voltage at the output of amplifier 2030 to about 3.4 volt. In this manner, the current through the diodes 2006, 2008 is limited to about 4.5 mA.

The signal summer 2002 is provided by four conventional power combiners using internal transformers 2100–2108. The five power combiners 2100–2108 reduce the twenty RF inputs to five combined RF signals, which are, in turn, reduced to a single SUMRF signal by another power combiner 2110.

The tissue TGC amplifier 2004, tissue RF filters 2008, and flow time-gain control amplifiers 2006 are illustrated in FIG. 10C. The sum RF signal is applied through blocking capacitor 2120 across terminating resistor 2122 to the tissue gain control amplifier 2004 and the flow time-gain control amplifier 2006. The tissue gain control amplifier 2004 is identical to the flow time-gain control amplifier 2006 except that the internal components of the two amplifiers are slightly different to provide the tissue gain control amplifier with a gain ranging between −7 and +33 db and the flow time-gain control amplifier with a gain varying between 0 and 50 db. The RF signal is applied through a coupling capacitor 2124 to the gate of a field-effect transistor 2126, which has low-noise, high-transconductance characteristics. The gain of FET 2126 is controlled by the value of source resistor 2128 and resistor 2130. FET 2126 is biased through resistors 2132, 2134, 2138, as explained in greater detail below.

The signal from FET 2126 is applied to the emitter of transistor 2140 biased by resistors 2142, 2144, 2148. Bypass capacitor 2150 grounds the base of transistor 2140 at the RF frequency. The collector of transistor 2140 is loaded with a low-Q, parallel tank circuit consisting of inductor 2152 and the interstage shunt capacitance which resonates at about 6 mHz. Diodes 2154, 2156 clamp the voltage swing of the collector to + and −0.7 volt to avoid overdriving subsequent stages.

The gain of the amplifier implemented by transistor 2140 is proportional to the impedance of a pair of PIN diodes 2160, 2162, which are connected to the collector of transistor 2140 through coupling capacitor 2164. The diodes 2160, 2162 are, in turn, connected to ground through bypass capacitor 2166, 2168. The current through the PIN diode 2160, 2162 is supplied through resistor 2170, 2172, as explained in greater detail below.

The bias for the FET 2126 is, as mentioned above, provided through resistor 2132. The DC bias current flowing through transistor 2140 and FET 2126 flows in sequence through resistor 2142 and inductor 2152. The voltage across resistor 2142 is sensed by transistor 2180 through voltage divider resistors 2182, 2184. When the current through transistor 2140 and FET 2126 increases, the voltage on the emitter of transistor 2180 decreases, thereby reducing the voltage on the gate of FET 2126 in order to reduce the flow of current through transistor 2140 and FET 2126. Conversely, if the flow of current through resistor 2142 is reduced, the voltage on the emitter of transistor 2180 increases, thereby causing an increase in the voltage applied to the gate of FET 2126. Bypass capacitor 2198 places the emitter of transistor 2180 at AC ground in order to prevent RF feedback to the FET 2126 and provide a path to ground from the collector of transistor 2140 for the diode 2154, 2156 and the inductor 2152.

The variable gain signal on the collector of transistor 2140 is applied to a transistor 2200 through resistor 2202. Transistor 2200 is connected essentially as an emitter follower since the value of resistor 2204 is substantially lower than the value of resistor 2206. Transistor 2200 drives the base of transistor 2210 through resistor 2212. Transistor 2210 is connected as an amplifier, the gain of which is determined by the collector load resistance and resistor 2214. Resistor 2216 is provided for biasing purposes, but it is effectively shunted at RF by capacitor 2218. Inductor 2220 is provided for the same purpose as inductor 2152 in the previous amplification stage, namely, to form a tank circuit with the interstage shunt capacitance for bandpass filtering. Similarly, diodes 2222, 2224 are, like diodes 2154, 2156, provided to avoid overdriving subsequent stages.

The gain of transistor 2210 is controlled by the resistance of PIN diodes 2230, 2232. Like the previous amplification stage, the diodes 2230, 2232 are connected to the collector of transistor 2210 through coupling capacitor 2234, and they are each connected to ground at RF by bypass capacitor 2236, 2238. The current through the diodes 2238, 2232 is supplied through respective resistors 2240, 2242.

The variable gain output from the transistor 2210 is applied to the base of transistor 2250 through resistor 2252. Transistor 2250 is connected essentially as an emitter follower since the value of resistor 2254 is substantially lower than the value of resistor 2256. Emitter follower transistor 2250 thus provides a relatively high input impedance to avoid loading transistor 2210, and it provides a relatively low output impedance. Capacitors 2258, 2260, along with resistors 2262, 2264, provide good power supply filtering and isolation of the amplifier stages from each other.

The control voltages for the attenuation diodes 2160, 2162, 2230, 2232 are derived from a TISSUE TGC that is applied to operational amplifier 2270 through the parallel combination of resistor 2272 in series with capacitor 2274 and resistor 2276 in series with potentiometer 2278. Potentiometer 2278 is adjusted to adjust the gain of the amplifier 2270.

The output of the operational amplifier 2270 is applied to the cathode of PIN diode 2160 through resistor 2170, as explained above. Feedback is provided through resistor 2280 so that the voltage across diode 2160 is proportional to the magnitude of the TISSUE TGC signal. Since diode current is an exponential function of diode voltage, this provides a log linear gain control function. Capacitor 2282 provides low-pass filtering for the operational amplifier 2270.

The output of operational amplifier 2270 is also applied to the input of operational amplifier 2384, having equal summing and feedback resistors 2386, 2388, respectively. Since the output of amplifier 2384 is equal and opposite to the output of amplifier 2270, amplifier 2384 applies the same current through PIN diode 2162 that amplifier 2270 applies through PIN diode 2160 in order to ensure a balanced operation. Pin diodes 2230 and 2232 are driven in the same fashion.

Operational amplifier 2270 also receives an offset voltage generated by potentiometer 2390 and applied through resistors 2392, 2394 to the input of operational amplifier 2270. Capacitor 2394 is provided to filter the offset voltage. By adjusting potentiometer 2390 and potentiometer 2278, both the slope and intercept of the impedance as a function of TISSUE TGC voltage can be adjusted. In this manner, the characteristics of the TISSUE TGC 1504 can be made different from the characteristics of the flow TGC circuit 1506.

Operational amplifier 2270 also receives a temperature compensation signal through summing resistor 2396. The temperature compensation signal is generated across PIN diode 2399, which is supplied with current through resistors 2400, 2402. Capacitor 2404 is provided for low-pass filtering. The temperature-induced voltage/current characteristics of PIN diode 2399 match those of PIN diode 2160, 2162, 2230, and 2232 in order to make the PIN diode 2160, 2162, 2230, 2232 insensitive to temperature variations.

The output of the flow TGC amplifier 1506 is applied to the base of transistor 2410 through resistor 2412. Transistor 2410 is essentially connected as an emitter follower, since the value of resistance 2412 is substantially less than the value of resistor 2414. Resistor 2412 acts as a parasitic suppressor to prevent oscillation of the transistor 2410 at high frequencies. Resistor 2414 provides the transistor 2410 with a sufficiently large input impedance to avoid loading the output stages of the flow TGC amplifier 1506. The signal on the emitter of transistor 2410 is applied through capacitor 2416 to the primary of a balun transformer 2418, which generates on its secondary the inverse of the FLOWSIG signal. Resistors 2420, 2422 reference the differential signals to ground.

The tissue RF filters 1508 are composed of two sections, one for 7.5 mHZ and one for 5 mHz. The RF signal at the output of the tissue TGC amplifier 1504 is output through two blocking capacitors 2430, 2432 to the bases of transistors 2434, 2436 through respective resistors 2438, 2440. The bases of the transistors 2438, 2440 are biased through voltage divider resistors 2442, 2444. The transistors 2434, 2436 are arranged in emitter follower configuration, with the input impedance being set primarily by the resistors 2446, 2448, respectively. Power is supplied to the transistors 2434, 2436 through resistor 2450, with capacitor 2452 providing low-pass filtering.

The 7.5 mHz filter 2452 is identical in topology to the 5 mHz filter 2454. Of course, the values used in the two filters 2452, 2454 are different because of their differing bandpass frequencies. However, because of the identical topology of the two filters 2452, 2454, corresponding components have been given the same reference numeral.

The output of the emitter follower transistor 2434 is applied to a 3-pole high-pass filter through capacitor 2454 and resistor 2456, which sets the source impedance to the filter. The 3-pole high-pass filter is formed by capacitor 2458 and inductors 2460, 2462. The 3-pole high-pass filter drives a 3-pole low-pass filter formed by inductor 2464 and capacitors 2466, 2468. Together, the high-pass and low-pass filters form a bandpass filter centered at the appropriate 7.5 mHz or 5 mHz frequency.

The outputs of the 3-pole low-pass filters for either the 7.5 mHz or the 5 mHz filter is selected from the Q7.5/5* and Q7.5*/5 frequency select input signals. These signals are applied to respective inputs of a comparator 2470, which are biased through resistors 2472, 2474, 2476. When the Q7.5/5* input is high and the Q7.5*/5 input is low, the output of comparator 2470 is high, thereby applying current through resistor 2478 along two paths. The first path is composed of resistor 2480, diode 2482, inductor 2464, and inductor 2462. The low impedance of the forward-biased diode 2482 provides a low-impedance shunting path to ground through capacitor 2484. At the same time, the high at the output of comparator 2470 is applied through resistor 2486 and RF choke 2488 to back-bias diode 2490, thereby opening the path from the 5 mHz filter to the output through capacitor 2492. Thus, the 5 mHz filter is shunted to ground, and its path to the tissue RF output is open-circuited.

The second path for current flowing through resistor 2478 is through resistor 2494, RF choke 2496, diode 2498, inductor 2464, and inductor 2462. The current flowing through diode 2492 reduces its impedance, thereby allowing the output of the 7.5 mHz filter to be applied to the TISSUE RF output through capacitor 2000. At the same time, the high at the output of comparator 2470 is applied through resistor 2002 to diode 2004, thereby back-biasing diode 2004 and opening the shunt path to ground through capacitor 2006. Thus, when the Q7.5/5* input to comparator 2470 is high and the Q7.5*/5 input is low, the output of the 7.5 mHz filter is applied to the TISSUE RF output.

When the Q7.5/5* input is low and the Q 7.5*/5 input is high, the output of comparator 2470 is negative. The negative voltage at the output of comparator 2470 causes current to flow through resistor 2486, RF choke 2488, diode 2490, inductor 2464, and inductor 2462, thereby connecting the output of the 5 mHz filter to the TISSUE RF output. At the same time, the low back-biases diode 2482 to open the shunt path to ground through capacitor 2484. The negative voltage at the output of comparator 2470 also causes current to flow through resistor 2002, diode 2004, inductor 2464, and inductor 2462 to forward-bias diode 2004, thereby shunting the output of the 7.5 mHz filter to ground through capacitor 2506. The negative voltage at the output of comparator 2470 also back-biases diode 2498, thereby open circuiting the connection between the 7.5 mHz filter and the TISSUE RF output. Thus, when the Q7.5/5* is low and the Q7.5*/5 input is high, the output of the 7.5 mHz filter is applied to the TISSUE RF output.

A schematic of the TGC generator 1510 is illustrated in FIG. 23. The TGC generator produces the control signals for the tissue TGC amplifier 1504, the flow TGC amplifier 1506, and the crossbar subsystem 58 (FIG. 1). The tissue gain control signal originates from TSL and TIN inputs from the delay controller 66 (FIG. 1). The TSL signal specifies the gain slope, i.e., how fast the tissue and crossbar gains decrease with time. The TIN signal sets the initial tissue and crossbar gains. The TSL signal and RET signals are applied to an operational amplifier 2520 through respective resistors 2522, 2524. The gain of the amplifier 2520 is set at unity by feedback resistor 2526 and voltage divider resistor 2528. Amplifier 2520 outputs a voltage indicative of the slope of the gain control signals.

The output of the operational amplifier 2520 is applied to a ramp boost pulse generator 2530 and a ramp generator 2532. The ramp boost pulse generator includes an operational amplifier 2536 having equal summing junction and feedback resistors 2538, 2540 to provide a gain of −1. The output of the operational amplifier 2536, which is at −TSL, is applied through resistor 2542 to capacitor 2544, which is thus charged to the negative of the TSL voltage. The voltage across capacitor 2544 is applied to a solid-state switch 2548, which is opened by the SKIN pulse. The solid-state switch 2548 thus outputs a boost pulse dropping from zero to the negative of the TSL voltage at the trailing edge of the SKIN pulse. The boost pulse is applied to the summing junction of amplifier 2550 through summing resistor 2552.

The output of ramp generator 2532 is also summed by operational amplifier 2550 through a summing resistor 2554. The inverse of the TSL voltage at the output of operational amplifier 2520 is applied to the inverting input of an operational amplifier 2556 through resistors 2558, 2560. Capacitor 2562 provides low-pass filtering to attenuate noise. Operational amplifier 2556 is configured as an integrator with a capacitor 2564 in its feedback path. A solid-state switch 2568 is connected in parallel with capacitor 2564 and is closed by the SKIN* pulse. During the SKIN pulse, the switch 2568 is closed, thereby short-circuiting the capacitor 2564 and causing operational amplifier 2556 to output zero volts. At the end of the SKIN pulse, the SKIN* input to switch 2568 goes high, thereby opening switch 2568 and allowing capacitor 2565 to charge negatively. Operational amplifier 2556 thus outputs a negative-going ramp which is summed with the boost pulse from switch 2548 through summing resistor 2554.

Operational amplifier 2550 also adds the initial TGC gain to the output of the ramp generator 2532 and the output of the boost pulse generator 2530. The initial tissue gain TIN signal and the RET signal are applied to the inputs of operational amplifier 2570 through respective resistors 2572, 2574. The gain of operational amplifier 2570 is set at unity, since feedback resistor 2576 and voltage divider resistor 2578 are equal to each other and to the resistors 2574, 2572. The TIN signal at the output of operational amplifier 2572 charges capacitor 2580 through resistor 2582, and the voltage across capacitor 2580 is applied through summing resistor 2584 to the summing junction of operational amplifier 2550.

The final input summed by the operational amplifier 2550 is a wedge compensation circuit that compensates for the attenuation through the coupling wedge that is attached to the transducer. A longer path through the coupling wedge corresponds to a longer SKIN pulse since there is a longer delay from the transmission of the pulse to the time that the pulse reaches the skin when the path through the wedge is longer. The wedge compensation signal is composed of two components. The first component is generated by applying +10 volts to a solid-state switch 2600, which is closed during the SKIN* low. Thus, 2600 is closed during the SKIN pulse. The +10 volts from the switch 2600 during the SKIN pulse is applied through resistor 2602 to an operational amplifier 2604 operating as an integrator by virtue of capacitor 2606 in its feedback loop. Capacitor 2606 is shunted by solid-state switch 2608 that is closed by the TXS* low. Thus, switch 2608 is closed during the TXS pulse, which is high for six microseconds prior to ultrasound signal being output by the transducer. Since the SKIN pulse is of a longer duration than the TXS pulse, the output of the amplifier 2604 remains at zero volts until the end of the TXS pulse. Thereafter, since switch 2600 remains closed by virtue of the longer duration of the SKIN pulse, operational amplifier 2604 integrates negatively. At the end of the SKIN pulse, switch 2600 opens, thereby preventing further integration and holding the output of operational amplifier 2604 constant. The output of operational amplifier 2604 is summed through resistor 2610, with the output of the other branch of the wedge compensation circuit. The other branch of the wedge compensation circuit is formed by a solid-state switch 2612 that receives −10 volts and is open during the TXS pulse. The switch 2602 is placed in series with a second solid-state switch 2614, which is closed when the SKIN* input is low. Thus, switch 2614 is closed during the SKIN pulse, and −10 volts is applied across resistor 2616 at the end of the TXS pulse for the remaining duration of the SKIN pulse. The signal generated across resistor 2616 is summed with the output from operational amplifier 2604 through resistor 2618. The wedge compensation signal is thus a signal that starts with an amplitude equal to the negative voltage to which the operational amplifier 2604 integrated during the previous wedge compensation pulse. At the start of the TXS and SKIN pulses, the output of operational amplifier 2604 is reset to zero, and, since switch 2612 remains open by virtue of the TXS pulse, the wedge compensation pulse is at zero volts until the end of the TXS pulse. At that point, switch 2612 closes, thereby generating a negative-pedestal. At the same time, operational amplifier 2604 begins incrementing negatively until the end of the SKIN pulse. At the end of the SKIN pulse, the pedestal is immediately removed by the opening of switch 2614, thereby leaving the wedge compensation pulse at a level corresponding to the output of the operational amplifier 2604 at the end of the integration period. The wedge compensation signal is applied through potentiometer 2620 and resistor 2622 to the summing junction of operational amplifier 2550. The duration of the SKIN pulse is equal to twice the transit time of the ultrasound signal through the coupling wedge. Thus, at the end of the SKIN pulse, tissue returns are being received at the transducer. The amplitude of the wedge compensation signal during the period that returns are received from tissue is thus inversely proportional to the length of the SKIN, which is, in turn, proportional to the thickness of the coupling wedge through which a given ultrasound beam must pass. In other words, a thicker path through the coupling wedge results in a more negative wedge compensation signal. The pedestal provided by the switches 2612, 2614 add a small step to the wedge compensation signal to compensate for the response of the PIN diodes in the time-gain control amplifiers.

The TXSECL signal and TXS*ECL signal are applied to the TCG generator 1510 differentially. A terminating resistor 2623 is connected between the TXS and TXS* inputs. The TXS and TXS* inputs are applied differentially to two translators 2624 and 2625 to generate buffered TTL level TXS and TXS* signals. Similarly, the SKIN and SKIN* signals are applied across terminating resistor 2626 to a pair of translators 2627, 2628 to generate TTL level SKIN and SKIN* signals used by the above-described circuitry.

As explained above, the operational amplifier 2550 sums the boost pulse from switch 2548, the tissue ramp signal from operational amplifier 2556, the initial gain signal from operational amplifier 2570, and the wedge compensation signal. A diode 2630 in the feedback path of operational amplifier 2550 clamps the output of the operational amplifier 2550 at 0.7 volt. Diode 2632, connected between the output of operational amplifier 2550 and feedback resistor 2634, places the voltage across resistor 2636 at zero volts when the output of amplifier 2550 is clamped at 0.7 volt by diode 2630. Thereafter, an increasing positive input to amplifier 2550 causes the anode of diode 2632 to increase negatively a corresponding amount. The voltage across resistor 2636 is thus a signal that starts at zero volts, but drops to a negative voltage at the start of the TXS and SKIN pulses. At the end of the SKIN pulse, the signal jumps positively and then starts incrementing positively until the signal reaches zero volts. The voltage across resistor 2636 is applied to amplifier 2640, having a gain of two, as set by the ratio of feedback resistor 2642 and summing resistor 2644. +10 volts applied through resistor 2646 causes an 8 volt negative offset. Diode 2648 and diode 2650, along with resistor 2652, limit the output of the amplifier 2640 to positive voltages. As a result, as the input rises from −6.5 volts to −4 volts, the output of operational amplifier 2640 falls from +5 volts to zero volts and remains at zero volts.

The output of operational amplifier 2640 is applied to operational amplifier 2660 through summing resistor 2662. An offset voltage is applied to the operational amplifier 2660 through resistor 2664. The gain of the operational amplifier 2660 is set at unity by feedback resistor 2666. The output of the operational amplifier 2660 is applied to the crossbar subsystem through resistor 2668. In order to provide a differential TGC signal to the crossbars, the output of operational amplifier 2660 is applied to an operational amplifier 2670 having a unitary gain as set by equal feedback and summing resistors 2672, 2674, respectively. Operational amplifier 2670 outputs the TGC signal through resistor 2676.

An operational amplifier 2680 receives two opposing inputs. The first input is the voltage across resistor 2636, which is applied to the operational amplifier 2680 through resistor 2682. The second input applied to the operational amplifier 2680 is the voltage across resistor 2652, which is applied through resistor 2684. The gain of amplifier 2680 for the voltage across resistor 2636 is set by the ratio of resistor 2686 to resistor 2682 at unity. The gain of the operational amplifier 2680 for the voltage across resistor 2652 is set at 0.5 by the ratio of feedback resistor 2686 to summing resistor 2684. During the SKIN pulse, if TIN is set for minimum gain, the voltage across resistor 2636 is at −6.5 volts and the voltage across resistor 2652 is at +5 volts. Because of the differing gains of these two signals, the output of operational amplifier 2680 is thus held at +4 volts. As the voltage across resistor 2636 rises from −6.5 volts, the voltage across resistor 2652 decreases correspondingly from +5 volts. However, until the voltage across resistor 2636 reaches −4 volts, the two signals applied to the operational amplifier 2680 cancel each other and the output remains at −4 volts. When the voltage across resistor 2636 rises above −4 volts, the voltage across resistor 2652 remains at zero volts. Thereafter, the output of operational amplifier 2680 starts to fall, reaching zero volts when the voltage across resistor 2636 reaches zero volts. Thus, the output of operational amplifier 2680 is constant while the crossbar gain is rising and, thereafter, decreases to zero volts from a negative voltage. The output of the operational amplifier 2680 is summed by an operational amplifier 2700 through summing resistor 2702. The gain of amplifier 2700 is set by feedback resistor 2704. The output of the amplifier 2700 is clamped at 0.7 volt by diode 2706, and diode 2708 clamps the negative voltage across resistor 2710 at zero volts. Resistor 2710 applies zero volts to operational amplifier 2712 when diode 2708 is back-biased. Amplifier 2712 has a unity gain set by the ratio of resistor 2714 to resistor 2716, with a −4 volt offset provided through resistor 2718.

The operational amplifier 2700 sums with the output from operational amplifier 2690 an array compensation signal. The array gain compensation is incorporated into both the tissue and flow time-gain control signals. The weighting function previously described causes the array gain to be relatively low for returns from relatively shallow sample sites and then increases as more transducer elements are added to the beam for deeper sample sites. The signal gain change is about 22 db at maximum depth, while the noise gain change is about 11 db. The tissue gain is compensated for 22 db to produce uniform axial gray scale, while the flow gain is compensated for 11 db to provide a uniform axial noise threshold. The array gain is such that an exponential waveform provides adequate gain compensation.

The time constant of the array gain is a function of the RF frequency. The 7.5*/5 and 7.5/5* signals indicative of the RF frequency are applied to a comparator 2750 through respective resistors 2752, 2754. The inputs to comparator 2750 are biased high through respective resistors 2756, 2758. The output of comparator 2750, which is biased high through resistor 2760, is an ARRAYT signal that is high when the operating RF frequency is 5 mHz.

The exponential array compensation signal is generated by a resistor capacitor circuit consisting of resistor 2760 and capacitor 2762. For 7.5 mHz operation, the low ARRAYT input to semiconductor switch 2764 places resistor 2766 in parallel with resistor 2760 to reduce the time constant of the RC circuit. During the TXS pulse, capacitor 2768 is discharged through resistor 2774 and diode 2782. Additionally, semiconductor switch 2776 is open. At the end of the TXS pulse, semiconductor switch 2772 opens and semiconductor switch 2776 closes, thereby allowing capacitor 2768 to apply a 10 volt step to substantially smaller capacitor 2762. Capacitor 2762 then charges exponentially through resistor 2760, and, in the 7.5 mHz mode, through resistor 2766. Operational amplifier 2780 is configured as a voltage follower to buffer the waveform generated across the resistor 2760. The output of operational amplifier 2780 is thus a decaying voltage starting at 10 volts at the end of the TXS pulse.

The output of voltage follower amplifier 2780 is applied to an operational amplifier 2790 operating as a buffer, with unity gain provided by equal feedback and summing resistors 2792, 2794, respectively. Capacitor 2796 is provided to delay the onset of compensation to suppress large echoes close to the transmit time. The output of the buffer amplifier 2792 is applied through summing resistor 2798 and potentiometer 2800, which, together, act as summing resistors. Potentiometer 2800 is adjusted to optimize tissue array compensation.

The flow TGC control signal is made up of three parts. The FG input from the delay controller 66 controls the maximum value of the flow gain, which is reached at the end of the time-gain controlled ramp in order to allow the operator to adjust the amount of flow noise speckle on the display. When the FG input is zero volts, the maximum flow gain is 50 db. When FG is +4.9 volts, the maximum flow gain is 0 db. The FSL input from the delay controller 66 determines how much of the tissue TGC ramp is used. When FSL is zero volts, all of the tissue ramp is used. When FSL is +3.9 to 2 volts, none of the tissue ramp is used and flow gain is affected only by FG and the array compensation signal. The FG input is applied to an operational amplifier 2820 through voltage divider resistors 2827, 2824. The inverted input of operational amplifier 2820 is tied to the return RET through resistor 2826. Feedback resistor 2828 sets the gain of the amplifier 2820 at unity so that it functions as a buffer. The output of amplifier 2820 is applied through a resistor 2830 to a capacitor 2832, which provides low-pass filtering and is used to apply the FG signal to the summing junction of an operational amplifier 2834 through summing resistor 2836. Operational amplifier 2834 also receives through summing resistor 2838 and potentiometer 2840 the array compensation signal from operational amplifier 2790. The gain of operational amplifier 2834 is set by the feedback resistor 2842. The output of operational amplifier 2834 is summed through summing resistor 2844 by an operational amplifier 2846, with the flow ramp derived from the FSL input. The FSL input is applied to operational amplifier 2850 through voltage divider resistors 2852, 2854. Amplifier 2850, like amplifier 2820, has its inverting input connected through resistor 2856 to the return RET input. The gain of operational amplifier 2850 is set at unity by feedback resistor 2858 so that amplifier 2850 functions as a buffer.

The output of operational amplifier 2850 is applied to another buffer formed by operational amplifier 2860 having unity gain set by equal feedback and summing resistors 2862, 2864, respectively. The output of buffer 2860 is returned to −10 volts through resistor 2870 and applied to capacitor 2872 through resistor 2874. The voltage across capacitor 2872 is thus equal to the inverse of the FSL input. The inverse of the FSL input is summed by operational amplifier 2876 through summing resistor 2878, along with the TGC ramp from operational amplifier 2680 through summing resistor 2880. Diode 2882 clamps the output of amplifier 2876 at 0.7 volt, and diode 2884 is back-biased until operational amplifier 2876 outputs a negative voltage, at which point feedback is established through diode 2884 and feedback resistor 2886. As a result, the voltage across resistor 2888 is zero until the sum of the −FSL input and TGC ramp exceeds zero volts. Thus, at the start of the pre-TGC ramp, the voltage across resistor 2888 will be negative. When the magnitude of the TGC ramp reaches a level that causes the current through resistor 2878 to exceed the current through resistor 2880 (as determined by the magnitude of the FSL input), the voltage across resistor 2888 will be clamped at zero volts terminating the flow TGC ramp. Thus, the magnitude of the FSL input determines how much of the TGC ramp will appear across resistor 2888. A large FSL input will keep the voltage across resistor 2888 at zero. A zero FSL input will allow all of the TGC ramp to appear across resistor 2888. The voltage across resistor 2888 is summed through resistor 2890 by operational amplifier 2846 along with the output from operational amplifier 2834. The gain of amplifier 2846 is set by resistor 2892, and diode 2894 clamps the output of amplifier 2846 to zero volts so that the output cannot exceed zero volts. +10 volts applied through resistor 2896 provides a 5 volt offset to the flow TGC signal.

Log Amp

The log amp 72 may be implemented by a variety of commercially available and well-known logarithmic amplifiers and is thus not explained in detail. The log amplifier compresses, detects, and filters the incoming RF signal so that the video output increases by 12.5 millivolts for each db increase in the tissue RF signal. As a result, a 40 db change in the RF signal results in a 0.5 volt change in the tissue video output TISS.

Clutter Canceller

Referring to FIGS. 11A and 2A, the clutter canceller receives the combined flow and tissue signals from the sum and weight. In the combined signal, the flow signals are about 40–50 db below the tissue signals.

The clutter canceller then attenuates the relatively stationary tissue signal while passing the doppler flow signals.

The flow signals are demodulated into I and Q components, so that all the information can be retained, for processing by the corner turning memory and flow processor.

Basically, the clutter canceller performs a "comb" filtering function, providing cancellation of signals at multiples of the pulse repetition frequencies such as the relatively stationary tissue signals, while passing the Doppler shifted components from the flow signals.

The pulse repetition frequencies for the 7.5 mHz ultrasound signals are 15.7 kHz for shallow, and 10.5 kHz for deep, and for the 5.0 mHz ultrasound signals are 7.9 kHz for shallow, and 5.2 kHz for deep.

A detailed description of one embodiment follows, where the combined signal is amplified in 3002, band limited in 3004, digitized in 3006, delayed in 3010, subtracted for cancelation in 3012, converted back to analog in 3016, amplified in 3020 and 3022, demodulated into I and Q components in 3024 and 3026, lowpass filtered in 3030 and 3032, amplified in 3034 and 3036, then again digitized.

The combined flow/tissue signal is input from the sum and weight subsystem into amplifier 3002, which in one embodiment has a gain of 5. The signal then passes through one of two bandpass filters 3004, one used when the system is operating at 5 kHz, the other when operating at 7.5 mHz. Both filters are designed to minimize spreading the symmetry of the combined signal. The signal then passes to A-to-D converters 3006, which are designed with enough resolution and range to preserve the very small flow signals in the presence of the comparatively large tissue signals.

The digitized signals are then routed through receivers 3008 and fed into delay circuit 3010. Adder 3012 also receives the digitized signals, along with the previous combined signal burst stored in delay circuit 3010. Adder 3012 subtracts the previous signal from the present signal so that the relatively stationary tissue signal will subtract out and be greatly attenuated. The flow information, which typically is gathered from seventeen responses, varies from one response to the next and will not subtract out as much as the stationary tissue signals. The signal is then passed through transmitters 3014 to the D-to-A converter 3016.

Adder 3012, delay circuit 3010, transmitter 3014, and D-to-A converter 3016 are clocked at a 20 mHz frequency, derived from a 60 mHz frequency which passes through divide-by-three logic 3018.

The output of D/A converter 3016 is sequentially fed into amplifiers 3020 and 3022, in one embodiment, each having a gain of four. The signal is then split and routed to I demodulator 3024 and Q 3026. The demodulators 3024, 3026 extract the low-frequency signal components of the carrier of the combined carrier signal. The demodulators are driven by a clock at 7.5 mHz, derived from a 30 mHz signal passing through divide-by-four logic 3028. The lowpass filters 3030, 3032, following the I and Q demodulators, attenuate the unwanted sum frequency and higher frequency components out of the balanced demodulators. The signals are then passed respectively through amplifier 3034 and 3036, which in one embodiment each have a gain of five. The outputs are then digitized and fed into the corner turning memory.

Figure 11F:
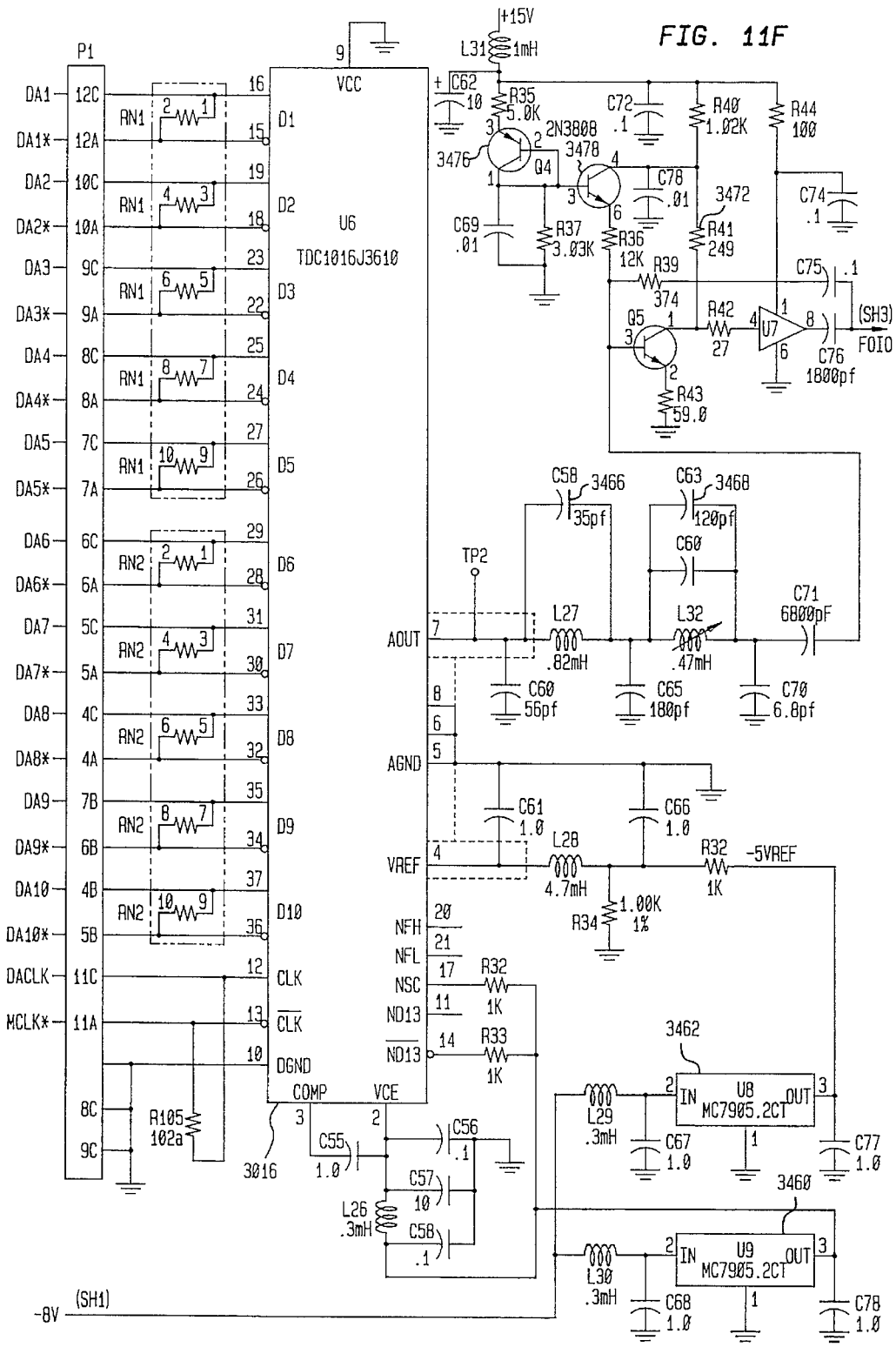
FIG. 11 is a block diagram and circuit schematic of the clutter canceller.

A more detailed description of clutter canceller 3000 circuit components, illustrated in FIGS. 11B through 11G, follows. Referring to FIG. 11B, the combined tissue and flow signal enters the clutter canceller through isolation transformer 3040. The isolation transformer 3040, along with transistors 3042, 3044, and 3046, buffer 3048, capacitors 3050, 3052, 3054, 3056, 3058 and 3060, resistors 3062, 3064, 3066, 3068, 3070, 3072, 3074, 3075, 3076, and 3078, and inductor 3080, comprise amplifier 3002. Transistor 3042 is emitter degenerated for setting the gain, gain being set by resistor 3062, emitter resistance, and resistor 3070. The collector current is monitored by the drop across resistor 3074, which is compared with the voltage at the base of transistor 3044. The voltage at the base of transistor 3044 is the voltage at the top of capacitor 3054 divided down by resistor 3078, transistor 3046 (connected as a temperature compensation diode), and resistor 3075. The current variations modify the emitter and hence collector currents of transistor 3044, thereby setting the bias on transistor 3042 so that its collector current is about 10 milliamps. The output of transistor 3042 is buffered through buffer 3048, a unity voltage gain current booster, used to provide a minimum load on transistor 3042, and have a low output impedance to drive the following circuits. Resistor 3068, together with the gain of 3042 sets the input impedance of the amplifier 3002.

The output of amplifier 3002 is split for entry into bandpass filters 3004. Only one of the two bandpass filters will be active at any one time, depending on whether the system is operating at a 5 kHz or 7.5 mHz ultrasound signal.

The 5 kHz/7.5 mHz selection signal enters the board from the backplane into comparator circuits 3082 and 3084 before being fed into bandpass filter 3004. The comparators 3082, 3084 are designed to select from the backplane signals. Resistors 3088, 3090, and 3092 set the differential state for 7.5 mHz in the absence of backplane signals. The signals are then input to the bandpass filter 3004 through resistor 3098 or 3100. Capacitors 3094 and 3096, together with resistors 3086 and 3260, isolate the comparators from the power lines.

The output of buffer 3048 within amplifier 3002 drives band switching diodes 3102 and 3104 of the bandpass filters 3112, 3114. Bandpass filter 3114, which is operational for a 7.5 mHz beam output, has a delay bandwidth of 3.9 to 10.3 mHz and a 3 db bandwidth of 5.6 to 8.4 mHz. Bandpass filter 3114, which is operational for a 5.0 mHz beam output has a delay bandwidth of 2.6 to 6.9 mHz and a 3 db bandwidth of 3.7 to 5.6 mHz. The filters are designed to minimize the spreading and preserve the symmetry of the combined signal burst. To preserve the shape of the signal burst, the delay across the band of frequencies in the burst is reasonably flat and the phase projection over the band of frequencies projects through some multiple of 180° at zero frequency. These specifically have zero transmission at direct current, a notch at frequencies below the passband and two notches above the pass band, with a final zero transmission level at infinity. The outputs of the filters are terminated at a resistance close to the design load to provide attenuation even when the filter is not being selected by the output diodes 3106 and 3108. The selected output is buffered through buffer 3110, a unity gain current buffer.

Bandpass filter 3114, for the 7.5 mHz beam, has a low-frequency attenuation greater than 30 db at 0 to 2.0 mHz and greater than 10 db at 2.0 to 3.8 mHz. Filter 3114 has a high-frequency attenuation greater than 20 db at 11.2 to 15 mHz and greater than 30 db at 15.0 to 50 mHz. Bandpass filter 3112, for the 5.0 mHz beam, has a low-frequency attenuation greater than 30 db at 0.0 to 1.3 mHz and greater than 10 db at 1.3 to 2.6 mHz. Bandpass filter 3112 has a high-frequency attenuation greater than 20 db at 8.8 to 10 mHz and greater than 30 db at 10 to 50 mHz. Bandpass filter 3112 is used for filtering the 5 kHz signal while bandpass filter 3114 is used for filtering the 7.5 mHz signal. The 5 kHz signal bandpass filter 3112 includes tuning inductors 3116, 3118, 3120, 3122, 3124, 3126 and 3166, along with capacitors 3130, 3132, 3134, 3136, 3138, 3140, 3142, 3144, 3146, 3148, 3150, 3152, 3154, and 3156, resistors 3160 and 3164. Resistors 3158 and 3162, and inductors 3158 and 3169 control current to the band switching diodes 3104 and 3108. The 7.5 mHz bandpass filter 3114 includes tuning inductors 3172, 3174, 3176, 3178, 3180, 3182 and 3222, along with capacitors 3186, 3188, 3190, 3192, 3194, 3196, 3198, 3200, 3202, 3204, 3206, 3208, 3210 and 3212, and resistor 3217. Inductors 3220 and 3224, together with resistors 3216 and 3218, control the diodes 3102 and 3106. Resistor 3066 provides source termination.

The output of buffer 3110 is input to the center tap of step-up transformer 3232. The output of the transformer is limited by fast, hot carrier diodes 3234, 3236, 3238, 3240, 3242 and 3244 connected to bias voltage resistors 3246 and 3248 forward biased diodes 3234 and 3236 and capacitors 3250 and 3252. The limiter is used for avoiding overdriving the A-to-D converter 3006 into a damage region. The A-to-D converter 3006 has 10-bit precision and backplane wiring is connected to produce a 2's complement to the ECL line receivers.

The clutter canceller uses a variety of power signals, including + and −15 volts, −8 volts, −5.4 volts, and +5 volts. To avoid power spikes throughout the system, many noise filters and isolation transformers and voltage regulators are used throughout the clutter canceller, including 3256 through 3320, 3450–3456.

Referring to FIG. 11C, the output of the A/D converter is input into receivers 3322, 3324, and 3326. In one embodiment, each signal line is terminated with a 100 ohm resistor to avoid noise and match input impedances. The output of the receivers is then routed into input registers 3328 and 3330, then routed to delay circuit 3010 and input pipeline registers 3332 and 3334.

Following on to FIG. 11D, the delay circuits 3010 are illustrated as a network of RAMs wherein signals alternatively are input into one of two halves of the RAM memory, while the adder circuity 3012 reads from the second half of RAM memory. In this manner, the adder 3012 reads data delayed one pulse repetition interval from the delay circuit 3010 and current data from receivers 3008.

Referring to FIG. 11E, the addresses for the RAM are generated from counters 3336, 3338 and 3340. The number to be loaded in the counters is a function of the frequency (5 mHz or 7.5 mHz) and the depth of scan (shallow or deep). The frequency select and depth select lines enter receiver 3344 before being output to a PAL 3342. The PAL 3342 generates an output that passes through TTL to ECL converters 3344, 3346 and 3348.

The counters are clocked at a 20 mHz rate output from an OR-gate 3350 (FIG. 11C) and count until a 'carry' output is generated from counter 3340. The carry signal sets flip-flop 3352, which causes the next initial count to be loaded into the counters. The flip-flop is then reset on the next clock cycle, and counting continues again until the next carry is generated. Flip-flop 3354 toggles during a counting operation when the memory half to be loaded must be toggled.

Referring back to FIG. 11D, the output of the counters provides an address input to address buffers 3356, 3358, 3360, 3362, 3364 and 3366. The output of flip-flop 3354 used for toggling between the two halves of the memory is input into OR gates 3368 and 3370. The memory includes twenty 4 k×1 bit RAMs. Ten memory chips 3372, 3374, 3376, 3378, 3380, 3382, 3384, 3386, 3388 and 3390, respectively, provide the ten bits of signal data stored in one half of memory, while another ten memory chips 3392, 3394, 3396, 3398, 3400, 3402, 3404, 3406, 3408, 3410 provide the ten bits for signal data in the other half of memory. A 10-bit signal from each half of the memory is input into multiplexers 3412, 3414 and 3416, wherein one half of the two 10-bit signals is selected as the output signal to the memory output registers 3418 and 3420.

Referring again to FIG. 11C, the output from memory shift registers 3418 and 3420 is input to adders 3422, 3424 and 3426. This input, representing a delayed signal, is subtracted from the data signals that enter adder 3422, 3424 and 3426 through pipeline registers 3332 and 3334, using 2's complement arithmetic. Additionally, a carry for the subtraction operation may be generated from a fast carry chip 3428. The difference which is output from adder 3012, shown as adder circuit 3422, 3424, 3426 and carry 3428, is input to driver 3014 shown as driver chips 3430, 3431 and 3432. Since the resulting signal is relatively small, the 10 LSB's out of the canceller are then transmitted to D to A converter 3016, FIG. 11F.

A 60 mHz clock signal enters the clutter canceller at receiver 3434, then passes through flip-flops 3436 and 3438, acting as divide-by-three logic 3018 to produce a 20 mHz clock signal. The 20 mHz clock signal then passes through delay element 3496, and combined in OR-gates 3442 and 3444 to generate clock signals for the clutter canceller circuits that have a lengthened duty factor, so that the clock signal approaches a square wave. The lengthened clock from 3444 is buffered for transmission to the A/D by 3434. The other diodes from 3442 are buffered by 3350 and 3440. The clock signal provided to the RAM chips passes through a delay circuit 3448 (FIG. 11D) to provide an additional delay of 20 nanoseconds to allow for propagation time delays throughout the clutter canceller and enable synchronous transmissions.

Referring again to FIG. 11E, voltage regulators 3450 and 3452 convert −8 v dc signals to −5.2 v dc signals for use with ECL circuit components. To reduce noise transmissions through the power lines, the ECL circuits use a voltage of −2 v dc as a pulldown voltage so that impedance from the power source more closely matches impedance in the lines. The −2 volts is derived from voltage regulator 3454 and current boost transistor 3456 from a −8 v dc input source.

Referring to FIG. 11F, the now attenuated signals enter D/A converter 3016 where the 10-bit 2's complement signal is converted into an analog voltage output ranging between ground and −1 v dc. A −8 v dc power signal is passed through voltage regulator 3460 to achieve a −5.2 v dc to drive the D/A convertor 3016. Additionally, the −8 v dc signal passes through a voltage regulator 3462 to produce a −5 v dc reference voltage for the D/A converter 3016. The analog voltage output, labeled $A_{out}$, passes through a 9 mHz Hertz elliptic filter 3466 and 3468, the latter tuned to the D/A clock frequency of 20.14 mHz before entering amplifier 3020.

The amplifier includes a transistor 3470 with a gain set by resistors 3472 and 3474. The bias on transistor 3470 is set by transistors 3476 and 3478. The output from transistor 3470 is fed into buffer 3480, which then acts as a voltage follower for providing low-impedance output. The feedback into the transistor 3070 sets the input impedance of amplifier 3020.

Referring to FIG. 11G, the output from amplifier 3020 is input into amplifier 3022, also having a gain of 4. Similar to amplifier 3020, amplifier 3022 includes a transistor 3482 with a gain set by the ratio of resistance between resistor 3484 and 3486. Transistor 3482 is biased by transistors 3488 and 3490. The output from transistor 3482 enters buffer 3492, also configured as a voltage follower for a low impedance output, fed back into transistor 3082 to set the impedance into 3022.

The output from amplifier 3022 is then split, entering into either buffer amplifier 3494 and I balanced demodulator 3496, or buffer amplifier 3498 and Q balanced demodulator 3500. The demodulators also receive a local oscillator input. The local oscillator signal is derived from a 30 mHz or 20 mHz signal input to the clutter canceller at receiver 3502 and then is divided into a 7.5 mHz or 5.0 mHz signal by flip-flop 3504 and 3506, depending on frequency of operation. A 7.5 mHz or 5.0 mHz signal for each demodulator passes through a series of amplifier gates 3508, 3510 and 3512, and 3514, 3516 and 3518, respectively. I demodulator 3496 and Q demodulator 3500 are driven by the 7.5 mHz or 5.0 mHz square wave input, which in effect acts as a polarity switch for reversing the polarity of the signal received from amplifier 3022. An in-phase signal gets full-wave rectified and has the dc term and all the harmonics of a full-wave rectified waveform. The signal applied to the 7.5 mHz or 5.0 mHz oscillator signal having a 90° phase shift, on the other hand, produces a sine wave reversed in-phase at either the MAX or the MIN and has no dc term, but all the harmonics of the full waveform.

The output of the I demodulator 3496 enters low-pass filter 3030, while the output of demodulator 3500 enters low-pass filter 3032. The low-pass filters attenuate the unwanted sum frequency and higher frequency components by attenuating the signal by 17 db at 2.5 mHz and by 43 db from 4 to 22 mHz. The respective outputs are further amplified at amplifiers 3034 and 3036. The filters have nearly flat delays that are matched in both amplitude and phase up to 9.0 mHz so the flow processing downstream can resolve forward from reverse flow. Amplifiers 3034 and 3036 in one embodiment are amplifiers with a gain of 5. The respective outputs pass through buffers 3520 and 3522 and routed to the A/D converter and to the corner turning memory.

A/D Board

Referring to FIG. 12A, the A/D board comprises tissue signal digitizing circuitry 4200, I signal digitizing circuitry 4202, and Q signal digitizing circuitry 4204. The tissue signal digitizing circuitry 4200 receives an analog tissue waveform from LOG AMP 72 of FIG. 2 and converts the waveform into a digitized tissue data stream. The I signal digitizing circuitry 4202 receives an analog I waveform from clutter canceller 74 of FIG. 2 and outputs a digitized I data stream. The Q signal digitizing circuitry 4204 receives an analog Q waveform from clutter canceller 74 and outputs a digitized Q data stream. The three data streams are fed into multiplexer circuitry 4206, which passes one of the three data streams to corner turning memory 80.

The A/D board 76 also comprises a 60.4 mHz oscillator 4208 which generates clock signals output to the timing and control subsystem and into frequency multiplier and divider circuitry 4306, 4308 and 4310. One function enabled by the 60.4 mHz oscillator 4208 is the reclocking of signals entering from the timing and control subsystem. Timing and control signals enter circuits such as wave A/B pulse train generator 4214 and reclocking circuitry 4216. These circuits 4214 and 4216 also receive synchronization clocks from latch 4272. The pulse streams having different phases enter latch 4278 from pulse generators 4220. The synchronization clocks for reclocking signals from the timing and control subsystem are generated by latch 4272 from the master clock, the 60 mHz oscillator 4208, after passing through frequency multiple divider circuitry 4212 and frequency division circuitry 4308.

The circuit schematics for the A/D board are shown in FIGS. 12B through 12E. Referring to FIGS. 12A and 12B, the tissue signal digitizing circuitry 4200 comprises a conventional amplifier circuit 4224 designed for a gain of −4, an inverting amplifier circuit 4226, and an A/D converter 4231. The high current inverting amplifier circuitry 4226 includes amplifiers 4228 and 4230 for driving the capacitive input of the flash A/D converter 4228.

A −2 volt voltage reference is input at pin 26 to A/D converter 4231. This reference voltage is generated by resistor 4232, regulating diode 4234, resistors 4235 through 4237, and capacitor 4238. This voltage reference is used by the A/D converter in each of digitizing circuitries 4200, 4202, and 4204. Amplifier 4240 and transistor 4242 and associated circuitry generate the offset voltage necessary to maintain the −2 volt reference voltage. Voltage regulator 4244 outputs a −5.2 volt power supply to A/D converter 4231. The conversion at the A/D converter 4248 is triggered by a convert signal input from D latch 4272 of FIG. 12E.

Referring to FIGS. 12A and 12B, the I signal digitizing circuitry 4202 includes a conventional amplifier 4224' having a gain of −4, a ±1 volt limiting circuit 4246, high current inverting amplifier 4226', and A/D converter 4248. The conventional amplifier 4224' is the same amplifier circuitry used for tissue signal digitizing circuit 4200.

The ±1 volt limiting circuitry 4246 reduces the recovery time that would occur at A/D 4248 if the input voltage were to exceed the maximum range. Limiting circuitry 4246 includes diodes 4250, 4252, 4254, and 4256, along with buffer 4258. The output of buffer 4258 is input into high current inverting amplifier 4226', which consists of identical circuitry as amplifier 4226 of the tissue signal digitizing circuitry 4200.

Just as for the tissue signal digitizing circuitry 4200, the I signal digitizing circuitry 4202, amplifier 4240', and transistor 4242 and associated circuitry generate the offset voltage required to maintain a −2 volt reference voltage at pin 26 of A/D converter 4248. By adjusting resistor 4260, the most significant bit output from A/D converter 4248 can be adjusted for force a fifty percent duty cycle. Voltage regulator 4244' generates a −5.2 volt reference to A/D converter 4248. The conversion at the A/D converter 4248 is triggered by a convert signal input from D latch 4272 of FIG. 12E.

Referring to FIGS. 12A and 12C, the Q signal digitizing circuitry 4204 comprises a conventional amplifier 4224' having a gain of −4, a ±1 volt limiting circuit 4250', a high current inverting amplifier 4226", and A/D converter 4262. The conventional amplifier 4224" comprises identical circuitry as amplifiers 4224 and 4224' of tissue signal digitizing circuitry 4200 and I signal digitizing circuitry 4202. The ±1 volt limiting circuitry 4246' is identical to circuitry 4246 of I signal digitizing circuitry 4202 and includes diodes 4250', 4252', 4254', and 4256', along with buffer 4258'. The high current inverting amplifier 4226" comprises circuitry identical to high current inverting amplifiers 4226 and 4226'.

Similarly, amplifier 4240" and transistor 4242" along with associated circuits generate an offset voltage required to maintain a −2.0 volt voltage reference at pin 26 of A/D converter 4262. Voltage regulator 4244" outputs a −5.2 voltage reference to A/D converter 4262. The conversion at the A/D converter 4262 is triggered by a convert signal input from D latch 4272 of FIG. 12E.

The digitized tissue streams output from each of A/D converters 4231, 4248, and 4262 are input into dual multiplexers 4264, 4266, 4268, and 4270. One bit from each of the three data streams enters each of the eight multiplexers. A select line output from D latch 4272 selects which of the three data streams passes through the multiplexers 4264, 4266, 4268, and 4270 into QAD TTL to ECL translators 4274 and 4276 for routing the data to corner turning memory 80.

Voltage regulator 4274, inverters 8280, 4284 and associated components form a 1.2 voltage reference across resistor 4270 and 4292. Switch 4284 is a CMOS switch controlled by the most significant bit of A/D converters 4248 and 4262. If the input of the A/D converter is −1 volt, the most significant bit of the A/D converter will oscillate at approximately a fifty percent duty cycle. This causes the output of the filter defined by resistor 4246 and capacitor 4288 to be approximately 0.6 volt. This voltage is compared to a reference voltage preset by resistor 4292.

An error integrator defined by resistors 4286 and 4294 and capacitor 4296 causes amplifier 4284 to output whatever DC voltage is required to force the average value of the most significant bit toggle to be equal and opposite to the preset voltage at resistor 4292. Similarly, the output at amplifier 4282 will be the required voltage to force the average value of the most significant bit toggle of A/D converter 4248 to be equal and opposite to the preset voltage at resistor 4290.

Referring to FIG. 12A and 12D, the 60.4 mHz oscillator 4208 is a conventional, common-base oscillator circuit with a tank circuit in the collector of transistor 4298. The 60.4 mHz signal is fed into frequency multiplier and divider circuits 4212 comprised of ECL circuit components. Additionally, the 60.4 mHz signal is AC coupled and referenced to ECL converters 4300, 4302, and 4304. The 60.4 mHz signal output from converter 4300 is routed to the delay controller 66. The 60.4 mHz signal output from converter 4302 is routed to the clutter canceller 74. The 60.4 mHz signal output from buffer 4304 is routed to the timing and control subsystem. Because the emitter coupling logic circuitry is used, pulldown resistors are used throughout the design at outputs to ECL components.

Frequency multiplier and divider circuits 4212 comprise ECL circuitry 4306 for multiplying the 60.4 mHz frequency times two. This 120.8 mHz signal is fed into a frequency division circuit 4308 for dividing the 120.8 mHz signal by two for the 7.5 mHz transducer and by three for the 5.0 mHz transducer. Thus, output from frequency multiplier and divider circuits 4312 is either a 60.4 mHz or 40 mHz signal, depending upon the status of the 5/7 select line entering from transmitter 56 at pins 70A and 70C of the backplane connector. An additional divide-by-2 or divide-by-3 circuit 4310 is also included to generate a 30 mHz signal when a 7.5 mHz transducer is selected and a 20 mHz signal when the 5.0 mHz transducer is selected.

The 60/40 mHz signal output from division circuit 4308 is input into frequency division circuitry 4222 (FIG. 12E), which comprises a divide-by-4 counter 4314. The outputs of counter 4314 generate a 15/10 signal, 30/20 signal, and a one of sixteen count signal which are input to buffer 4316 via ECL to TTL converters. The output of buffer 4316 is then input as a clock pulse to D latch 4272 and acts as a synchronization clock for reclocking signals.

Additionally the 60/40 mHz output from buffer 4316 is routed to counters 4318, 4320, 4322 and 4324. Output from D latch 4272 is a reclocked 30/20 mHz signal at $O_0$, a reclocked synchronization signal at $O_1$, a conversion pulse for A/D converters 4231, 4248, and 4262, a select signal for multiplexers 4264, 4266, 4268, and 4270, and pulses for reclocking timing and control signals at $O_5$, $O_6$ and $O_7$.

The inputs synchronized to the 60/40 clock input to D latch 4272 are generated from counters 4318, 4320, 4322, and 4324, along with flip-flops 4326, 4328, 4330, 332, 4334, and 4336.

Two signals entering from the timing and control subsystem which need to be reclocked are signals DSKIN and DXMIT. These signals enter reclocking circuitry 4216, along with the synchronization pulse streams output from D latch 4272. Referring to the DSKIN signal, the signal first is converted from ECL to TTL 4338. The converted signal then enters flip-flop 4340 along with the synchronization pulse. The DXMIT signal is converted from ECL to GTL at converter 4342, then enters flip-flop 4344, along with the synchronization stream from D latch 4272. The outputs from flip-flops 4340 and 4344 are input to flip-flop 4346 to generate a TXS signal from the DSKIN and DXMIT signals. The combined signal is converted from TTL to ECL by converter 4348, then output to sum and weight card 68. The reclocked DXMIT signal output from flip-flop 4344 is also input to TTL-to-ECL converter 4350, then output to a fiberoptic transmitter. Additionally, the DXMIT signal output from flip-flop 4344 is input to flip-flop 4352 of FIG. 26D, comprising part of the wave A/B pulse train generator 4214. The wave A/B pulse train generator 4214 generates eight pulses from the reclocked DXMIT signal. The pulse train is output via fiberoptic transmitter 4354 to transmitter 56 of FIG. 2A.

Fiber Optics Receiver

The fiber optic receiver board translates the Manchester data string to reduce noise coupling from the digital chassis. The Manchester string (FIG. 30) (described elsewhere) is received by the optic receiver which translates the optical signal to an analog voltage. The analog voltage is then applied to a differential comparator 4602. The output of the comparator is then applied to the differential TTL buffer 4604. The output of 4604 is then at the correct voltage level to be decoded properly on the transmitter and MUX cards (described elsewhere).

The inductors, capacitors and resistors shown at 4606, 4608 and 4610 are for board power filtering. The resistors 4612, 4614 and 4616 set the switching levels of the differential comparator 4602.

Timing and Control

A block diagram of the timing and control subsystem 80 (FIG. 2) is illustrated in FIG. 13A. The timing and control subsystem includes an A/D interface 5000, the function of which is to provide timing signals to the analog circuitry, to receive digital data indicative of the in-phase and quadrature components of the flow signal and the tissue data and to provide various timing signals to the remainder of the ultrasound imaging system. These timing signals are used to derive further timing signals by the sample site and pulse timing circuit 5002. The sample site and pulse timing circuit 5002 generates timing signals that reoccur at each sample site. A beam control circuit 5004 generates timing signals that reoccur during each beam, i.e., during the period that a relatively large number of sample sites are accessed.

The timing and control subsystem 80 also includes a corner turning memory 5006 and a memory control circuit 5008 which, as explained above with reference to FIG. 2, reorders the data received from the sample sites before outputting the data to the flow processor.

As mentioned above with reference to the description of the system block diagram, the ultrasound imaging system includes the capability of freezing an image on the CRT. For this purpose, a freeze control circuit 5010 is provided to generate the appropriate freeze signals at the proper time. Finally, a VME interface circuit 5012 is provided to allow the timing and control subsystem 80 to interface with the CPU 130 (FIG. 2).

The sample site and pulse timing circuits are illustrated in FIG. 61 and 62. With reference to FIG. 13B, a 60 mHz signal from the analog to digital converter subsystem 76 is applied to a binary counter 5020 which divides the 60 mHz signal down to a 15 mHz signal and a 7 ½ mHz signal at respective outputs. The 15 mHz signal is then inverted by inverter 5022 before being output to the interpolator subsystem (FIG. 2).

The 60 mHz signal from the A/D converter subsystem 76 is also applied to a pair of flip-flops 5024, 5026 that collectively divide the 60 mHz signal by three to generate a 20 mHz signal that is applied to the spectrum/velocity subsystem through inverter 5028. The 20 mHz signal is further divided by two by a third flip-flop 5030 to generate a 10 mHz signal at the output of buffer 5032. The frequency divider circuitry thus generates 20 mHz, 15 mHz, 10 mHz and 7.5 mHz reference timing signals.

The timing at each sample site is provided by an eight-stage Johnson counter implemented by a pair of multiplex/registers 5040, 5042. The multiplex/registers receive a clock signal of either 30 or 20 mHz and a A/D-sync signal from the analog to digital converter via the A/D circuit 5000. Basically, the multiplexer/registers 5040, 5042, in conjunction with inverter 5044 produce 16 different states designated by outputs JC (0)–JC (15) at each sample site JC(8)–JC(15) are the inverse of JC(0)–JC(7), respectively. Thus, the Johnson counter divides the period that a return from a sample at a given range bin is received into sixteen portions in order to generate various timing signals occurring at any one of sixteen points during which a sample is being received from a given range bin. The Johnson counter outputs JC (0:7) are applied to a PAL 5046 that also receives a DIG-PLAYBK signal which is software generated to designate that the received data is being output from a video cassette recorder or other data storage device. Finally, the PAL 5046 receives a flow processor load pulse FP-LD that designates when the data is being loaded into the flow processor. Using the DIG-PLAYBK and FP-LD signals, in combination with the Johnson counter outputs, the PAL 5046 generates a JC-1-FPAL output at the start of a range bin, a JC-9-FPAL at about the midpoint of a range bin and four other timing signals TF-PL, TF-SCLK, TF-SNYC and TF-PCLK at various other points during each range bin.

The A/D-SYNC pulse is also applied to a binary counter 5050 through an inverter 5052. The binary counter 5050 is clocked by the 30 or 20 mHz signal that is also used to clock the multiplexer/registers 5040, 5042. The binary counter is cleared by the A/D-SYNC pulse and thereafter begins incrementing at the 20 or 30 mHz rate to generate signals for the flow processor from inverters 5054, 5056, 5058 at half the clocked frequency, one-quarter of the clocked frequency and one-eighth the clock frequency, respectively. The binary counter 5050 also generates a sample A/D timing signal SA-AD-SYNC which is not used in normal operation, but is used to generate an A/D-SYNC pulse in a simulate mode.

The sample site and pulse timing circuit, as illustrated in FIG. 13B, also includes a binary counter 5056 which is clocked by the first stage of the Johnson counter JC-0-D and loaded with the two's complement of the number of pulses transmitted during the previous beam PR-FPSY (0:3) by the flow processor load FP-LD pulse. Thereafter, binary counter 5056 begins incrementing from the two's complement and FP-SC-CO pulse when the terminal count is reached. The binary counter 5056 is thus used for outputting date from the corner turning memory 5006 (FIG. 13A).

The sample site and pulse timing circuit 5002 (FIG. 13A) also includes the circuitry illustrated in FIG. 13C. This circuitry counts the number of sample sites (i.e. range bins) for each sample pulse and provides an eight-bit word indicative of the sample site from which a return is currently being received. The circuitry illustrated in FIG. 13C also counts the number of sample pulses as they are sequentially transmitted for each beam in order to determine when the last sample pulse has been transmitted. Finally, the circuitry generates an XMIT pulse which is applied to the analog circuitry to cause a pulse of ultrasound to be generated by the transducer.

The two's complement of the number of sample sites (i.e., range bins) for each sample pulse is output by a PAL 5070 based upon the frequency of the ultrasound energy (i.e., 5 kHz or 7.5 mHz) and the depth (DPTH) (0:1) to which the ultrasound examination is to be made. This depth is under software control. The two's complement of the number of sample sites is loaded into binary counters 5072, 5074, 5076 when the final counter 5076 generates a carry pulse. The carry pulse is applied to the preload inputs of the counters 5072, 5074, 5076 through inverter 5078. The counters 5072, 5074, 5076 are inhibited by a sample site count release input SS-CNT-REL until the appropriate time as explained in greater detail below. Thereafter, the binary counters 5072, 5074, 5076 increment once for each cycle of the Johnson counters as each JC-0-8 is generated until the terminal count of "FFFF" is reached after the number of JC-0-8 pulses equal to the number of range bins being used have been counted. Counter 5076 then generates a LAST-SS pulse and, as explained above, once again preloads the counters 5072, 5074, 5076. These counters 5072–5076 also output a 9-bit word SS (0:8) that identifies the sample site (i.e. range bin) from which data is currently being received and applied to the corner turning memory 5006. The carry pulse at the output of counter 5076 at the last sample site is also applied to the D input of a flip-flop 5080 which is then set on the next JC-0-8 pulse to generate a transmit sample site pulse SMTSS and an identical signal TB-XMTSS at the output of inverter 5082 functioning as a buffer. The Q+ output of flip-flop is also applied to one input of OR gate 5084. Since the flip-flop 5080 is clocked by the first JC (0) impulse after the last sample site, this JC (0) pulse occurs during the first sample site of the next beam. OR gate 5084 thus generates a FIRST-PULSE-BGN pulse indicative of the first sample site for the next beam.

As mentioned above, the circuitry illustrated in FIG. 13C also counts the number of sample pulses as they occur during each beam. The two's complement of the number of pulses in each beam is output by a PAL 5090 based upon a 61-bit word indicative of beam type BM-TYPE<0:5> and a PAD bit indicating whether the beam is a "PAD" beam, as explained in greater detail below. A pair of binary counters 5092, 5094 are preloaded with the two's complement of the number of pulses per beam when the carry output of counter 5094 goes low. The low, at the CC0 output of the binary counter 5094, is also applied to the K input of a flip-flop 5096, which applies a low to the CET input of counter 5092 to prevent the counter 5092 from incrementing on all of the JC-0-B pulses until the J input to flip-flop 5096 goes high. The J input to flip-flop 5096 does not go high until the sample site counter 5076 reaches the final sample site count. Thereafter, on the next JC-0-B pulse, flip-flop 5096 becomes set, thereby enabling counters 5092, 5094 to increment each time the sample site counters 5072, 5074, 5076 reach the terminal count. It is thus seen that the pulse counters 5092, 5094 ignore the first pulse and then increment once each sample pulse until the final sample pulse has been reached. As explained in greater detail below, the first sample pulse is ignored by the binary counters 5092, 5094 since the returns from the first sample pulse are used only to set up the operation of the clutter canceller and are not used to generate the display. The pulse counters 5092, 5094 thus output pulses at the end of each beam, either directly or through inverter 5096.

The number of sample pulses for each beam, in addition to being loaded into the counters 5092, 5094, is also stored in a register 5100 and output when the data stored in the corner turning memory from that sample pulse are output to the flow processor in order to align the data from a beam with the number of pulses in that beam. The register 5100 thus generates a 4-bit word PR-FPSY<0:3> upon each PR-FP-CK pulse to identify the number of pulses in each beam. In the event that the beam is a "PAD" beam, and 8-bit word indicative of the two's complement of the number of pulses in the PAD beam is output by a register 5102 and processed in the same manner as the output of PAL 5090.

The timing and control circuitry illustrated in FIG. 13C also generates a transmit pulse XMIT during the midpoint of processing the final sample site of a sample pulse. Accordingly, a high is applied to the data input of flip-flop 5104 during the last sample site count of each pulse. Thereafter, the JC-8-A pulse occurring during processing of that sample site sets flip-flop 5104 to generate a high XMIT which is terminated when flip-flop 5104 is reset by a subsequently generated XMIT-ENABLE.

As explained above with reference with FIG. 13A, the beam control circuit 5004 is illustrated in FIGS. 13D–G. With reference to FIG. 13D, an octal register 5110 is used to generate various timing and control signals when the display data is being generated by a video cassette recorder or other digital storage device based upon data VME-D<0:7> clocked into the register 5110 by a frame rate buffer control clock VRBUF-CTL-CK. The outputs of the register 5110 are three VCR playback rates PLY-RATE 0–2, a digital playback bit DIG-PLAYBK specifying the video playback mode, and a playback frame release PLYBK-FR-REL. The playback rate outputs and the digital playback mode designator outputs of the register 5110 are applied to a PAL 5112 along with three bits identifying the frame count of the digital data from frame counter 5114, a capture beam bit CAPTR-BEAM, a first pulse signal FIRST-PULS, and a beam detect input BEAM-DET. From these inputs, PAL 5112 generates a corner turning memory beam active signal CTM-BMACT and a capture beam detect CAP-BEAM-DET signal which inhibit the transfer of data into the corner turning memory. The PAL 5112 also generates a beam active signal BMACT signal which is applied through two inverters 5116–5118 to other portions of the timing and control circuitry and to the flow processor. The beam active signal BMACT is high whenever data are being received from a sample pulse. The PAL 5112 also generates an active frame ACTIV-FRM pulse which is inverted by inverter 5120 when in the digital storage mode and an ACTIVE-BM$_1$ signal through inverter 5122 which is applied to the flow processor.

At the start of each beam, an XMTSS signal is generated, as explained above with reference to FIG. 13C. This XMTSS pulse clocks a PAD input into flip-flop 5130 to prevent the PAL 5112 from generating a beam active signal BMACT whenever a PAD beam is being processed. The Q* output is applied to the clock input of flip-flop 5132 to set flip-flop 5132 and output an SS-CNT-REL high, which prevents data from being processed by the system for a short period each frame to allow the software in the CPU to examine the data to determine if any operating parameters must be changed. The flip-flop 5132 is then subsequently reset by the DIGPLY-BEAM$_1$ output of PAL 5112.

The timing and control system also includes a capture beam function which is used for diagnostic purposes in which data can be entered into the corner turning memory and then read out in a test mode. The process begins with the software generating through the VME interface 5012 a high capture beam pulse CAPTR-BEAM that is applied through OR-gate 5140 to remove the reset from flip-flips 5142, 5144. Thereafter, when the first beam FRST BEAM occurs, flip-flop 5142 is set through inverter 5146. Flip-flop 5142 then generates a one-frame signal ONE-FRAME. On the next FIRST-BEAM signal, flip-flop 5142 toggles, thereby removing the ONE-FRAME signal and clocking a one into flip-flop 5144. The low at the Q* output of flip-flop 5144 is then applied to the J input of flip-flop 5142 so that flip-flop 5142 ignores all subsequent FIRST-BEAM pulses. The flip-flop 5142, 5144 thus generate a single ONE-FRAME pulse between two adjacent FIRST-BEAM pulses after the occurrence of CAPTR-BEAM going high. During ONE-FRAME, the preset is removed from flip-flop 5146 and a reset is removed from flip-flop 5148. The following FIRST-PULSE then resets flip-flop 5146 if the output of a comparator 5150, assuming, for the minute, that the output of a comparator 5150 is high. The next "FIRST-PULSE" sets flip-flop 5148 and generates BEAM-DET through OR-gate 5152. On the next FIRST-BEAM, the ONE-FRAME output of flip-flop 5142 goes to zero, thus setting flip-flop 5146 and resetting flip-flop 5148. However, that FIRST-BEAM pulse also clocks ONE-FRAME into flip-flop 5144, thus keeping BEAM-DET high until the CAPTR-BEAM input goes low. Thus, when CAPTR-BEAM goes high, BEAM-DET goes high on the second FIRST-PULS of the next FIRST-BEAM and remains high until CAPTR-BEAM goes low. BEAM-DET goes high at the completion of captured beam data being written into the corner turning memory. The beam number to be captured is designated by a 8-bit word stored in register 5156 from the VME interface 5012. The capture beam data VME-D<0:7> is clocked into the register 5156 by a capture beam clock CAPT-BEAM-CK. Register 5156 applies the beam number to be captured to the comparator 5150, which also receives an 8-bit word BEAM<0:7> indicative of the beam data currently being entered into the corner turning memory. Thus, when the capture beam CAPTR-BEAM input has gone high, the procedure explained above occurs when the beam number currently being entered into the corner turning memory coincides with the beam number to captured. It is only possible to capture an image beam (i.e., not a velocity or spectrum beam) so that the comparator 5150 is only active when the IMAGE bit is low.

The circuitry illustrated in FIG. 13E basically functions to determine the beam number and the beam data that the corner turning memory will be acquiring next. The CPU applies through the VME interface 5012 an 8-bit word VME-D<0:7> to a register 5160, which is clocked into the register by a SCAN-CTL-CK pulse also from the VME interface 5012. The output of the register is a scan control signal SCAN-CTL<0:7> that specifies whether the data being input to the corner turning memory is for a velocity beam, a spectrum beam, or an image beam, and if a spectrum beam, whether it includes 128 or 256 sample sites. The scan control data from register 5160 also designate whether there is to be normal imaging, in which sixteen sample pulses are generated for each beam, or fast imaging, in which either four or eight pulses are generated for each beam, depending upon the ultrasound frequency. The scan control data are applied to a conventional microprocessor 5162 having an internal program and internal RAM, which also receives a 2-bit word indicative of the number of sample sites DPTH<0:1>, a bit identifying the ultrasound frequency, a FIRST-PULS pulse identifying the start of a beam, and a LAST-PULS identifying the end of a beam, which are generated, as explained above, with reference to FIG. 13C. The microprocessor 5162 is clocked at 7.5 mHz and it is interrupted to start at beam 1 by a RESTART-BEAM pulse or a system reset SYSRST. The microprocessor 5162 generates an 8-bit word that is applied to a buffer 5164, identifying the characteristics of the beam, such as the number of sample sites and the ultrasound frequency. The data from the buffer 5164 are once again stored in a buffer 5166 and applied to a third buffer 5168 upon a TYPE-CK pulse. The beam type data BM-TYP<0:5> is applied to other portions of the timing and control subsystem as well as to the flow processor through a buffer 5170 and drivers 5172, 5174.

The microprocessor 5162 also generates chip select signals and data which are applied to a decoder 5180 in order to generate various clock signals for clocking data into registers. For example, the decoder 5180 generates the PAD-CNT-CK pulse that clocks the scan data SCAN-D<0:7> into register 5102 in FIG. 13C.

The circuitry illustrated in FIG. 13F basically functions to identify the beam number (i.e., the position of the ultrasound beam across the transducer) for the image beam and the scan lines at the bottom of the CRT. The circuitry also generates a set of buffered Johnson counter outputs. More specifically, the CPU, through the VME interface 5012, generates an 8-bit word VME-D<0:7> that is applied to registers 5200, 5202, 5204. The data are clocked into register 5200 by a SAMP-A-CK pulse, into register 5202 by a SAMP-B-CK pulse, and into register 5204 by an IMAG-BM-CK. Each of these registers 5200–5204 is individually output enabled by register enables generated by a PAL 5206 based upon a number of inputs. These inputs include a 3-bit word PRE-TYPE<0:2> identifying the type of beam from register 5166 (FIG. 13E), a SINGLE-IMG-BM, allowing a single beam to be displayed across the entire screen for diagnostic purposes, a PAD-BM input that inhibits PAL 5206 from generating a PR-FP-CK pulse, and an FP-LD pulse in order to prevent register 5100 (FIG. 13C) from being updated at the end of a PAD beam, and it prevents the flow processor from being loaded. A LAST-PULSE-END pulse from the circuitry illustrated in FIG. 13C is also applied to the PAL 5206 to cause it to generate an FP-LD pulse when new data start being output from the corner turning memory. The FP-LD pulse is also generated by PAL 5206 upon receipt of an FP-SC-CO pulse from the circuitry illustrated in FIG. 13B. The output from the one enabled register 5200–5204 is applied to other portions of the timing and control subsystems as well as to the flow processor through a buffer 5210.

The Johnson counter outputs JC(0, 1, 3, 4, 6) are applied to a buffer 5212 to generate buffered Johnson counter outputs JC-0-A-D, JC-6-A, JC-3-A, JC-4-A and JC-1-A. The JC(7) signal is also buffered by driver 5214 to generate a JC-7-A output. Likewise, the JC(0) pulse is inverted by inverter 5216 to generate the JC-8-A output. Finally, an inverting buffer 5218 is used to generate the JC-12-A pulses from the JC(4) input.

The processing of each sample site return is done in four distinct states, as designated by a 2-bit section number SECTION<0:1>. As illustrated in FIG. 13G, a shift register 5230 is initially preloaded with a 4-bit word "0011" which is then recirculated through the shift register 5230 by the JC-0-A pulses. The two least significant bits of the shift register 5230 are used as the SECTION<0:1> output, which, since the register has been loaded with "0011," repetitively outputs the binary code for decimal 0, 1, 3, 2 to define the states. The state count is applied to the flow processor through drivers 5232, 5234 and to a PAL 5236. The PAL 5236 decodes the BM-TYPE<0:1> word to output an IMAGE low if the beam type word designates an image beam, a SPECTRUM low if the beam type word designates a spectrum beam, and a PAD low if the beam type word designates a PAD beam. The PAL 5236 also receives a 4-bit scanned control word SCAN-CTL<0:3> specifying whether the scan beams at the bottom of the CRT are either a velocity or spectrum beam, and if a spectrum beam, whether it is generated from 128 or 256 range bins. The durations of these states are a function of the number of range bins in each beam. For this purpose, the scan word SCAN-D<0:7> is applied to registers 5238, 5240. Registers 5238 record the two's complement of the number of range bins in states 0, 1 and 3 when an SECT-3QTR-CK pulse is applied to the clock input of register 5238. Register 5240 records the two's complement of the number of range bins used in state 2 when a SECT-LAST-Q2R-CK pulse is applied to the clock input of register 5240. Registers 5238, 5240 are alternately output enabled by a SEAT-LAST-Q2R-EN output from PAL 5236, which is applied directly to the output enable of register 5240 and to the output enable input of register 5238 through inverter 5242. The output of the selected register 5238 or 5240 is used to preload a pair of binary counters 5244, 5246 when the SECT-CNTR-LD output of the PAL 5236 goes low. When the counters 5244, 5246 reach the terminal count at the end of each state, a carry pulse is generated at the output of counter 5246 that causes PAL 5246 to switch to the next state by once again preloading the binary counters 5244, 5246 and allowing the shift register 5230 to increment through the SECT-SHFT-$S_0$ and SECT-SHFT-$S_1$ outputs of PAL 5236.

The analog-to-digital interface subsystem 5000 (FIG. 13A) is illustrated in FIGS. 13H–L. With reference to FIG. 13H, RS 232 data PT-RTS3B, PT-TXD3B are applied through hysteresis inverters 5260, 5262 to a pair of differential AND-gates 5264, 5266 acting as level shifters in order to generate complementary TXN-CMD, -TXN-CMD, and TXN-D1, -TXN-$D_1$ data which are applied to the delay control subsystem that controls the operation of the delay lines in the analog circuitry.

A set of pull-up resistors 5268 are used to bias the outputs of the AND-gates 5264, 5266.

The return data from the delay control subsystem are applied to a conventional level shifting circuit 5270 that has its inputs also biased high through a set of pull-up resistors 5272. The 2-bit output of the level shifting circuit 5270 is applied to the CPU as TP-RXD3B and TP-DCD3B bits.

It will be recalled that the FREQ bit is used to select an ultrasound frequency of either 5 kHz or 7.5 mHz. For this purpose, the FREQ bit is applied directly to NAND-gate 5276 and to NAND-gate 5278 through inverter 5280. Thus, when FREQ is low, NAND-gate 5278 is enabled, and when FREQ is high, NAND-gate 5276 is enabled. NAND-gate 5278 receives the output of an internal 40 mHz oscillator 5282, while NAND-gate 5276 receives the output of an internal 60 mHz oscillator 5284. The 60 mHz or 40 mHz output of the enabled NAND-gate 5276, 5278 is applied through NOR-gate 5286 to a toggling flip-flop 5288, dividing the incoming frequency by two. The 30 or 20 mHz signal from flip-flop 3288 SA-30#20 mHz is applied along with its complement, the 60 mHz output from oscillator 5284, and an SA-AD-SYNC pulse generated in the circuitry of FIG. 13B to synchronize the operation of the analog circuitry with the digital circuitry are applied to a multiplexer 5290. The multiplexer 5290 also receives 60 mHz, 30 mHz or 20 mHz, and analog-to-digital synchronization pulses from the delay control board through a level shifting circuit 5292. In normal operation, the AD-TIMING input is high to cause the multiplexer 5290 to output the timing signals generated in the delay control subsystem. However, in order to allow timing signals to be internally generated for test purposes, the multiplexer 5290 can generate the timing signals from the internal oscillators 5282, 5284.

It will be recalled from the explanation of the circuitry of FIG. 13C, that an XMIT pulse is generated during processing of the last sample site of each sample pulse in order to trigger the analog circuitry to once again generate a pulse of ultrasound. For this purpose, the XMIT pulse is applied through differential OR-gate 5294, acting as a level shifting circuit to generate complementary TXN-XMIT and -TXN-XMIT to illuminate an optical link to the analog circuitry for the purpose of triggering the transmission of an ultrasound pulse. Similarly, a SKIN pulse used to blank the analog front end from returns from the skin of the patient is applied to a differential AND-gate 5296 operating as a level shifter to generate complementary TXN-SKIN and -TXN-SKIN pulses. Finally, the circuitry of FIG. 13H includes an optical modulator for transmitting data from the digital circuitry to the analog circuitry. The data MANCHESTER are in the form of a serial data stream using a conventional Manchester data format in which the serial line changes state each clock pulse. The Manchester data are applied through NAND-gate 5298 acting as an inverter to the base of a transistor 5300. When MANCHESTER is low, transistor 5300 is turned on, thereby drawing current through resistor 5302 and diode 5304, thereby making TXN-MANCH low and preventing current from flowing through a photodiode (not shown). Capacitor 5306 is used to provide filtering. When MANCHESTER is high, transistor 5300 is turned off, thereby allowing current to flow through resistor 5302, a light-emitting diode (not shown), and resistor 5306. Capacitor 5308 is provided to increase the response time of the light-emitting diode.

The circuitry illustrated in FIG. 13I primarily functions to write data from the analog-to-digital converter subsystem to one of three registers, depending upon whether the data are tissue, in-phase flow data, or quadrature flow data. The data from the analog-to-digital converter subsystem is applied to the circuitry illustrated in FIG. 13I in complementary form and is converted by conventional level converters 5320, 5322. The input lines are biased by a set of terminating resistors 5324. The outputs of level converter 5320 are applied to four inputs of a multiplexer 5326 and the outputs of level converter 5322 are applied to four inputs of a multiplexer 5328. The other four inputs of each multiplexer 5326, 5328 are connected to ground potential. The multiplexers 5326, 5328 normally apply the incoming level converter data to a buffer 5330. However, when the SKIN input goes low, the multiplexers 5326, 5328 apply logical "zeros" to the inputs of the buffer 5330. It will be recalled that the SKIN pulse is generated at the time that an ultrasound return is received from the skin of the patient. By forcing the outputs of the multiplexers 5326, 5328 low at that time, the ultrasound imaging system ignores the returns from the skin of the patient.

The data at the output of the multiplexers 5326, 5328 are clocked into the buffer 5330 by the JC-1-A pulse at the start of each range bin processing. The JC-1-A pulse occurs when the quadrature data is being output by the analog-to-digital subsystem. The buffer 5330 thus stores an 8-bit digital word indicative of the quadrature data from a given sample site or range bin. Similarly, the outputs of the multiplexers 5326, 5328 are clocked into a register 5332 by the JC-12-A pulse when the in-phase flow data are output from the analog-to-digital subsystem. The register 5332 thus stores the in-phase flow data for a given sample site or range bin.

Finally, the outputs of the multiplexers 5326, 5328 are clocked into a register 5334 by the JC-6-A pulse that occurs when the analog-to-digital subsystem is outputting the tissue data. The register 5334 thus stores the tissue data from a given sample site or range bin.

The quadrature flow data stored in buffer 5330 is applied to a PROM 5336 which contains a look-up table of data that is complementary to the data from the buffer 5330 as well as the data itself. If the FLOW-DIR address input to PROM 5336 is low, the PROM 5336 merely outputs the same data as it receives from the buffer 5330. However, in the event that blood flow is in a negative direction, the FLOW-DIR input is high, thereby causing PROM 5336 to output the complement of the data from buffer 5330. The output of the PROM 5336 is clocked into a register 5338 by the JC-6-A pulse that clock the tissue data into register 5334. Thus, after the JC-12-A pulse occurs, the quadrature flow data Q-D<0:7>, in-phase flow data I-D<0:7>, and tissue data T-D<0:7> are output from the registers 5338, 5332, 5334, respectively.

Data from the corner turning memory are routed to the centroid subsystem 86, the flow processor 84, and the spectral velocity subsystem 98 by the circuitry illustrated in FIG. 13J. The data inputs to the corner turning memory are on the same bus as the outputs of the corner turning memory. This bus is connected to the registers 5334, 5332, 5338 (FIG. 13I) and to registers 5350, 5352, 5354, and these data are clocked in by the JC-3-A pulse. The registers 5350, 5352, 5354 are used in order to delay the data from the corner turning memory since it is used by the centroid, flow processor, and spectral velocity subsystems at a time delayed from when the data are output from the corner turning memory. The outputs from the registers 5350, 5352, 5354 are clocked into registers 5356, 5358, 5360, respectively, by the JC-1-FPAL pulse generated by the circuitry illustrated in FIG. 13B, which occurs a short time after the JC-1 pulse. The tissue data from register 5356 are continuously output to the centroid subsystem. In-phase flow data from the register 4358 are output to the flow processor on the JC-9-FPAL pulse and the quadrature flow data are output from the register 5360 on the same data bus that the in-phase flow data are output when the register 5360 is output enabled by the JC-1-FPAL pulse. The in-phase flow data are thus available to the flow processor during the Johnson counter $JC_1$–$JC_8$ states, while the quadrature flow data are available to the flow processor during the Johnson counter states $JC_9$–$JC_0$.

The in-phase flow data are also clocked into a register 5362 by the JC-1-FPAL pulse, and they are output to the spectral velocity subsystem at that time. The quadrature flow data are clocked into register 5364 by the same JC-9-FPAL pulse that clocks the in-phase flow data into the register 5362. On the following JC-1-FPAL pulse, the data from register 5364 are clocked into register 5366, which then outputs the quadrature flow data on the same line that the in-phase flow data were output from register 5362. The in-phase flow data are thus available to the spectral velocity subsystem during the JC-9-FPAL pulse, which lasts from Johnson counter states $JC_1$–$JC_8$, and the quadrature flow data are available to the spectral velocity subsystem during the JC-1-FPAL pulse, which lasts during the Johnson counter states $JC_9$–$JC_0$.

It will be recalled that the ultrasound energy passes from a set of transducers through a wedge before reaching the tissue of the patient. In order to prevent the imaging system from interpreting returns from the wedge material as returns from the patient, a delay is implemented while the ultrasound signal travels to and from the far surface of the wedge. For this function, as illustrated in FIG. 13K, a set of control signals are generated by a PAL 5370 from the two's complement of the sample site number SS<0:8>, a LAST-PULS signal present during the final sample pulse, the FREQ bit identifying the ultrasound frequency, and the JC-12-B pulse generated during each sample site or range bin processing. The PAL 5370 generates a GAIN-RESET low at the start of the LAST-PULS signal which resets a pair of binary counters 5372, 5374. Thereafter, during the processing of the final sample site of the last sample pulse, the GAIN-RESET output of PAL 5370 goes low, thereby loading the counters 5372, 5374 with data from a PROM 5376. PROM 5376 is addressed by seven bits of the beam number BEAM<1:7>, data indicative of the wedge angle WEDG<0:1>, and a bit identifying the frequency FREQ. Basically, the PROM 5376 determines the value of the delay required for the ultrasound to travel through the wedge and back based upon the ultrasound frequency, the angle of the wedge, and the beam number, since the magnitude of the delay is directly proportional to the transverse position of the beam. The PROM 5376 outputs the two's complement of the number of range bin pulses constituting the delay, and this value is loaded into the binary counters 5372, 5374. At the end of the final sample site processing, the FINAL-SS output of PAL 5370 goes high, thereby allowing the counters 5372, 5374 to increment each JC-12-B pulse. When the terminal count is reached, the carry output of counter 5374 goes high, thereby disabling counter 5372 through inverter 5378 so that the counters 5372, 5374 remain at their terminal count until the counters 5372, 5374 are reset. At the same time, the high at the carry output of the binary counter 5374 is applied to the D input of a flip-flop 5380, which is then set upon the next JC-12-B pulse, to generate the SKIN pulse. Thus, after a predetermined delay from the processing of the last sample site of the last sample pulse, the SKIN pulse is generated to blank the returns from the skin line, as explained above with reference to FIG. 68. The SKIN pulse terminates on the JC-12-B pulse occurring after the counters 5372, 5374 have been reset by a GAIN-RESET low at the output of PAL 5370.

PAL 5370 also generates an START-MANCH pulse just prior to the transmission of the first sample pulse of the subsequent beam in order to allow Manchester data to be transmitted from the digital subsystems to the analog subsystems. The start of the Manchester data transmission is a function of the frequency and number of sample sites SS<0:8>. For example, starting the transmission a given period of time prior to a transmit may require seven sample sites of processing at 7.5 mHz but only five sample sites of processing time at 5 kHz. The Manchester data contain seven bits that designate the transmitter power level, one bit that identifies the frequency, and eight bits that identify the beam number. Finally, the PAL 5370 generates a LATCH-BEAM pulse that informs the Manchester circuitry that a valid beam number is now being output from the circuitry illustrated in FIG. 65. It is generated when the final sample site is being processed, while LAST-PULSE is low.

The Manchester data are generated by the circuitry illustrated in FIG. 13L. Data designating the power of the transmitted ultrasound are clocked into a latch 5400 by a TRANS-PWR-CK pulse, which, along with the power data, is generated by the CPU. The power data output by the latch 5400 are clocked into a shift register 5402 along with the frequency bit FREQ at the same time that the beam number data BEAM<0:7> is clocked into a shift register 5404. When the START-MANCH input goes high, a flip-flop 5406 is set, thereby applying a high to the data input of flip-flop 5408. On the leading edge of the next 10 mHz clock pulse through inverters 5410, 5412, flip-flop 5408 is set to make MANCH-TIME go high, thereby enabling a binary counter 5414. The counter 5414 then increments with each 10 mHz clock pulse until the count of 16 is reached, at which time the carry output of counter 5414 goes high. On the next 10 mHz clock pulse, flip-flop 5416 is set, thereby generating LAST-BIT low, which resets flip-flop 5406 and loads the counter 5414 with zero. On the next 10 mHz clock pulse, a low is clocked to flip-flop 5408, thus making MANCH-TIME low and disabling the counter 5414. It is thus seen that when START-MANCH goes high, MANCH-TIME goes high for 17 mHz clock pulses.

During the time that MANCH-TIME is high, shift registers 5404, 5402 are placed in their shift, rather than load, modes and NAND-gate 5420 is enabled, thereby applying the 10 mHz clock pulses to a pair of exclusive OR-gates 5422, 5424. The clock pulse at the output of exclusive OR-gate 5422 clocks the shift registers 5404, 5402, thereby reading the power, frequency, and beam number data out of the shift registers 5404, 5402 in sequence. The serial data are applied to a flip-flop 5426, which is clocked by the 10 mHz clock pulses at the output of exclusive OR-gate 5422. The output of the flip-flop 5426 is, in turn, applied to an exclusive OR-gate 5428. Exclusive OR-gate 5428, in combination with flip-flops 5430, 5432, and exclusive OR-gate 5434 implement a conventional bi-phase encoding scheme, known as "Manchester" coding, in which, for each clock period, the data bit is output during the first half of the clock period, and the complement of the data is output during the second half of the clock period. As a result, the Manchester data change state at the clock frequency, thereby allowing the clock to be derived from the data stream. Exclusive OR-gate 5434 thus outputs Manchester data MANCHESTER to the analog subsystems, designating the transmit power level, transmit frequency, and beam number.

The VME interface subsystem 5012 (FIG. 13A) is illustrated in FIG. 13M. The twenty-four bits of the CPU address bus are applied to buffers 5450, 5452, 5454, which, in turn, output the address bits to other portions of the timing and control subsystem and to a PAL 5456 that decodes the address bus to provide various timing and control signals. These signals include a BARD-SEL-EXT bit that enables the transceivers of the VME interface, a WR-REGISTERS pulse that causes a decoder 5458 to decode the low-order address bits to generate various timing and control signals, and a CTM-SEL output applied to the corner turning memory through inverter 5460.

The low-order bits of the data bus V-D<0:7> are applied to a transceiver 5062, while the high-order data bits V-D<8:15> are applied to a second transceiver 5064. The transceiver 5062 is connected to other portions of the timing and control interface and to a register 5066 to generate various data bits for the remainder of the timing control subsystem. For example, the register 5066 generates a FREQ bit designating the ultrasound frequency, the DPTH<0:1> data designating the number of range bins used in the image beam, two bits of WEDG<0:1> data designating the angle of the wedge through which the ultrasound passes, a CAPTR-BEAM bit used in displaying a specified beam across the entire CRT for diagnostic purposes, as explained above with reference to FIG. 13D, and a SIM-MODE bit, used as explained below. Similarly, receiver 5064 is connected to other portions of the timing and control subsystem and to a register 5068 that also generates various data and control bits. The transceivers 5062, 5064 are bidirectional, and their direction is controlled by an output from PAL 5456. The transceivers 5062, 5064 are output enabled by the BRD-SCL-EXT output of the PAL 5456, as explained above.

As explained above, decoder 5458 decodes the low-order address bits to generate an XR-MODE-CK output that is applied to the clock input of a flip-flop 5070. The data input of flip-flop 5070 is connected to the eighth bit of the data bus in order to control flip-flop 5070 and generating an XMIT-ENABLE output. The data input to flip-flop 5070 is normally high, thus causing XMIT-ENABLE to be normally high, thereby allowing ultrasound transmissions to occur. However, in the "freeze" mode or when switching operating frequencies, the CPU applies a low to the data input of flip-flop 5070 and generates an XR-MOD-CK pulse through the low-order address bits to cause XMIT-ENABLE to go low, thereby preventing further transmissions.

The circuitry illustrated in FIG. 13M also receives a number of other timing and control inputs from the CPU. These include a BD-BDSTROB pulse that is applied through an octal buffer 5476 to the PAL 5456 to allow the PAL 5456 to generate chip enable signals when valid data are present on the data bus. A V-AS pulse is applied through buffer 5476 to allow the PAL 5456 to generate various enable signals when a valid address is present on the address bus. A V-WRITE bit is used by the PAL 5456 to control the direction of the transceivers 5062, 5064, depending upon whether data are being written into or read from the CPU. A V-SYSRST low is generated whenever a system reset occurs. This SYSRST bit is applied through buffer 5476 to an AND-gate 5478 through driver 5480 to generate an AC-OR-RST low whenever a system reset occurs. An ACT-OR-RST low is also generated whenever a V-ACFAIL low is applied through driver 5480, which occurs whenever power is removed from the system. By preventing transmissions from occurring when power is being removed from the system, various field effect transistors in the analog subsystem are protected and the transmit power designating data is reset to zero.

As mentioned above, the timing and control subsystem allows the imaging system to freeze an image on the CRT. The circuitry for implementing this function is illustrated in FIG. 13N. There are two types of freeze functions, a triggered freeze and a non-triggered freeze. In a triggered freeze, the system immediately restarts scanning from beam 1, and, after all of the beams have been generated, the returns from the beams are displayed as a single frame on the CRT.

In the non-triggered freeze mode, the frame being generated when the freeze occurs is continuously displayed on the CRT without restarting from the first beam when the freeze occurs. The freeze mode is designated by the outputs of a register 5500 by decoding the six low-order bits of the data bus VME-D<0:5>, which are written into the register 5500 by the JC-0-C pulse when NOR-gate 5502 is enabled by a WR-FRZ-CTL low. It will be recalled that the CRT display includes two scan lines, i.e., line A and line B, at the left- and right-hand lower portions of the CRT screen and an image frame filling the upper portion of the CRT screen. If the scrolling waveform on scan line A is to be frozen, register 5500 outputs a LINE-A-FRZ high. Similarly, if the scrolling waveform B is to be frozen, the register 5500 outputs a LINE-B-FRZ high. If the image frame is to be frozen, an IMAGE-FRZ high is generated. If both of the scrolling waveforms as well as the image are to be frozen, the register 5500 outputs an ALL-FRZ high. It is only possible to freeze the image if both of the scrolling waveforms are also frozen. Thus, an ALL-FRZ must be high in order to get an IMAGE-FRZ high. Finally, the register 5500 also outputs a TRIGGER-FRZ high if the trigger freeze mode is being selected.

The outputs from the register 5500 are further applied to a PAL 5504, which generates an R-ALL-FRZ that goes low on the JC-0-C pulse when both scan lines and the image are to be frozen, and an R-ALL-FRZ-DEL that is generated one JC-0-C pulse later than the R-ALL-FRZ pulse in the non-triggered mode and when the TRIG-DET output from flip-flop 5506 is generated in the triggered mode. PAL 5504 also generates an R-FRZ-A-DEL and an R-FRZ-B-DEL which are applied through drivers 5508, 5510 when the output of flip-flop 5506 goes high in the triggered freeze mode and one JC-0-C pulse after the corresponding freeze input goes high in the triggered mode. Finally, PAL 5504 generates a WFFRZ-COMP pulse when a freeze has been completed which is applied through AND-gate 5512 and driver 5514 to interrupt the CPU through the V-IRQ$_5$ output. The PAL 5504 also generates a TRIGGER-IMG which is high in the triggered freeze mode.

In the triggered freeze mode, the TRIGGER-FRZ output of register 5500 will be high and either LIN-A-FRZ, LIN-B-FRZ or IMAGE-FRZ will be high. The TRIGGER-FRZ output of register 5500 causes the TRIGGER-IMS output of PAL 5504 to be high. When ST-TRIG high is applied through driver 5520 to the clock input of flip-flop 5506, a TRIG-DET is generated and applied to PAL 5504. When the TRIG-DET occurs, PAL 5504 generates an R-ALL-FRZ-DEL high two JC-0-C pulses later, thereby clocking flip-flop 5524 and outputting an RESTART-BEAM low. This RESTART-BEAM low causes the starts imaging at beam 1. The R-ALL-FRZ-DEL also places a high on the data input of flip-flop 5526 and removes the reset from flip-flop 2528. The scan controller circuitry explained above then detects the RESTART-BEAM and generates a START-FRM-STRB low at the end of the current beam. This low sets flip-flop 5530, thereby applying a high to the data input of flip-flop 5532. At the end of the last pulse of each beam, the LAST-PULSE-END going high generates FIRST-BEAM low. After the end of the first beam, flip-flop 5526 is clocked, thereby generating FRZ-FRM and applying a high to the data input of flip-flop 5536. Flip-flop 5536 then generates a TI-FRZIM high through driver 5538. The data from the previous frame are then displayed on the CRT and will remain there until the image is removed by software control.

The corner turning memory is illustrated in FIG. 13O and includes two banks, one of which data are being written into while data are being read from the other bank. The first bank includes random access memories 5550, 5552, 5554. The second bank includes random access memories 5556, 5558, 5560. Each of the RAMs 5550–5560 stores eight thousand 8-bit words designated through a 14-bit address bus. The address for bank 0 memory is CTM$_0$-A<1:14>, while the address for bank 1 memory is CTM$_1$-A<1:14>. The RAMs in the first bank 5550–5554 are enabled by a CTM$_0$-OE low and, in the same manner, the RAMs 5556–5560 in the second bank are enabled by a CTM$_1$-OE low. The RAMs in both banks 5550–5560 are write enabled by a common CTM-WE input. However, since data cannot be written into the RAMs 5550–5560 unless their chip select inputs are low, data are only written into one bank of memory at a time. The bank 0 memories 5550–5554 are enabled by an IQ-M$_0$-CS low, while the RAMs 5556–5560 in the bank 1 are enabled by IQ-M$_1$-CS low. RAM 5550 in bank 0 and 5556 in bank 1 store the in-phase flow data I-D<0:7>, RAMs 5552 in bank 0 and 5558 in bank 1 store the quadrature flow data Q-D<0:7>, and RAMs 5554 in bank 0 and 5560 in bank 1 store the tissue data T-D<0:7>.

The control signals for the corner turning memory illustrated in FIG. 130 are generated by the circuitry illustrated in FIGS. 13P–R. With reference to FIG. 13P, a set of PALs 5570–5578 are used to generate various control and data signals from a set of other control, timing and data signals. PAL 5570 receives a corner turning memory select pulse CTM-SEL from the PAL 5456 (FIG. 13M) which is generated by the CPU 130 when data are to be written into the corner turning memory. Two bits of PREV-TYPE<0:1> data identify the beam type of the previous beam in order to align that beam type with data leaving the corner turning memory. A CTM-BMACT pulse is generated to allow data transfer to and from the corner turning memory when the beam is active (i.e., data from sample sites are being obtained). A LAST-PULSE pulse goes low when the system is processing returns from the last sample pulse of each beam. Similarly, a LAST-SS pulse is generated during the last sample site of each sample pulse. A PLS$_0$-CO pulse also occurs during the last sample pulse of each beam, but it occurs at a slightly later time from the LAST-PULSE.

The PAL 5570 generates output enables, loads, and enable control signals for a sample site counter that provides the addresses for the corner turning memory, as explained in greater detail below. The PAL 5570 also generates a PLS$_0$-LD pulse for loading a pulse counter with the two's complement of the number of sample pulses in each beam, as explained in greater detail below.

The PAL 5572 receives the Johnson counter state 4 JC-4-A as a timing signal, a SPECTRUM bit, which is low when the corner turning memory is being loaded with spectral data, a BRD-SCL-EXT that is high when data are to be transferred through the VME interface illustrated in FIG. 72, three bits of the VME address VME-A<16:18>, and the VME write bit VME-WRITE. The PAL 5572 decodes the VME-A<16:18> data and, using the other control signals and the JC-4-A pulse, generates the chip selects for the in-phase and quadrature corner turning memory for bank 0 IQ-M$_0$-CS, a memory chip select for the tissue data T-M$_0$-CS for bank 0 of the corner turning memory, a chip select IQ-M$_1$-CS for the in-phase and quadrature data in bank 1 of the corner turning memory, and a chip select T-M$_1$-CS for the tissue data in bank 1 of the corner turning memory. The functions of these signals were explained above with reference to FIG. 13O. The PAL 5572 also generates output enables $CTM_0$-OE and $CTM_1$-OE for banks 0 and 1 of the corner turning memory, respectively.

PAL 5574 receives a CAP-BEAM-DET bit from the PAL 5112 (FIG. 13D) to inhibit data from being stored in the corner turning memory in the "capture mode" in which images from a single beam are displayed across the CRT screen. The PAL 5574 also receives an SS-CO pulse when the last sample site of each sample pulse is written into or read out of the corner turning memory, as explained below with reference to FIG. 13Q. Finally, PAL 5574 receives an $MS-SS_1$-CO pulse on the Johnson counter JC-12-D pulse of the last sample site of each sample pulse. PAL 5574 outputs a TOGGLE low after each velocity or image beam, thereby allowing flip-flop 5580 to toggle by virtue of the high applied to its J input through inverter 5582 and the low applied to its K input. Thereafter, flip-flop 5580 toggles with each JC-12-A pulse to make $LD-BNK_0$ alternately high and low, thereby alternately selecting corner turning memory banks 0 and 1 for writing data into. For this purpose, the $LD-BNK_0$ output of flip-flop 5580 is applied to PALs 5570, 5572, 5574 and 5578 to determine which corner turning memory bank is to be accessed.

The PAL 5574 also outputs a BMACT-EDGE which enables OR-gate 5582 when the beam is active in order to apply the JC-12-A pulses to a flip-flop 5584. In the event that the PAL 5574 outputs a high, NEW-BEAM-EN, flip-flop 5584 becomes set, thereby outputting TC-BMACT through buffer 5586.

PAL 5576 receives the BDSTROB pulse from the VME interface (FIG. 13M) in order to allow data to be written into various memories and registers. The strobe is synchronized with either the JC-6-A pulses or the JC-3-A pulses, which are also applied to the PAL 5576. From these inputs, PAL 5576 generates an AD-REG-OE to output enable the registers containing the in-phase flow, quadrature flow, and tissue data registers (FIG. 13I) to allow them to output data for writing into the corner turning memory. The PAL 5576 then also generates a CTM-WE low to allow this data to be written into whichever bank of corner turning memory that has been designated by its respective chip select signal.

PAL 5578 receives the $LD-BNK_0$ signal to designate which memory bank of corner turning memory is being accessed as well as the CTM-BMAC bit, the LAST-PULSE bit, the LAST-SS bit, the JC-4-A pulses, the SPECTRUM bit, and the $MS-SS_1$-CO bits, all of which were explained above with reference to PALs 5570–5576. PAL 5578 also receives an $LS-SS_1$-CO pulse which goes low each time the binary counter for the four least significant sample site counter bits increments to terminal count, as explained in greater detail below with reference to FIG. 13Q.

PAL 5578 generates the control signals for the circuitry illustrated in FIG. 13Q. With reference also now to FIG. 13Q, the corner turning memory address is generated from a pulse counter 5600 that counts the number of sample pulses for each beam and three sample site counters 5602, 5604, 5606. The least significant address bits CTM-A<1:4> for bank 1 of the corner turning memory are output by the sample pulse counter 5600. The remaining bits CTM1-A<5:15> are output by the sample site counters 5602–5606.

The binary counter 5602 is preloaded with the two's complement of the number of sample pulses in each beam from a register 5610. Register 5610 is loaded with INIT-PLS-CNT data indicative of the number of sample pulses by the $PLS_1$-CK pulse from the PAL 5578 of FIG. 13P at the start of each beam. The INIT-PLS-CNT data are derived from the beam type data through PAL 5090 (FIG. 13C).

After PAL 5578 generates a PLS1-LD pulse to load the pulse counter 5600 with the two's complement of the number of sample pulses, counter 5600 increments with each JC-12-D pulse when the pulse counter 5600 is enabled by the $PLS_1$-EN bit output by PAL 5578. The pulse counter 5600 is output enabled by the CTM-SEL bit from the VME interface circuitry illustrated in FIG. 13M. Pulse counter 5600 outputs a $PLS_1$-CO pulse during the last sample pulse which is used by the circuitry illustrated in FIG. 13P, as explained above.

The sample site counters 5602, 5604, 5606 are similarly loaded with INIT-SS-CNT<0:8> data indicative of the two's complement of the number of sample sites for each sample pulse. Loading of the counters 5602–5606 is triggered by the SS1-LD pulse at the output of PAL 5578. The sample site counters 5602–5606 then begin incrementing with each JC-12-D pulse as long as they are enabled by a low $LS-SS_1$-EN bit from PAL 5578 (FIG. 13P). When counter 5602 reaches its terminal count, it outputs an $LS-SS_1$-CO pulse which is used by PAL 5578 to generate an $MS-SS_1$-EN low that enables counter 5604 and 5606 to increment once each time the counter 5602 reaches the terminal count. The carry output of counter 5600 is not used to increment binary counter 5602, nor is the carry output of counter of 5602 used to increment counter 5604, because data are written into the corner turning memory in a different order than it is read out of the corner turning memory. When data are written into the corner turning memory, the pulse counter is incremented once each time the sample site counters increment from the two's complement of the number of sample sites to their terminal count. When data is read out of the corner turning memory, the pulse counter increments from the two's complement of its initial count to its terminal count each time the sample site counters 5602–5606 increment by one.

The control circuitry for bank 0 of the corner turning memory is illustrated in FIG. 13R. Register 5620 operates in the same manner as register 5610. Likewise, pulse counter 5622 operates in the same manner as pulse counter 5600. Finally, sample site counters 5624, 5626, 5628 operate in the same manner as sample site counters 5602, 5604, 5606.

Table TC-A, below, lists the program design language (PDL) for the firmware for microprocessor 5162.

The control circuitry for bank 0 of the corner turning memory is illustrated in Figure 13R. Register 5620 operates in the same manner as register 5610. Likewise, pulse counter 5622 operates in the same manner as pulse counter 5600. Finally, sample site counters 5624, 5626, 5628 operate in the same manner as sample site counters 5602, 5604, 5606.

Table TC-A, below, lists the program design language (PDL) for the firmware for microprocessor 5162.

TABLE TC-A

```
MAIN:
    INITIALIZE    stack, ports
    REPEAT
        IF mode has changed
            CALL RECONFIGURE            ; reconfigure the system
        ENDIF
    END REPEAT
    STOP RECONFIGURE:
    SEPARATE    scan.ctl into fields
    ADJUST      data to ease forming the index
    INITIALIZE  configuration registers
    FORM        array index composed of (DUAL.BM, FAST, IMG,
                FREQ, DPTH)
    current beam = first beam image #
```

```
       IF scanline A data bits not equal to 0
           IF velocity
               increment velocity scanline count
           ELSE
05             increment spectra scanline count
               IF 257-point spectrum
                   store 257 in SPEC.POINTS
               ELSE
                   store 129 in SPEC.POINTS
10             ENDIF
           ENDIF
       ENDIF
       IF scanline B data bits not equal to 0
           IF velocity
15             increment velocity scanline count
           ELSE
               increment spectra scanline count
               IF 257 point spectrum
                   store 257 in SPEC.POINTS
20             ELSE
                   store 129 in SPEC.POINTS
               ENDIF
           ENDIF
       ENDIF
25     FORM      index offset of (SPEC.POINTS, DUAL.BM,
                 FAST.IMG, FREQ, DPTH)
                 IF spectra scanline count bits not equal to 0
                 If SPEC. POINTS bit 0
                 WRITE  section  0  =  section  0  timing
30                  (SPEC.POINTS, velocity scanline count)
                 WRITE  section  2  =  section  2  timing
                    (SPEC.POINTS, velocity scanline count)
                 IF scanline B data = velocity
                     SWAP   scanline A type and scanline B type
35               ENDIF
```

```
    IF continuous
        program counter for current node = CASE.CONTINUOUS
        Form array index of (SPEC.POINTS, FREQ, DPTH)
        IF spectra scanline count = 2
            Load pad count for image + 2 spectra
        ELSEIF velocity scanline count not equal to 0
            Load pad count for image + 1 velocity 1 spectra
                mode
        ELSE
            Load pad count for image + 1 spectra
        ENDIF
    ELSE
        Program counter for current mode = CASE.IMAGE.SPECTRUM
        IF spectra scanline count = 2
            Load pad count for image + 2 spectra
        ELSEIF velocity scanline count not equal to 0
            Load pad count for image + 1 velocity 1 spectra
                mode
        ELSE
            Load pad count for image + 1 spectra
        ENDIF
    ENDIF
ELSEIF velocity scanline count not equal to 0
    Write section 3QRT register = velocity section 0 timing
        count (FAST.IMG, FREQ, DPTH)
    Write section last quarter register = velocity section
        2 timing (FAST.IMG, FREQ, DPTH)
    Initial counter for scanline A/B = loop count for
        image and velocity mode (FAST.IMG, FREQ, DPTH)
    Current PAD pulse count = PAD pulse count for velocity
        beams
    PAD pulse count for PAD image beams = -(PAD pulse count
        for velocity beams +15)
    IF type for scanline A = 0
        store scanline B type intype for scanline A
    ENDIF
```

```
         IF type for scanline B = 0
             Store scanline á type in type for scanline B
         ENDIF
             Program counter for current mode = CASE.IMAGE.
05              VELOCITY
     ELSE
             Program counter for current mode = CASE.IMAGE.
                ONLY
             Write section 3QRT register with ECG section 0 count
10           Write section last quarter register with ECG section
                2 count
         ENDIF
             Write current PAD pulse count to PAD pulse register
             RETURN
15   CASE.IMAGE.ONLY:
         Type = IMG.TYPE
         Repeat until current beam number = first image beam #
             call Beamout (IMG.TYPE)
         END REPEAT
20   END CASE
     CASE.IMAGE.VELOCITY
         current counter = initial counter for scanline A/B
         type = IMG.TYPE
         repeat until current counter = 0
25       CALL Beamout (IMG.TYPE)
         decrement current counter
         END REPEAT
         CALL Beamout (scanline A type)
         IF fast imaging mode
30           CALL Beamout (PAD.TYPE)
         ENDIF
         current counter = initial counter
         REPEAT
             CALL Beamout (IMG.TYPE)
35           Decrement current counter
             IF current beam number = first image beam #
```

```
                IF current counter not equal to 0
                    current PAD pulse count = PAD pulse count for
                        PAD image beams
                    REPEAT until current counter = 0
                        CALL Beamout (PAD.TYPE)
                        Decrement current counter for scanline A/B
                    END REPEAT
                ENDIF
            ENDIF
        END REPEAT
        CALL Beamout (scanline B type)
        IF fast imaging mode
            IF current PAD pulse count <> PAD pulse count for
                velocity beams
                Current PAD pulse count = PAD pulse count for
                    velocity beams
            ENDIF
            CALL Beamout (PAD.TYPE)
        ENDIF
    ENDCASE
CASE.IMAGE.SPECTRUM:
    Type = IMG.TYPE
    REPEAT until current beam # = first image beam #
        CALL Beamout (PAD.TYPE)
    END REPEAT
    CALL Beamout (PAD.TYPE)
    current counter for scanline A/B = initial counter for
        scanline A/B
    REPEAT
        IF scanline A type bit 0
            CALL Beamout (scanline A type)
        ENDIF
        IF scanline B type bit 0
            CALL Beamout (scanline B type)
        ENDIF
        Decrement current counter for scanline A/B
```

```
          ENDCASE
          END REPEAT

CASE.CONTINUOUS.VELOCITY OR SPECTRUM
05            Current counter = intial counter
              REPEAT unitl current counter = 0
                  IF scanline A TYPE not equal to 0
                      CALL BEAMOUT (scanline A TYPE)
                      IF current counter = initial counter
10                        STROBE START FRAME
                      ENDIF
                  ENDIF
                  IF scanline B type not equal to 0
                      CALL BEAMOUT (scanline B type)
15                    If current counter = initial counter and scanline
                         A type = 0
                          STROBE start frame
                      ENDIF
                  ENDIF
20            END REPEAT
          END CASE

BEAMOUT:

25        REPEAT until restart frame flag = FALSE
          DO WHILE first pulse bit = 1
          DO WHILE first pulse bit = 0
              IF restart frame flag = false and restart beam bit = 0
                  restart frame flange = true
30                current beam # = first image beam #
                  TYPE.SAVE = TYPE
                  TYPE = IMAGE.TYPE
              ENDIF
              write beam type to register
35            IF type = image
                  Write current beam # to image beam register
```

```
            IF current beam # = first image beam #
                Strobe start frame clock
            ENDIF
            current beam # = current beam # + beam increment
05          IF current beam # > last beam #
                Strobe last image beam clock
                Current beam # = first beam #
                IF restart frame flag = true
                    IF spectra scanline count not equal to 0
10                      beam type = PAD type
                    ELSE
                        beam type = TYPE.SAVE
                    ENDIF
                ENDIF
15              ELSE
                    IF TYPE.SAVE not equal to 0
                        TYPE = TYPE.SAVE
                        TYPE.SAVE = 0
                    ELSE
20                      frame restart flag = false
                    ENDIF
                ENDIF
            ENDIF
        END DO
25  END DO
    END REPEAT
    RETURN
```

Flow Processor

A schematic of the flow processor 84 (FIG. 2) is illustrated in FIGS. 14A–D. It will be recalled that the flow processor 84 receives its inputs from the corner turning memory 80. More specifically, the corner turning memory contains 8-bit words indicative of the in-phase and quadrature returns from the sixteen samples at each sample site depth at a given beam location. Although the data are written into the corner turning memory 80 one sample at a time for the entire set of sample site depths (i.e., depth 1-N for sample 1, depth 1-N for sample 2, etc., where N is the maximum depth), the data samples are read out of the corner turning memory for each sample site depth (i.e., depth 1, samples 1–16, depth 2, samples 1–16, etc.). Basically, the flow processor divides the spectrum of the in-phase and quadrature flow signals into sixteen frequency bands corresponding to sixteen discrete values of sample site velocities. Each filter then outputs a 12-bit word indicative of the amplitude of each filter, thereby providing in-phase and quadrature returns from sound scatterers at each discrete velocity.

With reference to FIG. 14A, timing and control for the flow processor are provided by a sequencing circuit 6500 including a pair of counters 6502, 6504. The counters are incremented by a clock pulse generated from the PLP CLK applied through drivers 6506, 6508. Resistors 6510, 6512 and 6514, 6516 are provided to terminate the outputs of the drivers 6506, 6508, respectively.

The counters 6502, 6506 may be preset to a predetermined value by applying a low to their PE* inputs. (Note: The *is used throughout to designate the inverse of a logic level, i.e., PE*=PE.) The low is generated by the output of NOR-gate 6518 by the carry TC output of counter 6504 or whenever an FP SYNC pulse is applied to NOR-gate 6518 through driver 6520. The FP SYNCH pulse is asserted whenever the firt data sample of 16 for any depth is read out of the corner turning memory. Resistors 6522, 6524 are provided to terminate the output of driver 6520. The value to which the counters 6502, 6504 are preset is determined by a series of straps, generally indicated by reference numeral 6526, that are connected to either a logic "0" line 6528 or a logic "1" line 6530 generated by inverter 6532. The value to which the counters 6502, 6504 are preset is selected so that the counters 6502, 6504 generate an appropriate number of discrete 8-bit words in order to control the operation of the remaining portion of the flow processor. In one operational embodiment, the counters 6502, 6504 are preset to 192 so that the counters 6502, 6504 count through sixty-four clock pulses before reaching the 255 maximum count of the counters 6502, 6504. Counter 6504 then generates a high at its TC output, which once again presets the counters 6502, 6504 upon the leading edge of the FP SYNCH pulse.

The PLP CLK input is also applied through driver 6506 to a series of drivers 6536–6546, which are terminated by resistors 6548–6570. The outputs of the drivers 6536, 6546 are clock pulses that are applied to other portions of the flow processor circuitry.

The output of the counter 6502, 6504 is thus an 8-bit word sequencing through sixty-four states in synchronism with the PLP CLK input to the flow processor. Thus, as explained in greater detail below, the flow processor has an operating cycle of sixty-four PLP CLK pulses and the operation of the flow processor during each of these sixty-four pulses is determined by the 8-bit word generated by the counters 6502, 6504.

Figure 15A:
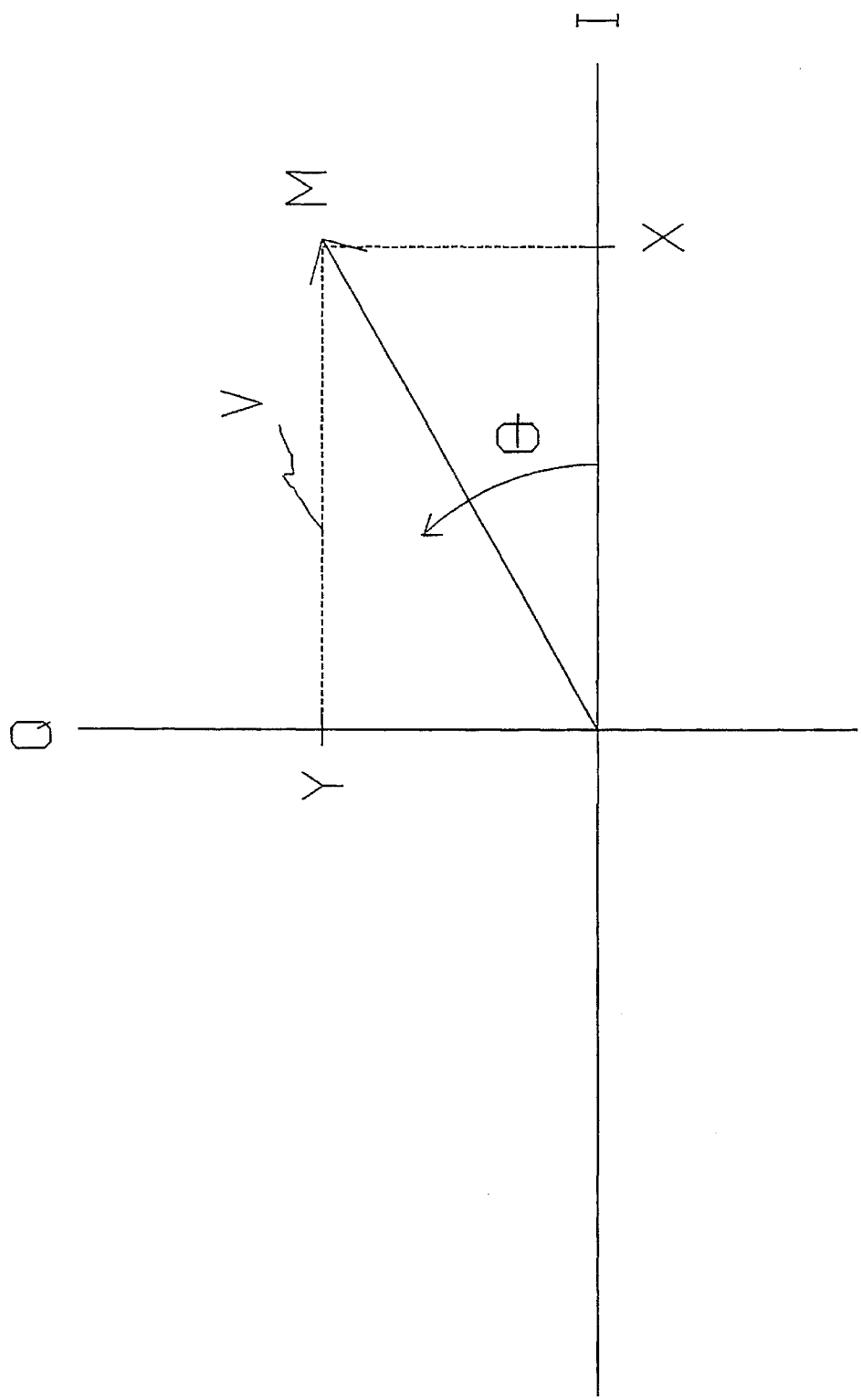
FIG. 15 is a timing diagram for the flow processor.

The theory of operation of the flow processor can best be explained with reference to FIG. 15A. An AC signal can be portrayed as a vector v rotating in a counterclockwise direction at an angular velocity of $2^n f$, where f is the frequency of the AC signal. At any point in time, the vector v will have a real component x and an imaginary component y, with the phase of the vector v being equal to $\ominus$. The real component x is thus equal to M cos $\ominus$, while the imaginary component is equal to M sine $\ominus$.

Figure 15B:
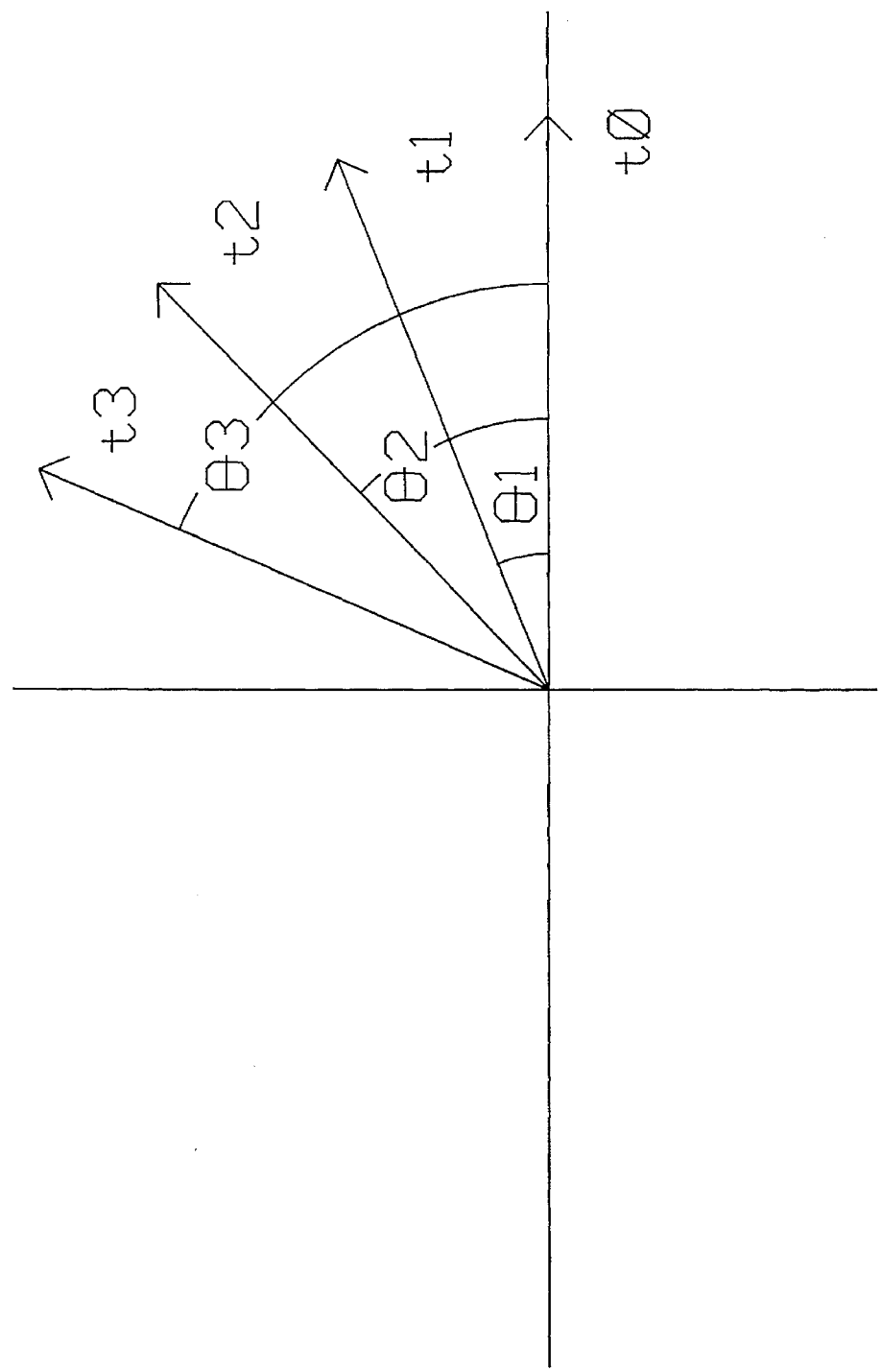
Figure 15C:
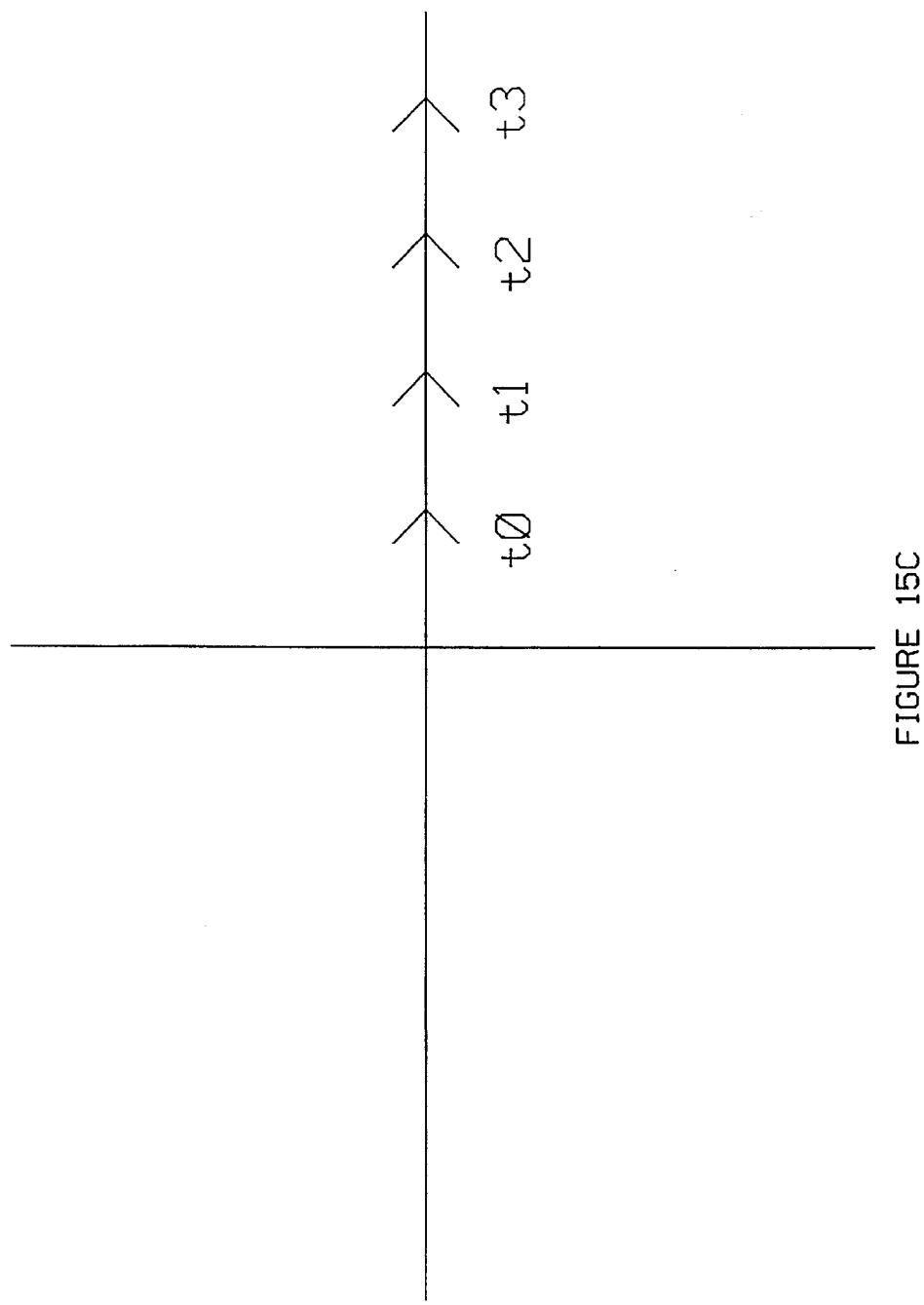
Figure 15D:
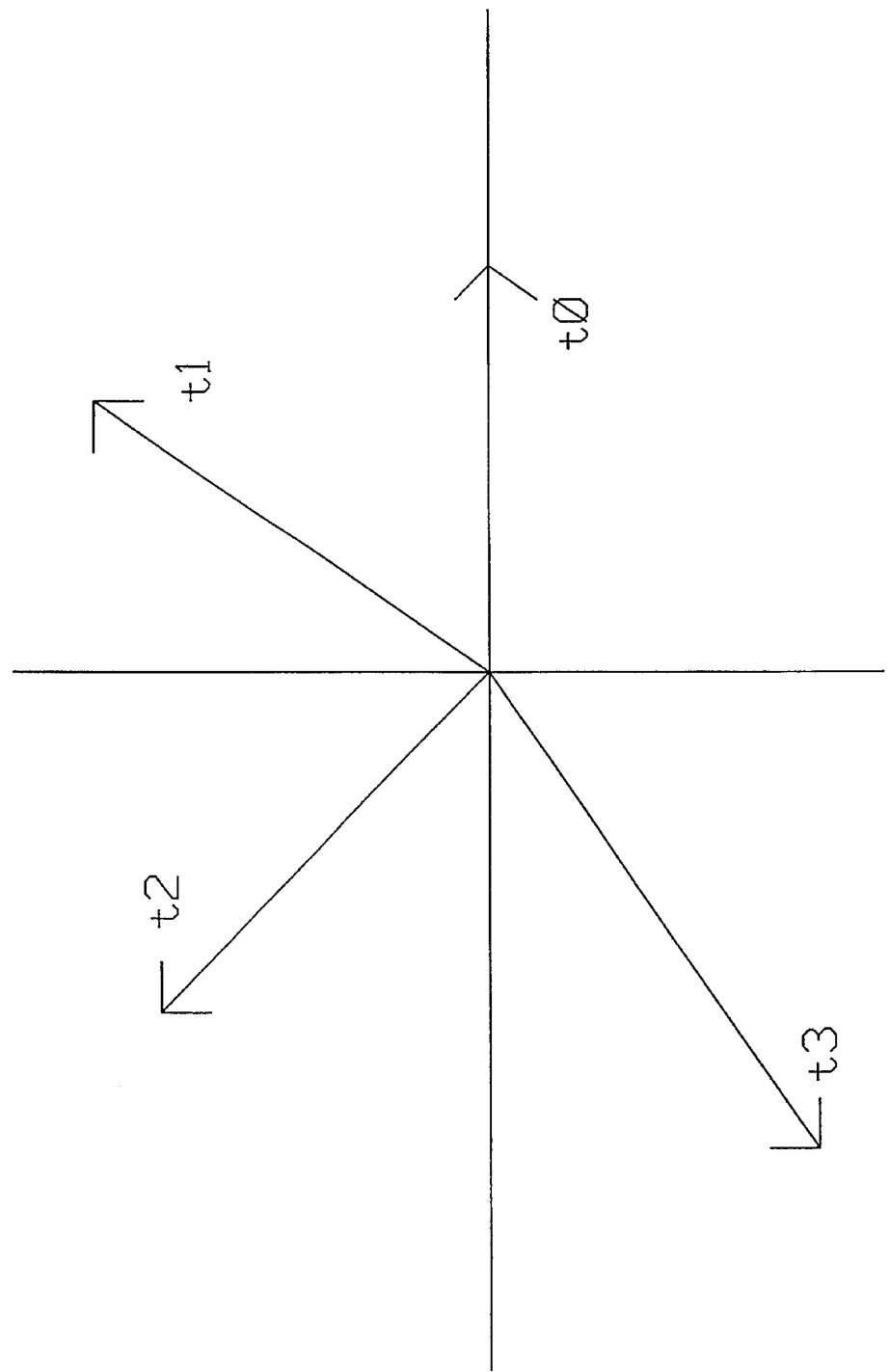
Figure 15E:
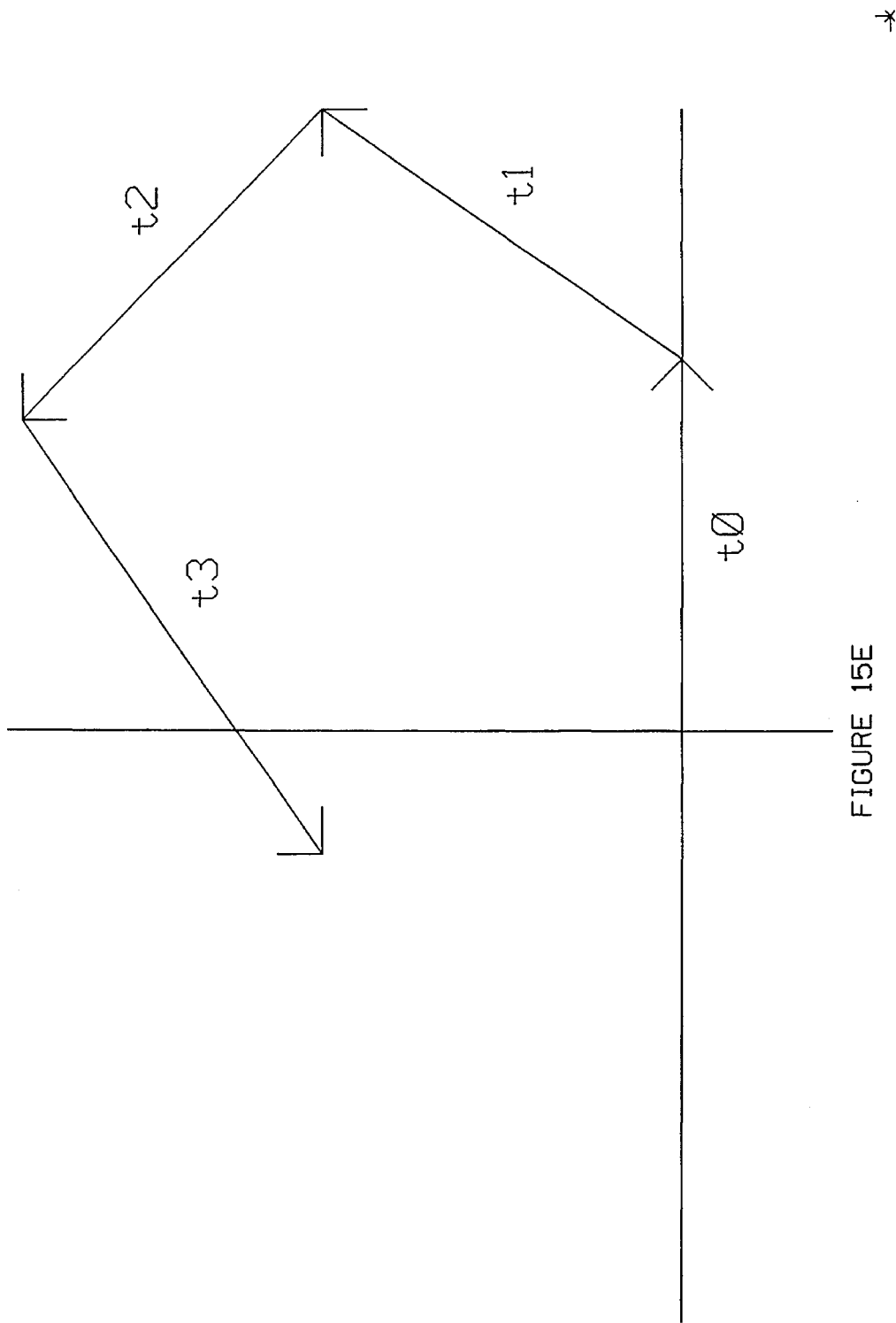

With reference to FIG. 15B, consider a signal vector at several points in time, $t_0$, $t_1$, $t_2$, $t_3$. The signal vectors illustrated in FIG. 15B can be thought of as corresponding to a sequence of samples of a signal having a constant frequency, such as Doppler returns from a sequence of samples reflected by blood moving at a single velocity. If one wanted to sum the returns from each of the samples, one could not perform this function merely by adding the signal vectors to each other since the changing phases of these signals would result in a zero result if a sufficient number of samples were used. However, the sample vectors $t_1$, $t_2$, $t_3$ can be placed in the same phase as the sample vector $t_0$ and then algebraically summed. The vectors are placed in the same phase by rotating each vector clockwise by its phase angle prior to the summation. This rotation is accomplished by multiplying the signal sample vectors by weight vectors which rotate clockwise with an angular velocity of $2^n f_o$, where $f_o$ is the filter center frequency. The result appears as illustrated in FIG. 15C. Note that the phase angles $\ominus_1$–$\ominus_3$ for a fixed sample rate are directly proportional to the frequency of the signal. As a result, multiplying a set of sample vectors by a set of coefficients will only allow the sample vectors to overlap if the sampled signal has the specific frequency of the filter. If the coefficients used in FIG. 15B are divided into a series of sample vectors derived from a signal having a frequency 4 $f_o$ (FIG. 15D), the sample vectors might be transposed to the positions illustrated, for example, in FIG. 15E. Since the sample vectors illustrated in FIG. 15E add in an essentially incoherent manner, it can be seen that, for a given set of coefficients (i.e., for frequency $f_o$), only the sample vectors from signals of a frequency $f_o$ will produce a non-zero output, assuming a sufficient number of samples are taken.

The flow processor 84 divides the in-phase and quadrature digital signals into a series of bandpass filters spaced 1 kHz apart from each other by first multiplying each digital sample by a coefficient corresponding to a signal having the frequency of each bandpass filter and then summing each product of sample and coefficient. In other words, the flow processor takes the first sample from the corner turning memory and multiplies it by coefficients of cos $2^n f_n T$, where f is 1 kHz and T is the period between samples, which, in one operational embodiment, is $\frac{1}{16}$ kHz, and n is zero. The flow processor then receives the second sample and multiplies it by coefficients of cos $2^n f_n T$ and sin 2 $f_n T$, where f is once again 1 kHz and n is 2. This product of sample and coefficients is then added to the previously obtained sample/ coefficient products. In like manner, the flow processor accumulates the product of the remaining fourteen samples and appropriate coefficients. The final accumulated sum is thus a measure of the magnitude of the 1 kHz spectral energy in the sixteen samples for a given depth. The flow processing circuitry also performs the previously described procedure, assuming that the signal is at 2 kHz, 3 kHz, 4 kHz, etc., thus producing indications of the spectral energy at 0–15 kHz in 1 kHz increments. The resulting spectrum is indicative of sixteen discrete velocity values at the sample site. In actuality, the above process is performed for both the in-phase and quadrature components of the flow signal, requiring a total of four multiplies for each flow signal sample.

Figure 15F:
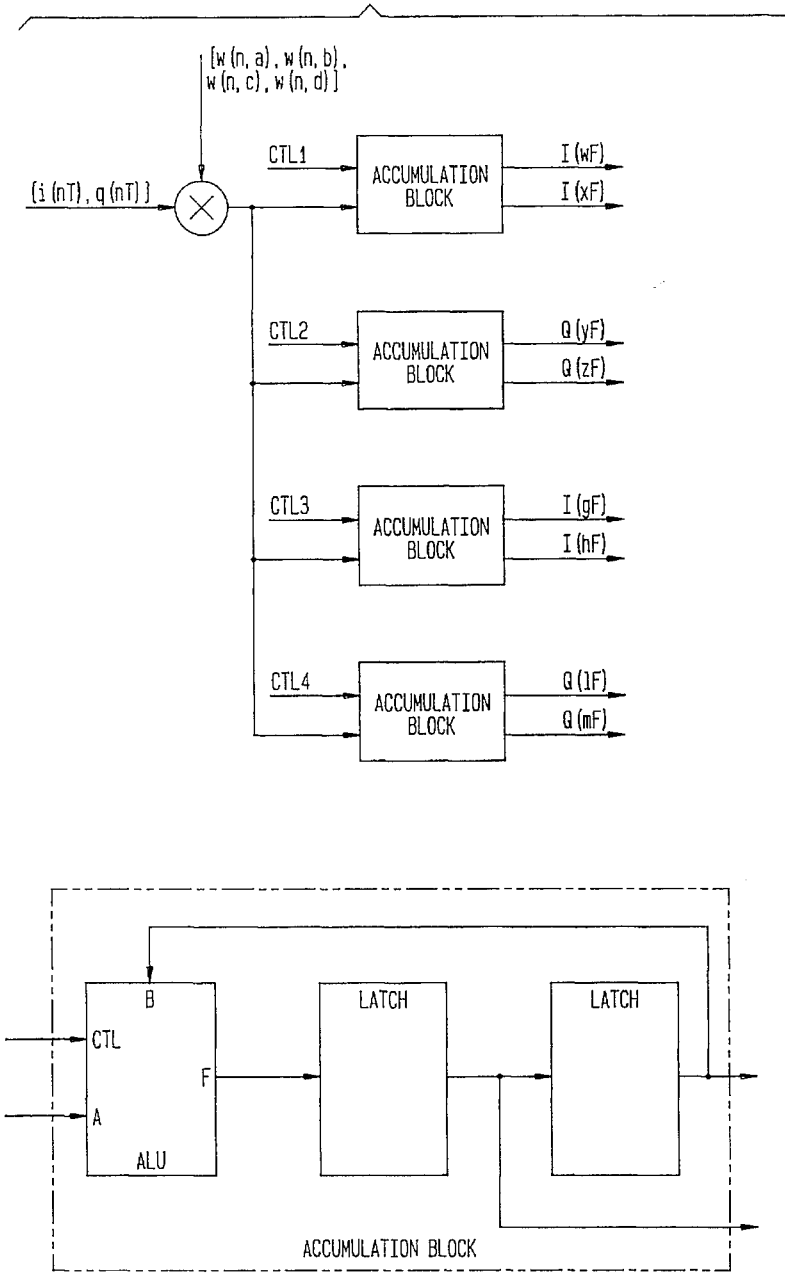

Only a limited number of weight values are required to compute the outputs for the sixteen filters. The weights are all of the form of cosines or sines of multiples of 22.5 degrees, so only five distinct weight magnitudes are possible. If the adder is replaced with an arithmetic logic unit (ALU), then only multiplies by positive coefficients are necessary, since the ALU can effectively negate the coefficient by performing a subtraction. Also, the ALU can perform a multiply-by-zero by selecting the accumulator feedback for output. Finally, the ALU provides a means of initializing the accumulator (by loading the latch with the multiplier output). With these points in mind, the flow processor is implemented with computational blocks, as shown in FIG. 15F. A single multiplier provides a parallel input into four accumulator pairs. The table below lists the arrangement of flow processor filter I and Q components into groups of four, where each group shares a single multiplier. In addition, the A and B pairs of each group share the same multiplier and ALU hardware by alternating computations between the A and B groups.

| FLOW PROCESSOR FILTER GROUPS ||||||||
| Even Board Groups |||| Odd Board Groups ||||
| 1B | 1A | 2B | 2A | 3B | 3A | 4B | 4A |
|---|---|---|---|---|---|---|---|
| I0 | I8 | I2 | I6 | I1 | I7 | I3 | I5 |
| Q0 | Q8 | Q2 | Q6 | Q3 | Q5 | Q1 | Q7 |
| I4 | I12 | I10 | I14 | I9 | I15 | I11 | I13 |
| Q4 | Q12 | Q10 | Q14 | Q11 | Q13 | I9 | Q15 |

The following is an explanation of how the four filter components of each group are able to share the same multiplier.

(1) The weights of groups 1A and 1B rotate in multiples of 90 degrees and thus are either 1 or zero in value. The multiplier weight is fixed at 1.0 and the ALU implements a sign change or multiply-by-zero.

(2) The weight vectors for groups 2A and 2B are at multiples of 90 degrees on even time increments and are multiples of 45 degrees on odd time increments. The 90 degree rotations are handled as in (1) above. Forty-five degree rotations always have a single sine and cosine magnitude. Thus, at odd time increments, the multiplier weight is a constant (0.7071), and the ALU implements sign changes as required.

(3) With the four odd filter component groups, the symmetry of the weight vectors is such that, within a group, the same multiplier magnitude is required at each time increment.

For odd n, the magnitude of $\cos(n*PI/8)$ can always be used for the $i(kT)$ multiplier and the magnitude $\sin(n*PI/8)$ can always be used for the $q(kT)$ multiplier. for even n, of value 0, 4, 8, or 12, the weight vectors are always on an I or Q axis, so the multiplier is always 1.0. For even n, of values 2, 6, 10, or 14, the weight vectors are always at 45 degree angles between the axes, resulting in a multiplier of 0.7071 for both the sin and cos terms.

Similar results apply for groups 3B, 4A, and 4B, sowing that the same multiplier coeffienct magnitudes can be used at each time increment for all filter components in a group. In each case, the ALU is used to implement a sign change for negative coefficients or a multiply-by-zero.

With reference now to FIG. 14B, the 8-bit quadrature and in-phase output of the corner turning memory is applied to a PROM 6580 that performs a multiplying function utilizing a look-up table. The PROM 6580 is continuously selected by a high at the output of inverter 6582. The three control bits for the PROM 6580 are generated from the outputs of the counters 6502, 6504 (FIG. 14A) by a set of PROMs 6586, 6588, 6590. The PROMs 6586-6590 generate a set of control signals on their outputs for each of the possible 64 states of their inputs. The outputs of the PROMs 6586–6590 are applied to respective latches 6592, 6594, 6596 upon the occurrence of the first PLP CLK 1 pulse.

Three bits output by latch 6592 designate one of five coefficients for the PROM 6580. Basically, the multi-control bits specify respective blocks of memory, each of which contains a set of data corresponding to the product of that coefficient and each of the possible values of flow signals. The output of PROM 6580 is thus the product of the selected coefficient and the flow signal, and it is output by the PROM 6580 upon the occurrence of the first PLP CLK pulse.

The product output of the PROM 6580 is recorded by a pair of latches 6600, 6602 upon the occurrence of the second PLP CLK 1 pulse. The latches 6600, 6602 then output their respective bits of the product to three arithmetic logic units 6604, 6606, 6608, each of which is operated by control signals generated by PROMs 6586 and 6588 through respective latches 6592, 6594. Basically, the arithmetic logic units 6604, 6606, 6608 perform one of three possible functions. First, they can simply pass the $B_0$–$B_3$ inputs to the $F_0$–$F_3$ outputs. Second, they can pass the $A_0$–$A_3$ inputs to the $F_0$–$F_3$ outputs. Third, they can apply the sum of the $B_0$–$B_3$ and $A_0$–$A_3$ inputs to the $F_0$–$F_3$ outputs. Fourth, they can apply the difference between the $A_0$–$A_3$ and $B_0$–$B_3$ inputs to the $F_0$–$F_3$ outputs. One of these four functions is selected by the control signals through the $S_0$–$S_3$ inputs. The outputs of the arithmetic logic units 6604, 6606, 6608 are applied to respective dual registers 6612, 6614, 6616. The arithmetic logic units 6604, 6606, 6608 are connected to fast-carry, look-ahead unit 6610. The look-ahead unit 6610 allows the three arithmetic logic units 6604–6608 to operate essentially simultaneously in order to minimize the calculation delay. Otherwise, it would be necessary for the first arithmetic logic unit to complete its calculation to determine whether it had a carry bit that would be used by the second arithmetic logic unit to perform its calculation. Under these circumstances, the three arithmetic logic units 6604–6608 would have to perform their calculations sequentially rather than simultaneously. The carry bit, which is active low, is input by each arithmetic logic unit 6604–6608 on the Cn* input. In the event that there is a carry, the propagate output P of each arithmetic logic unit 6604–6608 goes high. In the event that the carry is necessitated by a carry bit output by another arithmetic logic unit (i.e., 8+7 and a carry in), the generate G output goes high.

The operation of the circuit illustrated in FIG. 14B commences, as explained above, with the first PLP CLK 1 pulse, at which time a control word is clocked into the latches 6592, 6594, 6596. The control word then causes the PROM 6580 to multiply the in-phase flow signal for the first sample from the corner turning memory by a coefficient applicable to four filter I or Q components. The resulting product, $I_0$, is output by the PROM 6580. The second PLP CLK 1 pulse latches the $I_0$ product from the output of PROM 6580 into latch 6602. The $I_0$ product is then applied to the arithmetic logic units 6604, 6606, 6608 and fed directly to the outputs.

The second PLP CLK pulse also causes the first in-phase sample to be multiplied by the coefficient applicable to a second group of four filter components.

At the end of the second clock pulse, the arithmetic logic units 6604, 6606, 6608 have processed the first sample for the DC filter in-phase signal, $I_0$, and the first sample in-phase 8 kHz signal, $I_8$, is being output by the PROM 6580.

Upon the next PLP CLK 1 pulse, the $I_0$ signal for the first sample is clocked into the registers 6612a, 6614a, 6616a, while the $I_8$ data for the first sample is written into the latches 6600, 6602 and presented by the latches 6601, 6602 to the arithmetic logic units 6604, 6606, 6608, which then generate the product of $I_8$ and the negative of the first coefficient at their outputs. Thus, at the end of the third PLP CLK 1 pulse, the $I_0$ data for the first sample is latched into registers 6612a, 6614a, 6616a, and the arithmetic logic units 6604, 6606, 6608 are outputting the product of the $I_8$ data for the first sample and its coefficient.

Note the redundancy performed by the multiplier 6508. Since the coefficient $I_0$ data is the complement of the coefficient for the $I_8$ data, the same coefficient is used in both cases. However, the arithmetic logic units 6604, 6606, 6608 perform an A+B function when processing the $I_0$ data, but perform an A−B function when processing the $I_8$ data.

Upon the occurrence of the fourth PLP CLK 1 pulse, the $I_8$ data being output by the arithmetic logic unit 6604, 6606, 6608 are latched into registers 6612a, 6614a, 6616a, while the $I_0$ data formerly in the registers 6612a, 6614a, 6616a are latched into register 6612b, 6614b, 6616b. These later registers then apply the $I_0$ data for the first sample to the $A_0$–$A_3$ inputs of the arithmetic logic units 6604, 6606, 6608. Upon the occurrence of the fourth PLP CLK 1 pulse, the $I_0$ data for the second sample is applied to the multiplier 6580, thereby causing the multiplier 6580 to output the product of the second $I_0$ sample and its appropriate coefficient. This product is clocked into latches 6600, 6602 by the fourth PLP CLK 1 signal. Thus, at the end of the fourth PLP CLK 1 pulse, the $I_8$ data for the first sample is stored in registers 6612a, 6614a, 6616a, while the arithmetic logic units 6604, 6606, 6608 sum the $I_0$ data for the first sample with the $I_0$ data for the second sample.

Subsequent PLP CLK 1 pulses alternately apply new $I_0$ and $I_8$ data to the arithmetic logic units 6604, 6606, 6608 along with the sum of the accumulated prior $I_0$ and $I_8$ data. It is thus seen that it requires two PLP CLK 1 pulses to process each sample. Since there is a total of sixteen samples, processing all of these $I_0$ and $I_8$ samples requires thirty-two PLP CLK 1 pulses. The flow processor is implemented with two identical boards, both of which receive the same data of sixteen I and sixteen Q samples. F_ODD is wired low on oe board (by a backplane strap) to make it an "even board," and it computes the even filter outputs. The other board has F_ODD wired high, and it computes the odd filter outputs. During the following thirty-two PLP CLK 1 pulses, the $I_0$, $I_8$ data are written into a series of shift registers in parallel and then read out in serial, as explained in greater detail below. Also, during the remaining thirty-two PLP CLK 1 pulses, the circuitry illustrated in FIG. 14C (which is essentially identical to the circuitry in FIG. 14B) is active to process the sixteen samples for the data that are not processed in the circuitry illustrated in FIG. 14B. At the end of thirty-two PLP CLK 1 pulses, the registers 6612a, 6614a, 6616a contain the accumulated sums of the sixteen 18 samples, while the registers 6612b, 6614b, 6616b contain the accumulated sum of the sixteen $I_0$ samples. The outputs of the registers 6612b, 6614b, 6616b are applied to a set of shift registers, as explained in greater detail below.

The flow processor circuitry illustrated in FIG. 14B contains three additional ALUs 6620, 6622, 6624 in addition to the ALU 6626 processing the $I_0$, $I_8$, $I_1$ and $I_7$ data. The ALUs 6620, 6622, 6624 operate in substantially the same manner as the ALU 6626 to process the sixteen samples of other data. Specifically, the ALU 6620 processes the quadrature data for the DC and 8 kHz filters during the first thirty-two PLP CLK 1 pulses and the quadrature data for the 3 kHz and 5 kHz filters during the remaining thirty-two PLP CLK 1 pulses. The ALU 6622 processes the in-phase data for the 4 kHz and 12 kHz filters during the first thirty-two PLP CLK 1 pulses and the 9 kHZ and 15 kHz data during the remaining PLP CLK 1 pulses. Finally, the ALU 6624 processes the quadrature data for the 4 kHz and 12 kHz frequency components during the first thirty-two PLP CLK 1 pulses and the quadrature data for the 11 kHz and 13 kHz frequency components during the remaining thirty-two PLP CLK 1 pulses. Note, once again, that when the F ODD input is low, the even frequency components (i.e., $I_0$, $I_8$; $Q_0$, $Q_8$; $I_4$, $I_{12}$; $Q_4$, $Q_{12}$) are processed during the first thirty-two PLP CLK 1 pulses. All of these vectors have the same phase angle with respect to the applicable in-phase or quadrature axis. As a result, they all use the same absolute value of a multiplying coefficient. During the remaining thirty-two PLP CLK 1 pulses, when the F ODD input is high, the ODD kilohertz frequency components (i.e., $I_1$, $I_7$; $Q_3$, $Q_5$; $I_9$, $I_{15}$; $Q_{11}$, $Q_{13}$) are processed. Once again, all of these vectors have the same phase angle with respect to their respective in-phase and quadrature axis, thus once again allowing the same coefficients to be used.

The circuitry illustrated in FIG. 14C includes essentially the same circuitry as illustrated in FIG. 14B and operates in substantially the same manner. Consequently, for purposes of simplicity, the components of FIG. 14C have been designated with correspondingly numbered reference numerals that have been designated with a prime ('). The only substantive difference between the two circuits is that the PROM 6586 of FIG. 14B is used to generate an output enable (OE*) for the shift registers mentioned above, while the corresponding PROM 6586' is used instead to generate an EN-CP output for the shift registers.

The shift registers receiving the outputs from the circuitry illustrated in FIGS. 5B and C are shown in FIG. 14D. The outputs of the registers 6612b, 6614b, 6616b and 6612b', 6614b', 6616b' are applied to a set of twelve shift registers 6650–6672 in a bit-slicing arrangement in which the lowest order bit of each in-phase data is stored in shift registers 6672, while the highest order bit is stored in shift register 6650. Similarly, the quadrature data for all sixteen frequency components are stored in shift registers 6680–6702 in the same manner. The enable lines for the shift registers 6650–6702 are held high through respective inverters 6710–6732. The function of the shift registers 6650–6702 is controlled by the parallel/shift input (PL/SR*), which is applied to the shift registers 6650–6672 through driver 6740 and to the shift registers 6680–6702 by the driver 6742. When the PL/SR* line is high, data are shifted into the shift registers 6650–6672 by an SR CLK pulse applied through AND-gate 6744, acting as an inverter, and driver 6746. The SR CLK pulse is also applied to AND-gate 6748, which, when enabled by the EN-CP input from latch 592', is applied to the shift registers 6680–6702 through driver 6750. When the PL/SR* input is low, the shift registers 6650–6702 shift the data from the registers serially in response to SR CLK pulses. The outputs of the shift registers 6650–6702 are output in parallel when the output enable (OE*) input is low, thereby enabling respective output drivers 6760–6782 through driver 6784. Similarly, output drivers 6790–6812 are enabled by the OE* pulse through driver 6814. Resistors 6816, 6818 and 6820, 6822 terminate the outputs of drivers 6784, 6814, respectively. Similarly, resistors 6824, 6826 and 6828, 6830 terminate the outputs of drivers 6746 and 6750, respectively. Resistors 6832, 6834 and 6836, 6838 terminate the outputs of drivers 6740 and 6742, respectively.

It will be recalled that there are sixteen in-phase frequency components (i.e., $I_0$–$I_{16}$) and sixteen quadrature frequency components (i.e., $Q_0$–$Q_{16}$). The data for each of these in-phase and quadrature frequency components are a 12-bit word. The 12-bit word for the sixteen in-phase frequency components is stored in the twelve shift registers 6650–6672, each of which can store eight bits. Similarly, the sixteen 12-bit words for the quadrature frequency components are stored in the twelve 8-bit shift registers 6680–6702.

At the end of each processing frame of sixty-four PLP CLK pulses, the calculated filter values are simultaneously parallel loaded into the twenty-four ALS323 shift registers 6650–6702 for output to the centroid during the following processing frame. The shift registers are organized in a bit-slice manner, with the two registers at the left of FIG. 14D, 6650 and 6680, holding the most significant of the twelve bits for each of the eight filters computed by the board. The twelve registers at the top of the schematic hold the filter I components, and the twelve at the bottom hold the Q components.

The output enable control, from the MSB of control PROM 6586 (FIG. 14B), is used to tri-state enable all of the shift registers on the board onto the centroid interface through F244 buffers. During the first half of the processing frame (states 192 through 223 of the counter 6500, 6502), the board strapped for even filters is enabled onto the interface, and the odd board is enabled for the second half of the frame. While the F244s are enabled, the outputs of each of the eighter filters computed on a board are successively shifted out to the centroid.

A clock signal, SR CLK, received from the timing and control subsystem is used to time the shift register load and shift operations. The clock runs at one-fourth of the PLP CLK frequency, so that sixteen SR CLK pulses occur per processing frame. A parallel load control (PL/*SR), provided by the timing and control subsystem, causes the first SR CLK pulse following FP SYNCH to load the registers. Subsequent pulses do a right shift operation (up on FIG. 14D), with the exception of four pulses going to the Q registers of an odd board. All of the shift registers are wired so that right shifted data recirculates back through the register, with a full recirculation completed after eight right shifts. Data in the I registers of an odd board recirculates during the first half of a processing frame, while the board output is disabled. The second through fifth SR CLK pulses of each processing frame are gated off from the odd board Q shift registers by the EN-CP control output by the MSB of control PROM 6586 (FIG. 14C). This causes the order of data in the odd Q registers to be lined up with that of the odd I registers, so that both the I and Q components of filter 1 will be output first when the board is enabled.

Centroid, Tissue Integration, Threshold, and Merge

A block diagram of the centroid system is illustrated in FIGS. 16A–B. The purpose of the centroid system is to output a single 8-bit word indicative of the flow-indicative color or tissue gray scale from the thirty-two 12-bit words indicative of the in-phase and quadrature frequency components or 16 eight-bit words indicative of the tissue return at a given sample site. A beam timing circuit 7000 receives a clock, a beam active signal BMACT that designates when data for each beam are being output by the corner turning memory 80 (FIG. 1B), 8-bit beam number data BM<0:7> that specify which of the beams formed by the transducer elements is generating the data output from the corner turning memory 80, and 6-bit beam type BMTYP<0:5> from the timing and control system that provides certain operating parameter information. The beam timing system generates a range bin clear signal RBCLR to initialize the depth counters when the system begins interrogating at a new beam position. The beam timing circuit 7000 also generates a synchronization signal (SNLD) derived from the beam active signal, which is used to initialize various counters, as explained in greater detail below. The beam timing system also outputs a BMA<0:7> identifying the beam number. Basically, the beam timing circuit 7000 synchronizes the operation of the remaining portion of the centroid system.

A range and sample timing circuit generates signals indicative of the identity of various other items of data being processed in the centroid system. Specifically, the range and sample timing circuit 7002 generate an SNA<0:3> and SN<0:3> that identify the frequency component being applied to the centroid circuit (e.g., $I_0$, $Q_0$; $I_1$, $Q_1$; etc.) and an RBB<1:8>, which provides a digital indication of the "range bin" or depth of the sample site currently being processed. The range and sample timing circuit 7002 also generates a clock pulse RBCLK at the start of each range bin, i.e., at the start of receiving data from a new sample site. Since the SCLK clock pulse is produced for each of the sixteen frequency component data output by the flow processor at a given sample site, sixteen SCLK pulses are produced for each RBCLK pulse.

The centroid system also communicates with the CPU 130 (FIG. 2C), as explained in greater detail below, through a number of VME timing and control lines, the CPU address bus VA<0:23> and the CPU data bus VD<0:15>. These lines and buses are received by a VME address I/F and RAM sequencer 7004 and by a VME data interface 7006.

Finally, the 12-bit in-phase and quadrature flow signals are applied to a flow magnitude calculator 7008, which calculates the magnitude of the flow signal for each of the sixteen frequency components as the square root of the sum of the in-phase component squared and the quadrature component squared. The output of the flow magnitude calculator 7008 is a 12-bit signal indicative of the magnitude of the flow at a given velocity at a given sample site.

The flow magnitude signal output by the flow magnitude circuit 7008 is applied to a leveling circuit 7010 along with a 4-bit word (SNA) from the range and sample timing circuit 7002 identifying the frequency component (i.e., one of sixteen filters corresponding to the flow magnitude data). The purpose of the leveling circuit 7010 is to compensate for the cosine-shaped passband of the clutter canceller 74 (FIG. 2A). In other words, the clutter canceller inherently has a passband that attenuates the lower and higher frequency components with respect to the mid-frequency components. The leveling circuit 7010 applies a weighting value corresponding to each of the filter numbers (as indicated by the SNA data) and multiplies the flow magnitude data by that weighting function. The output of the leveling circuit 7010 is thus a 12-bit flow magnitude signal having the same value for the same magnitude of flow velocity at a sample site.

The output of the leveling circuit 7010 is applied to a bias circuit 7012 which thresholds the flow data to discriminate between flow data and noise. The bias circuit 7012 receives a threshold value from a set of random access memory (RAM) and registers 7014 in the form of a 12-bit word. The bias data are written into the RAM 7014 through the data bus output by the interface circuit 7006 at an address determined by the address bus and output by the VME address I/F and RAM sequencer 7004. The RAM and registers 7014 store a different bias value for each depth of sample site. In operation, the bias circuit 7012 subtracts the bias value from the data for each of the sixteen frequency components of the received signal (i.e., the sixteen filter outputs). Thresholding is accomplished downstream from the bias circuit 7012 by processing only outputs from the bias circuit 7012 that are larger than zero.

The output of the bias circuit 7012 is applied to both a delay circuit 7016 and a peak power frequency circuit 7018. The purpose of the delay circuit 7016 is to delay the bias-adjusted flow magnitude data for the 16 clock pulses needed to determine the frequency component having the largest power.

The centroid system also includes circuitry for determining the depth of a sample site with respect to a boundary separating two different depth ranges. As explained in greater detail below, the centroid circuit applies a cosine correction multiplier to the flow signals to compensate for the fact that the blood might not be flowing directly toward or away from the transducers. When the blood is flowing at an angle with respect to the ultrasound beam, the blood is actually flowing faster than indicated by its Doppler frequency. In fact, the true flow velocity is proportional to the Doppler frequency divided by the cosine of the angle between the beam axis and the longitudinal axis of the blood vessel. Under some circumstances, the angle between the beam and several blood vessels will differ at different depths. In order to optimize the accuracy of flow measurements under these circumstances, the centroid circuit is capable of implementing different cosine correction values at different sample site depths. Accordingly, a depth boundary is stored in the RAM and registers 7014 and output to a comparator 7020. The comparator also receives the sample site depth RBB from the range and sample timing circuit 102. In the event that the sample site depth is greater than the depth boundary (i.e., RBB>than RBND), comparator 7020 outputs a high to the VME address, I/F and RAM sequencer 7004 to cause the centroid system to utilize one cosine correction value rather than a value applicable to the other sample site depth range.

The peak power frequency circuit 7018 determines the frequency component (i.e., filter output) having the highest amplitude. As explained in greater detail below, the centroid system then calculates a centroid utilizing the amplitude of the peak power frequency and the amplitudes of the frequency components 1 kHz above and 1 kHz below the frequency of peak power.

The peak power frequency circuit 7018 first determines the frequency component of the flow spectrum having the largest magnitude. The spectrum is then shifted by an amount FPK so that the frequency component having the largest magnitude is at zero.

with reference now to FIG. 16B, the flow magnitude data FMB and FPK data specifying the shift in the centroid from the peak power frequency circuit 7018 are applied to both a denominator calculation and accumulation sequencer 7030 and a numerator calculation circuit 7032. The denominator calculation circuit calculates a value from the flow magnitude data given by the formula:

$$\underset{i=-8}{\overset{7}{\text{SUM}}} D_i \times F_i$$

$$D_{-1}, D_0, D_{+1} = 1$$

all other $D_i = 0$ where i=0 is the frequency component having the largest magnitude and i=−1 and +1 are the frequency components $F_{-1}, F_{+1}$, 1 kHz below and above that frequency component.

The numerator calculation circuit 7032 calculates a numerator given by the formula:

$$\underset{i=-8}{\overset{7}{\text{SUM}}} W_i \times F_i$$

$$W_{-1} = -1.5 \quad W_{+1} = 1.5$$

all other $W_i = 0$

The outputs of the denominator calculation and accumulation sequencer circuit 7030 and numerator calculation circuit 7032 are applied to a divide circuit 7034 that performs a calculation given by the formula:

$$C = \frac{\underset{i=-8}{\overset{7}{\text{SUM}}} W_i \times F_i}{\underset{i=-8}{\overset{7}{\text{SUM}}} D_i \times F_i}$$

The output of the divide circuit 7034 is a 6-bit word indicative of a single-frequency component representing the first moment centroid of all of the frequency components present in the sixteen samples at a given depth after the frequency spectrum has been shifted by an amount FPK. This 6-bit centroid value is applied to a spectral realign circuit 7036, which shifts the centroid value by the amount FPK frequency component data were shifted by the peak power frequency 7018. For this purpose, the peak power frequency FPK output by the peak power frequency circuit 7018 is delayed by two range clocks in delay circuit 7038 so that the centroid data for a given sample site depth are output by the divide circuit 7034 at the same time that the delay circuit 7038 applies data indicative of the amount of previously occurring shift corresponding to that sample site depth. In other words, the delay of two range clocks implemented by circuit 7038 compensates for the processing time of the denomination calculator and accumulation sequencer 7030, numerator calculation circuit 7032, and divide circuit 7034.

The output of the spectral realignment circuit 7036 is a digital value specifying the centroid as C=C'+ FPK, i.e., the centroid of the shifted frequency spectrum summed with the amount of the spectral shift. The centroid varies between a negative value indicative of a relatively high velocity in one direction and a positive value indicative of a relatively high velocity in the opposite direction. Data from the spectral realignment circuit 7036 indicative of a zero value is theoretically the dividing line between flow in opposite directions. However, because of problems caused by aliasing, it is possible for high-speed flow in one direction to manifest itself as relatively low-speed flow in the opposite direction. Basically, the use of a periodic sampling procedure results in a spectrum in which the Doppler signals repeat in the return spectrum at a repetition frequency equal to the sampling rate. Relatively high-speed flow can result in a Doppler shift that exceeds the sampling rate frequency, thereby causing overlap of the frequency spectrums. In order to minimize the problem of aliasing, the dividing line between flow in one direction and flow in the other direction can be manually set, thereby generating a 5-bit frequency boundary value FRBD which is applied to a forward/reverse boundary shift circuit 7040. The forward/reverse boundary shift circuit 7040 adds to the 6-bit centroid value an seventh bit indicative of the direction of flow. This seventh bit controls the color of the displayed flow return. Thus, a flow in one direction will result in the eighth bit being "1," thereby causing the flow signal to appear blue on the CRT. In contrast, a flow in the opposite direction will cause the eighth bit to be "0," thereby causing the flow returns to be red on the CRT.

The tissue data from the corner turning memory are also processed by the centroid system. More specifically, the tissue data are applied to a tissue average circuit 7042 that generates an 7-bit word indicative of the average of the magnitude of the tissue returns for the sixteen samples at a given sample site depth. The data indicative of the average tissue return are then applied to a tissue delay circuit 7044, which delays the tissue data to allow corresponding flow signals to catch up since the flow signals are delayed by processing the flow processor and the centroid circuit. Tissue average circuit 7042 and tissue delay circuit 7044 are the tissue integration 82 of FIG. 2B. As a result, the forward/reverse boundary shift 7040 outputs flow data for a sample site depth at the same time that the tissue delay circuit 7044 outputs tissue data for that same sample site depth.

Both the flow data from the forward/reverse boundary shift circuit 7040 and the tissue data from the tissue delay circuit 7044 are applied to a merge circuit 7046, which determines which of these data should be applied to a smoothing circuit 7048. The merge circuit 7046 is controlled by a test for flow power greater than the zero circuit 7050. Basically, the test for flow power greater than zero circuit 7050 examines the centroid denominator to determine if it is greater than zero. If so, the merge circuit 7046 (90 of FIG. 2B) applies the flow data from circuit 7040 to the smoothing circuit 7048. Otherwise, tissue data from the tissue delay circuit 7044 is applied to the smoothing circuit 7048. The merge circuit can also apply digital or tissue data from a digital storage device, such as a video cassette recorder, to the smoothing circuit 7048 when its playback PLYBCK input is high.

The smoothing circuit 7048 corrects for spurious instances of either tissue data in a field of flow data or flow data in a field of tissue data. Basically, the smoothing circuit 7048 assumes that a sample site must generate a flow signal (i.e., the magnitude of the output from that sample site must be greater than zero) if the sample sites on opposite sides of that sample site are generating flow signals. Similarly, if a sample site outputting flow data to the smoothing circuit 7048 is surrounded by sample sites having their tissue data output by the merge circuit 7046, the smoothing circuit 7048 replaces the flow signal for that sample site with tissue data. As a result, a flow pixel of one color does not appear on the CRT in the middle of uncolored tissue data. Similarly, uncolored single tissue pixel do not appear in the middle of a field of colored flow data.

The flow data from the smoothing circuit 7048 are processed by a cosine correction circuit 7052, while the tissue data from the smoothing circuit 7048 are processed by an array gain compensation circuit 7054. The cosine correction circuit multiplies the flow data by a coefficient COSC that is proportional to the inverse of the cosine of the angle between the beam axis and the longitudinal axis of the vessel. The cosine correction circuit 7052 thus allows the true blood flow velocity to be calculated when, as normally occurs, the blood is not moving directly toward the transducer.

The array gain compensation circuit 7054 adds to the tissue signal a coefficient that is a function of the gain of the beam. The gain of the beam is a function of the number of elements, which vary since the transducer has a dynamic aperture, as mentioned above.

The centroid beam timing circuit 7000 is illustrated in greater detail in FIG. 16C.

The timing circuitry synchronizes centroid processing functions to the timing and control systems beam, range bin, and sample timing and defines the centroid data output timing for the interpolator, spectrum/velocity, and digital storage boards. The basic timing signal is the timing board sample clock input TBSSCLK that is applied to an octal buffer 7100. The sample clock SCLK has a frequency of one-half the system operating frequency which is the rate for each sample site interrogated by the system. A clock having twice the sample clock frequency SSCLKX2 and four times the sample clock frequency SSCLKX4 is also applied to the octal buffer 7100. The sample clock SCLK is applied to an octal buffer 7102 to generate sample clock signals SCLKA-D for use throughout the centroid system. The inverse of the sample clock −SCLK is generated by applying the sample clock signal to an inverter 7104. Similarly, clock signals SCLKX4A and SCLKX4B, having a frequency of four times the sample clock frequency, are generated by applying the SCLKX4 to drivers 7106 and 7108.

The timing and control system also inputs a pair of beam active signals TC-BMACT and TB-BMACT, which are high during the entire period of time that a given ultrasound beam is interrogating a set of sample sites. The beam active signal indicates that valid beam data (i.e., data indicative of the flow or tissue at a set of sample sites in the ultrasound beam) are present.

Another input to the centroid beam timing circuit is a range bin clock RBCLKA that is generated to define the range bin interval for centroid processing functions. A range bin interval is the time during which all data samples for a particular sample site (i.e., value of depth) are processed by the centroid subsystem.

The centroid processing interval for the sample data for each sample site in a given ultrasound beam is initiated by the beam active signal TC-BMACT that is applied to a shift register 7110 through a driver 7112. Another beam active signal TB-BMACT clocks a pair of latches 7114, 7116 through driver 7118. Latch 7114 then stores eight bits TB-BM<0:7> that identify the beam number being processed. The beam number identifies the ultrasound beam being transmitted by the transducer as it steps across the transducer array. Latch 7116 stores the six bits TB-BT<0:5> identifying the beam type indicative of such parameters as the operating frequency of the transducer and the number of transducer elements forming the beam on transmit and receive. The beam number and beam type data are output by the latches 7114, 7116 to a latch 7120 and programmable array logic (PAL) 7122, which delays the data for a predetermined period in order to align the beam number and beam type data with the flow and tissue data for that beam as it is applied to the centroid board system. More specifically, the beam number and beam type data are applied to the centroid system when flow and tissue data are entered into the corner turning memory. The register 7120 and PAL 7122 delay the beam number and beam type data while the flow data are being processed by the filter processor 84 (FIG. 2B). The delayed beam number data output by latch 7120 is applied to a second latch 7124, which then outputs an 8-bit word BMA indicative of the beam number for which data are currently being processed in the centroid circuit. The three low-order bits of the delayed beam type data BTYA<0:2> is applied to an octal buffer 7126 that applies the beam type data CD-BMTYP<0:2> to other portions of the system. The three high-order beam type bits BTYA<3:5> are applied to other portions of the centroid subsystem, as explained in greater detail below.

The beam active signal BMADLY output by the driver 7112 to the shift register 7110 is delayed in the shift register 7110 for a predetermined period and then applied to a PAL 7130 that is clocked by the sample SCLK and used to delay the beam active signal by an amount determined by a 3-bit word generated by delay adjustment straps 7132. The PAL 7130 outputs a range bin aligned beam active signal RBA to shift registers 7134, 7136. Shift registers 7134, 7136, in turn, output a 12-bit word indicative of the number of range bin clock RBCLKA pulses occurring from the start of the beam active signal, which is applied to a PAL 7138. Shift register 7134 also generates an output applied through inverter 7140 that clocks latch 7124 a predetermined period after the start of a range bin clock RBCLKA in order to output the appropriate beam number from latch 7124.

The PAL 7138 utilizes the outputs of the shift registers 7134, 7136 to generate various initialization and data strobe signals that are either applied to other portions of the centroid circuitry or to a PAL 7142. PAL 7142 also receives the least significant three bits of the beam type data BTYA<0:3> since the timing of the initialization and data strobe signals depends upon the type of beam being used. PAL 7142 generates data strobe signals CD-DSTRBL and CS-VDSTRB that indicates when new data are being output by the centroid circuit and is used by the digital storage and spectral velocity subsystems, as explained in greater detail below. PAL 7142 also generates various beam active signals, CS-BMACT, CD-BMACT, and CI-BMACT, which are used by the interpolator and spectral velocity subsystems as well as by a digital storage device, such as a video cassette recorder. The SMBMACT output is also generated by the PAL 7142 and is used by the smoothing circuit in the centroid system. As indicated above, all of these beam active signals are used to identify the period during which flow returns from each beam are being input.

The strobe signal CO-DSTRBL output from the PAL 7142 to digital storage is gated by a signal output by a flip-flop 7146 in addition to a delayed 80 m active output by PAL 7138. The J and K inputs to flip-flop 7146 are generated by the PAL 7138, and it is clocked by the range bin clock RBCLKA. Flip-flop 7146 insures that only full pulse width strobe signals are output by PAL 7142, preventing a glitch from occurring when the delayed beam active goes low.

The remaining circuitry of the beam and timing circuitry 7000 is illustrated in FIG. 16D. This circuitry basically performs the functions of counting the number of sample and range bin clocks. The sample clock SCLKA is applied to a binary counter 7150, which generates a 4-bit output indicative of the frequency component of the flow data currently being applied to the centroid system. Counter 7150 is cleared by a negative-going SNCLRA pulse output by PAL 7152 after counter 7150 reaches a terminal count which equals the number of transmit pulses minus one. A negative-going SNCLR pulse also clears binary counter 7154 when it reaches the same terminal count. A negative going pulse SNLDL, occurring at a predetermined delay from the leading edge of each beam active, loads counter 7154 with its terminal count and synchronizes both counter 7154 and counter 7150 to the flow data as it is applied to the centroid system. The sample number data SNA are used to determine the leveling coefficients in the leveling circuit 7010, as explained in greater detail below. The SN data are used for determining the flow frequency, having the peak amplitude in the peak power frequency circuit 7018 and in the numerator and denominator calculation circuits 7030 and 7032, respectively. Since these later circuits are three sample clock pulses downstream from the leveling circuit 7010, the three sample clock delay of the sample number output by counter 7154 from the sample number output by counter 7150 causes the sample number to be properly aligned with the corresponding flow data frequency component. The delay of counter 7154 with respect to counter 7150 is determined by PAL 7152 from the beam type data BTYA.

PAL 7152 also generates a negative-going range bin clear signal RBCLR that is applied to a NOR-gate 7160. NOR-gate 7160 also receives the sample clock SCLKA and the double-frequency sample clock SCLKX2A to apply a high to flip-flop 7162 just prior to the end of the range bin clear pulse, which is then clocked into the flip-flop by the pulse SCLKX4A operating at four times the SCLKA frequency. Flip-flop 7162 then generates a negative-going zero STZEROST indicating the start of a range bin processing cycle, i.e., that data from a new range bin is being input.

Other range bin clocks signals are generated by a quad flip-flop 7164 from the output of the PAL 7152. The RBCLKA pulses are used to clock a range bin counter 7168 that generates output data RBA indicative of the range bin being processed. These RBA data are used to determine the bias levels subtracted from each of the sixteen flow magnitude frequency components in the bias circuit 7012. An AND-gate 7170 and flip-flop 7172 are used to expand the capacity of counter 7168 in order to count up to 480 range bins.

The range bin clock RBCLKA also increments a second range bin counter 7174 that, together with AND-gate 7176 and flip-flop 7178, outputs an 8-bit word RBB<1:8> indicative of the range bin which is used to determine a cosine coeffient used in the cosine correction circuit 7052 to correct for the geometry of the transducer with respect to the blood vessel in order to provide accurate flow data.

The processing cycle starts when the beam active signal TCBMACT goes high upon the leading edge of a sample clock pulse SCLK. After a predetermined number of sample clock pulses, as determined by the condition of the pipeline delay straps 7132, PAL 7130 outputs a negative-going RBA signal. Similarly, after a predetermined number of SCLK pulses, as determined by the position of the delay adjustment straps 7132, PAL 7130 outputs a negative-going SNLD pulse for one sample clock SCLK cycle. At that time, the sample number output by the binary counter 7154 (FIG. 16D) will be an n, where n is the number of samples minus one, which, in the embodiment described, is assumed to be fifteen. PAL 7152 also outputs a range bin clock RBCLK a predetermined period after the beam active signal, as determined by the delay adjustment straps 7132. At the same time, flip-flop 7162 is set by the negative-going RBCLR signal to designate the zero state ZEROST of the range processing cycle. The negative-going RBCLA pulse also resets the range bin counter 7168 and associated flip-flop 7172 to set the range bin data RBA at zero. When the beam active signal TC-BMACT goes high, the first tissue data is being latched into the centroid circuit while the flow data starts through the flow processor 84 (FIG. 2). After sixteen sample clock pulses SCLK, the flow processor 84 outputs in-phase and quadrature flow signals to the centroid circuit. During the next four sample clock pulses, the magnitude of the flow signal is calculated by the flow magnitude circuit 7008, the leveling circuit operates during the next clock pulse, and the bias circuit 7012 subtracts a bias value from the leveled flow magnitude data during the next sample clock. The frequency component having the peak power is calculated during the next four sample clock pulses by the peak power frequency circuit 7018. During the next range bin cycle, the numerator and denominator calculation occurs, followed by the normalization and divide calculation in the next range bin cycle. Finally, during the next range bin cycle, the spectral realignment is accomplished in the spectral realignment circuit 7036. During the next range bin clock, the flow data is applied to the merge circuit 1046.

The tissue data for the first data sample are processed by the tissue average circuit 7042 during the first sixteen sample clock pulses. Since the tissue average circuit 7042 then outputs the average tissue signal for the first range bin, it must be delayed by five range bin clock pulses in the tissue delay circuit 7044 so that the tissue data for the first range bin is applied to the merge circuit 7046 at the same time that the flow data to the first range bin is applied to the merge circuit 7046. During the next three range bin clocks, smoothing occurs at smoothing circuit 7048. Also, during the third range bin clock, the tissue data are processed by the array gain compensation circuit 7054, while the flow data are input to the cosine correction circuit 7052. During the next two range bin clock pulses, the cosine correction circuit 7052 processes the flow data, while the array gain compensation circuit 7054 delays the tissue data so that tissue and flow data for the same range bin merge during the next range bin clock pulse and are output to the interpolator and velocity processor during the range bin cycle.

The VME address I/F and RAM sequencer 7004 circuit is illustrated in FIG. 16E. Basically, the VME address I/F and RAM sequencer interfaces the CPU 130 (FIG. 2C) to the random access memory and registers 7014 (FIG. 16A). Address bits 16–23 of the CPU address bus are applied to a continuously enabled latch 7200. Similarly, the 14 and 15 bits of the address bus are applied to an octal buffer 7202. The fourteenth through twenty-third bits A<14:23> are output by the latch 7200 and buffer 7202 to a PAL address decoder 7204 and NOR-gate 7206 that generate various control signals, as described in greater detail below. One of these control signals is a negative-going latch strobe pulse LTCHSTR that is applied through inverter 7208 to a pair of octal latches 7210, 7212. Octal latches 7210, 7212, when strobed by the latch strobe signal, retain the first through eleventh bits V-A<1:11> of the CPU address bus.

Octal buffer 7202 also receives a number of timing and control signals from the CPU. These include a write signal V-WRITE that goes low to indicate that the CPU is attempting to write into the centroid random access memory. The CPU causes the V-BDSTROB input to go low when data are present on the CPU data bus. The CPU causes a PB-BDENA input to go low to enable the centroid random access memory to write or read data. Finally, a V-AS input goes low when the CPU outputs a valid address on its address bus.

The address of the centroid random access memory is output by a multiplexer 7220 and I/O PALs 7222, 7224. Data are stored in random access memory in four blocks, each of which is specified by the high-order A<10> and A<11> address bits. The data that are stored in the centroid RAM include data for the bias values, a first cosine correction coefficient, a second cosine correction coefficient, and a boundary depth separating the areas where the two cosine correction coefficients are applicable. Data for each of these variables are stored for each of the sixteen frequency components of the flow data for each of 512 range bins. The specific type of data (i.e., bias, cosine 1, cosine 2, or boundary) is designated by the A<10> and A<11> bits applied to the I/O PAL 7224. The I/O PAL 7224 then generates two high-order address bits RA<9> and RA<10>, which designate the block of the random access memory where the set of data for that variable is stored. At the same time, the I/O PAL 7224 designates a select signal for the multiplexers SEL<0:1> that causes the multiplexers 7220, 7222 to apply the lower order bits RA<0:8> to their outputs from one of three possible sources. The first source is the CPU address from the latches 7210, 7212. The second set of address bits are the beam number data BMA, which are used to store cosine correction data. Finally, the range bin number data RBA are used to designate the storage location of the bias values.

The I/O PAL 7204 is also used to generate various control and data strobe signals used by other portions of the centroid system. PAL 7204 outputs a control strobe CTLSTR that is used to clock CPU data from the CPU data bus into a latch to generate control signals, as explained in greater detail below. A latch strobe pulse LTCHSTR is used to cause data on the CPU data bus to be latched into an input register for writing into the centroid RAM, as described in greater detail below. The PAL 7204 also generates a write output VWRITE that designates that input data are to be applied to the centroid RAM through a transceiver. The VREAD and VTREN control signals are also used to enable various transceivers in the centroid board VME data and RAM interface circuit 7006, as describe in greater detail below. The I/O PAL also generates a number of strobe signals through a registered PAL 7228. PAL 7228 generates three strobe signals RBNDSTR, COSCSTR, and BIASSTR to latch the range bin, cosine correction, and bias data from the RAM into respective registers. The SEQWR and WRSTR strobes are used to read data from and write data into the centroid RAM, respectively.

PAL 7224 generates its output from input data consisting of the sample number data SN<0:3> three bits of beam type data BTYA<3.5> identifying the number of transmit pulses in a beam, the A<10> and A<11> address bits of the CPU, the sample clock SCLKA, the VREAD and VTREN control signals, and a RAMWPEND signal output by a flip-flop 7230. Flip-flop 7230 is set by a negative-going pulse applied by the PAL 7204 to the clock input of the flip-flop 7230 through inverter 7232 before the CPU attempts to write data into the centroid RAM. The output of the flip-flop 7230 then remains high until PAL 7228 generates a negative-going WPENDCL that resets the flip-flop 7230 after data have been written into the centroid RAM.

A similar flip-flop arrangement is used to generate the control signal VTREN that enables various transceivers. Specifically, flip-flop 7234 outputs a low VTREN signal upon the leading edge of the V-AS input from the CPU when a valid address is present on the address bus. Transceivers are then enabled to allow this address data to be applied to the address inputs of the RAM. At the end of the write cycle, flip-flop 7234 is set by a low generated by the PAL 7204 from various address bits of the CPU. It is thus seen that the VME address I/F and RAM sequencer 7004, as illustrated in FIG. 16E, applies appropriate address data to the address inputs of the RAM and generates appropriate control and strobe signals to route the address and data to the RAM.

The VME data interface circuit 7006 and the RAM and registers 7014 are illustrated in FIG. 16F. Data from the 16-bit data bus of the CPU are applied to bidirectional transceivers 7250, 7252, which allow CPU data to be applied to the RAM when the VWRITE input is high and otherwise allow data to be read by the CPU from the RAM. The outputs of the transceivers 7250, 7252 in either direction are enabled by a low VTREN input which, it will be recalled, is low whenever a valid address is being output by the CPU. When the CPU is writing data into the RAM 7254, 7256, the data at the output of the transceivers 7250, 7252 are stored in octal latches 7258, 7260 by a positive-going pulse at the output of inverter 7262 generated by the latch strobe pulse LTCHSTR from the PAL 7204 (FIG. 12). Octal latches 7258, 7260 then apply the data to the data inputs of the RAMs 7254, 7256, respectively.

When the CPUs are to receive data from the RAMs 7254, 7256, the RAMs 7254, 7256 output data to respective octal buffers 7266, 7268. Octal buffers 7266, 7268, in turn, apply the data to respective transceivers 7270, 7272 that output the data to the transceivers 7250, 7252 when enabled by a negative-going VREAD pulse. Octal latches 7258, 7260 output data to the RAM 7254, 7256 only when they are enabled by a low SEQWR, thereby designating that data are being written into the RAMs 7254, 7256. A high SEQWR applies a low to the output enable inputs of the RAMs 7254, 7256 through inverter 7278, thereby allowing data to be read from the RAMs 7254, 7256. stored in the RAMs 7254, 7256, namely, a bias value, two cosine correction coefficients, and boundary data dividing the depth bins into two ranges for which the respective cosine correction coefficients are applicable. The depth boundary stored in the RAM 7254 is applied through octal buffer 7266 to a comparison circuit 7280. Comparison circuit 7280 also receives an 8-bit word RBB<1:8> indicative of the range bin from which flow data are currently being received. In the event that the current range bin is greater than the boundary data, comparison circuit 7280 applies a low to the data input flip-flop 7282, which then outputs a high RGT upon the next negative-going range boundary strobe RBNDSTR from the PAL 7228 (FIG. 16E). The RGT signal is applied to the I/O PAL 7224 (FIG. 16E) to a low the PAL 7224 to designate which cosine correction coefficient should be read from memory through the address multiplexer to PAL 7220.

The bias data are read from RAM 7254 through octal buffer 7226 into a latch 7286 supplemented by a quad register 7288 to store the bias data upon receipt of a negative-going bias strobe BIASSTR from the registered PAL RAM strobe 7228 (FIG. 11). Similarly, cosine correction values are stored in latches 7290, 7292 upon receipt of a negative-going cosine correction strobe COSCSTR.

Finally, data from the CPU are applied through transceiver 7250 to an octal register 7294 and stored upon receipt of a negative-going control strobe pulse CTLSTR to generate a 5-bit word FRBD<0:4> indicative of the forward/reverse boundary, i.e., the frequency above which flow data frequency components are considered blood flow in one direction and below which are considered blood flow in the opposite direction. The register 7294 also generates one bit of data FREQ identifying the carrier frequency of the transmitted ultrasound as being either 5 kHz or 7.5 mHz. Finally, octal register 7294 generates two bits of data TBL<0:1> for the leveling circuit 7010 to disable the amplitude compensation function of the leveling circuit 7010 for test purposes.

As explained above with reference to FIG. 16A, the centroid system receives in-phase and quadrature flow data that are applied to a flow magnitude circuit 7008 that calculates the flow magnitude as the square root of the sum of the in-phase data squared and the quadrature data squared. As illustrated in FIG. 16G, the quadrature data is an 11-bit word FC-Q<0:10>, with a single bit FC-Q<11> identifying the sign of the quadrature flow data. Similarly, the in-phase flow data are in the form of an 11-bit word FC-I<0:10> and a single bit FC-I<11> identifying the sign of the in-phase flow data. The sine bits FC-Q<11> and FC-I<11> are applied to an input normalization PAL 7300 and are output by the PAL as respective Q sign QSGN and ISGN bits upon the leading edge of the high-frequency clock pulse SCLX4 at the output of driver 7302. Although the in-phase and quadrature flow data each consist of eleven bits, the actual magnitude calculation is performed using seven bits of data. In order to insure that these seven bits include the seven most significant bits of the flow data, the in-phase and quadrature data are shifted until the most significant bit is a "1," the flow magnitude calculation is then made, and the data are then shifted back the same number of bits to provide the correct flow magnitude value. Accordingly, the quadrature and in-phase flow data are applied to shift registers 7304, 7306, 7308. The data is then shifted through the shift registers 7304, 7308 with each pulse of the high-frequency sample clock SCLKX4 at the output of driver 7310. The most significant two bits of the quadrature data and the most significant bit of the in-phase data are applied to the PAL 7300, which outputs a 2-bit word ISCTL indicative of how many bits were shifted in order to place a "1" in either the 7-bit quadrature or in-phase data output from the shift registers 7304–7308. The ISCTL data are generated by a counter internal to the PAL 7300 that is reset by the ZEROST pulse from flip-flop 7162 (FIG. 16D) at the start of sampling at each range bin. When either of the most significant bits of the quadrature of in-phase data is "1," the shift control data ISCTL output by the PAL 7300 is applied to the shift registers 7304–7308 to prevent further shifting of the data. The data are then latched into registers 7310, 7312 upon the leading edge of the sample clock SCLK applied through driver 7314. The sign bits QSGN and ISGN are also latched into the PALs 7310, 7312.

The 7-bit in-phase and quadrature data and associated signs are applied to an EPROM 7318 containing a look-up table of the square root of the sum of each possible in-phase flow magnitude squared and each possible quadrature flow magnitude squared. The resulting output of the EPROM 7318 is an 8-bit word indicative of the flow magnitude after it has been normalized in the shift registers 7304–7308. The normalized flow magnitude data is then applied by the EPROM 7318 to output shift registers 7320, 7322, which shift the data back responsive to each SCLK4XD pulse by an amount designated by the OSCTL data. The OSCTL data are output by shift registers 7324, 7326, which receive the data ISCTL indicative of the amount of bits the data were shifted in the input shift registers 7304–7308. Shift registers 7324, 7326 delay the shift magnitude data so that when the flow magnitude data are being output by the EPROM 7318, the shift registers 7324, 7326 output data indicative of the number of bits the corresponding data were shifted in the input shift registers 7304–7308. Output shift registers 7320, 7322 thus output twelve bits of flow magnitude data FM with the same scale as the input flow data FC-Q and FC-I.

As explained above with reference to FIG. 16A, the flow magnitude data from the flow magnitude circuit 7008 is applied to a leveling circuit 7010 that compensates for frequency selective attenuation in the clutter canceller. The leveled flow magnitude signal is then output by the leveling circuit 7010 to a bias circuit 7012 that subtracts a predetermined bias value from the level flow signals. The leveling and bias circuits 7010 and 7012, respectively, are illustrated in further detail in FIG. 16G. As explained above, the clutter canceller inherently generates a signal having a larger magnitude at the middle frequency components and a reduced amplitude at the higher and lower frequency components. The leveling coefficients needed to restore the flow data frequency components to their true values are thus the inverse of this amplitude weighing function. Each coefficient is, then, a function of the frequency component. The frequency component (i.e., 0 to 15 kHz in 1 kHz steps) is identified by four bits of SNA<0:3> data that are applied to a PROM 7340 that contains a look-up table specifying a coefficient for each frequency component. The SNA data are generated by the sample number counter 7150 (FIG. 16D) from the sample clock SCLKA. The PROM 7340 also contains a look-up table containing equal data values that are selected by TBL data output by register 7294 (FIG. 16F) to perform internal tests by disabling the leveling function. In other words, the SNA data select a leveling coefficient corresponding to the frequency component of the flow data being output by the output shift registers 7320, 7322 (FIG. 16G). Alternately, leveling coefficients that are equal to each other may be used to disable the leveling function. The leveling coefficients are applied by the PROM 7340 to a 16-bit multiplier/accumulator 7342 which also receives the 12-bit flow magnitude signal. Upon being clocked by the sample clock SCLKB, the 16-bit multiplier/accumulator generates fourteen bits of data. The lowest twelve order bits are applied to adders 7344, 7346, 7348, while the two overflow bits OVFLW are applied to overflow correction PALs 7350, 7352. In the event that an overflow occurs, the leveled flow data with the bias values subtracted are considered to be all "1" so that, in the event of an overflow condition, PALs 7350, 7352 generate twelve FMA bits that are all "1." If no overflow occurs in the 16-bit multiplier/accumulator 7342, the adders 7344, 7346, 7348 subtract the bias value from the flow data. The adders 7344, 7348 perform a subtraction function since the bias data are inverted by the latch 7286 and register 7288 and the 2's complement of this inverted bias signal is added by the "1" applied to the carry CO input of the adder 7344. By adding the magnitude signal at the output of multiplier/accumulator 7342 to the 2's complement of the bias data, the adders 7344, 7346, 7348 output the difference between the magnitude and bias data. This difference data are then applied to the overflow PALs 7350, 7352 to output the leveled and bias-adjusted flow magnitude data FMA<0:11> to the peak power frequency circuit 7018 (FIG. 16A).

It will be recalled that the peak power frequency circuit 7018 shifts the frequency spectrum of the flow data until the frequency component with the largest magnitude is at the zero frequency point. By counting the number of frequency components that the spectrum must be shifted until the frequency component having the largest magnitude is at zero, the frequency component with the largest amplitude can be determined. The peak power frequency circuit 7018, as illustrated in FIG. 16H, receives the flow magnitude data FMA<0:11> and applies them to a pair of 8-bit registers/comparators 7370, 7372. The data are stored in the registers/comparators 7370, 7372 upon the occurrence of the sample clock SCLKB. As each flow magnitude word FMA is applied to the registers/comparators 7370, 7372, the registers/comparators 7370, 7372 generate respective "less than," "greater than" or "equal" signals indicative of the comparison between the currently data word and the previously input data word. A control input extending from the C/S0 output of register/comparator 7372 to the C/S1 input of register/comparator 7370 causes the register/comparator 7370 to default to the register/comparator 7372 in the event that the currently input data to register/comparator 7370 are greater than the previously entered data. As a result, the "less than," "greater than" and "equal" outputs of the registers 7370, 7372 can be tied together. These outputs from the registers/comparators 7370, 7372 are biased high through resistors 7374, 7376, 7378. The "greater than" outputs from the registers/comparators 7370, 7372 are applied to a latch 7380 that also receives the SN<0:3> data indicative of the frequency component of the flow data that is being applied to the registers/comparators 7370, 7372 and data BTYA<3:5> indicative of the number of frequency components (i.e., sixteen) being used.

The PAL 7380 performs two functions. First, if the SN data are zero (indicating that the flow data for the first frequency component are being input), it generates signals at the S0–S1 inputs to the registers/comparators 7370, 7372 to cause the first flow magnitude data to be loaded into the registers/comparators 7370, 7372. Second, if the "greater than" outputs of the registers/comparators 7370, 7372 are high, it latches the current SN data identifying the corresponding frequency component so that the PAL 7380 always retains the frequency component having the largest magnitude. After sixteen frequency components have been applied to the registers/comparators 7370, 7372, the stored SN value will be indicative of the flow data frequency component having the largest magnitude. These data are applied in the form of a 4-bit word to an octal latch 7382 and are stored there upon the occurrence of a range bin clock RBCLKB when flow data from the next range bin are to be processed. Thus, latch 7382 contains the flow magnitude frequency component having the largest magnitude at a given range bin, while flow data for the next range bin are being input to the registers/comparators 7370, 7372.

The output of the latch 7382 identifying the frequency component of maximum amplitude is applied to a shift register 7384 that delays the data for two range bin clock pulses RBCLKB, during which time the flow magnitude data FMA<0:11> applied to shift registers 7386, 7388 are shifted back by the sample clock pulses SCLKC the same number of bits that they had previously been shifted. For this purpose, the number of bits that the flow magnitude data must be shifted is identified by the DLY outputs of the PAL 7380. Shift registers 7386, 7388 then shift the twelve bits of flow magnitude data FMB over sixteen sample clock pulses SCLKC, while, at the same time, outputting FPKC data indicative of the frequency component of the corresponding flow data having the maximum amplitude as well as FKP data from the output of latch 7382 representing the frequency component of maximum amplitude for flow data to range bins subsequent to the flow data being output by the shift registers 7386, 7388.

As explained above with reference to FIG. 16B, the centroid system calculates a centroid by individually calculating a denominator and numerator from the flow magnitude data and then dividing the denominator by the numerator at 7034. The denominator calculation and accumulation sequencer circuit 7030 is illustrated in FIG. 16I. As explained above, the denominator is calculated by summing the flow magnitude data at the frequency component of maximum amplitude with the flow magnitude data having frequency components of 1 kHz less than and 1 kHz greater than the frequency component of maximum amplitude.

With reference to FIG. 16I, the operation of the denominator calculation circuit is controlled by a sequencer 7400 that receives control signals from a PAL 7402 and timing signals from a binary counter 7404. The NORMDET PAL 7402 is provided to normalize the denominator data, as explained in greater detail below.

The flow magnitude data FMB<0:11> are applied to accumulator PALs 7410, 7412, 7414 and are stored therein by the sample clock SCLKC. A fourth accumulator PAL 7416 operates in conjunction with a carry block 7418 to accumulate overflow from the PAL 7414.

As each frequency component of flow magnitude data FMB is applied to the PALs 7410, 7416, the data are either held or accumulated, depending upon whether the DENACC or HOLD inputs are high. If the HOLD input is high, the incoming flow magnitude data FMB are held in the PALs 7410, 7416, but do not accumulate. When the DENACC input is high, the flow magnitude data FMB accumulate with previously input flow magnitude data. Insofar as the denominator makes use of only the flow magnitude frequency component of maximum amplitude and the adjacent flow magnitude frequency components, the DENACC input goes high only when these frequency components are input to the denominator calculation circuit. When all of the flow magnitude data has been applied to the denominator calculation circuit, the DEN output of PAL 7400 goes low, thereby causing the PALs 7410, 7416 to present the denominator data to shift registers 7420, 7422. The function of shift registers 7420, 7422 is to shift the denominator so that the most significant bit of the denominator FP is shifted to the twelfth bit of the sixteen $F_p$ bits for the purpose of normalization. The NORMDET PAL 7402 receives the nine most significant bits of the denominator Fp and applies appropriate left and right shift signals to the normalization control PAL 7400, which, in turn, outputs two shift control bits SCTL to the shift/storage registers 7420, 7422 to control the shift direction. The shift/storage registers 7420, 7422 then output the normalized denominator Fp upon receipt of the SRLDEN from the normalization control pal 7400.

The centroid board numerator calculation circuit 7032 (FIG. 16B) calculates the numerator for the centroid processing and controls the normalization shifting for the numerator and denominator calculation. The centroid board numerator calculation circuit, as illustration in FIG. 16, includes a 16-bit multiplier/accumulator 7430 that receives the flow magnitude data FMB as well a 5-bit coefficient from PROM 7432. PROM 7432 generates the coefficient from four SN bits indicative of the frequency component of the flow data currently being entered and four bits of FPK data indicative of the frequency component of the flow magnitude signal having the peak amplitude. These data are loaded into the PROM 7432 by a negative-going SRLDEN pulse from the normalization control PAL 7400 (FIG. 16I). In operation, the numerator coefficient PROM 7432 outputs a value of −1.5 when the SN data are equal to the FPK data minus 1 (i.e., the flow magnitude data FMB being entered are for the 1 kHz frequency component less than the peak frequency component), zero when the SN data are equal to the FPK data (i.e., the flow magnitude FMB data peak frequency component is being entered), and 1.5 when the SN data are equal to the FPK data plus 1 (i.e., the flow magnitude signal FMB is for the frequency component 1 kHz above the peak frequency component). The numerator coefficient PROM 7432 outputs a zero coefficient at all other times.

The operation of the multiplier/accumulator 7430 is controlled by a shift register 7434 which is clocked just prior to the leading edge of each sample clock SCLKD when NOR-gate 7436 detects that the sample clock, the double clock SCLKX2A, and the quadruple sample clock SCLKX4B are all low. Shift register 7434 initially generates a numerator strobe signal NXYSTR that clocks the flow magnitude FMB for a given frequency component and the corresponding coefficient into the multiplier/accumulator. Just prior to the next sample clock SCLKD, shift register 7434 outputs a numerator product strobe NPRODSTR to the multiplier/accumulator 7430 that outputs the product to an output register in the multiplier/accumulator 7430. At the same time, a numerator product enable input NPRODEN goes low to enable the output of an octal buffer 7440 that outputs the four frequency component identifying bits FPK as the four low-order bits of the numerator N<0:3>.

The multiplier/accumulator 7430 and associated circuitry repeat the above-described sequence for each frequency component of flow magnitude data FMB. When the flow magnitude for the first frequency component is applied to the multiplier/accumulator 7430, numerator control PAL 7400 (FIG. 16K) outputs a high ACCUM input that causes the multiplier/accumulator to add the numerator product N for each succeeding frequency component to the numerator product N to the accumulated numerator products N for the preceding frequency components. However, since only two of the numerator products N are other than zero, the multiplier/accumulator accumulates only the two numerator products N. After all of the numerator products have been accumulated, they are applied to shift/storage registers 7444, 7446, 7448. The normalization control PAL 7400 (FIG. 16I) then outputs a shift register load enable SRLDEN that disables the numerator coefficient PROM 7432 (to prevent it from applying spurious coefficents to the multiplier/accumulator 7430) and enables the shift registers 7444, 7446, 7448 to be loaded with the numerator data N. The numerator data N is then shifted either right or left or held by the SCLKX4B clock under control of the 2-bit shift control data SCTL generated by the normalization control PAL 7400 (FIG. 16K). It will be recalled that the SCTL data is indicative of the direction that the denominator FP was shifted in the shift/storage registers 7420, 7422. Since the numerator is shifted in the registers 7444, 7446, 7448 at the same time and under control of the same signals that are used to shift the denominator FP in the registers 7420, 7422, the numerator and denominator have the same scale. The numerator N<0:22> is then output to the centroid board divide, shift and merge circuit 7034 (FIG. 16B) along with a load signal LDFPWR generated by NOR gate 7450 when normalization control PAL 7400 generates a numerator product enable NPRODEN and shift register 7434 generates a load pulse that is applied to the NOR-gate 7450 through inverter 7452.

The centroid board numerator calculation circuit also includes a shift register 7456 that generates the hold HOLD and accumulate DENACC control signals for the centroid board denominator calculation circuit (FIG. 16I). The shift register 7456 clocks two bits of data generated by the numerator coefficient PROM 7432, which indicate when the SN data are equal to the FPK data plus or minus 1. If so, the numerator coeffcent PROM 7432 outputs a "01" that is clocked to the shift register 7456 a number of stages accounting for the processing delay in the denominator calculation circuit (FIG. 16K). Shift register 7456 then generates a high DENACC to instruct the PALs 7410, 7416 (FIG. 16I) to accumulate the denominator data, and, at all other times, generates a hold HOLD output to cause the PALs 7410–7416 to hold the previously entered data without accumulating any additional data.

The centroid board divide, shift and merge circuit 7034 (FIG. 16B) is illustrated in further detail in FIG. 16L. The function of the divide, shift and merge circuitry is to calculate the centroid from the numerator and denominator data and to output either the centroid or tissue data (generated as described below), depending upon whether the flow magnitude denominator FP is greater than a predetermined value. Eight bits of the numerator data N<7:14> and seven bits of the denominator data FP<1:7> are applied to an EPROM 7460 that contains a look-up table for each of the possible numerator and denominator combinations addressing the EPROM 7460. The resulting centroid calculation is output to a register 7462 and clocked into the register 7462 by the range bin clock RBCLKB at the start of a centroid calculation for the next sample site. The output of the register 7462 is thus the centroid before it has been shifted back by the number of 1 kHZ frequency components that it was shifted in the peak power frequency circuit (FIG. 16H). This centroid calculation is applied to a peak frequency shift PROM 7464 containing a look-up table that adds the centroid value from the register 7462 to the peak frequency data FPKC indicative of the number of previous shifts that occurred to generate the true centroid at its output. The centroid is in modulo 16 form so that a peak frequency component of 17 kHz due to aliasing is recognized as a 1 kHz frequency component.

The centroid at the output of the peak frequency shift PROM 7464 is next applied to a forward/reverse boundary PROM 7466 that compares the centroid value to the forward/reverse boundary data FRBD<0:4> indicative of the frequency component separating flow in one direction from flow in the opposite direction. The forward/reverse boundary PROM 7466 applies the seven highest order bits of the centroid to the seven lowest order bits output from the PROM 7466. The high-order bit is set at a "1" for a centroid value above the FRBD data and at zero for a centroid value less than the FRBD data. The resulting centroid vector is latched into an octal register 7468 by the next range bin clock RBCLKB. It thus requires two range bin clocks for the data to progress through the divide, shift and merge. The first range bin clock RBCLKB clocks the output of the divide PROM 7460 into register 7462, while those same data, after being processed by PROM 7464 and PROM 7466, are clocked into the register 7468 during the next range bin clock RBCLKB. The output of the latch 7468 is a tri-state bus that can be either high, low or open.

The average tissue data TAVG<0:7> (generated as described below) are also applied to an octal buffer 7470 that also has a tri-state output bus. The output of the flow data register 7468 and the output of the tissue average register 7470 are both applied to a transceiver 7472 that couples either the flow or the tissue data (but not both) to a digital storage device, such as a video cassette recorder. The outputs of the registers 7468, 7470 are also applied as merge tissue flow data MTF to the smoothing circuit 7048 (FIG. 16B). Whether the MTF data correspond to the flow vector in register 7468 or the tissue data in buffer 7470 depends upon the condition of the output enable inputs to the register 7468 and buffer 7470. The output enable signals are, in turn, controlled by whether the denominator FP is larger than a predetermined magnitude.

The denominator data FP are applied to a PAL 7474, which outputs a low to the output of flip-flop 7476. Flip-flop 7476 then receives a load power signal LDFPWR from the numerator calculation circuit (FIG. 16L) that causes flip-flop 7476 to output a low FPEQ0 bit. Thus, in the event that the flow power data are greater than zero, flip-flop 7476 outputs a low FPEQ0 bit. It will be recalled that the FP data are basically the flow magnitude after a bias value has been subtracted from it. The bias value thus determines the threshold which the flow magnitude signal must exceed in order to cause flow data rather than tissue data to be displayed, as explained in greater detail below.

The FPEQ0 control bit is then applied to a merge control PAL 7478. Basically, PAL 7478 outputs a low tissue select bit TISSEL and a high flow select FLWSEL bit to output enable the tissue data buffer 7470 and disable the flow vector register 7468 in the event that the FPEQ0 bit is high (indicating that the flow power is below a predetermined value), if the FILT0 output from PROM 7464 is low (thus indicating that the centroid value is zero, indicative of no movement at the sample site), or if the beam type data BTYA indicates that the system is a fast imaging mode in which only tissue data are displayed. Otherwise, the PAL 7478 outputs a low flow select bit FLWSEL and a high tissue select TISSEL, thereby output enabling the flow vector register 7468 and disabling the output of the tissue data buffer 7470.

The tissue average circuit 7042 (FIG. 16B) receives sixteen tissue return samples for each range bin from the corner turning memory and produces a single tissue data word indicative of the average of these sixteen samples. As illustrated in FIG. 16M, each of the tissue data samples TC-T<0:7> is applied to a variable-length shift register 7480 which shifts the tissue data one bit for each sample clock SCLKD. The number of shifts required to progress through the shift register 7480 is controlled by jumpers 7482 biased high through a pull-up resistor block 7484. A number of other lines FDLY, SMTHEN . . . FC are also biased high through this pull-up block 7484. In this regard, a number of other lines throughout the system described herein are also biased high through pull-up resistors, which have been omitted for purposes of simplification.

The purpose of the shift register 7480 is to delay the tissue data for the number of sample clock pulses SCLKD required for the flow data to progress through the denomination calculation and accumulation sequencer 7030, the numerator calculation 7032, the divide circuit 7034, the spectral realignment circuit 7036, and the forward/reverse boundary shift 7040. This delay allows the tissue data from buffer 7470 (FIG. 16L) to be presented at the same time that the flow vector from register 7468 is output for the same range bin.

The delayed tissue is output by the shift register 7480 to accumulator PALs 7488, 7490, 7492, which, in conjunction with a carry block device 7494, add each tissue data sample to the previously input data samples. The first sample is loaded into the PALs 7488–7492 when the SNCLR control signal from the range boundary clock 7152 (FIG. 16D) goes low. The SNCLR line goes low a predetermined period after the start of each range bin processing cycle in order to account for the delay through shift register 7480.

The accumulated tissue data samples from accumulator PALs 7488, 7490, 7492 are then applied to a tissue averaging PAL 7496, which also receives three bits of beam type data BTYA indicative of the number of samples of tissue data that have been accumulated in the accumulator PALs 7488, 7490, 7492. The tissue averaging PAL then determines the average of the tissue samples by dividing the accumulator tissue sample data from PALs 7488–7492 by the number of samples indicated by the BTYA data. The tissue averaging PAL 7496 also sets the most significant bit of the tissue average data to "0," as explained in greater detail below. The tissue average data at the output of the PAL 7496 are then applied to a variable-length shift register 7498.

The shift register 7498 delays the tissue average data TAVG by a number of range block clock pulses RBCLKB corresponding to the number of range block clock pulses required for the flow data to be processed in the circuitry described above. As a result, the tissue average data TAVG for a given range block (i.e., sample site) are output to the smoothing circuit at the same time that the flow vector for the same range bin may be output to the smoothing circuit as merged tissue flow data MTF. The delay of the shift register 7498 is determined by the setting of straps 7499.

The function of the smoothing circuit 7048 is to be prevent imaging tissue data at one range bin surrounded by flow data at the adjacent range bins and to prevent flow data at one range bin from being imaged between tissue data in the adjacent range bins. As illustrated in FIG. 16N, the merged tissue flow data MTF<0:7> is applied to an octal register 7500 that is clocked by the range bin clock RBCLKC. On the next RBCLKC, the MTF data previously clocked into register 7500 are clocked into register 7502. On the next RBCLK pulse, the same data are clocked into register 7504. Registers 7500, 7502, 7504 thus contain the flow or tissue data for three succeeding range bins. The most significant bit from each of the registers 7500, 7502, 7504 will be zero if the data stored in the respective register are tissue and "1" if the data stored in the respective register are for flow. The sign of the flow data is given by the next-to-most-significant bit at the output of the respective register 7500, 7502, 7504.

The flow/tissue bits of registers 7500, 7502, 7504 are applied to a PAL 7506 that generates an AVGEN control bit in the event that the flow/tissue bit from register 7502 is different from both of the flow/tissue bits from the registers 7500, 7504. Under these circumstances, octal register 7508 outputs the average of the data in register 7500, 7504 upon the next range block clock RBCLKC instead of the data in the register 7504.

The average of the data in registers 7500, 7504 is obtained by applying the outputs of registers 7500, 7504 to adders 7510, 7512 since register 7500 can contain positive flow data while register 7504 can contain negative flow data (and register 7502 can contain tissue data), thus requiring that the signs of the flow data be taken into account. For this purpose, the S16 and S36 bits of register 7500, 7504, which contain the sign information, are also applied to the PAL 7506, which outputs sign SGN1 or SGN3 bits to the adder 7512. The adders 7510, 7512 thus output twice the average of the flow or tissue data in registers 7500 and 7504. On the next range block clock, these average data are clocked into register 7508, while the data that were previously in register 7502 are clocked into a buffer 7516 having a tri-state output.

In the event that the AVGEN output of PAL 7506 is low (indicating that average data should be output), register 7508 is output enabled, thereby making the tissue flow data TF equal to the average of the previously and succeeding samples. If average data are not required, the site 2 enable control signal SITETEN is generated by the PAL 7506 to output enable the register 7516. Register 7516 then outputs the data that was in the register 7502 rather than the average of the data that was then in register 7500 and 7504. The PAL 7506 also receives a smoothing enable control signal SMTHEN which can be disabled by use of a strap 7518. A beam active signal SM-BMACT is also applied to the PAL 7506 to indicate when the registers 7500, 7502, 7504 have been loaded with data.

As illustrated in FIG. 16B, the tissue data at the output of smoothing circuit 7048 are processed by an array gain compensation circuit 7054, while the flow data at the output of smoothing circuit 7048 are processed by a cosine correction circuit 7052. The gain-compensated tissue data from 7054 then merge with the cosine-corrected flow data from 7052. The array gain compensation circuit multiplies the tissue data by a scale factor corresponding to the gain of the transducer array, which is a function of the number of transducer elements used in the transducer array and the frequency of the transducer. The cosine correction circuit multiplies the flow signal by a cosine correction coefficient in order to obtain the true value of the flow velocity when the moving sound scatterers in the sample site are not moving directly along the axis of the beam toward or away from the transducer elements.

The cosine correction and array gain compensation circuit is shown in further detail in FIG. 16O. The most significant bit of the tissue/flow data TF is applied to a shift register 7520 in order to control whether the circuit processes tissue data or flow data since this bit is "0" for tissue "1" for flow. The shift register 7520 delays the flow/tissue indicator bit by two range bin clock pulses RBCLK in order to select either the flow data or tissue data after they have been cosine corrected or array gain compensated during the same two RBCLKD pulses.

The array gain compensation of the tissue data is accomplished by applying the tissue/flow data TF to an EPROM 7522 that also receives the beam number data BMA and a bit FREQ indicative of either 5 kHz or 7.5 mHz transducer carrier frequency. EPROM 7522 contains a look-up table of values equal to the gain-compensated tissue signal for each value of tissue signal, beam number and frequency. The gain-compensated tissue signal is then applied to a shift register 7524, which delays the gain-compensated tissue signals by two RBCLKD pulses to compensate for the processing time of the flow data. The register 7524 has a tri-state output bus.

The cosine correction of the flow data is accomplished by applying the tissue/flow data TF and a cosine correction coefficient COSC from the centroid board VME data and RAM interface (FIG. 16F) to a multiplier/accumulator 7528. On the first range bin clock pulse RBCLKD applied to the clock input of the multiplier/accumulator 7528, the cosine correction COSC data and tissue/flow data TF are latched into internal input registers and the flow data are multiplied by the cosine correction coefficient. Upon the next RBCLKD pulse, the product is latched to an internal output register in the multiplier/accumulator circuit 7528. The resulting product is then applied to an overflow correction PAL 7530 having a tri-state output bus.

Interpolator Subsystem

The interpolator subsystem 92 (FIG. 2B) receives the flow or tissue data from the merge circuit 90 and generates additional interpolated pixels in the image of the flow or tissue from the pixel values actually derived from flow or tissue data. A block diagram of the interpolator subsystem is illustrated in FIG. 17A. The interpolator subsystem 92 interfaces with the CPU through a VME interface circuit 7600 and is connected to the CPU address bus, data bus, and various control lines. VME interface circuit 7600 outputs various control signals to a timing and control logic circuit 7602 that also receives the beam active BMACT signal, the beam type BT data, a BM1 bit indicative of when data from the first beam is received, and a 15 mHz clock signal. All of these signals are derived from the timing and control subsystem forming part of the corner turning memory 80 (FIG. 2B).

The VME interface circuit 7600 outputs various data to a row and column address circuit 7604. These data include a SHRINK bit that designates when the image is to be displayed in half-size, a 2-bit depth DEPTH<0:1> value indicative of whether 240, 320, 360 or 480 range bins are to be used, image boundary data specifying the boundaries of the displayed image, and image origin data specifying the starting point of the displayed image. The row and column address circuit 7604 also receives various control signals from the timing and control logic circuits 7602.

The row and column address circuit 7604 outputs a 9-bit range address RA<0:8> and a 10-bit column address CA<0:9> indicative of the position of each pixel on the display. These addresses are received by a linear address conversion circuit 7608 which formats the address and outputs it in a 19-bit word to a graphics interface circuit 7610.

The flow or tissue data is applied to a centroid interface and self-test PROM 7612 that performs two basic functions. First, it stores the flow or tissue data for the previous beam in random access memory in order to calculate interpolated pixel data based upon the flow or tissue data for the current beam and for the previous beam. Second, it allows test data stored in a PROM to be substituted for the flow or tissue data for test purposes. The data from the centroid interface and self-test PROM 612 are received by a data processing circuit 7614 that actually calculates the interpolated pixel data. These interpolated data are applied with the pixel address data to the graphics interface circuit 7610. The graphics interface circuit 7610 then outputs a 19-bit address IM-A<0:18> and eight bits of data IM-D<0:7> to the image memory 94 (FIG. 2B). HANDSHAKE signals coordinate the transfer of data from the graphics interface circuit 7610 to the image memory 94. LED indicators 7616 are used to display the operating status of the graphics interface circuit 7610. The basic function of the graphics interface circuit 7610 is to store the data and then output them on a first-in, first-out ("FIFO") basis in order to match the rate of the interpolation to the acceptance rate of the image memory 94.

The column addressing portion of the row and column address 7604 is illustrated in FIG. 17B. Column address increment PROMs 7620, 7622, 7624 output a 12-bit increment value indicative of the horizontal spacing between successively interpolated pixels. The increment values are a function of the data on various inputs to the PROMs 7620, 7622, 7624. A 3-bit sequence word SEQ<2:4> allows the pixel addresses to increment through all pixels in a cell, where a cell is a small region of the image that is filled with pixels to represent the display for four measured data values. Three cycle bits CYC<0:2> specify a cell number, since the number of pixels can vary between cells. A 3-bit interpolation code INT<0:2> specifies the algorithm used to perform interpolation. A beam start signal BMSTAD causes the address to jump to the starting column each time a new beam occurs. Finally, a 2-bit depth DPTH<0:1> word identifies the number of range bins, which therefore specifies the vertical address jump that must occur at the beginning of each beam to position to the top of the display.

The increment values from the PROMs 7620, 7622, 7624 pass through divide-by-two PALs 7626, 7628. The PALs 7626, 7628 are controlled by the SHRINK input to divide the increment by two in the event that the image is to be displayed in half-size format. PALs 7626, 7628 then output the incremental value to column address accumulator PALs 7630, 7632, 7634, which form the column address. A negative-going image start IMSTAD bit causes the PALs 7626, 7628 to disable their outputs so that registers 7638, 7640, whose outputs are enabled by IMSTAD, will load the accumulator PALs 7630, 7632 with the image origin column address at the start of an image.

The starting point of the address VD<0:7> from the CPU is clocked into the registers 7638, 7640 by a negative-going load column image pulse LDCIM. The image origin data are output to the PALs 7630, 7632, 7634 by the image start bit IMSTAD at the same time that the increment values are disabled by the divide-by-two PALs 7626, 7628. Thus, at the start of each beam, the PALs 7630, 7632, 7634 receive data indicative of the starting point of the image. The PALs 7630, 7632, 7634, with the help of the carry look-ahead block 7642, cause the column addresses CA<0:10> to increment each ACUMSTRO pulse. The column addresses CA are then applied to a pair of magnitude comparators 7644, 7646, which also receive data from the CPUVD specifying the minimum and maximum column values. The column addresses and maximum adjust data are loaded into the comparator 7644 by a load column maximum pulse LDCMAX.

Similarly, the column addresses and the column address minimum values are loaded into comparator 7646 by the load column minimum pulse LDCMIN. In the event that the column address is less than the maximum address value, comparator 7644 outputs a high CLEMAX bit. OR-gate 7648 is used to add the two low-order bits of the address to the comparisons. The IP<Q input to the comparator 7644 is only functional when the data applied to the P and Q inputs are equal to each other. If the eight higher bits of the column address are equal to the maximum address data, and the CA<0> and CA<1> column address bits are both low, than the column address is, of necessity, less than or equal to the maximum value.

In the event that the column address data are greater than the minimum address data, comparator 7646 outputs a high CGEMIN bit. High CLEMAX and CGEMIN bits are thus indicative that the pixel is within its leftmost and rightmost position limits.

The portion of the row and column address circuitry 7604 that controls the row address of the pixels is illustrated in FIG. 17C. Row address increment PROMs 7650, 7652, 7654 receive the same SEQ, CYC, INT, DPH and BMSTAD data or signals that the column address increment PROMs 7620, 7622, 7624 received in FIG. 17B. However, the BMSTAD signal is used in the row address circuitry of FIG. 17C to force the PROM 7650, 7652, 7654 to output a large negative address at the start of each beam to jump from the bottom row of one vertical scan line to the first row of the next. In contrast, the column address increment PROMs 7620, 7622, 7624 use the BMSTAD signal to output the incremental value to move the pixel from one scan line to the next.

The outputs of the row address increment PROMs 7650, 7652, 7654 are likewise applied to divide-by-two PALs 7656, 7658, which divide the increments by two when the half-size "SHRINK" mode is selected by the SHRINK input. The row addressing circuit also utilizes a pair of registers 7660, 7662 to store the row starting address of the image when clocked by the LDRIM pulse. The PALs 7656, 7658 output the row increment, and the registers 7660, 7662 output the row starting address. Upon receipt of a negative-going IMSTAD pulse, these data are then loaded into row address accumulator PALs 7664, 7666, 7668, which output the row addresses. The row addresses are incremented at each ACUMSTO pulse if the ADINCEN control signal from the interpolator timing circuitry 7602 is low. The accumulator PALs 7664, 7666, 7668 perform their accumulating function with the aid of a carry look-ahead block 7670.

The accumulator row addresses at the outputs of the PALs 7664, 7666, 7668 are applied to a row address maximum comparator 7672 and a row address minimum comparator 7674, which also receive the maximum and minimum row address values VD from the CPU. The comparator 7672 outputs a high RLEMAX bit in the event that the row address is less than the maximum row address. Similarly, the comparator 7674 outputs a high RGEMIN in the event that the row address is greater than the minimum row address. Thus, the row address is within its upper and lower limits in the event that RLEMAX and RGEMIN are both high.

As explained above with reference to FIG. 17A, the row and column addresses are applied to a linear address conversion circuit 7608 that formats the addresses for use by the graphics interface circuit 7610. More specifically, the linear address conversion circuit, as illustrated in FIG. 17D, either applies the separate row and column addresses to the output of the linear address conversion circuit or it reformats the row and column data into a linear address in which the first row is designated by an address 0–639, the next row is designated by an address 640–1279, etc. The linear address conversion circuitry also allows the image to be displayed from right to left instead of from left to right when operating in the row/column mode.

The row address is applied to adders 7680, 7682 and exclusive OR-gate 7684 that multiply the row address RA<0:7> by five. The multiplication by five is accomplished by shifting the row address RA<0:7> by two bits to derive the RA<0:7> multiplied by 22 (i.e., 4) and then adding the resulting multiple RA<2:8> to the address RA<1:7> in adders 7680, 7682. A multiple of 640 times the row address RA<0:7> is then obtained by recognizing that making the three high-order bits five is equivalent to 0.640. The resulting multiple of 640× the row is added to the column in adders 7686, 7688, 7690. The resulting output from the adders 7686, 7688, 7690 is the column plus the product of 640 and the row number, thereby providing a linear address. This linear address is output to multiplexers 7692, 7694.

The column address CA<0:9> is applied to a image reverse logic PAL 7696 that outputs the complement of the column address when the VH1 input is high. The four high-order bits of the column address complement are applied to an adder 7698 that also receives at its "B" inputs the binary number "1010." Insofar as an 8-bit number having "1010" as its high order of bits is equal to 0.640, the adder 7698, when recombined with the low-order column address bits, outputs the difference between 640 and the column number. In the event that the IMREV input is low, the adder 7698 merely passes the column address. The purpose of the adder 7698 and image reverse logic PAL 7696 is to cause the column to start at the 640 position, (i.e., the right-hand side) and decrement from right to left. The reverse or normal column address is then applied to the multiplexers 7692, 7694. The multiplexers 7692, 7694 are controlled by a strap 7699 to either output the row/column data from the row and column addressing circuitry, or to output the linear address from the adders 7686–7690.

The centroid board interface circuit is illustrated in FIG. 17E. The flow or tissue data from the centroid subsystem are applied to an octal buffer 7700 that is output enabled by OR-gate 7702 whenever the self-test input SELFTEST is low and the active low RDRAM input is high. Thus, the octal buffer 7700 presents the centroid data through a storage register 7706 whenever the random access memories (described below) are not being read, or when the self-test mode has not been selected. The centroid data from buffer 7700 are also applied to previous beam storage RAM 7710 that is addressed by a sample site counter 7712 using AND-gate 7714 and flip-flop 7716 to extend the count to the ninth bit. The counter 7712 is incremented by a clock CLK1 pulse whenever the delayed beam active signal BMADLY signal is high when the centroid is outputting data. Thus, when the centroid subsystem is outputting data, counter 7712 increments to allow each item of data to be written into the RAM 7710. At that time, the WRRAM input to the RAM 7710 is active low. The counter 7712 is reset by the CLRSTCN pulse at the beginning of each beam. At the same time, the beam active delay removes the set from flip-flop 7716 and allows counter 7712 to increment. Whenever the CLRSTCN input is low, OR-gate 7720 is enabled, thereby allowing the clock CLK1 to pass through OR-gate 7720 and inverter 7722 to clock the flip-flop 7716.

The pipeline register 7706 contains two input registers and two output registers. The current centroid data are written into the first input register by the input register selected by the INP bits. The other register in the pipeline register 7706 stores the corresponding data from the previous beam that is output by RAM 7710. Pipeline register 7706 also contains two output registers that are selected by the MXPS bits. These output registers output the current and previous beam data for corresponding positions after a predetermined delay to compensate for the processing time of the current data.

The centroid interface circuit also contains a PROM 7726 that stores test data that are processed by the imaging system instead of actual data for test purposes. The test PROM 7726 is also addressed by the counter 7712 and flip-flop 7716 and it outputs its data to the pipeline register 7706. Since the octal buffer 7700, the PROM 7726, and the RAM 7710 all have outputs that are tri-state, the pipeline register 7706 may receive data from any of them. However, as mentioned above, when the RDRAM input is low, octal buffer 7700 is disabled and PROM 7726 and RAM 7710 are enabled. PROM 7726 is chosen to output test data when the SELFTEST input is high. RAM 7710 is chosen to output previous beam centroid data when the RDRAM signal is low. Whenever the RDRAM input is not low and the SELFTEST input is low, octal buffer 7700 is output enabled and the PROM 7726 and RAM 7710 are disabled, thereby allowing the octal buffer 7700 to output centroid data to the pipeline register 7706.

The data processing circuit 7614 for the centroid subsystem calculates the value of interpolated pixels using the values and corresponding addresses of centroid data. As illustrated in FIG. 17F, the centroid data for the current beam and the previous beam SPS are output from the centroid interface to a pipeline register 7730 and written into one of four registers selected by the MACIN bits. The pipeline register 7730 stores the centroid data for two successive sample sites of the current beam as well as the same sample sites for the previous beam. After a predetermined number of CLK2 pulses, each of the stored values is applied to an output register as selected by the MACMX input. The pipeline register 7730 first outputs the centroid data for the pixel that is closest to the pixel that is being interpolated. Each of the centroid data values is applied to a multiplier/accumulator 7732. Multiplier/accumulator 7732 also receives a weighting value calculated as described below.

The weighting values for the accumulator 7732 are stored in a PROM 7734 and are selected by the sequence number SEQ, the cycle number CYC, the interpolation algorithm INT, and the first beam FIRSTBM control signal. The weighting coefficients are output from the PROM 7734 to a series of AND-gates, generally indicated at 7736, which also receive a ZCOEF output from a PAL 7738. PAL 7738, by outputting a "0" ZCOEF, can make all of the weighting coefficients zero. The PAL 7738 also receives the two high-order bits of the output from the pipeline register 7730. The high-order bit MD<7> designates whether the centroid data are for tissue or flow, and this information is output as a PRDTYP bit to the high-order bit of an octal register 7740. The low-order bits of the octal register 7740 receive the accumulated product from the multiplier/accumulator 7732 to generate an 8-bit RD word, with the seventh bit designated whether the data are for tissue or flow. In the event that the data are for flow, the sign of the data, as indicated in the sixth bit MD<6>, is also used by the PAL 7738 to generate the MDSGN bit that is applied to the accumulator 7732. The output of the octal register 7740 is thus a value for an interpolated pixel lying somewhere within the cell formed by centroid data from two sample sites of a given beam and the same two sample sites of the previous beam. The timing of the accumulation interval is determined by the ACCUMST 0 signal, which is applied to the multiplier/accumulator 7732 through inverter 7742, and by an ACUMST 2 signal that clocks the output of the multiplier/accumulator into the octal register 7740.

As explained above with reference to FIG. 17A, the graphics interface circuit 7610 stores the addresses from the linear address conversion circuit 7608 and the interpolated data from the data processing circuit 7614 and outputs the addresses and data to the image memory 94 (FIG. 2B) in order to match the rate of interpolation to the operating rate of the image memory 94. The schematic of the graphics interface circuit 7610 is illustrated in FIG. 17G. The memory operates on a first-in, first-out (FIFO) principle in which data that are first written into memory are first output by the memory.

The eighteen bits of address from the linear address conversion circuit 7608 are stored in 64×4-bit FIFO memories 7750, 7752, 7754, 7756, 7758, each storing up to four address bits, so that a total of sixty-four addresses may be stored. Similarly, the pixel data R0 are stored in FIFO memories 7760, 7762, each of which can store up to sixty-four 4-bit words. Thus, the FIFO data memory 7760, 7762 can store up to sixty-four words of pixel data. As explained in greater detail below, the pixel data in any location in the memory 7760, 7762 control the location on the display screen identified by the address stored in the corresponding location of memory 7750, 7752, 7754, 7756, 7758.

The memories 7750–7758, 7760 and 7762 are put in a clear state by a beam clear BMCLR high applied to inverter 7764 when pixel data are not present. However, when pixel data and addresses are to be applied to the graphics interface circuit 7610, BMCLR goes low, thereby allowing the memories 7750–7762 to input and output data.

The memories 7750–7762 have two control bits, namely, a shift in SI input and a shift out SO input. The shift in inputs of the memory 7750, 7762 receives a FIFOWR bit from a control PAL 7766 through inverter 7768. A high FIFOWR is generated from the ACUMST 3 pulse when a number of conditions are met. First, it is necessary that the address being input to the graphics interface circuit 7610 be within the left, right, upper, and lower boundaries. Consequently, the CGEMIN, CLEMAX, RGEMIN, and RLEMAX control bits from the row and column addressing circuit 7604 are all checked for a high condition. Second, FIFO write enable FIFOWEN, which is generated by the interpolator board timing circuit, as explained below, must be low, which occurs basically when data are being applied to the interpolator subsystem 92. Third, the tenth bit of the column address CA<10> and the ninth bit of the row address R<9> must both be "0," thereby indicating that the data and addresses currently being input are not the final data and address bits. Fourth, the FREEZE input must be high, thereby indicating that the system is not in the freeze mode in which the displayed image is frozen rather than being updated in real time. Finally, the condition of the SHRINK input is checked. If SHRINK is low, then the CALSB and RALSB inputs are not checked. However, if the system is operating in the shrink mode (i.e., half frame), then the PAL 7756 will also check the status of the CALSB and RALSB bits to make sure that neither of them is one. It will be recalled that CALSB and RALSB are the least significant bits of the column and row addresses after the addresses have been divided by two in the shrink mode. In the shrink mode, these fractional addresses should not be displayed. For this reason, the PAL 7766 inhibits FIFORWR from being generated in the event that CALSB or RALSB is zero.

The control PAL 7766 also checks to make sure that the INRDY input is low. INRDY is generated by a PAL 7770 which checks the condition of the input ready IR status outputs of the memories 7750–7762, either directly or through AND-gates 7772, 7774 to make sure that they are all high. The input ready status outputs signify that the memories 7750–7762 are capable of accepting inputs. Similar output ready OR status bits are also applied to the PALs 7770, which output a not empty NEMPTY low to flip-flop 7776. Flip-Flop 7776 then outputs a low not empty NOTEMPTY on the leading edge of beam active BMACT whenever any of the memories 7750–7762 contain data in the output register. The final input checked by PAL 7766 in order to generate the FIFOWR pulse is the FIFO inhibit FIFOINH bit, which is generated by the control logic circuit 7602 when one or more of the memories 7750, 7762 does not contain data to be output.

In summary, if the row and column address is in the proper boundary, the freeze mode has not been selected and the memories 7750–7762 are in a condition to accept data, the addresses and pixel data are written into the memories 7750–7758 and 7760–7762, respectively, on each ACUMST 3 pulse. Addresses and data are then read out of the memories 7750–7758 and 7760–7762 on each MI-DACD pulse asserted by image memory 94 as it inputs data in the same order that the addresses and data were entered.

The operation of the above-described interpolator subsystem circuitry is largely controlled by the timing and control logic circuit 7602 (FIG. 17A), which is illustrated in greater detail in FIG. 17H. The interpolation process is initiated when control PAL 7780 detects the presence of the beam active C1-BMACT input from the timing and control subsystem through a buffer 7782. PAL 7780 then outputs a first beam FIRSTBM low, which is used by other portions of the interpolator circuit and by a register I/O PAL 7784 to generate various control signals, as explained in greater detail below. PAL 7780 also receives a TI-FRZIM control signal through buffer 7782 and generates a FREEZE output in response thereto in order to inhibit operation of the interpolator when the freeze mode is selected. The PAL 7780 synchronizes the start and end of FREEZE to the CI-BMACT leading edge.

Upon receipt of the first beam FIRSTBM output from PAL 7780, PAL 7784 generates various other control signals depending upon other inputs. PAL 7784 also outputs a cycle clear CYCCLR pulse synchronized to the CLK 3, which clears an interpolation cycle counter 7786. The counter 7786 is also cleared by a BMCLR pulse at the output of PAL 7788 when PAL 7788 detects the BMACT signal from buffer 7782. Binary counter 7786 then increments with each CLR-STON 6 pulse in order to generate a 3-bit cycle CYC<0:2> output that is used to indicate the current operating segment of the interpolation process.

In addition to generating the BMCLR output for the binary counter 7786 and other portions of the interpolation subsystem, PAL 7788 also generates start beam STRTBM and end beam ENDBM outputs to timing control PAL 7784. The STRTBM output goes low a predetermined delay after the BMACT input goes high in order to allow the first two measured pixel data values to be stored since interpolated pixel data cannot be calculated until then. PAL 7788 generates the negative-going end beam ENDBM output after the same delay has expired from the point where the BMACT goes low. PAL 7788 also outputs an accumulation start ACCSTRT bit to an accumulation cycle shift register 7790. Shift register 7790 thereafter shifts the high ACCSTRT bit from accumulator state zero ACUMST 0 to accumulator state three ACUMST 3 in order to provide four phases of accumulation cycle clocks for the interpolator circuitry.

The control signals generated by the PAL 7784 include the clear state counter CLRSTCN signal that is applied to the interpolation cycle counter 7786 through inverter 7792 and to the centroid interface (FIG. 34) through clear counter 7712 (FIG. 17E). PAL 7784 also generates a beam start address BMSTAD which is used by the column addressing and row addressing circuits (FIGS. 17B and 17C, respectively) to generate column and row address jumps at the beginning of each beam. An address increment enable ADINCEN is generated to allow the column and row addresses to be accumulated in order to incrementally increase the column and row addresses. Finally, PAL 7784 outputs an image start address bit IMSTAD which is applied to the row and column addressing circuits to load the addresses of the image origin in address accumulator PALs (FIGS. 17B and 17C).

The interpolator timing circuit also includes sequence state counters 7796, 7798 that generate 5-bit sequence SEQ<0:4> data used to specify the operating sequence of the interpolator. Basically, it requires thirty-two CLK 4 pulses to generate eight interpolated pixels. Counters 7796, 7798 are cleared by the CLRSTCN bit each time new data are received from the centroid subsystem. Counters 7796, 7798 then increment to thirty-two upon receipt of each CLK 4 pulse.

The control logic circuitry in timing and control logic circuit 7602 is illustrated in FIG. 17I. A 15 mHz clock is applied to a binary counter 7800 through inverter 7802 in order to generate potential clock frequencies of 15 mHz, 7.5 mHz, 3.75 mHz, and 1.875 mHz, which are applied to an interpolation code PAL 7804. PAL 7804 outputs one of these clock frequencies as the interpolator clock CLKOUT, and a 3-bit interpolation code INT<0:2>, and a 2-bit word BM<0:1> identifying the number of the beam. Operation of the interpolation code PAL 7804 is synchronized with a clock CLK 4 output by buffer 7806 and the first beam FIRSTBM output from PAL 7780 (FIG. 17H). The BMLO= 1> from PAL 7804 is incremented by the BMCLR signal from PAL 7788 (FIG. 17H) at the start of each scan line of data. Finally, the interpolation function may be disabled by a high interpolation off INTRP-OFF from the VME interface 7600, as explained below.

The beam type inputs to the interpolation code PAL 7804 are generated by a register 7808 that is clocked by the beam active TB-BMACT input through inverter 7810. Register 7808 thus delays the beam type inputs to account for processing delays of the flow processor and centroid. Register 7808 receives three beam type bits TV-BT<3:5> from the timing and control subsystem. The function of the shift register 7808 is to delay the beam type inputs so that they are output to the interpolation code PAL 7804 at the same time that the corresponding data are loaded into the interpolator.

The circuitry illustrated in FIG. 17I also includes a sequence control PAL 7814 that generates the control signals for the centroid interface circuit illustrated in FIG. 17E. Sequence control PAL 7814 receives a 5-bit sequence word SEQ<0:4>, the beam active BMACT input from the circuitry of FIG. 17H, and the clear state counter CLRSTCN output from the circuitry of FIG. 17H. Based primarily upon the SEQ data when BMACT is high, PAL 7814 generates the RDRAM output to allow data to be read from the random access memories 7726, 7710, storing self-test or previous beam data, the write RAM, WRRAM, signal to allow data to be stored in the RAMs 7726, 7710, the INP<0:1> signal that is used to specify in which input register in register 7706 input data are to be stored, and the multiplexer controls data MXPS<0:1> that specify from which register data are to be read out of the register 7706. PAL 7814 also generates 2-bit MACIN<0:1> data that specify which input register of register 7730 data are to be read in the circuitry of FIG. 17F. The register from which data are to be read from the register 7730 is specified by the MACMX<0:1> output from PROM 7816, based upon the sequence data SEQ<0:4>, the cycle number CYC<0:2>, the interpolation code INT<0:2>, and the first beam FIRSTBM input from the circuitry of FIG. 17H. Basically, MACMX is generated to output the four measured pixel data points in order to calculate interpolated pixel data. PROM 7816 also outputs a CYCEND bit that signifies when the end of an interpolation cell is reached and is input to the start control PAL 7788 and timing control PAL 7784 in FIG. 17H. PROM 7816 is also applied to the data inputs of a shift register 7818 which is clocked by the ACUMST 1 pulse whenever the interpolation code INT<0:2> specifies that the interpolation function is not being used. Register 7818 is used to delay the start of FIFO inhibit FIFOINH for an appropriate period.

The VME interface circuitry 7600 (FIG. 17A) is illustrated in greater detail in FIG. 17J. The central processing unit interfaces with the VME subsystem through an I/O PAL 7830 that is connected to the ten high-order address bits of the CPU V-A<14:23>, a write control signal V-WRITE, and a data strobe signal PB-DSTROB. The data bus of the CPU is connected to an octal buffer 7832.

I/O PAL 7830 outputs a number of control signals for controlling a portion of the row and column address circuitry 7604, some of which are applied through inverters 7834, 7836, 7838, 7840. More specifically, the LDCMAX signal is generated from the data strobe PB-DSTROB and a predetermined CPU address to load the maximum column value into comparator circuit 7644 (FIG. 17B). LDCMIN is generated in a similar manner to load the minimum column address into register 7646. In a similar manner, the LDRMAX and LDRMIN are generated by the data strobe PB-BDSTROB and appropriate CPU addresses to load row maximum and minimum values into comparator circuits 7672, 7674, respectively. The data strobe PB-DBSTROB and appropriate addresses are also used to generate LDCIM and LDRIM pulses that allow the CPU to load the column and row origin points for the image into register 7640 (FIG. 17B) and 7662 (FIG. 17C), respectively. Finally, I/O PAL 7830 is used to clock the CPU data from buffer 7832 into a register 7844 in order to generate several control signals from the CPU data bus. Specifically, register 7844 outputs an FREQ bit specifying whether the ultrasound carrier frequency is either 5 mHz or 7.5 mHz. It outputs a 2-bit DPTH word specifying the number of discrete range bins or sample sites (four possible values), a self-test SELFTS bit to implement a test mode, an INTRP-OFF bit to disable the interpolation function, a SHRINK output to reduce the size of the image to twenty-five percent, and an IMREV bit that is used to display data from right to left rather than from left to right in the normal mode.

The VME interface 7600 also includes three status light-emitting diodes (LED) 7850, 7852, 7854 for specifying the status of the graphics interface circuitry 7610. The LEDs 7850–7854 are controlled by an LED control PAL 7856 through respective drivers 7858, 7860, 7862. PAL 7856 receives the NOTEMPTY output from the flip-flop 7776 whenever the output registers of the address and data memories 7750–7762 contain addresses or data and the beam active BMACT input to flip-flop 7776 is high, thus indicating that graphics memory has not read all of the data from the memories 7750–7762. The NOTEMPTY input to PAL 7856 is clocked into an internal register by the CLK 1 pulse to generate an FNEMPTY low, thereby illuminating LED 7850. Thus, the normal operating state of the interpolation circuit LED 7850 should not be illuminated.

In the event that the input registers of the memories 7750–7762 are full when ACUMST1 is high, which occurs just before addresses and data are to be written into the memory 7750–7758 and 7760–7762, PAL 7770 outputs an FULL low. This FULL low causes LED control PAL 7856 to output a low FULL, thereby illuminating LED 7852. Thus, in normal operation, LED 7852 should not be illuminated.

The LED control PAL 7856 also receives the FIFO write FIFOWR signal from FIFO write control PAL 7766 (FIG. 17G), which occurs every fourth CLK1 pulse when addresses and data are being written into the memories 7750–7758 and 7760–7762. The SEQ<0:1> data are used to increase the duty cycle of the FIFOWR pulse to cause PAL 7856 to generate a relatively long FWR low output, thereby illuminating LED 7854. Thus, in normal operation, LED 7854 is illuminated.

Digital Storage Subsystem

Figure 18B:
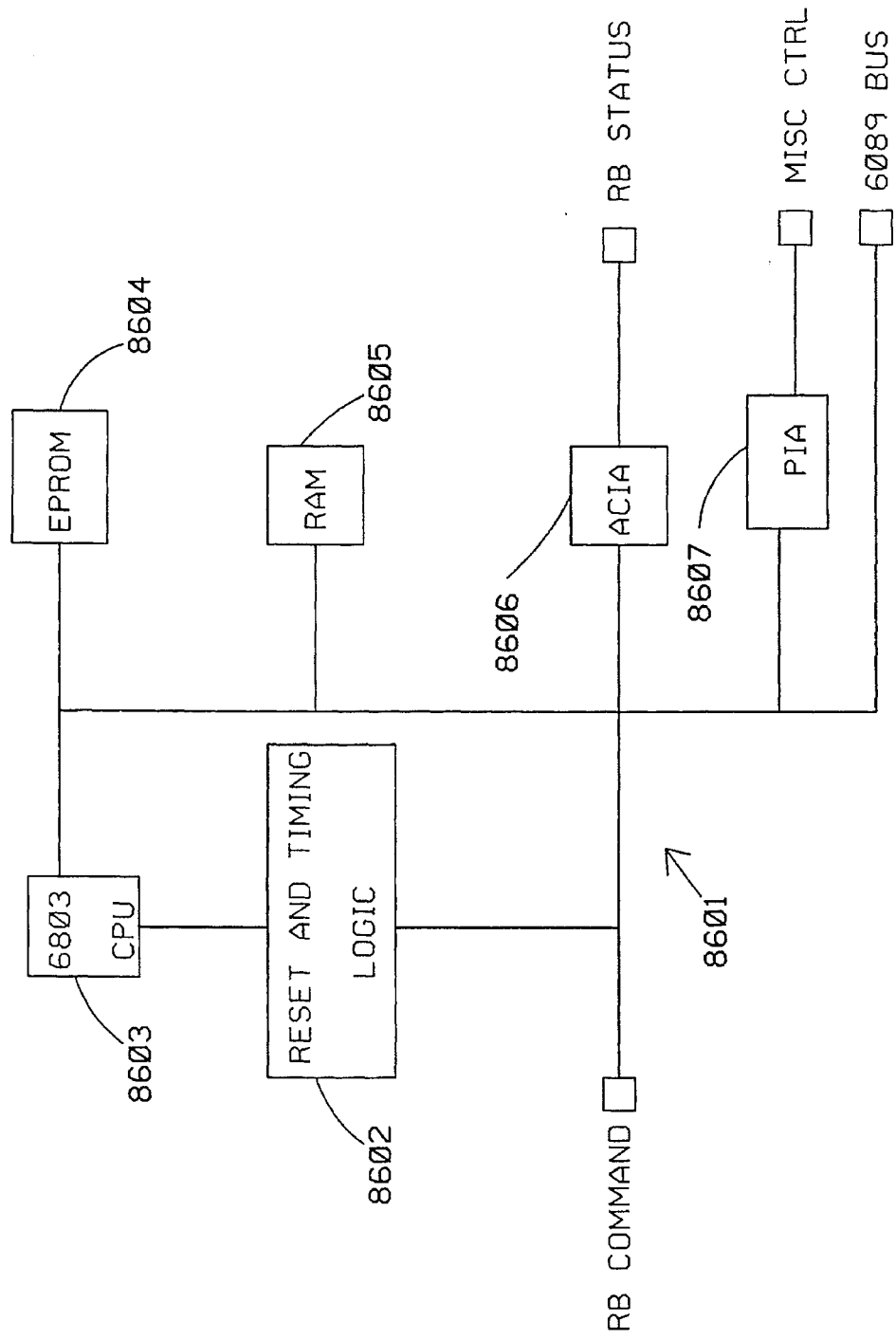
FIG. 18 is a block diagram and circuit schematic of the digital storage subsystem.

A block diagram of the digital storage subsystem 8600 is shown in FIG. 18A. FIGS. 18B through 18V show lower level block diagrams and circuit diagrams for the digital storage subsystem 8600. Because the use of only a VCR to record images causes a loss of resolution due to VCR bandwidth limitations, the digital storage subsystem is designed to be a means for maintaining the system's full resolution capability. Types of information stored by the digital storage subsystem 8600 include: patient history; real-time image sequences; frozen images; system configuration data; and examination protocols.

The subsystem 8600 enables users to record up to two hours of scan data in the preferred embodiment. The data can be archived for record-keeping purposes and subsequently recalled at a later date for examination. During recall, the preferred embodiment provides a limited set of post-processing capabilities, including cosine correction, post-processing curve modification and waveform/image measurements which require no real-time processing of data. The subsystem also can be a repository for user defined examination protocols.

With reference to FIG. 18A, the digital storage CPU 8601 receives commands from and sends status to the system CPU 130. In addition, CPU 8601 sends control information to and receives status information from the review buffer interface 8620, the frame buffer interface 8630, VCR record data processor 8680, and VCR playback processor 8650.

Information to be processed by the digital subsystem 8600 enters the frame buffer system interface 8750 or the VCR data playback processor 8650. Data enters via VCR playback processor 8650 when the VCR is being used for displaying images from a tape onto the monitor. During real-time imaging, the image sequences, system configuration data or operator entered information, such as patient history or examination protocols, enters subsystem 8600 via the frame buffer system interface 8750. Data input through frame buffer system interface 8750 or VCR playback processor 8650 is transferred to the review buffer 8100 via review buffer interface 8618.

In one embodiment, four types of data enter the frame buffer 8760 via the frame buffer system interface 8750: system CPU data, ECG data, image/velocity data, and spectrum data. Under CPU 8601 control, DMA controller 8610 manages data transfer to and from the frame buffer 8760 into the review buffer via review buffer interface 8620 and frame buffer interface 8630.

The digital storage subsystem 8600 operates in one of four modes: idle, playback, record, and cine loop. In the idle mode, no data transfers occur, although DMA controller 8610 refreshes the memory comprising the review buffer.

During a VCR playback, data is transferred from the review buffer 8100 into the frame buffer interface 8630 via review buffer interface 8620 for output to the graphics I/O subsystem for display.

During a VCR record operation, the data entering into frame buffer interface 8630 is transferred into the review buffer via review buffer interface 8620, then transferred to the VCR record data processor 8640 for output to the graphics I/O subsystem for display.

During the system's cine loop function, the data in the review buffer 8100 is the source of information to be displayed. In such case, the data is transferred from review buffer 8100 through review buffer interface 8620 and frame buffer interface buffer 8630 to the graphics I/O subsystem for display. The stored frames can be displayed in forward or reverse direction, and the end points can be moved to restrict the review buffer region that is output. All data transfers are managed by the DMA controller 8610 under the functional direction of CPU 8601.

Referring to FIGS. 18B, 18C, and 18D, the digital storage subsystem CPU 8601 includes reset and timing logic 8602, a conventional processing unit 8603, EPROM 8608, RAM 8605, a synchronous communication interface adapter 4606, and programmable interface adapter 4607.

Digital subsystem processor 8603 is a conventional microprocessor, which in one embodiment is a Motorola 6809 8-bit microprocessor. Processor 8603 uses an 8 mega-Hertz (mHz) clock 8608, also used by the DMA controller 8610. The digital storage subsystem 8600 receives commands from the system's CPU 130 through an RS-232 receiver 8662. The commands and command parameters are received into asynchronous command interface adapter 8606. Another RS-232 receiver 8664 performs a handshaking function with the system CPU during the command transfers.

Table DS-A, below, lists the commands from system CPU 130 supported by the digital storage subsystem.

TABLE DS-A

| Command | Description |
| --- | --- |
| mode command | Idle, record; playback; cine loop forward; cine loop reverse. |
| cine loop begin | Marks the Nth previous frame to the currently output frame as the cine loop begin point. N is the cine loop offset. |
| cine loop end | Marks the Nth previous frame to the currently output frame as the cine loop end point. |
| clear review buffer pointers | Empties the review buffer. |
| set frame length | The frame length is specified in 16 byte units by the ms/ls bytes of the parameter field. |
| return status | Command acknowledge; review buffer end; review buffer beginning; digital frame input; current mode; cine loop direction. |
| return review buffer output pointer | The msbyte and lsbyte of the response are the number of frames in the review buffer between the input pointer and the output pointer. |
| cine loop offset | Sets the offset, in frames, used with the cine loop begin command, cine loop end command, and cine loop clear command. The offset is currently limited to less than 4 by the control software. |
| set review buffer size | Sets the review buffer size in Mbytes. |
| cine loop clear | Clears frames from the review buffer that are older than the Nth frame before the current output frame. N is the cine loop offset parameter. |

Asynchronous command interface adapter 8606, a Motorola 6850 ACIA, receives data at a 9600 baud rate generated by a 4.9 mHz clock 8666 and a twelve-stage binary counter 8668. The asynchronous command interface adapter (ACIA) 8606 generates an interrupt request to processor 8603 whenever a command is received. Processor 8603 then reads the data bus of ACIA 8606 to identify the command parameters. The commands transmitted from CPU 130 to processor 8603 include the following: mode; cine loop begin; cine loop end; clear review buffer pointers; set frame buffer length for record mode; request processor 8603 status; return output pointer from the review buffer; set cine loop offset (to determine the frame of data the viewer selected from the monitor as opposed to the frame of data currently transmitted through the digital subsystem); set review buffer size (defaults to three megabytes); and cine loop clear.

The RS-232 receiver 8662, which receives the CPU 130 commands, also routes the incoming signals through a timing circuit 8668. The timing circuit includes a transistor normally shorted to ground by a capacitor with a pull-up resistor. On system power-up, however, CPU 130 sends a break character stream 100 milliseconds long, which allows the capacitor to time out, thereby switching the transistor on, which in turn generates a reset to the processor 8603.

The ACIA 8606 sends an acknowledge signal back to the system CPU 130 through an RS-232 transmitter 8665 along with a handshaking signal through an RS-232 transmitter 8667. The processor 8603 generates an enable signal for enabling the ACIA 8606 or the programmable interface adapter (PIA) 8607, a Motorola 6522 PIA. Processor 8603 also sends a read/write signal for specifying the direction of data on the DMA controller bus. The PIA 8607 in one embodiment is a Motorola 6522 interface adapter, which has two timers and four interrupt inputs. In this embodiment, three interrupts are used. One interrupt is generated by the DMABSY line, which signifies that a DMA transfer is complete. A second interrupt is generated by the SYNDET line, which signifies that a synchronization pulse has been detected for an incoming frame from the VCR playback data processor 8650. The third interrupt is generated by the line FBX_REQ, which signifies a request from the frame buffer interface to transfer data to the review buffer. Additional inputs to the PIA 8607 are a chip select line, a record FIFO half-full line (RFHFL), and a playback FIFO half full line (PBFHFL).

The PIA 8607 generates the higher addresses for selecting various memory chips within the review buffer. The lower addresses are provided through the DMA controller 8610. The PIA 8607 also generates miscellaneous control signals, such as a DMA reset to initialize the DMA after a data transfer, a stuff or strip mode line used by the synchronization detector, a frame buffer transfer initialization line, a synchronization clear line, a FIFO reset line, a frame buffer transfer complete line, and a DMA inhibit line.

Referring to FIG. 18D, the addresses output from processor 8603 enter into a dual demultiplexer 8670, which splits the addresses into four 16 kilobyte blocks of addresses. The highest addresses are for the EPROM 8604; the next highest block of addresses is not used. The third highest block of addresses is for RAM 8605. The lowest block of addresses is for an I/O space. The demultiplexer 8670 generates an enable signal to EPROM 8604, RAM 8605, or decoder 8672 to select each of the blocks of the addresses. The I/O space is further divided into 16-byte blocks by decoder 8672. This decoder 8672 is used to generate chip selects for the ACIA 8606, PIA 8607, DMA controller 8610, and a CRT controller used for generating video synchronization for recording data. The lowest 16-byte block is further broken down into individual addresses through decoder 8674. These addresses are used for providing three frame buffer address pointers, three frame buffer byte counter pointers, and two strobes to the sync-detect logic to enable processor 8603 to read the address of the synchronization pulse latched into a sync-detect latch. Data output from processor 8603 containing the frame buffer address pointers or frame buffer byte counters is loaded into the frame buffer interface through transceiver 8676.

Referring to FIGS. 18A and 18E, the DMA controller circuits 8610 include a four-channel DMA controller 8683. Channel 0 is used for routing data from the playback FIFOs to the review buffer. Channel 1 is used for routing data from the review buffer to the record FIFOs. Channel 2 is used for routing data from the frame buffer to the review buffer. Channel 3 is used for routing data from the review buffer to the frame buffer. The digital storage processor 8603 initializes the DMA controller 8683 by sending commands through a transceiver 8684. The direction of transceiver 8684 is set by the CPU 8603. During DMA controller transfers, transceiver 8684 is in a high impedance state so the data output from DMA controller 8683 enter into latch 8686, whereby addresses are put on the DMA bus.

The DMA controller 8683 is driven by a 4 mHz clock, which is derived from an 4 mHz clock signal input from clock 8608 into a flip-flop 8688 to divide the frequence by two. A 8 mHz signal is also input to flip-flop 8690 for synchronizing the ready input to DMA controller 8683 with the clock signal. The DMA controller 8683 also receives a chip select line and an I/O read or an I/O write signal from a three-state buffer 8692. The I/O read and I/O write signals are demultiplexed outputs from demultiplexer 8670 based upon the enable line and the read/write direction line output from the processor 8603.

When the DMA has completed a data transfer, PIA 8607 generates a DMA inhibit signal which is input into flip-flop 8694 to put the DMA controller 8683 on hold while the processor 8603 accesses the data bus. After the DMA controller has been initialized from processor 8603, one of four DMA acknowledge lines, corresponding to each of the four channels, is activated. The upper addresses are output through the data lines of DMA controller 8683 into an octal latch 8686, while the lower addresses are output through the address lines of DMA controller 8683. While the DMA transfer is occurring, flip-flop 8694 is generating a DMA busy signal input to the programmable interface adapter 8607. The DMA controller 8683 also refreshes the memory comprising the review buffer by disabling memory writes while enabling memory reads.

Referring to FIG. 28F, the review buffer interface includes data bus buffers 8696 and 8698, DMA address multiplexers 8700, 8702 and 8704, and dynamic memory timing logic. The least significant eighteen address bits are multiplexed into two 9-bit address blocks by multiplexers 8700, 8702 and 8704. A 200 nanosecond delay device 8606 is used to generate a row address strobe for the review buffer after a 40 nanosecond delay from the memory read and memory write lines input from the DMA controller. After another 40 nanoseconds, the delay device 8606 switches multiplexers 8700, 8702, and 8707 to transfer the upper 9-bit address blocks. After an additional 80 nanoseconds, the delay device 8606 generates column address strobes for the review buffer, thereby enabling data transferred through buffer 8696 for review buffer reads and 8698 for review buffer writes.

Referring to FIG. 18G, the frame buffer interface 8630 includes logic for inserting and stripping synchronization signals from data transfers between the frame buffer and review buffer. Referring to FIG. 18G, interface 8630 also includes circuitry for detecting a synchronization signal on a VCR playback when data is routed from VCR playback data processor 8650 through the review buffer interface 8620 into the frame buffer 8630. Referring to FIG. 20I, the frame buffer interface 8630 also includes frame buffer address counters and byte counters.

Referring to FIG. 18G, synchronization fields are added to a frame of data for frame buffer to review buffer data transfers, and stripped out on review buffer to frame buffer data transfers. The synchronization field includes five bytes of "F7" followed by one byte of "00." On data transfers from the frame buffer to the review buffer, the FBXINIT line resets flip-flop 8706 and the STF_NSTR line set for stuff mode enables output from octal buffers 8708. At this time, output from transceiver 8710 is disabled so that the F7s generated from buffers 8708 are output onto the data bus. The output of the data bus enters gate logic 8712, 8714, 8716 and 8718, which detects F7s and signals shift register 8720. After five sequential F7s, the output from shift register 8720 causes flip-flop 8722 to be set, which in turn causes octal buffer 8708 to generate an 00 signal. The output of flip-flop 8722 also activates a counter enable line (CTREN) and enables the frame buffer read and write strobes. Upon the next clock signal, buffers 8708 are disabled and frame buffer data is transferred through transceiver 8710 into the review buffer.

When the transfer is from the review buffer to the frame buffer, the transceiver 8710 is programmed to transmit data in the opposite direction and data coming off the data bus from the review buffer again enters synchronization field detection gates 8712, 8714, 8716, and 8718 to allow shift register 8720 to count the sync fields. After five bytes of F7 followed by one byte of 00, the output of transceiver 8710 is enabled and the data transfer from the review buffer to the frame buffer begins and the counter is enabled.

Figure 18L2:
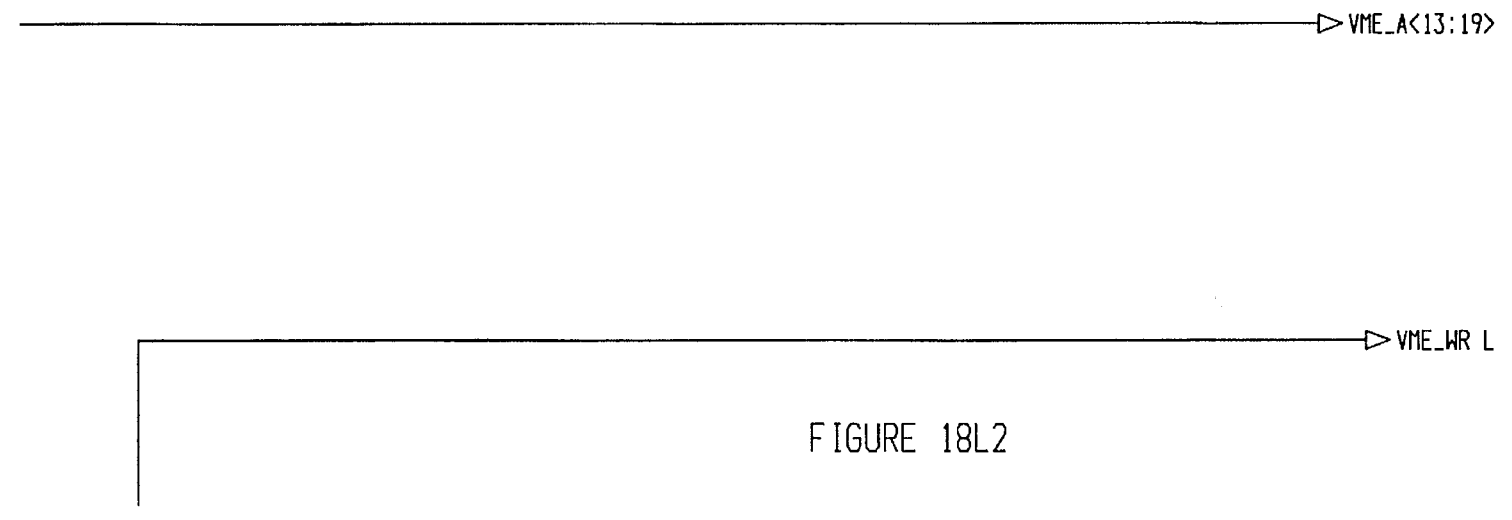
Figure 18H:
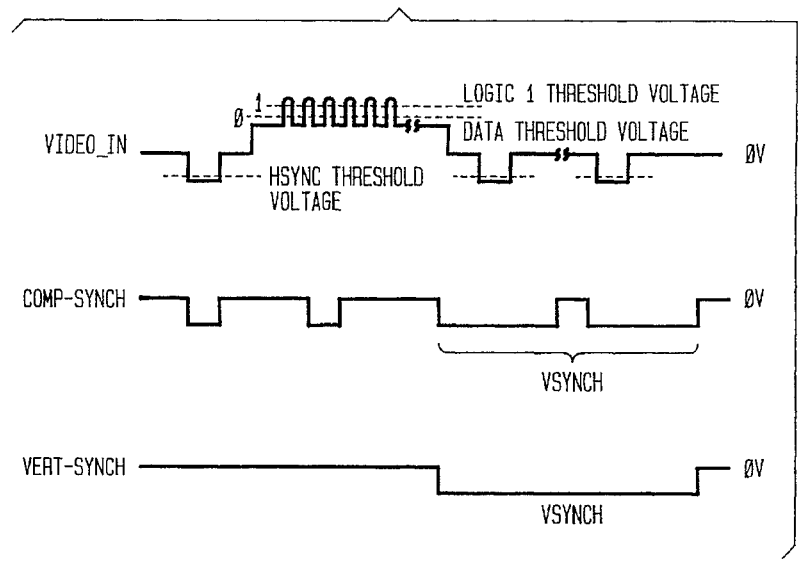

Referring to FIG. 18H, the output from synchronization detect gates 8712, 8714, 8716, and 8718 is also input into shift register 8722. The data on the bus in this case is data transferred for VCR playback. After the last synchronization field has been detected, flip-flop 8724 goes high, clocking registers 8726 and 8728 to capture the current address on the bus. The output of flip-flop 8724 also clocks flip-flop 8730 to send a synchronization detect status interrupt to the PIA 8607, which in turn causes processor 8603 to enable output from registers 8726 and 8728 so that the CPU can read the sync field address.

After a sync field stuff or strip or detect, flip-flop 8722 activates a counter enable signal. Referring to FIG. 18I, this counter enable signal activates address counters 8732, 8734, 8736, 8738, 8740 to count up from zero, thereby generating the least significant 18-bit address bits. Counter enable signal also activates byte counters 8742, 8744, 8786, 8748 to count down. The byte counters are only used on frame buffer to review buffer data transfers. During a frame buffer to review buffer data transfers, the address counters are loaded with zeros and the byte counter is loaded with the number of bytes to be transferred. When the byte counters count out to zero, an FBXTC signal is generated which is input to gates 8752 along with a data transfer acknowledge signal to signify an end of processing input into DMA controller 8683. During other data transfers, the address counters and byte counters are loaded with zeros at initialization.

The schematics for the frame buffer system interface 8750 are shown in FIGS. 18J through 18N and FIGS. 18P and 18Q. The schematics for the frame buffer are shown in FIGS. 18R through 18X. The frame buffer 8760 comprises two redundant frame buffers of 257 k by 8-bit RAM. The redundant buffers are used in a ping-pong fashion so that data can be read into a first frame buffer while being read out of a second frame buffer during one frame. Then, on the following frame, data is written into the second frame buffer while reading out of the first frame buffer. Each frame buffer is logically divided to store CPU data at addresses 0 through 600 and ECG data at addresses 601 through 700. Image/velocity data is stored in addresses 701 up to a variable address programmably selected. The next address greater than this variable address marks the starting address for spectrum data memory. Depending on the system mode, the system CPU sets the variable address to mark the end of the image/velocity data memory area.

Referring to FIG. 18J, arbiter 8762, a programmable array logic device, receives a data transfer request for each of the four types of data transfers and outputs a grant signal to initiate the transfer. Each grant output signal is an input to PAL 8764 for generating the memory cycle timing sequences during a data transfer.

Referring to FIG. 18L, a transfer of CPU data from the system CPU into a frame buffer is initiated by the system CPU. The system CPU activates each of the PB_BDENA, PB_BDSTROB, V_WRITE, and V_AS signals. These signals are received into the digital storage subsystem at octal buffer 8766, then input to PAL 8768, which generates the VME request signal input into arbiter 8762 of FIG. 18J. For a transfer of CPU data into the frame buffer, the data is input into transceiver 8770 and then transferred into octal buffer 8772 of FIG. 18M before entering frame buffer 8760. The address for each data item is sent over the VME bus and received at octal buffers 8774 and 8776 and then transferred into octal buffers 8778 and 8780 before being routed to frame buffer 8760. The VME request signal output from PAL 8768 of FIG. 20L triggers the transfer by being input to PAL 8762 via flip-flop 8782. Once PAL 8762 issues the VME grant, the grant signal resets flip-flop 8782.

Referring to FIG. 18L, control register 784 is used by the system CPU to set the start address of the spectrum data transfer (PR_SPEC), to request the reactive frame buffer to be toggled (VME_FOR_REQ), to set a status signal signifying a data transfer (SCAN_DATA_XFR), and to set a test signal (TEST ONE) which disables ECG, image velocity, and spectrum data requests during a VCR record so that a test pattern can be written into the frame buffer from the VME bus.

When the system CPU requests to read the frame buffer, the sequencing described above is the same, although the data is transferred from the frame buffer 8760 into octal register 8786 of FIG. 18M, then into transceiver 8770 of FIG. 18L before being transferred over the VME bus. The transfer through octal register 8786 is enabled by a VME_RDEN signal output from PAL 8768 of FIG. 18L and clocked by a VME_RD_DCLK signal output from PAL 8788 of FIG. 18K. The clock signal output from PAL 8788 is triggered from the memory cycle timing sequence of outputs from PAL 8764 of FIG. 18J.

Referring to FIGS. 18J, 18K, and 18N, an image/velocity data transfer is triggered by the centroid subsystem, which outputs a CD_DSTRB signal into flip-flop 8790, which, in turn, outputs an IMVEL_REQ signal to arbiter 8762. Flip-flop 8790 generates the IMVEL_REQ signal only when the SCAN_DATA_EN signal is active. The SCAN_DATA_EN signal is active when the SCAN_DATA_XFR signal output from control register 8784 of FIG. 18L is active. Arbiter 8762 issues a grant signal (IMVEL_GR) to enable the transfer, to reset flip-flop 8790, and to trigger PAL 8764 to output the memory cycle timing sequences for the data transfer. The image/velocity grant signal (IMVEL_GR) is input to PAL 8792 of FIG. 18K along with an IMVEL_STRB signal from the centroid subsystem. PAL 8792 then generates a write enable signal, a data clocking signal for a read operation, and image/velocity address increment signal. Referring to FIG. 18N, the IMVEL_STRB and the IMDEL_WREN signals enable the transfer of centroid data into the frame buffer via register 8794. The address for each data transfer is generated by binary counters 8796 through 8800. The counters are hardwired to generate an initial address of 700 for the first transfer. The IMVEL_INCR signal is then used for incrementing the address output from the counters 8796 through 8800. For a transfer of data from the frame buffer to the centroid subsystem, the data is transferred through register 8802 of FIG. 18N. Transfer through the register 8802 is enabled during playback and clocked based upon the memory cycle timing sequences output from PAL 8764 of FIG. 18J into PAL 8792 of FIG. 18K (IMVEL_RD_DCLK).

Referring to FIGS. 18J, 18K, and 18P, and ECG data transfer is initiated by a signal, SD_EDSTRB, from the ECG subsystem input into flip-flop 8804. Flip-flop 8804 activates an ECG_REQ input to PAL 8762, which in turn generates an ECG grant signal. The ECG grant signal resets flip-flop 8804, initiates the memory cycle timing sequences to be output from PAL 8764 and enables the data transfer. The memory cycle timing signals and the grant signal, along with the ECG_STRB signal from the ECG subsystem, are input to PAL 8792 to generate a clock for ECG reads, and enable for ECG writes, and an increment signal (ECG_INCR) for counting ECG addresses. Referring to FIG. 18P, ECG data entering from the spectrum velocity board enters register 8806. The transfer from register 8806 to the frame buffer is enabled by an ECG_WREN signal and clocked by an ECG_STRB signal. When the spectrum velocity board reads ECG data, the data is transferred from the frame buffer into the spectrum velocity subsystem via register 8808. Register 8808 is enabled during playback and is clocked by an ECG_RD_DCLK signal. Frame buffer addresses for reading and writing the ECG data are generated by counters 8008 through 8810 and buffer 8810[?]. The counters and buffer are hardwired to generate an initial address of 600, which is then incremented by the ECG_INCR signal output from PAL 8792.

Referring to FIGS. 18K, 18J, and 18Q, a spectrum data transfer is initiated by a T_SACT signal output from the spectrum velocity subsystem into flip-flop 8812 of FIG. 18J. For spectrum data transfers, one T_SACT signal triggers two sequential requests to arbiter 8762. Flip-flop 8812 generates the first request, and when granted, is reset by the grant signal. The grant signal then triggers flip-flop 8814 to generate the second request into PAL 8762. The grant signal, SPEC_GR triggers the memory cycle timing sequences and activates the data transfer. Referring to FIG. 18K, PAL 8788 receives the memory cycle timing signals to generate the read clock, write clock, write enable, and address increment signals. Referring to FIG. 20Q, the high bits for the initial address within the frame buffer for spectrum data are loaded into counters 8819 and 8820 from the system CPU via transceiver 8770 and register 8784 of FIG. 18L. The lower bytes are hardcoded to generate an initial output of zero. The SPEC_INCR then increments counters 8816 through 8820 to generate the sequential addresses. For a write of spectrum data from the spectrum velocity subsystem, the data enters registers 8822 and 8824 sequentially for each of the two bytes transferred per grant signal. Similarly, for a read from the frame buffer, the two bytes are sequentially transferred through registers 8826 and 8828 before being transferred to the spectrum velocity subsystem.

Referring to FIGS. 18R through 18X, the frame buffer comprises two redundant frame buffers with address and data multiplexing and frame buffer switching logic. Referring to FIG. 18R, PAL 8816 controls which frame buffer is linked to the frame buffer system interface 8750 and which is linked to the frame buffer interface 8630. The trailing edge signal TB_BM1, entering from the timing and control subsystem, after passing through register 8818, causes PAL 8816 to toggle as long as the FBX_BUSY signal is inactive. When the FBX_BUSY signal is active, a frame buffer transfer is in process, so no toggling occurs. The low-going edge of signal TB_BM1 causes an interrupt to the system's CPU (V_IRQ6). This interrupt is used on playback to allow one frame to be played through the system at a time. The service routine checks data in the frame buffer to see if a new mode or system reconfiguration is necessary.

When the SCAN_DATA_XFR input to PAL 8816 is active, the SCAN_DATA_EN output becomes active at the beginning of the following frame, causing data to be transferred between the frame buffer and the system in either direction. When a CPU data transfer is requested (VME_FR_REQ) and the corresponding VME grant signal becomes active, PAL 8816 outputs an FBX_REQ signal to interface adapter 8607 of FIG. 18C. At the same time as the FBX_REQ signal becomes active, the ADDR_SET output becomes active to initialize the address counters of FIGS. 18N, 18P, and 18Q. (Register 8818 receives a TB_BM1 input from the timing and control subsystem and a PLYBCK input also from the timing and control subsystem. The register 8818 outputs the input and also routes the output around to generate a second input and thereby generate a BM1 signal, a BM1 delay signal, a playback signal, and a playback delay signal, each of which is input to PAL 8816. PAL 8816 detects the first leading edge of the playback signal, then generates a first playback request output (FST_PLYB_REQ).

The frame buffer select signals (S1, S0) are input into several 2×1 multiplexers to select which timing and control signals are routed to which frame buffer. The read and write signals (FBWR, SWR, FBRD, SRD) are multiplexed by 2×1 multiplexer 8820 to generate the write signal and read signal for frame buffer 0 (WR0, RD0) and the write signal and read signal for frame buffer 1 (WR1, RD1). The ready signal from each frame buffer is multiplexed at 2×1 multiplexer 8822 to derive the frame buffer interface ready signal (FBRDY) and the frame buffer system interface ready signal (SRDY).

With reference to FIG. 18S, the address lines input from frame buffer system interface 8750 and frame buffer interface 8630 are multiplexed to derive frame buffer 0 address signals by 4×1 multiplexers 8824 through 8828. During a memory refresh cycle for frame buffer 0, counter 8830 increments the memory addresses.

Referring to FIG. 18T, counter 8832 is used to generate a memory refresh request signal. The request signal stays active until a refresh cycle signal (RCYO) is output from PAL 8834 to reset the counter 8832. PAL 8834 generates the select, enable, write, row access, and column access signals for frame buffer 0. When writing out from frame buffer 0, decoder 8836 decodes the frame buffer 0 write signal and frame buffer 0 chip column access select signal to determine which of buffers 8838 and 8840 are enabled. Buffer 8838 routes the data to the frame buffer system interface 8750, while buffer 8840 routes the data to the frame buffer interface 8630. For writing into the frame buffer 0, the data lines from frame buffer system interface 8750 and frame buffer interface 8630 are multiplexed by 2×1 multiplexers 8842 and 8844.

Referring to FIG. 18U, the memory for frame buffer 0 comprises eight 256 k by 1-bit RAMs 8846 through 8853. Referring to FIGS. 18V, 18W, and 18X, the address switching logic, data switch/control logic, and memory circuitry for frame buffer 1 are identical to that in FIGS. 18S, 18T, and 18U for frame buffer 0. The part numbers therefor have been numbered with the same numbers as the corresponding parts in FIGS. 18S, 18T, and 18U, but with a prime sign (').

Referring to FIGS. 18A and 18Y, the VCR record data processor is shown in block diagram format. The circuit schematics for the VCR record data processor 8640 are shown in FIGS. 18Z, 18AA, and 18BB. Referring to FIGS. 18Y, 18Z, 18AA, and 18BB, control signals from the CPU 8601 and the DMA controller 8610 are input into FIFO input control 8854. FIFO input control 8854 controls the addressing of RAMs 8858 and 8860 such that the RAMs function as a FIFO memory. When the FIFO reset signal from CPU 8601 is active, the FIFO input control 8854 is reset. When the I/O write signal and data transfer acknowledge signal from the DMA controller 8610 are active, FIFO input controller 8854 will enable buffer 8856 to pass data from the DMA controller bus into the record FIFO RAMs 8858 and 8860 or from the RAMs 8858 and 8860 through buffer 8856 and onto the DMA controller bus. The FIFO input control 8854, however, generates a wait signal output to the DMA controller 8610 when a data transfer is already in process to preclude the DMA controller 8610 from initiating another data transfer. When data is output from record FIFO memory 8858 and 8650, the data passes through register 8862, then into shift register 8864 for serializing the data. The timing signals for VCR record data processor transfer are generated by record timing generator 8866 of FIG. 18Y, which comprises the 24 mHz clock 8868 and binary counters 8870, 8872 of FIG. 18AA. The timing generator 8866 outputs a 12 mHz clock cycle and a 1.5 mHz clock signal.

Referring to FIG. 18AA, CRT controller 8874 receives control signals and data from CPU 8601 for generating a vertical synchronization, horizontal synchronization, and display enable signal. The record data which is input into shift register 8864 is serialized and shifted out into PAL 8645, which encodes the signal and inserts the horizontal and vertical synchronization signals. Counter 8876 is used to space the vertical synchronization signal within the record data stream by outputting a pulse into PAL 8877. The CRT controller 8874 produces a vertical synchronization signal that is too wide, so counter 8876 generates a sync signal four pulses wide instead of the 16-pulse width output from the controller 8874. When data is read from RAMs 8858 and 8860, a read signal (RRD) is output from FIFO input controller 8854 into a delay device 8878 which delays the signal by 160 nanoseconds. The delay device 8878 then generates a reset signal into flip-flop 8880 to reset FIFO input controller 8854.

Three data signals are output from encoder 8877. One is a stream of NRZ data, a second is a data available signal, and a third is a comparative synchronization signal. The outputs are prioritized by the encoder PAL 8877, so only one stream is active at a time. The three output lines are resistively summed together by resistors 8882, 8884, and 8886 before entering filter 8888. The active signal passes through filter 8888 and into buffer 8890 before being output to the graphics I/O subsystem.

Referring to FIG. 18AA, the + and −12 volt DC power signals for the digital storage subsystem are derived from + and −15 volt DC power signals transformed by voltage regulators 8892 and 8894.

Referring to FIGS. 18A and 18BB, the VCR playback data processor 8650 is illustrated in block diagram format. The circuit schematics for the VCR playback data processor 8650 are shown in FIGS. 18CC through FIGS. 18GG.

Referring to FIG. 18BB and 18CC, the video signal is input from the graphics I/O subsystem and passes through filter 8898 to reduce noise, then is input into buffer 8900. The output of the buffer 8900 is AC coupled into a diode network for clamping the tips of the horizontal synchronization signal to ground, thereby restoring a DC signal. The output of buffer 8900 also enters horizontal sync separator 8904, which comprises a comparator 8906 for stripping off the composite sync signal. The composite sync signal then passes into vertical synchronization separator 8908, which comprises a comparator 8910 to strip out the vertical synchronization signal.

FIG. 18HH illustrates below, the video input stream format and distinguishes the horizontal synchronization, the vertical synchronization, the data logic 0, and the data logic 1 signals.

The DC restored signal (FILTER_VIDIN) is input to threshold generator 8912. Referring to FIGS. 18CC, FIG. 18BB, FIG. 18HH and FIG. 18DD, the composite sync signal output from the horizontal synchronization separator 8904 is input into one-shots 8914 and 8916 of threshold generator 8912. One-shot 8914 triggers on the trailing edge of the composite sync signal, thereby turning on analog switch 8918 to clamp a portion of the video signal to ground and detect the horizontal sync threshold voltage shown in Table A. One-shot 8916 triggers on the leading edge of the composite sync signal and thereby turns on analog switch 8920 to sample the level of the horizontal synchronization and establish the thresholds for the video data signals, shown in Table C as logic 1 threshold voltage and data threshold voltage. The threshold voltage signals are then input into OP AMP 8922, acting as a comparator for detecting a DC signal, and then input into OP AMP 8924 to invert the signals before entering into comparators 8926 and 8928. The DC restored video signal (FILTER_VIDIN) also is input into comparators 8926 and 8928 to check the restored video signal for data by comparing the voltage levels of the video signal to the threshold voltage signals. Comparator 8926 detects the logic 1 threshold voltage and thus a logic 1 signal, whereas comparator 8928 detects the presence of any data.

Referring to FIG. 18BB and FIG. 18EE, the vertical synchronization signal is input into line counters 8930 and 8932, which are clocked by the composite sync signal. With each new vertical synchronization pulse, line counters 8930 and 8932 generate an SIEN output signal to enable the video input data to be shifted in. Referring to FIG. 18FF, the SIEN signal is input into FIFO input controller 8934. Referring to FIGS. 18AA and 18FF, a 24 mHz clock signal (PCLK) is output from clock 4868 of FIG. 18AA into phase offset generator 8936 of FIG. 18BB, which comprises flip-flops 8938 and 8949 of FIG. 18FF. The output of the flip-flops 8938 and 8940 are input into binary counter 8942, which generates a bit clock signal for clocking byte/line counter 8944. The output of counter 8944 is input into FIFO input controller 8934.

The bit clock is also used to clock shift register 8946. Shift register 8946 receives the serialized input signal (VIDIN_DATA) output from comparator 8926 of FIG. 18DD. This signal distinguishes between data logic level 1 and data logic level 0. Shift register 8946 converts the serial input stream into an 8-bit playback data stream output to parallel registers 8948 and 8950.

Referring to FIGS. 18BB, 18FF, and 18GG, the playback data output from registers 8948 and 8950 is input into playback FIFO 8952 of FIG. 18BB, which comprises buffer 8954, 2 k by 8-bit RAMs 8956 and 8958, FIFO RAM controller 8960, and octal buffer 8962. The playback data first enters into buffer 8954; then, when enabled by FIFO RAM controller 8962, outputs the data into RAMs 8956 and 8958. FIFO RAM controller 8960 receives inputs from digital storage CPU 8601 and DMA controller 8610.

A FIFO reset signal is input from the digital storage CPU 4601, while a data transfer acknowledge and an I/O read signal for initiating the transfer are input from DMA controller 4610. FIFO RAM controller 8960 additionally receives a playback data sampling input from PAL 8934 of FIG. 18FF, which signifies that data is available for transfer.

For transfers of data out of playback FIFO 8952, FIFO RAM controller 8960 addresses RAMs 8956 and 8958, thereby putting a byte of data at the inputs of buffer 8962. The FIFO RAM controller 8960 enables output from buffer 8962 and thus the data is transferred onto the DMA controller bus for a transfer into the review buffer interface. The data stream output from buffer 8962 of FIG. 18GG additionally is input into sync detector 8964 of FIG. 18BB, which comprises gates 8714, 8716, and 8718 of FIG. 18G for detecting the sync signal, F7F7F7F7F700.

A description of the firmware for CPU 8601 follows:
Main Program:

On hardware reset, in one embodiment the CPU 8603 is vectored to an assembly language routine called RESTART. This short routine initializes the direct page register in the CPU 8603, loads the address of the main program (MAIN) from a variable called COLD-START, and begins interpretation of MAIN. MAIN then initializes two stack pointers (RP and SP), calls the hardware initialization work INIT, and enters the main program loop. This infinite loop identifies the current operational mode and then calls the appropriate routine. Any change in mode results in exit from the called routine back to MAIN.
Hardware Initialization:

Hardware initialization is handled by the word INIT. This high-level word performs the following functions:

a) Initialize the ACIA 8606, PIA 8607, CRT controller 8874, and DMA controller 8683.

b) Clear the record and playback FIFOs.

c) Initialize working variables and arrays.

d) Start the command interrupt process.

e) Set the record mode as the default mode.

f) Start the DMA-Done interrupt process with a review buffer refresh cycle.

Idle Mode:

In IDLE-MODE, frame transfers are inhibited. The only functions performed are status checking, command processing, and sending responses to commands. Exit from idle mode occurs when a new mode is commanded.
Record Mode:

RECORD-MODE is entered from MAIN when a change to this mode is commanded. RECORD-INIT is first executed to select the DMA-done interrupt service routine for record mode, move the output pointer to the head of the review buffer, and clear the FIFOs. A loop, terminated by a mode change, is then entered which performs the following operations:

a) If a frame buffer transfer is not in progress, and if there is a pending request, then start a frame buffer to review buffer transfer.

b) If a frame is available, and if a VCR transfer is not in progress, then start a review buffer to VCR transfer and advance the output pointer forward.

c) Update internal status variables.

d) Process command if available in command buffer.

e) Send command response if available in response buffer.

Playback Mode:

PB-MODE is entered from MAIN with a mode change to playback mode. The initialization word, PB-INIT, is executed to select the DMA-Done interrupt service routine for playback, move the output pointer to the head of the review buffer, and clear the FIFOs. Then the VCR to review buffer transfer process is started with execution of VCR>. No other foreground actions are involved in transferring frames from the VCR to the review buffer. A loop, terminated on a mode change, is then entered to perform the following tasks:

a) If a review buffer to frame buffer transfer is not in progress, and if there is a pending request, and if a frame is available, then execute steps b, c, d; otherwise go to step e.

b) If more than 8 frames are buffered between the input pointer and output pointer in the review buffer, then advance the output pointer by one frame. This prevents excessive latency from input to output.

c) If the frame is not marked invalid, then start a review buffer to frame buffer transfer.

d) Advance the output pointer by one frame.

e) Update internal status variables.

f) Process command if available in command buffer.

g) Send command response if available in response buffer.

Cine Loop Mode:

A mode change to cine loop causes MAIN to call CINE-MODE. This routine calls CINE-INIT, which performs the same initialization as PB-INIT, in addition to setting the cine loop begin and end pointers to include all data in the review buffer. A loop, terminated by a mode change, is then entered which performs the following tasks:

a) If a frame buffer transfer is not in progress, and if a request is pending, and if a frame is available, then execute steps b, c, d; otherwise go to step e.

b) If the current frame is not marked invalid, then start a review buffer to frame buffer transfer.

c) If in cine loop forward mode, then advance the output pointer forward. If begin/end mode is enabled, then loop the output pointer from cine loop end to cine loop begin. Otherwise loop the output pointer from the end of the review buffer to the beginning of the review buffer.

d) If in cine loop reverse mode, then advance the output pointer in reverse. If begin/end mode is enabled, then loop the output pointer from cine loop begin to cine loop end. Otherwise loop the output pointer from the beginning of the review buffer to the end of the review buffer.

e) Update internal status variables.

f) Process command if available in command buffer.

g) Send command response if available in response buffer.

DMA-Done Interrupt Service Routine:

The DMA-Done interrupt routine handles frame transfers once they are enabled by the foreground routines FB>, >FB, VCR>, and >VCR. Separate service routines are used for record and playback modes (RM-ISR and PBM-ISR, respectively). This routine also manages the buffer pointers (RBIP, RBOP) and determines the block size of the transfer. The hardware restricts DMA to 64 K pages, so the block size is adjusted to prevent page crossing as well as for partial blocks at the end of a frame.

Record Mode DMA-Done:

DMA-Done vectors to the RM-ISR word in record mode. This routine performs the following functions:

a) Reset the DMA-Done request bit with CLR-CA1.

b) If an external EOP occurred on the last frame buffer transfer, then get the ending address, make an entry for the frame in the frame table, and clear the frame buffer DMA enable flag.

c) If VCR DMA is enabled, and if the record FIFO is less than ½ full, then DMA a block (2048 bytes or less) to the record FIFO and exit. If this was the last block in the frame, then clear the VCR DMA enable flag.

d) If the frame buffer DMA enable flag is set, then get a block (2048 bytes or less) from the frame buffer and exit.

e) If this step is reached, then both VCR and frame buffer DMA is not active. In this case, perform a dummy memory to memory transfer to refresh the review buffer RAM and exit.

Frame Table:

The frame table keeps track of frame starting addresses in the review buffer. Each table entry consists of 4 bytes. The first byte is a flag, which is set to −1 if the frame is determined to be invalid (too large, too small, or truncated by a mode change). The remaining three bytes are the address of the frame in the review buffer. Five 16-bit pointers to the frame table are used to select frames for output, enter frames in the frame table, and perform cine loop addressing. The pointers are described in detail below:

a) Input Pointer: IN-FRM points to a frame table entry that holds the starting address of the frame currently being input to the review buffer.

b) Output Pointer: OUT-FRM points to a frame table entry that holds the frame address of the next frame available for output. If OUT-FRM=IN-FRM, then the review buffer is empty.

c) End Pointer: END-FRM points to the oldest valid entry in the frame table. When old frames need to be dropped to allocate space for a new frame, END-FRM is advanced to free the memory.

d) Cine Loop Begin Pointer: CLB-FRM points to the cine loop begin frame table entry.

e) Cine Loop End Pointer: CLE-FRM points to the cine loop end frame table entry.

Review Buffer

A functional block diagram and system interface block diagram for the review buffer 9100 are shown in FIGS. 19A and 19B, respectively, with circuit diagrams shown in FIGS. 19C–19S. With reference to FIG. 19B, the review buffer provides dynamic memory for storing and retrieving data from the digital storage subsystem 8600 during system operation. During normal operation, the review buffer is used conceptually as a large FIFO memory device, where the oldest data are continuously being written over by new incoming data. When the operator selects to use an image replay loop capability, the contents of the review buffer 9100 memory modules 9101 are continuously sent to the frame buffer interface 8630 of the digital subsystem 8600 for continuously replaying the same image sequence on a monitor. During this image replay, the ability to write new data to the memory modules is inhibited.

When the operator selects to record output, the review buffer 9100 alternates between accepting new data from the digital subsystem 8600 and sending data to the digital subsystem VCR record interface 8640 for recording. During a digital playback, the review buffer alternates between taking data from the VCR playback interface 8650 and sending this data to the frame buffer interface 8630 for output to the monitors.

With reference to FIG. 19A, one embodiment of the review buffer 9100 includes memory modules 9101, a digital storage interface 9102, and a memory bank select line decoding logic 9103. Data enter the review buffer 9100 from the digital subsystem 8600 at digital storage interface 9102. A corresponding memory address accompanies the data signals, along with a row address strobe and write enable signal. A column address strobe enters memory bank select line decoding logic 9103. All these inputs are received by the memory modules 9101 for selecting a specific memory address to store the incoming data or to select a specific location whose contents are to be output. In one embodiment, there are four memory modules 9101 within the review buffer 9100. Each module includes 1 megatye of RAM organized into four banks. Each bank includes eight 256 k by 1-bit RAMs, with each RAM having nine address bits, one data-in bit, one data-out bit, a row address strobe pin, a column address strobe pin, and a write enable pin.

The review buffer 9100 circuit diagrams are shown in FIGS. 19C–19S. Referring to FIG. 19C, the signals from and to the digital subsystem 8600 enter the review buffer via a backplane connector. The data lines enter buffer 9111, then enter the memory modules 9101, while the address lines, bits 0–7, enter buffer 9109, then enter the memory modules 9101. Address line bit 8, row address strobe, and write enable signals similarly enter buffers 9158, 9159 and 9160, respectively, then enter the memory modules 9101. The column address strobe signal input from the digital subsystem includes five lines, four lines of which provide a 4-bit encoded signal to two decoders 9105 and 9107 which enable the fifth line, the actual column address strobe, to be routed to the selected memory bank. There are sixteen memory banks, four per memory module. Several resistor networks 9104, 9106, 9108, 9110 and 9112 eliminate noise on the lines by matching the end line impedance.

Still referring to FIG. 13C, data are output from memory modules 9101 to the digital subsystem via buffer 9113 and the backplane connector.

One embodiment for the circuits of the first memory module are illustrated in FIGS. 19D–G. Similar circuits for the second, third, and fourth memory modules are illustrated in FIGS. 19H–K, 19L–O, and 19R–S, respectively. Each memory module 9101 includes four banks. Referring to FIGS. 19D–G, the first bank of the first memory modules includes eight 256 k by 1 RAMs 9116, 9120, 9124, 9128, 9134, 9138, 9142 and 9146. The same column address strobe encoded signal selects each of the RAM chips in the same bank, while the specific RAM chip within the bank is selected with the row address strobe signal. Similarly, the second bank of the first memory module includes eight 256 k by 1 RAMs 9117, 9121, 9125, 9129, 9135, 9139, 9143 and 9147; the third bank includes eight 256 k by 1 RAMs 9118, 9122, 9126, 9130, 9136, 9140, 9144 and 9148; and the fourth bank includes eight 256 k by 1 RAMs 9119, 9123, 9127, 9131, 9137, 9141, 9145 and 9149. Each of the eight RAMs within a memory bank has a single data output line which corresponds to a specific bit of an 8-bit data word output from the memory module. For the first memory module, RAMs 9116–9118 correspond to bit 0; RAMs 9120–9123 correspond to bit 1; RAMs 9124–9127 correspond to bit 2; RAMs 9128–9131 correspond to bit 3; RAMs 9134–9137 correspond to bit 4; RAMs 9138–9141 correspond to bit 5; RAMs 9142–9145 correspond to bit 6; and RAMs 9146–9149 correspond to bit 7.

The address lines enter address line buffers 9114 and 9132 before entering each of the thirty-two RAM chips. Resistive networks 9115 and 9133 are positioned between buffers 9114 an 9132, respectively, to eliminate noise by matching the end line impedances.

The circuits for the second, third, and fourth memory modules, shown in FIGS. 19H–K, 19L–O, and 19R–S, respectively, have the same structure as the first memory module, shown in FIGS. 19D–G and described above, with only the part number references varying.

With reference to FIGS. 19H–K, the second memory module includes thirty-two 256 k by 1 RAMs 9152–9167 and 9170–9185, buffers 9150 and 9168, and resistor networks 9151 and 9169. With reference to FIGS. 19L–190, the third memory module includes thirty-two 256 k by 1 RAMs 9188–9203 and 9206–9221, buffers 9186 and 9204, and resistor networks 9187 and 9205. With reference to FIGS. 19P-S, the fourth memory module includes thirty-two 256 k by 1 RAMs 9224–9239 and 9242–9257, buffers 9222 and 9240, and resistor networks 9223 and 9241. The fourth memory module is an expansion option.

ECG Board

Referring to FIG. 2B, the function of the ECG board 104 is to amplify an ECG signal from a patient input through electrode leads, normalize the signal amplitude, detect the peak of the signal between sample times, convert the analog waveform into a 8-bit serial digital data string, and provide logic signals to indicate ECG board status, leads-off/defibrillation, and pacer. When electrodes are connected to the patient, the digital conversion is enabled by a convert signal and clock signal from the spectrum velocity subsystem. The digitized ECG data and an ECG board status signal then are output to the spectrum velocity subsystem.

An ECG display will appear on the monitor whenever the ECG status line is active and the spectrum velocity subsystem is installed. The status line is active whenever the ECG board is present in the system, electrodes are connected to a human body, and the ECG power supplies are operational.

The leads-off/debrillation signal becomes active when the ECG electrodes become disconnected or a defibrillator pulse is detected. The pacer signal becomes active if a pacemaker pulse is detected.

Audio Switch

Referring to FIG. 2B, the audio switch receives signals from the microphone, or spectrum signals from the spectrum velocity board, and sends them out to the video cassette recorder for recording. It then takes the signals from the VCR, or spectrum signals from the spectrum velocity board, and delivers them to the headphones and/or to the loud speakers through the speaker cutout relay. It contains a dual dynamic noise reduction circuit, and a dual analog multiplier for remote volume control, and a stereo power amplifier for driving the loudspeaker or headphones.

CPU Subsystem

Figure 20B:
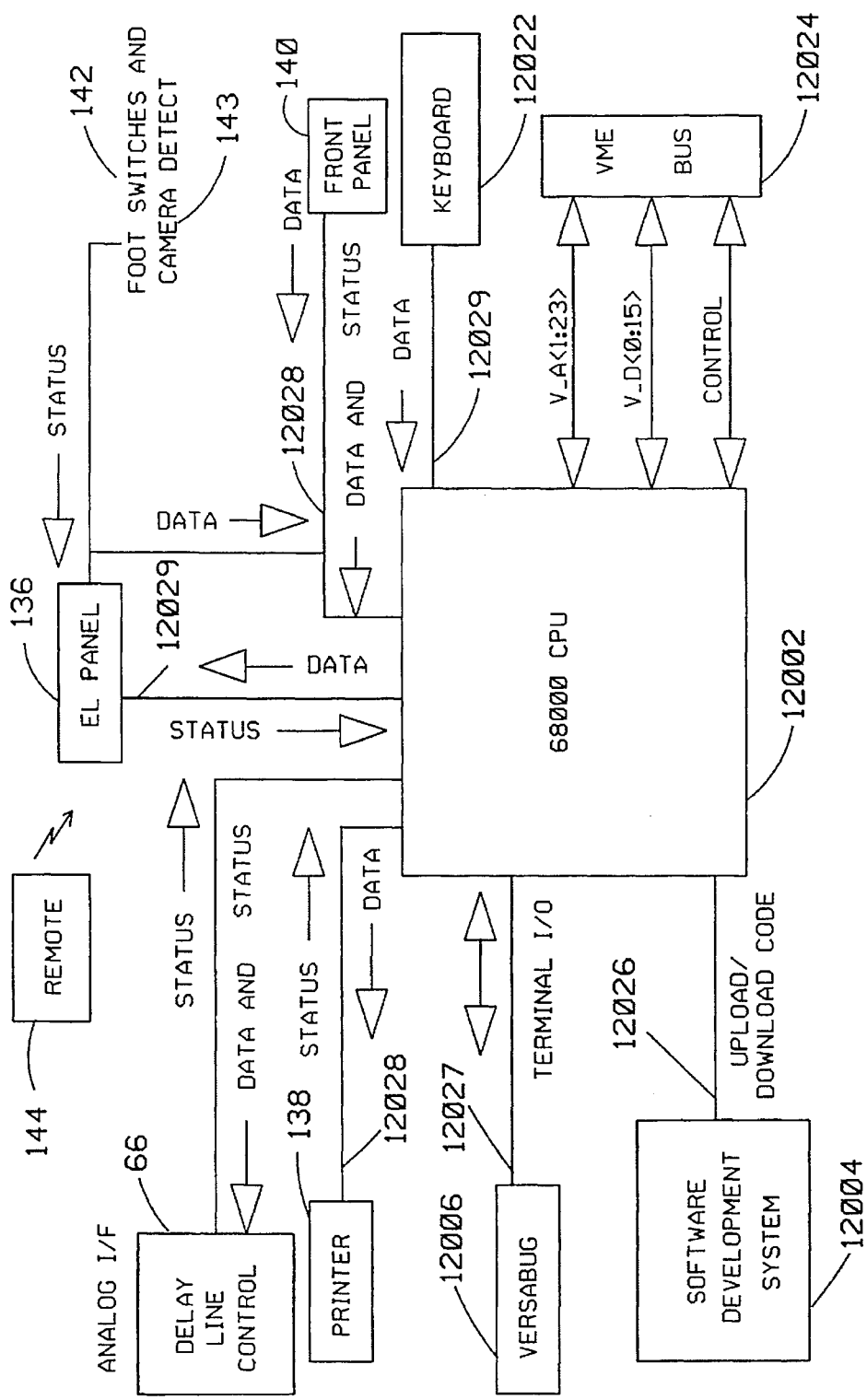
FIG. 20 is a block diagram of the system CPU subsystem.

A block diagram of the CPU subsystem 12002 is shown in FIG. 20A, while another block diagram, FIG. 20B, shows the CPU subsystem interfaces. With reference to FIG. 20A, the subsystem includes the central processing unit (CPU) 130. Although the type of CPU can vary, a standard off-the-shelf 16-bit microprocessor with 16-megabyte addressing capability and a 10 megaHertz (mHz) clock rate is shown in one embodiment. The CPU 130 provides the central coordination for all activities.

Referring to FIG. 20A, a read only memory (ROM), shown in this embodiment as 512 k bytes of EPROM 12038, stores the software, including the executable instructions, constant data, initialization data, and data to be downloaded to other subsystems over the VME Interface 12044. For storing variables, stacks, buffers, local data, and other data structures during operation, a random access memory (RAM), shown in this embodiment as 512 k bytes of dynamic RAM 12036, is used. To avoid losing certain data during a temporary power outage, nonvolatile RAM 12034 is used. The data stored in RAM 12034 include the system mode and several status bits from various peripherals.

Also included within the CPU subsystem 12002 are a time-of-day counter 12032, six serial I/O channels 12026–12031, a VME interface 12044, and two interrupt controllers 12040, 12041. The interrupt controllers 12040, 12041 field interrupts from the time-of-day counter 12032, peripherals (via the serial I/O channels 12026–12031), and other subsystems (via the VME interface 12044). In this embodiment, up to sixteen interrupt vectors can be fielded by the interrupt controllers 12040, 12041 and directed to the CPU 130. The VME interface 12044 links VME bus 12024, shown in FIG. 20B, to CPU 130.

With reference to FIG. 20B, the CPU subsystem interfaces to peripherals by serial I/O channels 12026–12031 and to other subsystems by the VME bus 12024. In one operational embodiment, the serial I/O channels 12026–12031 are standard RS 232 serial interfaces. Serial I/O channel 12026, a 19.2 kilo-baud channel, links the CPU to a software development system 12004, while serial I/O channel 12027, a 19.2 kilo-baud channel, links the CPU 130 to monitor/keyboard 12006. Both the monitor/keyboard 12006 and the software development system 12004 are test devices used only for system development and system testing.

Serial I/O channel 12028, a 9600 baud channel, links CPU 130 to printer 138, electroluminescent panel 136, foot switches 142, camera detect switch 143, and front panel 140. Channel 12028 carries printout data from CPU 130 to a standard off-the-shelf printer 138 and carries EL panel 136, front panel 140 foot switches (foot-activated switches resting on the floor) 142, and camera detect switch 143 inputs to CPU 130. Electroluminescent (EL) panel 136 displays system menus for users to monitor system status or examine input command options. EL panel 136 also contains an infrared receiver for accepting data from an infrared transmitter within remote 144. Remote 144 is a user-convenient wireless (or hardwired) input device and additionally comprises a track ball and several function keys to invoke specific menus, such as spectrum, velocity, flow angle, stenosis, and measurement. When remote 144 is hardwired to the system, a cable connects remote 144 to EL panel 136. Data transmitted from remote 144 to EL panel 136 is carried to CPU 130 over serial I/O channel 12028. Data input from front panel 140 includes, in one operational embodiment, detection of one of the following programmed function keys: audio volume, initialize, self-test, zoom, patient history, protocol, status, assist, video invert, frequency, tissue only, imaging, and digital playback. Serial I/O channel 12029, a 19.2 kilo-baud channel, carries data from a standard keyboard 12022 to CPU 130 and carries menu display data to EL panel 136.

Serial I/O channel 12031, a 19.2 kilo-baud channel, carries system status and data from CPU 130 to Delay Line Control subsystem 66, and carries subsystem status from subsystem 66 to CPU 130. As specified in more detail below, delay line control subsystem 66 comprises a microprocessor which CPU 130 accesses for specifying logic control function codes and for specifying the delay time for each of delay lines 64.

VME bus 12024 is a general purpose data path for carrying address, data, control signals, and power-forms. In one operational embodiment, VME bus 12024 comprises a series of ninety-six pin connectors on a backplane wherein each pin is specifically defined to a specific address line, data line, control line, or power/ground line. The control lines enable a "handshaking" capability for signaling when data lines provide valid data. Additionally, some control lines include several lines used for carrying interrupt signals from other subsystems to the interrupt controllers 12040, 12041. CPU 130 has access to the following subsystems via VME bus 12024: graphics I/O subsystem, graphics memory subsystem, spectrum velocity subsystem, centroid subsystem, interpolator, digital storage subsystem, and timing and control subsystem.

The system CPU 130 includes the following software interfaces:

Software Architecture

The software that executes in the Motorola 68000 CPU controls the entire system beginning at power-on. The following describes the architecture of this "system" software.

When power-on occurs, the CPU 130 vectors to the start of the system software. The CPU 130 is in supervisor mode. The system software first determines the cause of the CPU reset. Normally, it is because power has just been applied or the operator has pushed the reset button. If power has just been applied, then a series of power-on self-tests are run that test memory. Next, the system software initializes the data structures required by the real-time executive (Hunter & Ready, Inc.'s VRTX-68000 product). Then, the software jumps to the start of VRTX. At this point, VRTX initializes itself and starts the "default/self-test" task running in CPU user mode.

The default/self-test task creates the other tasks and the inter-task communication mailboxes and queues and initializes CPU board support chips (USARTs, interrupt controllers, and clock chip). The default/self-test task then starts up the other tasks and enables interrupts. After that, the default task lowers its priority and begins its self-test mode. In that mode, as the lowest priority task, it runs unobtrusive tests when no other task is running. If the system has been inactive for 5 minutes, the default/self-test task is allowed to disable and enable interrupts from the user controls. The software architecture is interrupt based. All tasks are usually ready to run and are waiting for an event to occur. The interrupt service routines therefore report events by posting to the mailboxes and queues that the tasks pend on.

The other tasks (besides the default/self-test task) each perform their own initialization and then pend on a mailbox or queue.

The main task is the operator request processing task (referred to as the "opt" task). The opt task first initializes itself and then checks if optional hardware is configured in the system. After initialization, the opr task waits for an operator input. When the input is received, the opr task validates the request, gives the operator visual feedback, and in certain cases, changes the configuration of the imaging hardware.

The clock task waits for a clock "tick" from the real-time clock interrupt or a message from the opt task. When activated, the clock task updates the displayed date and time and notifies the opt task when a variable has been unchanged for a certain time interval.

The print task waits for the opr task to send it something to print and then prints it at a low priority while the system continues to respond to user requests.

There is a shared graphics utility that uses a semaphore to grant access by a single task. The graphics utility provides a subset/superset of the standard "ACM Siggraph CORE" graphics commands. There is also a utility for saving and reporting error messages as well as directing output to a debug monitor.

The functional requirement that resulted in the above-mentioned architecture can be summarized as follows. The operator pushed a button on the system 10. The software must accept that input and determine if it is valid given the current operation mode of the system. If it is valid, some kind of feedback is given the operator, such as a change in the image, a graphics change, a text change, or an audio change. The system software may then write to a memory-mapped hardware interface to change the hardware configuration. The following section describes those interfaces.

Transducer Power

The S/W controls the power of the transducer. There is an 8-bit transducer power setting interface. The transducer power value will be adjustable by the operator in terms of db. The S/W converts the db value into an attenuation voltage code based on the current transducer operating frequency (i.e., 5.0 mHz or 7.5 mHz).

Freeze Control Register

This 8-bit register is used to control various forms of image and waveform freezes, including:
scanline A freeze control
scanline B freeze control
2D image freeze control
triggered/untriggered freeze control
all freeze

Transmit/Receive Mode Control Register

The S/W tells the H/W how many sample sites are in use, the current transducer frequency, and current wedge angle. The number of sample sites for the various penetration depths is defined within the H/W; the S/W supplies a 2-bit index for the H/W to select the proper value. The transducer frequency type is specified as a 2-bit code, but only 2 frequencies are currently supported. There are currently four wedge angles supported by the H/W; the proper wedge is selected via a 2-bit code. The S/W stores an 8-bit value.

Scan List Control Register

This interface consists of one byte register. The byte defines the current mode of operation for the scan list controller. The scan list controller will use this byte to determine which scan list control program to execute.
  a. scanline A function
     off
     256-point spectrum
     128-point spectrum
     velocity/flow
  b. scanline B function
     off
     256-point spectrum
     128-point spectrum
     velocity/flow
  c. continuous mode
     imaging+scanline A/B
     functions
     scanline A/B functions only
  d. faster imaging
     normal flow imaging
     faster imaging (TISSUE ONLY)
       (7 pulses @7.5 mHz)
       (5 pulses @5.0 mHz)

Scanline Beam Address Registers

This interface consists of two byte registers. The registers define the beam to be used for scanline A and scanline B functions. The S/W adjusts the beam numbers by a frequency-dependent offset and scale prior to downloading the values. The contents of the registers will be ignored when the associated scanline function is OFF.

Digital Power Supply Status

The system power supplies consist of two types: analog and digital. The analog power supplies status can be accessed via the analog interface. The digital power supplies can be accessed by writing a command word to address a specific power supply, waiting 25 usecs, and then addressing two reads (separated by 25 usecs) using the same I/O address as the command word). Only the data associated with the second read is to be used. NOTE: The S/W waits an additional 25 microseconds before attempting to repeat the digital power supply status access sequence.

Analog Interfaces—Receive Beamforming and Time-Gain Control

The S/W controls the "downloading" of TGC and delay control data to the analog H/W. The S/W controls this interface via a serial port dedicated to the analog H/W portion of the QD 1. The S/W downloads command and data bytes over PORT B of USART 3. Status data from the analog H/W is requested by the S/W by issuing a status request command followed by a serial port read request from PORT B of USART 3.

The S/W is required to set a command discrete (RTS) whenever it issues a command byte to the analog serial interface. The discrete will be reset for the transmission of data bytes. The analog H/W also issues a status discrete (DCD) to allow the S/W to determine whether the analog I/F is active (i.e., "awake") or inactive (i.e., "asleep"), The analog H/W requires approximately 10 msecs to "awaken" and stays "awake" approximately 100 msecs following the last S/W command, The capability to disable the analog H/W "sleep" mode is available to the S/W if a need arises, Rotary switch inputs to control the TGC may be received at approximately 1500 baud (150 characters/sec) or approximately 1 character every 7 msecs.

The following commands/data have been identified:

| COMMAND | DATA |
| --- | --- |
| block xfer termination | |
| write system status | transducer frequencey |
| | penetration depth |
| | single/dual beam mode |
| read status register | 5.0/7.5 mHz cable status |
| | 5/0/7.5 mHz relay status |
| | error detected status |
| | mode switching status |
| write LSB to register | load addr reg with LSB |
| write MSB to register | load addr reg with MSB |
| write byte via register | load data via addr reg |
| read byte via register | access data via addr reg |
| read power supply status | power supply XX status |
| write TGC initial offset | load TGC initial data |
| write TGC slope | load TGC slope data |
| write Doppler slope | load Doppler slope |
| write Doppler offset | load Doppler offset |
| write test mode 1 | dummy data |
| write test mode 2 | test command(s) |

-continued

| COMMAND | DATA |
| --- | --- |
| read current mode | returns system status |
| rear error status | read error registers |
| read last 32 commands | read last 32 commands |

Delay/Termination Ram

This interface consists of a 30 k byte list of data. Under normal system operation, the S/W does not need to directly interface with these arrays; however, the S/W may need to load various test/diagnostic data into these RAMs during H/W integration via the serial interface. The following discussion defines how this is done.

The analog interface contains an address register that is used to read/store bytes of data from/into the 30 k bytes of delay/termination RAM. The S/W loads the 16-bit address register wit the MSB and LSB bytes of the starting location of the following load operation. The S/W then sends a "write memory" command and the first byte of data to store. For each additional byte of data, the S/W simply issues the data bytes (the address register is incremented automatically by the H/W). At the end of a data block write, the S/W sets the RTS line active, which places the analog I/F into its normal condition of waiting for commands. If RTS is subsequently set inactive, the analog I/F will go to "sleep." A command is not necessary.

Time-Gain Control Tissue TGC

The S/W downloads an operator-adjustable TGC slope value and initial offset value each time either value is modified by the operator. The S/W issues "weighted" digital-to-analog (DAC) codes for both values.

Doppler (Flow) Gain

The S/W controls the download of an operator-controllable Doppler gain offset and slope bytes. The offset value will range from −55 db to 20 db in 1.0 db steps. The S/W downloads "weighted" digital-to-analog (DAC) codes for both values.

Write System Status

This command sequence is downloaded to the analog H/W at system initialization and whenever the transducer frequency or the penetration depth is changed by the operator. The analog H/W requires approximately 0.1–2 seconds to change operating modes.

Read Status Register

This command sequence is downloaded to the analog H/W whenever the S/W wants to determine the status of the analog initialization, the current transducer connection status, or the analog H/W detected error status. The S/W issues the command and then polls for the analog H/W interface to return the requested status byte.

Write LSB to Address Register

This command sequence is downloaded to the analog H/W when the S/W needs to set the least significant byte (LSB) of the analog H/W address register.

Write MSB to Address Register

This command sequence is downloaded to the analog H/W when the S/W needs to set the most significant byte (MSB) of the analog H/W address register.

Write Data Byte Via Address Register

This command sequence is downloaded to the analog H/W when the S/W needs to load a byte (or more) of data into the delay/termination/amplitude RAM. Each data byte will be stored at the location "pointed at" by the address register. The address register is incremented by 1 for each data byte transmitted. The S/W only needs to isolate one command byte followed by up to 30 k bytes of data. At the completion of the data transfer, the S/W must set RTS active.

Read Data Byte Via Address Register

This command sequence is downloaded to the analog H/W whenever the S/W wants to read the contents of one or more delay/termination/amplitude RAM bytes. The S/W specifies the number of bytes to be read. The byte to be accessed is "pointed at" by the address register. The S/W issues the command and then waits for the analog H/W interface to return the requested data byte(s). This access method is intended for special diagnostic testing.

Read Power Supply Status

This command sequence is downloaded to the analog H/W whenever the S/W wants to determine the status of a specific power supply. The S/W issues the command and then waits for the analog H/W interface to return the requested status byte.

Write TGC Slope

This command sequence is downloaded to the analog H/W when the S/W needs to update the TGC slope register of the analog H/W.

Write TGC Initial Offset

This command sequence is downloaded to he analog H/W when the S/W needs to update the TGC initial offset register of the analog H/W.

Write Doppler Slope

This command sequence is downloaded to the analog H/W when the S/W needs to update the Doppler (flow gain) slope register of the analog H/W.

Write Doppler Offset

This command sequence is downloaded to the analog H/W when the S/W needs to update the Doppler (flow gain) offset register of the analog H/W.

Write Test Mode 1

This command sequence is downloaded to the analog H/W when the S/W needs to enable/disable analog interface RAM access. On "power up," access to the RAM is not allowed; the S/W issues this command before it accesses the RAM.

Write Test Mode 2

This command sequence is downloaded to the analog H/W when the S/W needs to write test values to DACs via the analog I/F.

Read System Mode

This command sequence is downloaded to the analog H/W whenever the S/W needs to know the current transducer frequency, the penetration depth, or beam status currently in use by the analog H/W.

Block Transfer Termination

This command is downloaded to the analog H/W at the completion of a "write data byte via address register" command sequence. This command allows the analog H/W to terminate its load sequence and enable its "wake/ sleep timeout counter."

Read Error Registers

This command sequence is downloaded to the analog H/W whenever the S/W wants to determine the status of analog error status register. The S/W will issue the command and the error register index, and poll for the analog H/W interface to return the requested status byte.

Read Last 32 Analog I/F Commands

This command initiates the return of the previous 32 commands received by the analog I/F. The current command will be one of the 32 commands.

Spectrum Analysis Built-In Test

The S/W controls a number of test interfaces. Some of the test interfaces are at the physical board level (e.g., waveform board) instead of at the function level. Each test interface is defined separately.

Spectrum/Velocity Subsystem Test Control

The S/W is able to download test data bytes to both the spectrum H/W and the velocity/flow H/W. The test control data includes the following:
test mode
  non-test mode
  test mode active
test "beam type"
  spectrum A
  spectrum B
  velocity A
  velocity B
ECG active
  inactive
  active
audio control
  spectrum running
  video record with NO SPECTRUM
  (microphone recording possible)
  video playback
  all other modes

Corner Turning Memory

This interface consists of two memories, A and B, each consisting of an 8 k byte "tissue" section (expandable to 32 k bytes) and a 16 k word (16-bit) "I and Q" section (expandable to 32 k words). These memories are normally not modified by the S/W except during special test modes.

There are two test modes associated with the corner turning memory: beam capture and beam simulate.

The beam capture mode allows the capture of two successive beam (up to 16 pulses per beam) in memory A. This is done by storing the beam number to be captured into the capture beam number register (see below) and setting the capture beam bit in the in the transmit/receive mode control register. Logical memory A will contain the captured beam within 50 milliseconds; logical memory B will contain the beam preceding the captured beam. If the beam number doesn't occur (i.e., outside the valid range of beam numbers), the H/W defaults to the last two beams in the image. Note: The playback frame release bit in the playback control register is zero for this mode.

The beam simulate mode allows the S/W to preload corner turning memory with a test pattern to simulate simultaneously one image beam, one velocity beam, and one spectrum beam. This is done by setting the beam simulate bit in the transmit/receive mode control register and loading the memory with the desired pattern.

Flow Sensitivity

The S/W updates the flow threshold (sensitivity) whenever the user adjusts the flow sensitivity rotary switch. This interface consists of 512 word RAM; the H/W only uses the twelve least significant bits. The S/W loads up to 512 words of RAM with threshold values based on a threshold index ranging from 0 to 32.

High Resolution Analyzer

This interface allows the S/W to control the display of spectrum data on either one or two scrolling waveforms or the ECG waveform when no spectrum waveforms are present. The S/W defines the type of spectrum (128-pt vs. 256-pt) that will be displayed.

The S/W specifies the sample site the spectrum data is derived from for each scanline in use (A and/or B). The displayed waveform scale and the calculations to be performed must also be defined for each scanline in use.

A spectrum gain/threshold register is used to control either the spectrum gain interface or the spectrum threshold interface. The H/W reads the register once every 8 to 46 msecs and updates its own internal registers with the contents of this register. The S/W allows at least 46 msecs between a spectrum gain update and a spectrum threshold update. The spectrum threshold represents the spectral amplitude below which the spectrum will be zero. The S/W controls this interface via the "threshold" and "gain" rotary switch interface whenever a spectrum waveform is displayed.

Audio

This interface allows the S/W to control the volume of the spectrum stereo audio for the currently "active" scanline or the audio output from the VCR/digital recorder. The H/W assumes the currently active scanline is the scanline associated with the last updated scanline sample site register. In addition, the S/W must specify the PRF currently in use.

The S/W will control the audio via a "look-up" table of twenty 6-bit values. The PRF will be controlled via a 2-bit code.

Centroid Control Register

The S/W controls the selection of one of four clutter canceller gain-compensation tables and the flow separation. This interface allows the S/W to control these parameters. The flow separation data is also downloaded to the high resolution analyzer.

Real-Time Image Formation Digital Storage Overview

The optional video cassette recorder (VCR) on the QAD1 is used for two purposes. The first is to store the image monitor display in NTSC format that can be played back on any VCR (VHS format). The other use is to store raw data in a digital format that can be played back through the system almost as if one were scanning with a transducer. The advantages to the latter are image quality that is as high as when the original scanning took place and the ability to use most of the post processing functions to enhance the display. Additionally, the most recent data from a scan or digital playback is buffered and can be repeated over and over (cine loop function).

Video and digital data may exist on the same tape in any order. If videodata is read during digital playback, the data will not be recognized as valid and no image or waveform updates will occur until valid digital data is detected. If digital data is read during video playback, it will have a distinctive "flashing checkerboard" pattern which will not be confused with a blank or defective tape.

Composition

There are many pieces that make up the digital storage function. These are:

| | |
|---|---|
| Timing and control board | playback control register |
| Graphics I/O board | video control register |
| | VCR status register |
| | VCR interface H/W |
| Review buffer board | review buffer memory |
| Digital storage board | review buffer control firmware |
| | frame buffers |
| | frame buffer control register |
| | frame buffer interrupts |
| VCR | physical storage medium |
| System software (S/W) | digital storage control |
| | operator interface |

Digital Record

During digital record, the signal processing data and system status data are combined in the frame buffers. The H/W toggles the frame buffers so that one frame is being written out to the review buffer while the other is being filled with new data. An interrupt to the CPU 130 is generated when the frame buffers are toggled. From there it goes through the review buffer, is converted into NTSC format, and is written out to the VCR tape. When the system is not in a record or playback mode (i.e., normal scanning), the S/W will leave the review buffer in a record mode so that the most recent scan data is always stored in the review buffer.

Digital Playback

During digital playback, the data comes off the VCR tape in NTSC format, gets converted back into its original form, and enters the review buffer. The review buffer will always contain the most recent playback data. From there it goes to a frame buffer. The H/W will toggle access to the frame buffers so that the review buffer is writing data to one frame while the other frame is being read by the S/W and processed by the signal processing H/W for display on the image monitor. An interrupt is generated when the frame buffers are toggled. The S/W extracts the system status data from the frame buffer and uses it to reconfigure the system to the same mode that the system was in when the recording was made. During playback the data flow from the VCR can be interrupted and the data repeatedly taken from the review buffer. This is the "cine loop" function. It is possible for the S/W to invoke playback of the review buffer data without playing back the data from the VCR. This is known as "independent cine loop". Cine loop involving the VCR is referred to as "dependent cine loop" when a distinction needs to be made as to where the playback data originates.

Frame Buffer Control

The frame buffers consist of two logically distinct pieces of memory big enough to hold the largest frame of data. A "frame" is defined as the data necessary to update the image monitor once and its size will vary dependent upon what mode the system is in (freq, depth, spectrum, etc.). They allow one frame of data to be transferred to/from the review buffer while the other frame is being read/written by the signal processing H/W and the S/W. A frame of data may consist of the following types of data:

CPU data—system status ( freq, depth, switch settings, etc.)

ECG data imaging & velocity data spectrum data

Playback Control

Control of the direction and speed of the data stream is accomplished by the S/W using the playback control register. This is an interface that exists on the timing and control board. It controls the transfer of data between the review buffer and frame buffers and the timing signals that are used by the signal processing H/W (spectrum/velocity, interpolator, etc.).

Review Buffer Control

The review buffer consists of a number of logical frames of data. A maximum of 3 megabytes are available for the review buffer's use. Control of the review buffer by the system S/W consists of a set of commands sent/received via a USART which are interpreted and executed by the review buffer control firmware that resides on the digital storage board.

The review buffer can be put into any of four modes: idle, record, playback, and cine loop. These modes are independent of the state of the VCR. To record digital data onto the VCR, both the VCR and the review buffer must be placed in a "record" mode by the S/W. However, it is possible to record data into the review buffer without recording it onto the VCR.

During digital record, data from the frame buffers migrate into the review buffer and eventually output to the VCR. During digital playback, each frame of data is input from the VCR to the review buffer. The data is transferred to a frame buffer and remains in the review buffer until overwritten by a later frame.

When the review buffer is in cine loop mode, various commands can be sent to modify the direction and speed of the frames being transferred to the frame buffers. A "window" can be defined so that only a subset of the review buffer data is displayed.

VCR Control

The S/W can emulate the VCR's front panel buttons. The commands will be issued to the VCR via the video control register. These commands are: PLAY, RECORD, PAUSE, and STOP.

Cosine Correction

The S/W controls the loading of various cosine correction values into the H/W. The interface consists of three arrays: two 256-word cosine correction tables and one 256-byte sample site boundary table.

The "cosine LT" array contain the cosine correction values to be used by the H/W at each sample site within a specific beam until the "LT/GT" sample site is reached. The "cosine GT" array contains the cosine correction values AFTER the LT/GT sample site is reached. The "LT/GT sample site" array defines the sample site at which the H/W will switch from the cosine LT value to the cosine GT value. These three arrays allow the operator to set two cosine correction values for each beam (maximum of 256 beams).

The S/W modifies the cosine correction values as the operator makes adjustments. The cosine values range from 0 to $(32-(2^{-10}))$. It should be noted that the MSB must be zero, since the H/W performs a "two's complement" multiply. The default values are 1.0 (i.e., 400 HEX) for the cosine tables (GT and LT) and 0 for the LT/GT sample site table.

Interpolator Options

This word contains various discretes used to control functions within the interpolator card. The discretes control the following capabilities:
transducer frequency
penetration depth
interpolator test display mode
image shrink
image reversal
single/dual beam These discretes are to be SET to turn ON the associated function. The following definitions will describe the interpolator options:
operating frequency
sample site code
self-test pattern
interpolator test mode
 waveform normal operations
 display sample sites which fall exactly on a pixel
shrink/normal
normal/reverse

Interpolator Registers

The S/W tells the interpolator the absolute X,Y coordinates of the 2 D image area. The 2 D image area coordinate values change as the transducer frequency, wedge angle, display presentation and 2 D image size are changed. (Note: the H/W takes care of image orientation without the need for S/W intervention.) The scaling of each X,Y coordinate (column and row) is based on operating frequency.

Interpolation Algorithms

The S/W controls the generation of graphics "tick marks" and performs various "marker" range checks based on the current interpolations algorithm in use. There are currently two algorithms defined (i.e., two transducer frequencies).

The actual starting location of the interpolated image will vary with each mode of operation.

Special Measurements Trigger Control

The S/W downloads time delay counter, threshold, and waveform selection values associated to the operator-specified trigger point.

Velocity/Flow Processor Control

The S/W controls the collection and display of velocity/flow data via the following set of interfaces. The S/W downloads the following data to the H/W for EACH scanline in use:

| | |
|---|---|
| data processing mode | velocity data or flow/diameter data |
| waveform scale | normal or two times |
| vel/flow waveform control | on or off |
| starting sample site | 512 possible sample sites (must be >3) |
| range of sample sites | 1 to 255 sample sites between delimiters |
| flow separation | see high resolution analyzer of this section |

Image Memory

The S/W writes data directly into the image memory. The image memory is a 374 k byte area used to store color/gray scale data for the 640×480 pixels of the 2 D image color monitor. Each byte corresponds to a single pixel on the color monitor.

The image memory is arranged in 512 rows of 1024 pixels each. However, there is only storage for 768 pixels per row. To address a specific pixel's byte, the S/W adds an address format to the image memory base address.

Scrolling Waveform Memory

The S/W has no direct control over the placement of the two scrolling waveform areas. The H/W positions the waveforms to predefined starting columns. Both waveform areas will be positioned on the same row.

The S/W accesses the contents of the scrolling waveform memory to perform various calculations (e.g., % window, acceleration, min, mean, mode, max, etc.). The memory is organized as two 256×256-byte arrays. Waveforms that are only 128 pixels high use only one-half of the memory. The H/W combines two 256×256-byte areas into one 512×256 area when one waveform is active.

Unused portions of the waveform memory are blank filled by the H/W. The S/W keeps track of which portions of the memory are in use when accessing its contents. To access scrolling waveform memory, the S/W has to "decode" the physical scrolling memory address based on the contents of one or two "oldest" data column address registers, adjust the "decoded" column address by the desired column's address, and add the row address of the desired waveform value.

The S/W has access to the "oldest" data column pointer(s) used within the H/W for scrolling data storage. If the system is in a single (512) waveform mode, the "oldest" data column address will be available in the least significant nine bits of the upper left X axis zoom control register. If the system is in a dual (256) waveform mode, the oldest data column address for waveform A will be available in the least significant byte of the upper left X axis zoom control register; the oldest data column address for waveform B is available in the most significant byte.

Graphics Options and Zoom Control

The graphics options byte controls various image memory and waveform memory features. These control discretes are generally used within a given sequence of H/W instructions to perform a specific function (e.g., reverse the image). The following features are controlled by this byte:

number of active waveforms zoom status selective area clears zoom X axis location discretes Note: The S/W clears both the image memory and the scrolling waveform memories. Special H/W is provided for image memory clearing. Whenever the clear image memory enable discrete is set and the S/W is outputting a data value to the image memory, the H/W will write the value into all six "banks" of image memory. This allows the image memory to be cleared in 64 k write operations. There is no equivalent H/W for waveform memory.

When clearing image memory or scrolling waveform memory, the S/W freezes the corresponding interfaces (e.g., if the image memory is to be cleared, the interpolator must be frozen).

The times-2 zoom area discretes are updated whenever the zoom control registers are updated. Basically, the discretes tell the H/W the "zone" in which the upper left-hand corner of the "zoomed" box resides. These discretes are ONLY used during zoom mode.

The zoom control registers define the upper left-hand corner coordinates of the "times 2" zoom area. One register is assigned to the X address and another register assigned to Y. Each register is a two's complement, 16-bit value. If a negative address is received by the H/W, it refreshes the display with zero and continues to do so until both the X and Y addresses are positive (i.e., real screen), at which time the real data is output. The values can range from −640<X<320 and 0<Y<240. The upper left of the 2 D image monitor is defined as (0,0).

The S/W also updates a zoom shift count register whenever the zoom control registers are updated. The S/W downloads the one's complement of the result of the following equation:

result=(543−x)

The 543 represents the rightmost column of the scrolling waveform in the single waveform, 512 column mode. Whenever the X address is less than 32, the S/W must output the one's complement of 543.

Color and Gray Scale Mapping

This interface provides a mechanism for the S/W to control the post processing of image data and the "Gamma Correction" for the color monitor and various hand-held camera film types. This interface consists of two 256-byte color maps and a set of three 256-byte RGB intensity maps.

There are two color maps in the system. One of the color maps is used to map image memory values into the appropriate color (and shades of gray) for display on the color monitor. The other color map is used to map scrolling spectrum data and various scrolling waveforms into the appropriate colors (and shades of gray) for display on the color monitor. In one embodiment, only the image memory color map is accessible by the S/W.

The image memory color map is used to remap various image memory tissue/flow values from one RGB value to another. In addition, the map is used to remap any tissue/flow value to "green" as part of the "green tag" function. The S/W updates the image memory color map based on operator-selected/specified post-processing "curves."

The RGB maps contain gamma-corrected red, green, and blue color gun intensity values. The S/W downloads the appropriate "gamma-corrected" RGB values for the color monitor, video status (normal or inverse), or film type currently in use. The S/W supports two sets of color monitor gammma-corrected RGB values (normal and video inversion) and four sets of film type RGB values.

The image memory color map is divided into four sections. The first 120 bytes define the gray scale mapping (used for tissue and spectrum data). The second eight values are used for special colors (i.e., green tag, cursor color, graphics white, etc.). The third section (64 bytes) is used for forward flow color mapping. The last 64-byte section is used for the reverse flow mapping.

The RGB RAMs are divided into five sections. The first byte defines the background color of the image. The next 120 bytes define the gray scale mapping (used for tissue and spectrum data). The third section's values are used for special colors (i.e., green tag, cursor color, graphics white, etc.). The fourth section (64 bytes) is used for forward flow color mapping. The last 64-byte section is used for the reverse flow mapping.

Tag Level

The S/W controls the placement of a green tag within the 2 D image. The tag is used to highlight tissue or flow signal level(s) within the 2 D image data. The S/W updates the image memory color map RAM value associated with the selected level with the RGB index value for the green tag. By replacing the current value of the image memory color map with the RGB index value for GREEN, the H/W maps all tissue or flow pixels of the corresponding level(s) into the color green.

Typical data written into the scrolling waveform memories include the following:

blank or no spectrum data spectrum data velocity/flow/diameter waveform white fill spectrum green waveform fill velocity minimum waveform velocity mean waveform velocity maximum waveform diameter waveform flow waveform
spectrum minimum waveform
spectrum mean waveform
spectrum mode waveform
spectrum maximum waveform
ECG waveform
trigger The H/W writes the waveform values in a specific priority sequence. The lower priority waveforms are written before the higher priority waveforms (i.e., lower priority waveforms can be overwritten by higher priority waveforms). The waveform priority is listed below:

| | |
|---|---|
| spectrum maximum | HIGHEST PRIORITY |
| spectrum mode | |
| spectrum mean | |
| spectrum minimum | |
| flow | |
| diameter | |
| velocity maximum | |
| velocity mean | |
| velocity minimum | |
| spectrum green fill | |
| velocity/flow/diameter white fill | |
| trigger | |
| ECG | LOWEST PRIORITY |

2 D Image Monitor Control

The S/W generates various graphical and textual data for output to a 640×480 resolution RGB monitor. This monitor is used to display such things as the 2 D image, scrolling waveforms, TGC curves, and the post-processing color/gray bars.

In one embodiment, the S/W interfaces to this monitor via an NEC 7220 (same as Intel 82720) graphics controller chip. The S/W supports the generation of various vectors and alphnumeric characters. The reader is referred to the NEC 7220 User's Guide for a description of the interface.

The S/W supports multiple styles of non-destructive cursors simultaneously.

Text displayed on the color monitor is 8×8 pixels in a 10×10 pixel cell. This allows sixty-four characters across (640/10) and forty-eight rows of characters (480/10).

The S/W also controls the following interfaces associated with the 2 D image monitor:

graphics plane enable
graphics plane blanking
"real" vs. "test" pattern display source
NTSC loop back test enable
zoom (times 2)

The graphics plane control register selects which planes get modified by the NEC 7220 graphics controller chip. The graphics plane display register selects which planes are displayed.

Nonvolatile Storage

This interface is used to save various operator-specified system parameters (e.g., eight protocol sequence, user-defined annotations and patient histories, etc.). A 128 k (expandable to 192 k) byte block of nonvolatile RAM will be provided.

System Clock

In one embodiment, the S/W both sets and reads the time and date from a Motorola MC146818 Real Time clock plus RAM clock/calendar chip. The chip supplies the current time and date for display.

Stall Timer Circuit

The S/W resets a stall timer at least every eight cycles of the system clock chip's square wave output pin to prevent the system from being reset by the stall timer circuit. The S/W enables the stall timer by enabling output on the SQW pin. Once enabled, the S/W accesses the clock chip within every eight square wave cycles to reset the stall timer. If this is not done, the H/W resets the CPU.

Menu Monitor

The system has a second monitor for the display of various prompts and messages. The menu monitor emulates a "dumb terminal" ASCII code interface. The S/W has a serial interface with the menu monitor. There is no need for graphics on this monitor—only alphanumeric data. The display resolution is 72 characters by 25 lines.

| MENU MONITOR COMMANDS: | |
|---|---|
| COMMAND | DESCRIPTION |
| LOAD ATTRIBUTES | reverse video |
| | half intensity |
| | blink |
| | double height |
| | double width |
| | underline |
| | blank |
| | block graphic |
| RESET ATTRIBUTE BIT | resets most significant bit for attribute |
| SET ATTRIBUTE BIT | sets most significant bit for attribute |
| MOVE CURSOR | |
| HOME CURSOR | |
| CLEAR SCREEN & HOME CURSOR | |
| LINE FEED | |
| CARRIAGE RETURN | |

Front/Remove Panel

The system interfaces with an ASCII keyboard, a remote operator's panel, operator's console (front panel), and two foot switches via the front/remote panel interface. The interface consists of two RS-232 serial input ports. One port is for the ASCII keyboard and the other is used for the trackball, foot switches, rotary switches, and special function buttons. The two ports are described below.

ASCII Keyboard Serial Interface

The S/W supports one standard ASCII keyboard. The S/W accepts 128 separate standard ASCII command codes from the keyboard via a serial input port. The S/W supports a 9600 baud input rate. This data is input from port B of serial chip 2 (an AMD Am Z8530).

Operator Command Input Serial Interface

The S/W accepts a number of operator commands via a second serial input port. The port provides trackball, rotary switch, foot switch, and button data. All of the front panel buttons/switches and remote panel buttons/switches are "mapped" to this serial interface.

In one embodiment, this serial interface allows 128 different input codes. The S/W supports a 9600 baud input rate, although the infrared link limits the remote panel data rate to about 1500 baud. This data is input from port A of serial chip 2 (an AMD Am Z8530).

The S/W supports a trackball as a cursor control device. The S/W receives a limited number of ASCII codes from a trackball (e.g., up, down).

There are two rotary switches defined. They are multi-functioned and located on the remote panel. The current rotary switch assignments are:

Flow Gain/Flow Sensitivity/Flow Separation

TGC Slope/TGC Initial Offset/Transmit Power

There are two foot switches: VCR record and freeze. These switches will have duplicate buttons on the remote panel.

There are currently forty-three buttons divided between the front and remote panels. The remote panel buttons consist of exam intensive functions, while the front panel contains less frequently used functions. All but two of the buttons are single-stroke (not holddown) and must be released before they can be used again; the audio volume switches are "holddown" to emulate a rotary switch.

| LOCATION | CONTROL TYPE | FUNCTION |
|---|---|---|
| REMOTE | SINGLE | photo |
| | | freeze frame |
| | | image reverse |
| | | flow direction |
| | | transmit power |
| | | TGC initial offset |
| | | TGC slope |
| | | depth |
| | | flow gain |
| | | flow separation |
| | | flow sensitivity |
| | | trackball set |
| | | trigger |
| | | markers |
| | DIGITAL | digital record |
| | | VCR record |
| | ROTARY | rotary SW 2 clockwise |
| | | counterclockwise |
| | | rotary SW 1 clockwise |
| | | counterclockwise |
| | MENU | spectrum |
| | | flow/velocity |
| | | % stenosis |
| | | flow angle |
| | | measure |
| | | annotation |
| | | post-processing |
| | TRACKBALL | up |
| | | down |
| | | left |
| | | right |
| | | upper left |
| | | upper right |
| | | lower left |
| | | lower right |
| CRT BEZEL | SINGLE | camera in place |
| | | camera not here |
| FOOT SW | DIGITAL | VCR record |
| | SINGLE | freeze frame |
| FRONT | SINGLE | tissue only |
| | | video invert |
| | | frequency |
| | | SYS initialize |
| | | self-test |
| | | status |
| | | zoom |
| | DIGITAL | digital I/O |

-continued

| LOCATION | CONTROL TYPE | FUNCTION |
|---|---|---|
| | | video I/O |
| | | frame by frame |
| | | cine loop |
| | | forward |
| | | reverse |
| | | BEGIN/END |
| | ROTARY | audio volume clockwise |
| | | counterclockwise |
| | MENU | assist |
| | | protocols |
| | | patient history |

Optional Printer

The S/W supports the output of patient history data and defined protocol sequences to a dot matrix printer via a serial interface. The S/W treats the line printer interface as an ASCII device with NO special graphics features. The standard ASCII code is supported by the S/W. The serial interface utilizes pin 20 to indicate PRINTER READY/BUSY status to the CPU.

Video Control Register

The S/W controls a number of peripheral devices via a single control register and a single status register. The control register allows the S/W to take a photo using the optional built-in camera or control the operation of the optional VCR. This is a "write only" interface.

Peripheral Status

The S/W is able to determine the status of various devices via the peripheral status byte or the "DCD/CTS" USART status bits. The following paragraphs identify the status data available to the S/W.

VCR Register

The S/W is able to determine whether the VCR/digital recorder and/or the optional built-in camera H/W options are present via this byte. In addition, the VCR operational status can be read. Whenever a VCR operational status bit within this byte changes, the H/W will generate an interrupt. The H/W requires 65 microseconds to update the status register; multiple bits can be set.

USART Status Data

The S/W is able to determine the status of various H/W interfaces by examining the two status bits associated with each USART. Each USART can be programmed to generate an interrupt when the state of the status bits change.

Interrupts

This section describes the various external interrupts the CPU receives. The H/W supports sixteen separate interrupts via the level six 68000 interrupt and two interrupt chips (AMD Am519A). Each interrupt can be vectored to its own exception processing via an entry in the 68000's exception vector table. The currently assigned interrupts are listed below:

201 power fail
time-of-day clock chip
USART 1 (shared by both ports)
USART 2 (shared by both ports)
USART 3 (shared by both ports)
digital storage - frame buffer
freeze complete
60 Hz video sync (unused)
VCR status change
interpolator FIFO overflow (unused)
spectrum/velocity revisit (unused)

In addition, a level seven 68000 non-maskable interrupt will be generated by the reset/stall timeout H/W.

Power Fail

This interrupt is generated whenever an AC power failure is detected. The exact cause of the interrupt can be determined by the S/W by examining the interrupt status byte.

Time of Day Clock Chip

This interrupt, generated by the "time of day" clock chip, is used to provide both a moderately fine-grain clock for the real-time executive (VRTX by Hunter & Ready, Inc.), to update the displayed time and date, and to provide limited real-time executive timing capabilities.

Serial Inputs

In one embodiment, the system has three USART chips. Each chip is assigned its own interrupt vector. The S/W can "program" each chip to generate various interrupts (e.g., input character available, etc.). The S/W determines which type of interrupt was generated for each USART.

Digital Storage—Frame Buffer Interrupt

This interrupt occurs whenever the frame buffers are toggled. In "record" mode, the interrupt is used by the S/W to determine when it can write data into the frame buffer that is unique for each frame (i.e., sequence number and checksum). In "playback" mode, the interrupt is used by the S/W to determine when to interrogate the frame buffer for a new S/W status update. Based on a S/W-detected change in some unique data, a S/W status update can take place.

Freeze Complete

This interrupt is used by the S/W to determine when a requested freeze (triggered or untriggered) has occurred.

VCR Status Change

This interrupt is generated whenever the H/W detects a change in VCR status within the VCR status register.

Spectrum/Velocity Revisit

This interrupt is always active. The S/W can ignore the interrupt during normal operations. If the spectrum/velocity test mode discrete is set, the S/W downloads a test data byte to the spectrum test write register and/or the velocity test write register.

202

System Mode Change Sequence of Events

The S/W follows a fixed H/W control sequence whenever the frequency or depth of penetration is changed. The sequences are very similar and are listed below, in addition to sequences for the digital storage system.

FREQUENCY CHANGE freeze system
reduce transducer power to zero dbs
clear image memory
wait at least 100 ms's for transducer to discharge
disable transmitter power "enable" discrete
erase various graphics associated with "old" frequency
change S/W frequency status
change S/W depth of penetration status to SHALLOW
force "in use" sample site/beam numbers into valid range
update analog interface for new frequency and depth
update "T & C" card for new frequency and depth
update velocity processor card for new frequency
update interpolator options register for new frequency
update beam control registers (if required)
update PRF bits in audio interface
update interpolator control registers for new frequency
rewrite gray scale bar and green tag block in image memory
update various graphics associated with "new" frequency
wait for maximum assumed delay for analog interface
set TGC offset to frequency "preset" value
set TGC slope to frequency "preset" value
set Doppler gain to frequency "preset" value
set flow sensitivity (threshold) to frequency "preset" value and rewrite flow sensitivity color bar to image memory
set flow separation (alias) to frequency "preset" value and rewrite color bar to image memory
set audio to frequency "preset" value
poll for analog interface to complete initialization
check analog interface transducer cable status
check analog interface transducer relay status
if both statuses are valid, enable transmit power "enable" discrete
unfreeze the system

DEPTH CHANGE freeze the system
reduce transducer power to zero dbs
clear image memory
wait at least 100 ms's for transducer to discharge
disable transmitter power "enable" discrete
erase various graphics associated with "old" frequency
change S/W depth of penetration status
force "in use" sample site/beam numbers into valid range
update analog interface for new frequency and depth
update "T & C" card for new frequency and depth
update interpolator options register for new frequency
update beam control registers (if required)
update PRF bits in audio interface
update interpolator control registers for new frequency
rewrite gray scale bar and green tag block in image memory
rewrite flow sensitivity bar in image memory
rewrite flow separation bar in image memory
update various graphics associated with "new" frequency
wait for maximum assumed delay for analog interface
poll for analog interface to complete initialization
enable transmit power "enable" discrete
restore transmitter power to previous value
unfreeze the system

DIGITAL STORAGE INITIALIZATION initialize playback control register
- set frame speed to NORMAL
- set digital playback mode to OFF
initialize frame buffer control register
- set vme frame xfer to OFF
- set scan data xfer to OFF
- set spectrum data offset for current operating mode -continued initialize review buffer
- send BREAK to reset review buffer control processor
- wait for review buffer initialization to complete
- flush review buffer input USART
initialize frame buffers
- write current date and time
- write current system status data
put review buffer in IDLE mode
set review buffer frame size
set review buffer offset for cine loop BEGIN command
set review buffer memory size
clear review buffer
put review buffer in RECORD mode
send STOP command to VCR
initialize frame buffer control register
- set scan data xfer to ON
- read review buffer status to determine if review buffer functioning/installed
DIGITAL RECORD ( ON )

freeze the system
update frame buffer control register
- set scan data xfer to OFF
put review buffer in IDLE mode
clear review buffer
update system status data in frame buffer
- update file number
- initialize frame number
- set current date and time
send RECORD command to VCR
wait for VCR to get up to speed
put review buffer in RECORD mode
update frame buffer control register
- set scan data xfer to ON
unfreeze system
update spectrum velocity board control register
frame buffer ISR updates the frame number in the frame buffer each interrupt
DIGITAL RECORD ( OFF )

put review buffer in IDLE mode
update frame buffer control register
- set scan data xfer to OFF
send STOP command to VCR
put review buffer in RECORD mode
update spectrum velocity board control register
update frame buffer control register
- set scan data xfer to ON
DIGITAL PLAYBACK ( ON )

send PLAY command to VCR
save current system status
save current patient history data
update playback control register
- set frame ignore to ON
- met digital playback mode to OFF
put review buffer in IDLE mode
write invalid frame id in both frame buffers
clear the review buffer
update playback control register
- set digital playback mode to ON
update frame buffer control register
- set scan data xfer to ON
put review buffer in PLAY mode
invalidate current playback file number
disable time of day updates by clock task
enable frame buffer ISR to look for valid playback data
update video control register
update playback control register
- release frame to start frame buffer interrupts
if system is in freeze,, send PAUSE command to the VCR
when valid playback data enters the frame buffer, the ISR will detect it as a new playback session and cause the system to be reconfigured accordingly
DIGITAL PLAYBACK ( OFF )

disable the frame buffer ISR from monitoring digital playback data
put the review buffer in IDLE mode -continued clear the review buffer
update frame buffer control register
- set scan data xfer to ON
reconfigure system to state prior to digital playback
restore patient history data
enable time-of-day updates by clock task
update playback control register
- set frame speed to NORMAL
- set digital playback to OFF
- set frame ignore to OFF
put review buffer in RECORD mode
send STOP command to VCR
turn on transducer power
CHANGING PLAYBACK SESSIONS if system currently in digital playback, end of playback session will contain blank area. This will causes the frame buffer to NOT be updated. The frame buffer ISR will detect this and freeze the image and waveform area containing the last good data.
frame buffer ISR detects that the file number of the latest frame is different from the current playback file number
frame buffer ISR validates checksum for system status data in frame buffer
frame buffer ISR updates current playback file to file number contained in current frame
frame buffer ISR updates playback control register - set frame ignore to ON
reconfigure system based on system status data contained in latest frame buffer
frame buffer ISR updates playback control register set frame ignore to ON
initialize patient history exam results
update time of display on image monitor to time when recording was made
framed buffer ISR updates playback control register
- set frame ignore to OFF
SYSTEM RECONFIGURATION put review buffer in IDLE mode
clear review buffer
put review buffer in PLAY mode
turn off markers and trigger
freeze system
turn transducer power off
erase image monitor graphics
erase waveforms, if active
load system status data from frame buffer or save area
update image display area on image monitor
update frequency and depth settings on delay control board (analog control USART)
clear image memory
update frequency and depth settings on timing and control board
update interpolator control register
update interpolator options register
update frame buffer control register
- set spectrum data offset
set review buffer frame size ( LENGTH command
update audio control register
activate and suspend VELOCITY menu, if necessary
activate and suspend SPECTRUM menu, if necessary
update view labels on image monitor
if not in digital playback, restore transducer power
update H/W control regibters for switch settings
- tgc offset
- tgc slope
- flow separation
redraw image monitor graphics
update scan list control register
update spectrum/velocity test register
update ECG status
update graphics options register
freeze system
update spectrum threshold
update flow threshold
display tgc curve

Operator Interface and Peripherals

An operator communicates with the system 10 by using the buttons of remote control panel 144, rotary switches and trackball, a conventional keyboard, and front panel buttons. System output is to conventional CRT display monitors 120, 122, a conventional television, conventional VCRs 102, 124, EL panel 136, and printer 138. The remote, EL panel, and front panel are described below.

The remote control 144 is a hand-held device for remote control of the ultrasound flow imaging system by using either an infrared optical link or wired connection for communication. In one embodiment, the panel has 23 key switches, two optically encoded rotary switches, and a trackball. Panel legends are backlit for visibility in the dark. For an operator to input data or commands, power is provided by rechargeable NiCad batteries.

The remote control 144 transmits key codes to the ultrasound flow imaging system via an IR optical link or a wired connection. IR data is received by the IR receiver and then sent to the front panel 140 for decoding. The decoded keys are then transmitted to the CPU 130 via an RS-232 serial link. If the remote control 144 wired interface is used, the IR link is disabled to prevent interference with other systems that may be within control range.

In one embodiment, power for the remote control 144 is provided by a NiCad battery. After about 30 seconds of keyboard inactivity, the system reverts to an intermediate power state where the trackball and lights are turned off. The remote control 144 is reactivated by pressing any key. If about five minutes elapse without keyboard activity, the sleep mode is entered, which reduces the current drain and extends the battery life.

Digital Distribution

Referring to FIG. 29, one embodiment of the digital distribution subsystem 14300 includes coaxial cable connectors and pin connectors. The digital distribution subsystem plugs into the system backplane at pin connectors 14302 and 14303 for allowing cables to be routed to peripheral devices. Additionally, an audio board can be plugged into the digital distribution subsystem 14300 at pin connector 14301. Interfaces include interfaces for auxiliary power supplies, the system camera, the system monitor, the keyboard, the system boom, headphones, a microphone, an optional external VCR, and optional external monitor, optional external terminal or computers, the external printer, the VCR, and the ECG peripheral device.

Auxiliary power units for supplying ±15 volts DC, +5 volts, and −5.2 volts DC or other selective voltage levels can be connected to the system through a power line connector 14304. The system camera has five coaxial cable connections 14309–14313: one for carrying each of the red, green, and blue image signals 14309, 14310, and 14311, one for carrying the synchronization signal 14312, and a fifth for carrying an "expose" signal 14313. The "expose" signal allows the CPU to cause a picture to be taken. The system monitor similarly has four coaxial cable connections: 14314–14317, one for carrying each of the red, green, and blue image signals 14314, 14315, 14316 and a fourth for carrying the synchronization signal 14317.

In one embodiment, the connector for the front panel 140 is a 25-pin connector 14305 which contains two incoming RS-232 data lines and status, buffered IR data, hand-held camera status, and DC voltages to power the front panel.

In one embodiment, a 25-pin connector 14306 provides signals to EL panel 136, and to left and right audio speakers. Headphones may be hooked into the system at a 9-pin connector 14307 to listen to blood flow frequencies output from the spectrum velocity subsystem 1800. A microphone connection 14309 is included for allowing use of a microphone to dub in audio signals while videotaping images from the VCR.

In one embodiment, there are six coaxial cable connectors 14318–14323. Coaxial cable connector 14318 is for receiving the video output of an external VCR, while coaxial cable connector 14319 can be used for transmitting the VHF signal off the internal VCR to a standard television. Additional connectors for an external color monitor include a synchronization line connector 14320, blue image signal connector 14321, green image signal connector 14322, and red image signal connector 14323. Additionally, an auxiliary RS 232 port 14334 is provided which can be used for connecting an external monitor, terminal, or computer by providing two duplex RS-232 protocol ports.

A 25-pin connector 14324 receives a cable connected to printer 138 for the output of print data and the input of printer status.

There are eight connectors connecting the VCR 124 (shown in FIG. 11B) to the system. Four female connectors 14325–14328 for receiving four male connectors from VCR 124 provide an input track and an output track for each of the two audio channels on a VCR recording. Two coaxial cable connectors 14329 and 14330 receive cables connected to the VCR 124 for carrying the input and output video tracks of a VCR recording. The connector 14331 for receiving VHF output from VCR 124 enables playback of VCR video data to the television 1168. Fifteen pin connector 14332 receives a cable connected to VCR 124 for carrying VCR commands under system software control.

Twenty-five pin connector 14333 receives a cable connected to the ECG subsystem for receiving ECG data and status and for transmitting an ECG convert command.

Low Voltage Sensor PBC (AC Power Fail)

The low voltage sensor board senses the analog +5 volt power bus and the +15 volt power bus for low voltage. If a low value is sensed (as described below) then an alarm signal is sent to the timing and control board in the digital chassis which in turn inhibits the Manchester string that initiates a transmit pulse on the transmitter card to reduce the chance of a power down failure on the transmitter card.

The +5 and +15 volt power supplies, FIG. 32, are sensed through low pass filter at 14502 and 14500, respectively. The +5 volt is sensed at pin 6 of 14516 using level setting resistors 14510, 14512 and a select at test resistor 14514. The +15 volts is sensed at pin 3 of 14516 using level setting resistors 14504, 14506 and a select at test resistor 14508. If either output is set active by a low power bus sense then a low signal is applied to optical isolator 14518. The optical isolator isolates the analog and digital power supplies and signals to reduce noise coupling. The output of 14518 is then applied to 14522 and then in turn is applied to the timing and control card as described above.

We claim:

1. A system for ultrasound blood flow imaging, comprising:

a transducer having a plurality of transducer elements arranged in a linear array;

transmitter means having a plurality of respective transmitters connected to a plurality of elements of said transducer, said transmitters selectively generating an ultrasound electric signal in synchronism with each other to cause said transducer to output a beam of ultrasound energy;

a switch having an input terminal connected to each of said transducer elements, said switch selectively connecting a subset of adjacent transducer elements to respective output ports;

ultrasound processing means connected to the output ports of said switch, said ultrasound processing means summing the signals from ultrasound elements that are substantially equidistant from the center transducer element in said beam and outputting said sum signals on respective output lines;

delay line means connected to each output line of said ultrasound processing means, said delay lines of said ultrasound processing means by amounts which increase for delay line means connected to transducer elements toward the center of said beam, thereby focusing said ultrasound return signals at the center of said beam;

summing means adding the outputs of each channel of said delay line means to each other to generate a delayed output signal;

clutter canceller means removing components of said delayed output signal corresponding to ultrasound returns from non-moving ultrasound reflectors;

flow processor means receiving said delayed output signal from said summing means and calculating a single blood flow velocity approximating a range of blood flow velocities that correspond to the frequency spectrum of said delayed output signal;

image memory means storing each of said data indicative of a single blood flow velocity for a plurality of discrete sample sites in each of a plurality of ultrasound beams;

display means receiving the output of said image memory means, said display means providing a visual indication of the blood flow at the sample sites beneath said transducer as a function of depth; and control means controlling and coordinating the operation of said ultrasound imaging system.

2. The ultrasound imaging system of claim 1 wherein said transducer further comprises an ultrasound coupling wedge having a first coupling face in contact with said transducer elements, a second coupling face positioned at an angle with respect to said first face, and an ultrasound coupling medium positioned therebetween, said second face being adapted for contact with the skin of a patient in order to position said transducer elements at a fixed predetermined angle with respect to the skin of said patient.

3. The ultrasound imaging system of claim 2 wherein said coupling wedge comprises a hollow, wedge-shaped body defining a cavity filled with a fluid having low ultrasound attenuation and an acoustic impedance approximating the acoustic impedance of said patient, said wedge-shaped body having a pair of generally triangularly shaped side walls, an end wall, and two opposed, non-parallel, flexible membranes, each extending between said side surfaces and defining said first and second faces, respectively.

4. The ultrasound imaging system of claim 3 wherein said membranes have a thickness that is a multiple of one-quarter wavelength of the ultrasound signal.

5. The ultrasound imaging system of claim 3, further including a sound-absorbing material linking the inner surface of said end wall to absorb ultrasound signals reflected from the membrane covering the second face of said wedge-shaped body.

6. The ultrasound imaging system of claim 5 wherein the inner surface of said sound-absorbing material is angled toward one of said side walls so that any ultrasound reflected from said membrane and from the inner surface of said sound-absorbing material is reflected toward one of said side walls rather than toward said first or second faces.

7. The ultrasound imaging system of claim 2 wherein said switch disconnects said input terminal and said output port for a period of time that is proportional to the thickness of said wedge so that the portion of said system connected to said switches is blanked until ultrasound returns are received from sample sites beneath said wedge.

8. The ultrasound imaging system of claim 1 wherein said transmitter means comprises:

decoder means receiving serial data from said control means indicative of the power level of the transmitted ultrasound and the identity of the transmitters to be energized in each of a plurality of beams, said decoder means generating a first multi-bit word indicative of the power level of the ultrasound signal and a second multi-bit word identifying the transmitters to be energized;

power supply means generating a transmit voltage determined by said first multi-bit word;

signal-generating means outputting a predetermined number of transmit switching pulses having a predetermined repetition rate and pulse width characteristic; and respective pulse-generating means connected to each of said transducer elements, said pulse-generating means being selectively enabled by said second multi-bit word and, when enabled, outputting said ultrasound electric signal to its respective transducer element during said transmit switching pulses.

9. The ultrasound imaging system of claim 1 wherein ultrasound reflected from sample sites beneath said transducer elements is received in a plurality of beams identified by respective beam numbers, each of said beams being formed by N adjacent transducer elements, and wherein said switch further comprises:

transducer element selector means receiving a digital word from said control means indicative of one of said beam numbers and outputting a plurality of transducer element enable signals designating the transducer elements forming said beam; and N switching circuits, each of which has a plurality of inputs connected to one of said transducer elements and all transducer elements spaced multiples of N transducer elements from said transducer element, respectively, each of said switching circuits outputting the ultrasound signal from one of the transducer elements as designated by said transducer element selector means, whereby the ultrasound signals from all of said transducer elements are process in N channels.

10. The ultrasound imaging system of claim 1 wherein said delay line means comprise:

a tapped delay line receiving the output from said ultrasound processing means, said tapped delay line delaying the output of said ultrasound processing means by one of a plurality of fixed delay periods, each corresponding to respective delay line taps;

a variable delay line receiving an input from a tap of said fixed delay line, said variable delay line further delaying the output of said multiplexer by an amount determined by a plurality of control signals received from said control means in order to generate a delayed output signal; and delay control means generating said delay control signal as a function of both the depth from which an ultrasound return is being received and the distance between the center element of each beam and the element associated with the delay line channel.

11. The ultrasound imaging system of claim 10 wherein said variable delay line further includes impedance control means for varying the input and output impedance of said variable delay line to prevent signals from being reflected from the input and output of said delay line.

12. The ultrasound imaging system of claim 10 wherein said delay lines comprise:

a plurality of inductors connected in series; and a plurality of varactors connected between the junction between adjacent inductors and a control input line.

13. The ultrasound imaging system of claim 12 wherein said varactors are arranged in alternating polarity, with varactors connected with one polarity connected to a first control input line and varactors connected with the other polarity connected to a second control input line, said control input lines receiving respective control input signals having opposite polarities and equal absolute values.

14. The ultrasound imaging system of claim 10 wherein said tapped and variable delay lines are mounted on a circuit board, and wherein the taps of said tapped delay line are selectively applied to said variable delay lines by multiplexer means, said multiplexer means being controlled by the location that said circuit board is mounted in a larger circuit board, whereby the delay line channel associated with said tapped delay line is determined by the location of the circuit board containing said tapped delay line in said larger circuit board.

15. The ultrasound imaging system of claim 1 wherein said ultrasound processing means further includes a dynamic aperture circuit, comprising:

a plurality of variable gain circuits receiving respective inputs from each channel of said delay line means, each of said variable gain circuits generating an output bearing a ratio to the input that is determined by a respective gain control signal; and gain control means generating said gain control signals, said gain control means increasing the ratio between their output and input for variable gain circuits receiving inputs from delay line channels further away from the center of each beam as ultrasound returns from deeper sample sites are processed, whereby the aperture of said transducer becomes larger for increasingly deeper sample sites.

16. The ultrasound imaging system of claim 15 wherein said variable gain circuits are voltage-controlled attenuators.

17. The ultrasound imaging system of claim 15 wherein a plurality of variable gain circuits receive respective inputs from the outputs of the channels of said delay line means, each of said variable gain circuits generating an output bearing a ratio to the input that is determined by a respective gain control signal; and gain control means generating said gain control signals, said gain control means increasing the ratio between their output and input as a function of the elapse in time from the transmission of each ultrasound pulse, whereby the gain is increased for deeper sample sites.

18. The ultrasound imaging system of claim 15 further comprising:

an ultrasound coupling wedge having a first coupling face in contact with said transducer elements, a second coupling face positioned at an angle with respect to said first face, and an ultrasound coupling medium positioned therebetween, said second face being adapted for contact with the skin of a patient in order to position said transducer elements at a fixed predetermined angle with respect to the skin of a patient;

a plurality of variable gain circuits receiving respective inputs from the signals output by the channels of said delay line means, each of said variable gain circuits generating an output bearing a ratio to the input that is determined by a respective gain control signal; and gain control means generating gain control signals that make said ratio substantially zero for a period that is proportional to the thickness of said wedge, whereby the components of said system connected to said variable gain circuits are effectively blanked until ultrasound returns are received from sample sites beneath said wedge.

19. The ultrasound imaging system of claim 1 wherein said system further comprises memory means for reordering the data received from said clutter canceller means, said memory means comprising a digital memory receiving said data for each beam M sets of N ultrasound return samples, each of the N ultrasound return samples in each set being taken in succession from the same ultrasound transmission at N different discrete sample sites and each of the M sets of such return samples being taken at the same beam location from M successive ultrasound transmissions, said memory means outputting said data corresponding to N sets of M ultrasound return samples, all of the M ultrasound return samples in each set being output in succession and corresponding to output returns taken from M successive ultrasound transmissions at the same discrete sample site, and each of the N sets of such return samples being taken at said N respective sample sites, whereby data are written into said memory means in the sequence of data words $S_{1,1}; S_{1,2}; S_{1,3}; \ldots S_{1,N}; S_{2,1}; S_{2,2} \ldots S_{2,N}; \ldots S_{M1}; S_{M,2} \ldots S_{M,N}$ and read out from said memory means in the sequence of data words $S_{1,1}; S_{2,1}; S_{3,1} \ldots S_{M,1}; S_{1,2}; S_{2,2}; S_{3,2}; \ldots S_{M,2}; \ldots S_{1,N}; S_{2,N}; S_{3,N}; \ldots S_{M,N}$.

20. The ultrasound imaging system of claim 1 wherein said flow-processing means generates data indicative of the magnitude of each of a plurality of discrete frequency components in said delayed output signal, each of said discrete frequencies corresponding to a discrete blood flow velocity, said flow processor means further calculating said single blood flow velocity from said frequency component data receives successive sets of data, each corresponding to a plurality of ultrasound return samples taken from the same sample site, each of said ultrasound return samples having a frequency spectrum of $f_d, f_d \pm f_r, f_d \pm 2f_r, f_d \pm 3f_r \ldots f_d \pm Mf_r$, where $f_r$ is the repetition frequency of said ultrasound transmissions, and M is an integer greater than 1, and $f_d$ is the center frequency of said ultrasound electric signal, said flow processor comprising N band-pass filters, each having respective pass bands effectively centered at $f_o, f_o \pm f_r \ldots f_o \pm 2f_r \ldots f_o \pm 3f_r \ldots f_o \pm Mf_r$, where $f_o = (f_r/N)P$ and $P=0, 1, 2, \ldots N-1$, whereby the magnitude of the output of each band-pass filter is indicative of the velocity of moving sound scatterers at said sample site.

21. The ultrasound imaging system of claim 20, wherein said flow processor means receives successive sets of data, each corresponding to a plurality of ultrasound return samples taken from the same sample site, each of said ultrasound return samples having a frequency spectrum of $f_d, f_d \pm f_r, f_d \pm 2f_r, f_d \pm 3f_r, \ldots f_d \pm Mf_r$, where $f_r$ is the repetition frequency of said ultrasound transmissions, and M is an integer greater than 1 and $f_d$ is the center frequency of said ultrasound electric signal, said flow processor comprising N band-pass filters, each having respective pass bands effectively centered at $f_o$, $f_o \pm f_r$, ... $f_o \pm 2f_r$, ... $f_o \pm 3f_r$, ... $f_0 = Mf_r$, where $f_o = (f_r/N)P$ and $P = 0, 1, 2, \ldots N-1$, whereby the magnitude of the output of each band-pass filter is indicative of the velocity of moving sound scatterers at said sample site.

22. The ultrasound imaging system of claim 21 wherein said band-pass filters comprise a digital comb filter.

23. The ultrasound imaging system of claim 21 wherein said band-pass filters comprise:

multiplying means generating the products of each of said ultrasound return samples and 2N coefficients corresponding to $\cos 2\pi pf_o t$ and $\sin 2\pi f_o t$ where $t = Y(f_r)$ and $Y = 0, 1, 2, 3, 4 \ldots N-1$; and a plurality of accumulator means for adding the products from said multiplying means for each value of $f_o$ to all previous products for each value of $f_o$ so that, for each sample site, said accumulator means outputs an accumulated product for each value of $f_o$, whereby accumulated products correspond to respective magnitudes of flow velocity of moving sound scatterers.

24. The ultrasound imaging system of claim 23 wherein N is equal to 16, whereby said coefficients have only 5 unique absolute values, thereby reducing the complexity of multiplication and coefficient storage.

25. The ultrasound imaging system of claim 23 wherein said accumulator means are implemented with arithmetic logic units so that the output of said multiplying means can be set to zero thereby eliminating the need for negative and zero valued coefficients to be applied to said multiplying means.

26. The ultrasound imaging system of claim 25 wherein said accumulator means are grouped such that a single coefficient is used for the computation of the in-phase or quadrature outputs of four of said filters, thereby minimizing the number of required coefficients.

27. The ultrasound imaging system of claim 25 wherein said accumulator means are implemented with a pair of storage registers connected in series such that the multiplying means and arithmetic logic units can be time shared in order to reduce the required number of multiplying means and arithmetic logic units.

28. The ultrasound imaging system of claim 20 wherein said flow processor means further includes centroid means comprising:

amplitude-determining means receiving said flow velocity data and determining the amplitude of each of said discrete Doppler frequencies;

peak amplitude-detecting means for determining which of said Doppler frequencies has the maximum amplitude and for providing an output indicative thereof;

first calculating means receiving said flow velocity data and the output of said peak amplitude detection means, said first calculating means calculating a first value from said digital flow velocity data, said first value corresponding to the sum of the magnitudes of at least one discrete Doppler frequency above and at least one discrete Doppler frequency below the discrete Doppler frequency having the maximum amplitude;

second calculating means receiving said flow velocity data and the output of said peak power detection means, said second calculating means calculating a second value from said digital flow velocity data, said value corresponding to the sum of the magnitudes of the discrete Doppler frequency having the maximum amplitude and the magnitudes of at least one discrete Doppler frequency above and at least one discrete Doppler frequency below the discrete Doppler frequency having the maximum amplitude, and third calculating means calculating as said data indicative of a single blood flow velocity the ratio of said first value to said second value.

29. The ultrasound imaging system of claim 28, further including thresholding means substracting a fixed value from each spectral amplitude at said discrete Doppler frequencies and then outputting to said centroid means the magnitudes of all discrete Doppler frequencies having a magnitude greater than a predetermined value.

30. The ultrasound imaging system of claim 1, further including flow velocity correction means receiving said data indicative of a single blood flow velocity, said flow velocity correction means scaling the blood flow velocity corresponding to said flow velocity data by the cosine of an intercept angle approximating the angle between said ultrasound beam and the blood vessel being imaged, thereby providing a more accurate indication of the velocity of the blood in said vessel.

31. The ultrasound imaging system of claim 30, wherein said ultrasound beam passes through a coupling wedge positioned between said transducer and the skin of a patient, said coupling wedge positioning said transducer at a fixed angle with respect to the skin of said patient, and wherein said intercept angle is selected to correspond to said fixed coupling wedge angle.

32. The ultrasound imaging system of claim 30, further including means for selecting a specific intercept angle for each of a plurality of respective sample site ranges such that blood velocity may be accurately determined in a plurality of vessels positioned at different depths and having different angular orientations.

33. The ultrasound imaging system of claim 1 wherein said system measures blood flow velocity and tissue return average power at discrete physical locations along said transducer and at discrete sample sites, said system further displaying measured blood velocity or tissue power image components at discrete locations on said screen corresponding to said discrete physical locations and sample sites, said system further including interpolator means for displaying interpolated blood flow velocity image or tissue power components at discrete locations on said screen without measuring blood flow velocities or tissue power at physical locations and sample sites corresponding thereto, said interpolated image components being interspersed among said measured blood flow velocity or tissue power image components and being derived from the measured blood flow velocity or tissue power image components adjacent thereto.

34. The ultrasound imaging system of claim 1 wherein said system further provides tissue data indicative of the magnitude and position of ultrasound returns from non-moving tissue, and wherein said system further includes merge means receiving said data from said flow processor means and said tissue data, said merge means applying said data from said flow processor means to said image memory for beam locations and sample sites in which the magnitude of data from said flow processor is greater than a predetermined value and, if said flow processor data is not greater than said predetermined magnitude, said merge means applying said tissue data to said image memory for said beam locations and sample sites.

35. A crossbar switch adapted for use in an ultrasound imaging system for receiving a plurality of ultrasound beams through N adjacent transducer elements, said crossbar switch comprising:

transducer element selector means outputting a plurality of transducer element enable signals designating the transducer elements forming said beam; and N switching circuits, each of which has a plurality of inputs connected to one of said transducer elements and all transducer elements spaced multiples of N transducer elements from said transducer element, respectively, each of said switching circuits connecting the transducer element designated by said transducer element selector means to an output port, whereby all of said transducer elements may be processed in N channels.

36. A system for processing signals corresponding to reflected ultrasound received through a plurality of adjacent ultrasound transducer elements, comprising multiplexer means for summing the outputs of transducer elements positioned equidistant from a transducer element at the approximate center of said plurality of adjacent transducer elements, whereby said multiplexer means reduces by approximately fifty percent the number of channels required to process said ultrasound signals from said transducer elements.

37. In a delay line comprising a plurality of inductors connected in series, a plurality of varactors connected between the junction between adjacent inductors, and a control input line connected to said varactors to control the capacitance of said varactors and hence the delay of said delay line, the improvement comprising impedance control means for continuously varying the input and output impedance of said delay line as a function of said control signal so that the input and output impedance varies in accordance with the impedance of said delay line as the impedance of said delay line varies with the capacitance of said varactors.

38. A delay line comprising a plurality of inductors connected in series, a plurality of varactors connected between the junction between adjacent inductors, and a control input line, said varactors being arranged in alternating polarities, with varactors connected in one polarity connected to a first control input line and varactors connected in the other polarity connected to a second control input line.

39. In an ultrasound imaging system generating blood flow velocity data from a beam of ultrasound returns taken from different sample site depths through an ultrasound transducer having a plurality of transducer elements, said beam being centered about at least one transducer element, a dynamic aperture system comprising:

a plurality of variable gain circuits receiving respective signals from said transducer elements, each of said variable gain circuits generating an output bearing a ratio to the input that is determined by a respective gain control signal; and gain control means generating said gain control signals, said gain control means increasing the ratio between their output and input for signals from transducer elements further away from the center of each ultrasound beam as ultrasound returns from deeper sample sites are processed, whereby the aperture of said transducer becomes larger for sample sites of increasing depth.

40. The dynamic aperture system of claim 39 wherein said variable gain circuits are voltage-controlled attenuators.

41. In an ultrasound imaging system generating blood flow velocity data from a beam of ultrasound returns taken from different sample site depths, memory means for reordering said blood flow velocity data, comprising a digital memory receiving said blood flow velocity data for each beam of said ultrasound returns corresponding to M sets of N ultrasound return samples, each of the N ultrasound return samples in each set being taken in succession from the same ultrasound transmission at N different discrete sample site depths and each of the M sets of such return samples being taken at the same beam location from M successive ultrasound transmissions, said memory means outputting said data corresponding to N sets of M ultrasound return samples, all of the M ultrasound return samples in each set being output in succession and corresponding to ultrasound returns taken from said M successive ultrasound transmissions at the same discrete sample site depth, and each of the N sets of such return samples being taken at said N respective discrete sample site byte depths, whereby data are written into said memory means in the sequence of data words $S_{1,1}$; $S_{1,2}$; $S_{1,3}$; ... $S_{1,N}$; $S_{2,1}$; $S_{2,2}$ ... $S_{2,N}$; ... $S_{M,2}$ ... $S_{M,N}$ and read out from said memory means in the sequence of data words $S_{1,1}$; $S_{2,1}$; $S_{3,1}$; ... $S_{M,1}$; $S_{1,2}$; $S_{2,2}$; $S_{3,2}$; ... $S_{M,2}$; ... $S_{1,N}$; $S_{2,N}$; $S_{3,N}$; ... $S_{M,N}$.

42. In an ultrasound imaging system generating successive sets of data, each corresponding to a plurality of ultrasound return samples taken from the same sample site, said return samples having a frequency spectrum of $f_d$, $f_d \pm f_r$, $f_d \pm 2f_r$, $f_d + 3f_r$, ... $f_d \pm Mf_r$, where $f_r$ is the repetition frequency of said ultrasound transmissions and M is an integer greater than 1, a flow processor comprising N band-pass filters, each having respective pass bands centered at $f_o$, $f_o \pm f_r$, $f_o \pm 2f_r$, $f_o \pm 3f_r$ ... $f_o$ $Mf_r$, where $f_o = (f_r/N)P$ and P=0, 1, 3 ... N−1, whereby the magnitude of the output of each band-pass filter is indicative of the velocity of moving sound scatterers at said sample site.

43. The flow processor of claim 42 wherein said band-pass filters comprise a digital comb filter.

44. The flow processor of claim 42 wherein said band-pass filters comprise:

multiplying means generating the products of each of said ultrasound return samples and 2N coefficients corresponding to $\cos 2\pi f_o t$ and $\sin 2\pi f_o t$, where $t = Y/(f_r)$ and Y=0, 1, 2, 3, 4 ... N−1; and a plurality of accumulator means for adding the products from said multiplying means for each value of $f_o$ to all previous products for each value of $f_o$ to any previous products for each value of $f_o$ so that, for each sample site, said accumulator means outputs an accumulated product for each value of $f_o$, whereby said accumulated products correspond to respective magnitudes of flow velocity of moving sound scatterers at said sample site.

45. The ultrasound imaging system of claim 44 wherein N is equal to 16, whereby said coefficients have only 5 unique absolute values, thereby reducing the complexity of multiplication and coefficient storage.

46. The ultrasound imaging system of claim 44 wherein said accumulator means are implemented with arithmetic logic units so that the output of said multiplying means can be set to zero, thereby eliminating the need for negative and zero valued coefficients to be applied to said multiplying means.

47. The ultrasound imaging system of claim 44 wherein said accumulator means are grouped such that a single coefficient is used for the computation of the in-phase or quadrature outputs of four said filters, thereby minimizing the number of required coefficients.

48. The ultrasound imaging system of claim 46 wherein said accumulator means are implemented with a pair of storage registers connected in series such that the multiplying means and arithmetic logic units can be time shared in order to reduce the required number of multiplying means and arithmetic logic units.

49. In an ultrasound imaging system generating flow velocity data indicative of the magnitude of a plurality of discrete ultrasound Doppler frequencies, velocity-determining means receiving said flow velocity data and generating a word indicative of a single blood flow velocity that approximates a range of said ultrasound frequencies, said velocity-determining means comprising:

power-determining means receiving said flow velocity data and determining the power of each of said discrete Doppler frequencies;

peak power-detecting means for determining which of said Doppler frequencies has the maximum power and for providing an output indicative thereof;

first calculating means receiving said flow velocity data and the output of said peak power detection means, said first calculating means calculating a first value from said digital flow velocity data, said first value corresponding to the sum of the magnitude of at least one discrete Doppler frequency above and at least one discrete Doppler frequency below the discrete Doppler frequency having the maximum power;

second calculating means receiving said flow velocity data and the output of said peak power detection means, said second calculating means calculating a second value from said digital flow velocity data, said second value corresponding to the sum of the magnitude of at least one discrete Doppler frequency above and at least one discrete Doppler frequency below the discrete Doppler frequency having the maximum power; and third calculating means calculating as said data indicative of a single blood flow velocity the ratio of said first value to said second value.

50. In an ultrasound transducer adapted for use with an ultrasound imaging system transmitting and receiving a plurality of ultrasound signals from respective transducer elements arranged in a linear array, said ultrasound signals being coupled through a coupling wedge comprising a hollow, wedge-shaped body defining a cavity filled with a coupling fluid, said wedge-shaped body having a first wall in contact with said transducer elements, a second wall positioned at an angle with respect to said first wall and adapted to contact the skin of a patient in order to position said transducer elements at a fixed predetermined angle with respect to the skin of said patient, and a third wall extending between said first and second walls to form a triangle with said first and second walls, the improvement comprising a sound-absorbing material lining the inner surface of said third wall to absorb ultrasound signals reflected from said second wall back into said coupling fluid.

51. The transducer of claim 50 wherein said third wall and said sound-absorbing material are angled toward one of said side walls so that any ultrasound reflected from said sound-absorbing material is reflected toward one of said side walls rather than toward said first or second walls.

52. In an ultrasound transducer adapted for use with an ultrasound imaging system transmitting and receiving a plurality of ultrasound signals from respective transducer elements arranged in a linear array, said ultrasound signals being coupled through a coupling wedge comprising a hollow, wedge-shaped body defining a cavity filled with a coupling fluid, said wedge-shaped body having a first wall in contact with said transducer elements, a second wall positioned at an angle with respect to said first wall and adapted to contact the skin of a patient in order to position said transducer elements at a fixed predetermined angle with respect to the skin of said patient, a third wall extending between said first and second walls to form a triangle with said first and second walls, and two opposed, generally parallel, triangularly shaped side walls enclosing the volume between said first, second and third walls, the improvement comprising a configuration for said coupling wedge wherein said third wall is angled toward one of said side walls so that any ultrasound reflected from said third wall is reflected toward one of said side walls rather than toward said first or second walls.

\* \* \* \* \*